US011780845B2

(12) United States Patent
Touré et al.

(10) Patent No.: US 11,780,845 B2
(45) Date of Patent: Oct. 10, 2023

(54) FGFR INHIBITORS AND METHODS OF USE THEREOF

(71) Applicants: Relay Therapeutics, Inc., Cambridge, MA (US); D.E. Shaw Research, LLC, New York, NY (US)

(72) Inventors: Bakary-Barry Touré, Cambridge, MA (US); Heike Schoenherr, Cambridge, MA (US); Fabrizio Giordanetto, New York, NY (US); Demetri T. Moustakas, Cambridge, MA (US); Brandi M. Hudson, Cambridge, MA (US)

(73) Assignees: Relay Therapeutics, Inc., Cambridge, MA (US); D.E. Shaw Research, LLC, New York, NY (US)

( * ) Notice: Subject to any disclaimer, the term of this patent is extended or adjusted under 35 U.S.C. 154(b) by 0 days.

(21) Appl. No.: 18/162,127

(22) Filed: Jan. 31, 2023

(65) Prior Publication Data
US 2023/0192709 A1    Jun. 22, 2023

Related U.S. Application Data

(63) Continuation of application No. 17/595,257, filed as application No. PCT/US2020/032474 on May 12, 2020.

(60) Provisional application No. 63/011,469, filed on Apr. 17, 2020, provisional application No. 62/993,957, filed on Mar. 24, 2020, provisional application No. 62/846,991, filed on May 13, 2019.

(51) Int. Cl.
| | | |
|---|---|---|
| *C07D 487/04* | (2006.01) | |
| *C07D 487/22* | (2006.01) | |
| *C07D 491/048* | (2006.01) | |
| *C07D 498/22* | (2006.01) | |
| *C07D 519/00* | (2006.01) | |
| *C07D 498/02* | (2006.01) | |

(52) U.S. Cl.
CPC ......... *C07D 487/04* (2013.01); *C07D 487/22* (2013.01); *C07D 491/048* (2013.01); *C07D 498/02* (2013.01); *C07D 498/22* (2013.01); *C07D 519/00* (2013.01)

(58) Field of Classification Search
CPC .................................................. C07D 487/04
See application file for complete search history.

(56) References Cited

U.S. PATENT DOCUMENTS

| | | |
|---|---|---|
| 6,001,839 A | 12/1999 | Calderwood et al. |
| 6,140,332 A | 10/2000 | Traxler et al. |
| 6,180,636 B1 | 1/2001 | Traxler et al. |
| 7,323,469 B2 | 1/2008 | Bold et al. |
| 2006/0040965 A1 | 2/2006 | Farthing et al. |
| 2022/0194946 A1 | 6/2022 | Lescarbeau et al. |

FOREIGN PATENT DOCUMENTS

| | | |
|---|---|---|
| CN | 102286048 A | 12/2011 |
| EP | 1661896 A1 | 5/2006 |
| EP | 2657233 A1 | 10/2013 |
| EP | 3269370 A1 | 1/2018 |
| WO | WO-1998041525 A1 | 9/1998 |
| WO | WO-0140230 A1 | 6/2001 |
| WO | WO-200250306 A1 | 6/2002 |
| WO | WO-02100864 A1 | 12/2002 |
| WO | WO-2005121147 A1 | 12/2005 |
| WO | WO-2006004658 A2 | 1/2006 |
| WO | WO-2006004703 A2 | 1/2006 |
| WO | WO-2007079862 A1 | 7/2007 |
| WO | WO-2010126960 A1 | 11/2010 |
| WO | WO-2013078254 A1 | 5/2013 |
| WO | WO-2013085802 A1 | 6/2013 |
| WO | WO-2015107495 A1 | 7/2015 |
| WO | WO-2018049233 A1 | 3/2018 |
| WO | WO-2018057884 A1 | 3/2018 |
| WO | WO-2018136265 A1 | 7/2018 |
| WO | WO-2018172984 A1 | 9/2018 |
| WO | WO-2020231990 A1 | 11/2020 |
| WO | WO-2022109577 A1 | 5/2022 |

OTHER PUBLICATIONS

U.S. Appl. No. 17/595,257, filed Nov. 12, 2021.
Azoury et al., "Fibroblast Growth Factor Receptor 2 (FGFR2) Mutation Related Syndromic Craniosynostosis," Int. J. Biol. Sci. 2017; 13(12):1479-88.
Babina and Turner, "Advances and challenges in targeting FGFR signalling in cancer," Nat. Rev. Cancer. 2017; 17(5):318-32.
Chae et al., "Inhibition of the fibroblast growth factor receptor (FGFR) pathway: the current landscape and barriers to clinical application," Oncotarget. 2017; 8(9):16052-74.
Dardaei et al., "SHP2 inhibition restores sensitivity in ALK-rearranged non-small-cell lung cancer resistant to ALK inhibitors," Nat Med. 2018; 24(4):512-17.
Fedele et al., "SHP2 Inhibition Abrogates MEK inhibitor Resistance in Multiple Cancer Models," BioRxiv. 2018; 307876.
Formisano et al., "Aberrant FGFR signaling mediates resistance to CDK4/6 inhibitors in ER+ breast cancer," Nat. Comm. 2019; 10(1):1373-86.
Gagné-Sansfaçon et al., "SHP-2 phosphatase contributes to KRAS-driven intestinal oncogenesis but prevents colitis-associated cancer development," Oncotarget. 2016; 7(40):65676-95.
Gattineni et al., "Regulation of renal phosphate transport by FGF23 is mediated by FGFR1 and FGFR4," Am. J. Physiol. Renal Physiol. 2014; 306(3):F351-8.

(Continued)

*Primary Examiner* — Brian E McDowell
(74) *Attorney, Agent, or Firm* — Dechert LLP; Andrea L. C. Reid; Gang Wang

(57) ABSTRACT

The present disclosure relates to novel compounds and pharmaceutical compositions thereof, and methods for inhibiting the activity of FGFR enzymes with the compounds and compositions of the disclosure. The present disclosure further relates to, but is not limited to, methods for treating disorders associated with FGFR signaling with the compounds and compositions of the disclosure.

2 Claims, No Drawings

(56) References Cited

OTHER PUBLICATIONS

Han et al., "Conditional Deletion of Fgfr1 in the Proximal and Distal Tubule Identifies Distinct Roles in Phosphate and Calcium Transport," PLoS One. 2016; 11(2):e0147845.

International Search Report and Written Opinion from PCT/US20/32474 dated Jul. 6, 2020 (10 pages).

International Search Report and Written Opinion from PCT/US2021/072480, dated Jan. 19, 2022 (11 pages).

Katoh, "Fibroblast growth factor receptors as treatment targets in clinical oncology," Nat. Rev. Clin. Oncol. 2019; 16:105-22.

Porta et al. "FGFR a promising druggable target in cancer: Molecular biology and new drugs," Crit. Rev. Oncol. Hematol. 2017; 113:256-67.

Prahallad et al., "PTPN11 Is a Central Node in Intrinsic and Acquired Resistance to Targeted Cancer Drugs," Cell Rep. 2015; 12(12):1978-85.

Torres-Ayuso et al., "Shipping Out MEK Inhibitor Resistance with SHP2 Inhibitors," Cancer Discov. 2018; 8(10)-1210-12.

Turner and Grose, "Fibroblast growth factor signalling: from development to cancer," Nat. Rev. Cancer. 2010; 10(2):116-29.

Wu et al., "Identification of Targetable FGFR Gene Fusions in Diverse Cancers," Cancer Discov. 2013; 3(6):636-647.

Calvet et al., "Synthesis of Polysubstituted 5-Azaindoles via Palladium-Catalyzed Heteroannulation of Diarylalkynes," J. Org. Chem. 2011; 76(11):4734-40.

FGFR INHIBITORS AND METHODS OF USE THEREOF

CROSS-REFERENCE TO RELATED APPLICATIONS

This application is a continuation application of U.S. patent application Ser. No. 17/595,257, filed Nov. 12, 2021, which is the national stage of International (PCT) Patent Application No. PCT/US2020/032474, filed May 12, 2020, which claims the benefit of U.S. Provisional Application No. 62/846,991, filed on May 13, 2019; U.S. Provisional Application No. 62/993,957, filed on Mar. 24, 2020; and U.S. Provisional Application No. 63/011,469, filed on Apr. 17, 2020; the entirety of each of which is hereby incorporated by reference.

BACKGROUND

Fibroblast growth factor receptors (FGFR1, FGFR2, FGFR3, and FGFR4) are receptor tyrosine kinases consisting of an extracellular ligand binding domain and an intracellular tyrosine kinase domain. Binding of FGF ligands leads to receptor dimerization and a conformational change in the intracellular domain resulting in intermolecular transphosphorylation of the kinase domain and intracellular tail. Phosphorylated residues serve as docking sites for adaptor proteins that promote downstream signaling cascades leading to cellular behaviors including proliferation, survival, differentiation, migration, and angiogenesis. Deregulated FGFR signaling can occur via FGFR gene amplification or fusion, FGFR missense mutations, receptor overexpression resulting from dysregulation of epigenetic and/or transcriptional regulators, or upregulation of FGF ligands in the tumor microenvironment. FGFRs are expressed on many cell types; thus, aberrant FGFR signaling has been implicated in oncogenesis, tumor progression, and resistance to therapy across many tumor types. (For a review of FGFR signaling, see N. Turner and R. Grose, Nat. Rev. Cancer 2010, 10:116-129; and references cited therein.).

Pan-FGFR1-3 inhibitors have generated clinical responses in numerous FGFR-altered cancers, however on-target toxicity limits dosing of these inhibitors. One of the most common adverse effects of pan-FGFR inhibition is hyperphosphatemia. Regulation of phosphate reabsorption is mediated by FGFR3 and FGFR1. Thus, there is a need for FGFR-selective inhibitors that spare FGFR1. (J. Gattineni et al., *Am. J. Physiol. Renal Physiol.* 2014, 306:F351-F358; X. Han et al., *PLoS One* 2016, 11:e0147845.) Cancers harboring FGFR2 gene fusions as well as those with FGFR2 amplification and/or FGFR2 activating mutations have demonstrated responses to pan-FGFR inhibition, however the low rates and duration of responses suggest they were limited by toxicities. Thus, there is a need for FGFR2-selective inhibitor compounds and methods for treating cancers and other disorders with these compounds. (For reviews of pan-FGFR1-3 inhibitors and clinical responses, see I. S. Babina and N. C. Turner, *Nat. Rev. Cancer* 2017, 17:318-332; M. Katoh, *Nat. Rev. Clin. Oncol.* 2019, 16:105-122; and references cited therein.).

SUMMARY

In some embodiments, the present disclosure provides a compound of formula I-1:

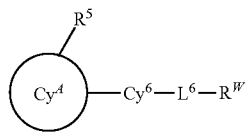

I-1 or a pharmaceutically acceptable salt thereof, wherein each of $Cy^A$, $Cy^6$, $L^6$, $R^5$, and $R^W$ is as defined in embodiments and classes and subclasses herein.

In some embodiments, the present disclosure provides a compound of formula I:

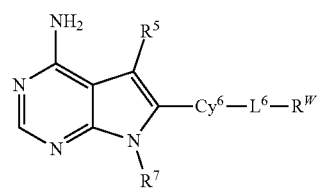

I or a pharmaceutically acceptable salt thereof, wherein each of $Cy^6$, $L^6$, $R^5$, $R^7$, and $R^W$ is as defined in embodiments and classes and subclasses herein.

In some embodiments, the present invention provides a pharmaceutical composition comprising a compound of formula I, or a pharmaceutically acceptable salt thereof, and a pharmaceutically acceptable carrier, adjuvant, or diluent. In some embodiments, the present invention provides a pharmaceutical composition comprising a compound of the disclosure, for example, a compound of formula I-1, or a pharmaceutically acceptable salt thereof, and a pharmaceutically acceptable carrier, adjuvant, or diluent.

In some embodiments, the present invention provides a method of treating a FGFR-mediated disorder comprising administering to a patient in need thereof a compound of formula I, or composition comprising said compound. In some embodiments, the present invention provides a method of treating a FGFR-mediated disorder comprising administering to a patient in need thereof a compound of the disclosure, for example, a compound of formula I-1, or composition comprising said compound.

In some embodiments, the present invention provides a process for providing a compound of formula I, or synthetic intermediates thereof. In some embodiments, the present invention provides a process for providing a compound of the disclosure, for example, a compound of formula I-1, or synthetic intermediates thereof.

In some embodiments, the present invention provides a process for providing pharmaceutical compositions comprising compounds of formula I. In some embodiments, the present invention provides a process for providing pharmaceutical compositions comprising compounds of the disclosure, for example, a compound of formula I-1.

DETAILED DESCRIPTION

1. General Description of Certain Embodiments of the Invention

Compounds of the present invention, and pharmaceutical compositions thereof, are useful as inhibitors of FGFR2. In some embodiments, the present invention provides a compound of formula I-1:

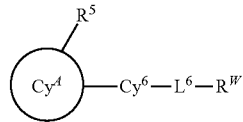

I-1 or a pharmaceutically acceptable salt thereof, wherein:

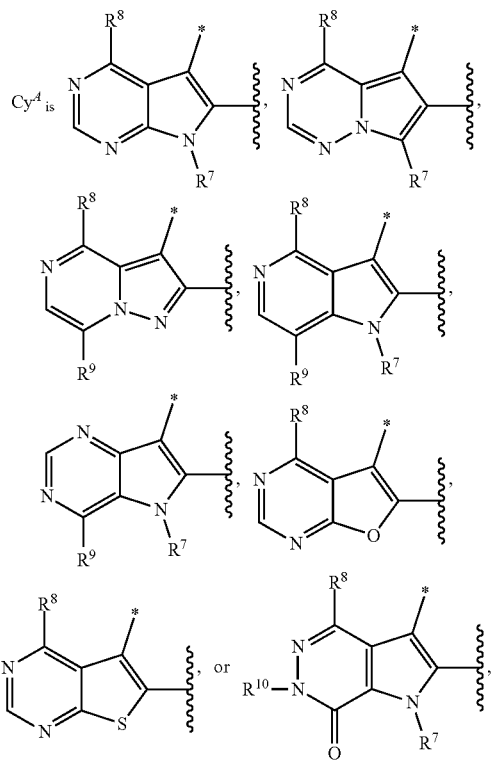

wherein ⁎ represents a bond to $R^5$ and ⁑ represents a bond to $Cy^6$;
$R^5$ is —$R^{5A}$-$L^5$-$R^{5B}$;
$R^{5A}$ is a bivalent radical of $R^B$, wherein $R^{5A}$ is substituted with m instances of $R^{5C}$ in addition to -$L^5$-$R^{5B}$;
$R^{5B}$ is hydrogen or $R^B$, wherein $R^{5B}$ is substituted with n instances of $R^{5D}$;
$Cy^6$ is phenylene; a bivalent saturated or partially unsaturated 3-14 membered carbocyclic ring; a bivalent saturated or partially unsaturated 3-14 membered heterocyclic ring having 1-4 heteroatoms independently selected from nitrogen, oxygen, and sulfur; or a 5-14 membered heteroarylene having 1-4 heteroatoms independently selected from nitrogen, oxygen, and sulfur; wherein $Cy^6$ is substituted with p instances of $R^6$ in addition to -$L^6$-$R^W$;
$R^W$ is halogen, —CN,

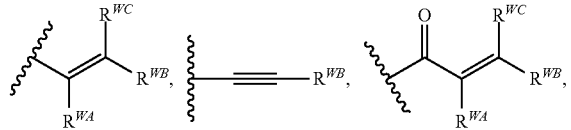

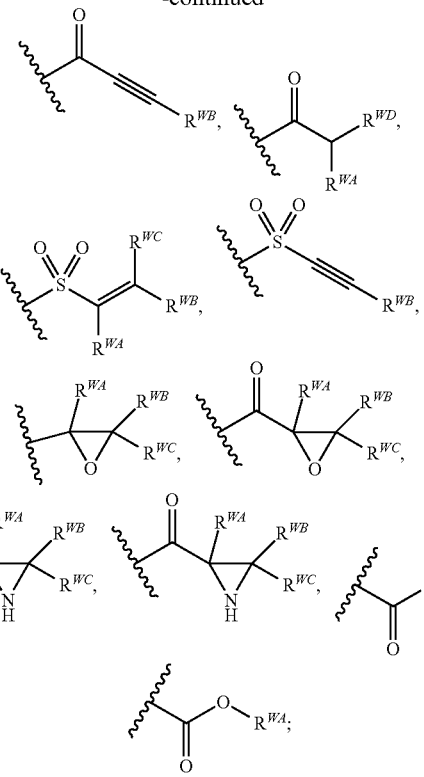

each instance of $R^6$ is independently $R^A$ or $R^B$, wherein $R^6$ is substituted by q instances of $R^C$; or
two instances of $R^6$, an instance of $R^6$ and an instance of $R^L$, an instance of $R^6$ and an instance of $R^{WA}$, or an instance of $R^6$ and an instance of $R^{7a}$ are taken together with their intervening atoms to form a 4-8 membered partially unsaturated or aromatic ring having 0-4 heteroatoms independently selected from nitrogen, oxygen, and sulfur; wherein said ring is substituted with r instances of $R^C$;
$R^7$ is H or $R^B$, wherein $R^7$ is substituted with t instances of $R^{7A}$;
$R^8$ is H, —$NR_2$, halogen, —OH, or $C_{1-6}$ aliphatic optionally substituted with 1-3 halogens;
$R^9$ is H, —$NR_2$, halogen, or $C_{1-6}$ aliphatic optionally substituted with 1-3 halogens;
$R^{10}$ is H or $C_{1-6}$ aliphatic optionally substituted with 1-3 halogens;
each of $L^5$ and $L^6$ is independently a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-6}$ cycloalkylene, 3-6 membered heterocycloalkylene, 5-6 membered heteroarylene, —NH—, —N($R^L$)—, —NHC(O)—, —N($R^L$)C(O)—, —C(O)NH—, —C(O)N($R^L$)—, —NHS(O)$_2$—, —N($R^L$)S(O)$_2$—, —S(O)$_2$NH—, —S(O)$_2$N($R^L$)—, —O—, —C(O)—, —OC(O)—, —C(O)O—, —S—, —S(O)—, or —S(O)$_2$—; wherein each of said $C_{3-6}$ cycloalkylene, 3-6 membered heterocycloalkylene, and 5-6 membered heteroarylene is optionally substituted with one instance of $R^A$ or $C_{1-6}$ aliphatic;
each of $R^{WA}$, $R^{WB}$, and $R^{WC}$ is independently hydrogen, deuterium, halogen, —CN, —C(O)R, —C(O)OR, —C(O)NR$_2$, —C(O)N(R)OR, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; or $R^{WA}$ and $R^{WB}$, $R^{WB}$ and $R^{WC}$, $R^{WA}$ and an instance of $R^L$, or $R^{WC}$ and an instance of $R^L$ are taken together with their intervening atoms to form a 4-7 membered saturated or partially unsaturated ring having 0-2 heteroatoms independently selected from nitrogen, oxygen, and sulfur; wherein said ring is substituted with w instances of $R^C$;

$R^{WD}$ is halogen or —OS(O)$_2$R;

each instance of $R^{5C}$, $R^{5D}$, $R^{7A}$, and $R^L$ is independently $R^A$ or $R^B$, and is substituted by u instances of $R^C$; or two instances of $R^{5C}$, one instance of $R^{5C}$ and one instance of $R^{5D}$, or two instances of $R^{5D}$ are taken together with their intervening atoms to form a 3-7 membered saturated, partially unsaturated, or aromatic ring having 0-4 heteroatoms independently selected from nitrogen, oxygen, and sulfur; wherein said ring is substituted with v instances of $R^C$;

each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —S(O)$_2$F, —OS(O)$_2$F, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each of m, n, p, q, r, t, u, v, and w is independently 0, 1, 2, 3, or 4.

In some embodiments, the present invention provides a compound of formula I:

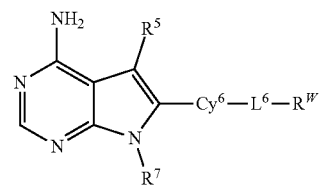

or a pharmaceutically acceptable salt thereof, wherein:

$R^5$ is —$R^{5A}$-$L^5$-$R^{5B}$;

$R^{5A}$ is a bivalent radical of $R^B$, wherein $R^{5A}$ is substituted with m instances of $R^{5C}$ in addition to -$L^5$-$R^{5B}$;

$R^{5B}$ is hydrogen or $R^B$, wherein $R^{5B}$ is substituted with n instances of $R^{5D}$;

$Cy^6$ is phenylene or a 6-membered heteroarylene having 1-3 nitrogen atoms, wherein $Cy^6$ is substituted with p instances of $R^6$ in addition to -$L^6$-$R^W$;

$R^W$ is halogen, —CN,

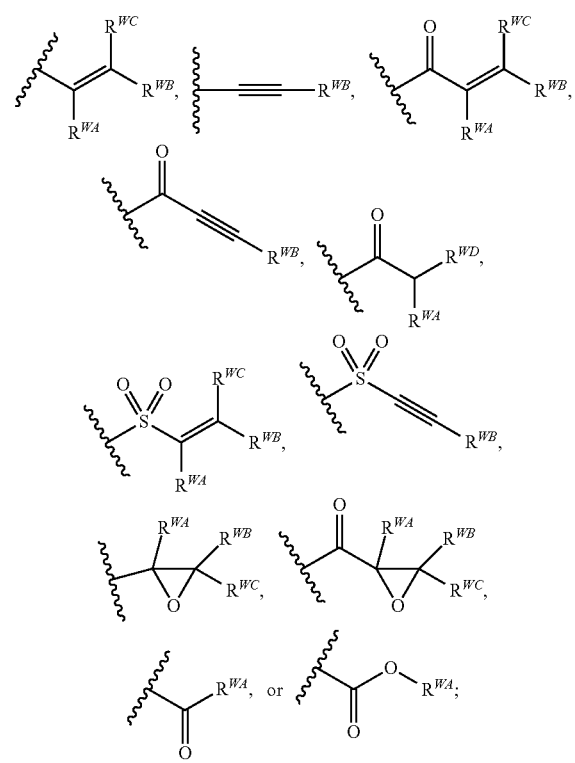

each instance of $R^6$ is independently $R^A$ or $R^B$, wherein $R^6$ is substituted by q instances of $R^C$; or two instances of $R^6$, or an instance of $R^6$ and an instance of $R^L$ are taken together with their intervening atoms to form a 4-7 membered partially unsaturated or aromatic ring having 0-4 heteroatoms independently selected from nitrogen, oxygen, and sulfur; wherein said ring is substituted with r instances of $R^C$;

$R^7$ is H or $R^B$, wherein $R^7$ is substituted with t instances of $R^{7A}$;

each of $L^5$ and $L^6$ is independently a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-5}$ cycloalkylene, 3-5 membered heterocycloalkylene, 5-6 membered heteroarylene, —NH—, —N($R^L$)—, —NHC(O)—, —N($R^L$)C(O)—, —C(O)NH—, —C(O)N($R^L$)—, —NHS(O)$_2$—, —N($R^L$)S(O)$_2$—, —S(O)$_2$NH—, —S(O)$_2$N($R^L$)—, —O—, —C(O)—, —OC(O)—, —C(O)O—, —S—, —S(O)—, or —S(O)$_2$—;

each of $R^{WA}$, $R^{WB}$, and $R^{WC}$ is independently hydrogen, halogen, —CN, —C(O)R, —C(O)OR, —C(O)NR$_2$, —C(O)N(R)OR, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; or $R^{WA}$ and $R^{WB}$, $R^{WB}$ and $R^{WC}$, $R^{WA}$ and an instance of $R^L$, or $R^{WC}$ and an instance of $R^L$ are taken together with their intervening atoms to form a 4-7 membered saturated or partially unsaturated ring having 0-2 heteroatoms independently selected from nitrogen, oxygen, and sulfur;

$R^{WD}$ is halogen or —OS(O)$_2$R;

each instance of $R^{5C}$, $R^{5D}$, $R^{7A}$, and $R^L$ is independently $R^A$ or $R^B$, and is substituted by u instances of $R^C$;

each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —S(O)$_2$F, —OS(O)$_2$F, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each of m, n, p, q, r, t, and u is independently 0, 1, 2, 3, or 4.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference. Chemical names, common names, and chemical structures may be used interchangeably to describe the same structure. If a chemical compound is referred to using both a chemical structure and a chemical name, and an ambiguity exists between the structure and the name, the structure predominates.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "alkyl", unless otherwise indicated, as used herein, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, wherein the one or more substituents are independently $C_1$-$C_{10}$ alkyl. Examples of "alkyl" groups include methyl, ethyl, propyl, isopropyl, butyl, iso-butyl, sec-butyl, tert-butyl, pentyl, hexyl, heptyl, cyclopropyl, cyclobutyl, cyclopentyl, cyclohexyl, cycloheptyl, norbornyl, and the like.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "$C_{1-8}$ (or $C_{1-6}$, or $C_{1-4}$) bivalent saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $—(CH_2)_n—$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl," used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but is not limited to, phenyl, biphenyl, naphthyl, anthracyl and the like, which may bear one or more substituents.

The terms "heteroaryl" or "heteroaromatic", unless otherwise defined, as used herein refers to a monocyclic aromatic 5-6 membered ring containing one or more heteroatoms, for example one to three heteroatoms, such as nitrogen, oxygen, and sulfur, or an 8-10 membered polycyclic ring system containing one or more heteroatoms, wherein at least one ring in the polycyclic ring system is aromatic, and the point of attachment of the polycyclic ring system is through a ring atom on an aromatic ring. A heteroaryl ring may be linked to adjacent radicals though carbon or nitrogen. Examples of heteroaryl rings include but are not limited to furan, thiophene, pyrrole, thiazole, oxazole, isothiazole, isoxazole, imidazole, pyrazole, triazole, pyridine, pyrimidine, indole, etc. For example, unless otherwise defined, 1,2,3,4-tetrahydroquinoline is a heteroaryl ring if its point of attachment is through the benzo ring, e.g.:

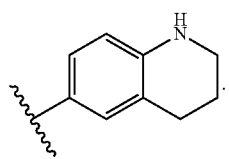 [SMILES: *c1ccc2c(c1)CCCN2]

The terms "heterocyclyl" or "heterocyclic group", unless otherwise defined, refer to a saturated or partially unsaturated 3-10 membered monocyclic or 7-14 membered polycyclic ring system, including bridged or fused rings, and whose ring system includes one to four heteroatoms, such as nitrogen, oxygen, and sulfur. A heterocyclyl ring may be linked to adjacent radicals through carbon or nitrogen.

The term "partially unsaturated" in the context of rings, unless otherwise defined, refers to a monocyclic ring, or a component ring within a polycyclic (e.g. bicyclic, tricyclic, etc.) ring system, wherein the component ring contains at least one degree of unsaturation in addition to those provided by the ring itself, but is not aromatic. Examples of partially unsaturated rings include, but are not limited to, 3,4-dihydro-2H-pyran, 3-pyrroline, 2-thiazoline, etc. Where a partially unsaturated ring is part of a polycyclic ring system, the other component rings in the polycyclic ring system may be saturated, partially unsaturated, or aromatic, but the point of attachment of the polycyclic ring system is on a partially unsaturated component ring. For example, unless otherwise defined, 1,2,3,4-tetrahydroquinoline is a partially unsaturated ring if its point of attachment is through the piperidino ring, e.g.:

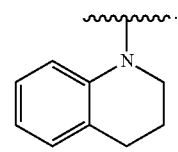

The term "saturated" in the context of rings, unless otherwise defined, refers to a 3-10 membered monocyclic ring, or a 7-14 membered polycyclic (e.g. bicyclic, tricyclic, etc.) ring system, wherein the monocyclic ring or the component ring that is the point of attachment for the polycyclic ring system contains no additional degrees of unsaturation in addition to that provided by the ring itself. Examples of monocyclic saturated rings include, but are not limited to, azetidine, oxetane, cyclohexane, etc. Where a saturated ring is part of a polycyclic ring system, the other component rings in the polycyclic ring system may be saturated, partially unsaturated, or aromatic, but the point of attachment of the polycyclic ring system is on a saturated component ring. For example, unless otherwise defined, 2-azaspiro[3.4]oct-6-ene is a saturated ring if its point of attachment is through the azetidino ring, e.g.:

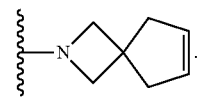

The terms "alkylene", "arylene", "cycloalkylene", "heteroarylene", "heterocycloalkylene", and the other similar terms with the suffix "-ylene" as used herein refers to a divalently bonded version of the group that the suffix modifies. For example, "alkylene" is a divalent alkyl group connecting the groups to which it is attached.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

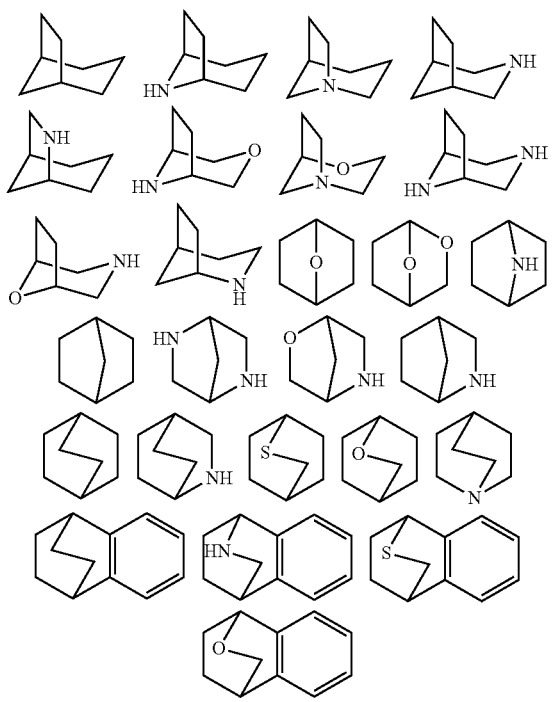

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^{\circ}$; $-(CH_2)_{0-4}OR^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}SR^{\circ}$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH=CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSiR^{\circ}_3$; $-(CH_2)_{0-4}OC(O)R^{\circ}$; $-OC(O)(CH_2)_{0-4}SR'$; $-SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-SC(S)SR^{\circ}$, $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR'$; $-(CH_2)_{0-4}OS(O)_2R^{\circ}$; $-S(O)_2NR^{\circ}_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NH)NR^{\circ}_2$; $-P(O)(OR^{\circ})R^{\circ}$; $-P(O)R^{\circ}_2$; $-OP(O)R^{\circ}_2$; $-OP(O)(OR^{\circ})_2$; $-SiR^{\circ}_3$; $-(C_{1-4}$ straight or branched)alkylene)$O-N(R^{\circ})_2$; or $-(C_{1-4}$ straight or branched) alkylene)$C(O)O-N(R^{\circ})_2$, wherein each $R^{\circ}$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, $-(CH_2)_{0-2}R^{\bullet}$, -(halo$R^{\bullet}$), $-(CH_2)_{0-2}OH$, $-(CH_2)_{0-2}OR^{\bullet}$, $-(CH_2)_{0-2}CH(OR^{\bullet})_2$; $-O(halo R^{\bullet})$, $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include $=O$ and $=S$.

Suitable divalent substituents on a saturated carbon atom of an "optionally substituted" group include the following: $=O$, $=S$, $=NNR*_2$, $=NNHC(O)R*$, $=NNHC(O)OR*$, $=NNHS(O)_2R*$, $=NR*$, $=NOR*$, $-O(C(R*_2))_{2-3}O-$, or $-S(C(R*2))_{2-3}S-$, wherein each independent occurrence of $R*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "isomer" as used herein refers to a compound having the identical chemical formula but different structural or optical configurations. The term "stereoisomer" as used herein refers to and includes isomeric molecules that have the same molecular formula but differ in positioning of atoms and/or functional groups in the space. All stereoisomers of the present compounds (e.g., those which may exist due to asymmetric carbons on various substituents), including enantiomeric forms and diastereomeric forms, are contemplated within the scope of this disclosure. Therefore, unless otherwise stated, single stereochemical isomers as well as mixtures of enantiomeric, diastereomeric, and geometric (or conformational) isomers of the present compounds are within the scope of the invention.

The term "tautomer" as used herein refers to one of two or more structural isomers which exist in equilibrium and which are readily converted from one isomeric form to another. It is understood that tautomers encompass valence tautomers and proton tautomers (also known as prototropic tautomers). Valence tautomers include interconversions by reorganization of some of the bonding electrons. Proton tautomers include interconversions via migration of a proton, such as keto-enol and imine-enamine isomerizations. Unless otherwise stated, all tautomers of the compounds of the invention are within the scope of the invention.

The term "isotopic substitution" as used herein refers to the substitution of an atom with its isotope. The term "isotope" as used herein refers to an atom having the same atomic number as that of atoms dominant in nature but having a mass number (neutron number) different from the mass number of the atoms dominant in nature. It is understood that a compound with an isotopic substitution refers to a compound in which at least one atom contained therein is substituted with its isotope. Atoms that can be substituted with its isotope include, but are not limited to, hydrogen, carbon, and oxygen. Examples of the isotope of a hydrogen atom include $^2$H (also represented as D) and $^3$H. Examples of the isotope of a carbon atom include $^{13}$C and $^{14}$C. Examples of the isotope of an oxygen atom include $^{18}$O. Unless otherwise stated, all isotopic substitution of the compounds of the invention are within the scope of the invention. Such compounds are useful, for example, as analytical tools, as probes in biological assays, or as therapeutic agents in accordance with the present invention. In certain embodiments, for example, a warhead moiety, R$^W$, of a provided compound comprises one or more deuterium atoms.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Exemplary pharmaceutically acceptable salts are found, e.g., in Berge, et al. (*J. Pharm. Sci.* 1977, 66(1), 1; and Gould, P. L., *Int. J. Pharmaceutics* 1986, 33, 201-217; (each hereby incorporated by reference in its entirety).

Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemi-maleate, hemifumarate, and hemisuccinate.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, e.g., to reduce or ameliorate the severity and/or duration of afflictions related to FGFR2 signaling, or one or more symptoms thereof, prevent the advancement of conditions or symptoms related to afflictions related to FGFR2 signaling, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The phrase "in need thereof" refers to the need for symptomatic or asymptomatic relief from conditions related to FGFR2 signaling activity or that may otherwise be relieved by the compounds and/or compositions of the disclosure.

3. Description of Exemplary Embodiments

As described above, in some embodiments, the present invention provides a compound of formula I-1:

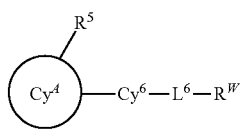

I-1 or a pharmaceutically acceptable salt thereof, wherein:

$Cy^A$ is

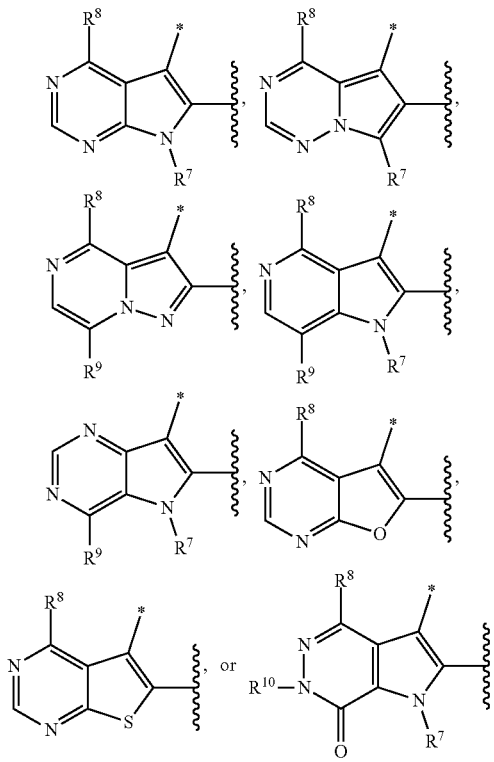

wherein ⁎ represents a bond to $R^5$ and ⌇ represents a bond to $Cy^6$;

$R^5$ is —$R^{5A}$-$L^5$-$R^{5B}$;

$R^{5A}$ is a bivalent radical of $R^B$, wherein $R^{5A}$ is substituted with m instances of $R^{5C}$ in addition to -$L^5$-$R^{5B}$;

$R^{5B}$ is hydrogen or $R^B$, wherein $R^{5B}$ is substituted with n instances of $R^{5D}$;

$Cy^6$ is phenylene; a bivalent saturated or partially unsaturated 3-14 membered carbocyclic ring; a bivalent saturated or partially unsaturated 3-14 membered heterocyclic ring having 1-4 heteroatoms independently selected from nitrogen, oxygen, and sulfur; or a 5-14 membered heteroarylene having 1-4 heteroatoms independently selected from nitrogen, oxygen, and sulfur; wherein $Cy^6$ is substituted with p instances of $R^6$ in addition to -$L^6$-$R^W$;

$R^W$ is halogen, —CN,

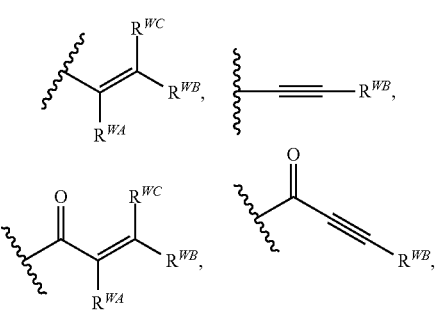

-continued

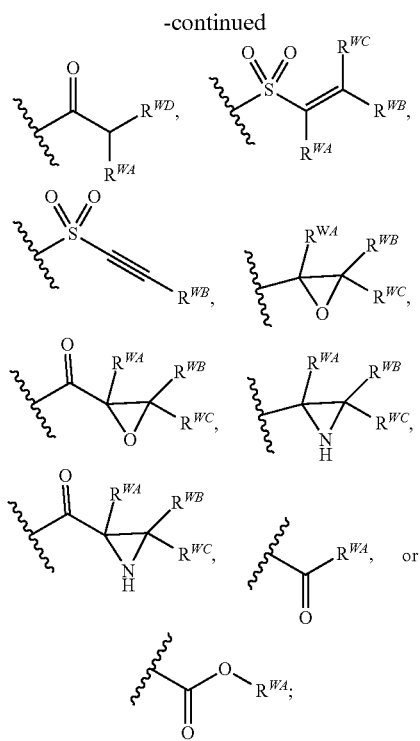

each instance of $R^6$ is independently $R^A$ or $R^B$, wherein $R^6$ is substituted by q instances of $R^C$; or
two instances of $R^6$, an instance of $R^6$ and an instance of $R^L$, an instance of $R^6$ and an instance of $R^{WA}$, or an instance of $R^6$ and an instance of $R^{7a}$ are taken together with their intervening atoms to form a 4-8 membered partially unsaturated or aromatic ring having 0-4 heteroatoms independently selected from nitrogen, oxygen, and sulfur; wherein said ring is substituted with r instances of $R^C$;

$R^7$ is H or $R^B$, wherein $R^7$ is substituted with t instances of $R^{7A}$;

$R^8$ is H, —$NR_2$, halogen, —OH, or $C_{1-6}$ aliphatic optionally substituted with 1-3 halogens;

$R^9$ is H, —$NR_2$, halogen, or $C_{1-6}$ aliphatic optionally substituted with 1-3 halogens;

$R^{10}$ is H or $C_{1-6}$ aliphatic optionally substituted with 1-3 halogens;

each of $L^5$ and $L^6$ is independently a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-6}$ cycloalkylene, 3-6 membered heterocycloalkylene, 5-6 membered heteroarylene, —NH—, —N($R^L$)—, —NHC(O)—, —N($R^L$)C(O)—, —C(O)NH—, —C(O)N($R^L$)—, —NHS(O)$_2$—, —N($R^L$)S(O)$_2$—, —S(O)$_2$NH—, —S(O)$_2$N($R^L$)—, —O—, —C(O)—, —OC(O)—, —C(O)O—, —S—, —S(O)—, or —S(O)$_2$—; wherein each of said $C_{3-6}$ cycloalkylene, 3-6 membered heterocycloalkylene, and 5-6 membered heteroarylene is optionally substituted with one instance of $R^A$ or $C_{1-6}$ aliphatic;

each of $R^{WA}$, $R^{WB}$, and $R^{WC}$ is independently hydrogen, deuterium, halogen, —CN, —C(O)R, —C(O)OR, —C(O)NR$_2$, —C(O)N(R)OR, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; or $R^{WA}$ and $R^{WB}$, $R^{WB}$ and $R^{WC}$, $R^{WA}$ and an instance of $R^L$, or $R^{WC}$ and an instance of $R^L$ are taken together with their intervening atoms to form a 4-7 membered saturated or partially unsaturated ring having 0-2 heteroatoms independently selected from nitrogen, oxygen, and sulfur; wherein said ring is substituted with w instances of $R^C$;

$R^{WD}$ is halogen or —OS(O)$_2$R;

each instance of $R^{5C}$, $R^{5D}$, $R^{7A}$, and $R^L$ is independently $R^A$ or $R^B$, and is substituted by u instances of $R^C$; or
two instances of $R^{5C}$, one instance of $R^{5C}$ and one instance of $R^{5D}$, or two instances of $R^{5D}$ are taken together with their intervening atoms to form a 3-7 membered saturated, partially unsaturated, or aromatic ring having 0-4 heteroatoms independently selected from nitrogen, oxygen, and sulfur; wherein said ring is substituted with v instances of $R^C$;

each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —S(O)$_2$F, —OS(O)$_2$F, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each of m, n, p, q, r, t, u, v, and w is independently 0, 1, 2, 3, or 4.

As defined generally above, Cy$^A$ is
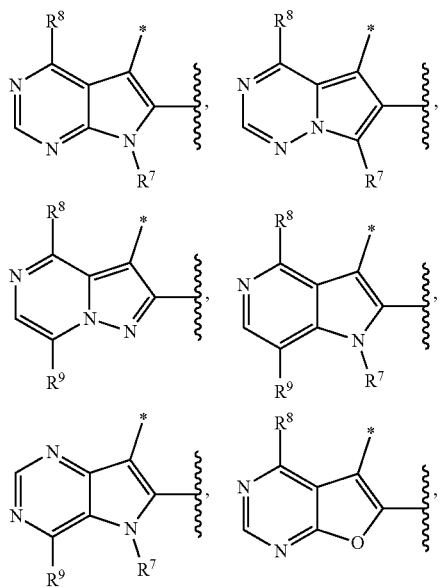
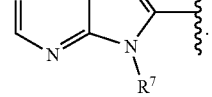
wherein ⁎ represents a bond to R$^5$ and represents a bond to Cy$^6$. In some embodiments, Cy$^A$ is
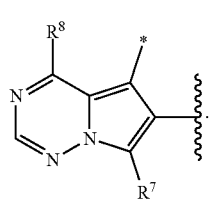
In some embodiments, Cy$^A$ is
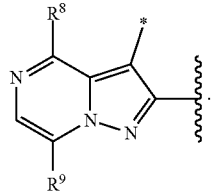
In some embodiments, Cy$^A$ is
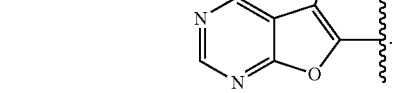
In some embodiments, Cy$^A$ is
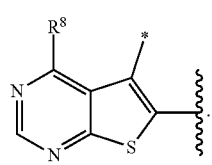
In some embodiments, Cy$^A$ is
In some embodiments, Cy$^A$ is
In some embodiments, Cy$^A$ is
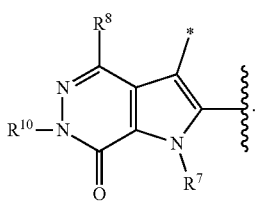

In some embodiments, Cy$^A$ is

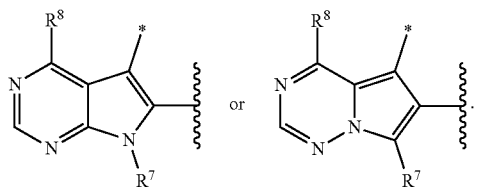

In some embodiments, Cy$^A$ is

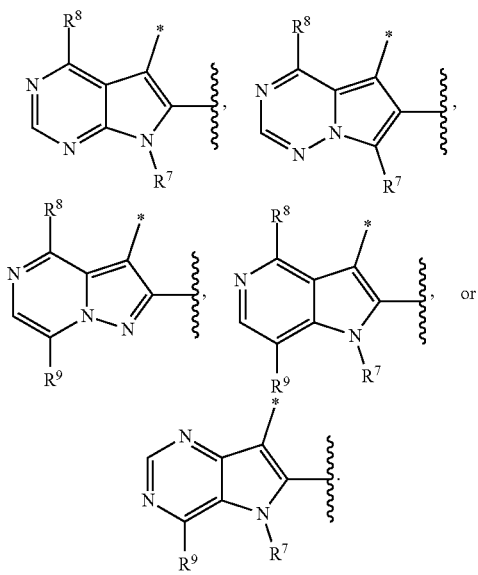

In some embodiments, Cy$^A$ is

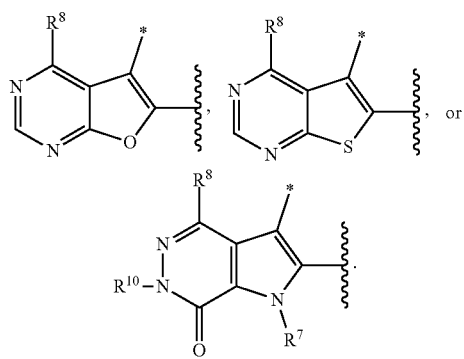

In some embodiments, Cy$^A$ is selected from the groups depicted in the compounds in Table 1.

As defined generally above, Cy$^6$ is phenylene; a bivalent saturated or partially unsaturated 3-14 membered carbocyclic ring; a bivalent saturated or partially unsaturated 3-14 membered heterocyclic ring having 1-4 heteroatoms independently selected from nitrogen, oxygen, and sulfur; or a 5-14 membered heteroarylene having 1-4 heteroatoms independently selected from nitrogen, oxygen, and sulfur; wherein Cy$^6$ is substituted with p instances of R$^6$ in addition to -L$^6$-R$^W$.

In some embodiments, Cy$^6$ is phenylene; a bivalent saturated or partially unsaturated 3-7 membered monocyclic carbocyclic ring; a bivalent saturated or partially unsaturated 8-14 membered bicyclic carbocyclic ring; a bivalent saturated or partially unsaturated 3-7 membered monocyclic heterocyclic ring having 1-4 heteroatoms independently selected from nitrogen, oxygen, and sulfur; or a bivalent saturated or partially unsaturated 8-14 membered bicyclic heterocyclic ring having 1-4 heteroatoms independently selected from nitrogen, oxygen, and sulfur; a 5-6 membered monocyclic heteroarylene having 1-4 heteroatoms independently selected from nitrogen, oxygen, and sulfur; or a 9-10 membered bicyclic heteroarylene having 1-4 heteroatoms independently selected from nitrogen, oxygen, and sulfur; wherein Cy$^6$ is substituted with p instances of R$^6$ in addition to -L$^6$-R$^W$.

In some embodiments, Cy$^6$ is a bivalent saturated or partially unsaturated 3-14 membered carbocyclic ring; wherein Cy$^6$ is substituted with p instances of R$^6$ in addition to -L$^6$-R$^W$. In some embodiments, Cy$^6$ is a bivalent saturated or partially unsaturated 3-7 membered monocyclic carbocyclic ring, or a bivalent saturated or partially unsaturated 8-14 membered bicyclic carbocyclic ring; wherein Cy$^6$ is substituted with p instances of R$^6$ in addition to -L$^6$-R$^W$. In some embodiments, Cy$^6$ is a bivalent saturated or partially unsaturated 3-7 membered monocyclic carbocyclic ring; wherein Cy$^6$ is substituted with p instances of R$^6$ in addition to -L$^6$-R$^W$. In some embodiments, Cy$^6$ is a bivalent saturated or partially unsaturated 8-14 membered bicyclic carbocyclic ring; wherein Cy$^6$ is substituted with p instances of R$^6$ in addition to -L$^6$-R$^W$.

In some embodiments, Cy$^6$ is a bivalent saturated or partially unsaturated 3-14 membered heterocyclic ring having 1-4 heteroatoms independently selected from nitrogen, oxygen, and sulfur; wherein Cy$^6$ is substituted with p instances of R$^6$ in addition to -L$^6$-R$^W$. In some embodiments, Cy$^6$ is a bivalent saturated or partially unsaturated 3-7 membered monocyclic heterocyclic ring having 1-4 heteroatoms independently selected from nitrogen, oxygen, and sulfur; or a bivalent saturated or partially unsaturated 8-14 membered bicyclic heterocyclic ring having 1-4 heteroatoms independently selected from nitrogen, oxygen, and sulfur; wherein Cy$^6$ is substituted with p instances of R$^6$ in addition to -L$^6$-R$^W$.

In some embodiments, Cy$^6$ is a bivalent saturated or partially unsaturated 3-7 membered monocyclic heterocyclic ring having 1-4 heteroatoms independently selected from nitrogen, oxygen, and sulfur; wherein Cy$^6$ is substituted with p instances of R$^6$ in addition to -L$^6$-R$^W$. In some embodiments, Cy$^6$ is a bivalent saturated or partially unsaturated 5-6 membered monocyclic heterocyclic ring having 1-2 heteroatoms independently selected from nitrogen, oxygen, and sulfur; wherein Cy$^6$ is substituted with p instances of R$^6$ in addition to -L$^6$-R$^W$. In some embodiments, Cy$^6$ is a bivalent pyrrolidine or dihydropyrrolidine ring; wherein Cy$^6$ is substituted with p instances of R$^6$ in addition to -L$^6$-R$^W$.

In some embodiments, Cy$^6$ is a 5-14 membered heteroarylene having 1-4 heteroatoms independently selected from nitrogen, oxygen, and sulfur; wherein Cy$^6$ is substituted with p instances of R$^6$ in addition to -L$^6$-R$^W$. In some embodiments, Cy$^6$ is a 5-6 membered monocyclic heteroarylene having 1-4 heteroatoms independently selected from nitrogen, oxygen, and sulfur; or a 9-10 membered bicyclic heteroarylene having 1-4 heteroatoms independently selected from nitrogen, oxygen, and sulfur; wherein Cy$^6$ is substituted with p instances of R$^6$ in addition to -L$^6$-R$^W$.

In some embodiments, Cy$^6$ is a 5-6 membered monocyclic heteroarylene having 1-4 heteroatoms independently selected from nitrogen, oxygen, and sulfur; wherein Cy$^6$ is substituted with p instances of $R^6$ in addition to -$L^6$-$R^W$. In some embodiments, $Cy^6$ is a 5-6 membered monocyclic heteroarylene having 1-2 nitrogen atoms; wherein $Cy^6$ is substituted with p instances of $R^6$ in addition to -$L^6$-$R^W$. In some embodiments, $Cy^6$ is a 5-membered monocyclic heteroarylene having 1-2 nitrogen atoms; wherein $Cy^6$ is substituted with p instances of $R^6$ in addition to -$L^6$-$R^W$.

In some embodiments, $Cy^6$ is a 9-10 membered bicyclic heteroarylene having 1-4 heteroatoms independently selected from nitrogen, oxygen, and sulfur; wherein $Cy^6$ is substituted with p instances of $R^6$ in addition to -$L^6$-$R^W$. In some embodiments, $Cy^6$ is a 9-10 membered bicyclic heteroarylene having 1-3 nitrogen atoms; wherein $Cy^6$ is substituted with p instances of $R^6$ in addition to -$L^6$-$R^W$.

In some embodiments, $Cy^6$ is selected from the groups depicted in the compounds in Table 1.

In some embodiments, -$Cy^6$-$L^6$-$R^W$ taken together is:

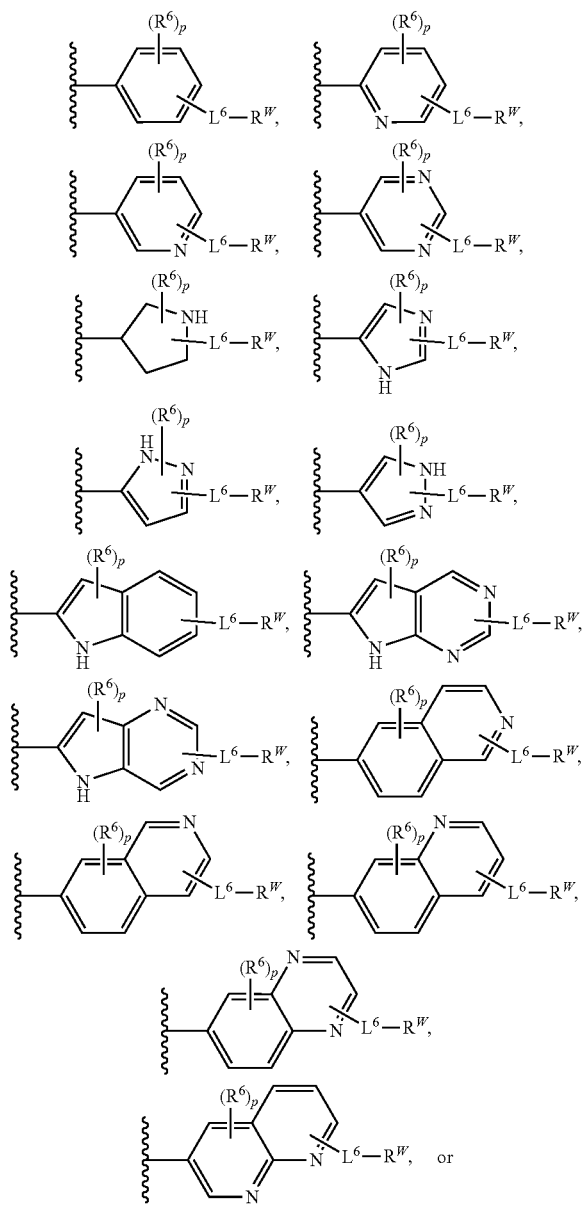

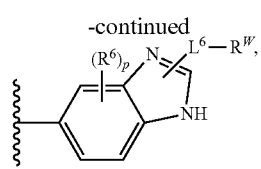

wherein each of $L^6$, $R^6$, $R^W$, and p is as defined in embodiments and classes and subclasses herein. In some embodiments, -$Cy^6$-$L^6$-$R^W$ taken together is:

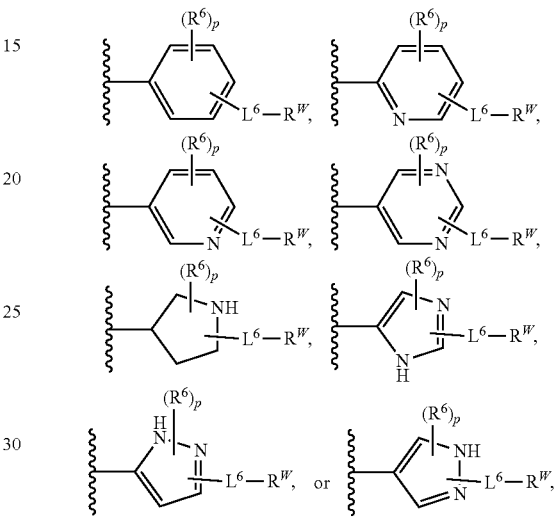

wherein each of $L^6$, $R^6$, $R^W$, and p is as defined in embodiments and classes and subclasses herein. In some embodiments, -$Cy^6$-$L^6$-$R^W$ taken together is:

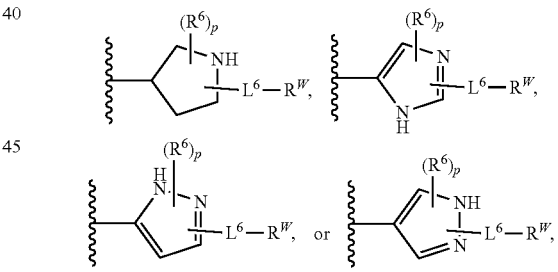

wherein each of $L^6$, $R^6$, $R^W$, and p is as defined in embodiments and classes and subclasses herein. In some embodiments, -$Cy^6$-$L^6$-$R^W$ taken together is:

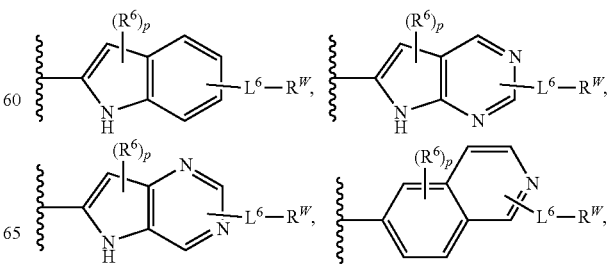

-continued

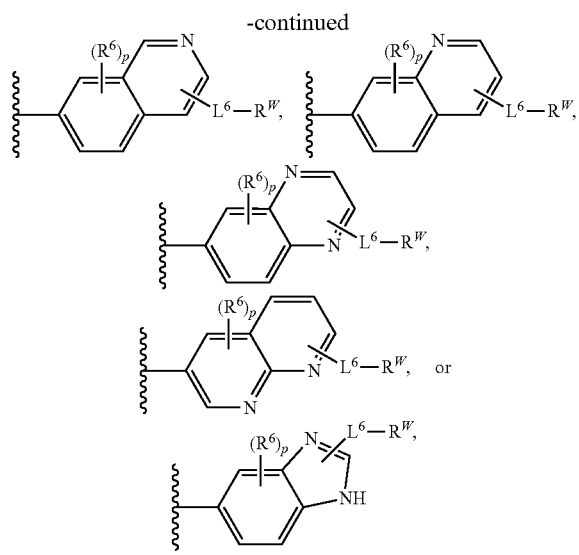

wherein each of $L^6$, $R^6$, $R^W$, and p is as defined in embodiments and classes and subclasses herein.

As defined generally above, each instance of $R^6$ is independently $R^A$ or $R^B$, wherein $R^6$ is substituted by q instances of $R^C$; or two instances of $R^6$, an instance of $R^6$ and an instance of $R^L$, an instance of $R^6$ and an instance of $R^{WA}$, or an instance of $R^6$ and an instance of $R^{7a}$ are taken together with their intervening atoms to form a 4-8 membered partially unsaturated or aromatic ring having 0-4 heteroatoms independently selected from nitrogen, oxygen, and sulfur; wherein said ring is substituted with r instances of $R^C$.

In some embodiments, two instances of $R^6$, an instance of $R^6$ and an instance of $R^L$, an instance of $R^6$ and an instance of $R^{WA}$, or an instance of $R^6$ and an instance of $R^{7a}$ are taken together with their intervening atoms to form a 4-8 membered partially unsaturated or aromatic ring having 0-4 heteroatoms independently selected from nitrogen, oxygen, and sulfur; wherein said ring is substituted with r instances of $R^C$.

In some embodiments, an instance of $R^6$ and an instance of $R^{WA}$ are taken together with their intervening atoms to form a 4-8 membered partially unsaturated or aromatic ring having 0-4 heteroatoms independently selected from nitrogen, oxygen, and sulfur; wherein said ring is substituted with r instances of $R^C$. In some embodiments, an instance of $R^6$ and an instance of $R^{7a}$ are taken together with their intervening atoms to form a 4-8 membered partially unsaturated or aromatic ring having 0-4 heteroatoms independently selected from nitrogen, oxygen, and sulfur; wherein said ring is substituted with r instances of $R^C$.

In some embodiments, an instance of $R^6$ and an instance of $R^{7a}$ are taken together with their intervening atoms to form a 4-8 membered partially unsaturated or aromatic ring having 0-4 heteroatoms independently selected from nitrogen, oxygen, and sulfur; wherein said ring is substituted with r instances of $R^C$. In some embodiments, an instance of $R^6$ and an instance of $R^{7a}$ are taken together with their intervening atoms to form a 4-8 membered partially unsaturated ring having one nitrogen atom; wherein said ring is optionally substituted with 1, 2, or 3 substituents independently selected from halogen, —CN, —O—($C_{1-4}$ alkyl), and —($C_{1-4}$ alkyl); wherein each $C_{1-4}$ alkyl is optionally substituted with 1, 2, or 3 fluoro. In some embodiments, an instance of $R^6$ and an instance of $R^{7a}$ are taken together with their intervening atoms to form a 4-8 membered partially unsaturated ring. In some embodiments, an instance of $R^6$ and an instance of $R^{7a}$ are taken together with their intervening atoms to form a 4-8 membered partially unsaturated ring having one nitrogen atom.

In some embodiments, each $R^6$ is selected from the groups depicted in the compounds in Table 1.

As defined generally above, $R^8$ is H, —$NR_2$, halogen, —OH, or $C_{1-6}$ aliphatic optionally substituted with 1-3 halogens. In some embodiments, $R^8$ is H. In some embodiments, $R^8$ is —$NR_2$. In some embodiments, $R^8$ is halogen. In some embodiments, $R^8$ is —OH. In some embodiments, $R^8$ is $C_{1-6}$ aliphatic optionally substituted with 1-3 halogens.

In some embodiments, $R^8$ is —$NH_2$. In some embodiments, $R^8$ is $C_{1-4}$ alkyl. In some embodiments, $R^8$ is methyl. In some embodiments, $R^8$ is —$NH_2$ or methyl. In some embodiments, $R^8$ is selected from the groups depicted in the compounds in Table 1.

As defined generally above, $R^9$ is H, —$NR_2$, halogen, or $C_{1-6}$ aliphatic optionally substituted with 1-3 halogens. In some embodiments, $R^9$ is H. In some embodiments, $R^9$ is —$NR_2$. In some embodiments, $R^9$ is —$NH_2$. In some embodiments, $R^9$ is halogen. In some embodiments, $R^9$ is $C_{1-6}$ aliphatic optionally substituted with 1-3 halogens. In some embodiments, $R^9$ is $C_{1-4}$ alkyl. In some embodiments, $R^9$ is selected from the groups depicted in the compounds in Table 1.

As defined generally above, $R^{10}$ is H or $C_{1-6}$ aliphatic optionally substituted with 1-3 halogens. In some embodiments, $R^{10}$ is H. In some embodiments, $R^{10}$ is $C_{1-6}$ aliphatic optionally substituted with 1-3 halogens. In some embodiments, $R^{10}$ is $C_{1-4}$ alkyl. In some embodiments, $R^{10}$ is methyl. In some embodiments, $R^{10}$ is H or methyl. In some embodiments, $R^{10}$ is selected from the groups depicted in the compounds in Table 1.

As defined generally above, $L^6$ is a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-6}$ cycloalkylene, 3-6 membered heterocycloalkylene, 5-6 membered heteroarylene, —NH—, —N($R^L$)—, —NHC(O)—, —N($R^L$)C(O)—, —C(O)NH—, —C(O)N($R^L$)—, —NHS(O)$_2$—, —N($R^L$)S(O)$_2$—, —S(O)$_2$NH—, —S(O)$_2$N($R^L$)—, —O—, —C(O)—, —OC(O)—, —C(O)O—, —S—, —S(O)—, or —S(O)$_2$—; wherein each of said $C_{3-6}$ cycloalkylene, 3-6 membered heterocycloalkylene, and 5-6 membered heteroarylene is optionally substituted with one instance of $R^A$ or $C_{1-6}$ aliphatic.

In some embodiments, $L^6$ is a $C_{3-6}$ cycloalkylene, 3-6 membered heterocycloalkylene, or 5-6 membered heteroarylene, each of which is optionally substituted with one instance of $R^A$ or $C_{1-6}$ aliphatic. In some embodiments, $L^6$ is a $C_{3-6}$ cycloalkylene, 3-6 membered heterocycloalkylene, or 5-6 membered heteroarylene.

In some embodiments, $L^6$ is selected from the groups depicted in the compounds in Table 1.

As defined generally above, each instance of $R^{5C}$ and $R^{5D}$ is independently $R^A$ or $R^B$, and is substituted by u instances of $R^C$; or two instances of $R^{5C}$, one instance of $R^{5C}$ and one instance of $R^{5D}$, or two instances of $R^{5D}$ are taken together with their intervening atoms to form a 3-7 membered saturated, partially unsaturated, or aromatic ring having 0-4 heteroatoms independently selected from nitrogen, oxygen, and sulfur; wherein said ring is substituted with v instances of $R^C$.

In some embodiments, two instances of $R^{5C}$ are taken together with their intervening atoms to form a 3-7 membered saturated, partially unsaturated, or aromatic ring having 0-4 heteroatoms independently selected from nitrogen, oxygen, and sulfur; wherein said ring is substituted with v instances of $R^C$.

In some embodiments, one instance of $R^{5C}$ and one instance of $R^{5D}$ are taken together with their intervening atoms to form a 3-7 membered saturated, partially unsaturated, or aromatic ring having 0-4 heteroatoms independently selected from nitrogen, oxygen, and sulfur; wherein said ring is substituted with v instances of $R^C$. In some embodiments, one instance of $R^{5C}$ and one instance of $R^{5D}$ are taken together with their intervening atoms to form a 3-7 membered saturated or partially unsaturated carbocyclic ring substituted with v instances of $R^C$.

In some embodiments, two instances of $R^{5D}$ are taken together with their intervening atoms to form a 3-7 membered saturated, partially unsaturated, or aromatic ring having 0-4 heteroatoms independently selected from nitrogen, oxygen, and sulfur; wherein said ring is substituted with v instances of $R^C$. In some embodiments, two instances of $R^{5D}$ are taken together with their intervening atoms to form a 3-7 membered saturated or partially unsaturated carbocyclic ring substituted with v instances of $R^C$.

In some embodiments, each instance of $R^{5C}$ and $R^{5D}$ is selected from the groups depicted in the compounds in Table 1.

As defined generally above, v is 0, 1, 2, 3, or 4. In some embodiments, v is 0. In some embodiments, v is 1. In some embodiments, v is 2. In some embodiments, v is 3. In some embodiments, v is 4. In some embodiments, v is 0 or 1. In some embodiments, v is 0, 1, or 2. In some embodiments, v is 0, 1, 2, or 3. In some embodiments, v is 1 or 2. In some embodiments, v is 1, 2, or 3. In some embodiments, v is 1, 2, 3, or 4. In some embodiments, v is 2 or 3. In some embodiments, v is 2, 3, or 4. In some embodiments, v is 3 or 4. In some embodiments, v is selected from the values represented in the compounds in Table 1.

As defined generally above, w is 0, 1, 2, 3, or 4. In some embodiments, w is 0. In some embodiments, w is 1. In some embodiments, w is 2. In some embodiments, w is 3. In some embodiments, w is 4. In some embodiments, w is 0 or 1. In some embodiments, w is 0, 1, or 2. In some embodiments, w is 0, 1, 2, or 3. In some embodiments, w is 1 or 2. In some embodiments, w is 1, 2, or 3. In some embodiments, w is 1, 2, 3, or 4. In some embodiments, w is 2 or 3. In some embodiments, w is 2, 3, or 4. In some embodiments, w is 3 or 4. In some embodiments, w is selected from the values represented in the compounds in Table 1.

In some embodiments, the present invention provides a compound of Formula I-1, wherein each of the variables is as defined in the description of Formula I or Formula I-2, below, and described in embodiments herein, both singly and in combination.

As described above, in some embodiments, the present invention provides a compound of formula I-2:

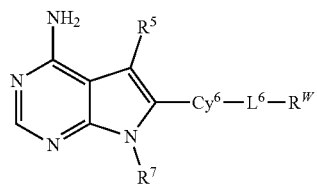

I-2 or a pharmaceutically acceptable salt thereof, wherein:
$R^5$ is —$R^{5A}$-$L^5$-$R^{5B}$;
$R^{5A}$ is a bivalent radical of $R^B$, wherein $R^{5A}$ is substituted with m instances of $R^{5C}$ in addition to -$L^5$-$R^{5B}$;
$R^{5B}$ is hydrogen or $R^B$, wherein $R^{5B}$ is substituted with n instances of $R^{5D}$;
$Cy^6$ is phenylene or a 6-membered heteroarylene having 1-3 nitrogen atoms, wherein $Cy^6$ is substituted with p instances of $R^6$ in addition to -$L^6$-$R^W$;
$R^W$ is halogen, —CN,

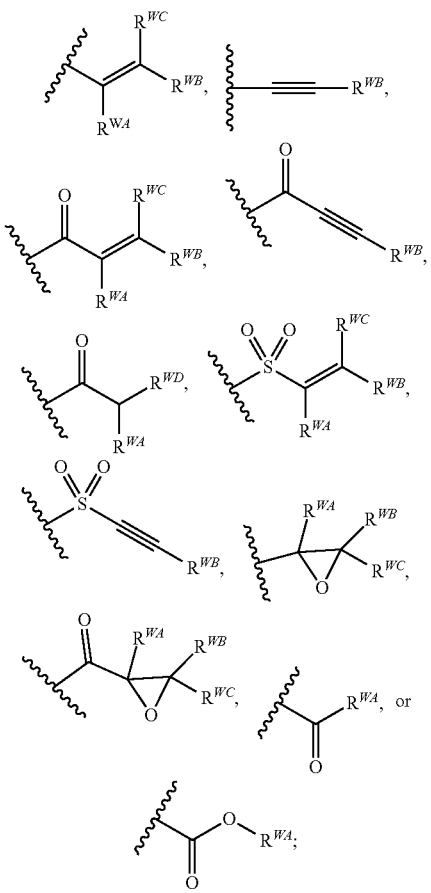

each instance of $R^6$ is independently $R^A$ or $R^B$, wherein $R^6$ is substituted by q instances of $R^C$; or
two instances of $R^6$, or an instance of $R^6$ and an instance of $R^L$ are taken together with their intervening atoms to form a 4-7 membered partially unsaturated or aromatic ring having 0-4 heteroatoms independently selected from nitrogen, oxygen, and sulfur; wherein said ring is substituted with r instances of $R^C$;
$R^7$ is H or $R^B$, wherein $R^7$ is substituted with t instances of $R^{7A}$;
each of $L^5$ and $L^6$ is independently a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-5}$ cycloalkylene, 3-5 membered heterocycloalkylene, 5-6 membered heteroarylene, —NH—, —N($R^L$)—, —NHC(O)—, —N($R^L$)C(O)—, —C(O)NH—, —C(O)N($R^L$)—, —NHS(O)$_2$—, —N($R^L$)S(O)$_2$—, —S(O)$_2$NH—, —S(O)$_2$N($R^L$)—, —O—, —C(O)—, —OC(O)—, —C(O)O—, —S—, —S(O)—, or —S(O)$_2$—;

each of $R^{WA}$, $R^{WB}$, and $R^{WC}$ is independently hydrogen, deuterium, halogen, —CN, —C(O)R, —C(O)OR, —C(O)NR$_2$, —C(O)N(R)OR, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; or $R^{WA}$ and $R^{WB}$, $R^{WB}$ and $R^{WC}$, $R^{WA}$ and an instance of $R^L$, or $R^{WC}$ and an instance of $R^L$ are taken together with their intervening atoms to form a 4-7 membered saturated or partially unsaturated ring having 0-2 heteroatoms independently selected from nitrogen, oxygen, and sulfur;

$R^{WD}$ is halogen or —OS(O)$_2$R;

each instance of $R^{5C}$, $R^{5D}$, $R^{7A}$, and $R^L$ is independently $R^A$ or $R^B$, and is substituted by u instances of $R^C$;

each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —S(O)$_2$F, —OS(O)$_2$F, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of m, n, p, q, r, t, and u is independently 0, 1, 2, 3, or 4.

As defined generally above, each of $R^{WA}$, $R^{WB}$, and $R^{WC}$ is independently hydrogen, deuterium, halogen, —CN, —C(O)R, —C(O)OR, —C(O)NR$_2$, —C(O)N(R)OR, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; or $R^{WA}$ and $R^{WB}$, $R$ and $R^{WC}$, $R^{WA}$ and an instance of $R^L$, or $R^{WC}$ and an instance of $R^L$ are taken together with their intervening atoms to form a 4-7 membered saturated or partially unsaturated ring having 0-2 heteroatoms independently selected from nitrogen, oxygen, and sulfur.

In some embodiments, each of $R^{WA}$, $R^{WB}$, and $R^{WC}$ is independently hydrogen, deuterium, halogen, —CN, —C(O)R, —C(O)OR, —C(O)NR$_2$, or —C(O)N(R)OR. In some embodiments, each of $R^{WA}$, $R^{WB}$, and $R^{WC}$ is independently hydrogen, deuterium, or optionally substituted $C_{1-6}$ aliphatic. In some embodiments, each of $R^{WA}$, $R^{WB}$, and $R^{WC}$ is independently hydrogen, deuterium, —$C_{1-4}$ alkyl, —($C_{1-4}$ alkyl)-O—($C_{1-4}$ alkyl), or —($C_{1-4}$ alkyl)-N($C_{1-4}$ alkyl)$_2$; wherein each $C_{1-4}$ alkyl is optionally substituted with 1, 2, or 3 fluoro. In some embodiments, each of $R^{WA}$, $R^{WB}$, and $R^{WC}$ is independently hydrogen, deuterium, or —$C_{1-4}$ alkyl optionally substituted with 1, 2, or 3 fluoro. In some embodiments, each of $R^{WA}$, $R^{WB}$, and $R^{WC}$ is independently hydrogen, deuterium, or —$C_{1-4}$ alkyl. In some embodiments, each of $R^{WA}$, $R^{WB}$, and $R^{WC}$ is independently hydrogen, deuterium, or —CH$_3$. In some embodiments, each of $R^{WA}$, $R^{WB}$, and $R^{WC}$ is independently hydrogen or deuterium. In some embodiments, each of $R^{WA}$, $R^{WB}$, and $R^{WC}$ is deuterium.

In some embodiments, the present invention provides a compound of Formula I-2, wherein each of the variables is as defined in the description of Formula I, below, and described in embodiments herein, both singly and in combination.

As described above, in some embodiments, the present invention provides a compound of formula I:

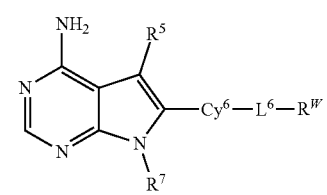

I or a pharmaceutically acceptable salt thereof, wherein:
$R^5$ is —$R^{5A}$-$L^5$-$R^{5B}$;
$R^{5A}$ is a bivalent radical of $R^B$, wherein $R^{5A}$ is substituted with m instances of $R^{5C}$ in addition to -$L^5$-$R^{5B}$;
$R^{5B}$ is hydrogen or $R^B$, wherein $R^{5B}$ is substituted with n instances of $R^{5D}$;
$Cy^6$ is phenylene or a 6-membered heteroarylene having 1-3 nitrogen atoms, wherein $Cy^6$ is substituted with p instances of $R^6$ in addition to -$L^6$-$R^W$;
$R^W$ is halogen, —CN,

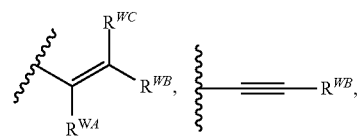

-continued each instance of $R^6$ is independently $R^A$ or $R^B$, wherein $R^6$ is substituted by q instances of $R^C$; or
  two instances of $R^6$, or an instance of $R^6$ and an instance of $R^L$ are taken together with their intervening atoms to form a 4-7 membered partially unsaturated or aromatic ring having 0-4 heteroatoms independently selected from nitrogen, oxygen, and sulfur; wherein said ring is substituted with r instances of $R^C$;
$R^7$ is H or $R^B$, wherein $R^7$ is substituted with t instances of $R^{7A}$;
each of $L^5$ and $L^6$ is independently a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-5}$ cycloalkylene, 3-5 membered heterocycloalkylene, 5-6 membered heteroarylene, —NH—, —N($R^L$)—, —NHC(O)—, —N($R^L$)C(O)—, —C(O)NH—, —C(O)N($R^L$)—, —NHS(O)$_2$—, —N($R^L$)S(O)$_2$—, —S(O)$_2$NH—, —S(O)$_2$N($R^L$)—, —O—, —C(O)—, —OC(O)—, —C(O)O—, —S—, —S(O)—, or —S(O)$_2$—;
each of $R^{WA}$, $R^{WB}$, and $R^{WC}$ is independently hydrogen, halogen, —CN, —C(O)R, —C(O)OR, —C(O)NR$_2$, —C(O)N(R)OR, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; or
$R^{WA}$ and $R^{WB}$, $R^{WB}$ and $R^{WC}$, $R^{WA}$ and an instance of $R^L$, or $R^{WC}$ and an instance of $R^L$ are taken together with their intervening atoms to form a 4-7 membered saturated or partially unsaturated ring having 0-2 heteroatoms independently selected from nitrogen, oxygen, and sulfur;
$R^{WD}$ is halogen or —OS(O)$_2$R;

each instance of $R^{5C}$, $R^{5D}$, $R^{7A}$, and $R^L$ is independently $R^A$ or $R^B$, and is substituted by u instances of $R^C$;
each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;
each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;
each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —S(O)$_2$F, —OS(O)$_2$F, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
each R is independently hydrogen, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and
each of m, n, p, q, r, t, and u is independently 0, 1, 2, 3, or 4.

As defined generally above, $R^{5A}$ is a bivalent radical of $R^B$, wherein $R^{5A}$ is substituted with m instances of $R^{5C}$ in addition to -$L^5$-$R^{5B}$. In some embodiments, $R^{5A}$ is a bivalent $C_{1-6}$ aliphatic substituted with m instances of $R^{5C}$ in addition to -$L^5$-$R^{5B}$. In some embodiments, $R^{5A}$ is phenylene substituted with m instances of $R^{5C}$ in addition to -$L^5$-$R^{5B}$. In some embodiments, $R^{5A}$ is a 5-6 membered monocyclic heteroarylene ring having 1-4 heteroatoms independently selected from nitrogen, oxygen, and sulfur; substituted with m instances of $R^{5C}$ in addition to -$L^5$-$R^{5B}$. In some embodiments, $R^{5A}$ is an 8-10 membered bicyclic heteroarylene ring having 1-4 heteroatoms independently selected from nitrogen, oxygen, and sulfur; substituted with m instances of $R^{5C}$ in addition to -$L^5$-$R^{5B}$. In some embodiments, $R^{5A}$ is a bivalent 3-7 membered saturated or partially unsaturated carbocyclic ring substituted with m instances of $R^{5C}$ in addition to -$L^5$-$R^{5B}$. In some embodiments, $R^{5A}$ is a bivalent 3-7 membered saturated or partially unsaturated monocyclic heterocyclic ring having 1-2 heteroatoms independently selected from nitrogen, oxygen, and sulfur; substituted with m instances of $R^{5C}$ in addition to -$L^5$-$R^{5B}$. In some embodiments, $R^{5A}$ is a bivalent 7-12 membered saturated or partially unsaturated bicyclic heterocyclic ring having 1-4 heteroatoms independently selected from nitrogen, oxygen, and sulfur; substituted with m instances of $R^{5C}$ in addition to -$L^5$-$R^{5B}$. In some embodiments, $R^{5A}$ is selected from the groups depicted in the compounds in Table 1.

As defined generally above, $L^5$ is a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-5}$ cycloalkylene, 3-5 membered heterocycloalkylene, 5-6 membered heteroarylene, —NH—, —N($R^L$)—, —NHC(O)—, —N($R^L$)C(O)—, —C(O)NH—, —C(O)N($R^L$)—, —NHS(O)$_2$—, —N($R^L$)S(O)$_2$—, —S(O)$_2$NH—, —S(O)$_2$N($R^L$)—, —O—, —C(O)—, —OC(O)—, —C(O)O—, —S—, —S(O)—, or —S(O)$_2$—. In some embodiments $L^5$ is a covalent bond. In some embodiments $L^5$ is a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-5}$ cycloalkylene, 3-5 membered heterocycloalkylene, 5-6 membered heteroarylene, —NH—, —N($R^L$)—, —NHC(O)—, —N($R^L$)C(O)—, —C(O)NH—, —C(O)N($R^L$)—, —NHS(O)$_2$—, —N($R^L$)S(O)$_2$—, —S(O)$_2$NH—, —S(O)$_2$N($R^L$)—, —O—, —C(O)—, —OC(O)—, —C(O)O—, —S—, —S(O)—, or —S(O)$_2$—.

In some embodiments, $L^5$ is a $C_{1-2}$ bivalent saturated or unsaturated, straight or branched hydrocarbon chain wherein one or two methylene units of the chain are optionally and independently replaced by —CH($R^L$)—, —C($R^L$)$_2$—, $C_{3-5}$ cycloalkylene, 3-5 membered heterocycloalkylene, 5-6 membered heteroarylene, —NH—, —N($R^L$)—, —NHC(O)—, —N($R^L$)C(O)—, —C(O)NH—, —C(O)N($R^L$)—, —NHS(O)$_2$—, —N($R^L$)S(O)$_2$—, —S(O)$_2$NH—, —S(O)$_2$N($R^L$)—, —O—, —C(O)—, —OC(O)—, —C(O)O—, —S—, —S(O)—, or —S(O)$_2$—. In some embodiments, $L^5$ is a $C_{1-2}$ bivalent saturated or unsaturated, straight or branched hydrocarbon chain wherein one or two methylene units of the chain are optionally and independently replaced by —O—, —C(O)—, —C(O)NH—, or —C(O)N($R^L$)—.

In some embodiments, $L^5$ is —O—, —C(O)—, —C(O)NH—, or —C(O)N($R^L$)—. In some embodiments, $L^5$ is —O—. In some embodiments, $L^5$ is —C(O)—. In some embodiments, $L^5$ is —C(O)NH—. In some embodiments, $L^5$ is —C(O)N($R^L$)—. In some embodiments, $L^5$ is selected from the groups depicted in the compounds in Table 1.

As defined generally above, $R^{5B}$ is hydrogen or $R^B$, wherein $R^{5B}$ is substituted with n instances of $R^{5D}$. In some embodiments, $R^{5B}$ is hydrogen. In some embodiments, $R^{5B}$ is $R^B$ substituted with n instances of $R^{5D}$. In some embodiments, $R^{5B}$ is $C_{1-6}$ aliphatic substituted with n instances of $R^{5D}$. In some embodiments, $R^{5B}$ is phenyl substituted with n instances of $R^{5D}$. In some embodiments, $R^{5B}$ is a 5-6 membered monocyclic heteroaryl ring having 1-4 heteroatoms independently selected from nitrogen, oxygen, and sulfur; substituted with n instances of $R^{5D}$. In some embodiments, $R^{5B}$ is an 8-10 membered bicyclic heteroaryl ring having 1-4 heteroatoms independently selected from nitrogen, oxygen, and sulfur; substituted with n instances of $R^{5D}$. In some embodiments, $R^{5B}$ is a 3-7 membered saturated or partially unsaturated carbocyclic ring substituted with n instances of $R^{5D}$. In some embodiments, $R^{5B}$ is a 3-7 membered saturated or partially unsaturated monocyclic heterocyclic ring having 1-2 heteroatoms independently selected from nitrogen, oxygen, and sulfur; substituted with n instances of $R^{5D}$. In some embodiments, $R^{5B}$ is a 7-12 membered saturated or partially unsaturated bicyclic heterocyclic ring having 1-4 heteroatoms independently selected from nitrogen, oxygen, and sulfur; substituted with n instances of $R^{5D}$.

In some embodiments, $R^{5B}$ is a 4-6 membered saturated or partially unsaturated monocyclic heterocyclic ring having 1-2 heteroatoms independently selected from nitrogen, oxygen, and sulfur; substituted with n instances of $R^{5D}$. In some embodiments, $R^{5B}$ is a 5-membered monocyclic heteroaryl ring having 1-3 heteroatoms independently selected from nitrogen, oxygen, and sulfur; substituted with n instances of $R^{5D}$. In some embodiments, $R^{5B}$ is a 6-membered monocyclic heteroaryl ring having 1-2 heteroatoms independently selected from nitrogen, oxygen, and sulfur; substituted with n instances of $R^{5D}$. In some embodiments, $R^{5B}$ is selected from the groups depicted in the compounds in Table 1.

As defined generally above, each instance of $R^{5C}$ is independently $R^A$ or $R^B$, and is substituted by u instances of $R^C$. In some embodiments, each instance of $R^{5C}$ is $R^A$. In some embodiments, each instance of $R^{5C}$ is independently selected from halogen, —CN, —OR, —S(O)$_2$NR$_2$, —C(O)R, —C(O)OR, —C(O)NR$_2$, —OC(O)R, and —N(R)C(O)R. In some embodiments, each instance of $R^{5C}$ is independently selected from halogen, —CN, —OR, and —C(O)NR$_2$. In some embodiments, each instance of $R^{5C}$ is independently selected from halogen, —CN, —O—($C_{1-4}$ alkyl), and —C(O)N($C_{1-4}$ alkyl)$_2$; wherein each $C_{1-4}$ alkyl is optionally substituted with 1, 2, or 3 halogens. In some embodiments, each instance of $R^{5C}$ is independently selected from halogen, —CN, —O—($C_{1-4}$ alkyl), and —C(O)N($C_{1-4}$ alkyl)$_2$.

In some embodiments, each instance of $R^{5C}$ is $R^B$, wherein $R^{5C}$ is substituted by u instances of $R^C$. In some embodiments, each instance of $R^{5C}$ is $R^B$, wherein $R^{5C}$ is substituted by one instance of $R^C$. In some embodiments, each instance of $R^{5C}$ is independently selected from $C_{1-6}$ aliphatic; phenyl; a 5-6 membered monocyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; each of which is optionally substituted by u instances of $R^C$.

In some embodiments, each instance of $R^{5C}$ is independently selected from $C_{1-6}$ aliphatic; a 3-7 membered saturated or partially unsaturated carbocyclic ring; and a 3-7 membered saturated or partially unsaturated monocyclic heterocyclic ring having 1-2 heteroatoms independently selected from nitrogen, oxygen, and sulfur; each of which is optionally substituted by u instances of $R^C$. In some embodiments, each instance of $R^{5C}$ is independently selected from $C_{1-4}$ aliphatic optionally substituted by one instance of $R^C$; a 3-5 membered saturated carbocyclic ring; and a 3-5 membered saturated monocyclic heterocyclic ring having 1 heteroatom independently selected from nitrogen, oxygen, and sulfur; each of which is optionally substituted with 1, 2, or 3 halogens. In some embodiments, each instance of $R^{5C}$ is independently selected from $C_{1-4}$ alkyl optionally substituted by one instance of —OH, —O—($C_{1-4}$ alkyl), or —N($C_{1-4}$ alkyl)$_2$; a 3-5 membered saturated carbocyclic ring; and a 3-5 membered saturated monocyclic heterocyclic ring having 1 oxygen atom; each of which is optionally substituted with 1, 2, or 3 fluoro or chloro.

In some embodiments, each instance of $R^{5C}$ is independently selected from halogen, —CN, —OR, —C(O)NR$_2$, and the following groups, each of which is optionally substituted by u instances of $R^C$: $C_{1-6}$ aliphatic; a 3-7 membered saturated or partially unsaturated carbocyclic ring; and a 3-7 membered saturated or partially unsaturated monocyclic heterocyclic ring having 1-2 heteroatoms independently selected from nitrogen, oxygen, and sulfur. In some embodiments, each instance of $R^{5C}$ is independently selected from halogen, —CN, and the following groups, each of which is optionally substituted with 1, 2, or 3 halogens: —O—($C_{1-4}$ alkyl), —C(O)N($C_{1-4}$ alkyl)$_2$, $C_{1-4}$ aliphatic optionally substituted by one instance of $R^C$; a 3-5 membered saturated carbocyclic ring; and a 3-5 membered saturated monocyclic heterocyclic ring having 1 heteroatom independently selected from nitrogen, oxygen, and sulfur. In some embodiments, each instance of $R^{5C}$ is independently selected from halogen, —CN, —O—($C_{1-4}$ alkyl), —C(O)N($C_{1-4}$ alkyl)$_2$, and the following groups, each of which is optionally substituted with 1, 2, or 3 fluoro or chloro: $C_{1-4}$ alkyl optionally substituted by one instance of —OH, —O—($C_{1-4}$ alkyl), or —N($C_{1-4}$ alkyl)$_2$; a 3-5 membered saturated carbocyclic ring; and a 3-5 membered saturated monocyclic heterocyclic ring having 1 oxygen atom. In some embodiments, $R^{5C}$ is selected from the groups depicted in the compounds in Table 1.

As defined generally above, each instance of $R^{5D}$ is independently $R^A$ or $R^B$, and is substituted by u instances of $R^C$. In some embodiments, each instance of $R^{5D}$ is $R^A$. In some embodiments, each instance of $R^{5D}$ is independently selected from halogen, —CN, —OR, —S(O)$_2$NR$_2$, —C(O)R, —C(O)OR, —C(O)NR$_2$, —OC(O)R, and —N(R)C(O)R. In some embodiments, each instance of $R^{5D}$ is independently selected from halogen, —CN, —OR, and —C(O)NR$_2$. In some embodiments, each instance of $R^{5D}$ is independently selected from halogen, —CN, —O—($C_{1-4}$ alkyl), and —C(O)N($C_{1-4}$ alkyl)$_2$; wherein each $C_{1-4}$ alkyl is optionally substituted with 1, 2, or 3 halogens. In some embodiments, each instance of $R^{5D}$ is independently selected from halogen, —CN, —O—($C_{1-4}$ alkyl), and —C(O)N($C_{1-4}$ alkyl)$_2$.

In some embodiments, each instance of $R^{5D}$ is $R^B$, wherein $R^{5D}$ is substituted by u instances of $R^C$. In some embodiments, each instance of $R^{5D}$ is $R^B$, wherein $R^{5D}$ is substituted by one instance of $R^C$. In some embodiments, each instance of $R^{5D}$ is independently selected from $C_{1-6}$ aliphatic; phenyl; a 5-6 membered monocyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; each of which is optionally substituted by u instances of $R^C$.

In some embodiments, each instance of $R^{5D}$ is independently selected from $C_{1-6}$ aliphatic; a 3-7 membered saturated or partially unsaturated carbocyclic ring; and a 3-7 membered saturated or partially unsaturated monocyclic heterocyclic ring having 1-2 heteroatoms independently selected from nitrogen, oxygen, and sulfur; each of which is optionally substituted by u instances of $R^C$. In some embodiments, each instance of $R^{5D}$ is independently selected from $C_{1-4}$ aliphatic optionally substituted by one instance of $R^C$; a 3-5 membered saturated carbocyclic ring; and a 3-5 membered saturated monocyclic heterocyclic ring having 1 heteroatom independently selected from nitrogen, oxygen, and sulfur; each of which is optionally substituted with 1, 2, or 3 halogens. In some embodiments, each instance of $R^{5D}$ is independently selected from $C_{1-4}$ alkyl optionally substituted by one instance of —OH, —O—($C_{1-4}$ alkyl), or —N($C_{1-4}$ alkyl)$_2$; a 3-5 membered saturated carbocyclic ring; and a 3-5 membered saturated monocyclic heterocyclic ring having 1 oxygen atom; each of which is optionally substituted with 1, 2, or 3 fluoro or chloro.

In some embodiments, each instance of $R^{5D}$ is independently selected from halogen, —CN, —OR, —C(O)NR$_2$, and the following groups, each of which is optionally substituted by u instances of $R^C$: $C_{1-6}$ aliphatic; a 3-7 membered saturated or partially unsaturated carbocyclic ring; and a 3-7 membered saturated or partially unsaturated monocyclic heterocyclic ring having 1-2 heteroatoms independently selected from nitrogen, oxygen, and sulfur. In some embodiments, each instance of $R^{5D}$ is independently selected from halogen, —CN, and the following groups, each of which is optionally substituted with 1, 2, or 3 halogens: —O—($C_{1-4}$ alkyl), —C(O)N($C_{1-4}$ alkyl)$_2$, $C_{1-4}$ aliphatic optionally substituted by one instance of $R^C$; a 3-5 membered saturated carbocyclic ring; and a 3-5 membered saturated monocyclic heterocyclic ring having 1 heteroatom independently selected from nitrogen, oxygen, and sulfur. In some embodiments, each instance of $R^{5D}$ is independently selected from halogen, —CN, —O—($C_{1-4}$ alkyl), —C(O)N($C_{1-4}$ alkyl)$_2$, and the following groups, each of which is optionally substituted with 1, 2, or 3 fluoro or chloro: $C_{1-4}$ alkyl optionally substituted by one instance of —OH, —O—($C_{1-4}$ alkyl), or —N($C_{1-4}$ alkyl)$_2$; a 3-5 membered saturated carbocyclic ring; and a 3-5 membered saturated monocyclic heterocyclic ring having 1 oxygen atom. In some embodiments, $R^{5D}$ is selected from the groups depicted in the compounds in Table 1.

As defined generally above, in some embodiments, the present invention provides a compound of Formula I wherein $R^5$ is —$R^{5A}$-$L^5$-$R^{5B}$. In some embodiments, $R^5$ (i.e. —$R^{5A}$-$L^5$-$R^{5B}$ taken together) is:

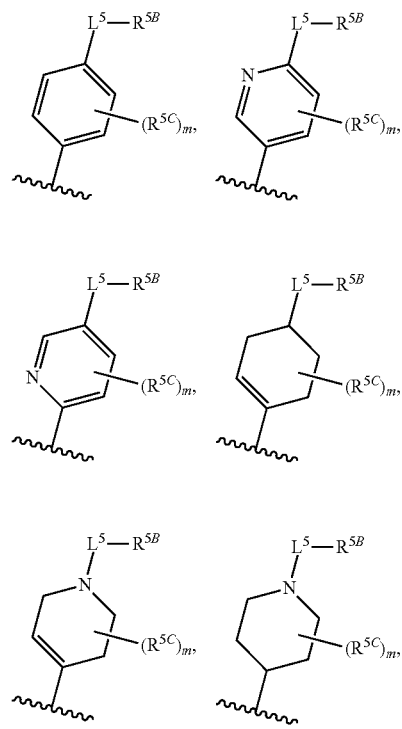

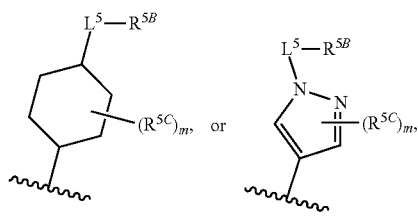

wherein each of $L^5$, $R^{5B}$, $R^{5C}$, and m is as defined in embodiments and classes and subclasses herein.

In some embodiments, $R^5$ (i.e. —$R^{5A}$-$L^5$-$R^{5B}$ taken together) is:

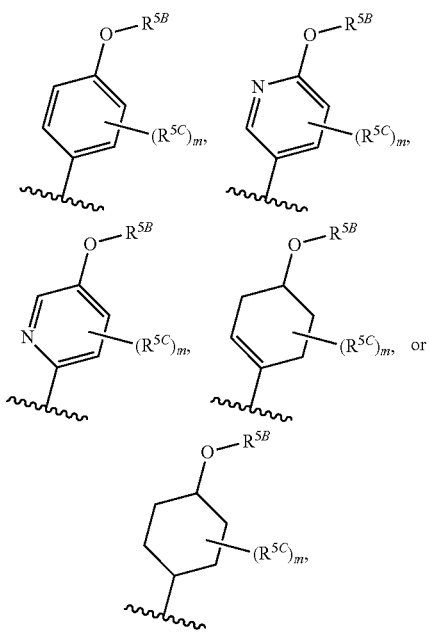

wherein each of $R^{5B}$, $R^{5C}$, and m is as defined in embodiments and classes and subclasses herein.

In some embodiments, $R^5$ (i.e. —$R^{5A}$-$L^5$-$R^{5B}$ taken together) is:

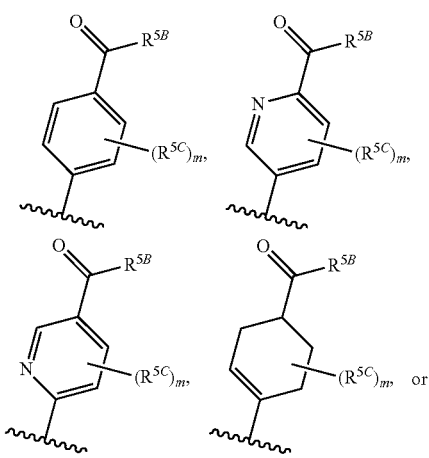

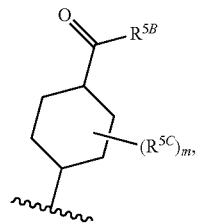

wherein each of $R^{5B}$, $R^{5C}$, and m is as defined in embodiments and classes and subclasses herein.

In some embodiments, $R^5$ (i.e. —$R^{5A}$-$L^5$-$R^{5B}$ taken together) is:

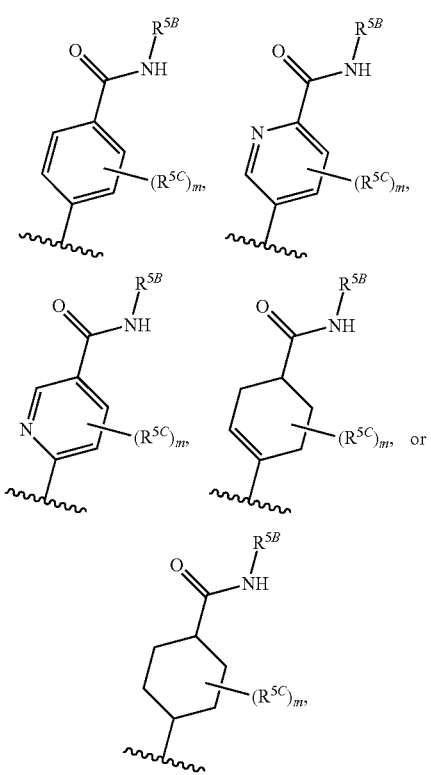

wherein each of $R^{5B}$, $R^{5C}$, and m is as defined in embodiments and classes and subclasses herein.

In some embodiments, $R^5$ (i.e. —$R^{5A}$-$L^5$-$R^{5B}$ taken together) is:

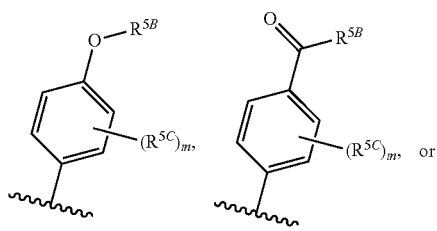

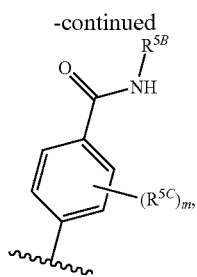

wherein each of $R^{5B}$, $R^{5C}$, and m is as defined in embodiments and classes and subclasses herein.

In some embodiments, $R^5$ (i.e. —$R^{5A}$-$L^5$-$R^{5B}$ taken together) is:

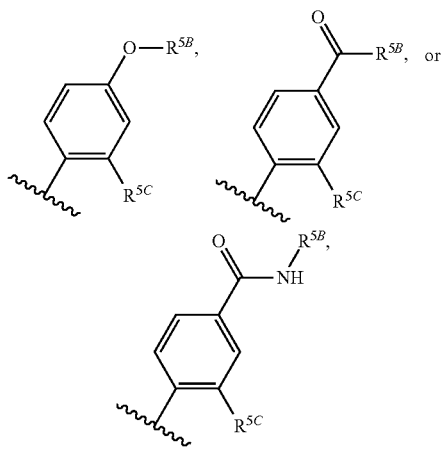

wherein each of $R^{5B}$ and $R^{5C}$ is as defined in embodiments and classes and subclasses herein.

In some embodiments, $R^5$ (i.e. —$R^{5A}$-$L^5$-$R^{5B}$ taken together) is:

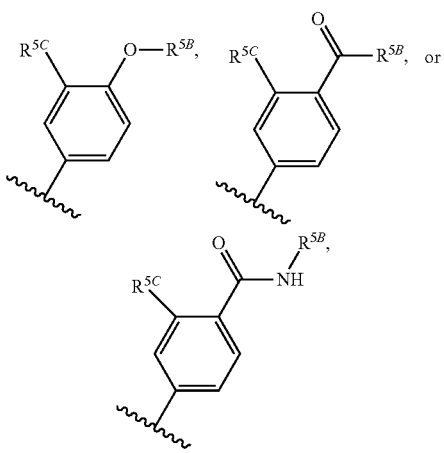

wherein each of $R^{5B}$ and $R^{5C}$ is as defined in embodiments and classes and subclasses herein.

In some embodiments, $R^5$ (i.e. —$R^{5A}$-$L^5$-$R^{5B}$ taken together) is selected from the groups depicted in the compounds in Table 1.

As defined generally above, $Cy^6$ is phenylene or a 6-membered heteroarylene having 1-3 nitrogen atoms, wherein $Cy^6$ is substituted with p instances of $R^6$ in addition to -$L^6$-$R^W$. In some embodiments, $Cy^6$ is phenylene substituted with p instances of $R^6$ in addition to -$L^6$-$R^W$. In some embodiments, $Cy^6$ is a 6-membered heteroarylene having 1-3 nitrogen atoms, wherein $Cy^6$ is substituted with p instances of $R^6$ in addition to -$L^6$-$R^W$. In some embodiments, $Cy^6$ is a 6-membered heteroarylene having 1-2 nitrogen atoms, substituted with p instances of $R^6$ in addition to -$L^6$-$R^W$. In some embodiments, $Cy^6$ is a 6-membered heteroarylene having 1 nitrogen atom, substituted with p instances of $R^6$ in addition to -$L^6$-$R^W$. In some embodiments, $Cy^6$ is a 6-membered heteroarylene having 2 nitrogen atoms, substituted with p instances of $R^6$ in addition to -$L^6$-$R^W$. In some embodiments, $Cy^6$ is a 6-membered heteroarylene having 2 nitrogen atoms, substituted only with -$L^6$-$R^W$. In some embodiments, $Cy^6$ is a 6-membered heteroarylene having 1-2 nitrogen atoms, substituted with p instances of $R^6$ in addition to -$L^6$-$R^W$, wherein $L^6$ is a covalent bond, and —$R^W$ is —CN or

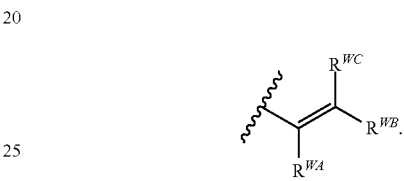

In some embodiments, $Cy^6$ is selected from the groups depicted in the compounds in Table 1.

As defined generally above, each instance of $R^6$ is independently $R^A$ or $R^B$, wherein $R^6$ is substituted by q instances of $R^C$; or two instances of $R^6$, or an instance of $R^6$ and an instance of $R^L$ are taken together with their intervening atoms to form a 4-7 membered partially unsaturated or aromatic ring having 0-4 heteroatoms independently selected from nitrogen, oxygen, and sulfur; wherein said ring is substituted with r instances of $R^C$. In some embodiments, each instance of $R^6$ is independently $R^A$ or $R^B$, wherein $R^6$ is substituted by q instances of $R^C$.

In some embodiments, two instances of $R^6$, or an instance of $R^6$ and an instance of $R^L$ are taken together with their intervening atoms to form a 4-7 membered partially unsaturated or aromatic ring having 0-4 heteroatoms independently selected from nitrogen, oxygen, and sulfur; wherein said ring is substituted with r instances of $R^C$. In some embodiments, two instances of $R^6$ are taken together with their intervening atoms to form a 4-7 membered partially unsaturated or aromatic ring having 0-4 heteroatoms independently selected from nitrogen, oxygen, and sulfur; wherein said ring is substituted with r instances of $R^C$.

In some embodiments, an instance of $R^6$ and an instance of $R^L$ are taken together with their intervening atoms to form a 4-7 membered partially unsaturated or aromatic ring having 0-4 heteroatoms independently selected from nitrogen, oxygen, and sulfur; wherein said ring is substituted with r instances of $R^C$. In some embodiments, an instance of $R^6$ and an instance of $R^L$ are taken together with their intervening atoms to form a 4-7 membered partially unsaturated ring having one nitrogen atom; wherein said ring is optionally substituted with 1, 2, or 3 substituents independently selected from halogen, —CN, —O—($C_{1-4}$ alkyl), and —($C_{1-4}$ alkyl); wherein each $C_{1-4}$ alkyl is optionally substituted with 1, 2, or 3 fluoro. In some embodiments, an instance of $R^6$ and an instance of $R^L$ are taken together with their intervening atoms to form a 4-7 membered partially unsaturated ring having one nitrogen atom.

In some embodiments, each instance of $R^6$ is $R^A$. In some embodiments, each instance of $R^6$ is independently selected from halogen, —CN, —OR, —S(O)$_2$NR$_2$, —C(O)R, —C(O)OR, —C(O)NR$_2$, —OC(O)R, and —N(R)C(O)R. In some embodiments, each instance of $R^6$ is independently selected from halogen, —CN, —OR, and —C(O)NR$_2$. In some embodiments, each instance of $R^6$ is independently selected from halogen, —CN, —O—(C$_{1-4}$ alkyl), and —C(O)N(C$_{1-4}$ alkyl)$_2$; wherein each C$_{1-4}$ alkyl is optionally substituted with 1, 2, or 3 halogens. In some embodiments, each instance of $R^6$ is independently selected from halogen, —CN, —O—(C$_{1-4}$ alkyl), and —C(O)N(C$_{1-4}$ alkyl)$_2$.

In some embodiments, each instance of $R^6$ is $R^B$, wherein $R^6$ is substituted by q instances of $R^C$. In some embodiments, each instance of $R^6$ is $R^B$, wherein $R^6$ is substituted by one instance of $R^C$. In some embodiments, each instance of $R^6$ is independently selected from C$_{1-6}$ aliphatic; phenyl; a 5-6 membered monocyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; each of which is optionally substituted by q instances of $R^C$.

In some embodiments, each instance of $R^6$ is independently selected from C$_{1-6}$ aliphatic; a 3-7 membered saturated or partially unsaturated carbocyclic ring; and a 3-7 membered saturated or partially unsaturated monocyclic heterocyclic ring having 1-2 heteroatoms independently selected from nitrogen, oxygen, and sulfur; each of which is optionally substituted by q instances of $R^C$. In some embodiments, each instance of $R^6$ is independently selected from C$_{1-4}$ aliphatic optionally substituted by one instance of $R^C$; a 3-5 membered saturated carbocyclic ring; and a 3-5 membered saturated monocyclic heterocyclic ring having 1 heteroatom independently selected from nitrogen, oxygen, and sulfur; each of which is optionally substituted with 1, 2, or 3 halogens. In some embodiments, each instance of $R^6$ is independently selected from C$_{1-4}$ alkyl optionally substituted by one instance of —OH, —O—(C$_{1-4}$ alkyl), or —N(C$_{1-4}$ alkyl)$_2$; a 3-5 membered saturated carbocyclic ring; and a 3-5 membered saturated monocyclic heterocyclic ring having 1 oxygen atom; each of which is optionally substituted with 1, 2, or 3 fluoro or chloro.

In some embodiments, each instance of $R^6$ is independently selected from halogen, —CN, —OR, —C(O)NR$_2$, and the following groups, each of which is optionally substituted by q instances of $R^C$: C$_{1-6}$ aliphatic; a 3-7 membered saturated or partially unsaturated carbocyclic ring; and a 3-7 membered saturated or partially unsaturated monocyclic heterocyclic ring having 1-2 heteroatoms independently selected from nitrogen, oxygen, and sulfur. In some embodiments, each instance of $R^6$ is independently selected from halogen, —CN, and the following groups, each of which is optionally substituted with 1, 2, or 3 halogens: —O—(C$_{1-4}$ alkyl), —C(O)N(C$_{1-4}$ alkyl)$_2$, C$_{1-4}$ aliphatic optionally substituted by one instance of $R^C$; a 3-5 membered saturated carbocyclic ring; and a 3-5 membered saturated monocyclic heterocyclic ring having 1 heteroatom independently selected from nitrogen, oxygen, and sulfur. In some embodiments, each instance of $R^6$ is independently selected from halogen, —CN, —O—(C$_{1-4}$ alkyl), —C(O)N(C$_{1-4}$ alkyl)$_2$, and the following groups, each of which is optionally substituted with 1, 2 or 3 fluoro or chloro: C$_{1-4}$ alkyl optionally substituted by one instance of —OH, —O—(C$_{1-4}$ alkyl), or —N(C$_{1-4}$ alkyl)$_2$; a 3-5 membered saturated carbocyclic ring; and a 3-5 membered saturated monocyclic heterocyclic ring having 1 oxygen atom. In some embodiments, $R^6$ is selected from the groups depicted in the compounds in Table 1.

As defined generally above, $L^6$ is a covalent bond, or a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-5}$ cycloalkylene, 3-5 membered heterocycloalkylene, 5-6 membered heteroarylene, —NH—, —N(R$^L$)—, —NHC(O)—, —N(R$^L$)C(O)—, —C(O)NH—, —C(O)N(R$^L$)—, —NHS(O)$_2$—, —N(R$^L$)S(O)$_2$—, —S(O)$_2$NH—, —S(O)$_2$N(R$^L$)—, —O—, —C(O)—, —OC(O)—, —C(O)O—, —S—, —S(O)—, or —S(O)$_2$—. In some embodiments, $L^6$ is a covalent bond. In some embodiments, $L^6$ is a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-5}$ cycloalkylene, 3-5 membered heterocycloalkylene, 5-6 membered heteroarylene, —NH—, —N(R$^L$)—, —NHC(O)—, —N(R$^L$)C(O)—, —C(O)NH—, —C(O)N(R$^L$)—, —NHS(O)$_2$—, —N(R$^L$)S(O)$_2$—, —S(O)$_2$NH—, —S(O)$_2$N(R$^L$)—, —O—, —C(O)—, —OC(O)—, —C(O)O—, —S—, —S(O)—, or —S(O)$_2$—.

In some embodiments, $L^6$ is a C$_{1-2}$ bivalent saturated or unsaturated, straight or branched hydrocarbon chain wherein one or two methylene units of the chain are optionally and independently replaced by —CH(R$^L$)—, —C(R$^L$)$_2$—, C$_{3-5}$ cycloalkylene, 3-5 membered heterocycloalkylene, 5-6 membered heteroarylene, —NH—, —N(R$^L$)—, —NHC(O)—, —N(R$^L$)C(O)—, —C(O)NH—, —C(O)N(R$^L$)—, —NHS(O)$_2$—, —N(R$^L$)S(O)$_2$—, —S(O)$_2$NH—, —S(O)$_2$N(R$^L$)—, —O—, —C(O)—, —OC(O)—, —C(O)O—, —S—, —S(O)—, or —S(O)$_2$—. In some embodiments, $L^6$ is a C$_{1-2}$ bivalent saturated or unsaturated, straight or branched hydrocarbon chain wherein one methylene unit of the chain is optionally replaced by —NH— or —N(R$^L$)—.

In some embodiments, $L^6$ is —NH— or —N(R$^L$)—. In some embodiments, $L^6$ is —NH—. In some embodiments, $L^6$ is —N(R$^L$)—. In some embodiments, $L^6$ is —NH— or —N(CH$_3$)—. In some embodiments, $L^6$ is —N(CH$_3$)—. In some embodiments, $L^6$ is selected from the groups depicted in the compounds in Table 1.

As defined generally above, $R^W$ is halogen, —CN,

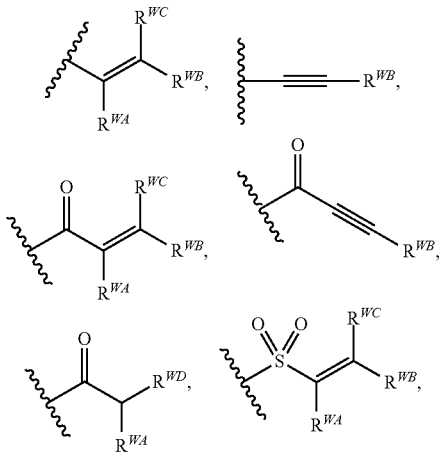

-continued
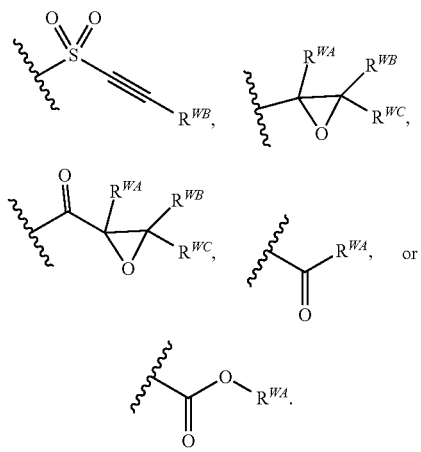
In some embodiments, $R^W$ is halogen, —CN,
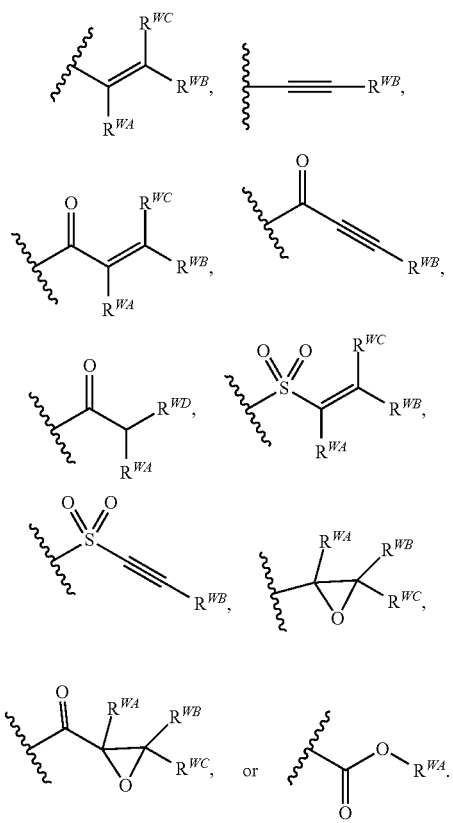
In some embodiments, $R^W$ is halogen. In some embodiments, $R^W$ is —CN. In some embodiments $R^W$ is
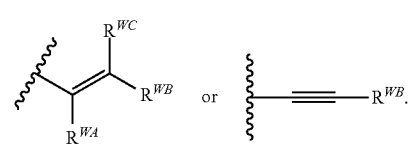
In some embodiments $R^W$ is
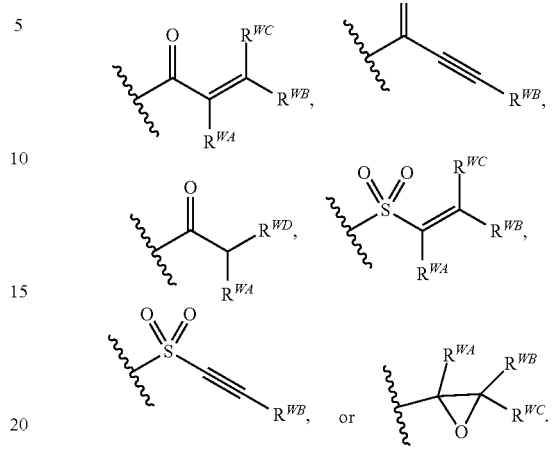
In some embodiments $R^W$ is
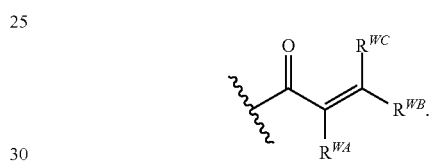
In some embodiments $R^W$ is
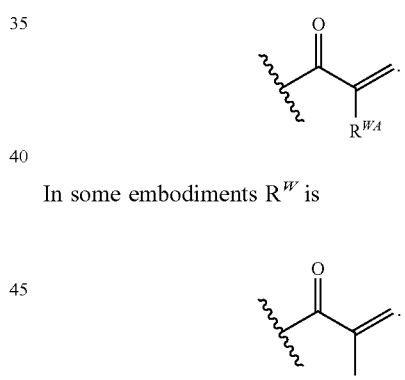
In some embodiments $R^W$ is
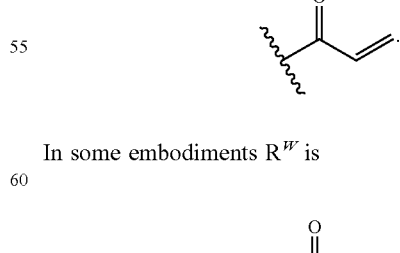

In some embodiments, $R^W$ is

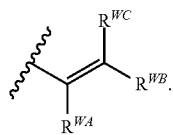

In some embodiments, $R^W$ is

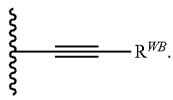

In some embodiments, $R^W$ is

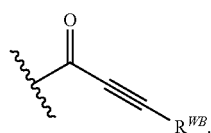

In some embodiments, $R^W$ is

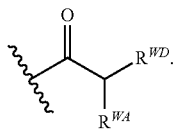

In some embodiments, $R^W$ is

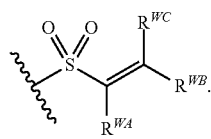

In some embodiments, $R^W$ is

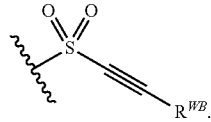

In some embodiments, $R^W$ is

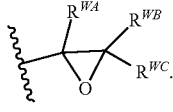

In some embodiments, $R^W$ is

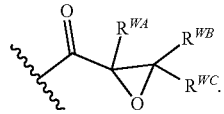

In some embodiments, $R^W$ is

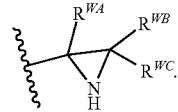

In some embodiments, $R^W$ is

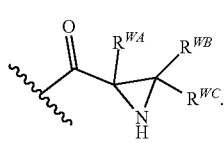

In some embodiments, $R^W$ is

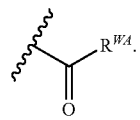

In some embodiments, $R^W$ is

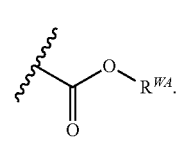

In some embodiments, $R^W$ is —CN,

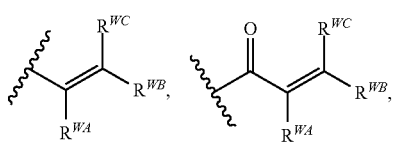

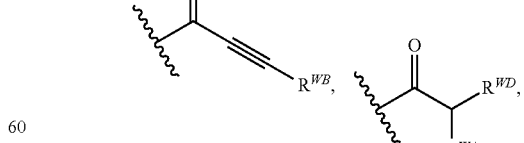

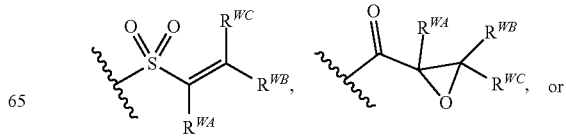

or

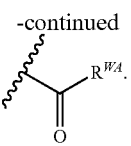

In some embodiments, $R^W$ is

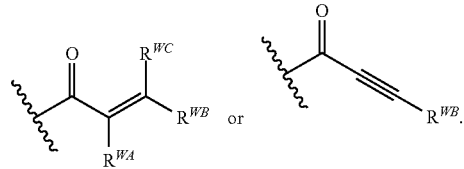

In some embodiments, $R^W$ is

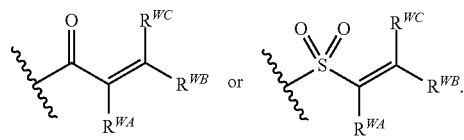

In some embodiments, $R^W$ is

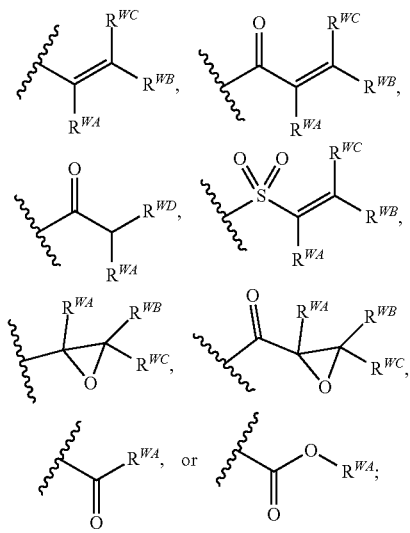

and $R^{WA}$ and $R^{WB}$, $R^{WB}$ and $R^{WC}$, $R^{WA}$ and an instance of $R^L$, or $R^{WC}$ and an instance of $R^L$ are taken together with their intervening atoms to form a 4-7 membered saturated or partially unsaturated ring having 0-2 heteroatoms independently selected from nitrogen, oxygen, and sulfur.

In some embodiments, $R^W$ is

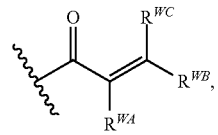

and $R^{WA}$ and $R^{WB}$ or $R^{WB}$ and $R^{WC}$ are taken together with their intervening atoms to form a 4-7 membered partially unsaturated ring having 0-1 heteroatom independently selected from nitrogen, oxygen, and sulfur. In some embodiments, $R^W$ is

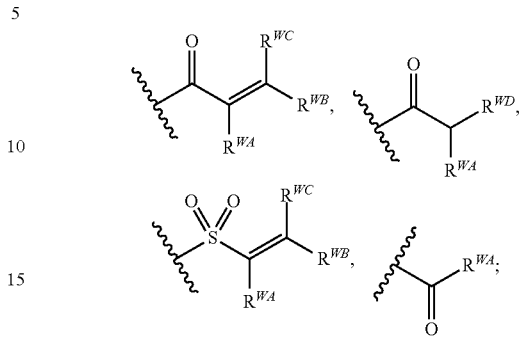

and $R^{WA}$ and an instance of $R^L$ are taken together with their intervening atoms to form a 4-7 membered saturated or partially unsaturated ring having 0-1 heteroatoms independently selected from nitrogen, oxygen, and sulfur. In some embodiments, $R^W$ is

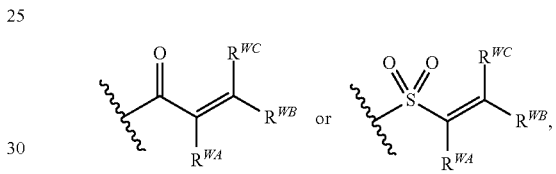

and $R^{WC}$ and an instance of $R^L$ are taken together with their intervening atoms to form a 4-7 membered partially unsaturated ring having 0-2 heteroatoms independently selected from nitrogen, oxygen, and sulfur. In some embodiments, $R^W$ is selected from the groups depicted in the compounds in Table 1.

Without wishing to be bound by any particular theory, it is believed that $R^W$ is a warhead group, particularly suitable for covalently binding to the sulfhydryl side chain moiety of a protein kinase, for example Cys491 of FGFR2. Thus, in some embodiments, $R^W$ is characterized in that it is capable of covalently binding to a cysteine residue, thereby irreversibly inhibiting a protein kinase. In some embodiments, the protein kinase is an FGFR. In certain embodiments, the protein kinase is FGFR2. In certain embodiments, the protein kinase is FGFR2, and the cysteine residue is Cys491.

As defined generally above, each of $R^{WA}$, $R^{WB}$, and $R^{WC}$ is independently hydrogen, halogen, —CN, —C(O)R, —C(O)OR, —C(O)NR$_2$, —C(O)N(R)OR, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; or $R^{WA}$ and $R^{WB}$, $R^{WB}$ and $R^{WC}$, $R^{WA}$ and an instance of $R^L$, or $R^{WC}$ and an instance of $R^L$ are taken together with their intervening atoms to form a 4-7 membered saturated or partially unsaturated ring having 0-2 heteroatoms independently selected from nitrogen, oxygen, and sulfur.

In some embodiments, each of $R^{WA}$, $R^{WB}$, and $R^{WC}$ is independently hydrogen, halogen, —CN, —C(O)R, —C(O)OR, —C(O)NR$_2$, —C(O)N(R)OR, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur. In some embodiments, $R^{WA}$ and $R^{WB}$, $R^{WB}$ and $R^{WC}$, $R^{WA}$ and an instance of $R^L$, or $R^{WC}$ and an instance of $R^L$ are taken together with their intervening atoms to form a 4-7 membered saturated or partially unsaturated ring having 0-2 heteroatoms independently selected from nitrogen, oxygen, and sulfur.

In some embodiments, each of $R^{WA}$, $R^{WB}$, and $R^{WC}$ is independently hydrogen, halogen, —CN, —C(O)R, —C(O)OR, —C(O)NR$_2$, or —C(O)N(R)OR. In some embodiments, each of $R^{WA}$, $R^{WB}$, and $R^{WC}$ is independently an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, each of $R^{WA}$, $R^{WB}$, and $R^{WC}$ is independently hydrogen or optionally substituted $C_{1-6}$ aliphatic. In some embodiments, each of $R^{WA}$, $R^{WB}$, and $R^{WC}$ is independently hydrogen or optionally substituted $C_{1-6}$ aliphatic. In some embodiments, each of $R^{WA}$, $R^{WB}$, and $R^{WC}$ is independently hydrogen, —$C_{1-4}$ alkyl, —($C_{1-4}$ alkyl)-O—($C_{1-4}$ alkyl), or —($C_{1-4}$ alkyl)-N($C_{1-4}$ alkyl)$_2$; wherein each $C_{1-4}$ alkyl is optionally substituted with 1, 2, or 3 fluoro. In some embodiments, each of $R^{WA}$, $R^{WB}$, and $R^{WC}$ is independently hydrogen or —$C_{1-4}$ alkyl optionally substituted with 1, 2, or 3 fluoro. In some embodiments, each of $R^{WA}$, $R^{WB}$, and $R^{WC}$ is independently hydrogen or —$C_{1-4}$ alkyl. In some embodiments, each of $R^{WA}$, $R^{WB}$, and $R^{WC}$ is independently hydrogen or —CH$_3$.

In some embodiments, $R^{WA}$ and R or R and $R^{WC}$ are taken together with their intervening atoms to form a 4-7 membered partially unsaturated ring having 0-1 heteroatom independently selected from nitrogen, oxygen, and sulfur. In some embodiments, $R^{WA}$ and $R^{WB}$ or $R^{WB}$ and $R^{WC}$ are taken together with their intervening atoms to form a 4-7 membered partially unsaturated carbocyclic ring. In some embodiments, $R^{WA}$ and an instance of $R^L$ are taken together with their intervening atoms to form a 4-7 membered saturated or partially unsaturated ring having 0-1 heteroatoms independently selected from nitrogen, oxygen, and sulfur. In some embodiments, $R^{WC}$ and an instance of $R^L$ are taken together with their intervening atoms to form a 4-7 membered partially unsaturated ring having 0-2 heteroatoms independently selected from nitrogen, oxygen, and sulfur. In some embodiments, $R^{WC}$ and an instance of $R^L$ are taken together with their intervening atoms to form a 5-6 membered partially unsaturated ring having 0-2 heteroatoms independently selected from nitrogen, oxygen, and sulfur. In some embodiments, each of $R^{WA}$, $R^{WB}$, and $R^{WC}$ is selected from the groups depicted in the compounds in Table 1.

As defined generally above, $R^{WD}$ is halogen or —OS(O)$_2$R. In some embodiments, $R^{WD}$ is halogen. In some embodiments, $R^{WD}$ is chloro or bromo. In some embodiments, $R^{WD}$ is chloro. In some embodiments, $R^{WD}$ is —OS(O)$_2$R. In some embodiments, $R^{WD}$ is —OS(O)$_2$-(optionally substituted $C_{1-3}$ alkyl). In some embodiments, $R^{WD}$ is —OS(O)$_2$CH$_3$ or —OS(O)$_2$CF$_3$. In some embodiments, $R^{WD}$ is —OS(O)$_2$-(optionally substituted phenyl). In some embodiments, $R^{WD}$ is selected from the groups depicted in the compounds in Table 1.

In some embodiments, -Cy$^6$-L$^6$-R$^W$ taken together is:

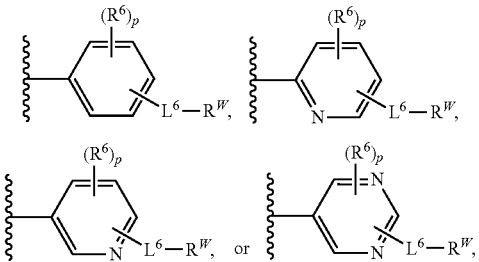

wherein each of L$^6$, R$^6$, R$^W$, and p is as defined in embodiments and classes and subclasses herein. In some embodiments, -Cy$^6$-L$^6$-R$^W$ taken together is:

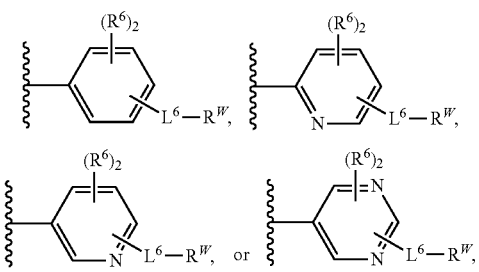

wherein each of L$^6$, R$^6$, and R$^W$ is as defined in embodiments and classes and subclasses herein. In some embodiments, -Cy$^6$-L$^6$-R$^W$ taken together is:

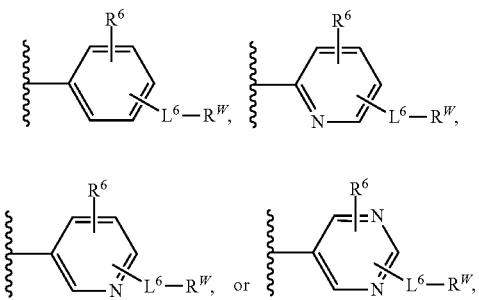

wherein each of L$^6$, R$^6$, and R$^W$ is as defined in embodiments and classes and subclasses herein. In some embodiments, -Cy$^6$-L$^6$-R$^W$ taken together is:

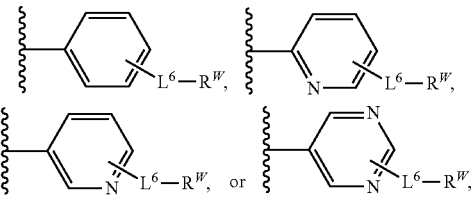

wherein each of L$^6$ and R$^W$ is as defined in embodiments and classes and subclasses herein.

In some embodiments, -Cy⁶-L⁶-R^W taken together is:

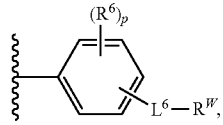

wherein each of L⁶, R⁶, R^W, and p is as defined in embodiments and classes and subclasses herein. In some embodiments, -Cy⁶-L⁶-R^W taken together is:

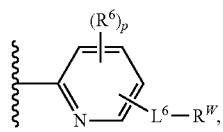

wherein each of L⁶, R⁶, R^W, and p is as defined in embodiments and classes and subclasses herein. In some embodiments, -Cy⁶-L⁶-R^W taken together is:

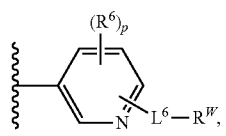

wherein each of L⁶, R⁶, R^W, and p is as defined in embodiments and classes and subclasses herein. In some embodiments, -Cy⁶-L⁶-R^W taken together is:

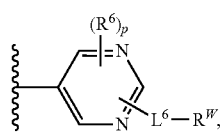

wherein each of L⁶, R⁶, R^W, and p is as defined in embodiments and classes and subclasses herein.
In some embodiments, -Cy⁶-L⁶-R^W taken together is:

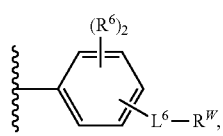

wherein each of L⁶, R⁶, and R^W is as defined in embodiments and classes and subclasses herein. In some embodiments, -Cy⁶-L⁶-R^W taken together is:

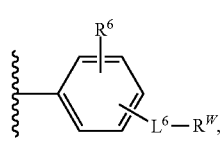

wherein each of L⁶, R⁶, and R^W is as defined in embodiments and classes and subclasses herein. In some embodiments, -Cy⁶-L⁶-R^W taken together is:

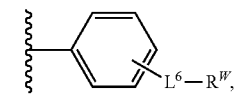

wherein each of L⁶ and R^W is as defined in embodiments and classes and subclasses herein.
In some embodiments, -Cy⁶-L⁶-R^W taken together is:

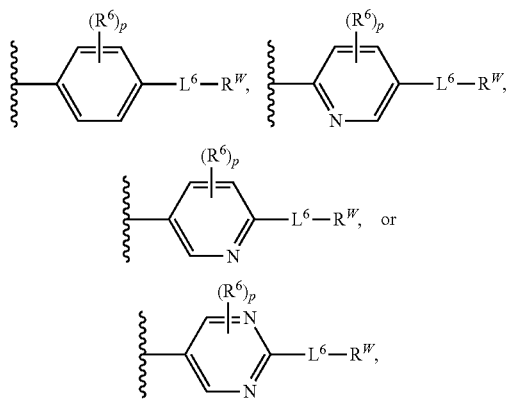

wherein each of L⁶, R⁶, R^W, and p is as defined in embodiments and classes and subclasses herein. In some embodiments, -Cy⁶-L⁶-R^W taken together is:

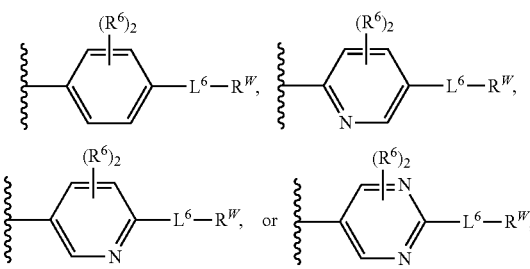

wherein each of L⁶, R⁶, and R^W is as defined in embodiments and classes and subclasses herein. In some embodiments, -Cy⁶-L⁶-R^W taken together is:

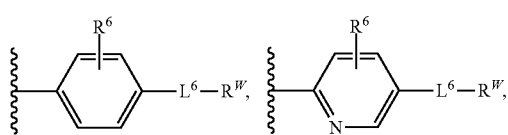

wherein each of L⁶, R⁶, and R^W is as defined in embodiments and classes and subclasses herein. In some embodiments, -Cy⁶-L⁶-R^W taken together is:

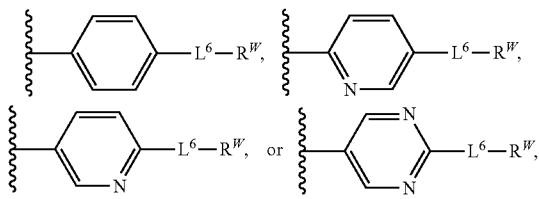

wherein each of $L^6$ and $R^W$ is as defined in embodiments and classes and subclasses herein.

In some embodiments, -$Cy^6$-$L^6$-$R^W$ taken together is:

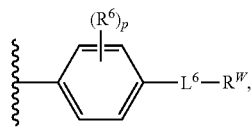

wherein each of $L^6$, $R^6$, $R^W$, and p is as defined in embodiments and classes and subclasses herein. In some embodiments, -$Cy^6$-$L^6$-$R^W$ taken together is:

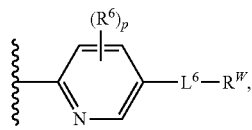

wherein each of $L^6$, $R^6$, $R^W$, and p is as defined in embodiments and classes and subclasses herein. In some embodiments, -$Cy^6$-$L^6$-$R^W$ taken together is:

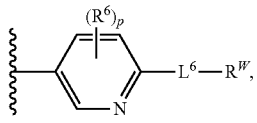

wherein each of $L^6$, $R^6$, $R^W$, and p is as defined in embodiments and classes and subclasses herein. In some embodiments, -$Cy^6$-$L^6$-$R^W$ taken together is:

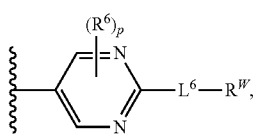

wherein each of $L^6$, $R^6$, $R^W$, and p is as defined in embodiments and classes and subclasses herein.

In some embodiments, -$Cy^6$-$L^6$-$R^W$ taken together is:

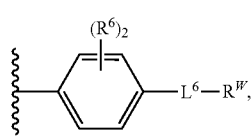

wherein each of $L^6$, $R^6$, and $R^W$ is as defined in embodiments and classes and subclasses herein. In some embodiments, -$Cy^6$-$L^6$-$R^W$ taken together is:

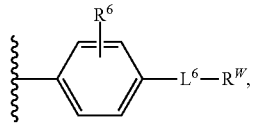

wherein each of $L^6$, $R^6$, and $R^W$ is as defined in embodiments and classes and subclasses herein. In some embodiments, -$Cy^6$-$L^6$-$R^W$ taken together is:

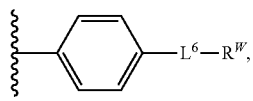

wherein each of $L^6$ and $R^W$ is as defined in embodiments and classes and subclasses herein.

In some embodiments, -$Cy^6$-$L^6$-$R^W$ is selected from the groups depicted in the compounds in Table 1.

As defined generally above, $R^7$ is H or $R^B$, wherein $R^7$ is substituted with t instances of $R^{7A}$. In some embodiments, $R^7$ is H. In some embodiments, $R^7$ is $R^B$, wherein $R^7$ is substituted with t instances of $R^{7A}$. In some embodiments, $R^7$ is $C_{1-6}$ aliphatic; phenyl; a 5-6 membered monocyclic heteroaryl ring having 1-4 heteroatoms independently selected from nitrogen, oxygen, and sulfur; a 3-7 membered saturated or partially unsaturated carbocyclic ring; or a 3-7 membered saturated or partially unsaturated monocyclic heterocyclic ring having 1-2 heteroatoms independently selected from nitrogen, oxygen, and sulfur; each of which is substituted with t instances of $R^{7A}$. In some embodiments, $R^7$ is $C_{1-6}$ aliphatic; a 3-7 membered saturated or partially unsaturated carbocyclic ring; or a 3-7 membered saturated or partially unsaturated monocyclic heterocyclic ring having 1-2 heteroatoms independently selected from nitrogen, oxygen, and sulfur; each of which is substituted with t instances of $R^{7A}$.

In some embodiments, $R^7$ is $C_{1-6}$ alkyl; a 3-7 membered saturated carbocyclic ring; or a 3-7 membered saturated monocyclic heterocyclic ring having 1-2 heteroatoms independently selected from nitrogen and oxygen; each of which is substituted with 0-1 instances of $R^{7A}$ and 0-3 halogens. In some embodiments, $R^7$ is $C_{1-6}$ alkyl substituted with 0-1 instances of $R^{7A}$ and 0-3 halogens. In some embodiments, $R^7$ is —$C_{1-4}$ alkyl, —($C_{1-4}$ alkyl)-OH, —($C_{1-4}$ alkyl)-O—($C_{1-4}$ alkyl), or —($C_{1-4}$ alkyl)-N($C_{1-4}$ alkyl)$_2$; wherein each $C_{1-4}$ alkyl is optionally substituted with 1, 2, or 3 fluoro. In some embodiments, $R^7$ is —$C_{1-4}$ alkyl, optionally substituted with 1, 2, or 3 fluoro. In some embodiments, $R^7$ is —$CH_3$. In some embodiments, $R^7$ is $C_{1-6}$ alkyl substituted with 0-1 instances of $R^B$ and 0-3 halogens.

In some embodiments, $R^7$ is a 3-7 membered saturated carbocyclic ring substituted with 0-1 instances of $R^{7A}$ and 0-3 halogens. In some embodiments, $R^7$ is a 3-7 membered saturated monocyclic heterocyclic ring having 1-2 heteroatoms independently selected from nitrogen and oxygen; which is substituted with 0-1 instances of $R^{7A}$ and 0-3 halogens. In some embodiments, $R^7$ is a 5-6 membered saturated monocyclic heterocyclic ring having 1 oxygen atom; which is substituted with 0-1 instances of $R^{7A}$ and 0-3 halogens. In some embodiments, $R^7$ is a 5-6 membered saturated monocyclic heterocyclic ring having 1 oxygen atom; which is substituted with 0-3 halogens and 0-1 group selected from —$C_{1-4}$ alkyl, —OH, —O—($C_{1-4}$ alkyl), or N($C_{1-4}$ alkyl)$_2$; wherein each $C_{1-4}$ alkyl is optionally substituted with 1, 2, or 3 fluoro. In some embodiments, $R^7$ is a 5-6 membered saturated monocyclic heterocyclic ring having 1 oxygen atom. In some embodiments, $R^7$ is selected from the groups depicted in the compounds in Table 1.

As defined generally above, m is 0, 1, 2, 3, or 4. In some embodiments, m is 0. In some embodiments, m is 1. In some embodiments, m is 2. In some embodiments, m is 3. In some embodiments, m is 4. In some embodiments, m is 0 or 1. In some embodiments, m is 0, 1, or 2. In some embodiments, m is 0, 1, 2, or 3. In some embodiments, m is 1 or 2. In some embodiments, m is 1, 2, or 3. In some embodiments, m is 1, 2, 3, or 4. In some embodiments, m is 2 or 3. In some embodiments, m is 2, 3, or 4. In some embodiments, m is 3 or 4. In some embodiments, m is selected from the values represented in the compounds in Table 1.

As defined generally above, n is 0, 1, 2, 3, or 4. In some embodiments, n is 0. In some embodiments, n is 1. In some embodiments, n is 2. In some embodiments, n is 3. In some embodiments, n is 4. In some embodiments, n is 0 or 1. In some embodiments, n is 0, 1, or 2. In some embodiments, n is 0, 1, 2, or 3. In some embodiments, n is 1 or 2. In some embodiments, n is 1, 2, or 3. In some embodiments, n is 1, 2, 3, or 4. In some embodiments, n is 2 or 3. In some embodiments, n is 2, 3, or 4. In some embodiments, n is 3 or 4. In some embodiments, n is selected from the values represented in the compounds in Table 1.

As defined generally above, p is 0, 1, 2, 3, or 4. In some embodiments, p is 0. In some embodiments, p is 1. In some embodiments, p is 2. In some embodiments, p is 3. In some embodiments, p is 4. In some embodiments, p is 0 or 1. In some embodiments, p is 0, 1, or 2. In some embodiments, p is 0, 1, 2, or 3. In some embodiments, p is 1 or 2. In some embodiments, p is 1, 2, or 3. In some embodiments, p is 1, 2, 3, or 4. In some embodiments, p is 2 or 3. In some embodiments, p is 2, 3, or 4. In some embodiments, p is 3 or 4. In some embodiments, p is selected from the values represented in the compounds in Table 1.

As defined generally above, q is 0, 1, 2, 3, or 4. In some embodiments, q is 0. In some embodiments, q is 1. In some embodiments, q is 2. In some embodiments, q is 3. In some embodiments, q is 4. In some embodiments, q is 0 or 1. In some embodiments, q is 0, 1, or 2. In some embodiments, q is 0, 1, 2, or 3. In some embodiments, q is 1 or 2. In some embodiments, q is 1, 2, or 3. In some embodiments, q is 1, 2, 3, or 4. In some embodiments, q is 2 or 3. In some embodiments, q is 2, 3, or 4. In some embodiments, q is 3 or 4. In some embodiments, q is selected from the values represented in the compounds in Table 1.

As defined generally above, r is 0, 1, 2, 3, or 4. In some embodiments, r is 0. In some embodiments, r is 1. In some embodiments, r is 2. In some embodiments, r is 3. In some embodiments, r is 4. In some embodiments, r is 0 or 1. In some embodiments, r is 0, 1, or 2. In some embodiments, r is 0, 1, 2, or 3. In some embodiments, r is 1 or 2. In some embodiments, r is 1, 2, or 3. In some embodiments, r is 1, 2, 3, or 4. In some embodiments, r is 2 or 3. In some embodiments, r is 2, 3, or 4. In some embodiments, r is 3 or 4. In some embodiments, r is selected from the values represented in the compounds in Table 1.

As defined generally above, t is 0, 1, 2, 3, or 4. In some embodiments, t is 0. In some embodiments, t is 1. In some embodiments, t is 2. In some embodiments, t is 3. In some embodiments, t is 4. In some embodiments, t is 0 or 1. In some embodiments, t is 0, 1, or 2. In some embodiments, t is 0, 1, 2, or 3. In some embodiments, t is 1 or 2. In some embodiments, t is 1, 2, or 3. In some embodiments, t is 1, 2, 3, or 4. In some embodiments, t is 2 or 3. In some embodiments, t is 2, 3, or 4. In some embodiments, t is 3 or 4. In some embodiments, t is selected from the values represented in the compounds in Table 1.

As defined generally above, u is 0, 1, 2, 3, or 4. In some embodiments, u is 0. In some embodiments, u is 1. In some embodiments, u is 2. In some embodiments, u is 3. In some embodiments, u is 4. In some embodiments, u is 0 or 1. In some embodiments, u is 0, 1, or 2. In some embodiments, u is 0, 1, 2, or 3. In some embodiments, u is 1 or 2. In some embodiments, u is 1, 2, or 3. In some embodiments, u is 1, 2, 3, or 4. In some embodiments, u is 2 or 3. In some embodiments, u is 2, 3, or 4. In some embodiments, u is 3 or 4. In some embodiments, u is selected from the values represented in the compounds in Table 1.

In some embodiments, the present invention provides a compound of formula I-1 comprising a pyrrolopyrimidine, pyrrolotriazine, pyrazolopyrazine, pyrrolopyridine, furopyrimidine, thienopyrimidine, or pyrrolopyridazinone thereby forming a compound of formulas Ia, Ib, Ic, Id, Ie, If, Ig, or Ih:

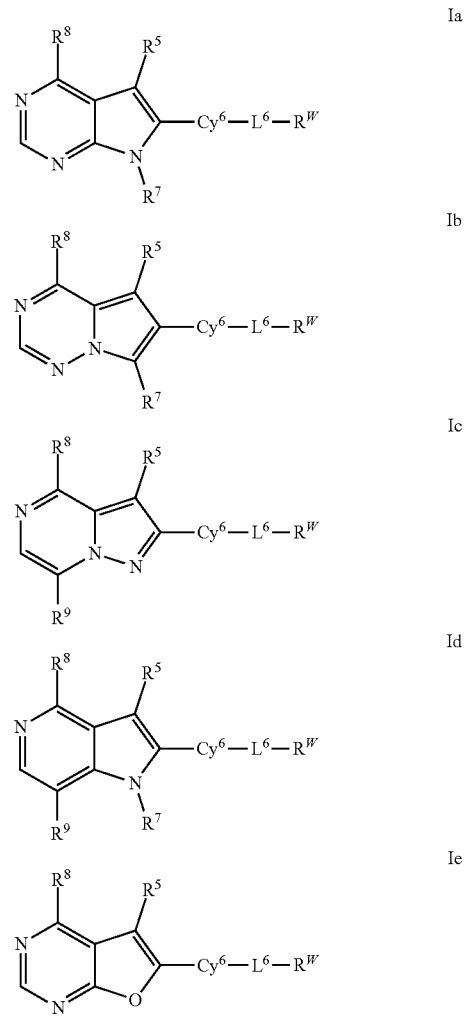

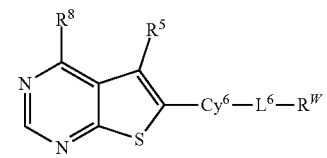
If

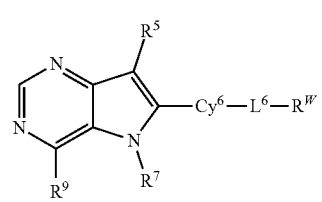
Ig

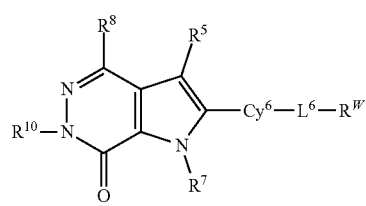
Ih or a pharmaceutically acceptable salt thereof, wherein each of $Cy^6$, $L^6$, $R^W$, $R^5$, $R^7$, $R^8$, $R^9$, and $R^{10}$ is as defined in embodiments and classes and subclasses herein.

In some embodiments, the present invention provides a compound of formula I-1 wherein $R^{5A}$ is phenylene, pyridinylene, or cyclohexenylene, thereby forming a compound of formulas II-1, III-1, IV-1, or V-1:

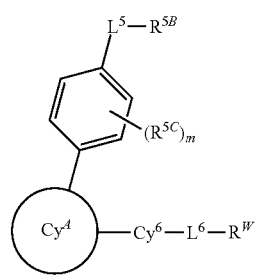
II-1

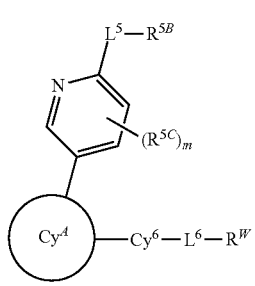
III-1

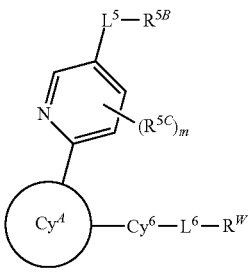
IV-1

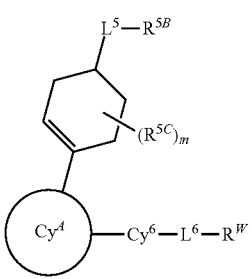
V-1 or a pharmaceutically acceptable salt thereof, wherein each of $Cy^A$, $Cy^6$, $L^5$, $L^6$, $R^{5B}$, $R^{5C}$, $R^W$, and m is as defined in embodiments and classes and subclasses herein.

In some embodiments, the present invention provides a compound of formula I-1 wherein $Cy^6$ is phenylene, pyridinylene, or pyrimidinylene, thereby forming a compound of formulas VI-1, VII-1, VIII-1, or IX-1:

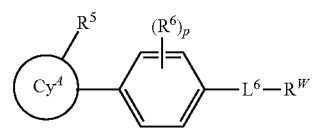
VI-1

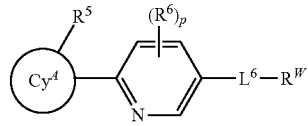
VII-1

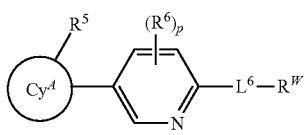
VIII-1

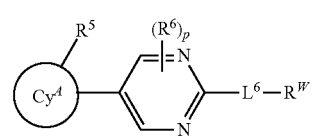
IX-1 or a pharmaceutically acceptable salt thereof, wherein each of $Cy^A$, $L^6$, $R^5$, $R^W$, $R^6$, and p is as defined in embodiments and classes and subclasses herein.

In some embodiments, the present invention provides a compound of formulas II-1, III-1, IV-1, or V-1 wherein $Cy^6$ is phenylene, thereby forming a compound of formulas X-1, XI-1, XII-1, or XIII-1, respectively:

X-1
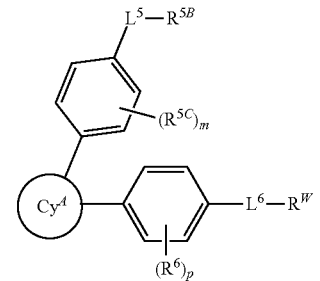

XI-1
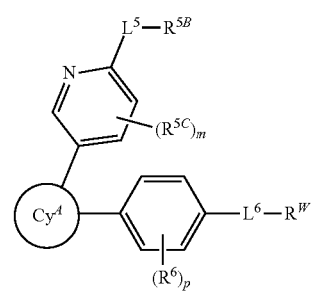

XII-1
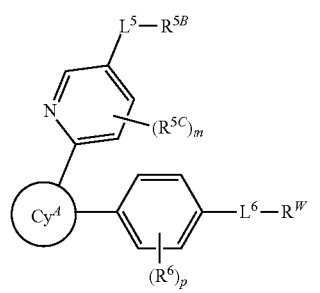

XIII-1
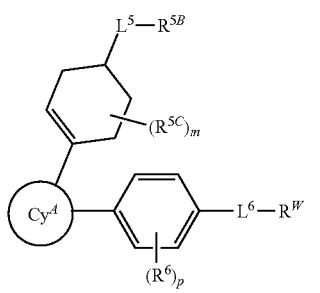

or a pharmaceutically acceptable salt thereof, wherein each of $Cy^A$, $L^5$, $L^6$, $R^{5B}$, $R^{5C}$, $R^W$, $R^6$, m, and p is as defined in embodiments and classes and subclasses herein.

For example, in some embodiments, the present invention provides a compound of formula X-1, XI-1, XII-1, or XIII-1:

X-1
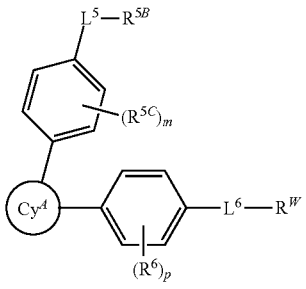

XI-1
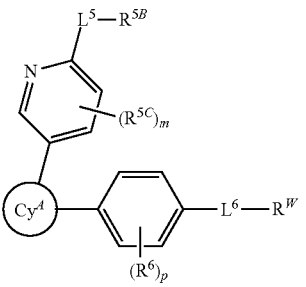

XII-1
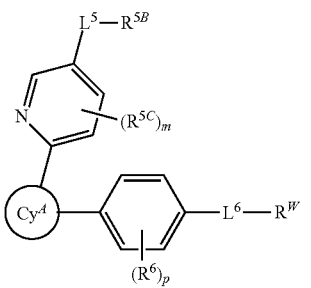

XIII-1
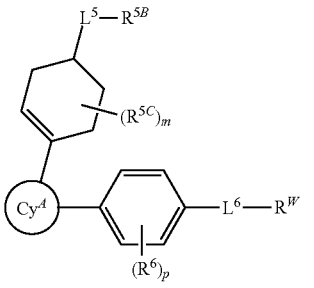

or a pharmaceutically acceptable salt thereof, wherein:
$Cy^A$ is

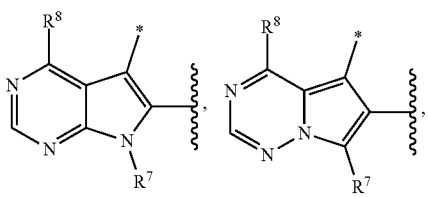

-continued

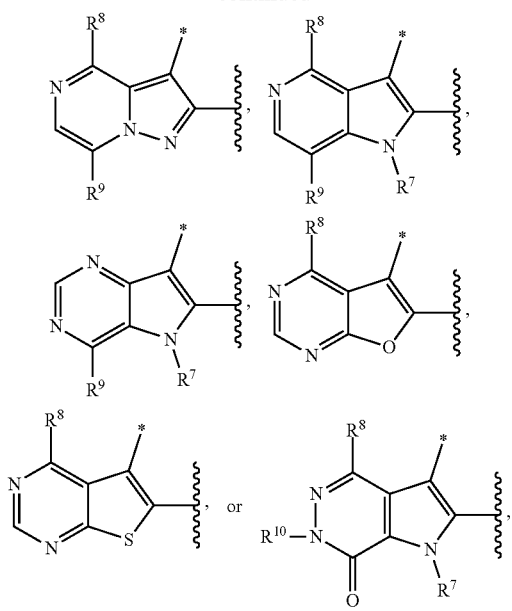

wherein the ⤴* of Cy$^A$ represents a bond to

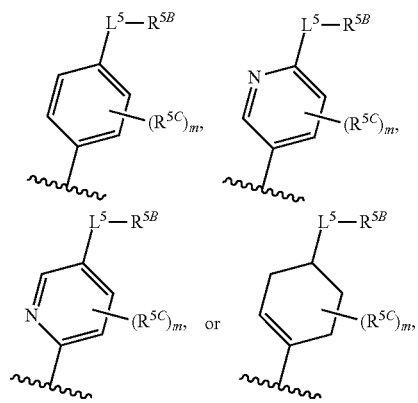

and ⤴⤵ of Cy$^A$ represents a bond to

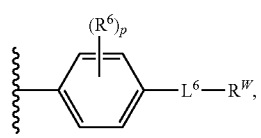

R$^{5B}$ is hydrogen or R$^B$, wherein R$^{5B}$ is substituted with n instances of R$^{5D}$;

R$^W$ is halogen, —CN,

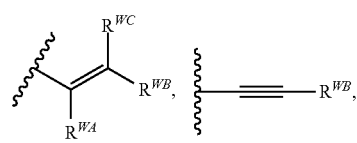

-continued

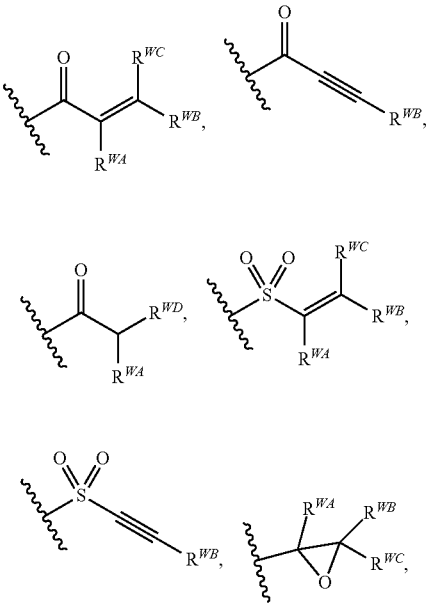

each instance of R$^6$ is independently R$^A$ or R$^B$, wherein R$^6$ is substituted by q instances of R$^C$; or two instances of R$^6$, or an instance of R$^6$ and an instance of R$^L$ are taken together with their intervening atoms to form a 4-7 membered partially unsaturated or aromatic ring having 0-4 heteroatoms independently selected from nitrogen, oxygen, and sulfur; wherein said ring is substituted with r instances of R$^C$;

R$^7$ is H or R$^B$, wherein R$^7$ is substituted with t instances of R$^{7A}$;

R$^8$ is H, —NR$_2$, halogen, —OH, or C$_{1-6}$ aliphatic optionally substituted with 1-3 halogens;

R$^9$ is H, —NR$_2$, halogen, or C$_{1-6}$ aliphatic optionally substituted with 1-3 halogens;

R$^{10}$ is H or C$_{1-6}$ aliphatic optionally substituted with 1-3 halogens;

each of L$^5$ and L$^6$ is independently a covalent bond, or a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-5}$ cycloalkylene, 3-5 membered heterocycloalkylene, 5-6 membered heteroarylene, —NH—, —N(R$^L$)—, —NHC(O)—, —N(R$^L$)C(O)—, —C(O)NH—, —C(O)N(R$^L$)—, —NHS(O)$_2$—, —N(R$^L$)

$S(O)_2$—, —$S(O)_2NH$—, —$S(O)_2N(R^L)$—, —O—, —C(O)—, —OC(O)—, —C(O)O—, —S—, —S(O)—, or —$S(O)_2$—;

- each of $R^{WA}$, $R^{WB}$, and $R^{WC}$ is independently hydrogen, halogen, —CN, —C(O)R, —C(O)OR, —C(O)$NR_2$, —C(O)N(R)OR, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; or
  $R^{WA}$ and $R^{WB}$, $R^{WB}$ and $R^{WC}$, $R^{WA}$ and an instance of $R^L$, or $R^{WC}$ and an instance of $R^L$ are taken together with their intervening atoms to form a 4-7 membered saturated or partially unsaturated ring having 0-2 heteroatoms independently selected from nitrogen, oxygen, and sulfur;
- $R^{WD}$ is halogen or —$OS(O)_2R$;
- each instance of $R^{5C}$, $R^{5D}$, $R^{7A}$, and $R^L$ is independently $R^A$ or $R^B$, and is substituted by u instances of $R^C$;
- each instance of $R^A$ is independently oxo, halogen, —CN, —$NO_2$, —OR, —SR, —$NR_2$, —$S(O)_2R$, —$S(O)_2NR_2$, —S(O)R, —$S(O)NR_2$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)$S(O)_2NR_2$, or —N(R)$S(O)_2R$;
- each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;
- each instance of $R^C$ is independently oxo, halogen, —CN, —$NO_2$, —OR, —SR, —$NR_2$, —$S(O)_2R$, —$S(O)_2NR_2$, —S(O)R, —$S(O)NR_2$, —$S(O)_2F$, —$OS(O)_2F$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)$S(O)_2NR_2$, —N(R)$S(O)_2R$, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
- each R is independently hydrogen, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and
- each of m, n, p, q, r, t, and u is independently 0, 1, 2, 3, or 4.

In some embodiments, the present invention provides a compound of formula X-1, XI-1, XII-1, or XIII-1:

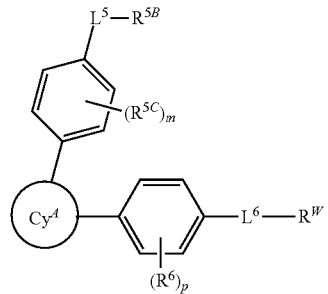

X-1

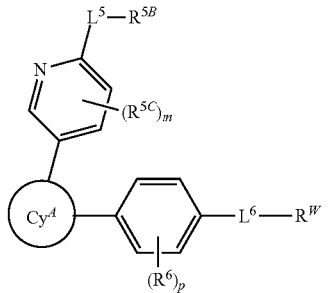

XI-1

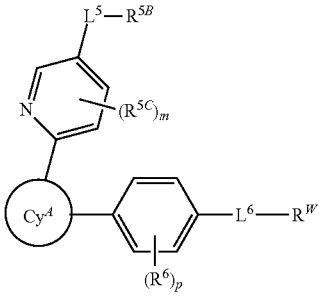

XII-1

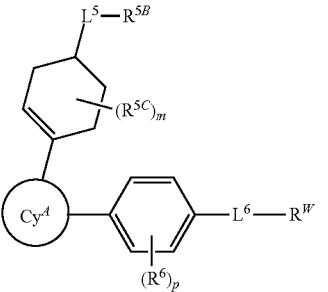

XIII-1 or a pharmaceutically acceptable salt thereof, wherein:
$Cy^A$ is

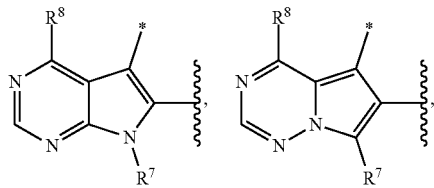

-continued

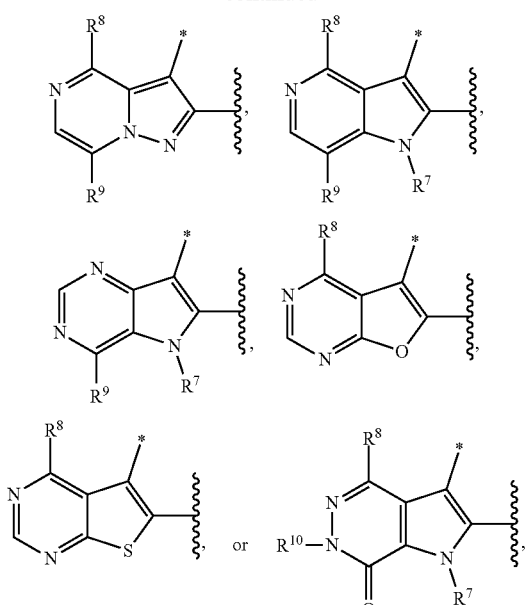

wherein the ✶ of Cy$^A$ represents a bond to

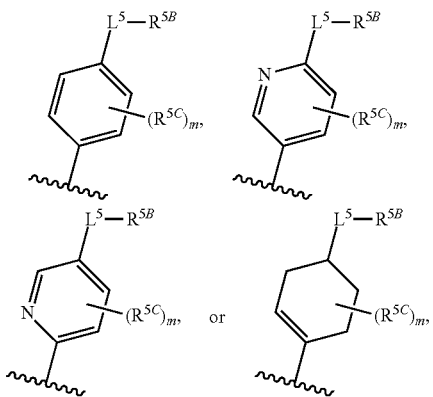

and ⤳ of Cy$^A$ represents a bond to

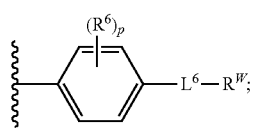

R$^{5B}$ is hydrogen or R$^B$, wherein R$^{5B}$ is substituted with n instances of R$^{5D}$;

R$^W$ is halogen, —CN,

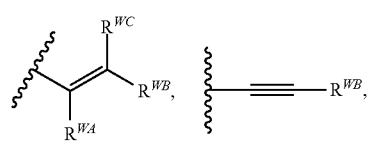

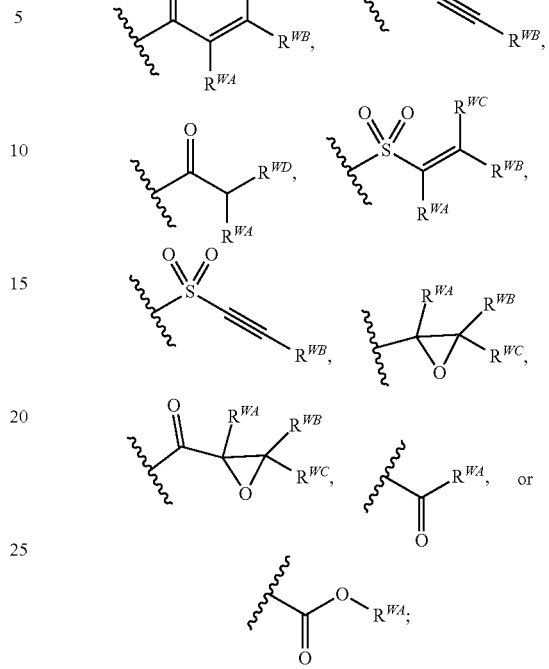

each instance of R$^6$ is independently R$^A$ or R$^B$, wherein R$^6$ is substituted by q instances of R$^C$; or
two instances of R$^6$, or an instance of R$^6$ and an instance of R$^L$ are taken together with their intervening atoms to form a 4-7 membered partially unsaturated or aromatic ring having 0-4 heteroatoms independently selected from nitrogen, oxygen, and sulfur; wherein said ring is substituted with r instances of R$^C$;

R$^7$ is H or R$^B$, wherein R$^7$ is substituted with t instances of R$^{7A}$;

R$^8$ is H, —NR$_2$, halogen, —OH, or C$_{1-6}$ aliphatic optionally substituted with 1-3 halogens;

R$^9$ is H, —NR$_2$, halogen, or C$_{1-6}$ aliphatic optionally substituted with 1-3 halogens;

R$^{10}$ is H or C$_{1-6}$ aliphatic optionally substituted with 1-3 halogens;

each of L$^5$ and L$^6$ is independently a covalent bond, or a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-5}$ cycloalkylene, 3-5 membered heterocycloalkylene, 5-6 membered heteroarylene, —NH—, —N(R$^L$)—, —NHC(O)—, —N(R$^L$)C(O)—, —C(O)NH—, —C(O)N(R$^L$)—, —NHS(O)$_2$—, —N(R$^L$)S(O)$_2$—, —S(O)$_2$NH—, —S(O)$_2$N(R$^L$)—, —O—, —C(O)—, —OC(O)—, —C(O)O—, —S—, —S(O)—, or —S(O)$_2$—;

each of R$^{WA}$, R$^{WB}$, and R$^{WC}$ is independently hydrogen, deuterium, halogen, —CN, —C(O)R, —C(O)OR, —C(O)NR$_2$, —C(O)N(R)OR, or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; or R$^{WA}$ and R$^{WB}$, R$^{WB}$ and R$^{WC}$, R$^{WA}$ and an instance of R$^L$, or R$^{WC}$ and an instance of R$^L$ are taken together with their intervening atoms to form a 4-7 membered saturated or partially unsaturated ring having 0-2 heteroatoms independently selected from nitrogen, oxygen, and sulfur;

R$^{WD}$ is halogen or —OS(O)$_2$R;

each instance of R$^{5C}$, R$^{5D}$, R$^{7A}$, and R$^L$ is independently R$^A$ or R$^B$, and is substituted by u instances of R$^C$;

each instance of R$^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of R$^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of R$^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —S(O)$_2$F, —OS(O)$_2$F, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of m, n, p, q, r, t, and u is independently 0, 1, 2, 3, or 4.

In some embodiments, the present invention provides a compound of formulas II-1, III-1, IV-1, or V-1 wherein Cy$^6$ is pyridinylene, thereby forming a compound of formulas XIV-1, XV-1, XVI-1, XVII-1, XVIII-1, XIX-1, XX-1, or XXI-1 respectively:

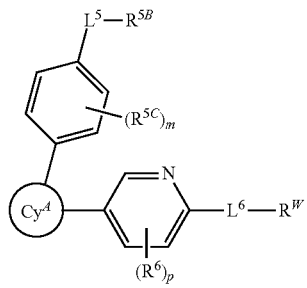

XIV-1

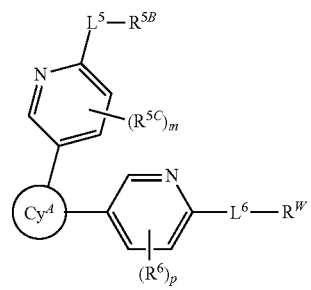

XV-1

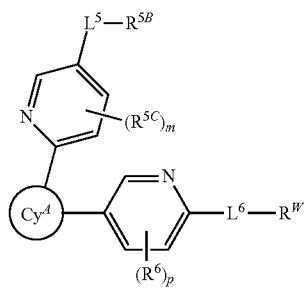

XVI-1

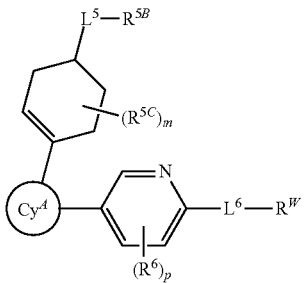

XVII-1

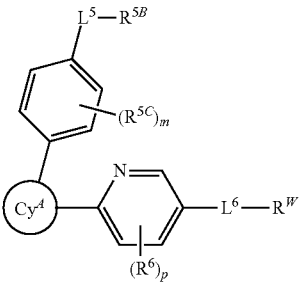

XVIII-1

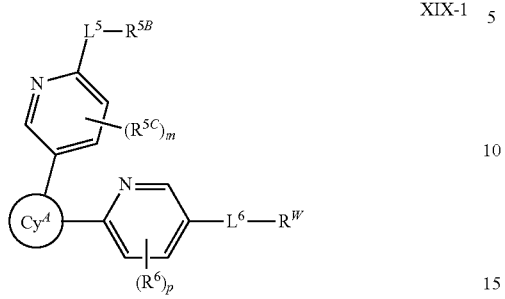

XIX-1

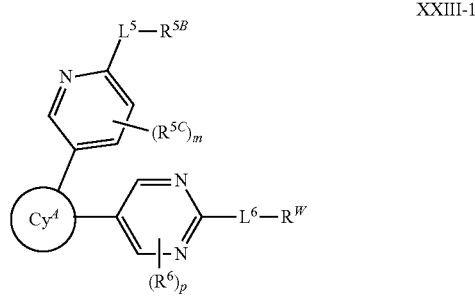

XXIII-1

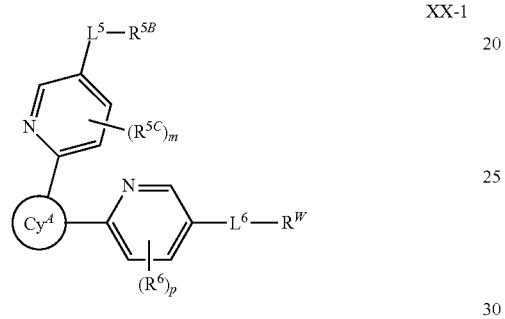

XX-1

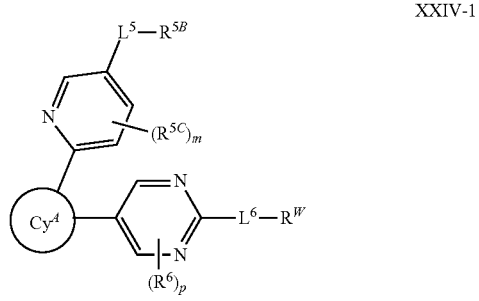

XXIV-1

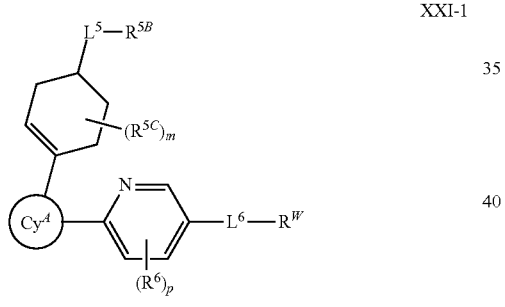

XXI-1

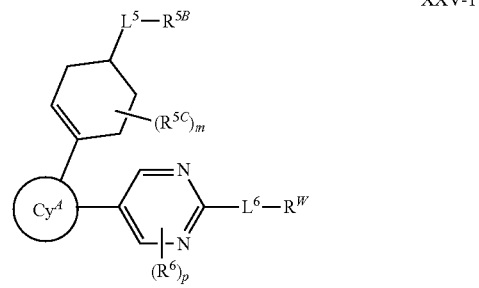

XXV-1 or a pharmaceutically acceptable salt thereof, wherein each of $Cy^A$, $L^5$, $L^6$, $R^{5B}$, $R^{5C}$, $R^W$, $R^6$, m, and p is as defined in embodiments and classes and subclasses herein.

In some embodiments, the present invention provides a compound of formulas II-1, III-1, IV-1, or V-1 wherein $Cy^6$ is pyrimidinylene, thereby forming a compound of formulas XXII-1, XXIII-1, XXIV-1, or XXV-1 respectively:

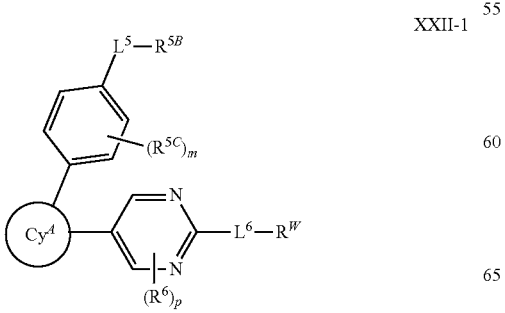

XXII-1 or a pharmaceutically acceptable salt thereof, wherein each of $Cy^A$, $L^5$, $L^6$, $R^{5B}$, $R^{5C}$, $R^W$, $R^6$, m, and p is as defined in embodiments and classes and subclasses herein.

In some embodiments, the present invention provides a compound of formula I-1, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1 wherein $Cy^A$ is 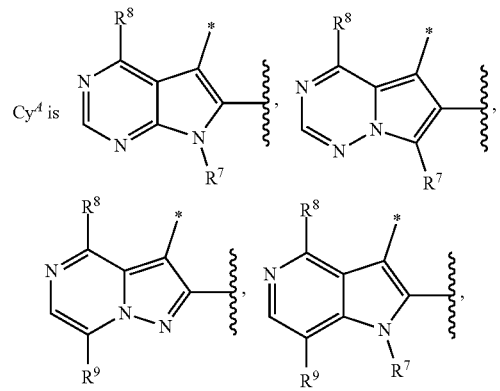

-continued

[chemical structures]

wherein ∕* represents a bond to R⁵ and ⋋* represents a bond to Cy⁶.

In some embodiments, the present invention provides a compound of formula I-1, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1 wherein Cy$^A$ is

[chemical structure]

wherein ∕* represents a bond to R⁵ and ⋋* represents a bond to Cy⁶.

In some embodiments, the present invention provides a compound of I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein L⁵ is —O—, —C(O)—, —C(O)NH—, or —C(O)N(R$^L$)—. In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1 wherein L⁵ is —O—. In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein L⁵ is —C(O)—. In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein L⁵ is —C(O)NH—. In some embodiments, the present invention provides a compound of I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein L⁵ is —C(O)N(R$^L$)—.

In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein L⁶ is —NH— or —N(R$^L$)—. In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein L⁶ is —NH—.

In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein m is 0 or 1. In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein m is 0. In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-I, wherein m is 1.

In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein p is 0 or 1. In some embodiments, the present invention provides a compound of I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein p is 0. In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein p is 1.

In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein R$^W$ is

[chemical structure showing carbonyl with R$^{WA}$, R$^{WB}$, R$^{WC}$ substituents]

In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIII-1, XXIV-1, or XXV-1, wherein R$^W$ is

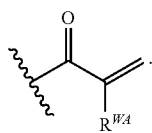

In some embodiments, the present invention provides a compound of formula I-1, Ia, Ib, Ic, Id, Ie, If, Ig, Ih, II-1, III-1, IV-1, V-1, VI-1, VII-1, VIII-1, IX-1, X-1, XI-1, XII-1, XIII-1, XIV-1, XV-1, XVI-1, XVII-1, XVIII-1, XIX-1, XX-1, XXI-1, XXII-1, XXIV-1, or XXV-1, wherein $R^W$ is

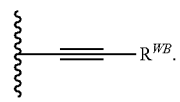

In some embodiments, the present invention provides a compound of formula I wherein $R^{5A}$ is phenylene, pyridinylene, or cyclohexenylene, thereby forming a compound of formulas II, III, IV, or V:

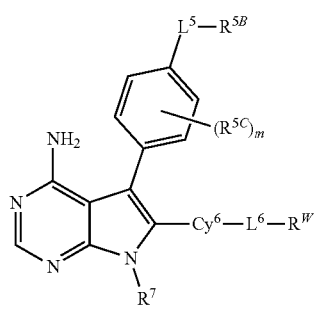

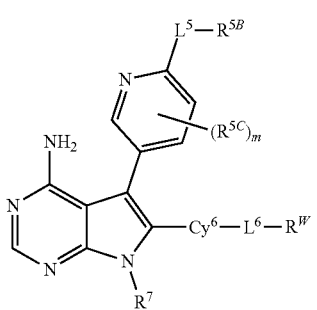

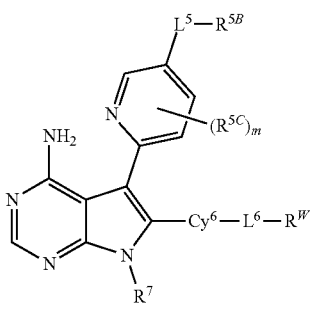

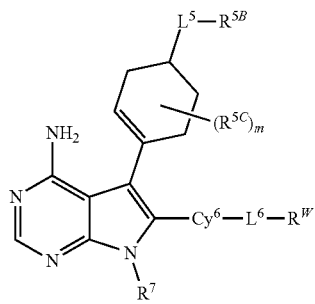

or a pharmaceutically acceptable salt thereof, wherein each of $Cy^6$, $L^5$, $L^6$, $R^{5B}$, $R^{5C}$, $R^W$, $R^7$, and m is as defined in embodiments and classes and subclasses herein.

In some embodiments, the present invention provides a compound of formula I wherein $Cy^6$ is phenylene, pyridinylene, or pyrimidinylene, thereby forming a compound of formulas VI, VII, VIII, or IX:

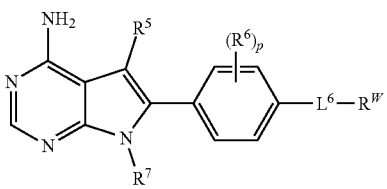

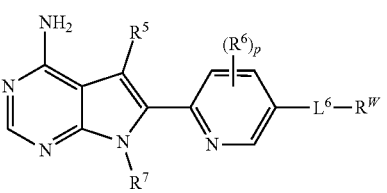

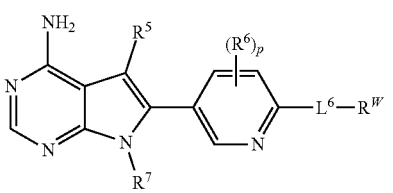

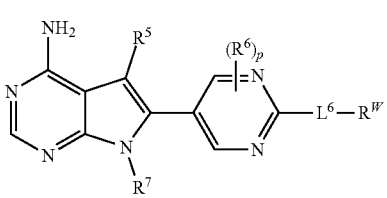

or a pharmaceutically acceptable salt thereof, wherein each of $L^6$, $R^5$, $R^W$, $R^6$, $R^7$, and p is as defined in embodiments and classes and subclasses herein.

In some embodiments, the present invention provides a compound of formulas II, III, IV, or V wherein $Cy^6$ is phenylene, thereby forming a compound of formulas X, XI, XII, or XIII, respectively:

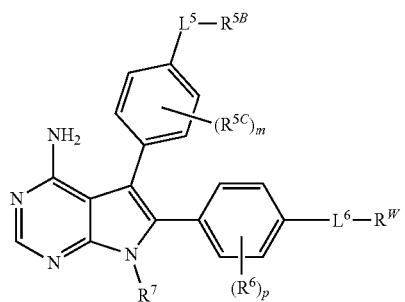

X

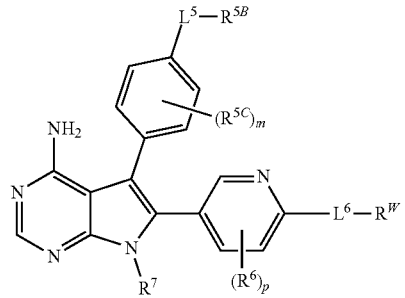

XIV

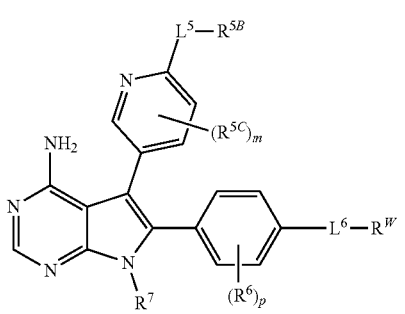

XI

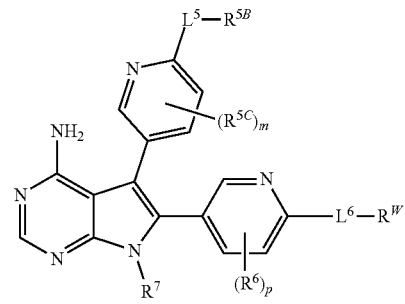

XV

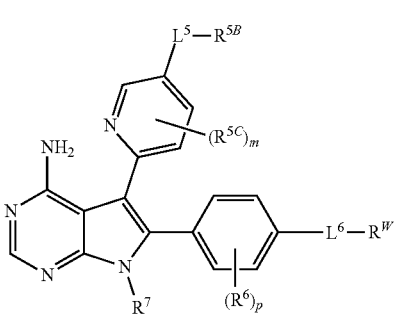

XII

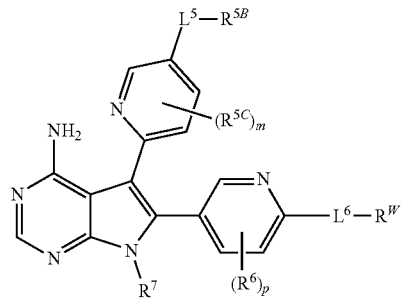

XVI

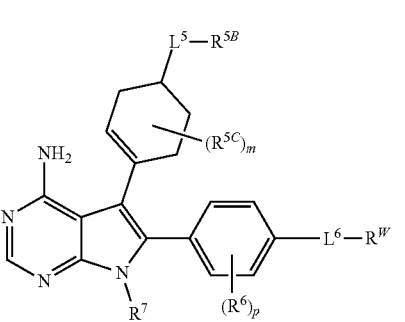

XIII

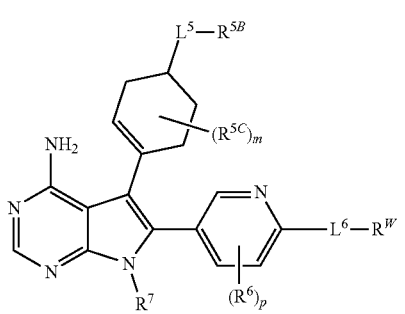

XVII or a pharmaceutically acceptable salt thereof, wherein each of $L^5$, $L^6$, $R^{5B}$, $R^{5C}$, $R^W$, $R^6$, $R^7$, m, and p is as defined in embodiments and classes and subclasses herein.

In some embodiments, the present invention provides a compound of formulas II, III, IV, or V wherein $Cy^6$ is pyridinylene, thereby forming a compound of formulas XIV, XV, XVI, XVII, XVIII, XIX, XX, or XXI respectively:

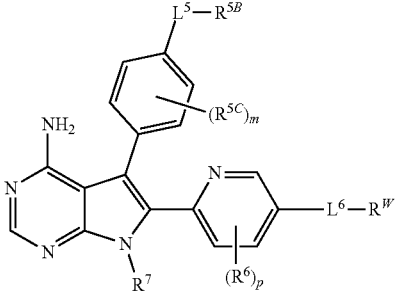

XVIII

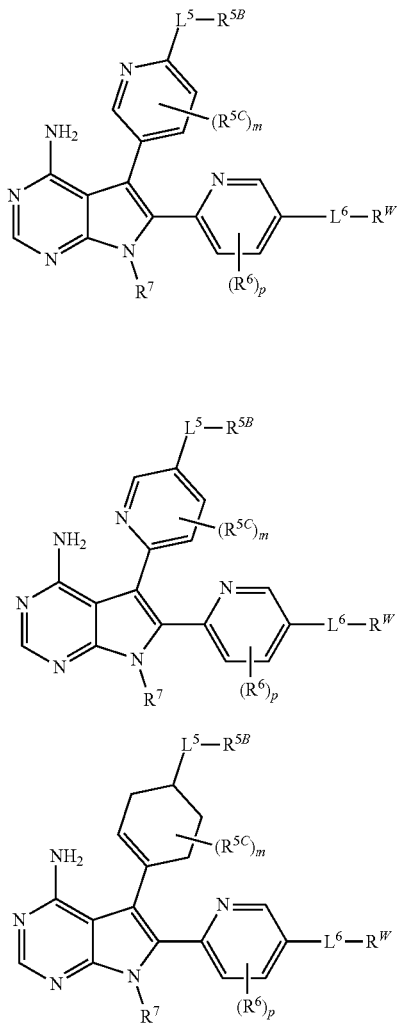

XIX

XX

XXI

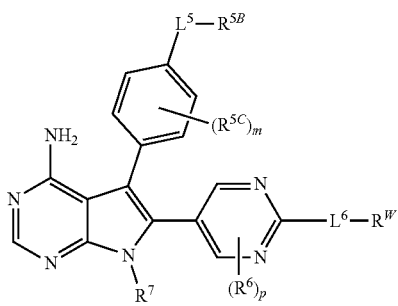

XXII or a pharmaceutically acceptable salt thereof, wherein each of $Cy^A$, $L^5$, $L^6$, $R^{5B}$, $R^{5C}$, $R^W$, $R^6$, m, and p is as defined in embodiments and classes and subclasses herein.

In some embodiments, the present invention provides a compound of formulas II, III, IV, or V wherein $Cy^6$ is pyrimidinylene, thereby forming a compound of formulas XXII, XXIII, XXIV, or XXV respectively:

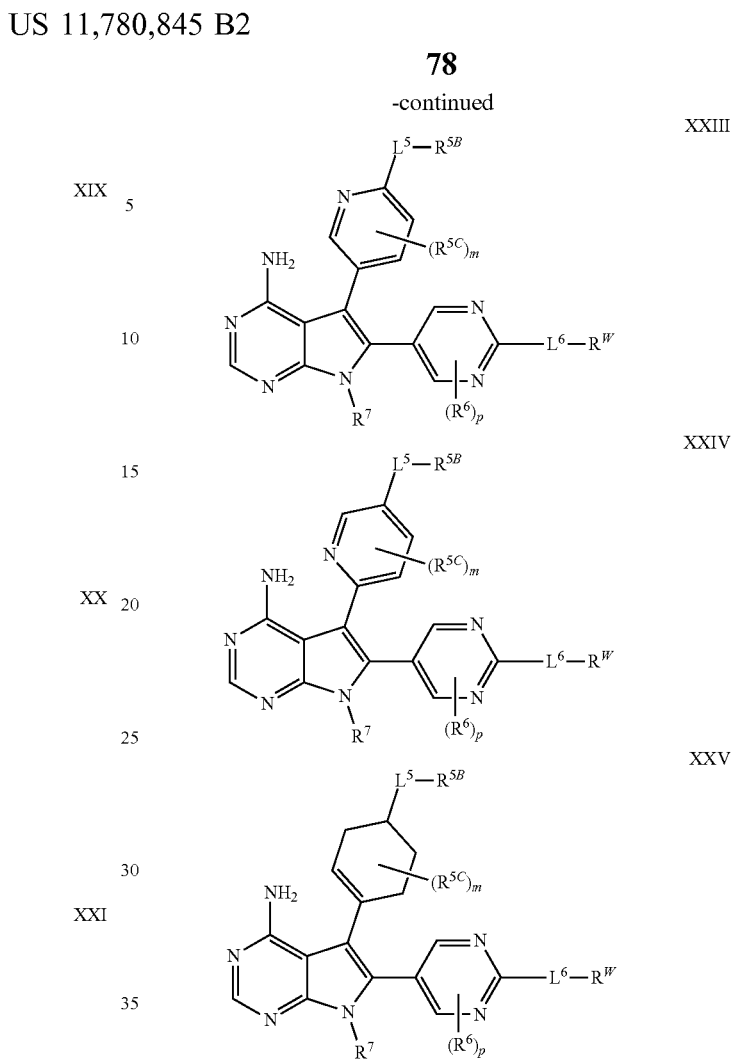

XXIII

XXIV

XXV or a pharmaceutically acceptable salt thereof, wherein each of $Cy^A$, $L^5$, $L^6$, $R^{5B}$, $R^{5C}$, $R^W$, $R^6$, m, and p is as defined in embodiments and classes and subclasses herein.

In some embodiments, the present invention provides a compound of formula I, II, III, IV, V, VI, VII, VIII, IX, X, XI, XII, or XIII, wherein $L^5$ is —O—, —C(O)—, —C(O)NH—, or —C(O)N($R^L$)—. In some embodiments, the present invention provides a compound of formula I, II, III, IV, V, VI, VII, VIII, IX, X, XI, XII, or XIII, wherein $L^5$ is —O—. In some embodiments, the present invention provides a compound of formula I, II, III, IV, V, VI, VII, VIII, IX, X, XI, XII, or XIII, wherein $L^5$ is —C(O)—. In some embodiments, the present invention provides a compound of formula I, II, III, IV, V, VI, VII, VIII, IX, X, XI, XII, or XIII, wherein $L^5$ is —C(O)NH—. In some embodiments, the present invention provides a compound of formula I, II, III, IV, V, VI, VII, VIII, IX, X, XI, XII, or XIII, wherein $L^5$ is —C(O)N($R^L$)—.

In some embodiments, the present invention provides a compound of formula I, II, III, IV, V, VI, VII, VIII, IX, X, XI, XII, or XIII, wherein $L^6$ is —NH— or —N($R^L$)—. In some embodiments, the present invention provides a compound of formula I, II, III, IV, V, VI, VII, VIII, IX, X, XI, XII, or XIII, wherein $L^6$ is —NH—.

In some embodiments, the present invention provides a compound of formula I, II, III, IV, V, VI, VII, VIII, IX, X, XI, XII, or XIII, wherein m is 0 or 1. In some embodiments, the present invention provides a compound of formula I, II, III, IV, V, VI, VII, VIII, IX, X, XI, XII, or XIII, wherein m is 0. In some embodiments, the present invention provides a compound of formula I, II, III, IV, V, VI, VII, VIII, IX, X, XI, XII, or XIII, wherein m is 1.

In some embodiments, the present invention provides a compound of formula I, II, III, IV, V, VI, VII, VIII, IX, X, XI, XII, or XIII, wherein p is 0 or 1. In some embodiments, the present invention provides a compound of formula I, II, III, IV, V, VI, VII, VIII, IX, X, XI, XII, or XIII, wherein p is 0. In some embodiments, the present invention provides a compound of formula I, II, III, IV, V, VI, VII, VIII, IX, X, XI, XII, or XIII, wherein p is 1.

In some embodiments, the present invention provides a compound of formula I, II, III, IV, V, VI, VII, VIII, IX, X, XI, XII, or XIII, wherein $R^W$ is

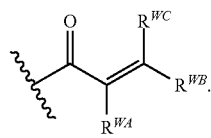

In some embodiments, the present invention provides a compound of formula I, II, III, IV, V, VI, VII, VIII, IX, X, XI, XII, or XIII, wherein $R^W$ is

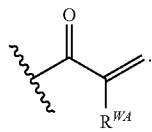

In some embodiments, the present invention provides a compound of formula I, II, III, IV, V, VI, VII, VIII, IX, X, XI, XII, or XIII, wherein $R^W$ is

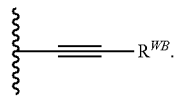

In some embodiments, the present invention provides a compound of XIV, XV, XVI, XVII, XVIII, XIX, XX, XXI, XXII, XXIII, XXIV, or XXV, wherein $L^5$ is —O—, —C(O)—, —C(O)NH—, or —C(O)N($R^L$)—. In some embodiments, the present invention provides a compound of formula XIV, XV, XVI, XVII, XVIII, XIX, XX, XXI, XXII, XXIII, XXIV, or XXV, wherein $L^5$ is —O—. In some embodiments, the present invention provides a compound of formula XIV, XV, XVI, XVII, XVIII, XIX, XX, XXI, XXII, XXIII, XXIV, or XXV, wherein $L^5$ is —C(O)—. In some embodiments, the present invention provides a compound of formula XIV, XV, XVI, XVII, XVIII, XIX, XX, XXI, XXII, XXIII, XXIV, or XXV, wherein $L^5$ is —C(O)NH—. In some embodiments, the present invention provides a compound of XIV, XV, XVI, XVII, XVIII, XIX, XX, XXI, XXII, XXIII, XXIV, or XXV, wherein $L^5$ is —C(O)N($R^L$)—.

In some embodiments, the present invention provides a compound of formula XIV, XV, XVI, XVII, XVIII, XIX, XX, XXI, XXII, XXIII, XXIV, or XXV, wherein $L^6$ is —NH— or —N($R^L$)—. In some embodiments, the present invention provides a compound of formula XIV, XV, XVI, XVII, XVIII, XIX, XX, XXI, XXII, XXIII, XXIV, or XXV, wherein $L^6$ is —NH—.

In some embodiments, the present invention provides a compound of formula XIV, XV, XVI, XVII, XVIII, XIX, XX, XXI, XXII, XXIII, XXIV, or XXV, wherein m is 0 or 1. In some embodiments, the present invention provides a compound of formula XIV, XV, XVI, XVII, XVIII, XIX, XX, XXI, XXII, XXIII, XXIV, or XXV, wherein m is 0. In some embodiments, the present invention provides a compound of formula XIV, XV, XVI, XVII, XVIII, XIX, XX, XXI, XXII, XXIII, XXIV, or XXV, wherein m is 1.

In some embodiments, the present invention provides a compound of formula XIV, XV, XVI, XVII, XVIII, XIX, XX, XXI, XXII, XXIII, XXIV, or XXV, wherein p is 0 or 1. In some embodiments, the present invention provides a compound of XIV, XV, XVI, XVII, XVIII, XIX, XX, XXI, XXII, XXIII, XXIV, or XXV, wherein p is 0. In some embodiments, the present invention provides a compound of formula XIV, XV, XVI, XVII, XVIII, XIX, XX, XXI, XXII, XXIII, XXIV, or XXV, wherein p is 1.

In some embodiments, the present invention provides a compound of formula XIV, XV, XVI, XVII, XVIII, XIX, XX, XXI, XXII, XXIII, XXIV, or XXV, wherein $R^W$ is

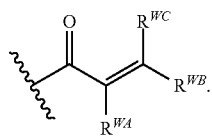

In some embodiments, the present invention provides a compound of formula XIV, XV, XVI, XVII, XVIII, XIX, XX, XXI, XXII, XXIII, XXIV, or XXV, wherein $R^W$ is

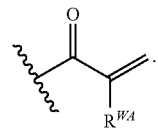

In some embodiments, the present invention provides a compound of formula XIV, XV, XVI, XVII, XVIII, XIX, XX, XXI, XXII, XXIII, XXIV, or XXV, wherein $R^W$ is

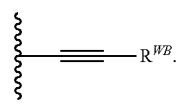

Examples of compounds of the present invention include those listed in the Tables and exemplification herein, or a pharmaceutically acceptable salt, stereoisomer, or mixture of stereoisomers thereof. In some embodiments, the present invention comprises a compound selected from those depicted in Table 1, below, or a pharmaceutically acceptable salt, stereoisomer, or mixture of stereoisomers thereof. In some embodiments, the present invention provides a compound set forth in Table 1, below, or a pharmaceutically acceptable salt thereof. In some embodiments, the present invention provides a compound set forth in Table 1, below.

TABLE 1
Representative Compounds of the Invention with Bioactivity Data.
| Example | Structure | Biochemical FGFR2 Caliper IC50 | Cell SNU-16 IC50 |
|---|---|---|---|
| 1 | 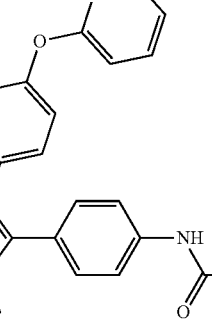 | A | A |
| 2 | 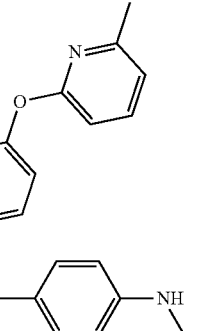 | C | |
| 3 | 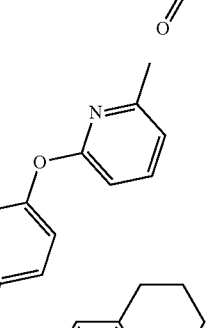 | A | |
| 4 | 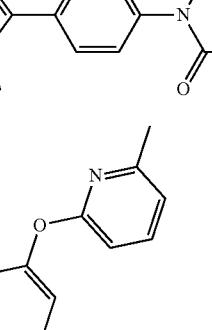 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 5 | 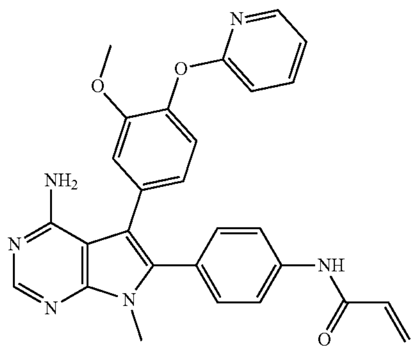 [SMILES: C=CC(=O)Nc1ccc(-c2c(-c3ccc(Oc4ccccn4)c(OC)c3)c3c(N)ncnc3n2C)cc1] | A | A |
| 6 | 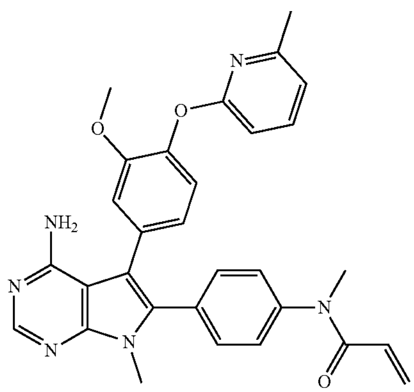 [SMILES: C=CC(=O)N(C)c1ccc(-c2c(-c3ccc(Oc4cccc(C)n4)c(OC)c3)c3c(N)ncnc3n2C)cc1] | B | |
| 7 | 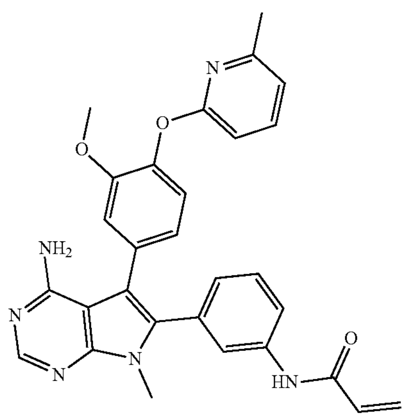 [SMILES: C=CC(=O)Nc1cccc(-c2c(-c3ccc(Oc4cccc(C)n4)c(OC)c3)c3c(N)ncnc3n2C)c1] | A | |
| 8 | 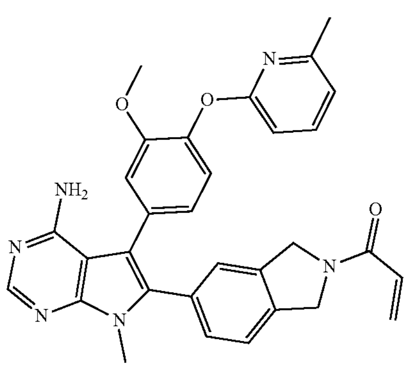 [SMILES: C=CC(=O)N1Cc2ccc(-c3c(-c4ccc(Oc5cccc(C)n5)c(OC)c4)c4c(N)ncnc4n3C)cc2C1] | A | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 9 | 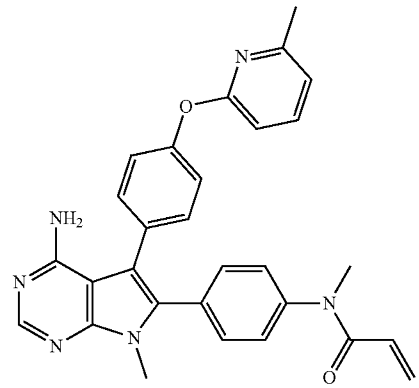 [SMILES: C=CC(=O)N(C)c1ccc(-c2c(-c3ccc(Oc4cccc(C)n4)cc3)c3c(N)ncnc3n2C)cc1] | A | |
| 10 | 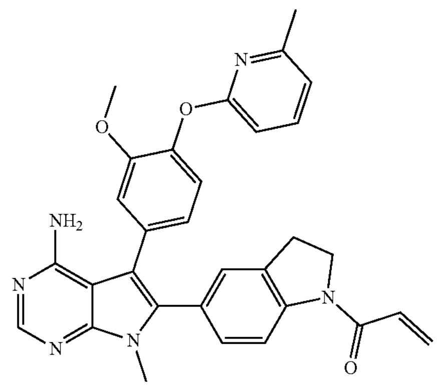 [SMILES: C=CC(=O)N1CCc2cc(-c3c(-c4ccc(Oc5cccc(C)n5)c(OC)c4)c4c(N)ncnc4n3C)ccc21] | A | |
| 11 | 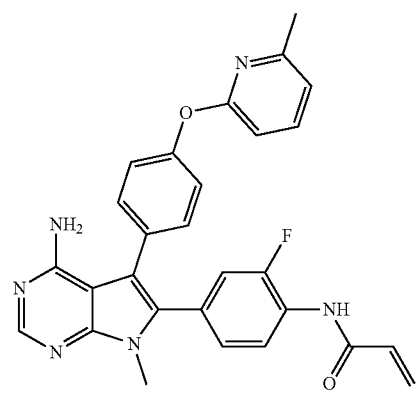 [SMILES: C=CC(=O)Nc1ccc(-c2c(-c3ccc(Oc4cccc(C)n4)cc3)c3c(N)ncnc3n2C)cc1F] | A | A |
| 12 | 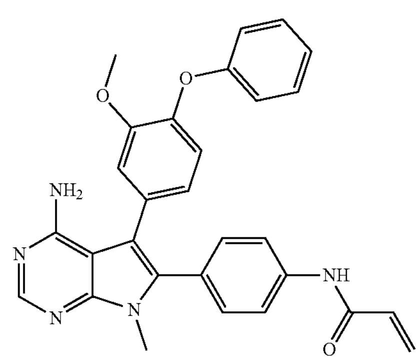 [SMILES: C=CC(=O)Nc1ccc(-c2c(-c3ccc(Oc4ccccc4)c(OC)c3)c3c(N)ncnc3n2C)cc1] | A | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 13 | 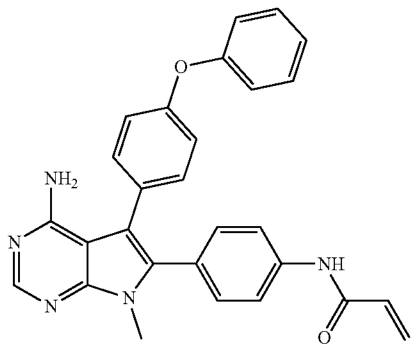 [SMILES: C=CC(=O)Nc1ccc(-c2c(-c3ccc(Oc4ccccc4)cc3)c3c(N)ncnc3n2C)cc1] | A | |
| 14 | 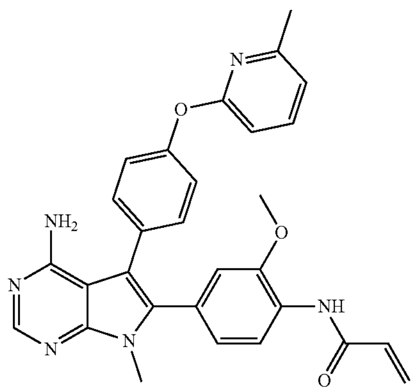 [SMILES: C=CC(=O)Nc1ccc(-c2c(-c3ccc(Oc4cccc(C)n4)cc3)c3c(N)ncnc3n2C)cc1OC] | A | A |
| 15 | 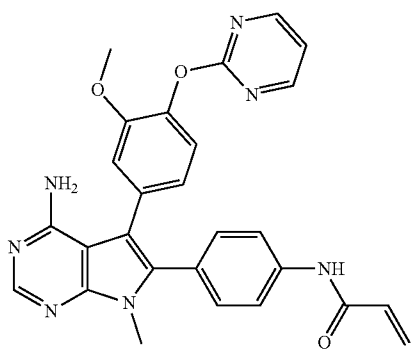 [SMILES: C=CC(=O)Nc1ccc(-c2c(-c3ccc(Oc4ncccn4)c(OC)c3)c3c(N)ncnc3n2C)cc1] | A | A |
| 16 | 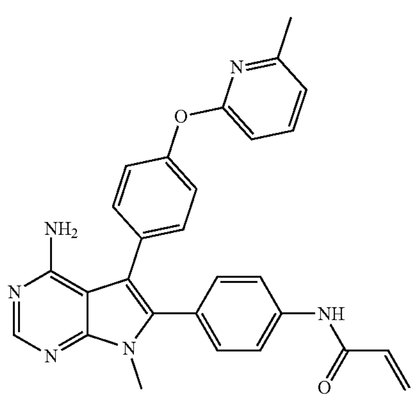 [SMILES: C=CC(=O)Nc1ccc(-c2c(-c3ccc(Oc4cccc(C)n4)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 17 | 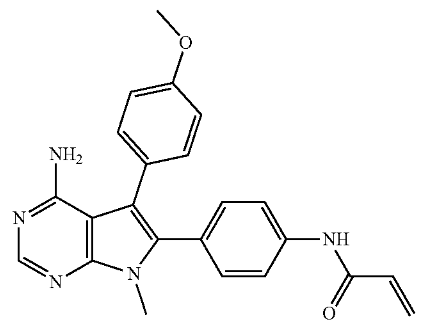 [SMILES: C=CC(=O)Nc1ccc(-c2c(-c3ccc(OC)cc3)c3c(N)ncnc3n2C)cc1] | A | |
| 18 | 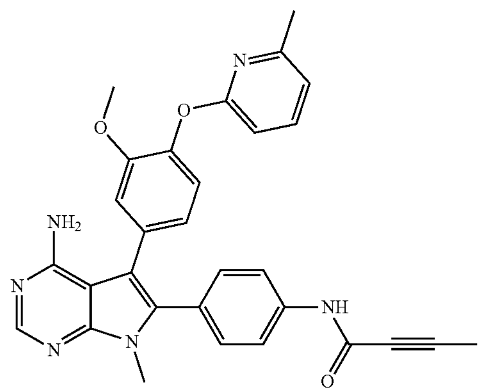 [SMILES: CC#CC(=O)Nc1ccc(-c2c(-c3ccc(Oc4cccc(C)n4)c(OC)c3)c3c(N)ncnc3n2C)cc1] | A | A |
| 19 | 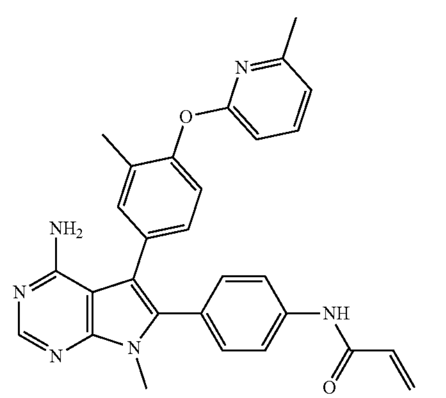 [SMILES: C=CC(=O)Nc1ccc(-c2c(-c3ccc(Oc4cccc(C)n4)c(C)c3)c3c(N)ncnc3n2C)cc1] | A | |
| 20 | 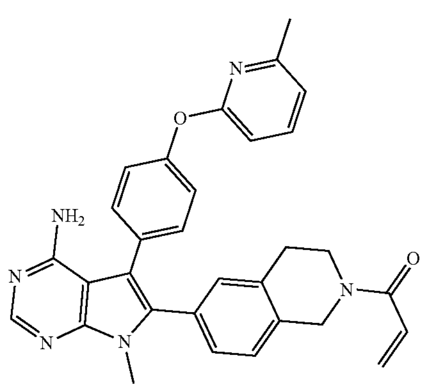 [SMILES: C=CC(=O)N1CCc2cc(-c3c(-c4ccc(Oc5cccc(C)n5)cc4)c4c(N)ncnc4n3C)ccc2C1] | B | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 21 | 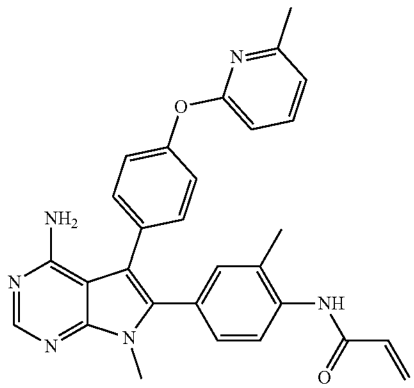 [SMILES: C=CC(=O)Nc1ccc(-c2c(-c3ccc(Oc4cccc(C)n4)cc3)c3c(N)ncnc3n2C)cc1C] | A | |
| 22 | 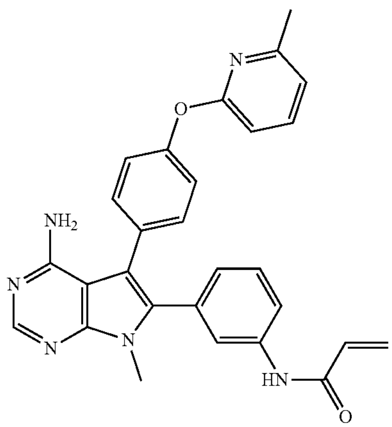 [SMILES: C=CC(=O)Nc1cccc(-c2c(-c3ccc(Oc4cccc(C)n4)cc3)c3c(N)ncnc3n2C)c1] | A | |
| 23 | 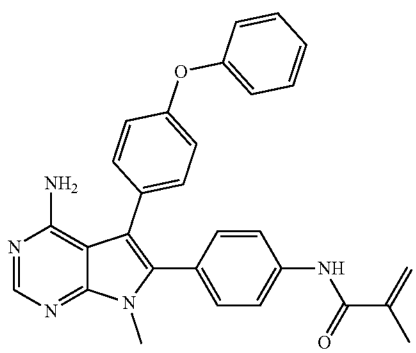 [SMILES: C=C(C)C(=O)Nc1ccc(-c2c(-c3ccc(Oc4ccccc4)cc3)c3c(N)ncnc3n2C)cc1] | C | |
| 24 | 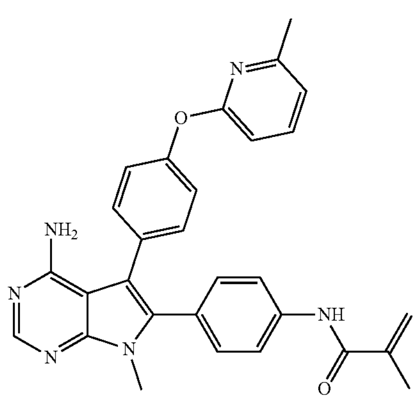 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 25 | 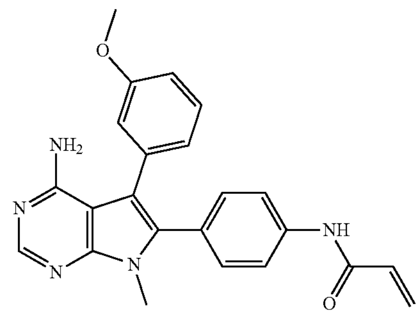 [SMILES: C=CC(=O)Nc1ccc(-c2c(-c3cccc(OC)c3)c3c(N)ncnc3n2C)cc1] | A | |
| 26 | 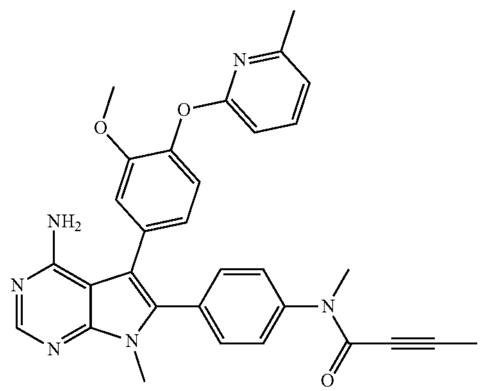 [SMILES: CC#CC(=O)N(C)c1ccc(-c2c(-c3ccc(Oc4cccc(C)n4)c(OC)c3)c3c(N)ncnc3n2C)cc1] | A | |
| 27 | 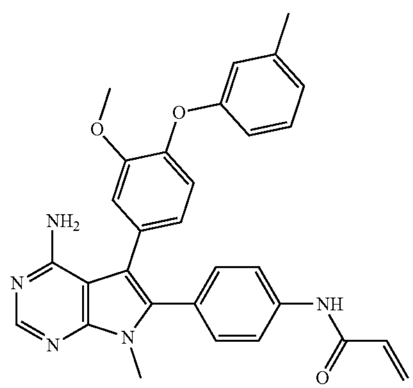 [SMILES: C=CC(=O)Nc1ccc(-c2c(-c3ccc(Oc4cccc(C)c4)c(OC)c3)c3c(N)ncnc3n2C)cc1] | A | |
| 28 | 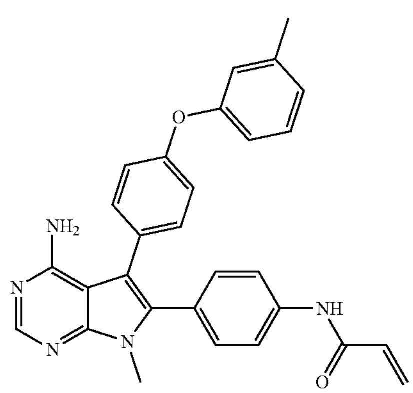 [SMILES: C=CC(=O)Nc1ccc(-c2c(-c3ccc(Oc4cccc(C)c4)cc3)c3c(N)ncnc3n2C)cc1] | A | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 29 | 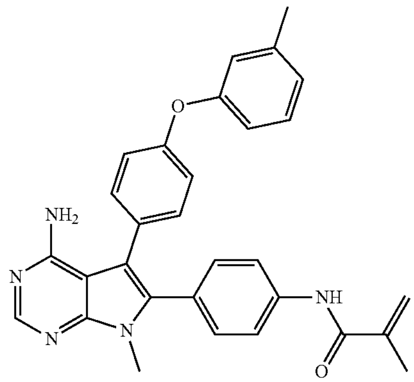 [SMILES: C=C(C)C(=O)Nc1ccc(-c2c(-c3ccc(Oc4cccc(C)c4)cc3)c3c(N)ncnc3n2C)cc1] | C | |
| 30 | 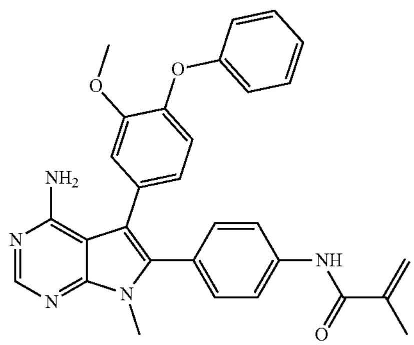 [SMILES: C=C(C)C(=O)Nc1ccc(-c2c(-c3ccc(Oc4ccccc4)c(OC)c3)c3c(N)ncnc3n2C)cc1] | C | |
| 31 | 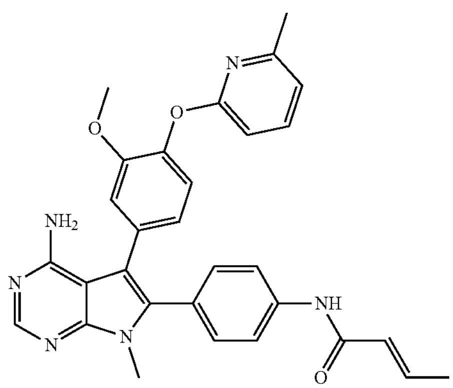 [SMILES: C/C=C/C(=O)Nc1ccc(-c2c(-c3ccc(Oc4cccc(C)n4)c(OC)c3)c3c(N)ncnc3n2C)cc1] | A | A |
| 32 | 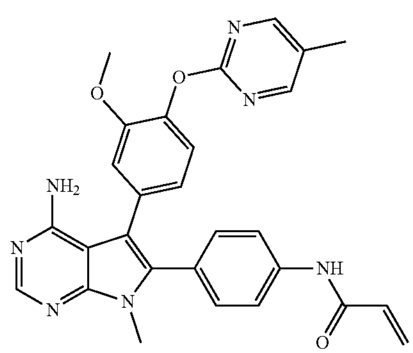 [SMILES: C=CC(=O)Nc1ccc(-c2c(-c3ccc(Oc4ncc(C)cn4)c(OC)c3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 33 | 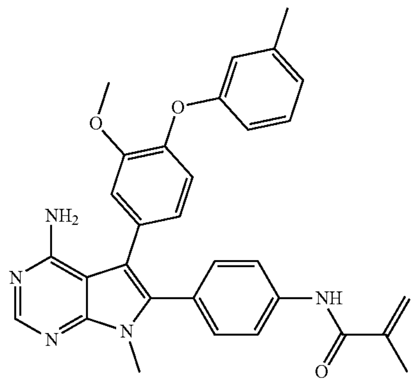 [SMILES: C=C(C)C(=O)Nc1ccc(-c2c(-c3ccc(Oc4cccc(C)c4)c(OC)c3)c3c(N)ncnc3n2C)cc1] | C | |
| 34 | 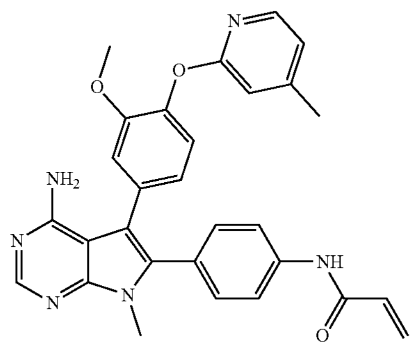 [SMILES: C=CC(=O)Nc1ccc(-c2c(-c3ccc(Oc4cc(C)ccn4)c(OC)c3)c3c(N)ncnc3n2C)cc1] | A | |
| 35 | 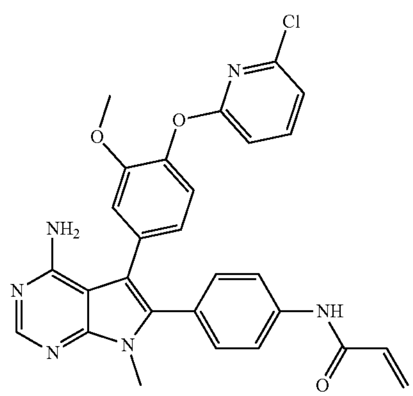 [SMILES: C=CC(=O)Nc1ccc(-c2c(-c3ccc(Oc4cccc(Cl)n4)c(OC)c3)c3c(N)ncnc3n2C)cc1] | A | A |
| 36 | 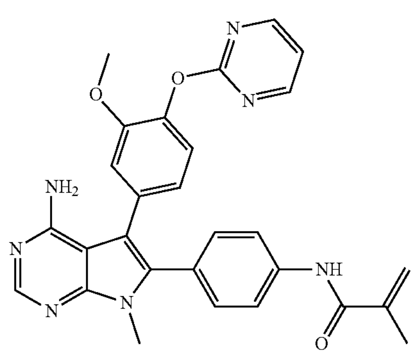 [SMILES: C=C(C)C(=O)Nc1ccc(-c2c(-c3ccc(Oc4ncccn4)c(OC)c3)c3c(N)ncnc3n2C)cc1] | C | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 37 | 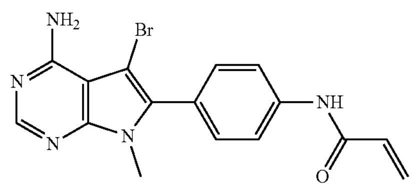 [SMILES: C=CC(=O)Nc1ccc(-c2c(Br)c3c(N)ncnc3n2C)cc1] | A | |
| 38 | 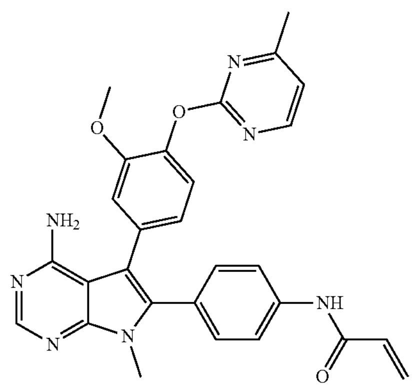 [SMILES: C=CC(=O)Nc1ccc(-c2c(-c3ccc(Oc4nccc(C)n4)c(OC)c3)c3c(N)ncnc3n2C)cc1] | A | A |
| 39 | 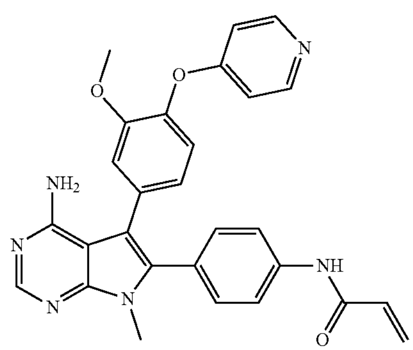 [SMILES: C=CC(=O)Nc1ccc(-c2c(-c3ccc(Oc4ccncc4)c(OC)c3)c3c(N)ncnc3n2C)cc1] | B | |
| 40 | 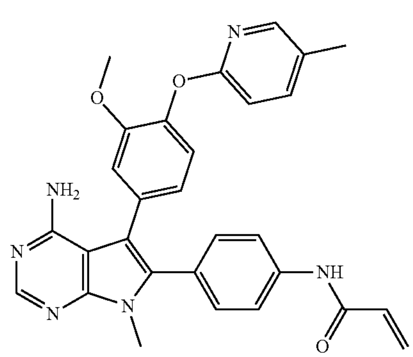 [SMILES: C=CC(=O)Nc1ccc(-c2c(-c3ccc(Oc4ccc(C)cn4)c(OC)c3)c3c(N)ncnc3n2C)cc1] | A | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 41 | 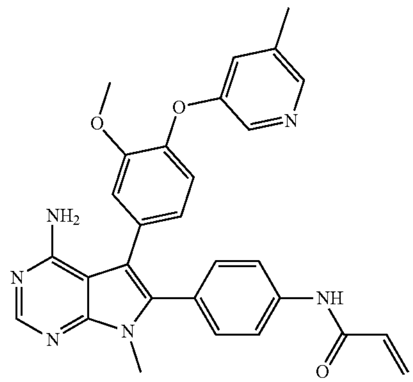 [SMILES: C=CC(=O)Nc1ccc(-c2c(-c3ccc(Oc4cncc(C)c4)c(OC)c3)c3c(N)ncnc3n2C)cc1] | A | |
| 42 | 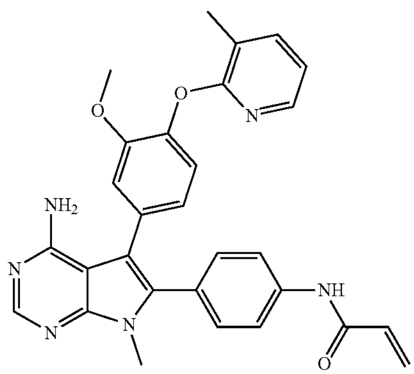 [SMILES: C=CC(=O)Nc1ccc(-c2c(-c3ccc(Oc4ncccc4C)c(OC)c3)c3c(N)ncnc3n2C)cc1] | A | |
| 43 | 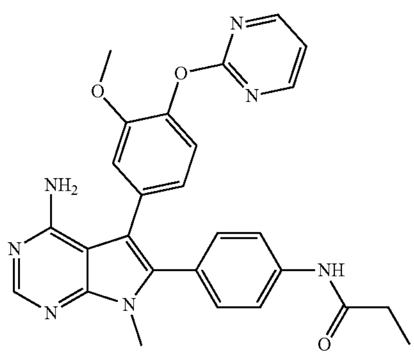 [SMILES: CCC(=O)Nc1ccc(-c2c(-c3ccc(Oc4ncccn4)c(OC)c3)c3c(N)ncnc3n2C)cc1] | D | |
| 44 | 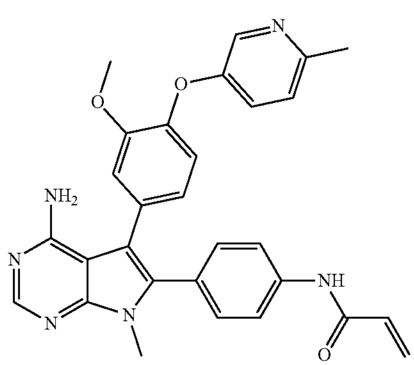 [SMILES: C=CC(=O)Nc1ccc(-c2c(-c3ccc(Oc4ccc(C)nc4)c(OC)c3)c3c(N)ncnc3n2C)cc1] | A | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 45 | 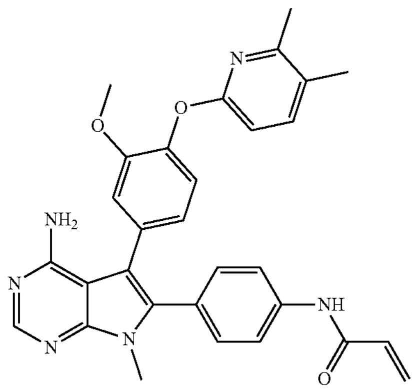 [SMILES: C=CC(=O)Nc1ccc(-c2c(-c3ccc(Oc4ccc(C)c(C)n4)c(OC)c3)c3c(N)ncnc3n2C)cc1] | A | A |
| 46 | 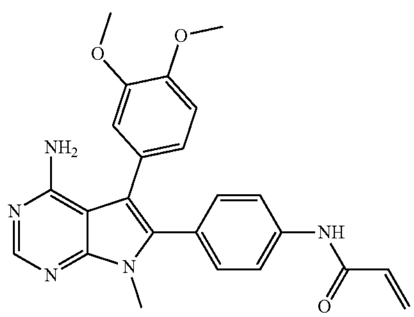 [SMILES: C=CC(=O)Nc1ccc(-c2c(-c3ccc(OC)c(OC)c3)c3c(N)ncnc3n2C)cc1] | A | |
| 47 | 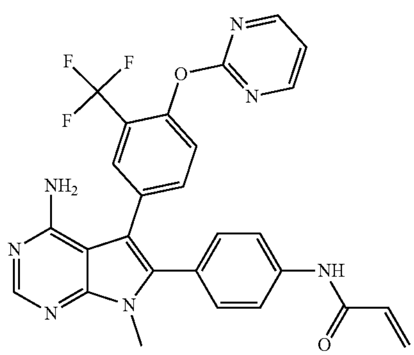 [SMILES: C=CC(=O)Nc1ccc(-c2c(-c3ccc(Oc4ncccn4)c(C(F)(F)F)c3)c3c(N)ncnc3n2C)cc1] | A | A |
| 48 | 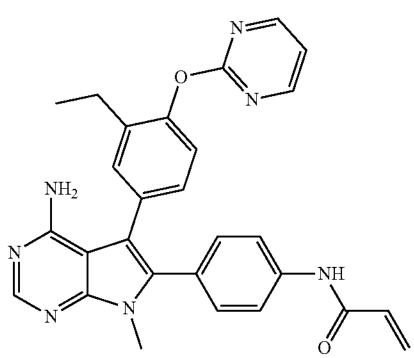 [SMILES: C=CC(=O)Nc1ccc(-c2c(-c3ccc(Oc4ncccn4)c(CC)c3)c3c(N)ncnc3n2C)cc1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 49 | 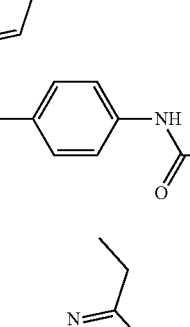 | A | A |
| 50 | 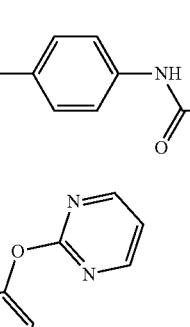 | A | A |
| 51 | 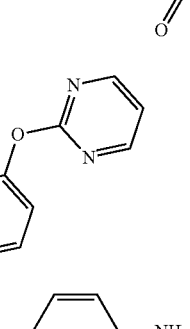 | A | A |
| 52 | 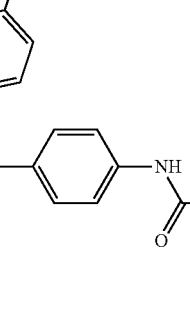 | A | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 53 | 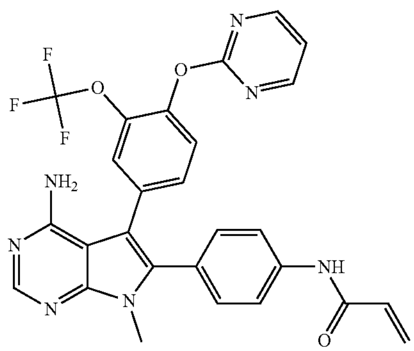 [SMILES: C=CC(=O)Nc1ccc(-c2c(-c3ccc(Oc4ncccn4)c(OC(F)(F)F)c3)c3c(N)ncnc3n2C)cc1] | A | A |
| 54 | 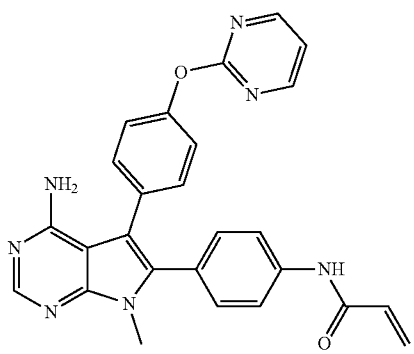 [SMILES: C=CC(=O)Nc1ccc(-c2c(-c3ccc(Oc4ncccn4)cc3)c3c(N)ncnc3n2C)cc1] | A | A |
| 55 | 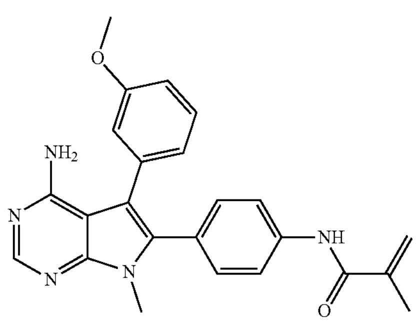 [SMILES: C=C(C)C(=O)Nc1ccc(-c2c(-c3cccc(OC)c3)c3c(N)ncnc3n2C)cc1] | C | |
| 56 | 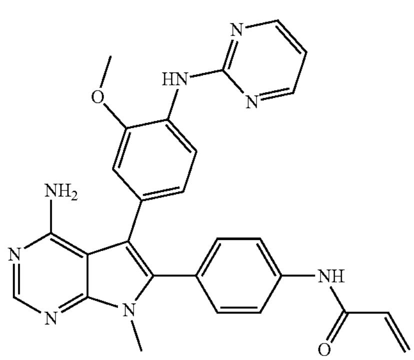 [SMILES: C=CC(=O)Nc1ccc(-c2c(-c3ccc(Nc4ncccn4)c(OC)c3)c3c(N)ncnc3n2C)cc1] | A | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 57 | 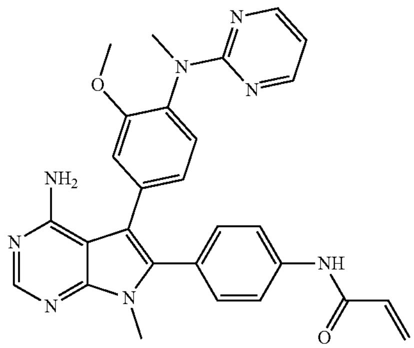 [SMILES: C=CC(=O)Nc1ccc(-c2c(-c3ccc(N(C)c4ncccn4)c(OC)c3)c3c(N)ncnc3n2C)cc1] | B | |
| 58 | 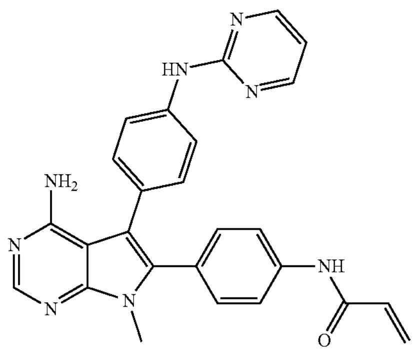 [SMILES: C=CC(=O)Nc1ccc(-c2c(-c3ccc(Nc4ncccn4)cc3)c3c(N)ncnc3n2C)cc1] | A | |
| 59 | 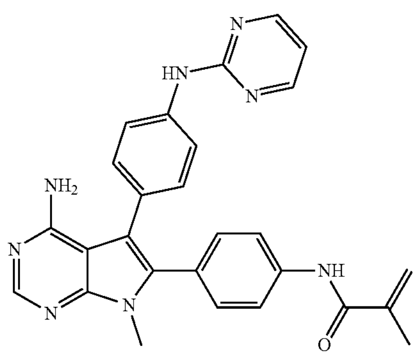 [SMILES: C=C(C)C(=O)Nc1ccc(-c2c(-c3ccc(Nc4ncccn4)cc3)c3c(N)ncnc3n2C)cc1] | B | |
| 60 | 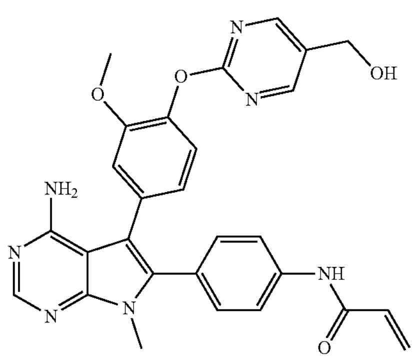 [SMILES: C=CC(=O)Nc1ccc(-c2c(-c3ccc(Oc4ncc(CO)cn4)c(OC)c3)c3c(N)ncnc3n2C)cc1] | A | C |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 61 | 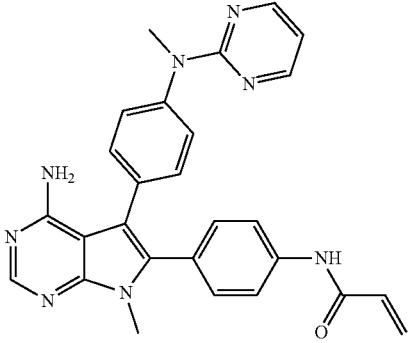 [SMILES: C=CC(=O)Nc1ccc(-c2c(-c3ccc(N(C)c4ncccn4)cc3)c3c(N)ncnc3n2C)cc1] | A | |
| 62 | 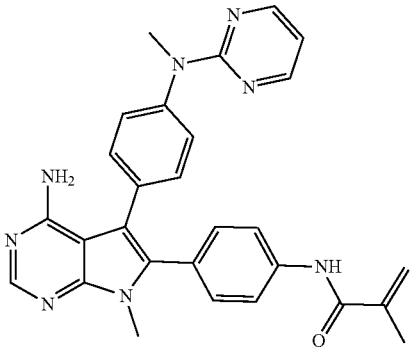 [SMILES: C=C(C)C(=O)Nc1ccc(-c2c(-c3ccc(N(C)c4ncccn4)cc3)c3c(N)ncnc3n2C)cc1] | D | |
| 63 | 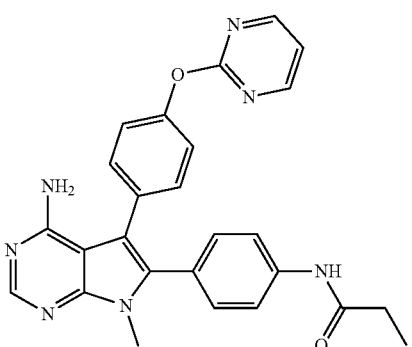 | D | |
| 64 | 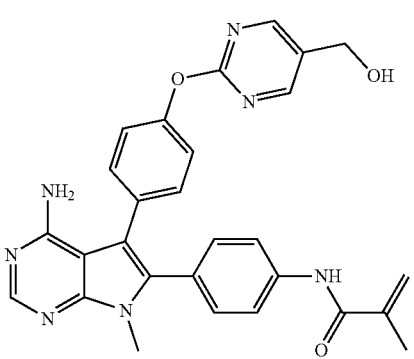 [SMILES: C=C(C)C(=O)Nc1ccc(-c2c(-c3ccc(Oc4ncc(CO)cn4)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 65 | 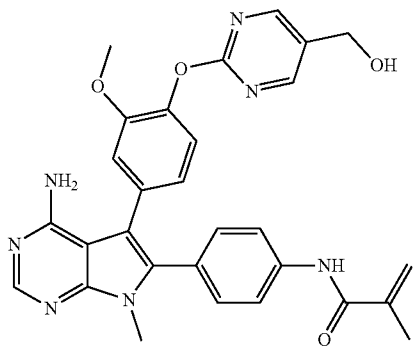 [SMILES: C=C(C)C(=O)Nc1ccc(-c2c(-c3ccc(Oc4ncc(CO)cn4)c(OC)c3)c3c(N)ncnc3n2C)cc1] | D | |
| 66 | 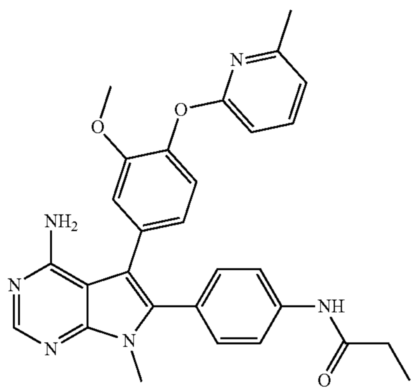 [SMILES: CCC(=O)Nc1ccc(-c2c(-c3ccc(Oc4cccc(C)n4)c(OC)c3)c3c(N)ncnc3n2C)cc1] | D | |
| 67 | 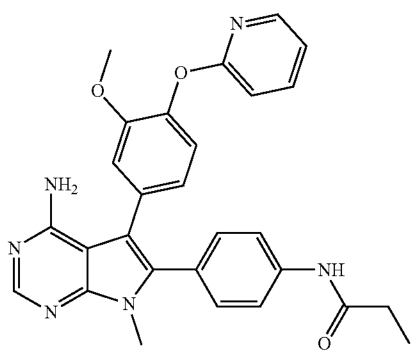 [SMILES: CCC(=O)Nc1ccc(-c2c(-c3ccc(Oc4ccccn4)c(OC)c3)c3c(N)ncnc3n2C)cc1] | D | |
| 68 | 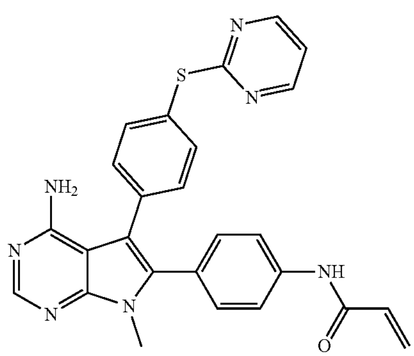 [SMILES: C=CC(=O)Nc1ccc(-c2c(-c3ccc(Sc4ncccn4)cc3)c3c(N)ncnc3n2C)cc1] | A | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 69 | 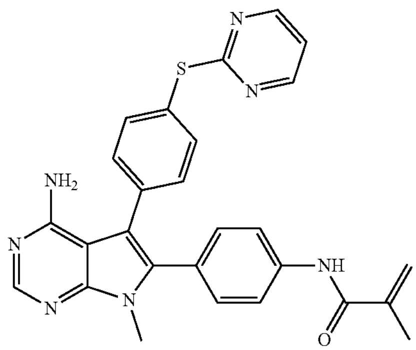 [SMILES: C=C(C)C(=O)Nc1ccc(-c2c(-c3ccc(Sc4ncccn4)cc3)c3c(N)ncnc3n2C)cc1] | C | C |
| 70 | 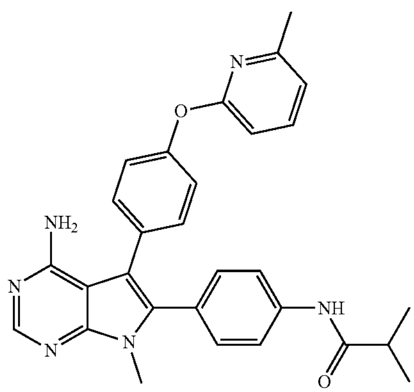 [SMILES: Cc1cccc(Oc2ccc(-c3c(-c4ccc(NC(=O)C(C)C)cc4)n(C)c4ncnc(N)c34)cc2)n1] | C | C |
| 71 | 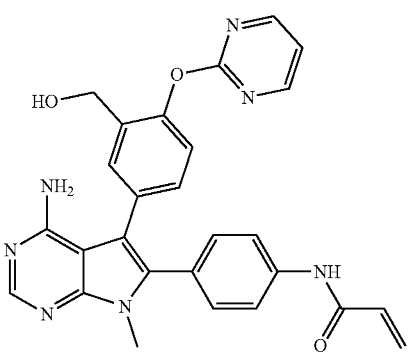 [SMILES: C=CC(=O)Nc1ccc(-c2c(-c3ccc(Oc4ncccn4)c(CO)c3)c3c(N)ncnc3n2C)cc1] | C | |
| 72 | 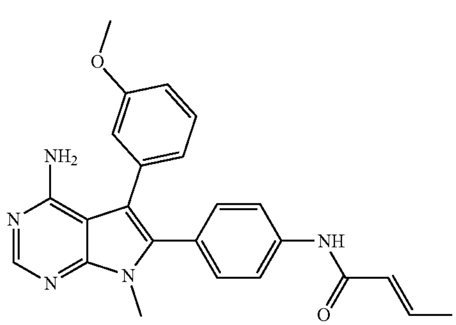 [SMILES: C/C=C/C(=O)Nc1ccc(-c2c(-c3cccc(OC)c3)c3c(N)ncnc3n2C)cc1] | C | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 73 | 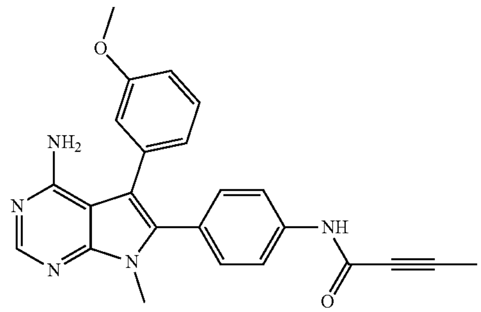 [SMILES: CC#CC(=O)Nc1ccc(-c2c(-c3cccc(OC)c3)c3c(N)ncnc3n2C)cc1] | B | |
| 74 | 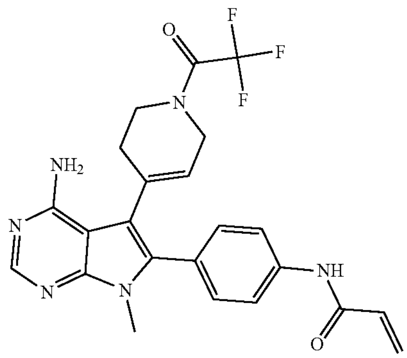 [SMILES: C=CC(=O)Nc1ccc(-c2c(C3=CCN(C(=O)C(F)(F)F)CC3)c3c(N)ncnc3n2C)cc1] | C | |
| 75 | 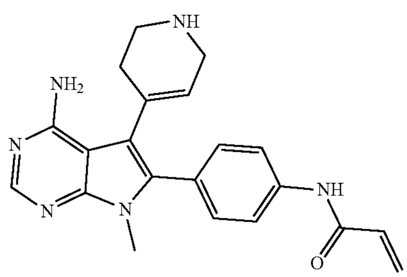 [SMILES: C=CC(=O)Nc1ccc(-c2c(C3=CCNCC3)c3c(N)ncnc3n2C)cc1] | C | |
| 76 | 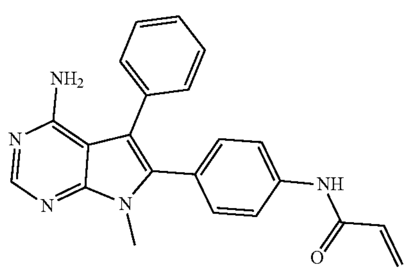 [SMILES: C=CC(=O)Nc1ccc(-c2c(-c3ccccc3)c3c(N)ncnc3n2C)cc1] | B | |
| 77 | 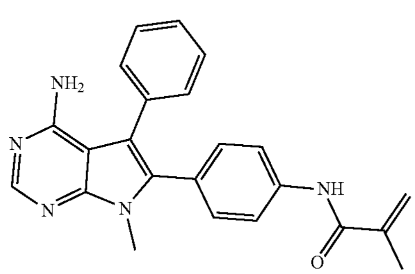 [SMILES: C=C(C)C(=O)Nc1ccc(-c2c(-c3ccccc3)c3c(N)ncnc3n2C)cc1] | | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 78 | 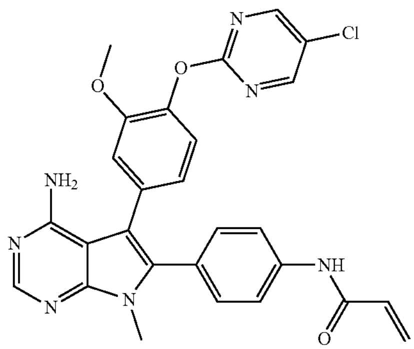 [SMILES: C=CC(=O)Nc1ccc(-c2c(-c3ccc(Oc4ncc(Cl)cn4)c(OC)c3)c3c(N)ncnc3n2C)cc1] | A | A |
| 79 | 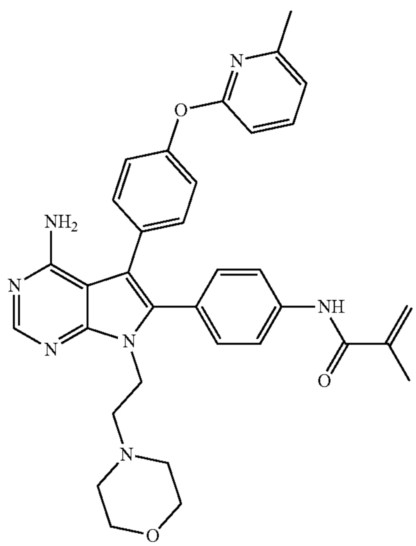 [SMILES: C=C(C)C(=O)Nc1ccc(-c2c(-c3ccc(Oc4cccc(C)n4)cc3)c3c(N)ncnc3n2CCN2CCOCC2)cc1] | B | |
| 80 | 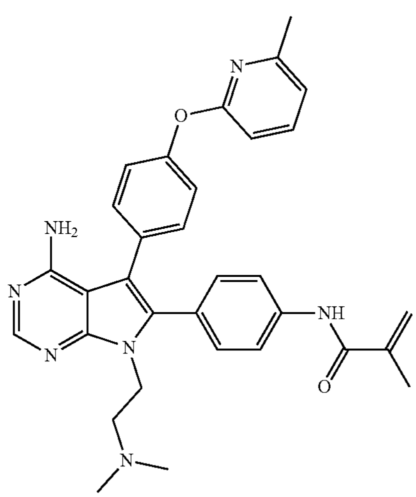 [SMILES: C=C(C)C(=O)Nc1ccc(-c2c(-c3ccc(Oc4cccc(C)n4)cc3)c3c(N)ncnc3n2CCN(C)C)cc1] | B | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 81 | 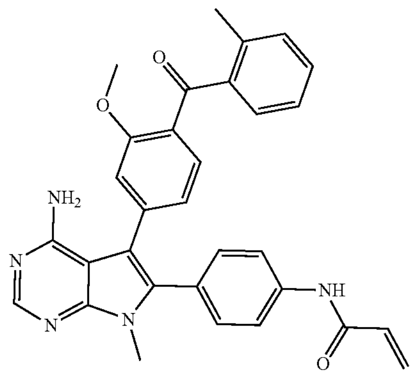 [SMILES: C=CC(=O)Nc1ccc(-c2c(-c3ccc(C(=O)c4ccccc4C)c(OC)c3)c3c(N)ncnc3n2C)cc1] | A | |
| 82 | 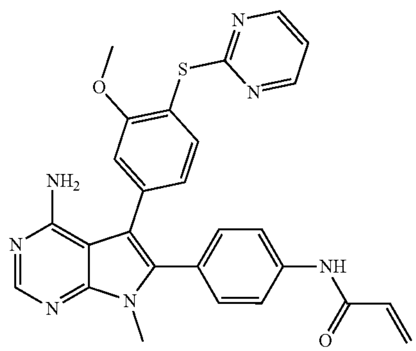 [SMILES: C=CC(=O)Nc1ccc(-c2c(-c3ccc(Sc4ncccn4)c(OC)c3)c3c(N)ncnc3n2C)cc1] | A | |
| 83 | 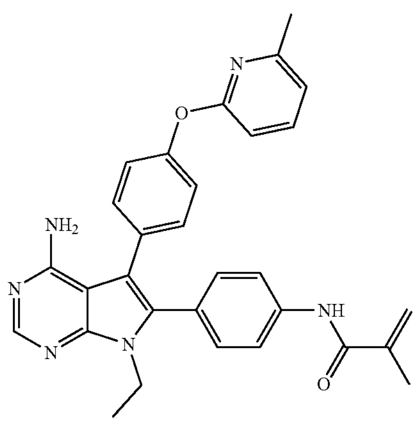 [SMILES: C=C(C)C(=O)Nc1ccc(-c2c(-c3ccc(Oc4cccc(C)n4)cc3)c3c(N)ncnc3n2CC)cc1] | A | A |
| 84 | 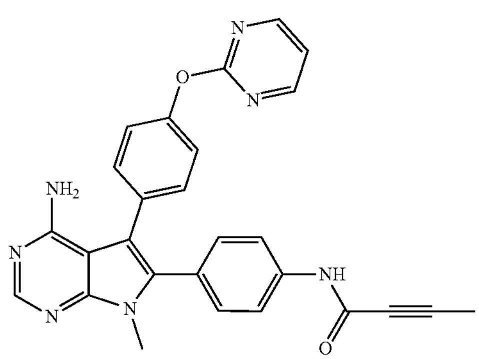 [SMILES: CC#CC(=O)Nc1ccc(-c2c(-c3ccc(Oc4ncccn4)cc3)c3c(N)ncnc3n2C)cc1] | A | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 85 | 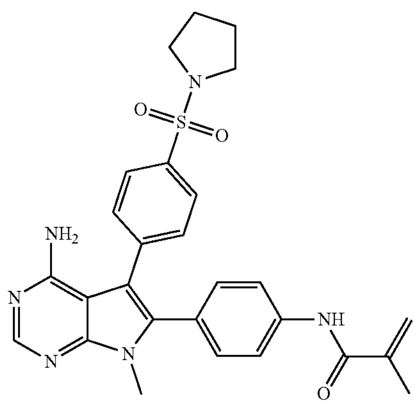 [SMILES: C=C(C)C(=O)Nc1ccc(-c2c(-c3ccc(S(=O)(=O)N4CCCC4)cc3)c3c(N)ncnc3n2C)cc1] | B | |
| 86 | 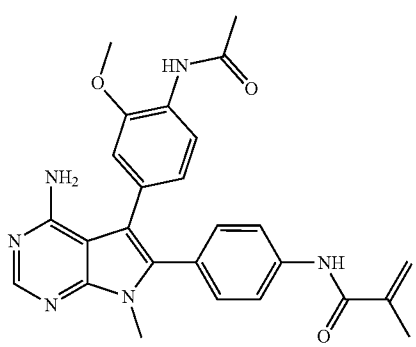 [SMILES: C=C(C)C(=O)Nc1ccc(-c2c(-c3ccc(NC(C)=O)c(OC)c3)c3c(N)ncnc3n2C)cc1] | D | C |
| 87 | 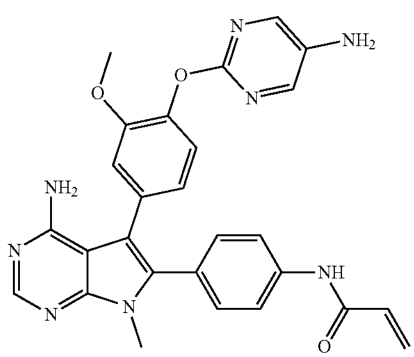 | A | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 88 | 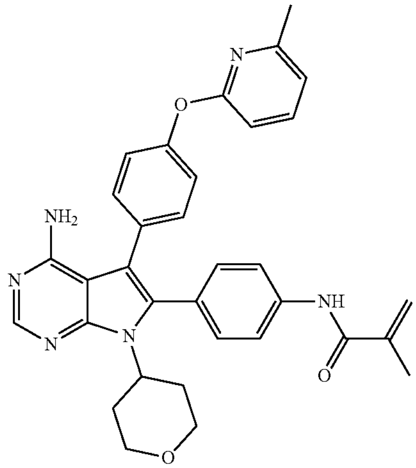 [SMILES: C=C(C)C(=O)Nc1ccc(-c2c(-c3ccc(Oc4cccc(C)n4)cc3)c3c(N)ncnc3n2C2CCOCC2)cc1] | B | |
| 89 | 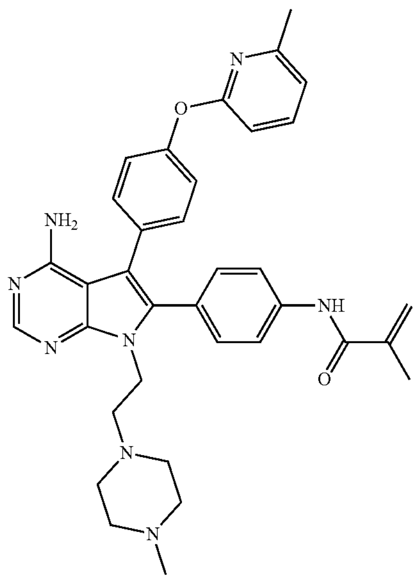 [SMILES: C=C(C)C(=O)Nc1ccc(-c2c(-c3ccc(Oc4cccc(C)n4)cc3)c3c(N)ncnc3n2CCN2CCN(C)CC2)cc1] | A | |
| 90 | 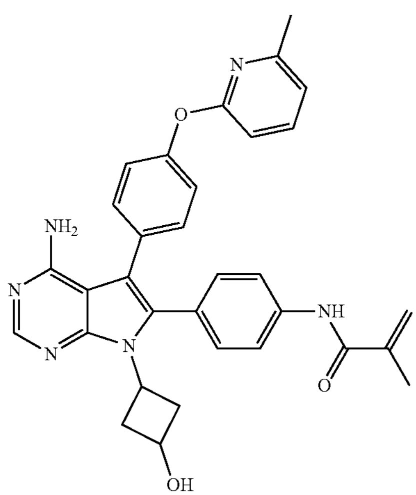 [SMILES: C=C(C)C(=O)Nc1ccc(-c2c(-c3ccc(Oc4cccc(C)n4)cc3)c3c(N)ncnc3n2C2CC(O)C2)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 91 | 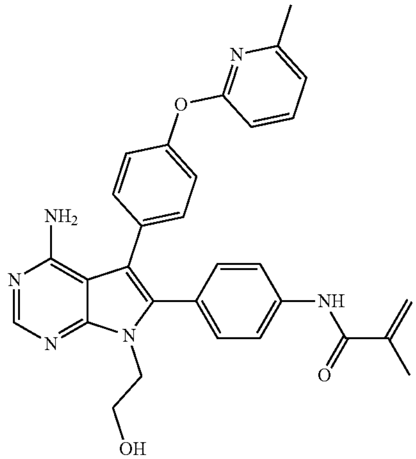 [SMILES: C=C(C)C(=O)Nc1ccc(-c2c(-c3ccc(Oc4cccc(C)n4)cc3)c3c(N)ncnc3n2CCO)cc1] | A | A |
| 92 | 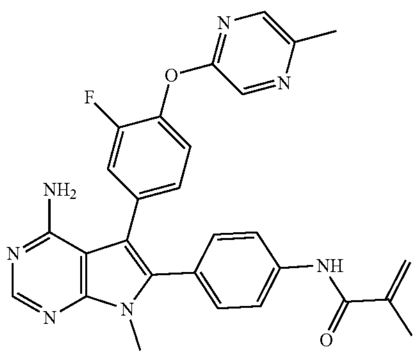 [SMILES: C=C(C)C(=O)Nc1ccc(-c2c(-c3ccc(Oc4cnc(C)cn4)c(F)c3)c3c(N)ncnc3n2C)cc1] | D | |
| 93 | 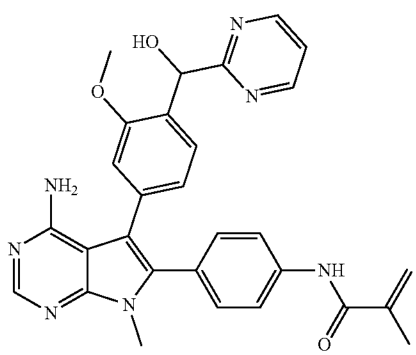 [SMILES: C=C(C)C(=O)Nc1ccc(-c2c(-c3ccc(C(O)c4ncccn4)c(OC)c3)c3c(N)ncnc3n2C)cc1] | C | |
| 94 | 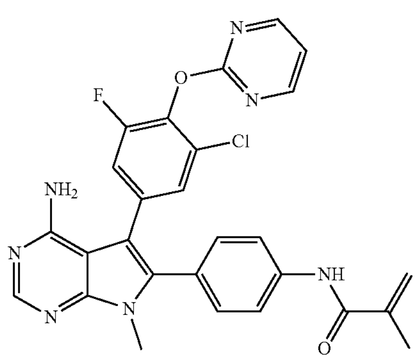 [SMILES: C=C(C)C(=O)Nc1ccc(-c2c(-c3cc(F)c(Oc4ncccn4)c(Cl)c3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 95 | 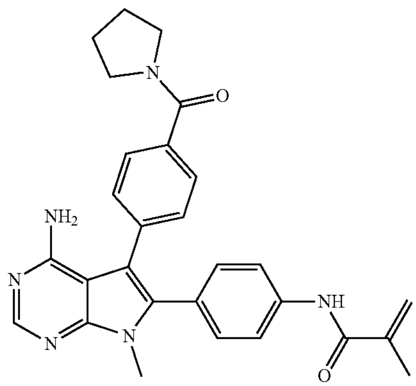 [SMILES: C=C(C)C(=O)Nc1ccc(-c2c(-c3ccc(C(=O)N4CCCC4)cc3)c3c(N)ncnc3n2C)cc1] | B | A |
| 96 | 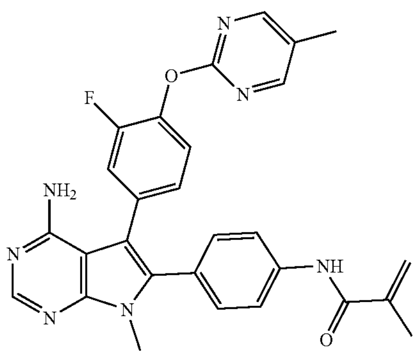 [SMILES: C=C(C)C(=O)Nc1ccc(-c2c(-c3ccc(Oc4ncc(C)cn4)c(F)c3)c3c(N)ncnc3n2C)cc1] | A | A |
| 97 | 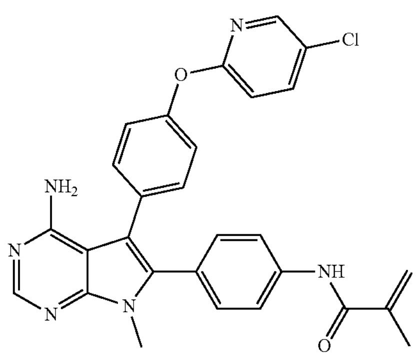 [SMILES: C=C(C)C(=O)Nc1ccc(-c2c(-c3ccc(Oc4ccc(Cl)cn4)cc3)c3c(N)ncnc3n2C)cc1] | C | |
| 98 | 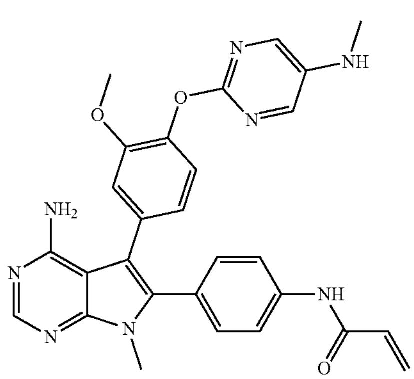 [SMILES: C=CC(=O)Nc1ccc(-c2c(-c3ccc(Oc4ncc(NC)cn4)c(OC)c3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 99 | 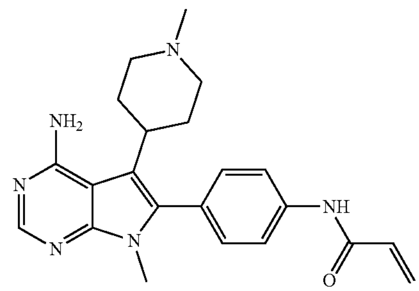 [SMILES: C=CC(=O)Nc1ccc(-c2c(C3CCN(C)CC3)c3c(N)ncnc3n2C)cc1] | D | |
| 100 | 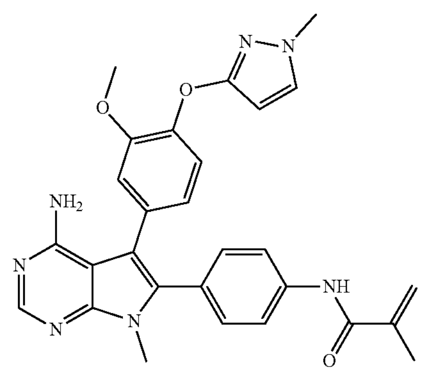 [SMILES: C=C(C)C(=O)Nc1ccc(-c2c(-c3ccc(Oc4ccn(C)n4)c(OC)c3)c3c(N)ncnc3n2C)cc1] | C | B |
| 101 | 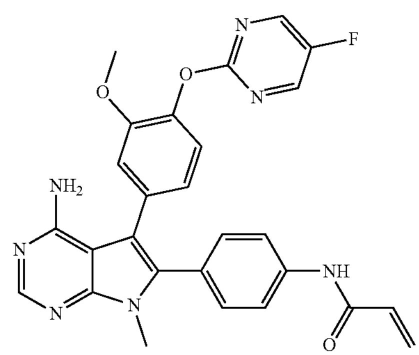 [SMILES: C=CC(=O)Nc1ccc(-c2c(-c3ccc(Oc4ncc(F)cn4)c(OC)c3)c3c(N)ncnc3n2C)cc1] | A | A |
| 102 | 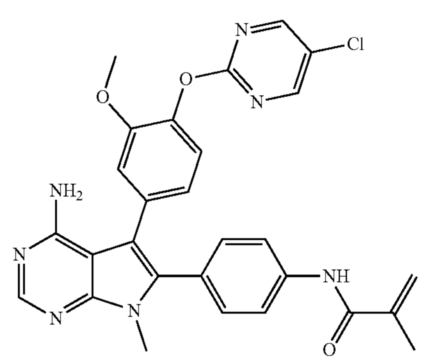 [SMILES: C=C(C)C(=O)Nc1ccc(-c2c(-c3ccc(Oc4ncc(Cl)cn4)c(OC)c3)c3c(N)ncnc3n2C)cc1] | B | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 103 | 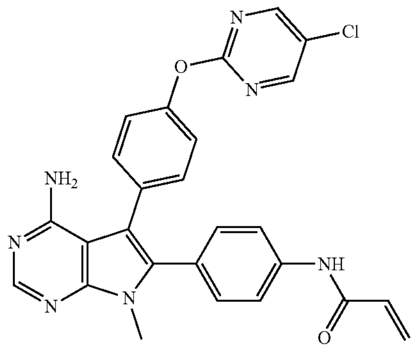 [SMILES: C=CC(=O)Nc1ccc(-c2c(-c3ccc(Oc4ncc(Cl)cn4)cc3)c3c(N)ncnc3n2C)cc1] | A | A |
| 104 | 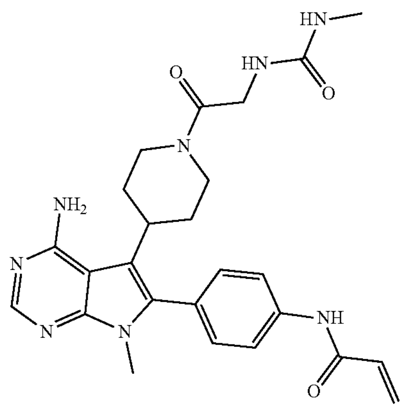 [SMILES: C=CC(=O)Nc1ccc(-c2c(C3CCN(C(=O)CNC(=O)NC)CC3)c3c(N)ncnc3n2C)cc1] | D | |
| 105 | 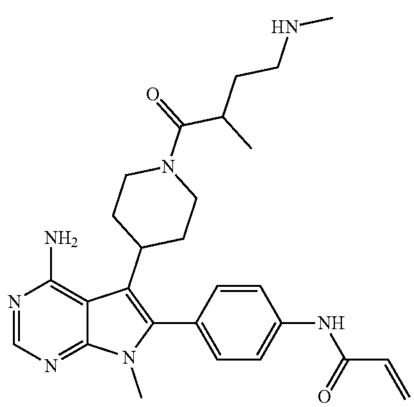 [SMILES: C=CC(=O)Nc1ccc(-c2c(C3CCN(C(=O)C(C)CCNC)CC3)c3c(N)ncnc3n2C)cc1] | C | |
| 106 | 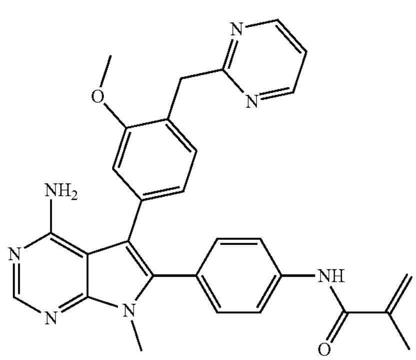 [SMILES: C=C(C)C(=O)Nc1ccc(-c2c(-c3ccc(Cc4ncccn4)c(OC)c3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 107 | 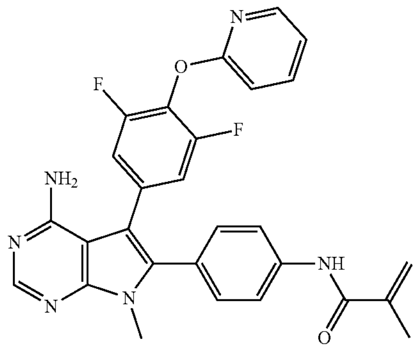 [SMILES: C=C(C)C(=O)Nc1ccc(-c2c(-c3cc(F)c(Oc4ccccn4)c(F)c3)c3c(N)ncnc3n2C)cc1] | C | |
| 108 | 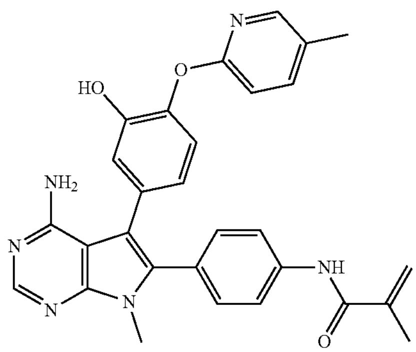 [SMILES: C=C(C)C(=O)Nc1ccc(-c2c(-c3ccc(Oc4ccc(C)cn4)c(O)c3)c3c(N)ncnc3n2C)cc1] | D | |
| 109 | 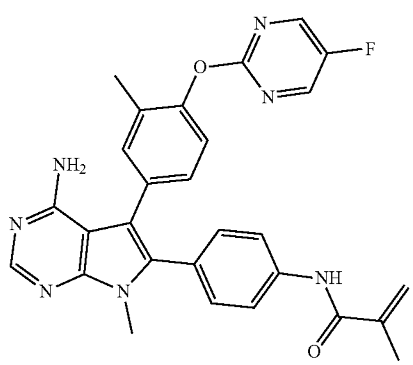 [SMILES: C=C(C)C(=O)Nc1ccc(-c2c(-c3ccc(Oc4ncc(F)cn4)c(C)c3)c3c(N)ncnc3n2C)cc1] | B | |
| 110 | 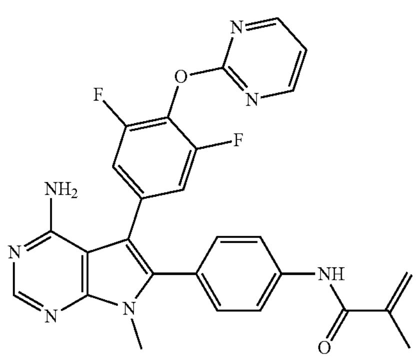 [SMILES: C=C(C)C(=O)Nc1ccc(-c2c(-c3cc(F)c(Oc4ncccn4)c(F)c3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 111 | 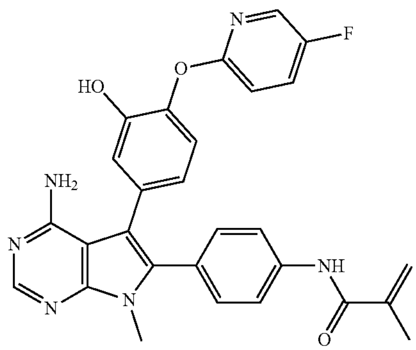 [SMILES: C=C(C)C(=O)Nc1ccc(-c2c(-c3ccc(Oc4ccc(F)cn4)c(O)c3)c3c(N)ncnc3n2C)cc1] | D | |
| 112 | 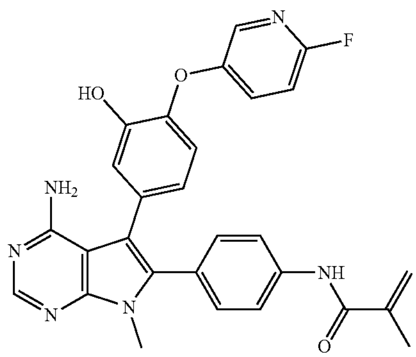 [SMILES: C=C(C)C(=O)Nc1ccc(-c2c(-c3ccc(Oc4ccc(F)nc4)c(O)c3)c3c(N)ncnc3n2C)cc1] | D | |
| 113 | 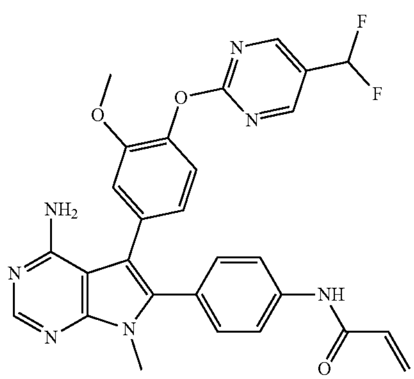 [SMILES: C=CC(=O)Nc1ccc(-c2c(-c3ccc(Oc4ncc(C(F)F)cn4)c(OC)c3)c3c(N)ncnc3n2C)cc1] | A | A |
| 114 | 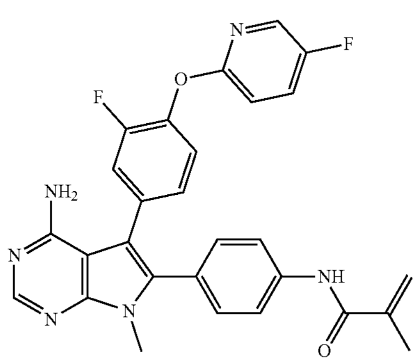 [SMILES: C=C(C)C(=O)Nc1ccc(-c2c(-c3ccc(Oc4ccc(F)cn4)c(F)c3)c3c(N)ncnc3n2C)cc1] | C | B |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 115 | 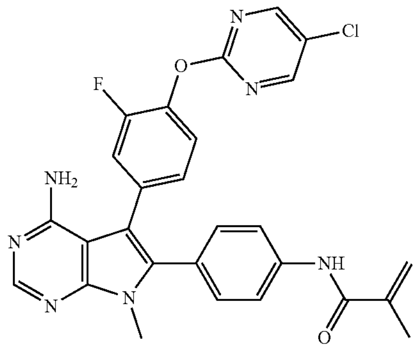 [SMILES: C=C(C)C(=O)Nc1ccc(-c2c(-c3ccc(Oc4ncc(Cl)cn4)c(F)c3)c3c(N)ncnc3n2C)cc1] | C | |
| 116 | 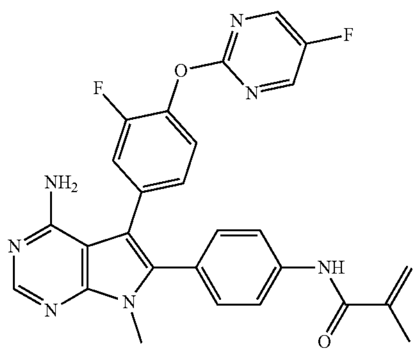 [SMILES: C=C(C)C(=O)Nc1ccc(-c2c(-c3ccc(Oc4ncc(F)cn4)c(F)c3)c3c(N)ncnc3n2C)cc1] | A | A |
| 117 | 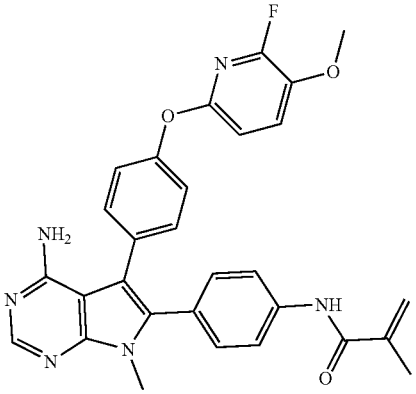 [SMILES: C=C(C)C(=O)Nc1ccc(-c2c(-c3ccc(Oc4ccc(OC)c(F)n4)cc3)c3c(N)ncnc3n2C)cc1] | C | B |
| 118 | 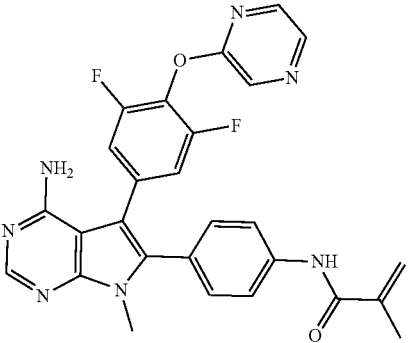 [SMILES: C=C(C)C(=O)Nc1ccc(-c2c(-c3cc(F)c(Oc4cnccn4)c(F)c3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 119 | 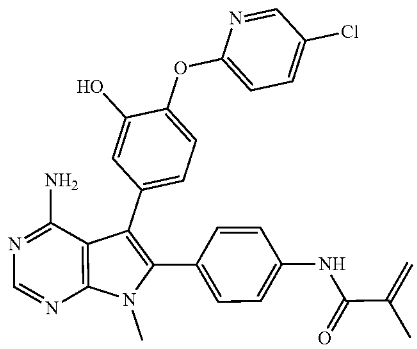 [SMILES: C=C(C)C(=O)Nc1ccc(-c2c(-c3ccc(Oc4ccc(Cl)cn4)c(O)c3)c3c(N)ncnc3n2C)cc1] | D | |
| 120 | 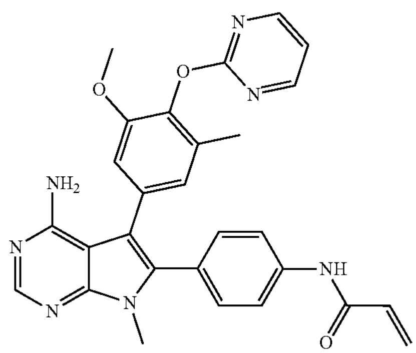 [SMILES: C=CC(=O)Nc1ccc(-c2c(-c3cc(C)c(Oc4ncccn4)c(OC)c3)c3c(N)ncnc3n2C)cc1] | A | A |
| 121 | 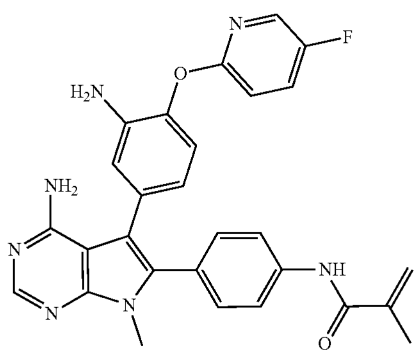 [SMILES: C=C(C)C(=O)Nc1ccc(-c2c(-c3ccc(Oc4ccc(F)cn4)c(N)c3)c3c(N)ncnc3n2C)cc1] | | |
| 122 | 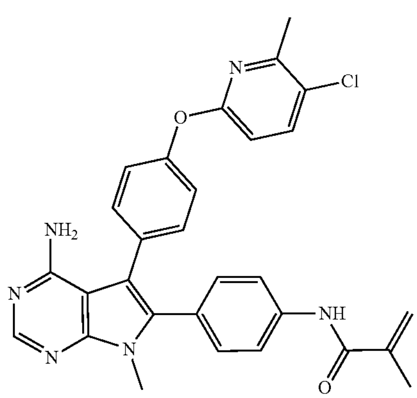 [SMILES: C=C(C)C(=O)Nc1ccc(-c2c(-c3ccc(Oc4ccc(Cl)c(C)n4)cc3)c3c(N)ncnc3n2C)cc1] | C | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 123 | 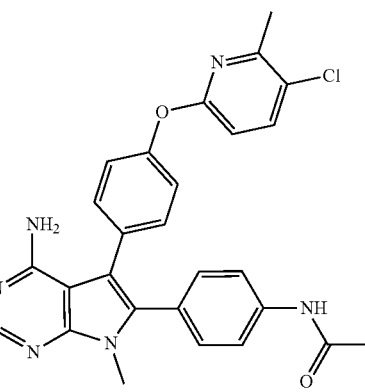 | A | A |
| 124 | 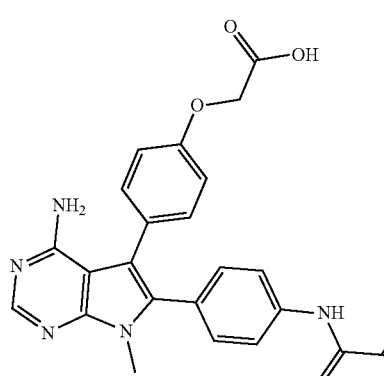 | D | |
| 125 | 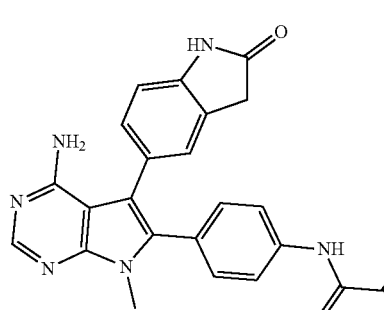 | D | |
| 126 | 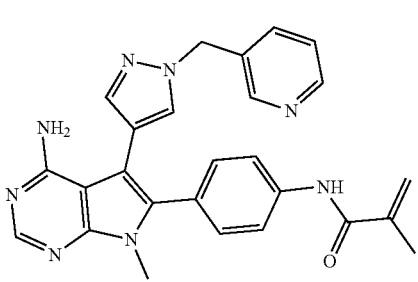 [SMILES: C=C(C)C(=O)Nc1ccc(-c2c(-c3cnn(Cc4cccnc4)c3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 127 | 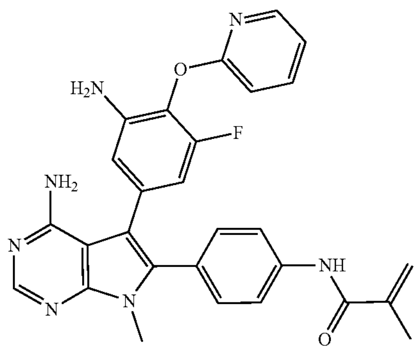 [SMILES: C=C(C)C(=O)Nc1ccc(-c2c(-c3cc(N)c(Oc4ccccn4)c(F)c3)c3c(N)ncnc3n2C)cc1] | B | |
| 128 | 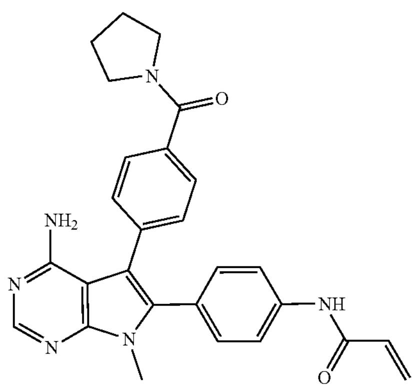 [SMILES: C=CC(=O)Nc1ccc(-c2c(-c3ccc(C(=O)N4CCCC4)cc3)c3c(N)ncnc3n2C)cc1] | A | A |
| 129 | 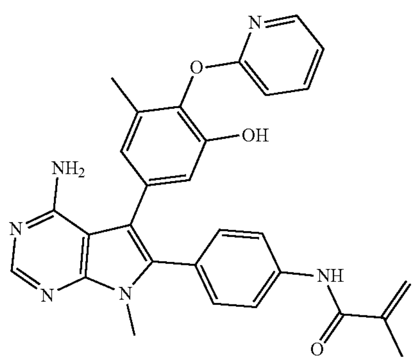 [SMILES: C=C(C)C(=O)Nc1ccc(-c2c(-c3cc(C)c(Oc4ccccn4)c(O)c3)c3c(N)ncnc3n2C)cc1] | C | |
| 130 | 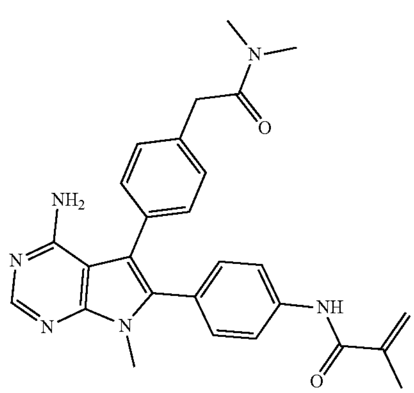 [SMILES: C=C(C)C(=O)Nc1ccc(-c2c(-c3ccc(CC(=O)N(C)C)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 131 | 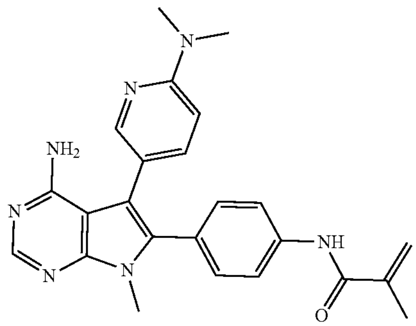 [SMILES: C=C(C)C(=O)Nc1ccc(-c2c(-c3ccc(N(C)C)nc3)c3c(N)ncnc3n2C)cc1] | D | |
| 132 | 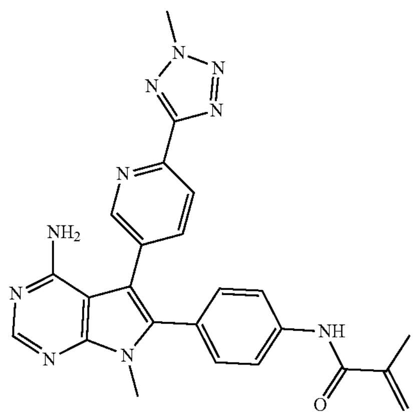 [SMILES: C=C(C)C(=O)Nc1ccc(-c2c(-c3ccc(-c4nnn(C)n4)nc3)c3c(N)ncnc3n2C)cc1] | D | |
| 133 | 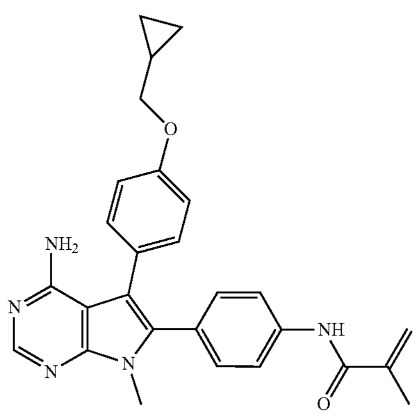 [SMILES: C=C(C)C(=O)Nc1ccc(-c2c(-c3ccc(OCC4CC4)cc3)c3c(N)ncnc3n2C)cc1] | B | |
| 134 | 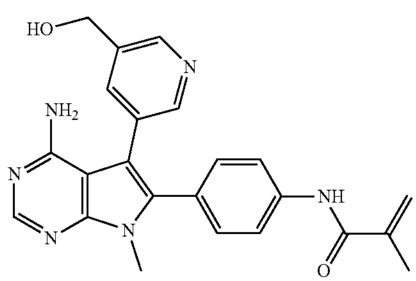 [SMILES: C=C(C)C(=O)Nc1ccc(-c2c(-c3cncc(CO)c3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 135 | 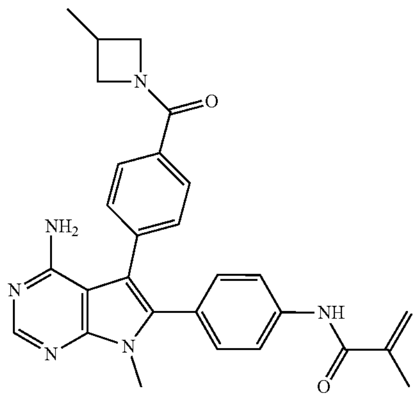 [SMILES: C=C(C)C(=O)Nc1ccc(-c2c(-c3ccc(C(=O)N4CC(C)C4)cc3)c3c(N)ncnc3n2C)cc1] | C | B |
| 136 | 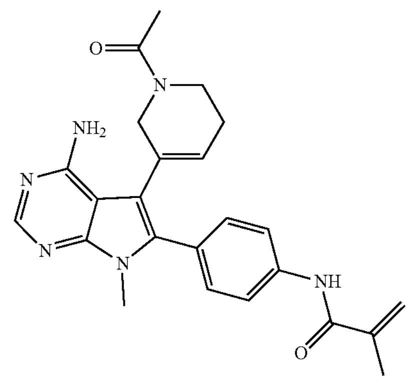 [SMILES: C=C(C)C(=O)Nc1ccc(-c2c(C3=CCCN(C(C)=O)C3)c3c(N)ncnc3n2C)cc1] | D | |
| 137 | 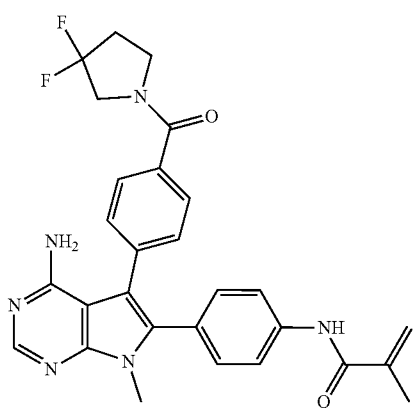 [SMILES: C=C(C)C(=O)Nc1ccc(-c2c(-c3ccc(C(=O)N4CCC(F)(F)C4)cc3)c3c(N)ncnc3n2C)cc1] | C | A |
| 138 | 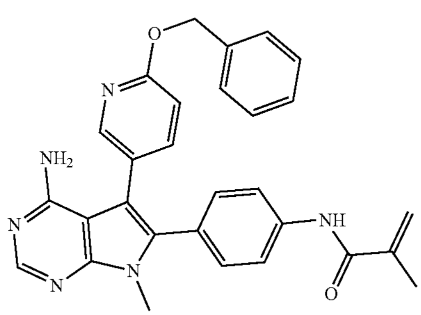 [SMILES: C=C(C)C(=O)Nc1ccc(-c2c(-c3ccc(OCc4ccccc4)nc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 139 | 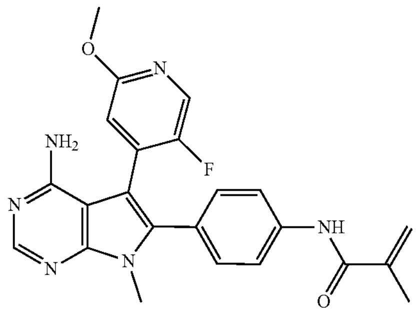 [SMILES: C=C(C)C(=O)Nc1ccc(-c2c(-c3cc(OC)ncc3F)c3c(N)ncnc3n2C)cc1] | D | |
| 140 | 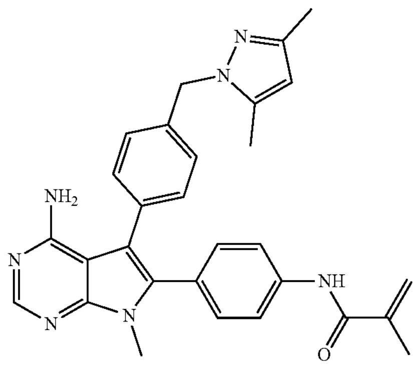 [SMILES: C=C(C)C(=O)Nc1ccc(-c2c(-c3ccc(Cn4nc(C)cc4C)cc3)c3c(N)ncnc3n2C)cc1] | C | B |
| 141 | 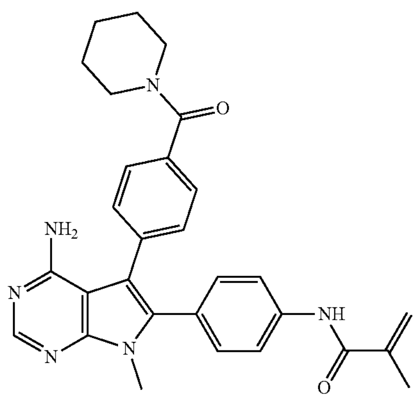 | A | A |
| 142 | 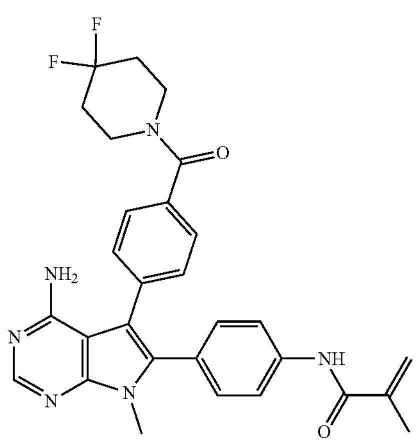 [SMILES: C=C(C)C(=O)Nc1ccc(-c2c(-c3ccc(C(=O)N4CCC(F)(F)CC4)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 143 | 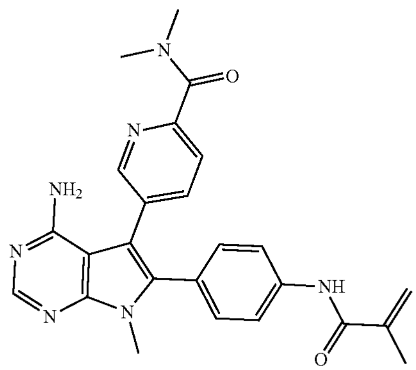 [SMILES: C=C(C)C(=O)Nc1ccc(-c2c(-c3ccc(C(=O)N(C)C)nc3)c3c(N)ncnc3n2C)cc1] | D | C |
| 144 | 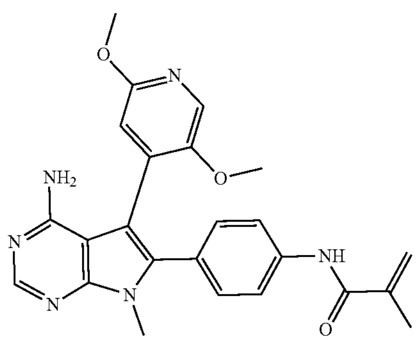 [SMILES: C=C(C)C(=O)Nc1ccc(-c2c(-c3cc(OC)ncc3OC)c3c(N)ncnc3n2C)cc1] | D | |
| 145 | 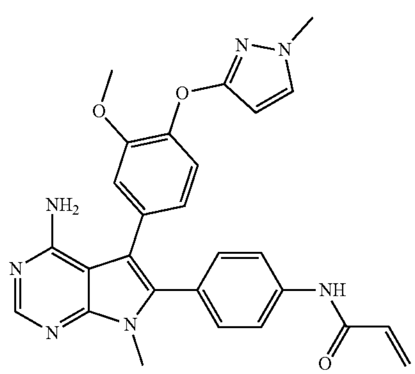 [SMILES: C=CC(=O)Nc1ccc(-c2c(-c3ccc(Oc4ccn(C)n4)c(OC)c3)c3c(N)ncnc3n2C)cc1] | A | A |
| 146 | 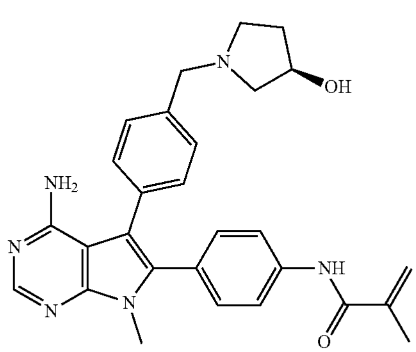 [SMILES: C=C(C)C(=O)Nc1ccc(-c2c(-c3ccc(CN4CC[C@@H](O)C4)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 147 | 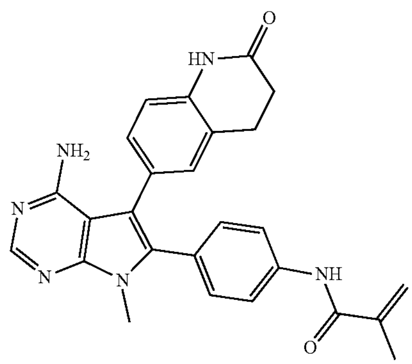 [SMILES: C=C(C)C(=O)Nc1ccc(-c2c(-c3ccc4c(c3)CCC(=O)N4)c3c(N)ncnc3n2C)cc1] | D | |
| 148 | 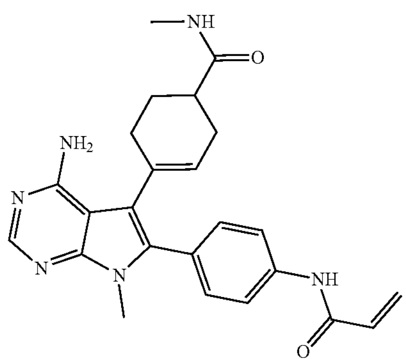 [SMILES: C=CC(=O)Nc1ccc(-c2c(C3=CCC(C(=O)NC)CC3)c3c(N)ncnc3n2C)cc1] | A | A |
| 149 | 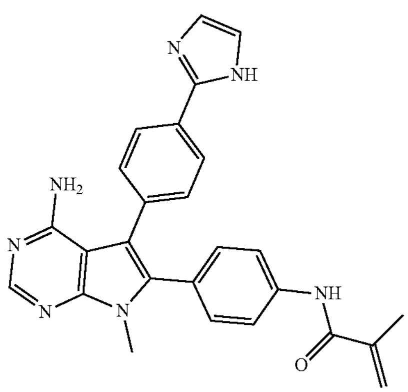 [SMILES: C=C(C)C(=O)Nc1ccc(-c2c(-c3ccc(-c4ncc[nH]4)cc3)c3c(N)ncnc3n2C)cc1] | C | |
| 150 | 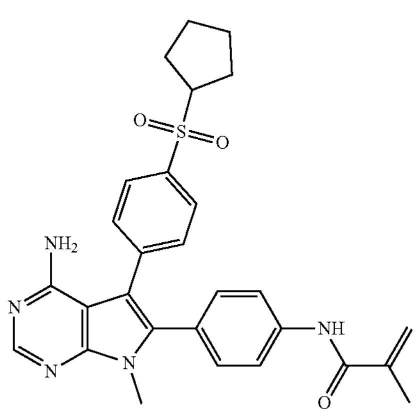 [SMILES: C=C(C)C(=O)Nc1ccc(-c2c(-c3ccc(S(=O)(=O)C4CCCC4)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 151 | 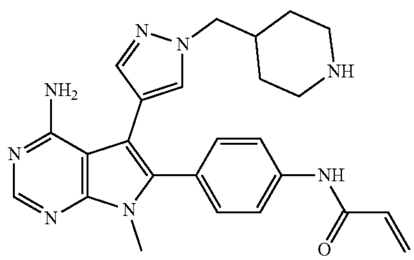 [SMILES: C=CC(=O)Nc1ccc(-c2c(-c3cnn(CC4CCNCC4)c3)c3c(N)ncnc3n2C)cc1] | C | |
| 152 | 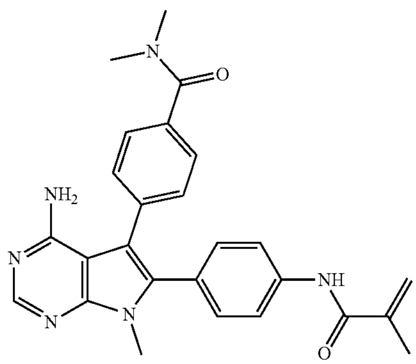 [SMILES: C=C(C)C(=O)Nc1ccc(-c2c(-c3ccc(C(=O)N(C)C)cc3)c3c(N)ncnc3n2C)cc1] | C | C |
| 153 | 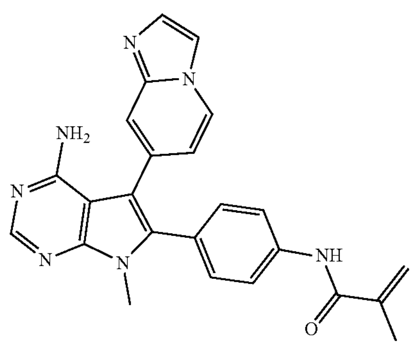 [SMILES: C=C(C)C(=O)Nc1ccc(-c2c(-c3ccn4ccnc4c3)c3c(N)ncnc3n2C)cc1] | D | |
| 154 | 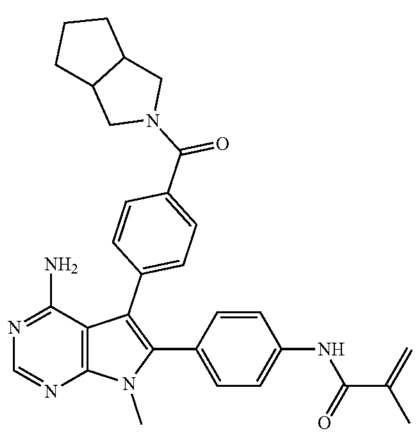 [SMILES: C=C(C)C(=O)Nc1ccc(-c2c(-c3ccc(C(=O)N4CC5CCCC5C4)cc3)c3c(N)ncnc3n2C)cc1] | B | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 155 | 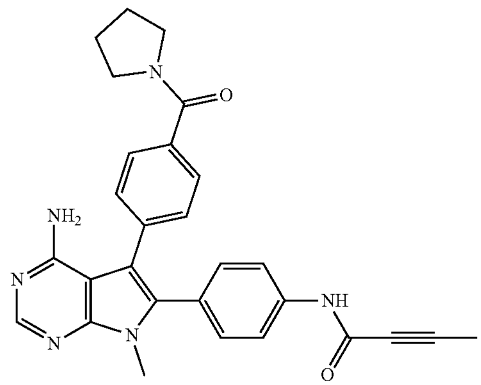 [SMILES: CC#CC(=O)Nc1ccc(-c2c(-c3ccc(C(=O)N4CCCC4)cc3)c3c(N)ncnc3n2C)cc1] | A | A |
| 156 | 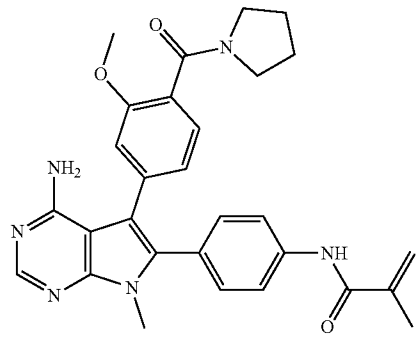 [SMILES: C=C(C)C(=O)Nc1ccc(-c2c(-c3ccc(C(=O)N4CCCC4)c(OC)c3)c3c(N)ncnc3n2C)cc1] | C | B |
| 157 | 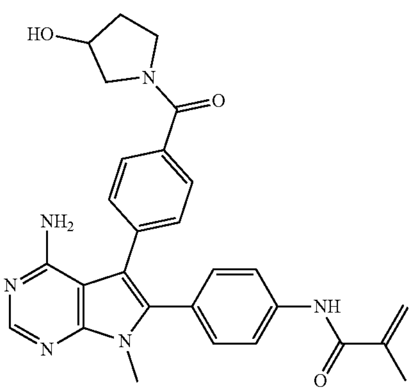 [SMILES: C=C(C)C(=O)Nc1ccc(-c2c(-c3ccc(C(=O)N4CCC(O)C4)cc3)c3c(N)ncnc3n2C)cc1] | C | C |
| 158 | 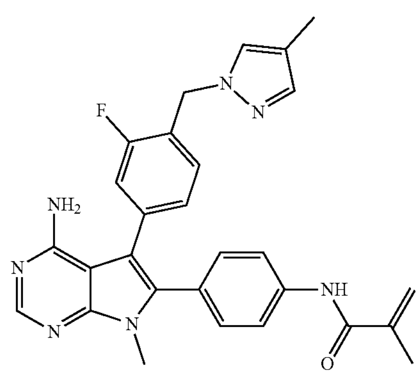 [SMILES: C=C(C)C(=O)Nc1ccc(-c2c(-c3ccc(Cn4cc(C)cn4)c(F)c3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 159 | 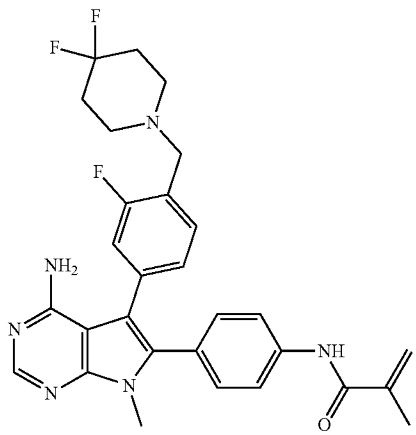 [SMILES: C=C(C)C(=O)Nc1ccc(-c2c(-c3ccc(CN4CCC(F)(F)CC4)c(F)c3)c3c(N)ncnc3n2C)cc1] | D | |
| 160 | 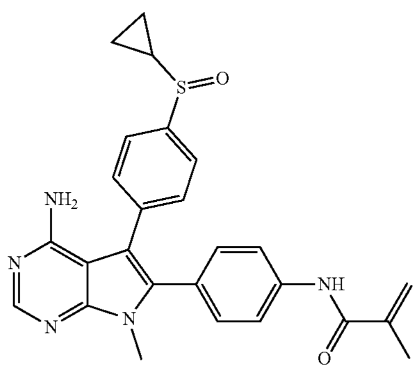 [SMILES: C=C(C)C(=O)Nc1ccc(-c2c(-c3ccc(S(=O)C4CC4)cc3)c3c(N)ncnc3n2C)cc1] | C | C |
| 161 | 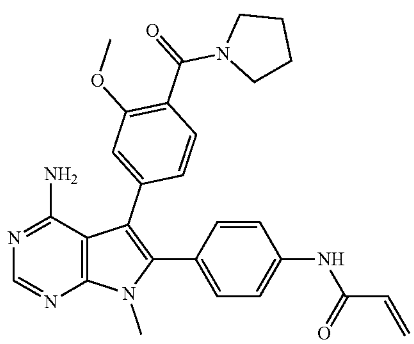 [SMILES: C=CC(=O)Nc1ccc(-c2c(-c3ccc(C(=O)N4CCCC4)c(OC)c3)c3c(N)ncnc3n2C)cc1] | A | A |
| 162 | 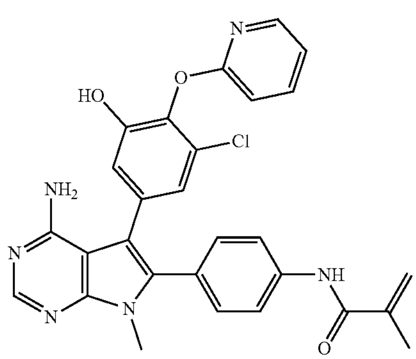 [SMILES: C=C(C)C(=O)Nc1ccc(-c2c(-c3cc(O)c(Oc4ccccn4)c(Cl)c3)c3c(N)ncnc3n2C)cc1] | C | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 163 | 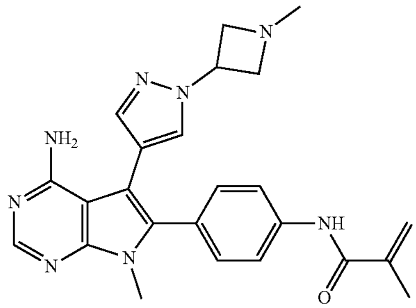 [SMILES: C=C(C)C(=O)Nc1ccc(-c2c(-c3cnn(C4CN(C)C4)c3)c3c(N)ncnc3n2C)cc1] | D | |
| 164 | 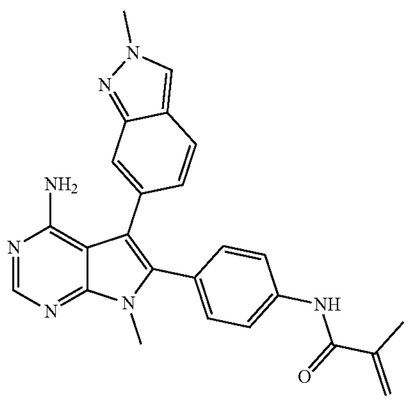 [SMILES: C=C(C)C(=O)Nc1ccc(-c2c(-c3ccc4cn(C)nc4c3)c3c(N)ncnc3n2C)cc1] | B | |
| 165 | 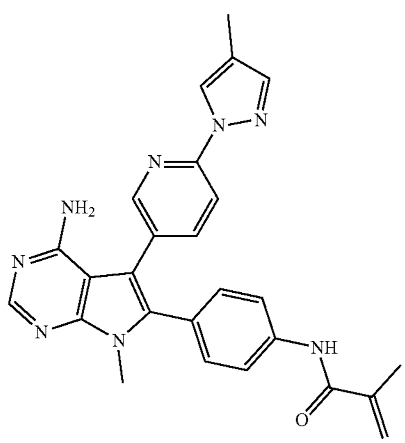 [SMILES: C=C(C)C(=O)Nc1ccc(-c2c(-c3ccc(-n4cc(C)cn4)nc3)c3c(N)ncnc3n2C)cc1] | C | |
| 166 | 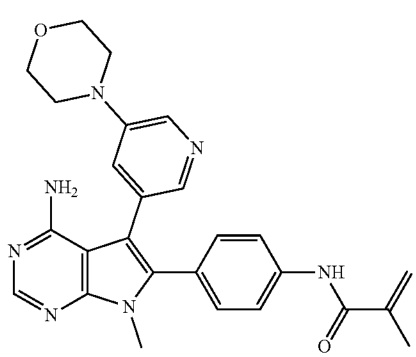 [SMILES: C=C(C)C(=O)Nc1ccc(-c2c(-c3cncc(N4CCOCC4)c3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 167 | 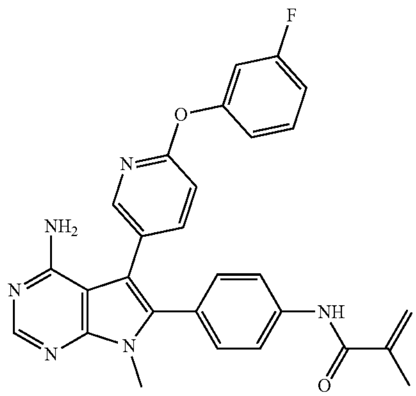 [SMILES: C=C(C)C(=O)Nc1ccc(-c2c(-c3ccc(Oc4cccc(F)c4)nc3)c3c(N)ncnc3n2C)cc1] | D | B |
| 168 | 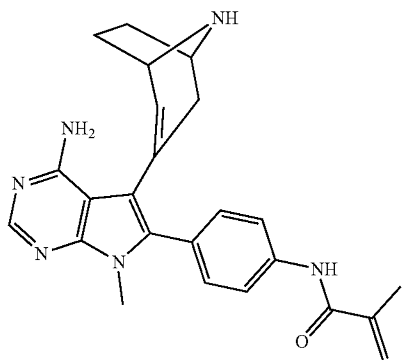 [SMILES: C=C(C)C(=O)Nc1ccc(-c2c(C3=CC4CCC(C3)N4)c3c(N)ncnc3n2C)cc1] | | B |
| 169 | 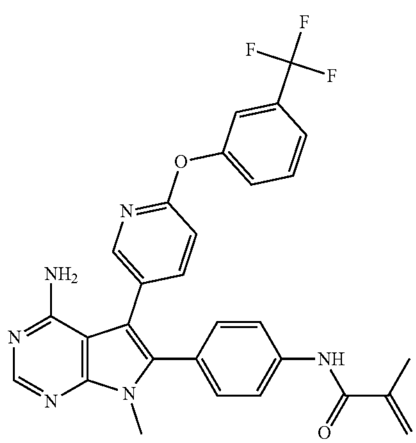 [SMILES: C=C(C)C(=O)Nc1ccc(-c2c(-c3ccc(Oc4cccc(C(F)(F)F)c4)nc3)c3c(N)ncnc3n2C)cc1] | D | C |
| 170 | 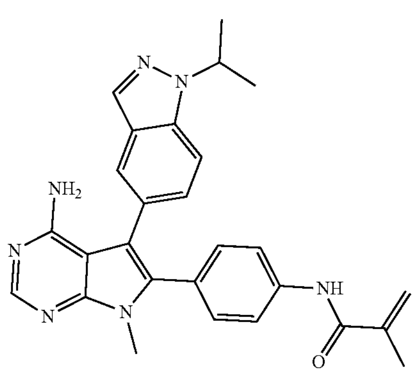 [SMILES: C=C(C)C(=O)Nc1ccc(-c2c(-c3ccc4c(cnn4C(C)C)c3)c3c(N)ncnc3n2C)cc1] | | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 171 | 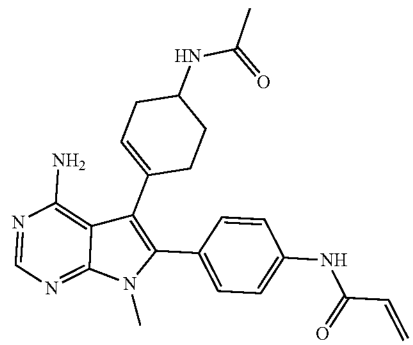 [SMILES: C=CC(=O)Nc1ccc(-c2c(C3=CCC(NC(C)=O)CC3)c3c(N)ncnc3n2C)cc1] | B | C |
| 172 | 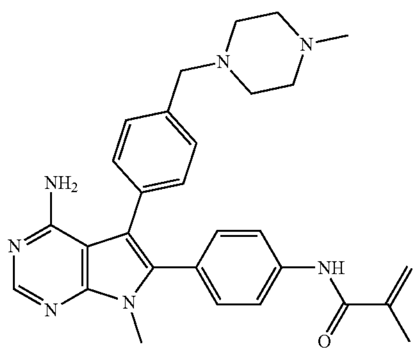 [SMILES: C=C(C)C(=O)Nc1ccc(-c2c(-c3ccc(CN4CCN(C)CC4)cc3)c3c(N)ncnc3n2C)cc1] | D | |
| 173 | 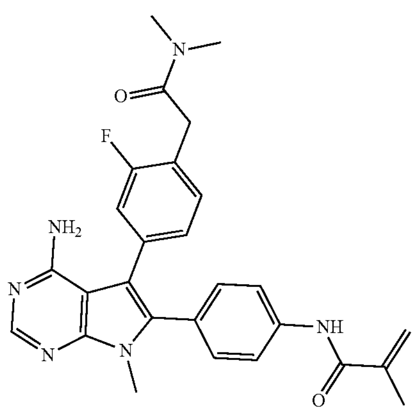 [SMILES: C=C(C)C(=O)Nc1ccc(-c2c(-c3ccc(CC(=O)N(C)C)c(F)c3)c3c(N)ncnc3n2C)cc1] | D | |
| 174 | 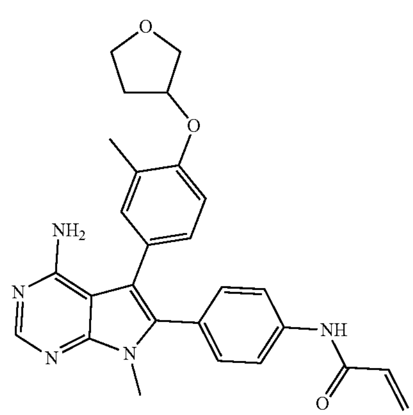 [SMILES: C=CC(=O)Nc1ccc(-c2c(-c3ccc(OC4CCOC4)c(C)c3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 175 | 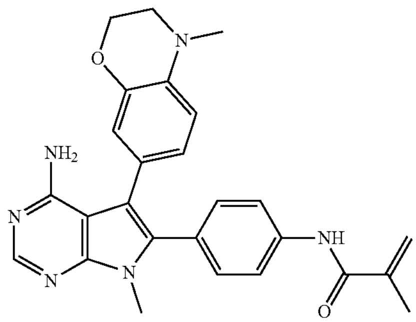 | A | |
| 176 | 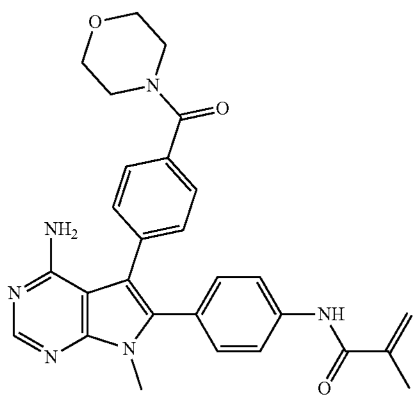 [SMILES: C=C(C)C(=O)Nc1ccc(-c2c(-c3ccc(C(=O)N4CCOCC4)cc3)c3c(N)ncnc3n2C)cc1] | D | C |
| 177 | 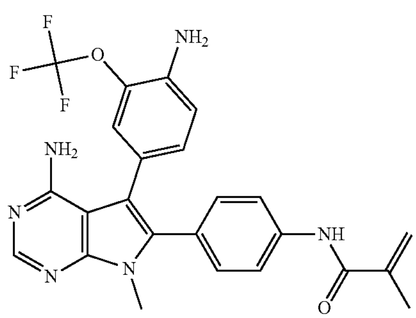 [SMILES: C=C(C)C(=O)Nc1ccc(-c2c(-c3ccc(N)c(OC(F)(F)F)c3)c3c(N)ncnc3n2C)cc1] | D | |
| 178 | 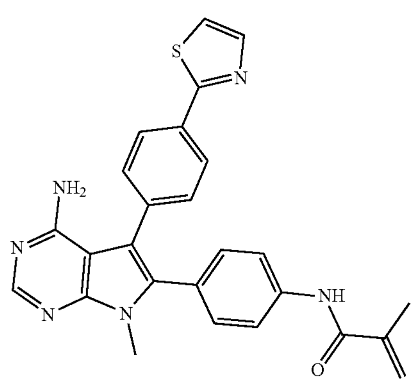 [SMILES: C=C(C)C(=O)Nc1ccc(-c2c(-c3ccc(-c4nccs4)cc3)c3c(N)ncnc3n2C)cc1] | C | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 179 | 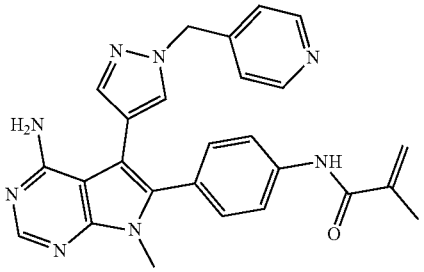 [SMILES: C=C(C)C(=O)Nc1ccc(-c2c(-c3cnn(Cc4ccncc4)c3)c3c(N)ncnc3n2C)cc1] | D | |
| 180 | 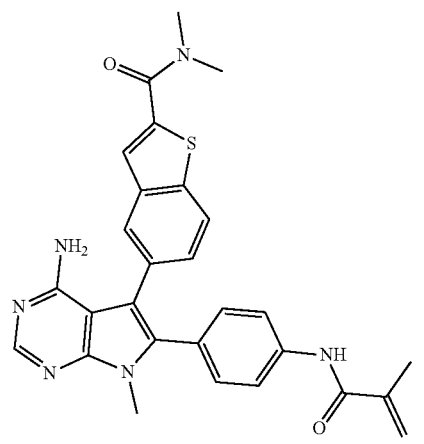 [SMILES: C=C(C)C(=O)Nc1ccc(-c2c(-c3ccc4sc(C(=O)N(C)C)cc4c3)c3c(N)ncnc3n2C)cc1] | C | B |
| 181 | 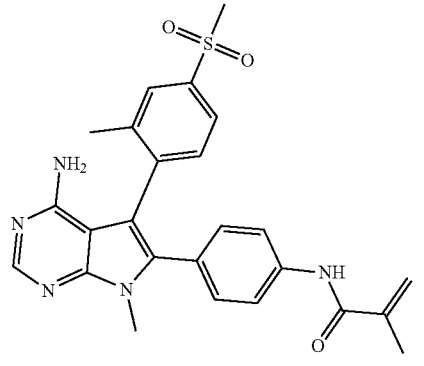 [SMILES: C=C(C)C(=O)Nc1ccc(-c2c(-c3ccc(S(C)(=O)=O)cc3C)c3c(N)ncnc3n2C)cc1] | D | |
| 182 | 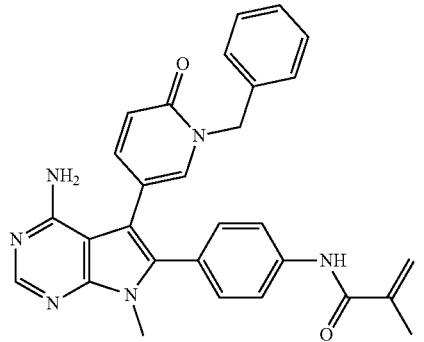 [SMILES: C=C(C)C(=O)Nc1ccc(-c2c(-c3ccc(=O)n(Cc4ccccc4)c3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 183 | 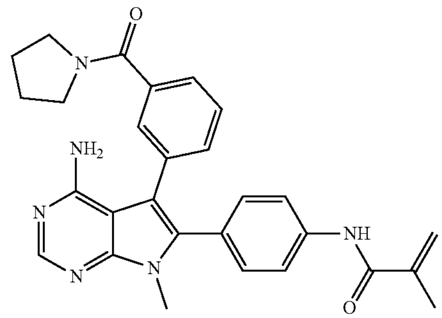 [SMILES: C=C(C)C(=O)Nc1ccc(-c2c(-c3cccc(C(=O)N4CCCC4)c3)c3c(N)ncnc3n2C)cc1] | D | |
| 184 | 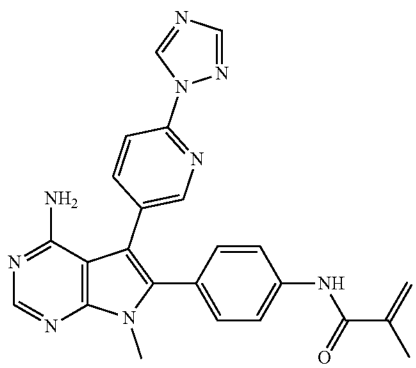 [SMILES: C=C(C)C(=O)Nc1ccc(-c2c(-c3ccc(-n4cncn4)nc3)c3c(N)ncnc3n2C)cc1] | D | |
| 185 | 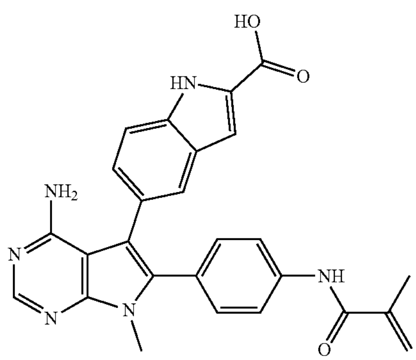 [SMILES: C=C(C)C(=O)Nc1ccc(-c2c(-c3ccc4[nH]c(C(=O)O)cc4c3)c3c(N)ncnc3n2C)cc1] | D | |
| 186 | 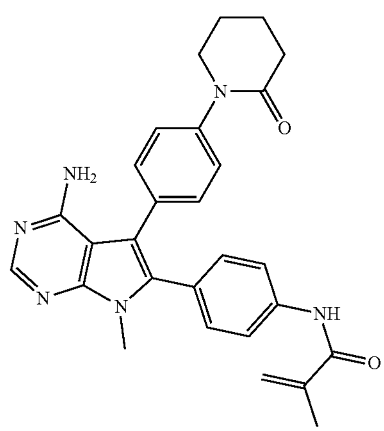 [SMILES: C=C(C)C(=O)Nc1ccc(-c2c(-c3ccc(N4CCCCC4=O)cc3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 187 | 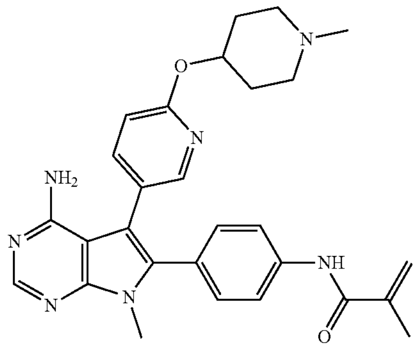 [SMILES: C=C(C)C(=O)Nc1ccc(-c2c(-c3ccc(OC4CCN(C)CC4)nc3)c3c(N)ncnc3n2C)cc1] | D | |
| 188 | 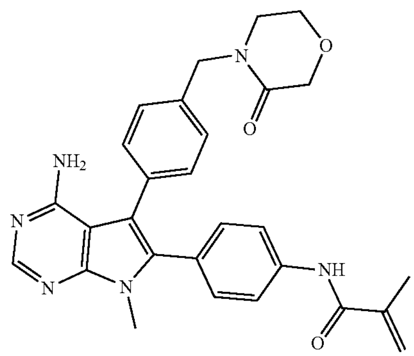 [SMILES: C=C(C)C(=O)Nc1ccc(-c2c(-c3ccc(CN4CCOCC4=O)cc3)c3c(N)ncnc3n2C)cc1] | D | C |
| 189 | 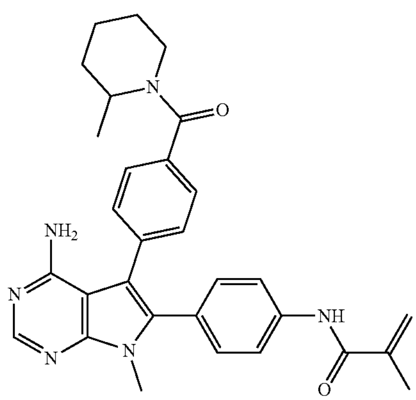 [SMILES: C=C(C)C(=O)Nc1ccc(-c2c(-c3ccc(C(=O)N4CCCCC4C)cc3)c3c(N)ncnc3n2C)cc1] | A | A |
| 190 | 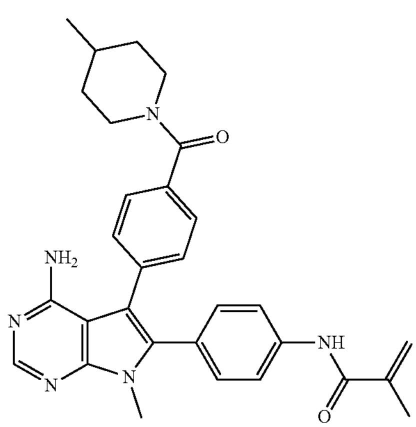 [SMILES: C=C(C)C(=O)Nc1ccc(-c2c(-c3ccc(C(=O)N4CCC(C)CC4)cc3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 191 | 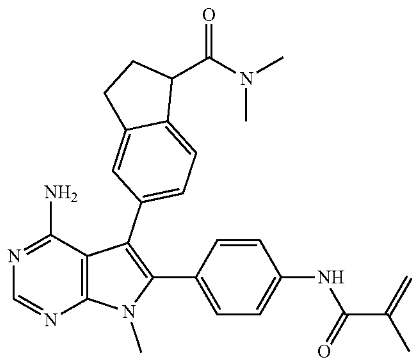 [SMILES: C=C(C)C(=O)Nc1ccc(-c2c(-c3ccc4c(c3)CCC4C(=O)N(C)C)c3c(N)ncnc3n2C)cc1] | D | |
| 192 | 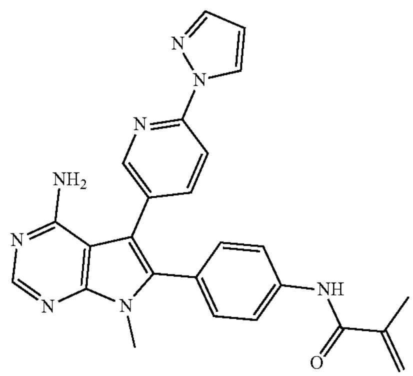 [SMILES: C=C(C)C(=O)Nc1ccc(-c2c(-c3ccc(-n4cccn4)nc3)c3c(N)ncnc3n2C)cc1] | D | |
| 193 | 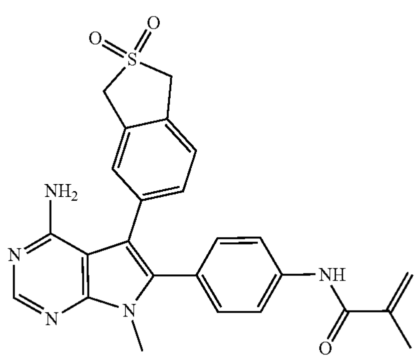 [SMILES: C=C(C)C(=O)Nc1ccc(-c2c(-c3ccc4c(c3)CS(=O)(=O)C4)c3c(N)ncnc3n2C)cc1] | D | |
| 194 | 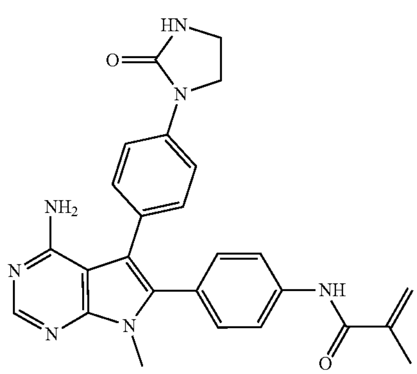 [SMILES: C=C(C)C(=O)Nc1ccc(-c2c(-c3ccc(N4CCNC4=O)cc3)c3c(N)ncnc3n2C)cc1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 195 | 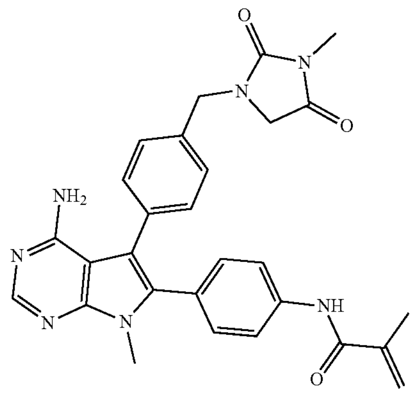 [SMILES: C=C(C)C(=O)Nc1ccc(-c2c(-c3ccc(CN4CC(=O)N(C)C4=O)cc3)c3c(N)ncnc3n2C)cc1] | | |
| 196 | 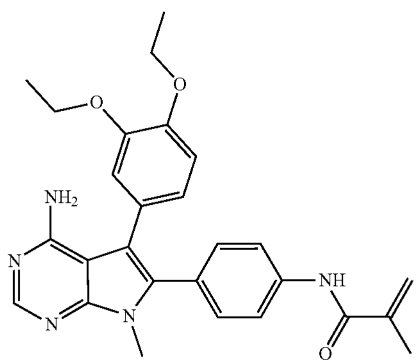 [SMILES: C=C(C)C(=O)Nc1ccc(-c2c(-c3ccc(OCC)c(OCC)c3)c3c(N)ncnc3n2C)cc1] | D | |
| 197 | 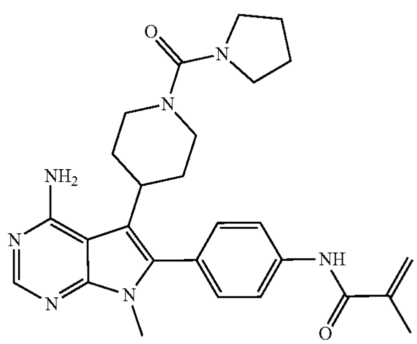 [SMILES: C=C(C)C(=O)Nc1ccc(-c2c(C3CCN(C(=O)N4CCCC4)CC3)c3c(N)ncnc3n2C)cc1] | D | C |
| 198 | 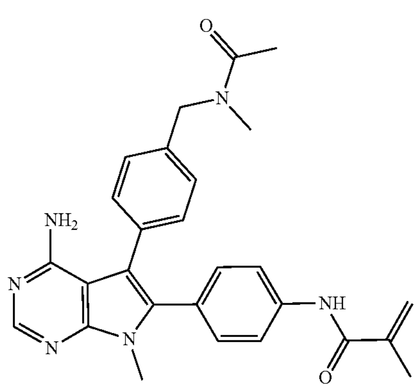 [SMILES: C=C(C)C(=O)Nc1ccc(-c2c(-c3ccc(CN(C)C(C)=O)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 199 | 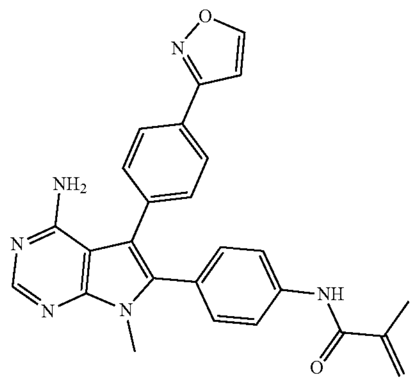 [SMILES: C=C(C)C(=O)Nc1ccc(-c2c(-c3ccc(-c4ccon4)cc3)c3c(N)ncnc3n2C)cc1] | C | C |
| 200 | 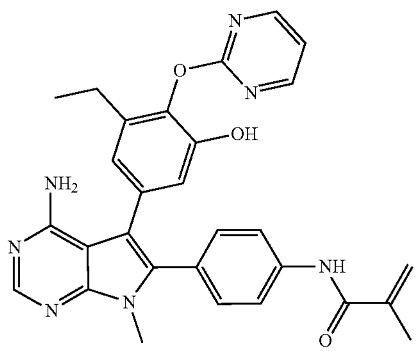 [SMILES: C=C(C)C(=O)Nc1ccc(-c2c(-c3cc(O)c(Oc4ncccn4)c(CC)c3)c3c(N)ncnc3n2C)cc1] | D | |
| 201 | 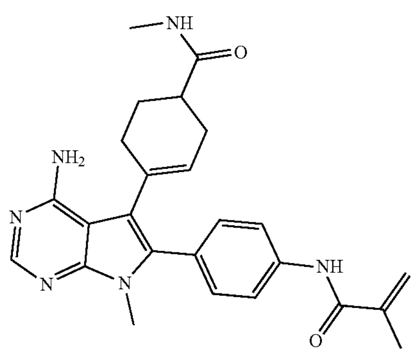 [SMILES: C=C(C)C(=O)Nc1ccc(-c2c(C3=CCC(C(=O)NC)CC3)c3c(N)ncnc3n2C)cc1] | D | C |
| 202 | 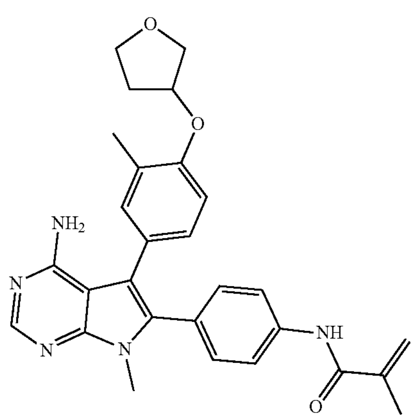 [SMILES: C=C(C)C(=O)Nc1ccc(-c2c(-c3ccc(OC4CCOC4)c(C)c3)c3c(N)ncnc3n2C)cc1] | C | B |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 203 | 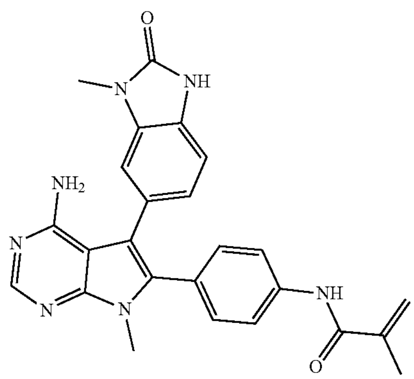 [SMILES: C=C(C)C(=O)Nc1ccc(-c2c(-c3ccc4[nH]c(=O)n(C)c4c3)c3c(N)ncnc3n2C)cc1] | D | |
| 204 | 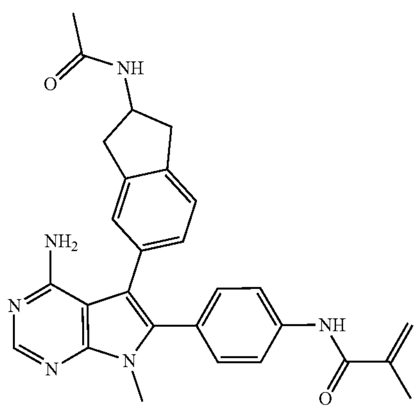 [SMILES: C=C(C)C(=O)Nc1ccc(-c2c(-c3ccc4c(c3)CC(NC(C)=O)C4)c3c(N)ncnc3n2C)cc1] | D | |
| 205 | 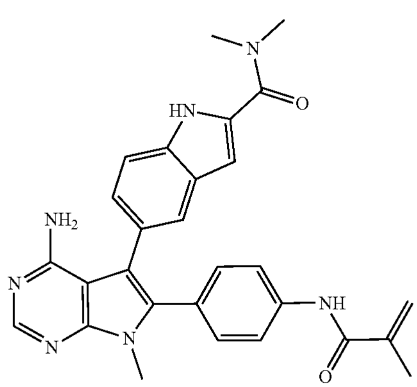 [SMILES: C=C(C)C(=O)Nc1ccc(-c2c(-c3ccc4[nH]c(C(=O)N(C)C)cc4c3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 206 | 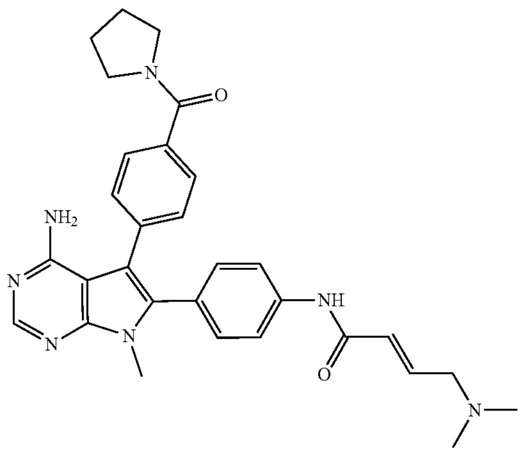 [SMILES: CN(C)C/C=C/C(=O)Nc1ccc(-c2c(-c3ccc(C(=O)N4CCCC4)cc3)c3c(N)ncnc3n2C)cc1] | A | B |
| 207 | 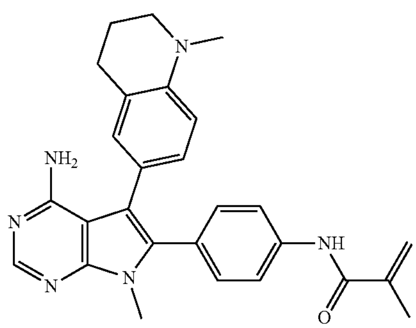 | C | C |
| 208 | 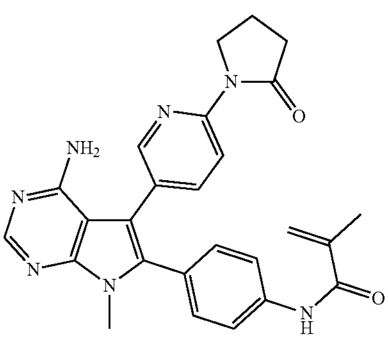 [SMILES: C=C(C)C(=O)Nc1ccc(-c2c(-c3ccc(N4CCCC4=O)nc3)c3c(N)ncnc3n2C)cc1] | D | |
| 209 | 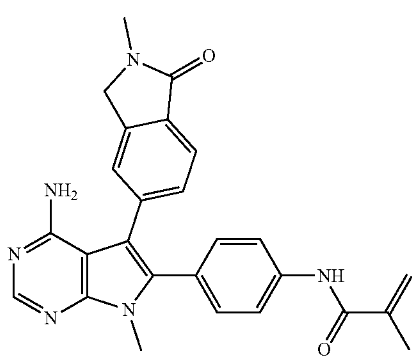 [SMILES: C=C(C)C(=O)Nc1ccc(-c2c(-c3ccc4c(c3)CN(C)C4=O)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 210 | 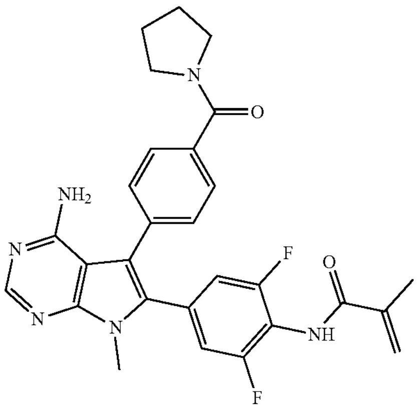 [SMILES: C=C(C)C(=O)Nc1c(F)cc(-c2c(-c3ccc(C(=O)N4CCCC4)cc3)c3c(N)ncnc3n2C)cc1F] | D | C |
| 211 | 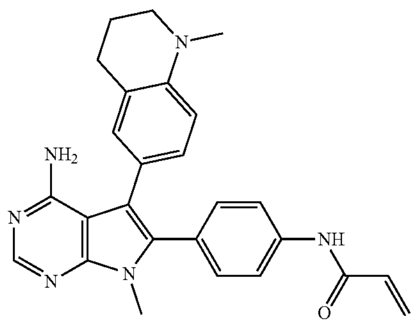 [SMILES: C=CC(=O)Nc1ccc(-c2c(-c3ccc4c(c3)CCCN4C)c3c(N)ncnc3n2C)cc1] | A | A |
| 212 | 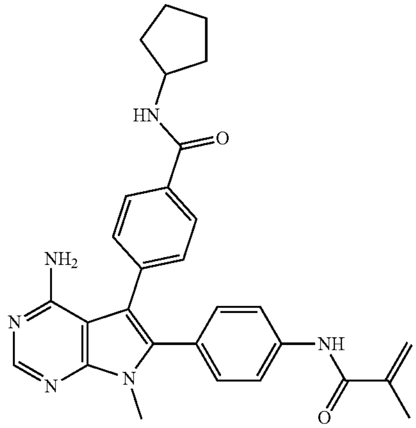 [SMILES: C=C(C)C(=O)Nc1ccc(-c2c(-c3ccc(C(=O)NC4CCCC4)cc3)c3c(N)ncnc3n2C)cc1] | A | A |
| 213 | 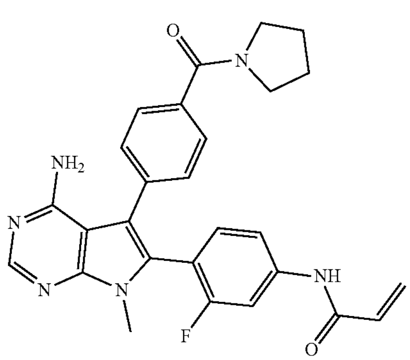 [SMILES: C=CC(=O)Nc1ccc(-c2c(-c3ccc(C(=O)N4CCCC4)cc3)c3c(N)ncnc3n2C)c(F)c1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 214 | 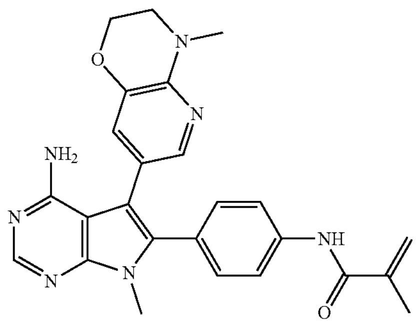 [SMILES: C=C(C)C(=O)Nc1ccc(-c2c(-c3cnc4c(c3)OCCN4C)c3c(N)ncnc3n2C)cc1] | B | |
| 215 | 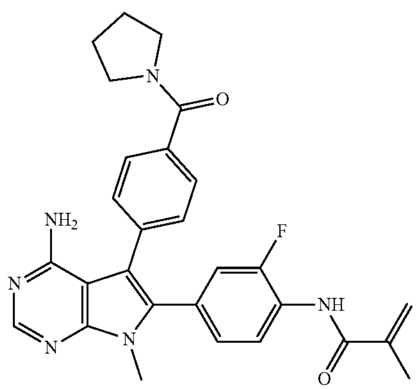 [SMILES: C=C(C)C(=O)Nc1ccc(-c2c(-c3ccc(C(=O)N4CCCC4)cc3)c3c(N)ncnc3n2C)cc1F] | C | C |
| 216 | 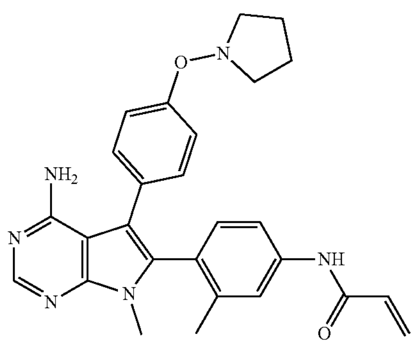 [SMILES: C=CC(=O)Nc1ccc(-c2c(-c3ccc(ON4CCCC4)cc3)c3c(N)ncnc3n2C)c(C)c1] | A | A |
| 217 | 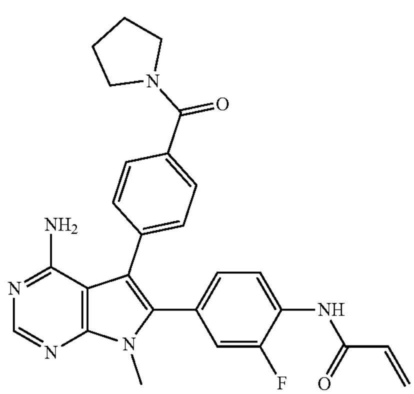 [SMILES: C=CC(=O)Nc1ccc(-c2c(-c3ccc(C(=O)N4CCCC4)cc3)c3c(N)ncnc3n2C)cc1F] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 218 | 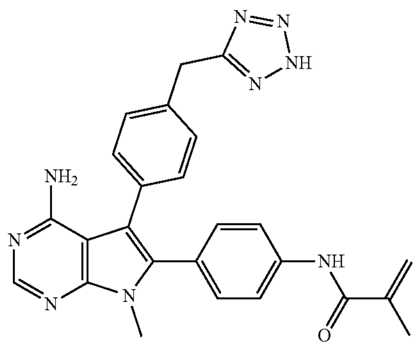 [SMILES: C=C(C)C(=O)Nc1ccc(-c2c(-c3ccc(Cc4nn[nH]n4)cc3)c3c(N)ncnc3n2C)cc1] | D | |
| 219 | 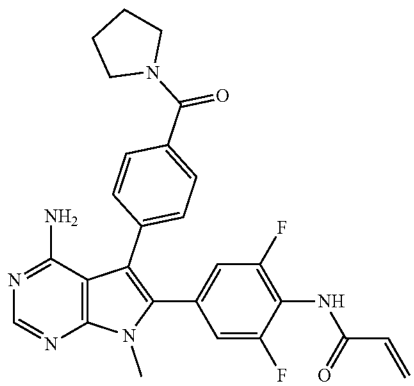 [SMILES: C=CC(=O)Nc1c(F)cc(-c2c(-c3ccc(C(=O)N4CCCC4)cc3)c3c(N)ncnc3n2C)cc1F] | A | A |
| 220 | 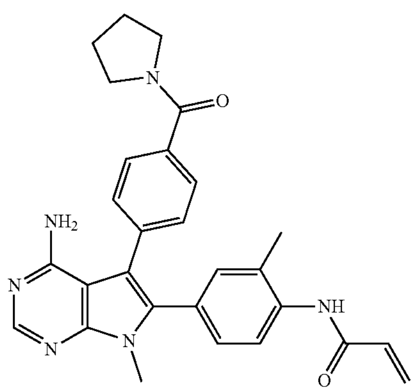 [SMILES: C=CC(=O)Nc1ccc(-c2c(-c3ccc(C(=O)N4CCCC4)cc3)c3c(N)ncnc3n2C)cc1C] | A | A |
| 221 | 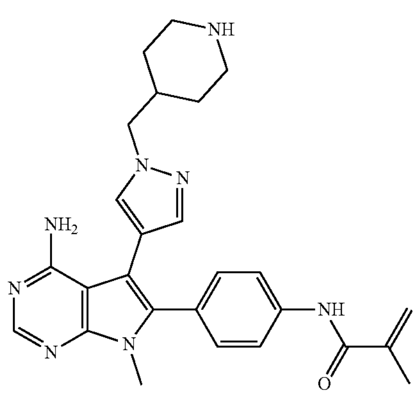 [SMILES: C=C(C)C(=O)Nc1ccc(-c2c(-c3cnn(CC4CCNCC4)c3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 222 | 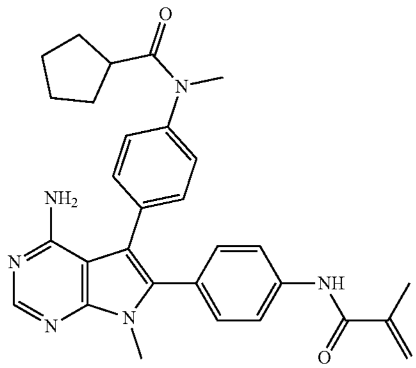 [SMILES: C=C(C)C(=O)Nc1ccc(-c2c(-c3ccc(N(C)C(=O)C4CCCC4)cc3)c3c(N)ncnc3n2C)cc1] | D | |
| 223 | 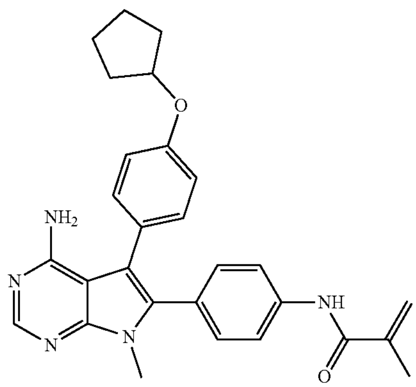 [SMILES: C=C(C)C(=O)Nc1ccc(-c2c(-c3ccc(OC4CCCC4)cc3)c3c(N)ncnc3n2C)cc1] | A | A |
| 224 | 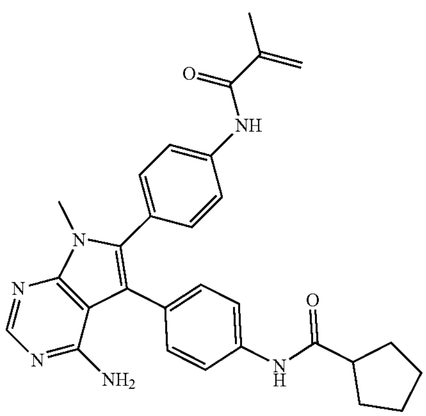 [SMILES: C=C(C)C(=O)Nc1ccc(-c2c(-c3ccc(NC(=O)C4CCCC4)cc3)c3c(N)ncnc3n2C)cc1] | A | A |
| 225 | 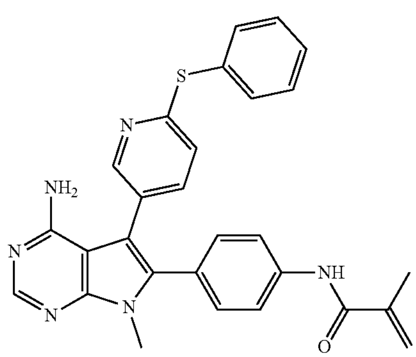 [SMILES: C=C(C)C(=O)Nc1ccc(-c2c(-c3ccc(Sc4ccccc4)nc3)c3c(N)ncnc3n2C)cc1] | C | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 226 | 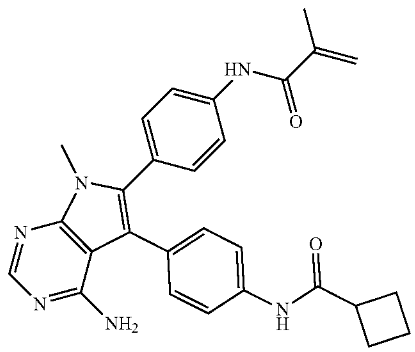 [SMILES: C=C(C)C(=O)Nc1ccc(-c2c(-c3ccc(NC(=O)C4CCC4)cc3)c3c(N)ncnc3n2C)cc1] | A | |
| 227 | 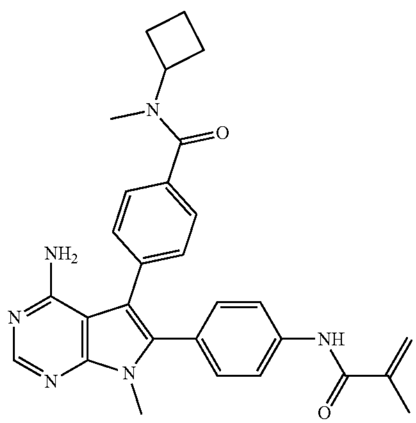 [SMILES: C=C(C)C(=O)Nc1ccc(-c2c(-c3ccc(C(=O)N(C)C4CCC4)cc3)c3c(N)ncnc3n2C)cc1] | B | B |
| 228 | 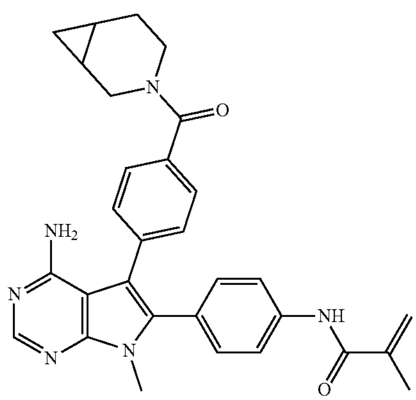 [SMILES: C=C(C)C(=O)Nc1ccc(-c2c(-c3ccc(C(=O)N4CCC5CC5C4)cc3)c3c(N)ncnc3n2C)cc1] | A | A |
| 229 | 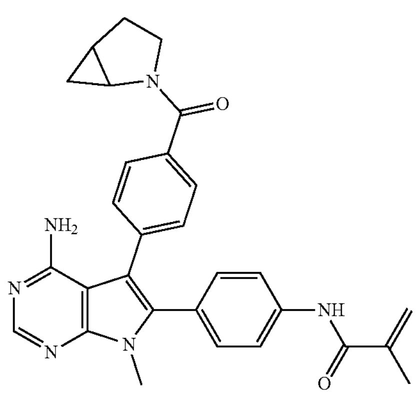 [SMILES: C=C(C)C(=O)Nc1ccc(-c2c(-c3ccc(C(=O)N4CCC5CC54)cc3)c3c(N)ncnc3n2C)cc1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 230 | 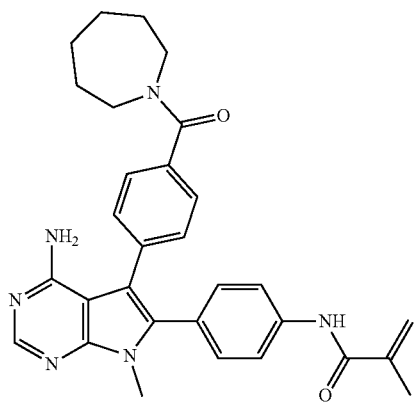 [SMILES: C=C(C)C(=O)Nc1ccc(-c2c(-c3ccc(C(=O)N4CCCCCC4)cc3)c3c(N)ncnc3n2C)cc1] | A | A |
| 231 | 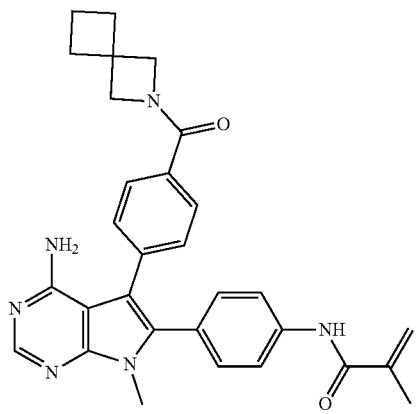 [SMILES: C=C(C)C(=O)Nc1ccc(-c2c(-c3ccc(C(=O)N4CC5(CCC5)C4)cc3)c3c(N)ncnc3n2C)cc1] | D | |
| 232 | 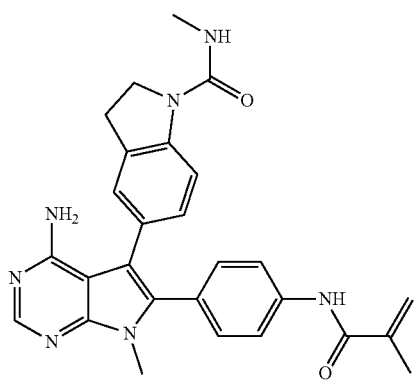 [SMILES: C=C(C)C(=O)Nc1ccc(-c2c(-c3ccc4c(c3)CCN4C(=O)NC)c3c(N)ncnc3n2C)cc1] | C | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 233 | 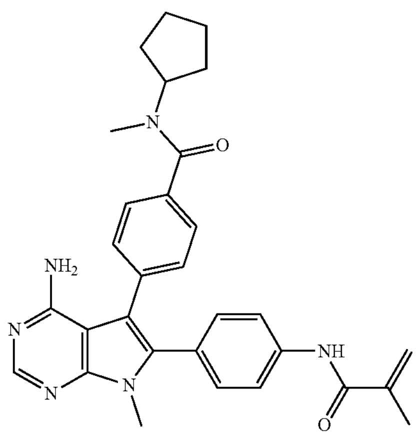 [SMILES: C=C(C)C(=O)Nc1ccc(-c2c(-c3ccc(C(=O)N(C)C4CCCC4)cc3)c3c(N)ncnc3n2C)cc1] | B | B |
| 234 | 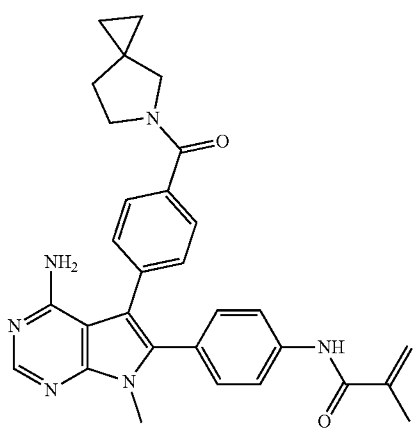 [SMILES: C=C(C)C(=O)Nc1ccc(-c2c(-c3ccc(C(=O)N4CCC5(CC5)C4)cc3)c3c(N)ncnc3n2C)cc1] | A | A |
| 235 | 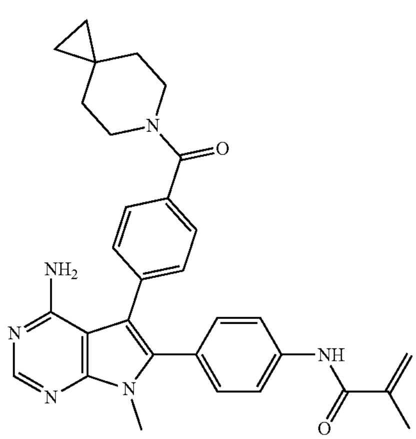 [SMILES: C=C(C)C(=O)Nc1ccc(-c2c(-c3ccc(C(=O)N4CCC5(CC4)CC5)cc3)c3c(N)ncnc3n2C)cc1] | | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 236 | 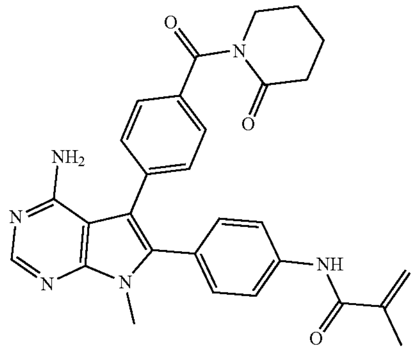 [SMILES: C=C(C)C(=O)Nc1ccc(-c2c(-c3ccc(C(=O)N4CCCCC4=O)cc3)c3c(N)ncnc3n2C)cc1] | B | B |
| 237 | 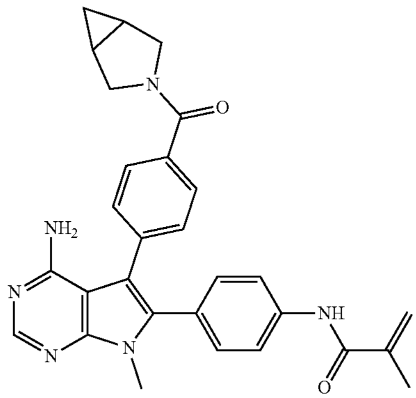 [SMILES: C=C(C)C(=O)Nc1ccc(-c2c(-c3ccc(C(=O)N4CC5CC5C4)cc3)c3c(N)ncnc3n2C)cc1] | B | B |
| 238 | 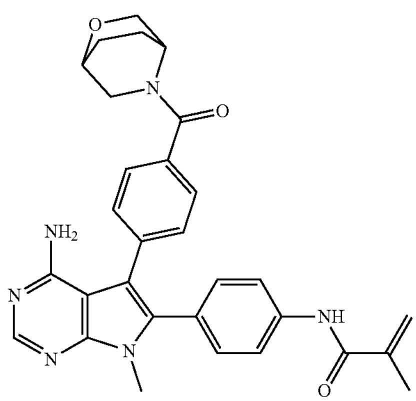 [SMILES: C=C(C)C(=O)Nc1ccc(-c2c(-c3ccc(C(=O)N4CC5CCC4CO5)cc3)c3c(N)ncnc3n2C)cc1] | C | C |
| 239 | 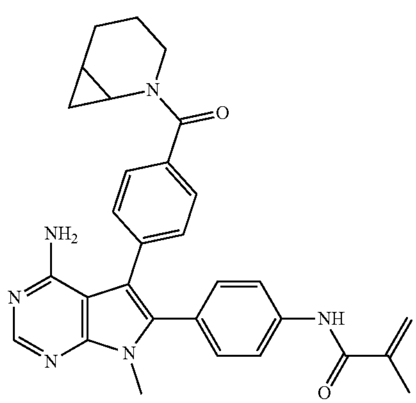 [SMILES: C=C(C)C(=O)Nc1ccc(-c2c(-c3ccc(C(=O)N4CCCC5CC54)cc3)c3c(N)ncnc3n2C)cc1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 240 | 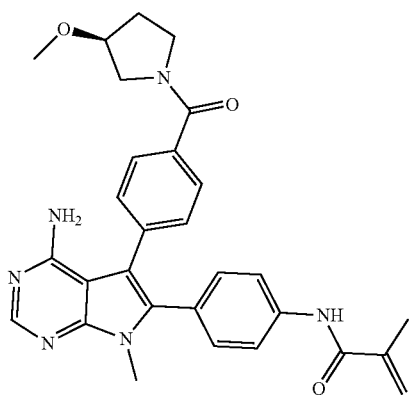 [SMILES: C=C(C)C(=O)Nc1ccc(-c2c(-c3ccc(C(=O)N4CC[C@H](OC)C4)cc3)c3c(N)ncnc3n2C)cc1] | D | |
| 241 | 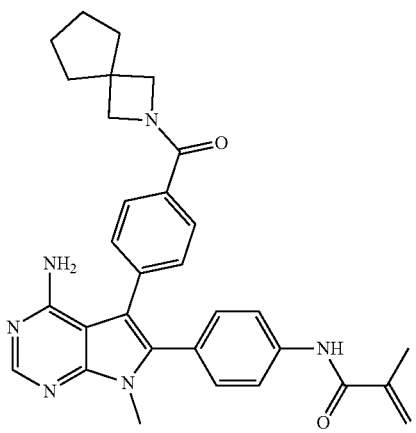 [SMILES: C=C(C)C(=O)Nc1ccc(-c2c(-c3ccc(C(=O)N4CC5(CCCC5)C4)cc3)c3c(N)ncnc3n2C)cc1] | D | C |
| 242 | 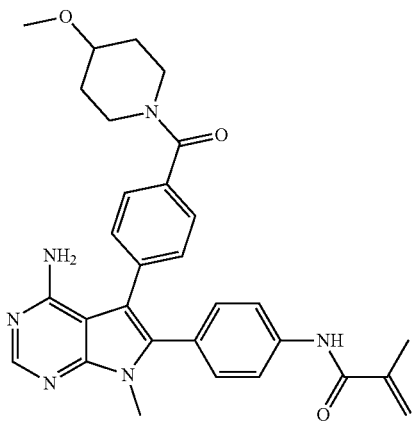 [SMILES: C=C(C)C(=O)Nc1ccc(-c2c(-c3ccc(C(=O)N4CCC(OC)CC4)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 243 | 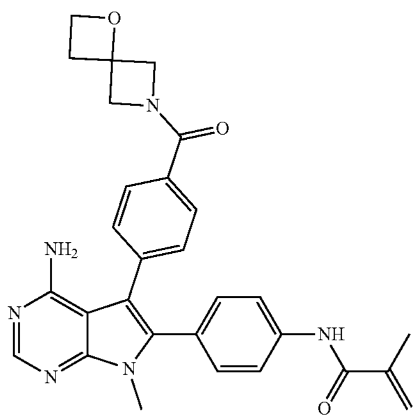 [SMILES: C=C(C)C(=O)Nc1ccc(-c2c(-c3ccc(C(=O)N4CC5(CCO5)C4)cc3)c3c(N)ncnc3n2C)cc1] | D | |
| 244 | 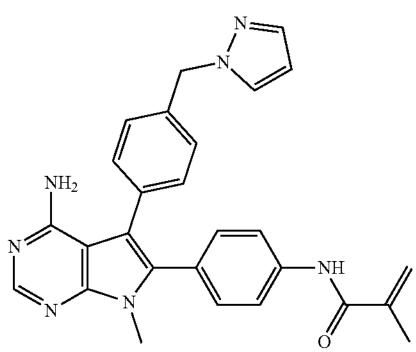 [SMILES: C=C(C)C(=O)Nc1ccc(-c2c(-c3ccc(Cn4cccn4)cc3)c3c(N)ncnc3n2C)cc1] | D | C |
| 245 | 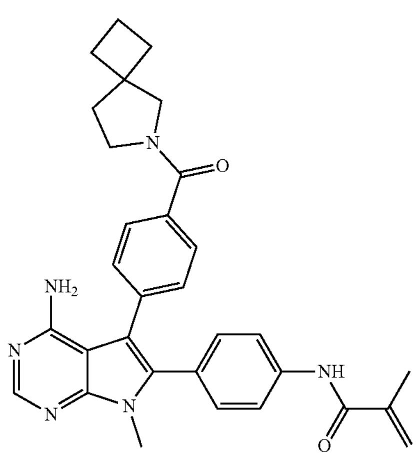 [SMILES: C=C(C)C(=O)Nc1ccc(-c2c(-c3ccc(C(=O)N4CCC5(CCC5)C4)cc3)c3c(N)ncnc3n2C)cc1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 246 | 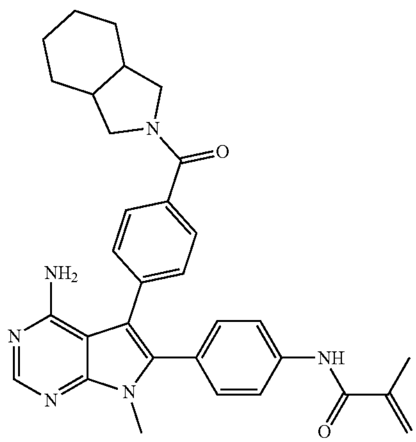 [SMILES: C=C(C)C(=O)Nc1ccc(-c2c(-c3ccc(C(=O)N4CC5CCCCC5C4)cc3)c3c(N)ncnc3n2C)cc1] | C | B |
| 247 | 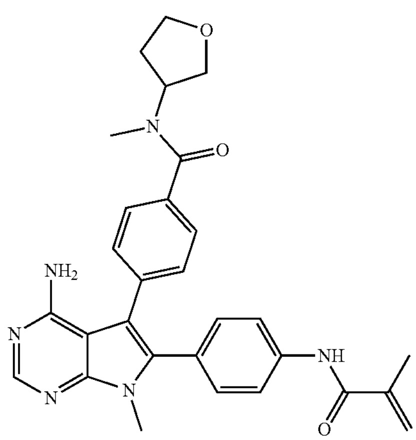 [SMILES: C=C(C)C(=O)Nc1ccc(-c2c(-c3ccc(C(=O)N(C)C4CCOC4)cc3)c3c(N)ncnc3n2C)cc1] | D | |
| 248 | 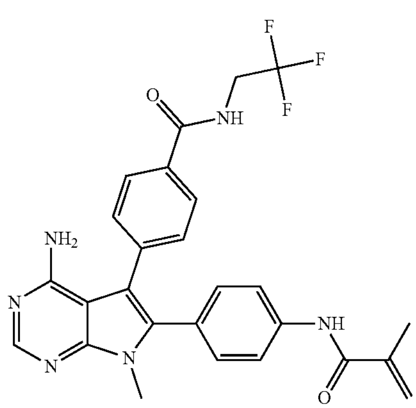 [SMILES: C=C(C)C(=O)Nc1ccc(-c2c(-c3ccc(C(=O)NCC(F)(F)F)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 249 | 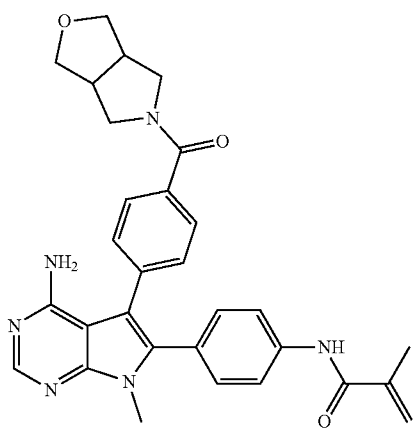 [SMILES: C=C(C)C(=O)Nc1ccc(-c2c(-c3ccc(C(=O)N4CC5COCC5C4)cc3)c3c(N)ncnc3n2C)cc1] | C | C |
| 250 | 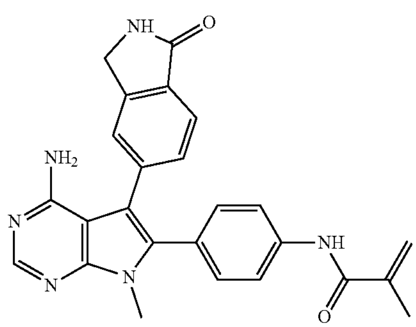 [SMILES: C=C(C)C(=O)Nc1ccc(-c2c(-c3ccc4c(c3)CNC4=O)c3c(N)ncnc3n2C)cc1] | | D |
| 251 | 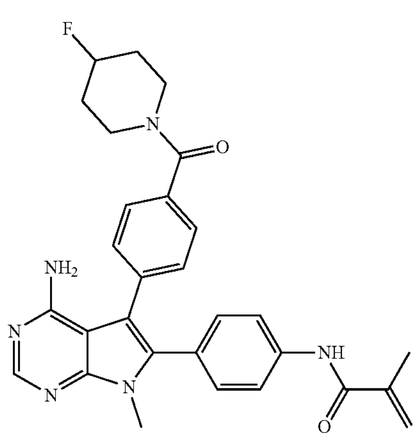 [SMILES: C=C(C)C(=O)Nc1ccc(-c2c(-c3ccc(C(=O)N4CCC(F)CC4)cc3)c3c(N)ncnc3n2C)cc1] | | C |

TABLE 1-continued

Representative Compounds of the Invention with Bioactivity Data.

| Example | Structure | Biochemical FGFR2 Caliper IC50 | Cell SNU-16 IC50 |
|---------|-----------|--------------------------------|------------------|
| 252 | 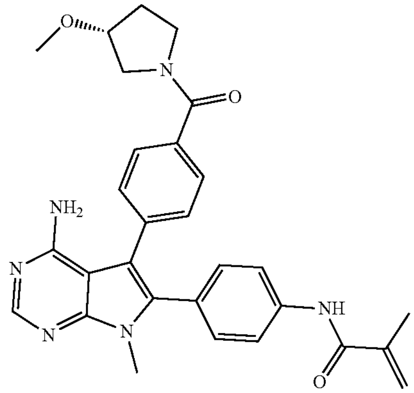 [SMILES: C=C(C)C(=O)Nc1ccc(-c2c(-c3ccc(C(=O)N4CC[C@@H](OC)C4)cc3)c3c(N)ncnc3n2C)cc1] | C | |
| 253 | 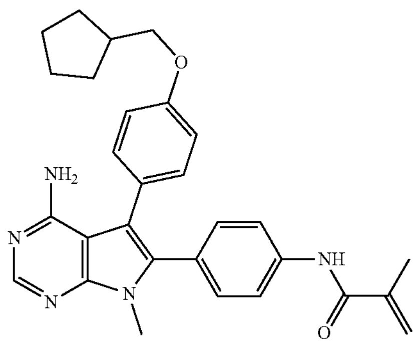 [SMILES: C=C(C)C(=O)Nc1ccc(-c2c(-c3ccc(OCC4CCCC4)cc3)c3c(N)ncnc3n2C)cc1] | C | |
| 254 | 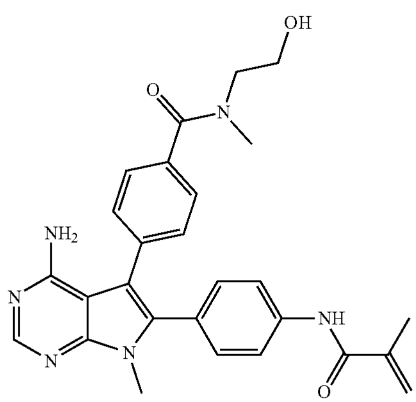 [SMILES: C=C(C)C(=O)Nc1ccc(-c2c(-c3ccc(C(=O)N(C)CCO)cc3)c3c(N)ncnc3n2C)cc1] | C | |
| 255 | 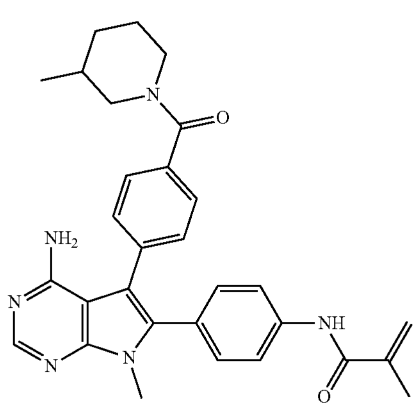 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 256 | 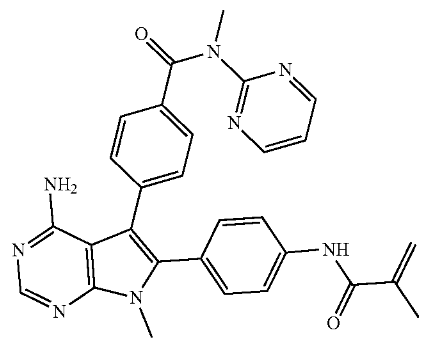 [SMILES: C=C(C)C(=O)Nc1ccc(-c2c(-c3ccc(C(=O)N(C)c4ncccn4)cc3)c3c(N)ncnc3n2C)cc1] | D | |
| 257 | 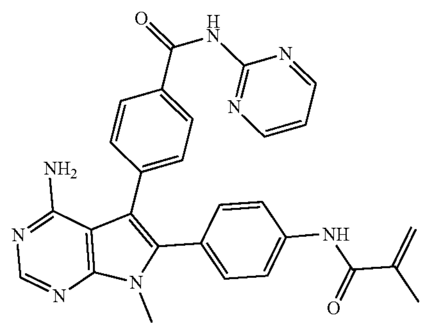 [SMILES: C=C(C)C(=O)Nc1ccc(-c2c(-c3ccc(C(=O)Nc4ncccn4)cc3)c3c(N)ncnc3n2C)cc1] | C | C |
| 258 | 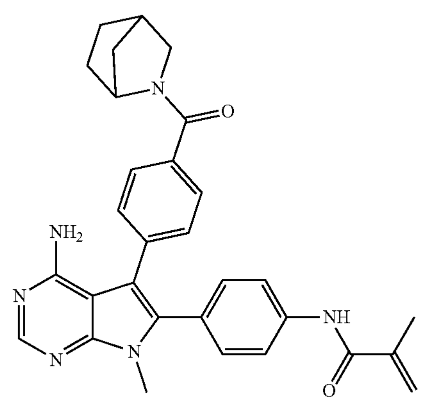 [SMILES: C=C(C)C(=O)Nc1ccc(-c2c(-c3ccc(C(=O)N4CC5CCC4C5)cc3)c3c(N)ncnc3n2C)cc1] | A | A |
| 259 | 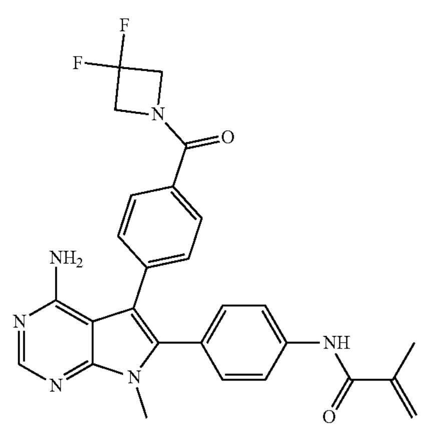 [SMILES: C=C(C)C(=O)Nc1ccc(-c2c(-c3ccc(C(=O)N4CC(F)(F)C4)cc3)c3c(N)ncnc3n2C)cc1] | D | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 260 | 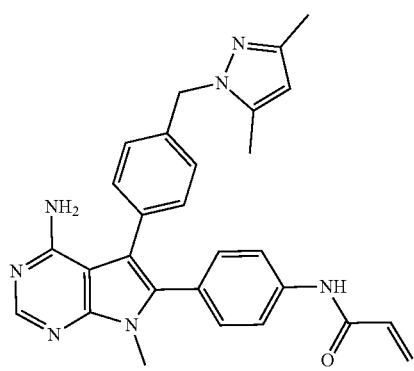 [SMILES: C=CC(=O)Nc1ccc(-c2c(-c3ccc(Cn4nc(C)cc4C)cc3)c3c(N)ncnc3n2C)cc1] | A | A |
| 261 | 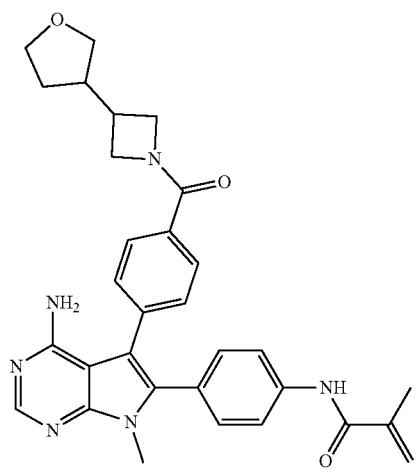 [SMILES: C=C(C)C(=O)Nc1ccc(-c2c(-c3ccc(C(=O)N4CC(C5CCOC5)C4)cc3)c3c(N)ncnc3n2C)cc1] | D | |
| 262 | 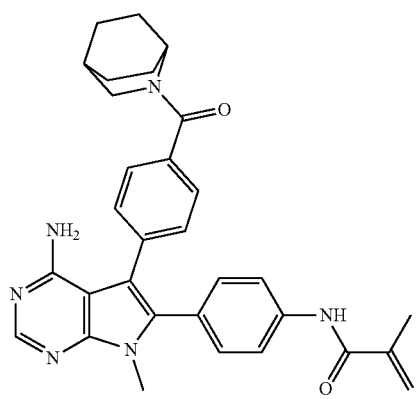 [SMILES: C=C(C)C(=O)Nc1ccc(-c2c(-c3ccc(C(=O)N4CC5CCC4CC5)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 263 | 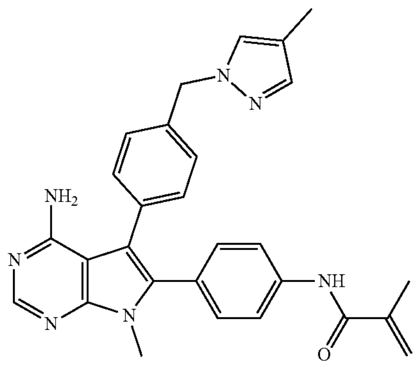 [SMILES: C=C(C)C(=O)Nc1ccc(-c2c(-c3ccc(Cn4cc(C)cn4)cc3)c3c(N)ncnc3n2C)cc1] | D | C |
| 264 | 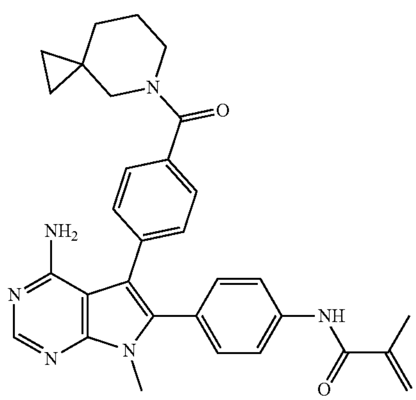 [SMILES: C=C(C)C(=O)Nc1ccc(-c2c(-c3ccc(C(=O)N4CCCC5(CC5)C4)cc3)c3c(N)ncnc3n2C)cc1] | B | A |
| 265 | 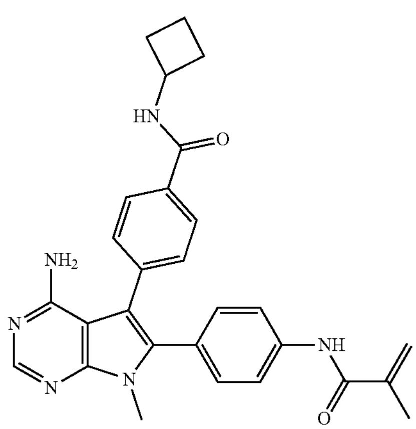 | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 266 | 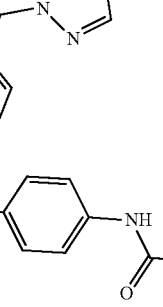 | D | C |
| 267 | 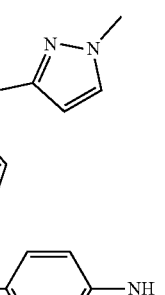 | A | A |
| 268 | 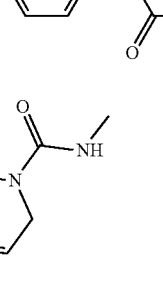 | D | |
| 269 | 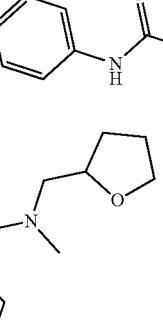 | D | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 270 | 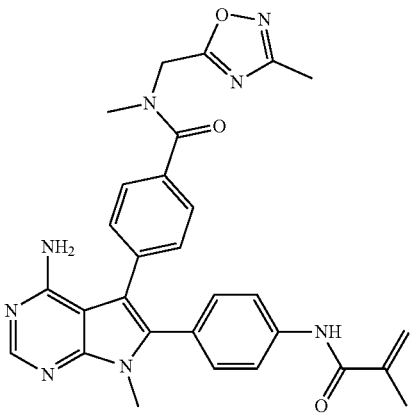 [SMILES: C=C(C)C(=O)Nc1ccc(-c2c(-c3ccc(C(=O)N(C)Cc4nc(C)no4)cc3)c3c(N)ncnc3n2C)cc1] | C | C |
| 271 | 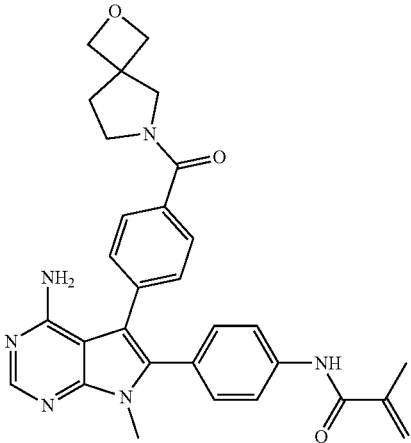 [SMILES: C=C(C)C(=O)Nc1ccc(-c2c(-c3ccc(C(=O)N4CCC5(COC5)C4)cc3)c3c(N)ncnc3n2C)cc1] | D | |
| 272 | 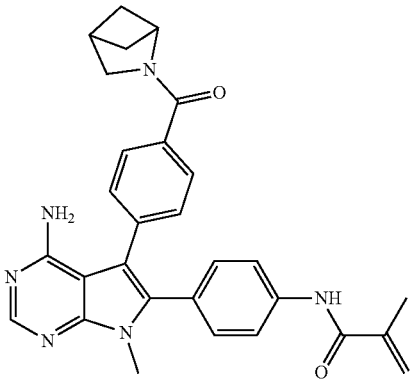 [SMILES: C=C(C)C(=O)Nc1ccc(-c2c(-c3ccc(C(=O)N4CC5CC4C5)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 273 | 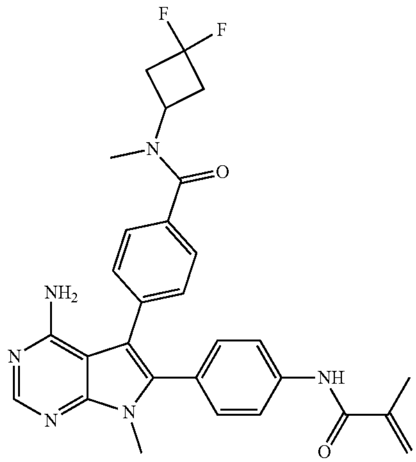 [SMILES: C=C(C)C(=O)Nc1ccc(-c2c(-c3ccc(C(=O)N(C)C4CC(F)(F)C4)cc3)c3c(N)ncnc3n2C)cc1] | C | |
| 274 | 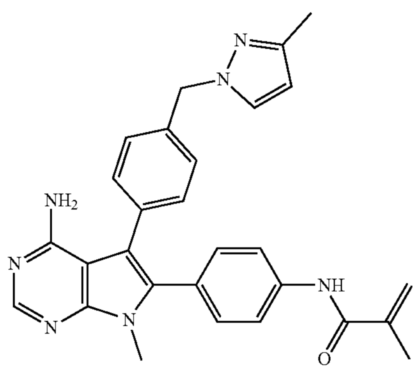 [SMILES: C=C(C)C(=O)Nc1ccc(-c2c(-c3ccc(Cn4ccc(C)n4)cc3)c3c(N)ncnc3n2C)cc1] | B | C |
| 275 | 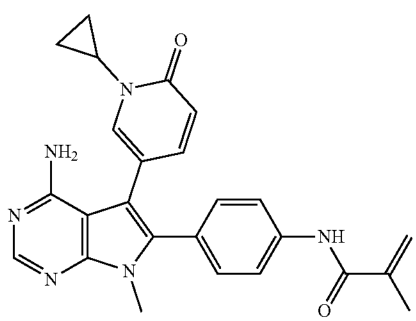 [SMILES: C=C(C)C(=O)Nc1ccc(-c2c(-c3ccc(=O)n(C4CC4)c3)c3c(N)ncnc3n2C)cc1] | D | |
| 276 | 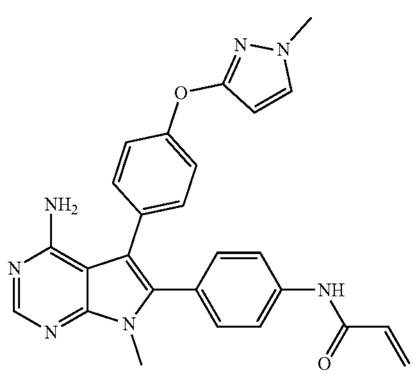 [SMILES: C=CC(=O)Nc1ccc(-c2c(-c3ccc(Oc4ccn(C)n4)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 277 | 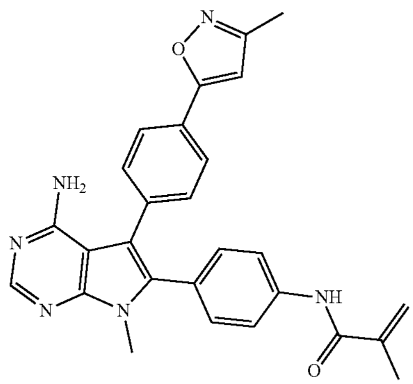 [SMILES: C=C(C)C(=O)Nc1ccc(-c2c(-c3ccc(-c4cc(C)no4)cc3)c3c(N)ncnc3n2C)cc1] | | C |
| 278 | 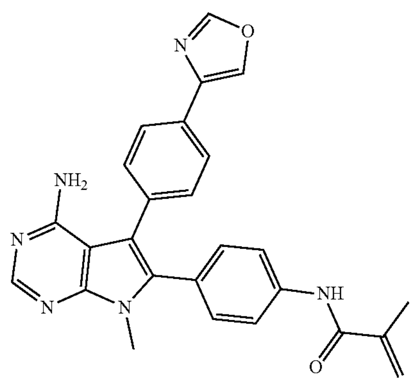 [SMILES: C=C(C)C(=O)Nc1ccc(-c2c(-c3ccc(-c4cocn4)cc3)c3c(N)ncnc3n2C)cc1] | | C |
| 279 | 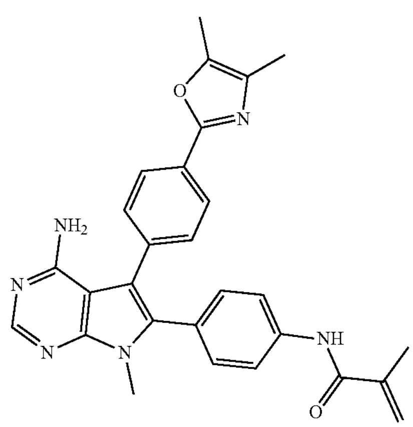 [SMILES: C=C(C)C(=O)Nc1ccc(-c2c(-c3ccc(-c4nc(C)c(C)o4)cc3)c3c(N)ncnc3n2C)cc1] | | B |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 280 | 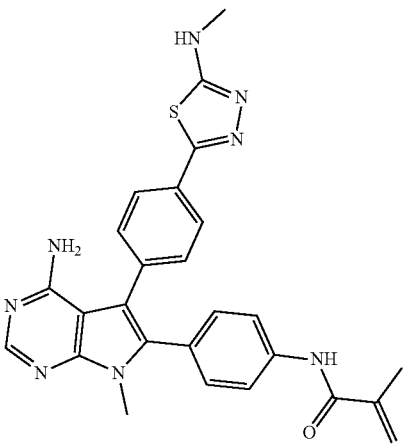 [SMILES: C=C(C)C(=O)Nc1ccc(-c2c(-c3ccc(-c4nnc(NC)s4)cc3)c3c(N)ncnc3n2C)cc1] | B | |
| 281 | 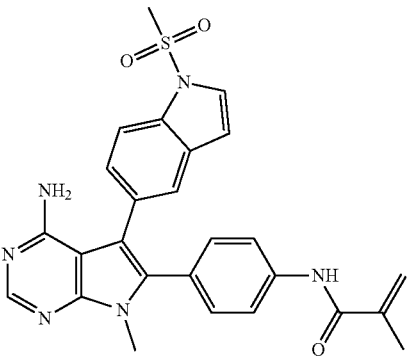 [SMILES: C=C(C)C(=O)Nc1ccc(-c2c(-c3ccc4c(ccn4S(C)(=O)=O)c3)c3c(N)ncnc3n2C)cc1] | D | |
| 282 | 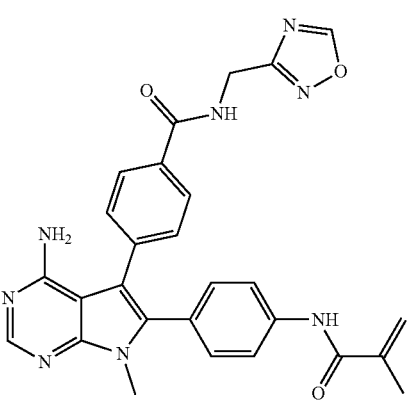 | B | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 283 | 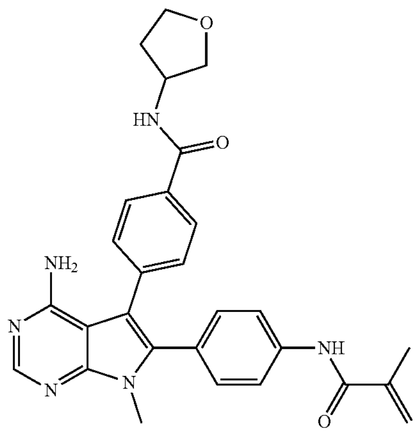 [SMILES: C=C(C)C(=O)Nc1ccc(-c2c(-c3ccc(C(=O)NC4CCOC4)cc3)c3c(N)ncnc3n2C)cc1] | A | A |
| 284 | 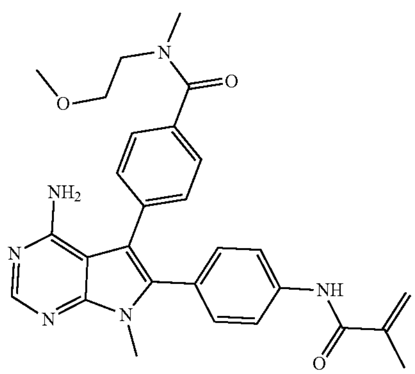 [SMILES: C=C(C)C(=O)Nc1ccc(-c2c(-c3ccc(C(=O)N(C)CCOC)cc3)c3c(N)ncnc3n2C)cc1] | | D |
| 285 | 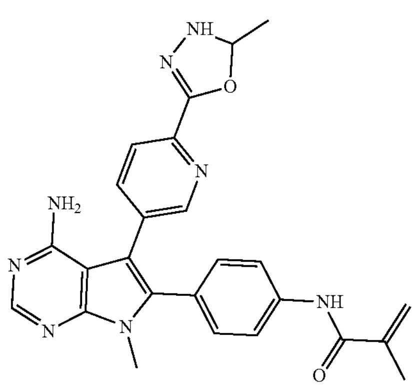 [SMILES: C=C(C)C(=O)Nc1ccc(-c2c(-c3ccc(C4=NNC(C)O4)nc3)c3c(N)ncnc3n2C)cc1] | | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 286 | 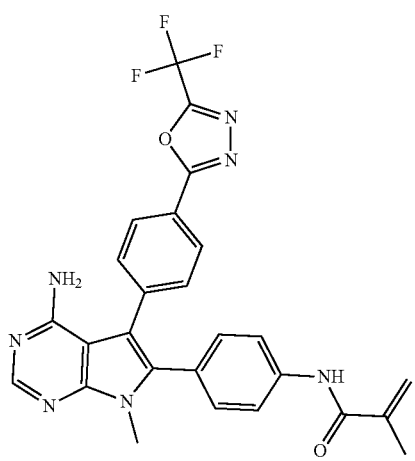 [SMILES: C=C(C)C(=O)Nc1ccc(-c2c(-c3ccc(-c4nnc(C(F)(F)F)o4)cc3)c3c(N)ncnc3n2C)cc1] | D | |
| 287 | 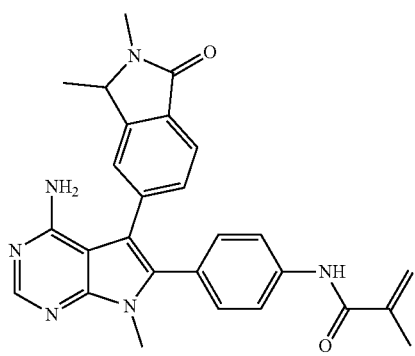 [SMILES: C=C(C)C(=O)Nc1ccc(-c2c(-c3ccc4c(c3)C(C)N(C)C4=O)c3c(N)ncnc3n2C)cc1] | D | |
| 288 | 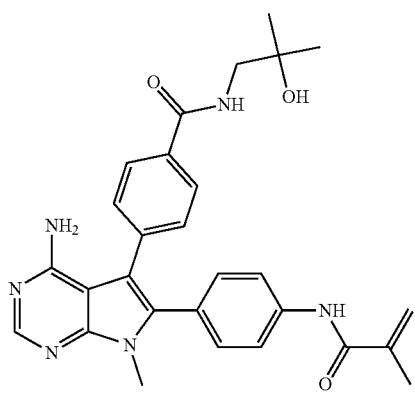 | A | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 289 | 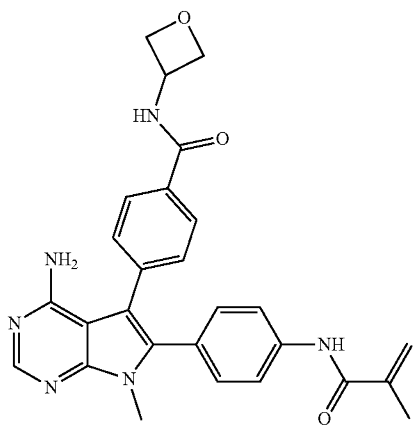 [SMILES: C=C(C)C(=O)Nc1ccc(-c2c(-c3ccc(C(=O)NC4COC4)cc3)c3c(N)ncnc3n2C)cc1] | C | C |
| 290 | 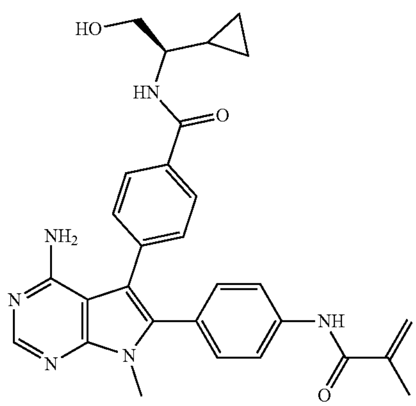 [SMILES: C=C(C)C(=O)Nc1ccc(-c2c(-c3ccc(C(=O)N[C@@H](CO)C4CC4)cc3)c3c(N)ncnc3n2C)cc1] | A | B |
| 291 | 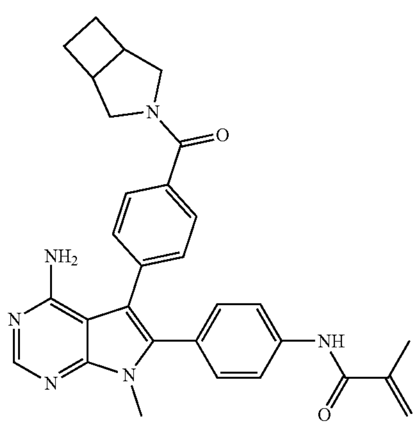 [SMILES: C=C(C)C(=O)Nc1ccc(-c2c(-c3ccc(C(=O)N4CC5CCC5C4)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 292 | 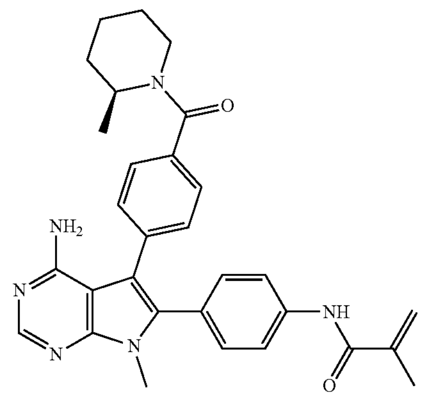 [SMILES: C=C(C)C(=O)Nc1ccc(-c2c(-c3ccc(C(=O)N4CCCC[C@@H]4C)cc3)c3c(N)ncnc3n2C)cc1] | A | A |
| 293 | 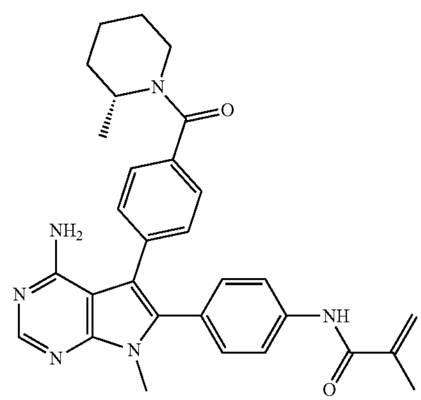 | A | A |
| 294 | 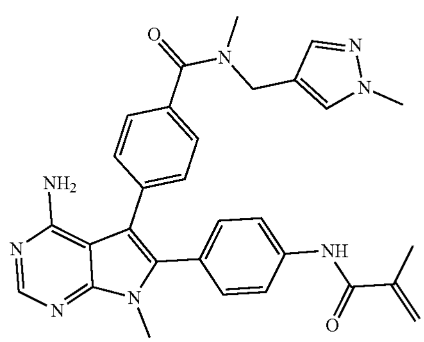 [SMILES: C=C(C)C(=O)Nc1ccc(-c2c(-c3ccc(C(=O)N(C)Cc4cnn(C)c4)cc3)c3c(N)ncnc3n2C)cc1] | D | C |
| 295 | 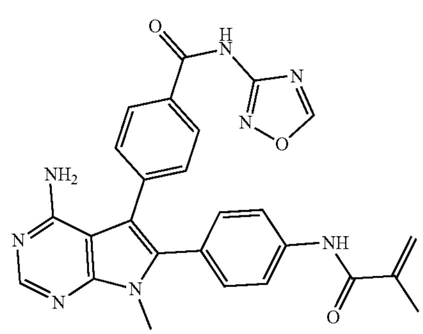 [SMILES: C=C(C)C(=O)Nc1ccc(-c2c(-c3ccc(C(=O)Nc4ncon4)cc3)c3c(N)ncnc3n2C)cc1] | D | C |

238
TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 296 | 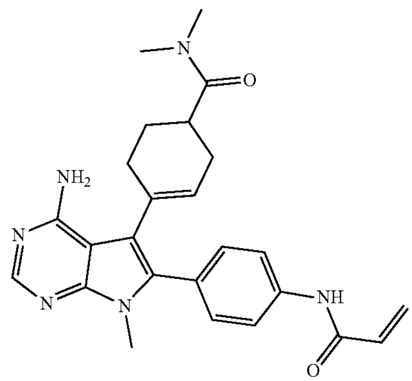 [SMILES: C=CC(=O)Nc1ccc(-c2c(C3=CCC(C(=O)N(C)C)CC3)c3c(N)ncnc3n2C)cc1] | A | A |
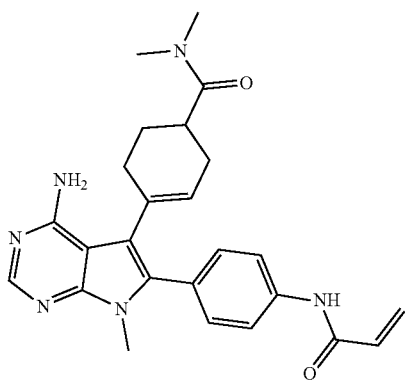
| 297 |  | A | A |
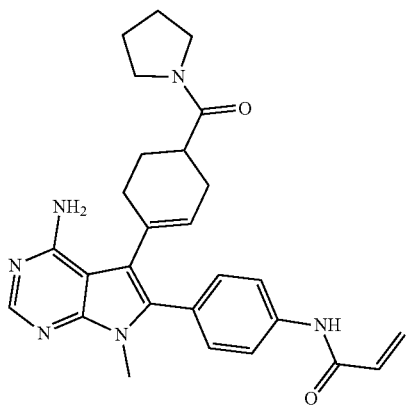 [SMILES: C=CC(=O)Nc1ccc(-c2c(C3=CCC(C(=O)N4CCCC4)CC3)c3c(N)ncnc3n2C)cc1]
| 298 |  | A | A |
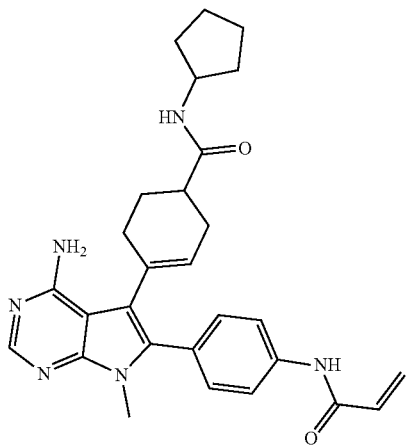 [SMILES: C=CC(=O)Nc1ccc(-c2c(C3=CCC(C(=O)NC4CCCC4)CC3)c3c(N)ncnc3n2C)cc1]

TABLE 1-continued

Representative Compounds of the Invention with Bioactivity Data.

| Example | Structure | Biochemical FGFR2 Caliper IC50 | Cell SNU-16 IC50 |
|---|---|---|---|
| 299 | 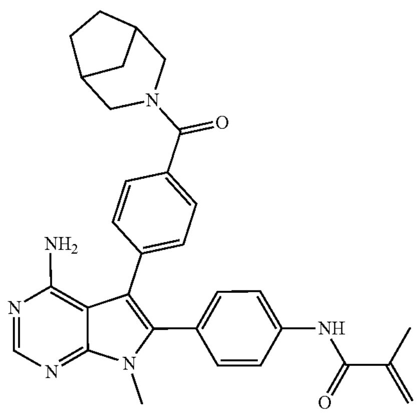 [SMILES: C=C(C)C(=O)Nc1ccc(-c2c(-c3ccc(C(=O)N4CC5CCC(C5)C4)cc3)c3c(N)ncnc3n2C)cc1] | A | A |
| 300 | 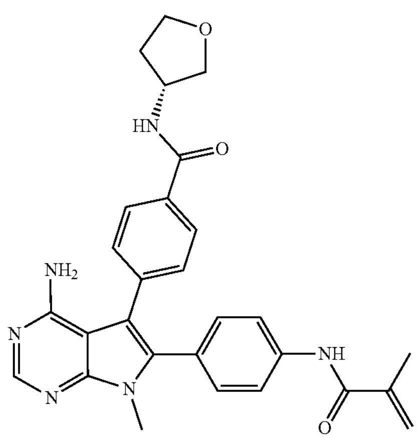 [SMILES: C=C(C)C(=O)Nc1ccc(-c2c(-c3ccc(C(=O)N[C@@H]4CCOC4)cc3)c3c(N)ncnc3n2C)cc1] | A | A |
| 301 | 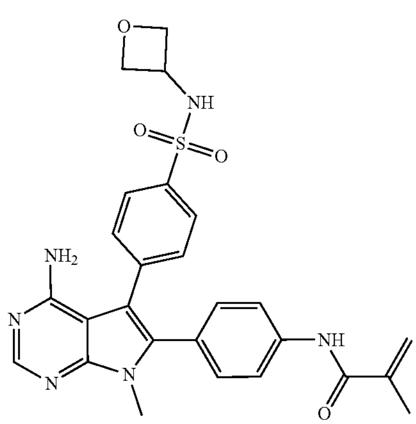 [SMILES: C=C(C)C(=O)Nc1ccc(-c2c(-c3ccc(S(=O)(=O)NC4COC4)cc3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 302 | 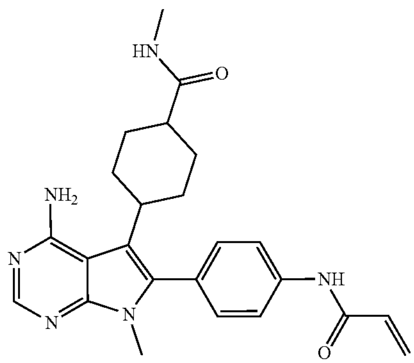 [SMILES: C=CC(=O)Nc1ccc(-c2c(C3CCC(C(=O)NC)CC3)c3c(N)ncnc3n2C)cc1] | D | C |
| 303 | 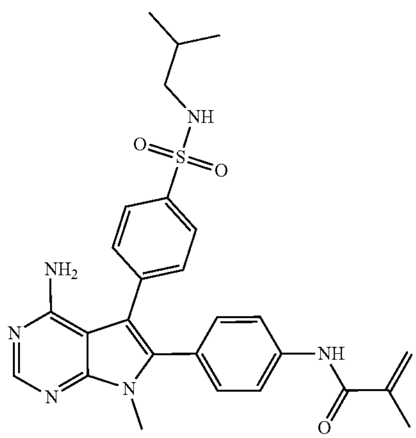 [SMILES: C=C(C)C(=O)Nc1ccc(-c2c(-c3ccc(S(=O)(=O)NCC(C)C)cc3)c3c(N)ncnc3n2C)cc1] | C | C |
| 304 | 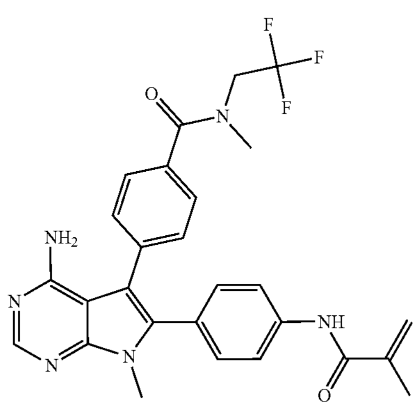 [SMILES: C=C(C)C(=O)Nc1ccc(-c2c(-c3ccc(C(=O)N(C)CC(F)(F)F)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 305 | 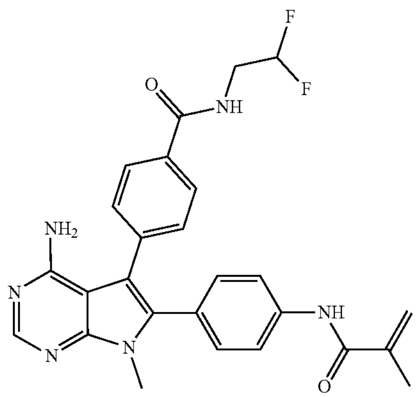 [SMILES: C=C(C)C(=O)Nc1ccc(-c2c(-c3ccc(C(=O)NCC(F)F)cc3)c3c(N)ncnc3n2C)cc1] | A | A |
| 306 | 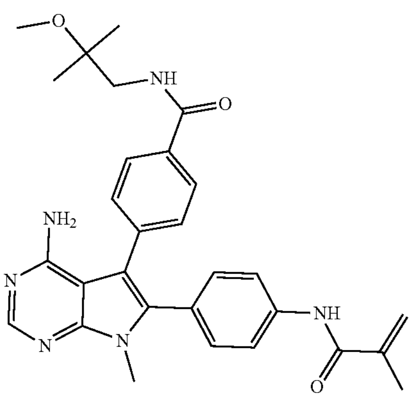 [SMILES: C=C(C)C(=O)Nc1ccc(-c2c(-c3ccc(C(=O)NCC(C)(C)OC)cc3)c3c(N)ncnc3n2C)cc1] | A | A |
| 307 | 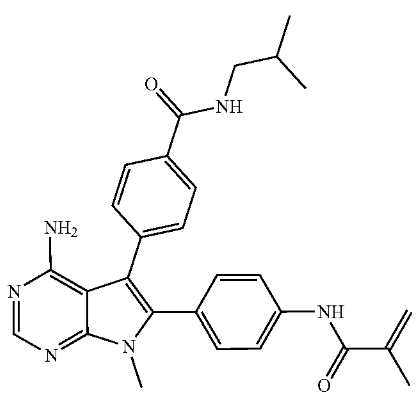 [SMILES: C=C(C)C(=O)Nc1ccc(-c2c(-c3ccc(C(=O)NCC(C)C)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 308 | 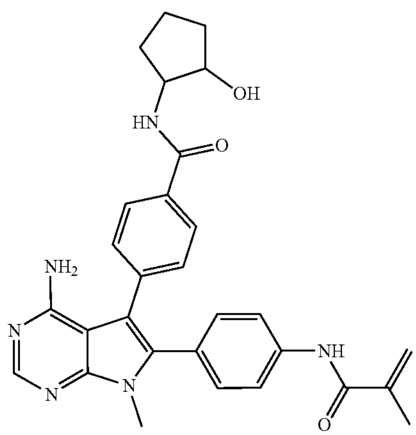 [SMILES: C=C(C)C(=O)Nc1ccc(-c2c(-c3ccc(C(=O)NC4CCCC4O)cc3)c3c(N)ncnc3n2C)cc1] | A | B |
| 309 | 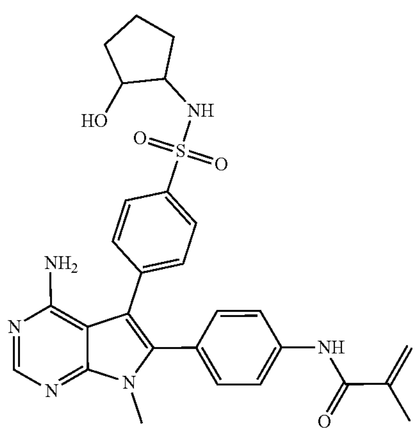 [SMILES: C=C(C)C(=O)Nc1ccc(-c2c(-c3ccc(S(=O)(=O)NC4CCCC4O)cc3)c3c(N)ncnc3n2C)cc1] | D | C |
| 310 | 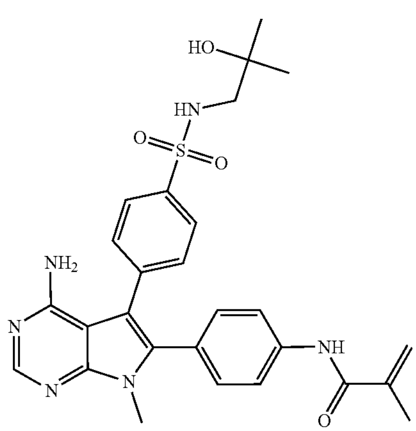 [SMILES: C=C(C)C(=O)Nc1ccc(-c2c(-c3ccc(S(=O)(=O)NCC(C)(C)O)cc3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 311 | 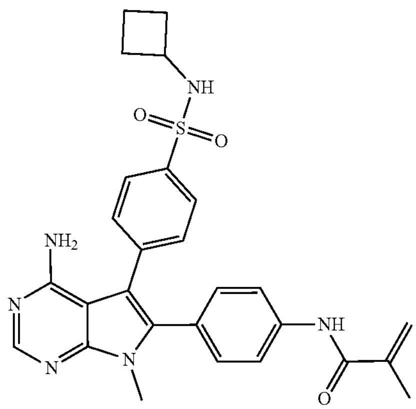 [SMILES: C=C(C)C(=O)Nc1ccc(-c2c(-c3ccc(S(=O)(=O)NC4CCC4)cc3)c3c(N)ncnc3n2C)cc1] | C | C |
| 312 | 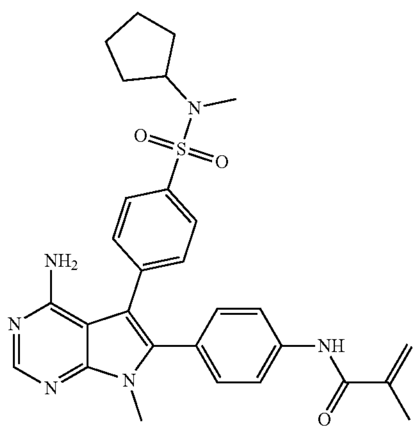 [SMILES: C=C(C)C(=O)Nc1ccc(-c2c(-c3ccc(S(=O)(=O)N(C)C4CCCC4)cc3)c3c(N)ncnc3n2C)cc1] | C | C |
| 313 | 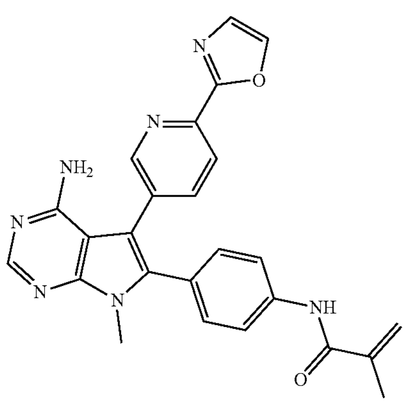 [SMILES: C=C(C)C(=O)Nc1ccc(-c2c(-c3ccc(-c4ncco4)nc3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 314 | 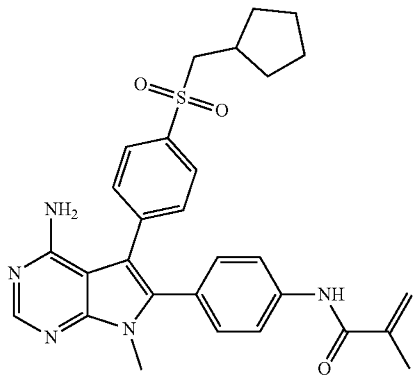 [SMILES: C=C(C)C(=O)Nc1ccc(-c2c(-c3ccc(S(=O)(=O)CC4CCCC4)cc3)c3c(N)ncnc3n2C)cc1] | C | C |
| 315 | 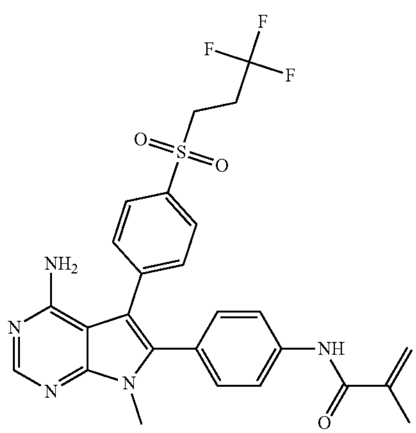 [SMILES: C=C(C)C(=O)Nc1ccc(-c2c(-c3ccc(S(=O)(=O)CCC(F)(F)F)cc3)c3c(N)ncnc3n2C)cc1] | C | C |
| 316 | 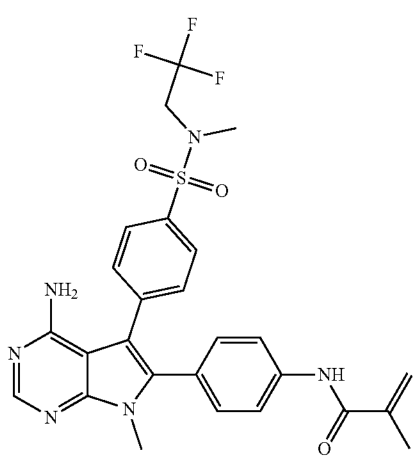 [SMILES: C=C(C)C(=O)Nc1ccc(-c2c(-c3ccc(S(=O)(=O)N(C)CC(F)(F)F)cc3)c3c(N)ncnc3n2C)cc1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 317 | 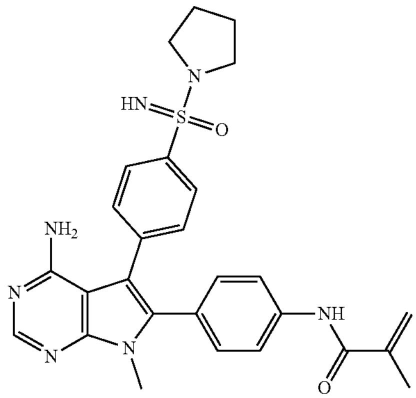 [SMILES: C=C(C)C(=O)Nc1ccc(-c2c(-c3ccc(S(=N)(=O)N4CCCC4)cc3)c3c(N)ncnc3n2C)cc1] | C | |
| 318 | 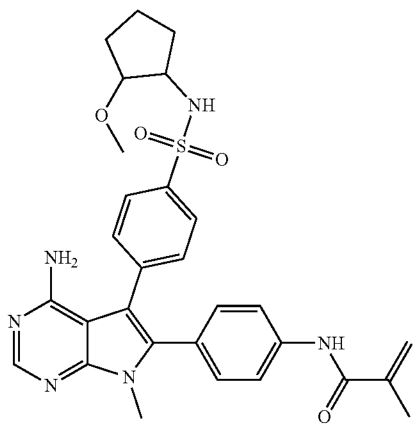 [SMILES: C=C(C)C(=O)Nc1ccc(-c2c(-c3ccc(S(=O)(=O)NC4CCCC4OC)cc3)c3c(N)ncnc3n2C)cc1] | D | C |
| 319 | 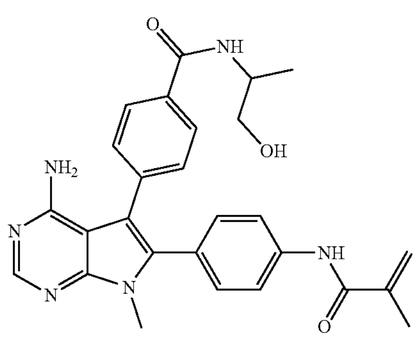 [SMILES: C=C(C)C(=O)Nc1ccc(-c2c(-c3ccc(C(=O)NC(C)CO)cc3)c3c(N)ncnc3n2C)cc1] | A | |
| 320 | 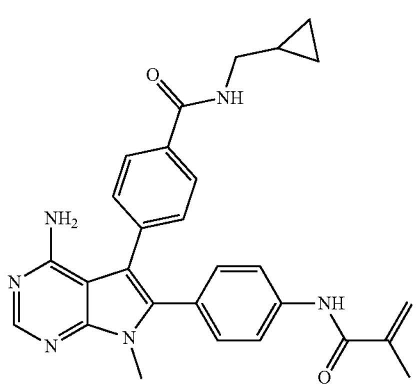 [SMILES: C=C(C)C(=O)Nc1ccc(-c2c(-c3ccc(C(=O)NCC4CC4)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 321 | 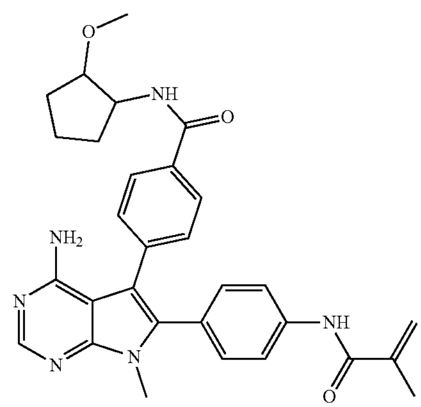 [SMILES: C=C(C)C(=O)Nc1ccc(-c2c(-c3ccc(C(=O)NC4CCCC4OC)cc3)c3c(N)ncnc3n2C)cc1] | B | B |
| 322 | 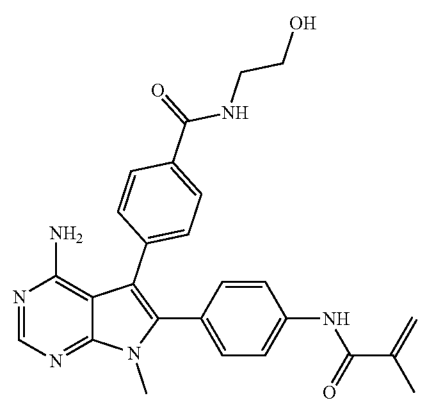 [SMILES: C=C(C)C(=O)Nc1ccc(-c2c(-c3ccc(C(=O)NCCO)cc3)c3c(N)ncnc3n2C)cc1] | C | |
| 323 | 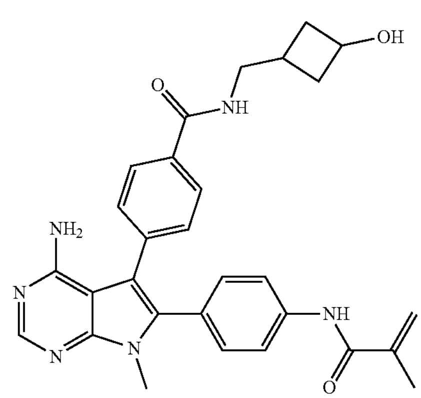 [SMILES: C=C(C)C(=O)Nc1ccc(-c2c(-c3ccc(C(=O)NCC4CC(O)C4)cc3)c3c(N)ncnc3n2C)cc1] | B | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 324 | 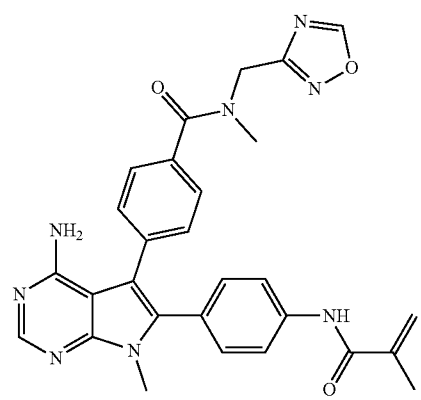 [SMILES: C=C(C)C(=O)Nc1ccc(-c2c(-c3ccc(C(=O)N(C)Cc4ncon4)cc3)c3c(N)ncnc3n2C)cc1] | D | C |
| 325 | 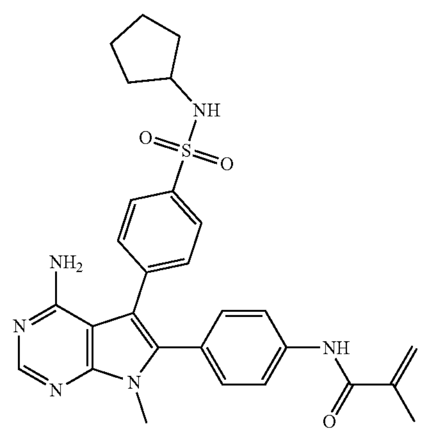 [SMILES: C=C(C)C(=O)Nc1ccc(-c2c(-c3ccc(S(=O)(=O)NC4CCCC4)cc3)c3c(N)ncnc3n2C)cc1] | D | |
| 326 | 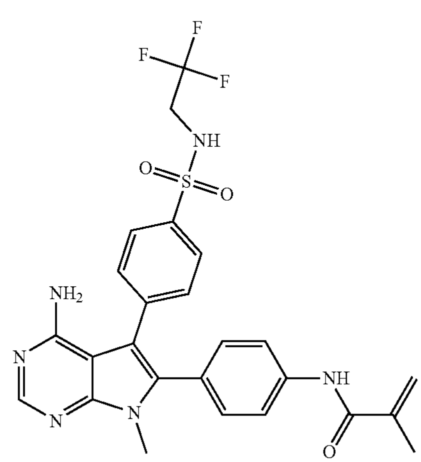 [SMILES: C=C(C)C(=O)Nc1ccc(-c2c(-c3ccc(S(=O)(=O)NCC(F)(F)F)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 327 | 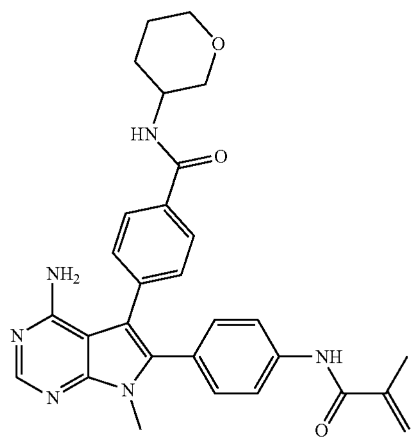 [SMILES: C=C(C)C(=O)Nc1ccc(-c2c(-c3ccc(C(=O)NC4CCCOC4)cc3)c3c(N)ncnc3n2C)cc1] | A | B |
| 328 | 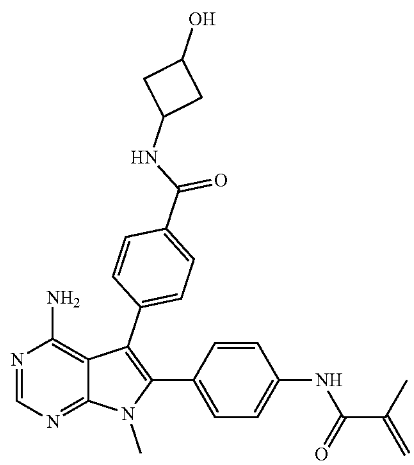 [SMILES: C=C(C)C(=O)Nc1ccc(-c2c(-c3ccc(C(=O)NC4CC(O)C4)cc3)c3c(N)ncnc3n2C)cc1] | C | |
| 329 | 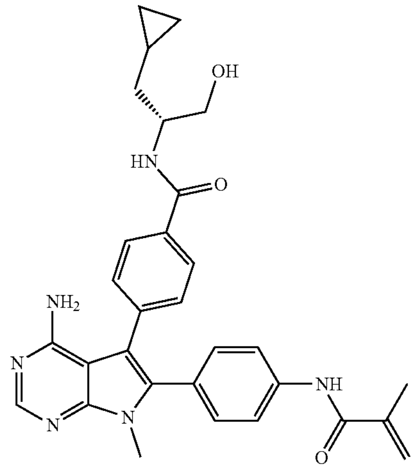 [SMILES: C=C(C)C(=O)Nc1ccc(-c2c(-c3ccc(C(=O)N[C@@H](CO)CC4CC4)cc3)c3c(N)ncnc3n2C)cc1] | A | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 330 | 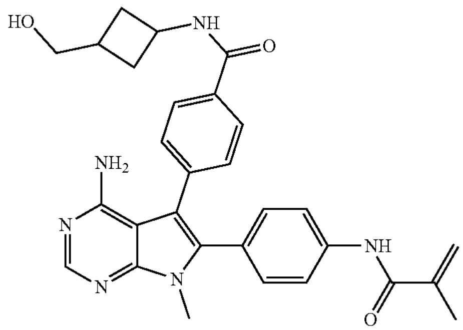 [SMILES: C=C(C)C(=O)Nc1ccc(-c2c(-c3ccc(C(=O)NC4CC(CO)C4)cc3)c3c(N)ncnc3n2C)cc1] | B | |
| 331 | 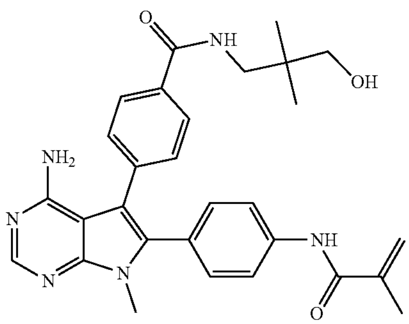 [SMILES: C=C(C)C(=O)Nc1ccc(-c2c(-c3ccc(C(=O)NCC(C)(C)CO)cc3)c3c(N)ncnc3n2C)cc1] | A | A |
| 332 | 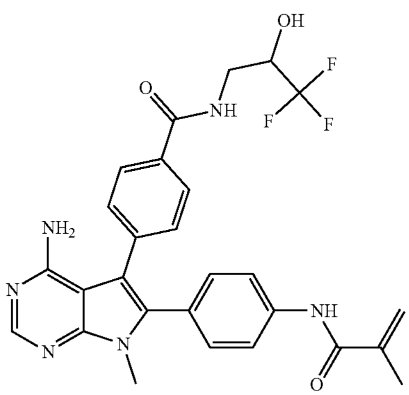 [SMILES: C=C(C)C(=O)Nc1ccc(-c2c(-c3ccc(C(=O)NCC(O)C(F)(F)F)cc3)c3c(N)ncnc3n2C)cc1] | A | C |
| 333 | 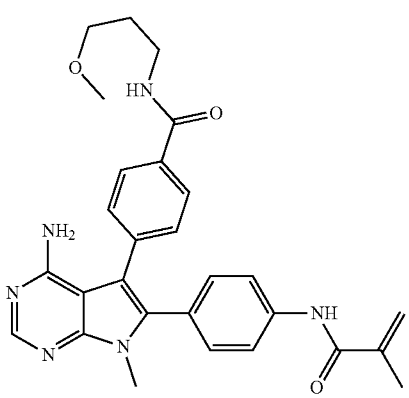 [SMILES: C=C(C)C(=O)Nc1ccc(-c2c(-c3ccc(C(=O)NCCCOC)cc3)c3c(N)ncnc3n2C)cc1] | B | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 334 | 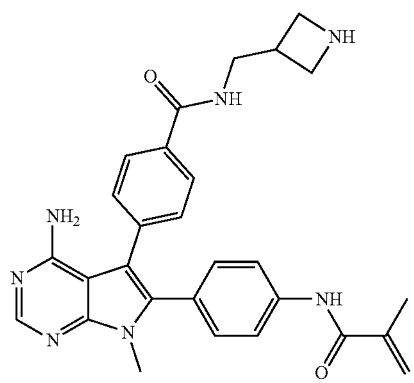 [SMILES: C=C(C)C(=O)Nc1ccc(-c2c(-c3ccc(C(=O)NCC4CNC4)cc3)c3c(N)ncnc3n2C)cc1] | C | |
| 335 | 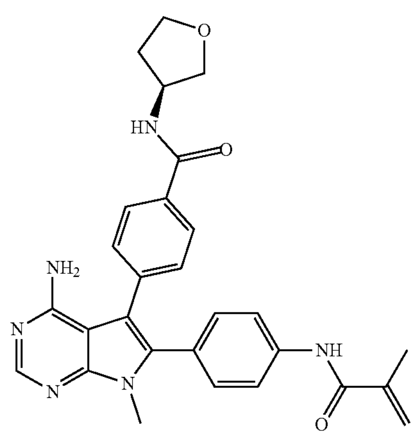 | C | C |
| 336 | 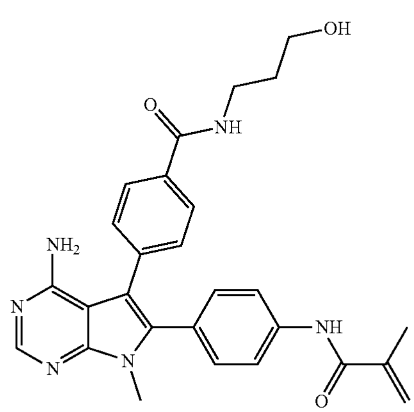 [SMILES: C=C(C)C(=O)Nc1ccc(-c2c(-c3ccc(C(=O)NCCCO)cc3)c3c(N)ncnc3n2C)cc1] | B | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 337 | 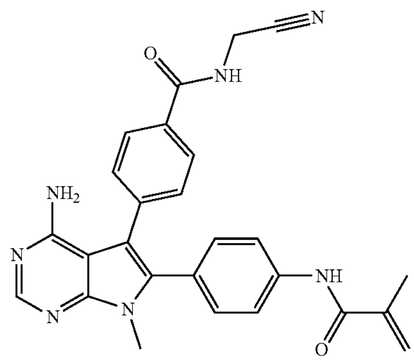 [SMILES: C=C(C)C(=O)Nc1ccc(-c2c(-c3ccc(C(=O)NCC#N)cc3)c3c(N)ncnc3n2C)cc1] | C | C |
| 338 | 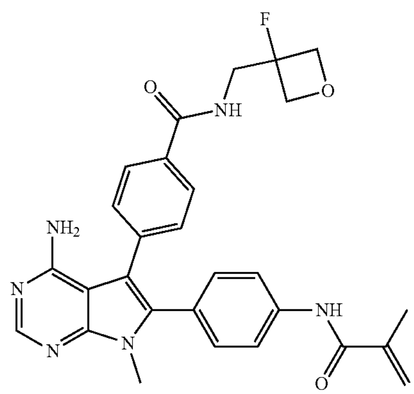 [SMILES: C=C(C)C(=O)Nc1ccc(-c2c(-c3ccc(C(=O)NCC4(F)COC4)cc3)c3c(N)ncnc3n2C)cc1] | A | A |
| 339 | 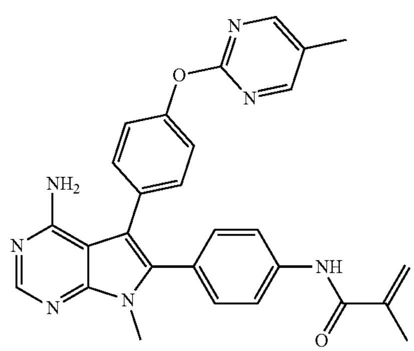 [SMILES: C=C(C)C(=O)Nc1ccc(-c2c(-c3ccc(Oc4ncc(C)cn4)cc3)c3c(N)ncnc3n2C)cc1] | B | A |
| 340 | 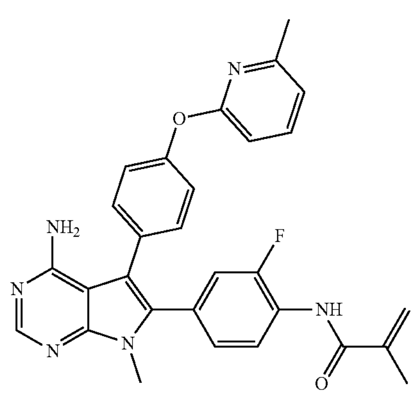 [SMILES: C=C(C)C(=O)Nc1ccc(-c2c(-c3ccc(Oc4cccc(C)n4)cc3)c3c(N)ncnc3n2C)cc1F] | A | A |

265
266
TABLE 1-continued
Representative Compounds of the Invention with Bioactivity Data.
| Example | Structure | Biochemical FGFR2 Caliper IC50 | Cell SNU-16 IC50 |
|---|---|---|---|
| 341 | 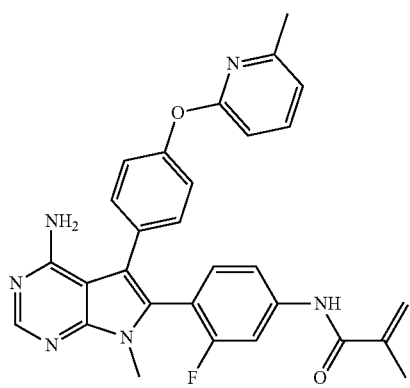 [SMILES: C=C(C)C(=O)Nc1ccc(-c2c(-c3ccc(Oc4cccc(C)n4)cc3)c3c(N)ncnc3n2C)c(F)c1] | A | A |
| 342 | 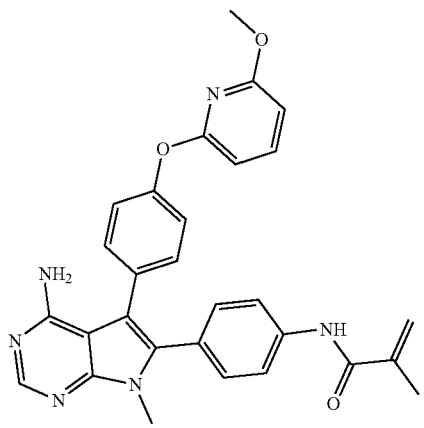 [SMILES: C=C(C)C(=O)Nc1ccc(-c2c(-c3ccc(Oc4cccc(OC)n4)cc3)c3c(N)ncnc3n2C)cc1] | A | A |
| 343 | 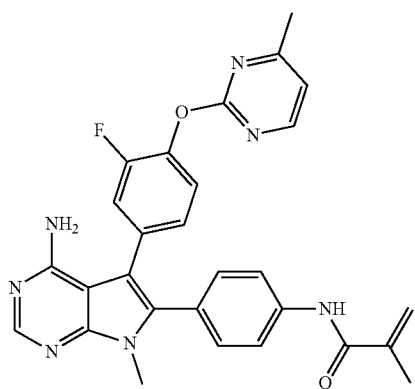 [SMILES: C=C(C)C(=O)Nc1ccc(-c2c(-c3ccc(Oc4nccc(C)n4)c(F)c3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 344 | 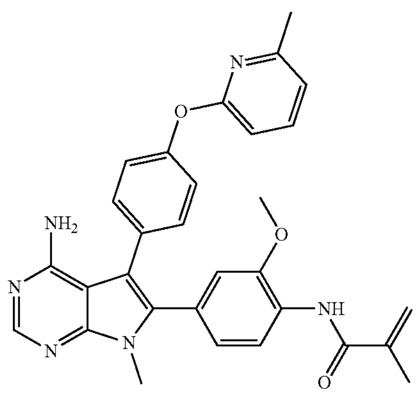 [SMILES: C=C(C)C(=O)Nc1ccc(-c2c(-c3ccc(Oc4cccc(C)n4)cc3)c3c(N)ncnc3n2C)cc1OC] | B | A |
| 345 | 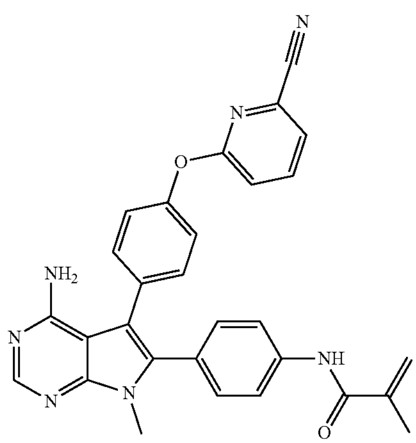 [SMILES: C=C(C)C(=O)Nc1ccc(-c2c(-c3ccc(Oc4cccc(C#N)n4)cc3)c3c(N)ncnc3n2C)cc1] | A | |
| 346 | 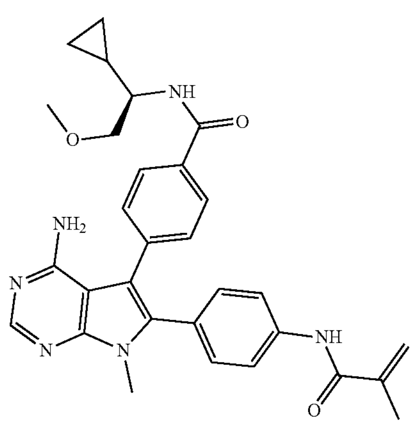 [SMILES: C=C(C)C(=O)Nc1ccc(-c2c(-c3ccc(C(=O)N[C@@H](COC)C4CC4)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 347 | 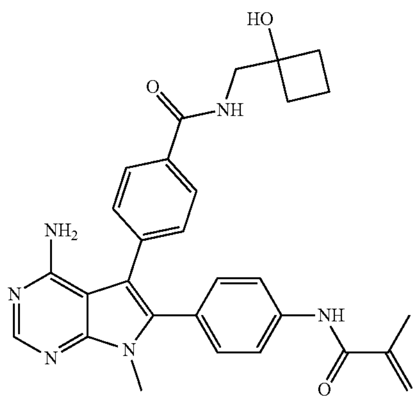 [SMILES: C=C(C)C(=O)Nc1ccc(-c2c(-c3ccc(C(=O)NCC4(O)CCC4)cc3)c3c(N)ncnc3n2C)cc1] | A | |
| 348 | 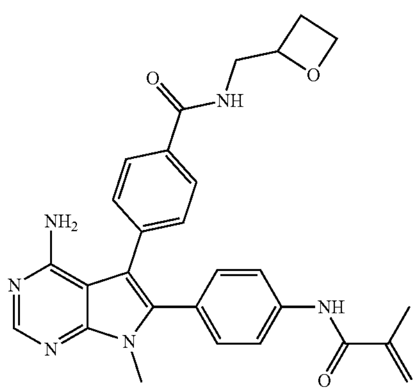 [SMILES: C=C(C)C(=O)Nc1ccc(-c2c(-c3ccc(C(=O)NCC4CCO4)cc3)c3c(N)ncnc3n2C)cc1] | A | C |
| 349 | 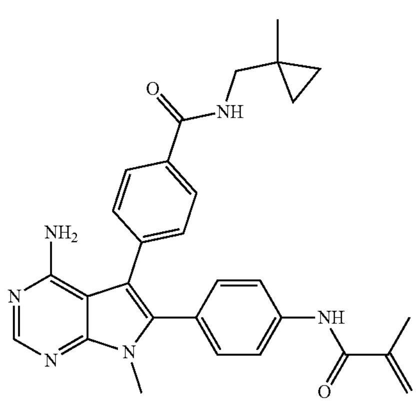 [SMILES: C=C(C)C(=O)Nc1ccc(-c2c(-c3ccc(C(=O)NCC4(C)CC4)cc3)c3c(N)ncnc3n2C)cc1] | A | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 350 | 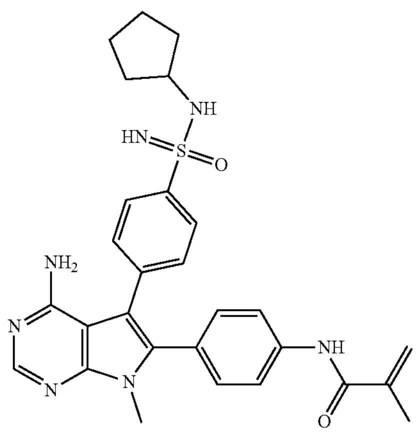 [SMILES: C=C(C)C(=O)Nc1ccc(-c2c(-c3ccc(S(=N)(=O)NC4CCCC4)cc3)c3c(N)ncnc3n2C)cc1] | D | |
| 351 | 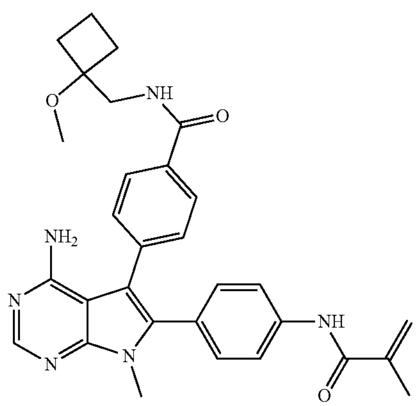 [SMILES: C=C(C)C(=O)Nc1ccc(-c2c(-c3ccc(C(=O)NCC4(OC)CCC4)cc3)c3c(N)ncnc3n2C)cc1] | A | A |
| 352 | 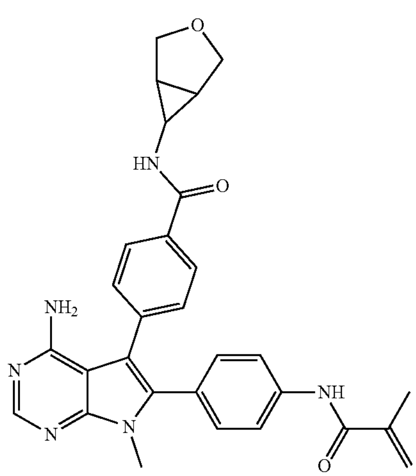 [SMILES: C=C(C)C(=O)Nc1ccc(-c2c(-c3ccc(C(=O)NC4C5COCC54)cc3)c3c(N)ncnc3n2C)cc1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 353 | 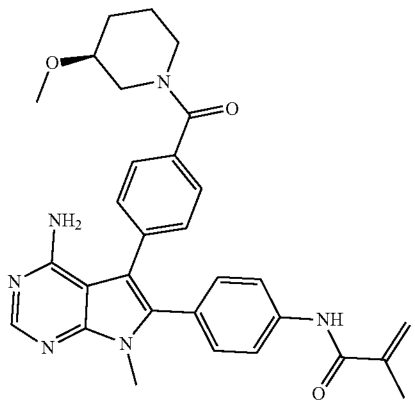 [SMILES: C=C(C)C(=O)Nc1ccc(-c2c(-c3ccc(C(=O)N4CCC[C@H](OC)C4)cc3)c3c(N)ncnc3n2C)cc1] | D | C |
| 354 | 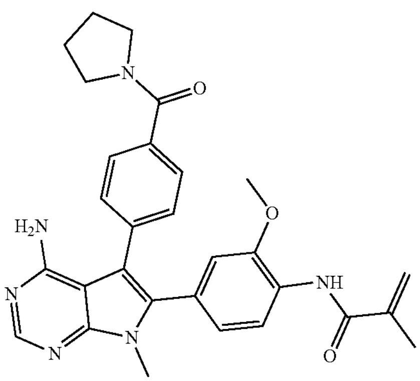 [SMILES: C=C(C)C(=O)Nc1ccc(-c2c(-c3ccc(C(=O)N4CCCC4)cc3)c3c(N)ncnc3n2C)cc1OC] | D | C |
| 355 | 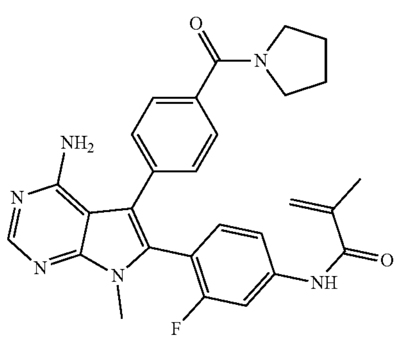 [SMILES: C=C(C)C(=O)Nc1ccc(-c2c(-c3ccc(C(=O)N4CCCC4)cc3)c3c(N)ncnc3n2C)c(F)c1] | A | A |
| 356 | 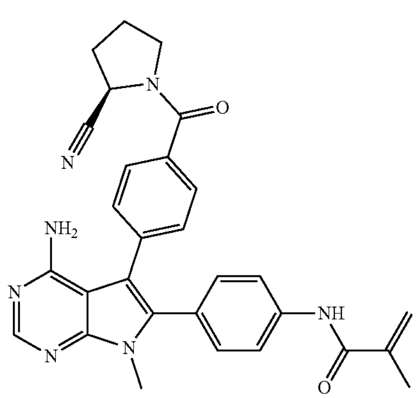 [SMILES: C=C(C)C(=O)Nc1ccc(-c2c(-c3ccc(C(=O)N4CCC[C@@H]4C#N)cc3)c3c(N)ncnc3n2C)cc1] | B | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 357 | 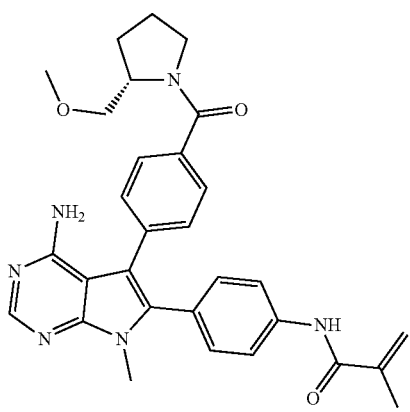 [SMILES: C=C(C)C(=O)Nc1ccc(-c2c(-c3ccc(C(=O)N4CCC[C@H]4COC)cc3)c3c(N)ncnc3n2C)cc1] | A | A |
| 358 | 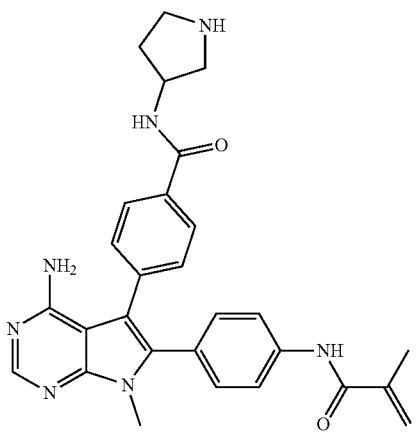 [SMILES: C=C(C)C(=O)Nc1ccc(-c2c(-c3ccc(C(=O)NC4CCNC4)cc3)c3c(N)ncnc3n2C)cc1] | A | |
| 359 | 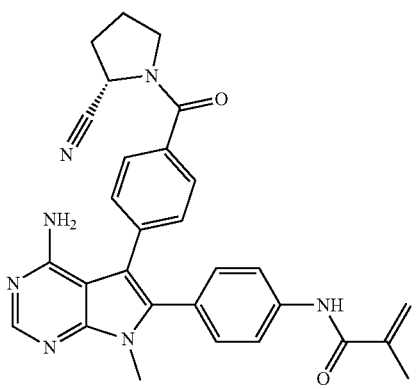 [SMILES: C=C(C)C(=O)Nc1ccc(-c2c(-c3ccc(C(=O)N4CCC[C@H]4C#N)cc3)c3c(N)ncnc3n2C)cc1] | A | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 360 | 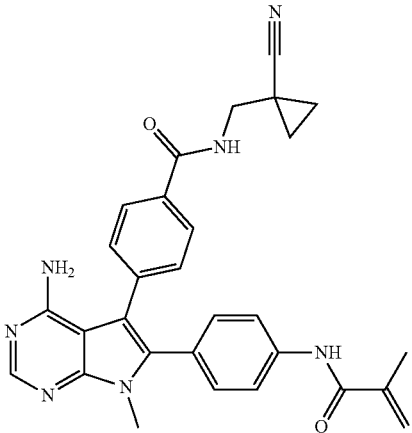 [SMILES: C=C(C)C(=O)Nc1ccc(-c2c(-c3ccc(C(=O)NCC4(C#N)CC4)cc3)c3c(N)ncnc3n2C)cc1] | A | |
| 361 | 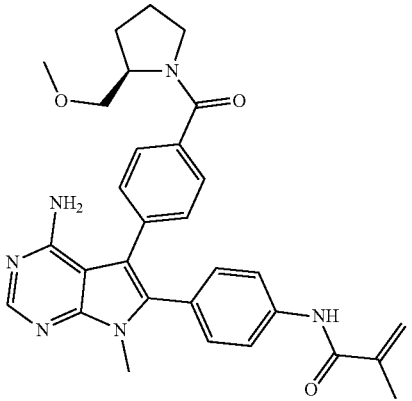 [SMILES: C=C(C)C(=O)Nc1ccc(-c2c(-c3ccc(C(=O)N4CCC[C@@H]4COC)cc3)c3c(N)ncnc3n2C)cc1] | C | C |
| 362 | 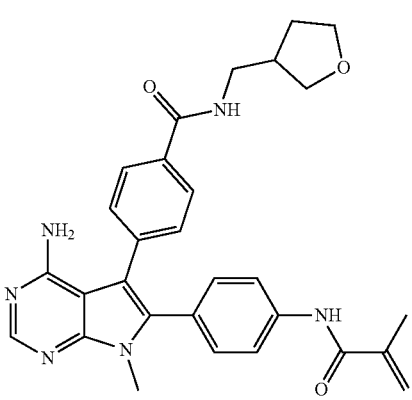 [SMILES: C=C(C)C(=O)Nc1ccc(-c2c(-c3ccc(C(=O)NCC4CCOC4)cc3)c3c(N)ncnc3n2C)cc1] | A | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 363 | 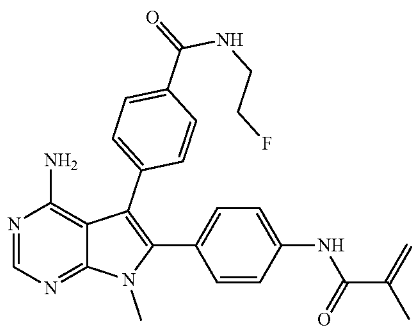 [SMILES: C=C(C)C(=O)Nc1ccc(-c2c(-c3ccc(C(=O)NCCF)cc3)c3c(N)ncnc3n2C)cc1] | A | |
| 364 | 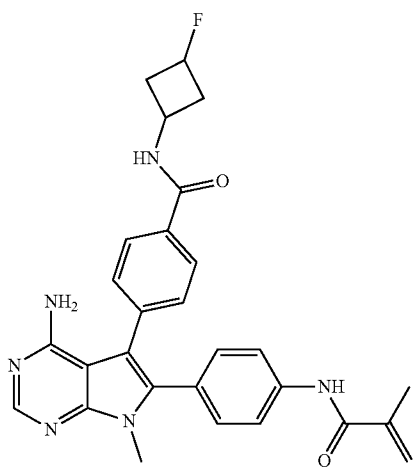 [SMILES: C=C(C)C(=O)Nc1ccc(-c2c(-c3ccc(C(=O)NC4CC(F)C4)cc3)c3c(N)ncnc3n2C)cc1] | A | |
| 365 | 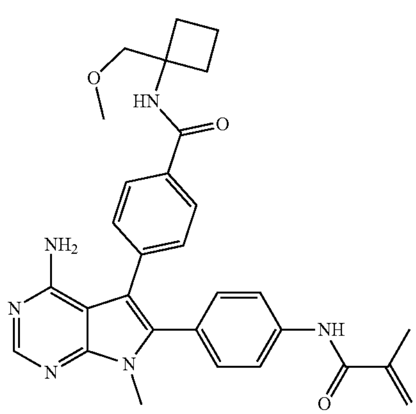 [SMILES: C=C(C)C(=O)Nc1ccc(-c2c(-c3ccc(C(=O)NC4(COC)CCC4)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 366 | 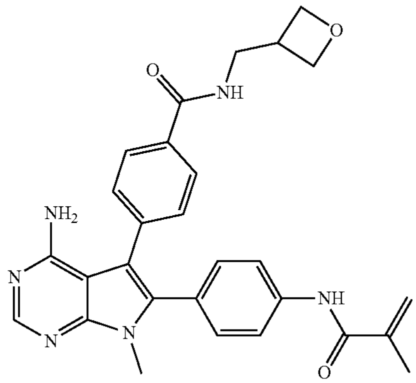 [SMILES: C=C(C)C(=O)Nc1ccc(-c2c(-c3ccc(C(=O)NCC4COC4)cc3)c3c(N)ncnc3n2C)cc1] | B | |
| 367 | 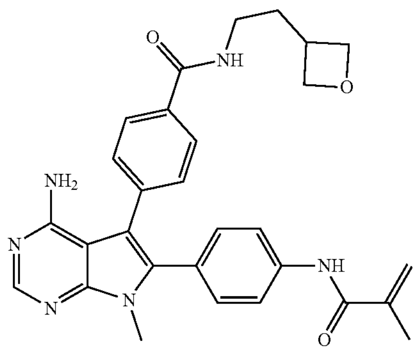 [SMILES: C=C(C)C(=O)Nc1ccc(-c2c(-c3ccc(C(=O)NCCC4COC4)cc3)c3c(N)ncnc3n2C)cc1] | C | |
| 368 | 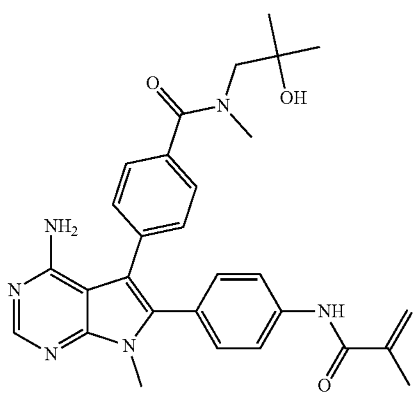 [SMILES: C=C(C)C(=O)Nc1ccc(-c2c(-c3ccc(C(=O)N(C)CC(C)(C)O)cc3)c3c(N)ncnc3n2C)cc1] | C | C |
| 369 | 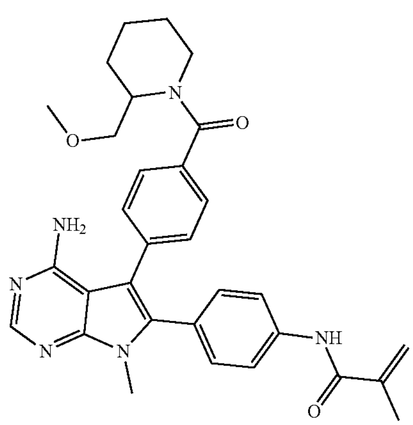 [SMILES: C=C(C)C(=O)Nc1ccc(-c2c(-c3ccc(C(=O)N4CCCCC4COC)cc3)c3c(N)ncnc3n2C)cc1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 370 | 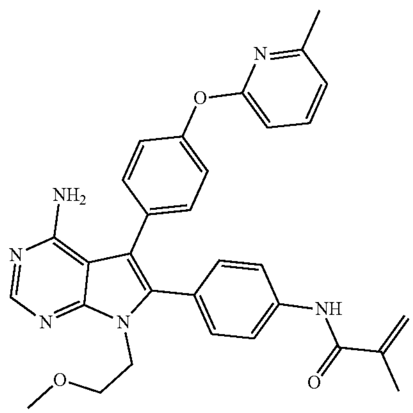 [SMILES: C=C(C)C(=O)Nc1ccc(-c2c(-c3ccc(Oc4cccc(C)n4)cc3)c3c(N)ncnc3n2CCOC)cc1] | A | A |
| 371 | 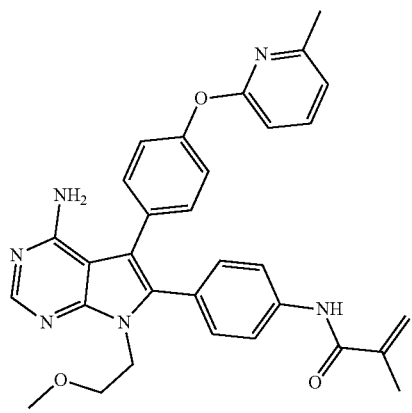 | A | A |
| 372 | 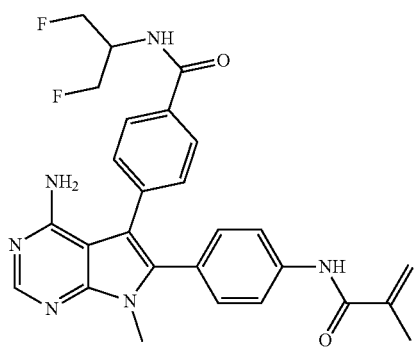 [SMILES: C=C(C)C(=O)Nc1ccc(-c2c(-c3ccc(C(=O)NC(CF)CF)cc3)c3c(N)ncnc3n2C)cc1] | A | C |
| | 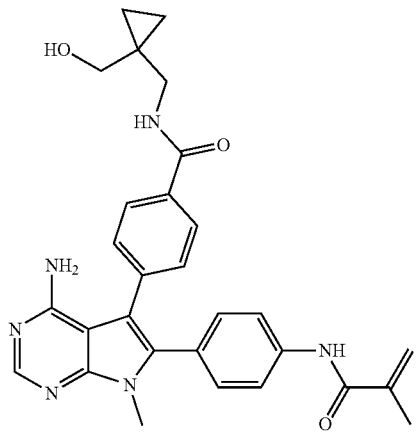 [SMILES: C=C(C)C(=O)Nc1ccc(-c2c(-c3ccc(C(=O)NCC4(CO)CC4)cc3)c3c(N)ncnc3n2C)cc1] | | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 373 | 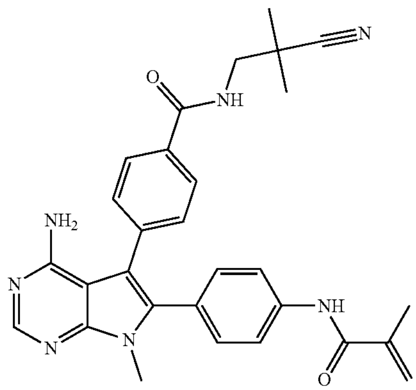 [SMILES: C=C(C)C(=O)Nc1ccc(-c2c(-c3ccc(C(=O)NCC(C)(C)C#N)cc3)c3c(N)ncnc3n2C)cc1] | A | A |
| 374 | 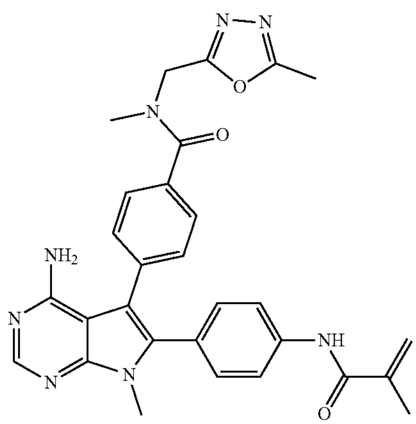 [SMILES: C=C(C)C(=O)Nc1ccc(-c2c(-c3ccc(C(=O)N(C)Cc4nnc(C)o4)cc3)c3c(N)ncnc3n2C)cc1] | D | C |
| 375 | 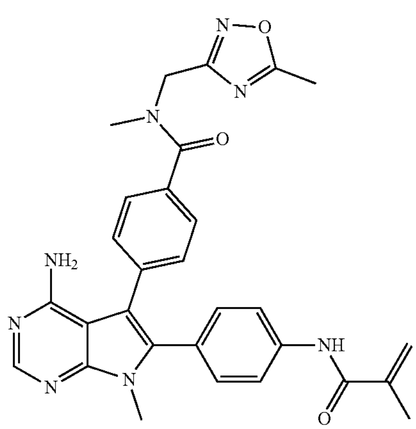 [SMILES: C=C(C)C(=O)Nc1ccc(-c2c(-c3ccc(C(=O)N(C)Cc4noc(C)n4)cc3)c3c(N)ncnc3n2C)cc1] | C | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 376 | 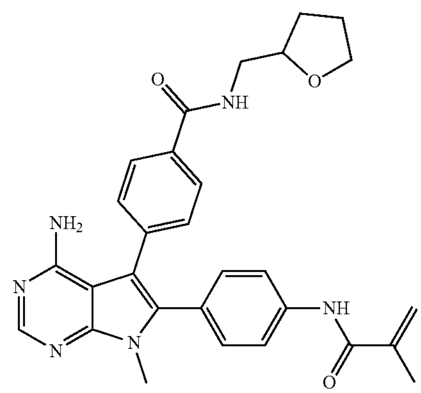 [SMILES: C=C(C)C(=O)Nc1ccc(-c2c(-c3ccc(C(=O)NCC4CCCO4)cc3)c3c(N)ncnc3n2C)cc1] | A | A |
| 377 | 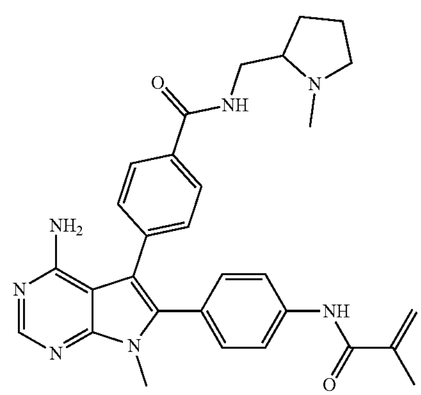 [SMILES: C=C(C)C(=O)Nc1ccc(-c2c(-c3ccc(C(=O)NCC4CCCN4C)cc3)c3c(N)ncnc3n2C)cc1] | C | C |
| 378 | 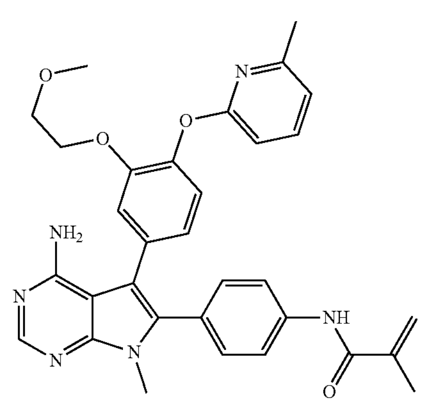 [SMILES: C=C(C)C(=O)Nc1ccc(-c2c(-c3ccc(Oc4cccc(C)n4)c(OCCOC)c3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 379 | 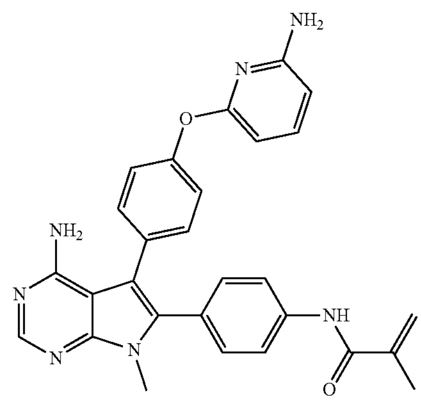 [SMILES: C=C(C)C(=O)Nc1ccc(-c2c(-c3ccc(Oc4cccc(N)n4)cc3)c3c(N)ncnc3n2C)cc1] | A | A |
| 380 | 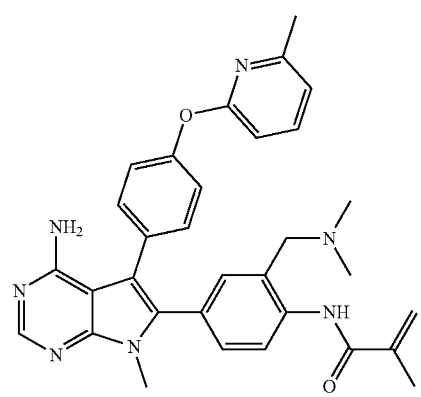 [SMILES: C=C(C)C(=O)Nc1ccc(-c2c(-c3ccc(Oc4cccc(C)n4)cc3)c3c(N)ncnc3n2C)cc1CN(C)C] | B | C |
| 381 | 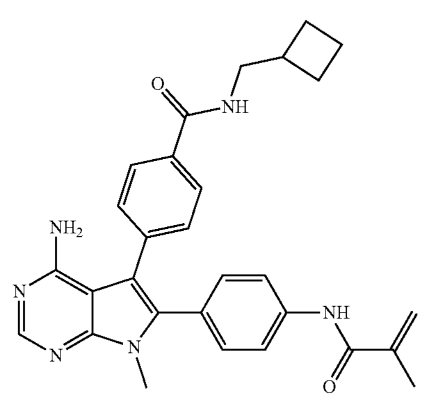 [SMILES: C=C(C)C(=O)Nc1ccc(-c2c(-c3ccc(C(=O)NCC4CCC4)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 382 | 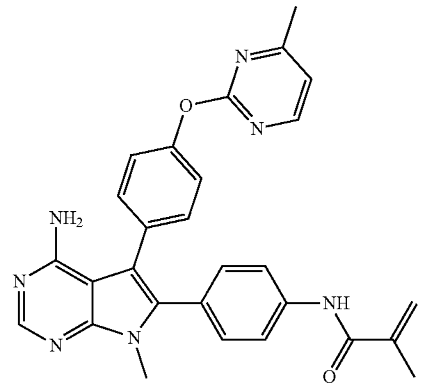 [SMILES: C=C(C)C(=O)Nc1ccc(-c2c(-c3ccc(Oc4nccc(C)n4)cc3)c3c(N)ncnc3n2C)cc1] | A | A |
| 383 | 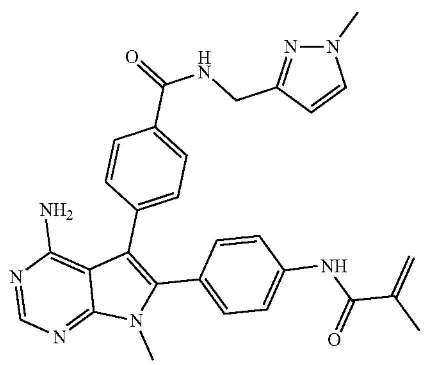 [SMILES: C=C(C)C(=O)Nc1ccc(-c2c(-c3ccc(C(=O)NCc4ccn(C)n4)cc3)c3c(N)ncnc3n2C)cc1] | D | C |
| 384 | 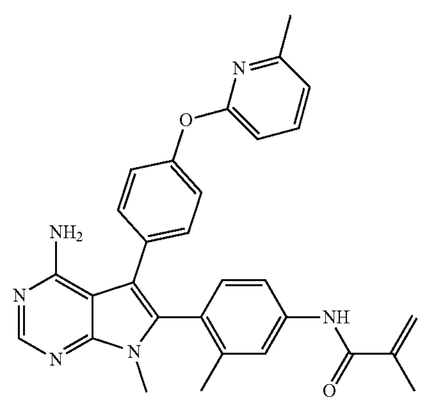 [SMILES: C=C(C)C(=O)Nc1ccc(-c2c(-c3ccc(Oc4cccc(C)n4)cc3)c3c(N)ncnc3n2C)c(C)c1] | A | A |
| 385 | 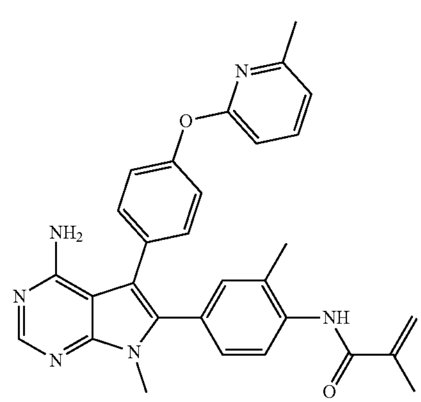 [SMILES: C=C(C)C(=O)Nc1ccc(-c2c(-c3ccc(Oc4cccc(C)n4)cc3)c3c(N)ncnc3n2C)cc1C] | B | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 386 | 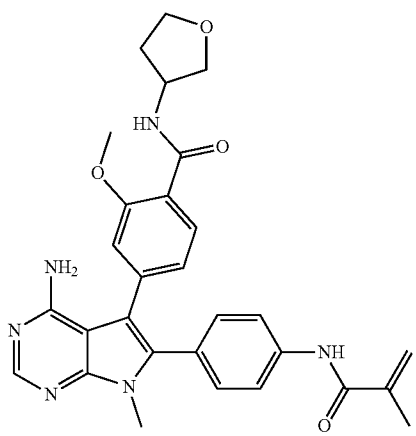 [SMILES: C=C(C)C(=O)Nc1ccc(-c2c(-c3ccc(C(=O)NC4CCOC4)c(OC)c3)c3c(N)ncnc3n2C)cc1] | A | B |
| 387 | 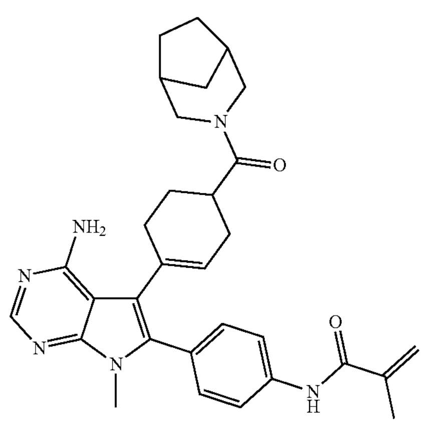 [SMILES: C=C(C)C(=O)Nc1ccc(-c2c(C3=CCC(C(=O)N4CC5CCC(C5)C4)CC3)c3c(N)ncnc3n2C)cc1] | B | A |
| 388 | 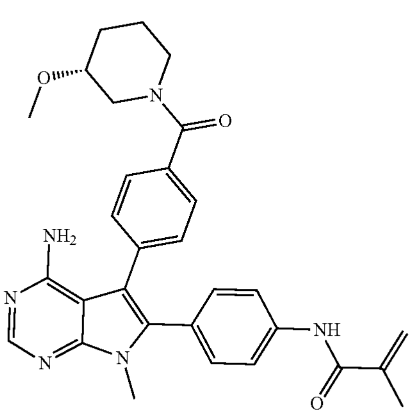 [SMILES: C=C(C)C(=O)Nc1ccc(-c2c(-c3ccc(C(=O)N4CCC[C@@H](OC)C4)cc3)c3c(N)ncnc3n2C)cc1] | C | B |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 389 | 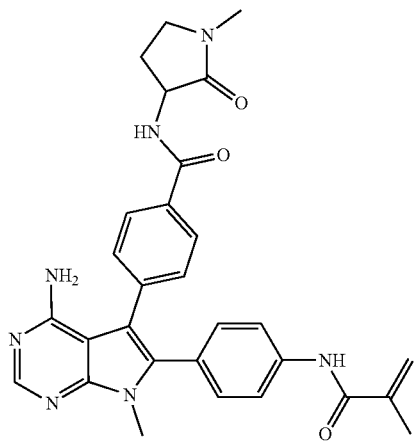 [SMILES: C=C(C)C(=O)Nc1ccc(-c2c(-c3ccc(C(=O)NC4CCN(C)C4=O)cc3)c3c(N)ncnc3n2C)cc1] | B | |
| 390 | 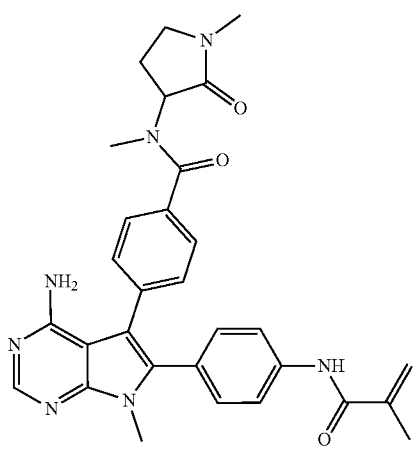 [SMILES: C=C(C)C(=O)Nc1ccc(-c2c(-c3ccc(C(=O)N(C)C4CCN(C)C4=O)cc3)c3c(N)ncnc3n2C)cc1] | D | |
| 391 | 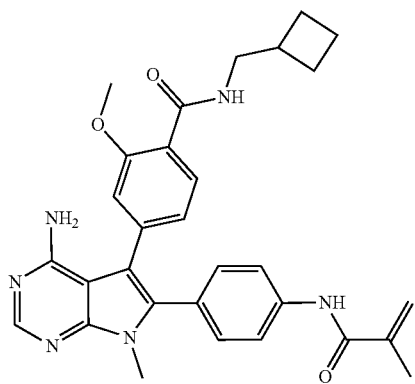 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 392 | 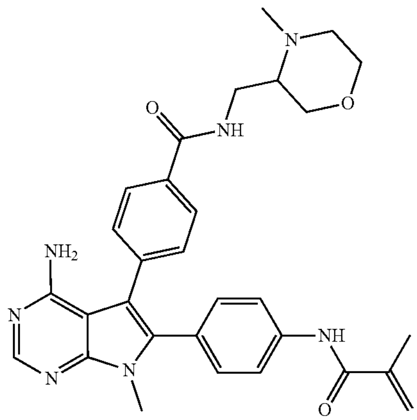 [SMILES: C=C(C)C(=O)Nc1ccc(-c2c(-c3ccc(C(=O)NCC4COCCN4C)cc3)c3c(N)ncnc3n2C)cc1] | D | |
| 393 | 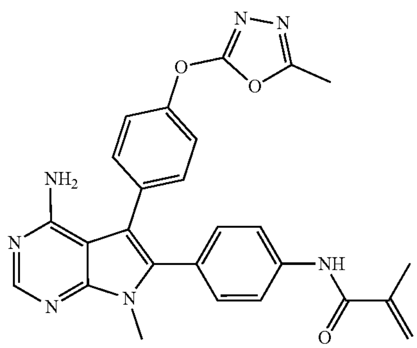 [SMILES: C=C(C)C(=O)Nc1ccc(-c2c(-c3ccc(Oc4nnc(C)o4)cc3)c3c(N)ncnc3n2C)cc1] | D | C |
| 394 | 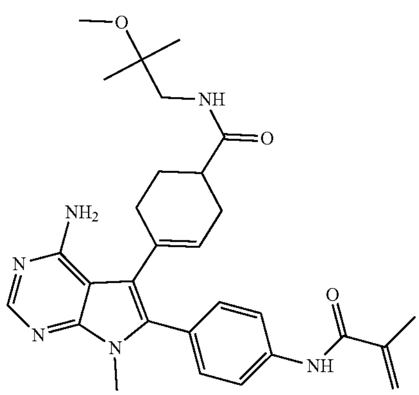 [SMILES: C=C(C)C(=O)Nc1ccc(-c2c(C3=CCC(C(=O)NCC(C)(C)OC)CC3)c3c(N)ncnc3n2C)cc1] | C | |
| 395 | 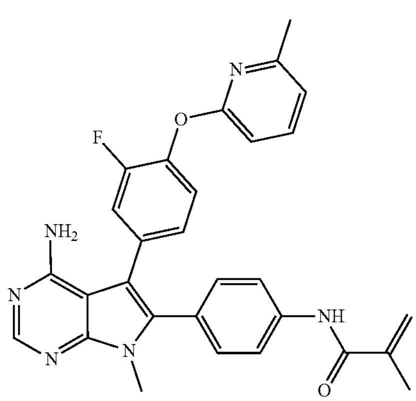 [SMILES: C=C(C)C(=O)Nc1ccc(-c2c(-c3ccc(Oc4cccc(C)n4)c(F)c3)c3c(N)ncnc3n2C)cc1] | A | A |

| | | US 11,780,845 B2 | |
|---|---|---|---|
299    300
TABLE 1-continued
Representative Compounds of the Invention with Bioactivity Data.
| Example | Structure | Biochemical FGFR2 Caliper IC50 | Cell SNU-16 IC50 |
|---|---|---|---|
| 396 | 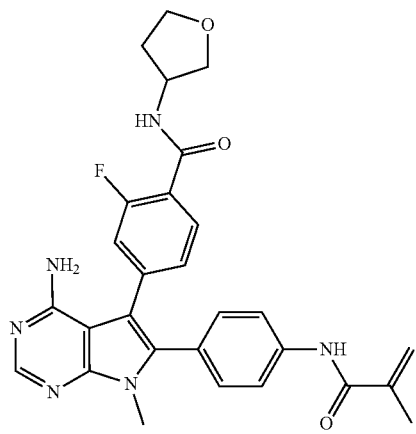 [SMILES: C=C(C)C(=O)Nc1ccc(-c2c(-c3ccc(C(=O)NC4CCOC4)c(F)c3)c3c(N)ncnc3n2C)cc1] | B | |
| 397 | 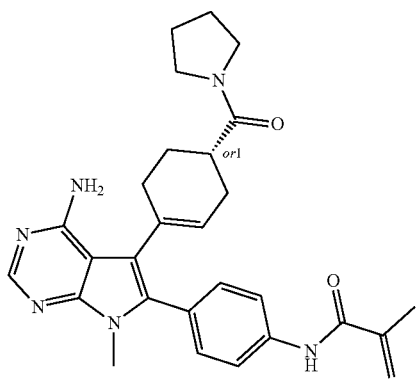 [SMILES: C=C(C)C(=O)Nc1ccc(-c2c(C3=CC[C@@H](C(=O)N4CCCC4)CC3)c3c(N)ncnc3n2C)cc1] | D | C |
| 398 | 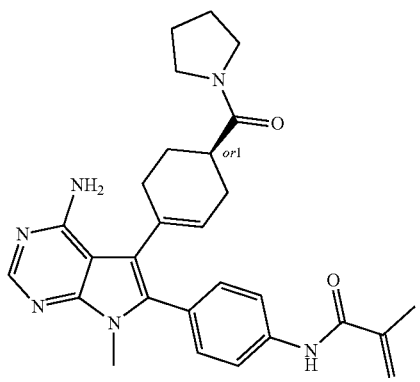 [SMILES: C=C(C)C(=O)Nc1ccc(-c2c(C3=CC[C@H](C(=O)N4CCCC4)CC3)c3c(N)ncnc3n2C)cc1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 399 | 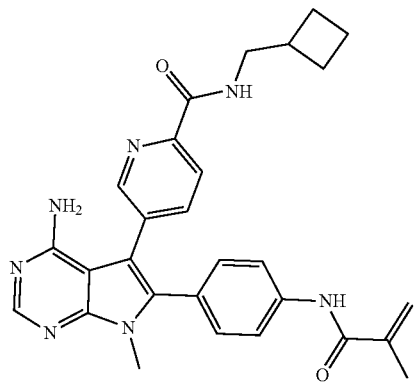 [SMILES: C=C(C)C(=O)Nc1ccc(-c2c(-c3ccc(C(=O)NCC4CCC4)nc3)c3c(N)ncnc3n2C)cc1] | B | A |
| 400 | 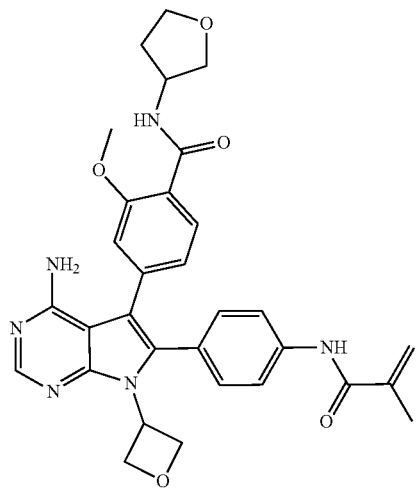 [SMILES: C=C(C)C(=O)Nc1ccc(-c2c(-c3ccc(C(=O)NC4CCOC4)c(OC)c3)c3c(N)ncnc3n2C2COC2)cc1] | B | |
| 401 | 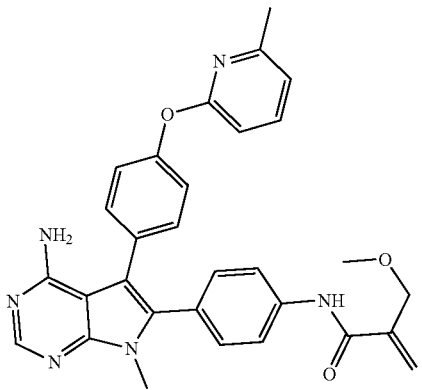 [SMILES: C=C(COC)C(=O)Nc1ccc(-c2c(-c3ccc(Oc4cccc(C)n4)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 402 | 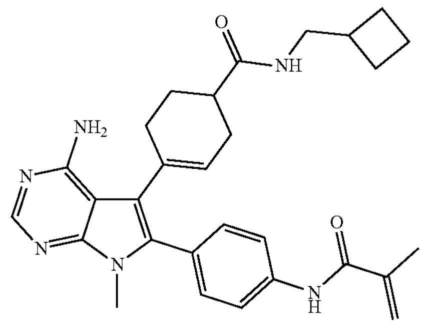 [SMILES: C=C(C)C(=O)Nc1ccc(-c2c(C3=CCC(C(=O)NCC4CCC4)CC3)c3c(N)ncnc3n2C)cc1] | B | |
| 403 | 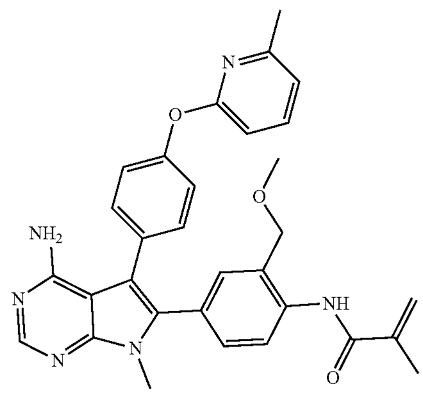 [SMILES: C=C(C)C(=O)Nc1ccc(-c2c(-c3ccc(Oc4cccc(C)n4)cc3)c3c(N)ncnc3n2C)cc1COC] | B | |
| 404 | 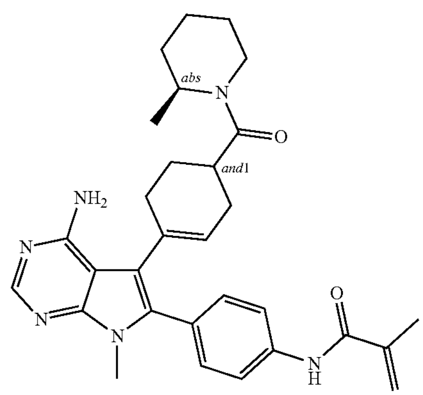 [SMILES: C=C(C)C(=O)Nc1ccc(-c2c(C3=CCC(C(=O)N4CCCC[C@@H]4C)CC3)c3c(N)ncnc3n2C)cc1] | B | |
| 405 | 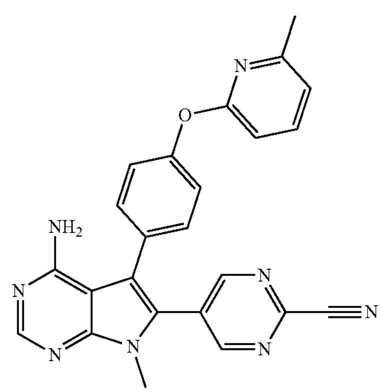 [SMILES: Cc1cccc(Oc2ccc(-c3c(-c4cnc(C#N)nc4)n(C)c4ncnc(N)c34)cc2)n1] | A | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 406 | 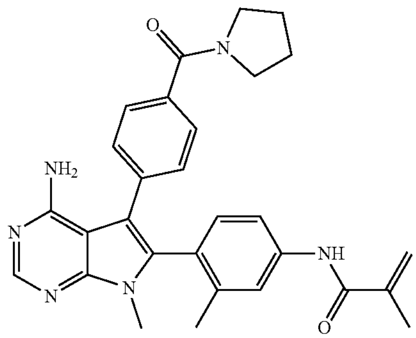 [SMILES: C=C(C)C(=O)Nc1ccc(-c2c(-c3ccc(C(=O)N4CCCC4)cc3)c3c(N)ncnc3n2C)c(C)c1] | A | A |
| 407 | 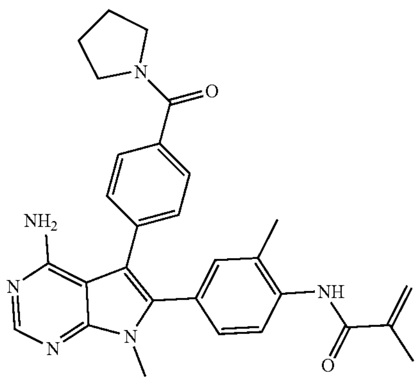 [SMILES: C=C(C)C(=O)Nc1ccc(-c2c(-c3ccc(C(=O)N4CCCC4)cc3)c3c(N)ncnc3n2C)cc1C] | D | |
| 408 | 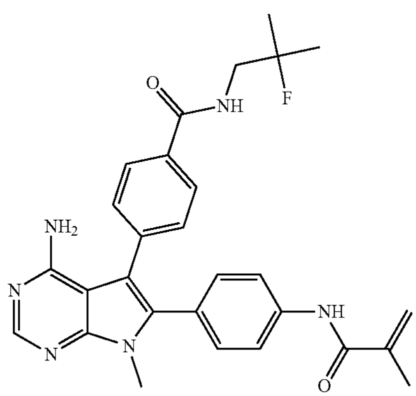 [SMILES: C=C(C)C(=O)Nc1ccc(-c2c(-c3ccc(C(=O)NCC(C)(C)F)cc3)c3c(N)ncnc3n2C)cc1] | A | A |
| 409 | 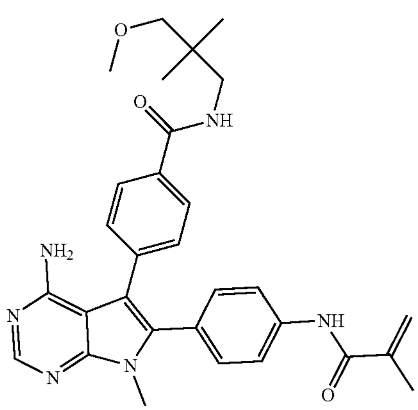 [SMILES: C=C(C)C(=O)Nc1ccc(-c2c(-c3ccc(C(=O)NCC(C)(C)COC)cc3)c3c(N)ncnc3n2C)cc1] | A | A |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 410 | 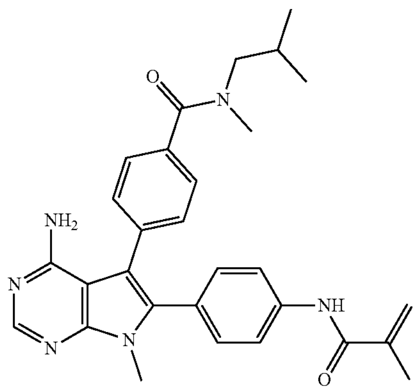 [SMILES: C=C(C)C(=O)Nc1ccc(-c2c(-c3ccc(C(=O)N(C)CC(C)C)cc3)c3c(N)ncnc3n2C)cc1] | A | A |
| 411 | 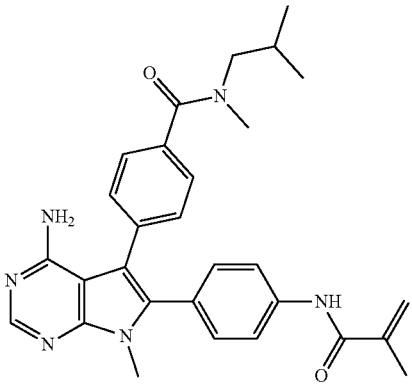 | C | C |
| 412 | 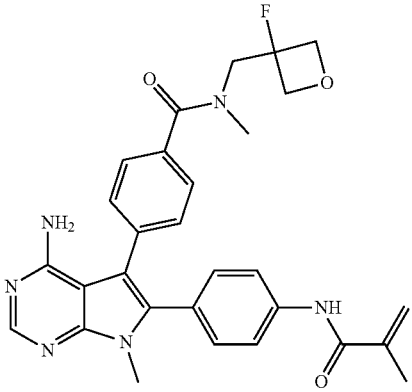 [SMILES: C=C(C)C(=O)Nc1ccc(-c2c(-c3ccc(C(=O)N(C)CC4(F)COC4)cc3)c3c(N)ncnc3n2C)cc1] | A | |
|     | 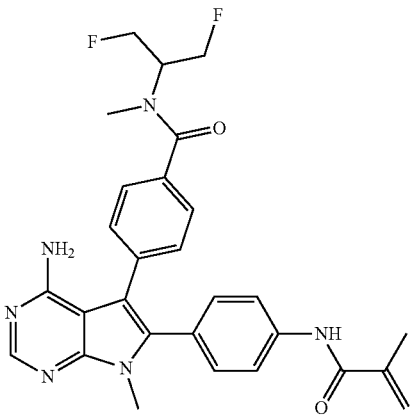 [SMILES: C=C(C)C(=O)Nc1ccc(-c2c(-c3ccc(C(=O)N(C)C(CF)CF)cc3)c3c(N)ncnc3n2C)cc1] | | |

309 310

TABLE 1-continued

Representative Compounds of the Invention with Bioactivity Data.

| Example | Structure | Biochemical FGFR2 Caliper IC50 | Cell SNU-16 IC50 |
|---|---|---|---|
| 413 | 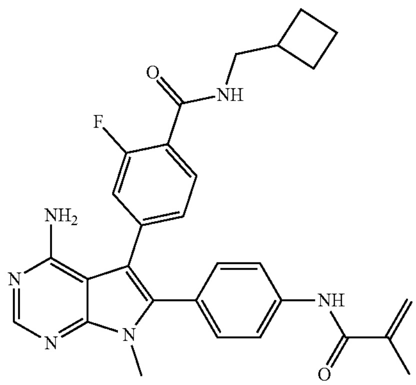 [SMILES: C=C(C)C(=O)Nc1ccc(-c2c(-c3ccc(C(=O)NCC4CCC4)c(F)c3)c3c(N)ncnc3n2C)cc1] | A | A |
| 414 | 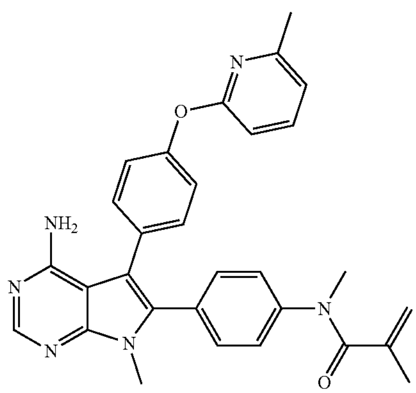 [SMILES: C=C(C)C(=O)N(C)c1ccc(-c2c(-c3ccc(Oc4cccc(C)n4)cc3)c3c(N)ncnc3n2C)cc1] | B | |
| 415 | 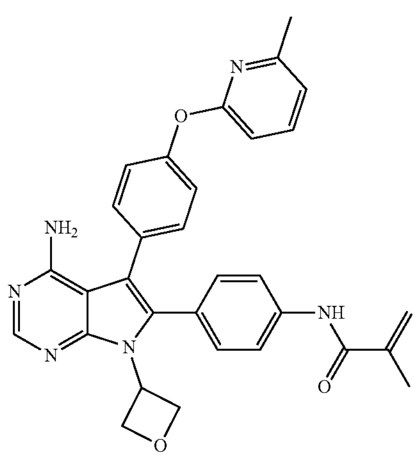 [SMILES: C=C(C)C(=O)Nc1ccc(-c2c(-c3ccc(Oc4cccc(C)n4)cc3)c3c(N)ncnc3n2C2COC2)cc1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 416 | 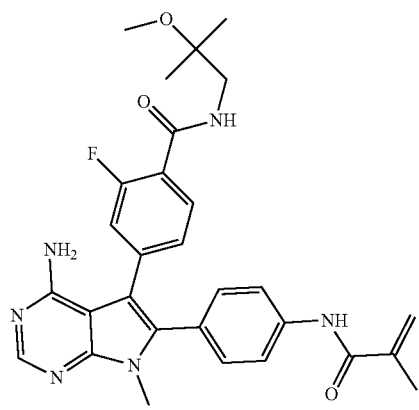 [SMILES: C=C(C)C(=O)Nc1ccc(-c2c(-c3ccc(C(=O)NCC(C)(C)OC)c(F)c3)c3c(N)ncnc3n2C)cc1] | A | A |
| 417 | 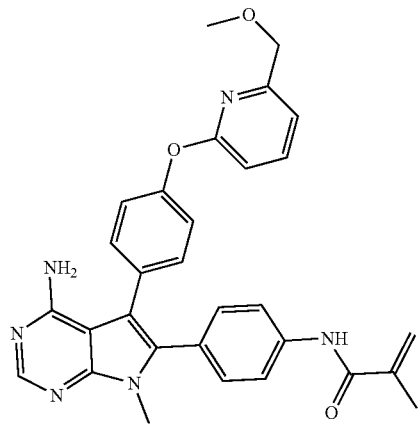 [SMILES: C=C(C)C(=O)Nc1ccc(-c2c(-c3ccc(Oc4cccc(COC)n4)cc3)c3c(N)ncnc3n2C)cc1] | A | A |
| 418 | 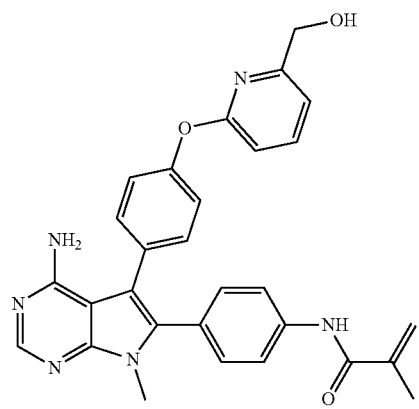 [SMILES: C=C(C)C(=O)Nc1ccc(-c2c(-c3ccc(Oc4cccc(CO)n4)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 419 | 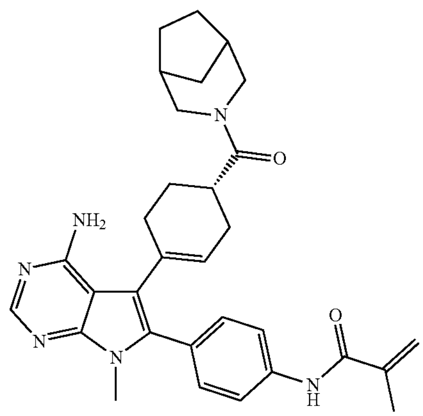 [SMILES: C=C(C)C(=O)Nc1ccc(-c2c(C3=CC[C@@H](C(=O)N4CC5CCC(C5)C4)CC3)c3c(N)ncnc3n2C)cc1] | A | A |
| 420 | 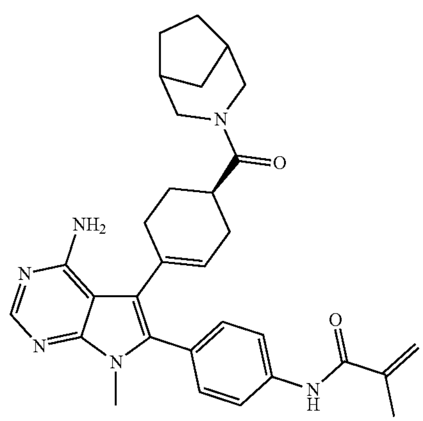 [SMILES: C=C(C)C(=O)Nc1ccc(-c2c(C3=CC[C@H](C(=O)N4CC5CCC(C5)C4)CC3)c3c(N)ncnc3n2C)cc1] | D | |
| 421 | 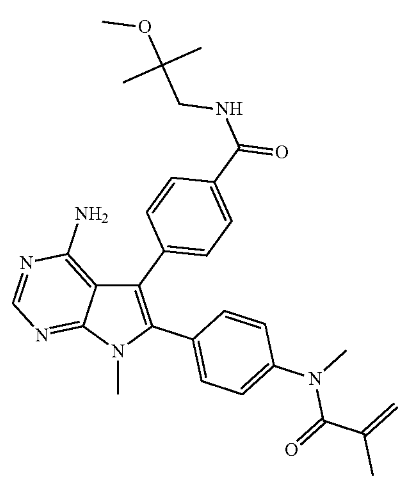 [SMILES: C=C(C)C(=O)N(C)c1ccc(-c2c(-c3ccc(C(=O)NCC(C)(C)OC)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 422 | 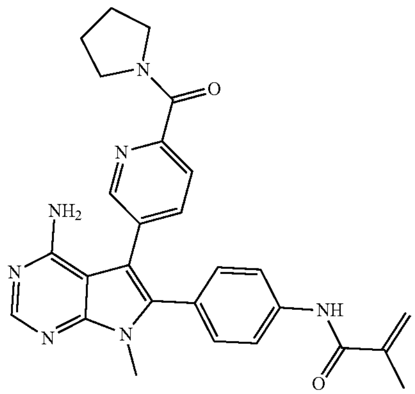 [SMILES: C=C(C)C(=O)Nc1ccc(-c2c(-c3ccc(C(=O)N4CCCC4)nc3)c3c(N)ncnc3n2C)cc1] | D | |
| 423 | 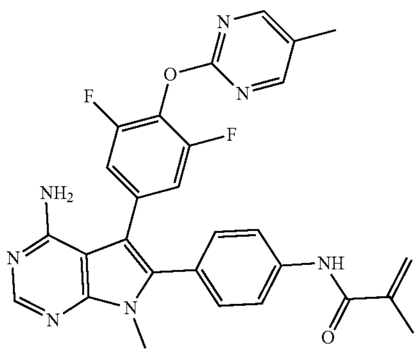 [SMILES: C=C(C)C(=O)Nc1ccc(-c2c(-c3cc(F)c(Oc4ncc(C)cn4)c(F)c3)c3c(N)ncnc3n2C)cc1] | A | B |
| 424 | 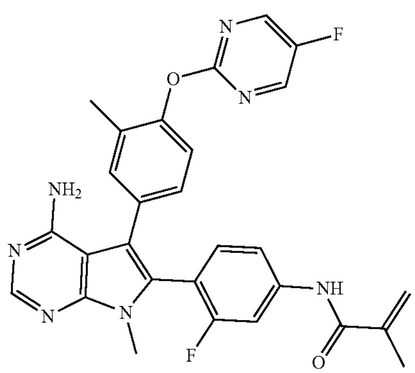 [SMILES: C=C(C)C(=O)Nc1ccc(-c2c(-c3ccc(Oc4ncc(F)cn4)c(C)c3)c3c(N)ncnc3n2C)c(F)c1] | A | A |
| 425 | 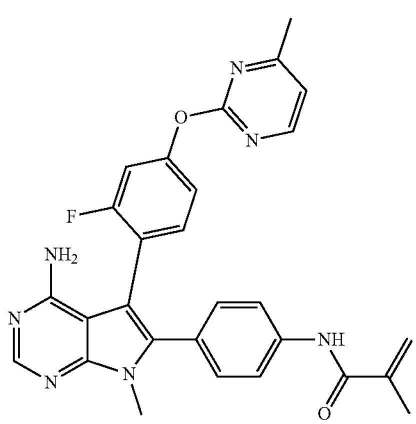 [SMILES: C=C(C)C(=O)Nc1ccc(-c2c(-c3ccc(Oc4nccc(C)n4)cc3F)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 426 | 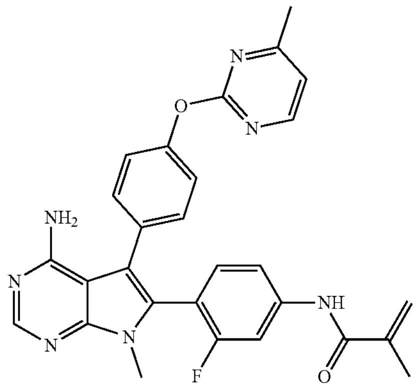 [SMILES: C=C(C)C(=O)Nc1ccc(-c2c(-c3ccc(Oc4nccc(C)n4)cc3)c3c(N)ncnc3n2C)c(F)c1] | A | A |
| 427 | 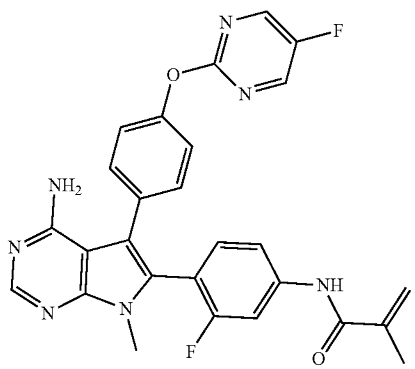 [SMILES: C=C(C)C(=O)Nc1ccc(-c2c(-c3ccc(Oc4ncc(F)cn4)cc3)c3c(N)ncnc3n2C)c(F)c1] | A | A |
| 428 | 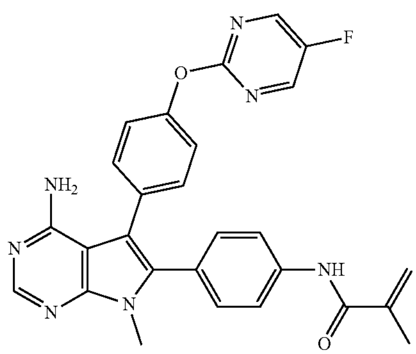 [SMILES: C=C(C)C(=O)Nc1ccc(-c2c(-c3ccc(Oc4ncc(F)cn4)cc3)c3c(N)ncnc3n2C)cc1] | A | A |
| 429 | 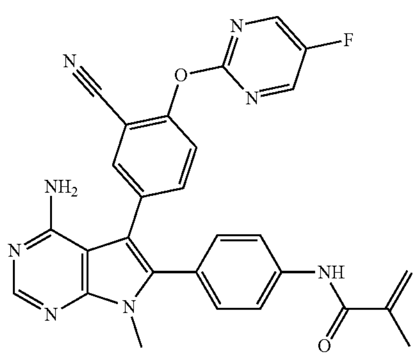 [SMILES: C=C(C)C(=O)Nc1ccc(-c2c(-c3ccc(Oc4ncc(F)cn4)c(C#N)c3)c3c(N)ncnc3n2C)cc1] | B | B |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 430 | 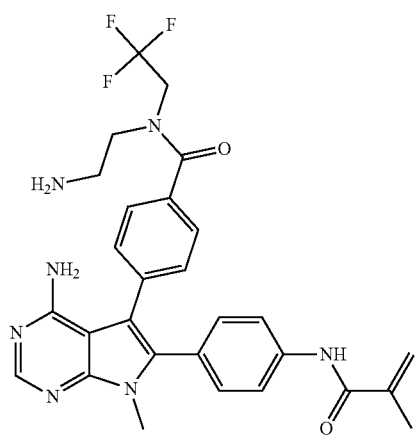 [SMILES: C=C(C)C(=O)Nc1ccc(-c2c(-c3ccc(C(=O)N(CCN)CC(F)(F)F)cc3)c3c(N)ncnc3n2C)cc1] | C | |
| 431 | 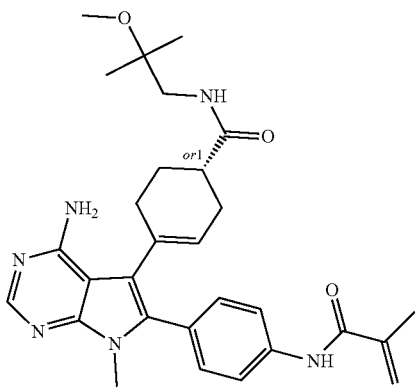 [SMILES: C=C(C)C(=O)Nc1ccc(-c2c(C3=CC[C@@H](C(=O)NCC(C)(C)OC)CC3)c3c(N)ncnc3n2C)cc1] | C | |
| 432 | 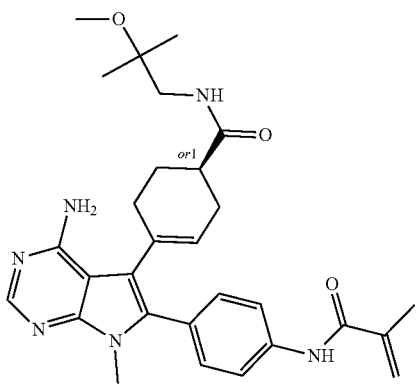 [SMILES: C=C(C)C(=O)Nc1ccc(-c2c(C3=CC[C@H](C(=O)NCC(C)(C)OC)CC3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 433 | 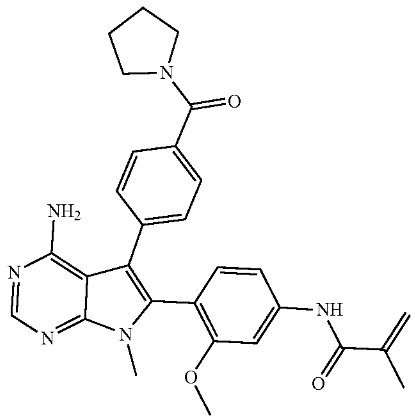 [SMILES: C=C(C)C(=O)Nc1ccc(-c2c(-c3ccc(C(=O)N4CCCC4)cc3)c3c(N)ncnc3n2C)c(OC)c1] | A | A |
| 434 | 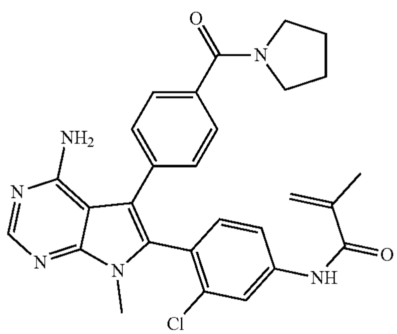 [SMILES: C=C(C)C(=O)Nc1ccc(-c2c(-c3ccc(C(=O)N4CCCC4)cc3)c3c(N)ncnc3n2C)c(Cl)c1] | A | A |
| 435 | 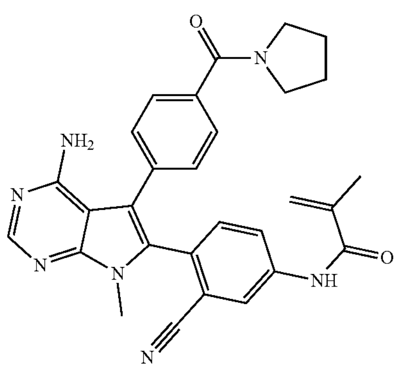 [SMILES: C=C(C)C(=O)Nc1ccc(-c2c(-c3ccc(C(=O)N4CCCC4)cc3)c3c(N)ncnc3n2C)c(C#N)c1] | A | B |
| 436 | 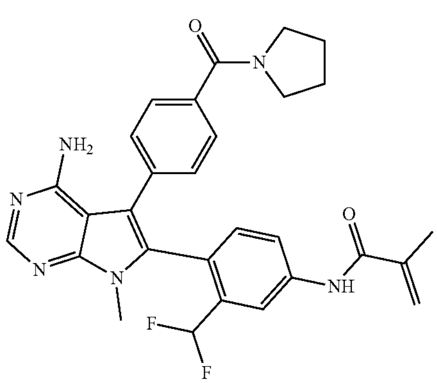 [SMILES: C=C(C)C(=O)Nc1ccc(-c2c(-c3ccc(C(=O)N4CCCC4)cc3)c3c(N)ncnc3n2C)c(C(F)F)c1] | A | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 437 | 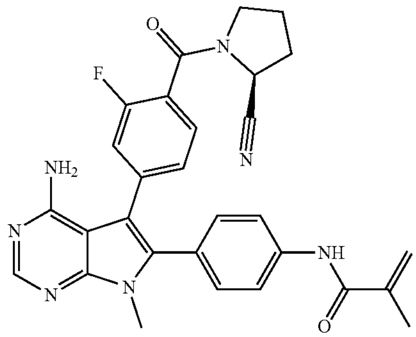 [SMILES: C=C(C)C(=O)Nc1ccc(-c2c(-c3ccc(C(=O)N4CCC[C@H]4C#N)c(F)c3)c3c(N)ncnc3n2C)cc1] | A | A |
| 438 | 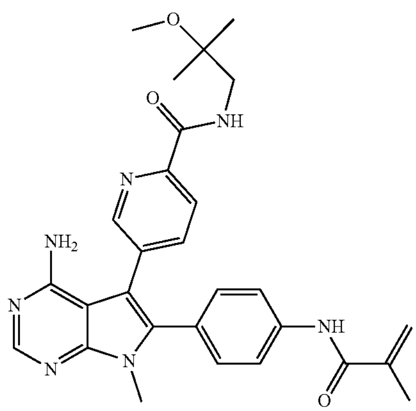 [SMILES: C=C(C)C(=O)Nc1ccc(-c2c(-c3ccc(C(=O)NCC(C)(C)OC)nc3)c3c(N)ncnc3n2C)cc1] | D | |
| 439 | 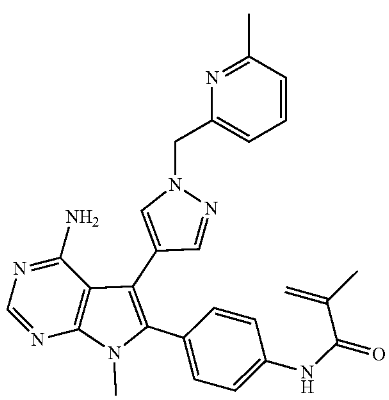 [SMILES: C=C(C)C(=O)Nc1ccc(-c2c(-c3cnn(Cc4cccc(C)n4)c3)c3c(N)ncnc3n2C)cc1] | D | |
| 440 | 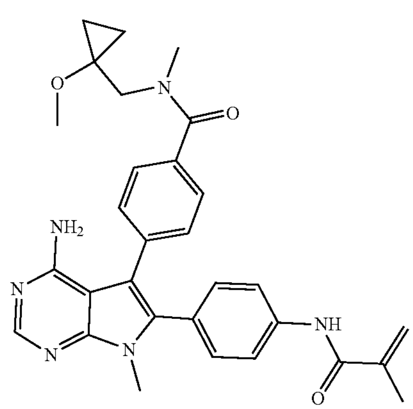 [SMILES: C=C(C)C(=O)Nc1ccc(-c2c(-c3ccc(C(=O)N(C)CC4(OC)CC4)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 441 | 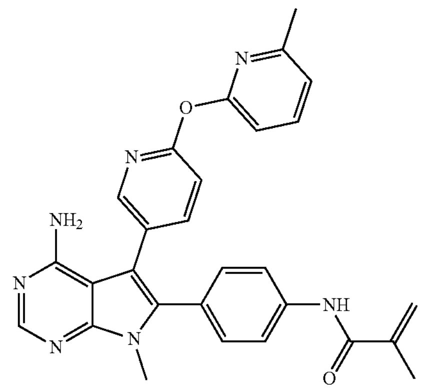 | C | C |
| 442 | 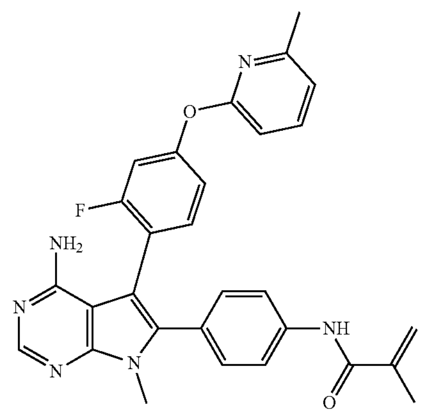 [SMILES: C=C(C)C(=O)Nc1ccc(-c2c(-c3ccc(Oc4cccc(C)n4)cc3F)c3c(N)ncnc3n2C)cc1] | A | A |
| 443 | 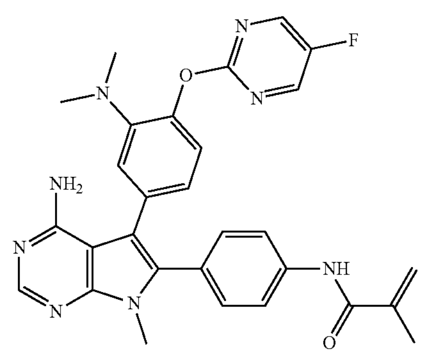 [SMILES: C=C(C)C(=O)Nc1ccc(-c2c(-c3ccc(Oc4ncc(F)cn4)c(N(C)C)c3)c3c(N)ncnc3n2C)cc1] | D | |
| 444 | 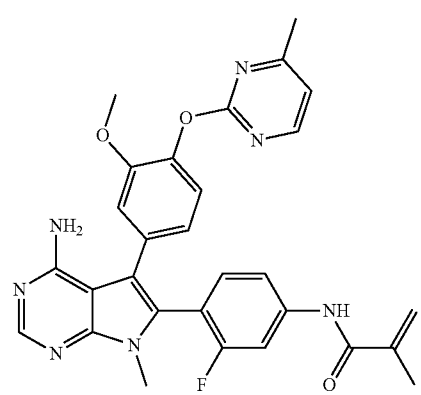 [SMILES: C=C(C)C(=O)Nc1ccc(-c2c(-c3ccc(Oc4nccc(C)n4)c(OC)c3)c3c(N)ncnc3n2C)c(F)c1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 445 | 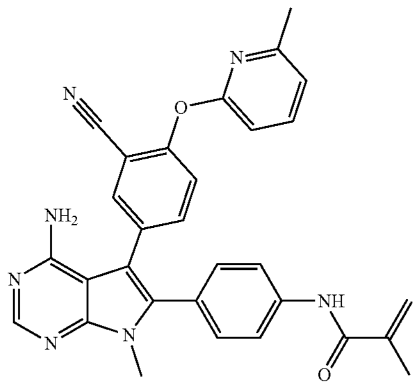 [SMILES: C=C(C)C(=O)Nc1ccc(-c2c(-c3ccc(Oc4cccc(C)n4)c(C#N)c3)c3c(N)ncnc3n2C)cc1] | A | A |
| 446 | 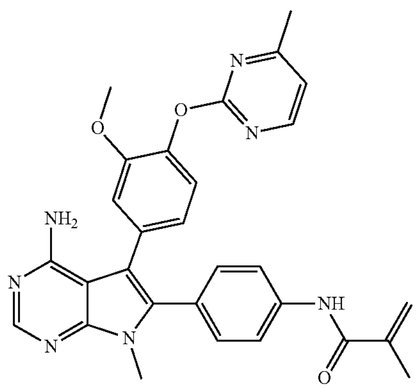 [SMILES: C=C(C)C(=O)Nc1ccc(-c2c(-c3ccc(Oc4nccc(C)n4)c(OC)c3)c3c(N)ncnc3n2C)cc1] | B | A |
| 447 | 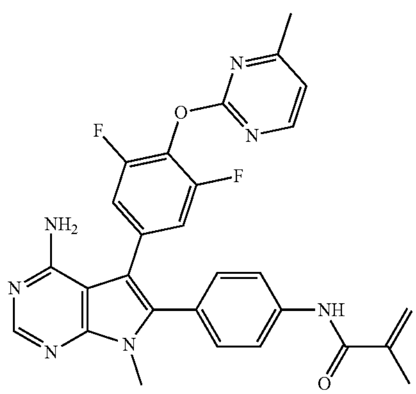 [SMILES: C=C(C)C(=O)Nc1ccc(-c2c(-c3cc(F)c(Oc4nccc(C)n4)c(F)c3)c3c(N)ncnc3n2C)cc1] | A | A |
| 448 | 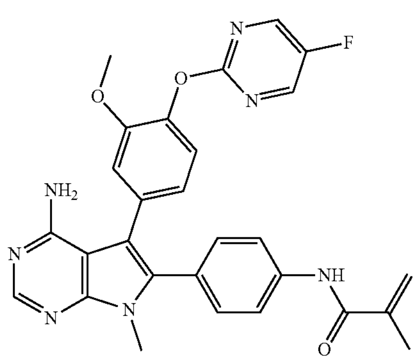 | C | B |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 449 | 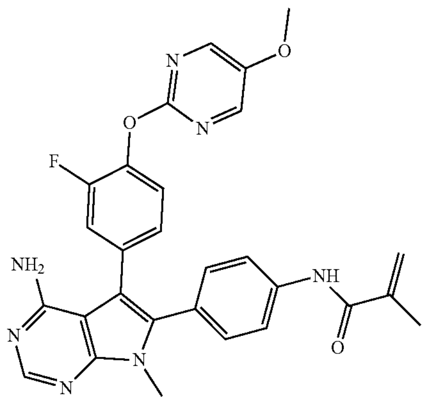 [SMILES: C=C(C)C(=O)Nc1ccc(-c2c(-c3ccc(Oc4ncc(OC)cn4)c(F)c3)c3c(N)ncnc3n2C)cc1] | C | B |
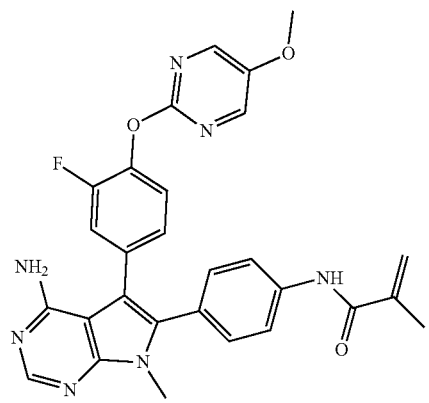
| | | | |
|---|---|---|---|
| 450 | | C | |
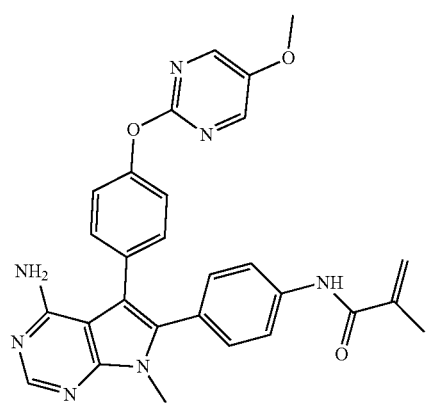 [SMILES: C=C(C)C(=O)Nc1ccc(-c2c(-c3ccc(Oc4ncc(OC)cn4)cc3)c3c(N)ncnc3n2C)cc1]
| | | | |
|---|---|---|---|
| 451 | | C | A |
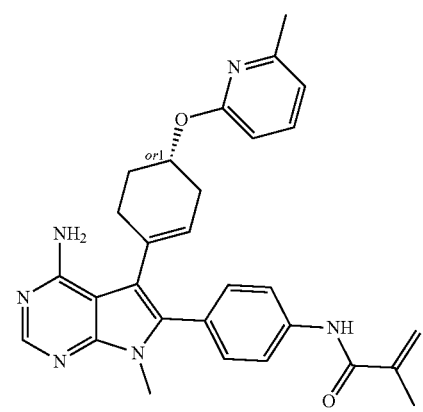 [SMILES: C=C(C)C(=O)Nc1ccc(-c2c(C3=CC[C@@H](Oc4cccc(C)n4)CC3)c3c(N)ncnc3n2C)cc1]

TABLE 1-continued

Representative Compounds of the Invention with Bioactivity Data.

| Example | Structure | Biochemical FGFR2 Caliper IC50 | Cell SNU-16 IC50 |
|---|---|---|---|
| 452 | 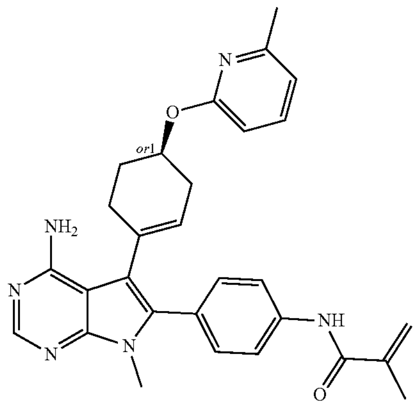 [SMILES: C=C(C)C(=O)Nc1ccc(-c2c(C3=CC[C@H](Oc4cccc(C)n4)CC3)c3c(N)ncnc3n2C)cc1] | D | C |
| 453 | 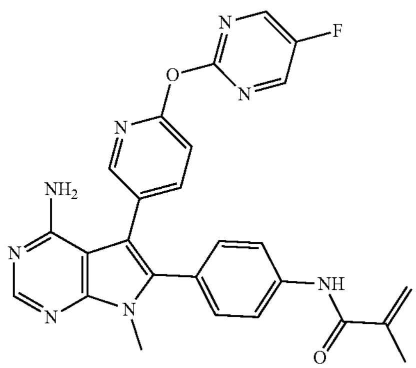 [SMILES: C=C(C)C(=O)Nc1ccc(-c2c(-c3ccc(Oc4ncc(F)cn4)nc3)c3c(N)ncnc3n2C)cc1] | D | |
| 454 | 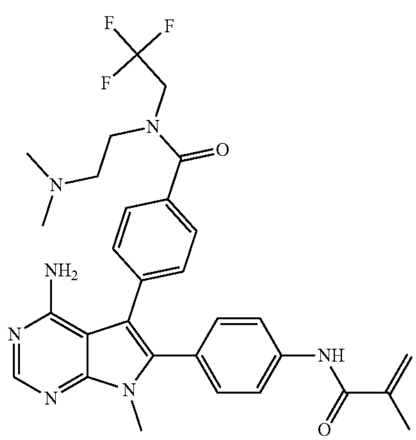 [SMILES: C=C(C)C(=O)Nc1ccc(-c2c(-c3ccc(C(=O)N(CCN(C)C)CC(F)(F)F)cc3)c3c(N)ncnc3n2C)cc1] | | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 455 | 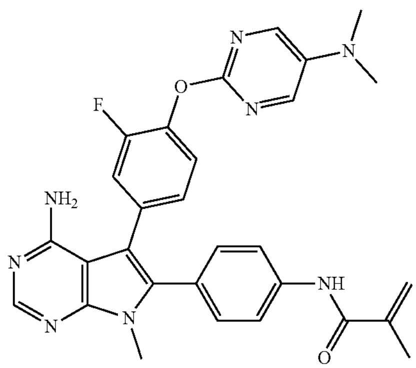 [SMILES: C=C(C)C(=O)Nc1ccc(-c2c(-c3ccc(Oc4ncc(N(C)C)cn4)c(F)c3)c3c(N)ncnc3n2C)cc1] | C | |
| 456 | 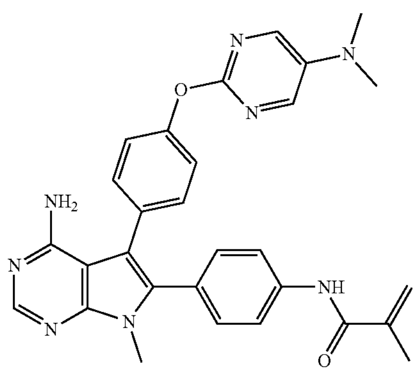 [SMILES: C=C(C)C(=O)Nc1ccc(-c2c(-c3ccc(Oc4ncc(N(C)C)cn4)cc3)c3c(N)ncnc3n2C)cc1] | C | |
| 457 | 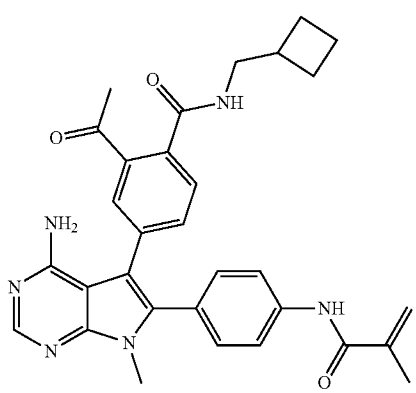 [SMILES: C=C(C)C(=O)Nc1ccc(-c2c(-c3ccc(C(=O)NCC4CCC4)c(C(C)=O)c3)c3c(N)ncnc3n2C)cc1] | B | |
| 458 | 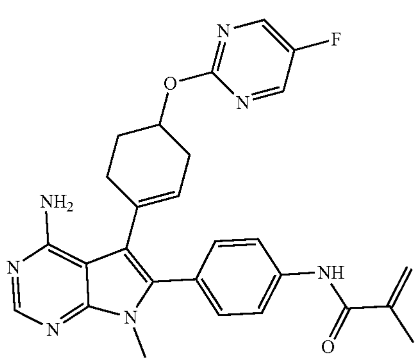 [SMILES: C=C(C)C(=O)Nc1ccc(-c2c(C3=CCC(Oc4ncc(F)cn4)CC3)c3c(N)ncnc3n2C)cc1] | B | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 459 | 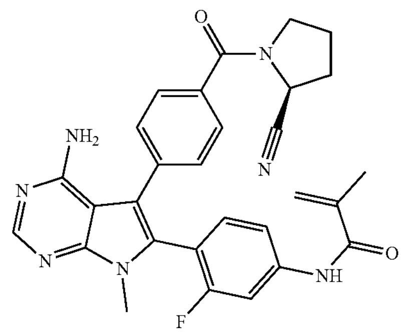 [SMILES: C=C(C)C(=O)Nc1ccc(-c2c(-c3ccc(C(=O)N4CCC[C@H]4C#N)cc3)c3c(N)ncnc3n2C)c(F)c1] | A | A |
| 460 | 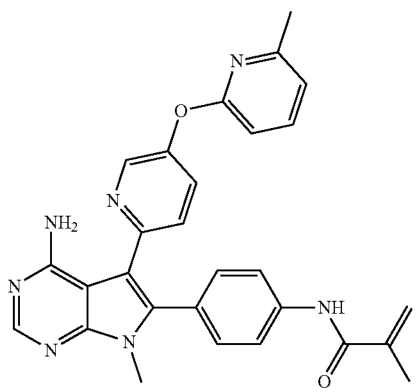 [SMILES: C=C(C)C(=O)Nc1ccc(-c2c(-c3ccc(Oc4cccc(C)n4)cn3)c3c(N)ncnc3n2C)cc1] | A | A |
| 461 | 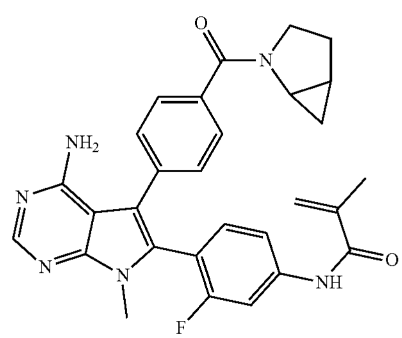 [SMILES: C=C(C)C(=O)Nc1ccc(-c2c(-c3ccc(C(=O)N4CCC5CC54)cc3)c3c(N)ncnc3n2C)c(F)c1] | A | A |
| 462 | 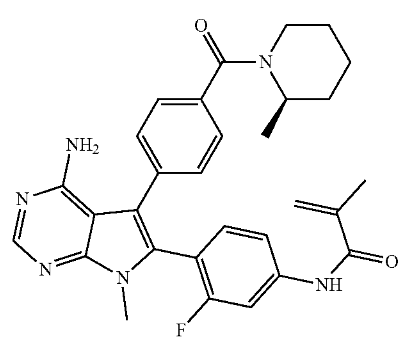 [SMILES: C=C(C)C(=O)Nc1ccc(-c2c(-c3ccc(C(=O)N4CCCC[C@H]4C)cc3)c3c(N)ncnc3n2C)c(F)c1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 463 | 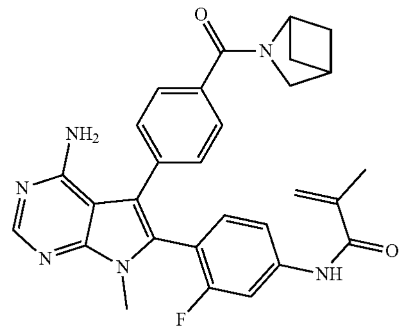 [SMILES: C=C(C)C(=O)Nc1ccc(-c2c(-c3ccc(C(=O)N4CC5CC4C5)cc3)c3c(N)ncnc3n2C)c(F)c1] | A | A |
| 464 | 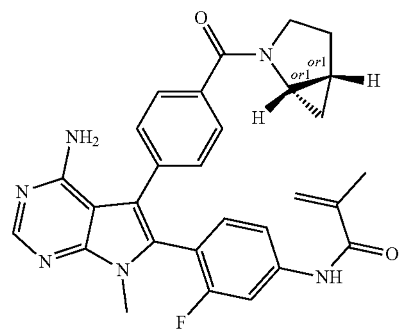 [SMILES: C=C(C)C(=O)Nc1ccc(-c2c(-c3ccc(C(=O)N4CC[C@@H]5C[C@@H]54)cc3)c3c(N)ncnc3n2C)c(F)c1] | A | A |
| 465 | 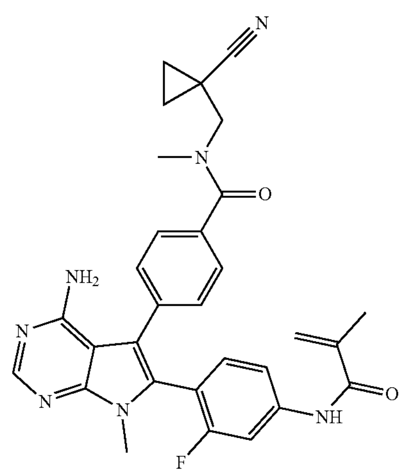 [SMILES: C=C(C)C(=O)Nc1ccc(-c2c(-c3ccc(C(=O)N(C)CC4(C#N)CC4)cc3)c3c(N)ncnc3n2C)c(F)c1] | A | A |
| 466 | 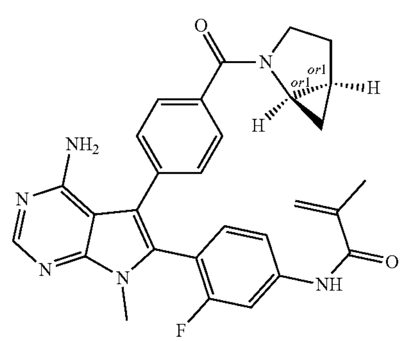 [SMILES: C=C(C)C(=O)Nc1ccc(-c2c(-c3ccc(C(=O)N4CC[C@H]5C[C@H]54)cc3)c3c(N)ncnc3n2C)c(F)c1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 467 | 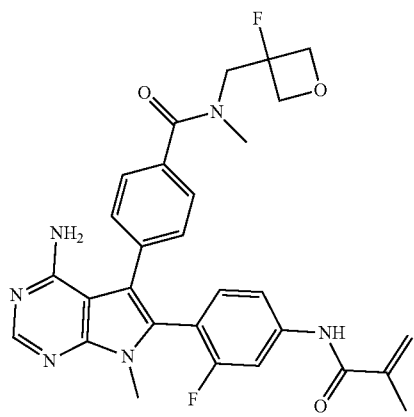 [SMILES: C=C(C)C(=O)Nc1ccc(-c2c(-c3ccc(C(=O)N(C)CC4(F)COC4)cc3)c3c(N)ncnc3n2C)c(F)c1] | B | |
| 468 | 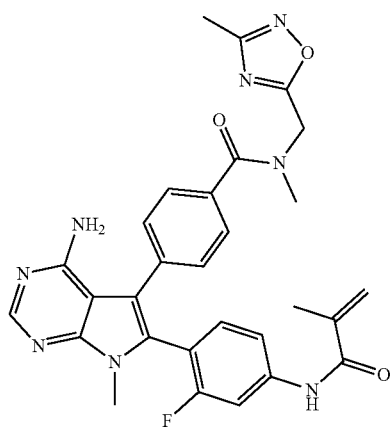 [SMILES: C=C(C)C(=O)Nc1ccc(-c2c(-c3ccc(C(=O)N(C)Cc4nc(C)no4)cc3)c3c(N)ncnc3n2C)c(F)c1] | A | A |
| 469 | 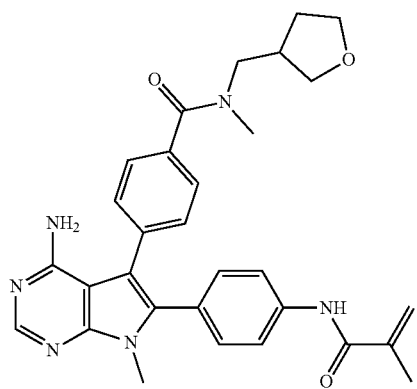 [SMILES: C=C(C)C(=O)Nc1ccc(-c2c(-c3ccc(C(=O)N(C)CC4CCOC4)cc3)c3c(N)ncnc3n2C)cc1] | C | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 470 | 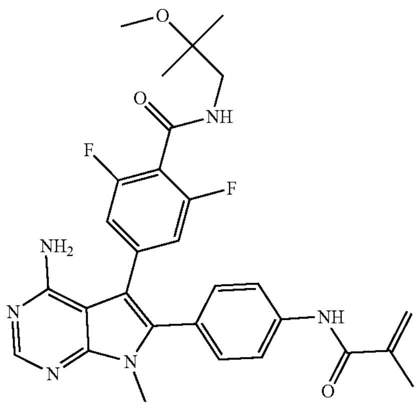 [SMILES: C=C(C)C(=O)Nc1ccc(-c2c(-c3cc(F)c(C(=O)NCC(C)(C)OC)c(F)c3)c3c(N)ncnc3n2C)cc1] | B | |
| 471 | 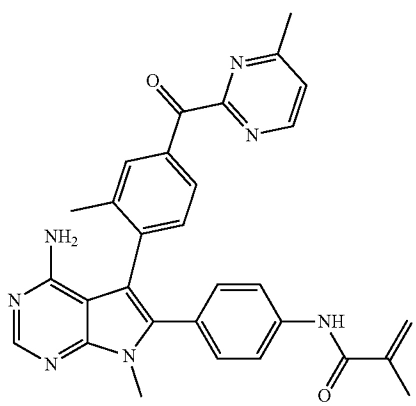 [SMILES: C=C(C)C(=O)Nc1ccc(-c2c(-c3ccc(C(=O)c4nccc(C)n4)cc3C)c3c(N)ncnc3n2C)cc1] | B | B |
| 472 | 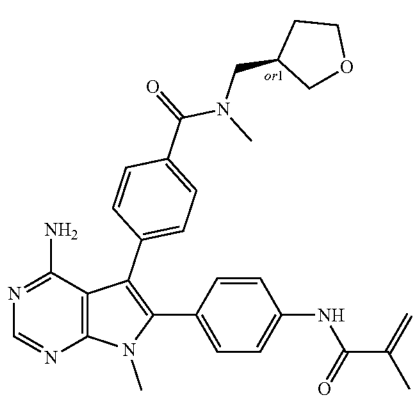 [SMILES: C=C(C)C(=O)Nc1ccc(-c2c(-c3ccc(C(=O)N(C)C[C@H]4CCOC4)cc3)c3c(N)ncnc3n2C)cc1] | C | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 473 | 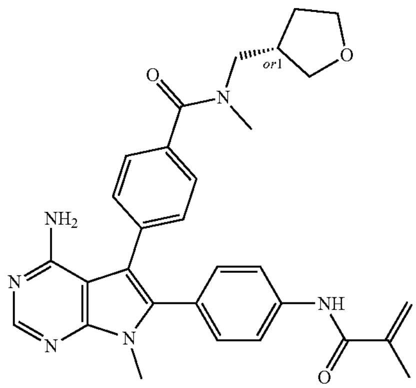 [SMILES: C=C(C)C(=O)Nc1ccc(-c2c(-c3ccc(C(=O)N(C)C[C@@H]4CCOC4)cc3)c3c(N)ncnc3n2C)cc1] | C | |
| 474 | 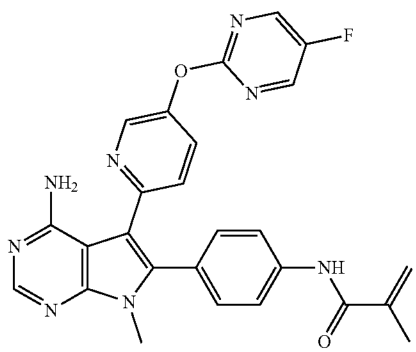 [SMILES: C=C(C)C(=O)Nc1ccc(-c2c(-c3ccc(Oc4ncc(F)cn4)cn3)c3c(N)ncnc3n2C)cc1] | A | A |
| 475 | 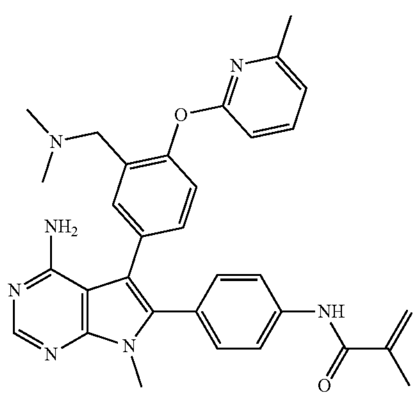 [SMILES: C=C(C)C(=O)Nc1ccc(-c2c(-c3ccc(Oc4cccc(C)n4)c(CN(C)C)c3)c3c(N)ncnc3n2C)cc1] | D | C |
| 476 | 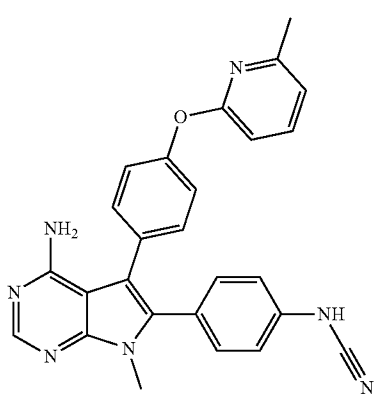 [SMILES: Cc1cccc(Oc2ccc(-c3c(-c4ccc(NC#N)cc4)n(C)c4ncnc(N)c34)cc2)n1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 477 | 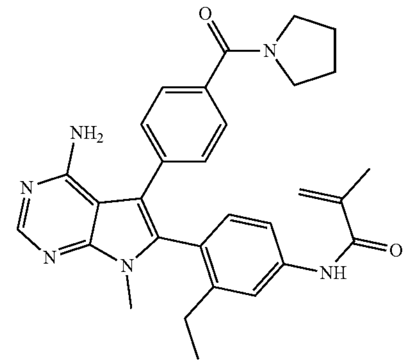 [SMILES: C=C(C)C(=O)Nc1ccc(-c2c(-c3ccc(C(=O)N4CCCC4)cc3)c3c(N)ncnc3n2C)c(CC)c1] | B | |
| 478 | 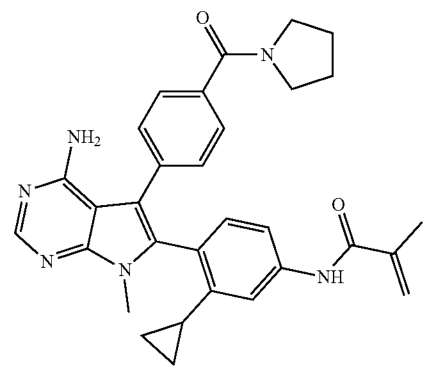 [SMILES: C=C(C)C(=O)Nc1ccc(-c2c(-c3ccc(C(=O)N4CCCC4)cc3)c3c(N)ncnc3n2C)c(C2CC2)c1] | B | |
| 479 | 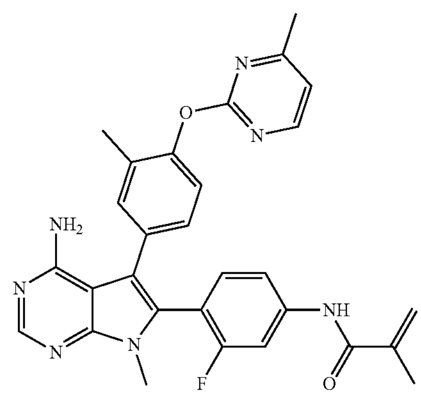 [SMILES: C=C(C)C(=O)Nc1ccc(-c2c(-c3ccc(Oc4nccc(C)n4)c(C)c3)c3c(N)ncnc3n2C)c(F)c1] | A | A |
| 480 | 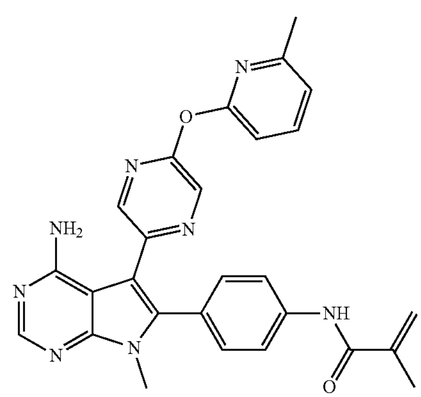 [SMILES: C=C(C)C(=O)Nc1ccc(-c2c(-c3cnc(Oc4cccc(C)n4)cn3)c3c(N)ncnc3n2C)cc1] | C | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 481 | 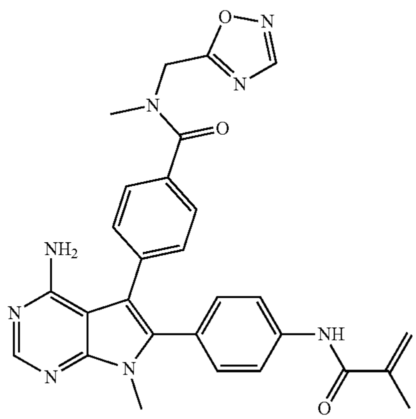 [SMILES: C=C(C)C(=O)Nc1ccc(-c2c(-c3ccc(C(=O)N(C)Cc4ncno4)cc3)c3c(N)ncnc3n2C)cc1] | D | |
| 482 | 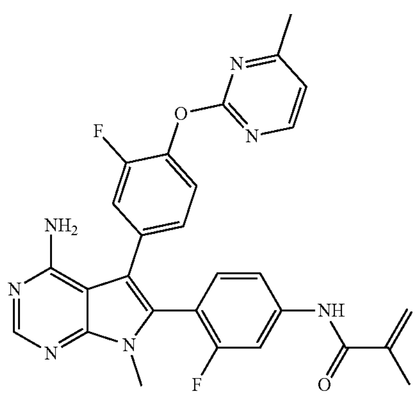 [SMILES: C=C(C)C(=O)Nc1ccc(-c2c(-c3ccc(Oc4nccc(C)n4)c(F)c3)c3c(N)ncnc3n2C)c(F)c1] | A | A |
| 483 | 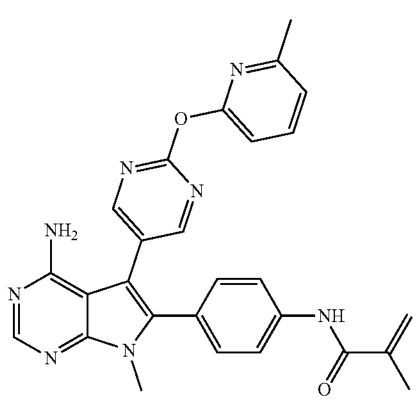 [SMILES: C=C(C)C(=O)Nc1ccc(-c2c(-c3cnc(Oc4cccc(C)n4)nc3)c3c(N)ncnc3n2C)cc1] | D | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 484 | 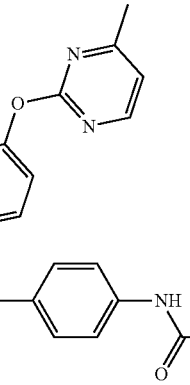 | A | A |
| 485 | 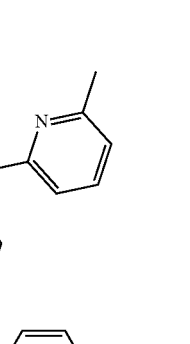 | A | A |
| 486 | 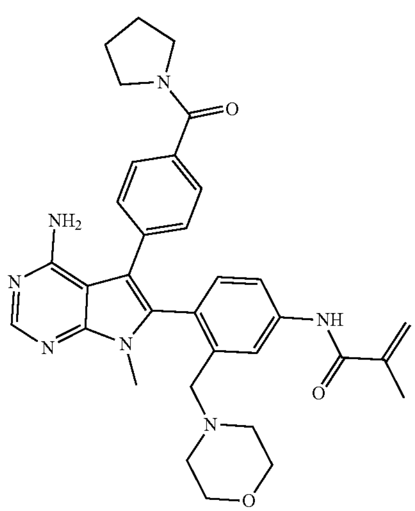 [SMILES: C=C(C)C(=O)Nc1ccc(-c2c(-c3ccc(C(=O)N4CCCC4)cc3)c3c(N)ncnc3n2C)c(CN2CCOCC2)c1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 487 | 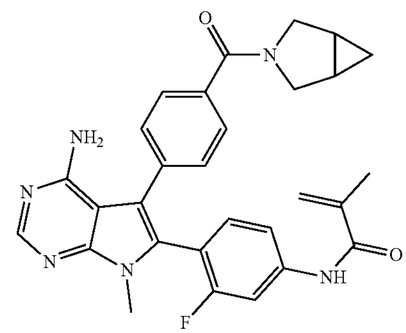 [SMILES: C=C(C)C(=O)Nc1ccc(-c2c(-c3ccc(C(=O)N4CC5CC5C4)cc3)c3c(N)ncnc3n2C)c(F)c1] | A | A |
| 488 | 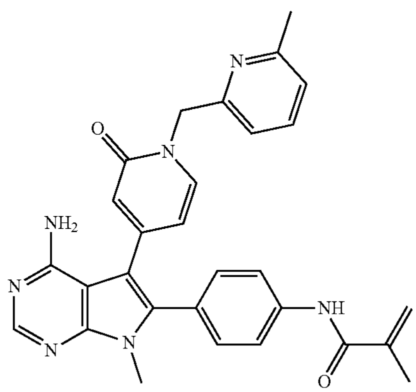 [SMILES: C=C(C)C(=O)Nc1ccc(-c2c(-c3ccn(Cc4cccc(C)n4)c(=O)c3)c3c(N)ncnc3n2C)cc1] | D | |
| 489 | 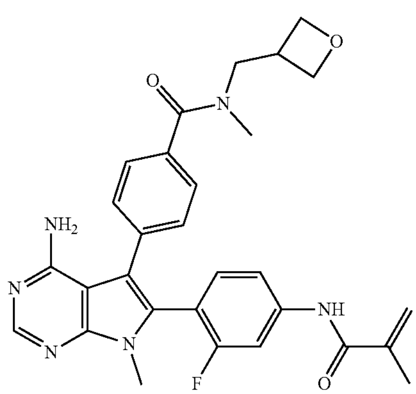 [SMILES: C=C(C)C(=O)Nc1ccc(-c2c(-c3ccc(C(=O)N(C)CC4COC4)cc3)c3c(N)ncnc3n2C)c(F)c1] | C | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 490 | 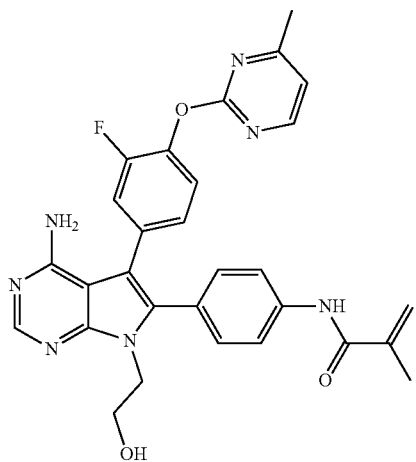 [SMILES: C=C(C)C(=O)Nc1ccc(-c2c(-c3ccc(Oc4nccc(C)n4)c(F)c3)c3c(N)ncnc3n2CCO)cc1] | A | A |
| 491 | 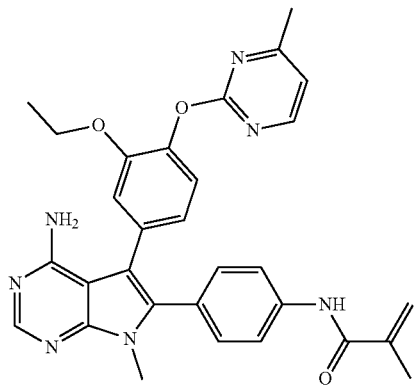 [SMILES: C=C(C)C(=O)Nc1ccc(-c2c(-c3ccc(Oc4nccc(C)n4)c(OCC)c3)c3c(N)ncnc3n2C)cc1] | D | |
| 492 | 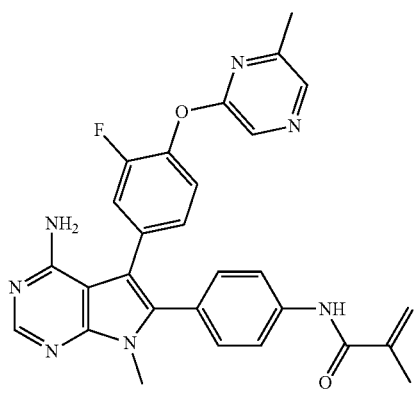 | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 493 | 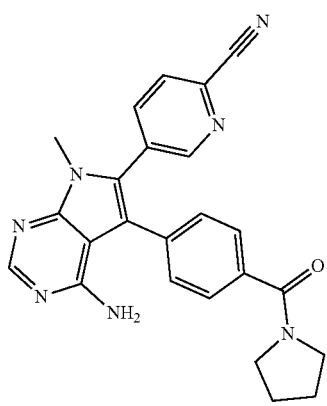 [SMILES: Cn1c(-c2ccc(C#N)nc2)c(-c2ccc(C(=O)N3CCCC3)cc2)c2c(N)ncnc21] | D | |
| 494 | 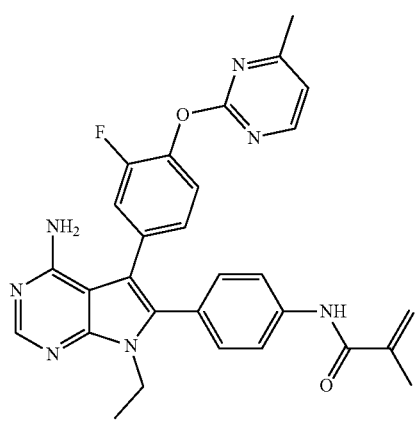 [SMILES: C=C(C)C(=O)Nc1ccc(-c2c(-c3ccc(Oc4nccc(C)n4)c(F)c3)c3c(N)ncnc3n2CC)cc1] | A | A |
| 495 | 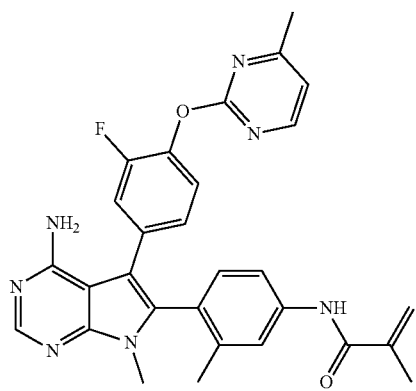 | A | A |

| Example | Structure | Biochemical FGFR2 Caliper IC50 | Cell SNU-16 IC50 |
|---|---|---|---|
| 496 | 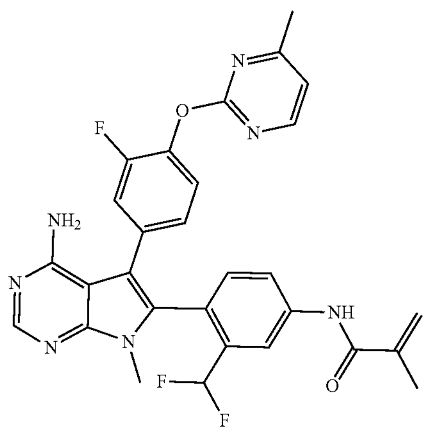 [SMILES: C=C(C)C(=O)Nc1ccc(-c2c(-c3ccc(Oc4nccc(C)n4)c(F)c3)c3c(N)ncnc3n2C)c(C(F)F)c1] | A | A |
| 497 | 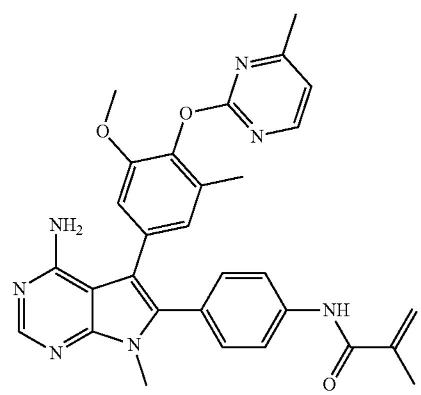 [SMILES: C=C(C)C(=O)Nc1ccc(-c2c(-c3cc(C)c(Oc4nccc(C)n4)c(OC)c3)c3c(N)ncnc3n2C)cc1] | B | A |
| 498 | 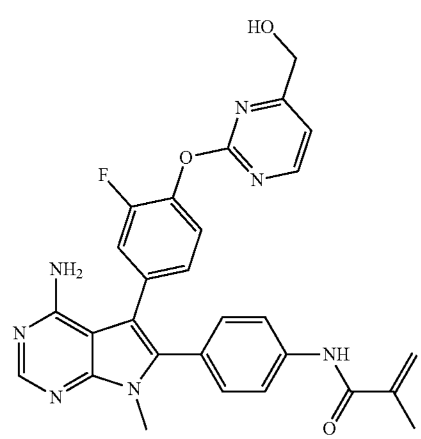 [SMILES: C=C(C)C(=O)Nc1ccc(-c2c(-c3ccc(Oc4nccc(CO)n4)c(F)c3)c3c(N)ncnc3n2C)cc1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 499 | 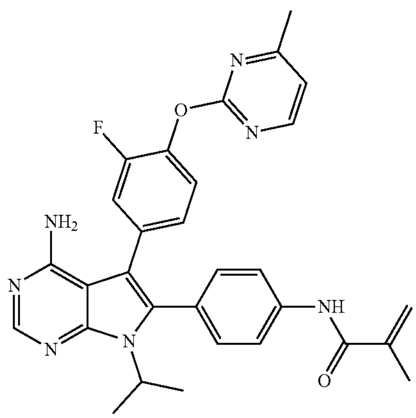 [SMILES: C=C(C)C(=O)Nc1ccc(-c2c(-c3ccc(Oc4nccc(C)n4)c(F)c3)c3c(N)ncnc3n2C(C)C)cc1] | A | A |
| 500 | 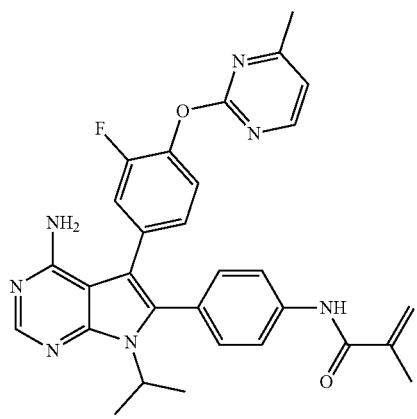 | A | A |
| 501 | 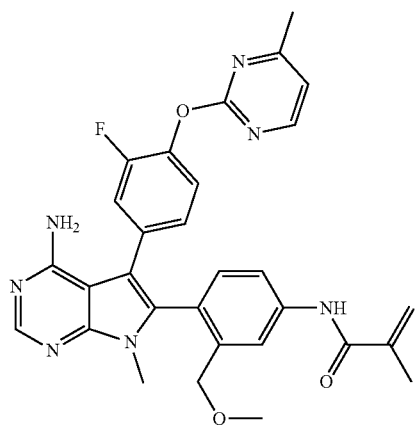 | D | |
| | 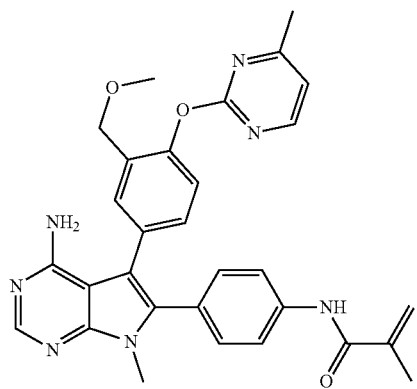 [SMILES: C=C(C)C(=O)Nc1ccc(-c2c(-c3ccc(Oc4nccc(C)n4)c(COC)c3)c3c(N)ncnc3n2C)cc1] | | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 502 | 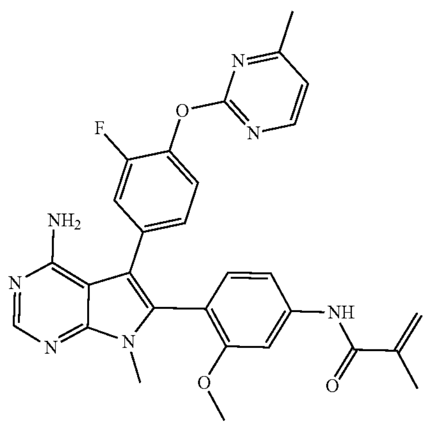 [SMILES: C=C(C)C(=O)Nc1ccc(-c2c(-c3ccc(Oc4nccc(C)n4)c(F)c3)c3c(N)ncnc3n2C)c(OC)c1] | A | A |
| 503 | 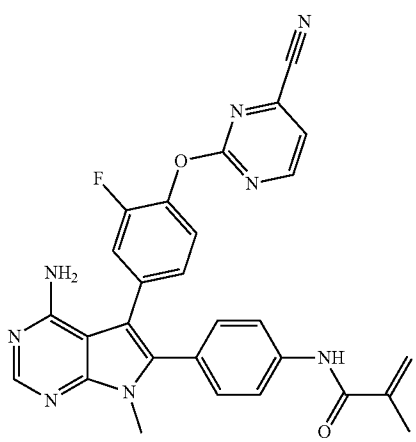 | A | A |
| 504 | 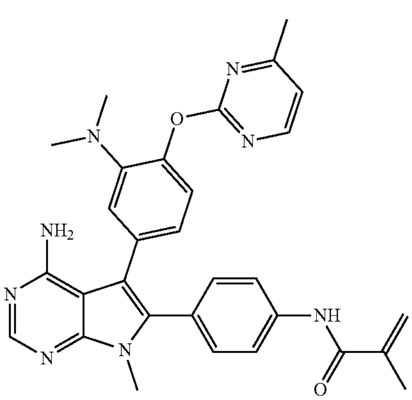 | D | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 505 | 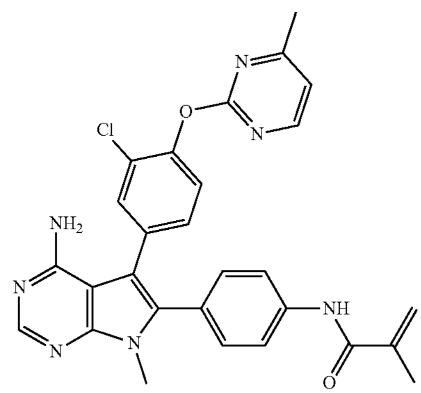 | A | A |
| 506 | 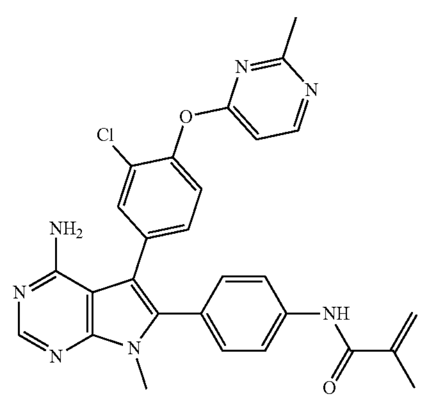 | C | C |
| 507 | 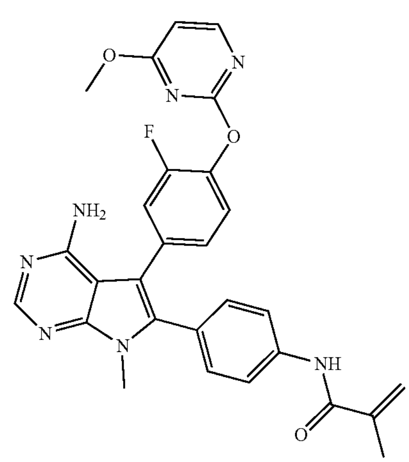 [SMILES: C=C(C)C(=O)Nc1ccc(-c2c(-c3ccc(Oc4nccc(OC)n4)c(F)c3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 508 | 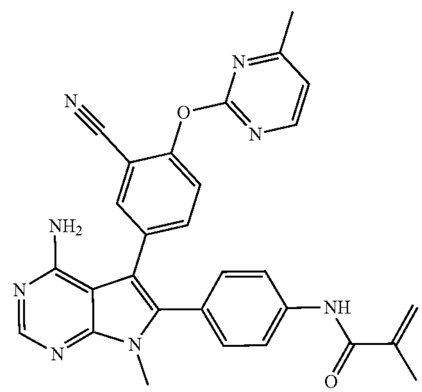 [SMILES: C=C(C)C(=O)Nc1ccc(-c2c(-c3ccc(Oc4nccc(C)n4)c(C#N)c3)c3c(N)ncnc3n2C)cc1] | A | A |
| 509 | 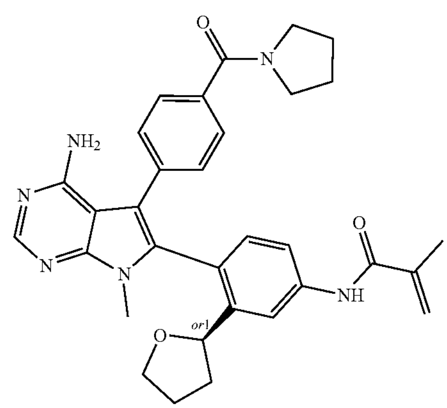 [SMILES: C=C(C)C(=O)Nc1ccc(-c2c(-c3ccc(C(=O)N4CCCC4)cc3)c3c(N)ncnc3n2C)c([C@H]2CCCO2)c1] | C | |
| 510 | 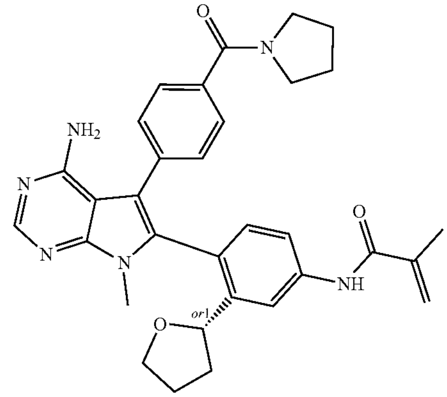 [SMILES: C=C(C)C(=O)Nc1ccc(-c2c(-c3ccc(C(=O)N4CCCC4)cc3)c3c(N)ncnc3n2C)c([C@@H]2CCCO2)c1] | A | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 511 | 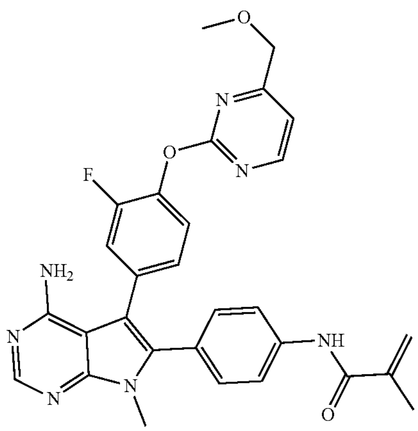 [SMILES: C=C(C)C(=O)Nc1ccc(-c2c(-c3ccc(Oc4nccc(COC)n4)c(F)c3)c3c(N)ncnc3n2C)cc1] | A | A |
| 512 | 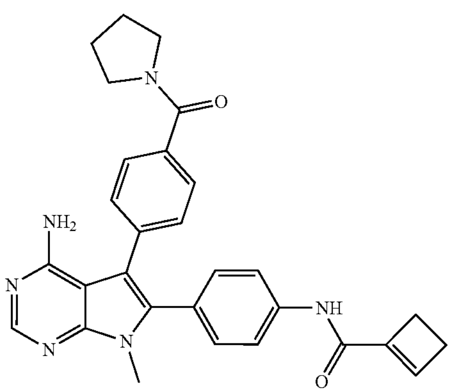 [SMILES: Cn1c(-c2ccc(NC(=O)C3=CCC3)cc2)c(-c2ccc(C(=O)N3CCCC3)cc2)c2c(N)ncnc21] | A | A |
| 513 | 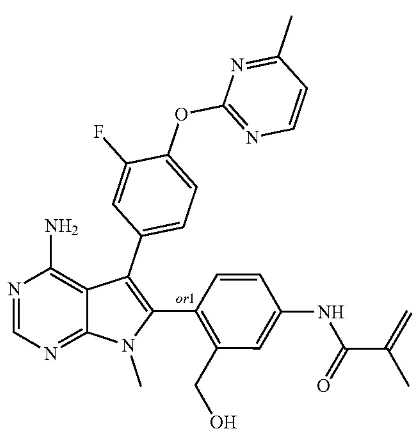 [SMILES: C=C(C)C(=O)Nc1ccc(-c2c(-c3ccc(Oc4nccc(C)n4)c(F)c3)c3c(N)ncnc3n2C)c(CO)c1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 514 | 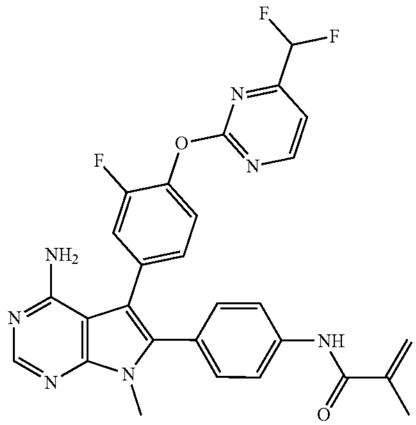 [SMILES: C=C(C)C(=O)Nc1ccc(-c2c(-c3ccc(Oc4nccc(C(F)F)n4)c(F)c3)c3c(N)ncnc3n2C)cc1] | A | A |
| 515 | 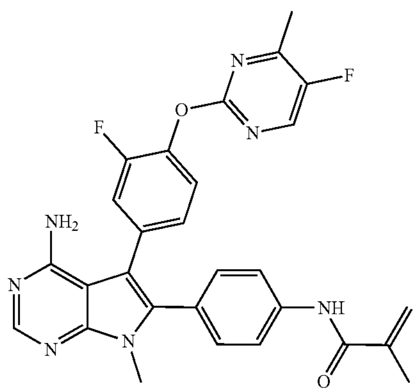 [SMILES: C=C(C)C(=O)Nc1ccc(-c2c(-c3ccc(Oc4ncc(F)c(C)n4)c(F)c3)c3c(N)ncnc3n2C)cc1] | A | A |
| 516 | 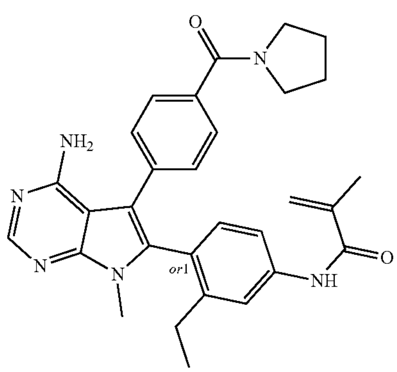 [SMILES: C=C(C)C(=O)Nc1ccc(-c2c(-c3ccc(C(=O)N4CCCC4)cc3)c3c(N)ncnc3n2C)c(CC)c1] | A | |
| 517 | 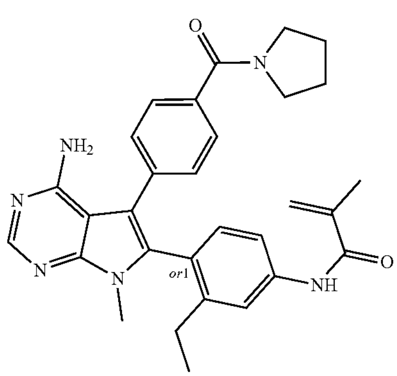 [SMILES: C=C(C)C(=O)Nc1ccc(-c2c(-c3ccc(C(=O)N4CCCC4)cc3)c3c(N)ncnc3n2C)c(CC)c1] | C | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 518 | 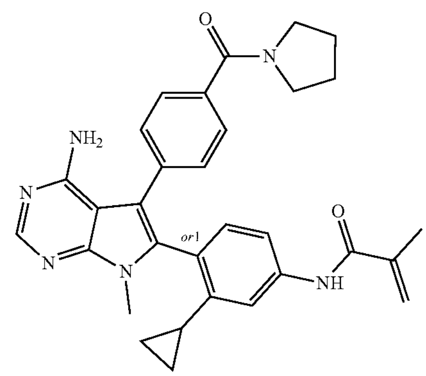 [SMILES: C=C(C)C(=O)Nc1ccc(-c2c(-c3ccc(C(=O)N4CCCC4)cc3)c3c(N)ncnc3n2C)c(C2CC2)c1] | A | |
| 519 | 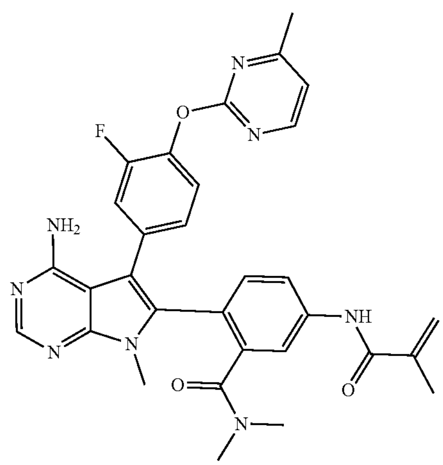 [SMILES: C=C(C)C(=O)Nc1ccc(-c2c(-c3ccc(Oc4nccc(C)n4)c(F)c3)c3c(N)ncnc3n2C)c(C(=O)N(C)C)c1] | D | |
| 520 | 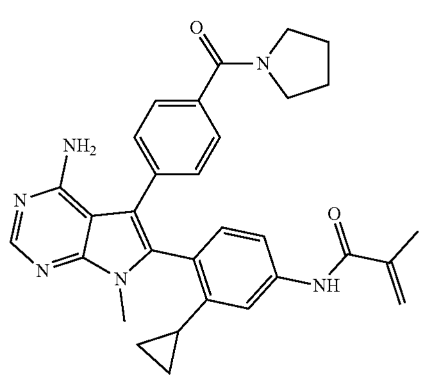 [SMILES: C=C(C)C(=O)Nc1ccc(-c2c(-c3ccc(C(=O)N4CCCC4)cc3)c3c(N)ncnc3n2C)c(C2CC2)c1] | B | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 521 | 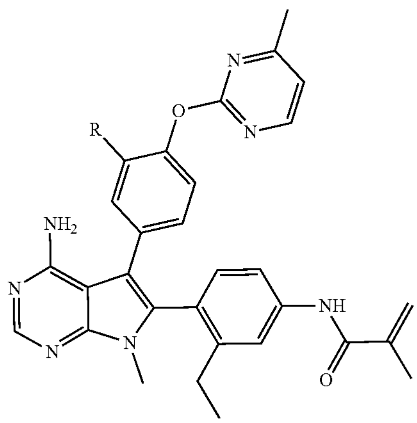 | A | A |
| 522 | 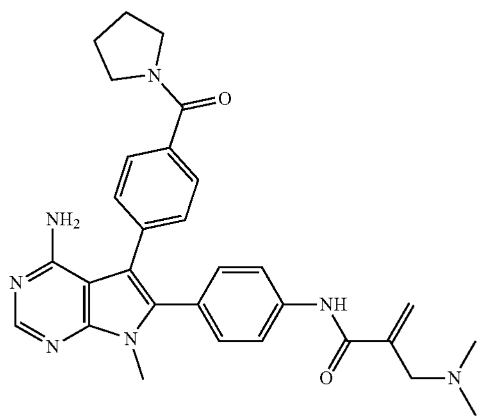 [SMILES: C=C(CN(C)C)C(=O)Nc1ccc(-c2c(-c3ccc(C(=O)N4CCCC4)cc3)c3c(N)ncnc3n2C)cc1] | A | A |
| 523 | 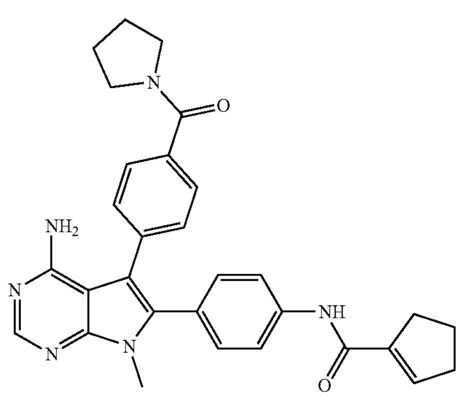 [SMILES: Cn1c(-c2ccc(NC(=O)C3=CCCC3)cc2)c(-c2ccc(C(=O)N3CCCC3)cc2)c2c(N)ncnc21] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 524 | 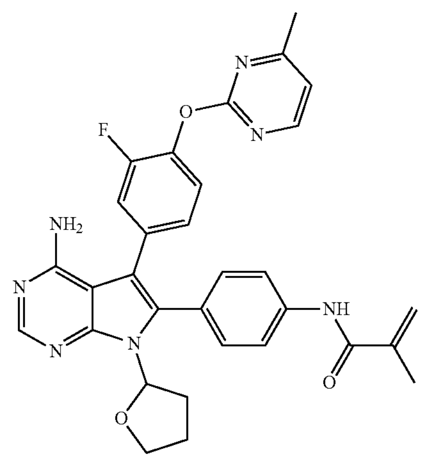 [SMILES: C=C(C)C(=O)Nc1ccc(-c2c(-c3ccc(Oc4nccc(C)n4)c(F)c3)c3c(N)ncnc3n2C2CCCO2)cc1] | A | A |
| 525 | 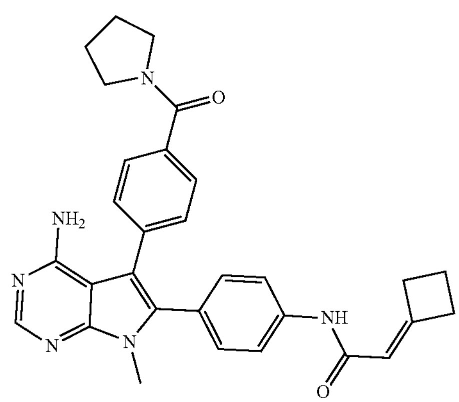 [SMILES: Cn1c(-c2ccc(NC(=O)C=C3CCC3)cc2)c(-c2ccc(C(=O)N3CCCC3)cc2)c2c(N)ncnc21] | D | |
| 526 | 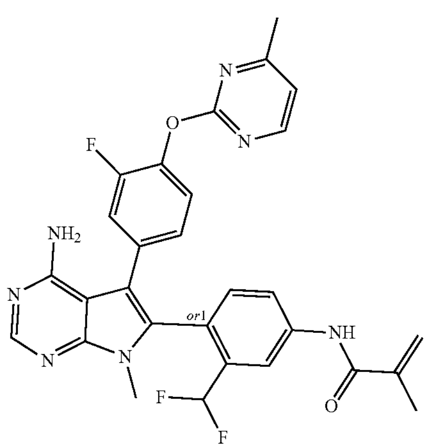 [SMILES: C=C(C)C(=O)Nc1ccc(-c2c(-c3ccc(Oc4nccc(C)n4)c(F)c3)c3c(N)ncnc3n2C)c(C(F)F)c1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 527 | 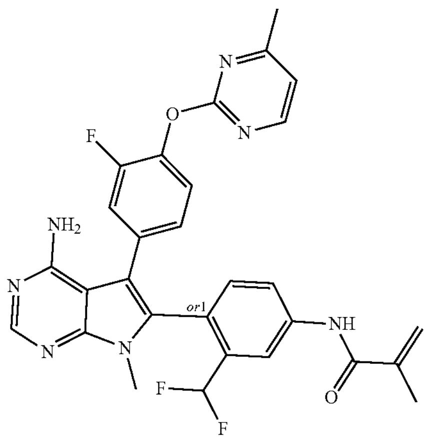 [SMILES: C=C(C)C(=O)Nc1ccc(-c2c(-c3ccc(Oc4nccc(C)n4)c(F)c3)c3c(N)ncnc3n2C)c(C(F)F)c1] | A | A |
| 528 | 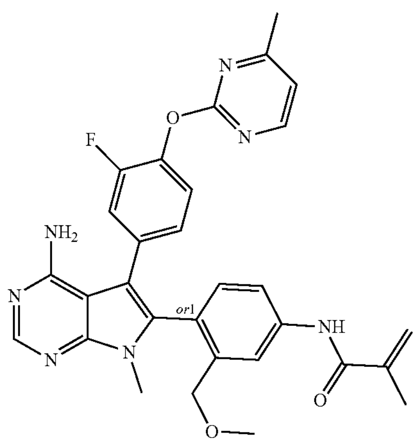 [SMILES: C=C(C)C(=O)Nc1ccc(-c2c(-c3ccc(Oc4nccc(C)n4)c(F)c3)c3c(N)ncnc3n2C)c(COC)c1] | A | |
| 529 | 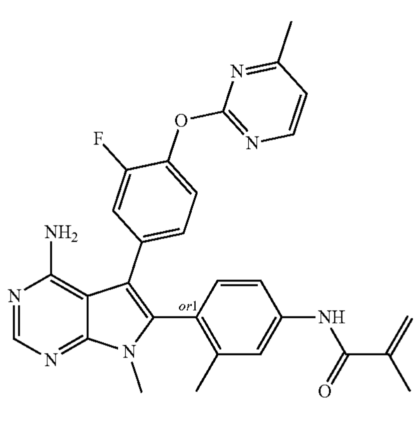 [SMILES: C=C(C)C(=O)Nc1ccc(-c2c(-c3ccc(Oc4nccc(C)n4)c(F)c3)c3c(N)ncnc3n2C)c(C)c1] | A | A |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 530 | 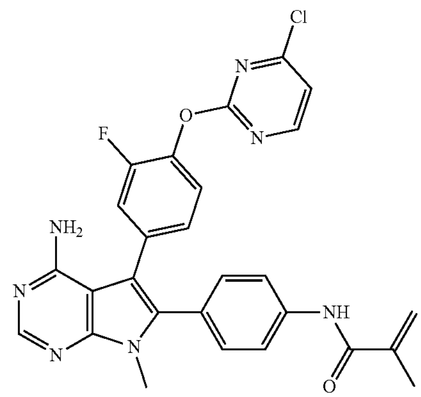 [SMILES: C=C(C)C(=O)Nc1ccc(-c2c(-c3ccc(Oc4nccc(Cl)n4)c(F)c3)c3c(N)ncnc3n2C)cc1] | A | A |
| 531 | 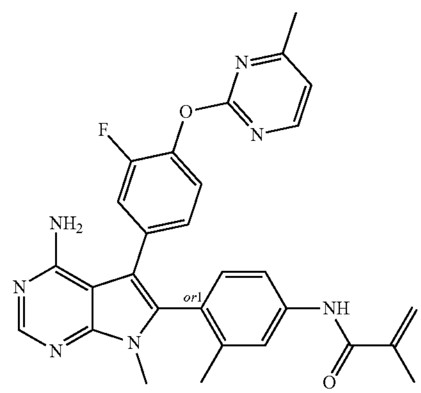 [SMILES: C=C(C)C(=O)Nc1ccc(-c2c(-c3ccc(Oc4nccc(C)n4)c(F)c3)c3c(N)ncnc3n2C)c(C)c1] | A | A |
| 532 | 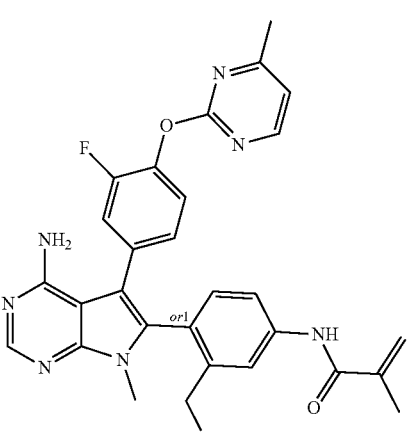 | A | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 533 | 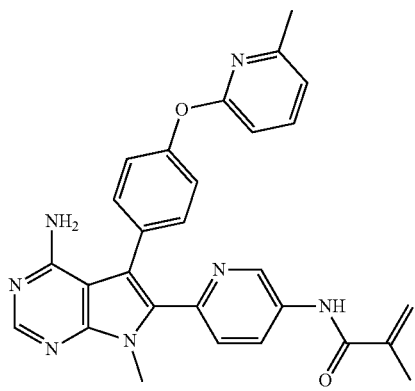 [SMILES: C=C(C)C(=O)Nc1ccc(-c2c(-c3ccc(Oc4cccc(C)n4)cc3)c3c(N)ncnc3n2C)nc1] | A | A |
| 534 | 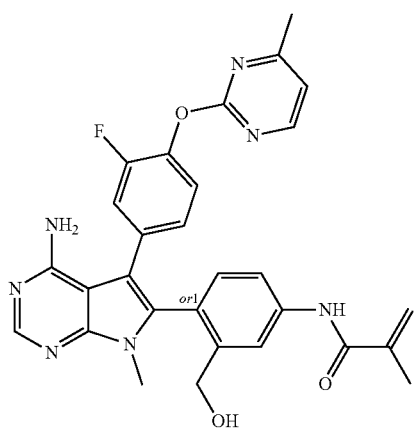 [SMILES: C=C(C)C(=O)Nc1ccc(-c2c(-c3ccc(Oc4nccc(C)n4)c(F)c3)c3c(N)ncnc3n2C)c(CO)c1] | A | |
| 535 | 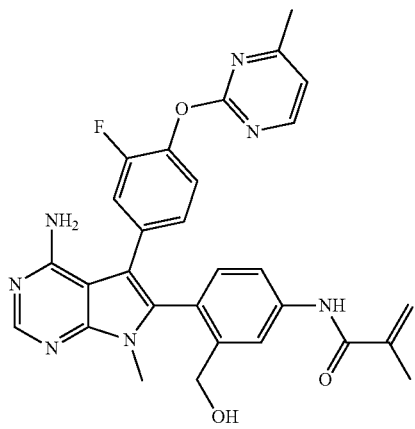 [SMILES: C=C(C)C(=O)Nc1ccc(-c2c(-c3ccc(Oc4nccc(C)n4)c(F)c3)c3c(N)ncnc3n2C)c(CO)c1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 536 | 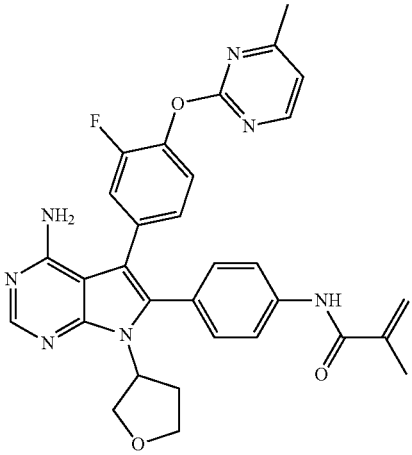 [SMILES: C=C(C)C(=O)Nc1ccc(-c2c(-c3ccc(Oc4nccc(C)n4)c(F)c3)c3c(N)ncnc3n2C2CCOC2)cc1] | A | |
| 537 | 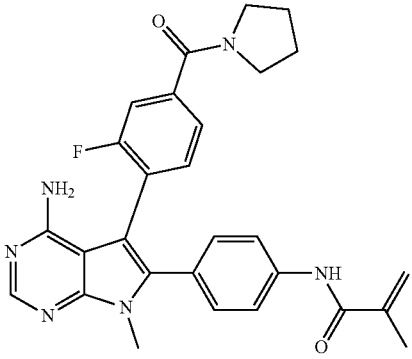 [SMILES: C=C(C)C(=O)Nc1ccc(-c2c(-c3ccc(C(=O)N4CCCC4)cc3F)c3c(N)ncnc3n2C)cc1] | B | A |
| 538 | 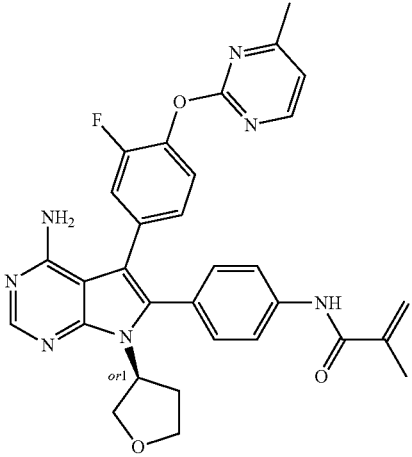 [SMILES: C=C(C)C(=O)Nc1ccc(-c2c(-c3ccc(Oc4nccc(C)n4)c(F)c3)c3c(N)ncnc3n2[C@H]2CCOC2)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 539 | 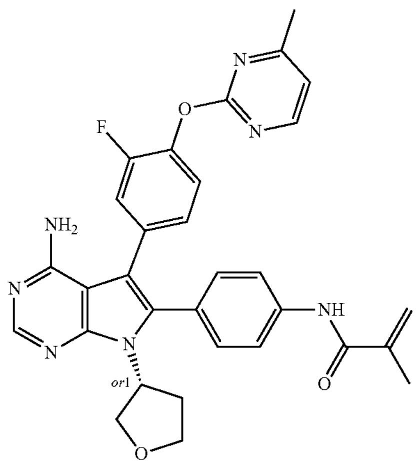 [SMILES: C=C(C)C(=O)Nc1ccc(-c2c(-c3ccc(Oc4nccc(C)n4)c(F)c3)c3c(N)ncnc3n2[C@@H]2CCOC2)cc1] | A | A |
| 540 | 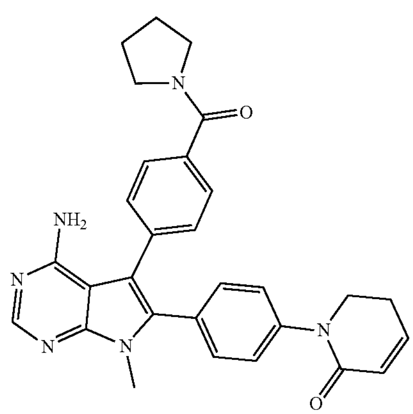 [SMILES: Cn1c(-c2ccc(N3CCC=CC3=O)cc2)c(-c2ccc(C(=O)N3CCCC3)cc2)c2c(N)ncnc21] | D | |
| 541 | 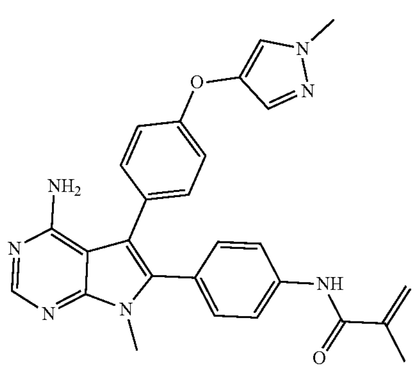 [SMILES: C=C(C)C(=O)Nc1ccc(-c2c(-c3ccc(Oc4cnn(C)c4)cc3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 542 | 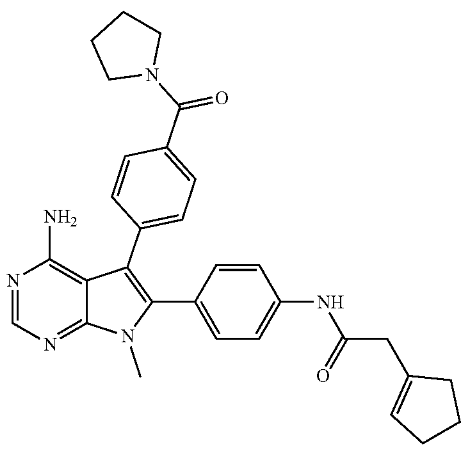 [SMILES: Cn1c(-c2ccc(NC(=O)CC3=CCCC3)cc2)c(-c2ccc(C(=O)N3CCCC3)cc2)c2c(N)ncnc21] | D | |
| 543 | 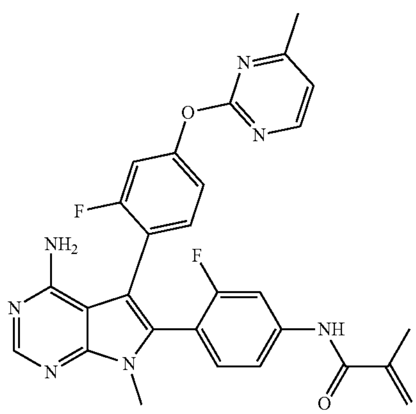 [SMILES: C=C(C)C(=O)Nc1ccc(-c2c(-c3ccc(Oc4nccc(C)n4)cc3F)c3c(N)ncnc3n2C)c(F)c1] | A | A |
| 544 | 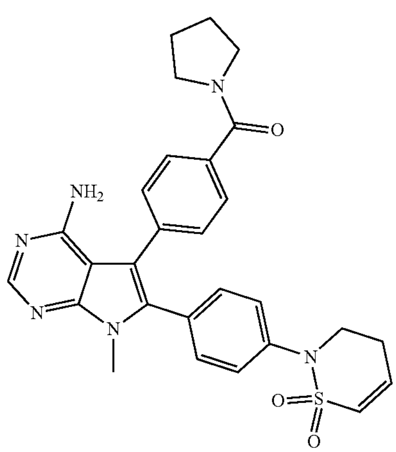 [SMILES: Cn1c(-c2ccc(N3CCC=CS3(=O)=O)cc2)c(-c2ccc(C(=O)N3CCCC3)cc2)c2c(N)ncnc21] | D | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 545 | 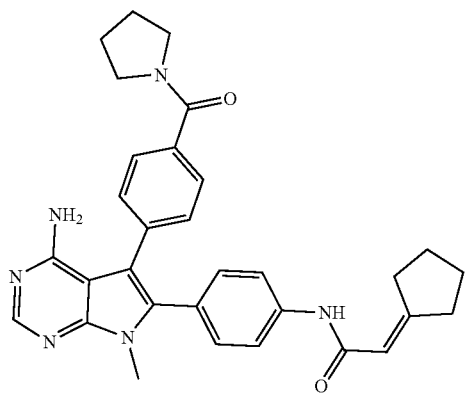 [SMILES: Cn1c(-c2ccc(NC(=O)C=C3CCCC3)cc2)c(-c2ccc(C(=O)N3CCCC3)cc2)c2c(N)ncnc21] | D | |
| 546 | 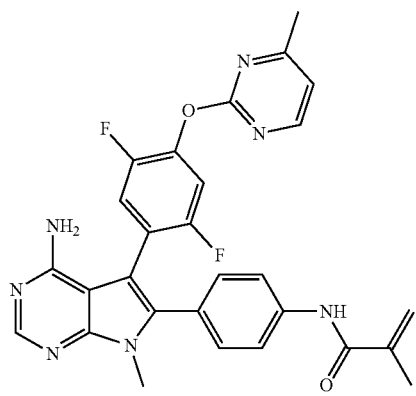 [SMILES: C=C(C)C(=O)Nc1ccc(-c2c(-c3cc(F)c(Oc4nccc(C)n4)cc3F)c3c(N)ncnc3n2C)cc1] | A | A |
| 547 | 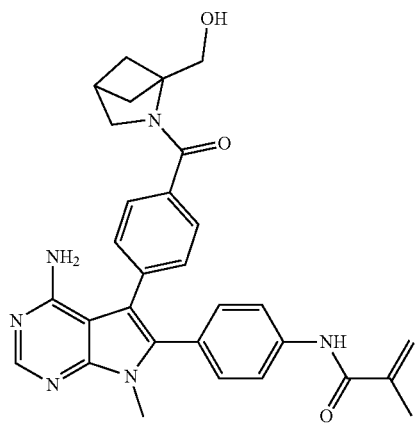 [SMILES: C=C(C)C(=O)Nc1ccc(-c2c(-c3ccc(C(=O)N4CC5CC4(CO)C5)cc3)c3c(N)ncnc3n2C)cc1] | C | |

| Example | Structure | Biochemical FGFR2 Caliper IC50 | Cell SNU-16 IC50 |
|---|---|---|---|
| 548 | 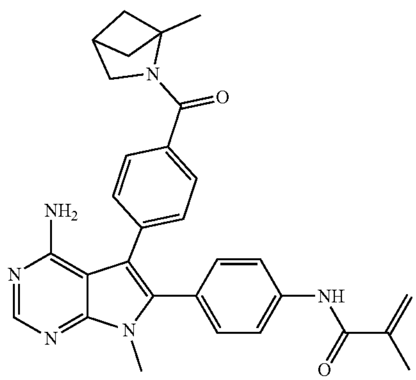 [SMILES: C=C(C)C(=O)Nc1ccc(-c2c(-c3ccc(C(=O)N4CC5CC4(C)C5)cc3)c3c(N)ncnc3n2C)cc1] | A | |
| 549 | 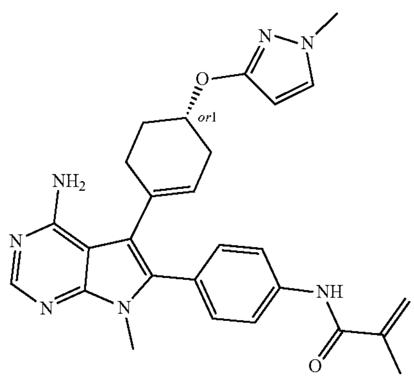 [SMILES: C=C(C)C(=O)Nc1ccc(-c2c(C3=CC[C@@H](Oc4ccn(C)n4)CC3)c3c(N)ncnc3n2C)cc1] | D | |
| 550 | 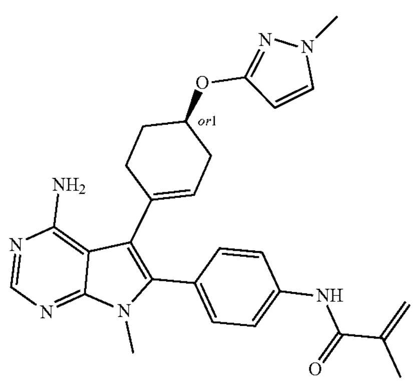 [SMILES: C=C(C)C(=O)Nc1ccc(-c2c(C3=CC[C@H](Oc4ccn(C)n4)CC3)c3c(N)ncnc3n2C)cc1] | B | A |
| 551 | 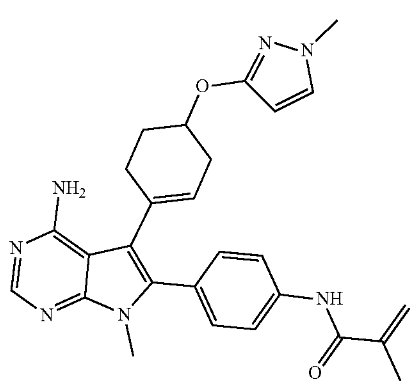 [SMILES: C=C(C)C(=O)Nc1ccc(-c2c(C3=CCC(Oc4ccn(C)n4)CC3)c3c(N)ncnc3n2C)cc1] | C | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 552 | 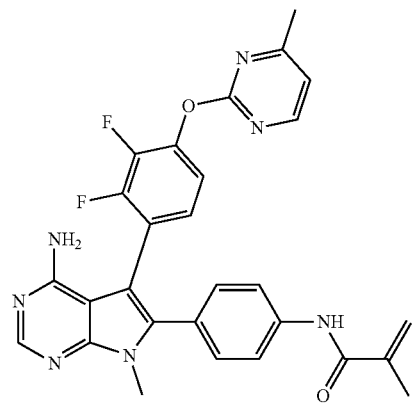 [SMILES: C=C(C)C(=O)Nc1ccc(-c2c(-c3ccc(Oc4nccc(C)n4)c(F)c3F)c3c(N)ncnc3n2C)cc1] | A | A |
| 553 | 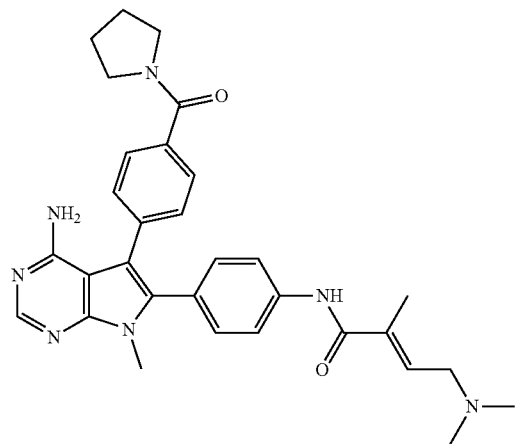 [SMILES: C/C(=C\CN(C)C)C(=O)Nc1ccc(-c2c(-c3ccc(C(=O)N4CCCC4)cc3)c3c(N)ncnc3n2C)cc1] | C | |
| 554 | 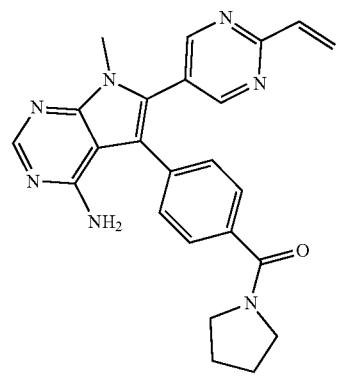 [SMILES: C=Cc1ncc(-c2c(-c3ccc(C(=O)N4CCCC4)cc3)c3c(N)ncnc3n2C)cn1] | C | C |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 555 | 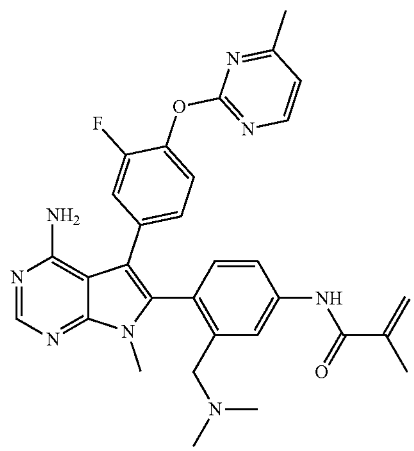 [SMILES: C=C(C)C(=O)Nc1ccc(-c2c(-c3ccc(Oc4nccc(C)n4)c(F)c3)c3c(N)ncnc3n2C)c(CN(C)C)c1] | A | |
| 556 | 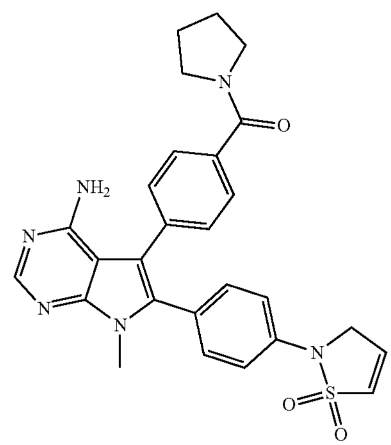 [SMILES: Cn1c(-c2ccc(N3CC=CS3(=O)=O)cc2)c(-c2ccc(C(=O)N3CCCC3)cc2)c2c(N)ncnc21] | C | |
| 557 | 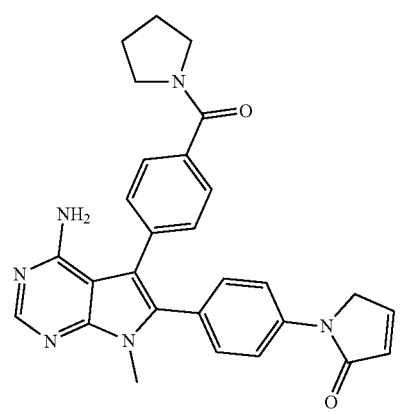 [SMILES: Cn1c(-c2ccc(N3CC=CC3=O)cc2)c(-c2ccc(C(=O)N3CCCC3)cc2)c2c(N)ncnc21] | D | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 558 | 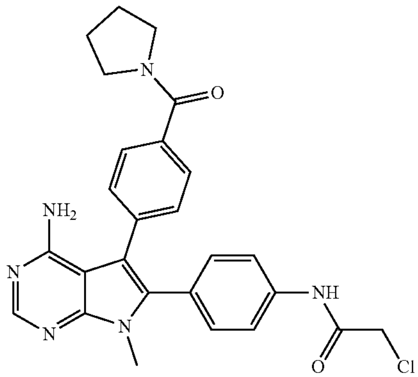 [SMILES: Cn1c(-c2ccc(NC(=O)CCl)cc2)c(-c2ccc(C(=O)N3CCCC3)cc2)c2c(N)ncnc21] | A | A |
| 559 | 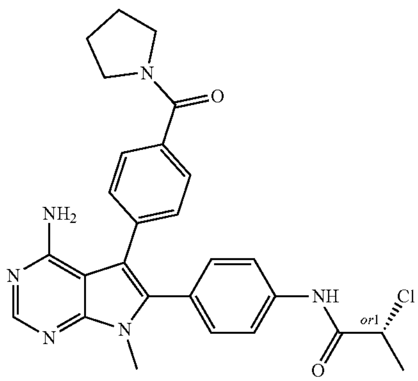 [SMILES: C[C@@H](Cl)C(=O)Nc1ccc(-c2c(-c3ccc(C(=O)N4CCCC4)cc3)c3c(N)ncnc3n2C)cc1] | C | C |
| 560 | 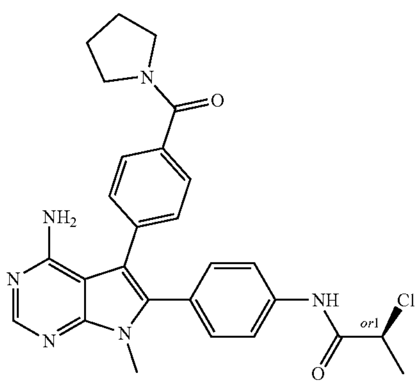 [SMILES: C[C@H](Cl)C(=O)Nc1ccc(-c2c(-c3ccc(C(=O)N4CCCC4)cc3)c3c(N)ncnc3n2C)cc1] | B | B |
| 561 | 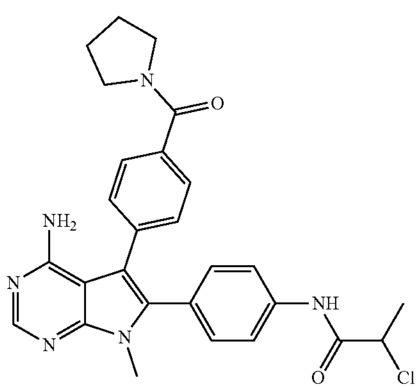 [SMILES: CC(Cl)C(=O)Nc1ccc(-c2c(-c3ccc(C(=O)N4CCCC4)cc3)c3c(N)ncnc3n2C)cc1] | C | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 562 | 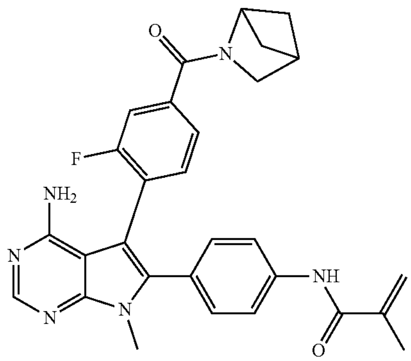 [SMILES: C=C(C)C(=O)Nc1ccc(-c2c(-c3ccc(C(=O)N4CC5CC4C5)cc3F)c3c(N)ncnc3n2C)cc1] | B | A |
| 563 | 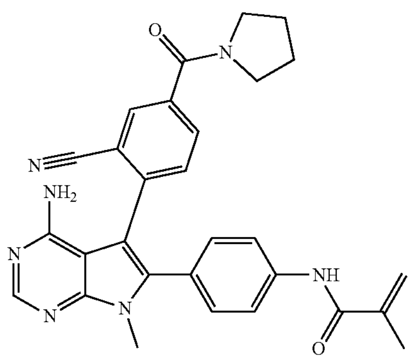 [SMILES: C=C(C)C(=O)Nc1ccc(-c2c(-c3ccc(C(=O)N4CCCC4)cc3C#N)c3c(N)ncnc3n2C)cc1] | D | C |
| 564 | 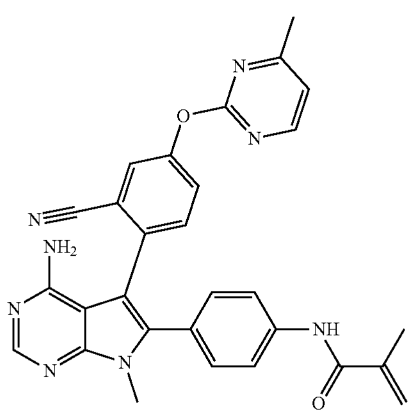 [SMILES: C=C(C)C(=O)Nc1ccc(-c2c(-c3ccc(Oc4nccc(C)n4)cc3C#N)c3c(N)ncnc3n2C)cc1] | D | C |
| 565 | 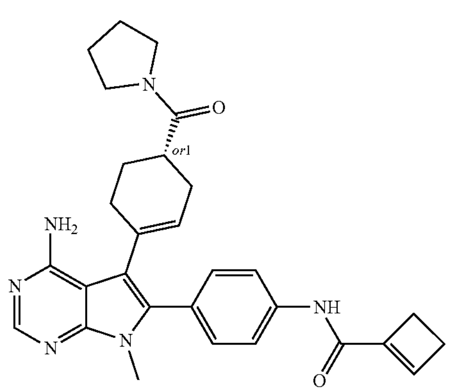 [SMILES: Cn1c(-c2ccc(NC(=O)C3=CCC3)cc2)c(C2=CC[C@@H](C(=O)N3CCCC3)CC2)c2c(N)ncnc21] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 566 | 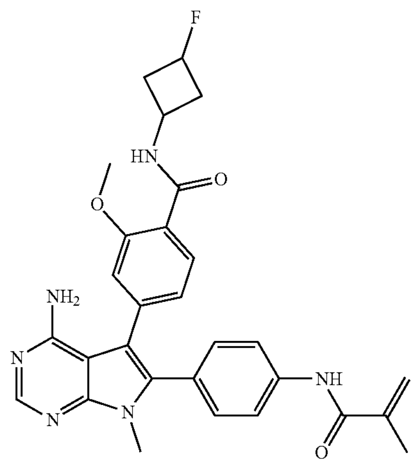 [SMILES: C=C(C)C(=O)Nc1ccc(-c2c(-c3ccc(C(=O)NC4CC(F)C4)c(OC)c3)c3c(N)ncnc3n2C)cc1] | A | A |
| 567 | 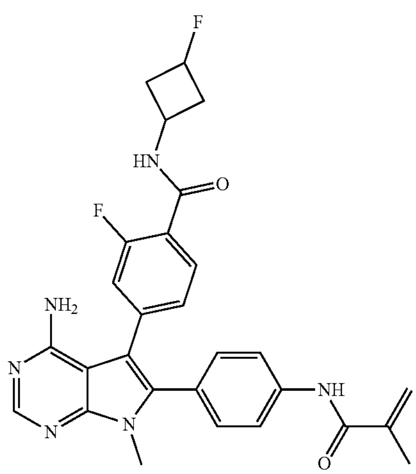 [SMILES: C=C(C)C(=O)Nc1ccc(-c2c(-c3ccc(C(=O)NC4CC(F)C4)c(F)c3)c3c(N)ncnc3n2C)cc1] | B | A |
| 568 | 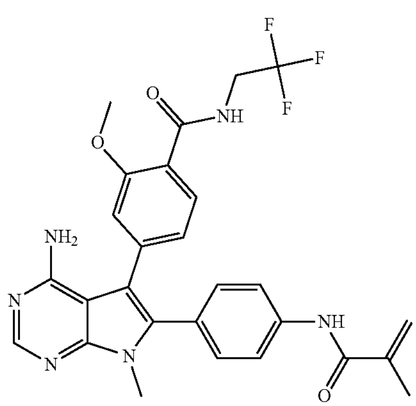 [SMILES: C=C(C)C(=O)Nc1ccc(-c2c(-c3ccc(C(=O)NCC(F)(F)F)c(OC)c3)c3c(N)ncnc3n2C)cc1] | A | A |

| Example | Structure | Biochemical FGFR2 Caliper IC50 | Cell SNU-16 IC50 |
|---|---|---|---|
| 569 | 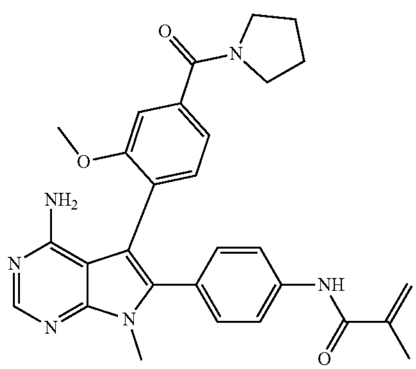 [SMILES: C=C(C)C(=O)Nc1ccc(-c2c(-c3ccc(C(=O)N4CCCC4)cc3OC)c3c(N)ncnc3n2C)cc1] | B | B |
| 570 | 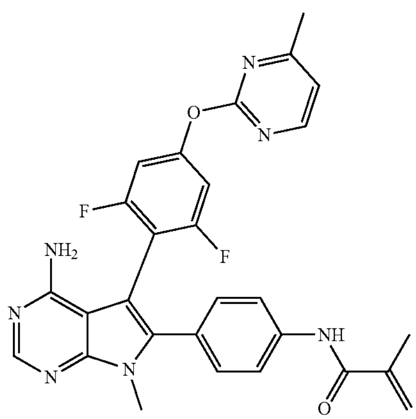 [SMILES: C=C(C)C(=O)Nc1ccc(-c2c(-c3c(F)cc(Oc4nccc(C)n4)cc3F)c3c(N)ncnc3n2C)cc1] | A | A |
| 571 | 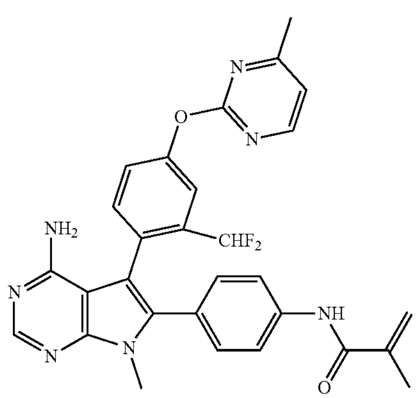 [SMILES: C=C(C)C(=O)Nc1ccc(-c2c(-c3ccc(Oc4nccc(C)n4)cc3C(F)F)c3c(N)ncnc3n2C)cc1] | D | C |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 572 | 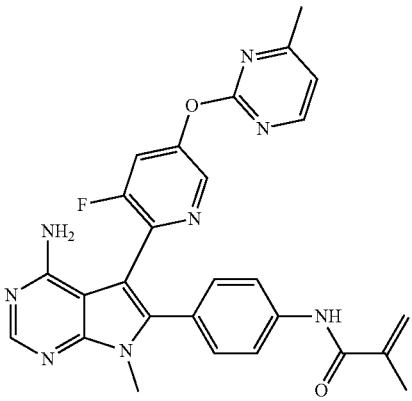 [SMILES: C=C(C)C(=O)Nc1ccc(-c2c(-c3ncc(Oc4nccc(C)n4)cc3F)c3c(N)ncnc3n2C)cc1] | A | A |
| 573 | 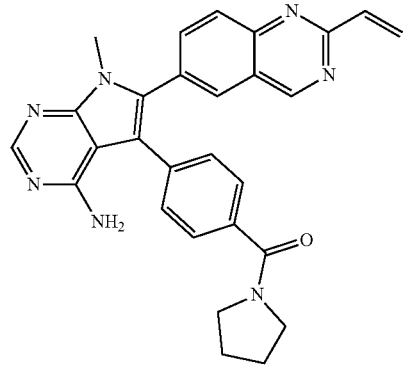 [SMILES: C=Cc1ncc2cc(-c3c(-c4ccc(C(=O)N5CCCC5)cc4)c4c(N)ncnc4n3C)ccc2n1] | D | C |
| 574 | 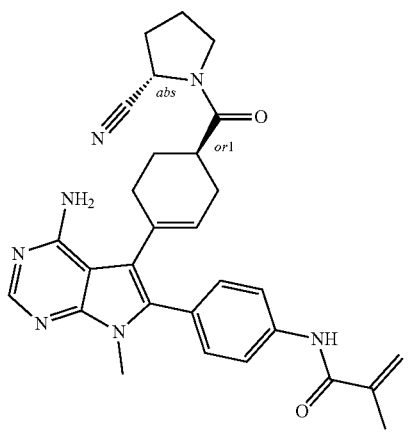 [SMILES: C=C(C)C(=O)Nc1ccc(-c2c(C3=CC[C@H](C(=O)N4CCC[C@H]4C#N)CC3)c3c(N)ncnc3n2C)cc1] | C | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 575 | 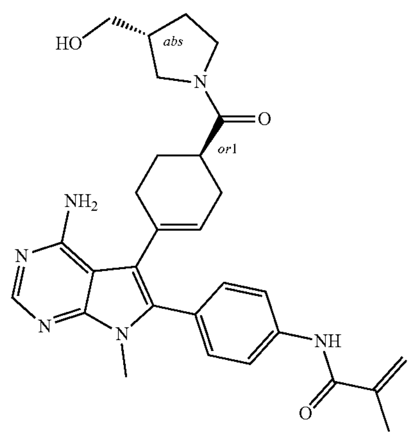 [SMILES: C=C(C)C(=O)Nc1ccc(-c2c(C3=CC[C@H](C(=O)N4CC[C@@H](CO)C4)CC3)c3c(N)ncnc3n2C)cc1] | D | |
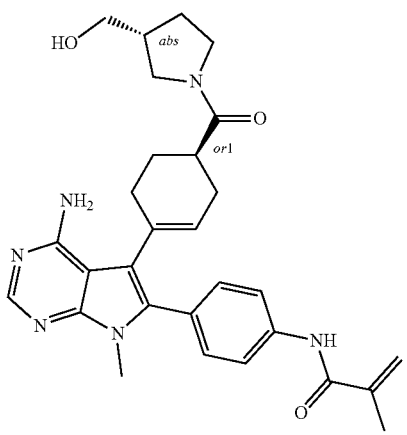
| 576 | | D | |
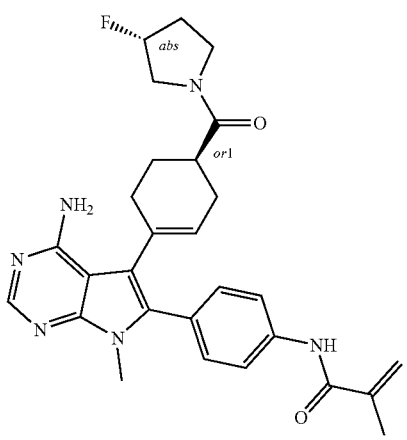 [SMILES: C=C(C)C(=O)Nc1ccc(-c2c(C3=CC[C@H](C(=O)N4CC[C@@H](F)C4)CC3)c3c(N)ncnc3n2C)cc1]
| 577 | | D | |
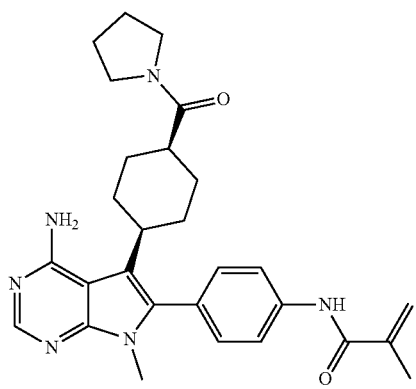 [SMILES: C=C(C)C(=O)Nc1ccc(-c2c([C@H]3CC[C@@H](C(=O)N4CCCC4)CC3)c3c(N)ncnc3n2C)cc1]

TABLE 1-continued
Representative Compounds of the Invention with Bioactivity Data.
| Example | Structure | Biochemical FGFR2 Caliper IC50 | Cell SNU-16 IC50 |
|---|---|---|---|
| 578 | 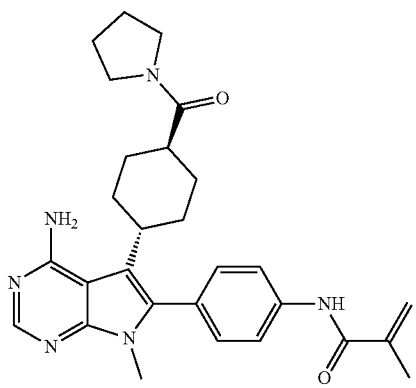 [SMILES: C=C(C)C(=O)Nc1ccc(-c2c([C@H]3CC[C@H](C(=O)N4CCCC4)CC3)c3c(N)ncnc3n2C)cc1] | D | |
| 579 | 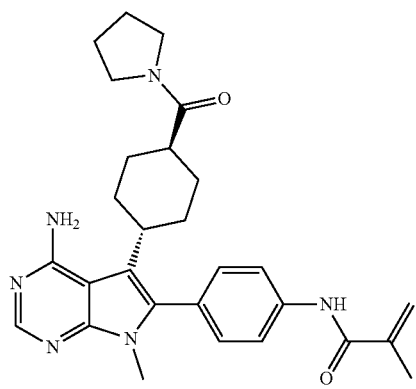 | C | |
| 580 | 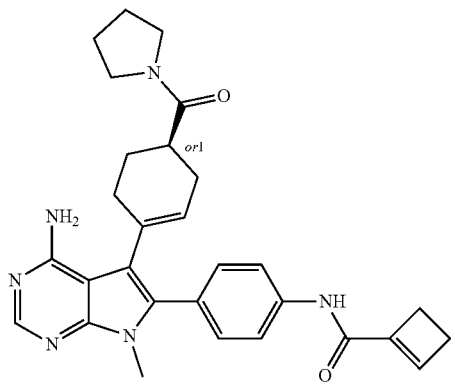 [SMILES: Cn1c(-c2ccc(NC(=O)C3=CCC3)cc2)c(C2=CC[C@H](C(=O)N3CCCC3)CC2)c2c(N)ncnc21] | D | |
| | 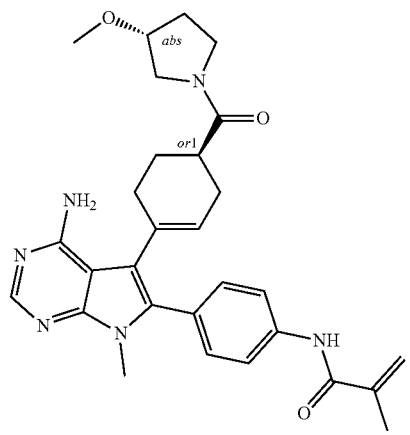 [SMILES: C=C(C)C(=O)Nc1ccc(-c2c(C3=CC[C@H](C(=O)N4CC[C@@H](OC)C4)CC3)c3c(N)ncnc3n2C)cc1] | | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 581 | 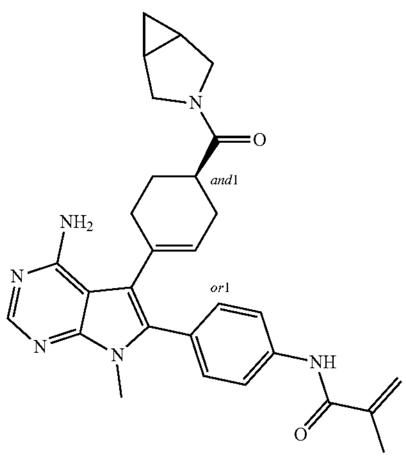 [SMILES: C=C(C)C(=O)Nc1ccc(-c2c(C3=CC[C@H](C(=O)N4CC5CC5C4)CC3)c3c(N)ncnc3n2C)cc1] | D | |
| 582 | 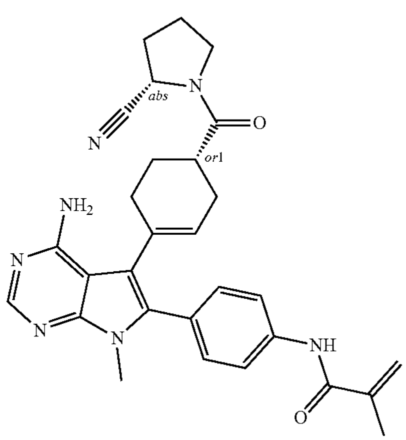 [SMILES: C=C(C)C(=O)Nc1ccc(-c2c(C3=CC[C@@H](C(=O)N4CCC[C@H]4C#N)CC3)c3c(N)ncnc3n2C)cc1] | A | A |
| 583 | 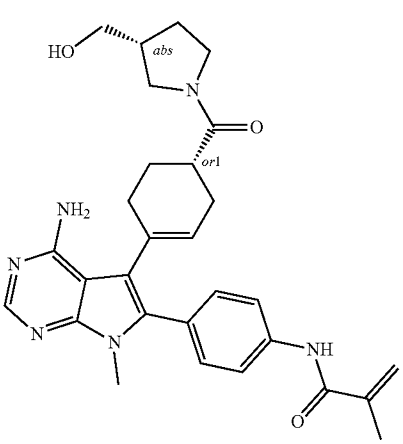 [SMILES: C=C(C)C(=O)Nc1ccc(-c2c(C3=CC[C@@H](C(=O)N4CC[C@@H](CO)C4)CC3)c3c(N)ncnc3n2C)cc1] | C | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 584 | 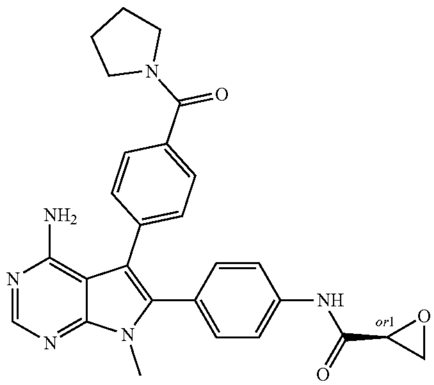 [SMILES: Cn1c(-c2ccc(NC(=O)[C@@H]3CO3)cc2)c(-c2ccc(C(=O)N3CCCC3)cc2)c2c(N)ncnc21] | B | C |
| 585 | 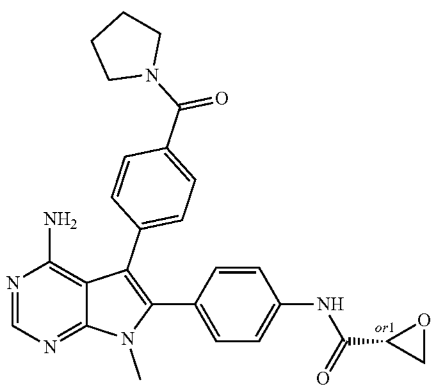 [SMILES: Cn1c(-c2ccc(NC(=O)[C@H]3CO3)cc2)c(-c2ccc(C(=O)N3CCCC3)cc2)c2c(N)ncnc21] | B | |
| 586 | 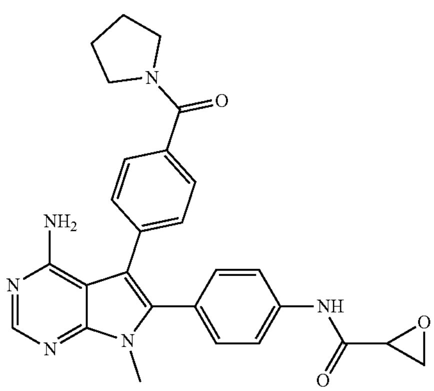 [SMILES: Cn1c(-c2ccc(NC(=O)C3CO3)cc2)c(-c2ccc(C(=O)N3CCCC3)cc2)c2c(N)ncnc21] | B | |
| 587 | 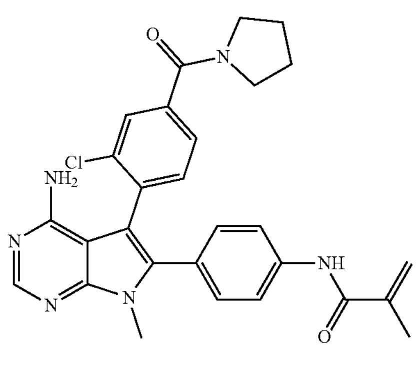 [SMILES: C=C(C)C(=O)Nc1ccc(-c2c(-c3ccc(C(=O)N4CCCC4)cc3Cl)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 588 | 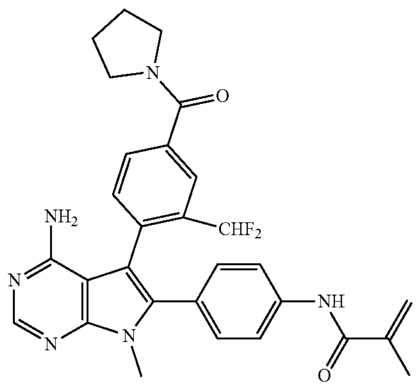 [SMILES: C=C(C)C(=O)Nc1ccc(-c2c(-c3ccc(C(=O)N4CCCC4)cc3C(F)F)c3c(N)ncnc3n2C)cc1] | D | |
| 589 | 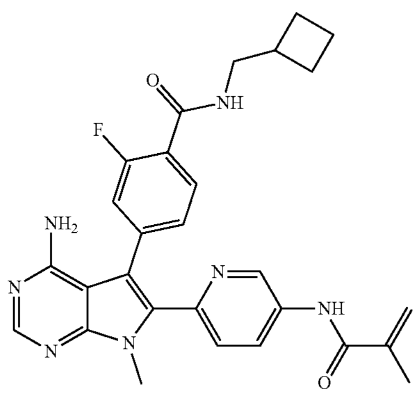 [SMILES: C=C(C)C(=O)Nc1ccc(-c2c(-c3ccc(C(=O)NCC4CCC4)c(F)c3)c3c(N)ncnc3n2C)nc1] | A | A |
| 590 | 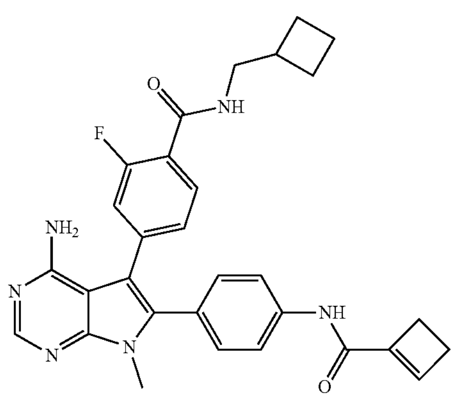 [SMILES: Cn1c(-c2ccc(NC(=O)C3=CCC3)cc2)c(-c2ccc(C(=O)NCC3CCC3)c(F)c2)c2c(N)ncnc21] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 591 | 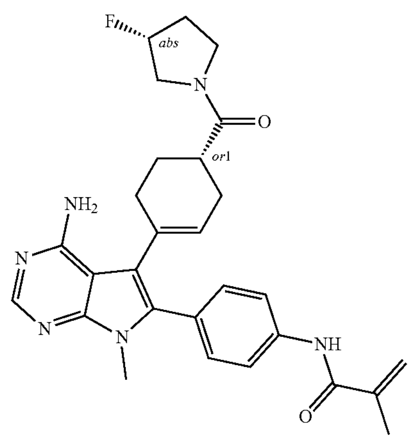 [SMILES: C=C(C)C(=O)Nc1ccc(-c2c(C3=CC[C@@H](C(=O)N4CC[C@@H](F)C4)CC3)c3c(N)ncnc3n2C)cc1] | B | |
| 592 | 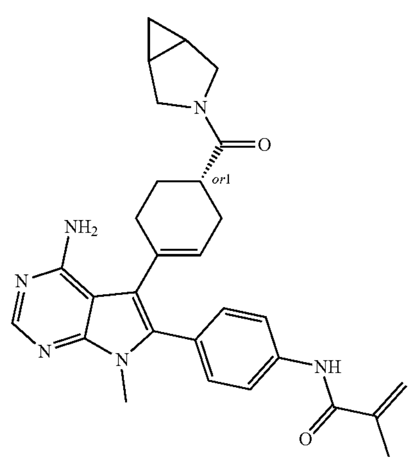 [SMILES: C=C(C)C(=O)Nc1ccc(-c2c(C3=CC[C@@H](C(=O)N4CC5CC5C4)CC3)c3c(N)ncnc3n2C)cc1] | A | A |
| 593 | 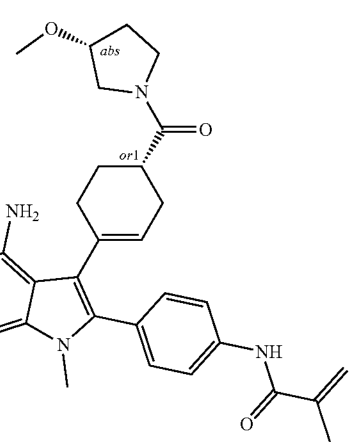 | C | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 594 | 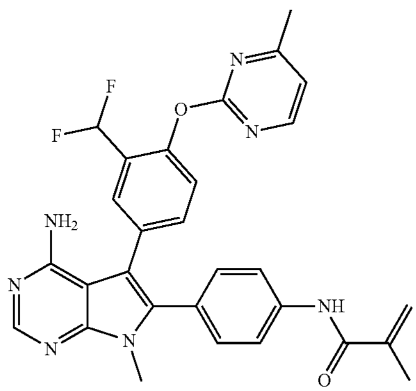 [SMILES: C=C(C)C(=O)Nc1ccc(-c2c(-c3ccc(Oc4nccc(C)n4)c(C(F)F)c3)c3c(N)ncnc3n2C)cc1] | B | A |
| 595 | 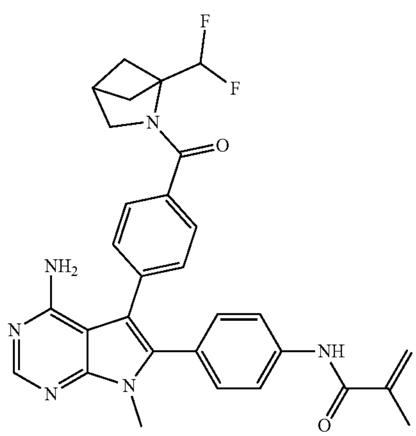 [SMILES: C=C(C)C(=O)Nc1ccc(-c2c(-c3ccc(C(=O)N4CC5CC4(C(F)F)C5)cc3)c3c(N)ncnc3n2C)cc1] | A | |
| 596 | 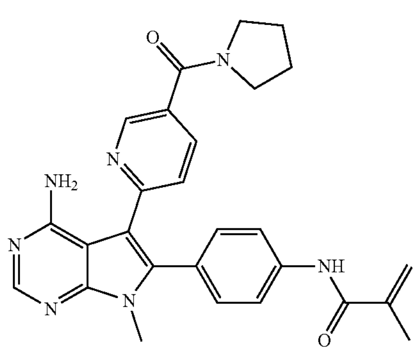 [SMILES: C=C(C)C(=O)Nc1ccc(-c2c(-c3ccc(C(=O)N4CCCC4)cn3)c3c(N)ncnc3n2C)cc1] | A | |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 597 | 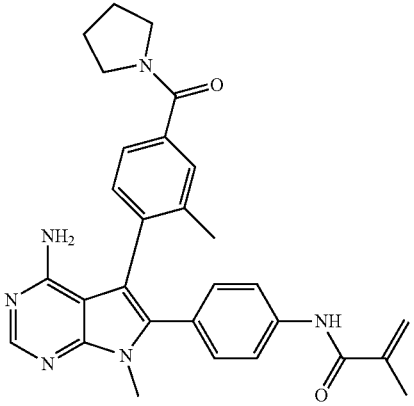 [SMILES: C=C(C)C(=O)Nc1ccc(-c2c(-c3ccc(C(=O)N4CCCC4)cc3C)c3c(N)ncnc3n2C)cc1] | D | |
| 598 | 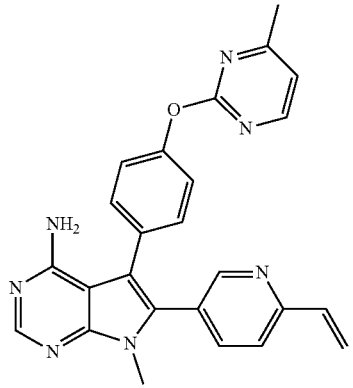 [SMILES: C=Cc1ccc(-c2c(-c3ccc(Oc4nccc(C)n4)cc3)c3c(N)ncnc3n2C)cn1] | B | C |
| 599 | 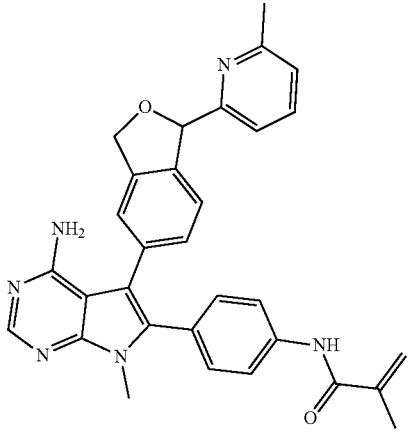 [SMILES: C=C(C)C(=O)Nc1ccc(-c2c(-c3ccc4c(c3)COC4c3cccc(C)n3)c3c(N)ncnc3n2C)cc1] | B | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 600 | 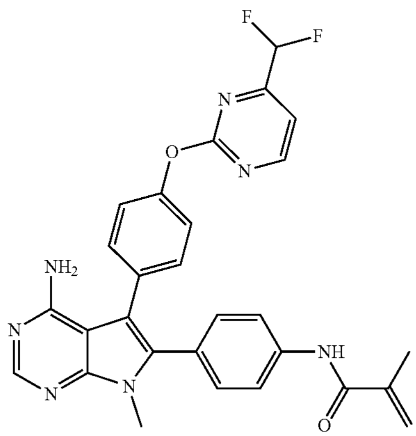 [SMILES: C=C(C)C(=O)Nc1ccc(-c2c(-c3ccc(Oc4nccc(C(F)F)n4)cc3)c3c(N)ncnc3n2C)cc1] | A | A |
| 601 | 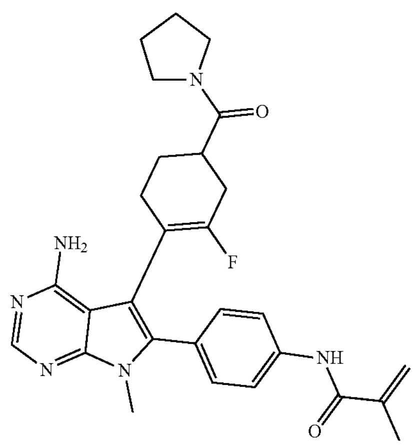 [SMILES: C=C(C)C(=O)Nc1ccc(-c2c(C3=C(F)CC(C(=O)N4CCCC4)CC3)c3c(N)ncnc3n2C)cc1] | D | C |
| 602 | 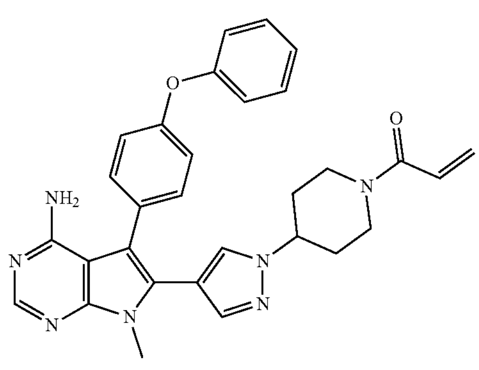 [SMILES: C=CC(=O)N1CCC(n2cc(-c3c(-c4ccc(Oc5ccccc5)cc4)c4c(N)ncnc4n3C)cn2)CC1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 603 | 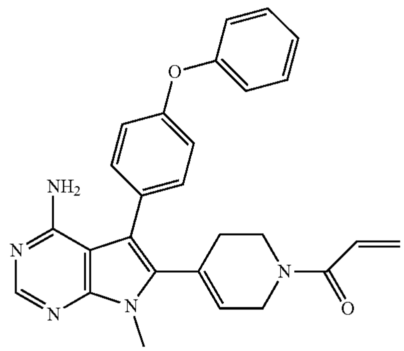 [SMILES: C=CC(=O)N1CC=C(c2c(-c3ccc(Oc4ccccc4)cc3)c3c(N)ncnc3n2C)CC1] | A | A |
| 604 | 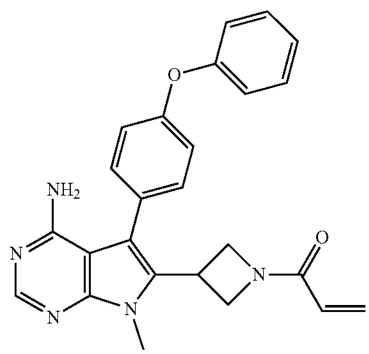 [SMILES: C=CC(=O)N1CC(c2c(-c3ccc(Oc4ccccc4)cc3)c3c(N)ncnc3n2C)C1] | A | |
| 605 | 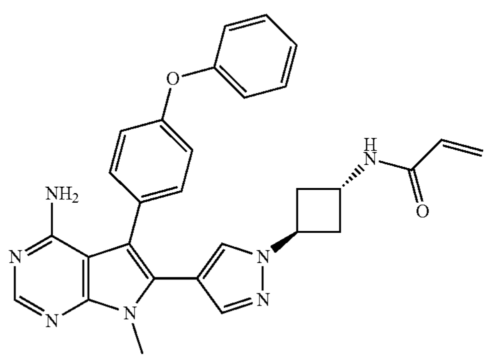 [SMILES: C=CC(=O)N[C@H]1C[C@H](n2cc(-c3c(-c4ccc(Oc5ccccc5)cc4)c4c(N)ncnc4n3C)cn2)C1] | A | |
| 606 | 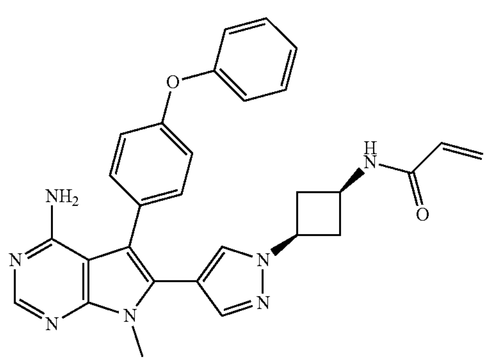 [SMILES: C=CC(=O)N[C@H]1C[C@@H](n2cc(-c3c(-c4ccc(Oc5ccccc5)cc4)c4c(N)ncnc4n3C)cn2)C1] | A | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 607 | 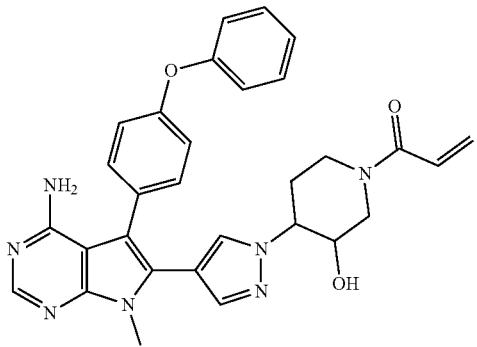 [SMILES: C=CC(=O)N1CCC(n2cc(-c3c(-c4ccc(Oc5ccccc5)cc4)c4c(N)ncnc4n3C)cn2)C(O)C1] | A | A |
| 608 | 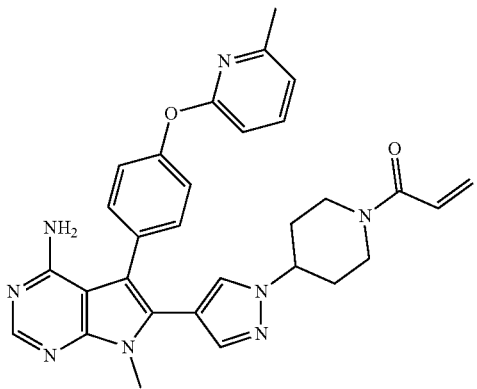 [SMILES: C=CC(=O)N1CCC(n2cc(-c3c(-c4ccc(Oc5cccc(C)n5)cc4)c4c(N)ncnc4n3C)cn2)CC1] | A | A |
| 609 | 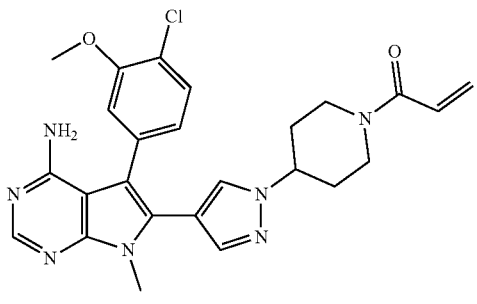 | | C |
| 610 | 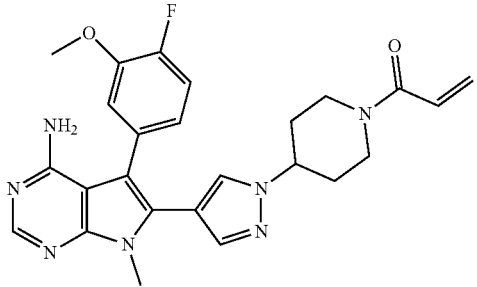 [SMILES: C=CC(=O)N1CCC(n2cc(-c3c(-c4ccc(F)c(OC)c4)c4c(N)ncnc4n3C)cn2)CC1] | | C |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 611 | 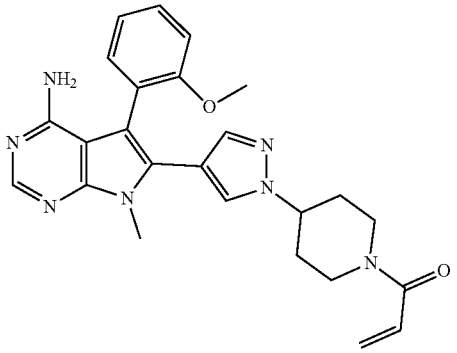 [SMILES: C=CC(=O)N1CCC(n2cc(-c3c(-c4ccccc4OC)c4c(N)ncnc4n3C)cn2)CC1] | D | |
| 612 | 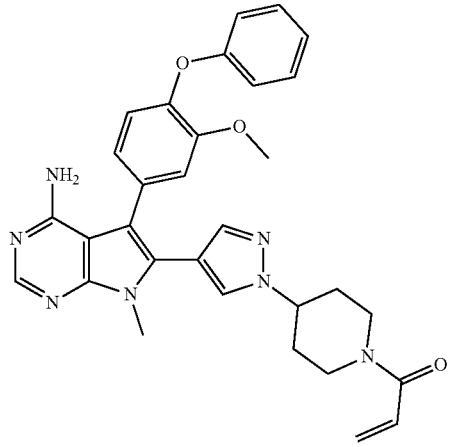 [SMILES: C=CC(=O)N1CCC(n2cc(-c3c(-c4ccc(Oc5ccccc5)c(OC)c4)c4c(N)ncnc4n3C)cn2)CC1] | B | |
| 613 | 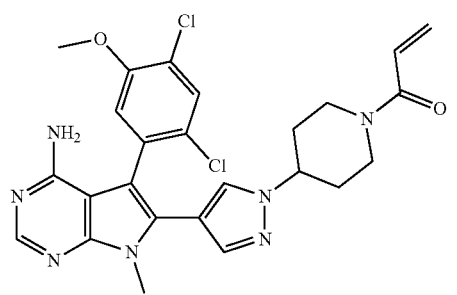 [SMILES: C=CC(=O)N1CCC(n2cc(-c3c(-c4cc(OC)c(Cl)cc4Cl)c4c(N)ncnc4n3C)cn2)CC1] | D | |
| 614 | 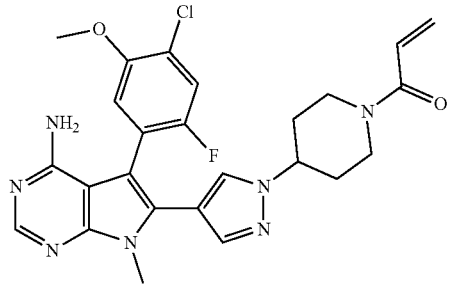 [SMILES: C=CC(=O)N1CCC(n2cc(-c3c(-c4cc(OC)c(Cl)cc4F)c4c(N)ncnc4n3C)cn2)CC1] | D | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 615 | 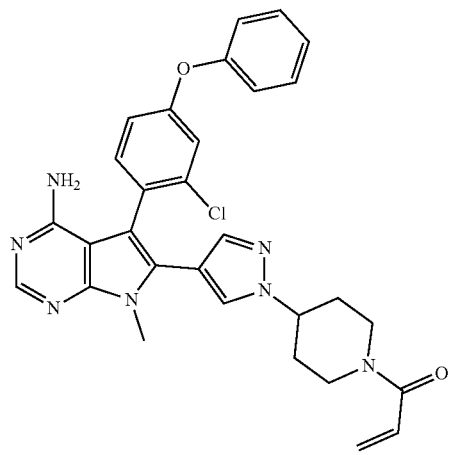 [SMILES: C=CC(=O)N1CCC(n2cc(-c3c(-c4ccc(Oc5ccccc5)cc4Cl)c4c(N)ncnc4n3C)cn2)CC1] | A | |
| 616 | 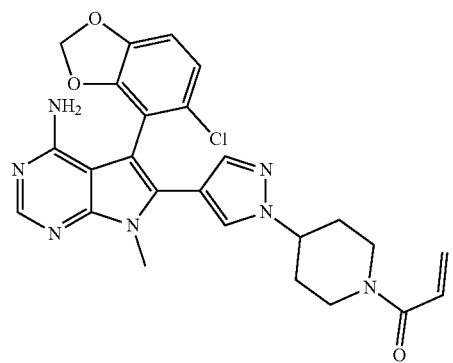 [SMILES: C=CC(=O)N1CCC(n2cc(-c3c(-c4c(Cl)ccc5c4OCO5)c4c(N)ncnc4n3C)cn2)CC1] | D | |
| 617 | 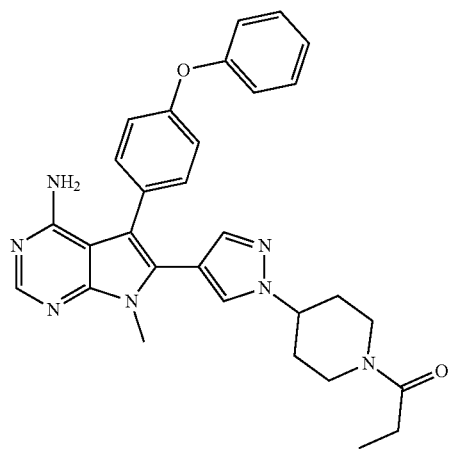 [SMILES: CCC(=O)N1CCC(n2cc(-c3c(-c4ccc(Oc5ccccc5)cc4)c4c(N)ncnc4n3C)cn2)CC1] | B | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 618 | 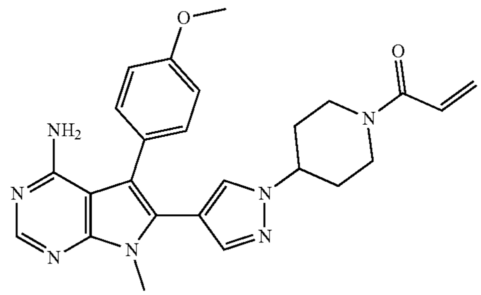 [SMILES: C=CC(=O)N1CCC(n2cc(-c3c(-c4ccc(OC)cc4)c4c(N)ncnc4n3C)cn2)CC1] | A | A |
| 619 | 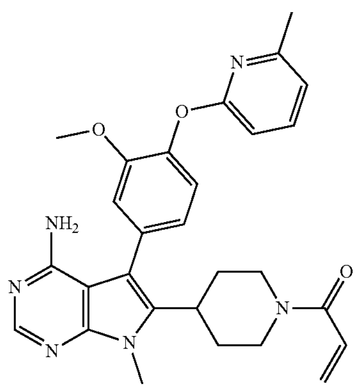 [SMILES: C=CC(=O)N1CCC(c2c(-c3ccc(Oc4cccc(C)n4)c(OC)c3)c3c(N)ncnc3n2C)CC1] | B | B |
| 620 | 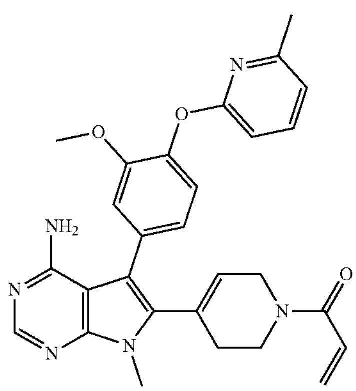 [SMILES: C=CC(=O)N1CC=C(c2c(-c3ccc(Oc4cccc(C)n4)c(OC)c3)c3c(N)ncnc3n2C)CC1] | A | A |
| 621 | 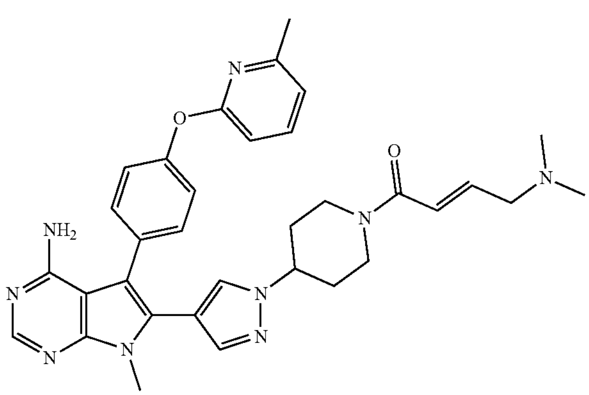 [SMILES: Cc1cccc(Oc2ccc(-c3c(-c4cnn(C5CCN(C(=O)/C=C/CN(C)C)CC5)c4)n(C)c4ncnc(N)c34)cc2)n1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 622 | 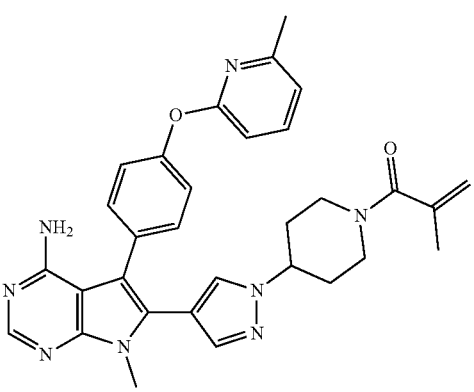 [SMILES: C=C(C)C(=O)N1CCC(n2cc(-c3c(-c4ccc(Oc5cccc(C)n5)cc4)c4c(N)ncnc4n3C)cn2)CC1] | C | D |
| 623 | 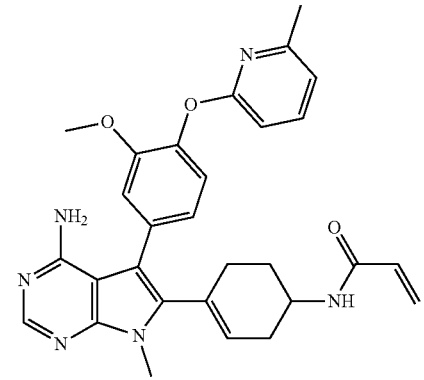 [SMILES: C=CC(=O)NC1CC=C(c2c(-c3ccc(Oc4cccc(C)n4)c(OC)c3)c3c(N)ncnc3n2C)CC1] | B | B |
| 624 | 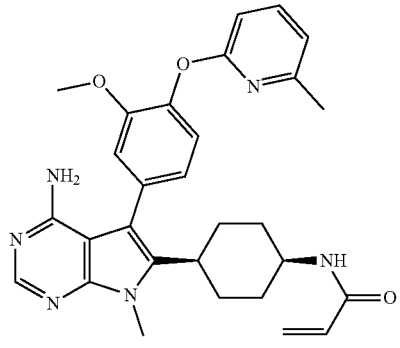 [SMILES: C=CC(=O)N[C@H]1CC[C@@H](c2c(-c3ccc(Oc4cccc(C)n4)c(OC)c3)c3c(N)ncnc3n2C)CC1] | D | |
| 625 | 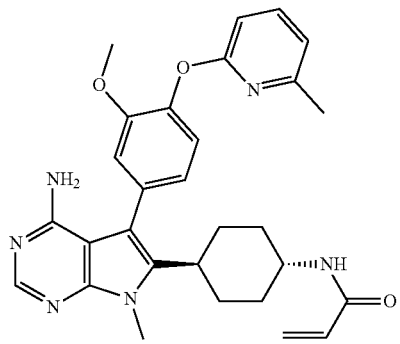 [SMILES: C=CC(=O)N[C@H]1CC[C@H](c2c(-c3ccc(Oc4cccc(C)n4)c(OC)c3)c3c(N)ncnc3n2C)CC1] | C | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 626 | 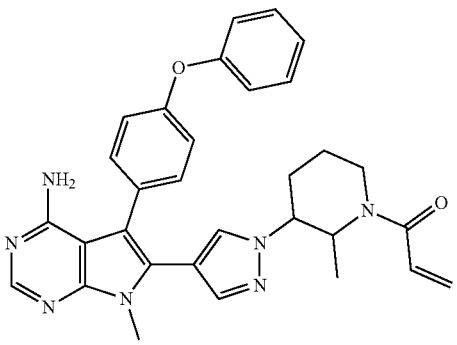 [SMILES: C=CC(=O)N1CCCC(n2cc(-c3c(-c4ccc(Oc5ccccc5)cc4)c4c(N)ncnc4n3C)cn2)C1C] | B | C |
| 627 | 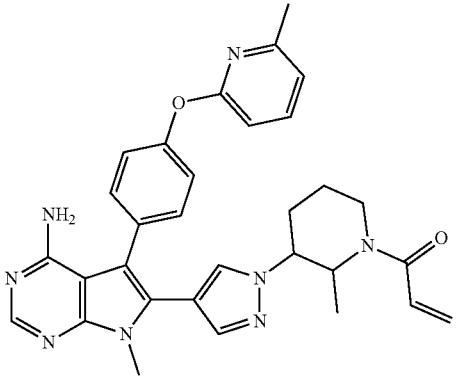 | A | A |
| 628 | 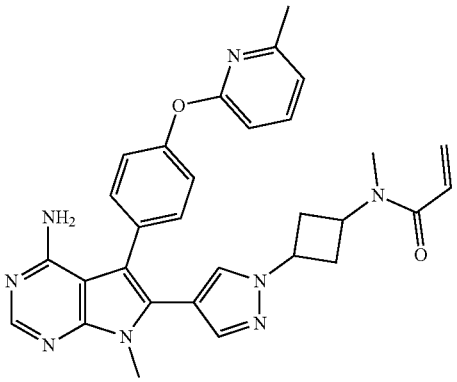 [SMILES: C=CC(=O)N(C)C1CC(n2cc(-c3c(-c4ccc(Oc5cccc(C)n5)cc4)c4c(N)ncnc4n3C)cn2)C1] | A | A |
| 629 | 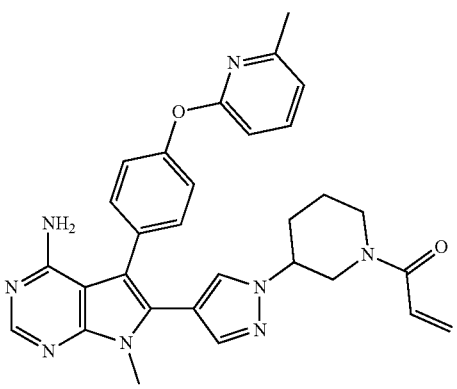 [SMILES: C=CC(=O)N1CCCC(n2cc(-c3c(-c4ccc(Oc5cccc(C)n5)cc4)c4c(N)ncnc4n3C)cn2)C1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 630 | 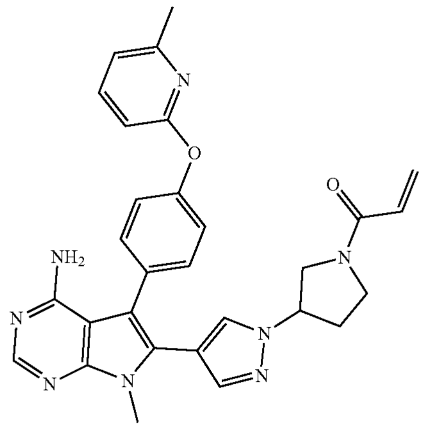 [SMILES: C=CC(=O)N1CCC(n2cc(-c3c(-c4ccc(Oc5cccc(C)n5)cc4)c4c(N)ncnc4n3C)cn2)C1] | A | A |
| 631 | 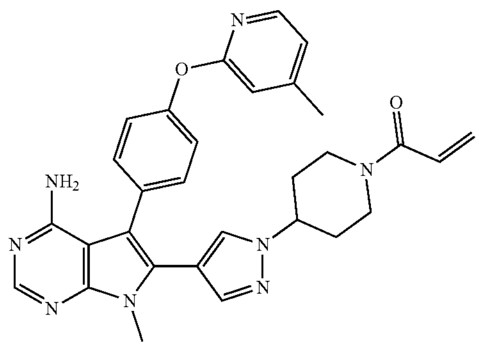 [SMILES: C=CC(=O)N1CCC(n2cc(-c3c(-c4ccc(Oc5cc(C)ccn5)cc4)c4c(N)ncnc4n3C)cn2)CC1] | B | B |
| 632 | 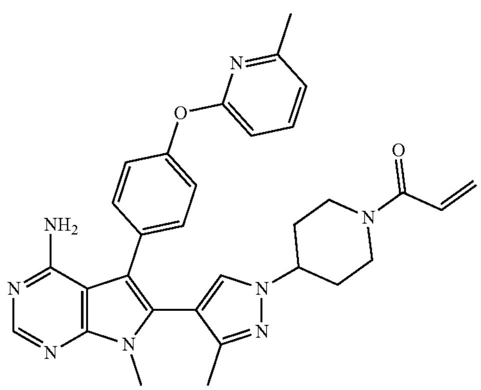 [SMILES: C=CC(=O)N1CCC(n2cc(-c3c(-c4ccc(Oc5cccc(C)n5)cc4)c4c(N)ncnc4n3C)c(C)n2)CC1] | A | A |
| 633 | 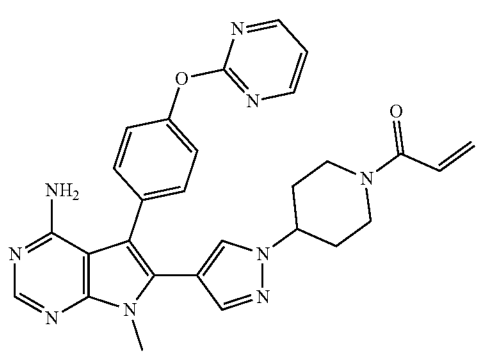 | B | B |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 634 | 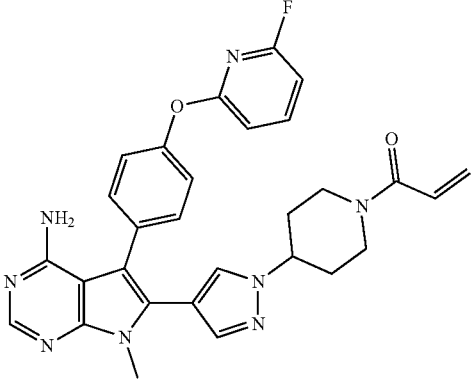 [SMILES: C=CC(=O)N1CCC(n2cc(-c3c(-c4ccc(Oc5cccc(F)n5)cc4)c4c(N)ncnc4n3C)cn2)CC1] | A | A |
| 635 | 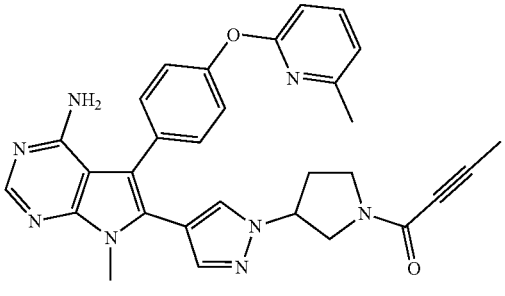 [SMILES: CC#CC(=O)N1CCC(n2cc(-c3c(-c4ccc(Oc5cccc(C)n5)cc4)c4c(N)ncnc4n3C)cn2)C1] | B | A |
| 636 | 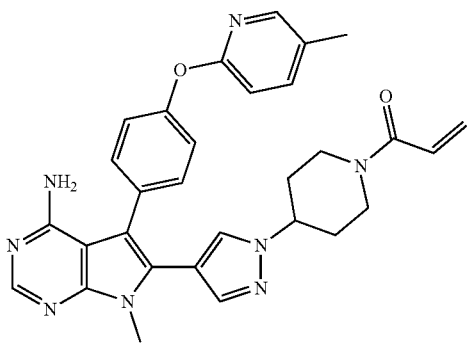 [SMILES: C=CC(=O)N1CCC(n2cc(-c3c(-c4ccc(Oc5ccc(C)cn5)cc4)c4c(N)ncnc4n3C)cn2)CC1] | B | A |
| 637 | 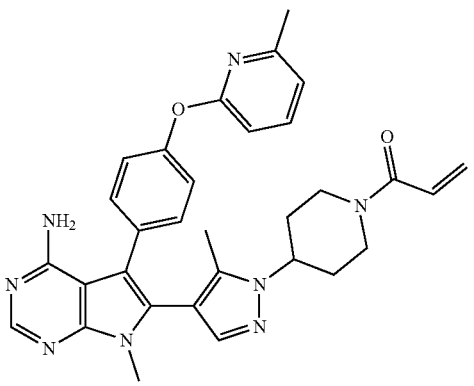 [SMILES: C=CC(=O)N1CCC(n2ncc(-c3c(-c4ccc(Oc5cccc(C)n5)cc4)c4c(N)ncnc4n3C)c2C)CC1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 638 | 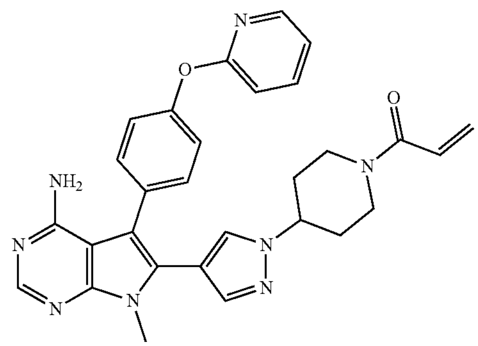 [SMILES: C=CC(=O)N1CCC(n2cc(-c3c(-c4ccc(Oc5ccccn5)cc4)c4c(N)ncnc4n3C)cn2)CC1] | A | A |
| 639 | 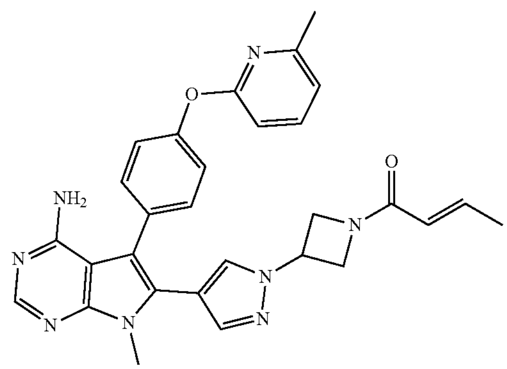 [SMILES: C/C=C/C(=O)N1CC(n2cc(-c3c(-c4ccc(Oc5cccc(C)n5)cc4)c4c(N)ncnc4n3C)cn2)C1] | A | A |
| 640 | 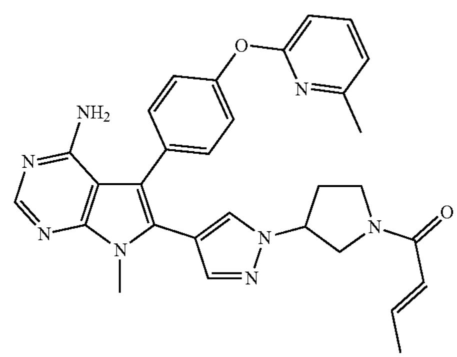 [SMILES: C/C=C/C(=O)N1CCC(n2cc(-c3c(-c4ccc(Oc5cccc(C)n5)cc4)c4c(N)ncnc4n3C)cn2)C1] | A | A |
| 641 | 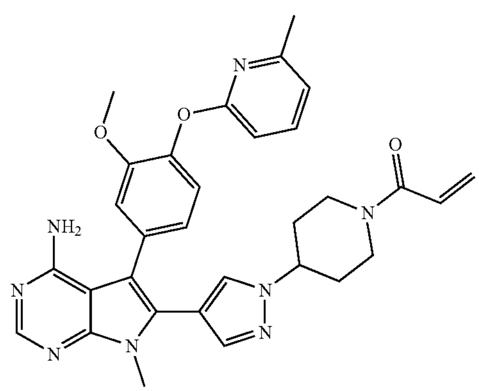 [SMILES: C=CC(=O)N1CCC(n2cc(-c3c(-c4ccc(Oc5cccc(C)n5)c(OC)c4)c4c(N)ncnc4n3C)cn2)CC1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 642 | 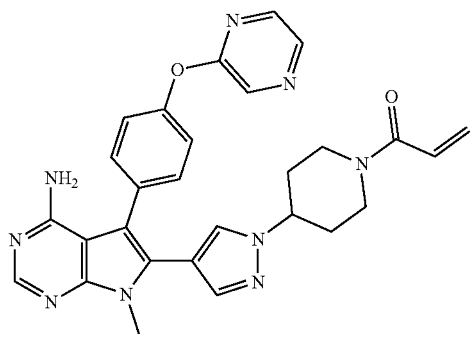 [SMILES: C=CC(=O)N1CCC(n2cc(-c3c(-c4ccc(Oc5cnccn5)cc4)c4c(N)ncnc4n3C)cn2)CC1] | C | B |
| 643 | 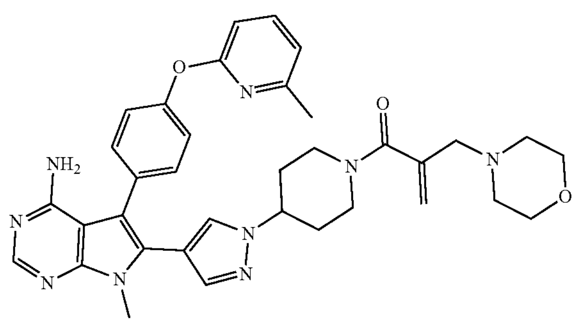 [SMILES: C=C(CN1CCOCC1)C(=O)N1CCC(n2cc(-c3c(-c4ccc(Oc5cccc(C)n5)cc4)c4c(N)ncnc4n3C)cn2)CC1] | C | C |
| 644 | 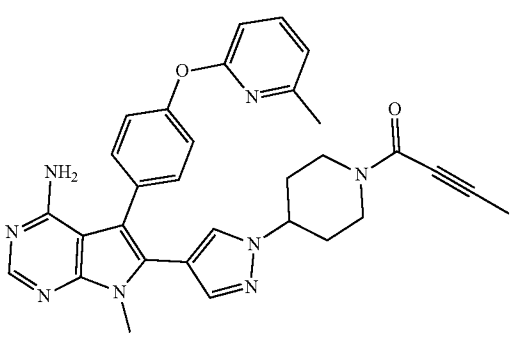 [SMILES: CC#CC(=O)N1CCC(n2cc(-c3c(-c4ccc(Oc5cccc(C)n5)cc4)c4c(N)ncnc4n3C)cn2)CC1] | C | C |
| 645 | 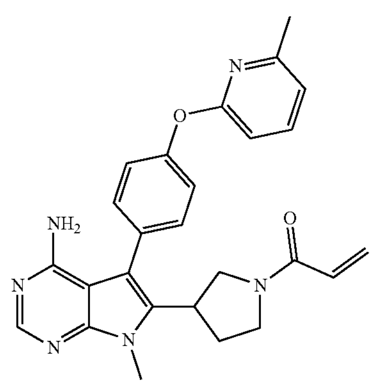 [SMILES: C=CC(=O)N1CCC(c2c(-c3ccc(Oc4cccc(C)n4)cc3)c3c(N)ncnc3n2C)C1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 646 | 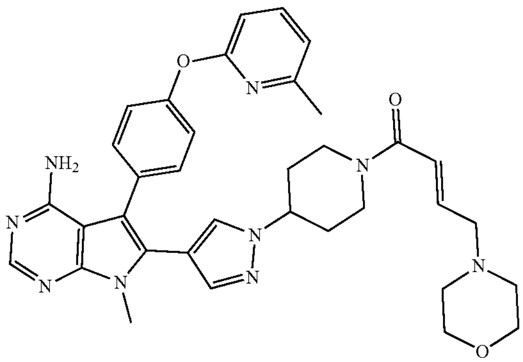 [SMILES: Cc1cccc(Oc2ccc(-c3c(-c4cnn(C5CCN(C(=O)/C=C/CN6CCOCC6)CC5)c4)n(C)c4ncnc(N)c34)cc2)n1] | B | B |
| 647 | 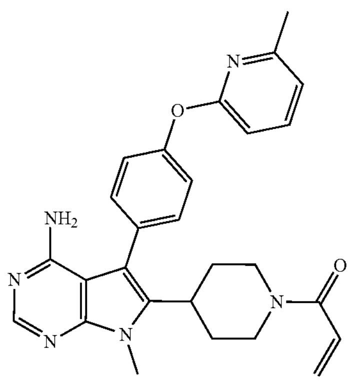 [SMILES: C=CC(=O)N1CCC(c2c(-c3ccc(Oc4cccc(C)n4)cc3)c3c(N)ncnc3n2C)CC1] | A | A |
| 648 | 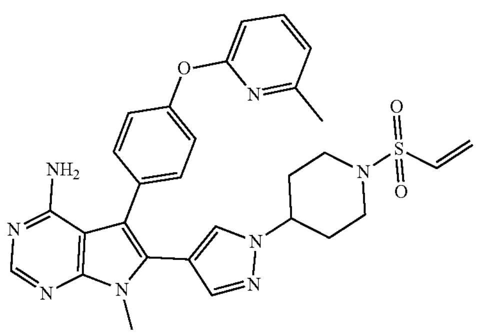 [SMILES: C=CS(=O)(=O)N1CCC(n2cc(-c3c(-c4ccc(Oc5cccc(C)n5)cc4)c4c(N)ncnc4n3C)cn2)CC1] | A | B |
| 649 | 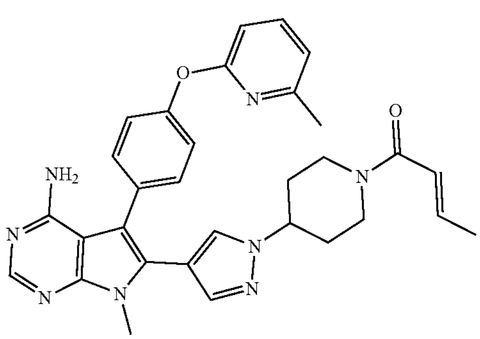 [SMILES: C/C=C/C(=O)N1CCC(n2cc(-c3c(-c4ccc(Oc5cccc(C)n5)cc4)c4c(N)ncnc4n3C)cn2)CC1] | B | C |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 650 | 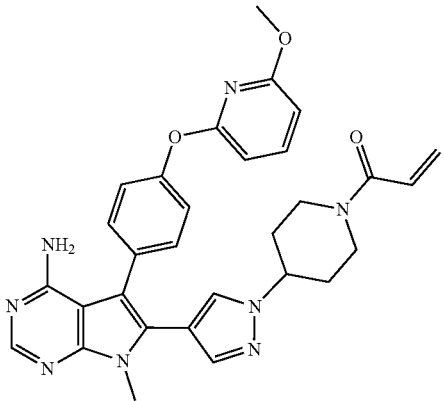 [SMILES: C=CC(=O)N1CCC(n2cc(-c3c(-c4ccc(Oc5cccc(OC)n5)cc4)c4c(N)ncnc4n3C)cn2)CC1] | A | A |
| 651 | 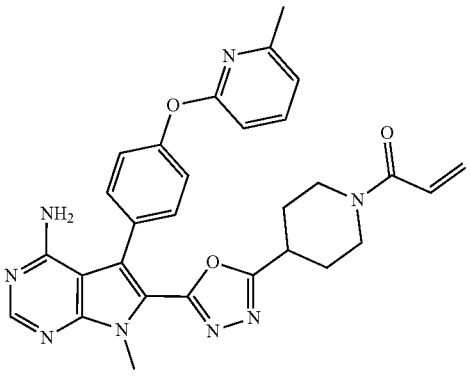 [SMILES: C=CC(=O)N1CCC(c2nnc(-c3c(-c4ccc(Oc5cccc(C)n5)cc4)c4c(N)ncnc4n3C)o2)CC1] | B | A |
| 652 | 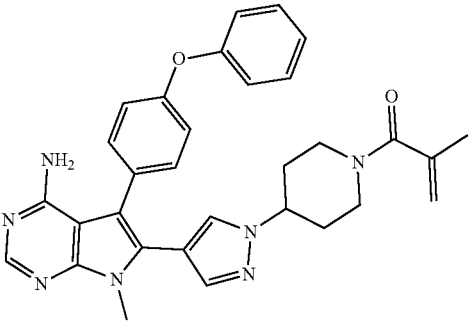 [SMILES: C=C(C)C(=O)N1CCC(n2cc(-c3c(-c4ccc(Oc5ccccc5)cc4)c4c(N)ncnc4n3C)cn2)CC1] | B | D |
| 653 | 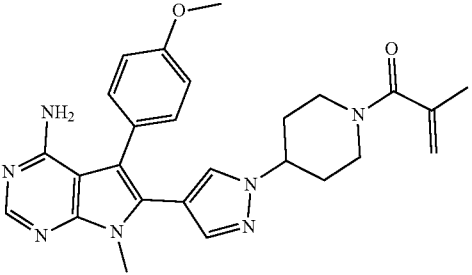 [SMILES: C=C(C)C(=O)N1CCC(n2cc(-c3c(-c4ccc(OC)cc4)c4c(N)ncnc4n3C)cn2)CC1] | C | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 654 | 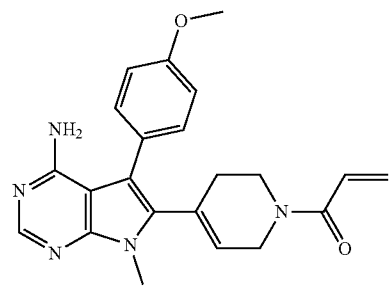 [SMILES: C=CC(=O)N1CC=C(c2c(-c3ccc(OC)cc3)c3c(N)ncnc3n2C)CC1] | A | A |
| 655 | 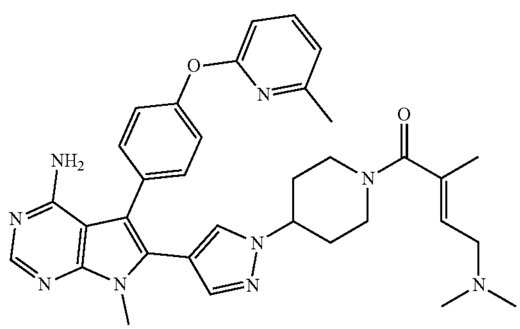 [SMILES: C/C(=C\CN(C)C)C(=O)N1CCC(n2cc(-c3c(-c4ccc(Oc5cccc(C)n5)cc4)c4c(N)ncnc4n3C)cn2)CC1] | C | D |
| 656 | 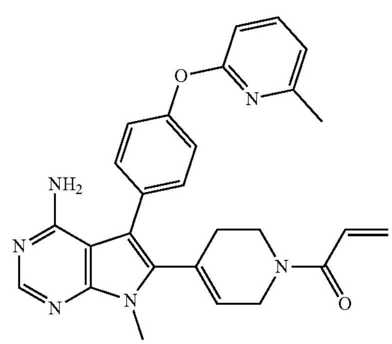 [SMILES: C=CC(=O)N1CC=C(c2c(-c3ccc(Oc4cccc(C)n4)cc3)c3c(N)ncnc3n2C)CC1] | A | A |
| 657 | 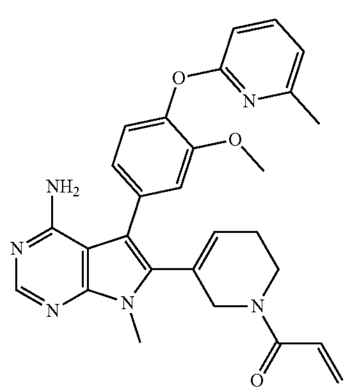 [SMILES: C=CC(=O)N1CCC=C(c2c(-c3ccc(Oc4cccc(C)n4)c(OC)c3)c3c(N)ncnc3n2C)C1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 658 | 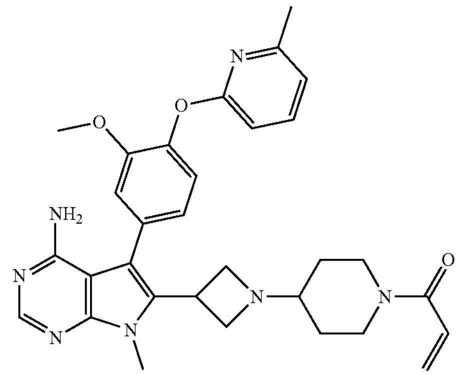 [SMILES: C=CC(=O)N1CCC(N2CC(c3c(-c4ccc(Oc5cccc(C)n5)c(OC)c4)c4c(N)ncnc4n3C)C2)CC1] | D | |
| 659 | 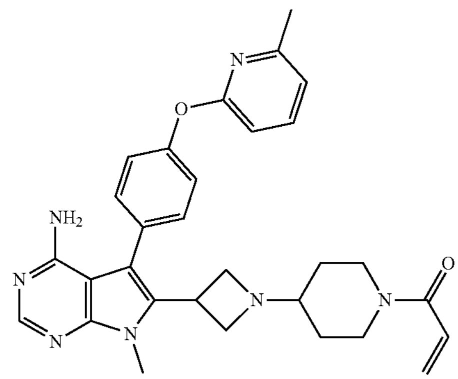 [SMILES: C=CC(=O)N1CCC(N2CC(c3c(-c4ccc(Oc5cccc(C)n5)cc4)c4c(N)ncnc4n3C)C2)CC1] | D | |
| 660 | 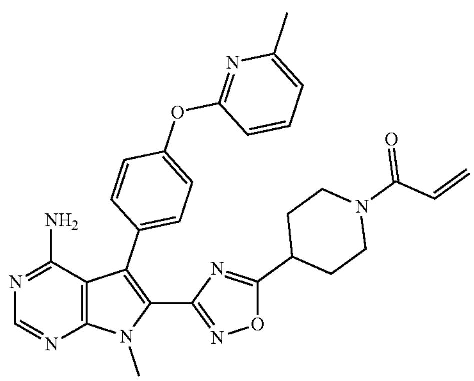 [SMILES: C=CC(=O)N1CCC(c2nc(-c3c(-c4ccc(Oc5cccc(C)n5)cc4)c4c(N)ncnc4n3C)no2)CC1] | A | A |
| 661 | 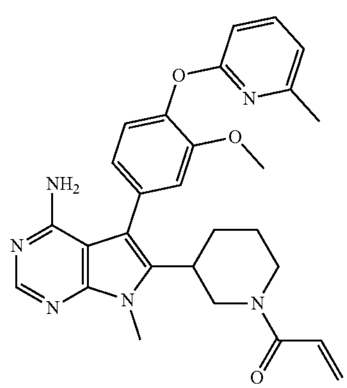 [SMILES: C=CC(=O)N1CCCC(c2c(-c3ccc(Oc4cccc(C)n4)c(OC)c3)c3c(N)ncnc3n2C)C1] | D | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 662 | 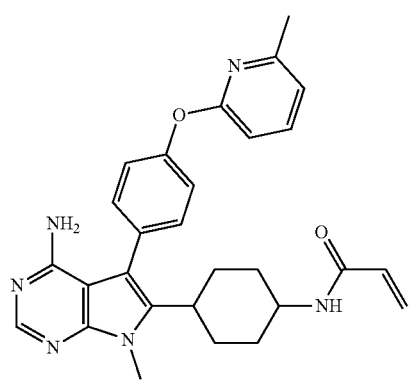 [SMILES: C=CC(=O)NC1CCC(c2c(-c3ccc(Oc4cccc(C)n4)cc3)c3c(N)ncnc3n2C)CC1] | B | C |
| 663 | 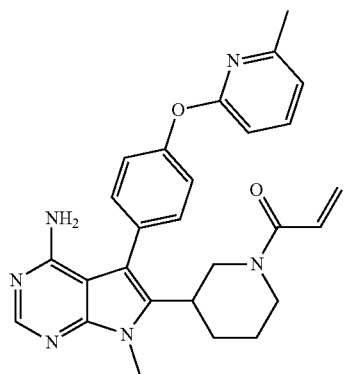 [SMILES: C=CC(=O)N1CCCC(c2c(-c3ccc(Oc4cccc(C)n4)cc3)c3c(N)ncnc3n2C)C1] | C | C |
| 664 | 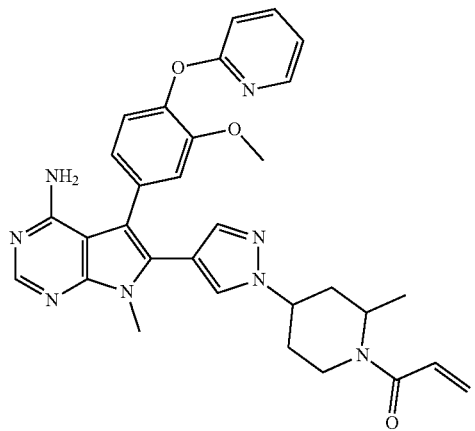 [SMILES: C=CC(=O)N1CCC(n2cc(-c3c(-c4ccc(Oc5ccccn5)c(OC)c4)c4c(N)ncnc4n3C)cn2)CC1C] | B | B |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 665 | 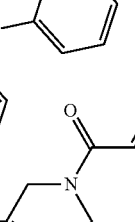 | B | C |
| 666 | 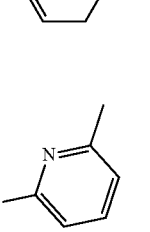 | A | A |
| 667 | 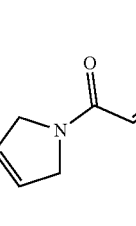 | B | B |
| 668 | 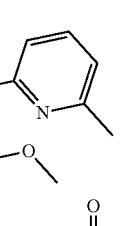 | A | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 669 | 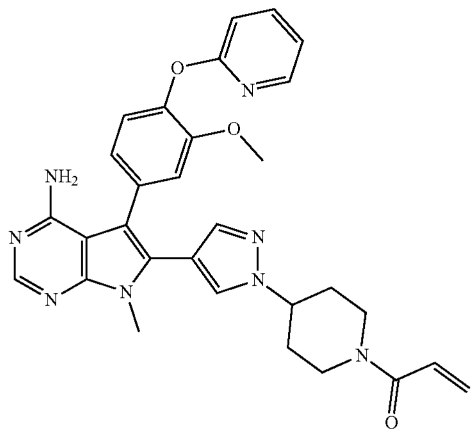 [SMILES: C=CC(=O)N1CCC(n2cc(-c3c(-c4ccc(Oc5ccccn5)c(OC)c4)c4c(N)ncnc4n3C)cn2)CC1] | C | C |
| 670 | 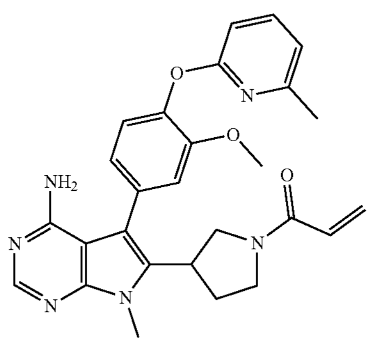 [SMILES: C=CC(=O)N1CCC(c2c(-c3ccc(Oc4cccc(C)n4)c(OC)c3)c3c(N)ncnc3n2C)C1] | C | C |
| 671 | 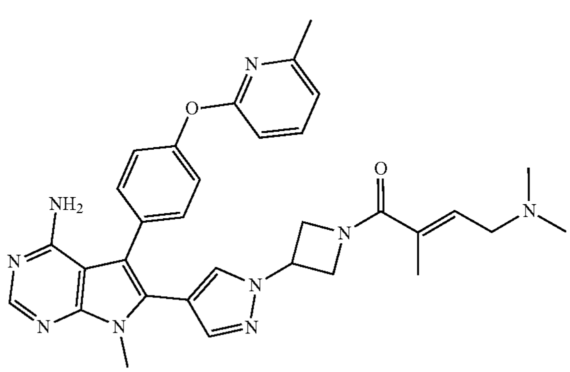 [SMILES: C/C(=C\CN(C)C)C(=O)N1CC(n2cc(-c3c(-c4ccc(Oc5cccc(C)n5)cc4)c4c(N)ncnc4n3C)cn2)C1] | C | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 672 | 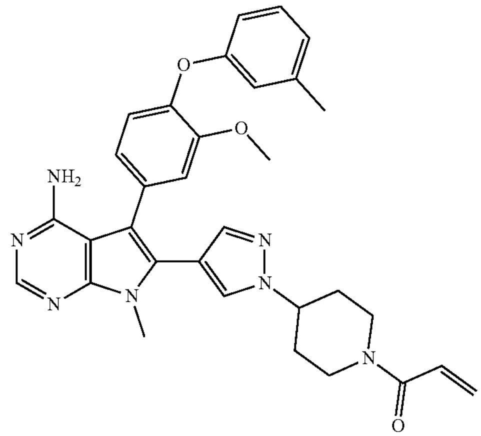 [SMILES: C=CC(=O)N1CCC(n2cc(-c3c(-c4ccc(Oc5cccc(C)c5)c(OC)c4)c4c(N)ncnc4n3C)cn2)CC1] | B | C |
| 673 | 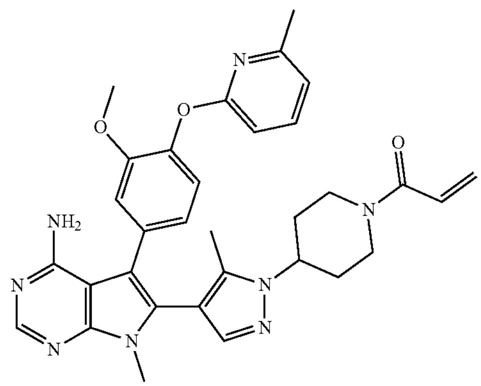 [SMILES: C=CC(=O)N1CCC(n2ncc(-c3c(-c4ccc(Oc5cccc(C)n5)c(OC)c4)c4c(N)ncnc4n3C)c2C)CC1] | A | A |
| 674 | 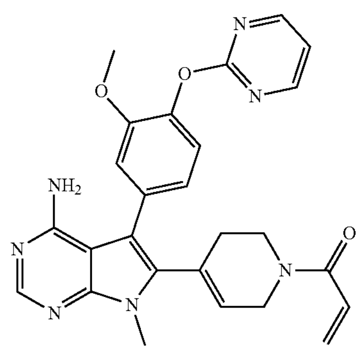 | A | A |
| 675 | 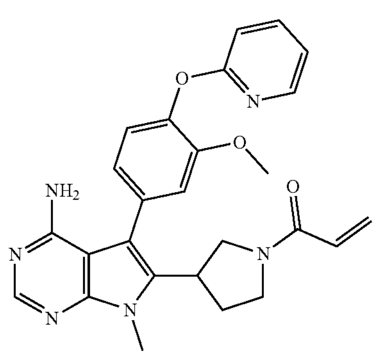 [SMILES: C=CC(=O)N1CCC(c2c(-c3ccc(Oc4ccccn4)c(OC)c3)c3c(N)ncnc3n2C)C1] | C | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 676 | 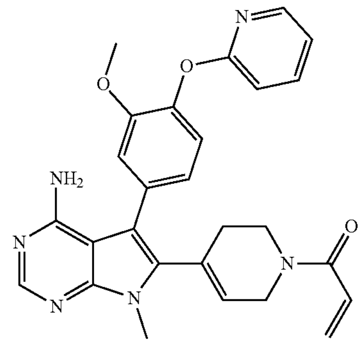 | A | A |
| 677 | 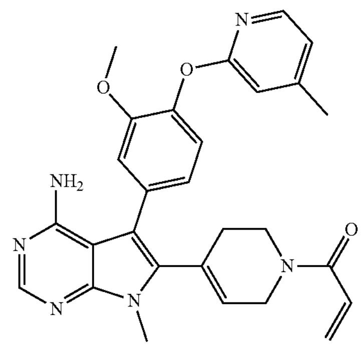 [SMILES: C=CC(=O)N1CC=C(c2c(-c3ccc(Oc4cc(C)ccn4)c(OC)c3)c3c(N)ncnc3n2C)CC1] | A | A |
| 678 | 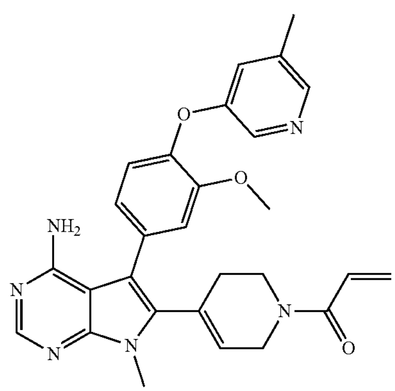 [SMILES: C=CC(=O)N1CC=C(c2c(-c3ccc(Oc4cncc(C)c4)c(OC)c3)c3c(N)ncnc3n2C)CC1] | A | B |
| 679 | 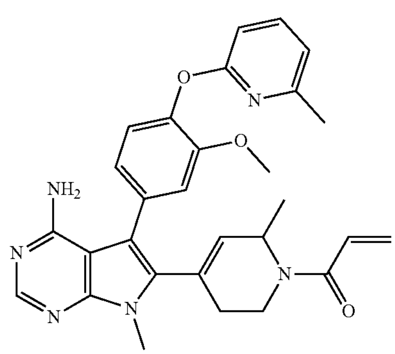 [SMILES: C=CC(=O)N1CCC(c2c(-c3ccc(Oc4cccc(C)n4)c(OC)c3)c3c(N)ncnc3n2C)=CC1C] | A | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 680 | 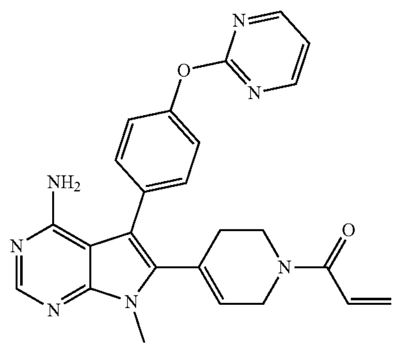 [SMILES: C=CC(=O)N1CC=C(c2c(-c3ccc(Oc4ncccn4)cc3)c3c(N)ncnc3n2C)CC1] | A | A |
| 681 | 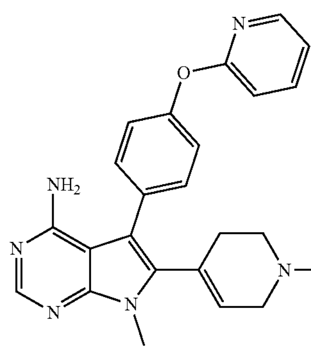 | A | A |
| 682 | 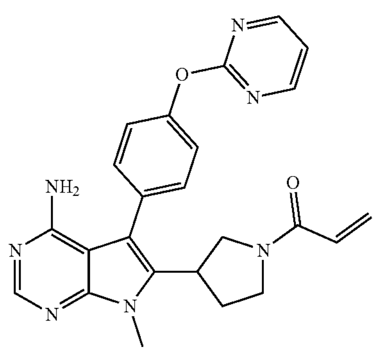 | B | A |
| 683 | 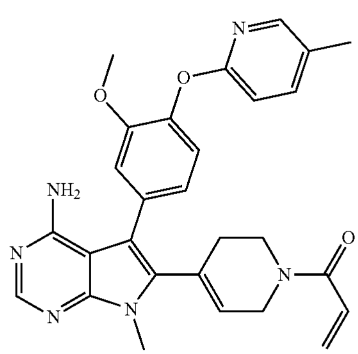 [SMILES: C=CC(=O)N1CC=C(c2c(-c3ccc(Oc4ccc(C)cn4)c(OC)c3)c3c(N)ncnc3n2C)CC1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 684 | 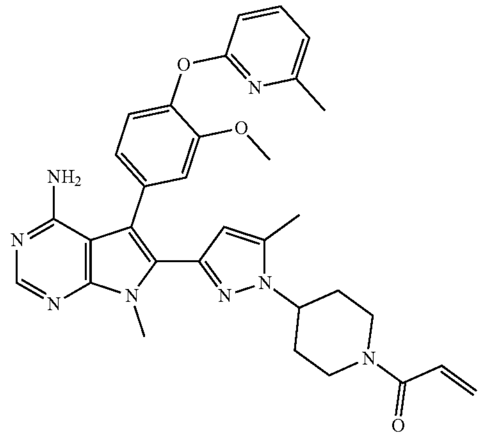 [SMILES: C=CC(=O)N1CCC(n2nc(-c3c(-c4ccc(Oc5cccc(C)n5)c(OC)c4)c4c(N)ncnc4n3C)cc2C)CC1] | D | D |
| 685 | 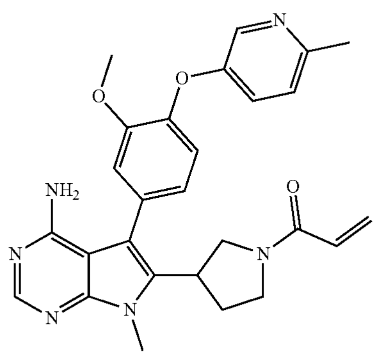 [SMILES: C=CC(=O)N1CCC(c2c(-c3ccc(Oc4ccc(C)nc4)c(OC)c3)c3c(N)ncnc3n2C)C1] | D | D |
| 686 | 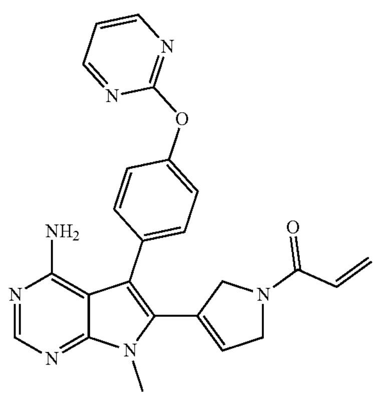 [SMILES: C=CC(=O)N1CC=C(c2c(-c3ccc(Oc4ncccn4)cc3)c3c(N)ncnc3n2C)C1] | A | A |
| 687 | 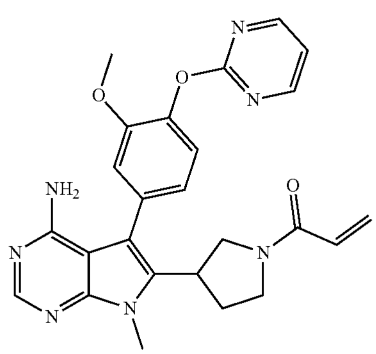 [SMILES: C=CC(=O)N1CCC(c2c(-c3ccc(Oc4ncccn4)c(OC)c3)c3c(N)ncnc3n2C)C1] | D | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 688 | 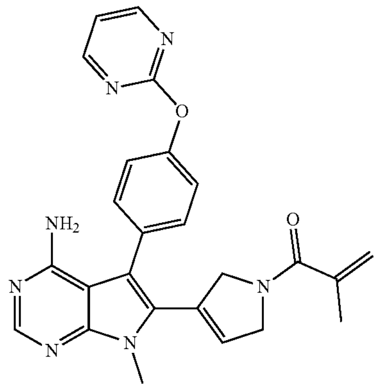 [SMILES: C=C(C)C(=O)N1CC=C(c2c(-c3ccc(Oc4ncccn4)cc3)c3c(N)ncnc3n2C)C1] | D | D |
| 689 | 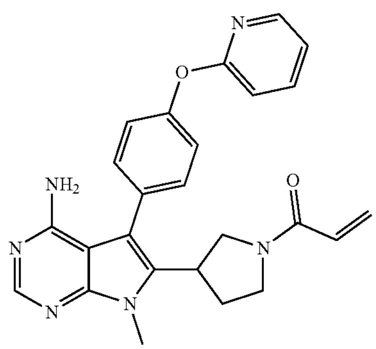 | A | A |
| 690 | 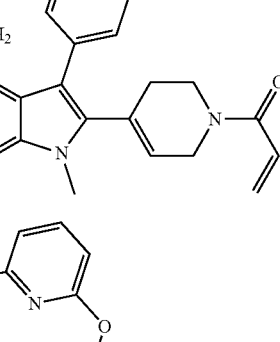 | A | A |
| 691 | 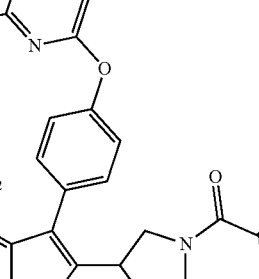 | C | D |

TABLE 1-continued

Representative Compounds of the Invention with Bioactivity Data.

| Example | Structure | Biochemical FGFR2 Caliper IC50 | Cell SNU-16 IC50 |
|---------|-----------|--------------------------------|------------------|
| 692 | 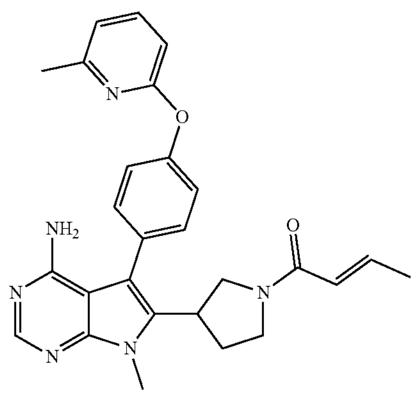 [SMILES: C/C=C/C(=O)N1CCC(c2c(-c3ccc(Oc4cccc(C)n4)cc3)c3c(N)ncnc3n2C)C1] | D | D |
| 693 | 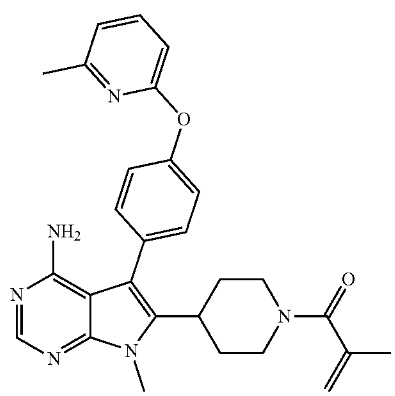 [SMILES: C=C(C)C(=O)N1CCC(c2c(-c3ccc(Oc4cccc(C)n4)cc3)c3c(N)ncnc3n2C)CC1] | C | D |
| 694 | 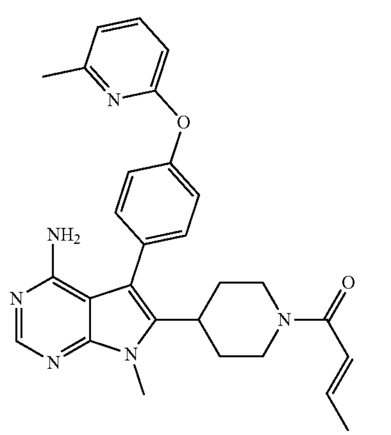 [SMILES: C/C=C/C(=O)N1CCC(c2c(-c3ccc(Oc4cccc(C)n4)cc3)c3c(N)ncnc3n2C)CC1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 695 | 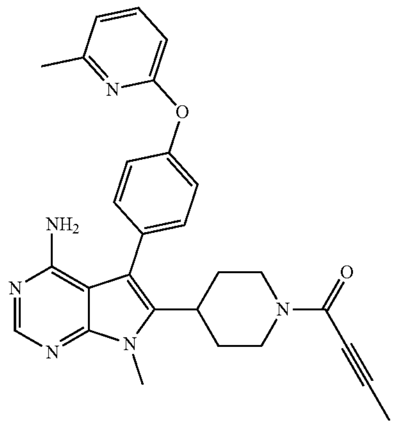 [SMILES: CC#CC(=O)N1CCC(c2c(-c3ccc(Oc4cccc(C)n4)cc3)c3c(N)ncnc3n2C)CC1] | B | A |
| 696 | 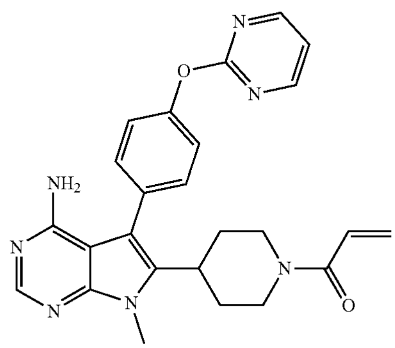 [SMILES: C=CC(=O)N1CCC(c2c(-c3ccc(Oc4ncccn4)cc3)c3c(N)ncnc3n2C)CC1] | C | B |
| 697 | 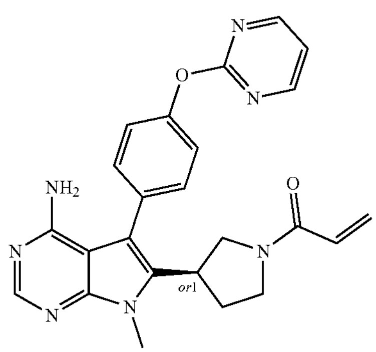 [SMILES: C=CC(=O)N1CC[C@@H](c2c(-c3ccc(Oc4ncccn4)cc3)c3c(N)ncnc3n2C)C1] | A | A |
| 698 | 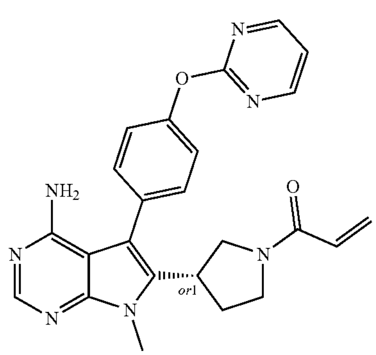 | C | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 699 | 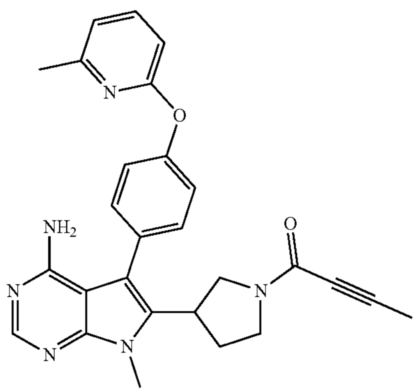 [SMILES: CC#CC(=O)N1CCC(c2c(-c3ccc(Oc4cccc(C)n4)cc3)c3c(N)ncnc3n2C)C1] | B | A |
| 700 | 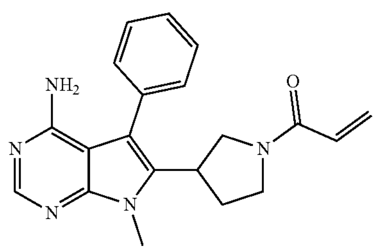 [SMILES: C=CC(=O)N1CCC(c2c(-c3ccccc3)c3c(N)ncnc3n2C)C1] | D | C |
| 701 | 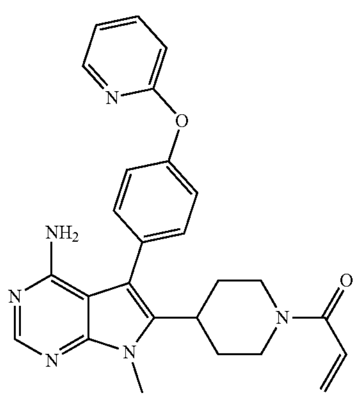 [SMILES: C=CC(=O)N1CCC(c2c(-c3ccc(Oc4ccccn4)cc3)c3c(N)ncnc3n2C)CC1] | A | A |
| 702 | 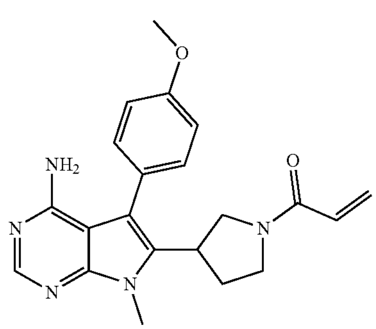 [SMILES: C=CC(=O)N1CCC(c2c(-c3ccc(OC)cc3)c3c(N)ncnc3n2C)C1] | C | B |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 703 | 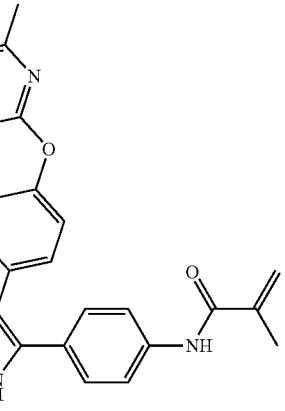 | A | A |
| 704 | 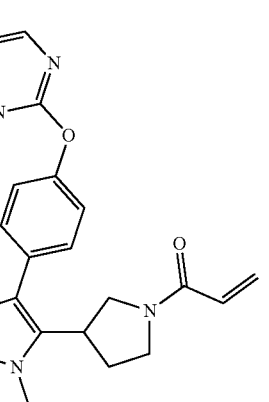 | C | B |
| 705 | 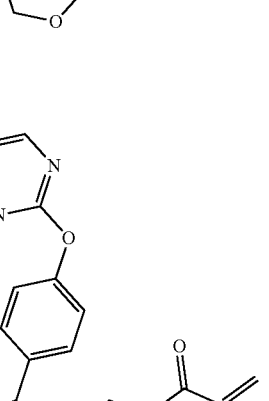 | B | A |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 706 | 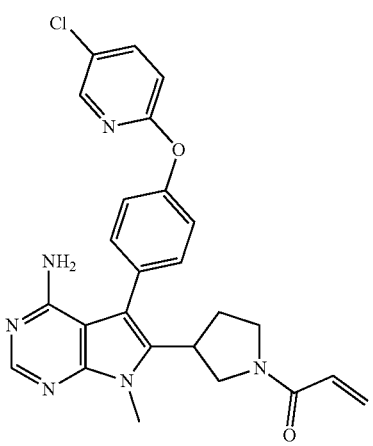 [SMILES: C=CC(=O)N1CCC(c2c(-c3ccc(Oc4ccc(Cl)cn4)cc3)c3c(N)ncnc3n2C)C1] | A | A |
| 707 | 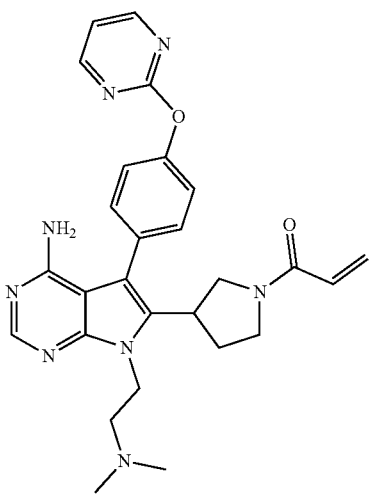 [SMILES: C=CC(=O)N1CCC(c2c(-c3ccc(Oc4ncccn4)cc3)c3c(N)ncnc3n2CCN(C)C)C1] | D | D |
| 708 | 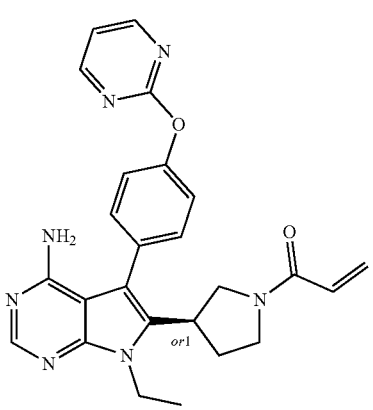 [SMILES: C=CC(=O)N1CC[C@@H](c2c(-c3ccc(Oc4ncccn4)cc3)c3c(N)ncnc3n2CC)C1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 709 | 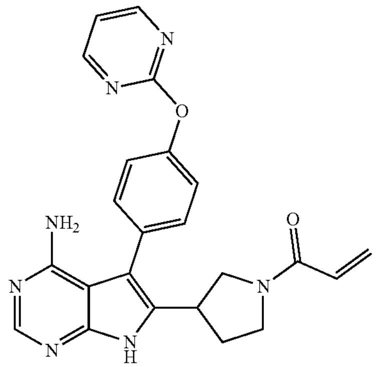 [SMILES: C=CC(=O)N1CCC(c2[nH]c3ncnc(N)c3c2-c2ccc(Oc3ncccn3)cc2)C1] | A | A |
| 710 | 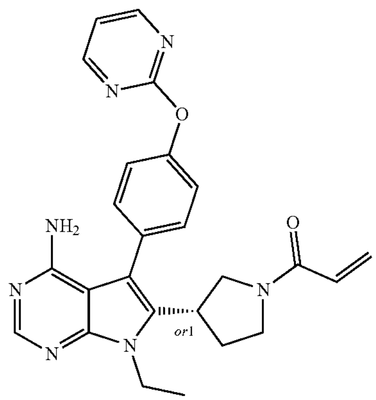 | C | B |
| 711 | 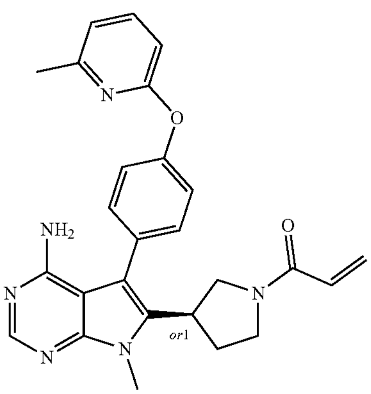 [SMILES: C=CC(=O)N1CC[C@@H](c2c(-c3ccc(Oc4cccc(C)n4)cc3)c3c(N)ncnc3n2C)C1] | A | A |
| 712 | 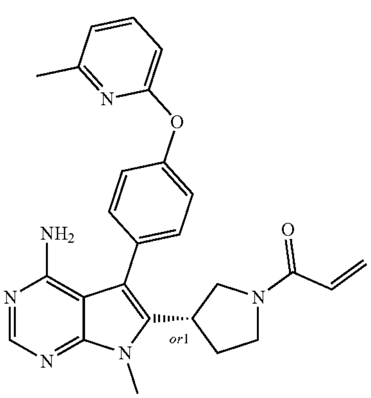 [SMILES: C=CC(=O)N1CC[C@H](c2c(-c3ccc(Oc4cccc(C)n4)cc3)c3c(N)ncnc3n2C)C1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 713 | 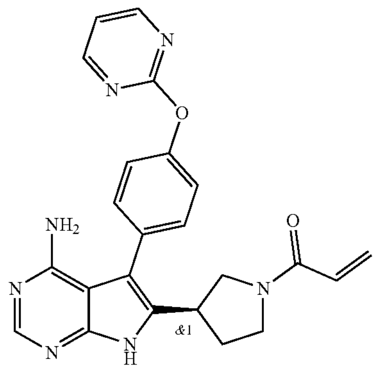 [SMILES: C=CC(=O)N1CC[C@@H](c2[nH]c3ncnc(N)c3c2-c2ccc(Oc3ncccn3)cc2)C1] | A | A |
| 714 | 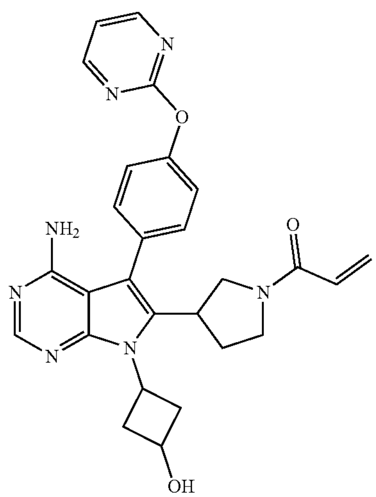 [SMILES: C=CC(=O)N1CCC(c2c(-c3ccc(Oc4ncccn4)cc3)c3c(N)ncnc3n2C2CC(O)C2)C1] | A | A |
| 715 | 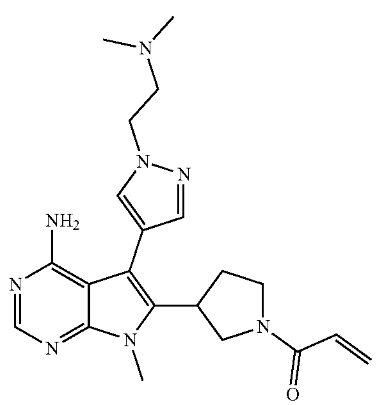 [SMILES: C=CC(=O)N1CCC(c2c(-c3cnn(CCN(C)C)c3)c3c(N)ncnc3n2C)C1] | D | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 716 | 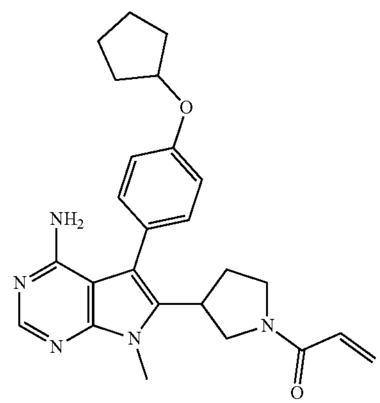 | A | A |
| 717 | 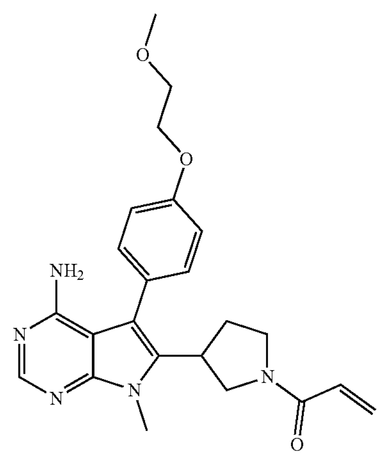 [SMILES: C=CC(=O)N1CCC(c2c(-c3ccc(OCCOC)cc3)c3c(N)ncnc3n2C)C1] | D | C |
| 718 | 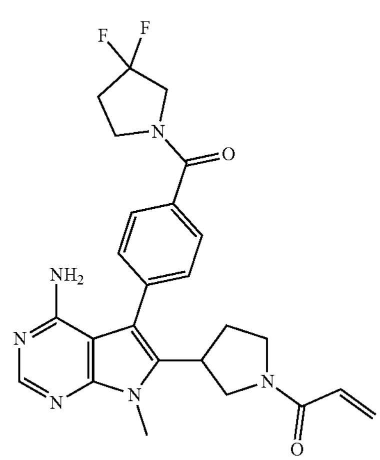 [SMILES: C=CC(=O)N1CCC(c2c(-c3ccc(C(=O)N4CCC(F)(F)C4)cc3)c3c(N)ncnc3n2C)C1] | C | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 719 | 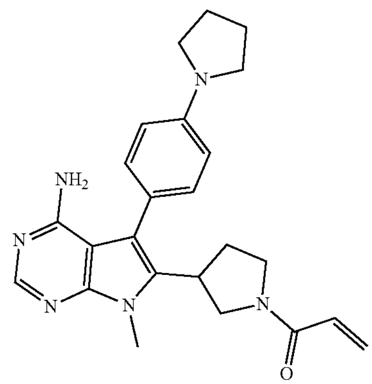 [SMILES: C=CC(=O)N1CCC(c2c(-c3ccc(N4CCCC4)cc3)c3c(N)ncnc3n2C)C1] | A | A |
| 720 | 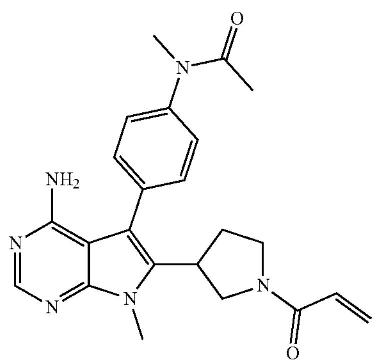 [SMILES: C=CC(=O)N1CCC(c2c(-c3ccc(N(C)C(C)=O)cc3)c3c(N)ncnc3n2C)C1] | D | D |
| 721 | 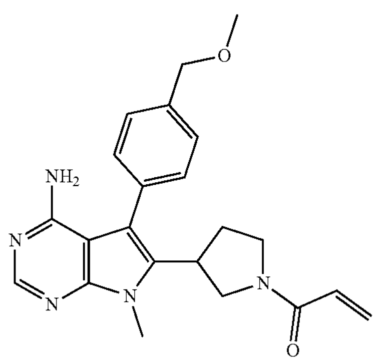 [SMILES: C=CC(=O)N1CCC(c2c(-c3ccc(COC)cc3)c3c(N)ncnc3n2C)C1] | C | C |
| 722 | 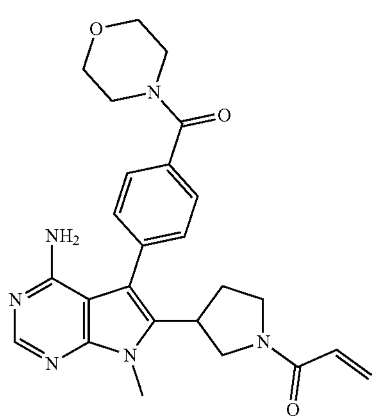 [SMILES: C=CC(=O)N1CCC(c2c(-c3ccc(C(=O)N4CCOCC4)cc3)c3c(N)ncnc3n2C)C1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 723 | 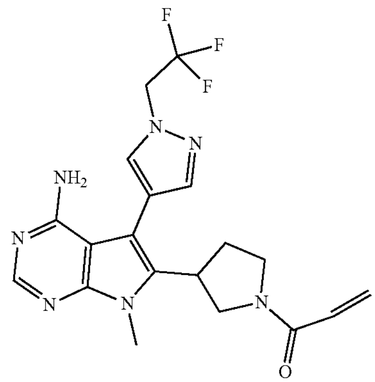 [SMILES: C=CC(=O)N1CCC(c2c(-c3cnn(CC(F)(F)F)c3)c3c(N)ncnc3n2C)C1] | D | D |
| 724 | 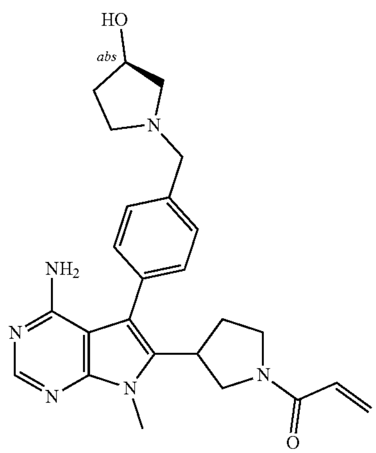 [SMILES: C=CC(=O)N1CCC(c2c(-c3ccc(CN4CC[C@@H](O)C4)cc3)c3c(N)ncnc3n2C)C1] | D | D |
| 725 | 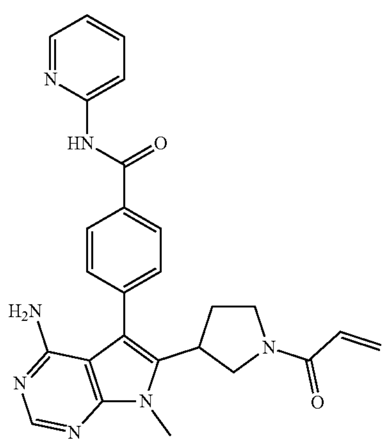 [SMILES: C=CC(=O)N1CCC(c2c(-c3ccc(C(=O)Nc4ccccn4)cc3)c3c(N)ncnc3n2C)C1] | A | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 726 | 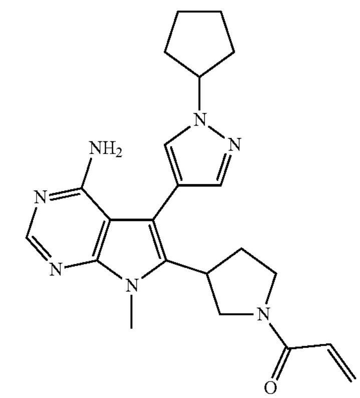 [SMILES: C=CC(=O)N1CCC(c2c(-c3cnn(C4CCCC4)c3)c3c(N)ncnc3n2C)C1] | D | D |
| 727 | 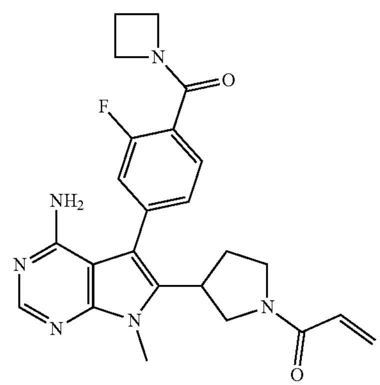 [SMILES: C=CC(=O)N1CCC(c2c(-c3ccc(C(=O)N4CCC4)c(F)c3)c3c(N)ncnc3n2C)C1] | D | D |
| 728 | 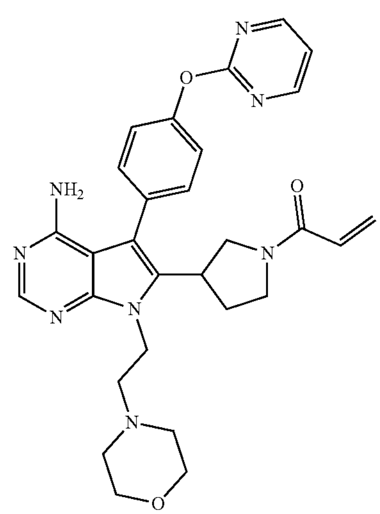 [SMILES: C=CC(=O)N1CCC(c2c(-c3ccc(Oc4ncccn4)cc3)c3c(N)ncnc3n2CCN2CCOCC2)C1] | D | D |

TABLE 1-continued

Representative Compounds of the Invention with Bioactivity Data.

| Example | Structure | Biochemical FGFR2 Caliper IC50 | Cell SNU-16 IC50 |
| --- | --- | --- | --- |
| 729 | 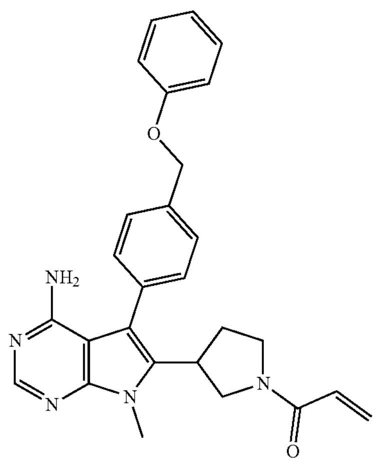 [SMILES: C=CC(=O)N1CCC(c2c(-c3ccc(COc4ccccc4)cc3)c3c(N)ncnc3n2C)C1] | B | B |
| 730 | 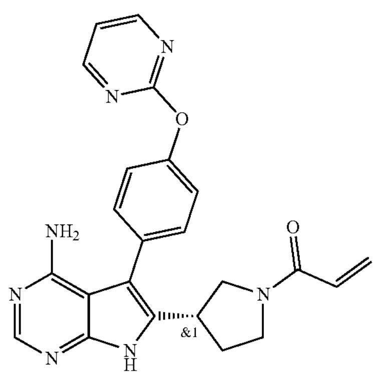 [SMILES: C=CC(=O)N1CC[C@H](c2[nH]c3ncnc(N)c3c2-c2ccc(Oc3ncccn3)cc2)C1] | C | D |
| 731 | 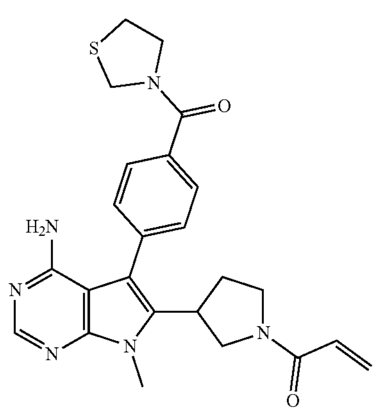 [SMILES: C=CC(=O)N1CCC(c2c(-c3ccc(C(=O)N4CCSC4)cc3)c3c(N)ncnc3n2C)C1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 732 | 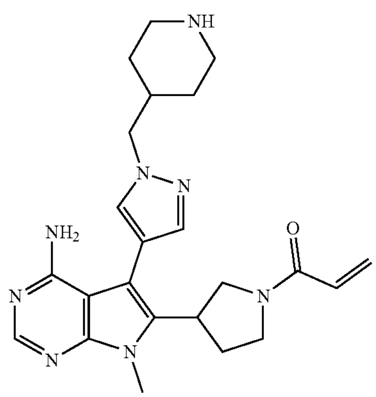 [SMILES: C=CC(=O)N1CCC(c2c(-c3cnn(CC4CCNCC4)c3)c3c(N)ncnc3n2C)C1] | B | D |
| 733 | 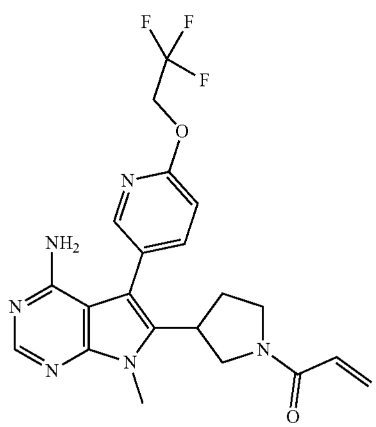 [SMILES: C=CC(=O)N1CCC(c2c(-c3ccc(OCC(F)(F)F)nc3)c3c(N)ncnc3n2C)C1] | C | C |
| 734 | 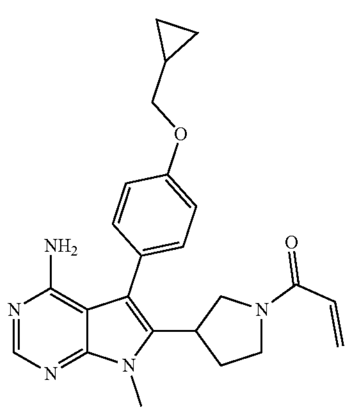 [SMILES: C=CC(=O)N1CCC(c2c(-c3ccc(OCC4CC4)cc3)c3c(N)ncnc3n2C)C1] | B | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 735 | 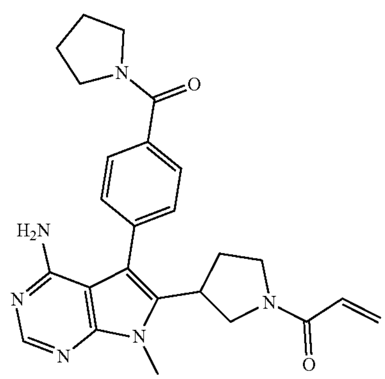 [SMILES: C=CC(=O)N1CCC(c2c(-c3ccc(C(=O)N4CCCC4)cc3)c3c(N)ncnc3n2C)C1] | C | C |
| 736 | 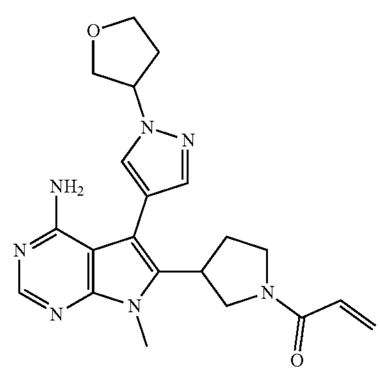 [SMILES: C=CC(=O)N1CCC(c2c(-c3cnn(C4CCOC4)c3)c3c(N)ncnc3n2C)C1] | D | D |
| 737 | 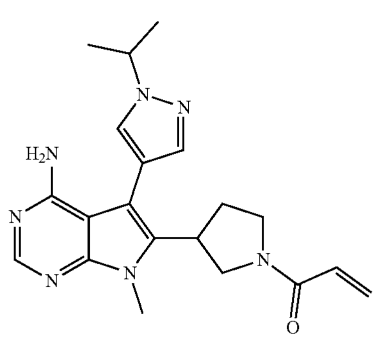 [SMILES: C=CC(=O)N1CCC(c2c(-c3cnn(C(C)C)c3)c3c(N)ncnc3n2C)C1] | D | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 738 | 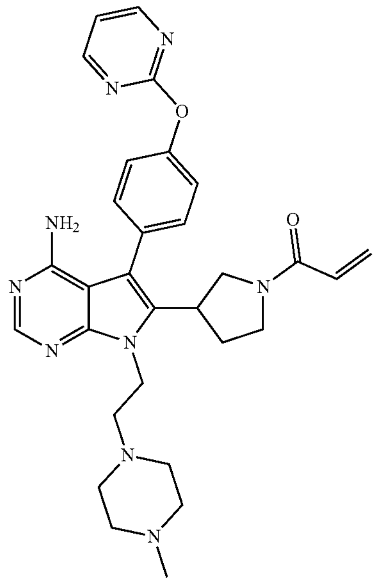 [SMILES: C=CC(=O)N1CCC(c2c(-c3ccc(Oc4ncccn4)cc3)c3c(N)ncnc3n2CCN2CCN(C)CC2)C1] | D | D |
| 739 | 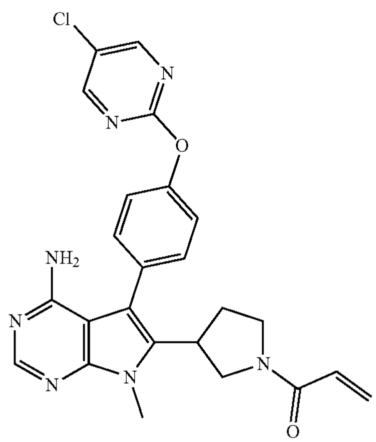 [SMILES: C=CC(=O)N1CCC(c2c(-c3ccc(Oc4ncc(Cl)cn4)cc3)c3c(N)ncnc3n2C)C1] | B | A |
| 740 | 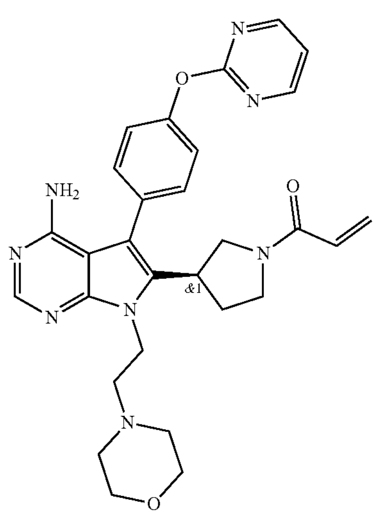 [SMILES: C=CC(=O)N1CC[C@@H](c2c(-c3ccc(Oc4ncccn4)cc3)c3c(N)ncnc3n2CCN2CCOCC2)C1] | D | D |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 741 | 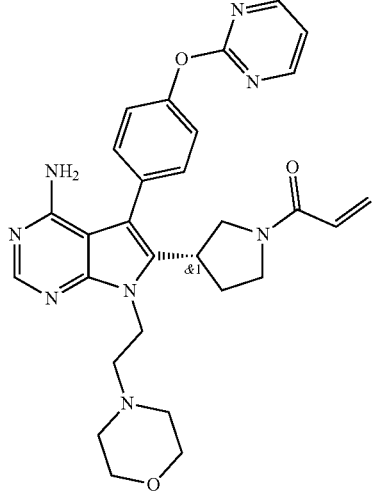 [SMILES: C=CC(=O)N1CC[C@H](c2c(-c3ccc(Oc4ncccn4)cc3)c3c(N)ncnc3n2CCN2CCOCC2)C1] | D | D |
| 742 | 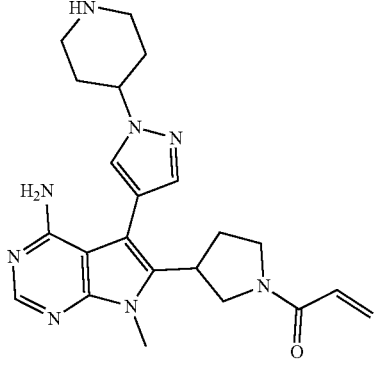 [SMILES: C=CC(=O)N1CCC(c2c(-c3cnn(C4CCNCC4)c3)c3c(N)ncnc3n2C)C1] | D | D |
| 743 | 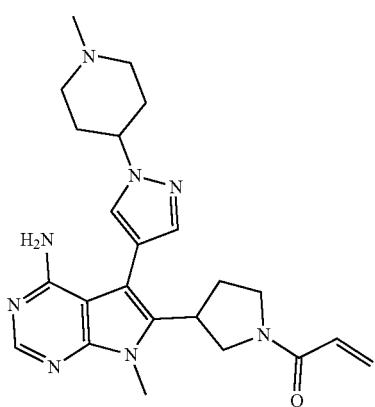 [SMILES: C=CC(=O)N1CCC(c2c(-c3cnn(C4CCN(C)CC4)c3)c3c(N)ncnc3n2C)C1] | C | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 744 | 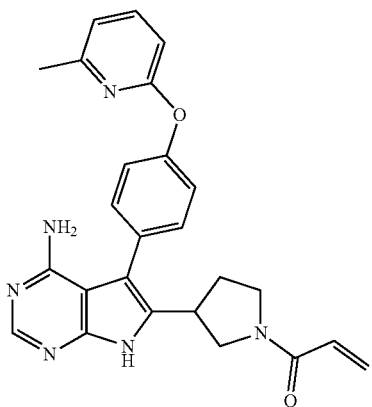 [SMILES: C=CC(=O)N1CCC(c2[nH]c3ncnc(N)c3c2-c2ccc(Oc3cccc(C)n3)cc2)C1] | A | A |
| 745 | 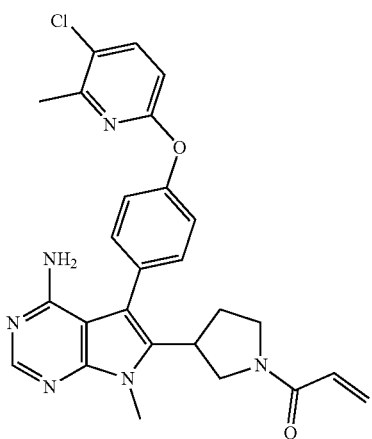 [SMILES: C=CC(=O)N1CCC(c2c(-c3ccc(Oc4ccc(Cl)c(C)n4)cc3)c3c(N)ncnc3n2C)C1] | D | D |
| 746 | 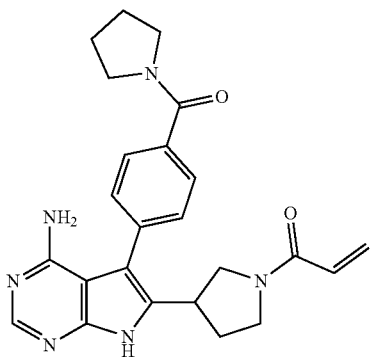 [SMILES: C=CC(=O)N1CCC(c2[nH]c3ncnc(N)c3c2-c2ccc(C(=O)N3CCCC3)cc2)C1] | A | C |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 747 | 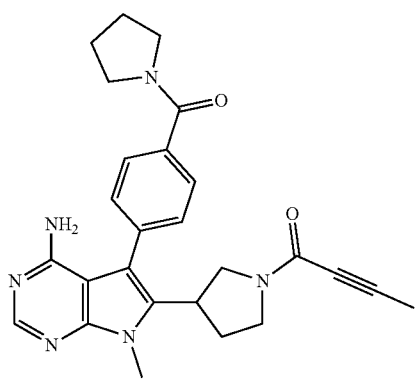 [SMILES: CC#CC(=O)N1CCC(c2c(-c3ccc(C(=O)N4CCCC4)cc3)c3c(N)ncnc3n2C)C1] | A | A |
| 748 | 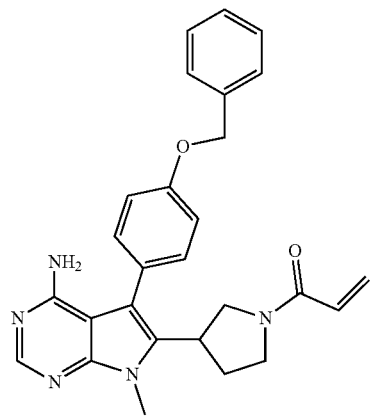 [SMILES: C=CC(=O)N1CCC(c2c(-c3ccc(OCc4ccccc4)cc3)c3c(N)ncnc3n2C)C1] | B | C |
| 749 | 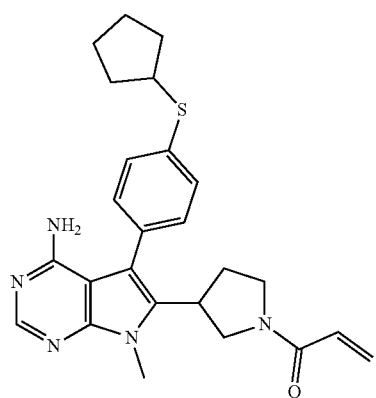 [SMILES: C=CC(=O)N1CCC(c2c(-c3ccc(SC4CCCC4)cc3)c3c(N)ncnc3n2C)C1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 750 | 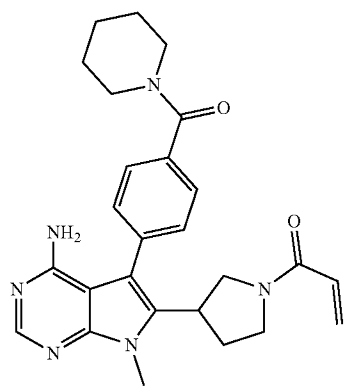 [SMILES: C=CC(=O)N1CCC(c2c(-c3ccc(C(=O)N4CCCCC4)cc3)c3c(N)ncnc3n2C)C1] | A | A |
| 751 | 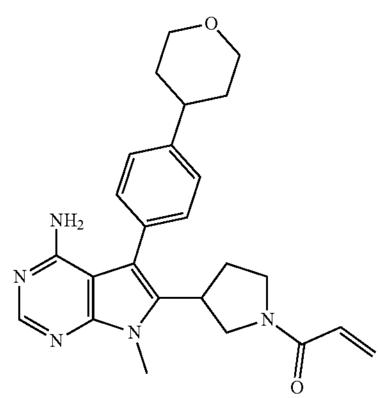 [SMILES: C=CC(=O)N1CCC(c2c(-c3ccc(C4CCOCC4)cc3)c3c(N)ncnc3n2C)C1] | C | B |
| 752 | 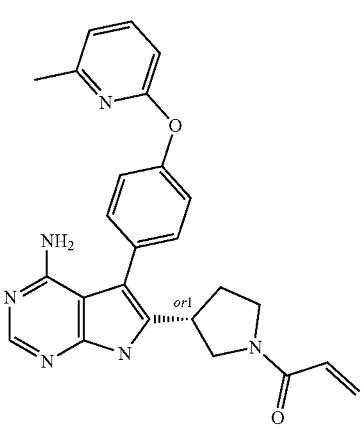 [SMILES: C=CC(=O)N1CC[C@@H](c2[nH]c3ncnc(N)c3c2-c2ccc(Oc3cccc(C)n3)cc2)C1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 753 | 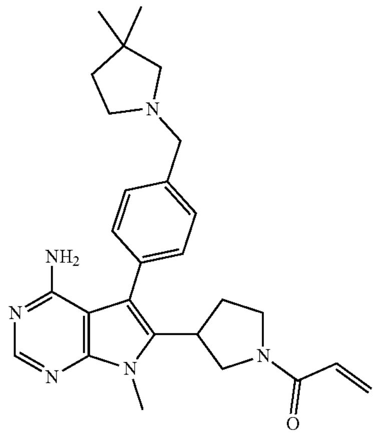 [SMILES: C=CC(=O)N1CCC(c2c(-c3ccc(CN4CCC(C)(C)C4)cc3)c3c(N)ncnc3n2C)C1] | D | D |
| 754 | 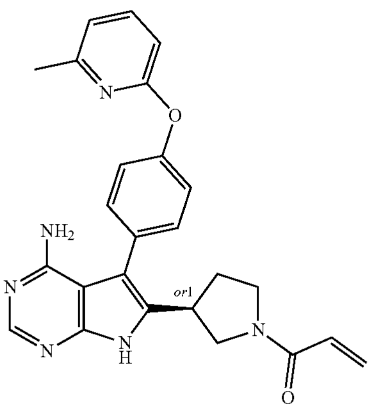 [SMILES: C=CC(=O)N1CC[C@H](c2[nH]c3ncnc(N)c3c2-c2ccc(Oc3cccc(C)n3)cc2)C1] | C | B |
| 755 | 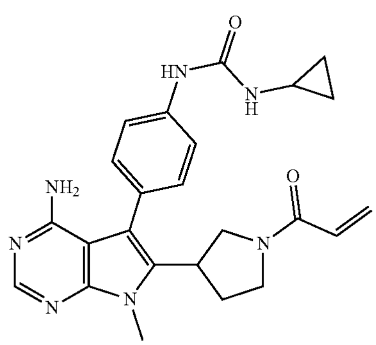 [SMILES: C=CC(=O)N1CCC(c2c(-c3ccc(NC(=O)NC4CC4)cc3)c3c(N)ncnc3n2C)C1] | A | D |
| 756 | 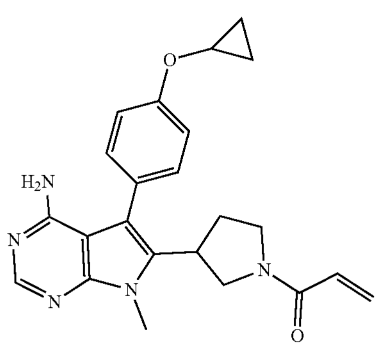 [SMILES: C=CC(=O)N1CCC(c2c(-c3ccc(OC4CC4)cc3)c3c(N)ncnc3n2C)C1] | B | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 757 | 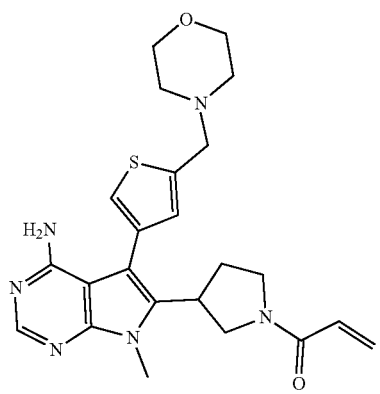 [SMILES: C=CC(=O)N1CCC(c2c(-c3csc(CN4CCOCC4)c3)c3c(N)ncnc3n2C)C1] | D | D |
| 758 | 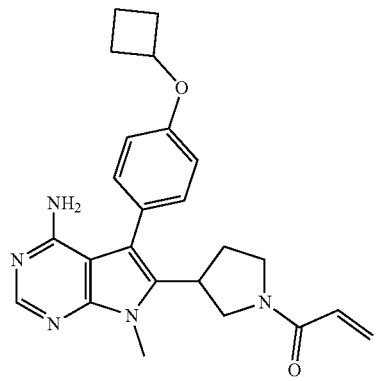 [SMILES: C=CC(=O)N1CCC(c2c(-c3ccc(OC4CCC4)cc3)c3c(N)ncnc3n2C)C1] | A | A |
| 759 | 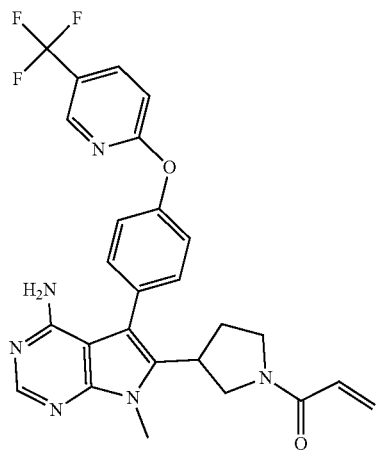 [SMILES: C=CC(=O)N1CCC(c2c(-c3ccc(Oc4ccc(C(F)(F)F)cn4)cc3)c3c(N)ncnc3n2C)C1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 760 | 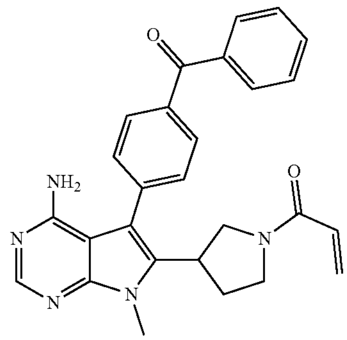 [SMILES: C=CC(=O)N1CCC(c2c(-c3ccc(C(=O)c4ccccc4)cc3)c3c(N)ncnc3n2C)C1] | A | A |
| 761 | 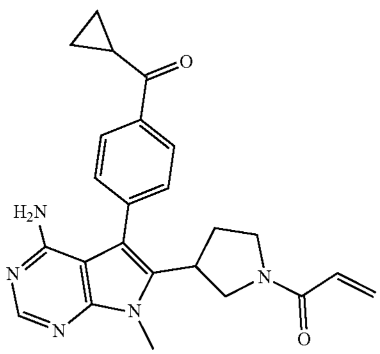 [SMILES: C=CC(=O)N1CCC(c2c(-c3ccc(C(=O)C4CC4)cc3)c3c(N)ncnc3n2C)C1] | B | B |
| 762 | 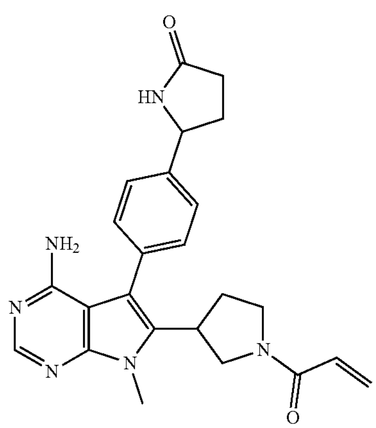 [SMILES: C=CC(=O)N1CCC(c2c(-c3ccc(C4CCC(=O)N4)cc3)c3c(N)ncnc3n2C)C1] | D | D |
| 763 | 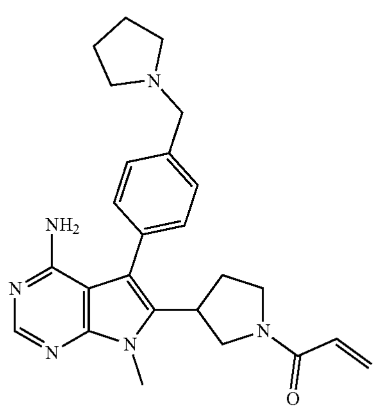 | C | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 764 | 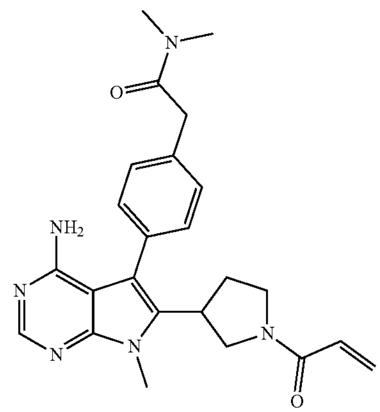 [SMILES: C=CC(=O)N1CCC(c2c(-c3ccc(CC(=O)N(C)C)cc3)c3c(N)ncnc3n2C)C1] | D | D |
| 765 | 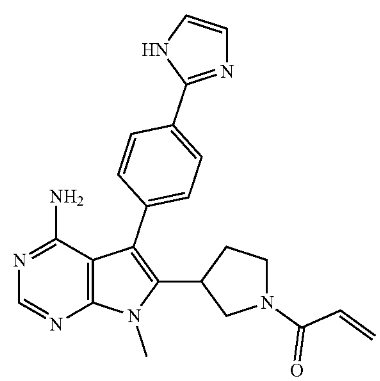 [SMILES: C=CC(=O)N1CCC(c2c(-c3ccc(-c4ncc[nH]4)cc3)c3c(N)ncnc3n2C)C1] | A | D |
| 766 | 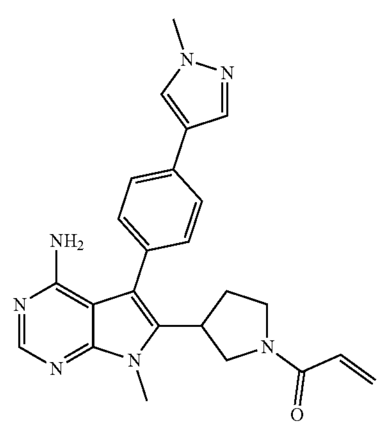 [SMILES: C=CC(=O)N1CCC(c2c(-c3ccc(-c4cnn(C)c4)cc3)c3c(N)ncnc3n2C)C1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 767 | 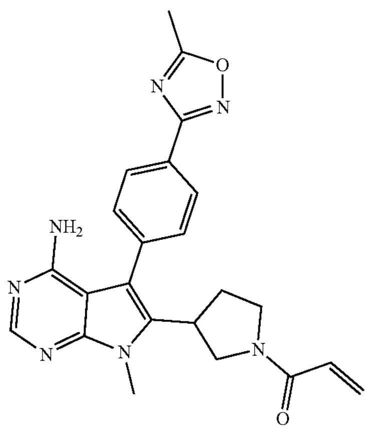 [SMILES: C=CC(=O)N1CCC(c2c(-c3ccc(-c4noc(C)n4)cc3)c3c(N)ncnc3n2C)C1] | C | B |
| 768 | 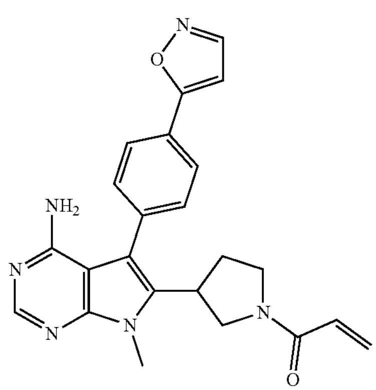 [SMILES: C=CC(=O)N1CCC(c2c(-c3ccc(-c4ccno4)cc3)c3c(N)ncnc3n2C)C1] | C | B |
| 769 | 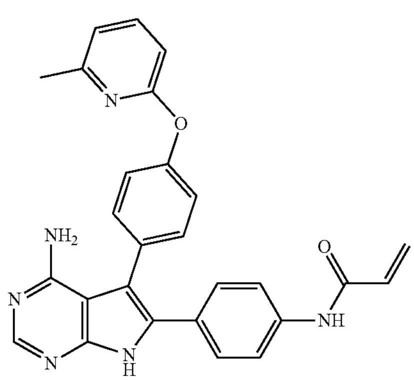 [SMILES: C=CC(=O)Nc1ccc(-c2[nH]c3ncnc(N)c3c2-c2ccc(Oc3cccc(C)n3)cc2)cc1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 770 | 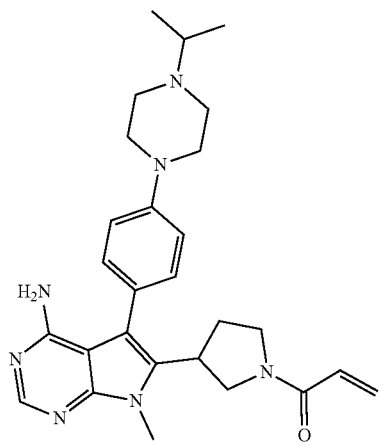 [SMILES: C=CC(=O)N1CCC(c2c(-c3ccc(N4CCN(C(C)C)CC4)cc3)c3c(N)ncnc3n2C)C1] | | D |
| 771 | 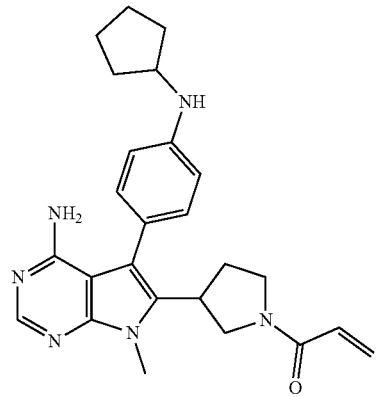 [SMILES: C=CC(=O)N1CCC(c2c(-c3ccc(NC4CCCC4)cc3)c3c(N)ncnc3n2C)C1] | D | D |
| 772 | 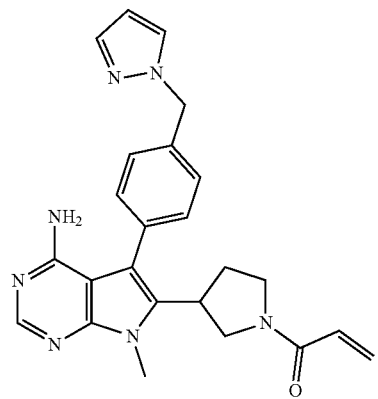 [SMILES: C=CC(=O)N1CCC(c2c(-c3ccc(Cn4cccn4)cc3)c3c(N)ncnc3n2C)C1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 773 | 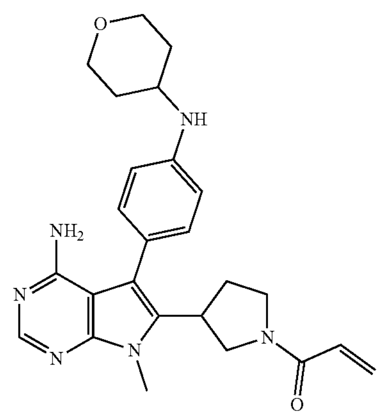 [SMILES: C=CC(=O)N1CCC(c2c(-c3ccc(NC4CCOCC4)cc3)c3c(N)ncnc3n2C)C1] | D | D |
| 774 | 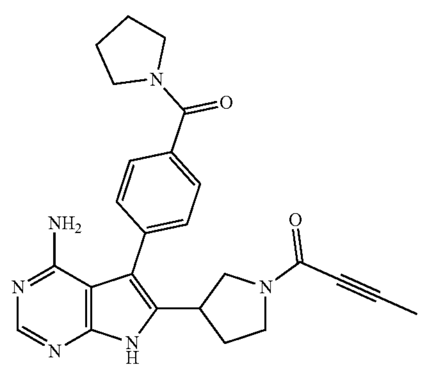 [SMILES: CC#CC(=O)N1CCC(c2[nH]c3ncnc(N)c3c2-c2ccc(C(=O)N3CCCC3)cc2)C1] | D | D |
| 775 | 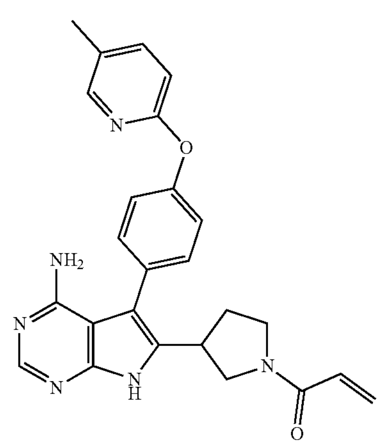 [SMILES: C=CC(=O)N1CCC(c2[nH]c3ncnc(N)c3c2-c2ccc(Oc3ccc(C)cn3)cc2)C1] | B | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 776 | 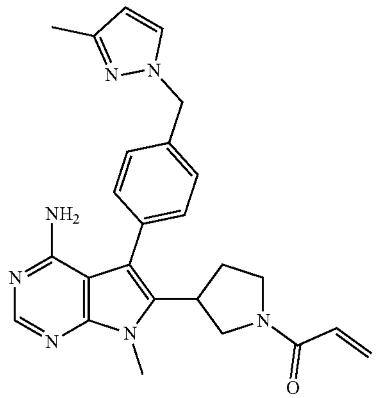 [SMILES: C=CC(=O)N1CCC(c2c(-c3ccc(Cn4ccc(C)n4)cc3)c3c(N)ncnc3n2C)C1] | A | A |
| 777 | 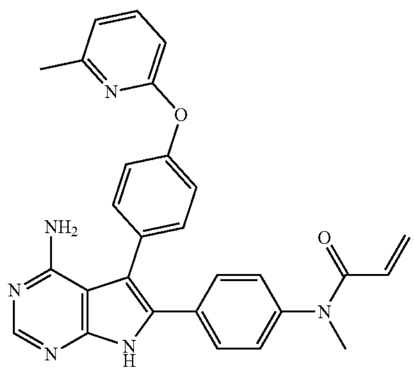 [SMILES: C=CC(=O)N(C)c1ccc(-c2[nH]c3ncnc(N)c3c2-c2ccc(Oc3cccc(C)n3)cc2)cc1] | D | D |
| 778 | 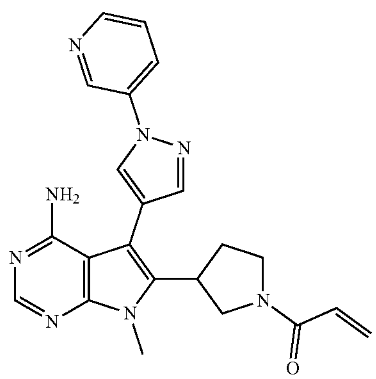 [SMILES: C=CC(=O)N1CCC(c2c(-c3cnn(-c4cccnc4)c3)c3c(N)ncnc3n2C)C1] | A | A |
| 779 | 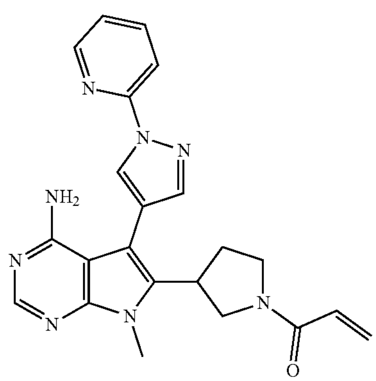 [SMILES: C=CC(=O)N1CCC(c2c(-c3cnn(-c4ccccn4)c3)c3c(N)ncnc3n2C)C1] | D | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 780 | 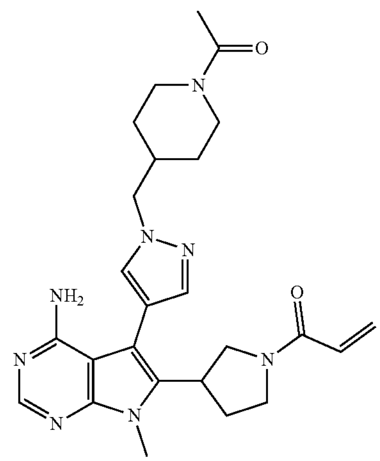 [SMILES: C=CC(=O)N1CCC(c2c(-c3cnn(CC4CCN(C(C)=O)CC4)c3)c3c(N)ncnc3n2C)C1] | C | C |
| 781 | 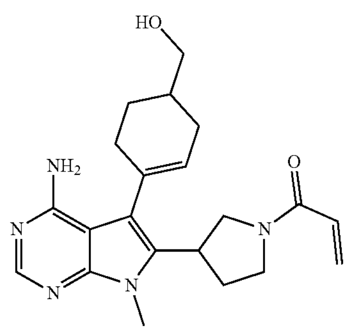 [SMILES: C=CC(=O)N1CCC(c2c(C3=CCC(CO)CC3)c3c(N)ncnc3n2C)C1] | D | D |
| 782 | 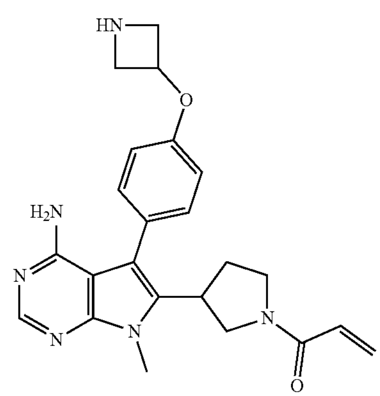 [SMILES: C=CC(=O)N1CCC(c2c(-c3ccc(OC4CNC4)cc3)c3c(N)ncnc3n2C)C1] | D | D |
| 783 | 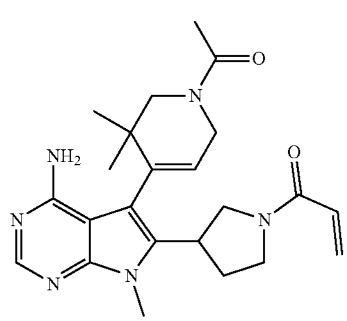 [SMILES: C=CC(=O)N1CCC(c2c(C3=CCN(C(C)=O)CC3(C)C)c3c(N)ncnc3n2C)C1] | B | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 784 | 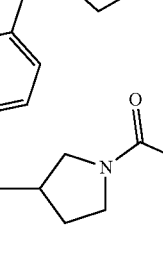 | D | D |
| 785 | 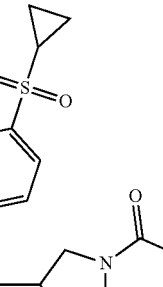 | A | A |
| 786 | 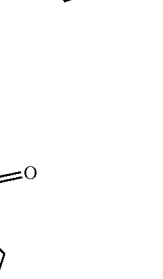 | C | D |
| 787 | 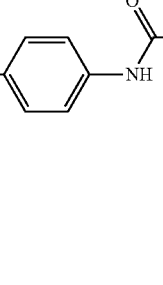 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 788 | 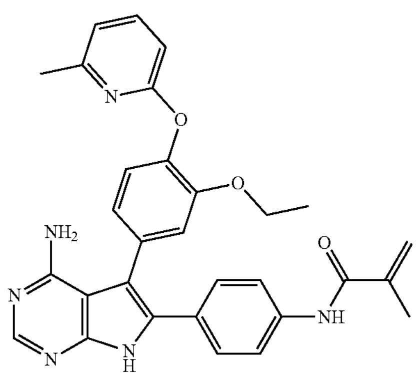 [SMILES: C=C(C)C(=O)Nc1ccc(-c2[nH]c3ncnc(N)c3c2-c2ccc(Oc3cccc(C)n3)c(OCC)c2)cc1] | A | A |
| 789 | 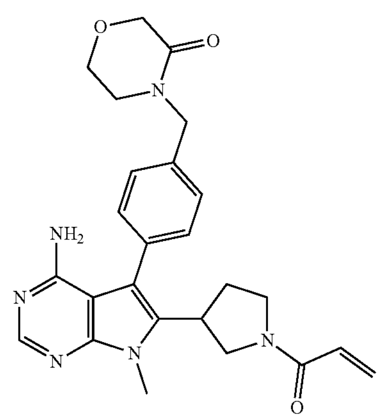 [SMILES: C=CC(=O)N1CCC(c2c(-c3ccc(CN4CCOCC4=O)cc3)c3c(N)ncnc3n2C)C1] | D | D |
| 790 | 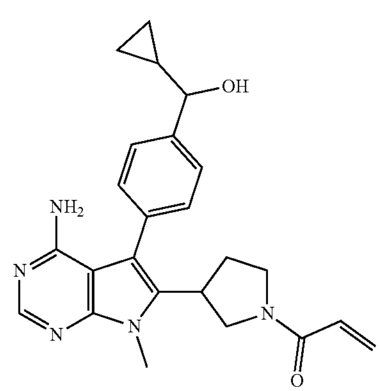 [SMILES: C=CC(=O)N1CCC(c2c(-c3ccc(C(O)C4CC4)cc3)c3c(N)ncnc3n2C)C1] | C | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 791 | 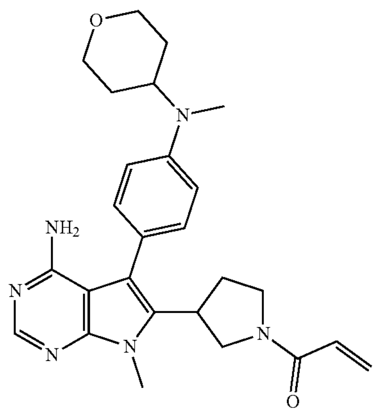 [SMILES: C=CC(=O)N1CCC(c2c(-c3ccc(N(C)C4CCOCC4)cc3)c3c(N)ncnc3n2C)C1] | C | C |
| 792 | 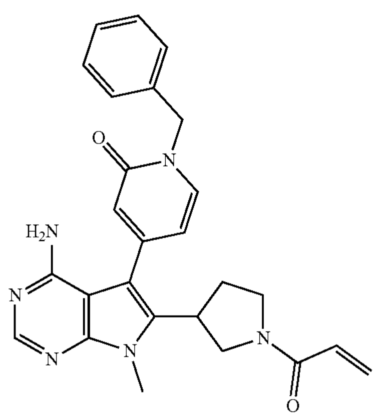 [SMILES: C=CC(=O)N1CCC(c2c(-c3ccn(Cc4ccccc4)c(=O)c3)c3c(N)ncnc3n2C)C1] | B | B |
| 793 | 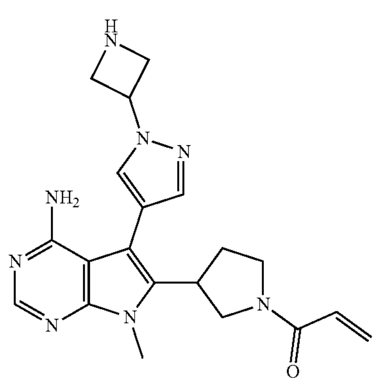 [SMILES: C=CC(=O)N1CCC(c2c(-c3cnn(C4CNC4)c3)c3c(N)ncnc3n2C)C1] | C | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 794 | 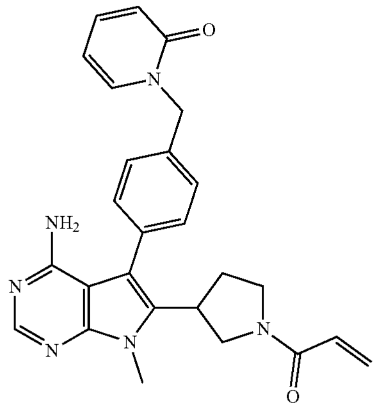 [SMILES: C=CC(=O)N1CCC(c2c(-c3ccc(Cn4ccccc4=O)cc3)c3c(N)ncnc3n2C)C1] | D | D |
| 795 | 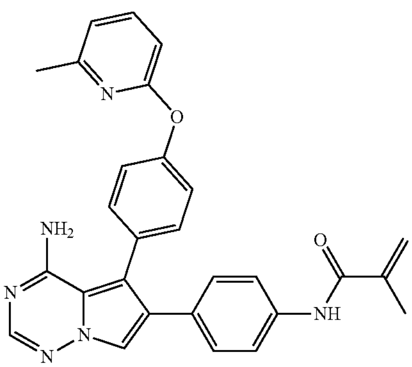 [SMILES: C=C(C)C(=O)Nc1ccc(-c2cn3ncnc(N)c3c2-c2ccc(Oc3cccc(C)n3)cc2)cc1] | D | D |
| 796 | 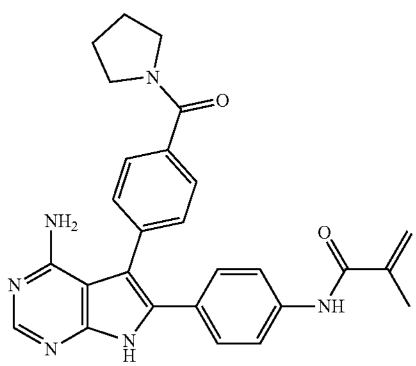 [SMILES: C=C(C)C(=O)Nc1ccc(-c2[nH]c3ncnc(N)c3c2-c2ccc(C(=O)N3CCCC3)cc2)cc1] | A | A |
| 797 | 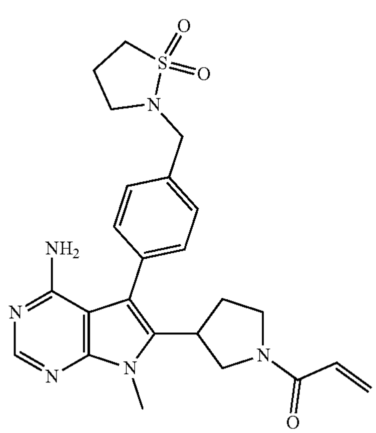 [SMILES: C=CC(=O)N1CCC(c2c(-c3ccc(CN4CCCS4(=O)=O)cc3)c3c(N)ncnc3n2C)C1] | C | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 798 | 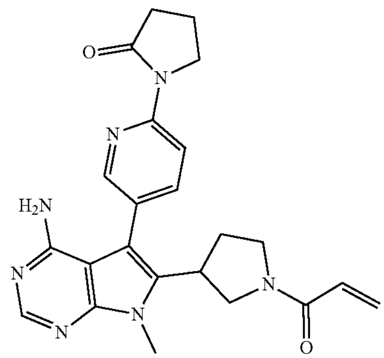 [SMILES: C=CC(=O)N1CCC(c2c(-c3ccc(N4CCCC4=O)nc3)c3c(N)ncnc3n2C)C1] | C | D |
| 799 | 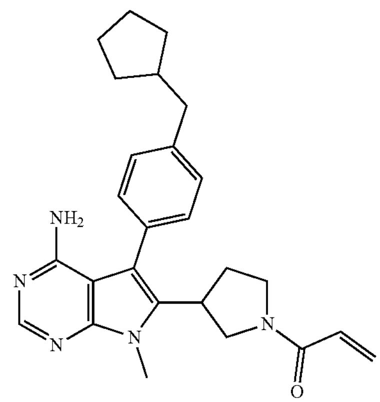 [SMILES: C=CC(=O)N1CCC(c2c(-c3ccc(CC4CCCC4)cc3)c3c(N)ncnc3n2C)C1] | C | C |
| 800 | 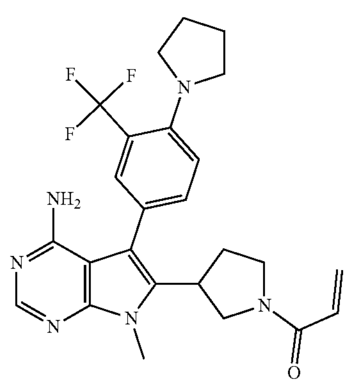 [SMILES: C=CC(=O)N1CCC(c2c(-c3ccc(N4CCCC4)c(C(F)(F)F)c3)c3c(N)ncnc3n2C)C1] | A | A |
| 801 | 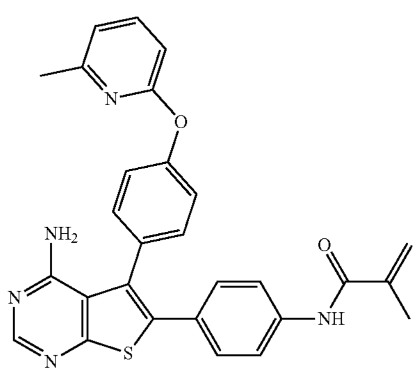 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 802 | 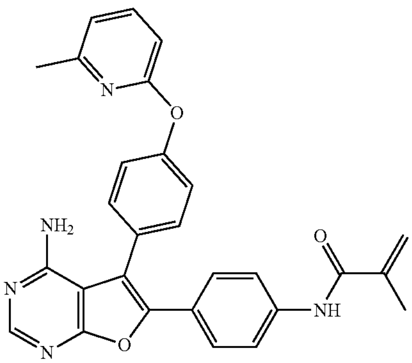 | D | D |
| 803 | 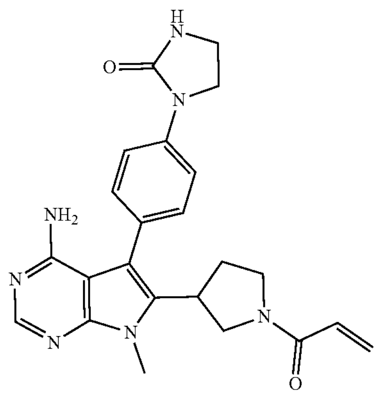 [SMILES: C=CC(=O)N1CCC(c2c(-c3ccc(N4CCNC4=O)cc3)c3c(N)ncnc3n2C)C1] | D | D |
| 804 | 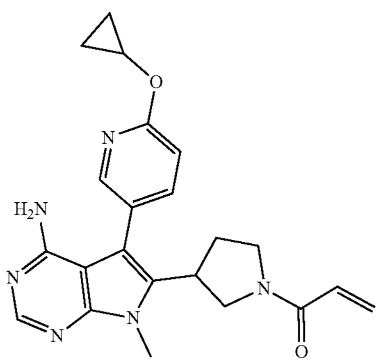 [SMILES: C=CC(=O)N1CCC(c2c(-c3ccc(OC4CC4)nc3)c3c(N)ncnc3n2C)C1] | B | D |
| 805 | 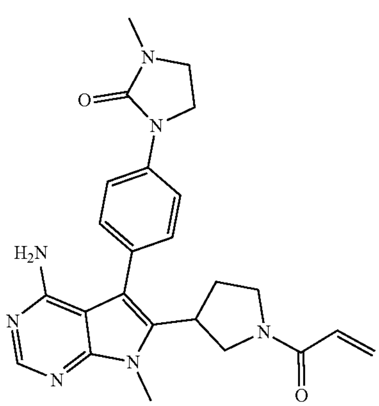 [SMILES: C=CC(=O)N1CCC(c2c(-c3ccc(N4CCN(C)C4=O)cc3)c3c(N)ncnc3n2C)C1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 806 | 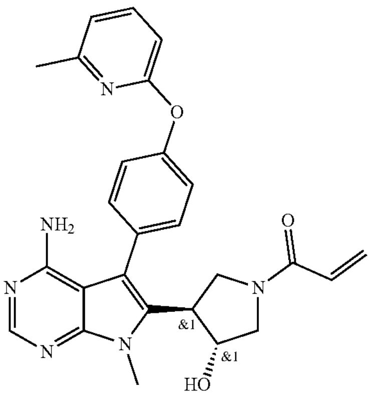 [SMILES: C=CC(=O)N1C[C@H](c2c(-c3ccc(Oc4cccc(C)n4)cc3)c3c(N)ncnc3n2C)[C@@H](O)C1] | A | B |
| 807 | 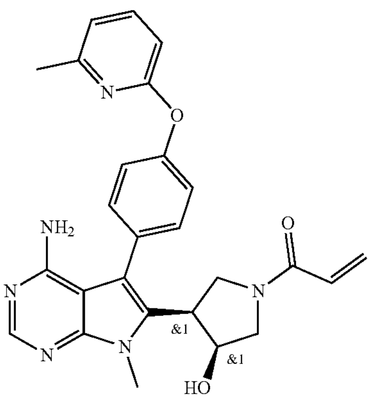 [SMILES: C=CC(=O)N1C[C@@H](O)[C@@H](c2c(-c3ccc(Oc4cccc(C)n4)cc3)c3c(N)ncnc3n2C)C1] | C | C |
| 808 | 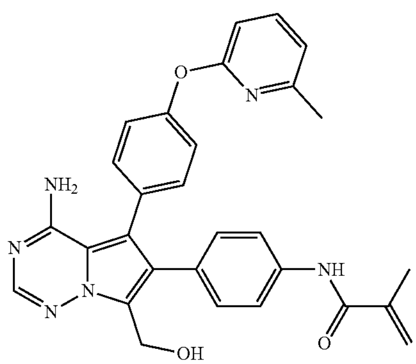 [SMILES: C=C(C)C(=O)Nc1ccc(-c2c(-c3ccc(Oc4cccc(C)n4)cc3)c3c(N)ncnn3c2CO)cc1] | B | B |
| 809 | 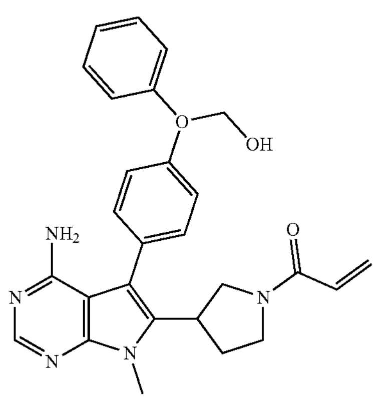 | A | A |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 810 | 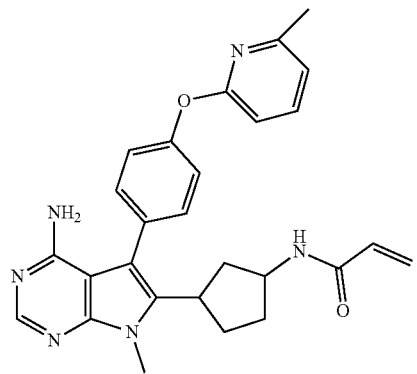 [SMILES: C=CC(=O)NC1CCC(c2c(-c3ccc(Oc4cccc(C)n4)cc3)c3c(N)ncnc3n2C)C1] | A | A |
| 811 | 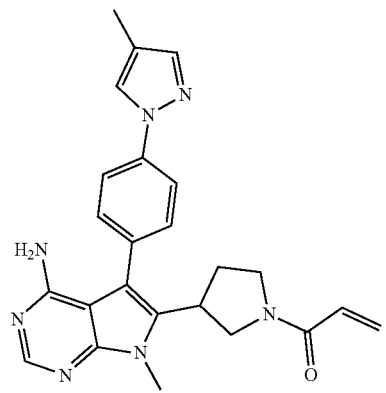 [SMILES: C=CC(=O)N1CCC(c2c(-c3ccc(-n4cc(C)cn4)cc3)c3c(N)ncnc3n2C)C1] | B | C |
| 812 | 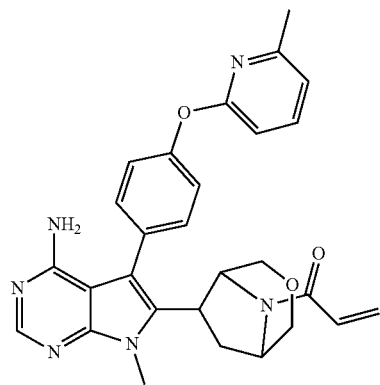 [SMILES: C=CC(=O)N1C2COCC1C(c1c(-c3ccc(Oc4cccc(C)n4)cc3)c3c(N)ncnc3n1C)C2] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 813 | 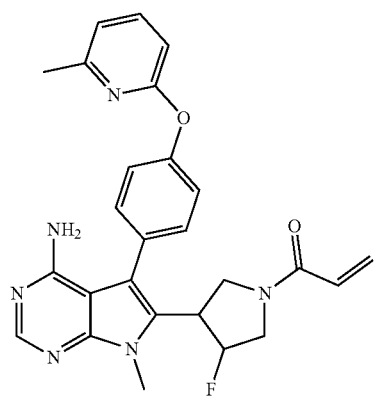 [SMILES: C=CC(=O)N1CC(F)C(c2c(-c3ccc(Oc4cccc(C)n4)cc3)c3c(N)ncnc3n2C)C1] | C | C |
| 814 | 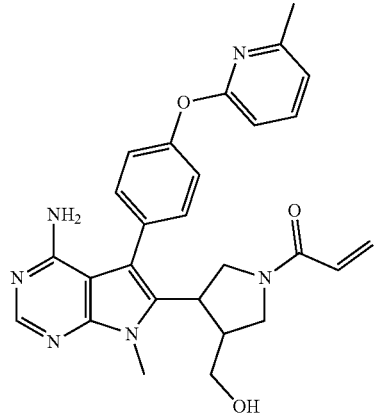 [SMILES: C=CC(=O)N1CC(CO)C(c2c(-c3ccc(Oc4cccc(C)n4)cc3)c3c(N)ncnc3n2C)C1] | A | A |
| 815 | 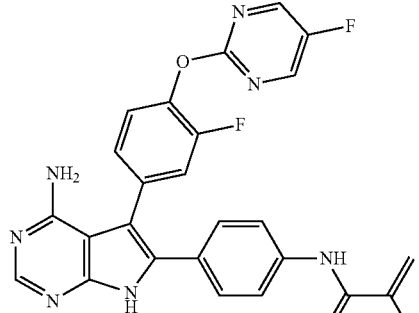 | C | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 816 | 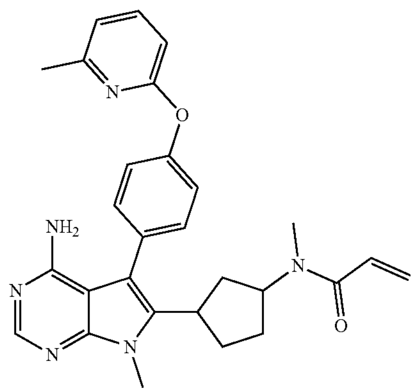 [SMILES: C=CC(=O)N(C)C1CCC(c2c(-c3ccc(Oc4cccc(C)n4)cc3)c3c(N)ncnc3n2C)C1] | C | B |
| 817 | 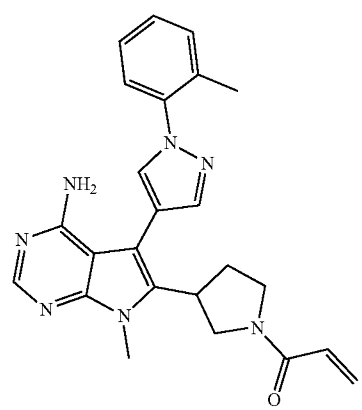 [SMILES: C=CC(=O)N1CCC(c2c(-c3cnn(-c4ccccc4C)c3)c3c(N)ncnc3n2C)C1] | B | B |
| 818 | 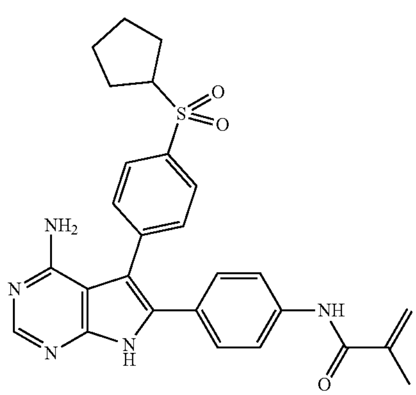 [SMILES: C=C(C)C(=O)Nc1ccc(-c2[nH]c3ncnc(N)c3c2-c2ccc(S(=O)(=O)C3CCCC3)cc2)cc1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 819 | 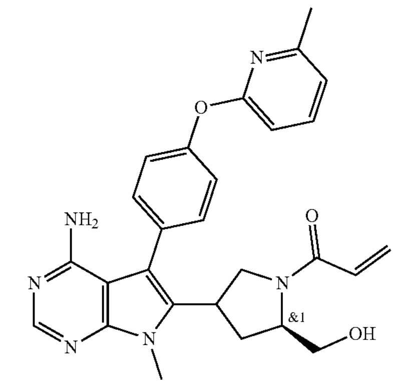 [SMILES: C=CC(=O)N1CC(c2c(-c3ccc(Oc4cccc(C)n4)cc3)c3c(N)ncnc3n2C)C[C@@H]1CO] | C | C |
| 820 | 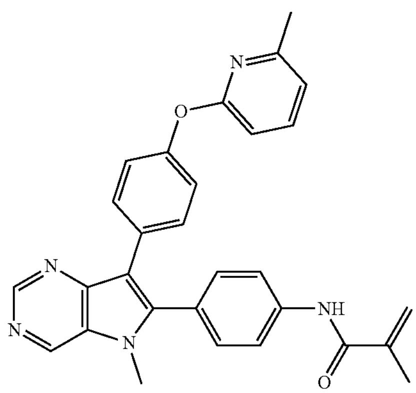 [SMILES: C=C(C)C(=O)Nc1ccc(-c2c(-c3ccc(Oc4cccc(C)n4)cc3)c3ncncc3n2C)cc1] | A | A |
| 821 | 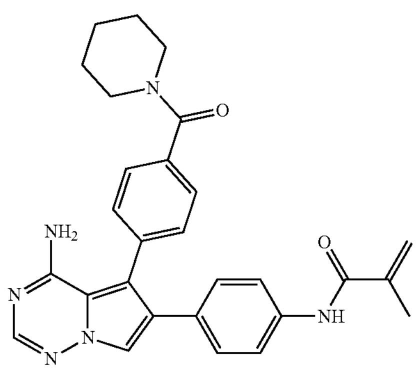 [SMILES: C=C(C)C(=O)Nc1ccc(-c2cn3ncnc(N)c3c2-c2ccc(C(=O)N3CCCCC3)cc2)cc1] | D | D |
| 822 | 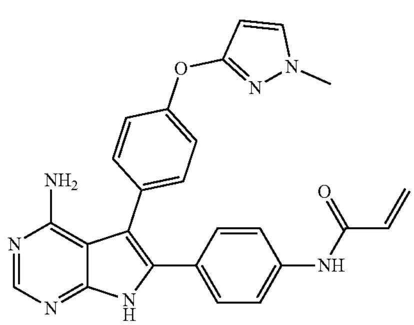 [SMILES: C=CC(=O)Nc1ccc(-c2[nH]c3ncnc(N)c3c2-c2ccc(Oc3ccn(C)n3)cc2)cc1] | C | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 823 | 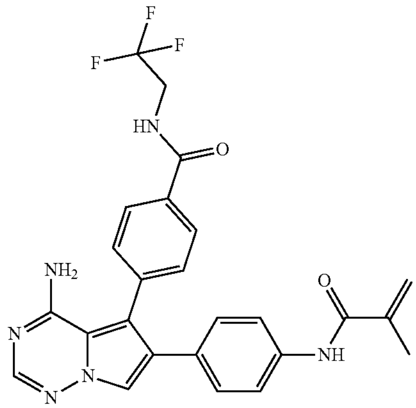 [SMILES: C=C(C)C(=O)Nc1ccc(-c2cn3ncnc(N)c3c2-c2ccc(C(=O)NCC(F)(F)F)cc2)cc1] | B | C |
| 824 | 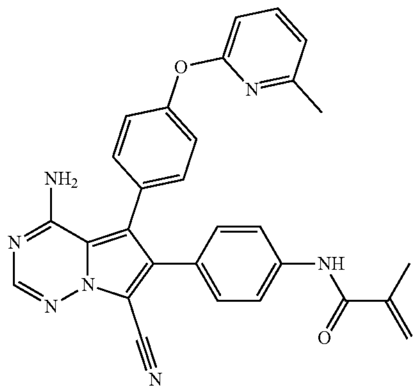 [SMILES: C=C(C)C(=O)Nc1ccc(-c2c(-c3ccc(Oc4cccc(C)n4)cc3)c3c(N)ncnn3c2C#N)cc1] | B | C |
| 825 | 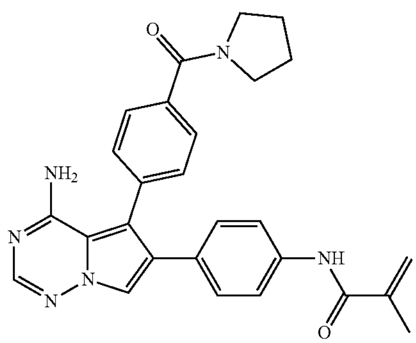 [SMILES: C=C(C)C(=O)Nc1ccc(-c2cn3ncnc(N)c3c2-c2ccc(C(=O)N3CCCC3)cc2)cc1] | B | A |
| 826 | 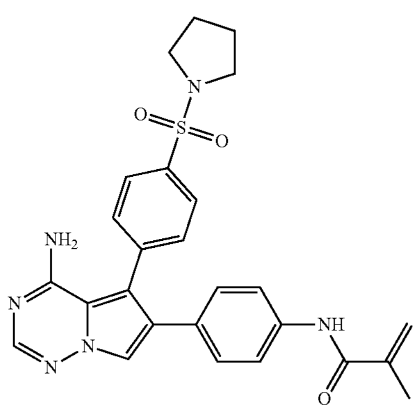 [SMILES: C=C(C)C(=O)Nc1ccc(-c2cn3ncnc(N)c3c2-c2ccc(S(=O)(=O)N3CCCC3)cc2)cc1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 827 | 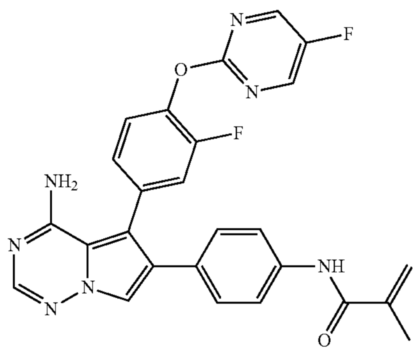 [SMILES: C=C(C)C(=O)Nc1ccc(-c2cn3ncnc(N)c3c2-c2ccc(Oc3ncc(F)cn3)c(F)c2)cc1] | D | D |
| 828 | 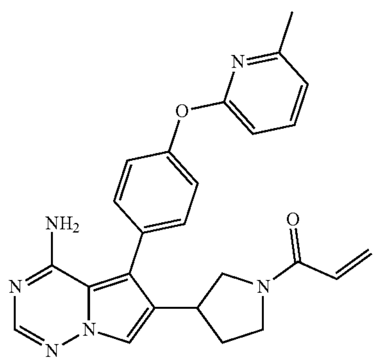 [SMILES: C=CC(=O)N1CCC(c2cn3ncnc(N)c3c2-c2ccc(Oc3cccc(C)n3)cc2)C1] | D | C |
| 829 | 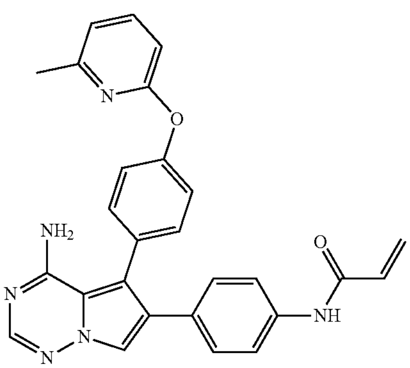 [SMILES: C=CC(=O)Nc1ccc(-c2cn3ncnc(N)c3c2-c2ccc(Oc3cccc(C)n3)cc2)cc1] | A | A |
| 830 | 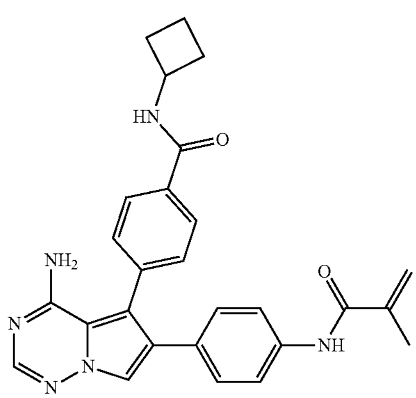 [SMILES: C=C(C)C(=O)Nc1ccc(-c2cn3ncnc(N)c3c2-c2ccc(C(=O)NC3CCC3)cc2)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 831 | 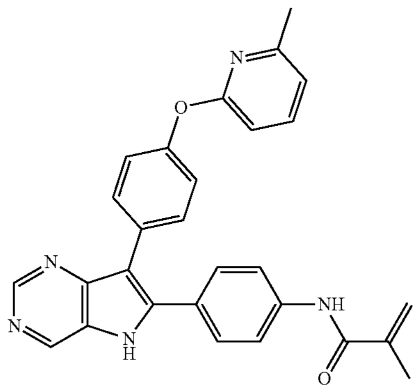 [SMILES: C=C(C)C(=O)Nc1ccc(-c2[nH]c3cncnc3c2-c2ccc(Oc3cccc(C)n3)cc2)cc1] | A | B |
| 832 | 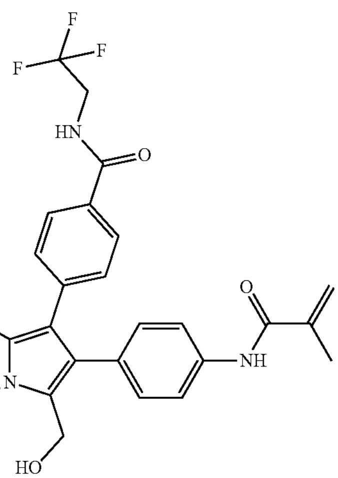 | D | D |
| 833 | 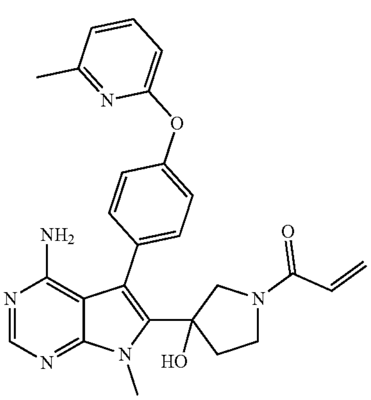 [SMILES: C=CC(=O)N1CCC(O)(c2c(-c3ccc(Oc4cccc(C)n4)cc3)c3c(N)ncnc3n2C)C1] | B | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 834 | 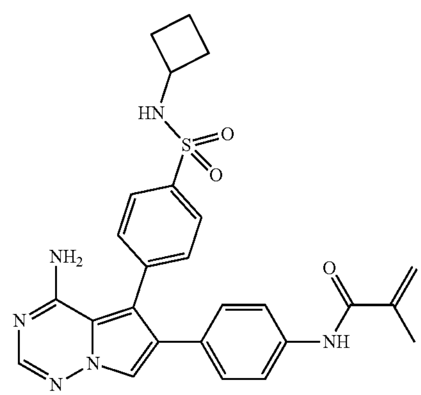 [SMILES: C=C(C)C(=O)Nc1ccc(-c2cn3ncnc(N)c3c2-c2ccc(S(=O)(=O)NC3CCC3)cc2)cc1] | C | C |
| 835 | 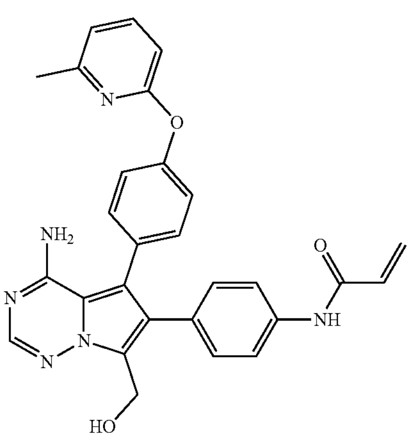 [SMILES: C=CC(=O)Nc1ccc(-c2c(-c3ccc(Oc4cccc(C)n4)cc3)c3c(N)ncnn3c2CO)cc1] | D | D |
| 836 | 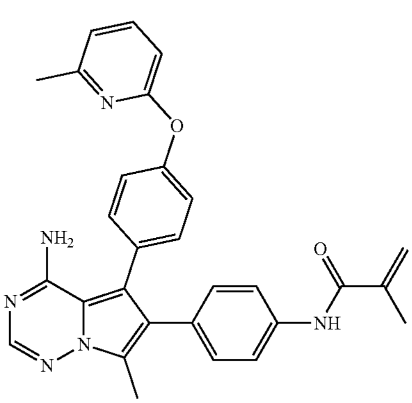 [SMILES: C=C(C)C(=O)Nc1ccc(-c2c(-c3ccc(Oc4cccc(C)n4)cc3)c3c(N)ncnn3c2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 837 | 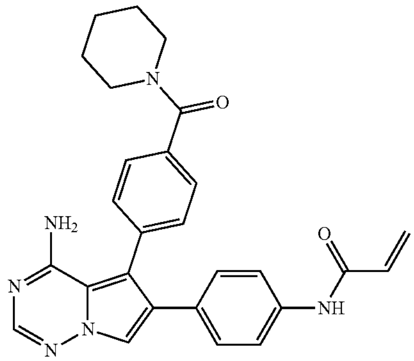 [SMILES: C=CC(=O)Nc1ccc(-c2cn3ncnc(N)c3c2-c2ccc(C(=O)N3CCCCC3)cc2)cc1] | A | A |
| 838 | 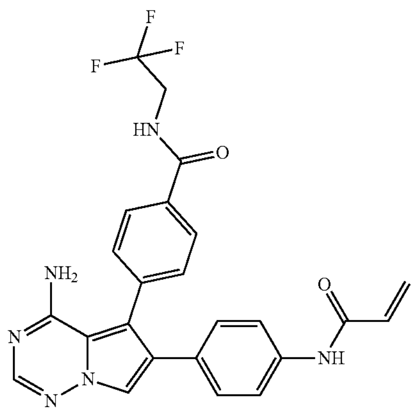 [SMILES: C=CC(=O)Nc1ccc(-c2cn3ncnc(N)c3c2-c2ccc(C(=O)NCC(F)(F)F)cc2)cc1] | A | A |
| 839 | 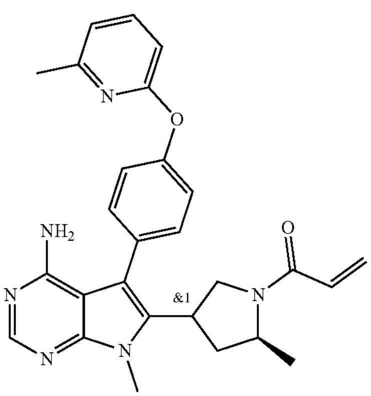 [SMILES: C=CC(=O)N1CC(c2c(-c3ccc(Oc4cccc(C)n4)cc3)c3c(N)ncnc3n2C)C[C@@H]1C] | A | A |
| 840 | 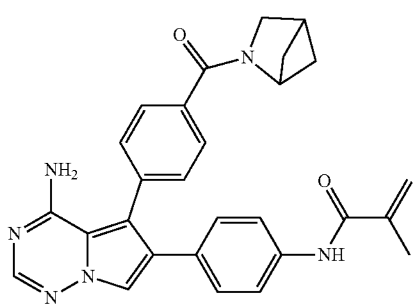 [SMILES: C=C(C)C(=O)Nc1ccc(-c2cn3ncnc(N)c3c2-c2ccc(C(=O)N3CC4CC3C4)cc2)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 841 | 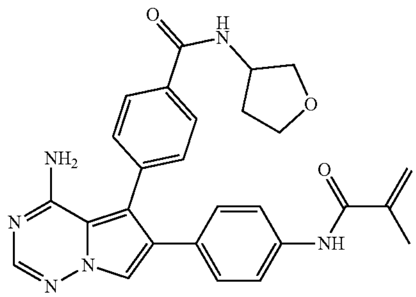 [SMILES: C=C(C)C(=O)Nc1ccc(-c2cn3ncnc(N)c3c2-c2ccc(C(=O)NC3CCOC3)cc2)cc1] | C | C |
| 842 | 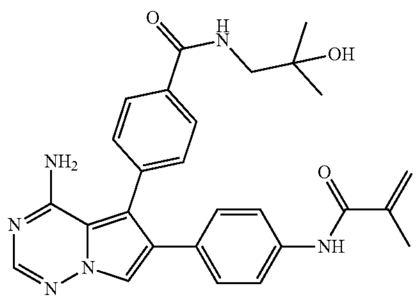 [SMILES: C=C(C)C(=O)Nc1ccc(-c2cn3ncnc(N)c3c2-c2ccc(C(=O)NCC(C)(C)O)cc2)cc1] | C | D |
| 843 | 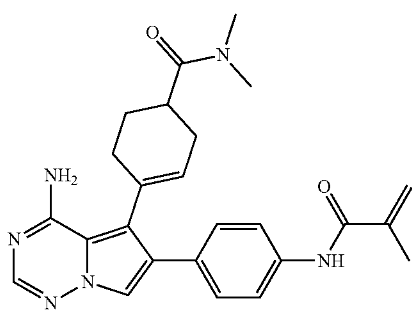 [SMILES: C=C(C)C(=O)Nc1ccc(-c2cn3ncnc(N)c3c2C2=CCC(C(=O)N(C)C)CC2)cc1] | C | C |
| 844 | 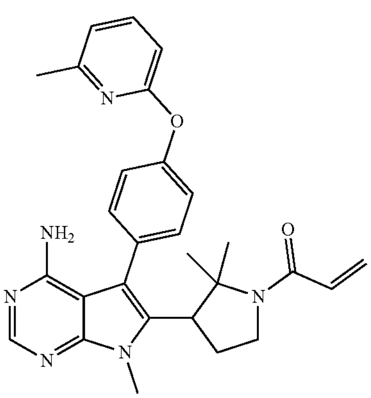 [SMILES: C=CC(=O)N1CCC(c2c(-c3ccc(Oc4cccc(C)n4)cc3)c3c(N)ncnc3n2C)C1(C)C] | D | D |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 845 | 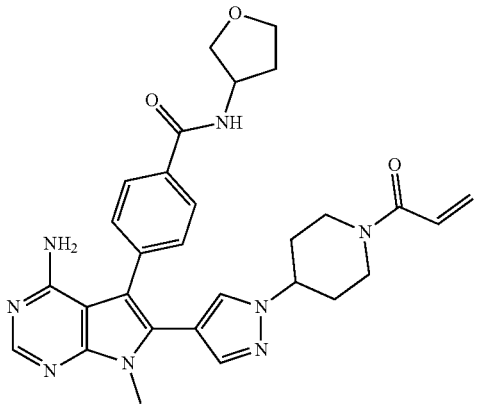 [SMILES: C=CC(=O)N1CCC(n2cc(-c3c(-c4ccc(C(=O)NC5CCOC5)cc4)c4c(N)ncnc4n3C)cn2)CC1] | C | C |
| 846 | 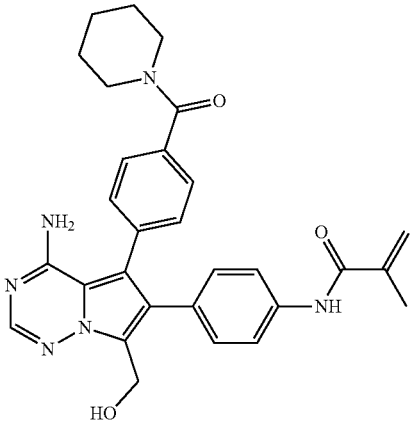 [SMILES: C=C(C)C(=O)Nc1ccc(-c2c(-c3ccc(C(=O)N4CCCCC4)cc3)c3c(N)ncnn3c2CO)cc1] | A | D |
| 847 | 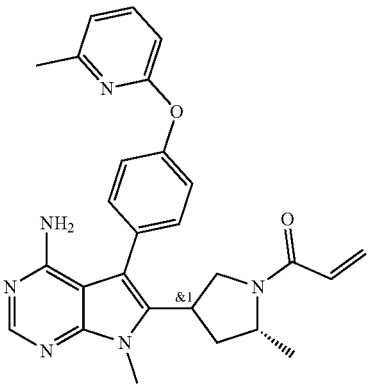 [SMILES: C=CC(=O)N1CC(c2c(-c3ccc(Oc4cccc(C)n4)cc3)c3c(N)ncnc3n2C)C[C@H]1C] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 848 | 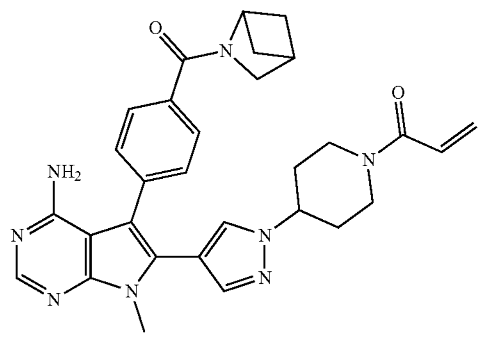 [SMILES: C=CC(=O)N1CCC(n2cc(-c3c(-c4ccc(C(=O)N5CC6CC5C6)cc4)c4c(N)ncnc4n3C)cn2)CC1] | B | B |
| 849 | 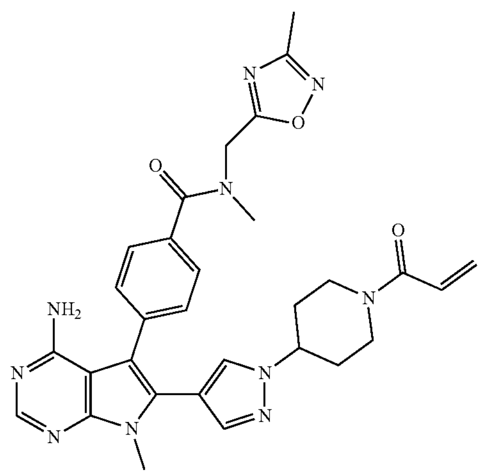 [SMILES: C=CC(=O)N1CCC(n2cc(-c3c(-c4ccc(C(=O)N(C)Cc5nc(C)no5)cc4)c4c(N)ncnc4n3C)cn2)CC1] | B | C |
| 850 | 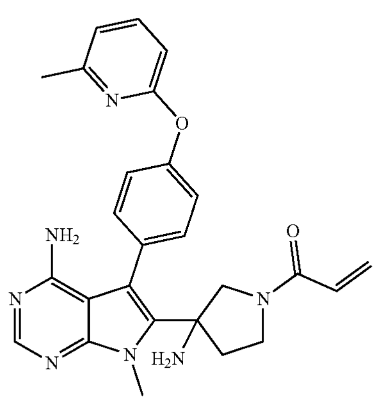 [SMILES: C=CC(=O)N1CCC(N)(c2c(-c3ccc(Oc4cccc(C)n4)cc3)c3c(N)ncnc3n2C)C1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 851 | 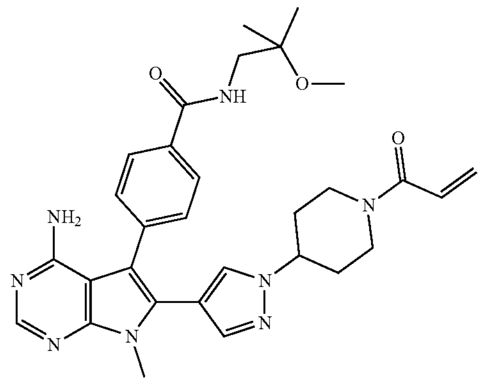 [SMILES: C=CC(=O)N1CCC(n2cc(-c3c(-c4ccc(C(=O)NCC(C)(C)OC)cc4)c4c(N)ncnc4n3C)cn2)CC1] | D | D |
| 852 | 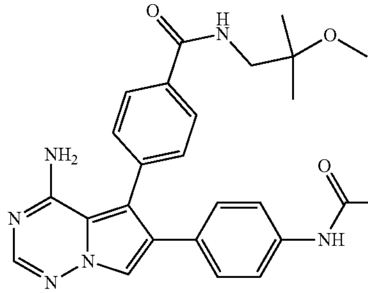 | C | D |
| 853 | 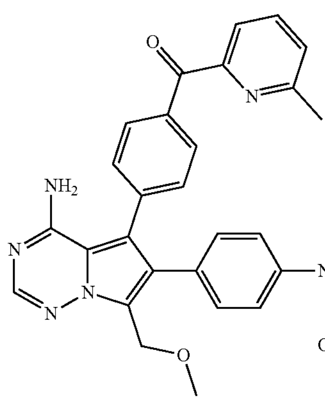 | C | B |
| 854 | 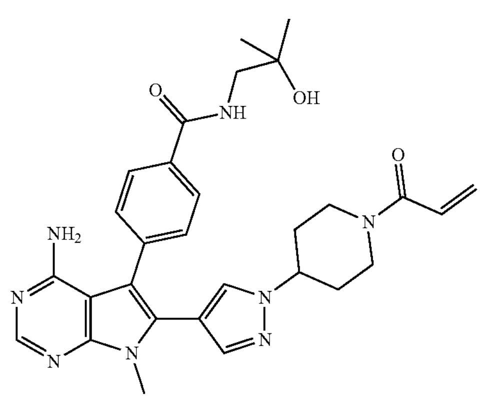 [SMILES: C=CC(=O)N1CCC(n2cc(-c3c(-c4ccc(C(=O)NCC(C)(C)O)cc4)c4c(N)ncnc4n3C)cn2)CC1] | B | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 855 | 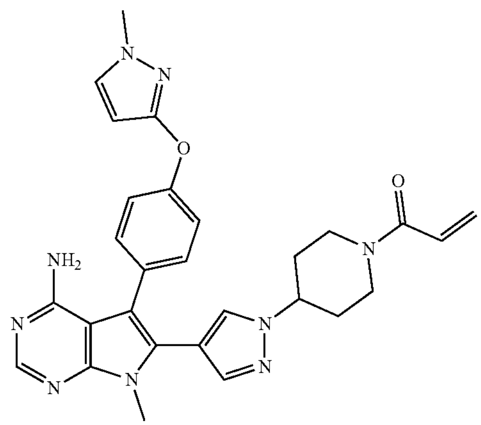 [SMILES: C=CC(=O)N1CCC(n2cc(-c3c(-c4ccc(Oc5ccn(C)n5)cc4)c4c(N)ncnc4n3C)cn2)CC1] | C | D |
| 856 | 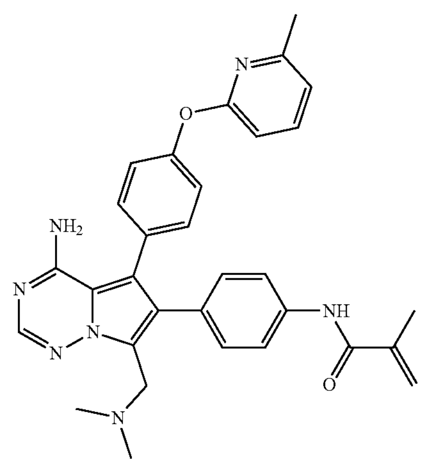 [SMILES: C=C(C)C(=O)Nc1ccc(-c2c(-c3ccc(Oc4cccc(C)n4)cc3)c3c(N)ncnn3c2CN(C)C)cc1] | C | C |
| 857 | 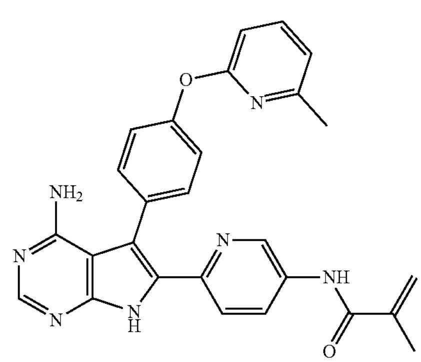 [SMILES: C=C(C)C(=O)Nc1ccc(-c2[nH]c3ncnc(N)c3c2-c2ccc(Oc3cccc(C)n3)cc2)nc1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 858 | 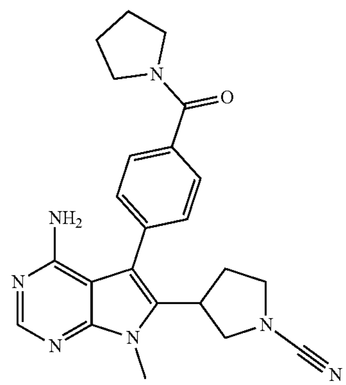 [SMILES: Cn1c(C2CCN(C#N)C2)c(-c2ccc(C(=O)N3CCCC3)cc2)c2c(N)ncnc21] | A | A |
| 859 | 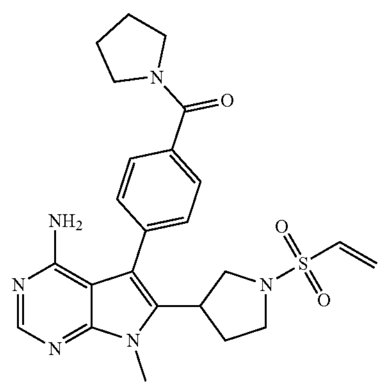 [SMILES: C=CS(=O)(=O)N1CCC(c2c(-c3ccc(C(=O)N4CCCC4)cc3)c3c(N)ncnc3n2C)C1] | D | D |
| 860 | 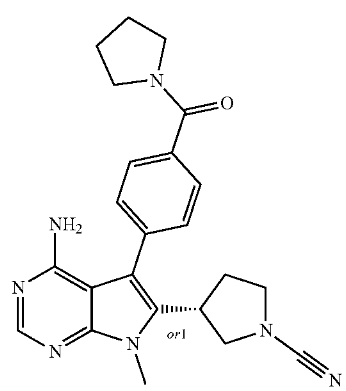 [SMILES: Cn1c([C@@H]2CCN(C#N)C2)c(-c2ccc(C(=O)N3CCCC3)cc2)c2c(N)ncnc21] | A | C |
| 861 | 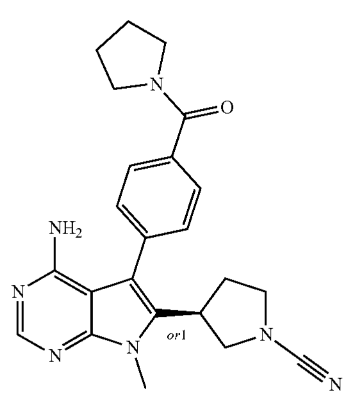 [SMILES: Cn1c([C@H]2CCN(C#N)C2)c(-c2ccc(C(=O)N3CCCC3)cc2)c2c(N)ncnc21] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 862 | 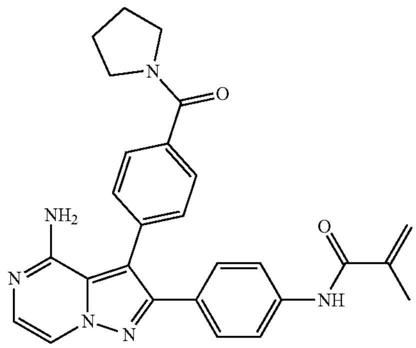 [SMILES: C=C(C)C(=O)Nc1ccc(-c2nn3ccnc(N)c3c2-c2ccc(C(=O)N3CCCC3)cc2)cc1] | D | D |
| 863 | 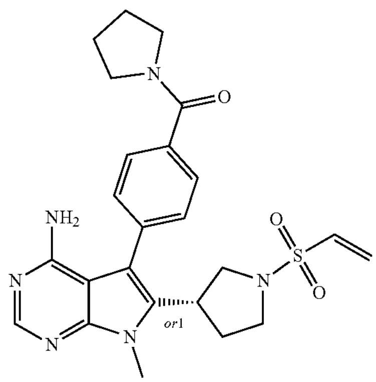 [SMILES: C=CS(=O)(=O)N1CC[C@H](c2c(-c3ccc(C(=O)N4CCCC4)cc3)c3c(N)ncnc3n2C)C1] | C | B |
| 864 | 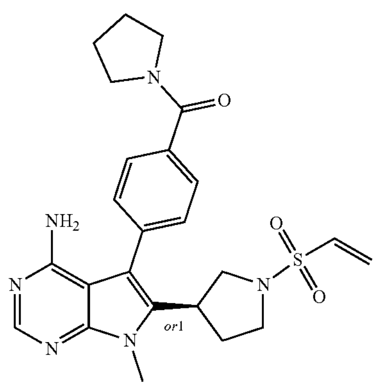 [SMILES: C=CS(=O)(=O)N1CC[C@@H](c2c(-c3ccc(C(=O)N4CCCC4)cc3)c3c(N)ncnc3n2C)C1] | A | B |
| 865 | 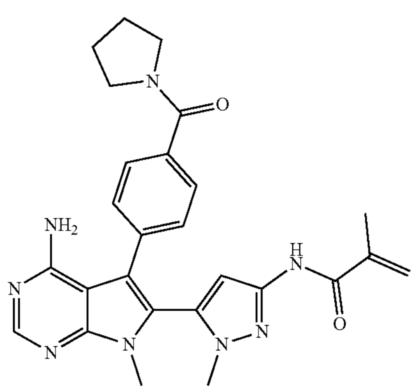 [SMILES: C=C(C)C(=O)Nc1cc(-c2c(-c3ccc(C(=O)N4CCCC4)cc3)c3c(N)ncnc3n2C)n(C)n1] | B | C |

US 11,780,845 B2
573                                                                                              574
TABLE 1-continued
Representative Compounds of the Invention with Bioactivity Data.
| Example | Structure | Biochemical FGFR2 Caliper IC50 | Cell SNU-16 IC50 |
|---|---|---|---|
| 866 | 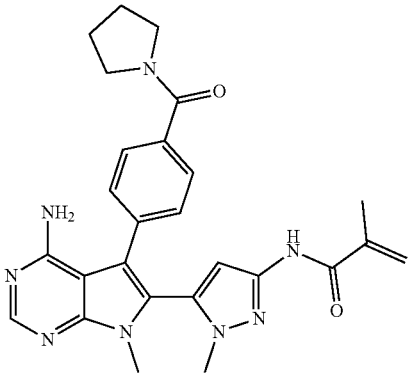 [SMILES: C=C(C)C(=O)Nc1cc(-c2c(-c3ccc(C(=O)N4CCCC4)cc3)c3c(N)ncnc3n2C)n(C)n1] | A | A |
| 867 | 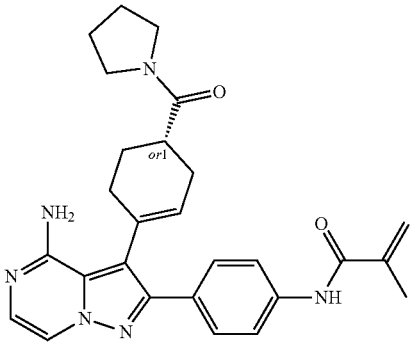 [SMILES: C=C(C)C(=O)Nc1ccc(-c2nn3ccnc(N)c3c2C2=CC[C@@H](C(=O)N3CCCC3)CC2)cc1] | A | A |
| 868 | 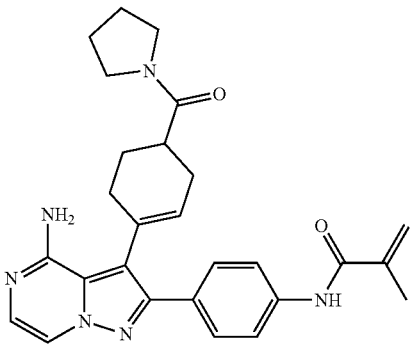 [SMILES: C=C(C)C(=O)Nc1ccc(-c2nn3ccnc(N)c3c2C2=CCC(C(=O)N3CCCC3)CC2)cc1] | D | D |
| 869 | 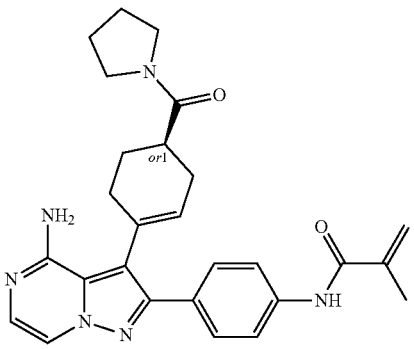 | D | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 870 | 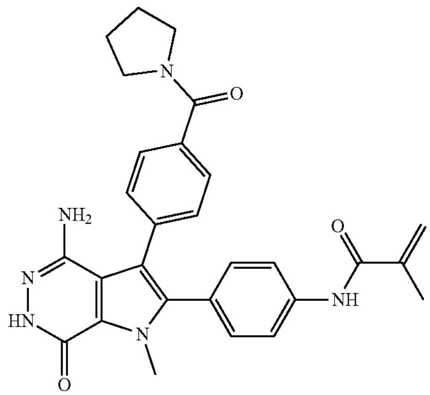 | D | B |
| 871 | 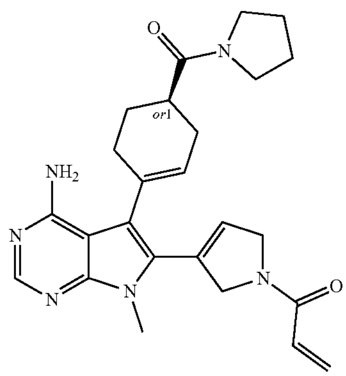 | C | C |
| 872 | 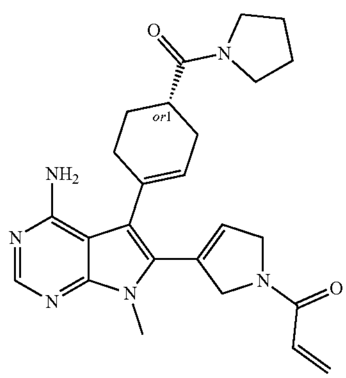 | B | B |
| 873 | 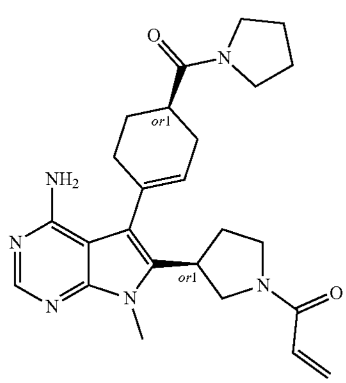 [SMILES: C=CC(=O)N1CC[C@H](c2c(C3=CC[C@H](C(=O)N4CCCC4)CC3)c3c(N)ncnc3n2C)C1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 874 | 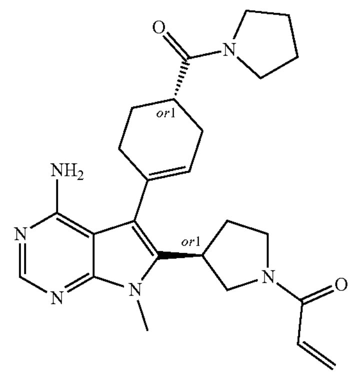 [SMILES: C=CC(=O)N1CC[C@H](c2c(C3=CC[C@@H](C(=O)N4CCCC4)CC3)c3c(N)ncnc3n2C)C1] | C | B |
| 875 | 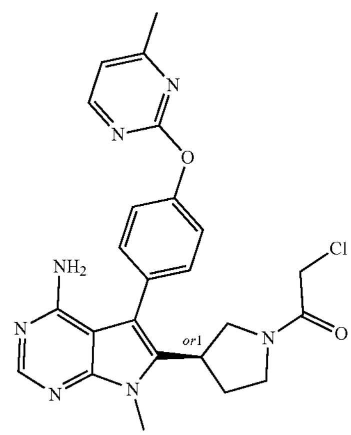 [SMILES: Cc1ccnc(Oc2ccc(-c3c([C@@H]4CCN(C(=O)CCl)C4)n(C)c4ncnc(N)c34)cc2)n1] | C | C |
| 876 | 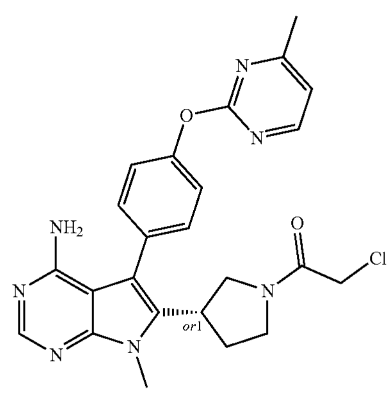 [SMILES: Cc1ccnc(Oc2ccc(-c3c([C@H]4CCN(C(=O)CCl)C4)n(C)c4ncnc(N)c34)cc2)n1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 877 | 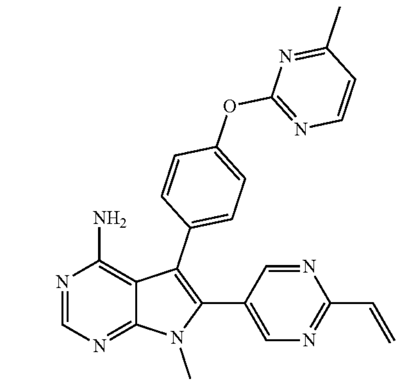 [SMILES: C=Cc1ncc(-c2c(-c3ccc(Oc4nccc(C)n4)cc3)c3c(N)ncnc3n2C)cn1] | B | C |
| 878 | 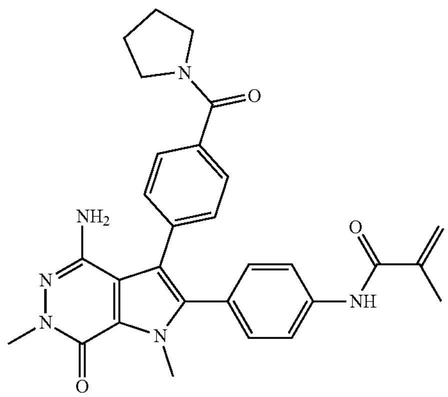 [SMILES: C=C(C)C(=O)Nc1ccc(-c2c(-c3ccc(C(=O)N4CCCC4)cc3)c3c(N)nn(C)c(=O)c3n2C)cc1] | B | A |
| 879 | 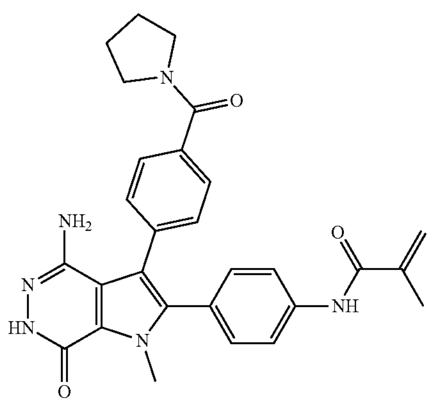 | D | D |
| 880 | 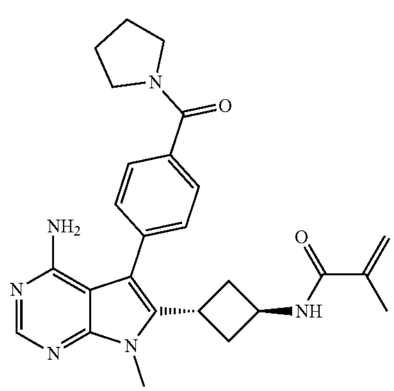 [SMILES: C=C(C)C(=O)N[C@H]1C[C@H](c2c(-c3ccc(C(=O)N4CCCC4)cc3)c3c(N)ncnc3n2C)C1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 881 | 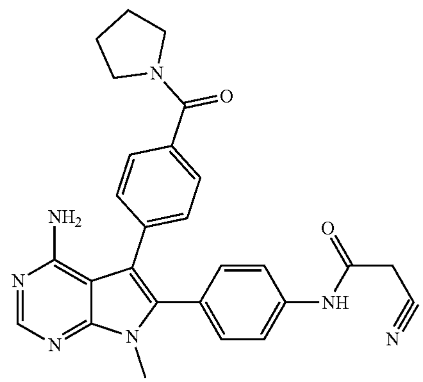 [SMILES: Cn1c(-c2ccc(NC(=O)CC#N)cc2)c(-c2ccc(C(=O)N3CCCC3)cc2)c2c(N)ncnc21] | D | D |
| 882 | 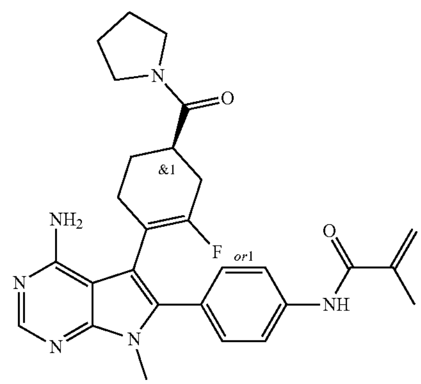 [SMILES: C=C(C)C(=O)Nc1ccc(-c2c(C3=C(F)C[C@H](C(=O)N4CCCC4)CC3)c3c(N)ncnc3n2C)cc1] | D | D |
| 883 | 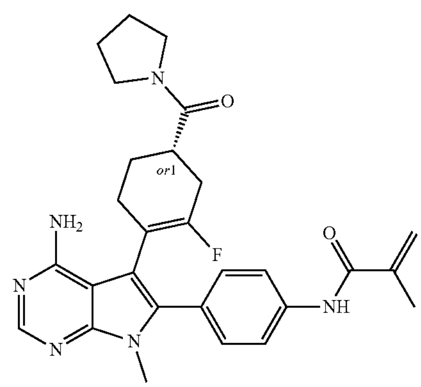 [SMILES: C=C(C)C(=O)Nc1ccc(-c2c(C3=C(F)C[C@@H](C(=O)N4CCCC4)CC3)c3c(N)ncnc3n2C)cc1] | D | D |
| 884 | 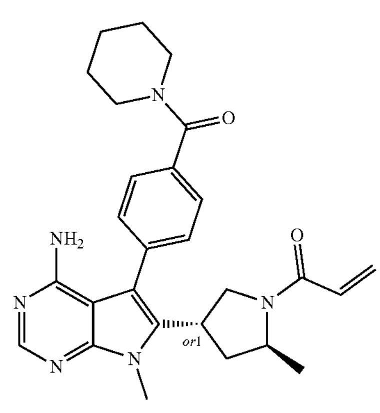 [SMILES: C=CC(=O)N1C[C@@H](c2c(-c3ccc(C(=O)N4CCCCC4)cc3)c3c(N)ncnc3n2C)C[C@@H]1C] | D | B |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 885 | 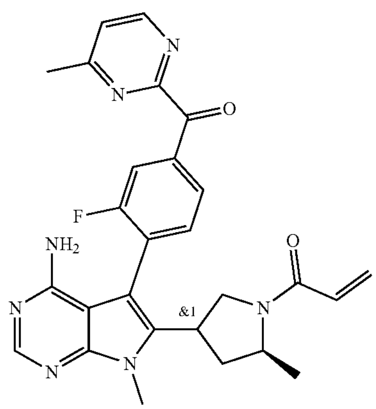 [SMILES: C=CC(=O)N1CC(c2c(-c3ccc(C(=O)c4nccc(C)n4)cc3F)c3c(N)ncnc3n2C)C[C@@H]1C] | D | D |
| 886 | 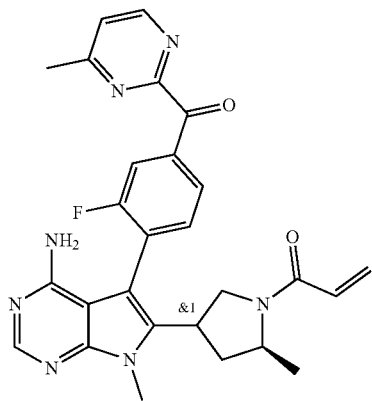 [SMILES: C=CC(=O)N1CC(c2c(-c3ccc(C(=O)c4nccc(C)n4)cc3F)c3c(N)ncnc3n2C)C[C@@H]1C] | C | A |
| 887 | 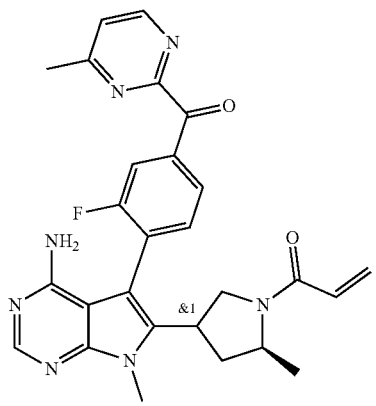 | D | D |
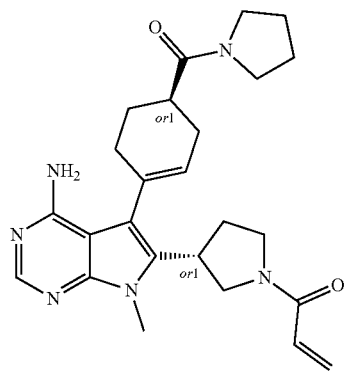 [SMILES: C=CC(=O)N1CC[C@@H](c2c(C3=CC[C@H](C(=O)N4CCCC4)CC3)c3c(N)ncnc3n2C)C1]

TABLE 1-continued

Representative Compounds of the Invention with Bioactivity Data.

| Example | Structure | Biochemical FGFR2 Caliper IC50 | Cell SNU-16 IC50 |
|---|---|---|---|
| 888 | 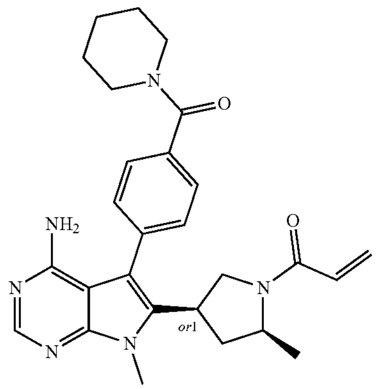 [SMILES: C=CC(=O)N1C[C@H](c2c(-c3ccc(C(=O)N4CCCCC4)cc3)c3c(N)ncnc3n2C)C[C@@H]1C] | D | D |
| 889 | 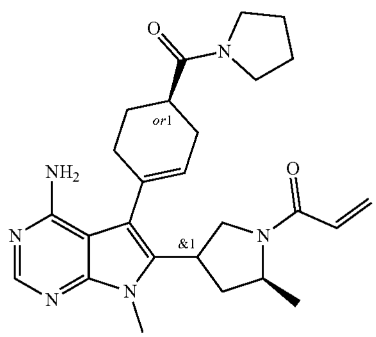 [SMILES: C=CC(=O)N1CC(c2c(C3=CC[C@H](C(=O)N4CCCC4)CC3)c3c(N)ncnc3n2C)C[C@@H]1C] | C | B |
| 890 | 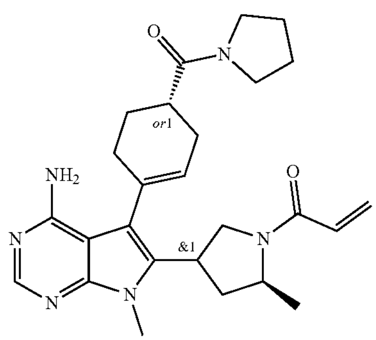 [SMILES: C=CC(=O)N1CC(c2c(C3=CC[C@@H](C(=O)N4CCCC4)CC3)c3c(N)ncnc3n2C)C[C@@H]1C] | D | D |
| 891 | 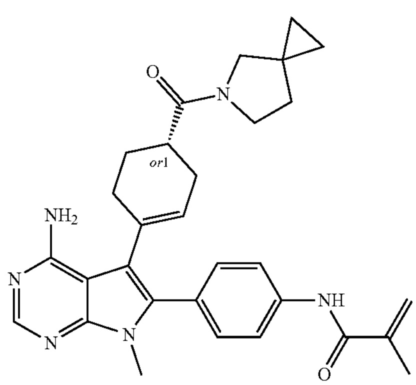 [SMILES: C=C(C)C(=O)Nc1ccc(-c2c(C3=CC[C@@H](C(=O)N4CCC5(CC5)C4)CC3)c3c(N)ncnc3n2C)cc1] | D | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 892 | 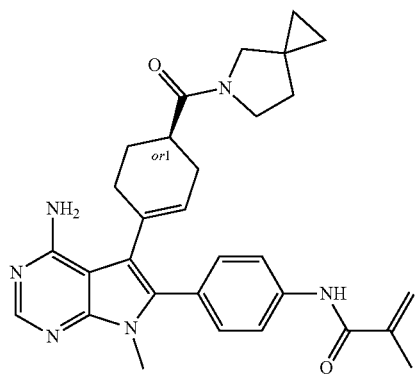 [SMILES: C=C(C)C(=O)Nc1ccc(-c2c(C3=CC[C@H](C(=O)N4CCC5(CC5)C4)CC3)c3c(N)ncnc3n2C)cc1] | B | A |
| 893 | 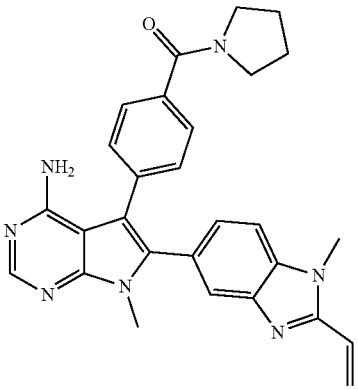 [SMILES: C=Cc1nc2cc(-c3c(-c4ccc(C(=O)N5CCCC5)cc4)c4c(N)ncnc4n3C)ccc2n1C] | D | D |
| 894 | 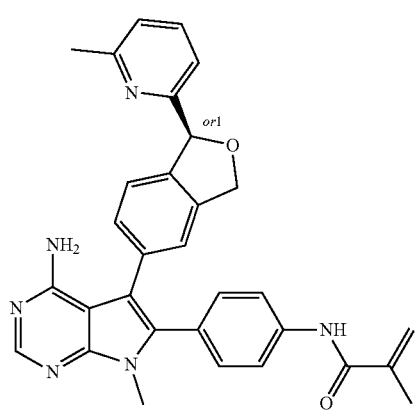 [SMILES: C=C(C)C(=O)Nc1ccc(-c2c(-c3ccc4c(c3)CO[C@@H]4c3cccc(C)n3)c3c(N)ncnc3n2C)cc1] | C | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 895 | 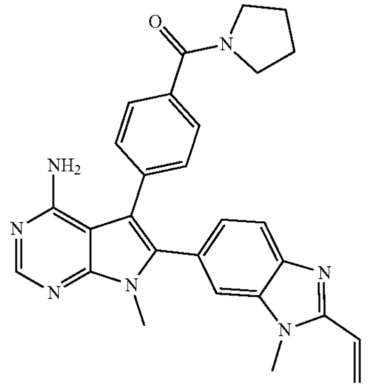 [SMILES: C=Cc1nc2ccc(-c3c(-c4ccc(C(=O)N5CCCC5)cc4)c4c(N)ncnc4n3C)cc2n1C] | D | D |
| 896 | 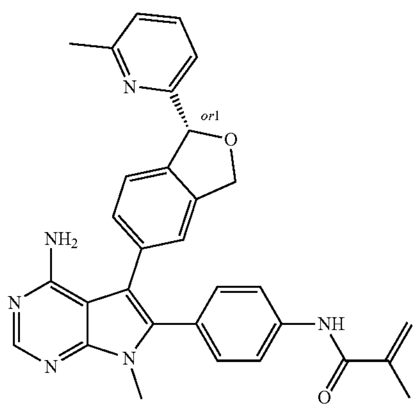 [SMILES: C=C(C)C(=O)Nc1ccc(-c2c(-c3ccc4c(c3)CO[C@H]4c3cccc(C)n3)c3c(N)ncnc3n2C)cc1] | B | C |
| 897 | 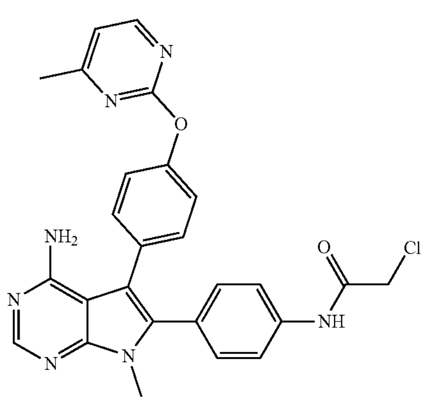 [SMILES: Cc1ccnc(Oc2ccc(-c3c(-c4ccc(NC(=O)CCl)cc4)n(C)c4ncnc(N)c34)cc2)n1] | B | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 898 | 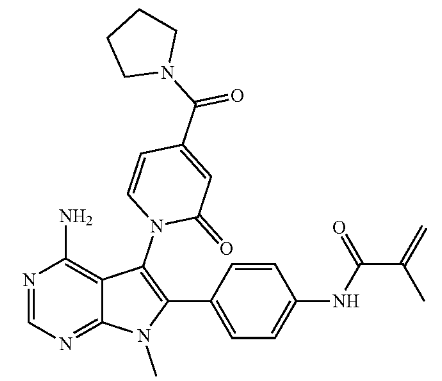 [SMILES: C=C(C)C(=O)Nc1ccc(-c2c(-n3ccc(C(=O)N4CCCC4)cc3=O)c3c(N)ncnc3n2C)cc1] | A | A |
| 899 | 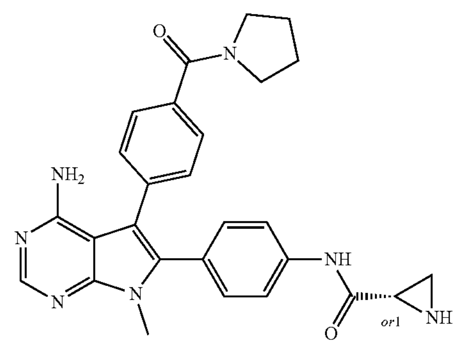 [SMILES: Cn1c(-c2ccc(NC(=O)[C@@H]3CN3)cc2)c(-c2ccc(C(=O)N3CCCC3)cc2)c2c(N)ncnc21] | D | D |
| 900 | 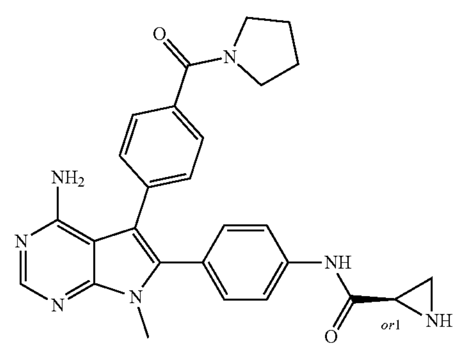 [SMILES: Cn1c(-c2ccc(NC(=O)[C@H]3CN3)cc2)c(-c2ccc(C(=O)N3CCCC3)cc2)c2c(N)ncnc21] | D | D |
| 901 | 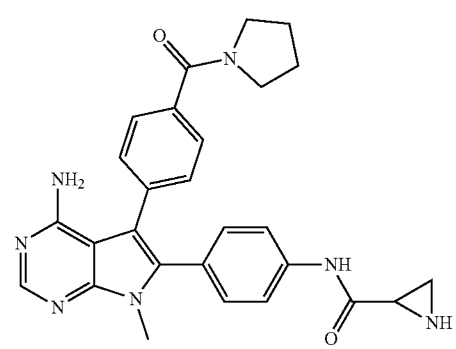 | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 902 | 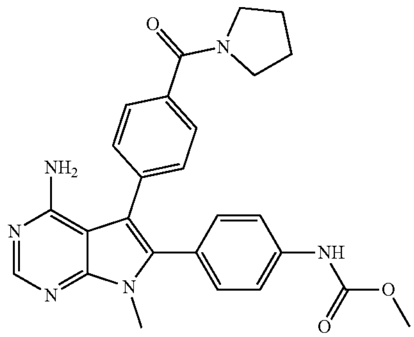 [SMILES: COC(=O)Nc1ccc(-c2c(-c3ccc(C(=O)N4CCCC4)cc3)c3c(N)ncnc3n2C)cc1] | D | D |
| 903 | 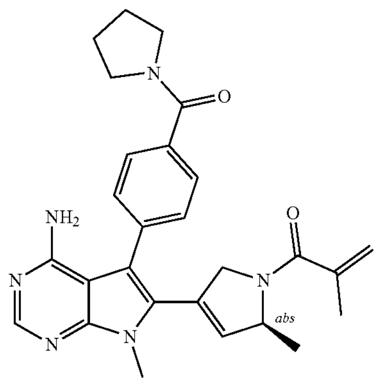 [SMILES: C=C(C)C(=O)N1CC(c2c(-c3ccc(C(=O)N4CCCC4)cc3)c3c(N)ncnc3n2C)=C[C@@H]1C] | D | D |
| 904 | 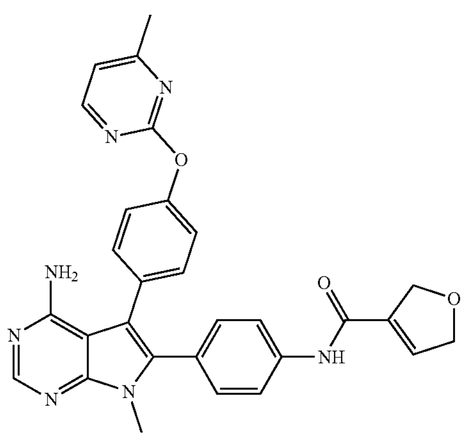 [SMILES: Cc1ccnc(Oc2ccc(-c3c(-c4ccc(NC(=O)C5=CCOC5)cc4)n(C)c4ncnc(N)c34)cc2)n1] | D | D |
| 905 | 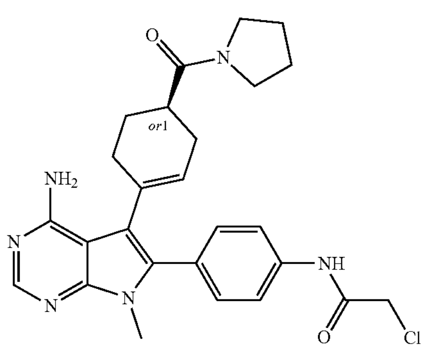 [SMILES: Cn1c(-c2ccc(NC(=O)CCl)cc2)c(C2=CC[C@H](C(=O)N3CCCC3)CC2)c2c(N)ncnc21] | B | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 906 | 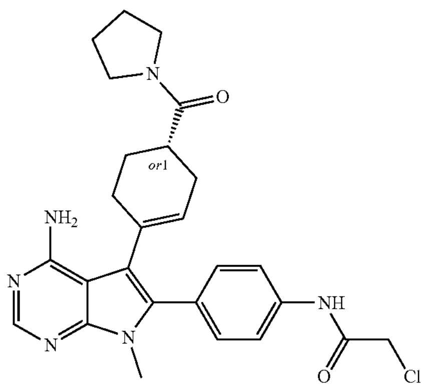 [SMILES: Cn1c(-c2ccc(NC(=O)CCl)cc2)c(C2=CC[C@@H](C(=O)N3CCCC3)CC2)c2c(N)ncnc21] | A | A |
| 907 | 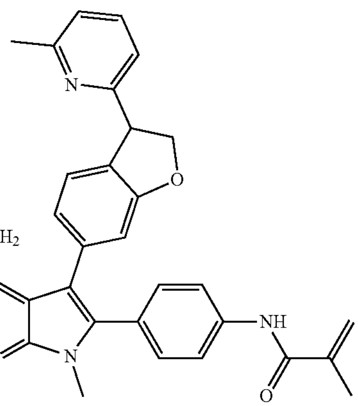 | A | A |
| 908 | 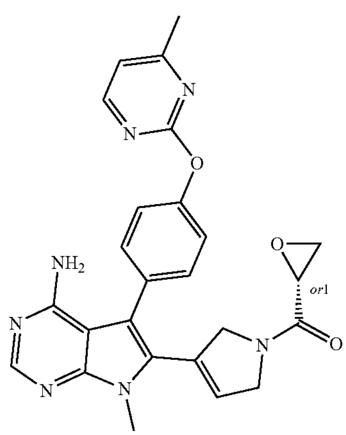 [SMILES: Cc1ccnc(Oc2ccc(-c3c(C4=CCN(C(=O)[C@H]5CO5)C4)n(C)c4ncnc(N)c34)cc2)n1] | B | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 909 | 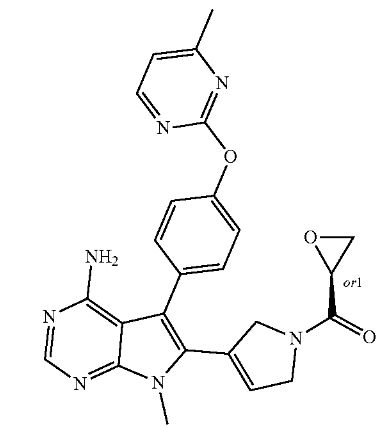 [SMILES: Cc1ccnc(Oc2ccc(-c3c(C4=CCN(C(=O)[C@@H]5CO5)C4)n(C)c4ncnc(N)c34)cc2)n1] | D | D |
| 910 | 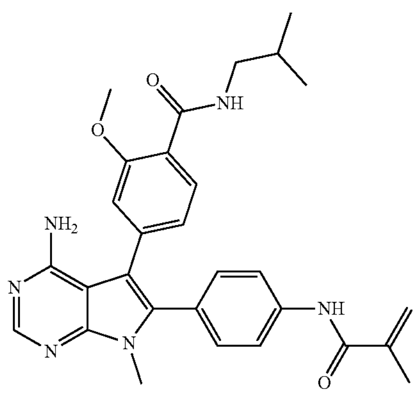 [SMILES: C=C(C)C(=O)Nc1ccc(-c2c(-c3ccc(C(=O)NCC(C)C)c(OC)c3)c3c(N)ncnc3n2C)cc1] | D | D |
| 911 | 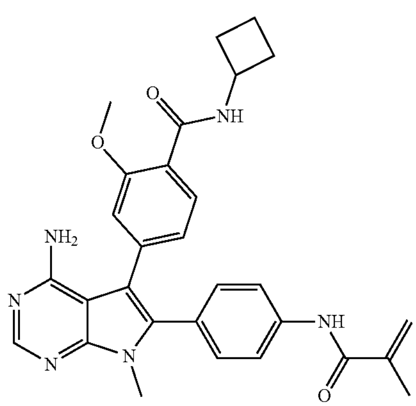 [SMILES: C=C(C)C(=O)Nc1ccc(-c2c(-c3ccc(C(=O)NC4CCC4)c(OC)c3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 912 | 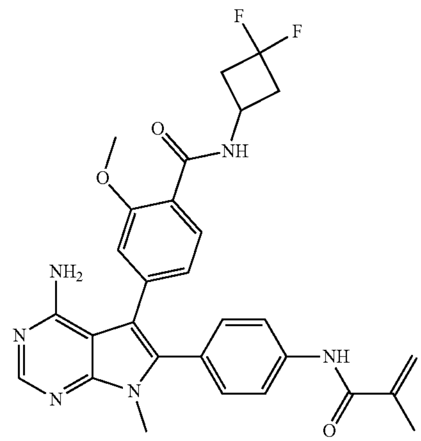 [SMILES: C=C(C)C(=O)Nc1ccc(-c2c(-c3ccc(C(=O)NC4CC(F)(F)C4)c(OC)c3)c3c(N)ncnc3n2C)cc1] | A | A |
| 913 | 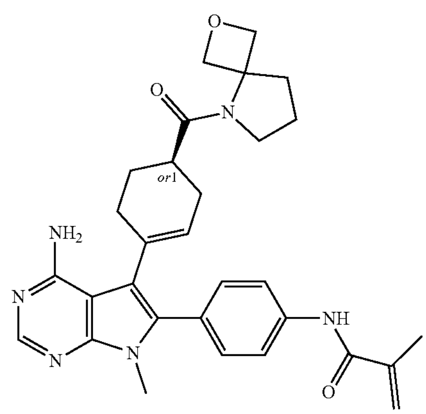 [SMILES: C=C(C)C(=O)Nc1ccc(-c2c(C3=CC[C@H](C(=O)N4CCCC45COC5)CC3)c3c(N)ncnc3n2C)cc1] | A | A |
| 914 | 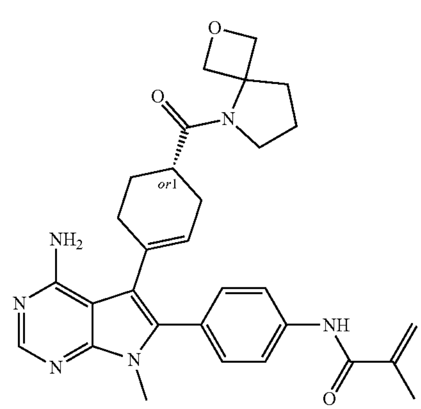 [SMILES: C=C(C)C(=O)Nc1ccc(-c2c(C3=CC[C@@H](C(=O)N4CCCC45COC5)CC3)c3c(N)ncnc3n2C)cc1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 915 | 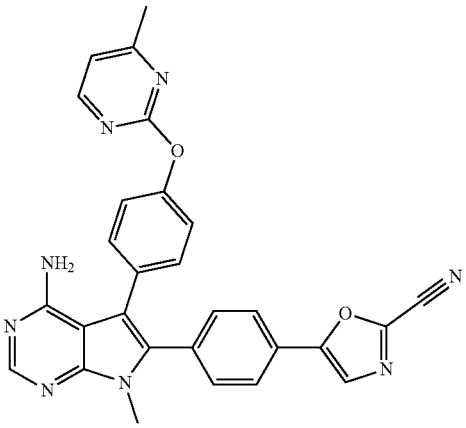 [SMILES: Cc1ccnc(Oc2ccc(-c3c(-c4ccc(-c5cnc(C#N)o5)cc4)n(C)c4ncnc(N)c34)cc2)n1] | D | C |
| 916 | 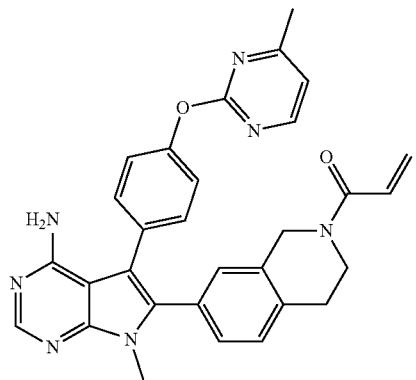 [SMILES: C=CC(=O)N1CCc2ccc(-c3c(-c4ccc(Oc5nccc(C)n5)cc4)c4c(N)ncnc4n3C)cc2C1] | D | B |
| 917 | 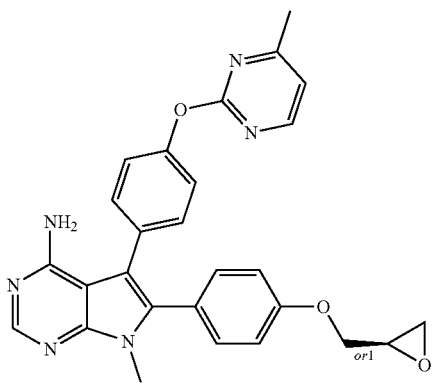 | B | B |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 918 | 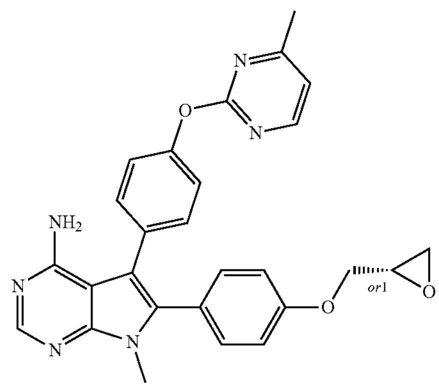 [SMILES: Cc1ccnc(Oc2ccc(-c3c(-c4ccc(OC[C@@H]5CO5)cc4)n(C)c4ncnc(N)c34)cc2)n1] | C | D |
| 919 | 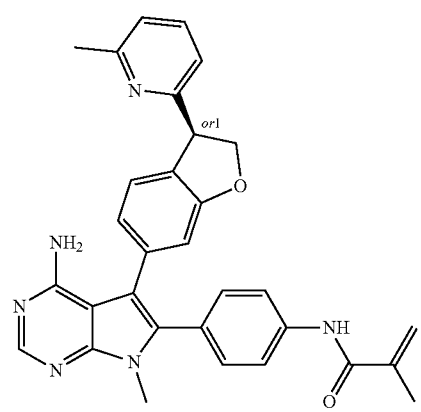 [SMILES: C=C(C)C(=O)Nc1ccc(-c2c(-c3ccc4c(c3)OC[C@@H]4c3cccc(C)n3)c3c(N)ncnc3n2C)cc1] | B | D |
| 920 | 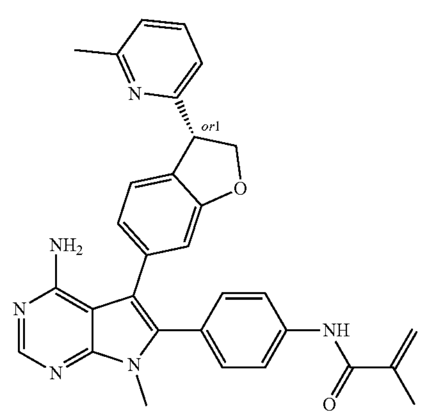 [SMILES: C=C(C)C(=O)Nc1ccc(-c2c(-c3ccc4c(c3)OC[C@H]4c3cccc(C)n3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 921 | 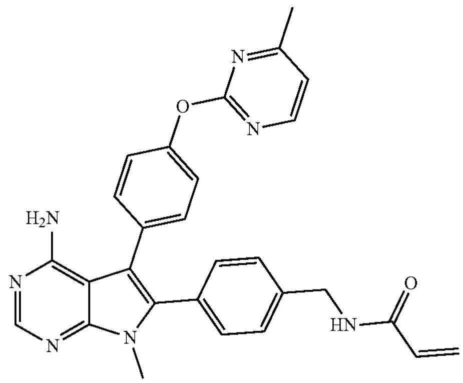 [SMILES: C=CC(=O)NCc1ccc(-c2c(-c3ccc(Oc4nccc(C)n4)cc3)c3c(N)ncnc3n2C)cc1] | D | C |
| 922 | 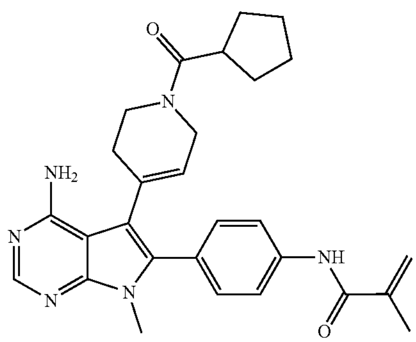 | C | C |
| 923 | 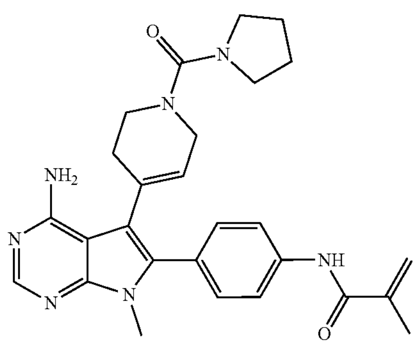 [SMILES: C=C(C)C(=O)Nc1ccc(-c2c(C3=CCN(C(=O)N4CCCC4)CC3)c3c(N)ncnc3n2C)cc1] | D | C |
| 924 | 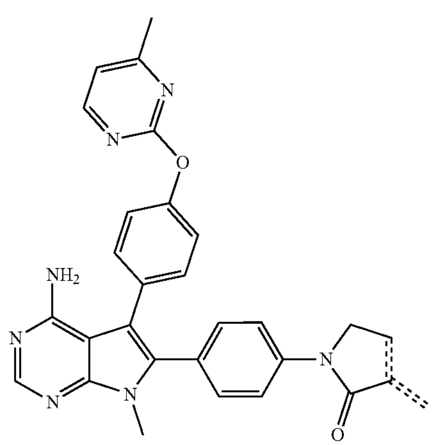 | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 925 | 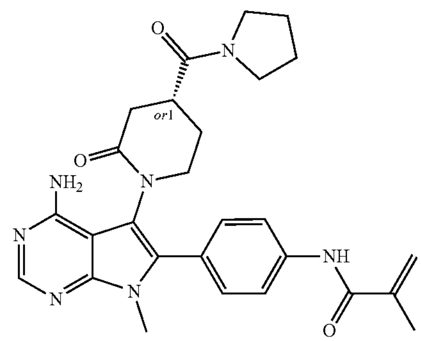 [SMILES: C=C(C)C(=O)Nc1ccc(-c2c(N3CC[C@@H](C(=O)N4CCCC4)CC3=O)c3c(N)ncnc3n2C)cc1] | A | A |
| 926 | 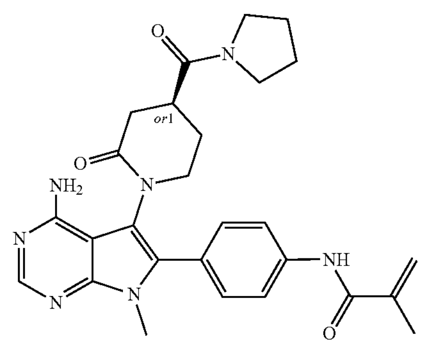 [SMILES: C=C(C)C(=O)Nc1ccc(-c2c(N3CC[C@H](C(=O)N4CCCC4)CC3=O)c3c(N)ncnc3n2C)cc1] | D | D |
| 927 | 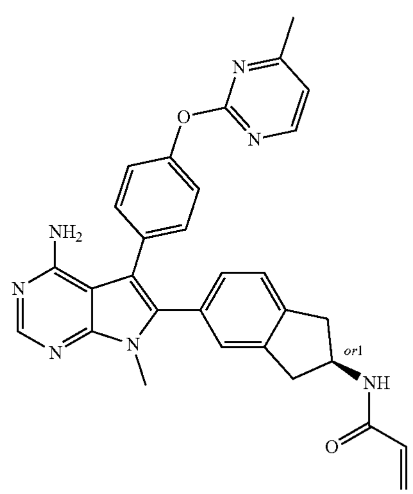 [SMILES: C=CC(=O)N[C@@H]1Cc2ccc(-c3c(-c4ccc(Oc5nccc(C)n5)cc4)c4c(N)ncnc4n3C)cc2C1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 928 | 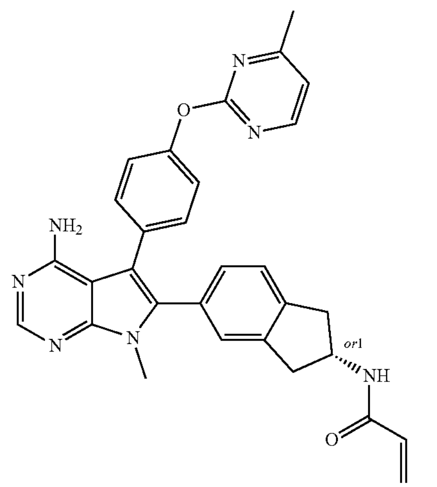 [SMILES: C=CC(=O)N[C@H]1Cc2ccc(-c3c(-c4ccc(Oc5nccc(C)n5)cc4)c4c(N)ncnc4n3C)cc2C1] | C | C |
| 929 | 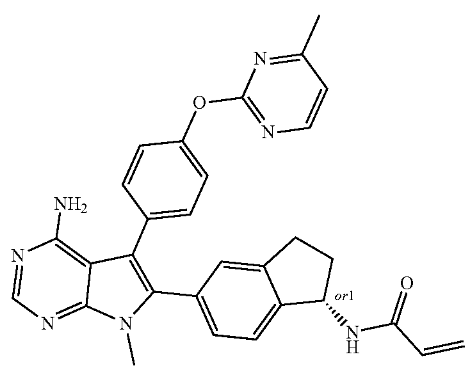 [SMILES: C=CC(=O)N[C@H]1CCc2cc(-c3c(-c4ccc(Oc5nccc(C)n5)cc4)c4c(N)ncnc4n3C)ccc21] | C | B |
| 930 | 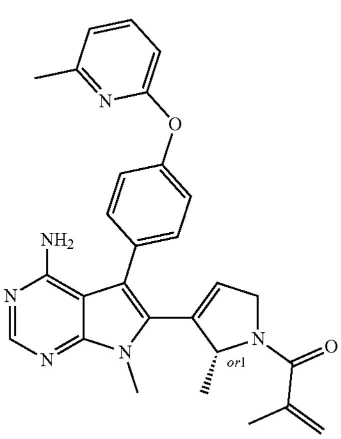 [SMILES: C=C(C)C(=O)N1CC=C(c2c(-c3ccc(Oc4cccc(C)n4)cc3)c3c(N)ncnc3n2C)[C@H]1C] | C | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 931 | 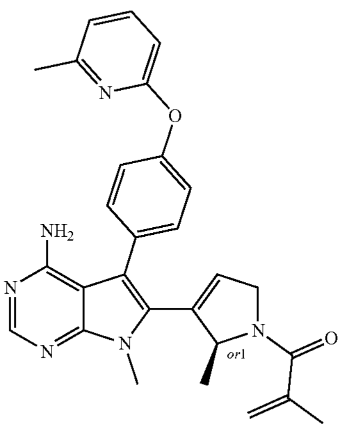 [SMILES: C=C(C)C(=O)N1CC=C(c2c(-c3ccc(Oc4cccc(C)n4)cc3)c3c(N)ncnc3n2C)[C@@H]1C] | C | D |
| 932 | 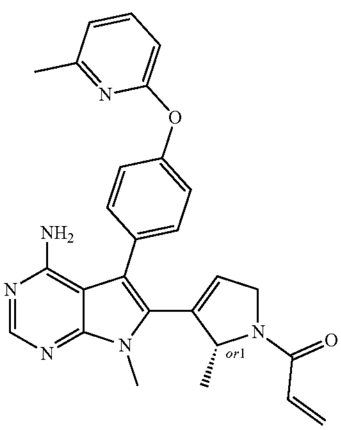 [SMILES: C=CC(=O)N1CC=C(c2c(-c3ccc(Oc4cccc(C)n4)cc3)c3c(N)ncnc3n2C)[C@H]1C] | B | C |
| 933 | 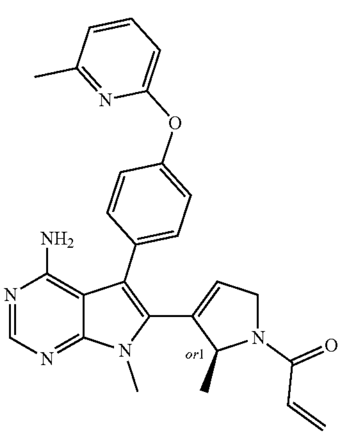 [SMILES: C=CC(=O)N1CC=C(c2c(-c3ccc(Oc4cccc(C)n4)cc3)c3c(N)ncnc3n2C)[C@@H]1C] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 934 | 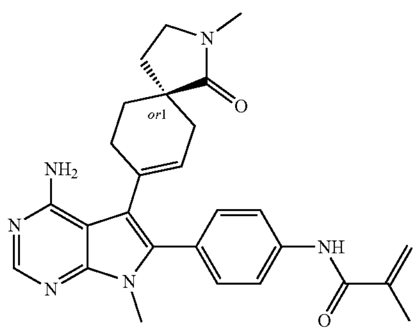 [SMILES: C=C(C)C(=O)Nc1ccc(-c2c(C3=CC[C@]4(CC3)CCN(C)C4=O)c3c(N)ncnc3n2C)cc1] | A | A |
| 935 | 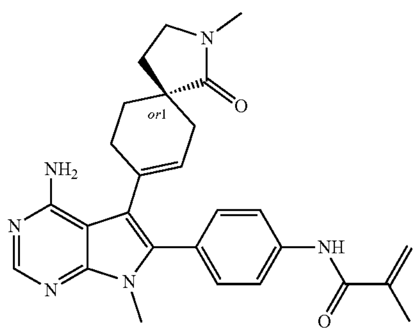 [SMILES: C=C(C)C(=O)Nc1ccc(-c2c(C3=CC[C@@]4(CC3)CCN(C)C4=O)c3c(N)ncnc3n2C)cc1] | D | D |
| 936 | 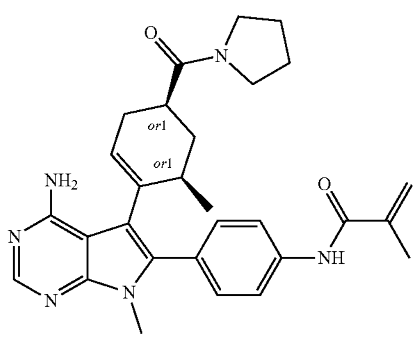 [SMILES: C=C(C)C(=O)Nc1ccc(-c2c(C3=CC[C@@H](C(=O)N4CCCC4)C[C@H]3C)c3c(N)ncnc3n2C)cc1] | D | C |
| 937 | 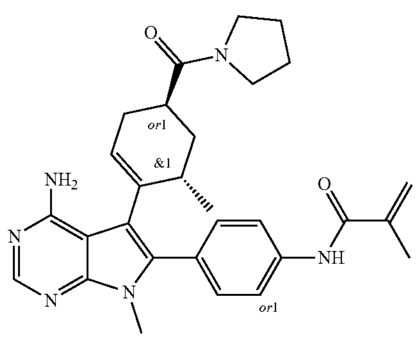 [SMILES: C=C(C)C(=O)Nc1ccc(-c2c(C3=CC[C@@H](C(=O)N4CCCC4)C[C@@H]3C)c3c(N)ncnc3n2C)cc1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 938 | 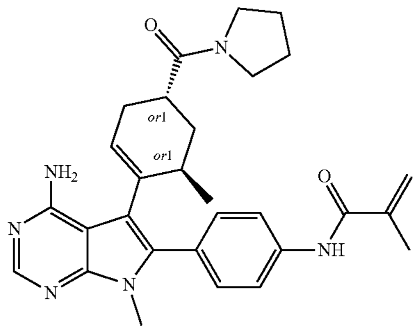 [SMILES: C=C(C)C(=O)Nc1ccc(-c2c(C3=CC[C@H](C(=O)N4CCCC4)C[C@H]3C)c3c(N)ncnc3n2C)cc1] | D | D |
| 939 | 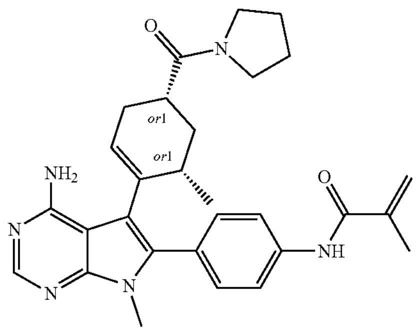 [SMILES: C=C(C)C(=O)Nc1ccc(-c2c(C3=CC[C@H](C(=O)N4CCCC4)C[C@@H]3C)c3c(N)ncnc3n2C)cc1] | D | D |
| 940 | 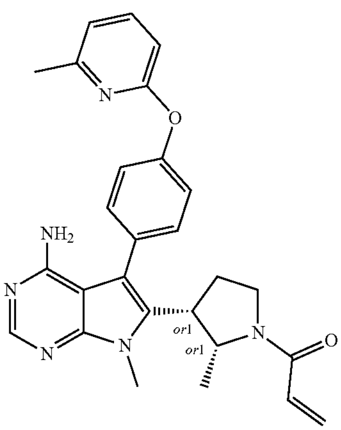 [SMILES: C=CC(=O)N1CC[C@@H](c2c(-c3ccc(Oc4cccc(C)n4)cc3)c3c(N)ncnc3n2C)[C@H]1C] | D | D |
| 941 | 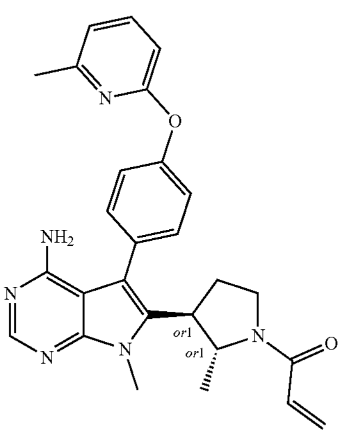 [SMILES: C=CC(=O)N1CC[C@H](c2c(-c3ccc(Oc4cccc(C)n4)cc3)c3c(N)ncnc3n2C)[C@H]1C] | C | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 942 | 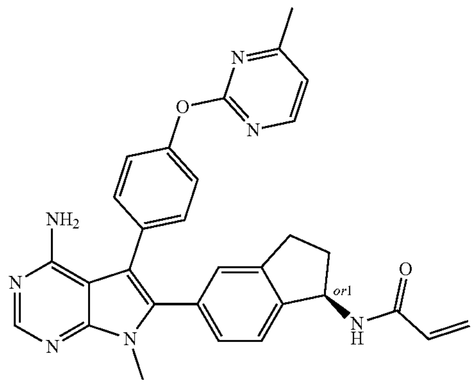 [SMILES: C=CC(=O)N[C@@H]1CCc2cc(-c3c(-c4ccc(Oc5nccc(C)n5)cc4)c4c(N)ncnc4n3C)ccc21] | C | C |
| 943 | 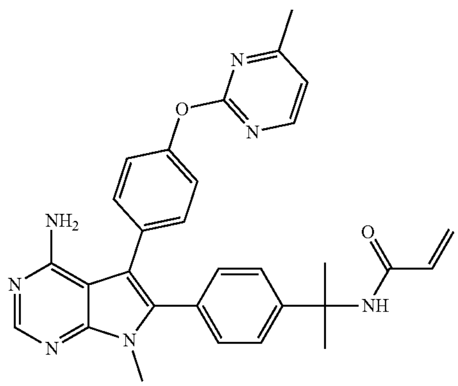 [SMILES: C=CC(=O)NC(C)(C)c1ccc(-c2c(-c3ccc(Oc4nccc(C)n4)cc3)c3c(N)ncnc3n2C)cc1] | C | C |
| 944 | 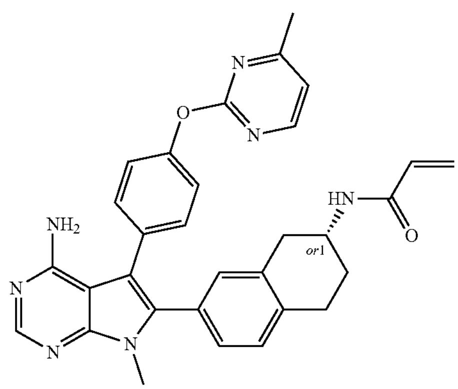 [SMILES: C=CC(=O)N[C@@H]1CCc2ccc(-c3c(-c4ccc(Oc5nccc(C)n5)cc4)c4c(N)ncnc4n3C)cc2C1] | D | D |
| 945 | 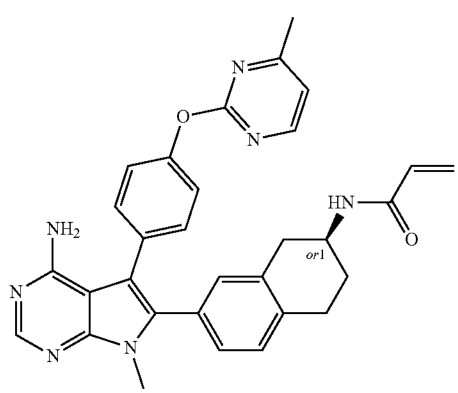 [SMILES: C=CC(=O)N[C@H]1CCc2ccc(-c3c(-c4ccc(Oc5nccc(C)n5)cc4)c4c(N)ncnc4n3C)cc2C1] | D | D |

| Example | Structure | Biochemical FGFR2 Caliper IC50 | Cell SNU-16 IC50 |
|---|---|---|---|
| 946 | 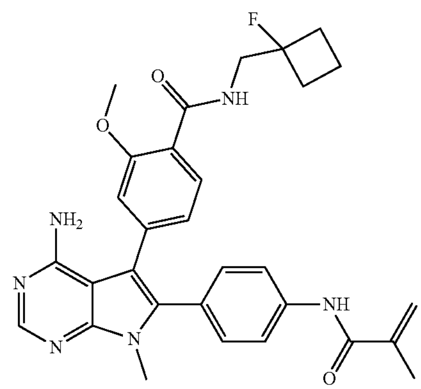 [SMILES: C=C(C)C(=O)Nc1ccc(-c2c(-c3ccc(C(=O)NCC4(F)CCC4)c(OC)c3)c3c(N)ncnc3n2C)cc1] | C | D |
| 947 | 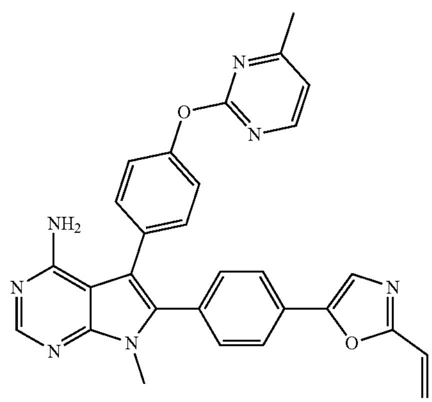 [SMILES: C=Cc1ncc(-c2ccc(-c3c(-c4ccc(Oc5nccc(C)n5)cc4)c4c(N)ncnc4n3C)cc2)o1] | A | A |
| 948 | 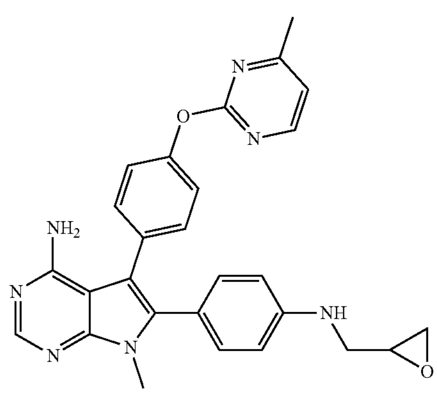 [SMILES: Cc1ccnc(Oc2ccc(-c3c(-c4ccc(NCC5CO5)cc4)n(C)c4ncnc(N)c34)cc2)n1] | D | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 949 | 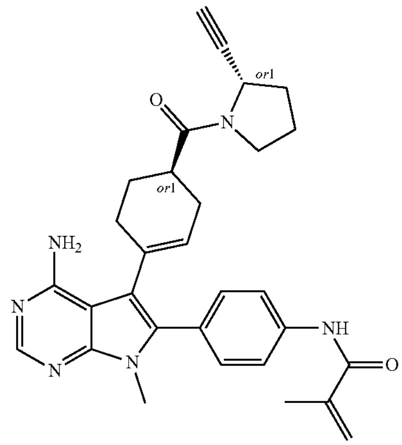 [SMILES: C#C[C@@H]1CCCN1C(=O)[C@H]1CC=C(c2c(-c3ccc(NC(=O)C(=C)C)cc3)n(C)c3ncnc(N)c23)CC1] | B | D |
| 950 | 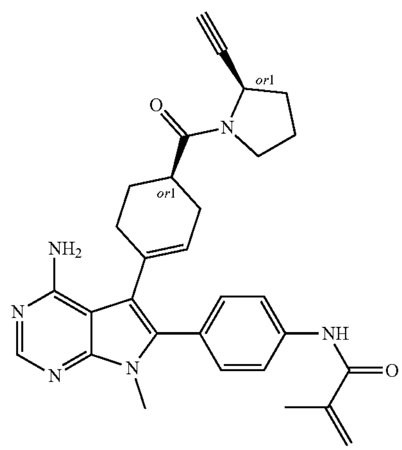 [SMILES: C#C[C@H]1CCCN1C(=O)[C@H]1CC=C(c2c(-c3ccc(NC(=O)C(=C)C)cc3)n(C)c3ncnc(N)c23)CC1] | D | D |
| 951 | 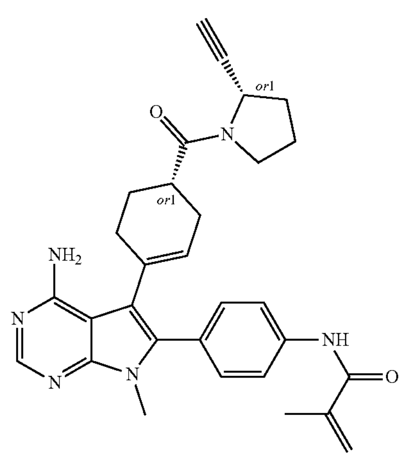 [SMILES: C#C[C@@H]1CCCN1C(=O)[C@@H]1CC=C(c2c(-c3ccc(NC(=O)C(=C)C)cc3)n(C)c3ncnc(N)c23)CC1] | C | B |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 952 | 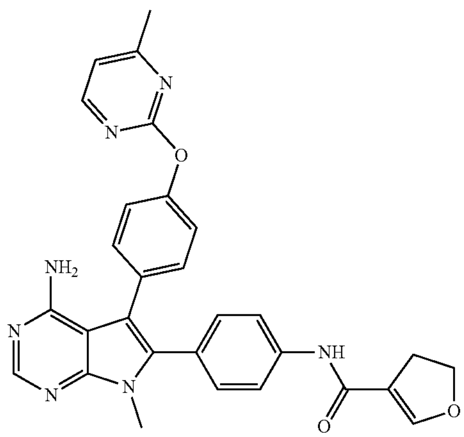 [SMILES: Cc1ccnc(Oc2ccc(-c3c(-c4ccc(NC(=O)C5=COCC5)cc4)n(C)c4ncnc(N)c34)cc2)n1] | A | A |
| 953 | 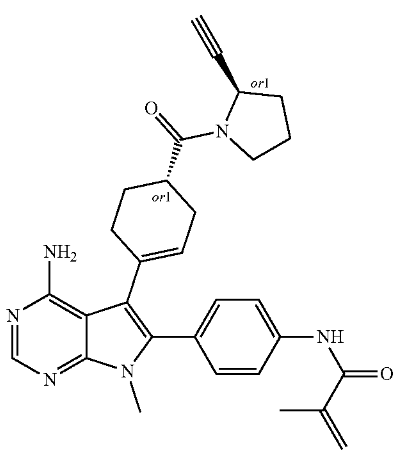 [SMILES: C#C[C@H]1CCCN1C(=O)[C@@H]1CC=C(c2c(-c3ccc(NC(=O)C(=C)C)cc3)n(C)c3ncnc(N)c23)CC1] | A | D |
| 954 | 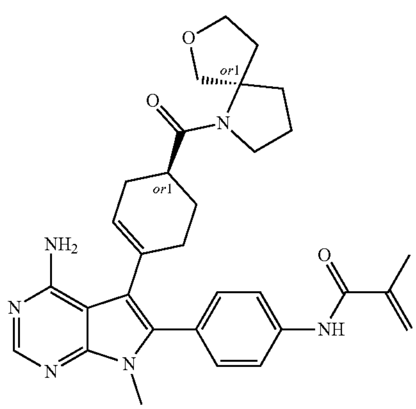 [SMILES: C=C(C)C(=O)Nc1ccc(-c2c(C3=CC[C@@H](C(=O)N4CCC[C@]45CCOC5)CC3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 955 | 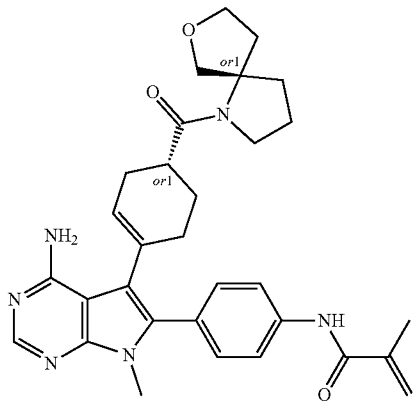 [SMILES: C=C(C)C(=O)Nc1ccc(-c2c(C3=CC[C@H](C(=O)N4CCC[C@@]45CCOC5)CC3)c3c(N)ncnc3n2C)cc1] | D | C |
| 956 | 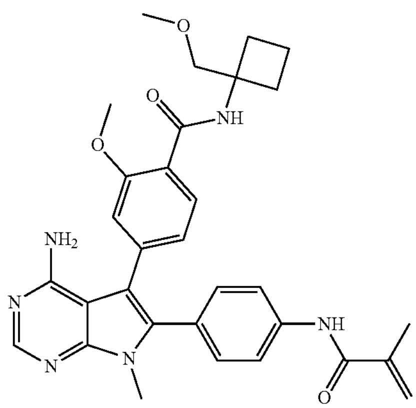 [SMILES: C=C(C)C(=O)Nc1ccc(-c2c(-c3ccc(C(=O)NC4(COC)CCC4)c(OC)c3)c3c(N)ncnc3n2C)cc1] | A | A |
| 957 | 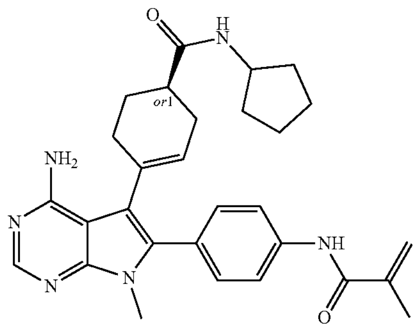 [SMILES: C=C(C)C(=O)Nc1ccc(-c2c(C3=CC[C@H](C(=O)NC4CCCC4)CC3)c3c(N)ncnc3n2C)cc1] | B | A |
| 958 | 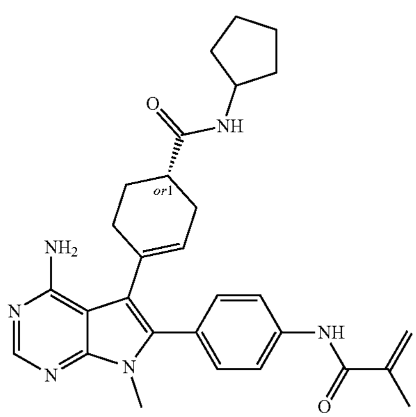 [SMILES: C=C(C)C(=O)Nc1ccc(-c2c(C3=CC[C@@H](C(=O)NC4CCCC4)CC3)c3c(N)ncnc3n2C)cc1] | C | A |

US 11,780,845 B2
627                                                                                           628
TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 959 | 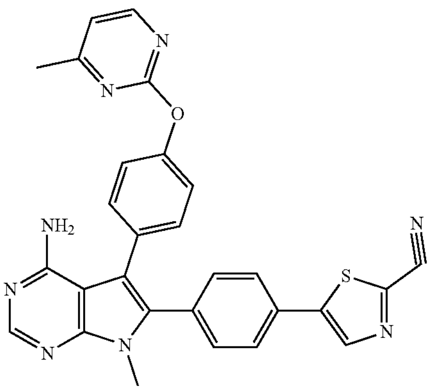 [SMILES: Cc1ccnc(Oc2ccc(-c3c(-c4ccc(-c5cnc(C#N)s5)cc4)n(C)c4ncnc(N)c34)cc2)n1] | C | A |
| 960 | 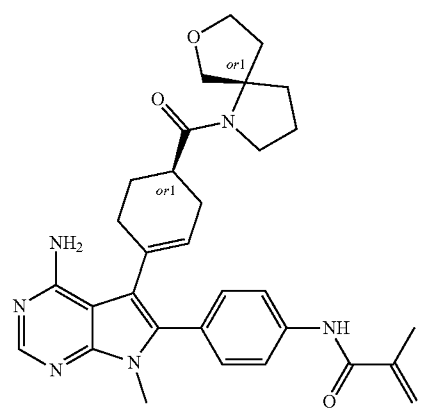 [SMILES: C=C(C)C(=O)Nc1ccc(-c2c(C3=CC[C@H](C(=O)N4CCC[C@@]45CCOC5)CC3)c3c(N)ncnc3n2C)cc1] | D | D |
| 961 | 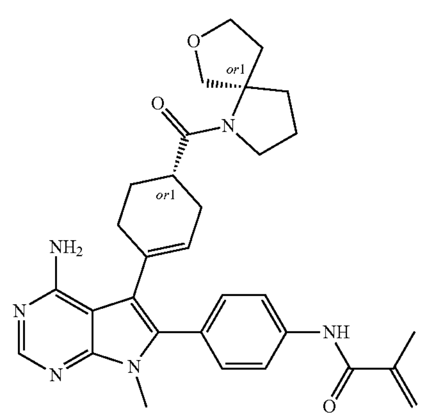 [SMILES: C=C(C)C(=O)Nc1ccc(-c2c(C3=CC[C@@H](C(=O)N4CCC[C@]45CCOC5)CC3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 962 | 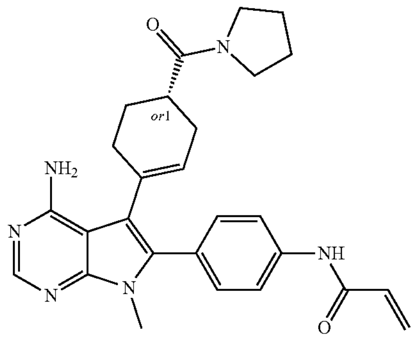 | A | A |
| 963 | 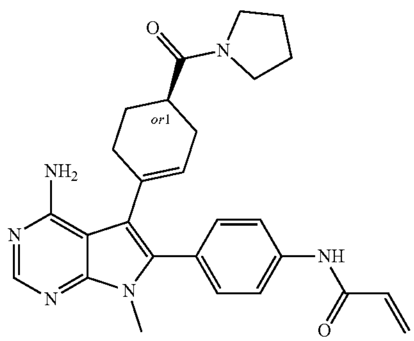 [SMILES: C=CC(=O)Nc1ccc(-c2c(C3=CC[C@H](C(=O)N4CCCC4)CC3)c3c(N)ncnc3n2C)cc1] | A | A |
| 964 | 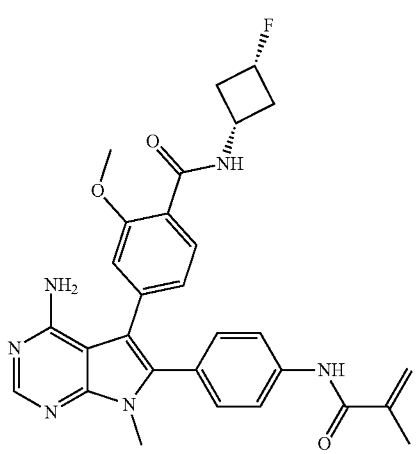 [SMILES: C=C(C)C(=O)Nc1ccc(-c2c(-c3ccc(C(=O)N[C@H]4C[C@@H](F)C4)c(OC)c3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 965 | 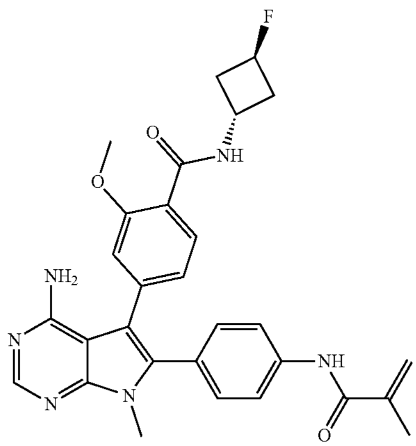 [SMILES: C=C(C)C(=O)Nc1ccc(-c2c(-c3ccc(C(=O)N[C@H]4C[C@H](F)C4)c(OC)c3)c3c(N)ncnc3n2C)cc1] | A | A |
| 966 | 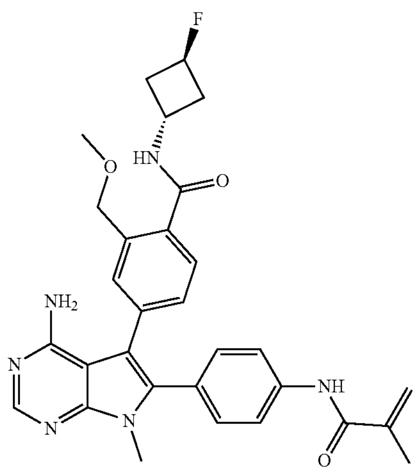 [SMILES: C=C(C)C(=O)Nc1ccc(-c2c(-c3ccc(C(=O)N[C@H]4C[C@H](F)C4)c(COC)c3)c3c(N)ncnc3n2C)cc1] | A | A |
| 967 | 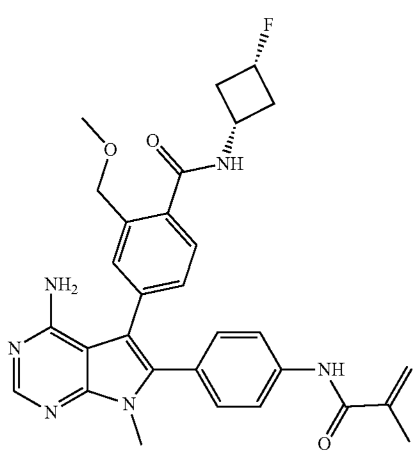 [SMILES: C=C(C)C(=O)Nc1ccc(-c2c(-c3ccc(C(=O)N[C@H]4C[C@@H](F)C4)c(COC)c3)c3c(N)ncnc3n2C)cc1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 968 | 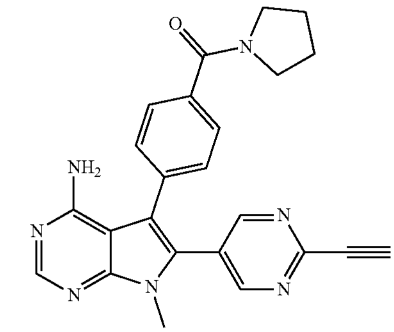 [SMILES: C#Cc1ncc(-c2c(-c3ccc(C(=O)N4CCCC4)cc3)c3c(N)ncnc3n2C)cn1] | C | C |
| 969 | 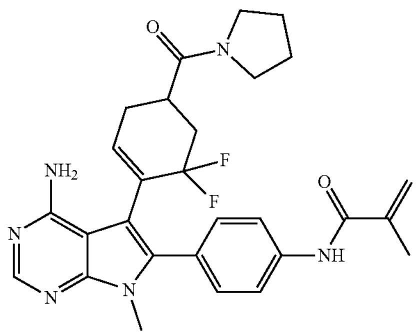 [SMILES: C=C(C)C(=O)Nc1ccc(-c2c(C3=CCC(C(=O)N4CCCC4)CC3(F)F)c3c(N)ncnc3n2C)cc1] | A | A |
| 970 | 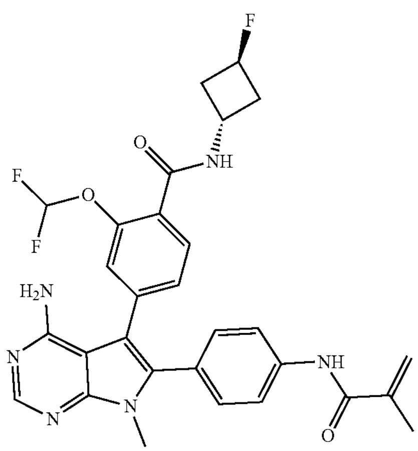 [SMILES: C=C(C)C(=O)Nc1ccc(-c2c(-c3ccc(C(=O)N[C@H]4C[C@H](F)C4)c(OC(F)F)c3)c3c(N)ncnc3n2C)cc1] | D | D |
| 971 | 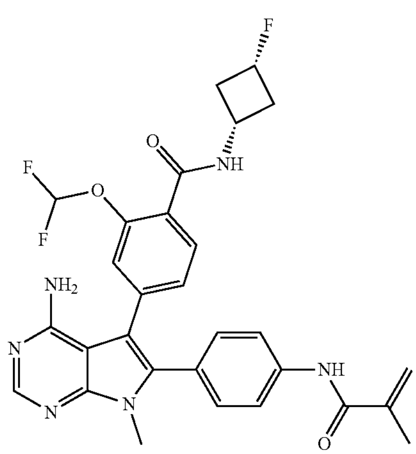 [SMILES: C=C(C)C(=O)Nc1ccc(-c2c(-c3ccc(C(=O)N[C@H]4C[C@@H](F)C4)c(OC(F)F)c3)c3c(N)ncnc3n2C)cc1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 972 | 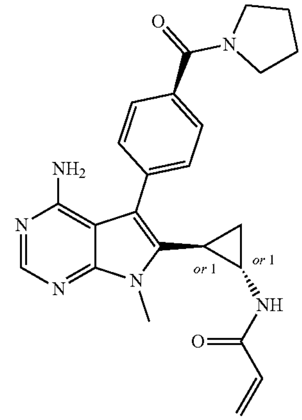 | D | D |
| 973 | 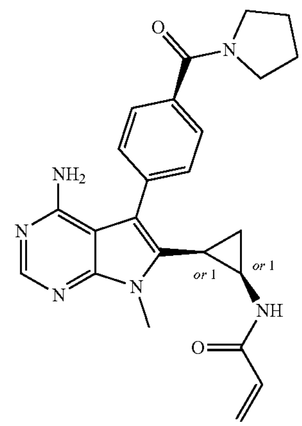 | C | D |
| 974 | 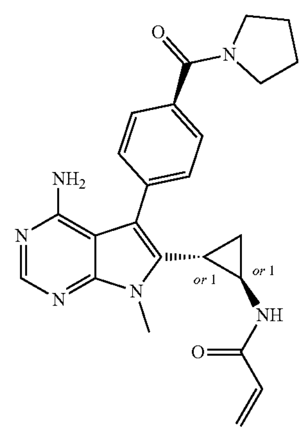 | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 975 | 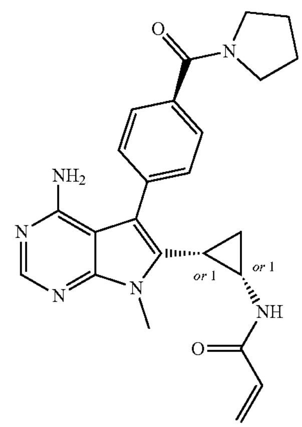 | D | D |
| 976 | 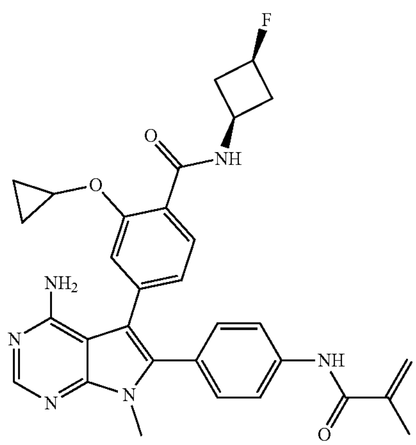 [SMILES: C=C(C)C(=O)Nc1ccc(-c2c(-c3ccc(C(=O)N[C@H]4C[C@@H](F)C4)c(OC4CC4)c3)c3c(N)ncnc3n2C)cc1] | D | D |
| 977 | 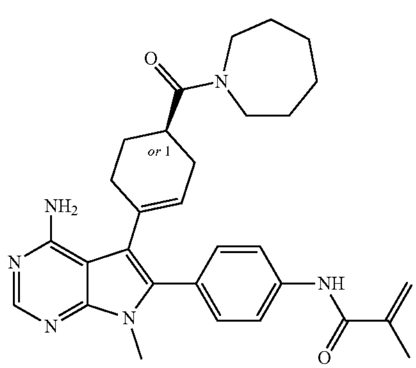 [SMILES: C=C(C)C(=O)Nc1ccc(-c2c(C3=CC[C@H](C(=O)N4CCCCCC4)CC3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 978 | 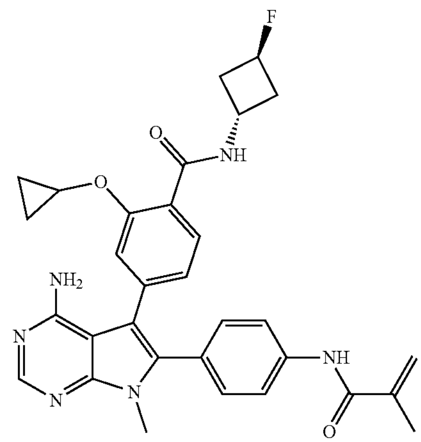 [SMILES: C=C(C)C(=O)Nc1ccc(-c2c(-c3ccc(C(=O)N[C@H]4C[C@H](F)C4)c(OC4CC4)c3)c3c(N)ncnc3n2C)cc1] | C | C |
| 979 | 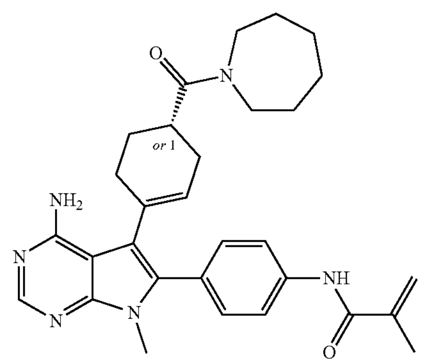 [SMILES: C=C(C)C(=O)Nc1ccc(-c2c(C3=CC[C@@H](C(=O)N4CCCCCC4)CC3)c3c(N)ncnc3n2C)cc1] | C | C |
| 980 | 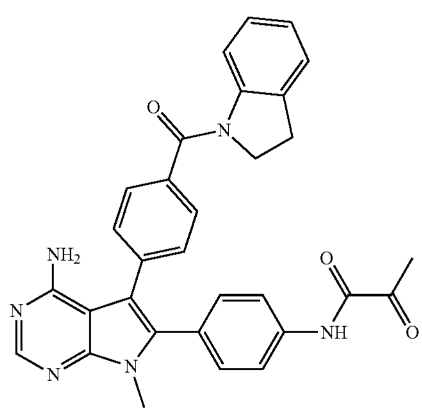 [SMILES: CC(=O)C(=O)Nc1ccc(-c2c(-c3ccc(C(=O)N4CCc5ccccc54)cc3)c3c(N)ncnc3n2C)cc1] | A | A |
| 981 | 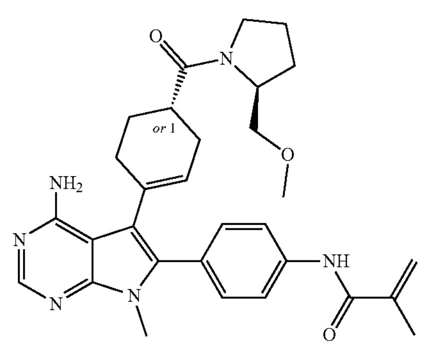 [SMILES: C=C(C)C(=O)Nc1ccc(-c2c(C3=CC[C@@H](C(=O)N4CCC[C@H]4COC)CC3)c3c(N)ncnc3n2C)cc1] | C | C |

US 11,780,845 B2
TABLE 1-continued
Representative Compounds of the Invention with Bioactivity Data.
| Example | Structure | Biochemical FGFR2 Caliper IC50 | Cell SNU-16 IC50 |
|---|---|---|---|
| 982 | 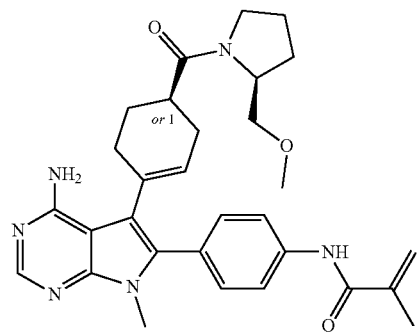 [SMILES: C=C(C)C(=O)Nc1ccc(-c2c(C3=CC[C@H](C(=O)N4CCC[C@H]4COC)CC3)c3c(N)ncnc3n2C)cc1] | D | C |
| 983 | 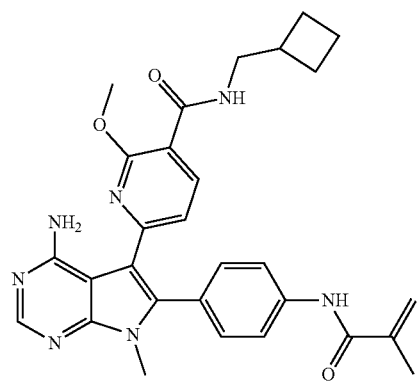 [SMILES: C=C(C)C(=O)Nc1ccc(-c2c(-c3ccc(C(=O)NCC4CCC4)c(OC)n3)c3c(N)ncnc3n2C)cc1] | A | A |
| 984 | 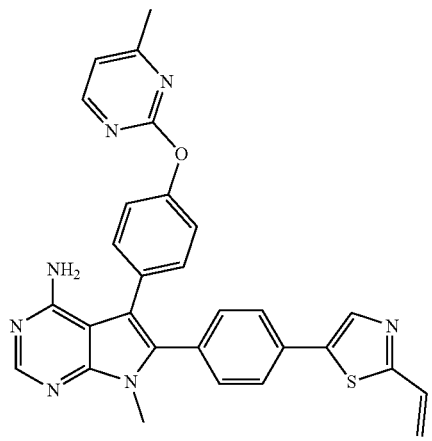 [SMILES: C=Cc1ncc(-c2ccc(-c3c(-c4ccc(Oc5nccc(C)n5)cc4)c4c(N)ncnc4n3C)cc2)s1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 985 | 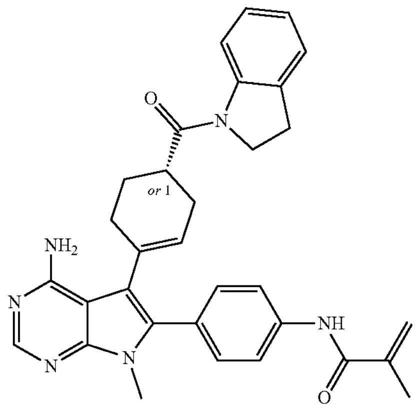 [SMILES: C=C(C)C(=O)Nc1ccc(-c2c(C3=CC[C@@H](C(=O)N4CCc5ccccc54)CC3)c3c(N)ncnc3n2C)cc1] | C | C |
| 986 | 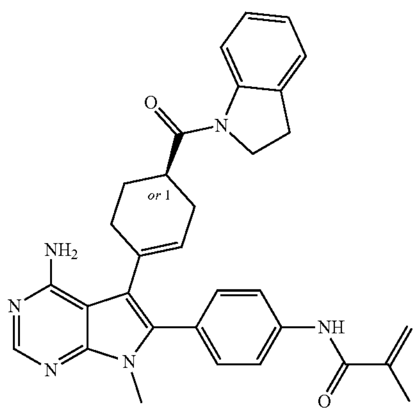 [SMILES: C=C(C)C(=O)Nc1ccc(-c2c(C3=CC[C@H](C(=O)N4CCc5ccccc54)CC3)c3c(N)ncnc3n2C)cc1] | C | C |
| 987 | 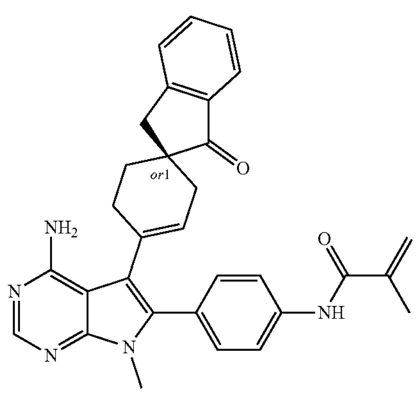 [SMILES: C=C(C)C(=O)Nc1ccc(-c2c(C3=CC[C@@]4(CC3)Cc3ccccc3C4=O)c3c(N)ncnc3n2C)cc1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 988 | 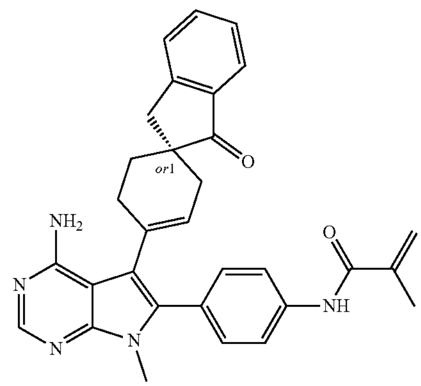 [SMILES: C=C(C)C(=O)Nc1ccc(-c2c(C3=CC[C@]4(CC3)Cc3ccccc3C4=O)c3c(N)ncnc3n2C)cc1] | C | A |
| 989 | 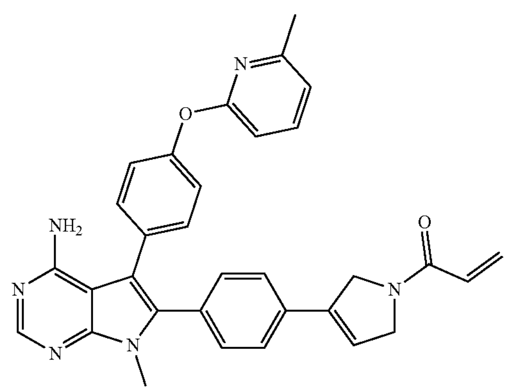 [SMILES: C=CC(=O)N1CC=C(c2ccc(-c3c(-c4ccc(Oc5cccc(C)n5)cc4)c4c(N)ncnc4n3C)cc2)C1] | D | C |
| 990 | 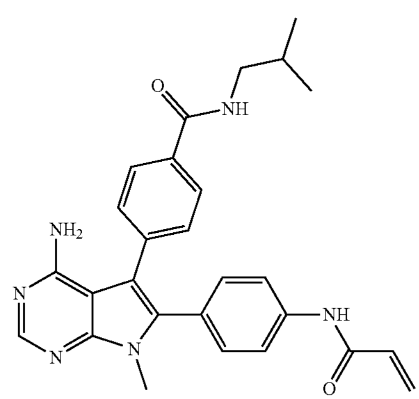 [SMILES: C=CC(=O)Nc1ccc(-c2c(-c3ccc(C(=O)NCC(C)C)cc3)c3c(N)ncnc3n2C)cc1] | A | A |
| 991 | 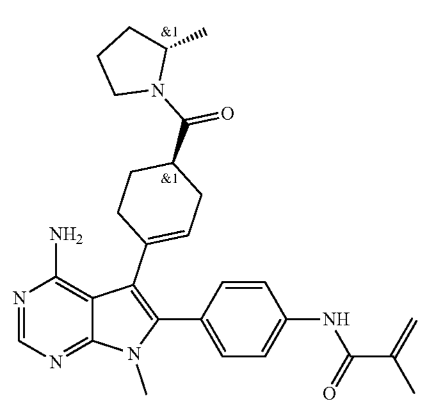 [SMILES: C=C(C)C(=O)Nc1ccc(-c2c(C3=CC[C@H](C(=O)N4CCC[C@@H]4C)CC3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 992 | 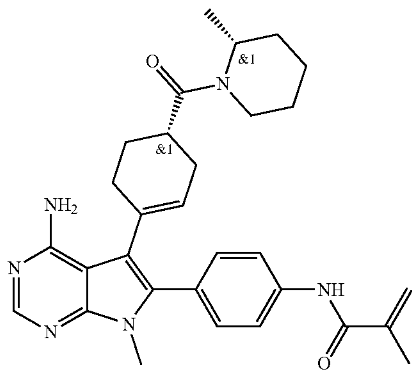 [SMILES: C=C(C)C(=O)Nc1ccc(-c2c(C3=CC[C@@H](C(=O)N4CCCC[C@H]4C)CC3)c3c(N)ncnc3n2C)cc1] | D | B |
| 993 | 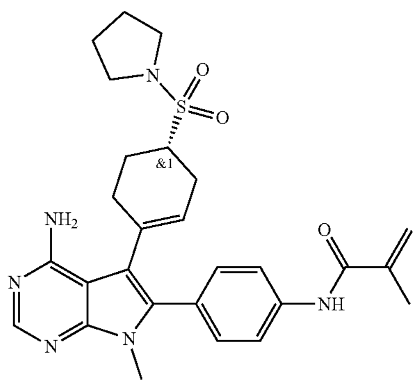 [SMILES: C=C(C)C(=O)Nc1ccc(-c2c(C3=CC[C@@H](S(=O)(=O)N4CCCC4)CC3)c3c(N)ncnc3n2C)cc1] | A | A |
| 994 | 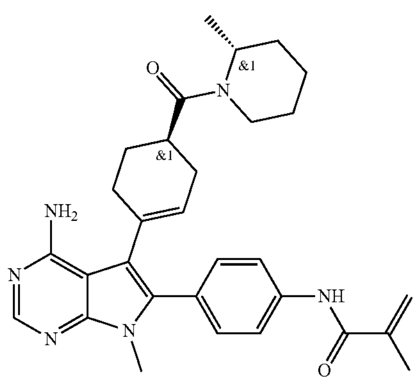 [SMILES: C=C(C)C(=O)Nc1ccc(-c2c(C3=CC[C@H](C(=O)N4CCCC[C@H]4C)CC3)c3c(N)ncnc3n2C)cc1] | D | B |
| 995 | 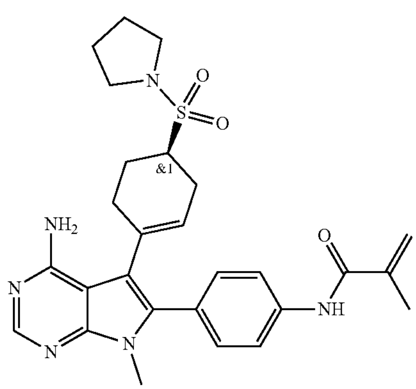 [SMILES: C=C(C)C(=O)Nc1ccc(-c2c(C3=CC[C@H](S(=O)(=O)N4CCCC4)CC3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 996 | 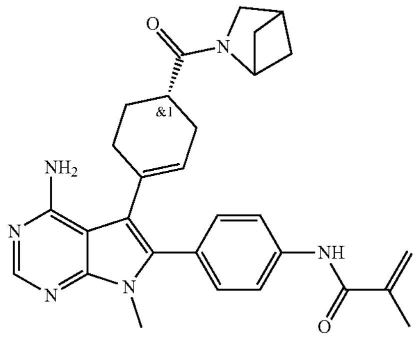 [SMILES: C=C(C)C(=O)Nc1ccc(-c2c(C3=CC[C@@H](C(=O)N4CC5CC4C5)CC3)c3c(N)ncnc3n2C)cc1] | C | B |
| 997 | 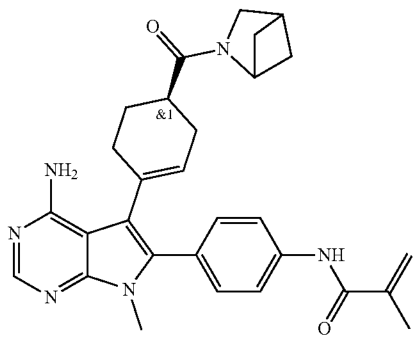 [SMILES: C=C(C)C(=O)Nc1ccc(-c2c(C3=CC[C@H](C(=O)N4CC5CC4C5)CC3)c3c(N)ncnc3n2C)cc1] | D | C |
| 998 | 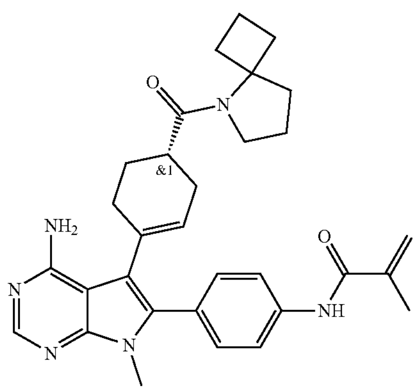 [SMILES: C=C(C)C(=O)Nc1ccc(-c2c(C3=CC[C@@H](C(=O)N4CCCC45CCC5)CC3)c3c(N)ncnc3n2C)cc1] | A | A |
| 999 | 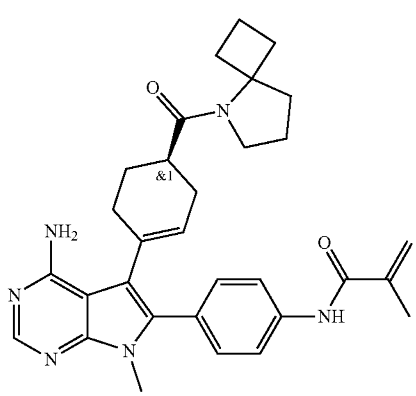 [SMILES: C=C(C)C(=O)Nc1ccc(-c2c(C3=CC[C@H](C(=O)N4CCCC45CCC5)CC3)c3c(N)ncnc3n2C)cc1] | A | A |

US 11,780,845 B2

651 652

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1000 | 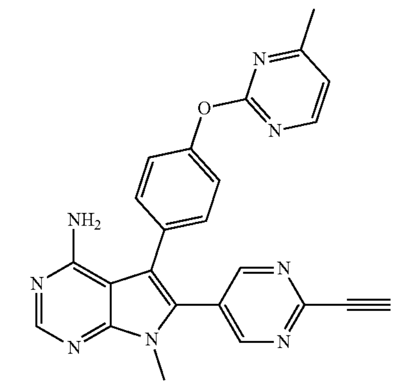 [SMILES: C#Cc1ncc(-c2c(-c3ccc(Oc4nccc(C)n4)cc3)c3c(N)ncnc3n2C)cn1] | D | C |
| 1001 | 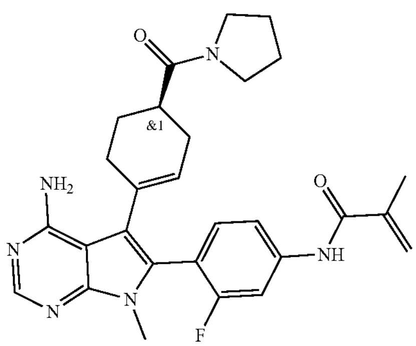 [SMILES: C=C(C)C(=O)Nc1ccc(-c2c(C3=CC[C@H](C(=O)N4CCCC4)CC3)c3c(N)ncnc3n2C)c(F)c1] | A | A |
| 1002 | 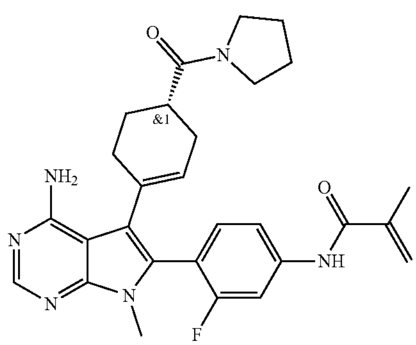 [SMILES: C=C(C)C(=O)Nc1ccc(-c2c(C3=CC[C@@H](C(=O)N4CCCC4)CC3)c3c(N)ncnc3n2C)c(F)c1] | A | A |
| 1003 | 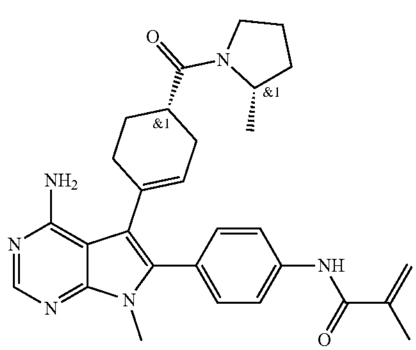 [SMILES: C=C(C)C(=O)Nc1ccc(-c2c(C3=CC[C@@H](C(=O)N4CCC[C@@H]4C)CC3)c3c(N)ncnc3n2C)cc1] | C | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1004 | 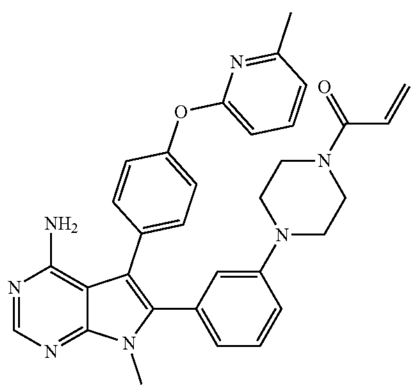 [SMILES: C=CC(=O)N1CCN(c2cccc(-c3c(-c4ccc(Oc5cccc(C)n5)cc4)c4c(N)ncnc4n3C)c2)CC1] | A | A |
| 1005 | 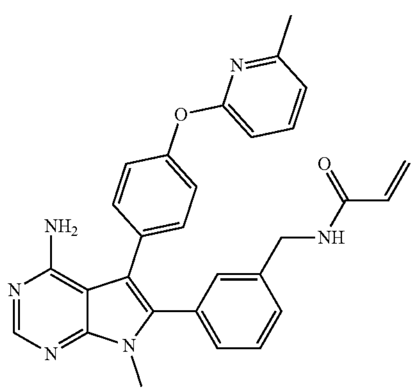 [SMILES: C=CC(=O)NCc1cccc(-c2c(-c3ccc(Oc4cccc(C)n4)cc3)c3c(N)ncnc3n2C)c1] | C | B |
| 1006 | 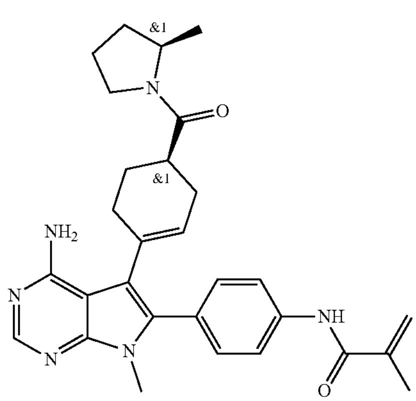 [SMILES: C=C(C)C(=O)Nc1ccc(-c2c(C3=CC[C@H](C(=O)N4CCC[C@H]4C)CC3)c3c(N)ncnc3n2C)cc1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1007 | 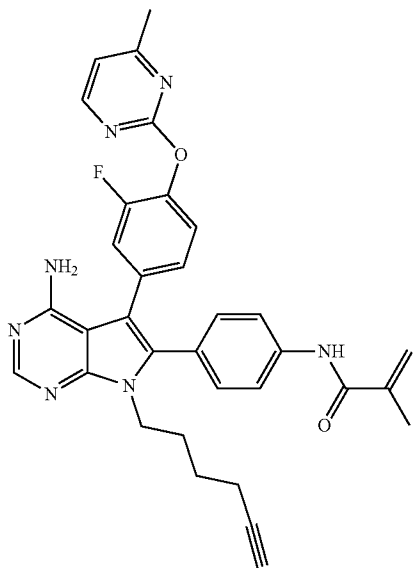 [SMILES: C#CCCCCn1c(-c2ccc(NC(=O)C(=C)C)cc2)c(-c2ccc(Oc3nccc(C)n3)c(F)c2)c2c(N)ncnc21] | A | A |
| 1008 | 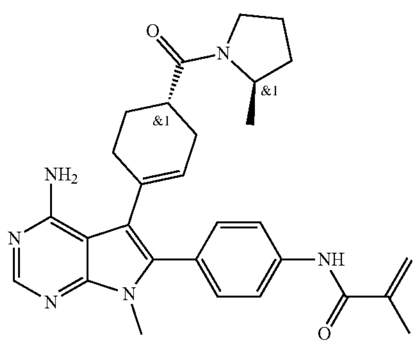 [SMILES: C=C(C)C(=O)Nc1ccc(-c2c(C3=CC[C@@H](C(=O)N4CCC[C@H]4C)CC3)c3c(N)ncnc3n2C)cc1] | B | B |
| 1009 | 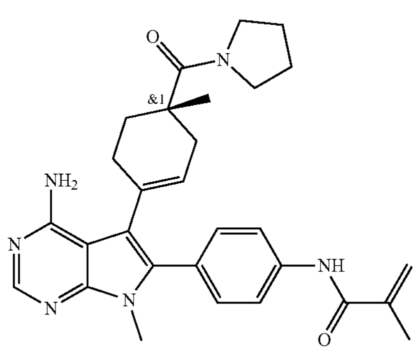 [SMILES: C=C(C)C(=O)Nc1ccc(-c2c(C3=CC[C@@](C)(C(=O)N4CCCC4)CC3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1010 | 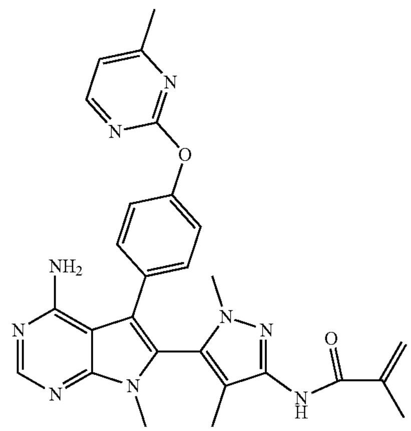 [SMILES: C=C(C)C(=O)Nc1nn(C)c(-c2c(-c3ccc(Oc4nccc(C)n4)cc3)c3c(N)ncnc3n2C)c1C] | D | C |
| 1011 | 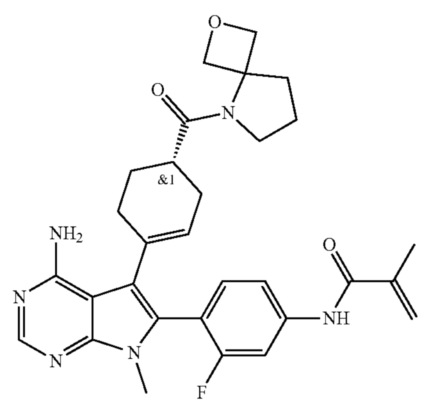 [SMILES: C=C(C)C(=O)Nc1ccc(-c2c(C3=CC[C@@H](C(=O)N4CCCC45COC5)CC3)c3c(N)ncnc3n2C)c(F)c1] | A | A |
| 1012 | 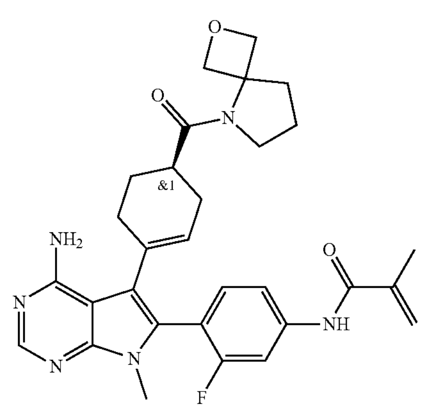 [SMILES: C=C(C)C(=O)Nc1ccc(-c2c(C3=CC[C@H](C(=O)N4CCCC45COC5)CC3)c3c(N)ncnc3n2C)c(F)c1] | C | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1013 | 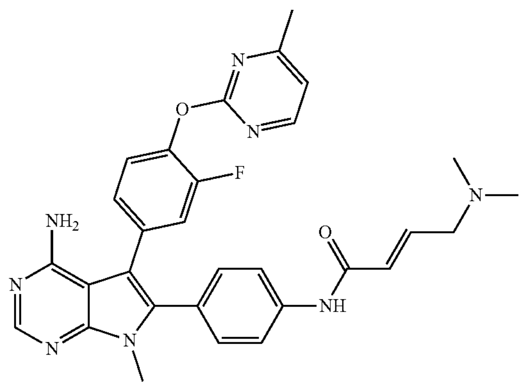 [SMILES: Cc1ccnc(Oc2ccc(-c3c(-c4ccc(NC(=O)/C=C/CN(C)C)cc4)n(C)c4ncnc(N)c34)cc2F)n1] | A | A |
| 1014 | 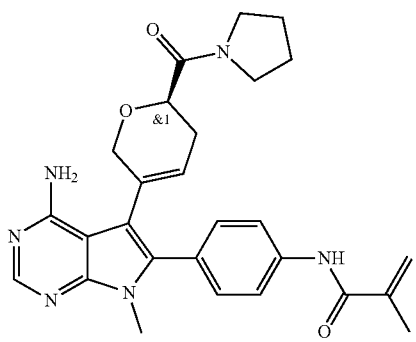 [SMILES: C=C(C)C(=O)Nc1ccc(-c2c(C3=CC[C@H](C(=O)N4CCCC4)OC3)c3c(N)ncnc3n2C)cc1] | A | A |
| 1015 | 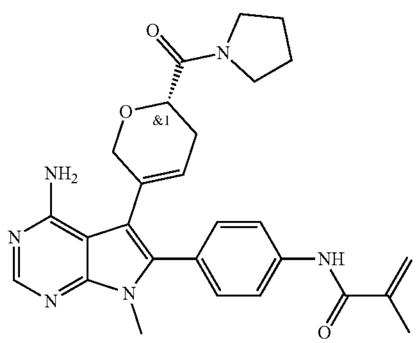 [SMILES: C=C(C)C(=O)Nc1ccc(-c2c(C3=CC[C@@H](C(=O)N4CCCC4)OC3)c3c(N)ncnc3n2C)cc1] | D | D |
| 1016 | 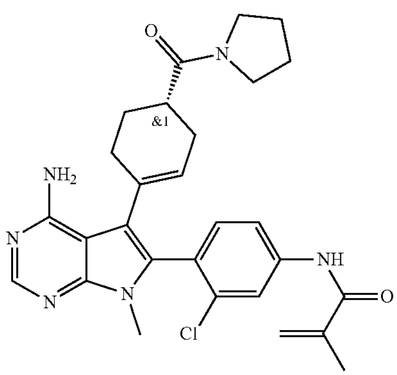 [SMILES: C=C(C)C(=O)Nc1ccc(-c2c(C3=CC[C@@H](C(=O)N4CCCC4)CC3)c3c(N)ncnc3n2C)c(Cl)c1] | D | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1017 | 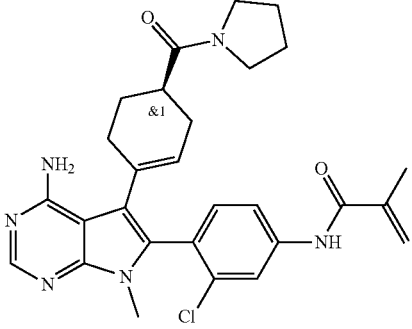 [SMILES: C=C(C)C(=O)Nc1ccc(-c2c(C3=CC[C@H](C(=O)N4CCCC4)CC3)c3c(N)ncnc3n2C)c(Cl)c1] | A | A |
| 1018 | 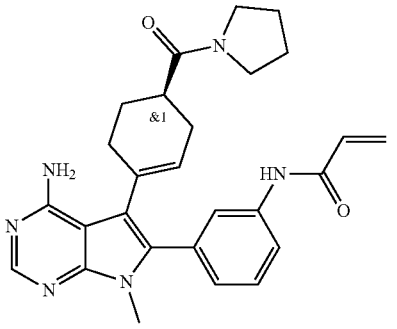 [SMILES: C=CC(=O)Nc1cccc(-c2c(C3=CC[C@H](C(=O)N4CCCC4)CC3)c3c(N)ncnc3n2C)c1] | A | A |
| 1019 | 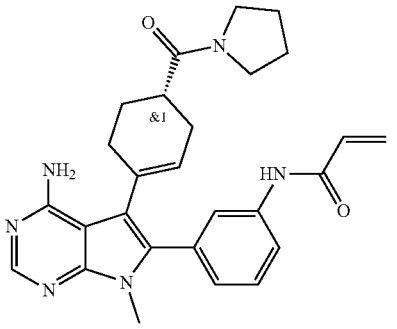 [SMILES: C=CC(=O)Nc1cccc(-c2c(C3=CC[C@@H](C(=O)N4CCCC4)CC3)c3c(N)ncnc3n2C)c1] | A | A |
| 1020 | 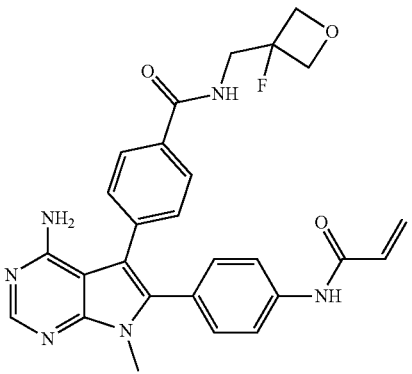 [SMILES: C=CC(=O)Nc1ccc(-c2c(-c3ccc(C(=O)NCC4(F)COC4)cc3)c3c(N)ncnc3n2C)cc1] | B | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1021 | 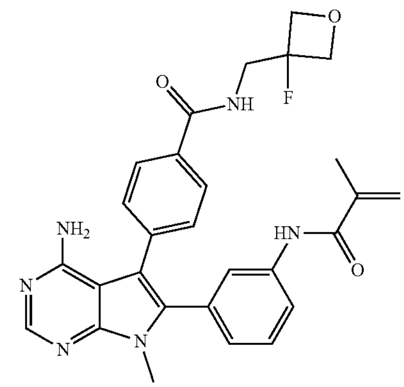 [SMILES: C=C(C)C(=O)Nc1cccc(-c2c(-c3ccc(C(=O)NCC4(F)COC4)cc3)c3c(N)ncnc3n2C)c1] | A | A |
| 1022 | 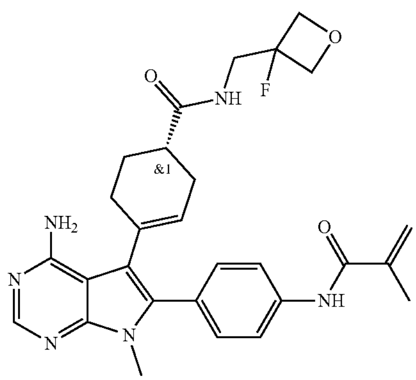 [SMILES: C=C(C)C(=O)Nc1ccc(-c2c(C3=CC[C@@H](C(=O)NCC4(F)COC4)CC3)c3c(N)ncnc3n2C)cc1] | C | D |
| 1023 | 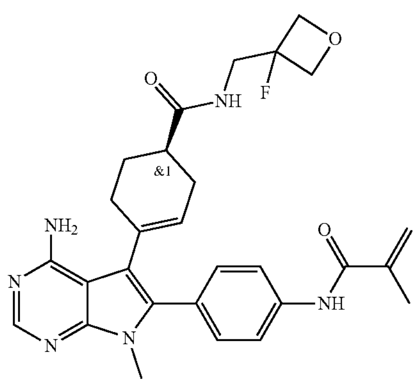 [SMILES: C=C(C)C(=O)Nc1ccc(-c2c(C3=CC[C@H](C(=O)NCC4(F)COC4)CC3)c3c(N)ncnc3n2C)cc1] | D | D |
| 1024 | 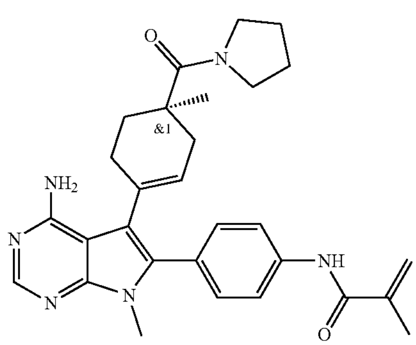 [SMILES: C=C(C)C(=O)Nc1ccc(-c2c(C3=CC[C@](C)(C(=O)N4CCCC4)CC3)c3c(N)ncnc3n2C)cc1] | C | C |

US 11,780,845 B2
TABLE 1-continued
Representative Compounds of the Invention with Bioactivity Data.
| Example | Structure | Biochemical FGFR2 Caliper IC50 | Cell SNU-16 IC50 |
|---|---|---|---|
| 1025 | 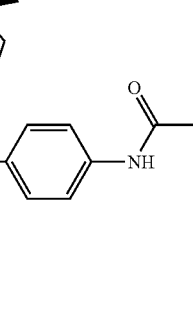 | D | D |
| 1026 | 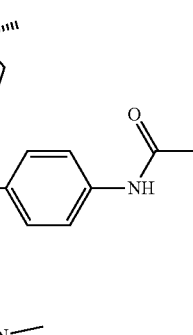 | D | D |
| 1027 | 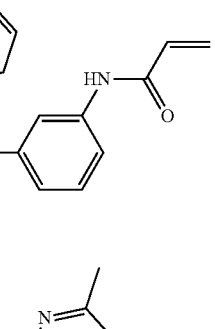 | D | D |
| 1028 | 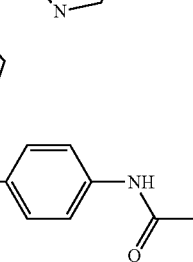 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1029 | 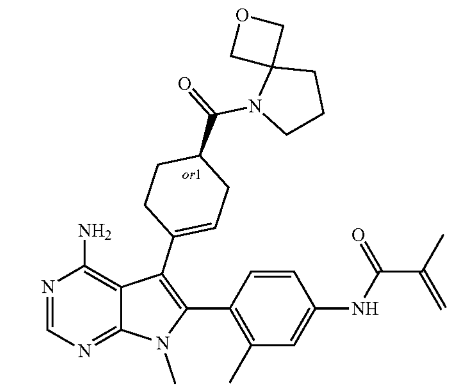 [SMILES: C=C(C)C(=O)Nc1ccc(-c2c(C3=CC[C@H](C(=O)N4CCCC45COC5)CC3)c3c(N)ncnc3n2C)c(C)c1] | D | C |
| 1030 | 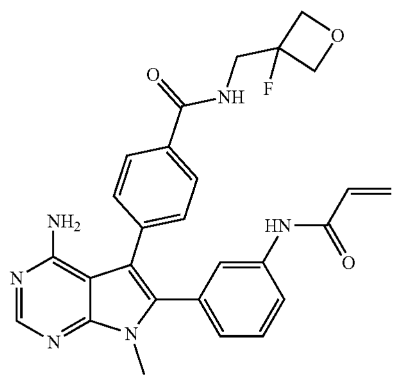 [SMILES: C=CC(=O)Nc1cccc(-c2c(-c3ccc(C(=O)NCC4(F)COC4)cc3)c3c(N)ncnc3n2C)c1] | A | A |
| 1031 | 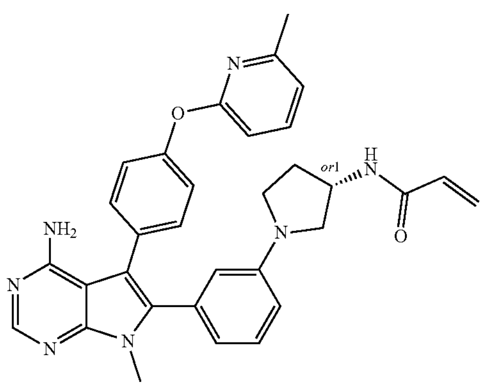 [SMILES: C=CC(=O)N[C@H]1CCN(c2cccc(-c3c(-c4ccc(Oc5cccc(C)n5)cc4)c4c(N)ncnc4n3C)c2)C1] | A | B |
| 1032 | 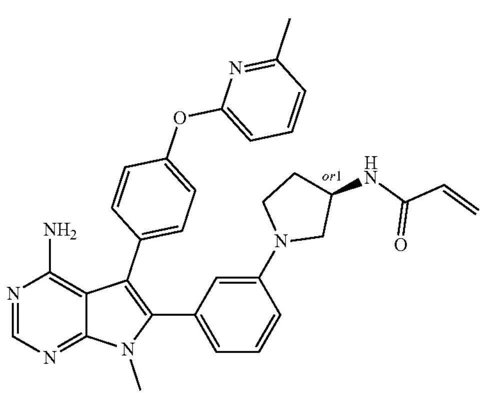 [SMILES: C=CC(=O)N[C@@H]1CCN(c2cccc(-c3c(-c4ccc(Oc5cccc(C)n5)cc4)c4c(N)ncnc4n3C)c2)C1] | C | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1033 | 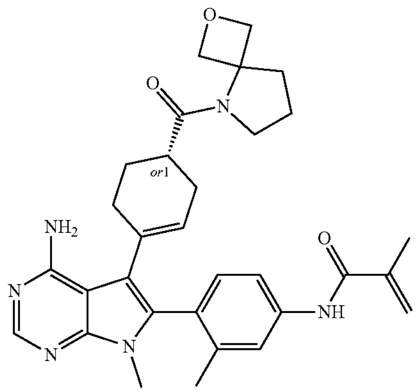 [SMILES: C=C(C)C(=O)Nc1ccc(-c2c(C3=CC[C@@H](C(=O)N4CCCC45COC5)CC3)c3c(N)ncnc3n2C)c(C)c1] | A | A |
| 1034 | 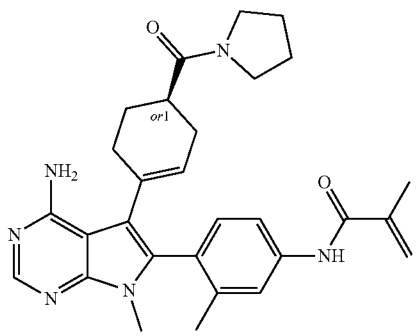 [SMILES: C=C(C)C(=O)Nc1ccc(-c2c(C3=CC[C@H](C(=O)N4CCCC4)CC3)c3c(N)ncnc3n2C)c(C)c1] | B | A |
| 1035 | 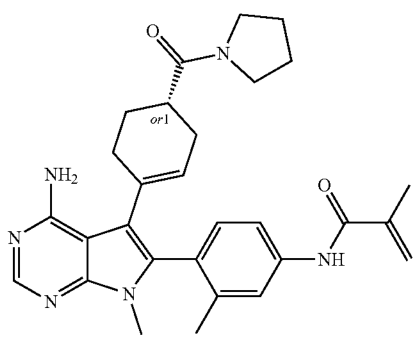 [SMILES: C=C(C)C(=O)Nc1ccc(-c2c(C3=CC[C@@H](C(=O)N4CCCC4)CC3)c3c(N)ncnc3n2C)c(C)c1] | A | A |
| 1036 | 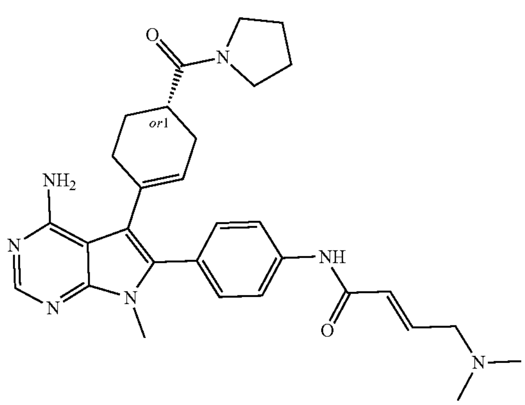 [SMILES: CN(C)C/C=C/C(=O)Nc1ccc(-c2c(C3=CC[C@@H](C(=O)N4CCCC4)CC3)c3c(N)ncnc3n2C)cc1] | C | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1037 | 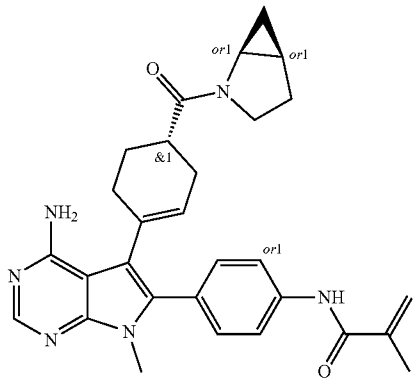 [SMILES: C=C(C)C(=O)Nc1ccc(-c2c(C3=CC[C@@H](C(=O)N4CC[C@@H]5C[C@@H]54)CC3)c3c(N)ncnc3n2C)cc1] | A | C |
| 1038 | 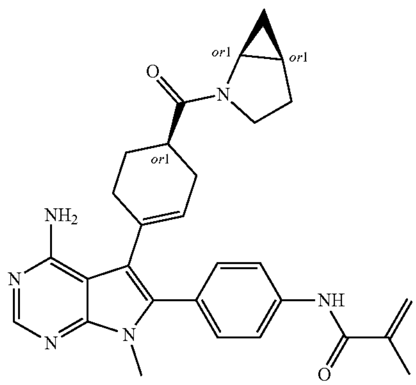 [SMILES: C=C(C)C(=O)Nc1ccc(-c2c(C3=CC[C@H](C(=O)N4CC[C@@H]5C[C@@H]54)CC3)c3c(N)ncnc3n2C)cc1] | A | A |
| 1039 | 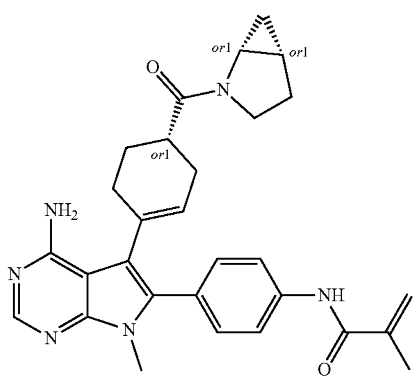 [SMILES: C=C(C)C(=O)Nc1ccc(-c2c(C3=CC[C@@H](C(=O)N4CC[C@H]5C[C@H]54)CC3)c3c(N)ncnc3n2C)cc1] | D | D |
| 1040 | 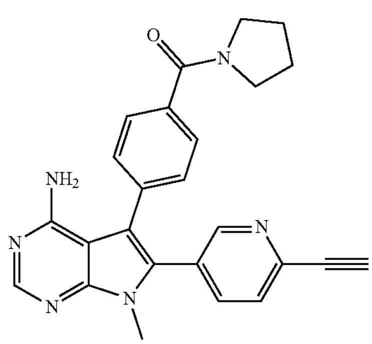 | D | C |

US 11,780,845 B2
TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 1041 | 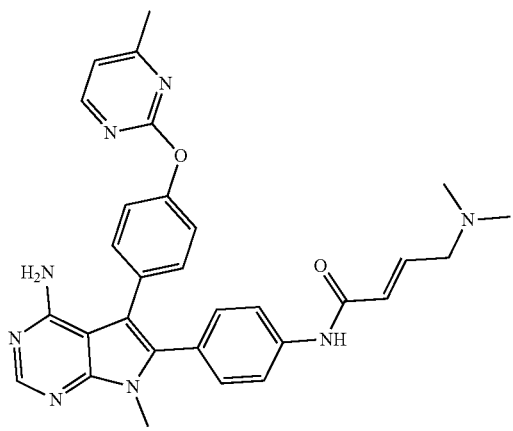 [SMILES: Cc1ccnc(Oc2ccc(-c3c(-c4ccc(NC(=O)/C=C/CN(C)C)cc4)n(C)c4ncnc(N)c34)cc2)n1] | B | A |
| 1042 | 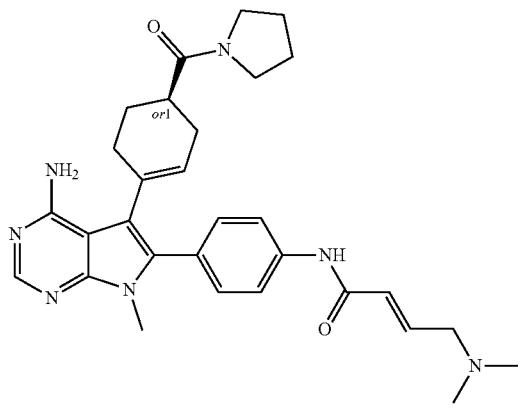 | A | A |
| 1043 | 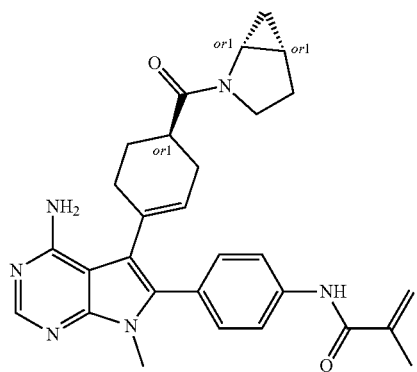 [SMILES: C=C(C)C(=O)Nc1ccc(-c2c(C3=CC[C@H](C(=O)N4CC[C@H]5C[C@H]54)CC3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1044 | 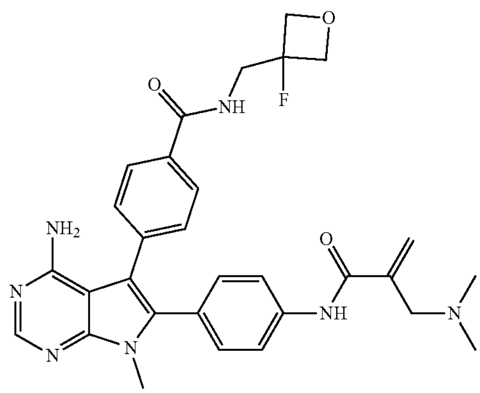 [SMILES: C=C(CN(C)C)C(=O)Nc1ccc(-c2c(-c3ccc(C(=O)NCC4(F)COC4)cc3)c3c(N)ncnc3n2C)cc1] | A | A |
| 1045 | 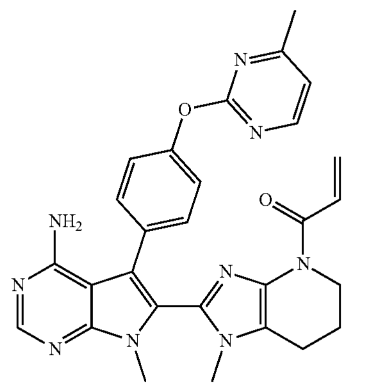 [SMILES: C=CC(=O)N1CCCc2c1nc(-c1c(-c3ccc(Oc4nccc(C)n4)cc3)c3c(N)ncnc3n1C)n2C] | D | D |
| 1046 | 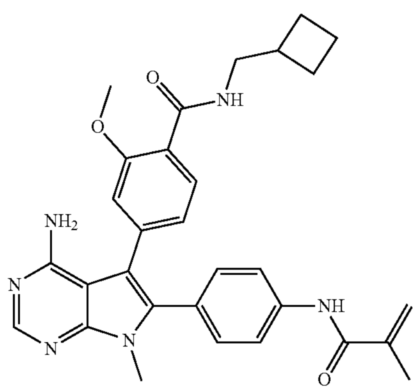 | D | D |
| 1047 | 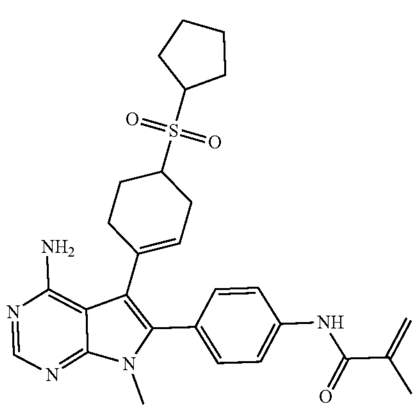 [SMILES: C=C(C)C(=O)Nc1ccc(-c2c(C3=CCC(S(=O)(=O)C4CCCC4)CC3)c3c(N)ncnc3n2C)cc1] | C | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1048 | 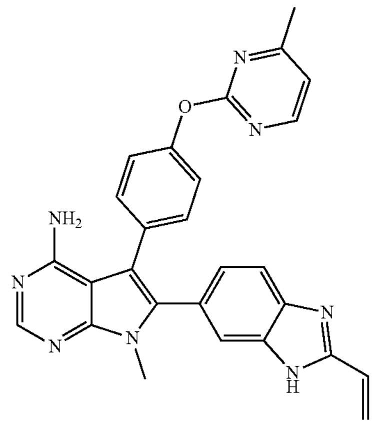 [SMILES: C=Cc1nc2ccc(-c3c(-c4ccc(Oc5nccc(C)n5)cc4)c4c(N)ncnc4n3C)cc2[nH]1] | C | B |
| 1049 | 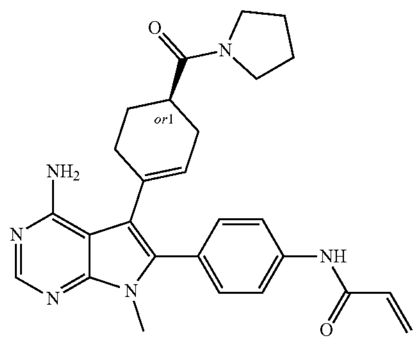 [SMILES: C=CC(=O)Nc1ccc(-c2c(C3=CC[C@H](C(=O)N4CCCC4)CC3)c3c(N)ncnc3n2C)cc1] | A | A |
| 1050 | 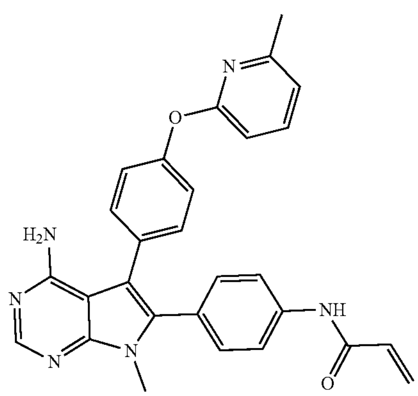 [SMILES: C=CC(=O)Nc1ccc(-c2c(-c3ccc(Oc4cccc(C)n4)cc3)c3c(N)ncnc3n2C)cc1] | C | C |
| 1051 | 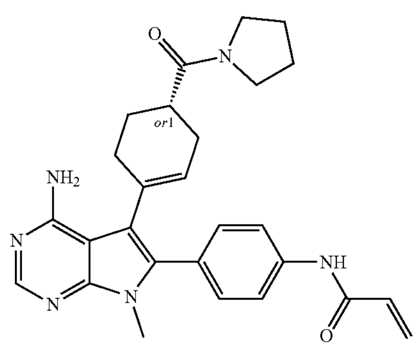 [SMILES: C=CC(=O)Nc1ccc(-c2c(C3=CC[C@@H](C(=O)N4CCCC4)CC3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1052 | 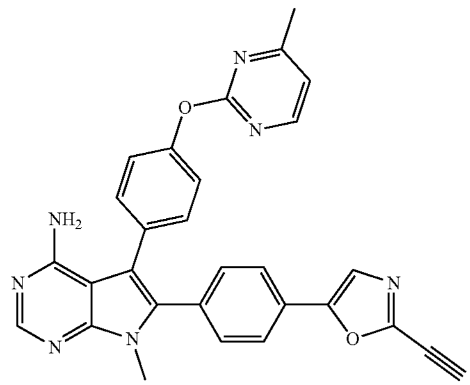 [SMILES: C#Cc1ncc(-c2ccc(-c3c(-c4ccc(Oc5nccc(C)n5)cc4)c4c(N)ncnc4n3C)cc2)o1] | D | D |
| 1053 | 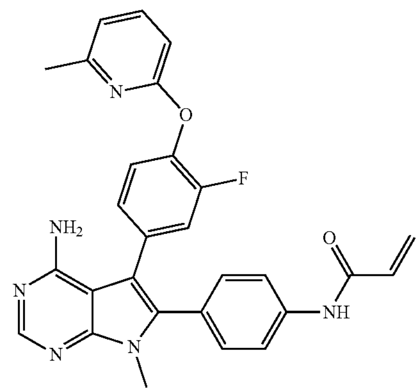 [SMILES: C=CC(=O)Nc1ccc(-c2c(-c3ccc(Oc4cccc(C)n4)c(F)c3)c3c(N)ncnc3n2C)cc1] | B | C |
| 1054 | 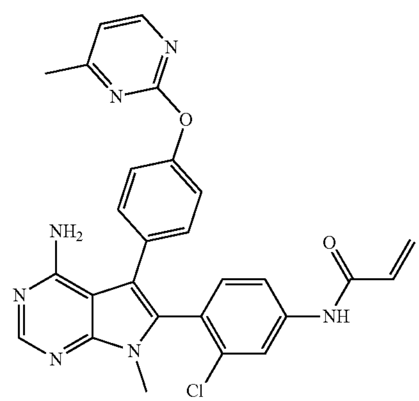 [SMILES: C=CC(=O)Nc1ccc(-c2c(-c3ccc(Oc4nccc(C)n4)cc3)c3c(N)ncnc3n2C)c(Cl)c1] | A | A |
| 1055 | 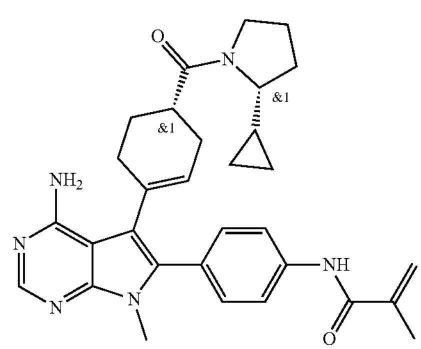 [SMILES: C=C(C)C(=O)Nc1ccc(-c2c(C3=CC[C@@H](C(=O)N4CCC[C@@H]4C4CC4)CC3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1056 | 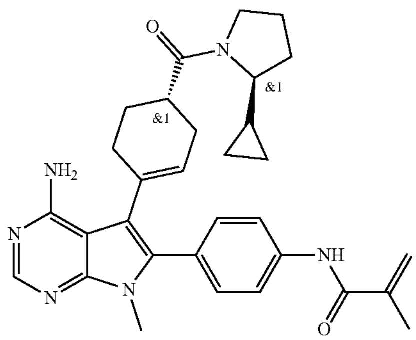 [SMILES: C=C(C)C(=O)Nc1ccc(-c2c(C3=CC[C@@H](C(=O)N4CCC[C@H]4C4CC4)CC3)c3c(N)ncnc3n2C)cc1] | C | A |
| 1057 | 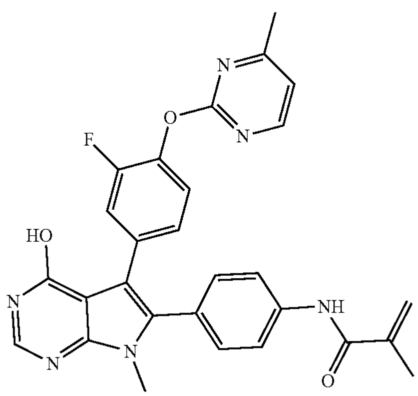 [SMILES: C=C(C)C(=O)Nc1ccc(-c2c(-c3ccc(Oc4nccc(C)n4)c(F)c3)c3c(O)ncnc3n2C)cc1] | A | A |
| 1058 | 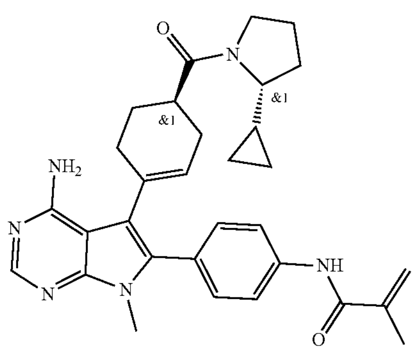 [SMILES: C=C(C)C(=O)Nc1ccc(-c2c(C3=CC[C@H](C(=O)N4CCC[C@@H]4C4CC4)CC3)c3c(N)ncnc3n2C)cc1] | D | D |
| 1059 | 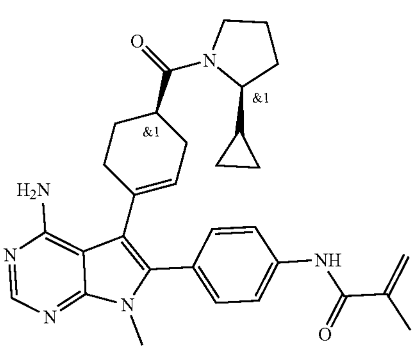 [SMILES: C=C(C)C(=O)Nc1ccc(-c2c(C3=CC[C@H](C(=O)N4CCC[C@H]4C4CC4)CC3)c3c(N)ncnc3n2C)cc1] | D | D |

683 684
TABLE 1-continued
Representative Compounds of the Invention with Bioactivity Data.
| Example | Structure | Biochemical FGFR2 Caliper IC50 | Cell SNU-16 IC50 |
|---|---|---|---|
| 1060 | 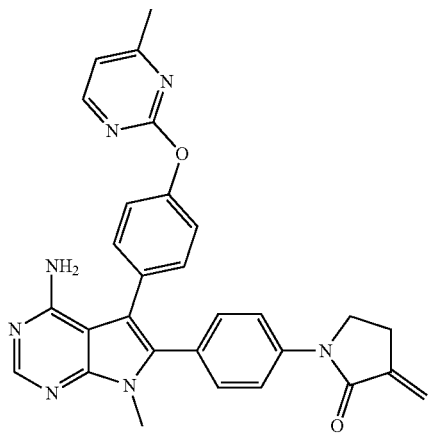 [SMILES: C=C1CCN(c2ccc(-c3c(-c4ccc(Oc5nccc(C)n5)cc4)c4c(N)ncnc4n3C)cc2)C1=O] | D | D |
| 1061 | 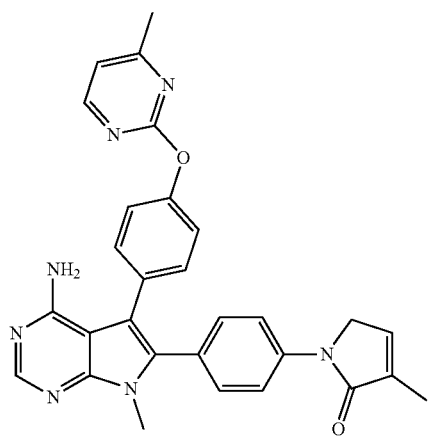 [SMILES: CC1=CCN(c2ccc(-c3c(-c4ccc(Oc5nccc(C)n5)cc4)c4c(N)ncnc4n3C)cc2)C1=O] | A | A |
| 1062 | 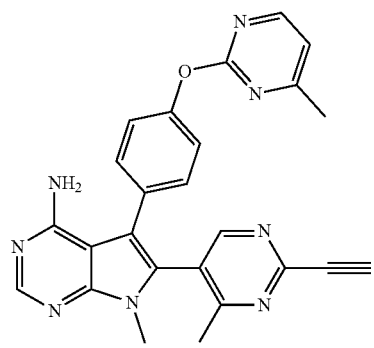 | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1063 | 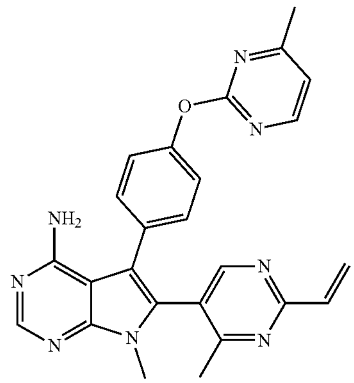 [SMILES: C=Cc1ncc(-c2c(-c3ccc(Oc4nccc(C)n4)cc3)c3c(N)ncnc3n2C)c(C)n1] | A | A |
| 1064 | 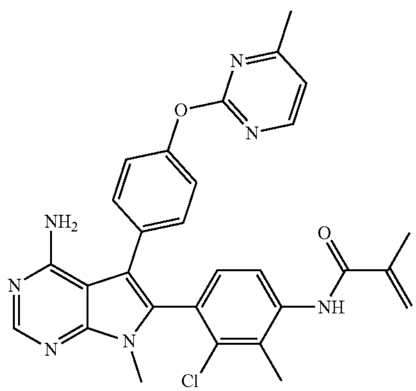 [SMILES: C=C(C)C(=O)Nc1ccc(-c2c(-c3ccc(Oc4nccc(C)n4)cc3)c3c(N)ncnc3n2C)c(Cl)c1C] | A | A |
| 1065 | 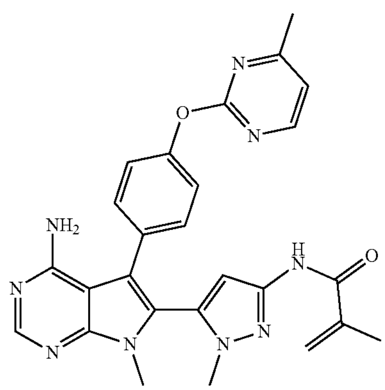 [SMILES: C=C(C)C(=O)Nc1cc(-c2c(-c3ccc(Oc4nccc(C)n4)cc3)c3c(N)ncnc3n2C)n(C)n1] | C | C |
| 1066 | 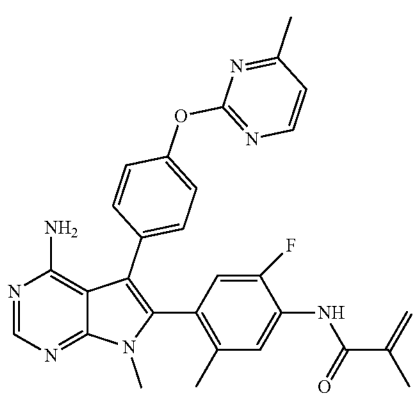 [SMILES: C=C(C)C(=O)Nc1cc(C)c(-c2c(-c3ccc(Oc4nccc(C)n4)cc3)c3c(N)ncnc3n2C)cc1F] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1067 | 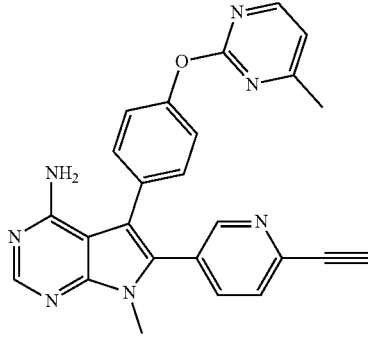 | A | A |
| 1068 | 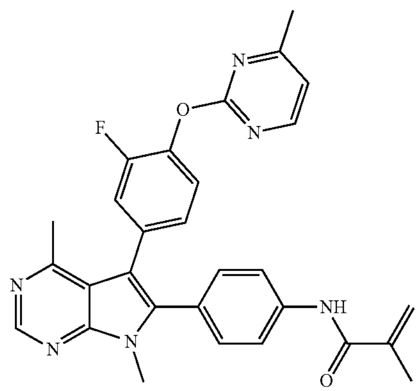 [SMILES: C=C(C)C(=O)Nc1ccc(-c2c(-c3ccc(Oc4nccc(C)n4)c(F)c3)c3c(C)ncnc3n2C)cc1] | A | A |
| 1069 | 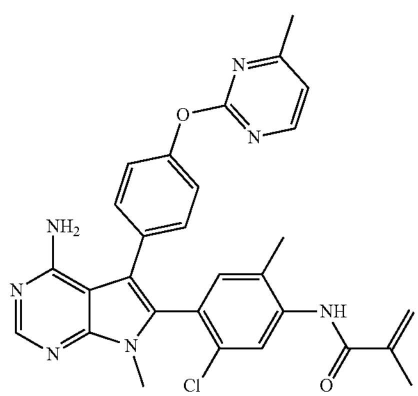 | C | C |
| 1070 | 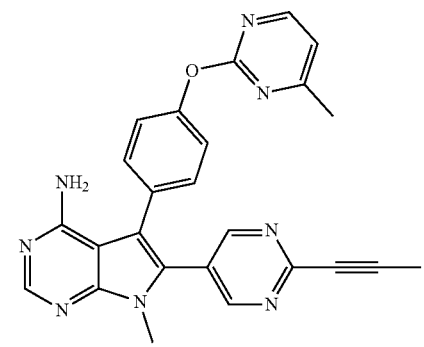 [SMILES: CC#Cc1ncc(-c2c(-c3ccc(Oc4nccc(C)n4)cc3)c3c(N)ncnc3n2C)cn1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1071 | 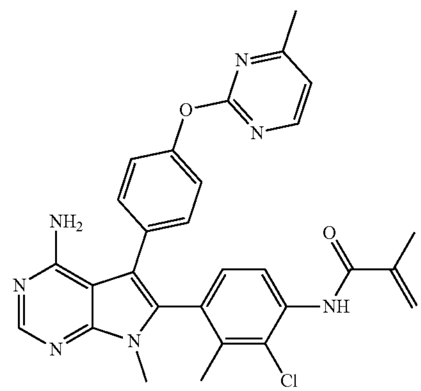 [SMILES: C=C(C)C(=O)Nc1ccc(-c2c(-c3ccc(Oc4nccc(C)n4)cc3)c3c(N)ncnc3n2C)c(C)c1Cl] | C | A |
| 1072 | 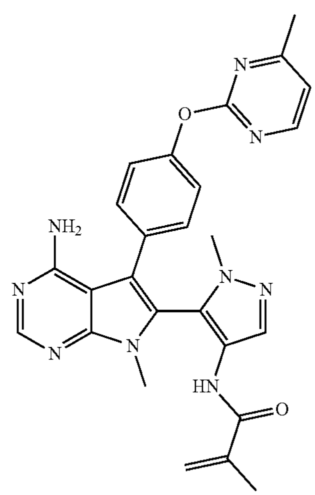 [SMILES: C=C(C)C(=O)Nc1cnn(C)c1-c1c(-c2ccc(Oc3nccc(C)n3)cc2)c2c(N)ncnc2n1C] | C | C |
| 1073 | 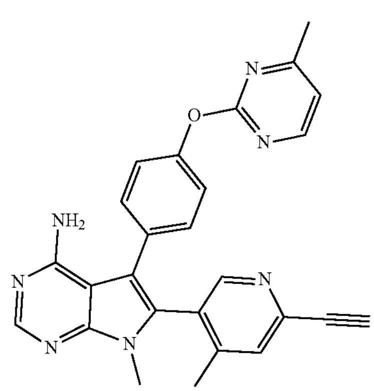 [SMILES: C#Cc1cc(C)c(-c2c(-c3ccc(Oc4nccc(C)n4)cc3)c3c(N)ncnc3n2C)cn1] | D | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1074 | 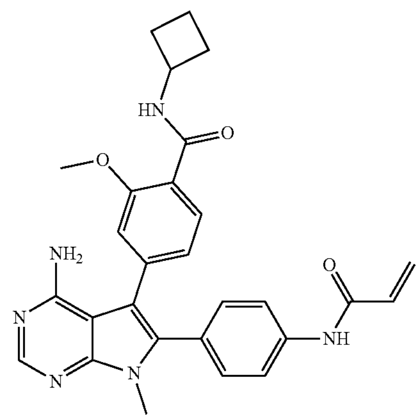 [SMILES: C=CC(=O)Nc1ccc(-c2c(-c3ccc(C(=O)NC4CCC4)c(OC)c3)c3c(N)ncnc3n2C)cc1] | A | A |
| 1075 | 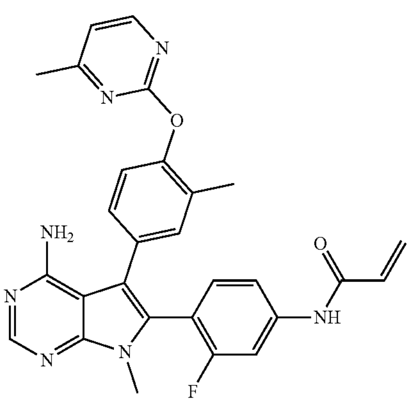 | A | |
| 1076 | 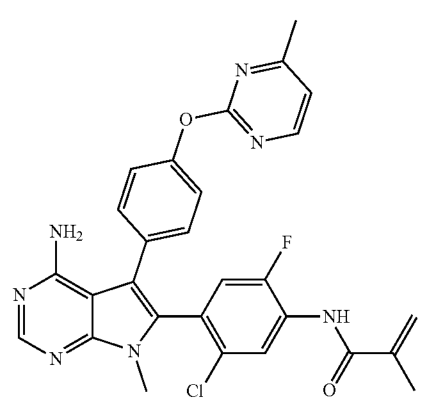 | A | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1077 | 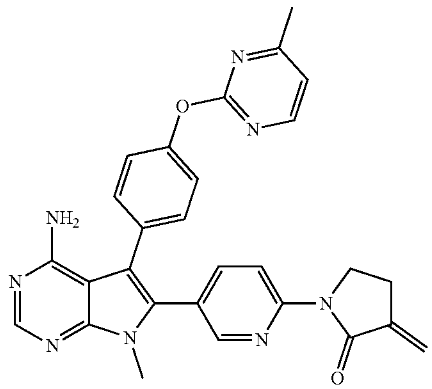 | A | A |
| 1078 | 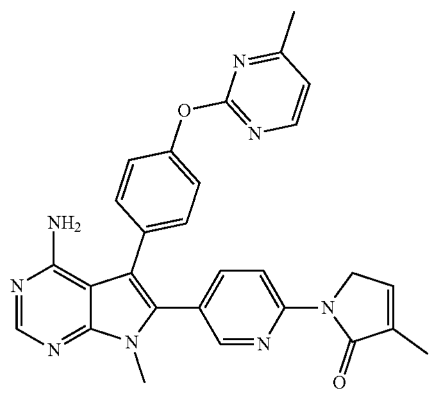 [SMILES: CC1=CCN(c2ccc(-c3c(-c4ccc(Oc5nccc(C)n5)cc4)c4c(N)ncnc4n3C)cn2)C1=O] | A | A |
| 1079 | 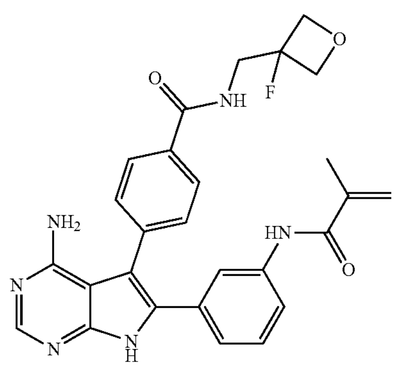 [SMILES: C=C(C)C(=O)Nc1cccc(-c2[nH]c3ncnc(N)c3c2-c2ccc(C(=O)NCC3(F)COC3)cc2)c1] | A | A |
| 1080 | 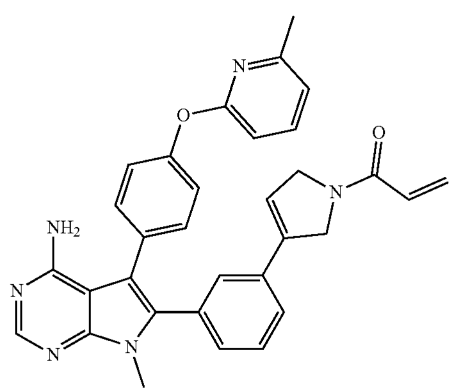 [SMILES: C=CC(=O)N1CC=C(c2cccc(-c3c(-c4ccc(Oc5cccc(C)n5)cc4)c4c(N)ncnc4n3C)c2)C1] | D | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1081 | 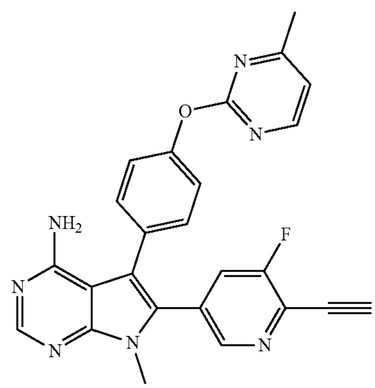 [SMILES: C#Cc1ncc(-c2c(-c3ccc(Oc4nccc(C)n4)cc3)c3c(N)ncnc3n2C)cc1F] | C | C |
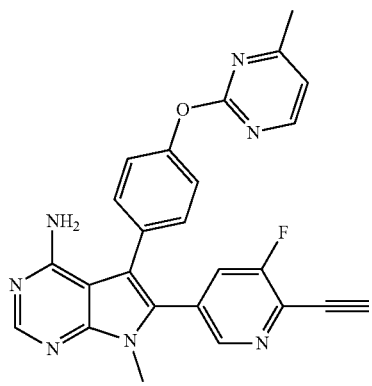
| | | | |
|---|---|---|---|
| 1082 | | A | A |
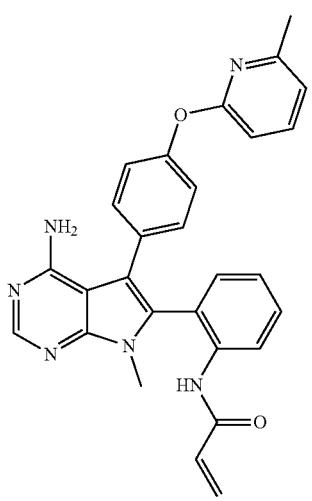 [SMILES: C=CC(=O)Nc1ccccc1-c1c(-c2ccc(Oc3cccc(C)n3)cc2)c2c(N)ncnc2n1C]
| | | | |
|---|---|---|---|
| 1083 | | C | D |
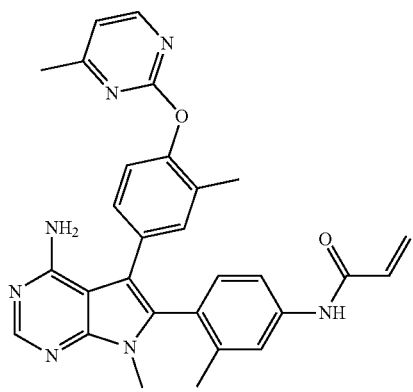 [SMILES: C=CC(=O)Nc1ccc(-c2c(-c3ccc(Oc4nccc(C)n4)c(C)c3)c3c(N)ncnc3n2C)c(C)c1]

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1084 | 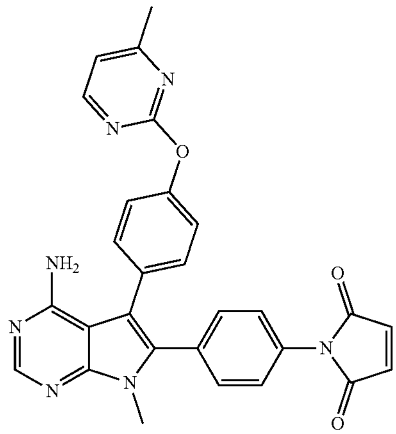 [SMILES: Cc1ccnc(Oc2ccc(-c3c(-c4ccc(N5C(=O)C=CC5=O)cc4)n(C)c4ncnc(N)c34)cc2)n1] | A | A |
| 1085 | 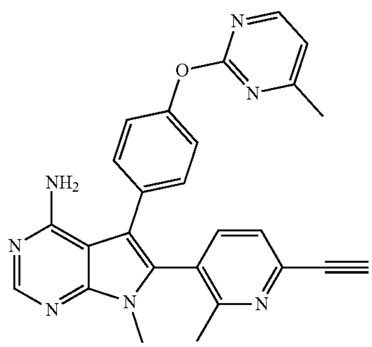 [SMILES: C#Cc1ccc(-c2c(-c3ccc(Oc4nccc(C)n4)cc3)c3c(N)ncnc3n2C)c(C)n1] | D | D |
| 1086 | 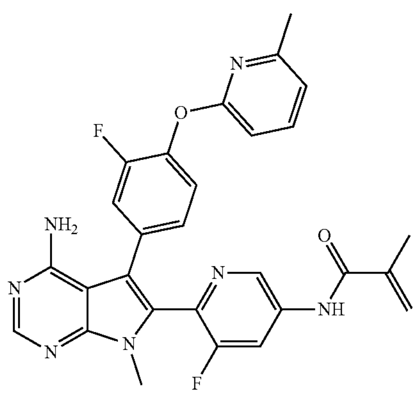 [SMILES: C=C(C)C(=O)Nc1cnc(-c2c(-c3ccc(Oc4cccc(C)n4)c(F)c3)c3c(N)ncnc3n2C)c(F)c1] | A | A |
| 1087 | 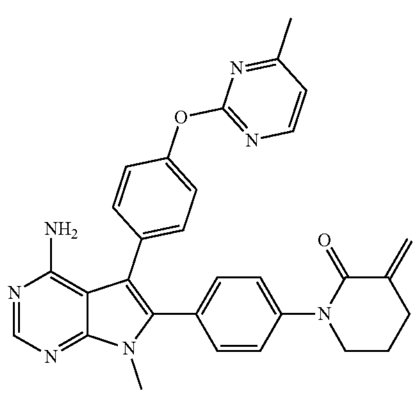 [SMILES: C=C1CCCN(c2ccc(-c3c(-c4ccc(Oc5nccc(C)n5)cc4)c4c(N)ncnc4n3C)cc2)C1=O] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1088 | 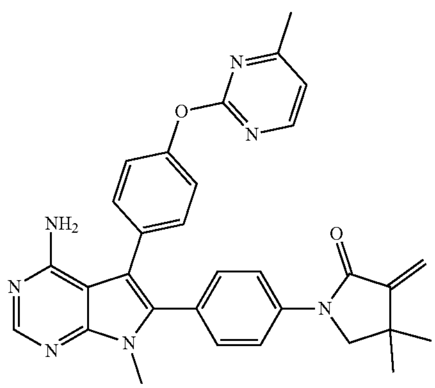 [SMILES: C=C1C(=O)N(c2ccc(-c3c(-c4ccc(Oc5nccc(C)n5)cc4)c4c(N)ncnc4n3C)cc2)CC1(C)C] | D | C |
| 1089 | 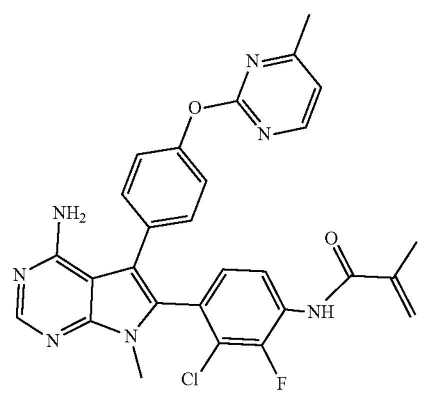 [SMILES: C=C(C)C(=O)Nc1ccc(-c2c(-c3ccc(Oc4nccc(C)n4)cc3)c3c(N)ncnc3n2C)c(Cl)c1F] | D | D |
| 1090 | 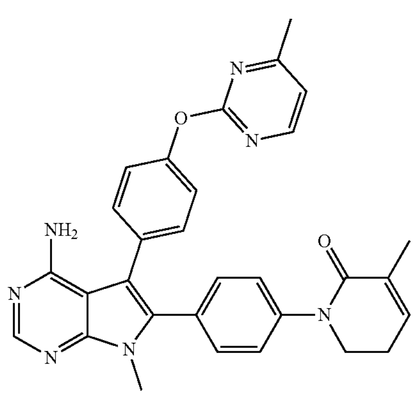 [SMILES: CC1=CCCN(c2ccc(-c3c(-c4ccc(Oc5nccc(C)n5)cc4)c4c(N)ncnc4n3C)cc2)C1=O] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1091 | 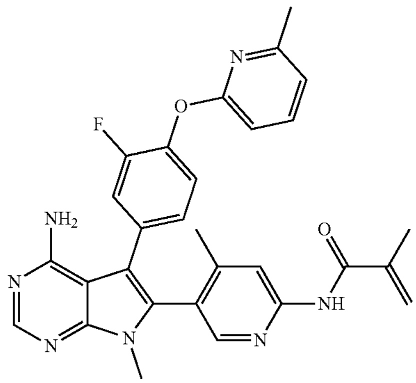 [SMILES: C=C(C)C(=O)Nc1cc(C)c(-c2c(-c3ccc(Oc4cccc(C)n4)c(F)c3)c3c(N)ncnc3n2C)cn1] | D | D |
| 1092 | 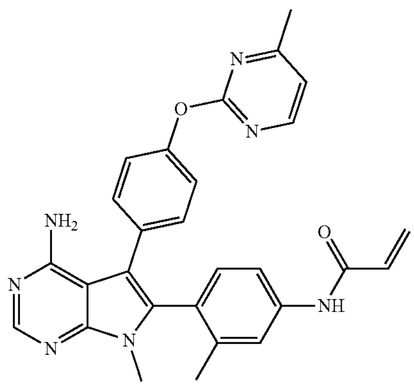 [SMILES: C=CC(=O)Nc1ccc(-c2c(-c3ccc(Oc4nccc(C)n4)cc3)c3c(N)ncnc3n2C)c(C)c1] | A | A |
| 1093 | 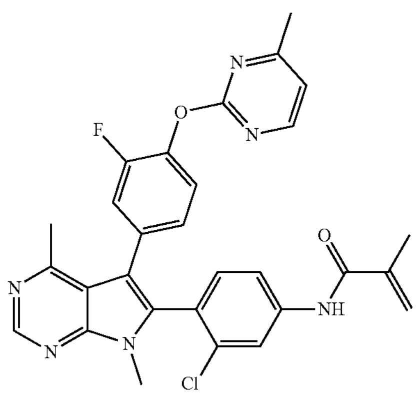 [SMILES: C=C(C)C(=O)Nc1ccc(-c2c(-c3ccc(Oc4nccc(C)n4)c(F)c3)c3c(C)ncnc3n2C)c(Cl)c1] | A | A |
| 1094 | 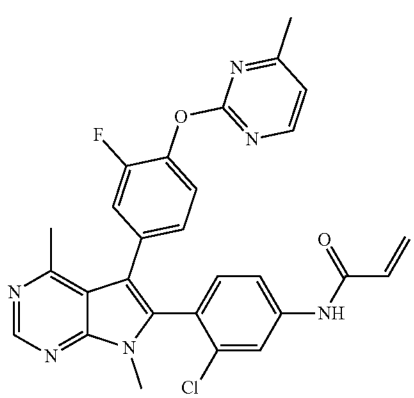 [SMILES: C=CC(=O)Nc1ccc(-c2c(-c3ccc(Oc4nccc(C)n4)c(F)c3)c3c(C)ncnc3n2C)c(Cl)c1] | A | A |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 1095 | 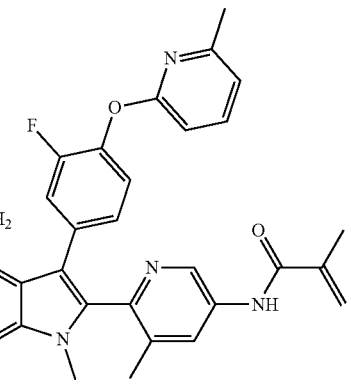 | A | A |
| 1096 | 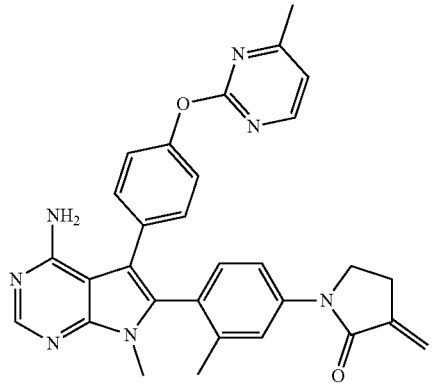 [SMILES: C=C1CCN(c2ccc(-c3c(-c4ccc(Oc5nccc(C)n5)cc4)c4c(N)ncnc4n3C)c(C)c2)C1=O] | A | A |
| 1097 | 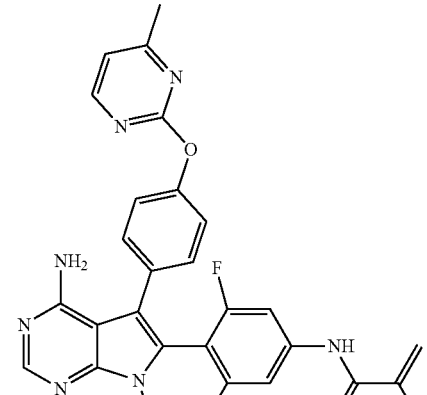 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1098 | 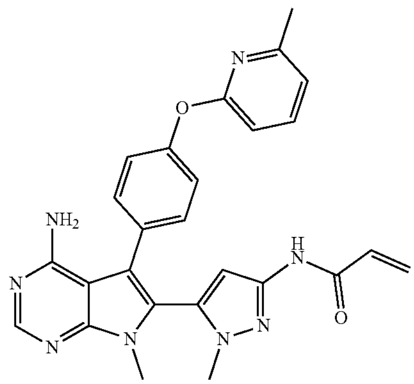 [SMILES: C=CC(=O)Nc1cc(-c2c(-c3ccc(Oc4cccc(C)n4)cc3)c3c(N)ncnc3n2C)n(C)n1] | A | A |
| 1099 | 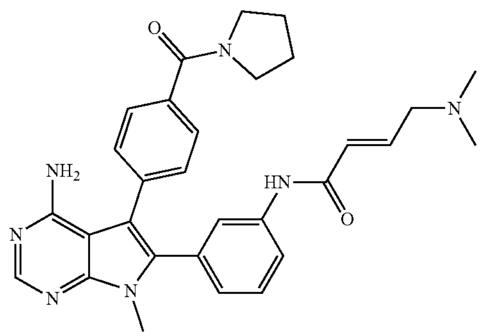 [SMILES: CN(C)C/C=C/C(=O)Nc1cccc(-c2c(-c3ccc(C(=O)N4CCCC4)cc3)c3c(N)ncnc3n2C)c1] | A | |
| 1100 | 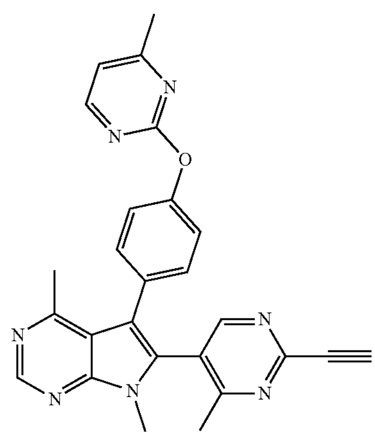 [SMILES: C#Cc1ncc(-c2c(-c3ccc(Oc4nccc(C)n4)cc3)c3c(C)ncnc3n2C)c(C)n1] | B | |
| 1101 | 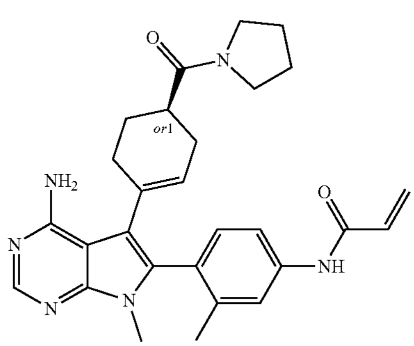 [SMILES: C=CC(=O)Nc1ccc(-c2c(C3=CC[C@H](C(=O)N4CCCC4)CC3)c3c(N)ncnc3n2C)c(C)c1] | A | |

TABLE 1-continued

Representative Compounds of the Invention with Bioactivity Data.

| Example | Structure | Biochemical FGFR2 Caliper IC50 | Cell SNU-16 IC50 |
| --- | --- | --- | --- |
| 1102 | 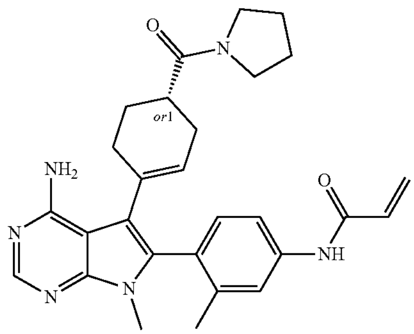 [SMILES: C=CC(=O)Nc1ccc(-c2c(C3=CC[C@@H](C(=O)N4CCCC4)CC3)c3c(N)ncnc3n2C)c(C)c1] | A | A |
| 1103 | 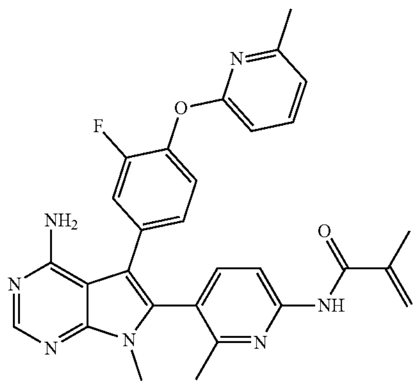 [SMILES: C=C(C)C(=O)Nc1ccc(-c2c(-c3ccc(Oc4cccc(C)n4)c(F)c3)c3c(N)ncnc3n2C)c(C)n1] | A | A |
| 1104 | 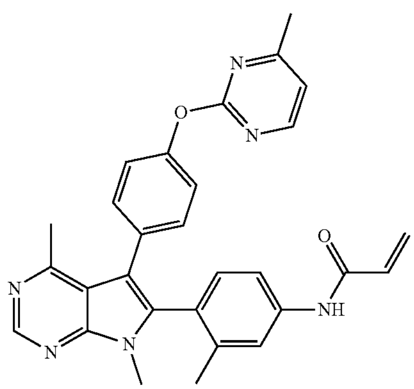 [SMILES: C=CC(=O)Nc1ccc(-c2c(-c3ccc(Oc4nccc(C)n4)cc3)c3c(C)ncnc3n2C)c(C)c1] | A | A |
| 1105 | 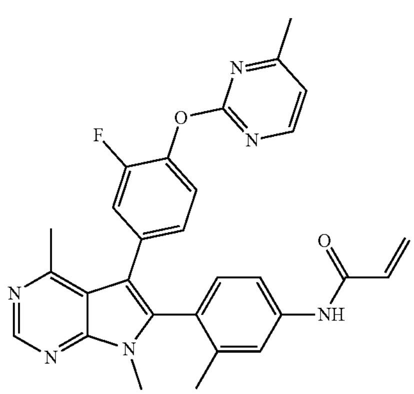 [SMILES: C=CC(=O)Nc1ccc(-c2c(-c3ccc(Oc4nccc(C)n4)c(F)c3)c3c(C)ncnc3n2C)c(C)c1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1106 | 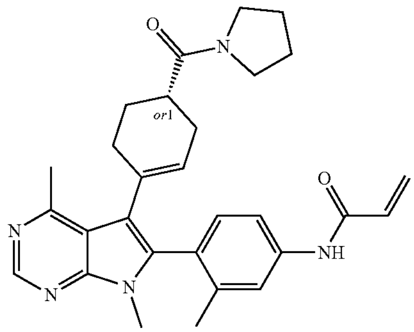 [SMILES: C=CC(=O)Nc1ccc(-c2c(C3=CC[C@@H](C(=O)N4CCCC4)CC3)c3c(C)ncnc3n2C)c(C)c1] | A | A |
| 1107 | 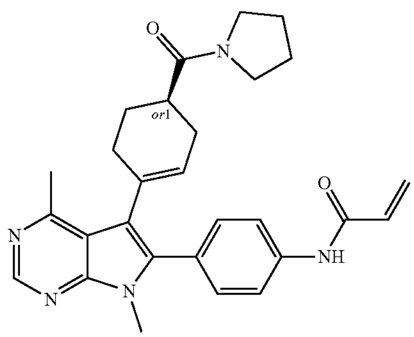 [SMILES: C=CC(=O)Nc1ccc(-c2c(C3=CC[C@H](C(=O)N4CCCC4)CC3)c3c(C)ncnc3n2C)cc1] | A | A |
| 1108 | 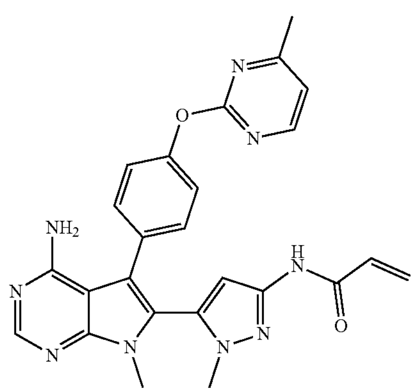 [SMILES: C=CC(=O)Nc1cc(-c2c(-c3ccc(Oc4nccc(C)n4)cc3)c3c(N)ncnc3n2C)n(C)n1] | A | A |
| 1109 | 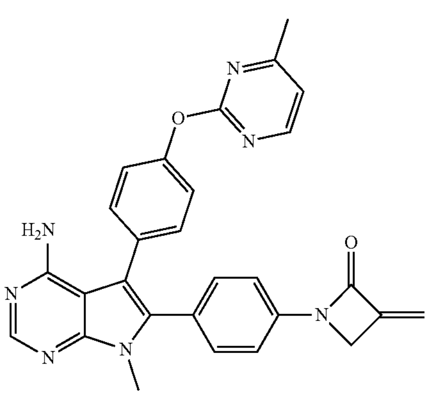 [SMILES: C=C1CN(c2ccc(-c3c(-c4ccc(Oc5nccc(C)n5)cc4)c4c(N)ncnc4n3C)cc2)C1=O] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1110 | 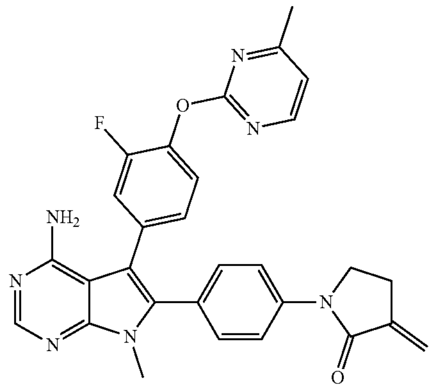 [SMILES: C=C1CCN(c2ccc(-c3c(-c4ccc(Oc5nccc(C)n5)c(F)c4)c4c(N)ncnc4n3C)cc2)C1=O] | A | A |
| 1111 | 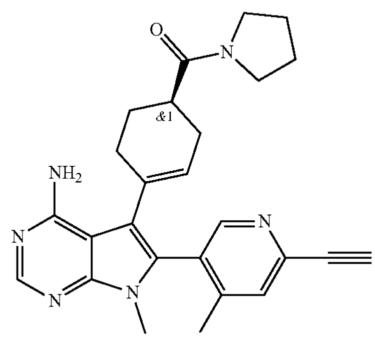 [SMILES: C#Cc1cc(C)c(-c2c(C3=CC[C@H](C(=O)N4CCCC4)CC3)c3c(N)ncnc3n2C)cn1] | A | A |
| 1112 | 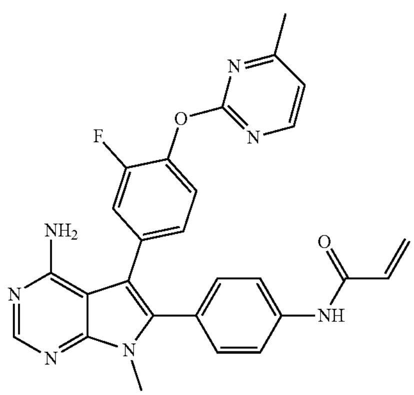 [SMILES: C=CC(=O)Nc1ccc(-c2c(-c3ccc(Oc4nccc(C)n4)c(F)c3)c3c(N)ncnc3n2C)cc1] | A | A |
| 1113 | 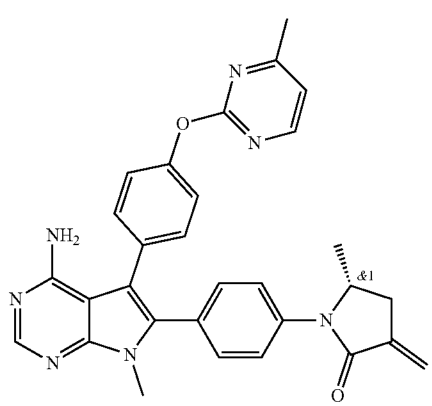 [SMILES: C=C1C[C@@H](C)N(c2ccc(-c3c(-c4ccc(Oc5nccc(C)n5)cc4)c4c(N)ncnc4n3C)cc2)C1=O] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1114 | 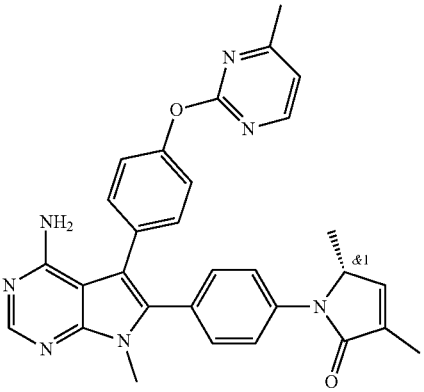 [SMILES: CC1=C[C@@H](C)N(c2ccc(-c3c(-c4ccc(Oc5nccc(C)n5)cc4)c4c(N)ncnc4n3C)cc2)C1=O] | C | A |
| 1115 | 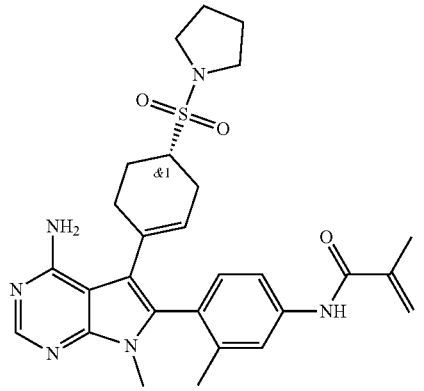 [SMILES: C=C(C)C(=O)Nc1ccc(-c2c(C3=CC[C@@H](S(=O)(=O)N4CCCC4)CC3)c3c(N)ncnc3n2C)c(C)c1] | D | D |
| 1116 | 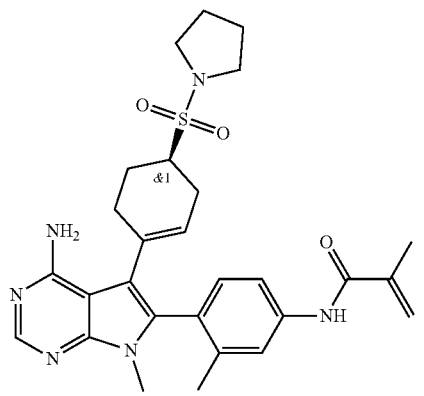 [SMILES: C=C(C)C(=O)Nc1ccc(-c2c(C3=CC[C@H](S(=O)(=O)N4CCCC4)CC3)c3c(N)ncnc3n2C)c(C)c1] | B | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1117 | 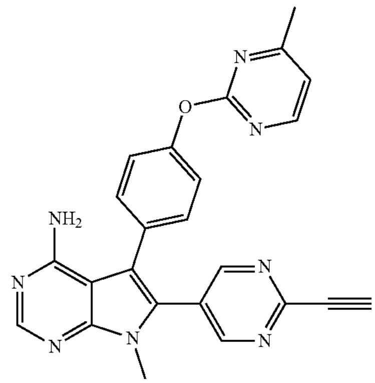 | B | A |
| 1118 | 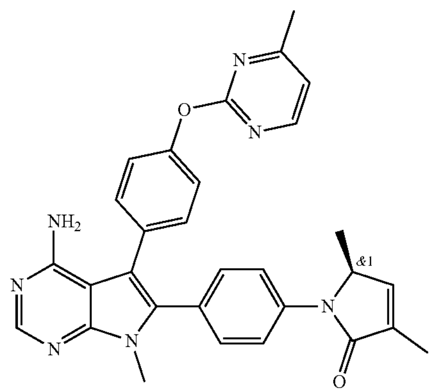 [SMILES: CC1=C[C@H](C)N(c2ccc(-c3c(-c4ccc(Oc5nccc(C)n5)cc4)c4c(N)ncnc4n3C)cc2)C1=O] | A | A |
| 1119 | 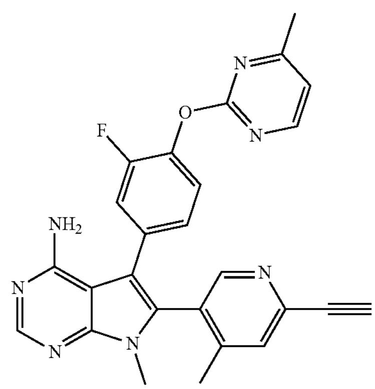 [SMILES: C#Cc1cc(C)c(-c2c(-c3ccc(Oc4nccc(C)n4)c(F)c3)c3c(N)ncnc3n2C)cn1] | D | C |
| 1120 | 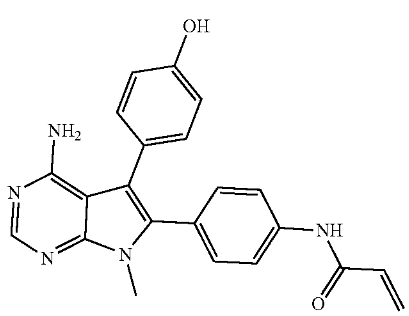 [SMILES: C=CC(=O)Nc1ccc(-c2c(-c3ccc(O)cc3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1121 | 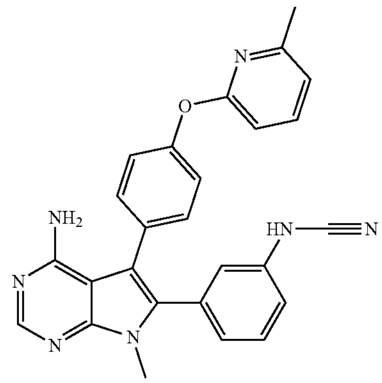 [SMILES: Cc1cccc(Oc2ccc(-c3c(-c4cccc(NC#N)c4)n(C)c4ncnc(N)c34)cc2)n1] | A | A |
| 1122 | 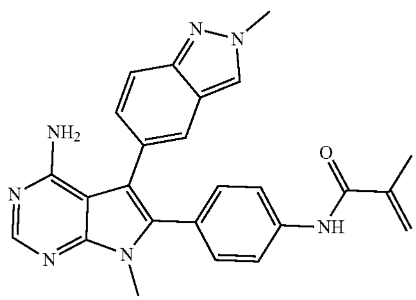 [SMILES: C=C(C)C(=O)Nc1ccc(-c2c(-c3ccc4nn(C)cc4c3)c3c(N)ncnc3n2C)cc1] | A | |
| 1123 | 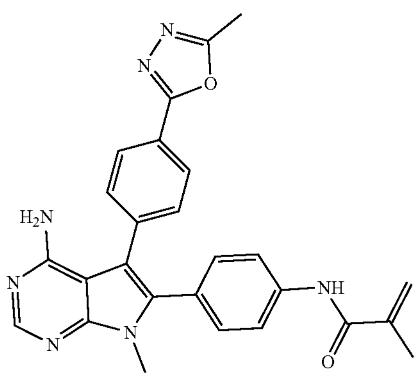 [SMILES: C=C(C)C(=O)Nc1ccc(-c2c(-c3ccc(-c4nnc(C)o4)cc3)c3c(N)ncnc3n2C)cc1] | D | C |
| 1124 | 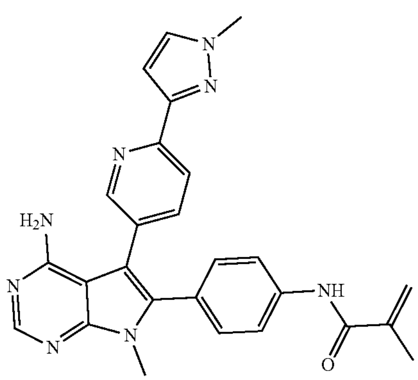 [SMILES: C=C(C)C(=O)Nc1ccc(-c2c(-c3ccc(-c4ccn(C)n4)nc3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1125 | 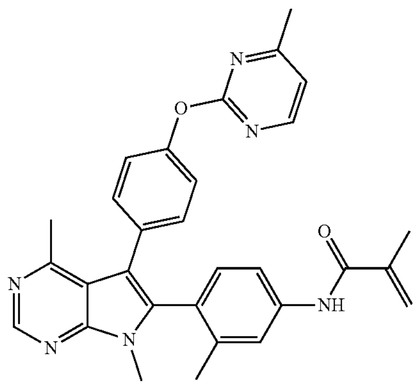 [SMILES: C=C(C)C(=O)Nc1ccc(-c2c(-c3ccc(Oc4nccc(C)n4)cc3)c3c(C)ncnc3n2C)c(C)c1] | D | D |
| 1126 | 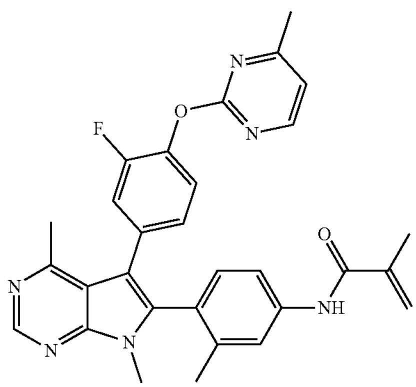 [SMILES: C=C(C)C(=O)Nc1ccc(-c2c(-c3ccc(Oc4nccc(C)n4)c(F)c3)c3c(C)ncnc3n2C)c(C)c1] | A | A |
| 1127 | 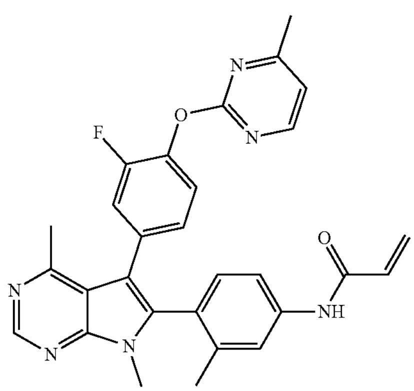 [SMILES: C=CC(=O)Nc1ccc(-c2c(-c3ccc(Oc4nccc(C)n4)c(F)c3)c3c(C)ncnc3n2C)c(C)c1] | A | A |
| 1128 | 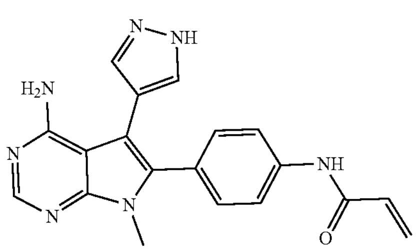 [SMILES: C=CC(=O)Nc1ccc(-c2c(-c3cn[nH]c3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1129 | 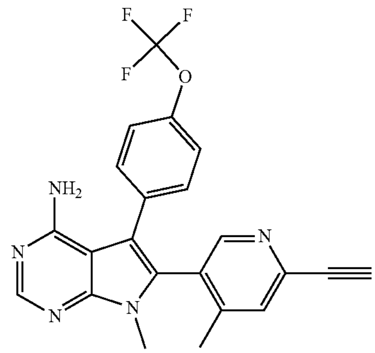 [SMILES: C#Cc1cc(C)c(-c2c(-c3ccc(OC(F)(F)F)cc3)c3c(N)ncnc3n2C)cn1] | A | |
| 1130 | 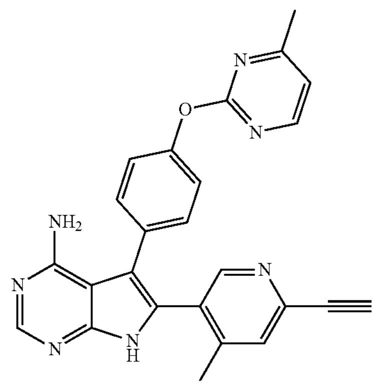 [SMILES: C#Cc1cc(C)c(-c2[nH]c3ncnc(N)c3c2-c2ccc(Oc3nccc(C)n3)cc2)cn1] | C | C |
| 1131 | 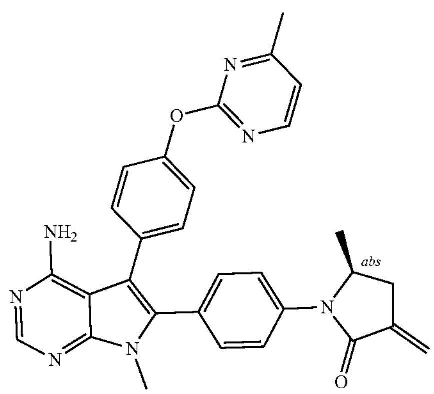 [SMILES: C=C1C[C@H](C)N(c2ccc(-c3c(-c4ccc(Oc5nccc(C)n5)cc4)c4c(N)ncnc4n3C)cc2)C1=O] | A | A |
| 1132 | 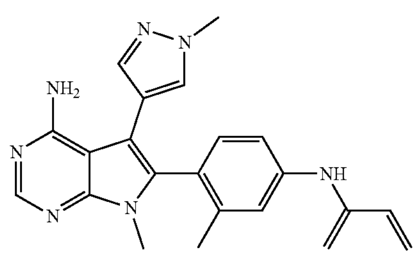 [SMILES: C=CC(=C)Nc1ccc(-c2c(-c3cnn(C)c3)c3c(N)ncnc3n2C)c(C)c1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1133 | 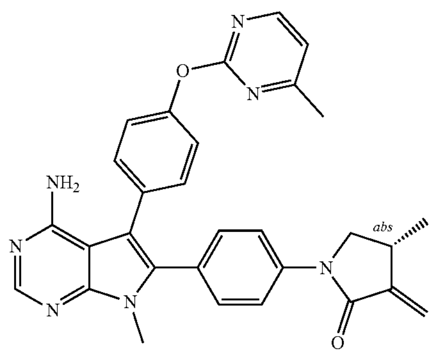 [SMILES: C=C1C(=O)N(c2ccc(-c3c(-c4ccc(Oc5nccc(C)n5)cc4)c4c(N)ncnc4n3C)cc2)C[C@@H]1C] | B | B |
| 1134 | 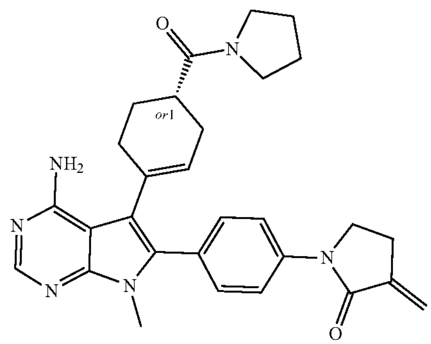 [SMILES: C=C1CCN(c2ccc(-c3c(C4=CC[C@@H](C(=O)N5CCCC5)CC4)c4c(N)ncnc4n3C)cc2)C1=O] | C | B |
| 1135 | 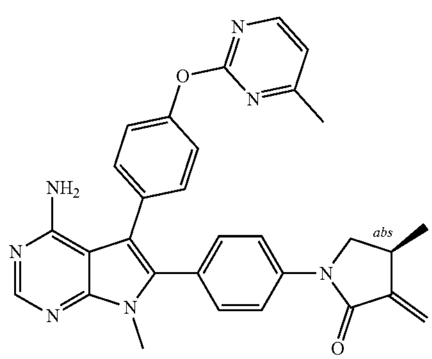 [SMILES: C=C1C(=O)N(c2ccc(-c3c(-c4ccc(Oc5nccc(C)n5)cc4)c4c(N)ncnc4n3C)cc2)C[C@H]1C] | C | B |
| 1136 | 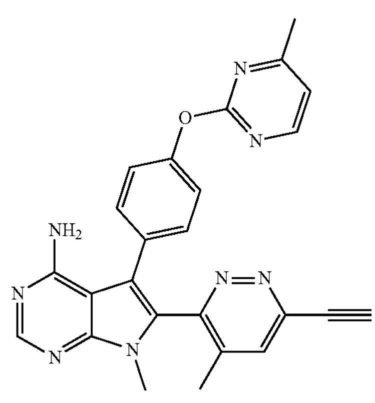 [SMILES: C#Cc1cc(C)c(-c2c(-c3ccc(Oc4nccc(C)n4)cc3)c3c(N)ncnc3n2C)nn1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1137 | 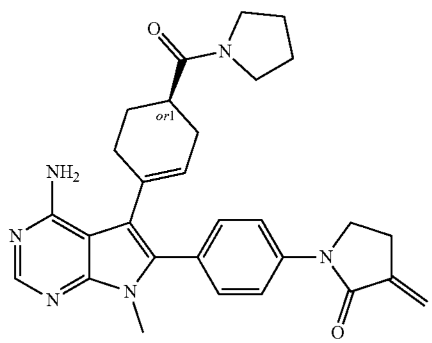 [SMILES: C=C1CCN(c2ccc(-c3c(C4=CC[C@H](C(=O)N5CCCC5)CC4)c4c(N)ncnc4n3C)cc2)C1=O] | C | B |
| 1138 | 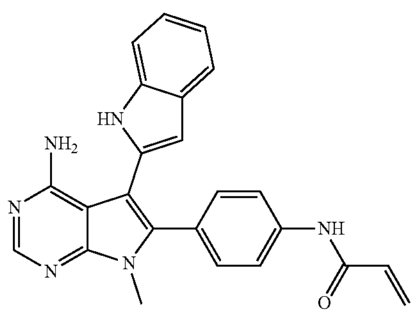 [SMILES: C=CC(=O)Nc1ccc(-c2c(-c3cc4ccccc4[nH]3)c3c(N)ncnc3n2C)cc1] | A | A |
| 1139 | 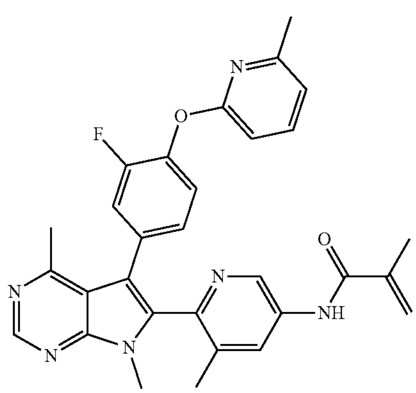 [SMILES: C=C(C)C(=O)Nc1cnc(-c2c(-c3ccc(Oc4cccc(C)n4)c(F)c3)c3c(C)ncnc3n2C)c(C)c1] | A | |
| 1140 | 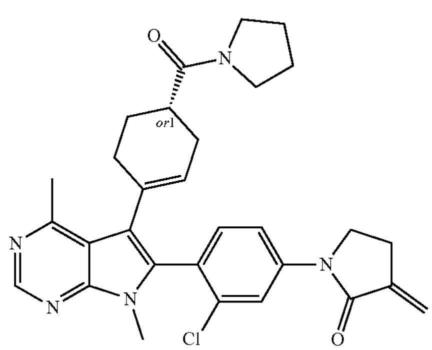 [SMILES: C=C1CCN(c2ccc(-c3c(C4=CC[C@@H](C(=O)N5CCCC5)CC4)c4c(C)ncnc4n3C)c(Cl)c2)C1=O] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1141 | 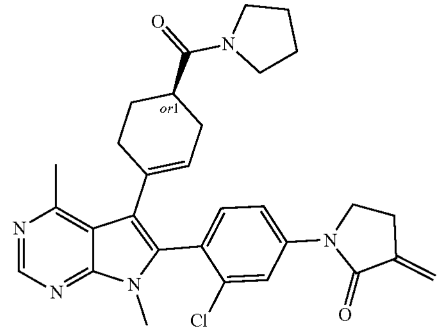 [SMILES: C=C1CCN(c2ccc(-c3c(C4=CC[C@H](C(=O)N5CCCC5)CC4)c4c(C)ncnc4n3C)c(Cl)c2)C1=O] | A | A |
| 1142 | 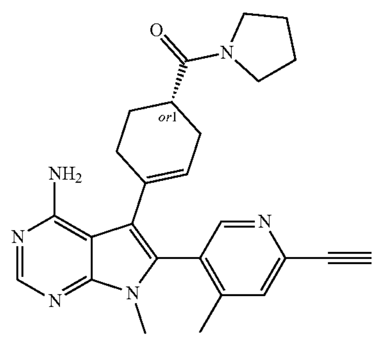 [SMILES: C#Cc1cc(C)c(-c2c(C3=CC[C@@H](C(=O)N4CCCC4)CC3)c3c(N)ncnc3n2C)cn1] | A | A |
| 1143 | 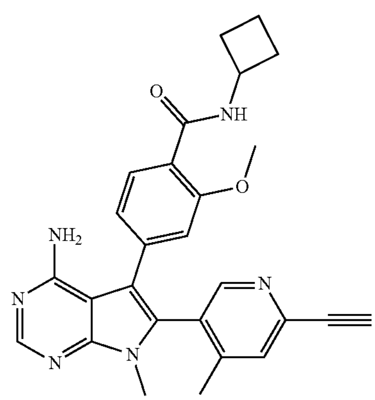 [SMILES: C#Cc1cc(C)c(-c2c(-c3ccc(C(=O)NC4CCC4)c(OC)c3)c3c(N)ncnc3n2C)cn1] | D | C |
| 1144 | 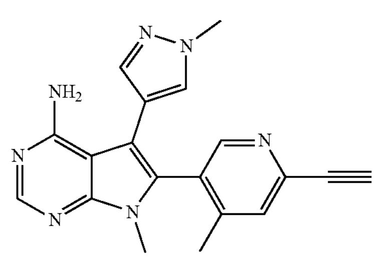 [SMILES: C#Cc1cc(C)c(-c2c(-c3cnn(C)c3)c3c(N)ncnc3n2C)cn1] | B | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1145 | 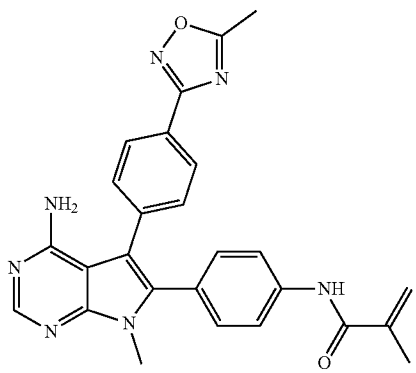 [SMILES: C=C(C)C(=O)Nc1ccc(-c2c(-c3ccc(-c4noc(C)n4)cc3)c3c(N)ncnc3n2C)cc1] | D | D |
| 1146 | 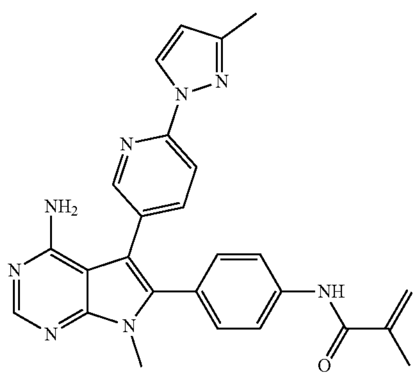 [SMILES: C=C(C)C(=O)Nc1ccc(-c2c(-c3ccc(-n4ccc(C)n4)nc3)c3c(N)ncnc3n2C)cc1] | C | |
| 1147 | 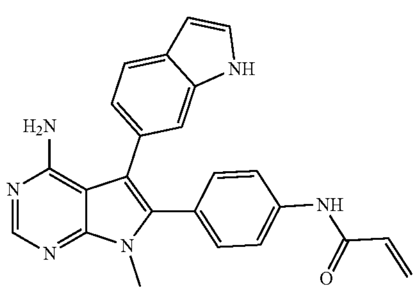 [SMILES: C=CC(=O)Nc1ccc(-c2c(-c3ccc4cc[nH]c4c3)c3c(N)ncnc3n2C)cc1] | D | |
| 1148 | 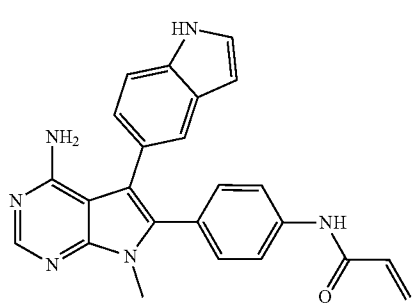 [SMILES: C=CC(=O)Nc1ccc(-c2c(-c3ccc4[nH]ccc4c3)c3c(N)ncnc3n2C)cc1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1149 | 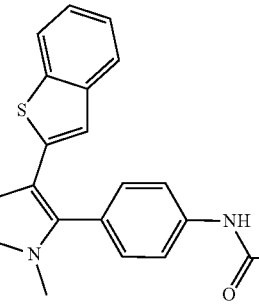 | A | |
| 1150 | 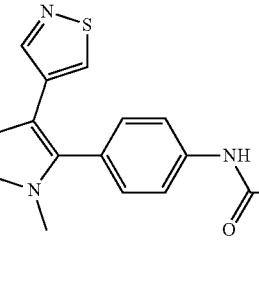 | A | |
| 1151 | 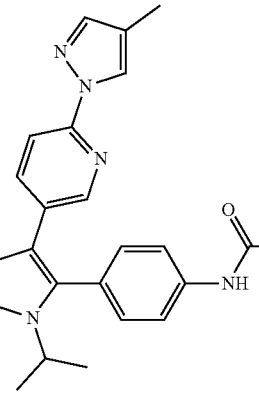 | B | C |
| 1152 | 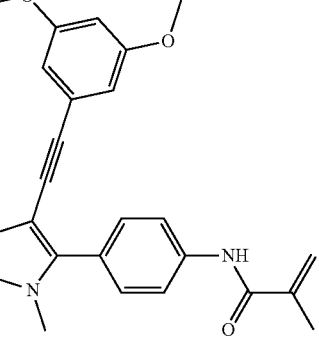 | D | |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|-------------------|
| 1153 | 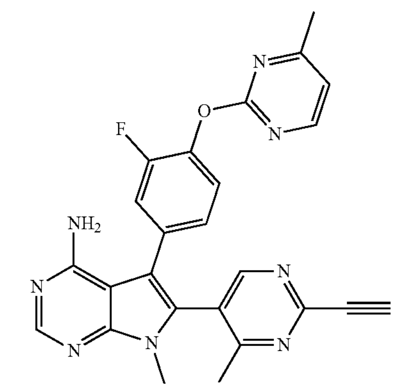 | A | B |
| 1154 | 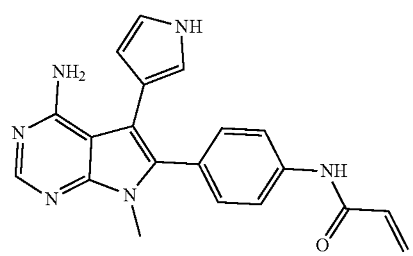 [SMILES: C=CC(=O)Nc1ccc(-c2c(-c3cc[nH]c3)c3c(N)ncnc3n2C)cc1] | A | A |
| 1155 | 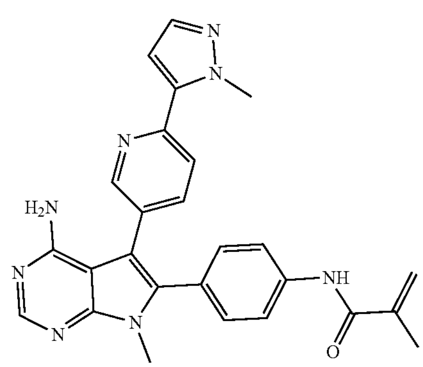 [SMILES: C=C(C)C(=O)Nc1ccc(-c2c(-c3ccc(-c4ccnn4C)nc3)c3c(N)ncnc3n2C)cc1] | A | A |
| 1156 | 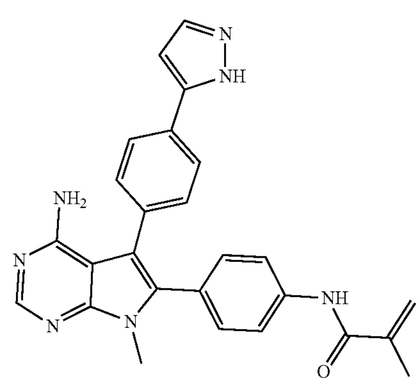 [SMILES: C=C(C)C(=O)Nc1ccc(-c2c(-c3ccc(-c4ccn[nH]4)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1157 | 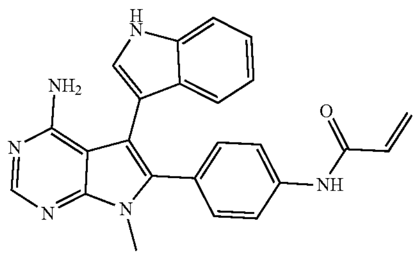 [SMILES: C=CC(=O)Nc1ccc(-c2c(-c3c[nH]c4ccccc34)c3c(N)ncnc3n2C)cc1] | C | C |
| 1158 | 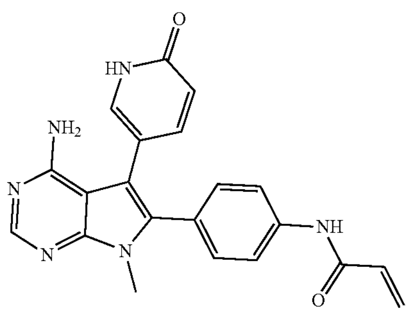 [SMILES: C=CC(=O)Nc1ccc(-c2c(-c3ccc(=O)[nH]c3)c3c(N)ncnc3n2C)cc1] | A | A |
| 1159 | 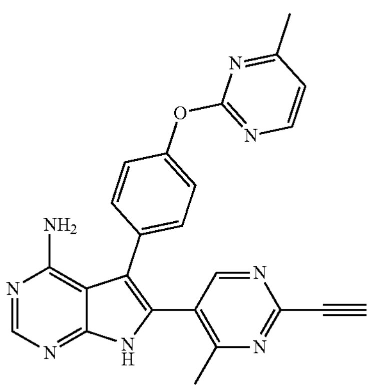 | C | |
| 1160 | 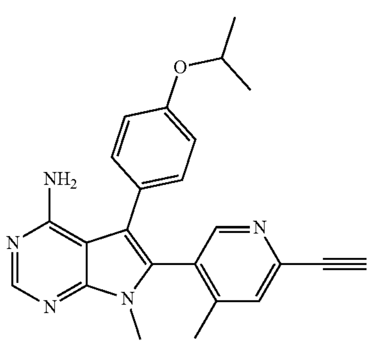 [SMILES: C#Cc1cc(C)c(-c2c(-c3ccc(OC(C)C)cc3)c3c(N)ncnc3n2C)cn1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1161 | 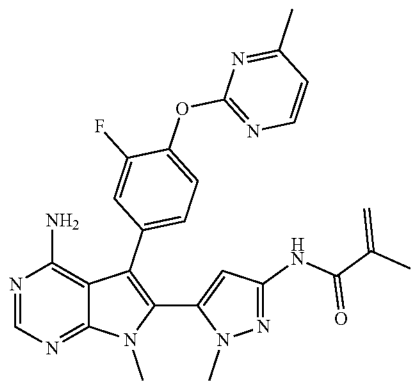 [SMILES: C=C(C)C(=O)Nc1cc(-c2c(-c3ccc(Oc4nccc(C)n4)c(F)c3)c3c(N)ncnc3n2C)n(C)n1] | A | A |
| 1162 | 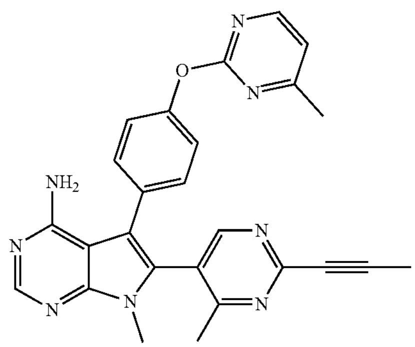 [SMILES: CC#Cc1ncc(-c2c(-c3ccc(Oc4nccc(C)n4)cc3)c3c(N)ncnc3n2C)c(C)n1] | A | A |
| 1163 | 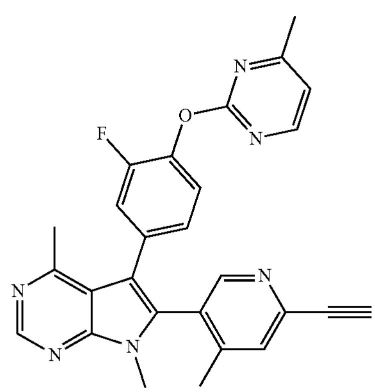 [SMILES: C#Cc1cc(C)c(-c2c(-c3ccc(Oc4nccc(C)n4)c(F)c3)c3c(C)ncnc3n2C)cn1] | A | A |
| 1164 | 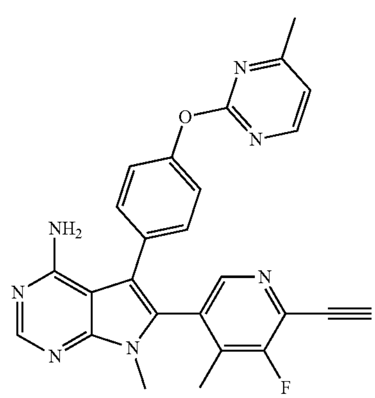 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1165 | 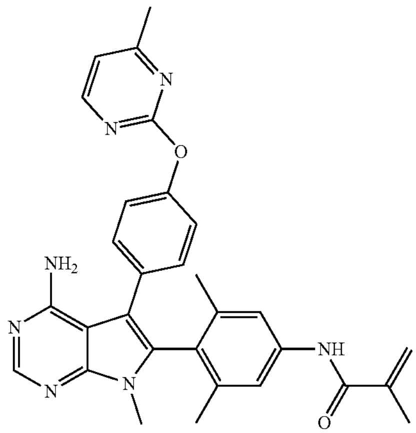 [SMILES: C=C(C)C(=O)Nc1cc(C)c(-c2c(-c3ccc(Oc4nccc(C)n4)cc3)c3c(N)ncnc3n2C)c(C)c1] | A | A |
| 1166 | 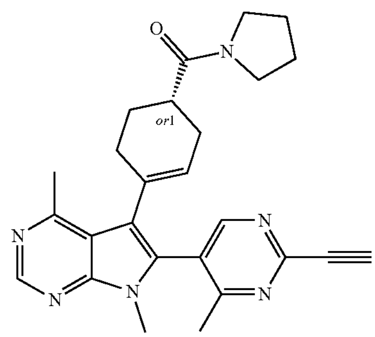 [SMILES: C#Cc1ncc(-c2c(C3=CC[C@@H](C(=O)N4CCCC4)CC3)c3c(C)ncnc3n2C)c(C)n1] | A | A |
| 1167 | 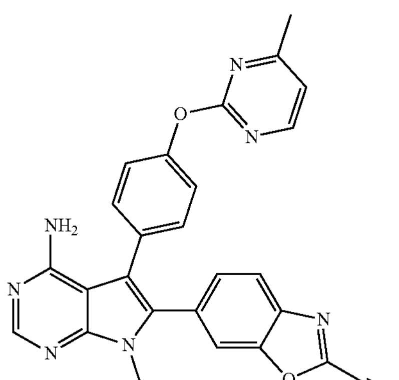 | A | A |
| 1168 | 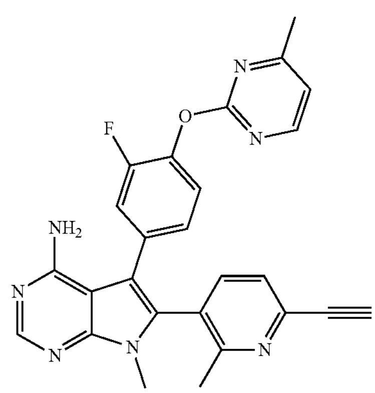 [SMILES: C#Cc1ccc(-c2c(-c3ccc(Oc4nccc(C)n4)c(F)c3)c3c(N)ncnc3n2C)c(C)n1] | A | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1169 | 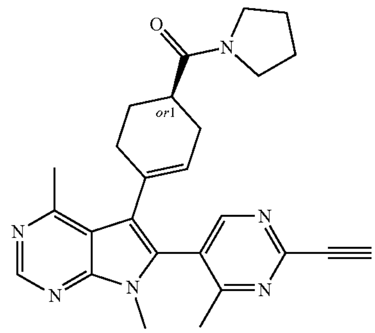 [SMILES: C#Cc1ncc(-c2c(C3=CC[C@H](C(=O)N4CCCC4)CC3)c3c(C)ncnc3n2C)c(C)n1] | A | A |
| 1170 | 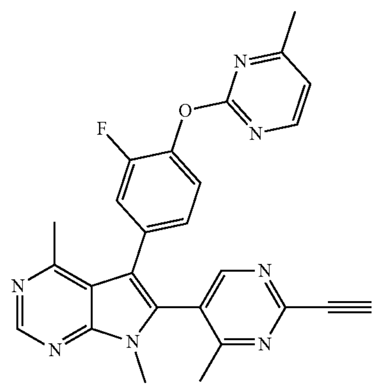 [SMILES: C#Cc1ncc(-c2c(-c3ccc(Oc4nccc(C)n4)c(F)c3)c3c(C)ncnc3n2C)c(C)n1] | A | A |
| 1171 | 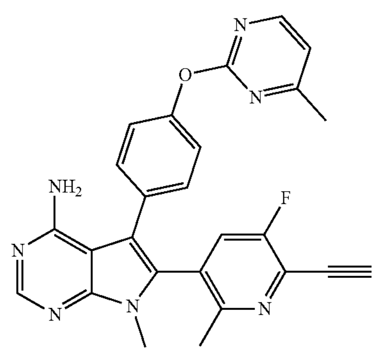 [SMILES: C#Cc1nc(C)c(-c2c(-c3ccc(Oc4nccc(C)n4)cc3)c3c(N)ncnc3n2C)cc1F] | A | A |
| 1172 | 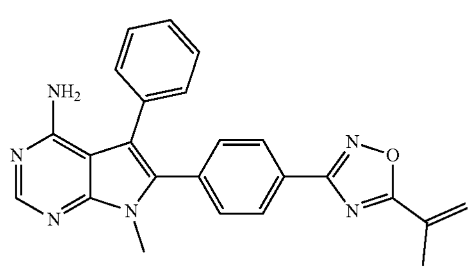 [SMILES: C=C(C)c1nc(-c2ccc(-c3c(-c4ccccc4)c4c(N)ncnc4n3C)cc2)no1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1173 | 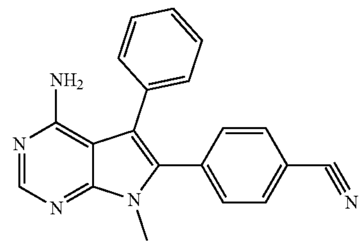 [SMILES: Cn1c(-c2ccc(C#N)cc2)c(-c2ccccc2)c2c(N)ncnc21] | D | |
| 1174 | 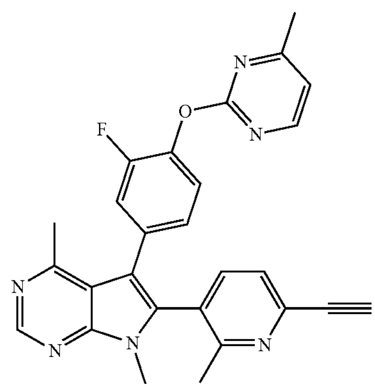 [SMILES: C#Cc1ccc(-c2c(-c3ccc(Oc4nccc(C)n4)c(F)c3)c3c(C)ncnc3n2C)c(C)n1] | D | |
| 1175 | 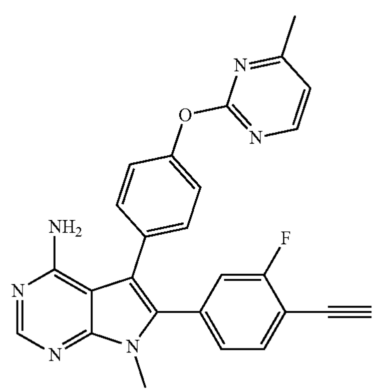 [SMILES: C#Cc1ccc(-c2c(-c3ccc(Oc4nccc(C)n4)cc3)c3c(N)ncnc3n2C)cc1F] | B | A |
| 1176 | 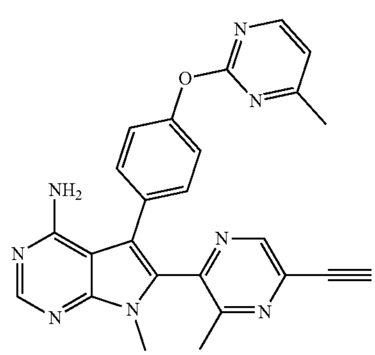 [SMILES: C#Cc1cnc(-c2c(-c3ccc(Oc4nccc(C)n4)cc3)c3c(N)ncnc3n2C)c(C)n1] | D | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1177 | 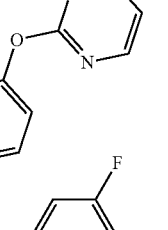 | A | A |
| 1178 | 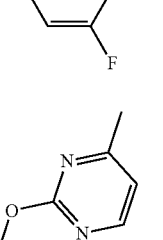 | D | |
| 1179 | 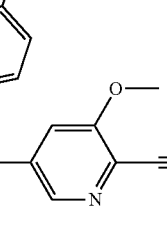 | A | A |
| 1180 | 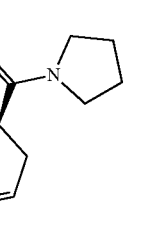 | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1181 | 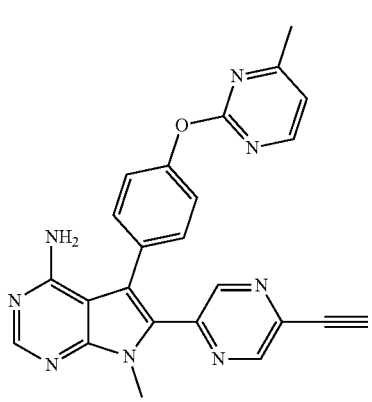 [SMILES: C#Cc1cnc(-c2c(-c3ccc(Oc4nccc(C)n4)cc3)c3c(N)ncnc3n2C)cn1] | A | A |
| 1182 | 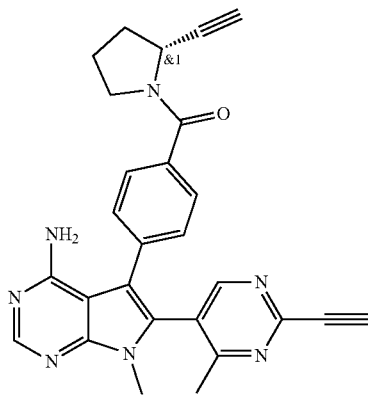 | A | A |
| 1183 | 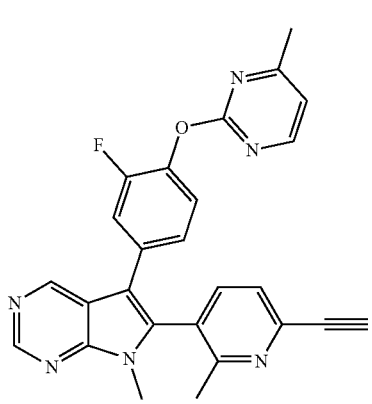 | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1184 | 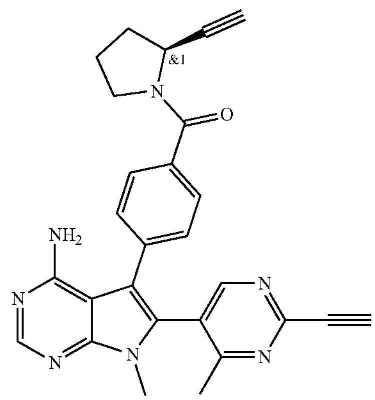 [SMILES: C#Cc1ncc(-c2c(-c3ccc(C(=O)N4CCC[C@H]4C#C)cc3)c3c(N)ncnc3n2C)c(C)n1] | D | D |
| 1185 | 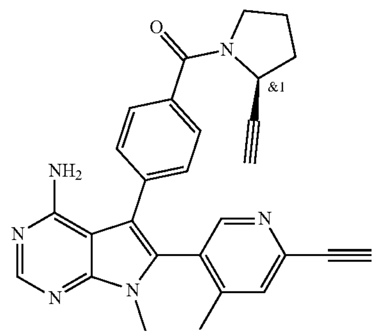 [SMILES: C#Cc1cc(C)c(-c2c(-c3ccc(C(=O)N4CCC[C@H]4C#C)cc3)c3c(N)ncnc3n2C)cn1] | A | A |
| 1186 | 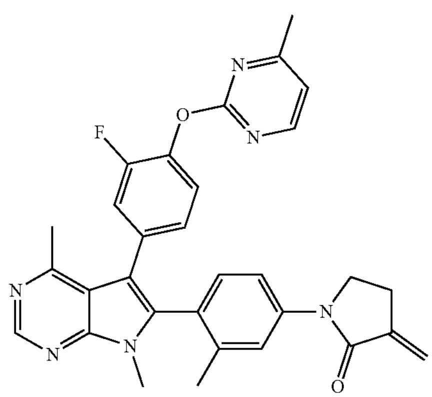 [SMILES: C=C1CCN(c2ccc(-c3c(-c4ccc(Oc5nccc(C)n5)c(F)c4)c4c(C)ncnc4n3C)c(C)c2)C1=O] | A | A |
| 1187 | 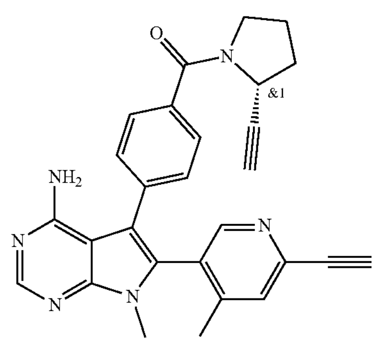 [SMILES: C#Cc1cc(C)c(-c2c(-c3ccc(C(=O)N4CCC[C@@H]4C#C)cc3)c3c(N)ncnc3n2C)cn1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1188 | 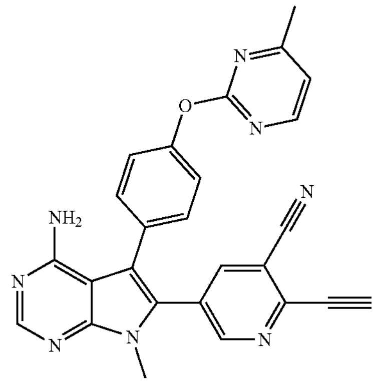 [SMILES: C#Cc1ncc(-c2c(-c3ccc(Oc4nccc(C)n4)cc3)c3c(N)ncnc3n2C)cc1C#N] | A | A |
| 1189 | 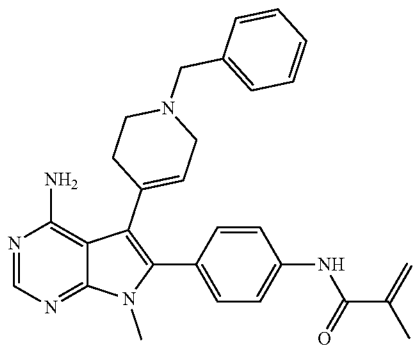 [SMILES: C=C(C)C(=O)Nc1ccc(-c2c(C3=CCN(Cc4ccccc4)CC3)c3c(N)ncnc3n2C)cc1] | A | A |
| 1190 | 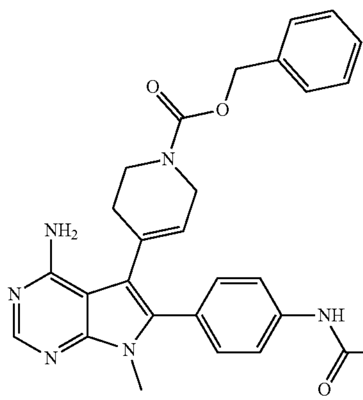 | D | |
| 1191 | 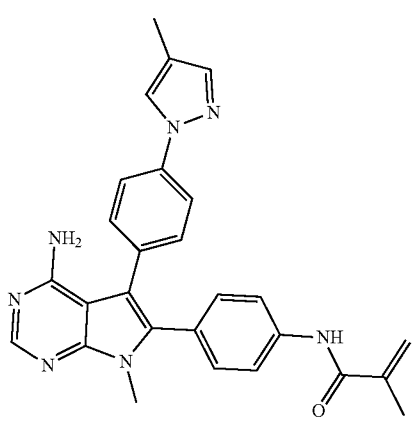 [SMILES: C=C(C)C(=O)Nc1ccc(-c2c(-c3ccc(-n4cc(C)cn4)cc3)c3c(N)ncnc3n2C)cc1] | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1192 | 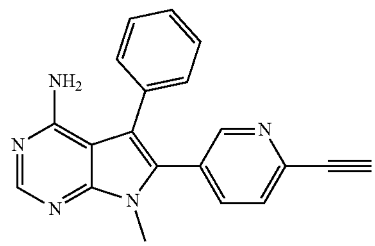 [SMILES: C#Cc1ccc(-c2c(-c3ccccc3)c3c(N)ncnc3n2C)cn1] | A | |
| 1193 | 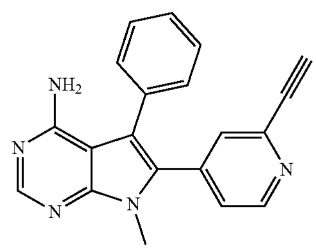 [SMILES: C#Cc1cc(-c2c(-c3ccccc3)c3c(N)ncnc3n2C)ccn1] | C | C |
| 1194 | 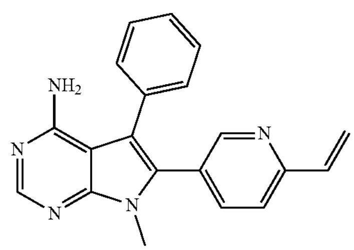 [SMILES: C=Cc1ccc(-c2c(-c3ccccc3)c3c(N)ncnc3n2C)cn1] | D | D |
| 1195 | 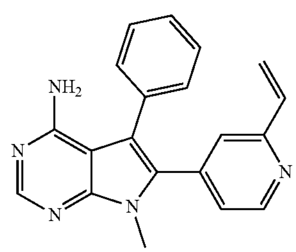 [SMILES: C=Cc1cc(-c2c(-c3ccccc3)c3c(N)ncnc3n2C)ccn1] | B | |
| 1196 | 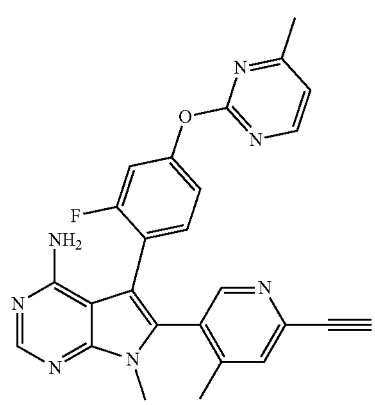 [SMILES: C#Cc1cc(C)c(-c2c(-c3ccc(Oc4nccc(C)n4)cc3F)c3c(N)ncnc3n2C)cn1] | C | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1197 | 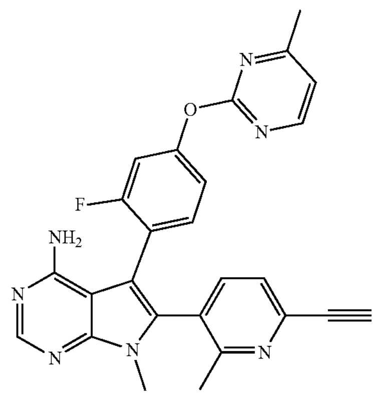 [SMILES: C#Cc1ccc(-c2c(-c3ccc(Oc4nccc(C)n4)cc3F)c3c(N)ncnc3n2C)c(C)n1] | A | A |
| 1198 | 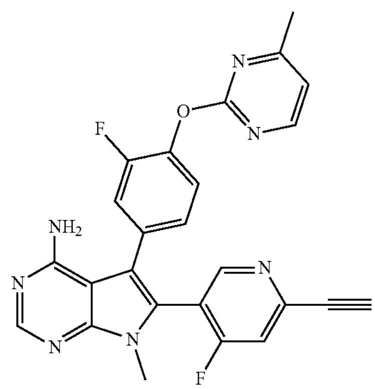 [SMILES: C#Cc1cc(F)c(-c2c(-c3ccc(Oc4nccc(C)n4)c(F)c3)c3c(N)ncnc3n2C)cn1] | A | A |
| 1199 | 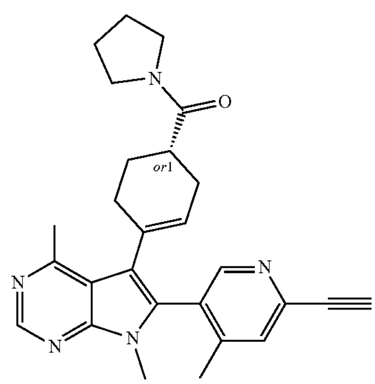 [SMILES: C#Cc1cc(C)c(-c2c(C3=CC[C@@H](C(=O)N4CCCC4)CC3)c3c(C)ncnc3n2C)cn1] | A | A |
| 1200 | 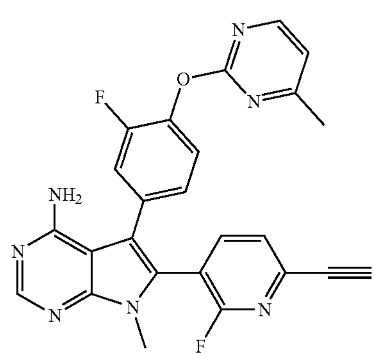 [SMILES: C#Cc1ccc(-c2c(-c3ccc(Oc4nccc(C)n4)c(F)c3)c3c(N)ncnc3n2C)c(F)n1] | D | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1201 | 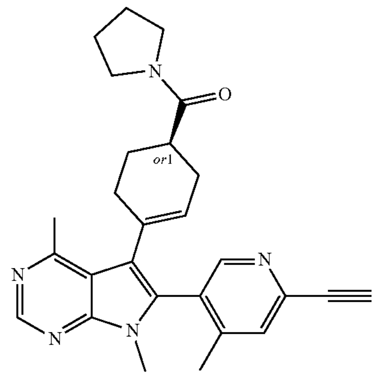 [SMILES: C#Cc1cc(C)c(-c2c(C3=CC[C@H](C(=O)N4CCCC4)CC3)c3c(C)ncnc3n2C)cn1] | A | A |
| 1202 | 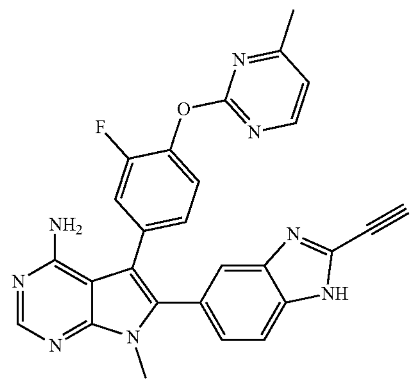 [SMILES: C#Cc1nc2cc(-c3c(-c4ccc(Oc5nccc(C)n5)c(F)c4)c4c(N)ncnc4n3C)ccc2[nH]1] | D | C |
| 1203 | 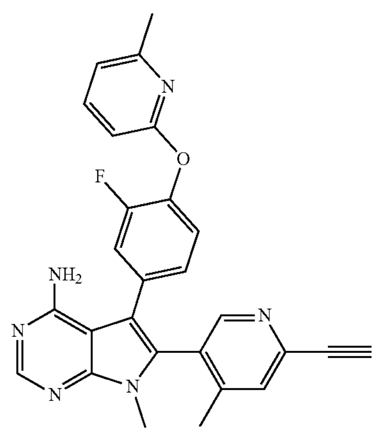 [SMILES: C#Cc1cc(C)c(-c2c(-c3ccc(Oc4cccc(C)n4)c(F)c3)c3c(N)ncnc3n2C)cn1] | A | A |
| 1204 | 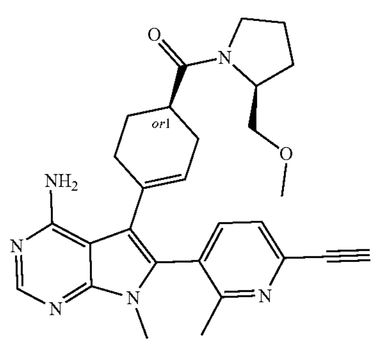 [SMILES: C#Cc1ccc(-c2c(C3=CC[C@H](C(=O)N4CCC[C@H]4COC)CC3)c3c(N)ncnc3n2C)c(C)n1] | A | A |

US 11,780,845 B2

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1205 | 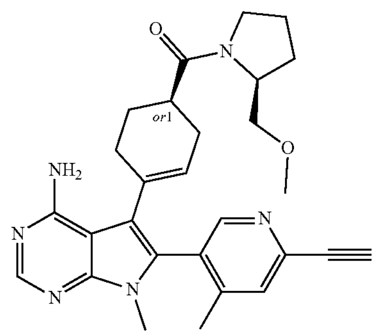 [SMILES: C#Cc1cc(C)c(-c2c(C3=CC[C@H](C(=O)N4CCC[C@H]4COC)CC3)c3c(N)ncnc3n2C)cn1] | C | C |
| 1206 | 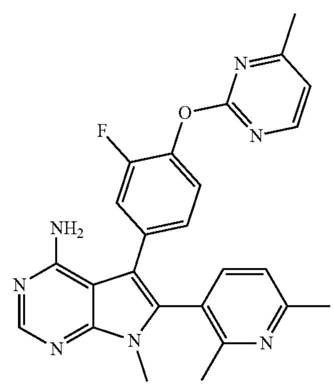 [SMILES: Cc1ccnc(Oc2ccc(-c3c(-c4ccc(C)nc4C)n(C)c4ncnc(N)c34)cc2F)n1] | C | C |
| 1207 | 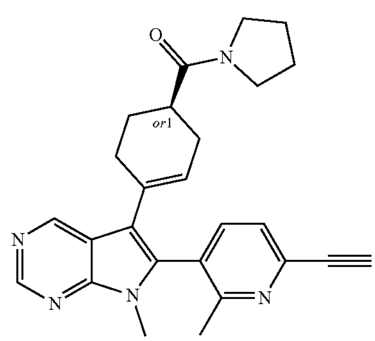 [SMILES: C#Cc1ccc(-c2c(C3=CC[C@H](C(=O)N4CCCC4)CC3)c3cncnc3n2C)c(C)n1] | D | D |
| 1208 | 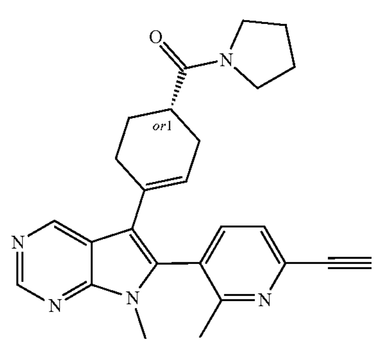 [SMILES: C#Cc1ccc(-c2c(C3=CC[C@@H](C(=O)N4CCCC4)CC3)c3cncnc3n2C)c(C)n1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1209 | 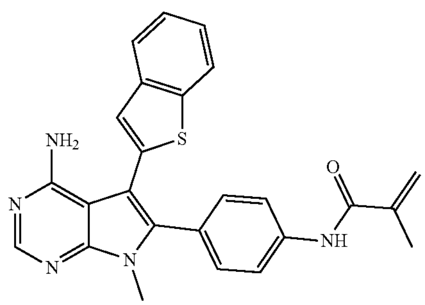 [SMILES: C=C(C)C(=O)Nc1ccc(-c2c(-c3cc4ccccc4s3)c3c(N)ncnc3n2C)cc1] | C | |
| 1210 | 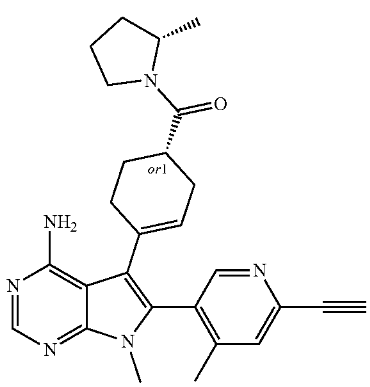 [SMILES: C#Cc1cc(C)c(-c2c(C3=CC[C@@H](C(=O)N4CCC[C@@H]4C)CC3)c3c(N)ncnc3n2C)cn1] | A | A |
| 1211 | 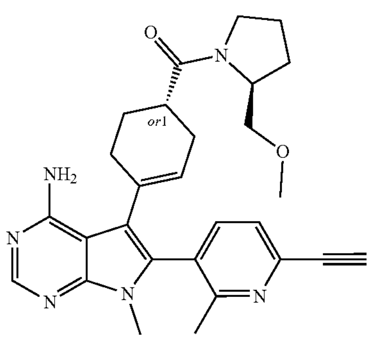 [SMILES: C#Cc1ccc(-c2c(C3=CC[C@@H](C(=O)N4CCC[C@H]4COC)CC3)c3c(N)ncnc3n2C)c(C)n1] | A | B |
| 1212 | 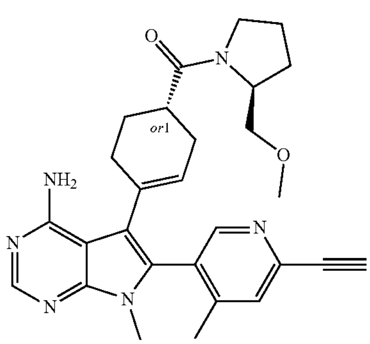 [SMILES: C#Cc1cc(C)c(-c2c(C3=CC[C@@H](C(=O)N4CCC[C@H]4COC)CC3)c3c(N)ncnc3n2C)cn1] | A | B |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1213 | 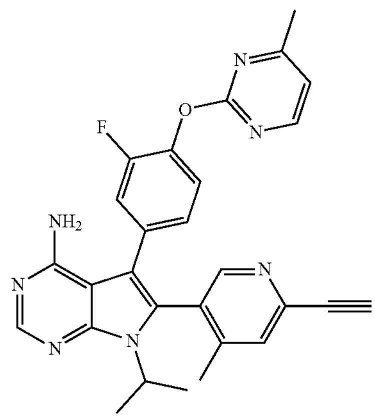 [SMILES: C#Cc1cc(C)c(-c2c(-c3ccc(Oc4nccc(C)n4)c(F)c3)c3c(N)ncnc3n2C(C)C)cn1] | A | A |
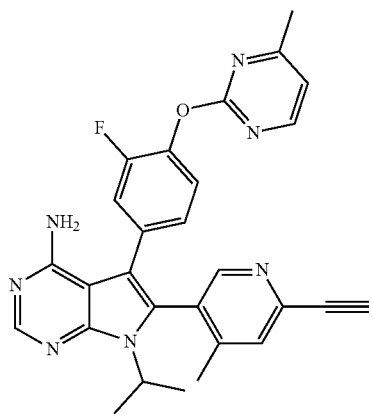
| | | | |
|---|---|---|---|
| 1214 | | A | A |
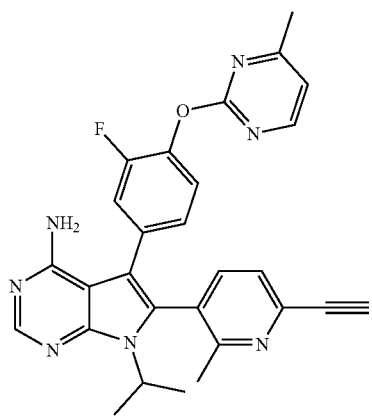 [SMILES: C#Cc1ccc(-c2c(-c3ccc(Oc4nccc(C)n4)c(F)c3)c3c(N)ncnc3n2C(C)C)c(C)n1]
| | | | |
|---|---|---|---|
| 1215 | | A | A |
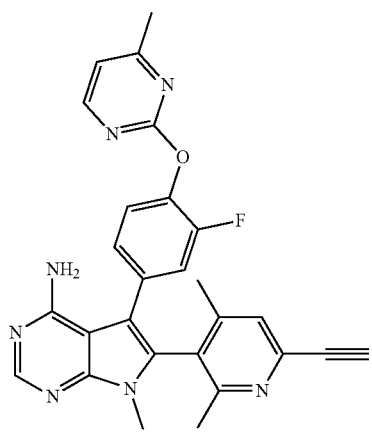 [SMILES: C#Cc1cc(C)c(-c2c(-c3ccc(Oc4nccc(C)n4)c(F)c3)c3c(N)ncnc3n2C)c(C)n1]

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1216 | 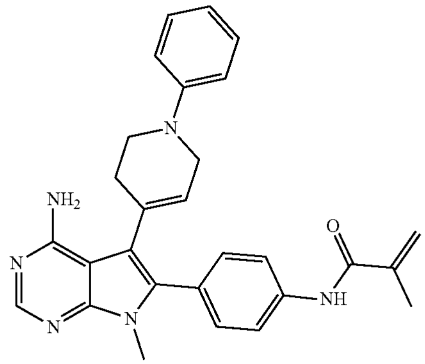 [SMILES: C=C(C)C(=O)Nc1ccc(-c2c(C3=CCN(c4ccccc4)CC3)c3c(N)ncnc3n2C)cc1] | D | |
| 1217 | 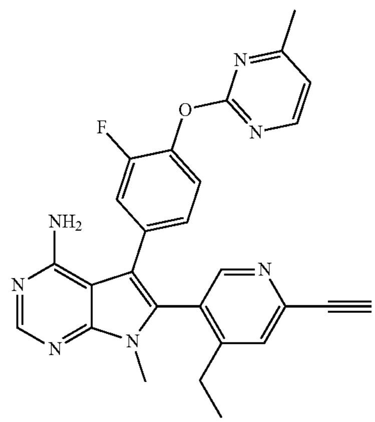 [SMILES: C#Cc1cc(CC)c(-c2c(-c3ccc(Oc4nccc(C)n4)c(F)c3)c3c(N)ncnc3n2C)cn1] | A | A |
| 1218 | 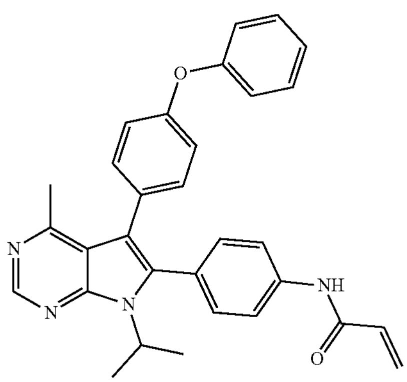 [SMILES: C=CC(=O)Nc1ccc(-c2c(-c3ccc(Oc4ccccc4)cc3)c3c(C)ncnc3n2C(C)C)cc1] | D | |
| 1219 | 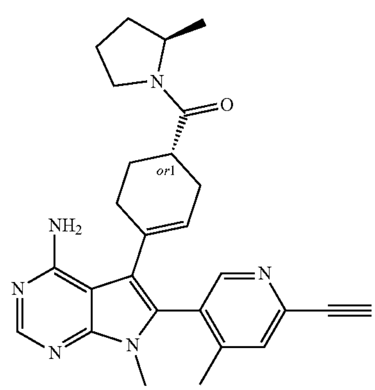 [SMILES: C#Cc1cc(C)c(-c2c(C3=CC[C@@H](C(=O)N4CCC[C@H]4C)CC3)c3c(N)ncnc3n2C)cn1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1220 | 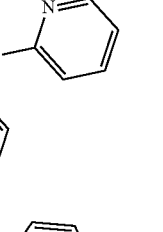 | A | |
| 1221 | 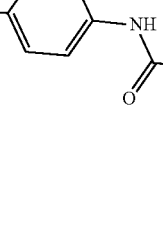 | C | |
| 1222 | 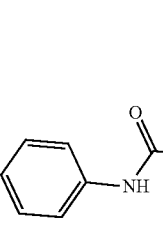 | D | |
| 1223 | 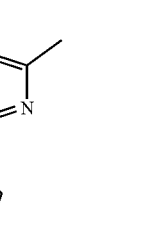 | D | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1224 | 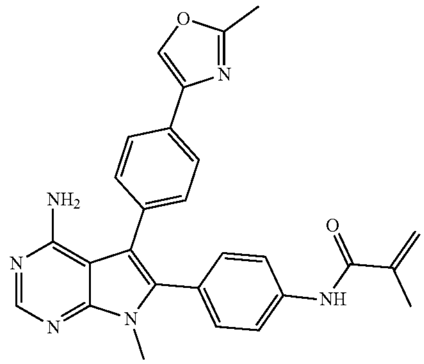 [SMILES: C=C(C)C(=O)Nc1ccc(-c2c(-c3ccc(-c4coc(C)n4)cc3)c3c(N)ncnc3n2C)cc1] | C | |
| 1225 | 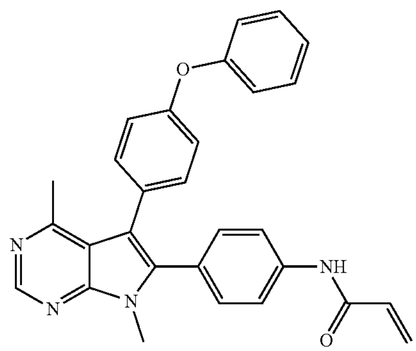 [SMILES: C=CC(=O)Nc1ccc(-c2c(-c3ccc(Oc4ccccc4)cc3)c3c(C)ncnc3n2C)cc1] | C | |
| 1226 | 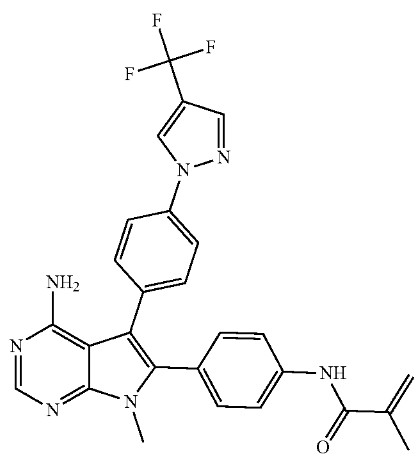 [SMILES: C=C(C)C(=O)Nc1ccc(-c2c(-c3ccc(-n4cc(C(F)(F)F)cn4)cc3)c3c(N)ncnc3n2C)cc1] | D | |
| 1227 | 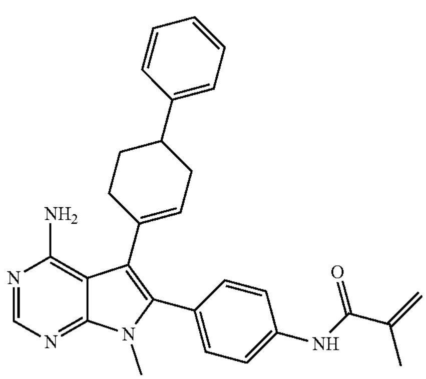 [SMILES: C=C(C)C(=O)Nc1ccc(-c2c(C3=CCC(c4ccccc4)CC3)c3c(N)ncnc3n2C)cc1] | D | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1228 | 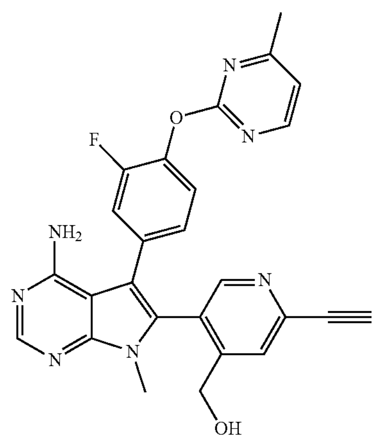 [SMILES: C#Cc1cc(CO)c(-c2c(-c3ccc(Oc4nccc(C)n4)c(F)c3)c3c(N)ncnc3n2C)cn1] | A | A |
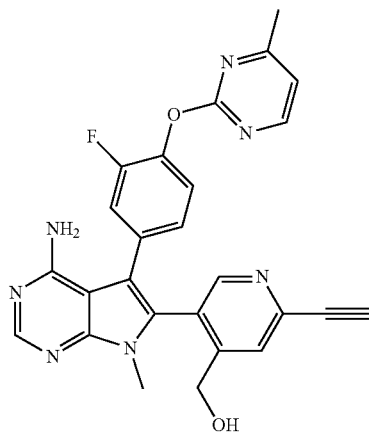
| | | | |
|---|---|---|---|
| 1229 | | A | A |
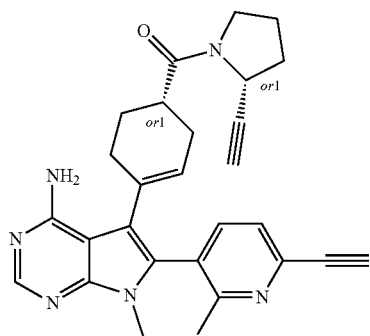 [SMILES: C#Cc1ccc(-c2c(C3=CC[C@@H](C(=O)N4CCC[C@@H]4C#C)CC3)c3c(N)ncnc3n2C)c(C)n1]
| | | | |
|---|---|---|---|
| 1230 | | A | A |
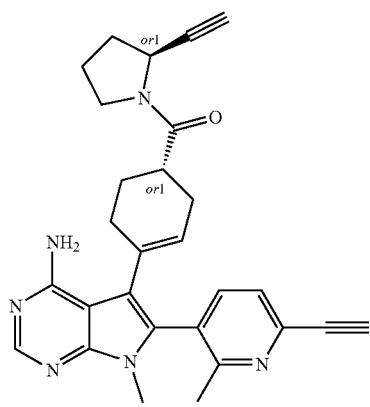 [SMILES: C#Cc1ccc(-c2c(C3=CC[C@@H](C(=O)N4CCC[C@H]4C#C)CC3)c3c(N)ncnc3n2C)c(C)n1]

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1231 | 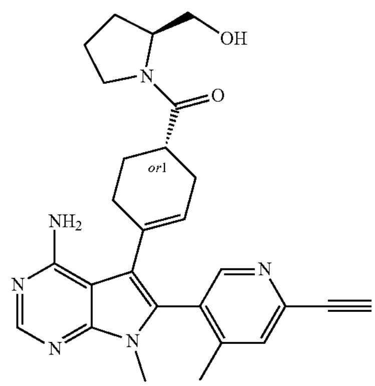 [SMILES: C#Cc1cc(C)c(-c2c(C3=CC[C@@H](C(=O)N4CCC[C@H]4CO)CC3)c3c(N)ncnc3n2C)cn1] | A | A |
| 1232 | 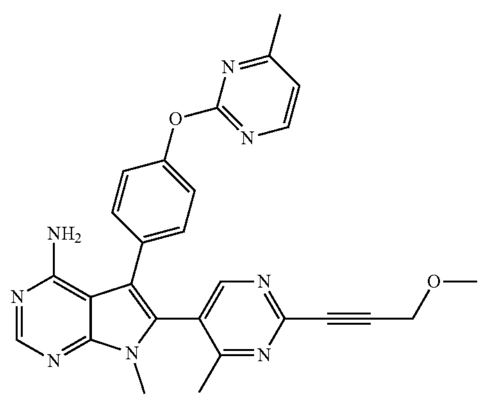 [SMILES: COCC#Cc1ncc(-c2c(-c3ccc(Oc4nccc(C)n4)cc3)c3c(N)ncnc3n2C)c(C)n1] | A | A |
| 1233 | 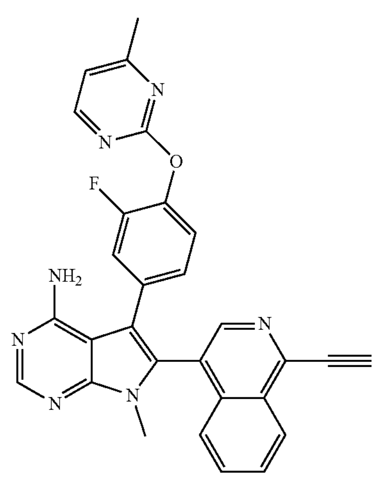 [SMILES: C#Cc1ncc(-c2c(-c3ccc(Oc4nccc(C)n4)c(F)c3)c3c(N)ncnc3n2C)c2ccccc12] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1234 | 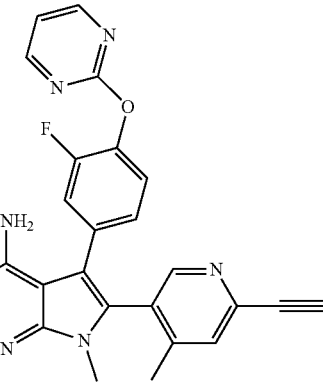 | A | A |
| 1235 | 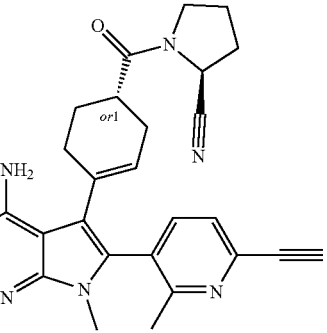 | A | A |
| 1236 | 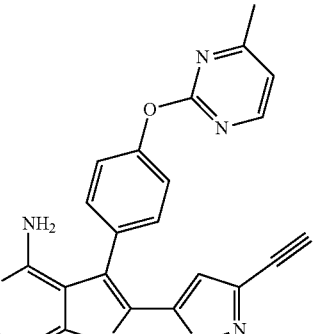 | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1237 | 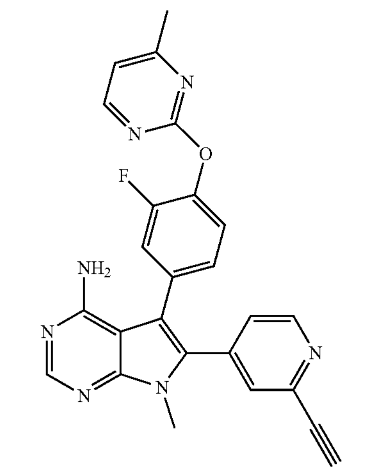 [SMILES: C#Cc1cc(-c2c(-c3ccc(Oc4nccc(C)n4)c(F)c3)c3c(N)ncnc3n2C)ccn1] | C | A |
| 1238 | 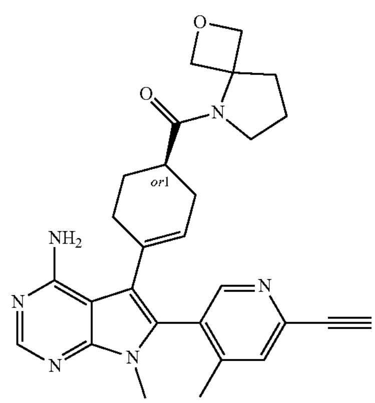 [SMILES: C#Cc1cc(C)c(-c2c(C3=CC[C@H](C(=O)N4CCCC45COC5)CC3)c3c(N)ncnc3n2C)cn1] | C | B |
| 1239 | 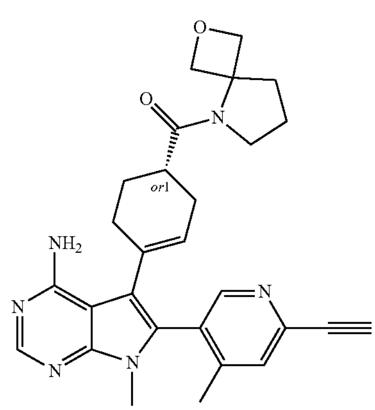 [SMILES: C#Cc1cc(C)c(-c2c(C3=CC[C@@H](C(=O)N4CCCC45COC5)CC3)c3c(N)ncnc3n2C)cn1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1240 | 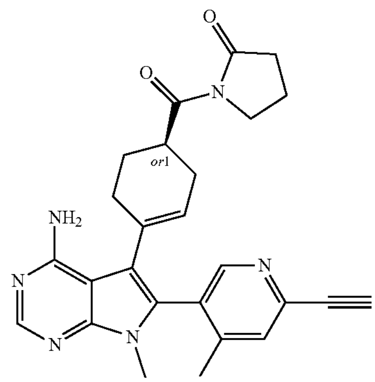 [SMILES: C#Cc1cc(C)c(-c2c(C3=CC[C@H](C(=O)N4CCCC4=O)CC3)c3c(N)ncnc3n2C)cn1] | B | B |
| 1241 | 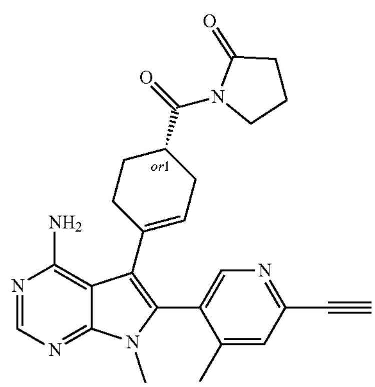 [SMILES: C#Cc1cc(C)c(-c2c(C3=CC[C@@H](C(=O)N4CCCC4=O)CC3)c3c(N)ncnc3n2C)cn1] | A | A |
| 1242 | 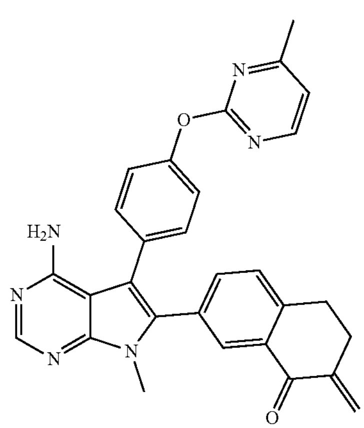 [SMILES: C=C1CCc2ccc(-c3c(-c4ccc(Oc5nccc(C)n5)cc4)c4c(N)ncnc4n3C)cc2C1=O] | B | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1243 | 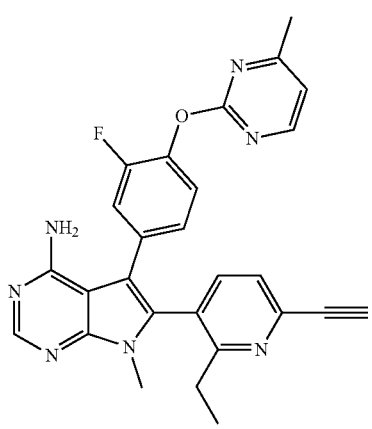 [SMILES: C#Cc1ccc(-c2c(-c3ccc(Oc4nccc(C)n4)c(F)c3)c3c(N)ncnc3n2C)c(CC)n1] | A | A |
| 1244 | 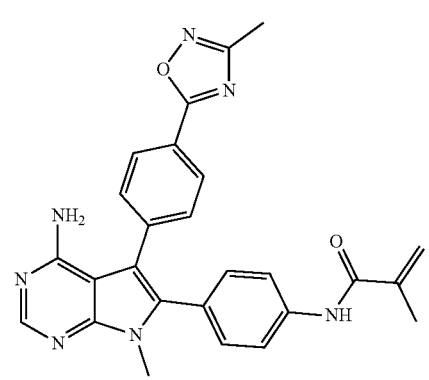 [SMILES: C=C(C)C(=O)Nc1ccc(-c2c(-c3ccc(-c4nc(C)no4)cc3)c3c(N)ncnc3n2C)cc1] | D | |
| 1245 | 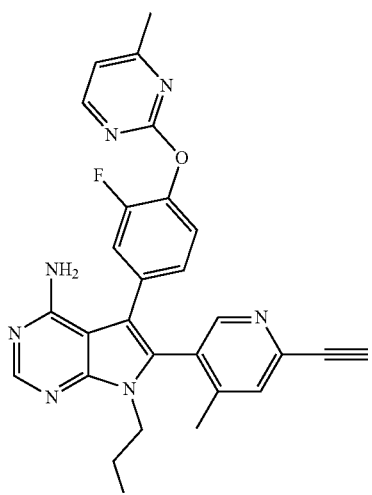 | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1246 | 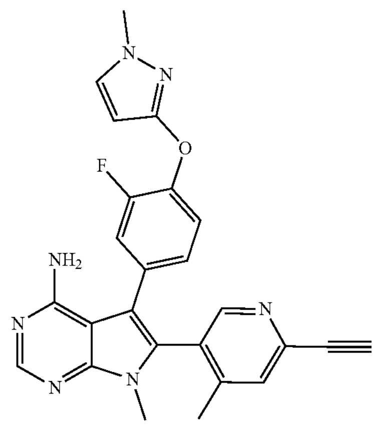 [SMILES: C#Cc1cc(C)c(-c2c(-c3ccc(Oc4ccn(C)n4)c(F)c3)c3c(N)ncnc3n2C)cn1] | A | A |
| 1247 | 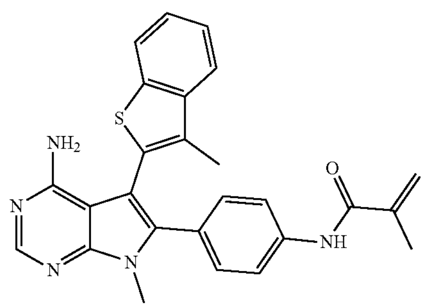 [SMILES: C=C(C)C(=O)Nc1ccc(-c2c(-c3sc4ccccc4c3C)c3c(N)ncnc3n2C)cc1] | D | |
| 1248 | 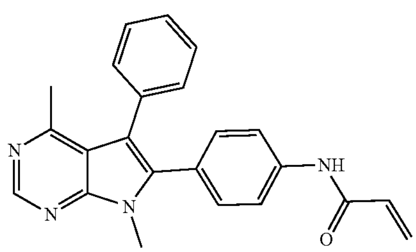 [SMILES: C=CC(=O)Nc1ccc(-c2c(-c3ccccc3)c3c(C)ncnc3n2C)cc1] | D | |
| 1249 | 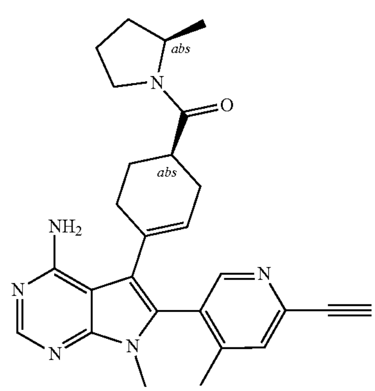 [SMILES: C#Cc1cc(C)c(-c2c(C3=CC[C@H](C(=O)N4CCC[C@H]4C)CC3)c3c(N)ncnc3n2C)cn1] | C | B |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1250 | 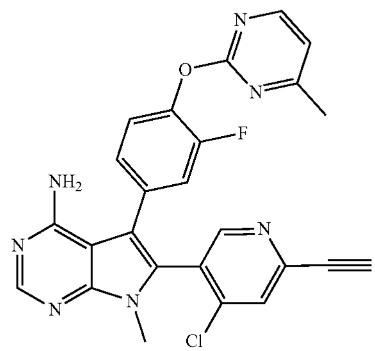 [SMILES: C#Cc1cc(Cl)c(-c2c(-c3ccc(Oc4nccc(C)n4)c(F)c3)c3c(N)ncnc3n2C)cn1] | A | A |
| 1251 | 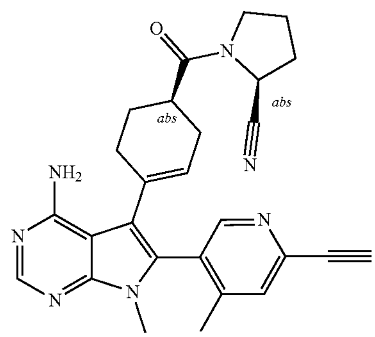 [SMILES: C#Cc1cc(C)c(-c2c(C3=CC[C@H](C(=O)N4CCC[C@H]4C#N)CC3)c3c(N)ncnc3n2C)cn1] | A | A |
| 1252 | 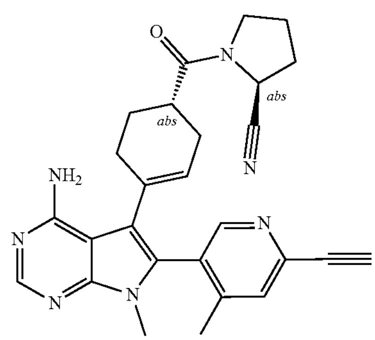 [SMILES: C#Cc1cc(C)c(-c2c(C3=CC[C@@H](C(=O)N4CCC[C@H]4C#N)CC3)c3c(N)ncnc3n2C)cn1] | A | A |
| 1253 | 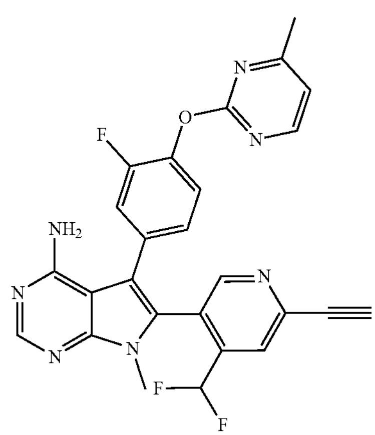 [SMILES: C#Cc1cc(C(F)F)c(-c2c(-c3ccc(Oc4nccc(C)n4)c(F)c3)c3c(N)ncnc3n2C)cn1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1254 | 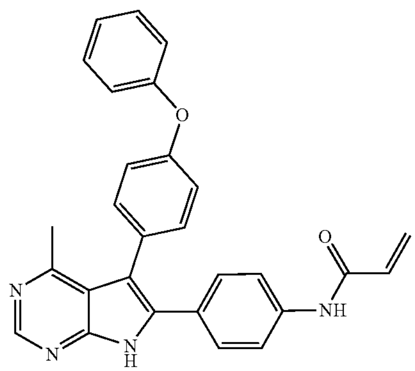 [SMILES: C=CC(=O)Nc1ccc(-c2[nH]c3ncnc(C)c3c2-c2ccc(Oc3ccccc3)cc2)cc1] | D | |
| 1255 | 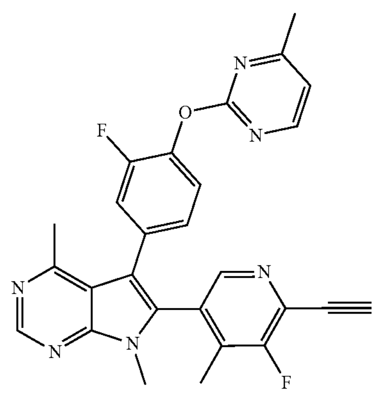 [SMILES: C#Cc1ncc(-c2c(-c3ccc(Oc4nccc(C)n4)c(F)c3)c3c(C)ncnc3n2C)c(C)c1F] | A | A |
| 1256 | 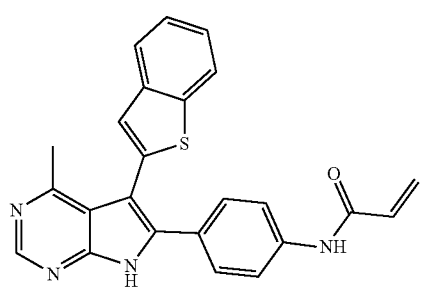 [SMILES: C=CC(=O)Nc1ccc(-c2[nH]c3ncnc(C)c3c2-c2cc3ccccc3s2)cc1] | D | |
| 1257 | 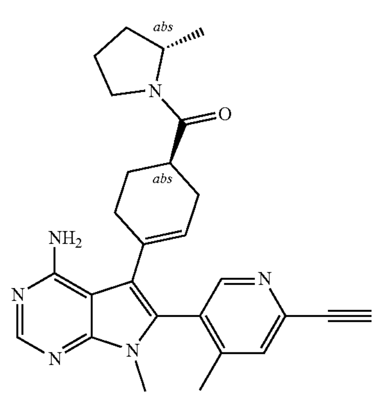 [SMILES: C#Cc1cc(C)c(-c2c(C3=CC[C@H](C(=O)N4CCC[C@@H]4C)CC3)c3c(N)ncnc3n2C)cn1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1258 | 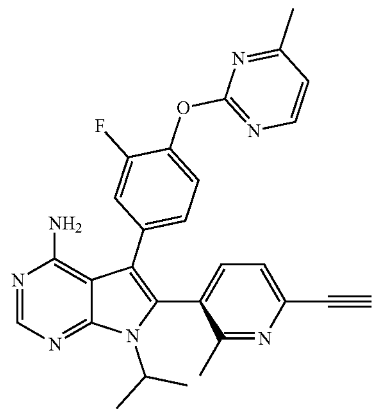 | A | A |
| 1259 | 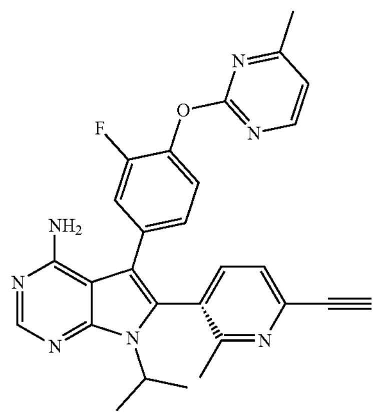 | A | A |
| 1260 | 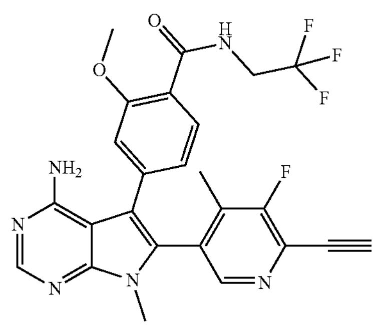 [SMILES: C#Cc1ncc(-c2c(-c3ccc(C(=O)NCC(F)(F)F)c(OC)c3)c3c(N)ncnc3n2C)c(C)c1F] | A | A |
| 1261 | 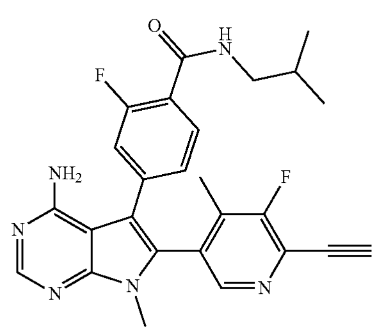 [SMILES: C#Cc1ncc(-c2c(-c3ccc(C(=O)NCC(C)C)c(F)c3)c3c(N)ncnc3n2C)c(C)c1F] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1262 | 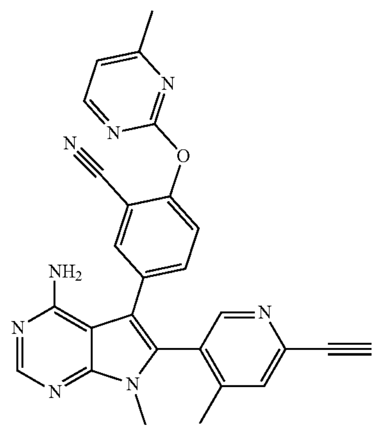 [SMILES: C#Cc1cc(C)c(-c2c(-c3ccc(Oc4nccc(C)n4)c(C#N)c3)c3c(N)ncnc3n2C)cn1] | A | A |
| 1263 | 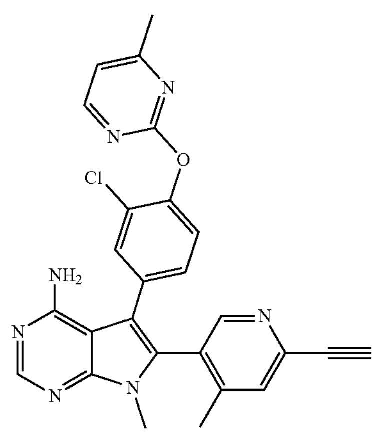 [SMILES: C#Cc1cc(C)c(-c2c(-c3ccc(Oc4nccc(C)n4)c(Cl)c3)c3c(N)ncnc3n2C)cn1] | A | A |
| 1264 | 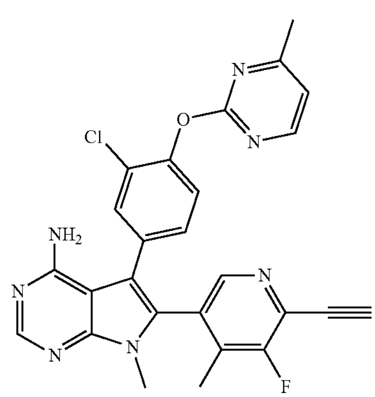 [SMILES: C#Cc1ncc(-c2c(-c3ccc(Oc4nccc(C)n4)c(Cl)c3)c3c(N)ncnc3n2C)c(C)c1F] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1265 | 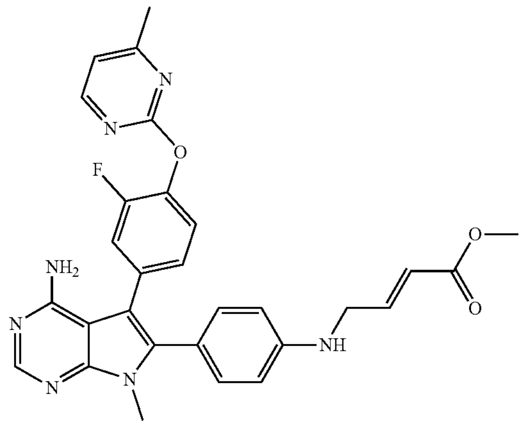 [SMILES: COC(=O)/C=C/CNc1ccc(-c2c(-c3ccc(Oc4nccc(C)n4)c(F)c3)c3c(N)ncnc3n2C)cc1] | A | B |
| 1266 | 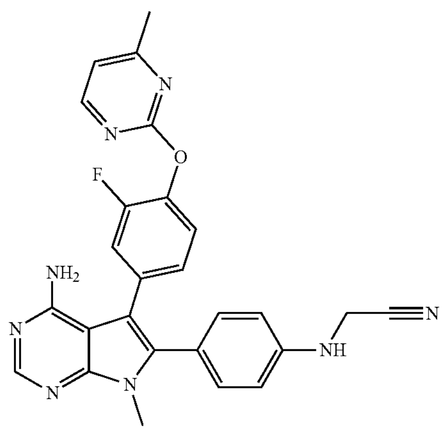 [SMILES: Cc1ccnc(Oc2ccc(-c3c(-c4ccc(NCC#N)cc4)n(C)c4ncnc(N)c34)cc2F)n1] | D | C |
| 1267 | 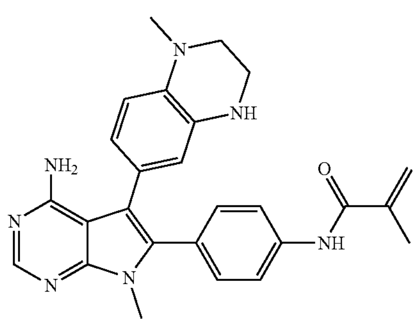 [SMILES: C=C(C)C(=O)Nc1ccc(-c2c(-c3ccc4c(c3)NCCN4C)c3c(N)ncnc3n2C)cc1] | D | D |
| 1268 | 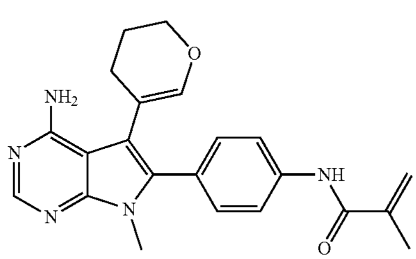 [SMILES: C=C(C)C(=O)Nc1ccc(-c2c(C3=COCCC3)c3c(N)ncnc3n2C)cc1] | D | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1269 | 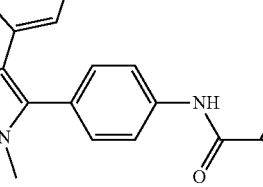 | D | D |
| 1270 | 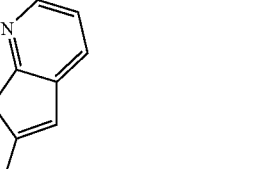 | C | C |
| 1271 | 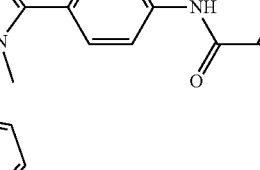 | D | D |
| 1272 | 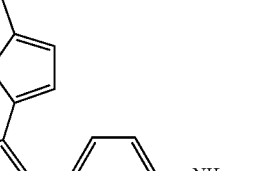 | D | D |
| 1273 | 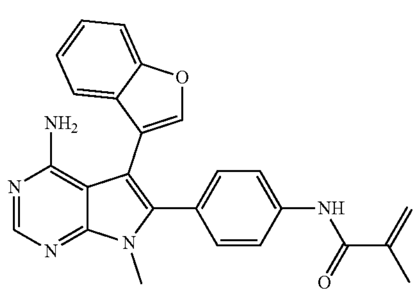 [SMILES: C=C(C)C(=O)Nc1ccc(-c2c(-c3coc4ccccc34)c3c(N)ncnc3n2C)cc1] | D | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1274 | 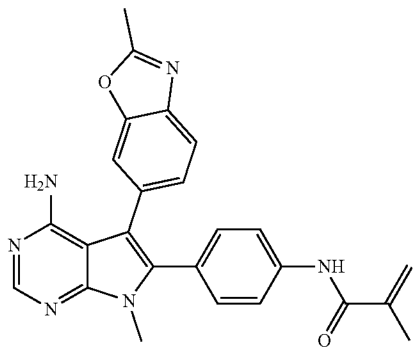 [SMILES: C=C(C)C(=O)Nc1ccc(-c2c(-c3ccc4nc(C)oc4c3)c3c(N)ncnc3n2C)cc1] | D | D |
| 1275 | 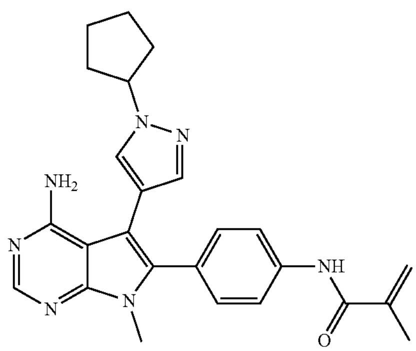 [SMILES: C=C(C)C(=O)Nc1ccc(-c2c(-c3cnn(C4CCCC4)c3)c3c(N)ncnc3n2C)cc1] | C | C |
| 1276 | 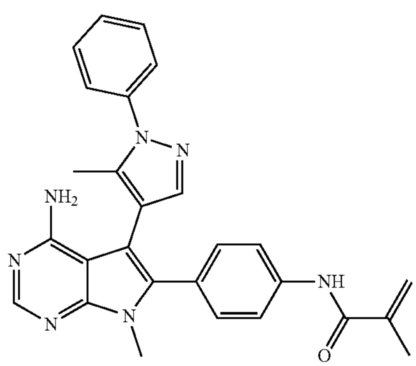 | D | D |
| 1277 | 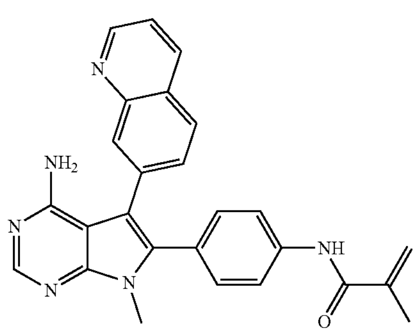 [SMILES: C=C(C)C(=O)Nc1ccc(-c2c(-c3ccc4cccnc4c3)c3c(N)ncnc3n2C)cc1] | C | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1278 | 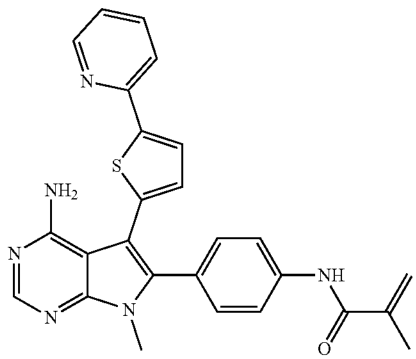 [SMILES: C=C(C)C(=O)Nc1ccc(-c2c(-c3ccc(-c4ccccn4)s3)c3c(N)ncnc3n2C)cc1] | C | C |
| 1279 | 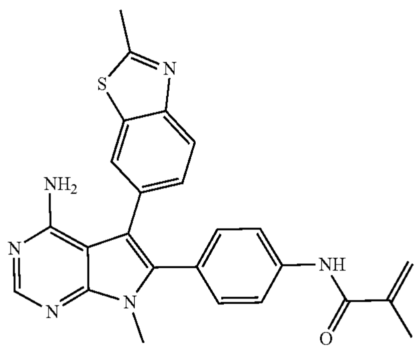 [SMILES: C=C(C)C(=O)Nc1ccc(-c2c(-c3ccc4nc(C)sc4c3)c3c(N)ncnc3n2C)cc1] | C | C |
| 1280 | 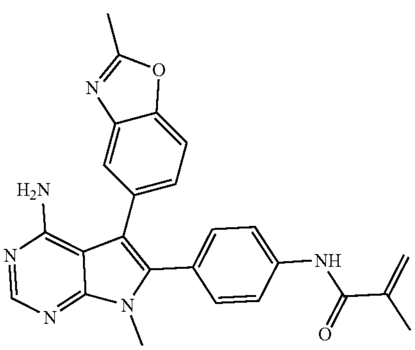 [SMILES: C=C(C)C(=O)Nc1ccc(-c2c(-c3ccc4oc(C)nc4c3)c3c(N)ncnc3n2C)cc1] | C | C |
| 1281 | 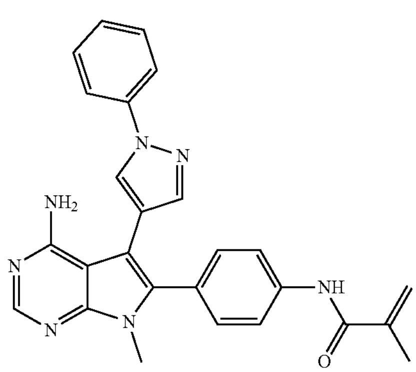 [SMILES: C=C(C)C(=O)Nc1ccc(-c2c(-c3cnn(-c4ccccc4)c3)c3c(N)ncnc3n2C)cc1] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1282 | 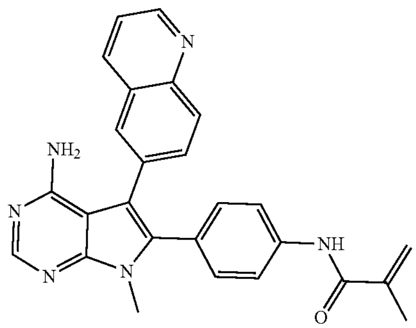 [SMILES: C=C(C)C(=O)Nc1ccc(-c2c(-c3ccc4ncccc4c3)c3c(N)ncnc3n2C)cc1] | D | D |
| 1283 | 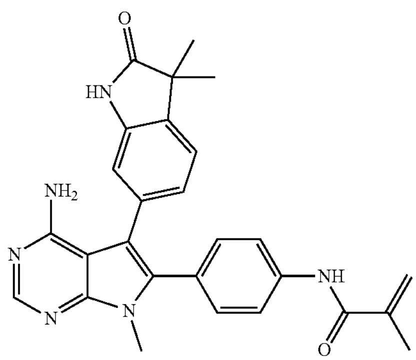 [SMILES: C=C(C)C(=O)Nc1ccc(-c2c(-c3ccc4c(c3)NC(=O)C4(C)C)c3c(N)ncnc3n2C)cc1] | D | D |
| 1284 | 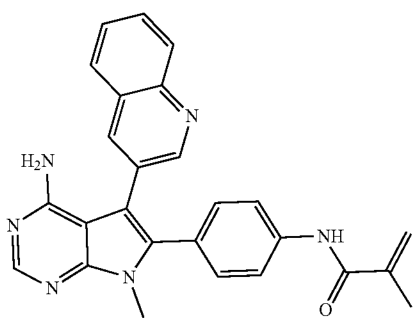 [SMILES: C=C(C)C(=O)Nc1ccc(-c2c(-c3cnc4ccccc4c3)c3c(N)ncnc3n2C)cc1] | D | D |
| 1285 | 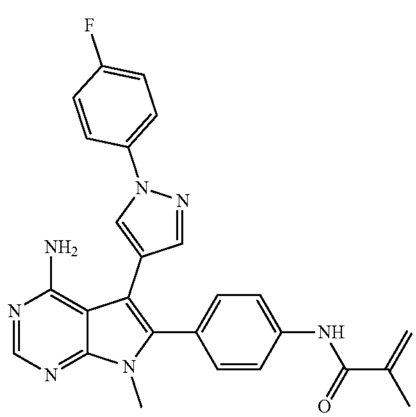 [SMILES: C=C(C)C(=O)Nc1ccc(-c2c(-c3cnn(-c4ccc(F)cc4)c3)c3c(N)ncnc3n2C)cc1] | C | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1286 | 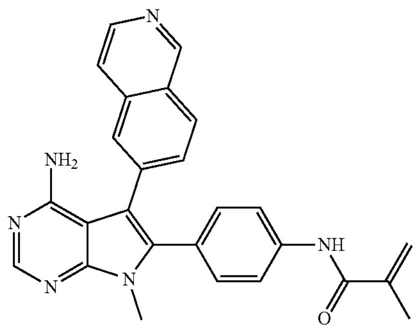 [SMILES: C=C(C)C(=O)Nc1ccc(-c2c(-c3ccc4cnccc4c3)c3c(N)ncnc3n2C)cc1] | C | C |
| 1287 | 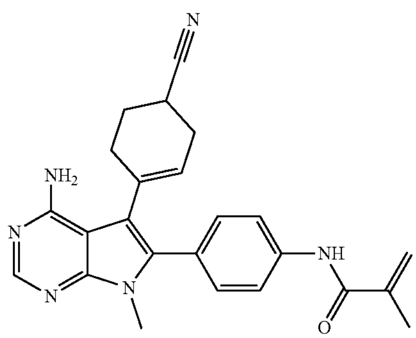 [SMILES: C=C(C)C(=O)Nc1ccc(-c2c(C3=CCC(C#N)CC3)c3c(N)ncnc3n2C)cc1] | D | D |
| 1288 | 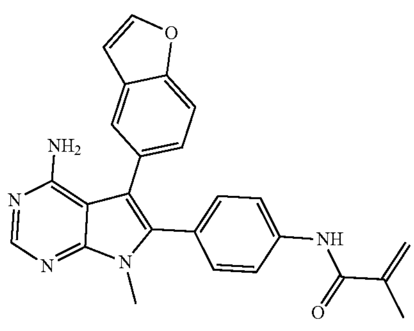 [SMILES: C=C(C)C(=O)Nc1ccc(-c2c(-c3ccc4occc4c3)c3c(N)ncnc3n2C)cc1] | D | D |
| 1289 | 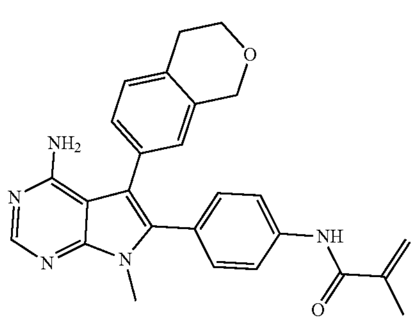 [SMILES: C=C(C)C(=O)Nc1ccc(-c2c(-c3ccc4c(c3)COCC4)c3c(N)ncnc3n2C)cc1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1290 | 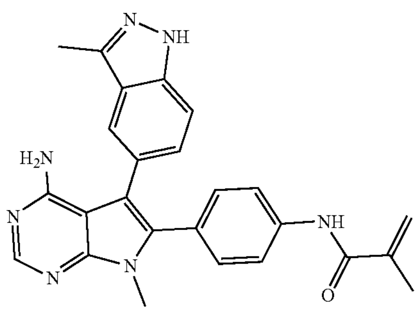 [SMILES: C=C(C)C(=O)Nc1ccc(-c2c(-c3ccc4[nH]nc(C)c4c3)c3c(N)ncnc3n2C)cc1] | D | D |
| 1291 | 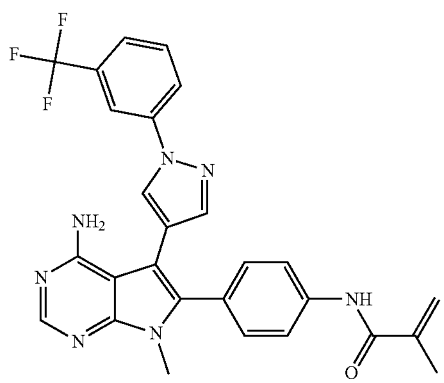 [SMILES: C=C(C)C(=O)Nc1ccc(-c2c(-c3cnn(-c4cccc(C(F)(F)F)c4)c3)c3c(N)ncnc3n2C)cc1] | D | D |
| 1292 | 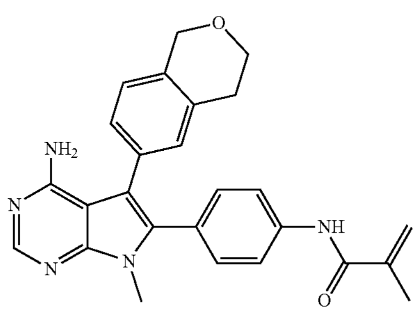 [SMILES: C=C(C)C(=O)Nc1ccc(-c2c(-c3ccc4c(c3)CCOC4)c3c(N)ncnc3n2C)cc1] | D | D |
| 1293 | 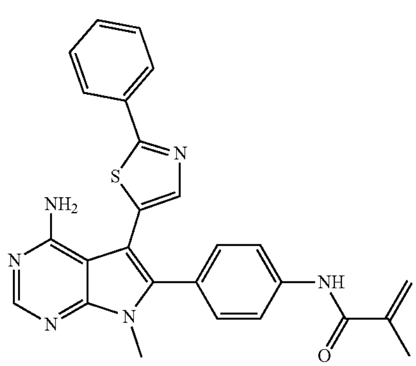 [SMILES: C=C(C)C(=O)Nc1ccc(-c2c(-c3cnc(-c4ccccc4)s3)c3c(N)ncnc3n2C)cc1] | B | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1294 | 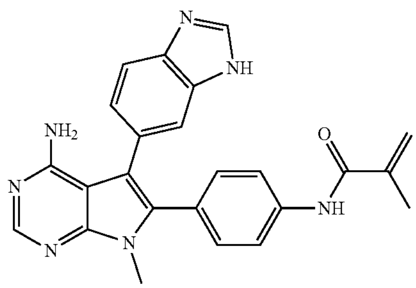 [SMILES: C=C(C)C(=O)Nc1ccc(-c2c(-c3ccc4nc[nH]c4c3)c3c(N)ncnc3n2C)cc1] | C | D |
| 1295 | 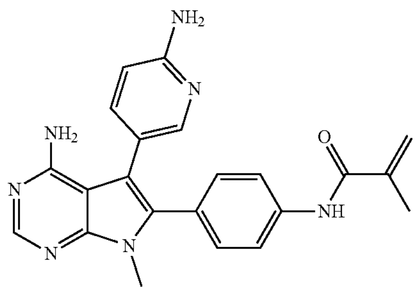 [SMILES: C=C(C)C(=O)Nc1ccc(-c2c(-c3ccc(N)nc3)c3c(N)ncnc3n2C)cc1] | D | D |
| 1296 | 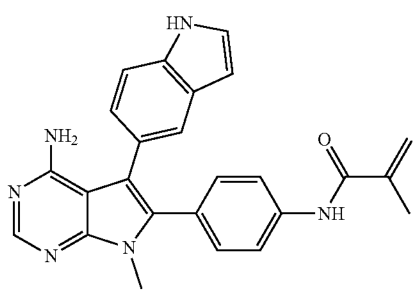 [SMILES: C=C(C)C(=O)Nc1ccc(-c2c(-c3ccc4[nH]ccc4c3)c3c(N)ncnc3n2C)cc1] | B | C |
| 1297 | 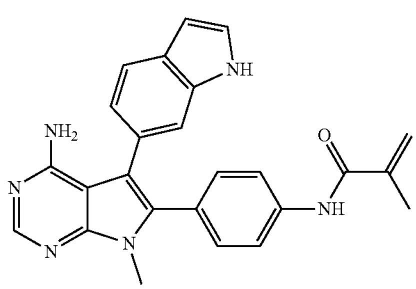 [SMILES: C=C(C)C(=O)Nc1ccc(-c2c(-c3ccc4cc[nH]c4c3)c3c(N)ncnc3n2C)cc1] | C | C |
| 1298 | 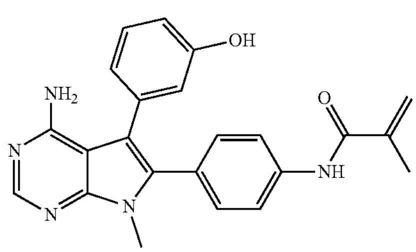 [SMILES: C=C(C)C(=O)Nc1ccc(-c2c(-c3cccc(O)c3)c3c(N)ncnc3n2C)cc1] | C | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1299 | 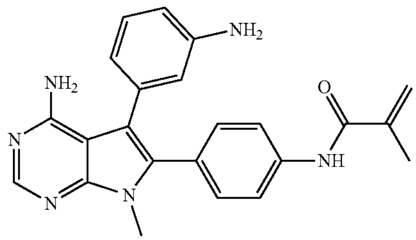 [SMILES: C=C(C)C(=O)Nc1ccc(-c2c(-c3cccc(N)c3)c3c(N)ncnc3n2C)cc1] | D | D |
| 1300 | 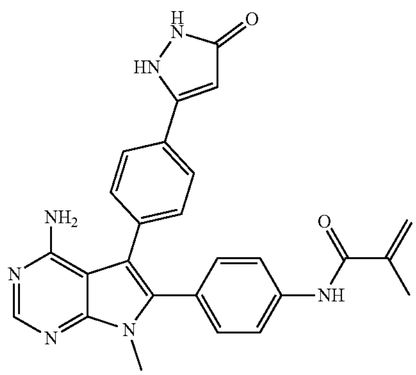 [SMILES: C=C(C)C(=O)Nc1ccc(-c2c(-c3ccc(-c4cc(=O)[nH][nH]4)cc3)c3c(N)ncnc3n2C)cc1] | D | D |
| 1301 | 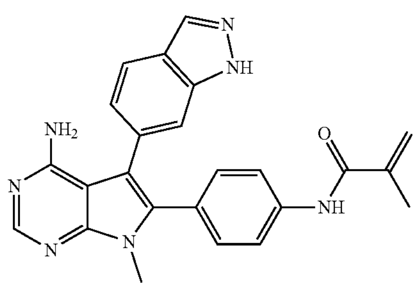 [SMILES: C=C(C)C(=O)Nc1ccc(-c2c(-c3ccc4cn[nH]c4c3)c3c(N)ncnc3n2C)cc1] | D | D |
| 1302 | 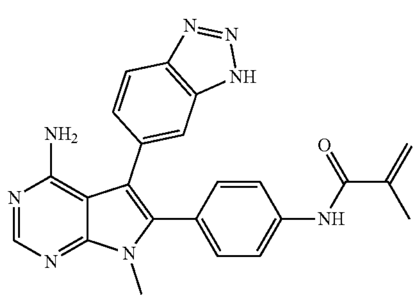 [SMILES: C=C(C)C(=O)Nc1ccc(-c2c(-c3ccc4nn[nH]c4c3)c3c(N)ncnc3n2C)cc1] | D | D |

| Example | Structure | Biochemical FGFR2 Caliper IC50 | Cell SNU-16 IC50 |
|---|---|---|---|
| 1303 | 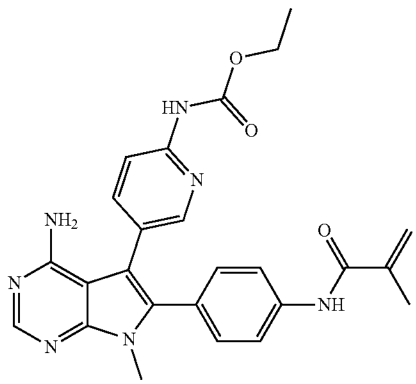 [SMILES: C=C(C)C(=O)Nc1ccc(-c2c(-c3ccc(NC(=O)OCC)nc3)c3c(N)ncnc3n2C)cc1] | D | D |
| 1304 | 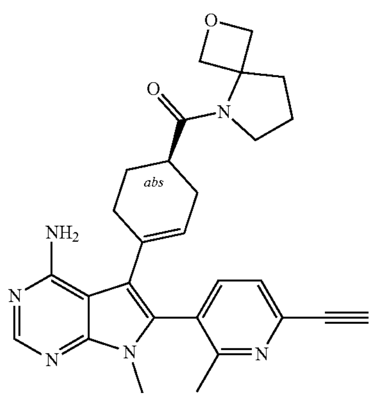 [SMILES: C#Cc1ccc(-c2c(C3=CC[C@H](C(=O)N4CCCC45COC5)CC3)c3c(N)ncnc3n2C)c(C)n1] | C | C |
| 1305 | 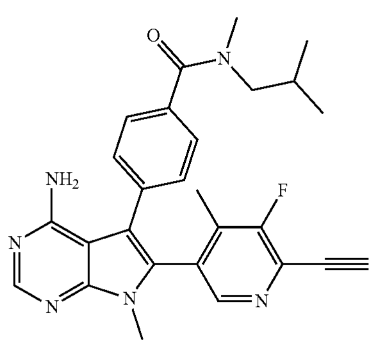 [SMILES: C#Cc1ncc(-c2c(-c3ccc(C(=O)N(C)CC(C)C)cc3)c3c(N)ncnc3n2C)c(C)c1F] | A | A |
| 1306 | 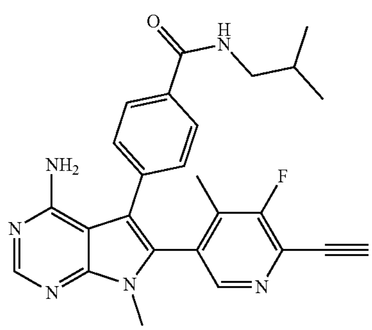 [SMILES: C#Cc1ncc(-c2c(-c3ccc(C(=O)NCC(C)C)cc3)c3c(N)ncnc3n2C)c(C)c1F] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1307 | 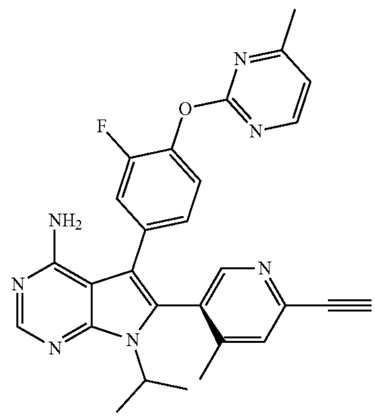 | A | A |
| 1308 | 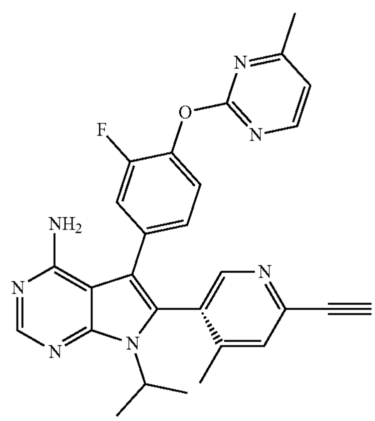 | A | A |
| 1309 | 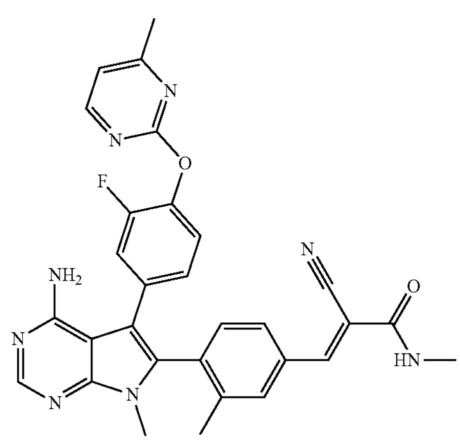 [SMILES: CNC(=O)/C(C#N)=C/c1ccc(-c2c(-c3ccc(Oc4nccc(C)n4)c(F)c3)c3c(N)ncnc3n2C)c(C)c1] | A | C |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 1310 | 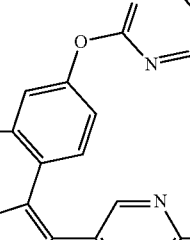 | A | A |
| 1311 | 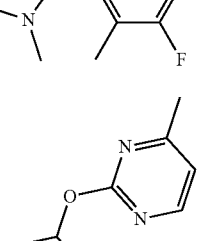 | A | C |
| 1312 | 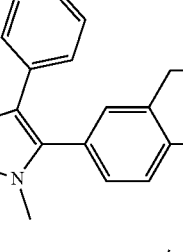 | C | B |
| 1313 | 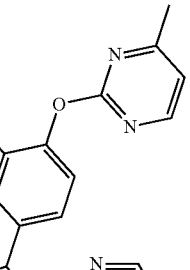 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1314 | 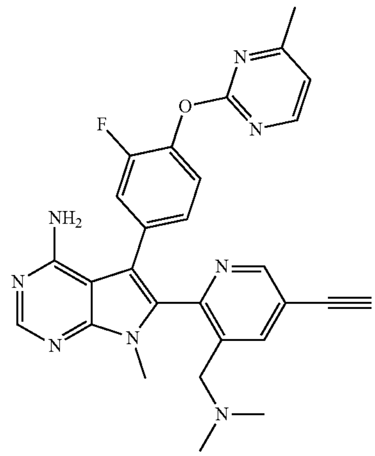 [SMILES: C#Cc1cnc(-c2c(-c3ccc(Oc4nccc(C)n4)c(F)c3)c3c(N)ncnc3n2C)c(CN(C)C)c1] | B | A |
| 1315 | 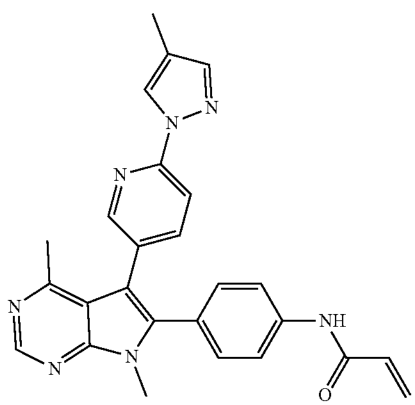 [SMILES: C=CC(=O)Nc1ccc(-c2c(-c3ccc(-n4cc(C)cn4)nc3)c3c(C)ncnc3n2C)cc1] | B | C |
| 1316 | 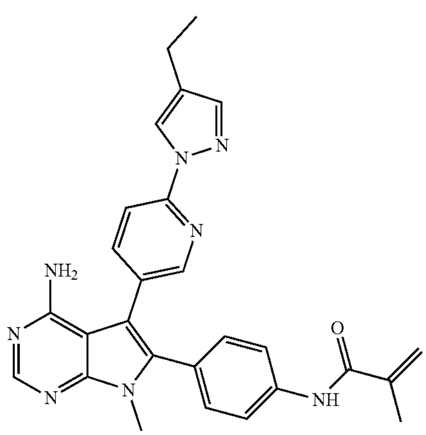 [SMILES: C=C(C)C(=O)Nc1ccc(-c2c(-c3ccc(-n4cc(CC)cn4)nc3)c3c(N)ncnc3n2C)cc1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1317 | 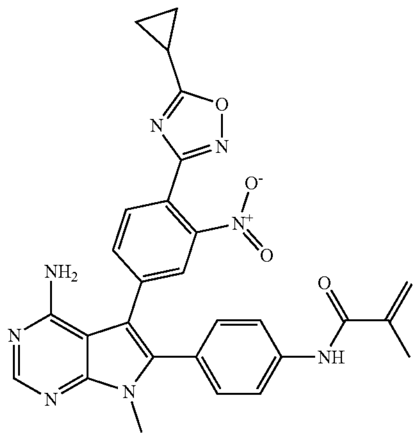 [SMILES: C=C(C)C(=O)Nc1ccc(-c2c(-c3ccc(-c4noc(C5CC5)n4)c([N+](=O)[O-])c3)c3c(N)ncnc3n2C)cc1] | D | |
| 1318 | 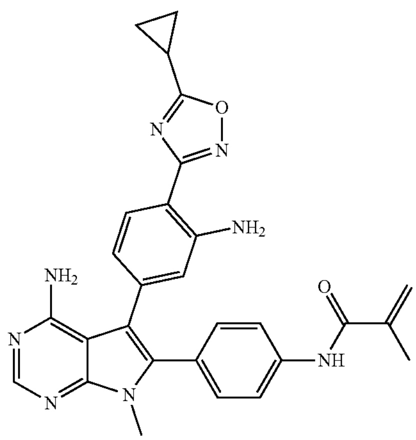 [SMILES: C=C(C)C(=O)Nc1ccc(-c2c(-c3ccc(-c4noc(C5CC5)n4)c(N)c3)c3c(N)ncnc3n2C)cc1] | D | |
| 1319 | 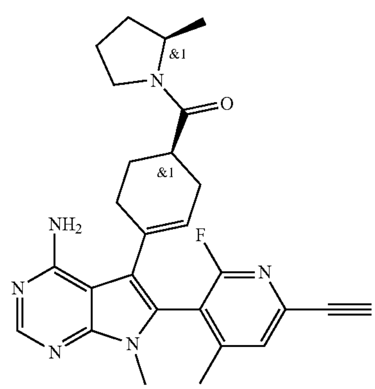 [SMILES: C#Cc1cc(C)c(-c2c(C3=CC[C@H](C(=O)N4CCC[C@H]4C)CC3)c3c(N)ncnc3n2C)c(F)n1] | A | A |

TABLE 1-continued
Representative Compounds of the Invention with Bioactivity Data.
| Example | Structure | Biochemical FGFR2 Caliper IC50 | Cell SNU-16 IC50 |
|---------|-----------|--------------------------------|------------------|
| 1320 | 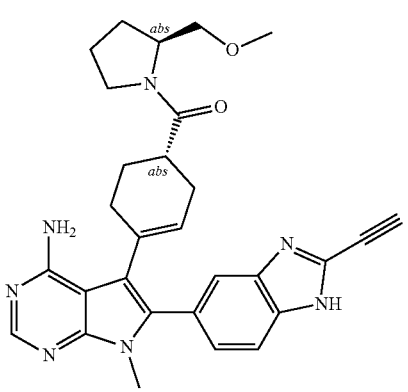 | A | C |
| 1321 | 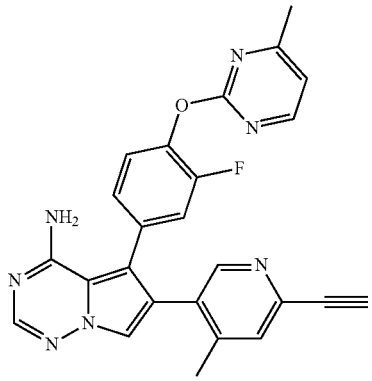 [SMILES: C#Cc1cc(C)c(-c2cn3ncnc(N)c3c2-c2ccc(Oc3nccc(C)n3)c(F)c2)cn1] | A | A |
| 1322 | 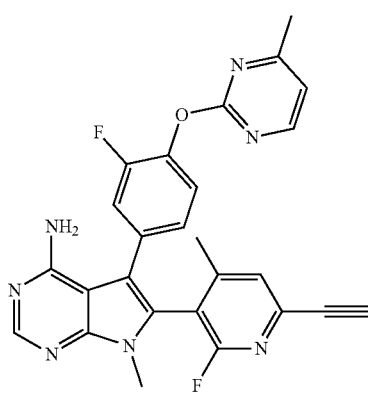 [SMILES: C#Cc1cc(C)c(-c2c(-c3ccc(Oc4nccc(C)n4)c(F)c3)c3c(N)ncnc3n2C)c(F)n1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1323 | 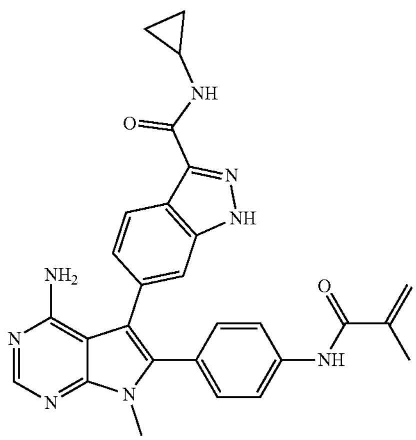 [SMILES: C=C(C)C(=O)Nc1ccc(-c2c(-c3ccc4c(C(=O)NC5CC5)n[nH]c4c3)c3c(N)ncnc3n2C)cc1] | D | D |
| 1324 | 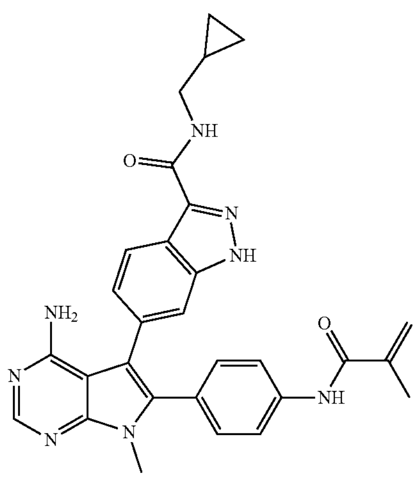 [SMILES: C=C(C)C(=O)Nc1ccc(-c2c(-c3ccc4c(C(=O)NCC5CC5)n[nH]c4c3)c3c(N)ncnc3n2C)cc1] | D | D |
| 1325 | 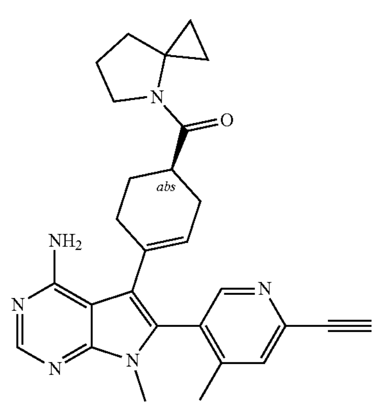 [SMILES: C#Cc1cc(C)c(-c2c(C3=CC[C@H](C(=O)N4CCCC45CC5)CC3)c3c(N)ncnc3n2C)cn1] | C | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1326 | 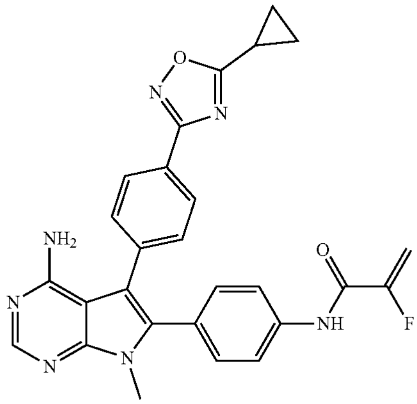 [SMILES: C=C(F)C(=O)Nc1ccc(-c2c(-c3ccc(-c4noc(C5CC5)n4)cc3)c3c(N)ncnc3n2C)cc1] | B | |
| 1327 | 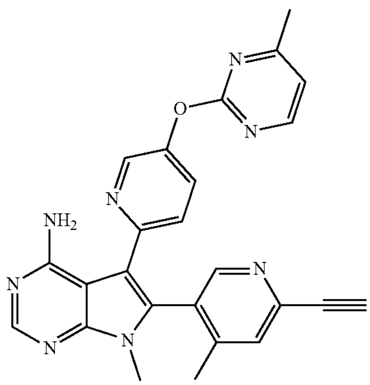 | A | A |
| 1328 | 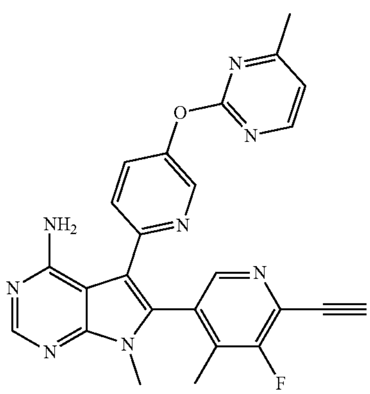 [SMILES: C#Cc1ncc(-c2c(-c3ccc(Oc4nccc(C)n4)cn3)c3c(N)ncnc3n2C)c(C)c1F] | A | A |
| 1329 | 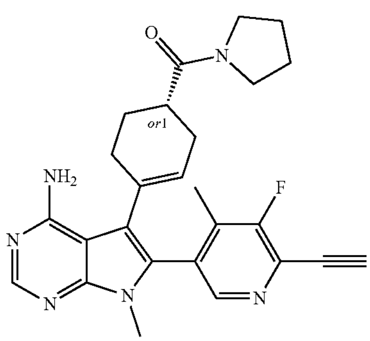 [SMILES: C#Cc1ncc(-c2c(C3=CC[C@@H](C(=O)N4CCCC4)CC3)c3c(N)ncnc3n2C)c(C)c1F] | C | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1330 | 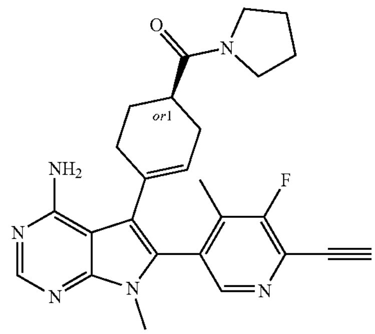 [SMILES: C#Cc1ncc(-c2c(C3=CC[C@H](C(=O)N4CCCC4)CC3)c3c(N)ncnc3n2C)c(C)c1F] | A | A |
| 1331 | 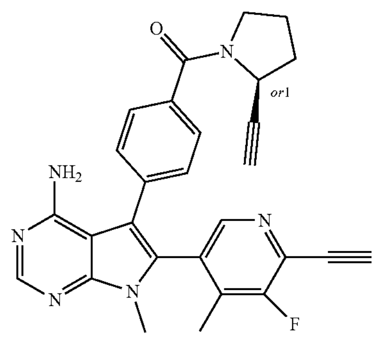 [SMILES: C#Cc1ncc(-c2c(-c3ccc(C(=O)N4CCC[C@H]4C#C)cc3)c3c(N)ncnc3n2C)c(C)c1F] | A | A |
| 1332 | 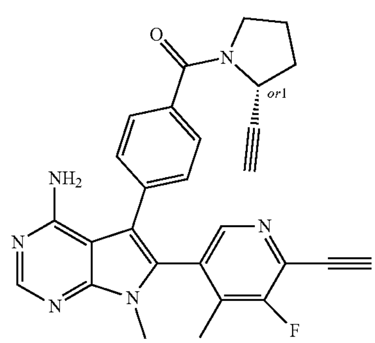 [SMILES: C#Cc1ncc(-c2c(-c3ccc(C(=O)N4CCC[C@@H]4C#C)cc3)c3c(N)ncnc3n2C)c(C)c1F] | A | A |
| 1333 | 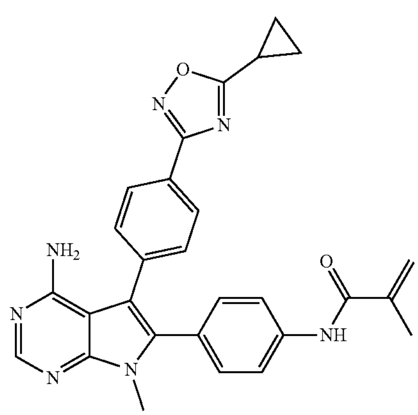 [SMILES: C=C(C)C(=O)Nc1ccc(-c2c(-c3ccc(-c4noc(C5CC5)n4)cc3)c3c(N)ncnc3n2C)cc1] | C | |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1334 | 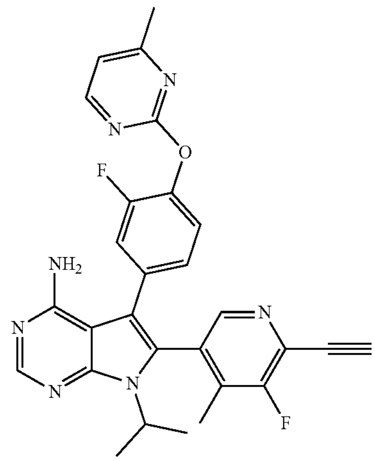 | A | A |
| 1335 | 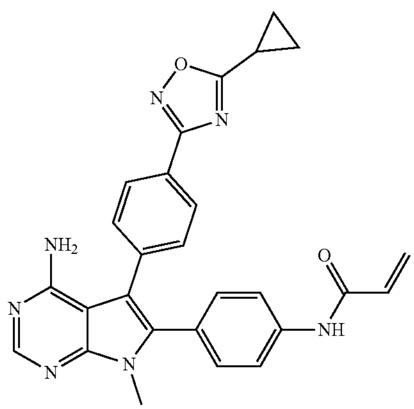 [SMILES: C=CC(=O)Nc1ccc(-c2c(-c3ccc(-c4noc(C5CC5)n4)cc3)c3c(N)ncnc3n2C)cc1] | A | |
| 1336 | 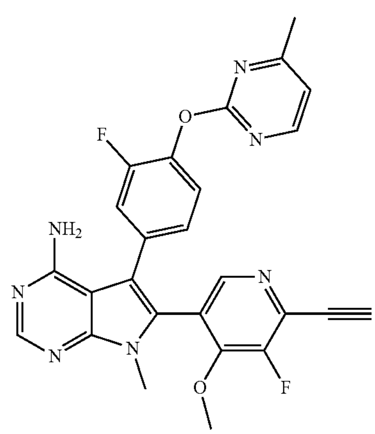 [SMILES: C#Cc1ncc(-c2c(-c3ccc(Oc4nccc(C)n4)c(F)c3)c3c(N)ncnc3n2C)c(OC)c1F] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1337 | 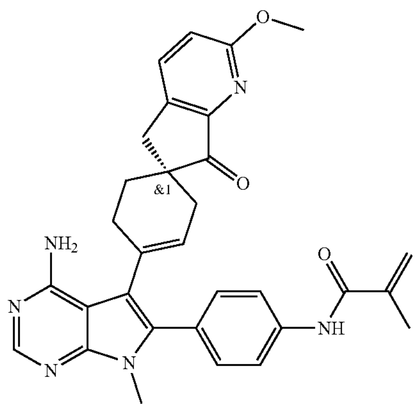 [SMILES: C=C(C)C(=O)Nc1ccc(-c2c(C3=CC[C@]4(CC3)Cc3ccc(OC)nc3C4=O)c3c(N)ncnc3n2C)cc1] | B | A |
| 1338 | 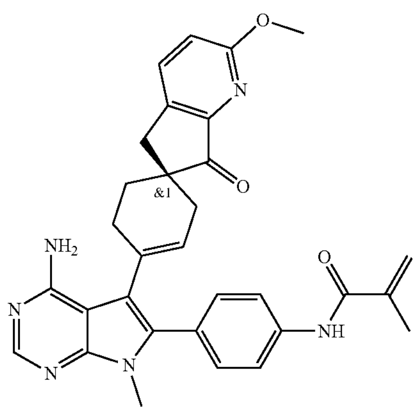 [SMILES: C=C(C)C(=O)Nc1ccc(-c2c(C3=CC[C@@]4(CC3)Cc3ccc(OC)nc3C4=O)c3c(N)ncnc3n2C)cc1] | D | D |
| 1339 | 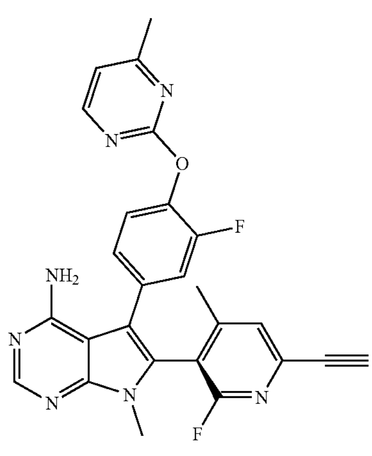 | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1340 | 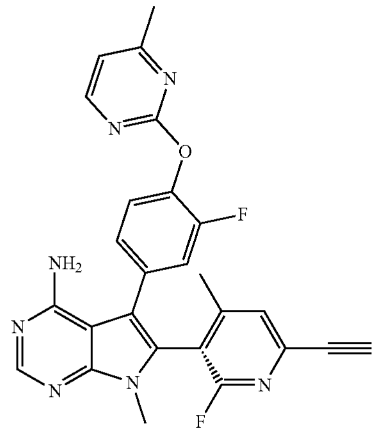 | A | A |
| 1341 | 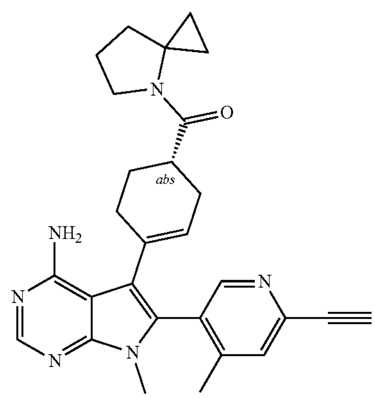 | A | C |
| 1342 | 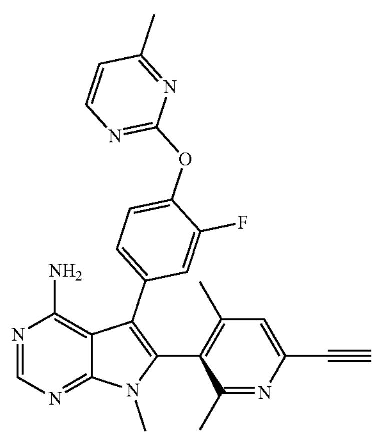 | A | A |
| 1343 | 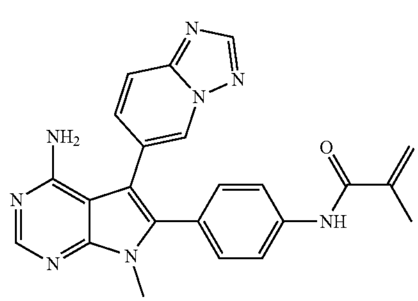 [SMILES: C=C(C)C(=O)Nc1ccc(-c2c(-c3ccc4ncnn4c3)c3c(N)ncnc3n2C)cc1] | D | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1344 | 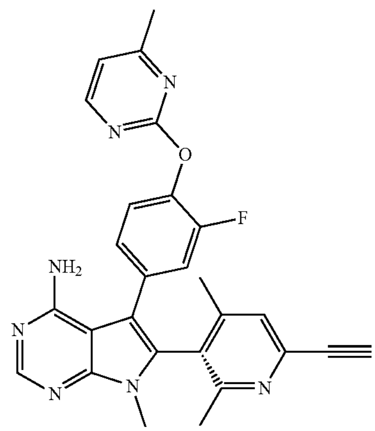 | A | A |
| 1345 | 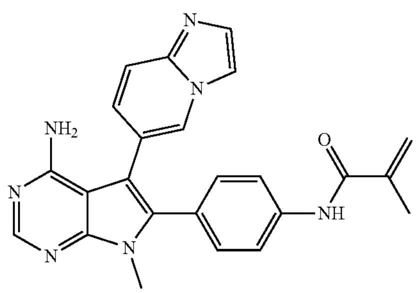 [SMILES: C=C(C)C(=O)Nc1ccc(-c2c(-c3ccc4nccn4c3)c3c(N)ncnc3n2C)cc1] | D | D |
| 1346 | 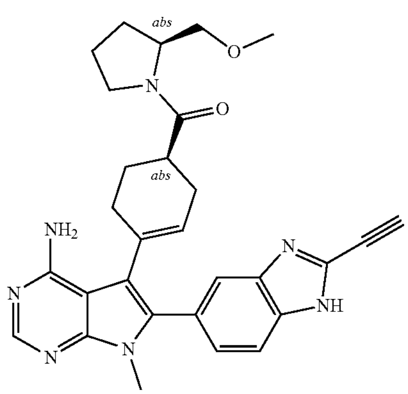 [SMILES: C#Cc1nc2cc(-c3c(C4=CC[C@H](C(=O)N5CCC[C@H]5COC)CC4)c4c(N)ncnc4n3C)ccc2[nH]1] | A | C |
| 1347 | 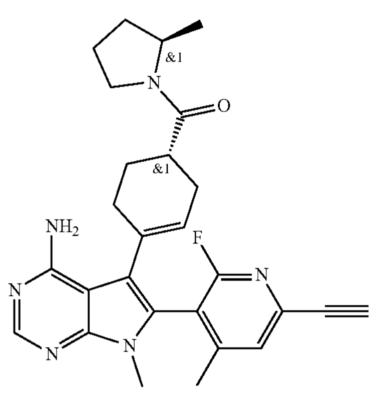 [SMILES: C#Cc1cc(C)c(-c2c(C3=CC[C@@H](C(=O)N4CCC[C@H]4C)CC3)c3c(N)ncnc3n2C)c(F)n1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1348 | 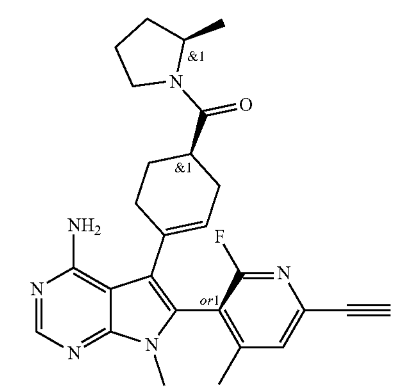 | B | A |
| 1349 | 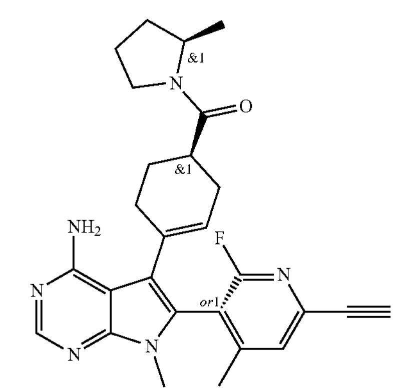 | A | A |
| 1350 | 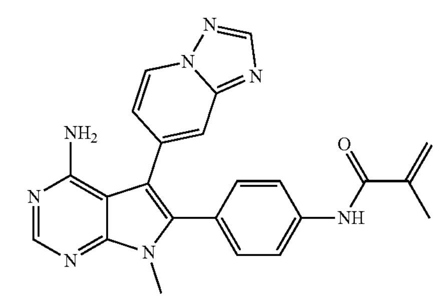 [SMILES: C=C(C)C(=O)Nc1ccc(-c2c(-c3ccn4ncnc4c3)c3c(N)ncnc3n2C)cc1] | D | D |
| 1351 | 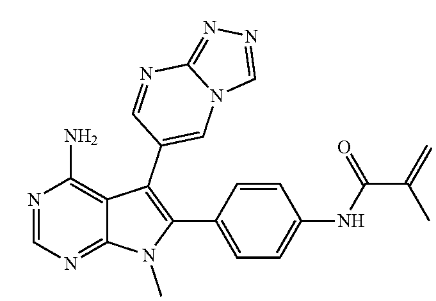 [SMILES: C=C(C)C(=O)Nc1ccc(-c2c(-c3cnc4nncn4c3)c3c(N)ncnc3n2C)cc1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1352 | 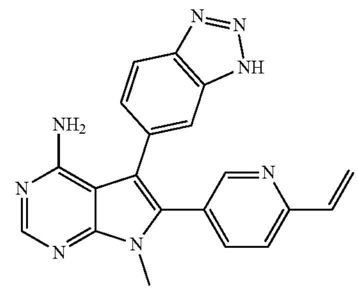 [SMILES: C=Cc1ccc(-c2c(-c3ccc4nn[nH]c4c3)c3c(N)ncnc3n2C)cn1] | A | A |
| 1353 | 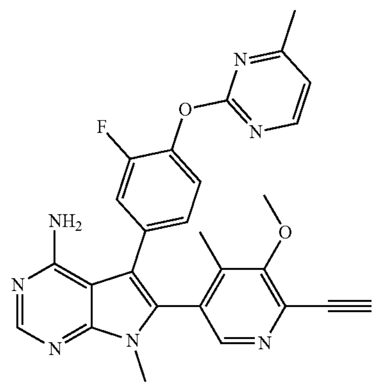 [SMILES: C#Cc1ncc(-c2c(-c3ccc(Oc4nccc(C)n4)c(F)c3)c3c(N)ncnc3n2C)c(C)c1OC] | A | A |
| 1354 | 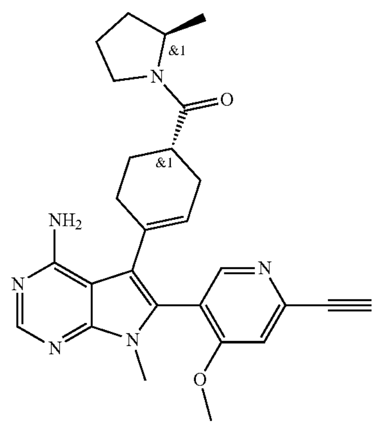 [SMILES: C#Cc1cc(OC)c(-c2c(C3=CC[C@@H](C(=O)N4CCC[C@H]4C)CC3)c3c(N)ncnc3n2C)cn1] | A | A |
| 1355 | 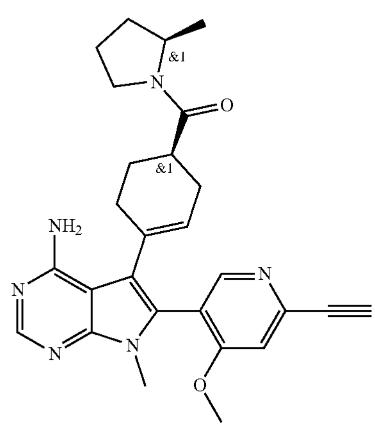 [SMILES: C#Cc1cc(OC)c(-c2c(C3=CC[C@H](C(=O)N4CCC[C@H]4C)CC3)c3c(N)ncnc3n2C)cn1] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1356 | 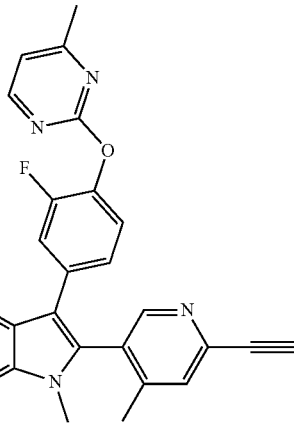 | A | A |
| 1357 | 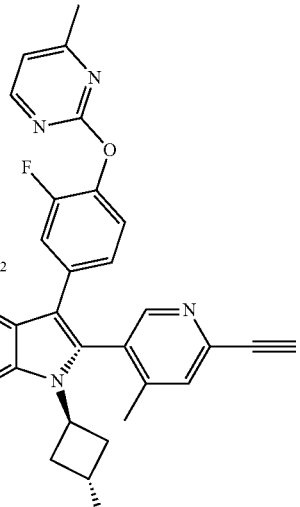 | A | A |
| 1358 | 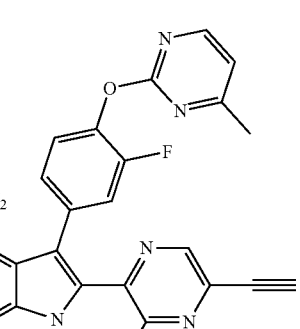 | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1359 | 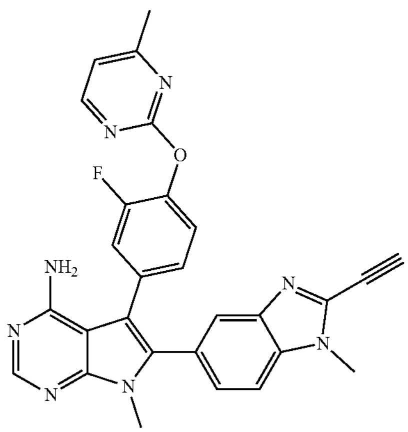 [SMILES: C#Cc1nc2cc(-c3c(-c4ccc(Oc5nccc(C)n5)c(F)c4)c4c(N)ncnc4n3C)ccc2n1C] | A | A |
| 1360 | 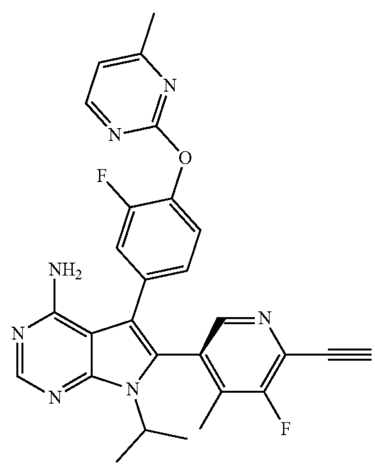 | A | A |
| 1361 | 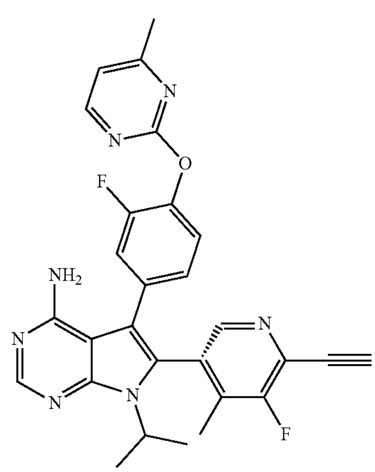 | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1362 | 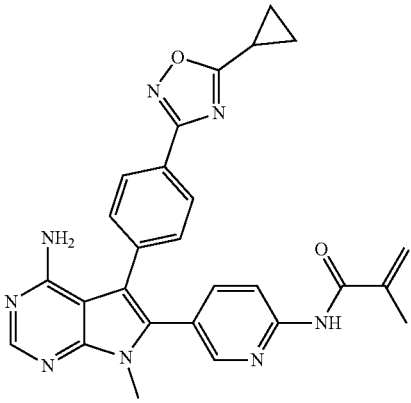 | B | |
| 1363 | 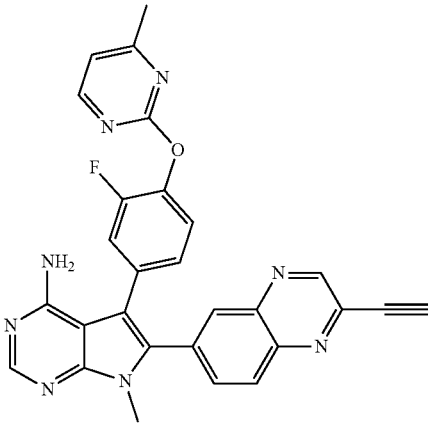 [SMILES: C#Cc1cnc2cc(-c3c(-c4ccc(Oc5nccc(C)n5)c(F)c4)c4c(N)ncnc4n3C)ccc2n1] | A | A |
| 1364 | 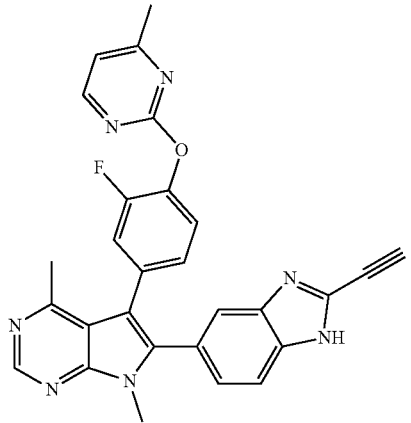 [SMILES: C#Cc1nc2cc(-c3c(-c4ccc(Oc5nccc(C)n5)c(F)c4)c4c(C)ncnc4n3C)ccc2[nH]1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1365 | 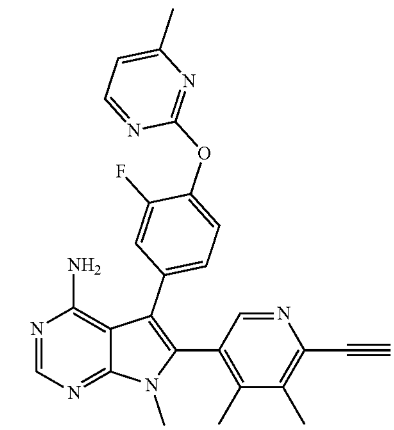 [SMILES: C#Cc1ncc(-c2c(-c3ccc(Oc4nccc(C)n4)c(F)c3)c3c(N)ncnc3n2C)c(C)c1C] | A | A |
| 1366 | 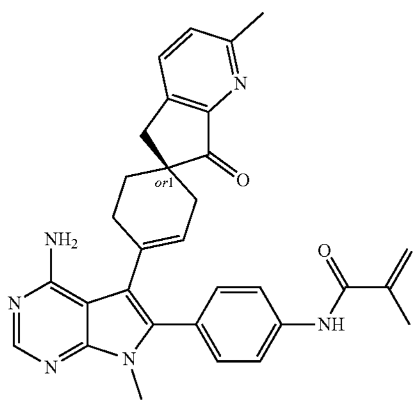 [SMILES: C=C(C)C(=O)Nc1ccc(-c2c(C3=CC[C@@]4(CC3)Cc3ccc(C)nc3C4=O)c3c(N)ncnc3n2C)cc1] | D | D |
| 1367 | 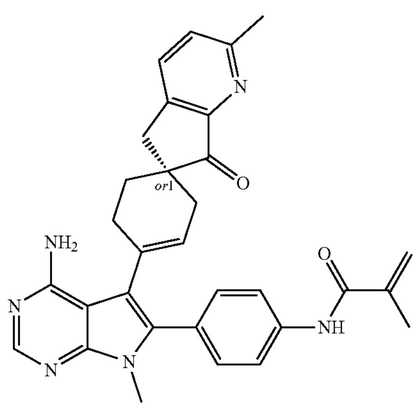 [SMILES: C=C(C)C(=O)Nc1ccc(-c2c(C3=CC[C@]4(CC3)Cc3ccc(C)nc3C4=O)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1368 | 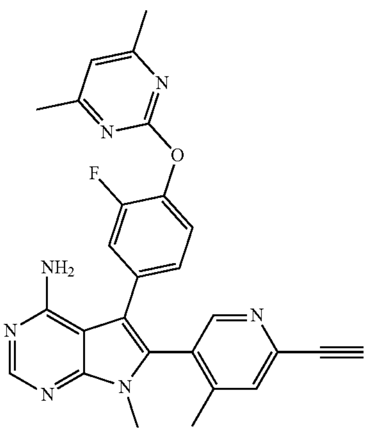 [SMILES: C#Cc1cc(C)c(-c2c(-c3ccc(Oc4nc(C)cc(C)n4)c(F)c3)c3c(N)ncnc3n2C)cn1] | A | A |
| 1369 | 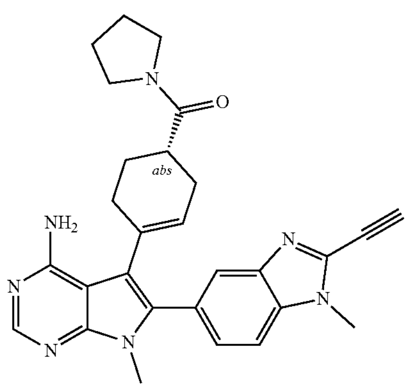 [SMILES: C#Cc1nc2cc(-c3c(C4=CC[C@@H](C(=O)N5CCCC5)CC4)c4c(N)ncnc4n3C)ccc2n1C] | A | A |
| 1370 | 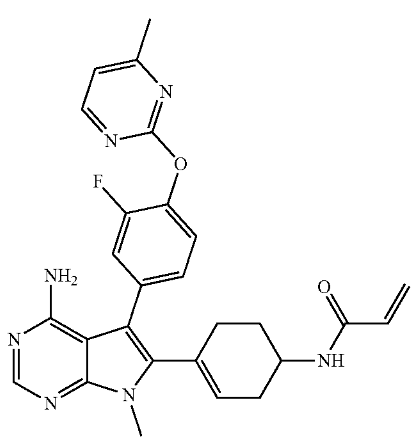 | B | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1371 | 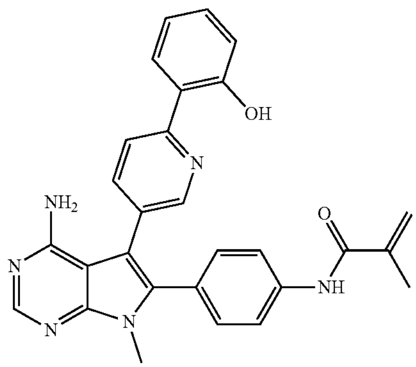 [SMILES: C=C(C)C(=O)Nc1ccc(-c2c(-c3ccc(-c4ccccc4O)nc3)c3c(N)ncnc3n2C)cc1] | D | C |
| 1372 | 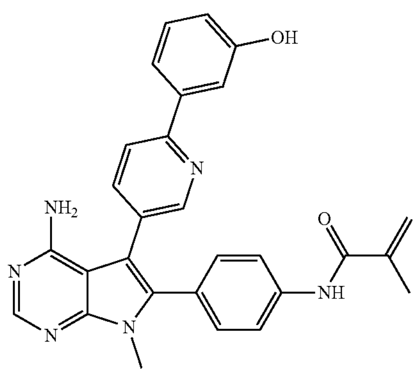 [SMILES: C=C(C)C(=O)Nc1ccc(-c2c(-c3ccc(-c4cccc(O)c4)nc3)c3c(N)ncnc3n2C)cc1] | D | D |
| 1373 | 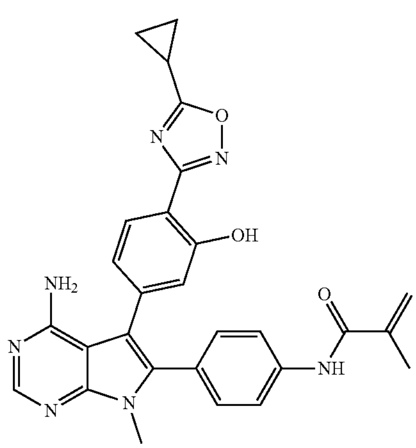 [SMILES: C=C(C)C(=O)Nc1ccc(-c2c(-c3ccc(-c4noc(C5CC5)n4)c(O)c3)c3c(N)ncnc3n2C)cc1] | A | B |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1374 | 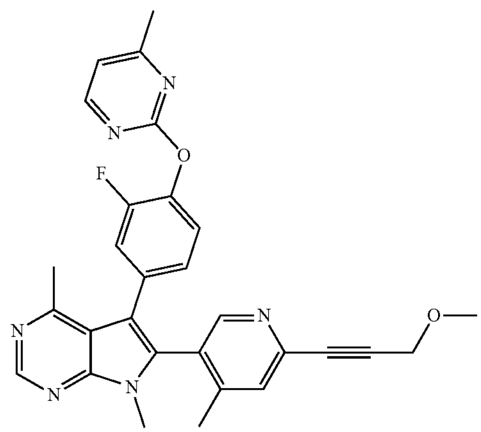 [SMILES: COCC#Cc1cc(C)c(-c2c(-c3ccc(Oc4nccc(C)n4)c(F)c3)c3c(C)ncnc3n2C)cn1] | C | B |
| 1375 | 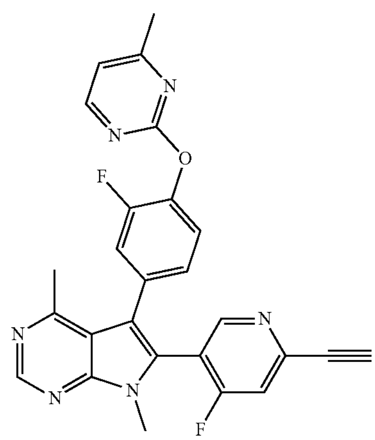 [SMILES: C#Cc1cc(F)c(-c2c(-c3ccc(Oc4nccc(C)n4)c(F)c3)c3c(C)ncnc3n2C)cn1] | A | A |
| 1376 | 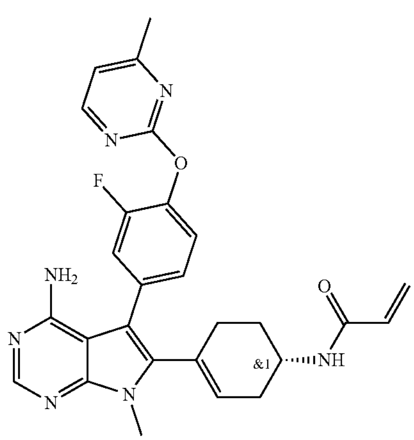 [SMILES: C=CC(=O)N[C@@H]1CC=C(c2c(-c3ccc(Oc4nccc(C)n4)c(F)c3)c3c(N)ncnc3n2C)CC1] | C | B |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1377 | 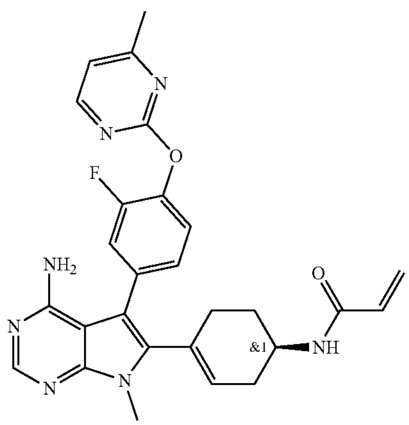 [SMILES: C=CC(=O)N[C@H]1CC=C(c2c(-c3ccc(Oc4nccc(C)n4)c(F)c3)c3c(N)ncnc3n2C)CC1] | C | C |
| 1378 | 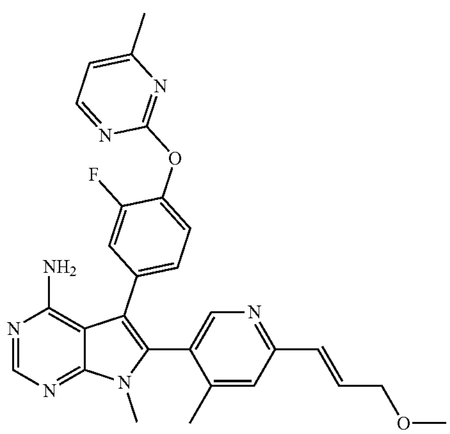 [SMILES: COC/C=C/c1cc(C)c(-c2c(-c3ccc(Oc4nccc(C)n4)c(F)c3)c3c(N)ncnc3n2C)cn1] | D | D |
| 1379 | 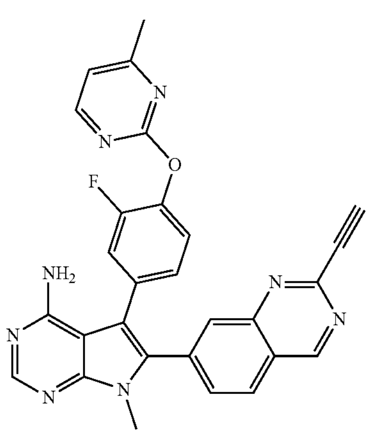 | B | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1380 | 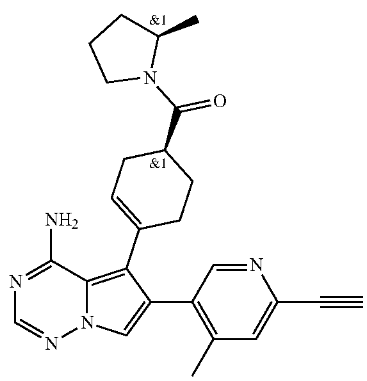 [SMILES: C#Cc1cc(C)c(-c2cn3ncnc(N)c3c2C2=CC[C@@H](C(=O)N3CCC[C@H]3C)CC2)cn1] | C | C |
| 1381 | 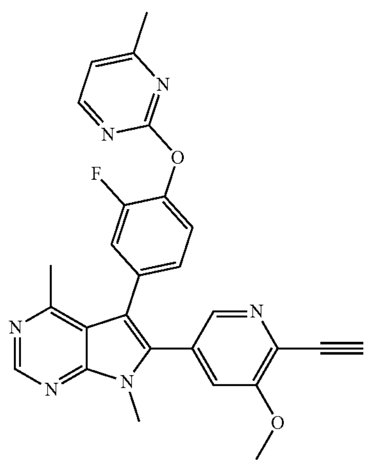 [SMILES: C#Cc1ncc(-c2c(-c3ccc(Oc4nccc(C)n4)c(F)c3)c3c(C)ncnc3n2C)cc1OC] | B | A |
| 1382 | 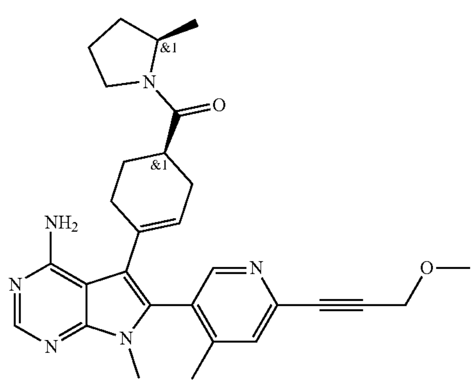 [SMILES: COCC#Cc1cc(C)c(-c2c(C3=CC[C@H](C(=O)N4CCC[C@H]4C)CC3)c3c(N)ncnc3n2C)cn1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1383 | 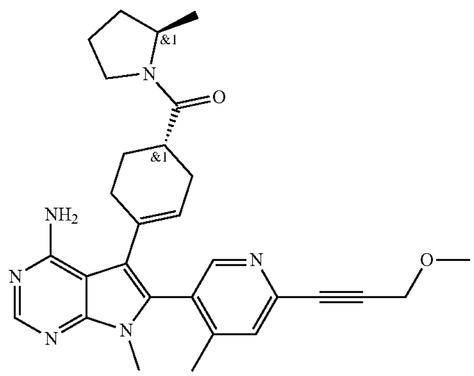 [SMILES: COCC#Cc1cc(C)c(-c2c(C3=CC[C@@H](C(=O)N4CCC[C@H]4C)CC3)c3c(N)ncnc3n2C)cn1] | C | C |
| 1384 | 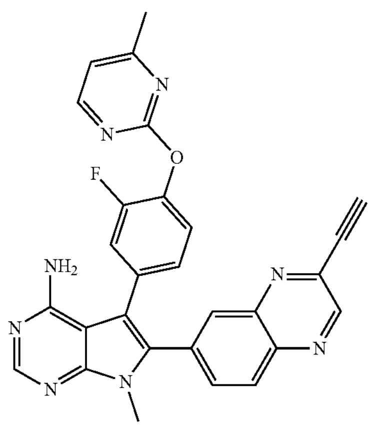 [SMILES: C#Cc1cnc2ccc(-c3c(-c4ccc(Oc5nccc(C)n5)c(F)c4)c4c(N)ncnc4n3C)cc2n1] | A | B |
| 1385 | 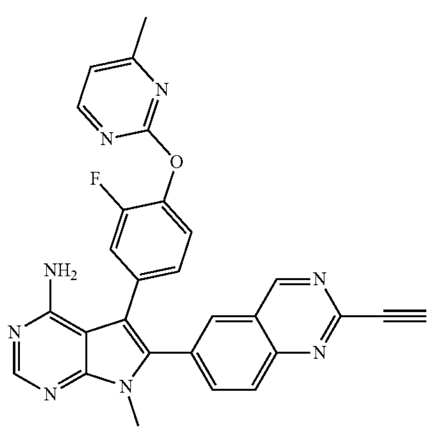 [SMILES: C#Cc1ncc2cc(-c3c(-c4ccc(Oc5nccc(C)n5)c(F)c4)c4c(N)ncnc4n3C)ccc2n1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1386 | 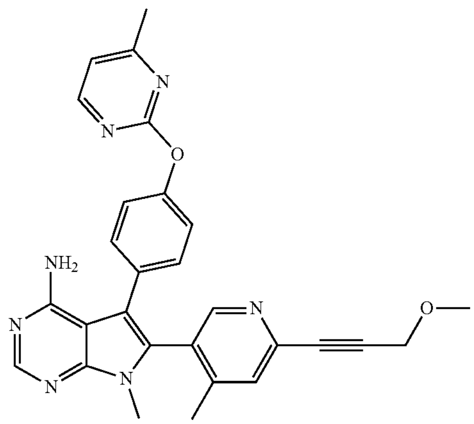 [SMILES: COCC#Cc1cc(C)c(-c2c(-c3ccc(Oc4nccc(C)n4)cc3)c3c(N)ncnc3n2C)cn1] | A | A |
| 1387 | 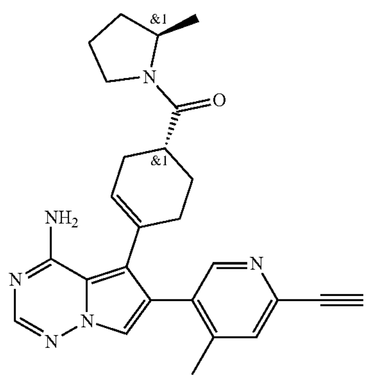 [SMILES: C#Cc1cc(C)c(-c2cn3ncnc(N)c3c2C2=CC[C@H](C(=O)N3CCC[C@H]3C)CC2)cn1] | D | D |
| 1388 | 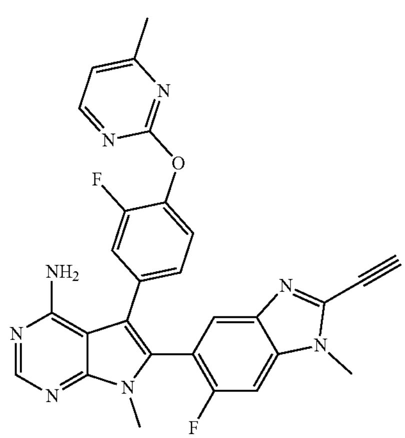 [SMILES: C#Cc1nc2cc(-c3c(-c4ccc(Oc5nccc(C)n5)c(F)c4)c4c(N)ncnc4n3C)c(F)cc2n1C] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1389 | 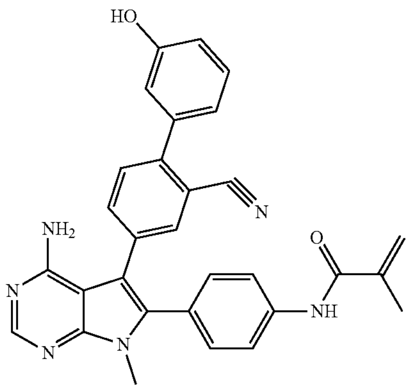 [SMILES: C=C(C)C(=O)Nc1ccc(-c2c(-c3ccc(-c4cccc(O)c4)c(C#N)c3)c3c(N)ncnc3n2C)cc1] | D | C |
| 1390 | 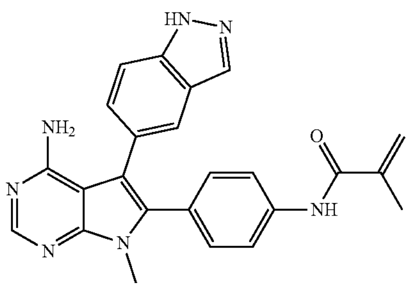 [SMILES: C=C(C)C(=O)Nc1ccc(-c2c(-c3ccc4[nH]ncc4c3)c3c(N)ncnc3n2C)cc1] | D | D |
| 1391 | 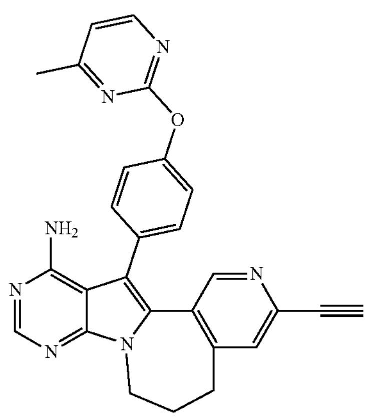 [SMILES: C#Cc1cc2c(cn1)-c1c(-c3ccc(Oc4nccc(C)n4)cc3)c3c(N)ncnc3n1CCC2] | A | A |
| 1392 | 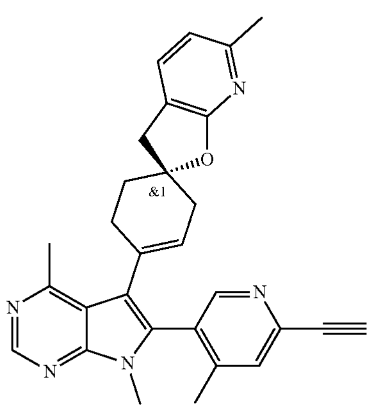 [SMILES: C#Cc1cc(C)c(-c2c(C3=CC[C@@]4(CC3)Cc3ccc(C)nc3O4)c3c(C)ncnc3n2C)cn1] | D | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1393 | 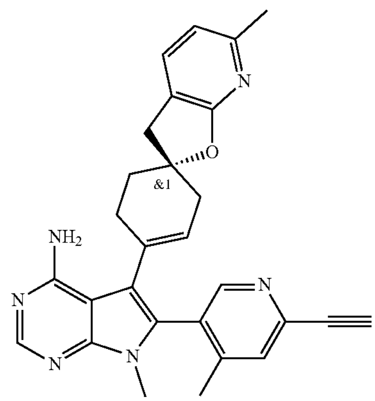 [SMILES: C#Cc1cc(C)c(-c2c(C3=CC[C@@]4(CC3)Cc3ccc(C)nc3O4)c3c(N)ncnc3n2C)cn1] | D | D |
| 1394 | 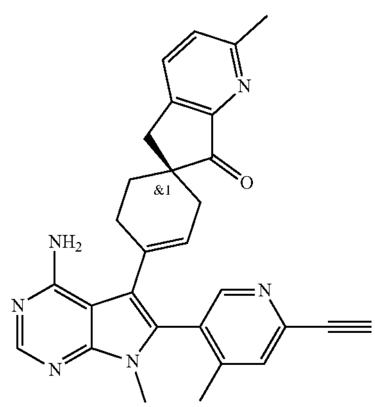 [SMILES: C#Cc1cc(C)c(-c2c(C3=CC[C@@]4(CC3)Cc3ccc(C)nc3C4=O)c3c(N)ncnc3n2C)cn1] | B | B |
| 1395 | 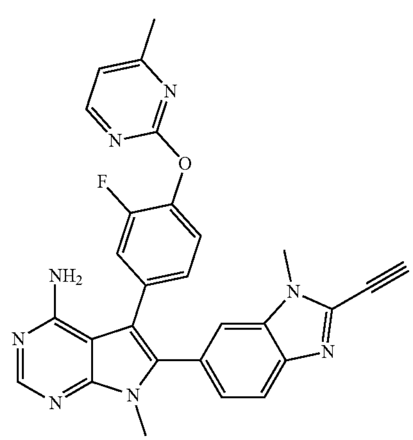 [SMILES: C#Cc1nc2ccc(-c3c(-c4ccc(Oc5nccc(C)n5)c(F)c4)c4c(N)ncnc4n3C)cc2n1C] | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1396 | 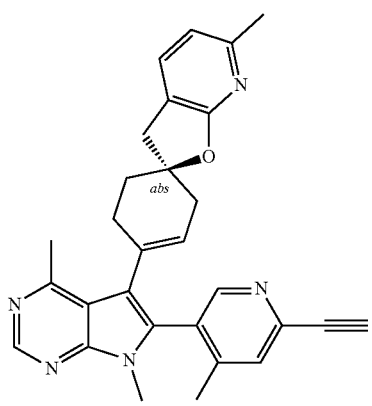 [SMILES: C#Cc1cc(C)c(-c2c(C3=CC[C@]4(CC3)Cc3ccc(C)nc3O4)c3c(C)ncnc3n2C)cn1] | C | D |
| 1397 | 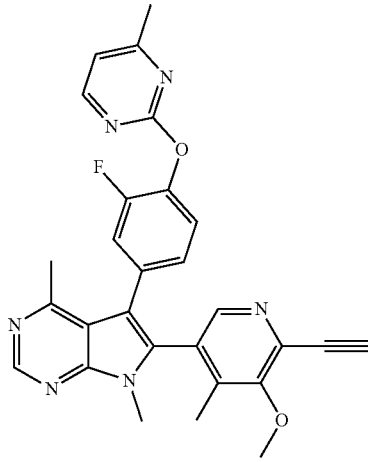 [SMILES: C#Cc1ncc(-c2c(-c3ccc(Oc4nccc(C)n4)c(F)c3)c3c(C)ncnc3n2C)c(C)c1OC] | C | A |
| 1398 | 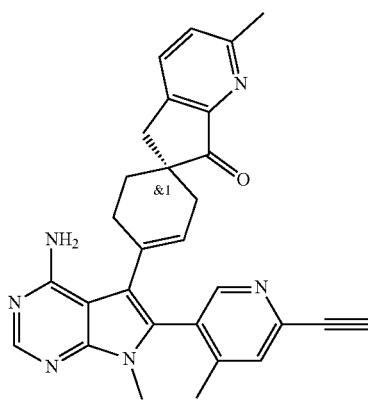 [SMILES: C#Cc1cc(C)c(-c2c(C3=CC[C@]4(CC3)Cc3ccc(C)nc3C4=O)c3c(N)ncnc3n2C)cn1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1399 | 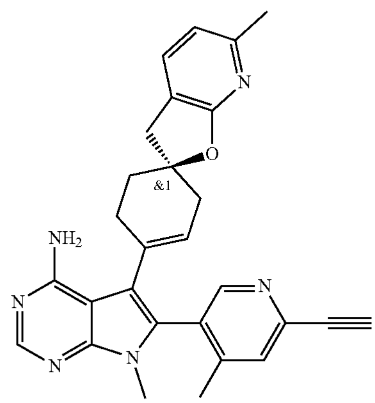 [SMILES: C#Cc1cc(C)c(-c2c(C3=CC[C@]4(CC3)Cc3ccc(C)nc3O4)c3c(N)ncnc3n2C)cn1] | A | B |
| 1400 | 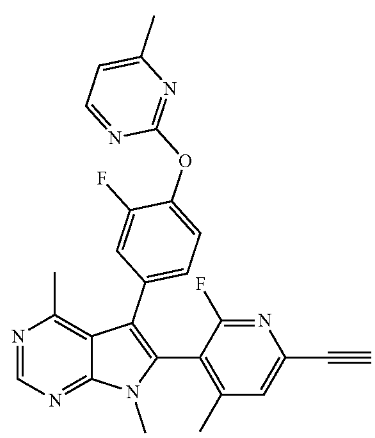 | A | A |
| 1401 | 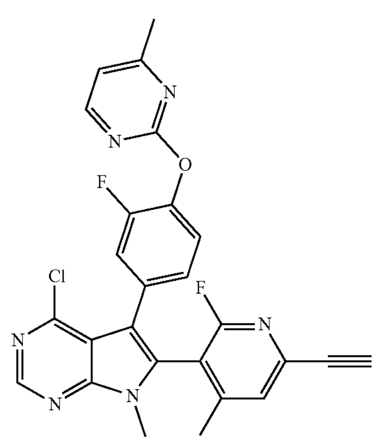 [SMILES: C#Cc1cc(C)c(-c2c(-c3ccc(Oc4nccc(C)n4)c(F)c3)c3c(Cl)ncnc3n2C)c(F)n1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1402 | 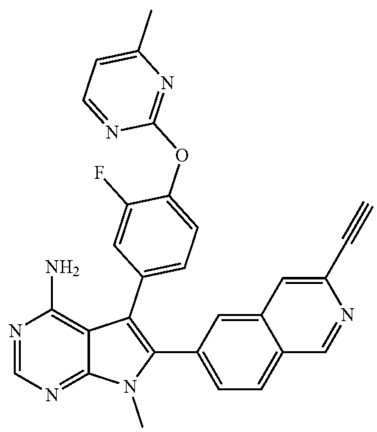 [SMILES: C#Cc1cc2cc(-c3c(-c4ccc(Oc5nccc(C)n5)c(F)c4)c4c(N)ncnc4n3C)ccc2cn1] | D | D |
| 1403 | 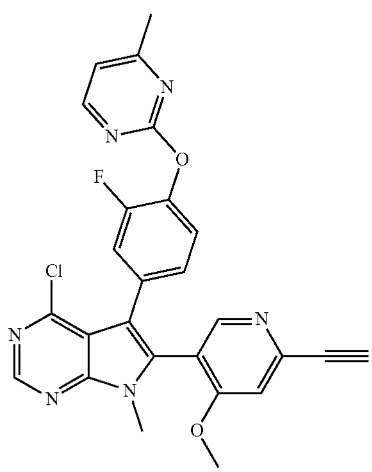 [SMILES: C#Cc1cc(OC)c(-c2c(-c3ccc(Oc4nccc(C)n4)c(F)c3)c3c(Cl)ncnc3n2C)cn1] | A | A |
| 1404 | 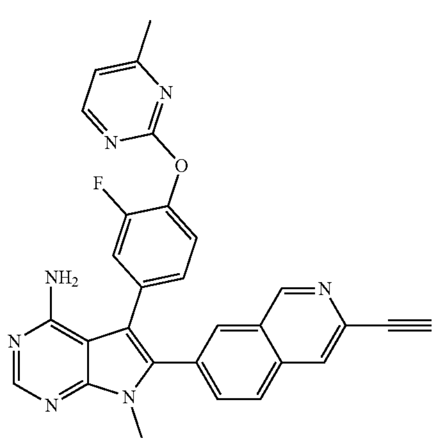 [SMILES: C#Cc1cc2ccc(-c3c(-c4ccc(Oc5nccc(C)n5)c(F)c4)c4c(N)ncnc4n3C)cc2cn1] | C | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1405 | 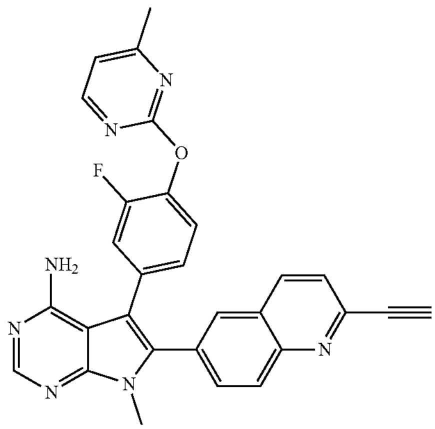 [SMILES: C#Cc1ccc2cc(-c3c(-c4ccc(Oc5nccc(C)n5)c(F)c4)c4c(N)ncnc4n3C)ccc2n1] | A | A |
| 1406 | 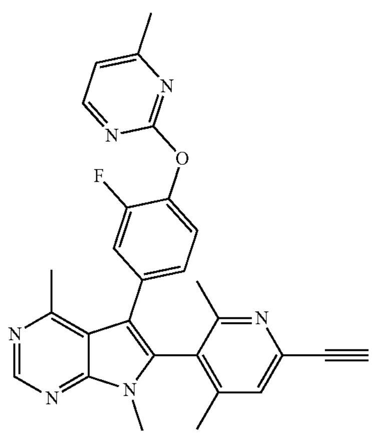 [SMILES: C#Cc1cc(C)c(-c2c(-c3ccc(Oc4nccc(C)n4)c(F)c3)c3c(C)ncnc3n2C)c(C)n1] | A | A |
| 1407 | 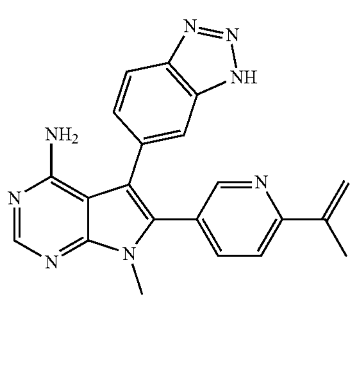 [SMILES: C=C(C)c1ccc(-c2c(-c3ccc4nn[nH]c4c3)c3c(N)ncnc3n2C)cn1] | C | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1408 | 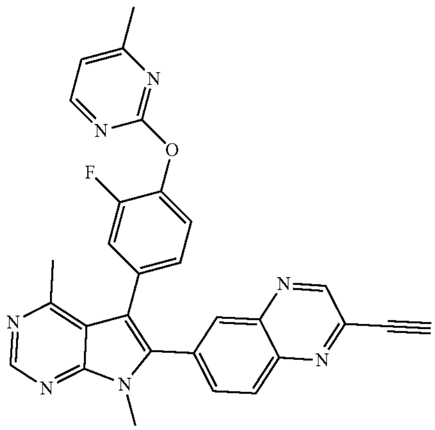 [SMILES: C#Cc1cnc2cc(-c3c(-c4ccc(Oc5nccc(C)n5)c(F)c4)c4c(C)ncnc4n3C)ccc2n1] | A | B |
| 1409 | 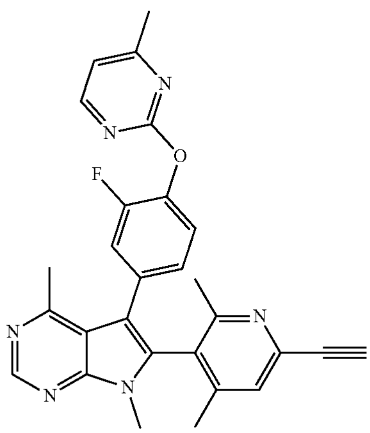 [SMILES: C#Cc1cc(C)c(-c2c(-c3ccc(Oc4nccc(C)n4)c(F)c3)c3c(C)ncnc3n2C)c(C)n1] | A | A |
| 1410 | 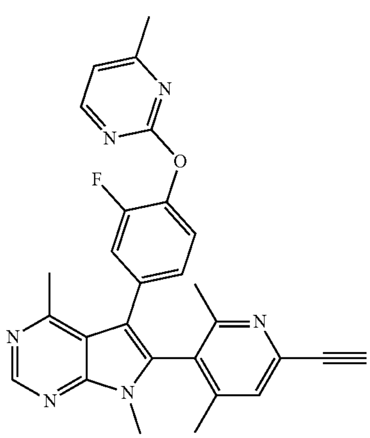 [SMILES: C#Cc1cc(C)c(-c2c(-c3ccc(Oc4nccc(C)n4)c(F)c3)c3c(C)ncnc3n2C)c(C)n1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1411 | 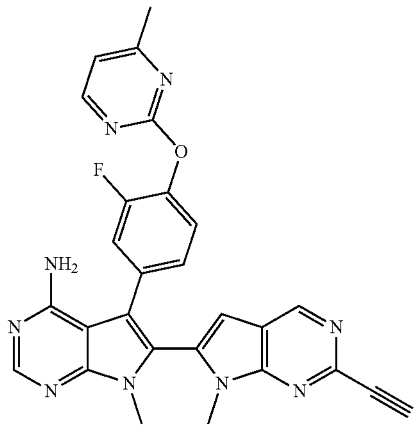 [SMILES: C#Cc1ncc2cc(-c3c(-c4ccc(Oc5nccc(C)n5)c(F)c4)c4c(N)ncnc4n3C)n(C)c2n1] | A | A |
| 1412 | 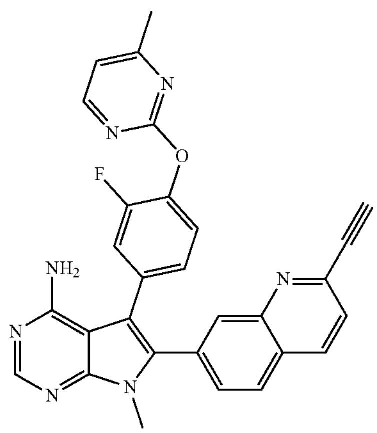 [SMILES: C#Cc1ccc2ccc(-c3c(-c4ccc(Oc5nccc(C)n5)c(F)c4)c4c(N)ncnc4n3C)cc2n1] | C | C |
| 1413 | 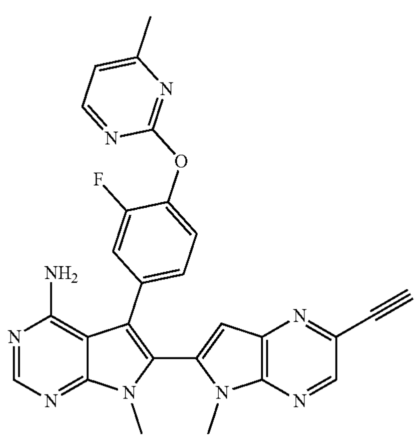 [SMILES: C#Cc1cnc2c(cc(-c3c(-c4ccc(Oc5nccc(C)n5)c(F)c4)c4c(N)ncnc4n3C)n2C)n1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1414 | Atropisomer 1 | A | A |
| 1415 | Atropisomer 2 | A | A |
| 1416 | Atropisomer 1 | A | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1417 | Atropisomer 2 | A | A |
| 1418 | 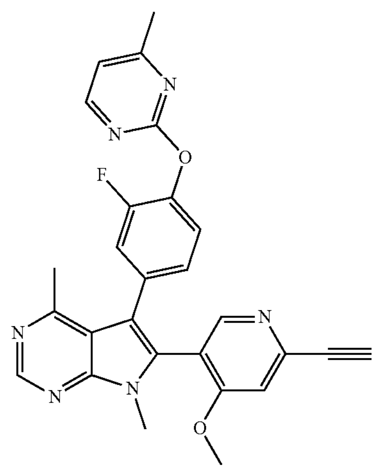 [SMILES: C#Cc1cc(OC)c(-c2c(-c3ccc(Oc4nccc(C)n4)c(F)c3)c3c(C)ncnc3n2C)cn1] | A | A |
| 1419 | 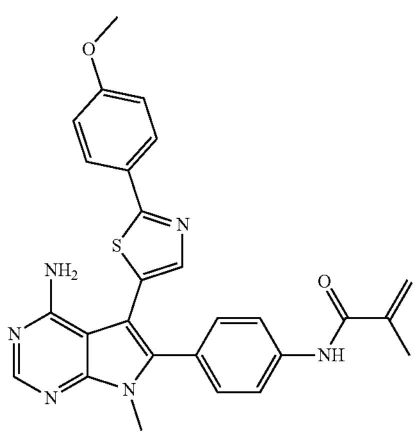 [SMILES: C=C(C)C(=O)Nc1ccc(-c2c(-c3cnc(-c4ccc(OC)cc4)s3)c3c(N)ncnc3n2C)cc1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1420 | 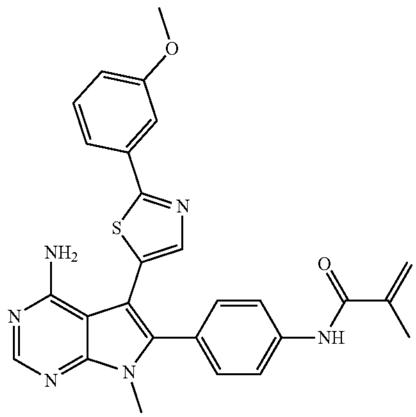 [SMILES: C=C(C)C(=O)Nc1ccc(-c2c(-c3cnc(-c4cccc(OC)c4)s3)c3c(N)ncnc3n2C)cc1] | C | C |
| 1421 | 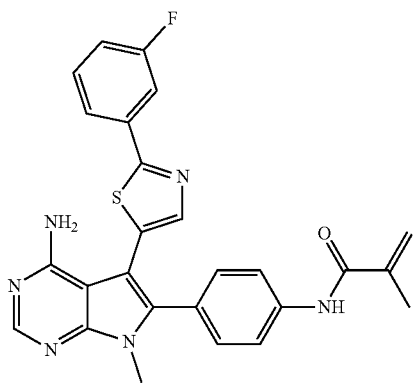 [SMILES: C=C(C)C(=O)Nc1ccc(-c2c(-c3cnc(-c4cccc(F)c4)s3)c3c(N)ncnc3n2C)cc1] | C | C |
| 1422 | 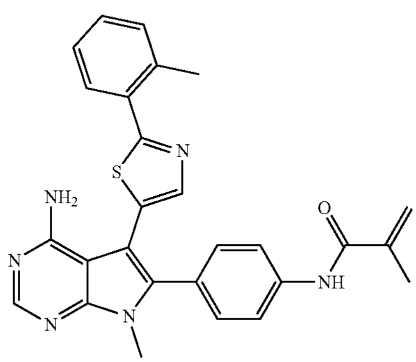 [SMILES: C=C(C)C(=O)Nc1ccc(-c2c(-c3cnc(-c4ccccc4C)s3)c3c(N)ncnc3n2C)cc1] | C | C |
| 1423 | 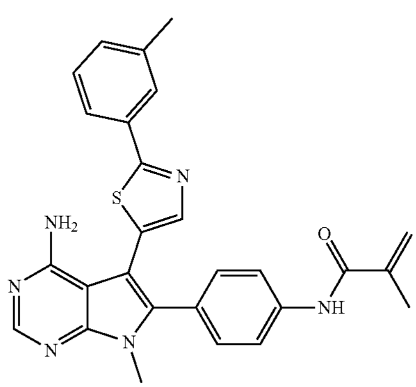 [SMILES: C=C(C)C(=O)Nc1ccc(-c2c(-c3cnc(-c4cccc(C)c4)s3)c3c(N)ncnc3n2C)cc1] | C | C |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1424 | 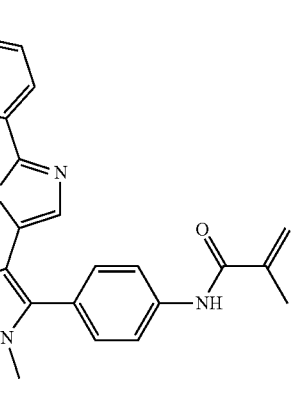 | B | C |
| 1425 | 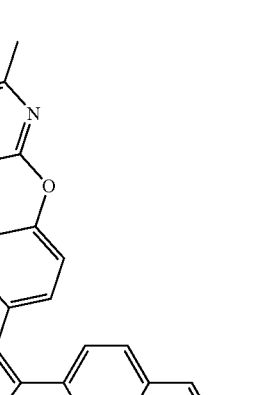 | D | D |
| 1426 | 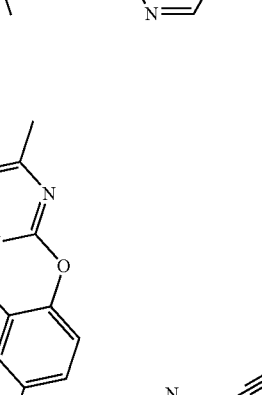 | A | A |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 1427 | 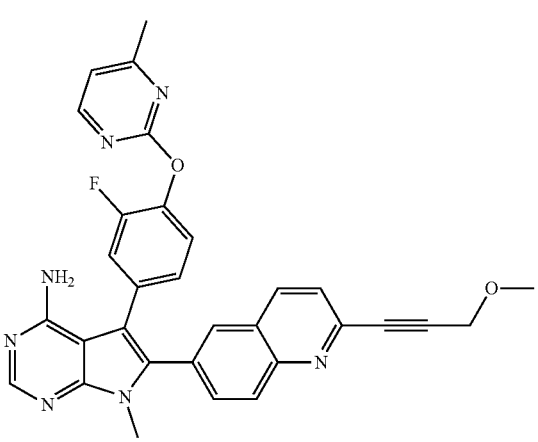 [SMILES: COCC#Cc1ccc2cc(-c3c(-c4ccc(Oc5nccc(C)n5)c(F)c4)c4c(N)ncnc4n3C)ccc2n1] | A | A |
| 1428 | 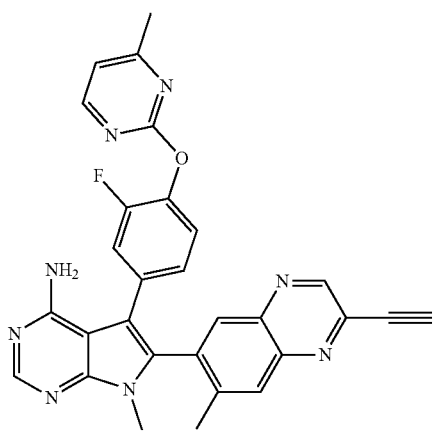 [SMILES: C#Cc1cnc2cc(-c3c(-c4ccc(Oc5nccc(C)n5)c(F)c4)c4c(N)ncnc4n3C)c(C)cc2n1] | A | A |
| 1429 | 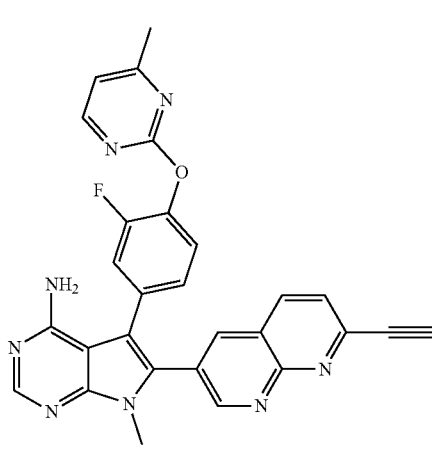 [SMILES: C#Cc1ccc2cc(-c3c(-c4ccc(Oc5nccc(C)n5)c(F)c4)c4c(N)ncnc4n3C)cnc2n1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1430 | 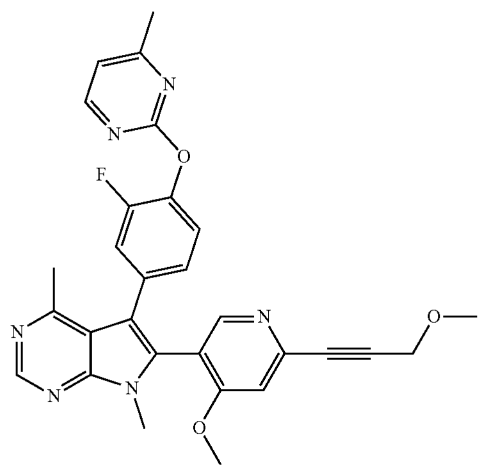 [SMILES: COCC#Cc1cc(OC)c(-c2c(-c3ccc(Oc4nccc(C)n4)c(F)c3)c3c(C)ncnc3n2C)cn1] | A | A |
| 1431 | 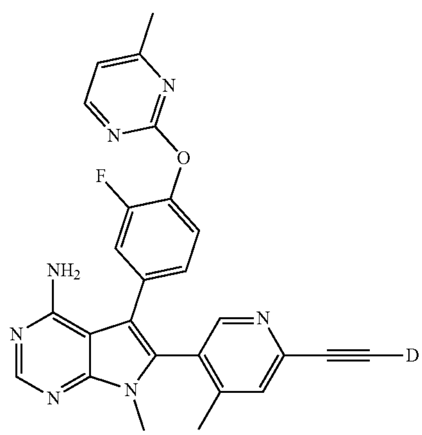 [SMILES: [2H]C#Cc1cc(C)c(-c2c(-c3ccc(Oc4nccc(C)n4)c(F)c3)c3c(N)ncnc3n2C)cn1] | A | A |
| 1432 | 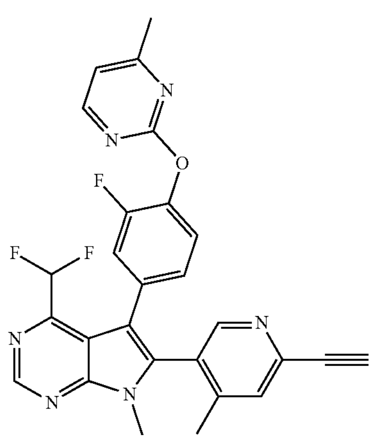 [SMILES: C#Cc1cc(C)c(-c2c(-c3ccc(Oc4nccc(C)n4)c(F)c3)c3c(C(F)F)ncnc3n2C)cn1] | D | D |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1433 | 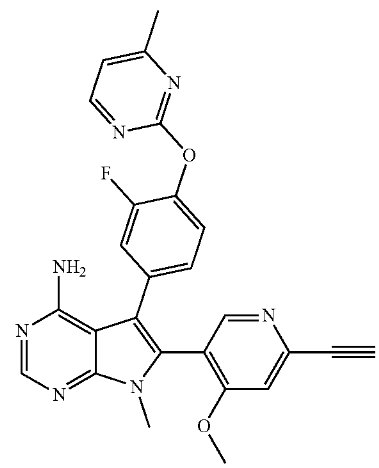 [SMILES: C#Cc1cc(OC)c(-c2c(-c3ccc(Oc4nccc(C)n4)c(F)c3)c3c(N)ncnc3n2C)cn1] | A | A |
| 1434 | 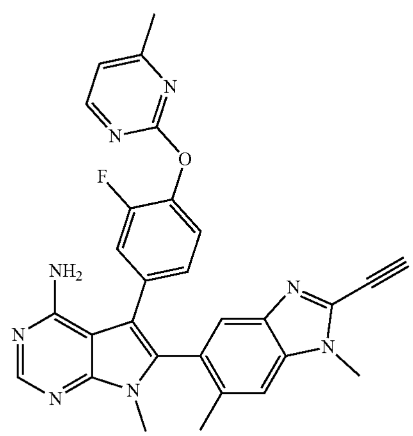 [SMILES: C#Cc1nc2cc(-c3c(-c4ccc(Oc5nccc(C)n5)c(F)c4)c4c(N)ncnc4n3C)c(C)cc2n1C] | A | A |
| 1435 | 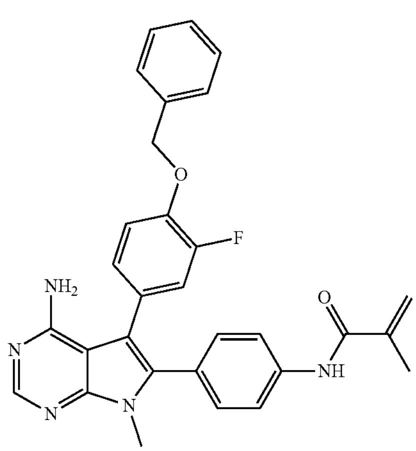 [SMILES: C=C(C)C(=O)Nc1ccc(-c2c(-c3ccc(OCc4ccccc4)c(F)c3)c3c(N)ncnc3n2C)cc1] | D | D |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1436 | 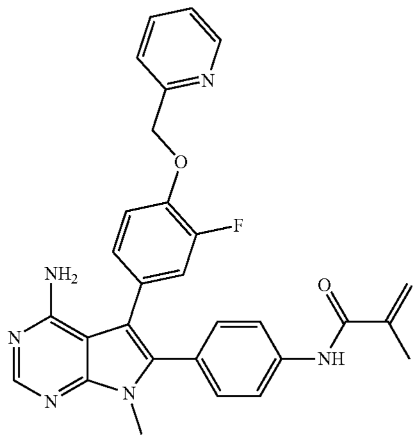 | D | D |
| 1437 | 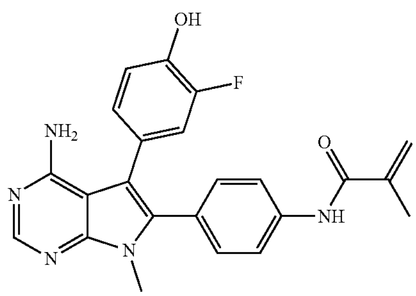 [SMILES: C=C(C)C(=O)Nc1ccc(-c2c(-c3ccc(O)c(F)c3)c3c(N)ncnc3n2C)cc1] | C | D |
| 1438 | 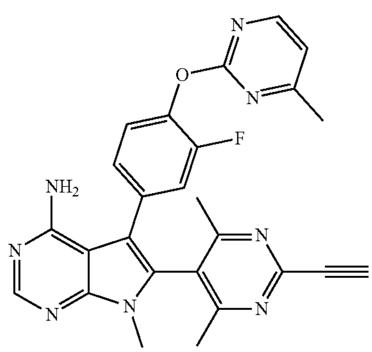 [SMILES: C#Cc1nc(C)c(-c2c(-c3ccc(Oc4nccc(C)n4)c(F)c3)c3c(N)ncnc3n2C)c(C)n1] | A | A |
| 1439 | 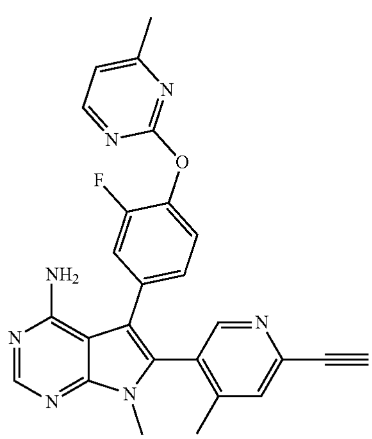 [SMILES: C#Cc1cc(C)c(-c2c(-c3ccc(Oc4nccc(C)n4)c(F)c3)c3c(N)ncnc3n2C)cn1] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1440 | 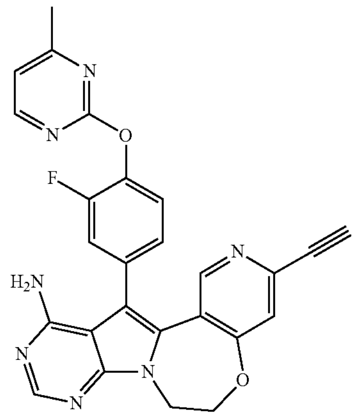 | A | A |
| 1441 | 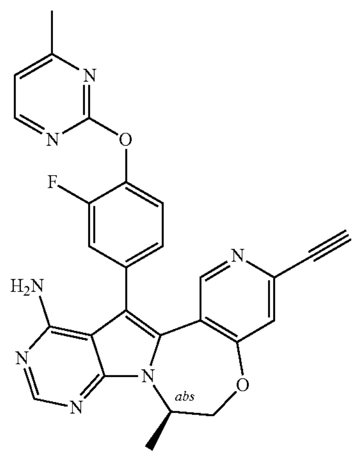 [SMILES: C#Cc1cc2c(cn1)-c1c(-c3ccc(Oc4nccc(C)n4)c(F)c3)c3c(N)ncnc3n1[C@H](C)CO2] | C | B |
| 1442 | 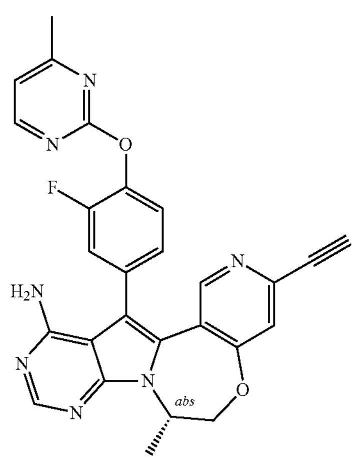 [SMILES: C#Cc1cc2c(cn1)-c1c(-c3ccc(Oc4nccc(C)n4)c(F)c3)c3c(N)ncnc3n1[C@@H](C)CO2] | D | C |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1443 | 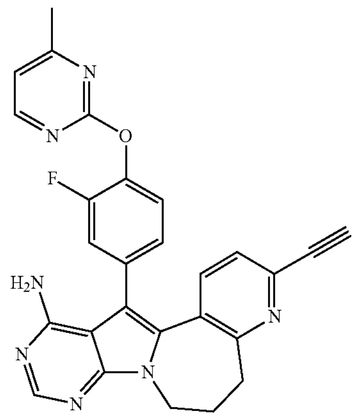 | B | A |
| 1444 | 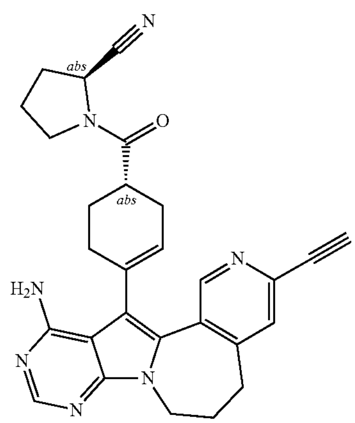 [SMILES: C#Cc1cc2c(cn1)-c1c(C3=CC[C@@H](C(=O)N4CCC[C@H]4C#N)CC3)c3c(N)ncnc3n1CCC2] | A | |
| 1445 | 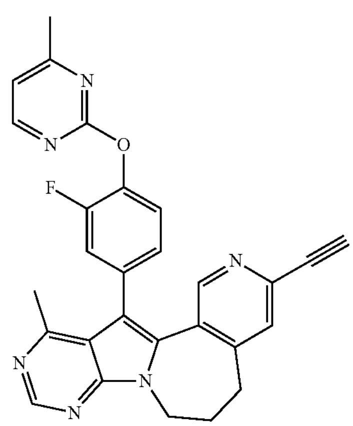 [SMILES: C#Cc1cc2c(cn1)-c1c(-c3ccc(Oc4nccc(C)n4)c(F)c3)c3c(C)ncnc3n1CCC2] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1446 | 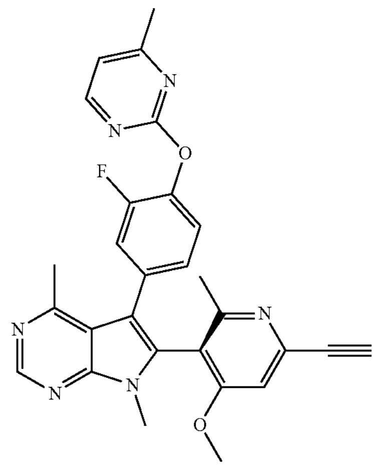 | A | A |
| 1447 | 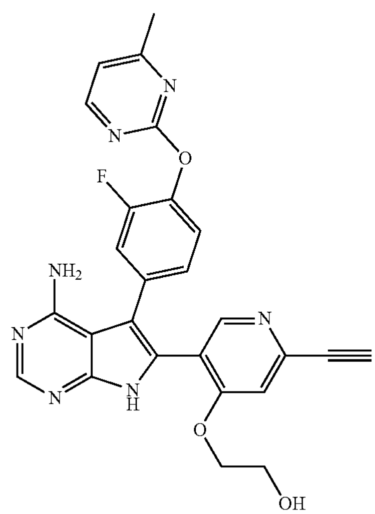 [SMILES: C#Cc1cc(OCCO)c(-c2[nH]c3ncnc(N)c3c2-c2ccc(Oc3nccc(C)n3)c(F)c2)cn1] | A | A |
| 1448 | 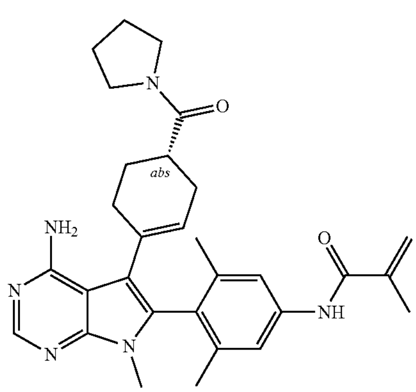 | | |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1449 | 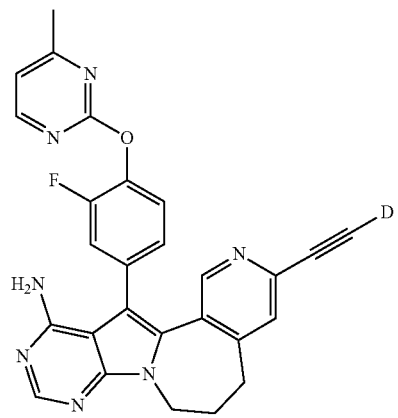 [SMILES: [2H]C#Cc1cc2c(cn1)-c1c(-c3ccc(Oc4nccc(C)n4)c(F)c3)c3c(N)ncnc3n1CCC2] | A | |
| 1450 | 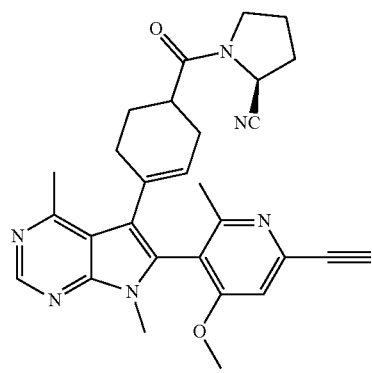 [SMILES: C#Cc1cc(OC)c(-c2c(C3=CCC(C(=O)N4CCC[C@H]4C#N)CC3)c3c(C)ncnc3n2C)c(C)n1] | | |
| 1451 | 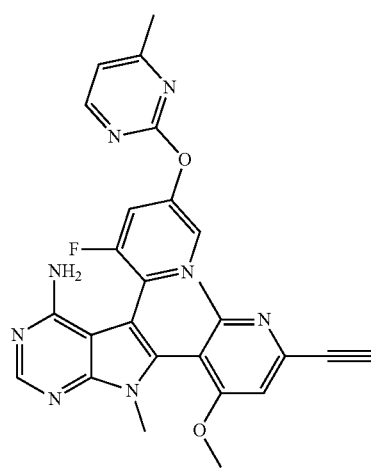 [SMILES: C#Cc1cc(OC)c(-c2c(-c3ncc(Oc4nccc(C)n4)cc3F)c3c(N)ncnc3n2C)c(C)n1] | A | |

903
904

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1452 | 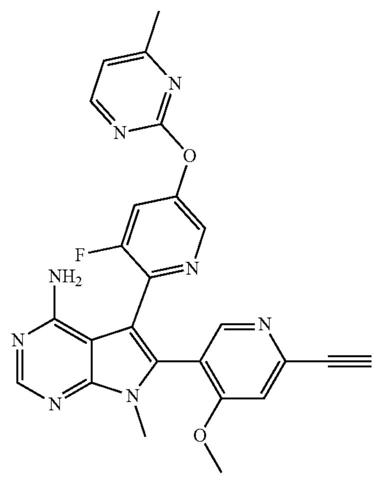 [SMILES: C#Cc1cc(OC)c(-c2c(-c3ncc(Oc4nccc(C)n4)cc3F)c3c(N)ncnc3n2C)cn1] | A | A |
| 1453 | 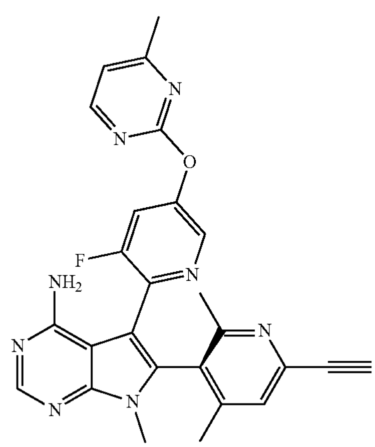 | A | A |
| 1454 | 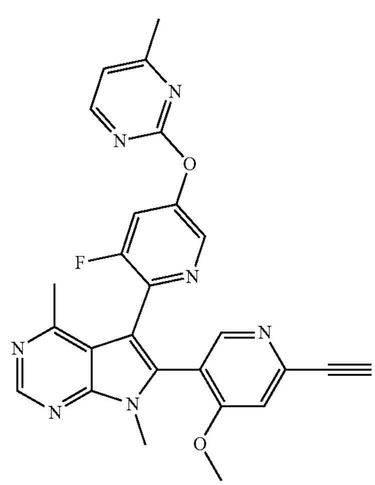 [SMILES: C#Cc1cc(OC)c(-c2c(-c3ncc(Oc4nccc(C)n4)cc3F)c3c(C)ncnc3n2C)cn1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1455 | 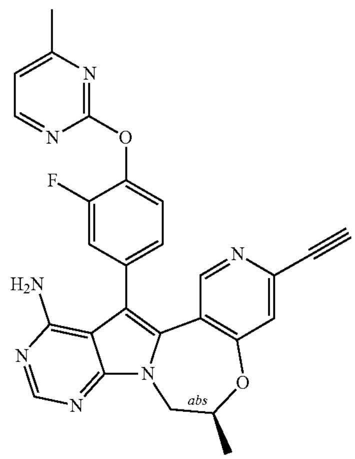 [SMILES: C#Cc1cc2c(cn1)-c1c(-c3ccc(Oc4nccc(C)n4)c(F)c3)c3c(N)ncnc3n1C[C@H](C)O2] | A | A |
| 1456 | 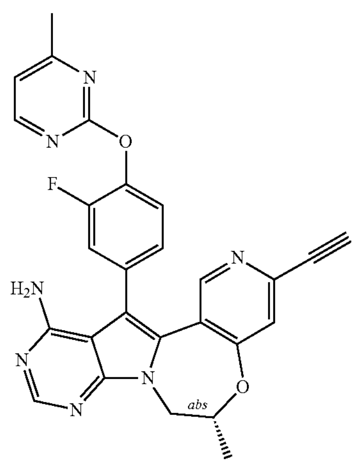 [SMILES: C#Cc1cc2c(cn1)-c1c(-c3ccc(Oc4nccc(C)n4)c(F)c3)c3c(N)ncnc3n1C[C@@H](C)O2] | A | A |
| 1457 | 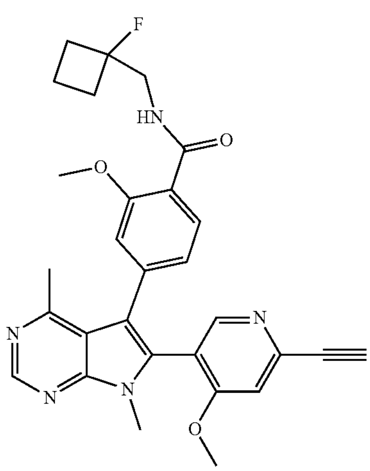 [SMILES: C#Cc1cc(OC)c(-c2c(-c3ccc(C(=O)NCC4(F)CCC4)c(OC)c3)c3c(C)ncnc3n2C)cn1] | B | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1458 | 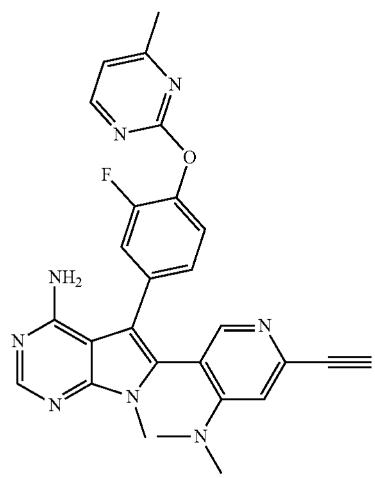 [SMILES: C#Cc1cc(N(C)C)c(-c2c(-c3ccc(Oc4nccc(C)n4)c(F)c3)c3c(N)ncnc3n2C)cn1] | A | A |
| 1459 | 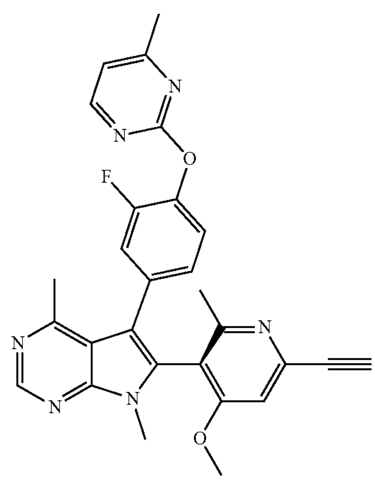 | A | A |
| 1460 | 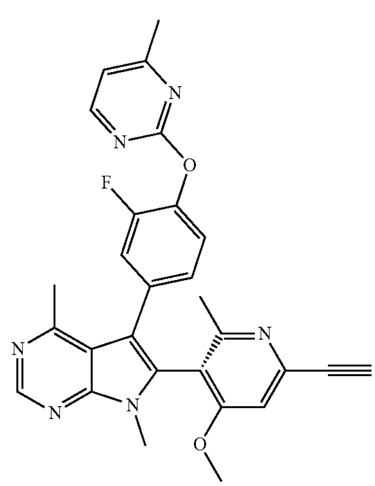 | D | C |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1461 | 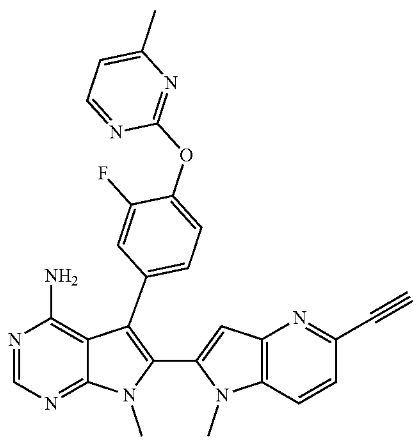 [SMILES: C#Cc1ccc2c(cc(-c3c(-c4ccc(Oc5nccc(C)n5)c(F)c4)c4c(N)ncnc4n3C)n2C)n1] | C | B |
| 1462 | 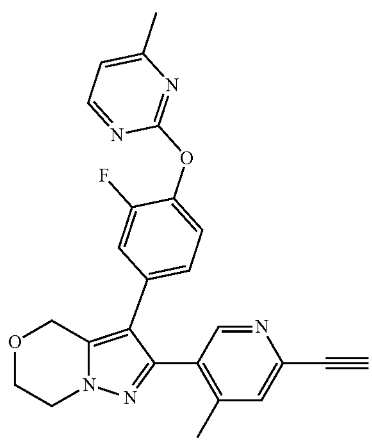 [SMILES: C#Cc1cc(C)c(-c2nn3c(c2-c2ccc(Oc4nccc(C)n4)c(F)c2)COCC3)cn1] | D | D |
| 1463 | 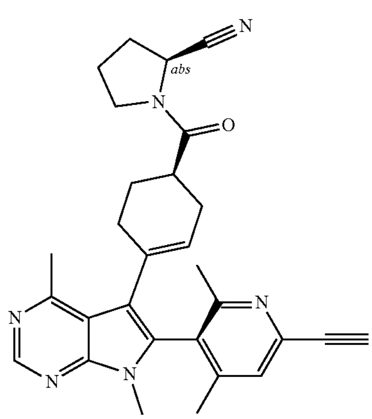 | B | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1464 | 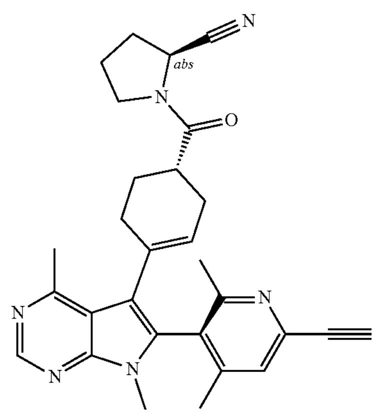 | C | C |
| 1465 | 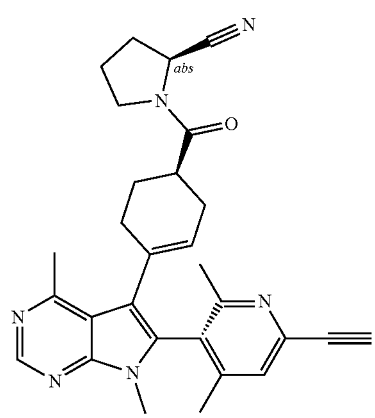 | A | A |
| 1466 | 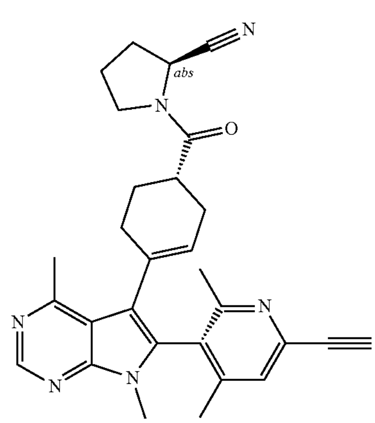 | B | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1467 | 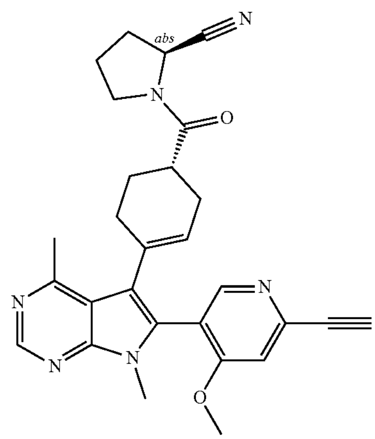 [SMILES: C#Cc1cc(OC)c(-c2c(C3=CC[C@@H](C(=O)N4CCC[C@H]4C#N)CC3)c3c(C)ncnc3n2C)cn1] | C | A |
| 1468 | 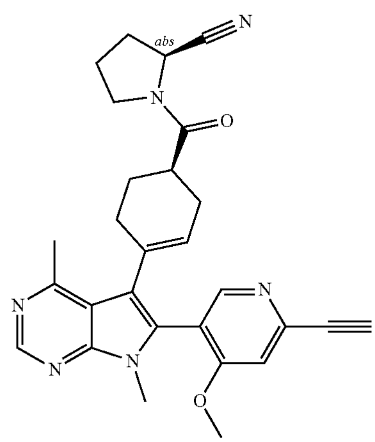 [SMILES: C#Cc1cc(OC)c(-c2c(C3=CC[C@H](C(=O)N4CCC[C@H]4C#N)CC3)c3c(C)ncnc3n2C)cn1] | A | A |
| 1469 | 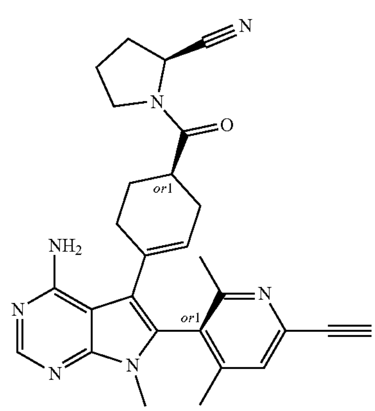 | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1470 | 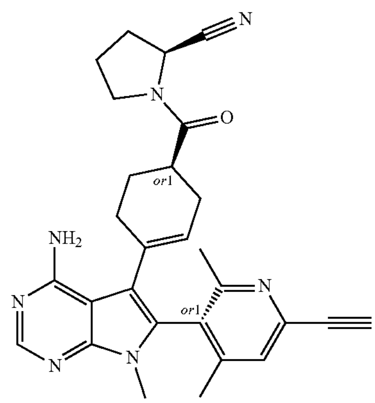 | A | A |
| 1471 | 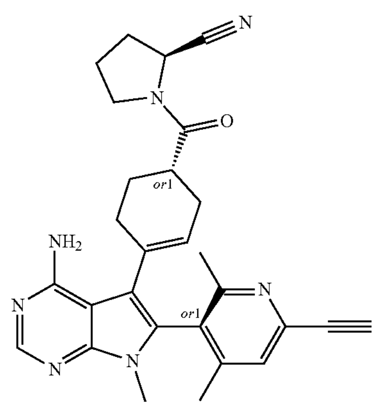 | A | A |
| 1472 | 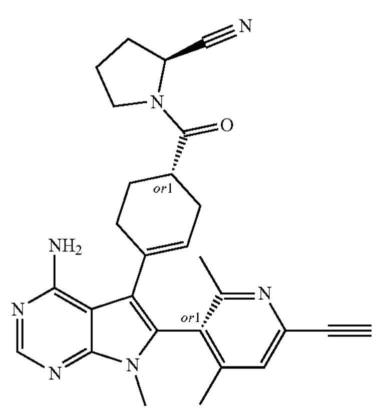 | A | A |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1473 | 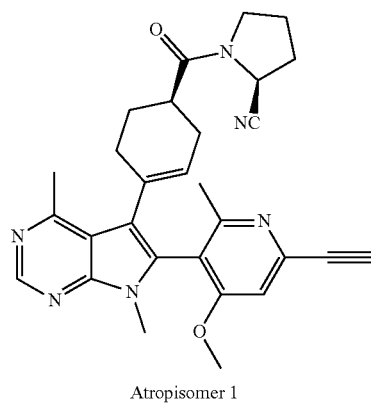 [SMILES: C#Cc1cc(OC)c(-c2c(C3=CC[C@H](C(=O)N4CCC[C@H]4C#N)CC3)c3c(C)ncnc3n2C)c(C)n1]<br>Atropisomer 1 | A | A |
| 1474 | 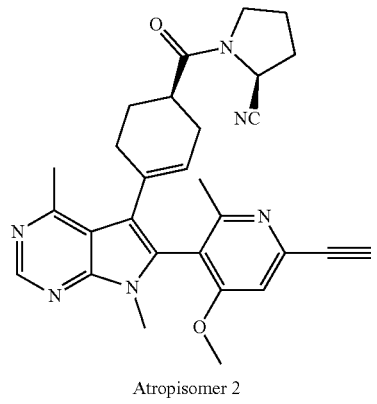 [SMILES: C#Cc1cc(OC)c(-c2c(C3=CC[C@H](C(=O)N4CCC[C@H]4C#N)CC3)c3c(C)ncnc3n2C)c(C)n1]<br>Atropisomer 2 | A | A |
| 1475 | 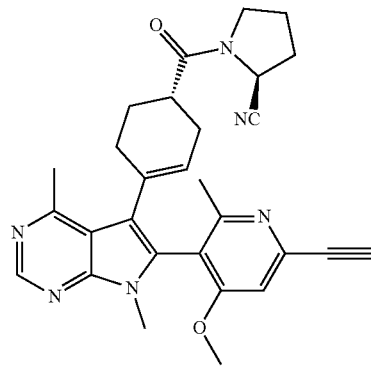<br>Atropisomer 1 | D | D |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1476 | 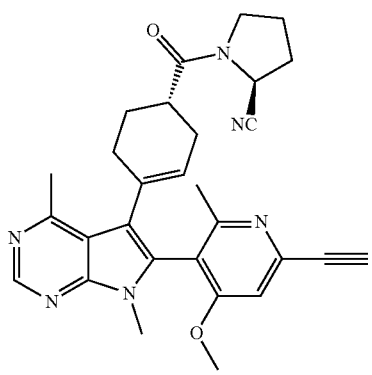<br>Atropisomer 2 | D | C |
| 1477 | 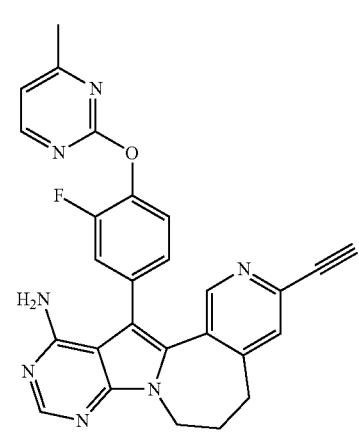 [SMILES: C#Cc1cc2c(cn1)-c1c(-c3ccc(Oc4nccc(C)n4)c(F)c3)c3c(N)ncnc3n1CCC2] | A | A |
| 1478 | 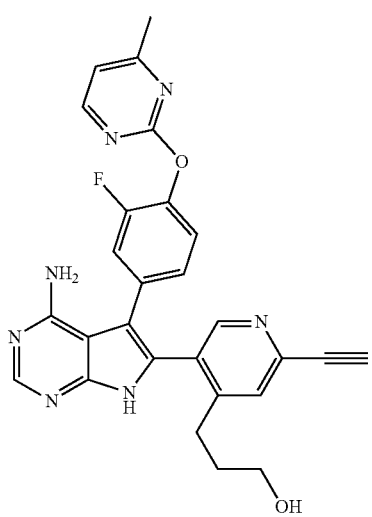 | C | B |

TABLE 1-continued
Representative Compounds of the Invention with Bioactivity Data.
| Example | Structure | Biochemical FGFR2 Caliper IC50 | Cell SNU-16 IC50 |
|---|---|---|---|
| 1479 | 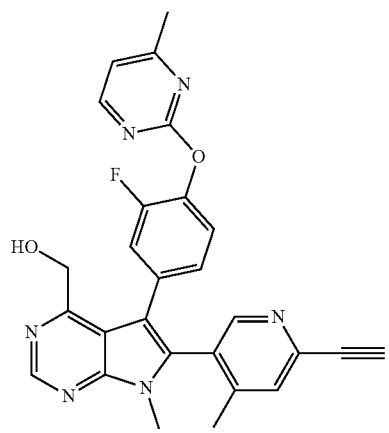 [SMILES: C#Cc1cc(C)c(-c2c(-c3ccc(Oc4nccc(C)n4)c(F)c3)c3c(CO)ncnc3n2C)cn1] | C | A |
| 1480 | 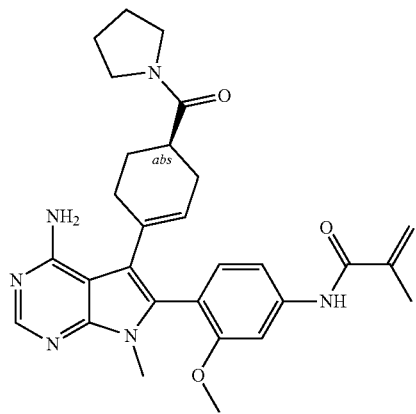 [SMILES: C=C(C)C(=O)Nc1ccc(-c2c(C3=CC[C@H](C(=O)N4CCCC4)CC3)c3c(N)ncnc3n2C)c(OC)c1] | D | C |
| 1481 | 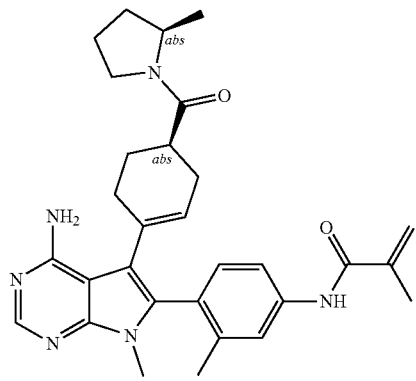 [SMILES: C=C(C)C(=O)Nc1ccc(-c2c(C3=CC[C@H](C(=O)N4CCC[C@H]4C)CC3)c3c(N)ncnc3n2C)c(C)c1] | C | B |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1482 | 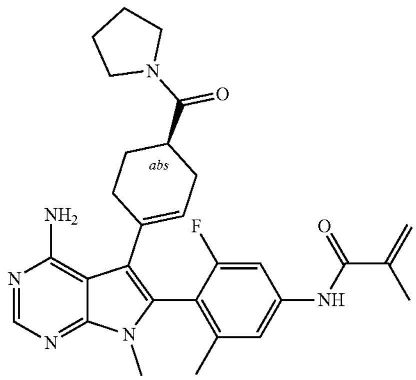 [SMILES: C=C(C)C(=O)Nc1cc(C)c(-c2c(C3=CC[C@H](C(=O)N4CCCC4)CC3)c3c(N)ncnc3n2C)c(F)c1] | A | A |
| 1483 | 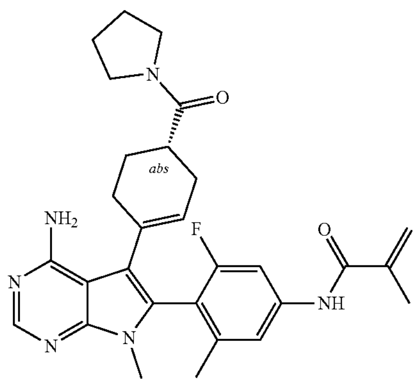 [SMILES: C=C(C)C(=O)Nc1cc(C)c(-c2c(C3=CC[C@@H](C(=O)N4CCCC4)CC3)c3c(N)ncnc3n2C)c(F)c1] | A | A |
| 1484 | atropisomer 1 | D | D |
| 1485 | atropisomer 2 | D | D |

TABLE 1-continued
Representative Compounds of the Invention with Bioactivity Data.
| Example | Structure | Biochemical FGFR2 Caliper IC50 | Cell SNU-16 IC50 |
|---------|-----------|-------------------------------|------------------|
| 1486 | 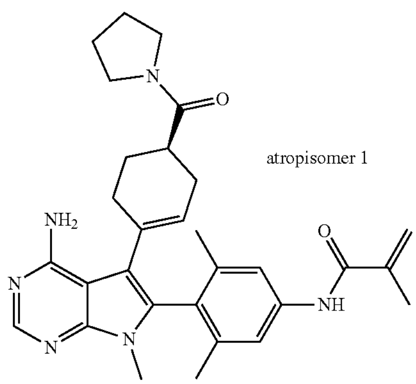 [SMILES: C=C(C)C(=O)Nc1cc(C)c(-c2c(C3=CC[C@H](C(=O)N4CCCC4)CC3)c3c(N)ncnc3n2C)c(C)c1] | D | D |
| 1487 | 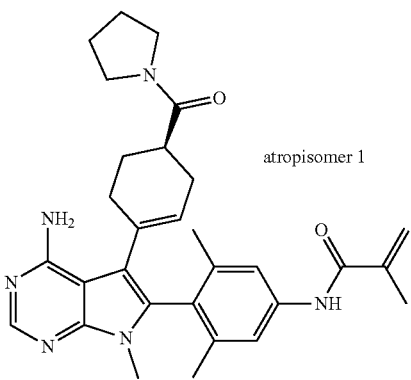 atropisomer 1 | D | D |
| 1488 | 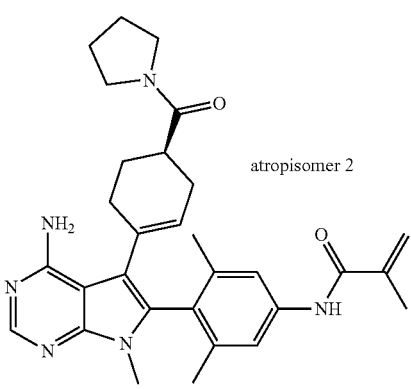 [SMILES: C=C(C)C(=O)Nc1cc(C)c(-c2c(C3=CC[C@H](C(=O)N4CCCC4)CC3)c3c(N)ncnc3n2C)c(C)c1] atropisomer 2 | C | C |
|  | 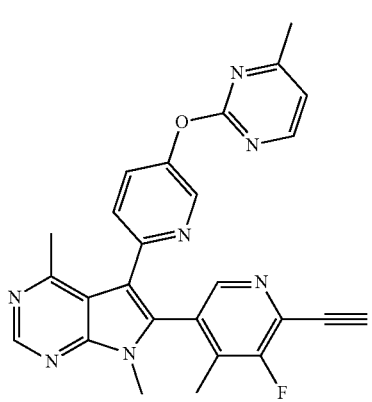 [SMILES: C#Cc1ncc(-c2c(-c3ccc(Oc4nccc(C)n4)cn3)c3c(C)ncnc3n2C)c(C)c1F] |  |  |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1489 | 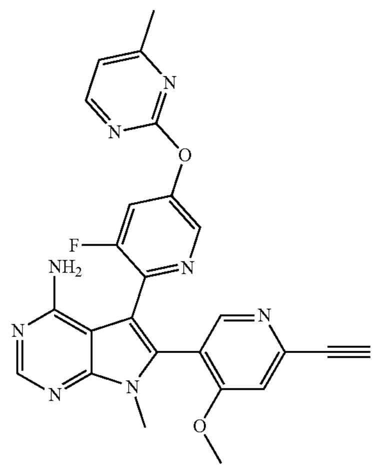 [SMILES: C#Cc1cc(OC)c(-c2c(-c3ncc(Oc4nccc(C)n4)cc3F)c3c(N)ncnc3n2C)cn1] | A | A |
| 1490 | 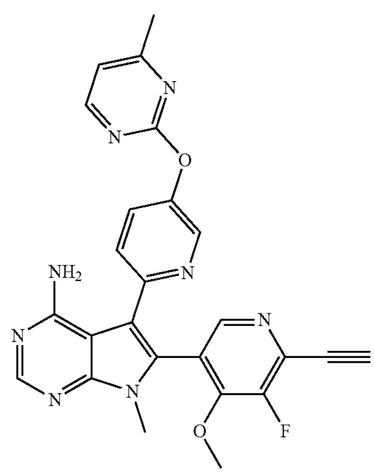 [SMILES: C#Cc1ncc(-c2c(-c3ccc(Oc4nccc(C)n4)cn3)c3c(N)ncnc3n2C)c(OC)c1F] | D | D |
| 1491 | 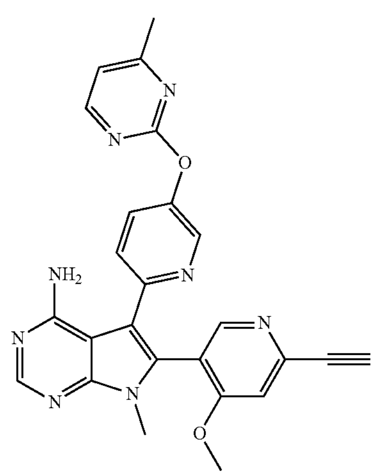 [SMILES: C#Cc1cc(OC)c(-c2c(-c3ccc(Oc4nccc(C)n4)cn3)c3c(N)ncnc3n2C)cn1] | A | A |

TABLE 1-continued

Representative Compounds of the Invention with Bioactivity Data.

| Example | Structure | Biochemical FGFR2 Caliper IC50 | Cell SNU-16 IC50 |
|---------|-----------|-------------------------------|------------------|
| 1492 | 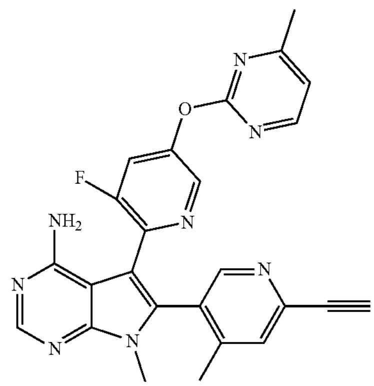 [SMILES: C#Cc1cc(C)c(-c2c(-c3ncc(Oc4nccc(C)n4)cc3F)c3c(N)ncnc3n2C)cn1] | A | A |
| 1493 | 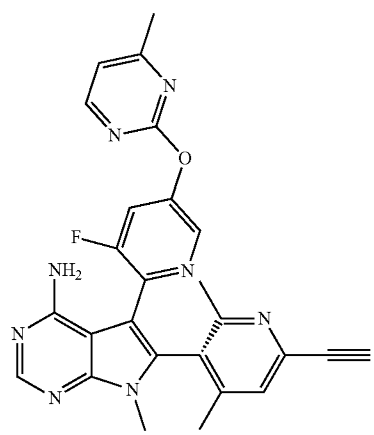 | A | A |
| 1494 | 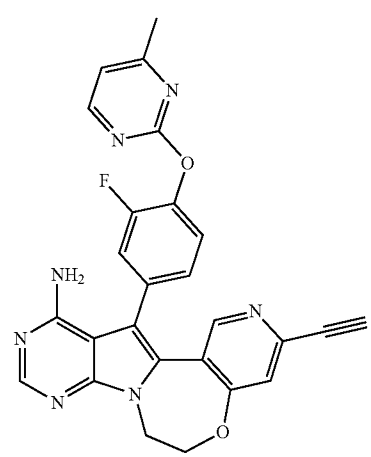 [SMILES: C#Cc1cc2c(cn1)-c1c(-c3ccc(Oc4nccc(C)n4)c(F)c3)c3c(N)ncnc3n1CCO2] | A | A |

TABLE 1-continued

Representative Compounds of the Invention with Bioactivity Data.

| Example | Structure | Biochemical FGFR2 Caliper IC50 | Cell SNU-16 IC50 |
|---|---|---|---|
| 1495 | 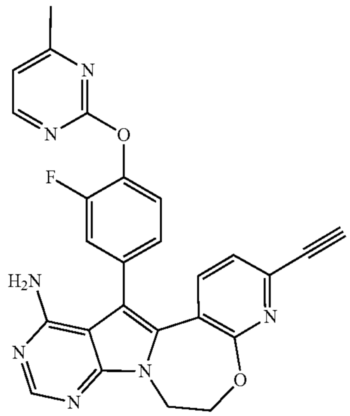 [SMILES: C#Cc1ccc2c(n1)OCCn1c-2c(-c2ccc(Oc3nccc(C)n3)c(F)c2)c2c(N)ncnc21] | A | A |
| 1496 | 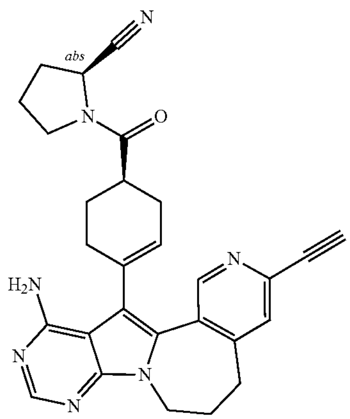 [SMILES: C#Cc1cc2c(cn1)-c1c(C3=CC[C@H](C(=O)N4CCC[C@H]4C#N)CC3)c3c(N)ncnc3n1CCC2] | C | |

In chemical structures in Table 1, above, when a stereocenter is depicted with a dashed or wedged bond and labeled "abs" (or unlabeled), the compound is essentially a single isomer at that stereocenter (rather than an equimolar mixture), and the absolute stereochemistry is as shown in the chemical structure. (See, for example, the structure of Example 146.) When a stereocenter is depicted with a dashed or wedged bond and also labeled "or 1", the compound is a single isomer at that stereocenter, but the absolute stereochemistry at that stereocenter has not been determined. (See, for example, the structures of Examples 397 and 398.) When a stereocenter is depicted with a dashed or wedged bond and also labeled "and 1" or "&1", the compound is a mixture of two isomers at that stereocenter: the structure as drawn, and the isomer in which that stereogenic center has the opposite configuration. (See, for example, the structure of Example 581.)

Certain compounds depicted in Table 1, above, exist in solution at room temperature as non-interconverting atropisomers across a biaryl bond. When one of the atoms of a biaryl bond is labeled as "or 1", this signifies that the compound exists in solution at room temperature as non-interconverting atropisomers, and the compound is essentially a single atropisomer (rather than an equimolar mixture). (See, for example, the structures of Examples 516 and 517.)

In some embodiments, the present invention provides a compound in Table 1, above, wherein the compound is denoted as having a Biochemical FGFR2 Caliper $IC_{50}$ of "A". In some embodiments, the present invention provides a compound in Table 1, above, wherein the compound is denoted as having a Biochemical FGFR2 Caliper $IC_{50}$ of "A" or "B". In some embodiments, the present invention provides a compound in Table 1, above, wherein the compound is denoted as having a Biochemical FGFR2 Caliper $IC_{50}$ of "A" or "B" or "C".

In some embodiments, the present invention provides a compound in Table 1, above, wherein the compound is denoted as having a Cell SNU-16 $IC_{50}$ of "A". In some embodiments, the present invention provides a compound in Table 1, above, wherein the compound is denoted as having a Cell SNU-16 $IC_{50}$ of "A" or "B". In some embodiments, the present invention provides a compound in Table 1, above, wherein the compound is denoted as having a Cell SNU-16 $IC_{50}$ of "A" or "B" or "C".

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation, and Administration

Pharmaceutically Acceptable Compositions

According to another embodiment, the invention provides a composition comprising a compound of this invention, or a pharmaceutically acceptable derivative thereof, and a pharmaceutically acceptable carrier, adjuvant, or vehicle. In some embodiments, the invention provides a pharmaceutical composition comprising a compound of this invention, and a pharmaceutically acceptable carrier. The amount of compound in compositions of this invention is such that is effective to measurably inhibit a FGFR2 protein kinase, or a mutant thereof, in a biological sample or in a patient. In certain embodiments, the amount of compound in compositions of this invention is such that it is effective to measurably inhibit a FGFR2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The terms "subject" and "patient," as used herein, means an animal (i.e., a member of the kingdom animal), preferably a mammal, and most preferably a human. In some embodiments, the subject is a human, mouse, rat, cat, monkey, dog, horse, or pig. In some embodiments, the subject is a human. In some embodiments, the subject is a mouse, rat, cat, monkey, dog, horse, or pig.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a FGFR2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal or vaginal administration. These can be prepared by mixing the agent with a suitable non-irritating excipient that is solid at room temperature but liquid at rectal or vaginal temperature and therefore will melt in the rectum or vagina to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the patient treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

The precise dose to be employed in the compositions will also depend on the route of administration and should be decided according to the judgment of the practitioner and each subject's circumstances. In specific embodiments of the disclosure, suitable dose ranges for oral administration of the compounds of the disclosure are generally about 1 mg/day to about 1000 mg/day. In some embodiments, the oral dose is about 1 mg/day to about 800 mg/day. In some embodiments, the oral dose is about 1 mg/day to about 500 mg/day. In some embodiments, the oral dose is about 1 mg/day to about 250 mg/day. In some embodiments, the oral dose is about 1 mg/day to about 100 mg/day. In some embodiments, the oral dose is about 5 mg/day to about 50 mg/day. In some embodiments, the oral dose is about 5 mg/day. In some embodiments, the oral dose is about 10 mg/day. In some embodiments, the oral dose is about 20 mg/day. In some embodiments, the oral dose is about 30 mg/day. In some embodiments, the oral dose is about 40 mg/day. In some embodiments, the oral dose is about 50 mg/day. In some embodiments, the oral dose is about 60 mg/day. In some embodiments, the oral dose is about 70 mg/day. In some embodiments, the oral dose is about 100 mg/day. It will be recognized that any of the dosages listed herein may constitute an upper or lower dosage range and may be combined with any other dosage to constitute a dosage range comprising an upper and lower limit.

In some embodiments, pharmaceutically acceptable compositions contain a provided compound and/or a pharmaceutically acceptable salt thereof at a concentration ranging from about 0.01 to about 90 wt %, about 0.01 to about 80 wt %, about 0.01 to about 70 wt %, about 0.01 to about 60 wt %, about 0.01 to about 50 wt %, about 0.01 to about 40 wt %, about 0.01 to about 30 wt %, about 0.01 to about 20 wt %, about 0.01 to about 2.0 wt %, about 0.01 to about 1 wt %, about 0.05 to about 0.5 wt %, about 1 to about 30 wt %, or about 1 to about 20 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

Pharmaceutically acceptable carriers are well-known to those skilled in the art, and include, e.g., adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient.

Examples of pharmaceutically acceptable carriers may include, e.g., water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remin on's: The Science and Practice of Pharmacy, 22nd Ed. (Allen, Loyd V., Jr ed., Pharmaceutical Press (2012)); Modern Pharmaceutics, $5^{th}$ Ed. (Alexander T. Florence, Juergen Siepmann, CRC Press (2009)); Handbook of Pharmaceutical Excipients, $7^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

The pharmaceutically acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, e.g., detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain wetting or emulsifying agents, or pH buffering agents.

Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, e.g., sweetening agents such as fructose, aspartame or saccharin; flavoring agents such as peppermint, oil of wintergreen, or cherry; coloring agents; and preservative agents, to provide a pharmaceutically palatable preparation.

Uses of Compounds and Pharmaceutically Acceptable Compositions

Compounds and compositions described herein are generally useful for the inhibition of a kinase or a mutant thereof. In some embodiments, the kinase inhibited by the compounds and compositions described herein is a fibroblast growth factor receptor (FGFR). In some embodiments, the kinase inhibited by the compounds and compositions described herein is one or more of FGFR1, FGFR2, FGFR3, and FGFR4. In some embodiments, the kinase inhibited by the compounds and compositions described herein is FGFR2.

Compounds or compositions of the disclosure can be useful in applications that benefit from inhibition of FGFR2 enzymes. For example, FGFR2 inhibitors of the present invention are useful for the treatment of proliferative diseases generally.

Activating FGFR2 gene fusions have been detected in numerous cancers including intrahepatic cholangiocarcinoma, hepatocellular carcinoma, breast cancer, prostate cancer, lung squamous cell carcinoma, thyroid cancer, gastric cancer, and ovarian cancer. (I. S. Babina and N. C. Turner, Nat. Rev. Cancer 2017, 17:318-332; Y-M Wu, et al. Cancer Discov. 3:636-647; and references cited therein.)

FGFR2 amplification has been described in gastric cancer, breast cancer, triple negative breast cancer, and rectal cancer. (I. S. Babina and N. C. Turner, Nat. Rev. Cancer 2017, 17:318-332; M. Katoh, Nat. Rev. Clin. Oncol. 2019, 16:105-122; and references cited therein.)

Activating FGFR2 mutations have been detected in endometrial carcinoma, non-small cell lung cancer, lung squamous cell carcinoma, gastric cancer, breast cancer, and urothelial cancers. The most common mutations include those in the intracellular kinase domain (e.g., N549K and K659N/M) and those in the extracellular domain (S252W and P253R). Resistance mutations that occur in FGFR2 from treatment with pan-FGFR1-3 inhibitors can also be targeted with FGFR2 inhibitors. These include V564F, E565A, N549K/H/T, and L617V. (I. S. Babina and N. C. Turner, Nat. Rev. Cancer 2017, 17:318-332; M. Katoh, Nat. Rev. Clin. Oncol. 2019, 16:105-122; R. Porta, et al. Crit. Rev. Oncol. Hematol. 2017, 113:256-267; and references cited therein).

Inhibition of FGFR2 also has anti-tumor activity in tumors with increased expression of FGFR2 ligands (FGFs1-4, 7, 8, 10, 21-23) (N. Turner and R. Grose, Nat. Rev. Cancer 2010, 10:116-129; and references cited therein).

Inhibition of FGFR2 also has anti-tumor activity in tumors with amplification or overexpression of the FGFR adaptor protein FRS2. (I. S. Babina and N. C. Turner, Nat. Rev. Cancer 2017, 17:318-332; and references cited therein.)

Selective inhibition of FGFR2 can generally be effective in indications where pan-FGFR1-3 inhibitors are effective. Such indications are described in I. S. Babina and N. C. Turner, Nat. Rev. Cancer 2017, 17:318-332; M. Katoh, Nat. Rev. Clin. Oncol. 2019, 16:105-122; R. Porta, et al. Crit. Rev. Oncol. Hematol. 2017, 113:256-267; and references cited therein.

Activating mutations in FGFR2 have also been detected in craniosynostotic syndromes including Crouzon, Apert, Pfeiffer, Antley-Bixler, Beare-Stevenson cutis gyrate, Jackson-Weiss, Bent Bone Dysplasia, and Seathre-Chotzen-like syndromes which result in the premature fusion of cranial sutures. (S. C. Azoury, et al. Int. J. Biol. Sci. 2017, 13:1479-1488; and references cited therein.) Inhibition of FGFR2 is also effective in such craniosynostotic syndromes.

The activity of a compound utilized in this invention as an inhibitor of an FGFR kinase, for example, FGFR2, or a mutant thereof, may be assayed in vitro, in vivo or in a cell line. In vitro assays include assays that determine inhibition of either the phosphorylation activity and/or the subsequent functional consequences, or ATPase activity of activated FGFR2, or a mutant thereof. Alternative in vitro assays quantitate the ability of the inhibitor to bind to FGFR2.

Inhibitor binding may be measured by radiolabeling the inhibitor prior to binding, isolating the inhibitor/FGFR2 complex and determining the amount of radiolabel bound. Alternatively, inhibitor binding may be determined by running a competition experiment where new inhibitors are incubated with FGFR2 bound to known radioligands. Representative in vitro and in vivo assays useful in assaying an FGFR2 inhibitor include those described and disclosed in the patent and scientific publications described herein. Detailed conditions for assaying a compound utilized in this invention as an inhibitor of FGFR2, or a mutant thereof, are set forth in the Examples below.

Treatment of Disorders

Provided compounds are inhibitors of FGFR2 and are therefore useful for treating one or more disorders associated with activity of FGFR2 or mutants thereof. Thus, in certain embodiments, the present invention provides a method of treating an FGFR2-mediated disorder in a subject comprising administering a therapeutically effective amount of a compound of the present invention, or a pharmaceutically acceptable salt thereof, or a pharmaceutically acceptable composition of either of the foregoing, to a subject in need thereof in certain embodiments, the present invention provides a method of treating an FGFR2-mediated disorder in a subject comprising administering a therapeutically effective amount of a compound of the present invention, or a pharmaceutically acceptable composition thereof, to a subject in need thereof.

As used herein, the term "FGFR2-mediated" disorders, diseases, and/or conditions means any disease or other deleterious condition in which FGFR2 or a mutant thereof is known to play a role. Accordingly, another embodiment of the present invention relates to treating or lessening the severity of one or more diseases in which FGFR2, or a mutant thereof, is known to play a role. Such FGFR2-mediated disorders include but are not limited to proliferative disorders (e.g. cancer) and craniosynostotic syndromes.

In some embodiments, the present invention provides a method for treating one or more disorders, wherein the disorders are selected from proliferative disorders and craniosynostotic syndromes, said method comprising administering to a patient in need thereof, a therapeutically effective amount of a compound of the present invention, or a pharmaceutically acceptable salt thereof, or a pharmaceutically acceptable composition of either of the foregoing. In some embodiments, the present invention provides a method for treating one or more disorders, wherein the disorders are selected from proliferative disorders and craniosynostotic syndromes, said method comprising administering to a patient in need thereof, a therapeutically effective amount of a compound of the present invention, or a pharmaceutically acceptable composition thereof.

In some embodiments, the present invention provides a method of treating a disorder in a subject, said method comprising administering a therapeutically effective amount of a compound of the present invention, or a pharmaceutically acceptable salt thereof, or a pharmaceutical composition of either of the foregoing, to a subject in need thereof, wherein the disorder is bile duct cancer, liver cancer, breast cancer, prostate cancer, lung cancer, thyroid cancer, gastric cancer, ovarian cancer, rectal cancer, endometrial cancer, or urothelial cancer. In some embodiments, the disorder is intrahepatic cholangiocarcinoma. In some embodiments, the disorder is hepatocellular carcinoma. In some embodiments, the disorder is lung squamous cell carcinoma or non-small cell lung cancer.

In some embodiments, the disorder is bile duct cancer. In some embodiments, the bile duct cancer is intrahepatic cholangiocarcinoma. In some embodiments, the disorder is liver cancer. In some embodiments, the liver cancer is hepatocellular carcinoma. In some embodiments, the disorder is lung cancer. In some embodiments, the lung cancer is lung squamous cell carcinoma or non-small cell lung cancer.

In some embodiments, the present invention provides a method of treating intrahepatic cholangiocarcinoma in a subject, said method comprising administering a therapeutically effective amount of a compound of the present invention, or a pharmaceutically acceptable salt thereof, or a pharmaceutical composition of either of the foregoing, to a subject in need thereof. In some embodiments, the present invention provides a method of treating hepatocellular carcinoma in a subject, said method comprising administering a therapeutically effective amount of a compound of the present invention, or a pharmaceutically acceptable salt thereof, or a pharmaceutical composition of either of the foregoing, to a subject in need thereof. In some embodiments, the present invention provides a method of treating lung squamous cell carcinoma or non-small cell lung cancer in a subject, said method comprising administering a therapeutically effective amount of a compound of the present invention, or a pharmaceutically acceptable salt thereof, or a pharmaceutical composition of either of the foregoing, to a subject in need thereof.

In some embodiments, the disorder is associated with FGFR2 signaling. FGFR2 and other receptor tyrosine kinases (RTKs) are known to have multiple upstream and downstream signaling pathways (see Turner and Grose, Nat. Rev. Cancer (2010)10, 116), and inhibition of FGFR2 can be used to treat disorders associated with aberrant signaling within those pathways. In some embodiments, the disorder is associated with FGF signaling, JAK-STAT signaling, PI3K-Akt signaling, PLC-gamma signaling, or MAPK signaling.

In some embodiments, the method of treatment comprises the steps of: i) identifying a subject in need of such treatment; (ii) providing a disclosed compound, or a pharmaceutically acceptable salt thereof and (iii) administering said provided compound in a therapeutically effective amount to treat, suppress and/or prevent the disease state or condition in a subject in need of such treatment.

In some embodiments, the method of treatment comprises the steps of: i) identifying a subject in need of such treatment; (ii) providing a composition comprising a disclosed compound, or a pharmaceutically acceptable salt thereof and (iii) administering said composition in a therapeutically effective amount to treat, suppress and/or prevent the disease state or condition in a subject in need of such treatment.

Another aspect of the invention provides a compound according to the definitions herein, or a pharmaceutically acceptable salt thereof, or a pharmaceutical composition of either of the foregoing, for use in the treatment of a disorder described herein. Another aspect of the invention provides the use of a compound according to the definitions herein, or a pharmaceutically acceptable salt thereof, or a pharmaceutical composition of either of the foregoing, for the treatment of a disorder described herein. Similarly, the invention provides the use of a compound according to the definitions herein, or a pharmaceutically acceptable salt thereof, for the preparation of a medicament for the treatment of a disorder described herein.

Proliferative Disorders

In some embodiments, the disorder is a proliferative disorder. In some embodiments, the proliferative disorder is cancer. In some embodiments, the proliferative disorder is leukemia, breast cancer, lung cancer, colorectal cancer, or a combination thereof. In some embodiments, the proliferative disorder is leukemia. In some embodiments, the proliferative disorder is breast cancer. In some embodiments, the proliferative disorder is lung cancer. In some embodiments, the proliferative disorder is colorectal cancer.

In some embodiments, the proliferative disorder is intrahepatic cholangiocarcinoma, hepatocellular carcinoma, breast cancer, prostate cancer, lung squamous cell carcinoma, thyroid cancer, gastric cancer, ovarian cancer, rectal cancer, endometrial carcinoma, non-small cell lung cancer, or urothelial cancer. In some embodiments, the proliferative disorder is intrahepatic cholangiocarcinoma, hepatocellular carcinoma, breast cancer, prostate cancer, lung squamous cell carcinoma, thyroid cancer, gastric cancer, or ovarian cancer. In some embodiments, the proliferative disorder is gastric cancer, breast cancer, triple negative breast cancer, or rectal cancer. In some embodiments, the proliferative disorder is endometrial carcinoma, non-small cell lung cancer, lung squamous cell carcinoma, gastric cancer, breast cancer, or urothelial cancer.

In some embodiments, the proliferative disorder is associated with one or more activating mutations in FGFR2. In some embodiments, the activating mutation in FGFR2 is a mutation to one or more of the intracellular kinase domain and the extracellular domain. In some embodiments, the activating mutation in FGFR2 is a mutation to the intracellular kinase domain. In some embodiments, the activating mutation in FGFR2 is a mutation to the extracellular domain. In some embodiments the activating mutation in FGFR2 is selected from N549K, K659N/M, S252W, P253R, and combinations thereof. In some embodiments the activating mutation in FGFR2 is N549K or K659N/M. In some embodiments the activating mutation in FGFR2 is N549K. In some embodiments the activating mutation in FGFR2 is K659N/M. In some embodiments the activating mutation in FGFR2 is S252W or P253R. In some embodiments the activating mutation in FGFR2 is S252W. In some embodiments the activating mutation in FGFR2 is P253R.

In some embodiments the proliferative disorder is associated with one or more resistance mutations in FGFR2. In some embodiments the resistance mutation in FGFR2 is selected from V564F, E565A, N549K/H/T, and L617V, and combinations thereof. In some embodiments the resistance mutation in FGFR2 is V564F. In some embodiments the resistance mutation in FGFR2 is E565A. In some embodiments the resistance mutation in FGFR2 is N549K/H/T. In some embodiments the resistance mutation in FGFR2 is L617V.

Routes of Administration and Dosage Forms

The compounds and compositions, according to the methods of the present invention, may be administered using any amount and any route of administration effective for treating or lessening the severity of the disorder (e.g. a proliferative disorder or craniosynostotic syndrome). The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Dosage Amounts and Regimens

In accordance with the methods of the present disclosure, the compounds of the disclosure are administered to the subject in a therapeutically effective amount, e.g., to reduce or ameliorate symptoms of the disorder in the subject. This amount is readily determined by the skilled artisan, based upon known procedures, including analysis of titration curves established in vivo and methods and assays disclosed herein.

In some embodiments, the methods comprise administration of a therapeutically effective dosage of the compounds of the disclosure. In some embodiments, the therapeutically effective dosage is at least about 0.0001 mg/kg body weight, at least about 0.001 mg/kg body weight, at least about 0.01 mg/kg body weight, at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the therapeutically effective dosage is in the range of about 0.1 mg to about 10 mg/kg body weight, about 0.1 mg to about 6 mg/kg body weight, about 0.1 mg to about 4 mg/kg body weight, or about 0.1 mg to about 2 mg/kg body weight.

In some embodiments the therapeutically effective dosage is in the range of about 1 to 500 mg, about 2 to 150 mg, about 2 to 120 mg, about 2 to 80 mg, about 2 to 40 mg, about 5 to 150 mg, about 5 to 120 mg, about 5 to 80 mg, about 10 to 150 mg, about 10 to 120 mg, about 10 to 80 mg, about 10 to 40 mg, about 20 to 150 mg, about 20 to 120 mg, about 20 to 80 mg, about 20 to 40 mg, about 40 to 150 mg, about 40 to 120 mg or about 40 to 80 mg.

In some embodiments, the methods comprise a single dosage or administration (e.g., as a single injection or deposition). Alternatively, in some embodiments, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

Inhibition of Protein Kinases

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting activity of FGFR2, or a mutant thereof, in a biological sample comprising the step of contacting said biological sample with a compound of this invention, or a composition comprising said compound. In certain embodiments, the invention relates to a method of reversibly inhibiting FGFR2, or a mutant thereof, activity in a biological sample comprising the step of contacting said biological sample with a compound of this invention, or a composition comprising said compound. In certain embodiments, the invention relates to a method of irreversibly inhibiting FGFR2, or a mutant thereof, activity in a biological sample comprising the step of contacting said biological sample with a compound of this invention, or a composition comprising said compound.

In some embodiments, the invention relates to a method of irreversibly inhibiting FGFR2, or a mutant thereof, wherein a compound of this invention forms a covalent bond with FGFR2, or a mutant thereof. In some embodiments, the invention relates to a method of irreversibly inhibiting FGFR2, or a mutant thereof, wherein a compound of this invention forms a covalent bond between $R^W$ of the compound and a cysteine of the FGFR2, or a mutant thereof. In some embodiments, the invention relates to a method of irreversibly inhibiting FGFR2, or a mutant thereof, wherein a compound of this invention forms a covalent bond between $R^W$ of the compound and Cys491 of the FGFR2, or a mutant thereof.

According to another embodiment, the invention relates to an FGFR2, or a mutant thereof, irreversibly inhibited by a compound of this invention. In some embodiments, the invention relates to an FGFR2, or a mutant thereof, covalently bonded to a compound of this invention. In some embodiments, the invention relates to an FGFR2, or a mutant thereof, covalently bonded to a compound of this invention, wherein the covalent bond is between $R^W$ of the compound and a cysteine of the FGFR2, or a mutant thereof. In some embodiments, the invention relates to an FGFR2, or a mutant thereof, covalently bonded to a compound of this invention, wherein the covalent bond is between $R^W$ of the compound and Cys491 of the FGFR2, or a mutant thereof.

In another embodiment, the invention provides a method of selectively inhibiting FGFR2 over one or more of FGFR1, FGFR3, and FGFR4. In some embodiments, a compound of the present invention is more than 5-fold selective over FGFR1, FGFR3, and FGFR4. In some embodiments, a compound of the present invention is more than 10-fold selective over FGFR1, FGFR3, and FGFR4. In some embodiments, a compound of the present invention is more than 50-fold selective over FGFR1, FGFR3, and FGFR4. In some embodiments, a compound of the present invention is more than 100-fold selective over FGFR1, FGFR3, and FGFR4. In some embodiments, a compound of the present invention is more than 200-fold selective over FGFR1, FGFR3, and FGFR4.

The term "biological sample", as used herein, includes, without limitation, cell cultures or extracts thereof biopsied material obtained from a mammal or extracts thereof and blood, saliva, urine, feces, semen, tears, or other body fluids or extracts thereof.

Inhibition of activity of FGFR2 (or a mutant thereof) in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of FGFR2, or a mutant thereof, in a patient comprising the step of administering to said patient a compound of the present invention, or a composition comprising said compound. According to certain embodiments, the invention relates to a method of reversibly or irreversibly inhibiting activity of one or more of FGFR2, or a mutant thereof, in a patient comprising the step of administering to said patient a compound of the present invention, or a composition comprising said compound. In some embodiments, the invention relates to a method of reversibly inhibiting activity of one or more of FGFR2, or a mutant thereof, in a patient comprising the step of administering to said patient a compound of the present invention, or a composition comprising said compound. In some embodiments, the invention relates to a method of irreversibly inhibiting activity of one or more of FGFR2, or a mutant thereof, in a patient comprising the step of administering to said patient a compound of the present invention, or a composition comprising said compound.

In some embodiments, the invention relates to a method of irreversibly inhibiting activity of one or more of FGFR2, or a mutant thereof, in a patient, comprising the step of administering to said patient a compound of the present invention, or a composition comprising said compound, wherein the compound forms a covalent bond with the FGFR2, or a mutant thereof. In some embodiments, the invention relates to a method of irreversibly inhibiting activity of one or more of FGFR2, or a mutant thereof, in a patient, comprising the step of administering to said patient a compound of the present invention, or a composition comprising said compound, wherein the compound forms a covalent bond between $R^W$ of the compound and a cysteine of the FGFR2, or a mutant thereof. In some embodiments, the invention relates to a method of irreversibly inhibiting activity of one or more of FGFR2, or a mutant thereof, in a patient, comprising the step of administering to said patient a compound of the present invention, or a composition comprising said compound, wherein the compound forms a covalent bond between $R^W$ of the compound and Cys491 of the FGFR2, or a mutant thereof.

According to another embodiment, the present invention provides a method for treating a disorder mediated by FGFR2, or a mutant thereof, in a patient in need thereof, comprising the step of administering to said patient a compound according to the present invention or pharmaceutically acceptable composition thereof. Such disorders are described in detail herein. In some embodiments, the present invention provides a method for treating a disorder mediated by FGFR2, or a mutant thereof, in a patient in need thereof, comprising the step of administering to said patient a compound according to the present invention or pharmaceutically acceptable composition thereof, wherein the compound reversibly inhibits the FGFR2, or a mutant thereof.

In some embodiments, the present invention provides a method for treating a disorder mediated by FGFR2, or a mutant thereof, in a patient in need thereof, comprising the step of administering to said patient a compound according to the present invention or pharmaceutically acceptable composition thereof, wherein the compound irreversibly inhibits the FGFR2, or a mutant thereof. In some embodiments, the present invention provides a method for treating a disorder mediated by FGFR2, or a mutant thereof, in a patient in need thereof, comprising the step of administering to said patient a compound according to the present invention or pharmaceutically acceptable composition thereof, wherein the compound forms a covalent bond with the FGFR2, or a mutant thereof. In some embodiments, the present invention provides a method for treating a disorder mediated by FGFR2, or a mutant thereof, in a patient in need thereof, comprising the step of administering to said patient a compound according to the present invention or pharmaceutically acceptable composition thereof, wherein the compound forms a covalent bond between $R^W$ of the compound and a cysteine of the FGFR2, or a mutant thereof. In some embodiments, the present invention provides a method for treating a disorder mediated by FGFR2, or a mutant thereof, in a patient in need thereof, comprising the step of administering to said patient a compound according to the present invention or pharmaceutically acceptable composition thereof, wherein the compound forms a covalent bond between $R^W$ of the compound and Cys491 of the FGFR2, or a mutant thereof.

According to another embodiment, the present invention provides a method of inhibiting signaling activity of FGFR2, or a mutant thereof, in a subject, comprising administering a therapeutically effective amount of a compound according to the present invention, or a pharmaceutically acceptable composition thereof, to a subject in need thereof. In some embodiments, the present invention provides a method of inhibiting FGFR2 signaling activity in a subject, comprising administering a therapeutically effective amount of a compound according to the present invention, or a pharmaceutically acceptable composition thereof, to a subject in need thereof.

In some embodiments, the present invention provides a method for treating a disorder mediated by FGFR2, or a mutant thereof, in a patient in need thereof, comprising the step of administering to said patient a compound according to the present invention or pharmaceutically acceptable composition thereof, wherein the compound reversibly inhibits the FGFR2, or a mutant thereof.

The compounds described herein can also inhibit FGFR2 function through incorporation into agents that catalyze the destruction of FGFR2. For example, the compounds can be incorporated into proteolysis targeting chimeras (PROTACs). A PROTAC is a bifunctional molecule, with one portion capable of engaging an E3 ubiquitin ligase, and the other portion having the ability to bind to a target protein meant for degradation by the cellular protein quality control machinery. Recruitment of the target protein to the specific E3 ligase results in its tagging for destruction (i.e., ubiquitination) and subsequent degradation by the proteasome. Any E3 ligase can be used. The portion of the PROTAC that engages the E3 ligase is connected to the portion of the PROTAC that engages the target protein via a linker which consists of a variable chain of atoms. Recruitment of FGFR2 to the E3 ligase will thus result in the destruction of the FGFR2 protein. The variable chain of atoms can include, for example, rings, heteroatoms, and/or repeating polymeric units. It can be rigid or flexible. It can be attached to the two portions described above using standard techniques in the art of organic synthesis.

Combination Therapies

Depending upon the particular disorder, condition, or disease, to be treated, additional therapeutic agents, that are normally administered to treat that condition, may be administered in combination with compounds and compositions of this invention. As used herein, additional therapeutic agents that are normally administered to treat a particular disease, or condition, are known as "appropriate for the disease, or condition, being treated."

Accordingly, in certain embodiments, the method of treatment comprises administering the compound or composition of the invention in combination with one or more additional therapeutic agents. In certain other embodiments, the methods of treatment comprise administering the compound or composition of the invention as the only therapeutic agent.

In some embodiments, the one or more additional therapeutic agents is selected from antibodies, antibody-drug conjugates, kinase inhibitors, immunomodulators, and histone deacetylase inhibitors. In some embodiments, the one or more additional therapeutic agent is selected from the following agents, or a pharmaceutically acceptable salt thereof: BCR-ABL inhibitors: e.g. imatinib, inilotinib, nilotinib, dasatinib, bosutinib, ponatinib, bafetinib, danusertib, saracatinib, PF03814735; ALK inhibitors (see Dardaei et al, 2018, Nat Med.; 24(4):512-517): e.g. crizotinib, NVP-TAE684, ceritinib, alectinib, brigatinib, entrecinib, lorlatinib; BRAF inhibitors (see Prahallad et al, 2015, Cell Rep. 12, 1978-1985): e.g. vemurafenib, dabrafenib; FGFR inhibitors: e.g. infigratinib, dovitinib, erdafitinib, BLU-554, AZD4547; FLT3 inhibitors: e.g. sunitinib, midostaurin, tanutinib, sorafenib, lestaurtinib, quizartinib, and crenolanib; MEK Inhibitors (see Fedele et al, 2018, BioRxiv 307876; Torres-Ayuso et al, 2018, Cancer Discov. 8, 1210-1212; and Wong et al, 2016, Oncotarget. 2016 Oct 4; 7(40): 65676-65695): e.g. trametinib, cobimetinib, binimetinib, selumetinib; ERK inhibitors: e.g. ulixertinib, MK-8353, LY-3214996; VEGF receptor inhibitors: e.g. bevacizumab, axitinib, aflibercept, brivanib, motesanib, pasireotide, sorafenib; Tyrosine kinase inhibitors: e.g. erlotinib, linifanib, sunitinib, pazopanib; Epidermal growth factor receptor (EGFR) inhibitors: gefitnib, osimertinib, cetuximab, panitumumab; HER2 receptor inhibitors: e.g. trastuzumab, neratinib, lapatinib, lapatinib; MET inhibitors: e.g. crizotinib, cabozantinib; CD20 antibodies: e.g. rituximab, tositumomab, ofatumumab; DNA Synthesis inhibitors: e.g. capecitabine, gemcitabine, nelarabine, hydroxycarbamide; Antineoplastic agents: e.g. oxaliplatin, cisplatin; HER dimerization inhibitors: e.g. pertuzumab; Human Granulocyte colony-stimulating factor (G-CSF) modulators: e.g. filgrastim; Immunomodulators: e.g. afutuzumab, lenalidomide, thalidomide, pomalidomide; CD40 inhibitors: e.g. dacetuzumab; Pro-apoptotic receptor agonists (PARAs): e.g. dulanermin; Heat Shock Protein (HSP) inhibitors: e.g. tanespimycin (17-allylamino-17-desmethoxygeldanamycin); Hedgehog antagonists: e.g. vismodegib; Proteasome inhibitors: e.g. bortezomib; PI3K inhibitors: e.g. pictilisib, dactolisib, buparlisib, taselisib, idelalisib, duvelisib, umbralisib; Phospholipase A2 inhibitors: e.g. anagrelide; BCL-2 inhibitors: e.g. venetoclax; Aromatase inhibitors: exemestane, letrozole, anastrozole, faslodex, tamoxifen; Topoisomerase I inhibitors: e.g. irinotecan, topotecan; Topoisomerase II inhibitors: e.g. etoposide, teniposide; mTOR inhibitors: e.g. temsirolimus, ridaforolimus, everolimus, sirolimus; Osteoclastic bone resorption inhibitors: e.g. zoledronic acid; CD33 Antibody Drug Conjugates: e.g. gemtuzumab ozogamicin; CD22 Antibody Drug Conjugates: e.g. inotuzumab ozogamicin; CD20 Antibody Drug Conjugates: e.g. ibritumomab tiuxetan; Somatostain analogs: e.g. octreotide; Interleukin-11 (IL-11): e.g. oprelvekin; Synthetic erythropoietin: e.g. darbepoetin alfa; Receptor Activator for Nuclear Factor κ B (RANK) inhibitors: e.g. denosumab; Thrombopoietin mimetic peptides: e.g. romiplostim; Cell growth stimulators: e.g. palifermin; Anti-Insulin-like Growth Factor-1 receptor (IGF-1R) antibodies: e.g. figitumumab; Anti-CS1 antibodies: e.g. elotuzumab; CD52 antibodies: e.g. alemtuzumab; CTLA-4 inhibitors: e.g. tremelimumab, ipilimumab; PD1 inhibitors: e.g. nivolumab, pembrolizumab; an immunoadhesin; e.g. pidilizumab, AMP-224; PDL1 inhibitors: e.g. MSB0010718C; YW243.55.570, MPDL3280A; MEDI-4736, MSB-0010718C, or MDX-1105; LAG-3 inhibitors: e.g. BMS-986016; GITR agonists; GITR fusion proteins and anti-GITR antibodies; Histone deacetylase inhibitors (HDI): e.g. voninostat; Anti-CTLA4 antibodies: e.g. tremelimumab, ipilimumab; Alkylating agents: e.g. temozolomide, dactinomycin, melphalan, altretamine carmustine, bendamustine, busulfan, carboplatin, lomustine, cisplatin, chlorambucil, cyclophosphamide, dacarbazine, altretamine, ifosfamide, procarbazine, mechlorethamine, mustine and mechloroethamine, streptozocin, thiotepa; Biologic response modifiers: e.g. *bacillus* calmette-guerin, denileukin diftitox; Anti-tumor antibiotics: e.g. doxorubicin, bleomycin, daunorubicin, daunorubicin liposomal, mitoxantrone, epirubicin, idarubicin, mitomycin C; Anti-microtubule agents: e.g. estramustine; Cathepsin K inhibitors: e.g. odanacatib; Epothilone analogs: e.g. ixabepilone; TpoR agonists: e.g. eltrombopag; Anti-mitotic agents: e.g. docetaxel; Adrenal steroid inhibitors: e.g. aminoglutethimide; Anti-androgens: e.g. nilutamide; Androgen Receptor inhibitors: e.g. enzalutamide, abiraterone acetate, orteronel, galeterone, and seviteronel, bicalutamide, flutamide; Androgens: e.g. fluoxymesterone; CDK1 inhibitors: e.g. alvocidib, palbociclib, ribociclib, trilaciclib, abemaciclib; Gonadotropin-releasing hormone (GnRH) receptor agonists: e.g. leuprolide or leuprolide acetate; Taxane anti-neoplastic agents: e.g. cabazitaxel, larotaxel; 5-HT1a receptor agonists: e.g. xaliproden; HPV vaccines: e.g. Cervarix® sold by GlaxoSmithKline, Gardasil® sold by Merck; Iron Chelating agents: e.g. deferasirox; Anti-metabolites: e.g. claribine, 5-fluorouracil, 6-thioguanine, pemetrexed, cytarabine, cytarabine liposomal, decitabine, hydroxyurea, fludarabine, floxuridine, cladribine, methotrexate, pentostatin; Bisphosphonates: e.g. pamidronate; Demethylating agents: e.g. 5-azacitidine, decitabine; Anti-tumor Plant Alkaloids: e.g. paclitaxel protein-bound; vinblastine, vincristine, vinorelbine, paclitaxel; Retinoids: e.g. alitretinoin, tretinoin, isotretinoin, bexarotene; Glucocorticosteroids: e.g. hydrocortisone, dexamethasone, prednisolone, prednisone, methylprednisolone; Cytokines: e.g. interleukin-2, interleukin-11 (oprevelkin), alpha interferon alfa (IFN-alpha); estrogen receptor downregulators: fulvestrant; Anti-estrogens: e.g. tamoxifen, toremifene; Selective estrogen receptor modulators (SERMs): e.g. raloxifene; Luteinizing hormone releasing hormone (LHRH) agonists: e.g. goserelin; Progesterones: e.g. megestrol; cytotoxic agents: arsenic trioxide, asparaginase (also known as L-asparaginase, *Erwinia* L-asparaginase; Anti-nausea drugs: e.g. NK-1 receptor antagonists (e.g. casopitant); Cytoprotective agents: e.g. amifostine, leucovorin; and Immune checkpoint inhibitors. The term "immune checkpoints" refers to a group of molecules on the cell surface of CD4 and CD8 T cells. Immune checkpoint molecules include, but are not limited to, Programmed Death 1 (PD-1), Cytotoxic T-Lymphocyte Antigen 4 (CTLA-4), B7H1, B7H4, OX-40, CD 137, CD40, and LAG3. Immunotherapeutic agents which can act as immune checkpoint inhibitors useful in the methods of the present disclosure, include, but are not limited to, inhibitors of PD-L1, PD-L2, CTLA4, TIM3, LAG3, VISTA, BTLA, TIGIT, LAIR1, CD 160, 2B4 and/or TGFR beta.

In some embodiments, the one or more additional therapeutic agent is selected from the following agents: anti-FGFR antibodies; cytotoxic agents; Estrogen Receptor-targeted or other endocrine therapies, immune-checkpoint inhibitors, CDK inhibitors, other Receptor Tyrosine Kinase inhibitors, BRAF inhibitors, MEK inhibitors, PI3K inhibitors, SHP2 inhibitors, and SRC inhibitors. (See M. Katoh, Nat. Rev. Clin. Oncol. 2019, 16:105-122; Y. K. Chae, et al. Oncotarget 2017, 8:16052-16074; L. Formisano et al., Nat. Comm. 2019, 10:1373-1386; and references cited therein.)

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Any of the compounds and/or compositions of the disclosure may be provided in a kit comprising the compounds and/or compositions. Thus, in some embodiments, the compound and/or composition of the disclosure is provided in a kit.

The disclosure is further described by the following non-limiting Examples.

EXAMPLES

Examples are provided herein to facilitate a more complete understanding of the disclosure. The following examples serve to illustrate the exemplary modes of making and practicing the subject matter of the disclosure. However, the scope of the disclosure is not to be construed as limited to specific embodiments disclosed in these examples, which are illustrative only.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to other classes and subclasses and species of each of these compounds, as described herein. Additional compounds of the invention were prepared by methods substantially similar to those described herein in the Examples and methods known to one skilled in the art.

In the description of the synthetic methods described below, unless otherwise stated, it is to be understood that all reaction conditions (for example, reaction solvent, atmosphere, temperature, duration, and workup procedures) are selected from the standard conditions for that reaction, unless otherwise indicated. In the general schemes, it is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated (for example, use of protecting groups or alternative reactions). The starting materials for the examples are either commercially available or are readily prepared by standard methods from known materials.

At least some of the compounds identified as "Intermediates" herein are contemplated as compounds of the disclosure.

In some embodiments, compounds of formula I are prepared according to the general procedure depicted in Scheme 1, below.

Scheme 1

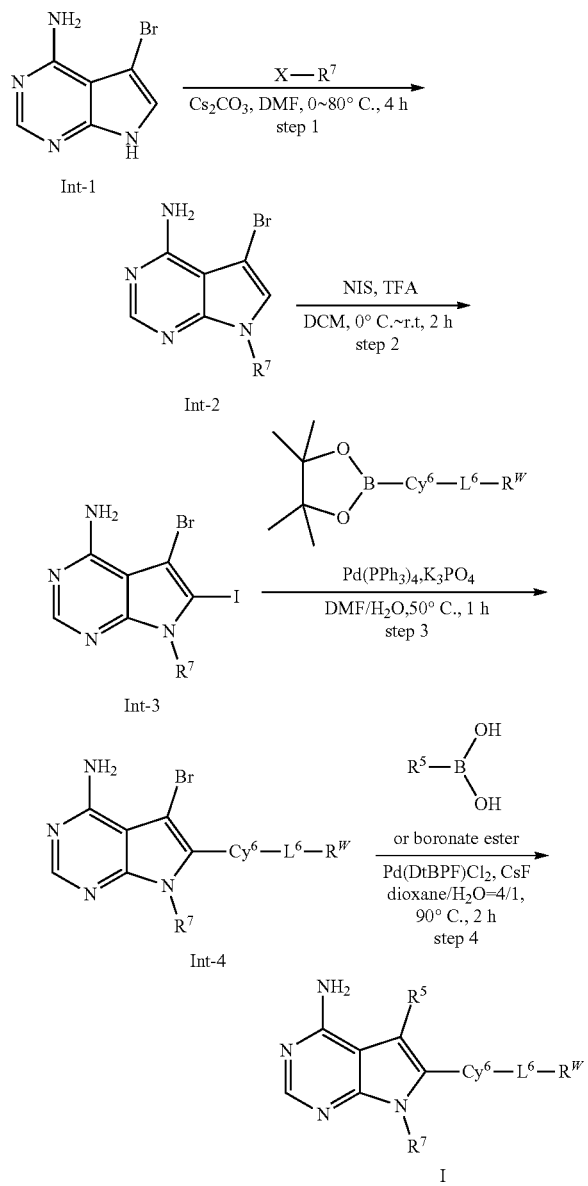

In some embodiments, Step 1 comprises the condensation of Int-1 with a compound of formula X—R⁷, thereby forming a compound of formula Int-2, wherein R⁷ is defined in embodiments herein and X is a leaving group.

In some embodiments, Step 2 comprises the iodination of a compound of formula Int-2. In some embodiments the reagent used is N-iodosuccinimide.

In some embodiments, Step 3 comprises the coupling of a compound of formula Int-3 with a synthon comprising Cy⁶-L⁶-R$^W$ functionalized with a suitable reactive group, thereby forming a compound of formula Int-4. In some embodiments the suitable reactive group is a boronate ester. In some embodiments, the suitable reactive group is a pinacol boronate.

In some embodiments, Step 4 comprises the coupling of a compound of formula Int-4 with a synthon comprising R⁵ functionalized with a suitable reactive group, thereby forming a compound of formula I. In some embodiments, the suitable reactive group is a boronic acid or boronate ester.

Example 1

N-(4-(4-amino-5-(3-methoxy-4-(pyrimidin-2-yloxy)phenyl)-7-methyl-7H-pyrrolo[2,3-d]pyrimidin-6-yl)phenyl)methacrylamide

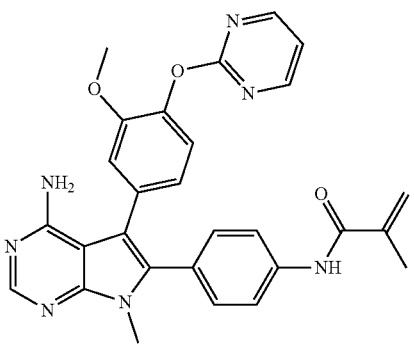 [SMILES: C=C(C)C(=O)Nc1ccc(-c2c(-c3ccc(Oc4ncccn4)c(OC)c3)c3c(N)ncnc3n2C)cc1]

5-bromo-7-methyl-7H-pyrrolo[2,3-d]pyrimidin-4-amine

Step 1: A round bottomed flask was charged with 5-bromo-7H-pyrrolo[2,3-d]pyrimidin-4-amine (3 g, 14.0 mmol), Cs₂CO₃ (9.10 g, 28.0 mmol), DMF (50 mL) and a stirbar. The mixture was cooled to 0° C. and iodomethane (1.98 g, 14.0 mmol) was added, and the solution was stirred for 3 h at 0° C. The reaction mixture was diluted with H₂O (300 mL), and the aqueous phase was extracted with EA (300 mL) three times. The combined organic layers were washed with brines, dried over sodium sulfate, filtered, and concentrated in vacuo. The resulting crude material was purified by silica gel chromatography (eluting with MeOH/DCM=1/80). Concentration in vacuo resulted in 5-bromo-7-methyl-7H-pyrrolo[2,3-d]pyrimidin-4-amine (2.20 g, 70%) as a yellow crystalline solid.

5-bromo-6-iodo-7-methyl-7H-pyrrolo[2,3-d]pyrimidin-4-amine

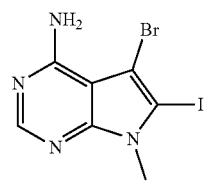

Step 2: A round bottomed flask was charged with 5-bromo-7-methyl-7H-pyrrolo[2,3-d]pyrimidin-4-amine (3 g, 13.2 mmol), TFA (7.52 g, 66.0 mmol), DCM (50 mL) and a stirbar. The mixture was cooled to 0° C. and 1-iodopyrrolidine-2,5-dione (2.96 g, 13.2 mmol) was added, and the solution was stirred for 2 h at room temperature. The reaction mixture was diluted with saturated Na₂SO₃ solution (100 mL). The pH of the solution was adjusted to 7-8 with saturated NaHCO₃ solution. The solid was filtered and washed with H₂O, then washed with a small amount of DCM and resulted in 5-bromo-6-iodo-7-methyl-7H-pyrrolo[2,3-d]pyrimidin-4-amine (3.70 g, 80%) as a white amorphous solid.

N-(4-(4-amino-5-bromo-7-methyl-7H-pyrrolo[2,3-d]pyrimidin-6-yl)phenyl)methacrylamide

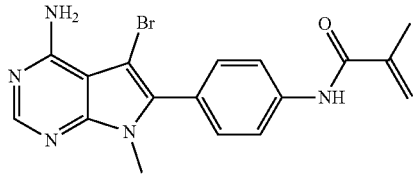 [SMILES: C=C(C)C(=O)Nc1ccc(-c2c(Br)c3c(N)ncnc3n2C)cc1]

Step 3: A resealable reaction vial was charged with 5-bromo-6-iodo-7-methyl-7H-pyrrolo[2,3-d]pyrimidin-4-amine (3.7 g, 10.51 mmol), N-(4-(4,4,5,5-tetramethyl-1,3,2-dioxaborolan-2-yl)phenyl)methacrylamide (3.7 g, 12.61 mmol), Pd(PPh₃)₄ (1.21 g, 1.05 mmol), K₃PO₄ (6.68 g, 31.53 mmol), DMF (50 mL), H₂O (3 mL) and a stirbar before being evacuated and purged with nitrogen three times. The mixture was stirred for 1 h at 50° C. The reaction mixture was concentrated in vacuo. The resulting crude material was purified by silica gel chromatography (eluting with MeOH/DCM=1/100~1/20). Concentration in vacuo resulted in N-(4-(4-amino-5-bromo-7-methyl-7H-pyrrolo[2,3-d]pyrimidin-6-yl)phenyl)methacrylamide (2.2 g, 54%) as an off-white amorphous solid.

N-(4-(4-amino-5-(3-methoxy-4-(pyrimidin-2-yloxy)phenyl)-7-methyl-7H-pyrrolo[2,3-d]pyrimidin-6-yl)phenyl)methacrylamide

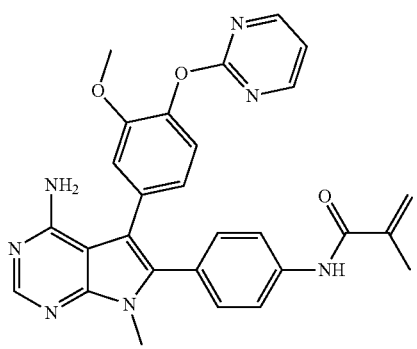 [SMILES: C=C(C)C(=O)Nc1ccc(-c2c(-c3ccc(Oc4ncccn4)c(OC)c3)c3c(N)ncnc3n2C)cc1]

Step 4: A resealable reaction vial was charged with N-(4-(4-amino-5-bromo methyl-7H-pyrrolo[2,3-d]pyrimidin-6-yl)phenyl)methacrylamide (120 mg, 0.31 mmol), 2-(2-methoxy-4-(4,4,5,5-tetramethyl-1,3,2-dioxaborolan-2-yl)phenoxy)pyrimidine (122 mg, 0.373 mmol), Pd(DtBPF)Cl₂ (20.1 mg, 0.031 mmol), CsF (240 mg, 0.930 mmol), DMF (4 mL), H₂O (0.5 mL) and a stirbar before being evacuated and purged with nitrogen three times. The mixture was stirred for 2 h at 90° C. The reaction mixture was concentrated in vacuo. The resulting crude material was purified by TLC (eluting with MeOH/DCM=1/15). Concentration in vacuo resulted in N-(4-(4-amino-5-(3-methoxy-4-(pyrimidin-2-yloxy)phenyl)-7-methyl-7H-pyrrolo[2,3-d]pyrimidin-6-yl)phenyl)methacrylamide (13.9 mg, 9%) as a white amorphous solid.

Example 2

Alternative route for N-(4-(4-amino-5-bromo-7-methyl-7H-pyrrolo[2,3-d]pyrimidin-6-yl)phenyl)methacrylamide

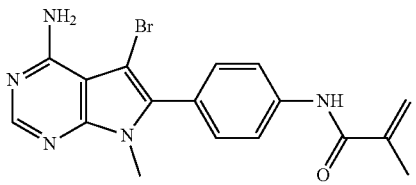 [SMILES: C=C(C)C(=O)Nc1ccc(-c2c(Br)c3c(N)ncnc3n2C)cc1]

6-(4-aminophenyl)-5-bromo-7-methyl-7H-pyrrolo[2,3-d]pyrimidin-4-amine

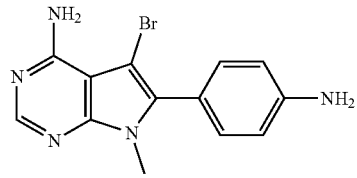 [SMILES: Cn1c(-c2ccc(N)cc2)c(Br)c2c(N)ncnc21]

Step 1: A round bottomed flask was charged with tert-butyl-4-(4-amino-5-bromo-7-methyl-7H-pyrrolo[2,3-d]pyrimidin-6-yl)phenylcarbamate (20 g, 47.8 mmol), DCM (240 mL) and a stirbar. TFA (60 mL) was added. The solution was stirred for 4 h at room temperature. The reaction mixture was basified with saturated Na₂CO₃ aqueous solution (40 mL), and the solids were filtered out and concentrated in vacuo. This resulted in 6-(4-aminophenyl)-5-bromo-7-methyl-7H-pyrrolo[2,3-d]pyrimidin-4-amine (14 g, 92.1%) as a off-white amorphous solid.

N-(4-(4-amino-5-bromo-7-methyl-7H-pyrrolo[2,3-d]pyrimidin-6-yl)phenyl)methacrylamide

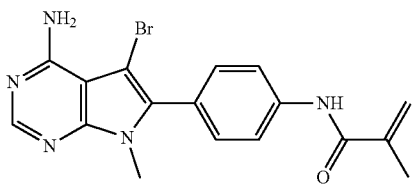 [SMILES: C=C(C)C(=O)Nc1ccc(-c2c(Br)c3c(N)ncnc3n2C)cc1]

Step 2: A resealable reaction vial was charged with 6-(4-aminophenyl)-5-bromo methyl-7H-pyrrolo[2,3-d]pyrimidin-4-amine (10.0 g, 31.4 mmol), DMF/Pyridine (4:1, 200 mL) and a stirbar before being evacuated and purged with nitrogen three times. And the solution was cooled to 0° C. Then methacryloyl chloride (4.0 g, 37.7 mmol) was dissolved in DMF (10 mL) and added to the above solution, and the mixture was stirred for 1 h at room temperature. The reaction mixture was diluted with $H_2O$ (200 mL), and the aqueous phase was extracted with ethyl acetate (200 mL) three times. The combined organic layers were washed with brine, dried over sodium sulfate, filtered, and concentrated in vacuo. The resulting crude material was recrystallized with MeCN. Concentration in vacuo resulted in N-(4-(4-amino-5-bromo-7-methyl-7H-pyrrolo[2,3-d]pyrimidin-6-yl)phenyl)methacrylamide (8.8 g, 73%) as an off-white amorphous solid.

Example 3

4-(4-amino-6-(4-methacrylamidophenyl)-7-methyl-7H-pyrrolo[2,3-d]pyrimidin-5-yl)-N-(oxetan-2-ylmethyl)benzamide

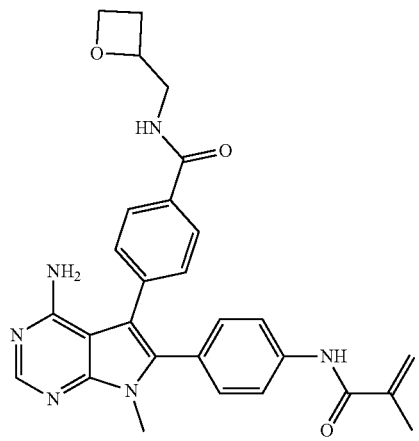 [SMILES: C=C(C)C(=O)Nc1ccc(-c2c(-c3ccc(C(=O)NCC4CCO4)cc3)c3c(N)ncnc3n2C)cc1]

Methyl 4-(4-amino-7-methyl-7H-pyrrolo[2,3-d]pyrimidin-5-yl)benzoate

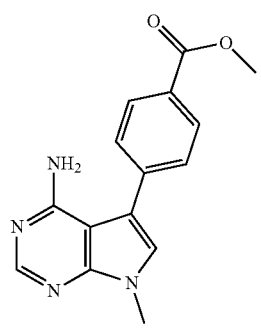 [SMILES: COC(=O)c1ccc(-c2cn(C)c3ncnc(N)c23)cc1]

Step 1: A resealable reaction vial was charged with 5-iodo-7-methyl-7H-pyrrolo[2,3-d]pyrimidin-4-amine (20 g, 72.9 mmol), [4-(methoxycarbonyl)phenyl]boronic acid (15.7 g, 87.4 mmol), Pd(DtBPF)Cl$_2$ (4.74 g, 7.29 mmol), CsF (33.1 g, 218 mmol), DMF (200 mL), $H_2O$ (25 mL) and a stirbar before being evacuated and purged with nitrogen three times. The mixture was stirred for 1 h at 90° C. The reaction mixture was diluted with $H_2O$ (500 mL), and the aqueous phase was extracted with DCM (200 mL) three times. The combined organic layers were washed with brines, dried over sodium sulfate, filtered, and concentrated in vacuo. The reaction mixture was added MeCN (10 mL) and filtered through a pad of Celite®, the pad was washed with MeCN. The filtrate was concentrated in vacuo and the resulting solid was methyl 4-{4-amino-7-methyl-7H-pyrrolo[2,3-d]pyrimidin-5-yl}benzoate (11.0 g, 38.9 mmol), obtained as a yellow amorphous solid.

Methyl 4-(4-amino-6-iodo-7-methyl-7H-pyrrolo[2,3-d]pyrimidin-5-yl)benzoate

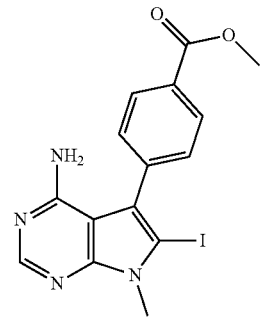 [SMILES: COC(=O)c1ccc(-c2c(I)n(C)c3ncnc(N)c23)cc1]

Step 2: A round bottomed flask was charged with methyl 4-{4-amino-7-methyl-7H-pyrrolo[2,3-d]pyrimidin-5-yl}benzoate (10.9 g, 38.6 mmol), DCM (200 mL), TFA (13.1 g, 115 mmol) and a stirbar. The mixture was cooled to 0° C., NIS (9.53 g, 42.4 mmol) was added, and the solution was stirred for 1 h at room temperature. The reaction mixture was diluted with Na$_2$SO$_3$ solution, and the aqueous phase was extracted with DCM (300 mL) three times. The combined organic layers were washed with brines, dried over sodium sulfate, filtered, and concentrated in vacuo. DCM (20 mL) was added and the reaction mixture was filtered through a pad of Celite®, the pad was washed with little DCM. The filtrate was concentrated in vacuo and the resulting solid was methyl 4-{4-amino-6-iodo-7-methyl-7H-pyrrolo[2,3-d]pyrimidin-5-yl}benzoate (12.0 g, 29.3 mmol), obtained as an off-white amorphous solid Methyl 4-(4-amino-6-(4-methacrylamidophenyl)-7-methyl-7H-pyrrolo[2,3-d]pyrimidin-5-yl)benzoate

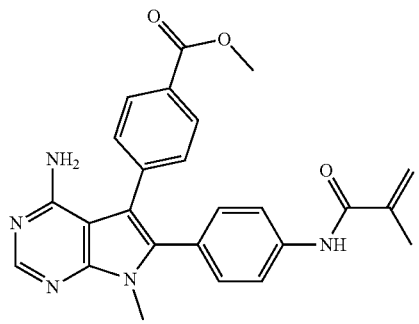 [SMILES: C=C(C)C(=O)Nc1ccc(-c2c(-c3ccc(C(=O)OC)cc3)c3c(N)ncnc3n2C)cc1]

Step 3: A resealable reaction vial was charged with methyl 4-{4-amino-6-iodo-7-methyl-7H-pyrrolo[2,3-d]pyrimidin-5-yl}benzoate (11.9 g, 29.1 mmol), 2-methyl-N-[4-(4,4,5,5-tetramethyl-1,3,2-dioxaborolan-2-yl)phenyl]prop-2-enamide (10.0 g, 34.9 mmol), Pd(dppf)Cl₂ (2.12 g, 2.91 mmol), K₃PO₄ (18.5 g, 87.3 mmol), DMF (100 mL), H₂O (12.5 mL) and a stirbar before being evacuated and purged with nitrogen three times. The mixture was stirred for 1 h at 90° C. The reaction mixture was diluted with H₂O (500 mL), and the aqueous phase was extracted with DCM (300 mL) three times. The combined organic layers were washed with brines, dried over sodium sulfate, filtered, and concentrated in vacuo. The resulting crude material was purified by silica gel chromatography (eluting with MeOH/DCM=1/40). Concentration in vacuo resulted in methyl 4-{4-amino-7-methyl-6-[4-(2-methylprop-2-enamido)phenyl]-7H-pyrrolo[2,3-d]pyrimidin-5-yl}benzoate (7.70 g, 17.4 mmol) as a yellow amorphous solid.

4-(4-amino-6-(4-methacrylamidophenyl)-7-methyl-7H-pyrrolo[2,3-d]pyrimidin-5-yl)benzoic acid

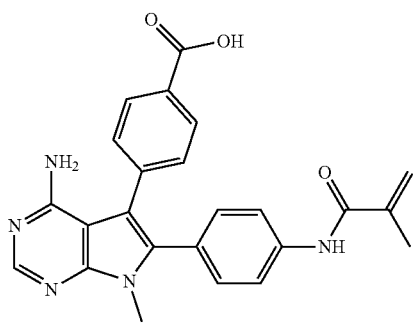 [SMILES: C=C(C)C(=O)Nc1ccc(-c2c(-c3ccc(C(=O)O)cc3)c3c(N)ncnc3n2C)cc1]

Step 4: A round bottomed flask was charged with methyl 4-{4-amino-7-methyl-6-[4-(2-methylprop-2-enamido)phenyl]-7H-pyrrolo[2,3-d]pyrimidin-5-yl}benzoate (7.65 g, 17.3 mmol), MeOH (40 mL), NaOH (2 N, 40 mL) and a stirbar. The solution was stirred for overnight at room temperature. The pH of the reaction mixture was adjusted to 6~7 with HCl (2 M). The reaction mixture was filtered through a pad of Celite®, the pad was washed with H₂O. The filtrate was concentrated in vacuo and the resulting solid was 4-{4-amino methyl-6-[4-(2-methylprop-2-enamido)phenyl]-7H-pyrrolo[2,3-d]pyrimidin-5-yl}benzoic acid (6.50 g, 15.2 mmol), obtained as a off-white amorphous solid.

4-(4-amino-6-(4-methacrylamidophenyl)-7-methyl-7H-pyrrolo[2,3-d]pyrimidin-5-yl)-N-(oxetan-2-ylmethyl)benzamide Step 5: A round bottomed flask was charged with 4-{4-amino-7-methyl-6-[4-(2-methylprop-2-enamido)phenyl]-7H-pyrrolo[2,3-d]pyrimidin-5-yl}benzoic acid (60 mg, 0.14 mmol), 1-(oxetan-2-yl)methanamine (13.4 mg, 0.15 mmol), HATU (58.7 mg, 0.15 mmol) DIEA (54.2 mg, 0.42 mmol) and a stirbar. Dimethylformamide (3 mL) was added, and the solution was stirred at 25° C. for 2 h. The resulting crude material was purified by HPLC (Column: XBridge Prep Phenyl OBD Column, 19×150 mm, 5 um, 13 nm). Lyophilization yielded 4-{4-amino-7-methyl-6-[4-(2-methylprop-2-enamido)phenyl]-7H-pyrrolo[2,3-d]pyrimidin-5-yl}-N-[(oxetan-2-yl)methyl]benzamide (20.0 mg, 0.040 mmol) as a off-white amorphous solid.

Additional compounds prepared according to the methods of Examples 1-3 are depicted in Table 2 below.

TABLE 2

Additional Exemplary Compounds

| Compound | Structure | Proton NMR | MS [M + 1] |
|---|---|---|---|
| N-(4-(4-amino-5-(3-methoxy-4-(6-methylpyridin-2-yloxy)phenyl)-7-methyl-7H-pyrrolo[2,3-d]pyrimidin-6-yl)phenyl)acrylamide | 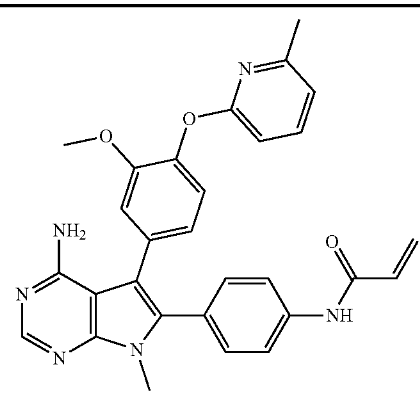 | ¹H NMR (400 MHz, DMSO-d₆) δ 10.29 (s, 1H), 8.21 (s, 1H), 7.72 (d, J = 8.5 Hz, 2H), 7.66 (t, J = 7.8 Hz, 1H), 7.38-7.31 (m, 2H), 7.07 (d, J = 8.1 Hz, 1H), 6.98-6.89 (m, 2H), 6.83 (dd, J = 8.0, 2.0 Hz, 1H), 6.64 (d, J = 8.2 Hz, 1H), 6.45 (dd, J = 17.0, 10.1 Hz, 1H), 6.28 (dd, J = 17.0, 2.0 Hz, 1H), 6.06 (s, 2H), 5.78 (dd, J = 10.0, 2.1 Hz, 1H), 3.63 (s, 3H), 3.54 (s, 3H), 2.30 (s, 3H). | |

TABLE 2-continued

Additional Exemplary Compounds

| Compound | Structure | Proton NMR | MS [M + 1] |
|---|---|---|---|
| N-(3-(4-amino-5-(3-methoxy-4-(6-methylpyridin-2-yloxy)phenyl)-7-methyl-7H-pyrrolo[2,3-d]pyrimidin-6-yl)phenyl)acrylamide | 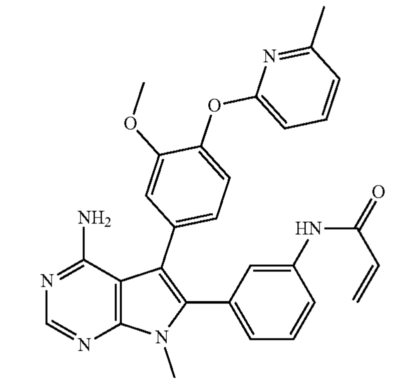 [SMILES: C=CC(=O)Nc1cccc(-c2c(-c3ccc(Oc4cccc(C)n4)c(OC)c3)c3c(N)ncnc3n2C)c1] | ¹H NMR (400 MHz, Methanol-d₄) δ 8.23 (s, 1H), 7.75 (t, J = 1.9 Hz, 1H), 7.67 (ddd, J = 8.2, 2.2, 1.0 Hz, 1H), 7.62 (dd, J = 8.3, 7.4 Hz, 1H), 7.42 (t, J = 7.9 Hz, 1H), 7.13 (ddt, J = 13.0, 7.8, 1.0 Hz, 2H), 6.99-6.90 (m, 3H), 6.58 (dt, J = 8.3, 0.8 Hz, 1H), 6.48-6.32 (m, 2H), 5.80 (dd, J = 9.3, 2.5 Hz, 1H), 3.74 (s, 3H), 3.57 (s, 3H), 2.39 (s, 3H). | 507.35 |
| N-(4-(4-amino-5-(3-methoxy-4-(6-methylpyridin-2-yloxy)phenyl)-7-methyl-7H-pyrrolo[2,3-d]pyrimidin-6-yl)phenyl)-N-methylacrylamide | 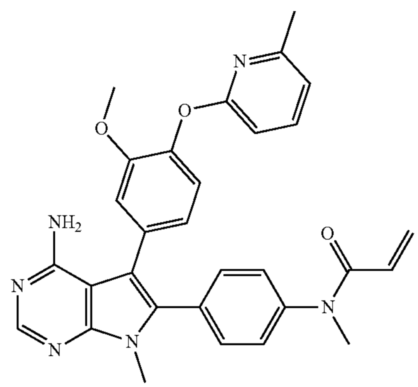 [SMILES: C=CC(=O)N(C)c1ccc(-c2c(-c3ccc(Oc4cccc(C)n4)c(OC)c3)c3c(N)ncnc3n2C)cc1] | ¹H NMR (400 MHz, DMSO-d₆) δ 8.41 (s, 1H), 7.65 (dd, J = 8.2, 7.3 Hz, 1H), 7.54-7.44 (m, 2H), 7.42-7.34 (m, 2H), 7.12 (d, J = 8.0 Hz, 1H), 7.01 (s, 2H), 6.96-6.91 (m, 2H), 6.88 (dd, J = 8.0, 2.0 Hz, 1H), 6.67-6.60 (m, 1H), 6.17 (dd, J = 16.8, 2.5 Hz, 1H), 6.08 (d, J = 11.3 Hz, 1H), 5.58-5.50 (m, 1H), 3.72 (s, 3H), 3.67(s, 3H), 3.28 (s, 3H), 2.29 (s, 3H). | 521.35 |
| N-(3-(4-amino-7-methyl-5-(4-(6-methylpyridin-2-yloxy)phenyl)-7H-pyrrolo[2,3-d]pyrimidin-6-yl)phenyl)acrylamide | 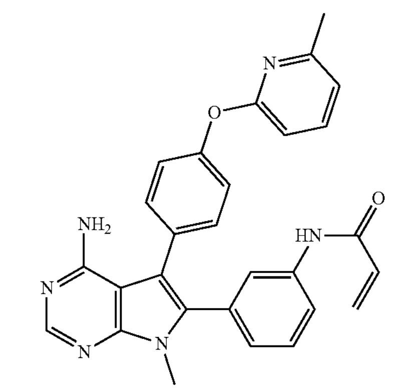 [SMILES: C=CC(=O)Nc1cccc(-c2c(-c3ccc(Oc4cccc(C)n4)cc3)c3c(N)ncnc3n2C)c1] | ¹H NMR (400 MHz, DMSO-d₆) δ 10.24 (s, 1H), 8.21 (s, 1H), 7.74-7.63 (m, 3H), 7.37 (t, J = 7.9 Hz, 1H), 7.33-7.23 (m, 2H), 7.17-6.97 (m, 4H), 6.75 (d, J = 8.2 Hz, 1H), 6.42 (dd, J = 16.9, 10.1 Hz, 1H), 6.26 (dd, J = 17.0, 2.1Hz, 1H), 5.96 (s, 1H), 5.77 (dd, J = 10.0, 2.1 Hz, 1H), 3.62 (s, 3H), 2.33 (s, 3H). | 477.30 |
| 1-(6-(4-amino-5-(3-methoxy-4-(6-methylpyridin-2-yloxy)phenyl)-7-methyl-7H-pyrrolo[2,3-d]pyrimidin-6-yl)-3,4-dihydroquinolin-1(2H)-yl)prop-2-en-1-one | 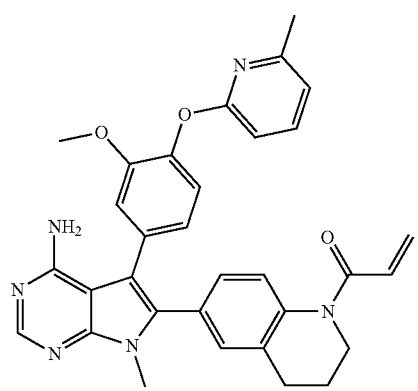 [SMILES: C=CC(=O)N1CCCc2cc(-c3c(-c4ccc(Oc5cccc(C)n5)c(OC)c4)c4c(N)ncnc4n3C)ccc21] | ¹H NMR (400 MHz, Chloroform-d₆) δ 8.31 (s, 1H), 7.59 (t, J = 7.8 Hz, 1H), 7.20 (s, 1H), 7.17-7.08 (m, 3H), 6.88 (dd, J = 7.6, 3.0 Hz, 2H), 6.83 (d, J = 2.0 Hz, 1H), 6.65 (d, J = 8.2 Hz, 1H), 6.61-6.44 (m, 2H), 5.74 (dd, J = 9.4, 2.7 Hz, 1H), 3.90 (t, J = 6.5 Hz, 2H), 3.82 (s, 3H), 3.64 (s, 3H), 2.73 (t, J = 6.5 Hz, 2H), 2.42 (s, 3H), 2.01 (p, J = 6.5 Hz, 2H). | 547.4 |

TABLE 2-continued

Additional Exemplary Compounds

| Compound | Structure | Proton NMR | MS [M + 1] |
|---|---|---|---|
| 1-(5-(4-amino-5-(3-methoxy-4-(6-methylpyridin-2-yloxy)phenyl)-7-methyl-7H-pyrrolo[2,3-d]pyrimidin-6-yl)indolin-1-yl)prop-2-en-1-one | 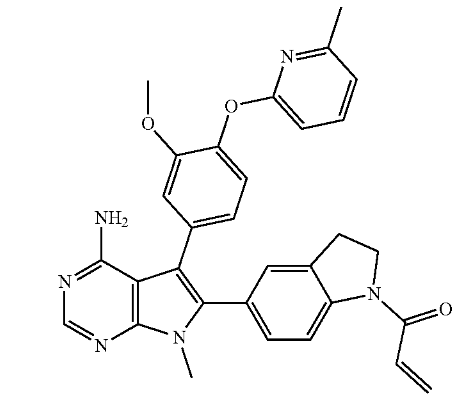 [SMILES: C=CC(=O)N1CCc2cc(-c3c(-c4ccc(Oc5cccc(C)n5)c(OC)c4)c4c(N)ncnc4n3C)ccc21] | $^1$H NMR (400 MHz, DMSO-d6) δ 8.39 (s, 1H), 8.18 (s, 1H), 7.66 (t, J = 7.7 Hz, 1H), 7.29 (s, 1H), 7.22 (d, J = 8.4 Hz, 1H), 7.08 (d, J = 8.0 Hz, 1H), 7.03 (d, J = 2.0 Hz, 1H), 6.93 (d, J = 7.4 Hz, 1H), 6.85-6.70 (m, 1H), 6.64 (d, J = 8.2 Hz, 1H), 6.32 (d, J = 16.5 Hz, 1H), 5.88-5.81 (m, 1H), 4.26 (t, 2H), 3.67 (s, 3H), 3.59 (s, 3H), 3.18 (d, J = 9.0 Hz, 2H), 2.31 (s, 3H). | 533.40 |
| 1-(5-(4-amino-5-(3-methoxy-4-(6-methylpyridin-2-yloxy)phenyl)-7-methyl-7H-pyrrolo[2,3-d]pyrimidin-6-yl)isoindolin-2-yl)prop-2-en-1-one | 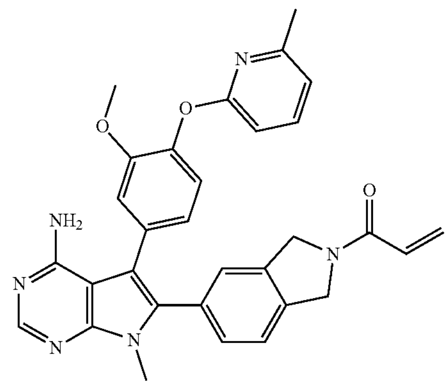 [SMILES: C=CC(=O)N1Cc2ccc(-c3c(-c4ccc(Oc5cccc(C)n5)c(OC)c4)c4c(N)ncnc4n3C)cc2C1] | $^1$H NMR (400 MHz, DMSO-d$_6$) δ 8.22 (s, 1H), 7.65 (t, J = 7.8 Hz, 1H), 7.43 (t, J = 3.9 Hz, 1H), 7.41-7.30 (m, 2H), 7.07 (dd, J = 8.1, 1.0 Hz, 1H), 7.00 (d, J = 2.0 Hz, 1H), 6.92 (d, J = 7.3 Hz, 1H), 6.81 (dd, J = 8.0, 1.6 Hz, 1H), 6.67 (ddt, J = 21.6, 8.0, 4.6 Hz, 2H), 6.23 (dt, J = 16.8, 2.2 Hz, 1H), 6.05 (s, 1H), 5.76 (ddd, J = 10.3, 3.7, 2.3 Hz, 1H), 5.00 (s, 1H), 4.95 (s, 1H), 4.73 (d, J = 17.7 Hz, 2H), 3.62 (d, J = 1.7 Hz, 3H), 3.56 (s, 3H), 2.29 (d, J = 3.6 Hz, 3H). | 533.40 |
| N-(4-(4-amino-7-methyl-5-(4-(6-methylpyridin-2-yloxy)phenyl)-7H-pyrrolo[2,3-d]pyrimidin-6-yl)phenyl)-N-methylacrylamide | 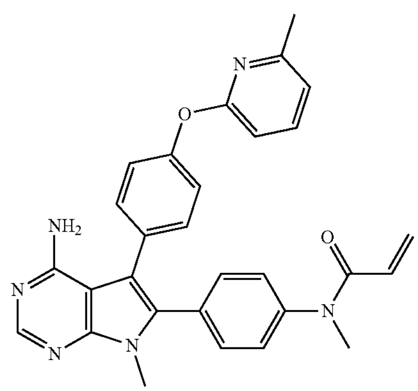 [SMILES: C=CC(=O)N(C)c1ccc(-c2c(-c3ccc(Oc4cccc(C)n4)cc3)c3c(N)ncnc3n2C)cc1] | $^1$H NMR (400 MHz, DMSO-d$_6$) δ 8.22 (s, 1H), 7.73 (dd, J = 8.1, 7.4 Hz, 1H), 7.48-7.40 (m, 2H), 7.37-7.22 (m, 4H), 7.14-6.96 (m, 3H), 6.78 (d, J = 8.1 Hz, 1H), 6.22-6.01 (m, 2H), 5.58 (dd, J = 9.9, 2.7 Hz, 1H), 3.65 (s, 3H), 3.27 (s, 3H), 2.33 (s, 3H). | 491.15 |
| 1-(6-(4-amino-7-methyl-5-(4-((6-methylpyridin-2-yl)oxy)phenyl)-7H-pyrrolo[2,3-d]pyrimidin-6-yl)-3,4-dihydroisoquinolin-2(1H)-yl)prop-2-en-1-one | 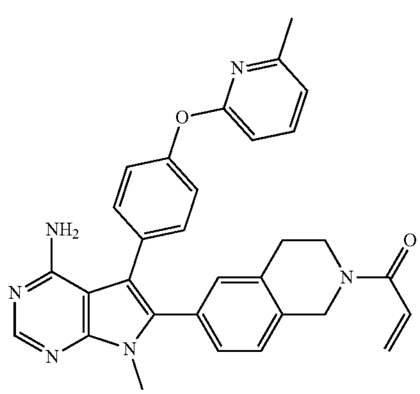 [SMILES: C=CC(=O)N1CCc2cc(-c3c(-c4ccc(Oc5cccc(C)n5)cc4)c4c(N)ncnc4n3C)ccc2C1] | $^1$H NMR (400 MHz, DMSO-d$_6$) δ 8.20 (s, 1H), 7.73 (t, J = 7.7 Hz, 1H), 7.30-7.15 (m, 5H), 7.13-7.06 (m, 2H), 7.01 (d, J = 7.4 Hz, 1H), 6.89 (dd, J = 16.7, 10.5 Hz, 1H), 6.77 (d, J = 8.2 Hz, 1H), 6.15 (dd, J = 16.7, 2.4 Hz, 1H), 5.88 (s, 2H), 5.72 (dd, J = 10.4, 2.4 Hz, 1H), 4.81 (s, 1H), 4.71 (s, 1H), 3.80 (d, J = 6.3 Hz, 2H), 3.62 (s, 3H), 2.83 (s, 2H), 2.33 (s, 3H). | 517.25 |

TABLE 2-continued

Additional Exemplary Compounds

| Compound | Structure | Proton NMR | MS [M + 1] |
|---|---|---|---|
| N-(4-(4-amino-7-methyl-5-(4-(6-methylpyridin-2-yloxy)phenyl)-7H-pyrrolo[2,3-d]pyrimidin-6-yl)-2-methylphenyl)acrylamide | 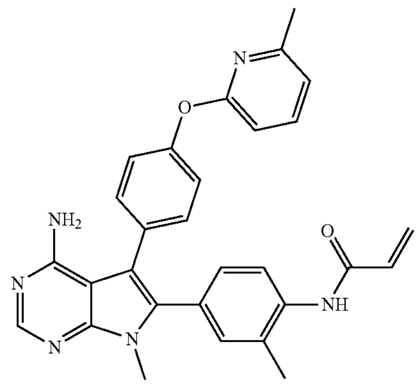 [SMILES: C=CC(=O)Nc1ccc(-c2c(-c3ccc(Oc4cccc(C)n4)cc3)c3c(N)ncnc3n2C)cc1C] | $^1$H NMR (400 MHz, DMSO-d$_6$) δ 9.48 (s, 1H), 8.20 (s, 1H), 7.73 (t, J = 7.7 Hz, 1H), 7.62 (d, J = 8.2 Hz, 1H), 7.32-7.25 (m, 2H), 7.23 (d, J = 2.0 Hz, 1H), 7.17 (dd, J = 8.3, 2.1 Hz, 1H), 7.15-7.07 (m, 2H), 7.01 (d, J = 7.3 Hz, 1H), 6.77 (d, J = 8.1 Hz, 1H), 6.57 (dd, J = 17.0, 10.2 Hz, 1H), 6.26 (dd, J = 17.0, 2.1 Hz, 1H), 6.14-5.86 (m, 1H), 5.77 (dd, J = 10.2, 2.0 Hz, 1H), 3.63 (s, 3H), 2.34 (s, 3H), 2.20 (s, 3H). | 491.35 |
| N-(4-(4-amino-7-methyl-5-(4-(6-methylpyridin-2-yloxy)phenyl)-7H-pyrrolo[2,3-d]pyrimidin-6-yl)-2-fluorophenyl)acrylamide | 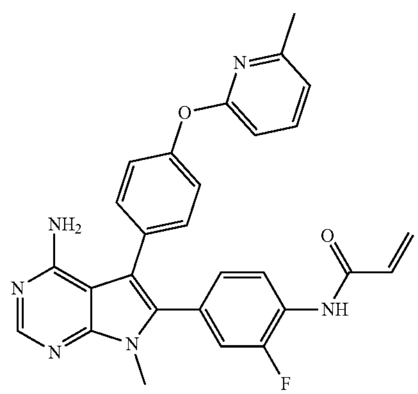 [SMILES: C=CC(=O)Nc1ccc(-c2c(-c3ccc(Oc4cccc(C)n4)cc3)c3c(N)ncnc3n2C)cc1F] | $^1$H NMR (400 MHz, Methanol-d$_4$) δ 8.21 (s, 1H), 8.15 (t, J = 8.1 Hz, 1H), 7.74 (dd, J = 8.2, 7.4 Hz, 1H), 7.37-7.33 (m, 2H), 7.23-7.16 (m, 2H), 7.16-7.08 (m, 2H), 7.03 (dt, J = 7.4, 0.7 Hz, 1H), 6.77 (dt, J = 8.2, 0.7 Hz, 1H), 6.58 (dd, J = 17.0, 10.2 Hz, 1H), 6.42 (dd, J = 17.0, 1.8 Hz, 1H), 5.83 (dd, J = 10.2, 1.8 Hz, 1H), 3.73 (s, 3H), 2.43 (s, 3H). | 495.30 |
| N-(4-(4-amino-7-methyl-5-(4-(6-methylpyridin-2-yloxy)phenyl)-7H-pyrrolo[2,3-d]pyrimidin-6-yl)-2-methoxyphenyl)acrylamide | 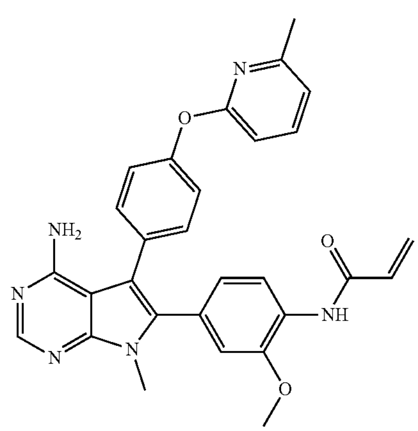 [SMILES: C=CC(=O)Nc1ccc(-c2c(-c3ccc(Oc4cccc(C)n4)cc3)c3c(N)ncnc3n2C)cc1OC] | $^1$H NMR (400 MHz, DMSO-d$_6$) δ 9.45 (s, 1H), 8.21 (s, 1H), 8.14 (d, J = 8.3 Hz, 1H), 7.74 (t, J = 7.8 Hz, 1H), 7.35-7.24 (m, 2H), 7.17-7.07 (m, 2H), 7.07-6.98 (m, 2H), 6.98-6.89 (m, 1H), 6.79 (d, J = 8.1 Hz, 1H), 6.73 (dd, J = 17.0, 10.2 Hz, 1H), 6.25 (dd, J = 17.1, 2.1 Hz, 1H), 5.92 (s, 1H), 5.73 (dd, J = 10.2, 2.1 Hz, 1H), 3.70 (d, J = 9.0 Hz, 6H), 2.34 (s, 3H). | 507.35 |

TABLE 2-continued

Additional Exemplary Compounds

| Compound | Structure | Proton NMR | MS [M + 1] |
|---|---|---|---|
| N-(4-(4-amino-7-methyl-5-(3-methyl-4-(6-methylpyridin-2-yloxy)phenyl)-7H-pyrrolo[2,3-d]pyrimidin-6-yl)phenyl)acrylamide | 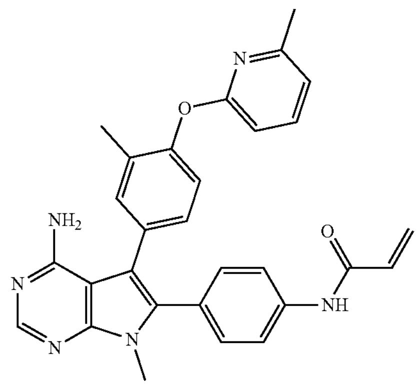 [SMILES: C=CC(=O)Nc1ccc(-c2c(-c3ccc(Oc4cccc(C)n4)c(C)c3)c3c(N)ncnc3n2C)cc1] | $^1$H NMR (400 MHz, DMSO-$d_6$) δ 10.28 (s, 1H), 8.19 (d, J = 1.9 Hz, 1H), 7.77-7.66 (m, 3H), 7.41-7.30 (m, 2H), 7.21 (d, J = 2.2 Hz, 1H), 7.07 (dd, J = 8.2, 2.2 Hz, 1H), 6.97 (dd, J = 7.8, 5.7 Hz, 2H), 6.69 (d, J = 8.1 Hz, 1H), 6.45 (dd, J = 16.9, 10.1 Hz, 1H), 6.27 (dd, J = 16.9, 2.1 Hz, 1H), 5.92 (s, 1H), 5.78 (dd, J = 10.1, 2.1 Hz, 1H), 3.62 (s, 3H), 2.32 (s, 3H), 2.06 (s, 3H). | 491.35 |
| N-(4-(4-amino-5-(3-methoxy-4-(pyrimidin-2-yloxy)phenyl)-7-methyl-7H-pyrrolo[2,3-d]pyrimidin-6-yl)phenyl)acrylamide | 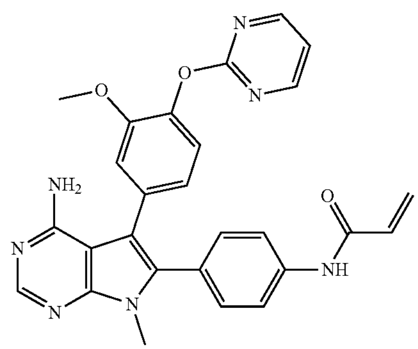 [SMILES: C=CC(=O)Nc1ccc(-c2c(-c3ccc(Oc4ncccn4)c(OC)c3)c3c(N)ncnc3n2C)cc1] | $^1$H NMR (400 MHz, Chloroform-d) δ 8.56 (d, J = 4.8 Hz, 2H), 8.40 (s, 1H), 7.66 (d, J = 8.2 Hz, 2H), 7.48 (s, 1H), 7.30 (d, J = 2.1 Hz, 1H), 7.17 (d, J = 8.1 Hz, 1H), 7.05 (t, J = 4.8 Hz, 1H), 6.94 (dd, J = 8.1, 2.0 Hz, 1H), 6.86 (d, J = 1.9 Hz, 1H), 6.49 (dd, J = 16.9, 1.3 Hz, 1H), 6.29 (dd, J = 16.9, 10.2 Hz, 1H), 5.83 (dd, J = 10.2, 1.3 Hz, 1H), 5.27 (s, 2H), 3.75 (s, 3H), 3.57 (s, 3H) | 494.15 |
| N-(4-(4-amino-5-(3-methoxy-4-(pyridin-2-yloxy)phenyl)-7-methyl-7H-pyrrolo[2,3-d]pyrimidin-6-yl)phenyl)acrylamide | 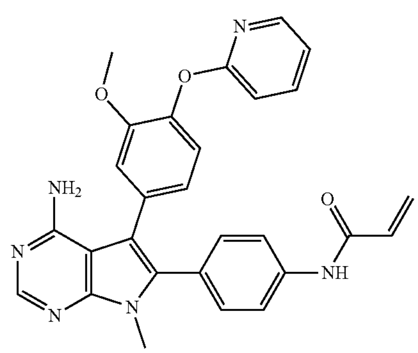 [SMILES: C=CC(=O)Nc1ccc(-c2c(-c3ccc(Oc4ccccn4)c(OC)c3)c3c(N)ncnc3n2C)cc1] | $^1$H NMR (400 MHz, Chloroform-d) δ 8.39 (s, 1H), 8.15 (ddd, J = 5.0, 2.0, 0.8 Hz, 1H), 7.72 (ddd, J = 8.3, 7.2, 2.0 Hz, 1H), 7.67 (d, J = 8.2 Hz, 2H), 7.44 (s, 1H), 7.30 (d, J = 1.9 Hz, 1H), 7.28 (s, 1H), 7.10 (d, J = 8.1 Hz, 1H), 7.00 (ddd, J = 7.2, 5.0, 0.9 Hz, 1H), 6.98-6.89 (m, 2H), 6.86 (d, J = 2.0 Hz, 1H), 6.48 (dd, J = 16.8, 1.2 Hz, 1H), 6.28 (dd, J = 16.8, 10.2 Hz, 1H), 5.83 (dd, J = 10.2, 1.2 Hz, 1H), 5.35 (s, 2H), 3.75 (s, 3H), 3.60 (s, 3H). | 493.15 |
| N-(4-(4-amino-5-(3-methoxy-4-(6-methylpyridin-2-yloxy)phenyl)-7-methyl-7H-pyrrolo[2,3-d]pyrimidin-6-yl)phenyl)but-3-enamide | 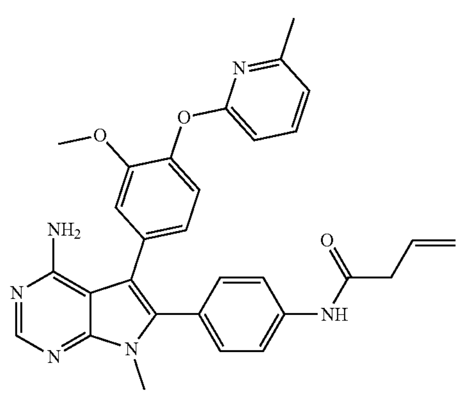 [SMILES: C=CCC(=O)Nc1ccc(-c2c(-c3ccc(Oc4cccc(C)n4)c(OC)c3)c3c(N)ncnc3n2C)cc1] | $^1$H NMR (400 MHz, DMSO-$d_6$) δ 10.10 (s, 1H), 8.20 (s, 1H), 7.73-7.60 (m, 3H), 7.35-7.28 (m, 2H), 7.07 (d, J = 8.0 Hz, 1H), 6.98-6.89 (m, 2H), 6.82 (dd, J = 8.1, 2.0 Hz, 1H), 6.64 (d, J = 8.2 Hz, 1H), 5.97 (ddt, J = 17.0, 10.1, 6.9 Hz, 1H), 5.19 (dq, J = 17.2, 1.8 Hz, 1H), 5.18-5.10 (m, 1H), 3.61 (s, 3H), 3.54 (s, 3H), 3.14 (dt, J = 7.0, 1.5 Hz, 2H), 2.30 (s, 3H). | 521.20 |

TABLE 2-continued

Additional Exemplary Compounds

| Compound | Structure | Proton NMR | MS [M + 1] |
|---|---|---|---|
| N-(4-(4-amino-5-(3-methoxy-4-(6-methylpyridin-2-yloxy)phenyl)-7-methyl-7H-pyrrolo[2,3-d]pyrimidin-6-yl)phenyl)but-2-ynamide | 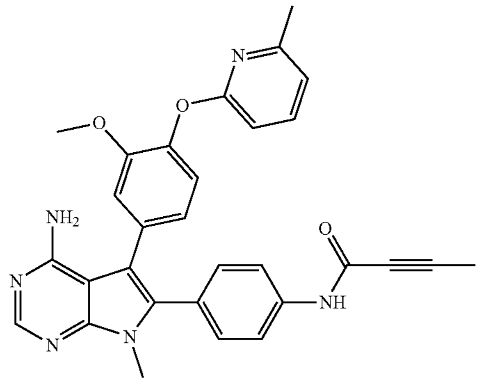 [SMILES: CC#CC(=O)Nc1ccc(-c2c(-c3ccc(Oc4cccc(C)n4)c(OC)c3)c3c(N)ncnc3n2C)cc1] | $^1$H NMR (400 MHz, DMSO-d$_6$) δ 10.75 (s, 1H), 8.20 (s, 1H), 7.70-7.54 (m, 3H), 7.32 (d, J = 8.2 Hz, 2H), 7.07 (d, J = 8.0 Hz, 1H), 7.02-6.88 (m, 2H), 6.82 (dd, J = 8.2, 1.9 Hz, 1H), 6.64 (d, J = 8.2 Hz, 1H), 6.02 (s, 2H), 3.57 (d, J = 32.6 Hz, 7H), 2.30 (s, 3H), 2.06 (s, 3H). | 519.35 |
| N-(4-(4-amino-5-(3-methoxy-4-(6-methylpyridin-2-yloxy)phenyl)-7-methyl-7H-pyrrolo[2,3-d]pyrimidin-6-yl)phenyl)-N-methylbut-2-ynamide | 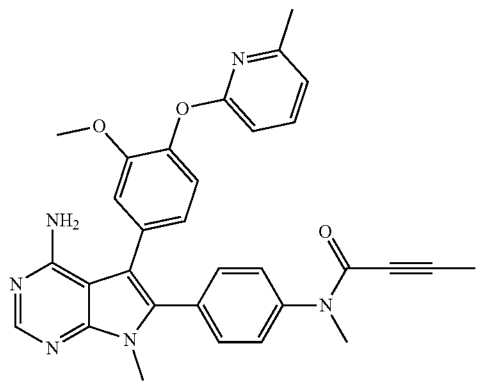 [SMILES: CC#CC(=O)N(C)c1ccc(-c2c(-c3ccc(Oc4cccc(C)n4)c(OC)c3)c3c(N)ncnc3n2C)cc1] | $^1$H NMR (400 MHz, DMSO-d$_6$) δ 8.22 (s, 1H), 7.66 (dd, J = 8.2, 7.3 Hz, 1H), 7.43 (s, 4H), 7.08 (d, J = 8.0 Hz, 1H), 6.97-6.90 (m, 2H), 6.87 (dd, J = 8.0, 1.9 Hz, 1H), 6.64 (d, J = 8.2 Hz, 1H), 6.06 (s, 2H), 3.65 (s, 3H), 3.53 (s, 4H), 3.23 (s, 2H), 2.30 (s, 3H), 2.11 (s, 1H), 1.66 (s, 2H). | 533.40 |
| N-(4-(4-amino-5-(3-methoxy-4-((6-methylpyridin-2-yl)oxy)phenyl)-7-methyl-7H-pyrrolo[2,3-d]pyrimidin-6-yl)phenyl)methacrylamide | 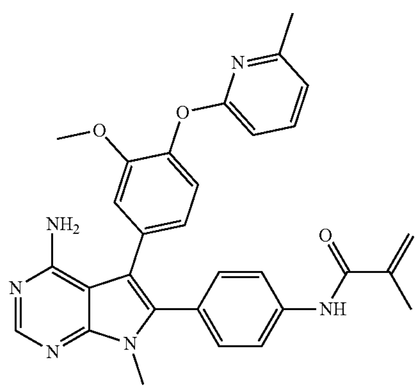 [SMILES: C=C(C)C(=O)Nc1ccc(-c2c(-c3ccc(Oc4cccc(C)n4)c(OC)c3)c3c(N)ncnc3n2C)cc1] | $^1$H NMR (400 MHz, DMSO-d$_6$) δ 9.91 (s, 1H), 8.21 (s, 1H), 7.77-7.70 (m, 2H), 7.70-7.62 (m, 1H), 7.36-7.29 (m, 2H), 7.07 (d, J = 8.1 Hz, 1H), 6.99-6.89 (m, 2H), 6.82 (dd, J = 8.1, 1.9 Hz, 1H), 6.64 (d, J = 8.2 Hz, 1H), 5.80 (s, 1H), 5.54 (s, 1H), 3.62 (s, 3H), 3.55 (s, 3H), 2.30 (s, 3H), 1.96 (t, J = 1.2 Hz, 3H). | 521.35 |
| (E)-N-(4-(4-amino-5-(3-methoxy-4-(6-methylpyridin-2-yloxy)phenyl)-7-methyl-7H-pyrrolo[2,3-d]pyrimidin-6-yl)phenyl)but-2-enamide | 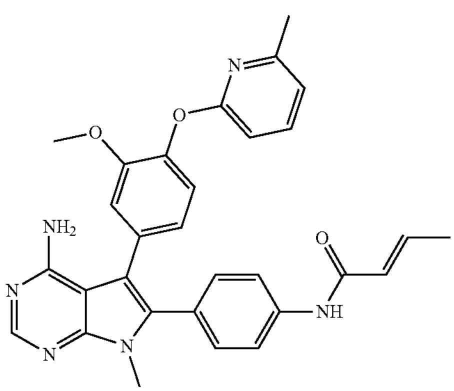 [SMILES: C/C=C/C(=O)Nc1ccc(-c2c(-c3ccc(Oc4cccc(C)n4)c(OC)c3)c3c(N)ncnc3n2C)cc1] | $^1$H NMR (400 MHz, DMSO-d$_6$) δ 10.09 (d, J = 5.7 Hz, 1H), 8.20 (s, 1H), 7.66 (ddd, J = 21.5, 8.6, 3.9 Hz, 3H), 7.32 (dd, J = 8.7, 3.2 Hz, 2H), 7.07 (dd, J = 8.0, 1.7 Hz, 1H), 6.98-6.89 (m, 2H), 6.88-6.75 (m, 2H), 6.64 (d, J = 8.2 Hz, 1H), 6.13 (dd, J = 15.1, 2.0 Hz, 1H), 6.0 (m, 1H), 5.25-5.10 (m, 1H), 3.62 (d, J = 3.0 Hz, 3H), 3.54 (s, 3H), 3.14 (dt, J = 6.8, 1.6 Hz, 1H), 2.30 (s, 3H), 1.88 (dd, J = 6.9, 1.6 Hz, 2H) | 521.35 |

TABLE 2-continued

Additional Exemplary Compounds

| Compound | Structure | Proton NMR | MS [M + 1] |
|---|---|---|---|
| N-(4-(4-amino-5-(3-methoxyphenyl)-7-methyl-7H-pyrrolo[2,3-d]pyrimidin-6-yl)phenyl)acrylamide | 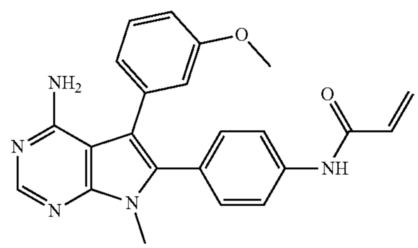 [SMILES: C=CC(=O)Nc1ccc(-c2c(-c3cccc(OC)c3)c3c(N)ncnc3n2C)cc1] | $^1$H NMR (400 MHz, DMSO-d$_6$) δ 10.27 (s, 1H), 8.19 (s, 1H), 7.72-7.64 (m, 2H), 7.34-7.24 (m, 3H), 6.90-6.78 (m, 2H), 6.76 (dd, J = 2.6, 1.6 Hz, 1H), 6.44 (dd, J = 17.0, 10.1 Hz, 1H), 6.27 (dd, J = 17.0, 2.1 Hz, 1H), 5.78 (dd, J = 10.1, 2.1 Hz, 3H), 3.67 (s, 3H), 3.60 (s, 3H). | 400.1 |
| N-(4-(4-amino-5-(3-methoxy-4-(m-tolyloxy)phenyl)-7-methyl-7H-pyrrolo[2,3-d]pyrimidin-6-yl)phenyl)acrylamide | 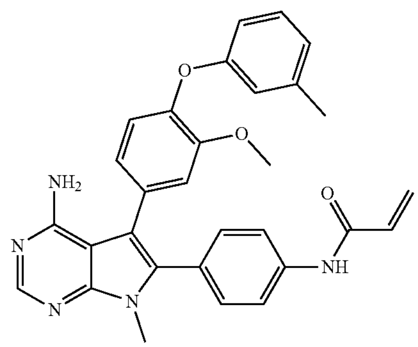 [SMILES: C=CC(=O)Nc1ccc(-c2c(-c3ccc(Oc4cccc(C)c4)c(OC)c3)c3c(N)ncnc3n2C)cc1] | . $^1$H NMR (400 MHz, DMSO-d$_6$) δ10.30 (s, 1H), 8.20 (s, 1H), 7.71 (d, J = 8.4 Hz, 2H), 7.32 (d, J = 8.4 Hz, 2H), 7.19 (t, J = 8.0 Hz, 1H), 6.90-6.97 (m, 2H), 6.76-6.88 (m, 2H), 6.71 (d, J = 2.0 Hz, 1H), 6.66-6.64 (m, 1H), 6.47-6.40 (m, 1H), 6.29-6.25 (m, 1H), 5.79-5.76 (m, 1H), 3.60 (d, J = 18.0 Hz, 6H), 2.27 (s, 3H). | 506.35 |
| N-(4-(4-amino-7-methyl-5-(4-(m-tolyloxy)phenyl)-7H-pyrrolo[2,3-d]pyrimidin-6-yl)phenyl)acrylamide | 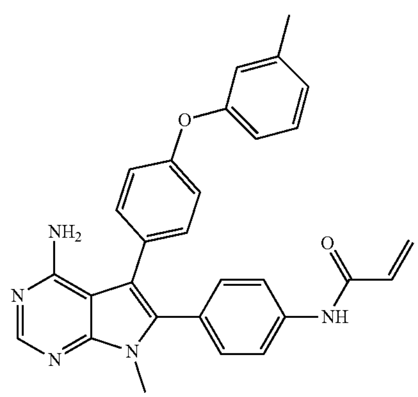 [SMILES: C=CC(=O)Nc1ccc(-c2c(-c3ccc(Oc4cccc(C)c4)cc3)c3c(N)ncnc3n2C)cc1] | $^1$H NMR (400 MHz, DMSO-d$_6$) δ 10.27 (s, 1H), 8.19 (s, 1H), 7.69 (d, J = 8.4 Hz, 2H), 7.35-7.17 (m, 6H), 7.02-6.80 (m, 5H), 6.44 (dd, J = 16.8, 10.0 Hz, 1H), 6.27 (dd, J = 16.8, 2.0 Hz, 1H), 6.16-5.66 (m, 2H), 3.61 (s, 3H), 2.30 (s, 3H). | 476.15 |
| N-(4-(4-amino-7-methyl-5-(4-((6-methylpyridin-2-yl)oxy)phenyl)-7H-pyrrolo[2,3-d]pyrimidin-6-yl)phenyl)methacrylamide | 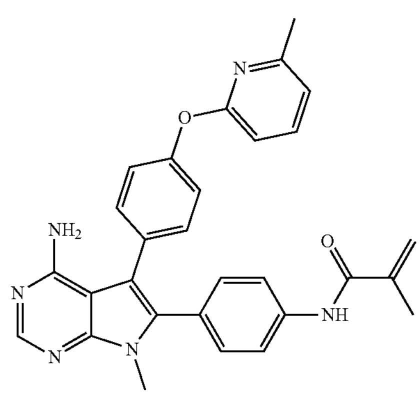 [SMILES: C=C(C)C(=O)Nc1ccc(-c2c(-c3ccc(Oc4cccc(C)n4)cc3)c3c(N)ncnc3n2C)cc1] | $^1$H NMR (400 MHz, DMSO-d$_6$) δ 9.90 (s, 1H), 8.20 (s, 1H), 7.73 (t, J = 8.1 Hz, 3H), 7.33-7.22 (m, 4H), 7.13-7.05 (m, 2H), 7.01 (d, J = 7.3 Hz, 1H), 6.78 (d, J = 8.2 Hz, 1H), 5.80 (t, J = 1.0 Hz, 1H), 5.53 (t, J = 1.4 Hz, 1H), 3.62 (s, 3H), 3.32 (d, J = 0.7 Hz, 1H), 2.35 (s, 3H), 1.95 (t, J = 1.2 Hz, 3H). | 491.2 |

TABLE 2-continued

Additional Exemplary Compounds

| Compound | Structure | Proton NMR | MS [M + 1] |
|---|---|---|---|
| N-(4-(4-amino-7-methyl-5-(4-(m-tolyloxy)phenyl)-7H-pyrrolo[2,3-d]pyrimidin-6-yl)phenyl) methacrylamide | 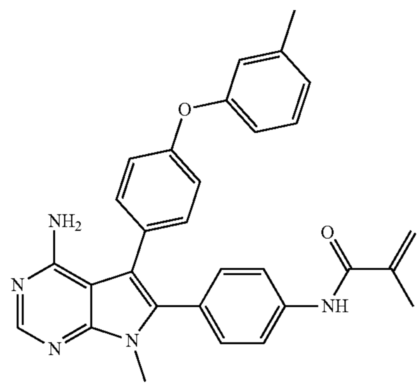 [SMILES: C=C(C)C(=O)Nc1ccc(-c2c(-c3ccc(Oc4cccc(C)c4)cc3)c3c(N)ncnc3n2C)cc1] | $^1$H NMR (400 MHz, DMSO-d$_6$) δ 9.91 (s, 1H), 8.19 (s, 1H), 7.71 (d, J = 8.2 Hz, 2H), 7.25 (dd, J = 18.4, 7.8 Hz, 5H), 6.95 (d, J = 8.2 Hz, 3H), 6.91-6.82 (m, 2H), 5.86 (s, 1H), 5.80 (s, 1H), 5.54 (s, 1H), 3.61 (s, 3H), 2.30 (s, 3H), 1.95 (s, 3H). | 490.15 |
| N-(4-(4-amino-5-(3-methoxy-4-phenoxyphenyl)-7-methyl-7H-pyrrolo[2,3-d]pyrimidin-6-yl)phenyl) methacrylamide | 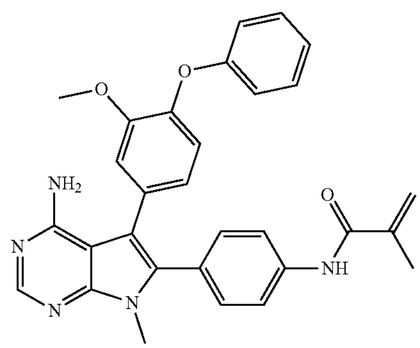 [SMILES: C=C(C)C(=O)Nc1ccc(-c2c(-c3ccc(Oc4ccccc4)c(OC)c3)c3c(N)ncnc3n2C)cc1] | $^1$H NMR (400 MHz, DMSO-d$_6$) δ 9.92 (s, 1H), 8.20 (s, 1H), 7.77-7.69 (m, 2H), 7.37-7.27 (m, 4H), 7.04 (t, J = 7.4 Hz, 1H), 7.00-6.93 (m, 2H), 6.93-6.86 (m, 2H), 6.80 (dd, J = 8.2, 2.0 Hz, 1H), 6.06 (s, 1H), 5.81 (s, 1H), 5.54 (d, J = 1.8 Hz, 1H), 3.60 (d, J = 10.8 Hz, 6H), 1.95 (d, J = 1.4 Hz, 3H). | 506.20 |
| N-(4-(4-amino-5-(3-methoxy-4-(m-tolyloxy)phenyl)-7-methyl-7H-pyrrolo[2,3-d]pyrimidin-6-yl)phenyl) methacrylamide | 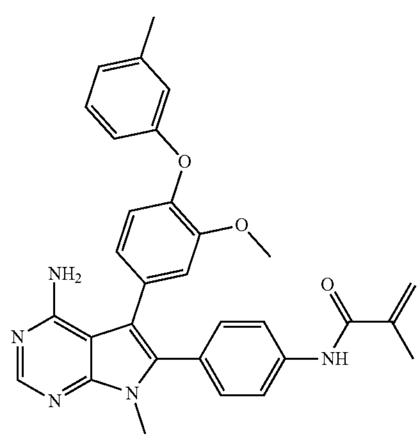 [SMILES: C=C(C)C(=O)Nc1ccc(-c2c(-c3ccc(Oc4cccc(C)c4)c(OC)c3)c3c(N)ncnc3n2C)cc1] | $^1$H NMR (400 MHz, DMSO-d6) δ 9.92 (s, 1H), 8.20 (s, 1H), 7.73 (d, J = 8.5 Hz, 2H), 7.30 (d, J = 8.4 Hz, 2H), 7.19 (t, J = 7.9 Hz, 1H), 6.98-6.90 (m, 2H), 6.85 (d, J = 7.5 Hz, 1H), 6.79 (dd, J = 8.1, 1.9 Hz, 1H), 6.71 (d, J = 2.3 Hz, 1H), 6.65 (dd, J = 8.2, 2.5 Hz, 1H), 6.04 (s, 2H), 5.80 (s, 1H), 5.54 (s, 1H), 3.60 (d, J = 12.6 Hz, 6H), 2.27 (s, 3H), 1.95 (s, 3H). | 519.23 |
| N-(4-(4-amino-5-(3-methoxy-4-((5-methylpyrimidin-2-yl)oxy)phenyl)-7-methyl-7H-pyrrolo[2,3-d]pyrimidin-6-yl)phenyl) acrylamide | 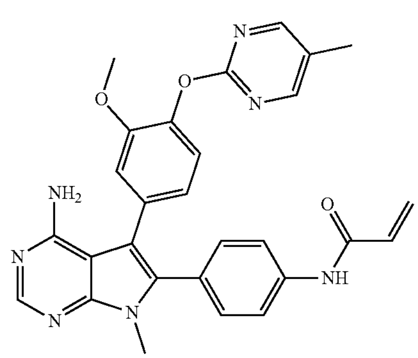 [SMILES: C=CC(=O)Nc1ccc(-c2c(-c3ccc(Oc4ncc(C)cn4)c(OC)c3)c3c(N)ncnc3n2C)cc1] | $^1$H NMR (400 MHz, DMSO-d6) δ 10.29 (s, 1H), 8.44 (d, J = 0.8 Hz, 2H), 8.21 (s, 1H), 7.73 (d, J = 8.4 Hz, 2H), 7.37 (d, J = 8.4 Hz, 2H), 7.14 (d, J = 8.0 Hz, 1H), 6.97 (d, J = 1.6 Hz, 1H), 6.86 (dd, J = 8.0, 2.0 Hz, 1H), 6.45 (dd, J = 16.8, 10.0 Hz, 1H), 6.32-6.21 (m, 1H), 5.79 (d, J = 11.6 Hz, 1H), 3.60 (s, 3H), 3.53 (s, 3H), 2.20 (s, 3H). | 508.20 |

TABLE 2-continued

Additional Exemplary Compounds

| Compound | Structure | Proton NMR | MS [M + 1] |
|---|---|---|---|
| N-(4-(4-amino-5-(3-methoxy-4-((4-methylpyridin-2-yl)oxy)phenyl)-7-methyl-7H-pyrrolo[2,3-d]pyrimidin-6-yl)phenyl)acrylamide | 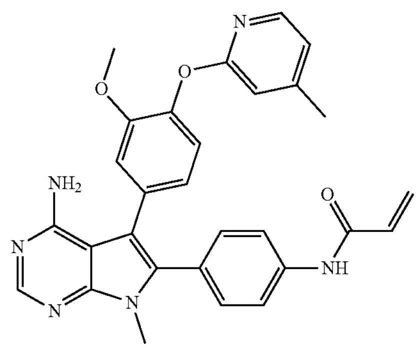 [SMILES: C=CC(=O)Nc1ccc(-c2c(-c3ccc(Oc4cc(C)ccn4)c(OC)c3)c3c(N)ncnc3n2C)cc1] | $^1$H NMR (400 MHz, DMSO-d6) δ 10.30 (s, 1H), 8.44 (s, 2H), 8.22 (s, 1H), 7.74 (d, J = 8.4 Hz, 2H), 7.38 (d, J = 8.4 Hz, 2H), 7.15 (d, J = 8.0 Hz, 1H), 6.97 (d, J = 2.0 Hz, 1H), 6.86 (d, J = 10.0 Hz, 1H), 6.46 (dd, J = 17.2, 10.0 Hz, 1H), 6.29 (d, J = 18.8 Hz, 1H), 5.79 (d, J = 12.0 Hz, 1H), 3.60 (s, 3H), 3.53 (s, 3H), 2.20 (s, 3H). | 507.25 |
| N-(4-(4-amino-5-(3-methoxy-4-(5-methylpyridin-3-yloxy)phenyl)-7-methyl-7H-pyrrolo[2,3-d]pyrimidin-6-yl)phenyl)acrylamide | 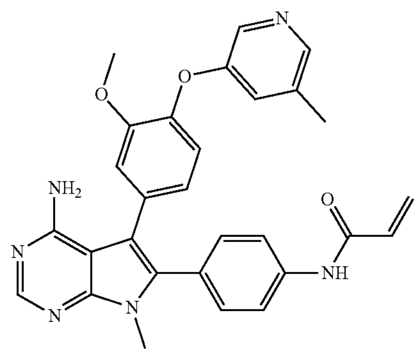 [SMILES: C=CC(=O)Nc1ccc(-c2c(-c3ccc(Oc4cncc(C)c4)c(OC)c3)c3c(N)ncnc3n2C)cc1] | $^1$H NMR (400 MHz, DMSO-d$_6$) δ 10.28 (s, 1H), 8.20 (s, 1H), 8.17-8.10 (m, 1H), 8.05 (d, J = 2.7 Hz, 1H), 7.78-7.66 (m, 2H), 7.38-7.26 (m, 2H), 7.12 (d, J = 2.5 Hz, 1H), 7.04 (d, J = 8.1 Hz, 1H), 6.98 (d, J = 1.9 Hz, 1H), 6.81 (dd, J = 8.1, 1.9 Hz, 1H), 6.45 (dd, J = 16.9, 10.1 Hz, 1H), 6.28 (dd, J = 17.0, 2.1 Hz, 1H), 5.78 (dd, J = 10.1, 2.1 Hz, 2H), 3.60 (d, J = 16.1 Hz, 6H), 2.27 (s, 3H). | 507.15 |
| N-(4-(4-amino-5-(3-methoxy-4-(pyridin-4-yloxy)phenyl)-7-methyl-7H-pyrrolo[2,3-d]pyrimidin-6-yl)phenyl)acrylamide | 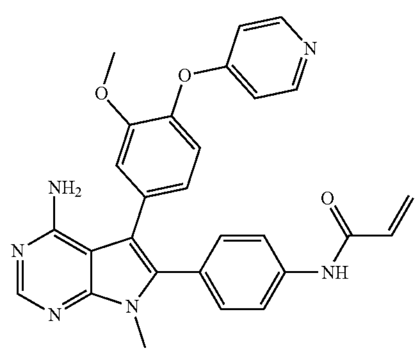 [SMILES: C=CC(=O)Nc1ccc(-c2c(-c3ccc(Oc4ccncc4)c(OC)c3)c3c(N)ncnc3n2C)cc1] | $^1$H NMR (400 MHz, DMSO-d6) δ 10.29 (s, 1H), 8.41 (d, J = 5.5 Hz, 2H), 8.21 (s, 1H), 7.72 (d, J = 8.4 Hz, 2H), 7.32 (d, J = 8.4 Hz, 2H), 7.13 (d, J = 8.0 Hz, 1H), 7.00 (d, J = 2.0 Hz, 1H), 6.95-6.79 (m, 3H), 6.52-6.38 (m, 1H), 6.36-6.20 (m, 1H), 6.14 (s, 2H), 5.86-5.70 (m, 1H), 3.63 (s, 3H), 3.57 (s, 3H). | 493.15 |
| N-(4-(4-amino-5-(4-((6-chloropyridin-2-yl)oxy)-3-methoxyphenyl)-7-methyl-7H-pyrrolo[2,3-d]pyrimidin-6-yl)phenyl)acrylamide | 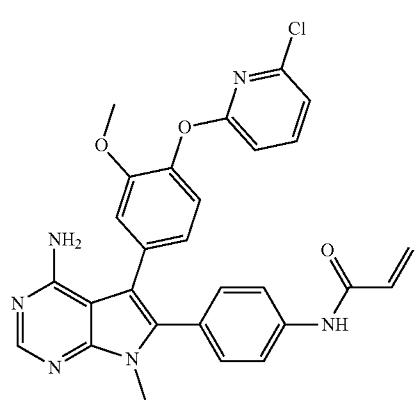 [SMILES: C=CC(=O)Nc1ccc(-c2c(-c3ccc(Oc4cccc(Cl)n4)c(OC)c3)c3c(N)ncnc3n2C)cc1] | $^1$H NMR (400 MHz, DMSO-d$_6$) δ10.28 (s, 1H), 8.21 (s, 1H), 7.84 (t, J = 14.6 Hz, 1H), 7.72 (d, J = 8.4 Hz, 2H), 7.33 (d, J = 8.8 Hz, 2H), 7.19 (d, J = 7.2 Hz, 1H), 7.14 (d, J = 8.0 Hz, 1H), 6.98 (s, 1H), 6.91 (d, J = 8.0 Hz, 1H), 6.85 (dd, J = 6.0 Hz, 1H), 6.41-6.43 (m, 1H), 6.25-6.29 (m, 1H), 5.82-6.18 (br, 1H), 3.62 (s, 3H), 3.55 (s, 3H), 2.78 (t, J = 12.0 Hz, 1H). | 527.30 |

TABLE 2-continued

Additional Exemplary Compounds

| Compound | Structure | Proton NMR | MS [M + 1] |
|---|---|---|---|
| N-(4-(4-amino-5-(4-((6-ethylpyridin-2-yl)oxy)-3-methoxyphenyl)-7-methyl-7H-pyrrolo[2,3-d]pyrimidin-6-yl)phenyl)acrylamide | 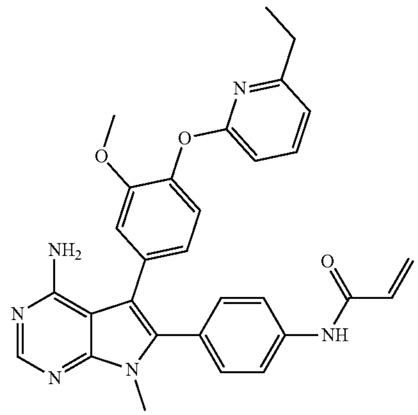 [SMILES: C=CC(=O)Nc1ccc(-c2c(-c3ccc(Oc4cccc(CC)n4)c(OC)c3)c3c(N)ncnc3n2C)cc1] | $^1$H NMR (400 MHz, Chloroform-d) δ 8.39 (s, 1H), 7.61 (dd, J = 26.2, 7.9 Hz, 3H), 7.47 (s, 1H), 7.09 (d, J = 7.9 Hz, 1H), 6.87 (d, J = 25.9 Hz, 3H), 6.62 (d, J = 8.3 Hz, 1H), 6.48 (d, J = 16.9 Hz, 1H), 6.29 (t, J = 13.8 Hz, 1H), 5.82 (d, J = 10.2 Hz, 1H), 5.22 (s, 2H), 3.76 (s, 3H), 3.59 (s, 3H), 2.69 (d, J = 8.0 Hz, 2H), 1.20 (t, J = 7.7 Hz, 3H). | 521.2 |
| N-(4-(4-amino-5-(4-((5,6-dimethylpyridin-2-yl)oxy)-3-methoxyphenyl)-7-methyl-7H-pyrrolo[2,3-d]pyrimidin-6-yl)phenyl)acrylamide | 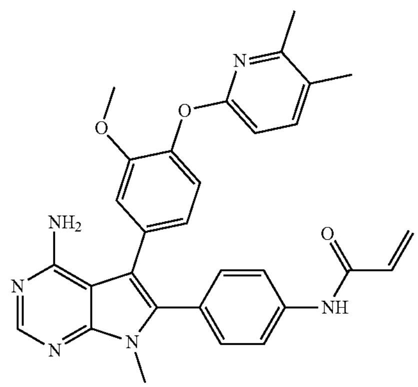 [SMILES: C=CC(=O)Nc1ccc(-c2c(-c3ccc(Oc4ccc(C)c(C)n4)c(OC)c3)c3c(N)ncnc3n2C)cc1] | $^1$H NMR (400 MHz, DMSO-d$_6$) δ 10.28 (s, 1H), 8.20 (s, 1H), 7.71 (d, J = 8.6 Hz, 2H), 7.50 (d, J = 8.4 Hz, 1H), 7.34 (d, J = 8.4 Hz, 2H), 7.03 (d, J = 8.0 Hz, 1H), 6.95 (d, J = 2.0 Hz, 1H), 6.81 (dd, J = 8.2, 1.8 Hz, 1H), 6.57 (d, J = 8.2 Hz, 1H), 6.45 (dd, J = 17.0, 10.0 Hz, 1H), 6.32-6.23 (m, 1H), 5.78 (d, J = 11.8 Hz, 1H), 3.62 (s, 3H), 3.54 (s, 3H), 2.25 (s, 3H), 2.17 (s, 3H), 1.24 (s, 1H). | 521.20 |
| N-(4-(4-amino-5-(3-methoxy-4-((4-methylpyrimidin-2-yl)oxy)phenyl)-7-methyl-7H-pyrrolo[2,3-d]pyrimidin-6-yl)phenyl)acrylamide | 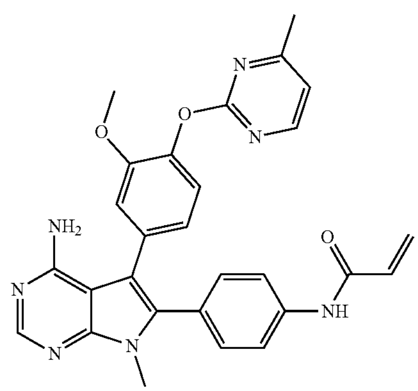 [SMILES: C=CC(=O)Nc1ccc(-c2c(-c3ccc(Oc4nccc(C)n4)c(OC)c3)c3c(N)ncnc3n2C)cc1] | $^1$H NMR (400 MHz, DMSO-d$_6$) δ 10.29 (s, 1H), 8.41 (d, J = 5.0 Hz, 1H), 8.21 (s, 1H), 7.73 (d, J = 8.6 Hz, 2H), 7.40-7.33 (m, 2H), 7.17-7.07 (m, 2H), 6.97 (d, J = 1.8 Hz, 1H), 6.86 (dd, J = 8.0, 2.0 Hz, 1H), 6.45 (dd, J = 17.0, 10.2 Hz, 1H), 6.28 (dd, J = 17.0, 2.0 Hz, 1H), 5.78 (dd, J = 10.2, 2.0 Hz, 1H), 3.61 (s, 3H), 3.53 (s, 3H), 2.40 (s, 3H). | 508.15 |
| N-(4-(4-amino-5-(3-methoxy-4-(5-methylpyridin-2-yloxy)phenyl)-7-methyl-7H-pyrrolo[2,3-d]pyrimidin-6-yl)phenyl)acrylamide | 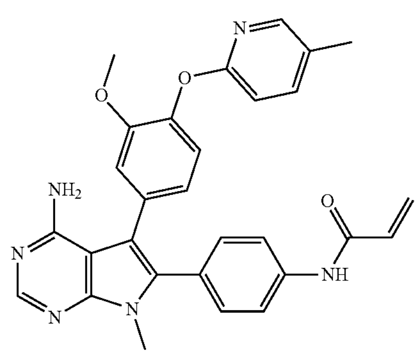 [SMILES: C=CC(=O)Nc1ccc(-c2c(-c3ccc(Oc4ccc(C)cn4)c(OC)c3)c3c(N)ncnc3n2C)cc1] | $^1$H NMR (400 MHz, DMSO-d$_6$) δ 10.29 (s, 1H), 8.20 (s, 1H), 7.91 (s, 1H), 7.71-7.73 (d, J = 8 Hz, 2H), 7.60-7.62 (d, J = 8 Hz, 1H), 7.34-7.36 (d, J = 8 Hz, 1H), 7.05-7.07 (d, J = 8Hz, 1H), 6.94 (s, 1H), 6.82-6.86 (m, 2H), 6.41-6.48 (m, 1H), 6.25-6.30 (m, 1H), 5.97 (s, 1H), 5.77-5.79 (d, J = 8 Hz, 1H), 3.60 (s, 3H), 3.53 (s, 3H), 2.21 (s, 3H). | 507.35 |

TABLE 2-continued

Additional Exemplary Compounds

| Compound | Structure | Proton NMR | MS [M + 1] |
|---|---|---|---|
| N-(4-(4-amino-5-(3-methoxy-4-((3-methylpyridin-2-yl)oxy)phenyl)-7-methyl-7H-pyrrolo[2,3-d]pyrimidin-6-yl)phenyl)acrylamide | 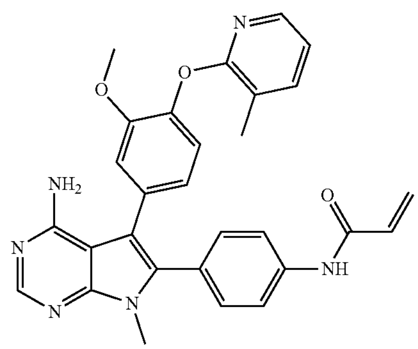 [SMILES: C=CC(=O)Nc1ccc(-c2c(-c3ccc(Oc4ncccc4C)c(OC)c3)c3c(N)ncnc3n2C)cc1] | $^1$H NMR (400 MHz, DMSO-d$_6$) δ 10.30 (s, 1H), 8.21 (s, 1H), 7.88 (d, J = 4.9 Hz, 1H), 7.73 (d, J = 8.2 Hz, 2H), 7.65 (d, J = 12 Hz, 1H), 7.35 (dd, J = 17.4, 8.2 Hz, 2H), 7.08 (dd, J = 8.1, 2.8 Hz, 1H), 7.01-6.92 (m, 2H), 6.88-6.80 (m, 1H), 6.45 (dd, J = 17.0, 10.0 Hz, 1H), 6.28 (dd, J = 16.9, 2.0 Hz, 1H), 5.99 (s, 2H), 5.78 (dd, J = 9.9, 2.1 Hz, 1H), 3.60 (d, J = 5.7 Hz, 3H), 3.53 (s, 3H), 2.30 (s, 3H). | 507.2 |
| N-(4-(4-amino-5-(3-methoxy-4-((6-methylpyridin-3-yl)oxy)phenyl)-7-methyl-7H-pyrrolo[2,3-d]pyrimidin-6-yl)phenyl)acrylamide | 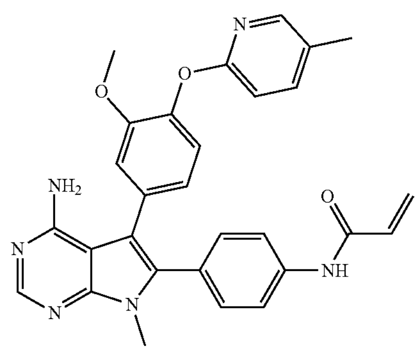 | $^1$H NMR (400 MHz, DMSO-d6) δ 10.28 (s, 1H), 8.20 (s, 1H), 8.13 (dd, J = 2.4, 1.2 Hz, 1H), 7.71 (d, J = 8.4 Hz, 2H), 7.38-121 (m, 2H), 7.26-7.16 (m, 1H), 7.06-6.93 (m, 2H), 6.79 (dd, J = 8.0, 2.0 Hz, 1H), 6.45 (dd, J = 17.2, 10.0 Hz, 1H), 6.28 (dd, J = 17.2, 2.0 Hz, 1H), 6.05 (s, 1H), 5.78 (dd, J = 10.0, 2.0 Hz, 1H), 3.62 (s, 3H), 3.59 (s, 3H), 2.42 (s, 3H). | 507.35 |
| N-(4-(4-amino-5-(3-methoxy-4-(pyrimidin-2-yloxy)phenyl)-7-methyl-7H-pyrrolo[2,3-d]pyrimidin-6-yl)phenyl)methacrylamide | 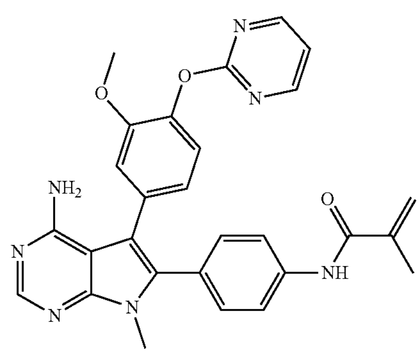 [SMILES: C=C(C)C(=O)Nc1ccc(-c2c(-c3ccc(Oc4ncccn4)c(OC)c3)c3c(N)ncnc3n2C)cc1] | $^1$H NMR (400 MHz, DMSO-d6) δ 9.93 (s, 1H), 8.62 (d, J = 4.8 Hz, 2H), 8.21 (s, 1H), 7.79-7.72 (m, 2H), 7.39-7.33 (m, 2H), 7.23 (t, J = 4.8 Hz, 1H), 7.17 (d, J = 8.1 Hz, 1H), 6.99 (d, J = 1.9 Hz, 1H), 6.86 (dd, J = 8.0, 2.0 Hz, 1H), 6.01 (s, 2H), 5.81 (s, 1H), 5.54 (s, 1H), 3.60 (s, 3H), 3.55 (s, 3H), 1.96 (s, 3H). | 508.30 |
| N-(4-(4-amino-5-(3-methoxy-4-(pyrimidin-2-yloxy)phenyl)-7-methyl-7H-pyrrolo[2,3-d]pyrimidin-6-yl)phenyl)propionamide | 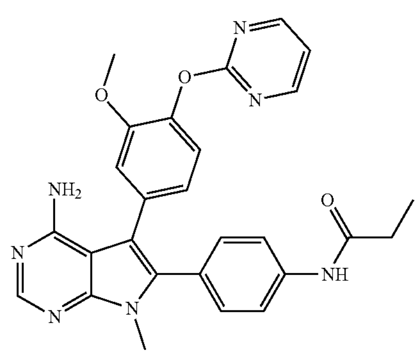 [SMILES: CCC(=O)Nc1ccc(-c2c(-c3ccc(Oc4ncccn4)c(OC)c3)c3c(N)ncnc3n2C)cc1] | $^1$H NMR (400 MHz, DMSO-d$_6$) δ 10.01 (s, 1H), 8.62 (d, J = 4.8 Hz, 2H), 8.21 (s, 1H), 7.65 (d, J = 8.4 Hz, 2H), 7.33 (d, J = 8.4 Hz, 2H), 7.23 (t, J = 4.8 Hz, 1H), 7.17 (d, J = 8.1 Hz, 1H), 6.98 (d, J = 2.0 Hz, 1H), 6.85 (dd, J = 8.0, 1.9 Hz, 1H), 5.97 (s, 2H), 3.56 (d, J = 17.7 Hz, 6H), 2.33 (q, J = 7.5 Hz, 2H), 1.09 (t, J = 7.5 Hz, 3H). | 496.3 |

TABLE 2-continued

Additional Exemplary Compounds

| Compound | Structure | Proton NMR | MS [M + 1] |
|---|---|---|---|
| N-(4-(4-amino-5-(3,4-dimethoxyphenyl)-7-methyl-7H-pyrrolo[2,3-d]pyrimidin-6-yl)phenyl)acrylamide | 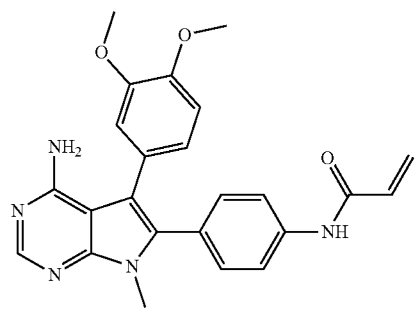 [SMILES: C=CC(=O)Nc1ccc(-c2c(-c3ccc(OC)c(OC)c3)c3c(N)ncnc3n2C)cc1] | $^1$H NMR (400 MHz, DMSO-d6) δ 10.26 (s, 1H), 8.18 (s, 1H), 7.69 (d, J = 8.4 Hz, 2H), 7.35-7.23 (m, 2H), 6.94 (d, J = 8.0 Hz, 1H), 6.77 (d, J = 8.0 Hz, 2H), 6.45 (dd, J = 17.2, 10.0 Hz, 1H), 6.28 (dd, J = 16.8, 2.0 Hz, 1H), 5.78 (dd, J = 10.0, 2.0 Hz, 1H), 3.75 (s, 3H), 3.60 (d, J = 0.8 Hz, 6H). | 430.30 |
| N-(4-(4-amino-5-(3-ethoxy-4-(pyrimidin-2-yloxy)phenyl)-7-methyl-7H-pyrrolo[2,3-d]pyrimidin-6-yl)phenyl)acrylamide | 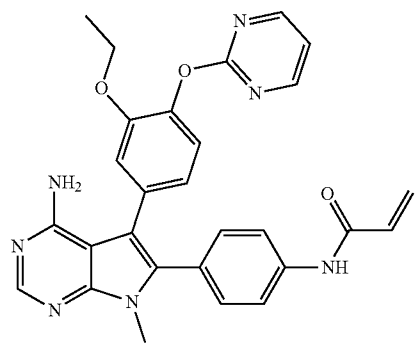 [SMILES: C=CC(=O)Nc1ccc(-c2c(-c3ccc(Oc4ncccn4)c(OCC)c3)c3c(N)ncnc3n2C)cc1] | $^1$H NMR (400 MHz, DMSO-d6) δ 10.29 (s, 1H), 8.62 (d, J = 4.8 Hz, 2H), 8.21 (s, 1H), 7.85-7.68 (m, 2H), 7.56-7.29 (m, 2H), 7.23 (t, J = 4.8 Hz, 1H), 7.18 (d, J = 8.1 Hz, 1H), 6.95 (d, J = 2.0 Hz, 1H), 6.91-6.81 (m, 1H), 6.51-6.39 (m, 1H), 6.35-6.21 (m, 1H), 5.98 (s, 2H), 5.82-5.73 (m, 1H), 3.88-3.74 (m, 2H), 3.60 (s, 3H), 0.93 (t, J = 7.0 Hz, 3H). | 508.35 |
| N-(4-(4-amino-5-(3-ethyl-4-(pyrimidin-2-yloxy)phenyl)-7-methyl-7H-pyrrolo[2,3-d]pyrimidin-6-yl)phenyl)acrylamide | 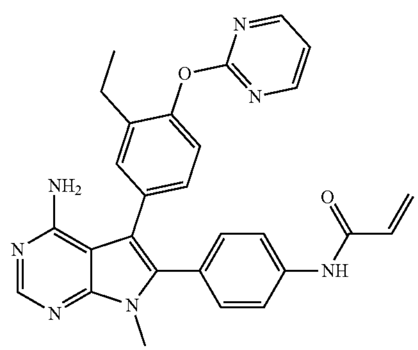 | $^1$H NMR (400 MHz, DMSO-d$_6$) δ 10.29 (s, 1H), 8.65 (d, J = 4.8 Hz, 2H), 8.21 (s, 1H), 7.72 (d, J = 8.4 Hz, 2H), 7.35 (d, J = 8.4 Hz, 2H), 7.30-7.18 (m, 2H), 7.18-7.03 (m, 2H), 6.45 (dd, J = 16.9, 10.1 Hz, 1H), 6.28 (dd, J = 17.0, 2.1 Hz, 1H), 5.96 (s, 1H), 5.78 (dd, J = 10.1, 2.1 Hz, 1H), 3.60 (s, 3H), 2.47-2.31 (m, 2H), 0.97 (t, J = 7.5 Hz, 3H). | 492.15 |
| N-(4-(4-amino-7-methyl-5-(4-(pyrimidin-2-yloxy)-3-(trifluoromethyl)phenyl)-7H-pyrrolo[2,3-d]pyrimidin-6-yl)phenyl)acrylamide | 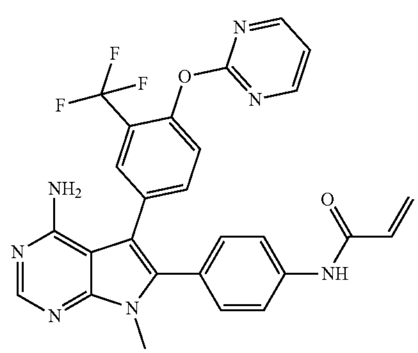 [SMILES: C=CC(=O)Nc1ccc(-c2c(-c3ccc(Oc4ncccn4)c(C(F)(F)F)c3)c3c(N)ncnc3n2C)cc1] | $^1$H NMR (400 MHz, DMSO-d$_6$) δ 10.32 (s, 1H), 8.72-8.66 (m, 2H), 8.23 (s, 1H), 7.74 (d, J = 8.3 Hz, 2H), 7.59-7.53 (m, 2H), 7.43 (d, J = 9.0 Hz, 1H), 7.39-7.30 (m, 3H), 6.45 (dd, J = 16.9, 10.1 Hz, 1H), 6.28 (dd, J = 16.7, 2.0 Hz, 1H), 6.03 (s, 2H), 5.83-5.75 (m, 1H), 3.59 (s, 3H). | 532.1 |

TABLE 2-continued

Additional Exemplary Compounds

| Compound | Structure | Proton NMR | MS [M + 1] |
|---|---|---|---|
| N-(4-(4-amino-5-(3-(dimethylamino)-4-(pyrimidin-2-yloxy)phenyl)-7-methyl-7H-pyrrolo[2,3-d]pyrimidin-6-yl)phenyl)acrylamide | 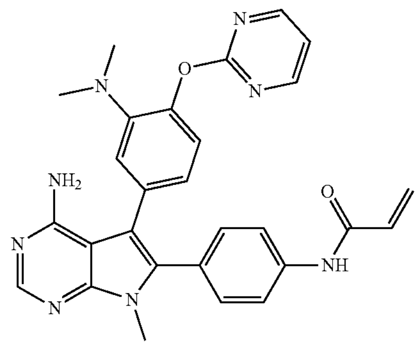 [SMILES: C=CC(=O)Nc1ccc(-c2c(-c3ccc(Oc4ncccn4)c(N(C)C)c3)c3c(N)ncnc3n2C)cc1] | $^1$H NMR (400 MHz, DMSO-d$_6$) δ 10.30 (s, 1H), 8.63 (d, J = 4.8 Hz, 2H), 8.20 (s, 1H), 7.73 (d, J = 8.4 Hz, 2H), 7.39-7.31 (m, 2H), 7.24 (t, J = 4.8 Hz, 1H), 7.07 (d, J = 8.0 Hz, 1H), 6.89-6.81 (m, 2H), 6.45 (dd, J = 16.8, 10.2 Hz, 1H), 6.28 (dd, J = 16.8, 2.2 Hz, 1H), 6.06 (s, 2H), 5.78 (dd, J = 10.0, 2.2 Hz, 1H), 3.60 (s, 3H), 2.53 (s, 6H). | 507.20 |
| N-(4-(4-amino-7-methyl-5-(4-(pyrimidin-2-yloxy)-3-(trifluoromethoxy)phenyl)-7H-pyrrolo[2,3-d]pyrimidin-6-yl)phenyl)acrylamide | 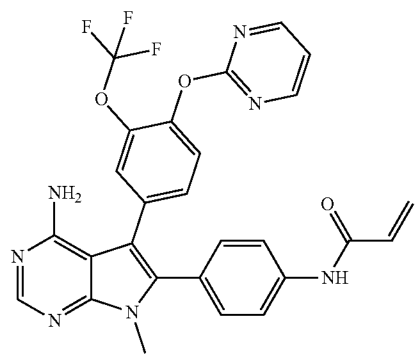 [SMILES: C=CC(=O)Nc1ccc(-c2c(-c3ccc(Oc4ncccn4)c(OC(F)(F)F)c3)c3c(N)ncnc3n2C)cc1] | $^1$H NMR (400 MHz, DMSO-d$_6$) δ 10.30 (s, 1H), 8.68 (d, J = 4.7 Hz, 2H), 8.23 (s, 1H), 7.74 (d, J = 8.5 Hz, 2H), 7.47 (d, J = 8.4 Hz, 1H), 7.40-7.19 (m, 6H), 6.53-6.36 (m, 1H), 6.30 (d, J = 2.0 Hz, 1H), 6.03 (s, 2H), 5.85-5.73 (m, 1H), 3.60 (s, 3H). | 548.25 |
| N-(4-(4-amino-5-(3-(hydroxymethyl)-4-(pyrimidin-2-yloxy)phenyl)-7-methyl-7H-pyrrolo[2,3-d]pyrimidin-6-yl)phenyl)acrylamide | 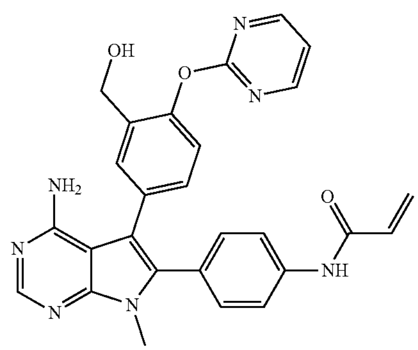 [SMILES: C=CC(=O)Nc1ccc(-c2c(-c3ccc(Oc4ncccn4)c(CO)c3)c3c(N)ncnc3n2C)cc1] | $^1$H NMR (400 MHz, DMSO-d$_6$) δ 10.26 (s, 1H), 10.04 (s, 1H), 8.52 (dd, J = 4.2, 2.8 Hz, 1H), 8.16 (s, 1H), 8.02 (dd, J = 6.5, 2.8 Hz, 1H), 7.69-7.62 (m, 2H), 7.26-7.19 (m, 2H), 6.98 (d, J = 7.9 Hz, 2H), 6.80 (d, J = 8.0 Hz, 1H), 6.46 (dd, J = 16.9, 10.1 Hz, 1H), 6.39 (dd, J = 6.5, 4.1 Hz, 1H), 6.29 (dd, J = 16.9, 2.1Hz, 1H), 5.79 (dd, J = 10.1, 2.1 Hz, 1H), 4.91 (s, 2H), 3.58 (s, 3H). | 494.3 |
| N-(4-(4-amino-5-(3-methoxy-4-(pyrimidin-2-ylthio)phenyl)-7-methyl-7H-pyrrolo[2,3-d]pyrimidin-6-yl)phenyl)acrylamide | 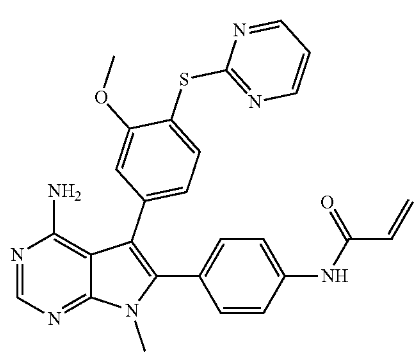 [SMILES: C=CC(=O)Nc1ccc(-c2c(-c3ccc(Sc4ncccn4)c(OC)c3)c3c(N)ncnc3n2C)cc1] | $^1$H NMR (400 MHz, DMSO-d6) δ 10.30 (s, 1H), 8.57 (d, J = 4.8 Hz, 2H), 8.23 (s, 1H), 7.81-7.70 (m, 2H), 7.53 (d, J = 8.0 Hz, 1H), 7.44-7.32 (m, 2H), 7.20 (m, J = 4.8 Hz, 1H), 7.01-6.83 (m, 2H), 6.46 (dd, J = 17.2, 10.0 Hz, 1H), 6.29 (dd, J = 17.2, 2.0 Hz, 1H), 6.02 (s, 1H), 5.79 (dd, J = 10.0, 2.0 Hz, 1H), 3.60 (d, J = 17.2 Hz, 6H). | 510.10 |

TABLE 2-continued

Additional Exemplary Compounds

| Compound | Structure | Proton NMR | MS [M + 1] |
|---|---|---|---|
| N-(4-(4-amino-5-(3-methoxy-4-(pyrimidin-2-ylamino)phenyl)-7-methyl-7H-pyrrolo[2,3-d]pyrimidin-6-yl)phenyl)acrylamide | 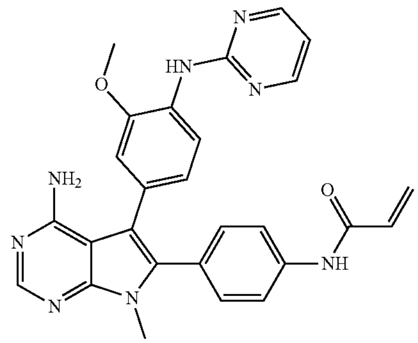 [SMILES: C=CC(=O)Nc1ccc(-c2c(-c3ccc(Nc4ncccn4)c(OC)c3)c3c(N)ncnc3n2C)cc1] | $^1$H NMR (400 MHz, DMSO-d$_6$) δ 10.26 (s, 1H), 8.46-8.47 (d, J = 4.8 Hz, 1H), 8.16-8.19 (m, 2H), 8.04 (s, 1H), 7.69-7.71 (d, J = 8 Hz, 2H), 7.33-7.35 (d, J = 8 Hz, 2H), 6.83-6.87 (m, 3H), 6.40-6.49 (m, 1H), 6.24-6.29 (m, 1H), 5.98 (s, 1H), 5.76-5.78 (m, 1H), 3.70 (s, 3H), 3.60 (s, 3H). | 493.30 |
| N-(4-(4-amino-5-(3-methoxy-4-(methyl(pyrimidin-2-yl)amino)phenyl)-7-methyl-7H-pyrrolo[2,3-d]pyrimidin-6-yl)phenyl)acrylamide | 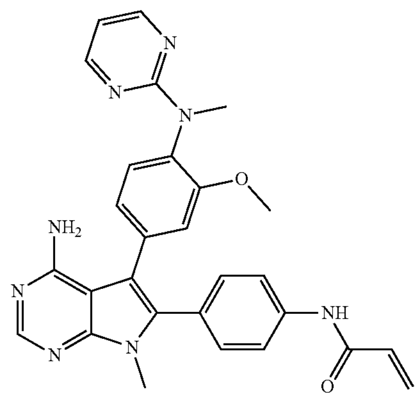 [SMILES: C=CC(=O)Nc1ccc(-c2c(-c3ccc(N(C)c4ncccn4)c(OC)c3)c3c(N)ncnc3n2C)cc1] | $^1$H NMR (400 MHz, DMSO-d$_6$) δ 10.29 (s, 1H), 8.29-8.31 (m, 2H), 8.19 (s, 1H), 7.75-7.77 (d, J = 8.2 Hz, 2H), 7.19-7.21 (d, J = 8.1 Hz, 1H), 6.85-6.92 (m, 2H), 6.64-6.69 (m, 1H), 6.42-6.49 (m, 1H), 6.25-6.31 (m, 1H), 6.01 (s, 1H), 5.77-5.80 (m, 1H), 3.56-3.59 (m, 6H), 3.30 (s, 3H). | 507.35 |
| N-(4-(4-amino-5-(3-methoxy-5-methyl-4-(pyrimidin-2-yloxy)phenyl)-7-methyl-7H-pyrrolo[2,3-d]pyrimidin-6-yl)phenyl)acrylamide | 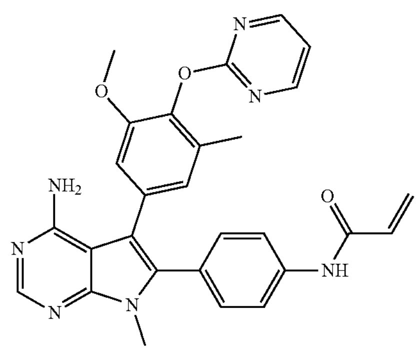 [SMILES: C=CC(=O)Nc1ccc(-c2c(-c3cc(C)c(Oc4ncccn4)c(OC)c3)c3c(N)ncnc3n2C)cc1] | $^1$H NMR (400 MHz, DMSO-d6) δ 10.29 (s, 1H), 8.61 (d, J = 4.8 Hz, 2H), 8.21 (s, 1H), 7.74 (d, J = 8.4 Hz, 2H), 7.39 (d, J = 8.5 Hz, 2H), 7.22 (t, J = 4.8 Hz, 1H), 6.85-6.77 (m, 2H), 6.45 (dd, J = 17.0, 10.1 Hz, 1H), 6.28 (dd, J = 16.9, 2.0 Hz, 1H), 5.78 (dd, J = 10.1, 2.0 Hz, 1H), 3.59 (s, 3H), 3.50 (s, 3H), 2.05 (s, 3H). | 508.25 |
| N-(4-(4-amino-7-methyl-5-(4-(pyrimidin-2-yloxy)phenyl)-7H-pyrrolo[2,3-d]pyrimidin-6-yl)phenyl)methacrylamide | 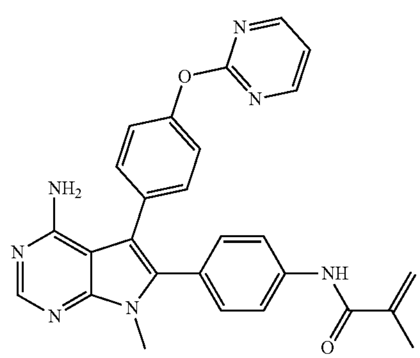 [SMILES: C=C(C)C(=O)Nc1ccc(-c2c(-c3ccc(Oc4ncccn4)cc3)c3c(N)ncnc3n2C)cc1] | $^1$H NMR (400 MHz, DMSO-d$_6$) δ 9.92 (s, 1H), 8.67 (d, J = 4.8 Hz, 2H), 8.21 (s, 1H), 7.78-7.70 (m, 2H), 7.35-7.25 (m, 5H), 7.25-7.17 (m, 2H), 5.83-5.78 (m, 1H), 5.56-5.51 (m, 1H), 3.60 (s, 3H), 1.95 (t, J = 1.2 Hz, 3H). | 478.10 |

TABLE 2-continued

Additional Exemplary Compounds

| Compound | Structure | Proton NMR | MS [M + 1] |
|---|---|---|---|
| N-(4-(4-amino-7-methyl-5-(4-(pyrimidin-2-ylthio)phenyl)-7H-pyrrolo[2,3-d]pyrimidin-6-yl)phenyl)acrylamide | 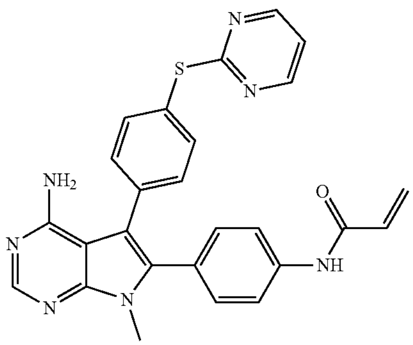 | $^1$H NMR (400 MHz, DMSO-d$_6$) δ 10.29 (s, 1H), 8.61 (d, J = 4.8 Hz, 2H), 8.22 (s, 1H), 7.71 (d, J = 8.6 Hz, 2H), 7.59 (d, J = 8.1 Hz, 2H), 7.36-7.29 (m, 4H), 7.25 (t, J = 4.8 Hz, 1H), 6.44 (dd, J = 17.0, 10.2 Hz, 1H), 6.28 (dd, J = 17.0, 2.0 Hz, 1H), 5.78 (dd, J = 10.1, 2.1 Hz, 1H), 3.61 (s, 3H). | 480.25 |
| N-(4-(4-amino-7-methyl-5-(4-(pyrimidin-2-ylthio)phenyl)-7H-pyrrolo[2,3-d]pyrimidin-6-yl)phenyl)methacrylamide | 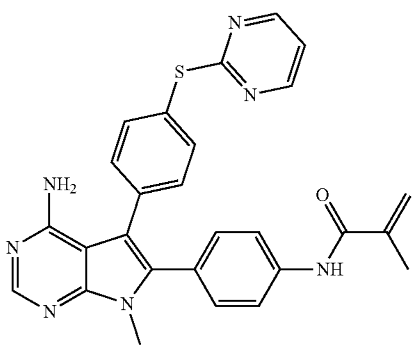 [SMILES: C=C(C)C(=O)Nc1ccc(-c2c(-c3ccc(Sc4ncccn4)cc3)c3c(N)ncnc3n2C)cc1] | $^1$H NMR (400 MHz, DMSO-d$_6$) δ 9.92 (s, 1H), 8.62 (d, J = 4.9 Hz, 2H), 8.22 (s, 1H), 7.74 (d, J = 8.6 Hz, 2H), 7.59 (d, J = 8.1 Hz, 2H), 7.37-7.28 (m, 4H), 7.25 (t, J = 4.8 Hz, 1H), 5.80 (s, 1H), 5.54 (s, 1H), 3.61 (s, 3H), 1.95 (s, 3H). | 494.25 |
| N-(4-(4-amino-7-methyl-5-(4-(pyrimidin-2-ylamino)phenyl)-7H-pyrrolo[2,3-d]pyrimidin-6-yl)phenyl)acrylamide | 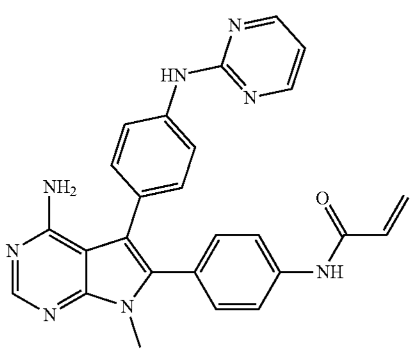 [SMILES: C=CC(=O)Nc1ccc(-c2c(-c3ccc(Nc4ncccn4)cc3)c3c(N)ncnc3n2C)cc1] | $^1$H NMR (400 MHz, DMSO-d$_6$) δ 10.26 (s, 1H), 9.73 (s, 1H), 8.48 (d, J = 4.8 Hz, 2H), 8.18 (s, 1H), 7.76 (d, J = 8.3 Hz, 4H), 7.68 (d, J = 8.3 Hz, 2H), 7.30 (d, J = 8.6 Hz, 2H), 7.16 (d, J = 8.6 Hz, 2H), 6.84 (t, J = 4.7 Hz, 1H), 6.44 (dd, J = 17.0, 10.1 Hz, 1H), 6.27 (dd, J = 17.0, 2.1 Hz, 1H), 5.77 (dd, J = 10.0, 2.1 Hz, 2H), 3.61 (s, 4H). | 463.25 |
| N-(4-(4-amino-7-methyl-5-(4-(pyrimidin-2-ylamino)phenyl)-7H-pyrrolo[2,3-d]pyrimidin-6-yl)phenyl)methacrylamide | 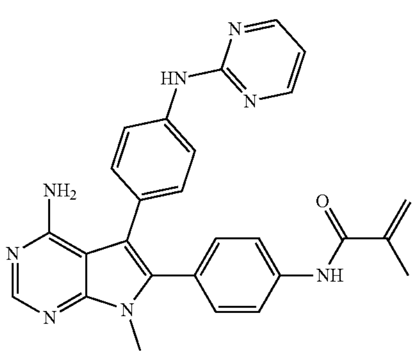 [SMILES: C=C(C)C(=O)Nc1ccc(-c2c(-c3ccc(Nc4ncccn4)cc3)c3c(N)ncnc3n2C)cc1] | $^1$H NMR (400 MHz, DMSO-d$_6$) δ 9.89 (s, 1H), 9.73 (s, 1H), 8.48 (d, J = 4.6 Hz, 2H), 8.19 (s, 1H), 8.02-7.52 (m, 5H), 7.22 (dd, J = 53.0, 7.6 Hz, 4H), 6.85 (s, 1H), 5.79 (s, 2H), 5.53 (s, 1H), 3.61 (s, 3H), 1.95 (s, 3H). | 477.30 |

TABLE 2-continued

Additional Exemplary Compounds

| Compound | Structure | Proton NMR | MS [M + 1] |
|---|---|---|---|
| N-(4-(4-amino-7-methyl-5-(4-(methyl(pyrimidin-2-yl)amino)phenyl)-7H-pyrrolo[2,3-d]pyrimidin-6-yl)phenyl)acrylamide | 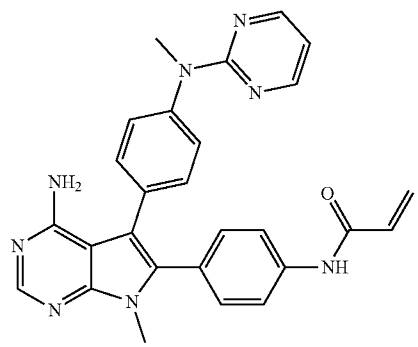 [SMILES: C=CC(=O)Nc1ccc(-c2c(-c3ccc(N(C)c4ncccn4)cc3)c3c(N)ncnc3n2C)cc1] | $^1$H NMR (400 MHz, DMSO-d$_6$) δ 10.29 (s, 1H), 8.39 (d, J = 4.8 Hz, 2H), 8.20 (s, 1H), 7.71 (d, J = 8.3 Hz, 2H), 7.42-7.32 (m, 4H), 7.26 (d, J = 8.2 Hz, 2H), 6.75 (t, J = 4.7 Hz, 1H), 6.44 (dd, J = 16.9, 10.1 Hz, 1H), 6.27 (dd, J = 17.0, 2.0 Hz, 1H), 5.78 (dd, J = 9.9, 2.0 Hz, 2H), 3.59 (s, 3H), 3.47 (s, 3H). | 477.25 |
| N-(4-(4-amino-7-methyl-5-(4-(methyl(pyrimidin-2-yl)amino)phenyl)-7H-pyrrolo[2,3-d]pyrimidin-6-yl)phenyl)methacrylamide | 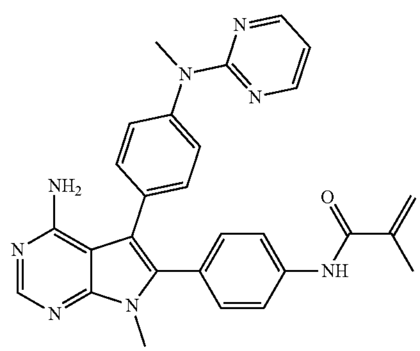 [SMILES: C=C(C)C(=O)Nc1ccc(-c2c(-c3ccc(N(C)c4ncccn4)cc3)c3c(N)ncnc3n2C)cc1] | $^1$H NMR (400 MHz, DMSO-d$_6$) δ 9.92 (s, 1H), 8.40 (d, J = 4.7 Hz, 2H), 8.20 (s, 1H), 7.74 (d, J = 8.4 Hz, 2H), 7.35 (t, J = 8.9 Hz, 4H), 7.26 (d, J = 8.3 Hz, 2H), 6.75 (t, J = 4.7 Hz, 1H), 5.80 (s, 2H), 5.54 (s, 1H), 3.59 (s, 3H), 3.47 (s, 3H), 1.95 (d, J = 1.3 Hz, 3H). | 491.30 |
| N-(4-(4-amino-5-(3-methoxy-4-(pyridin-2-yloxy)phenyl)-7-methyl-7H-pyrrolo[2,3-d]pyrimidin-6-yl)phenyl)propionamide | 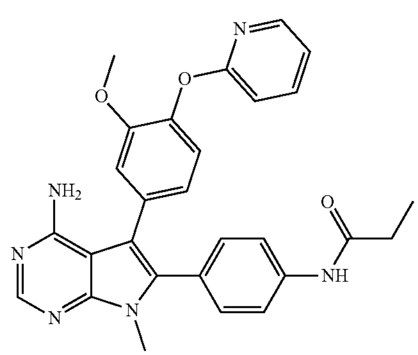 [SMILES: CCC(=O)Nc1ccc(-c2c(-c3ccc(Oc4ccccn4)c(OC)c3)c3c(N)ncnc3n2C)cc1] | $^1$H NMR (400 MHz, DMSO-d6) δ 10.01 (s, 1H), 8.21 (s, 1H), 8.11 (dd, J = 5.0, 1.9 Hz, 1H), 7.84-7.76 (m, 1H), 7.65 (d, J = 8.5 Hz, 2H), 7.32 (d, J = 8.6 Hz, 2H), 7.13-7.03 (m, 2H), 6.98-6.92 (m, 2H), 6.83 (dd, J = 8.0, 2.0 Hz, 1H), 5.99 (s, 2H), 3.59 (s, 3H), 3.54 (s, 3H), 2.34 (q, J = 7.6 Hz, 2H), 1.09 (t, J = 7.5 Hz, 3H). | 494.21 |
| N-(4-(4-amino-5-(3-methoxy-4-((6-methylpyridin-2-yl)oxy)phenyl)-7-methyl-7H-pyrrolo[2,3-d]pyrimidin-6-yl)phenyl)propionamide | 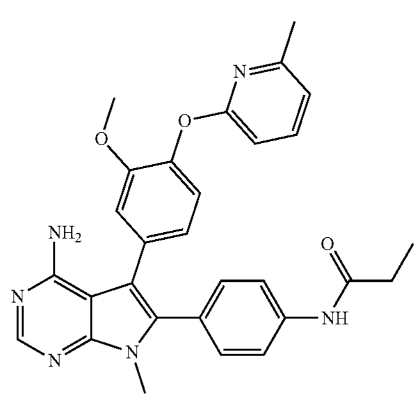 [SMILES: CCC(=O)Nc1ccc(-c2c(-c3ccc(Oc4cccc(C)n4)c(OC)c3)c3c(N)ncnc3n2C)cc1] | $^1$H NMR (400 MHz, DMSO-d6) δ 10.00 (s, 1H), 8.20 (s, 1H), 7.64 (d, J = 8.5 Hz, 3H), 7.30 (d, J = 8.2 Hz, 2H), 7.07 (d, J = 8.0 Hz, 1H), 6.98-6.89 (m, 2H), 6.82 (d, J = 7.9 Hz, 1H), 6.64 (d, J = 8.2 Hz, 1H), 6.01 (s, 2H), 3.61 (s, 3H), 3.54 (s, 3H), 2.32 (d, J = 14.9 Hz, 5H), 1.09 (t, J = 7.5 Hz, 3H). | 508.22 |

TABLE 2-continued

Additional Exemplary Compounds

| Compound | Structure | Proton NMR | MS [M + 1] |
|---|---|---|---|
| N-(4-(4-amino-7-methyl-5-(4-(pyrimidin-2-yloxy)phenyl)-7H-pyrrolo[2,3-d]pyrimidin-6-yl)phenyl)propionamide | 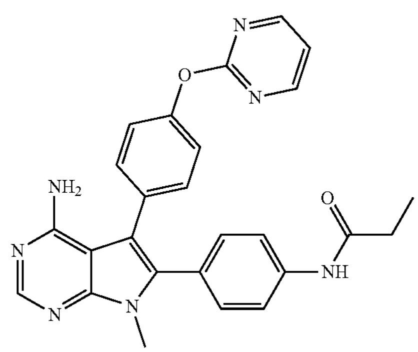 [SMILES: CCC(=O)Nc1ccc(-c2c(-c3ccc(Oc4ncccn4)cc3)c3c(N)ncnc3n2C)cc1] | ¹H NMR (400 MHz, DMSO-d6) δ 10.00 (s, 1H), 8.67 (d, J = 4.8 Hz, 2H), 8.20 (s, 1H), 7.67-7.60 (m, 2H), 7.33-7.25 (m, 5H), 7.24-7.17 (m, 2H), 5.90 (s, 2H), 3.59 (s, 3H), 2.33 (q, J = 7.5 Hz, 2H), 1.09 (t, J = 7.6 Hz, 3H). | 466.25 |
| N-(4-(4-amino-5-(4-((5-(hydroxymethyl)pyrimidin-2-yl)oxy)-3-methoxyphenyl)-7-methyl-7H-pyrrolo[2,3-d]pyrimidin-6-yl)phenyl)acrylamide | 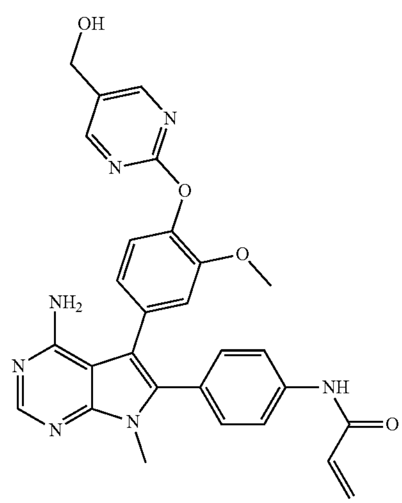 [SMILES: C=CC(=O)Nc1ccc(-c2c(-c3ccc(Oc4ncc(CO)cn4)c(OC)c3)c3c(N)ncnc3n2C)cc1] | ¹H NMR (400 MHz, Methanol-d4) δ 8.57 (s, 2H), 8.22 (s, 1H), 7.73 (d, J = 8.3 Hz, 2H), 7.36 (d, J = 8.4 Hz, 2H), 7.35 (s, 1H), 7.17 (d, J = 8.0 Hz, 1H), 7.00-6.92 (m, 2H), 6.47 (dd, J = 17.0, 9.4 Hz, 1H), 6.39 (dd, J = 17.2, 2.5 Hz, 1H), 5.81 (dd, J = 9.5, 2.4 Hz, 1H), 4.63 (s, 2H), 3.72 (s, 3H), 3.57 (s, 3H). | 524.30 |
| N-(4-(4-amino-5-(4-(5-(hydroxymethyl)pyrimidin-2-yloxy)phenyl)-7-methyl-7H-pyrrolo[2,3-d]pyrimidin-6-yl)phenyl)methacrylamide | 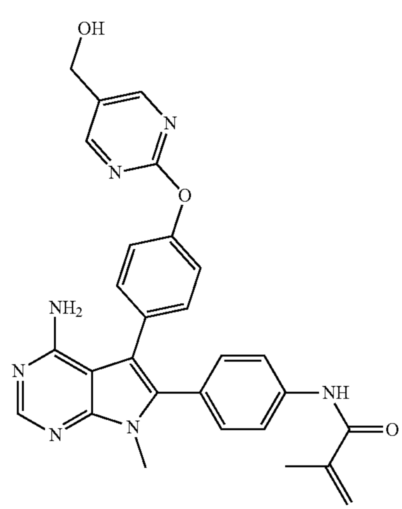 [SMILES: C=C(C)C(=O)Nc1ccc(-c2c(-c3ccc(Oc4ncc(CO)cn4)cc3)c3c(N)ncnc3n2C)cc1] | ¹H NMR (400 MHz, DMSO-d₆) δ 9.92 (s, 1H), 8.59 (s, 2H), 8.21 (s, 1H), 7.78-7.71 (m, 2H), 7.36-7.25 (m, 4H), 7.22-7.14 (m, 2H), 5.80 (t, J = 1.1 Hz, 2H), 5.54 (t, J = 1.5 Hz, 1H), 5.38 (t, J = 5.6 Hz, 1H), 4.49 (d, J = 5.5 Hz, 2H), 3.60 (s, 3H), 1.95 (d, J = 1.3 Hz, 3H). | 508.30 |

TABLE 2-continued

Additional Exemplary Compounds

| Compound | Structure | Proton NMR | MS [M + 1] |
|---|---|---|---|
| N-(4-(4-amino-7-methyl-5-(4-(pyrimidin-2-yloxy)phenyl)-7H-pyrrolo[2,3-d]pyrimidin-6-yl)phenyl)acrylamide | 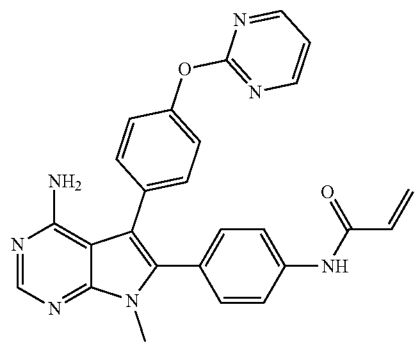 [SMILES: C=CC(=O)Nc1ccc(-c2c(-c3ccc(Oc4ncccn4)cc3)c3c(N)ncnc3n2C)cc1] | $^1$H NMR (400 MHz, DMSO-d$_6$) δ 10.29 (s, 1H), 8.67 (d, J = 4.8 Hz, 2H), 8.21 (s, 1H), 7.75-7.67 (m, 2H), 7.38-7.25 (m, 5H), 7.25-7.17 (m, 2H), 6.44 (dd, J = 16.8, 10.1 Hz, 1H), 6.28 (dd, J = 17.0, 2.2 Hz, 1H), 5.78 (dd, J = 10.1, 2.1 Hz, 1H), 3.60 (s, 3H). | 464.15 |
| N-(4-(4-amino-7-methyl-5-(4-(pyrimidin-2-yloxy)phenyl)-7H-pyrrolo[2,3-d]pyrimidin-6-yl)phenyl)but-2-ynamide | 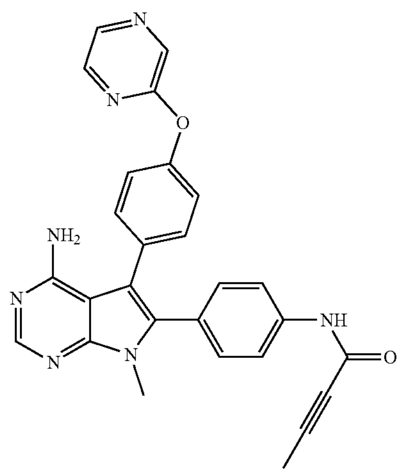 [SMILES: CC#CC(=O)Nc1ccc(-c2c(-c3ccc(Oc4cnccn4)cc3)c3c(N)ncnc3n2C)cc1] | $^1$H NMR (400 MHz, DMSO-d$_6$) δ 10.74 (s, 1H), 8.67 (d, J = 4.8 Hz, 2H), 8.20 (s, 1H), 7.63 (d, J = 8.3 Hz, 2H), 7.36-7.25 (m, 5H), 7.21 (d, J = 8.4 Hz, 2H), 5.89 (s, 2H), 3.59 (s, 3H), 2.07 (d, J = 9.3 Hz, 3H). | 476.2 |
| N-(4-(4-amino-5-(3-methoxyphenyl)-7-methyl-7H-pyrrolo[2,3-d]pyrimidin-6-yl)phenyl)methacrylamide | 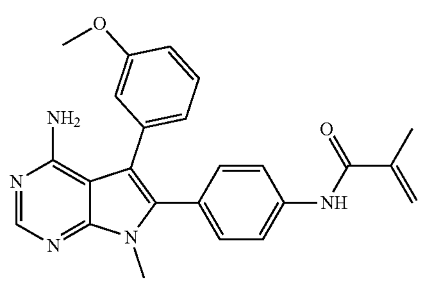 [SMILES: C=C(C)C(=O)Nc1ccc(-c2c(-c3cccc(OC)c3)c3c(N)ncnc3n2C)cc1] | $^1$H NMR (400 MHz, DMSO-d$_6$) δ 9.90 (s, 1H), 8.19 (s, 1H), 7.70 (d, J = 8.3 Hz, 2H), 7.27 (dd, J = 8.2, 5.8 Hz, 3H), 6.86 (dd, J = 8.3, 2.6 Hz, 1H), 6.81 (d, J = 7.5 Hz, 1H), 6.77 (t, J = 2.0 Hz, 1H), 5.78 (s, 2H), 5.53 (s, 1H), 3.67 (s, 3H), 3.60 (s, 3H), 1.95 (s, 3H). | 414.1 |
| (E)-N-(4-(4-amino-5-(3-methoxyphenyl)-7-methyl-7H-pyrrolo[2,3-d]pyrimidin-6-yl)phenyl)but-2-enamide | 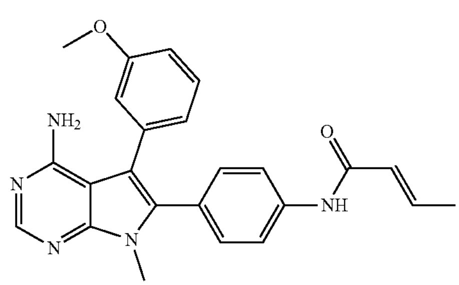 [SMILES: C/C=C/C(=O)Nc1ccc(-c2c(-c3cccc(OC)c3)c3c(N)ncnc3n2C)cc1] | $^1$H NMR (400 MHz, DMSO-d$_6$) δ 10.07 (s, 1H), 8.19 (s, 1H), 7.70-7.62 (m, 2H), 7.32-7.24 (m, 3H), 6.90-6.74 (m, 4H), 6.17-6.08 (m, 1H), 5.91 (s, 1H), 3.67 (s, 3H), 3.60 (s, 3H), 1.88 (dd, J = 6.8, 1.6 Hz, 3H). | 414.15 |

TABLE 2-continued

Additional Exemplary Compounds

| Compound | Structure | Proton NMR | MS [M + 1] |
|---|---|---|---|
| N-(4-(4-amino-5-(3-methoxyphenyl)-7-methyl-7H-pyrrolo[2,3-d]pyrimidin-6-yl)phenyl)but-2-ynamide | 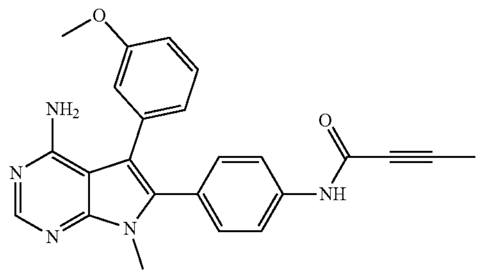 [SMILES: CC#CC(=O)Nc1ccc(-c2c(-c3cccc(OC)c3)c3c(N)ncnc3n2C)cc1] | ¹H NMR (400 MHz, DMSO-d₆) δ 10.73 (s, 1H), 8.19 (s, 1H), 7.60 (d, J = 8.4 Hz, 2H), 7.27 (dd, J = 8.4, 6.4 Hz, 3H), 6.86 (dd, J = 8.4, 2.8 Hz, 1H), 6.80 (d, J = 7.6 Hz, 1H), 6.78-6.73 (m, 1H), 5.91 (s, 1H), 3.67 (s, 3H), 3.59 (s, 3H), 2.06 (s, 3H). | 412.25 |
| N-(4-(4-amino-5-(4-(hydroxy(o-tolyl)methyl)-3-methoxyphenyl)-7-methyl-7H-pyrrolo[2,3-d]pyrimidin-6-yl)phenyl)acrylamide | 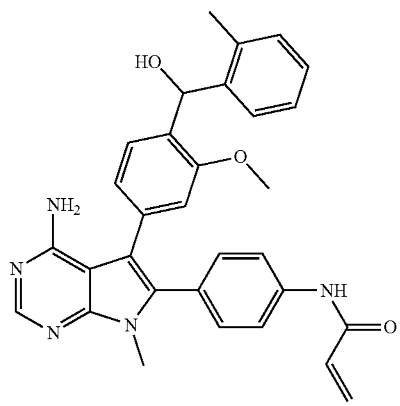 [SMILES: C=CC(=O)Nc1ccc(-c2c(-c3ccc(C(O)c4ccccc4C)c(OC)c3)c3c(N)ncnc3n2C)cc1] | ¹H NMR (400 MHz, DMSO-d₆) δ 10.28 (s, 1H), 8.22 (s, 1H), 7.71-7.43 (d, J = 8 Hz, 1H), 7.22-7.43 (m, 7H), 6.46-6.48 (m, J = 8 Hz, 1H), 6.26-6.44 (m, 2H), 5.77-5.80 (d, J = 8 Hz, 1H), 3.62 (s, 3H), 3.43 (s, 3H), 2.35 (s, 3H). | 518.20 |
| N-(4-(4-amino-7-methyl-5-phenyl-7H-pyrrolo[2,3-d]pyrimidin-6-yl)phenyl)acrylamide | 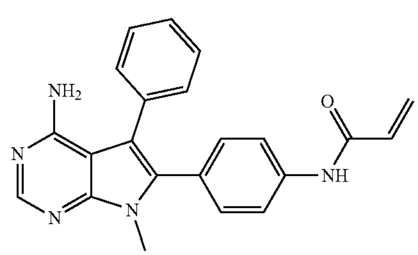 [SMILES: C=CC(=O)Nc1ccc(-c2c(-c3ccccc3)c3c(N)ncnc3n2C)cc1] | ¹H NMR (400 MHz, DMSO-d6) δ 10.25 (s, 1H), 8.20 (s, 1H), 7.67 (d, J = 8.7 Hz, 2H), 7.37 (dd, J = 8.1, 6.6 Hz, 2H), 7.34-7.18 (m, 5H), 6.43 (dd, J = 17.0, 10.1 Hz, 1H), 6.27 (dd, J = 17.0, 2.1 Hz, 1H), 5.78 (dd, J = 10.1, 2.0 Hz, 1H), 3.61 (s, 3H). | 370.25 |
| N-(4-(4-amino-7-methyl-5-phenyl-7H-pyrrolo[2,3-d]pyrimidin-6-yl)phenyl)methacrylamide | 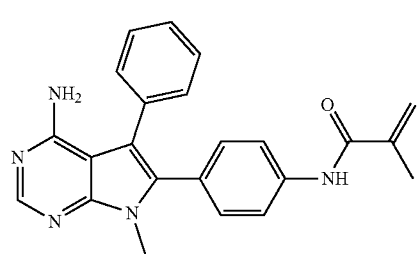 [SMILES: C=C(C)C(=O)Nc1ccc(-c2c(-c3ccccc3)c3c(N)ncnc3n2C)cc1] | ¹H NMR (400 MHz, DMSO-d6) δ 9.89 (s, 1H), 8.19 (s, 1H), 7.69 (d, J = 8.6 Hz, 2H), 7.36 (t, J = 7.4 Hz, 2H), 7.30-7.18 (m, 5H), 5.79 (s, 1H), 5.53 (s, 1H), 3.61 (s, 3H), 1.95 (t, J = 1.2 Hz, 3H). | 384.20 |

TABLE 2-continued

Additional Exemplary Compounds

| Compound | Structure | Proton NMR | MS [M + 1] |
|---|---|---|---|
| N-(4-(4-amino-7-ethyl-5-(4-((6-methylpyridin-2-yl)oxy)phenyl)-7H-pyrrolo[2,3-d]pyrimidin-6-yl)phenyl) methacrylamide | 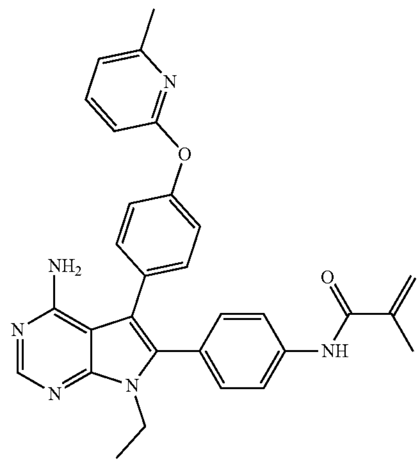 [SMILES: C=C(C)C(=O)Nc1ccc(-c2c(-c3ccc(Oc4cccc(C)n4)cc3)c3c(N)ncnc3n2CC)cc1] | ¹H NMR (400 MHz, DMSO-d₆) δ 9.91 (s, 1H), 8.20 (s, 1H), 7.73 (dd, J = 8.3, 6.6 Hz, 3H), 7.33-7.22 (m, 4H), 7.11-7.04 (m, 2H), 7.01 (d, J = 7.4 Hz, 1H), 6.77 (d, J = 8.1 Hz, 1H), 5.88 (s, 2H), 5.80 (s, 1H), 5.54 (s, 1H), 4.12 (q, J = 7.0 Hz, 2H), 2.34 (s, 3H), 1.95 (s, 3H), 1.14 (t, J = 7.1 Hz, 3H). | 505.2 |
| N-(4-(4-amino-7-(3-hydroxycyclobutyl)-5-(4-((6-methylpyridin-2-yl)oxy)phenyl)-7H-pyrrolo[2,3-d]pyrimidin-6-yl)phenyl) methacrylamide | 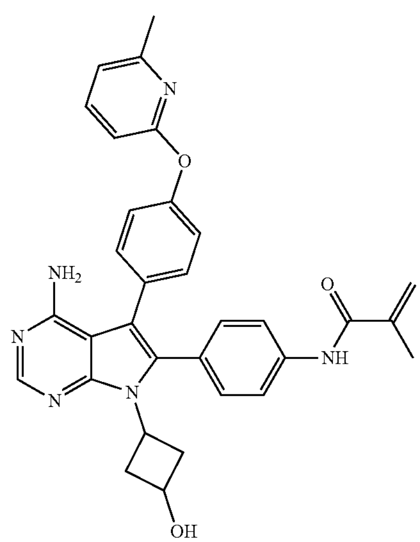 [SMILES: C=C(C)C(=O)Nc1ccc(-c2c(-c3ccc(Oc4cccc(C)n4)cc3)c3c(N)ncnc3n2C2CC(O)C2)cc1] | ¹H NMR (400 MHz, DMSO-d₆) δ 9.90 (s, 1H), 8.21 (s, 1H), 7.83-7.66 (m, 3H), 7.22 (t, J = 8.2 Hz, 5H), 7.11-6.95 (m, 4H), 6.77 (d, J = 8.1 Hz, 1H), 5.79 (s, 1H), 5.54 (d, J = 1.8 Hz, 1H), 5.22 (d, J = 5.8 Hz, 1H), 4.33-4.00 (m, 1H), 3.82 (h, J = 7.0 Hz, 1H), 3.10-2.90 (m, 2H), 2.34 (s, 4H), 1.95 (s, 3H), 1.87 (s, 2H). | 547.25 |

TABLE 2-continued

Additional Exemplary Compounds

| Compound | Structure | Proton NMR | MS [M + 1] |
|---|---|---|---|
| N-(4-(4-amino-7-(2-(4-methylpiperazin-1-yl)ethyl)-5-(4-((6-methylpyridin-2-yl)oxy)phenyl)-7H-pyrrolo[2,3-d]pyrimidin-6-yl)phenyl) methacrylamide | 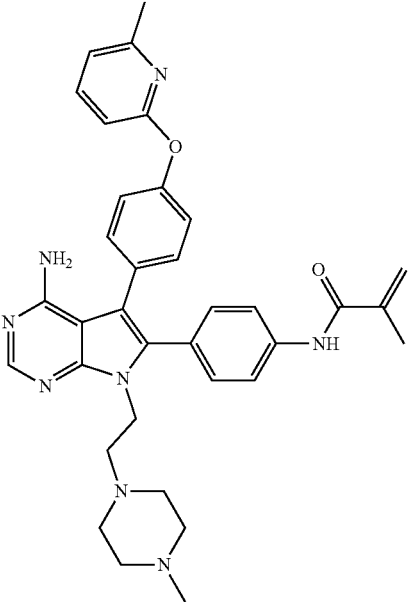 [SMILES: C=C(C)C(=O)Nc1ccc(-c2c(-c3ccc(Oc4cccc(C)n4)cc3)c3c(N)ncnc3n2CCN2CCN(C)CC2)cc1] | $^1$H NMR (400 MHz, DMSO-d$_6$) δ 9.90 (s, 1H), 8.19 (s, 1H), 7.73 (dt, J = 8.2, 3.4 Hz, 3H), 7.35-7.28 (m, 2H), 7.28-7.12 (m, 2H), 7.11-7.04 (m, 2H), 7.01 (d, J = 7.4 Hz, 1H), 6.77 (d, J = 8.2 Hz, 1H), 5.80 (t, J = 1.1 Hz, 1H), 5.53 (t, J = 1.4 Hz, 1H), 4.18 (t, J = 6.9 Hz, 2H), 2.47 (d, J = 1.0 Hz, 2H), 2.34 (s, 3H), 2.23 (s, 8H), 2.09 (s, 3H), 1.95 (t, J = 1.2 Hz, 3H). | 603.3 |
| N-(4-(4-amino-7-(2-hydroxyethyl)-5-(4-((6-methylpyridin-2-yl)oxy)phenyl)-7H-pyrrolo[2,3-d]pyrimidin-6-yl)phenyl) methacrylamide | 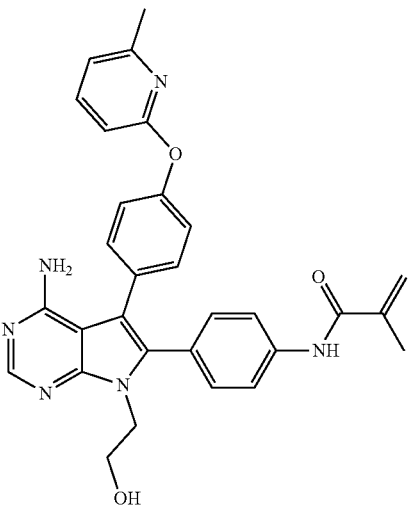 [SMILES: C=C(C)C(=O)Nc1ccc(-c2c(-c3ccc(Oc4cccc(C)n4)cc3)c3c(N)ncnc3n2CCO)cc1] | $^1$H NMR (400 MHz, DMSO-d6) δ 9.90 (s, 1H), 8.19 (s, 1H), 7.77-7.68 (m, 3H), 7.35-7.28 (m, 2H), 7.28-7.20 (m, 2H), 7.11-7.03 (m, 2H), 7.01 (d, J = 7.3 Hz, 1H), 6.77 (d, J = 8.2 Hz, 1H), 5.82-5.77 (m, 1H), 5.53 (t, J = 1.4 Hz, 1H), 4.90 (t, J = 5.6 Hz, 1H), 4.13 (t, J = 6.6 Hz, 2H), 3.58 (q, J = 6.4 Hz, 2H), 2.34 (s, 3H), 1.95 (t, J = 1.3 Hz, 3H). | 521.20 |

TABLE 2-continued

Additional Exemplary Compounds

| Compound | Structure | Proton NMR | MS [M + 1] |
|---|---|---|---|
| N-(4-(4-amino-5-(4-(6-methylpyridin-2-yloxy)phenyl)-7-(2-morpholinoethyl)-7H-pyrrolo[2,3-d]pyrimidin-6-yl)phenyl) methacrylamide | 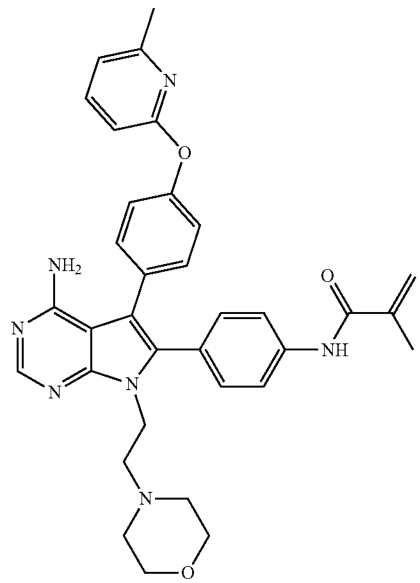 [SMILES: C=C(C)C(=O)Nc1ccc(-c2c(-c3ccc(Oc4cccc(C)n4)cc3)c3c(N)ncnc3n2CCN2CCOCC2)cc1] | $^1$H NMR (400 MHz, DMSO-d$_6$) δ 9.90 (s, 1H), 8.19 (s, 1H), 7.73 (dt, J = 7.7, 3.5 Hz, 3H), 7.36-7.29 (m, 2H), 7.29-7.22 (m, 2H), 7.13-7.06 (m, 2H), 7.01 (d, J = 7.4 Hz, 1H), 6.78 (d, J = 81 Hz, 1H), 5.91 (s, 1H), 5.81 (s, 1H), 5.53 (s, 1H), 4.21 (t, J = 7.0 Hz, 2H), 3.44 (t, J = 4.6 Hz, 4H), 2.48 (d, J = 7.0 Hz, 2H), 2.34 (s, 3H), 2.22 (t, J = 4.7 Hz, 4H), 1.95 (s, 3H). | 590.30 |
| N-(4-(4-amino-7-(2-(dimethylamino)ethyl)-5-(4-(6-methylpyridin-2-yloxy)phenyl)-7H-pyrrolo[2,3-d]pyrimidin-6-yl)phenyl) methacrylamide | 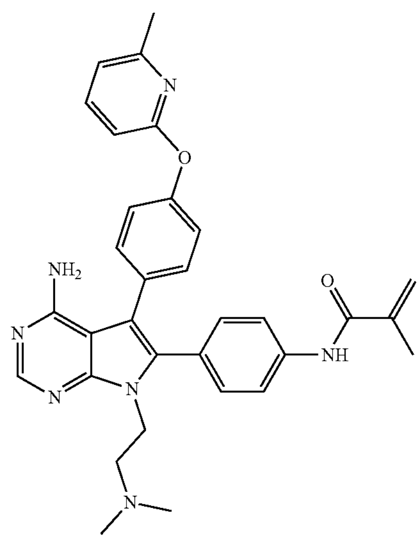 [SMILES: C=C(C)C(=O)Nc1ccc(-c2c(-c3ccc(Oc4cccc(C)n4)cc3)c3c(N)ncnc3n2CCN(C)C)cc1] | $^1$H NMR (400 MHz, DMSO-d$_6$) δ 9.90 (s, 1H), 8.20 (s, 1H), 7.73 (t, J = 7.6 Hz, 3H), 7.31 (d, J = 8.6 Hz, 2H), 7.28-7.20 (m, 2H), 7.12-7.05 (m, 2H), 7.01 (d, J = 7.4 Hz, 1H), 6.78 (d, J = 8.1 Hz, 1H), 5.90 (s, 1H), 5.80 (s, 1H), 5.53 (s, 1H), 4.20 (t, J = 1.0 Hz, 2H), 2.38 (t, J = 7.1 Hz, 2H), 2.34 (s, 3H), 2.01 (s, 6H), 1.97 (s, 3H). | 548.25 |
| N-(4-(4-amino-5-(4-((6-methylpyridin-2-yl)oxy)phenyl)-7H-pyrrolo[2,3-d]pyrimidin-6-yl)phenyl) methacrylamide | 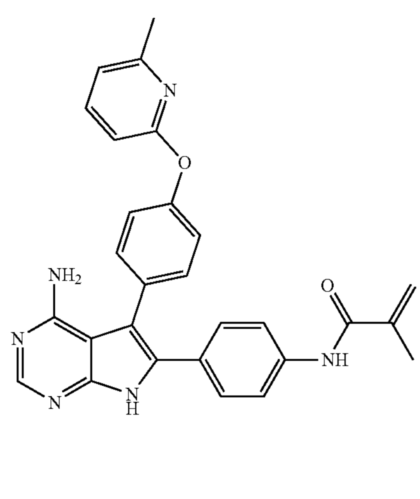 [SMILES: C=C(C)C(=O)Nc1ccc(-c2[nH]c3ncnc(N)c3c2-c2ccc(Oc3cccc(C)n3)cc2)cc1] | $^1$H NMR (400 MHz, DMSO-d$_6$) δ 12.07 (s, 1H), 9.83 (s, 1H), 8.12 (s, 1H), 7.77 (t, J = 7.8 Hz, 1H), 7.65-7.58 (m, 2H), 7.42-7.34 (m, 2H), 7.34-7.26 (m, 2H), 7.23-7.15 (m, 2H), 7.04 (d, J = 7.4 Hz, 1H), 6.85 (d, J = 8.2 Hz, 1H), 5.78 (s, 1H), 5.52 (t, J = 1.5 Hz, 1H), 2.38 (s, 3H), 1.94 (d, J = 1.3 Hz, 3H). | 477.3 |

TABLE 2-continued

Additional Exemplary Compounds

| Compound | Structure | Proton NMR | MS [M + 1] |
|---|---|---|---|
| N-(4-(4-amino-5-(4-((5-chloropyrimidin-2-yl)oxy)-3-methoxyphenyl)-7-methyl-7H-pyrrolo[2,3-d]pyrimidin-6-yl)phenyl)acrylamide | 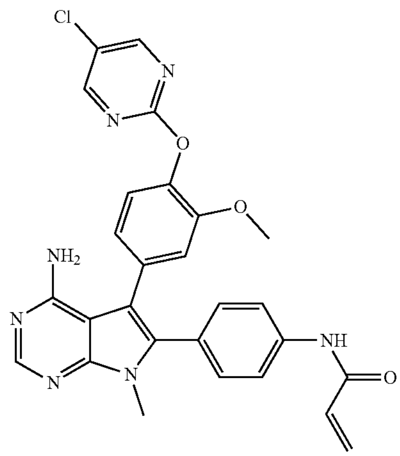 [SMILES: C=CC(=O)Nc1ccc(-c2c(-c3ccc(Oc4ncc(Cl)cn4)c(OC)c3)c3c(N)ncnc3n2C)cc1] | $^1$H NMR (400 MHz, DMSO-d$_6$) δ 10.29 (s, 1H), 8.73 (s, 2H), 8.23 (s, 1H), 7.73 (d, J = 8.6 Hz, 2H), 7.44-7.31 (m, 2H), 7.20 (d, J = 8.1 Hz, 1H), 6.99 (d, J = 1.9 Hz, 1H), 6.92-6.84 (m, 1H), 6.59-6.31 (m, 1H), 6.30-6.26 (m, 1H), 6.06 (s, 2H), 5.85-5.73 (m, 1H), 3.60 (s, 3H), 3.55 (s, 3H). | 528.20 |
| N-(4-(4-amino-5-(4-((5-aminopyrimidin-2-yl)oxy)-3-methoxyphenyl)-7-methyl-7H-pyrrolo[2,3-d]pyrimidin-6-yl)phenyl)acrylamide | 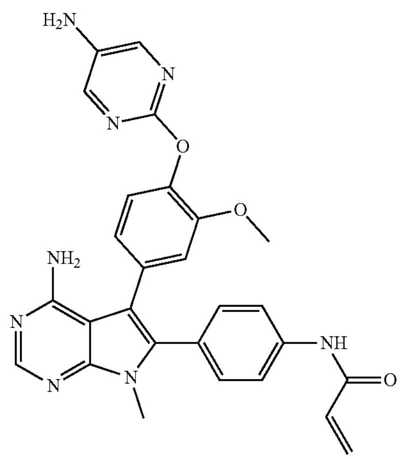 [SMILES: C=CC(=O)Nc1ccc(-c2c(-c3ccc(Oc4ncc(N)cn4)c(OC)c3)c3c(N)ncnc3n2C)cc1] | $^1$H NMR (400 MHz, DMSO-d$_6$) δ 10.26 (d, J = 14.0 Hz, 1H), 8.19 (d, J = 14.7 Hz, 1H), 7.93 (s, 2H), 7.81-7.58 (m, 2H), 7.48-7.20 (m, 2H), 7.06 (d, J = 8.0 Hz, 1H), 6.93 (d, J = 1.9 Hz, 1H), 6.88-6.80 (m, 1H), 6.50-6.40 (m, 1H), 6.35-6.22 (m, 1H), 5.78 (d, J = 10.1 Hz, 1H), 5.12 (s, 2H), 3.67-3.57 (m, 4H), 3.53 (s, 3H). | 509.20 |
| N-(4-(4-amino-5-(3-methoxy-4-(5-(methylamino)pyrimidin-2-yloxy)phenyl)-7-methyl-7H-pyrrolo[2,3-d]pyrimidin-6-yl)phenyl)acrylamide | 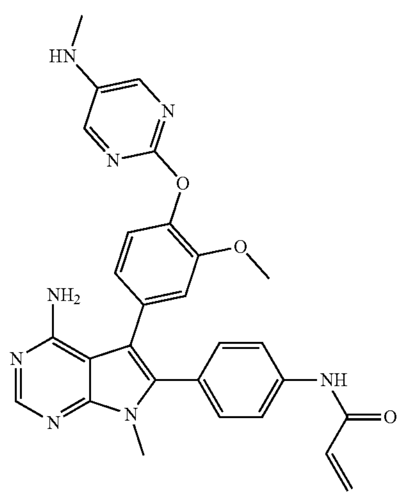 [SMILES: C=CC(=O)Nc1ccc(-c2c(-c3ccc(Oc4ncc(NC)cn4)c(OC)c3)c3c(N)ncnc3n2C)cc1] | $^1$H NMR (400 MHz, DMSO-d$_6$) δ 10.28 (s, 1H), 8.21 (s, 1H), 7.93 (s, 2H), 7.73 (d, J = 8.6 Hz, 2H), 7.43-7.32 (m, 2H), 7.07 (d, J = 8.0 Hz, 1H), 6.94 (d, J = 2.0 Hz, 1H), 6.83 (dd, J = 8.1, 1.9 Hz, 1H), 6.45 (dd, J = 17.0, 10.1 Hz, 1H), 6.28 (dd, J = 17.0, 2.1 Hz, 1H), 5.96 (s, 1H), 5.78 (dd, J = 10.1, 2.1 Hz, 1H), 5.70 (q, J = 5.2 Hz, 1H), 3.60 (s, 3H), 3.53 (s, 3H), 2.67 (d, J = 5.2 Hz, 3H). | 523.35 |

TABLE 2-continued

Additional Exemplary Compounds

| Compound | Structure | Proton NMR | MS [M + 1] |
|---|---|---|---|
| N-(4-(4-amino-5-(3-methoxy-4-(pyrimidin-2-ylmethyl)phenyl)-7-methyl-7H-pyrrolo[2,3-d]pyrimidin-6-yl)phenyl) methacrylamide | 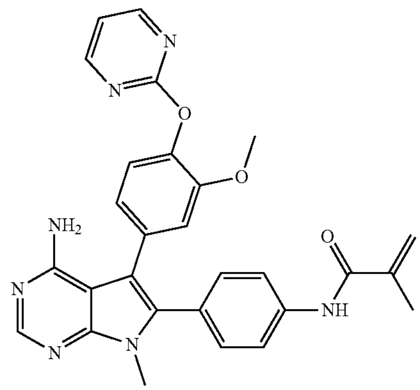 [SMILES: C=C(C)C(=O)Nc1ccc(-c2c(-c3ccc(Oc4ncccn4)c(OC)c3)c3c(N)ncnc3n2C)cc1] | $^1$H NMR (400 MHz, DMSO-d$_6$) δ 9.88 (s, 1H), 8.71-8.72 (d, J = 4 Hz, 2H), 8.19 (s, 1H), 7.70-7.72 (d, J = 8 Hz, 2H), 7.30-7.34 (m, 3H), 7.03-7.05 (d, J = 8 Hz, 1H), 6.77-6.82 (m, 2H), 5.53-5.81 (m, 3H), 4.17 (s, 2H), 3.57-3.58 (m, 6H), 1.95 (s, 3H). | 506.35 |
| N-(4-(4-amino-5-(4-(hydroxy(o-tolyl)methyl)-3-methoxyphenyl)-7-methyl-7H-pyrrolo[2,3-d]pyrimidin-6-yl)phenyl) acrylamide | 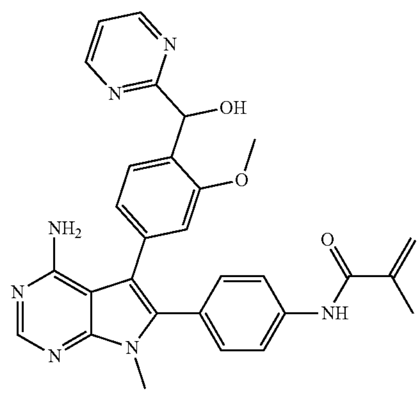 [SMILES: C=C(C)C(=O)Nc1ccc(-c2c(-c3ccc(C(O)c4ncccn4)c(OC)c3)c3c(N)ncnc3n2C)cc1] | $^1$H NMR (400 MHz, DMSO-d$_6$) δ 9.88 (s, 1H), 8.75-8.76 (d, J = 4 Hz, 2H), 8.19 (s, 1H), 7.70-7.72 (d, J = 8 Hz, 1H), 7.43-7.45 (d, J = 8 Hz, 1H), 7.30-7.37 (m, 3H), 6.78-6.87 (m, 1H), 6.77 (s, 1H), 5.99-6.01 (d, J = 8 Hz, 1H), 5.77-5.81 (m, 3H), 5.53 (s, 1H), 3.58 (s, 3H), 3.52 (s, 3H), 1.95 (s, 3H). | 522.25 |
| N-(4-(4-amino-5-(3-ethyl-5-hydroxy-4-(pyrimidin-2-yloxy)phenyl)-7-methyl-7H-pyrrolo[2,3-d]pyrimidin-6-yl)phenyl) methacrylamide | 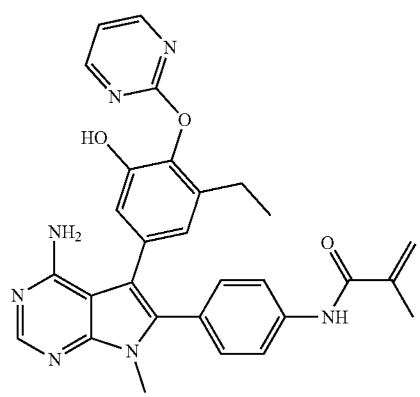 [SMILES: C=C(C)C(=O)Nc1ccc(-c2c(-c3cc(O)c(Oc4ncccn4)c(CC)c3)c3c(N)ncnc3n2C)cc1] | $^1$H NMR (400 MHz, DMSO-d6) δ 9.91 (d, J = 10.6 Hz, 1H), 9.54 (s, 1H), 8.64 (m, J = 19.1, 4.8 Hz, 2H), 8.17 (d, J = 17.0 Hz, 1H), 7.85-7.63 (m, 2H), 7.35 (d, J = 8.4 Hz, 2H), 7.20 (s, 1H), 6.92-6.48 (m, 2H), 5.81 (s, 1H), 5.54 (s, 1H), 3.59 (s, 3H), 2.39 (q, J = 7.5 Hz, 2H), 1.96 (d, J = 3.4 Hz, 3H), 1.02-0.91 (m, 3H). | 522.20 |
| N-(4-(4-amino-7-methyl-5-(4-(pyrrolidin-1-ylsulfonyl)phenyl)-7H-pyrrolo[2,3-d]pyrimidin-6-yl)phenyl) methacrylamide | 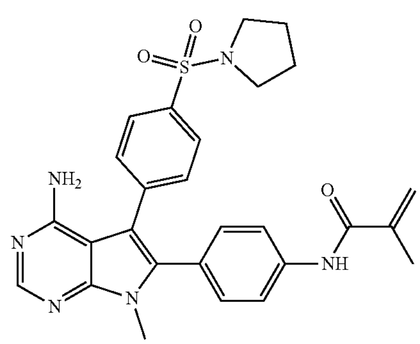 [SMILES: C=C(C)C(=O)Nc1ccc(-c2c(-c3ccc(S(=O)(=O)N4CCCC4)cc3)c3c(N)ncnc3n2C)cc1] | $^1$H NMR (400 MHz, DMSO-d6) δ 9.91 (s, 1H), 8.22 (s, 1H), 7.79-7.65 (m, 4H), 7.40 (d, J = 8.4 Hz, 2H), 7.25-7.17 (m, 2H), 6.03 (s, 2H), 5.79 (s, 1H), 5.54 (s, 1H), 3.63 (s, 3H), 3.21-3.00 (m, 4H), 1.95 (d, J = 1.6 Hz, 3H), 1.72-1.52 (m, 4H). | 517.20 |

TABLE 2-continued

Additional Exemplary Compounds

| Compound | Structure | Proton NMR | MS [M + 1] |
|---|---|---|---|
| N-(4-(5-(4-acetamido-3-methoxyphenyl)-4-amino-7-methyl-7H-pyrrolo[2,3-d]pyrimidin-6-yl)phenyl)methacrylamide | 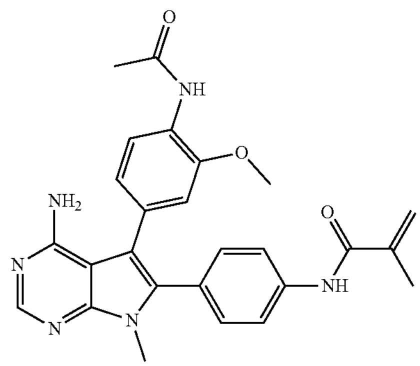 [SMILES: C=C(C)C(=O)Nc1ccc(-c2c(-c3ccc(NC(C)=O)c(OC)c3)c3c(N)ncnc3n2C)cc1] | $^1$H NMR (400 MHz, DMSO-d$_6$) δ 9.88 (s, 1H), 9.12 (s, 1H), 8.19 (s, 1H), 7.93 (d, J = 8.2 Hz, 1H), 7.76-7.54 (m, 2H), 7.40-7.18 (m, 2H), 6.94-6.65 (m, 2H), 5.80 (t, J = 1.1 Hz, 1H), 5.59-5.35 (m, 1H), 3.67 (s, 3H), 3.61 (s, 3H), 2.08 (s, 3H), 1.95 (d, J = 1.2 Hz, 3H). | 471.15 |
| N-(4-(4-amino-7-methyl-5-(4-(pyrrolidine-1-carbonyl)phenyl)-7H-pyrrolo[2,3-d]pyrimidin-6-yl)phenyl)methacrylamide | 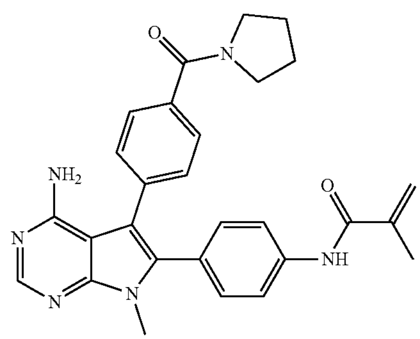 [SMILES: C=C(C)C(=O)Nc1ccc(-c2c(-c3ccc(C(=O)N4CCCC4)cc3)c3c(N)ncnc3n2C)cc1] | $^1$H NMR (400 MHz, DMSO-d$_6$) δ 9.90 (s, 1H), 8.21 (s, 1H), 7.77-7.66 (m, 2H), 7.55-7.43 (m, 2H), 7.33-7.20 (m, 4H), 5.92 (s, 1H), 5.83-5.77 (m, 1H), 5.53 (q, J = 1.4 Hz, 1H), 3.61 (s, 3H), 3.44 (dt, J = 16.1, 6.5 Hz, 4H), 1.95 (t, J = 1.3 Hz, 3H), 1.83 (dq, J = 18.0, 6.6 Hz, 4H). | 481.35 |
| N-(4-(4-amino-5-(3-fluoro-4-((5-fluoropyrimidin-2-yl)oxy)phenyl)-7-methyl-7H-pyrrolo[2,3-d]pyrimidin-6-yl)phenyl)methacrylamide | 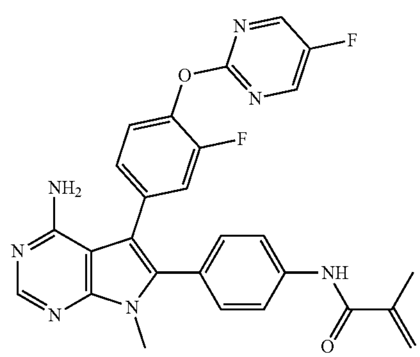 [SMILES: C=C(C)C(=O)Nc1ccc(-c2c(-c3ccc(Oc4ncc(F)cn4)c(F)c3)c3c(N)ncnc3n2C)cc1] | $^1$H NMR (400 MHz, DMSO-d6) δ 9.93 (s, 1H), 8.78 (s, 2H), 8.22 (s, 1H), 7.85-7.71 (m, 2H), 7.42-7.29 (m, 3H), 7.21 (dd, J = 11.6, 2.0 Hz, 1H), 7.12 (dd, J = 8.4, 2.0 Hz, 1H), 6.00 (s, 1H), 5.81 (s, 1H), 5.55 (s, 1H), 3.59 (s, 3H), 1.96 (d, J = 1.6 Hz, 2H). | 514.35 |
| N-(4-(4-amino-5-(3-fluoro-4-((5-fluoropyridin-2-yl)oxy)phenyl)-7-methyl-7H-pyrrolo[2,3-d]pyrimidin-6-yl)phenyl)methacrylamide | 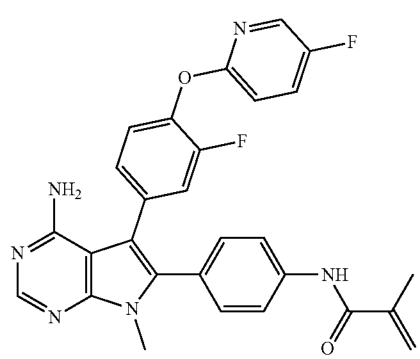 [SMILES: C=C(C)C(=O)Nc1ccc(-c2c(-c3ccc(Oc4ccc(F)cn4)c(F)c3)c3c(N)ncnc3n2C)cc1] | $^1$H NMR (400 MHz, DMSO-d6) δ 9.94 (s, 1H), 8.29 (s, 1H), 8.17 (d, J = 3.1 Hz, 1H), 7.86 (ddd, J = 9.0, 7.9, 3.1 Hz, 1H), 7.80-7.73 (m, 2H), 7.34 (s, 1H), 7.36-7.26 (m, 2H), 7.25-7.16 (m, 2H), 7.13-7.06 (m, 1H), 6.37 (s, 2H), 5.82 (s, 1H), 5.55 (d, J = 2.0 Hz, 1H), 3.62 (s, 3H), 1.96 (d, J = 1.2 Hz, 3H). | 513.20 |

TABLE 2-continued

Additional Exemplary Compounds

| Compound | Structure | Proton NMR | MS [M + 1] |
|---|---|---|---|
| N-(4-(4-amino-5-(3-fluoro-4-((5-methylpyrimidin-2-yl)oxy)phenyl)-7-methyl-7H-pyrrolo[2,3-d]pyrimidin-6-yl)phenyl)methacrylamide | 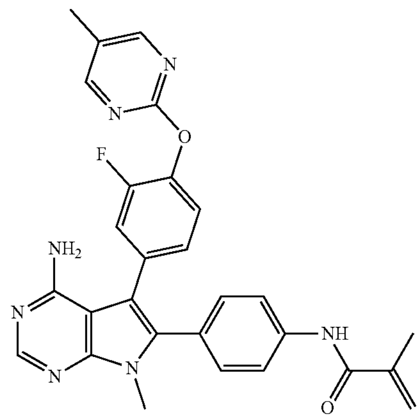 [SMILES: C=C(C)C(=O)Nc1ccc(-c2c(-c3ccc(Oc4ncc(C)cn4)c(F)c3)c3c(N)ncnc3n2C)cc1] | $^1$H NMR (400 MHz, DMSO-d$_6$) δ 10.30 (s, 1H), 8.42 (d, J = 5.6 Hz, 2H), 8.21 (s, 1H), 7.72 (d, J = 8.4 Hz, 2H), 7.31 (d, J = 8.4 Hz, 2H), 7.13 (d, J = 8.0 Hz, 1H), 7.01 (d, J = 2.0 Hz, 1H), 6.91-6.86 (m, 2H), 6.86-6.80 (m, 1H), 6.50-6.39 (m, 1H), 6.33-6.23 (m, 1H), 6.14 (s, 2H), 5.82-5.75 (m, 1H), 3.65-3.54 (d, J = 23.2 Hz, 6H). | 510.20 |
| N-(4-(4-amino-5-(3,5-difluoro-4-(pyrazin-2-yloxy)phenyl)-7-methyl-7H-pyrrolo[2,3-d]pyrimidin-6-yl)phenyl)methacrylamide | 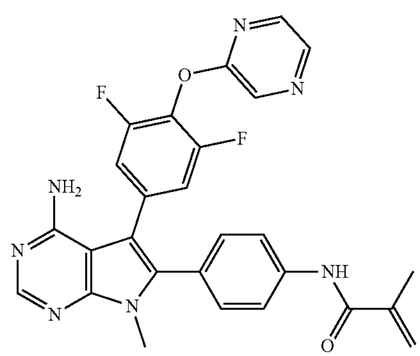 [SMILES: C=C(C)C(=O)Nc1ccc(-c2c(-c3cc(F)c(Oc4cnccn4)c(F)c3)c3c(N)ncnc3n2C)cc1] | $^1$H NMR (400 MHz, DMSO-d$_6$) δ 9.94 (s, 1H), 8.77 (d, J = 1.4 Hz, 1H), 8.48 (d, J = 2.7 Hz, 1H), 8.27 (dd, J = 2.7, 1.5 Hz, 1H), 8.22 (s, 1H), 7.78 (d, J = 8.5 Hz, 2H), 7.35 (d, J = 8.5 Hz, 2H), 7.09 (d, J = 8.8 Hz, 2H), 6.16 (s, 1H), 5.82 (s, 1H), 5.55 (s, 1H), 3.58 (s, 3H), 1.96 (s, 3H). | 514.20 |
| N-(4-(4-amino-5-(4-((5-chloropyrimidin-2-yl)oxy)-3-fluorophenyl)-7-methyl-7H-pyrrolo[2,3-d]pyrimidin-6-yl)phenyl)methacrylamide | 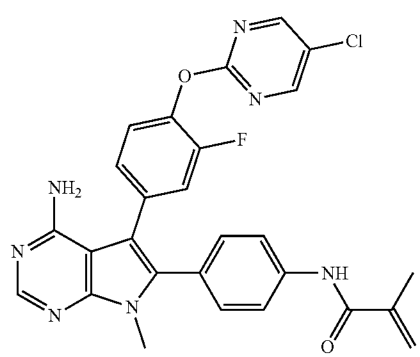 | $^1$H NMR (400 MHz, DMSO-d$_6$) δ 9.94 (s, 1H), 8.81 (s, 2H), 8.22 (s, 1H), 7.76 (d, J = 8.3 Hz, 2H), 7.47-7.30 (m, 3H), 7.23-7.06 (m, 2H), 5.81 (s, 1H), 5.55 (s, 1H), 3.59 (s, 3H), 1.96 (s, 3H). | 530.15 |
| N-(4-(4-amino-5-(3,5-difluoro-4-(pyridin-2-yloxy)phenyl)-7-methyl-7H-pyrrolo[2,3-d]pyrimidin-6-yl)phenyl)methacrylamide | 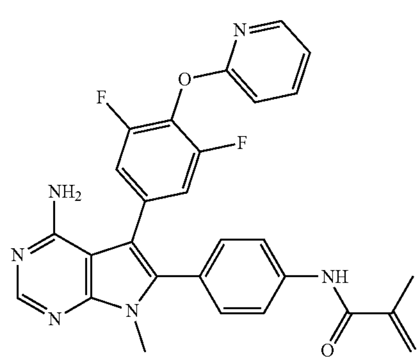 [SMILES: C=C(C)C(=O)Nc1ccc(-c2c(-c3cc(F)c(Oc4ccccn4)c(F)c3)c3c(N)ncnc3n2C)cc1] | $^1$H NMR (400 MHz, DMSO-d$_6$) δ 9.95 (s, 1H), 8.22 (s, 1H), 8.15 (d, J = 5.4 Hz, 1H), 7.92 (td, J = 8.4, 7.8, 2.2 Hz, 1H), 7.78 (d, J = 8.6 Hz, 2H), 7.35 (d, J = 8.4 Hz, 2H), 7.25-7.15 (m, 2H), 7.05 (d, J = 8.8 Hz, 2H), 6.13 (s, 1H), 5.82 (s, 1H), 5.55 (s, 1H), 3.58 (s, 3H), 1.96 (s, 3H). | 513.35 |

TABLE 2-continued

Additional Exemplary Compounds

| Compound | Structure | Proton NMR | MS [M + 1] |
|---|---|---|---|
| N-(4-(4-amino-5-(4-((5-fluoropyridin-2-yl)oxy)-3-hydroxyphenyl)-7-methyl-7H-pyrrolo[2,3-d]pyrimidin-6-yl)phenyl)methacrylamide | 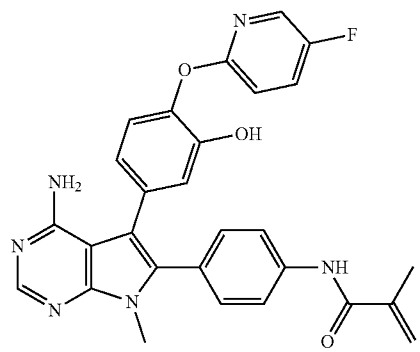 [SMILES: C=C(C)C(=O)Nc1ccc(-c2c(-c3ccc(Oc4ccc(F)cn4)c(O)c3)c3c(N)ncnc3n2C)cc1] | $^1$H NMR (400 MHz, DMSO-d$_6$) δ 9.92 (s, 1H), 9.61 (s, 1H), 8.23-8.10 (m, 2H), 7.81-7.71 (m, 3H), 7.31 (d, J = 8.4 Hz, 2H), 7.09-6.96 (m, 2H), 6.81 (d, J = 2.2 Hz, 1H), 6.70 (dd, J = 8.0, 2.2 Hz, 1H), 5.81 (s, 1H), 5.54 (s, 1H), 3.60 (s, 3H), 1.96 (s, 3H). | 511.20 |
| N-(4-(4-amino-5-(4-((5-fluoropyrimidin-2-yl)oxy)-3-methylphenyl)-7-methyl-7H-pyrrolo[2,3-d]pyrimidin-6-yl)phenyl)methacrylamide | 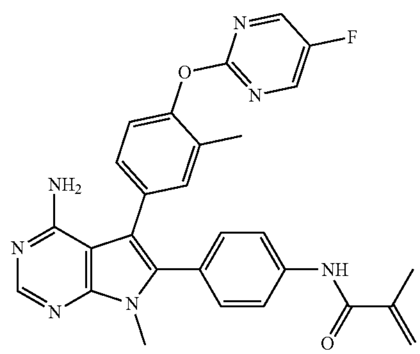 | 1H NMR (400 MHz, DMSO-d6) δ 9.91 (s, 1H), 8.74 (s, 2H), 8.20 (s, 1H), 7.77-7.71 (m, 2H), 7.37-7.30 (m, 2H), 7.25 (s, 1H), 7.11 (d, J = 1.3 Hz, 2H), 5.81 (s, 1H), 5.54 (s, 1H), 3.59 (s, 3H), 2.06 (s, 3H), 1.96 (t, J = 1.2 Hz, 3H). | 509.20 |
| N-(4-(4-amino-5-(3-hydroxy-4-((5-methylpyridin-2-yl)oxy)phenyl)-7-methyl-7H-pyrrolo[2,3-d]pyrimidin-6-yl)phenyl)methacrylamide | 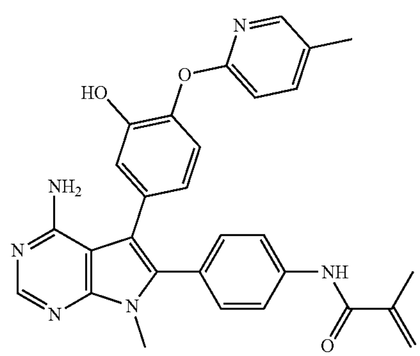 [SMILES: C=C(C)C(=O)Nc1ccc(-c2c(-c3ccc(Oc4ccc(C)cn4)c(O)c3)c3c(N)ncnc3n2C)cc1] | 1H NMR (400 MHz, DMSO-d6) δ 9.90 (d, J = 3.1 Hz, 1H), 9.51 (d, J = 6.1 Hz, 1H), 8.17 (d, J = 14.7 Hz, 1H), 7.98 (s, 0H), 7.73 (dd, J = 8.6, 6.1 Hz, 2H), 7.65-7.56 (m, 1H), 7.30 (dd, J = 13.8, 8.6 Hz, 2H), 6.94-6.76 (m, 4H), 5.82 (s, 1H), 5.55 (s, 1H), 3.60 (d, J = 4.6 Hz, 3H), 2.22 (s, 3H), 1.97 (dd, J = 3.1, 1.8 Hz, 3H). | 507.20 |
| N-(4-(4-amino-5-(3,5-difluoro-4-(pyrimidin-2-yloxy)phenyl)-7-methyl-7H-pyrrolo[2,3-d]pyrimidin-6-yl)phenyl)methacrylamide | 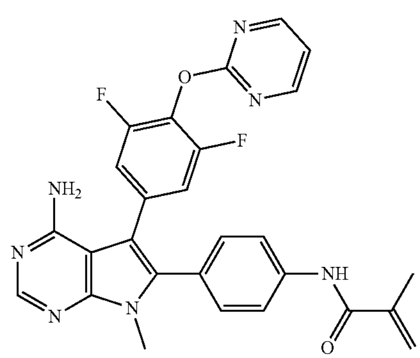 [SMILES: C=C(C)C(=O)Nc1ccc(-c2c(-c3cc(F)c(Oc4ncccn4)c(F)c3)c3c(N)ncnc3n2C)cc1] | 1H NMR (400 MHz, DMSO-d6) δ 9.95 (s, 1H), 8.72 (d, J = 4.8 Hz, 2H), 8.22 (s, 1H), 7.79 (d, J = 8.4 Hz, 2H), 7.42-7.33 (m, 3H), 7.08 (d, J = 8.8 Hz, 2H), 6.13 (s, 2H), 5.82 (s, 1H), 5.55 (s, 1H), 3.57 (s, 3H), 1.96 (s, 3H). | 514.35 |

TABLE 2-continued

Additional Exemplary Compounds

| Compound | Structure | Proton NMR | MS [M + 1] |
|---|---|---|---|
| N-(4-(4-amino-5-(4-((6-fluoro-5-methoxypyridin-2-yl)oxy)phenyl)-7-methyl-7H-pyrrolo[2,3-d]pyrimidin-6-yl)phenyl)methacrylamide | 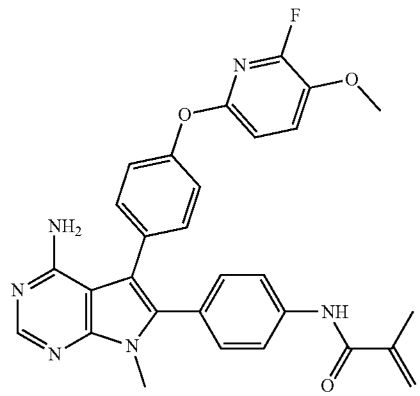 [SMILES: C=C(C)C(=O)Nc1ccc(-c2c(-c3ccc(Oc4ccc(OC)c(F)n4)cc3)c3c(N)ncnc3n2C)cc1] | ¹H NMR (400 MHz, DMSO-d₆) δ 9.90 (s, 1H), 8.20 (s, 1H), 7.86-7.65 (m, 3H), 7.28 (m, J = 12.2, 8.3 Hz, 4H), 7.11 (d, J = 8.3 Hz, 2H), 6.99-6.71 (m, 1H), 5.80 (s, 2H), 5.53 (s, 1H), 3.86 (s, 3H), 3.61 (s, 3H), 1.95 (s, 3H). | 525.15 |
| N-(4-(4-amino-5-(3-amino-4-((5-fluoropyridin-2-yl)oxy)phenyl)-7-methyl-7H-pyrrolo[2,3-d]pyrimidin-6-yl)phenyl)methacrylamide | 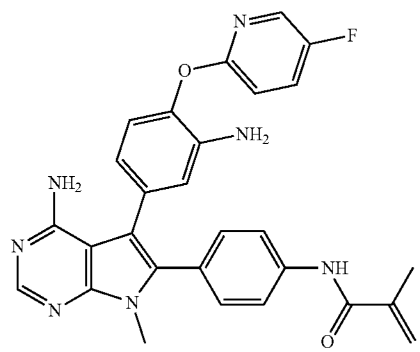 [SMILES: C=C(C)C(=O)Nc1ccc(-c2c(-c3ccc(Oc4ccc(F)cn4)c(N)c3)c3c(N)ncnc3n2C)cc1] | 1H NMR (400 MHz, DMSO-d6) δ 9.90 (s, 1H), 8.20-8.13 (m, 2H), 7.83-7.73 (m, 1H), 7.73 (d, J = 8.6 Hz, 2H), 7.32 (d, J = 8.6 Hz, 2H), 7.02 (dd, J = 9.1, 3.6 Hz, 1H), 6.87 (d, J = 8.1 Hz, 1H), 6.70 (d, J = 2.1 Hz, 1H), 6.41 (dd, J = 8.1, 2.1 Hz, 1H), 5.80 (s, 1H), 5.54 (s, 1H), 5.01 (s, 2H), 3.60 (s, 3H), 2.08 (s, 1H), 1.96 (s, 3H). | 510.20 |
| N-(4-(4-amino-5-(3-amino-5-fluoro-4-(pyridin-2-yloxy)phenyl)-7-methyl-7H-pyrrolo[2,3-d]pyrimidin-6-yl)phenyl)methacrylamide | 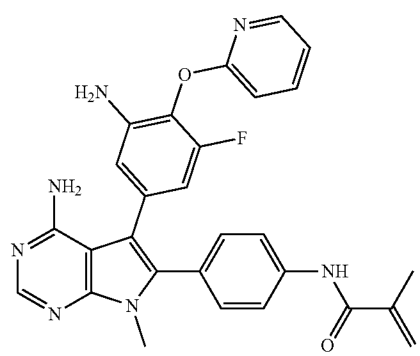 [SMILES: C=C(C)C(=O)Nc1ccc(-c2c(-c3cc(N)c(Oc4ccccn4)c(F)c3)c3c(N)ncnc3n2C)cc1] | ¹H NMR (400 MHz, DMSO-d₆) δ 9.92 (s, 1H), 8.25-8.07 (m, 2H), 7.91-7.70 (m, 3H), 7.35 (d, J = 8.4 Hz, 2H), 7.17-6.99 (m, 2H), 6.53 (s, 1H), 6.24 (dd, J = 10.8, 2.0 Hz, 1H), 5.82 (s, 1H), 5.54 (s, 1H), 5.34 (s, 2H), 3.59 (s, 3H), 1.96 (s, 3H). | 510.20 |
| N-(4-(4-amino-5-(4-((5-chloropyridin-2-yl)oxy)-3-hydroxyphenyl)-7-methyl-7H-pyrrolo[2,3-d]pyrimidin-6-yl)phenyl)methacrylamide | 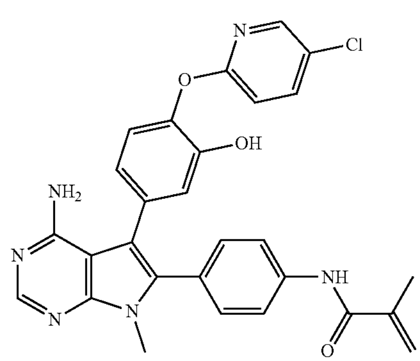 [SMILES: C=C(C)C(=O)Nc1ccc(-c2c(-c3ccc(Oc4ccc(Cl)cn4)c(O)c3)c3c(N)ncnc3n2C)cc1] | ¹H NMR (400 MHz, DMSO-d6) δ 9.91 (d, J = 4.6 Hz, 1H), 9.65 (d, J = 5.8 Hz, 1H), 8.25-8.10 (m, 2H), 7.92-7.85 (m, 1H), 7.73 (dd, J = 8.6, 6.5 Hz, 2H), 7.30 (dd, J = 11.6, 8.6 Hz, 2H), 7.07-6.92 (m, 2H), 6.92-6.77 (m, 2H), 6.20 (s, 1H), 5.82 (s, 1H), 5.55 (s, 1H), 3.60 (d, J = 1.5 Hz, 3H), 1.97 (d, J = 3.3 Hz, 3H). | 527.30 |

TABLE 2-continued

Additional Exemplary Compounds

| Compound | Structure | Proton NMR | MS [M + 1] |
|---|---|---|---|
| N-(4-(4-amino-5-(3-chloro-5-fluoro-4-(pyrimidin-2-yloxy)phenyl)-7-methyl-7H-pyrrolo[2,3-d]pyrimidin-6-yl)phenyl) methacrylamide | 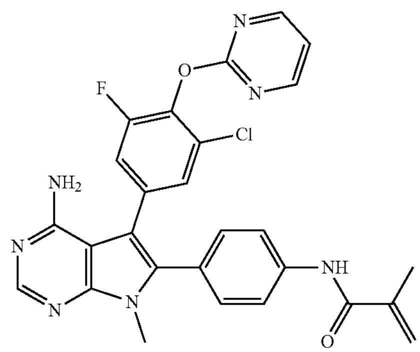 [SMILES: C=C(C)C(=O)Nc1ccc(-c2c(-c3cc(F)c(Oc4ncccn4)c(Cl)c3)c3c(N)ncnc3n2C)cc1] | 1H NMR (400 MHz, DMSO-d6) δ 9.96 (s, 1H), 8.71 (d, J = 4.8 Hz, 2H), 8.22 (s, 1H), 7.79 (d, J = 8.4 Hz, 2H), 7.40-7.34 (m, 3H), 7.28-7.17 (m, 2H), 5.83 (s, 1H), 5.55 (s, 1H), 3.57 (s, 3H), 1.96 (s, 3H). | 530.15 |
| N-(4-(4-amino-5-(3-hydroxy-5-methyl-4-(pyridin-2-yloxy)phenyl)-7-methyl-7H-pyrrolo[2,3-d]pyrimidin-6-yl)phenyl) methacrylamide | 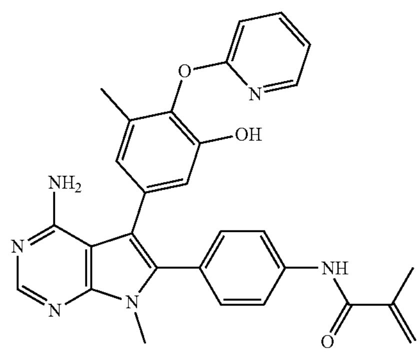 [SMILES: C=C(C)C(=O)Nc1ccc(-c2c(-c3cc(C)c(Oc4ccccn4)c(O)c3)c3c(N)ncnc3n2C)cc1] | $^1$H NMR (400 MHz, DMSO-d$_6$) δ 9.91 (s, 1H), 9.42 (s, 1H), 8.21-8.06 (m, 2H), 7.76 (p, J = 11.6, 9.8 Hz, 3H), 7.32 (dd, J = 16.8, 8.4 Hz, 2H), 7.11-6.88 (m, 2H), 6.71 (dd, J = 49.6, 10.1 Hz, 2H), 5.81 (s, 1H), 5.54 (s, 1H), 3.59 (d, J = 5.8 Hz, 3H), 2.15-1.89 (m, 6H). | 507.30 |
| N-(4-(4-amino-5-(3-fluoro-4-((5-methylpyrazin-2-yl)oxy)phenyl)-7-methyl-7H-pyrrolo[2,3-d]pyrimidin-6-yl)phenyl) methacrylamide | 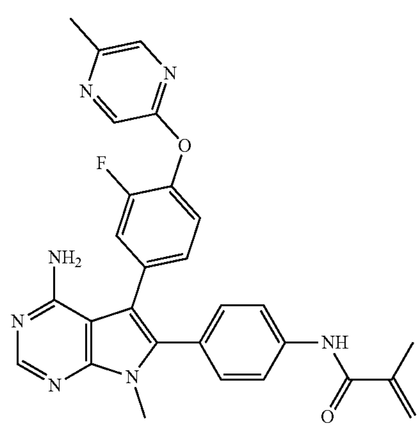 [SMILES: C=C(C)C(=O)Nc1ccc(-c2c(-c3ccc(Oc4cnc(C)cn4)c(F)c3)c3c(N)ncnc3n2C)cc1] | $^1$H NMR (400 MHz, DMSO-d6) δ 9.93 (s, 1H), 8.50 (d, J = 1.3 Hz, 1H), 8.21 (s, 1H), 8.11 (s, 1H), 7.75 (d, J = 8.6 Hz, 2H), 7.33 (dd, J = 8.5, 3.7 Hz, 3H), 7.19 (dd, J = 11.6, 2.0 Hz, 1H), 7.10 (d, J = 9.2 Hz, 1H), 6.02 (s, 2H), 5.81 (s, 1H), 5.54 (s, 1H), 3.59 (s, 3H), 2.45 (s, 3H), 1.96 (s, 3H). | 510.20 |
| N-(4-(4-amino-5-(3-methoxy-4-((1-methyl-1H-pyrazol-3-yl)oxy)phenyl)-7-methyl-7H-pyrrolo[2,3-d]pyrimidin-6-yl)phenyl) methacrylamide | 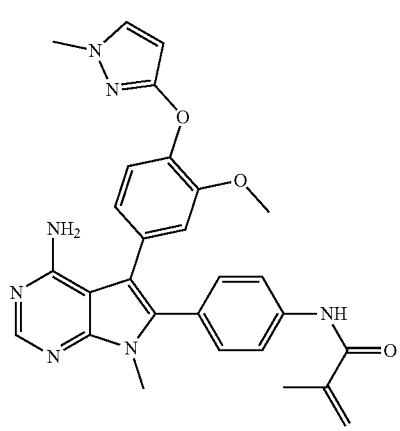 [SMILES: C=C(C)C(=O)Nc1ccc(-c2c(-c3ccc(Oc4ccn(C)n4)c(OC)c3)c3c(N)ncnc3n2C)cc1] | $^1$H NMR (400 MHz, DMSO-d$_6$) δ 9.89 (s, 1H), 8.19 (s, 1H), 7.72 (d, J = 8.7 Hz, 2H), 7.55 (d, J = 2.3 Hz, 1H), 7.30 (d, J = 8.6 Hz, 2H), 6.98 (d, J = 8.2 Hz, 1H), 6.92 (d, J = 2.1 Hz, 1H), 6.79-6.71 (m, 1H), 5.81 (s, 1H), 5.70 (d, J = 2.3 Hz, 1H), 5.54 (s, 1H), 3.71 (s, 3H), 3.64 (s, 3H), 3.60 (s, 3H), 2.00-1.89 (m, 3H). | 510.45 |

TABLE 2-continued

Additional Exemplary Compounds

| Compound | Structure | Proton NMR | MS [M + 1] |
|---|---|---|---|
| N-(4-(4-amino-5-(4-((5-chloropyrimidin-2-yl)oxy)phenyl)-7-methyl-7H-pyrrolo[2,3-d]pyrimidin-6-yl)phenyl) acrylamide | 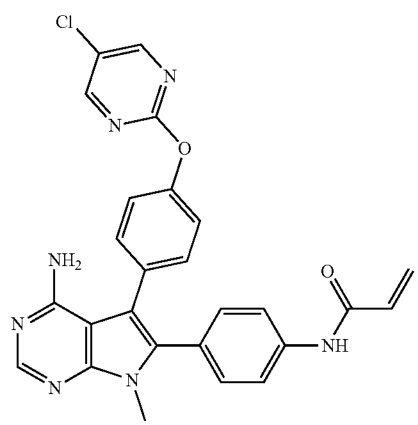 [SMILES: C=CC(=O)Nc1ccc(-c2c(-c3ccc(Oc4ncc(Cl)cn4)cc3)c3c(N)ncnc3n2C)cc1] | ¹H NMR (400 MHz, DMSO-d6) δ 10.28 (s, 1H), 8.78 (s, 2H), 8.21 (s, 1H), 7.71 (d, J = 8.4 Hz, 2H), 7.37-7.26 (m, 4H), 7.27-7.21 (m, 2H), 6.45 (dd, J = 17.2, 10.0 Hz, 1H), 6.28 (dd, J = 17.2, 2.0 Hz, 1H), 5.78 (dd, J = 10.0, 2.0 Hz, 2H), 3.60 (s, 3H). | 498.10 |
| N-(4-(4-amino-5-(4-((5-chloropyrimidin-2-yl)oxy)-3-methoxyphenyl)-7-methyl-7H-pyrrolo[2,3-d]pyrimidin-6-yl)phenyl) methacrylamide | 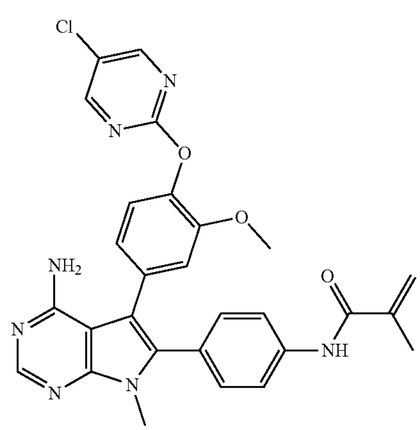 [SMILES: C=C(C)C(=O)Nc1ccc(-c2c(-c3ccc(Oc4ncc(Cl)cn4)c(OC)c3)c3c(N)ncnc3n2C)cc1] | ¹H NMR (400 MHz, DMSO-d6) δ 9.92 (s, 1H), 8.74 (s, 2H), 8.21 (s, 1H), 7.78-7.72 (m, 2H), 7.39-7.32 (m, 2H), 7.20 (d, J = 8.0 Hz, 1H), 7.00 (d, J = 1.9 Hz, 1H), 6.87 (dd, J = 8.1, 1.9 Hz, 1H), 5.98 (s, 2H), 5.81 (s, 1H), 5.54 (s, 1H), 3.58 (d, J = 14.3 Hz, 6H), 1.96 (s, 3H). | 542.15 |
| N-(4-(4-amino-5-(4-((5-chloro-6-methylpyridin-2-yl)oxy)phenyl)-7-methyl-7H-pyrrolo[2,3-d]pyrimidin-6-yl)phenyl) methacrylamide | 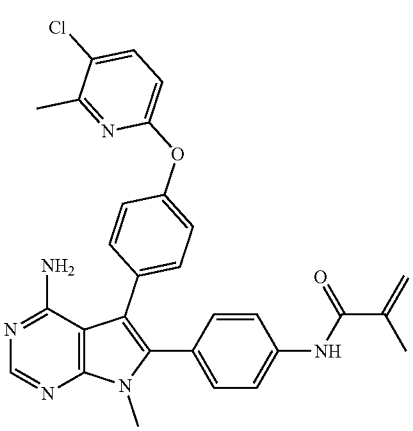 [SMILES: C=C(C)C(=O)Nc1ccc(-c2c(-c3ccc(Oc4ccc(Cl)c(C)n4)cc3)c3c(N)ncnc3n2C)cc1] | ¹H NMR (400 MHz, DMSO-d6) δ 9.90 (s, 1H), 8.20 (s, 1H), 7.89 (d, J = 8.6 Hz, 1H), 7.72 (d, J = 8.5 Hz, 2H), 7.28 (t, J = 8.4 Hz, 4H), 7.16-7.08 (m, 2H), 6.89 (d, J = 8.7 Hz, 1H), 5.94 (s, 3H), 5.80 (s, 1H), 5.54 (s, 1H), 3.62 (s, 3H), 2.40 (s, 3H), 1.95 (s, 3H). | 525.20 |

TABLE 2-continued

Additional Exemplary Compounds

| Compound | Structure | Proton NMR | MS [M + 1] |
|---|---|---|---|
| N-(4-(4-amino-5-(4-((5-chloropyridin-2-yl)oxy)phenyl)-7-methyl-7H-pyrrolo[2,3-d]pyrimidin-6-yl)phenyl)methacrylamide | 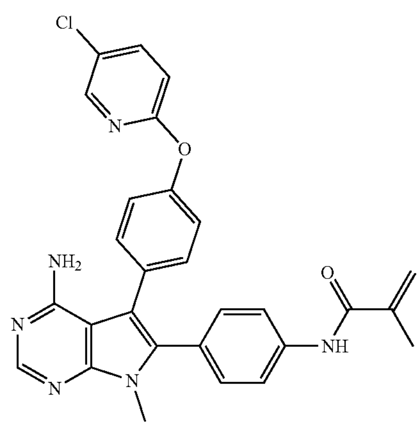 [SMILES: C=C(C)C(=O)Nc1ccc(-c2c(-c3ccc(Oc4ccc(Cl)cn4)cc3)c3c(N)ncnc3n2C)cc1] | $^1$H NMR (400 MHz, DMSO-d$_6$) δ 9.91 (s, 1H), 8.34-8.09 (m, 2H), 8.09-7.89 (m, 1H), 7.78-7.57 (m, 2H), 7.35-7.20 (m, 4H), 7.21-7.04 (m, 3H), 5.80 (d, J = 1.3 Hz, 3H), 5.54 (t, J = 1.4 Hz, 1H), 3.60 (d, J = 5.2 Hz, 3H), 1.95 (d, J = 1.2 Hz, 3H). | 511.15 |
| N-(4-(4-amino-5-(4-((5-chloro-6-methylpyridin-2-yl)oxy)phenyl)-7-methyl-7H-pyrrolo[2,3-d]pyrimidin-6-yl)phenyl)acrylamide | 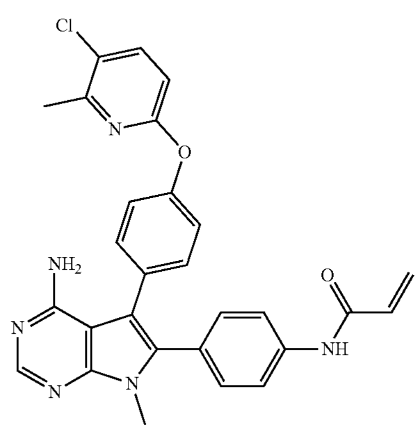 [SMILES: C=CC(=O)Nc1ccc(-c2c(-c3ccc(Oc4ccc(Cl)c(C)n4)cc3)c3c(N)ncnc3n2C)cc1] | $^1$H NMR (400 MHz, DMSO-d6) δ 10.26 (s, 1H), 8.20 (s, 1H), 7.88 (d, J = 8.6 Hz, 1H), 7.73-7.67 (m, 2H), 7.34-7.23 (m, 4H), 7.15-7.08 (m, 2H), 6.89 (d, J = 8.6 Hz, 1H), 6.44 (dd, J = 17.0, 10.1 Hz, 1H), 6.27 (dd, J = 16.9, 2.0 Hz, 1H), 5.96 (s, 2H), 5.78 (dd, J = 10.1, 2.1 Hz, 1H), 3.62 (s, 3H), 2.40 (s, 3H). | 511.20 |
| N-(4-(4-amino-5-(4-((5-(difluoromethyl)pyrimidin-2-yl)oxy)-3-methoxyphenyl)-7-methyl-7H-pyrrolo[2,3-d]pyrimidin-6-yl)phenyl)acrylamide | 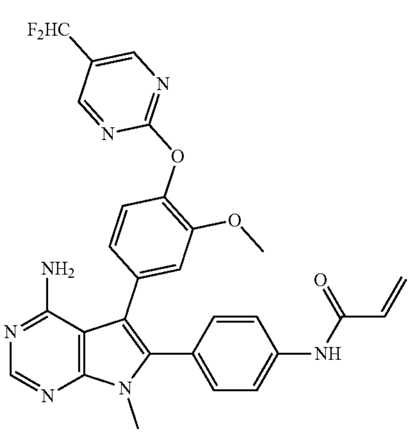 [SMILES: C=CC(=O)Nc1ccc(-c2c(-c3ccc(Oc4ncc(C(F)F)cn4)c(OC)c3)c3c(N)ncnc3n2C)cc1] | $^1$H NMR (400 MHz, DMSO-d$_6$) δ 10.29 (s, 1H), 8.87 (s, 2H), 8.22 (s, 1H), 7.73 (d, J = 8.3 Hz, 2H), 7.38 (d, J = 8.4 Hz, 2H), 7.22 (d, J = 8.0 Hz, 1H), 7.15 (s, 0H), 7.03-6.98 (m, 1H), 6.89 (dd, J = 8.0, 1.9 Hz, 1H), 6.45 (dd, J = 17.0, 10.1 Hz, 1H), 6.28 (dd, J = 16.9, 2.0 Hz, 1H), 6.00 (s, 2H), 5.78 (dd, J = 10.0, 2.1 Hz, 1H), 3.60 (s, 3H), 3.55 (s, 3H). | 544.2 |

TABLE 2-continued

Additional Exemplary Compounds

| Compound | Structure | Proton NMR | MS [M + 1] |
|---|---|---|---|
| N-(4-(4-amino-5-(4-((5-fluoropyrimidin-2-yl)oxy)-3-methoxyphenyl)-7-methyl-7H-pyrrolo[2,3-d]pyrimidin-6-yl)phenyl)acrylamide | 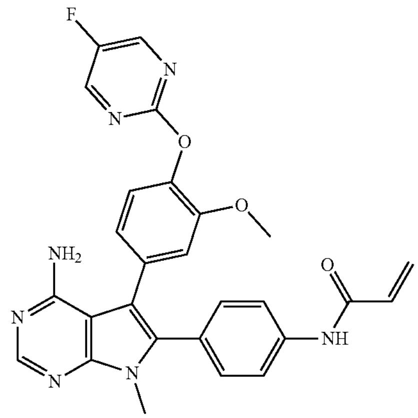 [SMILES: C=CC(=O)Nc1ccc(-c2c(-c3ccc(Oc4ncc(F)cn4)c(OC)c3)c3c(N)ncnc3n2C)cc1] | ¹H NMR (400 MHz, DMSO-d₆) δ 10.28 (s, 1H), 8.71 (s, 2H), 8.21 (s, 1H), 7.73 (d, J = 8.6 Hz, 2H), 7.40-7.34 (m, 2H), 7.18 (d, J = 8.2 Hz, 1H), 6.99 (d, J = 1.8 Hz, 1H), 6.87 (dd, J = 8.0, 2.0 Hz, 1H), 6.45 (dd, J = 17.0, 10.2 Hz, 1H), 6.28 (dd, J = 17.0, 2.0 Hz, 1H), 5.99 (s, 1H), 5.79 (dd, J = 10.2, 2.0 Hz, 1H), 3.60 (s, 3H), 3.55 (s, 3H). | 512.30 |
| N-(4-(4-amino-7-methyl-5-(2-methyl-4-(methylsulfonyl)phenyl)-7H-pyrrolo[2,3-d]pyrimidin-6-yl)phenyl)methacrylamide | 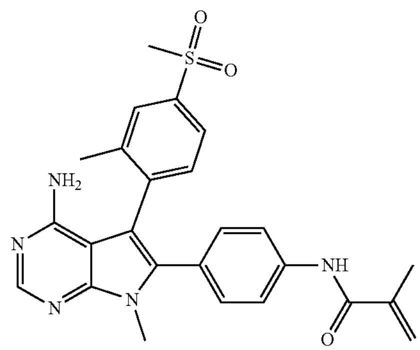 [SMILES: C=C(C)C(=O)Nc1ccc(-c2c(-c3ccc(S(C)(=O)=O)cc3C)c3c(N)ncnc3n2C)cc1] | ¹H NMR (400 MHz, DMSO-d₆) δ 9.87 (s, 1H), 8.21 (s, 1H), 7.80 (d, J = 2.0 Hz, 1H), 7.75-7.63 (m, 3H), 7.45 (d, J = 8.0 Hz, 1H), 7.22 (d, J = 8.6 Hz, 2H), 5.78 (s, 1H), 5.72 (s, 2H), 5.52 (s, 1H), 3.66 (s, 3H), 3.30 (s, 1H), 3.23 (s, 3H), 2.08 (s, 3H), 1.93 (s, 3H). | 476.30 |
| N-(4-(4-amino-7-methyl-5-(2-oxoindolin-5-yl)-7H-pyrrolo[2,3-d]pyrimidin-6-yl)phenyl)methacrylamide | 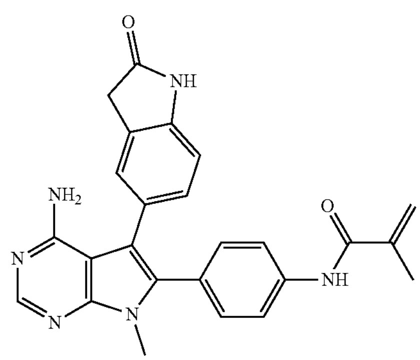 [SMILES: C=C(C)C(=O)Nc1ccc(-c2c(-c3ccc4c(c3)CC(=O)N4)c3c(N)ncnc3n2C)cc1] | ¹H NMR (400 MHz, DMSO-d₆) δ 10.40 (s, 1H), 9.88 (s, 1H), 8.17 (s, 1H), 7.69 (d, J = 8.3 Hz, 2H), 7.28 (d, J = 8.2 Hz, 2H), 7.10 (s, 1H), 7.03 (d, J = 8.0 Hz, 1H), 6.78 (d, J = 7.9 Hz, 1H), 5.79 (s, 1H), 5.53 (s, 1H), 3.59 (s, 3H), 3.44 (s, 2H), 1.95 (s, 3H). | 439.3 |
| N-(4-(4-amino-7-methyl-5-(4-(morpholine-4-carbonyl)phenyl)-7H-pyrrolo[2,3-d]pyrimidin-6-yl)phenyl)methacrylamide | 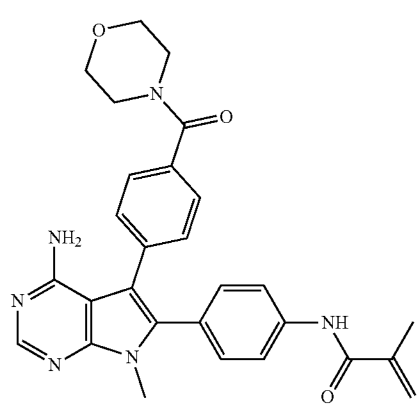 [SMILES: C=C(C)C(=O)Nc1ccc(-c2c(-c3ccc(C(=O)N4CCOCC4)cc3)c3c(N)ncnc3n2C)cc1] | ¹H NMR (400 MHz, DMSO-d₆) δ 9.89 (s, 1H), 8.21 (s, 1H), 7.74-7.67 (m, 2H), 7.41-7.34 (m, 2H), 7.30-7.22 (m, 4H), 5.98 (s, 1H), 5.80 (s, 1H), 5.54 (d, J = 1.7 Hz, 1H), 3.32 (s, HH), 1.95 (t, J = 1.2 Hz, 3H). | 497.20 |

TABLE 2-continued

Additional Exemplary Compounds

| Compound | Structure | Proton NMR | MS [M + 1] |
|---|---|---|---|
| 5-(4-amino-6-(4-methacrylamido-phenyl)-7-methyl-7H-pyrrolo[2,3-d]pyrimidin-5-yl)-N,N-dimethyl-1H-indole-2-carboxamide | 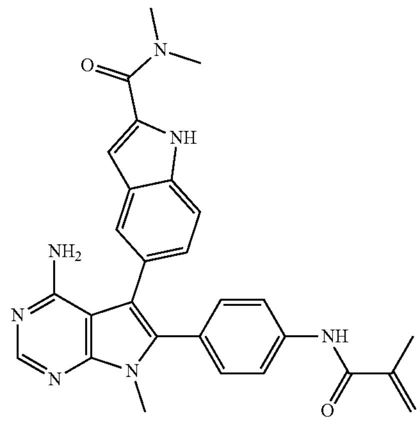 [SMILES: C=C(C)C(=O)Nc1ccc(-c2c(-c3ccc4[nH]c(C(=O)N(C)C)cc4c3)c3c(N)ncnc3n2C)cc1] | $^1$H NMR (400 MHz, DMSO-d$_6$) δ 11.60 (s, 1H), 9.83 (s, 1H), 8.18 (s, 1H), 7.68-7.61 (m, 2H), 7.50 (d, J = 1.6 Hz, 1H), 7.40 (d, J = 8.4 Hz, 1H), 7.31-7.24 (m, 2H), 7.07 (dd, J = 8.4, 1.6 Hz, 1H), 6.86 (d, J = 2.1 Hz, 1H), 5.77 (s, 1H), 5.51 (d, J = 1.9 Hz, 1H), 3.63 (s, 3H), 3.11 (s, 6H), 1.93 (t, J = 1.2 Hz, 3H). | 494.30 |
| N-(4-(4-amino-7-methyl-5-(6-(oxazol-2-yl)pyridin-3-yl)-7H-pyrrolo[2,3-d]pyrimidin-6-yl)phenyl) methacrylamide | 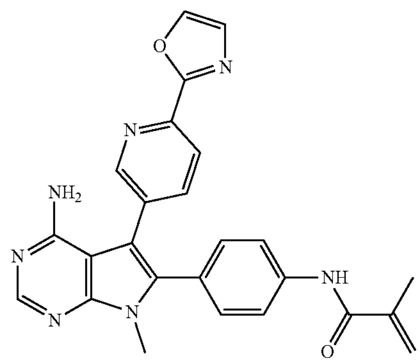 [SMILES: C=C(C)C(=O)Nc1ccc(-c2c(-c3ccc(-c4ncco4)nc3)c3c(N)ncnc3n2C)cc1] | $^1$H NMR (400 MHz, DMSO-d$_6$) δ 9.92 (s, 1H), 8.41 (d, J = 2.2 Hz, 1H), 8.28 (s, 1H), 8.23 (s, 1H), 8.05 (d, J = 8.1 Hz, 1H), 7.80-7.70 (m, 3H), 7.45 (s, 1H), 7.33-7.25 (m, 2H), 6.15 (s, 2H), 5.80 (s, 1H), 5.53 (t, J = 1.5 Hz, 1H), 3.62 (s, 3H), 1.95 (t, J = 1.3 Hz, 3H). | 452.1 |
| N-(4-(5-(6-(1H-1,2,4-triazol-1-yl)pyridin-3-yl)-4-amino-7-methyl-7H-pyrrolo[2,3-d]pyrimidin-6-yl)phenyl) methacrylamide | 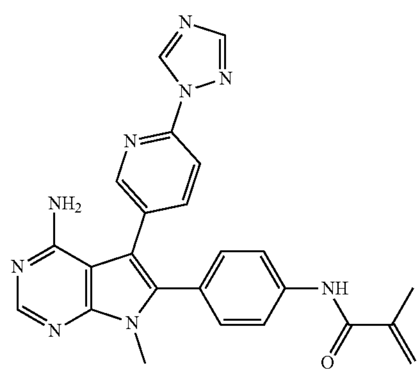 [SMILES: C=C(C)C(=O)Nc1ccc(-c2c(-c3ccc(-n4cncn4)nc3)c3c(N)ncnc3n2C)cc1] | $^1$H NMR (400 MHz, DMSO-d$_6$) δ 9.92 (s, 1H), 9.37 (s, 1H), 8.32-8.25 (m, 2H), 8.23 (s, 1H), 7.85 (s, 1H), 7.73 (d, J = 8.4 Hz, 2H), 7.31 (d, J = 8.4 Hz, 2H), 6.17 (s, 2H), 5.80 (s, 1H), 5.53 (s, 1H), 3.62 (s, 3H), 1.95 (s, 3H). | 452.30 |
| N-(4-(4-amino-7-methyl-5-(4-(3-methylisoxazol-5-yl)phenyl)-7H-pyrrolo[2,3-d]pyrimidin-6-yl)phenyl) methacrylamide | 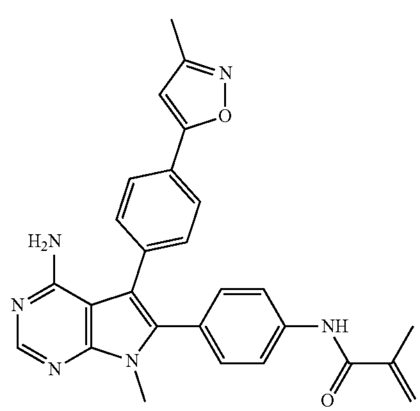 [SMILES: C=C(C)C(=O)Nc1ccc(-c2c(-c3ccc(-c4cc(C)no4)cc3)c3c(N)ncnc3n2C)cc1] | 1H NMR (400 MHz, DMSO-d6) δ 9.90 (s, 1H), 8.21 (s, 1H), 7.79 (d, J = 7.9 Hz, 2H), 7.71 (d, J = 8.3 Hz, 2H), 7.34 (d, J = 7.8 Hz, 2H), 7.28 (d, J = 8.2 Hz, 2H), 6.85 (s, 1H), 5.97 (s, 2H), 5.79 (s, 1H), 5.53 (s, 1H), 3.61 (s, 3H), 2.50 (s, 3H), 1.94 (s, 3H). | 465.30 |

TABLE 2-continued

Additional Exemplary Compounds

| Compound | Structure | Proton NMR | MS [M + 1] |
|---|---|---|---|
| N-(4-(4-amino-7-methyl-5-(1-(piperidin-4-ylmethyl)-1H-pyrazol-4-yl)-7H-pyrrolo[2,3-d]pyrimidin-6-yl)phenyl) acrylamide | 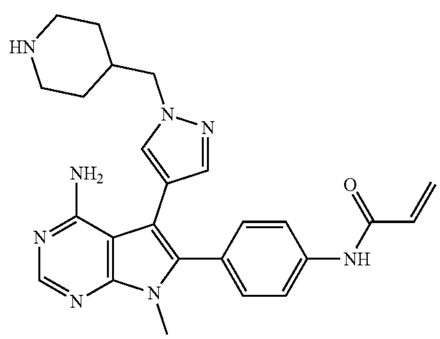 | $^1$H NMR (400 MHz, Methanol-$d_4$) δ 8.36 (s, 1H), 7.85-7.70 (m, 2H), 7.59-7.50 (m, 2H), 7.41-7.33 (m, 2H), 6.48 (dd, J = 17.0, 9.4 Hz, 2H), 8.85 (dd, J = 17.0, 2.5 Hz, 1H), 4.10 (dd, J = 9.4, 2.5 Hz, 2H), 3.80 (d, J = 7.1 Hz, 3H), 3.41 (s, 2H), 3.01 (d, J = 12.7 Hz, 2H), 2.20-2.01 (m, 1H), 1.81-1.61 (d, J = 14.0 Hz, 2H), 1.55-1.23 (m, 2H). | 457.3 |
| N-(4-(4-amino-5-(4-amino-3-(trifluoromethoxy) phenyl)-7-methyl-7H-pyrrolo[2,3-d]pyrimidin-6-yl)phenyl) methacrylamide | 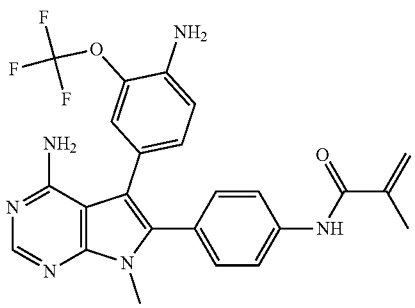 [SMILES: C=C(C)C(=O)Nc1ccc(-c2c(-c3ccc(N)c(OC(F)(F)F)c3)c3c(N)ncnc3n2C)cc1] | $^1$H NMR (400 MHz, DMSO-$d_6$) δ 9.88 (s, 1H), 8.17 (s, 1H), 7.71 (d, J = 8.3 Hz, 2H), 7.26 (d, J = 8.3 Hz, 2H), 6.95-6.89 (m, 2H), 6.78 (d, J = 8.7 Hz, 1H), 5.90 (s, 1H), 5.80 (s, 1H), 5.54 (s, 1H), 5.44 (s, 2H), 3.58 (s, 3H), 1.96 (s, 3H). | 483.15 |
| N-(4-(4-amino-5-(5-(hydroxymethyl) pyridin-3-yl)-7-methyl-7H-pyrrolo[2,3-d]pyrimidin-6-yl)phenyl) methacrylamide | 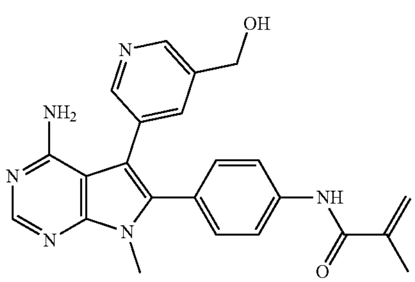 [SMILES: C=C(C)C(=O)Nc1ccc(-c2c(-c3cncc(CO)c3)c3c(N)ncnc3n2C)cc1] | $^1$H NMR (400 MHz, DMSO-$d_6$) δ 9.91 (s, 1H), 8.40 (d, J = 2.0 Hz, 1H), 8.24-8.17 (m, 2H), 7.71 (d, J = 8.3 Hz, 2H), 7.64 (d, J = 2.5 Hz, 1H), 7.27 (d, J = 8.4 Hz, 2H), 5.80 (s, 1H), 5.54 (s, 1H), 5.32 (t, J = 5.6 Hz, 1H), 4.53 (d, J = 5.6 Hz, 2H), 3.61 (s, 3H), 3.30 (s, 1H), 1.95 (s, 3H). | 415.2 |
| N-(4-(4-amino-5-(4-(2-(dimethylamino)-2-oxoethyl)phenyl)-7-methyl-7H-pyrrolo[2,3-d]pyrimidin-6-yl)phenyl) methacrylamide | 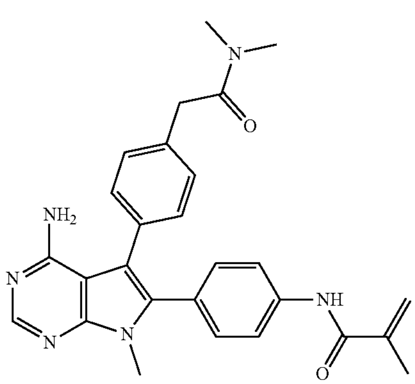 [SMILES: C=C(C)C(=O)Nc1ccc(-c2c(-c3ccc(CC(=O)N(C)C)cc3)c3c(N)ncnc3n2C)cc1] | $^1$H NMR (400 MHz, DMSO-$d_6$) δ 9.88 (s, 1H), 8.19 (s, 1H), 7.69 (d, J = 8.4 Hz, 2H), 7.27 (d, J = 8.4 Hz, 2H), 7.17-7.22 (m, 4H), 5.80 (s, 1H), 5.53 (s, 1H), 3.69 (s, 2H), 3.60 (s, 3H), 3.01 (s, 3H), 2.84 (s, 3H), 1.95 (s, 3H). | 469.20 |

TABLE 2-continued

Additional Exemplary Compounds

| Compound | Structure | Proton NMR | MS [M + 1] |
|---|---|---|---|
| N-(4-(4-amino-5-(4-(2-(dimethylamino)-2-oxoethyl)-3-fluorophenyl)-7-methyl-7H-pyrrolo[2,3-d]pyrimidin-6-yl)phenyl) methacrylamide | 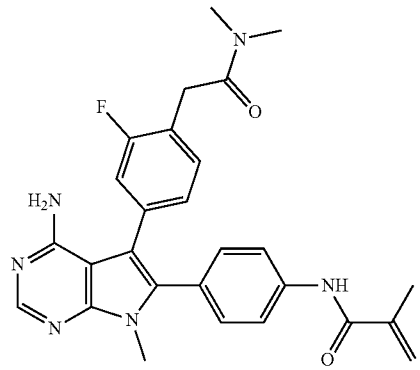 [SMILES: C=C(C)C(=O)Nc1ccc(-c2c(-c3ccc(CC(=O)N(C)C)c(F)c3)c3c(N)ncnc3n2C)cc1] | $^1$H NMR (400 MHz, DMSO-d$_6$) δ 9.90 (s, 1H), 8.20 (s, 1H), 7.75-7.69 (m, 2H), 7.33-7.26 (m, 2H), 7.22 (t, J = 7.9 Hz, 1H), 7.02 (dd, J = 7.7, 1.7 Hz, 1H), 6.97 (dd, J = 10.9, 1.7 Hz, 1H), 5.91-5.81 (s, 2H), 5.54 (d, J = 2.0 Hz, 1H), 3.70 (s, 2H), 3.59 (s, 3H), 3.05 (s, 3H), 2.85 (s, 3H), 1.95 (s, 3H). | 487.20 |
| N-(4-(4-amino-7-methyl-5-(1-(pyridin-3-ylmethyl)-1H-pyrazol-4-yl)-7H-pyrrolo[2,3-d]pyrimidin-6-yl)phenyl) methacrylamide | 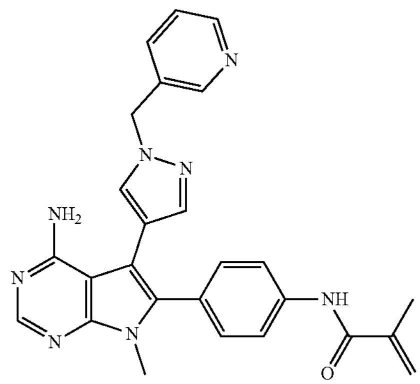 [SMILES: C=C(C)C(=O)Nc1ccc(-c2c(-c3cnn(Cc4cccnc4)c3)c3c(N)ncnc3n2C)cc1] | $^1$H NMR (400 MHz, DMSO-d$_6$) δ 9.92 (s, 1H), 8.52-8.43 (m, 2H), 8.16 (s, 1H), 7.84 (s, 1H), 7.74 (d, J = 8.5 Hz, 2H), 7.49-7.42 (m, 1H), 7.40-7.29 (m, 4H), 5.81 (s, 1H), 5.55 (s, 1H), 5.37 (s, 2H), 3.59 (s, 2H), 1.97 (s, 3H). | 465.4 |
| N-(4-(5-(4-((2H-tetrazol-5-yl)methyl)phenyl)-4-amino-7-methyl-7H-pyrrolo[2,3-d]pyrimidin-6-yl)phenyl) methacrylamide | 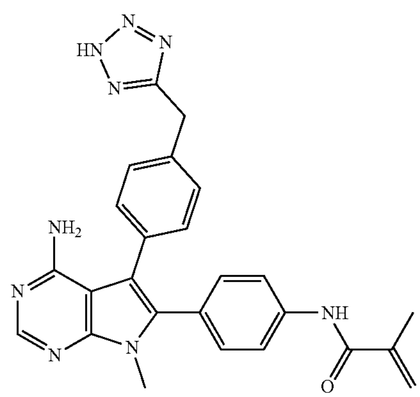 [SMILES: C=C(C)C(=O)Nc1ccc(-c2c(-c3ccc(Cc4nn[nH]n4)cc3)c3c(N)ncnc3n2C)cc1] | $^1$H NMR (400 MHz, Methanol-d$_4$) δ 8.20 (s, 1H), 7.68-7.62 (m, 2H), 7.27 (d, J = 8.1 Hz, 6H), 5.82 (s, 1H), 5.54 (s, 1H), 4.27 (s, 2H), 3.70 (s, 3H), 2.04 (t, J = 1.2 Hz, 3H), 1.33 (d, J = 15.8 Hz, 1H). | 466.20 |
| 2-(4-(4-amino-6-(4-methacrylamido-phenyl)-7-methyl-7H-pyrrolo[2,3-d]pyrimidin-5-yl)phenoxy) acetic acid | 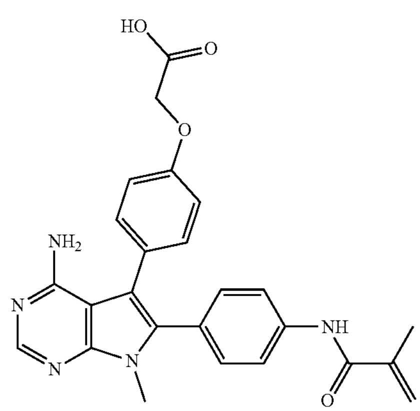 [SMILES: C=C(C)C(=O)Nc1ccc(-c2c(-c3ccc(OCC(=O)O)cc3)c3c(N)ncnc3n2C)cc1] | $^1$H NMR (400 MHz, DMSO-d$_6$) δ 13.02 (s, 1H), 9.88 (s, 1H), 8.18 (s, 1H), 7.69 (d, J = 8.3 Hz, 2H), 7.28 (dd, J = 12.5, 8.1 Hz, 2H), 7.17 (d, J = 8.2 Hz, 2H), 6.90 (d, J = 8.1 Hz, 2H), 5.80 (s, 1H), 5.53 (s, 1H), 4.65 (s, 2H), 3.60 (s, 3H), 1.95 (s, 3H). | 458.40 |

TABLE 2-continued

Additional Exemplary Compounds

| Compound | Structure | Proton NMR | MS [M + 1] |
|---|---|---|---|
| 4-(6-(4-acrylamidophenyl)-4-amino-7-methyl-7H-pyrrolo[2,3-d]pyrimidin-5-yl)-N-methylcyclohex-3-ene-1-carboxamide | 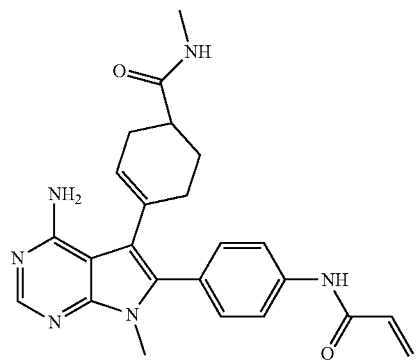 [SMILES: C=CC(=O)Nc1ccc(-c2c(C3=CCC(C(=O)NC)CC3)c3c(N)ncnc3n2C)cc1] | $^1$H NMR (400 MHz, DMSO-d$_6$) δ 10.31 (s, 1H), 8.10 (s, 1H), 7.78 (dd, J = 7.8, 5.9 Hz, 3H), 7.44 (d, J = 8.5 Hz, 2H), 6.48 (dd, J = 17.0, 10.1 Hz, 2H), 6.30 (dd, J = 17.0, 2.1 Hz, 1H), 5.83-5.74 (m, 2H), 3.57 (s, 3H), 2.57 (d, J = 4.5 Hz, 3H), 2.45 (q, J = 6.2 Hz, 3H), 2.29 (s, 1H), 2.24 (s, 2H), 1.89 (s, 2H), 1.65 (d, J = 6.2 Hz, 2H). | 431.25 |
| N-(4-(5-(1-acetyl-1,2,5,6-tetrahydropyridin-3-yl)-4-amino-7-methyl-7H-pyrrolo[2,3-d]pyrimidin-6-yl)phenyl)methacrylamide | 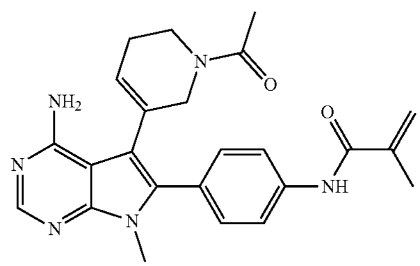 [SMILES: C=C(C)C(=O)Nc1ccc(-c2c(C3=CCCN(C(C)=O)C3)c3c(N)ncnc3n2C)cc1] | $^1$H NMR (400 MHz, DMSO-d$_6$) δ 9.96 (d, J = 6.3 Hz, 1H), 8.15 (d, J = 5.0 Hz, 1H), 7.82 (t, J = 8.2 Hz, 2H), 7.44 (dd, J = 10.6, 8.4 Hz, 2H), 6.35 (s, 2H), 6.05-5.81 (m, 2H), 5.56 (s, 1H), 3.78 (d, J = 34.2 Hz, 2H), 3.55 (t, J = 5.9 Hz, 4H), 3.48 (t, J = 5.7 Hz, 1H), 2.23 (d, J = 27.7 Hz, 2H), 1.99 (d, J = 11.9 Hz, 4H), 1.55 (s, 2H). | 431.25 |
| 5-(4-amino-6-(4-methacrylamido-phenyl)-7-methyl-7H-pyrrolo[2,3-d]pyrimidin-5-yl)-N,N-dimethylbenzo[b]thiophene-2-carboxamide | 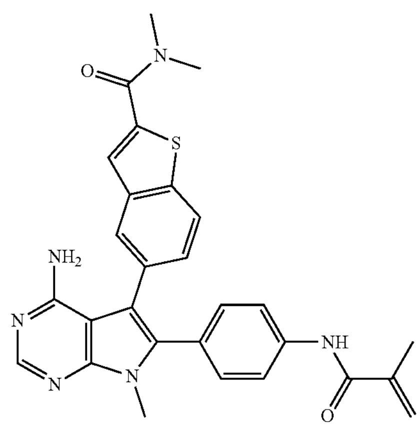 [SMILES: C=C(C)C(=O)Nc1ccc(-c2c(-c3ccc4sc(C(=O)N(C)C)cc4c3)c3c(N)ncnc3n2C)cc1] | $^1$H NMR (400 MHz, DMSO-d$_6$) δ 9.86 (s, 1H), 8.21 (s, 1H), 7.95 (d, J = 8.3 Hz, 1H), 7.84-7.77 (m, 2H), 7.71-7.64 (m, 2H), 7.32-7.23 (m, 3H), 5.78 (s, 1H), 5.52 (d, J = 1.9 Hz, 1H), 3.63 (s, 3H), 3.20 (s, 3H), 3.07 (s, 3H), 1.93 (s, 3H). | 511.2 |
| 5-(4-amino-6-(4-methacrylamido-phenyl)-7-methyl-7H-pyrrolo[2,3-d]pyrimidin-5-yl)-1H-indole-2-carboxylic acid | 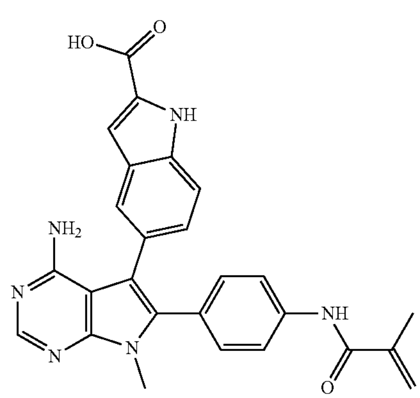 [SMILES: C=C(C)C(=O)Nc1ccc(-c2c(-c3ccc4[nH]c(C(=O)O)cc4c3)c3c(N)ncnc3n2C)cc1] | $^1$H NMR (400 MHz, DMSO-d$_6$) δ 13.45-12.25 (s, 1H), 11.85 (s, 1H), 9.85 (d, J = 12.7 Hz, 1H), 8.25 (d, J = 12.7 Hz, 1H), 7.78-7.65 (m, 2H), 7.54 (d, J = 1.6 Hz, 1H), 7.35 (d, J = 8.5 Hz, 1H), 7.35-7.20 (m, 2H), 7.20-7.01 (dd, J = 8.5, 1.7 Hz, 2H), 6.20-5.60 (d, J = 2.1 Hz, 2H), 5.60-5.40 (s, 1H), 3.65 (t, J = 1.5 Hz, 3H), 1.95 (d, J = 1.4 Hz, 3H). | 467.25 |

TABLE 2-continued

Additional Exemplary Compounds

| Compound | Structure | Proton NMR | MS [M + 1] |
|---|---|---|---|
| N-(4-(4-amino-7-methyl-5-(4-(thiazol-2-yl)phenyl)-7H-pyrrolo[2,3-d]pyrimidin-6-yl)phenyl)methacrylamide | 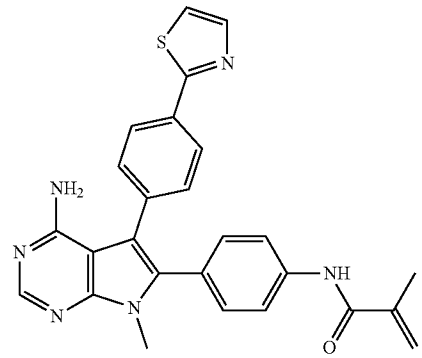 [SMILES: C=C(C)C(=O)Nc1ccc(-c2c(-c3ccc(-c4nccs4)cc3)c3c(N)ncnc3n2C)cc1] | $^1$H NMR (400 MHz, DMSO-d$_6$) δ 9.90 (s, 1H), 8.22 (s, 1H), 7.95-7.89 (m, 3H), 7.79 (d, J = 3.2 Hz, 1H), 7.72 (d, J = 8.3 Hz, 2H), 7.31 (dd, J = 18.0, 8.0 Hz, 4H), 5.79 (s, 2H), 5.53 (s, 1H), 3.62 (s, 3H), 1.94 (s, 3H), 1.18 (d, J = 13.5 Hz, 1H). | 467.20 |
| N-(4-(4-amino-7-methyl-5-(1-(pyridin-4-ylmethyl)-1H-pyrazol-4-yl)-7H-pyrrolo[2,3-d]pyrimidin-6-yl)phenyl)methacrylamide | 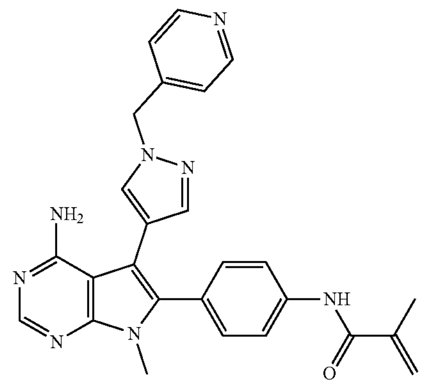 [SMILES: C=C(C)C(=O)Nc1ccc(-c2c(-c3cnn(Cc4ccncc4)c3)c3c(N)ncnc3n2C)cc1] | $^1$H NMR (400 MHz, DMSO-d$_6$) δ 9.96 (s, 1H), 8.54-8.48 (m, 2H), 8.17 (s, 1H), 7.83 (s, 1H), 7.78 (d, J = 8.4 Hz, 2H), 7.43 (s, 1H), 7.35 (d, J = 8.4 Hz, 2H), 6.96 (d, J = 5.4 Hz, 2H), 5.81 (s, 1H), 5.56 (s, 1H), 5.40 (s, 2H), 3.61 (s, 3H), 1.97 (s, 3H). | 465.2 |
| N-(4-(4-amino-5-(6-(benzyloxy)pyridin-3-yl)-7-methyl-7H-pyrrolo[2,3-d]pyrimidin-6-yl)phenyl)methacrylamide | 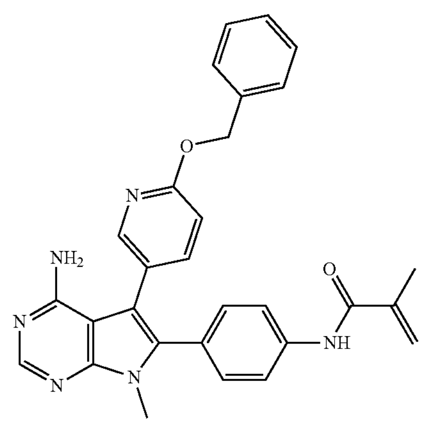 [SMILES: C=C(C)C(=O)Nc1ccc(-c2c(-c3ccc(OCc4ccccc4)nc3)c3c(N)ncnc3n2C)cc1] | $^1$H NMR (400 MHz, DMSO-d$_6$) δ 9.91 (s, 1H), 8.20 (s, 1H), 8.01 (d, J = 2.4 Hz, 1H), 7.76-7.68 (m, 2H), 7.57 (dd, J = 8.5, 2.4 Hz, 1H), 7.49-7.25 (m, 7H), 6.87 (d, J = 8.5 Hz, 1H), 5.94 (s, 1H), 5.81 (s, 1H), 5.54 (d, J = 1.9 Hz, 1H), 5.31 (s, 2H), 3.60 (s, 3H), 1.96 (t, J = 1.2 Hz, 3H). | 491.30 |
| N-(4-(4-amino-7-methyl-5-(3-methyl-4-(tetrahydrofuran-3-yloxy)phenyl)-7H-pyrrolo[2,3-d]pyrimidin-6-yl)phenyl)acrylamide | 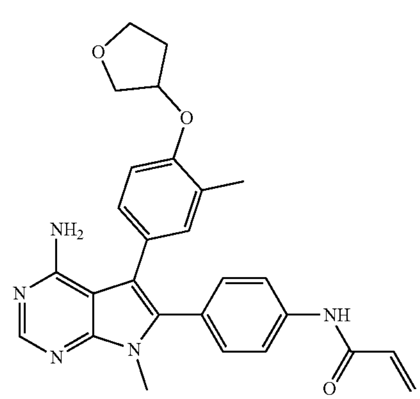 [SMILES: C=CC(=O)Nc1ccc(-c2c(-c3ccc(OC4CCOC4)c(C)c3)c3c(N)ncnc3n2C)cc1] | $^1$H NMR (400 MHz, DMSO-d$_6$) δ 10.24 (s, 1H), 8.17 (d, J = 2.2 Hz, 1H), 7.67 (d, J = 8.4 Hz, 2H), 7.33-7.22 (m, 2H), 7.09-6.96 (m, 2H), 6.88 (d, J = 8.4 Hz, 1H), 6.44 (dd, J = 16.9, 10.1 Hz, 1H), 6.27 (dd, J = 16.9, 2.1 Hz, 1H), 5.81-5.74 (m, 1H), 5.01 (d, J = 5.6 Hz, 1H), 3.94-3.72 (m, 4H), 3.59 (d, J = 5.5 Hz, 3H), 2.19 (dt, J = 14.5, 7.0 Hz, 1H), 2.09 (s, 3H), 1.99 (d, J = 14.4 Hz, 1H). | 470.30 |

TABLE 2-continued

Additional Exemplary Compounds

| Compound | Structure | Proton NMR | MS [M + 1] |
|---|---|---|---|
| N-(4-(4-amino-5-(4-((3,5-dimethyl-1H-pyrazol-1-yl)methyl)phenyl)-7-methyl-7H-pyrrolo[2,3-d]pyrimidin-6-yl)phenyl) methacrylamide | 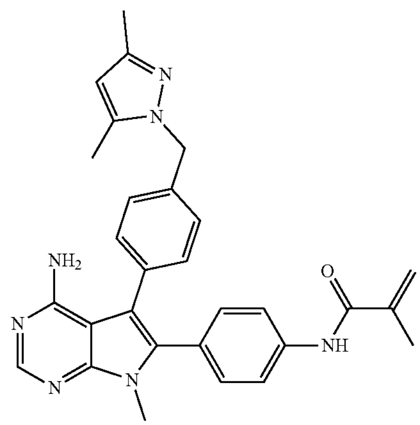 [SMILES: C=C(C)C(=O)Nc1ccc(-c2c(-c3ccc(Cn4nc(C)cc4C)cc3)c3c(N)ncnc3n2C)cc1] | $^1$H NMR (400 MHz, DMSO-d$_6$) δ 9.87 (s, 1H), 8.18 (s, 1H), 7.73-7.65 (m, 2H), 7.29-7.18 (m, 4H), 7.05 (d, J = 8.0 Hz, 2H), 5.99-5.75 (s, 3H), 5.55 (m, 1H), 5.20 (m, 2H), 3.65 (s, 3H), 2.15 (s, 3H), 2.10 (d, J = 0.7 Hz, 3H), 1.95 (s, 3H). | 492.3 |
| N-(4-(4-amino-7-methyl-5-(4-methyl-3,4-dihydro-2H-pyrido[3,2-b][1,4]oxazin-7-yl)-7H-pyrrolo[2,3-d]pyrimidin-6-yl)phenyl) methacrylamide | 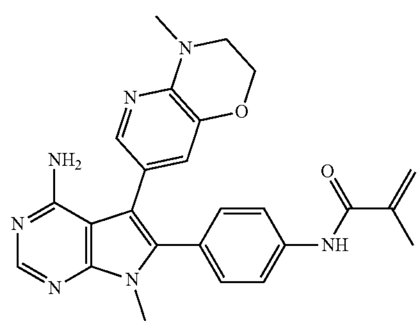 [SMILES: C=C(C)C(=O)Nc1ccc(-c2c(-c3cnc4c(c3)OCCN4C)c3c(N)ncnc3n2C)cc1] | $^1$H NMR (400 MHz, DMSO-d$_6$) δ 9.91 (s, 1H), 8.17 (s, 1H), 7.76-7.68 (m, 2H), 7.50 (d, J = 1.9 Hz, 1H), 7.33-7.26 (m, 2H), 6.78 (d, J = 2.0 Hz, 1H), 5.91 (s, 2H), 5.81 (s, 1H), 5.54 (d, J = 1.8 Hz, 1H), 4.20 (t, J = 4.5 Hz, 2H), 3.57 (s, 3H), 3.43 (t, J = 4.5 Hz, 2H), 3.01 (s, 3H), 1.96 (t, J = 1.2 Hz, 3H). | 456.35 |
| N-(4-(5-(2-acetamido-2,3-dihydro-1H-inden-5-yl)-4-amino-7-methyl-7H-pyrrolo[2,3-d]pyrimidin-6-yl)phenyl) methacrylamide | 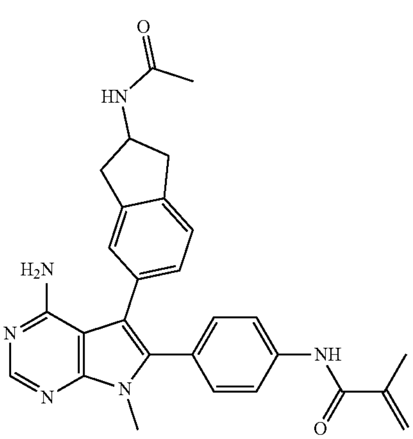 [SMILES: C=C(C)C(=O)Nc1ccc(-c2c(-c3ccc4c(c3)CC(NC(C)=O)C4)c3c(N)ncnc3n2C)cc1] | $^1$H NMR (400 MHz, DMSO-d$_6$) δ 9.88 (s, 1H), 8.20-8.12 (m, 2H), 7.69 (d, J = 8.4 Hz, 2H), 7.28 (d, J = 8.4 Hz, 2H), 7.19 (d, J = 7.7 Hz, 1H), 7.12 (s, 1H), 7.02 (d, J = 7.8 Hz, 1H), 5.80 (s, 1H), 5.53 (s, 1H), 4.45 (q, J = 6.8 Hz, 1H), 3.59 (s, 3H), 3.14 (td, J = 15.7, 7.6 Hz, 2H), 2.72 (td, J = 15.1, 5.8 Hz, 2H), 1.95 (s, 3H), 1.79 (s, 3H). | 481.30 |

TABLE 2-continued

Additional Exemplary Compounds

| Compound | Structure | Proton NMR | MS [M + 1] |
|---|---|---|---|
| N-(4-(4-amino-7-methyl-5-(4-((3-methyl-2,4-dioxoimidazolidin-1-yl)methyl)phenyl)-7H-pyrrolo[2,3-d]pyrimidin-6-yl)phenyl)methacrylamide | 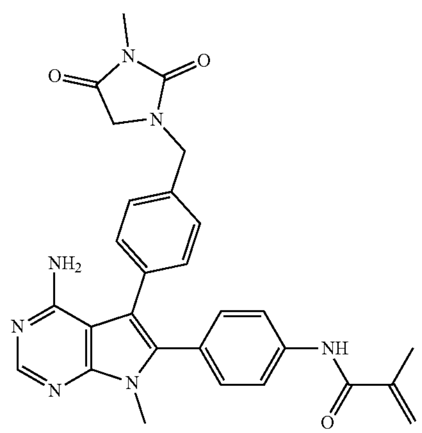 [SMILES: C=C(C)C(=O)Nc1ccc(-c2c(-c3ccc(CN4CC(=O)N(C)C4=O)cc3)c3c(N)ncnc3n2C)cc1] | $^1$H NMR (400 MHz, DMSO-d$_6$) δ 9.89 (s, 1H), 8.19 (s, 1H), 7.69 (d, J = 8.6 Hz, 2H), 7.30-7.19 (m, 6H), 5.80 (s, 1H), 5.53 (s, 1H), 4.50 (s, 2H), 3.91 (s, 2H), 3.60 (s, 3H), 2.88 (s, 3H), 1.95 (s, 3H). | 510.2 |
| N-(4-(4-amino-7-methyl-5-(6-(5-methyl-1,3,4-oxadiazol-2-yl)pyridin-3-yl)-7H-pyrrolo[2,3-d]pyrimidin-6-yl)phenyl)methacrylamide | 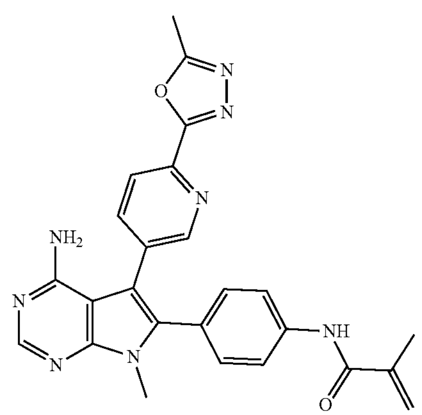 [SMILES: C=C(C)C(=O)Nc1ccc(-c2c(-c3ccc(-c4nnc(C)o4)nc3)c3c(N)ncnc3n2C)cc1] | $^1$H NMR (400 MHz, DMSO-d$_6$) δ 9.94 (s, 1H), 8.43 (d, J = 2.2 Hz, 1H), 8.24 (s, 1H), 8.09 (d, J = 8.1 Hz, 1H), 7.81 (dd, J = 8.1, 2.2 Hz, 1H), 7.77-7.70 (m, 2H), 7.32-7.25 (m, 2H), 6.20 (s, 2H), 5.80 (s, 1H), 5.54 (d, J = 1.7 Hz, 1H), 3.62 (s, 3H), 2.60 (s, 3H), 1.95 (d, J = 1.3 Hz, 3H). | 467.35 |
| N-(4-(4-amino-5-(4-(isoxazol-3-yl)phenyl)-7-methyl-7H-pyrrolo[2,3-d]pyrimidin-6-yl)phenyl)methacrylamide | 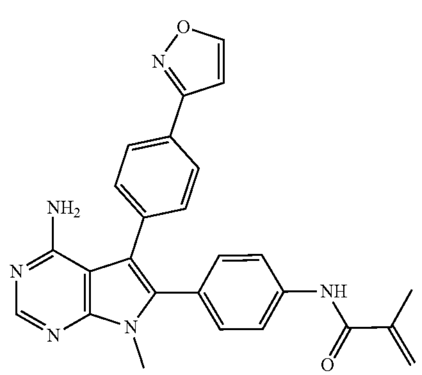 [SMILES: C=C(C)C(=O)Nc1ccc(-c2c(-c3ccc(-c4ccon4)cc3)c3c(N)ncnc3n2C)cc1] | $^1$H NMR (400 MHz, DMSO-d$_6$) δ 9.89 (s, 1H), 9.00 (d, J = 1.8 Hz, 1H), 8.22 (s, 1H), 7.90-7.84 (m, 2H), 7.75-7.68 (m, 2H), 7.39-7.32 (m, 2H), 7.32-7.25 (m, 2H), 7.15 (d, J = 1.7 Hz, 1H), 6.15-5.75 (s, 3H), 5.55-5.50 (m, 1H), 3.62 (s, 3H), 1.95 (s, 3H). | 451.2 |

TABLE 2-continued

Additional Exemplary Compounds

| Compound | Structure | Proton NMR | MS [M + 1] |
|---|---|---|---|
| N-(4-(4-amino-7-methyl-5-(6-(phenylthio)pyridin-3-yl)-7H-pyrrolo[2,3-d]pyrimidin-6-yl)phenyl)methacrylamide | 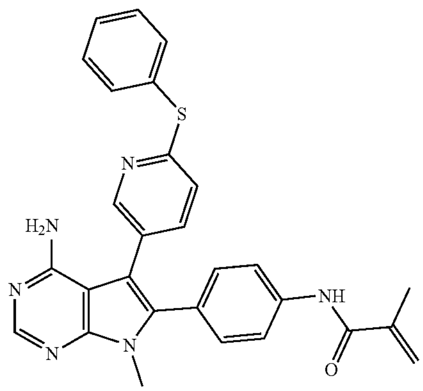 [SMILES: C=C(C)C(=O)Nc1ccc(-c2c(-c3ccc(Sc4ccccc4)nc3)c3c(N)ncnc3n2C)cc1] | $^1$H NMR (400 MHz, DMSO-d$_6$) δ 9.92 (s, 1H), 8.22-8.14 (m, 2H), 7.76-7.70 (m, 2H), 7.64-7.57 (m, 2H), 7.49 (dt, J = 7.2, 2.1 Hz, 4H), 7.30-7.23 (m, 2H), 6.92 (d, J = 8.3 Hz, 1H), 6.02 (s, 2H), 5.81 (s, 1H), 5.55 (s, 1H), 3.58 (s, 2H), 1.96 (d, J = 1.4 Hz, 3H). | 493.30 |
| N-(4-(4-amino-7-methyl-5-(1-methyl-1,2,3,4-tetrahydroquinolin-6-yl)-7H-pyrrolo[2,3-d]pyrimidin-6-yl)phenyl)acrylamide | 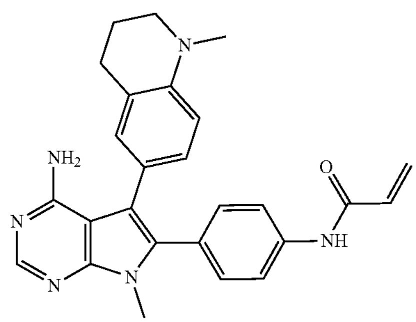 [SMILES: C=CC(=O)Nc1ccc(-c2c(-c3ccc4c(c3)CCCN4C)c3c(N)ncnc3n2C)cc1] | $^1$H NMR (400 MHz, DMSO-d$_6$) δ 10.24 (s, 1H), 8.15 (s, 1H), 7.68 (d, J = 8.3 Hz, 2H), 7.30 (d, J = 8.3 Hz, 2H), 6.86 (dd, J = 8.2, 2.1 Hz, 1H), 6.80 (d, J = 2.2 Hz, 1H), 6.53 (d, J = 8.4 Hz, 1H), 6.45 (dd, J = 17.0, 10.1 Hz, 1H), 6.27 (dd, J = 17.1, 2.1 Hz, 1H), 5.78 (dd, J = 10.0, 2.1 Hz, 1H), 3.58 (s, 3H), 3.19 (t, J = 5.6 Hz, 2H), 2.82 (s, 3H), 2.63 (t, J = 6.5 Hz, 2H), 1.87 (p, J = 6.1 Hz, 2H). | 439.30 |
| 5-(4-amino-6-(4-methacrylamidophenyl)-7-methyl-7H-pyrrolo[2,3-d]pyrimidin-5-yl)-N-methylindoline-1-carboxamide | | $^1$H NMR (400 MHz, DMSO-d$_6$) δ 9.87 (s, 1H), 8.17 (s, 1H), 7.78 (d, J = 8.2 Hz, 1H), 7.73-7.66 (m, 2H), 7.31-7.24 (m, 2H), 7.01 (d, J = 1.7 Hz, 1H), 6.95 (dd, J = 8.2, 1.9 Hz, 1H), 6.57 (q, J = 4.4 Hz, 1H), 5.80 (s, 1H), 5.53 (t, J = 1.5 Hz, 1H), 3.86 (t, J = 8.7 Hz, 2H), 3.60 (s, 3H), 3.07 (t, J = 8.7 Hz, 2H), 2.66 (d, J = 4.3 Hz, 3H), 1.95 (t, J = 1.2 Hz, 3H). | 482.30 |
| 5-(4-amino-6-(4-methacrylamidophenyl)-7-methyl-7H-pyrrolo[2,3-d]pyrimidin-5-yl)-N,N-dimethylpicolinamide | | $^1$H NMR (400 MHz, DMSO-d$_6$) δ 9.91 (s, 1H), 8.30 (s, 1H), 8.23 (s, 1H), 7.72 (t, J = 9.9 Hz, 3H), 7.51 (d, J = 7.9 Hz, 1H), 7.27 Hz, 2H), 6.16-6.10 (m, 2H), 5.81 (s, 1H), 5.54 (s, 1H), 3.62 (s, 3H), 2.99 (d, J = 4.8 Hz, 6H), 1.95 (s, 3H). | 456.25 |

TABLE 2-continued

Additional Exemplary Compounds

| Compound | Structure | Proton NMR | MS [M + 1] |
|---|---|---|---|
| N-(4-(4-amino-5-(4-(cyclopropyl-sulfinyl)phenyl)-7-methyl-7H-pyrrolo[2,3-d]pyrimidin-6-yl)phenyl) methacrylamide | 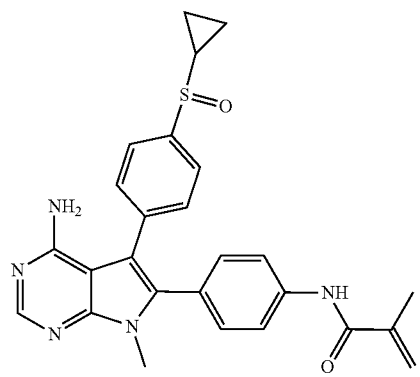 [SMILES: C=C(C)C(=O)Nc1ccc(-c2c(-c3ccc(S(=O)C4CC4)cc3)c3c(N)ncnc3n2C)cc1] | $^1$H NMR (400 MHz, DMSO-d$_6$) δ 9.90 (s, 1H), 8.22 (s, 1H), 7.71 (d, J = 8.5 Hz, 2H), 7.68-7.62 (m, 2H), 7.41 (d, J = 8.1Hz, 2H), 7.31-7.24 (m, 2H), 5.80 (s, 1H), 5.53 (s, 1H), 3.61 (s, 3H), 2.43 (s, 1H), 1.95 (s, 3H), 1.07-0.81 (m, 4H). | 472.1 |
| N-(4-(4-amino-7-methyl-5-(4-((N-methylacetamido) methyl)phenyl)-7H-pyrrolo[2,3-d]pyrimidin-6-yl)phenyl) methacrylamide | 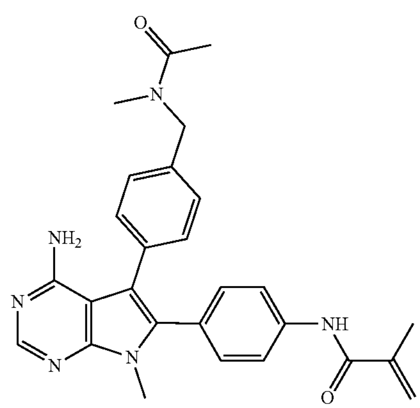 [SMILES: C=C(C)C(=O)Nc1ccc(-c2c(-c3ccc(CN(C)C(C)=O)cc3)c3c(N)ncnc3n2C)cc1] | $^1$H NMR (400 MHz, Methanol-d$_4$) δ 8.20 (d, J = 2.8 Hz, 1H), 7.66 (d, J = 8.2 Hz, 2H), 7.34 (d, J = 7.9 Hz, 1H), 7.31-7.22 (m, 5H), 5.81 (s, 1H), 5.54 (s, 1H), 4.63 (d, J = 15.5 Hz, 2H), 3.70 (d, J = 1.7 Hz, 3H), 3.04 (s, 2H), 2.94 (s, 1H), 2.18 (d, J = 6.6 Hz, 3H), 2.04 (s, 3H). | 469.35 |
| N-(4-(5-(6-(1H-pyrazol-1-yl)pyridin-3-yl)-4-amino-7-methyl-7H-pyrrolo[2,3-d]pyrimidin-6-yl)phenyl) methacrylamide | 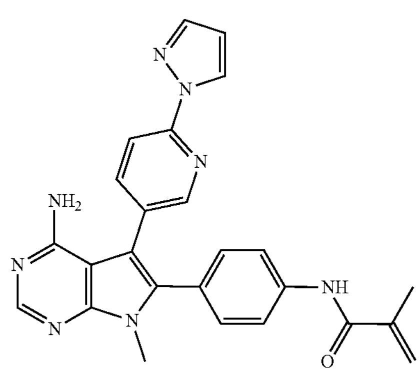 [SMILES: C=C(C)C(=O)Nc1ccc(-c2c(-c3ccc(-n4cccn4)nc3)c3c(N)ncnc3n2C)cc1] | $^1$H NMR (400 MHz, DMSO-d$_6$) δ 9.90 (s, 1H), 8.60 (d, J = 2.6 Hz, 1H), 8.24-8.18 (m, 2H), 7.89 (d, J = 8.4 Hz, 1H), 7.85-7.75 (m, 2H), 7.73 (d, J = 8.5 Hz, 2H), 7.30 (d, J = 8.5 Hz, 2H), 6.57 (t, J = 2.2 Hz, 1H), 6.12 (s, 2H), 5.79 (s, 1H), 5.53 (s, 1H), 3.62 (s, 3H), 1.94 (s, 3H). | 451.1 |

TABLE 2-continued

Additional Exemplary Compounds

| Compound | Structure | Proton NMR | MS [M + 1] |
|---|---|---|---|
| N-(4-(4-amino-7-methyl-5-(6-(3-(trifluoromethyl)phenoxy)pyridin-3-yl)-7H-pyrrolo[2,3-d]pyrimidin-6-yl)phenyl)methacrylamide | 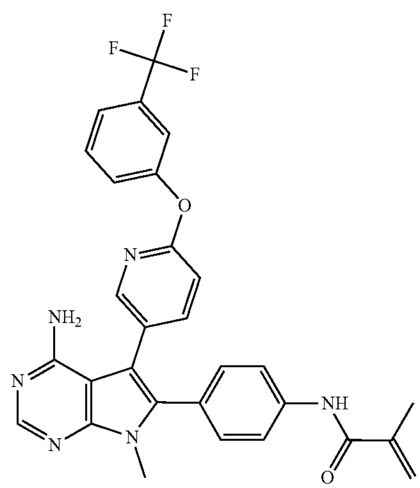 [SMILES: C=C(C)C(=O)Nc1ccc(-c2c(-c3ccc(Oc4cccc(C(F)(F)F)c4)nc3)c3c(N)ncnc3n2C)cc1] | $^1$H NMR (400 MHz, DMSO-d$_6$) δ 9.91 (s, 1H), 8.20 (s, 1H), 7.96 (d, J = 2.4 Hz, 1H), 7.74 (s, 1H), 7.74-7.65 (m, 2H), 7.64 (d, J = 8.0 Hz, 1H), 7.60-7.54 (m, 2H), 7.51 (d, J = 8.3 Hz, 1H), 7.32-7.25 (m, 2H), 7.10 (d, J = 8.4 Hz, 1H), 6.08 (s, 1H), 5.80 (s, 1H), 5.54 (s, 1H), 3.32 (s, 3H), 1.95 (s, 3H). | 545.25 |
| N-(4-(4-amino-5-(4-(4,5-dimethyloxazol-2-yl)phenyl)-7-methyl-7H-pyrrolo[2,3-d]pyrimidin-6-yl)phenyl)methacrylamide | 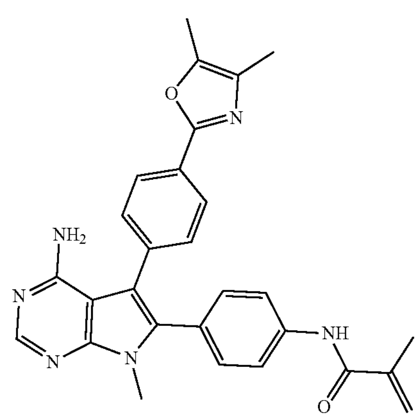 [SMILES: C=C(C)C(=O)Nc1ccc(-c2c(-c3ccc(-c4nc(C)c(C)o4)cc3)c3c(N)ncnc3n2C)cc1] | $^1$H NMR (400 MHz, DMSO-d$_6$) δ 9.89 (s, 1H), 8.21 (s, 1H), 7.87-7.80 (m, 2H), 7.74-7.67 (m, 2H), 7.35-7.28 (m, 2H), 7.31-7.23 (m, 2H), 5.94 (s, 2H), 5.82-5.77 (m, 1H), 5.55-5.50 (m, 1H), 3.62 (s, 3H), 2.31 (d, J = 1.2 Hz, 3H), 2.09 (d, J = 1.1 Hz, 3H), 1.95 (t, J = 1.2 Hz, 3H). | 479.35 |
| N-(4-(5-(4-acetamidocyclohex-1-enyl)-4-amino-7-methyl-7H-pyrrolo[2,3-d]pyrimidin-6-yl)phenyl)acrylamide | 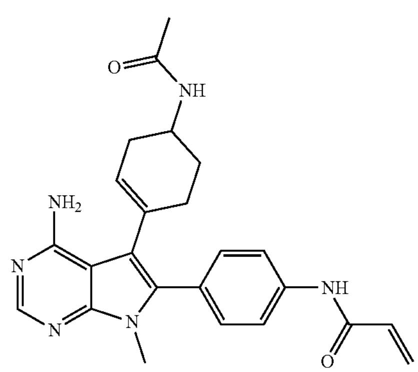 [SMILES: C=CC(=O)Nc1ccc(-c2c(C3=CCC(NC(C)=O)CC3)c3c(N)ncnc3n2C)cc1] | $^1$H NMR (400 MHz, DMSO-d$_6$) δ 10.31 (s, 1H), 8.12 (s, 1H), 7.85-7.76 (m, 2H), 7.74 (d, J = 7.3 Hz, 1H), 7.49-7.41 (m, 2H), 6.47 (dd, J = 17.0, 10.1 Hz, 1H), 6.36-6.21 (m, 3H), 5.80 (dd, J = 10.1, 2.1 Hz, 1H), 5.69 (d, J = 4.1 Hz, 1H), 3.80 (s, 1H), 3.57 (s, 3H), 2.34 (d, J = 16.4 Hz, 1H), 2.10-1.88 (m, 3H), 1.80 (s, 3H), 1.66 (d, J = 12.7 Hz, 1H), 1.46 (s, 1H). | 431.15 |

TABLE 2-continued

Additional Exemplary Compounds

| Compound | Structure | Proton NMR | MS [M + 1] |
|---|---|---|---|
| N-(4-(4-amino-5-(3,4-diethoxyphenyl)-7-methyl-7H-pyrrolo[2,3-d]pyrimidin-6-yl)phenyl)methacrylamide | 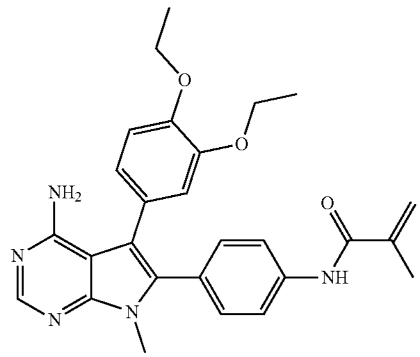 [SMILES: C=C(C)C(=O)Nc1ccc(-c2c(-c3ccc(OCC)c(OCC)c3)c3c(N)ncnc3n2C)cc1] | ¹H NMR (400 MHz, DMSO-d₆) δ 9.89 (s, 1H), 8.22 (s, 1H), 7.70 (d, J = 8.2 Hz, 2H), 7.28 (d, J = 8.2 Hz, 2H), 6.92 (d, J = 8.2 Hz, 1H), 6.79-6.70 (m, 2H), 6.13 (s, 1H), 5.80 (s, 1H), 5.54 (s, 1H), 4.01 (q, J = 1.0 Hz, 2H), 3.87 (q, J = 7.0 Hz, 2H), 3.33 (s, 3H), 1.95 (s, 3H), 1.32 (t, J = 7.0 Hz, 3H), 1.21 (t, J = 7.0 Hz, 3H). | 472.30 |
| N-(4-(4-amino-7-methyl-5-(2-oxo-1,2,3,4-tetrahydroquinolin-6-yl)-7H-pyrrolo[2,3-d]pyrimidin-6-yl)phenyl)methacrylamide | 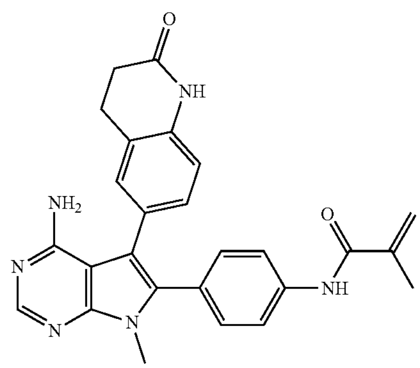 [SMILES: C=C(C)C(=O)Nc1ccc(-c2c(-c3ccc4c(c3)CCC(=O)N4)c3c(N)ncnc3n2C)cc1] | ¹H NMR (400 MHz, DMSO-d₆) δ 10.11 (s, 1H), 9.89 (s, 1H), 8.17 (s, 1H), 7.73-7.67 (m, 2H), 7.32-7.25 (m, 2H), 7.09 (d, J = 1.9 Hz, 1H), 6.98 (dd, J = 8.0, 2.0 Hz, 1H), 6.80 (d, J = 8.1 Hz, 1H), 5.80 (s, 2H), 5.54 (d, J = 1.9 Hz, 1H), 3.59 (s, 3H), 2.83 (t, J = 7.5 Hz, 2H), 2.44 (dd, J = 8.5, 6.5 Hz, 2H), 1.95 (d, J = 1.3 Hz, 3H). | 453.30 |
| N-(4-(4-amino-7-methyl-5-(4-(oxazol-4-yl)phenyl)-7H-pyrrolo[2,3-d]pyrimidin-6-yl)phenyl)methacrylamide | 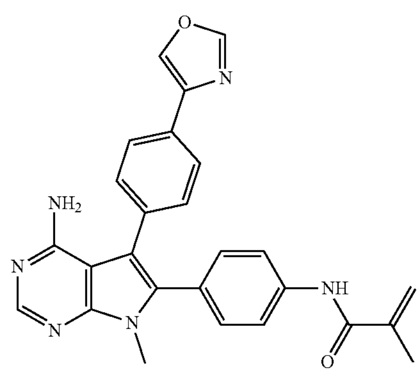 [SMILES: C=C(C)C(=O)Nc1ccc(-c2c(-c3ccc(-c4cocn4)cc3)c3c(N)ncnc3n2C)cc1] | ¹H NMR (400 MHz, DMSO-d₆) δ 9.88 (s, 1H), 8.62 (d, J = 1.0 Hz, 1H), 8.47 (d, J = 1.0 Hz, 1H), 8.20 (s, 1H), 7.80-7.74 (m, 2H), 7.74-7.66 (m, 2H), 7.32-7.22 (m, 4H), 5.79 (s, 1H), 5.55-5.50 (m, 1H), 3.61 (s, 3H), 1.95 (d, J = 1.2 Hz, 3H). | 451.35 |
| N-(4-(4-amino-7-methyl-5-(4-((3-oxomorpholino)methyl)phenyl)-7H-pyrrolo[2,3-d]pyrimidin-6-yl)phenyl)methacrylamide | 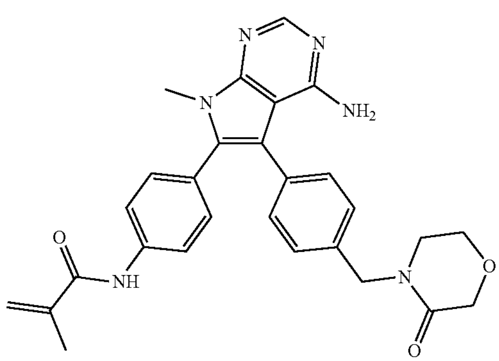 [SMILES: C=C(C)C(=O)Nc1ccc(-c2c(-c3ccc(CN4CCOCC4=O)cc3)c3c(N)ncnc3n2C)cc1] | ¹H NMR (400 MHz, DMSO-d₆) δ 9.88 (s, 1H), 8.19 (s, 1H), 7.69 (d, J = 8.4 Hz, 2H), 7.25 (d, J = 18.7 Hz, 6H), 6.12-5.75 (s, 1H), 5.55 (s, 1H), 4.55 (s, 2H), 4.15 (s, 2H), 3.91-3.75 (s, 2H), 3.60 (s, 3H), 3.29 (s, 2H), 1.95 (s, 3H). | 497.3 |

TABLE 2-continued

Additional Exemplary Compounds

| Compound | Structure | Proton NMR | MS [M + 1] |
|---|---|---|---|
| N-(4-(4-amino-7-methyl-5-(6-(2-methyl-2H-tetrazol-5-yl)pyridin-3-yl)-7H-pyrrolo[2,3-d]pyrimidin-6-yl)phenyl)methacrylamide | 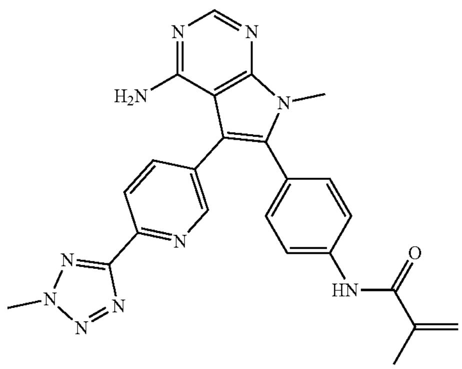 [SMILES: C=C(C)C(=O)Nc1ccc(-c2c(-c3ccc(-c4nnn(C)n4)nc3)c3c(N)ncnc3n2C)cc1] | ¹H NMR (400 MHz, DMSO-d₆) δ 9.92 (s, 1H), 8.45 (s, 1H), 8.24 (s, 1H), 8.09 (d, J = 8.1 Hz, 1H), 7.84-7.77 (m, 1H), 7.73 (d, J = 8.3 Hz, 2H), 7.29 (d, J = 8.2 Hz, 2H), 6.15 (s, 2H), 5.80 (s, 1H), 5.53 (s, 1H), 4.45 (s, 3H), 3.32 (s, 2H), 2.08 (s, 0H), 1.95 (s, 3H). | 467.30 |
| N-(4-(5-(4-(1H-imidazol-2-yl)phenyl)-4-amino-7-methyl-7H-pyrrolo[2,3-d]pyrimidin-6-yl)phenyl)methacrylamide | 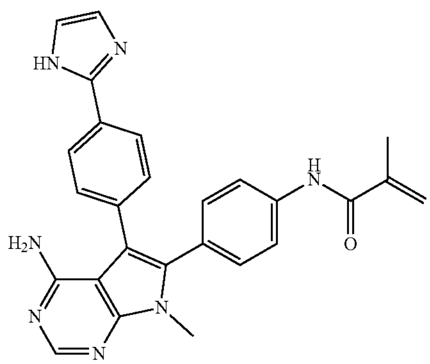 [SMILES: C=C(C)C(=O)Nc1ccc(-c2c(-c3ccc(-c4ncc[nH]4)cc3)c3c(N)ncnc3n2C)cc1] | ¹H NMR (400 MHz, DMSO-d₆) δ 12.47 (s, 1H), 9.88 (s, 1H), 8.21 (s, 1H), 7.92-7.85 (m, 2H), 7.73-7.67 (m, 2H), 7.32-7.22 (m, 5H), 7.03 (s, 1H), 5.97-5.90 (m, 1H), 5.79 (s, 1H), 5.53 (d, J = 2.0 Hz, 1H), 3.63 (s, 3H), 1.94 (s, 3H). | 450.30 |
| N-(4-(4-amino-5-(6-(3-fluorophenoxy)pyridin-3-yl)-7-methyl-7H-pyrrolo[2,3-d]pyrimidin-6-yl)phenyl)methacrylamide | 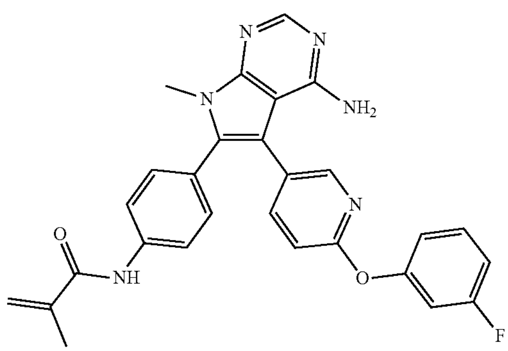 [SMILES: C=C(C)C(=O)Nc1ccc(-c2c(-c3ccc(Oc4cccc(F)c4)nc3)c3c(N)ncnc3n2C)cc1] | ¹H NMR (400 MHz, DMSO-d₆) δ 9.91 (s, 1H), 8.20 (s, 1H), 7.98 (d, J = 2.4 Hz, 1H), 7.76-7.70 (m, 2H), 7.67 (dd, J = 8.4, 2.5 Hz, 1H), 7.44 (q, J = 8.0 Hz, 1H), 7.32-7.25 (m, 2H), 7.11 (dt, J = 10.4, 2.4 Hz, 1H), 7.04 (dq, J = 8.3, 3.5, 2.3 Hz, 3H), 5.80 (s, 1H), 5.54 (s, 1H), 3.60 (s, 3H), 1.96 (s, 3H). | 495.15 |
| N-(4-(4-amino-7-methyl-5-(4-(5-(trifluoromethyl)-1,3,4-oxadiazol-2-yl)phenyl)-7H-pyrrolo[2,3-d]pyrimidin-6-yl)phenyl)methacrylamide | 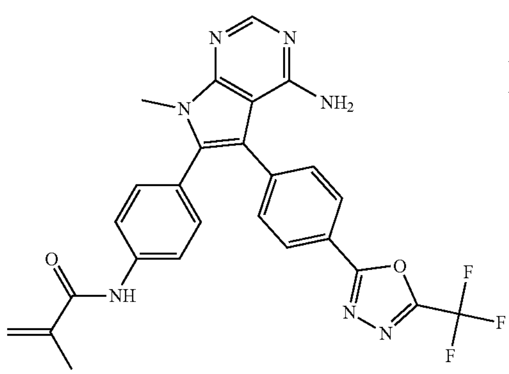 [SMILES: C=C(C)C(=O)Nc1ccc(-c2c(-c3ccc(-c4nnc(C(F)(F)F)o4)cc3)c3c(N)ncnc3n2C)cc1] | ¹H NMR (400 MHz, Methanol-d₄) δ 8.25 (s, 1H), 8.13-8.06 (m, 2H), 7.73-7.65 (m, 2H), 7.56-7.50 (m, 2H), 7.35-7.27 (m, 2H), 5.81 (s, 1H), 5.54 (d, J = 1.7 Hz, 1H), 3.72 (s, 3H), 2.04 (d, J = 1.3 Hz, 3H). | 520.3 |

TABLE 2-continued

Additional Exemplary Compounds

| Compound | Structure | Proton NMR | MS [M + 1] |
|---|---|---|---|
| N-(4-(4-amino-7-methyl-5-(5-morpholinopyridin-3-yl)-7H-pyrrolo[2,3-d]pyrimidin-6-yl)phenyl)methacrylamide | 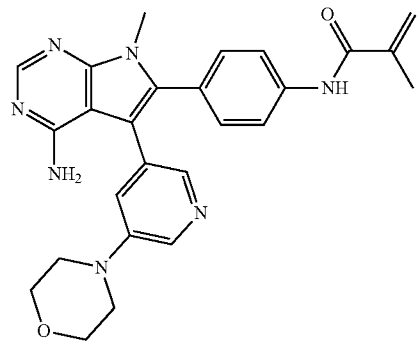 [SMILES: C=C(C)C(=O)Nc1ccc(-c2c(-c3cncc(N4CCOCC4)c3)c3c(N)ncnc3n2C)cc1] | ¹H NMR (400 MHz, DMSO-d₆) δ 9.92 (s, 1H), 8.22 (d, J = 11.4 Hz, 2H), 7.79 (s, 1H), 7.72 (d, J = 8.3 Hz, 2H), 7.29 (d, J = 8.2 Hz, 2H), 7.22 (d, J = 2.9 Hz, 1H), 6.12 (s, 2H), 5.80 (s, 1H), 5.54 (s, 1H), 3.75 (t, J = 4.8 Hz, 4H), 3.61 (s, 3H), 3.16 (t, J = 4.9 Hz, 4H), 1.96 (s, 3H). | 470.20 |
| N-(4-(4-amino-7-methyl-5-(6-(4-methyl-1H-pyrazol-1-yl)pyridin-3-yl)-7H-pyrrolo[2,3-d]pyrimidin-6-yl)phenyl)methacrylamide | 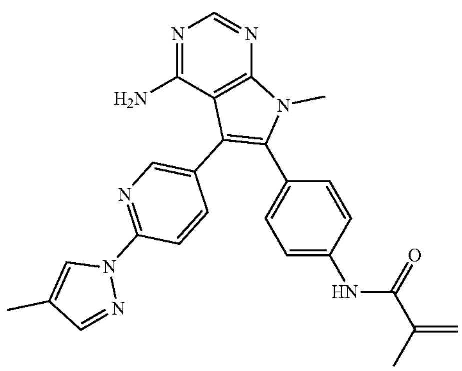 [SMILES: C=C(C)C(=O)Nc1ccc(-c2c(-c3ccc(-n4cc(C)cn4)nc3)c3c(N)ncnc3n2C)cc1] | ¹H NMR (400 MHz, DMSO-d₆) δ 9.90 (s, 1H), 8.37 (s, 1H), 8.22 (s, 1H), 8.17 (d, J = 2.2 Hz, 1H), 7.83 (d, J = 8.4 Hz, 1H), 7.79-7.69 (m, 3H), 7.64 (s, 1H), 7.29 (d, J = 8.5 Hz, 2H), 6.10 (s, 2H), 5.79 (s, 1H), 5.53 (s, 1H), 3.62 (s, 3H), 2.10 (s, 3H), 1.95 (s, 3H). | 465.30 |
| N-(4-(4-amino-7-methyl-5-(3-methyl-2-oxo-2,3-dihydro-1H-benzo[d]imidazol-5-yl)-7H-pyrrolo[2,3-d]pyrimidin-6-yl)phenyl)methacrylamide | 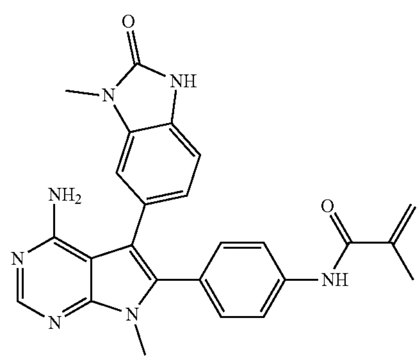 [SMILES: C=C(C)C(=O)Nc1ccc(-c2c(-c3ccc4[nH]c(=O)n(C)c4c3)c3c(N)ncnc3n2C)cc1] | ¹H NMR (400 MHz, DMSO-d₆) δ 10.86 (s, 1H), 9.86 (s, 1H), 8.18 (s, 1H), 7.71-7.63 (m, 2H), 7.32-7.26 (m, 2H), 6.98 (d, J = 1.6 Hz, 1H), 6.93 (d, J = 7.9 Hz, 1H), 6.83 (dd, J = 7.9, 1.6 Hz, 1H), 5.79 (s, 1H), 5.55-5.50 (m, 1H), 3.61 (s, 3H), 3.20 (s, 3H), 1.94 (t, J = 1.2 Hz, 3H) | 454.30 |
| N-(4-(4-amino-5-(4-(cyclopropylmethoxy)phenyl)-7-methyl-7H-pyrrolo[2,3-d]pyrimidin-6-yl)phenyl)methacrylamide | | ¹H NMR (400 MHz, DMSO-d₆) δ 9.88 (s, 1H), 8.17 (s, 1H), 7.72-7.65 (m, 2H), 7.26 (d, J = 8.4 Hz, 2H), 7.14 (d, J = 8.6 Hz, 2H), 6.90 (d, J = 8.3 Hz, 2H), 5.79 (s, 1H), 5.53 (s, 1H), 3.80 (d, J = 1.0 Hz, 2H), 3.60 (s, 3H), 1.95 (s, 3H), 1.20 (ddd, J = 12.5, 7.9, 5.0 Hz, 1H), 0.61-0.52 (m, 2H), 0.32 (dd, J = 4.8, 1.6 Hz, 2H). | 454.20 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N,N-dimethylbenzamide | 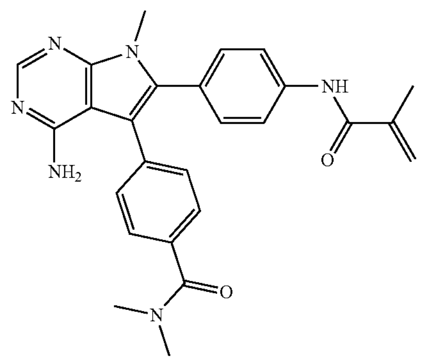 [SMILES: C=C(C)C(=O)Nc1ccc(-c2c(-c3ccc(C(=O)N(C)C)cc3)c3c(N)ncnc3n2C)cc1] | $^1$H NMR (400 MHz, DMSO-d$_6$) δ 9.89 (s, 1H), 8.22 (s, 1H), 7.75-7.67 (m, 2H), 7.40-7.34 (m, 2H), 7.30-7.23 (m, 4H), 6.02 (s, 2H), 5.80 (s, 1H), 5.53 (t, J = 1.5 Hz, 1H), 3.62 (s, 3H), 2.96 (s, 6H), 1.95 (d, J = 1.3 Hz, 3H). | 455.20 |
| N-(4-(4-amino-5-(1-benzyl-6-oxo-1,6-dihydropyridin-3-yl)-7-methyl-7H-pyrrolo[2,3-d]pyrimidin-6-yl)phenyl)methacrylamide | 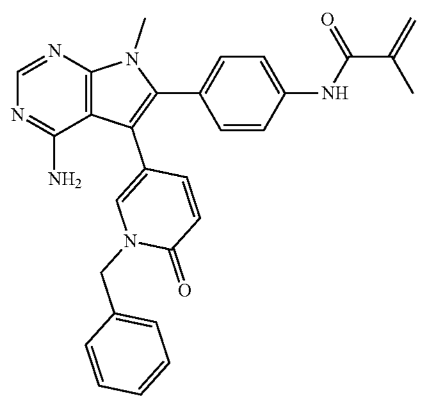 [SMILES: C=C(C)C(=O)Nc1ccc(-c2c(-c3ccc(=O)n(Cc4ccccc4)c3)c3c(N)ncnc3n2C)cc1] | $^1$H NMR (400 MHz, Methanol-d$_4$) δ 8.24 (s, 1H), 7.81-7.73 (m, 2H), 7.60 (d, J = 1.0 Hz, 1H), 7.41-7.26 (m, 7H), 6.49 (d, J = 1.9 Hz, 1H), 6.23 (dd, J = 7.0, 1.9 Hz, 1H), 5.85-5.80 (m, 1H), 5.56 (d, J = 1.8 Hz, 1H), 5.18 (s, 2H), 3.68 (s, 3H), 2.08-2.03 (m, 3H). | 491.30 |
| N-(4-(4-amino-5-(2,3-dimethyl-1-oxoisoindolin-5-yl)-7-methyl-7H-pyrrolo[2,3-d]pyrimidin-6-yl)phenyl)methacrylamide | 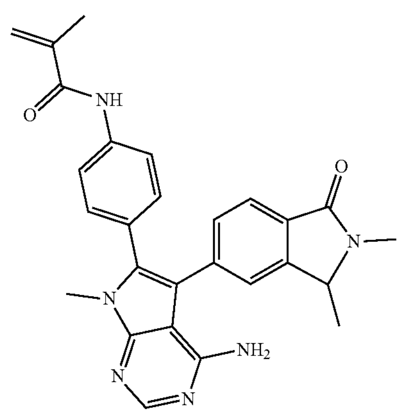 [SMILES: C=C(C)C(=O)Nc1ccc(-c2c(-c3ccc4c(c3)C(C)N(C)C4=O)c3c(N)ncnc3n2C)cc1] | $^1$H NMR (400 MHz, DMSO-d$_6$) δ 9.88 (s, 1H), 8.22 (s, 1H), 7.73-7.66 (m, 2H), 7.59 (d, J = 7.7 Hz, 1H), 7.44 (s, 1H), 7.28 (td, J = 7.5, 6.9, 1.7 Hz, 3H), 5.79 (s, 1H), 5.53 (s, 1H), 4.50 (q, J = 6.6 Hz, 1H), 3.63 (s, 3H), 2.99 (s, 3H), 1.95 (t, J = 1.3 Hz, 3H), 1.33 (d, J = 6.6 Hz, 3H). | 467.25 |
| N-(4-(4-amino-7-methyl-5-(4-(5-(methylamino)-1,3,4-thiadiazol-2-yl)phenyl)-7H-pyrrolo[2,3-d]pyrimidin-6-yl)phenyl)methacrylamide | 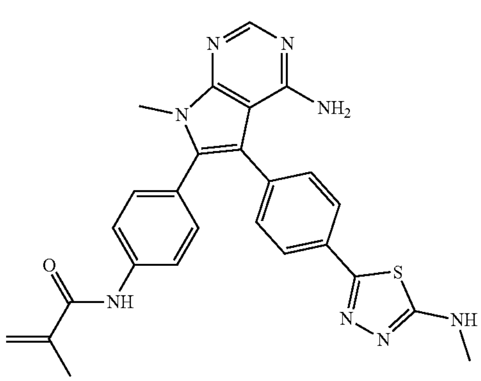 [SMILES: C=C(C)C(=O)Nc1ccc(-c2c(-c3ccc(-c4nnc(NC)s4)cc3)c3c(N)ncnc3n2C)cc1] | $^1$H NMR (400 MHz, DMSO-d$_6$) δ 9.90 (s, 1H), 8.21 (s, 1H), 7.87 (q, J = 4.8 Hz, 1H), 7.75-7.68 (m, 4H), 7.33-7.25 (m, 4H), 5.80 (s, 1H), 5.53 (t, J = 1.6 Hz, 1H), 3.61 (s, 3H), 2.93 (d, J = 4.8 Hz, 3H), 1.95 (d, J = 1.3 Hz, 3H). | 497.20 |

TABLE 2-continued

Additional Exemplary Compounds

| Compound | Structure | Proton NMR | MS [M + 1] |
|---|---|---|---|
| N-(4-(4-amino-7-methyl-5-(1-(methylsulfonyl)-1H-indol-5-yl)-7H-pyrrolo[2,3-d]pyrimidin-6-yl)phenyl)methacrylamide | 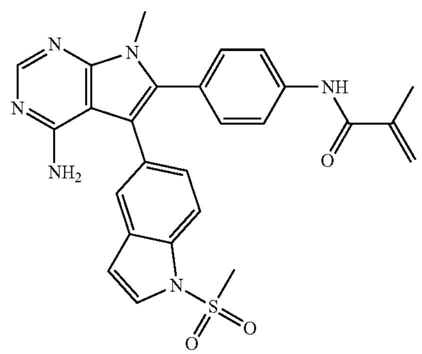 [SMILES: C=C(C)C(=O)Nc1ccc(-c2c(-c3ccc4c(ccn4S(C)(=O)=O)c3)c3c(N)ncnc3n2C)cc1] | $^1$H NMR (400 MHz, DMSO-$d_6$) δ 12.22 (s, 1H), 9.85 (s, 1H), 8.20 (s, 1H), 8.01 (s, 1H), 7.70-7.61 (m, 3H), 7.50 (d, J = 8.4 Hz, 1H), 7.31-7.24 (m, 2H), 7.14 (dd, J = 8.4, 1.7 Hz, 1H), 5.90 (s, 2H), 5.77 (s, 1H), 5.51 (t, J = 1.4 Hz, 1H), 3.63 (s, 3H), 3.02 (s, 3H), 1.93 (t, J = 1.2 Hz, 3H). | 501.35 |
| N-(4-(4-amino-7-methyl-5-(4-methyl-3,4-dihydro-2H-benzo[b][1,4]oxazin-7-yl)-7H-pyrrolo[2,3-d]pyrimidin-6-yl)phenyl)methacrylamide | 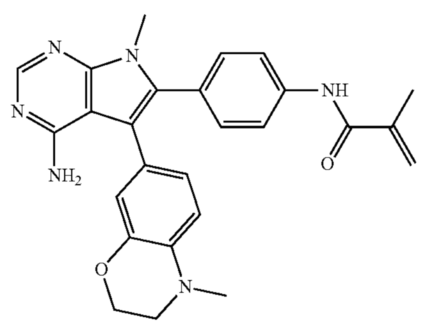 [SMILES: C=C(C)C(=O)Nc1ccc(-c2c(-c3ccc4c(c3)OCCN4C)c3c(N)ncnc3n2C)cc1] | $^1$H NMR (400 MHz, DMSO-$d_6$) δ 9.88 (s, 1H), 8.16 (s, 1H), 7.71 (d, J = 8.3 Hz, 2H), 7.28 (d, J = 8.3 Hz, 2H), 6.67 (s, 2H), 6.53 (s, 1H), 5.80 (s, 2H), 5.54 (s, 1H), 4.21 (t, J = 4.3 Hz, 2H), 3.31 (s, 2H), 3.24 (t, J = 4.5 Hz, 2H), 2.83 (s, 3H), 1.96 (s, 3H), 1.35-1.07 (m, 2H). | 455.30 |
| 5-(4-amino-6-(4-methacrylamido-phenyl)-7-methyl-7H-pyrrolo[2,3-d]pyrimidin-5-yl)-N,N-dimethyl-2,3-dihydro-1H-indene-1-carboxamide | 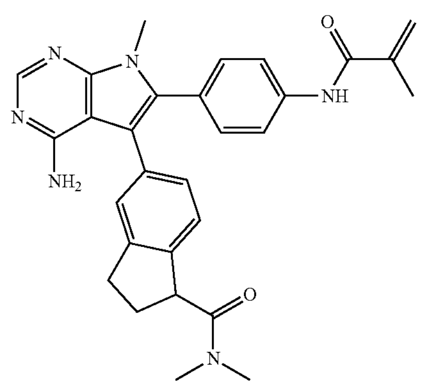 [SMILES: C=C(C)C(=O)Nc1ccc(-c2c(-c3ccc4c(c3)CCC4C(=O)N(C)C)c3c(N)ncnc3n2C)cc1] | $^1$H NMR (400 MHz, DMSO-$d_6$) δ 9.87 (s, 1H), 8.18 (s, 1H), 7.74-7.66 (m, 2H), 7.33-7.25 (m, 2H), 7.15 (s, 1H), 7.09-6.98 (m, 2H), 5.80 (s, 2H), 5.53 (t, J = 1.5 Hz, 1H), 4.43 (t, J = 8.0 Hz, 1H), 3.59 (s, 3H), 3.32 (s, 3H), 3.19 (s, 4H), 2.94 (dt, J = 12.1, 4.4 Hz, 1H), 2.25 (s, 2H), 1.98 (dt, J = 16.0, 8.3 Hz, 3H). | 495.3 |
| N-(4-(4-amino-5-(1-cyclopropyl-6-oxo-1,6-dihydropyridin-3-yl)-7-methyl-7H-pyrrolo[2,3-d]pyrimidin-6-yl)phenyl)methacrylamide | 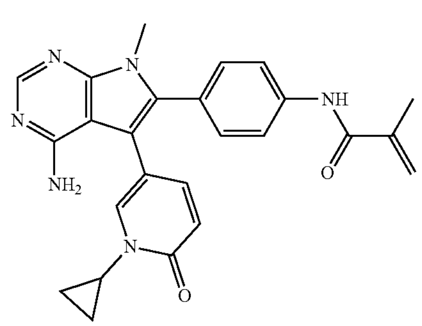 [SMILES: C=C(C)C(=O)Nc1ccc(-c2c(-c3ccc(=O)n(C4CC4)c3)c3c(N)ncnc3n2C)cc1] | $^1$H NMR (400 MHz, Chloroform-d) δ 8.40 (s, 1H), 7.67 (dd, J = 9.7, 3.0 Hz, 3H), 7.30 (d, J = 2.6 Hz, 1H), 7.27 (dd, J = 8.5, 2.0 Hz, 2H), 7.14 (d, J = 2.6 Hz, 1H), 6.56 (d, J = 9.3 Hz, 1H), 5.86 (s, 1H), 5.55 (q, J = 1.5 Hz, 1H), 5.07 (s, 2H), 3.72 (s, 3H), 3.33 (tt, J = 7.6, 4.2 Hz, 1H), 2.11 (d, J = 1.3 Hz, 3H), 1.12-1.02 (m, 2H), 0.70-0.61 (m, 2H). | 441.15 |

TABLE 2-continued

Additional Exemplary Compounds

| Compound | Structure | Proton NMR | MS [M + 1] |
|---|---|---|---|
| N-(4-(4-amino-7-methyl-5-(2-methyl-2H-indazol-6-yl)-7H-pyrrolo[2,3-d]pyrimidin-6-yl)phenyl)methacrylamide | 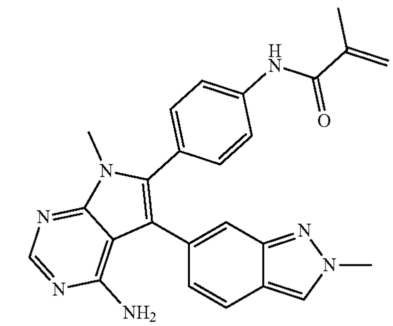 [SMILES: C=C(C)C(=O)Nc1ccc(-c2c(-c3ccc4cn(C)nc4c3)c3c(N)ncnc3n2C)cc1] | $^1$H NMR (400 MHz, DMSO-d$_6$) δ 9.86 (s, 1H), 8.33 (s, 1H), 8.20 (s, 1H), 7.71-7.62 (m, 3H), 7.42 (q, J = 1.2 Hz, 1H), 7.33-7.25 (m, 2H), 6.88 (dd, J = 8.5, 1.4 Hz, 1H), 5.78 (t, J = 1.1 Hz, 1H), 5.54-5.49 (m, 1H), 4.15 (s, 3H), 3.63 (s, 3H), 1.93 (t, J = 1.2 Hz, 3H). | 438.15 |
| N-(4-(4-amino-5-(4-(cyclopentylsulfonyl)phenyl)-7-methyl-7H-pyrrolo[2,3-d]pyrimidin-6-yl)phenyl)methacrylamide | 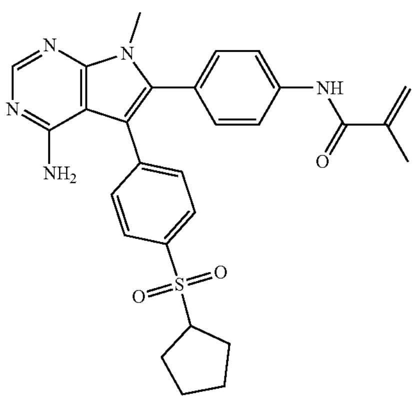 [SMILES: C=C(C)C(=O)Nc1ccc(-c2c(-c3ccc(S(=O)(=O)C4CCCC4)cc3)c3c(N)ncnc3n2C)cc1] | $^1$H NMR (400 MHz, DMSO-d$_6$) δ 9.91 (s, 1H), 8.23 (s, 1H), 7.84-7.77 (m, 2H), 7.75-7.68 (m, 2H), 7.47-7.40 (m, 2H), 7.27-7.21 (m, 2H), 6.01 (s, 0H), 5.80 (s, 1H), 5.54 (s, 1H), 3.82-3.70 (m, 1H), 3.62 (s, 3H), 1.95 (d, J = 1.5 Hz, 3H), 1.84 (d, J = 8.8 Hz, 4H), 1.57 (q, J = 6.7, 6.1 Hz, 4H). | 516.25 |
| N-(4-(4-amino-5-(6-(dimethylamino)pyridin-3-yl)-7-methyl-7H-pyrrolo[2,3-d]pyrimidin-6-yl)phenyl)methacrylamide | 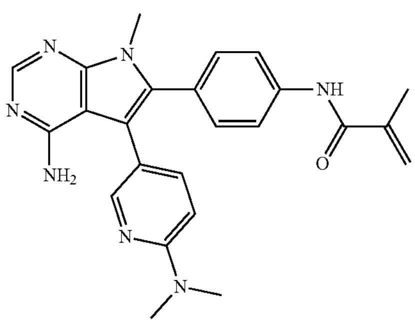 [SMILES: C=C(C)C(=O)Nc1ccc(-c2c(-c3ccc(N(C)C)nc3)c3c(N)ncnc3n2C)cc1] | $^1$H NMR (400 MHz, DMSO-d$_6$) δ 9.90 (s, 1H), 8.18 (s, 1H), 7.92 (d, J = 2.4 Hz, 1H), 7.71 (d, J = 8.6 Hz, 2H), 7.37 (dd, J = 8.7, 2.5 Hz, 1H), 7.29 (d, J = 8.6 Hz, 2H), 6.63 (d, J = 8.7 Hz, 1H), 5.80 (s, 1H), 5.72 (s, 1H), 5.54 (s, 1H), 3.59 (s, 3H), 3.01 (s, 6H), 1.95 (s, 3H). | 428.35 |
| N-(4-(4-amino-5-(3-fluoro-4-((4-methyl-1H-pyrazol-1-yl)methyl)phenyl)-7-methyl-7H-pyrrolo[2,3-d]pyrimidin-6-yl)phenyl)methacrylamide | 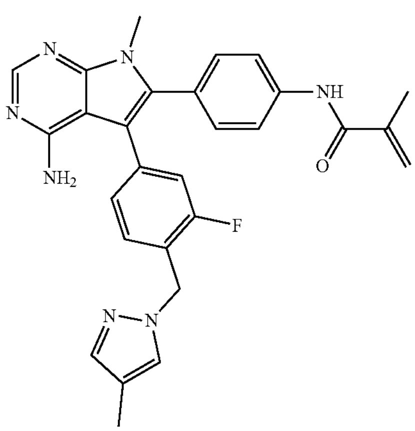 [SMILES: C=C(C)C(=O)Nc1ccc(-c2c(-c3ccc(Cn4cc(C)cn4)c(F)c3)c3c(N)ncnc3n2C)cc1] | $^1$H NMR (400 MHz, DMSO-d$_6$) δ 9.90 (s, 1H), 8.20 (s, 1H), 7.71 (d, J = 8.4 Hz, 2H), 7.56 (s, 1H), 7.30-7.24 (m, 3H), 7.02 (d, J = 11.5 Hz, 3H), 5.92 (s, 2H), 5.81 (s, 1H), 5.54 (s, 1H), 5.29 (s, 2H), 3.58 (s, 3H), 2.01 (s, 3H), 1.96 (s, 3H). | 496.35 |

TABLE 2-continued

Additional Exemplary Compounds

| Compound | Structure | Proton NMR | MS [M + 1] |
|---|---|---|---|
| N-(4-(4-amino-7-methyl-5-(2-methyl-1-oxoisoindolin-5-yl)-7H-pyrrolo[2,3-d]pyrimidin-6-yl)phenyl) methacrylamide | 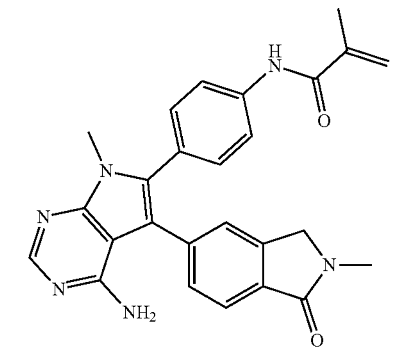 [SMILES: C=C(C)C(=O)Nc1ccc(-c2c(-c3ccc4c(c3)CN(C)C4=O)c3c(N)ncnc3n2C)cc1] | $^1$H NMR (400 MHz, DMSO-d$_6$) δ 9.88 (s, 1H), 8.21 (s, 1H), 7.72-7.65 (m, 2H), 7.55 (d, J = 7.9 Hz, 1H), 7.42 (d, J = 7.1 Hz, 2H), 7.26 (d, J = 8.5 Hz, 2H), 5.79-5.76 (s, 2H), 5.53 (d, J = 1.9 Hz, 1H), 4.45 (s, 2H), 3.62 (s, 3H), 3.06 (s, 3H), 1.94 (s, 3H). | 453.20 |
| N-(4-(4-amino-5-(4-((4,4-difluoropiperidin-1-yl)methyl)-3-fluorophenyl)-7-methyl-7H-pyrrolo[2,3-d]pyrimidin-6-yl)phenyl) methacrylamide | 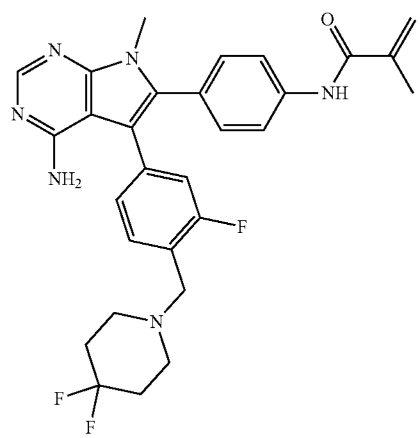 [SMILES: C=C(C)C(=O)Nc1ccc(-c2c(-c3ccc(CN4CCC(F)(F)CC4)c(F)c3)c3c(N)ncnc3n2C)cc1] | $^1$H NMR (400 MHz, Methanol-d$_4$) δ 8.22 (d, J = 1.9 Hz, 1H), 7.68 (dd, J = 8.7, 2.0 Hz, 2H), 7.43 (t, J = 7.8 Hz, 1H), 7.29 (dd, J = 8.7, 2.0 Hz, 2H), 7.13 (d, J = 7.7 Hz, 1H), 7.01 (d, J = 10.8 Hz, 1H), 5.82 (s, 1H), 5.55 (s, 1H), 3.72-3.65 (m, 5H), 3.33 (d, J = 9.1 Hz, 1H), 2.64 (d, J = 6.6 Hz, 4H), 2.07-1.95 (m, 7H). | 535.40 |
| N-(4-(4-amino-5-(2,2-dioxido-1,3-dihydrobenzo[c]thiophen-5-yl)-7-methyl-7H-pyrrolo[2,3-d]pyrimidin-6-yl)phenyl) methacrylamide | 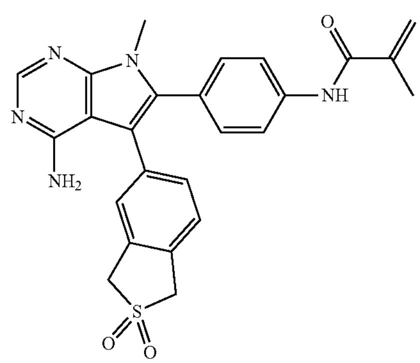 [SMILES: C=C(C)C(=O)Nc1ccc(-c2c(-c3ccc4c(c3)CS(=O)(=O)C4)c3c(N)ncnc3n2C)cc1] | $^1$H NMR (400 MHz, DMSO-d$_6$) δ 9.89 (s, 1H), 8.20 (s, 1H), 7.71 (d, J = 8.6 Hz, 2H), 7.36-7.25 (m, 4H), 7.19 (dd, J = 7.8, 1.8 Hz, 1H), 5.80 (s, 1H), 5.54 (d, J = 2.0 Hz, 1H), 4.48 (d, J = 4.6 Hz, 4H), 3.60 (s, 3H), 1.95 (s, 3H). | 474.15 |
| N-(4-(4-amino-5-(4-((3-hydroxypyrrolidin-1-yl)methyl)phenyl)-7-methyl-7H-pyrrolo[2,3-d]pyrimidin-6-yl)phenyl) methacrylamide | 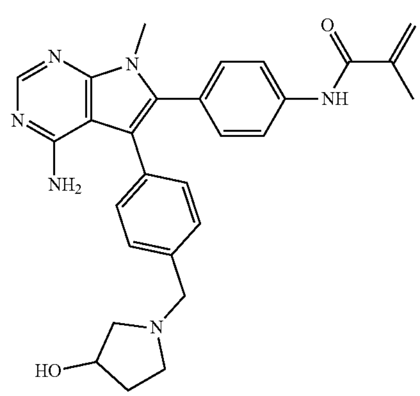 [SMILES: C=C(C)C(=O)Nc1ccc(-c2c(-c3ccc(CN4CCC(O)C4)cc3)c3c(N)ncnc3n2C)cc1] | $^1$H NMR (400 MHz, DMSO-d$_6$) δ 9.88 (s, 1H), 8.19 (s, 1H), 7.69 (d, J = 8.3 Hz, 2H), 7.27 (dd, J = 8.2, 4.7 Hz, 4H), 7.19 (d, J = 7.7 Hz, 2H), 5.86 (s, 2H), 5.53 (s, 1H), 4.67 (d, J = 4.6 Hz, 1H), 4.19 (d, J = 7.1 Hz, 1H), 3.61 (s, 3H), 3.54 (d, J = 5.5 Hz, 2H), 2.67 (dd, J = 9.6, 6.2 Hz, 1H), 2.57 (t, J = 7.7 Hz, 1H), 2.40 (q, J = 7.5 Hz, 1H), 2.30 (dd, J = 9.8, 3.6 Hz, 1H), 2.06-1.95 (m, 4H), 1.65-1.41 (m, 1H). | 483.3 |

TABLE 2-continued

Additional Exemplary Compounds

| Compound | Structure | Proton NMR | MS [M + 1] |
|---|---|---|---|
| N-(4-(4-amino-7-methyl-5-(4-((4-methylpiperazin-1-yl)methyl)phenyl)-7H-pyrrolo[2,3-d]pyrimidin-6-yl)phenyl) methacrylamide | 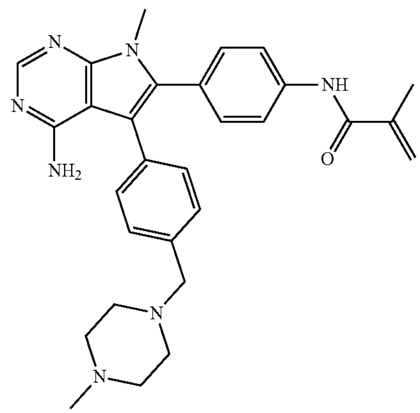 [SMILES: C=C(C)C(=O)Nc1ccc(-c2c(-c3ccc(CN4CCN(C)CC4)cc3)c3c(N)ncnc3n2C)cc1] | ¹H NMR (400 MHz, Methanol-d₄) δ 8.46 (s, 1H), 8.21 (s, 1H), 7.65 (d, J = 8.4 Hz, 2H), 7.36 (d, J = 7.9 Hz, 2H), 7.28 (t, J = 8.1 Hz, 4H), 5.81 (s, 1H), 5.55 (s, 1H), 3.68 (d, J = 18.2 Hz, 5H), 3.03 (s, 4H), 2.69 (s, 7H), 2.04 (s, 3H). | 496.35 |
| N-(4-(4-amino-5-(1-isopropyl-1H-indazol-5-yl)-7-methyl-7H-pyrrolo[2,3-d]pyrimidin-6-yl)phenyl) methacrylamide | 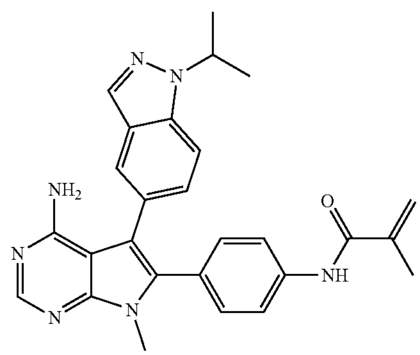 [SMILES: C=C(C)C(=O)Nc1ccc(-c2c(-c3ccc4c(cnn4C(C)C)c3)c3c(N)ncnc3n2C)cc1] | ¹H NMR (400 MHz, DMSO-d₆) δ 9.84 (s, 1H), 8.19 (s, 1H), 8.04 (s, 1H), 7.70-7.61 (m, 4H), 7.28 (d, J = 8.6 Hz, 2H), 7.21 (dd, J = 8.6, 1.6 Hz, 1H), 5.77 (s, 2H), 5.51 (s, 1H), 4.97 (p, J = 6.6 Hz, 1H), 3.62 (s, 3H), 1.93 (s, 3H), 1.49 (d, J = 6.6 Hz, 6H). | 466.30 |
| N-(4-(4-amino-7-methyl-5-(4-(2-oxopiperidin-1-yl)phenyl)-7H-pyrrolo[2,3-d]pyrimidin-6-yl)phenyl) methacrylamide | 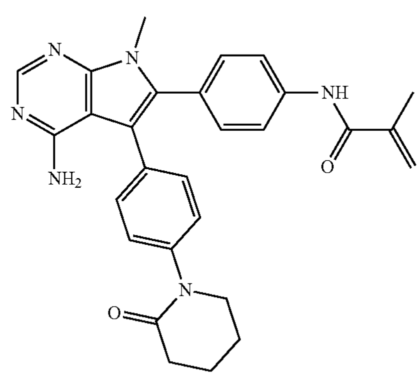 [SMILES: C=C(C)C(=O)Nc1ccc(-c2c(-c3ccc(N4CCCCC4=O)cc3)c3c(N)ncnc3n2C)cc1] | ¹H NMR (400 MHz, DMSO-d₆) δ 9.90 (s, 1H), 8.20 (s, 1H), 7.75-7.67 (m, 2H), 7.41-7.21 (m, 6H), 5.85 (m, 2H), 5.55 (d, J = 1.2 Hz, 1H), 3.65 (d, J = 8.1 Hz, 5H), 2.55-2.31 (t, J = 6.3 Hz, 2H), 1.95 (t, J = 1.2 Hz, 3H), 1.91-1.77 (m, 4H). | 481.3 |
| N-(4-(4-amino-7-methyl-5-(1-(1-methylazetidin-3-yl)-1H-pyrazol-4-yl)-7H-pyrrolo[2,3-d]pyrimidin-6-yl)phenyl) methacrylamide | 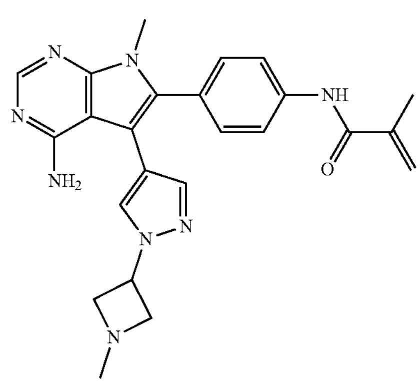 [SMILES: C=C(C)C(=O)Nc1ccc(-c2c(-c3cnn(C4CN(C)C4)c3)c3c(N)ncnc3n2C)cc1] | ¹H NMR (400 MHz, Chloroform-d) δ 8.38 (s, 1H), 7.63 (d, J = 8.3 Hz, 2H), 7.56 (s, 1H), 7.50 (s, 1H), 7.38 (s, 1H), 7.29 (s, 1H), 5.84 (s, 1H), 5.53 (d, J = 1.8 Hz, 1H), 5.08 (s, 2H), 4.87 (p, J = 6.9 Hz, 1H), 3.86-3.75 (m, 2H), 3.70 (s, 3H), 3.54-3.45 (m, 2H), 2.45 (s, 3H), 2.11 (s, 3H). | 443.20 |

TABLE 2-continued

Additional Exemplary Compounds

| Compound | Structure | Proton NMR | MS [M + 1] |
|---|---|---|---|
| N-(4-(4-amino-7-methyl-5-(6-(2-oxopyrrolidin-1-yl)pyridin-3-yl)-7H-pyrrolo[2,3-d]pyrimidin-6-yl)phenyl)methacrylamide | 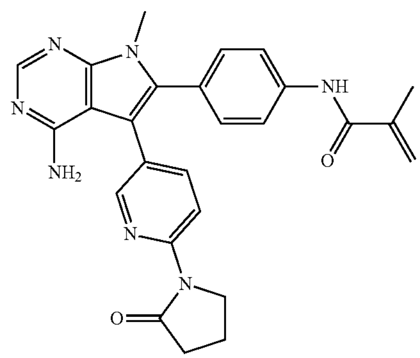 [SMILES: C=C(C)C(=O)Nc1ccc(-c2c(-c3ccc(N4CCCC4=O)nc3)c3c(N)ncnc3n2C)cc1] | ¹H NMR (400 MHz, DMSO-d₆) δ 9.90 (s, 1H), 8.28 (d, J = 8.6 Hz, 1H), 8.23-8.14 (m, 2H), 7.75-7.63 (m, 3H), 7.28 (d, J = 8.3 Hz, 2H), 5.95 (s, 2H), 5.80 (s, 1H), 5.54 (s, 1H), 3.97 (t, J = 7.1 Hz, 2H), 3.61 (s, 3H), 2.57 (t, J = 8.0 Hz, 2H), 2.04 (q, J = 7.5 Hz, 2H), 1.95 (s, 3H). | 468.35 |
| N-(4-(4-amino-5-(5-fluoro-2-methoxypyridin-4-yl)-7-methyl-7H-pyrrolo[2,3-d]pyrimidin-6-yl)phenyl)methacrylamide | 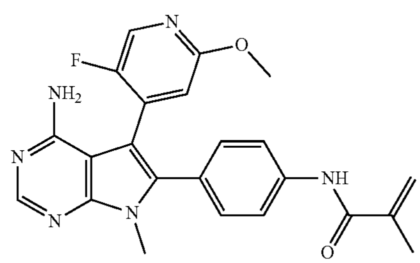 [SMILES: C=C(C)C(=O)Nc1ccc(-c2c(-c3cc(OC)ncc3F)c3c(N)ncnc3n2C)cc1] | ¹H NMR (400 MHz, DMSO-d₆) δ 9.92 (s, 1H), 8.21 (s, 1H), 8.04 (d, J = 1.4 Hz, 1H), 7.75-7.69 (m, 2H), 7.30-7.23 (m, 2H), 6.70 (d, J = 5.0 Hz, 1H), 6.16 (s, 2H), 5.81 (s, 1H), 5.54 (s, 1H), 3.82 (s, 3H), 3.62 (s, 3H), 1.95 (s, 3H). | 433.20 |
| N-(4-(4-amino-7-methyl-5-(4-(2-oxoimidazolidin-1-yl)phenyl)-7H-pyrrolo[2,3-d]pyrimidin-6-yl)phenyl)methacrylamide | 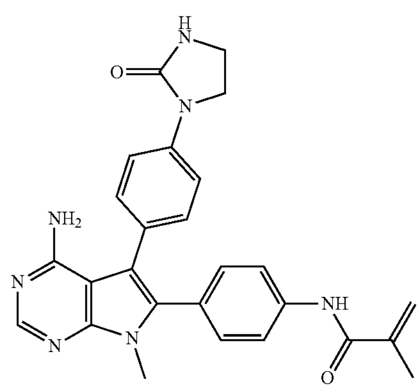 [SMILES: C=C(C)C(=O)Nc1ccc(-c2c(-c3ccc(N4CCNC4=O)cc3)c3c(N)ncnc3n2C)cc1] | ¹H NMR (400 MHz, DMSO-d₆) δ 9.88 (s, 1H), 8.18 (s, 1H), 7.69 (d, J = 8.6 Hz, 2H), 7.55 (d, J = 8.6 Hz, 2H), 7.31-7.24 (m, 2H), 7.18 (d, J = 8.6 Hz, 2H), 6.96 (s, 1H), 5.94 (s, 2H), 5.79 (s, 1H), 5.55-5.50 (m, 1H), 3.84 (dd, J = 9.2, 6.6 Hz, 2H), 3.40 (t, J = 7.9 Hz, 3H), 3.32 (s, 2H), 1.95 (s, 3H). | 468.30 |
| N-(4-(4-amino-5-(2,5-dimethoxypyridin-4-yl)-7-methyl-7H-pyrrolo[2,3-d]pyrimidin-6-yl)phenyl)methacrylamide | 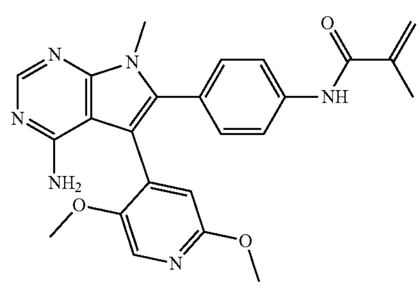 [SMILES: C=C(C)C(=O)Nc1ccc(-c2c(-c3cc(OC)ncc3OC)c3c(N)ncnc3n2C)cc1] | ¹H NMR (400 MHz, DMSO-d₆) δ 9.89 (s, 1H), 8.18 (s, 1H), 7.87 (s, 1H), 7.70 (d, J = 8.4 Hz, 2H), 7.23 (d, J = 8.4 Hz, 2H), 6.51 (s, 1H), 5.88 (s, 2H), 5.80 (s, 1H), 5.53 (s, 1H), 3.76 (s, 3H), 3.60 (d, J = 2.3 Hz, 6H), 1.95 (s, 3H). | 445.25 |

TABLE 2-continued

Additional Exemplary Compounds

| Compound | Structure | Proton NMR | MS [M + 1] |
|---|---|---|---|
| N-(4-(4-amino-5-(imidazo[1,2-a]pyridin-7-yl)-7-methyl-7H-pyrrolo[2,3-d]pyrimidin-6-yl)phenyl)methacrylamide | 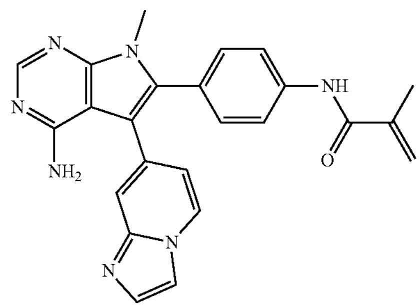 [SMILES: C=C(C)C(=O)Nc1ccc(-c2c(-c3ccn4ccnc4c3)c3c(N)ncnc3n2C)cc1] | $^1$H NMR (400 MHz, DMSO-d$_6$) δ 9.90 (s, 1H), 8.44 (d, J = 1.0 Hz, 1H), 8.21 (s, 1H), 7.89 (s, 1H), 7.72 (d, J = 8.5 Hz, 2H), 7.56-7.51 (m, 1H), 7.36-7.28 (m, 3H), 6.63 (dd, J = 7.0, 1.7 Hz, 1H), 6.15 (s, 2H), 5.78 (d, J = 11.5 Hz, 1H), 5.53 (s, 1H), 3.61 (s, 3H), 1.94 (s, 3H). | 424.25 |
| N-(4-(4-amino-7-methyl-5-(6-(1-methylpiperidin-4-yloxy)pyridin-3-yl)-7H-pyrrolo[2,3-d]pyrimidin-6-yl)phenyl)methacrylamide | 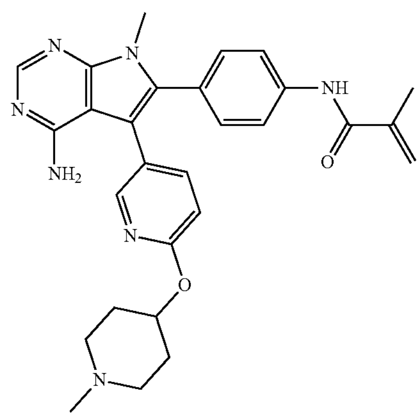 [SMILES: C=C(C)C(=O)Nc1ccc(-c2c(-c3ccc(OC4CCN(C)CC4)nc3)c3c(N)ncnc3n2C)cc1] | $^1$H NMR (400 MHz, DMSO-d$_6$) δ 9.90 (s, 1H), 8.20 (s, 1H), 7.97 (d, J = 2.5 Hz, 1H), 7.75-7.70 (m, 2H), 7.52 (dd, J = 8.5, 2.5 Hz, 1H), 7.32-7.24 (m, 2H), 6.75 (d, J = 8.5 Hz, 1H), 5.92 (s, 2H), 5.81 (s, 1H), 5.54 (s, 1H), 4.95 (tt, J = 8.8, 4.1 Hz, 1H), 3.60 (s, 3H), 2.66 (dd, J = 12.9, 5.5 Hz, 2H), 2.19-2.08 (m, 5H), 1.99-1.93 (m, 5H), 1.69 (ddt, J = 14.5, 9.2, 4.8 Hz, 2H). | 498.25 |
| N-(4-(4-amino-5-(8-azabicyclo[3.2.1]oct-2-en-3-yl)-7-methyl-7H-pyrrolo[2,3-d]pyrimidin-6-yl)phenyl)methacrylamide | 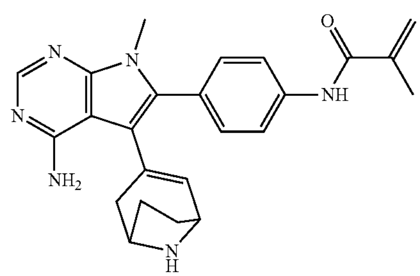 [SMILES: C=C(C)C(=O)Nc1ccc(-c2c(C3=CC4CCC(C3)N4)c3c(N)ncnc3n2C)cc1] | $^1$H NMR (400 MHz, Methanol-d$_4$) δ 8.37 (s, 1H), 7.90 (d, J = 8.4 Hz, 2H), 7.50 (d, J = 8.4 Hz, 2H), 6.21 (d, J = 5.6 Hz, 1H), 5.87 (s, 1H), 5.60 (s, 1H), 4.37 (t, J = 5.5 Hz, 1H), 4.10 (s, 1H), 3.75 (s, 3H), 2.93-2.84 (m, 1H), 2.31-2.12 (m, 4H), 2.07 (s, 3H), 1.99-1.90 (m, 1H), 1.57 (s, 1H), 1.30 (d, J = 13.5 Hz, 1H). | 415.30 |
| N-(4-(4-amino-5-(4-(6-methylpyridin-2-yloxy)phenyl)-7H-pyrrolo[2,3-d]pyrimidin-6-yl)phenyl)-N-methylacrylamide | 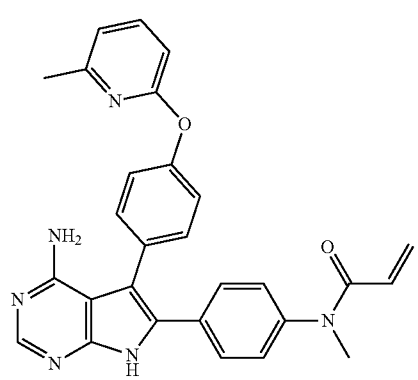 [SMILES: C=CC(=O)N(C)c1ccc(-c2[nH]c3ncnc(N)c3c2-c2ccc(Oc3cccc(C)n3)cc2)cc1] | $^1$H NMR (400 MHz, DMSO-d$_6$) δ 12.17 (s, 1H), 8.14 (s, 1H), 7.74-7.78 (m, 1H), 7.41-7.47 (m, 4H), 7.21-7.24 (m, 4H), 6.84-6.86 (d, J = 8 Hz, 1H), 5.17-6.18 (m, 5H), 3.23 (s, 3H), 2.36 (s, 3H). | 477.35 |

TABLE 2-continued

Additional Exemplary Compounds

| Compound | Structure | Proton NMR | MS [M + 1] |
|---|---|---|---|
| N-(4-(4-amino-5-(4-(pyrrolidine-1-carbonyl)phenyl)-7H-pyrrolo[2,3-d]pyrimidin-6-yl)phenyl)methacrylamide | 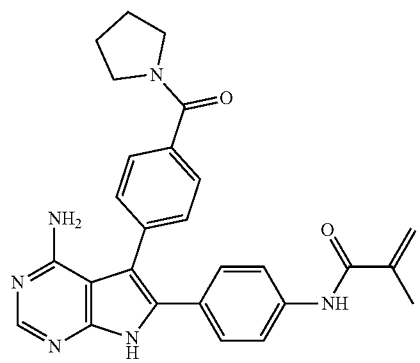 [SMILES: C=C(C)C(=O)Nc1ccc(-c2[nH]c3ncnc(N)c3c2-c2ccc(C(=O)N3CCCC3)cc2)cc1] | $^1$H NMR (400 MHz, DMSO-d6) δ 12.12 (s, 1H), 9.82 (s, 1H), 8.13 (s, 1H), 7.59 (d, J = 8.3 Hz, 4H), 7.39 (d, J = 8.1 Hz, 2H), 7.25 (d, J = 8.6 Hz, 2H), 5.79 (s, 1H), 5.52 (s, 1H), 3.48 (dt, J = 11.2, 6.4 Hz, 4H), 1.96-1.81 (m, 7H). | 467.30 |
| N-(4-(4-amino-7-methyl-5-(4-(pyrrolidine-1-carbonyl)phenyl)-7H-pyrrolo[2,3-d]pyrimidin-6-yl)phenyl)acrylamide | 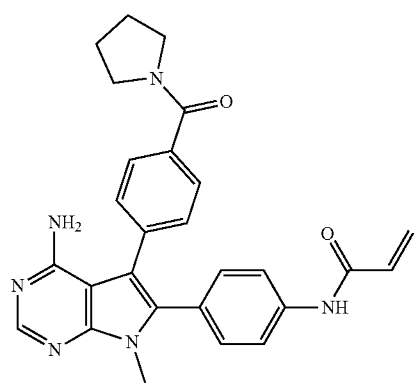 [SMILES: C=CC(=O)Nc1ccc(-c2c(-c3ccc(C(=O)N4CCCC4)cc3)c3c(N)ncnc3n2C)cc1] | $^1$H NMR (400 MHz, DMSO-d$_6$) δ 10.26 (s, 1H), 8.21 (s, 1H), 7.72-7.65 (m, 2H), 7.55-7.46 (m, 2H), 7.28 (dd, J = 8.6, 6.8 Hz, 4H), 6.44 (dd, J = 17.0, 10.2 Hz, 1H), 6.27 (dd, J = 17.0, 2.2 Hz, 1H), 5.78 (dd, J = 10.2, 2.2 Hz, 2H), 3.62 (s, 3H), 3.44 (dt, J = 17.8, 6.6 Hz, 4H), 1.84 (ddd, J = 17.8, 12.8, 6.8 Hz, 4H). | 467.20 |
| N-(4-(4-amino-7-methyl-5-(4-(pyrrolidine-1-carbonyl)phenyl)-7H-pyrrolo[2,3-d]pyrimidin-6-yl)phenyl)but-2-ynamide | 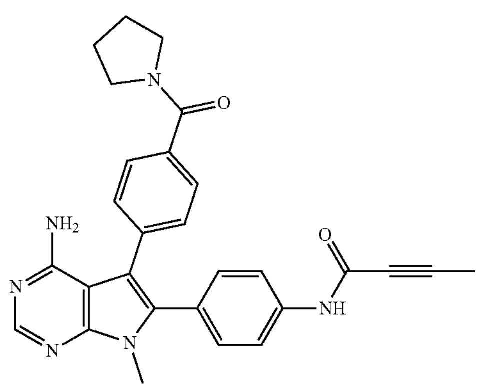 [SMILES: CC#CC(=O)Nc1ccc(-c2c(-c3ccc(C(=O)N4CCCC4)cc3)c3c(N)ncnc3n2C)cc1] | $^1$H NMR (400 MHz, DMSO-d$_6$) δ 10.72 (s, 1H), 8.21 (s, 2H), 7.59-7.61 (d, J = 8 Hz, 2H), 7.47-7.49 (d, J = 8 Hz, 2H), 7.26 (m, 4H), 5.91 (s, 1H), 3.59 (s, 3H), 3.16-3.45 (m, 4H), 2.05 (s, 3H), 1.82-1.86 (m, 4H). | 479.35 |
| N-(4-(4-amino-5-(3-ethoxy-4-((6-methylpyridin-2-yl)oxy)phenyl)-7H-pyrrolo[2,3-d]pyrimidin-6-yl)phenyl)methacrylamide | 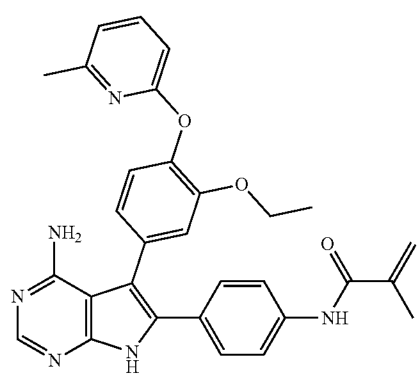 [SMILES: C=C(C)C(=O)Nc1ccc(-c2[nH]c3ncnc(N)c3c2-c2ccc(Oc3cccc(C)n3)c(OCC)c2)cc1] | $^1$H NMR (400 MHz, DMSO-d6) δ 12.05 (s, 1H), 9.83 (s, 1H), 8.13 (s, 1H), 7.70 (m, 1H), 7.66-7.60 (m, 2H), 7.39-7.30 (m, 2H), 7.18 (d, J = 8.0 Hz, 1H), 7.09 (d, J = 2.0 Hz, 1H), 7.01-6.90 (m, 2H), 6.74 (d, J = 8.4 Hz, 1H), 5.79 (s, 2H), 5.53 (s, 1H), 3.93-3.88 (m, 2H), 2.34 (s, 3H), 1.95 (s, 3H), 1.23-1.13 (m, 3H). | 521.25 |

TABLE 2-continued

Additional Exemplary Compounds

| Compound | Structure | Proton NMR | MS [M + 1] |
|---|---|---|---|
| N-(4-(4-amino-5-(3-methoxy-4-((6-methylpyridin-2-yl)oxy)phenyl)-7H-pyrrolo[2,3-d]pyrimidin-6-yl)phenyl)but-2-ynamide | 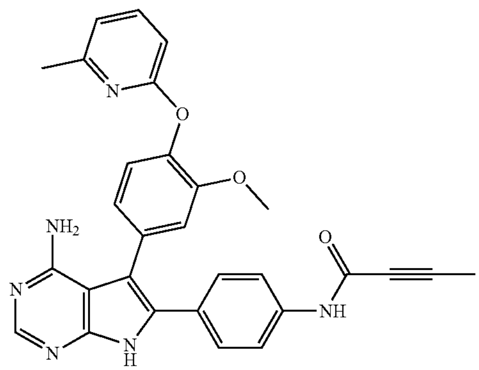 [SMILES: CC#CC(=O)Nc1ccc(-c2[nH]c3ncnc(N)c3c2-c2ccc(Oc3cccc(C)n3)c(OC)c2)cc1] | $^1$H NMR (400 MHz, DMSO-d6) δ 12.07 (s, 1H), 10.66 (s, 1H), 8.13 (s, 1H), 7.69 (t, J = 8.0 Hz, 1H), 7.53 (d, J = 8.8 Hz, 2H), 7.37-7.25 (m, 2H), 7.17 (d, J = 8.0 Hz, 1H), 7.10 (d, J = 2.0 Hz, 1H), 7.04-6.88 (m, 2H), 6.72 (d, J = 8.4 Hz, 1H), 5.84 (s, 2H), 3.62 (s, 3H), 2.34 (s, 3H), 2.05 (s, 3H). | 505.25 |
| N-(4-(4-amino-5-(4-((6-methylpyridin-2-yl)oxy)phenyl)-7H-pyrrolo[2,3-d]pyrimidin-6-yl)phenyl)acrylamide | 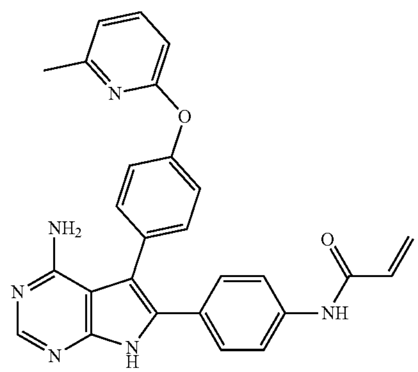 [SMILES: C=CC(=O)Nc1ccc(-c2[nH]c3ncnc(N)c3c2-c2ccc(Oc3cccc(C)n3)cc2)cc1] | $^1$H NMR (400 MHz, DMSO-d$_6$) δ 12.07 (s, 1H), 10.19 (s, 1H), 8.12 (s, 1H), 7.77 (t, J = 7.8 Hz, 1H), 7.60 (d, J = 8.6 Hz, 2H), 7.42-7.35 (m, 2H), 7.32 (d, J = 8.5 Hz, 2H), 7.23-7.16 (m, 2H), 7.04 (d, J = 7.3 Hz, 1H), 6.85 (d, J = 8.2 Hz, 1H), 6.43 (dd, J = 17.0, 10.1 Hz, 1H), 6.26 (dd, J = 17.0, 2.0 Hz, 1H), 5.76 (dd, J = 10.1, 2.0 Hz, 1H), 2.38 (s, 3H). | 463.4 |
| N-(4-(4-amino-5-(4-((6-methylpyridin-2-yl)oxy)phenyl)-7H-pyrrolo[2,3-d]pyrimidin-6-yl)phenyl)isobutyramide | 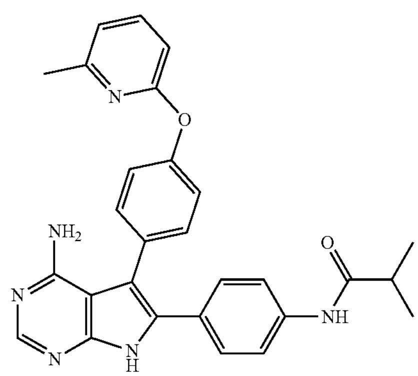 [SMILES: Cc1cccc(Oc2ccc(-c3c(-c4ccc(NC(=O)C(C)C)cc4)[nH]c4ncnc(N)c34)cc2)n1] | $^1$H NMR (400 MHz, DMSO-d$_6$) δ 12.05 (s, 1H), 9.87 (s, 1H), 8.12 (s, 1H), 7.76 (t, J = 7.8 Hz, 1H), 7.54 (d, J = 8.6 Hz, 2H), 7.40-7.33 (m, 2H), 7.31-7.25 (m, 2H), 7.22-7.15 (m, 2H), 7.04 (d, J = 7.4 Hz, 1H), 6.84 (d, J = 8.2 Hz, 1H), 5.74 (s, 2H), 2.59 (q, J = 6.7 Hz, 1H), 2.38 (s, 3H), 1.09 (d, J = 6.8 Hz, 6H). | 479.4 |
| N-(4-(4-amino-5-(4-(pyrrolidine-1-carbonyl)phenyl)-7H-pyrrolo[2,3-d]pyrimidin-6-yl)phenyl)acrylamide | 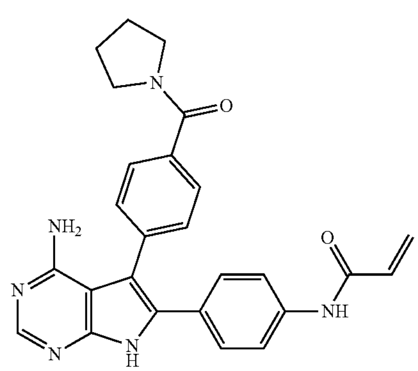 [SMILES: C=CC(=O)Nc1ccc(-c2[nH]c3ncnc(N)c3c2-c2ccc(C(=O)N3CCCC3)cc2)cc1] | $^1$H NMR (400 MHz, DMSO-d6) δ 10.26 (s, 1H), 8.20 (s, 1H), 7.88 (d, J = 8.6 Hz, 1H), 7.73-7.67 (m, 2H), 7.34-7.23 (m, 4H), 7.15-7.08 (m, 2H), 6.89 (d, J = 8.6 Hz, 1H), 6.44 (dd, J = 17.0, 10.1 Hz, 1H), 6.27 (dd, J = 16.9, 2.0 Hz, 1H), 5.96 (s, 2H), 5.78 (dd, J = 10.1, 2.1 Hz, 1H), 3.62 (s, 3H), 2.40 (s, 3H). | 453.30 |

TABLE 2-continued

Additional Exemplary Compounds

| Compound | Structure | Proton NMR | MS [M + 1] |
|---|---|---|---|
| N-(4-(4-amino-5-(4-((6-fluoropyridin-3-yl)oxy)-3-hydroxyphenyl)-7-methyl-7H-pyrrolo[2,3-d]pyrimidin-6-yl)phenyl)methacrylamide | 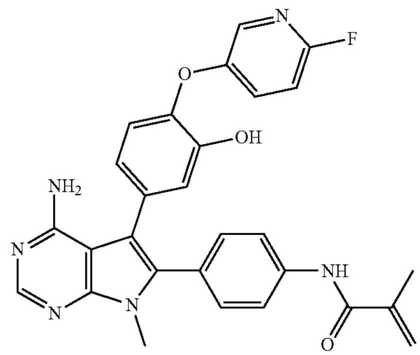 [SMILES: C=C(C)C(=O)Nc1ccc(-c2c(-c3ccc(Oc4ccc(F)nc4)c(O)c3)c3c(N)ncnc3n2C)cc1] | ¹H NMR (400 MHz, DMSO-d₆) δ 9.92 (s, 1H), 9.61 (s, 1H), 8.23-8.10 (m, 2H), 7.81-7.71 (m, 3H), 7.31 (d, J = 8.4 Hz, 2H), 7.09-6.96 (m, 2H), 6.81 (d, J = 2.2 Hz, 1H), 6.70 (dd, J = 8.0, 2.2 Hz, 1H), 5.81 (s, 1H), 3.60 (s, 3H), 1.96 (s, 3H). | 511.20 |
| N-(4-(4-amino-5-(3-methoxy-4-((1-methyl-1H-pyrazol-3-yl)oxy)phenyl)-7-methyl-7H-pyrrolo[2,3-d]pyrimidin-6-yl)phenyl)acrylamide | 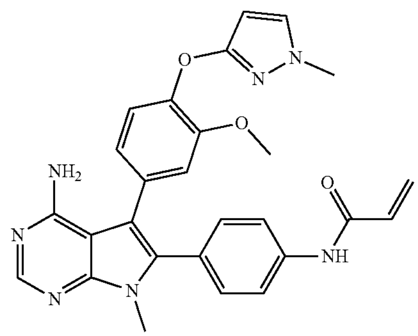 [SMILES: C=CC(=O)Nc1ccc(-c2c(-c3ccc(Oc4ccn(C)n4)c(OC)c3)c3c(N)ncnc3n2C)cc1] | ¹H NMR (400 MHz, DMSO-d6) δ 10.26 (s, 1H), 8.19 (d, J = 2.2 Hz, 1H), 7.78-7.60 (m, 3H), 7.55 (d, J = 2.3 Hz, 1H), 7.32 (d, J = 8.6 Hz, 2H), 7.01-6.95 (m, 1H), 6.92 (d, J = 2.0 Hz, 1H), 6.75 (m, J = 8.2, 2.2 Hz, 1H), 6.45 (m, J = 17.0, 10.1 Hz, 1H), 6.21-6.12 (m, 1H), 5.78 (dd, J = 10.1, 2.0 Hz, 1H), 5.69 (d, J = 2.3 Hz, 1H), 3.71 (s, 3H), 3.62 (d, J = 9.0 Hz, 6H). | 496.20 |
| N-(4-(4-amino-5-(3-methoxy-4-(pyrrolidine-1-carbonyl)phenyl)-7-methyl-7H-pyrrolo[2,3-d]pyrimidin-6-yl)phenyl)methacrylamide | 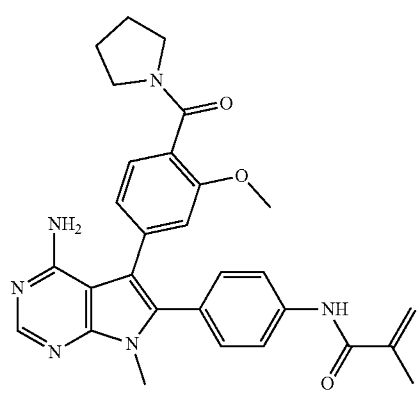 [SMILES: C=C(C)C(=O)Nc1ccc(-c2c(-c3ccc(C(=O)N4CCCC4)c(OC)c3)c3c(N)ncnc3n2C)cc1] | ¹H NMR (400 MHz, DMSO-d6) δ 9.89 (s, 1H), 8.22 (s, 1H), 7.72 (d, J = 8.4 Hz, 2H), 7.30 (d, J = 8.4 Hz, 2H), 7.14 (d, J = 7.6 Hz, 1H), 6.90 (s, 1H), 6.83 (d, J = 7.6 Hz, 1H), 6.11 (s, 1H), 5.82 (s, 1H), 5.54 (s, 1H), 3.63 (d, J = 12.4 Hz, 6H), 3.43 (t, J = 6.8 Hz, 2H), 3.16-3.13 (m, 2H), 1.96 (s, 3H), 1.87-1.77 (m, 4H). | 511.35 |
| N-(4-(4-amino-5-(3-methoxy-4-(pyrrolidine-1-carbonyl)phenyl)-7-methyl-7H-pyrrolo[2,3-d]pyrimidin-6-yl)phenyl)acrylamide | 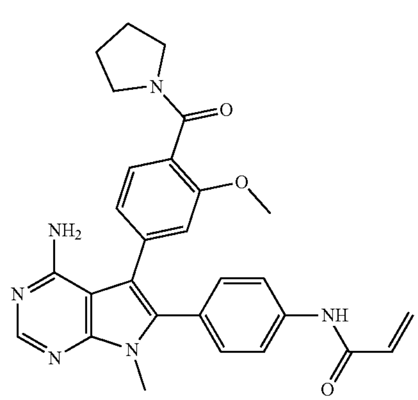 [SMILES: C=CC(=O)Nc1ccc(-c2c(-c3ccc(C(=O)N4CCCC4)c(OC)c3)c3c(N)ncnc3n2C)cc1] | ¹H NMR (400 MHz, DMSO-d₆) δ 10.27 (s, 1H), 8.21 (s, 1H), 7.70 (d, J = 8.4 Hz, 2H), 7.31 (d, J = 8.5 Hz, 2H), 7.14 (d, J = 7.6 Hz, 1H), 6.88 (d, J = 1.5 Hz, 1H), 6.82 (dd, J = 7.7, 1.4 Hz, 1H), 6.44 (dd, J = 17.0, 10.1 Hz, 1H), 6.27 (dd, J = 17.0, 2.1 Hz, 1H), 6.02 (s, 2H), 5.78 (dd, J = 10.0, 2.0 Hz, 1H), 3.62 (d, J = 6.3 Hz, 6H), 3.42 (t, J = 6.9 Hz, 2H), 3.13 (t, J = 6.5 Hz, 2H), 1.82 (dq, J = 19.6, 7.0 Hz, 4H). | 497.3 |

TABLE 2-continued

Additional Exemplary Compounds

| Compound | Structure | Proton NMR | MS [M + 1] |
|---|---|---|---|
| N-(4-(4-amino-7-methyl-5-(3-(pyrrolidine-1-carbonyl)phenyl)-7H-pyrrolo[2,3-d]pyrimidin-6-yl)phenyl)methacrylamide | 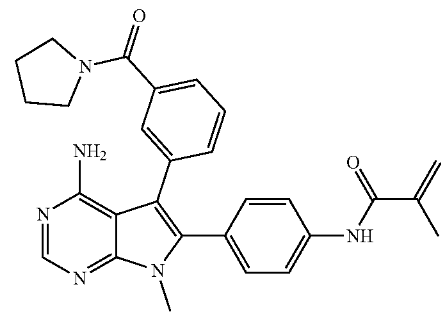 [SMILES: C=C(C)C(=O)Nc1ccc(-c2c(-c3cccc(C(=O)N4CCCC4)c3)c3c(N)ncnc3n2C)cc1] | ¹H NMR (400 MHz, DMSO-d6) δ 9.92 (s, 1H), 8.21 (s, 1H), 7.72 (d, J = 8.4 Hz, 2H), 7.53-7.35 (m, 3H), 7.25 (d, J = 8.4 Hz, 2H), 7.17 (d, J = 2.0 Hz, 1H), 5.78 (s, 1H), 5.54 (s, 1H), 3.61 (s, 3H), 3.37 (t, J = 7.0 Hz, 2H), 2.84 (t, J = 6.6 Hz, 2H), 1.95 (s, 3H), 1.81-1.73 (m, 2H), 1.67-1.59 (m, 2H). | 481.35 |
| N-(4-(4-amino-7-methyl-5-(1-(pyrrolidine-1-carbonyl)piperidin-4-yl)-7H-pyrrolo[2,3-d]pyrimidin-6-yl)phenyl)methacrylamide | 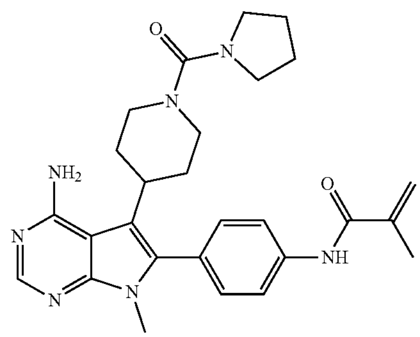 [SMILES: C=C(C)C(=O)Nc1ccc(-c2c(C3CCN(C(=O)N4CCCC4)CC3)c3c(N)ncnc3n2C)cc1] | ¹H NMR (400 MHz, DMSO-d6) δ 9.98 (s, 1H), 8.11 (s, 1H), 7.83 (d, J = 8.4 Hz, 2H), 7.35 (d, J = 8.3 Hz, 2H), 6.38 (s, 2H), 5.83 (s, 1H), 5.56 (s, 1H), 3.60 (d, J = 12.7 Hz, 2H), 3.36 (s, 3H), 3.18 (d, J = 6.3 Hz, 4H), 3.05 (s, 1H), 2.73 (t, J = 12.3 Hz, 2H), 1.98 (s, 3H), 1.72 (d, J = 4.9 Hz, 4H), 1.68-1.49 (m, 4H). | 488.25. |
| N-(4-(4-amino-7-methyl-5-(4-(3-methylazetidine-1-carbonyl)phenyl)-7H-pyrrolo[2,3-d]pyrimidin-6-yl)phenyl)methacrylamide | 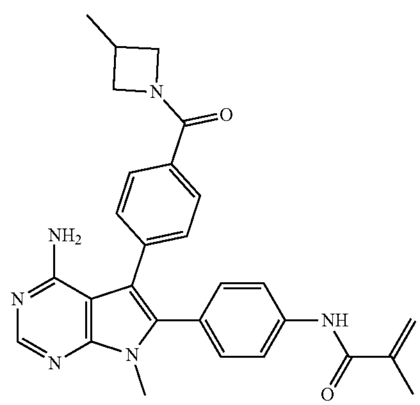 [SMILES: C=C(C)C(=O)Nc1ccc(-c2c(-c3ccc(C(=O)N4CC(C)C4)cc3)c3c(N)ncnc3n2C)cc1] | ¹H NMR (400 MHz, DMSO-d6) δ 9.89 (s, 1H), 8.21 (s, 1H), 7.74-7.67 (m, 2H), 7.63-7.57 (m, 2H), 7.27 (t, J = 8.4 Hz, 4H), 5.80 (s, 1H), 5.53 (t, J = 1.6 Hz, 1H), 4.42 (t, J = 8.3 Hz, 1H), 4.15 (t, J = 8.8 Hz, 1H), 3.88 (s, 1H), 3.61 (s, 3H), 3.32 (s, 1H), 2.75-2.66 (m, 1H), 1.95 (d, J = 1.2 Hz, 3H), 1.20 (d, J = 6.8 Hz, 3H). | 481.20 |
| N-(4-(4-amino-5-(4-(4,4-difluoropiperidine-1-carbonyl)phenyl)-7-methyl-7H-pyrrolo[2,3-d]pyrimidin-6-yl)phenyl)methacrylamide | 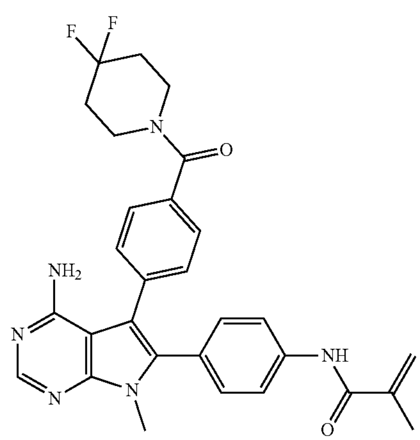 [SMILES: C=C(C)C(=O)Nc1ccc(-c2c(-c3ccc(C(=O)N4CCC(F)(F)CC4)cc3)c3c(N)ncnc3n2C)cc1] | ¹H NMR (400 MHz, DMSO-d₆) δ 9.90 (s, 1H), 8.21 (s, 1H), 7.81-7.64 (m, 2H), 7.41 (d, J = 8.1 Hz, 2H), 7.34-7.18 (m, 4H), 5.80 (s, 1H), 5.53 (s, 1H), 3.61 (s, 3H), 2.09-1.97 (m, 4H), 1.95 (d, J = 1.3 Hz, 3H). | 531.20 |

TABLE 2-continued

Additional Exemplary Compounds

| Compound | Structure | Proton NMR | MS [M + 1] |
|---|---|---|---|
| N-(4-(4-amino-5-(4-(3,3-difluoropyrrolidine-1-carbonyl)phenyl)-7-methyl-7H-pyrrolo[2,3-d]pyrimidin-6-yl)phenyl)methacrylamide | 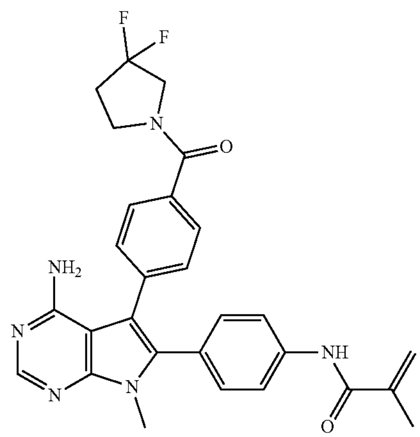 [SMILES: C=C(C)C(=O)Nc1ccc(-c2c(-c3ccc(C(=O)N4CCC(F)(F)C4)cc3)c3c(N)ncnc3n2C)cc1] | $^1$H NMR (400 MHz, DMSO-d$_6$) δ 9.89 (s, 1H), 8.21 (s, 1H), 7.74-7.67 (m, 2H), 7.51 (s, 2H), 7.30-7.23 (m, 2H), 5.98 (s, 2H), 5.80 (s, 1H), 5.53 (d, J = 1.8 Hz, 1H), 3.93 (s, 2H), 3.72 (t, J = 7.4 Hz, 2H), 3.61 (s, 3H), 2.50-2.32 (m, 2H), 1.95 (d, J = 1.2 Hz, 3H). | 517.35 |
| N-(4-(4-amino-7-methyl-5-(4-(octahydrocyclopenta[c]pyrrole-2-carbonyl)phenyl)-7H-pyrrolo[2,3-d]pyrimidin-6-yl)phenyl)methacrylamide | | $^1$H NMR (400 MHz, DMSO-d$_6$) δ 9.89 (s, 1H), 8.21 (s, 1H), 7.71 (d, J = 8.5 Hz, 2H), 7.45 (d, J = 7.9 Hz, 2H), 7.26 (dd, J = 8.4, 2.1 Hz, 4H), 5.93 (s, 1H), 5.80 (s, 1H), 5.53 (s, 1H), 3.69 (s, 1H), 3.61 (s, 4H), 3.22 (s, 2H), 2.62 (s, 2H), 1.95 (s, 3H), 1.84-1.60 (m, 3H), 1.60-1.20 (m, 3H). | 521.30 |
| N-(4-(4-amino-5-(4-(3-hydroxypyrrolidine-1-carbonyl)phenyl)-7-methyl-7H-pyrrolo[2,3-d]pyrimidin-6-yl)phenyl)methacrylamide | 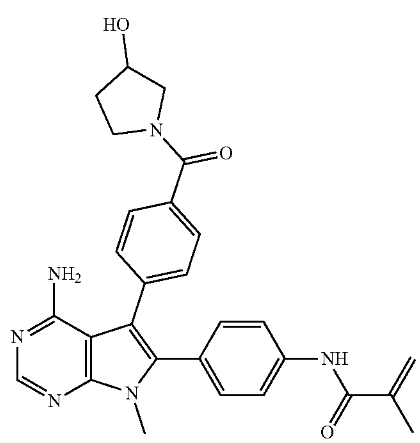 [SMILES: C=C(C)C(=O)Nc1ccc(-c2c(-c3ccc(C(=O)N4CCC(O)C4)cc3)c3c(N)ncnc3n2C)cc1] | $^1$H NMR (400 MHz, DMSO-d6) δ 9.89 (s, 1H), 8.21 (s, 1H), 7.71 (d, J = 8.4 Hz, 2H), 7.49 (dd, J = 8.3, 2.3 Hz, 2H), 7.27 (dd, J = 8.3, 1.8 Hz, 4H), 5.80 (s, 3H), 5.53 (t, J = 1.5 Hz, 1H), 4.96 (dd, J = 27.0, 3.5 Hz, 1H), 4.28 (d, J = 36.6 Hz, 1H), 3.66 (s, 3H), 3.32 (s, 3H), 3.24 (d, J = 11.0 Hz, 1H), 1.95 (t, J = 1.2 Hz, 5H). | 497.35 |

TABLE 2-continued

Additional Exemplary Compounds

| Compound | Structure | Proton NMR | MS [M + 1] |
|---|---|---|---|
| N-(4-(4-amino-7-methyl-5-(4-(piperidine-1-carbonyl)phenyl)-7H-pyrrolo[2,3-d]pyrimidin-6-yl)phenyl) methacrylamide | 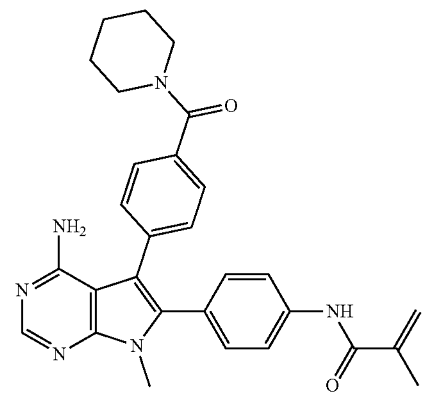 [SMILES: C=C(C)C(=O)Nc1ccc(-c2c(-c3ccc(C(=O)N4CCCCC4)cc3)c3c(N)ncnc3n2C)cc1] | $^1$H NMR (400 MHz, DMSO-d6) δ 9.89 (s, 1H), 8.21 (s, 1H), 7.74-7.68 (m, 2H), 7.34 (d, J = 8.2 Hz, 2H), 7.27 (dd, J = 8.3, 1.4 Hz, 4H), 5.95 (s, 2H), 5.80 (s, 1H), 5.54 (s, 1H), 3.68-3.36 (m, 7H), 1.96 (t, J = 1.2 Hz, 3H), 1.62 (d, J = 6.4 Hz, 2H), 1.51 (s, 4H). | 495.35 |
| N-(4-(4-amino-7-methyl-5-(1-(piperidin-4-ylmethyl)-1H-pyrazol-4-yl)-7H-pyrrolo[2,3-d]pyrimidin-6-yl)phenyl) methacrylamide | 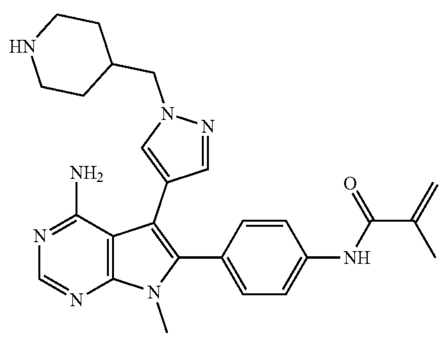 [SMILES: C=C(C)C(=O)Nc1ccc(-c2c(-c3cnn(CC4CCNCC4)c3)c3c(N)ncnc3n2C)cc1] | $^1$H NMR (400 MHz, Methanol-d$_4$) δ 8.37 (s, 1H), 7.77-7.70 (m, 2H), 7.59 (s, 1H), 7.54 (s, 1H), 7.40-7.33 (m, 2H), 5.84 (s, 1H), 5.58 (d, J = 1.8 Hz, 1H), 4.10 (d, J = 7.1 Hz, 2H), 3.79 (s, 3H), 3.46-3.37 (m, 2H), 2.96 (td, J = 12.9, 3.0 Hz, 2H), 2.16 (ddd, J = 11.4, 7.6, 3.9 Hz, 1H), 2.06 (s, 3H), 1.72-1.63 (m, 2H), 1.55-1.25 (m, 2H). | 471.35 |
| 4-(4-amino-6-(4-methacrylamido-phenyl)-7-methyl-7H-pyrrolo[2,3-d]pyrimidin-5-yl)-N-methylcyclohex-3-ene-1-carboxamide | 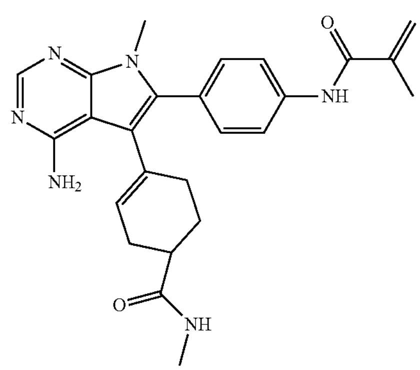 [SMILES: C=C(C)C(=O)Nc1ccc(-c2c(C3=CCC(C(=O)NC)CC3)c3c(N)ncnc3n2C)cc1] | $^1$H NMR (400 MHz, DMSO-d$_6$) δ 9.94 (s, 1H), 8.10 (s, 1H), 7.84-7.75 (m, 3H), 7.46-7.39 (m, 2H), 5.83 (s, 1H), 5.77 (s, 1H), 5.56 (d, J = 1.6 Hz, 1H), 3.57 (s, 3H), 2.57 (d, J = 4.5 Hz, 3H), 2.45 (q, J = 6.2 Hz, 1H), 2.29 (s, 1H), 2.24 (s, 1H), 1.98 (t, J = 1.2 Hz, 3H), 1.89 (s, 2H), 1.65 (d, J = 6.3 Hz, 2H). | 445.30 |
| N-(4-(4-amino-7-methyl-5-(3-methyl-4-(tetrahydrofuran-3-yloxy)phenyl)-7H-pyrrolo[2,3-d]pyrimidin-6-yl)phenyl) methacrylamide | 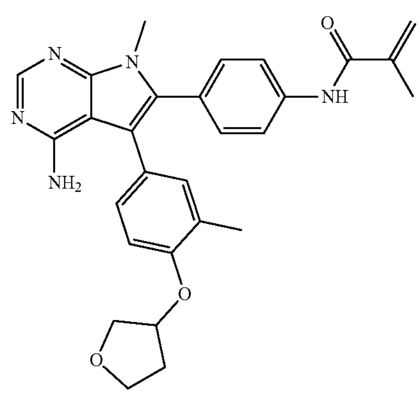 [SMILES: C=C(C)C(=O)Nc1ccc(-c2c(-c3ccc(OC4CCOC4)c(C)c3)c3c(N)ncnc3n2C)cc1] | $^1$H NMR (400 MHz, DMSO-d$_6$) δ 9.88 (s, 1H), 8.17 (s, 1H), 7.69 (d, J = 8.4 Hz, 2H), 7.28 (d, J = 8.3 Hz, 2H), 7.07 (s, 1H), 7.01 (d, J = 8.7 Hz, 1H), 6.88 (d, J = 8.4 Hz, 1H), 5.80 (s, 1H), 5.53 (s, 1H), 5.00 (d, J = 5.8 Hz, 1H), 3.94-3.72 (m, 4H), 3.59 (s, 3H), 2.20 (dq, J = 14.5, 7.7 Hz, 1H), 2.09 (s, 3H), 1.99 (d, J = 7.1 Hz, 1H), 1.95 (s, 3H), 1.16 (t, J = 13.1 Hz, 1H). | 484.35 |

TABLE 2-continued

Additional Exemplary Compounds

| Compound | Structure | Proton NMR | MS [M + 1] |
|---|---|---|---|
| N-(4-(4-amino-7-methyl-5-(1-methyl-1,2,3,4-tetrahydroquinolin-6-yl)-7H-pyrrolo[2,3-d]pyrimidin-6-yl)phenyl) methacrylamide | 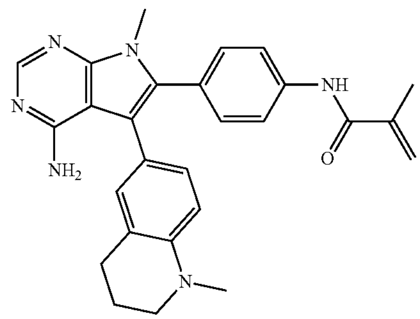 | $^1$H NMR (400 MHz, DMSO-d$_6$) δ 9.87 (s, 1H), 8.15 (s, 1H), 7.70 (d, J = 8.3 Hz, 2H), 7.29 (d, J = 8.3 Hz, 2H), 6.86 (dd, J = 8.3, 2.2 Hz, 1H), 6.81 (d, J = 2.2 Hz, 1H), 6.53 (d, J = 8.3 Hz, 1H), 5.80 (s, 1H), 5.53 (s, 1H), 3.58 (s, 3H) 3.20 (t, J = 5.6 Hz, 2H), 2.82 (s, 3H), 2.63 (t, J = 6.5 Hz, 2H), 1.95 (s, 3H), 1.87 (p, J = 6.2 Hz, 2H). | 453.40 |
| (E)-N-(4-(4-amino-7-methyl-5-(4-(pyrrolidine-1-carbonyl)phenyl)-7H-pyrrolo[2,3-d]pyrimidin-6-yl)phenyl)-4-(dimethylamino) but-2-enamide | 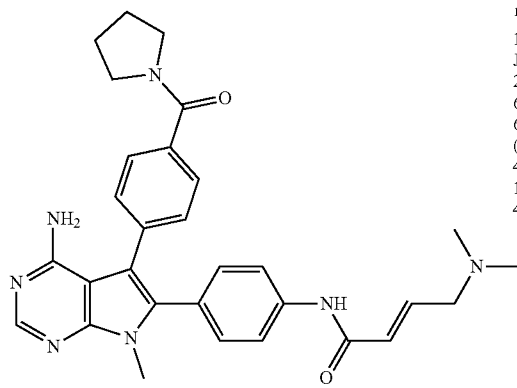 [SMILES: CN(C)C/C=C/C(=O)Nc1ccc(-c2c(-c3ccc(C(=O)N4CCCC4)cc3)c3c(N)ncnc3n2C)cc1] | $^1$H NMR (400 MHz, DMSO-d$_6$) δ 10.17 (s, 1H), 8.20 (s, 1H), 7.67 (d, J = 8.3 Hz, 2H), 7.49 (d, J = 7.9 Hz, 2H), 7.26 (dd, J = 8.3, 1.9 Hz, 4H), 6.74 (dt, J = 15.5, 5.8 Hz, 1H), 6.31-6.23 (m, 1H), 5.92 (s, 1H), 3.61 (s, 3H), 3.43 (dt, J = 17.9, 6.6 Hz, 4H), 3.28 (s, 1H), 3.09-3.03 (m, 1H), 2.18 (s, 6H), 1.89-1.78 (m, 4H). | 524.45 |
| N-(4-(4-amino-7-methyl-5-(4-(pyrrolidine-1-carbonyl)phenyl)-7H-pyrrolo[2,3-d]pyrimidin-6-yl)-2-methylphenyl) acrylamide | 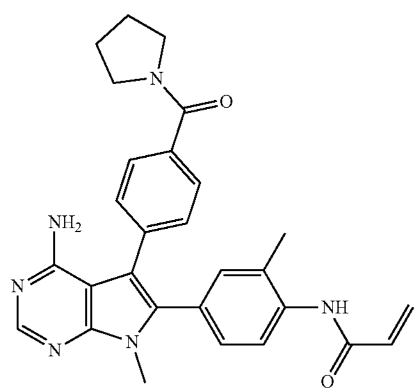 [SMILES: C=CC(=O)Nc1ccc(-c2c(-c3ccc(C(=O)N4CCCC4)cc3)c3c(N)ncnc3n2C)cc1C] | $^1$H NMR (400 MHz, DMSO-d$_6$) δ 9.47 (s, 1H), 8.21 (s, 1H), 7.60 (d, J = 8.2 Hz, 1H), 7.49 (d, J = 8.1 Hz, 2H), 7.28 (d, J = 8.1 Hz, 2H), 7.20 (d, J = 2.1 Hz, 1H), 7.13 (dd, J = 8.2, 2.1 Hz, 1H), 6.56 (dd, J = 16.9, 10.2 Hz, 1H), 6.26 (dd, J = 17.0, 2.0 Hz, 1H), 5.76 (dd, J = 10.1, 2.0 Hz, 2H), 3.43 (dt, J = 21.9, 6.5 Hz, 4H), 3.33 (s, 3H), 2.18 (s, 3H), 1.84 (dq, J = 18.5, 7.1 Hz, 4H). | 481.45 |
| N-(4-(4-amino-7-methyl-5-(4-(pyrrolidine-1-carbonyl)phenyl)-7H-pyrrolo[2,3-d]pyrimidin-6-yl)-2-fluorophenyl) acrylamide | 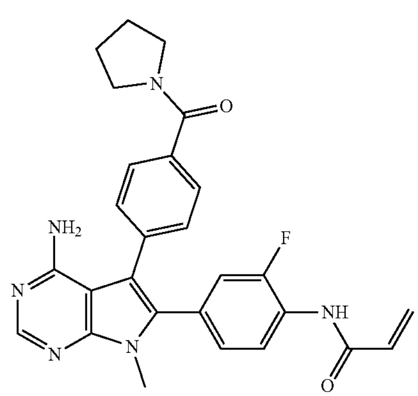 [SMILES: C=CC(=O)Nc1ccc(-c2c(-c3ccc(C(=O)N4CCCC4)cc3)c3c(N)ncnc3n2C)cc1F] | $^1$H NMR (400 MHz, DMSO-d$_6$) δ 10.04 (s, 1H), 8.22 (s, 1H), 8.08 (t, J = 8.3 Hz, 1H), 7.54-7.48 (m, 2H), 7.32-7.23 (m, 3H), 7.14 (dd, J = 8.3, 1.9 Hz, 1H), 6.64 (dd, J = 17.0, 10.2 Hz, 1H), 6.29 (dd, J = 17.0, 2.0 Hz, 1H), 5.79 (dd, J = 10.1, 2.0 Hz, 1H), 3.62 (s, 3H), 3.44 (dt, J = 19.1, 6.5 Hz, 4H), 1.85 (dp, J = 18.1, 6.7 Hz, 4H). | 485.1 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)-2,6-difluorophenyl)acrylamide | 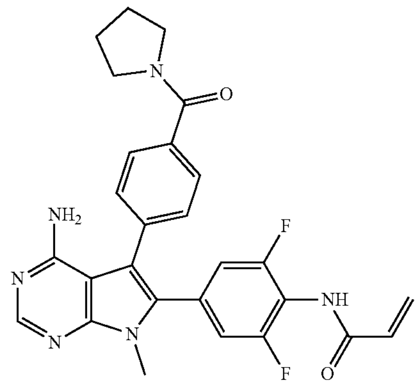 [SMILES: C=CC(=O)Nc1c(F)cc(-c2c(-c3ccc(C(=O)N4CCCC4)cc3)c3c(N)ncnc3n2C)cc1F] | ¹H NMR (400 MHz, DMSO-d₆) δ 9.99 (s, 1H), 8.23 (s, 1H), 7.53 (d, J = 7.9 Hz, 2H), 7.31 (d, J = 7.8 Hz, 2H), 7.18 (d, J = 8.4 Hz, 2H), 6.55-6.40 (m, 1H), 6.27 (dd, J = 17.2, 1.9 Hz, 1H), 5.82 (dd, J = 10.2, 1.9 Hz, 2H), 3.69 (s, 3H), 3.48 (q, J = 9.0, 6.9 Hz, 2H), 3.41 (t, J = 6.5 Hz, 2H), 1.90-1.79 (m, 4H). | 503.35 |
| N-(4-(4-amino-7-methyl-5-(4-(pyrrolidine-1-carbonyl)phenyl)-7H-pyrrolo[2,3-d]pyrimidin-6-yl)-3-methylphenyl)acrylamide | 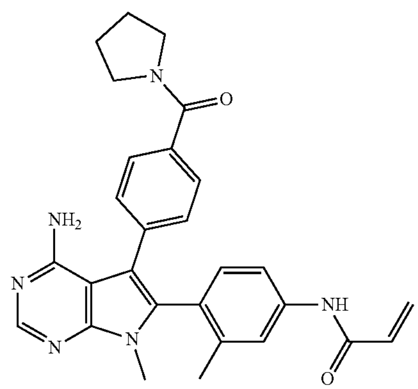 [SMILES: C=CC(=O)Nc1ccc(-c2c(-c3ccc(C(=O)N4CCCC4)cc3)c3c(N)ncnc3n2C)c(C)c1] | ¹H NMR (400 MHz, DMSO-d₆) δ 10.21 (s, 1H), 8.21 (s, 1H), 7.58 (d, J = 8.3 Hz, 2H), 7.49-7.42 (m, 2H), 7.27 (d, J = 8.1 Hz, 1H), 7.24-7.18 (m, 2H), 6.44 (dd, J = 17.0, 10.1 Hz, 1H), 6.27 (dd, J = 17.0, 2.1 Hz, 1H), 5.77 (dd, J = 10.0, 2.1 Hz, 1H), 3.41 (d, J = 6.3 Hz, 7H), 1.91 (s, 3H), 1.83 (dt, J = 18.0, 6.5 Hz, 4H). | 481.2 |
| N-(4-(4-amino-7-methyl-5-(4-(pyrrolidine-1-carbonyl)phenyl)-7H-pyrrolo[2,3-d]pyrimidin-6-yl)-3-fluorophenyl)acrylamide | 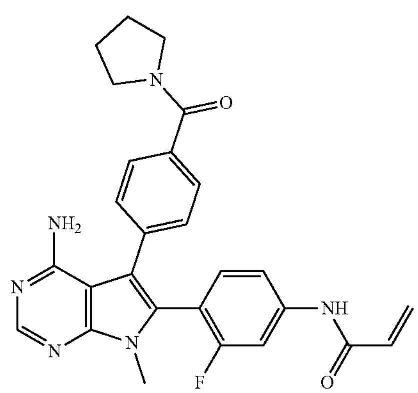 [SMILES: C=CC(=O)Nc1ccc(-c2c(-c3ccc(C(=O)N4CCCC4)cc3)c3c(N)ncnc3n2C)c(F)c1] | ¹H NMR (400 MHz, DMSO-d₆) δ 10.49 (s, 1H), 8.22 (s, 1H), 7.79 (dd, J = 12.2, 2.0 Hz, 1H), 7.49 (d, J = 7.8 Hz, 2H), 7.37 (dd, J = 8.5, 2.0 Hz, 1H), 7.32-7.24 (m, 2H), 7.24 (s, 1H), 6.43 (dd, J = 17.0, 10.0 Hz, 1H), 6.30 (dd, J = 17.0, 2.0 Hz, 1H), 6.03 (s, 2H), 5.82 (dd, J = 10.1, 2.1 Hz, 1H), 3.55 (s, 3H), 3.43 (dt, J = 18.4, 6.6 Hz, 4H), 1.83 (dq, J = 12.9, 6.8 Hz, 4H). | 485.35 |
| N-(4-(4-amino-7-methyl-5-(4-(pyrrolidine-1-carbonyl)phenyl)-7H-pyrrolo[2,3-d]pyrimidin-6-yl)-2-fluorophenyl)methacrylamide | 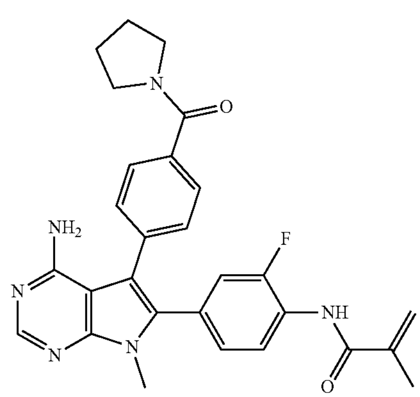 [SMILES: C=C(C)C(=O)Nc1ccc(-c2c(-c3ccc(C(=O)N4CCCC4)cc3)c3c(N)ncnc3n2C)cc1F] | ¹H NMR (400 MHz, DMSO-d₆) δ 9.61 (s, 1H), 8.22 (s, 1H), 7.59 (t, J = 8.2 Hz, 1H), 7.54-7.47 (m, 2H), 7.32-7.24 (m, 3H), 7.13 (dd, J = 8.3, 1.9 Hz, 1H), 5.88 (s, 1H), 5.56 (s, 1H), 3.65 (s, 3H), 3.44 (dt, J = 16.9, 6.5 Hz, 4H), 1.95 (s, 3H), 1.84 (dq, J = 18.5, 7.0 Hz, 4H). | 499.2 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)-2,6-difluorophenyl)methacrylamide | | $^1$H NMR (400 MHz, DMSO-d$_6$) δ 9.66 (s, 1H), 8.23 (s, 1H), 7.53 (d, J = 8.0 Hz, 2H), 7.31 (d, J = 7.9 Hz, 2H), 7.23-7.13 (m, 2H), 5.91 (s, 1H), 5.60 (s, 1H), 3.44 (dt, J = 19.8, 6.5 Hz, 4H), 3.33 (s, 2H), 1.94 (s, 3H), 1.84 (dq, J = 18.4, 6.7 Hz, 3H). | 517.35 |
| 4-(4-amino-6-(4-methacrylamidophenyl)-7-methyl-7H-pyrrolo[2,3-d]pyrimidin-5-yl)-N-cyclopentyl-N-methylbenzamide | | $^1$H NMR (400 MHz, DMSO-d$_6$) δ 9.89 (s, 1H), 8.21 (s, 1H), 7.73-7.67 (m, 2H), 7.32 (d, J = 7.8 Hz, 2H), 7.26 (dd, J = 8.4, 2.4 Hz, 4H), 6.33-5.71 (s, 3H), 5.53 (d, J = 1.8 Hz, 1H), 4.99-3.92 (s, 1H), 3.65 (s, 3H), 2.82 (s, 3H), 1.95 (d, J = 1.6 Hz, 3H), 1.90-1.58 (s, 6H), 1.57-1.33 (s, 2H). | 509.4 |
| 4-(4-amino-6-(4-methacrylamidophenyl)-7-methyl-7H-pyrrolo[2,3-d]pyrimidin-5-yl)-N-cyclopentylbenzamide | | $^1$H NMR (400 MHz, DMSO-d$_6$) δ 9.89 (s, 1H), 8.29-8.19 (m, 2H), 7.81 (d, J = 8.2 Hz, 2H), 7.79-7.66 (m, 2H), 7.27 (t, J = 8.4 Hz, 4H), 6.31-5.45 (s, 4H), 4.22 (q, J = 6.9 Hz, 1H), 3.65 (s, 3H), 1.95 (t, J = 1.2 Hz, 3H), 1.87 (s, 2H), 1.69 (s, 2H), 1.53 (q, J = 11.7, 8.4 Hz, 4H). | 495.35 |

TABLE 2-continued

Additional Exemplary Compounds

| Compound | Structure | Proton NMR | MS [M + 1] |
|---|---|---|---|
| N-(4-(5-(4-(2-azabicyclo[2.2.2]octane-2-carbonyl)phenyl)-4-amino-7-methyl-7H-pyrrolo[2,3-d]pyrimidin-6-yl)phenyl)methacrylamide | 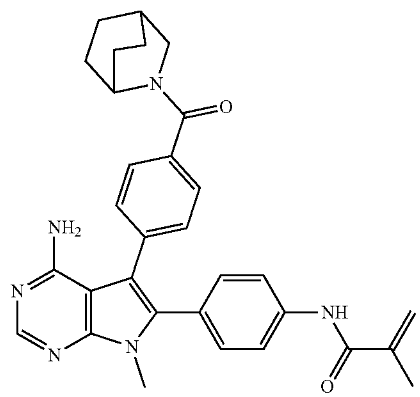 [SMILES: C=C(C)C(=O)Nc1ccc(-c2c(-c3ccc(C(=O)N4CC5CCC4CC5)cc3)c3c(N)ncnc3n2C)cc1] | $^1$H NMR (400 MHz, Methanol-d$_4$) δ 8.22 (s, 1H), 7.71-7.64 (m, 2H), 7.44-7.35 (m, 4H), 7.28 (dd, J = 9.4, 2.7 Hz, 2H), 5.81 (s, 1H), 5.54 (s, 1H), 3.70 (s, 4H), 3.58 (d, J = 2.5 Hz, 2H), 2.08-2.02 (m, 4H), 1.92 (s, 2H), 1.81-1.68 (m, 6H). | 521.40 |
| N-(4-(4-amino-5-(4-(azepane-1-carbonyl)phenyl)-7-methyl-7H-pyrrolo[2,3-d]pyrimidin-6-yl)phenyl)methacrylamide | 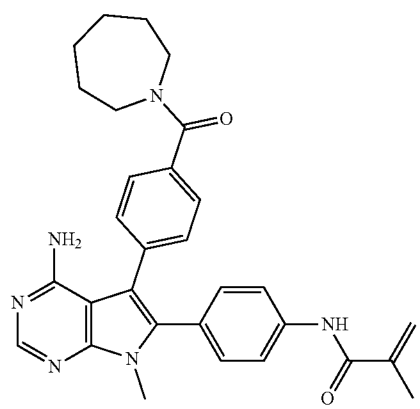 [SMILES: C=C(C)C(=O)Nc1ccc(-c2c(-c3ccc(C(=O)N4CCCCCC4)cc3)c3c(N)ncnc3n2C)cc1] | $^1$H NMR (400 MHz, DMSO-d$_6$) δ 9.89 (s, 1H), 8.20 (s, 1H), 7.73-7.67 (m, 2H), 7.32 (d, J = 8.1 Hz, 2H), 7.25 (dd, J = 8.3, 1.6 Hz, 4H), 5.93 (s, 2H), 5.79 (s, 1H), 5.53 (s, 1H), 3.62 (s, 3H), 3.55 (t, J = 5.7 Hz, 2H), 1.95 (d, J = 1.5 Hz, 3H), 1.70 (s, 2H), 1.55 (s, 6H). | 509.4 |
| N-(4-(5-(4-(2-azaspiro[3.3]heptane-2-carbonyl)phenyl)-4-amino-7-methyl-7H-pyrrolo[2,3-d]pyrimidin-6-yl)phenyl)methacrylamide | 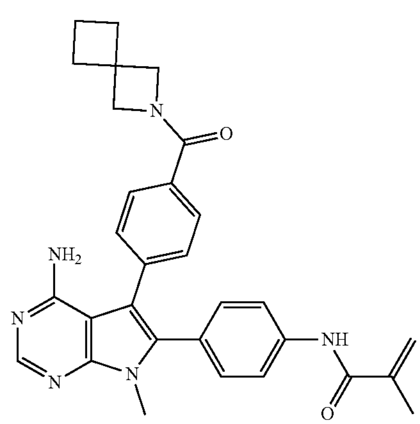 [SMILES: C=C(C)C(=O)Nc1ccc(-c2c(-c3ccc(C(=O)N4CC5(CCC5)C4)cc3)c3c(N)ncnc3n2C)cc1] | $^1$H NMR (400 MHz, DMSO-d$_6$) δ 9.90 (s, 1H), 8.21 (s, 1H), 7.74-7.68 (m, 2H), 7.62-7.56 (m, 2H), 7.31-7.23 (m, 4H), 5.80 (s, 1H), 5.54 (d, J = 1.9 Hz, 1H), 4.29 (s, 2H), 4.00 (s, 2H), 3.61 (s, 3H), 2.15 (t, J = 7.6 Hz, 4H), 1.95 (s, 3H), 1.86 (s, 1H), 1.76 (td, J = 7.8, 3.7 Hz, 2H). | 507.40 |

TABLE 2-continued

Additional Exemplary Compounds

| Compound | Structure | Proton NMR | MS [M + 1] |
|---|---|---|---|
| N-(4-(4-amino-7-methyl-5-(4-(2-oxopiperidine-1-carbonyl)phenyl)-7H-pyrrolo[2,3-d]pyrimidin-6-yl)phenyl) methacrylamide | 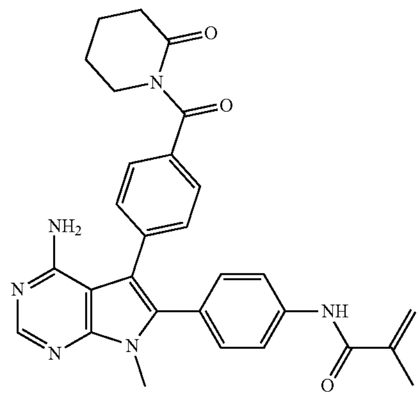 [SMILES: C=C(C)C(=O)Nc1ccc(-c2c(-c3ccc(C(=O)N4CCCCC4=O)cc3)c3c(N)ncnc3n2C)cc1] | ¹H NMR (400 MHz, DMSO-d₆) δ 9.91 (s, 1H), 8.21 (s, 1H), 7.72 (d, J = 8.6 Hz, 2H), 7.54 (d, J = 8.2 Hz, 2H), 7.27 (dd, J = 8.2, 5.8 Hz, 4H), 5.80 (s, 1H), 5.70 (s, 2H), 5.53 (s, 1H), 3.67 (t, J = 5.7 Hz, 2H), 3.61 (s, 3H), 2.50 (s, 2H) 1.95 (s, 3H), 1.87 (tt, J = 11.7, 6.3 Hz, 4H). | 509.25 |
| N-(4-(5-(4-(3-azabicyclo[4.1.0]heptane-3-carbonyl)phenyl)-4-amino-7-methyl-7H-pyrrolo[2,3-d]pyrimidin-6-yl)phenyl) methacrylamide | 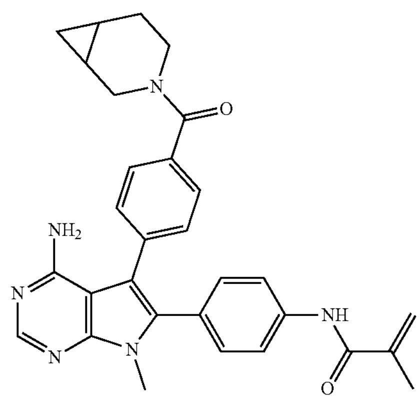 [SMILES: C=C(C)C(=O)Nc1ccc(-c2c(-c3ccc(C(=O)N4CCC5CC5C4)cc3)c3c(N)ncnc3n2C)cc1] | ¹H NMR (400 MHz, DMSO-d₆) δ 9.89 (s, 1H), 8.21 (s, 1H), 7.71 (d, J = 8.5 Hz, 2H), 7.32 (d, J = 7.9 Hz, 2H), 7.26 (d, J = 8.3 Hz, 4H), 5.95 (s, 2H), 5.80 (s, 1H), 5.53 (d, J = 1.7 Hz, 1H), 3.68 (d, J = 12.5 Hz, 2H), 3.61 (s, 4H), 3.08 (s, 1H), 1.95 (s, 4H), 1.70-1.64 (m, 1H), 1.06 (s, 2H), 0.64 (s, 1H), 0.21 (s, 1H). | 507.40 |
| N-(4-(5-(4-(2-azabicyclo[4.1.0]heptane-2-carbonyl)phenyl)-4-amino-7-methyl-7H-pyrrolo[2,3-d]pyrimidin-6-yl)phenyl) methacrylamide | 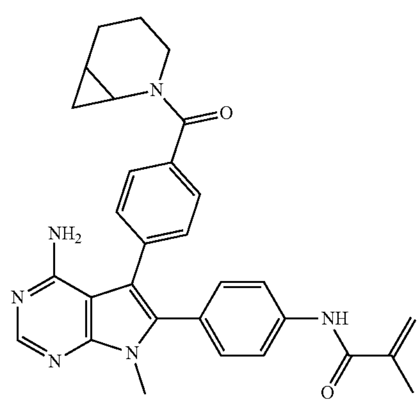 [SMILES: C=C(C)C(=O)Nc1ccc(-c2c(-c3ccc(C(=O)N4CCCC5CC54)cc3)c3c(N)ncnc3n2C)cc1] | ¹H NMR (400 MHz, DMSO-d₆) δ 9.89 (s, 1H), 8.20 (s, 1H), 7.73-7.66 (m, 2H), 7.52 (d, J = 7.9 Hz, 1H), 7.34 (d, J = 7.9 Hz, 1H), 7.26 (dd, J = 8.2, 4.2 Hz, 4H), 6.25-5.70 (m, 3H), 5.53 (t, J = 1.5 Hz, 1H), 4.05 (d, J = 12.6 Hz, 1H), 3.65 (d, J = 7.1 Hz, 3H), 3.02 (t, J = 12.6 Hz, 1H), 2.52 (t, J = 12.6 Hz, 1H), 1.95 (s, 3H), 1.85 (s, 2H), 1.83-1.55 (m, 1H), 1.35 (d, J = 13.8 Hz, 2H), 0.37 (s, 1H). | 507.4 |

TABLE 2-continued

Additional Exemplary Compounds

| Compound | Structure | Proton NMR | MS [M + 1] |
|---|---|---|---|
| N-(4-(4-amino-6-(4-methacrylamido-phenyl)-7-methyl-7H-pyrrolo[2,3-d]pyrimidin-5-yl)phenyl)cyclo-pentanecarbox-amide | 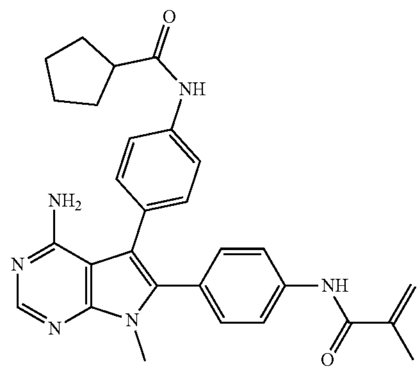 [SMILES: C=C(C)C(=O)Nc1ccc(-c2c(-c3ccc(NC(=O)C4CCCC4)cc3)c3c(N)ncnc3n2C)cc1] | $^1$H NMR (400 MHz, DMSO-d$_6$) δ 9.88 (d, J = 11.0 Hz, 2H), 8.18 (s, 1H), 7.72-7.65 (m, 2H), 7.62-7.55 (m, 2H), 7.29-7.22 (m, 2H), 7.18-7.11 (m, 2H), 5.80 (s, 1H), 5.53 (s, 1H), 3.61 (s, 3H), 2.76 (p, J = 7.8 Hz, 1H), 1.95 (d, J = 1.5 Hz, 3H), 1.85 (ddd, J = 14.1, 8.3, 4.3 Hz, 2H), 1.77-1.62 (m, 4H), 1.61-1.51 (m, 2H). | 495.20 |
| N-(4-(4-amino-6-(4-methacrylamido-phenyl)-7-methyl-7H-pyrrolo[2,3-d]pyrimidin-5-yl)phenyl)-N-methylcyclopentane-carboxamide | 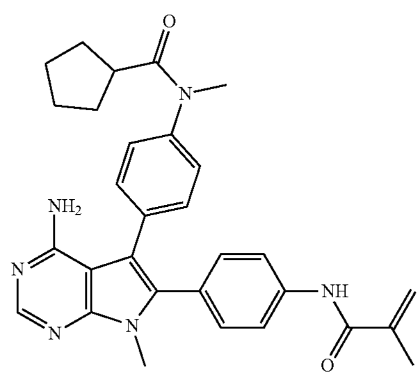 [SMILES: C=C(C)C(=O)Nc1ccc(-c2c(-c3ccc(N(C)C(=O)C4CCCC4)cc3)c3c(N)ncnc3n2C)cc1] | $^1$H NMR (400 MHz, DMSO-d$_6$) δ 9.89 (s, 1H), 8.20 (s, 1H), 7.80-7.62 (m, 2H), 7.36-7.19 (m, 6H), 5.78 (s, 1H), 5.53 (s, 1H), 3.63 (s, 3H), 3.17 (d, J = 2.9 Hz, 3H), 1.94 (t, J = 1.2 Hz, 3H), 1.65-1.30 (s, 9H). | 509.30 |
| N-(4-(5-(4-(3-azabicyclo[3.1.0]hexane-3-carbonyl)phenyl)4-amino-7-methyl-7H-pyrrolo[2,3-d]pyrimidin-6-yl)phenyl)methacrylamide | 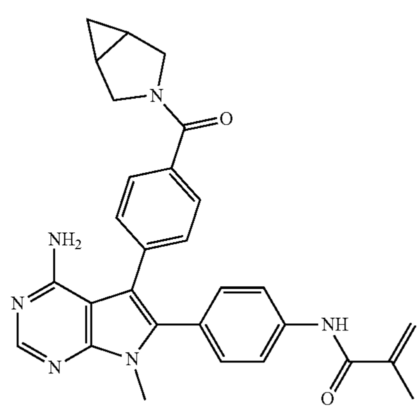 [SMILES: C=C(C)C(=O)Nc1ccc(-c2c(-c3ccc(C(=O)N4CC5CC5C4)cc3)c3c(N)ncnc3n2C)cc1] | $^1$H NMR (400 MHz, DMSO-d$_6$) δ 9.89 (s, 1H), 8.21 (s, 1H), 7.75 (d, J = 8.4 Hz, 2H), 7.45 (d, J = 7.9 Hz, 2H), 7.26 (dd, J = 8.2, 4.4 Hz, 4H), 6.25-5.75 (s, 2H), 5.53 (s, 1H), 3.95 (d, J = 11.9 Hz, 1H), 3.66 (d, J = 10.7 Hz, 1H), 3.58 (s, 3H), 3.38 (d, J = 10.8 Hz, 2H), 1.95 (s, 3H), 1.69-1.51 (m, 2H), 0.65 (q, J = 4.3 Hz, 1H), 0.08 (q, J = 4.3 Hz, 1H). | 493.35 |

TABLE 2-continued

Additional Exemplary Compounds

| Compound | Structure | Proton NMR | MS [M + 1] |
|---|---|---|---|
| N-(4-(5-(4-(5-azaspiro[2.4]heptane-5-carbonyl)phenyl)-4-amino-7-methyl-7H-pyrrolo[2,3-d]pyrimidin-6-yl)phenyl)methacrylamide | 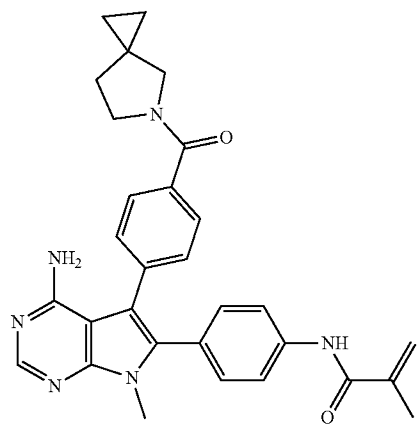 [SMILES: C=C(C)C(=O)Nc1ccc(-c2c(-c3ccc(C(=O)N4CCC5(CC5)C4)cc3)c3c(N)ncnc3n2C)cc1] | $^1$H NMR (400 MHz, DMSO-d$_6$) δ 9.90 (s, 1H), 8.20 (s, 1H), 7.70 (dd, J = 8.8, 3.4 Hz, 2H), 7.50 (dd, J = 12.8, 7.8 Hz, 2H), 7.26 (dt, J = 8.2, 4.5 Hz, 4H), 6.04 (s, 1H), 5.92-5.80 (s, 1H), 5.53 (s, 1H), 3.66-3.55 (m, 5H), 3.37 (d, J = 8.4 Hz, 2H), 1.95 (s, 3H), 1.81 (t, J = 7.1 Hz, 1H), 1.76 (t, J = 6.7 Hz, 1H), 0.54 (d, J = 3.4 Hz, 4H). | 507.45 |
| N-(4-(5-(4-(2-azabicyclo[3.1.0]hexane-2-carbonyl)phenyl)-4-amino-7-methyl-7H-pyrrolo[2,3-d]pyrimidin-6-yl)phenyl)methacrylamide | 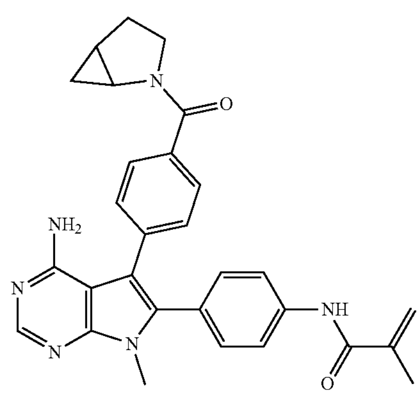 [SMILES: C=C(C)C(=O)Nc1ccc(-c2c(-c3ccc(C(=O)N4CCC5CC54)cc3)c3c(N)ncnc3n2C)cc1] | $^1$H NMR (400 MHz, DMSO-d$_6$) δ 9.89 (s, 1H), 8.21 (s, 1H), 7.70 (d, J = 8.4 Hz, 2H), 7.59 (d, J = 7.7 Hz, 2H), 7.44 (s, 1H), 7.28 (t, J = 8.9 Hz, 3H), 5.95 (s, 2H), 5.80 (s, 1H), 5.53 (s, 1H), 3.96 (d, J = 12.2 Hz, 1H), 3.61 (s, 3H), 3.31-3.21 (s, 1H), 3.13 (d, J = 12.0 Hz, 1H), 2.06 (s, 1H), 1.95 (s, 4H), 1.60 (s, 1H), 0.77 (t, J = 6.5 Hz, 2H). | 493.40 |
| N-(4-(5-(4-((1R,4R)-2-oxa-5-azabicyclo[2.2.2]octane-5-carbonyl)phenyl)-4-amino-7-methyl-7H-pyrrolo[2,3-d]pyrimidin-6-yl)phenyl)methacrylamide | 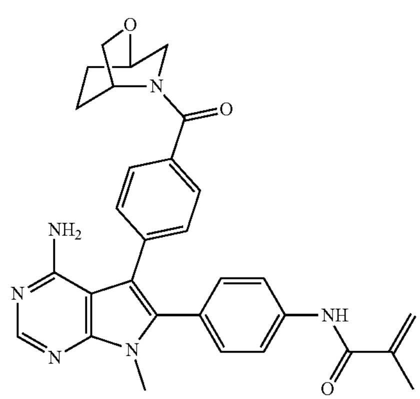 [SMILES: C=C(C)C(=O)Nc1ccc(-c2c(-c3ccc(C(=O)N4CC5CCC4CO5)cc3)c3c(N)ncnc3n2C)cc1] | $^1$H NMR (400 MHz, DMSO-d$_6$) δ 9.89 (s, 1H), 8.21 (d, J = 2.7 Hz, 1H), 7.75 (d, J = 8.3 Hz, 2H), 7.59-7.25 (d, J = 7.8 Hz, 2H), 7.23 (dd, J = 8.3, 4.7 Hz, 4H), 6.25-5.72 (s, 3H), 5.53 (s, 1H), 4.06 (d, J = 17.0 Hz, 2H), 3.95-3.72 (dd, J = 18.0, 9.0 Hz, 3H), 3.65 (m, 3H), 3.51 (d, J = 3.7 Hz, 1H), 2.05 (d, J = 10.8 Hz, 2H), 1.95 (s, 3H), 1.85-1.64 (m, 2H). | 523.35 |

TABLE 2-continued

Additional Exemplary Compounds

| Compound | Structure | Proton NMR | MS [M + 1] |
|---|---|---|---|
| N-(4-(4-amino-7-methyl-5-(4-(3-methylpiperidine-1-carbonyl)phenyl)-7H-pyrrolo[2,3-d]pyrimidin-6-yl)phenyl)methacrylamide | 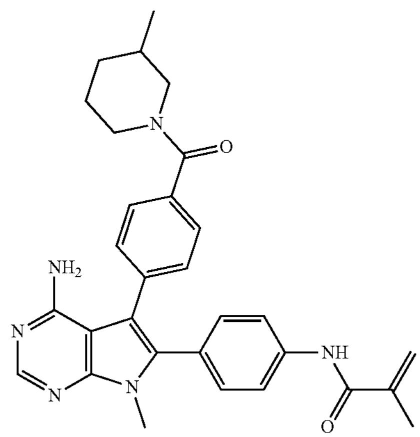 [SMILES: C=C(C)C(=O)Nc1ccc(-c2c(-c3ccc(C(=O)N4CCCC(C)C4)cc3)c3c(N)ncnc3n2C)cc1] | $^1$H NMR (400 MHz, DMSO-d$_6$) δ 9.89 (s, 1H), 8.21 (s, 1H), 7.74-7.67 (m, 2H), 7.36-7.22 (m, 6H), 5.79 (s, 1H), 5.53 (s, 1H), 4.28 (s, 1H), 3.62 (s, 4H), 2.96 (s, 1H), 1.95 (s, 3H), 1.78 (d, J = 12.6 Hz, 1H), 1.57 (s, 2H), 1.42 (d, J = 13.0 Hz, 1H), 1.17 (t, J = 11.1 Hz, 1H), 0.77 (s, 3H). | 509.40 |
| N-(4-(4-amino-7-methyl-5-(4-(4-methylpiperidine-1-carbonyl)phenyl)-7H-pyrrolo[2,3-d]pyrimidin-6-yl)phenyl)methacrylamide | 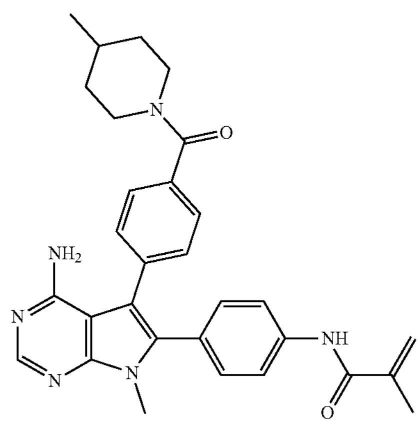 [SMILES: C=C(C)C(=O)Nc1ccc(-c2c(-c3ccc(C(=O)N4CCC(C)CC4)cc3)c3c(N)ncnc3n2C)cc1] | $^1$H NMR (400 MHz, DMSO-d$_6$) δ 9.90 (s, 1H), 8.20 (s, 1H), 7.70 (d, J = 8.6 Hz, 2H), 7.33 (d, J = 8.1 Hz, 2H), 7.26 (d, J = 8.3 Hz, 4H), 5.95 (s, 1H), 5.80 (s, 1H), 5.53 (s, 1H), 4.42 (s, 1H), 3.61 (s, 4H), 2.99 (s, 1H), 2.72 (s, 1H), 1.95 (s, 3H), 1.62 (s, 3H), 1.14-1.07 (m, 1H), 1.05 (s, 1H), 0.92 (d, J = 6.2 Hz, 3H). | 509.3 |
| N-(4-(4-amino-7-methyl-5-(4-(2-methylpiperidine-1-carbonyl)phenyl)-7H-pyrrolo[2,3-d]pyrimidin-6-yl)phenyl)methacrylamide | 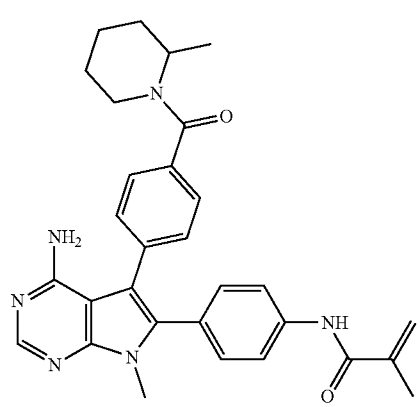 [SMILES: C=C(C)C(=O)Nc1ccc(-c2c(-c3ccc(C(=O)N4CCCCC4C)cc3)c3c(N)ncnc3n2C)cc1] | $^1$H NMR (400 MHz, DMSO-d$_6$) δ 9.89 (s, 1H), 8.20 (s, 1H), 7.70 (d, J = 8.4 Hz, 2H), 7.31 (d, J = 8.0 Hz, 2H), 7.26 (d, J = 9.0 Hz, 4H), 5.80 (s, 1H), 5.53 (s, 1H), 4.45 (s, 1H), 3.61 (s, 3H), 3.30 (s, 1H), 2.98 (s, 1H), 1.95 (s, 3H), 1.62 (dd, J = 19.7, 7.5 Hz, 5H), 1.36 (d, J = 12.8 Hz, 1H), 1.18 (d, J = 6.9 Hz, 3H). | 509.4 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-cyclobutyl-N-methylbenzamide | 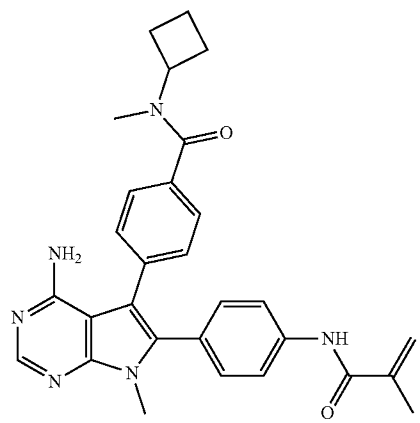 [SMILES: C=C(C)C(=O)Nc1ccc(-c2c(-c3ccc(C(=O)N(C)C4CCC4)cc3)c3c(N)ncnc3n2C)cc1] | $^1$H NMR (400 MHz, DMSO-d$_6$) δ 9.89 (s, 1H), 8.21 (s, 1H), 7.74-7.67 (m, 2H), 7.32-7.23 (m, 6H), 5.97 (s, 0H), 5.79 (s, 1H), 5.53 (d, J = 1.8 Hz, 1H), 4.32 (s, 1H), 3.62 (s, 3H), 2.93 (s, 3H), 2.22 (dq, J = 12.2, 9.4 Hz, 2H), 1.95 (s, 5H), 1.60 (s, 1H). | 495.35 |
| 4-(4-amino-6-(4-methacrylamido-phenyl)-7-methyl-7H-pyrrolo[2,3-d]pyrimidin-5-yl)-N-cyclobutylbenzamide | 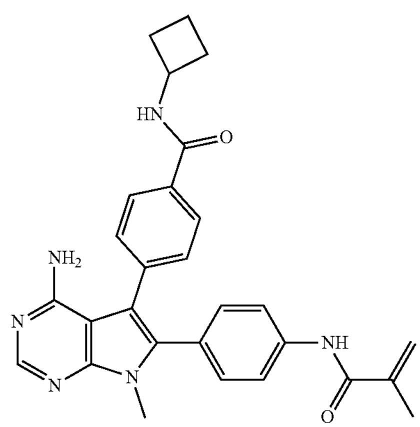 [SMILES: C=C(C)C(=O)Nc1ccc(-c2c(-c3ccc(C(=O)NC4CCC4)cc3)c3c(N)ncnc3n2C)cc1] | $^1$H NMR (400 MHz, DMSO-d$_6$) δ 9.90 (s, 1H), 8.59 (d, J = 7.6 Hz, 1H), 8.21 (s, 1H), 7.79 (d, J = 8.2 Hz, 2H), 7.73-7.67 (m, 2H), 7.32-7.23 (m, 4H), 5.92 (s, 2H), 5.79 (s, 1H), 5.54 (s, 1H), 4.40 (q, J = 8.2 Hz, 1H), 3.61 (s, 3H), 2.20 (d, J = 8.7 Hz, 3H), 2.12-1.98 (m, 2H), 1.95 (d, J = 1.4 Hz, 3H), 1.65 (td, J = 10.7, 9.4, 6.1Hz, 2H). | 481.35 |
| N-(4-(4-amino-6-(4-methacrylamido-phenyl)-7-methyl-7H-pyrrolo[2,3-d]pyrimidin-5-yl)phenyl)cyclo-butanecarboxamide | 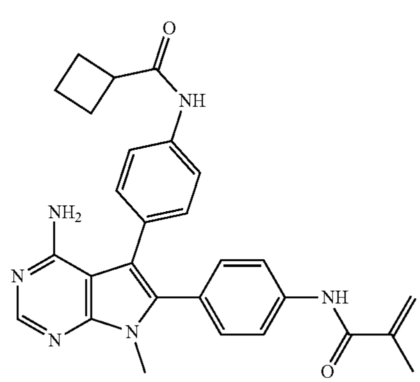 [SMILES: C=C(C)C(=O)Nc1ccc(-c2c(-c3ccc(NC(=O)C4CCC4)cc3)c3c(N)ncnc3n2C)cc1] | $^1$H NMR (400 MHz, DMSO-d$_6$) δ 9.88 (s, 1H), 9.76 (s, 1H), 8.18 (s, 1H), 7.69 (d, J = 8.3 Hz, 2H), 7.59 (d, J = 8.1 Hz, 2H), 7.25 (d, J = 8.2 Hz, 2H), 7.15 (d, J = 8.1 Hz, 2H), 5.79 (s, 1H), 5.58 (s, 1H), 5.53 (s, 1H), 3.61 (s, 3H), 3.26-3.17 (m, 1H), 2.22 (t, J = 9.5 Hz, 2H), 2.10 (d, J = 9.3 Hz, 2H), 1.95 (s, 4H), 1.80 (d, J = 10.6 Hz, 1H). | 481.20 |

TABLE 2-continued

Additional Exemplary Compounds

| Compound | Structure | Proton NMR | MS [M + 1] |
|---|---|---|---|
| N-(4-(5-(4-(5-azaspiro[2.5]octane-5-carbonyl)phenyl)-4-amino-7-methyl-7H-pyrrolo[2,3-d]pyrimidin-6-yl)phenyl)methacrylamide | 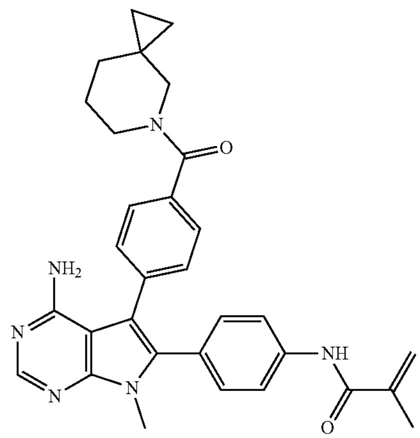 [SMILES: C=C(C)C(=O)Nc1ccc(-c2c(-c3ccc(C(=O)N4CCCC5(CC5)C4)cc3)c3c(N)ncnc3n2C)cc1] | $^1$H NMR (400 MHz, DMSO-d$_6$) δ 9.89 (s, 1H), 8.20 (s, 1H), 7.70 (d, J = 8.2 Hz, 2H), 7.26 (s, 6H), 5.79 (s, 2H), 5.53 (s, 1H), 3.62 (s, 3H), 3.39 (s, 2H), 3.30 (s, 1H), 3.09 (s, 1H), 1.95 (s, 3H), 1.60 (s, 2H), 1.46 (s, 2H), 0.46 (s, 1H), 0.29 (s, 2H), 0.11 (s, 1H). | 521.40 |
| N-(4-(5-(4-(6-azaspiro[2.5]octane-6-carbonyl)phenyl)-4-amino-7-methyl-7H-pyrrolo[2,3-d]pyrimidin-6-yl)phenyl)methacrylamide | 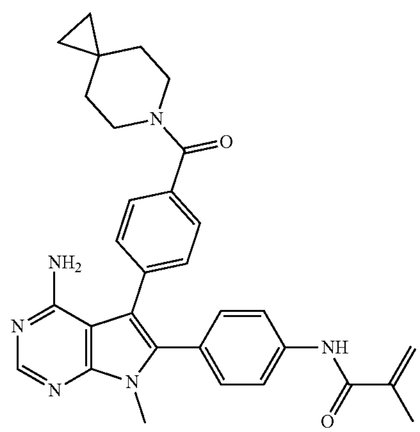 [SMILES: C=C(C)C(=O)Nc1ccc(-c2c(-c3ccc(C(=O)N4CCC5(CC4)CC5)cc3)c3c(N)ncnc3n2C)cc1] | $^1$H NMR (400 MHz, DMSO-d$_6$) δ 9.88 (s, 1H), 8.20 (s, 1H), 7.70 (d, J = 8.3 Hz, 2H), 7.41 (d, J = 7.8 Hz, 2H), 7.26 (dd, J = 8.4, 2.6 Hz, 4H), 6.25-5.75 (s, 2H), 5.53 (s, 1H), 3.85-3.35 (s, 7H), 1.95 (s, 3H), 1.35 (s, 4H), 0.35 (s, 4H). | 521.4 |
| N-(4-(4-amino-7-methyl-5-(1-oxoisoindolin-5-yl)-7H-pyrrolo[2,3-d]pyrimidin-6-yl)phenyl)methacrylamide | 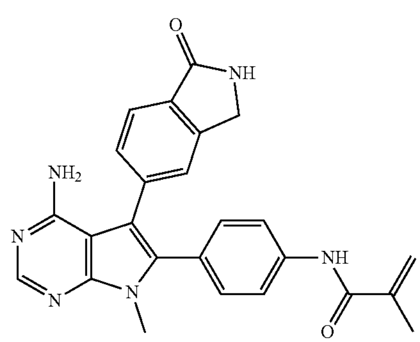 [SMILES: C=C(C)C(=O)Nc1ccc(-c2c(-c3ccc4c(c3)CNC4=O)c3c(N)ncnc3n2C)cc1] | $^1$H NMR (400 MHz, DMSO-d$_6$) δ 9.88 (s, 1H), 8.51 (s, 1H), 8.21 (s, 1H), 7.73-7.66 (m, 2H), 7.59 (d, J = 7.7 Hz, 1H), 7.43 (s, 1H), 7.35-7.23 (m, 3H), 5.91 (s, 2H), 5.79 (s, 1H), 5.53 (s, 1H), 4.33 (s, 2H), 3.62 (s, 3H), 1.95 (s, 3H). | 439.25 |

TABLE 2-continued

Additional Exemplary Compounds

| Compound | Structure | Proton NMR | MS [M + 1] |
|---|---|---|---|
| N-(4-(4-amino-5-(4-(cyclopentyloxy)phenyl)-7-methyl-7H-pyrrolo[2,3-d]pyrimidin-6-yl)phenyl)methacrylamide | 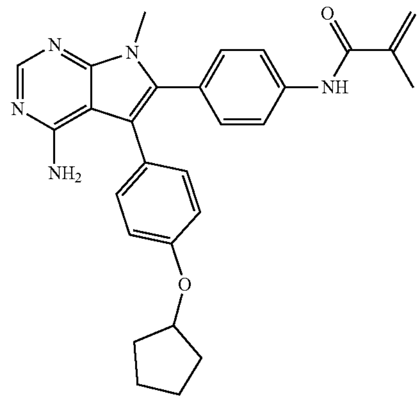 [SMILES: C=C(C)C(=O)Nc1ccc(-c2c(-c3ccc(OC4CCCC4)cc3)c3c(N)ncnc3n2C)cc1] | $^1$H NMR (400 MHz, DMSO-d$_6$) δ 9.88 (s, 1H), 8.17 (s, 1H), 7.73-7.66 (m, 2H), 7.30-7.23 (m, 2H), 7.18-7.09 (m, 2H), 6.92-6.83 (m, 2H), 5.80 (s, 1H), 5.53 (d, J = 1.9 Hz, 1H), 4.79 (td, J = 6.0, 3.0 Hz, 1H), 3.60 (s, 3H), 1.97-1.86 (m, 5H), 1.75-1.65 (m, 4H), 1.58 (q, J = 6.0, 3.6 Hz, 2H). | 468.30 |
| N-(4-(4-amino-5-(4-(cyclopentylmethoxy)phenyl)-7-methyl-7H-pyrrolo[2,3-d]pyrimidin-6-yl)phenyl)methacrylamide | | $^1$H NMR (400 MHz, DMSO-d$_6$) δ 9.88 (s, 1H), 8.17 (s, 1H), 7.72-7.66 (m, 2H), 7.29-7.23 (m, 2H), 7.17-7.10 (m, 2H), 6.94-6.87 (m, 2H), 5.79 (s, 1H), 5.53 (t, J = 1.5 Hz, 1H), 3.83 (d, J = 6.9 Hz, 2H), 3.60 (s, 3H), 2.28 (dq, J = 14.7, 7.4 Hz, 1H), 2.08 (s, 1H), 1.95 (t, J = 1.2 Hz, 3H), 1.76 (ddd, J = 11.9, 9.2, 4.7 Hz, 2H), 1.65-1.47 (m, 4H), 1.39-1.26 (m, 2H). | 482.35 |
| N-(4-(4-amino-7-methyl-5-(4-(octahydro-1H-isoindole-2-carbonyl)phenyl)-7H-pyrrolo[2,3-d]pyrimidin-6-yl)phenyl)methacrylamide | 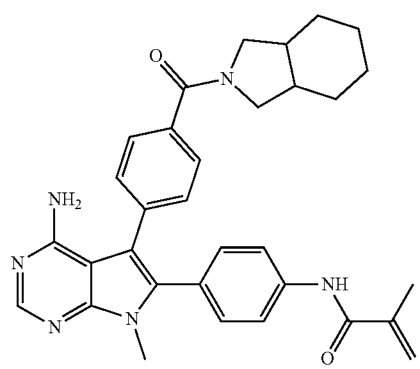 [SMILES: C=C(C)C(=O)Nc1ccc(-c2c(-c3ccc(C(=O)N4CC5CCCCC5C4)cc3)c3c(N)ncnc3n2C)cc1] | $^1$H NMR (400 MHz, DMSO-d$_6$) δ 9.92 (s, 1H), 8.37 (s, 1H), 7.72 (d, J = 8.6 Hz, 2H), 7.52 (d, J = 8.0 Hz, 2H), 7.27 (d, J = 8.0 Hz, 4H), 6.74 (s, 3H), 5.80 (s, 1H), 5.54 (s, 1H), 3.66 (s, 3H), 3.51-3.41 (m, 2H), 3.39-3.26 (m, 1H), 3.31 (s, 1H), 2.25 (d, J = 6.9 Hz, 1H), 2.16 (s, 1H), 1.95 (s, 3H), 1.49 (d, J = 9.3 Hz, 5H), 1.33-1.26 (m, 3H). | 535.50 |
| N-(4-(4-amino-5-(4-(4-fluoropiperidine-1-carbonyl)phenyl)-7-methyl-7H-pyrrolo[2,3-d]pyrimidin-6-yl)phenyl)methacrylamide | 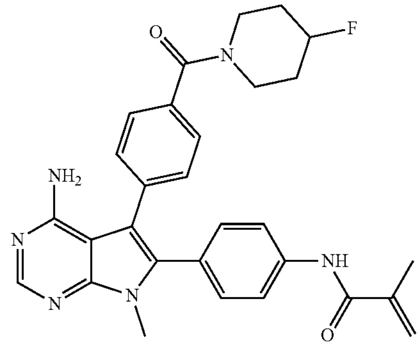 [SMILES: C=C(C)C(=O)Nc1ccc(-c2c(-c3ccc(C(=O)N4CCC(F)CC4)cc3)c3c(N)ncnc3n2C)cc1] | $^1$H NMR (400 MHz, DMSO-d$_6$) δ 9.91 (s, 1H), 8.29 (s, 1H), 7.75-7.68 (m, 2H), 7.41-7.34 (m, 2H), 7.27 (dd, J = 8.4, 2.4 Hz, 4H), 5.80 (s, 1H), 5.54 (s, 1H), 4.97 (s, 1H), 4.85 (s, 1H), 3.63 (s, 3H), 3.61 (s, 3H), 1.95 (s, 3H), 1.73 (s, 3H). | 513.40 |

TABLE 2-continued

Additional Exemplary Compounds

| Compound | Structure | Proton NMR | MS [M + 1] |
|---|---|---|---|
| N-(4-(4-amino-5-(4-(4-methoxypiperidine-1-carbonyl)phenyl)-7-methyl-7H-pyrrolo[2,3-d]pyrimidin-6-yl)phenyl)methacrylamide | 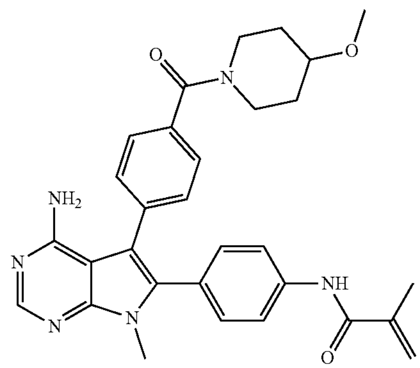 [SMILES: C=C(C)C(=O)Nc1ccc(-c2c(-c3ccc(C(=O)N4CCC(OC)CC4)cc3)c3c(N)ncnc3n2C)cc1] | $^1$H NMR (400 MHz, DMSO-d$_6$) δ 9.89 (s, 1H), 8.20 (s, 1H), 7.74-7.67 (m, 2H), 7.35 (d, J = 7.8 Hz, 2H), 7.26 (d, J = 8.1 Hz, 4H), 5.96 (s, 2H), 5.80 (s, 1H), 5.53 (s, 1H), 3.89 (s, 1H), 3.61 (s, 3H), 1.95 (s, 3H), 1.84 (s, 2H), 1.44 (s, 2H). | 525.45 |
| N-(4-(4-amino-5-(4-(3,3-difluoroazetidine-1-carbonyl)phenyl)-7-methyl-7H-pyrrolo[2,3-d]pyrimidin-6-yl)phenyl)methacrylamide | 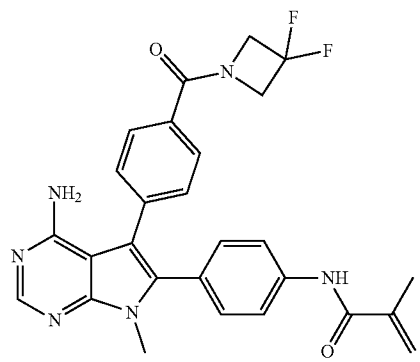 [SMILES: C=C(C)C(=O)Nc1ccc(-c2c(-c3ccc(C(=O)N4CC(F)(F)C4)cc3)c3c(N)ncnc3n2C)cc1] | $^1$H NMR (400 MHz, DMSO-d$_6$) δ 9.90 (s, 1H), 8.21 (s, 1H), 7.75-7.63 (m, 4H), 7.34-7.23 (m, 4H), 5.96 (s, 1H), 5.80 (t, J = 1.0 Hz, 1H), 5.54 (t, J = 1.4 Hz, 1H), 4.78 (s, 2H), 4.52 (s, 2H), 3.61 (s, 3H), 1.95 (t, J = 1.2 Hz, 3H). | 503.20 |
| 4-(4-amino-6-(4-methacrylamidophenyl)-7-methyl-7H-pyrrolo[2,3-d]pyrimidin-5-yl)-N-(2,2,2-trifluoroethyl)benzamide | | $^1$H NMR (400 MHz, DMSO-d$_6$) δ 9.92 (s, 1H), 9.09 (t, J = 6.3 Hz, 1H), 8.36 (s, 1H), 7.87 (d, J = 8.2 Hz, 2H), 7.76-7.68 (m, 2H), 7.33 (d, J = 8.2 Hz, 2H), 7.30-7.24 (m, 2H), 6.69 (s, 2H), 5.80 (s, 1H), 5.54 (s, 1H), 4.08 (td, J = 9.9, 6.3 Hz, 2H), 3.65 (s, 3H), 1.95 (s, 3H). | 509.35 |
| 4-(4-amino-6-(4-methacrylamidophenyl)-7-methyl-7H-pyrrolo[2,3-d]pyrimidin-5-yl)-N-(2-hydroxyethyl)-N-methylbenzamide | | $^1$H NMR (400 MHz, DMSO-d$_6$) δ 9.89 (s, 1H), 8.21 (s, 1H), 7.70 (d, J = 8.4 Hz, 2H), 7.38 (d, J = 7.9 Hz, 2H), 7.30-7.23 (m, 4H), 5.94 (s, 0H), 5.80 (s, 1H), 5.53 (s, 1H), 4.77 (s, 1H), 3.62 (s, 4H), 3.50 (s, 2H), 3.32 (s, 1H), 2.98 (s, 3H), 1.95 (s, 3H), 1.25 (s, 1H). | 485.35 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(2-methoxyethyl)-N-methylbenzamide | 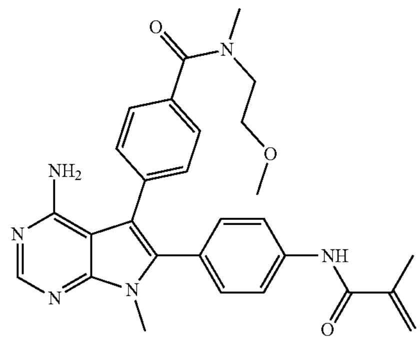 [SMILES: C=C(C)C(=O)Nc1ccc(-c2c(-c3ccc(C(=O)N(C)CCOC)cc3)c3c(N)ncnc3n2C)cc1] | $^1$H NMR (400 MHz, DMSO-d$_6$) δ 9.89 (s, 1H), 8.21 (s, 1H), 7.73-7.67 (m, 2H), 7.35 (d, J = 8.1 Hz, 2H), 7.26 (d, J = 8.2 Hz, 4H), 5.80 (s, 2H), 5.53 (s, 1H), 3.62 (s, 3H), 3.41 (s, 2H), 3.29 (s, 1H), 3.11 (s, 2H), 2.97 (s, 3H), 1.95 (d, J = 1.5 Hz, 3H). | 499.40 |
| (R)-N-(4-(4-amino-5-(4-(3-methoxypyrrolidine-1-carbonyl)phenyl)-7-methyl-7H-pyrrolo[2,3-d]pyrimidin-6-yl)phenyl) methacrylamide | 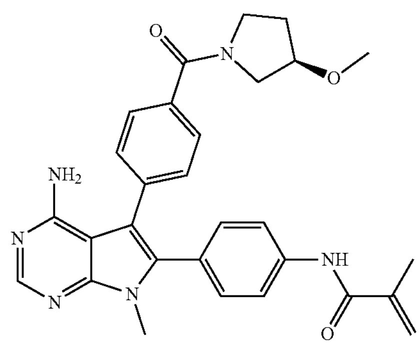 [SMILES: C=C(C)C(=O)Nc1ccc(-c2c(-c3ccc(C(=O)N4CC[C@@H](OC)C4)cc3)c3c(N)ncnc3n2C)cc1] | $^1$H NMR (400 MHz, Methanol-d$_4$) δ 8.22 (s, 1H), 7.67 (d, J = 8.4 Hz, 2H), 7.52 (dd, J = 8.2, 2.1 Hz, 2H), 7.38 (d, J = 8.0 Hz, 2H), 7.31-7.24 (m, 2H), 5.85 (s, 1H), 5.54 (d, J = 2.1 Hz, 1H), 4.20-4.00 (dq, J = 4.2, 2.3 Hz, 1H), 3.75 (s, 4H), 3.55 (s, 3H), 3.35 (dd, J = 7.7, 4.6 Hz, 2H), 3.25 (m, 2H), 2.31-1.89 (m, 5H). | 511.4 |
| (S)-N-(4-(4-amino-5-(4-(3-methoxypyrrolidine-1-carbonyl)phenyl)-7-methyl-7H-pyrrolo[2,3-d]pyrimidin-6-yl)phenyl) methacrylamide | 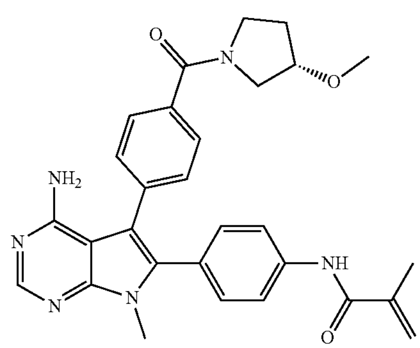 [SMILES: C=C(C)C(=O)Nc1ccc(-c2c(-c3ccc(C(=O)N4CC[C@H](OC)C4)cc3)c3c(N)ncnc3n2C)cc1] | $^1$H NMR (400 MHz, DMSO-d$_6$) δ 9.90 (s, 1H), 8.20 (s, 1H), 7.74-7.66 (m, 2H), 7.48 (dd, J = 7.9, 5.6 Hz, 2H), 7.26 (dd, J = 8.2, 1.7 Hz, 4H), 5.93 (s, 1H), 5.80 (s, 1H), 5.53 (t, J = 1.5 Hz, 1H), 3.97 (d, J = 32.6 Hz, 1H), 3.61 (s, 3H), 3.51 (d, J = 11.3 Hz, 3H), 3.26 (s, 2H), 3.17 (s, 2H), 2.01-1.92 (m, 5H). | 511.45 |
| N-(4-(5-(4-(2-azabicyclo[2.2.1]heptane-2-carbonyl)phenyl)-4-amino-7-methyl-7H-pyrrolo[2,3-d]pyrimidin-6-yl)phenyl) methacrylamide | 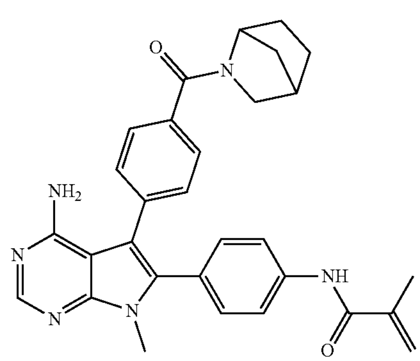 [SMILES: C=C(C)C(=O)Nc1ccc(-c2c(-c3ccc(C(=O)N4CC5CCC4C5)cc3)c3c(N)ncnc3n2C)cc1] | $^1$H NMR (400 MHz, Methanol-d$_4$) δ 8.22 (d, J = 1.7 Hz, 1H), 7.68 (dd, J = 8.7, 2.4 Hz, 2H), 7.50 (dd, J = 8.3, 2.8 Hz, 2H), 7.39 (dd, J = 11.2, 8.1 Hz, 2H), 7.29 (dq, J = 8.6, 2.1 Hz, 2H), 5.81 (s, 1H), 5.54 (s, 1H), 4.18 (s, 1H), 3.71 (d, J = 1.8 Hz, 3H), 3.55 (d, J = 11.3 Hz, 1H), 3.19 (dd, J = 11.3, 1.7 Hz, 1H), 2.70 (s, 1H), 2.08-2.02 (m, 3H), 1.80 (q, J = 12.8, 10.8 Hz, 3H), 1.70 (d, J = 10.3 Hz, 1H), 1.59 (s, 1H), 1.52 (d, J = 9.7 Hz, 1H). | 507.40 |

TABLE 2-continued

Additional Exemplary Compounds

| Compound | Structure | Proton NMR | MS [M + 1] |
|---|---|---|---|
| N-(4-(5-(4-(3-aza-bicyclo[3.2.1]octane-3-carbonyl)phenyl)-4-amino-7-methyl-7H-pyrrolo[2,3-d]pyrimidin-6-yl)phenyl)methacrylamide | 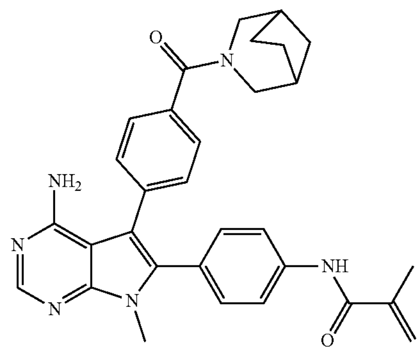 [SMILES: C=C(C)C(=O)Nc1ccc(-c2c(-c3ccc(C(=O)N4CC5CCC(C5)C4)cc3)c3c(N)ncnc3n2C)cc1] | $^1$H NMR (400 MHz, DMSO-d$_6$) δ 9.89 (s, 1H), 8.20 (s, 1H), 7.74-7.67 (m, 2H), 7.28 (q, J = 8.1 Hz, 6H), 5.94 (s, 2H), 5.80 (s, 1H), 5.53 (d, J = 2.0 Hz, 1H), 4.29 (s, 1H), 3.38 (s, 1H), 3.32 (s, 2H), 3.17 (s, 1H), 2.79 (s, 1H), 2.28-2.19 (m, 2H), 2.12 (s, 1H), 1.95 (d, J = 1.4 Hz, 3H), 1.60 (d, J = 10.5 Hz, 3H), 1.49 (s, 3H), 1.39 (s, 1H). | 521.40 |
| (R)-4-(4-amino-6-(4-methacrylamido-phenyl)-7-methyl-7H-pyrrolo[2,3-d]pyrimidin-5-yl)-N-(1-cyclopropyl-2-hydroxyethyl)benzamide | 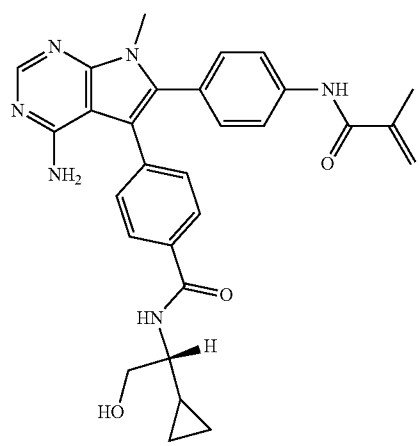 [SMILES: C=C(C)C(=O)Nc1ccc(-c2c(-c3ccc(C(=O)N[C@@H](CO)C4CC4)cc3)c3c(N)ncnc3n2C)cc1] | $^1$H NMR (400 MHz, DMSO-d$_6$) δ 9.89 (s, 1H), 8.21 (s, 1H), 8.14 (d, J = 8.4 Hz, 1H), 7.82 (d, J = 8.1 Hz, 2H), 7.70 (d, J = 8.5 Hz, 2H), 7.32-7.23 (m, 4H), 5.79 (s, 2H), 5.53 (s, 1H), 4.63 (t, J = 5.7 Hz, 1H), 3.62 (s, 3H), 3.58-3.39 (m, 3H), 1.95 (s, 3H), 0.98 (d, J = 8.1 Hz, 1H), 0.48-0.42 (m, 1H), 0.38-0.13 (m, 3H). | 511.40 |
| 4-(4-amino-6-(4-methacrylamido-phenyl)-7-methyl-7H-pyrrolo[2,3-d]pyrimidin-5-yl)-N-(pyrimidin-2-yl)benzamide | 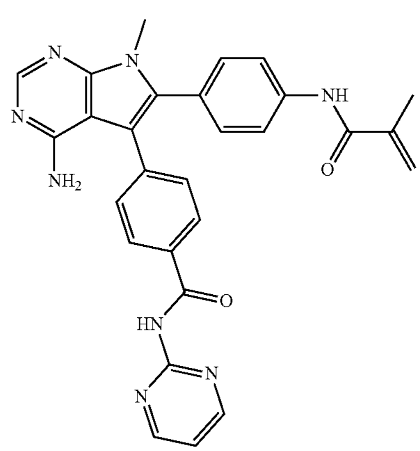 [SMILES: C=C(C)C(=O)Nc1ccc(-c2c(-c3ccc(C(=O)Nc4ncccn4)cc3)c3c(N)ncnc3n2C)cc1] | $^1$H NMR (400 MHz, DMSO-d$_6$) δ 9.91 (s, 1H), 8.73 (d, J = 4.8 Hz, 2H), 8.22 (s, 1H), 7.96-7.89 (m, 2H), 7.77-7.69 (m, 2H), 7.38-7.30 (m, 2H), 7.33-7.22 (m, 3H), 5.98 (s, 1H), 5.80 (t, J = 1.0 Hz, 1H), 5.53 (t, J = 1.4 Hz, 1H), 3.62 (s, 3H), 1.95 (t, J = 1.2 Hz, 3H). | 505.40 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-methyl-N-(pyrimidin-2-yl)benzamide | 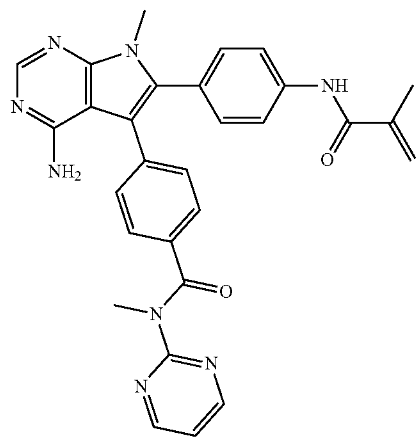 [SMILES: C=C(C)C(=O)Nc1ccc(-c2c(-c3ccc(C(=O)N(C)c4ncccn4)cc3)c3c(N)ncnc3n2C)cc1] | $^1$H NMR (400 MHz, DMSO-d$_6$) δ 9.92 (s, 1H), 8.52 (d, J = 4.8 Hz, 2H), 8.19 (s, 1H), 7.75-7.68 (m, 2H), 7.25-7.08 (m, 7H), 5.82 (d, J = 1.3 Hz, 2H), 5.56 (t, J = 1.4 Hz, 1H), 3.61 (s, 3H), 3.54 (s, 3H), 1.97 (d, J = 1.3 Hz, 3H), 1.24 (s, 1H). | 519.25 |
| 4-(4-amino-6-(4-methacrylamido-phenyl)-7-methyl-7H-pyrrolo[2,3-d]pyrimidin-5-yl)-N-methyl-N-(tetrahydrofuran-3-yl)benzamide | 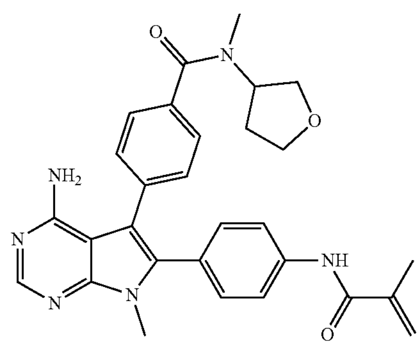 [SMILES: C=C(C)C(=O)Nc1ccc(-c2c(-c3ccc(C(=O)N(C)C4CCOC4)cc3)c3c(N)ncnc3n2C)cc1] | $^1$H NMR (400 MHz, DMSO-d$_6$) δ 9.93 (s, 1H), 8.40 (s, 1H), 7.73 (d, J = 8.4 Hz, 2H), 7.35 (s, 2H), 7.30-7.23 (m, 4H), 5.80 (s, 1H), 5.54 (s, 1H), 3.99-3.89 (m, 1H), 3.78 (dd, J = 9.6, 3.9 Hz, 1H), 3.67 (s, 3H), 3.42 (s, 1H), 2.87 (s, 3H), 2.11 (s, 1H), 1.95 (s, 3H). | 511.40 |
| N-(4-(5-(4-(2-azabicyclo[2.1.1]hexane-2-carbonyl)phenyl)-4-amino-7-methyl-7H-pyrrolo[2,3-d]pyrimidin-6-yl)phenyl)methacrylamide | 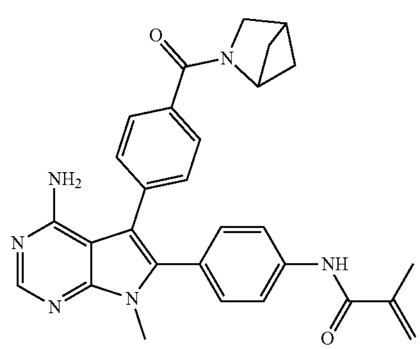 [SMILES: C=C(C)C(=O)Nc1ccc(-c2c(-c3ccc(C(=O)N4CC5CC4C5)cc3)c3c(N)ncnc3n2C)cc1] | $^1$H NMR (400 MHz, DMSO-d$_6$) δ 9.90 (s, 1H), 8.21 (s, 1H), 7.75-7.67 (m, 2H), 7.64 (d, J = 7.8 Hz, 1H), 7.40 (d, J = 7.7 Hz, 1H), 7.27 (d, J = 8.0 Hz, 4H), 5.95 (s, 1H), 5.80 (t, J = 1.0 Hz, 1H), 5.53 (t, J = 1.5 Hz, 1H), 4.69-4.33 (d, J = 6.8 Hz, 1H), 3.61 (s, 3H), 3.45 (d, J = 9.0 Hz, 2H), 2.93-2.84 (m, 1H), 1.95 (d, J = 1.2 Hz, 4H), 1.47 (s, 1H), 1.33 (s, 1H). | 493.25 |
| N-(4-(5-(4-(2-azaspiro[3.4]octane-2-carbonyl)phenyl)-4-amino-7-methyl-7H-pyrrolo[2,3-d]pyrimidin-6-yl)phenyl)methacrylamide | 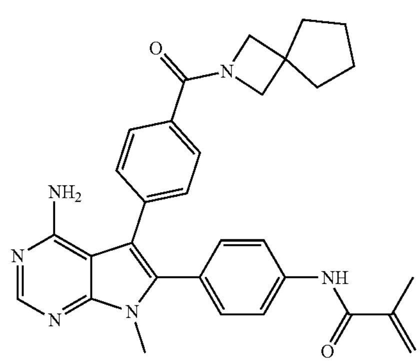 [SMILES: C=C(C)C(=O)Nc1ccc(-c2c(-c3ccc(C(=O)N4CC5(CCCC5)C4)cc3)c3c(N)ncnc3n2C)cc1] | $^1$H NMR (400 MHz, Methanol-d$_4$) δ 8.22 (s, 1H), 7.66 (dd, J = 10.2, 8.2 Hz, 4H), 7.42 (d, J = 7.9 Hz, 2H), 7.28 (d, J = 8.3 Hz, 2H), 5.81 (s, 1H), 5.54 (s, 1H), 4.22 (s, 2H), 4.02 (s, 2H), 3.70 (s, 3H), 2.05 (d, J = 4.9 Hz, 3H), 1.87 (d, J = 6.6 Hz, 4H), 1.68-1.64 (m, 4H). | 521.4 |

TABLE 2-continued

Additional Exemplary Compounds

| Compound | Structure | Proton NMR | MS [M + 1] |
|---|---|---|---|
| N-(4-(4-amino-5-(4-(hexahydro-1H-furo[3,4-c]pyrrole-5-carbonyl)phenyl)-7-methyl-7H-pyrrolo[2,3-d]pyrimidin-6-yl)phenyl)methacrylamide | 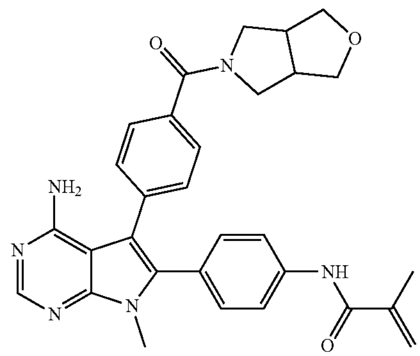 [SMILES: C=C(C)C(=O)Nc1ccc(-c2c(-c3ccc(C(=O)N4CC5COCC5C4)cc3)c3c(N)ncnc3n2C)cc1] | $^1$H NMR (400 MHz, Methanol-d$_4$) δ 8.22 (s, 1H), 7.69 (m, 2H), 7.55 (m, 2H), 7.39 (d, J = 8.1 Hz, 2H), 7.25 (m, 2H), 5.81 (s, 1H), 5.54 (d, J = 1.9 Hz, 1H), 4.05-3.72 (s, 4H), 3.70 (s, 5H), 3.55 (s, 1H), 3.42 (d, J = 11.6 Hz, 1H), 3.03 (s, 2H), 2.04 (d, J = 1.6 Hz, 3H). | 523.4 |
| 4-(4-amino-6-(4-methacrylamido-phenyl)-7-methyl-7H-pyrrolo[2,3-d]pyrimidin-5-yl)-N-methyl-N-((1-methyl-1H-pyrazol-4-yl)methyl)benzamide | 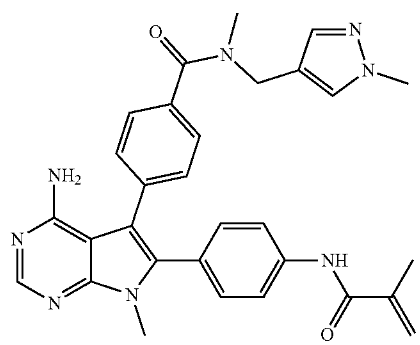 [SMILES: C=C(C)C(=O)Nc1ccc(-c2c(-c3ccc(C(=O)N(C)Cc4cnn(C)c4)cc3)c3c(N)ncnc3n2C)cc1] | $^1$H NMR (400 MHz, DMSO-d$_6$) δ 9.88 (s, 1H), 8.20 (s, 1H), 7.70 (d, J = 8.5 Hz, 2H), 7.58 (s, 1H), 7.37 (d, J = 8.0 Hz, 2H), 7.26 (dd, J = 8.1, 3.7 Hz, 4H), 5.80 (s, 2H), 5.56-5.51 (m, 1H), 4.44 (s, 1H), 4.28 (s, 1H), 3.80 (s, 3H), 3.61 (s, 3H), 2.87 (s, 3H), 1.95 (s, 3H). | 535.45 |
| 4-(4-amino-6-(4-methacrylamido-phenyl)-7-methyl-7H-pyrrolo[2,3-d]pyrimidin-5-yl)-N-(1,2,4-oxadiazol-3-yl)benzamide | 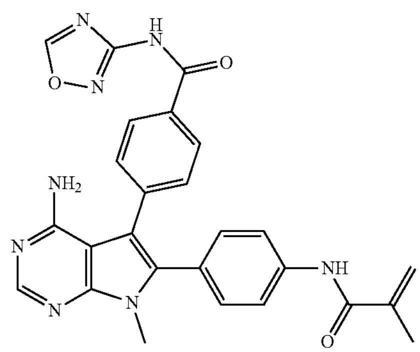 [SMILES: C=C(C)C(=O)Nc1ccc(-c2c(-c3ccc(C(=O)Nc4ncon4)cc3)c3c(N)ncnc3n2C)cc1] | $^1$H NMR (400 MHz, DMSO-d$_6$) δ 11.52 (s, 1H), 9.91 (s, 1H), 9.01 (s, 1H), 8.23 (s, 1H), 8.07-8.00 (m, 2H), 7.76-7.68 (m, 2H), 7.47-7.40 (m, 2H), 7.32-7.25 (m, 2H), 6.04 (s, 2H), 5.80 (s, 1H), 5.54 (d, J = 1.7 Hz, 1H), 3.62 (s, 3H), 1.95 (d, J = 1.2 Hz, 3H). | 495.2 |
| N-((1,2,4-oxadiazol-3-yl)methyl)-4-(4-amino-6-(4-methacrylamido-phenyl)-7-methyl-7H-pyrrolo[2,3-d]pyrimidin-5-yl)-N-methylbenzamide | 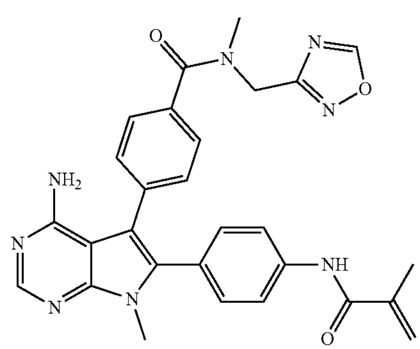 [SMILES: C=C(C)C(=O)Nc1ccc(-c2c(-c3ccc(C(=O)N(C)Cc4ncon4)cc3)c3c(N)ncnc3n2C)cc1] | $^1$H NMR (400 MHz, DMSO-d$_6$) δ 9.88 (s, 1H), 9.62 (s, 1H), 8.20 (d, J = 2.6 Hz, 1H), 7.73-7.67 (m, 2H), 7.44-7.37 (m, 2H), 7.26 (d, J = 8.5 Hz, 4H), 5.97 (s, 2H), 5.80 (s, 1H), 5.53 (s, 1H), 4.85 (s, 1H), 4.73 (s, 1H), 3.32 (s, 3H), 3.05 (s, 1H), 2.98 (s, 1H), 1.95 (t, J = 1.3 Hz, 3H). | 523.40 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-methyl-N-((3-methyl-1,2,4-oxadiazol-5-yl)methyl)benzamide | 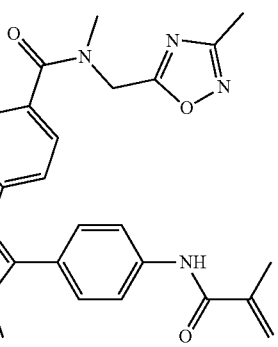 | ¹H NMR (400 MHz, DMSO-d₆) δ 9.88 (s, 1H), 8.20 (s, 1H), 7.70 (d, J = 8.3 Hz, 2H), 7.42 (s, 2H), 7.26 (d, J = 8.4 Hz, 3H), 5.80 (s, 1H), 5.53 (s, 1H), 4.91 (s, 2H), 3.61 (s, 3H), 3.29 (s, 1H), 3.11 (s, 3H), 2.35 (s, 3H), 1.95 (s, 3H). | 537.45 |
| N-(4-(5-(4-(2-oxa-6-azaspiro[3.4]octane-6-carbonyl)phenyl)-4-amino-7-methyl-7H-pyrrolo[2,3-d]pyrimidin-6-yl)phenyl)methacrylamide | 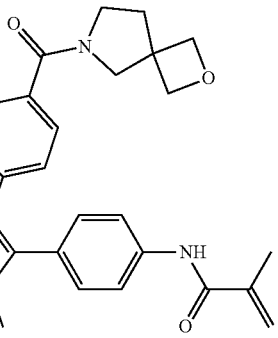 | ¹H NMR (400 MHz, DMSO-d₆) δ 9.90 (s, 1H), 8.21 (s, 1H), 7.71 (dd, J = 8.7, 3.5 Hz, 2H), 7.49 (t, J = 1.0 Hz, 2H), 7.27 (t, J = 7.5 Hz, 4H), 5.96 (s, 1H), 5.80 (t, J = 1.0 Hz, 1H), 5.56-5.51 (m, 1H), 4.62 (d, J = 6.0 Hz, 1H), 4.47 (q, J = 7.7, 6.8 Hz, 3H), 3.70 (s, 2H), 3.61 (s, 3H), 3.46 (q, J = 7.3 Hz, 2H), 2.14 (dt, J = 12.1, 7.0 Hz, 2H), 1.95 (t, J = 1.2 Hz, 3H). | 523.25 |
| N-{4-[4-amino-5-(4-(6-azaspiro[3.4]octane-6-carbonyl}phenyl)-7-methyl-7H-pyrrolo[2,3-d]pyrimidin-6-yl]phenyl}-2-methylprop-2-enamide | 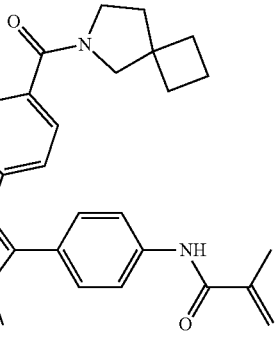 | ¹H NMR (400 MHz, DMSO-d₆) δ 9.93 (s, 1H), 8.38 (s, 1H), 7.73 (dd, J = 8.7, 2.7 Hz, 2H), 7.50 (d, J = 8.1 Hz, 2H), 7.31-7.23 (m, 4H), 6.80 (s, 2H), 5.80 (s, 1H), 5.54 (s, 1H), 3.43 (dd, J = 11.9, 5.6 Hz, 5H), 2.03 (s, 1H), 1.95 (s, 3H), 1.89 (dd, J = 18.8, 5.4 Hz, 8H). | 521.45 |
| N-(4-(5-(4-(3-azabicyclo[3.2.0]heptane-3-carbonyl)phenyl)-4-amino-7-methyl-7H-pyrrolo[2,3-d]pyrimidin-6-yl)phenyl)methacrylamide | 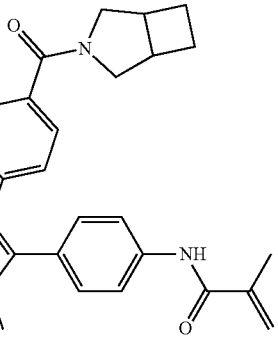 | ¹H NMR (400 MHz, DMSO-d₆) δ 9.89 (s, 1H), 8.21 (s, 1H), 7.74-7.67 (m, 2H), 7.52-7.45 (m, 2H), 7.31-7.23 (m, 4H), 5.80 (s, 2H), 5.53 (t, J = 1.4 Hz, 1H), 3.96 (s, 1H), 3.61 (s, 3H), 3.32 (s, 5H), 2.91 (s, 2H), 2.14 (s, 2H), 1.95 (d, J = 1.2 Hz, 3H), 1.60 (s, 2H). | 507.40 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-methyl-N-((tetrahydrofuran-2-yl)methyl)benzamide | 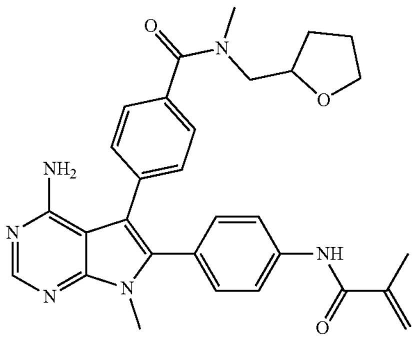 [SMILES: C=C(C)C(=O)Nc1ccc(-c2c(-c3ccc(C(=O)N(C)CC4CCCO4)cc3)c3c(N)ncnc3n2C)cc1] | ¹H NMR (400 MHz, DMSO-d₆) δ 9.88 (s, 1H), 8.21 (s, 1H), 7.74-7.67 (m, 2H), 7.33 (s, 2H), 7.26 (dd, J = 8.5, 2.9 Hz, 4H), 5.79 (s, 1H), 5.56-5.50 (m, 1H), 4.09 (s, 1H), 4.03 (s, 1H), 3.79 (s, 1H), 3.62 (s, 3H), 2.99 (s, 3H), 1.95 (d, J = 1.5 Hz, 3H), 1.54 (s, 1H). | 525.45 |
| N-{4-[4-amino-7-methyl-5-(4-{1-oxa-6-azaspiro[3.3]heptane-6-carbonyl}phenyl)-7H-pyrrolo[2,3-d]pyrimidin-6-yl]phenyl}-2-methylprop-2-enamide | 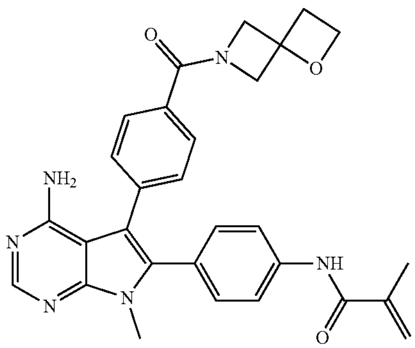 [SMILES: C=C(C)C(=O)Nc1ccc(-c2c(-c3ccc(C(=O)N4CC5(CCO5)C4)cc3)c3c(N)ncnc3n2C)cc1] | ¹H NMR (400 MHz, DMSO-d₆) δ 9.90 (s, 1H), 8.21 (s, 1H), 7.71 (d, J = 8.5 Hz, 2H), 7.60 (d, J = 8.2 Hz, 2H), 7.31-7.23 (m, 4H), 5.91 (s, 3H), 5.80 (s, 1H), 5.54 (s, 1H), 4.53 (s, 1H), 4.40 (t, J = 7.5 Hz, 2H), 4.31 (s, 1H), 4.12 (s, 1H), 3.61 (s, 3H), 2.83 (t, J = 7.4 Hz, 2H), 1.95 (s, 3H). | 509.35 |
| N-(4-(4-amino-7-methyl-5-(4-(3-(tetrahydrofuran-3-yl)azetidine-1-carbonyl)phenyl)-7H-pyrrolo[2,3-d]pyrimidin-6-yl)phenyl)methacrylamide | 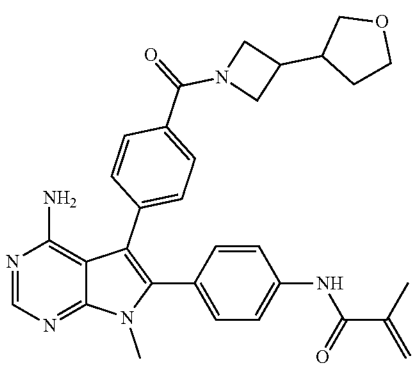 [SMILES: C=C(C)C(=O)Nc1ccc(-c2c(-c3ccc(C(=O)N4CC(C5CCOC5)C4)cc3)c3c(N)ncnc3n2C)cc1] | ¹H NMR (400 MHz, DMSO-d₆) δ 9.90 (s, 1H), 8.21 (s, 1H), 7.74-7.67 (m, 2H), 7.61 (d, J = 7.9 Hz, 2H), 7.27 (t, J = 8.6 Hz, 4H), 5.93 (s, 1H), 5.80 (s, 1H), 5.54 (s, 1H), 4.39 (d, J = 8.1 Hz, 1H), 4.20-3.90 (m, 2H), 3.73 (d, J = 7.4 Hz, 3H), 3.61 (s, 4H), 3.30 (s, 2H), 2.59 (s, 1H), 1.95 (s, 4H), 1.45 (s, 1H). | 537.35 |
| 4-(4-amino-6-(4-methacrylamido-phenyl)-7-methyl-7H-pyrrolo[2,3-d]pyrimidin-5-yl)-N-(3,3-difluorocyclobutyl)-N-methylbenzamide | 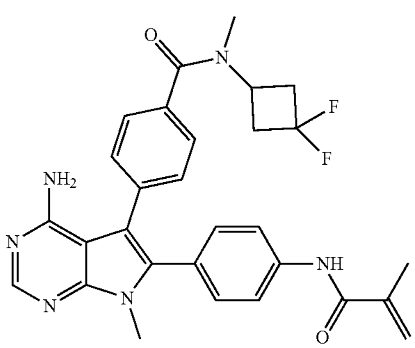 [SMILES: C=C(C)C(=O)Nc1ccc(-c2c(-c3ccc(C(=O)N(C)C4CC(F)(F)C4)cc3)c3c(N)ncnc3n2C)cc1] | ¹H NMR (400 MHz, DMSO-d₆) δ 9.89 (s, 1H), 8.21 (s, 1H), 7.74-7.67 (m, 2H), 7.37 (d, J = 7.7 Hz, 2H), 7.31-7.23 (m, 4H), 6.05 (s, 2H), 5.80 (s, 1H), 5.53 (d, J = 1.9 Hz, 1H), 4.45 (s, 1H), 3.62 (s, 3H), 3.01-2.69 (m, 7H), 1.95 (d, J = 1.5 Hz, 3H). | 531.40 |

TABLE 2-continued

Additional Exemplary Compounds

| Compound | Structure | Proton NMR | MS [M + 1] |
|---|---|---|---|
| 4-(6-(4-acrylamidophenyl)-4-amino-7-methyl-7H-pyrrolo[2,3-d]pyrimidin-5-yl)-N-methylcyclohexane-1-carboxamide | 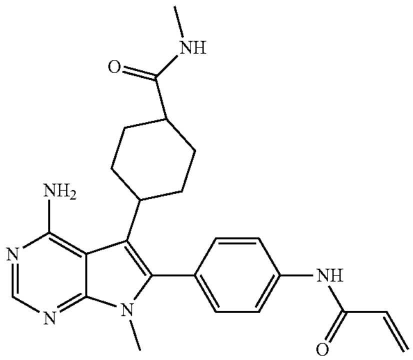 | ¹H NMR (400 MHz, DMSO-d₆) δ 10.33 (s, 1H), 8.07 (s, 1H), 7.89 (d, J = 4.4 Hz, 1H), 7.85-7.79 (m, 2H), 7.39-7.32 (m, 2H), 6.93 (s, 2H), 6.49 (dd, J = 17.0, 10.1 Hz, 1H), 6.31 (dd, J = 17.0, 2.0 Hz, 1H), 5.80 (dd, J = 10.0, 2.0 Hz, 1H), 3.43 (s, 3H), 2.60 (d, J = 4.6 Hz, 4H), 2.45 (s, 1H), 2.21-2.10 (m, 2H), 1.83 (d, J = 12.9 Hz, 2H), 1.52-1.39 (m, 4H). | 433.35 |
| 4-(6-(4-acrylamidophenyl)-4-amino-7-methyl-7H-pyrrolo[2,3-d]pyrimidin-5-yl)-N-cyclopentylcyclohex-3-enecarboxamide | 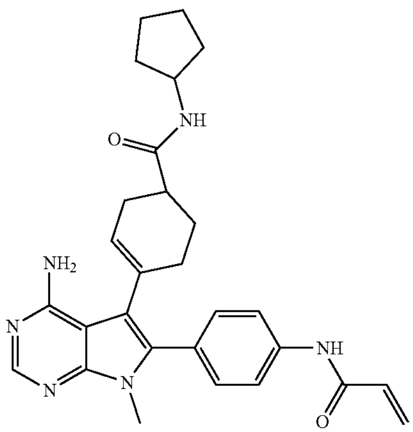 [SMILES: C=CC(=O)Nc1ccc(-c2c(C3=CCC(C(=O)NC4CCCC4)CC3)c3c(N)ncnc3n2C)cc1] | ¹H NMR (400 MHz, DMSO-d₆) δ 10.31 (s, 1H), 8.10 (s, 1H), 7.78 (dd, J = 8.2, 6.6 Hz, 3H), 7.48-7.40 (m, 2H), 6.47 (dd, J = 17.0, 10.1 Hz, 1H), 6.30 (dd, J = 17.0, 2.1 Hz, 1H), 5.83-5.75 (m, 2H), 3.99 (p, J = 6.8 Hz, 1H), 3.57 (s, 3H), 2.45 (t, J = 6.0 Hz, 1H), 2.28 (s, 1H), 2.19 (d, J = 17.9 Hz, 1H), 1.90-1.84 (m, 2H), 1.82-1.69 (m, 2H), 1.62 (s, 4H), 1.47 (q, J = 1.0 Hz, 2H), 1.35 (s, 1H), 1.32 (s, 1H). | 485.2 |
| N-(4-(4-amino-7-methyl-5-(4-(pyrrolidine-1-carbonyl)cyclohex-1-enyl)-7H-pyrrolo[2,3-d]pyrimidin-6-yl)phenyl)acrylamide | 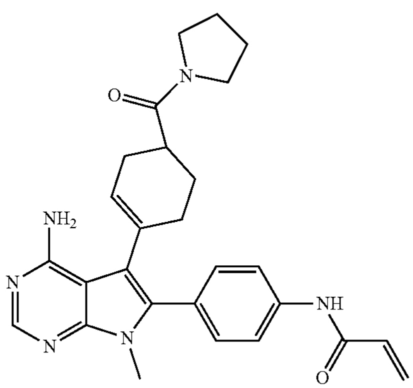 [SMILES: C=CC(=O)Nc1ccc(-c2c(C3=CCC(C(=O)N4CCCC4)CC3)c3c(N)ncnc3n2C)cc1] | ¹H NMR (400 MHz, DMSO-d₆) δ 10.30 (s, 1H), 8.10 (s, 1H), 7.82-7.75 (m, 2H), 7.49-7.42 (m, 2H), 6.47 (dd, J = 17.0, 10.1 Hz, 1H), 6.30 (dd, J = 17.0, 2.1 Hz, 1H), 5.83-5.73 (m, 2H), 3.58 (s, 3H), 3.51 (dt, J = 10.0, 6.6 Hz, 1H), 3.43 (dt, J = 10.0, 6.7 Hz, 1H), 3.32-3.20 (m, 2H), 2.82 (q, J = 6.0 Hz, 1H), 2.27 (d, J = 12.9 Hz, 2H), 1.89 (s, 4H), 1.76 (p, J = 6.7 Hz, 2H), 1.63 (d, J = 6.1 Hz, 2H). | 471.2 |
| 4-(6-(4-acrylamidophenyl)-4-amino-7-methyl-7H-pyrrolo[2,3-d]pyrimidin-5-yl)-N,N-dimethylcyclohex-3-enecarboxamide | 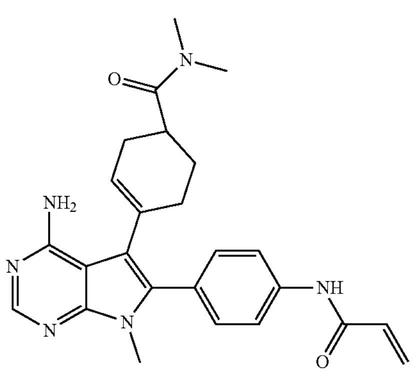 | ¹H NMR (400 MHz, DMSO-d₆) δ 10.30 (s, 1H), 8.10 (s, 1H), 7.82-7.75 (m, 2H), 7.49-7.41 (m, 2H), 6.47 (dd, J = 17.0, 10.1 Hz, 1H), 6.29 (dd, J = 17.0, 2.1 Hz, 1H), 5.83-5.73 (m, 2H), 3.58 (s, 3H), 3.02 (s, 3H), 3.08-2.97 (m, 1H), 2.82 (s, 3H), 2.27 (d, J = 12.9 Hz, 2H), 1.90 (s, 1H), 1.83 (d, J = 17.4 Hz, 1H), 1.61 (d, J = 6.0 Hz, 2H). | 445.2 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-methyl-5,6-dihydropyridine-1(2H)-carboxamide | 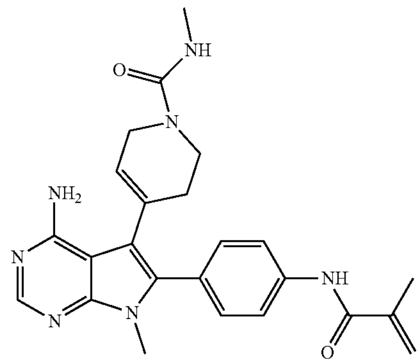 [SMILES: C=C(C)C(=O)Nc1ccc(-c2c(C3=CCN(C(=O)NC)CC3)c3c(N)ncnc3n2C)cc1] | ¹H NMR (400 MHz, DMSO-d₆) δ 9.95 (s, 1H), 8.13 (s, 1H), 7.84-7.78 (m, 2H), 7.44-7.38 (m, 2H), 6.34 (d, J = 4.5 Hz, 1H), 6.25 (s, 2H), 5.83 (s, 1H), 5.78 (s, 1H), 5.55 (d, J = 1.8 Hz, 1H), 3.91 (d, J = 3.3 Hz, 2H), 3.56 (s, 3H), 2.57 (d, J = 4.3 Hz, 3H), 1.97 (d, J = 1.4 Hz, 3H), 1.95 (s, 2H). | 446.35 |
| N-(4-(4-amino-5-(4-(pyrrolidin-1-ylsulfonyl)phenyl)-7H-pyrrolo[2,3-d]pyrimidin-6-yl)phenyl)methacrylamide | 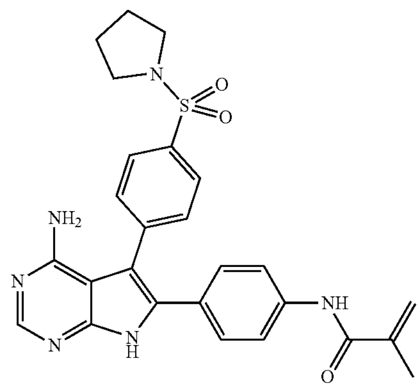 [SMILES: C=C(C)C(=O)Nc1ccc(-c2[nH]c3ncnc(N)c3c2-c2ccc(S(=O)(=O)N3CCCC3)cc2)cc1] | ¹H NMR (400 MHz, DMSO-d₆) δ 12.21 (s, 1H), 9.85 (s, 1H), 8.14 (s, 1H), 7.88-7.81 (m, 2H), 7.62-7.52 (m, 4H), 7.16 (d, J = 8.8 Hz, 2H), 5.86 (s, 2H), 5.78 (s, 1H), 5.52 (s, 1H), 3.24-3.12 (m, 2H), 1.94 (d, J = 1.2 Hz, 3H), 1.71-1.63 (m, 3H), 1.57 (s, 1H), 1.32 (q, J = 7.2 Hz, 1H), 0.94 (t, J = 12 Hz, 1H). | 503.15 |
| N-(4-(4-amino-5-(3-fluoro-4-((5-fluoropyrimidin-2-yl)oxy)phenyl)-7H-pyrrolo[2,3-d]pyrimidin-6-yl)phenyl)methacrylamide | 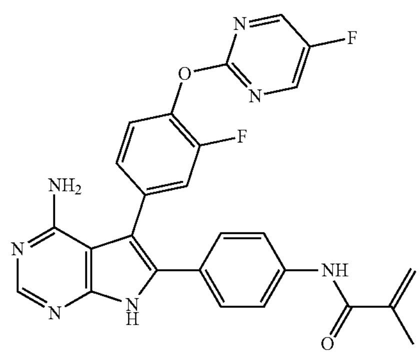 [SMILES: C=C(C)C(=O)Nc1ccc(-c2[nH]c3ncnc(N)c3c2-c2ccc(Oc3ncc(F)cn3)c(F)c2)cc1] | ¹H NMR (400 MHz, DMSO-d6) δ 12.14 (s, 1H), 9.85 (s, 1H), 8.81 (s, 2H), 8.14 (s, 1H), 7.68-7.61 (m, 2H), 7.48 (t, J = 8.4 Hz, 1H), 7.38-7.27 (m, 3H), 7.24 (dd, J = 8.3, 2.0 Hz, 1H), 5.80 (s, 1H), 5.75 (s, 1H), 5.53 (d, J = 1.6 Hz, 1H), 1.95 (s, 3H). | 500.35 |
| N-(4-(4-amino-7-methyl-5-(4-((1-methyl-1H-pyrazol-3-yl)oxy)phenyl)-7H-pyrrolo[2,3-d]pyrimidin-6-yl)phenyl)acrylamide | 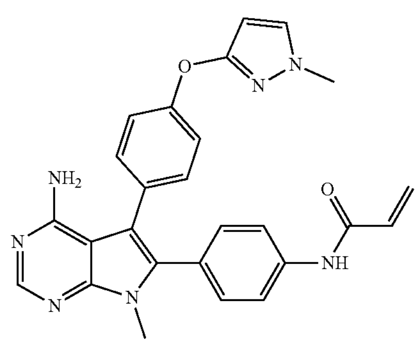 [SMILES: C=CC(=O)Nc1ccc(-c2c(-c3ccc(Oc4ccn(C)n4)cc3)c3c(N)ncnc3n2C)cc1] | ¹H NMR (400 MHz, DMSO-d6) δ 10.26 (s, 1H), 8.18 (s, 1H), 7.72-7.62 (m, 3H), 7.32-7.25 (m, 2H), 7.25-7.16 (m, 2H), 7.07-6.98 (m, 2H), 6.44 (dd, J = 17.0, 10.1 Hz, 1H), 6.27 (dd, J = 17.0, 2.1 Hz, 1H), 5.88 (d, J = 2.3 Hz, 1H), 5.78 (dd, J = 10.0, 2.1 Hz, 1H), 3.75 (s, 3H), 3.60 (s, 3H). | 466.30 |

TABLE 2-continued

Additional Exemplary Compounds

| Compound | Structure | Proton NMR | MS [M + 1] |
|---|---|---|---|
| N-(4-(5-(4-((1H-pyrazol-1-yl)methyl)phenyl)-4-amino-7-methyl-7H-pyrrolo[2,3-d]pyrimidin-6-yl)phenyl)methacrylamide | 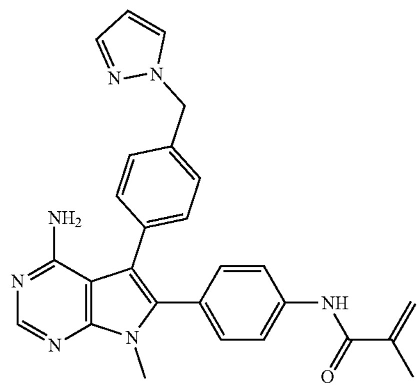 [SMILES: C=C(C)C(=O)Nc1ccc(-c2c(-c3ccc(Cn4cccn4)cc3)c3c(N)ncnc3n2C)cc1] | $^1$H NMR (400 MHz, DMSO-d$_6$) δ 9.88 (s, 1H), 8.19 (s, 1H), 7.84 (d, J = 22 Hz, 1H), 7.72-7.64 (m, 2H), 7.48 (d, J = 1.8 Hz, 1H), 7.31-7.20 (m, 4H), 7.14 (d, J = 8.0 Hz, 2H), 6.28 (t, J = 2.0 Hz, 1H), 5.80 (s, 2H), 5.53 (t, J = 1.6 Hz, 1H), 5.35 (s, 2H), 3.59 (s, 3H), 1.95 (t, J = 1.2 Hz, 3H). | 464.30 |
| N-(4-(4-amino-7-methyl-5-(4-((3-methyl-1H-pyrazol-1-yl)methyl)phenyl)-7H-pyrrolo[2,3-d]pyrimidin-6-yl)phenyl)methacrylamide | 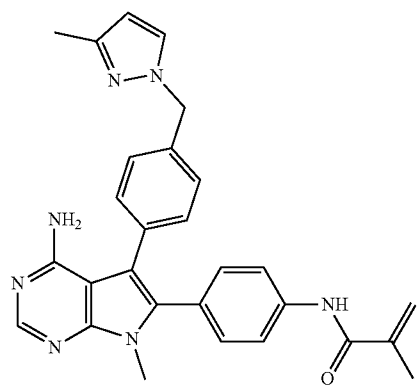 [SMILES: C=C(C)C(=O)Nc1ccc(-c2c(-c3ccc(Cn4ccc(C)n4)cc3)c3c(N)ncnc3n2C)cc1] | $^1$H NMR (400 MHz, DMSO-d6) δ 9.87 (s, 1H), 8.19 (s, 1H), 7.69 (dd, J = 5.4, 3.1 Hz, 3H), 7.30-7.18 (m, 4H), 7.14 (d, J = 8.2 Hz, 2H), 6.04 (d, J = 2.2 Hz, 1H), 5.91 (s, 2H), 5.80 (s, 1H), 5.53 (t, J = 1.5 Hz, 1H), 5.24 (s, 2H), 3.59 (s, 3H), 2.15 (s, 3H), 1.95 (t, J = 1.3 Hz, 3H). | 478.35 |
| N-(4-(4-amino-5-(4-((1-methyl-1H-pyrazol-3-yl)oxy)phenyl)-7H-pyrrolo[2,3-d]pyrimidin-6-yl)phenyl)acrylamide | 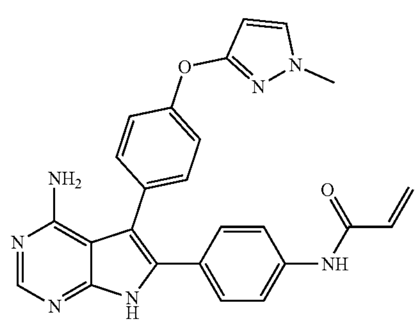 [SMILES: C=CC(=O)Nc1ccc(-c2[nH]c3ncnc(N)c3c2-c2ccc(Oc3ccn(C)n3)cc2)cc1] | $^1$H NMR (400 MHz, DMSO-d6) δ 11.75 (s, 1H), 10.13 (s, 1H), 8.12 (d, J = 13.8 Hz, 2H), 7.64 (d, J = 8.8 Hz, 2H), 7.59-7.52 (m, 2H), 7.46-7.39 (m, 2H), 7.23-7.14 (m, 3H), 6.57-6.37 (m, 1H), 6.31-6.11 (m, 1H), 5.96 (s, 2H), 5.81-5.69 (m, 1H), 3.80 (s, 3H). | 452.15 |
| N-(4-(4-amino-7-methyl-5-(4-((1-methyl-1H-pyrazol-3-yl)oxy)phenyl)-7H-pyrrolo[2,3-d]pyrimidin-6-yl)phenyl)methacrylamide | 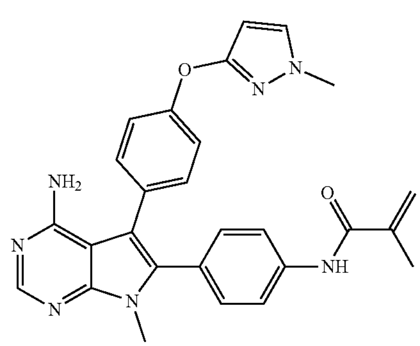 [SMILES: C=C(C)C(=O)Nc1ccc(-c2c(-c3ccc(Oc4ccn(C)n4)cc3)c3c(N)ncnc3n2C)cc1] | $^1$H NMR (400 MHz, DMSO-d6) δ 9.89 (s, 1H), 8.18 (s, 1H), 7.74-7.67 (m, 2H), 7.65 (d, J = 2.3 Hz, 1H), 7.31-7.23 (m, 2H), 7.23-7.16 (m, 2H), 7.06-6.98 (m, 2H), 5.88 (d, J = 2.3 Hz, 1H), 5.85-5.77 (m, 3H), 5.56-5.51 (m, 1H), 3.75 (s, 3H), 3.60 (s, 3H), 1.95 (d, J = 1.1 Hz, 3H). | 480.35 |

TABLE 2-continued

Additional Exemplary Compounds

| Compound | Structure | Proton NMR | MS [M + 1] |
|---|---|---|---|
| N-(4-(4-amino-7-methyl-5-(4-((4-methyl-1H-pyrazol-1-yl)methyl)phenyl)-7H-pyrrolo[2,3-d]pyrimidin-6-yl)phenyl) methacrylamide | 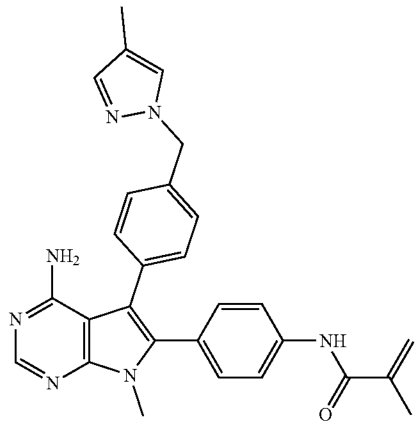 [SMILES: C=C(C)C(=O)Nc1ccc(-c2c(-c3ccc(Cn4cc(C)cn4)cc3)c3c(N)ncnc3n2C)cc1] | ¹H NMR (400 MHz, DMSO-d6) δ 9.88 (s, 1H), 8.19 (s, 1H), 7.72-7.65 (m, 2H), 7.58 (s, 1H), 7.27 (s, 2H), 7.27-7.17 (m, 3H), 7.13 (d, J = 8.1 Hz, 2H), 5.80 (s, 1H), 5.71 (s, 1H), 5.56-5.51 (m, 1H), 5.25 (s, 2H), 3.59 (s, 3H), 2.01 (s, 3H), 1.95 (d, J = 1.1 Hz, 3H). | 478.35 |
| N-(4-(4-amino-7-methyl-5-(4-((5-methyl-1H-pyrazol-1-yl)methyl)phenyl)-7H-pyrrolo[2,3-d]pyrimidin-6-yl)phenyl) methacrylamide | 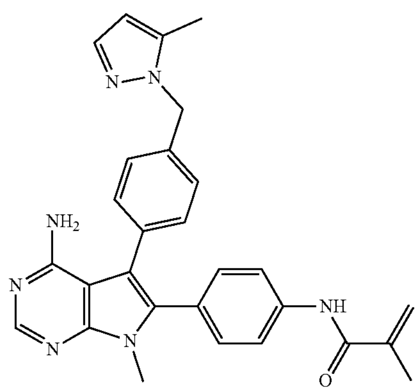 [SMILES: C=C(C)C(=O)Nc1ccc(-c2c(-c3ccc(Cn4nccc4C)cc3)c3c(N)ncnc3n2C)cc1] | ¹H NMR (400 MHz, DMSO-d6) δ 9.87 (s, 1H), 8.18 (s, 1H), 7.72-7.64 (m, 2H), 7.35 (d, J = 1.7 Hz, 1H), 7.29-7.17 (m, 4H), 7.04 (d, J = 7.9 Hz, 2H), 6.07 (d, J = 1.9 Hz, 1H), 5.96 (s, 1H), 5.80 (s, 1H), 5.78 (s, 1H), 5.53 (t, J = 1.5 Hz, 1H), 5.30 (s, 2H), 3.59 (s, 3H), 2.21 (s, 3H), 1.95 (d, J = 1.2 Hz, 3H). | 478.35 |
| N-(4-(4-amino-5-(4-(3,5-dimethyl-1H-pyrazol-1-yl)methyl)phenyl)-7-methyl-7H-pyrrolo[2,3-d]pyrimidin-6-yl)phenyl) acrylamide | 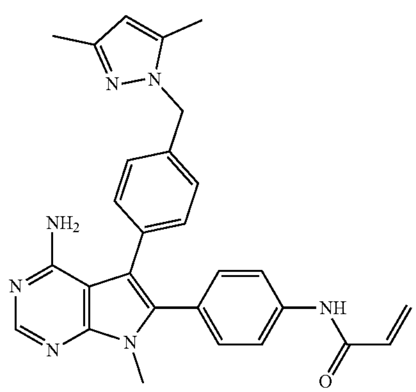 [SMILES: C=CC(=O)Nc1ccc(-c2c(-c3ccc(Cn4nc(C)cc4C)cc3)c3c(N)ncnc3n2C)cc1] | ¹H NMR (400 MHz, DMSO-d6) δ 10.24 (s, 1H), 8.18 (s, 1H), 7.70-7.63 (m, 2H), 7.30-7.21 (m, 2H), 7.24-7.16 (m, 2H), 7.04 (d, J = 8.1 Hz, 2H), 6.44 (dd, J = 17.0, 10.1 Hz, 1H), 6.27 (dd, J = 17.0, 2.1 Hz, 1H), 5.95 (s, 2H), 5.85 (s, 1H), 5.78 (dd, J = 10.0, 2.1 Hz, 1H), 5.19 (s, 2H), 3.59 (s, 3H), 2.14 (s, 3H), 2.10 (s, 3H). | 478.40 |
| N-((1,2,4-oxadiazol-3-yl)methyl)-4-(4-amino-6-(4-methacrylamido-phenyl)-7-methyl-7H-pyrrolo[2,3-d]pyrimidin-5-yl)benzamide | 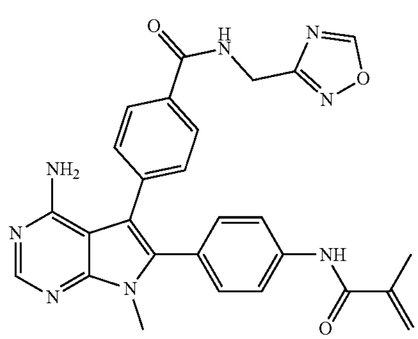 [SMILES: C=C(C)C(=O)Nc1ccc(-c2c(-c3ccc(C(=O)NCc4ncon4)cc3)c3c(N)ncnc3n2C)cc1] | ¹H NMR (400 MHz, DMSO-d₆) δ 9.89 (s, 1H), 9.55 (s, 1H), 9.16 (t, J = 5.8 Hz, 1H), 8.21 (s, 1H), 7.86-7.79 (m, 2H), 7.74-7.66 (m, 2H), 7.36-7.29 (m, 2H), 7.29-7.22 (m, 2H), 5.92 (s, 1H), 5.80 (s, 1H), 5.53 (t, J = 1.5 Hz, 1H), 4.62 (d, J = 5.7 Hz, 2H), 3.32 (s, 3H), 1.95 (d, J = 1.3 Hz, 3H). | 509.30 |

TABLE 2-continued

Additional Exemplary Compounds

| Compound | Structure | Proton NMR | MS [M + 1] |
|---|---|---|---|
| (S)-N-(4-(4-amino-7-methyl-5-(4-(2-methylpiperidine-1-carbonyl)phenyl)-7H-pyrrolo[2,3-d]pyrimidin-6-yl)phenyl) methacrylamide | 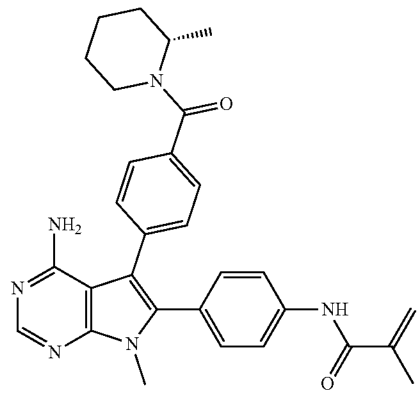 | ¹H NMR (400 MHz, DMSO-d₆) δ 9.89 (s, 1H), 8.20 (s, 1H), 7.70 (d, J = 8.6 Hz, 2H), 7.34-7.22 (m, 6H), 5.79 (s, 1H), 5.53 (s, 1H), 3.61 (s, 3H), 1.95 (t, J = 1.3 Hz, 3H), 1.61 (d, J = 16.0 Hz, 3H), 1.50 (s, 2H), 1.36 (d, J = 12.6 Hz, 1H), 1.18 (d, J = 1.0 Hz, 3H). | 509.45 |
| (R)-N-(4-(4-amino-7-methyl-5-(4-(2-methylpiperidine-1-carbonyl)phenyl)-7H-pyrrolo[2,3-d]pyrimidin-6-yl)phenyl) methacrylamide | 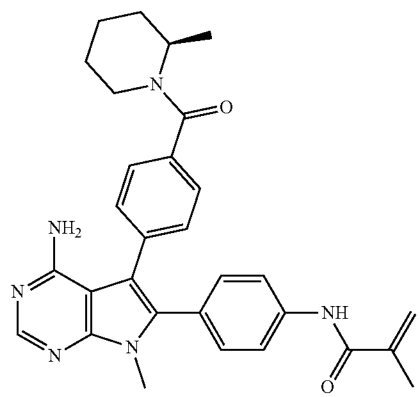 [SMILES: C=C(C)C(=O)Nc1ccc(-c2c(-c3ccc(C(=O)N4CCCC[C@H]4C)cc3)c3c(N)ncnc3n2C)cc1] | ¹H NMR (400 MHz, DMSO-d₆) δ 9.89 (s, 1H), 8.20 (s, 1H), 7.70 (d, J = 8.6 Hz, 2H), 7.34-7.22 (m, 6H), 5.79 (s, 1H), 5.53 (s, 1H), 3.61 (s, 3H), 2.98 (s, 1H), 1.95 (d, J = 1.3 Hz, 3H), 1.63 (s, 1H), 1.59 (s, 2H), 1.51 (s, 1H), 1.37 (s, 1H), 1.18 (d, J = 6.9 Hz, 3H). | 509.45 |
| 4-(4-amino-6-(4-methacrylamido-phenyl)-7-methyl-7H-pyrrolo[2,3-d]pyrimidin-5-yl)-N-(tetrahydrofuran-3-yl)benzamide | 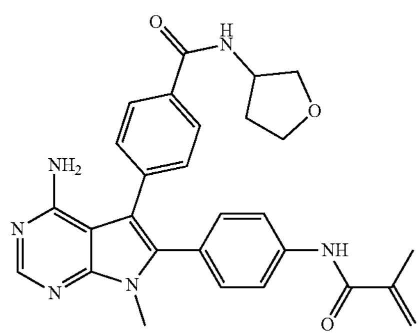 [SMILES: C=C(C)C(=O)Nc1ccc(-c2c(-c3ccc(C(=O)NC4CCOC4)cc3)c3c(N)ncnc3n2C)cc1] | ¹H NMR (400 MHz, DMSO-d₆) δ 9.90 (s, 1H), 8.51 (d, J = 6.5 Hz, 1H), 8.21 (s, 1H), 7.84-7.78 (m, 2H), 7.74-7.66 (m, 2H), 7.32-7.22 (m, 4H), 5.91 (s, 1H), 5.79 (s, 1H), 5.54 (d, J = 1.9 Hz, 1H), 4.44 (d, J = 8.0Hz, 1H), 3.84 (td, J = 8.7, 6.7 Hz, 2H), 3.71 (td, J = 8.1, 5.7 Hz, 1H), 3.61 (s, 3H), 3.57 (dd, J = 8.9, 4.4 Hz, 1H), 2.20-2.06 (m, 1H), 1.97-1.85 (m, 4H). | 497.20 |
| 4-(4-amino-6-(4-methacrylamido-phenyl)-7-methyl-7H-pyrrolo[2,3-d]pyrimidin-5-yl)-N-(2,2-difluoroethyl)benzamide | 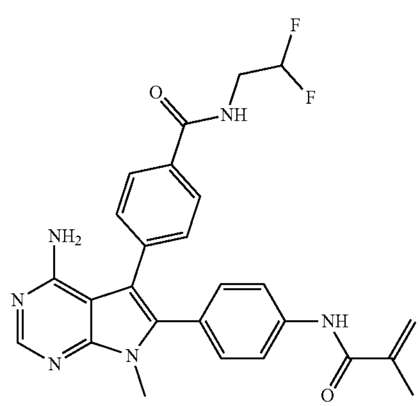 [SMILES: C=C(C)C(=O)Nc1ccc(-c2c(-c3ccc(C(=O)NCC(F)F)cc3)c3c(N)ncnc3n2C)cc1] | ¹H NMR (400 MHz, DMSO-d₆) δ 9.89 (s, 1H), 8.84 (t, J = 5.9 Hz, 1H), 8.21 (s, 1H), 7.83 (d, J = 7.9 Hz, 2H), 7.70 (d, J = 8.4 Hz, 2H), 7.31 (d, J = 8.0 Hz, 2H), 7.26 (d, J = 8.3 Hz, 2H), 6.33-5.63 (m, 4H), 5.53 (s, 1H), 3.72-3.61 (m, 3H), 3.32 (s, 2H), 1.95 (s, 3H). | 491.15 |

TABLE 2-continued

Additional Exemplary Compounds

| Compound | Structure | Proton NMR | MS [M + 1] |
| --- | --- | --- | --- |
| 4-(4-amino-6-(4-methacrylamido-phenyl)-7-methyl-7H-pyrrolo[2,3-d]pyrimidin-5-yl)-N-(2-hydroxy-2-methylpropyl)benzamide | 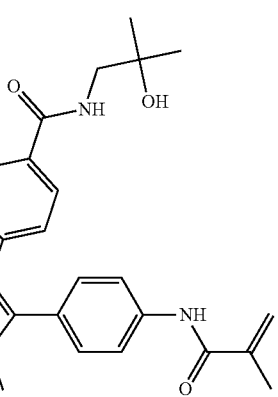 | $^1$H NMR (400 MHz, DMSO-d$_6$) δ 9.89 (s, 1H), 8.22 (d, J = 9.3 Hz, 2H), 7.85-7.79 (m, 2H), 7.74-7.66 (m, 2H), 7.33-7.23 (m, 4H), 5.92 (s, 1H), 5.80 (s, 1H), 5.56-5.51 (m, 1H), 4.53 (s, 1H), 3.61 (s, 3H), 3.24 (d, J = 6.1 Hz, 2H), 1.95 (d, J = 1.2 Hz, 3H), 1.10 (s, 6H). | 499.40 |
| 4-(4-amino-6-(4-methacrylamido-phenyl)-7-methyl-7H-pyrrolo[2,3-d]pyrimidin-5-yl)-N-(2-methoxy-2-methylpropyl)benzamide | 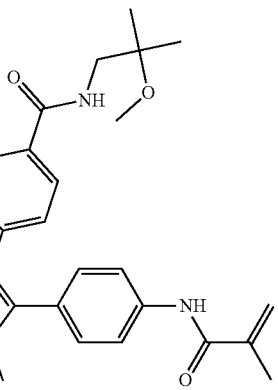 | $^1$H NMR (400 MHz, DMSO-d$_6$) δ 9.89 (s, 1H), 8.22 (d, J = 5.4 Hz, 2H), 7.84-7.77 (m, 2H), 7.74-7.67 (m, 2H), 7.33-7.24 (m, 4H), 5.90 (s, 1H), 5.80 (s, 1H), 5.53 (d, J = 1.9 Hz, 1H), 3.61 (s, 3H), 3.32 (d, J = 6.5 Hz, 1H), 3.15 (s, 3H), 1.95 (d, J = 1.3 Hz, 3H), 1.11 (s, 6H). | 513.50 |
| 4-(4-amino-6-(4-methacrylamido-phenyl)-7-methyl-7H-pyrrolo[2,3-d]pyrimidin-5-yl)-N-methyl-N-(2,2,2-trifluoroethyl)benzamide | 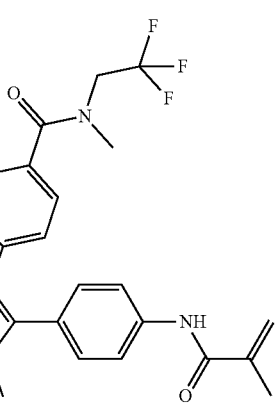 | $^1$H NMR (400 MHz, DMSO-d$_6$) δ 9.88 (s, 1H), 8.21 (s, 1H), 7.74-7.67 (m, 2H), 7.39 (s, 2H), 7.27 (dd, J = 13.3, 8.2 Hz, 4H), 5.98 (s, 2H), 5.80 (s, 1H), 5.53 (d, J = 1.8 Hz, 1H), 3.32 (s, 2H), 3.07 (s, 3H), 1.95 (t, J = 1.2 Hz, 3H). | 523.40 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(oxetan-3-yl)benzamide | 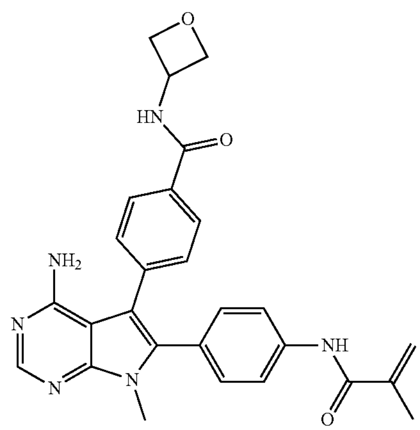 [SMILES: C=C(C)C(=O)Nc1ccc(-c2c(-c3ccc(C(=O)NC4COC4)cc3)c3c(N)ncnc3n2C)cc1] | ¹H NMR (400 MHz, DMSO-d₆) δ 9.90 (s, 1H), 9.08 (d, J = 6.4 Hz, 1H), 8.21 (s, 1H), 7.86-7.80 (m, 2H), 7.75-7.67 (m, 2H), 7.35-7.22 (m, 4H), 5.92-5.79 (s, 2H), 5.54 (t, J = 1.5 Hz, 1H), 4.99 (h, J = 6.9 Hz, 1H), 4.76 (dd, J = 7.5, 6.3 Hz, 2H), 4.58 (t, J = 6.4 Hz, 2H), 3.61 (s, 3H), 1.95 (d, J = 1.1 Hz, 3H). | 483.35 |
| 4-(4-amino-6-(4-methacrylamido-phenyl)-7-methyl-7H-pyrrolo[2,3-d]pyrimidin-5-yl)-N-isobutylbenzamide | 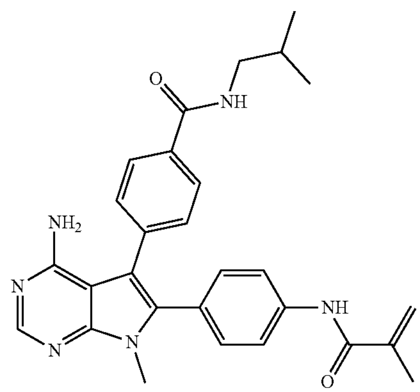 [SMILES: C=C(C)C(=O)Nc1ccc(-c2c(-c3ccc(C(=O)NCC(C)C)cc3)c3c(N)ncnc3n2C)cc1] | ¹H NMR (400 MHz, DMSO-d₆) δ 9.88 (s, 1H), 8.43 (t, J = 5.8 Hz, 1H), 8.21 (s, 1H), 7.79 (d, J = 8.0 Hz, 2H), 7.70 (d, J = 8.6 Hz, 2H), 7.28 (dd, J = 11.2, 8.4 Hz, 4H), 5.79 (s, 1H), 5.53 (s, 1H), 3.61 (s, 3H), 3.07 (t, J = 6.4 Hz, 2H), 1.95 (d, J = 1.2 Hz, 3H), 1.83 (dt, J = 13.6, 6.8 Hz, 1H), 0.89 (d, J = 6.7 Hz, 6H). | 483.40 |
| N-(4-(4-amino-5-(4-(N-cyclopentyl-sulfamoyl)phenyl)-7-methyl-7H-pyrrolo[2,3-d]pyrimidin-6-yl)phenyl)methacrylamide | 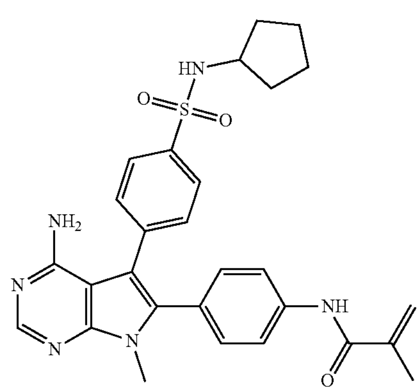 [SMILES: C=C(C)C(=O)Nc1ccc(-c2c(-c3ccc(S(=O)(=O)NC4CCCC4)cc3)c3c(N)ncnc3n2C)cc1] | ¹H NMR (400 MHz, DMSO-d₆) δ 9.90 (s, 1H), 8.22 (s, 1H), 7.77-7.66 (m, 4H), 7.57 (d, J = 7.7 Hz, 1H), 7.38 (d, J = 8.2 Hz, 2H), 7.22 (d, J = 8.5 Hz, 2H), 5.96 (s, 0H), 5.78 (s, 1H), 5.53 (s, 1H), 3.63 (s, 3H), 3.42 (q, J = 1.0 Hz, 1H), 3.32 (s, 1H), 1.94 (s, 3H), 1.53 (s, 3H), 1.37 (s, 2H), 1.21 (d, J = 6.0 Hz, 2H). | 531.35 |

TABLE 2-continued

Additional Exemplary Compounds

| Compound | Structure | Proton NMR | MS [M + 1] |
|---|---|---|---|
| N-(4-(4-amino-5-(4-(N-(2-hydroxy-2-methylpropyl)sulfamoyl)phenyl)-7-methyl-7H-pyrrolo[2,3-d]pyrimidin-6-yl)phenyl)methacrylamide | 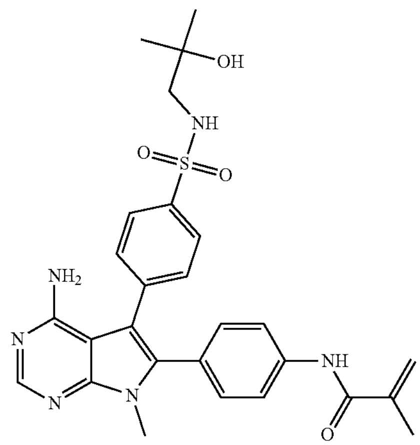 [SMILES: C=C(C)C(=O)Nc1ccc(-c2c(-c3ccc(S(=O)(=O)NCC(C)(C)O)cc3)c3c(N)ncnc3n2C)cc1] | $^1$H NMR (400 MHz, DMSO-d$_6$) δ 9.90 (s, 1H), 8.22 (s, 1H), 7.73 (t, J = 8.3 Hz, 4H), 7.45 (t, J = 6.5 Hz, 1H), 7.42-7.36 (m, 2H), 7.29-7.21 (m, 2H), 5.80 (s, 1H), 5.53 (t, J = 1.6 Hz, 1H), 4.38 (s, 1H), 3.61 (s, 3H), 3.32 (s, 2H), 2.66 (d, J = 6.5 Hz, 2H), 1.95 (t, J = 1.3 Hz, 3H), 1.03 (s, 6H). | 535.40 |
| N-(4-(4-amino-7-methyl-5-(4-(N-(2,2,2-trifluoroethyl)sulfamoyl)phenyl)-7H-pyrrolo[2,3-d]pyrimidin-6-yl)phenyl)methacrylamide | 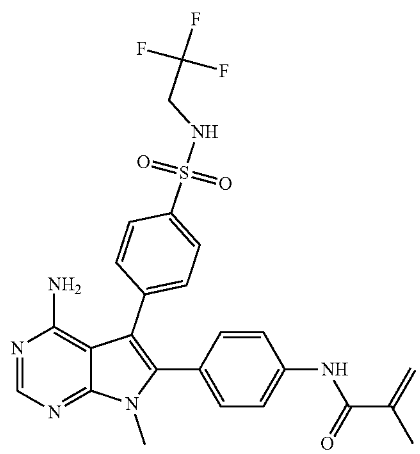 [SMILES: C=C(C)C(=O)Nc1ccc(-c2c(-c3ccc(S(=O)(=O)NCC(F)(F)F)cc3)c3c(N)ncnc3n2C)cc1] | $^1$H NMR (400 MHz, DMSO-d$_6$) δ 9.91 (s, 1H), 8.59 (s, 1H), 8.22 (s, 1H), 7.80-7.68 (m, 4H), 7.40 (d, J = 8.1 Hz, 2H), 7.26 (d, J = 8.3 Hz, 2H), 5.99 (s, 1H), 5.80 (s, 1H), 5.54 (s, 1H), 3.74 (d, J = 9.4 Hz, 2H), 3.69 (d, J = 9.5 Hz, 1H), 3.53 (s, 3H), 1.95 (s, 3H). | 545.30 |
| N-(4-(4-amino-5-(4-(N-isobutylsulfamoyl)phenyl)-7-methyl-7H-pyrrolo[2,3-d]pyrimidin-6-yl)phenyl)methacrylamide | 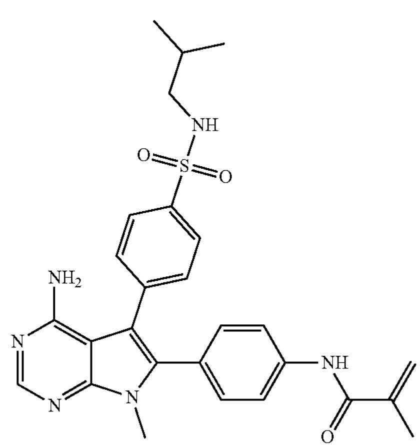 [SMILES: C=C(C)C(=O)Nc1ccc(-c2c(-c3ccc(S(=O)(=O)NCC(C)C)cc3)c3c(N)ncnc3n2C)cc1] | $^1$H NMR (400 MHz, DMSO-d$_6$) δ 9.89 (s, 1H), 8.22 (s, 1H), 7.75-7.68 (m, 4H), 7.55 (t, J = 6.1 Hz, 1H), 7.42-7.35 (m, 2H), 7.27-7.20 (m, 2H), 5.95 (s, 2H), 5.79 (d, J = 1.3 Hz, 1H), 5.56-5.51 (m, 1H), 3.62 (s, 3H), 2.58 (t, J = 6.4 Hz, 2H), 1.95 (t, J = 1.3 Hz, 3H), 1.58 (hept, J = 6.7 Hz, 1H), 0.78 (d, J = 6.7 Hz, 6H). | 519.40 |

TABLE 2-continued

Additional Exemplary Compounds

| Compound | Structure | Proton NMR | MS [M + 1] |
|---|---|---|---|
| N-(4-(4-amino-7-methyl-5-(4-(N-(oxetan-3-yl)sulfamoyl)phenyl)-7H-pyrrolo[2,3-d]pyrimidin-6-yl)phenyl)methacrylamide | 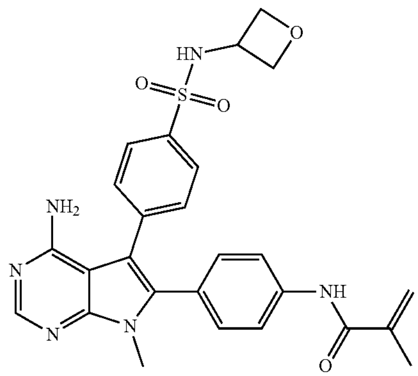 [SMILES: C=C(C)C(=O)Nc1ccc(-c2c(-c3ccc(S(=O)(=O)NC4COC4)cc3)c3c(N)ncnc3n2C)cc1] | ¹H NMR (400 MHz, DMSO-d₆) δ 9.91 (s, 1H), 8.49 (d, J = 7.4 Hz, 1H), 8.22 (s, 1H), 7.75-7.67 (m, 4H), 7.42-7.35 (m, 2H), 7.27-7.19 (m, 2H), 5.97 (m, 2H), 5.82-5.77 (m, 1H), 5.53 (t, J = 1.5 Hz, 1H), 4.46 (dd, J = 7.6, 5.6 Hz, 2H), 4.40 (q, J = 7.1 Hz, 1H), 4.21 (t, J = 6.0 Hz, 2H), 3.62 (s, 3H), 1.95 (t, J = 1.3 Hz, 3H). | 519.35 |
| N-(4-(4-amino-5-(4-(N-cyclopentyl-sulfamimidoyl)phenyl)-7-methyl-7H-pyrrolo[2,3-d]pyrimidin-6-yl)phenyl)methacrylamide | 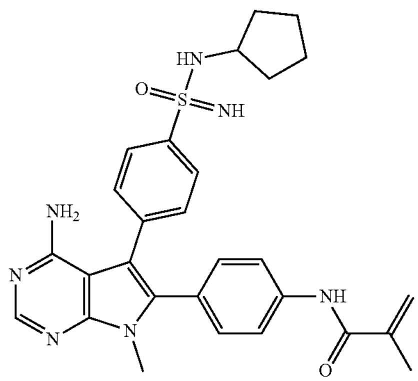 [SMILES: C=C(C)C(=O)Nc1ccc(-c2c(-c3ccc(S(=N)(=O)NC4CCCC4)cc3)c3c(N)ncnc3n2C)cc1] | ¹H NMR (400 MHz, DMSO-d₆) δ 9.89 (s, 1H), 8.21 (s, 1H), 7.85-7.79 (m, 2H), 7.68 (d, J = 8.6 Hz, 2H), 7.37-7.31 (m, 2H), 7.23 (d, J = 8.3 Hz, 2H), 6.85 (d, J = 8.0 Hz, 1H), 5.90 (br, 2H), 5.77 (s, 1H), 5.55 (s, 1H), 4.04 (s, 1H), 3.63 (s, 3H), 3.40-3.60 (m, 1H), 1.94 (t, J = 1.2 Hz, 3H), 1.49 (s, 4H), 1.33 (s, 2H), 1.15 (s, 2H). | 530.20 |
| N-(4-(4-amino-7-methyl-5-(4-(pyrrolidine-1-sulfonimidoyl)phenyl)-7H-pyrrolo[2,3-d]pyrimidin-6-yl)phenyl)methacrylamide | 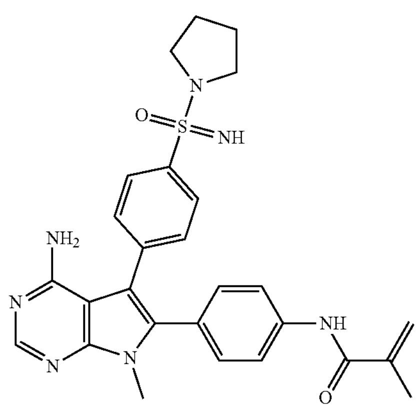 [SMILES: C=C(C)C(=O)Nc1ccc(-c2c(-c3ccc(S(=N)(=O)N4CCCC4)cc3)c3c(N)ncnc3n2C)cc1] | ¹H NMR (400 MHz, DMSO-d₆) δ 9.90 (s, 1H), 8.22 (s, 1H), 7.82-7.76 (m, 2H), 7.73-7.66 (m, 2H), 7.41-7.34 (m, 2H), 7.26-7.18 (m, 2H), 5.79 (s, 3H), 5.56-5.50 (m, 1H), 4.37 (s, 1H), 3.63 (s, 3H), 3.06 (d, J = 6.4 Hz, 4H), 1.95 (d, J = 1.3 Hz, 3H), 1.61-1.53 (m, 4H). | 516.30 |
| N-(4-(4-amino-5-(4-(N-cyclopentyl-N-methylsulfamoyl)phenyl)-7-methyl-7H-pyrrolo[2,3-d]pyrimidin-6-yl)phenyl)methacrylamide | 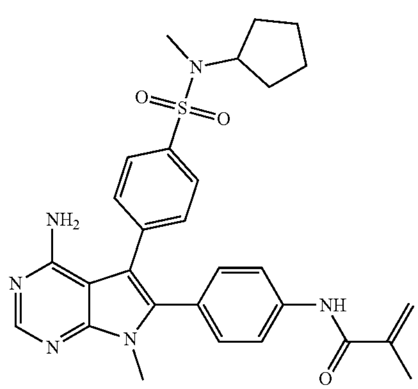 [SMILES: C=C(C)C(=O)Nc1ccc(-c2c(-c3ccc(S(=O)(=O)N(C)C4CCCC4)cc3)c3c(N)ncnc3n2C)cc1] | ¹H NMR (400 MHz, DMSO-d₆) δ 9.89 (s, 1H), 8.22 (s, 1H), 7.75-7.65 (m, 4H), 7.43-7.36 (m, 2H), 7.25-7.17 (m, 2H), 5.98 (s, 2H), 5.78 (t, J = 1.1 Hz, 1H), 5.56-5.51 (m, 1H), 4.17 (q, J = 8.0 Hz, 1H), 3.64 (s, 3H), 2.64 (s, 3H), 1.95 (d, J = 1.2 Hz, 3H), 1.52 (q, J = 5.0, 4.5 Hz, 2H), 1.42 (d, J = 11.8 Hz, 4H), 1.32-1.23 (m, 2H). | 545.40 |

TABLE 2-continued

Additional Exemplary Compounds

| Compound | Structure | Proton NMR | MS [M + 1] |
|---|---|---|---|
| N-(4-(4-amino-7-methyl-5-(4-(N-methyl-N-(2,2,2-trifluoroethyl)sulfamoyl)phenyl)-7H-pyrrolo[2,3-d]pyrimidin-6-yl)phenyl)methacrylamide | 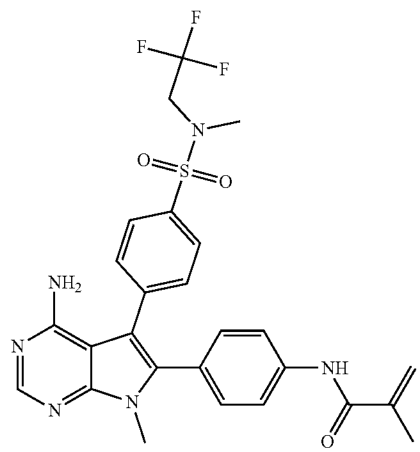 [SMILES: C=C(C)C(=O)Nc1ccc(-c2c(-c3ccc(S(=O)(=O)N(C)CC(F)(F)F)cc3)c3c(N)ncnc3n2C)cc1] | $^1$H NMR (400 MHz, DMSO-d$_6$) δ 9.91 (s, 1H), 8.23 (s, 1H), 7.83-7.76 (m, 2H), 7.76-7.69 (m, 2H), 7.45-7.38 (m, 2H), 7.29-7.21 (m, 2H), 5.83-5.78 (m, 1H), 5.54 (t, J = 1.4 Hz, 1H), 4.02 (q, J = 9.2 Hz, 2H), 3.62 (s, 3H), 2.83 (s, 3H), 1.96 (t, J = 1.2 Hz, 3H). | 559.40 |
| N-(4-(4-amino-5-(4-(cyclopentylmethyl-sulfonyl)phenyl)-7-methyl-7H-pyrrolo[2,3-d]pyrimidin-6-yl)phenyl)methacrylamide | 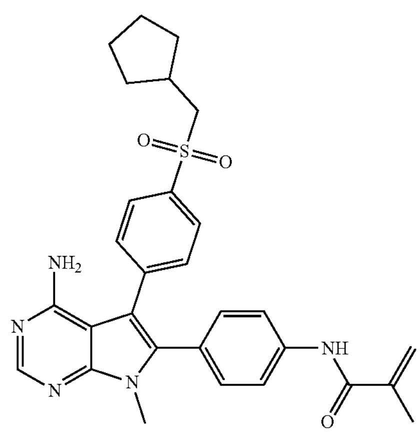 [SMILES: C=C(C)C(=O)Nc1ccc(-c2c(-c3ccc(S(=O)(=O)CC4CCCC4)cc3)c3c(N)ncnc3n2C)cc1] | $^1$H NMR (400 MHz, DMSO-d$_6$) δ 9.91 (s, 1H), 8.23 (s, 1H), 7.86-7.79 (m, 2H), 7.74-7.68 (m, 2H), 7.47-7.40 (m, 2H), 7.27-7.21 (m, 2H), 5.79 (s, 1H), 5.53 (d, J = 1.8 Hz, 1H), 3.62 (s, 3H), 3.37-3.27 (m, 2H), 2.10 (hept, J = 7.5 Hz, 1H), 1.95 (d, J = 1.1 Hz, 3H), 1.75-1.63 (m, 2H), 1.54 (qd, J = 9.4, 8.0, 3.0 Hz, 2H), 1.45 (qt, J = 7.1, 2.6 Hz, 2H), 1.16 (dq, J = 11.8, 7.7 Hz, 2H). | 530.4 |
| N-(4-(4-amino-7-methyl-5-(4-(3,3,3-trifluoropropyl-sulfonyl)phenyl)-7H-pyrrolo[2,3-d]pyrimidin-6-yl)phenyl)methacrylamide | 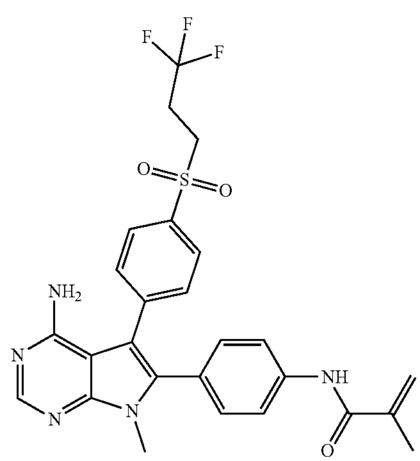 [SMILES: C=C(C)C(=O)Nc1ccc(-c2c(-c3ccc(S(=O)(=O)CCC(F)(F)F)cc3)c3c(N)ncnc3n2C)cc1] | $^1$H NMR (400 MHz, DMSO-d$_6$) δ 9.91 (s, 1H), 8.23 (s, 1H), 7.90-7.84 (m, 2H), 7.76-7.69 (m, 2H), 7.47-7.41 (m, 2H), 7.29-7.22 (m, 2H), 5.80 (s, 1H), 5.54 (d, J = 1.8 Hz, 1H), 3.61 (s, 4H), 3.65-3.57 (m, 1H), 2.73-2.58 (m, 2H), 1.95 (s, 3H). | 544.3 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(2-methoxycyclopentyl)benzamide | 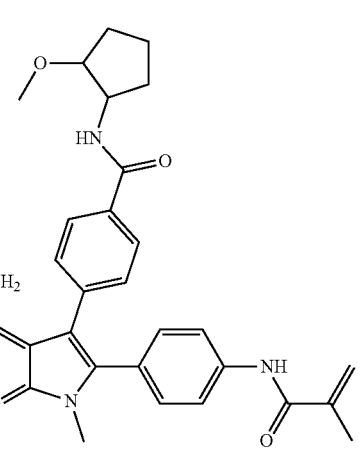 | $^{1}$H NMR (400 MHz, DMSO-d$_{6}$) δ 9.89 (s, 1H), 8.33 (d, J = 7.7 Hz, 1H), 8.21 (s, 1H), 7.79 (d, J = 7.9 Hz, 2H), 7.70 (d, J = 8.2 Hz, 2H), 7.28 (dd, J = 12.1, 8.1 Hz, 4H), 5.92 (s, 1H), 5.79 (s, 1H), 5.53 (s, 1H), 4.18 (dd, J = 11.6, 6.3 Hz, 1H), 3.69 (dd, J = 6.7, 3.4 Hz, 1H), 3.33 (s, 3H), 3.25 (s, 3H), 1.98 (d, J = 7.7 Hz, 1H), 1.95 (s, 3H), 1.88 (dq, J = 13.8, 7.0 Hz, 1H), 1.69 (s, 1H), 1.70-1.59 (m, 0H), 1.58 (s, 2H), 1.52 (dq, J = 14.1, 7.4, 6.3 Hz, 1H). | 525.40 |
| 4-(4-amino-6-(4-methacrylamido-phenyl)-7-methyl-7H-pyrrolo[2,3-d]pyrimidin-5-yl)-N-(2-hydroxycyclopentyl)benzamide | 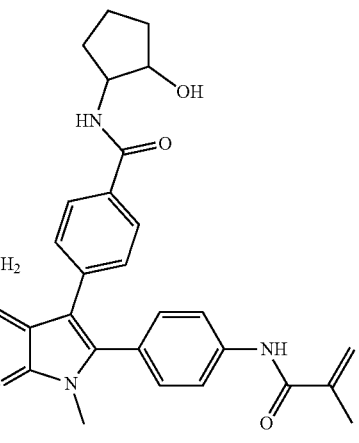 | $^{1}$H NMR (400 MHz, DMSO-d$_{6}$) δ 9.89 (s, 1H), 8.20 (d, J = 7.7 Hz, 2H), 7.83-7.76 (m, 2H), 7.73-7.67 (m, 2H), 7.32-7.22 (m, 4H), 5.90 (s, 1H), 5.79 (s, 1H), 5.53 (d, J = 2.0 Hz, 1H), 4.74 (d, J = 3.8 Hz, 1H), 3.98 (s, 2H), 3.61 (s, 3H), 2.03-1.92 (m, 4H), 1.91-1.78 (m, 1H), 1.65 (p, J = 7.8, 6.8 Hz, 2H), 1.47 (dd, J = 13.4, 7.0 Hz, 2H). | 511.25 |
| N-(4-(4-amino-5-(4-(N-(2-methoxycyclopentyl)sulfamoyl)phenyl)-7-methyl-7H-pyrrolo[2,3-d]pyrimidin-6-yl)phenyl)methacrylamide | 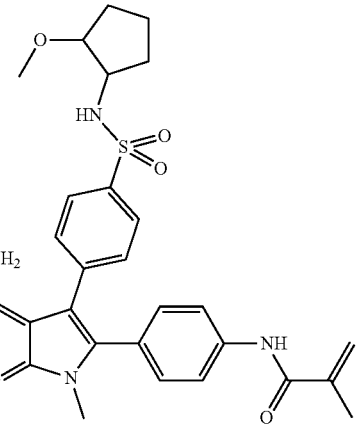 | $^{1}$H NMR (400 MHz, DMSO-d$_{6}$) δ 9.91 (s, 1H), 8.22 (s, 1H), 7.78-7.66 (m, 4H), 7.43-7.36 (m, 2H), 7.27-7.19 (m, 2H), 5.96 (s, 2H), 5.80-5.75 (m, 1H), 5.56-5.51 (m, 1H), 3.62 (s, 3H), 3.41-3.28 (m, 2H), 2.97 (s, 3H), 2.08 (s, 1H), 1.94 (d, J = 1.3 Hz, 3H), 1.76-1.57 (m, 1H), 1.61-1.44 (m, 1H), 1.48-1.36 (m, 3H), 1.21 (dt, J = 12.2, 6.4 Hz, 1H). | 561.45 |

TABLE 2-continued

Additional Exemplary Compounds

| Compound | Structure | Proton NMR | MS [M + 1] |
|---|---|---|---|
| N-(4-(4-amino-5-(4-(N-(2-hydroxycyclopentyl)sulfamoyl)phenyl)-7-methyl-7H-pyrrolo[2,3-d]pyrimidin-6-yl)phenyl)methacrylamide | 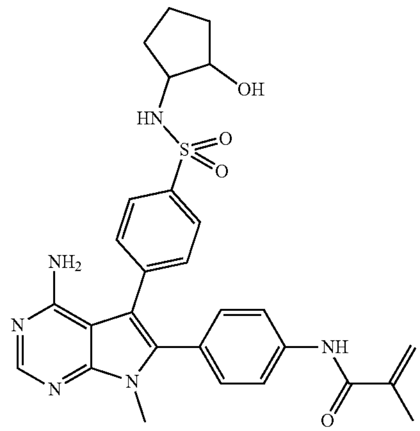 [SMILES: C=C(C)C(=O)Nc1ccc(-c2c(-c3ccc(S(=O)(=O)NC4CCCC4O)cc3)c3c(N)ncnc3n2C)cc1] | $^1$H NMR (400 MHz, DMSO-$d_6$) δ 9.90 (s, 1H), 8.22 (s, 1H), 7.78-7.67 (m, 4H), 7.50 (d, J = 7.5 Hz, 1H), 7.42-7.35 (m, 2H), 7.27-7.20 (m, 2H), 5.94 (s, 1H), 5.78 (s, 1H), 5.53 (s, 1H), 4.66 (d, J = 4.4 Hz, 1H), 3.75 (dt, J = 8.7, 4.5 Hz, 1H), 3.58 (s, 1H), 3.32 (s, 2H), 3.24-3.17 (m, 1H), 1.95 (t, J = 1.2 Hz, 3H), 1.77-1.64 (m, 1H), 1.63-1.49 (m, 1H), 1.49 (d, J = 7.3 Hz, 2H), 1.35 (dt, J = 11.7, 5.7 Hz, 1H), 1.11 (dt, J = 13.1, 6.6 Hz, 1H). | 547.35 |
| N-(4-(4-amino-5-(4-(N-cyclobutylsulfamoyl)phenyl)-7-methyl-7H-pyrrolo[2,3-d]pyrimidin-6-yl)phenyl)methacrylamide | 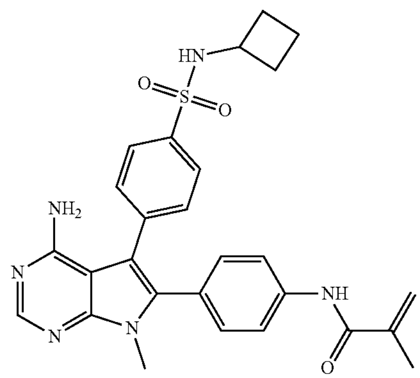 | $^1$H NMR (400 MHz, DMSO-$d_6$) δ 9.89 (s, 1H), 8.22 (s, 1H), 7.87 (d, J = 9.1 Hz, 1H), 7.75-7.65 (m, 4H), 7.38 (d, J = 8.3 Hz, 2H), 7.25-7.18 (m, 2H), 5.78 (s, 1H), 5.53 (s, 1H), 3.63 (s, 3H), 3.59 (d, J = 8.3 Hz, 0H), 3.32 (s, 1H), 1.94 (d, J = 1.5 Hz, 3H), 1.89-1.77 (m, 2H), 1.74-1.60 (m, 2H), 1.57-1.40 (m, 2H). | 517.35 |
| (R)-4-(4-amino-6-(4-methacrylamidophenyl)-7-methyl-7H-pyrrolo[2,3-d]pyrimidin-5-yl)-N-(tetrahydrofuran-3-yl)benzamide | | $^1$H NMR (400 MHz, DMSO-$d_6$) δ 9.89 (s, 1H), 8.51 (d, J = 6.5 Hz, 1H), 8.21 (s, 1H), 7.81 (d, J = 8.2 Hz, 2H), 7.70 (d, J = 8.6 Hz, 2H), 7.32-7.23 (m, 4H), 5.79 (s, 1H), 5.53 (s, 1H), 4.44 (d, J = 7.2 Hz, 1H), 3.89-3.79 (m, 2H), 3.73 (m, 1H), 3.68-3.61 (m, 3H), 3.56 (dd, J = 8.8, 4.4 Hz, 1H), 2.18-2.07 (m, 1H), 1.97-1.87 (m, 4H). | 497.20 |
| (S)-4-(4-amino-6-(4-methacrylamidophenyl)-7-methyl-7H-pyrrolo[2,3-d]pyrimidin-5-yl)-N-(tetrahydrofuran-3-yl)benzamide | | $^1$H NMR (400 MHz, Methanol-$d_4$) δ 8.23 (s, 1H), 7.83-7.78 (m, 2H), 7.70-7.64 (m, 2H), 7.40-7.35 (m, 2H), 7.30-7.25 (m, 2H), 5.87-5.77 (m, 1H), 5.54 (dt, J = 2.0, 1.0 Hz, 1H), 4.59 (ddt, J = 8.0, 6.0, 4.1 Hz, 1H), 4.02-3.94 (m, 2H), 3.86 (td, J = 8.3, 5.8 Hz, 1H), 3.77-3.69 (m, 4H), 2.38-2.23 (m, 1H), 2.04-1.93 (d, J = 1.3 Hz, 4H). | 497.20 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(3,3,3-trifluoro-2-hydroxypropyl)benzamide | 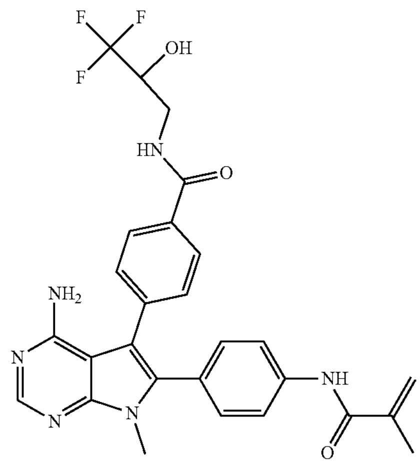 [SMILES: C=C(C)C(=O)Nc1ccc(-c2c(-c3ccc(C(=O)NCC(O)C(F)(F)F)cc3)c3c(N)ncnc3n2C)cc1] | ¹H NMR (400 MHz, DMSO-d₆) δ 9.90 (s, 1H), 8.70 (t, J = 5.7 Hz, 1H), 8.21 (s, 1H), 7.85-7.79 (m, 2H), 7.74-7.66 (m, 2H), 7.34-7.23 (m, 4H), 6.47 (d, J = 6.4 Hz, 1H), 5.92 (s, 1H), 5.79 (s, 1H), 5.53 (t, J = 1.4 Hz, 1H), 4.22-4.16 (m, 2H), 3.62 (s, 3H), 3.58 (d, J = 5.2 Hz, 1H), 1.95 (d, J = 1.2 Hz, 3H). | 539.20 |
| 4-(4-amino-6-(4-methacrylamido-phenyl)-7-methyl-7H-pyrrolo[2,3-d]pyrimidin-5-yl)-N-((3-fluorooxetan-3-yl)methyl)benzamide | 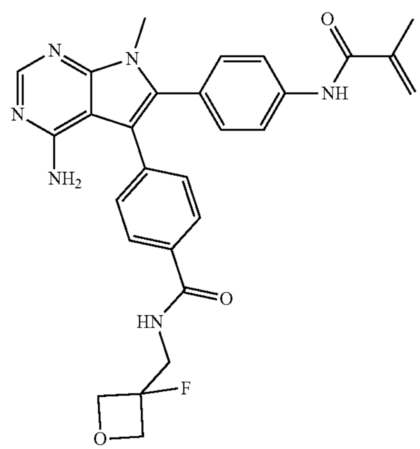 [SMILES: C=C(C)C(=O)Nc1ccc(-c2c(-c3ccc(C(=O)NCC4(F)COC4)cc3)c3c(N)ncnc3n2C)cc1] | ¹H NMR (400 MHz, DMSO-d₆) δ 9.89 (s, 1H), 8.78 (t, J = 6.0 Hz, 1H), 8.21 (s, 1H), 7.86-7.79 (m, 2H), 7.74-7.66 (m, 2H), 7.34-7.29 (m, 2H), 7.29-7.22 (m, 2H), 5.79 (s, 1H), 5.53 (d, J = 2.1 Hz, 1H), 4.70 (d, J = 8.0 Hz, 1H), 4.65 (q, J = 3.4 Hz, 2H), 4.59 (d, J = 8.0 Hz, 1H), 3.82 (d, J = 6.0 Hz, 1H), 3.77 (d, J = 6.0 Hz, 1H), 3.61 (s, 3H), 1.95 (t, J = 1.2 Hz, 3H). | 515.40 |
| 4-(4-amino-6-(4-methacrylamido-phenyl)-7-methyl-7H-pyrrolo[2,3-d]pyrimidin-5-yl)-N-((tetrahydrofuran-3-yl)methyl)benzamide | 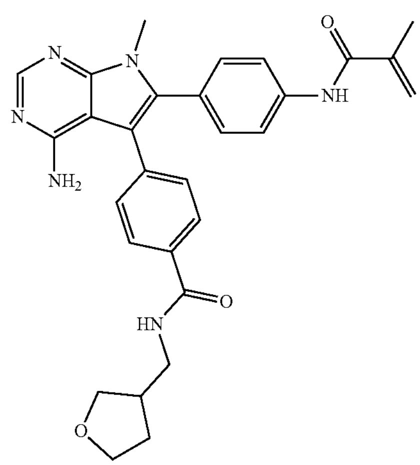 [SMILES: C=C(C)C(=O)Nc1ccc(-c2c(-c3ccc(C(=O)NCC4CCOC4)cc3)c3c(N)ncnc3n2C)cc1] | ¹H NMR (400 MHz, Chloroform-d) δ 8.40 (s, 1H), 7.71 (d, J = 7.9 Hz, 2H), 7.63-7.55 (m, 3H), 7.34 (d, J = 8.0 Hz, 2H), 7.25-7.19 (m, 2H), 6.39 (t, J = 5.5 Hz, 1H), 5.82 (s, 1H), 5.52 (d, J = 2.0 Hz, 1H), 5.03 (s, 2H), 3.95 (td, J = 8.3, 5.2 Hz, 1H), 3.86 (dd, J = 8.9, 6.9 Hz, 1H), 3.82-3.72 (m, 4H), 3.66 (dd, J = 8.9, 4.9 Hz, 1H), 3.50 (dd, J = 7.2, 5.3 Hz, 2H), 2.63 (p, J = 6.9 Hz, 1H), 2.19-2.05 (m, 4H), 1.78-1.66 (m, 1H). | 511.20 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-((1-hydroxycyclopropyl)methyl)benzamide | | $^1$H NMR (400 MHz, DMSO-d$_6$) δ 9.89 (s, 1H), 8.38 (t, J = 5.8 Hz, 1H), 8.21 (s, 1H), 7.86-7.79 (m, 2H), 7.74-7.66 (m, 2H), 7.33-7.23 (m, 4H), 5.80 (d, J = 1.4 Hz, 3H), 5.53 (t, J = 1.6 Hz, 1H), 5.40 (s, 1H), 3.67 (s, 3H), 3.42 (d, J = 5.7 Hz, 2H), 1.95 (t, J = 1.3 Hz, 3H), 0.55 (q, J = 2.2 Hz, 4H). | 497.40 |
| 4-(4-amino-6-(4-methacrylamido-phenyl)-7-methyl-7H-pyrrolo[2,3-d]pyrimidin-5-yl)-N-((1-hydroxycyclopropyl)methyl)benzamide | | $^1$H NMR (400 MHz, DMSO-d$_6$) δ 9.89 (s, 1H), 8.38 (t, J = 5.8 Hz, 1H), 8.21 (s, 1H), 7.86-7.79 (m, 2H), 7.74-7.66 (m, 2H), 7.33-7.23 (m, 4H), 5.80 (d, J = 1.4 Hz, 3H), 5.53 (t, J = 1.6 Hz, 1H), 5.40 (s, 1H), 3.67 (s, 3H), 3.42 (d, J = 5.7 Hz, 2H), 1.95 (t, J = 1.3 Hz, 3H), 0.55 (q, J = 2.2 Hz, 4H). | 497.40 |
| 4-(4-amino-6-(4-methacrylamido-phenyl)-7-methyl-7H-pyrrolo[2,3-d]pyrimidin-5-yl)-N-(3-hydroxy-2,2-dimethylpropyl)benzamide | 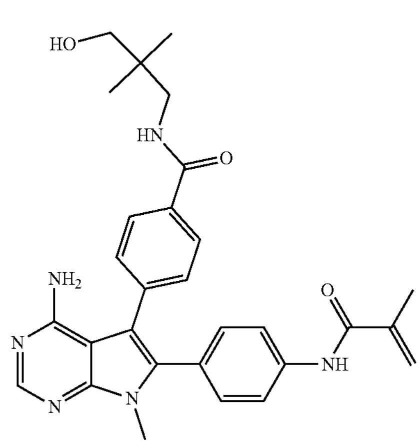 [SMILES: C=C(C)C(=O)Nc1ccc(-c2c(-c3ccc(C(=O)NCC(C)(C)CO)cc3)c3c(N)ncnc3n2C)cc1] | $^1$H NMR (400 MHz, DMSO-d$_6$) δ 9.90 (s, 1H), 8.38 (t, J = 6.2 Hz, 1H), 8.21 (s, 1H), 7.82-7.75 (m, 2H), 7.74-7.67 (m, 2H), 7.34-7.24 (m, 4H), 6.07-5.75 (m, 2H), 5.53 (t, J = 1.4 Hz, 1H), 4.58 (t, J = 6.1Hz, 1H), 3.61 (s, 3H), 3.17-3.09 (m, 4H), 1.95 (t, J = 1.2 Hz, 3H), 0.83 (s, 6H). | 513.30 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(3-(hydroxymethyl)cyclobutyl)benzamide | 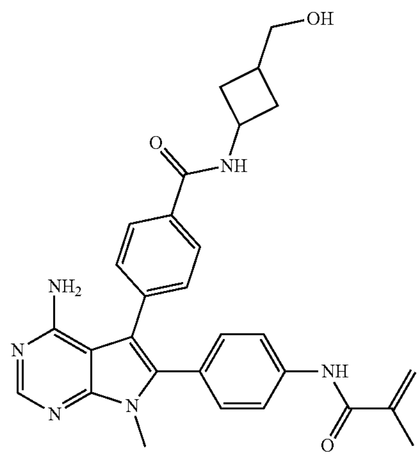 [SMILES: C=C(C)C(=O)Nc1ccc(-c2c(-c3ccc(C(=O)NC4CC(CO)C4)cc3)c3c(N)ncnc3n2C)cc1] | $^1$H NMR (400 MHz, DMSO-d$_6$) δ 9.90 (s, 1H), 8.53 (d, J = 7.5 Hz, 1H), 8.21 (s, 1H), 7.79 (dd, J = 8.4, 1.7 Hz, 2H), 7.73-7.67 (m, 2H), 7.32-7.22 (m, 4H), 5.79 (d, J = 1.3 Hz, 2H), 5.54 (d, J = 1.8 Hz, 1H), 4.51-4.38 (m, 1H), 4.27 (q, J = 8.4 Hz, 1H), 3.61 (s, 3H), 3.50-3.42 (m, 1H), 3.36 (t, J = 5.7 Hz, 2H), 2.25 (d, J = 8.8 Hz, 2H), 2.13-2.04 (m, 2H), 1.95 (d, J = 1.3 Hz, 3H), 1.82-1.70 (m, 1H). | 511.30 |
| 4-(4-amino-6-(4-methacrylamido-phenyl)-7-methyl-7H-pyrrolo[2,3-d]pyrimidin-5-yl)-N-(2-(oxetan-3-yl)ethyl)benzamide | 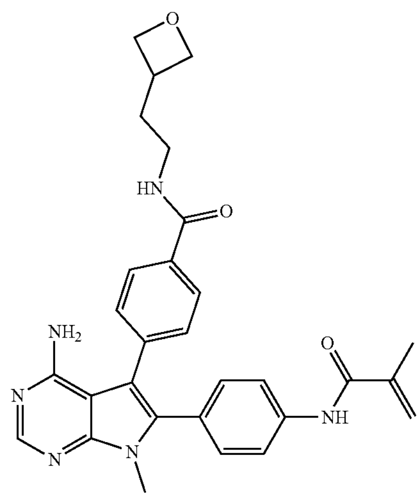 [SMILES: C=C(C)C(=O)Nc1ccc(-c2c(-c3ccc(C(=O)NCCC4COC4)cc3)c3c(N)ncnc3n2C)cc1] | $^1$H NMR (400 MHz, DMSO-d$_6$) δ 9.90 (s, 1H), 8.21 (s, 1H), 7.71 (d, J = 8.6 Hz, 2H), 7.49 (d, J = 7.3 Hz, 2H), 7.27 (d, J = 7.6 Hz, 4H), 5.80 (s, 2H), 5.53 (s, 1H), 4.67 (dd, J = 20.8, 5.0 Hz, 1H), 3.61 (s, 3H), 3.58-3.36 (m, 4H), 3.32-3.22 (m, 2H), 2.40-2.20 (m, 1H), 1.95 (t, J = 1.2 Hz, 3H), 1.88 (s, 1H), 1.64 (s, 1H). | 511.40 |
| 4-(4-amino-6-(4-methacrylamido-phenyl)-7-methyl-7H-pyrrolo[2,3-d]pyrimidin-5-yl)-N-(azetidin-3-ylmethyl)benzamide 2,2,2-trifluoroacetate | 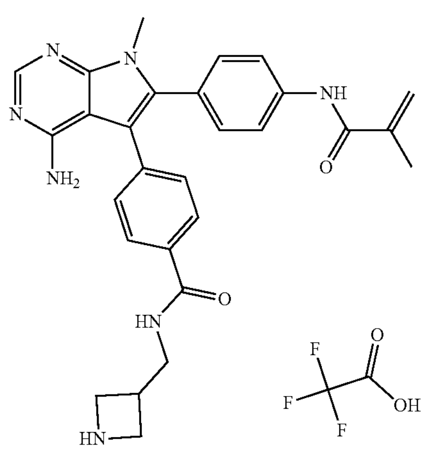 [SMILES: C=C(C)C(=O)Nc1ccc(-c2c(-c3ccc(C(=O)NCC4CNC4)cc3)c3c(N)ncnc3n2C)cc1 ; O=C(O)C(F)(F)F] | $^1$H NMR (400 MHz, DMSO-d$_6$) δ 9.95 (s, 1H), 8.68 (t, J = 5.8 Hz, 1H), 8.64-8.41 (m, 3H), 7.87-7.80 (m, 2H), 7.77-7.69 (m, 2H), 7.37-7.25 (m, 4H), 5.80 (s, 1H), 5.55 (d, J = 1.9 Hz, 1H), 3.95 (t, J = 10.1 Hz, 2H), 3.80 (q, J = 8.9, 7.9 Hz, 2H), 3.67 (s, 3H), 3.48 (t, J = 6.1 Hz, 2H), 3.01 (p, J = 7.5 Hz, 1H), 1.95 (t, J = 1.3 Hz, 3H). | 496.25 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(3-oxabicyclo[3.1.0]hexan-6-yl)benzamide | 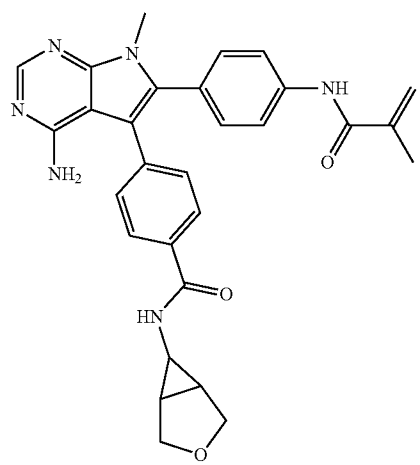 [SMILES: C=C(C)C(=O)Nc1ccc(-c2c(-c3ccc(C(=O)NC4C5COCC54)cc3)c3c(N)ncnc3n2C)cc1] | ¹H NMR (400 MHz, DMSO-d₆) δ 9.90 (s, 1H), 8.46 (d, J = 4.2 Hz, 1H), 8.21 (s, 1H), 7.79-7.73 (m, 2H), 7.73-7.66 (m, 2H), 7.32-7.22 (m, 4H), 5.90 (s, 1H), 5.79 (s, 1H), 5.56-5.51 (m, 1H), 3.86 (d, J = 8.4 Hz, 2H), 3.63 (d, J = 13.4 Hz, 5H), 2.59 (q, J = 2.9 Hz, 1H), 1.95 (t, J = 1.2 Hz, 3H),, 1.87 (s, 2H). | 509.40 |
| 4-(4-amino-6-(4-methacrylamido-phenyl)-7-methyl-7H-pyrrolo[2,3-d]pyrimidin-5-yl)-N-((1-methoxycyclobutyl)methyl)benzamide | 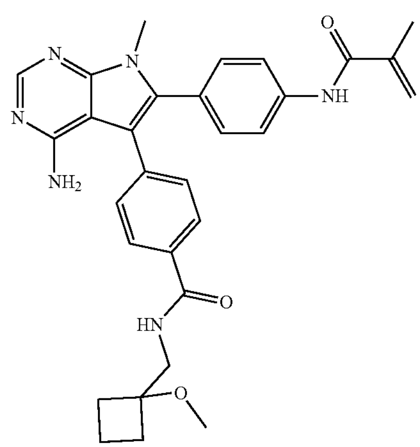 [SMILES: C=C(C)C(=O)Nc1ccc(-c2c(-c3ccc(C(=O)NCC4(OC)CCC4)cc3)c3c(N)ncnc3n2C)cc1] | ¹H NMR (400 MHz, DMSO-d₆) δ 9.89 (s, 1H), 8.27 (t, J = 6.1 Hz, 1H), 8.21 (s, 1H), 7.81 (d, J = 7.9 Hz, 2H), 7.70 (d, J = 8.3 Hz, 2H), 7.28 (dd, J = 11.9, 8.1 Hz, 4H), 5.80 (s, 2H), 5.53 (s, 1H), 3.53 (d, J = 6.0 Hz, 2H), 3.33 (s, 3H), 3.13 (s, 3H), 1.96 (d, J = 9.9 Hz, 7H), 1.70-1.64 (m, 1H), 1.63-1.54 (m, 1H). | 525.40 |
| 4-(4-amino-6-(4-methacrylamido-phenyl)-7-methyl-7H-pyrrolo[2,3-d]pyrimidin-5-yl)-N-(2-cyano-2-methylpropyl)benzamide | 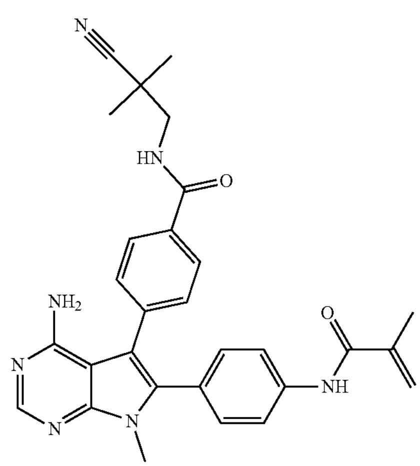 [SMILES: C=C(C)C(=O)Nc1ccc(-c2c(-c3ccc(C(=O)NCC(C)(C)C#N)cc3)c3c(N)ncnc3n2C)cc1] | ¹H NMR (400 MHz, DMSO-d₆) δ 9.89 (s, 1H), 8.78 (t, J = 6.4 Hz, 1H), 8.22 (s, 1H), 7.86-7.80 (m, 2H), 7.75-7.67 (m, 2H), 7.36-7.24 (m, 4H), 5.80 (s, 1H), 5.54 (d, J = 1.9 Hz, 1H), 3.61 (s, 3H), 3.46 (d, J = 6.4 Hz, 2H), 1.95 (d, J = 1.3 Hz, 3H), 1.33 (s, 6H). | 508.2 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(1-cyclopropyl-3-hydroxypropan-2-yl)benzamide | 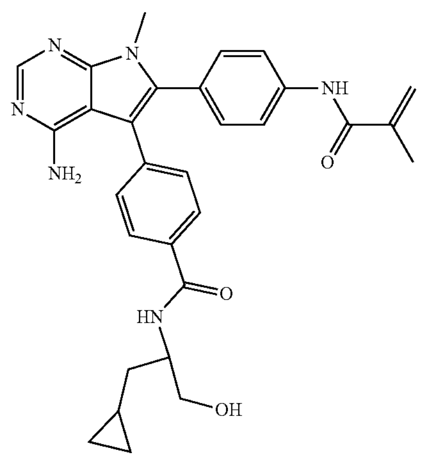 [SMILES: C=C(C)C(=O)Nc1ccc(-c2c(-c3ccc(C(=O)NC(CO)CC4CC4)cc3)c3c(N)ncnc3n2C)cc1] | $^1$H NMR (400 MHz, DMSO-$d_6$) δ 9.89 (s, 1H), 8.21 (s, 1H), 8.06 (d, J = 8.4 Hz, 1H), 7.85-7.78 (m, 2H), 7.74-7.67 (m, 2H), 7.32-7.23 (m, 4H), 5.95 (s, 2H), 5.79 (s, 1H), 5.56-5.51 (m, 1H), 4.63 (t, J = 5.8 Hz, 1H), 4.05-3.98 (m, 1H), 3.61 (s, 3H), 3.53-3.36 (m, 3H), 1.94 (d, J = 1.3 Hz, 3H), 1.44 (h, J = 7.4 Hz, 2H), 0.72 (s, 1H), 0.42-0.33 (m, 2H), 0.11 (d, J = 8.8 Hz, 1H). | 525.40 |
| 4-(4-amino-6-(4-methacrylamido-phenyl)-7-methyl-7H-pyrrolo[2,3-d]pyrimidin-5-yl)-N-(oxetan-3-ylmethyl)benzamide | 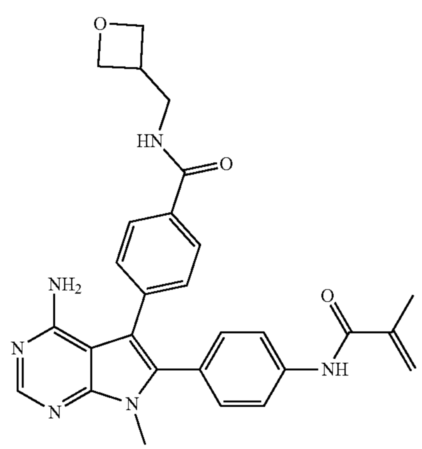 [SMILES: C=C(C)C(=O)Nc1ccc(-c2c(-c3ccc(C(=O)NCC4COC4)cc3)c3c(N)ncnc3n2C)cc1] | $^1$H NMR (400 MHz, DMSO-$d_6$) δ 9.90 (s, 1H), 8.60 (t, J = 5.7 Hz, 1H), 8.21 (s, 1H), 7.82-7.75 (m, 2H), 7.74-7.67 (m, 2H), 7.33-7.23 (m, 4H), 5.92 (s, 1H), 5.80 (t, J = 1.0 Hz, 1H), 5.54 (t, J = 1.5 Hz, 1H), 4.63 (dd, J = 7.8, 6.0 Hz, 2H), 4.34 (t, J = 6.0 Hz, 2H), 3.61 (s, 3H), 3.53 (dd, J = 6.9, 5.7 Hz, 2H), 3.16 (dq, J = 13.7, 6.9 Hz, 1H), 1.95 (t, J = 1.2 Hz, 3H). | 497.40 |
| 4-(4-amino-6-(4-methacrylamido-phenyl)-7-methyl-7H-pyrrolo[2,3-d]pyrimidin-5-yl)-N-(cyanomethyl)benzamide | 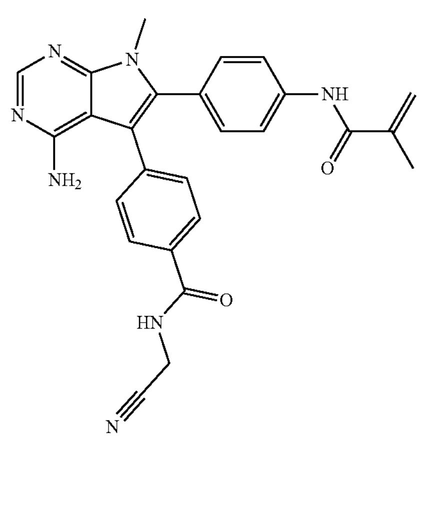 [SMILES: C=C(C)C(=O)Nc1ccc(-c2c(-c3ccc(C(=O)NCC#N)cc3)c3c(N)ncnc3n2C)cc1] | $^1$H NMR (400 MHz, DMSO-$d_6$) δ 9.89 (s, 1H), 9.18 (t, J = 5.5 Hz, 1H), 8.21 (s, 1H), 7.85-7.79 (m, 2H), 7.74-7.67 (m, 2H), 7.36-7.29 (m, 2H), 7.29-7.22 (m, 2H), 5.80 (s, 1H), 5.53 (t, J = 1.5 Hz, 1H), 4.30 (d, J = 5.4 Hz, 2H), 3.61 (s, 3H), 1.95 (t, J = 1.2 Hz, 3H). | 466.35 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(tetrahydro-2H-pyran-3-yl)benzamide | 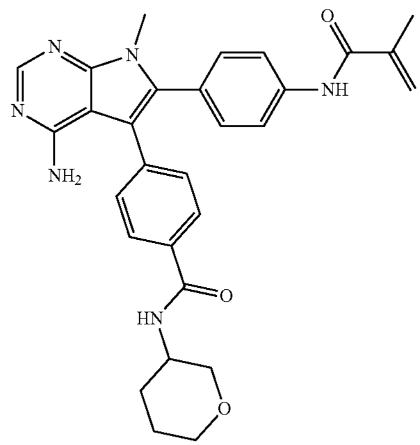 [SMILES: C=C(C)C(=O)Nc1ccc(-c2c(-c3ccc(C(=O)NC4CCCOC4)cc3)c3c(N)ncnc3n2C)cc1] | $^1$H NMR (400 MHz, DMSO-$d_6$) δ 9.90 (s, 1H), 8.20 (d, J = 6.9 Hz, 2H), 7.83-7.76 (m, 2H), 7.74-7.66 (m, 2H), 7.32-7.22 (m, 4H), 5.91 (s, 2H), 5.79 (s, 1H), 5.56-5.51 (m, 1H), 3.93-3.86 (m, 1H), 3.83-3.72 (m, 2H), 3.61 (s, 3H), 3.28-3.22 (m, 1H), 3.14 (dd, J = 10.7, 9.5 Hz, 1H), 1.95 (t, J = 1.2 Hz, 4H), 1.69 (s, 1H), 1.58 (t, J = 9.3 Hz, 2H). | 511.40 |
| 4-(4-amino-6-(4-methacrylamido-phenyl)-7-methyl-7H-pyrrolo[2,3-d]pyrimidin-5-yl)-N-(oxetan-2-ylmethyl)benzamide | 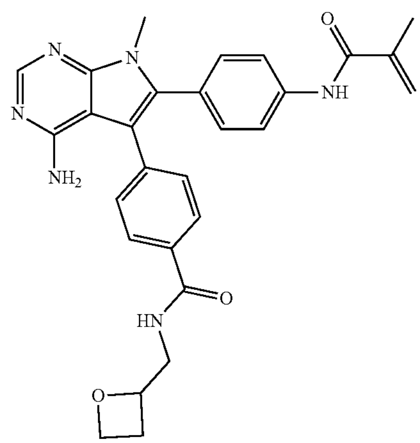 [SMILES: C=C(C)C(=O)Nc1ccc(-c2c(-c3ccc(C(=O)NCC4CCO4)cc3)c3c(N)ncnc3n2C)cc1] | $^1$H NMR (400 MHz, DMSO-$d_6$) δ 9.89 (s, 1H), 8.61 (t, J = 5.8 Hz, 1H), 8.21 (s, 1H), 7.82 (d, J = 8.3 Hz, 2H), 7.73-7.66 (m, 2H), 7.33-7.23 (m, 4H), 5.91 (s, 1H), 5.79 (s, 1H), 5.53 (s, 1H), 4.85-4.77 (m, 1H), 4.55-4.38 (m, 2H), 3.61 (s, 3H), 3.60-3.51 (m, 1H), 3.51-3.41 (m, 1H), 2.68-2.55 (m, 1H), 2.47-2.37 (m, 1H), 1.95 (d, J = 1.2 Hz, 3H). | 497.35 |
| 4-(4-amino-6-(4-methacrylamido-phenyl)-7-methyl-7H-pyrrolo[2,3-d]pyrimidin-5-yl)-N-(2-hydroxyethyl)benzamide | 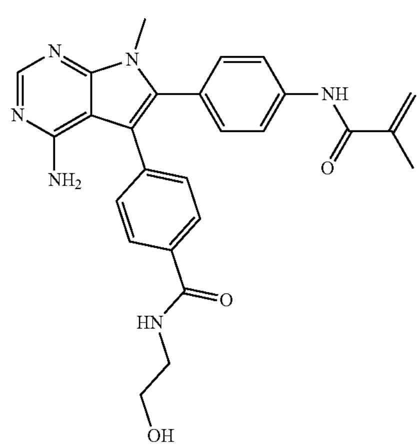 [SMILES: C=C(C)C(=O)Nc1ccc(-c2c(-c3ccc(C(=O)NCCO)cc3)c3c(N)ncnc3n2C)cc1] | $^1$H NMR (400 MHz, DMSO-$d_6$) δ 9.89 (s, 1H), 8.21 (s, 1H), 7.81 (d, J = 8.0 Hz, 2H), 7.73-7.66 (m, 2H), 7.27 (dd, J = 11.7, 8.3 Hz, 4H), 5.79 (s, 1H), 5.53 (s, 1H), 4.69 (t, J = 5.7 Hz, 1H), 3.61 (s, 3H), 3.50 (q, J = 6.2 Hz, 2H), 1.95 (s, 3H). | 471.35 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(3-hydroxypropyl)benzamide | 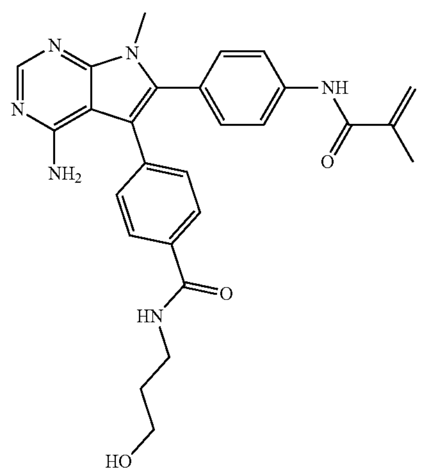 [SMILES: C=C(C)C(=O)Nc1ccc(-c2c(-c3ccc(C(=O)NCCCO)cc3)c3c(N)ncnc3n2C)cc1] | $^1$H NMR (400 MHz, DMSO-d$_6$) δ 9.89 (s, 1H), 8.42 (t, J = 5.6 Hz, 1H), 8.21 (s, 1H), 7.82-7.75 (m, 2H), 7.74-7.67 (m, 2H), 7.32-7.23 (m, 4H), 5.91 (s, 0H), 5.80 (s, 1H), 5.54 (d, J = 1.9 Hz, 1H), 4.46 (t, J = 5.2 Hz, 1H), 3.61 (s, 3H), 3.46 (q, J = 6.0 Hz, 2H), 3.34 (d, J = 6.0 Hz, 2H), 1.95 (t, J = 1.2 Hz, 3H), 1.67 (p, J = 6.6 Hz, 2H). | 485.35 |
| 4-(4-amino-6-(4-methacrylamido-phenyl)-7-methyl-7H-pyrrolo[2,3-d]pyrimidin-5-yl)-N-(3-methoxypropyl)benzamide | 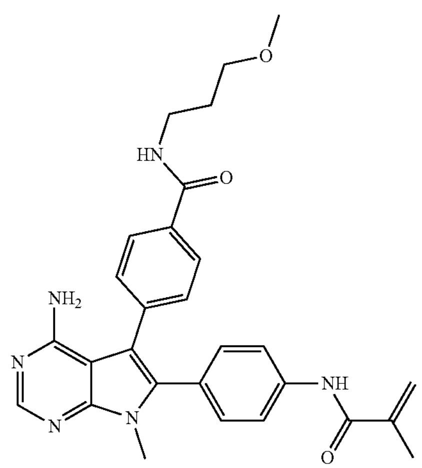 [SMILES: C=C(C)C(=O)Nc1ccc(-c2c(-c3ccc(C(=O)NCCCOC)cc3)c3c(N)ncnc3n2C)cc1] | $^1$H NMR (400 MHz, Chloroform-d) δ 8.40 (s, 1H), 7.75-7.68 (m, 2H), 7.65 (s, 1H), 7.62-7.55 (m, 2H), 7.37-7.29 (m, 2H), 7.26-7.18 (m, 2H), 6.96-6.88 (m, 1H), 5.82 (s, 1H), 5.51 (q, J = 1.6 Hz, 1H), 5.03 (s, 2H), 3.74 (s, 3H), 3.59 (q, J = 5.8 Hz, 4H), 3.41 (s, 3H), 2.09 (t, J = 1.2 Hz, 3H), 1.96-1.86 (m, 2H). | 499.25 |
| 4-(4-amino-6-(4-methacrylamido-phenyl)-7-methyl-7H-pyrrolo[2,3-d]pyrimidin-5-yl)-N-(1,3-difluoropropan-2-yl)benzamide | 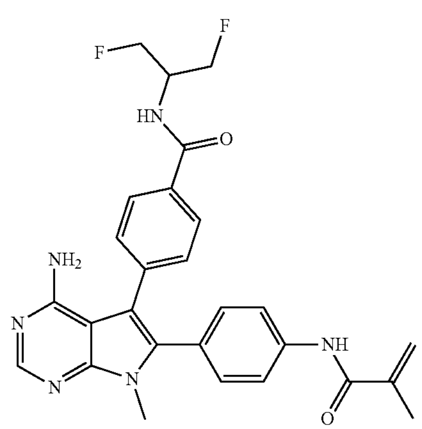 [SMILES: C=C(C)C(=O)Nc1ccc(-c2c(-c3ccc(C(=O)NC(CF)CF)cc3)c3c(N)ncnc3n2C)cc1] | $^1$H NMR (400 MHz, DMSO-d$_6$) δ 9.89 (s, 1H), 8.65 (d, J = 7.2 Hz, 1H), 8.21 (s, 1H), 7.87-7.81 (m, 2H), 7.74-7.67 (m, 2H), 7.35-7.29 (m, 2H), 7.29-7.23 (m, 2H), 5.94 (s, 1H), 5.80 (s, 1H), 5.53 (d, J = 1.9 Hz, 1H), 4.64 (t, J = 5.1 Hz, 2H), 4.53 (s, 3H), 3.62 (s, 3H), 1.95 (d, J = 1.2 Hz, 3H). | 505.20 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(pyrrolidin-3-yl)benzamide 2,2,2-trifluoroacetate | 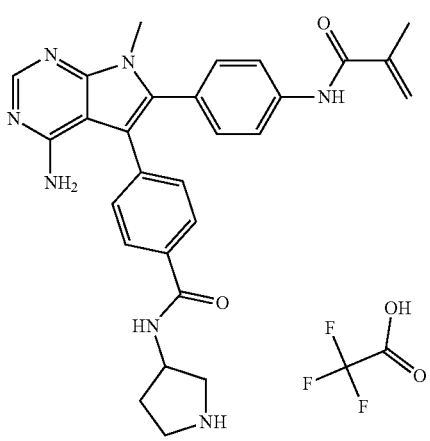 [SMILES: C=C(C)C(=O)Nc1ccc(-c2c(-c3ccc(C(=O)NC4CCNC4)cc3)c3c(N)ncnc3n2C)cc1 ; O=C(O)C(F)(F)F] | $^1$H NMR (400 MHz, DMSO-d$_6$) δ 9.95 (s, 1H), 8.84 (s, 2H), 8.60 (d, J = 6.2 Hz, 1H), 8.46 (d, J = 1.5 Hz, 1H), 7.87-7.80 (m, 2H), 7.76-7.70 (m, 2H), 7.37-7.31 (m, 2H), 7.31-7.24 (m, 2H), 5.80 (s, 1H), 5.55 (t, J = 1.5 Hz, 1H), 4.50 (hept, J = 6.0, 5.4 Hz, 1H), 3.67 (s, 3H), 3.41 (ddt, J = 28.8, 12.4, 6.4 Hz, 2H), 3.31-3.22 (m, 1H), 3.21-3.12 (m, 1H), 2.26-2.13 (m, 1H), 2.01 (dt, J = 13.1, 6.4 Hz, 1H), 1.95 (t, J = 1.2 Hz, 3H). | 496.40 |
| 4-(4-amino-6-(4-methacrylamido-phenyl)-7-methyl-7H-pyrrolo[2,3-d]pyrimidin-5-yl)-N-(cyclopropylmethyl)benzamide | 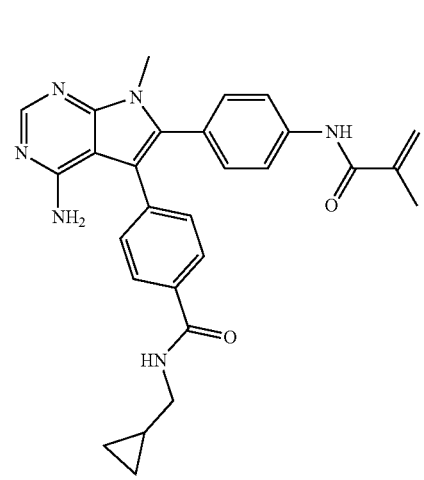 [SMILES: C=C(C)C(=O)Nc1ccc(-c2c(-c3ccc(C(=O)NCC4CC4)cc3)c3c(N)ncnc3n2C)cc1] | $^1$H NMR (400 MHz, DMSO-d$_6$) δ 9.89 (s, 1H), 8.67 (dd, J = 7.2, 3.8 Hz, 1H), 8.21 (s, 1H), 7.79 (dd, J = 8.3, 2.7 Hz, 2H), 7.70 (d, J = 8.6 Hz, 2H), 7.33-7.22 (m, 4H), 5.92 (s, 2H), 5.79 (s, 1H), 5.53 (d, J = 2.0 Hz, 1H), 3.97 (q, J = 7.9 Hz, 1H), 3.61 (s, 3H), 2.72 (ddd, J = 9.6, 6.5, 3.1 Hz, 1H), 2.46 (s, 1H), 2.33-2.20 (m, 1H), 1.94 (d, J = 1.4 Hz, 3H). | 481.35 |
| 4-(4-amino-6-(4-methacrylamido-phenyl)-7-methyl-7H-pyrrolo[2,3-d]pyrimidin-5-yl)-N-(1-(methoxymethyl)cyclobutyl)benzamide | 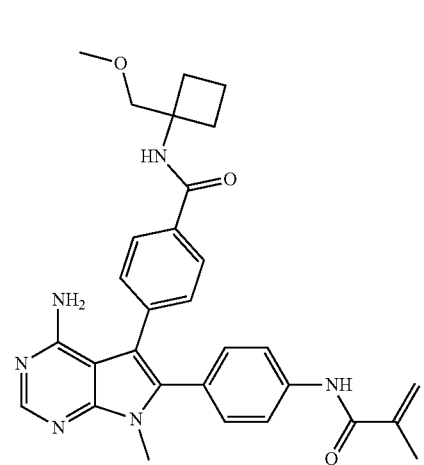 [SMILES: C=C(C)C(=O)Nc1ccc(-c2c(-c3ccc(C(=O)NC4(COC)CCC4)cc3)c3c(N)ncnc3n2C)cc1] | $^1$H NMR (400 MHz, DMSO-d$_6$) δ 9.89 (s, 1H), 8.34 (s, 1H), 8.21 (s, 1H), 7.84-7.78 (m, 2H), 7.74-7.66 (m, 2H), 7.30-7.22 (m, 4H), 5.80 (d, J = 1.3 Hz, 1H), 5.56-5.51 (m, 1H), 3.61 (d, J = 1.4 Hz, 5H), 3.31 (d, J = 13.6 Hz, 3H), 2.30-2.18 (m, 2H), 2.18-2.09 (m, 2H), 1.95 (d, J = 1.3 Hz, 3H), 1.85 (dd, J = 9.4, 4.8 Hz, 1H), 1.84-1.72 (m, 1H). | 525.40 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(3-fluorocyclobutyl)benzamide | 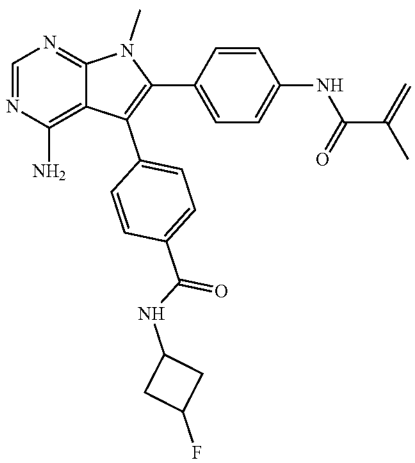 [SMILES: C=C(C)C(=O)Nc1ccc(-c2c(-c3ccc(C(=O)NC4CC(F)C4)cc3)c3c(N)ncnc3n2C)cc1] | $^1$H NMR (400 MHz, DMSO-d$_6$) δ 9.89 (s, 1H), 8.67 (dd, J = 7.2, 3.8 Hz, 1H), 8.21 (s, 1H), 7.79 (dd, J = 8.3, 2.7 Hz, 2H), 7.70 (d, J = 8.6 Hz, 2H), 7.33-7.22 (m, 4H), 5.92 (s, 2H), 5.79 (s, 1H), 5.53 (d, J = 2.0 Hz, 1H), 3.97 (q, J = 7.9 Hz, 1H), 3.61 (s, 3H), 2.72 (ddd, J = 9.6, 6.5, 3.1 Hz, 1H), 2.46 (s, 1H), 2.33-2.20 (m, 1H), 1.94 (d, J = 1.4 Hz, 3H). | 499.40 |
| 4-(4-amino-6-(4-methacrylamido-phenyl)-7-methyl-7H-pyrrolo[2,3-d]pyrimidin-5-yl)-N-((3-hydroxycyclobutyl)methyl)benzamide | 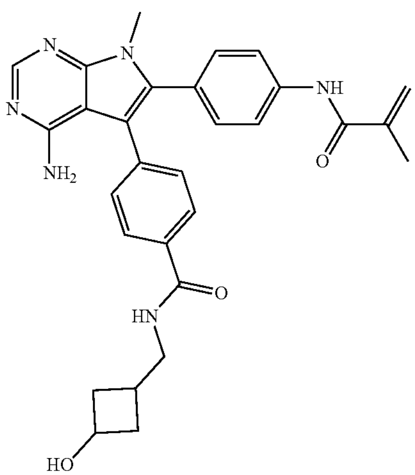 [SMILES: C=C(C)C(=O)Nc1ccc(-c2c(-c3ccc(C(=O)NCC4CC(O)C4)cc3)c3c(N)ncnc3n2C)cc1] | $^1$H NMR (400 MHz, DMSO-d$_6$) δ 9.89 (s, 1H), 8.43 (t, J = 5.9 Hz, 1H), 8.21 (s, 1H), 7.78 (d, J = 8.0 Hz, 2H), 7.70 (d, J = 8.5 Hz, 2H), 7.28 (dd, J = 10.3, 8.3 Hz, 4H), 5.79 (s, 3H), 5.53 (s, 1H), 4.92 (s, 1H), 3.91-3.83 (m, 1H), 3.61 (s, 3H), 3.25 (t, J = 6.2 Hz, 2H), 2.23 (p, J = 7.6, 7.1Hz, 2H), 1.95-1.90 (s, 4H), 1.59-1.47 (m, 2H), 1.24 (s, 0H). | 511.40 |
| 4-(4-amino-6-(4-methacrylamido-phenyl)-7-methyl-7H-pyrrolo[2,3-d]pyrimidin-5-yl)-N-((1-cyanocyclopropyl)methyl)benzamid | 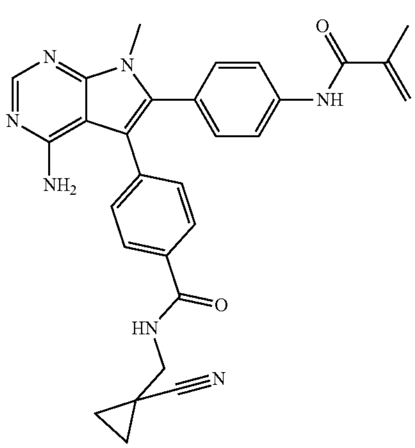 [SMILES: C=C(C)C(=O)Nc1ccc(-c2c(-c3ccc(C(=O)NCC4(C#N)CC4)cc3)c3c(N)ncnc3n2C)cc1] | $^1$H NMR (400 MHz, DMSO-d$_6$) δ 9.89 (s, 1H), 8.87 (t, J = 6.1 Hz, 1H), 8.21 (s, 1H), 7.86-7.79 (m, 2H), 7.74-7.66 (m, 2H), 7.35-7.29 (m, 2H), 7.29-7.23 (m, 2H), 5.92 (s, 2H), 5.79 (s, 1H), 5.53 (d, J = 2.0 Hz, 1H), 3.61 (s, 3H), 3.42 (d, J = 5.9 Hz, 2H), 1.94 (t, J = 1.3 Hz, 3H), 1.21 (q, J = 3.9, 2.9 Hz, 2H), 1.18-1.08 (m, 2H). | 506.40 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(3-hydroxycyclobutyl)benzamide | 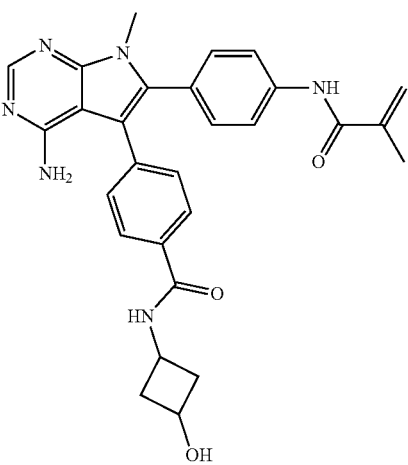 [SMILES: C=C(C)C(=O)Nc1ccc(-c2c(-c3ccc(C(=O)NC4CC(O)C4)cc3)c3c(N)ncnc3n2C)cc1] | $^1$He NMR (400 MHz, DMSO-d$_6$) δ 9.90 (s, 1H), 8.55 (t, J = 8.4 Hz, 1H), 8.21 (s, 1H), 7.79 (dd, J = 8.4, 2.0 Hz, 2H), 7.74-7.67 (m, 2H), 7.27 (td, J = 8.7, 2.2 Hz, 4H), 5.79 (s, 1H), 5.56-5.51 (m, 1H), 5.07 (d, J = 5.5 Hz, 1H), 3.86 (d, J = 7.7 Hz, 1H), 3.61 (s, 3H), 2.30-2.21 (m, 1H), 2.01-1.83 (m, 4H). | 497.35 |
| 4-(4-amino-6-(4-methacrylamido-phenyl)-7-methyl-7H-pyrrolo[2,3-d]pyrimidin-5-yl)-N-(1-hydroxypropan-2-yl)benzamide | 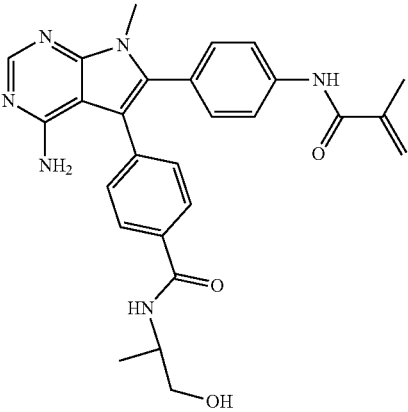 [SMILES: C=C(C)C(=O)Nc1ccc(-c2c(-c3ccc(C(=O)NC(C)CO)cc3)c3c(N)ncnc3n2C)cc1] | $^1$H NMR (400 MHz, DMSO-d$_6$) δ 9.89 (s, 1H), 8.21 (s, 1H), 8.07 (d, J = 8.2 Hz, 1H), 7.80 (d, J = 8.2 Hz, 2H), 7.70 (d, J = 8.5 Hz, 2H), 7.27 (t, J = 8.8 Hz, 4H), 5.89 (s, 2H), 5.79 (s, 1H), 5.53 (s, 1H), 4.69 (t, J = 5.8 Hz, 1H), 4.01 (q, J = 6.7 Hz, 1H), 3.61 (s, 3H), 3.45 (dt, J = 11.2, 5.8 Hz, 1H), 3.37-3.27 (m, 1H), 1.95 (t, J = 1.3 Hz, 3H), 1.12 (d, J = 6.7 Hz, 3H). | 485.40 |
| 4-(4-amino-6-(4-methacrylamido-phenyl)-7-methyl-7H-pyrrolo[2,3-d]pyrimidin-5-yl)-N-(1-(hydroxymethyl)cyclopropyl)methyl)benzamide | 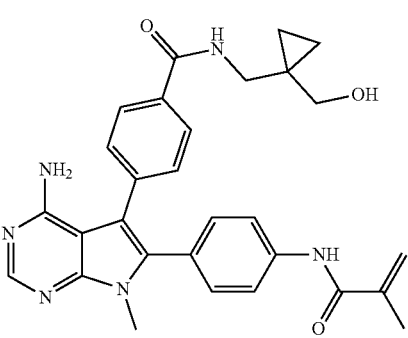 [SMILES: C=C(C)C(=O)Nc1ccc(-c2c(-c3ccc(C(=O)NCC4(CO)CC4)cc3)c3c(N)ncnc3n2C)cc1] | $^1$H NMR (400 MHz, Chloroform-d) δ 8.37 (s, 1H), 7.78-7.69 (m, 3H), 7.57 (d, J = 8.4 Hz, 2H), 7.30 (d, J = 8.0 Hz, 2H), 7.19 (d, J = 8.4 Hz, 2H), 7.13 (t, J = 5.9 Hz, 1H), 5.83 (s, 1H), 5.51 (d, J = 1.8 Hz, 1H), 5.09 (s, 2H), 3.73 (s, 3H), 3.51-3.43 (m, 4H), 2.08 (s, 3H), 0.60-0.49 (m, 4H). | 511.30 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-((4-methylmorpholin-3-yl)methyl)benzamide | 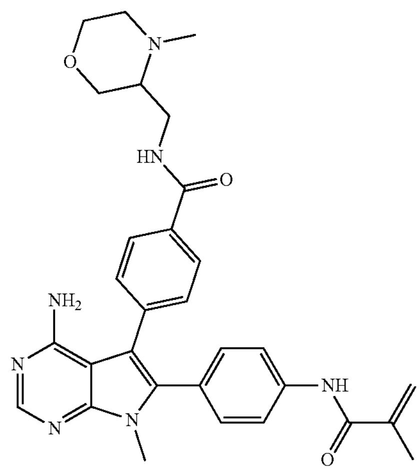 [SMILES: C=C(C)C(=O)Nc1ccc(-c2c(-c3ccc(C(=O)NCC4COCCN4C)cc3)c3c(N)ncnc3n2C)cc1] | $^1$H NMR (400 MHz, DMSO-d$_6$) δ 9.89 (s, 1H), 8.37 (t, J = 5.9 Hz, 1H), 8.21 (s, 1H), 7.81-7.74 (m, 2H), 7.73-7.66 (m, 2H), 7.33-7.23 (m, 4H), 5.79 (s, 1H), 5.53 (s, 1H), 3.74-3.62 (m, 2H), 3.61 (s, 3H), 3.57-3.41 (m, 2H), 3.23 (dd, J = 11.3, 9.3 Hz, 1H), 3.13 (dt, J = 13.3, 6.4 Hz, 1H), 2.63 (d, J = 11.7 Hz, 1H), 2.29 (s, 3H), 2.21-2.11 (m, 2H), 1.94 (t, J = 1.2 Hz, 3H). | 540.30 |
| 4-(4-amino-6-(4-methacrylamido-phenyl)-7-methyl-7H-pyrrolo[2,3-d]pyrimidin-5-yl)-N-(2-fluoroethyl)benzamide | 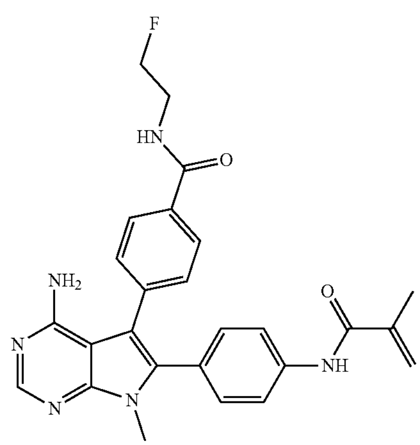 [SMILES: C=C(C)C(=O)Nc1ccc(-c2c(-c3ccc(C(=O)NCCF)cc3)c3c(N)ncnc3n2C)cc1] | $^1$H NMR (400 MHz, DMSO-d$_6$) δ 9.90 (s, 1H), 8.68 (d, J = 6.1 Hz, 1H), 8.21 (s, 1H), 7.82 (d, J = 7.9 Hz, 2H), 7.70 (d, J = 8.4 Hz, 2H), 7.28 (dd, J = 16.5, 8.1 Hz, 4H), 5.80 (s, 2H), 5.53 (s, 1H), 4.59 (t, J = 5.2 Hz, 1H), 4.47 (t, J = 5.2 Hz, 1H), 3.62 (s, 3H), 3.59 (d, J = 5.4 Hz, 1H), 3.59-3.50 (m, 1H), 1.95 (s, 3H). | 473.35 |
| 4-(4-amino-6-(4-methacrylamido-phenyl)-7-methyl-7H-pyrrolo[2,3-d]pyrimidin-5-yl)-N-(2-aminoethyl)-N-(2,2,2-trifluoroethyl)benzamide | 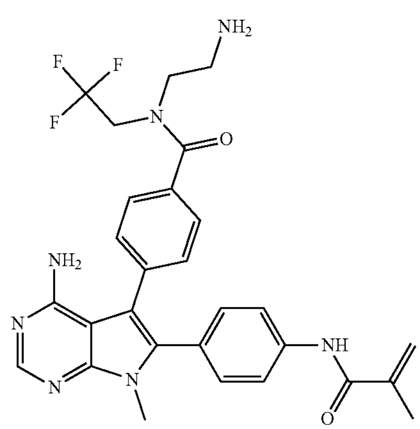 [SMILES: C=C(C)C(=O)Nc1ccc(-c2c(-c3ccc(C(=O)N(CCN)CC(F)(F)F)cc3)c3c(N)ncnc3n2C)cc1] | $^1$H NMR (400 MHz, DMSO-d$_6$) δ 9.95 (s, 1H), 8.46 (s, 1H), 7.86 (s, 3H), 7.73 (d, J = 8.5 Hz, 2H), 7.43 (d, J = 7.9 Hz, 2H), 7.29 (dd, J = 19.9, 8.0 Hz, 4H), 5.80 (s, 1H), 5.54 (d, J = 1.7 Hz, 1H), 4.25 (s, 2H), 3.68 (m, 5H), 3.08 (s, 2H), 1.94 (d, J = 1.5 Hz, 3H). | 552.2 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-((1-hydroxycyclobutyl)methyl)benzamide | 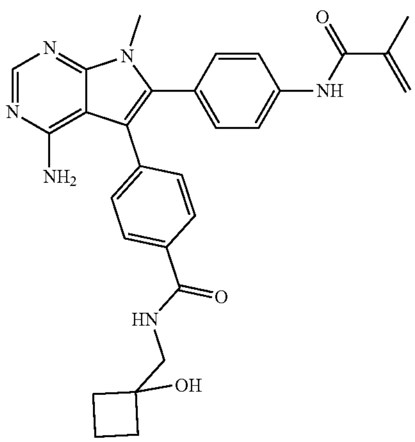 [SMILES: C=C(C)C(=O)Nc1ccc(-c2c(-c3ccc(C(=O)NCC4(O)CCC4)cc3)c3c(N)ncnc3n2C)cc1] | $^1$H NMR (400 MHz, DMSO-d$_6$) δ 9.89 (s, 1H), 8.31 (t, J = 5.9 Hz, 1H), 8.21 (s, 1H), 7.83 (d, J = 8.3 Hz, 2H), 7.74-7.67 (m, 2H), 7.33-7.23 (m, 4H), 5.92 (s, 2H), 5.79 (s, 1H), 5.53 (s, 1H), 5.15 (s, 1H), 3.61 (s, 3H), 3.41 (d, J = 6.0 Hz, 2H), 2.10-1.99 (m, 2H), 1.95 (d, J = 1.3 Hz, 3H), 1.89 (dd, J = 11.6, 8.9 Hz, 2H), 1.63 (d, J = 9.9 Hz, 1H), 1.48 (q, J = 9.2 Hz, 1H). | 511.40 |
| N-(4-(4-amino-5-(3-fluoro-4-((6-methylpyridin-2-yl)oxy)phenyl)-7-methyl-7H-pyrrolo[2,3-d]pyrimidin-6-yl)phenyl)methacrylamide | 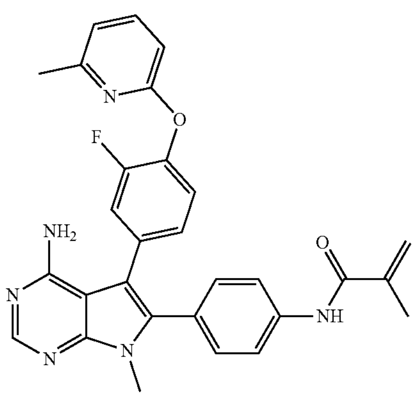 [SMILES: C=C(C)C(=O)Nc1ccc(-c2c(-c3ccc(Oc4cccc(C)n4)c(F)c3)c3c(N)ncnc3n2C)cc1] | $^1$H NMR (400 MHz, Methanol-d4) δ 8.22 (s, 1H), 7.75-7.71 (m, 3H), 7.35-7.33 (m, 1H), 7.22 (t, J = 8.4 Hz, 1H), 7.16-7.11 (m, 2H), 7.00 (d, J = 7.3 Hz, 1H), 6.81 (d, J = 8.2 Hz, 1H), 5.83 (s, 1H), 5.55 (s, 1H), 3.71 (s, 3H), 2.39 (s, 3H), 2.05 (s, 3H). | 509.30 |
| N-(4-(4-amino-5-(3-(2-methoxyethoxy)-4-((6-methylpyridin-2-yl)oxy)phenyl)-7-methyl-7H-pyrrolo[2,3-d]pyrimidin-6-yl)phenyl)methacrylamide | 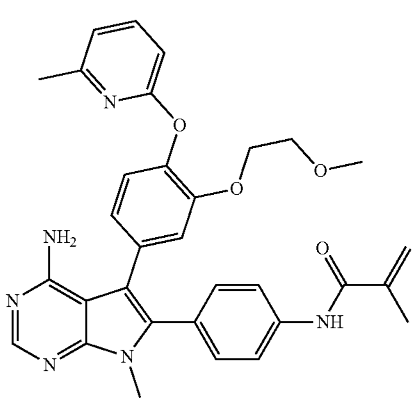 [SMILES: C=C(C)C(=O)Nc1ccc(-c2c(-c3ccc(Oc4cccc(C)n4)c(OCCOC)c3)c3c(N)ncnc3n2C)cc1] | $^1$H NMR (400 MHz, DMSO-d$_6$) δ 9.91 (s, 1H), 8.20 (s, 1H), 7.78-7.71 (m, 2H), 7.70-7.62 (m, 1H), 7.35-7.28 (m, 2H), 7.08 (d, J = 8.2 Hz, 1H), 6.97-6.90 (m, 2H), 6.84 (dd, J = 8.2, 2.0 Hz, 1H), 6.66 (d, J = 8.2 Hz, 1H), 5.79 (s, 1H), 5.53 (s, 1H), 3.88 (dd, J = 5.6, 3.8 Hz, 2H), 3.62 (s, 3H), 3.31-3.25 (m, 2H), 3.06 (s, 3H), 2.30 (s, 3H), 1.95 (d, J = 1.2 Hz, 3H). | 565.40 |

TABLE 2-continued

Additional Exemplary Compounds

| Compound | Structure | Proton NMR | MS [M + 1] |
|---|---|---|---|
| N-(4-(4-amino-7-methyl-5-(2-((6-methylpyridin-2-yl)oxy)pyrimidin-5-yl)-7H-pyrrolo[2,3-d]pyrimidin-6-yl)phenyl)methacrylamide | 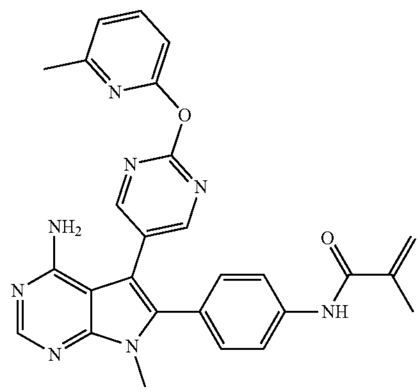 [SMILES: C=C(C)C(=O)Nc1ccc(-c2c(-c3cnc(Oc4cccc(C)n4)nc3)c3c(N)ncnc3n2C)cc1] | $^1$H NMR (400 MHz, DMSO-d$_6$) δ 9.94 (s, 1H), 8.39 (s, 2H), 8.21 (s, 1H), 7.91-7.64 (m, 3H), 7.31 (d, J= 8.6 Hz, 2H), 7.18 (d, J = 7.4 Hz, 1H), 7.01 (d, J = 8.0 Hz, 1H), 6.33 (s, 2H), 5.82 (s, 1H), 5.55 (d, J = 1.9 Hz, 1H), 3.60 (s, 3H), 2.42 (s, 3H), 1.96 (s, 3H). | 493.20 |
| N-(4-(4-amino-5-(3-fluoro-4-((4-methylpyrimidin-2-yl)oxy)phenyl)-7-methyl-7H-pyrrolo[2,3-d]pyrimidin-6-yl)phenyl)methacrylamide | 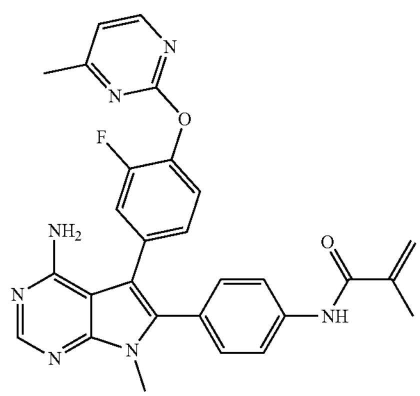 [SMILES: C=C(C)C(=O)Nc1ccc(-c2c(-c3ccc(Oc4nccc(C)n4)c(F)c3)c3c(N)ncnc3n2C)cc1] | $^1$H NMR (400 MHz, DMSO-d6) δ 9.92 (s, 1H), 8.47 (d, J = 5.0 Hz, 1H), 8.21 (s, 1H), 7.78-7.66 (m, 2H), 7.33 (m, J = 8.6, 2.3 Hz, 3H), 7.21-7.16 (m, 2H), 7.12 (s, 0H), 5.80 (s, 1H), 5.54 (d, J = 1.7 Hz, 1H), 3.59 (s, 3H), 2.42 (s, 3H), 1.95 (d, J = 1.2 Hz, 3H). | 510.20 |
| N-(4-(4-amino-7-methyl-5-(4-((4-methylpyrimidin-2-yl)oxy)phenyl)-7H-pyrrolo[2,3-d]pyrimidin-6-yl)phenyl)methacrylamide | 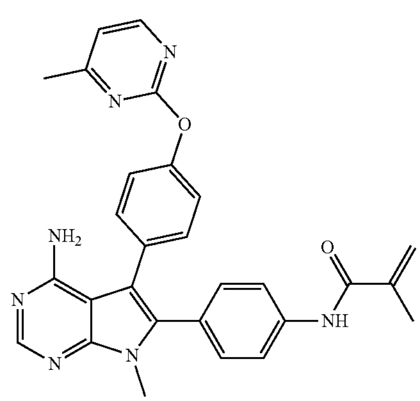 [SMILES: C=C(C)C(=O)Nc1ccc(-c2c(-c3ccc(Oc4nccc(C)n4)cc3)c3c(N)ncnc3n2C)cc1] | $^1$H NMR (400 MHz, DMSO-d6) δ 9.90 (s, 1H), 8.46 (d, J = 5.0 Hz, 1H), 8.20 (s, 1H), 7.82-7.68 (m, 2H), 7.37-7.26 (m, 4H), 7.24-7.12 (m, 3H), 5.79 (s, 1H), 5.53 (d, J = 1.8 Hz, 1H), 3.60 (s, 3H), 2.41 (s, 3H), 1.95 (t, J = 1.3 Hz, 3H). | 492.20 |

TABLE 2-continued

Additional Exemplary Compounds

| Compound | Structure | Proton NMR | MS [M + 1] |
|---|---|---|---|
| N-(4-(4-amino-7-methyl-5-(4-(5-methylpyrimidin-2-yloxy)phenyl)-7H-pyrrolo[2,3-d]pyrimidin-6-yl)phenyl) methacrylamide | 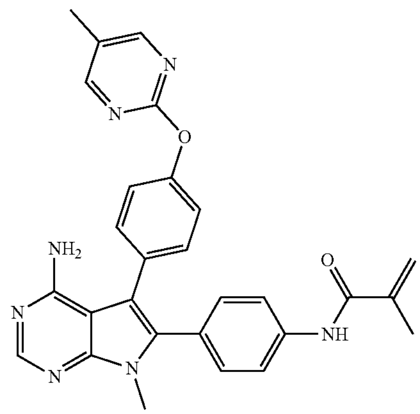 [SMILES: C=C(C)C(=O)Nc1ccc(-c2c(-c3ccc(Oc4ncc(C)cn4)cc3)c3c(N)ncnc3n2C)cc1] | $^1$H NMR (400 MHz, DMSO-d$_6$) δ 9.91 (s, 1H), 8.50 (d, J = 0.9 Hz, 2H), 8.20 (s, 1H), 7.81-7.67 (m, 2H), 7.39-7.25 (m, 4H), 7.25-7.12 (m, 2H), 6.2-5.67 (t, J = 1.0 Hz, 2H), 5.54 (t, J = 1.5 Hz, 1H), 3.60 (s, 3H), 2.22 (s, 3H), 1.95 (t, J = 1.2 Hz, 3H). | 492.20 |
| N-(4-(4-amino-7-(2-methoxyethyl)-5-(4-(6-methylpyridin-2-yloxy)phenyl)-7H-pyrrolo[2,3-d]pyrimidin-6-yl)phenyl) methacrylamide | 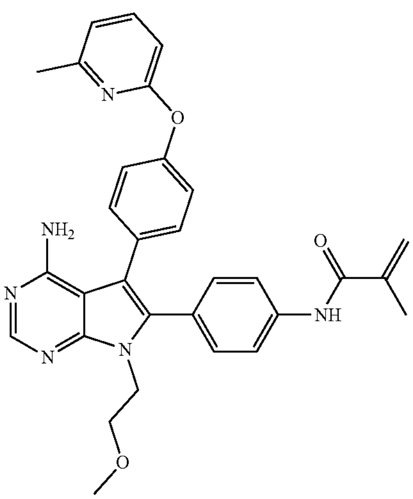 [SMILES: C=C(C)C(=O)Nc1ccc(-c2c(-c3ccc(Oc4cccc(C)n4)cc3)c3c(N)ncnc3n2CCOC)cc1] | $^1$H NMR (400 MHz, DMSO-d$_6$) δ 9.90 (s, 1H), 8.19 (s, 1H), 7.73 (dd, J = 8.4, 7.3 Hz, 3H), 7.34-7.27 (m, 2H), 7.31-7.21 (m, 2H), 7.10-7.03 (m, 2H), 7.01 (d, J = 7.4 Hz, 1H), 6.77 (d, J = 81 Hz, 1H), 5.82-5.77 (m, 1H), 5.69 (s, 1H), 5.53 (t, J = 1.4 Hz, 1H), 4.25 (t, J = 6.0 Hz, 2H), 3.50 (t, J = 6.0 Hz, 2H), 3.09 (s, 3H), 2.34 (s, 3H), 2.08 (s, 1H), 1.95 (t, J = 1.2 Hz, 3H). | 535.25 |
| N-(4-(4-amino-5-(4-(6-methylpyridin-2-yloxy)phenyl)-7-(oxetan-3-yl)-7H-pyrrolo[2,3-d]pyrimidin-6-yl)phenyl) methacrylamide | 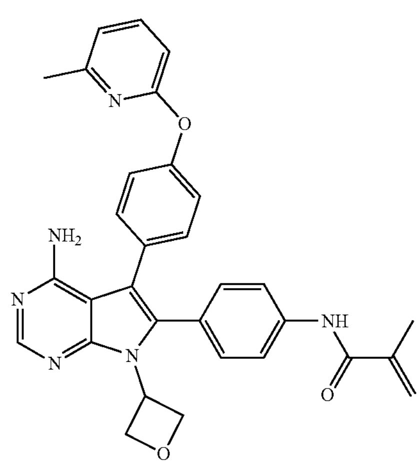 [SMILES: C=C(C)C(=O)Nc1ccc(-c2c(-c3ccc(Oc4cccc(C)n4)cc3)c3c(N)ncnc3n2C2COC2)cc1] | $^1$H NMR (400 MHz, DMSO-d$_6$) δ 9.91 (s, 1H), 8.20 (s, 1H), 7.77-7.68 (m, 3H), 7.24 (dd, J = 8.6, 3.1 Hz, 4H), 7.10-7.05 (m, 2H), 7.01 (d, J = 7.4 Hz, 1H), 6.78 (d, J = 8.1 Hz, 1H), 5.79 (s, 1H), 5.63-5.51 (m, 2H), 5.15 (t, J = 6.9 Hz, 2H), 4.61 (dd, J = 7.9, 6.2 Hz, 2H), 2.34 (s, 3H), 1.95 (d, J = 1.6 Hz, 3H). | 533.2 |

TABLE 2-continued

Additional Exemplary Compounds

| Compound | Structure | Proton NMR | MS [M + 1] |
|---|---|---|---|
| N-(4-(4-amino-7-methyl-5-(4-(6-methylpyridin-2-yloxy)phenyl)-7H-pyrrolo[2,3-d]pyrimidin-6-yl)-3-methylphenyl)methacrylamide | 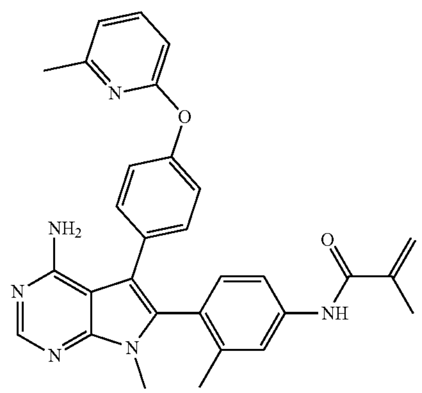 [SMILES: C=C(C)C(=O)Nc1ccc(-c2c(-c3ccc(Oc4cccc(C)n4)cc3)c3c(N)ncnc3n2C)c(C)c1] | ¹H NMR (400 MHz, DMSO-d₆) δ 9.83 (s, 1H), 8.20 (s, 1H), 7.71 (t, J = 7.8 Hz, 1H), 7.65-7.56 (m, 2H), 7.26 (d, J = 8.2 Hz, 1H), 7.24-7.16 (m, 2H), 7.09-7.02 (m, 2H), 7.00 (d, J = 7.3 Hz, 1H), 6.76 (d, J = 8.2 Hz, 1H), 5.79 (s, 1H), 5.52 (t, J = 1.5 Hz, 1H), 3.32 (s, 3H), 2.33 (s, 3H), 1.97-1.91 (m, 6H). | 505.25 |
| N-(4-(4-amino-7-methyl-5-(4-((6-methylpyridin-2-yl)oxy)phenyl)-7H-pyrrolo[2,3-d]pyrimidin-6-yl)-3-fluorophenyl)methacrylamide | 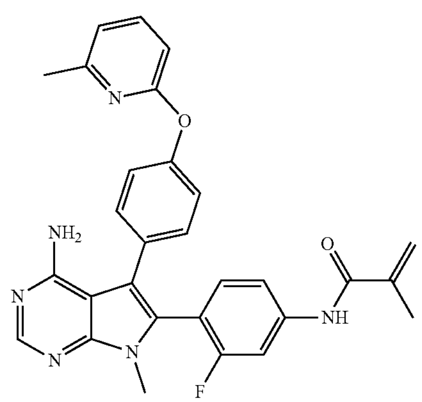 [SMILES: C=C(C)C(=O)Nc1ccc(-c2c(-c3ccc(Oc4cccc(C)n4)cc3)c3c(N)ncnc3n2C)c(F)c1] | ¹H NMR (400 MHz, DMSO-d₆) δ 10.11 (s, 1H), 8.21 (s, 1H), 7.81-7.69 (m, 2H), 7.51 (dd, J = 8.5, 2.0 Hz, 1H), 7.34-7.21 (m, 3H), 7.09 (d, J = 8.7 Hz, 2H), 7.02 (d, J = 7.4 Hz, 1H), 6.78 (d, J = 8.1 Hz, 1H), 5.82 (s, 1H), 5.58 (s, 1H), 3.55 (s, 3H), 2.34 (s, 3H), 1.95 (t, J = 1.3 Hz, 3H). | 509.50 |
| N-(4-(4-amino-7-methyl-5-(4-(6-methylpyridin-2-yloxy)phenyl)-7H-pyrrolo[2,3-d]pyrimidin-6-yl)-2-methylphenyl)methacrylamide | 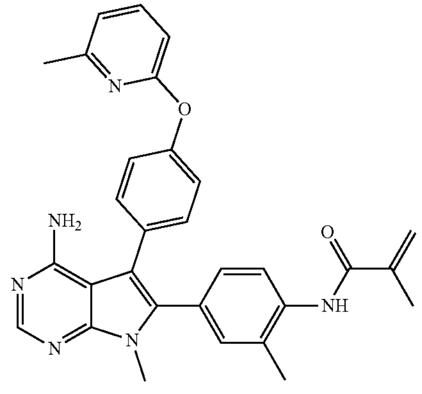 [SMILES: C=C(C)C(=O)Nc1ccc(-c2c(-c3ccc(Oc4cccc(C)n4)cc3)c3c(N)ncnc3n2C)cc1C] | ¹H NMR (400 MHz, DMSO-d₆) δ 9.31 (s, 1H), 8.19 (s, 1H), 7.72 (t, J = 7.8 Hz, 1H), 7.35 (d, J = 8.1 Hz, 1H), 7.30-7.21 (m, 3H), 7.16 (d, J = 8.2 Hz, 1H), 7.09 (d, J = 8.1 Hz, 2H), 7.01 (d, J = 7.4 Hz, 1H), 6.76 (d, J = 8.2 Hz, 1H), 5.85 (s, 1H), 5.50 (s, 1H), 3.32 (s, 2H), 2.34 (s, 3H), 2.17 (s, 3H), 1.96 (s, 3H). | 505.20 |

TABLE 2-continued

Additional Exemplary Compounds

| Compound | Structure | Proton NMR | MS [M + 1] |
|---|---|---|---|
| N-(4-(4-amino-7-methyl-5-(4-(6-methylpyridin-2-yloxy)phenyl)-7H-pyrrolo[2,3-d]pyrimidin-6-yl)-2-methoxyphenyl)methacrylamide | 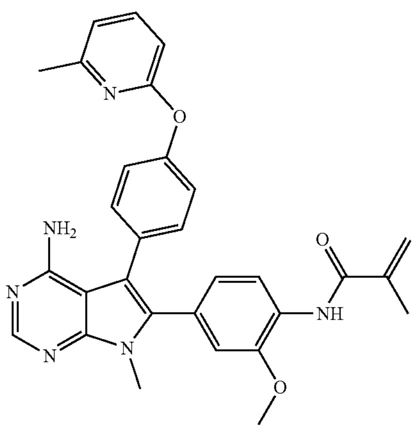 [SMILES: C=C(C)C(=O)Nc1ccc(-c2c(-c3ccc(Oc4cccc(C)n4)cc3)c3c(N)ncnc3n2C)cc1OC] | $^1$H NMR (400 MHz, DMSO-d$_6$) δ 8.79 (s, 1H), 8.20 (s, 1H), 7.92 (d, J = 8.2 Hz, 1H), 7.73 (t, J = 7.8 Hz, 1H), 7.33-7.25 (m, 2H), 7.13-7.06 (m, 2H), 7.04-6.93 (m, 3H), 6.79 (d, J = 8.1 Hz, 1H), 5.95 (s, 1H), 5.84 (s, 1H), 5.51 (d, J = 1.7 Hz, 1H), 3.69 (d, J = 6.4 Hz, 6H), 2.33 (s, 3H), 1.96 (d, J = 1.5 Hz, 3H). | 521.10 |
| N-(4-(4-amino-7-methyl-5-(4-((6-methylpyridin-2-yl)oxy)phenyl)-7H-pyrrolo[2,3-d]pyrimidin-6-yl)-2-fluorophenyl)methacrylamide | 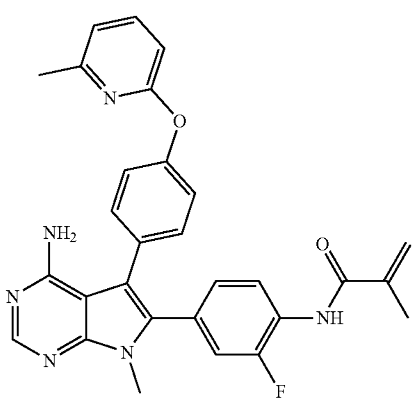 [SMILES: C=C(C)C(=O)Nc1ccc(-c2c(-c3ccc(Oc4cccc(C)n4)cc3)c3c(N)ncnc3n2C)cc1F] | $^1$H NMR (400 MHz, DMSO-d$_6$) δ 10.11 (s, 1H), 8.21 (s, 1H), 7.81-7.69 (m, 2H), 7.51 (dd, J = 8.6, 2.1 Hz, 1H), 7.27 (dd, J = 23.5, 8.5 Hz, 3H), 7.09 (d, J = 8.5 Hz, 1H), 7.02 (d, J = 7.4 Hz, 1H), 6.78 (d, J = 8.2 Hz, 1H), 5.82 (s, 1H), 5.58 (s, 1H), 3.55 (s, 3H), 2.34 (s, 3H), 1.95 (s, 3H). | 509.50 |
| N-(4-(4-amino-5-(4-((6-aminopyridin-2-yl)oxy)phenyl)-7-methyl-7H-pyrrolo[2,3-d]pyrimidin-6-yl)phenyl)methacrylamide | 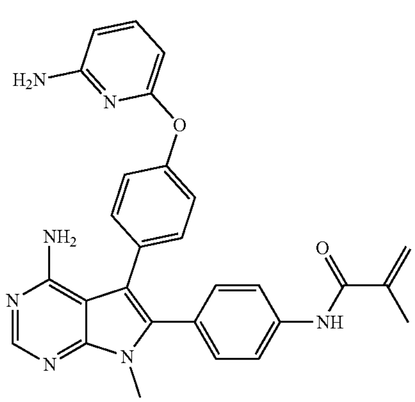 [SMILES: C=C(C)C(=O)Nc1ccc(-c2c(-c3ccc(Oc4cccc(N)n4)cc3)c3c(N)ncnc3n2C)cc1] | $^1$H NMR (400 MHz, DMSO-d6) δ 9.90 (s, 1H), 8.19 (s, 1H), 7.75-7.68 (m, 2H), 7.40 (t, J = 7.8 Hz, 1H), 7.33-7.27 (m, 2H), 7.27-7.19 (m, 2H), 7.05-6.97 (m, 2H), 6.18 (d, J = 7.9 Hz, 1H), 6.05-5.97 (m, 3H), 5.80 (s, 1H), 5.67 (s, 2H), 5.53 (t, J = 1.5 Hz, 1H), 3.60 (s, 3H), 1.95 (t, J = 1.3 Hz, 3H). | 492.25 |

TABLE 2-continued

Additional Exemplary Compounds

| Compound | Structure | Proton NMR | MS [M + 1] |
|---|---|---|---|
| N-(4-(4-amino-5-(4-((6-cyanopyridin-2-yl)oxy)phenyl)-7-methyl-7H-pyrrolo[2,3-d]pyrimidin-6-yl)phenyl) methacrylamide | 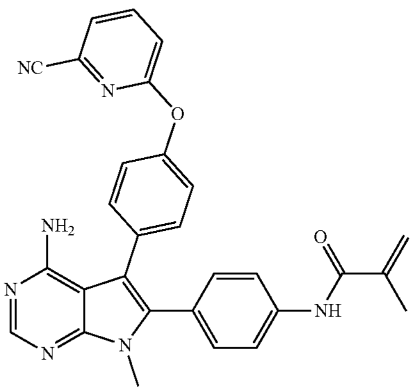 [SMILES: C=C(C)C(=O)Nc1ccc(-c2c(-c3ccc(Oc4cccc(C#N)n4)cc3)c3c(N)ncnc3n2C)cc1] | ¹H NMR (400 MHz, DMSO-d6) δ 9.90 (s, 1H), 8.21 (s, 1H), 8.09 (dd, J = 8.4, 7.2 Hz, 1H), 7.81 (d, J = 7.2 Hz, 1H), 7.77-7.67 (m, 2H), 7.41 (d, J = 8.4 Hz, 1H), 7.35-7.26 (m, 4H), 7.26-7.08 (m, 2H), 5.80 (s, 2H), 5.58-5.45 (m, 1H), 3.61 (s, 3H), 1.95 (t, J = 1.2 Hz, 3H). | 502.20 |
| N-(4-(4-amino-5-(4-((6-(hydroxymethyl)pyridin-2-yl)oxy)phenyl)-7-methyl-7H-pyrrolo[2,3-d]pyrimidin-6-yl)phenyl) methacrylamide | 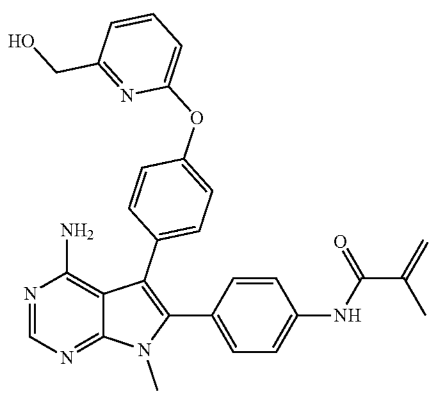 [SMILES: C=C(C)C(=O)Nc1ccc(-c2c(-c3ccc(Oc4cccc(CO)n4)cc3)c3c(N)ncnc3n2C)cc1] | ¹H NMR (400 MHz, DMSO-d₆) δ 9.89 (s, 1H), 8.21 (s, 1H), 7.85 (t, J = 7.8 Hz, 1H), 7.76-7.68 (m, 2H), 7.33-7.21 (m, 5H), 7.14-7.06 (m, 2H), 6.84 (d, J = 8.1 Hz, 1H), 5.93 (s, 2H), 5.80 (s, 1H), 5.54 (t, J = 1.5 Hz, 1H), 5.38 (t, J = 5.8 Hz, 1H), 4.42 (d, J = 5.0 Hz, 2H), 3.62 (s, 3H), 1.96 (d, J = 1.3 Hz, 3H). | 507.30 |
| N-(4-(4-amino-5-(4-((6-(methoxymethyl)pyridin-2-yl)oxy)phenyl)-7-methyl-7H-pyrrolo[2,3-d]pyrimidin-6-yl)phenyl) methacrylamide | 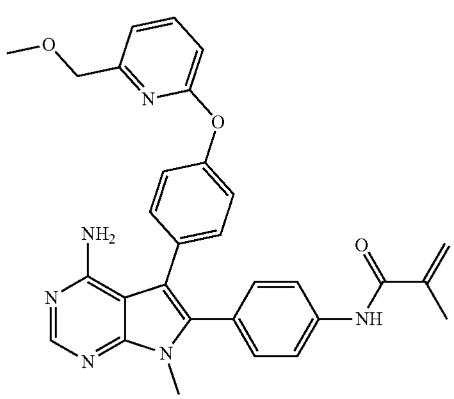 [SMILES: C=C(C)C(=O)Nc1ccc(-c2c(-c3ccc(Oc4cccc(COC)n4)cc3)c3c(N)ncnc3n2C)cc1] | ¹H NMR (400 MHz, DMSO-d₆) δ 9.89 (s, 1H), 8.20 (s, 1H), 7.86 (t, J = 7.8 Hz, 1H), 7.77-7.68 (m, 2H), 7.33-7.22 (m, 4H), 7.20-7.05 (m, 3H), 6.91 (d, J = 8.2 Hz, 1H), 5.80 (s, 1H), 5.56-5.51 (m, 1H), 4.35 (s, 2H), 3.62 (s, 3H), 3.33 (d, J = 6.5 Hz, 4H), 1.95 (t, J = 1.3 Hz, 3H). | 521.25 |

TABLE 2-continued

Additional Exemplary Compounds

| Compound | Structure | Proton NMR | MS [M + 1] |
|---|---|---|---|
| N-(4-(4-amino-5-(4-((6-methoxypyridin-2-yl)oxy)phenyl)-7-methyl-7H-pyrrolo[2,3-d]pyrimidin-6-yl)phenyl)methacrylamide | 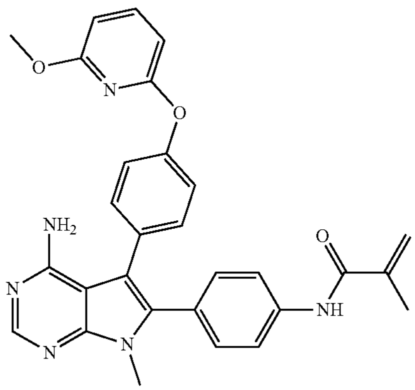 [SMILES: C=C(C)C(=O)Nc1ccc(-c2c(-c3ccc(Oc4cccc(OC)n4)cc3)c3c(N)ncnc3n2C)cc1] | $^1$H NMR (400 MHz, DMSO-d6) δ 9.90 (s, 1H), 8.20 (s, 1H), 7.75-7.62 (m, 3H), 7.33-7.19 (m, 4H), 7.15-7.01 (m, 2H), 6.52 (d, J = 7.9 Hz, 2H), 6.26-5.68 (m, 1H), 5.57-5.43 (m, 1H), 3.62 (s, 5H), 1.95 (d, J = 1.3 Hz, 3H). | 507.20 |
| N-(4-(4-amino-7-methyl-5-(4-((6-methylpyridin-2-yl)oxy)phenyl)-7H-pyrrolo[2,3-d]pyrimidin-6-yl)phenyl)-2-(methoxymethyl)acrylamide | 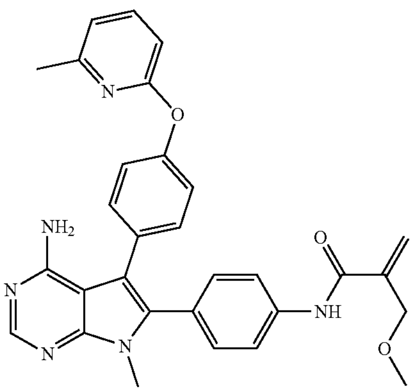 [SMILES: C=C(COC)C(=O)Nc1ccc(-c2c(-c3ccc(Oc4cccc(C)n4)cc3)c3c(N)ncnc3n2C)cc1] | $^1$H NMR (400 MHz, DMSO-d$_6$) δ 10.02 (s, 1H), 8.19 (s, 1H), 7.84-7.58 (m, 3H), 7.35-7.20 (m, 4H), 7.13-7.05 (m, 2H), 7.01 (d, J = 7.4 Hz, 1H), 6.78 (d, J = 8.1 Hz, 1H), 5.94 (s, 1H), 5.70 (s, 1H), 4.15 (s, 2H), 3.61 (s, 3H), 3.31 (d, J = 7.2 Hz, 3H), 2.34 (s, 3H). | 521.30 |
| N-(4-(4-amino-7-methyl-5-(4-((5-methyl-1,3,4-oxadiazol-2-yl)oxy)phenyl)-7H-pyrrolo[2,3-d]pyrimidin-6-yl)phenyl)methacrylamide | 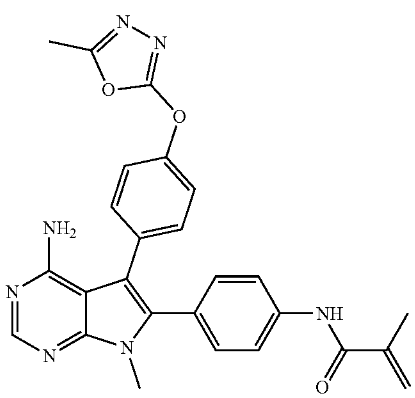 [SMILES: C=C(C)C(=O)Nc1ccc(-c2c(-c3ccc(Oc4nnc(C)o4)cc3)c3c(N)ncnc3n2C)cc1] | $^1$H NMR (400 MHz, Methanol-d4) δ 8.21 (s, 1H), 7.69-7.67 (m, 2H), 7.40 (s, 4H), 7.31-7.29 (m, 2H), 5.82 (s, 1H), 5.54 (d, J = 1.6 Hz, 1H), 3.71 (s, 3H), 2.50 (s, 3H), 2.04 (s, 3H). | 482.25 |
| 4-(4-amino-6-(4-methacrylamidophenyl)-7-methyl-7H-pyrrolo[2,3-d]pyrimidin-5-yl)-N-methyl-N-((5-methyl-1,3,4-oxadiazol-2-yl)methyl)benzamide | | $^1$H NMR (400 MHz, Chloroform-d) δ 8.40 (s, 1H), 7.62-7.56 (m, 3H), 7.48 (d, J = 8.0 Hz, 2H), 7.34 (d, J = 8.0 Hz, 2H), 7.23 (d, J = 8.4 Hz, 2H), 5.83 (s, 1H), 5.52 (s, 1H), 5.04 (s, 2H), 4.94 (s, 2H), 3.74 (s, 3H), 3.14 (s, 3H), 2.58 (s, 3H), 2.09 (t, J = 1.3 Hz, 3H) | 537.35 |

TABLE 2-continued

Additional Exemplary Compounds

| Compound | Structure | Proton NMR | MS [M + 1] |
|---|---|---|---|
| N-((1,2,4-oxadiazol-5-yl)methyl)-4-(4-amino-6-(4-methacrylamido-phenyl)-7-methyl-7H-pyrrolo[2,3-d]pyrimidin-5-yl)-N-methylbenzamide | 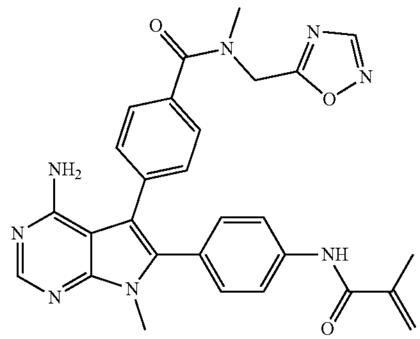 [SMILES: C=C(C)C(=O)Nc1ccc(-c2c(-c3ccc(C(=O)N(C)Cc4ncno4)cc3)c3c(N)ncnc3n2C)cc1] | $^1$H NMR (400 MHz, DMSO-d$_6$) δ 9.89 (s, 1H), 9.60 (s, 1H), 8.21 (s, 1H), 8.17-8.10 (m, 2H), 7.74-7.67 (m, 2H), 7.34-7.23 (m, 4H), 5.91 (s, 1H), 5.80 (s, 1H), 5.53 (t, J = 1.5 Hz, 1H), 4.15 (s, 2H), 3.62 (s, 3H), 3.07 (s, 3H), 1.95 (t, J = 1.3 Hz, 3H). | 523.20 |
| 4-(4-amino-6-(4-methacrylamido-phenyl)-7-methyl-7H-pyrrolo[2,3-d]pyrimidin-5-yl)-N-methyl-N-((5-methyl-1,2,4-oxadiazol-3-yl)methyl)benzamide | 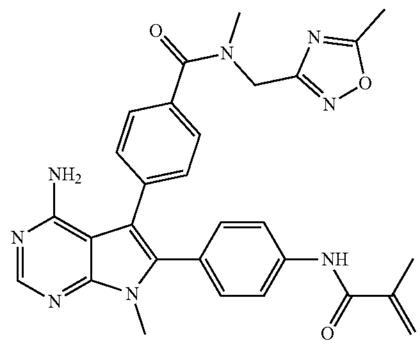 [SMILES: C=C(C)C(=O)Nc1ccc(-c2c(-c3ccc(C(=O)N(C)Cc4noc(C)n4)cc3)c3c(N)ncnc3n2C)cc1] | $^1$H NMR (400 MHz, DMSO-d$_6$) δ 9.89 (s, 1H), 8.20 (s, 1H), 7.70 (d, J = 8.6 Hz, 2H), 7.40 (d, J = 8.2 Hz, 2H), 7.26 (d, J = 8.4 Hz, 4H), 5.80 (s, 1H), 5.53 (s, 1H), 4.76 (s, 1H), 4.62 (s, 1H), 3.61 (s, 3H), 3.03 (s, 2H), 2.96 (s, 1H), 2.60 (s, 3H), 1.95 (t, J = 1.3 Hz, 3H). | 537.2 |
| (R)-4-(4-amino-6-(4-methacrylamido-phenyl)-7-methyl-7H-pyrrolo[2,3-d]pyrimidin-5-yl)-N-(1-cyclopropyl-2-methoxyethyl)benzamide | 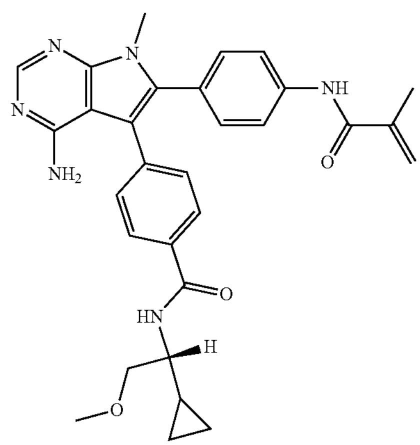 [SMILES: C=C(C)C(=O)Nc1ccc(-c2c(-c3ccc(C(=O)N[C@@H](COC)C4CC4)cc3)c3c(N)ncnc3n2C)cc1] | $^1$H NMR (400 MHz, DMSO-d$_6$) δ 9.89 (s, 1H), 8.27 (d, J = 8.5 Hz, 1H), 8.21 (s, 1H), 7.83-7.77 (m, 2H), 7.73-7.67 (m, 2H), 7.32-7.23 (m, 4H), 5.79 (s, 3H), 5.53 (d, J = 1.7 Hz, 1H), 3.68-3.61 (m, 4H), 3.48 (qd, J = 9.9, 6.2 Hz, 2H), 3..24(s, 3H), 1.95 (d, J = 1.2 Hz, 3H), 0.95 (dd, J = 8.1, 5.0 Hz, 1H), 0.45 (dt, J = 8.7, 4.1 Hz, 1H), 0.37-0.22 (m, 3H). | 525.30 |
| 4-(4-amino-6-(4-methacrylamido-phenyl)-7-methyl-7H-pyrrolo[2,3-d]pyrimidin-5-yl)-N-(2-hydroxy-2-methylpropyl)-N-methylbenzamide | 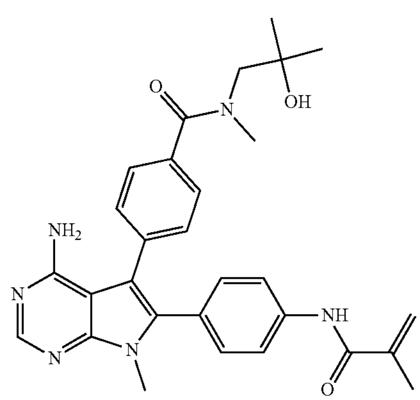 [SMILES: C=C(C)C(=O)Nc1ccc(-c2c(-c3ccc(C(=O)N(C)CC(C)(C)O)cc3)c3c(N)ncnc3n2C)cc1] | $^1$H NMR (400 MHz, Chloroform-d) δ 8.35 (s, 1H), 7.60 (d, J = 8.0 Hz, 3H), 7.44 (d, J = 7.8 Hz, 2H), 7.32 (d, J = 7.8 Hz, 2H), 7.22 (d, J = 8.3 Hz, 2H), 5.83 (s, 1H), 5.52 (d, J = 1.5 Hz, 1H), 3.75 (s, 3H), 3.62 (s, 2H), 3.14 (s, 3H), 2.09 (t, J = 1.2 Hz, 3H), 1.33 (s, 6H), 1.01 (s, 1H). | 513.45 |

TABLE 2-continued

Additional Exemplary Compounds

| Compound | Structure | Proton NMR | MS [M + 1] |
|---|---|---|---|
| N-(4-(4-amino-7-methyl-5-(4-((6-methylpyridin-2-yl)oxy)phenyl)-7H-pyrrolo[2,3-d]pyrimidin-6-yl)-2-(methoxymethyl)phenyl)methacrylamide | 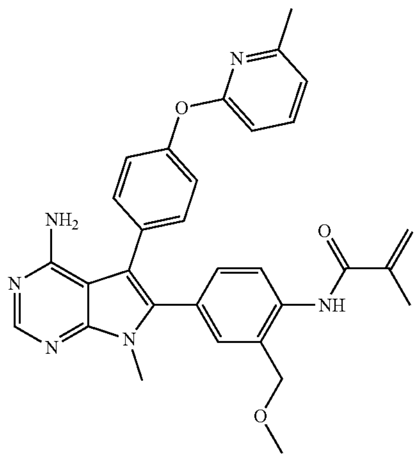 [SMILES: C=C(C)C(=O)Nc1ccc(-c2c(-c3ccc(Oc4cccc(C)n4)cc3)c3c(N)ncnc3n2C)cc1COC] | $^1$H NMR (400 MHz, DMSO-d$_6$) δ 9.38 (s, 1H), 8.20 (s, 1H), 7.85-7.63 (m, 2H), 7.51-7.18 (m, 4H), 7.15-7.06 (m, 2H), 7.01 (d, J = 7.4 Hz, 1H), 6.76 (d, J = 8.2 Hz, 1H), 5.85 (s, 1H), 5.54 (t, J = 1.6 Hz, 1H), 4.45 (s, 2H), 3.63 (s, 3H), 3.20 (s, 3H), 2.33 (d, J = 5.9 Hz, 3H), 1.98 (s, 3H). | 535.30 |
| N-(4-(4-amino-7-methyl-5-(4-((6-methylpyridin-2-yl)oxy)phenyl)-7H-pyrrolo[2,3-d]pyrimidin-6-yl)-2-((dimethylamino)methyl)phenyl)methacrylamide | 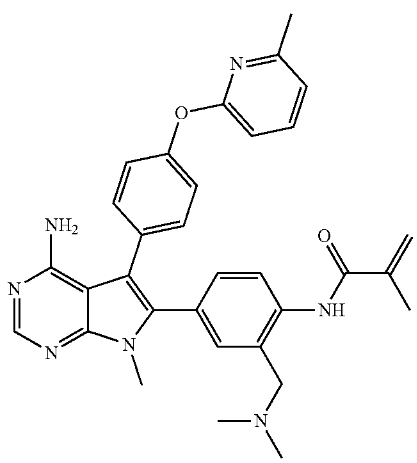 [SMILES: C=C(C)C(=O)Nc1ccc(-c2c(-c3ccc(Oc4cccc(C)n4)cc3)c3c(N)ncnc3n2C)cc1CN(C)C] | $^1$H NMR (400 MHz, DMSO-d6) δ 11.20 (s, 1H), 8.28 (d, J = 8.4 Hz, 1H), 8.19 (s, 1H), 7.72 (t, J = 7.8 Hz, 1H), 7.35 (dd, J = 8.5, 2.0 Hz, 1H), 7.27-7.20 (m, 2H), 7.10-7.04 (m, 3H), 7.01 (d, J = 7.3 Hz, 1H), 6.74 (d, J = 8.1 Hz, 1H), 5.85 (s, 1H), 5.71 (s, 2H), 5.54 (t, J = 1.6 Hz, 1H), 3.65 (s, 3H), 3.47 (s, 2H), 2.35 (s, 3H), 2.14 (s, 6H), 1.99 (s, 3H). | 548.30 |
| N-(4-(4-amino-7-methyl-5-(5-((6-methylpyridin-2-yl)oxy)pyrazin-2-yl)-7H-pyrrolo[2,3-d]pyrimidin-6-yl)phenyl)methacrylamide | 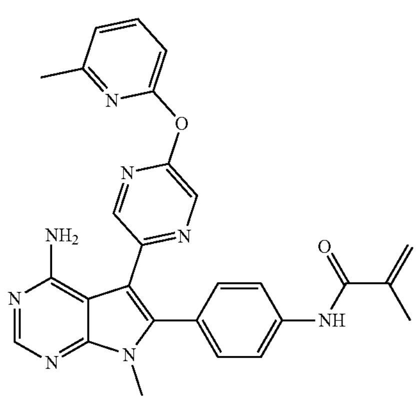 | $^1$H NMR (400 MHz, DMSO-d$_6$) δ 10.02 (s, 1H), 8.63 (s, 1H), 8.20 (s, 1H), 7.83 (dd, J = 31.7, 8.0 Hz, 3H), 7.66 (s, 1H), 7.59-7.28 (m, 4H), 7.12 (d, J = 7.4 Hz, 1H), 6.97 (d, J = 8.1 Hz, 1H), 5.83 (s, 1H), 5.56 (s, 1H), 3.57 (s, 3H), 2.35 (s, 3H), 1.97 (s, 3H). | 493.20 |

TABLE 2-continued

Additional Exemplary Compounds

| Compound | Structure | Proton NMR | MS [M + 1] |
|---|---|---|---|
| N-(4-(4-amino-5-(3-cyano-4-((6-methylpyridin-2-yl)oxy)phenyl)-7-methyl-7H-pyrrolo[2,3-d]pyrimidin-6-yl)phenyl) methacrylamide | 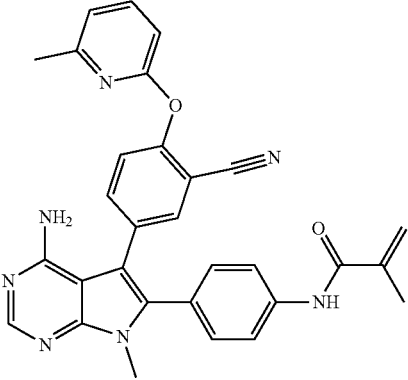 [SMILES: C=C(C)C(=O)Nc1ccc(-c2c(-c3ccc(Oc4cccc(C)n4)c(C#N)c3)c3c(N)ncnc3n2C)cc1] | $^1$H NMR (400 MHz, DMSO-d$_6$) δ: 9.92 (s, 1H), 8.27 (s, 1H), 7.82 (t, J = 7.8 Hz, 1H), 7.76 (d, J = 8.6 Hz, 2H), 7.71 (s, 1H), 7.47 (dd, J = 8.7, 2.2 Hz, 1H), 7.30 (d, J = 8.6 Hz, 2H), 7.23 (d, J = 8.6 Hz, 1H), 7.11 (d, J = 7.3 Hz, 1H), 6.97 (d, J = 8.1 Hz, 1H), 5.80 (s, 1H), 5.54 (s, 1H), 3.63 (s, 3H), 2.35 (s, 3H), 1.96 (s, 3H). 2.44 (s, 3H), 1.96 (d, J = 1.2 Hz, 3H). | 516.20 |
| 4-(4-amino-6-(4-methacrylamido-phenyl)-7-methyl-7H-pyrrolo[2,3-d]pyrimidin-5-yl)-2-fluoro-N-(tetrahydrofuran-3-yl)benzamide | 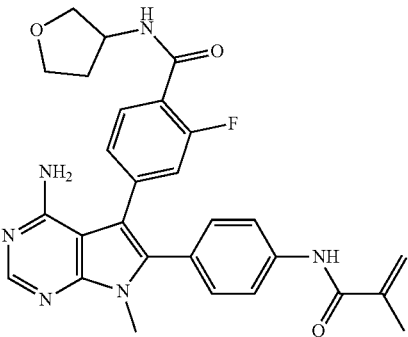 [SMILES: C=C(C)C(=O)Nc1ccc(-c2c(-c3ccc(C(=O)NC4CCOC4)c(F)c3)c3c(N)ncnc3n2C)cc1] | $^1$H NMR (400 MHz, Methanol-d4) δ 8.23 (s, 1H), 7.71-7.69 (m, 2H), 7.64 (t, J = 7.8 Hz, 1H), 7.31-7.27 (m, 2H), 7.21 (dd, J$_1$ = 8.0 Hz, J$_2$ = 1.2 Hz, 1H), 7.09 (dd, J = 11.6 Hz, J$_2$ = 1.2 Hz, 1H), 5.82 (t, J = 1.0 Hz, 1H), 5.55 (d, J = 1.8 Hz, 1H), 4.58-4.55 (m, 1H), 3.98-3.93 (m, 2H), 3.87-3.83 (m, 1H), 3.75-3.71 (m, 1H), 3.70 (s, 1H), 2.33-2.30 (m, 1H), 2.05 (s, 3H), 1.97-1.96 (m, 1H). | 515.35 |
| N-(4-(4-amino-7-methyl-5-(4-((6-methylpyridin-2-yl)oxy)phenyl)-7H-pyrrolo[2,3-d]pyrimidin-6-yl)phenyl) cyanamide | 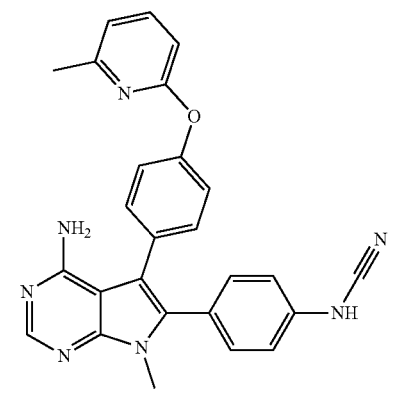 [SMILES: Cc1cccc(Oc2ccc(-c3c(-c4ccc(NC#N)cc4)n(C)c4ncnc(N)c34)cc2)n1] | $^1$H NMR (400 MHz, DMSO-d$_6$) δ 10.38 (s, 1H), 8.19 (s, 1H), 7.73 (t, J = 7.8 Hz, 1H), 7.33-7.28 (m, 2H), 7.28-7.21 (m, 2H), 7.13-7.05 (m, 2H), 7.02 (d, J = 7.3 Hz, 1H), 6.98-6.91 (m, 2H), 6.78 (d, J = 8.1 Hz, 1H), 5.90 (s, 2H), 3.60 (s, 3H), 2.35 (s, 3H). | 448.20 |
| 5-(4-amino-7-methyl-5-(4-((6-methylpyridin-2-yl)oxy)phenyl)-7H-pyrrolo[2,3-d]pyrimidin-6-yl)pyrimidine-2-carbonitrile | 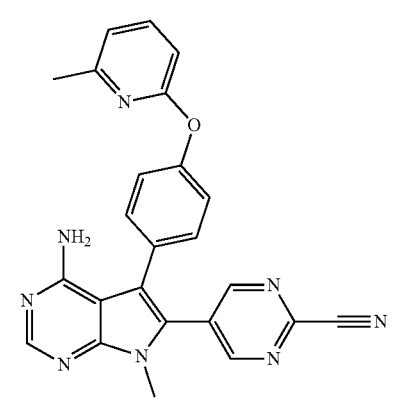 [SMILES: Cc1cccc(Oc2ccc(-c3c(-c4cnc(C#N)nc4)n(C)c4ncnc(N)c34)cc2)n1] | $^1$H NMR (400 MHz, DMSO-d$_6$) δ 8.97 (s, 2H), 8.26 (s, 1H), 7.75 (s, 1H), 7.47-7.26 (m, 2H), 7.25-7.10 (m, 2H), 7.04 (d, J = 7.4 Hz, 1H), 6.83 (d, J = 8.2 Hz, 1H), 3.76 (s, 3H), 2.36 (s, 3H). | 435.20 |

TABLE 2-continued

Additional Exemplary Compounds

| Compound | Structure | Proton NMR | MS [M + 1] |
|---|---|---|---|
| (S)-N-(4-(4-amino-5-(1-(4-(dimethylamino)-2-methylbutanoyl)piperidin-4-yl)-7-methyl-7H-pyrrolo[2,3-d]pyrimidin-6-yl)phenyl)acrylamide | 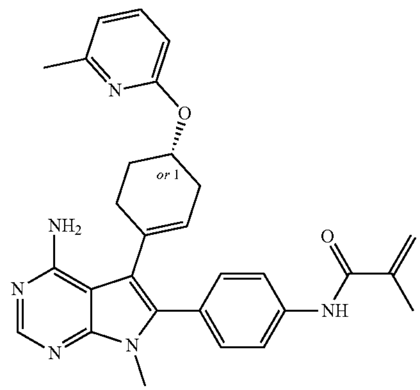 [SMILES: C=C(C)C(=O)Nc1ccc(-c2c(C3=CC[C@@H](Oc4cccc(C)n4)CC3)c3c(N)ncnc3n2C)cc1] | $^1$H NMR (400 MHz, Methanol-d4) δ 8.15 (s, 1H), 7.81-7.79 (m, 2H), 7.56-7.48 (m, 3H), 6.77 (d, J = 7.2 Hz, 1H), 6.56 (d, J = 8.4 Hz, 1H), 5.87-5.85 (m, 2H), 5.57-5.56 (m, 1H), 5.39-5.37 (m, 1H), 3.67 (s, 3H), 2.67-2.62 (m, 1H), 2.47-2.45 (m, 1H), 2.41 (s, 3H), 2.28-2.23 (m, 1H), 2.08 (s, 3H), 2.07-2.02 (m, 2H), 1.86 (d, J = 6.4 Hz, 1H). | 495.40 |
| (R)-N-(4-(4-amino-5-(1-(4-(dimethylamino)-2-methylbutanoyl)piperidin-4-yl)-7-methyl-7H-pyrrolo[2,3-d]pyrimidin-6-yl)phenyl)acrylamide | 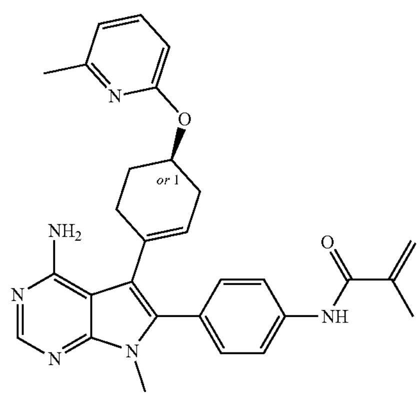 [SMILES: C=C(C)C(=O)Nc1ccc(-c2c(C3=CC[C@H](Oc4cccc(C)n4)CC3)c3c(N)ncnc3n2C)cc1] | $^1$H NMR (400 MHz, Methanol-d4) δ 8.15 (s, 1H), 7.81-7.79 (m, 2H), 7.56-7.48 (m, 3H), 6.78 (d, J = 7.2 Hz, 1H), 6.56 (d, J = 8.4 Hz, 1H), 5.87-5.85 (m, 2H), 5.57 (d, J = 1.7 Hz, 1H), 5.39-5.37 (m, 1H), 3.67 (s, 3H), 2.67-2.62 (m, 1H), 2.47-2.45 (m, 1H), 2.41 (s, 3H), 2.28-2.23 (m, 1H), 2.08 (s, 3H), 2.07-2.02 (m, 2H), 1.86 (m, 1H). | 495.40 |
| N-(4-(4-amino-7-methyl-5-(4-(pyrrolidine-1-carbonyl)phenyl)-7H-pyrrolo[2,3-d]pyrimidin-6-yl)-3-methylphenyl)methacrylamide | 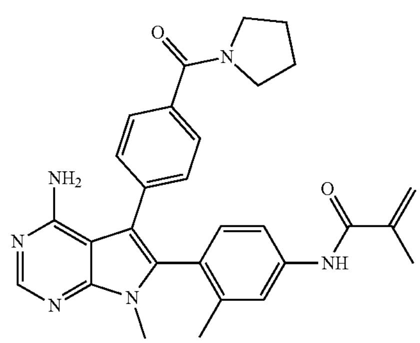 [SMILES: C=C(C)C(=O)Nc1ccc(-c2c(-c3ccc(C(=O)N4CCCC4)cc3)c3c(N)ncnc3n2C)c(C)c1] | $^1$H NMR (400 MHz, DMSO-d$_6$) δ 9.82 (s, 1H), 8.21 (s, 1H), 7.61 (s, 2H), 7.45 (d, J = 8.2 Hz, 2H), 7.23 (dd, J = 18.0, 8.2 Hz, 3H), 5.80 (s, 2H), 5.52 (s, 1H), 3.43 (s, 7H), 1.95 (s, 3H), 1.90 (s, 3H), 1.88-1.68 (m, 4H). | 495.30 |
| N-(4-(4-amino-7-methyl-5-(4-(pyrrolidine-1-carbonyl)phenyl)-7H-pyrrolo[2,3-d]pyrimidin-6-yl)-3-fluorophenyl)methacrylamide | 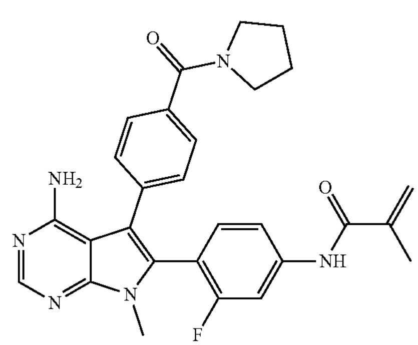 [SMILES: C=C(C)C(=O)Nc1ccc(-c2c(-c3ccc(C(=O)N4CCCC4)cc3)c3c(N)ncnc3n2C)c(F)c1] | $^1$H NMR (400 MHz, DMSO-d$_6$) δ 10.10 (s, 1H), 8.22 (s, 1H), 7.76 (dd, J = 12.4, 2.0 Hz, 1H), 7.48 (dd, J = 8.4, 1.6 Hz, 3H), 7.31-7.21 (m, 3H), 6.01 (s, 1H), 5.82 (s, 1H), 5.57 (s, 1H), 3.55 (s, 3H), 3.43 (dt, J = 17.2, 6.6 Hz, 4H), 1.95 (t, J = 1.2 Hz, 3H), 1.83 (dt, J = 17.8, 7.4 Hz, 4H). | 499.35 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)-2-methylphenyl)methacrylamide | 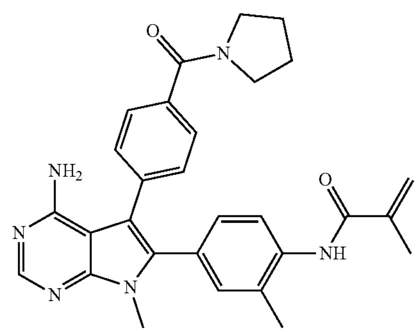 [SMILES: C=C(C)C(=O)Nc1ccc(-c2c(-c3ccc(C(=O)N4CCCC4)cc3)c3c(N)ncnc3n2C)cc1C] | ¹H NMR (400 MHz, DMSO-d₆) δ 9.31 (s, 1H), 8.21 (s, 1H), 7.63-7.40 (m, 2H), 7.34 (d, J = 8.1 Hz, 1H), 7.30-7.24 (m, 2H), 7.22 (d, J = 2.0 Hz, 1H), 7.12 (dd, J = 8.0, 2.0 Hz, 1H), 5.85 (s, 1H), 5.50 (s, 1H), 3.62 (s, 3H), 3.43 (d, J = 21.0 Hz, 4H), 2.15 (s, 3H), 1.96 (t, J = 1.2 Hz, 3H), 1.88-1.68 (m, 4H). | 495.30 |
| N-(4-(4-amino-7-methyl-5-(4-(pyrrolidine-1-carbonyl)phenyl)-7H-pyrrolo[2,3-d]pyrimidin-6-yl)-2-methoxyphenyl)methacrylamide | 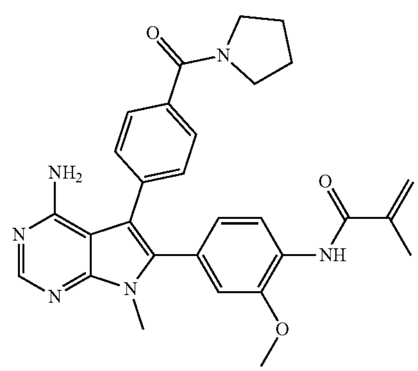 [SMILES: C=C(C)C(=O)Nc1ccc(-c2c(-c3ccc(C(=O)N4CCCC4)cc3)c3c(N)ncnc3n2C)cc1OC] | ¹H NMR (400 MHz, DMSO-d₆) δ 8.80 (s, 1H), 8.21 (s, 1H), 7.89 (d, J = 8.8 Hz, 1H), 7.53-7.47 (m, 2H), 7.33-7.26 (m, 2H), 6.94 (d, J = 6.6 Hz, 2H), 5.85 (s, 1H), 5.54-5.48 (m, 1H), 3.67 (d, J = 2.8 Hz, 6H), 3.44 (dt, J = 18.4, 6.6 Hz, 4H), 1.96 (d, J = 1.4 Hz, 3H), 1.90-1.79 (m, 4H). | 511.30 |
| 4-(4-amino-6-(4-methacrylamido-phenyl)-7-methyl-7H-pyrrolo[2,3-d]pyrimidin-5-yl)-N-methyl-N-(1-methyl-2-oxopyrrolidin-3-yl)benzamide | 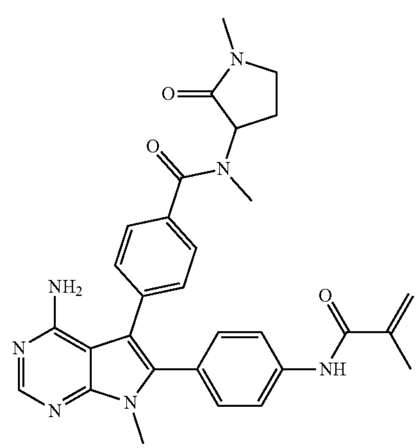 [SMILES: C=C(C)C(=O)Nc1ccc(-c2c(-c3ccc(C(=O)N(C)C4CCN(C)C4=O)cc3)c3c(N)ncnc3n2C)cc1] | ¹H NMR (400 MHz, DMSO-d₆) δ 9.88 (s, 1H), 8.20 (s, 1H), 7.74-7.66 (m, 2H), 7.38 (d, J = 7.7 Hz, 2H), 7.29-7.22 (m, 4H), 5.80 (s, 1H), 5.53 (s, 1H), 4.58 (t, J = 9.3 Hz, 1H), 3.61 (s, 3H), 3.32 (d, J = 8.7 Hz, 1H), 3.18 (d, J = 8.7 Hz, 1H), 2.77 (t, J = 13.3 Hz, 6H), 2.16 (s, 2H), 1.95 (s, 3H). | 538.35 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(1-methyl-2-oxopyrrolidin-3-yl)benzamide | 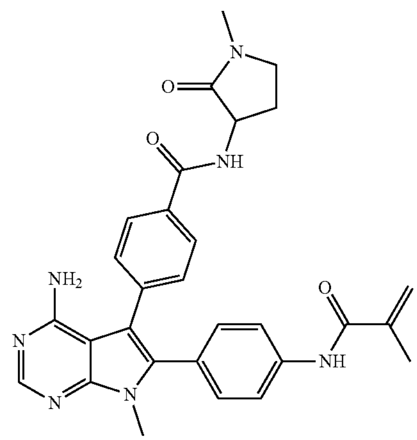 [SMILES: C=C(C)C(=O)Nc1ccc(-c2c(-c3ccc(C(=O)NC4CCN(C)C4=O)cc3)c3c(N)ncnc3n2C)cc1] | $^1$H NMR (400 MHz, DMSO-d$_6$) δ 9.88 (s, 1H), 8.72 (d, J = 8.4 Hz, 1H), 8.21 (s, 1H), 7.81 (d, J = 8.2 Hz, 2H), 7.72-7.66 (m, 2H), 7.29 (d, J = 8.1 Hz, 2H), 7.27-7.21 (m, 2H), 5.93 (s, 2H), 5.79 (s, 1H), 5.53 (s, 1H), 4.57 (q, J = 9.0 Hz, 1H), 3.62 (s, 3H), 3.34 (s, 2H), 2.77 (s, 3H), 2.32 (s, 1H), 1.94 (s, 4H). | 524.30 |
| N-(4-(4-amino-7-methyl-5-(6-(pyrrolidine-1-carbonyl)pyridin-3-yl)-7H-pyrrolo[2,3-d]pyrimidin-6-yl)phenyl)methacrylamide | 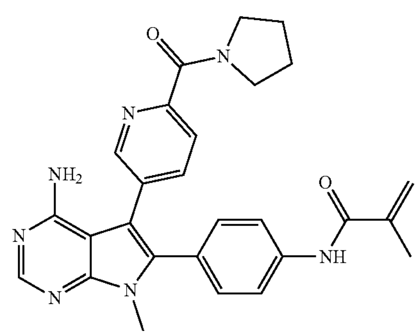 [SMILES: C=C(C)C(=O)Nc1ccc(-c2c(-c3ccc(C(=O)N4CCCC4)nc3)c3c(N)ncnc3n2C)cc1] | $^1$H NMR (400 MHz, DMSO-d$_6$) δ 9.91 (s, 1H), 8.31 (dd, J = 1.9, 1.1 Hz, 1H), 8.23 (s, 1H), 7.79-7.64 (m, 4H), 7.33-7.16 (m, 2H), 6.09 (s, 2H), 5.86-5.76 (m, 1H), 5.54 (q, J = 1.5 Hz, 1H), 3.63 (d, J = 10.6 Hz, 5H), 3.52-3.42 (m, 2H), 1.95 (t, J = 1.2 Hz, 3H), 1.83 (dqd, J = 5.1, 3.7, 1.7 Hz, 4H). | 482.35 |
| (R)-N-(4-(4-amino-5-(4-(2-(methoxymethyl)pyrrolidine-1-carbonyl)phenyl)-7-methyl-7H-pyrrolo[2,3-d]pyrimidin-6-yl)phenyl)methacrylamide | 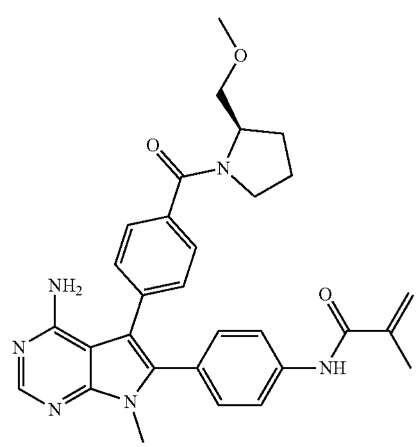 [SMILES: C=C(C)C(=O)Nc1ccc(-c2c(-c3ccc(C(=O)N4CCC[C@@H]4COC)cc3)c3c(N)ncnc3n2C)cc1] | $^1$H NMR (400 MHz, DMSO-d$_6$) δ 9.89 (s, 1H), 8.21 (s, 1H), 7.74-7.67 (m, 2H), 7.45 (d, J = 7.8 Hz, 2H), 7.26 (dd, J = 8.4, 2.8 Hz, 4H), 5.80 (s, 2H), 5.53 (t, J = 1.5 Hz, 1H), 4.25 (s, 1H), 3.62 (s, 4H), 3.50-3.35 (m, 3H), 3.30 (s, 2H), 2.91 (s, 1H), 2.04-1.95 (m, 1H), 1.95 (d, J = 1.2 Hz, 3H), 1.85 (s, 2H), 1.70 (s, 1H). | 525.40 |

TABLE 2-continued

Additional Exemplary Compounds

| Compound | Structure | Proton NMR | MS [M + 1] |
|---|---|---|---|
| (S)-N-(4-(4-amino-5-(4-(2-(methoxymethyl)pyrrolidine-1-carbonyl)phenyl)-7-methyl-7H-pyrrolo[2,3-d]pyrimidin-6-yl)phenyl)methacrylamide | 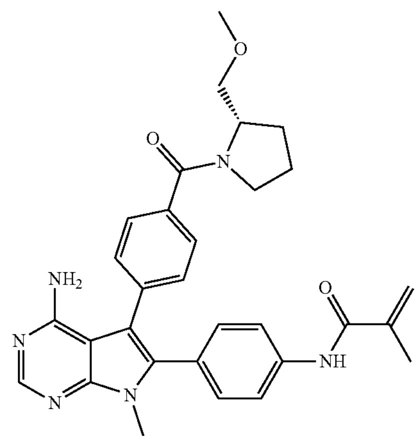 [SMILES: C=C(C)C(=O)Nc1ccc(-c2c(-c3ccc(C(=O)N4CCC[C@H]4COC)cc3)c3c(N)ncnc3n2C)cc1] | ¹H NMR (400 MHz, DMSO-d₆) δ 9.89 (s, 1H), 8.21 (s, 1H), 7.74-7.67 (m, 2H), 7.45 (d, J = 7.7 Hz, 2H), 7.26 (dd, J = 8.4, 2.8 Hz, 4H), 5.95 (s, 2H), 5.80 (s, 1H), 5.53 (d, J = 1.8 Hz, 1H), 4.25 (s, 1H), 4.04 (s, 0H), 3.62 (s, 3H), 3.42 (d, J = 7.1 Hz, 1H), 2.90 (s, 1H), 2.04-1.92 (m, 4H), 1.85 (s, 3H), 1.70 (s, 1H). | 525.45 |
| (R)-N-(4-(4-amino-5-(4-(2-cyanopyrrolidine-1-carbonyl)phenyl)-7-methyl-7H-pyrrolo[2,3-d]pyrimidin-6-yl)phenyl)methacrylamide | 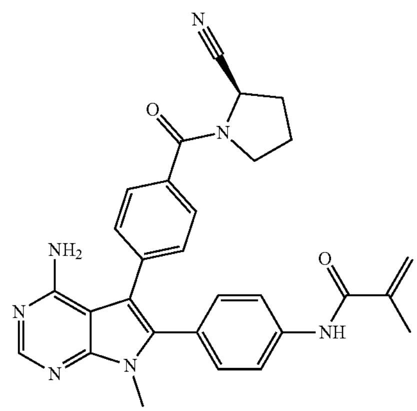 [SMILES: C=C(C)C(=O)Nc1ccc(-c2c(-c3ccc(C(=O)N4CCC[C@@H]4C#N)cc3)c3c(N)ncnc3n2C)cc1] | ¹H NMR (400 MHz, DMSO-d₆) δ 9.89 (s, 1H), 8.22 (s, 1H), 7.74-7.68 (m, 2H), 7.57 (d, J = 7.8 Hz, 2H), 7.33-7.23 (m, 4H), 5.80 (s, 1H), 5.53 (d, J = 2.0 Hz, 1H), 4.88 (t, J = 6.7 Hz, 1H), 3.70-3.60 (m, 4H), 3.59-3.50 (m, 1H), 2.33 (s, 1H), 2.18 (dq, J = 12.2, 6.1 Hz, 1H), 2.05-1.90 (m, 5H). | 506.20 |
| (R)-N-(4-(4-amino-5-(4-(3-methoxypiperidine-1-carbonyl)phenyl)-7-methyl-7H-pyrrolo[2,3-d]pyrimidin-6-yl)phenyl)methacrylamide | 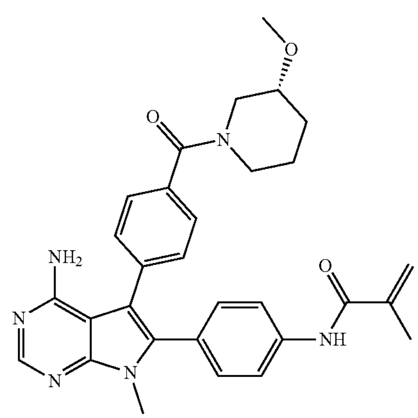 [SMILES: C=C(C)C(=O)Nc1ccc(-c2c(-c3ccc(C(=O)N4CCC[C@@H](OC)C4)cc3)c3c(N)ncnc3n2C)cc1] | ¹H NMR (400 MHz, DMSO-d₆) δ 9.89 (s, 1H), 8.24 (s, 1H), 7.70 (d, J = 8.3 Hz, 2H), 7.33 (s, 2H), 7.26 (dd, J = 8.3, 6.1 Hz, 4H), 6.14 (s, 2H), 5.79 (s, 1H), 5.53 (d, J = 1.6 Hz, 1H), 3.62 (s, 4H), 3.52 (s, 3H), 3.22 (s, 3H), 2.98 (s, 1H), 1.94 (d, J = 1.5 Hz, 3H), 1.67 (s, 3H), 1.42 (s, 1H). | 525.35 |

TABLE 2-continued

Additional Exemplary Compounds

| Compound | Structure | Proton NMR | MS [M + 1] |
|---|---|---|---|
| (S)-N-(4-(4-amino-5-(4-(3-methoxypiperidine-1-carbonyl)phenyl)-7-methyl-7H-pyrrolo[2,3-d]pyrimidin-6-yl)phenyl)methacrylamide | | ¹H NMR (400 MHz, DMSO-d₆) δ 9.88 (s, 1H), 8.20 (s, 1H), 7.69 (d, J = 8.4 Hz, 2H), 7.33 (d, J = 7.8 Hz, 2H), 7.30-7.22 (m, 4H), 5.95 (s, 0H), 5.79 (s, 1H), 5.53 (d, J = 1.8 Hz, 1H), 3.97-3.63 (m, 4H), 3.62-3.31 (m, 3H), 3.29-3.13 (m, 3H), 2.98 (s, 1H), 1.94 (t, J = 1.3 Hz, 3H), 1.85 (s, 1H), 1.67 (s, 1H), 1.57 (s, 1H), 1.41 (s, 1H). | 525.45 |
| 4-(4-amino-6-(4-methacrylamidophenyl)-7-methyl-7H-pyrrolo[2,3-d]pyrimidin-5-yl)-2-methoxy-N-(tetrahydrofuran-3-yl)benzamide | | ¹H NMR (400 MHz, DMSO-d₆) δ 9.91 (s, 1H), 8.19 (d, J = 14.1 Hz, 2H), 7.75-7.69 (m, 2H), 7.61 (d, J = 7.8 Hz, 1H), 7.34-7.26 (m, 2H), 6.93 (d, J = 1.5 Hz, 1H), 6.86 (dd, J = 7.8, 1.5 Hz, 1H), 6.02 (s, 2H), 5.81 (s, 1H), 5.54 (s, 1H), 4.43 (d, J = 1.0 Hz, 1H), 3.82 (td, J = 10.2, 9.7, 6.7 Hz, 2H), 3.71 (s, 3H), 3.71 (td, J = 8.2, 5.6 Hz, 1H), 3.60 (s, 3H), 3.55 (dd, J = 8.9, 4.0 Hz, 1H), 2.15 (dq, J = 12.6, 7.6 Hz, 1H), 1.95 (d, J = 1.2 Hz, 3H), 1.89-1.80 (m, 1H). | 527.30 |
| 4-(4-amino-6-(4-methacrylamidophenyl)-7-(oxetan-3-yl)-7H-pyrrolo[2,3-d]pyrimidin-5-yl)-2-methoxy-N-(tetrahydrofuran-3-yl)benzamide | | ¹H NMR (400 MHz, DMSO-d₆) δ 9.91 (s, 1H), 8.24-8.15 (m, 2H), 7.70 (d, J = 8.2 Hz, 2H), 7.59 (d, J = 7.8 Hz, 1H), 7.25 (d, J = 8.3 Hz, 2H), 6.93 (s, 1H), 6.84 (d, J = 7.9 Hz, 1H), 5.80 (s, 1H), 5.59-5.51 (m, 2H), 5.15 (t, J = 6.8 Hz, 2H), 4.60 (t, J = 6.9 Hz, 2H), 4.42 (s, 1H), 3.81 (td, J = 10.1, 9.6, 6.5 Hz, 2H), 3.70 (s, 4H), 3.54 (dd, J = 8.8, 4.0 Hz, 1H), 2.14 (dq, J = 14.6, 7.6 Hz, 1H), 1.95 (s, 3H), 1.84 (s, 1H). | 569.40 |

TABLE 2-continued

Additional Exemplary Compounds

| Compound | Structure | Proton NMR | MS [M + 1] |
|---|---|---|---|
| N-(4-(4-amino-5-(4-(2-cyanopyrrolidine-1-carbonyl)phenyl)-7-methyl-7H-pyrrolo[2,3-d]pyrimidin-6-yl)phenyl) methacrylamide | 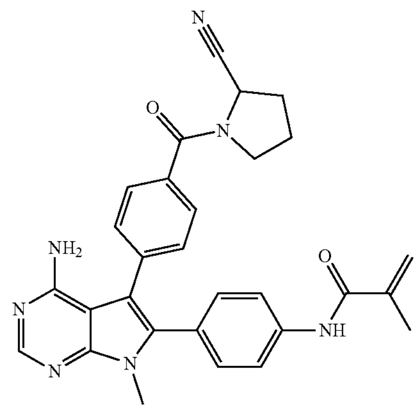 [SMILES: C=C(C)C(=O)Nc1ccc(-c2c(-c3ccc(C(=O)N4CCCC4C#N)cc3)c3c(N)ncnc3n2C)cc1] | ¹H NMR (400 MHz, DMSO-d₆) δ 9.89 (s, 1H), 8.21 (s, 1H), 7.70 (d, J = 8.6 Hz, 2H), 7.57 (d, J = 7.7 Hz, 2H), 7.28 (dd, J = 13.0, 8.2 Hz, 4H), 5.80 (s, 1H), 5.53 (s, 1H), 4.87 (s, 1H), 3.61 (s, 3H), 3.55 (s, 1H), 2.22-2.14 (m, 1H), 1.94 (d, J = 1.5 Hz, 3H). | 506.40 |
| 4-(4-amino-6-(4-methacrylamido-phenyl)-7-methyl-7H-pyrrolo[2,3-d]pyrimidin-5-yl)-N-(1,3-difluoropropan-2-yl)-N-methylbenzamide | 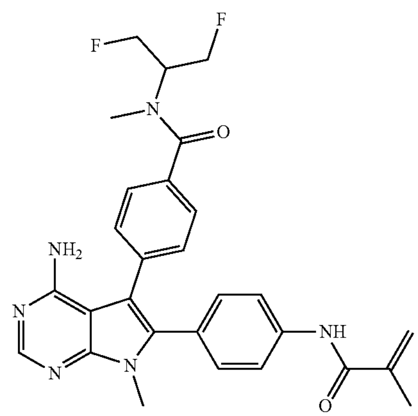 [SMILES: C=C(C)C(=O)Nc1ccc(-c2c(-c3ccc(C(=O)N(C)C(CF)CF)cc3)c3c(N)ncnc3n2C)cc1] | ¹H NMR (400 MHz, DMSO-d₆) δ 9.88 (s, 1H), 8.22 (s, 1H), 7.74-7.67 (m, 2H), 7.37 (s, 1H), 7.27 (dd, J = 8.7, 6.8 Hz, 5H), 5.80 (s, 1H), 5.53 (t, J = 1.5 Hz, 1H), 4.95-4.30 (dd, J = 8.7, 6.8 Hz, 5H), 3.62 (s, 3H), 2.96 (s, 3H), 1.95 (d, J = 1.2 Hz, 3H). | 519.4 |
| 4-(4-amino-6-(4-methacrylamido-phenyl)-7-methyl-7H-pyrrolo[2,3-d]pyrimidin-5-yl)-N-(2-(dimethylamino) tehyl)-N-(2,2,2-trifluoroethyl) benzamide | 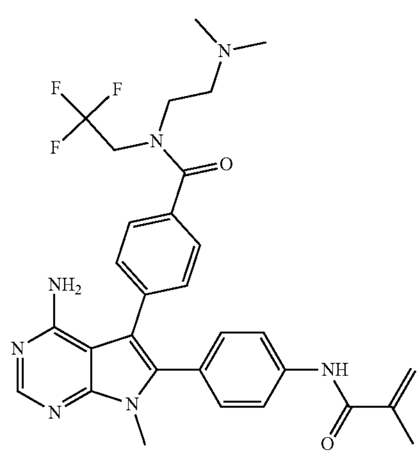 [SMILES: C=C(C)C(=O)Nc1ccc(-c2c(-c3ccc(C(=O)N(CCN(C)C)CC(F)(F)F)cc3)c3c(N)ncnc3n2C)cc1] | ¹H NMR (400 MHz, Chloroform-d) δ 8.41 (s, 1H), 7.56 (dd, J = 7.5, 5.7 Hz, 3H), 7.41 (d, J = 7.9 Hz, 2H), 7.35 (d, J = 8.2 Hz, 2H), 7.26-7.18 (m, 2H), 5.83 (d, J = 1.2 Hz, 1H), 5.52 (d, J = 1.6 Hz, 1H), 4.26 (s, 2H), 3.74 (s, 3H), 3.61 (s, 2H), 2.46 (s, 2H), 2.24-2.05 (m, 9H). | 580.3 |

TABLE 2-continued

Additional Exemplary Compounds

| Compound | Structure | Proton NMR | MS [M + 1] |
|---|---|---|---|
| N-(4-(4-amino-5-(4-(2-(methoxymethyl)piperidine-1-carbonyl)phenyl)-7-methyl-7H-pyrrolo[2,3-d]pyrimidin-6-yl)phenyl)methacrylamide | | $^1$H NMR (400 MHz, DMSO-d$_6$) δ 9.89 (s, 1H), 8.20 (s, 1H), 7.73-7.66 (m, 2H), 7.32 (d, J = 7.8 Hz, 2H), 7.29-7.22 (m, 4H), 5.94 (s, 2H), 5.79 (s, 1H), 5.53 (d, J = 1.9 Hz, 1H), 3.61 (s, 3H), 3.32 (s, 4H), 2.94 (s, 1H), 1.94 (t, J = 1.2 Hz, 3H), 1.57 (s, 4H), 1.38 (s, 1H). | 539.25 |
| 5-(4-amino-6-(4-methacrylamidophenyl)-7-methyl-7H-pyrrolo[2,3-d]pyrimidin-5-yl)-N-(cyclobutylmethyl)picolinamide | | $^1$H NMR (400 MHz, DMSO-d$_6$) δ 9.92 (s, 1H), 8.73 (t, J = 6.2 Hz, 1H), 8.33 (d, J = 2.1 Hz, 1H), 8.23 (s, 1H), 7.97 (d, J = 8.0 Hz, 1H), 7.77 (dd, J = 8.0, 2.2 Hz, 1H), 7.76-7.69 (m, 2H), 7.30-7.24 (m, 2H), 6.13 (s, 2H), 5.80 (s, 1H), 5.54 (s, 1H), 3.61 (s, 3H), 3.32 (d, J = 13.5 Hz, 1H), 2.55 (d, J = 7.4 Hz, 1H), 2.01-1.90 (m, 1H), 1.95 (s, 4H), 1.88-1.76 (m, 2H), 1.76-1.64 (m, 2H). | 496.30 |
| 4-(4-amino-6-(4-methacrylamidophenyl)-7-methyl-7H-pyrrolo[2,3-d]pyrimidin-5-yl)-N-(cyclobutylmethyl)benzamide | | $^1$H NMR (400 MHz, DMSO-d$_6$) δ 9.89 (s, 1H), 8.42 (t, J = 5.8 Hz, 1H), 8.21 (s, 1H), 7.78 (d, J = 8.0 Hz, 2H), 7.70 (d, J = 8.5 Hz, 2H), 7.28 (dd, J = 10.3, 8.3 Hz, 4H), 5.91-5.80 (s, 2H), 5.53 (s, 1H), 3.61 (s, 3H), 3.28 (t, J = 6.4 Hz, 3H), 2.05-1.94 (m, 1H), 1.99 (s, 2H), 1.95 (s, 2H), 1.82 (p, J = 7.2, 6.3 Hz, 2H), 1.71 (p, J = 8.6, 7.8 Hz, 2H). | 495.25 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(cyclobutylmethyl)-2-methoxybenzamide | 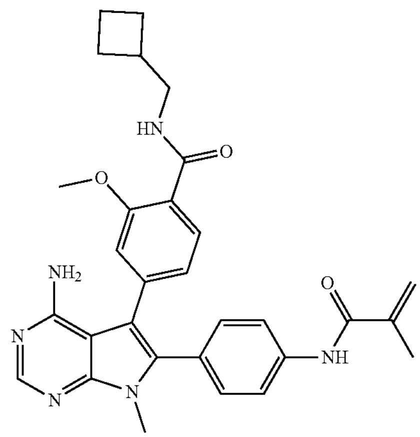 [SMILES: C=C(C)C(=O)Nc1ccc(-c2c(-c3ccc(C(=O)NCC4CCC4)c(OC)c3)c3c(N)ncnc3n2C)cc1] | $^1$H NMR (400 MHz, DMSO-$d_6$) δ 9.89 (s, 1H), 8.21 (s, 1H), 8.07 (t, J = 5.8 Hz, 1H), 7.75-7.69 (m, 2H), 7.66 (d, J = 7.9 Hz, 1H), 7.34-7.27 (m, 2H), 6.93 (d, J = 1.5 Hz, 1H), 6.86 (dd, J = 7.9, 1.5 Hz, 1H), 6.01 (s, 1H), 5.81 (s, 1H), 5.54 (s, 1H), 3.72 (s, 3H), 3.34-3.26 (m, 5H), 2.00 (dd, J = 8.5, 3.9 Hz, 1H), 1.96 (s, 4H), 1.90-1.78 (m, 2H), 1.1-1.73 (ddd, J = 17.0, 8.4, 4.5 Hz, 3H). | 525.30 |
| 2-acetyl-4-(4-amino-6-(4-methacrylamido-phenyl)-7-methyl-7H-pyrrolo[2,3-d]pyrimidin-5-yl)-N-(cyclobutylmethyl)benzamide | 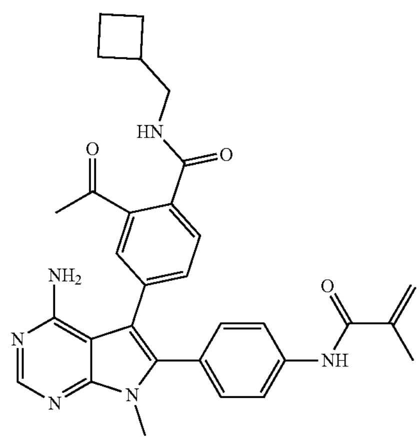 [SMILES: C=C(C)C(=O)Nc1ccc(-c2c(-c3ccc(C(=O)NCC4CCC4)c(C(C)=O)c3)c3c(N)ncnc3n2C)cc1] | $^1$H NMR (400 MHz, DMSO-$d_6$) δ 9.90 (s, 1H), 8.21 (s, 1H), 7.75-7.67 (m, 2H), 7.51 (d, J = 7.7 Hz, 1H), 7.45 (d, J = 1.4 Hz, 1H), 7.33-7.25 (m, 2H), 7.24 (dd, J = 7.7, 1.5 Hz, 1H), 6.20 (s, 1H), 5.79 (s, 1H), 5.53 (t, J = 1.5 Hz, 1H), 3.61 (s, 3H), 3.45 (dd, J = 14.0, 7.6 Hz, 1H), 3.38-3.28 (m, 1H), 2.74 (q, J = 7.6 Hz, 1H), 2.03-1.97 (m, 1H), 1.98 (s, 1H), 1.95 (t, J = 1.2 Hz, 3H), 1.84-1.72 (m, 4H), 1.51 (s, 3H). | 537.4 |
| 4-(4-amino-6-(4-methacrylamido-phenyl)-7-methyl-7H-pyrrolo[2,3-d]pyrimidin-5-yl)-N-(cyclobutylmethyl)-2-fluorobenzamide | 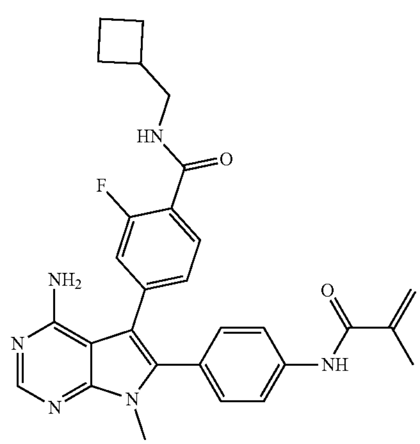 [SMILES: C=C(C)C(=O)Nc1ccc(-c2c(-c3ccc(C(=O)NCC4CCC4)c(F)c3)c3c(N)ncnc3n2C)cc1] | $^1$H NMR (400 MHz, DMSO-$d_6$) δ 9.92 (s, 1H), 8.25 (dt, J = 6.0, 2.9 Hz, 1H), 8.22 (s, 1H), 7.78-7.70 (m, 2H), 7.54 (t, J = 7.8 Hz, 1H), 7.33-7.25 (m, 2H), 7.10 (dd, J = 7.9, 1.6 Hz, 1H), 7.06 (dd, J = 11.4, 1.6 Hz, 1H), 5.81 (s, 1H), 5.54 (t, J = 1.5 Hz, 1H), 3.59 (s, 3H), 3.27 (dd, J = 1.0, 5.8 Hz, 2H), 2.48 (s, 1H), 2.04-1.92 (m, 5H), 1.89-1.77 (m, 2H), 1.80-1.65 (m, 2H). | 513.2 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-2-fluoro-N-(2-methoxy-2-methylpropyl) benzamide | 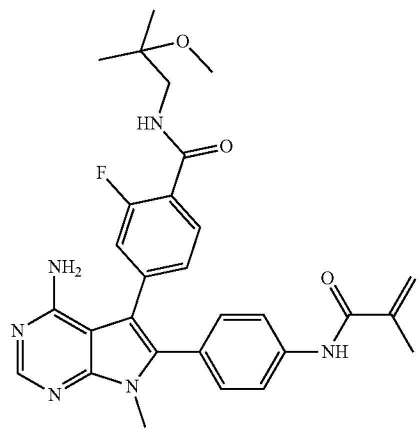 [SMILES: C=C(C)C(=O)Nc1ccc(-c2c(-c3ccc(C(=O)NCC(C)(C)OC)c(F)c3)c3c(N)ncnc3n2C)cc1] | $^1$H NMR (400 MHz, DMSO-d$_6$) δ 9.91 (s, 1H), 8.21 (s, 1H), 8.00 (q, J = 4.3, 2.8 Hz, 1H), 7.76-7.69 (m, 2H), 7.56 (t, J = 8.0 Hz, 1H), 7.32-7.25 (m, 2H), 7.12-7.03 (m, 2H), 5.80 (t, J = 1.0 Hz, 1H), 5.53 (t, J = 1.5 Hz, 1H), 3.59 (s, 3H), 3.31 (d, J = 6.0 Hz, 2H), 3.13 (s, 3H), 1.95 (t, J = 1.2 Hz, 3H), 1.12 (s, 6H). | 531.3 |
| 5-(4-amino-6-(4-methacrylamido-phenyl)-7-methyl-7H-pyrrolo[2,3-d]pyrimidin-5-yl)-N-(2-methoxy-2-methylpropyl) picolinamide | 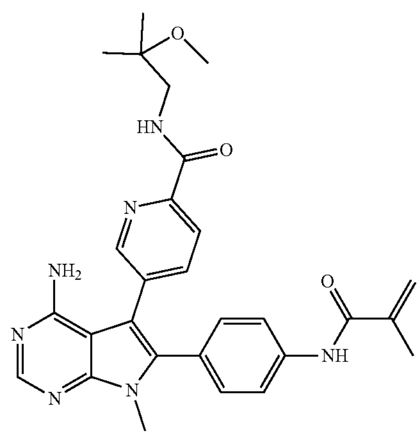 [SMILES: C=C(C)C(=O)Nc1ccc(-c2c(-c3ccc(C(=O)NCC(C)(C)OC)nc3)c3c(N)ncnc3n2C)cc1] | $^1$H NMR (400 MHz, DMSO-d$_6$) δ 9.91 (s, 1H), 8.37 (d, J = 2.1 Hz, 1H), 8.30 (t, J = 6.2 Hz, 1H), 8.22 (s, 1H), 7.99 (d, J = 8.0 Hz, 1H), 7.81-7.69 (m, 3H), 7.30-7.24 (m, 2H), 6.12 (s, 2H), 5.80 (s, 1H), 5.53 (s, 1H), 3.61 (s, 3H), 3.36 (d, J = 6.2 Hz, 2H), 3.15 (s, 3H), 1.95 (d, J = 1.3 Hz, 3H), 1.11 (s, 6H). | 514.40 |
| 4-(4-amino-6-(4-methacrylamido-phenyl)-7-methyl-7H-pyrrolo[2,3-d]pyrimidin-5-yl)-N-((1-methyl-1H-pyrazol-3-yl)methyl) benzamide | 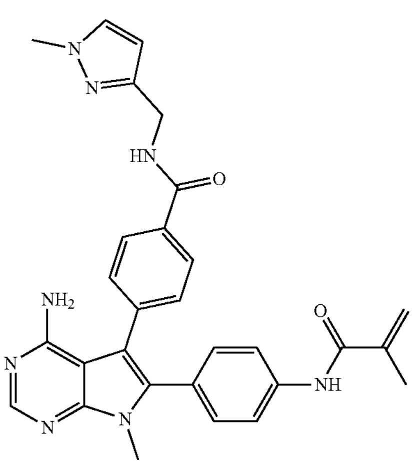 [SMILES: C=C(C)C(=O)Nc1ccc(-c2c(-c3ccc(C(=O)NCc4ccn(C)n4)cc3)c3c(N)ncnc3n2C)cc1] | $^1$H NMR (400 MHz, DMSO-d$_6$) δ 9.89 (s, 1H), 8.86 (t, J = 5.9 Hz, 1H), 8.21 (s, 1H), 7.83 (d, J = 8.0 Hz, 2H), 7.70 (d, J = 8.6 Hz, 2H), 7.56 (d, J = 2.2 Hz, 1H), 7.32-7.23 (m, 4H), 6.12 (d, J = 2.2 Hz, 1H), 5.91 (s, 2H), 5.80 (s, 1H), 5.53 (s, 1H), 4.39 (d, J = 5.8 Hz, 2H), 3.78 (s, 3H), 3.61 (s, 3H), 1.95 (s, 3H), 1.29 (s, 1H). | 521.25 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-((tetrahydrofuran-2-yl)methyl) benzamide | 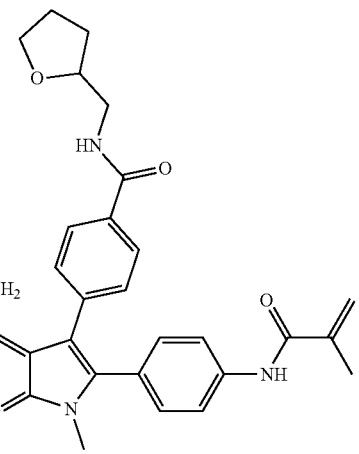 | $^1$H NMR (400 MHz, DMSO-$d_6$) δ 9.88 (s, 1H), 8.50 (t, J = 5.9 Hz, 1H), 8.22 (s, 1H), 7.84-7.77 (m, 2H), 7.74-7.66 (m, 2H), 7.32-7.23 (m, 4H), 5.80 (s, 1H), 5.53 (t, J = 1.5 Hz, 1H), 3.97 (p, J = 6.3 Hz, 1H), 3.82-3.73 (m, 1H), 3.67-3.57 (m, 1H), 3.62 (s, 3H), 3.25 (s, 2H), 1.95 (t, J = 1.2 Hz, 3H), 1.94-1.85 (m, 1H), 1.85-1.77 (m, 2H), 1.65-1.54 (m, 1H). | 511.3 |
| 4-(4-amino-6-(4-methacrylamido-phenyl)-7-methyl-7H-pyrrolo[2,3-d]pyrimidin-5-yl)-N-((1-methylpyrrolidin-2-yl)methyl) benzamide | 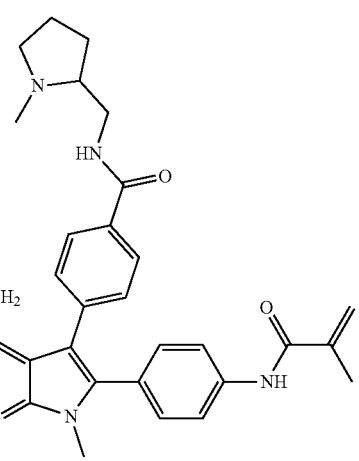 | $^1$H NMR (400 MHz, DMSO-$d_6$) δ 9.89 (s, 1H), 8.35 (s, 1H), 8.21 (s, 1H), 7.82-7.75 (m, 2H), 7.74-7.66 (m, 2H), 7.33-7.23 (m, 4H), 5.80 (d, J = 1.4 Hz, 1H), 5.56-5.51 (m, 1H), 3.61 (s, 3H), 3.46 (dt, J = 12.9, 5.0 Hz, 1H), 3.16 (s, 1H), 2.97 (s, 1H), 2.34 (s, 4H), 2.17 (s, 1H), 1.95 (t, J = 1.2 Hz, 3H), 1.85 (s, 1H), 1.63 (s, 3H). | 524.3 |
| N-(4-(4-amino-7-methyl-5-(4-(1-methyl-1H-pyrazol-3-yloxy)cyclohex-1-enyl)-7H-pyrrolo[2,3-d]pyrimidin-6-yl)phenyl) methacrylamide | 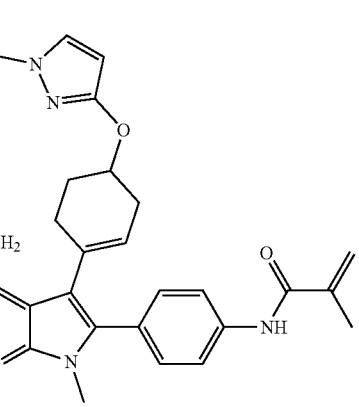 | $^1$H NMR (400 MHz, DMSO-$d_6$) δ 9.96 (s, 1H), 8.13 (s, 1H), 7.85-7.79 (m, 2H), 7.49-7.42 (m, 3H), 5.83 (s, 1H), 5.68 (dd, J = 11.6, 3.0 Hz, 2H), 5.58-5.53 (m, 1H), 4.83-4.74 (m, 1H), 3.66 (s, 3H), 3.59 (s, 3H), 2.55 (s, 1H), 2.33 (d, J = 18.3 Hz, 1H), 2.16-2.06 (m, 1H), 2.01-1.91 (m, 4H), 1.89 (q, J = 6.4 Hz, 1H), 1.80 (d, J = 9.1 Hz, 1H). | 484.4 |

TABLE 2-continued

Additional Exemplary Compounds

| Compound | Structure | Proton NMR | MS [M + 1] |
|---|---|---|---|
| (R)-N-(4-(4-amino-7-methyl-5-(4-(1-methyl-1H-pyrazol-3-yloxy)cyclohex-1-enyl)-7H-pyrrolo[2,3-d]pyrimidin-6-yl)phenyl)methacrylamide | 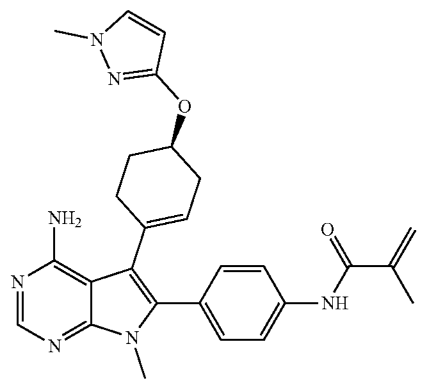 [SMILES: C=C(C)C(=O)Nc1ccc(-c2c(C3=CC[C@H](Oc4ccn(C)n4)CC3)c3c(N)ncnc3n2C)cc1] | $^1$H NMR (400 MHz, DMSO-d$_6$) δ 9.96 (s, 1H), 8.13 (s, 1H), 7.86-7.79 (m, 2H), 7.50-7.42 (m, 3H), 5.83 (d, J = 1.4 Hz, 1H), 5.72-5.64 (m, 2H), 5.56 (t, J = 1.5 Hz, 1H), 4.78 (q, J = 2.7 Hz, 1H), 3.66 (s, 3H), 3.58 (s, 3H), 2.55 (d, J = 8.1 Hz, 1H), 2.33 (d, J = 18.2 Hz, 1H), 2.18-2.06 (m, 1H), 2.03-1.93 (m, 4H), 1.89 (q, J = 6.3 Hz, 1H), 1.83-1.73 (m, 1H). | 484.3 |
| (S)-N-(4-(4-amino-7-methyl-5-(4-(1-methyl-1H-pyrazol-3-yloxy)cyclohex-1-enyl)-7H-pyrrolo[2,3-d]pyrimidin-6-yl)phenyl)methacrylamide | 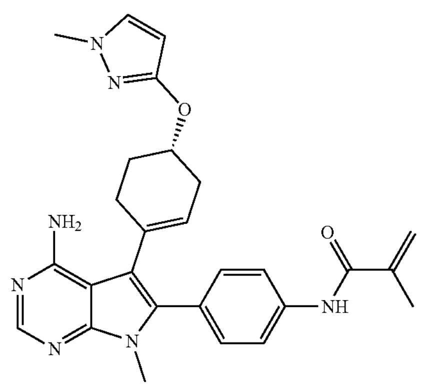 [SMILES: C=C(C)C(=O)Nc1ccc(-c2c(C3=CC[C@@H](Oc4ccn(C)n4)CC3)c3c(N)ncnc3n2C)cc1] | $^1$H NMR (400 MHz, DMSO-d$_6$) δ 9.96 (s, 1H), 8.13 (s, 1H), 7.86-7.79 (m, 2H), 7.49-7.42 (m, 3H), 5.83 (s, 1H), 5.71-5.64 (m, 2H), 5.56 (t, J = 1.5 Hz, 1H), 4.81-4.75 (m, 1H), 3.66 (s, 3H), 3.59 (s, 3H), 2.52 (s, 1H), 2.33 (d, J = 18.3 Hz, 1H), 2.12 (d, J = 17.4 Hz, 1H), 2.04-1.93 (m, 4H), 1.88 (q, J = 6.3 Hz, 1H), 1.80 (d, J = 8.6 Hz, 1H). | 484.3 |
| N-(4-(5-(4-(3-azabicyclo[3.2.1]octane-3-carbonyl)cyclohex-1-en-1-yl)-4-amino-7-methyl-7H-pyrrolo[2,3-d]pyrimidin-6-yl)phenyl)methacrylamide | 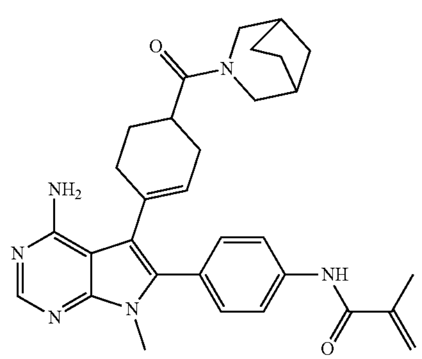 | $^1$H NMR (400 MHz, DMSO-d$_6$) δ 9.94 (s, 1H), 8.09 (s, 1H), 7.90-7.76 (m, 2H), 7.43 (d, J = 8.2 Hz, 2H), 6.52 (s, 2H), 5.83 (s, 1H), 5.75 (s, 1H), 5.55 (s, 1H), 4.17 (d, J = 12.6 Hz, 1H), 4.08 (d, J = 12.8 Hz, 0H), 3.73 (s, 1H), 3.58 (s, 3H), 3.14-3.02 (m, 2H), 2.57 (d, J = 12.0 Hz, 1H), 2.19 (s, 4H), 1.97 (s, 3H), 1.86 (s, 1H), 1.65 (s, 1H), 1.54 (s, 7H), 1.30 (s, 1H), 1.24 (s, 1H). | 525.35 |
| 4-(4-amino-6-(4-methacrylamido-phenyl)-7-methyl-7H-pyrrolo[2,3-d]pyrimidin-5-yl)-N-(2-methoxy-2-methylpropyl)cyclohex-3-ene-1-carboxamide | 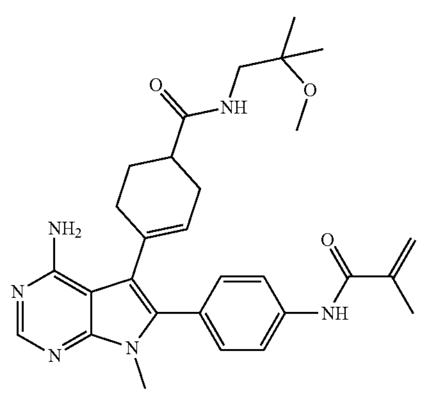 [SMILES: C=C(C)C(=O)Nc1ccc(-c2c(C3=CCC(C(=O)NCC(C)(C)OC)CC3)c3c(N)ncnc3n2C)cc1] | $^1$H NMR (400 MHz, DMSO-d$_6$) δ 10.01 (s, 1H), 8.38 (s, 1H), 8.26 (s, 1H), 7.90 (t, J = 6.1 Hz, 1H), 7.88-7.82 (m, 2H), 7.51-7.44 (m, 2H), 5.89 (s, 1H), 5.84 (s, 1H), 5.57 (d, J = 1.9 Hz, 1H), 3.67 (s, 3H), 3.25 (dd, J = 13.6, 6.8 Hz, 1H), 3.08 (s, 3H), 3.01 (dd, J = 13.6, 5.3 Hz, 1H), 2.74 (d, J = 4.7 Hz, 1H), 2.28 (s, 1H), 1.98 (d, J = 1.1 Hz, 3H), 1.92 (d, J = 12.0 Hz, 1H), 1.80 (d, J = 12.8 Hz, 2H), 1.66 (d, J = 11.7 Hz, 1H), 1.03 (d, J = 5.3 Hz, 6H). | 517.25 |

TABLE 2-continued

Additional Exemplary Compounds

| Compound | Structure | Proton NMR | MS [M + 1] |
|---|---|---|---|
| N-(4-(4-amino-7-methyl-5-(4-((S)-2-methylpiperidine-1-carbonyl)cyclohex-1-en-1-yl)-7H-pyrrolo[2,3-d]pyrimidin-6-yl)phenyl)methacrylamide | 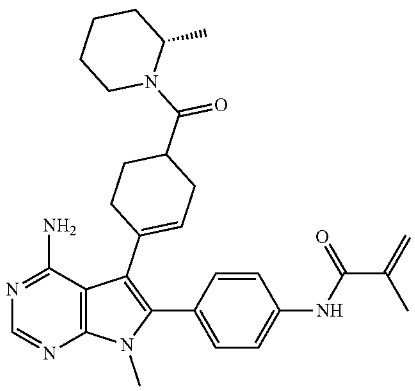 [SMILES: C=C(C)C(=O)Nc1ccc(-c2c(C3=CCC(C(=O)N4CCCC[C@@H]4C)CC3)c3c(N)ncnc3n2C)cc1] | $^1$H NMR (400 MHz, DMSO-d$_6$) δ 9.94 (d, J = 1.8 Hz, 1H), 8.10 (s, 1H), 7.84-7.77 (m, 2H), 7.46-7.40 (m, 2H), 6.54 (s, 2H), 5.83 (s, 1H), 5.80-5.73 (m, 1H), 5.55 (d, J = 2.0 Hz, 1H), 4.76 (s, 1H), 4.31 (s, 1H), 3.75 (d, J = 12.4 Hz, 1H), 3.58 (s, 3H), 3.07 (s, 1H), 3.01 (s, 1H), 2.60 (s, 2H), 2.31 (s, 1H), 2.23 (s, 2H), 2.08 (s, 1H), 1.98 (d, J = 1.5 Hz, 4H), 1.91 (s, 1H), 1.81 (d, J = 17.7 Hz, 1H), 1.60 (s, 6H), 1.51 (d, J = 14.5 Hz, 1H), 1.20 (s, 2H), 1.08-0.98 (m, 2H). | 513.35 |
| N-(4-(4-amino-5-(4-(5-fluoropyrimidin-2-yloxy)cyclohex-1-enyl)-7-methyl-7H-pyrrolo[2,3-d]pyrimidin-6-yl)phenyl)methacrylamide | 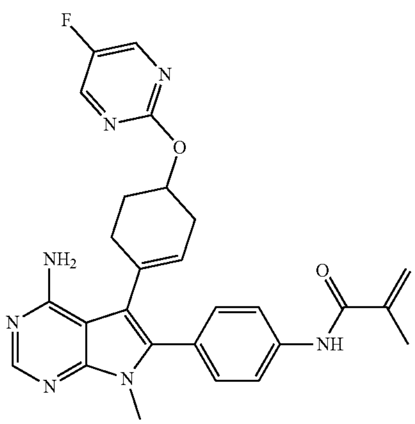 [SMILES: C=C(C)C(=O)Nc1ccc(-c2c(C3=CCC(Oc4ncc(F)cn4)CC3)c3c(N)ncnc3n2C)cc1] | $^1$H NMR (400 MHz, DMSO-d$_6$) δ 9.95 (s, 1H), 8.68 (s, 2H), 8.13 (s, 1H), 7.87-7.79 (m, 2H), 7.50-7.42 (m, 2H), 5.83 (t, J = 1.0 Hz, 1H), 5.74-5.67 (m, 1H), 5.55 (t, J = 1.5 Hz, 1H), 5.24-5.18 (m, 1H), 3.58 (s, 3H), 2.67-2.63 (s, 1H), 2.40 (s, 1H), 2.13-2.02 (m, 2H), 1.98 (t, J = 1.2 Hz, 3H), 1.93-1.83 (m, 2H). | 500.2 |
| 4-(4-amino-6-(4-methacrylamido-phenyl)-7-methyl-7H-pyrrolo[2,3-d]pyrimidin-5-yl)-N-(cyclobutylmethyl)cyclohex-3-ene-1-carboxamide | 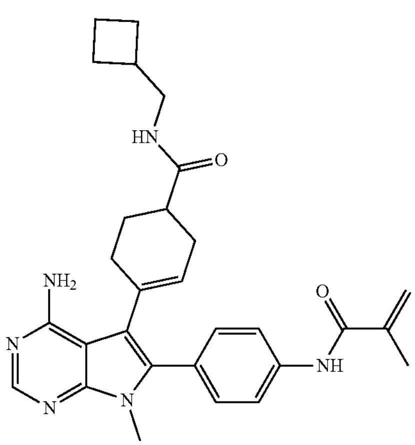 [SMILES: C=C(C)C(=O)Nc1ccc(-c2c(C3=CCC(C(=O)NCC4CCC4)CC3)c3c(N)ncnc3n2C)cc1] | 3$^1$H NMR (400 MHz, DMSO-d$_6$) δ 9.94 (s, 1H), 8.10 (s, 1H), 7.85-7.77 (m, 3H), 7.46-7.39 (m, 2H), 6.45 (s, 2H), 5.83 (s, 1H), 5.81-5.75 (m, 1H), 5.58-5.53 (m, 1H), 3.57 (s, 3H), 3.13 (dt, J = 13.0, 6.4 Hz, 1H), 3.02 (dt, J = 13.0, 6.0 Hz, 1H), 2.47 (t, J = 5.9 Hz, 1H), 2.43-2.33 (m, 1H), 2.35-2.26 (m, 1H), 2.22 (d, J = 5.3 Hz, 1H), 1.98 (d, J = 1.2 Hz, 3H), 1.98-1.86 (m, 4H), 1.85-1.70 (m, 2H), 1.68-1.55 (m, 4H). (m, 1H) | 499.30 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(2-fluoro-2-methylpropyl) benzamide | 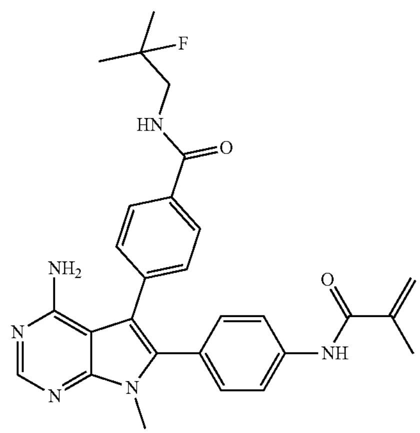 [SMILES: C=C(C)C(=O)Nc1ccc(-c2c(-c3ccc(C(=O)NCC(C)(C)F)cc3)c3c(N)ncnc3n2C)cc1] | $^1$H NMR (400 MHz, DMSO-d$_6$) δ 9.89 (s, 1H), 8.59 (t, J = 6.3 Hz, 1H), 8.21 (s, 1H), 7.96-7.79 (m, 2H), 7.76-7.60 (m, 2H), 7.43-6.93 (m, 4H), 5.79 (s, 1H), 5.53 (d, J = 1.8 Hz, 1H), 3.61 (s, 3H), 3.49 (d, J = 6.2 Hz, 1H), 3.44 (d, J = 6.2 Hz, 1H), 1.94 (t, J = 1.3 Hz, 3H), 1.35 (s, 3H), 1.29 (s, 3H). | 501.30 |
| N-(4-(4-amino-7-methyl-5-(4-((6-methylpyridin-2-yl)oxy)phenyl)-7H-pyrrolo[2,3-d]pyrimidin-6-yl)phenyl)-N-methylmethacryl amide | 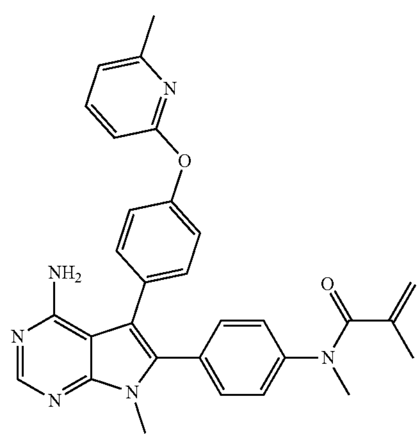 [SMILES: C=C(C)C(=O)N(C)c1ccc(-c2c(-c3ccc(Oc4cccc(C)n4)cc3)c3c(N)ncnc3n2C)cc1] | $^1$H NMR (400 MHz, DMSO-d$_6$) δ 8.21 (s, 1H), 7.79-7.69 (m, 1H), 7.39-7.32 (m, 2H), 7.32-7.26 (m, 2H), 7.26-7.19 (m, 2H), 7.13-7.05 (m, 2H), 7.02 (d, J = 7.3 Hz, 1H), 6.76 (d, J = 8.1 Hz, 1H), 5.93 (s, 2H), 5.04 (p, J = 1.6 Hz, 1H), 4.86 (t, J = 1.3 Hz, 1H), 3.62 (s, 3H), 3.27 (s, 3H), 2.35 (s, 3H), 1.69 (d, J = 1.3 Hz, 3H). | 505.25 |
| 4-(4-amino-7-methyl-6-(4-(N-methylmethacryl amido)phenyl)-7H-pyrrolo[2,3-d]pyrimidin-5-yl)-N-(2-methoxy-2-methylpropyl) benzamide | 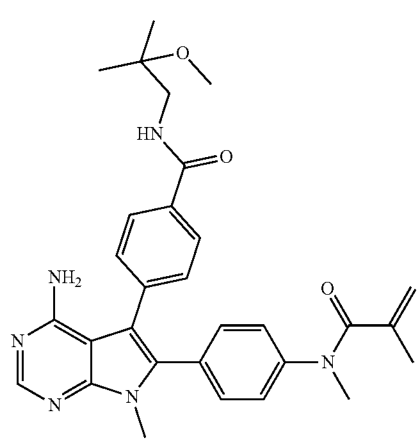 [SMILES: C=C(C)C(=O)N(C)c1ccc(-c2c(-c3ccc(C(=O)NCC(C)(C)OC)cc3)c3c(N)ncnc3n2C)cc1] | $^1$H NMR (400 MHz, DMSO-d$_6$) δ 8.22 (s, 2H), 7.86-7.76 (m, 2H), 7.39-7.19 (m, 6H), 5.95 (s, 2H), 5.09-5.04 (m, 1H), 4.86 (s, 1H), 3.62 (s, 3H), 3.34 (s, 2H), 3.27 (s, 3H), 3.15 (s, 3H), 1.70 (d, J = 1.5 Hz, 3H), 1.11 (s, 6H). | 527.25 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-2,6-difluoro-N-(2-methoxy-2-methylpropyl)benzamide | 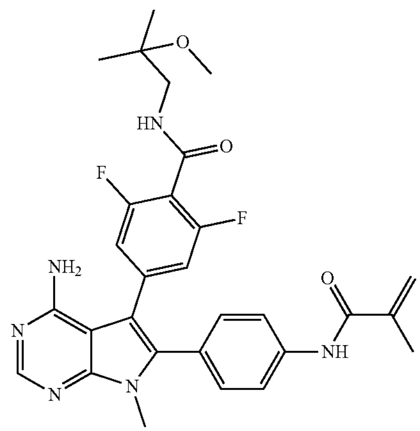 [SMILES: C=C(C)C(=O)Nc1ccc(-c2c(-c3cc(F)c(C(=O)NCC(C)(C)OC)c(F)c3)c3c(N)ncnc3n2C)cc1] | $^1$H NMR (400 MHz, DMSO-$d_6$) δ 9.94 (s, 1H), 8.50 (t, J = 6.1 Hz, 1H), 8.22 (s, 1H), 7.77 (d, J = 2.0 Hz, 1H), 7.38-7.28 (m, 2H), 6.94 (d, J = 8.1 Hz, 2H), 6.08 (s, 2H), 5.82 (s, 1H), 5.54 (s, 1H), 3.59 (s, 3H), 3.30 (d, J = 6.2 Hz, 2H), 3.12 (s, 3H), 1.96 (d, J = 1.2 Hz, 3H), 1.12 (s, 6H). | 549.45 |
| 4-(4-amino-6-(4-methacrylamido-phenyl)-7-methyl-7H-pyrrolo[2,3-d]pyrimidin-5-yl)-N-((3-fluorooxetan-3-yl)methyl)-N-methylbenzamide | 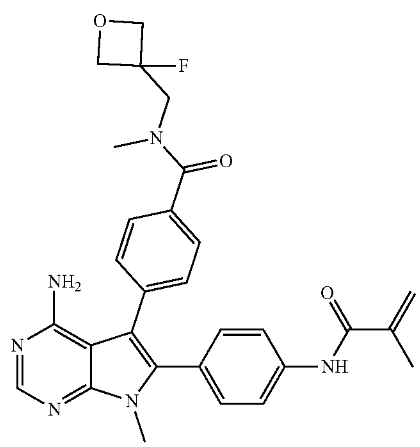 [SMILES: C=C(C)C(=O)Nc1ccc(-c2c(-c3ccc(C(=O)N(C)CC4(F)COC4)cc3)c3c(N)ncnc3n2C)cc1] | $^1$H NMR (400 MHz, DMSO-$d_6$) δ 9.88 (s, 1H), 8.21 (s, 1H), 7.77-7.65 (m, 2H), 7.37 (d, J = 7.8 Hz, 2H), 7.33-7.21 (m, 4H), 5.95 (s, 1H), 5.80 (t, J = 1.1 Hz, 1H), 5.53 (t, J = 1.5 Hz, 1H), 4.66 (d, J = 20.1 Hz, 4H), 4.06 (d, J = 22.7 Hz, 2H), 3.62 (s, 3H), 2.97 (s, 3H), 1.95 (t, J = 1.2 Hz, 3H). | 529.30 |
| 4-(4-amino-6-(4-methacrylamido-phenyl)-7-methyl-7H-pyrrolo[2,3-d]pyrimidin-5-yl)-N-(3-methoxy-2,2-dimethylpropyl)benzamide | 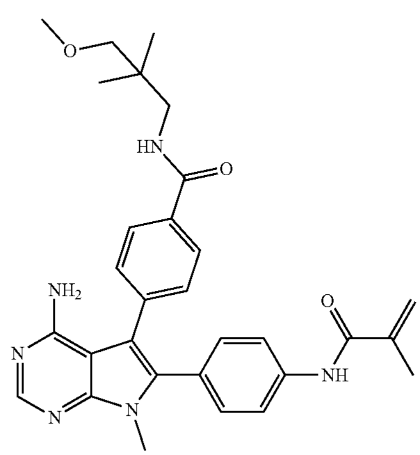 [SMILES: C=C(C)C(=O)Nc1ccc(-c2c(-c3ccc(C(=O)NCC(C)(C)COC)cc3)c3c(N)ncnc3n2C)cc1] | $^1$H NMR (400 MHz, DMSO-$d_6$) δ 9.89 (s, 1H), 8.22 (d, J = 12.8 Hz, 2H), 7.88-7.71 (m, 2H), 7.74-7.50 (m, 2H), 7.40-6.99 (m, 4H), 5.79 (s, 3H), 5.53 (d, J = 1.9 Hz, 1H), 3.61 (s, 3H), 3.32 (s, 3H), 3.26 (s, 2H), 3.17 (d, J = 6.3 Hz, 2H), 1.94 (d, J = 1.5 Hz, 3H), 0.86 (s, 6H). | 527.30 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)cyclohex-en-1-yl)-7H-pyrrolo[2,3-d]pyrimidin-6-yl)phenyl)methacrylamide | 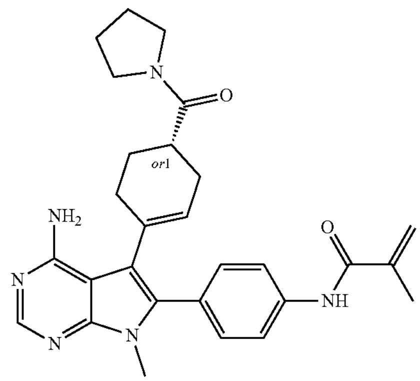 [SMILES: C=C(C)C(=O)Nc1ccc(-c2c(C3=CC[C@@H](C(=O)N4CCCC4)CC3)c3c(N)ncnc3n2C)cc1] | $^1$H NMR (400 MHz, DMSO-d$_6$) δ 9.93 (s, 1H), 8.10 (s, 1H), 7.84-7.77 (m, 2H), 7.47-7.39 (m, 2H), 6.51 (s, 2H), 5.83 (s, 1H), 5.77 (s, 1H), 5.55 (d, J = 1.9 Hz, 1H), 3.58 (s, 3H), 3.55-3.48 (m, 1H), 3.47-3.39 (m, 1H), 3.31-3.22 (m, 2H), 2.83 (t, J = 6.0 Hz, 1H), 2.26 (s, 2H), 1.98 (d, J = 1.3 Hz, 3H), 1.88 (dd, J = 13.4, 6.6 Hz, 4H), 1.77 (q, J = 6.7 Hz, 2H), 1.63 (d, J = 6.2 Hz, 2H). | 485.25 |
| N-(4-(4-amino-7-methyl-5-(4-(pyrrolidine-1-carbonyl)cyclohex-1-en-1-yl)-7H-pyrrolo[2,3-d]pyrimidin-6-yl)phenyl)methacrylamide | 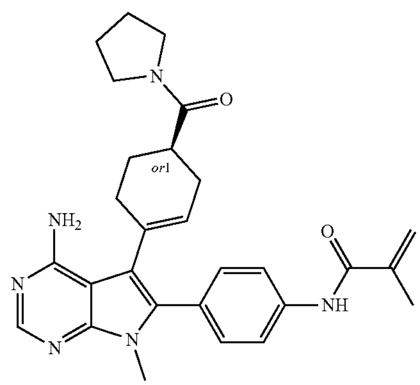 [SMILES: C=C(C)C(=O)Nc1ccc(-c2c(C3=CC[C@H](C(=O)N4CCCC4)CC3)c3c(N)ncnc3n2C)cc1] | $^1$H NMR (400 MHz, DMSO-d$_6$) δ 9.93 (s, 1H), 8.10 (s, 1H), 7.84-7.77 (m, 2H), 7.47-7.39 (m, 2H), 6.51 (s, 2H), 5.83 (s, 1H), 5.77 (s, 1H), 5.55 (d, J = 1.9 Hz, 1H), 3.58 (s, 3H), 3.55-3.48 (m, 1H), 3.47-3.39 (m, 1H), 3.31-3.22 (m, 2H), 2.83 (t, J = 6.0 Hz, 1H), 2.26 (s, 2H), 1.98 (d, J = 1.3 Hz, 3H), 1.88 (dd, J = 13.4, 6.6 Hz, 4H), 1.77 (q, J = 6.7 Hz, 2H), 1.63 (d, J = 6.2 Hz, 2H). | 485.25 |
| N-(4-(4-amino-5-(3-cyano-4-((5-fluoropyrimidin-2-yl)oxy)phenyl)-7-methyl-7H-pyrrolo[2,3-d]pyrimidin-6-yl)phenyl)methacrylamide | 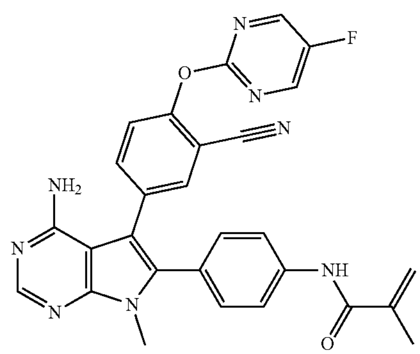 [SMILES: C=C(C)C(=O)Nc1ccc(-c2c(-c3ccc(Oc4ncc(F)cn4)c(C#N)c3)c3c(N)ncnc3n2C)cc1] | $^1$H NMR (400 MHz, DMSO-d6) δ 9.93 (s, 1H), 8.83 (s, 2H), 8.22 (s, 1H), 7.77 (d, J = 1.9 Hz, 1H), 7.76-7.73 (m, 2H), 7.55-7.53 (m, 1H), 7.45 (s, 1H), 7.33 (d, J = 8.6 Hz, 2H), 6.05 (s, 1H), 5.82 (s, 1H), 5.55 (s, 1H), 3.59 (s, 3H), 1.96 (t, J = 1.2 Hz, 3H). | 521.20 |
| N-(4-(4-amino-5-(3-methoxy-4-((4-methylpyrimidin-2-yl)oxy)phenyl)-7-methyl-7H-pyrrolo[2,3-d]pyrimidin-6-yl)phenyl)methacrylamide | 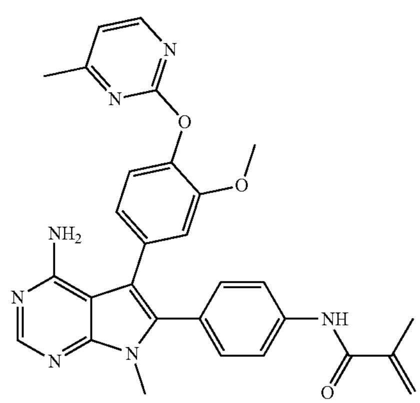 [SMILES: C=C(C)C(=O)Nc1ccc(-c2c(-c3ccc(Oc4nccc(C)n4)c(OC)c3)c3c(N)ncnc3n2C)cc1] | $^1$H NMR (400 MHz, DMSO-d$_6$) δ 9.90 (s, 1H), 8.41 (d, J = 5.0 Hz, 1H), 8.21 (s, 1H), 7.75 (d, 2H), 7.35 (d, 2H), 7.16-7.07 (m, 2H), 6.98 (d, J = 2.0 Hz, 1H), 6.85 (dd, J = 8.1, 1.9 Hz, 1H), 5.96 (s, 2H), 5.81 (s, 1H), 5.54 (s, 1H), 3.61 (s, 3H), 3.55 (s, 3H), 2.40 (s, 3H), 1.96 (s, 3H). | 528.20 |

TABLE 2-continued

Additional Exemplary Compounds

| Compound | Structure | Proton NMR | MS [M + 1] |
|---|---|---|---|
| N-(4-(4-amino-5-(4-((5-fluoropyrimidin-2-yl)oxy)phenyl)-7-methyl-7H-pyrrolo[2,3-d]pyrimidin-6-yl)phenyl)methacrylamide | 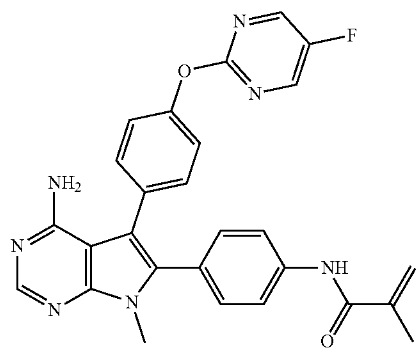 | $^1$H NMR (400 MHz, DMSO-d6) δ 9.90 (s, 1H), 8.76 (s, 2H), 8.20 (s, 1H), 7.73 (d, J = 8.7 Hz, 2H), 7.32-7.29 (m, 3H), 7.21 (d, J = 8.7 Hz, 2H), 5.80 (t, J = 1.1 Hz, 2H), 5.54 (t, J = 1.5 Hz, 1H), 3.60 (s, 3H), 1.95 (t, J = 1.2 Hz, 3H). | 496.15 |
| N-(4-(4-amino-5-(4-((5-fluoropyrimidin-2-yl)oxy)-3-methylphenyl)-7-methyl-7H-pyrrolo[2,3-d]pyrimidin-6-yl)-3-fluorophenyl)methacrylamide | 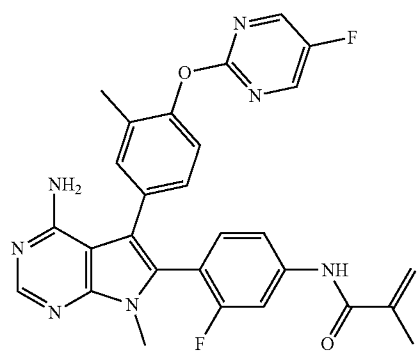 [SMILES: C=C(C)C(=O)Nc1ccc(-c2c(-c3ccc(Oc4ncc(F)cn4)c(C)c3)c3c(N)ncnc3n2C)c(F)c1] | $^1$H NMR (400 MHz, DMSO-$d_6$) δ 10.12 (s, 1H), 8.73 (s, 2H), 8.22 (s, 1H), 7.79 (dd, J = 12.4, 2.0 Hz, 1H), 7.53 (dd, J = 8.4, 2.0 Hz, 1H), 7.34 (t, J = 8.4 Hz, 1H), 7.24 (s, 1H), 7.11 (d, J = 2.3 Hz, 2H), 5.83 (s, 1H), 5.59 (s, 1H), 3.53 (s, 3H), 2.06 (s, 3H), 1.96 (t, J = 1.2 Hz, 3H). | 528.35 |
| N-(4-(4-amino-5-(3,5-difluoro-4-((5-methylpyrimidin-2-yl)oxy)phenyl)-7-methyl-7H-pyrrolo[2,3-d]pyrimidin-6-yl)phenyl)methacrylamide | 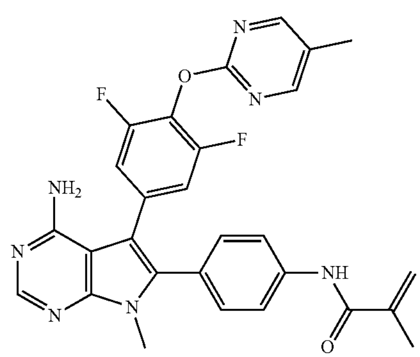 [SMILES: C=C(C)C(=O)Nc1ccc(-c2c(-c3cc(F)c(Oc4ncc(C)cn4)c(F)c3)c3c(N)ncnc3n2C)cc1] | $^1$H NMR (400 MHz, DMSO-$d_6$) δ 9.95 (s, 1H), 8.54 (s, 2H), 8.22 (s, 1H), 7.82-7.76 (m, 2H), 7.39-7.33 (m, 2H), 7.07 (d, J = 8.8 Hz, 2H), 6.12 (s, 2H), 5.83 (s, 1H), 5.56 (s, 1H), 3.58 (s, 3H), 2.24 (s, 3H), 1.97 (d, J = 1.2 Hz, 3H). | 528.15 |
| N-(4-(4-amino-5-(3,5-difluoro-4-((4-methylpyrimidin-2-yl)oxy)phenyl)-7-methyl-7H-pyrrolo[2,3-d]pyrimidin-6-yl)phenyl)methacrylamide | 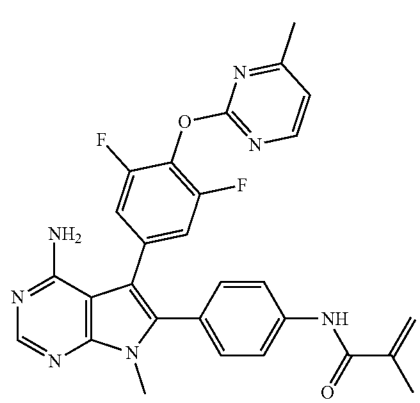 [SMILES: C=C(C)C(=O)Nc1ccc(-c2c(-c3cc(F)c(Oc4nccc(C)n4)c(F)c3)c3c(N)ncnc3n2C)cc1] | $^1$H NMR (400 MHz, DMSO-$d_6$) δ 9.94 (s, 1H), 8.51 (d, J = 5.0 Hz, 1H), 8.22 (s, 1H), 7.78 (d, J = 8.7 Hz, 2H), 7.34 (d, 2H), 7.24 (d, J = 5.0 Hz, 1H), 7.06 (d, J = 8.8 Hz, 2H), 6.12 (s, 2H), 5.82 (s, 1H), 5.54 (s, 1H), 3.59 (s, 3H), 2.44 (s, 3H), 1.96 (d, J = 1.2 Hz, 3H). | 520.25 |

TABLE 2-continued

Additional Exemplary Compounds

| Compound | Structure | Proton NMR | MS [M + 1] |
|---|---|---|---|
| N-(4-(4-amino-5-(4-((5-(dimethylamino)pyrimidin-2-yl)oxy)-3-fluorophenyl)-7-methyl-7H-pyrrolo[2,3-d]pyrimidin-6-yl)phenyl)methacrylamide | 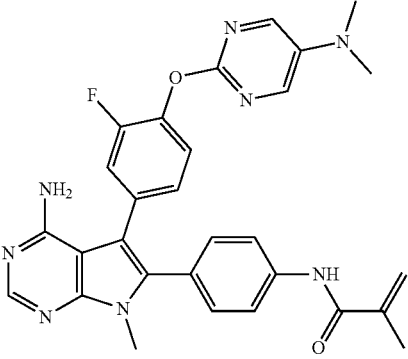 [SMILES: C=C(C)C(=O)Nc1ccc(-c2c(-c3ccc(Oc4ncc(N(C)C)cn4)c(F)c3)c3c(N)ncnc3n2C)cc1] | ¹H NMR (400 MHz, DMSO-d₆) δ 9.93 (s, 1H), 8.20 (d, J = 9.0 Hz, 3H), 7.87-7.65 (m, 2H), 7.45-7.24 (m, 3H), 7.21-7.03 (m, 2H), 5.68 (d, J = 108.0 Hz, 2H), 3.59 (s, 3H), 2.89 (s, 6H), 1.96 (s, 3H). | 539.30 |
| N-(4-(4-amino-5-(4-((5-methoxypyrimidin-2-yl)oxy)phenyl)-7-methyl-7H-pyrrolo[2,3-d]pyrimidin-6-yl)phenyl)methacrylamide | 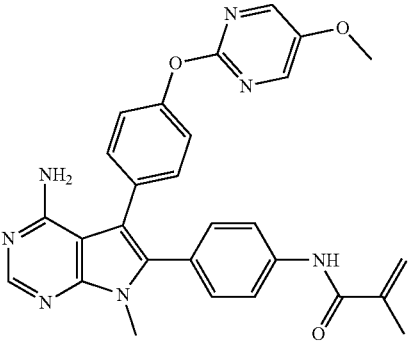 [SMILES: C=C(C)C(=O)Nc1ccc(-c2c(-c3ccc(Oc4ncc(OC)cn4)cc3)c3c(N)ncnc3n2C)cc1] | ¹H NMR (400 MHz, DMSO-d6) δ 9.91 (s, 1H), 8.43 (s, 2H), 8.20 (s, 1H), 7.73 (d, J = 8.6 Hz, 2H), 7.34-7.25 (m, 4H), 7.19-7.12 (m, 2H), 5.80 (s, 1H), 5.54 (d, J = 1.8 Hz, 1H), 3.86 (s, 3H), 3.60 (s, 3H), 1.95 (t, J = 1.3 Hz, 3H). | 508.20 |
| N-(4-(4-amino-5-(3-(dimethylamino)-4-((5-fluoropyrimidin-2-yl)oxy)phenyl)-7-methyl-7H-pyrrolo[2,3-d]pyrimidin-6-yl)phenyl)methacrylamide | 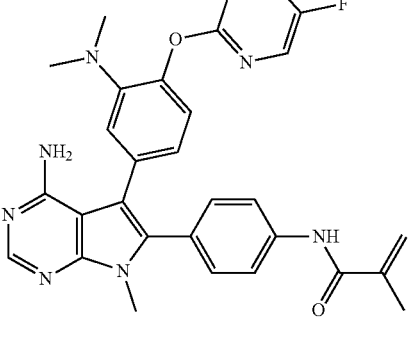 | ¹H NMR (400 MHz, DMSO-d₆) δ 9.91 (s, 1H), 8.72 (s, 2H), 8.20 (s, 1H), 7.91-7.63 (m, 2H), 7.34 (d, J = 8.6 Hz, 2H), 7.16-6.99 (m, 1H), 6.86 (s, 2H), 5.81 (s, 1H), 5.55 (d, J = 1.9 Hz, 1H), 3.59 (s, 3H), 2.55 (s, 6H), 1.96 (t, J = 1.2 Hz, 3H). | 539.30 |
| N-(4-(4-amino-5-(3-fluoro-4-((5-methoxypyrimidin-2-yl)oxy)phenyl)-7-methyl-7H-pyrrolo[2,3-d]pyrimidin-6-yl)phenyl)methacrylamide | 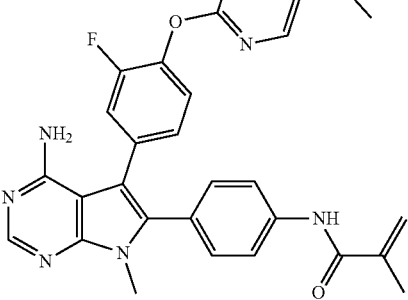 | ¹H NMR (400 MHz, DMSO-d6) δ 9.93 (s, 1H), 8.43 (s, 2H), 8.21 (s, 1H), 7.80-7.73 (m, 2H), 7.38-7.29 (m, 3H), 7.18 (dd, J = 11.6, 2.0 Hz, 1H), 7.10 (dd, J = 8.4, 2.0 Hz, 1H), 5.99 (s, 2H), 5.81 (s, 1H), 5.54 (d, J = 1.9 Hz, 1H), 3.86 (s, 3H), 3.59 (s, 3H), 1.96 (t, J = 1.2 Hz, 3H). | 526.20 |

TABLE 2-continued

Additional Exemplary Compounds

| Compound | Structure | Proton NMR | MS [M + 1] |
|---|---|---|---|
| N-(4-(4-amino-5-(4-((5-fluoropyrimidin-2-yl)oxy)phenyl)-7-methyl-7H-pyrrolo[2,3-d]pyrimidin-6-yl)-3-fluorophenyl)methacrylamide | 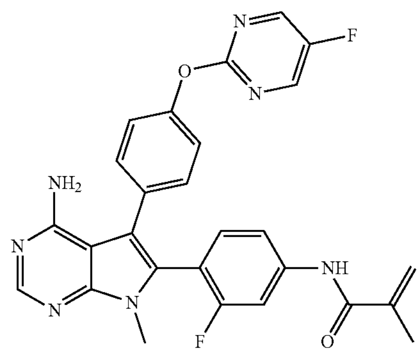 [SMILES: C=C(C)C(=O)Nc1ccc(-c2c(-c3ccc(Oc4ncc(F)cn4)cc3)c3c(N)ncnc3n2C)c(F)c1] | $^1$H NMR (400 MHz, DMSO-d$_6$) δ 10.12 (s, 1H), 8.76 (s, 2H), 8.22 (s, 1H), 7.82-7.73 (m, 1H), 7.56-7.49 (m, 1H), 7.36-7.24 (m, 3H), 7.24-7.19 (m, 2H), 5.83 (s, 1H), 5.59 (d, J = 2.1 Hz, 1H), 3.54 (s, 3H), 1.96 (t, J = 1.2 Hz, 3H). | 514.35 |
| N-(4-(4-amino-7-methyl-5-(4-((6-methylpyridin-2-yl)oxy)phenyl)-7H-pyrrolo[2,3-d]pyrimidin-6-yl)phenyl)-2-((dimethylamino)methyl)acrylamide | 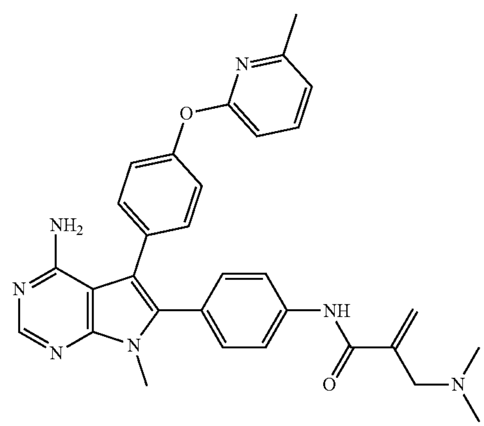 [SMILES: C=C(CN(C)C)C(=O)Nc1ccc(-c2c(-c3ccc(Oc4cccc(C)n4)cc3)c3c(N)ncnc3n2C)cc1] | $^1$H NMR (400 MHz, DMSO-d$_6$) δ 11.21 (s, 1H), 8.20 (s, 1H), 7.73 (t, J = 7.8 Hz, 1H), 7.66-7.62 (m, 2H), 7.35-7.29 (m, 2H), 7.28-7.23 (m, 2H), 7.13-7.06 (m, 2H), 7.01 (d, J = 7.3 Hz, 1H), 6.79 (d, J = 8.1 Hz, 1H), 6.02 (d, J = 1.8 Hz, 3H), 5.58 (d, J = 1.6 Hz, 1H), 3.62 (s, 3H), 3.23 (s, 2H), 2.35 (s, 3H), 2.25 (s, 6H). | 534.25 |
| N-(6-(4-amino-5-(4-((6-methylpyridin-2-yl)oxy)phenyl)-7H-pyrrolo[2,3-d]pyrimidin-6-yl)pyridin-3-yl)methacrylamide | 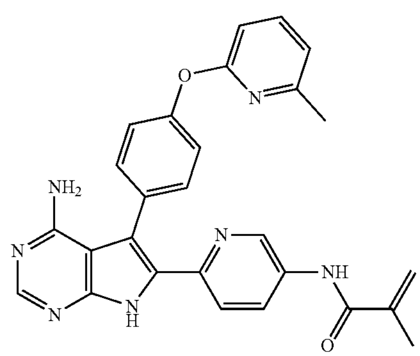 [SMILES: C=C(C)C(=O)Nc1ccc(-c2[nH]c3ncnc(N)c3c2-c2ccc(Oc3cccc(C)n3)cc2)nc1] | $^1$H NMR (400 MHz, DMSO-d$_6$) δ 12.09 (s, 1H), 10.04 (s, 1H), 8.90 (d, J = 2.5 Hz, 1H), 8.13 (s, 1H), 7.91 (dd, J = 8.8, 2.5 Hz, 1H), 7.78 (t, J = 7.8 Hz, 1H), 7.52-7.42 (m, 2H), 7.35-7.16 (m, 2H), 7.07 (t, J = 7.6 Hz, 2H), 6.88 (d, J = 8.1 Hz, 1H), 5.85 (s, 1H), 5.58 (s, 1H), 2.39 (s, 3H), 1.96 (t, J = 1.2 Hz, 3H). | 478.30 |
| N-(4-(4-amino-5-(2-fluoro-4-((6-methylpyridin-2-yl)oxy)phenyl)-7-methyl-7H-pyrrolo[2,3-d]pyrimidin-6-yl)phenyl)methacrylamide | 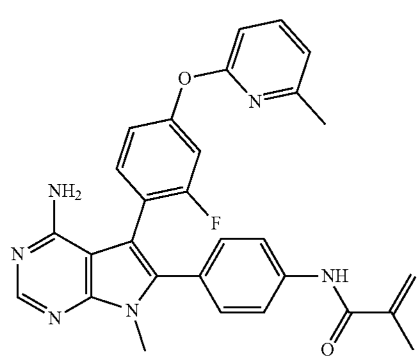 [SMILES: C=C(C)C(=O)Nc1ccc(-c2c(-c3ccc(Oc4cccc(C)n4)cc3F)c3c(N)ncnc3n2C)cc1] | $^1$H NMR (400 MHz, DMSO-d$_6$) δ 9.89 (s, 1H), 8.20 (s, 1H), 7.71 (d, J = 8.7 Hz, 3H), 7.40-7.21 (m, 3H), 7.12-7.00 (m, 2H), 6.96 (dd, J = 8.4, 2.4 Hz, 1H), 6.85 (d, J = 8.1 Hz, 1H), 5.80 (s, 3H), 5.53 (t, J = 1.5 Hz, 1H), 3.65 (s, 3H), 2.37 (s, 3H), 1.95 (t, J = 1.2 Hz, 3H). | 509.25 |

TABLE 2-continued

Additional Exemplary Compounds

| Compound | Structure | Proton NMR | MS [M + 1] |
|---|---|---|---|
| N-(4-(4-amino-7-methyl-5-(5-((6-methylpyridin-2-yl)oxy)pyridin-2-yl)-7H-pyrrolo[2,3-d]pyrimidin-6-yl)phenyl)methacrylamide | 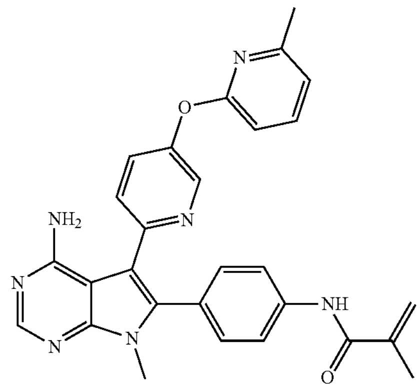 [SMILES: C=C(C)C(=O)Nc1ccc(-c2c(-c3ccc(Oc4cccc(C)n4)cn3)c3c(N)ncnc3n2C)cc1] | $^1$H NMR (400 MHz, DMSO-$d_6$) δ 8.41 (s, 1H), 7.65 (dd, J = 8.2, 7.3 Hz, 1H), 7.54-7.44 (m, 2H), 7.42-7.34 (m, 2H), 7.12 (d, J = 8.0 Hz, 1H), 7.01 (s, 2H), 6.96-6.91 (m, 2H), 6.88 (dd, J = 8.0, 2.0 Hz, 1H), 6.67-6.60 (m, 1H), 6.17 (dd, J = 16.8, 2.5 Hz, 1H), 6.08 (d, J = 11.3 Hz, 1H), 5.58-5.50 (m, 1H), 3.72 (s, 3H), 3.67 (s, 3H), 3.28 (s, 3H), 2.29 (s, 3H). | 492.25 |
| N-(4-(4-amino-5-(3-((dimethylamino)methyl)-4-((6-methylpyridin-2-yl)oxy)phenyl)-7-methyl-7H-pyrrolo[2,3-d]pyrimidin-6-yl)phenyl)methacrylamide | 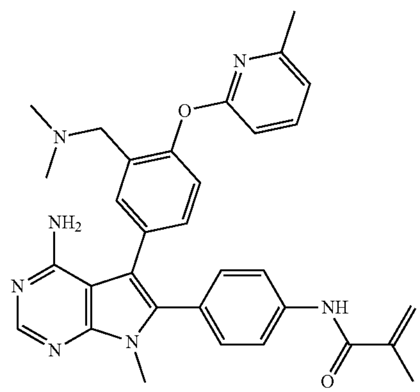 [SMILES: C=C(C)C(=O)Nc1ccc(-c2c(-c3ccc(Oc4cccc(C)n4)c(CN(C)C)c3)c3c(N)ncnc3n2C)cc1] | $^1$H NMR (400 MHz, DMSO-$d_6$) δ 9.88 (s, 1H), 8.20 (s, 1H), 7.76-7.66 (m, 3H), 7.35 (d, J = 2.4 Hz, 1H), 7.33-7.25 (m, 2H), 7.16 (dd, J = 8.4, 2.4 Hz, 1H), 6.99 (dd, J = 18.4, 7.8 Hz, 2H), 6.71 (d, J = 8.2 Hz, 1H), 5.98 (s, 2H), 5.79 (s, 1H), 5.53 (t, J = 1.6 Hz, 1H), 3.63 (s, 3H), 3.30 (s, 2H), 2.31 (s, 3H), 2.00 (s, 6H), 1.95 (t, J = 1.2 Hz, 3H). | 548.30 |
| N-(4-(4-amino-7-methyl-5-(1-((6-methylpyridin-2-yl)methyl)-2-oxo-1,2-dihydropyridin-4-yl)-7H-pyrrolo[2,3-d]pyrimidin-6-yl)phenyl)methacrylamide | 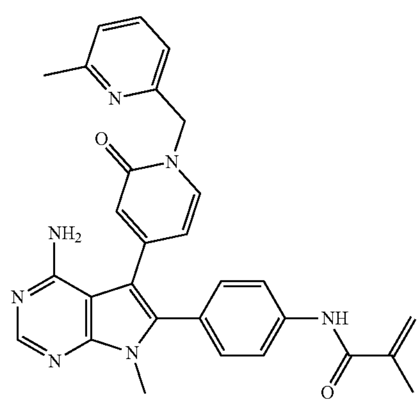 [SMILES: C=C(C)C(=O)Nc1ccc(-c2c(-c3ccn(Cc4cccc(C)n4)c(=O)c3)c3c(N)ncnc3n2C)cc1] | $^1$H NMR (400 MHz, DMSO-$d_6$) δ 9.96 (s, 1H), 8.22 (s, 1H), 7.85-7.76 (m, 2H), 7.69-7.61 (m, 2H), 7.39-7.31 (m, 2H), 7.15 (d, J = 7.6 Hz, 1H), 6.93 (d, J = 7.7 Hz, 1H), 6.32 (s, 2H), 6.21 (d, J = 1.9 Hz, 1H), 6.00 (dd, J = 1.0, 2.0 Hz, 1H), 5.82 (d, J = 1.3 Hz, 1H), 5.55 (d, J = 1.6 Hz, 1H), 5.09 (s, 2H), 3.59 (s, 3H), 2.44 (s, 3H), 1.97 (t, J = 1.2 Hz, 3H). | 506.20 |
| N-(4-(4-amino-7-methyl-5-(1-((6-methylpyridin-2-yl)methyl)-1H-pyrazol-4-yl)-7H-pyrrolo[2,3-d]pyrimidin-6-yl)phenyl)methacrylamide | 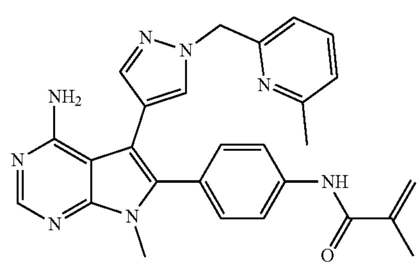 [SMILES: C=C(C)C(=O)Nc1ccc(-c2c(-c3cnn(Cc4cccc(C)n4)c3)c3c(N)ncnc3n2C)cc1] | $^1$H NMR (400 MHz, DMSO-$d_6$) δ 9.93 (s, 1H), 8.18 (s, 1H), 7.84 (s, 1H), 7.80-7.72 (m, 2H), 7.63 (t, J = 7.8 Hz, 1H), 7.39-7.31 (m, 3H), 7.15 (d, J = 7.8 Hz, 1H), 6.63 (d, J = 7.8 Hz, 1H), 6.06 (s, 2H), 5.84-5.79 (m, 1H), 5.56 (t, J = 1.4 Hz, 1H), 5.38 (s, 2H), 3.61 (s, 3H), 2.44 (s, 3H), 1.98 (t, J = 1.2 Hz, 3H). | 479.35 |

TABLE 2-continued

Additional Exemplary Compounds

| Compound | Structure | Proton NMR | MS [M + 1] |
|---|---|---|---|
| N-(4-(4-amino-5-(4-((S)-2-cyanopyrrolidine-1-carbonyl)phenyl)-7-methyl-7H-pyrrolo[2,3-d]pyrimidin-6-yl)-3-fluorophenyl)methacrylamide | 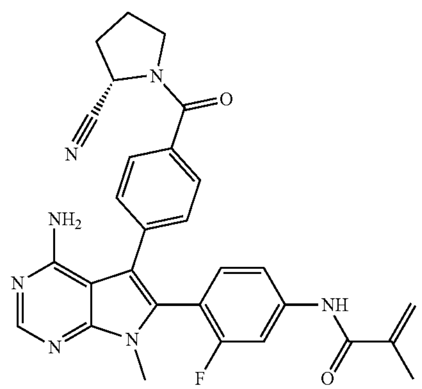 [SMILES: C=C(C)C(=O)Nc1ccc(-c2c(-c3ccc(C(=O)N4CCC[C@H]4C#N)cc3)c3c(N)ncnc3n2C)c(F)c1] | ¹H NMR (400 MHz, DMSO-d₆) δ 10.10 (s, 1H), 8.23 (s, 1H), 7.77 (dd, J = 12.5, 2.0 Hz, 1H), 7.57 (d, J = 7.8 Hz, 2H), 7.49 (dd, J = 8.5, 2.0 Hz, 1H), 7.32-7.22 (m, 3H), 5.82 (t, J = 1.0 Hz, 1H), 5.58 (d, J = 2.0 Hz, 1H), 4.87 (t, J = 6.6 Hz, 1H), 3.65 (s, 1H), 3.56 (s, 4H), 2.32 (s, 1H), 2.17 (ddd, J = 12.7, 11.5, 6.1 Hz, 1H), 1.95 (t, J = 1.3 Hz, 5H). | 524.2 |
| (S)-N-(4-(4-amino-5-(4-(2-cyanopyrrolidine-1-carbonyl)-3-fluorophenyl)-7-methyl-7H-pyrrolo[2,3-d]pyrimidin-6-yl)phenyl)methacrylamide | 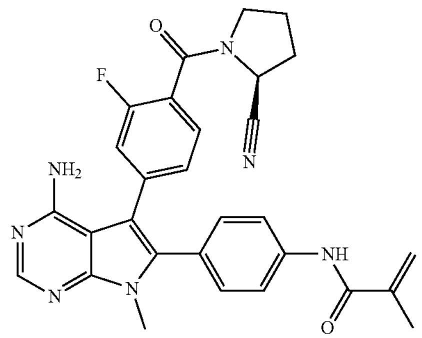 [SMILES: C=C(C)C(=O)Nc1ccc(-c2c(-c3ccc(C(=O)N4CCC[C@H]4C#N)c(F)c3)c3c(N)ncnc3n2C)cc1] | ¹H NMR (400 MHz, DMSO-d₆) δ 9.92 (s, 1H), 8.22 (s, 1H), 7.74 (d, J = 8.4 Hz, 2H), 7.42 (t, J = 7.5 Hz, 1H), 7.27 (d, J = 8.4 Hz, 2H), 7.08 (d, J = 9.3 Hz, 2H), 5.82 (s, 1H), 5.54 (s, 1H), 4.95-4.87 (m, 1H), 3.60 (s, 3H), 1.96 (s, 4H). | 524.40 |
| 4-(4-amino-6-(2-fluoro-4-methacrylamidophenyl)-7-methyl-7H-pyrrolo[2,3-d]pyrimidin-5-yl)-N-((3-fluorooxetan-3-yl)methyl)-N-methylbenzamide | | ¹H NMR (400 MHz, DMSO-d₆) δ 10.10 (s, 1H), 8.22 (s, 1H), 7.76 (dd, J = 12.5, 2.0 Hz, 1H), 7.49 (dd, J = 8.4, 2.0 Hz, 1H), 7.37 (s, 2H), 7.30-7.21 (m, 3H), 5.82 (s, 1H), 5.58 (s, 1H), 4.64 (s, 5H), 4.09 (s, 1H), 4.03 (s, 1H), 3.55 (s, 3H), 2.96 (s, 3H), 1.95 (d, J = 1.2 Hz, 3H). | 547.30 |
| 4-(4-amino-6-(2-fluoro-4-methacrylamidophenyl)-7-methyl-7H-pyrrolo[2,3-d]pyrimidin-5-yl)-N-methyl-N-((3-methyl-1,2,4-oxadiazol-5-yl)methyl)benzamide | | ¹H NMR (400 MHz, DMSO-d₆) δ 10.09 (s, 1H), 8.22 (s, 1H), 7.76 (dd, J = 12.4, 2.0 Hz, 1H), 7.48 (dd, J = 8.5, 2.0 Hz, 1H), 7.43 (s, 2H), 7.28 (s, 3H), 7.25 (d, J = 8.5 Hz, 1H), 6.04 (s, 2H), 5.83 (s, 1H), 5.58 (s, 1H), 4.91 (s, 2H), 3.55 (s, 3H), 3.10 (s, 3H), 2.35 (s, 3H), 1.95 (t, J = 1.3 Hz, 3H). | 555.30 |

TABLE 2-continued

Additional Exemplary Compounds

| Compound | Structure | Proton NMR | MS [M + 1] |
|---|---|---|---|
| 4-(4-amino-6-(2-fluoro-4-methacrylamido-phenyl)-7-methyl-7H-pyrrolo[2,3-d]pyrimidin-5-yl)-N-((1-cyanocyclopropyl)methyl)-N-methylbenzamide | 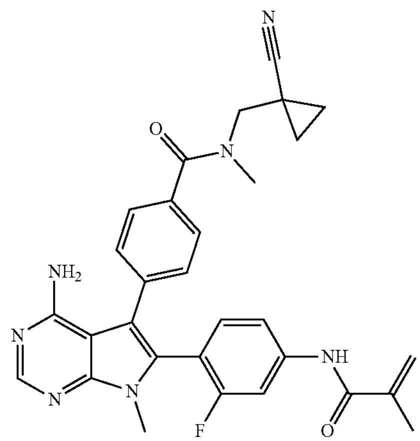 [SMILES: C=C(C)C(=O)Nc1ccc(-c2c(-c3ccc(C(=O)N(C)CC4(C#N)CC4)cc3)c3c(N)ncnc3n2C)c(F)c1] | $^1$H NMR (400 MHz, DMSO-$d_6$) δ 10.10 (s, 1H), 8.23 (s, 1H), 7.77 (dd, J = 12.5, 2.0 Hz, 1H), 7.49 (dd, J = 8.5, 2.0 Hz, 1H), 7.37 (d, J = 7.5 Hz, 2H), 7.28 (d, J = 8.2 Hz, 3H), 6.04 (s, 2H), 5.83 (s, 1H), 5.57 (s, 1H), 3.32 (s, 3H), 3.06 (s, 3H), 1.95 (d, J = 1.5 Hz, 3H), 1.29 (s, 2H), 1.16 (t, J = 13.2 Hz, 2H). | 538.40 |
| 4-(4-amino-6-(4-methacrylamido-phenyl)-7-methyl-7H-pyrrolo[2,3-d]pyrimidin-5-yl)-N-methyl-N-((tetrahydrofuran-3-yl)methyl)benzamide | 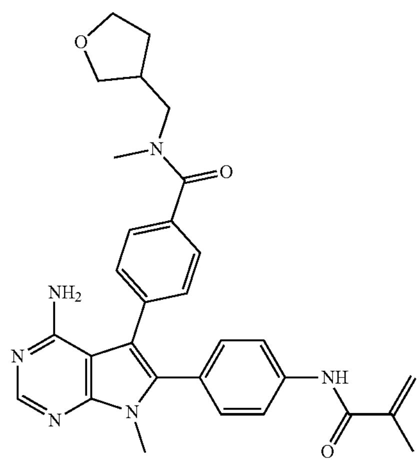 [SMILES: C=C(C)C(=O)Nc1ccc(-c2c(-c3ccc(C(=O)N(C)CC4CCOC4)cc3)c3c(N)ncnc3n2C)cc1] | $^1$H NMR (400 MHz, DMSO-$d_6$) δ 9.88 (s, 1H), 8.21 (s, 1H), 7.74-7.67 (m, 2H), 7.35 (s, 2H), 7.30-7.22 (m, 4H), 5.92 (s, 2H), 5.80 (s, 1H), 5.56-5.50 (m, 1H), 3.76 (s, 1H), 3.62 (s, 4H), 3.53 (s, 2H), 3.22 (s, 1H), 2.95 (s, 3H), 2.62 (s, 0.5H), 1.95 (d, J = 1.2 Hz, 3H), 1.82 (s, 0.5H), 1.60 (s, 0.5H), 1.31 (s, 0.5H). | 525.35 |
| 4-(4-amino-6-(4-methacrylamido-phenyl)-7-methyl-7H-pyrrolo[2,3-d]pyrimidin-5-yl)-N-isobutyl-N-methylbenzamide | 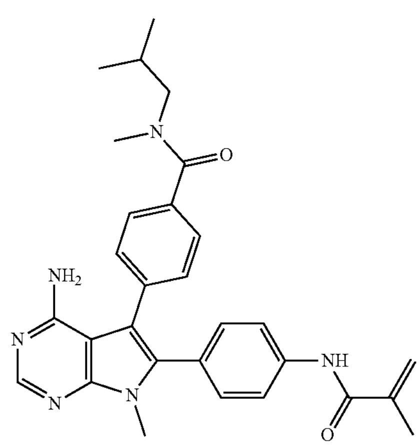 [SMILES: C=C(C)C(=O)Nc1ccc(-c2c(-c3ccc(C(=O)N(C)CC(C)C)cc3)c3c(N)ncnc3n2C)cc1] | $^1$H NMR (400 MHz, DMSO-$d_6$) δ 9.88 (s, 1H), 8.21 (s, 1H), 7.70 (d, J = 8.6 Hz, 2H), 7.35 (s, 2H), 7.27 (d, J = 7.9 Hz, 2H), 7.26 (s, 2H), 5.79 (s, 1H), 5.53 (t, J = 1.5 Hz, 1H), 3.62 (s, 3H), 3.28 (s, 1H), 3.05 (s, 1H), 2.92 (s, 3H), 2.03-1.85 (s, 1H), 1.95 (t, J = 1.2 Hz, 3H), 0.91 (d, J = 6.6 Hz, 3H), 0.68 (s, 3H). | 497.3 |

TABLE 2-continued

Additional Exemplary Compounds

| Compound | Structure | Proton NMR | MS [M + 1] |
|---|---|---|---|
| 4-(4-amino-6-(4-methacrylamido-phenyl)-7-methyl-7H-pyrrolo[2,3-d]pyrimidin-5-yl)-N-(1-methoxycyclopropyl)methyl)-N-methylbenzamide | 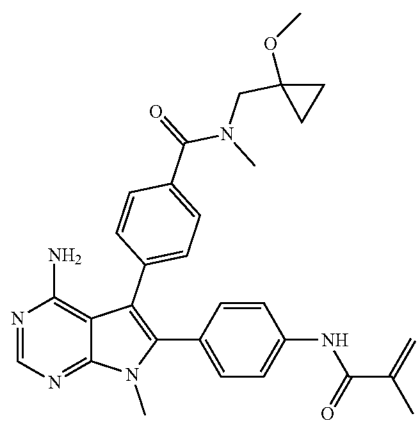 [SMILES: C=C(C)C(=O)Nc1ccc(-c2c(-c3ccc(C(=O)N(C)CC4(OC)CC4)cc3)c3c(N)ncnc3n2C)cc1] | ¹H NMR (400 MHz, Methanol-d₄) δ 8.23 (s, 1H), 7.67 (d, J = 8.3 Hz, 2H), 7.46-7.37 (m, 4H), 7.28 (d, J = 7.7 Hz, 2H), 5.81 (s, 1H), 5.54 (s, 1H), 3.83 (s, 1H), 3.71 (s, 3H), 3.59 (s, 1H), 3.39 (s, 2H), 3.11 (s, 3H), 2.86 (s, 1H), 2.04 (d, J = 1.3 Hz, 3H), 0.88 (s, 1H), 0.82 (s, 1H), 0.73 (s, 1H), 0.52 (s, 1H). | 525.45 |
| N-(4-(5-(4-((1R,5S)-2-azabicyclo[3.1.0]hexane-2-carbonyl)phenyl)-4-amino-7-methyl-7H-pyrrolo[2,3-d]pyrimidin-6-yl)-3-fluorophenyl)methacrylamide | 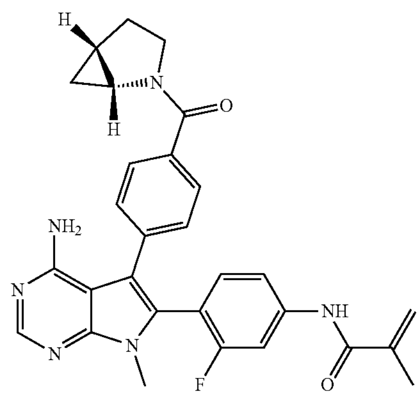 [SMILES: C=C(C)C(=O)Nc1ccc(-c2c(-c3ccc(C(=O)N4CC[C@H]5C[C@H]54)cc3)c3c(N)ncnc3n2C)c(F)c1] | ¹H NMR (400 MHz, DMSO-d₆) δ 10.11 (s, 1H), 8.23 (s, 1H), 7.77 (dd, J = 12.4, 2.0 Hz, 1H), 7.60 (d, J = 7.6 Hz, 1H), 7.49 (dd, J = 8.5, 2.0 Hz, 1H), 7.28 (d, J = 8.3 Hz, 3H), 6.05 (s, 2H), 5.83 (s, 1H), 5.58 (s, 1H), 3.97 (s, 1H), 3.56 (s, 3H), 3.14 (s, 1H), 2.06 (s, 1H), 1.96 (d, J = 1.2 Hz, 3H), 1.70 (s, 1H), 0.77 (s, 2H). | 511.30 |
| N-(4-(5-(4-((1S,5R)-2-azabicyclo[3.1.0]hexane-2-carbonyl)phenyl)-4-amino-7-methyl-7H-pyrrolo[2,3-d]pyrimidin-6-yl)-3-fluorophenyl)methacrylamide | 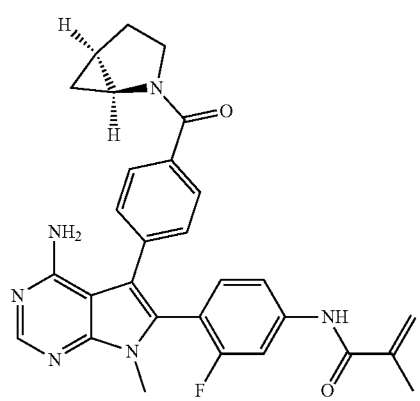 [SMILES: C=C(C)C(=O)Nc1ccc(-c2c(-c3ccc(C(=O)N4CC[C@@H]5C[C@@H]54)cc3)c3c(N)ncnc3n2C)c(F)c1] | ¹H NMR (400 MHz, DMSO-d₆) δ 10.11 (s, 1H), 8.23 (s, 1H), 7.77 (dd, J = 12.5, 2.0 Hz, 1H), 7.60 (d, J = 7.7 Hz, 1H), 7.49 (dd, J = 8.4, 2.0 Hz, 2H), 7.28 (d, J = 8.3 Hz, 3H), 6.03 (s, 1H), 5.83 (s, 1H), 5.58 (s, 1H), 3.97 (s, 1H), 3.56 (s, 4H), 3.14 (s, 1H), 2.06 (s, 1H), 1.96 (d, J = 1.2 Hz, 4H), 1.70 (s, 1H), 0.77 (s, 2H). | 511.30 |

TABLE 2-continued

Additional Exemplary Compounds

| Compound | Structure | Proton NMR | MS [M + 1] |
|---|---|---|---|
| N-(4-(5-(4-(2-azabicyclo[2.1.1]hexane-2-carbonyl)phenyl)-4-amino-7-methyl-7H-pyrrolo[2,3-d]pyrimidin-6-yl)-3-fluorophenyl)methacrylamide | 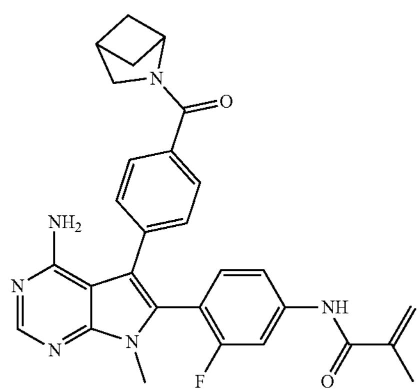 [SMILES: C=C(C)C(=O)Nc1ccc(-c2c(-c3ccc(C(=O)N4CC5CC4C5)cc3)c3c(N)ncnc3n2C)c(F)c1] | $^1$H NMR (400 MHz, DMSO-$d_6$) δ 10.09 (s, 1H), 8.22 (s, 1H), 7.77 (dd, J = 12.5, 2.0 Hz, 1H), 7.64 (d, J = 8.9 Hz, 1H), 7.49 (dd, J = 8.4, 2.0 Hz, 1H), 7.40 (d, J = 7.9 Hz, 1H), 7.26 (d, J = 7.3 Hz, 3H), 6.02 (s, 1H), 5.83 (s, 1H), 5.57 (s, 1H), 4.33 (d, J = 6.9 Hz, 1H), 3.55 (s, 3H), 3.44 (s, 2H), 2.89 (d, J = 17.1 Hz, 1H), 1.95 (s, 5H), 1.47 (s, 1H), 1.33 (s, 1H). | 511.40 |
| 4-(4-amino-6-(2-fluoro-4-methacrylamidophenyl)-7-methyl-7H-pyrrolo[2,3-d]pyrimidin-5-yl)-N-methyl-N-(oxetan-3-ylmethyl)benzamide | | $^1$H NMR (400 MHz, DMSO-$d_6$) δ 10.10 (s, 1H), 8.22 (s, 1H), 7.76 (dd, J = 12.6, 1.9 Hz, 1H), 7.48 (dd, J = 8.4, 2.0 Hz, 1H), 7.34 (d, J = 7.7 Hz, 2H), 7.25 (d, J = 7.8 Hz, 3H), 5.82 (s, 1H), 5.76 (s, 1H), 5.58 (s, 1H), 4.65 (s, 2H), 4.40 (s, 1H), 4.15 (s, 1H), 3.76 (s, 1H), 3.55 (s, 4H), 3.22 (s, 1H), 2.88 (s, 3H), 1.95 (s, 3H). | 529.30 |
| (R)-N-(4-(4-amino-7-methyl-5-(4-(2-methylpiperidine-1-carbonyl)phenyl)-7H-pyrrolo[2,3-d]pyrimidin-6-yl)-3-fluorophenyl)methacrylamide | 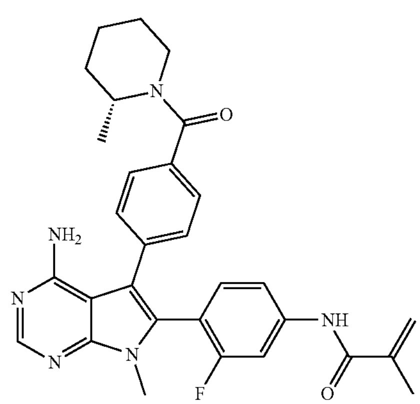 [SMILES: C=C(C)C(=O)Nc1ccc(-c2c(-c3ccc(C(=O)N4CCCC[C@H]4C)cc3)c3c(N)ncnc3n2C)c(F)c1] | $^1$H NMR (400 MHz, DMSO-$d_6$) δ 10.09 (s, 1H), 8.22 (s, 1H), 7.76 (dd, J = 12.5, 2.0 Hz, 1H), 7.48 (dd, J = 8.5, 2.0 Hz, 1H), 7.31 (d, J = 8.3 Hz, 2H), 7.29-7.21 (m, 3H), 6.02 (s, 1H), 5.82 (s, 1H), 5.57 (s, 1H), 3.55 (s, 5H), 2.98 (s, 1H), 1.95 (d, J = 1.3 Hz, 3H), 1.64 (d, J = 10.9 Hz, 1H), 1.59 (s, 3H), 1.51 (s, 1H), 1.36 (d, J = 12.8 Hz, 1H), 1.18 (d, J = 6.9 Hz, 3H). | 527.40 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)-3-(morpholinomethyl)phenyl)methacrylamide | 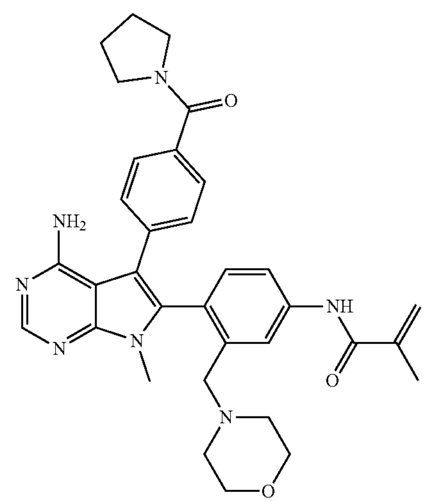 [SMILES: C=C(C)C(=O)Nc1ccc(-c2c(-c3ccc(C(=O)N4CCCC4)cc3)c3c(N)ncnc3n2C)c(CN2CCOCC2)c1] | $^1$H NMR (400 MHz, DMSO-$d_6$) δ 9.92 (s, 1H), 8.22 (s, 1H), 7.80 (dd, J = 8.3, 2.2 Hz, 1H), 7.75 (d, J = 22 Hz, 1H), 7.45 (d, J = 7.9 Hz, 2H), 7.41 (d, J = 8.3 Hz, 1H), 7.23 (d, J = 7.9 Hz, 2H), 6.02 (s, 2H), 5.83 (s, 1H), 5.54 (d, J = 1.9 Hz, 1H), 3.48-3.35 (m, 3H), 3.15 (d, J = 13.8 Hz, 1H), 2.75 (d, J = 13.7 Hz, 1H), 2.05 (d, J = 6.7 Hz, 2H), 1.96 (t, J = 1.2 Hz, 5H), 1.83 (dt, J = 19.2, 6.4 Hz, 3H). | 580.50 |
| N-(4-(4-amino-7-methyl-5-(4-(pyrrolidine-1-carbonyl)phenyl)-7H-pyrrolo[2,3-d]pyrimidin-6-yl)-3-(tetrahydrofuran-2-yl)phenyl)methacrylamide (atropisomer 1) | Atropisomer 1 | $^1$H NMR (400 MHz, Methanol-$d_4$) δ 8.24 (s, 1H), 7.84 (d, J = 2.2 Hz, 1H), 7.74 (dd, J = 8.3, 2.3 Hz, 1H), 7.55-7.48 (m, 2H), 7.38 (dd, J = 13.8, 8.2 Hz, 3H), 5.86-5.81 (m, 1H), 5.55 (d, J = 1.8 Hz, 1H), 4.47 (dd, J = 7.9, 6.8 Hz, 1H), 4.05 (q, J = 7.2 Hz, 1H), 3.75 (q, J = 7.6 Hz, 1H), 3.59 (t, J = 1.0 Hz, 2H), 3.55 (s, 3H), 3.47 (t, J = 6.6 Hz, 2H), 2.08-2.01 (m, 3H), 1.96 (dq, J = 27.5, 6.8 Hz, 5H), 1.87-1.74 (m, 1H), 1.61 (dq, J = 12.7, 7.0 Hz, 1H), 1.34 (dq, J = 12.5, 8.1Hz, 1H). | 551.40 |
| N-(4-(4-amino-7-methyl-5-(4-(pyrrolidine-1-carbonyl)phenyl)-7H-pyrrolo[2,3-d]pyrimidin-6-yl)-3-(tetrahydrofuran-2-yl)phenyl)methacrylamide (atropisomer 1) | Atropisomer 2 | $^1$H NMR (400 MHz, Methanol-$d_4$) δ 8.24 (s, 1H), 7.84 (d, J = 2.2 Hz, 1H), 7.74 (dd, J = 8.3, 2.3 Hz, 1H), 7.55-7.48 (m, 2H), 7.38 (dd, J = 13.8, 8.2 Hz, 3H), 5.86-5.81 (m, 1H), 5.55 (d, J = 1.8 Hz, 1H), 4.47 (dd, J = 7.9, 6.8 Hz, 1H), 3.91 (q, J = 7.2 Hz, 1H), 3.75 (q, J = 7.6 Hz, 1H), 3.59 (t, J = 7.0 Hz, 2H), 3.55 (s, 3H), 3.47 (t, J = 6.6 Hz, 2H), 2.08-2.01 (m, 3H), 1.96 (dq, J = 27.5, 6.8 Hz, 5H), 1.87-1.74 (m, 1H), 1.61 (dq, J = 12.7, 7.0 Hz, 1H), 1.34 (dq, J = 12.5, 8.1 Hz, 1H). | 551.40 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)-3-chlorophenyl) methacrylamide | 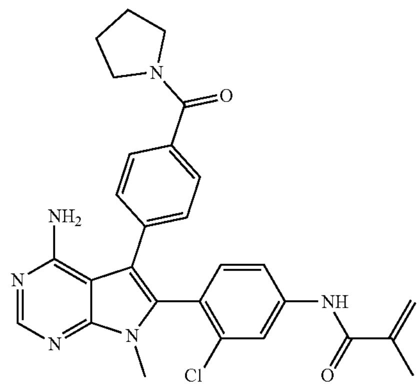 [SMILES: C=C(C)C(=O)Nc1ccc(-c2c(-c3ccc(C(=O)N4CCCC4)cc3)c3c(N)ncnc3n2C)c(Cl)c1] | $^1$H NMR (400 MHz, DMSO-d$_6$) δ 10.06 (s, 1H), 8.23 (s, 1H), 8.03 (d, J = 2.0 Hz, 1H), 7.65 (dd, J = 8.4, 2.1 Hz, 1H), 7.47 (d, J = 8.2 Hz, 2H), 7.33 (d, J = 8.4 Hz, 1H), 7.24 (d, J = 8.1 Hz, 2H), 6.02 (s, 1H), 5.83 (d, J = 1.4 Hz, 1H), 5.58 (s, 1H), 3.48 (s, 3H), 3.42 (dt, J = 18.3, 6.6 Hz, 4H), 1.98-1.93 (m, 3H), 1.83 (dt, J = 18.7, 6.6 Hz, 4H). | 515.35 |
| N-(4-(4-amino-7-methyl-5-(4-(pyrrolidine-1-carbonyl)phenyl)-7H-pyrrolo[2,3-d]pyrimidin-6-yl)-3-cyanophenyl) methacrylamide | 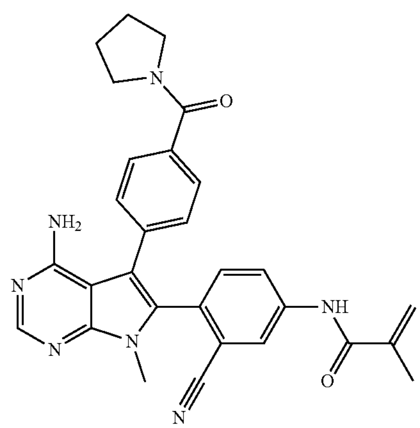 [SMILES: C=C(C)C(=O)Nc1ccc(-c2c(-c3ccc(C(=O)N4CCCC4)cc3)c3c(N)ncnc3n2C)c(C#N)c1] | $^1$H NMR (400 MHz, DMSO-d$_6$) δ 10.21 (s, 1H), 8.26 (s, 1H), 8.20 (d, J = 2.2 Hz, 1H), 8.03 (dd, J = 8.6, 2.3 Hz, 1H), 7.62 (d, J = 8.6 Hz, 1H), 7.49 (d, J = 7.9 Hz, 2H), 7.22 (d, J = 7.8 Hz, 2H), 6.12 (s, 1H), 5.86 (s, 1H), 5.61 (s, 1H), 3.56 (s, 3H), 3.49-3.38 (m, 4H), 1.96 (s, 3H), 1.88-1.78 (m, 4H). | 506.35 |
| N-(4-(4-amino-7-methyl-5-(4-(pyrrolidine-1-carbonyl)phenyl)-7H-pyrrolo[2,3-d]pyrimidin-6-yl)-3-(difluoromethyl)phenyl) methacrylamide | 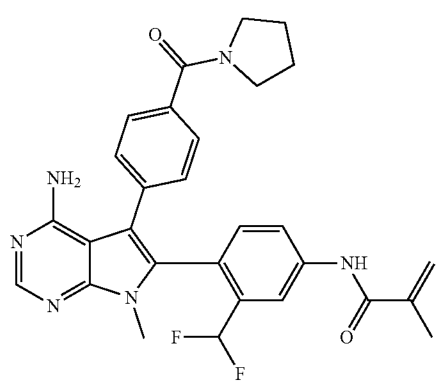 [SMILES: C=C(C)C(=O)Nc1ccc(-c2c(-c3ccc(C(=O)N4CCCC4)cc3)c3c(N)ncnc3n2C)c(C(F)F)c1] | $^1$H NMR (400 MHz, DMSO-d$_6$) δ 10.11 (s, 1H), 8.24 (s, 1H), 8.07 (d, J = 2.2 Hz, 1H), 8.00-7.93 (m, 1H), 7.52 (d, J = 8.4 Hz, 1H), 7.45 (d, J = 8.2 Hz, 2H), 7.23 (d, J = 8.1 Hz, 2H), 6.51 (d, J = 5.6 Hz, 1H), 6.02 (s, 1H), 5.86 (d, J = 1.3 Hz, 1H), 5.58 (d, J = 1.7 Hz, 1H), 3.44 (d, J = 13.6 Hz, 6H), 1.96 (t, J = 1.2 Hz, 3H), 1.82 (dq, J = 19.2, 6.7 Hz, 4H). | 531.25 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)-3-methoxyphenyl) methacrylamide | 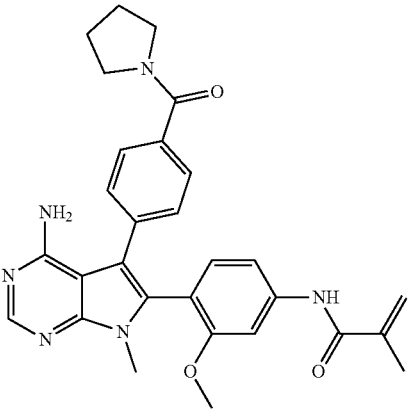 | $^1$H NMR (400 MHz, DMSO-$d_6$) δ 9.89 (s, 1H), 8.19 (s, 1H), 7.62 (d, J = 1.9 Hz, 1H), 7.49-7.43 (m, 2H), 7.26 (dd, J = 8.3, 1.9 Hz, 1H), 7.25-7.18 (m, 2H), 6.99 (d, J = 8.2 Hz, 1H), 5.92 (s, 1H), 5.81 (t, J = 1.0 Hz, 1H), 5.54 (t, J = 1.4 Hz, 1H), 3.70 (s, 3H), 3.47 (s, 4H), 3.45-3.37 (m,3H), 1.96 (t, J = 1.2 Hz, 3H), 1.83 (dt, J = 17.0, 6.4 Hz, 4H). | 511.40 |
| N-(4-(4-amino-7-methyl-5-(4-(pyrrolidine-1-carbonyl)phenyl)-7H-pyrrolo[2,3-d]pyrimidin-6-yl)-3-cyclopropylphenyl) methacrylamide | 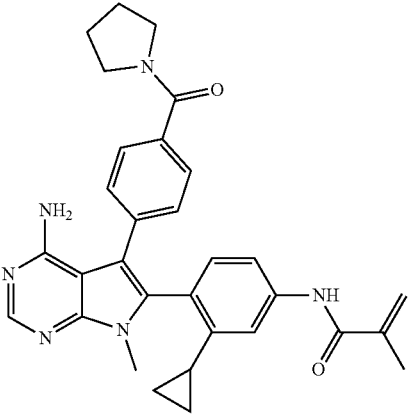 [SMILES: C=C(C)C(=O)Nc1ccc(-c2c(-c3ccc(C(=O)N4CCCC4)cc3)c3c(N)ncnc3n2C)c(C2CC2)c1] | $^1$H NMR (400 MHz, DMSO-$d_6$) δ 9.79 (s, 1H), 8.32 (s, 1H), 7.61 (dd, J = 8.3, 2.1 Hz, 1H), 7.50-7.43 (m, 2H), 7.28-7.16 (m, 4H), 5.80 (s, 1H), 5.53 (t, J = 1.6 Hz, 1H), 3.52 (s, 3H), 3.43 (dt, J = 17.2, 6.6 Hz, 4H), 1.94 (t, J = 1.2 Hz, 3H), 1.83 (dq, J = 18.6, 6.8 Hz, 4H), 1.52-1.40 (m, 1H), 0.84 (ddt, J = 10.2, 8.7, 4.0 Hz, 1H), 0.72-0.52 (m, 2H), 0.44-0.34 (m, 1H). | 521.4 |
| N-(4-(4-amino-7-methyl-5-(4-(pyrrolidine-1-carbonyl)phenyl)-7H-pyrrolo[2,3-d]pyrimidin-6-yl)-3-cyclopropylphenyl) methacrylamide | 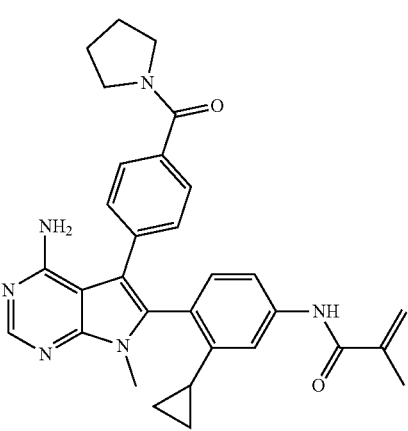

Atropisomer 1 | $^1$H NMR (400 MHz, DMSO-$d_6$) δ 9.78 (s, 1H), 8.29 (s, 1H), 7.60 (dd, J = 8.3, 2.1 Hz, 1H), 7.50-7.43 (m, 2H), 7.28-7.17 (m, 4H), 5.80 (s, 1H), 5.53 (t, J = 1.5 Hz, 1H), 3.52 (s, 3H), 3.43 (dt, J = 17.3, 6.6 Hz, 4H), 1.95 (d, J = 1.2 Hz, 3H), 1.90-1.75 (m, 4H), 1.46 (td, J = 8.5, 4.4 Hz, 1H), 0.84 (p, J = 4.9 Hz, 1H), 0.63 (ddt, J = 29.5, 9.2, 4.5 Hz, 2H), 0.39 (p, J = 4.8 Hz, 1H). | 521.3 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)-3-cyclopropylphenyl) methacrylamide | Atropisomer 2 | $^1$H NMR (400 MHz, DMSO-d$_6$) δ 9.77 (s, 1H), 8.21 (s, 1H), 7.59 (dd, J = 8.4, 2.1 Hz, 1H), 7.49-7.43 (m, 2H), 7.32-7.16 (m, 4H), 5.80 (s, 1H), 5.55-5.50 (m, 1H), 3.49 (s, 3H), 3.47-3.38 (m, 4H), 1.95 (t, J = 1.3 Hz, 3H), 1.83 (dq, J = 17.3, 6.5 Hz, 4H), 1.48 (td, J = 8.3, 4.5 Hz, 1H), 0.85 (s, 1H), 0.66 (d, J = 13.8 Hz, 1H), 0.58 (dt, J = 10.1, 5.2 Hz, 1H), 0.43-0.36 (m, 1H). | 521.3 |
| N-(4-(4-amino-7-methyl-5-(4-(pyrrolidine-1-carbonyl)phenyl)-7H-pyrrolo[2,3-d]pyrimidin-6-yl)-3-ethylphenyl) methacrylamide | | $^1$H NMR (400 MHz, DMSO-d$_6$) δ 9.85 (s, 1H), 8.21 (s, 1H), 7.70-7.61 (m, 2H), 7.48-7.42 (m, 2H), 7.32 (d, J = 8.3 Hz, 1H), 7.26-7.19 (m, 2H), 6.19-5.79 (m, 3H), 5.53 (t, J = 1.6 Hz, 1H), 3.48-3.35 (m, 7H), 2.29 (dt, J = 15.1, 7.4 Hz, 1H), 2.10 (dq, J = 15.0, 7.5 Hz, 1H), 1.96 (t, J = 1.2 Hz, 3H), 1.84 (dq, J = 18.9, 6.8 Hz, 4H), 0.83 (t, J = 7.5 Hz, 3H). | 509.3 |
| N-(4-(4-amino-7-methyl-5-(4-(pyrrolidine-1-carbonyl)phenyl)-7H-pyrrolo[2,3-d]pyrimidin-6-yl)-3-ethylphenyl) methacrylamide | Atropisomer 1 | $^1$H NMR (400 MHz, DMSO-d$_6$) δ 9.85 (s, 1H), 8.22 (s, 1H), 7.71-7.62 (m, 2H), 7.49-7.42 (m, 2H), 7.32 (d, J = 8.3 Hz, 1H), 7.23 (d, J = 8.2 Hz, 2H), 5.82 (s, 1H), 5.53 (t, J = 1.5 Hz, 1H), 3.48-3.35 (m, 7H), 2.30 (dt, J = 15.0, 7.5 Hz, 1H), 2.10 (dq, J = 14.9, 7.5 Hz, 1H), 1.96 (t, J = 1.2 Hz, 3H), 1.85 (dq, J = 18.9, 6.8 Hz, 4H), 0.83 (t, J = 7.5 Hz, 3H). | 509.3 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)-3-ethylphenyl)methacrylamide | Atropisomer 2 | $^1$H NMR (400 MHz, DMSO-$d_6$) δ 9.85 (s, 1H), 8.22 (s, 1H), 7.71-7.62 (m, 2H), 7.49-7.42 (m, 2H), 7.32 (d, J = 8.2 Hz, 1H), 7.23 (d, J = 8.2 Hz, 2H), 5.82 (s, 1H), 5.53 (t, J = 1.5 Hz, 1H), 3.48-3.35 (m, 7H), 2.30 (dt, J = 15.0, 7.5 Hz, 1H), 2.10 (dq, J = 14.9, 7.5 Hz, 1H), 1.96 (d, J = 1.2 Hz, 3H), 1.82 (dq, J = 18.6, 6.6 Hz, 4H), 0.83 (t, J = 7.5 Hz, 3H). | 509.3 |
| N-(4-(4-amino-7-methyl-5-(4-((4-methylpyrimidin-2-yl)oxy)phenyl)-7H-pyrrolo[2,3-d]pyrimidin-6-yl)-3-fluorophenyl)methacrylamide | 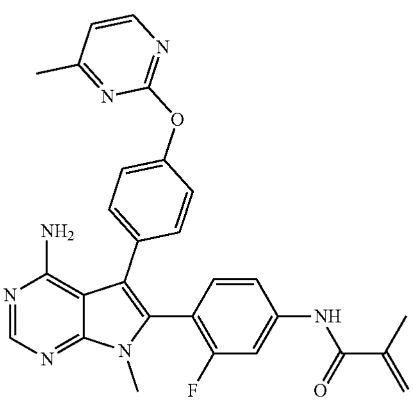 [SMILES: C=C(C)C(=O)Nc1ccc(-c2c(-c3ccc(Oc4nccc(C)n4)cc3)c3c(N)ncnc3n2C)c(F)c1] | $^1$H NMR (400 MHz, DMSO-$d_6$) δ 10.11 (s, 1H), 8.46 (d, J = 5.0 Hz, 1H), 8.22 (s, 1H), 7.80-7.76 (m, 1H), 7.53-7.51 (m, 1H), 7.36-7.26 (m, 3H), 7.23-7.13 (m, 3H), 5.82 (s, 1H), 5.58 (d, J = 1.8 Hz, 1H), 3.54 (s, 3H), 2.41 (s, 3H), 1.95 (t, J = 1.2 Hz, 3H). | 510.20 |
| N-(4-(4-amino-5-(2-fluoro-4-((4-methylpyrimidin-2-yl)oxy)phenyl)-7-methyl-7H-pyrrolo[2,3-d]pyrimidin-6-yl)phenyl)methacrylamide | 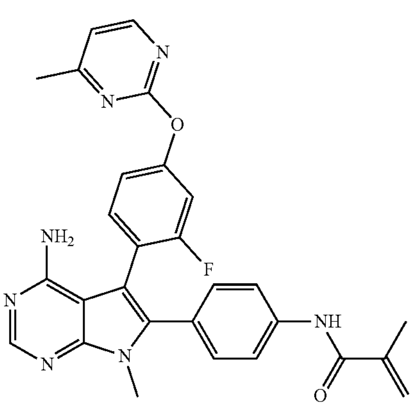 | $^1$H NMR (400 MHz, DMSO-$d_6$) δ 9.90 (s, 1H), 8.50 (d, J = 5.0 Hz, 1H), 8.21 (s, 1H), 7.76-7.66 (m, 2H), 7.38 (t, J = 8.5 Hz, 1H), 7.31-7.27 (m, 2H), 7.22-7.15 (m, 2H), 7.09-7.07 (m, 1H), 5.80 (d, J = 1.3 Hz, 1H), 5.53 (d, J = 1.7 Hz, 1H), 3.64 (s, 3H), 2.43 (s, 3H), 1.95 (t, J = 1.3 Hz, 3H). | 510.20 |

TABLE 2-continued

Additional Exemplary Compounds

| Compound | Structure | Proton NMR | MS [M + 1] |
|---|---|---|---|
| N-(4-(4-amino-5-(3-methoxy-4-((4-methylpyrimidin-2-yl)oxy)phenyl)-7-methyl-7H-pyrrolo[2,3-d]pyrimidin-6-yl)-3-fluorophenyl) methacrylamide | 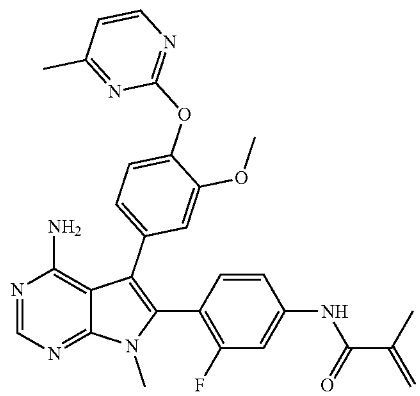 [SMILES: C=C(C)C(=O)Nc1ccc(-c2c(-c3ccc(Oc4nccc(C)n4)c(OC)c3)c3c(N)ncnc3n2C)c(F)c1] | $^1$H NMR (400 MHz, DMSO-d$_6$) δ 10.11 (s, 1H), 8.40 (d, J = 5.0 Hz, 1H), 8.23 (s, 1H), 7.80 (dd, J = 12.5, 2.0 Hz, 1H), 7.54 (dd, J = 8.4, 2.0 Hz, 1H), 7.36 (t, J = 8.5 Hz, 1H), 7.14 (d, J = 8.1 Hz, 1H), 7.09 (d, J = 5.1 Hz, 1H), 6.97 (d, J = 2.0 Hz, 1H), 6.85 (dd, J = 8.1, 2.0 Hz, 1H), 5.83 (s, 1H), 5.58 (s, 1H), 3.55 (d, J = 5.1 Hz, 6H), 2.39 (s, 3H), 1.96 (t, J = 1.2 Hz, 3H). | 540.25 |
| N-(4-(4-amino-5-(4-((5-fluoropyrimidin-2-yl)oxy)-3-methoxyphenyl)-7-methyl-7H-pyrrolo[2,3-d]pyrimidin-6-yl)phenyl) methacrylamide | 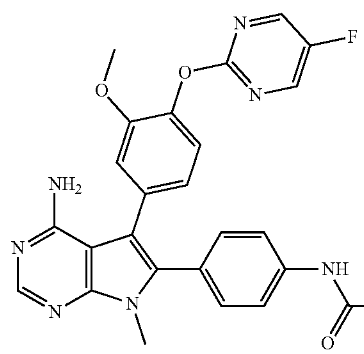 | $^1$H NMR (400 MHz, DMSO-d$_6$) δ 9.91 (s, 1H), 8.71 (s, 2H), 8.21 (s, 1H), 7.75 (d, J = 8.7 Hz, 2H), 7.35 (d, J = 8.6 Hz, 2H), 7.18 (d, J = 8.1 Hz, 1H), 6.99 (d, J = 2.0 Hz, 1H), 6.86 (dd, J = 8.1, 2.0 Hz, 1H), 5.81 (s, 1H), 5.54 (s, 1H), 3.60 (s, 3H), 3.56 (s, 3H), 1.96 (d, J = 1.3 Hz, 3H). | 526.20 |
| N-(4-(4-amino-7-methyl-5-(6-((6-methylpyridin-2-yl)oxy)pyridin-3-yl)-7H-pyrrolo[2,3-d]pyrimidin-6-yl)phenyl) methacrylamide | 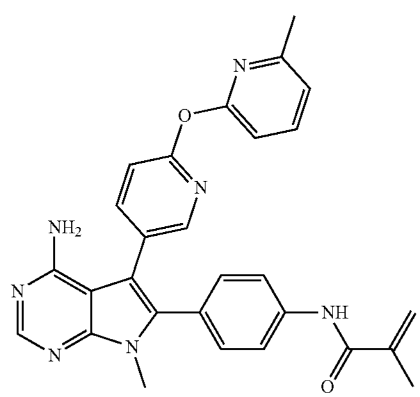 [SMILES: C=C(C)C(=O)Nc1ccc(-c2c(-c3ccc(Oc4cccc(C)n4)nc3)c3c(N)ncnc3n2C)cc1] | $^1$H NMR (400 MHz, DMSO-d$_6$) δ 9.91 (s, 1H), 8.21 (s, 1H), 7.99 (d, J = 2.4 Hz, 1H), 7.75 (t, J = 8.2 Hz, 4H), 7.42-7.24 (m, 2H), 7.08 (dd, J = 14.6, 7.9 Hz, 2H), 6.92 (d, J = 8.1 Hz, 1H), 5.80 (s, 1H), 5.54 (s, 1H), 3.61 (s, 3H), 2.38 (s, 3H), 1.96 (t, J = 1.3 Hz, 3H). | 492.30 |
| N-(4-(4-amino-5-(6-((5-fluoropyrimidin-2-yl)oxy)pyridin-3-yl)-7-methyl-7H-pyrrolo[2,3-d]pyrimidin-6-yl)phenyl) methacrylamide | 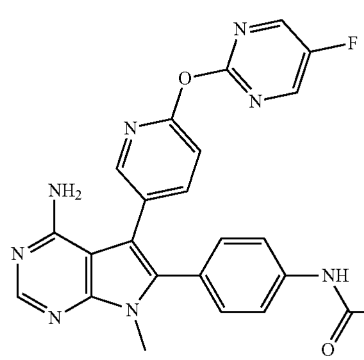 | $^1$H NMR (400 MHz, DMSO-d$_6$) δ 9.94 (s, 1H), 8.83 (s, 2H), 8.22 (s, 1H), 8.07 (d, J = 2.4 Hz, 1H), 7.76 (dd, J = 9.4, 2.5 Hz, 3H), 7.43-7.26 (m, 2H), 7.23 (s, 1H), 5.92 (d, J = 81.4 Hz, 3H), 5.55 (d, J = 1.8 Hz, 1H), 3.60 (s, 3H), 1.96 (t, J = 1.2 Hz, 3H). | 497.25 |

TABLE 2-continued

Additional Exemplary Compounds

| Compound | Structure | Proton NMR | MS [M + 1] |
|---|---|---|---|
| N-(4-(4-amino-5-(5-((5-fluoropyrimidin-2-yl)oxy)pyridin-2-yl)-7-methyl-7H-pyrrolo[2,3-d]pyrimidin-6-yl)phenyl)methacrylamide | 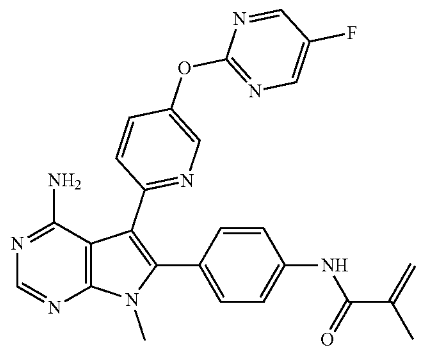 [SMILES: C=C(C)C(=O)Nc1ccc(-c2c(-c3ccc(Oc4ncc(F)cn4)cn3)c3c(N)ncnc3n2C)cc1] | ¹H NMR (400 MHz, DMSO-d₆) δ 10.02 (s, 1H), 8.78 (s, 2H), 8.60 (d, J = 2.8 Hz, 1H), 8.17 (s, 1H), 7.93-7.85 (m, 2H), 7.50 (dd, J = 8.8, 2.8 Hz, 1H), 7.46-7.38 (m, 2H), 6.94 (d, J = 8.8 Hz, 2H), 5.84 (t, J = 1.0 Hz, 1H), 5.57 (t, J = 1.6 Hz, 1H), 3.52 (s, 3H), 1.98 (t, J = 1.2 Hz, 3H). | 497.30 |
| N-(4-(4-amino-7-methyl-5-(2-methyl-4-((4-methylpyrimidin-2-yl)oxy)phenyl)-7H-pyrrolo[2,3-d]pyrimidin-6-yl)phenyl)methacrylamide | 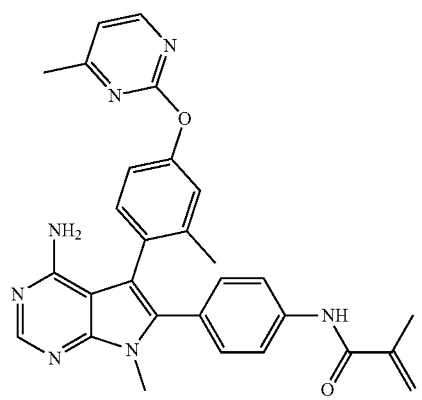 | ¹H NMR (400 MHz, DMSO-d₆) δ 9.88 (s, 1H), 8.47 (d, J = 5.0 Hz, 1H), 8.19 (s, 1H), 7.70 (d, J = 8.6 Hz, 2H), 7.28 (dd, J = 8.6, 2.3 Hz, 3H), 7.15 (d, J = 5.1 Hz, 1H), 7.10-7.00 (m, 2H), 5.78 (s, 1H), 5.53 (s, 1H), 3.66 (s, 3H), 2.42 (s, 3H), 1.97 (s, 3H), 1.94 (s, 3H). | 540.25 |
| N-(4-(5-((4R)-4-(3-azabicyclo[3.2.1]octane-3-carbonyl)cyclohex-1-en-1-yl)-4-amino-7-methyl-7H-pyrrolo[2,3-d]pyrimidin-6-yl)phenyl)methacrylamide | 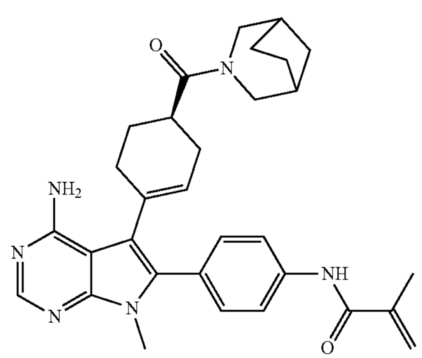 [SMILES: C=C(C)C(=O)Nc1ccc(-c2c(C3=CC[C@H](C(=O)N4CC5CCC(C5)C4)CC3)c3c(N)ncnc3n2C)cc1] | ¹H NMR (400 MHz, DMSO-d₆) δ 9.94 (s, 1H), 8.09 (s, 1H), 7.90-7.76 (m, 2H), 7.43 (d, J = 8.2 Hz, 2H), 6.52 (s, 2H), 5.83 (s, 1H), 5.75 (s, 1H), 5.55 (s, 1H), 4.17 (d, J = 12.6 Hz, 1H), 4.08 (d, J = 12.8 Hz, 0H), 3.73 (s, 1H), 3.58 (s, 3H), 3.14-3.02 (m, 2H), 2.57 (d, J = 12.0 Hz, 1H), 2.19 (s, 4H), 1.97 (s, 3H), 1.86 (s, 1H), 1.65 (s, 1H), 1.54 (s, 7H), 1.30 (s, 1H), 1.24 (s, 1H). | 525.30 |
| N-(4-(5-((4S)-4-(3-azabicyclo[3.2.1]octane-3-carbonyl)cyclohex-1-en-1-yl)-4-amino-7-methyl-7H-pyrrolo[2,3-d]pyrimidin-6-yl)phenyl)methacrylamide | 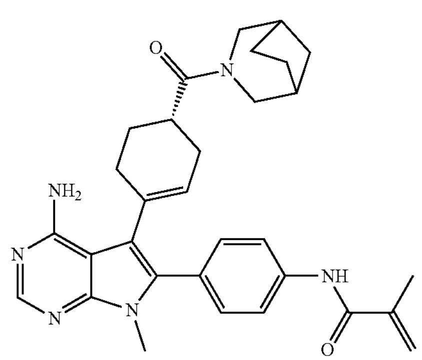 [SMILES: C=C(C)C(=O)Nc1ccc(-c2c(C3=CC[C@@H](C(=O)N4CC5CCC(C5)C4)CC3)c3c(N)ncnc3n2C)cc1] | ¹H NMR (400 MHz, DMSO-d₆) δ 9.94 (s, 1H), 8.09 (s, 1H), 7.90-7.76 (m, 2H), 7.43 (d, J = 8.2 Hz, 2H), 6.52 (s, 2H), 5.83 (s, 1H), 5.75 (s, 1H), 5.55 (s, 1H), 4.17 (d, J = 12.6 Hz, 1H), 4.08 (d, J = 12.8 Hz, 0H), 3.73 (s, 1H), 3.58 (s, 3H), 3.14-3.02 (m, 2H), 2.57 (d, J = 12.0 Hz, 1H), 2.19 (s, 4H), 1.97 (s, 3H), 1.86 (s, 1H), 1.65 (s, 1H), 1.54 (s, 7H), 1.30 (s, 1H), 1.24 (s, 1H). | 525.30 |

TABLE 2-continued

Additional Exemplary Compounds

| Compound | Structure | Proton NMR | MS [M + 1] |
|---|---|---|---|
| (R)-4-(4-amino-6-(4-methacrylamido-phenyl)-7-methyl-7H-pyrrolo[2,3-d]pyrimidin-5-yl)-N-(2-methoxy-2-methylpropyl)cyclohex-3-ene-1-carboxamide | 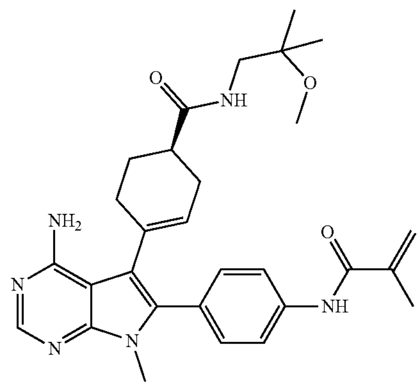 [SMILES: C=C(C)C(=O)Nc1ccc(-c2c(C3=CC[C@H](C(=O)NCC(C)(C)OC)CC3)c3c(N)ncnc3n2C)cc1] | $^1$H NMR (400 MHz, DMSO-d$_6$) δ 9.94 (s, 1H), 8.10 (s, 1H), 7.85-7.77 (m, 2H), 7.70 (t, J = 6.2 Hz, 1H), 7.47-7.39 (m, 2H), 6.44 (s, 1H), 5.83 (t, J = 1.1 Hz, 1H), 5.78 (s, 1H), 5.58-5.53 (m, 1H), 3.57 (s, 3H), 3.19 (dd, J = 13.6, 6.5 Hz, 1H), 3.08 (s, 3H), 3.03 (dd, J = 13.6, 5.6 Hz, 1H), 2.61 (d, J = 6.3 Hz, 1H), 2.29 (s, 1H), 2.21 (d, J = 18.0 Hz, 1H), 1.98 (t, J = 1.2 Hz, 3H), 1.90 (s, 2H), 1.66 (d, J = 6.1 Hz, 2H), 1.03 (d, J = 4.0 Hz, 6H). | 517.25 |
| (S)-4-(4-amino-6-(4-methacrylamido-phenyl)-7-methyl-7H-pyrrolo[2,3-d]pyrimidin-5-yl)-N-(2-methoxy-2-methylpropyl)cyclohex-3-ene-1-carboxamide | 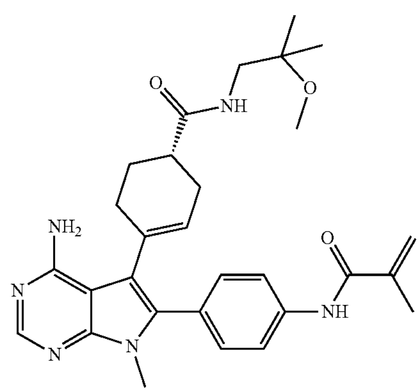 | $^1$H NMR (400 MHz, DMSO-d$_6$) δ 9.94 (s, 1H), 8.12 (s, 1H), 7.85-7.77 (m, 2H), 7.70 (t, J = 6.0 Hz, 1H), 7.47-7.39 (m, 2H), 6.50 (s, 1H), 5.86-5.76 (m, 2H), 5.55 (t, J = 1.4 Hz, 1H), 3.58 (s, 3H), 3.19 (dd, J = 13.6, 6.5 Hz, 1H), 3.08 (s, 3H), 3.03 (dd, J = 13.6, 5.6 Hz, 1H), 2.65-2.58 (m, 1H), 2.26 (d, J = 22.4 Hz, 2H), 1.98 (t, J = 1.2 Hz, 3H), 1.94-1.87 (m, 2H), 1.66 (s, 2H), 1.24 (s, 0H), 1.03 (d, J = 4.0 Hz, 6H). | 517.30 |
| (S)-4-(4-amino-6-(4-methacrylamido-phenyl)-7-methyl-7H-pyrrolo[2,3-d]pyrimidin-5-yl)-N-methyl-N-((tetrahydrofuran-3-yl)methyl)benzamide | 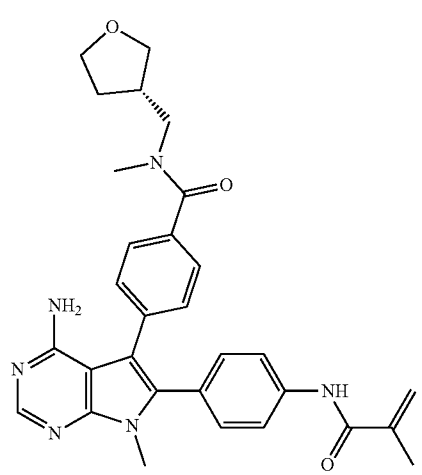 [SMILES: C=C(C)C(=O)Nc1ccc(-c2c(-c3ccc(C(=O)N(C)C[C@@H]4CCOC4)cc3)c3c(N)ncnc3n2C)cc1] | $^1$H NMR (400 MHz, Methanol-d$_4$) δ 8.22 (s, 1H), 7.71-7.64 (m, 2H), 7.40 (s, 5H), 7.28 (d, J = 8.2 Hz, 2H), 5.81 (s, 1H), 5.54 (s, 1H), 3.96-3.87 (m, 1H), 3.80 (d, J = 7.6 Hz, 2H), 3.71 (s, 3H), 3.60 (d, J = 6.9 Hz, 3H), 3.10 (s, 1H), 3.05 (s, 2H), 2.77 (s, 1H), 2.11 (s, 1H), 2.04 (t, J = 1.3 Hz, 3H), 1.76 (s, 1H). | 525.30 |

TABLE 2-continued

Additional Exemplary Compounds

| Compound | Structure | Proton NMR | MS [M + 1] |
|---|---|---|---|
| (R)-4-(4-amino-6-(4-methacrylamido-phenyl)-7-methyl-7H-pyrrolo[2,3-d]pyrimidin-5-yl)-N-methyl-N-((tetrahydrofuran-3-yl)methyl) benzamide | 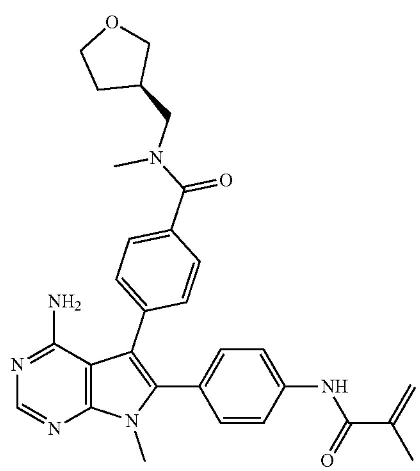 [SMILES: C=C(C)C(=O)Nc1ccc(-c2c(-c3ccc(C(=O)N(C)C[C@H]4CCOC4)cc3)c3c(N)ncnc3n2C)cc1] | $^1$H NMR (400 MHz, Methanol-d$_4$) δ 8.22 (s, 1H), 7.71-7.64 (m, 2H), 7.40 (s, 5H), 7.28 (d, J = 8.2 Hz, 2H), 5.81 (s, 1H), 5.54 (s, 1H), 3.96-3.87 (m, 1H), 3.80 (d, J = 7.6 Hz, 2H), 3.71 (s, 3H), 3.60 (d, J = 6.9 Hz, 3H), 3.10 (s, 1H), 3.05 (s, 2H), 2.77 (s, 1H), 2.11 (s, 1H), 2.04 (t, J = 1.3 Hz, 3H), 1.76 (s, 1H). | 525.30 |
| N-(4-(5-(4-(2-azabicyclo[3.1.0]hexane-2-carbonyl)phenyl)-4-amino-7-methyl-7H-pyrrolo[2,3-d]pyrimidin-6-yl)-3-fluorophenyl) methacrylamide | 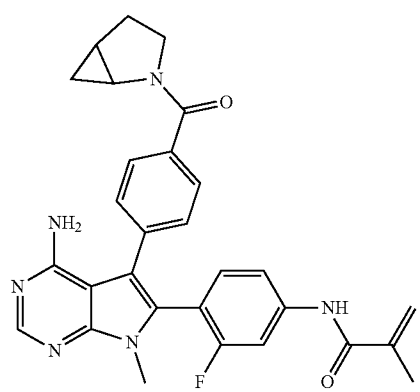 [SMILES: C=C(C)C(=O)Nc1ccc(-c2c(-c3ccc(C(=O)N4CCC5CC54)cc3)c3c(N)ncnc3n2C)c(F)c1] | $^1$H NMR (400 MHz, DMSO-d$_6$) δ 10.09 (s, 1H), 8.22 (s, 1H), 7.76 (dd, J = 12.5, 2.0 Hz, 1H), 7.59 (d, J = 7.8 Hz, 1H), 7.48 (dd, J = 8.4, 2.1 Hz, 2H), 7.28 (d, J = 8.6 Hz, 3H), 6.03 (s, 1H), 5.82 (d, J = 1.1 Hz, 1H), 5.58 (s, 1H), 3.95 (d, J = 10.7 Hz, 1H), 3.55 (s, 3H), 3.13 (s, 2H), 2.05 (s, 1H), 1.95 (d, J = 1.3 Hz, 4H), 1.69 (s, 4H), 1.59 (s, 1H), 0.76 (s, 2H). | 511.35 |
| N-(4-(5-(4-(3-azabicyclo[3.1.0]hexane-3-carbonyl)phenyl)-4-amino-7-methyl-7H-pyrrolo[2,3-d]pyrimidin-6-yl)-3-fluorophenyl) methacrylamide | 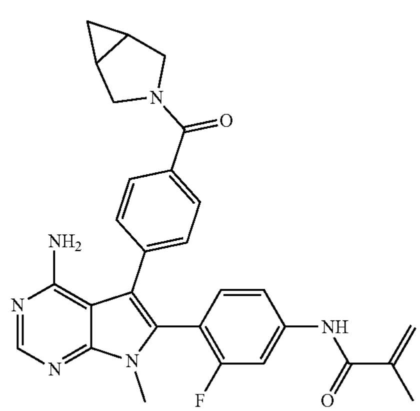 [SMILES: C=C(C)C(=O)Nc1ccc(-c2c(-c3ccc(C(=O)N4CC5CC5C4)cc3)c3c(N)ncnc3n2C)c(F)c1] | $^1$H NMR (400 MHz, DMSO-d$_6$) δ 10.10 (s, 1H), 8.22 (s, 1H), 7.77 (dd, J = 12.5, 2.0 Hz, 1H), 7.49 (dd, J = 8.5, 2.0 Hz, 1H), 7.41 (d, J = 8.1 Hz, 2H), 7.31-7.20 (m, 3H), 5.83 (s, 1H), 5.76 (s, 1H), 5.58 (d, J = 2.0 Hz, 1H), 3.95 (d, J = 11.9 Hz, 1H), 3.66 (d, J = 10.0 Hz, 1H), 3.55 (s, 3H), 3.3-3.2 (m, 2H), 1.95 (t, J = 1.2 Hz, 3H), 1.54 (s, 2H), 0.68-0.59 (m, 1H), 0.07 (q, J = 4.3 Hz, 1H). | 511.30 |

TABLE 2-continued

Additional Exemplary Compounds

| Compound | Structure | Proton NMR | MS [M + 1] |
|---|---|---|---|
| N-(4-(4-amino-5-(3-fluoro-4-((2-methylpyrimidin-4-yl)oxy)phenyl)-7-methyl-7H-pyrrolo[2,3-d]pyrimidin-6-yl)phenyl)methacrylamide | 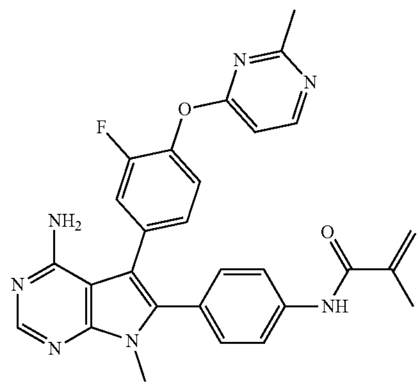 [SMILES: C=C(C)C(=O)Nc1ccc(-c2c(-c3ccc(Oc4ccnc(C)n4)c(F)c3)c3c(N)ncnc3n2C)cc1] | $^1$H NMR (400 MHz, DMSO-d$_6$) δ 9.92 (s, 1H), 8.60 (d, J = 5.8 Hz, 1H), 8.21 (s, 1H), 7.78-7.72 (m, 2H), 7.35 (t, J = 8.3 Hz, 1H), 7.33-7.28 (m, 2H), 7.21 (dd, J = 11.4, 2.1 Hz, 1H), 7.10 (d, J = 8.1 Hz, 1H), 7.03 (d, J = 5.7 Hz, 1H), 6.05 (s, 2H), 5.80 (s, 1H), 5.54 (s, 1H), 3.62 (s, 3H), 2.46 (s, 3H), 1.95 (s, 3H). | 510.20 |
| N-(4-(4-amino-5-(3-fluoro-4-((6-methylpyrazin-2-yl)oxy)phenyl)-7-methyl-7H-pyrrolo[2,3-d]pyrimidin-6-yl)phenyl)methacrylamide | 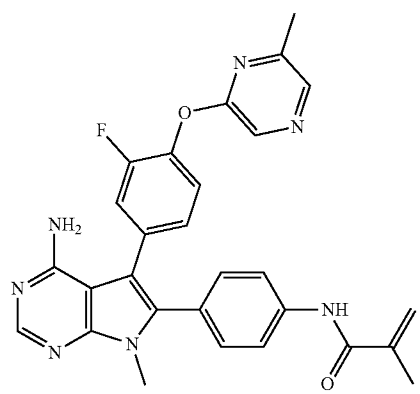 [SMILES: C=C(C)C(=O)Nc1ccc(-c2c(-c3ccc(Oc4cncc(C)n4)c(F)c3)c3c(N)ncnc3n2C)cc1] | $^1$H NMR (400 MHz, DMSO-d$_6$) δ 9.91 (s, 1H), 8.45-8.14 (m, 3H), 7.81-7.70 (m, 2H), 7.42-7.24 (m, 3H), 7.24-7.02 (m, 2H), 6.27-5.90 (m, 1H), 5.80 (t, J = 1.1 Hz, 1H), 5.54 (t, J = 1.5 Hz, 1H), 3.61 (s, 3H), 2.35 (s, 3H), 1.96 (t, J = 1.2 Hz, 3H). | 510.20 |
| N-(4-(4-amino-5-(4-((4-chloropyrimidin-2-yl)oxy)-3-fluorophenyl)-7-methyl-7H-pyrrolo[2,3-d]pyrimidin-6-yl)phenyl)methacrylamide | 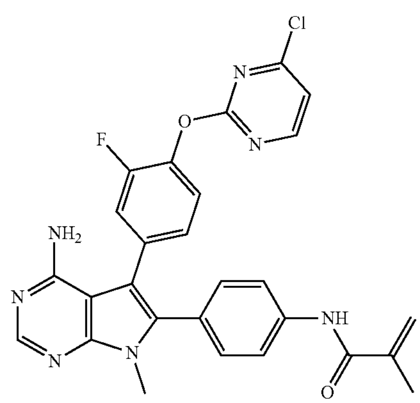 [SMILES: C=C(C)C(=O)Nc1ccc(-c2c(-c3ccc(Oc4nccc(Cl)n4)c(F)c3)c3c(N)ncnc3n2C)cc1] | $^1$H NMR (400 MHz, DMSO-d$_6$) δ 9.93 (s, 1H), 8.66 (d, J = 5.2 Hz, 1H), 8.22 (s, 1H), 7.76 (d, J = 8.5 Hz, 2H), 7.54 (d, J = 5.3 Hz, 1H), 7.42 (t, J = 8.4 Hz, 1H), 7.33 (d, J = 8.5 Hz, 2H), 7.23 (d, J = 13.3 Hz, 1H), 7.13 (d, J = 8.4 Hz, 1H), 6.21-5.90 (m, 1H), 5.5.81 (s, 1H), 5.55 (s, 1H), 3.60 (s, 3H), 1.96 (s, 3H). | 530.20 |

TABLE 2-continued

Additional Exemplary Compounds

| Compound | Structure | Proton NMR | MS [M + 1] |
|---|---|---|---|
| N-(4-(4-amino-5-(4-((4-(difluoromethyl)pyrimidin-2-yl)oxy)-3-fluorophenyl)-7-methyl-7H-pyrrolo[2,3-d]pyrimidin-6-yl)phenyl)methacrylamide | 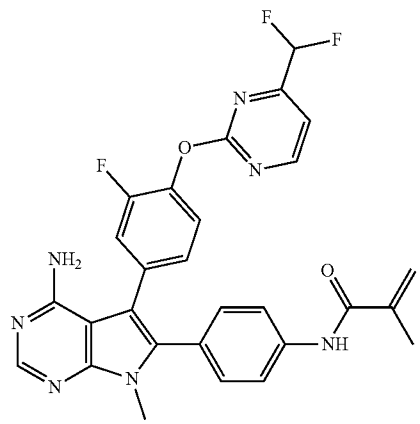 [SMILES: C=C(C)C(=O)Nc1ccc(-c2c(-c3ccc(Oc4nccc(C(F)F)n4)c(F)c3)c3c(N)ncnc3n2C)cc1] | $^1$H NMR (400 MHz, DMSO-d$_6$) δ 9.93 (s, 1H), 8.90 (d, J = 4.9 Hz, 1H), 8.22 (s, 1H), 7.80-7.72 (m, 2H), 7.59 (d, J = 5.0 Hz, 1H), 7.42 (t, J = 8.4 Hz, 1H), 7.37-7.29 (m, 2H), 7.23 (dd, J = 11.4, 2.0 Hz, 1H), 7.15-7.06 (m, 1H), 6.88 (d, J = 54.0 Hz, 1H), 5.99 (s, 1H), 5.81 (t, J = 1.1 Hz, 1H), 5.54 (t, J = 1.5 Hz, 1H), 3.60 (s, 3H), 1.96 (t, J = 1.2 Hz, 3H). | 546.40 |
| N-(4-(4-amino-5-(3-fluoro-4-((4-methoxypyrimidin-2-yl)oxy)phenyl)-7-methyl-7H-pyrrolo[2,3-d]pyrimidin-6-yl)phenyl)methacrylamide | 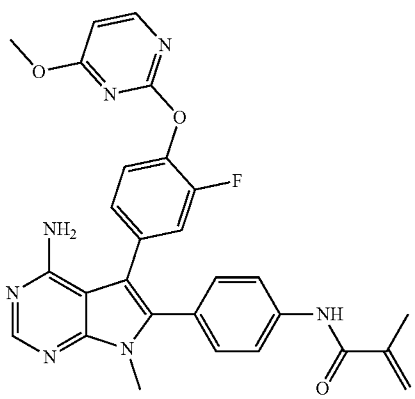 [SMILES: C=C(C)C(=O)Nc1ccc(-c2c(-c3ccc(Oc4nccc(OC)n4)c(F)c3)c3c(N)ncnc3n2C)cc1] | $^1$H NMR (400 MHz, DMSO-d$_6$) δ 9.92 (s, 1H), 8.34 (d, J = 5.7 Hz, 1H), 8.21 (s, 1H), 7.74 (d, J = 8.6 Hz, 2H), 7.45-7.24 (m, 3H), 7.20 (t, J = 11.4, 2.0 Hz, 1H), 7.11 (d, J = 8.2 Hz, 1H), 6.72 (d, J = 5.7 Hz, 1H), 5.81 (s, 1H), 5.55 (s, 1H), 3.81 (s, 3H), 3.60 (s, 3H), 1.96 (t, J = 1.2 Hz, 3H). | 526.25 |
| N-(4-(4-amino-5-(4-((4-cyanopyrimidin-2-yl)oxy)-3-fluorophenyl)-7-methyl-7H-pyrrolo[2,3-d]pyrimidin-6-yl)phenyl)methacrylamide | 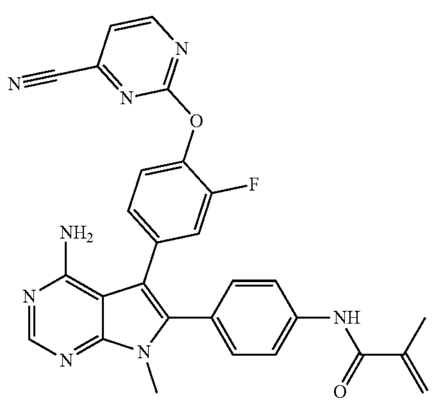 [SMILES: C=C(C)C(=O)Nc1ccc(-c2c(-c3ccc(Oc4nccc(C#N)n4)c(F)c3)c3c(N)ncnc3n2C)cc1] | $^1$H NMR (400 MHz, DMSO-d$_6$) δ 9.92 (s, 1H), 9.03 (d, J = 4.8 Hz, 1H), 8.22 (s, 1H), 7.97 (d, J = 4.8 Hz, 1H), 7.79-7.72 (m, 2H), 7.42 (t, J = 8.4 Hz, 1H), 7.33 (d, J = 8.6 Hz, 2H), 7.25 (dd, J = 11.4, 2.0 Hz, 1H), 7.14 (dd, J = 8.2, 1.8 Hz, 1H), 6.01 (s, 2H), 5.81 (s, 1H), 5.54 (s, 1H), 3.59 (s, 3H), 1.96 (t, J = 1.4 Hz, 3H). | 521.25 |

TABLE 2-continued

Additional Exemplary Compounds

| Compound | Structure | Proton NMR | MS [M + 1] |
|---|---|---|---|
| N-(4-(4-amino-5-(3-fluoro-4-((4-(hydroxymethyl)pyrimidin-2-yl)oxy)phenyl)-7-methyl-7H-pyrrolo[2,3-d]pyrimidin-6-yl)phenyl)methacrylamide | 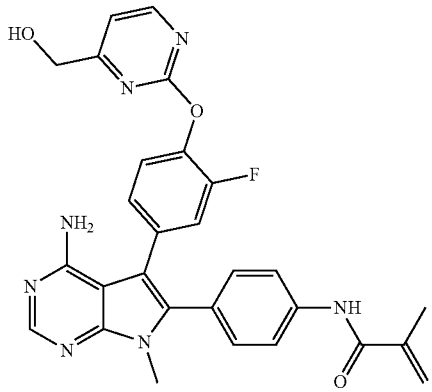 [SMILES: C=C(C)C(=O)Nc1ccc(-c2c(-c3ccc(Oc4nccc(CO)n4)c(F)c3)c3c(N)ncnc3n2C)cc1] | $^1$H NMR (400 MHz, DMSO-d$_6$) δ 9.93 (s, 1H), 8.61 (d, J = 5.0 Hz, 1H), 8.21 (s, 1H), 7.80-7.72 (m, 2H), 7.34 (dd, J = 8.3, 5.4 Hz, 4H), 7.19 (dd, J = 11.4, 2.0 Hz, 1H), 7.11 (dt, J = 8.3, 1.4 Hz, 1H), 5.84-5.79 (m, 1H), 5.67 (t, J = 6.0 Hz, 1H), 5.54 (t, J = 1.5 Hz, 1H), 4.50 (d, J = 5.9 Hz, 2H), 3.60 (s, 3H), 3.32 (s, 2H), 1.96 (t, J = 1.2 Hz, 3H). | 526.10 |
| N-(4-(4-amino-5-(3-fluoro-4-((4-(methoxymethyl)pyrimidin-2-yl)oxy)phenyl)-7-methyl-7H-pyrrolo[2,3-d]pyrimidin-6-yl)phenyl)methacrylamide | 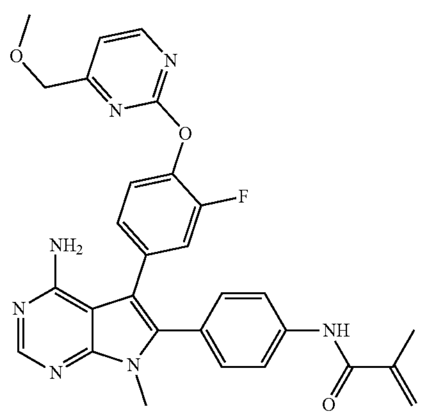 [SMILES: C=C(C)C(=O)Nc1ccc(-c2c(-c3ccc(Oc4nccc(COC)n4)c(F)c3)c3c(N)ncnc3n2C)cc1] | $^1$H NMR (400 MHz, DMSO-d$_6$) δ 9.93 (s, 1H), 8.63 (d, J = 5.0 Hz, 1H), 8.21 (s, 1H), 7.79-7.73 (m, 2H), 7.41-7.31 (m, 2H), 7.32 (d, J = 2.0 Hz, 1H), 7.28 (d, J = 5.0 Hz, 1H), 7.19 (dd, J = 11.4, 2.0 Hz, 1H), 7.11 (dd, J = 8.4, 2.1 Hz, 1H), 5.98 (s, 2H), 5.81 (s, 1H), 5.54 (s, 1H), 4.45 (s, 2H), 3.60 (s, 3H), 3.39 (s, 3H), 1.96 (s, 3H). | 540.20 |
| N-(4-(4-amino-5-(3-fluoro-4-((5-fluoro-4-methylpyrimidin-2-yl)oxy)phenyl)-7-methyl-7H-pyrrolo[2,3-d]pyrimidin-6-yl)phenyl)methacrylamide | 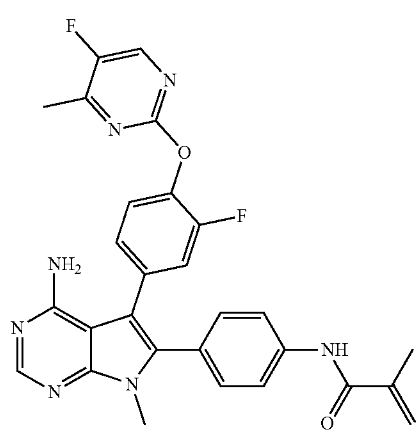 [SMILES: C=C(C)C(=O)Nc1ccc(-c2c(-c3ccc(Oc4ncc(F)c(C)n4)c(F)c3)c3c(N)ncnc3n2C)cc1] | $^1$H NMR (400 MHz, DMSO-d$_6$) δ 9.92 (s, 1H), 8.57 (d, J = 1.4 Hz, 1H), 8.21 (s, 1H), 7.80-7.71 (m, 2H), 7.41-7.30 (m, 3H), 7.20 (dd, J = 11.5, 2.0 Hz, 1H), 7.14-7.08 (m, 1H), 5.98 (s, 1H), 5.81 (t, J = 1.1 Hz, 1H), 5.54 (t, J = 1.5 Hz, 1H), 3.60 (s, 3H), 2.43 (d, J = 2.5 Hz, 3H), 1.96 (t, J = 1.2 Hz, 3H). | 528.40 |

TABLE 2-continued

Additional Exemplary Compounds

| Compound | Structure | Proton NMR | MS [M + 1] |
|---|---|---|---|
| N-(4-(4-amino-5-(3-chloro-4-((4-methylpyrimidin-2-yl)oxy)phenyl)-7-methyl-7H-pyrrolo[2,3-d]pyrimidin-6-yl)phenyl)methacrylamide | 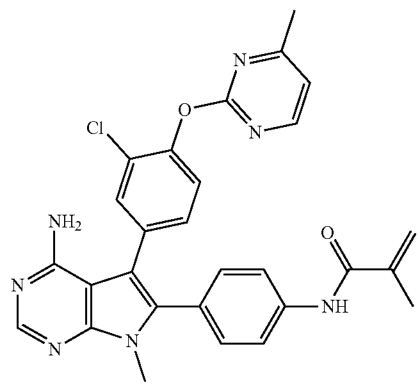 [SMILES: C=C(C)C(=O)Nc1ccc(-c2c(-c3ccc(Oc4nccc(C)n4)c(Cl)c3)c3c(N)ncnc3n2C)cc1] | $^1$H NMR (400 MHz, DMSO-d$_6$) δ 9.93 (s, 1H), 8.47 (d, J = 5.0 Hz, 1H), 8.22 (s, 1H), 7.77 (d, J = 8.5 Hz, 2H), 7.41 (d, J = 2.1 Hz, 1H), 7.34 (d, J = 8.4 Hz, 3H), 7.30-7.20 (m, 1H), 7.18 (d, J = 5.0 Hz, 1H), 5.97 (s, 1H), 5.81 (s, 1H), 5.54 (s, 1H), 3.60 (s, 3H), 2.43 (s, 3H), 1.96 (d, J = 1.2 Hz, 3H). | 526.15 |
| N-(4-(4-amino-7-methyl-5-(3-methyl-4-((4-methylpyrimidin-2-yl)oxy)phenyl)-7H-pyrrolo[2,3-d]pyrimidin-6-yl)phenyl)methacrylamide | 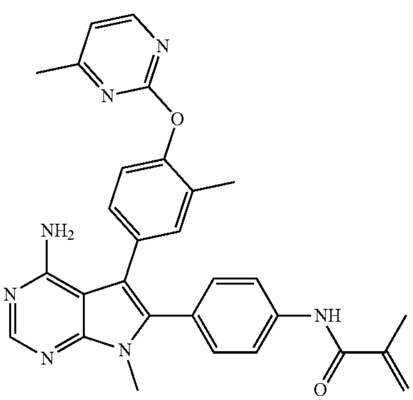 [SMILES: C=C(C)C(=O)Nc1ccc(-c2c(-c3ccc(Oc4nccc(C)n4)c(C)c3)c3c(N)ncnc3n2C)cc1] | $^1$H NMR (400 MHz, DMSO-d$_6$) δ 9.90 (s, 1H), 8.44 (d, J = 5.0 Hz, 1H), 8.20 (s, 1H), 7.74 (d, J = 8.7 Hz, 2H), 7.33 (d, J = 8.7 Hz, 2H), 7.24 (d, J = 2.0 Hz, 1H), 7.14-7.05 (m, 3H), 5.80 (d, J = 1.3 Hz, 2H), 5.54 (s, 1H), 3.60 (s, 3H), 2.41 (s, 3H), 2.04 (s, 3H), 1.95 (d, J = 1.3 Hz, 3H). | 506.25 |
| N-(4-(4-amino-5-(3-(methoxymethyl)-4-((4-methylpyrimidin-2-yl)oxy)phenyl)-7-methyl-7H-pyrrolo[2,3-d]pyrimidin-6-yl)phenyl)methacrylamide | 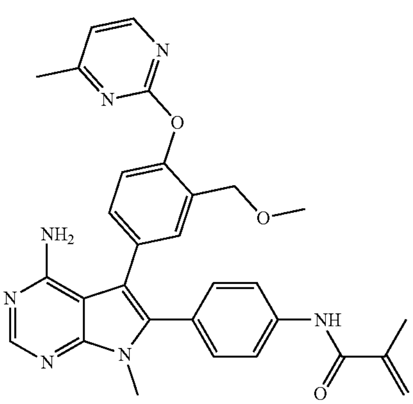 [SMILES: C=C(C)C(=O)Nc1ccc(-c2c(-c3ccc(Oc4nccc(C)n4)c(COC)c3)c3c(N)ncnc3n2C)cc1] | $^1$H NMR (400 MHz, DMSO-d$_6$) δ 9.90 (s, 1H), 8.44 (d, J = 5.0 Hz, 1H), 8.21 (s, 1H), 7.73 (d, J = 8.3 Hz, 2H), 7.39-7.26 (m, 3H), 7.23-7.21 (m, 1H), 7.17-7.09 (m, 2H), 5.79 (s, 2H), 5.53 (s, 1H), 4.29 (s, 2H), 3.61 (s, 3H), 3.08 (s, 3H), 2.41 (s, 3H), 1.95 (s, 3H). | 536.40 |

TABLE 2-continued

Additional Exemplary Compounds

| Compound | Structure | Proton NMR | MS [M + 1] |
|---|---|---|---|
| N-(4-(4-amino-5-(3-cyano-4-((4-methylpyrimidin-2-yl)oxy)phenyl)-7-methyl-7H-pyrrolo[2,3-d]pyrimidin-6-yl)phenyl)methacrylamide | 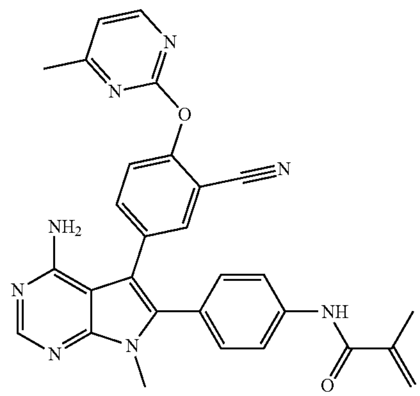 [SMILES: C=C(C)C(=O)Nc1ccc(-c2c(-c3ccc(Oc4nccc(C)n4)c(C#N)c3)c3c(N)ncnc3n2C)cc1] | $^1$H NMR (400 MHz, DMSO-d$_6$) δ 9.95 (s, 1H), 8.52 (d, J = 5.0 Hz, 1H), 8.24 (s, 1H), 7.82-7.69 (m, 3H), 7.53 (t, J = 8.6, 2.2 Hz, 1H), 7.41 (d, J = 8.6 Hz, 1H), 7.33 (d, J = 8.6 Hz, 2H), 7.25 (d, J = 5.1 Hz, 1H), 5.81 (s, 1H), 5.55 (s, 1H), 3.60 (s, 3H), 2.45 (s, 3H), 1.96 (t, J = 1.3 Hz, 3H). | 517.25 |
| N-(4-(4-amino-5-(3-(dimethylamino)-4-((4-methylpyrimidin-2-yl)oxy)phenyl)-7-methyl-7H-pyrrolo[2,3-d]pyrimidin-6-yl)phenyl)methacrylamide | 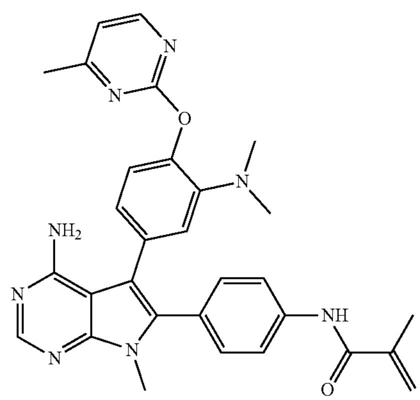 [SMILES: C=C(C)C(=O)Nc1ccc(-c2c(-c3ccc(Oc4nccc(C)n4)c(N(C)C)c3)c3c(N)ncnc3n2C)cc1] | $^1$H NMR (400 MHz, DMSO-d$_6$) δ 9.91 (s, 1H), 8.43 (d, J = 5.0 Hz, 1H), 8.20 (s, 1H), 7.84-7.58 (m, 2H), 7.43-7.27 (m, 2H), 7.10 (d, J = 5.0 Hz, 1H), 7.05-6.97 (m, 1H), 6.83 (d, J = 6.7 Hz, 2H), 5.81 (s, 1H), 5.54 (s, 1H), 3.60 (s, 3H), 2.55 (s, 6H), 2.40 (s, 3H), 1.96 (s, 3H). | 535.45 |
| N-(4-(4-amino-5-(3-ethoxy-4-((4-methylpyrimidin-2-yl)oxy)phenyl)-7-methyl-7H-pyrrolo[2,3-d]pyrimidin-6-yl)phenyl)methacrylamide | 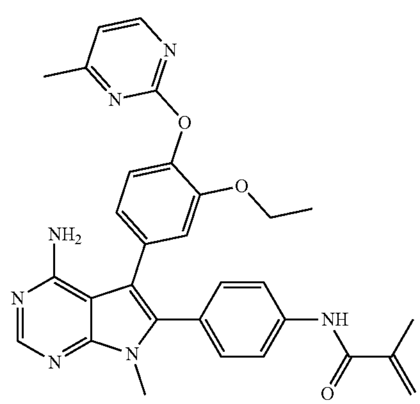 | $^1$H NMR (400 MHz, DMSO-d$_6$) δ 9.90 (s, 1H), 8.42 (d, J = 5.0 Hz, 1H), 8.21 (s, 1H), 7.74 (d, J = 8.6 Hz, 2H), 7.34 (d, J = 8.6 Hz, 2H), 7.18-7.05 (m, 2H), 6.94 (d, J = 2.0 Hz, 1H), 6.84 (dd, J = 8.1, 1.9 Hz, 1H), 5.80 (s, 1H), 5.54 (s, 1H), 3.81 (d, J = 7.0 Hz, 2H), 3.61 (s, 3H), 2.44-2.31 (m, 3H), 1.96 (t, J = 1.3 Hz, 3H), 0.94 (t, J = 6.9 Hz, 3H). | 536.45 |

TABLE 2-continued

Additional Exemplary Compounds

| Compound | Structure | Proton NMR | MS [M + 1] |
|---|---|---|---|
| N-(4-(4-amino-5-(3-methoxy-5-methyl-4-((4-methylpyrimidin-2-yl)oxy)phenyl)-7-methyl-7H-pyrrolo[2,3-d]pyrimidin-6-yl)phenyl) methacrylamide | 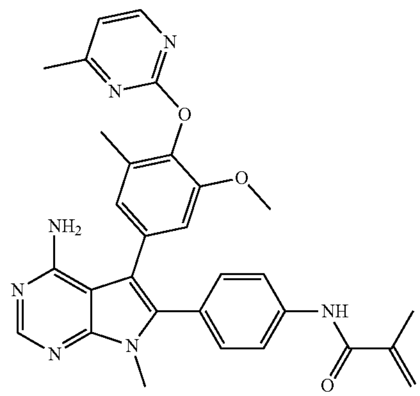 [SMILES: C=C(C)C(=O)Nc1ccc(-c2c(-c3cc(C)c(Oc4nccc(C)n4)c(OC)c3)c3c(N)ncnc3n2C)cc1] | $^1$H NMR (400 MHz, DMSO-d$_6$) δ 9.91 (s, 1H), 8.39 (d, J = 5.0 Hz, 1H), 8.20 (s, 1H), 7.87-7.69 (m, 2H), 7.43-7.30 (m, 2H), 7.09 (d, J = 5.0 Hz, 1H), 6.84-6.77 (m, 2H), 5.81 (s, 2H), 5.54 (d, J = 1.5 Hz, 1H), 3.60 (s, 3H), 3.50 (s, 3H), 2.41 (s, 3H), 2.03 (s, 3H), 1.96 (s, 3H). | 536.45 |
| N-(4-(4-amino-5-(3-fluoro-4-((4-methylpyrimidin-2-yl)oxy)phenyl)-7-methyl-7H-pyrrolo[2,3-d]pyrimidin-6-yl)-3-fluorophenyl) methacrylamide | 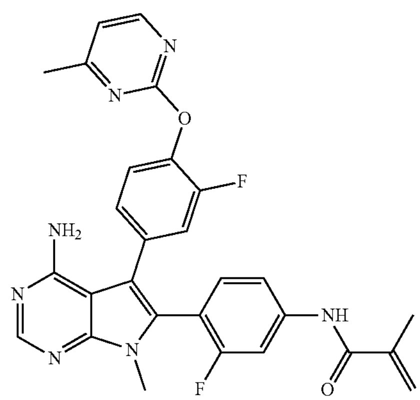 | $^1$H NMR (400 MHz, DMSO-d$_6$) δ 10.14 (s, 1H), 8.47 (d, J = 5.0 Hz, 1H), 8.23 (s, 1H), 7.80 (dd, J = 12.5, 2.0 Hz, 1H), 7.55 (dd, J = 8.5, 2.0 Hz, 1H), 7.35 (td, J = 8.4, 2.4 Hz, 2H), 7.22-7.16 (m, 2H), 7.13-7.08 (m, 1H), 6.07 (s, 2H), 5.83 (s, 1H), 5.59 (s, 1H), 3.54 (s, 3H), 2.42 (s, 3H), 1.96 (t, J = 1.2 Hz, 3H). | 528.35 |
| N-(4-(4-amino-7-methyl-5-(3-methyl-4-((4-methylpyrimidin-2-yl)oxy)phenyl)-7H-pyrrolo[2,3-d]pyrimidin-6-yl)-3-fluorophenyl) methacrylamide | 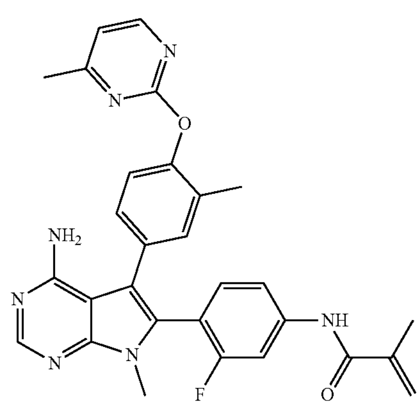 [SMILES: C=C(C)C(=O)Nc1ccc(-c2c(-c3ccc(Oc4nccc(C)n4)c(C)c3)c3c(N)ncnc3n2C)c(F)c1] | $^1$H NMR (400 MHz, DMSO-d$_6$) δ 10.13 (s, 1H), 8.44 (d, J = 5.0 Hz, 1H), 8.22 (s, 1H), 7.80 (dd, J = 12.4, 1.9 Hz, 1H), 7.53 (dd, J = 8.5, 2.0 Hz, 1H), 7.35 (t, J = 8.4 Hz, 1H), 7.23 (s, 1H), 7.14 (d, J = 4.0 Hz, 1H), 7.16-7.09 (m, 2H), 5.97 (s, 1H), 5.84 (s, 1H), 5.59 (s, 1H), 3.54 (s, 3H), 2.42 (s, 3H), 2.04 (s, 3H), 1.96 (d, J = 1.5 Hz, 3H). | 524.35 |

TABLE 2-continued

Additional Exemplary Compounds

| Compound | Structure | Proton NMR | MS [M + 1] |
|---|---|---|---|
| N-(4-(4-amino-5-(3-fluoro-4-((4-methylpyrimidin-2-yl)oxy)phenyl)-7-methyl-7H-pyrrolo[2,3-d]pyrimidin-6-yl)-3-(hydroxymethyl)phenyl)methacrylamide | | $^1$H NMR (400 MHz, DMSO-d$_6$) δ 9.94 (s, 1H), 8.46 (d, J = 5.0 Hz, 1H), 8.22 (s, 1H), 7.91 (d, J = 2.2 Hz, 1H), 7.74 (dd, J = 8.3, 2.3 Hz, 1H), 7.36-7.27 (m, 2H), 7.20-7.11 (m, 2H), 7.08 (dd, J = 8.4, 2.0 Hz, 1H), 6.05 (s, 1H), 5.83 (s, 1H), 5.54 (s, 1H), 5.17 (t, J = 5.3 Hz, 1H), 4.17 (dd, J = 13.9, 5.3 Hz, 1H), 4.02 (dd, J = 13.8, 5.3 Hz, 1H), 2.41 (s, 3H), 1.96 (d, J = 1.6 Hz, 3H). | 540.40 |
| N-(4-(4-amino-5-(3-fluoro-4-((4-methylpyrimidin-2-yl)oxy)phenyl)-7-methyl-7H-pyrrolo[2,3-d]pyrimidin-6-yl)-3-(hydroxymethyl)phenyl)methacrylamide | Atropisomer A | $^1$H NMR (400 MHz, Chloroform-d) δ 8.41-8.32 (m, 2H), 7.82 (dd, J = 8.3, 2.2 Hz, 1H), 7.71-7.64 (m, 2H), 7.33 (d, J = 8.3 Hz, 1H), 7.22 (t, J = 8.2 Hz, 1H), 7.06 (t, J = 8.2 Hz, 2H), 6.95 (d, J = 5.1 Hz, 1H), 5.85 (s, 1H), 5.60 (s, 1H), 5.54 (d, J = 1.7 Hz, 1H), 4.36 (d, J = 13.2 Hz, 1H), 4.25 (d, J = 13.2 Hz, 1H), 3.59 (s, 3H), 2.51 (s, 3H), 2.13-2.08 (m, 3H). | 540.40 |
| N-(4-(4-amino-5-(3-fluoro-4-((4-methylpyrimidin-2-yl)oxy)phenyl)-7-methyl-7H-pyrrolo[2,3-d]pyrimidin-6-yl)-3-(hydroxymethyl)phenyl)methacrylamide | Atropisomer B | $^1$H NMR (400 MHz, Chloroform-d) δ 8.39 (s, 1H), 8.34 (d, J = 5.0 Hz, 1H), 7.82 (dd, J = 8.3, 2.1 Hz, 1H), 7.71-7.64 (m, 2H), 7.33 (d, J = 8.3 Hz, 1H), 7.21 (t, J = 8.2 Hz, 1H), 7.06 (t, J = 8.0 Hz, 2H), 6.94 (d, J = 5.0 Hz, 1H), 5.85 (s, 1H), 5.53 (d, J = 1.6 Hz, 2H), 4.36 (d, J = 13.3 Hz, 1H), 4.25 (d, J = 13.3 Hz, 1H), 3.59 (s, 3H), 2.51 (s, 3H), 2.10 (t, J = 1.2 Hz, 3H). | 540.45 |

TABLE 2-continued

Additional Exemplary Compounds

| Compound | Structure | Proton NMR | MS [M + 1] |
|---|---|---|---|
| N-(4-(4-amino-5-(3-fluoro-4-((4-methylpyrimidin-2-yl)oxy)phenyl)-7-methyl-7H-pyrrolo[2,3-d]pyrimidin-6-yl)-3-(methoxymethyl)phenyl)methacrylamide | | ¹H NMR (400 MHz, DMSO-d₆) δ 9.95 (s, 1H), 8.45 (d, J = 5.0 Hz, 1H), 8.22 (s, 1H), 7.86-7.76 (m, 2H), 7.38 (d, J = 8.3 Hz, 1H), 7.31 (t, J = 8.4 Hz, 1H), 7.20-7.10 (m, 2H), 7.07 (dd, J = 8.3, 2.2 Hz, 1H), 6.06 (s, 1H), 5.84 (t, J = 1.1 Hz, 1H), 5.54 (t, J = 1.5 Hz, 1H), 4.12 (d, J = 12.7 Hz, 1H), 3.91 (d, J = 12.7 Hz, 1H), 3.42 (s, 3H), 3.10 (s, 3H), 2.40 (s, 3H), 1.96 (t, J = 1.2 Hz, 3H). | 554.25 |
| N-(4-(4-amino-5-(3-fluoro-4-((4-methylpyrimidin-2-yl)oxy)phenyl)-7-methyl-7H-pyrrolo[2,3-d]pyrimidin-6-yl)-3-(methoxymethyl)phenyl)methacrylamide | Atropisomer A | ¹H NMR (400 MHz, Chloroform-d) δ 8.41 (s, 1H), 8.35 (d, J = 5.0 Hz, 1H), 7.89-7.82 (m, 1H), 7.64-7.56 (m, 2H), 7.32 (d, J = 8.3 Hz, 1H), 7.22 (t, J = 8.2 Hz, 1H), 7.06 (d, J = 10.7 Hz, 2H), 6.94 (d, J = 5.0 Hz, 1H), 5.84 (s, 1H), 5.53 (s, 1H), 5.37 (s, 1H), 4.14 (d, J = 12.4 Hz, 1H), 3.99 (d, J = 12.3 Hz, 1H), 3.57 (s, 3H), 3.21 (s, 3H), 2.50 (s, 3H), 2.10 (t, J = 1.2 Hz, 3H). | 554.45 |
| N-(4-(4-amino-5-(3-fluoro-4-((4-methylpyrimidin-2-yl)oxy)phenyl)-7-methyl-7H-pyrrolo[2,3-d]pyrimidin-6-yl)-3-(methoxymethyl)phenyl)methacrylamide | 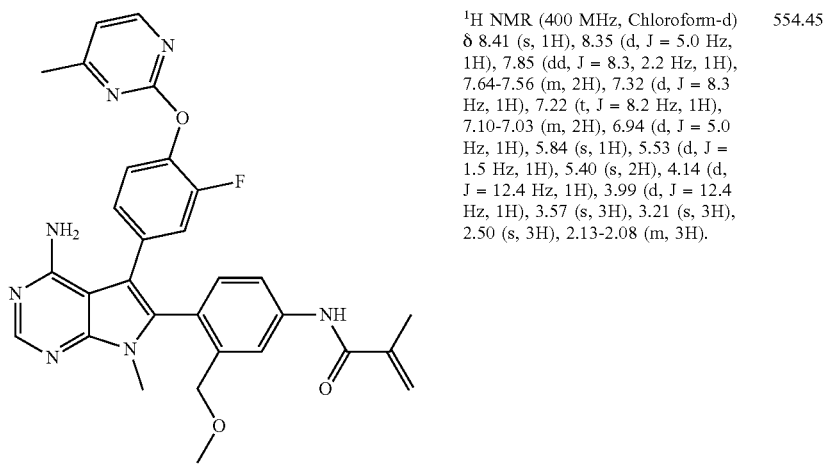  Atropisomer B | ¹H NMR (400 MHz, Chloroform-d) δ 8.41 (s, 1H), 8.35 (d, J = 5.0 Hz, 1H), 7.85 (dd, J = 8.3, 2.2 Hz, 1H), 7.64-7.56 (m, 2H), 7.32 (d, J = 8.3 Hz, 1H), 7.22 (t, J = 8.2 Hz, 1H), 7.10-7.03 (m, 2H), 6.94 (d, J = 5.0 Hz, 1H), 5.84 (s, 1H), 5.53 (d, J = 1.5 Hz, 1H), 5.40 (s, 2H), 4.14 (d, J = 12.4 Hz, 1H), 3.99 (d, J = 12.4 Hz, 1H), 3.57 (s, 3H), 3.21 (s, 3H), 2.50 (s, 3H), 2.13-2.08 (m, 3H). | 554.45 |

TABLE 2-continued

Additional Exemplary Compounds

| Compound | Structure | Proton NMR | MS [M + 1] |
|---|---|---|---|
| N-(4-(4-amino-5-(3-fluoro-4-(4-methylpyrimidin-2-yloxy)phenyl)-7-methyl-7H-pyrrolo[2,3-d]pyrimidin-6-yl)-3-ethylphenyl)methacrylamide | 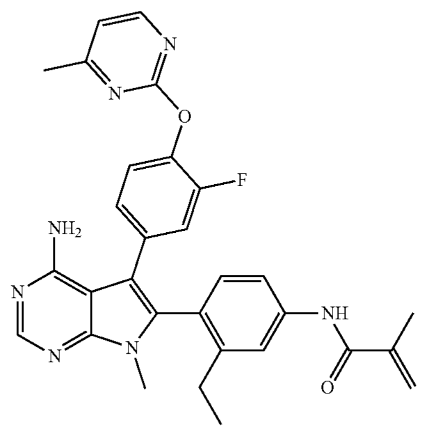 | $^1$H NMR (400 MHz, DMSO-$d_6$) δ 9.89 (s, 1H), 8.47 (d, J = 5.1 Hz, 1H), 8.23 (s, 1H), 7.70 (d, J = 6.2 Hz, 2H), 7.39-7.28 (m, 2H), 7.18 (d, J = 5.1 Hz, 1H), 7.13 (d, J = 11.3 Hz, 1H), 7.07 (d, J = 8.7 Hz, 1H), 5.82 (s, 1H), 5.54 (s, 1H), 2.40 (s, 3H), 2.17 (dd, J = 14.9, 7.2 Hz, 1H), 1.97 (s, 3H), 0.90 (t, J = 7.6 Hz, 3H). | 538.25 |
| 2-(4-amino-5-(3-fluoro-4-(4-methylpyrimidin-2-yloxy)phenyl)-7-methyl-7H-pyrrolo[2,3-d]pyrimidin-6-yl)-5-methacrylamido-N,N-dimethylbenzamide | 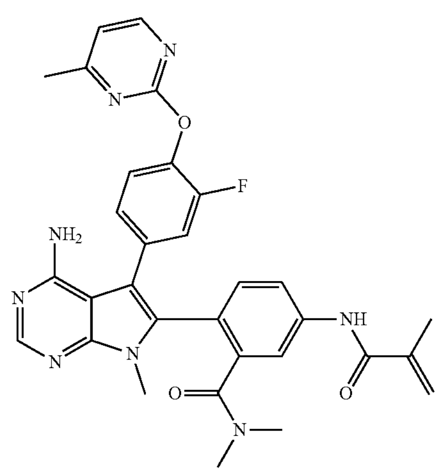 [SMILES: C=C(C)C(=O)Nc1ccc(-c2c(-c3ccc(Oc4nccc(C)n4)c(F)c3)c3c(N)ncnc3n2C)c(C(=O)N(C)C)c1] | $^1$H NMR (400 MHz, DMSO-$d_6$) δ 10.04 (s, 1H), 8.45 (d, J = 5.0 Hz, 1H), 8.20 (s, 1H), 7.85 (dd, J = 8.5, 2.3 Hz, 1H), 7.72 (d, J = 2.1 Hz, 1H), 7.64 (d, J = 8.3 Hz, 1H), 7.34 (t, J = 8.4 Hz, 1H), 7.17 (d, J = 5.1 Hz, 1H), 7.12-7.05 (m, 1H), 7.03 (d, J = 8.6 Hz, 1H), 5.85 (d, J = 1.2 Hz, 1H), 5.57 (d, J = 1.8 Hz, 1H), 3.45 (s, 3H), 2.71 (s, 3H), 2.37 (s, 3H), 2.30 (s, 3H), 1.96 (t, J = 1.2 Hz, 3H). | 581.3 |
| N-(4-(4-amino-5-(3-(difluoromethyl)-4-(4-methylpyrimidin-2-yloxy)phenyl)-7-methyl-7H-pyrrolo[2,3-d]pyrimidin-6-yl)phenyl)methacrylamide | 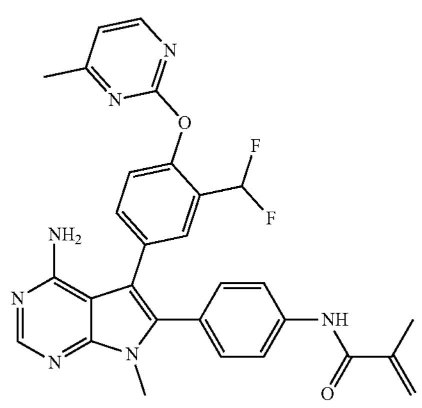 [SMILES: C=C(C)C(=O)Nc1ccc(-c2c(-c3ccc(Oc4nccc(C)n4)c(C(F)F)c3)c3c(N)ncnc3n2C)cc1] | $^1$H NMR (400 MHz, Methanol-$d_4$) δ 8.43 (d, J = 5.1 Hz, 1H), 8.23 (s, 1H), 7.71 (d, J = 8.3 Hz, 2H), 7.58 (s, 1H), 7.48 (d, J = 8.6 Hz, 1H), 7.33 (d, J = 8.3 Hz, 2H), 7.25 (d, J = 8.4 Hz, 1H), 7.18 (d, J = 5.1 Hz, 1H), 7.00-6.71 (m, 1H), 5.83 (s, 1H), 5.55 (s, 1H), 3.72 (s, 3H), 2.51 (s, 3H), 2.05 (s, 3H). | 542.2 |

TABLE 2-continued

Additional Exemplary Compounds

| Compound | Structure | Proton NMR | MS [M + 1] |
|---|---|---|---|
| N-(4-(4-amino-5-(3-fluoro-4-((4-methylpyrimidin-2-yl)oxy)phenyl)-7-methyl-7H-pyrrolo[2,3-d]pyrimidin-6-yl)-3-(difluoromethyl)phenyl) methacrylamide | | ¹H NMR (400 MHz, DMSO-d₆) δ 10.14 (s, 1H), 8.46 (d, J = 5.0 Hz, 1H), 8.24 (s, 1H), 8.13 (d, J = 1.9 Hz, 1H), 7.99 (d, J = 8.4 Hz, 1H), 7.55 (d, J = 8.4 Hz, 1H), 7.32 (t, J = 8.4 Hz, 1H), 7.22-7.14 (m, 2H), 7.07 (dd, J = 8.3, 2.1 Hz, 1H), 6.58 (s, 1H), 6.06 (s, 1H), 5.86 (s, 1H), 5.58 (d, J = 1.8 Hz, 1H), 3.42 (s, 3H), 2.40 (s, 3H), 1.97 (d, J = 1.2 Hz, 3H). | 560.40 |
| N-(4-(4-amino-5-(3-fluoro-4-((4-methylpyrimidin-2-yl)oxy)phenyl)-7-methyl-7H-pyrrolo[2,3-d]pyrimidin-6-yl)-3-(difluoromethyl)phenyl) methacrylamide | Atropisomer A | ¹H NMR (400 MHz, Chloroform-d) δ 8.43 (s, 1H), 8.36 (d, J = 5.0 Hz, 1H), 8.03 (d, J = 8.4 Hz, 1H), 7.80 (s, 1H), 7.71 (s, 1H), 7.39 (d, J = 8.3 Hz, 1H), 7.23 (t, J = 8.2 Hz, 1H), 7.09-7.00 (m, 2H), 6.94 (d, J = 5.0 Hz, 1H), 6.31 (s, 1H), 5.87 (s, 1H), 5.56 (d, J = 1.5 Hz, 1H), 5.29 (s, 2H), 3.57 (s, 3H), 2.50 (s, 3H), 2.11 (dd, J = 1.6, 0.9 Hz, 3H). | 560.35 |
| N-(4-(4-amino-5-(3-fluoro-4-((4-methylpyrimidin-2-yl)oxy)phenyl)-7-methyl-7H-pyrrolo[2,3-d]pyrimidin-6-yl)-3-(difluoromethyl)phenyl) methacrylamide | Atropisomer B | ¹H NMR (400 MHz, Chloroform-d) δ 8.42 (s, 1H), 8.36 (d, J = 5.0 Hz, 1H), 8.03 (d, J = 8.4 Hz, 1H), 7.80 (d, J = 2.2 Hz, 1H), 7.72 (s, 1H), 7.39 (d, J = 8.4 Hz, 1H), 7.23 (t, J = 8.3 Hz, 1H), 7.09-7.00 (m, 2H), 6.94 (d, J = 5.0 Hz, 1H), 6.31 (s, 1H), 5.87 (s, 1H), 5.56 (q, J = 1.6 Hz, 1H), 5.40 (s, 2H), 3.58 (s, 3H), 2.50 (s, 3H), 2.11 (d, J = 1.3 Hz, 3H). | 560.40 |

TABLE 2-continued

Additional Exemplary Compounds

| Compound | Structure | Proton NMR | MS [M + 1] |
|---|---|---|---|
| N-(4-(4-amino-5-(3-fluoro-4-((4-methylpyrimidin-2-yl)oxy)phenyl)-7-methyl-7H-pyrrolo[2,3-d]pyrimidin-6-yl)-3-((dimethylamino)methyl)phenyl)methacrylamide | 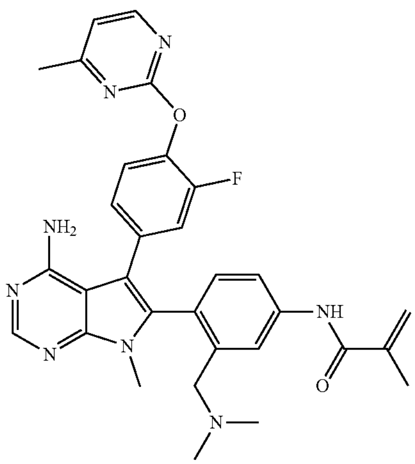 [SMILES: C=C(C)C(=O)Nc1ccc(-c2c(-c3ccc(Oc4nccc(C)n4)c(F)c3)c3c(N)ncnc3n2C)c(CN(C)C)c1] | $^1$H NMR (400 MHz, DMSO-$d_6$) δ 9.93 (s, 1H), 8.45 (d, J = 5.0 Hz, 1H), 8.21 (d, J = 7.9 Hz, 1H), 7.86 (s, 1H), 7.79 (d, J = 8.3 Hz, 1H), 7.37 (d, J = 8.3 Hz, 1H), 7.30 (t, J = 8.4 Hz, 1H), 7.16 (d, J = 5.0 Hz, 1H), 7.11 (d, J = 11.5 Hz, 1H), 7.06 (d, J = 8.3 Hz, 1H), 6.07 (s, 2H), 5.84 (s, 1H), 5.53 (s, 1H), 3.4 (d, J = 14.1 Hz, 3H), 3.15 (d, J = 14.1 Hz, 1H), 2.79 (d, J = 14.0 Hz, 1H), 2.39 (s, 3H), 1.95 (d, J = 5.1 Hz, 9H). | 567.30 |
| N-(4-(4-amino-5-(3-fluoro-4-((4-methylpyrimidin-2-yl)oxy)phenyl)-7-methyl-7H-pyrrolo[2,3-d]pyrimidin-6-yl)-3-methoxyphenyl)methacrylamide | 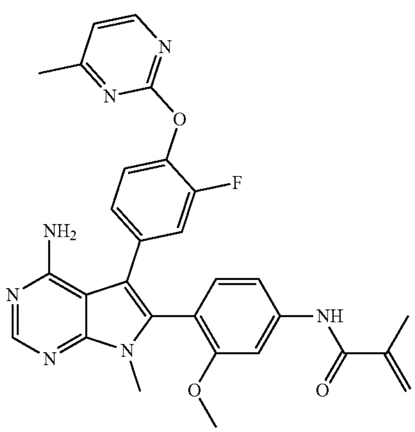 [SMILES: C=C(C)C(=O)Nc1ccc(-c2c(-c3ccc(Oc4nccc(C)n4)c(F)c3)c3c(N)ncnc3n2C)c(OC)c1] | $^1$H NMR (400 MHz, DMSO-$d_6$) δ 9.93 (s, 1H), 8.47 (d, J = 5.1 Hz, 1H), 8.20 (s, 1H), 7.63 (d, J = 1.9 Hz, 1H), 7.38-7.27 (m, 2H), 7.18 (d, J = 5.0 Hz, 1H), 7.15-7.08 (m, 2H), 7.08-7.01 (m, 1H), 6.00 (s, 2H), 5.82 (s, 1H), 5.55 (s, 1H), 3.71 (s, 3H), 3.47 (s, 3H), 2.41 (s, 3H), 1.96 (t, J = 1.2 Hz, 3H). | 540.25 |
| N-(4-(4-amino-5-(3-fluoro-4-((4-methylpyrimidin-2-yl)oxy)phenyl)-7-methyl-7H-pyrrolo[2,3-d]pyrimidin-6-yl)-3-methylphenyl)methacrylamide | 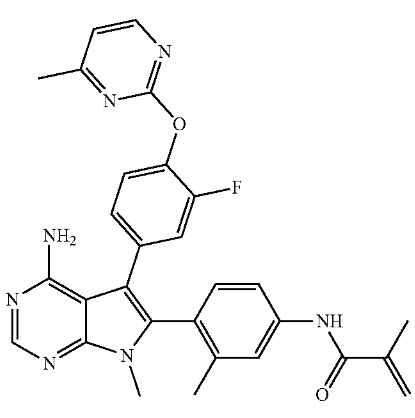 [SMILES: C=C(C)C(=O)Nc1ccc(-c2c(-c3ccc(Oc4nccc(C)n4)c(F)c3)c3c(N)ncnc3n2C)c(C)c1] | $^1$H NMR (400 MHz, DMSO-$d_6$) δ 9.86 (s, 1H), 8.47 (d, J = 5.0 Hz, 1H), 8.22 (s, 1H), 7.69-7.59 (m, 2H), 7.36-7.27 (m, 2H), 7.18 (d, J = 5.1 Hz, 1H), 7.12 (dd, J = 11.5, 2.1 Hz, 1H), 7.06 (dd, J = 8.4, 2.1 Hz, 1H), 6.04 (s, 2H), 5.81 (s, 1H), 5.54 (s, 1H), 3.43 (s, 3H), 2.41 (s, 3H), 1.96 (d, J = 1.4 Hz, 6H). | 524.25 |

TABLE 2-continued

Additional Exemplary Compounds

| Compound | Structure | Proton NMR | MS [M + 1] |
|---|---|---|---|
| N-(4-(4-amino-5-(3-fluoro-4-((4-methylpyrimidin-2-yl)oxy)phenyl)-7-methyl-7H-pyrrolo[2,3-d]pyrimidin-6-yl)-3-methylphenyl)methacrylamide | Atropisomer A | ¹H NMR (400 MHz, DMSO-d₆) δ 9.85 (s, 1H), 8.47 (d, J = 5.0 Hz, 1H), 8.22 (s, 1H), 7.69-7.60 (m, 2H), 7.32 (t, J = 7.7 Hz, 2H), 7.18 (d, J = 5.0 Hz, 1H), 7.15-7.09 (m, 1H), 7.06 (d, J = 8.6 Hz, 1H), 5.81 (s, 2H), 5.53 (s, 1H), 3.43 (s, 3H), 2.41 (s, 3H), 1.96 (s, 6H). | 524.25 |
| N-(4-(4-amino-5-(3-fluoro-4-((4-methylpyrimidin-2-yl)oxy)phenyl)-7-methyl-7H-pyrrolo[2,3-d]pyrimidin-6-yl)-3-methylphenyl)methacrylamide | Atropisomer B | ¹H NMR (400 MHz, DMSO-d₆) δ 9.85 (s, 1H), 8.47 (d, J = 5.1 Hz, 1H), 8.23 (s, 1H), 7.69-7.60 (m, 2H), 7.32 (dd, J = 8.5, 7.1 Hz, 2H), 7.18 (d, J = 5.1 Hz, 1H), 7.12 (d, J = 12.5 Hz, 1H), 7.06 (d, J = 8.4 Hz, 1H), 5.81 (s, 2H), 5.53 (s, 1H), 3.43 (s, 3H), 2.41 (s, 3H), 1.96 (s, 6H). | 524.25 |
| N-(4-(4-amino-5-(3-fluoro-4-(4-methylpyrimidin-2-yloxy)phenyl)-7-isopropyl-7H-pyrrolo[2,3-d]pyrimidin-6-yl)phenyl)methacrylamide | 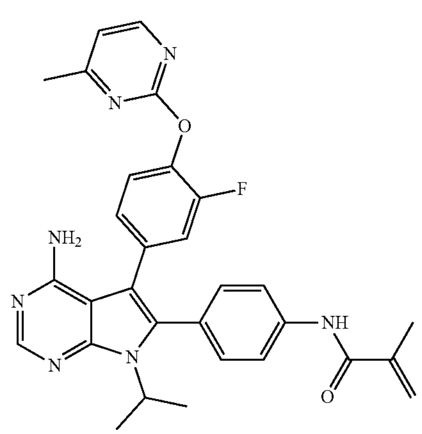 [SMILES: C=C(C)C(=O)Nc1ccc(-c2c(-c3ccc(Oc4nccc(C)n4)c(F)c3)c3c(N)ncnc3n2C(C)C)cc1] | ¹H NMR (400 MHz, DMSO-d₆) δ 9.94 (s, 1H), 8.47 (d, J = 5.0 Hz, 1H), 8.19 (s, 1H), 7.80-7.73 (m, 2H), 7.35-7.27 (m, 3H), 7.23-7.15 (m, 2H), 7.10 (dd, J = 8.3, 2.0 Hz, 1H), 5.81 (s, 1H), 5.54 (t, J = 1.5 Hz, 1H), 4.33 (p, J = 6.8 Hz, 1H), 2.41 (s, 3H), 1.96 (t, J = 1.3 Hz, 3H), 1.59 (d, J = 6.8 Hz, 6H). | 538.2 |

TABLE 2-continued

Additional Exemplary Compounds

| Compound | Structure | Proton NMR | MS [M + 1] |
|---|---|---|---|
| N-(4-(4-amino-7-ethyl-5-(3-fluoro-4-(4-methylpyrimidin-2-yloxy)phenyl)-7H-pyrrolo[2,3-d]pyrimidin-6-yl)phenyl)methacrylamide | 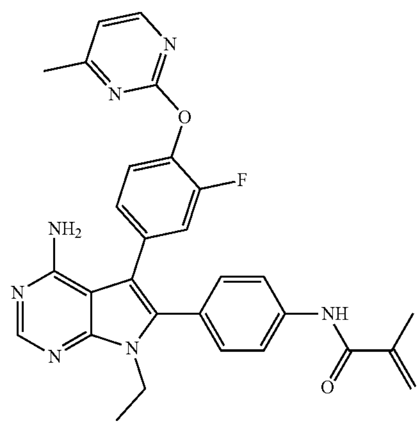 [SMILES: C=C(C)C(=O)Nc1ccc(-c2c(-c3ccc(Oc4nccc(C)n4)c(F)c3)c3c(N)ncnc3n2CC)cc1] | $^1$H NMR (400 MHz, DMSO-d$_6$) δ 9.94 (s, 1H), 8.47 (d, J = 5.0 Hz, 1H), 8.21 (s, 1H), 7.81-7.74 (m, 2H), 7.38-7.28 (m, 3H), 7.23-7.15 (m, 2H), 7.11 (dd, J = 8.3, 2.1 Hz, 1H), 5.81 (s, 1H), 5.54 (t, J = 1.5 Hz, 1H), 4.10 (q, J = 7.0 Hz, 2H), 2.42 (s, 3H), 1.96 (d, J = 1.4 Hz, 3H), 1.22-1.10 (m, 3H). | 524.4 |
| N-(4-(4-amino-5-(3-fluoro-4-(4-methylpyrimidin-2-yloxy)phenyl)-7-(2-hydroxyethyl)-7H-pyrrolo[2,3-d]pyrimidin-6-yl)phenyl)methacrylamide | 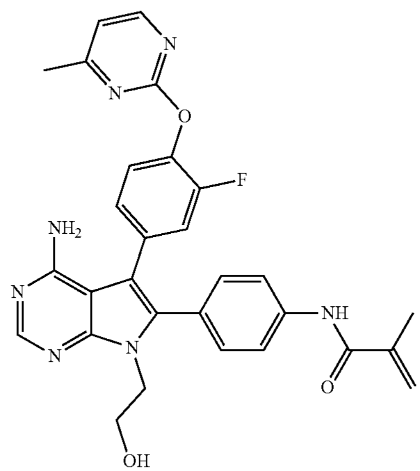 [SMILES: C=C(C)C(=O)Nc1ccc(-c2c(-c3ccc(Oc4nccc(C)n4)c(F)c3)c3c(N)ncnc3n2CCO)cc1] | $^1$H NMR (400 MHz, DMSO-d$_6$) δ 9.93 (s, 1H), 8.47 (d, J = 5.0 Hz, 1H), 8.21 (s, 1H), 7.79-7.72 (m, 2H), 7.37 (s, 1H), 7.39-7.29 (m, 2H), 7.21-7.13 (m, 2H), 7.10 (dd, J = 8.1, 2.0 Hz, 1H), 5.99 (s, 2H), 5.81 (s, 1H), 5.54 (d, J = 1.9 Hz, 1H), 4.90 (t, J = 5.5 Hz, 1H), 4.11 (t, J = 6.6 Hz, 2H), 3.58 (t, J = 6.2 Hz, 2H), 2.42 (s, 3H), 1.96 (t, J = 1.2 Hz, 3H). | 540.40 |
| N-(4-(4-amino-5-(3-fluoro-4-((4-methylpyrimidin-2-yl)oxy)phenyl)-7-(tetrahydrofuran-3-yl)-7H-pyrrolo[2,3-d]pyrimidin-6-yl)phenyl)methacrylamide | 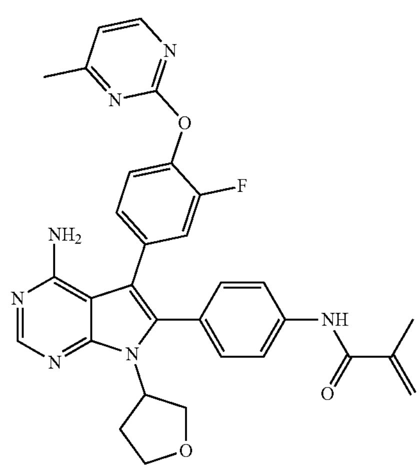 [SMILES: C=C(C)C(=O)Nc1ccc(-c2c(-c3ccc(Oc4nccc(C)n4)c(F)c3)c3c(N)ncnc3n2C2CCOC2)cc1] | $^1$H NMR (400 MHz, DMSO-d$_6$) δ 9.96 (s, 1H), 8.47 (d, J = 5.0 Hz, 1H), 8.22 (s, 1H), 7.78 (d, J = 8.3 Hz, 2H), 7.32 (dd, J = 8.5, 3.5 Hz, 3H), 7.24-7.15 (m, 2H), 7.11 (dd, J = 8.2, 2.0 Hz, 1H), 5.80 (s, 1H), 5.54 (s, 1H), 4.75-4.62 (m, 1H), 4.18 (dt, J = 14.4, 8.0 Hz, 2H), 3.96 (t, J = 8.2 Hz, 1H), 3.83 (q, J = 7.3 Hz, 1H), 2.77 (dq, J = 14.1, 7.3 Hz, 1H), 2.41 (s, 3H), 2.24-2.11 (m, 1H), 1.96 (s, 3H). | 566.45 |

TABLE 2-continued

Additional Exemplary Compounds

| Compound | Structure | Proton NMR | MS [M + 1] |
|---|---|---|---|
| N-(4-(4-amino-5-(3-fluoro-4-((4-methylpyrimidin-2-yl)oxy)phenyl)-7-(tetrahydrofuran-2-yl)-7H-pyrrolo[2,3-d]pyrimidin-6-yl)phenyl)methacrylamide | 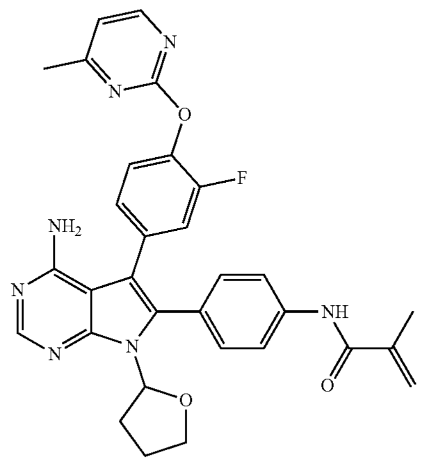 [SMILES: C=C(C)C(=O)Nc1ccc(-c2c(-c3ccc(Oc4nccc(C)n4)c(F)c3)c3c(N)ncnc3n2C2CCCO2)cc1] | ¹H NMR (400 MHz, DMSO-d₆) δ 9.94 (s, 1H), 8.47 (d, J = 5.1 Hz, 1H), 8.21 (s, 1H), 7.74 (d, J = 8.3 Hz, 2H), 7.31 (d, J = 8.6 Hz, 3H), 7.25-7.15 (m, 2H), 7.11 (d, J = 8.2 Hz, 1H), 5.94 (s, 2H), 5.81 (s, 1H), 5.54 (s, 1H), 4.09 (d, J = 7.7 Hz, 1H), 3.78 (s, 1H), 2.81 (s, 1H), 2.41 (s, 3H), 2.20 (d, J = 29.2 Hz, 2H), 1.95 (s, 3H), 1.89 (s, 1H). | 566.45 |
| N-(6-(4-amino-7-methyl-5-(4-((6-methylpyridin-2-yl)oxy)phenyl)-7H-pyrrolo[2,3-d]pyrimidin-6-yl)pyridin-3-yl)methacrylamide | 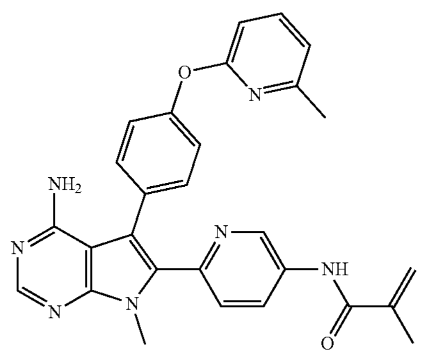 [SMILES: C=C(C)C(=O)Nc1ccc(-c2c(-c3ccc(Oc4cccc(C)n4)cc3)c3c(N)ncnc3n2C)nc1] | ¹H NMR (400 MHz, DMSO-d₆) δ 10.09 (s, 1H), 9.02-8.97 (m, 1H), 8.22 (s, 1H), 8.00 (dd, J = 8.6, 2.6 Hz, 1H), 7.74 (dd, J = 8.2, 7.4 Hz, 1H), 7.33-7.25 (m, 2H), 7.17-7.06 (m, 3H), 7.02 (d, J = 7.4 Hz, 1H), 6.81 (d, J = 8.2 Hz, 1H), 5.86 (t, J = 1.0 Hz, 1H), 5.59 (t, J = 1.6 Hz, 1H), 3.77 (s, 3H), 2.36 (s, 3H), 1.96 (t, J = 1.2 Hz, 3H). | 492.20 |
| 1-(4-(4-amino-7-methyl-5-(4-(pyrrolidine-1-carbonyl)phenyl)-7H-pyrrolo[2,3-d]pyrimidin-6-yl)phenyl)-1H-pyrrol-2(5H)-one | 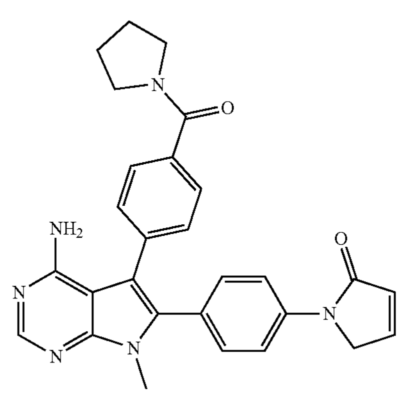 [SMILES: Cn1c(-c2ccc(N3CC=CC3=O)cc2)c(-c2ccc(C(=O)N3CCCC3)cc2)c2c(N)ncnc21] | ¹H NMR (400 MHz, DMSO-d₆) δ 8.21 (s, 1H), 7.82 (d, J = 8.5 Hz, 2H), 7.49 (d, J = 8.0 Hz, 3H), 7.35 (d, J = 8.4 Hz, 2H), 7.28 (d, J = 7.8 Hz, 2H), 6.25 (dt, J = 6.1, 1.9 Hz, 1H), 5.92 (s, 2H), 4.61 (d, J = 2.0 Hz, 2H), 3.62 (s, 3H), 3.44 (dt, J = 13.7, 6.5 Hz, 4H), 1.85 (dt, J = 11.2, 6.2 Hz, 3H), 1.79 (d, J = 6.8 Hz, 1H). | 479.20 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)phenyl)cyclopent-1-ene-1-carboxamide | 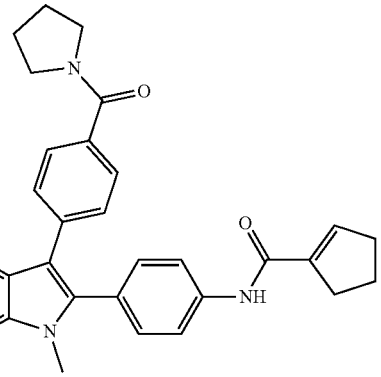 | $^1$H NMR (400 MHz, DMSO-d$_6$) δ 9.74 (s, 1H), 8.20 (s, 1H), 7.73-7.67 (m, 2H), 7.52-7.45 (m, 2H), 7.26 (dd, J = 8.5, 3.0 Hz, 4H), 6.70 (p, J = 2.2 Hz, 1H), 5.93 (s, 2H), 3.61 (s, 3H), 3.43 (dt, J = 16.5, 6.4 Hz, 4H), 2.57 (tt, J = 6.9, 2.2 Hz, 2H), 2.51 (tt, J = 6.9, 2.2 Hz, 2H), 1.97-1.76 (m, 6H). | 507.40 |
| 5-(4-amino-7-methyl-5-(4-(pyrrolidine-1-carbonyl)phenyl)-7H-pyrrolo[2,3-d]pyrimidin-6-yl)picolinonitrile | 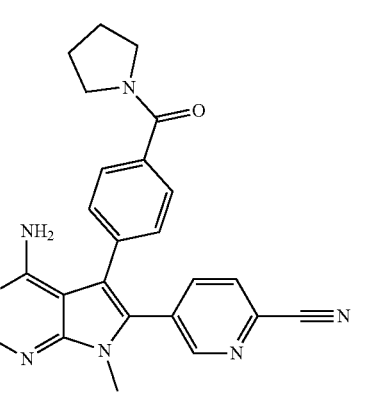 | $^1$H NMR (400 MHz, DMSO-d$_6$) δ 8.73 (d, J = 5.1 Hz, 1H), 8.26 (s, 1H), 7.97 (s, 1H), 7.62 (dd, J = 5.1, 1.7 Hz, 1H), 7.54 (d, J = 8.0 Hz, 2H), 7.30 (d, J = 8.0 Hz, 2H), 3.73 (s, 3H), 3.47 (t, J = 6.8 Hz, 2H), 3.41 (t, J = 6.3 Hz, 2H), 1.84 (dt, J = 19.3, 6.8 Hz, 4H). | 424.30 |
| (4-(4-amino-6-(4-(1,1-dioxidoisothiazol-2(3H)-yl)phenyl)-7-methyl-7H-pyrrolo[2,3-d]pyrimidin-5-yl)phenyl)(pyrrolidin-1-yl)methanone | 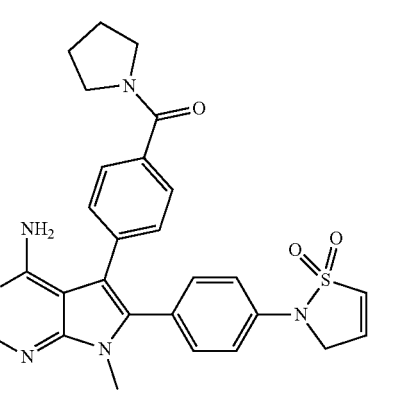 | $^1$H NMR (400 MHz, DMSO-d$_6$) δ 8.21 (d, J = 2.0 Hz, 1H), 7.50 (d, J = 7.8 Hz, 2H), 7.39 (dd, J = 13.6, 8.3 Hz, 4H), 7.28 (t, J = 1.0 Hz, 4H), 5.96 (s, 1H), 4.62 (s, 2H), 3.61 (s, 3H), 3.43 (dt, J = 13.0, 6.5 Hz, 4H), 1.84 (dt, J = 18.6, 6.9 Hz, 4H). | 515.35 |
| (4-(4-amino-6-(4-(1,1-dioxido-3,4-dihydro-2H-1,2-thiazin-2-yl)phenyl)-7-methyl-7H-pyrrolo[2,3-d]pyrimidin-5-yl)phenyl)(pyrrolidin-1-yl)methanone | 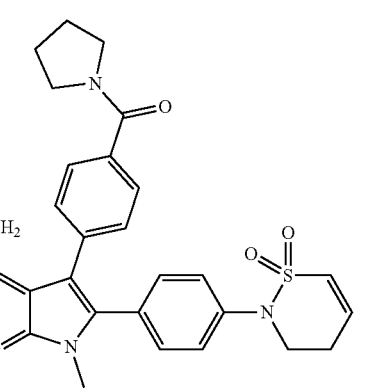 | $^1$H NMR (400 MHz, DMSO-d$_6$) δ 8.21 (s, 1H), 7.49 (d, J = 7.8 Hz, 2H), 7.41-7.18 (m, 6H), 5.93 (dd, J = 80.2, 10.4 Hz, 4H), 4.52-4.21 (m, 2H), 3.86 (d, J = 4.3 Hz, 2H), 3.62 (s, 3H), 3.43 (dt, J = 20.3, 6.5 Hz, 4H), 1.84 (dt, J = 18.5, 6.7 Hz, 4H). | 529.25 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)phenyl)cyclobut-1-ene-1-carboxamide | 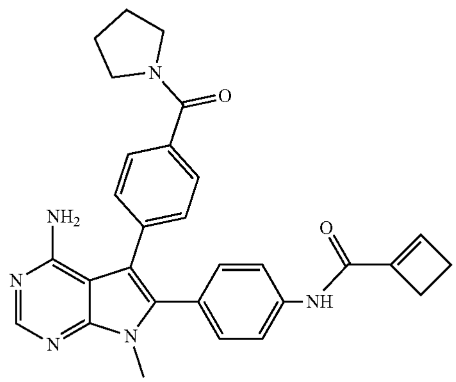 [SMILES: Cn1c(-c2ccc(NC(=O)C3=CCC3)cc2)c(-c2ccc(C(=O)N3CCCC3)cc2)c2c(N)ncnc21] | $^1$H NMR (400 MHz, DMSO-d$_6$) δ 9.83 (s, 1H), 8.21 (s, 1H), 7.74-7.67 (m, 2H), 7.52-7.45 (m, 2H), 7.31-7.21 (m, 4H), 6.80 (d, J = 1.3 Hz, 1H), 5.93 (s, 2H), 3.62 (s, 3H), 3.44 (dt, J = 18.5, 6.5 Hz, 4H), 2.74-2.68 (m, 2H), 2.46-2.40 (m, 2H), 1.83 (dq, J = 18.0, 6.9 Hz, 4H). | 493.20 |
| 1-(4-(4-amino-7-methyl-5-(4-(pyrrolidine-1-carbonyl)phenyl)-7H-pyrrolo[2,3-d]pyrimidin-6-yl)phenyl)-5,6-dihydropyridin-2(1H)-one | 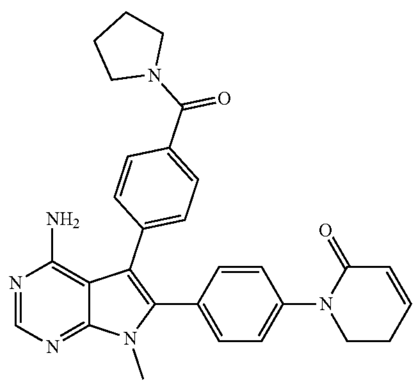 [SMILES: Cn1c(-c2ccc(N3CCC=CC3=O)cc2)c(-c2ccc(C(=O)N3CCCC3)cc2)c2c(N)ncnc21] | $^1$H NMR (400 MHz, DMSO-d$_6$) δ 8.21 (s, 1H), 7.55-7.45 (m, 2H), 7.42-7.25 (m, 6H), 6.83 (dt, J = 9.7, 4.2 Hz, 1H), 5.91 (dt, J = 9.7, 1.8 Hz, 3H), 3.83 (t, J = 6.9 Hz, 2H), 3.63 (s, 3H), 3.44 (dt, J = 13.7, 6.5 Hz, 4H), 2.48 (d, J = 10.1 Hz, 1H), 1.84 (dq, J = 18.2, 6.8 Hz, 4H). | 493.30 |
| N-(4-(4-amino-7-methyl-5-(4-(pyrrolidine-1-carbonyl)phenyl)-7H-pyrrolo[2,3-d]pyrimidin-6-yl)phenyl)-2-cyclobutylidene-acetamide | 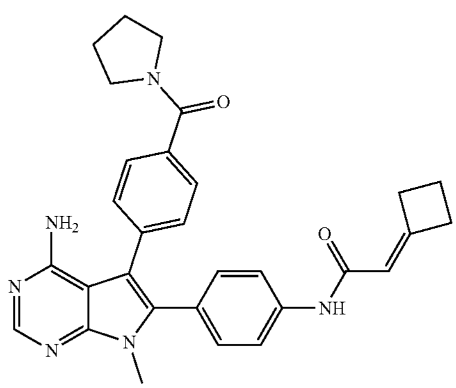 [SMILES: Cn1c(-c2ccc(NC(=O)C=C3CCC3)cc2)c(-c2ccc(C(=O)N3CCCC3)cc2)c2c(N)ncnc21] | $^1$H NMR (400 MHz, DMSO-d$_6$) δ 9.90 (s, 1H), 8.20 (s, 1H), 7.66-7.56 (m, 2H), 7.54-7.42 (m, 2H), 7.32-7.15 (m, 4H), 5.81 (t, J = 2.3 Hz, 1H), 3.61 (s, 3H), 3.47-3.32 (m, 4H), 3.10 (t, J = 8.2 Hz, 2H), 2.83 (t, J = 7.9 Hz, 2H), 2.05 (p, J = 7.9 Hz, 2H), 1.92-1.75 (m, 4H). | 507.30 |
| N-(4-(4-amino-7-methyl-5-(4-(pyrrolidine-1-carbonyl)phenyl)-7H-pyrrolo[2,3-d]pyrimidin-6-yl)phenyl)-2-cyclopentylidene acetamide | 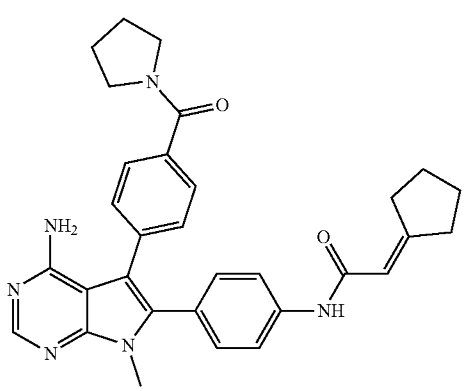 [SMILES: Cn1c(-c2ccc(NC(=O)C=C3CCCC3)cc2)c(-c2ccc(C(=O)N3CCCC3)cc2)c2c(N)ncnc21] | $^1$H NMR (400 MHz, DMSO-d$_6$) δ 9.93 (s, 1H), 8.20 (s, 1H), 7.67-7.60 (m, 2H), 7.52-7.45 (m, 2H), 7.29-7.20 (m, 4H), 6.01 (q, J = 2.4 Hz, 1H), 5.93 (s, 2H), 3.61 (s, 3H), 3.43 (dt, J = 15.8, 6.4 Hz, 4H), 2.75 (t, J = 7.2 Hz, 2H), 2.43 (t, J = 7.2 Hz, 2H), 1.84 (dp, J = 17.8, 6.6 Hz, 4H), 1.64 (dp, J = 34.2, 7.0 Hz, 4H). | 521.40 |

TABLE 2-continued

Additional Exemplary Compounds

| Compound | Structure | Proton NMR | MS [M + 1] |
|---|---|---|---|
| N-(4-(4-amino-7-methyl-5-(4-(pyrrolidine-1-carbonyl)phenyl)-7H-pyrrolo[2,3-d]pyrimidin-6-yl)phenyl)-2-((dimethylamino)methyl)acrylamide | 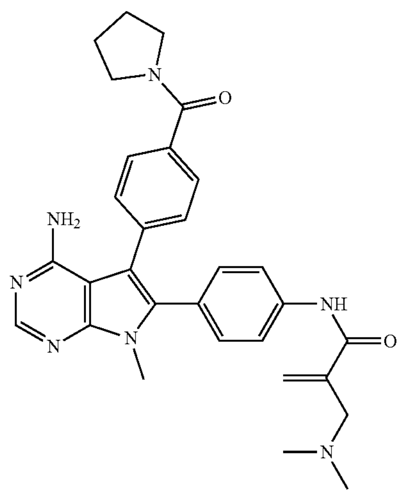 [SMILES: C=C(CN(C)C)C(=O)Nc1ccc(-c2c(-c3ccc(C(=O)N4CCCC4)cc3)c3c(N)ncnc3n2C)cc1] | $^1$H NMR (400 MHz, DMSO-d$_6$) δ 11.22 (s, 1H), 8.21 (s, 1H), 7.71-7.59 (m, 2H), 7.54-7.44 (m, 2H), 7.28 (t, J = 8.0 Hz, 4H), 6.02 (s, 2H), 5.59 (s, 1H), 3.62 (s, 3H), 3.62-3.41 (m, 4H), 3.23 (s, 2H), 2.25 (s, 6H), 1.89-1.80 (m, 4H). | 524.35 |
| (E)-N-(4-(4-amino-7-methyl-5-(4-(pyrrolidine-1-carbonyl)phenyl)-7H-pyrrolo[2,3-d]pyrimidin-6-yl)phenyl)-4-(dimethylamino)-2-methylbut-2-enamide | 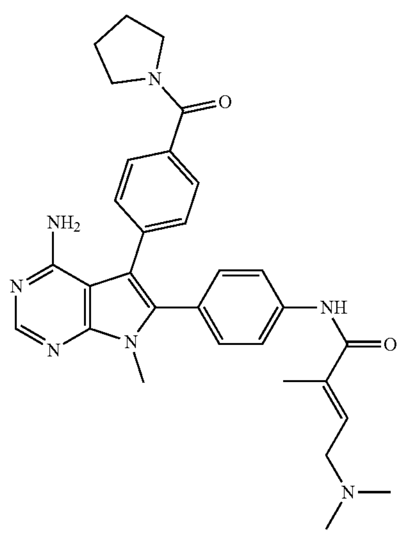 [SMILES: C/C(=C\CN(C)C)C(=O)Nc1ccc(-c2c(-c3ccc(C(=O)N4CCCC4)cc3)c3c(N)ncnc3n2C)cc1] | $^1$H NMR (400 MHz, DMSO-d6) δ 9.81 (s, 1H), 8.20 (s, 1H), 7.70 (d, J = 8.0 Hz, 2H), 7.49 (d, J = 8.2 Hz, 2H), 7.28-7.05 (m, 4H), 6.89 (t, J = 1.6Hz, 1H), 6.03-5.80 (m 1H), 3.60 (s, 3H), 3.47-3.41 (m, 4H), 3.04 (d, J = 6.0 Hz, 2H), 2.20 (s, 6H), 1.87 (s, 3H), 1.85-1.72 (m, 4H). | 538.30 |
| N-(4-(4-amino-5-(2-fluoro-4-(pyrrolidine-1-carbonyl)phenyl)-7-methyl-7H-pyrrolo[2,3-d]pyrimidin-6-yl)phenyl)methacrylamide | 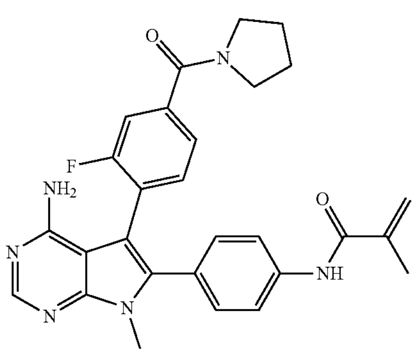 [SMILES: C=C(C)C(=O)Nc1ccc(-c2c(-c3ccc(C(=O)N4CCCC4)cc3F)c3c(N)ncnc3n2C)cc1] | $^1$H NMR (400 MHz, DMSO-d$_6$) δ 9.87 (s, 1H), 8.20 (s, 1H), 7.71-7.64 (m, 2H), 7.36-7.30 (m, 3H), 7.27-7.21 (m, 2H), 5.92 (s, 2H), 5.80 (d, J = 1.4 Hz, 1H), 5.53 (t, J = 1.4 Hz, 1H), 3.65 (s, 3H), 3.45 (q, J = 7.2 Hz, 4H), 1.95 (t, J = 1.2 Hz, 3H), 1.92-1.77 (m, 4H). | 499.25 |

TABLE 2-continued

Additional Exemplary Compounds

| Compound | Structure | Proton NMR | MS [M + 1] |
|---|---|---|---|
| N-(4-(4-amino-5-(2,3-difluoro-4-(4-methylpyrimidin-2-yl)oxy)phenyl)-7-methyl-7H-pyrrolo[2,3-d]pyrimidin-6-yl)phenyl) methacrylamide | 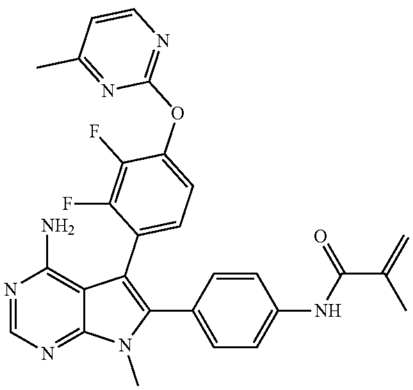 [SMILES: C=C(C)C(=O)Nc1ccc(-c2c(-c3ccc(Oc4nccc(C)n4)c(F)c3F)c3c(N)ncnc3n2C)cc1] | $^1$H NMR (400 MHz, DMSO-d$_6$) δ 9.92 (s, 1H), 8.51 (d, J = 5.0 Hz, 1H), 8.21 (s, 1H), 7.75 (d, J = 8.4 Hz, 2H), 7.42-6.94 (m, 5H), 6.04 (s, 2H), 5.80 (s, 1H), 5.54 (s, 1H), 3.64 (s, 3H), 2.43 (s, 3H), 1.95 (s, 3H). | 528.30 |
| N-(4-(4-amino-5-(2,5-difluoro-4-(4-methylpyrimidin-2-yl)oxy)phenyl)-7-methyl-7H-pyrrolo[2,3-d]pyrimidin-6-yl)phenyl) methacrylamide | 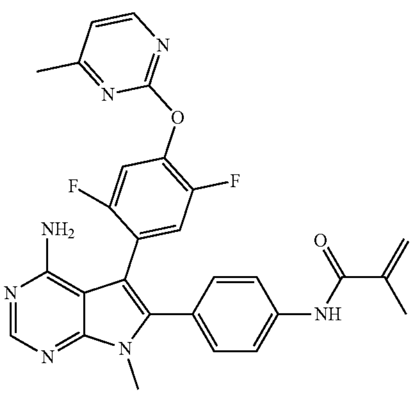 [SMILES: C=C(C)C(=O)Nc1ccc(-c2c(-c3cc(F)c(Oc4nccc(C)n4)cc3F)c3c(N)ncnc3n2C)cc1] | $^1$H NMR (400 MHz, DMSO-d$_6$) δ 9.92 (s, 1H), 8.51 (d, J = 5.0 Hz, 1H), 8.21 (s, 1H), 7.81-7.71 (m, 2H), 7.43-7.27 (m, 4H), 7.22 (d, J = 5.1 Hz, 1H), 6.00 (s, 2H), 5.85-5.77 (m, 1H), 5.54 (t, J = 1.5 Hz, 1H), 3.63 (s, 3H), 2.43 (s, 3H), 1.96 (t, J = 1.3 Hz, 3H). | 528.30 |
| N-(4-(4-amino-7-methyl-5-(4-((1-methyl-1H-pyrazol-4-yl)oxy)phenyl)-7H-pyrrolo[2,3-d]pyrimidin-6-yl)phenyl) methacrylamide | 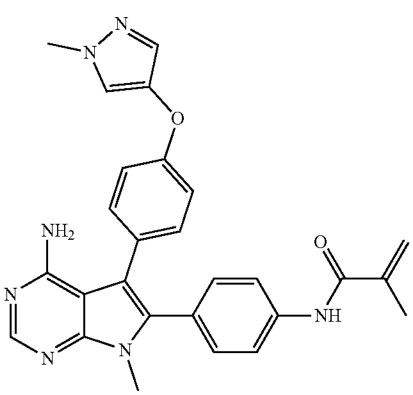 [SMILES: C=C(C)C(=O)Nc1ccc(-c2c(-c3ccc(Oc4cnn(C)c4)cc3)c3c(N)ncnc3n2C)cc1] | $^1$H NMR (400 MHz, DMSO-d$_6$) δ 9.89 (s, 1H), 8.18 (s, 1H), 7.77 (s, 1H), 7.74-7.67 (m, 2H), 7.39 (s, 1H), 7.30-7.23 (m, 2H), 7.23-7.15 (m, 2H), 7.00-6.92 (m, 2H), 5.80 (s, 2H), 5.54 (d, J = 1.8 Hz, 1H), 3.81 (s, 3H), 3.59 (s, 3H),, 1.95 (d, J = 1.5 Hz, 3H). | 480.35 |
| N-(4-(4-amino-7-methyl-5-(4-(1-methyl-2-azabicyclo[2.1.1]hexane-2-carbonyl)phenyl)-7H-pyrrolo[2,3-d]pyrimidin-6-yl)phenyl) methacrylamide | | $^1$H NMR (400 MHz, DMSO-d$_6$) δ 9.88 (s, 1H), 8.21 (s, 1H), 7.73-7.67 (m, 2H), 7.50 (d, J = 7.7 Hz, 2H), 7.29-7.22 (m, 4H), 5.80 (s, 1H), 5.53 (t, J = 1.5 Hz, 1H), 3.62 (s, 3H), 3.40 (s, 2H), 2.71 (d, J = 3.1 Hz, 1H), 1.95 (d, J = 1.4 Hz, 3H), 1.76 (d, J = 4.8 Hz, 2H), 1.60 (s, 3H), 1.50 (dd, J = 4.5, 1.9 Hz, 2H). | 507.3 |

TABLE 2-continued

Additional Exemplary Compounds

| Compound | Structure | Proton NMR | MS [M + 1] |
|---|---|---|---|
| N-(4-(4-amino-5-(4-(1-(hydroxymethyl)-2-azabicyclo[2.1.1]hexane-2-carbonyl)phenyl)-7-methyl-7H-pyrrolo[2,3-d]pyrimidin-6-yl)phenyl)methacrylamide | | $^1$H NMR (400 MHz, DMSO-d$_6$) δ 9.90 (s, 1H), 8.21 (s, 1H), 7.71 (d, J = 8.6 Hz, 2H), 7.57 (d, J = 7.9 Hz, 2H), 7.27 (dd, J = 8.4, 3.0 Hz, 4H), 5.80 (s, 1H), 5.53 (s, 1H), 5.12 (t, J = 6.5 Hz, 1H), 3.93 (d, J = 6.4 Hz, 2H), 3.62 (s, 3H), 3.46 (s, 2H), 2.74 (d, J = 3.2 Hz, 1H), 1.95 (s, 3H), 1.93-1.87 (m, 2H), 1.47 (dd, J = 4.6, 1.8 Hz, 2H). | 523.2 |
| N-(4-(4-amino-5-(2-fluoro-4-((4-methylpyrimidin-2-yl)oxy)phenyl)-7-methyl-7H-pyrrolo[2,3-d]pyrimidin-6-yl)-3-fluorophenyl)methacrylamide | 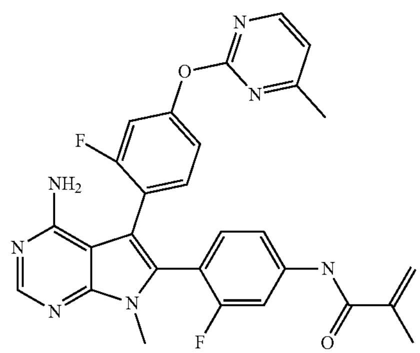 [SMILES: C=C(C)C(=O)Nc1ccc(-c2c(-c3ccc(Oc4nccc(C)n4)cc3F)c3c(N)ncnc3n2C)c(F)c1] | $^1$H NMR (400 MHz, DMSO-d$_6$) δ 10.10 (s, 1H), 8.49 (d, J = 5.0 Hz, 1H), 8.22 (s, 1H), 7.77 (dd, J = 12.5, 2.0 Hz, 1H), 7.50 (dd, J = 8.5, 2.0 Hz, 1H), 7.26 (t, J = 8.4 Hz, 2H), 7.18 (d, J = 5.0 Hz, 2H), 7.07 (d, J = 8.3 Hz, 1H), 5.82 (s, 1H), 5.58 (s, 1H), 3.57 (s, 3H), 2.42 (s, 3H), 1.95 (d, J = 1.2 Hz, 3H). | 528.40 |
| (4-(4-amino-7-methyl-6-(2-vinylpyrimidin-5-yl)-7H-pyrrolo[2,3-d]pyrimidin-5-yl)phenyl)(pyrrolidin-1-yl)methanone | 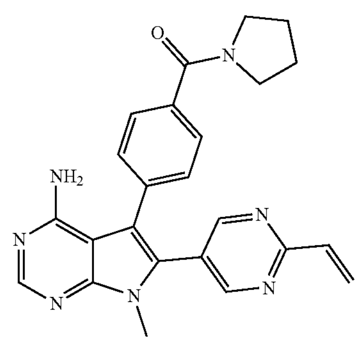 [SMILES: C=Cc1ncc(-c2c(-c3ccc(C(=O)N4CCCC4)cc3)c3c(N)ncnc3n2C)cn1] | $^1$H NMR (400 MHz, DMSO-d$_6$) δ 8.75 (s, 2H), 8.25 (s, 1H), 7.54 (d, J = 7.9 Hz, 2H), 7.33 (d, J = 7.9 Hz, 2H), 6.84 (dd, J = 17.3, 10.5 Hz, 1H), 6.57 (dd, J = 17.3, 2.0 Hz, 1H), 5.81 (dd, J = 10.5, 2.0 Hz, 1H), 3.72 (s, 3H), 3.45 (dt, J = 16.8, 6.5 Hz, 4H), 1.84 (dq, J = 18.7, 6.8 Hz, 4H). | 462.35 |
| N-(4-(4-amino-7-methyl-5-(4-(pyrrolidine-1-carbonyl)phenyl)-7H-pyrrolo[2,3-d]pyrimidin-6-yl)phenyl)-2-chloroacetamide | 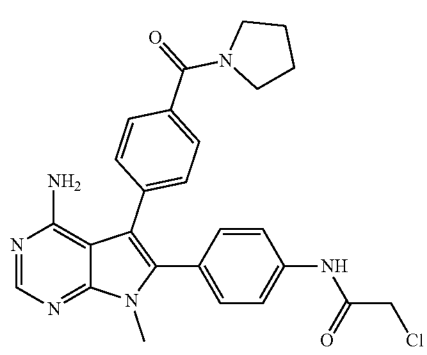 [SMILES: Cn1c(-c2ccc(NC(=O)CCl)cc2)c(-c2ccc(C(=O)N3CCCC3)cc2)c2c(N)ncnc21] | $^1$H NMR (400 MHz, DMSO-d$_6$) δ 10.43 (s, 1H), 8.21 (s, 1H), 7.68 (s, 3H), 7.61 (d, J = 8.1 Hz, 2H), 7.49 (d, J = 7.7 Hz, 2H), 7.28 (dd, J = 15.1, 7.9 Hz, 4H), 5.94 (s, 2H), 4.27 (s, 2H), 3.61 (s, 3H), 3.45 (dd, J = 16.0, 8.9 Hz, 4H), 1.84 (dd, J = 18.3, 6.3 Hz, 5H). | 489.35 |

TABLE 2-continued

Additional Exemplary Compounds

| Compound | Structure | Proton NMR | MS [M + 1] |
|---|---|---|---|
| (R)-N-(4-(4-amino-5-(3-fluoro-4-((4-methylpyrimidin-2-yl)oxy)phenyl)-7-(tetrahydrofuran-3-yl)-7H-pyrrolo[2,3-d]pyrimidin-6-yl)phenyl) methacrylamide | 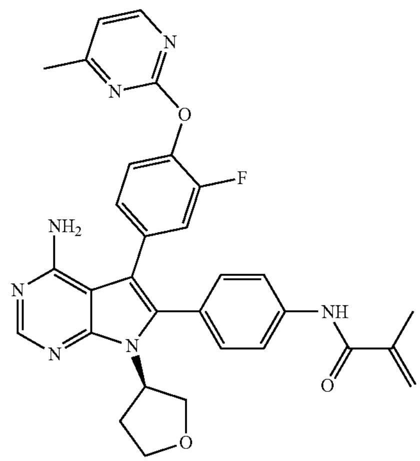 [SMILES: C=C(C)C(=O)Nc1ccc(-c2c(-c3ccc(Oc4nccc(C)n4)c(F)c3)c3c(N)ncnc3n2[C@@H]2CCOC2)cc1] | $^1$H NMR (400 MHz, DMSO-d$_6$) δ 9.94 (s, 1H), 8.47 (d, J = 5.0 Hz, 1H), 8.21 (s, 1H), 7.81-7.74 (m, 2H), 7.37-7.28 (m, 3H), 7.24-7.15 (m, 2H), 7.11 (dd, J = 8.2, 2.0 Hz, 1H), 5.95 (s, 1H), 5.80 (s, 1H), 5.54 (d, J = 1.8 Hz, 1H), 4.68 (p, J = 8.2 Hz, 1H), 4.18 (dt, J = 15.3, 8.2 Hz, 2H), 3.96 (t, J = 8.2 Hz, 1H), 3.83 (q, J = 7.5 Hz, 1H), 2.77 (dq, J = 14.1, 7.2 Hz, 1H), 2.41 (s, 3H), 2.17 (dd, J = 10.1, 4.9 Hz, 1H), 1.96 (t, J = 1.2 Hz, 3H). | 566.25 |
| (S)-N-(4-(4-amino-5-(3-fluoro-4-((4-methylpyrimidin-2-yl)oxy)phenyl)-7-(tetrahydrofuran-3-yl)-7H-pyrrolo[2,3-d]pyrimidin-6-yl)phenyl) methacrylamide | 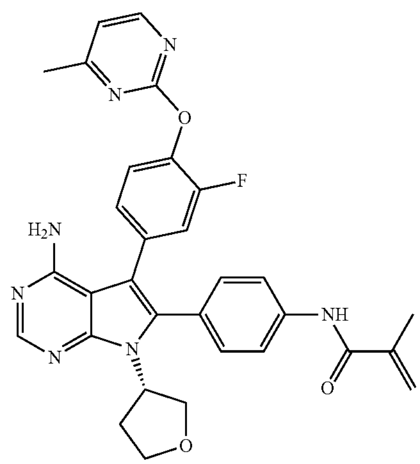 [SMILES: C=C(C)C(=O)Nc1ccc(-c2c(-c3ccc(Oc4nccc(C)n4)c(F)c3)c3c(N)ncnc3n2[C@H]2CCOC2)cc1] | $^1$H NMR (400 MHz, DMSO-d$_6$) δ 9.95 (s, 1H), 8.47 (d, J = 5.0 Hz, 1H), 8.24 (s, 1H), 7.81-7.74 (m, 2H), 7.37-7.28 (m, 3H), 7.25-7.15 (m, 2H), 7.14-7.07 (m, 1H), 6.12 (s, 1H), 5.80 (s, 1H), 5.55 (d, J = 1.9 Hz, 1H), 4.68 (q, J = 8.3 Hz, 1H), 4.24-4.12 (m, 2H), 3.97 (t, J = 8.2 Hz, 1H), 3.83 (q, J = 7.4 Hz, 1H), 2.76 (dq, J = 14.2, 7.3 Hz, 1H), 2.41 (s, 3H), 2.19 (s, 1H), 1.96 (t, J = 1.2 Hz, 3H). | 566.20 |
| N-(4-(4-amino-7-methyl-5-(4-(pyrrolidine-1-carbonyl)phenyl)-7H-pyrrolo[2,3-d]pyrimidin-6-yl)phenyl)-2-(cyclopent-1-en-1-yl)acetamide | 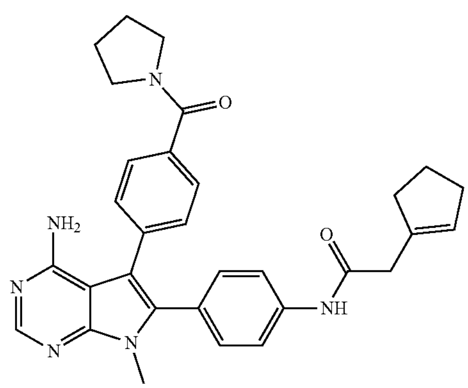 [SMILES: Cn1c(-c2ccc(NC(=O)CC3=CCCC3)cc2)c(-c2ccc(C(=O)N3CCCC3)cc2)c2c(N)ncnc21] | $^1$H NMR (400 MHz, DMSO-d$_6$) δ 10.06 (s, 1H), 8.20 (s, 1H), 7.64-7.57 (m, 2H), 7.52-7.45 (m, 2H), 7.29-7.21 (m, 4H), 5.92 (s, 2H), 5.52 (s, 1H), 3.60 (s, 3H), 3.43 (dt, J = 18.2, 6.4 Hz, 4H), 3.13 (s, 2H), 2.30 (t, J = 7.6 Hz, 4H), 1.84 (tdd, J = 12.4, 7.0, 3.8 Hz, 6H). | 521.35 |

TABLE 2-continued

Additional Exemplary Compounds

| Compound | Structure | Proton NMR | MS [M + 1] |
|---|---|---|---|
| 2-((4-(4-amino-5-(3-fluoro-4-((4-methylpyrimidin-2-yl)oxy)phenyl)-7-methyl-7H-pyrrolo[2,3-d]pyrimidin-6-yl)phenyl)amino)acetonitrile | 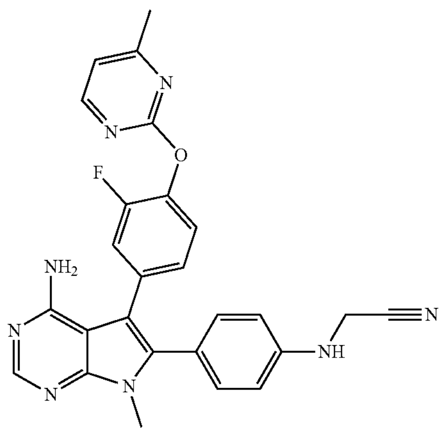 [SMILES: Cc1ccnc(Oc2ccc(-c3c(-c4ccc(NCC#N)cc4)n(C)c4ncnc(N)c34)cc2F)n1] | $^1$H NMR (400 MHz, CDCl$_3$): δ 8.41-8.36 (m, 2H), 8.21 (s, 1H), 7.48 (s, 1H), 7.41-7.38 (m, 2H), 7.31-7.28 (m, 2H), 6.96 (s, 1H), 5.14 (s, 2H), 4.28 (m, 2H), 3.21 (s, 1H), 2.85-2.81 (m, 2H), 2.54 (s, 3H), 2.40-2.36 (m, 2H) | 460.3 |
| methyl (2E)-4-{[4-(4-amino-5-{3-fluoro-4-[(4-methylpyrimidin-2-yl)oxy]phenyl}-7-methyl-7H-pyrrolo[2,3-d]pyrimidin-6-yl)phenyl]amino}but-2-enoate | 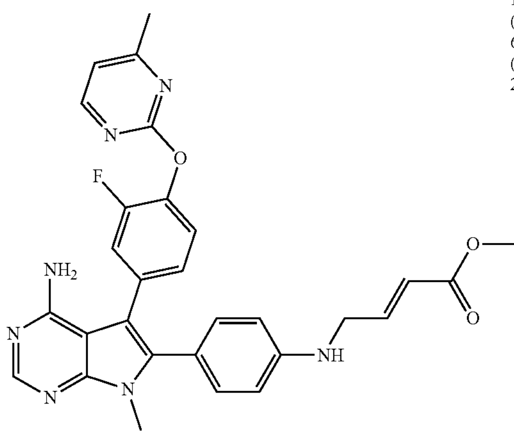 | $^1$H NMR (400 MHz, CD$_3$OD): δ 8.42 (d, J = 5.2 Hz, 1H), 8.19 (s, 1H), 7.29-7.25 (m, 1H), 7.18-7.02 (m, 6H), 6.65 (d, J = 8.4 Hz, 2H), 6.03 (d, J = 15.6 Hz, 1H), 3.99-3.97 (m, 2H), 3.71 (s, 3H), 3.68 (s, 3H), 2.51 (s, 3H). | 540.3 |
| N-[(3S)-1-[3-(4-amino-7-methyl-5-{4-[(6-methylpyridin-2-yl)oxy]phenyl}-7H-pyrrolo[2,3-d]pyrimidin-6-yl)phenyl]pyrrolidin-3-yl]prop-2-enamide | 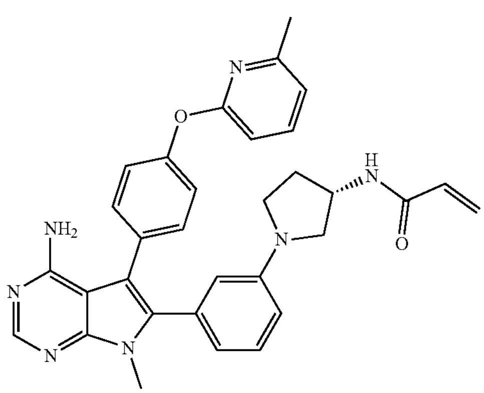 | $^1$H NMR (400 MHz, CDCl$_3$): δ 8.37 (s, 1 H), 7.62-7.54 (m, 1H), 7.33-7.26 (m, 2H), 7.08-7.04 (m, 2H), 6.93-6.88 (m, 2H), 6.70-6.62 (m, 2H), 6.59-6.52 (m, 1H), 6.38-6.25 (m, 2H), 6.10-5.99 (m, 1H), 5.93-5.83 (m, 1H), 5.05-4.96 (m, 2H), 4.76-4.63 (m, 1H), 3.75 (s, 3H) 3.53-3.45 (m, 1H), 3.39-3.05 (m, 3H), 2.45 (s, 3H), 2.36-2.26 (m, 1H), 2.06-1.96 (m, 1H). | 546.1 |

TABLE 2-continued

Additional Exemplary Compounds

| Compound | Structure | Proton NMR | MS [M + 1] |
|---|---|---|---|
| N-[(3R)-1-[3-(4-amino-7-methyl-5-{4-[(6-methylpyridin-2-yl)oxy]phenyl}-7H-pyrrolo[2,3-d]pyrimidin-6-yl)phenyl]pyrrolidin-3-yl]prop-2-enamide | 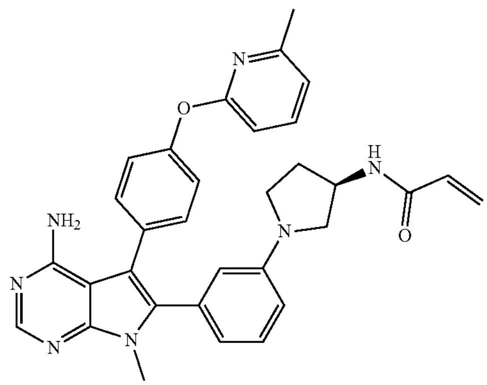 | $^1$H NMR (400 MHz, CDCl$_3$): δ 8.37 (s, 1 H), 7.62-7.54 (m, 1H), 7.33-7.26 (m, 2H), 7.08-7.04 (m, 2H), 6.93-6.88 (m, 2H), 6.70-6.62 (m, 2H), 6.59-6.52 (m, 1H), 6.38-6.25 (m, 2H), 6.10-5.99 (m, 1H), 5.93-5.83 (m, 1H), 5.05-4.96 (m, 2H), 4.76-4.63 (m, 1H), 3.75 (s, 3H) 3.53-3.45 (m, 1H), 3.39-3.05 (m, 3H), 2.45 (s, 3H), 2.36-2.26 (m, 1H), 2.06-1.96 (m, 1H) | 546.1 |
| 1-{4-[3-(4-amino-7-methyl-5-{4-[(6-methylpyridin-2-yl)oxy]phenyl}-7H-pyrrolo[2,3-d]pyrimidin-6-yl)phenyl]piperazin-1-yl}prop-2-en-1-one hydrochloride | 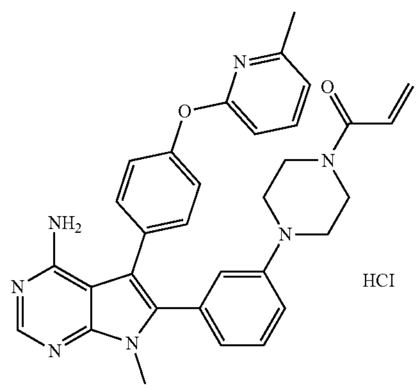 | $^1$H NMR (400 MHz, DMSO-d$_6$) δ 8.57 (s, 1H), 7.73-7.70 (m, 1H), 7.63-7.60 (d, J = 8.0 Hz, 1H), 7.49-7.45 (m, 2H), 7.35-7.28 (m, 3H), 7.32-7.28 (m, 3H), 7.14-7.10 (m, 2H), 7.02-7.00 (d, J = 7.6 Hz, 1H), 6.79-6.76 (m, 1H), 6.69-6.59 (m, 1H), 6.49 (s, 1H), 6.23-6.15 (m, 1H), 5.75-5.70 (m, 1H), 4.69 (s, 1H), 4.55-4.47 (d, J = 32.4 Hz, 2H), 4.32 (s, 1H), 3.75-3.73 (d, J = 6.8 Hz, 3H), 2.31-2.29 (d, J = 7.2 Hz, 3H). | 529.3 |
| N-{[3-(4-amino-7-methyl-5-{4-[(6-methylpyridin-2-yl)oxy]phenyl}-7H-pyrrolo[2,3-d]pyrimidin-6-yl)phenyl]methyl}prop-2-enamide hydrochloride | 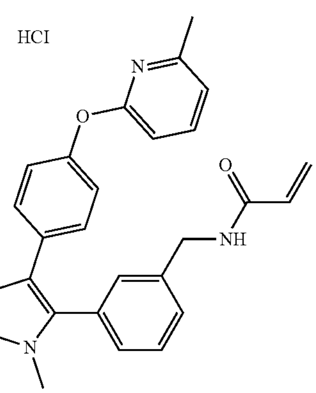 | $^1$H NMR (400 MHz, DMSO-d$_6$): δ 8.71-8.67 (m, 1H), 8.58 (s, 1H), 7.76 (t, J = 7.8 Hz, 1H), 7.44-7.20 (m, 6H), 7.15-7.00 (m, 3H), 6.81 (d, J = 8.0 Hz, 1H), 6.32-6.23 (m, 1H), 6.16-6.05 (m, 1H), 5.61 (dd, J = 2.1, 10.0 Hz, 1H), 4.36 (d, J = 6.0 Hz, 2H), 3.69 (s, 3H), 2.37 (s, 3H). | 491.1 |

TABLE 2-continued

Additional Exemplary Compounds

| Compound | Structure | Proton NMR | MS [M + 1] |
|---|---|---|---|
| N-[2-(4-amino-7-methyl-5-{4-[(6-methylpyridin-2-yl)oxy]phenyl}-7H-pyrrolo[2,3-d]pyrimidin-6-yl)phenyl]prop-2-enamide hydrochloride | 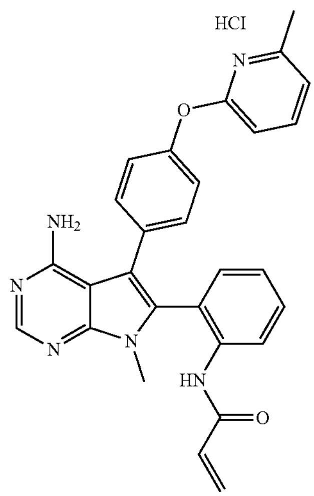 | $^1$H NMR (400 MHz, CD$_3$OD): δ 8.10 (s, 1H), 7.66-7.55 (m, 2H), 7.40-7.32 (m, 2H), 7.28-7.19 (m, 1H), 7.11 (br d, J = 7.8 Hz, 2H), 6.90 (t, J = 7.2 Hz, 3H), 6.63 (d, J = 8.4 Hz, 1H), 6.17-5.99 (m, 2H), 5.58-5.50 (m, 1H), 5.10 (s, 1H), 4.88-4.82 (m, 4H), 4.51 (s, 11H), 3.54 (s, 4H), 2.36-2.27 (m, 3H) | 477.2 |
| N-[5-(4-amino-7-methyl-5-{4-[(4-methylpyrimidin-2-yl)oxy]phenyl}-7Hpyrrolo[2,3-d]pyrimidin-6-yl)-1-methyl-1H-pyrazol-3-yl]prop-2-enamide | 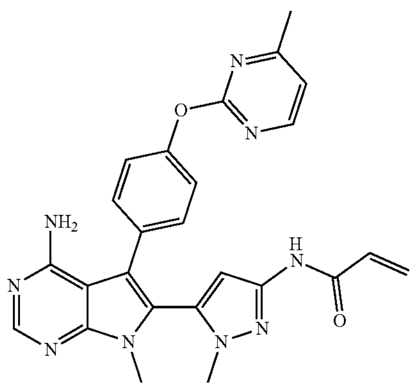 | $^1$HNMR (400 MHz, Methanol-d$_4$): δ 8.30 (d, J = 5.0 Hz, 1H), 8.14 (s, 1H), 7.29 (d, J = 8.4 Hz, 2H), 7.13 (d, J = 8.8 Hz, 2H), 7.02 (d, J = 5.0 Hz, 1H), 6.82 (s, 1H), 6.40-6.23 (m, 2H), 5.68 (dd, J = 2.4, 9.8 Hz, 1H), 4.50 (s, 4H), 3.61-3.56 (m, 3H), 2.38 (s, 3H). | 482.3 |
| N-[5-(4-amino7-methyl-5-{4-[(6-methylpyridin-2-yl)oxy]phenyl}-7H-pyrrolo[2,3-d]pyrimidin-6-yl)-1-methyl-1H-pyrazol-3-yl]prop-2-enamide | 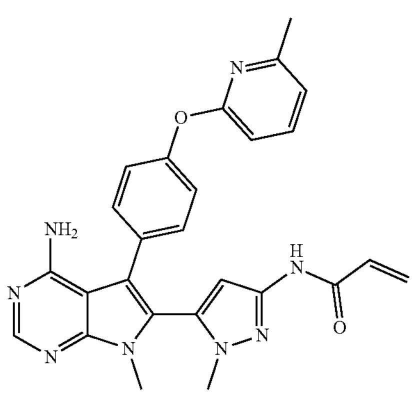 | $^1$HNMR (400 MHz, DMSO-d$_6$): δ 10.73 (s, 1H), 8.28 (s, 1H), 7.85 (t, J = 7.6 Hz, 1H), 7.62 (d, J = 2.0 Hz, 1H), 7.54-7.45 (m, 3H), 7.35 (d, J = 8.4 Hz, 2H), 7.13 (d, J = 7.6 Hz, 1H), 7.00-6.94 (m, 1H), 6.93-6.87 (m, 1H), 6.58 (d, J = 2.4 Hz, 1H), 4.01 (s, 3H), 3.88-3.75 (m, 4H), 2.45 (s, 3H). | 481.3 |

TABLE 2-continued

Additional Exemplary Compounds

| Compound | Structure | Proton NMR | MS [M + 1] |
|---|---|---|---|
| [3-[4-amino-7-methyl-5-[4-[(6-methyl-2-pyridyl)oxy]phenyl]pyrrolo[2,3-d]pyrimidin-6-yl]phenyl]cyanamide | 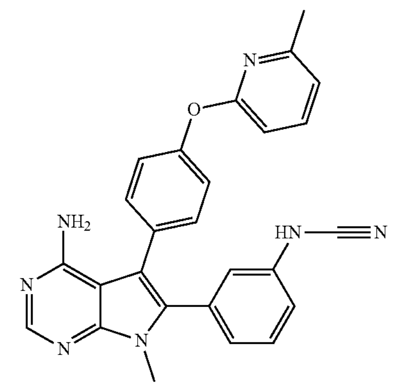 [SMILES: Cc1cccc(Oc2ccc(-c3c(-c4cccc(NC#N)c4)n(C)c4ncnc(N)c34)cc2)n1] | ¹H NMR (400 MHz, DMSO-d₆) δ 8.20 (s, 1H), 7.72 (t, J = 7.6 Hz, 1H), 7.38 (t, J = 8.0 Hz, 1H), 7.2 (d, J = 8.8 Hz, 2H), 7.09 (d, J = 7.6 Hz, 2H), 7.04-7.00 (m, 2H), 6.98-6.93 (m, 1H), 6.81 (s, 1H), 6.77 (d, J = 8.0 Hz, 1H), 5.93 (br, 1H), 3.60 (s, 3H), 2.35 (s, 3H). | 448.2 |
| 4-{4-amino-7-methyl-6-[3-(prop-2-enamido)phenyl]-7H-pyrrolo[2,3-d]pyrimidin-5-yl}-N-[(3-fluorooxetan-3-yl)methyl]benzamide | 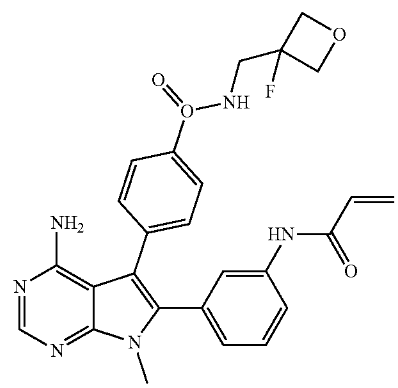 | ¹H NMR (400 MHz, DMSO-d₆) δ 10.24 (s, 1H), 8.83-8.77 (m, 1H), 8.22 (s, 1H), 7.82 (d, J = 8.0 Hz, 2H), 7.73-7.64 (m, 2H), 7.38-7.29 (m, 3H), 6.99 (d, J = 7.6 Hz, 1H), 6.47-6.35 (m, 1H), 6.30-6.21 (m, 1H), 5.98 (s, 1H), 5.79-5.73 (m, 1H), 4.73-4.55 (m, 4H), 3.82 (d, J = 6.0 Hz, 1H), 3.76 (d, J = 6.0 Hz 1H), 3.60 (s, 3H). | 501.1 |
| 4-{4-amino-7-methyl-6-[4-(prop-2-enamido)phenyl]-7H-pyrrolo[2,3-d]pyrimidin-5-yl}-N-[(3-fluorooxetan-3-yl)methyl]benzamide | 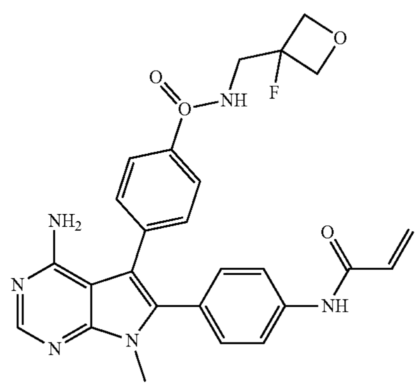 | ¹H NMR (400 MHz, DMSO-d₆): δ 10.27 (s, 1H), 8.82-8.74 (m, 1H), 8.20 (s, 1H), 7.82 (d, J = 8.0 Hz, 2H), 7.67 (d, J = 8.0 Hz, 2H), 7.33-7.24 (m, 4H), 6.48-6.38 (m, 1H), 6.30-6.23 (m, 1H), 5.93 (br, 1H), 5.80-5.74 (m, 1H), 4.71-4.52 (m, 4H), 3.83-3.73 (m, 2H), 3.60 (s, 3H). | 501.1 |
| 4-[4-amino-6-[3-(2-methylprop-2-enoylamino)phenyl]-7H-pyrrolo[2,3-d]pyrimidin-5-yl]-N-[(3-fluorooxetan-3-yl)methyl]benzamide | 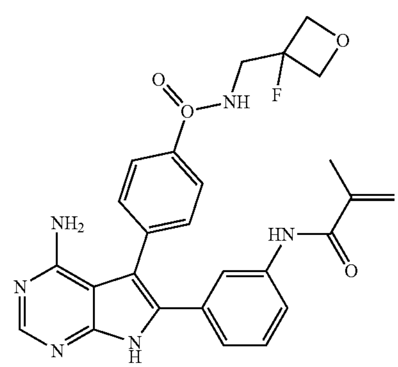 | ¹HNMR (400 MHz, DMSO-d₆): δ 12.16 (br, 1H), 9.81 (s, 1H), 8.86 (t, J = 6.0 Hz, 1H), 8.14 (s, 1H), 7.92 (d, J = 8.4 Hz, 2H), 7.81 (s, 1H), 7.57 (d, J = 8.0 Hz, 1H), 7.42 (d, J = 8.4 Hz, 2H), 7.21 (m, 1H), 6.89 (d, J = 8.0 Hz, 1H), 5.75 (s, 1H), 5.51 (s, 1H), 4.74-4.59 (m, 4H), 3.82 (dd, J = 19.6 Hz, 6.6 Hz, 2H), 1.92 (s, 3H). | 501.1 |

TABLE 2-continued

Additional Exemplary Compounds

| Compound | Structure | Proton NMR | MS [M + 1] |
|---|---|---|---|
| 4-{4-amino-7-methyl-6-[3-(2-methylprop-2-enamido)phenyl]-7H-pyrrolo[2,3-d]pyrimidin-5-yl}-N-[(3-fluorooxetan-3-yl)methyl]benzamide | | $^1$HNMR (400 MHz, DMSO-d$_6$): δ 9.88 (s, 1H), 8.81-8.78 (m, 1H), 8.22 (s, 1H), 7.82 (d, J = 8.4 Hz, 2H), 7.72 (d, J = 8.8 Hz, 2H), 7.34-7.29 (m, 3H), 6.95 (d, J = 7.6 Hz, 1H), 5.78 (s, 1H), 5.52 (s, 1H), 4.70-4.57 (m, 4H), 3.82-3.75 (m, 2H), 3.60 (s, 3H), 1.93 (s, 3H). | 515.1. |
| (2E)-N-(3-{4-amino-7-methyl-5-[4-(pyrrolidine-1-carbonyl)phenyl]-7H-pyrrolo[2,3-d]pyrimidin-6-yl}phenyl)-4-(dimethylamino)but-2-enamide hydrochloride | 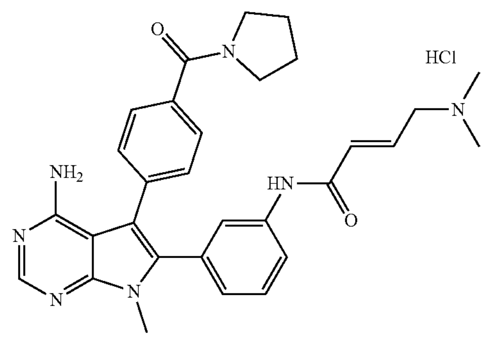 [SMILES: CN(C)C/C=C/C(=O)Nc1cccc(-c2c(-c3ccc(C(=O)N4CCCC4)cc3)c3c(N)ncnc3n2C)c1 ; Cl] | $^1$H NMR (400 MHz, DMSO-d$_6$): δ 10.99 (s, 1H), 10.72 (s, 1H), 8.60 (s, 1H), 7.77-7.73 (m, 2H), 7.49 (d, J = 8.4 Hz, 2H), 7.72 (d, J = 8.8 Hz, 2H), 7.43-7.39 (m, 1H), 7.28 (d, J = 8.4 Hz, 2H), 7.07 (d, J = 7.6 Hz, 1H), 6.83-6.76 (m, 1H), 6.50 (d, J = 7.2 Hz, 1H), 3.92-3.89 (m, 2H), 3.71 (s, 3H), 3.45-3.40 (m, 4H), 2.74 (d, J = 4.0 Hz, 6H), 1.88-1.76 (m, 4H). | 524.4 |
| 4-[4-amino-6-(4-{2-[(dimethylamino)methyl]prop-2-enamido}phenyl)-7-methyl-7H-pyrrolo[2,3-d]pyrimidin-5-yl]-N-[(3-fluorooxetan-3-yl)methyl]benzamide | 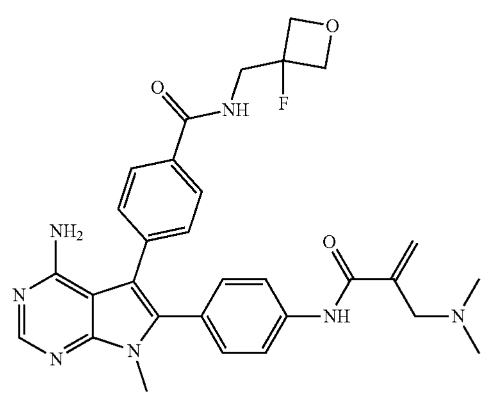 [SMILES: C=C(CN(C)C)C(=O)Nc1ccc(-c2c(-c3ccc(C(=O)NCC4(F)COC4)cc3)c3c(N)ncnc3n2C)cc1] | $^1$H NMR (400 MHz, DMSO-d$_6$): δ 8.83-8.74 (m, 1H), 8.16 (s, 1H), 7.80 (d, J = 8.0 Hz, 2H), 7.28 (d, J = 8.0 Hz, 2H), 6.99 (d, J = 8.0 Hz, 2H), 6.58 (d, J = 8.0 Hz, 2H), 6.30-6.20 (m, 1H), 5.83 (br, 1H), 5.36 (s, 1H), 5.12 (s, 1H), 4.74-4.53 (m, 4H), 3.89-3.70 (m, 4H), 3.57 (s, 3H), 2.91-2.78 (d, J = 16.0 Hz, 6H). | 558.2 |
| 4-{4-amino-7-methyl-6-[4-(prop-2-enamido)phenyl]-7H-pyrrolo[2,3-d]pyrimidin-5-yl}-N-(2-methylpropyl)benzamide | 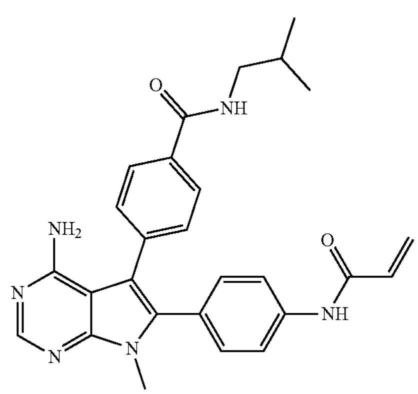 [SMILES: C=CC(=O)Nc1ccc(-c2c(-c3ccc(C(=O)NCC(C)C)cc3)c3c(N)ncnc3n2C)cc1] | $^1$H NMR (400 MHz, DMSO-d$_6$): δ 8.40 (s, 1H), 7.81 (d, J = 8.4 Hz, 2H), 7.71 (d, J = 8.8 Hz, 2H), 7.40 (d, J = 8.4 Hz, 2H), 7.30 (d, J = 8.4 Hz, 2H), 6.47-6.34 (m, 2H), 5.81-5.78 (m, 2H), 3.8 (s, 3H), 3.19 (d, J = 6.8 Hz, 1H), 1.95-1.88 (m, 1H), 0.95 (d, J = 6.4 Hz, 6H). | 469.2 |

TABLE 2-continued

Additional Exemplary Compounds

| Compound | Structure | Proton NMR | MS [M + 1] |
|---|---|---|---|
| (1S)-4-{4-amino-7-methyl-6-[4-(2-methylprop-2-enamido)phenyl]-7H-pyrrolo[2,3-d]pyrimidin-5-yl}-N-[(3-fluorooxetan-3-yl)methyl]cyclohex-3-ene-1-carboxamide | 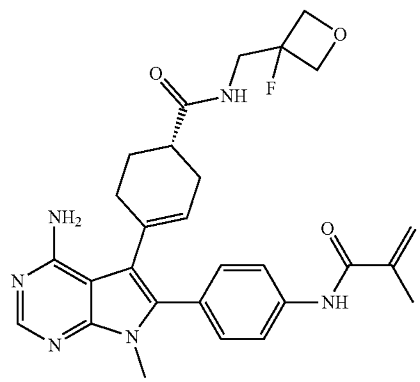 [SMILES: C=C(C)C(=O)Nc1ccc(-c2c(C3=CC[C@@H](C(=O)NCC4(F)COC4)CC3)c3c(N)ncnc3n2C)cc1] | $^1$H NMR (400 MHz, DMSO-d$_6$): δ 9.95 (s, 1H), 8.35-8.24 (m, 1H), 8.10 (s, 1H), 7.81 (d, J = 12.0 Hz, 2H), 7.43 (d, J = 12.0 Hz, 2H), 6.60-6.24 (m, 2H), 5.92-5.72 (m, 2H), 5.55 (s, 1H), 4.68-4.43 (m, 4H), 3.63-3.53 (m, 4H), 2.59-2.53 (m, 1H), 2.38-2.16 (m, 2H), 1.97 (s, 3H), 1.91-1.84 (m, 2H), 1.75-1.60 (m, 2H). | 519.1 |
| (1R)-4-{4-amino-7-methyl-6-[4-(2-methylprop-2-enamido)phenyl]-7H-pyrrolo[2,3-d]pyrimidin-5-yl}-N-[(3-fluorooxetan-3-yl)methyl]cyclohex-3-ene-1-carboxamide | 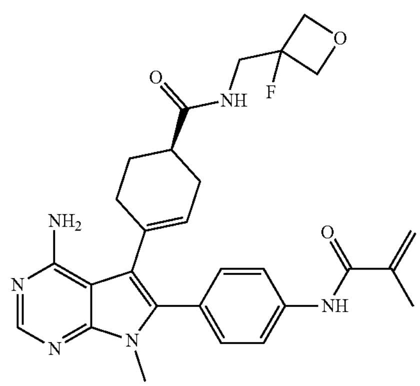 [SMILES: C=C(C)C(=O)Nc1ccc(-c2c(C3=CC[C@H](C(=O)NCC4(F)COC4)CC3)c3c(N)ncnc3n2C)cc1] | $^1$H NMR (400 MHz, DMSO-d$_6$): δ 9.96 (s, 1H), 8.26 (t, J = 6.0 Hz, 1H), 8.10 (s, 1H), 7.81 (d, J = 8.4 Hz, 2H), 7.43 (d, J = 8.4 Hz, 2H), 6.44 (br s, 2H), 5.88-5.70 (m, 2H), 5.55 (s, 1H), 4.64-4.46 (m, 4H), 3.62-3.53 (m, 4H), 2.59-2.54 (m, 1H), 2.39-2.16 (m, 2H), 1.97 (s, 3H), 1.93-83 (m, 2H), 1.72-1.60 (m, 2H). | 519.1 |
| N-{3-[4-amino-7-methyl-5-(1-methyl-1,2,3,4-tetrahydroquinolin-6-yl)-7H-pyrrolo[2,3-d]pyrimidin-6-yl]phenyl}prop-2-enamide hydrochloride | 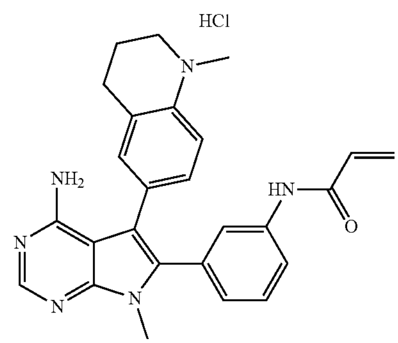 [SMILES: Cl ; C=CC(=O)Nc1cccc(-c2c(-c3ccc4c(c3)CCCN4C)c3c(N)ncnc3n2C)c1] | $^1$H NMR (400 MHz, DMSO-d$_6$): δ 10.60-10.32 (m, 1H), 8.59-8.40 (m, 1H), 7.78 (s, 1H), 7.70 (d, J = 7.6 Hz, 1H), 7.42-7.33 (m, 1H), 7.06-7.00 (m, 1H), 6.93-6.84 (m, 2H), 6.59 (d, J = 8.4 Hz, 1H), 6.52-6.41 (m, 1H), 6.25 (dd, J = 1.6, 16.8 Hz, 1H), 5.80-5.71 (m, 1H), 3.65-3.64 (m, 3H), 3.27-3.16 (m, 2H), 2.83 (s, 3H), 2.68-2.59 (m, 2H), 1.86 (m, 2H) | 439.1 |
| N-(3-{4-amino-7-methyl-5-[(4S)-4-(pyrrolidine-1-carbonyl)cyclohex-1-en-1-yl]-7H-pyrrolo[2,3-d]pyrimidin-6-yl}phenyl)prop-2-enamide | 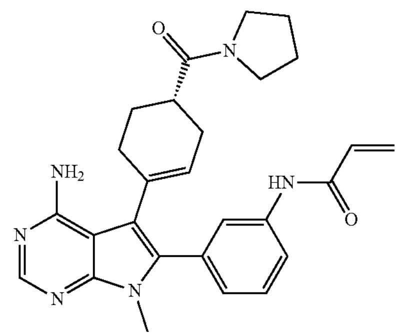 [SMILES: C=CC(=O)Nc1cccc(-c2c(C3=CC[C@@H](C(=O)N4CCCC4)CC3)c3c(N)ncnc3n2C)c1] | $^1$H NMR (400 MHz, DMSO-d$_6$): δ 10.27 (s, 1H), 8.11 (s, 1H), 7.90 (s, 1H), 7.66 (dd, J = 8.0 Hz, 1H), 7.44 (t, J = 8.0 Hz, 1H), 7.20 (d, J = 7.6 Hz, 1H), 6.530 (br, 2H), 6.491-6.423 (m, 1H), 6.35-6.21 (m, 1H), 5.83-5.71 (m, 2H), 3.69-3.53 (m, 3H), 3.52-3.40 (m, 2H), 3.42-3.40 (m, 1H), 3.29-3.20 (m, 2H), 2.81 (m, 1H), 2.37-2.13 (m, 2H), 1.98-1.58 (m, 8H). | 471.1 |

TABLE 2-continued

Additional Exemplary Compounds

| Compound | Structure | Proton NMR | MS [M + 1] |
|---|---|---|---|
| N-(3-{4-amino-7-methyl-5-[(4R)-4-(pyrrolidine-1-carbonyl)cyclohex-1-en-1-yl]-7H-pyrrolo[2,3-d]pyrimidin-6-yl}phenyl)prop-2-enamide | 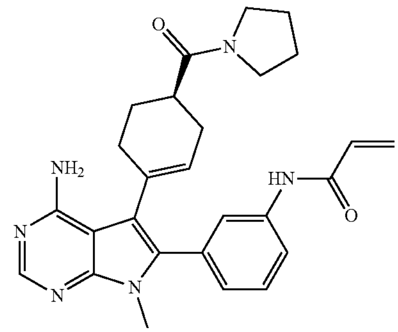 [SMILES: C=CC(=O)Nc1cccc(-c2c(C3=CC[C@H](C(=O)N4CCCC4)CC3)c3c(N)ncnc3n2C)c1] | $^1$H NMR (400 MHz, DMSO-d$_6$): δ 10.28 (s, 1H), 8.11 (s, 1H), 7.90 (s, 1H), 7.67 (dd, J = 8.0 Hz, 1H), 7.44 (t, J = 8.0 Hz, 1H), 7.20 (d, J = 7.6 Hz, 1H), 6.526 (br, 2H), 6.493-6.425 (m, 1H), 6.33-6.22 (m, 1H), 5.85-5.69 (m, 2H), 3.60 (s, 3H), 3.52-3.40 (m, 4H), 3.34-3.20 (m, 3H), 2.88-2.74 (m, 1H), 2.38-2.14 (m, 2H), 2.01-1.56 (m, 8H). | 471.1 |
| N-(4-{4-amino-7-methyl-5-[(1R)-3'-oxo-1',3'-dihydrospiro[cyclohexane-1,2'-inden]-3-en-4-yl]-7H-pyrrolo[2,3-d]pyrimidin-6-yl}phenyl)-2-methylprop-2-enamide | 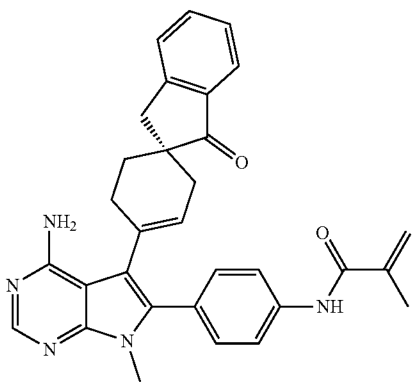 [SMILES: C=C(C)C(=O)Nc1ccc(-c2c(C3=CC[C@]4(CC3)Cc3ccccc3C4=O)c3c(N)ncnc3n2C)cc1] | $^1$H NMR (400 MHz, Methanol-d$_4$) δ 8.16 (s, 1H), 7.83 (d, J = 8.8 Hz, 2H), 7.75-7.64 (m, 2H), 7.58-7.48 (m, 3H), 7.47-7.39 (m, 1H), 5.98 (s, 1H), 5.87 (s, 1H), 5.58 (d, J = 0.8 Hz, 1H), 3.68 (s, 3H), 3.01 (s, 2H), 2.70-2.43 (m, 1H), 2.37-2.17 (m, 2H), 2.09 (s, 3H), 2.06-1.96 (m, 1H), 1.86-1.78 (m, 1H), 1.69-1.56 (m, 1H). | 504.1 |
| N-(4-{4-amino-7-methyl-5-[(1S)-3'-oxo-1',3'-dihydrospiro[cyclohexane-1,2'-inden]-3-en-4-yl]-7H-pyrrolo[2,3-d]pyrimidin-6-yl}phenyl)-2-methylprop-2-enamide | 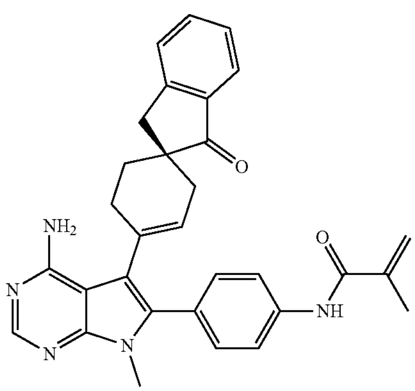 [SMILES: C=C(C)C(=O)Nc1ccc(-c2c(C3=CC[C@@]4(CC3)Cc3ccccc3C4=O)c3c(N)ncnc3n2C)cc1] | $^1$HNMR (400 MHz, Methanol-d$_4$) δ 8.06 (s, 1H), 7.79-7.66 (m, 2H), 7.64-7.50 (m, 2H), 7.46-7.36 (m, 3H), 7.35-7.28 (m, 1H), 5.87 (s, 1H), 5.75 (s, 1H), 5.46 (d, J = 0.8 Hz, 1H), 3.58 (s, 3H), 2.89 (s, 2H), 2.55-2.34 (m, 1H), 2.27-2.04 (m, 2H), 1.97 (s, 3H), 1.94-1.87 (m, 1H), 1.72-1.66 (m, 1H), 1.58-1.47 (m, 1H). | 504.1 |
| N-(4-{4-amino-5-[(1R)-2'-methoxy-7'-oxo-5',7'-dihydrospiro[cyclohexane-1,6'-cyclopenta[b]pyridin]-3-en-4-yl]-7-methyl-7H-pyrrolo[2,3-d]pyrimidin-6-yl}phenyl)-2-methylprop-2-enamide | | $^1$H NMR (400 MHz, DMSO-d$_6$): δ 9.97 (s, 1H), 8.13 (s, 1H), 7.93 (d, J = 8.4 Hz, 1H), 7.84 (d, J = 8.4 Hz, 2H), 7.48 (d, J = 8.4 Hz, 2H), 7.12 (d, J = 8.4 Hz, 1H), 6.51 (br, 2H), 5.87-5.78 (m, 2H), 5.56 (s, 1H), 3.88 (s, 3H), 3.60 (s, 3H), 2.89-2.74 (m, 2H), 2.47-2.42 (m, 2H), 2.14-2.09 (m, 2H), 2.05-1.98 (m, 4H), 1.83-1.66 (m, 1H), 1.58-1.45 (m, 1H). | 535.1 |

TABLE 2-continued

Additional Exemplary Compounds

| Compound | Structure | Proton NMR | MS [M + 1] |
|---|---|---|---|
| N-(4-{4-amino-5-[(1S)-2'-methoxy-7'-oxo-5',7'-dihydrospiro[cyclohexane-1,6'-cyclopenta[b]pyridin]-3-en-4-yl]-7-methyl-7H-pyrrolo[2,3-d]pyrimidin-6-yl}phenyl)-2-methylprop-2-enamide | | $^1$H NMR (400 MHz, DMSO-d$_6$): δ 9.99 (s, 1H), 8.13 (s, 1H), 7.94 (d, J = 8.4 Hz, 1H), 7.85 (d, J = 8.8 Hz, 2H), 7.48 (d, J = 8.4 Hz, 2H), 7.13 (d, J = 8.4 Hz, 1H), 6.53 (br, 2H), 5.90-5.80 (m, 2H), 5.56 (s, 1H), 3.89 (s, 3H), 3.61 (s, 3H), 2.92-2.77 (m, 2H), 2.47-2.43 (m, 1H), 2.14-2.10 (m, 2H), 2.02-1.99 (m, 4H), 1.81-1.69 (m, 1H), 1.57-1.46 (m, 1H). | 535.1 |
| N-(4-{4-amino-7-methyl-5-[(1R)-2'-methyl-7'-oxo-5',7'-dihydrospiro[cyclohexane-1,6'-cyclopenta[b]pyridin]-3-en-4-yl]-7H-pyrrolo[2,3-d]pyrimidin-6-yl}phenyl)-2-methylprop-2-enamide | 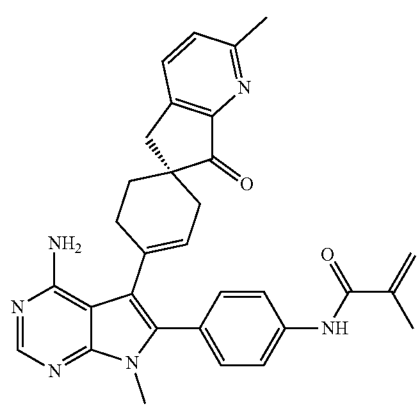 [SMILES: C=C(C)C(=O)Nc1ccc(-c2c(C3=CC[C@]4(CC3)Cc3ccc(C)nc3C4=O)c3c(N)ncnc3n2C)cc1] | $^1$H NMR (400 MHz, CDCl$_3$): δ 8.33 (s, 1H), 7.79-7.67 (m, 3H), 7.61 (s, 1H), 7.44 (d, J = 8.4 Hz, 2H), 7.35 (d, J = 8.0 Hz, 1H), 5.96 (br, 1H), 5.86 (s, 1H), 5.54 (s, 1H), 3.70 (s, 3H), 2.93 (s, 2H), 2.68 (s, 3H), 2.61-2.56 (m, 1H), 2.45-2.15 (m, 3H), 2.12 (s, 3H), 2.05-1.92 (m, 1H), 1.89-1.78 (m, 1H) | 519.1 |
| N-(4-{4-amino-7-methyl-5-[(1S)-2'-methyl-7'-oxo-5',7'-dihydrospiro[cyclohexane-1,6'-cyclopenta[b]pyridin]-3-en-4-yl]-7H-pyrrolo[2,3-d]pyrimidin-6-yl}phenyl)-2-methylprop-2-enamide | 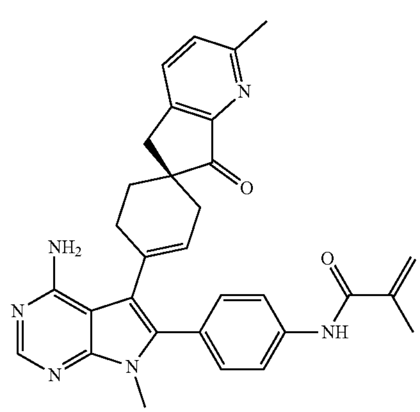 [SMILES: C=C(C)C(=O)Nc1ccc(-c2c(C3=CC[C@@]4(CC3)Cc3ccc(C)nc3C4=O)c3c(N)ncnc3n2C)cc1] | $^1$H NMR (400 MHz, CDCl$_3$): δ 8.28 (s, 1H), 7.79-7.69 (m, 3H), 7.65 (s, 1H), 7.43 (d, J = 8.4 Hz, 2H), 7.36 (d, J = 8.0 Hz, 1H), 5.96 (s, 1H), 5.86 (s, 1H), 5.54 (s, 1H), 3.72 (s, 3H), 2.94 (s, 2H), 2.68 (s, 3H), 2.59-2.53 (m, 1H), 2.43-2.26 (m, 3H), 2.12 (s, 3H), 2.02-1.92 (m, 1H), 1.82-1.71 (m, 1H). | 519.1 |

Scheme 2

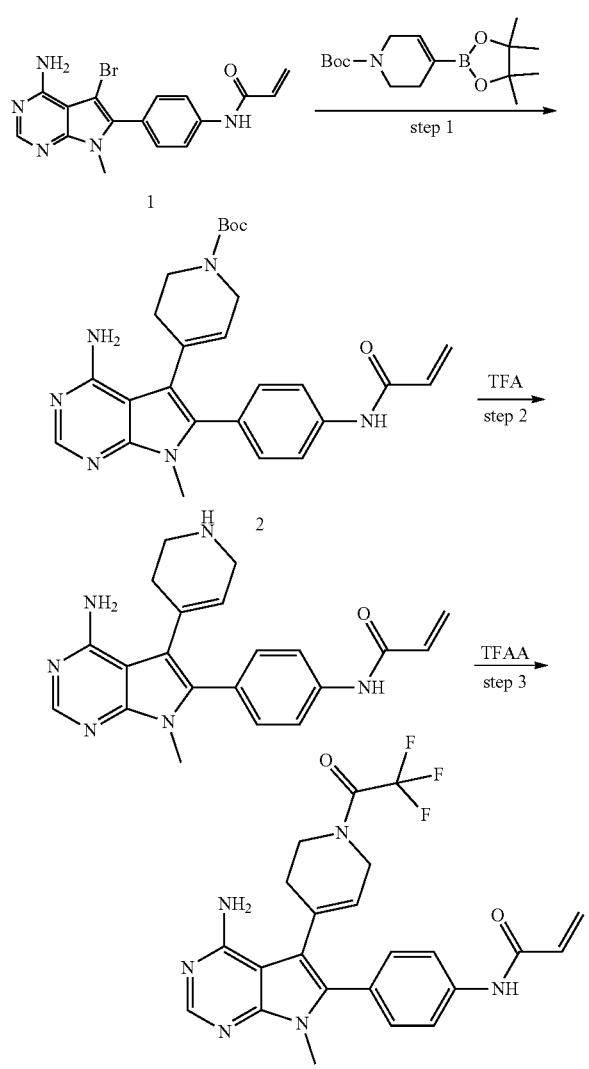

Example 4

N-(4-(4-amino-7-methyl-5-(1-(2,2,2-trifluoroacetyl)-1,2,3,6-tetrahydropyridin-4-yl)-7H-pyrrolo[2,3-d]pyrimidin-6-yl)phenyl)acrylamide

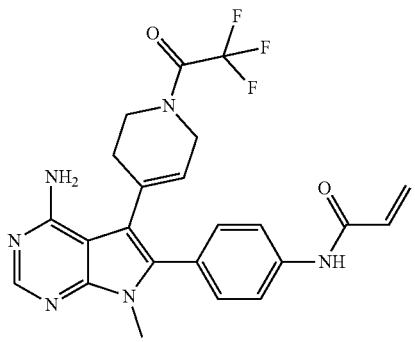 [SMILES: C=CC(=O)Nc1ccc(-c2c(C3=CCN(C(=O)C(F)(F)F)CC3)c3c(N)ncnc3n2C)cc1]

tert-butyl 4-(6-(4-acrylamidophenyl)-4-amino-7-methyl-7H-pyrrolo[2,3-d]pyrimidin-5-yl)-3,6-dihydropyridine-1(2H)-carboxylate

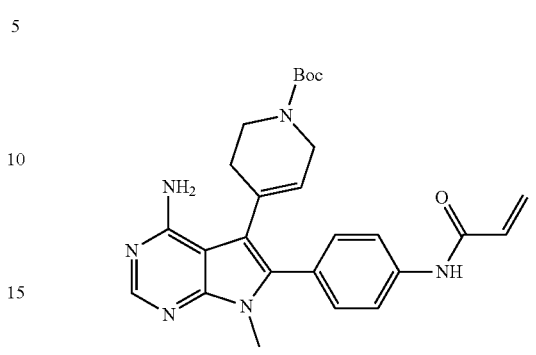

Step 1: A round bottomed flask was charged with N-(4-{4-amino-5-bromo-7-methyl-7H-pyrrolo[2,3-d]pyrimidin-6-yl}phenyl)prop-2-enamide (200 mg, 537 µmol), tert-butyl 4-(4,4,5,5-tetramethyl-1,3,2-dioxaborolan-2-yl)-1,2,3,6-tetrahydropyridine-1-carboxylate (199 mg, 644 µmol), Pd(dtbpf)Cl2 (34.9 mg, 53.7 µmol), K3PO4 (341 mg, 1.61 mmol), 5 mL of DMF and a stirbar. The solution was stirred at 90° C. for 2 h. The reaction mixture was diluted with water (50 mL), and the aqueous phase was extracted with dichloromethane (20 mL) three times. The combined organic layers were washed with brine, dried over sodium sulfate, filtered, and concentrated in vacuo. The resulting crude material was purified by silica gel chromatography (2 g column; eluting with heptanes/ethyl acetate; 3:1). Concentration in vacuo resulted in tert-butyl 4-{4-amino-7-methyl-6-[4-(prop-2-enamido)phenyl]-7H-pyrrolo[2,3-d]pyrimidin-5-yl}-1,2,3,6-tetrahydropyridine-1-carboxylate (121 mg, 48%) as a yellow oil.

N-(4-(4-amino-7-methyl-5-(1,2,3,6-tetrahydropyridin-4-yl)-7H-pyrrolo[2,3-d]pyrimidin-6-yl)phenyl)acrylamide

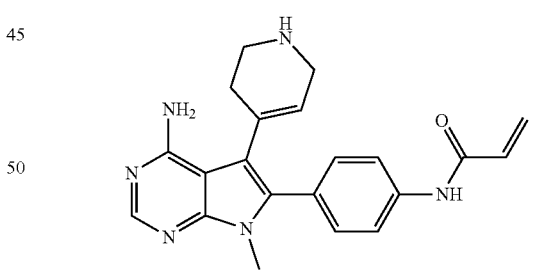

Step 2: A round bottomed flask was charged with tert-butyl 4-{4-amino-7-methyl-6-[4-(prop-2-enamido)phenyl]-7H-pyrrolo[2,3-d]pyrimidin-5-yl}-1,2,3,6-tetrahydropyridine-1-carboxylate (30 mg, 63.2 µmol), 0.2 mL of TFA, 0.8 mL of DCM and a stirbar. The solution was stirred at room temperature for 1 h. The reaction mixture was filtered, and concentrated in vacuo. The resulting crude material was purified by HPLC (acetonitrile/water/0.1% formic acid). Lyophilization yielded N-{4-[4-amino-7-methyl-5-(1,2,3,6-tetrahydropyridin-4-yl)-7H-pyrrolo[2,3-d]pyrimidin-6-yl]phenyl}prop-2-enamide (16.8 mg, 71%) as a white amorphous solid.

N-(4-(4-amino-7-methyl-5-(1-(2,2,2-trifluoroacetyl)-1,2,3,6-tetrahydropyridin-4-yl)-7H-pyrrolo[2,3-d]pyrimidin-6-yl)phenyl)acrylamide

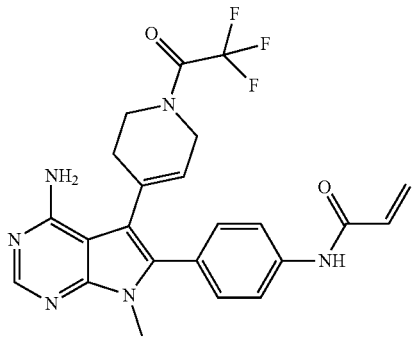 [SMILES: C=CC(=O)Nc1ccc(-c2c(C3=CCN(C(=O)C(F)(F)F)CC3)c3c(N)ncnc3n2C)cc1]

Step 3: A round bottomed flask was charged with N-{4-[4-amino-7-methyl-5-(1,2,3,6-tetrahydropyridin-4-yl)-7H-pyrrolo[2,3-d]pyrimidin-6-yl]phenyl}prop-2-enamide (40 mg, 106 μmol), TEA (32.1 mg, 318 μmol), DMAP (1.29 mg, 10.6 μmol), 5 mL of DCM and a stir bar. TFAA was added dropwise at 0° C. The solution was stirred at room temperature for 1 h. The reaction mixture was diluted with water (30 mL), and the aqueous phase was extracted with dichloromethane (20 mL) three times. The combined organic layers were washed with brine, dried over sodium sulfate, filtered, and concentrated in vacuo. The resulting crude material was purified by HPLC (acetonitrile/water/0.1% formic acid). Lyophilization yielded N-(4-{4-amino-7-methyl-5-[1-(2,2,2-trifluoroacetyl)-1,2,3,6-tetrahydropyridin-4-yl]-7H-pyrrolo[2,3-d]pyrimidin-6-yl}phenyl)prop-2-enamide (27.9 mg, 37%) as a white amorphous solid.

Additional compounds prepared according to the methods of Example 4 are depicted in Table 3 below.

TABLE 3

Additional Exemplary Compounds

| Compound | Structure | Proton NMR | MS [M + 1] |
|---|---|---|---|
| N-(4-(4-amino-7-methyl-5-(1-(2,2,2-trifluoroacetyl)-1,2,3,6-tetrahydropyridin-4-yl)-7H-pyrrolo[2,3-d]pyrimidin-6-yl)phenyl)acrylamide | 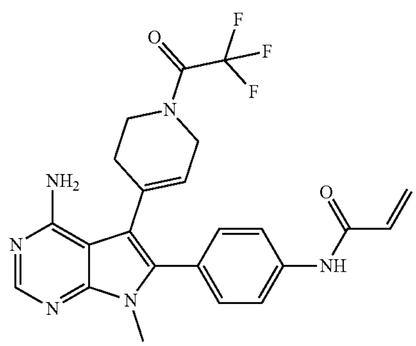 [SMILES: C=CC(=O)Nc1ccc(-c2c(C3=CCN(C(=O)C(F)(F)F)CC3)c3c(N)ncnc3n2C)cc1] | $^1$H NMR (400 MHz, DMSO-d6) δ 10.33 (d, J = 2.8 Hz, 1H), 8.14 (d, J = 1.2 Hz, 1H), 7.87-7.68 (m, 2H), 7.47-7.39 (m, 2H), 6.49-6.28 (m, 3H), 5.85-5.70 (m, 2H), 4.30-4.09 (m, 2H), 3.65-3.52 (m, 5H), 2.09 (s, 2H). | 471.1 |
| N-(4-(4-amino-7-methyl-5-(1,2,3,6-tetrahydropyridin-4-yl)-7H-pyrrolo[2,3-d]pyrimidin-6-yl)phenyl)acrylamide | 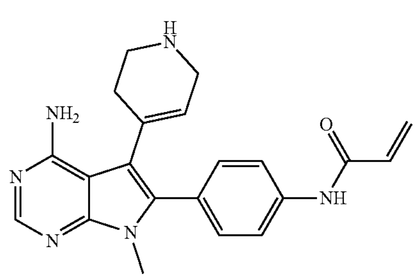 [SMILES: C=CC(=O)Nc1ccc(-c2c(C3=CCNCC3)c3c(N)ncnc3n2C)cc1] | $^1$H NMR (400 MHz, DMSO-d6) δ 10.30 (d, J = 28.0 Hz, 1H), 8.21-8.08 (m, 1H), 7.80-7.56 (m, 2H), 7.44-7.39 (m, 2H), 6.56-6.05 (m, 2H), 5.80 (d, J = 10.4 Hz, 1H), 3.57-3.46 (m, 4H), 3.16 (d, J = 46.0 Hz, 2H), 2.77-2.63 (m, 2H), 2.00 (m, J = 46.4 Hz, 2H). | 375.2 |

Scheme 3
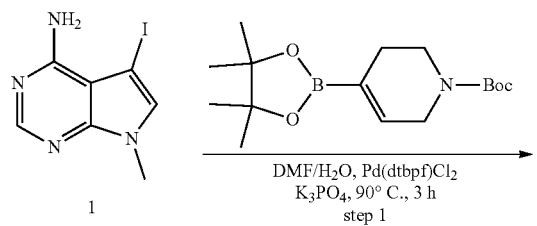
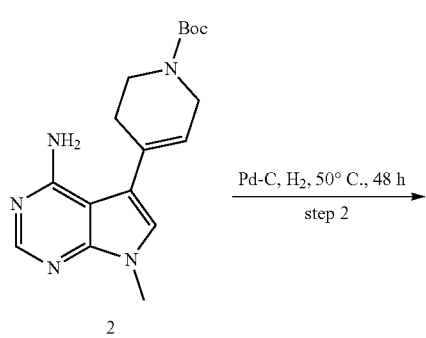
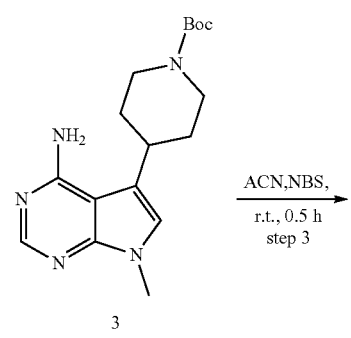
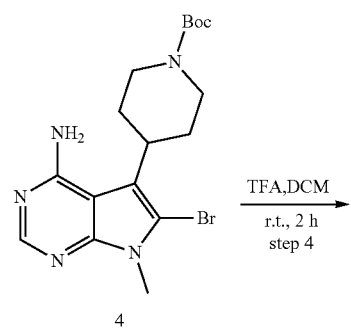
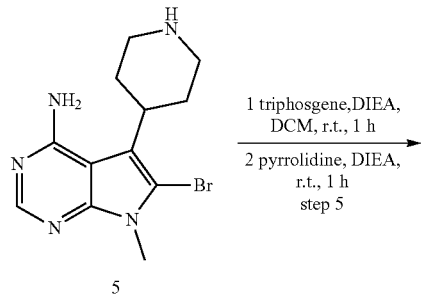
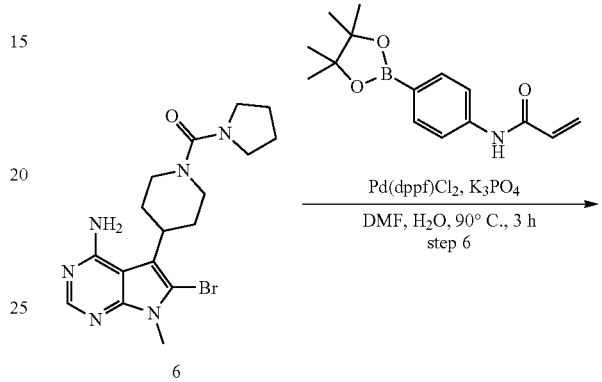
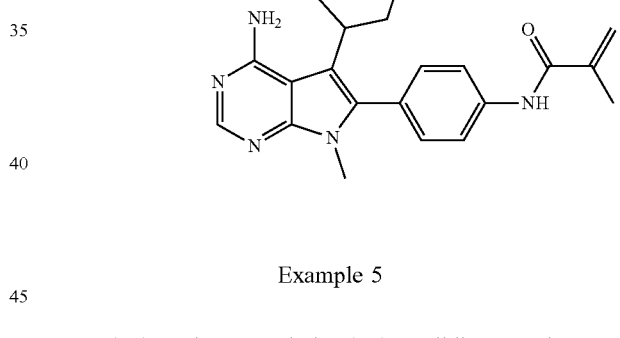
Example 5
N-(4-(4-amino-7-methyl-5-(1-(pyrrolidine-1-carbonyl)piperidin-4-yl)-7H-pyrrolo[2,3-d]pyrimidin-6-yl)phenyl)methacrylamide
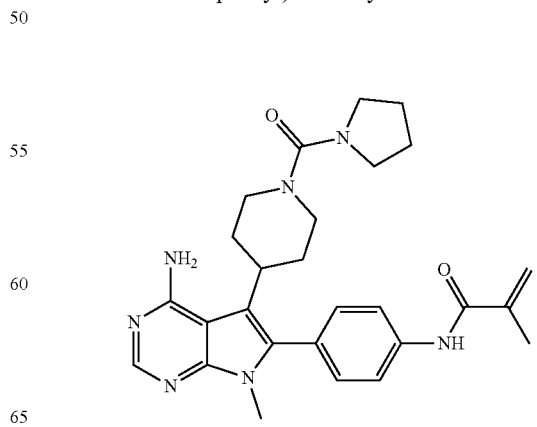

1303 tert-butyl 4-(4-amino-7-methyl-7H-pyrrolo[2,3-d]pyrimidin-5-yl)-3,6-dihydropyridine-1(2H)-carboxylate

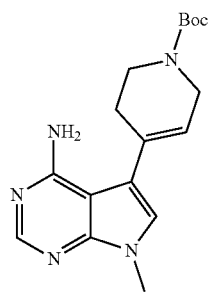 [SMILES: Cn1cc(C2=CCN(C(=O)OC(C)(C)C)CC2)c2c(N)ncnc21]

Step 1: A round bottomed flask was charged with 5-iodo-7-methyl-7H-pyrrolo[2,3-d]pyrimidin-4-amine (3.00 g, 10.9 mmol), tert-butyl 4-(4,4,5,5-tetramethyl-1,3,2-dioxaborolan-2-yl)-1,2,3,6-tetrahydropyridine-1-carboxylate (4.01 g, 13.0 mmol), Pd(dtbpf)Cl$_2$ (710 mg, 1.09 mmol), K$_3$PO$_4$ (6.91 g, 32.6 mmol) and a stirbar. DMF (45 mL) and H$_2$O (3 mL) was added, and the solution was stirred for 3 h at 90° C. The mixture was diluted with EtOAc (300 mL) and washed with water (3*100 mL), the organic phase was concentrated and the crude product was purified by silica gel column with DCM:MeOH=25:1 to afford tert-butyl 4-{4-amino-7-methyl-7H-pyrrolo[2,3-d]pyrimidin-5-yl}-1,2,3,6-tetrahydropyridine-1-carboxylate (2.97 g, 83%) as brown oil.

tert-butyl 4-(4-amino-7-methyl-7H-pyrrolo[2,3-d]pyrimidin-5-yl)piperidine-1-carboxylate

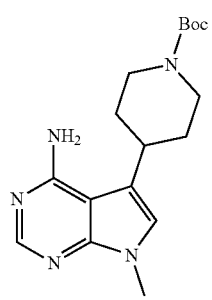 [SMILES: Cn1cc(C2CCN(C(=O)OC(C)(C)C)CC2)c2c(N)ncnc21]

Step 2: A round bottomed flask was charged with tert-butyl 4-{4-amino-7-methyl-7H-pyrrolo[2,3-d]pyrimidin-5-yl}-1,2,3,6-tetrahydropyridine-1-carboxylate (1.70 g, 5.16 mmol), Pd/C (326 mg, 154 μmol), and a stirbar. MeOH (50 mL) was added, and the solution was stirred at 50° C. for 48 h under H$_2$. The mixture was filtered and washed with MeOH for 5 times, the filtration was concentrated and obtained tert-butyl 4-{4-amino-7-methyl-7H-pyrrolo[2,3-d]pyrimidin-5-yl}piperidine-1-carboxylate (900 mg, 53%) as brown oil.

1304 tert-butyl 4-(4-amino-6-bromo-7-methyl-7H-pyrrolo[2,3-d]pyrimidin-5-yl)piperidine-1-carboxylate

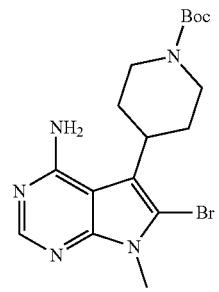 [SMILES: Cn1c(Br)c(C2CCN(C(=O)OC(C)(C)C)CC2)c2c(N)ncnc21]

Step 3: A round bottomed flask was charged with tert-butyl 4-{4-amino-7-methyl-7H-pyrrolo[2,3-d]pyrimidin-5-yl}piperidine-1-carboxylate (800 mg, 2.41 mmol), NBS (428 mg, 2.41 mmol and a stirbar. ACN (20 mL) was added, and the solution was stirred at 25° C. for 0.5 h. The mixture was concentrated under reduced pressure and obtained the product tert-butyl 4-{4-amino-6-bromo-7-methyl-7H-pyrrolo[2,3-d]pyrimidin-5-yl}piperidine-1-carboxylate (500 mg, 51%) as brown solid. The crude product was used next step without further purification.

6-bromo-7-methyl-5-(piperidin-4-yl)-7H-pyrrolo[2,3-d]pyrimidin-4-amine

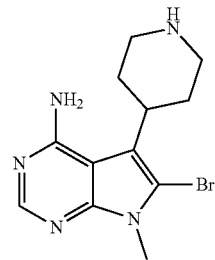 [SMILES: Cn1c(Br)c(C2CCNCC2)c2c(N)ncnc21]

Step 4: A round bottomed flask was charged with tert-butyl 4-{4-amino-6-bromo-7-methyl-7H-pyrrolo[2,3-d]pyrimidin-5-yl}piperidine-1-carboxylate (500 mg, 1.21 mmol), DCM (5 mL) and a stirbar. TFA (0.5 mL) was added, and the solution was stirred at 25° C. for 2 h. The mixture was concentrated under reduced pressure, and diluted with DCM (30 mL), washed with saturated NaHCO$_3$ aq. (3*15 mL), the organic phase was concentrated and obtained the product 6-bromo-7-methyl-5-(piperidin-4-yl)-7H-pyrrolo[2,3-d]pyrimidin-4-amine (310 mg, 83%) as brown oil.

1305
(4-(4-amino-6-bromo-7-methyl-7H-pyrrolo[2,3-d]pyrimidin-5-yl)(piperidin-1-yl)(pyrrolidin-1-yl)methanone

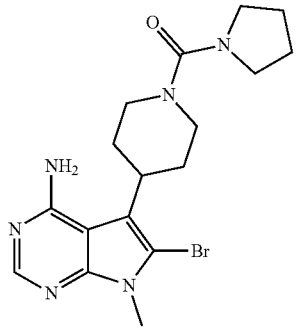 [SMILES: Cn1c(Br)c(C2CCN(C(=O)N3CCCC3)CC2)c2c(N)ncnc21]

Step 5: A round bottomed flask was charged with 6-bromo-7-methyl-5-(piperidin-4-yl)-7H-pyrrolo[2,3-d]pyrimidin-4-amine (280 mg, 902 μmol), DIEA (580 mg, 4.50 mmol), DCM (10 mL) and a stirbar. triphosgene (106 mg, 360 μmol) was added, and the solution was stirred for 1 h at room temperature, then pyrrolidine (512 mg, 7.21 mmol) was added and stirred for 1 h at room temperature. The solvent was removed and the crude product was purified by C18 Flash to afford 6-bromo-7-methyl-5-[1-(pyrrolidine-1-carbonyl)piperidin-4-yl]-7H-pyrrolo[2,3-d]pyrimidin-4-amine (160 mg, 21%) as off-white solid.

1306
N-(4-(4-amino-7-methyl-5-(1-(pyrrolidine-1-carbonyl)piperidin-4-yl)-7H-pyrrolo[2,3-d]pyrimidin-6-yl)phenyl)methacrylamide

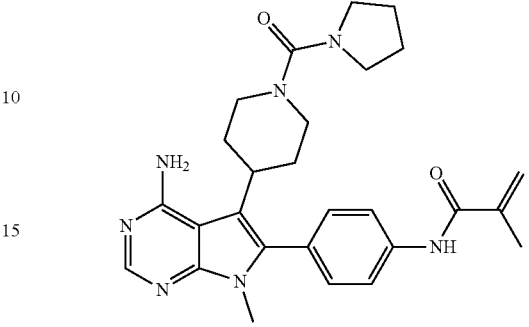

Step 6: A resealable reaction vial was charged with 6-bromo-7-methyl-5-[1-(pyrrolidine-1-carbonyl)piperidin-4-yl]-7H-pyrrolo[2,3-d]pyrimidin-4-amine (140 mg, 0.34 mmol), N-(4-(4,4,5,5-tetramethyl-1,3,2-dioxaborolan-2-yl)phenyl)acrylamide (112 mg, 0.41 mmol), Pd(dppf)Cl$_2$ (25.1 mg, 34.3 μmol), K$_3$PO$_4$ (216 mg, 1.02 mmol), and a stirbar before being evacuated and purged with nitrogen three times. DMF (1 mL) and H$_2$O (0.1 mL) was added, and the mixture was stirred 3 h at 90° C. The resulted mixture was purified through C18 Column. The resulting crude material was purified by HPLC. Lyophilization yielded N-(4-{4-amino-7-methyl-5-[1-(pyrrolidine-1-carbonyl)piperidin-4-yl]-7H-pyrrolo[2,3-d]pyrimidin-6-yl}phenyl)-2-methylprop-2-enamide (24.3 mg, 15%) as a white amorphous solid.

Additional compounds prepared according to the methods of Example 5 are depicted in Table 4 below.

TABLE 4

Exemplary Compound

| Compound | Structure | Proton NMR | MS [M + 1] |
|---|---|---|---|
| N-(4-(4-amino-7-methyl-5-(1-(pyrrolidine-1-carbonyl)piperidin-4-yl)-7H-pyrrolo[2,3-d]pyrimidin-6-yl)phenyl)methacrylamide | 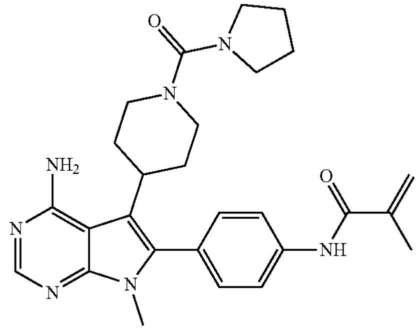 [SMILES: C=C(C)C(=O)Nc1ccc(-c2c(C3CCN(C(=O)N4CCCC4)CC3)c3c(N)ncnc3n2C)cc1] | $^1$H NMR (400 MHz, DMSO-d$_6$) δ 9.98 (s, 1H), 8.11 (s, 1H), 7.83 (d, J = 8.4 Hz, 2H), 7.35 (d, J = 8.3 Hz, 2H), 6.38 (s, 2H), 5.83 (s, 1H), 5.56 (s, 1H), 3.58-3.61 (m, 2H), 3.55 (s, 3H), 3.26-3.38 (m, 4H), 3.02-3.05 (m, 1H), 2.68-2.76 (m, 2H), 2.08 (s, 3H), 1.63-1.66 (m, 4H), 1.48-1.57 (m, 4H). | 488.3 |

Scheme 4

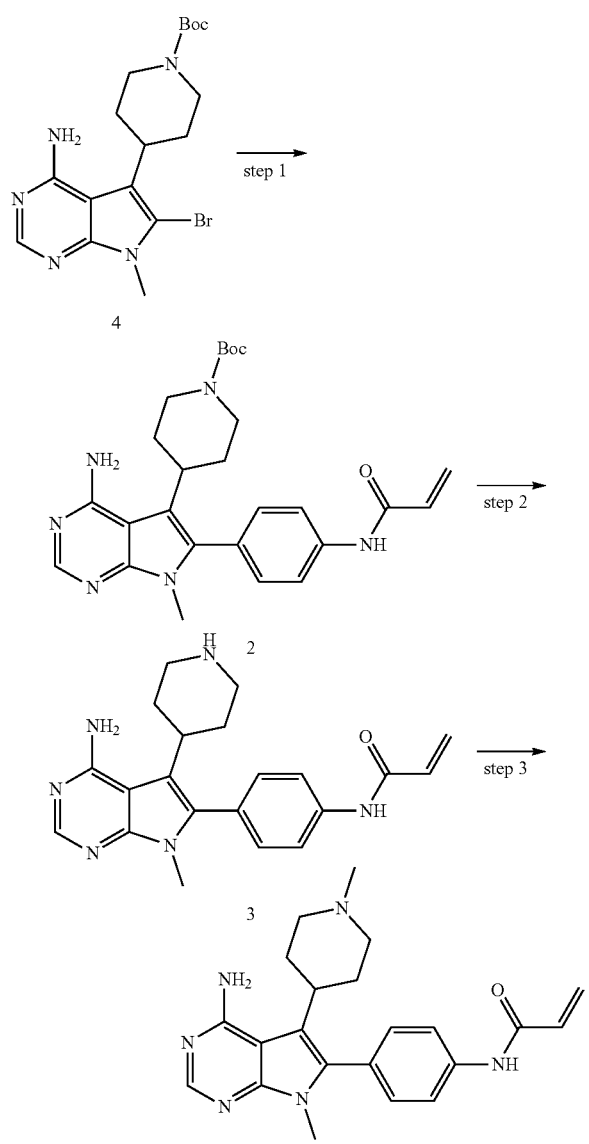

Example 6

N-(4-(4-amino-7-methyl-5-(1-methylpiperidin-4-yl)-7H-pyrrolo[2,3-d]pyrimidin-6-yl)phenyl)acrylamide

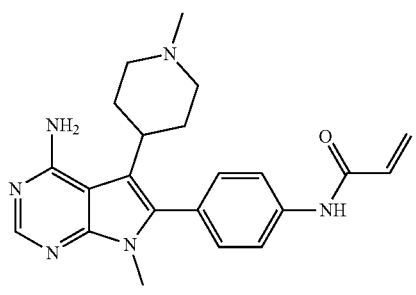 [SMILES: C=CC(=O)Nc1ccc(-c2c(C3CCN(C)CC3)c3c(N)ncnc3n2C)cc1]

tert-butyl 4-(6-(4-acrylamidophenyl)-4-amino-7-methyl-7H-pyrrolo[2,3-d]pyrimidin-5-yl)piperidine-1-carboxylate

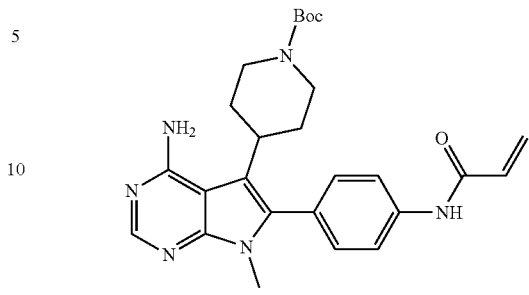

Step 1: A round bottomed flask was charged with tert-butyl 4-(4-amino-6-bromo methyl-7H-pyrrolo[2,3-d]pyrimidin-5-yl)piperidine-1-carboxylate (700 mg, 1.7 mmol), N-(4-(4,4,5,5-tetramethyl-1,3,2-dioxaborolan-2-yl)phenyl)acrylamide (559 mg, 2.0 mmol), Pd(dtbpf)Cl2 (124 mg, 0.17 mmol), $K_3PO_4$ (1.08 g, 5.1 mmol) and a stirbar. DMF (10 mL) and $H_2O$ (1 mL) was added, and the solution was stirred for 3 h at 90° C. The mixture was diluted with EtOAc (100 mL) and washed with water (3*100 mL), the organic phase was concentrated and the crude product was purified by silica gel column with DCM:MeOH=25:1 to afford tert-butyl 4-(6-(4-acrylamidophenyl)-4-amino-7-methyl-7H-pyrrolo[2,3-d]pyrimidin-5-yl)piperidine-1-carboxylate (340 mg, 42%) as yellow solid.

tert-butyl 4-(4-amino-7-methyl-7H-pyrrolo[2,3-d]pyrimidin-5-yl)piperidine-1-carboxylate

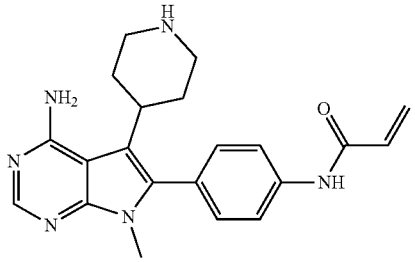 [SMILES: C=CC(=O)Nc1ccc(-c2c(C3CCNCC3)c3c(N)ncnc3n2C)cc1]

Step 2: A round bottomed flask was charged with tert-butyl 4-(6-(4-acrylamidophenyl)-4-amino-7-methyl-7H-pyrrolo[2,3-d]pyrimidin-5-yl)piperidine-1-carboxylate (340 mg, 0.71 mmol), DCM (5 mL) and a stirbar. TFA (0.5 mL) was added, and the solution was stirred at 25° C. for 2 h. The mixture was concentrated under reduced pressure, and diluted with DCM (30 mL), washed with saturated $NaHCO_3$ aq. (3*15 mL), the organic phase was concentrated and obtained the product tert-butyl 4-(4-amino-7-methyl-7H-pyrrolo[2,3-d]pyrimidin-5-yl)piperidine-1-carboxylate (240 mg, 89%) as brown oil.

N-(4-(4-amino-7-methyl-5-(1-methylpiperidin-4-yl)-7H-pyrrolo[2,3-d]pyrimidin-6 yl)phenyl) acrylamide

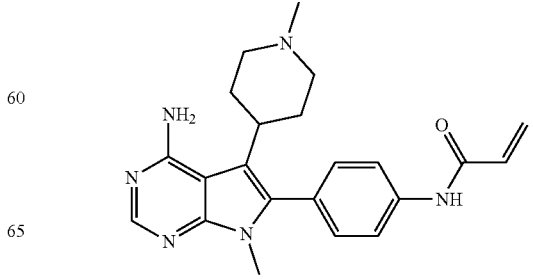

Step 3: A round bottomed flask was charged with tert-butyl 4-(4-amino-7-methyl-7H-pyrrolo[2,3-d]pyrimidin-5-yl)piperidine-1-car-boxylate (120 mg, 0.32 mmol), NaBH(OAc)$_3$ (81 mg, 0.38 mmol), (CH$_2$O)n (20 mg, 0.64 mmol) and a stirbar. DCM (5 mL) and AcOH (0.5 mL) was added, and the solution was stirred overnight at room temperature. The reaction mixture was diluted with water (50 mL), and the aqueous phase was extracted with DCM (20 mL) three times. The combined organic layers dried over sodium sulfate, filtered, and concentrated in vacuo. The resulting crude material was purified by HPLC. Lyophilization yielded N-(4-{4-amino-7-methyl-5-[1-(pyrrolidine-1-carbonyl)piperidin-4-yl]-7H-pyrrolo[2,3-d]pyrimidin-6-yl}phenyl)-2-methylprop-2-enamide (8 mg, 6%) as a white amorphous solid.

Additional compounds prepared according to the methods of Example 6 are depicted in Table 5 below.

TABLE 5

Exemplary Compound

| Compound | Structure | Proton NMR | MS [M + 1] |
|---|---|---|---|
| N-(4-(4-amino-7-methyl-5-(1-methylpiperidin-4-yl)-7H-pyrrolo[2,3-d]pyrimidin-6-yl)phenyl)acrylamide | 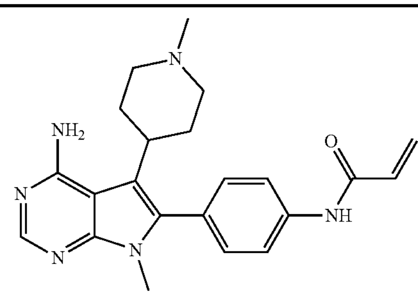 | $^1$H NMR (400 MHz, DMSO-d6) δ 10.35 (s, 1H), 8.11 (s, 1H), 7.85-7.78 (m, 2H), 7.40-7.29 (m, 2H), 6.49 (dd, J = 17.0, 10.1 Hz, 1H), 6.37-6.28 (m, 3H), 5.81 (dd, J = 10.0, 2.0 Hz, 1H), 3.37 (s, 3H), 2.75 (d, J = 10.9 Hz, 3H), 2.50-2.31 (m, 3H), 2.14 (s, 3H), 1.93-1.91 (m, 2H), 1.65 (s, 4H). | 391.2 |

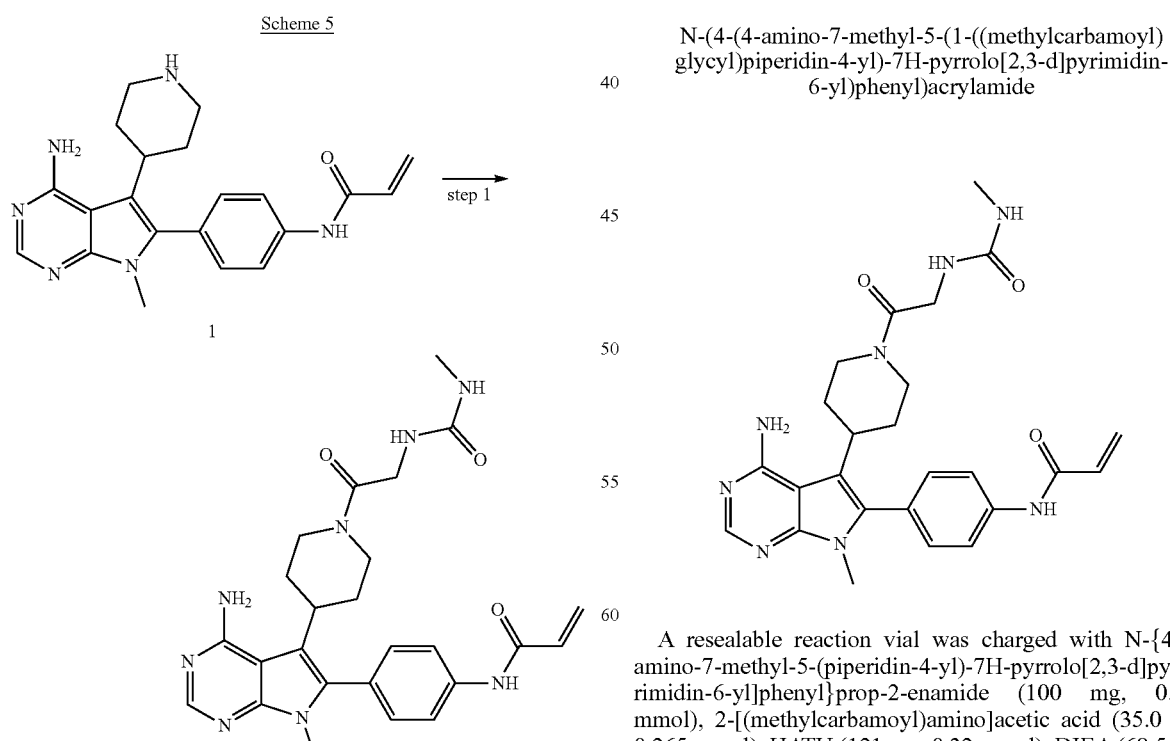

Scheme 5

Example 7

N-(4-(4-amino-7-methyl-5-(1-((methylcarbamoyl)glycyl)piperidin-4-yl)-7H-pyrrolo[2,3-d]pyrimidin-6-yl)phenyl)acrylamide A resealable reaction vial was charged with N-{4-[4-amino-7-methyl-5-(piperidin-4-yl)-7H-pyrrolo[2,3-d]pyrimidin-6-yl]phenyl}prop-2-enamide (100 mg, 0.265 mmol), 2-[(methylcarbamoyl)amino]acetic acid (35.0 mg, 0.265 mmol), HATU (121 mg, 0.32 mmol), DIEA (68.5 mg, 0.53 mmmol), and a stirbar. Dimethylformamide (5 mL) was added, and the mixture was stirred for 1 h at r.t. The reaction mixture was diluted with water (10 mL), and the aqueous phase was extracted with dichloromethane (15 mL) three times. The combined organic layers were washed with brine, dried over sodium sulfate, filtered, and concentrated in vacuo. The resulting crude material was purified by HPLC (acetonitrile/water/0.1% formic acid). Lyophilization yielded N-{4-[4-amino-7-methyl-5-(1-{2-[(methylcarbamoyl)amino]acetyl}piperidin-4-yl)-7H-pyrrolo[2,3-d]pyrimidin-6-yl]phenyl}prop-2-enamide (6.00 mg, 5%) as a white amorphous solid.

Additional compounds prepared according to the methods of Example 7 are depicted in Table 6 below.

TABLE 6

Additional Exemplary Compounds

| Compound | Structure | Proton NMR | MS [M + 1] |
|---|---|---|---|
| N-(4-(4-amino-7-methyl-5-(1-((methylcarbamoyl)glycyl)piperidin-4-yl)-7H-pyrrolo[2,3-d]pyrimidin-6-yl)phenyl)acrylamide | 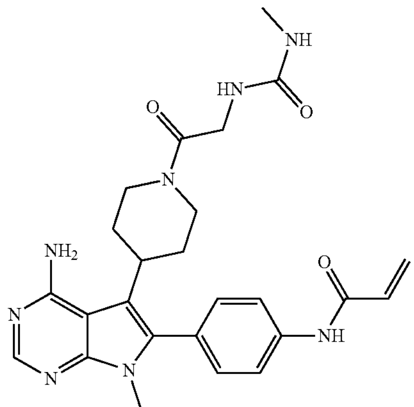 [SMILES: C=CC(=O)Nc1ccc(-c2c(C3CCN(C(=O)CNC(=O)NC)CC3)c3c(N)ncnc3n2C)cc1] | $^1$H NMR (400 MHz, DMSO-d6) δ 10.35 (s, 1H), 8.10 (s, 1H), 7.79 (d, J = 8.3 Hz, 2H), 7.34 (d, J = 8.2 Hz, 2H), 6.47 (dd, J = 17.0, 10.2 Hz, 1H), 6.39 (s, 2H), 6.30 (d, J = 16.8 Hz, 1H), 6.10 (s, 1H), 5.92 (s, 1H), 5.80 (d, J = 10.5 Hz, 1H), 3.78-3.66 (m, 3H), 3.45-3.37 (m, 1H), 3.31 (s, 3H), 3.21-3.08 (m, 2H), 2.55-2.53 (m, 1H), 2.51 (s, 3H), 1.86-1.73 (m, 2H), 1.45-1.24 (m, 2H). | 491.2 |
| (R)-N-(4-(4-amino-5-(1-(4-(dimethylamino)-2-methylbutanoyl)piperidin-4-yl)-7-methyl-7H-pyrrolo[2,3-d]pyrimidin-6-yl)phenyl)acrylamide | 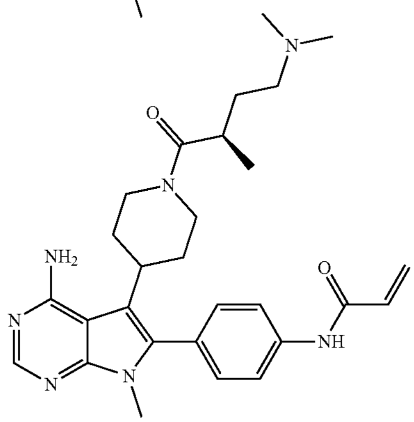 | $^1$H NMR (400 MHz, DMSO-d6) δ 10.31 (s, 1H), 8.10 (s, 1H), 7.79 (d, J = 8.0 Hz, 2H), 7.32 (t, J = 7.2 Hz, 2H), 6.53-6.42 (m, 3H), 6.30 (dd, J = 16.8, 2.1 Hz, 1H), 5.80 (dd, J = 10.0, 2.0 Hz, 1H), 4.37 (s, 1H), 3.88 (s, 1H), 3.28 (s, 3H), 3.09 (t, J = 13.6 Hz, 1H), 2.75-2.61 (m, 2H), 2.06 (s, 4H), 2.01 (s, 4H), 1.76-1.48 (m, 4H), 1.29-1.22 (m, 3H), 0.91-0.82 (m, 3H). | 504.4 |

Example 8

Scheme 6

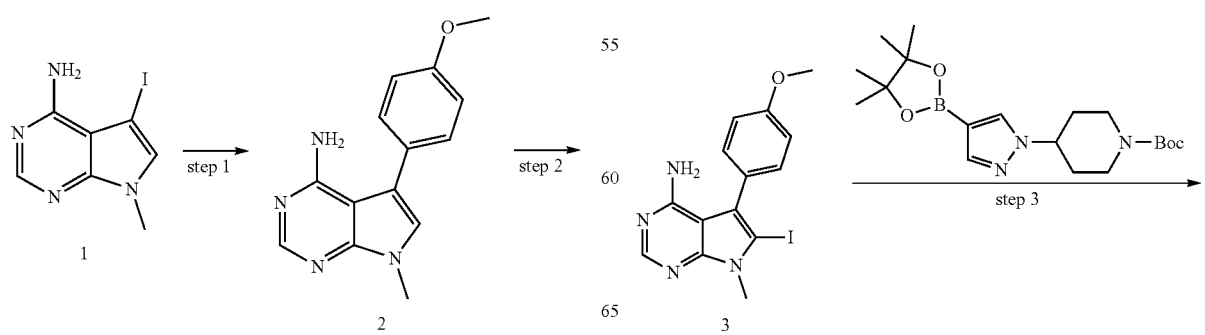

-continued

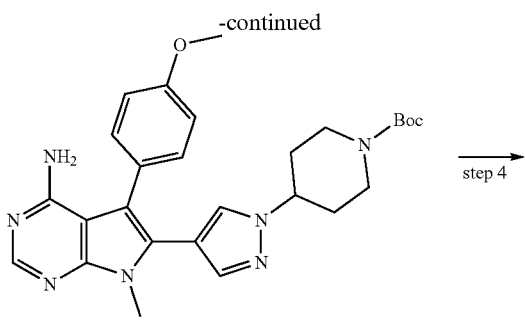

4


5

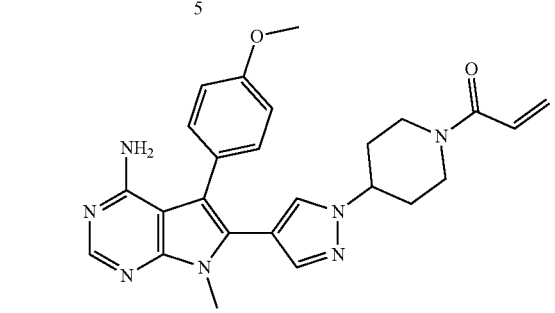

5-(4-methoxyphenyl)-7-methyl-7H-pyrrolo[2,3-d]pyrimidin-4-amine

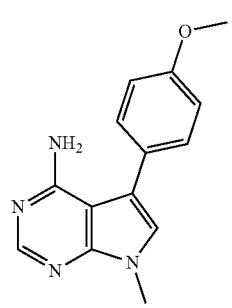 [SMILES: COc1ccc(-c2cn(C)c3ncnc(N)c23)cc1]

Step 1: A resealable reaction vial was charged with 5-iodo-7-methyl-7H-pyrrolo[2,3-d]pyrimidin-4-amine (20 g, 72.9 mmol), (4-methoxyphenyl)boronic acid (13.3 g, 87.5 mmol), Pd(DtBPF)Cl₂ (4.74 g, 7.29 mmol), CsF (33.1 g, 218 mmol), DMF (200 mL), H₂O (25 mL) and a stir bar before being evacuated and purged with nitrogen three times. The mixture was stirred for 1 h at 90° C. The reaction mixture was diluted with H₂O (500 mL), and the aqueous phase was extracted with DCM (200 mL) three times. The combined organic layers were washed with brines, dried over sodium sulfate, filtered, and concentrated in vacuo. The reaction mixture was added MeCN (10 mL) and filtered through a pad of Celite®, the pad was washed with MeCN. The filtrate was concentrated in vacuo and the resulting solid was 5-(4-methoxyphenyl)-7-methyl-7H-pyrrolo[2,3-d]pyrimidin-4-amine (10.2 g, 55%), obtained as a yellow amorphous solid.

6-iodo-5-(4-methoxyphenyl)-7-methyl-7H-pyrrolo[2,3-d]pyrimidin-4-amine

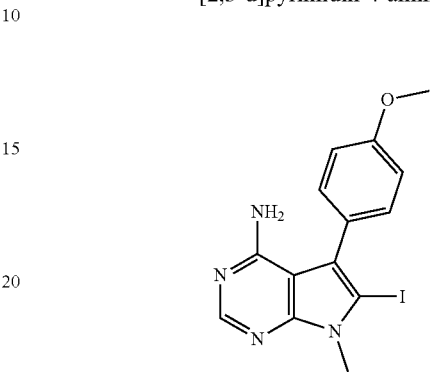

Step 2: A round bottomed flask was charged with 5-(4-methoxyphenyl)-7-methyl-7H-pyrrolo[2,3-d]pyrimidin-4-amine (9.8 g, 38.5 mmol), DCM (200 mL), TFA (13.1 g, 115 mmol) and a stir bar. The mixture was cooled to 0° C., NIS (9.53 g, 42.4 mmol) was added, and the solution was stirred for 1 h at room temperature. The reaction mixture was diluted with Na₂SO₃ solution, and the aqueous phase was extracted with DCM (300 mL) three times. The combined organic layers were washed with brines, dried over sodium sulfate, filtered, and concentrated in vacuo. DCM (20 mL) was added and the reaction mixture was filtered through a pad of Celite®, the pad was washed with little DCM. The filtrate was concentrated in vacuo and the resulting solid was 6-iodo-5-(4-methoxyphenyl)-7-methyl-7H-pyrrolo[2,3-d]pyrimidin-4-amine (10.9 g, 74%), obtained as an off-white amorphous solid.

tert-butyl 4-(4-(4-amino-5-(4-methoxyphenyl)-7-methyl-7H-pyrrolo[2,3-d]pyrimidin 6-yl)-1H-pyrazol-1-yl)piperidine-1-carboxylate

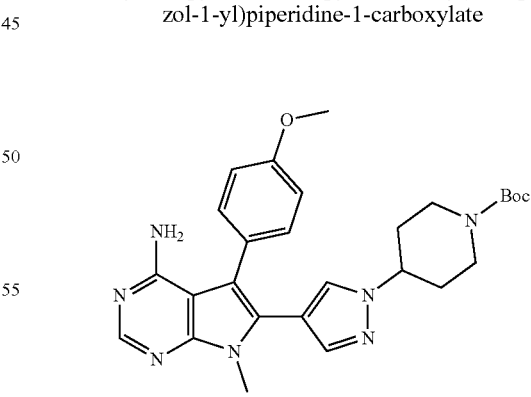

Step 3: A resealable reaction vial was charged with 6-iodo-5-(4-methoxyphenyl)-7-methyl-7H-pyrrolo[2,3-d]pyrimidin-4-amine (1 g, 2.63 mmol), tert-butyl 4-(4-(4,4,5,5-tetramethyl-1,3,2-dioxaborolan-2-yl)-1H-pyrazol-1-yl)piperidine-1-carboxylate (1.2 g, 3.16 mmol), Pd(dppf)Cl₂ (190 mg, 0.26 mmol), K₃PO₄ (1.5 g, 6.9 mmol), DMF (20 mL), H₂O (2 mL) and a stir bar before being evacuated and purged with nitrogen three times. The mixture was stirred for 1 h at 90° C. The reaction mixture was diluted with H₂O (100 mL), and the aqueous phase was extracted with DCM (100 mL) three times. The combined organic layers were washed with brines, dried over sodium sulfate, filtered, and concentrated in vacuo. The resulting crude material was purified by silica gel chromatography (eluting with MeOH/DCM=1/40). Concentration in vacuo resulted in tert-butyl 4-(4-(4-amino-5-(4-methoxyphenyl)-7-methyl-7H-pyrrolo[2,3-d]pyrimidin-6-yl)-1H-pyrazol-1-yl)piperidine-1-carboxylate (800 mg, 61%) as a yellow solid.

5-(4-methoxyphenyl)-7-methyl-6-(1 (piperidin-4-yl)-1H-pyrazol-4-yl)-7H-pyrrolo[2,3-d]pyrimidin-4-amine trifluoroacetate salt

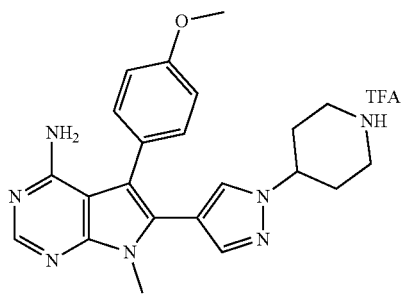 [SMILES: COc1ccc(-c2c(-c3cnn(C4CCNCC4)c3)n(C)c3ncnc(N)c23)cc1 ; "TFA"]

Step 4: A round bottomed flask was charged with tert-butyl 4-(4-(4-amino-5-(4-methoxyphenyl)-7-methyl-7H-pyrrolo[2,3-d]pyrimidin-6-yl)-1H-pyrazol-1-yl)piperidine-1-carboxylate (800 mg, 1.6 mmol), DCM (20 mL) and a stir bar. TFA (5 mL) was added. The reaction mixture was stirred for 1 h at room temperature. The solvent was removed in vacuo resulted in 5-(4-methoxyphenyl)-7 methyl-6-(1 (piperidin-4-yl)-1H-pyrazol-4-yl)-7H-pyrrolo[2,3-d]pyrimidin-4-amine trifluoracetate salt (795 mg, 100%) as a dark oil.

1-(4-(4-(4-amino-5-(4-methoxyphenyl)-7-methyl-7H-pyrrolo[2,3-d]pyrimidin-6-yl)-1H-pyrazol-1-yl) piperidin-1-yl)prop-2-en-1-one

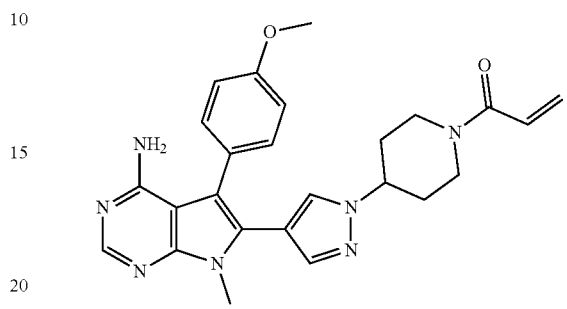

Step 5: A round bottomed flask was charged with 5-(4-methoxyphenyl)-7-methyl-6-(1-(piperidin-4-yl)-1H-pyrazol-4-yl)-7H-pyrrolo[2,3-d]pyrimidin-4-amine trifluoroacetate salt (120 mg, 0.24 mmol), Et₃N (72.9 mg, 0.72 mmol) DCM (10 mL) and a stir bar. The mixture was cooled to −30° C., prop-2-enoyl chloride (21.6 mg, 0.24 mmol) was added dropwise and the solution was stirred for 0.5 h at −30° C. The reaction mixture was quenched with MeOH, and concentrated in vacuo. The resulting crude material was purified by prep-HPLC. Lyophilization yielded 1-(4-(4-(4-amino-5-(4-methoxyphenyl)-7-methyl-7H-pyrrolo[2,3-d]pyrimidin-6-yl)-1H-pyrazol-1-yl)piperidin-1-yl)prop-2-en-1-one (33 mg, 30%) as a white amorphous solid.

Additional compounds prepared according to the methods of Example 8 are depicted in Table 7 below.

TABLE 7

Additional Exemplary Compounds

| Compound | Structure | Proton NMR | MS [M + 1] |
|---|---|---|---|
| 1-(4-(4-(4-amino-7-methyl-5-(4-phenoxyphenyl)-7H-pyrrolo[2,3-d]pyrimidin-6-yl)-1H-pyrazol-1-yl)piperidin-1-yl)propan-1-one | 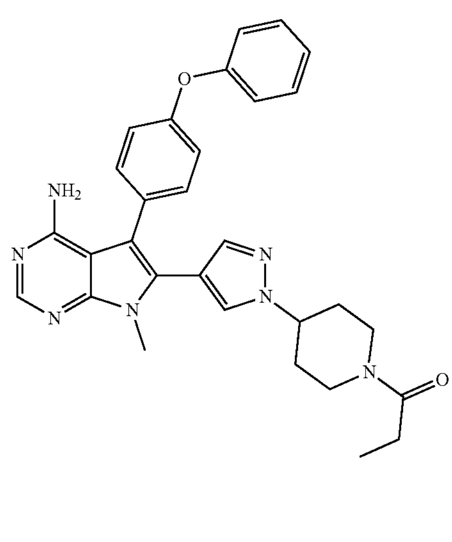 [SMILES: CCC(=O)N1CCC(n2cc(-c3c(-c4ccc(Oc5ccccc5)cc4)c4c(N)ncnc4n3C)cn2)CC1] | ¹H NMR (400 MHz, DMSO-d6) δ 1.63-1.88 (m, 2H), 2.01 (t, J = 14.8 Hz, 2H), 2.35 (q, J = 7.6 Hz, 2H), 2.73 (t, J = 12.4 Hz, 1H), 3.16 (t, J = 12.8 Hz, 1H), 3.70 (s, 3H), 3.93 (d, J = 14.0 Hz, 1H), 4.43 (td, J = 5.6, 11.5 Hz, 2H), 5.85 (s, 1H), 7.02-7.07 (m, 2H), 7.07-7.12 (m, 2H), 7.17 (t, J = 7.2 Hz, 1H), 7.27-7.35 (m, 2H), 7.39-7.46 (m, 3H), 7.89 (s, 1H), 8.15 (s, 1H). | 522.23 |

TABLE 7-continued

Additional Exemplary Compounds

| Compound | Structure | Proton NMR | MS [M + 1] |
|---|---|---|---|
| 1-(4-(4-(4-amino-5-(4-methoxyphenyl)-7-methyl-7H-pyrrolo[2,3-d]pyrimidin-6-yl)-1H-pyrazol-1-yl)piperidin-1-yl)prop-2-en-1-one | 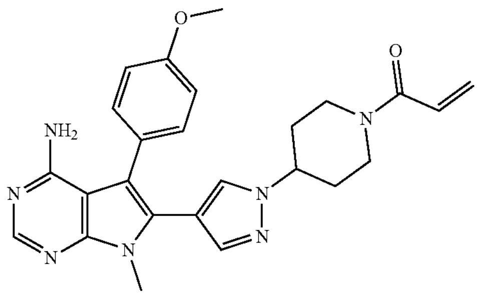 [SMILES: C=CC(=O)N1CCC(n2cc(-c3c(-c4ccc(OC)cc4)c4c(N)ncnc4n3C)cn2)CC1] | $^1$H NMR (400 MHz, DMSO-d6) δ 8.18 (s, 1H), 7.95 (s, 1H), 7.36 (s, 1H), 7.29-7.21 (m, 2H), 7.04-6.96 (m, 2H), 6.85 (m, 1H), 6.12 (m, 1H), 5.70 (m, 1H), 4.47 (t, J = 7.2 Hz, 2H), 4.13 (d, J = 13.6 Hz, 1H), 3.79 (s, 3H), 3.70 (s, 3H), 3.24 (d, J = 13.6 Hz, 1H), 2.83 (t, J = 12.4 Hz, 1H), 2.04 (d, J = 12.4 Hz, 2H), 1.79 (d, J = 16.8 Hz, 2H). | 458.22 |
| 1-(3-(4-(4-amino-7-methyl-5-(4-((6-methylpyridin-2-yl)oxy)phenyl)-7H-pyrrolo[2,3-d]pyrimidin-6-yl)-1H-pyrazol-1-yl)-2-methylpiperidin-1-yl)prop-2-en-1-one | 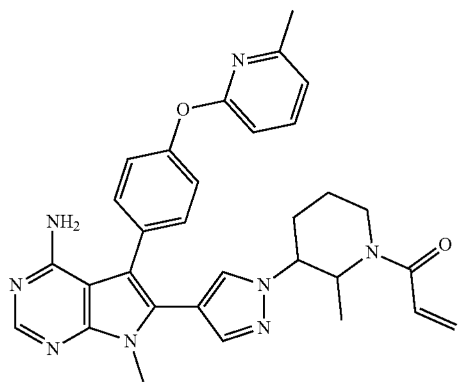 [SMILES: C=CC(=O)N1CCCC(n2cc(-c3c(-c4ccc(Oc5cccc(C)n5)cc4)c4c(N)ncnc4n3C)cn2)C1C] | $^1$H NMR (400 MHz, DMSO-d$_6$) δ 8.16 (s, 1H), 7.77 (s, 1H), 7.80-7.72 (m, 1H), 7.48 (s, 1H), 7.38-7.25 (m, 2H), 7.16-7.10 (m, 2H), 7.05 (d, J = 7.4 Hz, 1H), 6.82 (d, J = 8.2 Hz, 1H), 6.66 (s, 1H), 6.01 (d, J = 16.4 Hz, 1H), 5.60 (d, J = 10.4 Hz, 1H), 5.01 (s, 1H), 4.38 (s, 1H), 4.07 (s, 1H), 3.66 (s, 3H), 3.32 (s, 1H), 3.07 (s, 1H), 2.37 (s, 3H), 2.15 (s, 2H), 1.49 (s, 1H), 1.38 (s, 1H), 1.31 (d, J = 6.8 Hz, 3H). | 549.25 |
| 1-(3-(4-(4-amino-7-methyl-5-(4-phenoxyphenyl)-7H-pyrrolo[2,3-d]pyrimidin-6-yl)-1H-pyrazol-1-yl)-2-methylpiperidin-1-yl)prop-2-en-1-one | 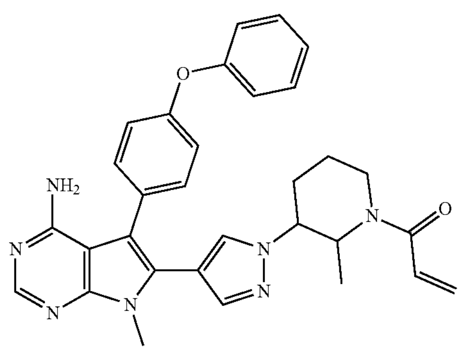 [SMILES: C=CC(=O)N1CCCC(n2cc(-c3c(-c4ccc(Oc5ccccc5)cc4)c4c(N)ncnc4n3C)cn2)C1C] | $^1$H NMR (400 MHz, DMSO-d$_6$) δ 8.16 (s, 1H), 7.77 (s, 1H), 7.80-7.72 (m, 1H), 7.48 (s, 1H), 7.38-7.25 (m, 2H), 7.16-7.10 (m, 2H), 7.05 (d, J = 7.4 Hz, 1H), 6.82 (d, J = 8.2 Hz, 1H), 6.66 (s, 1H), 6.01 (d, J = 16.4 Hz, 1H), 5.60 (d, J = 10.4 Hz, 1H), 5.01 (s, 1H), 4.38 (s, 1H), 4.07 (s, 1H), 3.66 (s, 3H), 3.32 (s, 1H), 3.07 (s, 1H), 2.15 (s, 2H), 1.49 (s, 1H), 1.38 (s, 1H), 1.31 (d, J = 6.8 Hz, 3H). | 534.25 |
| 1-(3-(4-(4-amino-7-methyl-5-(4-((6-methylpyridin-2-yl)oxy)phenyl)-7H-pyrrolo[2,3-d]pyrimidin-6-yl)-1H-pyrazol-1-yl)piperidin-1-yl)prop-2-en-1-one | 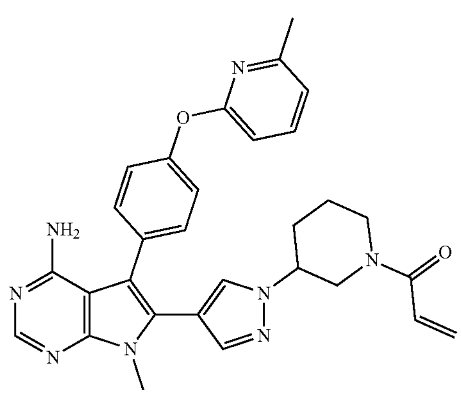 [SMILES: C=CC(=O)N1CCCC(n2cc(-c3c(-c4ccc(Oc5cccc(C)n5)cc4)c4c(N)ncnc4n3C)cn2)C1] | $^1$H NMR (400 MHz, DMSO-d6) δ 8.16 (s, 1H), 7.96 (s, 1H), 7.79-7.71 (m, 1H), 7.47 (s, 1H), 7.38-7.31 (m, 2H), 7.16 (d, J = 8.4 Hz, 2H), 7.03 (d, J = 7.2 Hz, 1H), 6.82 (d, J = 8.4 Hz, 2H), 6.38-5.91 (m, 1H), 5.67 (dd, J = 10.4, 32.3 Hz, 1H), 4.51-3.93 (m, 3H), 3.70 (s, 3H), 3.56 (s, 0H), 3.17 (s, 1H), 2.98 (s, 0H), 2.36 (s, 3H), 2.09 (d, J = 17.2 Hz, 2H), 1.77 (s, 1H), 1.50 (s, 1H). | 535.25 |

TABLE 7-continued

Additional Exemplary Compounds

| Compound | Structure | Proton NMR | MS [M + 1] |
|---|---|---|---|
| 1-(4-(4-(4-amino-7-methyl-5-(4-(6-methylpyridin-2-yl)oxy)phenyl)-7H-pyrrolo[2,3-d]pyrimidin-6-yl)-1H-pyrazol-1-yl)piperidin-1-yl)-2-methylprop-2-en-1-one | 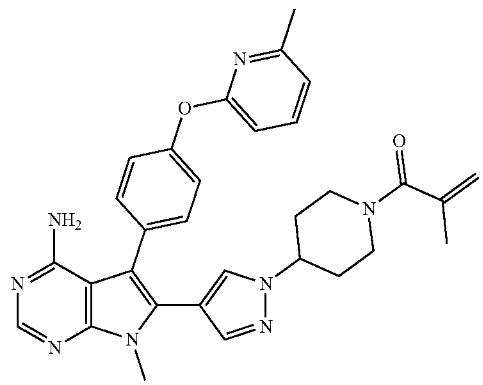 [SMILES: C=C(C)C(=O)N1CCC(n2cc(-c3c(-c4ccc(Oc5cccc(C)n5)cc4)c4c(N)ncnc4n3C)cn2)CC1] | $^1$H NMR (400 MHz, DMSO-d6) δ 8.16 (s, 1H), 7.95 (s, 1H), 7.74 (t, J = 8.0 Hz, 1H), 7.44 (s, 1H), 7.34 (d, J = 8.4 Hz, 2H), 7.15 (d, J = 8.4 Hz, 2H), 7.03 (d, J = 7.6 Hz, 1H), 6.80 (d, J = 8.4 Hz, 1H), 5.17 (s, 1H), 5.00 (s, 1H), 4.46 (t, J = 11.6 Hz, 1H), 3.94 (s, 1H), 3.70 (s, 3H), 2.84 (s, 1H), 2.35 (s, 3H), 2.04 (d, J = 12.8 Hz, 2H), 1.86 (s, 3H), 1.79 (d, J = 12.8 Hz, 2H). | 549.26 |
| (E)-1-(4-(4-(4-amino-7-methyl-5-(4-(6-methylpyridin-2-yl)oxy)phenyl)-7H-pyrrolo[2,3-d]pyrimidin-6-yl)-1H-pyrazol-1-yl)piperidin-1-yl)-4-(dimethylamino)but-2-en-1-one | 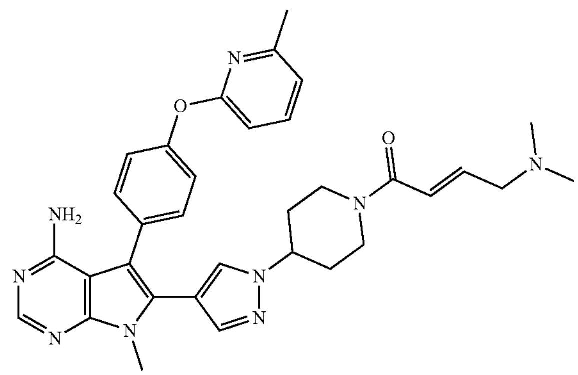 [SMILES: Cc1cccc(Oc2ccc(-c3c(-c4cnn(C5CCN(C(=O)/C=C/CN(C)C)CC5)c4)n(C)c4ncnc(N)c34)cc2)n1] | $^1$H NMR (400 MHz, DMSO-d6) δ 8.15 (s, 1H), 7.95 (s, 1H), 7.75 (t, J = 8.0 Hz, 1H), 7.44 (s, 1H), 7.34 (d, J = 8.4 Hz, 2H), 7.14 (d, J = 8.4 Hz, 2H), 7.03 (d, J = 7.6 Hz, 1H), 6.80 (d, J = 8.4 Hz, 1H), 6.62 (d, J = 2.8 Hz, 2H), 4.45 (s, 2H), 4.13 (s, 1H), 3.69 (s, 3H), 3.02 (d, J = 4.0 Hz, 2H), 2.80 (s, 2H), 2.35 (s, 3H), 2.14 (s, 6H), 2.03 (s, 2H), 1.78 (s, 3H). | 592.41 |
| 1-(3-(4-(4-amino-7-methyl-5-(4-((6-methylpyridin-2-yl)oxy)phenyl)-7H-pyrrolo[2,3-d]pyrimidin-6-yl)-1H-pyrazol-1-yl)pyrrolidin-1-yl)prop-2-en-1-one | 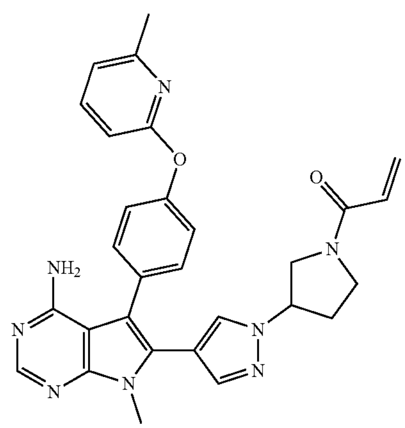 [SMILES: C=CC(=O)N1CCC(n2cc(-c3c(-c4ccc(Oc5cccc(C)n5)cc4)c4c(N)ncnc4n3C)cn2)C1] | $^1$H NMR (400 MHz, DMSO-d6) δ 8.16 (s, 1H), 7.98 (d, J = 18.1 Hz, 1H), 7.78-7.75 (m, 1H), 7.50-7.44 (m, 1H), 7.37-7.30 (m, 2H), 7.14 (dd, J = 8.6, 1.9 Hz, 2H), 7.03 (d, J = 7.4 Hz, 1H), 6.82 (d, J = 8.2 Hz, 1H), 6.57 (dt, J = 16.7, 10.6 Hz, 1H), 6.14 (ddd, J = 16.7, 5.5, 2.4 Hz, 1H), 5.66 (ddd, J = 12.8, 10.3, 2.4 Hz, 1H), 5.09-4.96 (m, 1H), 3.92-3.78 (m, 1H), 3.70 (s, 5H), 3.62-3.42 (m, 3H), 2.36 (s, 4H). | 521.20 |
| 1-(4-(3-(4-amino-7-methyl-5-(4-((6-methylpyridin-2-yl)oxy)phenyl)-7H-pyrrolo[2,3-d]pyrimidin-6-yl)-1,2,4-oxadiazol-5-yl)piperidin-1-yl)prop-2-en-1-one | 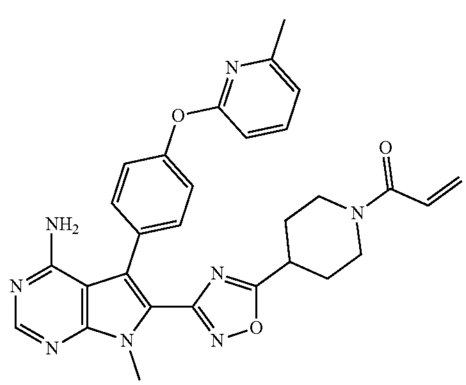 [SMILES: C=CC(=O)N1CCC(c2nc(-c3c(-c4ccc(Oc5cccc(C)n5)cc4)c4c(N)ncnc4n3C)no2)CC1] | $^1$H NMR (400 MHz, DMSO-d$_6$) δ 8.26 (s, 1H), 7.76 (t, J = 7.7 Hz, 1H), 7.42 (d, J = 8.2 Hz, 2H), 7.17 (d, J = 8.1 Hz, 2H), 7.05 (d, J = 7.4 Hz, 1H), 6.79 (dd, J = 17.3, 9.7 Hz, 2H), 6.09 (dd, J = 16.6, 2.5 Hz, 1H), 5.66 (dd, J = 10.3, 2.5 Hz, 1H), 4.15 (d, J = 13.0 Hz, 1H), 3.92 (s, 2H), 3.22 (d, J = 45.6 Hz, 4H), 3.03 (d, J = 12.4 Hz, 1H), 2.37 (s, 3H), 2.12-1.96 (m, 2H), 1.64 (s, 2H). | 537.40 |

TABLE 7-continued

Additional Exemplary Compounds

| Compound | Structure | Proton NMR | MS [M + 1] |
|---|---|---|---|
| 1-(4-5-(4-amino-7-methyl-5-(4-(6-methylpyridin-2-yl)oxy)phenyl)-7H-pyrrolo[2,3-d]pyrimidin-6-yl)-1,3,4-oxadiazol-2-yl)piperidin-1-yl)prop-2-en-1-one | 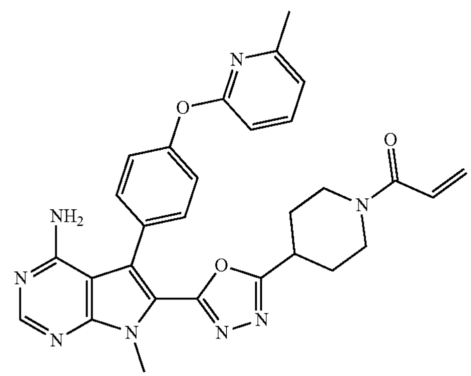 [SMILES: C=CC(=O)N1CCC(c2nnc(-c3c(-c4ccc(Oc5cccc(C)n5)cc4)c4c(N)ncnc4n3C)o2)CC1] | $^1$H NMR (400 MHz, DMSO-$d_6$) δ 1.41-1.68 (m, 2H), 1.80-1.92 (m, 2H), 2.38 (s, 3H), 2.92-3.00 (m, 1H), 3.10-3.26 (m, 2H), 3.85-3.98 (m, 1H), 4.04 (s, 3H), 4.04-4.09 (m, 1H), 5.63 (dd, J = 2.8 Hz, 1H), 6.07 (dd, J = 2.4 Hz, 1H), 6.70-6.77 (m, 1H), 6.83 (d, J = 8.0 Hz, 1H), 7.06 (d, J = 12 Hz, 1H), 7.24 (d, J = 11.2 Hz, 1H), 7.48 (d, J = 4.8 Hz, 1H), 7.79 (t, J = 15.6 Hz, 1H), 8.28 (s, 1H) | 537.40 |
| 1-(4-(4-(4-amino-7-methyl-5-(4-(6-methylpyridin-2-yl)oxy)phenyl)-7H-pyrrolo[2,3-d]pyrimidin-6-yl)-3-methyl-1H-pyrazol-1-yl)piperidin-1-yl)prop-2-en-1-one | 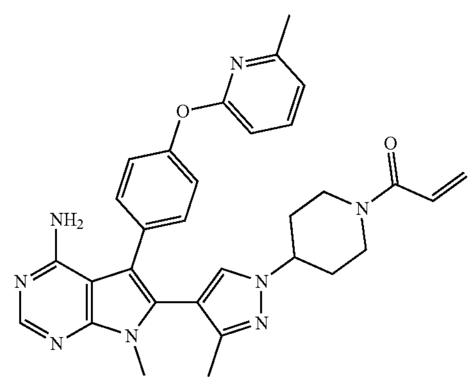 [SMILES: C=CC(=O)N1CCC(n2cc(-c3c(-c4ccc(Oc5cccc(C)n5)cc4)c4c(N)ncnc4n3C)c(C)n2)CC1] | $^1$H NMR (400 MHz, DMSO-$d_6$) δ 8.18 (s, 1H), 8.01 (s, 1H), 7.77-7.70 (m, 1H), 7.25 (d, J = 8.5 Hz, 2H), 7.11 (d, J = 8.6 Hz, 2H), 7.01 (d, J = 7.4 Hz, 1H), 6.89-6.75 (m, 2H), 6.12 (dd, J = 16.7, 2.4 Hz, 1H), 5.71-5.66 (m, 1H), 4.49 (d, J = 12.4 Hz, 1H), 4.39 (d, J = 11.2 Hz, 1H), 4.14 (d, J = 13.5 Hz, 1H), 3.55 (s, 3H), 3.32 (s, 2H), 3.23 (s, 1H), 2.83 (t, J = 13.1 Hz, 1H), 2.34 (s, 3H), 2.07 (d, J = 10.1 Hz, 2H), 1.88-1.75 (m, 2H), 1.70 (s, 3H). | 549.40 |
| 1-(4-(4-(4-amino-7-methyl-5-(4-(5-methylpyridin-2-yl)oxy)phenyl)-7H-pyrrolo[2,3-d]pyrimidin-6-yl)-1H-pyrazol-1-yl)piperidin-1-yl)prop-2-en-1-one | 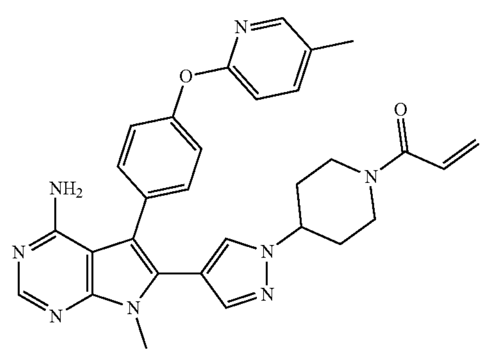 [SMILES: C=CC(=O)N1CCC(n2cc(-c3c(-c4ccc(Oc5ccc(C)cn5)cc4)c4c(N)ncnc4n3C)cn2)CC1] | $^1$H NMR (400 MHz, DMSO-d6) δ 8.16 (s, 1H), 8.03 (dd, J = 2.1, 1.1 Hz, 1H), 7.94 (d, J = 0.7 Hz, 1H), 7.71 (dd, J = 8.2, 2.5 Hz, 1H), 7.45 (d, J = 0.7 Hz, 1H), 7.37-7.29 (m, 2H), 7.17-7.09 (m, 2H), 6.99 (d, J = 8.3 Hz, 1H), 6.85 (dd, J = 16.7, 10.4 Hz, 1H), 6.12 (dd, J = 16.7, 2.4 Hz, 1H), 5.69 (dd, J = 10.4, 2.4 Hz, 1H), 4.51-4.41 (m, 2H), 4.14 (d, J = 13.9 Hz, 1H), 3.70 (s, 3H), 3.23 (t, J = 12.9 Hz, 1H), 2.84 (t, J = 12.5 Hz, 1H), 2.27 (s, 3H), 2.04 (s, 2H), 1.78 (t, J = 13.6 Hz, 2H). | 535.3 |
| 1-(4-(4-(4-amino-7-methyl-5-(4-((4-methylpyridin-2-yl)oxy)phenyl)-7H-pyrrolo[2,3-d]pyrimidin-6-yl)-1H-pyrazol-1-yl)piperidin-1-yl)prop-2-en-1-one | 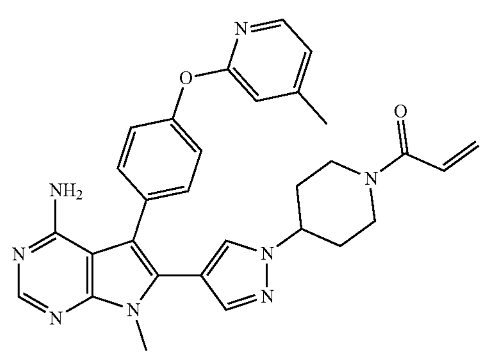 [SMILES: C=CC(=O)N1CCC(n2cc(-c3c(-c4ccc(Oc5cc(C)ccn5)cc4)c4c(N)ncnc4n3C)cn2)CC1] | $^1$H NMR (400 MHz, DMSO-$d_6$) δ 8.16 (s, 1H), 8.05 (d, J = 5.2 Hz, 1H), 7.95 (s, 1H), 7.45 (s, 1H), 7.36-7.31 (m, 2H), 7.16-7.12 (m, 2H), 7.02-6.99 (m, 1H), 6.91 (s, 1H), 6.85 (dd, J = 16.7, 10.5 Hz, 1H), 6.12 (dd, J = 16.7, 2.5 Hz, 1H), 5.69 (dd, J = 10.4, 2.4 Hz, 1H), 4.46 (t, J = 10.8 Hz, 1H), 4.14 (d, J = 13.7 Hz, 1H), 3.70 (s, 3H), 3.21 (d, J = 12.9 Hz, 1H), 2.83 (t, J = 12.6 Hz, 1H), 2.35 (s, 4H), 2.04 (s, 2H), 1.80 (d, J = 13.6 Hz, 2H). | 535.40 |

TABLE 7-continued

Additional Exemplary Compounds

| Compound | Structure | Proton NMR | MS [M + 1] |
|---|---|---|---|
| 1-(4-(4-(4-amino-5-(4-((6-fluoropyridin-2-yl)oxy)phenyl)-7-methyl-7H-pyrrolo[2,3-d]pyrimidin-6-yl)-1H-pyrazol-1-yl)piperidin-1-yl)prop-2-en-1-one | 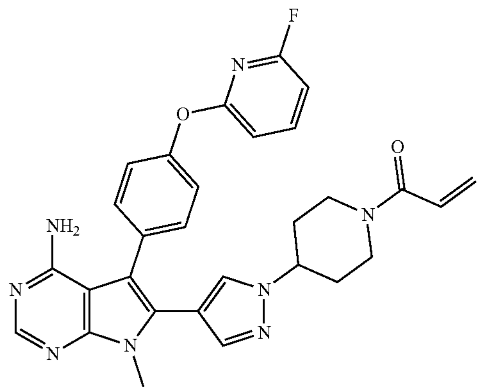 [SMILES: C=CC(=O)N1CCC(n2cc(-c3c(-c4ccc(Oc5cccc(F)n5)cc4)c4c(N)ncnc4n3C)cn2)CC1] | $^1$H NMR (400 MHz, DMSO-d6) δ 8.17 (s, 1H), 8.05 (q, J = 8.1 Hz, 1H), 7.92 (s, 1H), 7.46 (s, 1H), 7.42-7.34 (m, 2H), 7.27-7.19 (m, 2H), 6.97 (dd, J = 7.9, 1.7 Hz, 1H), 6.92 (dd, J = 7.9, 2.4 Hz, 1H), 6.84 (dd, J = 16.7, 10.5 Hz, 1H), 6.12 (dd, J = 16.7, 2.4 Hz, 1H), 5.85 (s, 2H), 5.69 (dd, J = 10.4, 2.4 Hz, 1H), 4.46 (ddd, J = 15.3, 11.3, 3.9 Hz, 1H), 4.14 (d, J = 13.8 Hz, 1H), 3.70 (s, 3H), 3.22 (t, J = 12.9 Hz, 1H), 2.83 (t, J = 12.6 Hz, 1H), 2.05 (d, J = 12.4 Hz, 2H), 1.79 (t, J = 12.8 Hz, 2H). | 539.3 |
| 1-(4-(4-(4-amino-5-(4-((6-methoxypyridin-2-yl)oxy)phenyl)-7-methyl-7H-pyrrolo[2,3-d]pyrimidin-6-yl)-1H-pyrazol-1-yl)piperidin-1-yl)ethan-1-one | 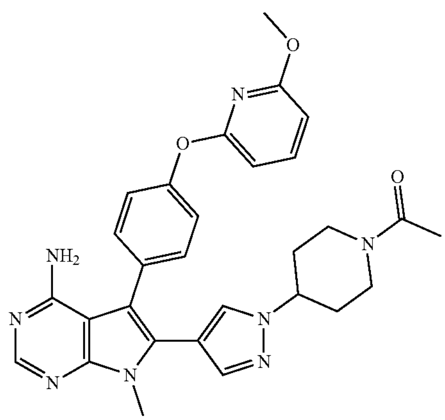 [SMILES: COc1cccc(Oc2ccc(-c3c(-c4cnn(C5CCN(C(C)=O)CC5)c4)n(C)c4ncnc(N)c34)cc2)n1] | $^1$H NMR (400 MHz, DMSO-d$_6$) δ 8.16 (s, 1H), 7.98 (s, 1H), 7.76 (t, J = 7.9 Hz, 1H), 7.41-7.30 (m, 3H), 7.25-7.16 (m, 2H), 6.85 (dd, J = 16.7, 10.4 Hz, 1H), 6.55 (dd, J = 7.9, 5.0 Hz, 2H), 6.12 (dd, J = 16.6, 2.5 Hz, 1H), 5.69 (dd, J = 10.5, 2.4 Hz, 1H), 4.47 (td, J = 12.2, 11.3, 6.8 Hz, 2H), 4.14 (d, J = 13.6 Hz, 1H), 3.69 (d, J = 15.3 Hz, 6H), 3.21 (d, J = 13.0 Hz, 1H), 2.83 (t, J = 12.6 Hz, 1H), 2.04 (d, J = 12.5 Hz, 2H), 1.89-1.65 (m, 2H). | 551.35 |
| 1-(4-(4-(4-amino-7-methyl-5-(4-(pyridin-2-yloxy)phenyl)-7H-pyrrolo[2,3-d]pyrimidin-6-yl)-1H-pyrazol-1-yl)piperidin-1-yl)prop-2-en-1-one | 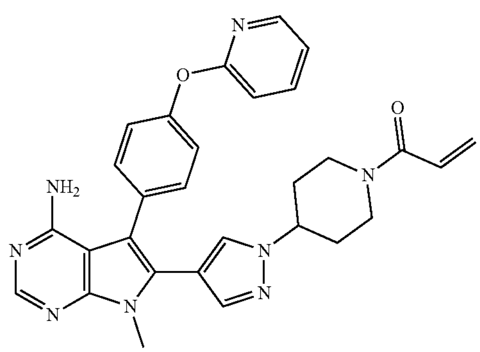 [SMILES: C=CC(=O)N1CCC(n2cc(-c3c(-c4ccc(Oc5ccccn5)cc4)c4c(N)ncnc4n3C)cn2)CC1] | $^1$H NMR (400 MHz, DMSO-d$_6$) δ 8.25-8.13 (m, 2H), 7.94 (s, 1H), 7.88 (ddd, J = 8.2, 7.2, 2.0 Hz, 1H), 7.46 (s, 1H), 7.38-7.30 (m, 2H), 7.22-7.11 (m, 3H), 7.07 (dd, J = 8.3, 1.0 Hz, 1H), 6.84 (dd, J = 16.7, 10.5 Hz, 1H), 6.12 (dd, J = 16.7, 2.4 Hz, 1H), 5.86 (s, 1H), 5.69 (dd, J = 10.5, 2.4 Hz, 1H), 4.47 (td, J = 11.1, 5.5 Hz, 2H), 4.14 (d, J = 13.8 Hz, 1H), 3.70 (s, 3H), 3.23 (t, J = 12.9 Hz, 1H), 2.83 (t, J = 12.7 Hz, 1H), 2.12-1.98 (m, 2H), 1.78 (t, J = 12.9 Hz, 2H). | 521.35 |
| 1-(4-(4-(4-amino-7-methyl-5-(4-(pyrimidin-2-yloxy)phenyl)-7H-pyrrolo[2,3-d]pyrimidin-6-yl)-1H-pyrazol-1-yl)piperidin-1-yl)prop-2-en-1-one | 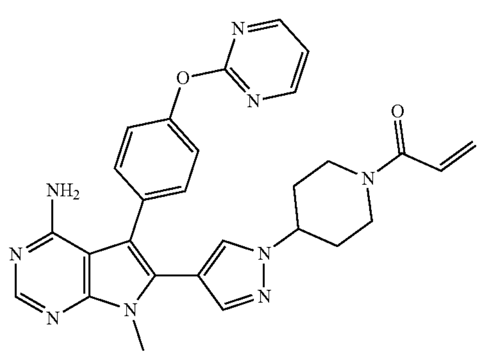 [SMILES: C=CC(=O)N1CCC(n2cc(-c3c(-c4ccc(Oc5ncccn5)cc4)c4c(N)ncnc4n3C)cn2)CC1] | $^1$H NMR (400 MHz, DMSO-d6) δ 8.68 (d, J = 4.8 Hz, 2H), 8.17 (s, 1H), 7.96 (s, 1H), 7.48 (d, J = 0.7 Hz, 1H), 7.39 (d, J = 8.5 Hz, 2H), 7.34-7.23 (m, 3H), 6.85 (dd, J = 16.7, 10.5 Hz, 1H), 6.13 (dd, J = 16.6, 2.4 Hz, 1H), 5.70 (dd, J = 10.4, 2.4 Hz, 1H), 4.49 (d, J = 12.4 Hz, 2H), 4.15 (d, J = 13.7 Hz, 1H), 3.70 (s, 3H), 3.24 (s, 1H), 2.84 (t, J = 12.3 Hz, 1H), 2.07 (d, J = 12.4 Hz, 2H), 1.81 (d, J = 14.3 Hz, 2H). | 522.2 |

TABLE 7-continued

Additional Exemplary Compounds

| Compound | Structure | Proton NMR | MS [M + 1] |
|---|---|---|---|
| 1-(4-(4-(4-amino-7-methyl-5-(4-(pyrazin-2-yloxy)phenyl)-7H-pyrrolo[2,3-d]pyrimidin-6-yl)-1H-pyrazol-1-yl)piperidin-1-yl)prop-2-en-1-one | 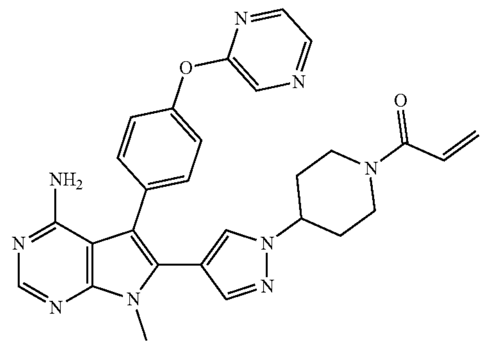 [SMILES: C=CC(=O)N1CCC(n2cc(-c3c(-c4ccc(Oc5cnccn5)cc4)c4c(N)ncnc4n3C)cn2)CC1] | 1H NMR (400 MHz, DMSO-d6) δ 8.58 (d, J = 1.4 Hz, 1H), 8.41 (d, J = 2.7 Hz, 1H), 8.26 (dd, J = 2.7, 1.4 Hz, 1H), 8.17 (s, 1H), 7.94 (d, J = 0.7 Hz, 1H), 7.46 (d, J = 0.7 Hz, 1H), 7.42-7.35 (m, 2H), 7.31-7.23 (m, 2H), 6.85 (dd, J = 16.7, 10.4 Hz, 1H), 6.12 (dd, J = 16.7, 2.4 Hz, 1H), 5.69 (dd, J = 10.5, 2.4 Hz, 1H), 4.47 (m, 2H), 4.14 (d, J = 13.5 Hz, 1H), 3.70 (s, 3H), 3.23 (t, J = 12.9 Hz, 1H), 2.84 (t, J = 12.8 Hz, 1H), 2.04 (s, 2H), 1.80 (d, J = 13.6 Hz, 2H). | 522.2 |
| N-(3-(4-(4-amino-7-methyl-5-(4-((6-methylpyridin-2-yl)oxy)phenyl)-7H-pyrrolo[2,3-d]pyrimidin-6-yl)-1H-pyrazol-1-yl)cyclobutyl)-N-methylacrylamide | 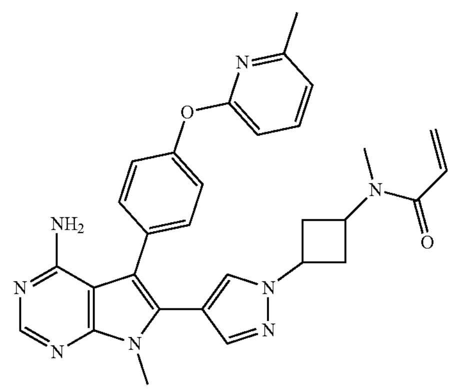 [SMILES: C=CC(=O)N(C)C1CC(n2cc(-c3c(-c4ccc(Oc5cccc(C)n5)cc4)c4c(N)ncnc4n3C)cn2)C1] | 1H NMR (400 MHz, DMSO-d6) δ 8.17 (d, J = 1.4 Hz, 1H), 8.02 (s, 1H), 7.75 (td, J = 7.7, 2.3 Hz, 1H), 7.50 (d, J = 12.4 Hz, 1H), 7.36 (dd, J = 8.7, 2.6 Hz, 2H), 7.18-7.14 (m, 2H), 7.04-7.00 (m, 1H), 6.82 (dd, J = 8.1, 3.2 Hz, 1H), 6.19-5.57 (m, 3H), 5.14 (d, J = 106.7 Hz, 1H), 4.90 (dt, J = 9.0, 4.8 Hz, 1H) 3.71 (d, J = 2.7 Hz, 3H), 3.16-2.91 (m, 3H), 2.90-2.54 (m, 6H), 2.35 (s, 3H). | 535.40 |
| 1-(4-(4-(4-amino-7-methyl-5-(4-(6-methylpyridin-2-yl)oxy)phenyl)-7H-pyrrolo[2,3-d]pyrimidin-6-yl)-5-methyl-1H-pyrazol-1-yl)piperidin-1- | 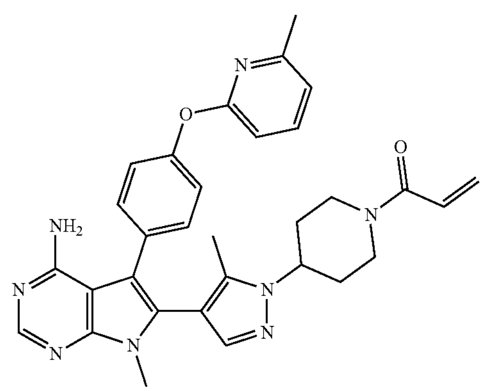 [SMILES: C=CC(=O)N1CCC(n2ncc(-c3c(-c4ccc(Oc5cccc(C)n5)cc4)c4c(N)ncnc4n3C)c2C)CC1] | $^1$H NMR (400 MHz, DMSO-d$_6$) δ 8.18 (s, 1H), 7.74 (t, J = 7.8 Hz, 1H), 7.67 (s, 1H), 7.22 (d, J = 8.2 Hz, 2H), 7.10 (d, J = 8.2 Hz, 2H), 7.02 (d, J = 7.4 Hz, 1H), 6.85 (dd, J = 16.8, 10.6 Hz, 1H), 6.79 (d, J = 8.2 Hz, 1H), 6.12 (dd, J = 16.8, 2.4 Hz, 1H), 6.01 (s, 2H), 5.69 (dd, J = 10.4, 2.4 Hz, 1H), 4.50 (d, J = 13.2 Hz, 1H), 4.40 (s, 1H), 4.16 (d, J = 13.6 Hz, 1H), 3.58 (s, 3H), 3.20 (t, J = 12.2 Hz, 1H), 2.79 (s, 1H), 2.35 (s, 3H), 1.83 (s, 4H), 1.78 (s, 3H). | 549.25 |
| (E)-2-(4-(4-(4-amino-7-methyl-5-(4-((6-methylpyridin-2-yl)oxy)phenyl)-7H-pyrrolo[2,3-d]pyrimidin-6-yl)-1H-pyrazol-1-yl)piperidine-1-carbonyl)but-2-enenitrile | 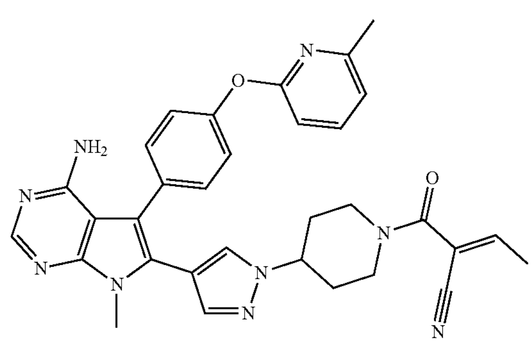 [SMILES: C/C=C(\C#N)C(=O)N1CCC(n2cc(-c3c(-c4ccc(Oc5cccc(C)n5)cc4)c4c(N)ncnc4n3C)cn2)CC1] | $^1$H NMR (400 MHz, DMSO-d$_6$) δ 1.82-1.93 (m, 3H), 2.07-2.09 (m, 5H), 2.25-2.36 (m, 5 H), 2.80-3.08 (br, 1H), 3.70 (s, 3H), 3.82-4.70 (m, 3H), 5.50-6.10 (br, 1 H), 6.69-6.92 (m, 1H), 6.92-7.16 (m, 4H), 7.33-7.36 (m , 2H), 7.45 (s, 1H), 7.72-7.80 (m, 1H), 7.97 (s, 1H), 8.10 (s, 1H). | 574.40 |

TABLE 7-continued

Additional Exemplary Compounds

| Compound | Structure | Proton NMR | MS [M + 1] |
|---|---|---|---|
| 1-(3-(4-(4-amino-7-methyl-5-(4-((6-Methylpyridin-2-yl)oxy)phenyl)-7H-pyrrolo[2,3-d]pyrimidin-6-yl)-1H-pyrazol-1-yl)pyrrolidin-1-yl)but-2-yn-1-one | 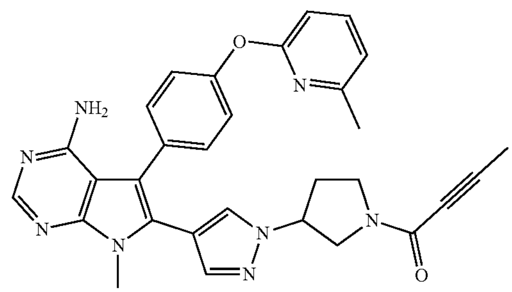 [SMILES: CC#CC(=O)N1CCC(n2cc(-c3c(-c4ccc(Oc5cccc(C)n5)cc4)c4c(N)ncnc4n3C)cn2)C1] | ¹H NMR (400 MHz, DMSO-d6) δ 2.00 (d, J = 14.4 Hz, 3H), 2.36 (s, 5H), 3.31 (s, 1H), 3.49 (m, 1H), 3.62-3.80 (m, 5H), 3.88-4.05 (m, 1H), 5.04 (s, 1H), 6.82 (d, J = 8.4 Hz, 1H), 7.03 (d, J = 7.6 Hz, 1H), 7.11-7.19 (m, 2H), 7.30-7.39 (m, 2H), 7.48 (d, J = 2.8 Hz, 1H), 7.75 (t, J = 7.6 Hz, 1H), 7.99 (d, J = 9.6 Hz, 1H), 8.17 (d, J = 0.8 Hz, 1H). | 533.23 |
| (E)-1-(3-(4-(4-amino-7-methyl-5-(4-((6-methylpyridn-2-yl)oxy)phenyl)-7H-pyrrolo[2,3-d]pyrimidin-6-yl)-1H-pyrazol-1-yl)pyrrolidin-1-yl)but-2-en-1-one | 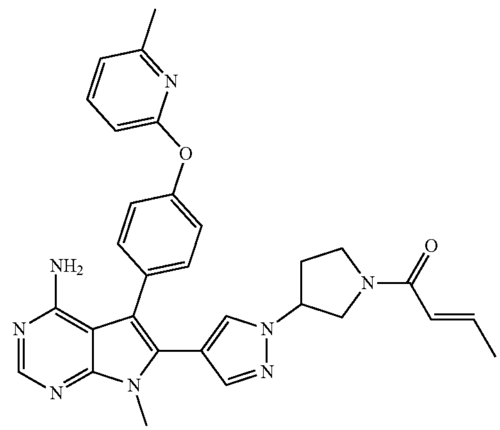 [SMILES: C/C=C/C(=O)N1CCC(n2cc(-c3c(-c4ccc(Oc5cccc(C)n5)cc4)c4c(N)ncnc4n3C)cn2)C1] | ¹H NMR (400 MHz, DMSO-d6) δ 1.82 (m, 3H), 2.36 (s, 5H), 3.51 (m, 1H), 3.70 (s, 4H), 3.80-4.05 (m, 1H), 4.95-5.11 (m, 1H), 6.25 (m, 1H), 6.64-6.73 (m, 1H), 6.82 (d, J = 8.4 Hz, 1H), 7.03 (d, J = 7.2 Hz, 1H), 7.11-7.18 (m, 2H), 7.34 (m, 2H), 7.48 (d, J = 4.4 Hz, 1H), 7.72-7.79 (m, 1H), 7.96 (d, J = 26.4 Hz, 1H), 8.16 (d, J = 0.8 Hz, 1H). | 535.2 |
| (E)-1-(3-(4-(4-amino-7-methyl-5-(4-(6-methylpyridin-2-yl)oxy)phenyl)-7H-pyrrolo[2,3-d]pyrimidin-6-yl)-1H-pyrazol-1-yl)azetidin-1-yl)-4-(dimethylamino)-2-methylbut-2-en-1-one | 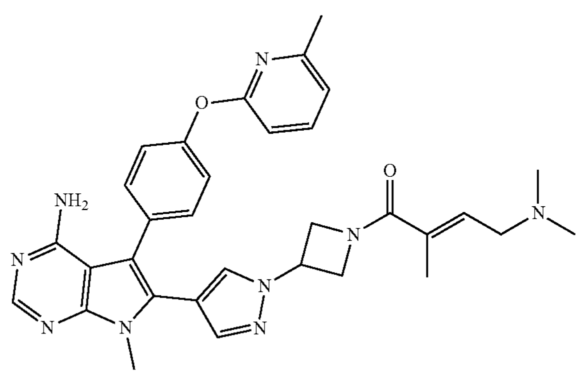 [SMILES: C/C(=C\CN(C)C)C(=O)N1CC(n2cc(-c3c(-c4ccc(Oc5cccc(C)n5)cc4)c4c(N)ncnc4n3C)cn2)C1] | 1H NMR (400 MHz, DMSO-d6) δ 8.15 (d, J = 11.3 Hz, 2H), 7.76 (t, J = 7.8 Hz, 1H), 7.51 (s, 1H), 7.40-7.32 (m, 2H), 7.20-7.12 (m, 2H), 7.03 (d, J = 7.4 Hz, 1H), 6.82 (d, J = 8.2 Hz, 1H), 5.92 (td, J = 6.5, 1.6 Hz, 2H), 5.27 (ddd, J = 13.4, 8.2, 5.2 Hz, 1H), 4.70-4.05 (m, 4H), 3.71 (s, 3H), 3.31 (s, 1H), 2.98 (d, J = 6.5 Hz, 2H), 2.36 (s, 3H), 2.14 (s, 6H), 1.75 (d, J = 1.4 Hz, 3H). | 578.45 |
| (E)-1-(3-(4-(4-amino-7-methyl-5-(4-((6-methylpyridin-2-yl)oxy)phenyl)-7H-pyrrolo[2,3-d]pyrimidin-6-yl)-1H-pyrazol-1-yl)azetidin-1-yl)but-2-en-1-one | 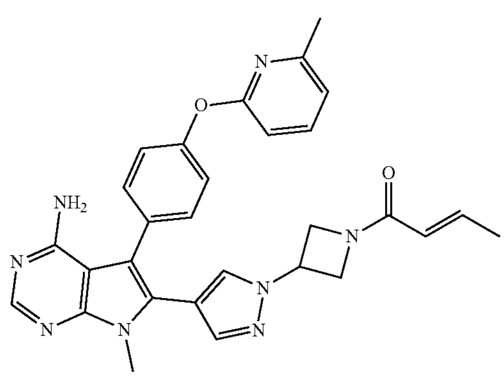 [SMILES: C/C=C/C(=O)N1CC(n2cc(-c3c(-c4ccc(Oc5cccc(C)n5)cc4)c4c(N)ncnc4n3C)cn2)C1] | ¹H NMR (400 MHz, DMSO-d₆) δ 1.82-1.84 (m, 4H), 2.36 (s, 1H), 3.71 (s, 1H), 4.12-4.19 (m, 1H), 4.31-4.58 (m, 2H), 4.61-4.69 (m, 1 H), 5.27-5.33 (m, 1H), 6.01-6.06 (m, 1 H), 6.66-6.68 (m, 1H), 6.82 (d, J = 8.0 Hz, 1H), 7.03 (d, J = 8.0 Hz, 1H), 7.15 (dd, J = 2.0 Hz, 2H), 7.35 (dd, J = 2.0 Hz, 2H), 7.52 (s, 1H), 7.76 (t, J = 15.6 Hz, 1H), 8.13 (s, 1H), 8.17 (s, 1H). | 521.20 |

TABLE 7-continued

Additional Exemplary Compounds

| Compound | Structure | Proton NMR | MS [M + 1] |
|---|---|---|---|
| 1-(4-(4-(4-amino-7-methyl-5-(4-((6-methylpyridin-2-yl)oxy)phenyl)-7H-pyrrolo[2,3-d]pyrimidin-6-yl)-1H-pyrazol-1-yl)piperidin-1-yl)-2-(morpholinomethyl)prop-2-en-1-one | 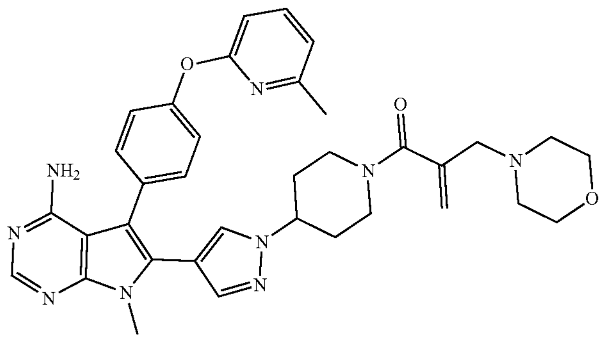 [SMILES: C=C(CN1CCOCC1)C(=O)N1CCC(n2cc(-c3c(-c4ccc(Oc5cccc(C)n5)cc4)c4c(N)ncnc4n3C)cn2)CC1] | $^1$H NMR (400 MHz, DMSO-$d_6$) δ 1.81 (s, 2H), 2.04 (d, J = 12.5 Hz, 2H), 2.35 (s, 4H), 2.37 (s, 3H), 2.85 (s, 1H), 3.10 (s, 1H), 3.22 (s, 1H), 3.54 (t, J = 4.8 Hz, 4H), 3.70 (s, 3H), 3.98 (s, 1H), 4.38-4.51 (m, 2H), 5.20 (s, 1H), 5.35 (s, 1H), 6.81 (d, J = 8.0 Hz, 1H), 7.03 (d, J = 7.2 Hz, 1H), 7.12-7.18 (m, 2H), 7.32-7.38 (m, 2H), 7.47 (d, J = 0.8 Hz, 1H), 7.75 (m, 1H), 7.94 (s, 1H), 8.16 (s, 1H). | 634.5 |
| 1-(4-(4-(4-amino-7-methyl-5-(4-(6-methylpyridin-2-yl)oxy)phenyl)-7H-pyrrolo[2,3-d]pyrimidin-6-yl)-1H-pyrazol-1-yl)piperidin-1-yl)but-2-yn-1-one | 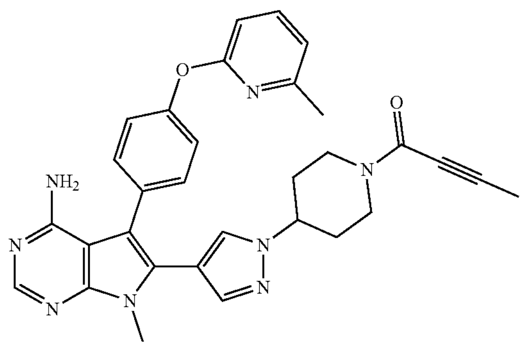 [SMILES: CC#CC(=O)N1CCC(n2cc(-c3c(-c4ccc(Oc5cccc(C)n5)cc4)c4c(N)ncnc4n3C)cn2)CC1] | $^1$H NMR (400 MHz, DMSO-$d_6$) δ 1.73 (m, 1H), 1.86 (m, 1H), 2.03 (s, 4H), 2.10 (d, J = 13.2 Hz, 1H), 2.36 (s, 3H), 2.80-2.92 (m, 1H), 3.27 (d, J = 2.8 Hz, 1H), 3.70 (s, 3H), 4.34 (m, 2H), 4.41-4.52 (m, 1H), 6.21 (d, J = 273.6 Hz, 1H), 6.81 (d, J = 8.4 Hz, 1H), 7.03 (d, J = 7.2 Hz, 1H), 7.10-7.21 (m, 2H), 7.31-7.40 (m, 2H), 7.44 (d, J = 0.7 Hz, 1H), 7.75 (dd, J = 7.3, 8.2 Hz, 1H), 7.97 (s, 1H), 8.16 (s, 1H). | 547.25 |
| (E)-1-(4-(4-(4-amino-7-methyl-5-(4-((6-methylpyridin-2-yl)oxy)phenyl)-7H-pyrrolo[2,3-d]pyrimidin-6-yl)-1H-pyrazol-1-yl)piperidin-1-yl)but-2-en-1-one | 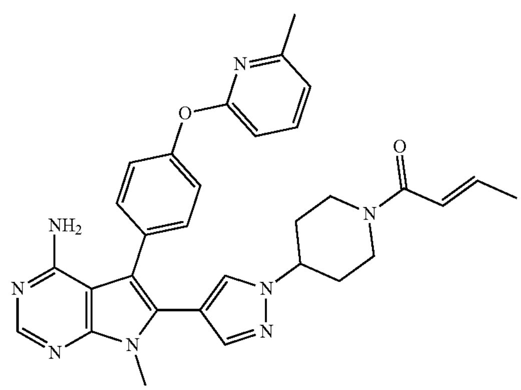 [SMILES: C/C=C/C(=O)N1CCC(n2cc(-c3c(-c4ccc(Oc5cccc(C)n5)cc4)c4c(N)ncnc4n3C)cn2)CC1] | $^1$H NMR (400 MHz, DMSO-$d_6$) δ 8.16 (s, 1H), 7.94 (d, J = 0.7 Hz, 1H), 7.75 (dd, J = 8.2, 7.4 Hz, 1H), 7.44 (d, J = 0.7 Hz, 1H), 7.37-7.32 (m, 2H), 7.17-7.13 (m, 2H), 7.03 (d, J = 7.3 Hz, 1H), 6.80 (d, J = 8.1 Hz, 1H), 6.75-6.64 (m, 1H), 6.54 (dd, J = 14.9, 1.7 Hz, 1H), 6.20-5.50 (m, 1H), 4.53-4.37 (m, 2H), 4.14 (s, 1H), 3.70 (s, 3H), 3.24-3.12 (m, 1H), 2.78 (s, 1H), 2.36 (s, 3H), 2.14-1.98 (m, 2H), 1.84 (dd, J = 6.7, 1.5 Hz, 3H), 1.77 (s, 2H). | 549.25 |
| (E)-1-(4-(4-(4-amino-7-methyl-5-(4-((6-methylpyridin-2-yl)oxy)phenyl)-7H-pyrrolo[2,3-d]pyrimidin-6-yl)-1H-pyrazol-1-yl)piperidin-1-yl)-4-morpholinobut-2-en-1-one | 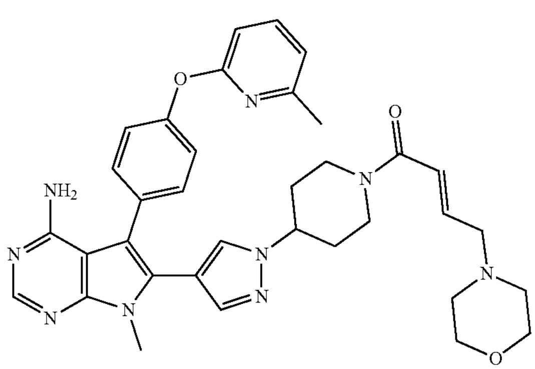 [SMILES: Cc1cccc(Oc2ccc(-c3c(-c4cnn(C5CCN(C(=O)/C=C/CN6CCOCC6)CC5)c4)n(C)c4ncnc(N)c34)cc2)n1] | $^1$H NMR (400 MHz, DMSO-$d_6$) δ 1.79 (d, J = 18.2 = 4 Hz, 2H), 2.06 (d, J = 16.0 Hz, 2H), 2.36 (s, 6H), 3.09 (d, J = 5.6 Hz, 4H), 3.58 (t, J = 4.8 Hz, 4H), 3.70 (s, 3H), 4.12 (d, J = 13.6 Hz, 1H), 4.46 (m, 2H), 5.84 (s, 1H), 6.53-6.72 (m, 2H), 6.80 (d, J = 8.0 Hz, 1H), 7.03 (d, J = 7.2 Hz, 1H), 7.15 (d, J = 8.5 Hz, 2H), 7.24-7.40 (m, 2H), 7.44 (s, 1H), 7.95 (s, 1H), 8.15 (d, J = 4.4 Hz, 2H) | 634.3 |

TABLE 7-continued

Additional Exemplary Compounds

| Compound | Structure | Proton NMR | MS [M + 1] |
|---|---|---|---|
| (E)-1-(4-(4-(4-amino-7-methyl-5-(4-(6-methylpyridin-2-yl)oxy)phenyl)-7H-pyrrolo[2,3-d]pyrimidin-6-yl)-1H-pyrazol-1-yl)piperidin-1-yl)-4-(dimethylamino)-2-methylbut-2-en-1-one | 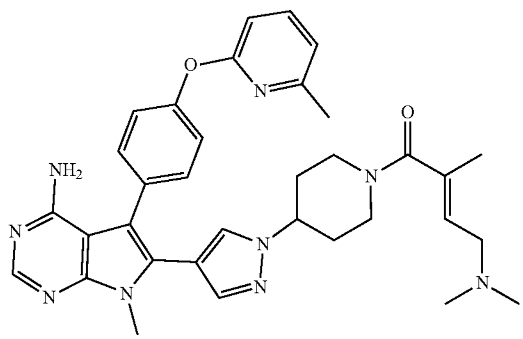 [SMILES: C/C(=C\CN(C)C)C(=O)N1CCC(n2cc(-c3c(-c4ccc(Oc5cccc(C)n5)cc4)c4c(N)ncnc4n3C)cn2)CC1] | $^1$H NMR (400 MHz, DMSO-d$_6$) δ 8.16 (s, 1H), 7.97 (s, 1H), 7.75 (t, J = 7.8 Hz, 1H), 7.45 (s, 1H), 7.37-7.31 (m, 2H), 7.19-7.13 (m, 2H), 7.03 (d, J = 7.3 Hz, 1H), 6.81 (d, J = 8.1 Hz, 1H), 5.51 (td, J = 6.6, 1.7 Hz, 2H), 4.60-4.33 (m, 1H), 4.38-3.79 (m, 1H), 3.70 (s, 3H), 3.34 (s, 1H), 2.93 (d, J = 6.7 Hz, 4H), 2.35 (s, 3H), 2.13 (s, 6H), 2.04 (d, J = 12.7 Hz, 2H), 1.88-1.72 (m, 5H). | 606.45 |
| 1-(4-(4-(4-amino-7-methyl-5-(4-phenoxyphenyl)-7H-pyrrolo[2,3-d]pyrimidin-6-yl)-1H-pyrazol-1-yl)piperidin-1-yl)-2-methylprop-2-en-1-one | 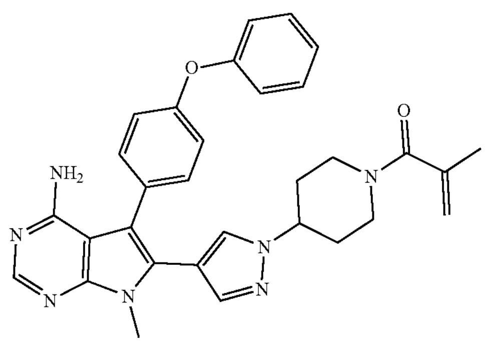 [SMILES: C=C(C)C(=O)N1CCC(n2cc(-c3c(-c4ccc(Oc5ccccc5)cc4)c4c(N)ncnc4n3C)cn2)CC1] | $^1$H NMR (400 MHz, DMSO-d$_6$) δ 8.15 (s, 1H), 7.91 (s, 1H), 7.49-7.38 (m, 3H), 7.36-7.28 (m, 2H), 7.17 (t, J = 7.4 Hz, 1H), 7.11-7.07 (m, 2H), 7.07-7.02 (m, 2H), 5.84 (s, 2H), 5.24-5.12 (m, 1H), 5.01 (t, J = 1.3 Hz, 1H), 4.51-4.34 (m, 2H), 3.91 (d, J = 28.7 Hz, 1H), 3.70 (s, 3H), 3.22 (s, 1H), 2.86 (s, 1H), 2.04 (d, J = 12.6 Hz, 2H), 1.88 (d, J = 1.4 Hz, 3H), 1.78 (tt, J = 12.2, 6.1 Hz, 2H). | 534.40 |
| 1-(4-(4-(4-amino-5-(4-methoxyphenyl)-7-methyl-7H-pyrrolo[2,3-d]pyrimidin-6-yl)-1H-pyrazol-1-yl)piperidin-1-yl)-2-methylprop-2-en-1-one | 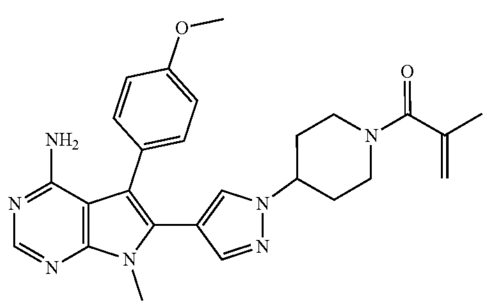 [SMILES: C=C(C)C(=O)N1CCC(n2cc(-c3c(-c4ccc(OC)cc4)c4c(N)ncnc4n3C)cn2)CC1] | $^1$H NMR (400 MHz, DMSO-d$_6$) δ 8.14 (s, 1H), 7.94 (s, 1H), 7.36 (s, 1H), 7.28-7.22 (m, 2H), 7.07-6.90 (m, 2H), 5.76 (s, 2H), 5.26-5.14 (m, 1H), 5.01 (t, J = 1.3 Hz, 1H), 4.44 (ddt, J = 11.1, 8.0, 4.0 Hz, 2H), 3.97 (s, 1H), 3.79 (s, 3H), 3.70 (s, 3H), 3.03 (d, J = 139.1 Hz, 2H), 2.04 (d, J = 12.5 Hz, 2H), 1.88 (d, J = 1.4Hz, 3H), 1.78 (qd, J = 12.1, 4.4 Hz, 2H). | 472.35 |
| 7-methyl-5-(4-(6-methylpyridin-2-yl)oxy)phenyl)-(vinylsulfonyl)piperidin-4-yl)-1H-pyrazol-4-yl)-7H-pyrrolo[2,3-d]pyrimidin-4-amine | 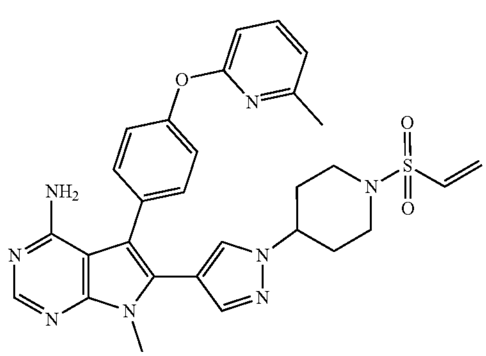 [SMILES: C=CS(=O)(=O)N1CCC(n2cc(-c3c(-c4ccc(Oc5cccc(C)n5)cc4)c4c(N)ncnc4n3C)cn2)CC1] | $^1$H NMR (400 MHz, DMSO-d$_6$) δ 8.16 (s, 1H), 7.97-7.94 (m, 1H), 7.75 (dd, J = 8.2, 7.3 Hz, 1H), 7.46 (d, J = 0.7 Hz, 1H), 7.38-7.32 (m, 2H), 7.20-7.12 (m, 2H), 7.03 (d, J = 7.3 Hz, 1H), 6.91-6.79 (m, 2H), 6.21-6.09 (m, 2H), 5.85 (s, 2H), 4.33 (dt, J = 7.2, 4.1 Hz, 0H), 3.70 (s, 3H), 3.60 (d, J = 12.4 Hz, 2H), 2.84 (td, J = 12.2, 2.7 Hz, 2H), 2.36 (s, 3H), 2.10 (d, J = 12.9 Hz, 2H), 1.95 (qd, J = 12.0, 4.2 Hz, 2H). | 571.15 |

TABLE 7-continued

Additional Exemplary Compounds

| Compound | Structure | Proton NMR | MS [M + 1] |
|---|---|---|---|
| 1-(4-(4-(4-amino-5-(3-methoxy-4-((6-methylpyridin-2-yl)oxy)phenyl)-7-methyl-7H-pyrrolo[2,3-d]pyrimidin-6-yl)-1H-pyrazol-1-yl)piperidin-1-yl)prop-2-en-1-one | 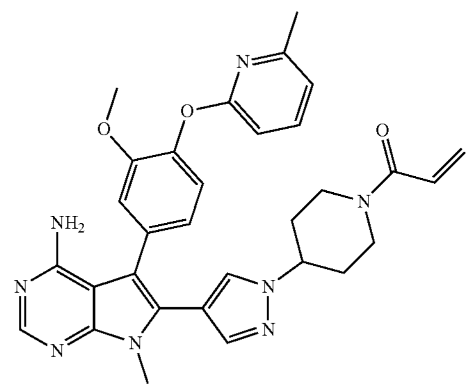 [SMILES: C=CC(=O)N1CCC(n2cc(-c3c(-c4ccc(Oc5cccc(C)n5)c(OC)c4)c4c(N)ncnc4n3C)cn2)CC1] | $^1$H NMR (400 MHz, DMSO-d$_6$) δ 8.17 (s, 1H), 7.98 (s, 1H), 7.67 (dd, J = 8.2, 7.4 Hz, 1H), 7.49 (d, J = 0.8 Hz, 1H), 7.14 (d, J = 8.0 Hz, 1H), 7.03 (d, J = 2.0 Hz, 1H), 6.97-6.90 (m, 2H), 6.85 (dd, J = 16.8, 10.6 Hz, 1H), 6.66 (d, J = 8.2 Hz, 1H), 6.12 (dd, J = 16.8, 2.6 Hz, 1H), 5.93 (s, 2H), 5.69 (dd, J = 10.6, 2.4 Hz, 1H), 4.54-4.43 (m, 2H), 4.15 (d, J = 13.8 Hz, 1H), 3.70 (s, 3H), 3.61 (s, 3H), 3.23 (t, J = 13.4 Hz, 1H), 2.83 (t, J = 12.4 Hz, 1H), 2.32 (s, 3H), 2.06 (d, J = 18.0 Hz, 2H), 1.87-1.71 (m, 2H). | 565.25 |
| 1-(4-(4-(4-amino-5-(3-methoxy-4-(m-tolyloxy)phenyl)-7-methyl-7H-pyrrolo[2,3-d]pyrimidin-6-yl)-1H-pyrazol-1-yl)piperidin-1-yl)prop-2-en-1-one | 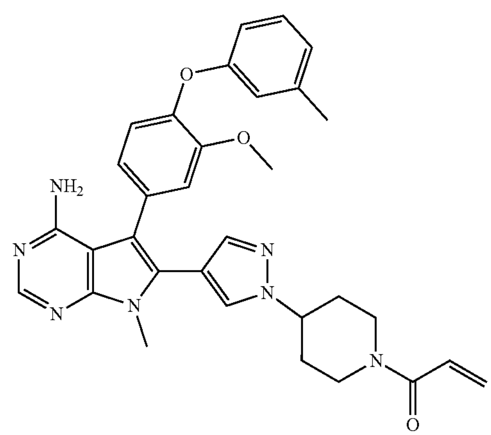 [SMILES: C=CC(=O)N1CCC(n2cc(-c3c(-c4ccc(Oc5cccc(C)c5)c(OC)c4)c4c(N)ncnc4n3C)cn2)CC1] | $^1$H NMR (400 MHz, DMSO-d$_6$) δ 1.79 (m, 2H), 2.03 (s, 2H), 2.29 (s, 3H), 2.83 (m, 1H), 3.23 (m, 1H), 3.67 (d, J = 20.4 Hz, 6H), 4.14 (d, J = 14.0 Hz, 1H), 4.40-4.54 (m, 2H), 5.69 (m, 1H), 6.12 (m, 1H), 6.66 (m, 1H), 6.76-6.91 (m, 4H), 7.02 (m, 2H), 7.20 (d, J = 8.0 Hz, 1H), 7.47 (s, 1H), 7.95 (s, 1H), 8.16 (s, 1H). | 564.45 |
| 1-(4-(4-(4-amino-5-(3-methoxy-4-(pyridin-2-yloxy)phenyl)-7-methyl-7H-pyrrolo[2,3-d]pyrimidin-6-yl)-1H-pyrazol-1-yl)piperidin-1-yl)prop-2-en-1-one | 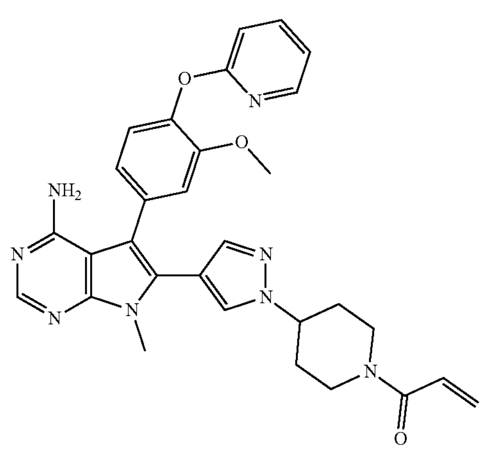 [SMILES: C=CC(=O)N1CCC(n2cc(-c3c(-c4ccc(Oc5ccccn5)c(OC)c4)c4c(N)ncnc4n3C)cn2)CC1] | $^1$H NMR (400 MHz, DMSO-d6) δ 8.17 (s, 1H), 8.11 (dd, J = 5.2, 2.0 Hz, 1H), 7.96 (s, 1H), 7.82 (ddd, J = 8.4, 7.2, 2.1 Hz, 1H), 7.52 (s, 1H), 7.17 (d, J = 8.0 Hz, 1H), 7.08 (ddd, J = 7.2, 4.9, 0.9 Hz, 1H), 7.03-6.92 (m, 3H), 6.85 (dd, J = 16.7, 10.5 Hz, 1H), 6.12 (dd, J = 16.7, 2.4 Hz, 1H), 5.95 (s, 1H), 5.69 (dd, J = 10.4, 2.4 Hz, 1H), 4.57-4.36 (m, 2H), 4.13 (t, J = 11.7 Hz, 1H), 3.69 (s, 3H), 3.60 (s, 3H), 3.29-3.14 (m, 1H), 2.84 (t, J = 12.7 Hz, 1H), 2.05 (s, 2H), 1.79 (t, J = 13.1 Hz, 2H). | 551.20 |

TABLE 7-continued

Additional Exemplary Compounds

| Compound | Structure | Proton NMR | MS [M + 1] |
|---|---|---|---|
| 1-(4-(3-(4-amino-5-(3-methoxy-4-((6-methylpyridin-2-yl)oxy)phenyl)-7-methyl-7H-pyrrolo[2,3-d]pyrimidin-6-yl)-5-methyl-1H-pyrazol-1-yl)piperidin-1-yl)prop-2-en-1-one | 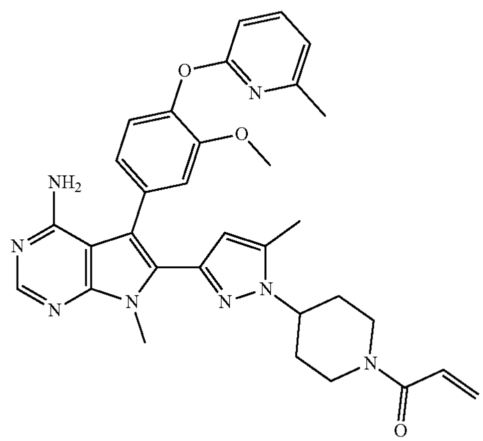 [SMILES: C=CC(=O)N1CCC(n2nc(-c3c(-c4ccc(Oc5cccc(C)n5)c(OC)c4)c4c(N)ncnc4n3C)cc2C)CC1] | ¹H NMR (400 MHz, DMSO-d6) δ 8.22 (s, 1H), 7.69 (t, J = 7.7 Hz, 1H), 7.15 (d, J = 8.0 Hz, 1H), 7.11 (d, J = 1.9 Hz, 1H), 7.00-6.92 (m, 2H), 6.84 (dd, J = 16.7, 10.5 Hz, 1H), 6.69 (d, J = 8.2 Hz, 1H), 6.12 (dd, J = 16.7, 2.4 Hz, 2H), 5.86 (s, 1H), 5.68 (dd, J = 10.4, 2.5 Hz, 1H), 4.57-4.43 (m, 2H), 4.16 (d, J = 13.7 Hz, 1H), 3.84 (s, 3H), 3.63 (s, 3H), 3.25 (d, J = 12.7 Hz, 1H), 2.86 (t, J = 12.0 Hz, 1H), 2.30 (d, J = 17.8 Hz, 6H), 1.90 (d, J = 22.3 Hz, 4H). | 579.45 |
| 1-(4-(4-(4-amino-5-(3-methoxy-4-((6-methylpyridin-2-yl)oxy)phenyl)-7-methyl-7H-pyrrolo[2,3-d]pyrimidin-6-yl)-5-methyl-1H-pyrazol-1-yl)piperidin-1-yl)prop-2-en-1-one | 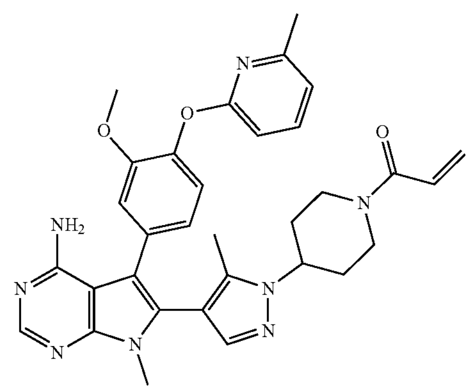 [SMILES: C=CC(=O)N1CCC(n2ncc(-c3c(-c4ccc(Oc5cccc(C)n5)c(OC)c4)c4c(N)ncnc4n3C)c2C)CC1] | ¹H NMR (400 MHz, DMSO-d₆) δ 8.19 (s, 1H), 7.73-7.63 (m, 2H), 7.13 (d, J = 8.0 Hz, 1H), 6.94 (d, J = 7.3 Hz, 1H), 6.90-6.78 (m, 3H), 6.68 (d, J = 8.2 Hz, 1H), 6.12 (dd, J = 16.6, 2.4 Hz, 2H), 5.69 (dd, J = 10.5, 2.4 Hz, 1H), 4.56-4.35 (m, 2H), 4.17 (d, J = 13.7 Hz, 1H), 3.60 (s, 3H), 3.47 (s, 3H), 3.20 (t, J = 13.1 Hz, 1H), 2.79 (s, 1H), 2.31 (s, 3H), 1.78 (s, 7H). | 579.45 |
| 1-(4-(4-(4-amino-5-(3-methoxy-4-(6-methylpyridin-2-yloxy)phenyl)-7-methyl-7H-pyrrolo[2,3-d]pyrimidin-6-yl)-1H-pyrazol-1-yl)-2-methylpiperidin-1-yl)prop-2-en-1-one | 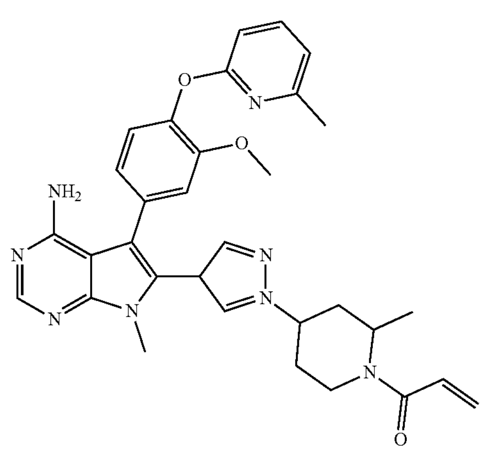 | ¹H NMR (400 MHz, DMSO-d₆) δ 8.17 (d, J = 1.3 Hz, 1H), 8.04 (s, 1H), 7.71-7.62 (m, 1H), 7.53 (s, 1H), 7.13 (dd, J = 9.2, 8.0 Hz, 1H), 7.04 (dd, J = 6.3, 1.9 Hz, 1H), 6.97-6.88 (m, 2H), 6.88-6.70 (m, 1H), 6.66 (dd, J = 8.3, 4.5 Hz, 1H), 6.10 (dd, J = 16.6, 2.4 Hz, 1H), 5.95 (s, 1H), 5.72-5.62 (m, 1H), 4.46 (s, 1H), 4.06 (s, 1H), 3.69 (s, 3H), 3.62 (d, J = 3.7 Hz, 3H), 2.31 (d, J = 1.9 Hz, 3H), 2.28-2.18 (m, 1H), 2.07 (dd, J = 16.7, 8.8 Hz, 2H), 1.32-1.18 (m, 1H), 0.84 (d, J = 6.8 Hz, 2H). | 578.677 |

TABLE 7-continued

Additional Exemplary Compounds

| Compound | Structure | Proton NMR | MS [M + 1] |
|---|---|---|---|
| 1-(4-(4-amino-5-(3-methoxy-4-(pyrimidin-2-yloxy)phenyl)-7-methyl-7H-pyrrolo[2,3-d]pyrimidin-6-yl)-3,6-dihydropyridin-1(2H)-yl)prop-2-en-1-one | 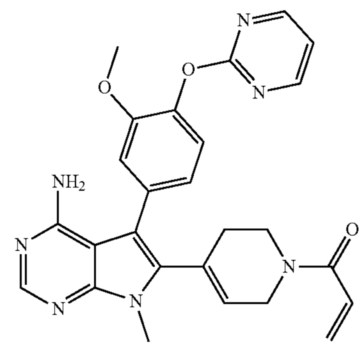 [SMILES: C=CC(=O)N1CC=C(c2c(-c3ccc(Oc4ncccn4)c(OC)c3)c3c(N)ncnc3n2C)CC1] | $^1$H NMR (400 MHz, DMSO-d$_6$) δ 8.64 (d, J = 4.8 Hz, 2H), 8.17 (s, 1H), 7.30-7.22 (m, 2H), 7.10 (s, 1H), 6.98 (d, J = 8.1 Hz, 1H), 6.80 (ddd, J = 28.0, 16.6, 10.4 Hz, 1H), 6.31-5.87 (m, 3H), 5.69 (t, J = 8.7 Hz, 1H), 4.20 (d, J = 31.7 Hz, 2H), 3.66 (d, J = 5.4 Hz, 8H), 2.18 (s, 2H). | 484.25 |
| 1-(4-(4-amino-5-(4-((6-ethylpyridin-2-yl)oxy)-3-methoxyphenyl)-7-methyl-7H-pyrrolo[2,3-d]pyrimidin-6-yl)-3,6-dihydropyridin-1(2H)-yl)prop-2-en-1-one | 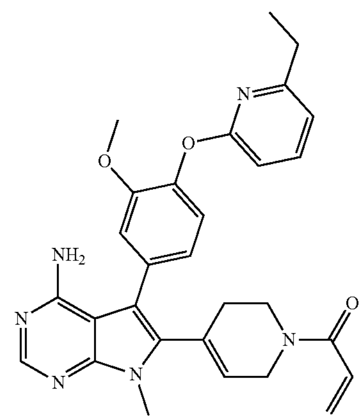 [SMILES: C=CC(=O)N1CC=C(c2c(-c3ccc(Oc4cccc(CC)n4)c(OC)c3)c3c(N)ncnc3n2C)CC1] | 1H NMR (400 MHz, DMSO-d6) δ 8.17 (s, 1H), 7.69 (t, J = 7.8 Hz, 1H), 7.18 (d, J = 8.0 Hz, 1H), 7.08 (s, 1H), 6.95 (dd, J = 11.4, 7.8 Hz, 2H), 6.75 (dd, J = 38.1, 9.5 Hz, 2H), 6.38-5.84 (m, 3H), 5.69 (t, J = 9.3 Hz, 1H), 4.42-4.06 (m, 2H), 3.66 (d, J = 3.1 Hz, 8H), 2.57 (q, J = 7.5 Hz, 2H), 2.18 (s, 2H), 1.08 (t, J = 7.5 Hz, 3H). | 511.25 |
| 1-(4-(4-amino-5-(3-methoxy-4-(5-methylpyridin-2-yl)oxy)phenyl)-7-methyl-7H-pyrrolo[2,3-d]pyrimidin-6-yl)-3,6-dihydropyridin-1(2H)-yl)prop-2-en-1-one | 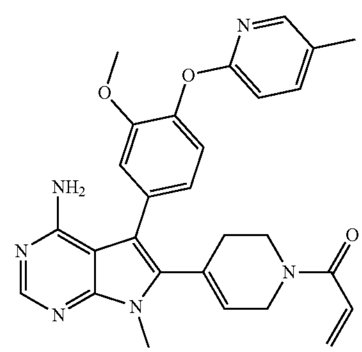 [SMILES: C=CC(=O)N1CC=C(c2c(-c3ccc(Oc4ccc(C)cn4)c(OC)c3)c3c(N)ncnc3n2C)CC1] | $^1$H NMR (400 MHz, DMSO-d$_6$) δ 8.17 (s, 1H), 7.94 (s, 1H), 7.64 (dd, J = 8.5, 2.4 Hz, 1H), 7.16 (d, J = 8.1 Hz, 1H), 7.07 (s, 1H), 6.95 (d, J = 8.1 Hz, 1H), 6.90-6.71 (m, 2H), 6.30-5.85 (m, 3H), 5.68 (d, J = 9.9 Hz, 1H), 4.20 (d, J = 32.5 Hz, 2H), 3.66 (d, J = 3.5 Hz, 8H), 2.24 (s, 3H), 2.17 (s, 2H). | 497.35 |
| 1-(4-(4-amino-5-(3-methoxy-4-((5-methylpyridin-3-yl)oxy)phenyl)-7-methyl-7H-pyrrolo[2,3-d]pyrimidin-6-yl)-3,6-dihydropyridin-1(2H)-yl)prop-2-en-1-one | 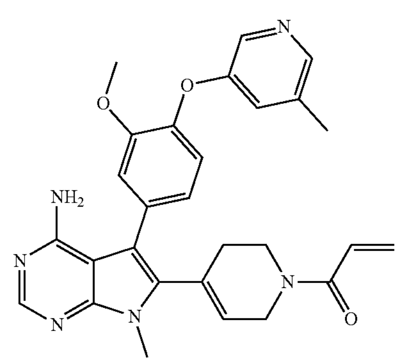 [SMILES: C=CC(=O)N1CC=C(c2c(-c3ccc(Oc4cncc(C)c4)c(OC)c3)c3c(N)ncnc3n2C)CC1] | $^1$H NMR (400 MHz, DMSO-d$_6$) δ 8.18-8.07 (m, 3H), 7.18-7.08 (m, 3H), 6.96 (dd, J = 8.0, 1.9 Hz, 1H), 6.79 (ddd, J = 26.9, 16.6, 10.4 Hz, 1H), 6.17-6.07 (m, 2H), 5.96 (d, J = 18.9 Hz, 1H), 5.74-5.64 (m, 1H), 4.19 (d, J = 33.2 Hz, 2H), 3.71 (s, 3H), 3.66 (s, 5H), 2.29 (s, 3H), 2.16 (s, 2H), 2.08 (s, 1H). | 497.20 |

TABLE 7-continued

Additional Exemplary Compounds

| Compound | Structure | Proton NMR | MS [M + 1] |
|---|---|---|---|
| 1-(3-(4-amino-7-methyl-5-(4-(pyrimidin-2-yloxy)phenyl)-7H-pyrrolo[2,3-d]pyrimidin-6-yl)-2,5-dihydro-1H-pyrrol-1-yl)prop-2-en-1-one | 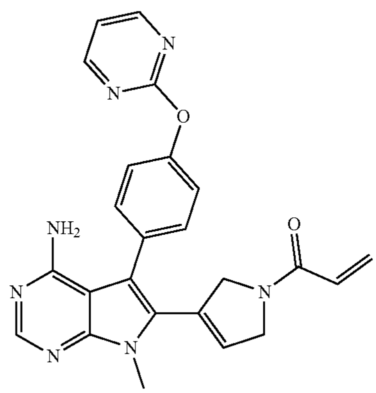 [SMILES: C=CC(=O)N1CC=C(c2c(-c3ccc(Oc4ncccn4)cc3)c3c(N)ncnc3n2C)C1] | $^1$H NMR (400 MHz, DMSO-d$_6$) δ 8.68 (dd, J = 12.3, 4.7 Hz, 2H), 8.19 (d, J = 1.1 Hz, 1H), 7.51-7.41 (m, 2H), 7.38-7.27 (m, 3H), 6.62-6.25 (m, 2H), 6.15 (dd, J = 16.8, 2.4 Hz, 1H), 5.89 (s, 2H), 5.69 (ddd, J = 14.8, 10.2, 2.4 Hz, 1H), 4.56 (dt, J = 4.8, 2.4 Hz, 1H), 4.35-4.22 (m, 2H), 4.05 (q, J = 2.4 Hz, 1H), 3.78 (d, J = 4.1 Hz, 3H). | 440.15 |
| 1-(3-(4-amino-7-methyl-5-(4-(pyrimidin-2-yloxy)phenyl)-7H-pyrrolo[2,3-d]pyrimidin-6-yl)-2,5-dihydro-1H-pyrrol-1-yl)-2-methylprop-2-en-1-one | 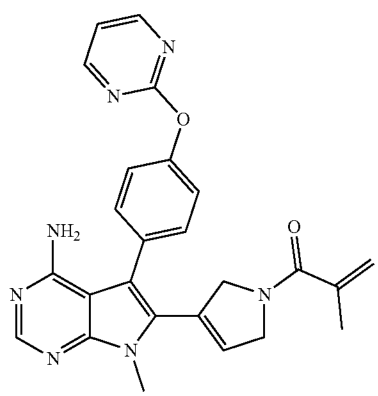 [SMILES: C=C(C)C(=O)N1CC=C(c2c(-c3ccc(Oc4ncccn4)cc3)c3c(N)ncnc3n2C)C1] | $^1$H NMR (400 MHz, DMSO-d$_6$) δ 8.69 (t, J = 4.6 Hz, 2H), 8.18 (s, 1H), 7.49-7.41 (m, 2H), 7.38-7.28 (m, 3H), 6.28 (dd, J = 39.5, 2.3 Hz, 1H), 5.86 (s, 2H), 5.32-4.93 (m, 2H), 4.50-4.28 (m, 2H), 4.06 (d, J = 10.4 Hz, 2H), 3.79 (d, J = 4.9 Hz, 3H), 1.90-1.72 (m, 3H). | 454.15 |
| 4-(6-(1-(1-acryloylpiperidin-4-yl)-1H-pyrazol-4-yl)-4-amino-7-methyl-7H-pyrrolo[2,3-d]pyrimidin-5-yl)-N-(2-hydroxy-2-methylpropyl)benzamide | 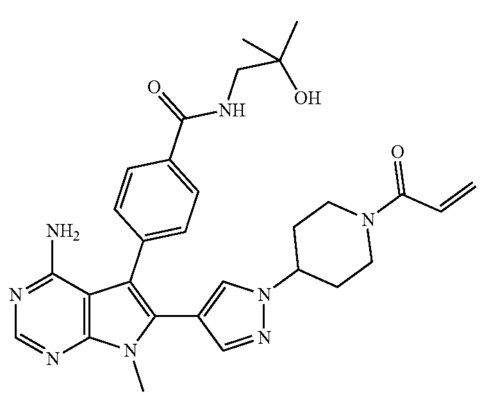 [SMILES: C=CC(=O)N1CCC(n2cc(-c3c(-c4ccc(C(=O)NCC(C)(C)O)cc4)c4c(N)ncnc4n3C)cn2)CC1] | $^1$H NMR (400 MHz, DMSO-d$_6$) δ 8.27 (t, J = 6.1 Hz, 1H), 8.18 (s, 1H), 8.00 (s, 1H), 7.92-7.81 (m, 2H), 7.43-7.35 (m, 3H), 6.84 (dd, J = 16.7, 10.5 Hz, 1H), 6.12 (dd, J = 16.7, 2.4 Hz, 1H), 5.82 (s, 1H), 5.69 (dd, J = 10.5, 2.4 Hz, 1H), 4.55 (s, 1H), 4.51-4.43 (m, 1H), 4.13 (d, J = 13.6 Hz, 1H), 3.69 (s, 3H), 3.27 (d, J = 6.2 Hz, 2H), 2.82 (d, J = 12.1 Hz, 1H), 2.05 (d, J = 12.7 Hz, 2H), 1.79 (s, 2H), 1.12 (s, 6H). | 543.35 |

TABLE 7-continued

Additional Exemplary Compounds

| Compound | Structure | Proton NMR | MS [M + 1] |
|---|---|---|---|
| 4-(6-(1-(1-acryloylpiperidin-4-yl)-1H-pyrazol-4-yl)-4-amino-7-methyl-7H-pyrrolo[2,3-d]pyrimidin-5-yl)-N-(tetrahydrofuran-3-yl)benzamide | 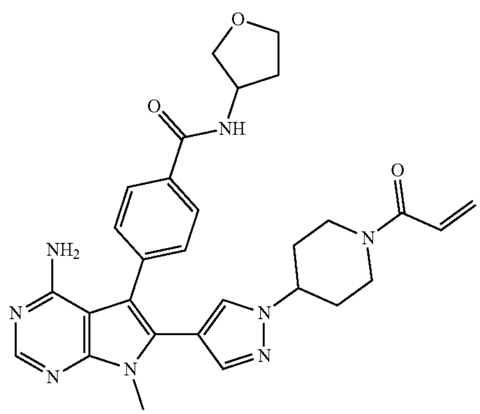 [SMILES: C=CC(=O)N1CCC(n2cc(-c3c(-c4ccc(C(=O)NC5CCOC5)cc4)c4c(N)ncnc4n3C)cn2)CC1] | ¹H NMR (400 MHz, DMSO-d₆) δ 8.57 (d, J = 6.4 Hz, 1H), 8.17 (s, 1H), 8.00 (s, 1H), 7.92-7.86 (m, 2H), 7.43-7.33 (m, 3H), 6.85 (dd, J = 16.7, 10.5 Hz, 1H), 6.12 (dd, J = 16.7, 2.4 Hz, 1H), 5.83-5.69 (dd, J = 10.4, 2.4 Hz, 2H), 4.52-4.41 (m, 3H), 4.14 (d, J = 13.6 Hz, 1H), 3.87 (dd, J = 8.8, 6.5 Hz, 2H), 3.73 (td, J = 8.1, 5.8Hz, 1H), 3.68 (s, 3H), 3.59 (dd, J = 8.8, 4.3 Hz, 1H), 3.23 (t, J = 13.1 Hz, 1H), 2.83 (t, J = 12.9 Hz, 1H), 2.16 (dq, J = 12.4, 7.5 Hz, 1H), 2.05 (d, J = 12.4 Hz, 2H), 1.94 (tt, J = 12.4, 5.6 Hz, 1H), 1.78 (d, J = 13.0 Hz, 2H). | 541.25 |
| 1-(4-(4-(5-(4-(2-azabicyclo[2.1.1]hexane-2-carbonyl)phenyl)-4-amino-7-methyl-7H-pyrrolo[2,3-d]pyrimidin-6-yl)-1H-pyrazol-1-yl)piperidin-1-yl)prop-2-en-1-one | 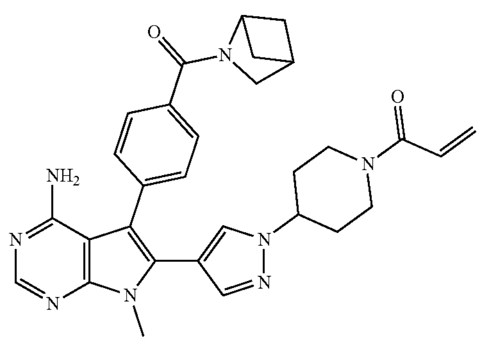 [SMILES: C=CC(=O)N1CCC(n2cc(-c3c(-c4ccc(C(=O)N5CC6CC5C6)cc4)c4c(N)ncnc4n3C)cn2)CC1] | ¹H NMR (400 MHz, DMSO-d₆) δ 8.17 (s, 1H), 7.92 (s, 1H), 7.69 (d, J = '1.'1 Hz, 1H), 7.46 (d, J = 7.8 Hz, 1H), 7.44-7.33 (m, 3H), 6.84 (dd, J = 16.7, 10.4 Hz, 1H), 6.12 (dd, J = 16.7, 2.5 Hz, 1H), 5.87 (s, 1H), 5.69 (dd, J = 10.5, 2.4 Hz, 1H), 4.50-4.40 (m, 2H), 4.13 (d, J = 13.8 Hz, 1H), 3.69 (s, 3H), 3.47 (s, 2H), 3.32-3.17 (m, 1H), 2.89 (s, 1H), 2.81 (d, J = 12.3 Hz, 1H), 2.10-1.95 (m, 5H), 1.77 (s, 2H), 1.49 (s, 1H), 1.36 (s, 1H). | 537.45 |
| 4-(6-(1-(1-acryloylpiperidin-4-yl)-1H-pyrazol-4-yl)-4-amino-7-methyl-7H-pyrrolo[2,3-d]pyrimidin-5-yl)-N-methyl-N-((3-methyl-1,2,4-oxadiazol-5-yl)methyl)benzamide | 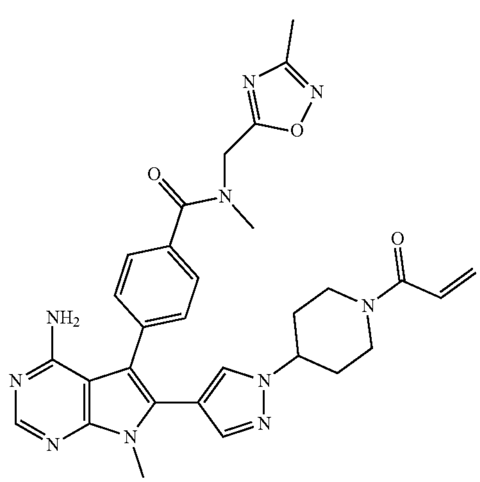 [SMILES: C=CC(=O)N1CCC(n2cc(-c3c(-c4ccc(C(=O)N(C)Cc5nc(C)no5)cc4)c4c(N)ncnc4n3C)cn2)CC1] | ¹H NMR (400 MHz, DMSO-d₆) δ 8.17 (s, 1H), 7.92 (s, 1H), 7.39 (d, J = 14.2 Hz, 5H), 6.84 (dd, J = 16.7, 10.5 Hz, 1H), 6.11 (dd, J = 16.7, 2.4 Hz, 1H), 5.89 (s, 1H), 5.69 (dd, J = 10.5, 2.4 Hz, 1H), 4.94 (s, 2H), 4.45 (s, 2H), 4.12 (d, J = 13.8 Hz, 1H), 3.69 (s, 3H), 3.17 (d, J = 33.9 Hz, 4H), 2.82 (t, J = 12.9 Hz, 1H), 2.37 (s, 3H), 2.05 (d, J = 26.0 Hz, 2H), 1.78 (d, J = 13.9 Hz, 2H). | 581.30 |

TABLE 7-continued

Additional Exemplary Compounds

| Compound | Structure | Proton NMR | MS [M + 1] |
|---|---|---|---|
| 1-(4-(4-(4-amino-7-methyl-5-(4-((1-methyl-1H-pyrazol-3-yl)oxy)phenyl)-7H-pyrrolo[2,3-d]pyrimidin-6-yl)-1H-pyrazol-1-yl)piperidin-1-yl)prop-2-en-1-one | 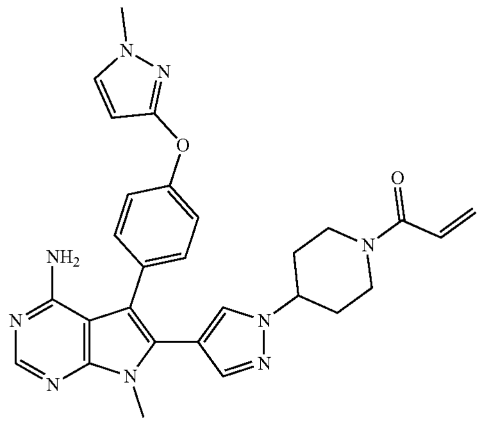 [SMILES: C=CC(=O)N1CCC(n2cc(-c3c(-c4ccc(Oc5ccn(C)n5)cc4)c4c(N)ncnc4n3C)cn2)CC1] | ¹H NMR (400 MHz, DMSO-d₆) δ 8.15 (s, 1H), 7.92 (s, 1H), 7.83 (s, 1H), 7.55 (s, 1H), 7.46-7.38 (m, 2H), 7.26 (s, 1H), 7.20-7.16 (m, 2H), 6.87-6.80 (m, 1H), 6.11 (dd, J = 16.7, 2.4 Hz, 1H), 6.07-5.99 (m, 1H), 5.70-5.66 (m, 1H), 4.56-4.38 (m, 2H), 4.18-4.09 (m, 1H), 3.79 (s, 3H), 3.74 (s, 3H), 3.21 (t, J = 12.7 Hz, 1H), 2.81 (t, J = 12.7 Hz, 1H), 2.02 (d, J = 12.5 Hz, 2H), 1.84-1.68 (m, 2H). | 524.35 |
| 4-(6-(1-(1-acryloylpiperidin-4-yl)-1H-pyrazol-4-yl)-4-amino-7-methyl-7H-pyrrolo[2,3-d]pyrimidin-5-yl)-N-(2-methoxy-2-methylpropyl)benzamide | 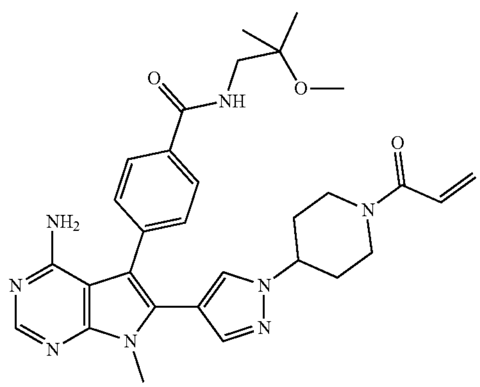 [SMILES: C=CC(=O)N1CCC(n2cc(-c3c(-c4ccc(C(=O)NCC(C)(C)OC)cc4)c4c(N)ncnc4n3C)cn2)CC1] | ¹H NMR (400 MHz, DMSO-d₆) δ 8.17 (s, 1H), 8.00 (s, 2H), 7.88 (d, J = 7.9 Hz, 2H), 7.43-7.35 (m, 3H), 6.84 (dd, J = 16.8, 10.7 Hz, 1H), 6.12 (d, J = 16.6 Hz, 1H), 5.69 (d, J = 10.8 Hz, 2H), 4.48 (d, J = 14.5 Hz, 1H), 4.13 (s, 1H) 3.68 (s, 3H), 3.40-3.23 (s, 3H), 3.16 (s, 3H), 2.83 (s, 1H), 2.04 (s, 2H), 1.79 (s, 2H), 1.13 (s, 6H). | 557.45 |
| 1-(4-{4-[4-amino-5-(2-chloro-4-phenoxyphenyl)-7-methyl-7H-pyrrolo[2,3-d]pyrimidin-6-yl]-1H-pyrazol-1-yl}piperidin-1-yl)prop-2-en-1-one | 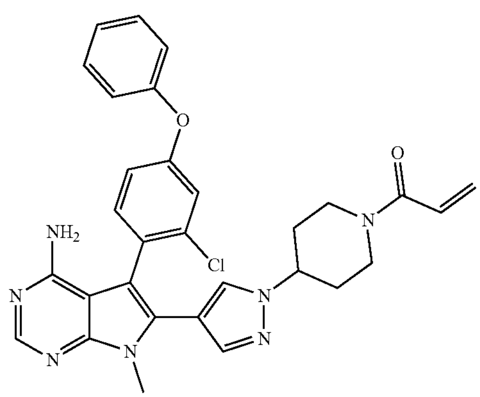 [SMILES: C=CC(=O)N1CCC(n2cc(-c3c(-c4ccc(Oc5ccccc5)cc4Cl)c4c(N)ncnc4n3C)cn2)CC1] | ¹H NMR (400 MHz, DMSO-d₆) δ 8.15 (s, 1H), 7.88 (s, 1H), 7.47 (t, J = 7.7 Hz, 1H), 7.40 (d, J = 8.4 Hz, 1H), 7.33 (s, 1H), 7.28-7.14 (m, 4H), 7.00 (dd, J = 8.4, 2.6 Hz, 1H), 6.85 (dd, J = 16.7, 10.4 Hz, 1H), 6.13 (dd, J = 16.8, 2.4 Hz, 1H), 5.77 (s, 2H), 4.47 (tt, J = 11.4, 4.1 Hz, 2H), 4.14 (d, J = 13.7 Hz, 1H), 3.76 (s, 3H), 3.24 (t, J = 12.8 Hz, 1H), 2.85 (t, J = 12.7 Hz, 1H), 2.03 (s, 2H), 1.78 (t, J = 12.6 Hz, 2H). | 554.05 |
| 1-(4-{4-[4-amino-5-(3-methoxy-4-phenoxyphenyl)-7-methyl-7H-pyrrolo[2,3-d]pyrimidin-6-yl]-1H-pyrazol-1-yl}piperidin-1-yl)prop-2-en-1-one; formic acid | 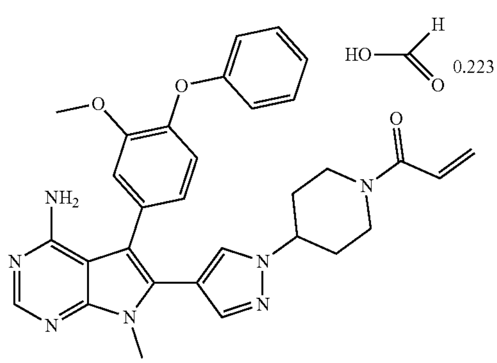 | ¹H NMR (400 MHz, DMSO-d₆) δ 8.17 (s, 1H), 7.92 (s, 1H), 7.49 (s, 1H), 7.34 (t, J = 7.7 Hz, 2H), 7.10-7.00 (m, 3H), 7.00-6.79 (m, 4H), 6.13 (dd, J = 16.7, 2.4 Hz, 1H), 5.70 (dd, J = 10.4, 2.4 Hz, 1H), 4.49 (tt, J = 11.6, 4.1 Hz, 2H), 4.14 (d, J = 13.8 Hz, 1H), 3.71 (s, 3H), 3.65 (s, 3H), 3.24 (t, J = 12.9 Hz, 1H), 2.85 (t, J = 12.7 Hz, 1H), 2.03 (s, 2H), 1.80 (t, J = 12.6 Hz, 2H). | 595.66 |

TABLE 7-continued

Additional Exemplary Compounds

| Compound | Structure | Proton NMR | MS [M + 1] |
|---|---|---|---|
| 1-(4-{4-amino-5-(4-chloro-3-methoxyphenyl)-7-methyl-7H-pyrrolo[2,3-d]pyrimidin-6-yl]-1H-pyrazol-1-yl}piperidin-1-yl)prop-2-en-1-one | | $^1$H NMR (400 MHz, DMSO-$d_6$) δ 8.16 (s, 1H), 7.98 (d, J = 0.8 Hz, 1H), 7.46-7.39 (m, 2H), 7.00 (d, J = 1.9 Hz, 1H), 6.91-6.85 (m, 1H), 6.89-6.80 (m, 1H), 6.12 (dd, J = 16.7, 2.4 Hz, 1H), 5.92 (s, 2H), 5.70 (dd, J = 10.5, 2.4 Hz, 1H), 4.53-4.43 (m, 1H), 4.14 (d, J = 14.0 Hz, 1H), 3.76 (s, 3H), 3.67 (s, 3H), 3.23 (t, J = 13.2 Hz, 1H), 2.84 (t, J = 12.9 Hz, 1H), 2.04 (d, J = 12.8 Hz, 2H), 1.80 (s, 2H). | 491.98 |
| 1-(4-{4-amino-5-(2-methoxyphenyl)-7-methyl-7H-pyrrolo[2,3-d]pyrimidin-6-yl]-1H-pyrazol-1-yl}piperidin-1-yl)prop-2-en-1-one | | $^1$H NMR (400 MHz, DMSO-$d_6$) δ 8.12 (s, 1H), 7.87 (s, 1H), 7.40 (t, J = 7.8 Hz, 1H), 7.29 (s, 1H), 7.20 (d, J = 7.3 Hz, 1H), 7.12 (d, J = 8.3 Hz, 1H), 7.00 (t, J = 7.4 Hz, 1H), 6.84 (dd, J = 16.7, 10.5 Hz, 1H), 6.12 (dd, J = 16.5, 2.4 Hz, 1H), 5.69 (dd, J = 10.3, 2.4 Hz, 1H), 5.57 (s, 2H), 4.42 (dt, J = 15.2, 5.3 Hz, 2H), 4.12 (d, J = 13.8 Hz, 1H), 3.73 (s, 3H), 3.64 (s, 3H), 2.82 (t, J = 12.9 Hz, 3H), 2.02 (d, J = 12.5 Hz, 2H), 1.81-1.70 (m, 2H). | 457.538 |
| 1-(4-{4-amino-5-(5-chloro-2H-1,3-benzodioxol-4-yl)-7-methyl-7H-pyrrolo[2,3-d]pyrimidin-6-yl]-1H-pyrazol-1-yl}piperidin-1-yl)prop-2-en-1-one | | $^1$H NMR (400 MHz, DMSO-$d_6$) δ 8.27 (s, 1H), 7.96 (s, 1H), 7.37 (s, 1H), 7.04 (d, J = 8.4 Hz, 2H), 7.00 (d, J = 8.4 Hz, 1H), 6.85 (dd, J = 16.7, 10.5 Hz, 1H), 6.12 (dd, J = 16.7, 2.4 Hz, 1H), 6.01 (d, J = 1.0 Hz, 1H), 5.96 (d, J = 1.0 Hz, 1H), 5.70 (dd, J = 10.5, 2.4 Hz, 1H), 4.53-4.43 (m, 2H), 4.13 (d, J = 13.8 Hz, 1H), 3.80 (s, 3H), 3.25 (d, J = 13.6 Hz, 1H), 2.83 (t, J = 12.6 Hz, 1H), 2.04 (d, J = 12.5 Hz, 2H), 1.79 (s, 2H). | 505.96 |

Example 9

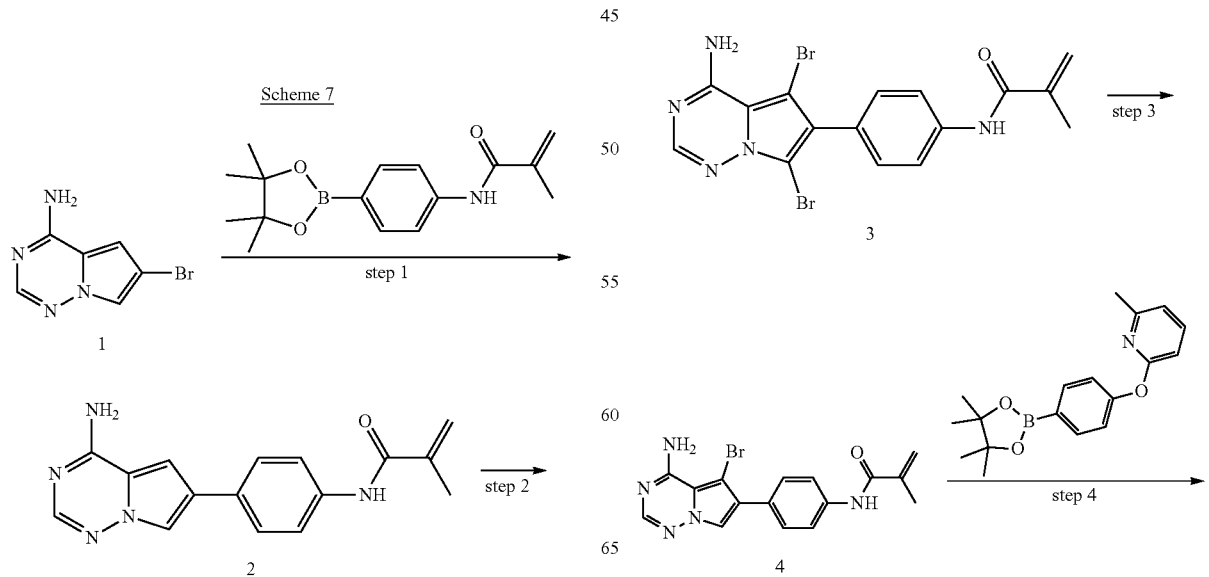

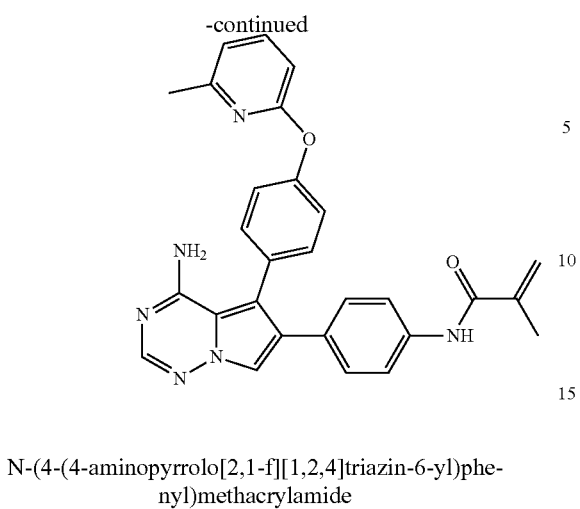

N-(4-(4-aminopyrrolo[2,1-f][1,2,4]triazin-6-yl)phenyl)methacrylamide

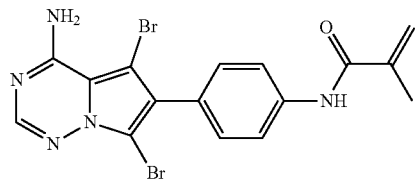 [SMILES: C=C(C)C(=O)Nc1ccc(-c2c(Br)c3c(N)ncnn3c2Br)cc1]

Step 1: A resealable reaction vial was charged with 6-bromopyrrolo[2,1-f][1,2,4]triazin-4-amine (500 mg, 2.34 mmol), 2-methyl-N-{4-(4,4,5,5-tetramethyl-1,3,2-dioxaborolan-2-yl)phenyl}prop-2-enamide (804 mg, 2.80 mmol), K3PO4 (1.48 g, 7.02 mmol), Pd(dppf)Cl$_2$ (171 mg, 234 µmol) and a stir bar before being evacuated and purged with nitrogen three times. DMF/H$_2$O (10 mL) was added, and the mixture was stirred at 90° C. for 1 h. The reaction mixture was diluted with water (20 mL), and the aqueous phase was extracted with dichloromethane (20 mL) three times. The combined organic layers were washed with brine, dried over sodium sulfate, filtered, and concentrated in vacuo. The resulting crude material was purified by prep-TLC (eluting with dichloromethane/methanol; 15:1). Concentration in vacuo resulted in N-(4-{4-aminopyrrolo[2,1-f][1,2,4]triazin-6-yl}phenyl)-2-methylprop-2-enamide (280 mg, 34%) as an off-white amorphous solid.

N-(4-{4-amino-5,7-dibromopyrrolo[2,1-f][1,2,4]triazin-6-yl}phenyl)-2-methylprop-2-enamide

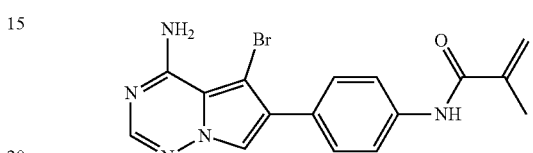

Step 2: A round bottomed flask was charged with N-(4-{4-aminopyrrolo[2,1-f][1,2,4]triazin-6-yl}phenyl)-2-methylprop-2-enamide (260 mg, 886 µmol), dimethylformamide (5 mL) was added, then NBS (313 mg, 1.77 mmol) was added at 0° C., and the solution was stirred for 1 h at 0° C. The reaction mixture was diluted with Na2SO3 (a.q.) (10 mL), and the aqueous phase was extracted with dichloromethane (10 mL) three times. The combined organic layers were washed with brine, dried over sodium sulfate, filtered, and concentrated in vacuo. The resulting crude material was purified by prep-TLC (eluting with dichloromethane/methanol; 20:1). Concentration in vacuo resulted in N-(4-{4-amino-5,7-dibromopyrrolo[2,1-f][1,2,4]triazin-6-yl}phenyl)-2-methylprop-2-enamide (350 mg, 87%) as an orange amorphous solid.

N-(4-(4-amino-5-bromopyrrolo[2,1-f][1,2,4]triazin-6-yl)phenyl)methacrylamide

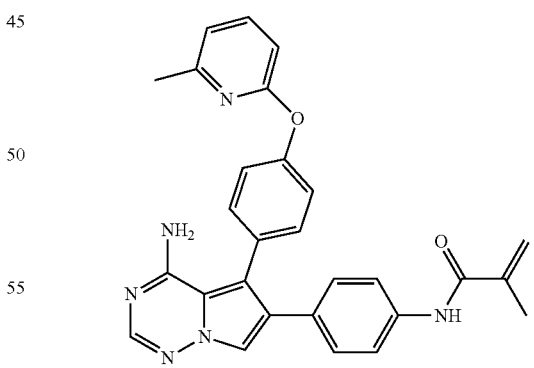

Step 3: A resealable reaction vial was charged with N-(4-{4-amino-5,7-dibromopyrrolo[2,1-f][1,2,4]triazin-6-yl}phenyl)-2-methylprop-2-enamide (300 mg, 665 µmol), tetrahydrofuran (6 mL) was added, and a stirbar before being evacuated and purged with nitrogen three times. At −78° C. n-BuLi (0.8 mL, 2 mmol) was added, and the mixture was stirred at −78° C. for 5 min. The reaction mixture was diluted with water (5 mL), and the aqueous phase was extracted with dichloromethane (5 mL) three times. The combined organic layers were washed with brine, dried over sodium sulfate, filtered, and concentrated in vacuo. The resulting crude material was purified by TLC (eluting with dichloromethane/methanol; 15:1). Concentration in vacuo resulted in N-(4-{4-amino-5-bromopyrrolo[2,1-f][1,2,4]triazin-6-yl}phenyl)-2-methylprop-2-enamide (100 mg, 40%) as an off-white amorphous solid.

N-(4-(4-amino-5-(4-((6-methylpyridin-2-yl)oxy)phenyl)pyrrolo[2,1-f][1,2,4]triazin-6-yl)phenyl)methacrylamide Step 4: A resealable reaction vial was charged with N-(4-{4-amino-5-bromopyrrolo[2,1-f][1,2,4]triazin-6-yl}phenyl)-2-methylprop-2-enamide (90.0 mg, 241 µmol), 2-methyl-6-[4-(4,4,5,5-tetramethyl-1,3,2-dioxaborolan-2-yl)phenoxy]pyridine (82.4 mg, 265 µmol), K$_3$PO$_4$ (153 mg, 722 µmol), Pd(dppf)Cl$_2$ (17.6 mg, 24.1 µmol), DMF/H$_2$O (4 mL) was added, and a stirbar before being evacuated and purged with nitrogen three times, and the mixture was stirred at 90° C. for 1 h. The reaction mixture was diluted with water (10 mL), and the aqueous phase was extracted with dichloromethane (10 mL) three times. The combined organic layers were washed with brine, dried over sodium sulfate, filtered, and concentrated in vacuo. The resulting crude material was purified by HPLC (Column: XBridge Prep OBD C18 Column, 30×150 mm 5 um; Mobile Phase A:undefined, Mobile Phase B:undefined; Flow rate:60 mL/min; Gradient:35 B to 50 B in 8 min; 220 nm; RT1:7.54; RT2:; Injection Volumn: ml; Number Of Runs:;). Lyophilization yielded N-[4-(4-amino-5-{4-[(6-methylpyridin-2-yl)oxy]phenyl}pyrrolo[2,1-f][1,2,4]triazin-6-yl)phenyl]-2-methylprop-2-enamide (7.62 mg, 6%) as an off-white amorphous solid.

Additional compounds prepared according to the methods of Example 9 are depicted in Table 8 below.

TABLE 8

Additional Exemplary Compounds

| Compound | Structure | Proton NMR | MS [M + 1] |
|---|---|---|---|
| N-(4-(4-amino-5-(4-((6-methylpyridin-2-yl)oxy)phenyl)pyrrolo[2,1-f][1,2,4]triazin-6-yl)phenyl) methacrylamide | 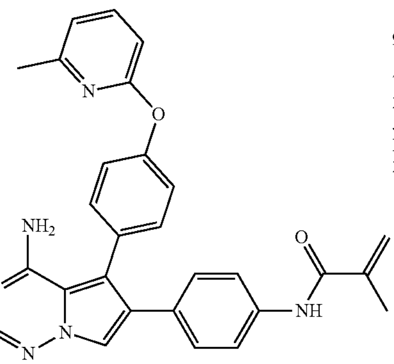 | $^1$H NMR (400 MHz, DMSO-d$_6$) δ 9.76 (s, 1H), 8.03 (s, 1H), 7.90 (s, 1H), 7.77 (t, J = 7.8 Hz, 1H), 7.60-7.53 (m, 2H), 7.41-7.34 (m, 2H), 7.23-7.13 (m, 4H), 7.05 (d, J = 7.4 Hz, 1H), 6.85 (d, J = 8.1 Hz, 1H), 5.77 (s, 1H), 5.50 (s, 1H), 2.38 (s, 3H), 1.94 (s, 3H). | 477.20 |
| N-(4-(4-amino-5-(4-(pyrrolidine-1-carbonyl)phenyl)pyrrolo[2,1-f][1,2,4]triazin-6-yl)phenyl) methacrylamide | 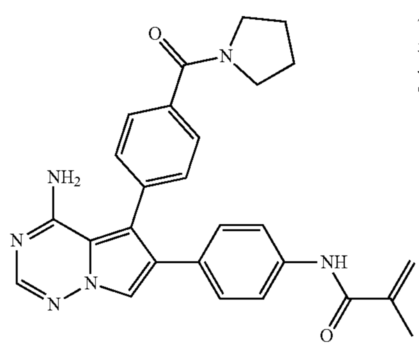 | $^1$H NMR (400 MHz, DMSO-d$_6$) δ 9.73 (s, 1H), 8.03 (s, 1H), 7.91 (s, 1H), 7.64-7.51 (m, 4H), 7.42-7.36 (m, 2H), 7.14-7.08 (m, 2H), 5.77 (d, J = 1.3 Hz, 1H), 5.50 (t, J = 1.5 Hz, 1H), 3.48 (dt, J = 13.3, 6.3 Hz, 4H), 2.01-1.71 (m, 7H). | 467.35 |
| N-(4-(4-amino-5-(4-(pyrrolidin-1-ylsulfonyl)phenyl)pyrrolo[2,1-f][1,2,4]triazin-6-yl)phenyl) methacrylamide | 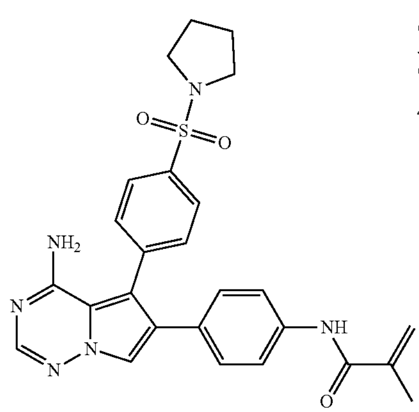 | $^1$H NMR (400 MHz, DMSO-d$_6$) δ 9.75 (s, 1H), 8.04 (s, 1H), 7.94 (s, 1H), 7.85 (d, J = 8.2 Hz, 2H), 7.54 (dd, J = 8.4, 5.8 Hz, 4H), 7.01 (d, J = 8.6 Hz, 2H), 5.76 (s, 1H), 5.50 (s, 1H), 3.25-3.13 (m, 4H), 1.96-1.89 (m, 3H), 1.77-1.57 (m, 4H). | 503.35 |

TABLE 8-continued

Additional Exemplary Compounds

| Compound | Structure | Proton NMR | MS [M + 1] |
|---|---|---|---|
| N-(4-(4-amino-5-(3-fluoro-4-((5-fluoropyrimidin-2-yl)oxy)phenyl)pyrrolo[2,1-f][1,2,4]triazin-6-yl)phenyl)methacrylamide | 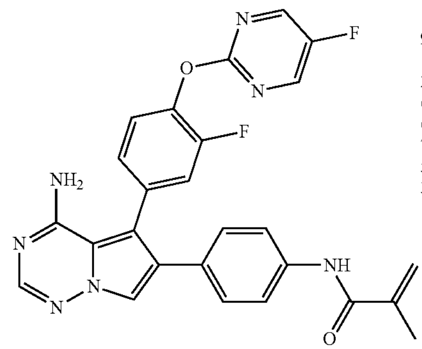 | ¹H NMR (400 MHz, DMSO-d₆) δ 9.77 (s, 1H), 8.81 (s, 2H), 8.02 (s, 1H), 7.93 (s, 1H), 7.62-7.56 (m, 2H), 7.49 (t, J = 8.3 Hz, 1H), 7.36 (dd, J = 11.2, 2.0 Hz, 1H), 7.24 (dd, J = 8.3, 2.1 Hz, 1H), 7.21-7.10 (m, 2H), 5.79 (s, 1H), 5.54-5.45 (m, 1H), 1.95 (t, J = 1.3 Hz, 3H). | 500.30 |
| 1-(3-(4-amino-5-(4-((6-methylpyridin-2-yl)oxy)phenyl)pyrrolo[2,1-f][1,2,4]triazin-6-yl)pyrrolidin-1-yl)prop-2-en-1-one | 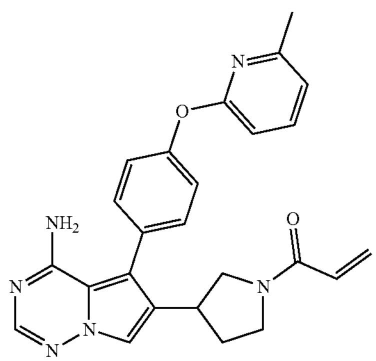 [SMILES: C=CC(=O)N1CCC(c2cn3ncnc(N)c3c2-c2ccc(Oc3cccc(C)n3)cc2)C1] | ¹H NMR (400 MHz, DMSO-d₆) δ 7.86 (d, J = 1.5 Hz, 1H), 7.84-7.72 (m, 2H), 7.45 (dd, J = 8.6, 2.6 Hz, 2H), 7.29-7.19 (m, 2H), 7.05 (d, J = 7.4 Hz, 1H), 6.86 (d, J = 8.1 Hz, 1H), 6.55 (ddd, J = 16.8, 13.5, 10.3 Hz, 1H), 6.12 (dt, J = 16.9, 2.0 Hz, 1H), 5.65 (ddd, J = 9.8, 6.9, 2.4 Hz, 1H), 4.70 (d, J = 8.6 Hz, 1H), 3.91-3.59 (m, 2H), 3.59-3.42 (m, 1H), 3.37 (s, 1H), 3.28-3.14 (m, 2H), 2.37 (d, J = 3.0 Hz, 3H), 2.25-1.85 (m, 2H). | 441.30 |
| N-(4-(4-amino-5-(4-((6-methylpyridin-2-yl)oxy)phenyl)pyrrolo[2,1-f][1,2,4]triazin-6-yl)phenyl)acrylamide | 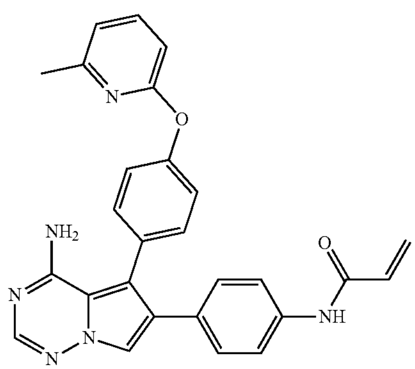 [SMILES: C=CC(=O)Nc1ccc(-c2cn3ncnc(N)c3c2-c2ccc(Oc3cccc(C)n3)cc2)cc1] | ¹H NMR (400 MHz, DMSO-d₆) δ 10.12 (s, 1H), 8.03 (s, 1H), 7.90 (s, 1H), 7.81-7.73 (m, 1H), 7.56 (d, J = 8.6 Hz, 2H), 7.44-7.32 (m, 2H), 7.24-7.13 (m, 4H), 7.05 (d, J = 7.4 Hz, 1H), 6.84 (d, J = 8.1 Hz, 1H), 6.42 (dd, J = 16.9, 10.1 Hz, 1H), 6.24 (dd, J = 17.0, 2.0 Hz, 1H), 5.75 (dd, J = 10.1, 2.1 Hz, 1H), 2.38 (s, 3H). | 463.30 |
| N-(4-(4-amino-7-methyl-5-(4-((6-methylpyridin-2-yl)oxy)phenyl)pyrrolo[2,1-f][1,2,4]triazin-6-yl)phenyl)methacrylamide | 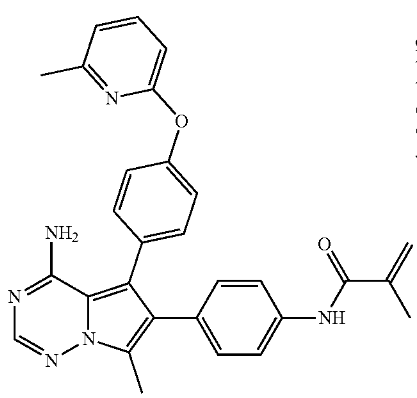 | ¹H NMR (400 MHz, DMSO-d₆) δ 9.78 (s, 1H), 7.96 (s, 1H), 7.83-7.71 (m, 1H), 7.64-7.57 (m, 2H), 7.35-7.24 (m, 2H), 7.16-7.06 (m, 4H), 7.02 (d, J = 7.4 Hz, 1H), 6.80 (d, J = 8.1 Hz, 1H), 5.77 (t, J = 1.1 Hz, 1H), 5.60-5.39 (m, 1H), 2.46 (s, 3H), 2.35 (s, 3H), 1.94 (d, J = 1.2 Hz, 3H). | 491.30 |

Example 10
Scheme 8.
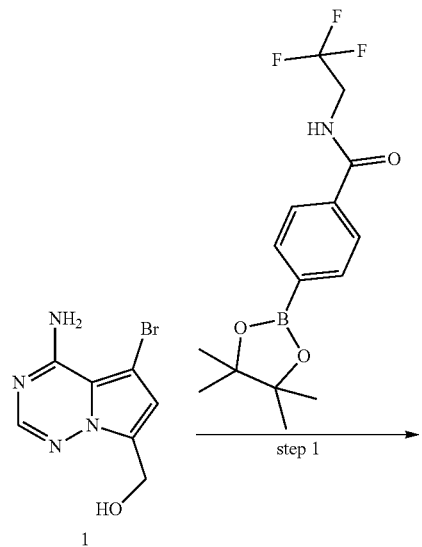
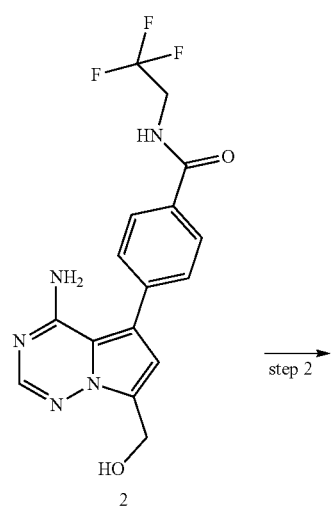
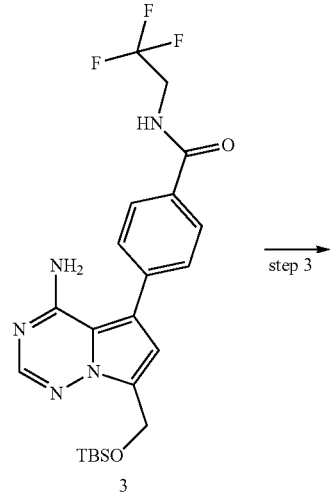
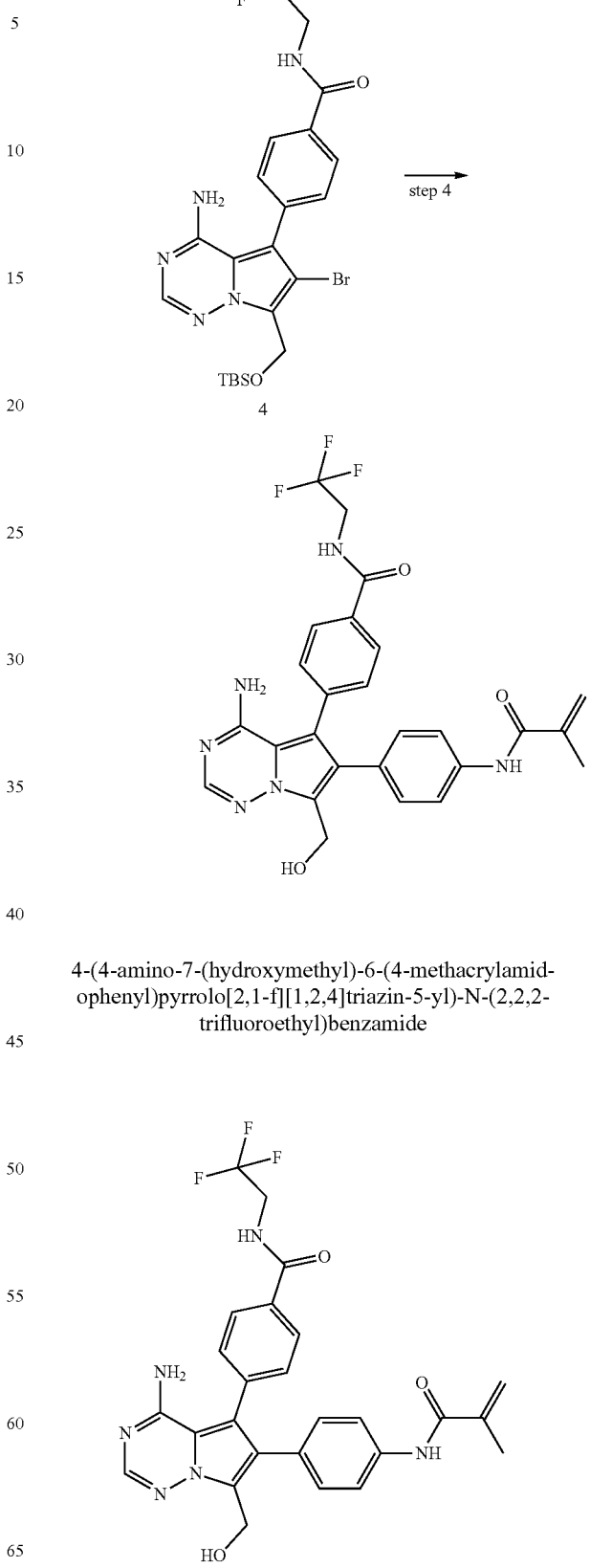
4-(4-amino-7-(hydroxymethyl)-6-(4-methacrylamidophenyl)pyrrolo[2,1-f][1,2,4]triazin-5-yl)-N-(2,2,2-trifluoroethyl)benzamide

4-(4-amino-7-(hydroxymethyl)pyrrolo[2,1-f][1,2,4]triazin-5-yl)-N-(2,2,2-trifluoroethyl)benzamide

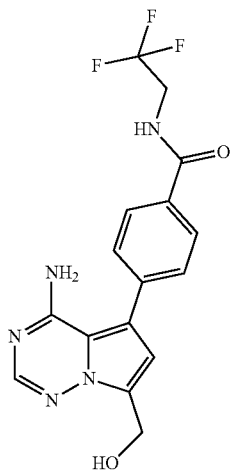 [SMILES: Nc1ncnn2c(CO)cc(-c3ccc(C(=O)NCC(F)(F)F)cc3)c12]

Step 1: A resealable reaction vial was charged with (4-amino-5-bromopyrrolo[2,1-f][1,2,4]triazin-7-yl)methanol (600 mg, 2.49 mmol), 4-(4,4,5,5-tetramethyl-1,3,2-dioxaborolan-2-yl)-N-(2,2,2-trifluoroethyl)benzamide (983 mg, 2.99 mmol), Pd(dtbpf)Cl$_2$ (162 mg, 249 µmol), CsF (1.14 g, 7.47 mmol), DMF:water=16:1 (8 mL) and a stir bar before being evacuated and purged with nitrogen three times. The solution was stirred for 2 h at 90° C. The reaction mixture was quenched with water, extracted with DCM. The organic phase was separated and dried over Na$_2$SO$_4$, filtered and concentrated in vacuo. The resulting crude material was purified by prep-TLC. Concentration in vacuo resulted in 4-(4-amino-7-(hydroxymethyl)pyrrolo[2,1-f][1,2,4]triazin-5-yl)-N-(2,2,2-trifluoroethyl)benzamide (400 mg, 44%) as a yellow oil.

4-(4-amino-7-(((tert-butyldimethylsilyl)oxy)methyl)pyrrolo[2,1-f][1,2,4]triazin-5-yl)-N-(2,2,2-trifluoroethyl)benzamide

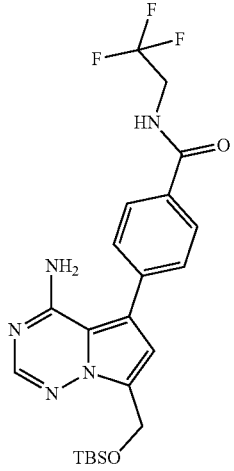 [SMILES: CC(C)(C)[Si](C)(C)OCc1cc(-c2ccc(C(=O)NCC(F)(F)F)cc2)c2c(N)ncnn12]

Step 2: A resealable reaction vial was charged with 4-(4-amino-7-(hydroxymethyl)pyrrolo[2,1-f][1,2,4]triazin-5-yl)-N-(2,2,2-trifluoroethyl)benzamide (380 mg, 1.04 mmol), Imidazole (283 mg, 4.16 mmol), DMF (5 mL) and a stir bar. TBSCl (314 mg, 2.08 mmol) was added, and the solution was stirred for 1 h at room temperature. The resulted mixture was purified through C18 Column. Concentration in vacuo resulted in 4-(4-amino-7-(((tert-butyldimethylsilyl)oxy)methyl)pyrrolo[2,1-f][1,2,4]triazin-5-yl)-N-(2,2,2-trifluoroethyl)benzamide (420 mg, 84%) as a yellow amorphous solid.

4-(4-amino-6-bromo-7-(((tert-butyldimethylsilyl)oxy)methyl)pyrrolo[2,1-f][1,2,4]triazin-5-yl)-N-(2,2,2-trifluoroethyl)benzamide

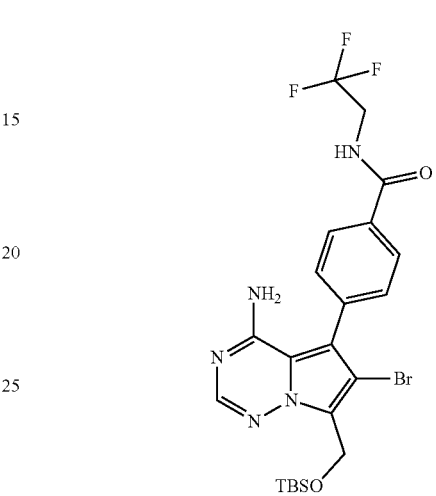

Step 3: A round bottomed flask was charged with 4-(4-amino-7-(((tert-butyldimethylsilyl)oxy)methyl)pyrrolo[2,1-f][1,2,4]triazin-5-yl)-N-(2,2,2-trifluoroethyl)benzamide (400 mg, 0.84 mmol), dimethylformamide (5 mL) and a stir bar. NBS (225 mg, 1.00 mmol) was added, and the solution was stirred for 1 h at room temperature. The reaction mixture was quenched with water, extracted with DCM. The organic phase was separated and dried over Na$_2$SO$_4$, filtered and concentrated in vacuo. The resulting crude material was purified by silica gel chromatography. Concentration in vacuo resulted in 4-(4-amino-6-bromo-7-(((tert-butyldimethylsilyl)oxy)methyl)pyrrolo[2,1-f][1,2,4]triazin-5-yl)-N-(2,2,2-trifluoroethyl)benzamide (450 mg, 94%) as a yellow amorphous solid.

6-{5-[2-(tert-butyldimethylsilyl)ethynyl]-3-methylpyrazin-2-yl}-7-methyl-5-{4-[(4-methylpyrimidin-2-yl)oxy]phenyl}-7H-pyrrolo[2,3-d]pyrimidin-4-amine

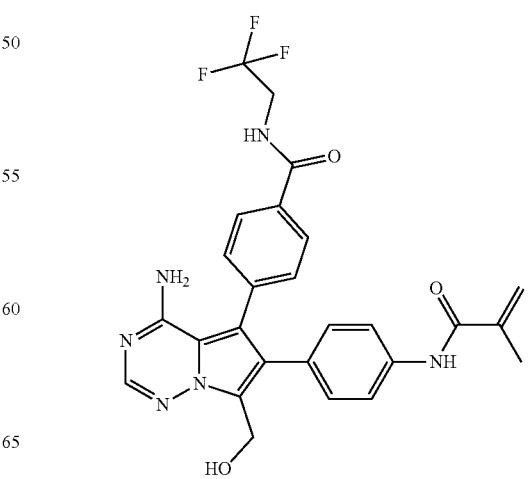

Step 4: A resealable reaction vial was charged with 4-(4-amino-6-bromo-7-(((tert-butyldimethylsilyl)oxy)methyl)pyrrolo[2,1-f][1,2,4]triazin-5-yl)-N-(2,2,2-trifluoroethyl)benzamide (200 mg, 0.36 mmol), N-(4-(4,4,5,5-tetramethyl-1,3,2-dioxaborolan-2-yl)phenyl)methacrylamide (124 mg, 0.43 mmol), Pd(dtbpf)Cl$_2$ (23.4 mg, 36 µmol), CsF (164 mg, 1.08 mmol), DMF:water=16:1 (4 mL) and a stir bar before being evacuated and purged with nitrogen three times. The solution was stirred for 2 h at 90° C. under N$_2$. The reaction mixture was quenched with water, extracted with DCM. The organic phase was collected and dried over Na$_2$SO$_4$, filtered and concentrated in vacuo. The resulting crude material was purified by Prep-HPLC (Column: XBridge Prep OBD C18 Column, 19*250 mm, 5 um; Mobile Phase A:Water(10 MMOL/L NH$_4$HCO$_3$), Mobile Phase B:ACN; Flow rate:25 mL/min; Gradient:20 B to 50 B in 8 min; 220 nm; RT1:7.23;). Lyophilization yielded 4-(4-amino-7-(hydroxymethyl)-6-(4-methacrylamidophenyl)pyrrolo[2,1-f][1,2,4]triazin-5-yl)-N-(2,2,2-trifluoroethyl)benzamide (30.4 mg, 16%) as an off-white amorphous solid.

Additional compounds prepared according to the methods of Example 10 are depicted in Table 9 below.

TABLE 9

Additional Exemplary Compounds

| Compound | Structure | Proton NMR | MS [M + 1] |
|---|---|---|---|
| N-(4-(4-amino-7-cyano-5-(4-((6-methylpyridin-2-yl)oxy)phenyl)pyrrolo[2,1-f][1,2,4]triazin-6-yl)phenyl)methacrylamide | 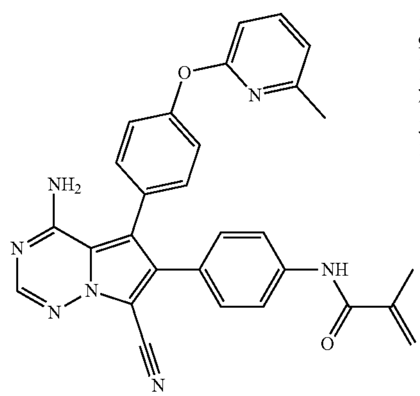 | $^1$H NMR (400 MHz, DMSO-d$_6$) δ 9.88 (s, 1H), 8.46 (s, 1H), 8.20 (s, 1H), 7.80-7.63 (m, 3H), 7.36 (d, J = 8.4 Hz, 2H), 7.25-7.14 (m, 4H), 7.04 (d, J = 7.3 Hz, 1H), 6.84 (d, J = 8.2 Hz, 1H), 5.79 (s, 1H), 5.53 (s, 1H), 2.36 (s, 3H), 1.94 (s, 3H). | 502.35 |
| N-(4-(4-amino-7-(hydroxymethyl)-5-(4-(6-methylpyridin-2-yl)oxy)phenyl)pyrrolo[2,1-f][1,2,4]triazin-6-yl)phenyl)methacrylamide | 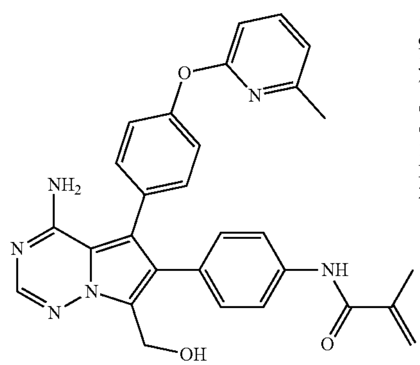 | $^1$H NMR (400 MHz, DMSO-d$_6$) δ 9.78 (s, 1H), 7.99 (s, 1H), 7.75 (t, J = 7.8 Hz, 1H), 7.64-7.55 (m, 2H), 7.32-7.26 (m, 2H), 7.22-7.10 (m, 4H), 7.03 (d, J = 7.4 Hz, 1H), 6.81 (d, J = 8.1 Hz, 1H), 5.77 (s, 1H), 5.51 (s, 1H), 5.17 (t, J = 5.0 Hz, 1H), 4.69 (d, J = 4.9 Hz, 2H), 2.36 (s, 3H), 1.94 (s, 3H). | 507.35 |
| N-(4-(4-amino-7-(hydroxymethyl)-5-(4-((6-methylpyridin-2-yl)oxy)phenyl)pyrrolo[2,1-f][1,2,4]triazin-6-yl)phenyl)acrylamide | 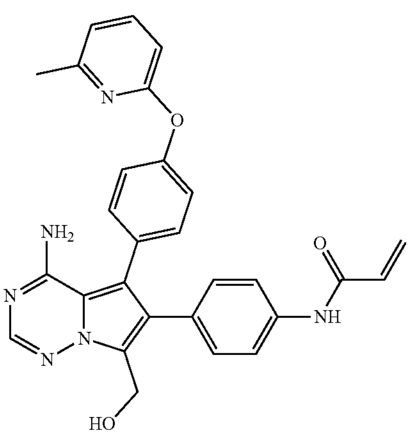 [SMILES: C=CC(=O)Nc1ccc(-c2c(-c3ccc(Oc4cccc(C)n4)cc3)c3c(N)ncnn3c2CO)cc1] | $^1$H NMR (400 MHz, DMSO-d$_6$) δ 10.14 (s, 1H), 7.99 (s, 1H), 7.75 (t, J = 7.7 Hz, 1H), 7.63-7.56 (m, 2H), 7.33-7.25 (m, 2H), 7.24-7.17 (m, 2H), 7.17-7.09 (m, 2H), 7.03 (d, J = 7.3 Hz, 1H), 6.81 (d, J = 8.1 Hz, 1H), 6.43 (dd, J = 17.0, 10.1 Hz, 1H), 6.25 (dd, J = 17.0, 2.1 Hz, 1H), 5.75 (dd, J = 10.1, 2.1 Hz, 1H), 5.16 (t, J = 5.0 Hz, 1H), 4.69 (d, J = 5.0 Hz, 2H), 2.36 (s, 3H). | 493.35 |

TABLE 9-continued

Additional Exemplary Compounds

| Compound | Structure | Proton NMR | MS [M + 1] |
|---|---|---|---|
| 4-(4-amino-7-(hydroxymethyl)-6-(4-methacrylamido-phenyl)pyrrolo[2,1-f][1,2,4]triazin-5-yl)-N-(2,2,2-trifluoroethyl)benzamide | 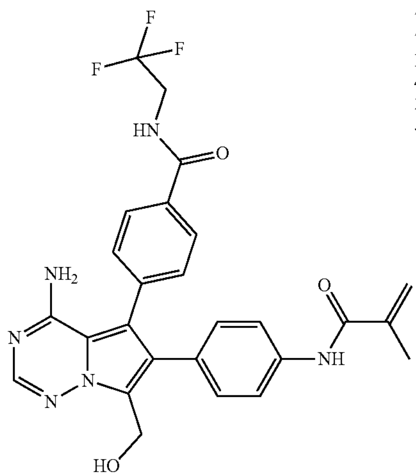 [SMILES: C=C(C)C(=O)Nc1ccc(-c2c(-c3ccc(C(=O)NCC(F)(F)F)cc3)c3c(N)ncnn3c2CO)cc1] | 1H NMR (400 MHz, DMSO-d6) δ 9.76 (s, 1H), 9.13 (s, 1H), 8.01 (s, 1H), 7.93-7.83 (m, 2H), 7.61-7.54 (m, 2H), 7.43-7.30 (m, 2H), 7.18-7.08 (m, 2H), 5.77 (d, J = 1.2 Hz, 1H), 5.51 (s, 0H), 5.16 (t, J = 4.9 Hz, 1H), 4.68 (d, J = 5.0 Hz, 2H), 4.19-4.00 (m, 2H), 1.93 (t, J = 1.2 Hz, 3H). | 525 |
| N-(4-(4-amino-7-(hydroxymethyl)-5-(4-(piperidine-1-carbonyl)phenyl)pyrrolo[2,1-f][1,2,4]triazin-6-yl)phenyl)methacrylamide | 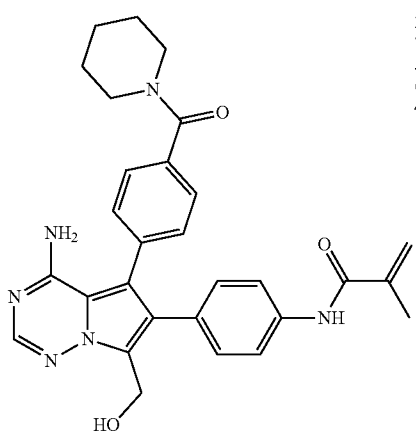 | $^1$H NMR (400 MHz, DMSO-d$_6$) δ 9.76 (s, 1H), 7.99 (s, 1H), 7.60-7.53 (m, 2H), 7.37 (d, J = 8.1 Hz, 2H), 7.32-7.26 (m, 2H), 7.15-7.09 (m, 2H), 5.77 (s, 1H), 5.50 (d, J = 1.9 Hz, 1H), 5.17 (s, 1H), 4.68 (s, 2H), 3.57- 3.35 (d, J = 2.8 Hz, 4H), 1.93 (t, J = 1.2 Hz, 3H), 1.69-1.40 (m, 6H). | 511.40 |
| N-(4-(4-amino-7-(methoxymethyl)-5-(4-((6-methylpyridin-2-yl)oxy)phenyl)pyrrolo[2,1-f][1,2,4]triazin-6-yl)phenyl)methacrylamide | 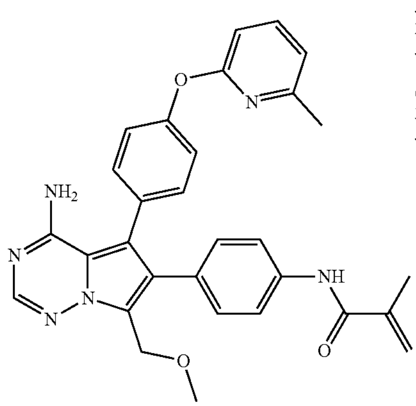 | $^1$H NMR (400 MHz, DMSO-d$_6$) δ 9.78 (s, 1H), 8.00 (s, 1H), 7.74 (t, J = 7.7 Hz, 1H), 7.61 (d, J = 8.6 Hz, 2H), 7.36-7.25 (m, 2H), 7.12 (d, J = 8.3 Hz, 4H), 7.03 (d, J = 7.4 Hz, 1H), 6.81 (d, J = 8.1 Hz, 1H), 5.77 (s, 1H), 5.50 (s, 1H), 4.60 (s, 2H), 3.31 (s, 3H), 2.35 (s, 3H), 1.94 (d, J = 1.3 Hz, 3H). | 521.40 |

TABLE 9-continued

Additional Exemplary Compounds

| Compound | Structure | Proton NMR | MS [M + 1] |
|---|---|---|---|
| N-(4-(4-amino-7-((dimethylamino)methyl)-5-(4-((6-methylpyridin-2-yl)oxy)phenyl)pyrrolo[2,1-f][1,2,4]triazin-6-yl)phenyl)methacrylamide | 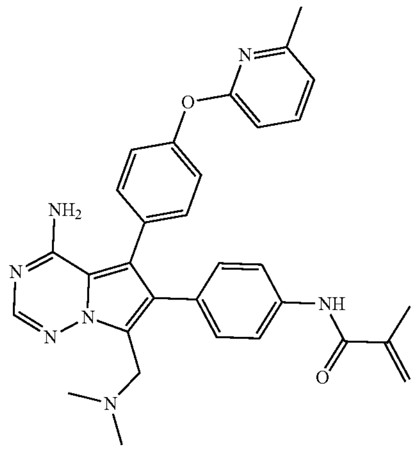 [SMILES: C=C(C)C(=O)Nc1ccc(-c2c(-c3ccc(Oc4cccc(C)n4)cc3)c3c(N)ncnn3c2CN(C)C)cc1] | $^1$H NMR (400 MHz, DMSO-$d_6$) δ 9.74 (s, 1H), 7.96 (s, 1H), 7.79-7.70 (m, 1H), 7.62-7.56 (m, 2H), 7.34-7.26 (m, 2H), 7.26-7.20 (m, 2H), 7.15-7.07 (m, 2H), 7.03 (d, J = 7.4 Hz, 1H), 6.80 (d, J = 8.1 Hz, 1H), 5.77 (s, 1H), 5.50 (t, J = 1.5 Hz, 1H), 3.71 (s, 2H), 2.36 (s, 3H), 2.11 (s, 6H), 1.94 (d, J = 1.2 Hz, 3H). | 534.35 |

Example 11

Scheme 9

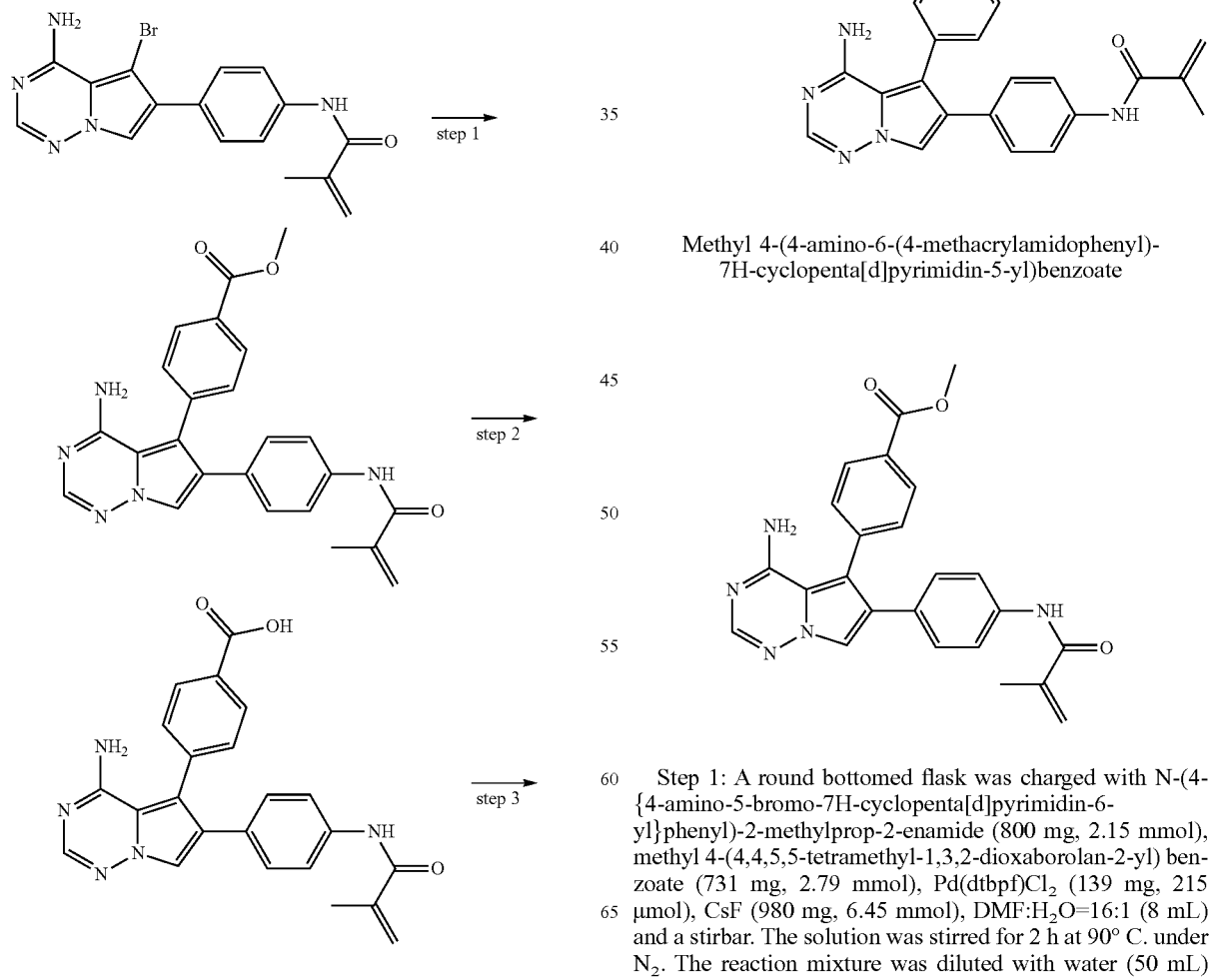

Methyl 4-(4-amino-6-(4-methacrylamidophenyl)-7H-cyclopenta[d]pyrimidin-5-yl)benzoate Step 1: A round bottomed flask was charged with N-(4-{4-amino-5-bromo-7H-cyclopenta[d]pyrimidin-6-yl}phenyl)-2-methylprop-2-enamide (800 mg, 2.15 mmol), methyl 4-(4,4,5,5-tetramethyl-1,3,2-dioxaborolan-2-yl) benzoate (731 mg, 2.79 mmol), Pd(dtbpf)Cl$_2$ (139 mg, 215 µmol), CsF (980 mg, 6.45 mmol), DMF:H$_2$O=16:1 (8 mL) and a stirbar. The solution was stirred for 2 h at 90° C. under N$_2$. The reaction mixture was diluted with water (50 mL)

and extracted with EtOAc (50 mL) three times. The combined organic layers were washed with brine, dried over sodium sulfate, filtered, and concentrated in vacuo. The resulting crude material was purified by silica gel chromatography. Concentration in vacuo resulted in methyl 4-{4-amino-6-[4-(2-methylprop-2-enamido)phenyl]-7H-cyclopenta[d]pyrimidin-5-yl}benzoate (600 mg, 56%) as an off-white amorphous solid.

4-(4-amino-6-(4-methacrylamidophenyl)-7H-cyclopenta[d]pyrimidin-5-yl)benzoic acid

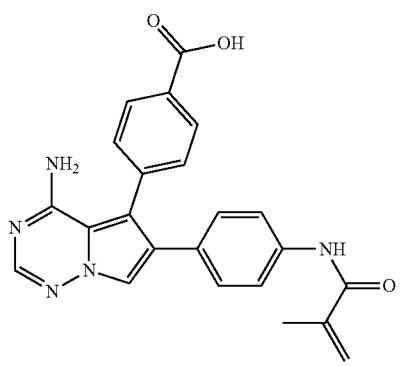 [SMILES: C=C(C)C(=O)Nc1ccc(-c2cn3ncnc(N)c3c2-c2ccc(C(=O)O)cc2)cc1]

Step 2: A round bottomed flask was charged with methyl 4-{4-amino-6-[4-(2-methylprop-2-enamido)phenyl]-7H-cyclopenta[d]pyrimidin-5-yl}benzoate (580 mg, 1.35 mmol), THF:LiOH (2M)=1:1 (6 mL) and a stirbar. The solution was stirred for 3 h at r.t. The pH value of the solution was adjusted to 6~7 with aq.HCl. The product was precipitated by the addition of HCl and dried. This resulted in 4-{4-amino-6-[4-(2-methylprop-2-enamido)phenyl]-7H-cyclopenta[d]pyrimidin-5-yl}benzoic acid (350 mg, 63%) as an off-white amorphous solid.

4-(4-amino-6-(4-methacrylamidophenyl)pyrrolo[2,1-f][1,2,4]triazin-5-yl)-N-(2-hydroxy-2-methylpropyl)benzamide

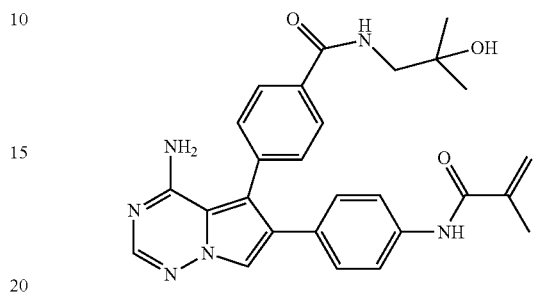

Step 3: A resealable reaction vial was charged with 4-{4-amino-6-[4-(2-methylprop-2-enamido)phenyl]-7aH-cyclopenta[d]pyrimidin-5-yl}benzoic acid (60 mg, 145 µmol), 1-amino-2-methylpropan-2-ol (15.5 mg, 174 µmol), HATU (55.2 mg, 145 µmol), DIEA (37.4 mg, 290 µmol), dimethylformamide (10 mL) and a stirbar. The mixture was stirred for 1 h at r.t. The reaction mixture was quenched with water and purified by HPLC (Column: XBridge Prep C18 OBD Column, 5 um, 19*150 mm; Mobile Phase A:Water(10 MMOL/L $NH_4HCO_3$), Mobile Phase B:ACN; Flow rate:25 mL/min; Gradient:15 B to 50 B in 7 min; 254/220 nm; RT1:7.58;). Lyophilization yielded 4-{4-amino-6-[4-(2-methylprop enamido)phenyl]pyrrolo[2,1-f][1,2,4]triazin-5-yl}-N-(2-hydroxy-2-methylpropyl)benzamide (40.2 mg, 56.4%) as a white amorphous solid.

Additional compounds prepared according to the methods of Example 11 are depicted in Table 10 below.

TABLE 10

Additional Exemplary Compounds

| Compound | Structure | Proton NMR | MS [M + 1] |
|---|---|---|---|
| 4-(4-amino-6-(4-methacrylamidophenyl)pyrrolo[2,1-f][1,2,4]triazin-5-yl)-N-(2,2,2-trifluoroethyl)benzamide | | $^1$H NMR (400 MHz, DMSO-$d_6$) δ 9.74 (s, 1H), 9.18 (t, J = 6.3 Hz, 1H), 8.03 (s, 1H), 8.00-7.89 (m, 3H), 7.59-7.51 (m, 2H), 7.51-7.37 (m, 2H), 7.14-7.03 (m, 2H), 5.77 (d, J = 1.1 Hz, 1H), 5.50 (t, J = 1.5 Hz, 1H), 4.12 (qd, J = 9.7, 6.1 Hz, 2H), 1.93 (t, J = 1.2 Hz, 3H). | 485.25 |

TABLE 10-continued

Additional Exemplary Compounds

| Compound | Structure | Proton NMR | MS [M + 1] |
|---|---|---|---|
| N-(4-(4-amino-5-(4-(piperidine-1-carbonyl)phenyl)pyrrolo[2,1-f][1,2,4]triazin-6-yl)phenyl)methacrylamide | 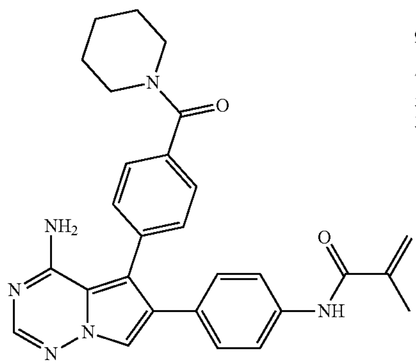 | ¹H NMR (400 MHz, DMSO-d₆) δ 9.74 (s, 1H), 8.02 (s, 1H), 7.91 (s, 1H), 7.63-7.50 (m, 2H), 7.50-7.28 (m, 4H), 7.17-7.03 (m, 2H), 5.77 (s, 1H), 5.57-5.46 (m, 1H), 3.48 (d, J = 89.5 Hz, 4H), 1.75-1.37 (m, 6H). | 481.40 |
| N-(4-(4-amino-5-(4-(piperidine-1-carbonyl)phenyl)pyrrolo[2,1-f][1,2,4]triazin-6-yl)phenyl)acrylamide | 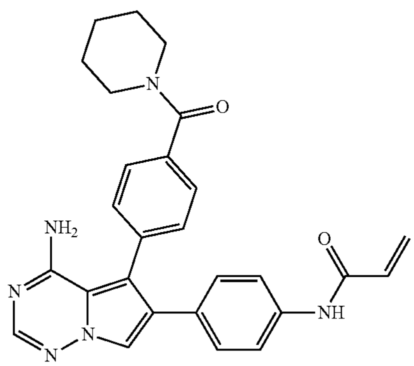 [SMILES: C=CC(=O)Nc1ccc(-c2cn3ncnc(N)c3c2-c2ccc(C(=O)N3CCCCC3)cc2)cc1] | ¹H NMR (400 MHz, DMSO-d₆) δ 10.11 (s, 1H), 8.02 (s, 1H), 7.91 (s, 1H), 7.55-7.48 (m, 2H), 7.44 (d, J= 8.2 Hz, 2H), 7.39 (d, J = 8.1 Hz, 2H), 7.14-7.03 (m, 2H), 6.56-6.35 (m, 1H), 6.24 (dd, J = 17.0, 2.1 Hz, 1H), 5.74 (dd, J = 10.1, 2.1 Hz, 1H), 3.59 (s, 4H), 1.64 (s, 2H), 1.54 (s, 4H). | 467.35 |
| 4-(6-(4-acrylamidophenyl)-4-aminopyrrolo[2,1-f][1,2,4]triazin-5-yl)-N-(2,2,2-trifluoroethyl)benzamide | 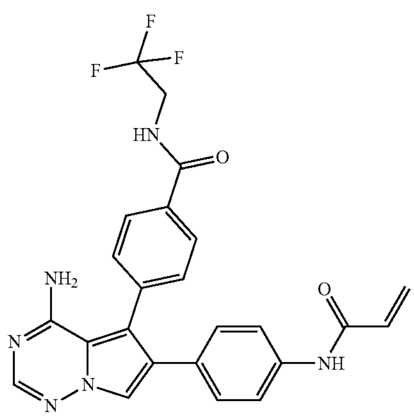 [SMILES: C=CC(=O)Nc1ccc(-c2cn3ncnc(N)c3c2-c2ccc(C(=O)NCC(F)(F)F)cc2)cc1] | ¹H NMR (400 MHz, DMSO-d₆) δ 10.11 (s, 1H), 9.18 (t, J = 6.3 Hz, 1H), 8.03 (s, 1H), 8.01-7.89 (m, 3H), 7.56-7.50 (m, 2H), 7.50-7.33 (m, 2H), 7.17-7.05 (m, 2H), 6.41 (dd, J = 17.0, 10.1 Hz, 1H), 6.24 (dd, J = 17.0, 2.1 Hz, 1H), 5.74 (dd, J = 10.0, 2.1 Hz, 1H), 4.21-4.03 (m, 2H). | 481.30 |
| 4-(4-amino-6-(4-methacrylamidophenyl)pyrrolo[2,1-f][1,2,4]triazin-5-yl)-N-cyclobutyl-benzamide | 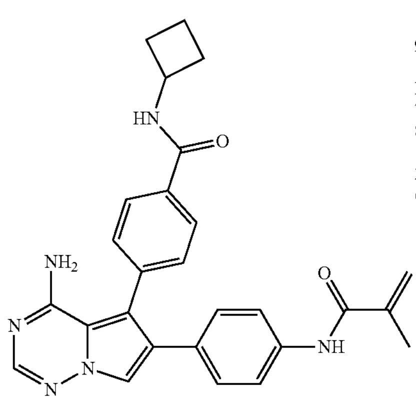 | ¹H NMR (400 MHz, DMSO-d₆) δ 9.75 (s, 1H), 8.70 (d, J = 7.4 Hz, 1H), 8.03 (s, 1H), 7.91 (d, J = 8.3 Hz, 3H), 7.53 (d, J = 8.5 Hz, 2H), 7.42 (d, J = 7.9 Hz, 2H), 7.10 (d, J = 8.5 Hz, 2H), 5.76 (s, 1H), 5.50 (s, 1H), 4.53-4.26 (m, 1H), 2.22 (s, 2H), 2.09 (t, J = 10.6 Hz, 2H), 1.93 (s, 3H), 1.68 (s, 2H). | 467.35 |

TABLE 10-continued

Additional Exemplary Compounds

| Compound | Structure | Proton NMR | MS [M + 1] |
|---|---|---|---|
| N-(4-(4-amino-5-(4-(N-cyclobutylsulfamoyl)phenyl)pyrrolo[2,1-f][1,2,4]triazin-6-yl)phenyl)methacrylamide | 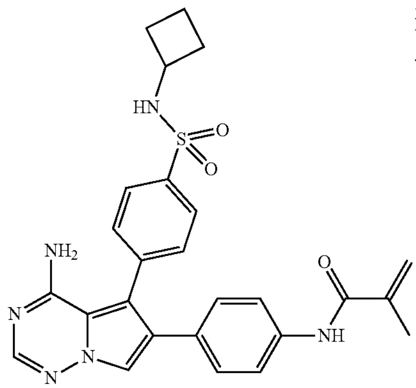 | $^1$H NMR (400 MHz, DMSO-$d_6$) δ 9.75 (s, 1H), 8.04 (s, 1H), 7.98 (s, 1H), 7.93 (s, 1H), 7.87-7.80 (m, 2H), 7.55-7.49 (m, 4H), 7.08-7.01 (m, 2H), 5.75 (s, 1H), 5.50 (t, J = 1.5 Hz, 1H), 3.68 (s, 1H), 2.02-1.85 (m, 5H), 1.79-1.65 (m, 2H), 1.63-1.38 (m, 2H). | 503.35 |
| 4-(4-amino-6-(4-methacrylamidophenyl)pyrrolo[2,1-f][1,2,4]triazin-5-yl)-N,N-dimethylcyclohex-3-ene-1-carboxamide | 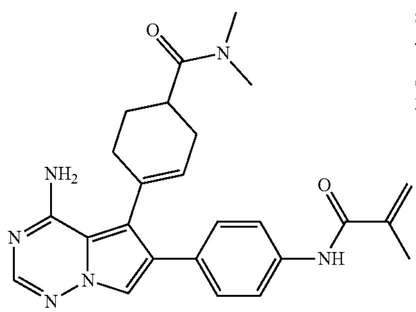 | $^1$H NMR (400 MHz, DMSO-$d_6$) δ 9.82 (s, 1H), 7.90 (s, 1H), 7.78 (s, 1H), 7.75-7.66 (m, 2H), 7.54 (d, J = 8.3 Hz, 2H), 7.25 (s, 1H), 5.90 (d, J = 4.4 Hz, 1H), 5.81 (t, J = 1.1 Hz, 1H), 5.52 (t, J = 1.5 Hz, 1H), 3.20 (d, J = 13.7 Hz, 1H), 3.06 (s, 3H), 2.85 (s, 3H), 2.36 (s, 2H), 1.97 (t, J = 1.2 Hz, 3H), 1.90 (s, 2H), 1.77 (s, 1H). | 445.35 |
| 4-(4-amino-6-(4-methacrylamidophenyl)pyrrolo[2,1-f][1,2,4]triazin-5-yl)-N-(2-hydroxy-2-methylpropyl)benzamide | 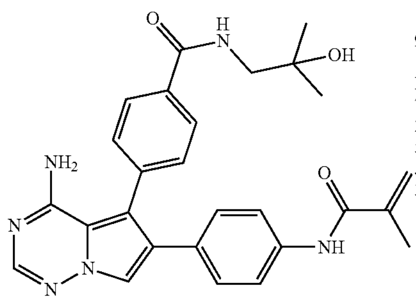 | $^1$H NMR (400 MHz, DMSO-$d_6$) δ 9.74 (s, 1H), 8.34 (t, J = 6.2 Hz, 1H), 8.03 (s, 1H), 7.93 (d, J = 8.5 Hz, 3H), 7.56-7.48 (m, 2H), 7.45-7.39 (m, 2H), 7.18-7.06 (m, 2H), 5.76 (d, J = 1.4 Hz, 1H), 5.53-5.43 (m, 1H), 4.56 (s, 1H), 3.28 (d, J = 6.1 Hz, 2H), 1.92 (t, J = 1.2 Hz, 3H), 1.12 (s, 6H). | 485.35 |
| 4-(4-amino-6-(4-methacrylamidophenyl)pyrrolo[2,1-f][1,2,4]triazin-5-yl)-N-(tetrahydrofuran-3-yl)benzamide | 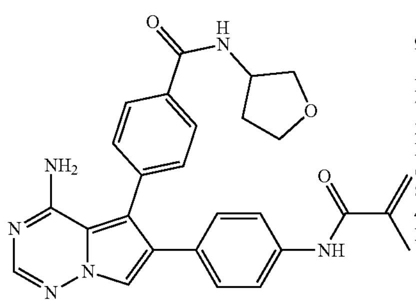 | $^1$H NMR (400 MHz, DMSO-$d_6$) δ 9.74 (s, 1H), 8.62 (d, J = 6.4 Hz, 1H), 8.03 (s, 1H), 7.93 (d, J = 8.0 Hz, 3H), 7.62-7.49 (m, 2H), 7.46-7.39 (m, 2H), 7.14-7.04 (m, 2H), 5.76 (s, 1H), 5.49 (t, J = 1.5 Hz, 1H), 4.51-4.41 (m, 1H), 3.87 (dd, J = 9.0, 6.6 Hz, 2H), 3.73 (td, J = 8.1, 5.7 Hz, 1H), 3.61 (dd, J = 8.9, 4.4 Hz, 1H), 2.16 (dq, J = 12.6, 7.6 Hz, 1H), 1.99-1.81 (m, 4H). | 483.15 |

TABLE 10-continued

Additional Exemplary Compounds

| Compound | Structure | Proton NMR | MS [M + 1] |
|---|---|---|---|
| N-(4-(5-(4-(2-azabicyclo[2.1.1]hexane-2-carbonyl)phenyl)-4-aminopyrrolo[2,1-f][1,2,4]triazin-6-yl)phenyl)methacrylamide | 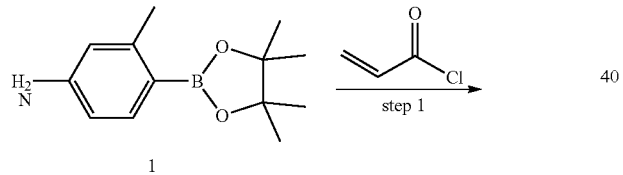 | $^1$H NMR (400 MHz, DMSO-$d_6$) δ 9.74 (s, 1H), 8.02 (s, 1H), 7.91 (s, 1H), 7.73 (d, J = 7.8 Hz, 1H), 7.57-7.47 (m, 3H), 7.39 (d, J = 7.3 Hz, 2H), 7.17-7.06 (m, 2H), 5.77 (d, J = 1.5 Hz, 1H), 5.49 (t, J = 1.5 Hz, 1H), 4.55 (dd, J = 147.8, 7.0 Hz, 1H), 3.48 (d, J = 10.6 Hz, 2H), 2.91 (d, J = 16.9 Hz, 1H), 2.05-1.84 (m, 5H), 1.51 (s, 1H), 1.37 (s, 1H). | 479.35 |
| 4-(4-amino-6-(4-methacrylamidophenyl)pyrrolo [2,1-f][1,2,4]triazin-5-yl)-N-(2-methoxy-2-methylpropyl)benzamide | 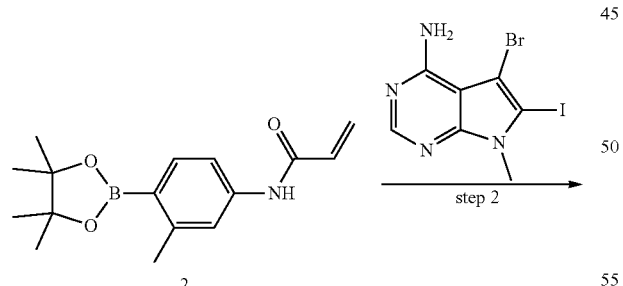 | $^1$H NMR (400 MHz, DMSO-$d_6$) δ 9.74 (s, 1H), 8.33 (t, J = 6.2 Hz, 1H), 8.03 (s, 1H), 7.95-7.88 (m, 3H), 7.54 (d, J = 8.8 Hz, 2H), 7.43 (d, J = 1.9 Hz, 2H), 7.15-7.06 (m, 2H), 5.76 (s, 1H), 5.49 (s, 1H), 3.35 (d, J = 6.2 Hz, 2H), 3.16 (s, 3H), 1.92 (t, J = 1.2 Hz, 3H), 1.13 (s, 6H). | 499.25 |

Example 12

Scheme 10

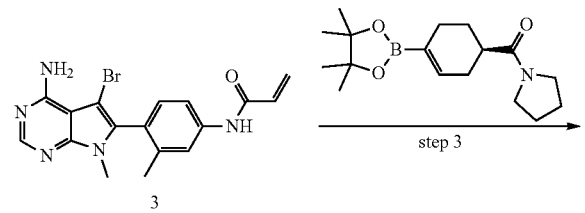

N-(3-methyl-4-(4,4,5,5-tetramethyl-1,3,2-dioxaborolan-2-yl)phenyl)acrylamide

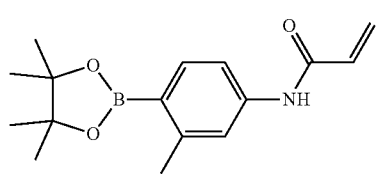 [SMILES: C=CC(=O)Nc1ccc(B2OC(C)(C)C(C)(C)O2)c(C)c1]

Step 1: A round bottomed flask was charged with 3-methyl-4-(4,4,5,5-tetramethyl-1,3,2-dioxaborolan-2-yl) aniline (10 g, 42.8 mmol), prop-2-enoyl chloride (3.87 g, 42.8 mmol), pyridine (10.1 g, 128 mmol), dichloromethane (150 mL) and a stirbar. The solution was stirred for 1 h at 0° C. The reaction mixture was quenched with water, extracted with DCM. The organic phase was dried over Na$_2$SO$_4$, filtered and evaporated in vacuo. The resulting crude material was purified by silica gel chromatography. Concentration in vacuo resulted in N-(3-methyl-4-(4,4,5,5-tetramethyl-1,3,2-dioxaborolan-2-yl)phenyl)acrylamide (12 g, 98%) as a yellow oil.

N-(4-(4-amino-5-bromo-7-methyl-7H-pyrrolo[2,3-d]pyrimidin-6-yl)-3-methylphenyl)acrylamide

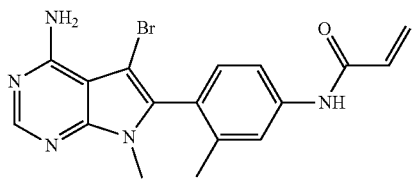 [SMILES: C=CC(=O)Nc1ccc(-c2c(Br)c3c(N)ncnc3n2C)c(C)c1]

Step 2: A round bottomed flask was charged with N-[3-methyl-4-(4,4,5,5-tetramethyl-1,3,2-dioxaborolan-2-yl)phenyl]prop-2-enamide (1 g, 3.48 mmol), 5-bromo-6-iodo-7-methyl-7H-pyrrolo[2,3-d]pyrimidin-4-amine (1.22 g, 3.48 mmol), Pd(dppf)Cl$_2$ (254 mg, 348 μmol), K$_3$PO$_4$ (2.20 g, 10.4 mmol), DMF/H$_2$O (16:1) (15 mL) and a stirbar. The solution was stirred for 2 h at 50° C. The reaction mixture was quenched with water, extracted with DCM. The organic phase was washed with brine three times, dried over Na$_2$SO$_4$, filtered and evaporated in vacuo. The resulting crude material was purified by silica gel chromatography. Concentration in vacuo resulted in N-(4-(4-amino-5-bromo-7-methyl-7H-pyrrolo[2,3-d]pyrimidin-6-yl)-3-methylphenyl)acrylamide (440 mg, 33%) as an off-white amorphous solid.

(R)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)acrylamide

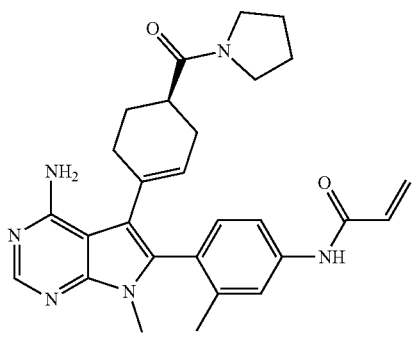 [SMILES: C=CC(=O)Nc1ccc(-c2c(C3=CC[C@H](C(=O)N4CCCC4)CC3)c3c(N)ncnc3n2C)c(C)c1]

Step 3: A resealable reaction vial was charged with N-(4-{4-amino-5-bromo-7-methyl-7H-pyrrolo[2,3-d]pyrimidin-6-yl}-3-methylphenyl)prop-2-enamide (200 mg, 517 μmol), 1-[(1R)-4-(4,4,5,5-tetramethyl-1,3,2-dioxaborolan-2-yl)cyclohex-3-ene-1-carbonyl]pyrrolidine (156 mg, 517 μmol), Pd(pddf)Cl$_2$ (37.8 mg, 517 μmol), Na$_2$CO$_3$ (164 mg, 1.55 mmol), DMF (10 mL) and a stirbar before being evacuated and purged with nitrogen three times. The mixture was stirred for 2 h at 90° C. The reaction mixture was quenched with water, extracted with DCM. The organic phase was washed with brine three times, dried over Na$_2$SO$_4$, filtered and evaporated in vacuo. The resulting crude material was purified by prep-HPLC (Column: YMC-Actus Triart C$_{18}$, 30*250, 5 um; Mobile Phase A:Water(10 MMOL/L NH$_4$HCO$_3$), Mobile Phase B:ACN; Flow rate:50 mL/min; Gradient:40 B to 62 B in 8 min; 220 nm; RT1: 6.83;). Lyophilization yielded (R)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)acrylamide(40 mg, 16%) as an off-white amorphous solid.

(S)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)acrylamide

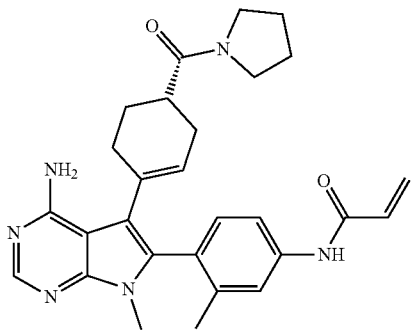

Step 4: A resealable reaction vial was charged with N-(4-{4-amino-5-bromo-7-methyl-7H-pyrrolo[2,3-d]pyrimidin-6-yl}-3-methylphenyl)prop-2-enamide (240 mg, 621 μmol), Pd(dppf)Cl$_2$ (45.4 mg, 62.1 μmol), Na$_2$CO$_3$ (197 mg, 1.86 mmol), 1-[(1S)-4-(4,4,5,5-tetramethyl-1,3,2-dioxaborolan-2-yl)cyclohex-3-ene-1-carbonyl]pyrrolidine (189240 mg, 621 μmol), dimethylformamide/H$_2$O (8 mL) and a stirbar before being evacuated and purged with nitrogen three times. The mixture was stirred for 2 h at 90° C. The reaction mixture was quenched with water, extracted with DCM. The organic phase was washed with brine three times, dried over Na$_2$SO$_4$, filtered and evaporated in vacuo. The resulting crude material was purified by prep-HPLC (Column: YMC-Actus Triart C18, 30*250, 5 um; Mobile Phase A:Water(10 MMOL/L NH$_4$HCO$_3$), Mobile Phase B:ACN; Flow rate:50 mL/min; Gradient:40 B to 60 B in 8 min; 220 nm; RT1:7.67; RT2:; Injection Volumn: ml; Number Of Runs:;). Lyophilization yielded (S)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)acrylamide (39 mg, 14%) as an off-white amorphous solid.

Additional compounds prepared according to the methods of Example 12 are depicted in Table 11 below.

TABLE 11

Additional Exemplary Compounds

| Compound | Structure | Proton NMR | MS [M + 1] |
|---|---|---|---|
| N-(4-(5-methyl-7-(4-((6-methylpyridin-2-yl)oxy)phenyl)-5H-pyrrolo[3,2-d]pyrimidin-6-yl)phenyl)methacrylamide | 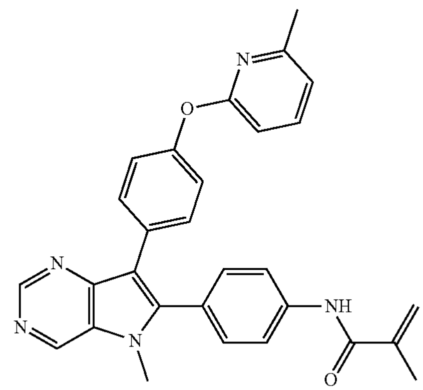 [SMILES: C=C(C)C(=O)Nc1ccc(-c2c(-c3ccc(Oc4cccc(C)n4)cc3)c3ncncc3n2C)cc1] | ¹H NMR (400 MHz, DMSO-d₆) δ 10.03 (s, 1H), 9.16 (s, 1H), 8.94 (s, 1H), 7.88 (d, J = 8.4 Hz, 2H), 7.72 (t, J = 7.8 Hz, 1H), 7.48 (dd, J = 20.9, 8.5 Hz, 4H), 7.08-6.96 (m, 3H), 6.75 (d, J = 8.2 Hz, 1H), 5.85 (s, 1H), 5.57 (s, 1H), 3.75 (s, 3H), 2.34 (s, 3H), 1.98 (s, 3H). | 476.15 |
| N-(4-(4-amino-7-oxo-3-(4-(pyrrolidine-1-carbonyl)phenyl)-6,7-dihydro-1H-pyrrolo[2,3-d]pyridazin-2-yl)phenyl)methacrylamide | 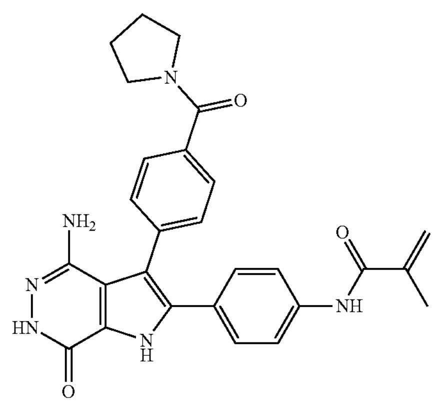 [SMILES: C=C(C)C(=O)Nc1ccc(-c2[nH]c3c(=O)[nH]nc(N)c3c2-c2ccc(C(=O)N3CCCC3)cc2)cc1] | ¹H NMR (400 MHz, DMSO-d₆) δ 12.72 (s, 1H), 11.38 (s, 1H), 9.83 (s, 1H), 7.62-7.54 (m, 4H), 7.45-7.35 (m, 2H), 7.28-7.21 (m, 2H), 5.78 (s, 1H), 5.52 (s, 1H), 4.55 (s, 2H), 3.46 (dt, J = 23.1, 6.3 Hz, 4H), 1.98-1.80 (m, 7H). | 483.25 |
| N-(4-(4-amino-1-methyl-7-oxo-3-(4-(pyrrolidine-1-carbonyl)phenyl)-6,7-dihydro-1H-pyrrolo[2,3-d]pyridazin-2-yl)phenyl)methacrylamide | 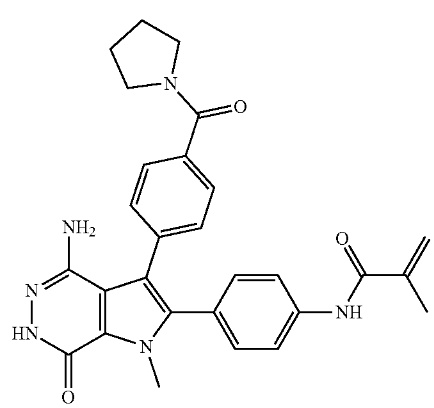 [SMILES: C=C(C)C(=O)Nc1ccc(-c2c(-c3ccc(C(=O)N4CCCC4)cc3)c3c(N)n[nH]c(=O)c3n2C)cc1] | ¹H NMR (400 MHz, DMSO-d₆) δ 11.41 (s, 1H), 9.91 (s, 1H), 7.69 (d, J = 8.2 Hz, 2H), 7.47 (d, J = 7.7 Hz, 2H), 7.26 (dd, J = 12.9, 8.1 Hz, 4H), 5.79 (s, 1H), 5.53 (s, 1H), 4.59 (s, 2H), 3.98 (s, 3H), 3.45 (t, J = 1.0 Hz, 2H), 1.93 (s, 3H), 1.82 (dt, J = 18.4, 7.0 Hz, 4H). | 497.35 |

TABLE 11-continued

Additional Exemplary Compounds

| Compound | Structure | Proton NMR | MS [M + 1] |
|---|---|---|---|
| N-(4-(4-amino-1,6-dimethyl-7-oxo-3-(4-(pyrrolidine-1-carbonyl)phenyl)-6,7-dihydro-1H-pyrrolo[2,3-d]pyridazin-2-yl)phenyl)methacrylamide | 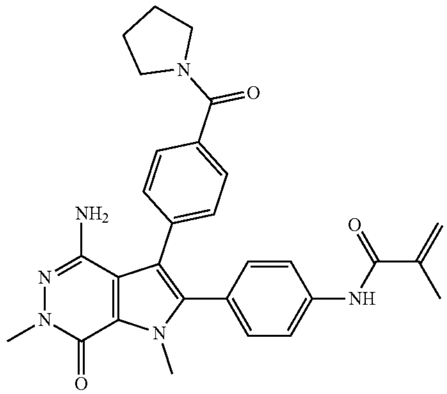 [SMILES: C=C(C)C(=O)Nc1ccc(-c2c(-c3ccc(C(=O)N4CCCC4)cc3)c3c(N)nn(C)c(=O)c3n2C)cc1] | ¹H NMR (400 MHz, DMSO-d₆) δ 9.90 (s, 1H), 7.73-7.66 (m, 2H), 7.47 (d, J = 8.1 Hz, 2H), 7.31-7.21 (m, 4H), 5.79 (s, 1H), 5.53 (s, 1H), 4.72 (s, 2H), 3.98 (s, 3H), 3.55 (s, 3H), 3.45 (t, J = 6.8 Hz, 2H), 3.37 (t, J = 6.4 Hz, 2H), 1.94 (s, 3H), 1.84 (m, J = 18.4 Hz, 4H). | 511.25 |
| N-(4-(4-amino-7-methyl-5-(2-oxo-4-(pyrrolidine-1-carbonyl)pyridin-1(2H)-yl)-7H-pyrrolo[2,3-d]pyrimidin-6-yl)phenyl)methacrylamide | 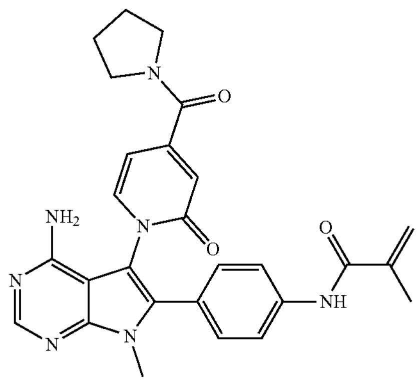 [SMILES: C=C(C)C(=O)Nc1ccc(-c2c(-n3ccc(C(=O)N4CCCC4)cc3=O)c3c(N)ncnc3n2C)cc1] | ¹H NMR (400 MHz, DMSO-d₆) δ 9.93 (s, 1H), 8.21 (s, 1H), 7.84-7.71 (m, 2H), 7.44 (d, J = 1.0 Hz, 1H), 7.36-7.25 (m, 2H), 6.49 (d, J = 1.7 Hz, 1H), 6.32 (s, 2H), 6.14 (dd, J = 7.0, 1.8 Hz, 1H), 5.88-5.79 (m, 1H), 5.54 (d, J = 1.8 Hz, 1H), 3.65 (s, 3H), 3.40 (td, J = 11.7, 11.3, 5.5 Hz, 3H), 1.95 (d, J = 1.2 Hz, 3H), 1.89-1.80 (m, 4H). | 498.25 |
| (R)-N-(4-(4-amino-7-methyl-5-(2-methyl-4-(pyrrolidine-1-carbonyl)cyclohex-1-en-1-yl)-7H-pyrrolo[2,3-d]pyrimidin-6-yl)phenyl)methacrylamide | | ¹H NMR (400 MHz, Methanol-d₄) 8.15 (s, 1H), 7.82-7.75 (m, 2H), 7.46 (d, J = 8.3 Hz, 2H), 5.97 (s, 1H), 5.85 (t, J = 1.0 Hz, 1H), 5.59-5.53 (m, 1H), 3.67 (s, 4H), 3.60-3.45 (m, 1H), 3.49-3.35 (m, 2H), 2.98 (s, 1H), 2.46 (d, J = 9.9 Hz, 1H), 2.37 (s, 1H), 2.07 (t, J = 1.2 Hz, 3H), 2.01-1.90 (m, 5H), 1.72 (s, 1H), 1.55 (d, J = 12.8 Hz, 1H), 0.90 (s, 3H). | 499.25 |
| (R)-N-(4-(4-amino-7-methyl-5-(2-methyl-4-(pyrrolidine-1-carbonyl)cyclohex-1-en-1-yl)-7H-pyrrolo[2,3-d]pyrimidin-6-yl)phenyl)methacrylamide | | ¹H NMR (400 MHz, Methanol-d₄) 8.15 (s, 1H), 7.78 (d, J = 8.3 Hz, 2H), 7.46 (d, J = 8.3 Hz, 2H), 5.97 (s, 1H), 5.87-5.82 (m, 1H), 5.56 (q, J = 1.6 Hz, 1H), 3.67 (s, 4H), 3.60-3.51 (m, 1H), 3.50-3.35 (m, 2H), 2.98 (s, 1H), 2.60-2.46 (d, J = 10.4 Hz, 1H), 2.37 (s, 1H), 2.07 (t, J = 1.3 Hz, 3H), 2.00 (p, J = 6.5 Hz, 2H), 1.95-1.85 (m, 2H), 1.80-1.60 (s, 1H), 1.59-1.50 (m, 1H), 1.1-0.45 (m, 3H). | 499.25 |

TABLE 11-continued

Additional Exemplary Compounds

| Compound | Structure | Proton NMR | MS [M + 1] |
| --- | --- | --- | --- |
| (S)-N-(4-(4-amino-7-methyl-5-(2-methyl-4-(pyrrolidine-1-carbonyl)cyclohex-1-en-1-yl)-7H-pyrrolo[2,3-d]pyrimidin-6-yl)phenyl)methacrylamide | | 1H NMR (400 MHz, Methanol-$d_4$) 8.15 (s, 1H), 7.83-7.75 (m, 2H), 7.52-7.45 (m, 2H), 6.03 (t, J = 3.1 Hz, 1H), 5.85 (t, J = 0.9 Hz, 1H), 5.57 (d, J = 1.9 Hz, 1H), 3.66 (s, 3H), 3.63 (s, 1H), 3.62-3.49 (m, 1H), 3.48-3.35 (m, 2H), 2.75 (s, 1H), 2.49 (s, 1H), 2.37 (s, 1H), 2.07 (t, J = 1.2 Hz, 3H), 1.99 (q, J = 6.6 Hz, 3H), 1.95-1.85 (m, 2H), 1.84 (s, 1H), 1.55 (q, J = 11.1 Hz, 1H), 0.74 (d, J = 7.1 Hz, 3H). | 499.20 |
| (S)-N-(4-(4-amino-7-methyl-5-(2-methyl-4-(pyrrolidine-1-carbonyl)cyclohex-1-en-1-yl)-7H-pyrrolo[2,3-d]pyrimidin-6-yl)phenyl)methacrylamide | | $^1$H NMR (400 MHz, Methanol-$d_4$) 8.15 (s, 1H), 7.83-7.75 (m, 2H), 7.51-7.45 (m, 2H), 6.06-6.00 (m, 1H), 5.85 (t, J = 1.0 Hz, 1H), 5.57 (q, J = 1.8 Hz, 1H), 3.66 (s, 3H), 3.61-3.48 (m, 2H), 3.43-3.35 (m, 2H), 3.13-2.71 (s, 1H), 2.75 (s, 1H), 2.37 (s, 1H), 2.10-1.91 (m, 6H), 1.89 (dd, J = 10.4, 4.4 Hz, 2H), 1.84 (s, 1H), 1.62-1.49 (m, 1H), 0.74 (d, J = 7.1 Hz, 3H). | 499.30 |
| (S)-N-(4-(4-amino-5-(2-fluoro-4-(pyrrolidine-1-carbonyl)cyclohex-1-en-1-yl)-7-methyl-7H-pyrrolo[2,3-d]pyrimidin-6-yl)phenyl)methacrylamide | 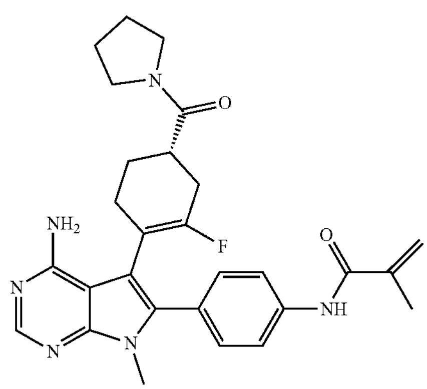 [SMILES: C=C(C)C(=O)Nc1ccc(-c2c(C3=C(F)C[C@@H](C(=O)N4CCCC4)CC3)c3c(N)ncnc3n2C)cc1] | $^1$H NMR (400 MHz, Methanol-$d_4$) 8.15 (d, J = 11.9 Hz, 1H), 7.84-7.75 (m, 2H), 7.48-7.40 (m, 2H), 5.85 (s, 1H), 5.57 (s, 1H), 3.69 (d, J = 5.4 Hz, 3H), 3.67-3.50 (m, 1H), 3.52-3.36 (m, 2H), 3.16 (d, J = 1.7 Hz, 2H), 2.48 (t, J = 16.7 Hz, 2H), 2.15 (s, 1H), 2.10-1.69 (m, 10H). | 503.25 |
| (R)-N-(4-(4-amino-5-(2-fluoro-4-(pyrrolidine-1-carbonyl)cyclohex-1-en-1-yl)-7-methyl-7H-pyrrolo[2,3-d]pyrimidin-6-yl)phenyl)methacrylamide | 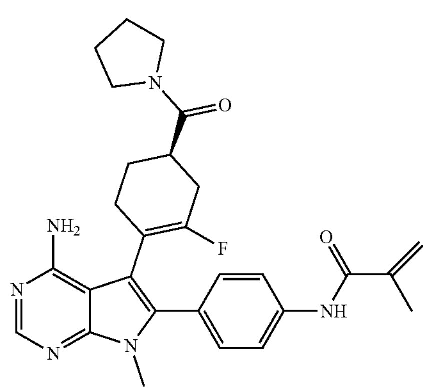 [SMILES: C=C(C)C(=O)Nc1ccc(-c2c(C3=C(F)C[C@H](C(=O)N4CCCC4)CC3)c3c(N)ncnc3n2C)cc1] | $^1$H NMR (400 MHz, Methanol-$d_4$) 8.16 (d, J = 8.6 Hz, 1H), 7.84-7.75 (m, 2H), 7.48-7.40 (m, 2H), 5.85 (t, J = 1.0 Hz, 1H), 5.57 (d, J = 2.0 Hz, 1H), 3.69 (d, J = 3.1 Hz, 3H), 3.67-3.55 (m, 1H), 3.55-3.35 (m, 3H), 3.16 (s, 1H), 2.50 (d, J = 11.2 Hz, 2H), 2.15 (s, 1H), 2.07 (t, J = 1.2 Hz, 3H), 1.99 (p, J = 6.5 Hz, 2H), 1.94-1.86 (m, 4H), 1.69 (s, 1H). | 503.25 |

TABLE 11-continued

Additional Exemplary Compounds

| Compound | Structure | Proton NMR | MS [M + 1] |
|---|---|---|---|
| (R)-N-(4-(4-amino-7-methyl-5-(2-methyl-1-oxo-2-azaspiro[4.5]dec-7-en-8-yl)-7H-pyrrolo[2,3-d]pyrimidin-6-yl)phenyl)methacrylamide | 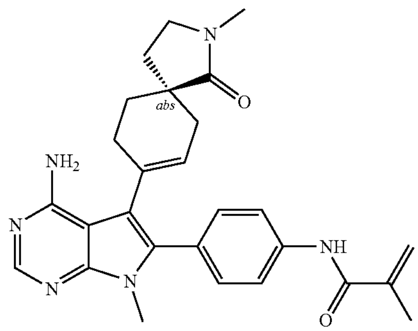 [SMILES: C=C(C)C(=O)Nc1ccc(-c2c(C3=CC[C@]4(CC3)CCN(C)C4=O)c3c(N)ncnc3n2C)cc1] | ¹H NMR (400 MHz, DMSO-d₆) δ 9.95 (s, 1H), 8.11 (s, 1H), 7.84-7.77 (m, 2H), 7.47-7.41 (m, 2H), 6.65 (s, 1H), 5.83 (s, 1H), 5.71 (d, J = 4.0 Hz, 1H), 5.56 (d, J = 1.8 Hz, 1H), 3.59 (s, 3H), 3.26 (ddt, J = 9.7, 7.1, 3.4 Hz, 2H), 2.73 (s, 3H), 2.27 (d, J = 17.7 Hz, 1H), 2.17-2.01 (m, 2H), 1.97 (s, 3H), 1.90 (s, 1H), 1.87-1.72 (m, 3H), 1.45-1.31 (m, 1H). | 471.25 |
| N-(4-(4-amino-7-methyl-5-(3-(6-methylpyridin-2-yl)-2,3-dihydrobenzofuran-6-yl)-7H-pyrrolo[2,3-d]pyrimidin-6-yl)phenyl)methacrylamide | 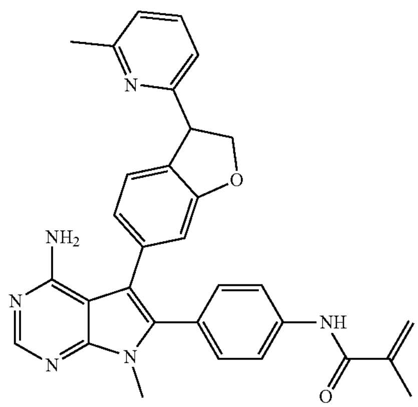 [SMILES: C=C(C)C(=O)Nc1ccc(-c2c(-c3ccc4c(c3)OCC4c3cccc(C)n3)c3c(N)ncnc3n2C)cc1] | ¹H NMR (400 MHz, DMSO-d₆) δ 9.90 (s, 1H), 8.18 (s, 1H), 7.77-7.64 (m, 3H), 7.34-7.24 (m, 2H), 7.21-7.12 (m, 2H), 7.06 (d, J = 7.6 Hz, 1H), 6.73 (d, J = 1.5 Hz, 1H), 6.69 (dd, J = 16.4, 1.5 Hz, 1H), 6.25-5.61 (m, 2H), 5.61-5.50 (m, 1H), 4.97-4.68 (m, 3H), 3.58 (s, 3H), 2.45 (s, 3H), 1.95 (t, J = 1.2 Hz, 3H). | 517.25 |
| (R)-N-(4-(4-amino-7-methyl-5-(3-(6-methylpyridin-2-yl)-2,3-dihydrobenzofuran-6-yl)-7H-pyrrolo[2,3-d]pyrimidin-6-yl)phenyl)methacrylamide | 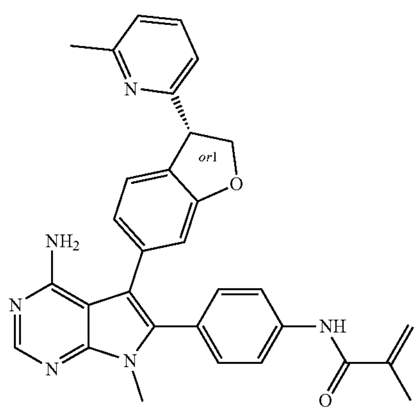 [SMILES: C=C(C)C(=O)Nc1ccc(-c2c(-c3ccc4c(c3)OC[C@H]4c3cccc(C)n3)c3c(N)ncnc3n2C)cc1] | ¹H NMR (400 MHz, DMSO-d₆) δ 9.90 (s, 1H), 8.18 (s, 1H), 7.78-7.63 (m, 3H), 7.39-7.25 (m, 2H), 7.13 (t, J = 7.0 Hz, 2H), 7.06 (d, J = 7.6 Hz, 1H), 6.72 (dd, J = 7.6, 1.5 Hz, 1H), 6.67 (d, J = 1.4 Hz, 1H), 5.80 (s, 1H), 5.54 (d, J = 1.9 Hz, 1H), 5.00-4.69 (m, 3H), 3.58 (s, 3H), 2.45 (s, 3H), 1.95 (d, J = 1.4 Hz, 3H). | 517.25 |
| (S)-N-(4-(4-amino-7-methyl-5-(3-(6-methylpyridin-2-yl)-2,3-dihydrobenzofuran-6-yl)-7H-pyrrolo[2,3-d]pyrimidin-6-yl)phenyl)methacrylamide | 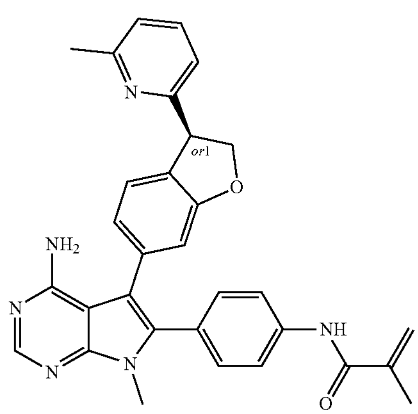 [SMILES: C=C(C)C(=O)Nc1ccc(-c2c(-c3ccc4c(c3)OC[C@@H]4c3cccc(C)n3)c3c(N)ncnc3n2C)cc1] | ¹H NMR (400 MHz, DMSO-d₆) δ 9.90 (s, 1H), 8.18 (s, 1H), 7.79-7.61 (m, 3H), 7.33-7 27 (m, 2H), 7.13 (t, J = 7.0 Hz, 2H), 7.06 (d, J = 7.6 Hz, 1H), 6.72 (dd, J = 7.6, 1.5 Hz, 1H), 6.67 (d, J = 1.5 Hz, 1H), 5.80 (s, 1H), 5.54 (t, J = 1.6 Hz, 1H), 4.98-4.74 (m, 3H), 3.58 (s, 3H), 2.45 (s, 3H), 1.96 (t, J = 1.2 Hz, 3H). | 517.25 |

TABLE 11-continued

Additional Exemplary Compounds

| Compound | Structure | Proton NMR | MS [M + 1] |
|---|---|---|---|
| (S)-N-(4-(4-amino-7-methyl-5-(1-(6-methylpyridin-2-yl)-1,3-dihydroisobenzofuran-5-yl)-7H-pyrrolo[2,3-d]pyrimidin-6-yl)phenyl)methacrylamide | 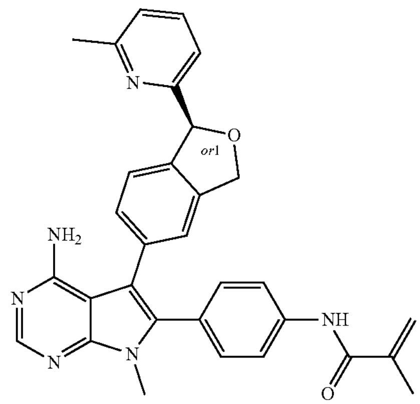 [SMILES: C=C(C)C(=O)Nc1ccc(-c2c(-c3ccc4c(c3)CO[C@@H]4c3cccc(C)n3)c3c(N)ncnc3n2C)cc1] | $^1$H NMR (400 MHz, DMSO-d$_6$) δ 9.88 (s, 1H), 8.20 (s, 1H), 7.74-7.62 (m, 3H), 7.33-7.19 (m, 5H), 7.19-7.09 (m, 2H), 6.68-5.38 (m, 5H), 5.29 (dd, J = 12.7, 2.8 Hz, 1H), 5.14 (d, J = 12.6 Hz, 1H), 3.59 (s, 3H), 2.50 (s, 3H), 1.94 (d, J = 1.4 Hz, 3H). | 517.25 |
| (R)-N-(4-(4-amino-7-methyl-5-(1-(6-methylpyridin-2-yl)-1,3-dihydroisobenzofuran-5-yl)-7H-pyrrolo[2,3-d]pyrimidin-6-yl)phenyl)methacrylamide | 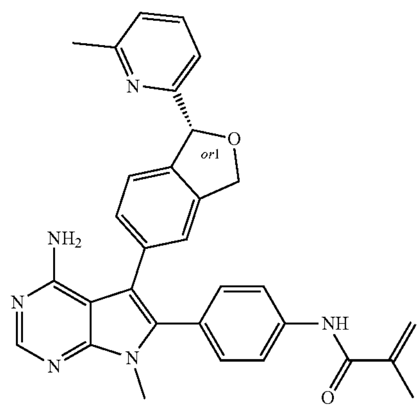 [SMILES: C=C(C)C(=O)Nc1ccc(-c2c(-c3ccc4c(c3)CO[C@H]4c3cccc(C)n3)c3c(N)ncnc3n2C)cc1] | $^1$H NMR (400 MHz, DMSO-d$_6$) δ 9.88 (s, 1H), 8.20 (s, 1H), 7.81-7.61 (m, 3H), 7.35-7.10 (m, 7H), 6.75-5.41 (m, 5H), 5.29 (dd, J = 12.8, 2.8 Hz, 1H), 5.14 (d, J = 12.6 Hz, 1H), 3.59 (s, 3H), 2.50 (s, 3H), 1.94 (s, 3H). | 517.30 |
| (S)-N-(4-(4-amino-7-methyl-5-(2-methyl-1-oxo-2-azaspiro[4.5]dec-7-en-8-yl)-7H-pyrrolo[2,3-d]pyrimidin-6-yl)phenyl)methacrylamide | 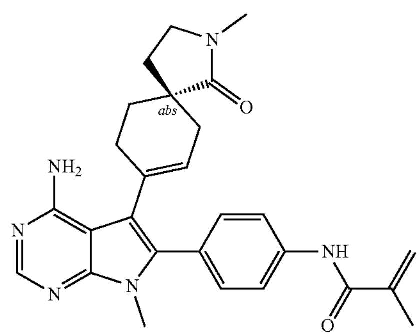 [SMILES: C=C(C)C(=O)Nc1ccc(-c2c(C3=CC[C@@]4(CC3)CCN(C)C4=O)c3c(N)ncnc3n2C)cc1] | $^1$H NMR (400 MHz, DMSO-d$_6$) δ 9.95 (s, 1H), 8.10 (s, 1H), 7.83-7.77 (m, 2H), 7.47-7.41 (m, 2H), 6.61 (s, 2H), 5.83 (s, 1H), 5.72 (d, J = 3.8 Hz, 1H), 5.55 (s, 1H), 3.58 (s, 3H), 3.32-3.21 (m, 2H), 2.73 (s, 3H), 2.27 (d, J = 17.4 Hz, 1H), 2.15-2.01 (m, 2H), 1.97 (s, 3H), 1.90 (s, 1H), 1.87-1.72 (m, 3H), 1.45-1.31 (m, 1H). | 471.25 |
| (R)-N-(4-(5-(4-(5-azaspiro[2.4]heptane-5-carbonyl)cyclohexan-1-yl)-4-amino-7-methyl-7H-pyrrolo[2,3-d]pyrimidin-6-yl)phenyl)methacrylamide | 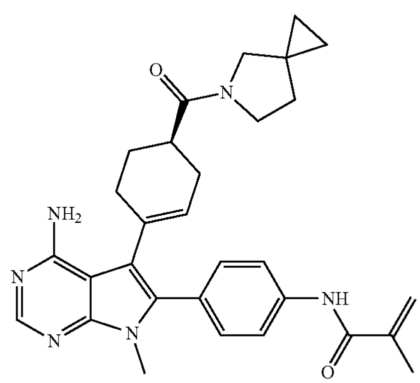 [SMILES: C=C(C)C(=O)Nc1ccc(-c2c(C3=CC[C@H](C(=O)N4CCC5(CC5)C4)CC3)c3c(N)ncnc3n2C)cc1] | $^1$H NMR (400 MHz, DMSO-d$_6$) δ 9.94 (s, 1H), 8.10 (s, 1H), 7.81 (dd, J = 8.7, 2.5 Hz, 2H), 7.43 (dd, J = 8.4, 3.6 Hz, 2H), 6.51 (s, 2H), 5.83 (s, 1H), 5.77 (s, 1H), 5.55 (s, 1H), 3.67 (t, J = 7.3 Hz, 1H), 3.58 (d, J = 1.8 Hz, 3H), 3.32-3.21 (m, 1H), 2.88 (t, J = 6.0 Hz, 1H), 2.28 (s, 2H), 1.98 (s, 3H), 1.90 (s, 2H), 1.82 (d, J = 4.4 Hz, 1H), 1.75-1.68 (m, 2H), 1.63 (dd, J = 15.1, 6.7 Hz, 2H), 0.63-0.53 (m, 4H). | 511.30 |

TABLE 11-continued

Additional Exemplary Compounds

| Compound | Structure | Proton NMR | MS [M + 1] |
|---|---|---|---|
| (S)-N-(4-(5-(4-(5-azaspiro[2.4]heptane-5-carbonyl)cyclohexan-1-yl)-4-amino-7-methyl-7H-pyrrolo[2,3-d]pyrimidin-6-yl)phenyl)methacrylamide | 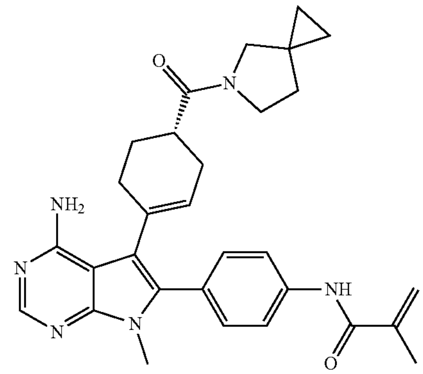 [SMILES: C=C(C)C(=O)Nc1ccc(-c2c(C3=CC[C@@H](C(=O)N4CCC5(CC5)C4)CC3)c3c(N)ncnc3n2C)cc1] | $^1$H NMR (400 MHz, DMSO-$d_6$) δ 9.94 (s, 1H), 8.10 (s, 1H), 7.81 (dd, J = 8.7, 2.6 Hz, 2H), 7.43 (dd, J = 8.6, 3.5 Hz, 2H), 6.51 (s, 2H), 5.83 (s, 1H), 5.77 (s, 1H), 5.55 (s, 1H), 3.71-3.60 (m, 1H), 3.58 (d, J = 1.9 Hz, 3H), 3.42 (dd, J = 17.0, 11.4 Hz, 1H), 3.32-3.13 (m, 1H), 2.73 (q, J = 6.0 Hz, 1H), 2.28 (s, 2H), 1.98 (s, 3H), 1.90 (s, 2H), 1.82 (dt, J = 10.1, 4.6 Hz, 1H), 1.72 (td, J = 1.0, 4.0 Hz, 1H), 1.63 (dd, J = 14.8, 6.3 Hz, 2H), 0.61 (d, J = 6.4 Hz, 1H), 0.56 (d, J = 5.7 Hz, 3H). | 511.35 |
| (S)-N-(4-(4-amino-7-methyl-5-(4-(pyrrolidine-1-carbonyl)cyclohex-1-en-1-yl)-7H-pyrrolo[2,3-d]pyrimidin-6-yl)phenyl)-2-chloroacetamide | 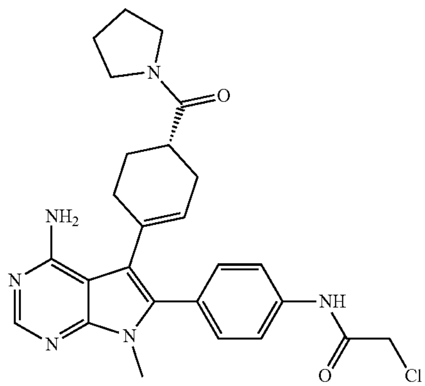 [SMILES: Cn1c(-c2ccc(NC(=O)CCl)cc2)c(C2=CC[C@@H](C(=O)N3CCCC3)CC2)c2c(N)ncnc21] | $^1$H NMR (400 MHz, DMSO-$d_6$) δ 10.48 (s, 1H), 8.10 (s, 1H), 7.88-7.75 (m, 2H), 7.57-7.40 (m, 2H), 6.55 (s, 1H), 5.77 (d, J = 3.1 Hz, 1H), 4.29 (s, 2H), 3.58 (s, 3H), 3.56-3.48 (m, 1H), 3.48-3.40 (m, 1H), 3.32-3.23 (m, 3H), 2.82 (q, J = 6.0 Hz, 1H), 2.38-2.10 (m, 2H), 1.87 (h, J = 6.4 Hz, 4H), 1.76 (p, J = 6.3 Hz, 2H), 1.63 (d, J = 5.9 Hz, 2H). | 493.20 |
| (R)-N-(4-(4-amino-7-methyl-5-(4-(pyrrolidine-1-carbonyl)cyclohex-1-en-1-yl)-7H-pyrrolo[2,3-d]pyrimidin-6-yl)phenyl)-2-chloroacetamide | 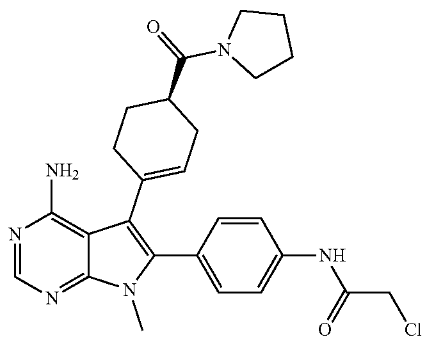 [SMILES: Cn1c(-c2ccc(NC(=O)CCl)cc2)c(C2=CC[C@H](C(=O)N3CCCC3)CC2)c2c(N)ncnc21] | $^1$H NMR (400 MHz, DMSO-$d_6$) δ 10.48 (s, 1H), 8.10 (s, 1H), 7.85-7.69 (m, 2H), 7.53-7.44 (m, 2H), 6.55 (s, 1H), 5.76 (d, J = 4.0 Hz, 1H), 4.29 (s, 2H), 3.58 (s, 3H), 3.51 (dt, J = 10.1, 6.7 Hz, 1H), 3.47-3.41 (m, 1H), 3.32 (d, J = 9.3 Hz, 3H), 2.83 (p, J = 5.9 Hz, 1H), 2.37-2.14 (m, 2H), 1.87 (p, J = 6.8 Hz, 4H), 1.76 (p, J = 6.3 Hz, 2H), 1.63 (d, J = 6.1 Hz, 2H). | 493.20 |
| (S)-N-(4-(4-amino-7-methyl-5-(6-(pyrrolidine-1-carbonyl)-5,6-dihydro-2H-pyran-3-yl)-7H-pyrrolo[2,3-d]pyrimidin-6-yl)phenyl)methacrylamide | 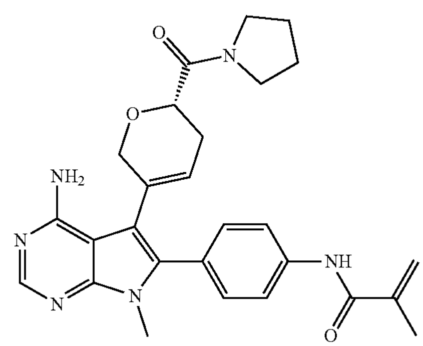 [SMILES: C=C(C)C(=O)Nc1ccc(-c2c(C3=CC[C@@H](C(=O)N4CCCC4)OC3)c3c(N)ncnc3n2C)cc1] | $^1$H NMR (400 MHz, DMSO-$d_6$) δ 9.99 (s, 1H), 8.12 (s, 1H), 7.81 (d, J = 8.2 Hz, 2H), 7.42 (d, J = 8.4 Hz, 2H), 6.63 (s, 2H), 5.94 (d, J = 4.2 Hz, 1H), 5.82 (s, 1H), 5.56 (s, 1H), 4.55 (t, J = 5.0 Hz, 1H), 3.77 (d, J = 2.9 Hz, 2H), 3.55 (s, 3H), 3.50 (s, 3H), 3.29 (td, J = 6.8, 3.1 Hz, 2H), 2.45 (d, J = 17.9 Hz, 1H), 2.31 (dt, J = 17.1, 4.2 Hz, 1H), 1.97 (s, 3H), 1.79 (dp, J = 24.9, 6.9 Hz, 4H), 1.19 (s, 1H). | 487.30 |

TABLE 11-continued

_Additional Exemplary Compounds_

| Compound | Structure | Proton NMR | MS [M + 1] |
|---|---|---|---|
| (R)-N-(4-(4-amino-7-methyl-5-(6-(pyrrolidine-1-carbonyl)-5,6-dihydro-2H-pyran-3-yl)-7H-pyrrolo[2,3-d]pyrimidin-6-yl)phenyl)methacrylamide | 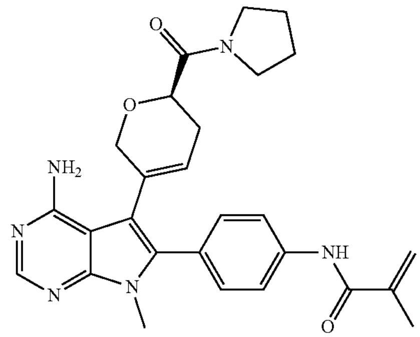 [SMILES: C=C(C)C(=O)Nc1ccc(-c2c(C3=CC[C@H](C(=O)N4CCCC4)OC3)c3c(N)ncnc3n2C)cc1] | $^1$H NMR (400 MHz, DMSO-d$_6$) δ 9.98 (s, 1H), 8.11 (s, 1H), 7.85-7.78 (m, 2H), 7.46-7.39 (m, 2H), 6.55 (s, 2H), 5.94 (s, 1H), 5.85-5.80 (m, 1H), 5.56 (d, J = 1.8 Hz, 1H), 4.54 (t, J = 5.0 Hz, 1H), 3.77 (s, 2H), 3.55 (s, 3H), 3.52-3.41 (m, 2H), 3.39-3.28 (m, 3H), 2.43 (s, 1H), 2.29 (s, 1H), 1.97 (s, 3H), 1.77 (ddt, J = 24.2, 11.8, 5.5 Hz, 4H), 1.19 (s, 1H). | 487.20 |
| N-(4-(4-amino-7-methyl-5-(1-(pyrrolidine-1-carbonyl)-1,2,3,6-tetrahydropyridin-4-yl)-7H-pyrrolo[2,3-d]pyrimidin-6-yl)phenyl)methacrylamide | 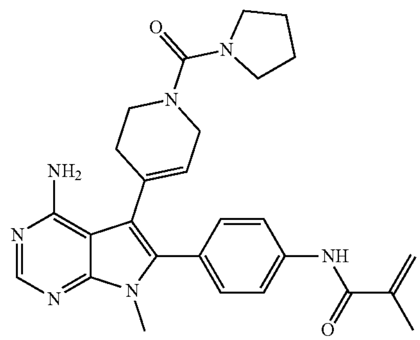 [SMILES: C=C(C)C(=O)Nc1ccc(-c2c(C3=CCN(C(=O)N4CCCC4)CC3)c3c(N)ncnc3n2C)cc1] | $^1$H NMR (400 MHz, DMSO-d$_6$) δ 9.97 (s, 1H), 8.13 (s, 1H), 7.84-7.78 (m, 2H), 7.46-7.39 (m, 2H), 6.3 (s, 1H), 5.81 (d, J = 11.2 Hz, 2H), 5.56 (s, 1H), 3.83 (d, J = 3.3 Hz, 2H), 3.57 (s, 3H), 3.23 (s, 1H), 1.97 (d, J = 1.2 Hz, 5H), 1.77-1.70 (m, 4H). | 486.25 |
| N-(4-(4-amino-5-(1-(cyclopentanecarbonyl)-1,2,3,6-tetrahydropyridin-4-yl)-7-methyl-7H-pyrrolo[2,3-d]pyrimidin-6-yl)phenyl)methacrylamide | 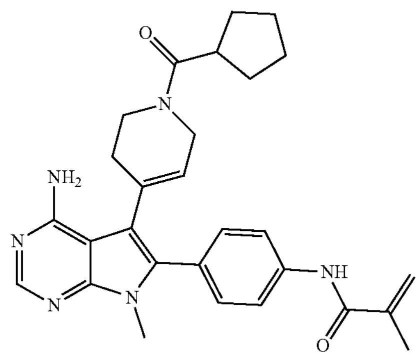 [SMILES: C=C(C)C(=O)Nc1ccc(-c2c(C3=CCN(C(=O)C4CCCC4)CC3)c3c(N)ncnc3n2C)cc1] | $^1$H NMR (400 MHz, DMSO-d$_6$) δ 9.97 (s, 1H), 8.13 (s, 1H), 7.84-7.78 (m, 2H), 7.46-7.39 (m, 2H), 6.3 (s, 1H), 5.81 (d, J = 11.2 Hz, 2H), 5.56 (s, 1H), 3.83 (d, J = 3.3 Hz, 2H), 3.57 (s, 3H), 3.23 (s, 1H), 2.45 (s, 1H), 1.97 (d, J = 1.2 Hz, 5H), 1.77-1.70 (m, 4H). | 485.25 |
| N-(4-(4-amino-5-((R)-4-((S)-2-ethynylpyrrolidine-1-carbonyl)cyclohex-1-enyl)-7-methyl-7H-pyrrolo[2,3-d]pyrimidin-6-yl)phenyl)methacrylamide | 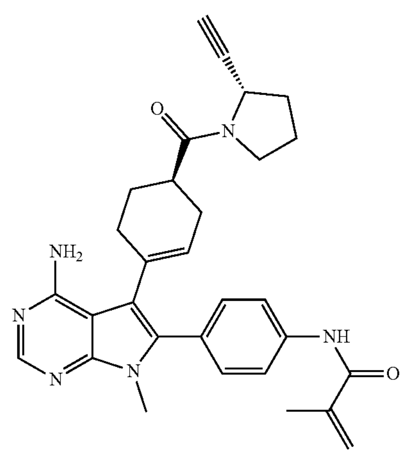 [SMILES: C#C[C@@H]1CCCN1C(=O)[C@H]1CC=C(c2c(-c3ccc(NC(=O)C(=C)C)cc3)n(C)c3ncnc(N)c23)CC1] | 1H NMR (400 MHz, Methanol-d4) δ 8.15 (d, J = 3.5 Hz, 1H), 7.91-7.65 (m, 2H), 7.54-7.38 (m, 2H), 5.94 (s, 1H), 5.89-5.73 (m, 1H), 5.64-5.44 (m, 1H), 4.90-4.65 (m, 1H), 3.70-3.60 (m, 3H), 3.60-3.50 (m, 1H), 3.50-3.40 (m, 1H), 3.10-2.88 (m, 1H), 2.88-2.60 (m, 1H), 2.55-2.30 (m, 2H), 2.30-2.10 (m, 2H), 2.10-1.98 (m, 7H), 1.90-1.80 (m, 1H), 1.80-1.70 (m, 1H), 1.40-1.30 (m, 1H). | 509.25 |

TABLE 11-continued

Additional Exemplary Compounds

| Compound | Structure | Proton NMR | MS [M + 1] |
|---|---|---|---|
| N-(4-{4-amino-5-[(4R)-4-[(2R)-2-ethynylpyrrolidine-1-carbonyl]cyclohex-1-en-1-yl]-7-methyl-7H-pyrrolo[2,3-d]pyrimidin-6-yl}phenyl)-2-methylprop-2-enamide | 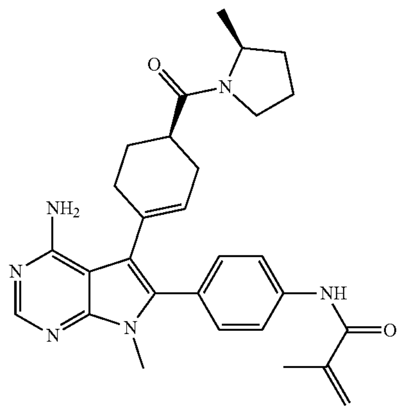 [SMILES: C=C(C)C(=O)Nc1ccc(-c2c(C3=CC[C@H](C(=O)N4CCC[C@@H]4C)CC3)c3c(N)ncnc3n2C)cc1] | 1H NMR (400 MHz, Methanol-d4) δ 8.14 (d, J = 3.4 Hz, 1H), 7.79 (dq, J = 9.1, 2.5 Hz, 2H), 7.47 (dd, J = 8.7, 2.1 Hz, 2H), 5.93 (d, J = 9.6 Hz, 1H), 5.85 (dt, J = 2.0, 1.0 Hz, 1H), 5.59-5.54 (m, 1H), 4.77-4.71 (m, 1H), 3.70-3.65 (m, 3H), 3.65-3.55 (m, 1H), 3.55-3.40 (m, 1H), 3.20-2.55 (m, 2H), 2.53-2.30 (m, 2H), 2.20-2.10 (m, 2H) 2.10-1.93 (m, 7H), 1.90-1.60 (m, 2H), 1.40-1.30 (m, 1H). | 509.25 |
| N-(4-{4-amino-7-methyl-5-[(4S)-4-{2-oxa-5-azaspiro[3.4]octane-5-carbonyl}cyclohex-1-en-1-yl]-7H-pyrrolo[2,3-d]pyrimidin-6-yl}phenyl)-2-methylprop-2-enamide | 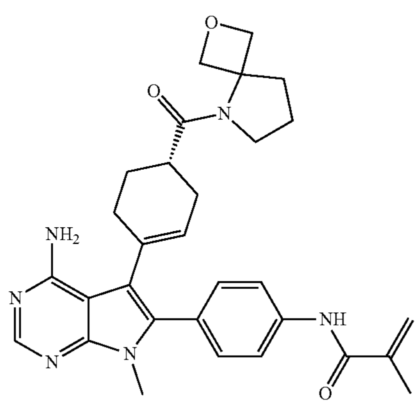 [SMILES: C=C(C)C(=O)Nc1ccc(-c2c(C3=CC[C@@H](C(=O)N4CCCC45COC5)CC3)c3c(N)ncnc3n2C)cc1] | ¹H NMR (400 MHz, DMSO-d₆) δ 9.96 (s, 1H), 8.11 (s, 1H), 7.84-7.78 (m, 2H), 7.47-7.38 (m, 2H), 6.48 (s, 2H), 5.83-5.79 (m, 2H), 5.56 (d, J = 2.0 Hz, 1H), 5.33-5.28 (m, 2H), 4.18 (dd, J = 4.9, 3.0 Hz, 2H), 3.58 (s, 3H), 3.55 (dt, J = 9.6, 6.1 Hz, 1H), 3.46 (dt, J = 9.6, 6.8 Hz, 1H), 2.85 (s, 1H), 2.40-2.30 (m, 1H), 2.30-2.10 (m, 3H), 2.0-1.80 (m, 5H), 1.80-1.50 (m, 4H). | 527.30 |
| N-{4-[4-amino-7-methyl-5-(4-{7-oxa-1-azaspiro[4.4]nonane-1-carbonyl}cyclohex-1-en-1-yl)-7H-pyrrolo[2,3-d]pyrimidin-6-yl]phenyl}-2-methylprop-2-enamide | 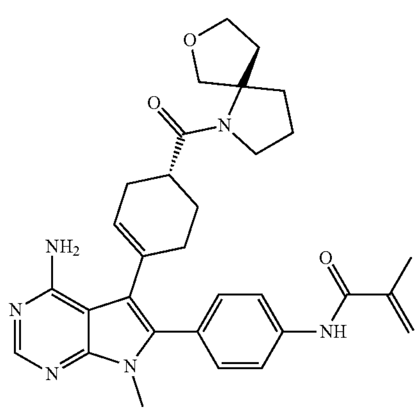 | ¹H NMR (400 MHz, Methanol-d₄) δ 8.13 (s, 1H), 7.85-7.72 (m, 2H), 7.52-7.42 (m, 2H), 5.93 (s, 1H), 5.85 (s, 1H), 5.57 (s, 1H), 4.15 (q, J = 7.7 Hz, 1H), 3.99 (d, J = 8.1 Hz, 1H), 3.92 (td, J = 7.8, 5.1 Hz, 1H), 3.66 (s, 5H), 3.53-3.43 (m, 1H), 2.87 (t, J = 6.0 Hz, 1H), 2.73 (ddd, J = 12.6, 7.9, 5.1 Hz, 1H), 2.38 (q, J = 19.0 Hz, 2H), 2.13-1.90 (m, 8H), 1.89-1.66 (m, 4H), 1.31 (s, 1H). | 541.25 |

TABLE 11-continued

Additional Exemplary Compounds

| Compound | Structure | Proton NMR | MS [M + 1] |
|---|---|---|---|
| N-{4-[4-amino-7-methyl-5-(4-{7-oxa-1-azaspiro[4.4]nonane-1-carbonyl}cyclohex-1-en-1-yl)-7H-pyrrolo[2,3-d]pyrimidin-6-yl]phenyl}-2-methylprop-2-enamide | 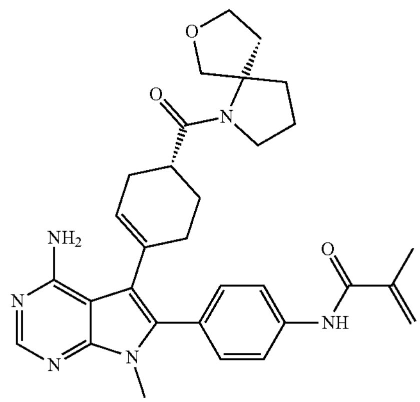 | $^1$H NMR (400 MHz, Methanol-d$_4$) δ 8.13 (s, 1H), 7.82-7.73 (m, 2H), 7.53-7.41 (m, 2H), 5.93 (s, 1H), 5.85 (s, 1H), 5.57 (s, 1H), 4.15 (q, J = 7.7 Hz, 1H), 3.99 (d, J = 8.1 Hz, 1H), 3.92 (td, J = 7.8, 5.1 Hz, 1H), 3.66 (s, 5H), 3.53-3.41 (m, 1H), 2.96-2.81 (m, 1H), 2.73 (ddd, J = 12.6, 7.9, 5.1 Hz, 1H), 2.38 (q, J = 19.0 Hz, 2H), 2.07 (d, J = 1.2 Hz, 3H), 2.02 (q, J = 8.5, 7.3 Hz, 3H), 1.98-1.81 (m, 2H), 1.81-1.71 (m, 4H), 1.31 (s, 1H). | 541.25 |
| N-(4-(4-amino-5-(6,6-difluoro-4-(pyrrolidine-1-carbonyl)cyclohex-1-en-1-yl)-7-methyl-7H-pyrrolo[2,3-d]pyrimidin-6-yl)phenyl)methacrylamide | 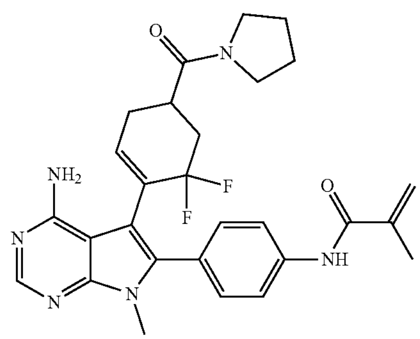 [SMILES: C=C(C)C(=O)Nc1ccc(-c2c(C3=CCC(C(=O)N4CCCC4)CC3(F)F)c3c(N)ncnc3n2C)cc1] | $^1$H NMR (400 MHz, Methanol-d$_4$) δ 8.16 (s, 1H), 7.76 (d, J = 8.4 Hz, 2H), 7.40 (d, J = 8.4 Hz, 2H), 6.32 (s, 1H), 5.87-5.82 (m, 1H), 5.59-5.54 (m, 1H), 5.20 (s, 1H), 3.63 (s, 3H), 3.59 (s, 2H), 3.44 (t, J = 6.9 Hz, 2H), 3.40 (s, 1H), 2.47 (s, 2H), 2.31 (s, 1H), 2.09-1.97 (m, 5H), 2.00-1.87 (m, 2H). | 521.30 |
| N-[4-(4-amino-5-{4-[(2R)-2-ethynylpyrrolidine-1-carbonyl]cyclohex-1-en-1-yl}-7-methyl-7H-pyrrolo[2,3-d]pyrimidin-6-yl)phenyl]-2-methylprop-2-enamide | 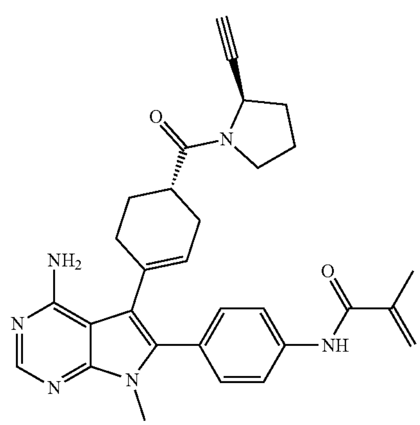 [SMILES: C#C[C@H]1CCCN1C(=O)[C@@H]1CC=C(c2c(-c3ccc(NC(=O)C(=C)C)cc3)n(C)c3ncnc(N)c23)CC1] | $^1$H NMR (400 MHz, Methanol-d$_4$) δ 8.14 (d, J = 3.4 Hz, 1H), 7.82-7.74 (m, 2H), 7.47 (dt, J = 8.7, 2.1 Hz, 2H), 5.93 (d, J = 9.7 Hz, 1H), 5.85 (dt, J = 2.1, 1.0 Hz, 1H), 5.57 (d, J = 1.8 Hz, 1H), 4.74 (dd, J = 24.7, 7.0 Hz, 1H), 3.67 (d, J = 1.8 Hz, 3H), 3.59 (t, J = 8.8 Hz, 1H), 3.45-3.35 (m, 1H), 3.20-2.55 (m, 2H), 2.50-2.30 (m, 2H), 2.25-1.98 (m, 9H), 1.90-1.70 (m, 2H). | 509.25 |

TABLE 11-continued

Additional Exemplary Compounds

| Compound | Structure | Proton NMR | MS [M + 1] |
|---|---|---|---|
| N-(4-(4-amino-5-((S)-4-((S)-2-ethynylpyrrolidine-1-carbonyl)cyclohex-1-enyl)-7-methyl-7H-pyrrolo[2,3-d]pyrimidin-6-yl)phenyl) methacrylamide | 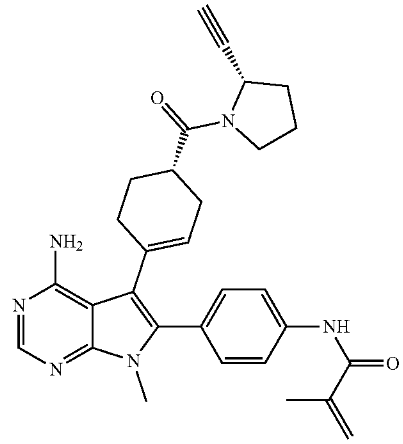 [SMILES: C#C[C@@H]1CCCN1C(=O)[C@@H]1CC=C(c2c(-c3ccc(NC(=O)C(=C)C)cc3)n(C)c3ncnc(N)c23)CC1] | ¹H NMR (400 MHz, Methanol-d₄) δ 8.14 (d, J = 3.4 Hz, 1H), 7.82-7.74 (m, 2H), 7.47 (dt, J = 8.7, 2.1 Hz, 2H), 5.93 (d, J = 9.7 Hz, 1H), 5.85 (dt, J = 2.1, 1.0 Hz, 1H), 5.57 (d, J = 1.8 Hz, 1H), 4.74 (dd, J = 24.7, 7.0 Hz, 1H), 3.67 (d, J = 1.8 Hz, 3H), 3.59 (t, J = 8.8 Hz, 1H), 3.45-3.35 (m, 1H), 3.20-2.55 (m, 2H), 2.50-2.30 (m, 2H), 2.25-1.98 (m, 9H), 1.90-1.70 (m, 2H). | 509.25 |
| N-{4-[4-amino-7-methyl-5-(4-{2-oxa-5-azaspiro[3.4]octane-5-carbonyl}cyclohex-1-en-1-yl)-7H-pyrrolo[2,3-d]pyrimidin-6-yl]phenyl}-2-methylprop-2-enamide | 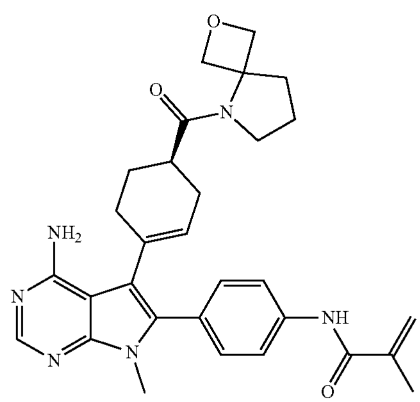 [SMILES: C=C(C)C(=O)Nc1ccc(-c2c(C3=CC[C@H](C(=O)N4CCCC45COC5)CC3)c3c(N)ncnc3n2C)cc1] | ¹H NMR (400 MHz, DMSO-d₆) δ 9.96 (s, 1H), 8.12 (s, 1H), 7.84-7.77 (m, 2H), 7.47-7.40 (m, 2H), 6.52 (s, 1H), 5.83 (s, 1H), 5.78 (s, 1H), 5.56 (t, J = 1.5 Hz, 1H), 5.33 (d, J = 4.9 Hz, 1H), 5.28 (d, J = 4.9 Hz, 1H), 4.18 (dd, J = 4.9, 3.1 Hz, 2H), 3.59 (s, 3H), 3.57-3.50 (m, 1H), 3.46 (dt, J = 9.7, 6.8 Hz, 1H), 2.89-2.81 (m, 1H), 2.33 (s, 1H), 2.30-2.14 (m, 3H), 1.97 (t, J = 1.2 Hz, 3H), 1.92-1.86 (m, 2H), 1.72 (q, J = 6.7 Hz, 2H), 1.64 (s, 2H). | 527.25 |
| N-{4-[4-amino-7-methyl-5-(4-{7-oxa-1-azaspiro[4.4]nonane-1-carbonyl}cyclohex-1-en-1-yl)-7H-pyrrolo[2,3-d]pyrimidin-6-yl]phenyl}-2-methylprop-2-enamide | 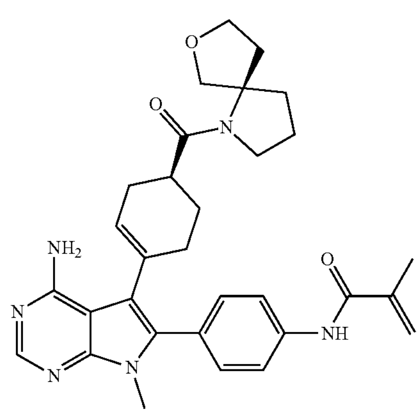 [SMILES: C=C(C)C(=O)Nc1ccc(-c2c(C3=CC[C@@H](C(=O)N4CCC[C@]45CCOC5)CC3)c3c(N)ncnc3n2C)cc1] | ¹H NMR (400 MHz, Chloroform-d) δ 8.31 (s, 1H), 7.72-7.65 (m, 2H), 7.62 (s, 1H), 7.47-7.39 (m, 2H), 6.35-5.95 (m, 2H), 5.90-5.75 (s, 1H), 5.65-5.45 (m, 1H), 4.13 (q, J = 8.0 Hz, 1H), 4.02-3.92 (m, 2H), 3.70 (s, 3H), 3.64 (t, J = 8.2 Hz, 1H), 3.55-3.45 (m, 1H), 3.43 (d, J = 8.0 Hz, 1H), 2.81 (s, 1H), 2.64 (ddd, J = 11.5, 7.5, 3.3 Hz, 1H), 2.51 (d, J = 18.0 Hz, 1H), 2.35-2.25 (m, 1H), 2.15-2.10 (m, 3H), 2.10-1.82 (m, 6H), 1.80-1.70 (m, 3H). | 541.30 |

TABLE 11-continued

_Additional Exemplary Compounds_

| Compound | Structure | Proton NMR | MS [M + 1] |
|---|---|---|---|
| N-{4-[4-amino-7-methyl-5-(4-{7-oxa-1-azaspiro[4.4]nonane-1-carbonyl}cyclohex-1-en-1-yl)-7H-pyrrolo[2,3-d]pyrimidin-6-yl]phenyl}-2-methylprop-2-enamide | 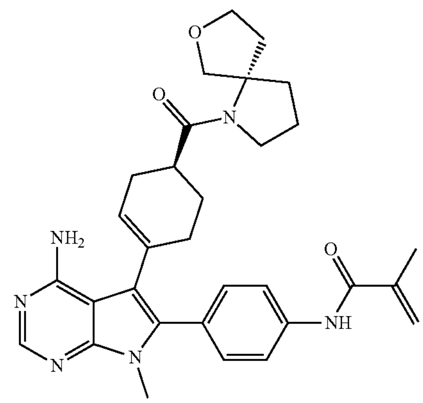 [SMILES: C=C(C)C(=O)Nc1ccc(-c2c(C3=CC[C@@H](C(=O)N4CCC[C@@]45CCOC5)CC3)c3c(N)ncnc3n2C)cc1] | $^1$H NMR (400 MHz, Chloroform-d) δ 8.32 (s, 1H), 7.76-7.65 (m, 3H), 7.46-7.39 (m, 2H), 5.96-5.87 (m, 3H), 5.54 (d, J = 1.7 Hz, 1H), 4.18 (q, J = 8.0 Hz, 1H), 3.98 (td, J = 8.0, 3.7 Hz, 1H), 3.88 (d, J = 8.0 Hz, 1H), 3.70 (s, 3H), 3.55 (dtd, J = 15.7, 10.0, 9.6, 6.8 Hz, 2H), 3.42 (d, J = 8.0 Hz, 1H), 2.77 (tt, J = 7.9, 3.8 Hz, 2H), 2.59-2.40 (m, 1H), 2.40-2.25 (m, 1H), 2.10-2.15 (m, 3H), 2.10-1.82 (m, 6H), 1.80-1.72 (m, 3H). | 541.30 |
| (S)-N-(4-(4-amino-7-methyl-5-(4-(pyrrolidine-1-carbonyl)cyclohex-1-en-1-yl)-7H-pyrrolo[2,3-d]pyrimidin-6-yl)phenyl)acrylamide | 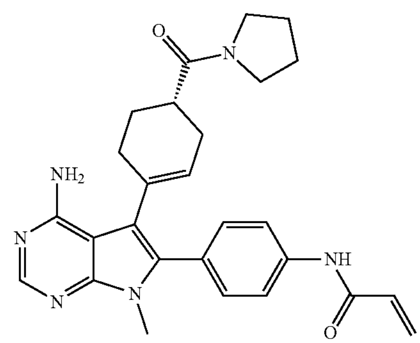 [SMILES: C=CC(=O)Nc1ccc(-c2c(C3=CC[C@@H](C(=O)N4CCCC4)CC3)c3c(N)ncnc3n2C)cc1] | $^1$H NMR (400 MHz, DMSO-d$_6$) δ 10.31 (s, 1H), 8.10 (s, 1H), 7.78 (d, J = 8.7 Hz, 2H), 7.49-7.42 (m, 2H), 6.47 (dd, J = 17.0, 10.1 Hz, 2H), 6.29 (dd, J = 17.0, 2.0 Hz, 1H), 5.79 (dd, J = 10.1, 2.1 Hz, 1H), 5.76 (s, 1H), 3.60 (s, 3H), 3.54-3.47 (m, 1H), 3.47-3.37 (m, 1H), 3.30-3.20 (m, 2H), 2.83 (t, J = 5.9 Hz, 1H), 2.26 (s, 2H), 1.91-1.81 (m, 4H), 1.76 (q, J = 6.6 Hz, 2H), 1.63 (d, J = 6.2 Hz, 2H). | 471.20 |
| (R)-N-(4-(4-amino-7-methyl-5-(4-(pyrrolidine-1-carbonyl)cyclohex-1-en-1-yl)-7H-pyrrolo[2,3-d]pyrimidin-6-yl)phenyl)acrylamide | 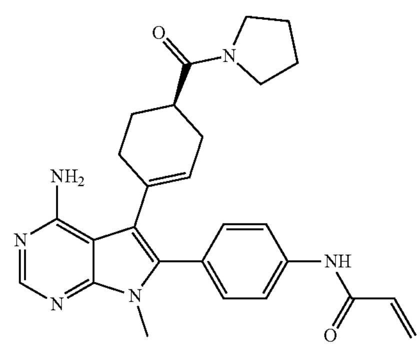 [SMILES: C=CC(=O)Nc1ccc(-c2c(C3=CC[C@H](C(=O)N4CCCC4)CC3)c3c(N)ncnc3n2C)cc1] | $^1$H NMR (400 MHz, DMSO-d$_6$) δ 10.31 (s, 1H), 8.09 (s, 1H), 7.82-7.75 (m, 2H), 7.48-7.42 (m, 2H), 6.47 (dd, J = 17.0, 10.1 Hz, 2H), 6.29 (dd, J = 17.0, 2.0 Hz, 1H), 5.79 (dd, J = 10.1, 2.0 Hz, 1H), 5.76 (s, 1H), 3.58 (s, 3H), 3.56-3.47 (m, 1H), 3.47-3.37 (m, 1H), 3.31-3.20 (m, 2H), 2.82 (t, J = 5.9 Hz, 1H), 2.26 (s, 2H), 1.90-1.81 (m, 4H), 1.76 (p, J = 6.6 Hz, 2H), 1.63 (d, J = 5.7 Hz, 2H). | 471.20 |
| (S)-N-(4-(4-amino-7-methyl-5-(4-(pyrrolidin-1-ylsulfonyl)cyclohex-1-en-1-yl)-7H-pyrrolo[2,3-d]pyrimidin-6-yl)phenyl)methacrylamide | 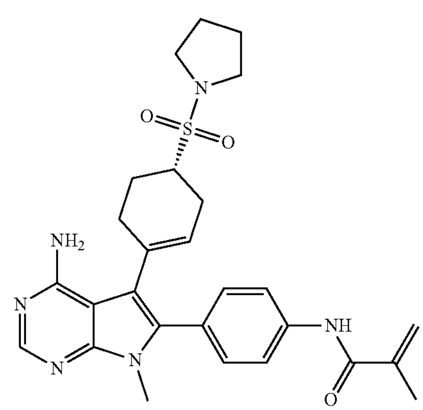 [SMILES: C=C(C)C(=O)Nc1ccc(-c2c(C3=CC[C@@H](S(=O)(=O)N4CCCC4)CC3)c3c(N)ncnc3n2C)cc1] | 1H NMR (400 MHz, DMSO-d6) δ 9.96 (s, 1H), 8.13 (s, 1H), 7.81 (d, J = 2.0 Hz, 2H), 7.49-7.37 (m, 2H), 6.42 (s, 1H), 5.84 (s, 1H), 5.71 (d, J = 4.8 Hz, 1H), 5.55 (t, J = 1.5 Hz, 1H), 3.62 (s, 1H), 3.58 (s, 3H), 3.42-3.22 (m, 4H), 2.47-2.31 (m, 2H), 2.10 (d, J = 12.2 Hz, 1H), 2.03-1.90 (m, 5H), 1.90-1.75 (m, 4H), 1.63 (s, 1H). | 521.25 |

TABLE 11-continued

Additional Exemplary Compounds

| Compound | Structure | Proton NMR | MS [M + 1] |
| --- | --- | --- | --- |
| (R)-N-(4-(4-amino-7-methyl-5-(4-(pyrrolidin-1-ylsulfonyl)cyclohex-1-en-1-yl)-7H-pyrrolo[2,3-d]pyrimidin-6-yl)phenyl)methacrylamide | 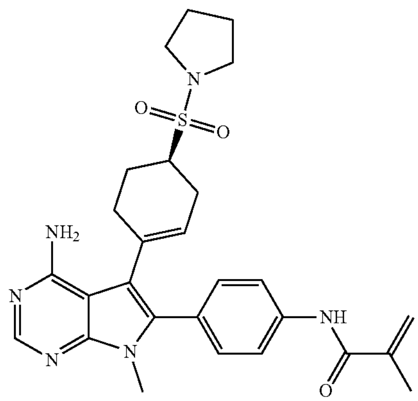 [SMILES: C=C(C)C(=O)Nc1ccc(-c2c(C3=CC[C@H](S(=O)(=O)N4CCCC4)CC3)c3c(N)ncnc3n2C)cc1] | 1H NMR (400 MHz, DMSO-d6) δ 9.96 (s, 1H), 8.13 (s, 1H), 7.81 (d, J = 2.0 Hz, 2H), 7.49-7.37 (m, 2H), 6.42 (s, 1H), 5.84 (s, 1H), 5.71 (d, J = 4.8 Hz, 1H), 5.55 (t, J = 1.5 Hz, 1H), 3.62 (s, 1H), 3.58 (s, 3H), 3.42-3.22 (m, 4H), 2.47-2.31 (m, 2H), 2.10 (d, J = 12.2 Hz, 1H), 2.03-1.90 (m, 5H), 1.90-1.75 (m, 4H), 1.63 (s, 1H). | 521.25 |
| N-(4-(4-amino-5-(4-(cyclopentylsulfonyl)cyclohex-1-en-1-yl)-7-methyl-7H-pyrrolo[2,3-d]pyrimidin-6-yl)phenyl)methacrylamide | 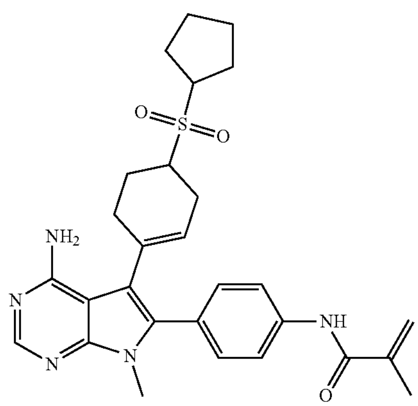 [SMILES: C=C(C)C(=O)Nc1ccc(-c2c(C3=CCC(S(=O)(=O)C4CCCC4)CC3)c3c(N)ncnc3n2C)cc1] | $^1$H NMR (400 MHz, Chloroform-d) δ 8.33 (s, 1H), 7.69 (t, J = 8.4 Hz, 3H), 7.38 (d, J = 8.2 Hz, 2H), 5.92 (s, 1H), 5.87 (s, 1H), 5.55 (s, 3H), 3.68 (s, 3H), 3.50 (m, J = 8.2 Hz, 1H), 3.20 (d, J = 7.6 Hz, 1H), 2.73 (s, 1H), 2.66 (s, 1H), 2.31 (d, J = 15.8 Hz, 1H), 2.12 (s, 3H), 2.01 (d, J = 19.2 Hz, 6H), 1.85 (s, 3H), 1.70 (d, J = 8.4 Hz, 2H). | 520.25 |
| (S)-4-(4-amino-6-(4-methacrylamidophenyl)-7-methyl-7H-pyrrolo[2,3-d]pyrimidin-5-yl)-N-cyclopentylcyclohex-3-ene-1-carboxamide | 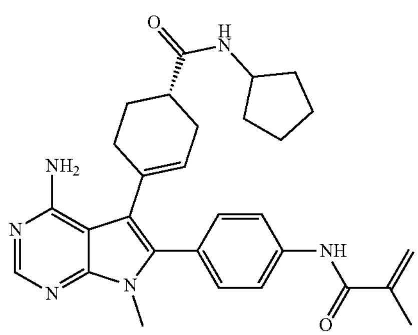 [SMILES: C=C(C)C(=O)Nc1ccc(-c2c(C3=CC[C@@H](C(=O)NC4CCCC4)CC3)c3c(N)ncnc3n2C)cc1] | $^1$H NMR (400 MHz, DMSO-d$_6$) δ 9.96 (s, 1H), 8.11 (s, 1H), 7.80 (t, J = 7.9 Hz, 3H), 7.43 (d, J = 8.6 Hz, 2H), 6.52 (s, 1H), 5.83 (s, 1H), 5.78 (s, 1H), 5.56 (s, 1H), 3.98 (q, J = 6.9 Hz, 1H), 3.57 (s, 3H), 2.45 (s, 1H), 2.28 (s, 1H), 2.21 (s, 1H), 1.98 (s, 3H), 1.88 (s, 2H), 1.76 (dt, J = 12.8, 6.6 Hz, 2H), 1.62 (dd, J = 12.4, 5.7 Hz, 2H), 1.47 (q, J = 6.8 Hz, 2H), 1.39-1.31 (m, 1H), 1.34-1.22 (m, 1H). | 499.25 |
| (R)-4-(4-amino-6-(4-methacrylamidophenyl)-7-methyl-7H-pyrrolo[2,3-d]pyrimidin-5-yl)-N-cyclopentylcyclohex-3-ene-1-carboxamide | 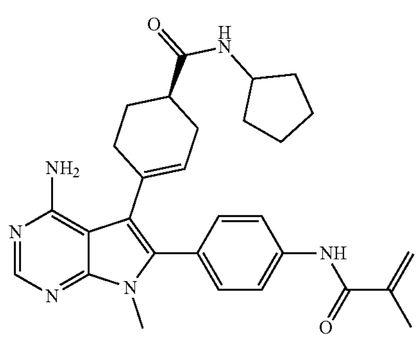 [SMILES: C=C(C)C(=O)Nc1ccc(-c2c(C3=CC[C@H](C(=O)NC4CCCC4)CC3)c3c(N)ncnc3n2C)cc1] | $^1$H NMR (400 MHz, DMSO-d$_6$) δ 9.96 (s, 1H), 8.11 (s, 1H), 7.80 (t, J = 7.9 Hz, 3H), 7.46-7.39 (m, 2H), 6.52 (s, 1H), 5.83 (s, 1H), 5.78 (s, 1H), 5.56 (s, 1H), 3.98 (q, J = 6.8 Hz, 1H), 3.57 (s, 3H), 2.44 (s, 1H), 2.28 (s, 1H), 2.21 (s, 1H), 1.98 (d, J = 1.2 Hz, 3H), 1.88 (s, 2H), 1.76 (dt, J = 12.5, 6.5 Hz, 2H), 1.61 (dt, J = 13.2, 6.0 Hz, 3H), 1.47 (q, J = 1.0 Hz, 2H), 1.35 (s, 2H), 1.31 (dd, J = 13.2, 6.9 Hz, 1H). | 499.25 |

TABLE 11-continued

Additional Exemplary Compounds

| Compound | Structure | Proton NMR | MS [M + 1] |
|---|---|---|---|
| 4-(4-amino-6-(4-methacrylamido phenyl)-7-methyl-7H-pyrrolo[2,3-d]pyrimidin-5-yl)-N-(3,3-difluorocyclobutyl)-2-methoxybenzamide | 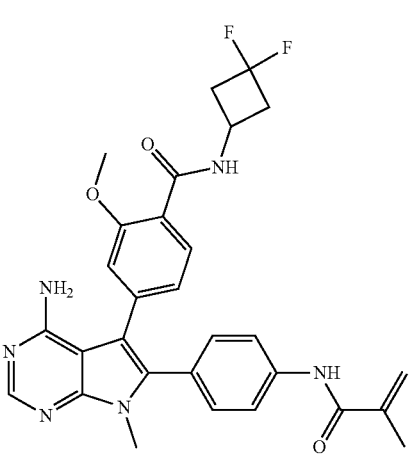 [SMILES: C=C(C)C(=O)Nc1ccc(-c2c(-c3ccc(C(=O)NC4CC(F)(F)C4)c(OC)c3)c3c(N)ncnc3n2C)cc1] | $^1$H NMR (400 MHz, DMSO-$d_6$) δ 9.91 (s, 1H), 8.47 (d, J = 6.8 Hz, 1H), 8.22 (s, 1H), 7.76-7.69 (m, 2H), 7.62 (d, J = 7.9 Hz, 1H), 7.35-7.27 (m, 2H), 6.93 (d, J = 1.5 Hz, 1H), 6.87 (dd, J = 7.8, 1.5 Hz, 1H), 6.01 (s, 1H), 5.81 (s, 1H), 5.54 (t, J = J = 1.5 Hz, 1H), 4.30-4.21 (m, 1H), 3.71 (s, 3H), 3.61 (s, 3H), 3.00-2.85 (m, 2H), 2.82-2.68 (m, 2H), 2.08 (s, 1H), 1.96 (d, J = 1.2 Hz, 3H). | 547.25 |
| 4-(4-amino-6-(4-methacrylamido phenyl)-7-methyl-7H-pyrrolo[2,3-d]pyrimidin-5-yl)-N-cyclobutyl-2-methoxybenzamide | 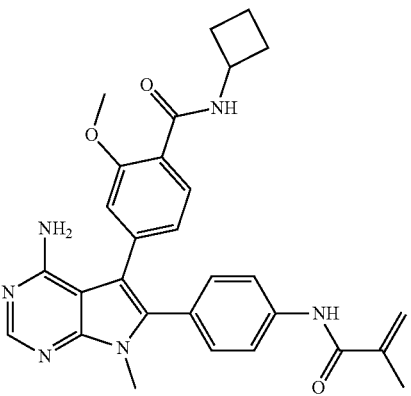 [SMILES: C=C(C)C(=O)Nc1ccc(-c2c(-c3ccc(C(=O)NC4CCC4)c(OC)c3)c3c(N)ncnc3n2C)cc1] | $^1$H NMR (400 MHz, DMSO-$d_6$) δ 9.91 (s, 1H), 8.23 (d, J = 11.7 Hz, 2H), 7.76-7.68 (m, 2H), 7.60 (d, J = 7.8 Hz, 1H), 7.34-7.26 (m, 2H), 6.92 (d, J = 1.5 Hz, 1H), 6.85 (dd, J = 7.9, 1.5 Hz, 1H), 6.01 (s, 1H), 5.81 (d, J = 1.3 Hz, 1H), 5.57-5.51 (m, 1H), 4.39 (h, J = 8.2 Hz, 1H), 3.72 (s, 3H), 3.60 (s, 3H), 2.21 (dtt, J = 8.9, 6.9, 3.0 Hz, 2H), 2.06-1.93 (m, 5H), 1.66 (tt, J = 10.5, 6.3 Hz, 2H). | 511.45 |
| 4-(4-amino-6-(4-methacrylamido phenyl)-7-methyl-7H-pyrrolo[2,3-d]pyrimidin-5-yl)-N-((1s,3s)-3-fluorocyclobutyl)-2-(methoxymethyl)benzamide | 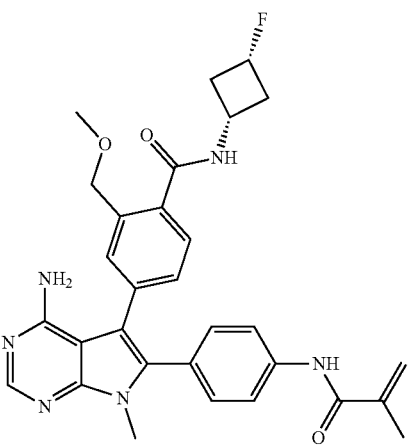 [SMILES: C=C(C)C(=O)Nc1ccc(-c2c(-c3ccc(C(=O)N[C@H]4C[C@@H](F)C4)c(COC)c3)c3c(N)ncnc3n2C)cc1] | $^1$H NMR (400 MHz, DMSO-$d_6$) δ 9.90 (s, 1H), 8.65 (d, J = 6.9 Hz, 1H), 8.21 (s, 1H), 7.71 (d, J = 8.5 Hz, 2H), 7.40 (d, J = 7.8 Hz, 1H), 7.35 (d, J = 1.8 Hz, 1H), 7.29 (d, J = 8.5 Hz, 2H), 7.20 (dd, J = 7.9, 1.8 Hz, 1H), 5.85 (s, 1H), 5.79 (s, 1H), 5.54 (s, 1H), 5.32-5.14 (m, 1H), 4.51 (s, 2H), 4.45 (s, 1H), 3.60 (s, 3H), 3.16 (s, 3H), 2.53-2.35 (m, 4H), 1.95 (s, 3H). | 543.25 |

TABLE 11-continued

Additional Exemplary Compounds

| Compound | Structure | Proton NMR | MS [M + 1] |
|---|---|---|---|
| 4-(4-amino-6-(4-methacrylamido phenyl)-7-methyl-7H-pyrrolo[2,3-d]pyrimidin-5-yl)-2-(difluoromethoxy)-N-((1r,3r)-3-fluorocyclobutyl) benzamide | 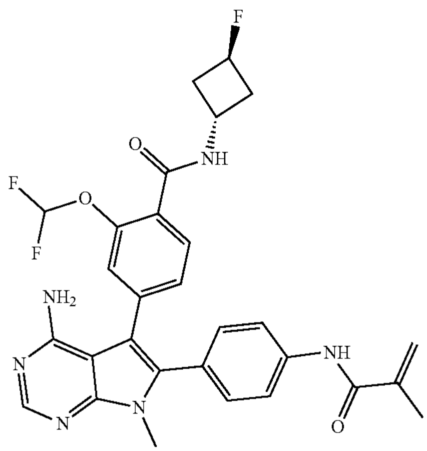 [SMILES: C=C(C)C(=O)Nc1ccc(-c2c(-c3ccc(C(=O)N[C@H]4C[C@H](F)C4)c(OC(F)F)c3)c3c(N)ncnc3n2C)cc1] | ¹H NMR (400 MHz, DMSO-d₆) δ 9.93 (s, 1H), 8.62 (d, J = 1.0 Hz, 1H), 8.22 (s, 1H), 7.78-7.70 (m, 2H), 7.47 (d, J = 7.9 Hz, 1H), 7.34-7.26 (m, 2H), 7.17-7.01 (m, 3H), 6.01 (s, 2H), 5.80 (d, J = 1.3 Hz, 1H), 5.55 (d, J = 1.7 Hz, 1H), 5.31 (ddd, J = 10.5, 6.4, 4.2 Hz, 1H), 5.17 (ddd, J = 11.0, 6.6, 4.3 Hz, 1H), 3.59 (s, 3H), 2.55 (dd, J = 9.2, 4.2 Hz, 1H), 2.51-2.29 (m, 2H), 1.95 (d, J = 1.2 Hz, 3H). | 565.25 |
| 4-(4-amino-6-(4-methacrylamido phenyl)-7-methyl-7H-pyrrolo[2,3-d]pyrimidin-5-yl)-N-((1r,3r)-3-fluorocyclobutyl)-2-(methoxymethyl) benzamide | 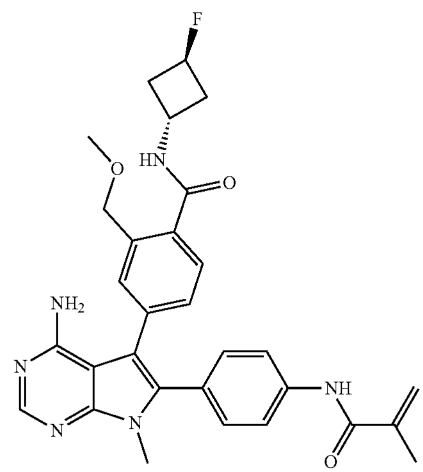 [SMILES: C=C(C)C(=O)Nc1ccc(-c2c(-c3ccc(C(=O)N[C@H]4C[C@H](F)C4)c(COC)c3)c3c(N)ncnc3n2C)cc1] | ¹H NMR (400 MHz, DMSO-d₆) δ 9.90 (s, 1H), 8.62 (d, J = 7.5 Hz, 1H), 8.21 (s, 1H), 7.71 (dd, J = 8.7, 2.2 Hz, 2H), 7.40 (d, J = 7.8 Hz, 1H), 7.35 (d, J = 1.8 Hz, 1H), 7.33-7.25 (m, 2H), 7.20 (dd, J = 7.8, 1.8 Hz, 1H), 5.98 (s, 1H), 5.79 (s, 1H), 5.54 (d, J = 2.0 Hz, 1H), 4.92-4.78 (p, J = 6.8 Hz, 1H), 4.51 (s, 2H), 3.92 (p, J = 7.9 Hz, 1H), 3.60 (s, 3H), 3.16 (s, 3H), 2.73 (ddq, J = 12.7, 6.0, 3.1 Hz, 2H), 2.29-2.11 (m, 2H), 1.95 (d, J = 1.2 Hz, 3H). | 543.25 |
| 4-(4-amino-6-(4-methacrylamido phenyl)-7-methyl-7H-pyrrolo[2,3-d]pyrimidin-5-yl)-N-((1s,3s)-3-fluorocyclobutyl)-2-methoxybenzamide | 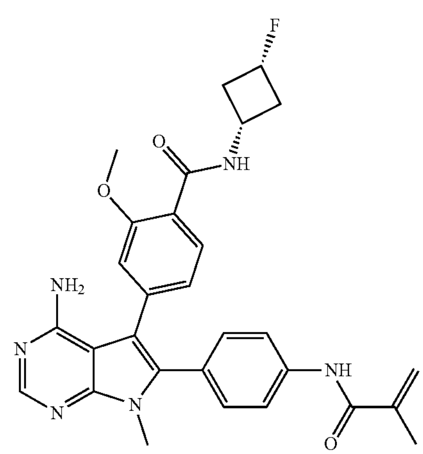 [SMILES: C=C(C)C(=O)Nc1ccc(-c2c(-c3ccc(C(=O)N[C@H]4C[C@@H](F)C4)c(OC)c3)c3c(N)ncnc3n2C)cc1] | ¹H NMR (400 MHz, DMSO-d₆) δ 9.91 (s, 1H), 8.32 (d, J = 7.7 Hz, 1H), 8.21 (s, 1H), 7.72 (d, J = 8.3 Hz, 2H), 7.59 (d, J = 7.8 Hz, 1H), 7.30 (d, J = 8.7 Hz, 2H), 6.92 (s, 1H), 6.86 (d, J = 7.8 Hz, 1H), 6.01 (s, 2H), 5.81 (s, 1H), 5.54 (s, 1H), 5.02-4.65 (m, 1H), 3.96 (q, J = 8.0 Hz, 1H), 3.66 (d, J = 43.5 Hz, 6H), 2.72 (dd, J = 11.6, 5.5 Hz, 2H), 2.37-2.11 (m, 2H), 1.95 (s, 3H). | 529.25 |

TABLE 11-continued

Additional Exemplary Compounds

| Compound | Structure | Proton NMR | MS [M + 1] |
|---|---|---|---|
| 4-(4-amino-6-(4-methacrylamido phenyl)-7-methyl-7H-pyrrolo[2,3-d]pyrimidin-5-yl)-N-((1r,3r)-3-fluorocyclobutyl)-2-methoxybenzamide | 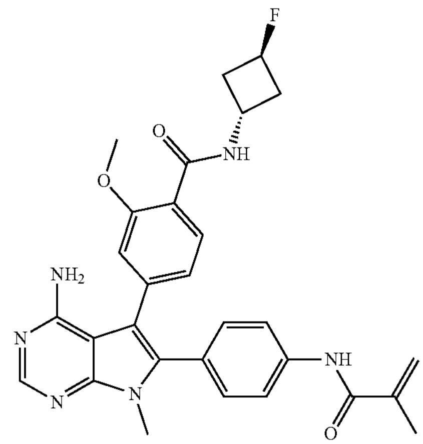 [SMILES: C=C(C)C(=O)Nc1ccc(-c2c(-c3ccc(C(=O)N[C@H]4C[C@H](F)C4)c(OC)c3)c3c(N)ncnc3n2C)cc1] | ¹H NMR (400 MHz, DMSO-d₆) δ 9.91 (s, 1H), 8.32 (d, J = 7.7 Hz, 1H), 8.21 (s, 1H), 7.72 (d, J = 8.3 Hz, 2H), 7.59 (d, J = 7.8 Hz, 1H), 7.30 (d, J = 8.7 Hz, 2H), 6.92 (s, 1H), 6.86 (d, J = 7.8 Hz, 1H), 6.01 (s, 2H), 5.81 (s, 1H), 5.54 (s, 1H), 5.02-4.65 (m, 1H), 3.96 (q, J = 8.0 Hz, 1H), 3.66 (d, J = 43.5 Hz, 6H), 2.72 (dd, J = 11.6, 5.5 Hz, 2H), 2.37-2.11 (m, 2H), 1.95 (s, 3H). | 529.25 |
| 4-(4-amino-6-(4-methacrylamido phenyl)-7-methyl-7H-pyrrolo[2,3-d]pyrimidin-5-yl)-2-methoxy-N-(1-(methoxymethyl) cyclobutyl) benzamide | 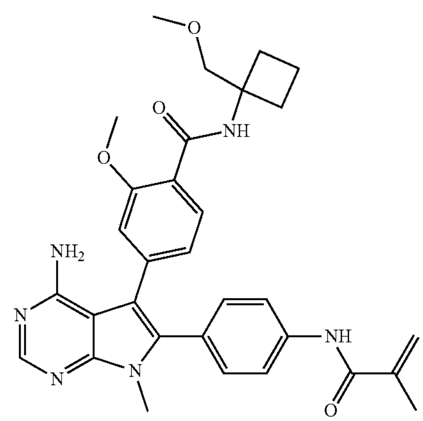 [SMILES: C=C(C)C(=O)Nc1ccc(-c2c(-c3ccc(C(=O)NC4(COC)CCC4)c(OC)c3)c3c(N)ncnc3n2C)cc1] | ¹H NMR (400 MHz, DMSO-d₆) δ 9.94 (s, 1H), 8.40 (s, 1H), 8.14 (s, 1H), 7.75 (t, J = 8.1 Hz, 3H), 7.35-7.27 (m, 2H), 7.04-6.99 (m, 1H), 6.86 (dd, J = 7.9, 1.5 Hz, 1H), 5.81 (s, 1H), 5.55 (d, J = 1.6 Hz, 1H), 3.77 (s, 3H), 3.67 (s, 3H), 3.58 (s, 2H), 3.33 (s, 3H), 2.43-2.33 (m, 2H), 2.07 (s, 2H), 1.95 (d, J = 1.5 Hz, 3H), 1.93-1.72 (m, 2H). | 555.25 |
| 4-(4-amino-6-(4-methacrylamido phenyl)-7-methyl-7H-pyrrolo[2,3-d]pyrimidin-5-yl)-N-isobutyl-2-methoxybenzamide | 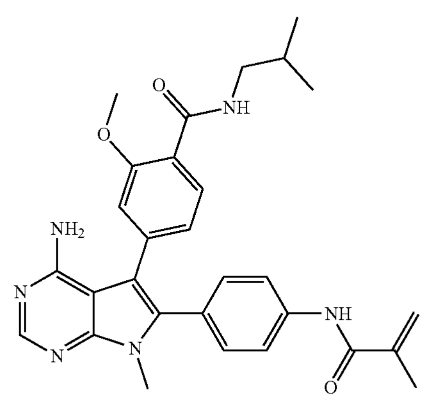 [SMILES: C=C(C)C(=O)Nc1ccc(-c2c(-c3ccc(C(=O)NCC(C)C)c(OC)c3)c3c(N)ncnc3n2C)cc1] | ¹H NMR (400 MHz, DMSO-d₆) δ 9.91 (s, 1H), 8.21 (s, 1H), 8.10 (t, J = 5.9 Hz, 1H), 7.76-7.69 (m, 2H), 7.65 (d, J = 7.9 Hz, 1H), 7.34-7.27 (m, 2H), 6.94 (d, J = 1.5 Hz, 1H), 6.86 (dd, J = 7.9, 1.5 Hz, 1H), 6.02 (s, 1H), 5.81 (s, 1H), 5.54 (d, J = 1.9 Hz, 1H), 3.72 (s, 3H), 3.60 (s, 3H), 3.10 (t, J = 6.4 Hz, 2H), 1.95 (t, J = 1.2 Hz, 3H), 1.81 (hept, J = 6.7 Hz, 1H), 0.89 (d, J = 6.7 Hz, 6H). | 513.30 |

TABLE 11-continued

Additional Exemplary Compounds

| Compound | Structure | Proton NMR | MS [M + 1] |
| --- | --- | --- | --- |
| 4-(4-amino-6-(4-methacrylamido phenyl)-7-methyl-7H-pyrrolo[2,3-d]pyrimidin-5-yl)-2-(difluoromethoxy)-N-((1s,3s)-3-fluorocyclobutyl) benzamide | 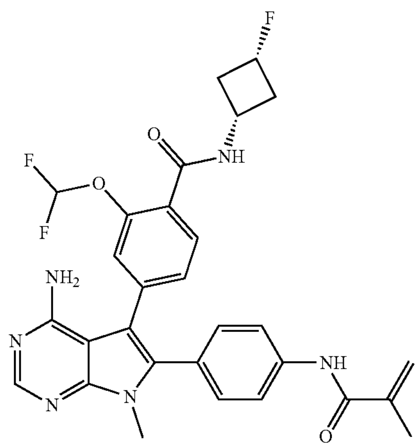 [SMILES: C=C(C)C(=O)Nc1ccc(-c2c(-c3ccc(C(=O)N[C@H]4C[C@@H](F)C4)c(OC(F)F)c3)c3c(N)ncnc3n2C)cc1] | $^1$H NMR (400 MHz, DMSO-d$_6$) δ 9.93 (s, 1H), 8.58 (d, J = 7.7 Hz, 1H), 8.22 (s, 1H), 7.74-7.73 (d, J = 6.8 Hz, 2H), 7.46 (d, J = 7.8 Hz, 1H), 7.33-7.25 (m, 2H), 7.13-6.84 (dd, J = 7.9, 1.6 Hz, 3H), 6.03 (s, 1H), 5.80 (s, 1H), 5.54 (t, J = 1.5 Hz, 1H), 4.78 (p, J = 7.0 Hz, 1H), 3.93 (q, J = 8.0 Hz, 1H), 3.59 (s, 3H), 2.73 (dq, J = 9.6, 3.0 Hz, 1H), 2.27-2.06 (m, 2H), 1.95 (t, J = 1.2 Hz, 3H), | 565.20 |
| 4-(4-amino-6-(4-methacrylamido phenyl)-7-methyl-7H-pyrrolo[2,3-d]pyrimidin-5-yl)-2-cyclopropoxy-N-((1s,3s)-3-fluorocyclobutyl) benzamide | 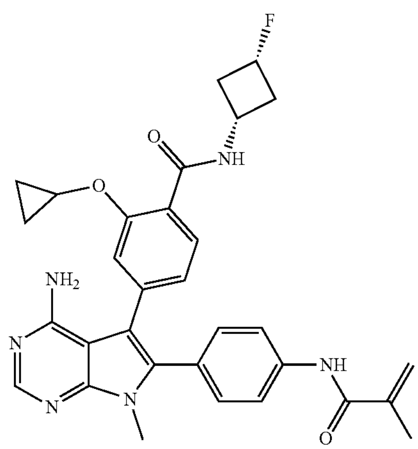 [SMILES: C=C(C)C(=O)Nc1ccc(-c2c(-c3ccc(C(=O)N[C@H]4C[C@@H](F)C4)c(OC4CC4)c3)c3c(N)ncnc3n2C)cc1] | $^1$H NMR (400 MHz, DMSO-d$_6$) δ 9.92 (s, 1H), 8.22 (s, 1H), 8.16 (d, J = 7.0 Hz, 1H), 7.81-7.66 (m, 2H), 7.55 (d, J = 7.9 Hz, 1H), 7.39-7.28 (m, 2H), 7.23 (d, J = 1.6 Hz, 1H), 6.91 (dd, J = 7.8, 1.5 Hz, 1H), 5.85-5.75 (m, 1H), 5.58-5.51 (m, 1H), 5.23 (dddd, J = 56.7, 10.2, 6.5, 3.8 Hz, 1H), 4.48 (q, J = 7.7 Hz, 1H), 3.73 (tt, J = 6.1, 3.0 Hz, 1H), 3.61 (s, 3H), 2.48-2.38 (m, 2H), 2.38-2.28 (m, 2H), 1.96 (t, J = 1.3 Hz, 3H), 0.66 (t, J = 5.8 Hz, 2H), 0.61 (d, J = 3.2 Hz, 2H). | 555.25 |
| 4-(4-amino-6-(4-methacrylamido phenyl)-7-methyl-7H-pyrrolo[2,3-d]pyrimidin-5-yl)-2-cyclopropoxy-N-((1r,3r)-3-fluorocyclobutyl) benzamide | 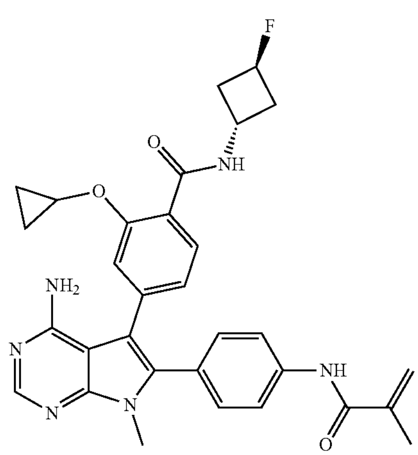 [SMILES: C=C(C)C(=O)Nc1ccc(-c2c(-c3ccc(C(=O)N[C@H]4C[C@H](F)C4)c(OC4CC4)c3)c3c(N)ncnc3n2C)cc1] | $^1$H NMR (400 MHz, DMSO-d$_6$) δ 9.92 (s, 1H), 8.22 (s, 1H), 8.12 (d, J = 7.7 Hz, 1H), 7.82-7.67 (m, 2H), 7.54 (d, J = 7.8 Hz, 1H), 7.34-7.26 (m, 2H), 7.22 (d, J = 1.5 Hz, 1H), 6.90 (dd, J = 7.9, 1.5 Hz, 1H), 5.81 (t, J = 1.1 Hz, 1H), 5.54 (t, J = 1.4 Hz, 1H), 4.84 (dp, J = 56.8, 6.8 Hz, 1H), 3.92 (dt, J = 15.3, 7.6 Hz, 1H), 3.72 (dq, J = 6.2, 3.0 Hz, 1H), 3.61 (s, 3H), 2.81-2.64 (m, 2H), 2.29-2.03 (m, 2H), 1.95 (t, J = 1.2 Hz, 3H), 0.64 (dd, J = 24.4, 4.7 Hz, 4H). | 555.30 |

TABLE 11-continued

Additional Exemplary Compounds

| Compound | Structure | Proton NMR | MS [M + 1] |
| --- | --- | --- | --- |
| 4-(4-amino-6-(4-methacrylamido phenyl)-7-methyl-7H-pyrrolo[2,3-d]pyrimidin-5-yl)-N-(1-fluorocyclobutyl) methyl)-2-methoxybenzamide | 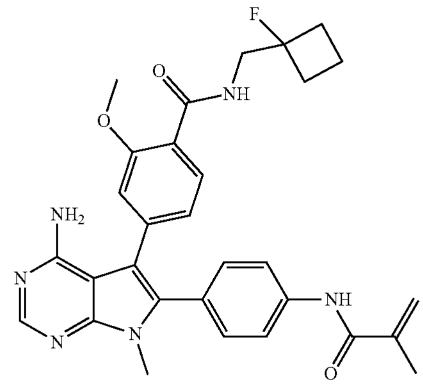 [SMILES: C=C(C)C(=O)Nc1ccc(-c2c(-c3ccc(C(=O)NCC4(F)CCC4)c(OC)c3)c3c(N)ncnc3n2C)cc1] | $^1$H NMR (400 MHz, DMSO-d$_6$) δ 9.91 (s, 1H), 8.24 (d, J = 18.2 Hz, 2H), 7.75-7.68 (m, 3H), 7.33-7.27 (m, 2H), 6.95 (d, J = 1.4 Hz, 1H), 6.87 (dd, J = 7.9, 1.5 Hz, 1H), 6.04 (s, 2H), 5.81 (s, 1H), 5.54 (s, 1H), 3.73 (s, 3H), 3.71-3.60 (m, 2H), 3.60 (s, 3H), 2.26-2.13 (m, 4H), 2.08 (s, 1H), 1.95 (t, J = 1.2 Hz, 3H), 1.75 (dd, J = 11.4, 6.3 Hz, 1H), 1.53 (q, J = 8.8 Hz, 1H). | 543.30 |
| 6-(4-amino-6-(4-methacrylamido phenyl)-7-methyl-7H-pyrrolo[2,3-d]pyrimidin-5-yl)-N-(cyclobutylmethyl)-2-methoxynicotinamide | 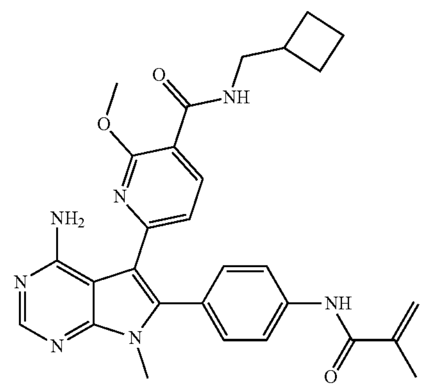 | 1H NMR (400 MHz, DMSO-d6) δ 9.99 (s, 1H), 8.18 (d, J = 11.9 Hz, 2H), 7.86-7.69 (m, 3H), 7.40-7.28 (m, 4H), 6.55 (d, J = 7.9 Hz, 1H), 5.83 (s, 1H), 5.56 (d, J = 1.9 Hz, 1H), 4.03 (s, 3H), 3.55 (s, 3H), 3.28 (d, J = 6.3 Hz, 2H), 2.53 (s, 1H), 1.82 (q, J = 6.7, 6.2 Hz, 2H), 1.77-1.67 (m, 2H). | 526.30 |
| (R)-N-(4-(4-amino-7-methyl-5-(4-(pyrrolidine-1-carbonyl)cyclohex-1-en-1-yl)-7H-pyrrolo[2,3-d]pyrimidin-6-yl)-3-chlorophenyl) methacrylamide | 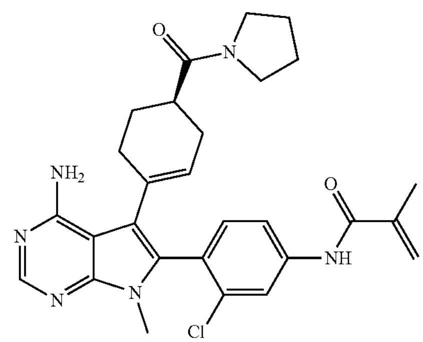 [SMILES: C=C(C)C(=O)Nc1ccc(-c2c(C3=CC[C@H](C(=O)N4CCCC4)CC3)c3c(N)ncnc3n2C)c(Cl)c1] | $^1$H NMR (400 MHz, DMSO-d$_6$) δ 10.12 (s, 1H), 8.11 (d, J = 3.9 Hz, 1H), 8.07 (d, J = 2.0 Hz, 1H), 7.74 (ddd, J = 8.4, 3.5, 2.1 Hz, 1H), 7.37 (dd, J = 8.4, 6.3 Hz, 1H), 6.55 (d, J = 47.7 Hz, 2H), 5.87 (s, 1H), 5.75-5.63 (m, 1H), 5.60 (s, 1H), 3.51-3.41 (m, 2H), 3.40 (d, J = 2.0 Hz, 3H), 3.27 (ddt, J = 12.1, 8.4, 4.6 Hz, 2H), 2.75 (qt, J = 7.7, 3.4 Hz, 1H), 2.34-2.03 (m, 3H), 1.97 (s, 4H), 1.84 (qd, J = 6.7, 3.3 Hz, 2H), 1.76 (qd, J = 6.7, 2.2 Hz, 2H), 1.71-1.45 (m, 2H). | 519.20 |
| (R)-N-(4-(4-amino-7-methyl-5-(4-(pyrrolidine-1-carbonyl)cyclohex-1-en-1-yl)-7H-pyrrolo[2,3-d]pyrimidin-6-yl)-3-fluorophenyl) methacrylamide | 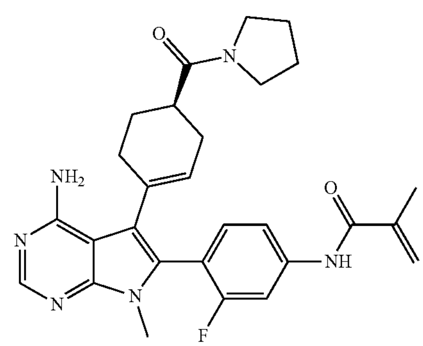 [SMILES: C=C(C)C(=O)Nc1ccc(-c2c(C3=CC[C@H](C(=O)N4CCCC4)CC3)c3c(N)ncnc3n2C)c(F)c1] | $^1$H NMR (400 MHz, DMSO-d$_6$) δ 10.15 (s, 1H), 8.12 (s, 1H), 7.83 (dd, J = 12.6, 2.0 Hz, 1H), 7.59 (dd, J = 8.4, 2.1Hz, 1H), 7.37 (t, J = 8.5 Hz, 1H), 6.57 (s, 1H), 5.86 (s, 1H), 5.69 (s, 1H), 5.60 (s, 1H), 3.55-3.40 (m, 5H), 3.28 (d, J = 6.5 Hz, 1H), 2.79 (t, J = 6.1 Hz, 1H), 2.21 (d, J = 17.2 Hz, 2H), 1.97 (d, J = 1.3 Hz, 3H), 1.81 (dq, J = 35.8, 6.8 Hz, 4H), 1.63 (s, 2H). | 503.25 |

TABLE 11-continued

Additional Exemplary Compounds

| Compound | Structure | Proton NMR | MS [M + 1] |
|---|---|---|---|
| (R)-N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)methacrylamide | 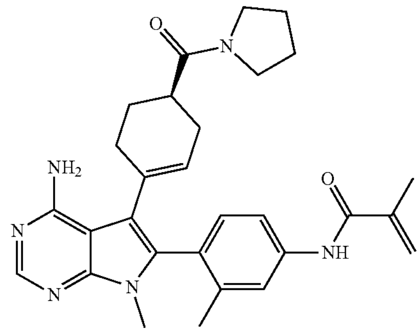 [SMILES: C=C(C)C(=O)Nc1ccc(-c2c(C3=CC[C@H](C(=O)N4CCCC4)CC3)c3c(N)ncnc3n2C)c(C)c1] | $^1$H NMR (400 MHz, DMSO-d$_6$) δ 9.87 (s, 1H), 8.10 (s, 1H), 7.71 (t, J = 2.7 Hz, 1H), 7.62 (ddd, J = 8.0, 5.6, 2.2 Hz, 1H), 7.18 (dd, J = 8.3, 6.6 Hz, 1H), 6.48 (d, J = 17.0 Hz, 2H), 5.91-5.79 (m, 1H), 5.66 (ddt, J = 14.5, 4.1, 2.2 Hz, 1H), 5.54 (t, J = 1.5 Hz, 1H), 3.56-3.39 (m, 2H), 3.34 (s, 3H), 3.27 (q, J = 6.9 Hz, 2H), 2.73 (p, J = 6.3 Hz, 1H), 2.21 (q, J = 15.7, 12.1 Hz, 2H), 2.06 (s, 3H), 2.01-1.80 (m, 7H), 1.80-1.70 (m, 2H), 1.56 (q, J = 7.9, 7.0 Hz, 2H). | 499.35 |
| (R)-N-(4-(5-(4-(2-oxa-5-azaspiro[3.4]octane-5-carbonyl)cyclohexan-1-yl)-4-amino-7-methyl-7H-pyrrolo[2,3-d]pyrimidin-6-yl)-3-fluorophenyl)methacrylamide | 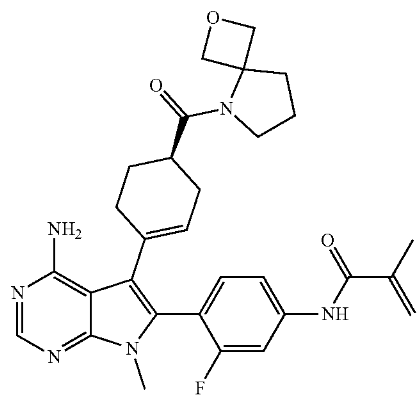 [SMILES: C=C(C)C(=O)Nc1ccc(-c2c(C3=CC[C@H](C(=O)N4CCCC45COC5)CC3)c3c(N)ncnc3n2C)c(F)c1] | $^1$H NMR (400 MHz, DMSO-d$_6$) δ 10.16 (s, 1H), 8.14 (s, 1H), 7.84 (dd, J = 12.6, 2.0 Hz, 1H), 7.59 (dd, J = 8.4, 2.0 Hz, 1H), 7.37 (t, J = 8.5 Hz, 1H), 6.55 (s, 2H), 5.86 (t, J = 1.1 Hz, 1H), 5.71 (s, 1H), 5.60 (d, J = 1.9 Hz, 1H), 5.30 (dd, J = 13.7, 4.9 Hz, 2H), 4.19 (d, J = 4.9 Hz, 2H), 3.60-3.43 (m, 5H), 2.97-2.78 (m, 1H), 2.44-2.07 (m, 4H), 1.98 (t, J = 1.2 Hz, 5H), 1.70 (dq, J = 19.5, 7.6, 7.1 Hz, 4H). | 545.25 |
| (S)-N-(4-(5-(4-(2-oxa-5-azaspiro[3.4]octane-5-carbonyl)cyclohexan-1-yl)-4-amino-7-methyl-7H-pyrrolo[2,3-d]pyrimidin-6-yl)-3-fluorophenyl)methacrylamide | 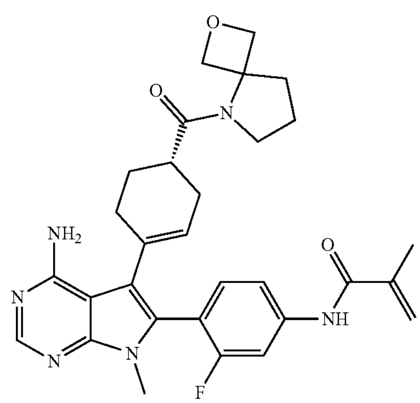 [SMILES: C=C(C)C(=O)Nc1ccc(-c2c(C3=CC[C@@H](C(=O)N4CCCC45COC5)CC3)c3c(N)ncnc3n2C)c(F)c1] | $^1$H NMR (400 MHz, DMSO-d$_6$) δ 10.16 (s, 1H), 8.14 (s, 1H), 7.84 (dd, J = 12.6, 2.0 Hz, 1H), 7.59 (dd, J = 8.5, 2.0 Hz, 1H), 7.37 (t, J = 8.5 Hz, 1H), 6.55 (s, 2H), 5.86 (t, J = 1.0 Hz, 1H), 5.71 (s, 1H), 5.60 (d, J = 1.8 Hz, 1H), 5.30 (dd, J = 13.7, 4.9 Hz, 2H), 4.19 (d, J = 4.9 Hz, 2H), 3.61-3.40 (m, 5H), 2.93-2.78 (m, 1H), 2.37-2.13 (m, 4H), 1.98 (t, J = 1.2 Hz, 5H), 1.70 (td, J = 15.9, 14.6, 7.9 Hz, 4H). | 545.25 |
| (R)-N-(4-(5-(4-(2-oxa-5-azaspiro[3.4]octane-5-carbonyl)cyclohexan-1-yl)-4-amino-7-methyl-7H-pyrrolo[2,3-d]pyrimidin-6-yl)-3-methylphenyl)methacrylamide | 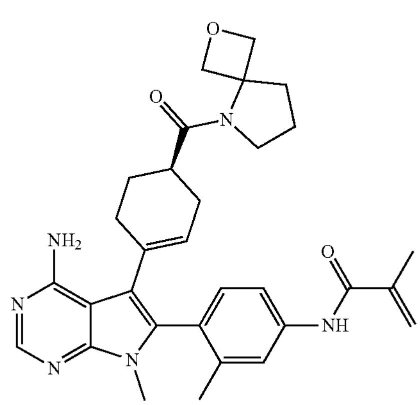 [SMILES: C=C(C)C(=O)Nc1ccc(-c2c(C3=CC[C@H](C(=O)N4CCCC45COC5)CC3)c3c(N)ncnc3n2C)c(C)c1] | 1H NMR (400 MHz, DMSO-d6) δ 9.87 (s, 1H), 8.11 (s, 1H), 7.73-7.70 (m, 1H), 7.63-7.62 (m, 1H), 7.20-7.17 (m, 1H), 6.51 (d, J = 28.6 Hz, 2H), 5.83 (s, 1H), 5.68 (d, J = 10.9 Hz, 1H), 5.55 (t, J = 1.5 Hz, 1H), 5.31-5.26 (m, 2H), 4.18-4.17 (m, 2H), 3.54-3.47 (m, 1H), 3.47-3.38 (m, 1H), 3.34 (s, 3H), 2.74 (d, J = 12.8 Hz, 1H), 2.35-2.24 (m, 1H), 2.23-2.16 (m, 3H), 2.06 (s, 3H), 1.97 (t, J = 1.2 Hz, 4H), 1.93-1.79 (m, 1H), 1.70 (p, J = 6.7 Hz, 2H), 1.58 (d, J = 5.2 Hz, 2H). | 541.35 |

TABLE 11-continued

Additional Exemplary Compounds

| Compound | Structure | Proton NMR | MS [M + 1] |
|---|---|---|---|
| (S)-N-(4-(5-(4-(2-oxa-5-azaspiro[3.4]octane-5-carbonyl)cyclohexan-1-yl)-4-amino-7-methyl-7H-pyrrolo[2,3-d]pyrimidin-6-yl)-3-methylphenyl)methacrylamide | 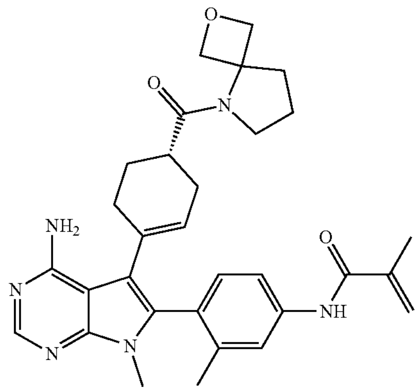 [SMILES: C=C(C)C(=O)Nc1ccc(-c2c(C3=CC[C@@H](C(=O)N4CCCC45COC5)CC3)c3c(N)ncnc3n2C)c(C)c1] | 1H NMR (400 MHz, DMSO-d6) δ 9.87 (s, 1H), 8.11 (s, 1H), 7.73-7.70 (m, 1H), 7.63-7.62 (m, 1H), 7.20-7.17 (m, 1H), 6.51 (d, J = 28.6 Hz, 2H), 5.83 (s, 1H), 5.68 (d, J = 10.9 Hz, 1H), 5.55 (t, J = 1.5 Hz, 1H), 5.31-5.26 (m, 2H), 4.18-4.17 (m, 2H), 3.54-3.47 (m, 1H), 3.47-3.38 (m, 1H), 3.34 (s, 3H), 2.74 (d, J = 12.8 Hz, 1H), 2.35-2.24 (m, 1H), 2.23-2.16 (m, 3H), 2.06 (s, 3H), 1.97 (t, J = 1.2 Hz, 4H), 1.93-1.79 (m, 1H), 1.70 (p, J = 6.7 Hz, 2H), 1.58 (d, J = 5.2 Hz, 2H). | 541.30 |
| (S)-N-(4-(4-amino-7-methyl-5-(4-(pyrrolidine-1-carbonyl)cyclohex-1-en-1-yl)-7H-pyrrolo[2,3-d]pyrimidin-6-yl)-3-fluorophenyl)methacrylamide | 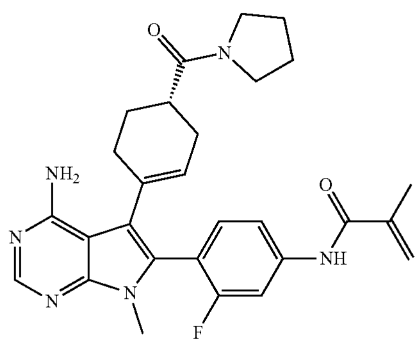 [SMILES: C=C(C)C(=O)Nc1ccc(-c2c(C3=CC[C@@H](C(=O)N4CCCC4)CC3)c3c(N)ncnc3n2C)c(F)c1] | $^1$H NMR (400 MHz, DMSO-d$_6$) δ 10.15 (s, 1H), 8.12 (s, 1H), 7.83 (dd, J = 12.5, 2.0 Hz, 1H), 7.59 (dd, J = 8.5, 2.0 Hz, 1H), 7.37 (t, J = 8.4 Hz, 1H), 6.60 (s, 2H), 5.86 (s, 1H), 5.69 (s, 1H), 5.60 (s, 1H), 3.55-3.40 (m, 5H), 3.28 (d, J = 6.5 Hz, 1H), 2.83-2.76 (m, 1H), 2.21 (d, J = 16.9 Hz, 2H), 1.98 (t, J = 1.2 Hz, 3H), 1.87 (p, J = 6.8 Hz, 2H), 1.76 (p, J = 6.8 Hz, 2H), 1.63 (s, 2H). | 503.25 |
| (S)-N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)methacrylamide | 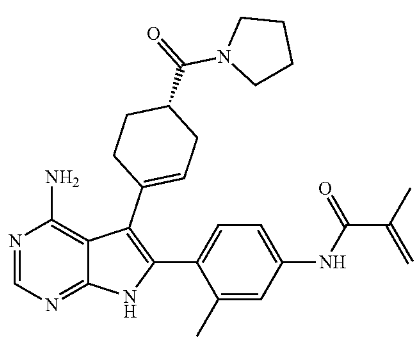 [SMILES: C=C(C)C(=O)Nc1ccc(-c2[nH]c3ncnc(N)c3c2C2=CC[C@@H](C(=O)N3CCCC3)CC2)c(C)c1] | 1H NMR (400 MHz, DMSO-d6) δ 9.86 (s, 1H), 8.10 (s, 1H), 7.71 (d, J = 2.4 Hz, 1H), 7.61 (t, J = 8.2, 2.3 Hz, 1H), 7.18 (t, J = 8.3, 6.6 Hz, 1H), 6.50 (s, 2H), 5.87-5.78 (m, 1H), 5.64 (s, 1H), 5.54 (d, J = 1.8 Hz, 1H), 3.52-3.38 (m, 2H), 3.33-3.22 (m, 5H), 2.73 (t, J = 6.1 Hz, 1H), 2.25 (t, J = 42.5, 23.2 Hz, 2H), 2.06 (s, 3H), 1.97 (d, J = 1.2 Hz, 4H), 1.93-1.80 (m, 3H), 1.75 (p, J = 6.7 Hz, 2H), 1.56 (d, J = 6.1 Hz, 2H). | 499.30 |
| (S)-N-(4-(4-amino-7-methyl-5-(4-methyl-4-(pyrrolidine-1-carbonyl)cyclohex-1-en-1-yl)-7H-pyrrolo[2,3-d]pyrimidin-6-yl)phenyl)methacrylamide | isomer 1 | $^1$H NMR (400 MHz, DMSO-d$_6$) δ 9.88 (s, 1H), 8.12 (s, 1H), 7.80-7.72 (m, 2H), 7.32-7.24 (m, 2H), 5.86-5.78 (m, 2H), 5.76 (s, 2H), 5.56-5.51 (m, 1H), 3.58 (s, 3H), 3.39 (s, 4H), 2.74 (d, J = 16.0 Hz, 1H), 2.05-1.82 (m, 7H), 1.77-1.55 (m, 5H), 1.16 (s, 3H). | 499.30 |

TABLE 11-continued

Additional Exemplary Compounds

| Compound | Structure | Proton NMR | MS [M + 1] |
|---|---|---|---|
| (S)-N-(4-(4-amino-7-methyl-5-(4-methyl-4-(pyrrolidine-1-carbonyl)cyclohex-1-en-1-yl)-7H-pyrrolo[2,3-d]pyrimidin-6-yl)phenyl)methacrylamide | 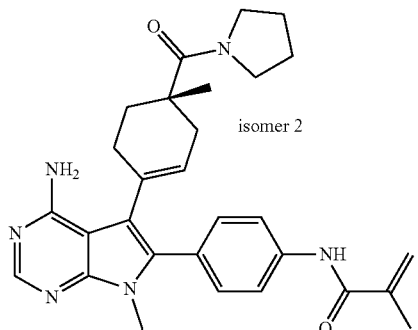 isomer 2 | $^1$H NMR (400 MHz, DMSO-d$_6$) δ 9.88 (s, 1H), 8.13 (s, 1H), 7.80-7.72 (m, 2H), 7.32-7.24 (m, 2H), 6.05-5.65 (m, 3H), 5.56-5.51 (m, 1H), 3.59 (s, 3H), 3.41 (s, 4H), 2.75 (d, J = 16.7 Hz, 1H), 2.08-1.89 (m, 7H), 1.75 (s, 4H), 1.63 (dd, J = 12.6, 6.4 Hz, 1H), 1.16 (s, 3H). | 499.30 |
| (S)-N-(4-(4-amino-7-methyl-5-(4-methyl-4-(pyrrolidine-1-carbonyl)cyclohex-1-en-1-yl)-7H-pyrrolo[2,3-d]pyrimidin-6-yl)phenyl)methacrylamide | 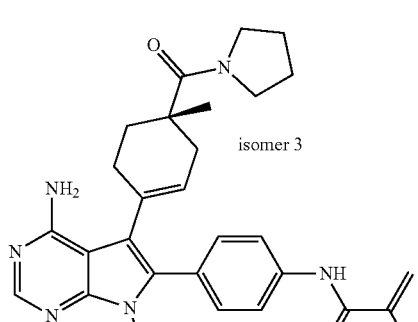 isomer 3 | $^1$H NMR (400 MHz, DMSO-d$_6$) δ 9.95 (s, 1H), 8.08 (s, 1H), 7.84-7.76 (m, 2H), 7.45-7.37 (m, 2H), 6.53 (s, 2H), 5.83 (s, 1H), 5.78 (d, J = 4.5 Hz, 1H), 5.56 (t, J = 1.5 Hz, 1H), 3.57 (s, 4H), 3.33 (s, 3H), 2.77 (d, J = 14.8 Hz, 1H), 2.11 (d, J = 13.6 Hz, 1H), 1.98 (d, J = 1.2 Hz, 3H), 1.90 (d, J = 17.3 Hz, 1H), 1.77 (s, 6H), 1.44 (s, 1H), 1.21 (s, 3H). | 499.30 |
| (S)-N-(4-(4-amino-7-methyl-5-(4-methyl-4-(pyrrolidine-1-carbonyl)cyclohex-1-en-1-yl)-7H-pyrrolo[2,3-d]pyrimidin-6-yl)phenyl)methacrylamide | 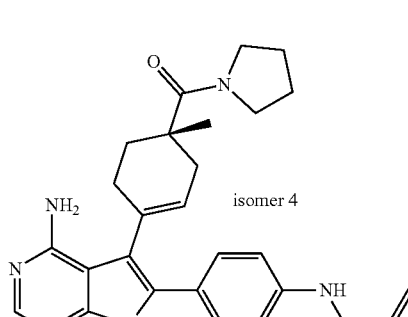 isomer 4 | $^1$H NMR (400 MHz, DMSO-d$_6$) δ 9.95 (s, 1H), 8.08 (s, 1H), 7.84-7.77 (m, 2H), 7.45-7.37 (m, 2H), 6.52 (s, 2H), 5.83 (t, J = 1.1 Hz, 1H), 5.81-5.75 (m, 1H), 5.56 (t, J = 1.5 Hz, 1H), 3.57 (s, 4H), 3.50 (s, 3H), 2.82-2.73 (m, 1H), 2.12 (d, J = 13.7 Hz, 1H), 1.97 (t, J = 1.2 Hz, 3H), 1.90 (d, J = 17.1 Hz, 1H), 1.77 (s, 6H), 1.70-1.37 (m, 1H), 1.21 (s, 3H). | 499.30 |
| (S)-N-(4-(4-amino-7-methyl-5-(4-(pyrrolidine-1-carbonyl)cyclohex-1-en-1-yl)-7H-pyrrolo[2,3-d]pyrimidin-6-yl)-3-chlorophenyl)methacrylamide | 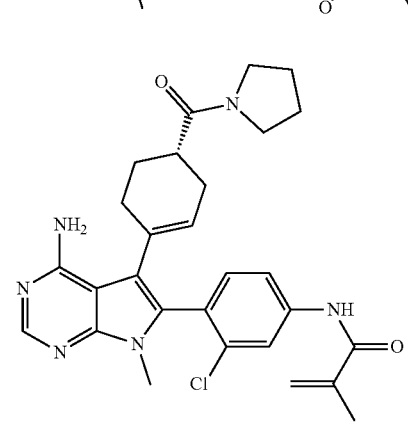 | $^1$H NMR (400 MHz, DMSO-d$_6$) δ 10.13 (s, 1H), 8.15-8.03 (m, 2H), 7.74 (ddd, J = 8.4, 3.6, 2.2 Hz, 1H), 7.37 (dd, J = 8.4, 6.4 Hz, 1H), 6.55 (d, J = 48.7 Hz, 2H), 5.87 (s, 1H), 5.78-5.60 (m, 2H), 3.54-3.41 (m, 2H), 3.40 (d, J = 2.0 Hz, 3H), 3.27 (ddt, J = 12.1, 8.4, 4.5 Hz, 2H), 2.75 (tt, J = 9.5, 4.2 Hz, 1H), 2.36-2.03 (m, 3H), 1.97 (s, 4H), 1.84 (qd, J = 6.7, 3.3 Hz, 2H), 1.76 (qd, J = 6.8, 2.2 Hz, 2H), 1.70-1.44 (m, 2H). | 519.20 |

TABLE 11-continued

Additional Exemplary Compounds

| Compound | Structure | Proton NMR | MS [M + 1] |
|---|---|---|---|
| (R)-N-(4-(5-(4-(6-azaspiro[3.4]octane-6-carbonyl)cyclohexan-1-yl)-4-amino-7-methyl-7H-pyrrolo[2,3-d]pyrimidin-6-yl)phenyl)methacrylamide | 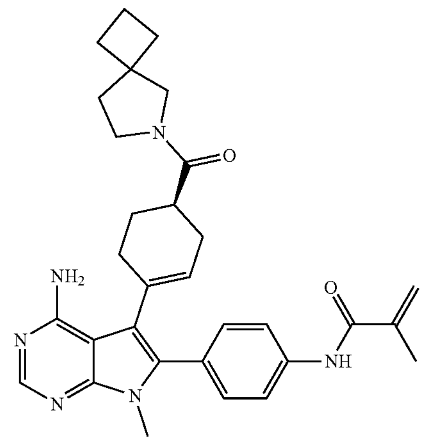 [SMILES: C=C(C)C(=O)Nc1ccc(-c2c(C3=CC[C@H](C(=O)N4CCC5(CCC5)C4)CC3)c3c(N)ncnc3n2C)cc1] | 1H NMR (400 MHz, Methanol-d4) 8.14 (s, 1H), 7.81-7.75 (m, 2H), 7.49-7.43 (m, 2H), 5.93 (s, 1H), 5.85 (t, J = 0.9 Hz, 1H), 5.57 (d, J = 1.7 Hz, 1H), 3.66 (s, 3H), 3.64-3.49 (m, 2H), 3.28-3.17 (m, 2H), 2.88-2.80 (m, 1H), 2.43 (t, J = 11.5 Hz, 1H), 2.35 (s, 1H), 2.16-1.98 (m, 7H), 1.96-1.86 (s, 1H), 1.86-1.68 (s, 7H), 1.28 (s, 1H). | 525.30 |
| (S)-N-(4-(5-(4-(6-azaspiro[3.4]octane-6-carbonyl)cyclohexan-1-yl)-4-amino-7-methyl-7H-pyrrolo[2,3-d]pyrimidin-6-yl)phenyl)methacrylamide | 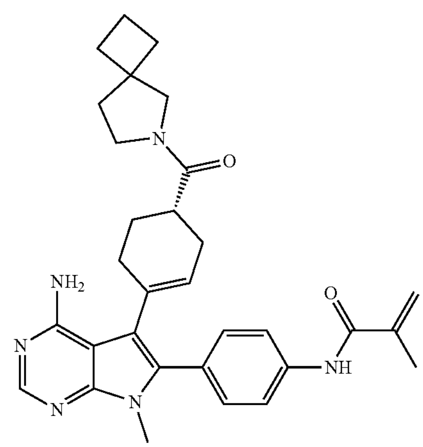 [SMILES: C=C(C)C(=O)Nc1ccc(-c2c(C3=CC[C@@H](C(=O)N4CCC5(CCC5)C4)CC3)c3c(N)ncnc3n2C)cc1] | 1H NMR (400 MHz, Methanol-d4) 8.14 (s, 1H), 7.82-7.74 (m, 2H), 7.46 (d, J = 8.2 Hz, 2H), 5.93 (s, 1H), 5.85 (t, J = 1.0 Hz, 1H), 5.57 (d, J = 1.5 Hz, 1H), 3.66 (s, 3H), 3.64-3.50 (m, 2H), 3.28-3.17 (m, 2H), 2.84 (t, J = 6.2 Hz, 1H), 2.42 (s, 1H), 2.35 (s, 1H), 2.16-1.98 (m, 7H), 1.96-1.85 (m, 1H), 1.81 (q, J = 6.6 Hz, 2H), 1.76 (s, 5H), 1.28 (s, 1H). | 525.30 |
| N-(4-(4-amino-5-(4-(indoline-1-carbonyl)phenyl)-7-methyl-7H-pyrrolo[2,3-d]pyrimidin-6-yl)phenyl)methacrylamide | 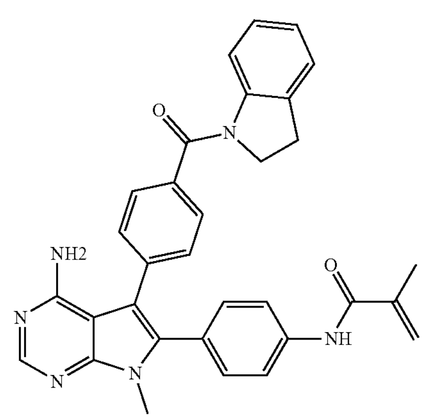 [SMILES: C=C(C)C(=O)Nc1ccc(-c2c(-c3ccc(C(=O)N4CCc5ccccc54)cc3)c3c(N)ncnc3n2C)cc1] | $^1$H NMR (400 MHz, DMSO-d$_6$) δ 9.92 (s, 1H), 8.22 (s, 1H), 7.73 (d, J = 8.5 Hz, 2H), 7.55 (d, J = 7.7 Hz, 2H), 7.35-7.24 (m, 5H), 7.16 (s, 1H), 7.02 (s, 1H), 5.80 (s, 1H), 5.54 (s, 1H), 4.05 (t, J = 8.3 Hz, 2H), 3.62 (s, 3H), 3.08 (t, J = 8.2 Hz, 2H), 1.95 (d, J = 1.3 Hz, 3H). | 529.25 |

TABLE 11-continued

Additional Exemplary Compounds

| Compound | Structure | Proton NMR | MS [M + 1] |
|---|---|---|---|
| (S)-N-(4-(4-amino-5-(4-(indoline-1-carbonyl)cyclohex-1-enyl)-7-methyl-7H-pyrrolo[2,3-d]pyrimidin-6-yl)phenyl) methacrylamide | 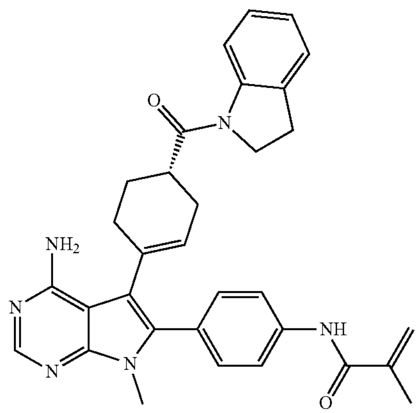 [SMILES: C=C(C)C(=O)Nc1ccc(-c2c(C3=CC[C@@H](C(=O)N4CCc5ccccc54)CC3)c3c(N)ncnc3n2C)cc1] | $^1$H NMR (400 MHz, DMSO-d$_6$) δ 9.95 (s, 1H), 8.13 (d, J = 8.7 Hz, 2H), 7.82 (d, J = 8.6 Hz, 2H), 7.52-7.39 (m, 2H), 7.23 (d, J = 7.4 Hz, 1H), 7.14 (t, J = 7.7 Hz, 1H), 6.99 (t, J = 7.4 Hz, 1H), 6.57 (s, 2H), 5.83 (d, J = 7.2 Hz, 2H), 5.55 (s, 1H), 4.32-4.02 (m, 2H), 3.59 (s, 3H), 3.14 (t, J = 8.5 Hz, 2H), 3.01 (s, 1H), 2.37 (s, 2H), 1.98 (t, J = 1.2 Hz, 5H), 1.75 (s, 2H). | 533.25 |
| (R)-N-(4-(4-amino-5-(4-(indoline-1-carbonyl)cyclohex-1-enyl)-7-methyl-7H-pyrrolo[2,3-d]pyrimidin-6-yl)phenyl) methacrylamide | 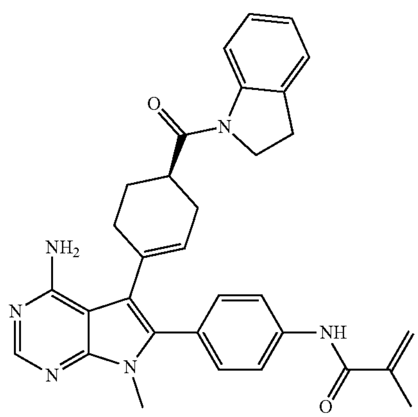 [SMILES: C=C(C)C(=O)Nc1ccc(-c2c(C3=CC[C@H](C(=O)N4CCc5ccccc54)CC3)c3c(N)ncnc3n2C)cc1] | $^1$H NMR (400 MHz, DMSO-d$_6$) δ 9.95 (s, 1H), 8.13 (d, J = 8.7 Hz, 2H), 7.82 (d, J = 8.6 Hz, 2H), 7.52-7.39 (m, 2H), 7.23 (d, J = 7.4 Hz, 1H), 7.14 (t, J = 7.7 Hz, 1H), 6.99 (t, J = 7.4 Hz, 1H), 6.57 (s, 2H), 5.83 (d, J = 7.2 Hz, 2H), 5.55 (s, 1H), 4.32-4.02 (m, 2H), 3.59 (s, 3H), 3.14 (t, J = 8.5 Hz, 2H), 3.01 (s, 1H), 2.37 (s, 2H), 1.98 (t, J = 1.2 Hz, 5H), 1.75 (s, 2H). | 533.30 |
| N-(4-(4-amino-7-methyl-5-((S)-4-((R)-2-methylpiperidine-1-carbonyl)cyclohex-1-en-1-yl)-7H-pyrrolo[2,3-d]pyrimidin-6-yl)phenyl) methacrylamide | 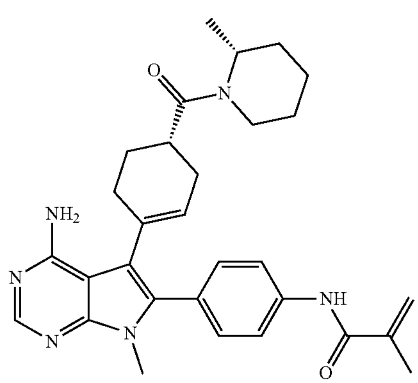 [SMILES: C=C(C)C(=O)Nc1ccc(-c2c(C3=CC[C@@H](C(=O)N4CCCC[C@H]4C)CC3)c3c(N)ncnc3n2C)cc1] | $^1$H NMR (400 MHz, DMSO-d$_6$) δ 9.95 (s, 1H), 8.10 (s, 1H), 7.81 (d, J = 8.5 Hz, 2H), 7.43 (d, J = 8.3 Hz, 2H), 6.54 (s, 2H), 5.83 (s, 1H), 5.79-5.71 (m, 1H), 5.55 (s, 1H), 4.74 (s, 1H), 4.30 (s, 1H), 3.58 (s, 3H), 3.05 (dd, J = 31.8, 9.0 Hz, 2H), 2.36-2.11 (m, 2H), 1.97 (s, 3H), 1.87-1.70 (m, 2H), 1.72-1.34 (m, 7H), 1.35-1.12 (m, 2H), 1.05 (d, J = 6.9 Hz, 2H). | 513.30 |

TABLE 11-continued

Additional Exemplary Compounds

| Compound | Structure | Proton NMR | MS [M + 1] |
|---|---|---|---|
| N-(4-(5-((S)-4-((1s,5r)-2-azabicyclo[3.1.0]hexane-2-carbonyl)cyclohex-1-en-1-yl)-4-amino-7-methyl-7H-pyrrolo[2,3-d]pyrimidin-6-yl)phenyl)methacrylamide | 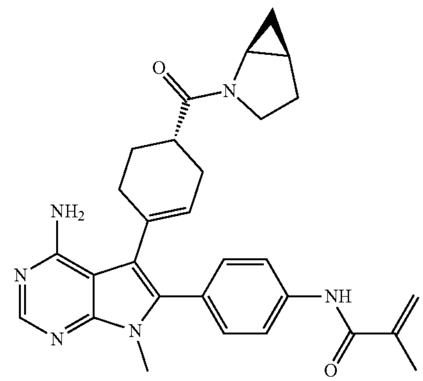 [SMILES: C=C(C)C(=O)Nc1ccc(-c2c(C3=CC[C@@H](C(=O)N4CC[C@@H]5C[C@@H]54)CC3)c3c(N)ncnc3n2C)cc1] | ¹H NMR (400 MHz, DMSO-d₆) δ 9.96 (d, J = 2.1 Hz, 1H), 8.10 (s, 1H), 7.81 (dt, J = 8.8, 2.2 Hz, 2H), 7.49-7.40 (m, 2H), 6.55 (s, 1H), 5.84 (t, J = 1.0 Hz, 1H), 5.78 (d, J = 9.9 Hz, 1H), 5.56 (d, J = 1.7 Hz, 1H), 3.80-3.65 (m, 1H), 3.59 (s, 4H), 3.17 (dd, J = 19.5, 9.2 Hz, 1H), 2.96 (dt, J = 12.5, 8.6 Hz, 1H), 2.44-2.20 (m, 2H), 2.19-1.99 (m, 1H), 1.98 (d, J = 1.2 Hz, 3H), 1.95-1.73 (m, 3H), 1.75-1.48 (m, 2H), 0.85-0.67 (m, 1H), 0.61-0.47 (m, 1H). | 497.25 |
| (S)-N-(4-(5-(4-(2-azabicyclo[2.1.1]hexane-2-carbonyl)cyclohex-1-en-1-yl)-4-amino-7-methyl-7H-pyrrolo[2,3-d]pyrimidin-6-yl)phenyl)methacrylamide | 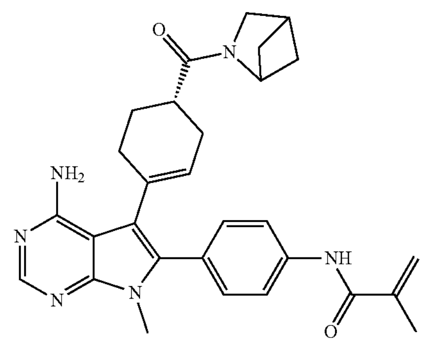 [SMILES: C=C(C)C(=O)Nc1ccc(-c2c(C3=CC[C@@H](C(=O)N4CC5CC4C5)CC3)c3c(N)ncnc3n2C)cc1] | 1H NMR (400 MHz, DMSO-d6) δ 9.95 (d, J = 1.8 Hz, 1H), 8.10 (d, J = 2.3 Hz, 1H), 7.81 (dd, J = 8.7, 2.2 Hz, 2H), 7.43 (dd, J = 8.7, 3.1 Hz, 2H), 6.55 (s, 1H), 5.83 (s, 1H), 5.77 (d, J = 6.0 Hz, 1H), 5.55 (s, 1H), 4.56 (dd, J = 21.1, 7.0 Hz, 1H), 3.58 (s, 3H), 3.51-3.41 (m, 1H), 3.24 (d, J = 4.3 Hz, 1H), 2.98-2.78 (m, 2H), 2.73 (q, J = 6.1 Hz, 1H), 2.37-2.13 (m, 2H), 1.98 (d, J = 1.2 Hz, 4H), 1.90 (s, 3H), 1.66 (d, J = 6.2 Hz, 1H), 1.58 (s, 1H), 1.38-1.19 (m, 2H). | 497.25 |
| N-(4-(4-amino-5-((S)-4-((S)-2-(methoxymethyl)pyrrolidine-1-carbonyl)cyclohex-1-en-1-yl)-7-methyl-7H-pyrrolo[2,3-d]pyrimidin-6-yl)phenyl)methacrylamide | 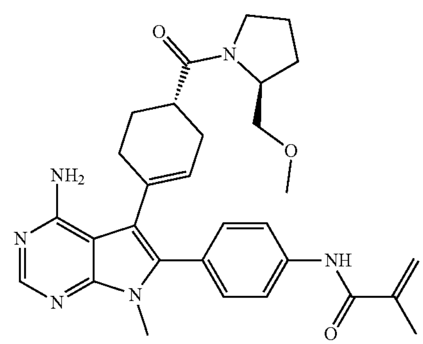 [SMILES: C=C(C)C(=O)Nc1ccc(-c2c(C3=CC[C@@H](C(=O)N4CCC[C@H]4COC)CC3)c3c(N)ncnc3n2C)cc1] | 1H NMR (400 MHz, DMSO-d6) δ 9.94 (s, 1H), 8.10 (d, J = 5.0 Hz, 1H), 7.84-7.76 (m, 2H), 7.53-7.39 (m, 2H), 6.59 (s, 2H), 5.85-5.81 (m, 1H), 5.77 (s, 1H), 5.55 (d, J = 1.7 Hz, 1H), 4.08 (dd, J = 7.4, 3.7 Hz, 1H), 3.58 (s, 3H), 3.56-3.47 (m, 1H), 3.46-3.35 (m, 2H), 3.28 (d, J = 4.0 Hz, 1H), 3.18 (s, 3H), 2.93-2.81 (m, 1H), 2.39-2.27 (m, 0H), 2.20 (d, J = 18.4 Hz, 1H), 1.98 (t, J = 1.3 Hz, 3H), 1.95-1.74 (m, 6H), 1.63 (d, J = 18.3 Hz, 2H). | 529.30 |
| (S)-N-(4-(4-amino-5-(4-(azepane-1-carbonyl)cyclohex-1-en-1-yl)-7-methyl-7H-pyrrolo[2,3-d]pyrimidin-6-yl)phenyl)methacrylamide | 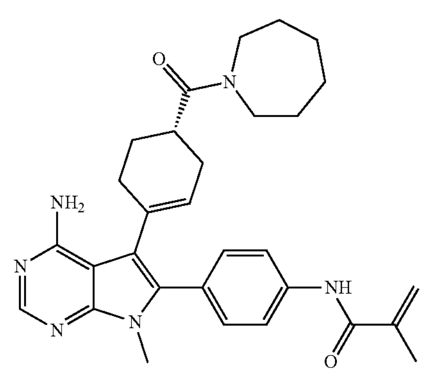 [SMILES: C=C(C)C(=O)Nc1ccc(-c2c(C3=CC[C@@H](C(=O)N4CCCCCC4)CC3)c3c(N)ncnc3n2C)cc1] | ¹H NMR (400 MHz, DMSO-d₆) δ 9.93 (s, 1H), 8.10 (s, 1H), 7.80 (d, J = 8.7 Hz, 2H), 7.43 (d, J = 8.6 Hz, 2H), 6.52 (s, 2H), 5.83 (s, 1H), 5.76 (s, 1H), 5.55 (s, 1H), 3.58 (s, 3H), 3.55-3.33 (m, 4H), 2.96 (s, 1H), 2.24 (t, J = 17.8 Hz, 2H), 1.97 (d, J = 1.3 Hz, 3H), 1.92 (s, 1H), 1.87 (s, 1H), 1.67 (d, J = 6.0 Hz, 2H), 1.61 (d, J = 6.5 Hz, 4H), 1.48 (s, 4H). | 513.35 |

TABLE 11-continued

Additional Exemplary Compounds

| Compound | Structure | Proton NMR | MS [M + 1] |
|---|---|---|---|
| (R)-N-(4-(5-(4-(2-azabicyclo[2.1.1]hexane-2-carbonyl)cyclohex-1-en-1-yl)-4-amino-7-methyl-7H-pyrrolo[2,3-d]pyrimidin-6-yl)phenyl)methacrylamide | 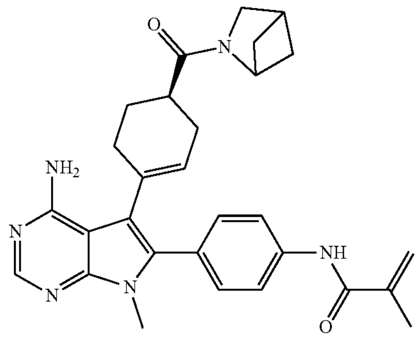 [SMILES: C=C(C)C(=O)Nc1ccc(-c2c(C3=CC[C@H](C(=O)N4CC5CC4C5)CC3)c3c(N)ncnc3n2C)cc1] | 1H NMR (400 MHz, DMSO-d6) δ 9.95 (d, J = 1.8 Hz, 1H), 8.10 (d, J = 2.3 Hz, 1H), 7.81 (dd, J = 8.7, 2.2 Hz, 2H), 7.43 (dd, J = 8.7, 3.1 Hz, 2H), 6.55 (s, 1H), 5.83 (s, 1H), 5.77 (d, J = 6.0 Hz, 1H), 5.55 (s, 1H), 4.56 (dd, J = 21.1, 7.0 Hz, 1H), 3.58 (s, 3H), 3.51-3.41 (m, 1H), 3.24 (d, J = 4.3 Hz, 1H), 2.98-2.78 (m, 2H), 2.73 (q, J = 6.1 Hz, 1H), 2.37-2.13 (m, 2H), 1.98 (d, J = 1.2 Hz, 4H), 1.90 (s, 3H), 1.66 (d, J = 6.2 Hz, 1H), 1.58 (s, 1H), 1.38-1.19 (m, 2H). | 497.25 |
| N-(4-(4-amino-5-((R)-4-((S)-2-(methoxymethyl)pyrrolidine-1-carbonyl)cyclohex-1-en-1-yl)-7-methyl-7H-pyrrolo[2,3-d]pyrimidin-6-yl)phenyl)methacrylamide | 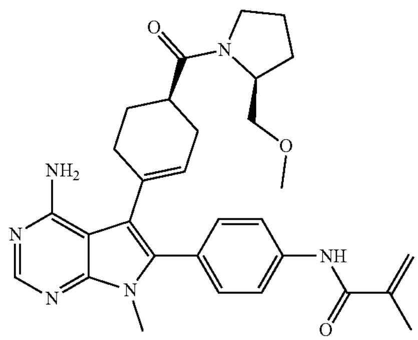 [SMILES: C=C(C)C(=O)Nc1ccc(-c2c(C3=CC[C@H](C(=O)N4CCC[C@H]4COC)CC3)c3c(N)ncnc3n2C)cc1] | 1H NMR (400 MHz, DMSO-d6) δ 9.94 (s, 1H), 8.10 (d, J = 5.0 Hz, 1H), 7.84-7.76 (m, 2H), 7.53-7.39 (m, 2H), 6.59 (s, 2H), 5.85-5.81 (m, 1H), 5.77 (s, 1H), 5.55 (d, J = 1.7 Hz, 1H), 4.08 (dd, J = 7.4, 3.7 Hz, 1H), 3.58 (s, 3H), 3.56-3.47 (m, 1H), 3.46-3.35 (m, 2H), 3.28 (d, J = 4.0 Hz, 1H), 3.18 (s, 3H), 2.93-2.81 (m, 1H), 2.39-2.27 (m, 0H), 2.20 (d, J = 18.4 Hz, 1H), 1.98 (t, J = 1.3 Hz, 3H), 1.95-1.74 (m, 6H), 1.63 (d, J = 18.3 Hz, 2H). | 529.30 |
| (R)-N-(4-(4-amino-5-(4-(azepane-1-carbonyl)cyclohex-1-en-1-yl)-7-methyl-7H-pyrrolo[2,3-d]pyrimidin-6-yl)phenyl)methacrylamide | 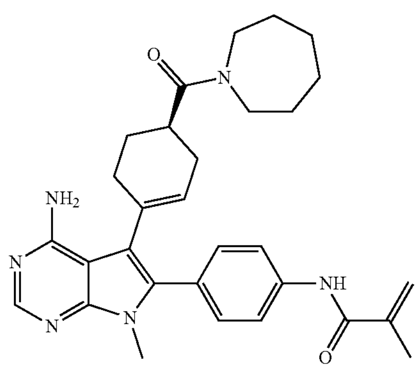 [SMILES: C=C(C)C(=O)Nc1ccc(-c2c(C3=CC[C@H](C(=O)N4CCCCCC4)CC3)c3c(N)ncnc3n2C)cc1] | $^1$H NMR (400 MHz, DMSO-d$_6$) δ 9.93 (s, 1H), 8.11 (s, 1H), 7.80 (d, J = 8.7 Hz, 2H), 7.43 (d, J = 8.6 Hz, 2H), 6.57 (s, 2H) 5.83 (s, 1H), 5.76 (s, 1H), 5.55 (s, 1H), 3.58 (s, 3H), 3.53-3.41 (m, 2H), 3.44-3.30 (m, 2H), 2.96 (s, 1H), 2.39-2.04 (m, 2H), 1.97 (d, J = 1.3 Hz, 3H), 1.87 (s, 2H), 1.67 (d, J = 5.8 Hz, 2H), 1.60 (d, J = 6.5 H, 4H), 1.49 (s, 4H). | 513.30 |
| N-(4-(4-amino-7-methyl-5-((R)-4-((R)-2-methylpiperidine-1-carbonyl)cyclohex-1-en-1-yl)-7H-pyrrolo[2,3-d]pyrimidin-6-yl)phenyl)methacrylamide | 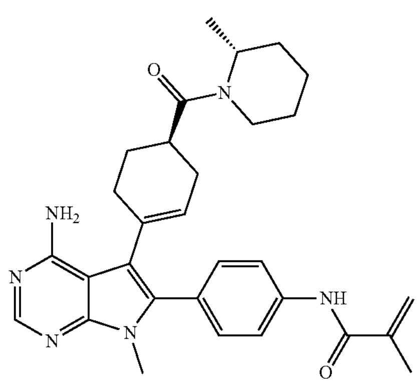 [SMILES: C=C(C)C(=O)Nc1ccc(-c2c(C3=CC[C@H](C(=O)N4CCCC[C@H]4C)CC3)c3c(N)ncnc3n2C)cc1] | $^1$H NMR (400 MHz, DMSO-d$_6$) δ 9.94 (s, 1H), 8.09 (s, 1H), 7.87-7.75 (m, 2H), 7.51-7.29 (m, 2H), 6.57 (s, 2H), 5.83 (t, J = 1.1 Hz, 1H), 5.76 (t, J = 1.9 Hz, 1H), 5.55 (s, 1H), 4.77 (s, 1H), 4.28-3.67 (m, 1H), 3.58 (s, 3H), 3.15-2.58 (m, 2H), 2.42-2.11 (m, 2H), 1.97 (d, J = 1.2 Hz, 3H), 1.80 (d, J = 13.6 Hz, 2H), 1.68-1.41 (m, 7H), 1.11 (dd, J = 78.3, 6.8 Hz, 4H). | 513.30 |

TABLE 11-continued

Additional Exemplary Compounds

| Compound | Structure | Proton NMR | MS [M + 1] |
| --- | --- | --- | --- |
| N-(4-(5-((R)-4-((1s,5r)-2-azabicyclo[3.1.0]hexane-2-carbonyl)cyclohex-1-en-1-yl)-4-amino-7-methyl-7H-pyrrolo[2,3-d]pyrimidin-6-yl)phenyl)methacrylamide | 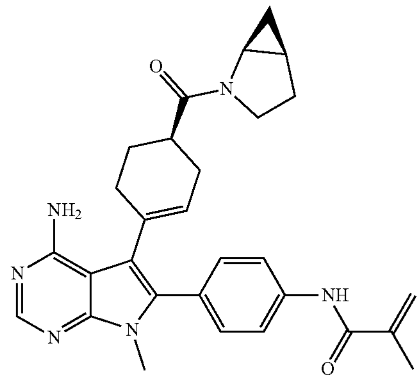 [SMILES: C=C(C)C(=O)Nc1ccc(-c2c(C3=CC[C@H](C(=O)N4CC[C@@H]5C[C@@H]54)CC3)c3c(N)ncnc3n2C)cc1] | ¹H NMR (400 MHz, DMSO-d₆) δ 9.95 (s, 1H), 8.10 (d, J = 1.0 Hz, 1H), 7.91-7.64 (m, 2H), 7.44 (dq, J = 8.7, 2.1, 1.5 Hz, 2H), 6.71-6.31 (m, 1H), 5.83 (s, 1H), 5.77 (d, J = 3.6 Hz, 1H), 5.56 (t, J = 1.4 Hz, 1H), 3.72-3.61 (m, 1H), 3.59 (d, J = 0.9 Hz, 3H), 3.49 (d, J = 5.9 Hz, 1H), 3.18-2.64 (m, 2H), 2.45-2.19 (m, 2H), 2.19-1.77 (m, 8H), 1.69 (dd, J = 13.2, 6.6 Hz, 2H), 1.55 (dd, J = 28.9, 6.9 Hz, 1H), 0.88-0.73 (m, 1H), 0.63-0.51 (m, 1H). | 497.25 |
| N-(4-(5-((S)-4-((1r,5s)-2-azabicyclo[3.1.0]hexane-2-carbonyl)cyclohex-1-en-1-yl)-4-amino-7-methyl-7H-pyrrolo[2,3-d]pyrimidin-6-yl)phenyl)methacrylamide | 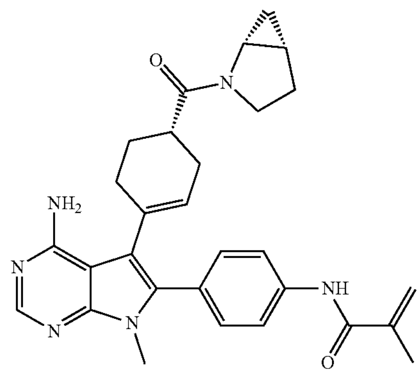 [SMILES: C=C(C)C(=O)Nc1ccc(-c2c(C3=CC[C@@H](C(=O)N4CC[C@H]5C[C@H]54)CC3)c3c(N)ncnc3n2C)cc1] | ¹H NMR (400 MHz, DMSO-d₆) δ 9.95 (s, 1H), 8.10 (d, J = 1.0 Hz, 1H), 7.89-7.72 (m, 2H), 7.53-7.32 (m, 2H), 6.52 (s, 1H), 5.84 (d, J = 1.3 Hz, 1H), 5.77 (s, 1H), 5.56 (d, J = 1.9 Hz, 1H), 3.75-3.63 (m, 1H), 3.59 (d, J = 0.9 Hz, 3H), 3.49 (q, J = 6.5, 5.8 Hz, 1H), 3.22-2.63 (m, 2H), 2.41-2.14 (m, 2H), 2.13-2.01 (m, 1H), 2.00-1.97 (m, 3H), 1.96-1.81 (d, J = 6.3 Hz, 2H), 1.75-1.63 (m, 2H), 1.61-1.45 (m, 1H), 0.86-0.77 (m, 1H), 0.62-0.48 (m, 1H). | 497.30 |
| N-(4-(5-((R)-4-((1r,5s)-2-azabicyclo[3.1.0]hexane-2-carbonyl)cyclohex-1-en-1-yl)-4-amino-7-methyl-7H-pyrrolo[2,3-d]pyrimidin-6-yl)phenyl)methacrylamide | 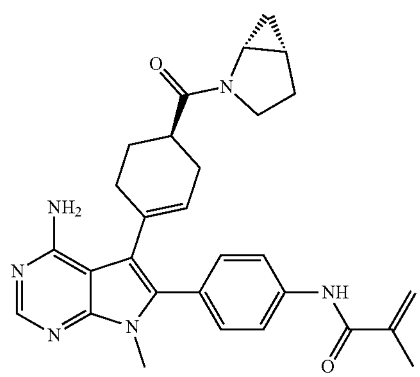 [SMILES: C=C(C)C(=O)Nc1ccc(-c2c(C3=CC[C@H](C(=O)N4CC[C@H]5C[C@H]54)CC3)c3c(N)ncnc3n2C)cc1] | ¹H NMR (400 MHz, DMSO-d₆) δ 9.95 (s, 1H), 8.10 (s, 1H), 7.81 (dt, J = 8.8, 2.1 Hz, 2H), 7.44 (d, J = 8.3 Hz, 2H), 6.54 (s, 1H), 5.83 (s, 1H), 5.77 (d, J = 9.8 Hz, 1H), 5.55 (s, 1H), 3.80-3.65 (m, 1H), 3.58 (s, 4H), 3.23-3.07 (m, 1H), 2.96-2.63 (m, 1H), 2.32 (q, J = 18.6, 18.0 Hz, 2H), 1.98 (m, 4H), 1.94-1.74 (m, 3H), 1.67 (ddd, J = 21.7, 11.2, 5.8 Hz, 2H), 0.77 (q, J = 7.4, 6.7 Hz, 1H), 0.69 (q, J = 6.7 Hz, 0H), 0.59-0.43 (m, 1H). | 497.25 |
| N-(4-(4-amino-7-methyl-5-((S)-4-((R)-2-methylpyrrolidine-1-carbonyl)cyclohex-1-en-1-yl)-7H-pyrrolo[2,3-d]pyrimidin-6-yl)phenyl)methacrylamide | 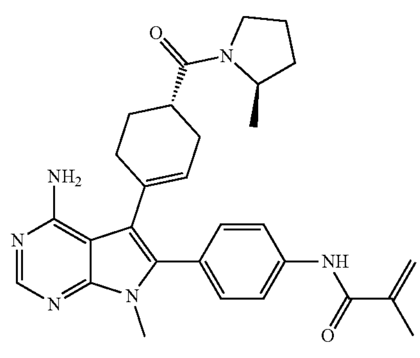 [SMILES: C=C(C)C(=O)Nc1ccc(-c2c(C3=CC[C@@H](C(=O)N4CCC[C@H]4C)CC3)c3c(N)ncnc3n2C)cc1] | ¹H NMR (400 MHz, DMSO-d₆) δ 9.94 (s, 1H), 8.09 (d, J = 4.8 Hz, 1H), 7.80 (d, J = 8.3 Hz, 2H), 7.47-7.39 (m, 2H), 6.59 (s, 2H), 5.83 (s, 1H), 5.77 (s, 1H), 5.55 (s, 1H), 4.03 (q, J = 9.6, 8.8 Hz, 1H), 3.58 (d, J = 2.2 Hz, 3H), 3.48 (q, J = 7.3, 6.4 Hz, 1H), 3.32 (s, 1H), 2.82 (s, 1H), 2.32 (d, J = 17.2 Hz, 1H), 2.20 (d, J = 17.1 Hz, 1H), 1.97 (s, 3H), 1.96-1.73 (m, 5H), 1.61 (s, 2H), 1.47 (s, 1H), 1.14 (d, J = 6.4 Hz, 1H), 1.04 (d, J = 6.3 Hz, 2H). | 499.25 |

TABLE 11-continued

Additional Exemplary Compounds

| Compound | Structure | Proton NMR | MS [M + 1] |
|---|---|---|---|
| N-(4-(4-amino-7-methyl-5-((S)-4-(S)-2-methylpyrrolidine-1-carbonyl)cyclohex-1-en-1-yl)-7H-pyrrolo[2,3-d]pyrimidin-6-yl)phenyl)methacrylamide | 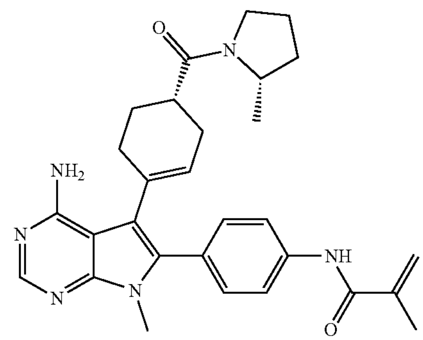 [SMILES: C=C(C)C(=O)Nc1ccc(-c2c(C3=CC[C@@H](C(=O)N4CCC[C@@H]4C)CC3)c3c(N)ncnc3n2C)cc1] | ¹H NMR (400 MHz, DMSO-d₆) δ 9.95 (s, 1H), 8.10 (d, J = 4.7 Hz, 1H), 7.84-7.77 (m, 2H), 7.43 (dd, J = 8.7, 2.1 Hz, 2H), 6.62 (s, 2H), 5.83 (s, 1H), 5.76 (d, J = 3.8 Hz, 1H), 5.55 (d, J = 1.9 Hz, 1H), 4.10-3.97 (m, 1H), 3.58 (d, J = 2.2 Hz, 3H), 3.48 (q, J = 6.8, 6.2 Hz, 1H), 2.83 (q, J = 5.4 Hz, 1H), 2.32 (d, J = 16.7 Hz, 1H), 2.20 (d, J = 18.7 Hz, 1H), 2.00-1.86 (m, 4H), 1.84 (s, 3H), 1.66-1.57 (m, 2H), 1.52-1.41 (m, 2H), 1.14 (d, J = 6.3 Hz, 1H), 1.05 (d, J = 6.2 Hz, 3H). | 499.30 |
| N-(4-(4-amino-5-((S)-4-((R)-2-cyclopropyl pyrrolidine-1-carbonyl)cyclohex-1-en-1-yl)-7-methyl-7H-pyrrolo[2,3-d]pyrimidin-6-yl)phenyl)methacrylamide | 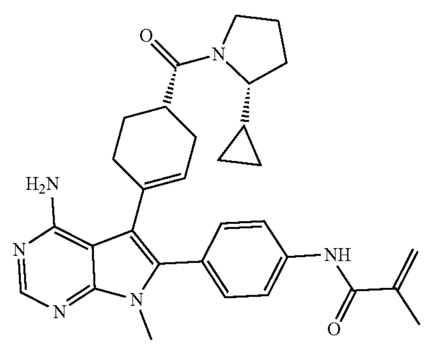 | ¹H NMR (400 MHz, DMSO-d6) 9.93 (s, 1H), 8.09 (d, J = 8.0 Hz, 1H), 7.83-7.77 (m, 2H), 7.43 (dd, J = 8.7, 2.7 Hz, 2H), 6.63-6.45 (m, 2H), 5.83 (t, J = 2.9 Hz, 1H), 5.77 (s, 1H), 5.57-5.52 (m, 1H), 3.80 (t, J = 7.5 Hz, 1H), 3.60-3.50 (s, 3H), 3.50-3.40 (s, 2H), 2.86 (s, 1H), 2.40-2.10 (m, 2H), 2.00-1.95 (s, 3H), 1.95-1.65 (m, 6H), 1.65-1.50 (s, 2H), 1.00-0.75 (m, 1H), 0.53-0.41 (m, 1H), 0.32-0.13 (m, 2H), 0.10 (dt, J = 9.8, 4.3 Hz, 1H), (m, 2H), 2.00-1.95 (s, 3H), 1.95-1.65 (m, 6H), 1.65-1.50 (s, 2H), 1.00-0.75 (m, 1H), 0.53-0.41 (m, 1H), 0.32-0.13 (m, 2H), 0.10 (dt, J = 9.8, 4.3 Hz, 1H). | 525.25 |
| N-(4-(4-amino-7-methyl-5-((R)-4-((R)-2-methylpyrrolidine-1-carbonyl)cyclohex-1-en-1-yl)-7H-pyrrolo[2,3-d]pyrimidin-6-yl)phenyl)methacrylamide | 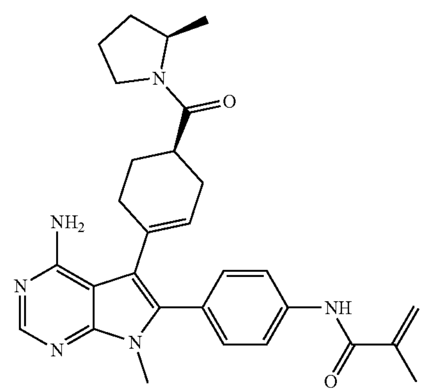 [SMILES: C=C(C)C(=O)Nc1ccc(-c2c(C3=CC[C@H](C(=O)N4CCC[C@H]4C)CC3)c3c(N)ncnc3n2C)cc1] | ¹H NMR (400 MHz, DMSO-d₆) δ 9.95 (s, 1H), 8.10 (d, J = 3.7 Hz, 1H), 7.81 (dd, J = 8.3, 3.9 Hz, 2H), 7.43 (dd, J = 8.7, 2.5 Hz, 2H), 6.46 (s, 2H), 5.83 (s, 1H), 5.75 (s, 1H), 5.55 (s, 1H), 4.05-3.96 (m, 1H), 3.58 (d, J = 1.9 Hz, 4H), 3.46-3.39 (m, 1H), 2.77 (s, 1H), 2.27-2.22 (m, 2H), 1.94 (d, J = 22.2 Hz, 8H), 1.60 (s, 2H), 1.49 (d, J = 7.6 Hz, 1H), 1.09 (dd, J = 8.2, 6.2 Hz, 3H). | 499.30 |
| N-(4-(4-amino-7-methyl-5-((R)-4-(S)-2-methylpyrrolidine-1-carbonyl)cyclohex-1-en-1-yl)-7H-pyrrolo[2,3-d]pyrimidin-6-yl)phenyl)methacrylamide | 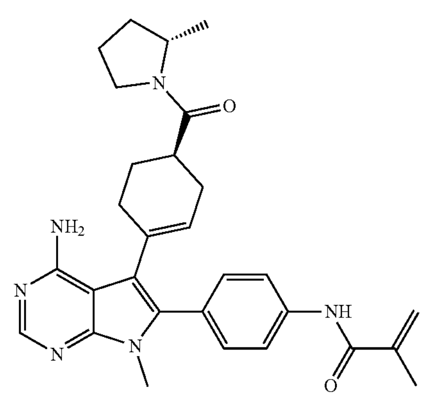 [SMILES: C=C(C)C(=O)Nc1ccc(-c2c(C3=CC[C@H](C(=O)N4CCC[C@@H]4C)CC3)c3c(N)ncnc3n2C)cc1] | ¹H NMR (400 MHz, DMSO-d₆) δ 9.95 (d, J = 2.0 Hz, 1H), 8.11 (d, J = 3.8 Hz, 1H), 7.81 (dq, J = 9.1, 2.1 Hz, 2H), 7.43 (dd, J = 8.8, 2.5 Hz, 2H), 6.46 (s, 2H), 5.83 (s, 1H), 5.79-5.72 (m, 1H), 5.55 (d, J = 1.9 Hz, 1H), 4.01 (td, J = 6.6, 2.7 Hz, 1H), 3.58 (d, J = 1.9 Hz, 3H), 3.44 (t, J = 7.9 Hz, 1H), 2.76 (dd, J = 12.2, 6.3 Hz, 1H), 2.25 (s, 2H), 1.97 (t, J = 1.2 Hz, 4H), 1.90 (s, 3H), 1.81 (s, 2H), 1.61 (s, 2H), 1.52-1.45 (m, 1H), 1.09 (dd, J = 8.2, 6.3 Hz, 3H). | 499.30 |

TABLE 11-continued

Additional Exemplary Compounds

| Compound | Structure | Proton NMR | MS [M + 1] |
|---|---|---|---|
| N-(4-(4-amino-5-((S)-4-((S)-2-cyclopropyl pyrrolidine-1-carbonyl)cyclohex-1-en-1-yl)-7-methyl-7H-pyrrolo[2,3-d]pyrimidin-6-yl)phenyl) methacrylamide | 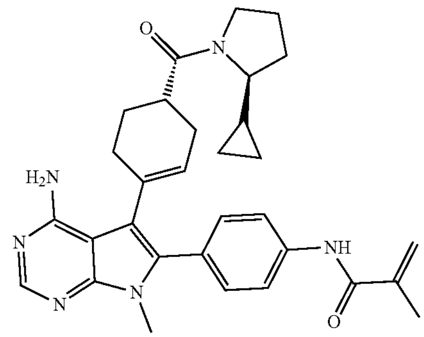 | $^1$H NMR (400 MHz, DMSO-d6) 9.94 (s, 1H), 8.11 (d, J = 2.6 Hz, 1H), 7.81 (dd, J = 8.5, 5.9 Hz, 2H), 7.43 (d, J = 8.4 Hz, 2H), 6.44 (s, 1H), 5.83 (s, 1H), 5.79-5.73 (m, 1H), 5.55 (t, J = 1.5 Hz, 1H), 3.75 (t, J = 7.0 Hz, 1H), 3.58 (d, J = 1.8 Hz, 3H), 3.55 (s, 1H), 3.55-3.42 (m, 1H), 2.78 (s, 1H), 2.27 (s, 1H), 2.22 (s, 1H), 1.97 (d, J = 1.3 Hz, 9H), 1.79 (d, J = 1.3 Hz, 3H) 0.91 (d, J = 7.8 Hz, 1H), 0.50 (dd, J = 9.6, 4.9 Hz, 1H), 0.35 (dddt, J = 27.8, 13.4, 9.3, 4.6 Hz, 2H), 0.13 (dt, J = 9.5, 4.8 Hz, 1H). | 525.25 |
| N-(4-(4-amino-5-((R)-4-((R)-2-cyclopropyl pyrrolidine-1-carbonyl)cyclohex-1-en-1-yl)-7-methyl-7H-pyrrolo[2,3-d]pyrimidin-6-yl)phenyl) methacrylamide | 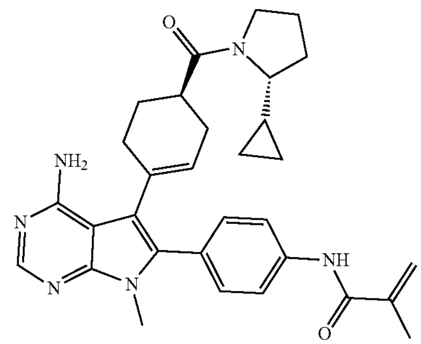 [SMILES: C=C(C)C(=O)Nc1ccc(-c2c(C3=CC[C@H](C(=O)N4CCC[C@@H]4C4CC4)CC3)c3c(N)ncnc3n2C)cc1] | 1H NMR (400 MHz, DMSO-d6) δ 9.95 (s, 1H), 8.09 (d, J = 8.2 Hz, 1H), 7.85-7.73 (m, 2H), 7.45-4.41 (m, 2H), 6.65 (s, 2H), 5.82 (d, J = 4.9 Hz, 1H), 5.77 (s, 1H), 5.55 (d, J = 1.8 Hz, 1H), 3.81-3.79 (m, 1H), 3.58 (s, 5H), 2.86 (s, 1H), 2.42-2.14 (m, 2H), 1.97 (d, J = 1.3 Hz, 2H), 1.88-1.67 (m, 4H), 1.67-1.55 (m, 2H), 0.87-0.85 (m, 1H), 0.47 (d, J = 4.3 Hz, 1H), 0.38-0.14 (m, 2H), 0.09 (d, J = 4.8 Hz, 1H). | 525.30 |
| N-(4-(4-amino-5-((R)-4-((S)-2-cyclopropyl pyrrolidine-1-carbonyl)cyclohex-1-en-1-yl)-7-methyl-7H-pyrrolo[2,3-d]pyrimidin-6-yl)phenyl) methacrylamide | 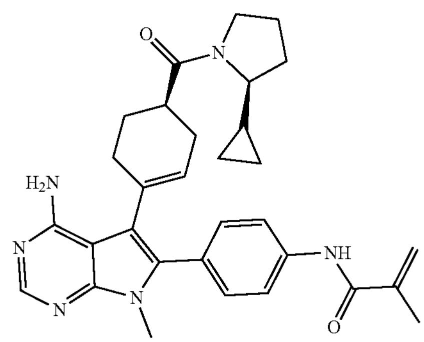 [SMILES: C=C(C)C(=O)Nc1ccc(-c2c(C3=CC[C@H](C(=O)N4CCC[C@H]4C4CC4)CC3)c3c(N)ncnc3n2C)cc1] | 1H NMR (400 MHz, DMSO-d6) δ 9.95 (s, 1H), 8.10 (d, J = 2.8 Hz, 1H), 7.87-7.75 (m, 2H), 7.43 (d, J = 8.3 Hz, 2H), 6.44 (s, 2H), 5.83 (s, 1H), 5.76 (s, 1H), 5.55 (d, J = 1.8 Hz, 1H), 3.74 (t, J = 7.2 Hz, 1H), 3.58 (d, J = 2.1 Hz, 4H), 3.46-3.40 (m, 1H), 2.79 (d, J = 7.2 Hz, 1H), 2.24 (d, J = 20.6 Hz, 2H), 2.02-1.88 (m, 6H), 1.89-1.50 (m, 5H), 0.95-0.86 (m, 1H), 0.55-0.25 (m, 3H), 0.15-0.11 (m, 1H). | 525.30 |
| N-(4-(4-amino-3-(3-fluoro-4-((4-methylpyrimidin-2-yl)oxy)phenyl)-1-methyl-1H-pyrrolo[3,2-c]pyridin-2-yl)phenyl) methacrylamide | 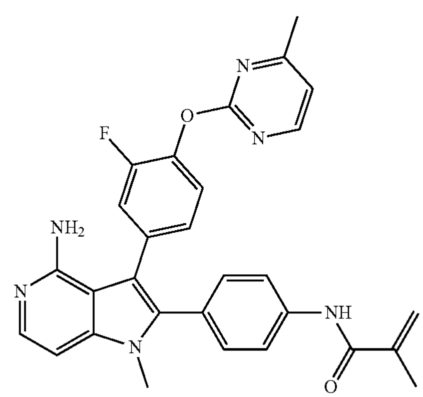 [SMILES: C=C(C)C(=O)Nc1ccc(-c2c(-c3ccc(Oc4nccc(C)n4)c(F)c3)c3c(N)nccc3n2C)cc1] | $^1$H NMR (400 MHz, DMSO-d$_6$) δ 9.92 (s, 1H), 8.48 (d, J = 5.0 Hz, 1H), 7.78-7.69 (m, 3H), 7.37-7.27 (m, 3H), 7.24-7.16 (m, 2H), 7.16-7.09 (m, 1H), 6.88 (d, J = 6.0 Hz, 1H), 5.80 (s, 1H), 5.54 (s, 1H), 5.15 (s, 2H), 3.57 (s, 3H), 2.42 (s, 3H), 1.96 (s, 3H). | 509.20 |

TABLE 11-continued

Additional Exemplary Compounds

| Compound | Structure | Proton NMR | MS [M + 1] |
|---|---|---|---|
| 4-(4-amino-2-(4-methacrylamidophenyl)-1-methyl-1H-pyrrolo[3,2-c]pyridin-3-yl)-N-(cyclobutylmethyl)-2-methoxybenzamide | 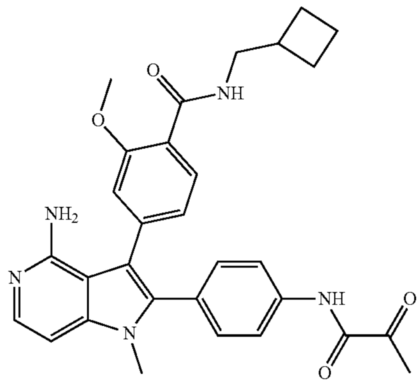 [SMILES: COc1cc(-c2c(-c3ccc(NC(=O)C(C)=O)cc3)n(C)c3ccnc(N)c23)ccc1C(=O)NCC1CCC1] | ¹H NMR (400 MHz, DMSO-d₆) δ 9.89 (s, 1H), 8.10 (t, J = 5.8 Hz, 1H), 7.75-7.66 (m, 3H), 7.64 (d, J = 7.8 Hz, 1H), 7.31-7.23 (m, 2H), 6.95 (d, J = 1.6 Hz, 1H), 6.91-6.84 (m, 2H), 5.80 (t, J = 1.2 Hz, 1H), 5.53 (t, J = 1.6 Hz, 1H), 5.18 (s, 2H), 3.73 (s, 3H), 3.57 (s, 3H), 3.29 (m, J = 12.0 Hz, 2H), 2.54 (d, J = 7.6 Hz, 1H), 2.04-1.92 (m, 5H), 1.89-1.78 (m, 2H), 1.78-1.65 (m, 2H). | 524.25 |
| N-(4-(4-amino-1-methyl-3-(4-((6-methylpyridin-2-yl)oxy)phenyl)-1H-pyrrolo[3,2-c]pyridin-2-yl)phenyl)acrylamide | 0.5 FA | 1H NMR (400 MHz, DMSO-d6) δ 10.26 (s, 1H), 8.15 (d, J = 1.2 Hz, 1H), 7.80-7.62 (m, 4H), 7.34-7.23 (m, 4H), 7.11-7.06 (m, 2H), 7.02 (d, J = 7.4 Hz, 1H), 6.99 (s, 1H), 6.77 (d, J = 8.1 Hz, 1H), 6.48-6.41 (m, 1H), 6.29-6.25 (m, 1H), 5.79-5.76 (m, 1H), 5.52 (s, 2H), 3.62 (s, 3H), 2.35 (s, 4H). | 476.20 |
| (S)-N-(4-(4-amino-1-methyl-3-(4-(pyrrolidine-1-carbonyl)cyclohex-1-en-1-yl)-1H-pyrrolo[3,2-c]pyridin-2-yl)phenyl)acrylamide | 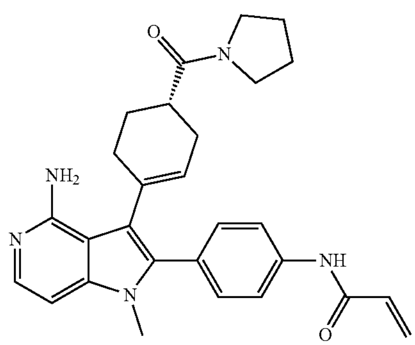 [SMILES: C=CC(=O)Nc1ccc(-c2c(C3=CC[C@@H](C(=O)N4CCCC4)CC3)c3c(N)nccc3n2C)cc1] | 1H NMR (400 MHz, DMSO-d6) δ 10.30 (s, 1H), 7.78 (d, J = 8.3 Hz, 2H), 7.62 (d, J = 5.9 Hz, 1H), 7.43 (d, J = 8.5 Hz, 2H), 6.74 (d, J = 6.2 Hz, 1H), 6.51-6.44 (m, 1H), 6.32-6.27 (m, 1H), 5.83-5.74 (m, 2H), 5.69 (s, 2H), 3.55 (d, J = 1.9 Hz, 3H), 3.52-3.41 (m, 1H), 3.30-3.22 (m, 2H), 2.79-2.64 (m, 1H), 2.38-2.16 (m, 2H), 2.04-1.82 (m, 4H), 1.76 (p, J = 6.6 Hz, 2H), 1.61 (d, J = 30.7 Hz, 2H). | 470.20 |
| (R)-N-(4-(4-amino-1-methyl-3-(4-(pyrrolidine-1-carbonyl)cyclohex-1-en-1-yl)-1H-pyrrolo[3,2-c]pyridin-2-yl)phenyl)acrylamide | 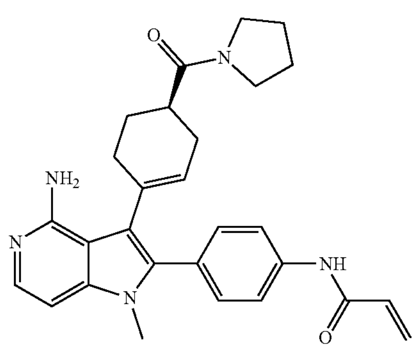 [SMILES: C=CC(=O)Nc1ccc(-c2c(C3=CC[C@H](C(=O)N4CCCC4)CC3)c3c(N)nccc3n2C)cc1] | 1H NMR (400 MHz, DMSO-d6) δ 10.30 (s, 1H), 7.78 (d, J = 8.3 Hz, 2H), 7.62 (d, J = 5.9 Hz, 1H), 7.43 (d, J = 8.5 Hz, 2H), 6.74 (d, J = 6.2 Hz, 1H), 6.51-6.44 (m, 1H), 6.32-6.27 (m, 1H), 5.83-5.74 (m, 2H), 5.69 (s, 2H), 3.55 (d, J = 1.9 Hz, 3H), 3.52-3.41 (m, 1H), 3.30-3.22 (m, 2H), 2.79-2.64 (m, 1H), 2.38-2.16 (m, 2H), 2.04-1.82 (m, 4H), 1.76 (p, J = 6.6 Hz, 2H), 1.61 (d, J = 30.7 Hz, 2H). | 470.25 |

TABLE 11-continued

Additional Exemplary Compounds

| Compound | Structure | Proton NMR | MS [M + 1] |
|---|---|---|---|
| (E)-N-(4-(4-amino-5-(3-fluoro-4-((4-methylpyrimidin-2-yl)oxy)phenyl)-7-methyl-7H-pyrrolo[2,3-d]pyrimidin-6-yl)phenyl)-4-(dimethylamino)but-2-enamide | 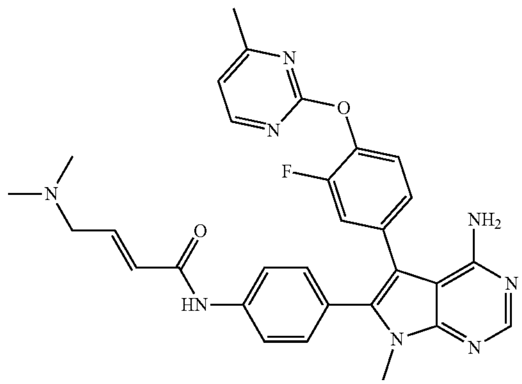 [SMILES: Cc1ccnc(Oc2ccc(-c3c(-c4ccc(NC(=O)/C=C/CN(C)C)cc4)n(C)c4ncnc(N)c34)cc2F)n1] | $^1$H NMR (400 MHz, DMSO-d$_6$) δ 10.22 (s, 1H), 8.48 (d, J = 5.0 Hz, 1H), 8.21 (s, 1H), 7.72 (d, J = 8.2 Hz, 2H), 7.33 (d, J = 8.4 Hz, 3H), 7.23-7.15 (m, 2H), 7.15-7.07 (m, 1H), 6.76 (dt, J = 15.1, 5.9 Hz, 1H), 6.29 (d, J = 15.4 Hz, 1H), 5.98 (s, 2H), 3.60 (s, 3H), 3.12 (d, J = 5.9 Hz, 2H), 2.42 (s, 3H), 2.22 (s, 6H). | 553.25 |
| (R,E)-N-(4-(4-amino-7-methyl-5-(4-(pyrrolidine-1-carbonyl)cyclohex-1-en-1-yl)-7H-pyrrolo[2,3-d]pyrimidin-6-yl)phenyl)-4-(dimethylamino)but-2-enamide | 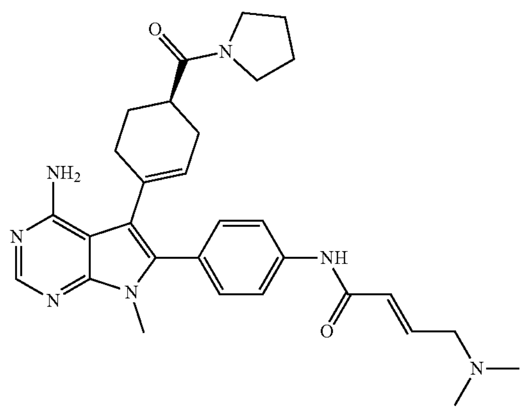 [SMILES: CN(C)C/C=C/C(=O)Nc1ccc(-c2c(C3=CC[C@H](C(=O)N4CCCC4)CC3)c3c(N)ncnc3n2C)cc1] | $^1$H NMR (400 MHz, DMSO-d$_6$) δ 10.23 (s, 1H), 8.10 (d, J = 1.8 Hz, 1H), 7.78 (d, J = 8.2 Hz, 2H), 7.51-7.38 (m, 2H), 6.77 (dt, J = 15.3, 5.9 Hz, 1H), 6.53 (s, 2H), 6.32 (d, J = 15.4 Hz, 1H), 5.84-5.72 (m, 1H), 3.58 (s, 3H), 3.56-3.47 (m, 1H), 3.47-3.39 (m, 1H), 3.27 (dd, J = 16.0, 9.3 Hz, 3H), 3.11 (d, J = 5.9 Hz, 2H), 2.84 (q, J = 6.0 Hz, 1H), 2.27 (d, J = 14.7 Hz, 2H), 2.22 (s, 6H), 1.87 (dt, J = 13.3, 6.4 Hz, 4H), 1.76 (p, J = 6.7 Hz, 2H), 1.63 (q, J = 6.4 Hz, 2H). | 528.40 |
| (S,E)-N-(4-(4-amino-7-methyl-5-(4-(pyrrolidine-1-carbonyl)cyclohex-1-en-1-yl)-7H-pyrrolo[2,3-d]pyrimidin-6-yl)phenyl)-4-(dimethylamino)but-2-enamide | 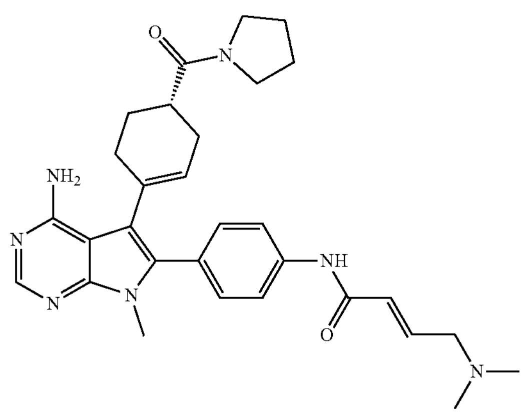 [SMILES: CN(C)C/C=C/C(=O)Nc1ccc(-c2c(C3=CC[C@@H](C(=O)N4CCCC4)CC3)c3c(N)ncnc3n2C)cc1] | $^1$H NMR (400 MHz, DMSO-d$_6$) δ 10.23 (s, 1H), 8.10 (d, J = 1.7 Hz, 1H), 7.77 (d, J = 8.2 Hz, 2H), 7.47-7.40 (m, 2H), 6.77 (dt, J = 15.4, 5.9 Hz, 1H), 6.53 (s, 2H), 6.31 (d, J = 15.3 Hz, 1H), 5.76 (d, J = 4.5 Hz, 1H), 3.58 (d, J = 1.8 Hz, 3H), 3.56-3.48 (m, 1H), 3.47-3.38 (m, 1H), 3.32-3.21 (m, 1H), 3.10 (d, J = 5.8 Hz, 2H), 2.83 (p, J = 6.0 Hz, 1H), 2.40-2.23 (m, 2H), 2.21 (s, 6H), 1.87 (dt, J = 13.2, 6.4 Hz, 4H), 1.76 (p, J = 6.5 Hz, 2H), 1.63 (d, J = 6.3 Hz, 2H). | 528.35 |

TABLE 11-continued

Additional Exemplary Compounds

| Compound | Structure | Proton NMR | MS [M + 1] |
|---|---|---|---|
| (E)-N-(4-(4-amino-7-methyl-5-(4-((4-methylpyrimidin-2-yl)oxy)phenyl)-7H-pyrrolo[2,3-d]pyrimidin-6-yl)phenyl)-4-(dimethylamino)but-2-enamide | 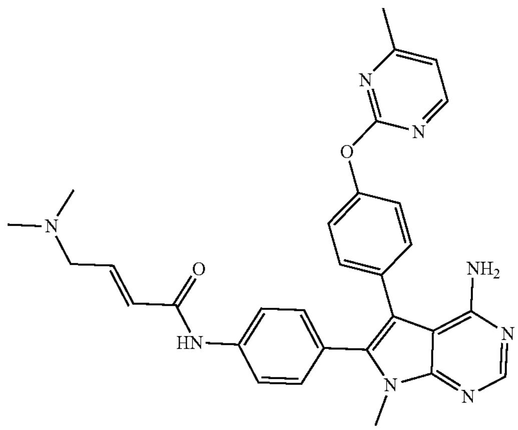 [SMILES: Cc1ccnc(Oc2ccc(-c3c(-c4ccc(NC(=O)/C=C/CN(C)C)cc4)n(C)c4ncnc(N)c34)cc2)n1] | $^1$H NMR (400 MHz, DMSO-d$_6$) δ 10.18 (s, 1H), 8.47 (d, J = 5.0 Hz, 1H), 8.20 (s, 1H), 7.74-7.67 (m, 2H), 7.36-7.24 (m, 4H), 7.23-7.07 (m, 4H), 6.75 (dt, J = 15.4, 5.8 Hz, 1H), 6.28 (dt, J = 15.4, 1.6 Hz, 1H), 5.90 (s, 2H), 3.60 (s, 3H), 3.07 (dd, J = 5.9, 1.6 Hz, 2H), 2.41 (s, 3H), 2.19 (s, 7H). | 535.35 |
| (S)-N-(4-(4-amino-7-methyl-5-(4-(pyrrolidin-1-ylsulfonyl)cyclohex-1-en-1-yl)-7H-pyrrolo[2,3-d]pyrimidin-6-yl)-3-methylphenyl)methacrylamide | 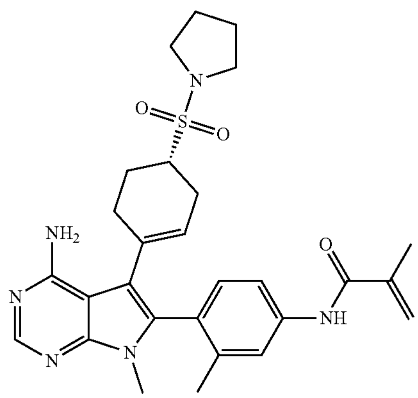 [SMILES: C=C(C)C(=O)Nc1ccc(-c2c(C3=CC[C@@H](S(=O)(=O)N4CCCC4)CC3)c3c(N)ncnc3n2C)c(C)c1] | $^1$H NMR (400 MHz, DMSO-d$_6$) δ 9.87 (s, 1H), 8.12 (s, 1H), 7.72 (dd, J = 13.0, 2.2 Hz, 1H), 7.63 (ddd, J = 13.1, 8.3, 2.2 Hz, 1H), 7.18 (dd, J = 12.5, 8.3 Hz, 1H), 6.35 (s, 2H), 5.83 (t, J = 1.1 Hz, 1H), 5.62 (s, 1H), 5.59-5.50 (m, 1H), 3.54 (d, J = 15.4 Hz, 1H), 3.34 (s, 3H), 3.31-3.24 (m, 4H), 2.37 (d, J = 30.0 Hz, 2H), 2.10-2.02 (m, 5H), 1.97 (t, J = 1.3 Hz, 3H), 1.95-1.79 (m, 5H), 1.56 (p, J = 10.8 Hz, 1H). | 535.25 |
| (R)-N-(4-(4-amino-7-methyl-5-(4-(pyrrolidin-1-ylsulfonyl)cyclohex-1-en-1-yl)-7H-pyrrolo[2,3-d]pyrimidin-6-yl)-3-methylphenyl)methacrylamide | 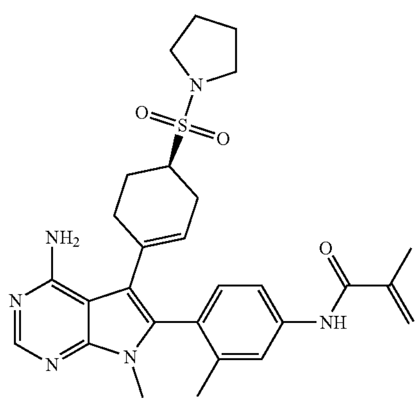 [SMILES: C=C(C)C(=O)Nc1ccc(-c2c(C3=CC[C@H](S(=O)(=O)N4CCCC4)CC3)c3c(N)ncnc3n2C)c(C)c1] | $^1$H NMR (400 MHz, DMSO-d$_6$) δ 9.92 (s, 1H), 8.40 (s, 1H), 7.78 (d, J = 2.1 Hz, 3H), 7.20 (dd, J = 9.9, 8.3 Hz, 1H), 5.84 (s, 1H), 5.71 (s, 1H), 5.56 (d, J = 1.9 Hz, 1H), 3.43 (d, J = 1.6 Hz, 4H), 3.31-3.23 (m, 4H), 2.42 (s, 2H), 2.06 (d, J = 3.6 Hz, 4H), 1.97 (t, J = 1.2 Hz, 4H), 1.94-1.82 (m, 5H), 1.60 (s, 1H). | 535.25 |
| (R)-N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)acrylamide | 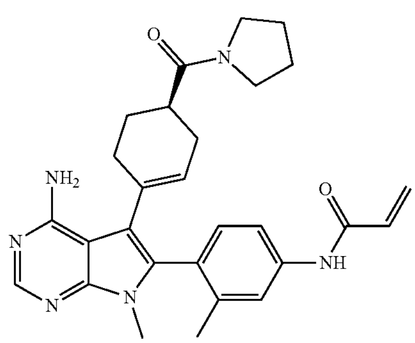 [SMILES: C=CC(=O)Nc1ccc(-c2c(C3=CC[C@H](C(=O)N4CCCC4)CC3)c3c(N)ncnc3n2C)c(C)c1] | 1H NMR (400 MHz, DMSO-d6) 10.24 (d, J = 1.5 Hz, 1H), 8.10 (s, 1H), 7.78-7.64 (m, 1H), 7.59 (ddd, J = 7.9, 5.5, 2.1 Hz, 1H), 7.20 (dd, J = 8.3, 6.5 Hz, 1H), 6.47 (dd, J = 17.0, 10.1 Hz, 2H), 6.29 (dd, J = 16.9, 2.0 Hz, 1H), 5.79 (dd, J = 10.1, 2.1 Hz, 1H), 5.67 (d, J = 15.5 Hz, 1H), 3.53-3.37 (m, 2H), 3.34 (s, 3H), 3.27 (q, J = 6.9 Hz, 2H), 2.73 (p, J = 6.2 Hz, 1H), 2.21 (q, J = 18.5 Hz, 2H), 1.93 (d, J = 14.5 Hz, 3H), 1.89-1.80 (m, 4H), 1.80-1.68 (m, 2H), 1.57 (d, J = 6.3 Hz, 2H). | 485.15 |

TABLE 11-continued

Additional Exemplary Compounds

| Compound | Structure | Proton NMR | MS [M + 1] |
|---|---|---|---|
| (S)-N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl) acrylamide | 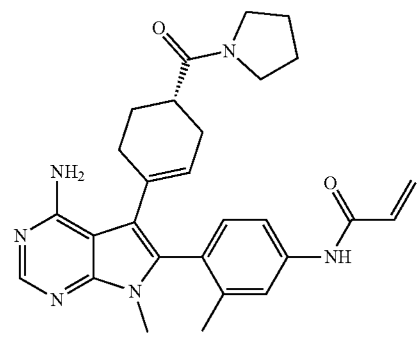 [SMILES: C=CC(=O)Nc1ccc(-c2c(C3=CC[C@@H](C(=O)N4CCCC4)CC3)c3c(N)ncnc3n2C)c(C)c1] | 1H NMR (400 MHz, DMSO-d6) 10.24 (d, J = 1.5 Hz, 1H), 8.10 (s, 1H), 7.78-7.64 (m, 1H), 7.59 (ddd, J = 7.9, 5.5, 2.1 Hz, 1H), 7.20 (dd, J = 8.3, 6.5 Hz, 1H), 6.47 (dd, J = 17.0, 10.1 Hz, 2H), 6.29 (dd, J = 16.9, 2.0 Hz, 1H), 5.79 (dd, J = 10.1, 2.1 Hz, 1H), 5.67 (d, J = 15.5 Hz, 1H), 3.53-3.37 (m, 2H), 3.34 (s, 3H), 3.27 (q, J = 6.9 Hz, 2H), 2.73 (p, J = 6.2 Hz, 1H), 2.21 (q, J = 18.5 Hz, 2H), 1.93 (d, J = 14.5 Hz, 3H), 1.89-1.80 (m, 4H), 1.80-1.68 (m, 2H), 1.57 (d, J = 6.3 Hz, 2H). | 485.15 |
| N-(4-(4-amino-7-methyl-5-(4-(4-methyl-1H-pyrazol-1-yl)phenyl)-7H-pyrrolo[2,3-d]pyrimidin-6-yl)phenyl) methacrylamide | 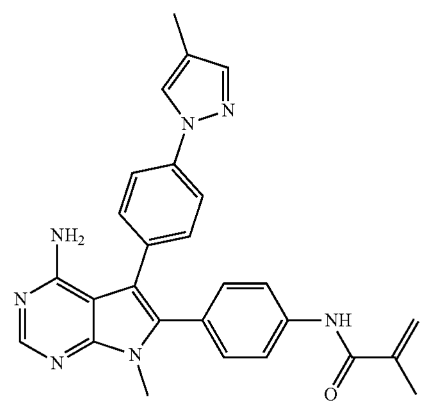 [SMILES: C=C(C)C(=O)Nc1ccc(-c2c(-c3ccc(-n4cc(C)cn4)cc3)c3c(N)ncnc3n2C)cc1] | $^1$H NMR (400 MHz, DMSO-d$_6$) δ 9.89 (s, 1H), 8.26 (s, 1H), 8.20 (s, 1H), 7.79-7.66 (m, 4H), 7.56 (s, 1H), 7.34-7.25 (m, 4H), 5.89 (s, 2H), 5.79 (t, J = 1.0 Hz, 1H), 5.53 (t, J = 1.5 Hz, 1H), 3.62 (s, 3H), 2.10 (s, 3H), 1.94 (t, J = 1.2 Hz, 3H). | 464.10 |
| N-(4-(4-amino-7-methyl-5-(6-(3-methyl-1H-pyrazol-1-yl)pyridin-3-yl)-7H-pyrrolo[2,3-d]pyrimidin-6-yl)phenyl) methacrylamide | 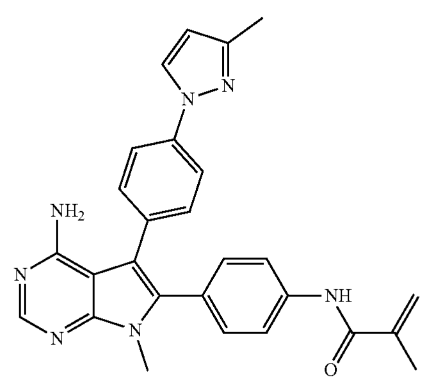 [SMILES: C=C(C)C(=O)Nc1ccc(-c2c(-c3ccc(-n4ccc(C)n4)cc3)c3c(N)ncnc3n2C)cc1] | $^1$H NMR (400 MHz, DMSO-d$_6$) δ 9.90 (s, 1H), 8.47 (d, J = 2.5 Hz, 1H), 8.25-8.15 (m, 2H), 7.80 (dd, J = 8.4, 0.8 Hz, 1H), 7.77-7.68 (m, 3H), 7.33-7.25 (m, 2H), 6.37 (d, J = 2.5 Hz, 1H), 6.09 (s, 2H), 5.82-5.77 (m, 1H), 5.55-5.50 (m, 1H), 3.62 (s, 3H), 2.29 (s, 3H), 1.95 (t, J = 1.2 Hz, 3H). | 465.30 |

TABLE 11-continued

Additional Exemplary Compounds

| Compound | Structure | Proton NMR | MS [M + 1] |
|---|---|---|---|
| N-(4-(4-amino-7-methyl-5-(4-(4-(trifluoromethyl)-1H-pyrazol-1-yl)phenyl)-7H-pyrrolo[2,3-d]pyrimidin-6-yl)phenyl)methacrylamide | 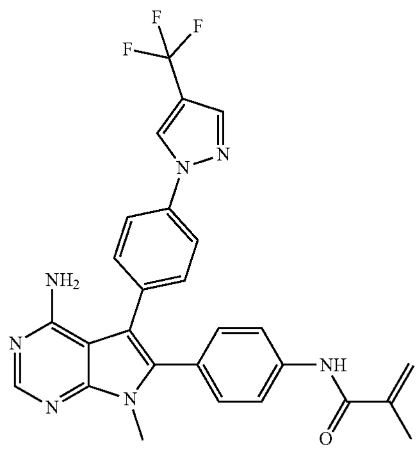 [SMILES: C=C(C)C(=O)Nc1ccc(-c2c(-c3ccc(-n4cc(C(F)(F)F)cn4)cc3)c3c(N)ncnc3n2C)cc1] | $^1$H NMR (400 MHz, DMSO-d$_6$) δ 9.89 (s, 1H), 9.20-9.15 (m, 1H), 8.21 (d, J = 1.2 Hz, 2H), 7.91-7.83 (m, 2H), 7.75-7.68 (m, 2H), 7.41-7.34 (m, 2H), 7.33-7.25 (m, 2H), 5.95 (s, 2H), 5.81-5.76 (m, 1H), 5.56-5.50 (m, 1H), 3.62 (s, 3H), 1.95 (t, J = 1.3 Hz, 3H). | 518.30 |
| N-(4-(4-amino-7-methyl-5-(6-(1-methyl-1H-pyrazol-3-yl)pyridin-3-yl)-7H-pyrrolo[2,3-d]pyrimidin-6-yl)phenyl)methacrylamide | 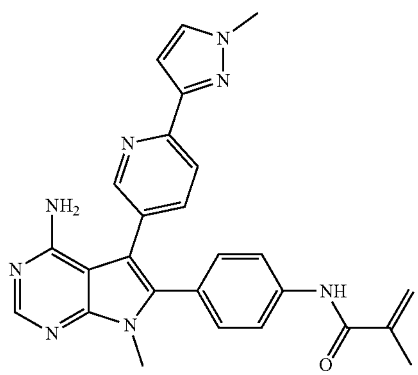 [SMILES: C=C(C)C(=O)Nc1ccc(-c2c(-c3ccc(-c4ccn(C)n4)nc3)c3c(N)ncnc3n2C)cc1] | $^1$H NMR (400 MHz, DMSO-d$_6$) δ 9.91 (s, 1H), 8.35-8.30 (m, 1H), 8.22 (s, 1H), 7.85 (dd, J = 8.2, 0.9 Hz, 1H), 7.79-7.69 (m, 3H), 7.63 (dd, J = 8.2, 2.3 Hz, 1H), 7.29 (d, J = 8.6 Hz, 2H), 6.77 (d, J = 2.2 Hz, 1H), 6.02 (s, 1H), 5.79 (s, 1H), 5.53 (s, 1H), 3.91 (s, 3H), 3.62 (s, 3H), 1.94 (t, J = 1.3 Hz, 3H). | 465.20 |
| N-(4-(4-amino-7-methyl-5-(6-(1-methyl-1H-pyrazol-5-yl)pyridin-3-yl)-7H-pyrrolo[2,3-d]pyrimidin-6-yl)phenyl)methacrylamide | 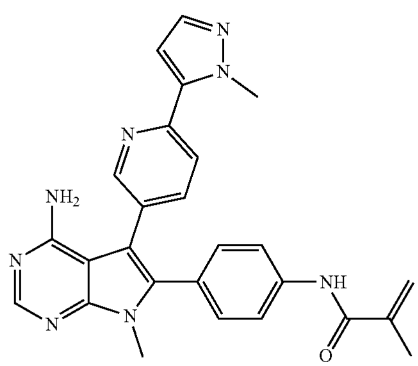 [SMILES: C=C(C)C(=O)Nc1ccc(-c2c(-c3ccc(-c4ccnn4C)nc3)c3c(N)ncnc3n2C)cc1] | $^1$H NMR (400 MHz, DMSO-d$_6$) δ 9.92 (s, 1H), 8.44 (dd, J = 2.3, 0.9 Hz, 1H), 8.23 (s, 1H), 7.81-7.70 (m, 3H), 7.69 (dd, J = 8.2, 2.3 Hz, 1H), 7.48 (d, J = 2.0 Hz, 1H), 7.35-7.28 (m, 2H), 6.80 (d, J = 2.0 Hz, 1H), 6.10 (s, 2H), 5.80 (t, J = 1.1 Hz, 1H), 5.54 (t, J = 1.4 Hz, 1H), 4.14 (s, 3H), 3.62 (s, 3H), 1.95 (t, J = 1.2 Hz, 3H). | 460.30 |
| N-(4-(5-(4-(1H-pyrazol-5-yl)phenyl)-4-amino-7-methyl-7H-pyrrolo[2,3-d]pyrimidin-6-yl)phenyl)methacrylamide | 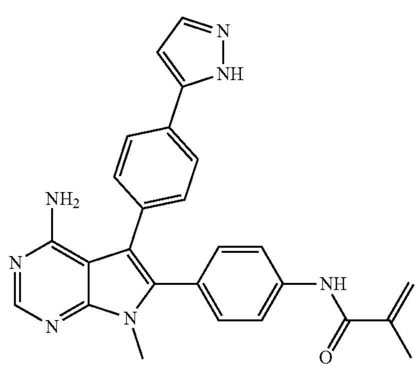 [SMILES: C=C(C)C(=O)Nc1ccc(-c2c(-c3ccc(-c4ccn[nH]4)cc3)c3c(N)ncnc3n2C)cc1] | $^1$H NMR (400 MHz, DMSO-d$_6$) δ 12.87 (1H, s), 9.88 (1H, s), 8.21 (1H, s), 7.84-7.62 (5H, m), 7.32-8211; 7.23 (4H, m), 6.72 (1H, d, J = 2.2 Hz), 5.79 (3H, s), 5.52 (1H, t, J = 1.5 Hz), 3.63 (3H, s), 1.95 (3H, d, J = 1.2 Hz) | 450.30 |

TABLE 11-continued

Additional Exemplary Compounds

| Compound | Structure | Proton NMR | MS [M + 1] |
| --- | --- | --- | --- |
| N-(4-(4-amino-7-methyl-5-(4-(5-methyl-1,2,4-oxadiazol-3-yl)phenyl)-7H-pyrrolo[2,3-d]pyrimidin-6-yl)phenyl)methacrylamide | 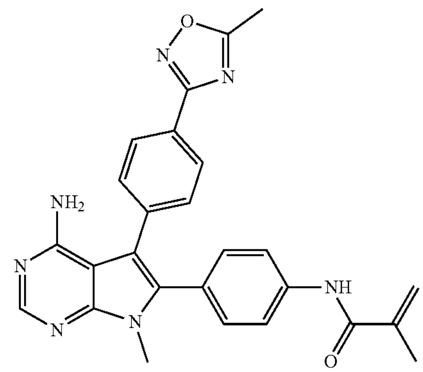 [SMILES: C=C(C)C(=O)Nc1ccc(-c2c(-c3ccc(-c4noc(C)n4)cc3)c3c(N)ncnc3n2C)cc1] | ¹H NMR (400 MHz, DMSO-d₆) δ 9.89 (s, 1H), 8.22 (s, 1H), 7.94 (d, J = 7.8 Hz, 2H), 7.71 (d, J = 8.2 Hz, 2H), 7.38 (d, J = 7.9 Hz, 2H), 7.27 (d, J = 8.2 Hz, 2H), 5.96 (s, 2H), 5.79 (s, 1H), 5.53 (s, 1H), 3.62 (s, 3H), 3.31 (s, 1H), 2.66 (s, 3H), 1.95 (s, 3H). | 466.35 |
| N-(4-(4-amino-7-methyl-5-(4-(5-methyl-1,3,4-oxadiazol-2-yl)phenyl)-7H-pyrrolo[2,3-d]pyrimidin-6-yl)phenyl)methacrylamide | 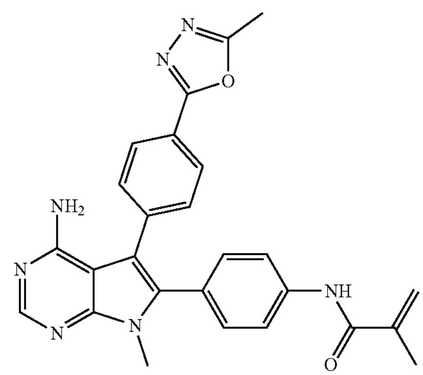 [SMILES: C=C(C)C(=O)Nc1ccc(-c2c(-c3ccc(-c4nnc(C)o4)cc3)c3c(N)ncnc3n2C)cc1] | ¹H NMR (400 MHz, DMSO-d₆) δ 9.91 (s, 1H), 8.22 (s, 1H), 7.92 (d, J = 7.9 Hz, 2H), 7.71 (d, J = 8.3 Hz, 2H), 7.40 (d, J = 7.9 Hz, 2H), 7.27 (d, J = 8.3 Hz, 2H), 5.99 (s, 2H), 5.79 (s, 1H), 5.53 (s, 1H), 3.62 (s, 3H), 3.32 (s, 1H), 2.57 (s, 3H), 1.95 (s, 3H). | 466.20 |
| N-(4-(4-amino-7-methyl-5-(2-methyl-2H-indazol-5-yl)-7H-pyrrolo[2,3-d]pyrimidin-6-yl)phenyl)methacrylamide | 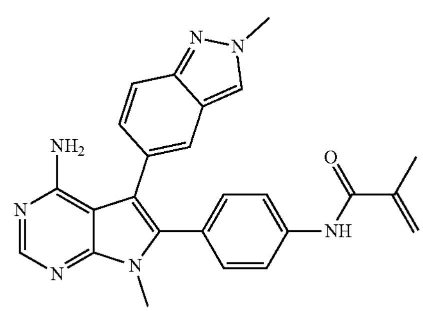 [SMILES: C=C(C)C(=O)Nc1ccc(-c2c(-c3ccc4nn(C)cc4c3)c3c(N)ncnc3n2C)cc1] | ¹H NMR (400 MHz, DMSO-d₆) δ 9.85 (s, 1H), 8.29 (s, 1H), 8.19 (s, 1H), 7.65 (d, J = 8.4 Hz, 2H), 7.55 (d, J = 9.2 Hz, 1H), 7.27 (d, J = 8.3 Hz, 2H), 7.07 (dd, J = 8.8, 1.8 Hz, 1H), 5.77 (s, 1H), 5.52 (s, 1H), 4.15 (s, 3H), 3.64 (s, 3H), 1.93 (s, 3H). | 438.15 |
| N-(4-(4-amino-7-methyl-5-(1,2,3,6-tetrahydro-[1,1'-biphenyl]-4-yl)-7H-pyrrolo[2,3-d]pyrimidin-6-yl)phenyl)methacrylamide | 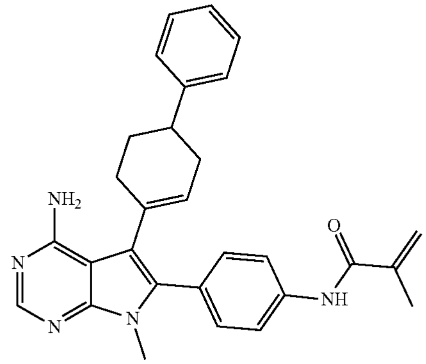 [SMILES: C=C(C)C(=O)Nc1ccc(-c2c(C3=CCC(c4ccccc4)CC3)c3c(N)ncnc3n2C)cc1] | ¹H NMR (400 MHz, DMSO-d₆) δ 9.97 (s, 1H), 8.14 (s, 1H), 7.88-7.80 (m, 2H), 7.50-7.42 (m, 2H), 7.34-7.23 (m, 4H), 7.23-7.14 (m, 1H), 6.29 (s, 1H), 5.89-5.82 (m, 2H), 5.56 (t, J = 1.4 Hz, 1H), 3.58 (s, 3H), 2.82 (dd, J = 10.7, 5.7 Hz, 1H), 2.42 (d, J = 17.3 Hz, 1H), 2.28 (d, J = 16.6 Hz, 1H), 2.14 (s, 1H), 1.98 (t, J = 1.2 Hz, 3H), 1.92 (d, J = 4.8 Hz, 1H), 1.77 (s, 2H). | 464.30 |

TABLE 11-continued

Additional Exemplary Compounds

| Compound | Structure | Proton NMR | MS [M + 1] |
|---|---|---|---|
| N-(4-(4-amino-7-methyl-5-(4-(3-methyl-1,2,4-oxadiazol-5-yl)cyclohex-1-en-1-yl)-7H-pyrrolo[2,3-d]pyrimidin-6-yl)phenyl)methacrylamide | 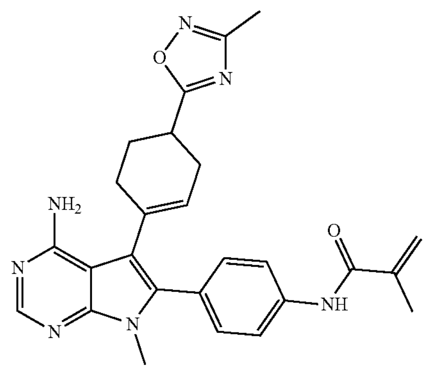 [SMILES: C=C(C)C(=O)Nc1ccc(-c2c(C3=CCC(c4nc(C)no4)CC3)c3c(N)ncnc3n2C)cc1] | $^1$H NMR (400 MHz, DMSO-d$_6$) δ 9.95 (s, 1H), 8.12 (s, 1H), 7.80 (d, J = 8.5 Hz, 2H), 7.42 (d, J = 8.3 Hz, 2H), 5.82 (d, J = 8.1 Hz, 2H), 5.55 (s, 1H), 3.58 (s, 3H), 3.45 (s, 1H), 2.69-2.57 (m, 2H), 2.33 (s, 3H), 1.98 (s, 3H), 1.95-1.76 (m, 4H). | 470.25 |
| N-(4-(4-amino-5-(benzo[b]thiophen-2-yl)-7-methyl-7H-pyrrolo[2,3-d]pyrimidin-6-yl)phenyl)methacrylamide | 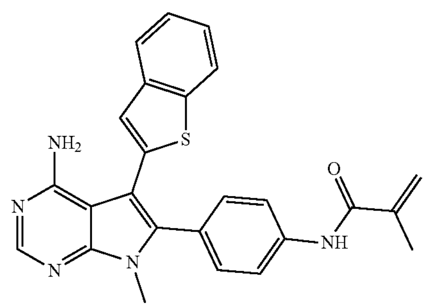 [SMILES: C=C(C)C(=O)Nc1ccc(-c2c(-c3cc4ccccc4s3)c3c(N)ncnc3n2C)cc1] | $^1$H NMR (400 MHz, DMSO-d$_6$) δ 9.90 (s, 1H), 8.23 (s, 1H), 7.85 (dd, J = 18.2, 7.7 Hz, 2H), 7.76-7.69 (m, 2H), 7.42-7.32 (m, 4H), 7.32 (td, J = 7.5, 1.5 Hz, 1H), 6.22 (s, 2H), 5.79 (s, 1H), 5.53 (s, 1H), 3.62 (s, 3H), 1.94 (d, J = 1.2 Hz, 3H). | 440.10 |
| N-(4-(4-amino-7-methyl-5-(4-phenylthiophen-2-yl)-7H-pyrrolo[2,3-d]pyrimidin-6-yl)phenyl)methacrylamide | 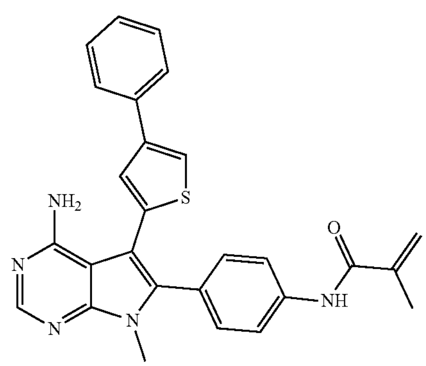 [SMILES: C=C(C)C(=O)Nc1ccc(-c2c(-c3cc(-c4ccccc4)cs3)c3c(N)ncnc3n2C)cc1] | $^1$H NMR (400 MHz, DMSO-d$_6$) δ 9.92 (s, 1H), 8.22 (s, 1H), 7.82 (d, J = 1.6 Hz, 1H), 7.76 (dd, J = 8.5, 2.5 Hz, 2H), 7.70 (d, J = 7.6 Hz, 2H), 7.53 (d, J = 1.6 Hz, 1H), 7.41 (dt, J = 7.9, 3.3 Hz, 4H), 7.30 (t, J = 7.4 Hz, 1H), 6.13 (s, 2H), 5.80 (s, 1H), 5.53 (s, 1H), 3.61 (s, 3H), 1.95 (s, 3H). | 466.20 |
| N-(4-(4-amino-7-methyl-5-(3-methylbenzo[b]thiophen-2-yl)-7H-pyrrolo[2,3-d]pyrimidin-6-yl)phenyl)methacrylamide | 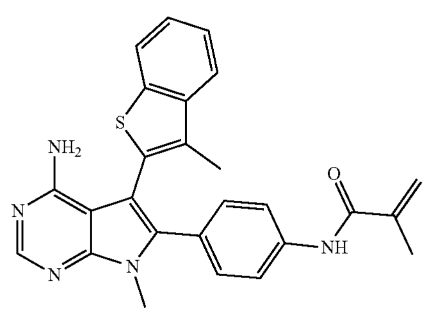 [SMILES: C=C(C)C(=O)Nc1ccc(-c2c(-c3sc4ccccc4c3C)c3c(N)ncnc3n2C)cc1] | $^1$H NMR (400 MHz, DMSO-d$_6$) δ 9.85 (s, 1H), 8.22 (s, 1H), 7.94-7.86 (m, 1H), 7.79-7.70 (m, 1H), 7.70-7.59 (m, 2H), 7.46-7.35 (m, 2H), 7.35-7.26 (m, 2H), 5.76 (t, J = 1.1 Hz, 1H), 5.55-5.46 (m, 1H), 3.68 (s, 3H), 2.07 (s, 3H), 1.92 (t, J = 1.3 Hz, 3H). | 454.05 |

TABLE 11-continued

Additional Exemplary Compounds

| Compound | Structure | Proton NMR | MS [M + 1] |
| --- | --- | --- | --- |
| N-(4-(4-amino-7-methyl-5-(4-(3-methyl-1,2,4-oxadiazol-5-yl)phenyl)-7H-pyrrolo[2,3-d]pyrimidin-6-yl)phenyl)methacrylamide | 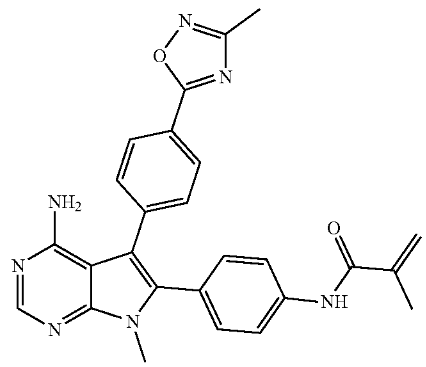 [SMILES: C=C(C)C(=O)Nc1ccc(-c2c(-c3ccc(-c4nc(C)no4)cc3)c3c(N)ncnc3n2C)cc1] | $^1$H NMR (400 MHz, DMSO-d$_6$) δ 9.91 (s, 1H), 8.23 (s, 1H), 8.07-7.99 (m, 2H), 7.76-7.68 (m, 2H), 7.46-7.38 (m, 2H), 7.32-7.24 (m, 2H), 6.02 (s, 2H), 5.80 (t, J = 1.1 Hz, 1H), 5.53 (t, J = 1.5 Hz, 1H), 3.62 (s, 3H), 2.41 (s, 3H), 1.95 (d, J = 1.3 Hz, 3H). | 466.25 |
| N-(4-(4-amino-7-methyl-5-(4-(2-methyloxazol-4-yl)phenyl)-7H-pyrrolo[2,3-d]pyrimidin-6-yl)phenyl)methacrylamide | 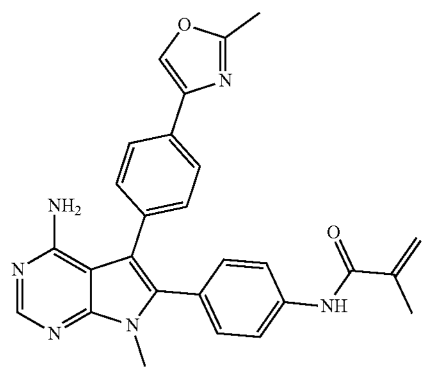 [SMILES: C=C(C)C(=O)Nc1ccc(-c2c(-c3ccc(-c4coc(C)n4)cc3)c3c(N)ncnc3n2C)cc1] | $^1$H NMR (400 MHz, Chloroform-d) δ 8.39 (s, 1H), 7.81 (s, 1H), 7.66 (d, J = 7.8 Hz, 2H), 7.58 (d, J = 8.5 Hz, 3H), 7.33-7.22 (m, 3H), 5.81 (s, 1H), 5.50 (s, 1H), 5.10 (s, 2H), 3.75 (s, 3H), 2.53 (s, 3H), 2.08 (s, 3H), 1.91 (s, 1H). | 465.30 |
| N-(4-(4-amino-5-(6-(4-ethyl-1H-pyrazol-1-yl)pyridin-3-yl)-7-methyl-7H-pyrrolo[2,3-d]pyrimidin-6-yl)phenyl)methacrylamide | 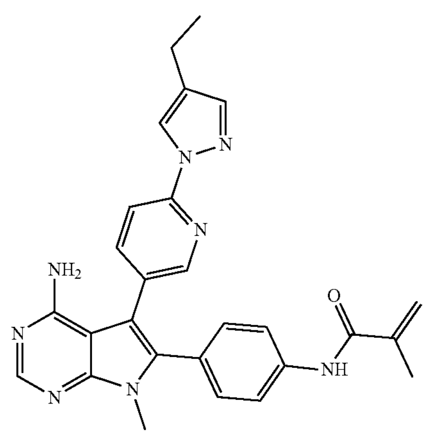 [SMILES: C=C(C)C(=O)Nc1ccc(-c2c(-c3ccc(-n4cc(CC)cn4)nc3)c3c(N)ncnc3n2C)cc1] | $^1$H NMR (400 MHz, Chloroform-d) δ 8.42 (s, 1H), 8.30 (ddd, J = 4.7, 2.1, 0.9 Hz, 2H), 7.92 (dd, J = 8.5, 0.8 Hz, 1H), 7.70 (dd, J = 8.5, 2.3 Hz, 1H), 7.66-.56 (m, 4H), 7.29-7.21 (m, 2H), 5.82 (s, 1H), 5.52 (d, J = 1.7 Hz, 1H), 5.01 (s, 2H), 3.76 (s, 3H), 2.59 (q, J = 7.5 Hz, 2H), 2.09 (dd, J = 1.6, 0.9 Hz, 3H), 1.27 (t, J = 7.6 Hz, 3H). | 479.35 |
| N-(4-(4-amino-7-methyl-5-(1H-pyrazol-4-yl)-7H-pyrrolo[2,3-d]pyrimidin-6-yl)phenyl)acrylamide | 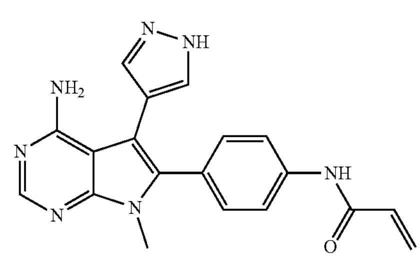 [SMILES: C=CC(=O)Nc1ccc(-c2c(-c3cn[nH]c3)c3c(N)ncnc3n2C)cc1] | $^1$H NMR (400 MHz, DMSO-d$_6$) δ 12.89 (s, 1H), 10.28 (s, 1H), 8.17 (d, J = 1.3 Hz, 1H), 7.54 (dd, J = 143.2, 8.2 Hz, 6H), 6.46 (dd, J = 16.9, 10.0 Hz, 1H), 6.29 (dt, J = 16.9, 1.7 Hz, 1H), 5.94 (s, 2H), 5.79 (d, J = 10.2 Hz, 1H), 3.58 (s, 3H). | 360.10 |

TABLE 11-continued

Additional Exemplary Compounds

| Compound | Structure | Proton NMR | MS [M + 1] |
|---|---|---|---|
| N-(4-(4-amino-7-methyl-5-(1H-pyrrol-3-yl)-7H-pyrrolo[2,3-d]pyrimidin-6-yl)phenyl)acrylamide | 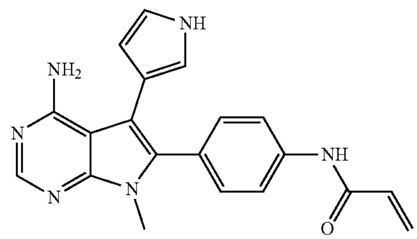 [SMILES: C=CC(=O)Nc1ccc(-c2c(-c3cc[nH]c3)c3c(N)ncnc3n2C)cc1] | $^1$H NMR (400 MHz, DMSO-d$_6$) δ 10.87 (s, 1H), 10.24 (s, 1H), 8.13 (s, 1H), 7.72-7.65 (m, 2H), 7.40-7.32 (m, 2H), 6.79 (q, J = 2.4 Hz, 1H), 6.65 (q, J = 2.0 Hz, 1H), 6.45 (dd, J = 17.0, 10.1 Hz, 1H), 6.28 (dd, J = 17.0, 2.0 Hz, 1H), 5.99 (q, J = 2.4 Hz, 1H), 5.78 (dd, J = 10.0, 2.1 Hz, 1H), 3.56 (s, 3H). | 359.15 |
| N-(4-(4-amino-5-(1H-indol-3-yl)-7-methyl-7H-pyrrolo[2,3-d]pyrimidin-6-yl)phenyl)acrylamide | 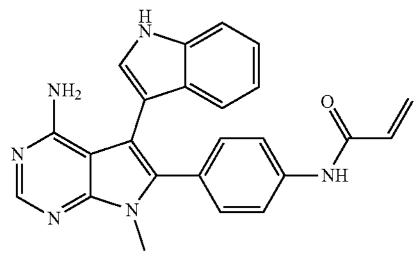 [SMILES: C=CC(=O)Nc1ccc(-c2c(-c3c[nH]c4ccccc34)c3c(N)ncnc3n2C)cc1] | $^1$H NMR (400 MHz, DMSO-d$_6$) δ 11.24-11.19 (m, 1H), 10.19 (s, 1H), 8.17 (s, 1H), 7.60 (d, J = 8.3 Hz, 2H), 7.40 (d, J = 8.1 Hz, 1H), 7.36-7.27 (m, 3H), 7.18 (d, J = 8.0 Hz, 1H), 7.09 (t, J = 7.6 Hz, 1H), 6.93 (t, J = 7.5 Hz, 1H), 6.41 (dd, J = 16.9, 10.1 Hz, 1H), 6.24 (dd, J = 16.9, 2.1 Hz, 1H), 5.75 (dd, J = 10.0, 2.1 Hz, 2H), 3.66 (s, 3H). | 409.15 |
| N-(4-(4-amino-5-(isothiazol-4-yl)-7-methyl-7H-pyrrolo[2,3-d]pyrimidin-6-yl)phenyl)acrylamide | 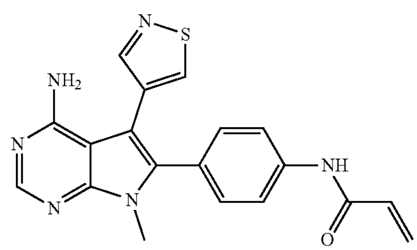 [SMILES: C=CC(=O)Nc1ccc(-c2c(-c3cnsc3)c3c(N)ncnc3n2C)cc1] | $^1$H NMR (400 MHz, DMSO-d$_6$) δ 10.29 (s, 1H), 8.87 (s, 1H), 8.28 (s, 1H), 8.21 (s, 1H), 7.75-7.68 (m, 2H), 7.35-7.28 (m, 2H), 6.45 (dd, J = 17.0, 10.1 Hz, 1H), 6.28 (dd, J = 17.0, 2.0 Hz, 1H), 6.01 (s, 1H), 5.79 (dd, J = 10.1, 2.1 Hz, 1H), 3.60 (s, 3H). | 377.10 |
| N-(4-(4-amino-5-(1H-indol-2-yl)-7-methyl-7H-pyrrolo[2,3-d]pyrimidin-6-yl)phenyl)acrylamide | 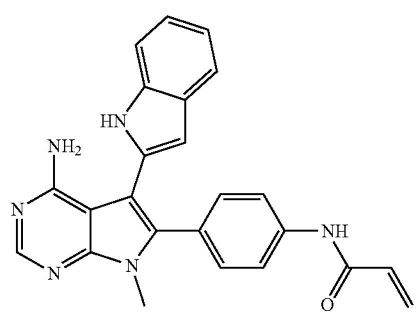 [SMILES: C=CC(=O)Nc1ccc(-c2c(-c3cc4ccccc4[nH]3)c3c(N)ncnc3n2C)cc1] | $^1$H NMR (400 MHz, DMSO-d$_6$) δ 11.13 (s, 1H), 10.25 (s, 1H), 8.22 (s, 1H), 7.69 (d, J = 8.3 Hz, 2H), 7.49 (d, J = 7.8 Hz, 1H), 7.40 (d, J = 8.5 Hz, 2H), 7.31 (d, J = 8.0 Hz, 1H), 7.11-7.03 (m, 1H), 6.99 (t, J = 7.4 Hz, 1H), 6.55-6.21 (m, 3H), 6.10 (s, 2H), 5.77 (dd, J = 10.0, 2.0 Hz, 1H), 3.66 (s, 3H). | 409.10 |
| N-(4-(4-amino-7-methyl-5-(6-oxo-1,6-dihydropyridin-3-yl)-7H-pyrrolo[2,3-d]pyrimidin-6-yl)phenyl)acrylamide | 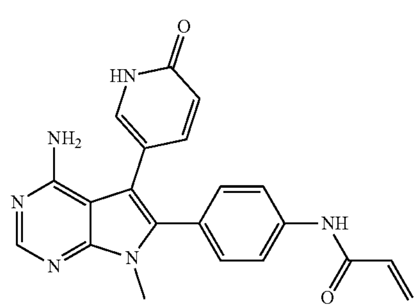 [SMILES: C=CC(=O)Nc1ccc(-c2c(-c3ccc(=O)[nH]c3)c3c(N)ncnc3n2C)cc1] | $^1$H NMR (400 MHz, DMSO-d$_6$) δ 11.52 (s, 1H), 10.28 (s, 1H), 8.17 (s, 1H), 7.77-7.71 (m, 2H), 7.37-7.25 (m, 2H), 7.21 (dd, J = 9.4, 2.6 Hz, 1H), 7.14 (d, J = 2.5 Hz, 1H), 6.46 (dd, J = 17.0, 10.1 Hz, 1H), 6.33-6.25 (m, 2H), 6.12 (s, 2H), 5.79 (dd, J = 10.1, 2.0 Hz, 1H), 3.58 (s, 3H). | 387.15 |

TABLE 11-continued

Additional Exemplary Compounds

| Compound | Structure | Proton NMR | MS [M + 1] |
|---|---|---|---|
| N-(4-(4-amino-5-(1H-indol-5-yl)-7-methyl-7H-pyrrolo[2,3-d]pyrimidin-6-yl)phenyl)acrylamide | 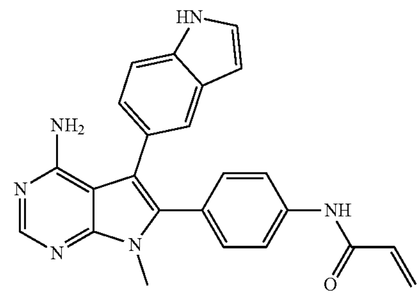 [SMILES: C=CC(=O)Nc1ccc(-c2c(-c3ccc4[nH]ccc4c3)c3c(N)ncnc3n2C)cc1] | $^1$H NMR (400 MHz, DMSO-d$_6$) δ 11.17 (s, 1H), 10.20 (s, 1H), 8.17 (s, 1H), 7.62 (d, J = 8.3 Hz, 2H), 7.43 (d, J = 1.6 Hz, 1H), 7.37 (d, J = 8.7 Hz, 2H), 7.30 (d, J = 8.6 Hz, 2H), 6.96 (dd, J = 8.3, 1.7 Hz, 1H), 6.47-6.36 (m, 2H), 6.25 (dd, J = 16.9, 2.1 Hz, 1H), 5.76 (dd, J = 10.0, 2.1 Hz, 1H), 3.63 (s, 3H). | 409.15 |
| N-(4-(4-amino-5-(4-hydroxyphenyl)-7-methyl-7H-pyrrolo[2,3-d]pyrimidin-6-yl)phenyl)acrylamide | 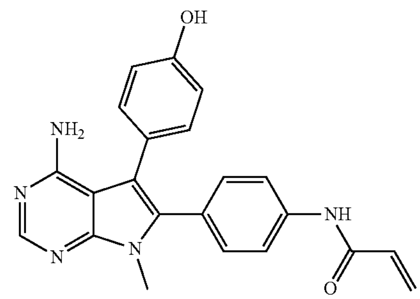 [SMILES: C=CC(=O)Nc1ccc(-c2c(-c3ccc(O)cc3)c3c(N)ncnc3n2C)cc1] | $^1$H NMR (400 MHz, DMSO-d$_6$) δ 10.24 (s, 1H), 9.49 (s, 1H), 8.16 (s, 1H), 7.67 (d, J = 8.5 Hz, 2H), 7.31-7.24 (m, 2H), 7.08-7.00 (m, 2H), 6.78-6.71 (m, 2H), 6.44 (dd, J = 17.0, 10.1 Hz, 1H), 6.27 (dd, J = 17.0, 2.1 Hz, 1H), 5.78 (dd, J = 10.0, 2.1 Hz, 1H), 3.60 (s, 3H). | 386.15 |
| N-(4-(4-amino-7-methyl-5-(1-methyl-1H-pyrazol-4-yl)-7H-pyrrolo[2,3-d]pyrimidin-6-yl)phenyl)acrylamide | 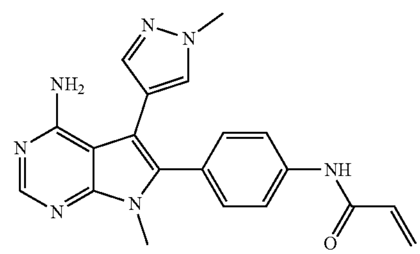 [SMILES: C=CC(=O)Nc1ccc(-c2c(-c3cnn(C)c3)c3c(N)ncnc3n2C)cc1] | $^1$H NMR (400 MHz, DMSO-d$_6$) δ 10.27 (s, 1H), 8.16 (s, 1H), 7.84-7.59 (m, 3H), 7.39-7.31 (m, 2H), 7.27 (d, J = 0.9 Hz, 1H), 6.46 (dd, J = 17.0, 10.1 Hz, 1H), 6.28 (dd, J = 17.0, 2.0 Hz, 1H), 6.01 (s, 2H), 5.79 (dd, J = 10.1, 2.1 Hz, 1H), 3.81 (s, 3H), 3.56 (s, 3H). | 374.10 |
| N-(4-(4-amino-5-(benzo[b]thiophen-2-yl)-7-methyl-7H-pyrrolo[2,3-d]pyrimidin-6-yl)phenyl)acrylamide | 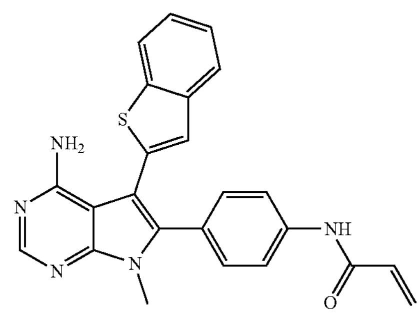 [SMILES: C=CC(=O)Nc1ccc(-c2c(-c3cc4ccccc4s3)c3c(N)ncnc3n2C)cc1] | $^1$H NMR (400 MHz, DMSO-d$_6$) δ 10.28 (s, 1H), 8.23 (s, 1H), 7.90-7.79 (m, 2H), 7.75-7.67 (m, 2H), 7.45-7.37 (m, 2H), 7.41-7.32 (m, 2H), 7.32 (ddd, J = 8.5, 7.1, 1.5 Hz, 1H), 6.43 (dd, J = 17.0, 10.1 Hz, 1H), 6.27 (dd, J = 17.0, 2.0 Hz, 2H), 5.77 (dd, J = 10.1, 2.1 Hz, 1H), 3.62 (s, 3H). | 426.10 |
| N-(4-(4-amino-5-(1H-indol-6-yl)-7-methyl-7H-pyrrolo[2,3-d]pyrimidin-6-yl)phenyl)acrylamide | 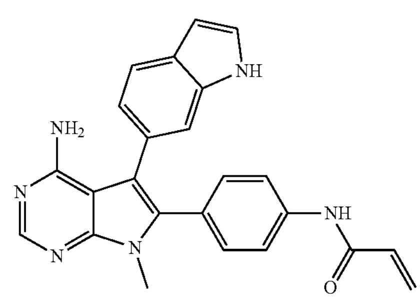 [SMILES: C=CC(=O)Nc1ccc(-c2c(-c3ccc4cc[nH]c4c3)c3c(N)ncnc3n2C)cc1] | $^1$H NMR (400 MHz, DMSO-d$_6$) δ 11.07 (t, J = 2.3 Hz, 1H), 10.21 (s, 1H), 8.18 (s, 1H), 7.67-7.60 (m, 2H), 7.53 (d, J = 8.1 Hz, 1H), 7.36-7.26 (m, 3H), 7.23 (q, J = 1.0 Hz, 1H), 6.91 (dd, J = 8.1, 1.5 Hz, 1H), 6.47 & #8211; 6.36 (m, 2H), 6.25 (dd, J = 17.0, 2.1 Hz, 1H), 5.76 (dd, J = 10.0, 2.1 Hz, 2H), 3.63 (s, 3H). | 409.15 |

TABLE 11-continued

Additional Exemplary Compounds

| Compound | Structure | Proton NMR | MS [M + 1] |
|---|---|---|---|
| N-(4-(4-amino-7-methyl-5-(1-phenyl-1,2,3,6-tetrahydropyridin-4-yl)-7H-pyrrolo[2,3-d]pyrimidin-6-yl)phenyl)methacrylamide | 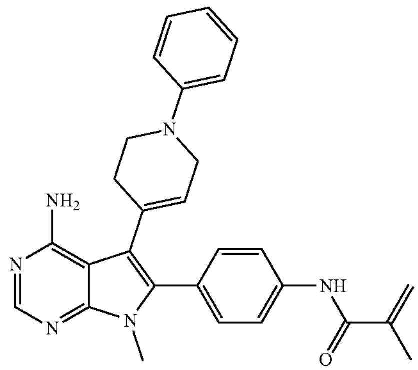 [SMILES: C=C(C)C(=O)Nc1ccc(-c2c(C3=CCN(c4ccccc4)CC3)c3c(N)ncnc3n2C)cc1] | ¹H NMR (400 MHz, DMSO-d₆) δ 9.94 (s, 1H), 8.15 (s, 1H), 7.80 (d, J = 7.9 Hz, 2H), 7.43 (d, J = 8.3 Hz, 2H), 7.20 (t, J = 7.7 Hz, 2H), 6.91 (d, J = 8.2 Hz, 2H), 6.73 (t, J = 7.2 Hz, 1H), 6.26 (s, 2H), 5.92 (s, 1H), 5.82 (s, 1H), 5.55 (s, 1H), 3.84 (s, 2H), 3.58 (s, 3H), 2.16-2.05 (m, 4H), 1.97 (s, 3H). | 465.25 |
| benzyl 4-(4-amino-6-(4-methacrylamidophenyl)-7-methyl-7H-pyrrolo[2,3-d]pyrimidin-5-yl)-3,6-dihydropyridine-1(2H)-carboxylate | 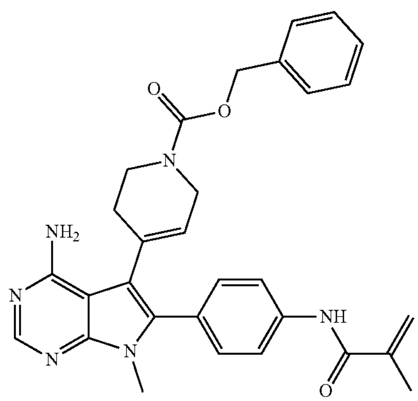 [SMILES: C=C(C)C(=O)Nc1ccc(-c2c(C3=CCN(C(=O)OCc4ccccc4)CC3)c3c(N)ncnc3n2C)cc1] | ¹H NMR (400 MHz, DMSO-d₆) δ 9.96 (s, 1H), 8.14 (s, 1H), 7.83 (dd, J = 8.7, 2.3 Hz, 2H), 7.53-7.27 (m, 7H), 6.33 (s, 2H), 5.80 (d, J = 21.2 Hz, 2H), 5.55 (s, 1H), 5.09 (s, 2H), 4.06 (s, 2H), 3.56 (s, 3H), 3.46 (s, 2H), 1.99 (d, J = 11.6 Hz, 5H). | 523.20 |
| N-(4-(4-amino-5-(1-benzyl-1,2,3,6-tetrahydropyridin-4-yl)-7-methyl-7H-pyrrolo[2,3-d]pyrimidin-6-yl)phenyl)methacrylamide | 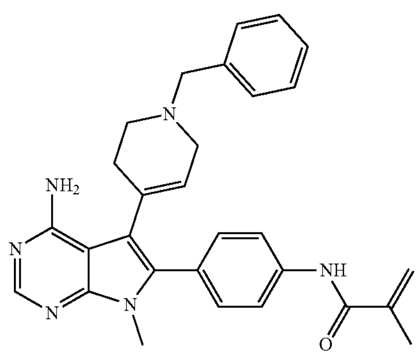 [SMILES: C=C(C)C(=O)Nc1ccc(-c2c(C3=CCN(Cc4ccccc4)CC3)c3c(N)ncnc3n2C)cc1] | ¹H NMR (400 MHz, DMSO-d₆) δ 9.98 (s, 1H), 8.14 (s, 1H), 7.87-7.80 (m, 2H), 7.47-7.40 (m, 2H), 7.33 (d, J = 5.1 Hz, 4H), 7.27 (s, 1H), 6.26 (s, 2H), 5.81 (d, J = 25.0 Hz, 2H), 5.56 (t, J = 1.5 Hz, 1H), 3.56 (s, 5H), 3.34 (s, 2H), 3.10 (s, 2H), 1.98 (d, J = 1.3 Hz, 5H). | 479.25 |
| N-(4-(4-amino-5-(3-fluoro-4-((6-methylpyridin-2-yl)oxy)phenyl)-7-methyl-7H-pyrrolo[2,3-d]pyrimidin-6-yl)phenyl)acrylamide | 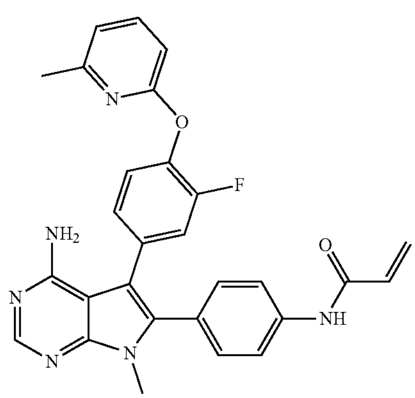 [SMILES: C=CC(=O)Nc1ccc(-c2c(-c3ccc(Oc4cccc(C)n4)c(F)c3)c3c(N)ncnc3n2C)cc1] | ¹H NMR (400 MHz, DMSO-d₆) δ 10.29 (s, 1H), 8.21 (s, 1H), 7.81-7.67 (m, 3H), 7.37-7.29 (m, 2H), 7.26 (t, J = 8.4 Hz, 1H), 7.16 (dd, J = 11.5, 2.0 Hz, 1H), 7.07 (dd, J = 8.5, 2.0 Hz, 1H), 7.00 (d, J = 7.3 Hz, 1H), 6.86 (d, J = 8.2 Hz, 1H), 6.45 (dd, J = 17.0, 10.1 Hz, 1H), 6.28 (dd, J = 17.0, 2.1 Hz, 1H), 5.78 (dd, J = 10.1, 2.1 Hz, 1H), 3.62 (s, 3H), 2.30 (s, 3H). | 495.20 |

TABLE 11-continued

Additional Exemplary Compounds

| Compound | Structure | Proton NMR | MS [M + 1] |
|---|---|---|---|
| 4-(6-(4-acrylamidophenyl)-4-amino-7-methyl-7H-pyrrolo[2,3-d]pyrimidin-5-yl)-N-cyclobutyl-2-methoxybenzamide | 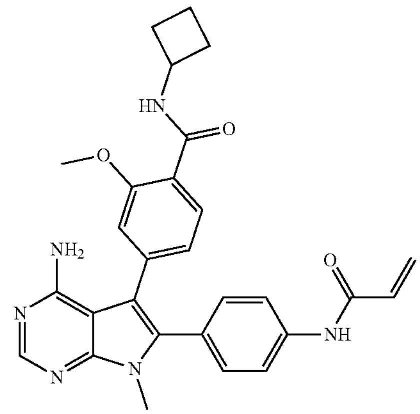 [SMILES: C=CC(=O)Nc1ccc(-c2c(-c3ccc(C(=O)NC4CCC4)c(OC)c3)c3c(N)ncnc3n2C)cc1] | $^1$H NMR (300 MHz, DMSO-$d_6$) δ 10.29 (s, 1H), 8.22 (d, J = 3.3 Hz, 1H), 7.71 (d, J = 8.6 Hz, 2H), 7.60 (d, J = 7.8 Hz, 1H), 7.32 (d, J = 8.6 Hz, 2H), 6.95-6.81 (m, 2H), 6.45 (dd, J = 17.0, 9.9 Hz, 1H), 6.28 (dd, J = 17.0, 2.2 Hz, 1H), 5.79 (dd, J = 9.9, 2.2 Hz, 1H), 4.39 (q, J = 8.3 Hz, 1H), 3.70 (s, 3H), 3.60 (s, 3H), 2.21 (s, 2H), 1.98 (q, J = 9.7 Hz, 2H), 1.76-1.53 (m, 2H). | 497.20 |
| N-(4-(4-amino-7-methyl-5-(3-methyl-4-((4-methylpyrimidin-2-yl)oxy)phenyl)-7H-pyrrolo[2,3-d]pyrimidin-6-yl)-3-fluorophenyl)acrylamide | 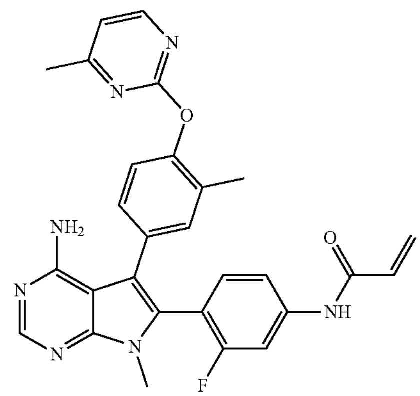 [SMILES: C=CC(=O)Nc1ccc(-c2c(-c3ccc(Oc4nccc(C)n4)c(C)c3)c3c(N)ncnc3n2C)c(F)c1] | $^1$H NMR (400 MHz, DMSO-$d_6$) δ 10.52 (s, 1H), 8.43 (d, J = 5.0 Hz, 1H), 8.22 (s, 1H), 7.81 (dd, J = 12.1, 2.0 Hz, 1H), 7.44-7.27 (m, 2H), 7.22 (s, 1H), 7.15-7.02 (m, 3H), 6.44 (dd, J = 17.0, 10.0 Hz, 1H), 6.31 (dd, J = 17.0, 2.1 Hz, 1H), 5.82 (dd, J = 10.0, 2.0 Hz, 1H), 3.53 (s, 3H), 2.41 (s, 3H), 2.03 (s, 3H). | 510.15 |
| N-(4-(4-amino-7-methyl-5-(4-((4-methylpyrimidin-2-yl)oxy)phenyl)-7H-pyrrolo[2,3-d]pyrimidin-6-yl)-3-chlorophenyl)acrylamide | 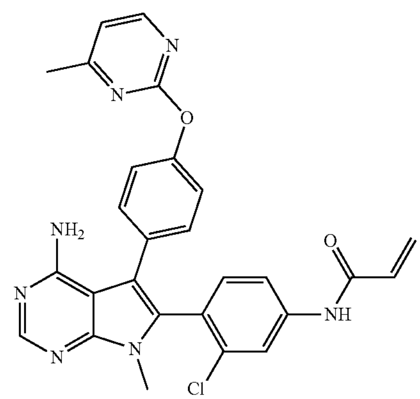 [SMILES: C=CC(=O)Nc1ccc(-c2c(-c3ccc(Oc4nccc(C)n4)cc3)c3c(N)ncnc3n2C)c(Cl)c1] | $^1$H NMR (300 MHz, DMSO-$d_6$) δ 10.49 (s, 1H), 8.45 (d, J = 5.0 Hz, 1H), 8.22 (s, 1H), 8.07 (d, J = 2.0 Hz, 1H), 7.57 (dd, J = 8.4, 2.1 Hz, 1H), 7.41 (d, J = 8.4 Hz, 1H), 7.27 (d, J = 8.6 Hz, 2H), 7.20-7.05 (m, 3H), 6.50-6.25 (m, 2H), 5.83 (dd, J = 9.8, 2.3 Hz, 1H), 3.48 (s, 3H), 2.40 (s, 3H). | 512.10 |

Example 13

Scheme 11

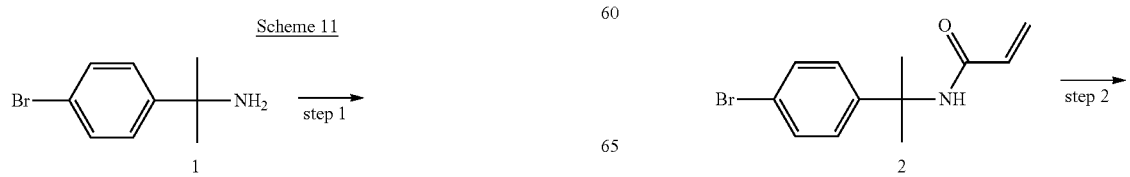

-continued

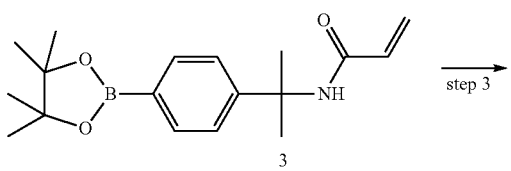

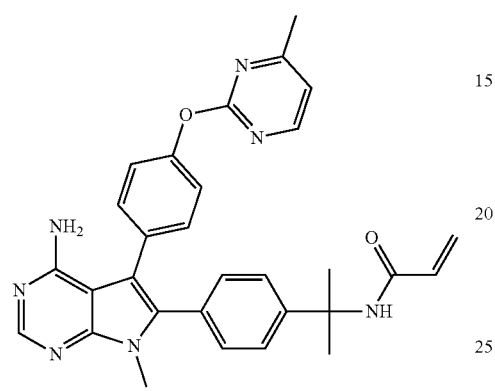

N-(2-(4-bromophenyl) propan-2-yl) acrylamide

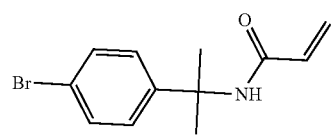

Step 1: To a stirred solution/mixture of 2-(4-bromophenyl) propan-2-amine (1.50 g, 7.006 mmol) and TEA (2.13 g, 21.018 mmol) in DCM (30 mL) was added acryloyl chloride (0.63 g, 7.006 mmol) dropwise in portions at 0 degrees C. under nitrogen atmosphere. The mixture was stirred for 1 h at 0 degrees C. The resulting mixture was extracted with $CH_2Cl_2$. The combined organic layers were washed with brines, dried over anhydrous $Na_2SO_4$. After filtration, the filtrate was concentrated under reduced pressure to afford N-(2-(4-bromophenyl) propan-2-yl) acrylamide (500 mg, 27%) as a yellow solid.

N-(2-(4-(4,4,5,5-tetramethyl-1,3,2-dioxaborolan-2-yl)phenyl)propan-2-yl)acrylamide

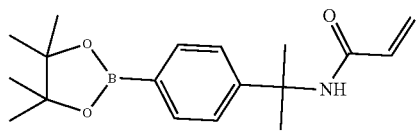 [SMILES: C=CC(=O)NC(C)(C)c1ccc(B2OC(C)(C)C(C)(C)O2)cc1]

Step 2: A solution/mixture of N-[2-(4-bromophenyl)propan-2-yl]prop-2-enamide (470.00 mg, 1.753 mmol), bis(pinacolato)diboron (667.63 mg, 2.629 mmol), AcOK (516.05 mg, 5.258 mmol) and Pd(dppf)Cl2 (128.25 mg, 0.175 mmol) in DMF (10 mL) was stirred for 2 h at 80 degrees C. under nitrogen atmosphere. The resulting mixture was extracted with EtOAc. The combined organic layers were washed with brines, dried over anhydrous $Na_2SO_4$. After filtration, the filtrate was concentrated under reduced pressure. The residue was purified by silica gel column chromatography, eluted with PE/EtOAc=4/1 to afford N-(2-(4-(4,4,5,5-tetramethyl-1,3,2-dioxaborolan-2-yl)phenyl)propan-2-yl)acrylamide (400 mg, 72%) as a off-white solid.

N-(2-(4-(4-amino-7-methyl-5-(4-(4-methylpyrimidin-2-yloxy)phenyl)-7H-pyrrolo[2,3-d]pyrimidin-6-yl)phenyl)propan-2-yl)acrylamide

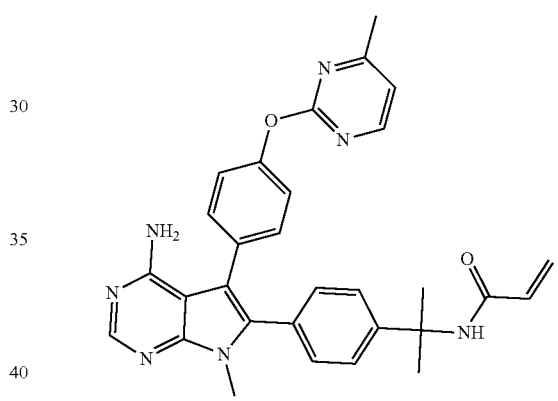

Step 3: A solution/mixture of 6-iodo-7-methyl-5-[4-[(4-methylpyrimidin-2-yl)oxy]phenyl]pyrrolo[2,3-d]pyrimidin-4-amine (200.00 mg, 0.44 mmol), N-[2-[4-(4,4,5,5-tetramethyl-1,3,2-dioxaborolan-2-yl)phenyl]propan-2-yl]prop-2-enamide (165.1 mg, 0.52 mmol), $K_3PO_4$ (277.9 mg, 1.31 mmol) and Pd(dppf)Cl$_2$ (31.9 mg, 0.04 mmol) in DMF (4 mL) and H$_2$O (1 mL) was stirred for 1 h at 90 degrees C. under nitrogen atmosphere. The resulting mixture was extracted with EtOAc. The combined organic layers were washed with brines, dried over anhydrous Na$_2$SO$_4$. After filtration, the filtrate was concentrated under reduced pressure. The crude product was purified by HPLC (Column: XBridge Shield RP18 OBD Column, 5 um, 19*150 mm; Mobile Phase A:Water(10 mM NH$_4$HCO$_3$), Mobile Phase B:ACN; Flow rate:25 mL/min; Gradient:25 B to 43 B in 7 min; 220/254 nm; RT1:6.25; RT2:; Injection Volumn: ml; Number Of Runs::). Lyophilization yielded N-(2-(4-(4-amino-7-methyl-5-(4-(4-methylpyrimidin-2-yloxy)phenyl)-7H-pyrrolo[2,3-d]pyrimidin-6-yl)phenyl)propan-2-yl)acrylamide (51 mg, 22.3%) as a off-white amorphous solid.

Additional compounds prepared according to the methods of Example 13 are depicted in Table 12 below.

TABLE 12

Additional Exemplary Compounds

| Compound | Structure | Proton NMR | MS [M + 1] |
|---|---|---|---|
| 7-(4-amino-5-(3-methoxy-4-(6-methylpyridin-2-yloxy)phenyl)-7-methyl-7H-pyrrolo[2,3-d]pyrimidin-6-yl)-3,4-dihydropyrido[1,2-a]pyrimidin-2-one | 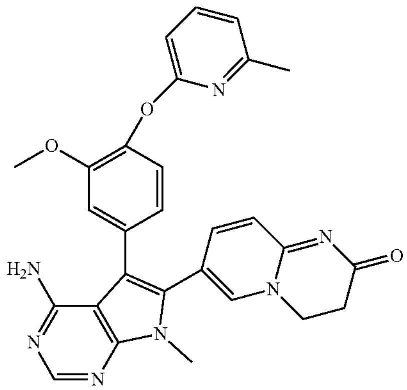 [SMILES: COc1cc(-c2c(C3=CN4CCC(=O)N=C4C=C3)n(C)c3ncnc(N)c23)ccc1Oc1cccc(C)n1] | $^1$H NMR (400 MHz, Chloroform-d) δ 8.41 (s, 1H), 7.61 (t, J = 7.7 Hz, 1H), 7.53 (dd, J = 9.2, 2.1 Hz, 1H), 7.20-7.13 (m, 2H), 7.05 (d, J = 9.2 Hz, 1H), 6.94-6.84 (m, 3H), 6.73 (d, J = 8.2 Hz, 1H), 5.20 (s, 2H), 4.20 (t, J = 7.4 Hz, 2H), 3.80 (s, 3H), 3.74 (s, 3H), 2.74 (t, J = 7.4 Hz, 2H), 2.40 (s, 3H). | 508.00 |
| 1-(4-(4-amino-5-(3-methoxy-4-((6-methylpyridin-2-yl)oxy)phenyl)-7-methyl-7H-pyrrolo[2,3-d]pyrimidin-6-yl)-6-methyl-3,6-dihydropyridin-1(2H)-yl)prop-2-en-1-one | 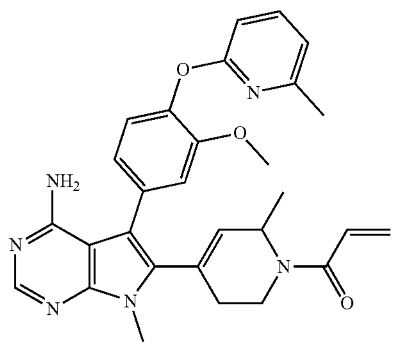 [SMILES: C=CC(=O)N1CCC(c2c(-c3ccc(Oc4cccc(C)n4)c(OC)c3)c3c(N)ncnc3n2C)=CC1C] | $^1$H NMR (400 MHz, DMSO-d$_6$) δ 8.17 (s, 1H), 7.67 (td, J = 7.7, 2.1 Hz, 1H), 7.18 (dd, J = 8.0, 6.2 Hz, 1H), 7.10-7.05 (m, 1H), 7.00-6.92 (m, 2H), 6.86-6.73 (m, 1H), 6.68 (t, J = 7.6 Hz, 1H), 6.09 (dt, J = 34.3, 19.4 Hz, 2H), 5.86 (s, 1H), 5.67 (d, J = 11.0 Hz, 1H), 4.93-4.61 (m, 1H), 4.48 (s, 1H), 4.14-3.73 (m, 1H), 3.67 (s, 6H), 3.25-2.64 (m, 1H), 2.30 (d, J = 3.1 Hz, 3H), 1.96 (dd, J = 67.9, 16.5 Hz, 1H), 1.31-0.80 (m, 3H). | 511.40 |
| 1-(3-(4-amino-5-(3-methoxy-4-(6-methylpyridin-2-yl)oxy)phenyl)-7-methyl-7H-pyrrolo[2,3-d]pyrimidin-6-yl)-2,5-dihydro-1H-pyrrol-1-yl)prop-2-en-1-one | 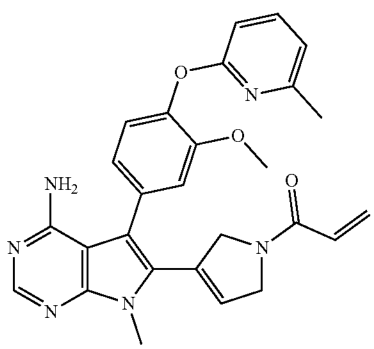 [SMILES: C=CC(=O)N1CC=C(c2c(-c3ccc(Oc4cccc(C)n4)c(OC)c3)c3c(N)ncnc3n2C)C1] | $^1$H NMR (400 MHz, DMSO-d$_6$) δ 8.19 (s, 1H), 7.67 (td, J = 7.7, 4.7 Hz, 1H), 7.25-7.12 (m, 2H), 7.04-6.90 (m, 2H), 6.68 (dd, J = 8.2, 3.6 Hz, 1H), 6.58 (dd, J = 16.7, 10.3 Hz, 1H), 6.42-6.10 (m, 3H), 6.02 (s, 1H), 5.68 (ddd, J = 16.3, 10.2, 2.4 Hz, 1H), 4.56 (p, J = 2.5 Hz, 1H), 4.33 (s, 2H), 4.05 (p, J = 22 Hz, 1H), 3.79 (d, J = 2.9 Hz, 3H), 3.69 (s, 3H), 2.30 (d, J = 11.6 Hz, 3H). | 483.20 |
| N-(4-(4-amino-5-(4-((6-methylpyridin-2-yl)oxy)phenyl)-7H-pyrrolo[2,3-d]pyrimidin-6-yl)phenyl)methacrylamide | 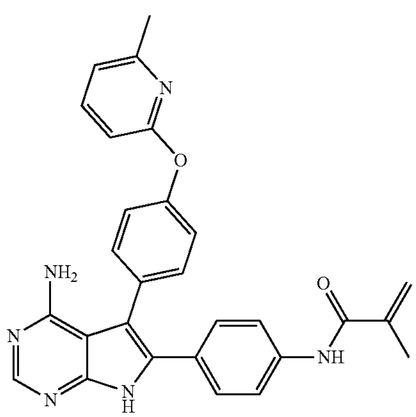 [SMILES: C=C(C)C(=O)Nc1ccc(-c2[nH]c3ncnc(N)c3c2-c2ccc(Oc3cccc(C)n3)cc2)cc1] | $^1$H NMR (400 MHz, DMSO-d$_6$) δ 12.07 (s, 1H), 9.83 (s, 1H), 8.12 (s, 1H), 7.77 (t, J = 7.8 Hz, 1H), 7.65-7.57 (m, 2H), 7.42-7.35 (m, 2H), 7.38-7.26 (m, 2H), 7.23-7.15 (m, 2H), 7.04 (d, J = 7.4 Hz, 1H), 6.85 (d, J = 8.1 Hz, 1H), 5.78 (s, 2H), 5.52 (t, J = 1.5 Hz, 1H), 2.38 (s, 3H), 1.94 (d, J = 1.3 Hz, 3H). | 477.30 |

TABLE 12-continued

Additional Exemplary Compounds

| Compound | Structure | Proton NMR | MS [M + 1] |
|---|---|---|---|
| N-(4-(4-amino-5-(4-((6-methylpyridin-2-yl)oxy)phenyl)furo[2,3-d]pyrimidin-6-yl)phenyl)methacrylamide | 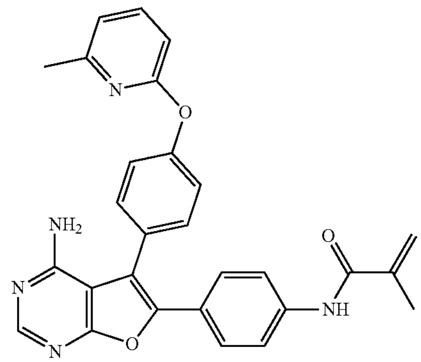 | $^1$H NMR (400 MHz, DMSO-d$_6$) δ 10.03 (s, 1H), 8.27 (s, 1H), 7.93 (d, J = 8.2 Hz, 2H), 7.75 (t, J = 7.8 Hz, 1H), 7.50 (dd, J = 8.4, 5.2 Hz, 4H), 7.11 (d, J = 8.4 Hz, 2H), 7.03 (d, J = 7.4 Hz, 1H), 6.81 (d, J = 8.2 Hz, 1H), 5.84 (s, 1H), 5.56 (s, 1H), 2.33 (s, 3H), 1.98 (s, 3H). | 478.30 |
| N-(4-(4-amino-5-(4-((6-methylpyridin-2-yl)oxy)phenyl)-7H-pyrrolo[2,3-d]pyrimidin-6-yl)phenyl)-N-methylacrylamide | 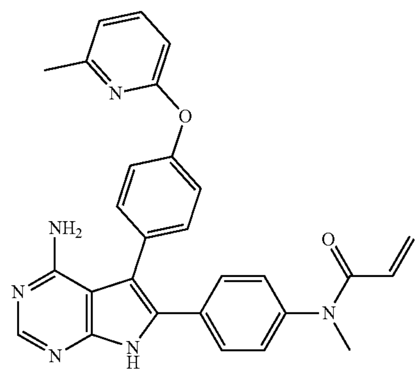 [SMILES: C=CC(=O)N(C)c1ccc(-c2[nH]c3ncnc(N)c3c2-c2ccc(Oc3cccc(C)n3)cc2)cc1] | $^1$H NMR (400 MHz, DMSO-d$_6$) δ 12.17 (s, 1H), 8.14 (s, 1H), 7.77 (t, J = 7.7 Hz, 1H), 7.44 (dd, J = 15.1, 8.2 Hz, 4H), 7.23 (dd, J = 8.2, 5.9 Hz, 4H), 7.04 (d, J = 7.3 Hz, 1H), 6.86 (d, J = 8.2 Hz, 1H), 6.24-5.44 (m, 5H), 3.24 (s, 3H), 2.37 (s, 3H). | 477.35 |
| N-(4-(4-amino-5-(4-(pyrrolidine-1-carbonyl)phenyl)-7H-pyrrolo[2,3-d]pyrimidin-6-yl)phenyl)methacrylamide | 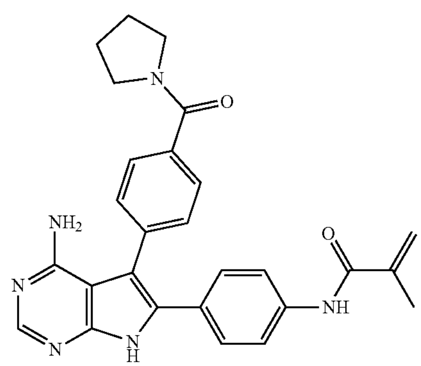 [SMILES: C=C(C)C(=O)Nc1ccc(-c2[nH]c3ncnc(N)c3c2-c2ccc(C(=O)N3CCCC3)cc2)cc1] | $^1$H NMR (400 MHz, DMSO-d$_6$) δ 12.12 (s, 1H), 9.82 (s, 1H), 8.13 (s, 1H), 7.59 (d, J = 8.3 Hz, 4H), 7.39 (d, J = 8.1 Hz, 2H), 7.25 (d, J = 8.7 Hz, 2H), 5.79 (s, 1H), 5.52 (s, 1H), 3.48 (dt, J = 11.2, 6.4 Hz, 4H), 1.94 (s, 3H), 1.87 (dq, J = 13.0, 6.8 Hz, 4H). | 467.30 |
| N-(4-(4-amino-5-(3-ethoxy-4-((6-methylpyridin-2-yl)oxy)phenyl)-7H-pyrrolo[2,3-d]pyrimidin-6-yl)phenyl)methacrylamide | 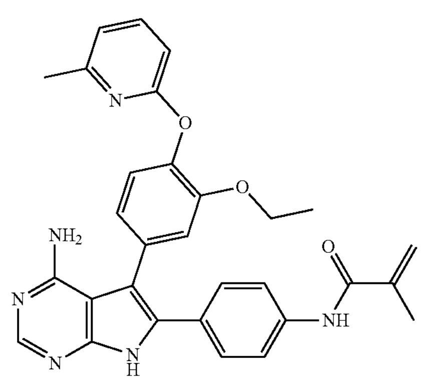 [SMILES: C=C(C)C(=O)Nc1ccc(-c2[nH]c3ncnc(N)c3c2-c2ccc(Oc3cccc(C)n3)c(OCC)c2)cc1] | 1H NMR (400 MHz, DMSO-d6) δ 12.05 (s, 1H), 9.83 (s, 1H), 8.13 (s, 1H), 7.70 (t, J = 7.7 Hz, 1H), 7.66-7.60 (m, 2H), 7.39-7.30 (m, 2H), 7.18 (d, J = 8.0 Hz, 1H), 7.09 (d, J = 1.9 Hz, 1H), 7.01-6.90 (m, 2H), 6.74 (d, J = 8.2 Hz, 1H), 5.79 (s, 2H), 5.53 (t, J = 1.5 Hz, 1H), 3.91 (q, J = 6.9 Hz, 2H), 2.34 (s, 3H), 1.95 (d, J = 1.5 Hz, 3H), 1.27-1.07 (m, 1H), 1.00 (t, J = 6.9 Hz, 3H). | 521.25 |

TABLE 12-continued

Additional Exemplary Compounds

| Compound | Structure | Proton NMR | MS [M + 1] |
|---|---|---|---|
| N-(4-(4-amino-5-(3-methoxy-4-((6-methylpyridin-2-yl)oxy)phenyl)-7H-pyrrolo[2,3-d]pyrimidin-6-yl)phenyl)but-2-ynamide | 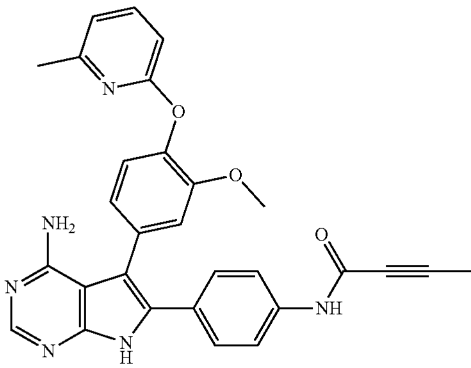 [SMILES: CC#CC(=O)Nc1ccc(-c2[nH]c3ncnc(N)c3c2-c2ccc(Oc3cccc(C)n3)c(OC)c2)cc1] | 1H NMR (400 MHz, DMSO-d6) δ 12.07 (s, 1H), 10.66 (s, 1H), 8.13 (s, 1H), 7.74-7.65 (m, 1H), 7.53 (d, J = 8.7 Hz, 2H), 7.38-7.29 (m, 2H), 7.21-7.06 (m, 2H), 7.02-6.88 (m, 2H), 6.72 (d, J = 8.2 Hz, 1H), 5.84 (s, 1H), 3.62 (s, 2H), 2.34 (s, 3H), 2.05 (s, 2H). | 505.25 |
| N-(4-(4-amino-5-(4-((6-methylpyridin-2-yl)oxy)phenyl)-7H-pyrrolo[2,3-d]pyrimidin-6-yl)phenyl)acrylamide | 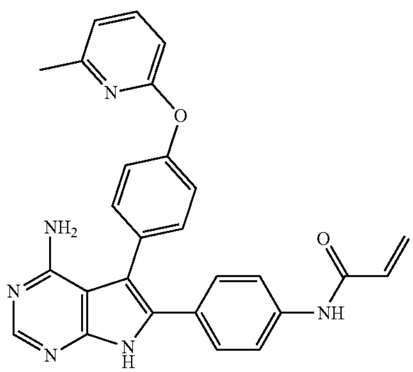 [SMILES: C=CC(=O)Nc1ccc(-c2[nH]c3ncnc(N)c3c2-c2ccc(Oc3cccc(C)n3)cc2)cc1] | $^1$H NMR (400 MHz, DMSO-d$_6$) δ 12.07 (s, 1H), 10.19 (s, 1H), 8.12 (s, 1H), 7.77 (t, J = 7.8 Hz, 1H), 7.60 (d, J = 8.6 Hz, 2H), 7.41-7.36 (m, 2H), 7.32 (d, J = 8.6 Hz, 2H), 7.22-7.16 (m, 2H), 7.04 (d, J = 7.3 Hz, 1H), 6.85 (d, J = 8.2 Hz, 1H), 6.43 (dd, J = 17.0, 10.1 Hz, 1H), 6.26 (dd, J = 17.0, 2.0 Hz, 1H), 5.76 (dd, J = 10.1, 2.0 Hz, 2H), 2.38 (s, 3H). | 463.40 |
| N-(4-(4-amino-5-(4-((6-methylpyridin-2-yl)oxy)phenyl)-7H-pyrrolo[2,3-d]pyrimidin-6-yl)phenyl)isobutyramide | 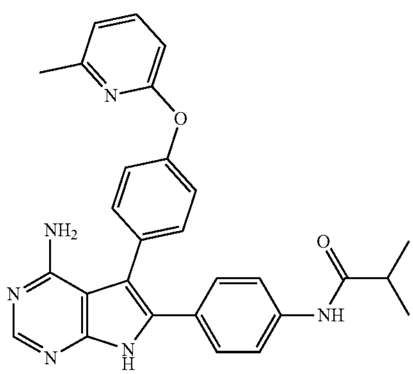 [SMILES: Cc1cccc(Oc2ccc(-c3c(-c4ccc(NC(=O)C(C)C)cc4)[nH]c4ncnc(N)c34)cc2)n1] | $^1$H NMR (400 MHz, DMSO-d$_6$) δ 12.05 (s, 1H), 9.87 (s, 1H), 8.12 (s, 1H), 7.76 (t, J = 7.8 Hz, 1H), 7.54 (d, J = 8.7 Hz, 2H), 7.39-7.35 (m, 2H), 7.28 (d, J = 8.6 Hz, 2H), 7.19 (d, J = 8.4 Hz, 2H), 7.04 (d, J = 7.4 Hz, 1H), 6.84 (d, J = 8.2 Hz, 1H), 5.75 (s, 1H), 2.79-2.57 (m, 1H), 2.38 (s, 3H), 1.09 (d, J = 6.8 Hz, 6H). | 479.45 |
| N-(4-(4-amino-5-(4-(pyrrolidine-1-carbonyl)phenyl)-7H-pyrrolo[2,3-d]pyrimidin-6-yl)phenyl)acrylamide | 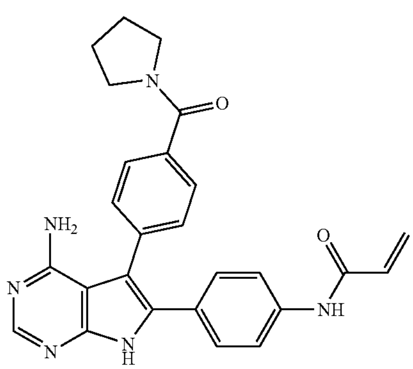 [SMILES: C=CC(=O)Nc1ccc(-c2[nH]c3ncnc(N)c3c2-c2ccc(C(=O)N3CCCC3)cc2)cc1] | $^1$H NMR (400 MHz, DMSO-d$_6$) δ 12.12 (s, 1H), 10.20 (s, 1H), 8.13 (s, 1H), 7.62-7.54 (m, 4H), 7.45-7.36 (m, 2H), 7.31-7.23 (m, 2H), 6.42 (dd, J = 17.0, 10.1 Hz, 1H), 6.25 (dd, J = 17.0, 2.1 Hz, 1H), 5.76 (dd, J = 10.0, 2.1 Hz, 2H), 3.54-3.43 (m, 4H), 2.08 (s, 1H), 1.88 (dt, J = 12.6, 6.7 Hz, 4H). | 453.30 |

TABLE 12-continued

Additional Exemplary Compounds

| Compound | Structure | Proton NMR | MS [M + 1] |
|---|---|---|---|
| 1-(6-(4-amino-7-methyl-5-(4-((6-methylpyridin-2-yl)oxy)phenyl)-7H-pyrrolo[2,3-d]pyrimidin-6-yl)-3-oxa-8-azabicyclo[3.2.1]octan-8-yl)prop-2-en-1-one | 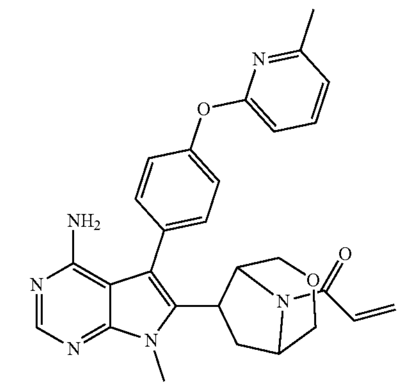 [SMILES: C=CC(=O)N1C2COCC1C(c1c(-c3ccc(Oc4cccc(C)n4)cc3)c3c(N)ncnc3n1C)C2] | $^1$H NMR (400 MHz, DMSO-d$_6$) δ 8.11 (d, J = 3.2 Hz, 1H), 7.77 (t, J = 7.7 Hz, 1H), 7.45-7.09 (m, 4H), 7.05 (d, J = 7.4 Hz, 1H), 6.87 (dd, J = 10.3, 8.2 Hz, 1H), 6.65 (ddd, J = 35.0, 16.7, 10.3 Hz, 1H), 6.24 (ddd, J = 16.7, 4.8, 2.4 Hz, 1H), 5.70 (td, J = 10.5, 2.4 Hz, 1H), 4.68 (s, 1H), 4.50 (d, J = 16.1 Hz, 2H), 3.95 (dt, J = 24.1, 7.3 Hz, 1H), 3.77-3.67 (m, 5H), 3.67-3.52 (m, 2H), 3.44 (dd, J = 10.8, 6.1 Hz, 1H), 2.37 (d, J = 2.4 Hz, 3H), 2.31-2.06 (m, 2H). | 497.35 |
| N-(4-(4-amino-5-(4-((6-methylpyridin-2-yl)oxy)phenyl)thieno[2,3-d]pyrimidin-6-yl)phenyl)methacrylamide | 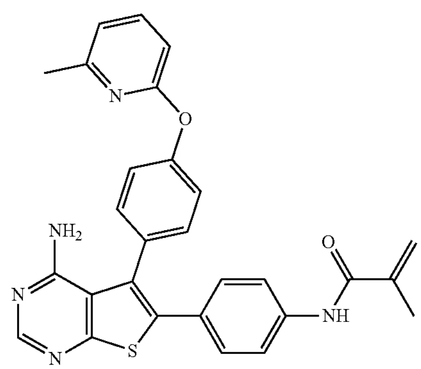 | $^1$H NMR (400 MHz, DMSO-d$_6$) δ 10.00 (s, 1H), 8.35 (s, 1H), 7.85 (d, J = 8.3 Hz, 2H), 7.74 (t, J = 7.8 Hz, 1H), 7.39 (d, J = 8.2 Hz, 2H), 7.29 (d, J = 8.5 Hz, 2H), 7.03 (t, J = 7.6 Hz, 3H), 6.79 (d, J = 8.1 Hz, 1H), 5.83 (s, 1H), 5.56 (s, 1H), 2.33 (s, 3H), 1.97 (s, 3H). | 494.30 |
| N-(4-(4-amino-5-(4-(pyrrolidin-1-ylsulfonyl)phenyl)-7H-pyrrolo[2,3-d]pyrimidin-6-yl)phenyl)methacrylamide | 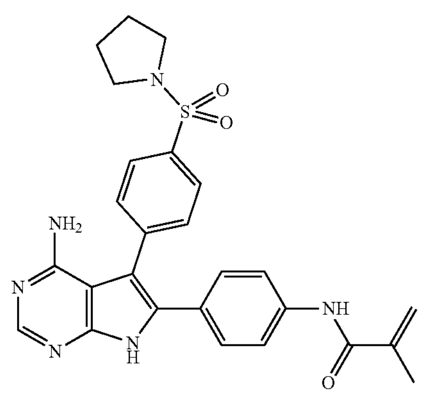 [SMILES: C=C(C)C(=O)Nc1ccc(-c2[nH]c3ncnc(N)c3c2-c2ccc(S(=O)(=O)N3CCCC3)cc2)cc1] | 1H NMR (400 MHz, DMSO-d6) δ 12.21 (s, 1H), 9.85 (s, 1H), 8.14 (s, 1H), 7.88-7.81 (m, 2H), 7.62-7.52 (m, 4H), 7.16 (d, J = 8.8 Hz, 2H), 5.86 (s, 2H), 5.78 (s, 1H), 5.52 (s, 1H), 3.24-3.12 (m, 2H), 1.94 (d, J = 1.2 Hz, 3H), 1.71-1.63 (m, 3H), 1.57 (s, 1H), 1.32 (q, J = 7.2 Hz, 1H), 0.94 (t, J = 7.2 Hz, 1H). | 503.2 |
| N-(4-(4-amino-5-(3-fluoro-4-((5-fluoropyrimidin-2-yl)oxy)phenyl)-7H-pyrrolo[2,3-d]pyrimidin-6-yl)phenyl)methacrylamide | 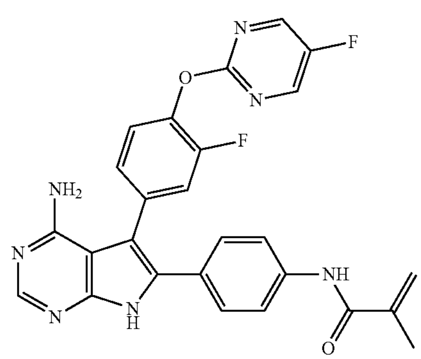 [SMILES: C=C(C)C(=O)Nc1ccc(-c2[nH]c3ncnc(N)c3c2-c2ccc(Oc3ncc(F)cn3)c(F)c2)cc1] | $^1$H NMR (400 MHz, DMSO-d$_6$) δ 12.14 (s, 1H), 9.85 (s, 1H), 8.81 (s, 2H), 8.14 (s, 1H), 7.70-7.59 (m, 2H), 7.48 (t, J = 8.4 Hz, 1H), 7.38-7.26 (m, 3H), 7.24 (dd, J = 8.3, 2.0 Hz, 1H), 5.80 (s, 3H), 5.53 (d, J = 1.7 Hz, 1H), 1.95 (s, 3H). | 500.35 |

TABLE 12-continued

Additional Exemplary Compounds

| Compound | Structure | Proton NMR | MS [M + 1] |
|---|---|---|---|
| N-(4-(7-(4-((6-methylpyridin-2-yl)oxy)phenyl)-5H-pyrrolo[3,2-d]pyrimidin-6-yl)phenyl)methacrylamide | 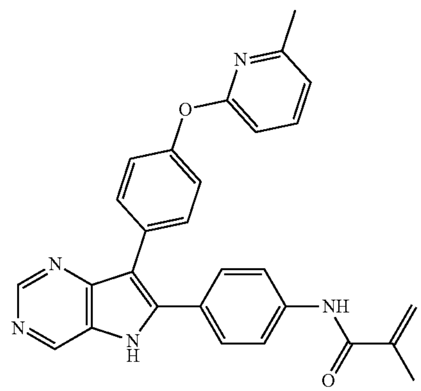 [SMILES: C=C(C)C(=O)Nc1ccc(-c2[nH]c3cncnc3c2-c2ccc(Oc3cccc(C)n3)cc2)cc1] | ¹H NMR (400 MHz, DMSO-d6) δ 12.24 (s, 1H), 9.99 (s, 1H), 8.91 (s, 1H), 8.86 (s, 1H), 7.83-7.76 (m, 2H), 7.75 (t, J = 7.8 Hz, 1H), 7.58-7.50 (m, 4H), 7.17-7.10 (m, 2H), 7.02 (d, J = 7.4 Hz, 1H), 6.80 (d, J = 8.2 Hz, 1H), 5.83 (s, 1H), 5.56 (s, 1H), 2.36 (s, 3H), 1.97 (d, J = 1.2 Hz, 3H). | 462.3 |
| N-(4-(4-amino-5-(4-((1-methyl-1H-pyrazol-3-yl)oxy)phenyl)-7H-pyrrolo[2,3-d]pyrimidin-6-yl)phenyl)acrylamide | 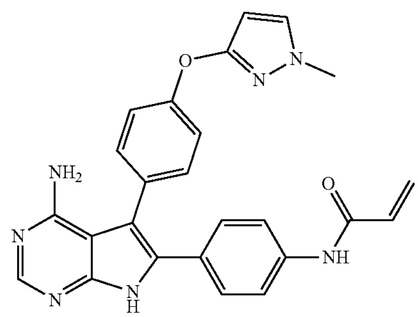 [SMILES: C=CC(=O)Nc1ccc(-c2[nH]c3ncnc(N)c3c2-c2ccc(Oc3ccn(C)n3)cc2)cc1] | 1H NMR (400 MHz, DMSO-d6) δ 11.75 (s, 1H), 10.13 (s, 1H), 8.12 (d, J = 13.8 Hz, 1H), 7.64 (d, J = 8.8 Hz, 2H), 7.59-7.52 (m, 2H), 7.46-7.39 (m, 2H), 7.23-7.14 (m, 3H), 6.57-6.37 (m, 1H), 6.24 (m, J = 17.0, 2.1 Hz, 1H), 5.96 (s, 2H), 5.81-5.69 (m, 1H), 3.80 (s, 3H). | 452 |
| N-(6-(4-amino-5-(4-((6-methylpyridin-2-yl)oxy)phenyl)-7H-pyrrolo[2,3-d]pyrimidin-6-yl)pyridin-3-yl)methacrylamide | 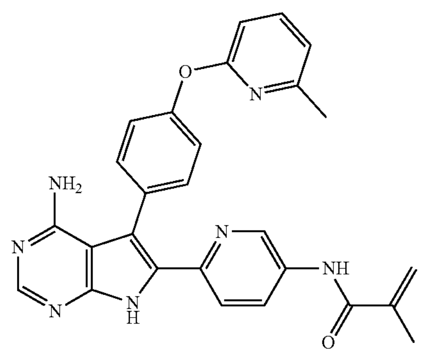 [SMILES: C=C(C)C(=O)Nc1ccc(-c2[nH]c3ncnc(N)c3c2-c2ccc(Oc3cccc(C)n3)cc2)nc1] | ¹H NMR (400 MHz, DMSO-d₆) δ 12.09 (s, 1H), 10.04 (s, 1H), 8.90 (d, J = 2.5 Hz, 1H), 8.13 (s, 1H), 7.91 (dd, J = 8.8, 2.5 Hz, 1H), 7.78 (t, J = 7.8 Hz, 1H), 7.50-7.42 (m, 2H), 7.28-7.20 (m, 2H), 7.07 (t, J = 7.6 Hz, 2H), 6.88 (d, J = 8.1 Hz, 1H), 5.85 (s, 2H), 5.58 (s, 1H), 2.39 (s, 3H), 1.96 (t, J = 1.2 Hz, 3H). | 478.30 |
| N-(4-(4-amino-7-methyl-5-(4-(pyrrolidine-1-carbonyl)phenyl)-7H-pyrrolo[2,3-d]pyrimidin-6-yl)phenyl)aziridine-2-carboxamide | 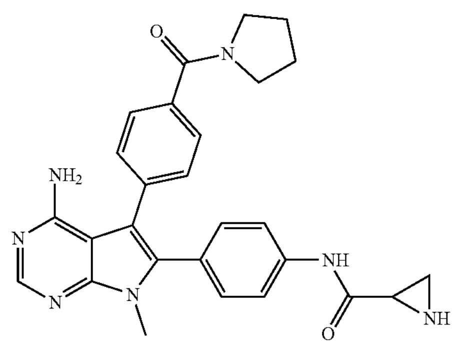 [SMILES: Cn1c(-c2ccc(NC(=O)C3CN3)cc2)c(-c2ccc(C(=O)N3CCCC3)cc2)c2c(N)ncnc21] | ¹H NMR (400 MHz, Methanol-d₄) δ 8.22 (s, 1H), 7.55-7.49 (m, 2H), 7.43 (d, J = 8.3 Hz, 2H), 7.40-7.29 (m, 4H), 4.33 (dd, J = 5.6, 2.6 Hz, 1H), 3.99 (t, J = 5.8 Hz, 1H), 3.69 (s, 3H), 3.61 (t, J = 6.9 Hz, 2H), 3.50 (t, J = 6.6 Hz, 2H), 3.45 (dd, J = 6.0, 2.7 Hz, 1H), 1.97 (dq, J = 25.9, 6.8 Hz, 4H). | 482.20 |

TABLE 12-continued

Additional Exemplary Compounds

| Compound | Structure | Proton NMR | MS [M + 1] |
|---|---|---|---|
| (R)-N-(4-(4-amino-7-methyl-5-(4-(pyrrolidine-1-carbonyl)phenyl)-7H-pyrrolo[2,3-d]pyrimidin-6-yl)phenyl)aziridine-2-carboxamide | 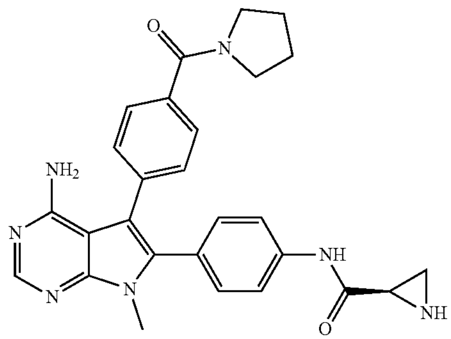 [SMILES: Cn1c(-c2ccc(NC(=O)[C@H]3CN3)cc2)c(-c2ccc(C(=O)N3CCCC3)cc2)c2c(N)ncnc21] | $^1$H NMR (400 MHz, Methanol-$d_4$) δ 8.22 (s, 1H), 7.55-7.49 (m, 2H), 7.43 (d, J = 8.3 Hz, 2H), 7.40-7.29 (m, 4H), 4.33 (dd, J = 5.6, 2.6 Hz, 1H), 3.99 (t, J = 5.8 Hz, 1H), 3.69 (s, 3H), 3.61 (t, J = 6.9 Hz, 2H), 3.50 (t, J = 6.6 Hz, 2H), 3.45 (dd, J = 6.0, 2.7 Hz, 1H), 1.97 (dq, J = 25.9, 6.8 Hz, 4H). | 482.20 |
| (S)-N-(4-(4-amino-7-methyl-5-(4-(pyrrolidine-1-carbonyl)phenyl)-7H-pyrrolo[2,3-d]pyrimidin-6-yl)phenyl)aziridine-2-carboxamide | 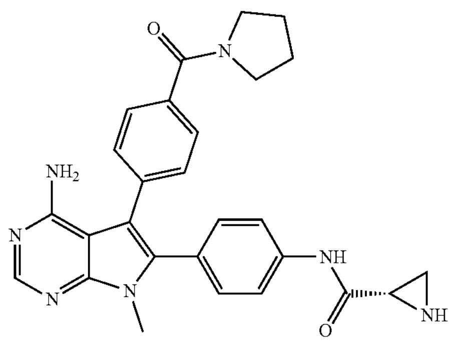 [SMILES: Cn1c(-c2ccc(NC(=O)[C@@H]3CN3)cc2)c(-c2ccc(C(=O)N3CCCC3)cc2)c2c(N)ncnc21] | $^1$H NMR (400 MHz, Methanol-$d_4$) δ 8.22 (s, 1H), 7.55-7.49 (m, 2H), 7.43 (d, J = 8.3 Hz, 2H), 7.40-7.29 (m, 4H), 4.33 (dd, J = 5.6, 2.6 Hz, 1H), 3.99 (t, J = 5.8 Hz, 1H), 3.69 (s, 3H), 3.61 (t, J = 6.9 Hz, 2H), 3.50 (t, J = 6.6 Hz, 2H), 3.45 (dd, J = 6.0, 2.7 Hz, 1H), 1.97 (dq, J = 25.9, 6.8 Hz, 4H). | 482.20 |
| (4-(4-amino-7-methyl-6-(1-methyl-2-vinyl-1H-benzo[d]imidazol-6-yl)-7H-pyrrolo[2,3-d]pyrimidin-5-yl)phenyl)(pyrrolidin-1-yl)methanone | 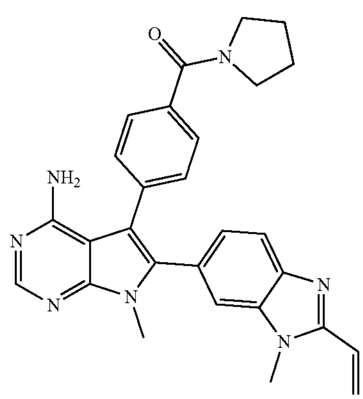 [SMILES: C=Cc1nc2ccc(-c3c(-c4ccc(C(=O)N5CCCC5)cc4)c4c(N)ncnc4n3C)cc2n1C] | $^1$H NMR (400 MHz, DMSO-$d_6$) δ 8.23 (s, 1H), 7.62 (d, J = 1.6 Hz, 1H), 7.57 (d, J = 8.3 Hz, 1H), 7.48-7.42 (m, 2H), 7.31-7.25 (m, 2H), 7.12-7.05 (m, 1H), 7.04 (dd, J = 16.1, 10.0 Hz, 1H), 6.43 (dd, J = 17.1, 2.1 Hz, 1H), 5.94 (s, 1H), 5.73 (dd, J = 11.0, 2.0 Hz, 1H), 3.80 (s, 3H), 3.64 (s, 3H), 3.41 (dt, J = 24.1, 6.5 Hz, 4H), 1.82 (dq, J = 19.1, 6.8 Hz, 4H). | 478.25 |
| (S)-N-(5-(4-amino-7-methyl-5-(4-(pyrrolidine-1-carbonyl)phenyl)-7H-pyrrolo[2,3-d]pyrimidin-6-yl)-1-methyl-1H-pyrazol-3-yl)methacrylamide | 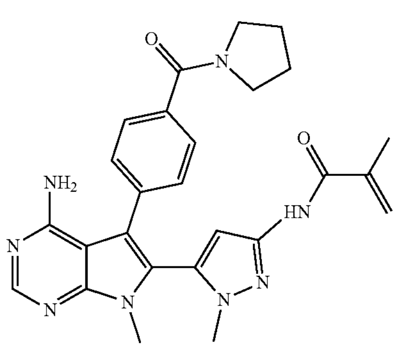 [SMILES: C=C(C)C(=O)Nc1cc(-c2c(-c3ccc(C(=O)N4CCCC4)cc3)c3c(N)ncnc3n2C)n(C)n1] | $^1$H NMR (400 MHz, Chloroform-d) δ 8.43 (s, 1H), 8.13 (s, 1H), 7.59 (d, J = 7.9 Hz, 2H), 7.36 (d, J = 7.7 Hz, 2H), 7.05 (s, 1H), 5.89 (s, 1H), 5.53 (d, J = 1.8 Hz, 1H), 5.20 (s, 2H), 3.74 (s, 3H), 3.68 (t, J = 6.9 Hz, 2H), 3.47 (t, J = 6.5 Hz, 2H), 3.25 (s, 3H), 2.09 (s, 3H), 1.97 (dp, J = 24.7, 6.7 Hz, 4H). | 485.20 |

TABLE 12-continued

Additional Exemplary Compounds

| Compound | Structure | Proton NMR | MS [M + 1] |
|---|---|---|---|
| (4-(4-amino-7-methyl-6-(1-methyl-2-vinyl-1H-benzo[d]imidazol-5-yl)-7H-pyrrolo[2,3-d]pyrimidin-5-yl)phenyl)(pyrrolidin-1-yl)methanone | 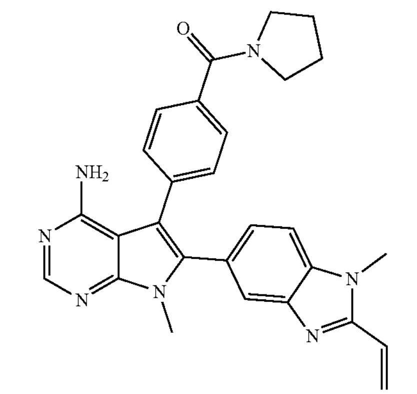 [SMILES: C=Cc1nc2cc(-c3c(-c4ccc(C(=O)N5CCCC5)cc4)c4c(N)ncnc4n3C)ccc2n1C] | $^1$H NMR (400 MHz, DMSO-d$_6$) δ 8.22 (s, 1H), 7.62-7.53 (m, 2H), 7.48-7.41 (m, 2H), 7.30-7.23 (m, 2H), 7.16 (dd, J = 8.3, 1.5 Hz, 1H), 7.04 (dd, J = 17.1, 11.0 Hz, 1H), 6.41 (dd, J = 17.1, 2.1 Hz, 1H), 5.92 (s, 2H), 5.72 (dd, J = 11.0, 2.1 Hz, 1H), 3.85 (s, 3H), 3.61 (s, 3H), 3.41 (dt, J = 18.5, 6.5 Hz, 4H), 1.81 (dq, J = 20.2, 6.8 Hz, 4H). | 478.25 |
| (S)-N-(4-(4-amino-7-methyl-5-(2-oxo-4-(pyrrolidine-1-carbonyl)piperidin-1-yl)-7H-pyrrolo[2,3-d]pyrimidin-6-yl)phenyl)methacrylamide | 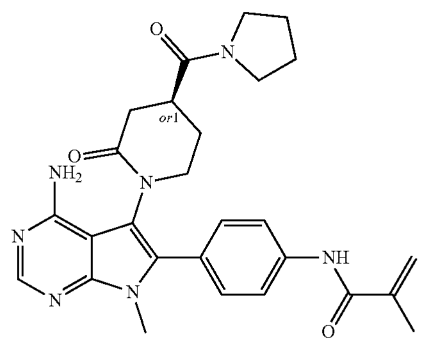 [SMILES: C=C(C)C(=O)Nc1ccc(-c2c(N3CC[C@H](C(=O)N4CCCC4)CC3=O)c3c(N)ncnc3n2C)cc1] | $^1$H NMR (400 MHz, DMSO-d$_6$) δ 9.98 (s, 1H), 8.10 (s, 1H), 7.88-7.80 (m, 2H), 7.42-7.33 (m, 2H), 6.91 (s, 2H), 5.83 (t, J = 1.1 Hz, 1H), 5.59-5.53 (m, 1H), 3.62 (s, 3H), 3.53 (dt, J = 10.2, 6.6 Hz, 1H), 3.45-3.33 (m, 2H), 3.32-3.29 (m, 1H), 3.15 (s, 1H), 2.95 (dd, J = 11.4, 4.9 Hz, 1H), 2.49-2.32 (m, 2H), 1.98 (d, J = 1.2 Hz, 4H), 1.88 (p, J = 6.2 Hz, 2H), 1.79 (p, J = 7.8, 7.1 Hz, 2H), 1.68 (s, 1H), 1.24 (s, 1H). | 502.25 |
| (R)-N-(4-(4-amino-7-methyl-5-(2-oxo-4-(pyrrolidine-1-carbonyl)piperidin-1-yl)-7H-pyrrolo[2,3-d]pyrimidin-6-yl)phenyl)methacrylamide | 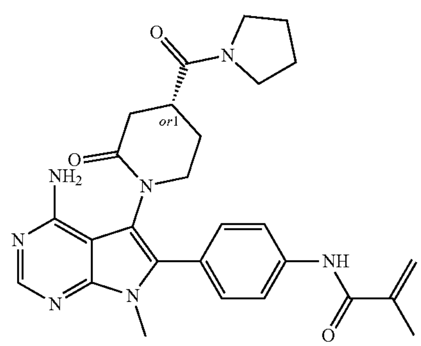 [SMILES: C=C(C)C(=O)Nc1ccc(-c2c(N3CC[C@@H](C(=O)N4CCCC4)CC3=O)c3c(N)ncnc3n2C)cc1] | $^1$H NMR (400 MHz, DMSO-d$_6$) δ 9.98 (s, 1H), 8.10 (s, 1H), 7.88-7.80 (m, 2H), 7.43-7.33 (m, 2H), 6.93 (s, 1H), 5.83 (t, J = 1.0 Hz, 1H), 5.59-5.53 (m, 1H), 3.62 (s, 3H), 3.53 (dt, J = 10.3, 6.6 Hz, 1H), 3.45-3.33 (m, 2H), 3.32 (s, 1H), 3.15 (s, 1H), 2.99-2.91 (m, 1H), 2.47-2.33 (m, 2H), 1.98 (d, J = 1.2 Hz, 4H), 1.88 (d, J = 6.6 Hz, 2H), 1.80 (d, J = 6.5 Hz, 2H), 1.73-1.61 (m, 1H), 1.24 (s, 1H). | 502.25 |
| N-(4-(4-amino-7-methyl-5-(4-(4-methylpyrimidin-2-yloxy)phenyl)-7H-pyrrolo[2,3-d]pyrimidin-6-yl)phenyl)-2-chloroacetamide | 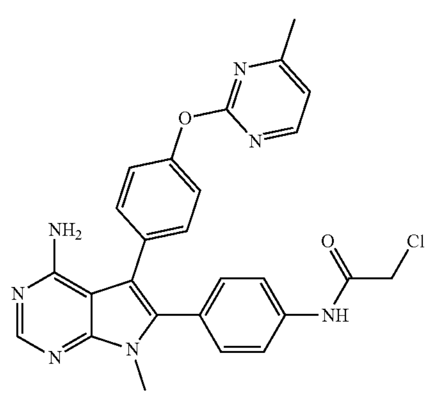 [SMILES: Cc1ccnc(Oc2ccc(-c3c(-c4ccc(NC(=O)CCl)cc4)n(C)c4ncnc(N)c34)cc2)n1] | $^1$H NMR (400 MHz, Methanol-d$_4$) δ 8.41 (d, J = 5.1 Hz, 1H), 8.21 (s, 1H), 7.66 (d, J = 8.5 Hz, 2H), 7.35 (t, J = 9.3 Hz, 4H), 7.24-7.06 (m, 3H), 4.21 (s, 2H), 3.71 (s, 3H), 2.50 (s, 3H). | 500.30 |

TABLE 12-continued

Additional Exemplary Compounds

| Compound | Structure | Proton NMR | MS [M + 1] |
|---|---|---|---|
| 7-methyl-5-(4-(4-methylpyrimidin-2-yloxy)phenyl)-6-(2-vinylpyrimidin-5-yl)-7H-pyrrolo[2,3-d]pyrimidin-4-amine | 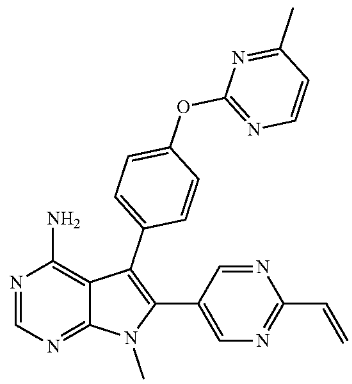 [SMILES: C=Cc1ncc(-c2c(-c3ccc(Oc4nccc(C)n4)cc3)c3c(N)ncnc3n2C)cn1] | $^1$H NMR (400 MHz, Chloroform-d) δ 8.66 (s, 2H), 8.44-8.36 (m, 2H), 7.40-7.30 (m, 2H), 7.38-7.23 (m, 2H), 6.98-6.86 (m, 2H), 6.68 (dd, J = 17.4, 1.7 Hz, 1H), 5.82 (dd, J = 10.6, 1.7 Hz, 1H), 5.16 (s, 2H), 3.81 (s, 3H), 2.53 (s, 3H). | 437.25 |
| (R)-(3-(4-amino-7-methyl-5-(4-(4-methylpyrimidin-2-yl)oxy)phenyl)-7H-pyrrolo[2,3-d]pyrimidin-6-yl)-2,5-dihydro-1H-pyrrol-1-yl)(oxiran-2-yl)methanone | 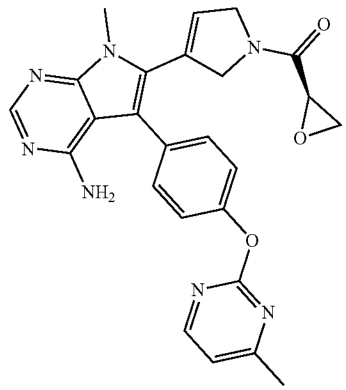 [SMILES: Cc1ccnc(Oc2ccc(-c3c(C4=CCN(C(=O)[C@H]5CO5)C4)n(C)c4ncnc(N)c34)cc2)n1] | $^1$H NMR (400 MHz, Methanol-d$_4$) δ 8.44 (dd, J = 5.1, 3.5 Hz, 1H), 8.19 (d, J = 2.8 Hz, 1H), 7.58-7.48 (m, 2H), 7.38-7.27 (m, 2H), 7.16 (dd, J = 5.1, 2.3 Hz, 1H), 6.25 (dt, J = 23.2, 2.0 Hz, 1H), 4.82-4.61 (m, 1H), 4.49-4.29 (m, 2H), 4.20 (d, J = 3.9 Hz, 1H), 3.87 (d, J = 13.1 Hz, 3H), 3.60 (ddd, J = 90.2, 4.3, 2.4 Hz, 1H), 2.94 (ddd, J = 36.6, 6.4, 4.3 Hz, 1H), 2.81 (ddd, J = 28.6, 6.4, 2.4 Hz, 1H), 2.52 (d, J = 2.1 Hz, 3H). | 470.20 |
| (S)-(3-(4-amino-7-methyl-5-((4-methylpyrimidin-2-yl)oxy)phenyl)-7H-pyrrolo[2,3-d]pyrimidin-6-yl)-2,5-dihydro-1H-pyrrol-1-yl)(oxiran-2-yl)methanone | | $^1$H NMR (400 MHz, Methanol-d$_4$) δ 8.44 (dd, J = 5.1, 3.5 Hz, 1H), 8.19 (d, J = 2.8 Hz, 1H), 7.58-7.48 (m, 2H), 7.38-7.27 (m, 2H), 7.16 (dd, J = 5.1, 2.3 Hz, 1H), 6.25 (dt, J = 23.2, 2.0 Hz, 1H), 4.82-4.61 (m, 1H), 4.49-4.29 (m, 2H), 4.20 (d, J = 3.9 Hz, 1H), 3.87 (d, J = 13.1 Hz, 3H), 3.60 (ddd, J = 90.2, 4.3, 2.4 Hz, 1H), 2.94 (ddd, J = 36.6, 6.4, 4.3 Hz, 1H), 2.81 (ddd, J = 28.6, 6.4, 2.4 Hz, 1H), 2.52 (d, J = 2.1 Hz, 3H). | 470.20 |
| N-(4-(4-amino-7-methyl-5-(4-(pyrrolidine-1-carbonyl)phenyl)-7H-pyrrolo[2,3-d]pyrimidin-6-yl)phenyl)-2-cyanoacetamide | 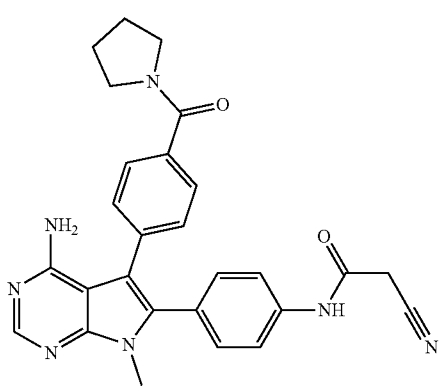 [SMILES: Cn1c(-c2ccc(NC(=O)CC#N)cc2)c(-c2ccc(C(=O)N3CCCC3)cc2)c2c(N)ncnc21] | 1H NMR (400 MHz, DMSO-d6) δ 10.42 (s, 1H), 8.21 (s, 1H), 7.57 (d, J = 8.3 Hz, 2H), 7.49 (d, J = 8.1 Hz, 2H), 7.33-7.22 (m, 4H), 6.00 (s, 2H), 3.92 (s, 2H), 3.61 (s, 3H), 3.44 (dt, J = 19.1, 6.5 Hz, 4H), 1.84 (dq, J = 18.4, 6.8 Hz, 4H). | 480.20 |

TABLE 12-continued

Additional Exemplary Compounds

| Compound | Structure | Proton NMR | MS [M + 1] |
|---|---|---|---|
| N-(4-(4-amino-7-methyl-5-(4-(4-methylpyrimidin-2-yloxy)phenyl)-7H-pyrrolo[2,3-d]pyrimidin-6-yl)phenyl)-4,5-dihydrofuran-3-carboxamide | 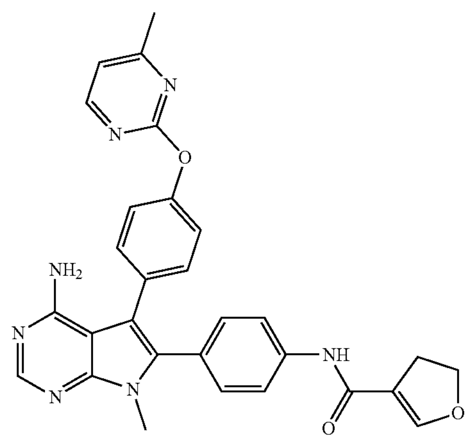 [SMILES: Cc1ccnc(Oc2ccc(-c3c(-c4ccc(NC(=O)C5=COCC5)cc4)n(C)c4ncnc(N)c34)cc2)n1] | ¹H NMR (400 MHz, DMSO-d₆) δ 9.47 (s, 1H), 8.47 (d, J = 5.0 Hz, 1H), 8.20 (s, 1H), 7.75-7.64 (m, 2H), 7.51 (d, J = 1.9 Hz, 1H), 7.29 (d, J = 8.4 Hz, 4H), 7.21-7.14 (m, 3H), 5.90 (s, 1H), 4.52 (t, J = 9.7 Hz, 2H), 3.61 (s, 3H), 3.06-2.75 (m, 2H), 2.41 (s, 3H). | 520.25 |
| N-(4-(4-amino-7-methyl-5-(4-((4-methylpyrimidin-2-yl)oxy)phenyl)-7H-pyrrolo[2,3-d]pyrimidin-6-yl)phenyl)-2,5-dihydrofuran-3-carboxamide | 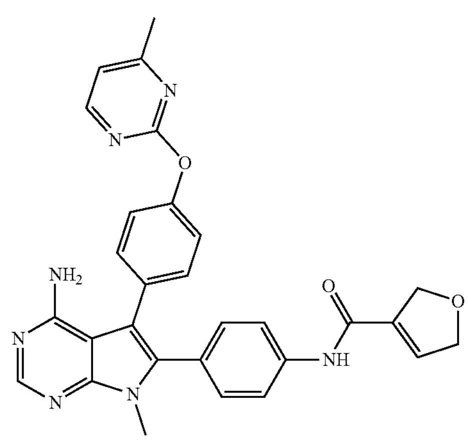 [SMILES: Cc1ccnc(Oc2ccc(-c3c(-c4ccc(NC(=O)C5=CCOC5)cc4)n(C)c4ncnc(N)c34)cc2)n1] | ¹H NMR (400 MHz, DMSO-d₆) δ 10.05 (s, 1H), 8.46 (d, J = 5.0 Hz, 1H), 8.21 (s, 1H), 7.75-7.68 (m, 2H), 7.37-7.25 (m, 4H), 7.22-7.12 (m, 3H), 6.97-6.92 (m, 1H), 5.93 (s, 2H), 4.77 (h, J = 2.9 Hz, 4H), 3.61 (s, 3H), 2.41 (s, 3H). | 520.20 |
| 5-(4-(4-amino-7-methyl-5-(4-(4-methylpyrimidin-2-yloxy)phenyl)-7H-pyrrolo[2,3-d]pyrimidin-6-yl)phenyl)thiazole-2-carbonitrile | 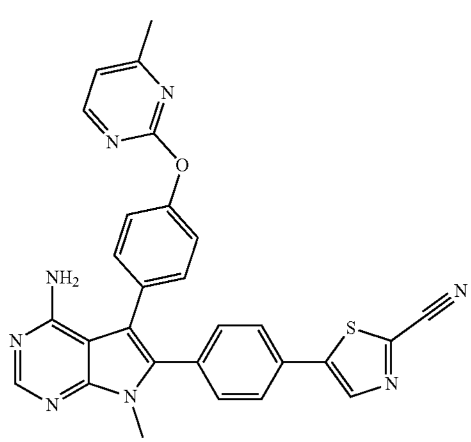 | ¹H NMR (400 MHz, DMSO-d₆) δ 8.72 (s, 1H), 8.47 (d, J = 5.0 Hz, 1H), 8.23 (s, 1H), 7.86 (d, J = 8.3 Hz, 2H), 7.53 (d, J = 8.3 Hz, 2H), 7.33 (d, J = 8.5 Hz, 2H), 7.24-7.19 (m, 2H), 7.16 (d, J = 5.0 Hz, 1H), 3.67 (s, 3H), 2.41 (s, 3H). | 517.20 |

TABLE 12-continued

Additional Exemplary Compounds

| Compound | Structure | Proton NMR | MS [M + 1] |
|---|---|---|---|
| 5-(4-(4-amino-7-methyl-5-(4-((4-methylpyrimidin-2-yl)oxy)phenyl)-7H-pyrrolo[2,3-d]pyrimidin-6-yl)phenyl)oxazole-2-carbonitrile | 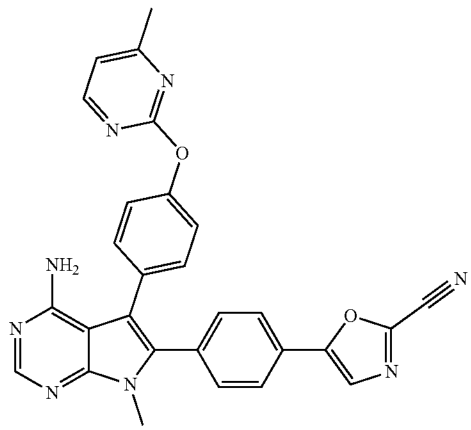 | $^1$H NMR (400 MHz, DMSO-d$_6$) δ 8.47 (d, J = 5.0 Hz, 1H), 8.23 (s, 1H), 8.17 (s, 1H), 7.88 (d, J = 8.2 Hz, 2H), 7.55 (d, J = 8.1 Hz, 2H), 7.31 (d, J = 8.2 Hz, 2H), 7.23-7.13 (m, 3H), 5.98 (s, 1H), 3.67 (s, 3H), 2.41 (s, 3H). | 501.15 |
| 7-methyl-5-(4-((4-methylpyrimidin-2-yl)oxy)phenyl)-6-(4-(2-vinylthiazol-5-yl)phenyl)-7H-pyrrolo[2,3-d]pyrimidin-4-amine | 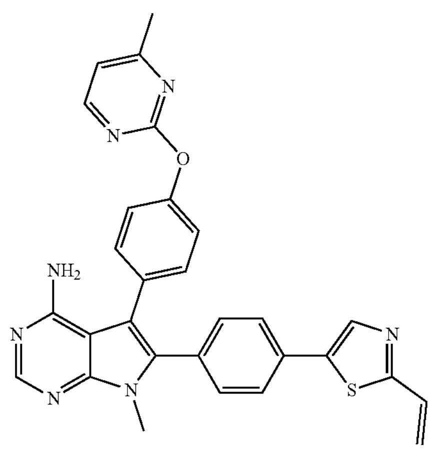 [SMILES: C=Cc1ncc(-c2ccc(-c3c(-c4ccc(Oc5nccc(C)n5)cc4)c4c(N)ncnc4n3C)cc2)s1] | $^1$H NMR (400 MHz, Chloroform-d) δ 8.42-8.36 (m, 2H), 7.99 (s, 1H), 7.63-7.55 (m, 2H), 7.38-7.30 (m, 4H), 7.26-7.16 (m, 2H), 6.99-6.88 (m, 2H), 6.09 (d, J = 17.5 Hz, 1H), 5.61 (d, J = 10.9 Hz, 1H), 5.27 (s, 2H), 3.80 (s, 3H), 2.52 (s, 3H). | 518.25 |
| 6-(4-(2-chlorooxazol-5-yl)phenyl)-7-methyl-5-(4-((4-methylpyrimidin-2-yl)oxy)phenyl)-7H-pyrrolo[2,3-d]pyrimidin-4-amine | 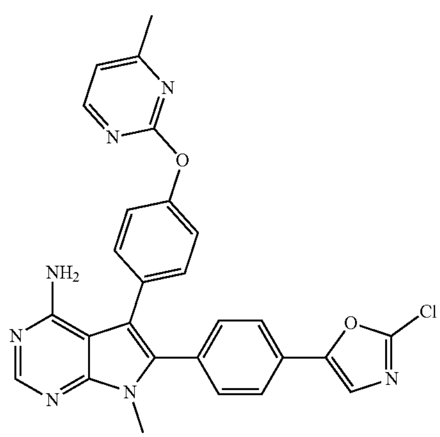 [SMILES: Cc1ccnc(Oc2ccc(-c3c(-c4ccc(-c5cnc(Cl)o5)cc4)n(C)c4ncnc(N)c34)cc2)n1] | 1H NMR (400 MHz, DMSO-d6) δ 8.47 (d, J = 5.0 Hz, 1H), 8.23 (s, 1H), 7.86 (s, 1H), 7.76-7.69 (m, 2H), 7.53-7.46 (m, 2H), 7.34-7.27 (m, 2H), 7.23-7.13 (m, 3H), 3.66 (s, 3H), 2.41 (s, 3H), 1.24 (s, 1H). | 510.15 |

TABLE 12-continued

Additional Exemplary Compounds

| Compound | Structure | Proton NMR | MS [M + 1] |
|---|---|---|---|
| 6-(4-(2-ethynyloxazol-5-yl)phenyl)-7-methyl-5-(4-((4-methylpyrimidin-2-yl)oxy)phenyl)-7H-pyrrolo[2,3-d]pyrimidin-4-amine | 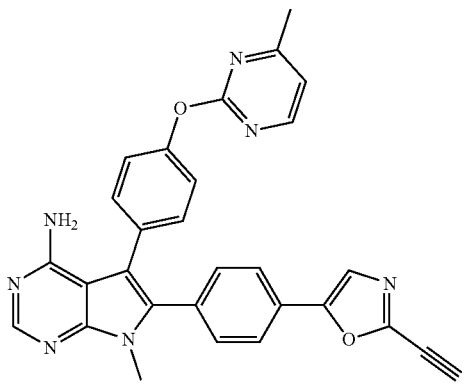 [SMILES: C#Cc1ncc(-c2ccc(-c3c(-c4ccc(Oc5nccc(C)n5)cc4)c4c(N)ncnc4n3C)cc2)o1] | 1H NMR (400 MHz, DMSO-d6) 8.46 (s, 1H), 8.23 (s, 1H), 7.89 (s, 1H), 7.80-7.75 (m, 2H), 7.50 (s, 2H), 7.31 (m, 2H), 7.19 (s, 3H), 5.95 (s, 1H), 4.97 (s, 1H), 3.66 (s, 3H), 2.41 (s, 3H). | 500.15 |
| 6-(2-fluoropyrimidin-5-yl)-7-methyl-5-(4-((4-methylpyrimidin-2-yl)oxy)phenyl)-7H-pyrrolo[2,3-d]pyrimidin-4-amine | 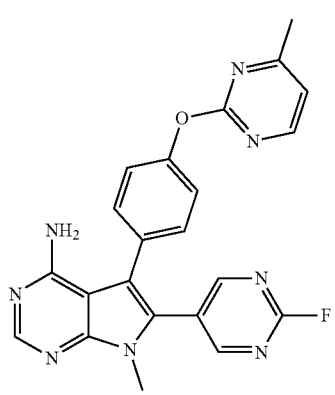 [SMILES: Cc1ccnc(Oc2ccc(-c3c(-c4cnc(F)nc4)n(C)c4ncnc(N)c34)cc2)n1] | 1H NMR (400 MHz, DMSO-d6) δ 8.85 (d, J = 1.5 Hz, 2H), 8.48 (d, J = 5.0 Hz, 1H), 8.25 (s, 1H), 7.44-7.31 (m, 2H), 7.26-7.21 (m, 2H), 5.81 (s, 1H), 7.17 (d, J = 5.0 Hz, 1H), 3.70 (s, 3H), 2.42 (s, 3H). | 429.10 |
| (S)-7-methyl-5-(4-((4-methylpyrimidin-2-yl)oxy)phenyl)-6-(4-(oxiran-2-ylmethoxy)phenyl)-7H-pyrrolo[2,3-d]pyrimidin-4-amine | 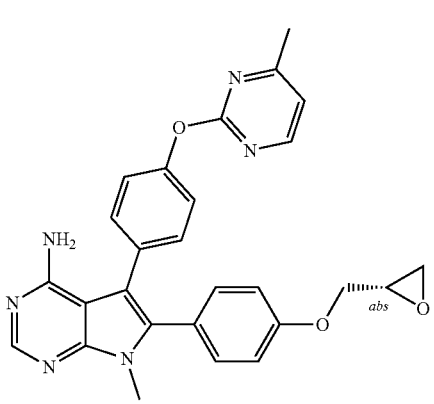 [SMILES: Cc1ccnc(Oc2ccc(-c3c(-c4ccc(OC[C@@H]5CO5)cc4)n(C)c4ncnc(N)c34)cc2)n1] | $^1$H NMR (400 MHz, DMSO-d$_6$) δ 8.47 (d, J = 5.0 Hz, 1H), 8.20 (s, 1H), 7.39-7.23 (m, 4H), 7.22-7.09 (m, 3H), 7.07-6.92 (m, 2H), 5.82 (d, J = 52.7 Hz, 2H), 4.36 (dd, J = 11.3, 2.8 Hz, 1H), 3.86 (dd, J = 11.4, 6.6 Hz, 1H), 3.58 (s, 3H), 3.17 (d, J = 5.3 Hz, 1H), 2.85 (t, J = 4.7 Hz, 1H), 2.76-2.61 (m, 1H), 2.42 (s, 3H). | 481.20 |

TABLE 12-continued

Additional Exemplary Compounds

| Compound | Structure | Proton NMR | MS [M + 1] |
|---|---|---|---|
| 1-(4-(4-amino-7-methyl-5-(4-((4-methylpyrimidin-2-yl)oxy)phenyl)-7H-pyrrolo[2,3-d]pyrimidin-6-yl)phenyl)azetidin-2-one | 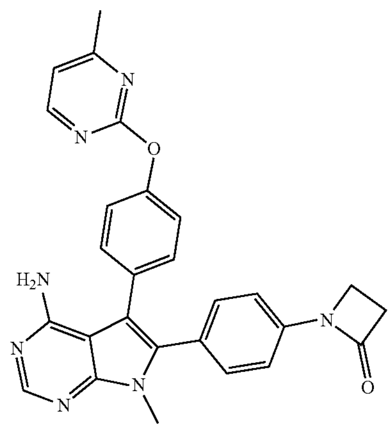 [SMILES: Cc1ccnc(Oc2ccc(-c3c(-c4ccc(N5CCC5=O)cc4)n(C)c4ncnc(N)c34)cc2)n1] | 1H NMR (400 MHz, DMSO-d6) δ 8.47 (d, J = 5.0 Hz, 1H), 8.21 (s, 1H), 7.37 (s, 4H), 7.31-7.25 (m, 2H), 7.21-7.14 (m, 3H), 5.84 (d, J = 60.6 Hz, 1H), 3.65 (t, J = 4.5 Hz, 2H), 3.60 (s, 3H), 3.09 (t, J = 4.5 Hz, 2H), 2.41 (s, 3H). | 478.15 |
| 7-methyl-5-(4-((4-methylpyrimidin-2-yl)oxy)phenyl)-6-(4-((oxiran-2-ylmethyl)amino)phenyl)-7H-pyrrolo[2,3-d]pyrimidin-4-amine | 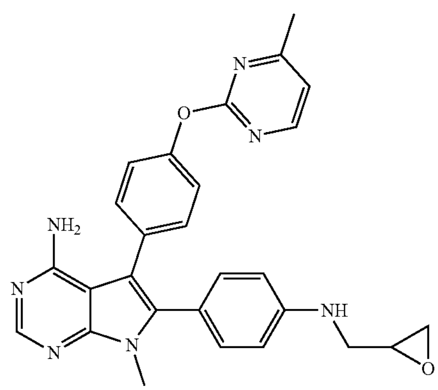 [SMILES: Cc1ccnc(Oc2ccc(-c3c(-c4ccc(NCC5CO5)cc4)n(C)c4ncnc(N)c34)cc2)n1] | 1H NMR (400 MHz, DMSO-d6) δ 8.47 (d, J = 5.0 Hz, 1H), 8.17 (s, 1H), 7.33-7.24 (m, 2H), 7.21-7.12 (m, 3H), 7.11-7.00 (m, 2H), 6.64 (d, J = 8.5 Hz, 2H), 6.14 (t, J = 5.6 Hz, 1H), 5.81 (s, 1H), 3.58 (s, 3H), 3.40-3.33 (m, 1H), 3.09 (td, J = 7.6, 6.2, 3.5 Hz, 2H), 2.75 (dd, J = 5.1, 3.9 Hz, 1H), 2.60 (dd, J = 5.1, 2.3 Hz, 1H), 2.42 (s, 3H), | 480.15 |
| (R)-7-methyl-5-(4-((4-methylpyrimidin-2-yl)oxy)phenyl)-6-(4-(oxiran-2-ylmethoxy)phenyl)-7H-pyrrolo[2,3-d]pyrimidin-4-amine | 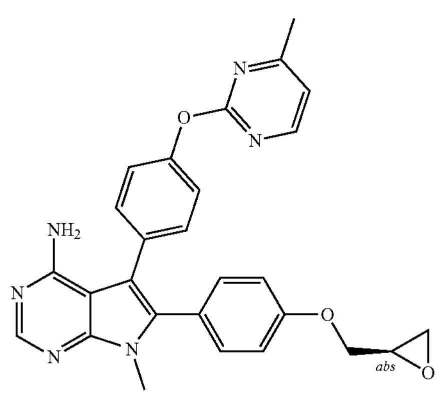 [SMILES: Cc1ccnc(Oc2ccc(-c3c(-c4ccc(OC[C@H]5CO5)cc4)n(C)c4ncnc(N)c34)cc2)n1] | $^1$H NMR (400 MHz, DMSO-d$_6$) δ 8.47 (d, J = 5.0 Hz, 1H), 8.20 (s, 1H), 7.38-7.22 (m, 4H), 7.22-7.11 (m, 3H), 7.07-6.97 (m, 2H), 4.36 (dd, J = 11.4, 2.8 Hz, 1H), 3.86 (dd, J = 11.3, 6.6 Hz, 1H), 3.58 (s, 3H), 3.31 (s, 1H), 2.85 (dd, J = 5.1, 4.2 Hz, 1H), 2.72 (dd, J = 5.1, 2.7 Hz, 1H), 2.41 (s, 3H). | 481.25 |

TABLE 12-continued

Additional Exemplary Compounds

| Compound | Structure | Proton NMR | MS [M + 1] |
|---|---|---|---|
| 7-methyl-5-(4-(4-methylpyrimidin-2-yl)oxy)phenyl)-6-(4-(2-vinyloxazol-5-yl)phenyl)-7H-pyrrolo[2,3-d]pyrimidin-4-amine | 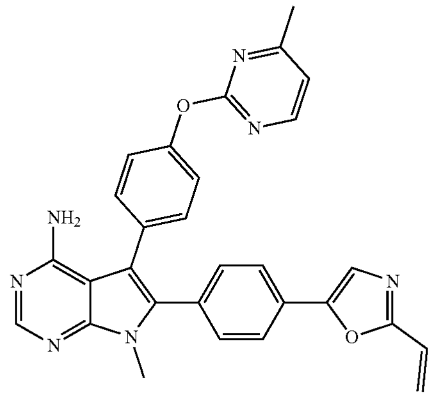 [SMILES: C=Cc1ncc(-c2ccc(-c3c(-c4ccc(Oc5nccc(C)n5)cc4)c4c(N)ncnc4n3C)cc2)o1] | $^1$H NMR (400 MHz, DMSO-d$_6$) δ 8.46 (d, J = 5.0 Hz, 1H), 8.22 (s, 1H), 7.84-7.76 (m, 3H), 7.51-7.45 (m, 2H), 7.35-7.27 (m, 2H), 7.23-7.12 (m, 3H), 6.70 (dd, J = 17.6, 11.2 Hz, 1H), 6.26 (dd, J = 17.6, 1.1 Hz, 1H), 6.03 (s, 1H), 5.91 (s, 1H), 5.79-5.72 (m, 1H), 3.66 (s, 3H), 2.40 (s, 3H). | 502.15 |
| methyl (4-(4-amino-7-methyl-5-(4-(pyrrolidine-1-carbonyl)phenyl)-7H-pyrrolo[2,3-d]pyrimidin-6-yl)phenyl) carbamate | 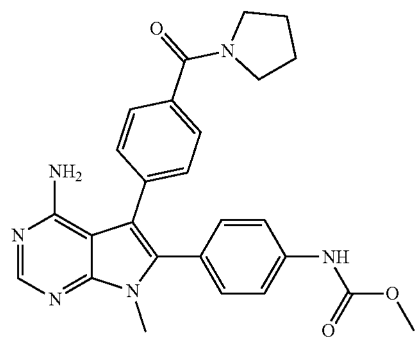 [SMILES: COC(=O)Nc1ccc(-c2c(-c3ccc(C(=O)N4CCCC4)cc3)c3c(N)ncnc3n2C)cc1] | $^1$H NMR (400 MHz, DMSO-d$_6$) δ 9.80 (s, 1H), 8.20 (s, 1H), 7.48 (dd, J = 8.7, 7.1 Hz, 4H), 7.32-7.18 (m, 4H), 3.67 (s, 3H), 3.60 (s, 3H), 3.43 (dt, J = 16.5, 6.5 Hz, 4H), 1.83 (dq, J = 18.3, 6.7 Hz, 4H). | 471.25 |
| 1-(7-(4-amino-7-methyl-5-(4-((4-methylpyrimidin-2-yl)oxy)phenyl)-7H-pyrrolo[2,3-d]pyrimidin-6-yl)-3,4-dihydroisoquinolin-2(1H)-yl)prop-2-en-1-one | 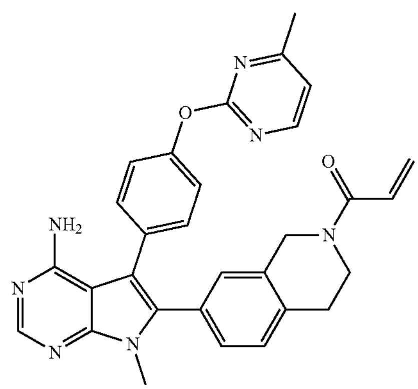 [SMILES: C=CC(=O)N1CCc2ccc(-c3c(-c4ccc(Oc5nccc(C)n5)cc4)c4c(N)ncnc4n3C)cc2C1] | $^1$H NMR (400 MHz, DMSO-d$_6$) δ 8.46 (d, J = 5.0 Hz, 1H), 8.20 (s, 1H), 7.36-7.26 (m, 2H), 7.25-7.09 (m, 6H), 6.89 (dd, J = 16.6, 10.6 Hz, 1H), 6.15 (dd, J = 16.7, 2.4 Hz, 1H), 5.72 (dd, J = 10.4, 2.4 Hz, 1H), 4.76 (d, J = 41.4 Hz, 2H), 3.78 (dt, J = 24.4, 5.9 Hz, 2H), 3.61 (s, 3H), 2.94-2.71 (m, 2H), 2.41 (s, 3H). | 518.20 |
| (R)-N-(7-(4-amino-7-methyl-5-(4-((4-methylpyrimidin-2-yl)oxy)phenyl)-7H-pyrrolo[2,3-d]pyrimidin-6-yl)-1,2,3,4-tetrahydronaphthalen-2-yl)acrylamide | 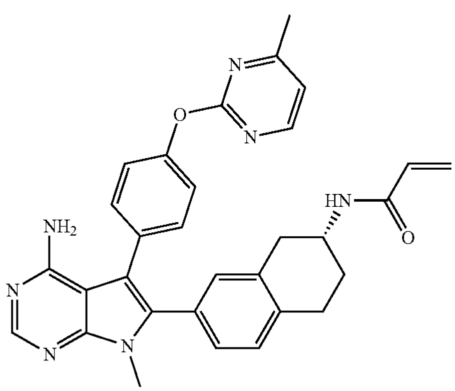 [SMILES: C=CC(=O)N[C@@H]1CCc2ccc(-c3c(-c4ccc(Oc5nccc(C)n5)cc4)c4c(N)ncnc4n3C)cc2C1] | $^1$H NMR (400 MHz, DMSO-d$_6$) δ 8.46 (d, J = 5.0 Hz, 1H), 8.23-8.14 (m, 2H), 7.38-7.29 (m, 2H), 7.24-7.07 (m, 6H), 6.26 (dd, J = 17.1, 10.0 Hz, 1H), 6.10 (dd, J = 17.1, 2.4 Hz, 1H), 5.97-5.69 (m, 1H), 5.59 (dd, J = 10.1, 2.4 Hz, 1H), 4.03 (s, 1H), 3.61 (s, 3H), 2.97 (dd, J = 16.6, 5.3 Hz, 1H), 2.85 (d, J = 11.2 Hz, 2H), 2.71-2.57 (m, 2H), 2.41 (s, 3H), 1.97 (d, J = 12.0 Hz, 1H), 1.76-1.62 (m, 1H). | 532.25 |

TABLE 12-continued

Additional Exemplary Compounds

| Compound | Structure | Proton NMR | MS [M + 1] |
|---|---|---|---|
| (S)-N-(7-(4-amino-7-methyl-5-(4-((4-methylpyrimidin-2-yl)oxy)phenyl)-7H-pyrrolo[2,3-d]pyrimidin-6-yl)-1,2,3,4-tetrahydronaphthalen-2-yl)acrylamide | 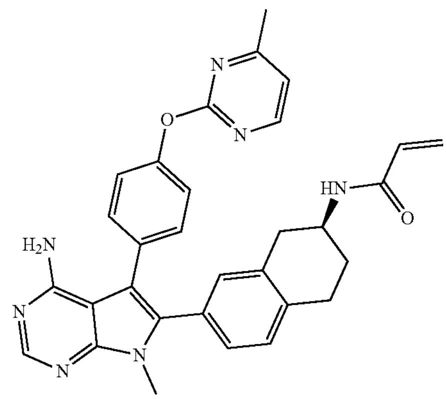 [SMILES: C=CC(=O)N[C@H]1CCc2ccc(-c3c(-c4ccc(Oc5nccc(C)n5)cc4)c4c(N)ncnc4n3C)cc2C1] | $^1$H NMR (400 MHz, DMSO-d$_6$) δ 8.46 (d, J = 5.0 Hz, 1H), 8.19 (d, J = 4.2 Hz, 2H), 7.35-7.27 (m, 2H), 7.26-7.08 (m, 6H), 6.33-6.23 (m, 1H), 6.12 (d, J = 2.3 Hz, 1H), 6.08 (d, J = 2.4 Hz, 1H), 5.59 (dd, J = 10.1, 2.4 Hz, 1H), 4.03 (s, 1H), 3.61 (s, 3H), 2.97 (dd, J = 16.5, 5.3 Hz, 1H), 2.85 (d, J = 11.2 Hz, 2H), 2.84-2.57 (m, 2H), 2.41 (s, 3H), 1.98 (d, J = 11.9 Hz, 1H), 1.67 (p, J = 9.8 Hz, 1H). | 532.25 |
| (S)-N-(5-(4-amino-7-methyl-5-(4-(4-methylpyrimidin-2-yl)oxy)phenyl)-7H-pyrrolo[2,3-d]pyrimidin-6-yl)-2,3-dihydro-1H-inden-1-yl)acrylamide | 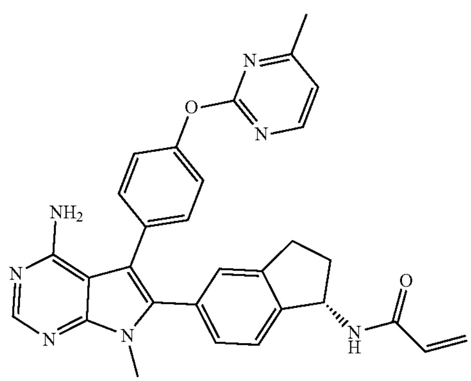 [SMILES: C=CC(=O)N[C@H]1CCc2cc(-c3c(-c4ccc(Oc5nccc(C)n5)cc4)c4c(N)ncnc4n3C)ccc21] | 1H NMR (400 MHz, DMSO-d6) δ 8.55 (d, J = 8.3 Hz, 1H), 8.46 (d, J = 5.0 Hz, 1H), 8.20 (s, 1H), 7.35-7.26 (m, 3H), 7.25-7.14 (m, 5H), 6.32-6.12 (m, 2H), 5.81 (s, 1H), 5.63 (dd, J = 9.9, 2.5 Hz, 1H), 5.39 (q, J = 8.0 Hz, 1H), 3.59 (s, 3H), 2.99-2.88 (m, 1H), 2.83 (dt, J = 16.2, 8.3 Hz, 1H), 2.45 (dt, J = 8.0, 3.8 Hz, 1H), 2.41 (s, 3H), 1.82 (dq, J = 12.5, 8.7 Hz, 1H). | 518.25 |
| (R)-N-(5-(4-amino-7-methyl-5-(4-((4-methylpyrimidin-2-yl)oxy)phenyl)-7H-pyrrolo[2,3-d]pyrimidin-6-yl)-2,3-dihydro-1H-inden-1-yl)acrylamide | 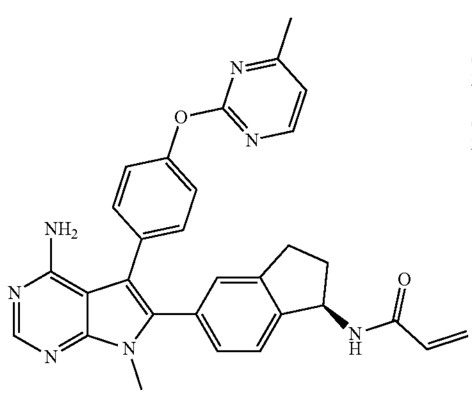 | $^1$H NMR (400 MHz, DMSO-d$_6$) δ 8.20 (s, 1H), 7.73 (t, J = 7.7 Hz, 1H), 7.30-7.15 (m, 5H), 7.13-7.06 (m, 2H), 7.01 (d, J = 7.4 Hz, 1H), 6.89 (dd, J = 16.7, 10.5 Hz, 1H), 6.77 (d, J = 8.2 Hz, 1H), 6.15 (dd, J = 16.7, 2.4 Hz, 1H), 5.88 (s, 2H), 5.72 (dd, J = 10.4, 2.4 Hz, 1H), 4.81 (s, 1H), 4.71 (s, 1H), 3.80 (d, J = 6.3 Hz, 2H), 3.62 (s, 3H), 2.83 (s, 2H), 2.33 (s, 3H). | 517.25 |

TABLE 12-continued

Additional Exemplary Compounds

| Compound | Structure | Proton NMR | MS [M + 1] |
| --- | --- | --- | --- |
| (R)-N-(5-(4-amino-7-methyl-5-(4-((4-methylpyrimidin-2-yl)oxy)phenyl)-7H-pyrrolo[2,3-d]pyrimidin-6-yl)-2,3-dihydro-1H-inden-2-yl)acrylamide | 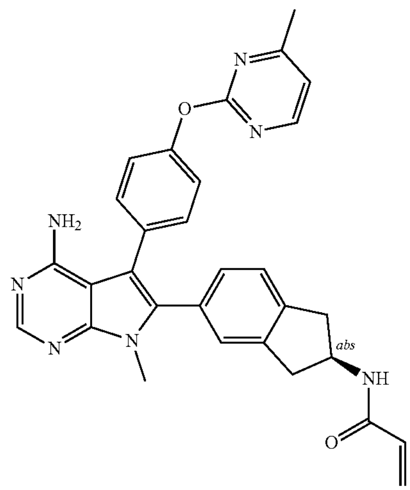 [SMILES: C=CC(=O)N[C@@H]1Cc2ccc(-c3c(-c4ccc(Oc5nccc(C)n5)cc4)c4c(N)ncnc4n3C)cc2C1] | 1H NMR (400 MHz, DMSO-d6) δ 8.49-8.41 (m, 2H), 8.20 (s, 1H), 7.34-7.23 (m, 4H), 7.21-7.13 (m, 4H), 6.26-6.06 (m, 2H), 5.88 (s, 1H), 5.58 (dd, J = 9.9, 2.5 Hz, 1H), 4.56 (q, J = 6.6 Hz, 1H), 3.59 (s, 3H), 3.23 (ddd, J = 16.2, 12.9, 7.6 Hz, 2H), 2.81 (ddd, J = 16.8, 11.8, 5.6 Hz, 2H), 2.41 (s, 3H). | 518.20 |
| (S)-N-(5-(4-amino-7-methyl-5-(4-((4-methylpyrimidin-2-yl)oxy)phenyl)-7H-pyrrolo[2,3-d]pyrimidin-6-yl)-2,3-dihydro-1H-inden-2-yl)acrylamide | 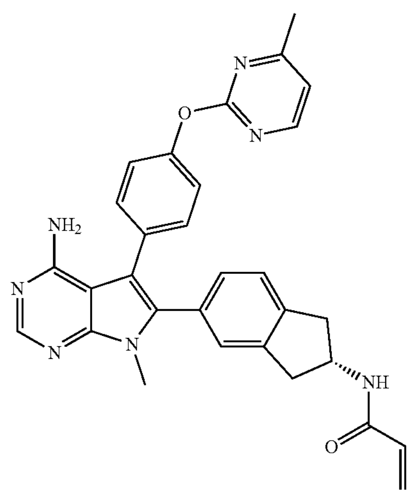 [SMILES: C=CC(=O)N[C@H]1Cc2ccc(-c3c(-c4ccc(Oc5nccc(C)n5)cc4)c4c(N)ncnc4n3C)cc2C1] | 1H NMR (400 MHz, DMSO-d6) δ 8.49-8.41 (m, 2H), 8.20 (s, 1H), 7.34-7.23 (m, 4H), 7.21-7.13 (m, 4H), 6.26-6.06 (m, 2H), 5.88 (s, 1H), 5.58 (dd, J = 9.9, 2.5 Hz, 1H), 4.56 (q, J = 6.6 Hz, 1H), 3.59 (s, 3H), 3.23 (ddd, J = 16.2, 12.9, 7.6 Hz, 2H), 2.81 (ddd, J = 16.8, 11.8, 5.6 Hz, 2H), 2.41 (s, 3H). | 518.25 |
| 1-(2-(4-amino-7-methyl-5-(4-((4-methylpyrimidin-2-yl)oxy)phenyl)-7H-pyrrolo[2,3-d]pyrimidin-6-yl)-1-methyl-1,5,6,7-tetrahydro-4H-imidazo[4,5-b]pyridin-4-yl)prop-2-en-1-one | 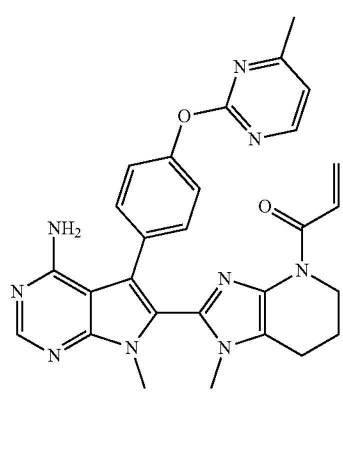 [SMILES: C=CC(=O)N1CCCc2c1nc(-c1c(-c3ccc(Oc4nccc(C)n4)cc3)c3c(N)ncnc3n1C)n2C] | $^1$H NMR (400 MHz, DMSO-d$_6$) δ 8.47 (d, J = 5.0 Hz, 1H), 8.25 (s, 1H), 7.74 (dd, J = 28.0 Hz, 1H), 7.31 (d, J = 8.2 Hz, 2H), 7.25 (d, J = 8.4 Hz, 2H), 7.16 (d, J = 5.2 Hz, 1H), 6.25 (d, J = 16.0 Hz, 1H), 5.77-5.69 (m, 1H), 3.83 (s, 2H), 3.66 (s, 3H), 2.99 (s, 3H), 2.58 (t, J = 6.4 Hz, 2H), 2.40 (s, 3H), 1.94 (s, 2H). | 522.25 |

TABLE 12-continued

Additional Exemplary Compounds

| Compound | Structure | Proton NMR | MS [M + 1] |
|---|---|---|---|
| N-(4-(4-amino-7-methyl-5-(4-((4-methylpyrimidin-2-yl)oxy)phenyl)-7H-pyrrolo[2,3-d]pyrimidin-6-yl)benzyl)acrylamide | 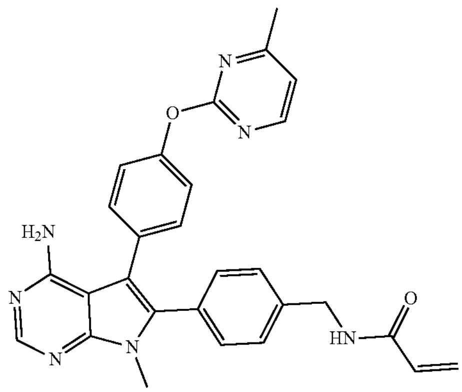 [SMILES: C=CC(=O)NCc1ccc(-c2c(-c3ccc(Oc4nccc(C)n4)cc3)c3c(N)ncnc3n2C)cc1] | 1H NMR (400 MHz, DMSO-d6) δ 8.65 (t, J = 6.1 Hz, 1H), 8.46 (d, J = 5.0 Hz, 1H), 8.20 (s, 1H), 7.36 (d, J = 8.2 Hz, 2H), 7.33-7.27 (m, 4H), 7.21-7.13 (m, 3H), 6.30 (dd, J = 17.1, 10.1 Hz, 1H), 6.14 (dd, J = 17.1, 2.2 Hz, 1H), 5.89 (s, 1H), 5.64 (dd, J = 10.1, 2.3 Hz, 1H), 4.40 (d, J = 6.0 Hz, 2H), 3.59 (s, 3H), 2.41 (s, 3H). | 492.20 |
| N-(2-(4-(4-amino-7-methyl-5-(4-((4-methylpyrimidin-2-yl)oxy)phenyl)-7H-pyrrolo[2,3-d]pyrimidin-6-yl)phenyl)propan-2-yl)acrylamide | 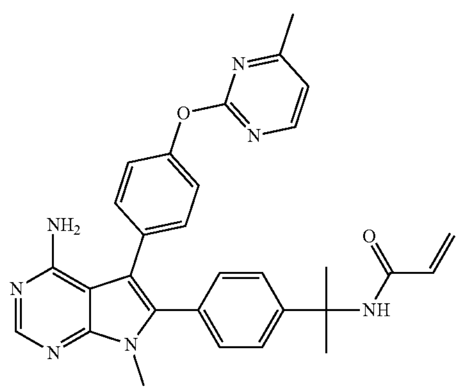 [SMILES: C=CC(=O)NC(C)(C)c1ccc(-c2c(-c3ccc(Oc4nccc(C)n4)cc3)c3c(N)ncnc3n2C)cc1] | $^1$H NMR (400 MHz, DMSO-d$_6$) δ 9.48 (s, 1H), 8.20 (s, 1H), 7.73 (t, J = 7.7 Hz, 1H), 7.62 (d, J = 8.2 Hz, 1H), 7.32-7.25 (m, 2H), 7.23 (d, J = 2.0 Hz, 1H), 7.17 (dd, J = 8.3, 2.1 Hz, 1H), 7.15-7.07 (m, 2H), 7.01 (d, J = 7.3 Hz, 1H), 6.77 (d, J = 8.1 Hz, 1H), 6.57 (dd, J = 17.0, 10.2 Hz, 1H), 6.26 (dd, J = 17.0, 2.1 Hz, 1H), 6.14-5.86 (m, 1H), 5.77 (dd, J = 10.2, 2.0 Hz, 1H), 3.63 (s, 3H), 2.34 (s, 3H), 2.20 (s, 3H). | 491.35 |
| 7-methyl-5-(4-((4-methylpyrimidin-2-yl)oxy)phenyl)-6-(2-vinyl-1H-benzo[d]imidazol-6-yl)-7H-pyrrolo[2,3-d]pyrimidin-4-amine | 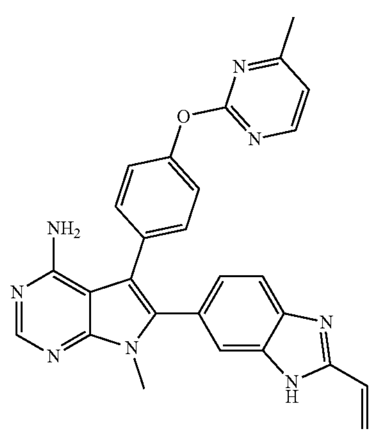 [SMILES: C=Cc1nc2ccc(-c3c(-c4ccc(Oc5nccc(C)n5)cc4)c4c(N)ncnc4n3C)cc2[nH]1] | $^1$H NMR (400 MHz, DMSO-d$_6$) δ 12.74 (d, J = 14.7 Hz, 1H), 8.44 (d, J = 5.0 Hz, 1H), 8.22 (s, 1H), 7.62 (s, 1H), 7.55-7.34 (m, 1H), 7.34-7.24 (m, 2H), 7.21-7.04 (m, 4H), 6.77 (dd, J = 17.8, 11.2 Hz, 1H), 6.28 (d, J = 17.8 Hz, 1H), 5.88 (s, 1H), 5.69 (d, J = 11.4 Hz, 1H), 3.61 (s, 3H), 2.39 (s, 3H). | 475.20 |

TABLE 12-continued

Additional Exemplary Compounds

| Compound | Structure | Proton NMR | MS [M + 1] |
|---|---|---|---|
| N-(4-(4-amino-5-(3-fluoro-4-((4-methylpyrimidin-2-yl)oxy)phenyl)-7-(hex-5-yn-1-yl)-7H-pyrrolo[2,3-d]pyrimidin-6-yl)phenyl)methacrylamide | 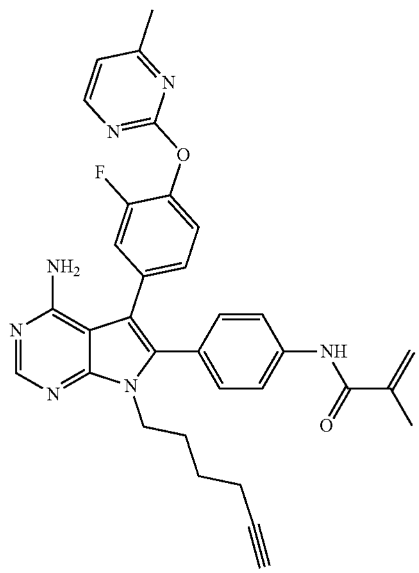 [SMILES: C#CCCCCn1c(-c2ccc(NC(=O)C(=C)C)cc2)c(-c2ccc(Oc3nccc(C)n3)c(F)c2)c2c(N)ncnc21] | $^1$H NMR (400 MHz, DMSO-d$_6$) δ 9.94 (s, 1H), 8.47 (d, J = 5.0 Hz, 1H), 8.21 (s, 1H), 7.76 (d, J = 8.7 Hz, 2H), 7.37-7.28 (m, 3H), 7.24-7.15 (m, 2H), 7.11 (d, J = 8.1 Hz, 1H), 6.01 (s, 2H), 5.81 (s, 1H), 5.54 (s, 1H), 4.11 (t, J = 7.2 Hz, 2H), 2.70 (t, J = 2.7 Hz, 1H), 2.42 (s, 3H), 2.04 (td, J = 1.0, 2.6 Hz, 2H), 1.96 (t, J = 1.2 Hz, 3H), 1.60 (q, J = 7.4 Hz, 2H), 1.26 (q, J = 7.3 Hz, 2H). | 576.25 |
| N-(4-(5-(3-fluoro-4-((4-methylpyrimidin-2-yl)oxy)phenyl)-4-hydroxy-7-methyl-7H-pyrrolo[2,3-d]pyrimidin-6-yl)phenyl)methacrylamide | 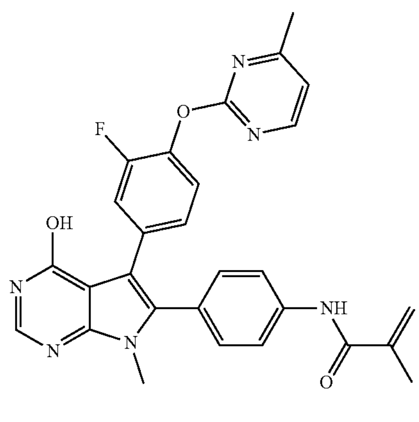 | $^1$H NMR (400 MHz, DMSO-d$_6$) δ 12.04 (d, J = 3.8 Hz, 1H), 9.95 (s, 1H), 8.47 (d, J = 5.0 Hz, 1H), 8.00 (d, J = 3.7 Hz, 1H), 7.82-7.70 (m, 2H), 7.38-7.23 (m, 3H), 7.20-7.11 (m, 2H), 7.06-6.99 (m, 1H), 5.81 (d, J = 1.4 Hz, 1H), 5.54 (t, J = 1.5 Hz, 1H), 3.57 (s, 3H), 2.42 (s, 3H), 1.96 (t, J = 1.2 Hz, 3H). | 511.20 |
| N-(4-(4-amino-7-methyl-5-(4-((4-methylpyrimidin-2-yl)oxy)phenyl)-7H-pyrrolo[2,3-d]pyrimidin-6-yl)-5-chloro-2-fluorophenyl)methacrylamide | 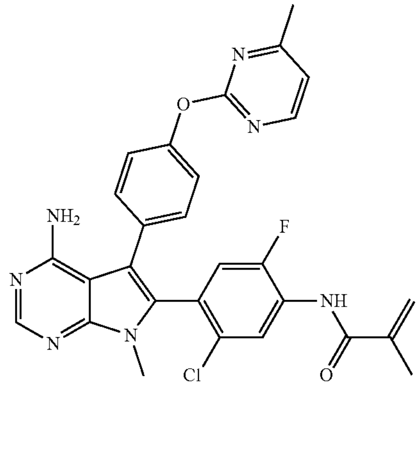 | 1H NMR (400 MHz, DMSO-d6) 9.78 (s, 1H), 8.46 (d, J = 5.0 Hz, 1H), 8.23 (s, 1H), 7.93 (d, J = 7.0 Hz, 1H), 7.52 (d, J = 10.5 Hz, 1H), 7.32-7.25 (m, 2H), 7.23-7.12 (m, 3H), 6.38-5.88 (s, 1H), 5.88 (s, 1H), 5.60 (s, 1H), 3.51 (s, 3H), 2.40 (s, 3H), 1.95 (d, J = 1.3 Hz, 3H). | 544.15 |

TABLE 12-continued

Additional Exemplary Compounds

| Compound | Structure | Proton NMR | MS [M + 1] |
|---|---|---|---|
| N-(4-(4-amino-7-methyl-5-(4-((4-methylpyrimidin-2-yl)oxy)phenyl)-7H-pyrrolo[2,3-d]pyrimidin-6-yl)-3-chloro-2-fluorophenyl)methacrylamide | 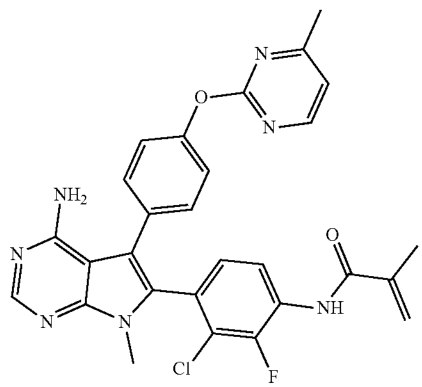 [SMILES: C=C(C)C(=O)Nc1ccc(-c2c(-c3ccc(Oc4nccc(C)n4)cc3)c3c(N)ncnc3n2C)c(Cl)c1F] | $^1$H NMR (400 MHz, DMSO-d$_6$) δ 8.21 (s, 1H), 7.42 (s, 4H), 7.30 (d, J = 8.5 Hz, 2H), 7.22-7.12 (m, 3H), 5.82 (d, J = 1.6 Hz, 1H), 4.27 (s, 2H), 3.61 (s, 3H), 2.41 (s, 3H). | 544.30 |
| N-(4-(4-amino-7-methyl-5-(4-((4-methylpyrimidin-2-yl)oxy)phenyl)-7H-pyrrolo[2,3-d]pyrimidin-6-yl)-5-chloro-2-methylphenyl)methacrylamide | 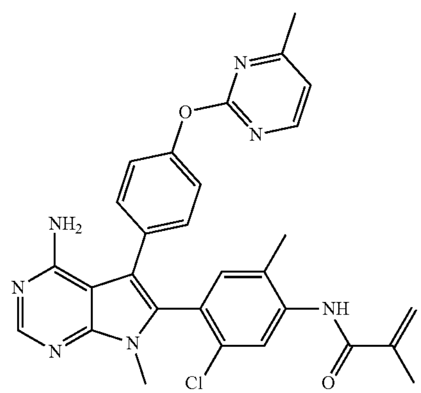 [SMILES: C=C(C)C(=O)Nc1cc(Cl)c(-c2c(-c3ccc(Oc4nccc(C)n4)cc3)c3c(N)ncnc3n2C)cc1C] | 1H NMR (400 MHz, DMSO-d6) 9.38 (s, 1H), 8.45 (d, J = 5.0 Hz, 1H), 8.22 (s, 1H), 7.68 (s, 1H), 7.34 (s, 1H), 7.32-7.25 (m, 2H), 7.22-7.11 (m, 3H), 5.95 (s, 2H), 5.55 (t, J = 1.5 Hz, 1H), 3.48 (s, 3H), 2.40 (s, 3H), 2.18 (s, 3H), 1.97 (t, J = 1.3 Hz, 3H). | 540.15 |
| N-(4-(4-amino-7-methyl-5-(4-((4-methylpyrimidin-2-yl)oxy)phenyl)-7H-pyrrolo[2,3-d]pyrimidin-6-yl)-2-fluoro-5-methylphenyl)methacrylamide | 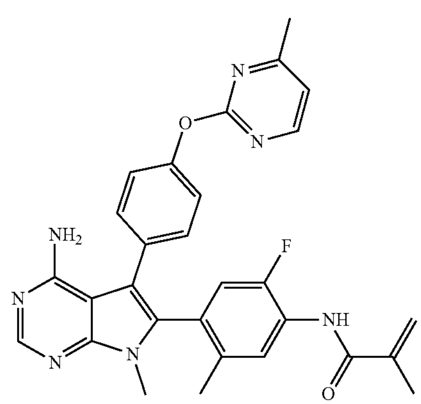 [SMILES: C=C(C)C(=O)Nc1cc(C)c(-c2c(-c3ccc(Oc4nccc(C)n4)cc3)c3c(N)ncnc3n2C)cc1F] | 1H NMR (400 MHz, DMSO-d6) 9.88 (s, 1H), 8.57-8.39 (m, 2H), 7.85-7.59 (m, 1H), 7.35 (dd, J = 8.4, 1.5 Hz, 1H), 7.31-7.25 (m, 2H), 7.24-7.19 (m, 2H), 7.16 (d, J = 5.0 Hz, 1H), 5.90 (s, 1H), 5.62 (d, J = 1.8 Hz, 1H), 3.58 (s, 3H), 2.41 (s, 3H), 1.96 (d, J = 1.2 Hz, 3H). | 524.35 |

TABLE 12-continued

Additional Exemplary Compounds

| Compound | Structure | Proton NMR | MS [M + 1] |
|---|---|---|---|
| N-(4-(4-amino-7-methyl-5-((4-methylpyrimidin-2-yl)oxy)phenyl)-7H-pyrrolo[2,3-d]pyrimidin-6-yl)-2-chloro-3-methylphenyl)methacrylamide | | ¹H NMR (400 MHz, DMSO-d₆) δ 9.39 (s, 1H), 8.45 (d, J = 5.0 Hz, 1H), 8.23 (s, 1H), 7.61 (d, J = 8.1 Hz, 1H), 7.38 (d, J = 8.3 Hz, 1H), 7.29-7.22 (m, 2H), 7.19-7.11 (m, 3H), 5.92 (s, 2H), 5.56 (t, J = 1.5 Hz, 1H), 3.45 (s, 3H), 2.40 (s, 3H), 2.06 (s, 3H), 1.97 (t, J = 1.2 Hz, 3H). | 540.20 |
| N-(4-(4-amino-7-methyl-5-((4-methylpyrimidin-2-yl)oxy)phenyl)-7H-pyrrolo[2,3-d]pyrimidin-6-yl)-3-chloro-2-methylphenyl)methacrylamide | | ¹H NMR (400 MHz, DMSO-d₆) δ 9.63 (s, 1H), 8.44 (d, J = 5.0 Hz, 1H), 8.23 (s, 1H), 7.38-7.24 (m, 4H), 7.20-7.11 (m, 3H), 5.88 (s, 1H), 5.55 (t, J = 1.5 Hz, 1H), 3.46 (s, 3H), 2.40 (s, 3H), 2.27 (s, 3H), 1.96 (t, J = 1.2 Hz, 3H). | 540.20 |
| N-(3-chloro-4-(5-(3-fluoro-4-((4-methylpyrimidin-2-yl)oxy)phenyl)-4,7-dimethyl-7H-pyrrolo[2,3-d]pyrimidin-6-yl)phenyl)methacrylamide | | 1H NMR (400 MHz, DMSO-d6) δ 10.13 (s, 1H), 8.77 (s, 1H), 8.47 (d, J = 5.0 Hz, 1H), 8.07 (d, J = 2.0 Hz, 1H), 7.72 (dd, J = 8.5, 2.1 Hz, 1H), 7.47 (d, J = 8.4 Hz, 1H), 7.31 (t, J = 6.0 Hz, 1H), 7.18 (d, J = 5.1 Hz, 1H), 7.14 (d, J = 8.2 Hz, 1H), 5.84 (s, 1H), 5.59 (s, 1H), 3.58 (s, 3H), 2.41 (d, J = 8.0 Hz, 6H), 1.96 (d, J = 1.3 Hz, 3H). | 543.20 |

TABLE 12-continued

Additional Exemplary Compounds

| Compound | Structure | Proton NMR | MS [M + 1] |
|---|---|---|---|
| N-(3-chloro-4-(5-(3-fluoro-4-((4-methylpyrimidin-2-yl)oxy)phenyl)-4,7-dimethyl-7H-pyrrolo[2,3-d]pyrimidin-6-yl)phenyl)acrylamide | 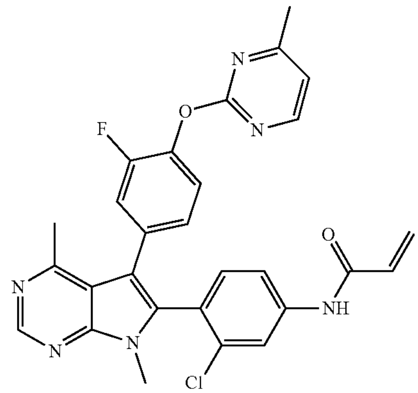 [SMILES: C=CC(=O)Nc1ccc(-c2c(-c3ccc(Oc4nccc(C)n4)c(F)c3)c3c(C)ncnc3n2C)c(Cl)c1] | 1H NMR (400 MHz, DMSO-d6) δ 10.51 (s, 1H), 8.77 (s, 1H), 8.47 (d, J = 5.0 Hz, 1H), 8.08 (d, J = 2.1 Hz, 1H), 7.61 (dd, J = 8.5, 2.0 Hz, 1H), 7.49 (d, J = 8.4 Hz, 1H), 7.38-7.25 (m, 2H), 7.16 (dd, J = 16.1, 6.7 Hz, 2H), 6.43 (dd, J = 16.9, 10.0 Hz, 1H), 6.31 (dd, J = 17.0, 2.1 Hz, 1H), 5.84 (dd, J = 9.9, 2.1 Hz, 1H), 3.58 (s, 3H), 2.41 (d, J = 8.9 Hz, 6H). | 529.20 |
| 1-(4-(4-amino-7-methyl-5-(4-((4-methylpyrimidin-2-yl)oxy)phenyl)-7H-pyrrolo[2,3-d]pyrimidin-6-yl)phenyl)-3-methyleneazetidin-2-one | 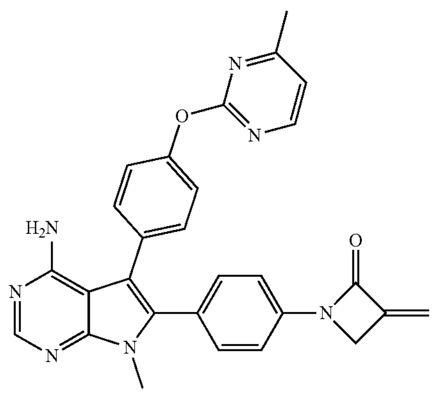 [SMILES: C=C1CN(c2ccc(-c3c(-c4ccc(Oc5nccc(C)n5)cc4)c4c(N)ncnc4n3C)cc2)C1=O] | $^1$H NMR (400 MHz, DMSO-d$_6$) δ 8.40 (d, J = 11.7 Hz, 1H), 8.13 (s, 1H), 7.63 (d, J = 2.7 Hz, 1H), 6.59 (s, 2H), 5.69 (d, J = 30.0 Hz, 2H), 4.42 (d, J = 1.1 Hz, 1H), 3.51-3.38 (m, 2H), 3.37 (d, J = 1.4 Hz, 3H), 3.28 (s, 0H), 2.75 (s, 0H), 2.68 (p, J = 1.8 Hz, 1H), 2.34 (p, J = 1.9 Hz, 1H), 2.20 (d, J = 7.1 Hz, 2H), 1.93 (d, J = 9.1 Hz, 2H), 1.85 (q, J = 6.1 Hz, 1H), 1.82-1.69 (m, 2H), 1.60 (d, J = 7.0 Hz, 2H). | 490.15 |
| 1-(4-(4-amino-7-methyl-5-(4-((4-methylpyrimidin-2-yl)oxy)phenyl)-7H-pyrrolo[2,3-d]pyrimidin-6-yl)phenyl)-3-methyl-1,5-dihydro-2H-pyrrol-2-one | 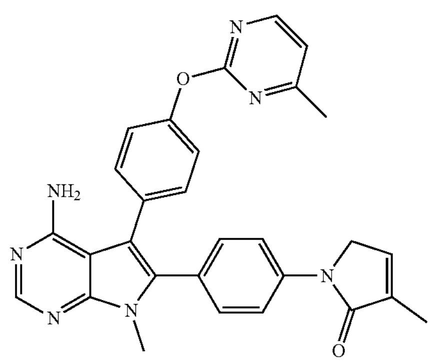 [SMILES: CC1=CCN(c2ccc(-c3c(-c4ccc(Oc5nccc(C)n5)cc4)c4c(N)ncnc4n3C)cc2)C1=O] | $^1$H NMR (400 MHz, Methanol-d$_4$) δ 8.41 (d, J = 5.1 Hz, 1H), 8.22 (s, 1H), 7.90-7.80 (m, 2H), 7.42-7.34 (m, 4H), 7.22-7.12 (m, 3H), 7.03 (q, J = 1.8 Hz, 1H), 4.45 (p, J = 2.0 Hz, 2H), 3.72 (s, 3H), 2.50 (s, 3H), 1.94 (q, J = 1.9 Hz, 3H). | 504.20 |
| N-(6-(4-amino-5-(3-fluoro-4-((6-methylpyridin-2-yl)oxy)phenyl)-7-methyl-7H-pyrrolo[2,3-d]pyrimidin-6-yl)-5-methylpyridin-3-yl)methacrylamide | 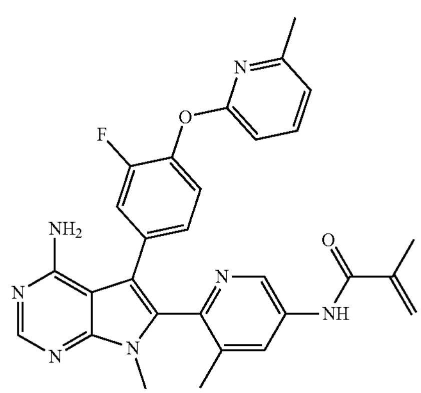 [SMILES: C=C(C)C(=O)Nc1cnc(-c2c(-c3ccc(Oc4cccc(C)n4)c(F)c3)c3c(N)ncnc3n2C)c(C)c1] | $^1$H NMR (400 MHz, DMSO-d$_6$) δ 10.10 (s, 1H), 8.90 (d, J = 2.4 Hz, 1H), 8.24 (s, 1H), 8.03 (d, J = 2.4 Hz, 1H), 7.78-7.71 (m, 1H), 7.24 (t, J = 8.4 Hz, 1H), 7.07-6.95 (m, 3H), 6.86 (d, J = 8.2 Hz, 1H), 6.21 (s, 1H), 5.87 (s, 1H), 5.60 (s, 1H), 3.51 (s, 3H), 2.30 (s, 3H), 1.97 (t, J = 1.2 Hz, 3H), 1.83 (s, 3H). | 524.35 |

TABLE 12-continued

Additional Exemplary Compounds

| Compound | Structure | Proton NMR | MS [M + 1] |
|---|---|---|---|
| N-(6-(4-amino-5-(3-fluoro-4-((6-methylpyridin-2-yl)oxy)phenyl)-7-methyl-7H-pyrrolo[2,3-d]pyrimidin-6-yl)-5-fluoropyridin-3-yl)methacrylamide | 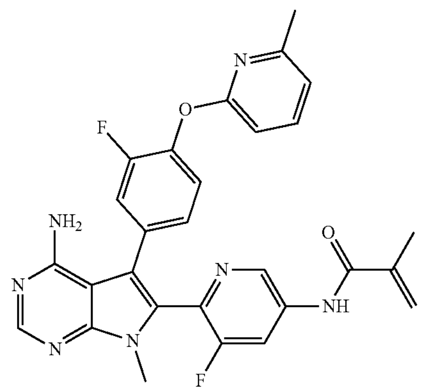 [SMILES: C=C(C)C(=O)Nc1cnc(-c2c(-c3ccc(Oc4cccc(C)n4)c(F)c3)c3c(N)ncnc3n2C)c(F)c1] | $^1$H NMR (400 MHz, DMSO-d$_6$) δ 10.40 (s, 1H), 8.89-8.84 (m, 1H), 8.25 (s, 1H), 8.13 (dd, J = 11.9, 2.0 Hz, 1H), 7.75 (dd, J = 8.2, 7.3 Hz, 1H), 7.27 (t, J = 8.4 Hz, 1H), 7.14 (dd, J = 11.5, 2.1 Hz, 1H), 7.07-6.98 (m, 2H), 6.86 (d, J = 8.2 Hz, 1H), 6.22 (s, 1H), 5.90 (s, 1H), 5.68-5.63 (m, 1H), 3.65 (s, 3H), 2.31 (s, 3H), 1.97 (t, J = 1.2 Hz, 3H). | 528.35 |
| N-(5-(4-amino-5-(3-fluoro-4-((6-methylpyridin-2-yl)oxy)phenyl)-7-methyl-7H-pyrrolo[2,3-d]pyrimidin-6-yl)-6-methylpyridin-2-yl)methacrylamide | 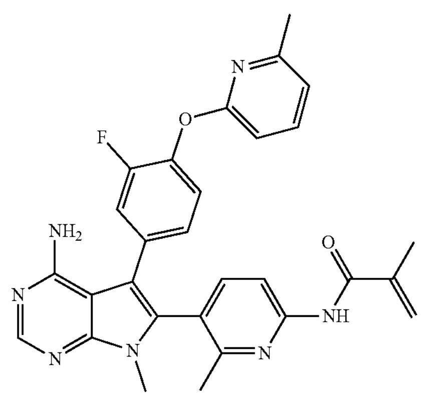 [SMILES: C=C(C)C(=O)Nc1ccc(-c2c(-c3ccc(Oc4cccc(C)n4)c(F)c3)c3c(N)ncnc3n2C)c(C)n1] | 1H NMR (400 MHz, DMSO-d6) δ 10.32 (d, J = 13.1 Hz, 1H), 8.23 (s, 1H), 8.11-8.00 (m, 1H), 7.82 (d, J = 8.5 Hz, 1H), 7.73 (dd, J = 8.2, 7.4 Hz, 1H), 7.25 (t, J = 8.4 Hz, 1H), 7.13 (dd, J = 11.6, 2.0 Hz, 1H), 7.07-6.97 (m, 2H), 6.84 (d, J = 8.2 Hz, 1H), 6.13 (s, 1H), 5.94 (s, 1H), 5.58-5.53 (m, 1H), 3.50 (s, 3H), 2.28 (s, 3H), 2.10 (s, 3H), 1.96 (t, J = 1.2 Hz, 3H). | 524.21 |
| N-(5-(4-amino-5-(3-fluoro-4-((6-methylpyridin-2-yl)oxy)phenyl)-7-methyl-7H-pyrrolo[2,3-d]pyrimidin-6-yl)-4-methylpyridin-2-yl)methacrylamide | 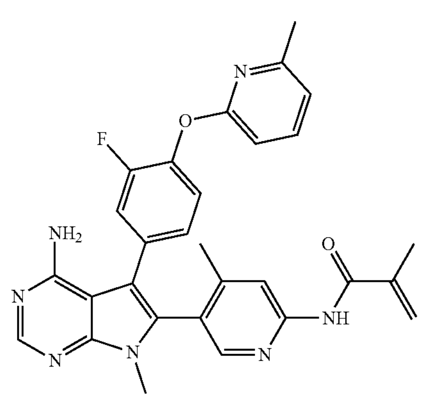 [SMILES: C=C(C)C(=O)Nc1cc(C)c(-c2c(-c3ccc(Oc4cccc(C)n4)c(F)c3)c3c(N)ncnc3n2C)cn1] | 1H NMR (400 MHz, DMSO-d6) δ 10.35 (s, 1H), 8.23 (s, 1H), 8.03 (d, J = 8.4 Hz, 1H), 7.82 (d, J = 8.5 Hz, 1H), 7.77-7.69 (m, 1H), 7.25 (t, J = 8.4 Hz, 1H), 7.13 (dd, J = 11.5, 2.1 Hz, 1H), 7.05-6.97 (m, 2H), 6.85 (d, J = 8.2 Hz, 1H), 5.94 (s, 1H), 5.58-5.53 (m, 1H), 3.50 (s, 3H), 2.28 (s, 3H), 2.09 (s, 3H), 1.96 (t, J = 1.2 Hz, 3H). | 524.21 |

TABLE 12-continued

Additional Exemplary Compounds

| Compound | Structure | Proton NMR | MS [M + 1] |
|---|---|---|---|
| N-(4-(4-amino-7-methyl-5-(4-((4-methylpyrimidin-2-yl)oxy)phenyl)-7H-pyrrolo[2,3-d]pyrimidin-6-yl)-3-fluoro-5-methylphenyl)methacrylamide | 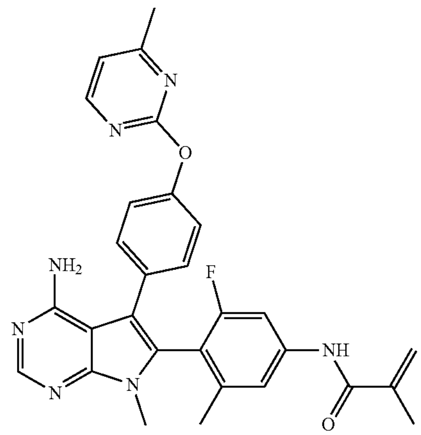 [SMILES: C=C(C)C(=O)Nc1cc(C)c(-c2c(-c3ccc(Oc4nccc(C)n4)cc3)c3c(N)ncnc3n2C)c(F)c1] | 1H NMR (400 MHz, DMSO-d6) δ 10.03 (s, 1H), 8.46 (d, J = 5.0 Hz, 1H), 8.22 (s, 1H), 7.66 (dd, J = 11.6, 2.0 Hz, 1H), 7.44-7.42 (m, 1H), 7.26-7.22 (m, 2H), 7.21-7.13 (m, 3H), 6.01 (s, 1H), 5.82 (s, 1H), 5.57 (s, 1H), 3.45 (s, 3H), 2.40 (s, 3H), 1.96-1.89 (m, 6H). | 524.25 |
| N-(4-(5-(3-fluoro-4-((4-methylpyrimidin-2-yl)oxy)phenyl)-7-methyl-7H-pyrrolo[2,3-d]pyrimidin-6-yl)-3-methylphenyl)acrylamide | 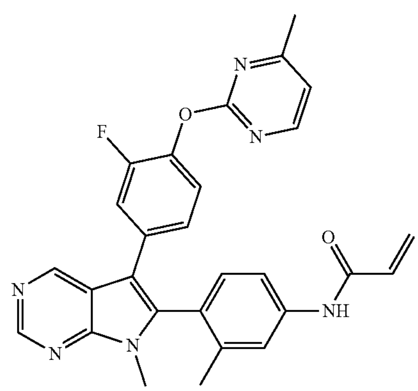 [SMILES: C=CC(=O)Nc1ccc(-c2c(-c3ccc(Oc4nccc(C)n4)c(F)c3)c3cncnc3n2C)c(C)c1] | $^1$H NMR (400 MHz, DMSO-d$_6$) δ 10.32 (s, 1H), 9.23 (s, 1H), 8.94 (s, 1H), 8.46 (d, J = 5.0 Hz, 1H), 7.76-7.67 (m, 2H), 7.42 (d, J = 8.3 Hz, 1H), 7.32 (t, J = 8.4 Hz, 1H), 7.26-7.15 (m, 3H), 6.47 (dd, J = 17.0, 10.1 Hz, 1H), 6.30 (dd, J = 17.0, 2.1 Hz, 1H), 5.80 (dd, J = 10.1, 2.1 Hz, 1H), 3.55 (s, 3H), 2.42 (s, 3H), 2.00 (s, 3H). | 495.20 |
| N-(4-(4-amino-7-methyl-5-(4-((4-methylpyrimidin-2-yl)oxy)phenyl)-7H-pyrrolo[2,3-d]pyrimidin-6-yl)-3-methylphenyl)acrylamide | 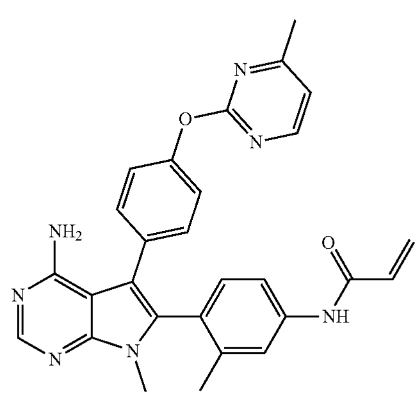 [SMILES: C=CC(=O)Nc1ccc(-c2c(-c3ccc(Oc4nccc(C)n4)cc3)c3c(N)ncnc3n2C)c(C)c1] | $^1$H NMR (400 MHz, DMSO-d6) 10.22 (s, 1H), 8.45 (d, J = 4.3 Hz, 1H), 8.21 (d, J = 3.0 Hz, 1H), 7.60 (d, J = 13.2 Hz, 2H), 7.35-7.28 (m, 1H), 7.28-7.22 (m, 2H), 7.15 (d, J = 7.4 Hz, 3H), 6.45 (dd, J = 17.9, 9.9 Hz, 1H), 6.27 (d, J = 16.8 Hz, 1H), 5.78 (d, J = 10.2 Hz, 1H), 5.56 (s, 1H), 3.39 (s, 3H), 2.40 (d, J = 3.0 Hz, 3H), 1.97 (d, J = 3.0 Hz, 3H). | 492.20 |

TABLE 12-continued

Additional Exemplary Compounds

| Compound | Structure | Proton NMR | MS [M + 1] |
|---|---|---|---|
| N-(4-(4-amino-5-(3-fluoro-4-((4-methylpyrimidin-2-yl)oxy)phenyl)-7-methyl-7H-pyrrolo[2,3-d]pyrimidin-6-yl)-3-methylphenyl)acrylamide | 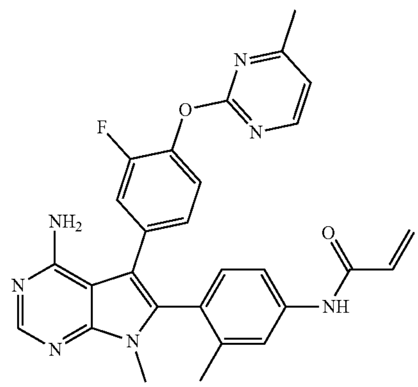 [SMILES: C=CC(=O)Nc1ccc(-c2c(-c3ccc(Oc4nccc(C)n4)c(F)c3)c3c(N)ncnc3n2C)c(C)c1] | ¹H NMR (400 MHz, DMSO-d6) 10.24 (s, 1H), 8.47 (d, J = 5.0 Hz, 1H), 8.22 (s, 1H), 7.66-7.57 (m, 2H), 7.32 (t, J = 8.4 Hz, 2H), 7.17 (d, J = 5.0 Hz, 1H), 7.12 (dd, J = 11.6, 2.1 Hz, 1H), 7.06 (dd, J = 8.4, 2.0 Hz, 1H), 6.45 (dd, J = 17.0, 10.1 Hz, 1H), 6.27 (dd, J = 17.0, 2.1 Hz, 1H), 6.08-6.01 (m, 1H), 5.78 (dd, J = 10.0, 2.1 Hz, 1H), 3.43 (s, 3H), 2.41 (s, 3H), 1.96 (s, 3H). | 510.10 |
| 6-(2,6-dimethylpyridin-3-yl)-5-(3-fluoro-4-((4-methylpyrimidin-2-yl)oxy)phenyl)-7-methyl-7H-pyrrolo[2,3-d]pyrimidin-4-amine | 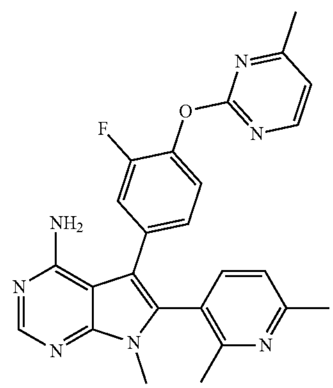 [SMILES: Cc1ccnc(Oc2ccc(-c3c(-c4ccc(C)nc4C)n(C)c4ncnc(N)c34)cc2F)n1] | ¹H NMR (400 MHz, DMSO-d₆) δ 8.47 (d, J = 5.0 Hz, 1H), 8.24 (s, 1H), 7.72 (d, J = 7.8 Hz, 1H), 7.33 (t, J = 8.4 Hz, 1H), 7.24-7.11 (m, 3H), 7.08-7.01 (m, 1H), 3.44 (s, 3H), 2.48 (s, 3H), 2.41 (s, 3H), 2.12 (s, 3H). | 456.20 |
| (2E)-3-[4-(4-amino-5-{3-fluoro-4-[(4-methylpyrimidin-2-yl)oxy]phenyl}-7-methyl-7H-pyrrolo[2,3-d]pyrimidin-6-yl)-3-methylphenyl]-2-cyano-N-methylprop-2-enamide | 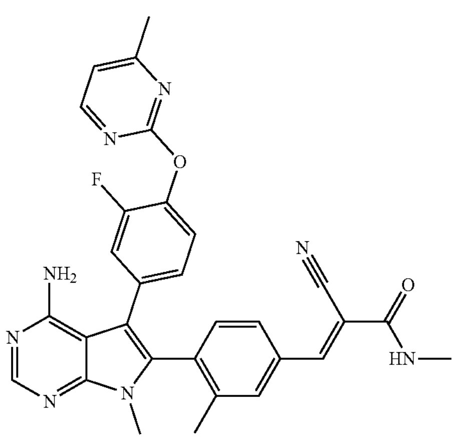 [SMILES: CNC(=O)/C(C#N)=C/c1ccc(-c2c(-c3ccc(Oc4nccc(C)n4)c(F)c3)c3c(N)ncnc3n2C)c(C)c1] | ¹H NMR (400 MHz, DMSO-d₆) δ 8.46 (d, J = 5.0 Hz, 1H), 8.41 (d, J = 4.6 Hz, 1H), 8.24 (s, 1H), 8.17 (s, 1H), 7.94-7.89 (m, 1H), 7.86 (d, J = 1.8 Hz, 1H), 7.62 (s, 1H), 7.32 (t, J = 8.4 Hz, 1H), 7.21-7.11 (m, 2H), 7.06 (ddd, J = 8.3, 2.1, 0.8 Hz, 1H), 6.09 (s, 1H), 3.46 (s, 3H), 2.77 (d, J = 4.5 Hz, 3H), 2.40 (s, 3H), 2.04 (s, 3H). | 549.35 |

TABLE 12-continued

Additional Exemplary Compounds

| Compound | Structure | Proton NMR | MS [M + 1] |
|---|---|---|---|
| (E)-5-(3-fluoro-4-((4-methylpyrimidin-2-yl)oxy)phenyl)-6-(6-(3-methoxyprop-1-en-1-yl)-4-methylpyridin-3-yl)-7-methyl-7H-pyrrolo[2,3-d]pyrimidin-4-amine | 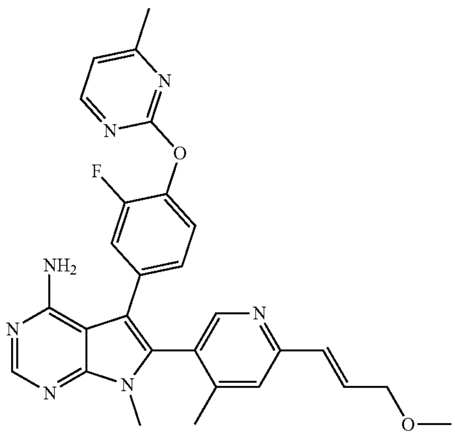 [SMILES: COC/C=C/c1cc(C)c(-c2c(-c3ccc(Oc4nccc(C)n4)c(F)c3)c3c(N)ncnc3n2C)cn1] | $^1$H NMR (400 MHz, DMSO-d$_6$) δ 2.01 (s, 3H), 2.40 (s, 3H), 3.46 (s, 3H), 4.11 (d, J = 5.1 Hz, 2H), 6.68 (s, 1H), 6.79-6.88 (m, 1H), 7.05 (d, J = 8.3 Hz, 1H), 7.12-7.21 (m, 2H), 7.32 (t, J = 8.4 Hz, 1H), 7.43 (s, 1H), 8.23 (s, 1H), 8.46 (d, J = 4.9 Hz, 2H). | 512.4 |
| N-(4-(4-amino-5-(3-fluoro-4-((4-methylpyrimidin-2-yl)oxy)phenyl)-7-methyl-7H-pyrrolo[2,3-d]pyrimidin-6-yl)cyclohex-3-en-1-yl)acrylamide | 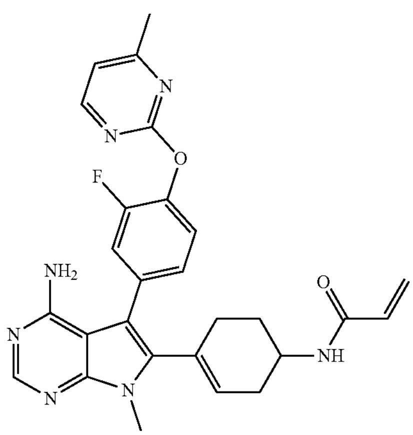 [SMILES: C=CC(=O)NC1CC=C(c2c(-c3ccc(Oc4nccc(C)n4)c(F)c3)c3c(N)ncnc3n2C)CC1] | $^1$H NMR (400 MHz, DMSO-d$_6$) δ 8.50 (d, J = 5.0 Hz, 1H), 8.17 (s, 1H), 8.08 (d, J = 7.5 Hz, 1H), 7.43 (t, J = 8.4 Hz, 1H), 7.32 (dd, J = 11.5, 2.1 Hz, 1H), 7.26-7.17 (m, 2H), 6.22 (dd, J = 17.0, 10.0 Hz, 1H), 6.07 (dd, J = 17.1, 2.3 Hz, 2H), 5.84 (d, J = 4.4 Hz, 1H), 5.57 (dd, J = 10.0, 2.4 Hz, 1H), 3.91 (s, 1H), 3.66 (s, 3H), 2.42 (m, 4H), 2.21 (s, 1H), 2.08 (d, J = 15.5 Hz, 2H), 1.78 (d, J = 25.3 Hz, 1H), 1.53 (dd, J = 11.5, 5.2 Hz, 1H). | 500.10 |
| (R)-N-(4-(4-amino-5-(3-fluoro-4-((4-methylpyrimidin-2-yl)oxy)phenyl)-7-methyl-7H-pyrrolo[2,3-d]pyrimidin-6-yl)cyclohex-3-en-1-yl)acrylamide | 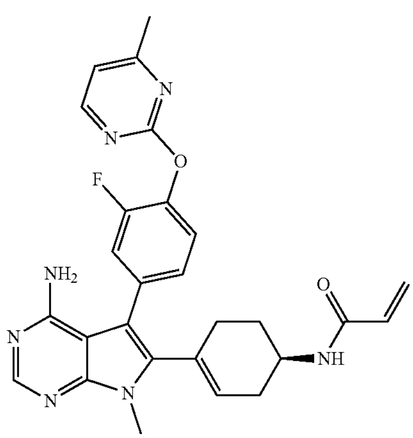 [SMILES: C=CC(=O)N[C@H]1CC=C(c2c(-c3ccc(Oc4nccc(C)n4)c(F)c3)c3c(N)ncnc3n2C)CC1] | $^1$H NMR (400 MHz, DMSO-d$_6$) δ 8.50 (d, J = 5.0 Hz, 1H), 8.16 (s, 1H), 8.07 (d, J = 7.5 Hz, 1H), 7.43 (t, J = 8.4 Hz, 1H), 7.32 (dd, J = 11.4, 2.1 Hz, 1H), 7.26-7.17 (m, 2H), 6.22 (dd, J = 17.1, 10.1 Hz, 1H), 6.07 (dd, J = 17.1, 2.4 Hz, 1H), 6.00 (s, 1H), 5.83 (d, J = 4.6 Hz, 1H), 5.56 (dd, J = 10.1, 2.3 Hz, 1H), 3.91 (s, 1H), 3.65 (s, 3H), 2.42 (s, 3H), 2.27 (d, J = 45.4 Hz, 1H), 2.08 (d, J = 15.3 Hz, 2H), 1.89-1.73 (m, 1H), 1.54 (dd, J = 11.3, 5.2 Hz, 1H). | 500.25 |

TABLE 12-continued

Additional Exemplary Compounds

| Compound | Structure | Proton NMR | MS [M + 1] |
|---|---|---|---|
| (S)-N-(4-(4-amino-5-(3-fluoro-4-((4-methylpyrimidin-2-yl)oxy)phenyl)-7-methyl-7H-pyrrolo[2,3-d]pyrimidin-6-yl)cyclohex-3-en-1-yl)acrylamide | 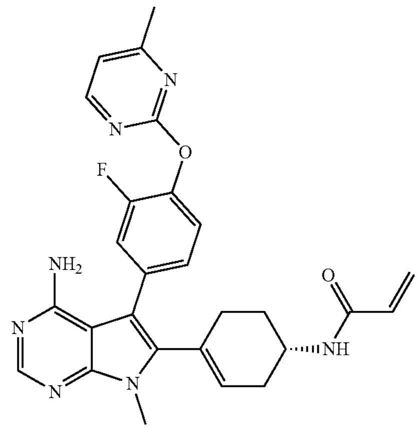 [SMILES: C=CC(=O)N[C@@H]1CC=C(c2c(-c3ccc(Oc4nccc(C)n4)c(F)c3)c3c(N)ncnc3n2C)CC1] | $^1$H NMR (400 MHz, DMSO-d$_6$) δ 8.50 (d, J = 5.0 Hz, 1H), 8.16 (s, 1H), 8.06 (d, J = 7.5 Hz, 1H), 7.43 (t, J = 8.3 Hz, 1H), 7.33 (d, J = 2.0 Hz, 1H), 7.21 (dd, J = 13.1, 6.7 Hz, 2H), 6.22 (dd, J = 17.1, 10.1 Hz, 1H), 6.07 (dd, J = 17.1, 2.3 Hz, 1H), 5.98 (s, 1H), 5.84 (s, 1H), 5.56 (dd, J = 10.0, 2.4 Hz, 1H), 3.91 (s, 1H), 3.65 (s, 3H), 2.42 (s, 4H), 2.21 (s, 1H), 2.15-1.97 (m, 2H), 1.83 (d, J = 11.9 Hz, 1H), 1.54 (dd, J = 11.5, 5.2 Hz, 1H). | 500.25 |
| 7-(4-amino-7-methyl-5-(4-((4-methylpyrimidin-2-yl)oxy)phenyl)-7H-pyrrolo[2,3-d]pyrimidin-6-yl)-2-methylene-3,4-dihydronaphthalen-1(2H)-one | 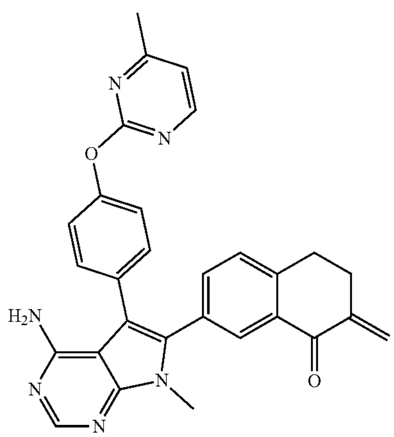 [SMILES: C=C1CCc2ccc(-c3c(-c4ccc(Oc5nccc(C)n5)cc4)c4c(N)ncnc4n3C)cc2C1=O] | $^1$H NMR (400 MHz, DMSO-d$_6$) δ 8.46 (d, J = 5.0 Hz, 1H), 8.22 (s, 1H), 7.91 (d, J = 1.9 Hz, 1H), 7.60 (dd, J = 7.9, 2.0 Hz, 1H), 7.44 (d, J = 8.0 Hz, 1H), 7.35-7 27 (m, 2H), 7.22-7.10 (m, 3H), 6.05 (d, J = 2.1 Hz, 1H), 5.93 (s, 2H), 5.56 (d, J = 1.9 Hz, 1H), 3.61 (s, 3H), 3.02 (t, J = 6.4 Hz, 2H), 2.90-2.82 (m, 2H), 2.40 (s, 3H). | 489.30 |
| 6-(4-amino-7-methyl-5-(4-((4-methylpyrimidin-2-yl)oxy)phenyl)-7H-pyrrolo[2,3-d]pyrimidin-6-yl)-2-methylene-3,4-dihydronaphthalen-1(2H)-one | 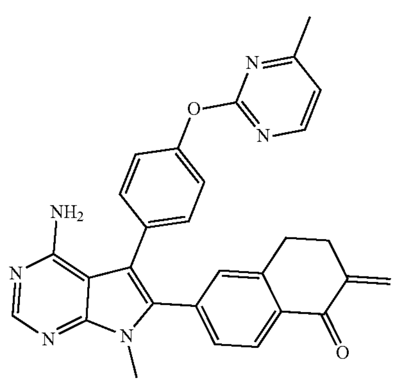 [SMILES: C=C1CCc2cc(-c3c(-c4ccc(Oc5nccc(C)n5)cc4)c4c(N)ncnc4n3C)ccc2C1=O] | $^1$H NMR (400 MHz, DMSO-d$_6$) δ 8.46 (d, J = 5.0 Hz, 1H), 8.24 (s, 1H), 7.93 (d, J = 8.1 Hz, 1H), 7.42 (d, J = 1.7 Hz, 1H), 7.36 (dd, J = 8.0, 1.7 Hz, 1H), 7.35-7.27 (m, 2H), 7.24-7.13 (m, 3H), 6.06 (d, J = 2.1 Hz, 1H), 5.99 (s, 2H), 5.56 (d, J = 2.0 Hz, 1H), 3.68 (s, 3H), 2.96 (t, J = 6.3 Hz, 2H), 2.84 (t, J = 6.1 Hz, 2H), 2.41 (s, 3H). | 489.35 |

Example 14

Scheme 12

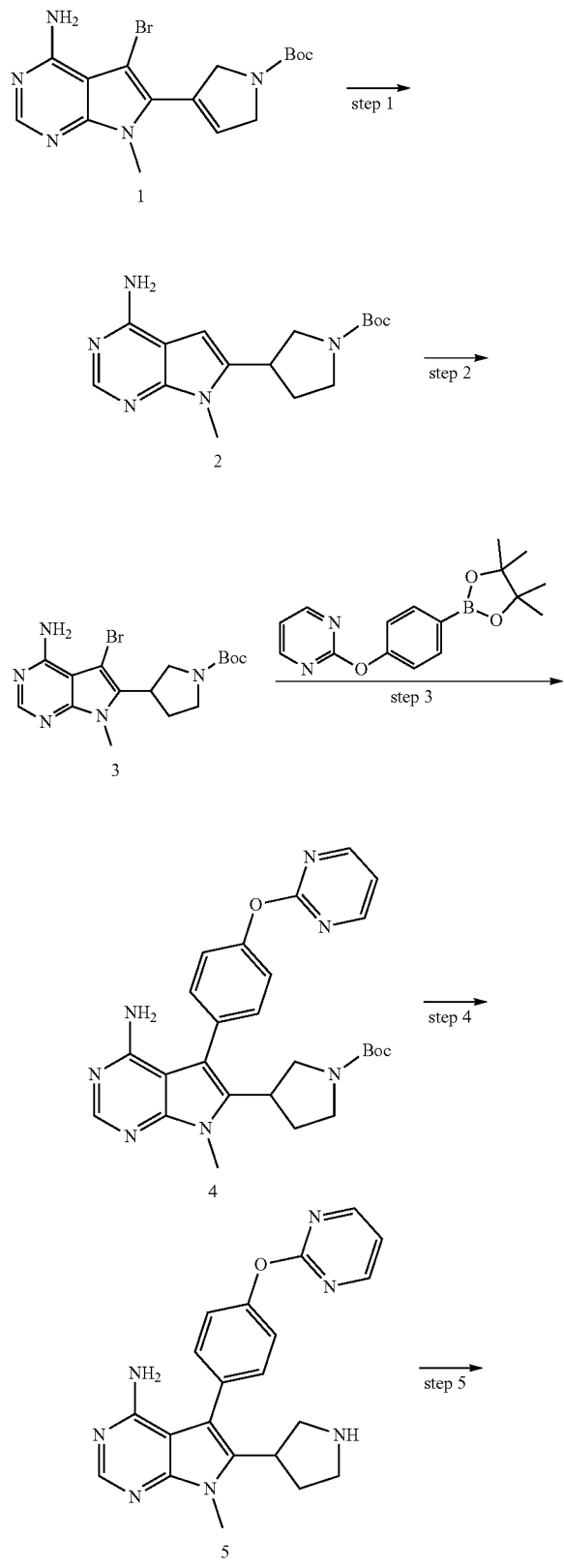

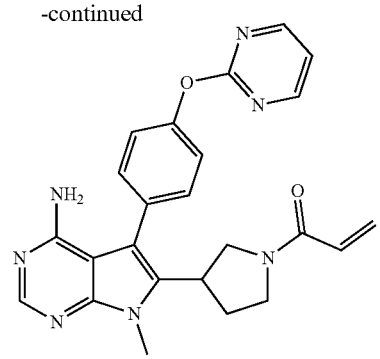

tert-butyl 3-(4-amino-7-methyl-7H-pyrrolo[2,3-d]pyrimidin-6-yl)pyrrolidine carboxylate

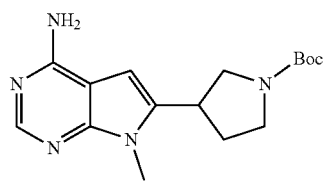 [SMILES: Cn1c(C2CCN(C(=O)OC(C)(C)C)C2)cc2c(N)ncnc21]

Step 1: A resealable reaction vial was charged with tert-butyl 3-{4-amino-5-bromo-7-methyl-7H-pyrrolo[2,3-d]pyrimidin-6-yl}-2,5-dihydro-1H-pyrrole-1-carboxylate (1.2 g, 3.07 mmol), Pd—C (120 mg, 1.2 mol) and a stir bar before being evacuated and purged with hydrogen three times. MeOH (20 mL) was added, and the mixture was stirred overnight at 50° C. The reaction mixture was filtered through a pad of Celite®, the pad was washed with water, and the filtrate was concentrated in vacuo resulting in tert-butyl 3-{4-amino-7-methyl-7H-pyrrolo[2,3-d]pyrimidin-6-yl}pyrrolidine-1-carboxylate (0.9 g, 91.8%) as a off-white solid.

tert-butyl 3-(4-amino-5-bromo-7-methyl-7H-pyrrolo[2,3-d]pyrimidin-6-yl)pyrrolidine-1-carboxylate

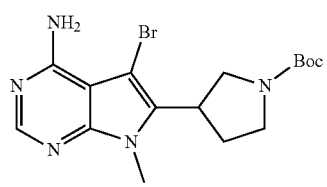 [SMILES: Cn1c(C2CCN(C(=O)OC(C)(C)C)C2)c(Br)c2c(N)ncnc21]

Step 2: A round bottomed flask was charged with tert-butyl 3-{4-amino-7-methyl-7H-pyrrolo[2,3-d]pyrimidin-6-yl}pyrrolidine-1-carboxylate (300 mg, 945 µmol), NBS (168 mg, 945 µmol), and a stirbar. Dichloromethane (5 mL) was added, and the solution was stirred 30 min at r.t. The reaction mixture was diluted with water (10 mL), and the aqueous phase was extracted with dichloromethane (10 mL) three times. The combined organic layers were washed with brine, dried over sodium sulfate, filtered, and concentrated in vacuo resulted in tert-butyl 3-{4-amino-5-bromo-7-methyl-7H-pyrrolo[2,3-d]pyrimidin-6-yl}-pyrrolidine-1-carboxylate (230 mg, 61.4%) as a light yellow solid.

1505 tert-butyl 3-(4-amino-7-methyl-5-(4-(pyrimidin-2-yloxy)phenyl)-7H-pyrrolo[2,3-d]pyrimidin-6-yl)pyrrolidine-1-carboxylate

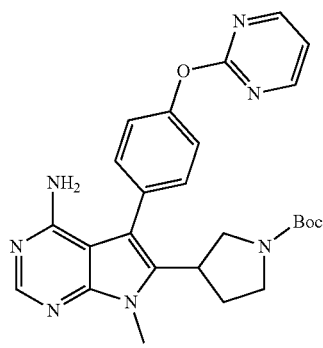 [SMILES: Cn1c(C2CCN(C(=O)OC(C)(C)C)C2)c(-c2ccc(Oc3ncccn3)cc2)c2c(N)ncnc21]

Step 3: A resealable reaction vial was charged with tert-butyl 3-{4-amino-5-bromo-7-methyl-7H-pyrrolo[2,3-d]pyrimidin-6-yl}pyrrolidine-1-carboxylate (200 mg, 504 μmol), 2-[4-(4,4,5,5-tetramethyl-1,3,2-dioxaborolan-2-yl)phenoxy]pyrimidine (165 mg, 554 μmol), Pd(dtbpf)Cl$_2$ (32.8 mg, 50.4 μmol), K3PO4 (320 mg, 1.51 mmol), and a stirbar before being evacuated and purged with nitrogen three times. DMF/water (2 mL) was added, and the mixture was stirred 2 h at 90° C. The reaction mixture was diluted with water (10 mL), and the aqueous phase was extracted with dichloromethane (10 mL) three times. The combined organic layers were washed with brine, dried over sodium sulfate, filtered, and concentrated in vacuo. The resulting crude material was purified by silica gel chromatography (5 g column; eluting with dichloromethane/methanol/0.1% triethylamine; ratio). Concentration in vacuo resulted in tert-butyl 3-{4-amino-7-methyl-5-[4-(pyrimidin-2-yloxy)phenyl]-7H-pyrrolo[2,3-d]pyrimidin-6-yl}pyrrolidine-1-carboxylate (100 mg, 40.7%) as a light brown solid.

7-methyl-5-(4-(pyrimidin-2-yloxy)phenyl)-6-(pyrrolidin-3-yl)-7H-pyrrolo[2,3-d]pyrimidin-4-amine

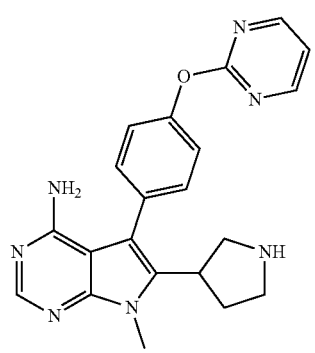 [SMILES: Cn1c(C2CCNC2)c(-c2ccc(Oc3ncccn3)cc2)c2c(N)ncnc21]

1506

Step 4: A round bottomed flask was charged with tert-butyl 3-{4-amino-7-methyl-5-[4-(pyrimidin-2-yloxy)phenyl]-7H-pyrrolo[2,3-d]pyrimidin-6-yl}pyrrolidine-1-carboxylate (200 mg, 410 μmol), and a stirbar. TFA/DCM (1/4 mL) was added, and the solution was stirred 30 min at r.t. The reaction mixture was concentrated in vacuo. Then dissolved in saturated NaHCO$_3$, extracted with DCM for three times. The combined organic layers was dried with anhydrous Na$_2$SO$_4$. Filtered and evaporated to give 7-methyl-5-[4-(pyrimidin-2-yloxy)phenyl]-6-(pyrrolidin-3-yl)-7H-pyrrolo[2,3-d]pyrimidin-4-amine (150 mg, 94.4%) as a off-white solid.

1-(3-(4-amino-7-methyl-5-(4-(pyrimidin-2-yloxy)phenyl)-7H-pyrrolo[2,3-d]pyrimidin-6-yl)pyrrolidin-1-yl)prop-2-en-1-one

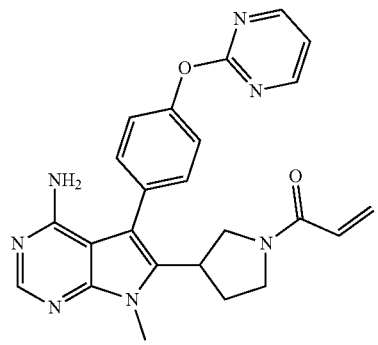

Step 5: A round bottomed flask was charged with 7-methyl-5-[4-(pyrimidin-2-yloxy)phenyl]-6-(pyrrolidin-3-yl)-7H-pyrrolo[2,3-d]pyrimidin-4-amine (50 mg, 129 μmol), TEA (39.0 mg, 387 μmol), dichloromethane (4 mL) and a stirbar. Prop-2-enoyl chloride (10.4 mg, 116 μmol) was added at −30° C., and the solution was stirred for 30 min at −30° C. The reaction mixture was filtered through a pad of Celite®, the pad was washed with DCM, and the filtrate was concentrated in vacuo. The resulting crude material was purified by HPLC (acetonitrile/water/0.1% formic acid). Lyophilization yielded 1-(3-{4-amino-7-methyl-5-[4-(pyrimidin-2-yloxy)phenyl]-7H-pyrrolo[2,3-d]pyrimidin-6-yl}pyrrolidin-1-yl)prop-2-en-1-one (5.92 mg, 11.6%1) as a white amorphous solid.

Additional compounds prepared according to the methods of Example 14 are depicted in Table 13 below.

TABLE 13

*Additional Exemplary Compounds*

| Compound | Structure | Proton NMR | MS [M + 1] |
|---|---|---|---|
| 1-[4-(4-amino-5-{3-methoxy-4-[(6-methylpyridin-2-yl)oxy]phenyl}-7-methyl-7H-pyrrolo[2,3-d]pyrimidin-6-yl)piperidin-1-yl]prop-2-en-1-one | 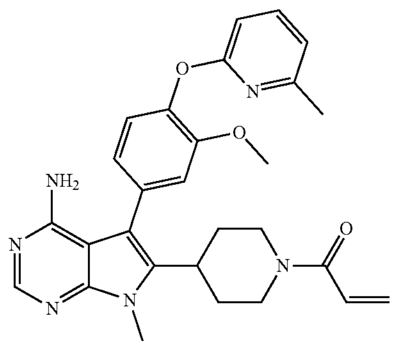 [SMILES: C=CC(=O)N1CCC(c2c(-c3ccc(Oc4cccc(C)n4)c(OC)c3)c3c(N)ncnc3n2C)CC1] | $^1$H NMR (400 MHz, DMSO-d$_6$) δ 8.10 (s, 1H), 7.68 (t, J = 7.7 Hz, 1H), 7.17 (d, J = 8.0 Hz, 1H), 7.10-7.05 (m, 1H), 6.94 (d, J = 7.3 Hz, 2H), 6.76 (dd, J = 16.7, 10.5 Hz, 1H), 6.64 (d, J = 8.2 Hz, 1H), 6.04 (dd, J = 16.7, 2.4 Hz, 1H), 5.61 (dd, J = 10.4, 2.5 Hz, 2H), 4.47 (s, 1H), 4.13-4.06 (m, 1H), 3.77 (s, 3H), 3.67 (s, 3H), 3.09 (s, 2H), 2.64 (s, 2H), 2.31 (s, 3H), 1.83 (s, 2H), 1.57 (s, 2H). | 498.587 |
| 1-(4-(4-amino-7-methyl-5-(4-((6-methylpyridin-2-yl)oxy)phenyl)-7H-pyrrolo[2,3-d]pyrimidin-6-yl)piperidin-1-yl)prop-2-en-1-one | 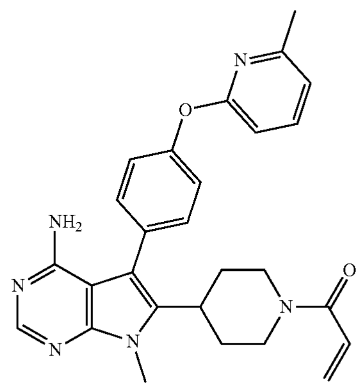 [SMILES: C=CC(=O)N1CCC(c2c(-c3ccc(Oc4cccc(C)n4)cc3)c3c(N)ncnc3n2C)CC1] | $^1$H NMR (400 MHz, Chloroform-d) δ 8.30 (s, 1H), 7.66 (t, J = 7.7 Hz, 1H), 7.35 (d, J = 8.5 Hz, 2H), 7.21 (d, J = 8.3 Hz, 2H), 6.97 (d, J = 7.4 Hz, 1H), 6.76 (d, J = 8.1 Hz, 1H), 6.58 (dd, J = 16.8, 10.6 Hz, 1H), 6.28 (dd, J = 16.8, 2.0 Hz, 1H), 5.70 (dd, J = 10.5, 2.0 Hz, 1H), 4.87-4.83 (m, 2H), 4.79 (s, 1H), 4.08 (d, J = 13.6 Hz, 1H), 3.88 (s, 3H), 3.18-3.03 (m, 2H), 2.64 (s, 1H), 2.50 (s, 3H), 1.83 (s, 2H), 1.75 (s, 2H). | 469.25 |
| 1-[3-(4-amino-7-methyl-5-{4-[(6-methylpyridin-2-yl)oxy]phenyl}-7H-pyrrolo[2,3-d]pyrimidin-6-yl)piperidin-1-yl]prop-2-en-1-one | 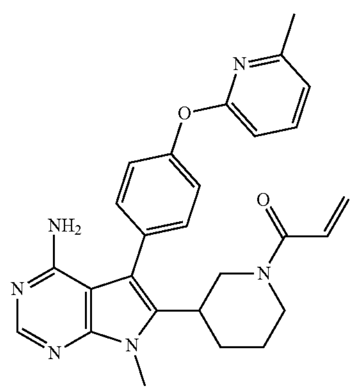 [SMILES: C=CC(=O)N1CCCC(c2c(-c3ccc(Oc4cccc(C)n4)cc3)c3c(N)ncnc3n2C)C1] | $^1$H NMR (400 MHz, DMSO-d$_6$) δ 8.27 (s, 1H), 7.77 (t, J = 7.7 Hz, 1H), 7.44 (d, J = 7.3 Hz, 2H), 7.23 (d, J = 8.1 Hz, 2H), 7.05 (d, J = 7.3 Hz, 1H), 6.87 (d, J = 9.1 Hz, 1H), 6.84-6.75 (m, 1H), 6.08 (t, J = 17.7 Hz, 1H), 5.67 (t, J = 9.9 Hz, 1H), 4.51-4.45 (d, J = 12.5 Hz, 1H), 4.15-4.07 (d, J = 13.4 Hz, 1H), 3.84 (s, 3H), 3.17-3.07 (m, 1H), 2.97 (s, 1H), 2.87-2.61 (t, J = 12.2 Hz, 1H), 2.42-2.35 (s, 3H), 1.90 (d, J = 12.6 Hz, 1H), 1.67 (s, 2H), 1.41 (d, J = 13.9 Hz, 2H), 1.18 (t, J = 7.3 Hz, 1H). | 469.35 |
| 1-[5-(4-amino-7-methyl-5-{4-[(6-methylpyridin-2-yl)oxy]phenyl}-7H-pyrrolo[2,3-d]pyrimidin-6-yl)-1,2,3,6-tetrahydropyridin-1-yl]prop-2-en-1-one | 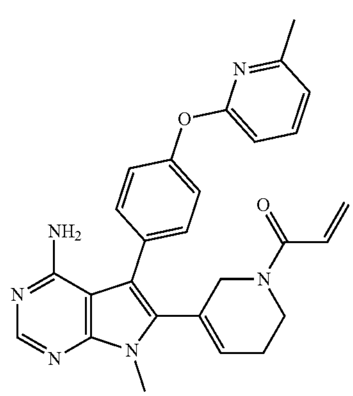 [SMILES: C=CC(=O)N1CCC=C(c2c(-c3ccc(Oc4cccc(C)n4)cc3)c3c(N)ncnc3n2C)C1] | $^1$H NMR (400 MHz, Chloroform-d) δ 8.34 (s, 1H), 7.64 (t, J = 7.8 Hz, 1H), 7.41 (d, J = 8.1 Hz, 2H), 7.22 (d, J = 8.6 Hz, 2H), 6.95 (d, J = 7.4 Hz, 1H), 6.75 (d, J = 8.1 Hz, 1H), 6.67-6.56 (m, 1H), 6.33-6.20 (d, J = 16.6 Hz, 1H), 6.03 (s, 1H), 5.75 (d, J = 10.6 Hz, 1H), 5.61 (d, J = 10.4 Hz, 1H), 5.44 (s, 1H), 4.14 (s, 1H), 3.91 (s, 1H), 3.79 (s, 3H), 3.77 (s, 1H), 3.64 (s, 1H), 2.48 (s, 3H), 2.43 (s, 1H), 2.39 (s, 1H). | 467.35 |

TABLE 13-continued

Additional Exemplary Compounds

| Compound | Structure | Proton NMR | MS [M + 1] |
|---|---|---|---|
| 1-[3-(4-amino-7-methyl-5-{4-[(6-methylpyridin-2-yl)oxy]phenyl}-7H-pyrrolo[2,3-d]pyrimidin-6-yl)-2,5-dihydro-1H-pyrrol-1-yl]prop-2-en-1-one | 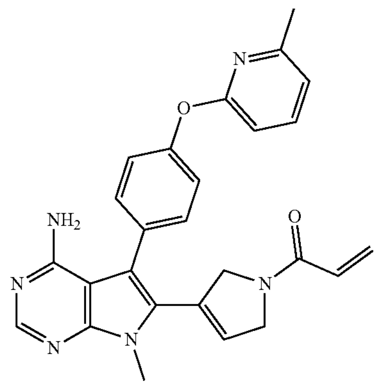 [SMILES: C=CC(=O)N1CC=C(c2c(-c3ccc(Oc4cccc(C)n4)cc3)c3c(N)ncnc3n2C)C1] | ¹H NMR (400 MHz, Chloroform-d) δ 8.36 (d, J = 3.2 Hz, 1H), 7.70-7.59 (m, 1H), 7.40 (dd, J = 11.3, 8.3 Hz, 2H), 7.23 (dd, J = 11.3, 8.2 Hz, 2H), 6.96 (d, J = 7.3 Hz, 1H), 6.79-6.70 (m, 1H), 6.47-6.37 (m, 1H), 6.24-6.11 (m, 1H), 5.96 (s, 1H), 5.79-5.64 (m, 1H), 5.02 (s, 2H), 4.52 (s, 2H), 4.32 (s, 1H), 4.22 (s, 1H), 3.88 (d, J = 10.2 Hz, 3H), 2.49 (d, J = 9.9 Hz, 3H). | 453.30 |
| 1-(4-(4-amino-7-methyl-5-(4-((6-methylpyridin-2-yl)oxy)phenyl)-7H-pyrrolo[2,3-d]pyrimidin-6-yl)-3,6-dihydropyridin-1(2H)-yl)prop-2-en-1-one | 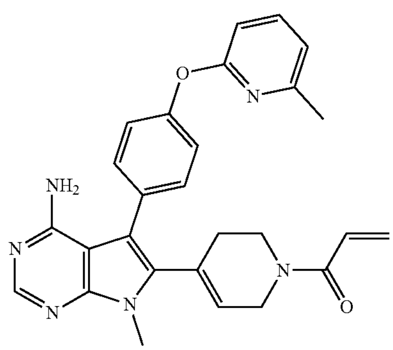 [SMILES: C=CC(=O)N1CC=C(c2c(-c3ccc(Oc4cccc(C)n4)cc3)c3c(N)ncnc3n2C)CC1] | 1H NMR (400 MHz, DMSO-d6) δ 8.16 (s, 1H), 7.75 (t, J = 7.8 Hz, 1H), 7.39 (d, J = 8.1 Hz, 2H), 7.18 (d, J = 8.1 Hz, 2H), 7.03 (d, J = 7.3 Hz, 1H), 6.88-6.70 (m, 2H), 6.12 (d, J = 16.7 Hz, 1H), 5.97 (s, 1H), 5.92 (s, 1H), 5.69 (t, J = 9.4 Hz, 1H), 4.23 (s, 1H), 4.14 (s, 1H), 3.66 (m, 5H), 2.36 (s, 3H), 2.13 (s, 2H). | 467.2 |
| 1-(3-(4-amino-5-(3-methoxy-4-((6-methylpyridin-2-yl)oxy)phenyl)-7-methyl-7H-pyrrolo[2,3-d]pyrimidin-6-yl)pyrrolidin-1-yl)prop-2-en-1-one | 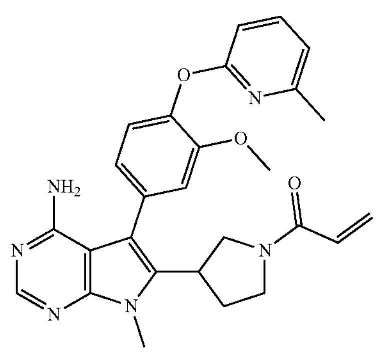 [SMILES: C=CC(=O)N1CCC(c2c(-c3ccc(Oc4cccc(C)n4)c(OC)c3)c3c(N)ncnc3n2C)C1] | ¹H NMR (400 MHz, DMSO-d₆) δ 8.13 (d, J = 1.6 Hz, 1H), 7.67 (t, J = 7.8 Hz, 1H), 7.26-7.07 (m, 2H), 6.96 (dd, J = 15.4, 7.5 Hz, 3H), 6.70 (dd, J = 8.2, 5.8 Hz, 1H), 6.58-6.39 (m, 1H), 6.10 (dd, J = 16.9, 2.6 Hz, 1H), 5.69-5.57 (m, 1H), 3.97 (t, J = 9.2 Hz, 1H), 3.79 (d, J = 6.4 Hz, 4H), 3.73-3.63 (m, 4H), 3.55 (dq, J = 17.8, 9.8, 9.2 Hz, 2H), 2.30 (d, J = 5.6 Hz, 3H), 2.21-1.89 (m, 2H). | 485.15 |
| 1-(3-(4-amino-5-(3-methoxy-4-((6-methylpyridin-2-yl)oxy)phenyl)-7-methyl-7H-pyrrolo[2,3-d]pyrimidin-6-yl)piperidin-1-yl)prop-2-en-1-one | 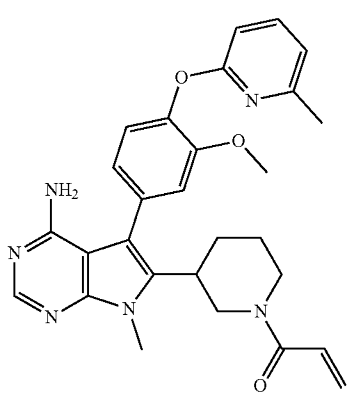 [SMILES: C=CC(=O)N1CCCC(c2c(-c3ccc(Oc4cccc(C)n4)c(OC)c3)c3c(N)ncnc3n2C)C1] | 1H NMR (400 MHz, DMSO-d6) δ 8.13 (s, 1H), 7.69 (t, J = 7.8 Hz, 1H), 7.20 (d, J = 8.0 Hz, 1H), 7.14 (s, 1H), 7.00 (d, J = 8.1 Hz, 1H), 6.95 (d, J = 7.3 Hz, 1H), 6.88-6.71 (m, 2H), 6.09 (t, J = 17.2 Hz, 1H), 5.68 (d, J = 10.9 Hz, 1H), 4.57-4.47 (d, 1H), 4.19-4.09 (d, 1H), 3.81 (s, 3H), 3.71 (s, 3H), 3.17-2.98 (d, 2H), 2.72-2.43 (d, 1H), 2.28 (s, 3H), 1.94 (d, J = 12.6 Hz, 1H), 1.71 (s, 2H), 1.41 (s, 1H). | 499.2 |

TABLE 13-continued

Additional Exemplary Compounds

| Compound | Structure | Proton NMR | MS [M + 1] |
| --- | --- | --- | --- |
| 1-(4-(4-amino-5-(4-methoxyphenyl)-7-methyl-7H-pyrrolo[2,3-d]pyrimidin-6-yl)-3,6-dihydropyridin-1(2H)-yl)prop-2-en-1-one | 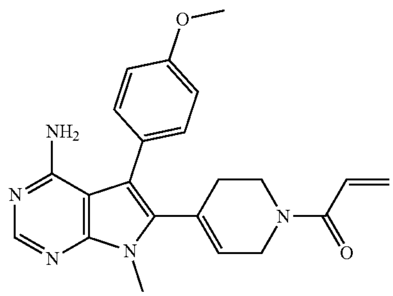 [SMILES: C=CC(=O)N1CC=C(c2c(-c3ccc(OC)cc3)c3c(N)ncnc3n2C)CC1] | 1H NMR (400 MHz, DMSO-d6) δ 8.21 (s, 1H), 7.33-7.25 (m, 2H), 7.06-6.99 (m, 2H), 6.79 (ddd, J = 21.6, 16.7, 10.4 Hz, 1H), 6.13 (dt, J = 16.7, 3.6 Hz, 1H), 5.92 (d, 1H), 5.75-5.64 (m, 1H), 4.22 (s, 1H), 4.13 (s, 1H), 3.80 (s, 3H), 3.66 (m, 5H), 2.08 (s, 2H). | 390.2 |
| 1-(5-(4-amino-5-(3-methoxy-4-((6-methylpyridin-2-yl)oxy)phenyl)-7-methyl-7H-pyrrolo[2,3-d]pyrimidin-6-yl)-3,6-dihydropyridin-1(2H)-yl)prop-2-en-1-one | 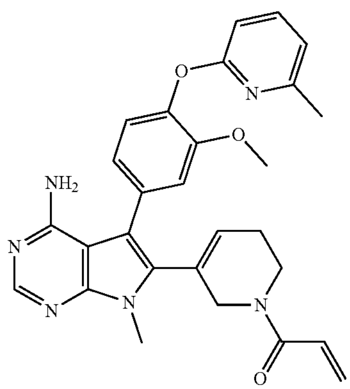 [SMILES: C=CC(=O)N1CCC=C(c2c(-c3ccc(Oc4cccc(C)n4)c(OC)c3)c3c(N)ncnc3n2C)C1] | 1H NMR (400 MHz, DMSO-d6) δ 8.18 (s, 1H), 7.66 (dt, J = 11.8, 7.8 Hz, 1H), 7.17 (m, 1H), 7.11 (d, J = 1.9 Hz, 1H), 7.02-6.91 (m, 2H), 6.85 (dd, J = 16.6, 10.4 Hz, 1H), 6.70 (d, J = 8.3 Hz, 1H), 6.31 (dd, J = 16.6, 10.4 Hz, 1H), 6.20-5.95 (m, J = 16.1 Hz, 3H), 5.75-5.52 (d, J = 10.5 Hz, 1H), 4.01 (s, 2H), 3.71-3.62 (m, 8H), 2.30 (d, J = 2.6 Hz, 5H). | 497.3 |
| 1-(3-(4-amino-7-methyl-5-(4-(pyrimidin-2-yloxy)phenyl)-7H-pyrrolo[2,3-d]pyrimidin-6-yl)pyrrolidin-1-yl)prop-2-en-1-one | 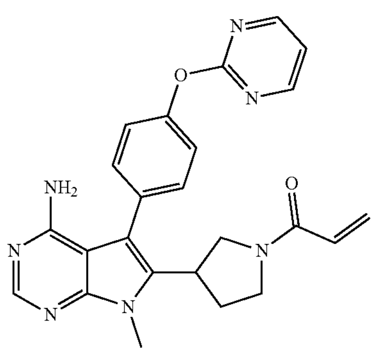 [SMILES: C=CC(=O)N1CCC(c2c(-c3ccc(Oc4ncccn4)cc3)c3c(N)ncnc3n2C)C1] | $^1$H NMR (400 MHz, DMSO-d6) δ 8.69 (t, J = 4.5 Hz, 2H), 8.13 (d, J = 1.8 Hz, 1H), 7.49-7.42 (m, 2H), 7.36-7.28 (m, 3H), 6.51 (ddd, J = 34.2, 16.8, 10.4 Hz, 1H), 6.11 (ddd, J = 16.8, 5.6, 2.4 Hz, 1H), 5.70-5.59 (m, 1H), 3.95 (t, J = 9.2 Hz, 1H), 3.80 (d, J = 6.8 Hz, 3H), 3.77-3.45 (m, 1H), 2.27-1.97 (m, 2H). | 442.25 |
| 1-(4-(4-amino-7-methyl-5-(4-(pyridin-2-yloxy)phenyl)-7H-pyrrolo[2,3-d]pyrimidin-6-yl)-3,6-dihydropyridin-1(2H)-yl)prop-2-en-1-one | 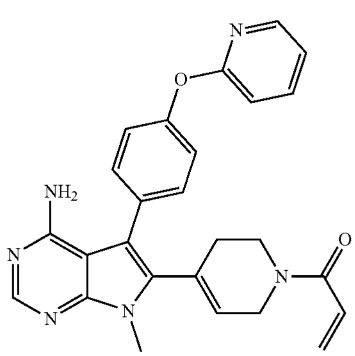 [SMILES: C=CC(=O)N1CC=C(c2c(-c3ccc(Oc4ccccn4)cc3)c3c(N)ncnc3n2C)CC1] | 1H NMR (400 MHz, DMSO-d6) δ 8.23-8.10 (m, 2H), 7.92-7.82 (m, 1H), 7.39 (d, J = 7.9 Hz, 2H), 7.25-7.10 (m, 3H), 7.06 (d, J = 8.3 Hz, 1H), 6.78 (ddd, J = 25.5, 16.6, 10.4 Hz, 1H), 6.12 (dt, J = 16.4, 3.7 Hz, 1H), 5.94 (d, J = 24.1 Hz, 2H), 5.69 (t, J = 9.0 Hz, 1H), 4.26-4.08 (m, 2H), 3.63 (d, J = 12.5 Hz, 4H), 2.13 (s, 2H). | 453.1 |

TABLE 13-continued

Additional Exemplary Compounds

| Compound | Structure | Proton NMR | MS [M + 1] |
| --- | --- | --- | --- |
| 1-(4-(4-amino-7-methyl-5-(4-(pyrimidin-2-yloxy)phenyl)-7H-pyrrolo[2,3-d]pyrimidin-6-yl)-3,6-dihydropyridin-1(2H)-yl)prop-2-en-1-one | 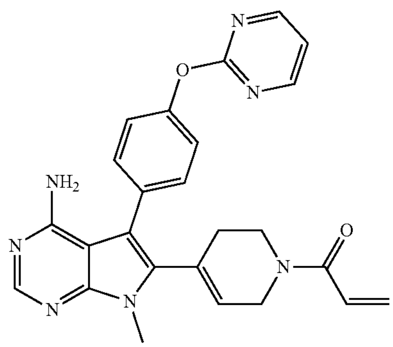 [SMILES: C=CC(=O)N1CC=C(c2c(-c3ccc(Oc4ncccn4)cc3)c3c(N)ncnc3n2C)CC1] | ¹H NMR (400 MHz, DMSO-d6) δ 8.69 (d, J = 4.7 Hz, 2H), 8.17 (s, 1H), 7.43 (d, J = 8.0 Hz, 2H), 7.30 (q, J = 4.0, 3.2 Hz, 3H), 6.80 (ddd, J = 26.5, 16.7, 10.5 Hz, 1H), 6.12 (d, J = 16.8 Hz, 1H), 5.99 (s, 1H), 5.93 (s, 1H), 5.69 (t, J = 9.7 Hz, 1H), 4.23 (s, 1H), 4.14 (s, 1H), 3.66 (s, 3H), 3.62 (s, 0H), 3.07 (s, 1H), 2.15 (s, 2H), 1.17 (t, J = 7.3 Hz, 1H). | 454.3 |
| 1-(4-(4-amino-5-(3-methoxy-4-(pyridin-2-yloxy)phenyl)-7-methyl-7H-pyrrolo[2,3-d]pyrimidin-6-yl)-3,6-dihydropyridin-1(2H)-yl)prop-2-en-1-one | 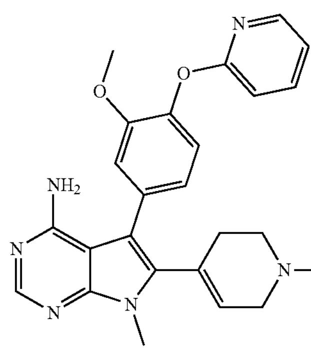 | 1H NMR (400 MHz, DMSO-d6) δ 8.20-8.06 (m, 2H), 7.88-7.75 (m, 1H), 7.20 (d, J = 8.0 Hz, 1H), 7.09 (dd, J = 7.0, 4.8 Hz, 2H), 6.97 (d, J = 8.2 Hz, 2H), 6.80 (ddd, J = 27.3, 16.6, 10.3 Hz, 1H), 6.05 (dd, J = 56.4, 20.5 Hz, 3H), 5.68 (d, J = 9.0 Hz, 1H), 4.20 (d, J = 31.9 Hz, 2H), 3.66 (d, J = 3.0 Hz, 8H), 2.18 (s, 2H). | 483.35 |
| 1-(4-(4-amino-5-(3-methoxy-4-((4-methylpyridin-2-yl)oxy)phenyl)-7-methyl-7H-pyrrolo[2,3-d]pyrimidin-6-yl)-3,6-dihydropyridin-1(2H)-yl)prop-2-en-1-one | 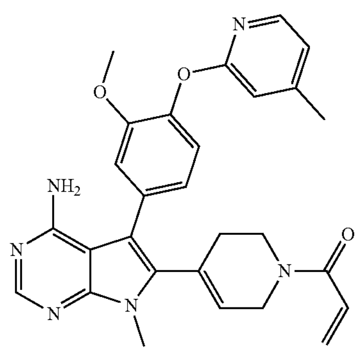 [SMILES: C=CC(=O)N1CC=C(c2c(-c3ccc(Oc4cc(C)ccn4)c(OC)c3)c3c(N)ncnc3n2C)CC1] | 1H NMR (400 MHz, DMSO-d6) δ 8.17 (s, 1H), 7.97 (d, J = 5.1 Hz, 1H), 7.17 (d, J = 8.0 Hz, 1H), 7.08 (s, 1H), 7.01-6.88 (m, 2H), 6.86-6.76 (m, 2H), 6.05 (dd, J = 56.6, 19.7 Hz, 3H), 5.68 (d, J = 9.2 Hz, 1H), 4.20 (d, J = 33.4 Hz, 2H), 2.33 (s, 3H), 2.18 (s, 2H). | 497.4 |
| 1-(3-(4-amino-7-methyl-5-(4-(pyridin-2-yloxy)phenyl)-7H-pyrrolo[2,3-d]pyrimidin-6-yl)pyrrolidin-1-yl)prop-2-en-1-one | 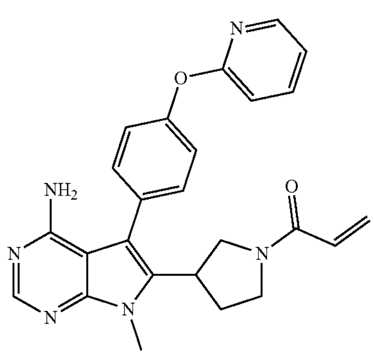 | 1H NMR (400 MHz, DMSO-d6) δ 8.31-8.14 (m, 2H), 7.90 (ddd, J = 9.0, 7.2, 2.0 Hz, 1H), 7.56-7.38 (m, 2H), 7.26-7.21 (m, 2H), 7.19 (s, 1H), 7.10 (dd, J = 8.3, 2.7 Hz, 1H), 6.50 (ddd, J = 36.0, 16.8, 10.3 Hz, 1H), 6.11 (dt, J = 16.8, 2.7 Hz, 1H), 5.64 (td, J = 9.9, 2.4 Hz, 1H), 4.03-3.66 (m, 5H), 3.64-3.23 (m, 5H), 2.35-1.94 (m, 2H). | 441 |

TABLE 13-continued

Additional Exemplary Compounds

| Compound | Structure | Proton NMR | MS [M + 1] |
|---|---|---|---|
| 1-(3-(4-amino-5-(3-methoxy-4-(pyridin-2-yloxy)phenyl)-7-methyl-7H-pyrrolo[2,3-d]pyrimidin-6-yl)pyrrolidin-1-yl)prop-2-en-1-one | 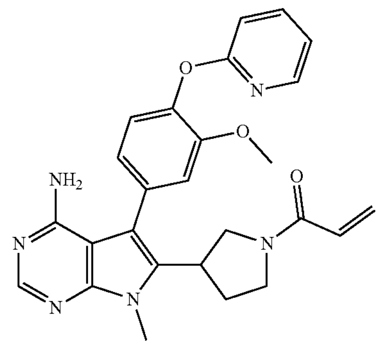 | 1H NMR (400 MHz, DMSO-d6) δ 8.13 (s, 2H), 7.82 (t, J = 8.1 Hz, 1H), 7.27-6.94 (m, 5H), 6.64-6.37 (m, 1H), 6.11 (d, J = 16.6 Hz, 1H), 5.64 (t, J = 10.5 Hz, 2H), 3.99-3.75 (m, 5H), 3.69 (s, 4H), 3.66-3.48 (m, 2H), 2.37-1.96 (m, 2H). | 471.20 |
| 1-(3-(4-amino-5-(3-methoxy-4-(pyrimidin-2-yloxy)phenyl)-7-methyl-7H-pyrrolo[2,3-d]pyrimidin-6-yl)pyrrolidin-1-yl)prop-2-en-1-one | 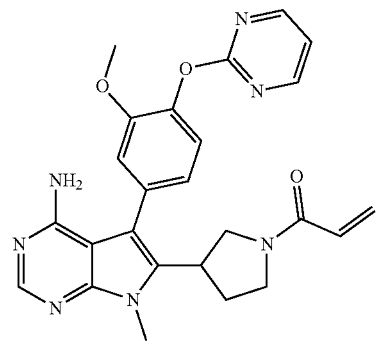 [SMILES: C=CC(=O)N1CCC(c2c(-c3ccc(Oc4ncccn4)c(OC)c3)c3c(N)ncnc3n2C)C1] | 1H NMR (400 MHz, DMSO-d6) δ 8.64 (t, J = 4.8 Hz, 2H), 8.14 (s, 1H), 7.37-7.19 (m, 2H), 7.12 (s, 1H), 7.01 (dd, J = 7.9, 1.9 Hz, 1H), 4.00-3.82 (m, 1H), 3.80 (d, J = 6.4 Hz, 3H), 3.69 (s, 4H), 3.63 (t, J = 10.3 Hz, 1H), 3.33 (s, 1H), 2.35-1.95 (m, 2H). | 472 |
| 1-(3-(4-amino-5-(3-methoxy-4-(6-methylpyridin-3-yl)oxy)phenyl)-7-methyl-7H-pyrrolo[2,3-d]pyrimidin-6-yl)pyrrolidin-1-yl)prop-2-en-1-one | 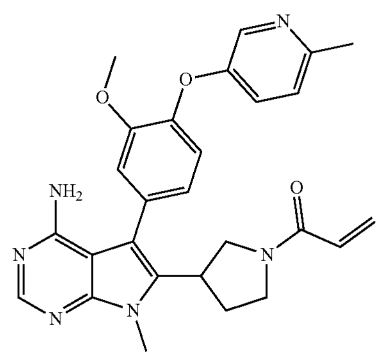 [SMILES: C=CC(=O)N1CCC(c2c(-c3ccc(Oc4ccc(C)nc4)c(OC)c3)c3c(N)ncnc3n2C)C1] | 1H NMR (400 MHz, DMSO-d6) δ 8.20 (dd, J = 12.7, 2.9 Hz, 1H), 8.12 (d, J = 2.1 Hz, 1H), 7.32-7.17 (m, 2H), 7.17-7.04 (m, 2H), 6.96 (d, J = 8.1 Hz, 1H), 6.60-6.38 (m, 1H), 6.10 (dd, J = 16.8, 2.5 Hz, 1H), 5.76-5.54 (m, 2H), 3.92 (t, J = 9.1 Hz, 1H), 3.56 (s, 1H), 2.44 (s, 3H), 2.31-2.22 (m, 1H), 2.08 (s, 2H). | 485.35 |
| 1-(3-(4-amino-7-methyl-5-(4-((6-methylpyridin-2-yl)oxy)phenyl)-7H-pyrrolo[2,3-d]pyrimidin-6-yl)pyrrolidin-1-yl)but-2-yn-1-one | 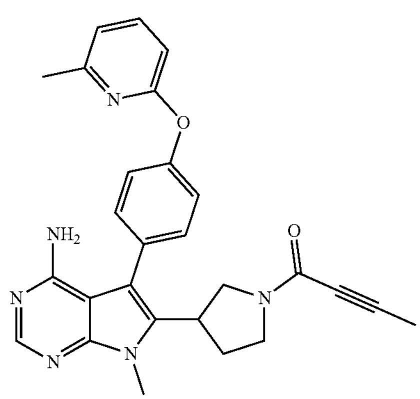 [SMILES: CC#CC(=O)N1CCC(c2c(-c3ccc(Oc4cccc(C)n4)cc3)c3c(N)ncnc3n2C)C1] | ¹H NMR (400 MHz, DMSO-d₆) δ 8.12 (d, J = 2.1 Hz, 1H), 7.76 (td, J = 7.7, 2.9 Hz, 1H), 7.40 (dd, J = 8.6, 3.3 Hz, 2H), 7.21 (dd, J = 8.1, 5.6 Hz, 2H), 7.04 (d, J = 7.3 Hz, 1H), 6.85 (dd, J = 8.2, 2.9 Hz, 1H), 5.78 (s, 1H), 3.92-3.65 (m, 5H), 3.50 (dt, J = 18.9, 9.8 Hz, 2H), 3.28-3.14 (m, 1H), 2.36 (s, 3H), 2.19 (d, J = 6.9 Hz, 1H), 1.97 (d, J = 19.3 Hz, 4H). | 467.25 |

TABLE 13-continued

Additional Exemplary Compounds

| Compound | Structure | Proton NMR | MS [M + 1] |
| --- | --- | --- | --- |
| (E)-1-(3-(4-amino-7-methyl-5-(4-((6-methylpyridin-2-yl)oxy)phenyl)-7H-pyrrolo[2,3-d]pyrimidin-6-yl)pyrrolidin-1-yl)but-2-en-1-one | 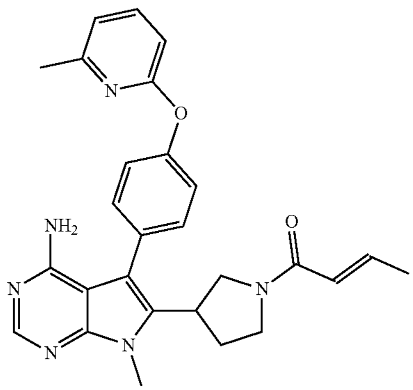 [SMILES: C/C=C/C(=O)N1CCC(c2c(-c3ccc(Oc4cccc(C)n4)cc3)c3c(N)ncnc3n2C)C1] | 1H NMR (400 MHz, DMSO-d6) δ 8.12 (d, J = 2.7 Hz, 1H), 7.76 (t, J = 7.8 Hz, 1H), 7.41 (dd, J = 8.6, 3.8 Hz, 2H), 7.19 (dd, J = 8.2, 5.7 Hz, 2H), 7.04 (d, J = 7.3 Hz, 1H), 6.84 (dd, J = 8.2, 2.6 Hz, 1H), 6.65 (ddt, J = 13.7, 10.7, 6.7 Hz, 1H), 6.17 (ddd, J = 31.7, 14.9, 1.9 Hz, 1H), 5.78 (s, 1H), 3.98-3.85 (m, 1H), 3.79 (d, J = 8.4 Hz, 4H), 3.63 (d, J = 9.9 Hz, 1H), 3.53 (d, J = 10.2 Hz, 1H), 3.48-3.39 (m, 1H), 2.36 (d, J = 4.2 Hz, 3H), 2.26-1.91 (m, 2H), 1.80 (td, J = 6.9, 1.6 Hz, 3H). | 469 |
| 1-(3-(4-amino-7-methyl-5-(4-((6-methylpyridin-2-yl)oxy)phenyl)-7H-pyrrolo[2,3-d]pyrimidin-6-yl)pyrrolidin-1-yl)-2-methylprop-2-en-1-one | 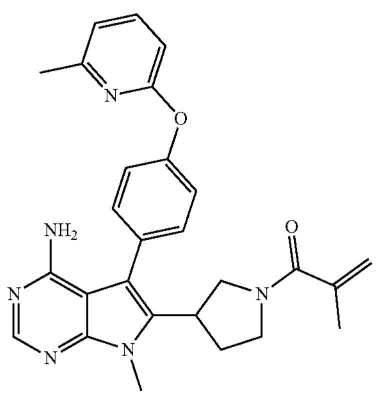 [SMILES: C=C(C)C(=O)N1CCC(c2c(-c3ccc(Oc4cccc(C)n4)cc3)c3c(N)ncnc3n2C)C1] | 1H NMR (400 MHz, DMSO-d6) δ 8.12 (s, 1H), 7.76 (q, J = 7.5 Hz, 1H), 7.62-7.33 (m, 2H), 7.21 (d, J = 8.0 Hz, 2H), 7.04 (d, J = 7.4 Hz, 1H), 6.84 (s, 1H), 5.61 (s, 1H), 5.22 (d, J = 18.1 Hz, 1H), 5.05 (d, J = 52.4 Hz, 1H), 3.78 (s, 3H), 3.71 (d, J = 9.5 Hz, 2H), 3.34 (s, 2H), 3.34 (s, 1H), 2.36 (s, 3H), 2.19 (s, 1H), 1.99 (dt, J = 21.1, 10.0 Hz, 1H), 1.81 (d, J = 14.3 Hz, 3H). | 469.30 |
| 1-(4-(4-amino-7-methyl-5-(4-((6-methylpyridin-2-yl)oxy)phenyl)-7H-pyrrolo[2,3-d]pyrimidin-6-yl)piperidin-1-yl)-2-methylprop-2-en-1-one | 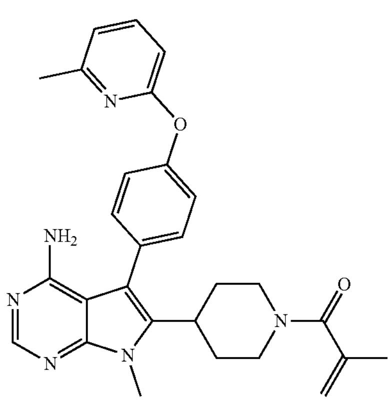 [SMILES: C=C(C)C(=O)N1CCC(c2c(-c3ccc(Oc4cccc(C)n4)cc3)c3c(N)ncnc3n2C)CC1] | 1H NMR (400 MHz, DMSO-d6) δ 8.10 (s, 1H), 7.76 (t, J = 7.8 Hz, 1H), 7.39 (d, J = 8.2 Hz, 2H), 7.20 (d, J = 8.2 Hz, 2H), 7.05 (d, J = 7.4 Hz, 1H), 6.80 (d, J = 8.1 Hz, 1H), 5.08 (s, 1H), 4.80 (s, 1H), 4.36 (s, 1H), 3.78 (s, 3H), 3.20 (t, J = 12.4 Hz, 1H), 3.06 (s, 1H), 2.37 (s, 3H), 1.78 (s, 4H), 1.50 (d, J = 10.0 Hz, 2H). | 483.35 |

TABLE 13-continued

Additional Exemplary Compounds

| Compound | Structure | Proton NMR | MS [M + 1] |
| --- | --- | --- | --- |
| (E)-1-(4-(4-amino-7-methyl-5-(4-((6-methylpyridin-2-yl)oxy)phenyl)-7H-pyrrolo[2,3-d]pyrimidin-6-yl)piperidin-1-yl)but-2-en-1-one | 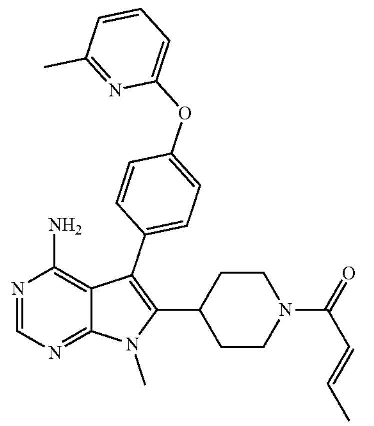 [SMILES: C/C=C/C(=O)N1CCC(c2c(-c3ccc(Oc4cccc(C)n4)cc3)c3c(N)ncnc3n2C)CC1] | 1H NMR (400 MHz, DMSO-d6) δ 8.10 (s, 1H), 7.76 (t, J = 7.8 Hz, 1H), 7.43-7.32 (m, 2H), 7.24-7.13 (m, 2H), 7.04 (d, J = 7.4 Hz, 1H), 6.81 (d, J = 8.2 Hz, 1H), 6.63 (dq, J = 13.4, 6.7 Hz, 1H), 6.46 (dd, J = 14.8, 1.9 Hz, 1H), 4.48 (s, 1H), 4.09 (d, J = 13.1 Hz, 1H), 3.77 (s, 3H), 3.16 (t, J = 12.3 Hz, 1H), 3.03 (s, 1H), 2.58 (s, 1H), 2.36 (s, 3H), 1.87-1.72 (m, 5H), 1.52 (d, J = 16.1 Hz, 2H). | 483.25 |
| 1-(4-(4-amino-7-methyl-5-(4-((6-methylpyridin-2-yl)oxy)phenyl)-7H-pyrrolo[2,3-d]pyrimidin-6-yl)piperidin-1-yl)but-2-yn-1-one | 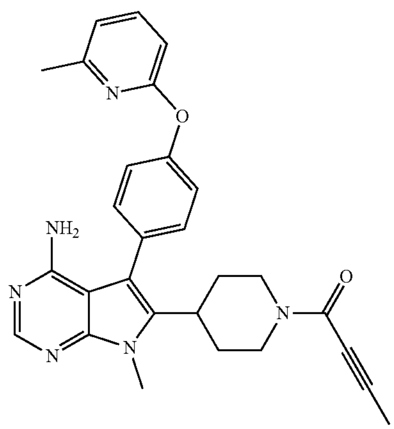 [SMILES: CC#CC(=O)N1CCC(c2c(-c3ccc(Oc4cccc(C)n4)cc3)c3c(N)ncnc3n2C)CC1] | 1H NMR (400 MHz, DMSO-d6) δ 8.10 (s, 1H), 7.76 (t, J = 7.8 Hz, 1H), 7.38 (d, J = 8.3 Hz, 2H), 7.31-7.15 (m, 2H), 7.04 (d, J = 7.3 Hz, 1H), 6.82 (d, J = 8.1 Hz, 1H), 4.39-4.20 (m, 2H), 3.78 (s, 3H), 3.23-3.07 (m, 2H), 2.66 (dd, J = 13.5, 10.8 Hz, 1H), 2.36 (s, 3H), 2.00 (s, 3H), 1.90-1.73 (m, 2H), 1.50 (dtd, J = 37.5, 12.7, 4.2 Hz, 2H). | 481.35 |
| 1-(4-(4-amino-7-methyl-5-(4-(pyrimidin-2-yloxy)phenyl)-7H-pyrrolo[2,3-d]pyrimidin-6-yl)piperidin-1-yl)prop-2-en-1-one | 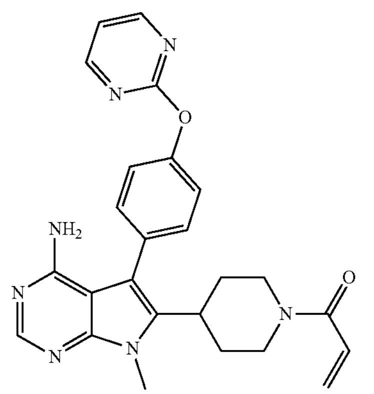 [SMILES: C=CC(=O)N1CCC(c2c(-c3ccc(Oc4ncccn4)cc3)c3c(N)ncnc3n2C)CC1] | 1H NMR (400 MHz, DMSO-d6) δ 8.69 (d, J = 4.8 Hz, 2H), 8.14 (s, 1H), 7.42 (d, J = 8.0 Hz, 2H), 7.35-7.21 (m, 3H), 6.76 (dd, J = 16.7, 10.3 Hz, 1H), 6.17-5.90 (m, 1H), 5.63 (d, J = 10.7 Hz, 1H), 4.49 (s, 1H), 4.10 (s, 1H), 3.79 (s, 3H), 2.65 (d, J = 19.5 Hz, 3H), 1.81 (s, 2H), 1.54 (s, 2H). | 456 |
| 1-(3-(4-amino-7-methyl-5-phenyl-7H-pyrrolo[2,3-d]pyrimidin-6-yl)pyrrolidin-1-yl)prop-2-en-1-one | 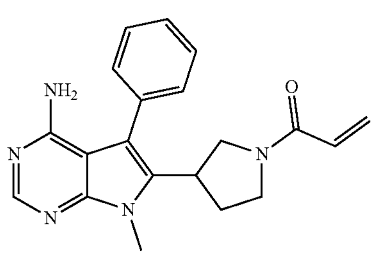 [SMILES: C=CC(=O)N1CCC(c2c(-c3ccccc3)c3c(N)ncnc3n2C)C1] | $^1$H NMR (400 MHz, DMSO-d$_6$) δ 8.11 (d, J = 1.9 Hz, 1H), 7.53-7.36 (m, 5H), 6.46 (ddd, J = 40.1, 16.8, 10.3 Hz, 1H), 6.08 (ddd, J = 16.8, 4.7, 2.4 Hz, 1H), 5.63 (ddd, J = 12.9, 10.3, 2.5 Hz, 1H), 3.78 (d, J = 6.5 Hz, 4H), 3.66 (s, 1H), 3.50 (s, 2H), 3.25 (s, 1H), 2.31-1.71 (m, 2H). | 348.15 |

TABLE 13-continued

Additional Exemplary Compounds

| Compound | Structure | Proton NMR | MS [M + 1] |
|---|---|---|---|
| 1-(4-(4-amino-7-methyl-5-(4-(pyridin-2-yloxy)phenyl)-7H-pyrrolo[2,3-d]pyrimidin-6-yl)piperidin-1-yl)prop-2-en-1-one | 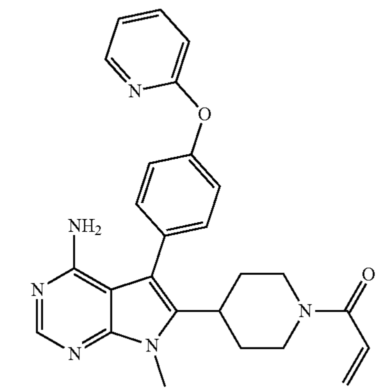 [SMILES: C=CC(=O)N1CCC(c2c(-c3ccc(Oc4ccccn4)cc3)c3c(N)ncnc3n2C)CC1] | ¹H NMR (400 MHz, DMSO-d₆) δ 8.23 (ddd, J = 4.9, 2.1, 0.8 Hz, 1H), 8.11 (s, 1H), 7.90 (ddd, J = 8.3, 7.2, 2.1 Hz, 1H), 7.42-7.34 (m, 2H), 7.25-7.15 (m, 3H), 7.07 (dt, J = 8.2, 0.9 Hz, 1H), 6.77 (dd, J = 16.7, 10.5 Hz, 1H), 6.05 (dd, J = 16.7, 2.5 Hz, 1H), 5.63 (dd, J = 10.5, 2.5 Hz, 2H), 4.48 (d, J = 12.7 Hz, 1H), 4.08 (d, J = 13.5 Hz, 1H), 3.78 (s, 3H), 3.23-3.12 (m, 1H), 3.06 (t, J = 12.8 Hz, 1H), 2.62 (t, J = 12.6 Hz, 1H), 1.81 (d, J = 12.9 Hz, 2H), 1.58-1.48 (m, 2H). | 455.25 |
| (R)-1-(3-(4-amino-7-methyl-5-(4-(pyrimidin-2-yloxy)phenyl)-7H-pyrrolo[2,3-d]pyrimidin-6-yl)pyrrolidin-1-yl)prop-2-en-1-one | 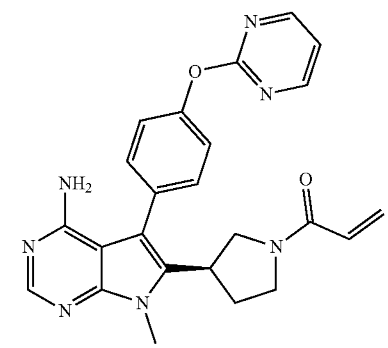 [SMILES: C=CC(=O)N1CC[C@@H](c2c(-c3ccc(Oc4ncccn4)cc3)c3c(N)ncnc3n2C)C1] | ¹H NMR (400 MHz, DMSO-d6) δ 8.69 (t, J = 4.5 Hz, 2H), 8.15 (d, J = 1.1 Hz, 1H), 7.49-7.42 (m, 2H), 7.32 (dd, J = 7.6, 2.9 Hz, 3H), 6.51 (ddd, J = 34.7, 16.8, 10.3 Hz, 1H), 6.11 (ddd, J = 16.8, 5.7, 2.4 Hz, 1H), 5.65 (ddd, J = 12.4, 10.4, 2.5 Hz, 1H), 4.00-3.91 (m, 0H), 3.81 (d, J = 6.5 Hz, 3H), 3.78-3.45 (m, 3H), 3.34-3.24 (m, 0H), 2.22 (tt, J = 10.7, 5.9 Hz, 0H), 2.13 (d, J = 8.3 Hz, 1H), 2.04 (dt, J = 21.0, 11.0 Hz, 0H), 1.24 (s, 1H), 1.18 (t, J = 7.2 Hz, 0H), 0.89 (s, 1H). | 442.25 |
| (S)-1-(3-(4-amino-7-methyl-5-(4-(pyrimidin-2-yloxy)phenyl)-7H-pyrrolo[2,3-d]pyrimidin-6-yl)pyrrolidin-1-yl)prop-2-en-1-one | 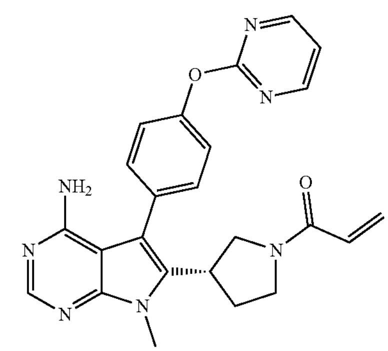 [SMILES: C=CC(=O)N1CC[C@H](c2c(-c3ccc(Oc4ncccn4)cc3)c3c(N)ncnc3n2C)C1] | ¹H NMR (400 MHz, DMSO-d6) δ 8.69 (t, J = 4.5 Hz, 2H), 8.13 (d, J = 1.8 Hz, 1H), 7.49-7.42 (m, 2H), 7.32 (dd, J = 6.5, 3.5 Hz, 3H), 6.51 (ddd, J = 34.2, 16.8, 10.3 Hz, 1H), 6.11 (ddd, J = 16.8, 5.7, 2.4 Hz, 1H), 5.87 (s, 2H), 5.64 (ddd, J = 12.4, 10.4, 2.5 Hz, 1H), 3.80 (d, J = 6.7 Hz, 3H), 3.78-3.61 (m, 1H), 3.54 (dtd, J = 24.3, 10.1, 9.6, 6.2 Hz, 1H), 3.34-3.24 (m, 0H), 2.28-1.94 (m, 2H). | 442.25 |
| 1-(3-(4-amino-5-(4-methoxyphenyl)-7-methyl-7H-pyrrolo[2,3-d]pyrimidin-6-yl)pyrrolidin-1-yl)prop-2-en-1-one | 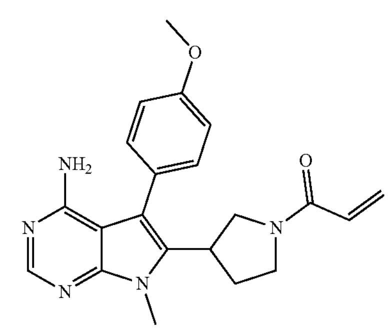 [SMILES: C=CC(=O)N1CCC(c2c(-c3ccc(OC)cc3)c3c(N)ncnc3n2C)C1] | ¹H NMR (400 MHz, DMSO-d₆) δ 8.10 (d, J = 1.7 Hz, 1H), 7.30 (d, J = 8.2 Hz, 2H), 7.03 (d, J = 8.3 Hz, 2H), 6.47 (ddd, J = 40.7, 16.8, 10.3 Hz, 1H), 6.09 (ddd, J = 16.8, 5.6, 2.4 Hz, 1H), 5.63 (ddd, J = 14.6, 10.3, 2.5 Hz, 2H), 3.81 (d, J = 1.1 Hz, 3H), 3.77 (d, J = 6.0 Hz, 4H), 3.66 (q, J = 8.7, 7.2 Hz, 1H), 3.52 (d, J = 9.7 Hz, 2H), 2.35-1.70 (m, 2H). | 378.15 |

TABLE 13-continued

Additional Exemplary Compounds

| Compound | Structure | Proton NMR | MS [M + 1] |
|---|---|---|---|
| 1-(3-(4-amino-7-ethyl-5-(4-(pyrimidin-2-yloxy)phenyl)-7H-pyrrolo[2,3-d]pyrimidin-6-yl)pyrrolidin-1-yl)prop-2-en-1-one | 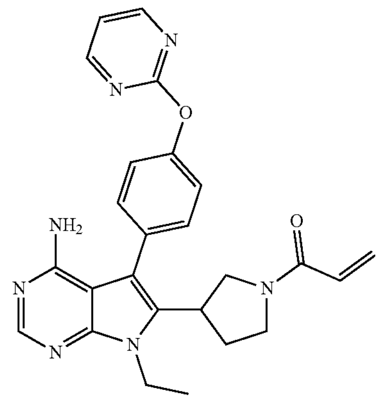 [SMILES: C=CC(=O)N1CCC(c2c(-c3ccc(Oc4ncccn4)cc3)c3c(N)ncnc3n2CC)C1] | $^1$H NMR (400 MHz, DMSO-d6) δ 8.69 (t, J = 5.0 Hz, 2H), 8.13 (d, J = 1.6 Hz, 1H), 7.50-7.43 (m, 2H), 7.31 (dd, J = 6.0, 3.6 Hz, 3H), 6.49 (ddd, J = 30.9, 16.8, 10.3 Hz, 1H), 6.10 (ddd, J = 16.8, 5.9, 2.5 Hz, 1H), 5.64 (td, J = 10.0, 2.4 Hz, 1H), 4.31 (t, J = 3.2 Hz, 1H), 4.29 (s, 2H), 3.76 (s, 1H), 3.66 (t, J = 9.2 Hz, 1H), 3.61-3.51 (m, 1H), 3.49 (t, J = 9.8 Hz, 1H), 3.32-3.24 (m, 1H), 2.27-2.11 (m, 1H), 2.11-1.90 (m, 1H), 1.35 (td, J = 7.0, 3.7 Hz, 3H). | 456.3 |
| 1-(3-(4-amino-7-(3-hydroxycyclobutyl)-5-(4-(pyrimidin-2-yloxy)phenyl)-7H-pyrrolo[2,3-d]pyrimidin-6-yl)pyrrolidin-1-yl)prop-2-en-1-one | 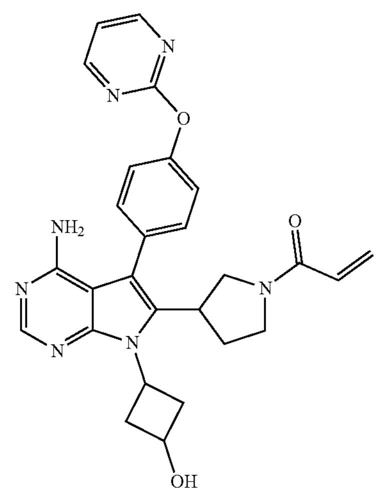 [SMILES: C=CC(=O)N1CCC(c2c(-c3ccc(Oc4ncccn4)cc3)c3c(N)ncnc3n2C2CC(O)C2)C1] | 1H NMR (400 MHz, Chloroform-d) δ 8.63 (t, J = 3.9 Hz, 2H), 8.26 (d, J = 6.1 Hz, 1H), 7.39 (q, J = 8.9, 8.3 Hz, 4H), 7.14 (t, J = 4.8 Hz, 1H), 6.60-6.15 (m, 2H), 5.88-5.54 (m, 1H), 4.72-4.46 (m, 1H), 4.27 (dd, J = 13.0, 6.6 Hz, 1H), 4.11-3.88 (m, 1H), 3.80 (d, J = 8.2 Hz, 1H), 3.59 (tt, J = 19.8, 9.5 Hz, 3H), 3.37-2.99 (m, 2H), 2.20 (q, J = 10.3, 9.6 Hz, 2H), 2.05 (d, J = 9.7 Hz, 1H), 1.28 (s, 1H). | 498 |
| 1-(3-(4-amino-7-(2-(4-methylpiperazin-1-yl)ethyl)-5-(4-(pyrimidin-2-yloxy)phenyl)-7H-pyrrolo[2,3-d]pyrimidin-6-yl)pyrrolidin-1-yl)prop-2-en-1-one | 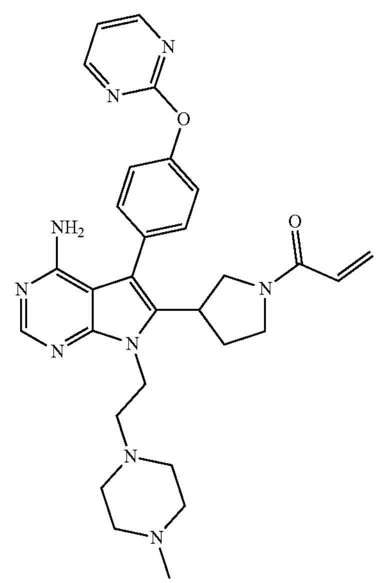 [SMILES: C=CC(=O)N1CCC(c2c(-c3ccc(Oc4ncccn4)cc3)c3c(N)ncnc3n2CCN2CCN(C)CC2)C1] | $^1$H NMR (400 MHz, Chloroform-d) δ 8.62 (t, J = 4.8 Hz, 2H), 8.31 (d, J = 3.2 Hz, 1H), 7.44 (d, J = 8.2 Hz, 2H), 7.37-7.29 (m, 2H), 7.12 (q, J = 4.4 Hz, 1H), 6.43-6.33 (m, 1H), 6.28 (dd, J = 16.8, 9.8 Hz, 1H), 5.75-5.64 (m, 1H), 4.73 (s, 2H), 4.42 (dd, J = 14.1, 7.2 Hz, 2H), 3.97-3.72 (m, 1H), 3.68-3.32 (m, 4H), 2.96-2.78 (m, 2H), 2.71 (d, J = 24.7 Hz, 8H), 2.41 (d, J = 27.9 Hz, 3H), 2.32-2.19 (m, 2H), 1.28 (s, 1H). | 554.30 |

TABLE 13-continued

Additional Exemplary Compounds

| Compound | Structure | Proton NMR | MS [M + 1] |
|---|---|---|---|
| 1-(3-(4-amino-5-(4-(pyrimidin-2-yloxy)phenyl)-7-(tetrahydro-2H-pyran-4-yl)-7H-pyrrolo[2,3-d]pyrimidin-6-yl)pyrrolidin-1-yl)prop-2-en-1-one | 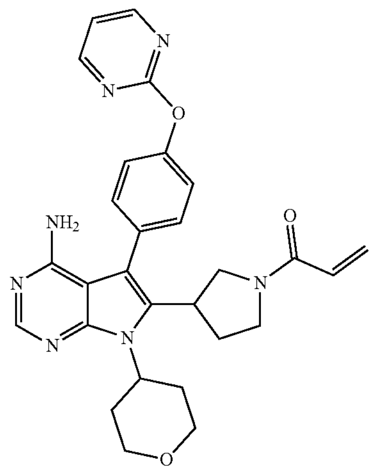 [SMILES: C=CC(=O)N1CCC(c2c(-c3ccc(Oc4ncccn4)cc3)c3c(N)ncnc3n2C2CCOCC2)C1] | $^1$H NMR (400 MHz, DMSO-d6) δ 8.69 (t, J = 4.5 Hz, 2H), 8.11 (s, 1H), 7.46 (d, J = 8.1 Hz, 2H), 7.31 (td, J = 6.1, 5.0, 2.0 Hz, 3H), 6.60 (dd, J = 16.8, 10.3 Hz, 1H), 6.13 (ddd, J = 16.7, 8.6, 2.4 Hz, 1H), 5.66 (ddd, J = 19.8, 10.2, 2.4 Hz, 1H), 4.43 (s, 1H), 4.00 (d, J = 11.1 Hz, 2H), 3.80 (s, 2H), 3.72 (s, 0H), 3.57-3.48 (m, 2H), 3.51-3.38 (m, 1H), 3.38-3.25 (m, 1H), 3.04 (d, J = 14.2 Hz, 2H), 2.21 (dd, J = 12.7, 6.6 Hz, 0H), 1.93 (t, J = 10.5 Hz, 0H), 1.74 (d, J = 13.8 Hz, 2H). | 512.4 |
| 1-(3-(4-amino-7-(2-morpholinoethyl)-5-(4-(pyrimidin-2-yloxy)phenyl)-7H-pyrrolo[2,3-d]pyrimidin-6-yl)pyrrolidin-1-yl)prop-2-en-1-one | 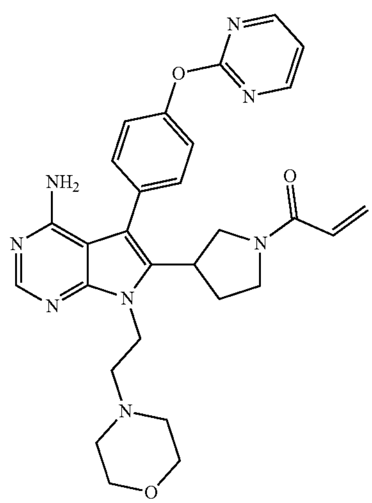 | $^1$H NMR (400 MHz, DMSO-d$_6$) δ 8.69 (t, J = 5.0 Hz, 2H), 8.12 (s, 1H), 7.46 (d, J = 8.1 Hz, 2H), 7.32 (d, J = 7.8 Hz, 3H), 6.48 (ddd, J = 30.4, 16.8, 10.3 Hz, 1H), 6.16-6.05 (m, 1H), 5.88-5.31 (m, 2H), 4.35 (q, J = 5.9, 4.8 Hz, 2H), 4.13-3.84 (m, 1H), 3.68 (dd, J = 23.6, 9.2 Hz, 2H), 3.64-3.44 (m, 6H), 3.34 (s, 2H), 2.72-2.50 (m, 4H), 2.40-1.47 (m, 2H). | 541.45 |
| 1-(3-(4-amino-7-(2-(dimethylamino)ethyl)-5-(4-(pyrimidin-2-yloxy)phenyl)-7H-pyrrolo[2,3-d]pyrimidin-6-yl)pyrrolidin-1-yl)prop-2-en-1-one | 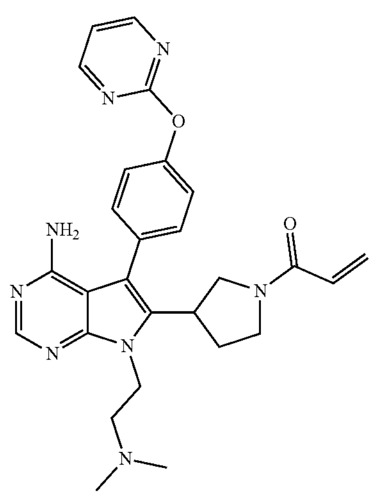 [SMILES: C=CC(=O)N1CCC(c2c(-c3ccc(Oc4ncccn4)cc3)c3c(N)ncnc3n2CCN(C)C)C1] | $^1$H NMR (400 MHz, Chloroform-d) δ 8.61 (t, J = 4.6 Hz, 2H), 8.32 (d, J = 2.1 Hz, 1H), 7.50-7.40 (m, 2H), 7.36-7.30 (m, 2H), 7.12 (td, J = 4.8, 2.4 Hz, 1H), 6.47-6.36 (m, 1H), 6.36-6.19 (m, 1H), 5.68 (ddd, J = 15.8, 8.6, 3.7 Hz, 1H), 4.70 (s, 2H), 4.41 (dp, J = 21.2, 6.9 Hz, 2H), 4.15-3.73 (m, 2H), 3.57 (dtd, J = 39.7, 19.1, 17.7, 8.6 Hz, 3H), 2.77 (t, J = 7.2 Hz, 2H), 2.37 (d, J = 10.1 Hz, 6H), 2.31-1.98 (m, 2H). | 499.25 |

TABLE 13-continued

Additional Exemplary Compounds

| Compound | Structure | Proton NMR | MS [M + 1] |
| --- | --- | --- | --- |
| 1-(3-(4-amino-5-(4-(pyrimidin-2-yloxy)phenyl)-7H-pyrrolo[2,3-d]pyrimidin-6-yl)pyrrolidin-1-yl)prop-2-en-1-one | 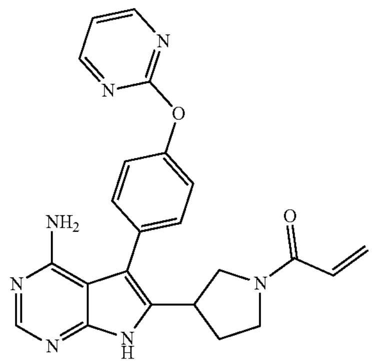 | $^1$H NMR (400 MHz, DMSO-d$_6$) δ 11.86 (d, J = 2.0 Hz, 1H), 8.69 (d, J = 4.8 Hz, 2H), 8.10 (s, 1H), 7.47 (dd, J = 8.5, 3.5 Hz, 2H), 7.41-7.23 (m, 3H), 6.59 (ddd, J = 16.8, 10.3, 2.4 Hz, 1H), 6.15 (dd, J = 16.8, 2.5 Hz, 1H), 5.67 (ddd, J = 10.7, 8.7, 2.5 Hz, 2H), 4.01 (t, J = 8.9 Hz, 1H), 3.90-3.81 (m, 1H), 3.78-3.50 (m, 2H), 3.42 (dd, J = 10.7, 6.2 Hz, 1H), 2.42-2.03 (m, 2H). | 428.25 |
| rel-(R)-1-(3-(4-amino-7-ethyl-5-(4-(pyrimidin-2-yloxy)phenyl)-7H-pyrrolo[2,3-d]pyrimidin-6-yl)pyrrolidin-1-yl)prop-2-en-1-one | 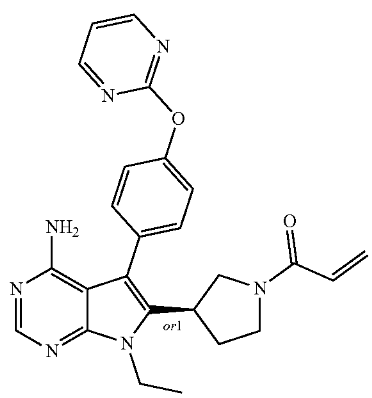 [SMILES: C=CC(=O)N1CC[C@@H](c2c(-c3ccc(Oc4ncccn4)cc3)c3c(N)ncnc3n2CC)C1] | $^1$H NMR (400 MHz, DMSO-d6) δ 8.69 (t, J = 5.0 Hz, 2H), 8.14 (d, J = 1.0 Hz, 1H), 7.47 (d, J = 8.0 Hz, 2H), 7.31 (dd, J = 6.3, 3.9 Hz, 3H), 6.49 (ddd, J = 31.1, 16.8, 10.3 Hz, 1H), 6.10 (ddd, J = 16.9, 5.9, 2.4 Hz, 1H), 5.64 (td, J = 10.0, 2.5 Hz, 1H), 4.30 (d, J = 6.8 Hz, 2H), 3.85 (dd, J = 11.8, 8.0 Hz, 1H), 3.61-3.51 (m, 1H), 3.49 (t, J = 9.7 Hz, 1H), 3.27 (d, J = 11.4 Hz, 1H), 2.18 (ddt, J = 26.2, 14.2, 7.0 Hz, 1H), 1.99-1.90 (m, 1H), 1.35 (td, J = 7.2, 3.8 Hz, 3H). | 456.3 |
| rel-(S)-1-(3-(4-amino-7-ethyl-5-(4-(pyrimidin-2-yloxy)phenyl)-7H-pyrrolo[2,3-d]pyrimidin-6-yl)pyrrolidin-1-yl)prop-2-en-1-one | 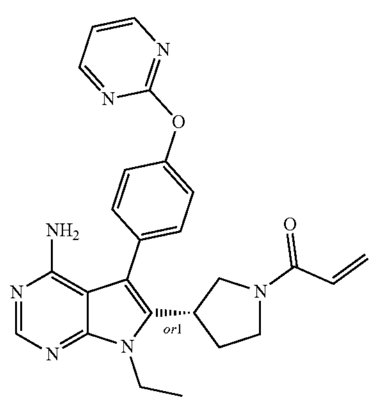 [SMILES: C=CC(=O)N1CC[C@H](c2c(-c3ccc(Oc4ncccn4)cc3)c3c(N)ncnc3n2CC)C1] | $^1$H NMR (400 MHz, DMSO-d6) δ 8.69 (t, J = 5.1 Hz, 2H), 8.15 (s, 1H), 7.47 (d, J = 8.1 Hz, 2H), 7.31 (td, J = 5.7, 4.9, 2.0 Hz, 3H), 6.49 (ddd, J = 31.5, 16.8, 10.3 Hz, 1H), 6.10 (ddd, J = 16.8, 5.9, 2.4 Hz, 1H), 5.64 (td, J = 10.0, 2.5 Hz, 1H), 4.31 (d, J = 7.5 Hz, 2H), 3.66 (t, J = 9.1 Hz, 2H), 3.51 (dt, J = 19.2, 9.5 Hz, 1H), 2.29-2.13 (m, 1H), 2.07 (d, J = 9.5 Hz, 1H), 1.96 (q, J = 10.4 Hz, 1H), 1.35 (td, J = 7.1, 3.5 Hz, 3H). | 456.3 |

TABLE 13-continued

Additional Exemplary Compounds

| Compound | Structure | Proton NMR | MS [M + 1] |
|---|---|---|---|
| (R)-1-(3-(4-amino-7-(2-morpholinoethyl)-5-(4-(pyrimidin-2-yloxy)phenyl)-7H-pyrrolo[2,3-d]pyrimidin-6-yl)pyrrolidin-1-yl)prop-2-en-1-one | 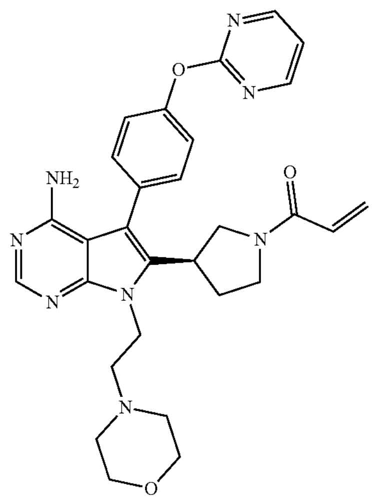 [SMILES: C=CC(=O)N1CC[C@@H](c2c(-c3ccc(Oc4ncccn4)cc3)c3c(N)ncnc3n2CCN2CCOCC2)C1] | $^1$H NMR (400 MHz, DMSO-d$_6$) δ 8.69 (t, J = 5.0 Hz, 2H), 8.12 (d, J = 1.9 Hz, 1H), 7.46 (d, J = 8.2 Hz, 2H), 7.31 (dq, J = 7.0, 2.5, 1.9 Hz, 3H), 6.48 (ddd, J = 31.7, 16.8, 10.3 Hz, 1H), 6.10 (ddd, J = 16.8, 5.5, 2.4 Hz, 1H), 5.64 (ddd, J = 10.3, 6.4, 2.4 Hz, 1H), 4.36 (s, 2H), 4.02-3.83 (m, 1H), 3.82-3.62 (m, 2H), 3.60-3.45 (m, 6H), 3.32 (s, 1H), 2.71-2.66 (m, 2H), 2.48 (s, 3H), 2.22 (ddt, J = 35.7, 12.7, 6.6 Hz, 1H), 1.99 (dq, J = 44.7, 10.4 Hz, 1H). | 541.45 |
| (S)-1-(3-(4-amino-7-(2-morpholinoethyl)-5-(4-(pyrimidin-2-yloxy)phenyl)-7H-pyrrolo[2,3-d]pyrimidin-6-yl)pyrrolidin-1-yl)prop-2-en-1-one | 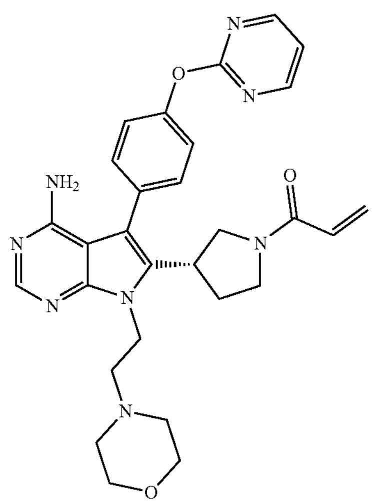 [SMILES: C=CC(=O)N1CC[C@H](c2c(-c3ccc(Oc4ncccn4)cc3)c3c(N)ncnc3n2CCN2CCOCC2)C1] | $^1$H NMR (400 MHz, DMSO-d$_6$) δ 8.69 (t, J = 5.0 Hz, 2H), 8.12 (d, J = 1.9 Hz, 1H), 7.46 (d, J = 8.0 Hz, 2H), 7.31 (dd, J = 6.1, 3.7 Hz, 3H), 6.48 (ddd, J = 31.6, 16.7, 10.2 Hz, 1H), 6.10 (ddd, J = 16.9, 5.6, 2.5 Hz, 1H), 5.64 (ddd, J = 10.0, 6.6, 2.4 Hz, 1H), 4.37 (d, J = 8.7 Hz, 2H), 4.03-3.84 (m, 1H), 3.83-3.63 (m, 2H), 3.60-3.45 (m, 6H), 3.30 (d, J = 13.6 Hz, 1H), 2.68 (q, J = 6.0, 5.5 Hz, 2H), 2.56-2.43 (m, 3H), 2.33-2.11 (m, 1H), 1.99 (dq, J = 44.8, 10.6 Hz, 1H). | 541.45 |
| (R)-1-(3-(4-amino-5-(4-(pyrimidin-2-yloxy)phenyl)-7H-pyrrolo[2,3-d]pyrimidin-6-yl)pyrrolidin-1-yl)prop-2-en-1-one | 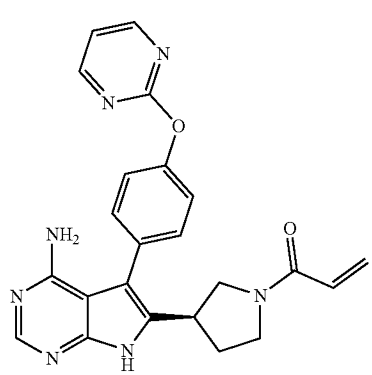 [SMILES: C=CC(=O)N1CC[C@@H](c2[nH]c3ncnc(N)c3c2-c2ccc(Oc3ncccn3)cc2)C1] | $^1$H NMR (400 MHz, DMSO-d$_6$) δ 11.86 (s, 1H), 8.69 (d, J = 4.8 Hz, 2H), 8.10 (s, 1H), 7.47 (dd, J = 8.5, 3.5 Hz, 2H), 7.39-7.19 (m, 3H), 6.59 (ddd, J = 16.8, 10.3, 2.5 Hz, 1H), 6.15 (dd, J = 16.7, 2.5 Hz, 1H), 5.97-5.53 (m, 2H), 4.14-3.39 (m, 5H), 2.44-1.99 (m, 2H). | 428.15 |

TABLE 13-continued

Additional Exemplary Compounds

| Compound | Structure | Proton NMR | MS [M + 1] |
|---|---|---|---|
| (S)-1-(3-(4-amino-5-(4-(pyrimidin-2-yloxy)phenyl)-7H-pyrrolo[2,3-d]pyrimidin-6-yl)pyrrolidin-1-yl)prop-2-en-1-one | 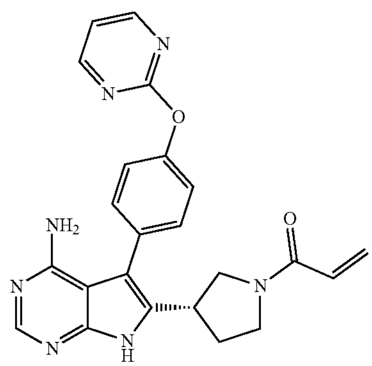 [SMILES: C=CC(=O)N1CC[C@H](c2[nH]c3ncnc(N)c3c2-c2ccc(Oc3ncccn3)cc2)C1] | $^1$H NMR (400 MHz, DMSO-d$_6$) δ 11.87 (s, 1H), 8.69 (d, J = 4.8 Hz, 2H), 8.11 (s, 1H), 7.47 (dd, J = 8.5, 3.5 Hz, 2H), 7.43-7.24 (m, 3H), 6.59 (ddd, J = 16.8, 10.3, 2.5 Hz, 1H), 6.15 (dd, J = 16.8, 2.5 Hz, 1H), 5.67 (ddd, J = 10.7, 8.7, 2.5 Hz, 2H), 4.16-3.37 (m, 5H), 2.42-2.00 (m, 2H). | 428.15 |
| 1-(3-(4-amino-5-(4-(cyclopropylmethoxy)phenyl)-7-methyl-7H-pyrrolo[2,3-d]pyrimidin-6-yl)pyrrolidin-1-yl)prop-2-en-1-one | 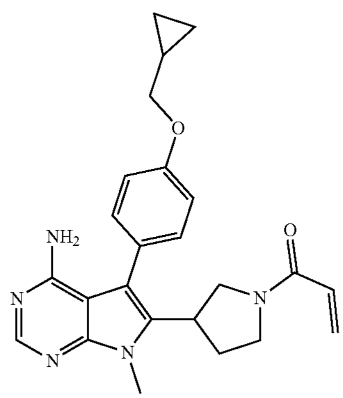 [SMILES: C=CC(=O)N1CCC(c2c(-c3ccc(OCC4CC4)cc3)c3c(N)ncnc3n2C)C1] | $^1$H NMR (400 MHz, DMSO-d$_6$) δ 8.10 (d, J = 1.7 Hz, 1H), 7.27 (d, J = 8.1 Hz, 2H), 7.01 (d, J = 8.1 Hz, 2H), 6.47 (ddd, J = 39.8, 16.8, 10.2 Hz, 1H), 6.09 (ddd, J = 16.8, 5.4, 2.5 Hz, 1H), 5.63 (ddd, J = 15.4, 10.3, 2.5 Hz, 1H), 3.89 (dd, J = 17.8, 8.0 Hz, 2H), 3.77 (d, J = 5.8 Hz, 4H), 3.77-3.58 (m, 1H), 3.55-3.44 (m, 2H), 3.26 (d, J = 10.8 Hz, 1H), 2.00 (dt, J = 45.8, 9.7 Hz, 2H), 1.25 (m, 1H), 0.64-0.55 (m, 2H), 0.35 (dd, J = 4.7, 2.3 Hz, 2H). | 418.20 |
| 1-(3-(5-(1-((1-acetylpiperidin-4-yl)methyl)-1H-pyrazol-4-yl)-4-amino-7-methyl-7H-pyrrolo[2,3-d]pyrimidin-6-yl)pyrrolidin-1-yl)prop-2-en-1-one | 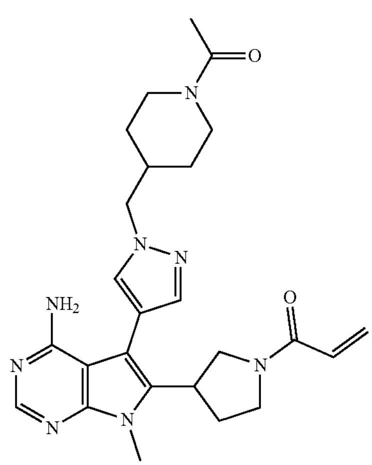 [SMILES: C=CC(=O)N1CCC(c2c(-c3cnn(CC4CCN(C(C)=O)CC4)c3)c3c(N)ncnc3n2C)C1] | $^1$H NMR (400 MHz, DMSO-d$_6$) 8.09 (d, J = 1.3 Hz, 1H), 7.88-7.82 (m, 1H), 7.51 (d, J = 6.1 Hz, 1H), 6.62-6.40 (m, 1H), 6.13 (dd, J = 16.7, 2.4 Hz, 1H), 5.71-5.61 (m, 2H), 4.34 (d, J = 13.1 Hz, 1H), 4.06 (d, J = 7.4 Hz, 2H), 3.93 (q, J = 9.4 Hz, 0H), 3.76 (d, J = 5.6 Hz, 3H), 3.68 (s, 2H), 3.53 (q, J = 8.1 Hz, 1H), 3.32 (s, 2H), 3.30 (s, 1H), 2.95 (t, J = 13.0 Hz, 1H), 2.47 (d, J = 12.2 Hz, 1H), 2.16 (s, 3H), 1.97 (t, J = 2.2 Hz, 3H), 1.45 (s, 2H), 1.16-0.98 (m, 2H). | 477.50 |

TABLE 13-continued

Additional Exemplary Compounds

| Compound | Structure | Proton NMR | MS [M + 1] |
|---|---|---|---|
| 1-(3-(4-amino-7-methyl-5-(1-(piperidin-4-ylmethyl)-1H-pyrazol-4-yl)-7H-pyrrolo[2,3-d]pyrimidin-6-yl)pyrrolidin-1-yl)prop-2-en-1-one | 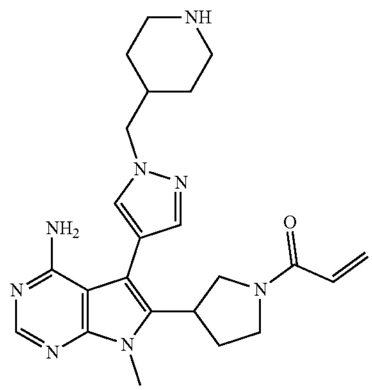 [SMILES: C=CC(=O)N1CCC(c2c(-c3cnn(CC4CCNCC4)c3)c3c(N)ncnc3n2C)C1] | ¹H NMR (400 MHz, DMSO-d₆) δ 8.08 (d, J = 2.6 Hz, 1H), 7.89-7.81 (m, 1H), 7.49 (q, J = 3.8 Hz, 1H), 6.47 (ddd, J = 39.8, 16.8, 10.2 Hz, 1H), 6.09 (ddd, J = 16.8, 5.4, 2.5 Hz, 1H), 5.90 (bar, 1H), 5.62 (s, 1H), 4.00 (d, J = 7.6 Hz, 2H), 3.82-3.62 (m, 5H), 3.55-3.40 (m, 2H), 3.20 (m, 1H), 2.89 (d, J = 11.3 Hz, 1H), 2.79 (s, 1H), 2.36 (d, J = 16.4 Hz, 2H), 2.21 (s, 1H), 2.07 (s, 1H), 1.92 (s, 1H), 1.82 (s, 1H), 1.36 (s, 2H), 1.15 (s, 1H), 1.04 (d, J = 12.9 Hz, 1H). | 435.20 |
| 1-(3-(4-amino-5-(4-(cyclopropane carbonyl)phenyl)-7-methyl-7H-pyrrolo[2,3-d]pyrimidin-6-yl)pyrrolidin-1-yl)prop-2-en-1-one | 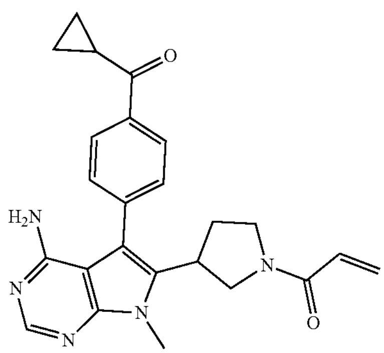 [SMILES: C=CC(=O)N1CCC(c2c(-c3ccc(C(=O)C4CC4)cc3)c3c(N)ncnc3n2C)C1] | ¹H NMR (400 MHz, DMSO-d₆) 8.17-8.10 (m, 3H), 7.55 (d, J = 7.9 Hz, 2H), 6.46 (ddd, J = 38.7, 16.7, 10.3 Hz, 1H), 6.08 (ddd, J = 16.7, 6.1, 2.5 Hz, 1H), 5.61 (ddd, J = 20.0, 10.2, 2.5 Hz, 2H), 4.03-3.74 (m, 5H), 3.69 (t, J = 9.0 Hz, 2H), 3.57 (t, J = 9.9 Hz, 1H), 3.00-2.92 (m, 1H), 2.28-1.84 (m, 2H), 1.07 (d, J = 6.3 Hz, 4H). | 416.20 |
| 1-(3-(4-amino-5-(4-(2-methoxyethoxy)phenyl)-7-methyl-7H-pyrrolo[2,3-d]pyrimidin-6-yl)pyrrolidin-1-yl)prop-2-en-1-one | 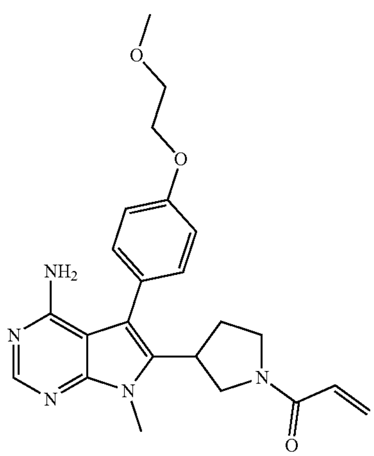 [SMILES: C=CC(=O)N1CCC(c2c(-c3ccc(OCCOC)cc3)c3c(N)ncnc3n2C)C1] | ¹H NMR (400 MHz, DMSO-d₆) δ 8.10 (d, J = 1.6 Hz, 1H), 7.29 (d, J = 8.1 Hz, 2H), 7.03 (d, J = 8.2 Hz, 2H), 6.51-6.42 (dd, J = 16.8, 10.3 Hz, 1H), 6.09 (ddd, J = 16.7, 5.3, 2.4 Hz, 1H), 5.63 (ddd, J = 14.2, 10.3, 2.5 Hz, 2H), 4.18-4.11 (m, 2H), 3.97-3.88 (m, 4H), 3.77-3.70 (d, J = 4.6 Hz, 5H), 3.70-3.58 (m, 3H), 3.57-3.41 (m, 1H), 2.19 (s, 1H), 2.00 (dt, J = 46.6, 9.6 Hz, 1H). | 422.20 |
| 1-(3-(4-amino-5-(4-cyclopropoxy phenyl)-7-methyl-7H-pyrrolo[2,3-d]pyrimidin-6-yl)pyrrolidin-1-yl)prop-2-en-1-one | 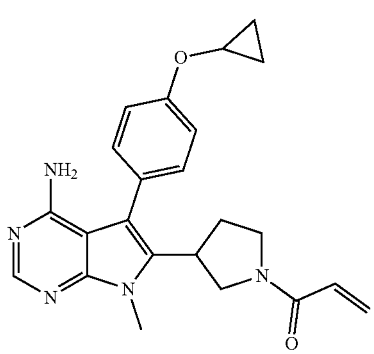 | ¹H NMR (400 MHz, DMSO-d6) 8.10 (d, J = 1.7 Hz, 1H), 7.31 (d, J = 8.2 Hz, 2H), 7.14 (d, J = 8.2 Hz, 2H), 6.46 (ddd, J = 45.8, 16.7, 10.2 Hz, 1H), 6.09 (ddd, J = 16.8, 7.0, 2.5 Hz, 1H), 5.79-5.51 (m, 2H), 3.89 (dt, J = 6.1, 2.6 Hz, 1H), 3.82-3.53 (m, 4H), 3.32 (s, 3H), 3.27-3.15 (m, 1H), 2.34-1.81 (m, 2H), 1.24 (s, 1H), 0.80 (t, J = 5.7 Hz, 2H), 0.70 (d, J = 3.5 Hz, 2H). | 404.20 |

TABLE 13-continued

Additional Exemplary Compounds

| Compound | Structure | Proton NMR | MS [M + 1] |
|---|---|---|---|
| 1-(3-(4-amino-7-methyl-5-(1-(tetrahydrofuran-3-yl)-1H-pyrazol-4-yl)-7H-pyrrolo[2,3-d]pyrimidin-6-yl)pyrrolidin-1-yl)prop-2-en-1-one | 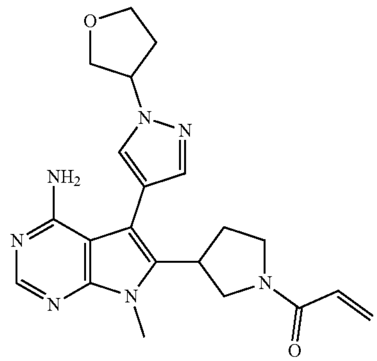 [SMILES: C=CC(=O)N1CCC(c2c(-c3cnn(C4CCOC4)c3)c3c(N)ncnc3n2C)C1] | $^1$H NMR (400 MHz, DMSO-d$_6$) δ 8.09 (d, J = 1.5 Hz, 1H), 7.88 (s, 1H), 7.52 (d, J = 7.5 Hz, 1H), 6.50 (ddd, J = 43.5, 16.8, 10.3 Hz, 1H), 6.11 (dt, J = 16.8, 2.6 Hz, 1H), 5.85-5.40 (bar, 2H), 5.64 (td, J = 10.8, 2.5 Hz, 1H), 5.05 (t, J = 5.3 Hz, 1H), 3.98 (ddd, J = 19.1, 10.3, 6.6 Hz, 3H), 3.95-3.78 (m, 2H), 3.76 (s, 3H), 3.76-3.62 (m, 1H), 3.62-3.46 (m, 2H), 3.38 (t, J = 10.1 Hz, 1H), 2.36 (dtd, J = 17.9, 9.2, 8.5, 3.1 Hz, 2H), 2.22 (s, 1H), 2.16-1.94 (m, 1H). | 408.20 |
| 1-(3-{4-amino-5-[4-(cyclopentylsulfanyl)phenyl]-7-methyl-7H-pyrrolo[2,3-d]pyrimidin-6-yl}pyrrolidin-1-yl)prop-2-en-1-one | 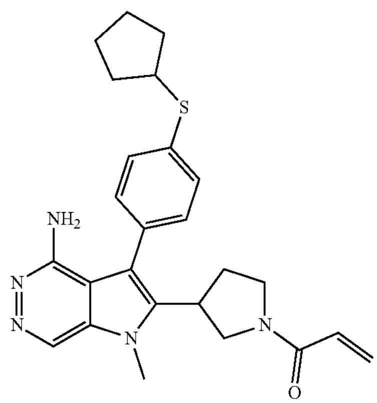 [SMILES: C=CC(=O)N1CCC(c2c(-c3ccc(SC4CCCC4)cc3)c3c(N)nncc3n2C)C1] | 1H NMR (400 MHz, DMSO-d6) 8.11 (d, J = 1.8 Hz, 1H), 7.43-7.37 (m, 2H), 7.32 (d, J = 7.2 Hz, 2H), 6.52-6.39 (dd, J = 16.8, 10.3 Hz, 1H), 6.09 (ddd, J = 16.8, 6.4, 2.4 Hz, 1H), 5.62 (ddd, J = 18.5, 10.3, 2.5 Hz, 3H), 3.90 (t, J = 9.1 Hz, 1H), 3.81-3.73 (m, 5H), 3.66 (q, J = 10.1, 9.4 Hz, 1H), 3.59-3.52 (m, 1H), 3.48-3.24 (m, 1H), 2.10-1.88 (m, 4H), 1.76-1.52 (m, 6H). | 448.19 |
| N-(4-{4-amino-7-methyl-6-[1-(prop-2-enoyl)pyrrolidin-3-yl]-7H-pyrrolo[2,3-d]pyrimidin-5-yl}phenyl)-N-methylacetamide | 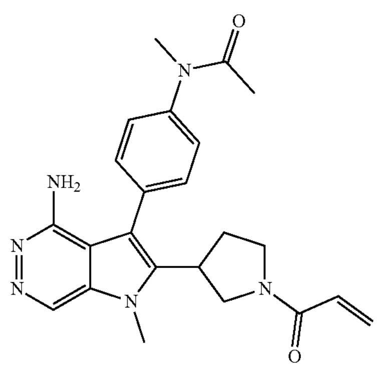 [SMILES: C=CC(=O)N1CCC(c2c(-c3ccc(N(C)C(C)=O)cc3)c3c(N)nncc3n2C)C1] | 1H NMR (400 MHz, DMSO-d$_6$) 8.12 (d, J = 2.7 Hz, 1H), 7.42 (t, J = 6.4 Hz, 4H), 6.45 (ddd, J = 49.5, 16.8, 10.3 Hz, 1H), 6.08 (dd, J = 16.8, 2.4 Hz, 1H), 5.62 (ddd, J = 14.9, 10.3, 2.5 Hz, 3H), 4.17-3.40 (m, 7H), 3.22 (s, 3H), 1.95 (s, 3H), 1.85 (s, 2H). | 419.25 |
| 1-(3-{4-amino-7-methyl-5-[1-(piperidin-4-yl)-1H-pyrazol-4-yl]-7H-pyrrolo[2,3-d]pyrimidin-6-yl}pyrrolidin-1-yl)prop-2-en-1-one | 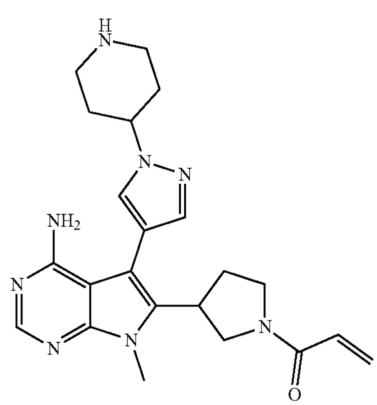 [SMILES: C=CC(=O)N1CCC(c2c(-c3cnn(C4CCNCC4)c3)c3c(N)ncnc3n2C)C1] | $^1$H NMR (400 MHz, DMSO-d) δ 8.14-8.06 (m, 1H), 7.87 (d, J = 3.0 Hz, 1H), 7.58-7.46 (m, 1H), 6.65-6.33 (m, 1H), 6.11 (d, J = 16.8 Hz, 1H), 5.83-5.49 (m, 2H), 4.50 (s, 1H), 4.21 (s, 1H), 3.87 (dt, J = 18.6, 8.5 Hz, 1H), 3.75 (d, J = 1.0 Hz, 5H), 3.64 (dt, J = 17.7, 9.1 Hz, 1H), 3.04 (t, J = 8.0 Hz, 1H), 2.79 (d, J = 13.0 Hz, 2H), 2.38-2.06 (m, 3H), 1.97 (d, J = 11.8 Hz, 2H), 1.83 (d, J = 12.1 Hz, 2H). | 421.25 |

TABLE 13-continued

Additional Exemplary Compounds

| Compound | Structure | Proton NMR | MS [M + 1] |
|---|---|---|---|
| 1-(3-{4-amino-5-[1-(azetidin-3-yl)-1H-pyrazol-4-yl]-7-methyl-7H-pyrrolo[2,3-d]pyrimidin-6-yl}pyrrolidin-1-yl)prop-2-en-1-one; trifluoroacetic acid salt | 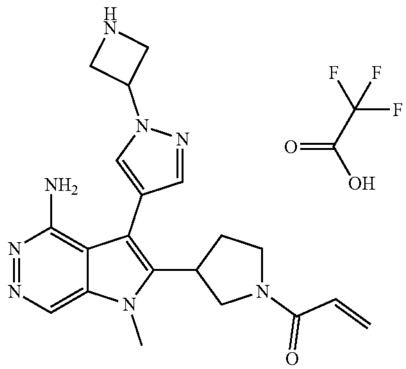 [SMILES: C=CC(=O)N1CCC(c2c(-c3cnn(C4CNC4)c3)c3c(N)nncc3n2C)C1 ; O=C(O)C(F)(F)F] | 1H NMR (400 MHz, DMSO-d6) 9.10-8.95 (s, 2H), 8.45-8.39 (m, 1H), 7.99 (d, J = 2.0 Hz, 1H), 7.73 (d, J = 10.1 Hz, 1H), 6.53-6.41 (dd, J = 16.8, 10.3 Hz, 1H), 6.11 (dd, J = 16.8, 2.4 Hz, 1H), 5.66 (ddd, J = 12.8, 10.2, 2.5 Hz, 1H), 5.41 (td, J = 7.5, 3.7 Hz, 1H), 4.41 (m, 4H), 3.86 (d, J = 6.2 Hz, 4H), 3.81-3.58 (m, 2H), 3.58-3.33 (dt, J = 12.0, 7.7 Hz, 2H), 2.31-1.93 (m, 2H), 1.08 (s, 1H). | 3293.25 |
| 1-(3-(4-amino-5-(4-(cyclopentyloxy)phenyl)-7-methyl-7H-pyrrolo[2,3-d]pyrimidin-6-yl)pyrrolidin-1-yl)prop-2-en-1-one | 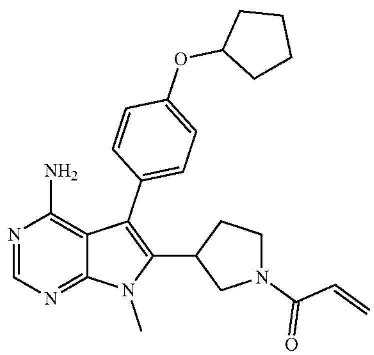 [SMILES: C=CC(=O)N1CCC(c2c(-c3ccc(OC4CCCC4)cc3)c3c(N)ncnc3n2C)C1] | 1H NMR (400 MHz, DMSO-d6) 8.10 (d, J = 1.6 Hz, 1H), 7.26 (d, J = 8.3 Hz, 2H), 6.97 (d, J = 8.1 Hz, 2H), 6.45 (ddd, J = 49.5, 16.8, 10.3 Hz, 1H), 6.08 (ddd, J = 16.8, 7.7, 2.5 Hz, 1H), 5.62 (ddd, J = 19.2, 10.3, 2.5 Hz, 1H), 4.86 (q, J = 4.6, 3.2 Hz, 1H), 3.95-3.73 (m, 4H), 3.65 (d, J = 9.8 Hz, 1H), 3.54-3.45 (m, 1H), 3.32 (s, 4H), 2.24-1.88 (m, 4H), 1.76 (d, J = 12.6 Hz, 4H), 1.60 (d, J = 9.0 Hz, 2H). | 432.35 |
| 1-(3-(4-amino-5-(4-(3,3-difluoropyrrolidine-1-carbonyl)phenyl)-7-methyl-7H-pyrrolo[2,3-d]pyrimidin-6-yl)pyrrolidin-1-yl)prop-2-en-1-one | 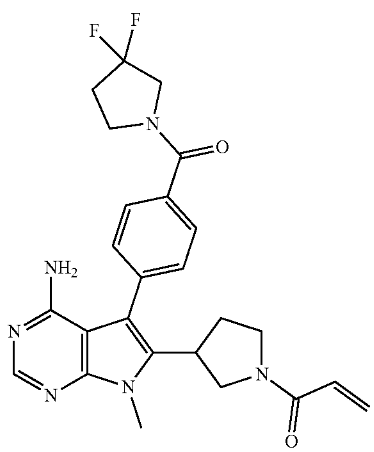 [SMILES: C=CC(=O)N1CCC(c2c(-c3ccc(C(=O)N4CCC(F)(F)C4)cc3)c3c(N)ncnc3n2C)C1] | $^1$H NMR (400 MHz, Methanol-$d_4$) δ 8.14 (d, J = 2.0 Hz, 1H), 7.68 (s, 2H), 7.55 (d, J = 7.9 Hz, 2H), 6.53 (t, J = 13.7 Hz, 1H), 6.25-6.16 (m, 1H), 5.70 (dd, J = 17.9, 10.5 Hz, 1H), 4.04 (s, 2H), 4.02-3.91 (m, 6H), 3.88 (d, J = 4.8 Hz, 4H), 2.50 (s, 2H), 2.28 (s, 1H), 2.23-2.04 (m, 1H). | 481.35 |
| (R)-1-(3-(4-amino-5-(4-(methoxymethyl)phenyl)-7-methyl-7H-pyrrolo[2,3-d]pyrimidin-6-yl)pyrrolidin-1-yl)prop-2-en-1-one | 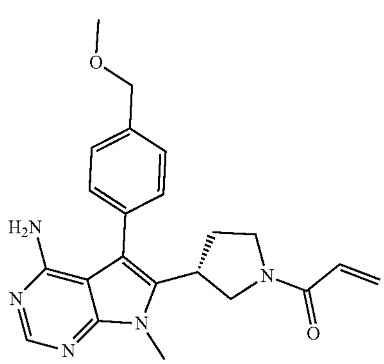 [SMILES: C=CC(=O)N1CC[C@@H](c2c(-c3ccc(COC)cc3)c3c(N)ncnc3n2C)C1] | $^1$H NMR (400 MHz, DMSO-$d_6$) δ 8.12 (d, J = 1.9 Hz, 2H), 7.39 (q, J = 7.8 Hz, 8H), 6.51 (dd, J = 16.8, 10.3 Hz, 1H), 6.40 (dd, J = 16.8, 10.3 Hz, 1H), 6.08 (ddd, J = 16.8, 5.7, 2.5 Hz, 2H), 5.62 (ddd, J = 15.9, 10.3, 2.5 Hz, 2H), 4.48 (s, 4H), 3.92 (t, J = 9.1 Hz, 1H), 3.78 (s, 4H), 3.75-3.64 (m, 1H), 3.67-3.57 (m, 1H), 3.53 (s, 1H), 3.51 (s, 1H), 3.49-3.41 (m, 1H), 3.36-3.25 (m, 9H), 3.28-3.20 (m, 1H), 2.20 (dt, J = 12.5, 6.7 Hz, 1H), 2.15-1.89 (m, 2H). | 392.10 |

TABLE 13-continued

Additional Exemplary Compounds

| Compound | Structure | Proton NMR | MS [M + 1] |
| --- | --- | --- | --- |
| 1-(3-{4-amino-7-methyl-5-[1-(1-methylpiperidin-4-yl)-1H-pyrazol-4-yl]-7H-pyrrolo[2,3-d]pyrimidin-6-yl}pyrrolidin-1-yl)prop-2-en-1-one | 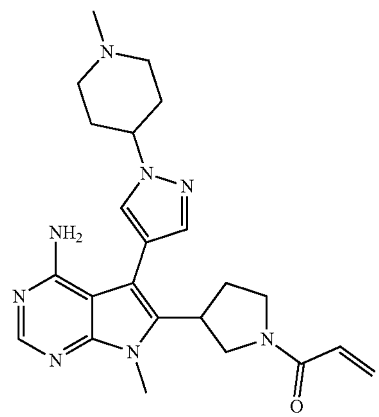 [SMILES: C=CC(=O)N1CCC(c2c(-c3cnn(C4CCN(C)CC4)c3)c3c(N)ncnc3n2C)C1] | $^1$H NMR (400 MHz, Methanol-d$_4$) δ 8.11 (s, 1H), 7.84 (d, J = 3.3 Hz, 1H), 7.57 (d, J = 6.3 Hz, 1H), 6.56-6.43 (ddd, J = 16.7, 10.4 Hz, 1H), 6.30-6.19 (m, 1H), 5.78-5.67 (m, 1H), 4.26 (s, 1H), 3.99-3.86 (m, 1H), 3.84 (d, J = 2.7 Hz, 4H), 3.75 (d, J = 7.5 Hz, 1H), 3.69-3.57 (m, 2H), 3.02 (d, J = 11.4 Hz, 2H), 2.36 (s, 3H), 2.32 (s, 3H), 2.34-2.25 (m, 3H), 2.12 (d, J = 12.1 Hz, 2H), 2.05 (s, 1H). | 435.20 |
| 1-(3-{4-amino-7-methyl-5-[1-(2,2,2-trifluoroethyl)-1H-pyrazol-4-yl]-7H-pyrrolo[2,3-d]pyrimidin-6-yl}pyrrolidin-1-yl)prop-2-en-1-one | 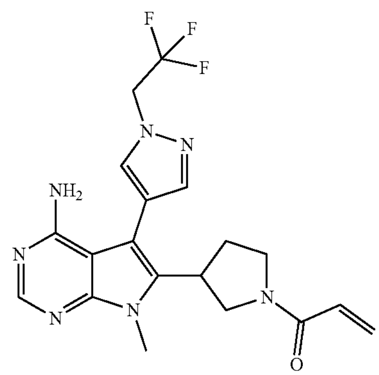 [SMILES: C=CC(=O)N1CCC(c2c(-c3cnn(CC(F)(F)F)c3)c3c(N)ncnc3n2C)C1] | $^1$H NMR (400 MHz, DMSO-d$_6$) δ 8.11 (s, 1H), 7.99 (s, 1H), 7.67 (d, J = 4.6 Hz, 1H), 6.62-6.36 (m, 1H), 6.12 (ddd, J = 16.7, 4.7, 2.4 Hz, 1H), 5.76 (s, 1), 0 (d, J = 44.9 Hz, 1H), 5.17 (q, J = 9.0 Hz, 2H), 3.93 (t, J = 9.0 Hz, 1H), 3.87-3.74 (m, 4H), 3.68 (t, J = 9.1 Hz, 1H), 3.61-3.45 (m, 3H), 2.29-1.89 (m, 2H). | 420.15 |
| 1-(3-(4-amino-7-methyl-5-(4-(morpholine-4-carbonyl)phenyl)-7H-pyrrolo[2,3-d]pyrimidin-6-yl)pyrrolidin-1-yl)prop-2-en-1-one | 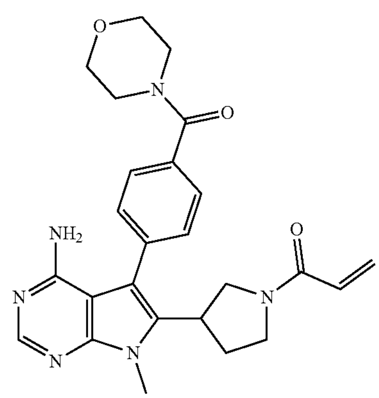 [SMILES: C=CC(=O)N1CCC(c2c(-c3ccc(C(=O)N4CCOCC4)cc3)c3c(N)ncnc3n2C)C1] | $^1$H NMR (400 MHz, DMSO-d$_6$) δ 8.13 (d, J = 3.0 Hz, 1H), 7.50 (d, J = 7.8 Hz, 2H), 7.46 (d, J = 4.8 Hz, 2H), 6.51-6.42 (dd, J = 16.7, 10.3 Hz, 1H), 6.07 (ddd, J = 16.9, 7.1, 2.4 Hz, 1H), 5.68-5.57 (m, 3H), 3.91 (t, J = 9.2 Hz, 4H), 3.79-3.31 (d, J = 16.0 Hz, 11H), 3.27 (s, 1H), 2.23 (s, 1H), 2.10 (s, 1H). | 461.20 |
| 1-(3-(4-amino-5-(4-(hydroxymethyl)cyclohex-1-en-1-yl)-7-methyl-7H-pyrrolo[2,3-d]pyrimidin-6-yl)pyrrolidin-1-yl)prop-2-en-1-one | 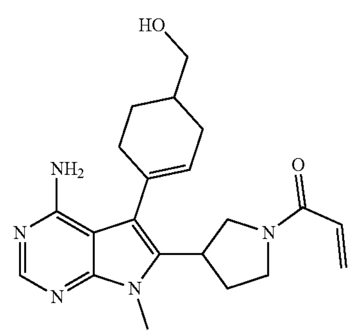 [SMILES: C=CC(=O)N1CCC(c2c(C3=CCC(CO)CC3)c3c(N)ncnc3n2C)C1] | $^1$H NMR (400 MHz, DMSO-d$_6$) 8.06 (d, J = 1.3 Hz, 1H), 6.62 (dd, J = 16.8, 10.3 Hz, 1H), 6.01 (s, 3H), 5.76 (s, 2H), 4.52 (t, J = 4.9 Hz, 1H), 4.01 (s, 2H), 3.69 (d, J = 6.0 Hz, 5H), 3.36 (d, J = 5.7 Hz, 2H), 2.21 (s, 5H), 1.87 (s, 3H), 1.40 (s, 1H). | 382.40 |

TABLE 13-continued

Additional Exemplary Compounds

| Compound | Structure | Proton NMR | MS [M + 1] |
|---|---|---|---|
| 1-(3-(4-amino-7-methyl-5-(1-(pyridin-3-yl)-1H-pyrazol-4-yl)-7H-pyrrolo[2,3-d]pyrimidin-6-yl)pyrrolidin-1-yl)prop-2-en-1-one | 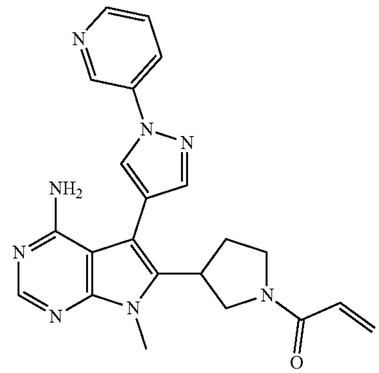 [SMILES: C=CC(=O)N1CCC(c2c(-c3cnn(-c4cccnc4)c3)c3c(N)ncnc3n2C)C1] | ¹H NMR (400 MHz, DMSO-d₆) 9.15 (t, J = 2.5 Hz, 1H), 8.69 (d, J = 11.2 Hz, 1H), 8.54 (dt, J = 4.6, 1.5 Hz, 1H), 8.27 (d, J = 7.8 Hz, 1H), 8.12 (s, 1H), 7.86 (d, J = 4.0 Hz, 1H), 7.57 (dd, J = 8.4, 4.8 Hz, 1H), 6.48 (ddd, J = 29.3, 16.7, 10.3 Hz, 1H), 6.01 (ddd, J = 16.7, 6.1, 2.5 Hz, 1H), 5.87 (s, 1H), 5.56 (ddd, J = 16.3, 10.3, 2.5 Hz, 1H), 3.94 (t, J = 9.0 Hz, 2H), 3.88-3.63 (m, 5H), 3.52 (ddt, J = 29.1, 19.5, 8.3 Hz, 1H), 2.25 (s, 1H), 2.12 (dt, J = 36.2, 10.9 Hz, 1H). | 415.40 |
| 1-[3-(4-amino-5-{4-[(3,3-dimethylpyrrolidin-1-yl)methyl]phenyl}-7-methyl-7H-pyrrolo[2,3-d]pyrimidin-6-yl)pyrrolidin-1-yl]prop-2-en-1-one | 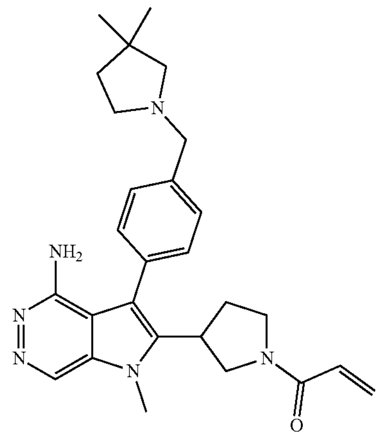 [SMILES: C=CC(=O)N1CCC(c2c(-c3ccc(CN4CCC(C)(C)C4)cc3)c3c(N)nncc3n2C)C1] | 1H NMR (400 MHz, DMSO-d6) 8.11 (d, J = 2.0 Hz, 1H), 7.36 (ddd, J = 26.6, 8.1, 2.7 Hz, 4H), 6.51-6.37 (dd, J = 16.8, 10.3 Hz, 1H), 6.08 (ddd, J = 16.8, 6.5, 2.5 Hz, 1H), 5.64-5.58 (dd, J = 10.3, 2.5 Hz, 2H), 3.94-3.85 (m, 1H), 3.81-3.69 (m, 4H), 3.69-3.62 (s, 3H), 3.58-3.21 (m, 3H), 3.18 (s, 1H), 2.58 (td, J = 7.0, 3.2 Hz, 2H), 2.29 (d, J = 2.2 Hz, 2H), 2.21-1.88 (m, 2H), 1.54 (t, J = 7.0 Hz, 2H), 1.24 (s, 1H), 1.06 (d, J = 1.4 Hz, 5H). | 459.25 |
| 1-(3-(4-amino-5-(4-(azetidine-1-carbonyl)-3-fluorophenyl)-7-methyl-7H-pyrrolo[2,3-d]pyrimidin-6-yl)pyrrolidin-1-yl)prop-2-en-1-one | 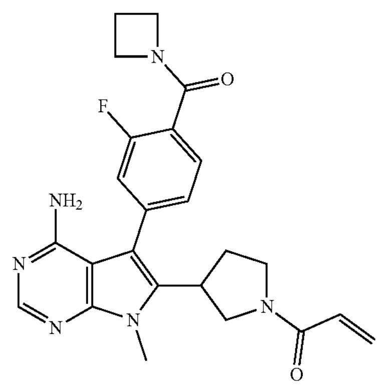 [SMILES: C=CC(=O)N1CCC(c2c(-c3ccc(C(=O)N4CCC4)c(F)c3)c3c(N)ncnc3n2C)C1] | ¹H NMR (400 MHz, DMSO-d₆) δ 8.13 (d, J = 2.6 Hz, 1H), 7.56 (q, J = 7.1 Hz, 1H), 7.30 (ddd, J = 17.0, 10.0, 1.7 Hz, 2H), 6.49 (ddd, J = 29.8, 16.8, 10.4 Hz, 1H), 6.09 (dt, J = 16.8, 3.0 Hz, 1H), 5.64 (td, J = 10.5, 2.4 Hz, 2H), 4.11-4.03 (m, 4H), 3.94 (t, J = 9.3 Hz, 1H), 3.82-3.66 (m, 5H), 3.62-3.47 (m, 1H), 2.27 (p, J = 7.6 Hz, 2H), 2.07 (dd, J = 19.2, 9.6 Hz, 1H), 2.03-1.91 (m, 1H). | 449.25 |
| 1-(3-(4-amino-5-(4-benzoylphenyl)-7-methyl-7H-pyrrolo[2,3-d]pyrimidin-6-yl)pyrrolidin-1-yl)prop-2-en-1-one | 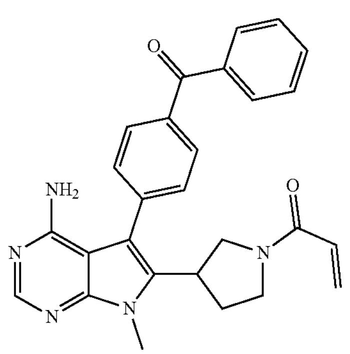 [SMILES: C=CC(=O)N1CCC(c2c(-c3ccc(C(=O)c4ccccc4)cc3)c3c(N)ncnc3n2C)C1] | ¹H NMR (400 MHz, DMSO-d₆) δ 8.14 (d, J = 2.4 Hz, 1H), 7.83 (ddd, J = 12.3, 8.9, 6.7 Hz, 4H), 7.71 (t, J = 7.4 Hz, 1H), 7.64-7.53 (m, 4H), 6.47 (ddd, J = 38.4, 16.7, 10.3 Hz, 1H), 6.07 (dt, J = 16.8, 2.8 Hz, 1H), 5.90-5.33 (bar, 1H), 5.61 (ddd, J = 16.5, 10.3, 2.5 Hz, 1H), 4.00-3.68 (m, 6H), 3.65-3.54 (m, 1H), 3.54-3.37 (m, 1H), 2.24 (s, 1H), 2.18-1.97 (m, 1H). | 452.15 |

TABLE 13-continued

Additional Exemplary Compounds

| Compound | Structure | Proton NMR | MS [M + 1] |
|---|---|---|---|
| 1-(3-(4-amino-7-methyl-5-(5-(morpholinomethyl)thiophen-3-yl)-7H-pyrrolo[2,3-d]pyrimidin-6-yl)pyrrolidin-1-yl)prop-2-en-1-one | 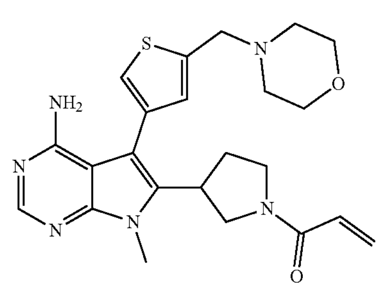 [SMILES: C=CC(=O)N1CCC(c2c(-c3csc(CN4CCOCC4)c3)c3c(N)ncnc3n2C)C1] | $^1$H NMR (400 MHz, DMSO-d6) 8.10 (d, J = 1.7 Hz, 1H), 7.44 (dd, J = 4.5, 1.5 Hz, 1H), 7.00 (d, J = 5.3 Hz, 1H), 6.48 (ddd, J = 50.3, 16.8, 10.3 Hz, 1H), 6.10 (dd, J = 16.7, 2.5 Hz, 2H), 5.80-5.50 (m, 2H), 3.92 (t, J = 9.0 Hz, 1H), 3.76 (d, J = 5.7 Hz, 4H), 3.71 (d, J = 4.0 Hz, 3H), 3.58 (t, J = 4.6 Hz, 4H), 3.51 (d, J = 10.1 Hz, 1H), 3.32 (s, 1H), 2.41 (d, J = 5.8 Hz, 4H), 2.32-2.11 (m, 1H), 2.10-1.89 (m, 1H). | 453.20 |
| 1-(3-(4-amino-7-methyl-5-(1-(pyridin-2-yl)-1H-pyrazol-4-yl)-7H-pyrrolo[2,3-d]pyrimidin-6-yl)pyrrolidin-1-yl)prop-2-en-1-one | 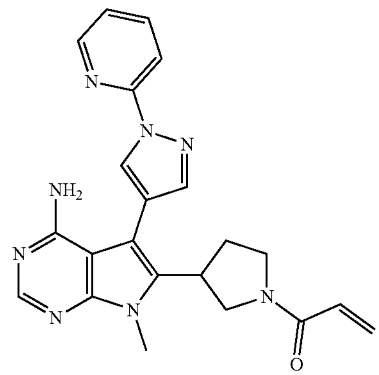 [SMILES: C=CC(=O)N1CCC(c2c(-c3cnn(-c4ccccn4)c3)c3c(N)ncnc3n2C)C1] | $^1$H NMR (400 MHz, DMSO-d$_6$) 8.65 (d, J = 4.4 Hz, 1H), 8.49 (d, J = 4.9 Hz, 1H), 8.12 (d, J = 1.6 Hz, 1H), 8.07-7.95 (m, 2H), 7.88 (d, J = 3.3 Hz, 1H), 7.38 (td, J = 5.5, 4.8, 2.9 Hz, 1H), 6.49 (td, J = 17.4, 10.2 Hz, 1H), 6.04 (dt, J = 16.7, 2.2 Hz, 1H), 5.57 (ddd, J = 15.5, 10.2, 2.5 Hz, 1H), 3.97 (s, 1H), 4.07-3.72 (m, 5H), 3.72-3.37 (m, 2H), 2.20-2.02 (m, 2H). | 415.40 |
| 1-(3-(4-amino-5-(1-isopropyl-1H-pyrazol-4-yl)-7-methyl-7H-pyrrolo[2,3-d]pyrimidin-6-yl)pyrrolidin-1-yl)prop-2-en-1-one | 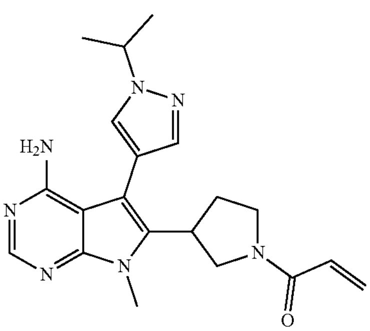 [SMILES: C=CC(=O)N1CCC(c2c(-c3cnn(C(C)C)c3)c3c(N)ncnc3n2C)C1] | $^1$H NMR (400 MHz, DMSO-d$_6$) 8.09 (s, 1H), 7.87 (s, 1H), 7.48 (d, J = 6.5 Hz, 1H), 6.50 (ddd, J = 46.6, 16.8, 10.3 Hz, 1H), 6.11 (ddd, J = 16.8, 4.3, 2.5 Hz, 1H), 5.64 (ddd, J = 12.5, 10.2, 2.5 Hz, 1H), 4.53 (p, J = 6.6 Hz, 1H), 3.89 (t, J = 9.1 Hz, 1H), 3.82-3.66 (m, 5H), 3.56 (tq, J = 17.0, 8.9 Hz, 2H), 3.37 (d, J = 10.8 Hz, 0H), 2.26-1.93 (m, 2H), 1.44 (d, J = 6.7 Hz, 6H),. | 380.25 |
| 1-(3-(4-amino-7-methyl-5-(1-(o-tolyl)-1H-pyrazol-4-yl)-7H-pyrrolo[2,3-d]pyrimidin-6-yl)pyrrolidin-1-yl)prop-2-en-1-one | 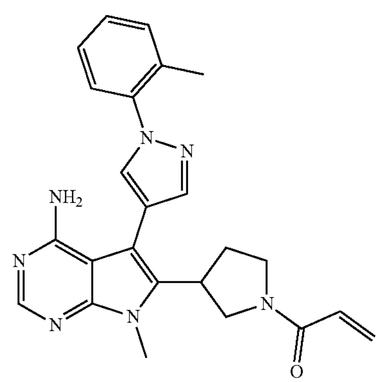 [SMILES: C=CC(=O)N1CCC(c2c(-c3cnn(-c4ccccc4C)c3)c3c(N)ncnc3n2C)C1] | $^1$H NMR (400 MHz, DMSO-d6) δ 8.24-8.01 (m, 2H), 7.77 (d, J = 8.3 Hz, 1H), 7.54-7.27 (m, 3H), 6.51 (ddd, J = 31.5, 16.7, 10.3 Hz, 1H), 6.10 (dt, J = 16.8, 2.2 Hz, 1H), 5.63 (ddd, J = 10.3, 5.7, 2.5 Hz, 2H), 4.00-3.67 (m, 4H), 3.65-3.39 (m, 3H), 3.33-3.17 (m, 2H), 2.34-2.00 (m, 5H). | 428.35 |

TABLE 13-continued

Additional Exemplary Compounds

| Compound | Structure | Proton NMR | MS [M + 1] |
|---|---|---|---|
| 1-{3-[4-amino-5-(4-{[(3R)-3-hydroxypyrrolidin-1-yl]methyl}phenyl)-7-methyl-7H-pyrrolo[2,3-d]pyrimidin-6-yl]pyrrolidin-1-yl}prop-2-en-1-one | 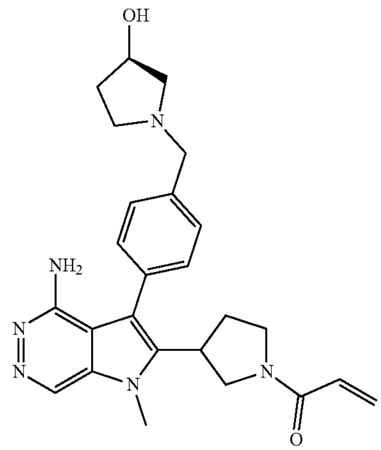 [SMILES: C=CC(=O)N1CCC(c2c(-c3ccc(CN4CC[C@@H](O)C4)cc3)c3c(N)nncc3n2C)C1] | 1H NMR (400 MHz, DMSO-d6) 8.11 (d, J = 2.0 Hz, 1H), 7.39 (d, J = 7.9 Hz, 4H), 6.38 (dd, J = 16.8, 10.0 Hz, 1H), 6.08 (ddd, J = 16.7, 7.3, 2.5 Hz, 1H), 5.68-5.56 (m, 3H), 4.69 (s, 1H), 4.21 (s, 1H), 3.90-3.42 (t, J = 9.0 Hz, 9H), 3.32-3.23 (m, 1H), 2.72 (s, 1H), 2.58 (s, 1H), 2.44 (s, 1H), 2.06-1.89 (m, 3H), 1.56 (s, 1H). | 447.25 |
| 1-(3-(4-amino-7-methyl-5-(4-(pyrrolidine-1-carbonyl)phenyl)-7H-pyrrolo[2,3-d]pyrimidin-6-yl)pyrrolidin-1-yl)prop-2-en-1-one | 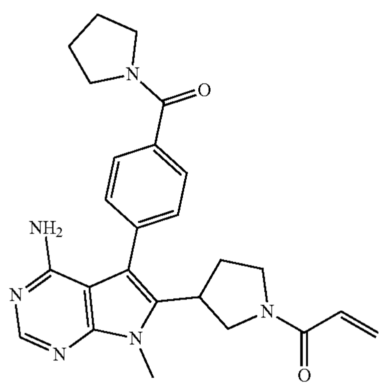 [SMILES: C=CC(=O)N1CCC(c2c(-c3ccc(C(=O)N4CCCC4)cc3)c3c(N)ncnc3n2C)C1] | $^1$H NMR (400 MHz, DMSO-d$_6$) 8.13 (d, J = 2.6 Hz, 1H), 7.60 (t, J = 7.3 Hz, 2H), 7.44 (dd, J = 8.3, 3.3 Hz, 2H), 6.46 (ddd, J = 40.8, 16.8, 10.3 Hz, 1H), 6.07 (dt, J = 16.8, 2.2 Hz, 1H), 5.62 (ddd, J = 14.8, 10.3, 2.5 Hz, 1H), 3.92 (t, J = 9.2 Hz, 1H), 3.79 (d, J = 12 Hz, 4H), 3.76-3.64 (m, 2H), 3.60-3.47 (m, 2H), 3.48 (s, 5H), 3.45 (s, 0H), 2.21 (s, 1H), 2.08 (dd, J = 19.3, 9.4 Hz, 1H), 2.01-1.80 (m, 4H). | 445.25 |
| 4-{4-amino-7-methyl-6-[1-(prop-2-enoyl)pyrrolidin-3-yl]-7H-pyrrolo[2,3-d]pyrimidin-5-yl}-N-(pyridin-2-yl)benzamide | 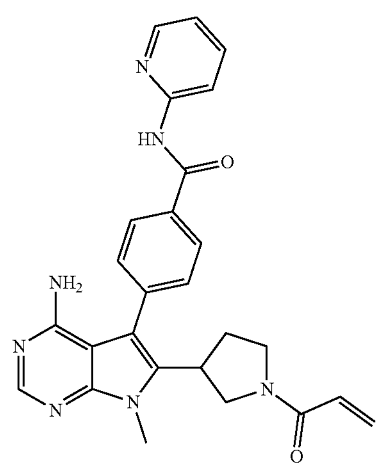 [SMILES: C=CC(=O)N1CCC(c2c(-c3ccc(C(=O)Nc4ccccn4)cc3)c3c(N)ncnc3n2C)C1] | $^1$H NMR (400 MHz, DMSO-d$_6$) δ 10.81 (s, 1H), 8.41 (d, J = 4.9 Hz, 1H), 8.21 (d, J = 8.4 Hz, 1H), 8.17-8.08 (m, 3H), 7.91-7.82 (m, 1H), 7.53 (d, J = 7.8 Hz, 2H), 7.22-7.15 (m, 1H), 6.59-6.40 (m, 1H), 6.15-6.05 (m, 1H), 5.63 (t, J = 11.4 Hz, 2H), 3.81 (d, J = 7.0 Hz, 6H), 3.57 (t, J = 9.6 Hz, 2H), 2.21 (s, 1H), 2.10 (d, J = 12.5 Hz, 1H). | 468.20 |

TABLE 13-continued

Additional Exemplary Compounds

| Compound | Structure | Proton NMR | MS [M + 1] |
|---|---|---|---|
| 1-(3-(4-amino-5-(1-cyclopentyl-1H-pyrazol-4-yl)-7-methyl-7H-pyrrolo[2,3-d]pyrimidin-6-yl)pyrrolidin-1-yl)prop-2-en-1-one | 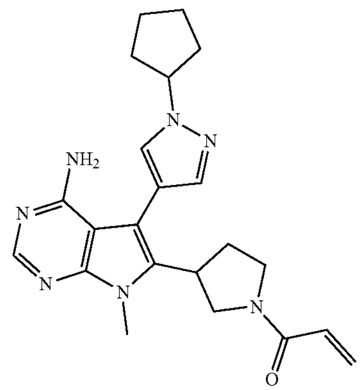 [SMILES: C=CC(=O)N1CCC(c2c(-c3cnn(C4CCCC4)c3)c3c(N)ncnc3n2C)C1] | $^1$H NMR (400 MHz, DMSO-$d_6$) δ 8.09 (d, J = 1.4 Hz, 1H), 7.87 (s, 1H), 7.48 (d, J = 62 Hz, 1H), 6.50 (ddd, J = 46.7, 16.8, 10.3 Hz, 1H), 6.11 (ddd, J = 16.8, 4.0, 2.5 Hz, 1H), 5.64 (ddd, J = 12.5, 10.2, 2.5 Hz, 1H), 4.73 (p, J = 6.7 Hz, 2H), 3.93-3.46 (m, 8H), 2.28-1.50 (m, 10H). | 406.30 |
| 1-[3-(4-amino-7-methyl-5-{4-[4-(propan-2-yl)piperazin-1-yl]phenyl}-7H-pyrrolo[2,3-d]pyrimidin-6-yl)pyrrolidin-1-yl]prop-2-en-1-one | 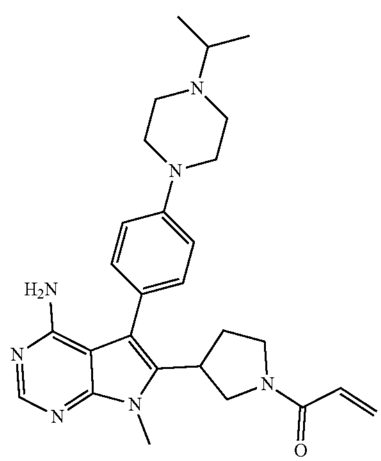 [SMILES: C=CC(=O)N1CCC(c2c(-c3ccc(N4CCN(C(C)C)CC4)cc3)c3c(N)ncnc3n2C)C1] | $^1$H NMR (400 MHz, Methanol-$d_4$) δ 8.11 (s, 1H), 7.29 (d, J = 8.6 Hz, 2H), 7.08 (s, 2H), 6.36-6.23 (m, 1H), 6.23-6.14 (m, 1H), 5.76-5.61 (m, 1H), 3.84 (s, 5H), 3.68 (s, 2H), 3.61 (s, 2H), 3.59-3.39 (m, 2H), 3.32 (d, J = 1.7 Hz, 1H), 2.80 (s, 5H), 2.34-1.97 (m, 2H), 1.18 (d, J = 6.5 Hz, 6H). | 474.45 |
| 1-(3-(4-amino-5-(4-(azetidin-3-yloxy)phenyl)-7-methyl-7H-pyrrolo[2,3-d]pyrimidin-6-yl)pyrrolidin-1-yl)prop-2-en-1-one | 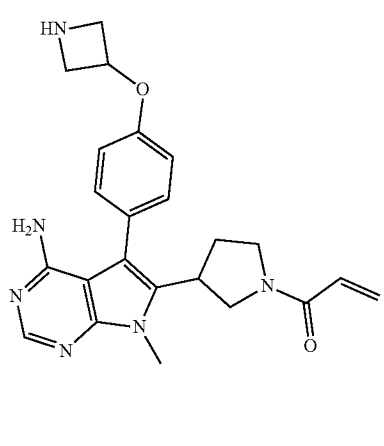 [SMILES: C=CC(=O)N1CCC(c2c(-c3ccc(OC4CNC4)cc3)c3c(N)ncnc3n2C)C1] | $^1$H NMR (400 MHz, Methanol-$d_4$) δ 8.12 (d, J = 7.3 Hz, 1H), 7.57 (dd, J = 8.1, 2.3 Hz, 1H), 7.50 (dd, J = 8.2, 2.4 Hz, 1H), 7.27-7.20 (m, 1H), 7.04 (ddd, J = 8.0, 5.5, 2.6 Hz, 1H), 4.99 (dt, J = 21.0, 6.5 Hz, 1H), 4.12-4.00 (m, 1H), 3.84 (d, J = 1.1 Hz, 3H), 3.68 (dd, J = 9.6, 6.4 Hz, 1H), 3.64-3.57 (m, 1H), 3.51 (t, J = 6.9 Hz, 3H), 3.43 (q, J = 7.2 Hz, 2H), 3.24-3.05 (m, 1H), 2.56-2.38 (m, 2H), 2.17-1.84 (m, 3H). | 419.30 |

TABLE 13-continued

Additional Exemplary Compounds

| Compound | Structure | Proton NMR | MS [M + 1] |
|---|---|---|---|
| 1-(3-{4-amino-7-methyl-5-[4-(pyrrolidin-1-yl)phenyl]-7H-pyrrolo[2,3-d]pyrimidin-6-yl}pyrrolidin-1-yl)prop-2-en-1-one | 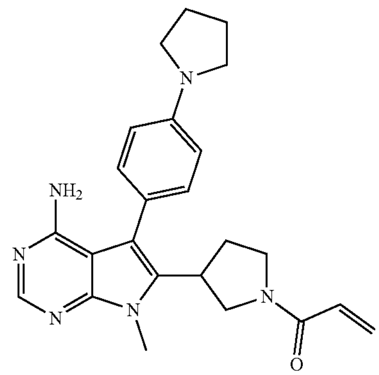 [SMILES: C=CC(=O)N1CCC(c2c(-c3ccc(N4CCCC4)cc3)c3c(N)ncnc3n2C)C1] | $^1$H NMR (400 MHz, Methanol-$d_4$) δ 8.21 (s, 1H), 8.11 (d, J = 1.4 Hz, 1H), 7.23-7.14 (m, 2H), 6.71-6.63 (m, 2H), 6.52 (dd, J = 16.8, 10.4 Hz, 1H), 6.36-6.10 (m, 1H), 5.66 (ddd, J = 37.9, 10.4, 2.1 Hz, 1H), 3.85 (s, 5H), 3.82-3.62 (m, 2H), 3.66-3.45 (dd, J = 12.3, 7.8 Hz, 4H), 3.36 (s, 1H), 2.28 (s, 2H), 2.07 (td, J = 7.5, 6.3, 4.2 Hz, 5H). | 417.20 |
| (R)-1-(3-(4-amino-5-(1-(2-(dimethylamino)ethyl)-1H-pyrazol-4-yl)-7-methyl-7H-pyrrolo[2,3-d]pyrimidin-6-yl)pyrrolidin-1-yl)prop-2-en-1-one | 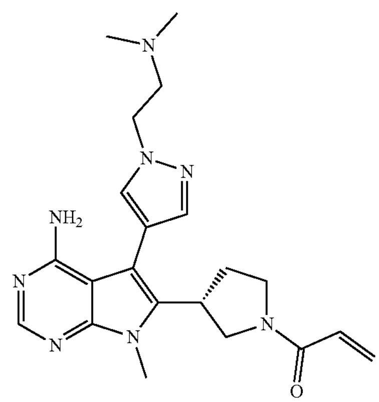 [SMILES: C=CC(=O)N1CC[C@@H](c2c(-c3cnn(CCN(C)C)c3)c3c(N)ncnc3n2C)C1] | $^1$H NMR (400 MHz, DMSO-$d_6$) δ 8.08 (d, J = 1.6 Hz, 1H), 7.82 (s, 1H), 7.48 (d, J = 8.2 Hz, 1H), 6.52 (ddd, J = 35.3, 16.7, 10.3 Hz, 1H), 6.12 (dt, J = 16.8, 2.1 Hz, 1H), 5.65 (td, J = 10.2, 2.5 Hz, 1H), 4.23 (t, J = 6.1 Hz, 2H), 3.93 (t, J = 8.9 Hz, 1H), 3.84-3.61 (m, 5H), 3.61-3.45 (m, 1H), 3.40-3.29 (m, 0H), 2.61 (t, J = 6.2 Hz, 2H), 2.14 (d, J = 1.7 Hz, 8H). | 409.25 |
| 1-(3-(5-(1-acetyl-3,3-dimethyl-1,2,3,6-tetrahydropyridin-4-yl)-4-amino-7-methyl-7H-pyrrolo[2,3-d]pyrimidin-6-yl)pyrrolidin-1-yl)prop-2-en-1-one | 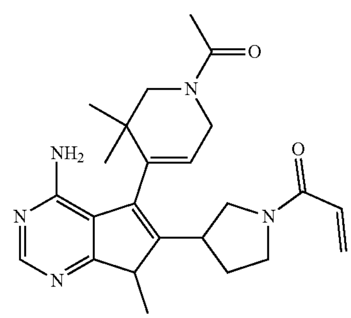 [SMILES: C=CC(=O)N1CCC(C2=C(C3=CCN(C(C)=O)CC3(C)C)c3c(N)ncnc3C2C)C1] | $^1$H NMR (400 MHz, Methanol-$d_4$) δ 8.08 (s, 1H), 7.35-7.26 (m, 1H), 6.61 (ddd, J = 15.4, 7.8, 3.3 Hz, 1H), 6.44 (d, J = 12.0 Hz, 1H), 6.12 (dt, J = 15.7, 3.6 Hz, 1H), 4.23-4.07 (dd, J = 11.4, 6.4 Hz, 3H), 3.92-3.79 (m, 1H), 3.78 (d, J = 3.7 Hz, 4H), 3.73 (s, 1H), 3.71-3.60 (m, 1H), 3.44 (dd, J = 19.4, 4.4 Hz, 2H), 2.59-2.40 (dd, J = 12.0, 6.0 Hz, 1H), 2.28-2.06 (m, 1H), 2.16 (dd, J = 6.0, 4.1 Hz, 3H), 1.16 (dd, J = 19.4, 4.7 Hz, 6H). | 423.20 |
| 1-(3-(4-amino-5-(6-cyclopropoxypyridin-3-yl)-7-methyl-7H-pyrrolo[2,3-d]pyrimidin-6-yl)pyrrolidin-1-yl)prop-2-en-1-one | 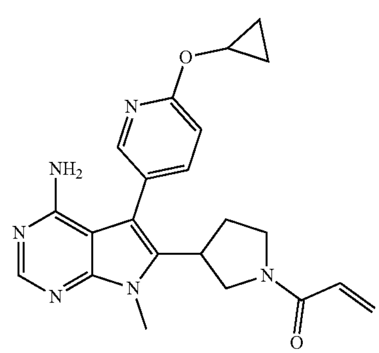 [SMILES: C=CC(=O)N1CCC(c2c(-c3ccc(OC4CC4)nc3)c3c(N)ncnc3n2C)C1] | $^1$H NMR (400 MHz, DMSO-d6) 8.20 (dd, J = 5.9, 2.4 Hz, 1H), 8.13 (s, 1H), 7.71 (dt, J = 8.4, 2.3 Hz, 1H), 6.93 (d, J = 8.4 Hz, 1H), 6.47 (ddd, J = 38.4, 16.7, 10.2 Hz, 1H), 6.09 (dt, J = 16.8, 2.8 Hz, 1H), 5.63 (ddd, J = 13.1, 10.2, 2.5 Hz, 3H), 4.25 (td, J = 6.1, 3.4 Hz, 1H), 3.81-3.59 (m, 5H), 3.51 (m, 2H), 3.26 (s, 1H), 2.28-1.59 (m, 2H), 0.90-0.57 (m, 4H). | 405.25 |

TABLE 13-continued

Additional Exemplary Compounds

| Compound | Structure | Proton NMR | MS [M + 1] |
|---|---|---|---|
| 1-(3-(4-amino-7-methyl-5-(4-(pyrrolidin-1-yl)-3-(trifluoromethyl)phenyl)-7H-pyrrolo[2,3-d]pyrimidin-6-yl)pyrrolidin-1-yl)prop-2-en-1-one | 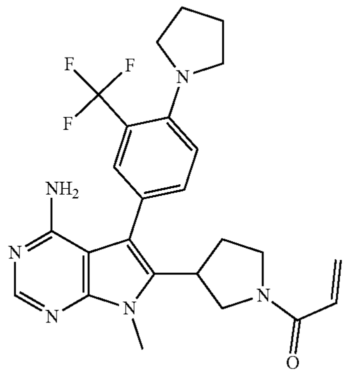 [SMILES: C=CC(=O)N1CCC(c2c(-c3ccc(N4CCCC4)c(C(F)(F)F)c3)c3c(N)ncnc3n2C)C1] | $^1$H NMR (400 MHz, DMSO-d$_6$) δ 8.11 (d, J = 1.5 Hz, 1H), 7.58-7.30 (m, 2H), 7.11 (d, J = 8.6 Hz, 1H), 6.73-6.25 (m, 1H), 6.08 (ddd, J = 16.8, 9.1, 2.5 Hz, 1H), 5.62 (ddd, J = 20.0, 10.3, 2.3 Hz, 3H), 3.77 (d, J = 5.8 Hz, 4H), 3.65 (q, J = 8.8 Hz, 1H), 3.51 (dt, J = 21.3, 9.3 Hz, 1H), 3.36 (s, 4H), 2.39-1.96 (m, 2H), 1.92 (d, J = 6.0 Hz, 5H). | 485.35 |
| 1-(4-(6-(1-acryloylpyrrolidin-3-yl)-4-amino-7-methyl-7H-pyrrolo[2,3-d]pyrimidin-5-yl)phenyl)-3-cyclopropylurea | 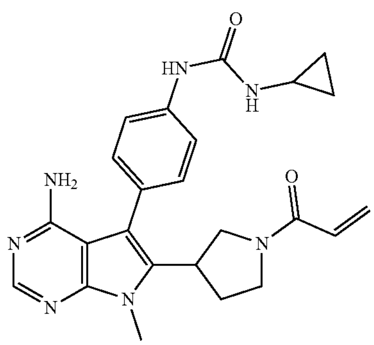 [SMILES: C=CC(=O)N1CCC(c2c(-c3ccc(NC(=O)NC4CC4)cc3)c3c(N)ncnc3n2C)C1] | $^1$H NMR (400 MHz, DMSO-d$_6$) δ 8.45 (s, 1H), 8.10 (d, J = 1.7 Hz, 1H), 7.57-7.44 (m, 2H), 7.23 (d, J = 8.2 Hz, 2H), 6.59-6.37 (m, 2H), 6.09 (ddd, J = 16.8, 4.2, 2.5 Hz, 1H), 5.63 (ddd, J = 13.1, 10.3, 2.5 Hz, 1H), 3.96-3.38 (m, 8H), 2.56 (dt, J = 7.1, 3.5 Hz, 1H), 2.31-1.94 (m, 2H), 0.65 (td, J = 6.9, 4.7 Hz, 2H), 0.47-0.38 (m, 2H). | 446.35 |
| 5-(4-(6-1-acryloylpyrrolidin-3-yl)-4-amino-7-methyl-7H-pyrrolo[2,3-d]pyrimidin-5-yl)phenyl)pyrrolidin-2-one | 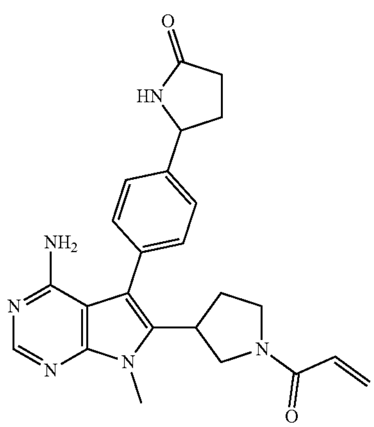 [SMILES: C=CC(=O)N1CCC(c2c(-c3ccc(C4CCC(=O)N4)cc3)c3c(N)ncnc3n2C)C1] | $^1$H NMR (400 MHz, DMSO-d$_6$) δ 8.12 (t, J = 2.9 Hz, 2H), 7.39 (d, J = 2.5 Hz, 4H), 6.62-6.28 (m, 1H), 6.14-6.04 (m, 1H), 5.63 (ddd, J = 14.3, 10.2, 2.4 Hz, 2H), 4.75 (t, J = 1.0 Hz, 1H), 3.91 (t, J = 9.2 Hz, 1H), 3.79 (d, J = 6.8 Hz, 3H), 3.74 (s, 2H), 3.66 (d, J = 9.8 Hz, 1H), 3.54 (s, 1H), 2.30-2.20 (m, 2H), 2.20 (s, 1H), 2.09 (d, J = 8.3 Hz, 1H), 2.03-1.69 (m, 3H). | 431.25 |
| 4-(6-(1-acryloylpyrrolidin-3-yl)-4-amino-7-methyl-7H-pyrrolo[2,3-d]pyrimidin-5-yl)-1-benzylpyridin-2(1H)-one | 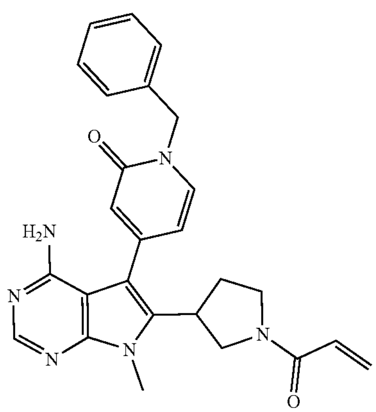 [SMILES: C=CC(=O)N1CCC(c2c(-c3ccn(Cc4ccccc4)c(=O)c3)c3c(N)ncnc3n2C)C1] | $^1$H NMR (400 MHz, Methanol-d$_4$) δ 8.16 (d, J = 1.0 Hz, 1H), 7.78 (dd, J = 11.1, 6.8 Hz, 1H), 7.45-7.35 (m, 4H), 7.39-7.29 (m, 1H), 6.65-6.42 (m, 3H), 6.31-6.20 (m, 1H), 5.72 (ddd, J = 22.8, 10.4, 2.0 Hz, 1H), 5.25 (s, 2H), 4.08-3.43 (m, 8H), 2.44-2.18 (m, 2H). | 455.35 |

TABLE 13-continued

Additional Exemplary Compounds

| Compound | Structure | Proton NMR | MS [M + 1] |
|---|---|---|---|
| 1-(4-(6-(1-acryloylpyrrolidin-3-yl)-4-amino-7-methyl-7H-pyrrolo[2,3-d]pyrimidin-5-yl)phenyl)imidazolidin-2-one | 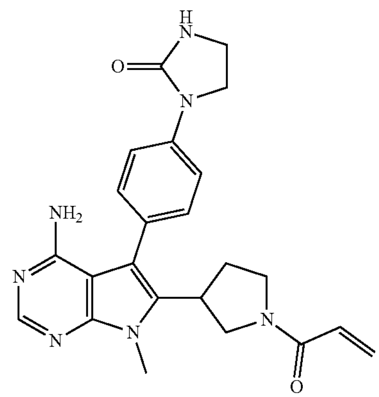 [SMILES: C=CC(=O)N1CCC(c2c(-c3ccc(N4CCNC4=O)cc3)c3c(N)ncnc3n2C)C1] | $^1$H NMR (400 MHz, DMSO-d$_6$) δ 8.11 (d, J = 1.8 Hz, 1H), 7.66 (d, J = 8.1 Hz, 2H), 7.31 (d, J = 8.2 Hz, 2H), 7.02 (s, 1H), 6.48 (ddd, J = 33.0, 16.7, 10.3 Hz, 1H), 6.14-6.04 (m, 1H), 5.68-5.57 (m, 2H), 3.92 (dt, J = 15.5, 8.6 Hz, 2H), 3.78 (d, J = 6.3 Hz, 4H), 3.50 (s, 3H), 3.43 (t, J = 8.1 Hz, 2H), 3.27 (s, 1H), 2.20 (d, J = 12.5 Hz, 1H), 2.06 (s, 1H). | 432.25 |
| 1-(3-(4-amino-7-methyl-5-(4-(pyrrolidin-1-ylmethyl)phenyl)-7H-pyrrolo[2,3-d]pyrimidin-6-yl)pyrrolidin-1-yl)prop-2-en-1-one | 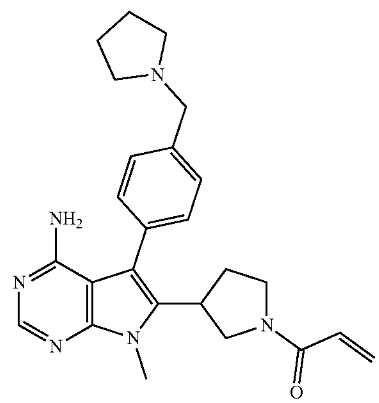 | $^1$H NMR (400 MHz, DMSO-d$_6$) δ 8.11 (d, J = 2.1 Hz, 1H), 7.36 (ddd, J = 28.1, 7.8, 4.0 Hz, 4H), 6.66-6.22 (m, 1H), 6.08 (ddd, J = 16.9, 6.5, 2.4 Hz, 1H), 5.61 (ddd, J = 20.5, 10.3, 2.5 Hz, 1H), 3.81-3.71 (m, 4H), 3.68-3.63 (m, 1H), 3.63 (s, 2H), 3.59-3.42 (m, 1H), 3.26 (dd, J = 19.8, 9.4 Hz, 1H), 2.46 (s, 5H), 2.21 (s, 1H), 2.16-1.97 (m, 1H), 1.72 (d, J = 6.0 Hz, 4H). | 431.50 |
| (R)-1-(3-(4-amino-5-(4-(benzyloxy)phenyl)-7-methyl-7H-pyrrolo[2,3-d]pyrimidin-6-yl)pyrrolidin-1-yl)prop-2-en-1-one | 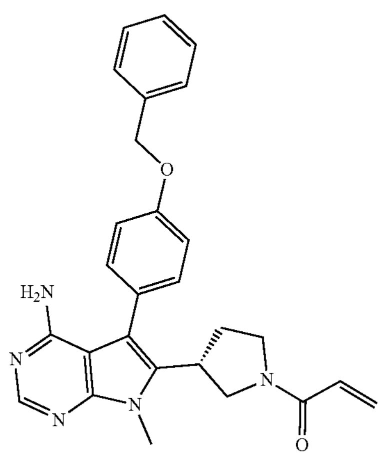 [SMILES: C=CC(=O)N1CC[C@@H](c2c(-c3ccc(OCc4ccccc4)cc3)c3c(N)ncnc3n2C)C1] | $^1$H NMR (400 MHz, DMSO-d$_6$) δ 8.11 (d, J = 1.6 Hz, 1H), 7.54-7.28 (m, 7H), 7.11 (d, J = 8.0 Hz, 2H), 6.52 (dd, J = 16.8, 10.3 Hz, 1H), 6.10 (ddd, J = 16.8, 5.7, 2.4 Hz, 1H), 5.63 (ddd, J = 15.0, 10.3, 2.5 Hz, 1H), 5.14 (s, 2H), 3.97-3.88 (m, 0H), 3.77 (d, J = 5.9 Hz, 4H), 3.70-3.58 (m, 1H), 3.57-3.40 (m, 1H), 3.27 (s, 1H), 2.26-1.87 (m, 2H). | 454.35 |

TABLE 13-continued

Additional Exemplary Compounds

| Compound | Structure | Proton NMR | MS [M + 1] |
|---|---|---|---|
| 2-(4-(6-(1-acryloylpyrrolidin-3-yl)-4-amino-7-methyl-7H-pyrrolo[2,3-d]pyrimidin-5-yl)phenyl)-N,N-dimethylacetamide | 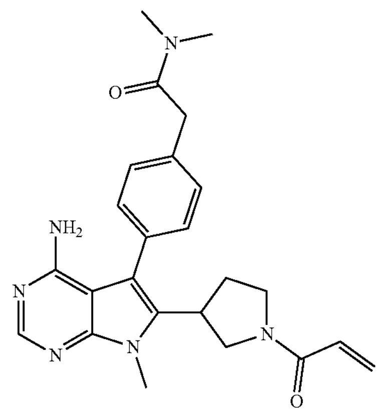 [SMILES: C=CC(=O)N1CCC(c2c(-c3ccc(CC(=O)N(C)C)cc3)c3c(N)ncnc3n2C)C1] | ¹H NMR (400 MHz, DMSO-d₆) δ 8.11 (d, J = 2.0 Hz, 1H), 7.32 (d, J = 2.5 Hz, 4H), 6.45 (dd, J = 41.8, 10.3 Hz, 1H), 6.09 (ddd, J = 16.7, 6.1, 2.4 Hz, 1H), 5.63 (ddd, J = 13.5, 10.3, 2.5 Hz, 1H), 3.92 (t, J = 9.2 Hz, 1H), 3.81-3.74 (m, 6H), 3.72-3.63 (m, 1H), 3.51 (dd, J = 20.4, 10.0 Hz, 1H), 3.03 (s, 3H), 2.99 (s, 1H), 2.86 (s, 3H), 2.20 (d, J = 7.3 Hz, 1H), 2.09 (t, J = 10.3 Hz, 1H). | 433.25 |
| 1-(3-(4-amino-7-methyl-5-(6-(2,2,2-trifluoroethoxy)pyridin-3-yl)-7H-pyrrolo[2,3-d]pyrimidin-6-yl)pyrrolidin-1-yl)prop-2-en-1-one | 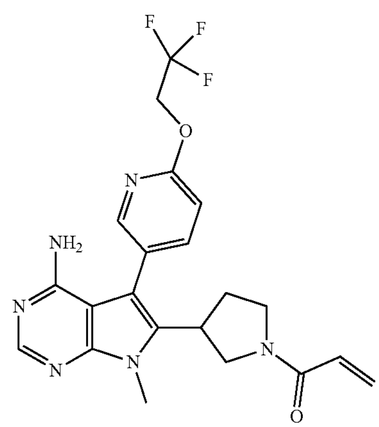 [SMILES: C=CC(=O)N1CCC(c2c(-c3ccc(OCC(F)(F)F)nc3)c3c(N)ncnc3n2C)C1] | ¹H NMR (400 MHz, DMSO-d₆) δ 8.20 (t, J = 2.9 Hz, 1H), 8.12 (d, J = 1.5 Hz, 1H), 7.80 (dd, J = 8.3, 2.9 Hz, 1H), 7.06 (d, J = 8.4 Hz, 1H), 6.51-6.41 (dd, J = 16.7, 10.2 Hz, 1H), 6.09 (dt, J = 16.9, 3.1 Hz, 1H), 5.80-5.50 (bar, 2H), 5.63 (ddd, J = 15.3, 10.2, 2.5 Hz, 1H), 5.01 (q, J = 9.1 Hz, 2H), 3.93 (t, J = 9.1 Hz, 1H), 3.79 (d, J = 6.8 Hz, 4H), 3.67 (s, 1H), 3.56-3.43 (m, 1H), 3.31-3.22 (m, 1H), 2.25-1.89 (m, 2H). | 447.10 |
| 1-(4-(6-(1-acryloylpyrrolidin-3-yl)-4-amino-7-methyl-7H-pyrrolo[2,3-d]pyrimidin-5-yl)phenyl)-3-methylimidazolidin-2-one | 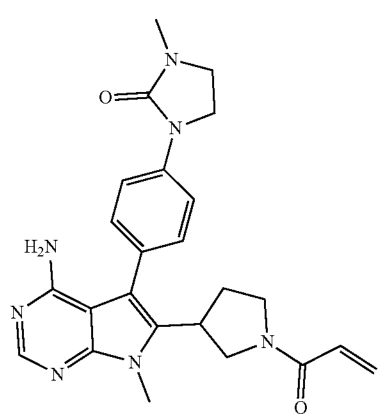 [SMILES: C=CC(=O)N1CCC(c2c(-c3ccc(N4CCN(C)C4=O)cc3)c3c(N)ncnc3n2C)C1] | ¹H NMR (400 MHz, DMSO-d₆) δ 8.11 (d, J = 1.8 Hz, 1H), 7.68 (d, J = 8.3 Hz, 2H), 7.32 (d, J = 8.1 Hz, 2H), 6.48 (ddd, J = 33.2, 16.8, 10.3 Hz, 1H), 6.09 (ddd, J = 16.8, 5.4, 2.5 Hz, 1H), 5.62 (ddd, J = 14.2, 10.3, 2.5 Hz, 1H), 3.94 (t, J = 9.0 Hz, 1H), 3.80 (dd, J = 21.6, 7.2 Hz, 5H), 3.65 (tt, J = 18.0, 8.7 Hz, 1H), 3.57-3.42 (m, 2H), 3.30-3.15 (m, 1H), 2.79 (s, 3H), 2.24-2.17 (m, 1H), 2.12-1.91 (m, 1H). | 446.30 |

TABLE 13-continued

Additional Exemplary Compounds

| Compound | Structure | Proton NMR | MS [M + 1] |
|---|---|---|---|
| 1-(3-(4-amino-5-(4-(2-hydroxy-1-phenylethyl)phenyl)-7-methyl-7H-pyrrolo[2,3-d]pyrimidin-6-yl)pyrrolidin-1-yl)prop-2-en-1-one | 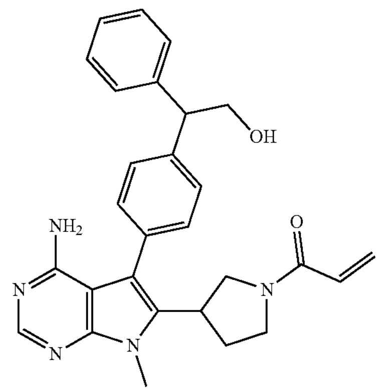 [SMILES: C=CC(=O)N1CCC(c2c(-c3ccc(C(CO)c4ccccc4)cc3)c3c(N)ncnc3n2C)C1] | $^1$H NMR (400 MHz, DMSO-d$_6$) δ 8.10 (d, J = 2.7 Hz, 1H), 7.41-7.35 (m, 2H), 7.34-7.26 (m, 6H), 7.20 (tt, J = 5.6, 2.8 Hz, 1H), 6.51-6.37 (ddd, J = 16.9, 10.3, 3.9 Hz, 1H), 6.08 (ddd, J = 16.8, 13.8, 2.3 Hz, 1H), 5.69-5.52 (ddd, J = 10.3, 4.6, 2.4 Hz, 1H), 4.81 (t, J = 5.3 Hz, 1H), 4.16 (t, J = 7.2 Hz, 1H), 4.08-3.94 (m, 2H), 3.80-3.68 (m, 4H), 3.66-3.41 (m, 3H), 3.24 (dd, J = 11.9, 8.0 Hz, 1H), 2.18-1.91 (t, J = 10.7 Hz, 2H). | 468.20 |
| 1-(3-(4-amino-5-(4-(cyclopropylsulfonyl)phenyl)-7-methyl-7H-pyrrolo[2,3-d]pyrimidin-6-yl)pyrrolidin-1-yl)prop-2-en-1-one | 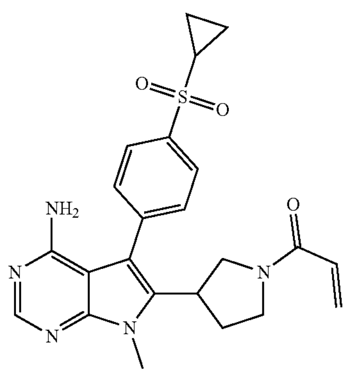 [SMILES: C=CC(=O)N1CCC(c2c(-c3ccc(S(=O)(=O)C4CC4)cc3)c3c(N)ncnc3n2C)C1] | $^1$H NMR (400 MHz, DMSO-d$_6$) δ 8.15 (d, J = 2.1 Hz, 1H), 7.96 (dd, J = 8.4, 2.9 Hz, 2H), 7.65 (d, J = 7.9 Hz, 2H), 6.59-6.40 (dd, J = 16.8, 10.3 Hz, 1H), 6.10 (ddd, J = 16.8, 4.0, 2.5 Hz, 1H), 5.64 (ddd, J = 14.4, 10.2, 2.4 Hz, 1H), 3.94-3.72 (m, 3H), 3.71-3.55 (m, 3H), 3.55-3.44 (m, 1H), 3.27 (s, 1H), 2.96-2.87 (m, 1H), 2.21 (d, J = 6.7 Hz, 1H), 2.12 (t, J = 10.3 Hz, 1H), 1.27-1.15 (m, 2H), 1.09 (dt, J = 8.2, 2.7 Hz, 2H). | 452.15 |
| (R)-1-(3-(4-amino-7-methyl-5-(4-(tetrahydro-2H-pyran-4-yl)phenyl)-7H-pyrrolo[2,3-d]pyrimidin-6-yl)pyrrolidin-1-yl)prop-2-en-1-one | 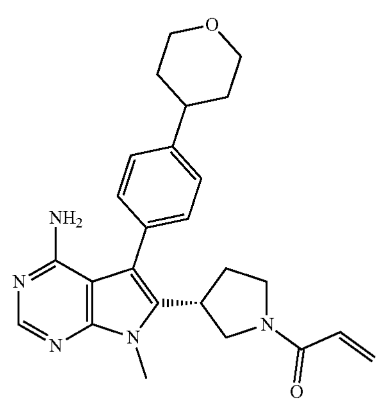 [SMILES: C=CC(=O)N1CC[C@@H](c2c(-c3ccc(C4CCOCC4)cc3)c3c(N)ncnc3n2C)C1] | $^1$H NMR (400 MHz, DMSO-d$_6$) δ 8.11 (d, J = 2.0 Hz, 1H), 7.35 (q, J = 7.3, 6.7 Hz, 4H), 6.51 (dd, J = 16.8, 10.3 Hz, 1H), 6.38 (dd, J = 16.8, 10.3 Hz, 0H), 6.08 (ddd, J = 16.8, 10.2, 2.5 Hz, 1H), 5.62 (ddd, J = 20.1, 10.2, 2.5 Hz, 1H), 4.01-3.93 (m, 2H), 3.93-3.84 (m, 1H), 3.79 (s, 2H), 3.77 (s, 2H), 3.76-3.59 (m, 1H), 3.58-3.44 (m, 2H), 3.43 (d, J = 2.8 Hz, 1H), 3.36-3.21 (m, 1H), 2.89-2.79 (m, 1H), 2.10 (s, 1H), 2.08 (s, 1H), 1.97 (p, J = 10.9, 10.3 Hz, 1H), 1.72 (dq, J = 16.5, 12.6 Hz, 4H). | 432.35 |

TABLE 13-continued

Additional Exemplary Compounds

| Compound | Structure | Proton NMR | MS [M + 1] |
|---|---|---|---|
| 1-(3-{4-amino-7-methyl-5-[4-(phenoxymethyl)phenyl]-7H-pyrrolo[2,3-d]pyrimidin-6-yl}pyrrolidin-1-yl)prop-2-en-1-one | 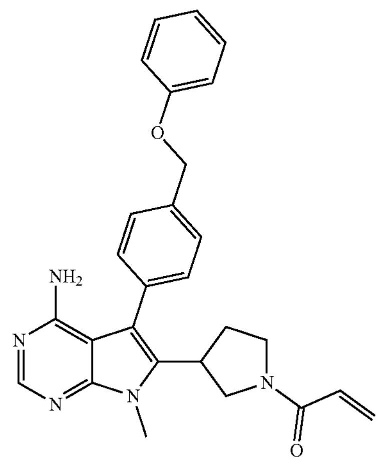 [SMILES: C=CC(=O)N1CCC(c2c(-c3ccc(COc4ccccc4)cc3)c3c(N)ncnc3n2C)C1] | $^1$H NMR (400 MHz, DMSO-d$_6$) δ 8.12 (d, J = 1.7 Hz, 1H), 7.56 (d, J = 7.8 Hz, 2H), 7.43 (d, J = 7.7 Hz, 2H), 7.32 (t, J = 7.7 Hz, 2H), 7.06 (d, J = 8.0 Hz, 2H), 6.97 (t, J = 7.3 Hz, 1H), 6.47 (ddd, J = 37.4, 16.8, 10.3 Hz, 1H), 6.09 (ddd, J = 16.6, 7.2, 2.4 Hz, 1H), 5.63 (ddd, J = 15.7, 10.1, 2.5 Hz, 1H), 5.17 (s, 2H), 3.94 (t, J = 9.2 Hz, 1H), 3.79 (d, J = 6.2 Hz, 4H), 3.66 (q, J = 9.3 Hz, 1H), 3.60-3.42 (m, 2H), 3.28 (d, J = 11.6 Hz, 1H), 2.08 (s, 4H), 1.16 (dt, J = 26.1, 13.1 Hz, 1H). | 454.20 |
| 1-(3-(4-amino-5-(4-cyclobutoxyphenyl)-7-methyl-7H-pyrrolo[2,3-d]pyrimidin-6-yl)pyrrolidin-1-yl)prop-2-en-1-one | 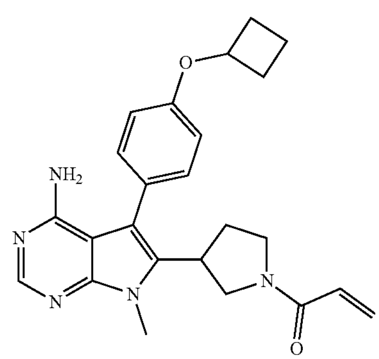 [SMILES: C=CC(=O)N1CCC(c2c(-c3ccc(OC4CCC4)cc3)c3c(N)ncnc3n2C)C1] | 1H NMR (400 MHz, DMSO-d6) 8.10 (d, J = 1.7 Hz, 1H), 7.27 (d, J = 8.1 Hz, 2H), 6.92 (d, J = 8.1 Hz, 2H), 6.46 (ddd, J = 46.5, 16.8, 10.3 Hz, 1H), 6.09 (ddd, J = 16.8, 7.0, 2.5 Hz, 1H), 5.83-4.98 (m, 2H), 4.72 (q, J = 7.1 Hz, 1H), 3.93-3.60 (m, 5H), 3.32 (s, 3H), 3.31-3.23 (m, 1H), 2.48-2.00 (m, 5H), 1.87-1.60 (m, 2H). | 418.25 |
| 1-(3-(4-amino-5-(4-(cyclopentylamino)phenyl)-7-methyl-7H-pyrrolo[2,3-d]pyrimidin-6-yl)pyrrolidin-1-yl)prop-2-en-1-one | 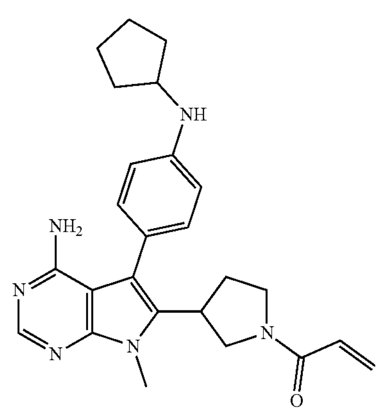 [SMILES: C=CC(=O)N1CCC(c2c(-c3ccc(NC4CCCC4)cc3)c3c(N)ncnc3n2C)C1] | $^1$H NMR (400 MHz, DMSO-d$_6$) δ 8.08 (d, J = 1.8 Hz, 1H), 7.05 (d, J = 7.7 Hz, 2H), 6.63 (d, J = 8.0 Hz, 2H), 6.48 (ddd, J = 41.0, 16.7, 10.3 Hz, 1H), 6.09 (ddd, J = 16.8, 7.6, 2.4 Hz, 1H), 5.83-5.76 (m, 1H), 5.62 (ddd, J = 17.7, 10.2, 2.5 Hz, 1H), 3.95-3.70 (m, 6H), 3.70-3.42 (m, 1H), 3.28 (d, J = 10.9 Hz, 1H), 2.25-1.85 (m, 4H), 1.72-1.67 (m, 2H), 1.60-1.44 (m, 4H), 1.29-0.99 (m, 1H). | 431.35 |

TABLE 13-continued

Additional Exemplary Compounds

| Compound | Structure | Proton NMR | MS [M + 1] |
|---|---|---|---|
| 1-(3-(5-(4-(1H-imidazol-2-yl)phenyl)-4-amino-7-methyl-7H-pyrrolo[2,3-d]pyrimidin-6-yl)pyrrolidin-1-yl)prop-2-en-1-one | 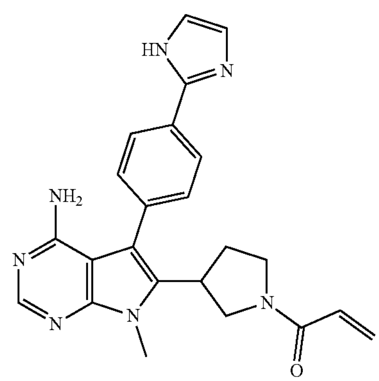 [SMILES: C=CC(=O)N1CCC(c2c(-c3ccc(-c4ncc[nH]4)cc3)c3c(N)ncnc3n2C)C1] | $^1$H NMR (400 MHz, DMSO-d$_6$) δ 12.58 (s, 1H), 8.13 (d, J = 1.8 Hz, 1H), 8.02 (d, J = 8.2 Hz, 2H), 7.45 (d, J = 7.9 Hz, 2H), 7.29 (d, J = 2.0 Hz, 1H), 7.07 (s, 1H), 6.47 (ddd, J = 27.8, 16.8, 10.3 Hz, 1H), 6.07 (ddd, J = 16.8, 5.9, 2.5 Hz, 1H), 5.60 (ddd, J = 19.1, 10.3, 2.5 Hz, 2H), 3.97 (t, J = 9.3 Hz, 0H), 3.80 (d, J = 6.6 Hz, 4H), 3.68 (d, J = 9.0 Hz, 1H), 3.60-3.49 (m, 2H), 2.04 (dq, J = 33.4, 11.2 Hz, 2H). | 414.15 |
| 1-[3-(4-amino-7-methyl-5-{4-[(1H-pyrazol-1-yl)methyl]phenyl}-7H-pyrrolo[2,3-d]pyrimidin-6-yl)pyrrolidin-1-yl]prop-2-en-1-one | 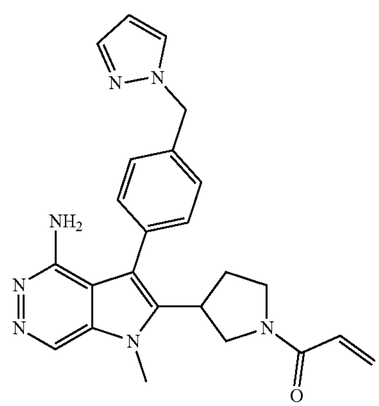 [SMILES: C=CC(=O)N1CCC(c2c(-c3ccc(Cn4cccn4)cc3)c3c(N)nncc3n2C)C1] | 1H NMR (400 MHz, Methanol-d4) 8.14 (d, J = 0.8 Hz, 1H), 7.80 (d, J = 2.3 Hz, 1H), 7.57 (d, J = 2.0 Hz, 1H), 7.46-7.38 (m, 2H), 7.32 (d, J = 8.1 Hz, 2H), 6.50 (dd, J = 16.8, 10.4 Hz, 1H), 6.39 (t, J = 2.2 Hz, 1H), 6.32-6.21 (td, J = 16.4, 2.1 Hz, 2H), 5.73-5.66 (dd, J = 10.3, 2.2 Hz, 1H), 5.51 (s, 1H), 5.45 (d, J = 2.6 Hz, 2H), 3.98-3.75 (m, 5H), 3.78-3.35 (m, 3H), 2.35-2.05 (s, 2H). | 428.25 |
| 1-(3-(4-amino-7-methyl-5-(4-(1-methyl-1H-pyrazol-4-yl)phenyl)-7H-pyrrolo[2,3-d]pyrimidin-6-yl)pyrrolidin-1-yl)prop-2-en-1-one | 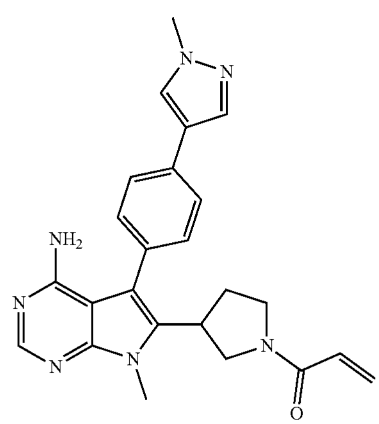 [SMILES: C=CC(=O)N1CCC(c2c(-c3ccc(-c4cnn(C)c4)cc3)c3c(N)ncnc3n2C)C1] | $^1$H NMR (400 MHz, DMSO-d$_6$) δ 8.19 (s, 1H), 8.12 (d, J = 1.8 Hz, 1H), 7.92 (s, 1H), 7.66 (d, J = 7.8 Hz, 2H), 7.36 (d, J = 7.8 Hz, 2H), 6.51-6.43 (dd, J = 16.8, 10.3 Hz, 1H), 6.07 (ddd, J = 16.7, 8.1, 2.5 Hz, 1H), 5.61 (ddd, J = 20.9, 10.3, 2.4 Hz, 2H), 3.95 (t, J = 9.2 Hz, 0H), 3.89 (s, 3H), 3.79 (d, J = 6.2 Hz, 4H), 3.67 (q, J = 12.0, 10.8 Hz, 1H), 3.56 (t, J = 10.1 Hz, 2H), 3.54-3.27 (d, J = 8.1 Hz, 1H), 2.25-1.95 (m, 1H). | 428.15 |

TABLE 13-continued

Additional Exemplary Compounds

| Compound | Structure | Proton NMR | MS [M + 1] |
|---|---|---|---|
| 1-(3-(4-amino-7-methyl-5-(4-(5-methyl-1,2,4-oxadiazol-3-yl)phenyl)-7H-pyrrolo[2,3-d]pyrimidin-6-yl)pyrrolidin-1-yl)prop-2-en-1-one | 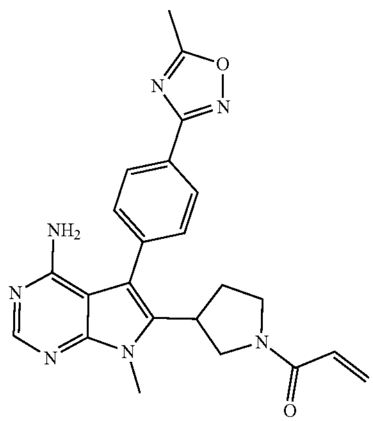 [SMILES: C=CC(=O)N1CCC(c2c(-c3ccc(-c4noc(C)n4)cc3)c3c(N)ncnc3n2C)C1] | ¹H NMR (400 MHz, DMSO-d₆) δ 8.14 (d, J = 1.7 Hz, 1H), 8.07 (d, J = 8.2 Hz, 2H), 7.57 (d, J = 8.2 Hz, 2H), 6.51-6.42 (dd, J = 16.7, 10.3 Hz, 1H), 6.06 (ddd, J = 16.8, 7.1, 2.4 Hz, 1H), 5.63 (dd, J = 10.3, 2.5 Hz, 1H), 5.57 (dd, J = 10.2, 2.5 Hz, 1H), 3.99-3.90 (m, 1H), 3.81 (d, J = 6.6 Hz, 5H), 3.69 (d, J = 8.6 Hz, 1H), 3.58 (d, J = 9.8 Hz, 1H), 3.50-3.28 (d, J = 10.1 Hz, 1H), 2.70 (s, 3H), 2.26-2.19 (m, 1H), 2.11-1.94 (m, 1H). | 430.15 |
| 1-(3-(4-amino-5-(4-(0,1-dioxidoisothiazolidin-2-yl)methyl)phenyl)-7-methyl-7H-pyrrolo[2,3-d]pyrimidin-6-yl)pyrrolidin-1-yl)prop-2-en-1-one | 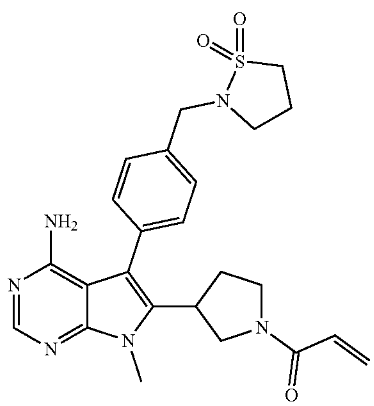 [SMILES: C=CC(=O)N1CCC(c2c(-c3ccc(CN4CCCS4(=O)=O)cc3)c3c(N)ncnc3n2C)C1] | ¹H NMR (400 MHz, DMSO-d6) 8.12 (d, J = 2.2 Hz, 1H), 7.53-7.30 (m, 4H), 6.45 (ddd, J = 46.4, 16.7, 10.3 Hz, 1H), 6.08 (dt, J = 16.7, 2.4 Hz, 1H), 5.62 (ddd, J = 15.1, 10.2, 2.4 Hz, 1H), 5.58-4.92 (s, 1H), 4.23-4.09 (m, 2H), 4.00-3.72 (m, 4H), 3.70-3.35 (m, 2H), 3.33 (s, 1H), 3.28 (t, J = 7.7 Hz, 3H), 3.14 (td, J = 6.8, 2.3 Hz, 2H), 2.24 (p, J = 7.0 Hz, 3H), 2.09 (dt, J = 14.1, 8.2 Hz, 1H), 1.96 (dq, J = 21.2, 10.5 Hz, 1H). | 481.25 |
| 1-(3-(4-amino-5-(4-(cyclopentylmethyl)phenyl)-7-methyl-7H-pyrrolo[2,3-d]pyrimidin-6-yl)pyrrolidin-1-yl)prop-2-en-1-one | 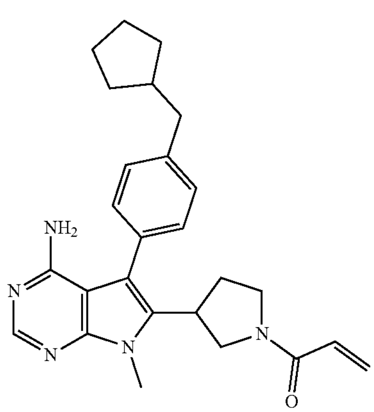 [SMILES: C=CC(=O)N1CCC(c2c(-c3ccc(CC4CCCC4)cc3)c3c(N)ncnc3n2C)C1] | ¹H NMR (400 MHz, DMSO-d₆) δ 8.10 (d, J = 2.2 Hz, 1H), 7.28 (d, J = 2.6 Hz, 4H), 6.44 (ddd, J = 55.7, 16.7, 10.3 Hz, 1H), 6.08 (ddd, J = 16.7, 7.0, 2.4 Hz, 1H), 5.61 (ddd, J = 20.9, 10.2, 2.5 Hz, 2H), 3.92-3.73 (m, 4H), 3.64 (t, J = 9.1 Hz, 1H), 3.58-3.38 (m, 2H), 3.29-3.22 (m, 1H), 2.64 (d, J = 7.5 Hz, 2H), 2.28-1.85 (m, 3H), 1.76-1.44 (m, 6H), 1.20 (q, J = 10.2, 9.3 Hz, 2H). | 430.35 |

TABLE 13-continued

Additional Exemplary Compounds

| Compound | Structure | Proton NMR | MS [M + 1] |
|---|---|---|---|
| 1-(3-(4-amino-7-methyl-5-(4-((tetrahydro-2H-pyran-4-yl)amino)phenyl)-7H-pyrrolo[2,3-d]pyrimidin-6-yl)pyrrolidin-1-yl)prop-2-en-1-one | 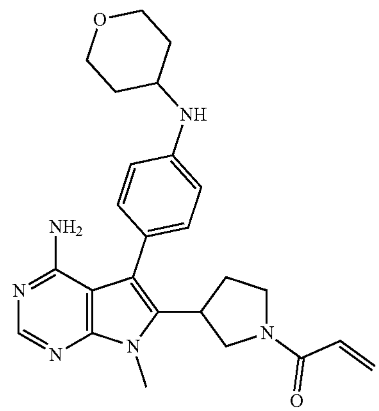 [SMILES: C=CC(=O)N1CCC(c2c(-c3ccc(NC4CCOCC4)cc3)c3c(N)ncnc3n2C)C1] | ¹H NMR (400 MHz, DMSO-d₆) δ 8.11 (d, J = 2.0 Hz, 1H), 7.35 (q, J = 7.3, 6.7 Hz, 4H), 6.51 (dd, J = 16.8, 10.3 Hz, 1H), 6.38 (dd, J = 16.8, 10.3 Hz, 1H), 6.08 (ddd, J = 16.8, 10.2, 2.5 Hz, 1H), 5.71 (ddd, J = 18.2, 10.2, 2.5 Hz, 1H), 5.62 (ddd, J = 20.1, 10.2, 2.5 Hz, 1H), 4.01-3.93 (m, 2H), 3.93-3.84 (m, 1H), 3.79 (s, 2H), 3.77 (s, 2H), 3.76-3.59 (m, 1H), 3.58-3.44 (m, 2H), 3.43 (d, J = 2.8 Hz, 1H), 3.36-3.21 (m, 1H), 2.89-2.79 (m, 1H), 2.10 (s, 1H), 2.08 (s, 1H), 1.97 (p, J = 10.9, 10.3 Hz, 1H), 1.72 (dq, J = 16.5, 12.6 Hz, 4H). | 447.35 |
| 1-(4-(6-(1-acryloylpyrrolidin-3-yl)-4-amino-7-methyl-7H-pyrrolo[2,3-d]pyrimidin-5-yl)benzyl)pyridin-2(1H)-one | 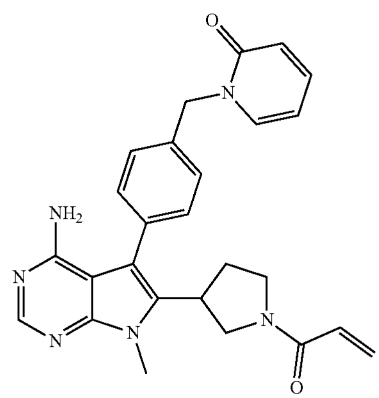 [SMILES: C=CC(=O)N1CCC(c2c(-c3ccc(Cn4ccccc4=O)cc3)c3c(N)ncnc3n2C)C1] | ¹H NMR (400 MHz, DMSO-d6) 8.11 (d, J = 2.0 Hz, 1H), 7.83 (dd, J = 6.9, 2.0 Hz, 1H), 7.46 (ddt, J = 8.7, 6.6, 1.9 Hz, 1H), 7.36 (d, J = 5.3 Hz, 4H), 6.56-6.34 (m, 2H), 6.31-6.23 (m, 1H), 6.08 (ddd, J = 16.8, 11.7, 2.4 Hz, 1H), 5.62 (ddd, J = 19.2, 10.3, 2.5 Hz, 1H), 5.18 (d, J = 1.7 Hz, 2H), 3.92-3.75 (m, 4H), 3.75-3.40 (m, 4H), 3.30-3.18 (m, 2H), 2.27-1.87 (m, 2H). | 455.30 |
| 1-[3-(4-amino-5-{4-[cyclopropyl(hydroxy)methyl]phenyl}-7-methyl-7H-pyrrolo[2,3-d]pyrimidin-6-yl)pyrrolidin-1-yl]prop-2-en-1-one | 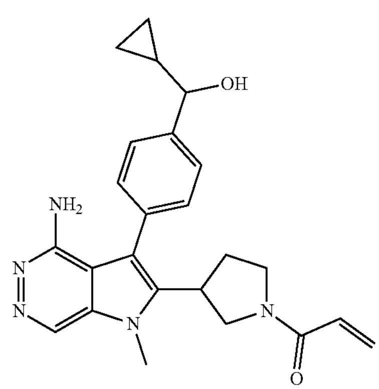 [SMILES: C=CC(=O)N1CCC(c2c(-c3ccc(C(O)C4CC4)cc3)c3c(N)nncc3n2C)C1] | 1H NMR (400 MHz, DMSO-d6) 8.12 (d, J = 2.2 Hz, 1H), 7.50 (d, J = 7.7 Hz, 2H), 7.38-7.31 (m, 2H), 6.53-6.43 (ddd, J = 16.9, 10.4, 3.3 Hz, 1H), 6.09 (ddd, J = 16.9, 8.8, 2.5 Hz, 1H), 5.76-5.63 (ddd, J = 16.5, 10.3, 2.4 Hz, 2H), 5.25 (dd, J = 4.5, 2.3 Hz, 1H), 4.06 (dd, J = 7.4, 4.4 Hz, 1H), 3.92 (t, J = 9.2 Hz, 1H), 3.79 (d, J = 6.5 Hz, 4H), 3.73-3.51 (dd, J = 21.7, 11.0 Hz, 3H), 3.31-3.21 (m, 1H), 2.20-1.93 (m, 2H), 1.13-1.06 (m, 1H), 0.44 (td, J = 12.9, 6.6 Hz, 4H). | 418.30 |

TABLE 13-continued

Additional Exemplary Compounds

| Compound | Structure | Proton NMR | MS [M + 1] |
|---|---|---|---|
| 1-[3-(4-amino-7-methyl-5-{4-[(3-methyl-1H-pyrazol-1-yl)methyl]phenyl}-7H-pyrrolo[2,3-d]pyrimidin-6-yl)pyrrolidin-1-yl]prop-2-en-1-one | 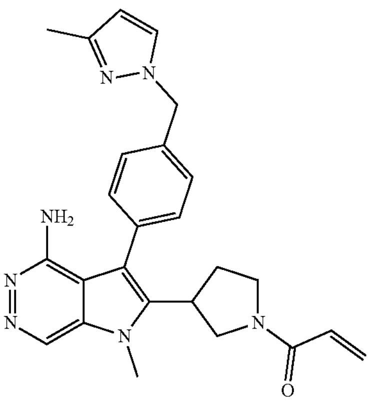 [SMILES: C=CC(=O)N1CCC(c2c(-c3ccc(Cn4ccc(C)n4)cc3)c3c(N)nncc3n2C)C1] | 1H NMR (400 MHz, DMSO-d6) 8.11 (t, J = 2.1 Hz, 1H), 7.73 (t, J = 2.6 Hz, 1H), 7.41-7.32 (m, 2H), 7.25 (dd, J = 8.3, 3.4 Hz, 1H), 7.14 (dd, J = 8.1, 3.7 Hz, 1H), 6.57-6.32 (m, 1H), 6.15-6.07 (m, 1H), 6.11-6.03 (m, 1H), 5.62 (ddt, J = 15.8, 10.3, 2.6 Hz, 1H), 5.38 (s, 1H), 5.32 (d, J = 2.7 Hz, 1H), 3.81-3.75 (m, 3H), 3.79-3.56 (m, 2H), 3.58-3.41 (m, 2H), 3.32-3.15 (m, 1H), 2.20 (dd, J = 21.3, 2.3 Hz, 3H), 2.10-1.89 (m, 2H). | 442.25 |
| 1-(3-(4-amino-7-methyl-5-(4-(4-methyl-1H-pyrazol-1-yl)phenyl)-7H-pyrrolo[2,3-d]pyrimidin-6-yl)pyrrolidin-1-yl)prop-2-en-1-one | 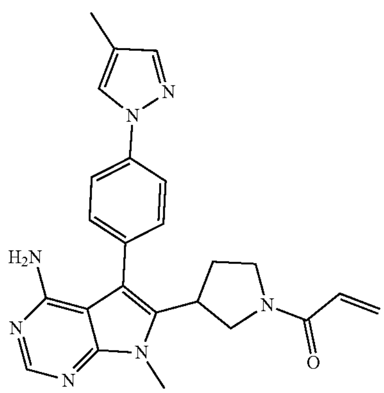 [SMILES: C=CC(=O)N1CCC(c2c(-c3ccc(-n4cc(C)cn4)cc3)c3c(N)ncnc3n2C)C1] | $^1$H NMR (400 MHz, DMSO-d$_6$) δ 8.34 (s, 1H), 8.12 (d, J = 1.7 Hz, 1H), 7.87 (d, J = 8.1 Hz, 2H), 7.60 (s, 1H), 7.47 (d, J = 8.2 Hz, 2H), 6.47 (ddd, J = 31.9, 16.7, 10.2 Hz, 1H), 6.06 (ddd, J = 16.8, 7.5, 2.5 Hz, 1H), 5.60 (ddd, J = 21.7, 10.2, 2.5 Hz, 2H), 3.94 (d, J = 9.1 Hz, 1H), 3.79 (d, J = 6.3 Hz, 3H), 3.67 (q, J = 9.1 Hz, 1H), 3.60-3.45 (m, 1H), 3.29 (d, J = 10.7 Hz, 1H), 2.33 (d, J = 2.2 Hz, 1H), 2.13 (s, 5H). | 428.25 |
| 1-(3-(4-amino-7-methyl-5-(4-((5-(trifluoromethyl)pyridin-2-yl)oxy)phenyl)-7H-pyrrolo[2,3-d]pyrimidin-6-yl)pyrrolidin-1-yl)prop-2-en-1-one | 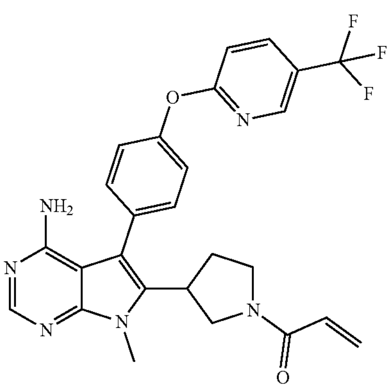 [SMILES: C=CC(=O)N1CCC(c2c(-c3ccc(Oc4ccc(C(F)(F)F)cn4)cc3)c3c(N)ncnc3n2C)C1] | 1H NMR (400 MHz, DMSO-d6) 8.68-8.58 (m, 1H), 8.27 (dt, J = 8.7, 2.8 Hz, 1H), 8.13 (d, J = 2.1 Hz, 1H), 7.47 (d, J = 8.1 Hz, 2H), 7.32 (dd, J = 9.1, 4.1 Hz, 3H), 6.51 (ddd, J = 32.6, 16.8, 10.3 Hz, 1H), 6.13 (t, J = 1.9 Hz, 1H), 6.09-5.57 (m, 2H), 4.00-3.76 (m, 4H), 3.75-3.34 (m, 3H), 3.31 (s, 1H), 2.40-1.94 (m, 2H). | 509.20 |
| 1-(3-(4-amino-5-(4-(cyclopentanecarbonyl)phenyl)-7-methyl-7H-pyrrolo[2,3-d]pyrimidin-6-yl)pyrrolidin-1-yl)prop-2-en-1-one | 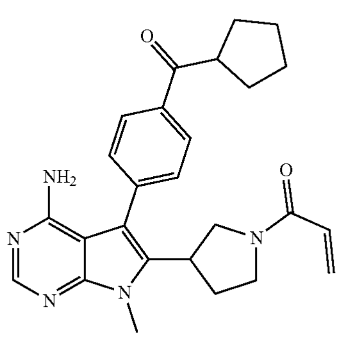 [SMILES: C=CC(=O)N1CCC(c2c(-c3ccc(C(=O)C4CCCC4)cc3)c3c(N)ncnc3n2C)C1] | $^1$H NMR (400 MHz, DMSO-d$_6$) δ 8.14 (d, J = 1.8 Hz, 1H), 8.06 (d, J = 7.9 Hz, 2H), 7.53 (d, J = 7.9 Hz, 2H), 6.55-6.35 (dd, J = 16.7, 10.3 Hz, 1H), 6.07 (ddd, J = 16.8, 7.0, 2.4 Hz, 1H), 5.63-5.58 (dd, J = 10.2, 2.5 Hz, 1H), 3.96-3.87 (m, 1H), 3.80 (d, J = 6.6 Hz, 4H), 3.77 (s, 1H), 3.68 (d, J = 8.9 Hz, 1H), 3.48 (t, J = 9.8 Hz, 1H), 3.27 (s, 1H), 2.21 (d, J = 7.3 Hz, 1H), 2.11 (s, 1H), 1.95 (s, 1H), 1.92 (d, J = 8.1 Hz, 1H), 1.80 (s, 2H), 1.64 (td, J = 8.4, 7.0, 4.9 Hz, 4H). | 444.20 |

TABLE 13-continued

Additional Exemplary Compounds

| Compound | Structure | Proton NMR | MS [M + 1] |
| --- | --- | --- | --- |
| 1-(5-(6-(1-acryloylpyrrolidin-3-yl)-4-amino-7-methyl-7H-pyrrolo[2,3-d]pyrimidin-5-yl)pyridin-2-yl)pyrrolidin-2-one | 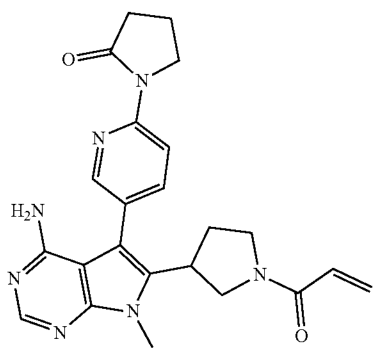 [SMILES: C=CC(=O)N1CCC(c2c(-c3ccc(N4CCCC4=O)nc3)c3c(N)ncnc3n2C)C1] | $^1$H NMR (400 MHz, DMSO-d$_6$) δ 8.39 (t, J = 6.8 Hz, 2H), 8.13 (d, J = 1.7 Hz, 1H), 7.86-7.78 (m, 1H), 6.47 (ddd, J = 32.7, 16.8, 10.3 Hz, 1H), 6.13-6.04 (m, 1H), 5.68-5.57 (m, 3H), 4.05-3.95 (t, J = 9.2 Hz, 3H), 3.79 (d, J = 6.8 Hz, 3H), 3.76-3.60 (m, 2H), 3.52 (dt, J = 16.6, 9.1 Hz, 2H), 3.27 (s, 1H), 2.61 (t, J = 8.0 Hz, 2H), 2.13-1.90 (m, 4H). | 432.35 |
| 1-(3-(4-amino-5-(4-(isoxazol-5-yl)phenyl)-7-methyl-7H-pyrrolo[2,3-d]pyrimidin-6-yl)pyrrolidin-1-yl)prop-2-en-1-one | 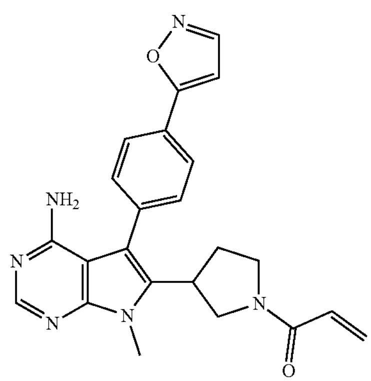 [SMILES: C=CC(=O)N1CCC(c2c(-c3ccc(-c4ccno4)cc3)c3c(N)ncnc3n2C)C1] | $^1$H NMR (400 MHz, DMSO-d$_6$) δ 8.70 (d, J = 1.9 Hz, 1H), 8.14 (d, J = 1.8 Hz, 1H), 7.97 (d, J = 8.1 Hz, 2H), 7.55 (d, J = 8.0 Hz, 2H), 7.10 (d, J = 2.0 Hz, 1H), 6.51-6.42 (dd, J = 16.8, 10.2 Hz, 1H), 6.11-6.01 (m, 1H), 5.63-5.53 (m, 1H), 3.95 (t, J = 9.1 Hz, 1H), 3.80 (d, J = 6.7 Hz, 4H), 3.69 (s, 1H), 3.57 (t, J = 9.6 Hz, 1H), 3.53 (s, 1H), 3.52-3.43 (m, 1H), 3.28 (d, J = 9.7 Hz, 1H), 2.21-1.97 (m, 2H). | 415.15 |
| 4-[(4-{4-amino-7-methyl-6-[1-(prop-2-enoyl)pyrrolidin-3-yl]-7H-pyrrolo[2,3-d]pyrimidin-5-yl}phenyl)methyl]morpholin-3-one | 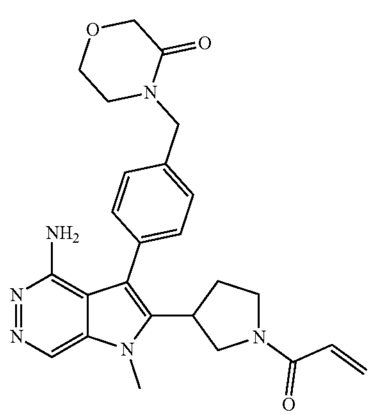 [SMILES: C=CC(=O)N1CCC(c2c(-c3ccc(CN4CCOCC4=O)cc3)c3c(N)nncc3n2C)C1] | 1H NMR (400 MHz, DMSO-d6) 8.12 (d, J = 2.2 Hz, 1H), 7.36 (qd, J = 8.2, 3.7 Hz, 4H), 6.51-6.39 (dd, J = 16.8, 10.3 Hz, 1H), 6.08 (dt, J = 16.8, 2.9 Hz, 1H), 5.84-5.47 (s, 2H), 4.63 (s, 2H), 4.15 (s, 2H), 3.94-3.83 (m, 2H), 3.84-3.62 (m, 5H), 3.54 (dt, J = 8.0, 5.6 Hz, 2H), 3.52-3.21 (m, 3H), 2.21-1.91 (m, 3H). | 461.30 |

TABLE 13-continued

Additional Exemplary Compounds

| Compound | Structure | Proton NMR | MS [M + 1] |
|---|---|---|---|
| 1-(3-(4-amino-5-(4-((5-chloropyrimidin-2-yl)oxy)phenyl)-7-methyl-7H-pyrrolo[2,3-d]pyrimidin-6-yl)pyrrolidin-1-yl)prop-2-en-1-one | 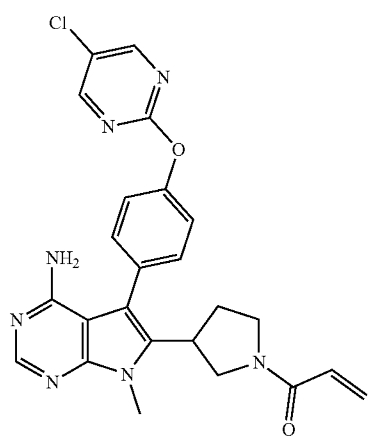 [SMILES: C=CC(=O)N1CCC(c2c(-c3ccc(Oc4ncc(Cl)cn4)cc3)c3c(N)ncnc3n2C)C1] | ¹H NMR (400 MHz, DMSO-d₆) δ 8.80 (d, J = 3.5 Hz, 2H), 8.13 (d, J = 1.7 Hz, 1H), 7.50-7.44 (m, 2H), 7.35 (d, J = 8.6 Hz, 2H), 6.51 (ddd, J = 33.8, 16.7, 10.3 Hz, 2H), 6.11 (ddd, J = 16.8, 5.5, 2.4 Hz, 1H), 5.74-5.44 (m, 3H), 4.01-3.91 (m, 1H), 3.80 (d, J = 6.8 Hz, 3H), 3.74-3.52 (m, 3H), 3.35 (d, J = 11.1 Hz, 1H), 2.20-2.04 (m, 2H). | 476.20 |
| 1-(3-(4-amino-5-(4-((5-chloropyridin-2-yl)oxy)phenyl)-7-methyl-7H-pyrrolo[2,3-d]pyrimidin-6-yl)pyrrolidin-1-yl)prop-2-en-1-one | 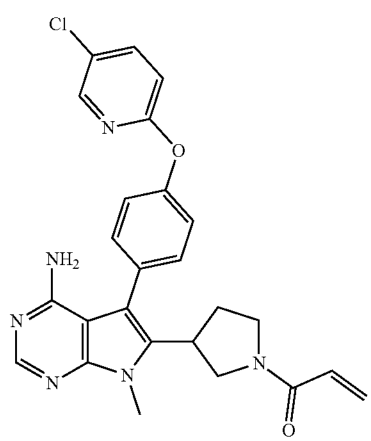 [SMILES: C=CC(=O)N1CCC(c2c(-c3ccc(Oc4ccc(Cl)cn4)cc3)c3c(N)ncnc3n2C)C1] | 1H NMR (400 MHz, DMSO-d6) δ 8.28 (dd, J = 7.5, 2.7 Hz, 1H), 8.13 (d, J = 2.2 Hz, 1H), 8.00 (dt, J = 8.8, 2.5 Hz, 1H), 7.47-7.37 (m, 2H), 7.25 (dd, J = 8.6, 3.1 Hz, 2H), 7.22-7.15 (m, 1H), 6.50 (ddd, J = 33.1, 16.8, 10.3 Hz, 1H), 6.11 (dt, J = 16.8, 2.3 Hz, 1H), 5.64 (td, J = 10.2, 2.5 Hz, 1H), 3.95 (t, J = 9.2 Hz, 1H), 3.84-3.68 (m, 5H), 3.62-3.47 (m, 2H), 2.28-1.91 (m, 2H). | 475.1 |
| 1-(3-(4-amino-5-(4-((5-chloro-6-methylpyridin-2-yl)oxy)phenyl)-7-methyl-7H-pyrrolo[2,3-d]pyrimidin-6-yl)pyrrolidin-1-yl)prop-2-en-1-one | 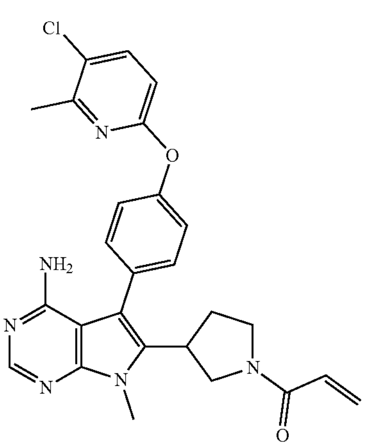 [SMILES: C=CC(=O)N1CCC(c2c(-c3ccc(Oc4ccc(Cl)c(C)n4)cc3)c3c(N)ncnc3n2C)C1] | 1H NMR (400 MHz, Chloroform-d) δ 8.32 (d, J = 2.5 Hz, 1H), 7.68 (dd, J = 8.6, 1.8 Hz, 1H), 7.38 (d, J = 7.8 Hz, 2H), 7.23 (t, J = 7.2 Hz, 2H), 6.80 (t, J = 8.6 Hz, 1H), 6.48-6.22 (m, 2H), 5.69 (ddd, J = 15.2, 9.2, 3.0 Hz, 1H), 4.87 (s, 1H), 4.02 (dd, J = 11.4, 7.2 Hz, 0H), 3.92-3.80 (m, 3H), 3.80-3.47 (m, 2H), 2.53 (d, J = 4.4 Hz, 3H), 2.25 (q, J = 7.2 Hz, 1H), 2.03 (s, 1H). | 490.2 |

| Compound | Structure | Proton NMR | MS [M + 1] |
|---|---|---|---|
| (R)-1-(3-(4-amino-7-methyl-5-(4-(6-methylpyridin-2-yl)oxy)phenyl)-7H-pyrrolo[2,3-d]pyrimidin-6-yl)pyrrolidin-1-yl)prop-2-en-1-one | 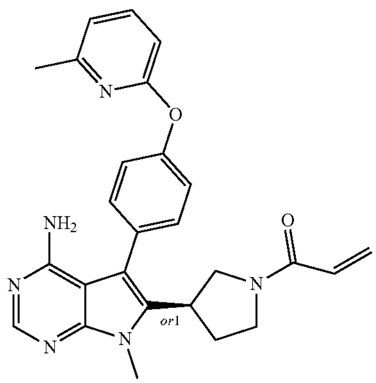 [SMILES: C=CC(=O)N1CC[C@@H](c2c(-c3ccc(Oc4cccc(C)n4)cc3)c3c(N)ncnc3n2C)C1] | $^1$H NMR (400 MHz, DMSO-d$_6$) δ 8.14 (d, J = 1.1 Hz, 1H), 7.79-7.72 (m, 1H), 7.45-7.39 (m, 2H), 7.20 (dd, J = 8.5, 3.7 Hz, 2H), 7.04 (d, J = 7.3 Hz, 1H), 6.84 (dd, J = 8.1, 4.2 Hz, 1H), 6.49 (ddd, J = 33.6, 16.8, 10.3 Hz, 1H), 6.10 (dt, J = 16.6, 2.0 Hz, 1H), 5.69-5.51 (m, 2H), 3.95 (t, J = 9.2 Hz, 1H), 3.80 (d, J = 6.5 Hz, 4H), 3.70-3.47 (m, 3H), 2.36 (d, J = 3.8 Hz, 3H), 2.27-1.93 (m, 2H). | 455.20 |
| (S)-1-(3-(4-amino-7-methyl-5-(4-(6-methylpyridin-2-yl)oxy)phenyl)-7H-pyrrolo[2,3-d]pyrimidin-6-yl)pyrrolidin-1-yl)prop-2-en-1-one | 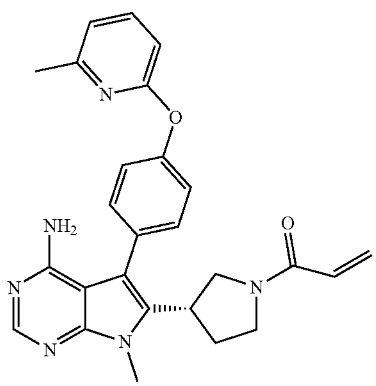 [SMILES: C=CC(=O)N1CC[C@H](c2c(-c3ccc(Oc4cccc(C)n4)cc3)c3c(N)ncnc3n2C)C1] | $^1$H NMR (400 MHz, DMSO-d$_6$) δ 8.12 (d, J = 2.0 Hz, 1H), 7.78-7.72 (m, 1H), 7.46-7.36 (m, 2H), 7.19 (dd, J = 8.6, 3.9 Hz, 2H), 7.04 (d, J = 7.4 Hz, 1H), 6.84 (dd, J = 8.1, 4.1 Hz, 1H), 6.49 (ddd, J = 33.2, 16.7, 10.2 Hz, 1H), 6.10 (dd, J = 16.7, 2.3 Hz, 1H), 5.63 (ddd, J = 10.8, 9.0, 2.4 Hz, 1H), 3.95 (t, J = 9.0 Hz, 1H), 3.79 (d, J = 6.8 Hz, 4H), 3.53 (dq, J = 18.8, 9.7 Hz, 2H), 2.36 (d, J = 3.8 Hz, 3H), 2.27-1.94 (m, 2H). | 455.20 |
| 1-(3-(4-amino-5-(4-((6-methylpyridin-2-yl)oxy)phenyl)-7H-pyrrolo[2,3-d]pyrimidin-6-yl)pyrrolidin-1-yl)prop-2-en-1-one | 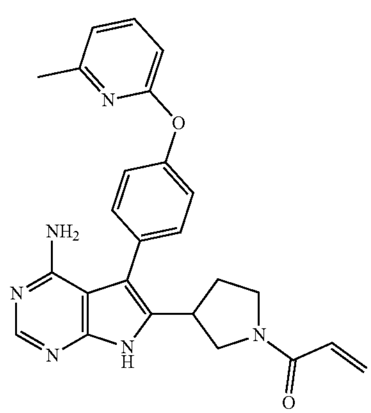 [SMILES: C=CC(=O)N1CCC(c2[nH]c3ncnc(N)c3c2-c2ccc(Oc3cccc(C)n3)cc2)C1] | $^1$H NMR (400 MHz, DMSO-d$_6$) δ 11.82 (d, J = 2.6 Hz, 1H), 8.09 (s, 1H), 7.76 (t, J = 7.8 Hz, 1H), 7.49-7.36 (m, 2H), 7.22 (dd, J = 8.5, 2.1 Hz, 2H), 7.04 (d, J = 7.4 Hz, 1H), 6.85 (d, J = 8.1 Hz, 1H), 6.58 (ddd, J = 16.7, 10.3, 3.8 Hz, 1H), 6.15 (dd, J = 16.7, 2.5 Hz, 1H), 5.67 (ddd, J = 10.6, 8.5, 2.5 Hz, 2H), 3.99 (t, J = 8.8 Hz, 1H), 3.89-3.77 (m, 1H), 3.77-3.60 (m, 1H), 3.54 (dt, J = 11.0, 5.4 Hz, 1H), 3.42 (d, J = 6.8 Hz, 1H), 2.37 (s, 3H), 2.36-2.07 (m, 2H). | 441.30 |

TABLE 13-continued

Additional Exemplary Compounds

| Compound | Structure | Proton NMR | MS [M + 1] |
|---|---|---|---|
| (S)-1-(3-(4-amino-5-(4-((6-methylpyridin-2-yl)oxy)phenyl)-7H-pyrrolo[2,3-d]pyrimidin-6-yl)pyrrolidin-1-yl)prop-2-en-1-one | 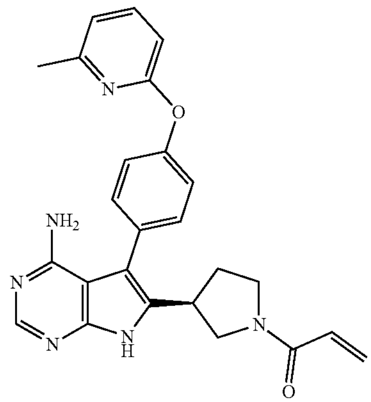 [SMILES: C=CC(=O)N1CC[C@H](c2[nH]c3ncnc(N)c3c2-c2ccc(Oc3cccc(C)n3)cc2)C1] | ¹H NMR (400 MHz, DMSO-d₆) δ 11.82 (s, 1H), 8.09 (s, 1H), 7.76 (t, J = 7.8 Hz, 1H), 7.43 (dd, J = 8.5, 3.5 Hz, 2H), 7.27-7.19 (m, 2H), 7.04 (d, J = 7.4 Hz, 1H), 6.85 (d, J = 8.1 Hz, 1H), 6.59 (ddd, J = 16.8, 10.3, 3.9 Hz, 1H), 6.15 (dd, J = 16.8, 2.5 Hz, 1H), 5.76 (s, 1H), 5.67 (ddd, J = 10.7, 8.5, 2.5 Hz, 1H), 4.06-3.78 (m, 1H), 3.77-3.60 (m, 1H), 3.54 (dt, J = 11.2, 5.4 Hz, 1H), 3.42 (d, J = 6.9 Hz, 1H), 2.37 (s, 3H), 2.37-2.10 (m, 2H). | 441.30 |
| (R)-1-(3-(4-amino-5-(4-((6-methylpyridin-2-yl)oxy)phenyl)-7H-pyrrolo[2,3-d]pyrimidin-6-yl)pyrrolidin-1-yl)prop-2-en-1-one | 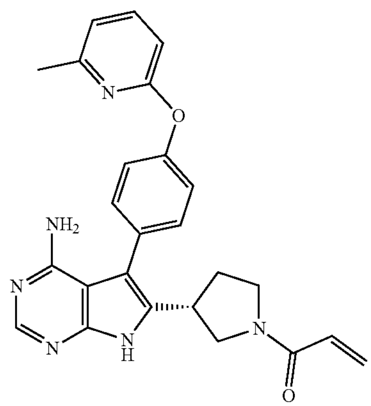 [SMILES: C=CC(=O)N1CC[C@@H](c2[nH]c3ncnc(N)c3c2-c2ccc(Oc3cccc(C)n3)cc2)C1] | ¹H NMR (400 MHz, DMSO-d₆) δ 11.92-11.73 (m, 1H), 8.09 (s, 1H), 7.76 (t, J = 7.8 Hz, 1H), 7.43 (dd, J = 8.4, 3.5 Hz, 2H), 7.27-7.16 (m, 2H), 7.04 (d, J = 7.4 Hz, 1H), 6.85 (d, J = 8.1 Hz, 1H), 6.58 (ddd, J = 16.8, 10.3, 3.8 Hz, 1H), 6.15 (dd, J = 16.7, 2.5 Hz, 1H), 5.90-5.75 (m, 2H), 5.67 (ddd, J = 10.6, 8.5, 2.5 Hz, 1H), 4.08-3.78 (m, 1H), 3.68 (dt, J = 28.8, 11.1 Hz, 1H), 3.55 (td, J = 10.7, 6.7 Hz, 1H), 3.50-3.39 (m, 1H), 2.37 (s, 3H), 2.30 (q, J = 8.9, 7.8 Hz, 0H), 2.23-2.08 (m, 1H). | 441.25 |
| 1-(3-(4-amino-7-methyl-5-(4-(piperidine-1-carbonyl)phenyl)-7H-pyrrolo[2,3-d]pyrimidin-6-yl)pyrrolidin-1-yl)prop-2-en-1-one | 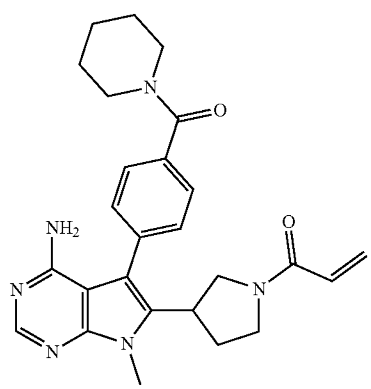 [SMILES: C=CC(=O)N1CCC(c2c(-c3ccc(C(=O)N4CCCCC4)cc3)c3c(N)ncnc3n2C)C1] | ¹H NMR (400 MHz, DMSO-d6) δ 8.13 (d, J = 2.8 Hz, 1H), 7.45 (d, J = 6.8 Hz, 4H), 6.46 (ddd, J = 40.4, 16.8, 10.4 Hz, 1H), 6.08 (dt, J = 16.8, 2.4 Hz, 1H), 5.62 (ddd, J = 12.9, 10.4, 2.4 Hz, 1H), 3.96-3.87 (m, 0H), 3.79 (d, J = 7.6 Hz, 3H), 3.69 (q, J = 8.2 Hz, 1H), 3.61-3.44 (m, 1H), 2.23 (s, 1H), 2.03 (ddt, J = 50.6, 20.8, 10.4 Hz, 2H), 1.67-1.61 (m, 2H), 1.54 (s, 5H). | 459.3 |
| 1-(3-(4-amino-5-(4-(pyrrolidine-1-carbonyl)phenyl)-7H-pyrrolo[2,3-d]pyrimidin-6-yl)pyrrolidin-1-yl)prop-2-en-1-one | 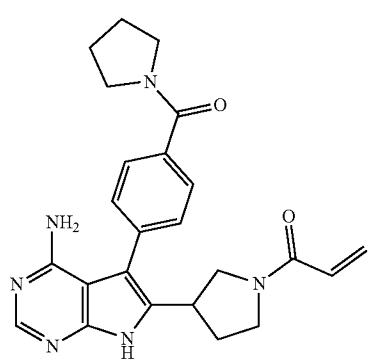 [SMILES: C=CC(=O)N1CCC(c2[nH]c3ncnc(N)c3c2-c2ccc(C(=O)N3CCCC3)cc2)C1] | ¹H NMR (400 MHz, DMSO-d₆) δ 11.88 (s, 1H), 8.10 (d, J = 1.0 Hz, 1H), 7.72-7.60 (m, 2H), 7.45 (dd, J = 8.1, 3.6 Hz, 2H), 6.58 (ddd, J = 16.7, 10.3, 4.3 Hz, 1H), 6.14 (dd, J = 16.7, 2.5 Hz, 1H), 5.67 (ddd, J = 10.8, 8.8, 2.5 Hz, 3H), 3.83 (q, J = 9.2 Hz, 1H), 3.76-3.59 (m, 1H), 3.59-3.38 (m, 6H), 2.39-2.05 (m, 2H), 1.86 (dq, J = 19.0, 6.8 Hz, 4H). | 431.15 |

TABLE 13-continued

Additional Exemplary Compounds

| Compound | Structure | Proton NMR | MS [M + 1] |
|---|---|---|---|
| 1-(3-(4-amino-5-(4-(pyrrolidine-1-carbonyl)phenyl)-7H-pyrrolo[2,3-d]pyrimidin-6-yl)pyrrolidin-1-yl)but-2-yn-1-one | 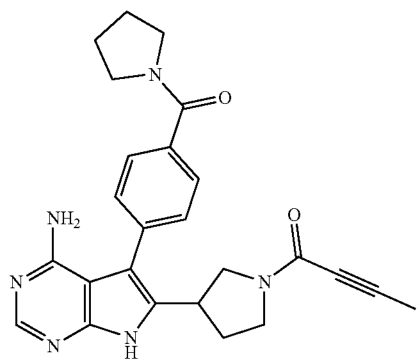 [SMILES: CC#CC(=O)N1CCC(c2[nH]c3ncnc(N)c3c2-c2ccc(C(=O)N3CCCC3)cc2)C1] | $^1$H NMR (400 MHz, DMSO-d$_6$) δ 12.02-11.71 (m, 1H), 8.10 (d, J = 22 Hz, 1H), 7.64 (dd, J = 7.9, 4.8 Hz, 2H), 7.44 (dd, J = 7.9, 5.7 Hz, 2H), 5.68 (d, J = 65.3 Hz, 2H), 3.98-3.80 (m, 1H), 3.77-3.58 (m, 2H), 3.50 (t, J = 6.7 Hz, 4H), 3.38 (d, J = 11.0 Hz, 1H), 3.28-3.20 (m, 1H), 2.35-2.11 (m, 2H), 2.02 (s, 1H), 1.98 (s, 2H), 1.87 (dq, J = 19.0, 6.7 Hz, 4H). | 443.25 |
| 1-(3-(4-amino-7-methyl-5-(4-(pyrrolidine-1-carbonyl)phenyl)-7H-pyrrolo[2,3-d]pyrimidin-6-yl)pyrrolidin-1-yl)but-2-yn-1-one | 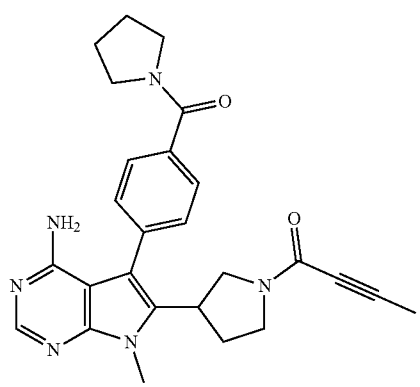 [SMILES: CC#CC(=O)N1CCC(c2c(-c3ccc(C(=O)N4CCCC4)cc3)c3c(N)ncnc3n2C)C1] | $^1$H NMR (400 MHz, Chloroform-d) δ 8.32 (d, J = 3.3 Hz, 1H), 7.68 (t, J = 9.1 Hz, 2H), 7.43 (d, J = 8.1 Hz, 2H), 4.86 (s, 2H), 3.99-3.82 (m, 5H), 3.69 (dt, J = 21.4, 8.0 Hz, 5H), 3.65-3.47 (m, 4H), 2.24-2.10 (m, 2H), 2.07-1.93 (m, 6H), 1.86 (s, 6H). | 457.35 |
| 1-(3-(4-amino-5-(4-((5-methylpyridin-2-yl)oxy)phenyl)-7H-pyrrolo[2,3-d]pyrimidin-6-yl)pyrrolidin-1-yl)prop-2-en-1-one | 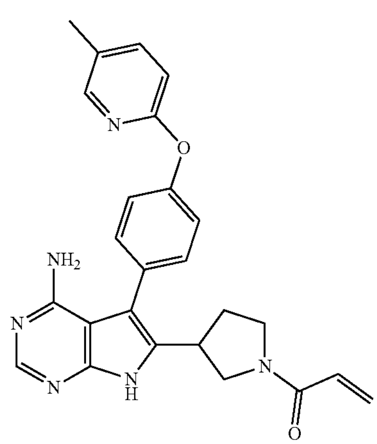 [SMILES: C=CC(=O)N1CCC(c2[nH]c3ncnc(N)c3c2-c2ccc(Oc3ccc(C)cn3)cc2)C1] | $^1$H NMR (400 MHz, DMSO-d$_6$) δ 11.82 (d, J = 2.5 Hz, 1H), 8.07 (dd, J = 19.5, 1.7 Hz, 2H), 7.71 (dd, J = 8.3, 2.5 Hz, 1H), 7.41 (dd, J = 8.5, 3.7 Hz, 2H), 7.24-7.16 (m, 2H), 7.02 (d, J = 8.3 Hz, 1H), 6.58 (ddd, J = 16.8, 10.3, 2.8 Hz, 1H), 6.15 (dd, J = 16.8, 2.5 Hz, 1H), 5.75 (s, 1H), 5.67 (ddd, J = 10.8, 8.7, 2.5 Hz, 2H), 3.99 (dd, J = 9.9, 7.9 Hz, 1H), 3.87-3.77 (m, 1H), 3.75-3.59 (m, 1H), 3.54 (tt, J = 12.8, 6.9 Hz, 1H), 3.41 (dd, J = 9.5, 6.1 Hz, 1H), 2.27 (s, 4H), 2.22-2.05 (m, 2H). | 441.15 |

TABLE 13-continued

Additional Exemplary Compounds

| Compound | Structure | Proton NMR | MS [M + 1] |
|---|---|---|---|
| 1-(3-{4-amino-5-[4-(azetidin-3-yloxy)phenyl]-7-methyl-7H-pyrrolo[2,3-d]pyrimidin-6-yl}pyrrolidin-1-yl)prop-2-en-1-one; trifluoroacetic acid salt | 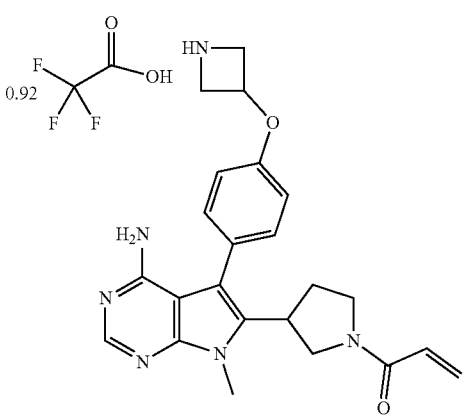 | $^1$H NMR (400 MHz, DMSO-d$_6$) δ 9.27 (d, J = 52.2 Hz, 2H), 8.58-8.34 (m, 1H), 7.35 (d, J = 8.3 Hz, 2H), 6.97 (d, J = 8.0 Hz, 2H), 6.44 (ddd, J = 53.6, 16.7, 10.3 Hz, 1H), 6.09 (ddd, J = 16.8, 4.6, 2.4 Hz, 1H), 5.64 (ddd, J = 13.9, 10.3, 2.4 Hz, 1H), 5.15 (t, J = 6.1 Hz, 1H), 4.50 (s, 2H), 4.07 (d, J = 10.2 Hz, 2H), 3.97-3.43 (m, 7H), 3.28 (dt, J = 12.0, 9.1 Hz, 1H), 2.31-1.85 (m, 2H). | 419.30 |
| N-(3-(4-amino-7-methyl-5-(4-((6-methylpyridin-2-yl)oxy)phenyl)-7H-pyrrolo[2,3-d]pyrimidin-6-yl)cyclopentyl)acrylamide | 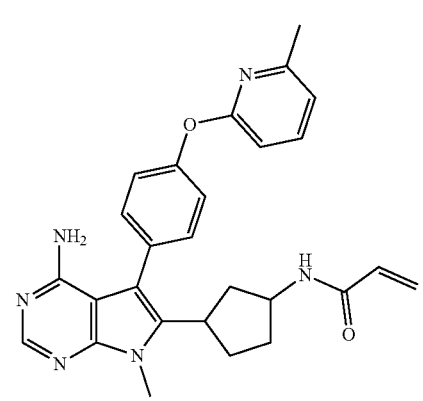 [SMILES: C=CC(=O)NC1CCC(c2c(-c3ccc(Oc4cccc(C)n4)cc3)c3c(N)ncnc3n2C)C1] | 1H NMR (400 MHz, DMSO-d6) δ 8.15 (d, J = 12.7 Hz, 2H), 7.77 (td, J = 7.7, 1.6 Hz, 1H), 7.39 (d, J = 8.3 Hz, 2H), 7.26-7.19 (m, 2H), 7.05 (d, J = 7.3 Hz, 1H), 6.85 (dd, J = 8.2, 4.6 Hz, 1H), 6.24-6.15 (m, 1H), 6.06 (dd, J = 17.1, 2.4 Hz, 1H), 5.56 (ddd, J = 10.0, 3.7, 2.4 Hz, 1H), 4.27-4.03 (m, 1H), 3.81 (d, J = 10.3 Hz, 3H), 3.65 (d, J = 43.2 Hz, 1H), 2.37 (s, 3H), 2.18 (s, 1H), 2.12-1.77 (m, 3H), 1.68 (q, J = 12.0 Hz, 1H), 1.62-1.48 (m, 1H). | 469 |
| N-(3-(4-amino-7-methyl-5-(4-((6-methylpyridin-2-yl)oxy)phenyl)-7H-pyrrolo[2,3-d]pyrimidin-6-yl)cyclopentyl)-N-methylacrylamide | 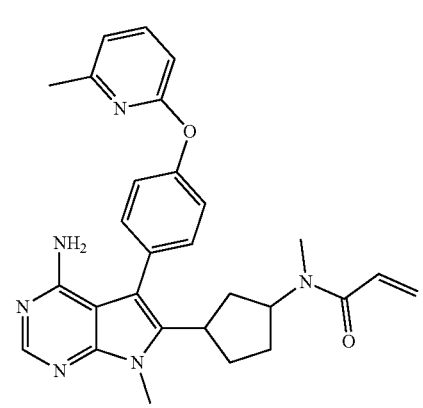 [SMILES: C=CC(=O)N(C)C1CCC(c2c(-c3ccc(Oc4cccc(C)n4)cc3)c3c(N)ncnc3n2C)C1] | $^1$H NMR (400 MHz, DMSO-d$_6$) δ 8.10 (s, 1H), 7.77 (t, J = 7.7 Hz, 1H), 7.43 (d, J = 7.9 Hz, 2H), 7.22 (d, J = 8.0 Hz, 2H), 7.04 (d, J = 7.4 Hz, 1H), 6.84 (d, J = 8.1 Hz, 1H), 6.06 (t, J = 15.7 Hz, 1H), 5.63 (s, 2H), 4.69 (d, J = 173.3 Hz, 1H), 3.78 (s, 3H), 3.43 (d, J = 10.4 Hz, 1H), 2.67 (d, J = 54.3 Hz, 3H), 2.35 (s, 3H), 2.11-1.50 (m, 6H). | 483.20 |

TABLE 13-continued

Additional Exemplary Compounds

| Compound | Structure | Proton NMR | MS [M + 1] |
|---|---|---|---|
| 1-((2R)-4-(4-amino-7-methyl-5-(4-((6-methylpyridin-2-yl)oxy)phenyl)-7H-pyrrolo[2,3-d]pyrimidin-6-yl)-2-(hydroxymethyl)pyrrolidin-1-yl)prop-2-en-1-one | 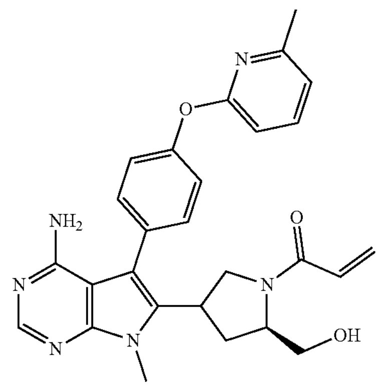 [SMILES: C=CC(=O)N1CC(c2c(-c3ccc(Oc4cccc(C)n4)cc3)c3c(N)ncnc3n2C)C[C@@H]1CO] | 1H NMR (400 MHz, DMSO-d6) δ 8.13 (s, 1H), 7.75 (t, J = 7.8 Hz, 1H), 7.42 (d, J = 8.6 Hz, 2H), 7.21 (d, J = 8.6 Hz, 2H), 7.03 (d, J = 7.2 Hz, 1H), 6.88-6.80 (m, 1H), 6.53 (dd, J = 16.4, 10.4 Hz, 1H), 6.11 (d, J = 17.0 Hz, 1H), 5.64 (dd, J = 10.4, 2.4 Hz, 1H), 4.07 (s, 1H), 3.98 (s, 1H), 3.82 (d, J = 7.4 Hz, 3H), 3.58-3.46 (m, 2H), 2.35 (s, 3H). | 485.22 |
| 1-(3-(4-amino-7-methyl-5-(4-((6-methylpyridin-2-yl)oxy)phenyl)-7H-pyrrolo[2,3-d]pyrimidin-6-yl)-4-(hydroxymethyl)pyrrolidin-1-yl)prop-2-en-1-one | 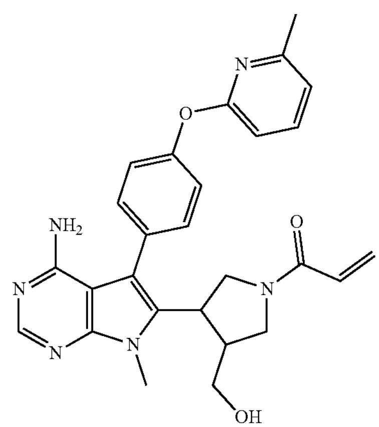 [SMILES: C=CC(=O)N1CC(CO)C(c2c(-c3ccc(Oc4cccc(C)n4)cc3)c3c(N)ncnc3n2C)C1] | ¹H NMR (400 MHz, DMSO-d₆) δ 8.11 (d, J = 1.2 Hz, 1H), 7.75 (td, J = 7.8, 3.3 Hz, 1H), 7.49-7.28 (m, 2H), 7.16 (ddd, J = 19.5, 8.4, 3.9 Hz, 2H), 7.04 (d, J = 7.3 Hz, 1H), 6.82 (dd, J = 8.1, 1.9 Hz, 1H), 6.42 (dd, J = 16.7, 10.3 Hz, 1H), 6.20 (dd, J = 16.8, 10.1 Hz, 1H), 6.04-5.58 (ddd, J = 10.2, 3.9, 2.5 Hz, 2H), 4.62 (dt, J = 15.6, 5.0 Hz, 1H), 3.95 (dq, J = 37.7, 8.1 Hz, 1H), 3.79 (s, 3H), 3.62 (ddd, J = 17.2, 11.4, 7.4 Hz, 1H), 3.52-3.35 (m, 1H), 3.18 (dq, J = 10.2, 5.1 Hz, 1H), 3.12-3.00 (m, 1H), 2.84-2.65 (m, 1H), 2.36 (d, J = 7.9 Hz, 3H), 2.08 (s, 2H). | 485.40 |
| 1-(3-(4-amino-7-methyl-5-(4-(methyl(tetrahydro-2H-pyran-4-yl)amino)phenyl)-7H-pyrrolo[2,3-d]pyrimidin-6-yl)pyrrolidin-1-yl)prop-2-en-1-one | 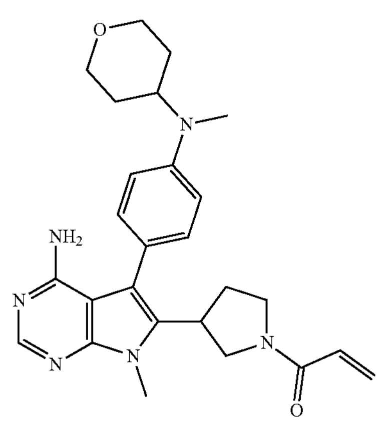 [SMILES: C=CC(=O)N1CCC(c2c(-c3ccc(N(C)C4CCOCC4)cc3)c3c(N)ncnc3n2C)C1] | ¹H NMR (400 MHz, DMSO-d₆) δ 8.11 (d, J = 2.0 Hz, 1H), 7.35 (q, J = 7.3, 6.7 Hz, 4H), 6.51 (dd, J = 16.8, 10.3 Hz, 1H), 6.38 (dd, J = 16.8, 10.3 Hz, 0H), 6.08 (ddd, J = 16.8, 10.2, 2.5 Hz, 1H), 5.71 (ddd, J = 18.2, 10.2, 2.5 Hz, 1H), 5.62 (ddd, J = 20.1, 10.2, 2.5 Hz, 1H), 4.01-3.93 (m, 2H), 3.93-3.84 (m, 1H), 3.79 (s, 2H), 3.77 (s, 2H), 3.76-3.59 (m, 1H), 3.58-3.44 (m, 2H), 3.43 (d, J = 2.8 Hz, 1H), 3.36-3.21 (m, 1H), 2.89-2.79 (m, 1H), 2.78 (d, J = 7.0 Hz, 3H), 2.10 (s, 1H), 2.08 (s, 1H), 1.97 (p, J = 10.9, 10.3 Hz, 1H), 1.72 (dq, J = 16.5, 12.6 Hz, 4H). | 461.35 |

TABLE 13-continued

Additional Exemplary Compounds

| Compound | Structure | Proton NMR | MS [M + 1] |
|---|---|---|---|
| 3-(4-amino-7-methyl-5-(4-(pyrrolidine-1-carbonyl)phenyl)-7H-pyrrolo[2,3-d]pyrimidin-6-yl)pyrrolidine-1-carbonitrile | 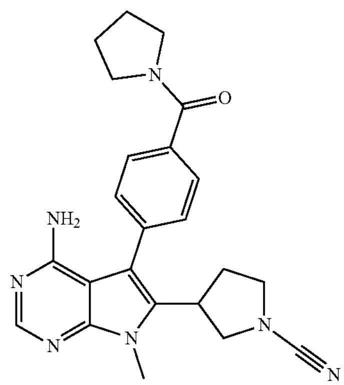 | ¹H NMR (400 MHz, DMSO-d₆) δ 8.13 (s, 1H), 7.67-7.60 (m, 2H), 7.48-7.41 (m, 2H), 5.59 (s, 2H), 3.79 (s, 3H), 3.73 (td, J = 9.2, 8.7, 6.9 Hz, 1H), 3.66 (t, J = 8.8 Hz, 1H), 3.55-3.42 (m, 5H), 3.46-3.33 (m, 2H), 2.15 (ddd, J = 14.4, 7.3, 4.8 Hz, 1H), 2.06-1.80 (m, 5H). | 416.20 |
| (S)-3-(4-amino-7-methyl-5-(4-(pyrrolidine-1-carbonyl)phenyl)-7H-pyrrolo[2,3-d]pyrimidin-6-yl)pyrrolidine-1-carbonitrile | 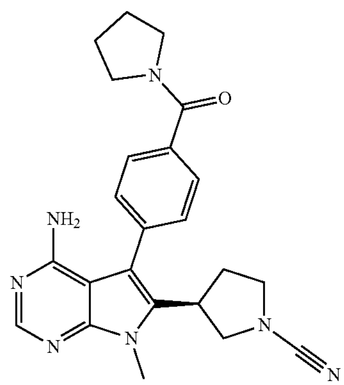 [SMILES: Cn1c([C@H]2CCN(C#N)C2)c(-c2ccc(C(=O)N3CCCC3)cc2)c2c(N)ncnc21] | ¹H NMR (400 MHz, DMSO-d₆) δ 8.13 (s, 1H), 7.67-7.60 (m, 2H), 7.48-7.41 (m, 2H), 5.59 (s, 2H), 3.79 (s, 3H), 3.73 (td, J = 9.2, 8.7, 6.9 Hz, 1H), 3.66 (t, J = 8.8 Hz, 1H), 3.55-3.42 (m, 5H), 3.46-3.33 (m, 2H), 2.15 (ddd, J = 14.4, 7.3, 4.8 Hz, 1H), 2.06-1.80 (m, 5H). | 416.20 |
| (R)-3-(4-amino-7-methyl-5-(4-(pyrrolidine-1-carbonyl)phenyl)-7H-pyrrolo[2,3-d]pyrimidin-6-yl)pyrrolidine-1-carbonitrile | 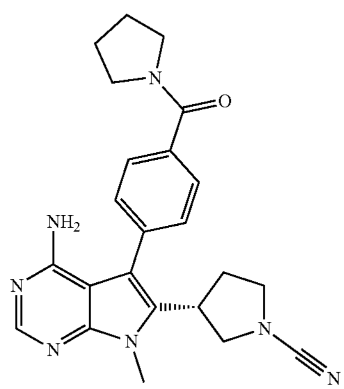 | ¹H NMR (400 MHz, DMSO-d₆) δ 8.13 (s, 1H), 7.67-7.60 (m, 2H), 7.48-7.41 (m, 2H), 5.59 (s, 2H), 3.79 (s, 3H), 3.73 (td, J = 9.2, 8.7, 6.9 Hz, 1H), 3.66 (t, J = 8.8 Hz, 1H), 3.55-3.42 (m, 5H), 3.46-3.33 (m, 2H), 2.15 (ddd, J = 14.4, 7.3, 4.8 Hz, 1H), 2.06-1.80 (m, 5H). | 416.20 |
| (4-(4-amino-7-methyl-6-(1-(vinylsulfonyl)pyrrolidin-3-yl)-7H-pyrrolo[2,3-d]pyrimidin-5-yl)phenyl)(pyrrolidin-1-yl)methanone | 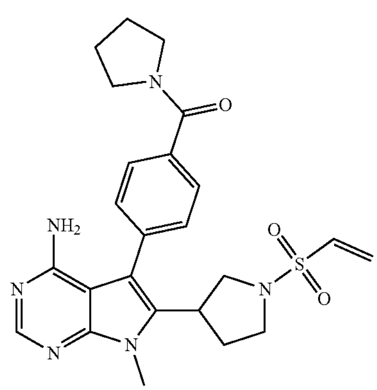 [SMILES: C=CS(=O)(=O)N1CCC(c2c(-c3ccc(C(=O)N4CCCC4)cc3)c3c(N)ncnc3n2C)C1] | ¹H NMR (400 MHz, DMSO-d₆) δ 8.12 (s, 1H), 7.66-7.59 (m, 2H), 7.46-7.40 (m, 2H), 6.74 (dd, J = 16.5, 10.0 Hz, 1H), 6.12 (d, J = 10.0 Hz, 1H), 6.04 (d, J = 16.5 Hz, 1H), 5.58 (s, 1H), 3.78 (s, 3H), 3.67 (q, J = 9.4, 8.9 Hz, 1H), 3.49 (ddd, J = 13.2, 8.5, 6.2 Hz, 5H), 3.32-3.25 (m, 1H), 3.18 (td, J = 10.0, 6.6 Hz, 1H), 3.10 (t, J = 10.1 Hz, 1H), 2.17 (dq, J = 12.8, 7.0, 6.2 Hz, 1H), 2.01-1.81 (m, 5H). | 481.20 |

TABLE 13-continued

Additional Exemplary Compounds

| Compound | Structure | Proton NMR | MS [M + 1] |
|---|---|---|---|
| (R)-(4-(4-amino-7-methyl-6-(1-(vinylsulfonyl)pyrrolidin-3-yl)-7H-pyrrolo[2,3-d]pyrimidin-5-yl)phenyl)(pyrrolidin-1-yl)methanone | 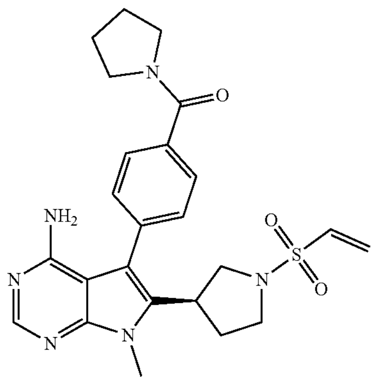 [SMILES: C=CS(=O)(=O)N1CC[C@@H](c2c(-c3ccc(C(=O)N4CCCC4)cc3)c3c(N)ncnc3n2C)C1] | $^1$H NMR (400 MHz, DMSO-d$_6$) δ 8.12 (s, 1H), 7.66-7.59 (m, 2H), 7.46-7.40 (m, 2H), 6.74 (dd, J = 16.5, 10.0 Hz, 1H), 6.12 (d, J = 10.0 Hz, 1H), 6.04 (d, J = 16.5 Hz, 1H), 5.58 (s, 1H), 3.78 (s, 3H), 3.67 (q, J = 9.4, 8.9 Hz, 1H), 3.49 (ddd, J = 13.2, 8.5, 6.2 Hz, 5H), 3.32-3.25 (m, 1H), 3.18 (td, J = 10.0, 6.6 Hz, 1H), 3.10 (t, J = 10.1 Hz, 1H), 2.17 (dq, J = 12.8, 7.0, 6.2 Hz, 1H), 2.01-1.81 (m, 5H). | 481.20 |
| (S)-(4-(4-amino-7-methyl-6-(1-(vinylsulfonyl)pyrrolidin-3-yl)-7H-pyrrolo[2,3-d]pyrimidin-5-yl)phenyl)(pyrrolidin-1-yl)methanone | 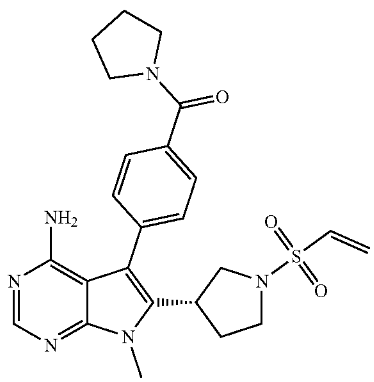 | $^1$H NMR (400 MHz, DMSO-d$_6$) δ 8.12 (s, 1H), 7.66-7.59 (m, 2H), 7.46-7.40 (m, 2H), 6.74 (dd, J = 16.5, 10.1 Hz, 1H), 6.12 (d, J = 10.0 Hz, 1H), 6.04 (d, J = 16.6 Hz, 1H), 5.60 (s, 1H), 3.78 (s, 3H), 3.67 (q, J = 9.9, 9.5 Hz, 1H), 3.49 (ddd, J = 13.2, 8.5, 6.3 Hz, 5H), 3.32-3.25 (m, 1H), 3.18 (td, J = 10.1, 6.7 Hz, 1H), 3.10 (t, J = 10.1 Hz, 1H), 2.17 (dt, J = 12.9, 7.1 Hz, 1H), 2.01-1.81 (m, 5H). | 481.20 |
| 1-((R)-3-(4-amino-7-methyl-5-((R)-4-(pyrrolidine-1-carbonyl)cyclohex-1-en-1-yl)-7H-pyrrolo[2,3-d]pyrimidin-6-yl)pyrrolidin-1-yl)prop-2-en-1-one | 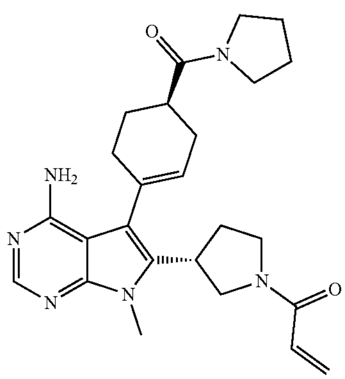 [SMILES: C=CC(=O)N1CC[C@@H](c2c(C3=CC[C@H](C(=O)N4CCCC4)CC3)c3c(N)ncnc3n2C)C1] | 1H NMR (400 MHz, DMSO-d6) δ 8.01 (s, 1H), 6.62 (dt, J = 16.7, 11.2 Hz, 1H), 6.46 (s, 1H), 6.17 (dt, J = 16.8, 2.5 Hz, 1H), 5.69 (td, J = 10.0, 2.6 Hz, 1H), 4.05-3.80 (m, 2H), 3.68 (d, J = 5.9 Hz, 5H), 3.61-3.44 (m, 3H), 3.43-3.36 (m, 1H), 3.30 (d, J = 6.9 Hz, 2H), 2.91 (s, 1H), 2.23 (q, J = 36.2, 32.0 Hz, 6H), 1.90 (p, J = 6.7 Hz, 3H), 1.79 (p, J = 6.8 Hz, 3H). | 449.25 |
| (S)-1-(3-(4-amino-7-methyl-5-(4-(pyrrolidine-1-carbonyl)cyclohex-1-en-1-yl)-7H-pyrrolo[2,3-d]pyrimidin-6-yl)-2,5-dihydro-1H-pyrrol-1-yl)prop-2-en-1-one | 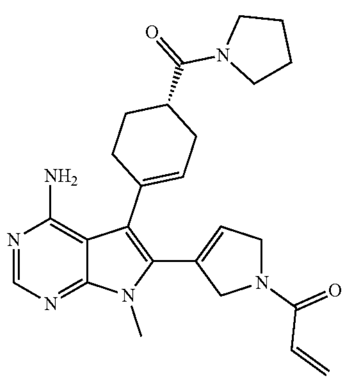 [SMILES: C=CC(=O)N1CC=C(c2c(C3=CC[C@@H](C(=O)N4CCCC4)CC3)c3c(N)ncnc3n2C)C1] | 1H NMR (400 MHz, DMSO-d6) δ 8.08 (s, 1H), 6.62 (dt, J = 17.4, 9.1 Hz, 3H), 6.21 (d, J = 16.1 Hz, 2H), 5.75 (d, J = 9.3 Hz, 2H), 4.53 (dd, J = 88.7, 39.5 Hz, 4H), 3.73 (s, 3H), 3.63-3.47 (m, 2H), 3.31 (s, 2H), 2.96 (d, J = 9.2 Hz, 1H), 2.30 (s, 2H), 2.17 (d, J = 7.2 Hz, 2H), 1.85 (dq, J = 36.4, 6.8 Hz, 6H). | 447.25 |

TABLE 13-continued

Additional Exemplary Compounds

| Compound | Structure | Proton NMR | MS [M + 1] |
|---|---|---|---|
| (R)-1-(3-(4-amino-7-methyl-5-(4-((4-methylpyrimidin-2-yl)oxy)phenyl)-7H-pyrrolo[2,3-d]pyrimidin-6-yl)pyrrolidin-1-yl)-2-chloroethan-1-one | 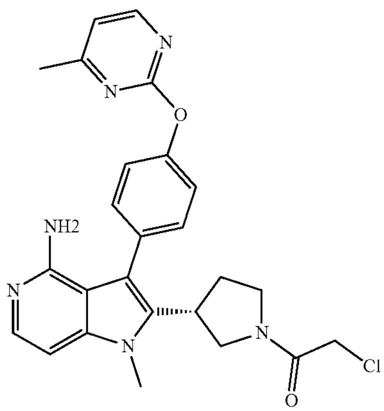 [SMILES: Cc1ccnc(Oc2ccc(-c3c([C@@H]4CCN(C(=O)CCl)C4)n(C)c4ccnc(N)c34)cc2)n1] | $^1$H NMR (400 MHz, DMSO-d$_6$) δ 8.49 (dd, J = 4.9, 3.1 Hz, 1H), 8.13 (d, J = 2.8 Hz, 1H), 7.44 (d, J = 8.0 Hz, 2H), 7.30 (d, J = 8.0 Hz, 2H), 7.18 (d, J = 5.0 Hz, 1H), 4.37-4.08 (m, 2H), 3.93-3.41 (m, 7H), 3.25 (s, 1H), 2.43 (s, 3H), 2.36-1.92 (m, 2H). | 478.25 |
| (R)-1-(3-(4-amino-7-methyl-5-(4-(pyrrolidine-1-carbonyl)cyclohex-1-en-1-yl)-7H-pyrrolo[2,3-d]pyrimidin-6-yl)-2,5-dihydro-1H-pyrrol-1-yl)prop-2-en-1-one | 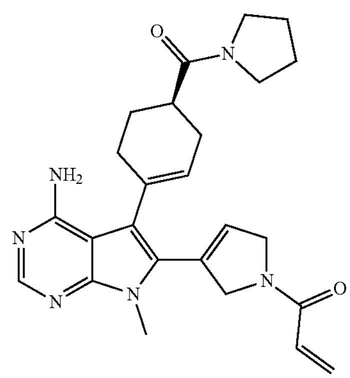 [SMILES: C=CC(=O)N1CC=C(c2c(C3=CC[C@H](C(=O)N4CCCC4)CC3)c3c(N)ncnc3n2C)C1] | 1H NMR (400 MHz, DMSO-d6) δ 8.08 (s, 1H), 6.62 (dt, J = 17.4, 9.1 Hz, 3H), 6.21 (d, J = 16.1 Hz, 2H), 5.75 (d, J = 9.3 Hz, 2H), 4.53 (dd, J = 88.7, 39.5 Hz, 4H), 3.73 (s, 3H), 3.63-3.47 (m, 2H), 3.31 (s, 2H), 2.96 (d, J = 9.2 Hz, 1H), 2.30 (s, 2H), 2.17 (d, J = 7.2 Hz, 2H), 1.85 (dq, J = 36.4, 6.8 Hz, 6H). | 447.25 |
| (S)-1-(3-(4-amino-7-methyl-5-(4-((4-methylpyrimidin-2-yl)oxy)phenyl)-7H-pyrrolo[2,3-d]pyrimidin-6-yl)pyrrolidin-1-yl)-2-chloroethan-1-one | 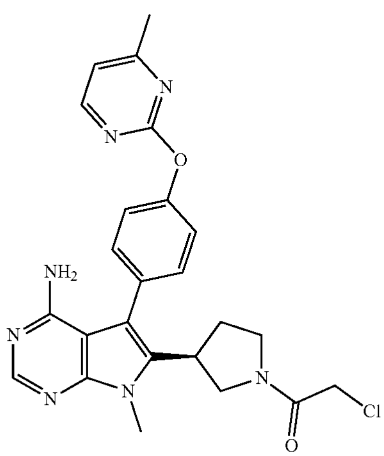 [SMILES: Cc1ccnc(Oc2ccc(-c3c([C@H]4CCN(C(=O)CCl)C4)n(C)c4ncnc(N)c34)cc2)n1] | $^1$H NMR (400 MHz, DMSO-d$_6$) δ 8.49 (dd, J = 5.0, 3.0 Hz, 1H), 8.13 (d, J = 2.8 Hz, 1H), 7.44 (d, J = 8.0 Hz, 2H), 7.30 (d, J = 7.8 Hz, 2H), 7.18 (d, J = 5.0 Hz, 1H), 5.60 (s, 1H), 4.37-4.09 (m, 2H), 3.66 (dd, J = 105.6, 8.9 Hz, 7H), 3.28 (d, J = 23.2 Hz, 1H), 2.43 (s, 3H), 2.31-1.96 (m, 2H). | 478.25 |

TABLE 13-continued

Additional Exemplary Compounds

| Compound | Structure | Proton NMR | MS [M + 1] |
|---|---|---|---|
| 1-((R)-3-(4-amino-7-methyl-5-((S)-4-(pyrrolidine-1-carbonyl)cyclohex-1-en-1-yl)-7H-pyrrolo[2,3-d]pyrimidin-6-yl)pyrrolidin-1-yl)prop-2-en-1-one | 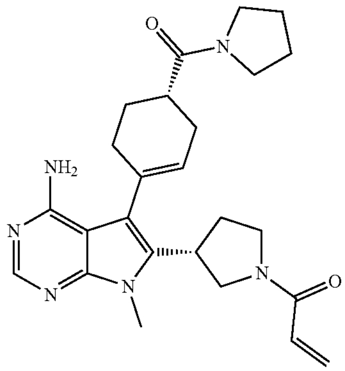 [SMILES: C=CC(=O)N1CC[C@@H](c2c(C3=CC[C@@H](C(=O)N4CCCC4)CC3)c3c(N)ncnc3n2C)C1] | 1H NMR (400 MHz, DMSO-d6) δ 8.01 (s, 1H), 6.62 (dt, J = 16.7, 11.2 Hz, 1H), 6.46 (s, 1H), 6.17 (dt, J = 16.8, 2.5 Hz, 1H), 5.69 (td, J = 10.0, 2.6 Hz, 1H), 4.05-3.80 (m, 2H), 3.68 (d, J = 5.9 Hz, 5H), 3.61-3.44 (m, 3H), 3.43-3.36 (m, 1H), 3.30 (d, J = 6.9 Hz, 2H), 2.91 (s, 1H), 2.23 (q, J = 36.2, 32.0 Hz, 6H), 1.90 (p, J = 6.7 Hz, 3H), 1.79 (p, J = 6.8 Hz, 3H). | 449.25 |
| 1-((S)-3-(4-amino-7-methyl-5-((S)-4-(pyrrolidine-1-carbonyl)cyclohex-1-en-1-yl)-7H-pyrrolo[2,3-d]pyrimidin-6-yl)pyrrolidin-1-yl)prop-2-en-1-one | 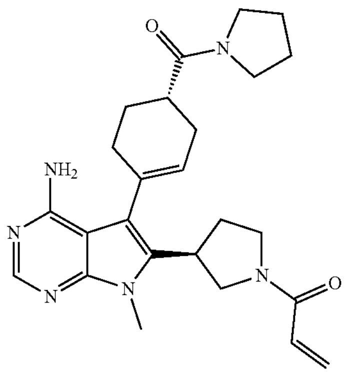 [SMILES: C=CC(=O)N1CC[C@H](c2c(C3=CC[C@@H](C(=O)N4CCCC4)CC3)c3c(N)ncnc3n2C)C1] | $^1$H NMR (400 MHz, DMSO-d$_6$) δ 8.01 (s, 1H), 6.63 (dd, J = 16.7, 10.3 Hz, 1H), 6.43 (s, 1H), 6.24-6.05 (m, 1H), 5.69 (dt, J = 8.9, 2.9 Hz, 2H), 3.99 (s, 1H), 3.68 (d, J = 7.9 Hz, 6H), 3.61-3.45 (m, 2H), 3.41 (d, J = 9.5 Hz, 1H), 3.31 (d, J = 9.9 Hz, 2H), 2.90 (s, 1H), 2.44-2.31 (m, 1H), 2.24 (d, J = 19.4 Hz, 3H), 2.11 (d, J = 18.0 Hz, 2H), 1.89 (q, J = 6.7, 6.2 Hz, 3H), 1.79 (p, J = 6.7 Hz, 2H). | 449.25 |
| 1-((S)-3-(4-amino-7-methyl-5-((R)-4-(pyrrolidine-1-carbonyl)cyclohex-1-en-1-yl)-7H-pyrrolo[2,3-d]pyrimidin-6-yl)pyrrolidin-1-yl)prop-2-en-1-one | 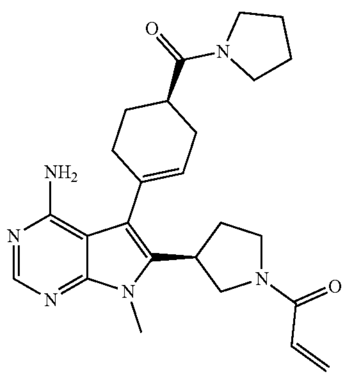 [SMILES: C=CC(=O)N1CC[C@H](c2c(C3=CC[C@H](C(=O)N4CCCC4)CC3)c3c(N)ncnc3n2C)C1] | $^1$H NMR (400 MHz, DMSO-d$_6$) δ 8.02 (s, 1H), 6.62 (dt, J = 16.6, 11.1 Hz, 1H), 6.45 (s, 1H), 6.17 (dt, J = 16.8, 2.6 Hz, 1H), 5.69 (td, J = 11.1, 10.0, 3.6 Hz, 2H), 4.12-3.36 (m, 10H), 3.30 (s, 1H), 2.91 (s, 1H), 2.47-1.95 (m, 6H), 1.85 (dq, J = 36.9, 6.8 Hz, 6H). | 449.30 |
| 1-[4-(4-amino-5-{3-methoxy-4-[(6-methylpyridin-2-yl)oxy]phenyl}-7-methyl-7H-pyrrolo[2,3-d]pyrimidin-6-yl)piperidin-1-yl]prop-2-en-1-one | 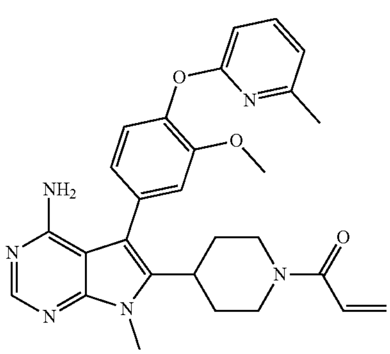 [SMILES: C=CC(=O)N1CCC(c2c(-c3ccc(Oc4cccc(C)n4)c(OC)c3)c3c(N)ncnc3n2C)CC1] | $^1$H NMR (400 MHz, DMSO-d$_6$) δ 8.10 (s, 1H), 7.68 (t, J = 7.7 Hz, 1H), 7.17 (d, J = 8.0 Hz, 1H), 7.10-7.05 (m, 1H), 6.94 (d, J = 7.3 Hz, 2H), 6.76 (dd, J = 16.7, 10.5 Hz, 1H), 6.64 (d, J = 8.2 Hz, 1H), 6.04 (dd, J = 16.7, 2.4 Hz, 1H), 5.61 (dd, J = 10.4, 2.5 Hz, 2H), 4.47 (s, 1H), 4.13-4.06 (m, 1H), 3.77 (s, 3H), 3.67 (s, 3H), 3.09 (s, 2H), 2.64 (s, 2H), 2.31 (s, 3H), 1.83 (s, 2H), 1.57 (s, 2H). | 498.587 |

TABLE 13-continued

Additional Exemplary Compounds

| Compound | Structure | Proton NMR | MS [M + 1] |
|---|---|---|---|
| N-((1r,4r)-4-(4-amino-5-(3-methoxy-4-(6-methylpyridin-2-yloxy)phenyl)-7-methyl-7H-pyrrolo[2,3-d]pyrimidin-6-yl)cyclohexyl)acrylamide | 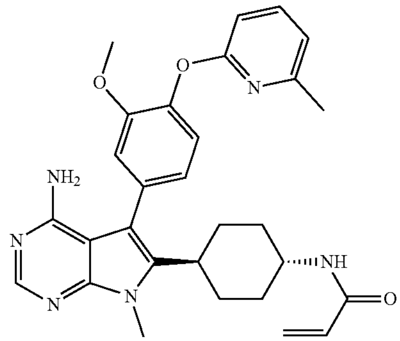 [SMILES: C=CC(=O)N[C@H]1CC[C@H](c2c(-c3ccc(Oc4cccc(C)n4)c(OC)c3)c3c(N)ncnc3n2C)CC1] | $^1$H NMR (400 MHz, Methanol-d$_4$) δ 8.11 (s, 1H), 7.71 (t, J = 7.8 Hz, 1H), 7.24 (d, J = 8.0 Hz, 1H), 7.13 (d, J = 2.0 Hz, 1H), 7.05 (dd, J = 8.0, 1.9 Hz, 1H), 6.97 (d, J = 7.3 Hz, 1H), 6.71 (d, J = 8.3 Hz, 1H), 6.22 (d, J = 6.0 Hz, 2H), 5.65 (t, J = 6.0 Hz, 1H), 4.60 (s, 1H), 3.87 (s, 3H), 3.78 (s, 3H), 3.70 (s, 1H), 2.98 (t, J = 12.5 Hz, 1H), 2.42 (s, 3H), 2.01 (d, J = 14.2 Hz, 2H), 1.94 (s, 2H), 1.81 (d, J = 12.7 Hz, 1H), 1.75 (d, J = 12.6 Hz, 1H), 1.45-1.29 (m, 2H). | 512.614 |
| N-((1s,4s)-4-(4-amino-5-(3-methoxy-4-(6-methylpyridin-2-yloxy)phenyl)-7-methyl-7H-pyrrolo[2,3-d]pyrimidin-6-yl)cyclohexyl)acrylamide | 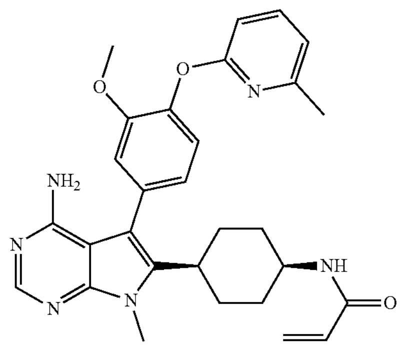 [SMILES: C=CC(=O)N[C@H]1CC[C@@H](c2c(-c3ccc(Oc4cccc(C)n4)c(OC)c3)c3c(N)ncnc3n2C)CC1] | $^1$H NMR (400 MHz, Methanol-d$_4$) δ 8.11 (s, 1H), 7.71 (t, J = 7.8 Hz, 1H), 7.24 (d, J = 8.0 Hz, 1H), 7.13 (d, J = 2.0 Hz, 1H), 7.05 (dd, J = 8.0, 1.9 Hz, 1H), 6.97 (d, J = 7.3 Hz, 1H), 6.71 (d, J = 8.3 Hz, 1H), 6.22 (d, J = 6.0 Hz, 2H), 5.65 (t, J = 6.0 Hz, 1H), 4.60 (s, 1H), 3.87 (s, 3H), 3.78 (s, 3H), 3.70 (s, 1H), 2.98 (t, J = 12.5 Hz, 1H), 2.42 (s, 3H), 2.01 (d, J = 14.2 Hz, 2H), 1.94 (s, 2H), 1.81 (d, J = 12.7 Hz, 1H), 1.75 (d, J = 12.6 Hz, 1H), 1.45-1.29 (m, 2H). | 512.614 |
| 1-[4-(4-amino-5-{3-methoxy-4-[(6-methylpyridin-2-yl)oxy]phenyl}-7-methyl-7H-pyrrolo[2,3-d]pyrimidin-6-yl)-1,2,3,6-tetrahydropyridin-1-yl]prop-2-en-1-one | 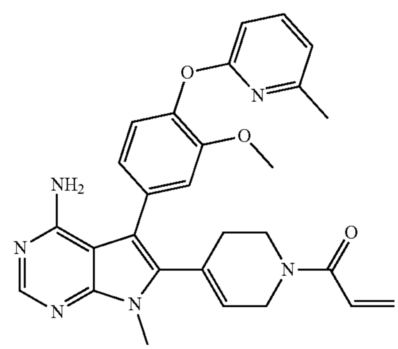 [SMILES: C=CC(=O)N1CC=C(c2c(-c3ccc(Oc4cccc(C)n4)c(OC)c3)c3c(N)ncnc3n2C)CC1] | $^1$H NMR (400 MHz, DMSO-d$_6$) δ 8.17 (s, 1H), 7.68 (t, J = 7.7 Hz, 1H), 7.17 (d, J = 8.0 Hz, 1H), 7.09 (d, J = 2.6 Hz, 1H), 6.95 (dd, J = 9.6, 7.6 Hz, 2H), 6.79 (ddd, J = 26.2, 16.7, 10.4 Hz, 1H), 6.67 (d, J = 8.2 Hz, 1H), 6.12 (dq, J = 16.7, 2.5 Hz, 1H), 6.05 (s, 2H), 5.73-5.64 (m, 1H), 4.25 (s, 1H), 4.16 (d, J = 3.3 Hz, 1H), 3.69-3.60 (m, 8H), 2.31 (s, 3H), 2.17 (d, J = 11.8 Hz, 2H). | 496.571 |
| N-(4-(4-amino-5-(3-methoxy-4-(6-methylpyridin-2-yloxy)phenyl)-7-methyl-7H-pyrrolo[2,3-d]pyrimidin-6-yl)cyclohex-3-enyl)acrylamide | 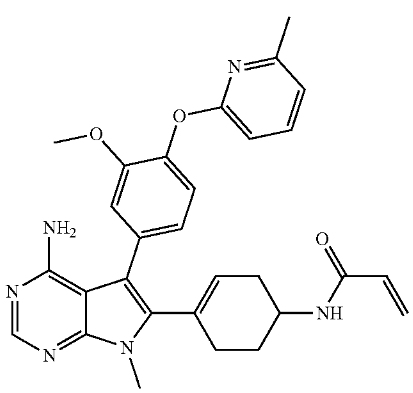 [SMILES: C=CC(=O)NC1CC=C(c2c(-c3ccc(Oc4cccc(C)n4)c(OC)c3)c3c(N)ncnc3n2C)CC1] | $^1$H NMR (400 MHz, DMSO-d$_6$) δ 8.16 (s, 1H), 8.08 (d, J = 7.6 Hz, 1H), 7.72-7.64 (m, 1H), 7.18 (d, J = 8.0 Hz, 1H), 7.11 (d, J = 1.9 Hz, 1H), 7.01-6.91 (m, 2H), 6.68 (d, J = 8.2 Hz, 1H), 6.22 (dd, J = 17.1, 10.0 Hz, 1H), 6.09 (dd, J = 17.1, 2.4 Hz, 2H), 5.86 (dt, J = 4.9, 2.4 Hz, 1H), 5.58 (dd, J = 10.0, 2.4 Hz, 1H), 3.93 (q, J = 8.9 Hz, 1H), 3.72 (s, 3H), 3.67 (s, 3H), 2.48-2.38 (m, 1H), 2.30 (s, 3H), 2.21 (d, J = 10.1 Hz, 1H), 2.13-2.01 (m, 2H), 1.87-1.79 (m, 1H), 1.52 (qd, J = 11.2, 5.2 Hz, 1H). | 510.598 |

TABLE 13-continued

Additional Exemplary Compounds

| Compound | Structure | Proton NMR | MS [M + 1] |
|---|---|---|---|
| 1-(3-(4-amino-7-methyl-5-(4-(6-methylpyridin-2-yloxy)phenyl)-7H-pyrrolo[2,3-d]pyrimidin-6-yl)pyrrolidin-1-yl)prop-2-en-1-one | 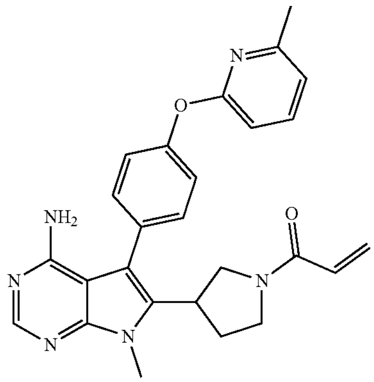 [SMILES: C=CC(=O)N1CCC(c2c(-c3ccc(Oc4cccc(C)n4)cc3)c3c(N)ncnc3n2C)C1] | $^1$H NMR (400 MHz, DMSO-$d_6$) δ 8.12 (d, J = 2.1 Hz, 1H), 7.80-7.71 (m, 1H), 7.45-7.38 (m, 2H), 7.19 (dd, J = 8.6, 3.9 Hz, 2H), 7.04 (d, J = 7.3 Hz, 1H), 6.84 (dd, J = 8.2, 4.1 Hz, 1H), 6.49 (ddd, J = 33.0, 16.8, 10.3 Hz, 1H), 6.10 (dt, J = 16.8, 1.9 Hz, 1H), 5.63 (ddd, J = 10.8, 8.9, 2.5 Hz, 2H), 4.00-3.91 (m, 1H), 3.79 (d, J = 6.8 Hz, 4H), 3.68 (t, J = 9.3 Hz, 1H), 3.53 (dq, J = 18.9, 9.5 Hz, 2H), 2.36 (d, J = 3.8 Hz, 3H), 2.28-2.20 (m, 1H), 2.17-1.93 (m, 1H). | 454.534 |
| N-(4-(4-amino-7-methyl-5-(4-(6-methylpyridin-2-yloxy)phenyl)-7H-pyrrolo[2,3-d]pyrimidin-6-yl)cyclohexyl)acrylamide | 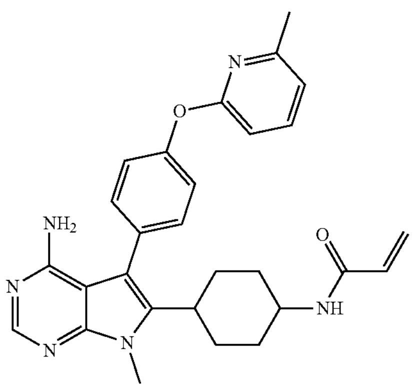 [SMILES: C=CC(=O)NC1CCC(c2c(-c3ccc(Oc4cccc(C)n4)cc3)c3c(N)ncnc3n2C)CC1] | $^1$H NMR (400 MHz, Chloroform-d) δ 8.25 (s, 1H), 7.67 (t, J = 7.7 Hz, 1H), 7.47-7.39 (m, 2H), 7.30-7.23 (m, 2H), 6.97 (d, J = 7.4 Hz, 1H), 6.81 (d, J = 8.1 Hz, 1H), 6.21 (dd, J = 16.9, 1.4 Hz, 1H), 5.97 (dd, J = 16.9, 10.3 Hz, 1H), 5.80-5.72 (m, 1H), 5.56 (dd, J = 10.3, 1.4 Hz, 1H), 5.36 (d, J = 7.2 Hz, 1H), 4.26-4.19 (m, 1H), 3.87 (s, 3H), 2.92 (dd, J = 16.9, 10.3 Hz, 1H), 2.44 (s, 3H), 1.94 (d, J = 11.5 Hz, 2H), 1.74 (d, J = 11.2 Hz, 2H). | 482.588 |

Example 15

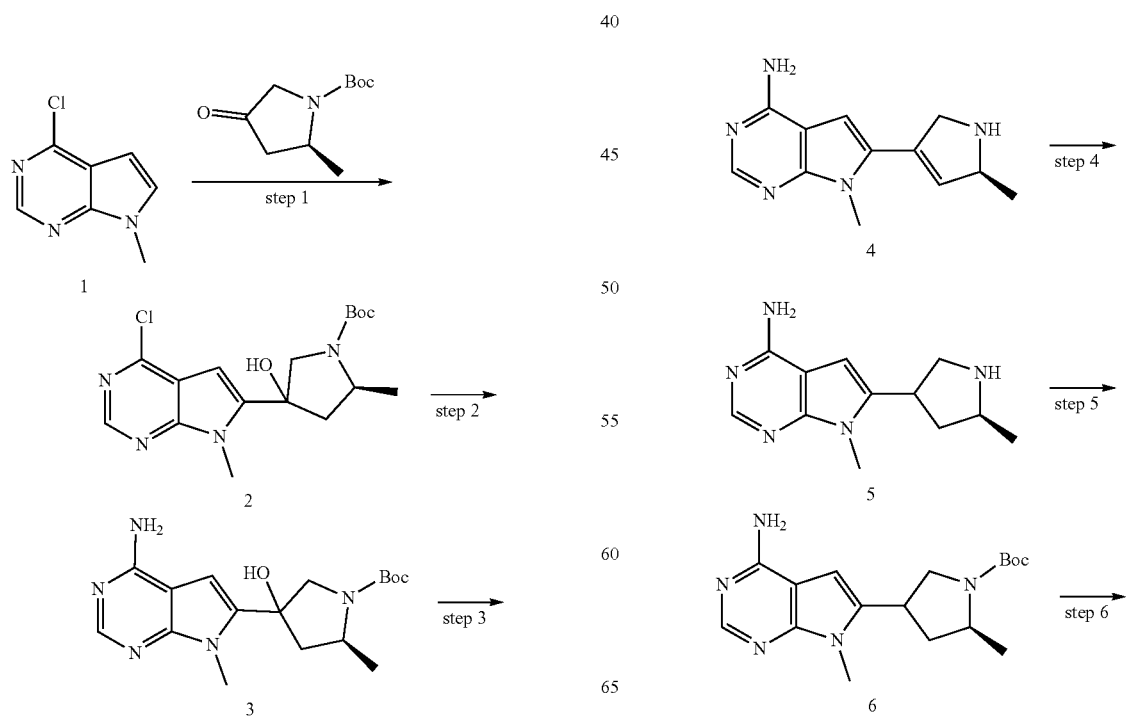

1595
-continued

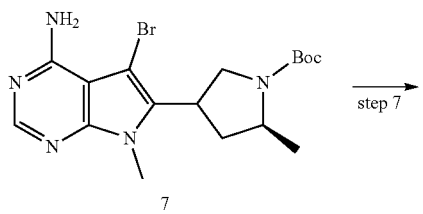

7

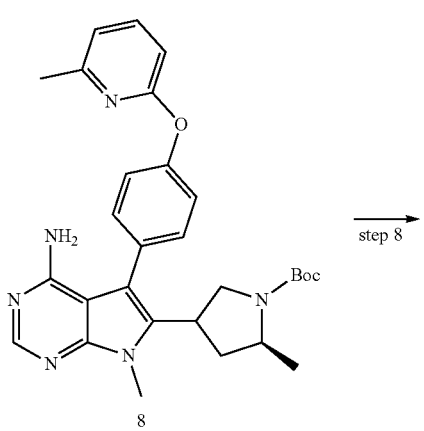

8

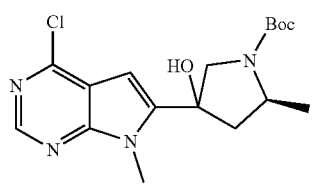 [SMILES: C[C@H]1CC(O)(c2cc3c(Cl)ncnc3n2C)CN1C(=O)OC(C)(C)C]

9

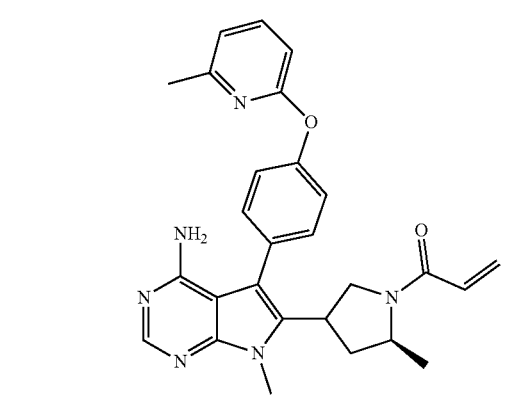

1596 tert-butyl (2S)-4-(4-chloro-7-methyl-7H-pyrrolo[2,3-d]pyrimidin-6-yl)-4-hydroxy-2-methylpyrrolidine-1-carboxylate

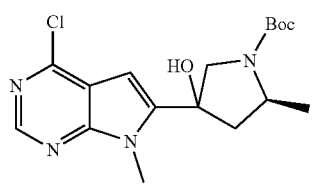 [SMILES: C[C@H]1CC(O)(c2cc3c(Cl)ncnc3n2C)CN1C(=O)OC(C)(C)C]

Step 1: A round bottomed flask was charged with 4-chloro-7-methyl-7H-pyrrolo[2,3-d]pyrimidine (1.7 g, 10.18 mmol), THF (30 mL) and a stir bar. LDA (7.63 mL, 15.26 mmol, 2M) was added dropwise the above solution at −78° C., after stirring for 1 h at same temperature, tert-butyl (S)-2-methyl-4-oxopyrrolidine-1-carboxylate (4.05 g, 20.35 mmol) in THF (10 mL) was added at −78° C., and the mixture was warmed to r.t. for 1 h. The mixture was quenched with Sat. NH4Cl (10 mL), and extracted with EtOAc(40 mL) for 3 times, the combine organic phases was washed with brine, dried over Na₂SO₄, and combined under reduced pressure. The resulting crude product was purified by silica gel chromatography (eluting with PE/EtOAc=2:1) to afford tert-butyl (2S)-4-(4-chloro-7-methyl-7H-pyrrolo[2,3-d]pyrimidin-6-yl)-4-hydroxy-2-methylpyrrolidine-1-carboxylate (550 mg, 1.50 mmol, 15%) as an off-white solid.

tert-butyl (2S)-4-(4-amino-7-methyl-7H-pyrrolo[2,3-d]pyrimidin-6-yl)-4-hydroxy methylpyrrolidine-1-carboxylate

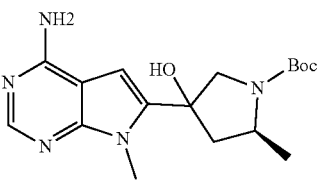 [SMILES: C[C@H]1CC(O)(c2cc3c(N)ncnc3n2C)CN1C(=O)OC(C)(C)C]

Step 2: Into a 50 mL unseal tube was charged with tert-butyl (2S)-4-(4-chloro-7-methyl-7H-pyrrolo[2,3-d]pyrimidin-6-yl)-4-hydroxy-2-methylpyrrolidine-1-carboxylate (550 mg, 1.50 mmol), NH3/H2O (10 mL, 25%~30%) and 1,4-dioxane (10 mL), sealed tube and the mixture solution was stirred at 100° C. for 12 h. The tube was cooled to r.t. and the mixture was poured out, the solvent was concentrated, the crude product was washed with DCM (100 mL) for 3 times, concentrated and afford tert-butyl (2S)-4-(4-amino-7-methyl-7H-pyrrolo[2,3-d]pyrimidin-6-yl)-4-hydroxy-2-methylpyrrolidine-1-carboxylate (400 mg, 77%) as off-white solid.

(S)-7-methyl-6-(5-methyl-2,5-dihydro-1H-pyrrol-3-yl)-7H-pyrrolo[2,3-d]pyrimidin-4-amine

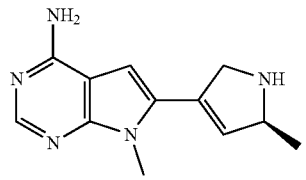 [SMILES: C[C@H]1C=C(c2cc3c(N)ncnc3n2C)CN1]

Step 3: A round bottomed flask was charged with tert-butyl (2S)-4-(4-amino-7-methyl-7H-pyrrolo[2,3-d]pyrimidin-6-yl)-4-hydroxy-2-methylpyrrolidine-1-carboxylate (380 mg, 1.09 mmol), HCl (5 mL) and a stir bar. The mixture was stirred at 100° C. for 2 h. After cooling to r. t., the resulting mixture was concentrated and diluted with water (10 mL), adjust pH to 7-8, and extracted with DCM (20 mL) for 3 times. The organic phase was combined and concentrated under reduced pressure to afford crude product (S)-7-methyl-6-(5-methyl-2,5-dihydro-1H-pyrrol-3-yl)-7H-pyrrolo[2,3-d]pyrimidin-4-amine (330 mg) as brown solid.

7-methyl-6-((5S)-5-methylpyrrolidin-3-yl)-7H-pyrrolo[2,3-d]pyrimidin-4-amine

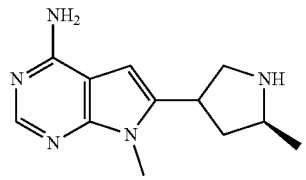 [SMILES: C[C@H]1CC(c2cc3c(N)ncnc3n2C)CN1]

Step 4: A resealable reaction via was charged with (S)-7-methyl-6-(5-methyl-2,5-dihydro-1H-pyrrol-3-yl)-7H-pyrrolo[2,3-d]pyrimidin-4-amine (330 mg, crude), Pd/C (30 mg) and MeOH (10 mL) and a stir bar. The mixture was evacuated and purged with nitrogen three times, then evacuated and purged with hydrogen five times. The mixture was stirred at 50° C. for overnight. Then the mixture was filtered, the filter cake was washed with MeOH for 5 times, concentrated the organic phase to afford 7-methyl-6-((5S)-5-methylpyrrolidin-3-yl)-7H-pyrrolo[2,3-d]pyrimidin-4-amine (220 mg, 63% for two steps) as brown solid.

tert-butyl (2S)-4-(4-amino-7-methyl-7H-pyrrolo[2,3-d]pyrimidin-6-yl)-2-methylpyrrolidine-1-carboxylate

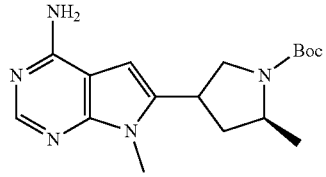 [SMILES: C[C@H]1CC(c2cc3c(N)ncnc3n2C)CN1C(=O)OC(C)(C)C]

Step 5: A round bottomed flask was charged with 7-methyl-6-((5S)-5-methylpyrrolidin-3-yl)-7H-pyrrolo[2,3-d]pyrimidin-4-amine (220 mg, 0.95 mmol), TEA (288 mg, 2.85 mmol) MeOH (5 mL) and a stir bar. Boc2O (308 mg, 1.42 mmol) was added, and the solution was stirred for 12 h at room temperature. The mixture was diluted with water (10 mL), extracted with DCM (50 mL) for 3 times. The organic phase was combined and washed with brine, dried over with $Na_2SO_4$, concentrated in vacuo, the crude product was purified by prep-TLC with DCM/MeOH (20:1) to afford tert-butyl (2S)-4-(4-amino-7-methyl-7H-pyrrolo[2,3-d]pyrimidin-6-yl)-2-methylpyrrolidine-1-carboxylate (190 mg, 60%) as brown solid.

tert-butyl (2S)-4-(4-amino-5-bromo-7-methyl-7H-pyrrolo[2,3-d]pyrimidin-6-yl)-2-methylpyrrolidine-1-carboxylate

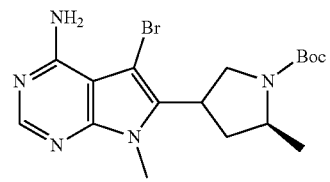 [SMILES: C[C@H]1CC(c2c(Br)c3c(N)ncnc3n2C)CN1C(=O)OC(C)(C)C]

Step 6: A round bottomed flask was charged with tert-butyl (2S)-4-{4-amino-7-methyl-7H-pyrrolo[2,3-d]pyrimidin-6-yl}-2-methylpyrrolidine-1-carboxylate (180 mg, 543 μmol), dimethylformamide (15 mL) and a stirbar. NBS (101 mg, 570 μmol), was added, and the solution was stirred at 0° C. for 1 h. The mixture was diluted with DCM (50 mL), washed with water and brine, dried with anhydrous $Na_2SO_4$, concentrated under recuded pressure, the crude product was purified by prep-TLC with DCM:MEOH (12:1) to afford tert-butyl (2S)-4-{4-amino-5-bromo-7-methyl-7H-pyrrolo[2,3-d]pyrimidin-6-yl}-2-methylpyrrolidine-1-carboxylate (200 mg, 85%) as brown solid.

tert-butyl (2S)-4-(4-amino-7-methyl-5-(4-((6-methylpyridin-2-yl)oxy)phenyl)-7H-pyrrolo[2,3-d]pyrimidin-6-yl)-2-methylpyrrolidine-1-carboxylate

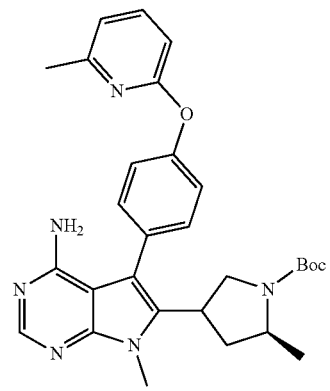 [SMILES: Cc1cccc(Oc2ccc(-c3c(C4C[C@H](C)N(C(=O)OC(C)(C)C)C4)n(C)c4ncnc(N)c34)cc2)n1]

Step 7: A resealable reaction via was charged with tert-butyl (2S)-4-{4-amino-5-bromo-7-methyl-7H-pyrrolo[2,3-d]pyrimidin-6-yl}-2-methylpyrrolidine-1-carboxylate (200 mg, 487 μmol), 2-methyl-6-[4-(4,4,5,5-tetramethyl-1,3,2-dioxaborolan-2-yl)phenoxy]pyridine (181 mg, 584 μmol), K3PO4 (309 mg, 1.46 mmol), Pd(DtBPF)Cl2 (47.5 mg, 73.0 μmol), and a stirbar before being evacuated and purged with nitrogen three times. DMF:water=16:1 (10 mL) was added, and the solution was stirred for 1 h at 90° C. The mixture was diluted with EtOAc (50 mL), washed with water and brine for 3 times respectively. The organic phase was dried with anhydrous Na₂SO₄, concentrated under reduced pressure. The crude product was purified by C18 flash chromatography to afford tert-butyl (2S)-4-(4-amino-7-methyl-5-{4-[(6-methylpyridin-2-yl)oxy]phenyl}-7H-pyrrolo[2,3-d]pyrimidin-6-yl)-2-methylpyrrolidine-1-carboxylate (140 mg, 56%) as light brown oil 7-methyl-5-(4-((6-methylpyridin-2-yl)oxy)phenyl)-6-((5S)-5-methylpyrrolidin-3-yl)-7H-pyrrolo[2,3-d]pyrimidin-4-amine

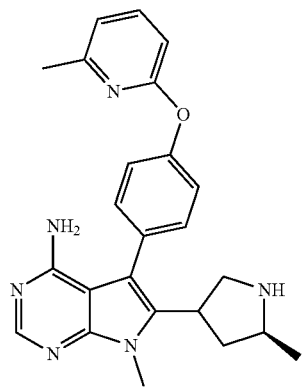 [SMILES: Cc1cccc(Oc2ccc(-c3c(C4CN[C@@H](C)C4)n(C)c4ncnc(N)c34)cc2)n1]

Step 8: A round bottomed flask was charged with tert-butyl (2S)-4-(4-amino-7-methyl-5-{4-[(6-methylpyridin-2-yl)oxy]phenyl}-7H-pyrrolo[2,3-d]pyrimidin-6-yl)-2-methylpyrrolidine-1-carboxylate (140 mg, 272 μmol), TFA/DCM (1:4 V/V, 15 mL) and a stirbar. The solution was stirred at r.t. for 3 h. The solvent was removed and the crude product was diluted with DCM and adjust pH to 7 with Na2CO3 aq. The organic phase was concentrated to afford 7-methyl-5-{4-[(6-methylpyridin-2-yl)oxy]phenyl}-6-[(5S)-5-methylpyrrolidin-3-yl]-7H-pyrrolo[2,3-d]pyrimidin-4-amine (90.0 mg, 100%) which was used to next step without purification.

1-((2S)-4-(4-amino-7-methyl-5-(4-((6-methylpyridin-2-yl)oxy)phenyl)-7H-pyrrolo[2,3-d]pyrimidin-6-yl)-2-methylpyrrolidin-1-yl)prop-2-en-1-one

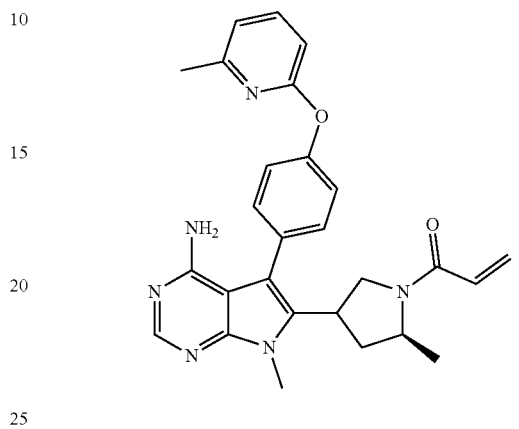

Step 9: A round bottomed flask was charged with TEA (65.7 mg, 651 μmol), prop-2-enoyl chloride (15.6 mg, 173 μmol), 7-methyl-5-{4-[(6-methylpyridin-2-yl)oxy]phenyl}-6-[(5S)-5-methylpyrrolidin-3-yl]-7H-pyrrolo[2,3-d]pyrimidin-4-amine (90.0 mg, 217 μmol) and a stirbar. Dichloromethane (5 mL) was added, and the solution was stirred at −65° C. for 0.5 h. The mixture was quenched with MeOH, and concentrated. The crude product was purified by prep-HPLC (Column: XBridge Shield RP18 OBD Column, 30*150 mm, 5 um; Mobile Phase A:Water(10 MMOL/L NH₄HCO₃), Mobile Phase B:ACN; Flow rate:60 mL/min; Gradient:25 B to 50 B in 8 min; 220 nm; RT1:7.23) to afford 1-[(2S)-4-(4-amino-7-methyl-5-{4-[(6-methylpyridin-2-yl)oxy]phenyl}-7H-pyrrolo[2,3-d]pyrimidin-6-yl)-2-methylpyrrolidin-1-yl]prop-2-en-1-one (38.3 mg, 38%) as white solid.

Additional compounds prepared according to the methods of Example 15 are depicted in Table 14 below.

TABLE 14

Additional Exemplary Compounds

| Compound | Structure | Proton NMR | MS [M + 1] |
|---|---|---|---|
| 1-((2R)-4-(4-amino-7-methyl-5-(4-((6-methylpyridin-2-yl)oxy)phenyl)-7H-pyrrolo[2,3-d]pyrimidin-6-yl)-2-methylpyrrolidin-1-yl)prop-2-en-1-one | 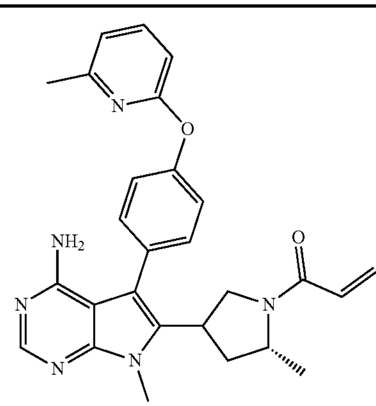 | ¹H NMR (400 MHz, DMSO-d₆) δ 8.11 (s, 1H), 7.75 (t, J = 7.8 Hz, 1H), 7.43 (d, J = 8.0 Hz, 2H), 7.22 (d, J = 8.1 Hz, 2H), 7.02 (d, J = 7.4 Hz, 1H), 6.83 (d, J = 8.2 Hz, 1H), 6.50 (dd, J = 16.7, 10.4 Hz, 1H), 6.11 (t, J = 15.2 Hz, 1H), 5.62 (d, J = 10.7 Hz, 1H), 4.00 (s, 2H), 3.79 (s, 3H), 3.47-3.34 (m, J = 2.8 Hz, 1H), 2.32 (s, 4H), 1.65 (d, J = 9.8 Hz, 1H), 1.24 (s, 1H), 1.12 (d, J = 6.6 Hz, 3H). | 469.40 |

TABLE 14-continued

Additional Exemplary Compounds

| Compound | Structure | Proton NMR | MS [M + 1] |
|---|---|---|---|
| 1-((2S)-4-(4-amino-7-methyl-5-(4-((6-methylpyridin-2-yl)oxy)phenyl)-7H-pyrrolo[2,3-d]pyrimidin-6-yl)-2-methylpyrrolidin-1-yl)prop-2-en-1-one | 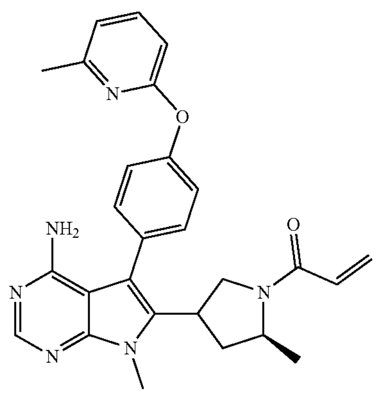 [SMILES: C=CC(=O)N1CC(c2c(-c3ccc(Oc4cccc(C)n4)cc3)c3c(N)ncnc3n2C)C[C@@H]1C] | $^1$H NMR (400 MHz, DMSO-d$_6$) δ 8.12 (s, 1H), 7.75 (t, J = 7.8 Hz, 1H), 7.44 (d, J = 8.1 Hz, 2H), 7.27-7.18 (m, 2H), 7.03 (d = 7.3 Hz, 1H), 6.83 (d, J = 8.2 Hz, 1H), 6.64-6.43 (m, 1H), 6.17-6.07 (m, 1H), 5.75-5.38 (m, 2H), 4.24-3.94 (m, 2H), 3.79 (d, J = 3.8 Hz, 3H), 3.68-3.36 (m, 2H), 2.34-2.32 (m, 4H), 1.81-1.60 (m, 1H), 1.22-1.06 (m, 3H). | 469.20 |
| 1-(3-(4-amino-7-methyl-5-(4-((6-methylpyridin-2-yl)oxy)phenyl)-7H-pyrrolo[2,3-d]pyrimidin-6-yl)-2,2-dimethylpyrrolidin-1-yl)prop-2-en-1-one | 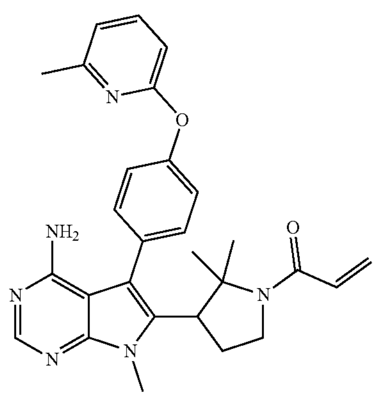 [SMILES: C=CC(=O)N1CCC(c2c(-c3ccc(Oc4cccc(C)n4)cc3)c3c(N)ncnc3n2C)C1(C)C] | $^1$H NMR (400 MHz, DMSO-d$_6$) δ 8.11 (s, 1H), 7.76 (t, J = 7.7 Hz, 1H), 7.43 (d, J = 8.0 Hz, 1H), 7.38 (d, J = 8.2 Hz, 1H), 7.17 (t, J = 8.8 Hz, 2H), 7.03 (d, J = 7.4 Hz, 1H), 6.85 (d, J = 8.2 Hz, 1H), 6.42 (dd, J = 16.5, 10.4 Hz, 1H), 6.03 (d, J = 16.6 Hz, 1H), 5.52 (d, J = 10.3 Hz, 1H), 3.80 (s, 3H), 3.61 (t, J = 8.6 Hz, 1H), 3.59 (s, 1H), 2.33 (s, 3H), 2.15 (s, 2H), 1.46 (s, 3H), 1.16 (s, 4H). | 483.40 |
| (R)-1-(3-(4-amino-7-methyl-5-(4-((6-methylpyridin-2-yl)oxy)phenyl)-7H-pyrrolo[2,3-d]pyrimidin-6-yl)-2-methyl-2,5-dihydro-1H-pyrrol-1-yl)-2-methylprop-2-en-1-one | 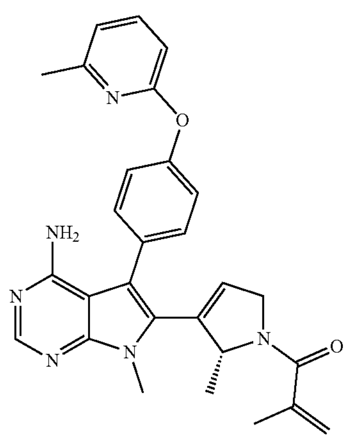 [SMILES: C=C(C)C(=O)N1CC=C(c2c(-c3ccc(Oc4cccc(C)n4)cc3)c3c(N)ncnc3n2C)[C@H]1C] | $^1$H NMR (400 MHz, DMSO-d$_6$) δ 8.19 (s, 1H), 7.76 (dt, J = 12.1, 7.7 Hz, 1H), 7.44-7.37 (m, 2H), 7.23 (t, J = 5.3 Hz, 2H), 7.04 (t, J = 8.5 Hz, 1H), 6.82 (t, J = 9.7 Hz, 1H), 6.25 (d, J = 57.7 Hz, 1H), 5.94 (s, 2H), 5.33-4.74 (m, 2H), 4.57-4.19 (m, 3H), 3.75 (d, J = 4.7 Hz, 3H), 2.37 (s, 3H), 1.84 (s, 2H), 1.73 (s, 1H), 1.21 (d, J = 27.1 Hz, 1H), 0.96 (dd, J = 25.8, 6.3 Hz, 3H). | 481.25 |

TABLE 14-continued

Additional Exemplary Compounds

| Compound | Structure | Proton NMR | MS [M + 1] |
|---|---|---|---|
| (S)-1-(3-(4-amino-7-methyl-5-(4-((6-methylpyridin-2-yl)oxy)phenyl)-7H-pyrrolo[2,3-d]pyrimidin-6-yl)-2-methyl-2,5-dihydro-1H-pyrrol-1-yl)-2-methylprop-2-en-1-one | 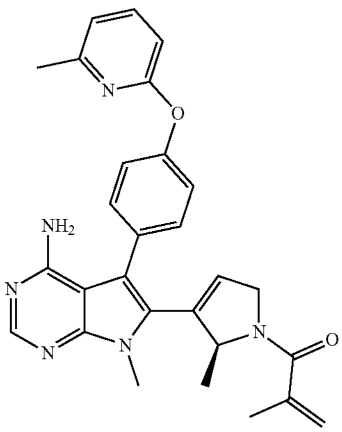 [SMILES: C=C(C)C(=O)N1CC=C(c2c(-c3ccc(Oc4cccc(C)n4)cc3)c3c(N)ncnc3n2C)[C@@H]1C] | $^1$H NMR (400 MHz, DMSO-d$_6$) δ 8.18 (s, 1H), 7.76 (dt, J = 12.1, 7.8 Hz, 1H), 7.44-7.37 (m, 2H), 7.23 (dd, J = 8.8, 3.0 Hz, 2H), 7.04 (t, J = 8.5 Hz, 1H), 6.82 (t, J = 9.7 Hz, 1H), 6.24 (d, J = 57.7 Hz, 1H), 5.94 (s, 2H), 5.31-4.75 (m, 2H), 4.60-4.17 (m, 3H), 3.75 (d, J = 5.0 Hz, 3H), 2.37 (s, 3H), 1.79 (d, J = 45.3 Hz, 3H), 0.96 (dd, J = 26.0, 6.3 Hz, 3H). | 481.25 |
| (R)-1-(3-(4-amino-7-methyl-5-(4-((6-methylpyridin-2-yl)oxy)phenyl)-7H-pyrrolo[2,3-d]pyrimidin-6-yl)-2-methyl-2,5-dihydro-1H-pyrrol-1-yl)prop-2-en-1-one | 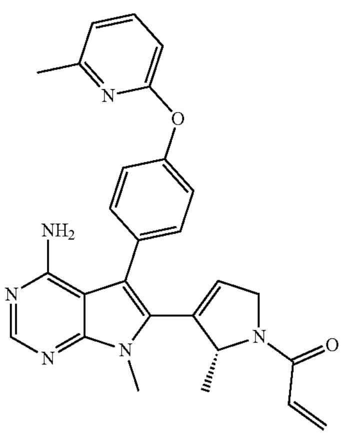 [SMILES: C=CC(=O)N1CC=C(c2c(-c3ccc(Oc4cccc(C)n4)cc3)c3c(N)ncnc3n2C)[C@H]1C] | $^1$H NMR (400 MHz, DMSO-d$_6$) δ 8.19 (d, J = 2.0 Hz, 1H), 7.75 (t, J = 7.7 Hz, 1H), 7.41 (t, J = 8.0 Hz, 2H), 7.22 (dd, J = 8.8, 2.3 Hz, 2H), 7.03 (d, J = 7.4 Hz, 1H), 6.80 (d, J = 8.1 Hz, 1H), 6.60-6.22 (m, 2H), 6.15 (ddd, J = 16.8, 5.1, 2.5 Hz, 1H), 5.97 (s, 2H), 5.66 (ddd, J = 22.4, 10.1, 2.5 Hz, 1H), 4.60-4.15 (m, 3H), 3.75 (d, J = 4.6 Hz, 3H), 2.36 (d, J = 8.8 Hz, 3H), 1.01 (dd, J = 6.2, 4.3 Hz, 3H). | 467.25 |
| (S)-1-(3-(4-amino-7-methyl-5-(4-((6-methylpyridin-2-yl)oxy)phenyl)-7H-pyrrolo[2,3-d]pyrimidin-6-yl)-2-methyl-2,5-dihydro-1H-pyrrol-1-yl)prop-2-en-1-one | 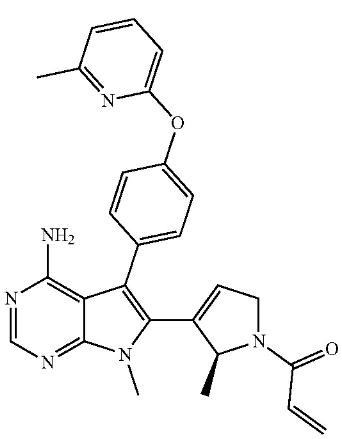 [SMILES: C=CC(=O)N1CC=C(c2c(-c3ccc(Oc4cccc(C)n4)cc3)c3c(N)ncnc3n2C)[C@@H]1C] | $^1$H NMR (400 MHz, DMSO-d$_6$) δ 8.19 (d, J = 2.0 Hz, 1H), 7.75 (t, J = 7.7 Hz, 1H), 7.41 (t, J = 8.0 Hz, 2H), 7.22 (dd, J = 8.8, 2.3 Hz, 2H), 7.03 (d, J = 7.3 Hz, 1H), 6.80 (d, J = 8.1 Hz, 1H), 6.55 (dd, J = 16.7, 10.3 Hz, 1H), 6.35-5.84 (m, 3H), 5.66 (ddd, J = 22.4, 10.2, 2.5 Hz, 1H), 4.60-4.14 (m, 3H), 3.75 (d, J = 4.6 Hz, 3H), 2.36 (d, J = 8.8 Hz, 3H), 1.01 (dd, J = 6.2, 4.4 Hz, 3H). | 467.15 |

TABLE 14-continued

Additional Exemplary Compounds

| Compound | Structure | Proton NMR | MS [M + 1] |
|---|---|---|---|
| 1-((2R,3R)-3-(4-amino-7-methyl-5-(4-((6-methylpyridin-2-yl)oxy)phenyl)-7H-pyrrolo[2,3-d]pyrimidin-6-yl)-2-methylpyrrolidin-1-yl)prop-2-en-1-one | 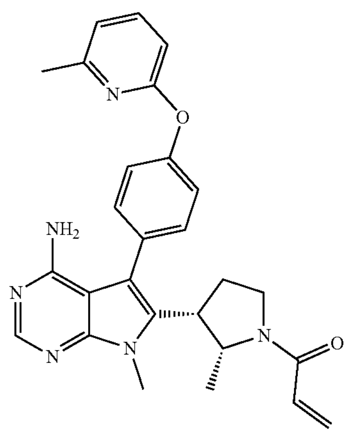 [SMILES: C=CC(=O)N1CC[C@@H](c2c(-c3ccc(Oc4cccc(C)n4)cc3)c3c(N)ncnc3n2C)[C@H]1C] | ¹H NMR (400 MHz, DMSO-d₆) δ 8.11 (d, J = 0.9 Hz, 1H), 7.77 (t, J = 7.7 Hz, 1H), 7.40 (td, J = 5.7, 2.7 Hz, 2H), 7.19 (tt, J = 8.2, 2.2 Hz, 2H), 7.04 (dd, J = 7.4, 2.1 Hz, 1H), 6.85 (d, J = 8.1 Hz, 1H), 6.71 (dd, J = 16.6, 10.3 Hz, 1H), 6.51 (dd, J = 16.7, 10.3 Hz, 1H), 6.15-5.43 (ddd, J = 16.8, 12.1, 2.5 Hz, 2H), 4.55 (dp, J = 31.3, 6.6 Hz, 1H), 3.89-3.62 (m, 5H), 3.42-3.33 (m, 1H), 2.35 (d, J = 3.6 Hz, 3H), 1.85 (dtd, J = 22.6, 12.4, 6.1 Hz, 2H), 0.83 (d, J = 6.5 Hz, 3H). | 469.20 |
| 1-((2S,3S)-3-(4-amino-7-methyl-5-(4-((6-methylpyridin-2-yl)oxy)phenyl)-7H-pyrrolo[2,3-d]pyrimidin-6-yl)-2-methylpyrrolidin-1-yl)prop-2-en-1-one | 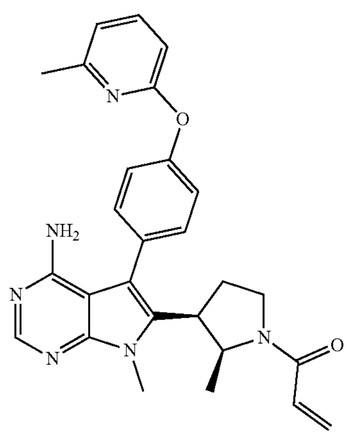 [SMILES: C=CC(=O)N1CC[C@H](c2c(-c3ccc(Oc4cccc(C)n4)cc3)c3c(N)ncnc3n2C)[C@@H]1C] | ¹H NMR (400 MHz, DMSO-d₆) δ 8.22 (s, 1H), 7.65 (t, J = 7.8 Hz, 1H), 7.43 (t, J = 3.9 Hz, 1H), 7.41-7.30 (m, 2H), 7.07 (dd, J = 8.1, 1.0 Hz, 1H), 7.00 (d, J = 2.0 Hz, 1H), 6.92 (d, J = 7.3 Hz, 1H), 6.81 (dd, J = 8.0, 1.6 Hz, 1H), 6.67 (ddt, J = 21.6, 8.0, 4.6 Hz, 2H), 6.23 (dt, J = 16.8, 2.2 Hz, 1H), 6.05 (s, 1H), 5.76 (ddd, J = 10.3, 3.7, 2.3 Hz, 1H), 5.00 (s, 1H), 4.95 (s, 1H), 4.73 (d, J = 17.7 Hz, 2H), 3.62 (d, J = 1.7 Hz, 3H), 3.56 (s, 3H), 2.29 (d, J = 3.6 Hz, 3H). | 533.40 |
| (S)-1-(4-(4-amino-7-methyl-5-(4-(pyrrolidine-1-carbonyl)phenyl)-7H-pyrrolo[2,3-d]pyrimidin-6-yl)-2-methyl-2,5-dihydro-1H-pyrrol-1-yl)-2-methylprop-2-en-1-one | 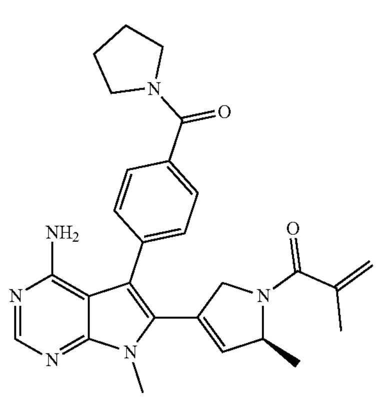 [SMILES: C=C(C)C(=O)N1CC(c2c(-c3ccc(C(=O)N4CCCC4)cc3)c3c(N)ncnc3n2C)=C[C@@H]1C] | ¹H NMR (400 MHz, DMSO-d₆) δ 8.18 (s, 1H), 7.61 (d, J = 8.0 Hz, 2H), 7.43 (d, J = 7.7 Hz, 2H), 6.27-6.18 (m, 1H), 6.10 (s, 1H), 5.21 (d, J = 10.5 Hz, 1H), 5.07 (s, 1H), 4.89 (s, 1H), 4.17-4.03 (m, 1H), 3.98 (d, J = 14.4 Hz, 1H), 3.77 (s, 3H), 3.50 (t, J = 6.7 Hz, 2H), 3.44 (t, J = 6.4 Hz, 2H), 1.87 (dq, J = 17.8, 6.5 Hz, 5H), 1.70 (s, 2H), 1.26 (d, J = 6.4 Hz, 2H), 1.19 (d, J = 6.3 Hz, 1H). | 471.30 |

TABLE 14-continued

Additional Exemplary Compounds

| Compound | Structure | Proton NMR | MS [M + 1] |
|---|---|---|---|
| 1-((2S,4R)-4-(4-amino-7-methyl-5-(4-(piperidine-1-carbonyl)phenyl)-7H-pyrrolo[2,3-d]pyrimidin-6-yl)-2-methylpyrrolidin-1-yl)prop-2-en-1-one | 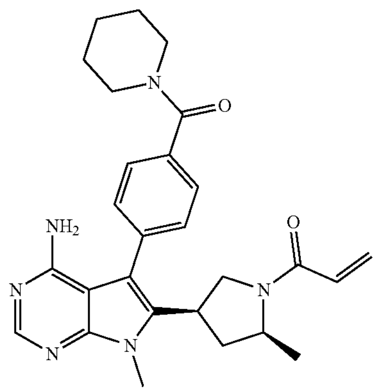 [SMILES: C=CC(=O)N1C[C@H](c2c(-c3ccc(C(=O)N4CCCCC4)cc3)c3c(N)ncnc3n2C)C[C@@H]1C] | ¹H NMR (400 MHz, DMSO-d₆) δ 8.13 (s, 1H), 7.48 (s, 4H), 6.52 (ddd, J = 27.6, 16.6, 10.2 Hz, 1H), 6.20-5.95 (m, 1H), 5.85-5.13 (m, 3H), 4.22-3.90 (m, 2H), 3.80 (s, 3H), 3.71-3.51 (m, 3H), 3.44 (t, J = 10.9 Hz, 1H), 3.14 (t, J = 11.7 Hz, 1H), 2.39-2.23 (m, 1H), 1.84-1.62 (m, 3H), 1.55 (t, J = 10.8 Hz, 5H), 1.06 (d, J = 6.3 Hz, 3H). | 473.30 |
| 1-((2S,4R)-4-(4-amino-5-(2-fluoro-4-((4-methylpyrimidin-2-yl)oxy)phenyl)-7-methyl-7H-pyrrolo[2,3-d]pyrimidin-6-yl)-2-methylpyrrolidin-1-yl)prop-2-en-1-one | 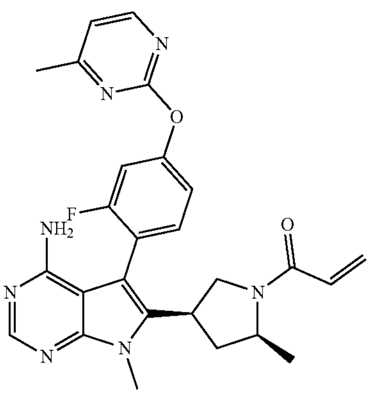 [SMILES: C=CC(=O)N1C[C@H](c2c(-c3ccc(Oc4nccc(C)n4)cc3F)c3c(N)ncnc3n2C)C[C@@H]1C] | ¹H NMR (400 MHz, DMSO-d₆) δ 8.57-8.43 (m, 1H), 8.14 (s, 1H), 7.50 (td, J = 8.5, 3.8 Hz, 1H), 7.36 (ddt, J = 10.0, 4.8, 2.4 Hz, 1H), 7.27-7.13 (m, 2H), 6.75-6.41 (m, 1H), 6.19-5.98 (m, 1H), 5.80-5.33 (m, 3H), 4.36-3.91 (m, 2H), 3.80 (d, J = 4.0 Hz, 3H), 3.69-3.53 (m, 1H), 3.42 (dd, J = 20.4, 10.2 Hz, 1H), 2.42 (d, J = 8.0 Hz, 4H), 2.04-1.38 (m, 1H), 1.24-1.00 (m, 3H). | 488.25 |
| 1-((2S,4S)-4-(4-amino-7-methyl-5-(4-(piperidine-1-carbonyl)phenyl)-7H-pyrrolo[2,3-d]pyrimidin-6-yl)-2-methylpyrrolidin-1-yl)prop-2-en-1-one | 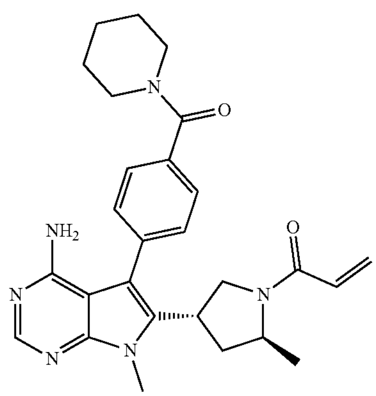 [SMILES: C=CC(=O)N1C[C@@H](c2c(-c3ccc(C(=O)N4CCCCC4)cc3)c3c(N)ncnc3n2C)C[C@@H]1C] | ¹H NMR (400 MHz, DMSO-d₆) δ 8.13 (d, J = 1.5 Hz, 1H), 7.45 (dd, J = 5.9, 3.0 Hz, 4H), 6.49 (ddd, J = 69.2, 16.7, 10.3 Hz, 1H), 6.11 (ddd, J = 16.4, 13.1, 2.5 Hz, 1H), 5.63 (ddd, J = 21.8, 10.2, 2.5 Hz, 3H), 4.22 (dt, J = 39.9, 7.0 Hz, 1H), 3.92 (dd, J = 15.7, 7.8 Hz, 2H), 3.79 (d, J = 11.1 Hz, 3H), 3.70 (dd, J = 12.5, 9.0 Hz, 1H), 3.56 (d, J = 17.7 Hz, 3H), 3.42 (d, J = 12.6 Hz, 1H), 2.37-2.06 (m, 1H), 1.95 (dd, J = 12.4, 6.8 Hz, 1H), 1.58 (d, J = 41.4 Hz, 6H), 1.24 (s, 1H), 1.14 (dd, J = 10.0, 6.4 Hz, 3H). | 473.30 |
| 1-((2S)-4-(4-amino-7-methyl-5-((R)-4-(pyrrolidine-1-carbonyl)cyclohex-1-en-1-yl)-7H-pyrrolo[2,3-d]pyrimidin-6-yl)-2-methylpyrrolidin-1-yl)prop-2-en-1-one | 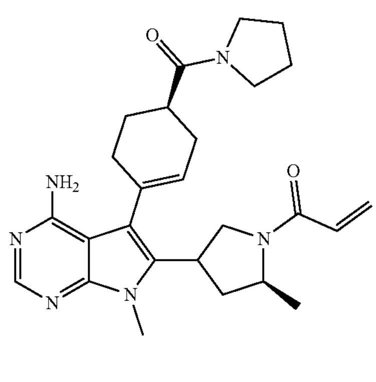 [SMILES: C=CC(=O)N1CC(c2c(C3=CC[C@H](C(=O)N4CCCC4)CC3)c3c(N)ncnc3n2C)C[C@@H]1C] | ¹H NMR (400 MHz, DMSO-d₆) δ 8.02 (d, J = 16.1 Hz, 1H), 6.63 (ddd, J = 26.2, 16.6, 10.2 Hz, 1H), 6.46 (s, 1H), 6.16 (td, J = 16.7, 2.6 Hz, 1H), 5.88-5.49 (m, 2H), 4.44-3.96 (m, 2H), 3.67 (d, J = 5.2 Hz, 2H), 3.52 (q, J = 8.8, 7.4 Hz, 3H), 3.32 (d, J = 5.6 Hz, 2H), 2.94 (s, 1H), 2.43 (d, J = 6.3 Hz, 1H), 2.37-2.19 (m, 3H), 2.18-1.99 (m, 2H), 1.89 (q, J = 6.6 Hz, 3H), 1.80 (h, J = 8.1, 7.0 Hz, 3H), 1.27 (dt, J = 18.0, 6.3 Hz, 3H). | 463.30 |

TABLE 14-continued
Additional Exemplary Compounds
| Compound | Structure | Proton NMR | MS [M + 1] |
|---|---|---|---|
| 1-((2S)-4-(4-amino-7-methyl-5-((S)-4-(pyrrolidine-1-carbonyl) cyclohex-1-en-1-yl)-7H-pyrrolo[2,3-d]pyrimidin-6-yl)-2-methylpyrrolidin-1-yl)prop-2-en-1-one | 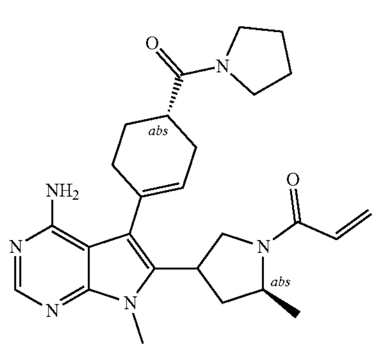 [SMILES: C=CC(=O)N1CC(c2c(C3=CC[C@@H](C(=O)N4CCCC4)CC3)c3c(N)ncnc3n2C)C[C@@H]1C] | $^1$H NMR (400 MHz, DMSO-$d_6$) δ 8.02 (d, J = 16.7 Hz, 1H), 6.64 (td, J = 16.7, 10.5 Hz, 1H), 6.49 (s, 1H), 6.28-6.03 (m, 1H), 5.87-5.58 (m, 2H), 4.16 (d, J = 74.3 Hz, 2H), 3.67 (d, J = 4.2 Hz, 4H), 3.53 (s, 3H), 3.31 (s, 2H), 2.94 (s, 1H), 2.33 (s, 1H), 2.27 (s, 4H), 1.89 (q, J = 6.7 Hz, 4H), 1.80 (q, J = 6.7 Hz, 3H), 1.27 (dd, J = 21.1, 7.7 Hz, 3H). | 463.35 |
Example 16
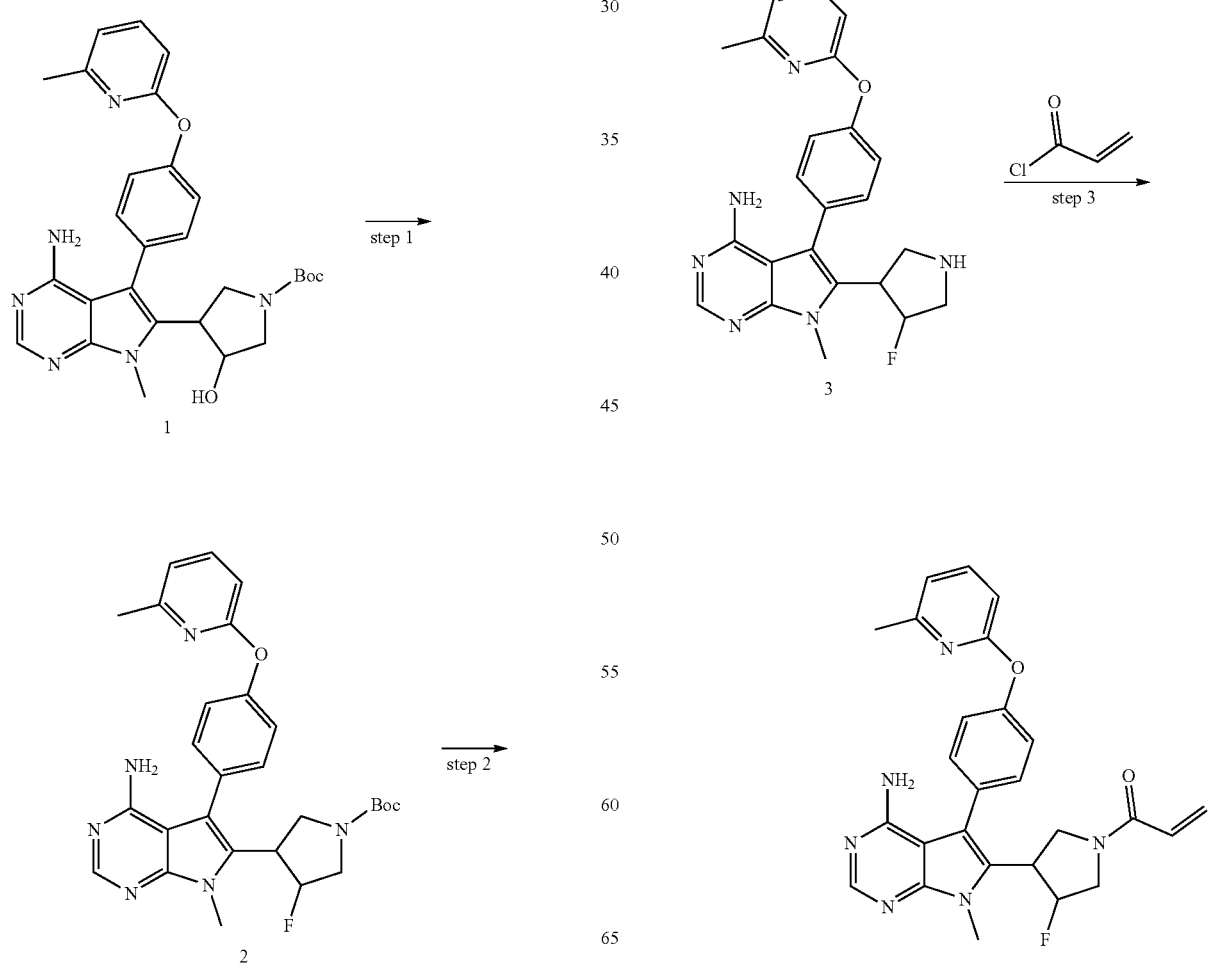
Scheme 13

1611 tert-butyl 3-(4-amino-7-methyl-5-(4-((6-methylpyridin-2-yl)oxy)phenyl)-7H-pyrrolo[2,3-d]pyrimidin-6-yl)-4-fluoropyrrolidine-1-carboxylate

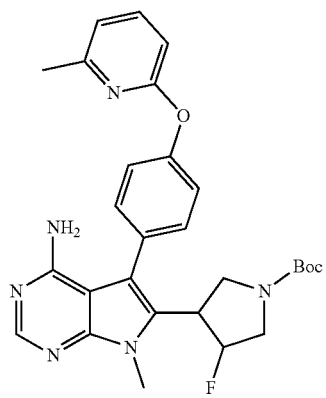 [SMILES: Cc1cccc(Oc2ccc(-c3c(C4CN(C(=O)OC(C)(C)C)CC4F)n(C)c4ncnc(N)c34)cc2)n1]

Step 1: A round bottomed flask was charged with tert-butyl 3-(4-amino-7-methyl-5-(4-((6-methylpyridin-2-yl)oxy)phenyl)-7H-pyrrolo[2,3-d]pyrimidin-6-yl)-4-hydroxypyrrolidine-1-carboxylate (200 mg, 0.39 mmol), DCM (10 mL) and a stir bar. DAST (74.8 mg, 0.46 mmol) was added, and the solution was stirred for 3 h at 0° C. The reaction mixture was quenched with water, extracted with DCM, dried over $Na_2SO_4$, concentrated in vacuo. The resulting crude material was purified by silica gel chromatography. Concentration in vacuo resulted in tert-butyl 3-(4-amino-7-methyl-5-(4-((6-methylpyridin-2-yl)oxy)phenyl)-7H-pyrrolo[2,3-d]pyrimidin-6-yl)-4-fluoropyrrolidine-1-carboxylate (127 mg, 63%) as an yellow solid.

6-(4-fluoropyrrolidin-3-yl)-7-methyl-5-(4-((6-methylpyridin-2-yl)oxy)phenyl)-7H-pyrrolo[2,3-d]pyrimidin-4-amine

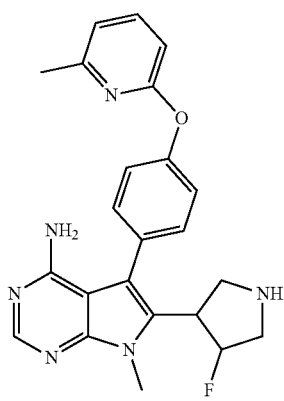 [SMILES: Cc1cccc(Oc2ccc(-c3c(C4CNCC4F)n(C)c4ncnc(N)c34)cc2)n1]

1612

Step 2: A resealable reaction via was charged with tert-butyl 3-(4-amino-7-methyl-5-(4-((6-methylpyridin-2-yl)oxy)phenyl)-7H-pyrrolo[2,3-d]pyrimidin-6-yl)-4-fluoropyrrolidine-1-carboxylate (127 mg, 0.24 mmol), DCM (5 mL) and a stir bar. TFA (2 mL) was added, and the solution was stirred for 1 h at 25° C. The reaction mixture was concentrated, diluted with water, adjust pH value to 7 with Sat. Na2CO3, extracted with DCM, dried over $Na_2SO_4$, concentrated in vacuo. The resulting crude material was purified by prep-TLC. Concentration in vacuo resulted in 6-(4-fluoropyrrolidin-3-yl)-7-methyl-5-(4-((6-methylpyridin-2-yl)oxy)phenyl)-7H-pyrrolo[2,3-d]pyrimidin-4-amine (77 mg, 77%) as a brown solid.

1-(3-(4-amino-7-methyl-5-(4-((6-methylpyridin-2-yl)oxy)phenyl)-7H-pyrrolo[2,3-d]pyrimidin-6-yl)-4-fluoropyrrolidin-1-yl)prop-2-en-1-one

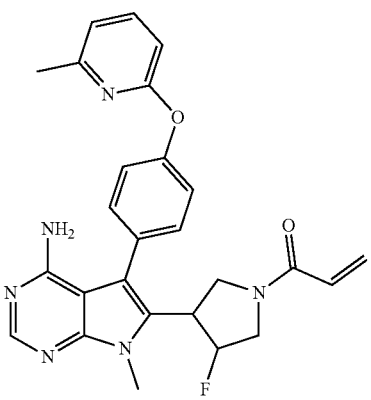 [SMILES: C=CC(=O)N1CC(F)C(c2c(-c3ccc(Oc4cccc(C)n4)cc3)c3c(N)ncnc3n2C)C1]

Step 3: A round bottomed flask was charged with 6-(4-fluoropyrrolidin-3-yl)-7-methyl-5-(4-((6-methylpyridin-2-yl)oxy)phenyl)-7H-pyrrolo[2,3-d]pyrimidin-4-amine (77 mg, 180 µmol), TEA (55.8 mg, 0.55 mmol) DCM (5 mL) and a stir bar. acryloyl chloride (13.2 mg, 147 µmol) was added, and the solution was stirred for 0.5 h at −35° C. The reaction mixture was quenched with MeOH, the resulting mixture was concentrated, crude material was purified by prep-HPLC. Lyophilization to afford 1-(3-(4-amino-7-methyl-5-(4-((6-methylpyridin-2-yl)oxy)phenyl)-7H-pyrrolo[2,3-d]pyrimidin-6-yl)-4-fluoropyrrolidin-1-yl)prop-2-en-1-one (5.2 mg, 6%) as a white amorphous solid.

Additional compounds prepared according to the methods of Example 16 are depicted in Table 15 below.

TABLE 15
Additional Exemplary Compounds
| Compound | Structure | Proton NMR | MS [M + 1] |
|---|---|---|---|
| 1-(3-(4-amino-7-methyl-5-(4-((6-methylpyridin-2-yl)oxy)phenyl)-7H-pyrrolo[2,3-d]pyrimidin-6-yl)-4-fluoropyrrolidin-1-yl)prop-2-en-1-one | 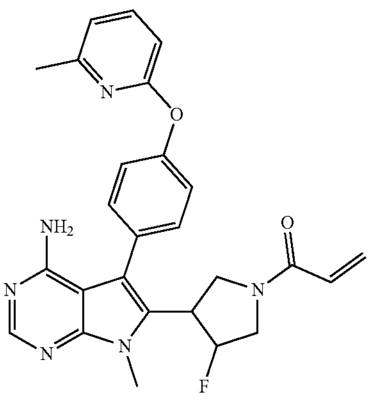 [SMILES: C=CC(=O)N1CC(F)C(c2c(-c3ccc(Oc4cccc(C)n4)cc3)c3c(N)ncnc3n2C)C1] | $^1$H NMR (400 MHz, DMSO-d$_6$) δ 8.46 (s, 1H), 7.76 (td, J = 7.8, 4.4 Hz, 1H), 7.42 (s, 3H), 7.18 (s, 2H), 7.06 (dd, J = 7.3, 2.7 Hz, 1H), 6.87 (t, J = 8.1 Hz, 1H), 6.38 (ddd, J = 50.2, 16.7, 10.3 Hz, 1H), 6.07 (dt, J = 16.7, 2.8 Hz, 1H), 5.62 (td, J = 10.1, 2.4 Hz, 1H), 5.46 (ddd, J = 52.8, 19.4, 4.3 Hz, 1H), 4.58-3.27 (m, 8H), 2.39 (d, J = 1.4 Hz, 3H). | 473.20 |
Example 17
Scheme 14
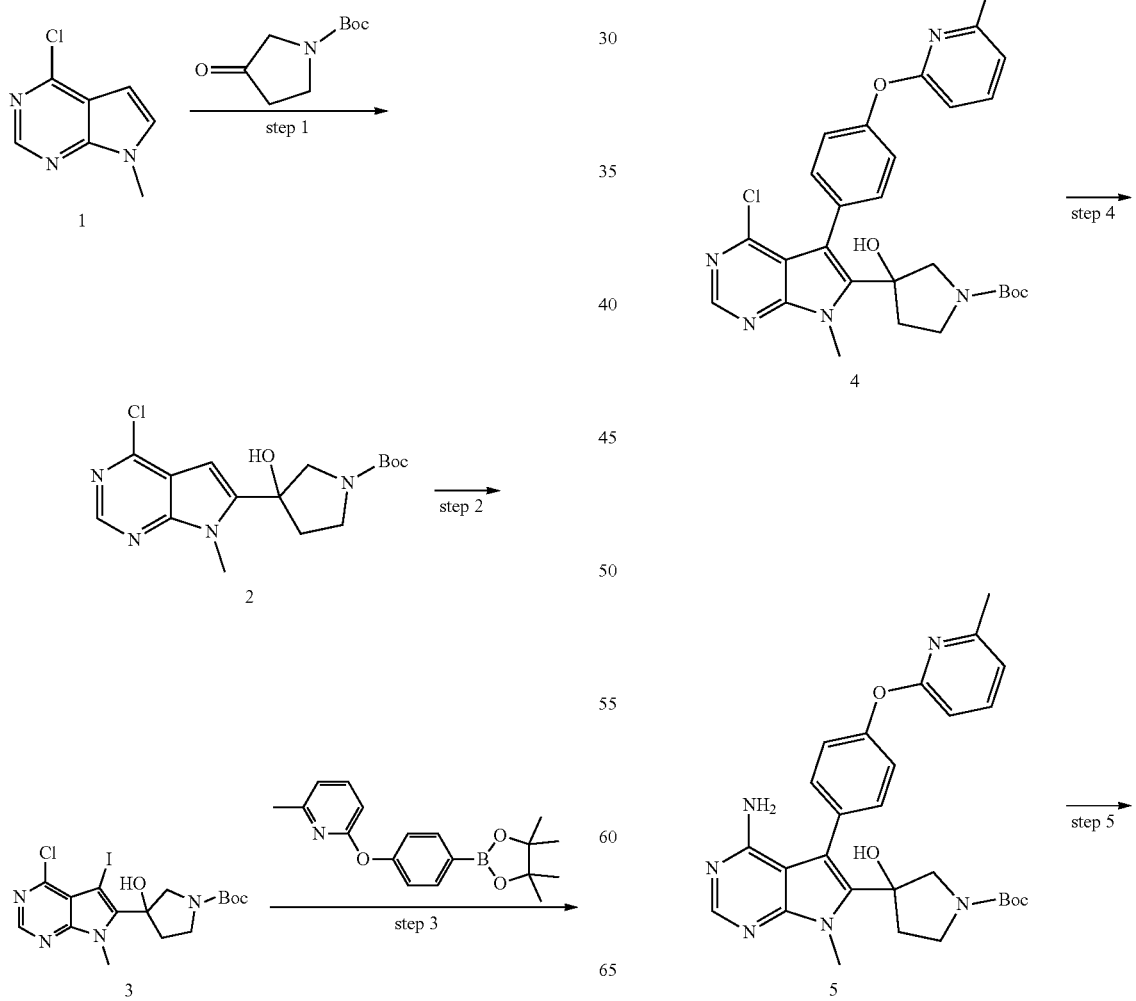

1615
-continued

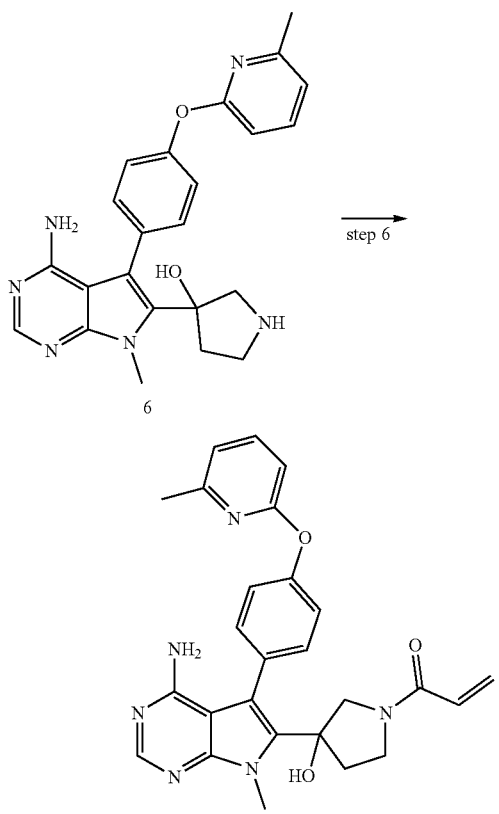

6 tert-butyl 3-(4-chloro-7-methyl-7H-pyrrolo[2,3-d]pyrimidin-6-yl)-3-hydroxypyrrolidine-1-carboxylate

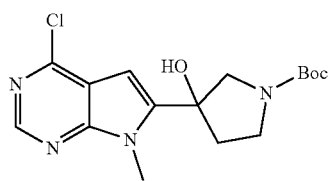 [SMILES: Cn1c(C2(O)CCN(C(=O)OC(C)(C)C)C2)cc2c(Cl)ncnc21]

Step 1: A resealable reaction vial was charged with 4-chloro-7-methyl-7H-pyrrolo[2,3-d]pyrimidine (5 g, 29.9 mmol), tetrahydrofuran (200 mL) and a stirbar before being evacuated and purged with nitrogen three times. LDA (30 mL, 59.9 mmol) was added dropwise at −78° C., and the mixture was stirred for 30 min at −78° C. tert-butyl 3-oxopyrrolidine-1-carboxylate (17 g, 89.8 mmol) in 100 mL of THF was added dropwise, the mixture was stirred for 1 h at −78° C. The mixture was warmed to r.t. and the reaction mixture was diluted with H$_2$O (300 mL), and the aqueous phase was extracted with EA (300 mL) three times. The combined organic layers were washed with brines, dried over sodium sulfate, filtered, and concentrated in vacuo. The resulting crude material was purified by silica gel chromatography (eluting with PE/EA=10/1). Concentration in vacuo resulted in tert-butyl 3-(4-chloro-7-{[2-(trimethylsilyl)ethoxy]methyl}-7H-pyrrolo[2,3-d]pyrimidin-6-yl)-3-hydroxypyrrolidine-1-carboxylate (2.20 g, 20.9%) as light yellow solid.

1616 tert-butyl 3-(4-chloro-5-iodo-7-methyl-7H-pyrrolo[2,3-d]pyrimidin-6-yl)-3-hydroxypyrrolidine-1-carboxylate

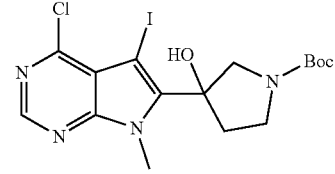 [SMILES: Cn1c(C2(O)CCN(C(=O)OC(C)(C)C)C2)c(I)c2c(Cl)ncnc21]

Step 2: A round bottomed flask was charged with tert-butyl 3-{4-chloro-7-methyl-7H-pyrrolo[2,3-d]pyrimidin-6-yl}-3-hydroxypyrrolidine-1-carboxylate (976 mg, 2.76 mmol), NIS (621 mg, 2.76 mmol), TFA (943 mg, 8.28 mmol) and a stirbar. DCM (20 mL) was added, and the solution was stirred at r.t. for 3 h under nitrogen protection. The mixture was quenched with saturated Na$_2$S$_2$O$_3$ aq. (10 mL), and extracted with DCM (3*40 mL), the organic phase was combined and the dried with anhydrous Na$_2$SO$_4$, concentrated under reduced pressure, the crude product was purified by C18 Flahs to afford tert-butyl 3-{4-chloro-5-iodo-7-methyl-7H-pyrrolo[2,3-d]pyrimidin-6-yl}-3-hydroxypyrrolidine-1-carboxylate (980 mg, 73.9%) as white solid tert-butyl 3-(4-chloro-7-methyl-5-(4-((6-methylpyridin-2-yl)oxy)phenyl)-7H-pyrrolo[2,3-d]pyrimidin-6-yl)-3-hydroxypyrrolidine-1-carboxylate

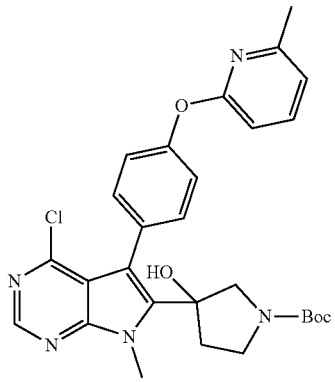 [SMILES: Cc1cccc(Oc2ccc(-c3c(C4(O)CCN(C(=O)OC(C)(C)C)C4)n(C)c4ncnc(Cl)c34)cc2)n1]

Step 3: A resealable reaction vial was charged with tert-butyl 3-{4-chloro-5-iodo-7-methyl-7H-pyrrolo[2,3-d]pyrimidin-6-yl}-3-hydroxypyrrolidine-1-carboxylate (800 mg, 1.67 mmol), 2-methyl-6-[4-(4,4,5,5-tetramethyl-1,3,2-dioxaborolan-2-yl)phenoxy]pyridine (519 mg, 1.67 mmol), Pd(PPh3)2Cl2 (175 mg, 250 μmol) K3PO4 (1.06 g, 5.01 mmol) and a stirbar. DMF/H2O (25 mL) was added, and the solution was stirred at 50° C. for 1 h. The mixture was diluted with EtOAc(100 mL), and washed with water (3*50 mL), the organic phase was concentrated and the crude product was purified by C18 flash and further purified by prep-TLC with EA:PE=2:1 to afford tert-butyl 3-(4-chloro-7-methyl-5-{4-[(6-methylpyridin-2-yl)oxy]phenyl}-7H-pyrrolo[2,3-d]pyrimidin-6-yl)-3-hydroxypyrrolidine-1-carboxylate (140 mg, 15.6%) as light yellow solid.

tert-butyl 3-(4-amino-7-methyl-5-(4-((6-methylpyridin-2-yl)oxy)phenyl)-7H-pyrrolo[2,3-d]pyrimidin-6-yl)-3-hydroxypyrrolidine-1-carboxylate

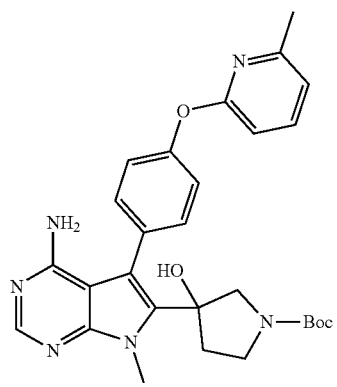 [SMILES: Cc1cccc(Oc2ccc(-c3c(C4(O)CCN(C(=O)OC(C)(C)C)C4)n(C)c4ncnc(N)c34)cc2)n1]

Step 4: A resealable reaction vial was charged with tert-butyl 3-(4-chloro-7-methyl-5-{4-[(6-methylpyridin-2-yl)oxy]phenyl}-7H-pyrrolo[2,3-d]pyrimidin-6-yl)-3-hydroxypyrrolidine-1-carboxylate (120 mg, 223 µmol), $NH_3H_2O$ (1.82 g, 52.0 mmol), and a stirbar. Dioxane (1.5 mL) was added, seal tube and the solution was stirred at 100° C. for 10 h. The mixture was concentrated and the crude product was purified by C18 flash to afford tert-butyl 3-(4-amino-7-methyl-5-{4-[(6-methylpyridin-2-yl)oxy]phenyl}-7H-pyrrolo[2,3-d]pyrimidin-6-yl)-3-hydroxypyrrolidine-1-carboxylate (62.4 mg, 54.2%) as light yellow oil.

3-(4-amino-7-methyl-5-(4-((6-methylpyridin-2-yl)oxy)phenyl)-7H-pyrrolo[2,3-d]pyrimidin-6-yl)pyrrolidin-3-ol

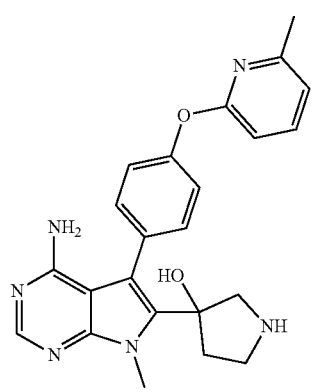 [SMILES: Cc1cccc(Oc2ccc(-c3c(C4(O)CCNC4)n(C)c4ncnc(N)c34)cc2)n1]

Step 5: A round bottomed flask was charged with tert-butyl 3-(4-amino-7-methyl-5-{4-[(6-methylpyridin-2-yl)oxy]phenyl}-7H-pyrrolo[2,3-d]pyrimidin-6-yl)-3-hydroxypyrrolidine-1-carboxylate (80.0 mg, 154 µmol), TFA (52.6 mg, 462 µmol), and a stirbar. DCM (25 mL) was added, and the solution was stirred at r.t. for 5 h. The mixture was diluted with water, and adjust the pH to 7 with $Na_2CO_3$, the mixture was extracted with DCM (8*40 mL), the organic phase was concentrated and the crude product 3-(4-amino-7-methyl-5-{4-[(6-methylpyridin-2-yl)oxy]phenyl}-7H-pyrrolo[2,3-d]pyrimidin-6-yl)pyrrolidin-3-ol (60.0 mg, 93.6%) was used for next step without purification.

1-(3-(4-amino-7-methyl-5-(4-((6-methylpyridin-2-yl)oxy)phenyl)-7H-pyrrolo[2,3-d]pyrimidin-6-yl)-3-hydroxypyrrolidin-1-yl)prop-2-en-1-one

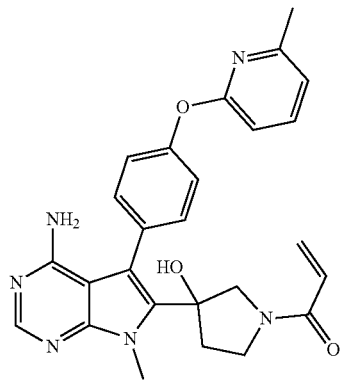 [SMILES: C=CC(=O)N1CCC(O)(c2c(-c3ccc(Oc4cccc(C)n4)cc3)c3c(N)ncnc3n2C)C1]

Step 6: A round bottomed flask was charged with 3-(4-amino-7-methyl-5-{4-[(6-methylpyridin-2-yl)oxy]phenyl}-7H-pyrrolo[2,3-d]pyrimidin-6-yl)pyrrolidin-3-ol (40 mg, 96.0 µmol), TEA (29.0 mg, 288 µmol), DCM (15 mL) and a stirbar. prop-2-enoyl chloride (6.95 mg, 76.8 µmol, 3.4 mL) was added, and the solution was stirred at −45° C. for 0.5 h. The mixture was quenched with MeOH, and the solvent was removed, the crude product was purified by HPLC(Column: XBridge Prep OBD C18 Column, 19*250 mm, 5 um) to afford 1-[3-(4-amino-7-methyl-5-{4-[(6-methylpyridin-2-yl)oxy]phenyl}-7H-pyrrolo[2,3-d]pyrimidin-6-yl)-3-hydroxypyrrolidin-1-yl]prop-2-en-1-one (10.5 mg, 23.2%) as white solid.

Characterization data for the compound prepared according to the methods of Example 17 are provided in Table 16 below.

TABLE 16
Exemplary Compound
| Compound | Structure | Proton NMR | MS [M + 1] |
|---|---|---|---|
| 1-(3-(4-amino-7-methyl-5-(4-((6-methylpyridin-2-yl)oxy)phenyl)-7H-pyrrolo[2,3-d]pyrimidin-6-yl)-3-hydroxypyrrolidin-1-yl)prop-2-en-1-one | 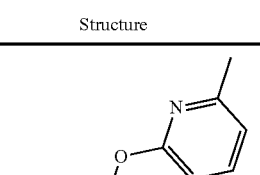 | $^1$H NMR (400 MHz, DMSO-$d_6$) δ 8.14 (s, 1H), 7.76 (t, J = 7.6 Hz, 1H), 7.52-7.43(m, 2H), 7.24-7.21(m, 2H), 7.04 (dd, J = 7.4, 1.9 Hz, 1H), 6.84 (d, J = 8.2 Hz, 1H), 6.61-6.25 (m, 1H), 6.15-6.05 (m, 1H), 5.88-5.83 (m, 1H), 5.65-5.59 (m, 1H), 3.96 (d, J = 4.9 Hz, 3H), 3.89-3.81 (m, 1H), 3.69-3.53 (m, 1H), 3.47-3.41 (m, 1H), 3.29-3.22 (m, 1H), 2.36-2.30 (m, 3H), 2.21-2.10 (m, 1H), 2.16-1.88 (m, 1H). | 471.20 |
Example 18
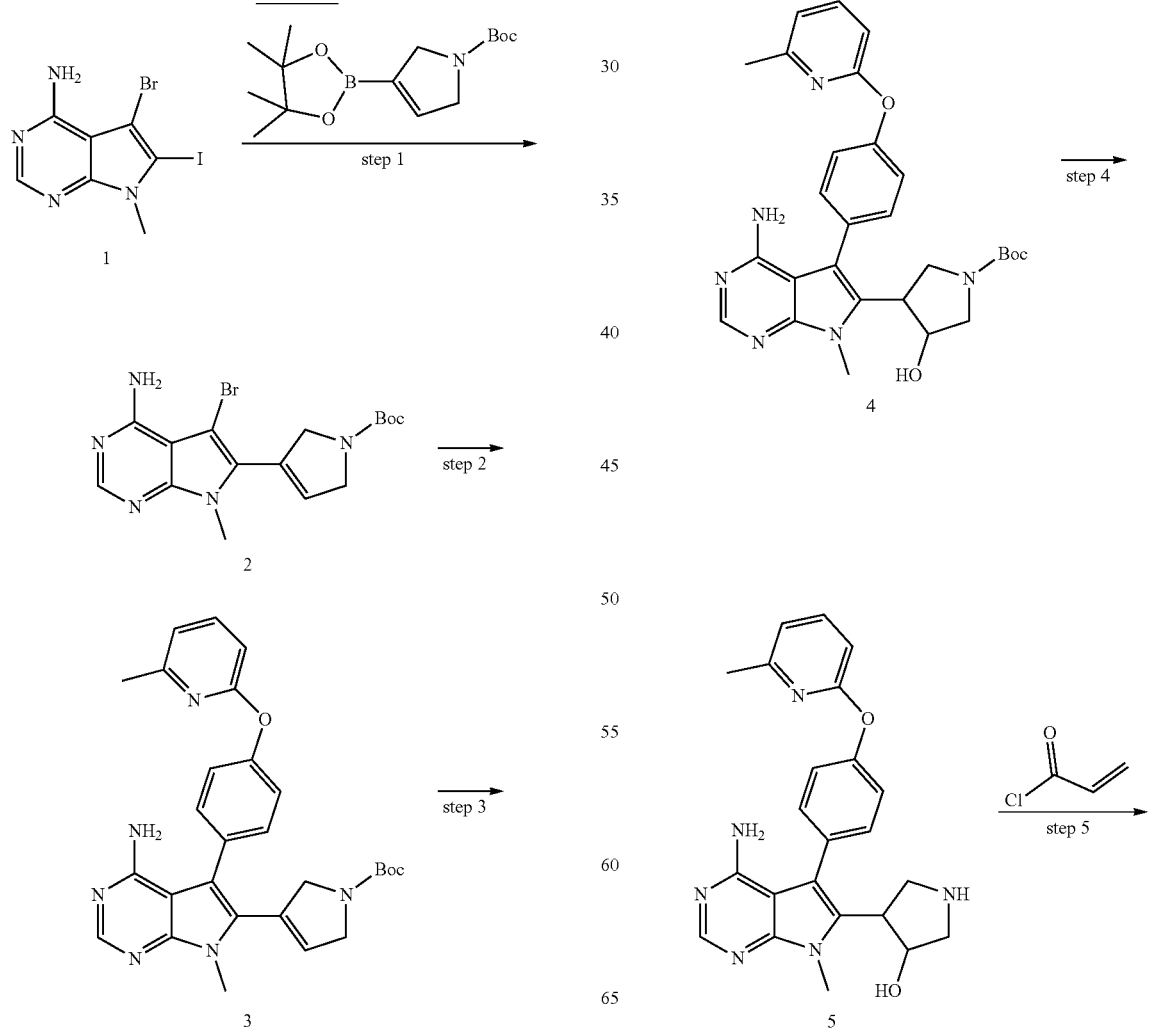

1621
-continued

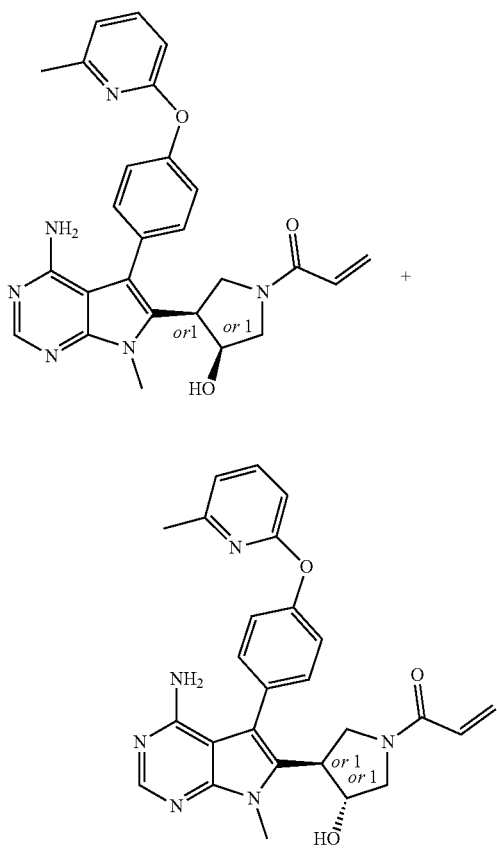

tert-butyl 3-(4-amino-5-bromo-7-methyl-7H-pyrrolo[2,3-d]pyrimidin-6-yl)-2,5-dihydro-1H-pyrrole-1-carboxylate

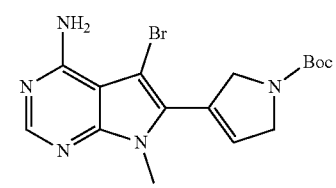 [SMILES: Cn1c(C2=CCN(C(=O)OC(C)(C)C)C2)c(Br)c2c(N)ncnc21]

Step 1: A round bottomed flask was charged with 5-bromo-6-iodo-7-methylpyrrolo[2,3-d]pyrimidin-4-amine (3 g, 8.50 mmol), tert-butyl 3-(4,4,5,5-tetramethyl-1,3,2-dioxaborolan-2-yl)-2,5-dihydropyrrole-1-carboxylate (3.01 g, 10.20 mmol), Pd(PPh3)4 (982 mg, 850 μmol), K3PO4 (5.41 g, 25.5 mmol) and a stir bar. Dimethylformamide/water (40 mL, v/v=16:1) was added, and the solution was stirred for 2 h at 50° C. The reaction mixture was quenched with water, extracted with DCM, dried over Na2SO4, concentrated in vacuo. The resulting crude material was purified by silica gel chromatography. Concentration in vacuo resulted in tert-butyl 3-(4-amino-5-bromo-7-methyl-7H-pyrrolo[2,3-d]pyrimidin-6-yl)-2,5-dihydro-1H-pyrrole-1-carboxylate (2 g, 60%) as a yellow solid.

tert-butyl 3-(4-amino-7-methyl-5-(4-((6-methylpyridin-2-yl)oxy)phenyl)-7H-pyrrolo[2,3-d]pyrimidin-6-yl)-2,5-dihydro-1H-pyrrole-1-carboxylate

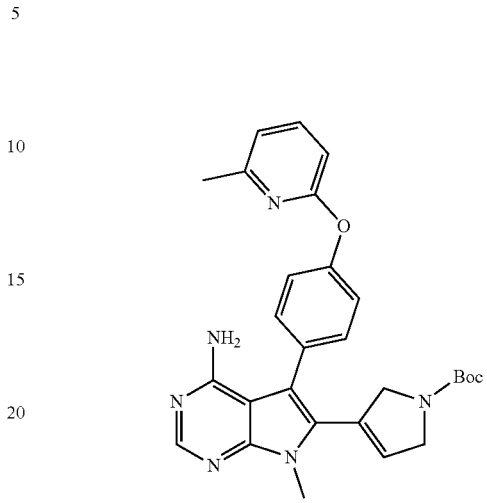

Step 2: A resealable reaction via was charged with tert-butyl 3-[4-amino-5-bromo-7-methylpyrrolo[2,3-d]pyrimidin-6-yl]-2,5-dihydropyrrole-1-carboxylate (600 mg, 1.52 mmol), 2-methyl-6-[4-(4,4,5,5-tetramethyl-1,3,2-dioxaborolan-2-yl)phenoxy]pyridine (568 mg, 1.83 mmol), Pd(DtBPF)Cl2 (99 mg, 152 μmol), K3PO4 (0.97 g, 4.56 mmol) and a stir bar before being evacuated and purged with nitrogen three times. DMF:water=16:1 (10 mL) was added, and the solution was stirred for 3 h at 90° C. The reaction mixture was quenched with water, extracted with DCM, dried over Na2SO4, concentrated in vacuo. The resulting crude material was purified by silica gel chromatography. Concentration in vacuo resulted in tert-butyl 3-(4-amino-7-methyl-5-[4-[(6-methylpyridin-2-yl)oxy]phenyl]pyrrolo[2,3-d]pyrimidin-6-yl)-2,5-dihydropyrrole-1-carboxylate (510 mg, 67%) as an off-white solid.

tert-butyl 3-(4-amino-7-methyl-5-(4-((6-methylpyridin-2-yl)oxy)phenyl)-7H-pyrrolo[2,3-d]pyrimidin-6-yl)-4-hydroxypyrrolidine-1-carboxylate

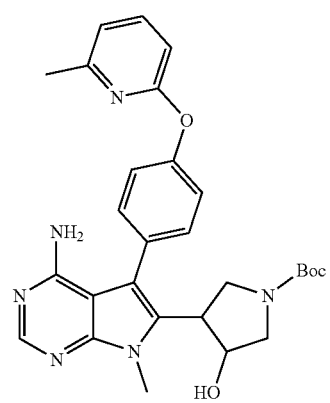 [SMILES: Cc1cccc(Oc2ccc(-c3c(C4CN(C(=O)OC(C)(C)C)CC4O)n(C)c4ncnc(N)c34)cc2)n1]

Step 3: A round bottomed flask was charged with tert-butyl 3-(4-amino-7-methyl-5-[4-[(6-methylpyridin-2-yl)oxy]phenyl]pyrrolo[2,3-d]pyrimidin-6-yl)-2,5-dihydropyrrole carboxylate (450 mg, 0.90 mmol), THF (10 mL) and a stir bar. BH3-THF (9.03 mL, 9.03 mmol, 1M in THF) was added at 0° C., and the solution was stirred for 2 h at room temperature. Then NaOH (9.03 mL, 9.03 mmol, 1M in H$_2$O) and H2O2 (0.21 mL, 30% in water) was added and stirred for another 2 hours. The reaction mixture was quenched with water, and adjusted pH value to 7 with HCl (2M), extracted with DCM, dried over Na$_2$SO$_4$, concentrated in vacuo. The resulting crude material was purified by silica gel chromatography. Concentration in vacuo resulted in tert-butyl 3-(4-amino-7-methyl-5-[4-[(6-methylpyridin-2-yl)oxy]phenyl]pyrrolo[2,3-d]pyrimidin-6-yl)-4-hydroxypyrrolidine-1-carboxylate (160 mg, 34%) as a brown amorphous solid.

4-(4-amino-7-methyl-5-(4-((6-methylpyridin-2-yl)oxy)phenyl)-7H-pyrrolo[2,3-d]pyrimidin-6-yl)pyrrolidin-3-ol

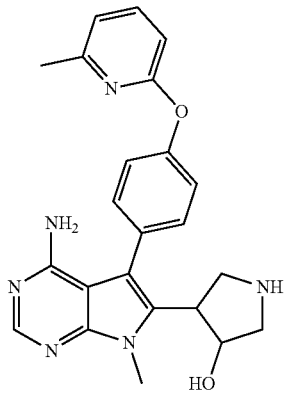 [SMILES: Cc1cccc(Oc2ccc(-c3c(C4CNCC4O)n(C)c4ncnc(N)c34)cc2)n1]

Step 4: A resealable reaction via was charged with tert-butyl 3-(4-amino-7-methyl-5-[4-[(6-methylpyridin-2-yl)oxy]phenyl]pyrrolo[2,3-d]pyrimidin-6-yl)-4-hydroxypyrrolidine-1-carboxylate (160 mg, 0.31 mmol), DCM (5 mL) and a stir bar. TFA (2 mL) was added, and the solution was stirred for 1 h at 25° C. The reaction mixture was concentrated, diluted with water, adjust pH value to 7 with Sat. Na2CO3, extracted with DCM, dried over Na$_2$SO$_4$, concentrated in vacuo. The resulting crude material was purified by prep-TLC. Concentration in vacuo resulted in 4-(4-amino-7-methyl-5-(4-((6-methylpyridin-2-yl)oxy)phenyl)-7H-pyrrolo[2,3-d]pyrimidin-6-yl)pyrrolidin-3-ol (100 mg, 78%) as a brown solid.

1-(3-(4-amino-7-methyl-5-(4-((6-methylpyridin-2-yl)oxy)phenyl)-7H-pyrrolo[2,3-d]pyrimidin-6-yl)-4-hydroxypyrrolidin-1-yl)prop-2-en-1-one

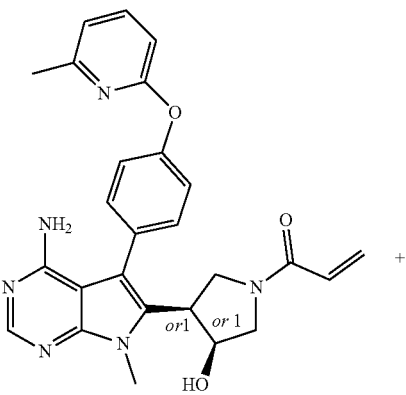

1

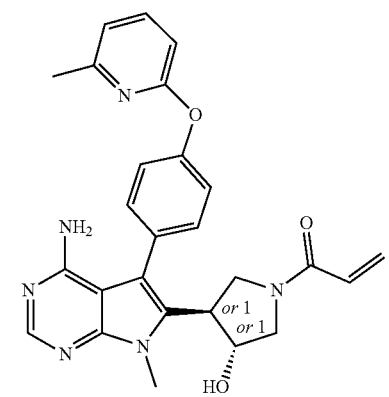

2

Step 5: A round bottomed flask was charged with 4-(4-amino-7-methyl-5-(4-((6-methylpyridin-2-yl)oxy)phenyl)-7H-pyrrolo[2,3-d]pyrimidin-6-yl)pyrrolidin-3-ol (82 mg, 170 μmol), TEA (52.8 mg, 0.52 mmol) DCM (5 mL) and a stir bar. acryloyl chloride (12.8 mg, 142 μmol) was added, and the solution was stirred for 0.5 h at −35° C. The reaction mixture was quenched with MeOH, the resulting mixture was concentrated, crude material was purified by prep-HPLC (Column: Xselect CSH OBD Column 30*150 mm 5 um, n; Mobile Phase A:Water(0.1% FA), Mobile Phase B:ACN; Flow rate:60 mL/min; Gradient:5 B to 27 B in 7 min; 220 nm; RT1:6.10,6.80; RT2). Lyophilization afforded 1-(3-(4-amino-7-methyl-5-(4-((6-methylpyridin-2-yl)oxy)phenyl)-7H-pyrrolo[2,3-d]pyrimidin-6-yl)-4-hydroxypyrrolidin-1-yl)prop-2-en-1-one (47.4 mg, 57%) include: 1 (19.1 mg) as a white amorphous solid, and 2 (28.3 mg) as a white solid.

Additional compounds prepared according to the methods of Example 18 are depicted in Table 17 below.

TABLE 17

Additional Exemplary Compounds

| Compound | Structure | Proton NMR | MS [M + 1] |
|---|---|---|---|
| 1-((3R,4S)-3-(4-amino-7-methyl-5-(4-((6-methylpyridin-2-yl)oxy)phenyl)-7H-pyrrolo[2,3-d]pyrimidin-6-yl)-4-hydroxypyrrolidin-1-yl)prop-2-en-1-one | 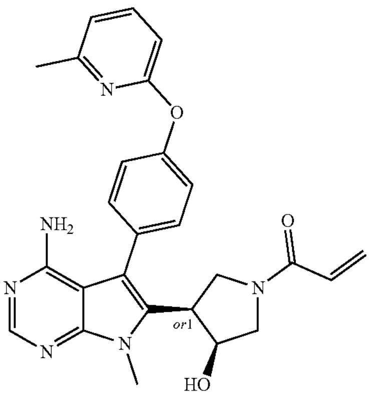 [SMILES: C=CC(=O)N1C[C@@H](O)[C@@H](c2c(-c3ccc(Oc4cccc(C)n4)cc3)c3c(N)ncnc3n2C)C1] | $^1$H NMR (400 MHz, DMSO-d$_6$) δ 8.42 (s, 1H), 7.76 (td, J = 7.8, 3.2 Hz, 1H), 7.44 (d, J = 8.4 Hz, 2H), 7.21 (d, J = 7.8 Hz, 2H), 7.05 (d, J = 7.4 Hz, 1H), 6.85 (t, J = 7.1 Hz, 1H), 6.41 (ddd, J = 59.1, 16.7, 10.2 Hz, 1H), 6.18-5.98 (m, 1H), 5.62 (t, J = 11.2 Hz, 1H), 4.42 (dd, J = 18.5, 7.3 Hz, 1H), 4.05-3.89 (m, 3H), 3.76 (s, 3H), 3.42-3.08 (m, 2H), 2.38 (s, 3H). | 471.30 |
| 1-((3R,4R)-3-(4-amino-7-methyl-5-(4-((6-methylpyridin-2-yl)oxy)phenyl)-7H-pyrrolo[2,3-d]pyrimidin-6-yl)-4-hydroxypyrrolidin-1-yl)prop-2-en-1-one | 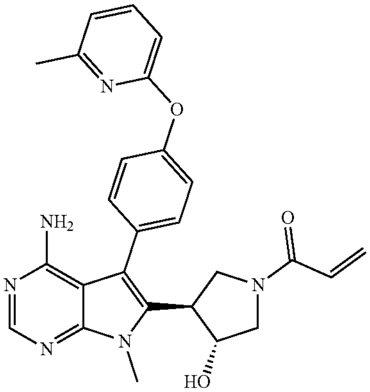 [SMILES: C=CC(=O)N1C[C@H](c2c(-c3ccc(Oc4cccc(C)n4)cc3)c3c(N)ncnc3n2C)[C@@H](O)C1] | $^1$H NMR (400 MHz, DMSO-d$_6$) δ 8.40 (d, J = 2.1 Hz, 1H), 7.77 (td, J = 7.8, 3.7 Hz, 1H), 7.49 (ddd, J = 9.4, 6.7, 2.9 Hz, 2H), 7.34-7.18 (m, 2H), 7.06 (dd, J = 7.3, 2.4 Hz, 1H), 6.86 (d, J = 8.1 Hz, 1H), 6.43 (ddd, J = 104.5, 16.8, 10.3 Hz, 1H), 6.18-5.90 (m, 2H), 5.63 (ddd, J = 26.1, 10.2, 2.4 Hz, 1H), 4.05 (d, J = 4.3 Hz, 3H), 3.93-3.78 (m, 1H), 3.71-3.22 (m, 3H), 2.38 (d, J = 11.5 Hz, 3H), 2.34-2.10 (m, 1H), 2.00 (dt, J = 38.0, 10.5 Hz, 1H). | 471.30 |

Example 19

Scheme 16

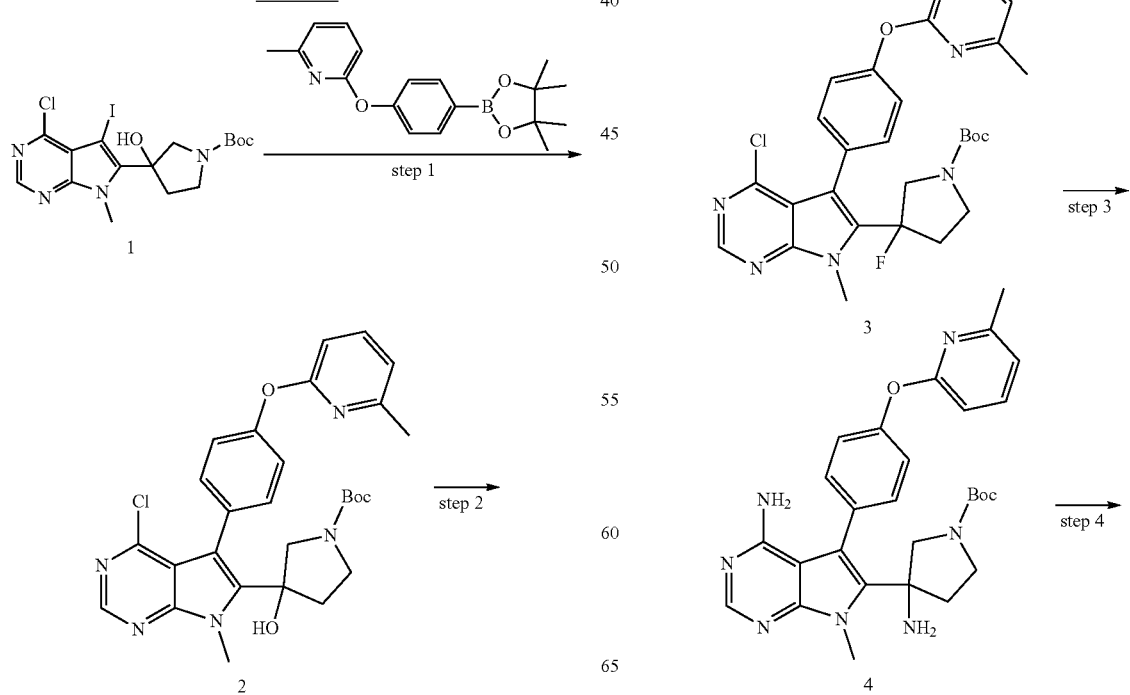

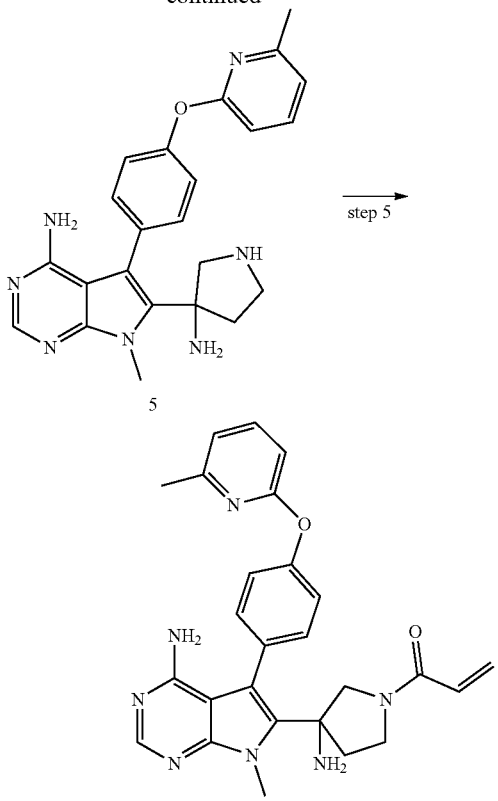

tert-butyl 3-(4-chloro-7-methyl-5-(4-((6-methylpyridin-2-yl)oxy)phenyl)-7H-pyrrolo[2,3-d]pyrimidin-6-yl)-3-hydroxypyrrolidine-1-carboxylate Step 1: A resealable reaction vial was charged with tert-butyl 3-(4-chloro-5-iodo-7-methyl-7H-pyrrolo[2,3-d]pyrimidin-6-yl)-3-hydroxypyrrolidine-1-carboxylate (700 mg, 1.46 mmol), 2-methyl-6-[4-(4,4,5,5-tetramethyl-1,3,2-dioxaborolan-2-yl)phenoxy]pyridine (546 mg, 1.75 mmol), Pd(PPh3)2Cl2 (102 mg, 146 µmol) K3PO4 (929 mg, 4.38 mmol) and a stirbar. DMF/H2O (25 mL) was added, and the solution was stirred at 50° C. for 1 h. The mixture was diluted with EtOAc(100 mL), and washed with water (3*50 mL), the organic phase was concentrated and the crude product was purified by C18 flash and further purified by prep-TLC with EA:PE=2:1 to afford tert-butyl 3-(4-chloro-7-methyl-5-{4-[(6-methylpyridin-2-yl)oxy]phenyl}-7H-pyrrolo[2,3-d]pyrimidin-6-yl)-3-hydroxypyrrolidine-1-carboxylate (100 mg, 18.7%) as light yellow solid.

tert-butyl 3-(4-chloro-7-methyl-5-(4-((6-methylpyridin-2-yl)oxy)phenyl)-7H-pyrrolo[2,3-d]pyrimidin-6-yl)-3-fluoropyrrolidine-1-carboxylate

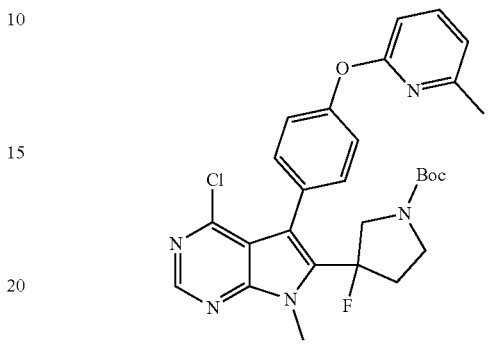

Step 2: A round bottomed flask was charged with tert-butyl 3-(4-chloro-7-methyl-5-{4-[(6-methylpyridin-2-yl)oxy]phenyl}-7H-pyrrolo[2,3-d]pyrimidin-6-yl)-3-hydroxy-pyrrolidine-1-carboxylate (90.0 mg, 167 µmol), DAST (4.00 mg, 24.8 µmol), and a stirbar. dichloromethane (10 mL) was added, and the solution was stirred at r.t. for 2 h. The mixture was quenched with NaHCO3 aq (10 mL) and extracted with DCM (30 mL) for 3 times, the organic phases was concentrated, the crude product was purified by prep-TLC (PE:EA=1:1) to afford tert-butyl 3-(4-chloro-7-methyl-5-{4-[(6-methylpyridin-2-yl)oxy]phenyl}-7H-pyrrolo[2,3-d]pyrimidin-6-yl)-3-fluoropyrrolidine-1-carboxylate (40.0 mg, 44%) as brown solid.

tert-butyl 3-amino-3-(4-amino-7-methyl-5-(4-((6-methylpyridin-2-yl)oxy)phenyl)-7H-pyrrolo[2,3-d]pyrimidin-6-yl)pyrrolidine-1-carboxylate

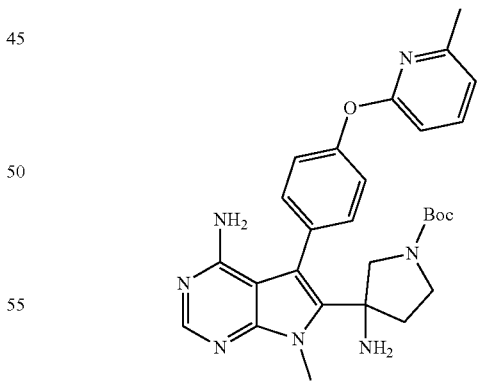

Step 3: A sealed tube was charged with tert-butyl 3-(4-chloro-7-methyl-5-{4-[(6-methylpyridin-2-yl)oxy]phenyl}-7H-pyrrolo[2,3-d]pyrimidin-6-yl)-3-fluoropyrrolidine-1-carboxylate (40.0 mg, 74.3 µmol), NH3H2O/1,4-dioxane (46 mL, v/v=1:1) and a stirbar, sealed the tube and the mixture was stirred for 18 h at 100° C. The mixture was concentrated and the crude product was purified by C18 FLASH to afford tert-butyl 3-amino-3-(4-amino-7-methyl-

1629

5-{4-[(6-methylpyridin-2-yl)oxy]phenyl}-7H-pyrrolo[2,3-d]pyrimidin-6-yl)pyrrolidine-1-carboxylate (26.0 mg, 68%) as yellow oil 6-(3-aminopyrrolidin-3-yl)-7-methyl-5-(4-((6-methylpyridin-2-yl)oxy)phenyl)-7H-pyrrolo[2,3-d]pyrimidin-4-amine

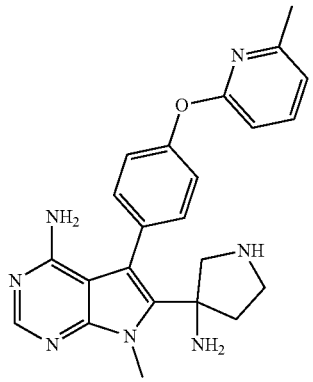 [SMILES: Cc1cccc(Oc2ccc(-c3c(C4(N)CCNC4)n(C)c4ncnc(N)c34)cc2)n1]

Step 4: A resealable reaction vial was charged with A round bottomed flask was charged with tert-butyl 3-amino-3-(4-amino-7-methyl-5-{4-[(6-methylpyridin-2-yl)oxy]phenyl}-7H-pyrrolo[2,3-d]pyrimidin-6-yl)pyrrolidine-1-carboxylate (26.0 mg, 50.4 μmol), TFA/DCM (5 mL, v/v=1:2) and a stirbar, the solution was stirred at r.t. for 2 h. The mixture was concentrated and the crude product was purified by C18 FLASH to afford 3-(4-amino-7-methyl-5-{4-[(6-methylpyridin-2-yl)oxy]phenyl}-7H-pyrrolo[2,3-d]pyrimidin-6-yl)pyrrolidin-3-amine (15.0 mg, 72%) as yellow oil.

1630

1-(3-amino-3-(4-amino-7-methyl-5-(4-((6-methylpyridin-2-yl)oxy)phenyl)-7H-pyrrolo[2,3-d]pyrimidin-6-yl)pyrrolidin-1-yl)prop-2-en-1-one

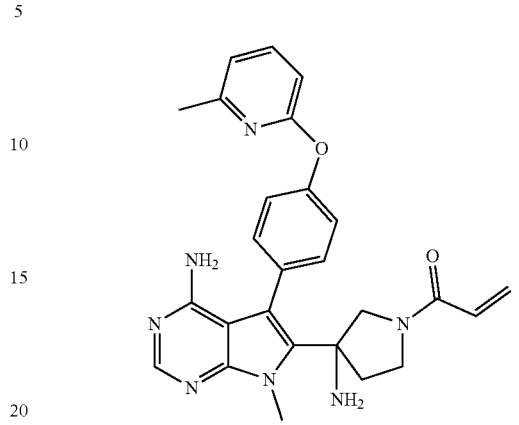

Step 5: A round bottomed flask was charged with 3-(4-amino-7-methyl-5-{4-[(6-methylpyridin-2-yl)oxy]phenyl}-7H-pyrrolo[2,3-d]pyrimidin-6-yl)pyrrolidin-3-amine (15.0 mg, 36.1 μmol), prop-2-enoyl chloride (2.60 mg, 28.8 μmol), TEA (10.9 mg, 108 μmol) and a stirbar. dichloromethane (1 mL) was added, and the solution was stirred at −65° C. for 0.5 h. The mixture was quenched with MeOH, and concentrated under reduced pressure, the crude product was purified by HPLC(Column: XBridge Shield RP18 OBD Column, 30*150 mm, 5 um; Mobile Phase A:undefined, Mobile Phase B:undefined; Flow rate:60 mL/min; Gradient:2 B to 22 B in 8 min; 220 nm) to afford 1-[3-amino-3-(4-amino-7-methyl-5-{4-[(6-methylpyridin-2-yl)oxy]phenyl}-7H-pyrrolo[2,3-d]pyrimidin-6-yl)pyrrolidin-1-yl]prop-2-en-1-one (3.00 mg, 18%) as white solid.

Characterization data for the compound prepared according to the methods of Example 19 are provided in Table 18 below.

TABLE 18

Exemplary Compound

| Compound | Structure | Proton NMR | MS [M + 1] |
|---|---|---|---|
| 1-(3-amino-3-(4-amino-7-methyl-5-(4-((6-methylpyridin-2-yl)oxy)phenyl)-7H-pyrrolo[2,3-d]pyrimidin-6-yl)pyrrolidin-1-yl)prop-2-en-1-one | 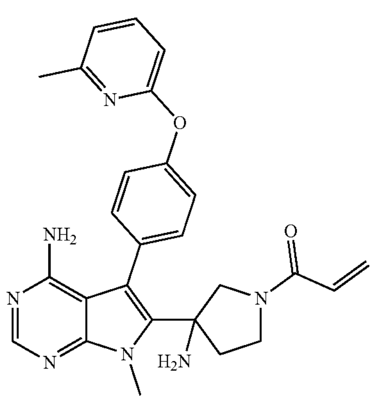 | $^1$H NMR (400 MHz, DMSO-$d_6$) δ 8.12 (s, 1H), 7.80-7.74 (m, 1H), 7.58-7.46 (m, 2H), 7.26-7.15 (m, 2H), 7.04 (dd, J = 7.4, 3.6 Hz, 1H), 6.89-6.82 (m, 1H), 6.58-6.51 (m, 1H), 6.28-6.17 (m, 1H), 6.14-6.03 (m, 1H), 5.66-5.54 (m, 1H), 4.00 (d, J = 4.5 Hz, 3H), 3.80-3.57 (m, 2H), 3.53-3.37 (m, 2H), 2.44-2.24 (m, 4H), 2.17-1.95 (m, 2H). | 470.25 |

Example 20

Scheme 17

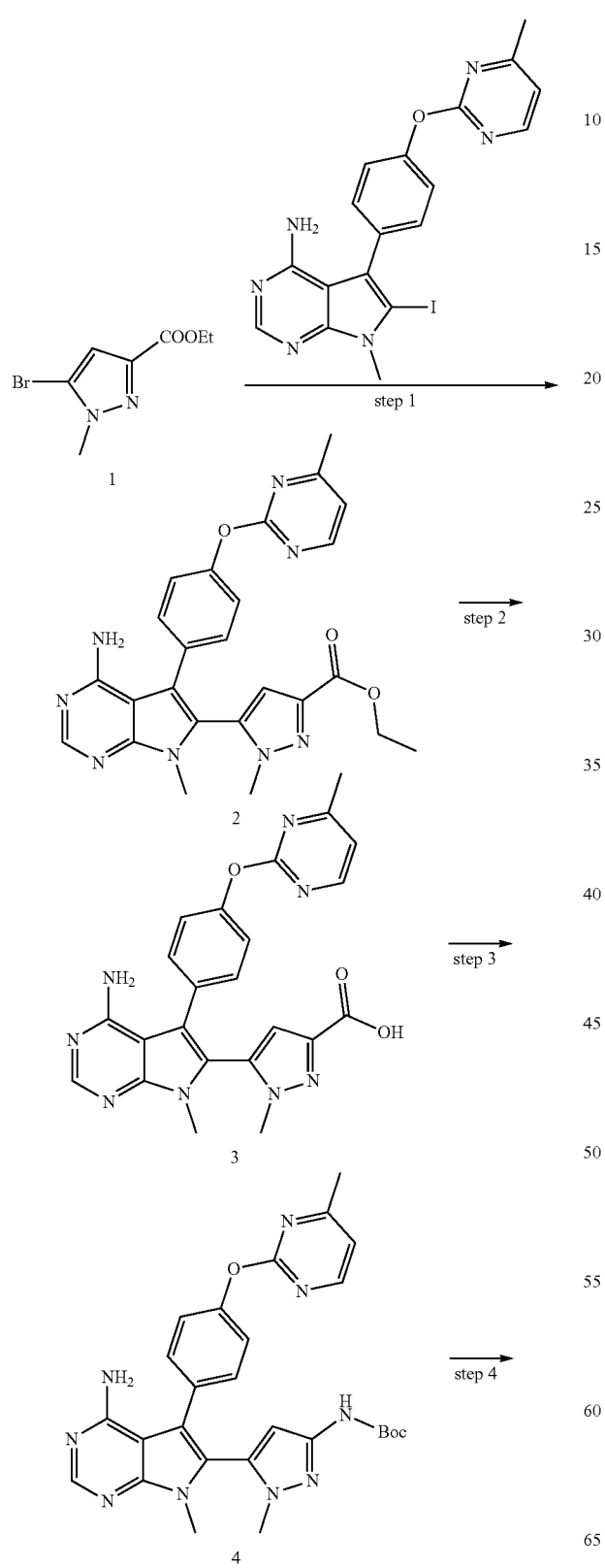

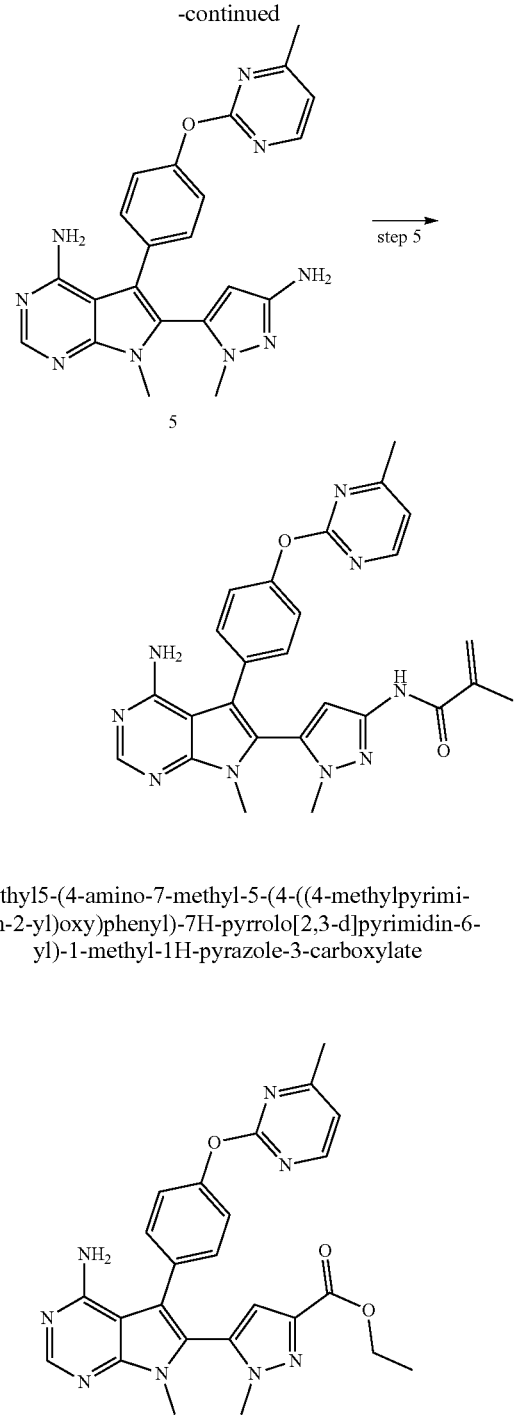

Ethyl 5-(4-amino-7-methyl-5-(4-((4-methylpyrimidin-2-yl)oxy)phenyl)-7H-pyrrolo[2,3-d]pyrimidin-6-yl)-1-methyl-1H-pyrazole-3-carboxylate Step 1: A round bottomed flask was charged with 4,4,4',4',5,5,5',5'-octamethyl-2,2'-bi(1,3,2-dioxaborolane) (610 mg, 2.4 mmol), ethyl 5-bromo-1-methyl-1H-pyrazole-3-carboxylate (464 mg, 2 mmol) 6-iodo-7-methyl-5-(4-((4-methylpyrimidin-2-yl)oxy)phenyl)-7H-pyrrolo[2,3-d]pyrimidin-4-amine (916 mg, 2 mmol), K3PO4 (1.27 g, 6 mmol), DMF/H2O (8:1, 10 mL), and a stirbar before being evacuated and purged with nitrogen three times. The mixture was stirred for 4 h at 90° C. After cooling, the mixture was diluted with water, extracted with DCM, dried over Na2SO4, evaporated in vacuum, the residue was purified by C18 column chromatography (Mobile Phase A:Water(0.05%

TFA), Mobile Phase B:ACN; Flow rate:30 mL/min; Gradient:0 B % to 45 B % in 25 min; 254 nm;) to afford ethyl 5-(4-amino-7-methyl-5-(4-((4-methylpyrimidin-2-yl)oxy)phenyl)-7H-pyrrolo[2,3-d]pyrimidin-6-yl)-1-methyl-1H-pyrazole-3-carboxylate (100 mg, 10%) as an off-white solid.

5-(4-amino-7-methyl-5-(4-((4-methylpyrimidin-2-yl)oxy)phenyl)-7H-pyrrolo[2,3-d]pyrimidin-6-yl)-1-methyl-1H-pyrazole-3-carboxylic acid

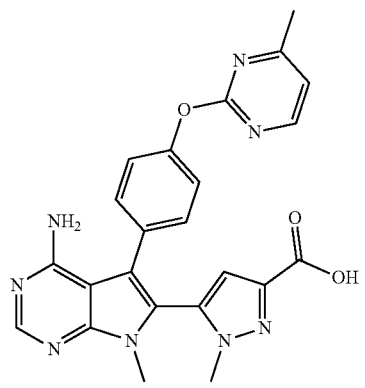 [SMILES: Cc1ccnc(Oc2ccc(-c3c(-c4cc(C(=O)O)nn4C)n(C)c4ncnc(N)c34)cc2)n1]

Step 2: A round bottomed flask was charged with ethyl 5-(4-amino-7-methyl-5-(4-((4-methylpyrimidin-2-yl)oxy)phenyl)-7H-pyrrolo[2,3-d]pyrimidin-6-yl)-1-methyl-1H-pyrazole-3-carboxylate (550 mg, 1.14 mmol), NaOH (136 mg, 3.40 mmol), MeOH (10 mL), H₂O (5 mL) and a stirbar. The mixture was stirred for 1 h at r.t. The mixture was concentrated under reduced pressure, and adjust pH to 3 with HCl (1N), filtered and dried under reduced pressure to afford 5-(4-amino-7-methyl-5-(4-((4-methylpyrimidin-2-yl)oxy)phenyl)-7H-pyrrolo[2,3-d]pyrimidin-6-yl)-1-methyl-1H-pyrazole-3-carboxylic acid (350 mg, 67%) as off-white solid.

tert-butyl (5-(4-amino-7-methyl-5-(4-((4-methylpyrimidin-2-yl)oxy)phenyl)-7H-pyrrolo[2,3-d]pyrimidin-6-yl)-1-methyl-1H-pyrazol-3-yl)carbamate

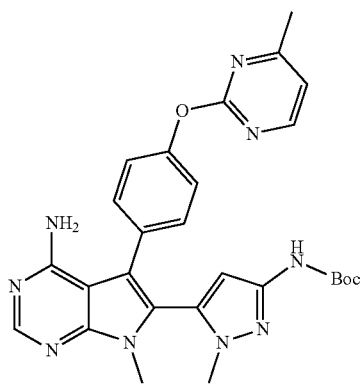 [SMILES: Cc1ccnc(Oc2ccc(-c3c(-c4cc(NC(=O)OC(C)(C)C)nn4C)n(C)c4ncnc(N)c34)cc2)n1]

Step 3: A round bottomed flask was charged with 5-(4-amino-7-methyl-5-(4-((4-methylpyrimidin-2-yl)oxy)phenyl)-7H-pyrrolo[2,3-d]pyrimidin-6-yl)-1-methyl-1H-pyrazole-3-carboxylic acid (310 mg, 0.68 mmol), DPPA (280 mg, 1.02 mmol), TEA (138 mg, 1.36 mmol), DMSO/ᵗBuOH (1:2, 24 mL) and a stirbar before being evacuated and purged with nitrogen three times. The mixture was stirred for 4 h at 90° C. After cooling, the mixture was quenched with water, extracted with DCM, dried over Na₂SO₄, evaporated in vacuo, the residue was purified by C18 column chromatography (Mobile Phase A:Water(0.05% TFA), Mobile Phase B:ACN; Flow rate:30 mL/min; Gradient:0 B % to 60 B % in 35 min; 254 nm; to afford (5-(4-amino-7-methyl-5-(4-((4-methylpyrimidin-2-yl)oxy)phenyl)-7H-pyrrolo[2,3-d]pyrimidin-6-yl)-1-methyl-1H-pyrazol-3-yl)carbamate (60 mg, 8.3%) as an off-white solid.

6-(3-amino-1-methyl-1H-pyrazol-5-yl)-7-methyl-5-(4-((4-methylpyrimidin-2-yl)oxy)phenyl)-7H-pyrrolo[2,3-d]pyrimidin-4-amine

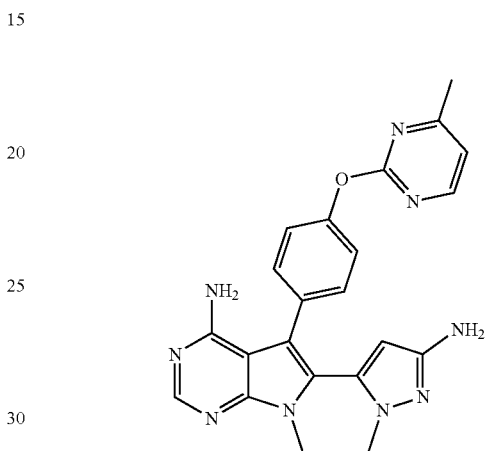

Step 4: A round bottomed flask was charged with 2-chloro-4-methylpyrimidine (60 mg, 0.11 mmol), TFA (0.4 mL), DCM (4 mL) and a stirbar. The reaction mixture was stirred for 1 h at r.t. The mixture was concentrated and dissolved with DCM (20 mL), washed with saturated NaHCO3 aqueous solution and brine, dried over Na₂SO₄, evaporated in vacuum, the residue was purified by C18 column chromatography (Mobile Phase A:Water(0.05% TFA), Mobile Phase B:ACN; Flow rate:30 mL/min; Gradient:0 B % to 60 B % in 35 min; 254 nm; to afford 6-(3-amino-1-methyl-1H-pyrazol-5-yl)-7-methyl-5-(4-((4-methylpyrimidin-2-yl)oxy)phenyl)-7H-pyrrolo[2,3-d]pyrimidin-4-amine (35 mg, 74%) as a yellow solid.

N-(5-(4-amino-7-methyl-5-(4-((4-methylpyrimidin-2-yl)oxy)phenyl)-7H-pyrrolo[2,3-d]pyrimidin-6-yl)-1-methyl-1H-pyrazol-3-yl)methacrylamide

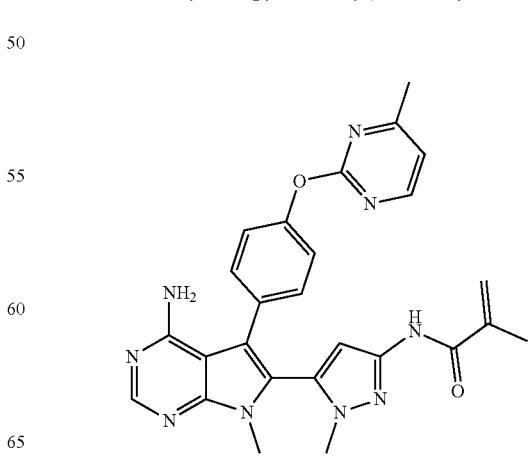

Step 5: A round bottomed flask was charged with 6-(3-amino-1-methyl-1H-pyrazol-5-yl)-7-methyl-5-(4-((4-methylpyrimidin-2-yl)oxy)phenyl)-7H-pyrrolo[2,3-d]pyrimidin-4-amine (70 mg, 0.16 mmol), Na$_2$CO$_3$ (34 mg, 0.32 mmol), ACN (20 mL) and a stirbar. Methacryloyl chloride (14.6 mg, 0.14 mmol) was added dropwise at −30° C., and the mixture was stirred for 1 h. then the mixture was quenched with MeOH at −30° C., and diluted with water(10 mL), extracted with DCM (20 mL*3), the organic phase was combined and washed with brine for two times, dried over Na$_2$SO$_4$, concentrated in vacuum, the residue was purified by HPLC and lyophilization to afford N-(5-(4-amino-7-methyl-5-(4-((4-methylpyrimidin-2-yl)oxy)phenyl)-7H-pyrrolo[2,3-d]pyrimidin-6-yl)-1-methyl-1H-pyrazol-3-yl)methacrylamide (12.5 mg, 15%) as a white solid.

Additional compounds prepared according to the methods of Example 20 are depicted in Table 19 below.

TABLE 19

Additional Exemplary Compounds

| Compound | Structure | Proton NMR | MS [M + 1] |
|---|---|---|---|
| N-(5-(4-amino-7-methyl-5-(4-((4-methylpyrimidin-2-yl)oxy)phenyl)-7H-pyrrolo[2,3-d]pyrimidin-6-yl)-1-methyl-1H-pyrazol-3-yl)methacrylamide | 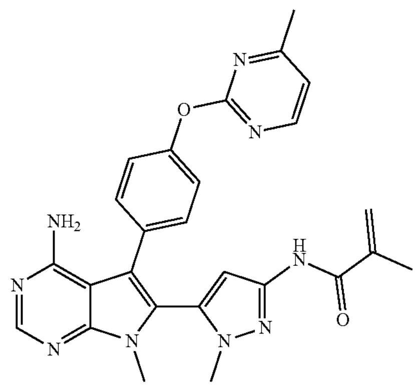 [SMILES: C=C(C)C(=O)Nc1cc(-c2c(-c3ccc(Oc4nccc(C)n4)cc3)c3c(N)ncnc3n2C)n(C)n1] | $^1$H NMR (400 MHz, DMSO-d$_6$) δ 10.43 (s, 1H), 8.48(d, J = 4.2 Hz, 1H), 8.25 (s, 1H), 7.31 (d, J = 8.4 Hz, 2H), 7.24 (d, J = 8.8 Hz, 2H), 7.16 (d, J = 4.2 Hz, 1H), 6.84 (s, 1H), 5.87(s, 1H), 5.49 (s, 1H), 3.59(s, 3H), 3.27(s, 3H), 2.41(s, 3H), 1.93(s, 3H). | 496.10 |
| N-(5-(4-amino-7-methyl-5-(4-((4-methylpyrimidin-2-yl)oxy)phenyl)-7H-pyrrolo[2,3-d]pyrimidin-6-yl)-1-methyl-1H-pyrazol-4-yl)methacrylamide | 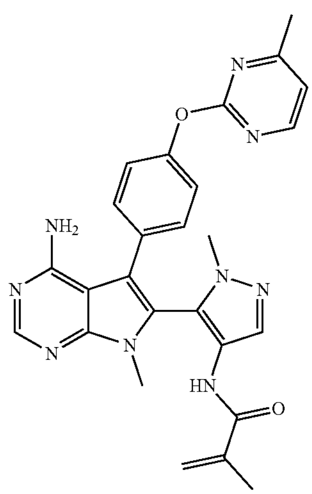 [SMILES: C=C(C)C(=O)Nc1cnn(C)c1-c1c(-c2ccc(Oc3nccc(C)n3)cc2)c2c(N)ncnc2n1C] | $^1$H NMR (400 MHz, DMSO-d$_6$) δ 9.53 (s, 1H), 8.47(d, J = 4.8 Hz, 1H), 8.24 (s, 1H), 7.72(s, 1H), 7.37 (d, J = 8.4 Hz, 2H), 7.22-7.15 (m, 3H), 5.60(s, 1H), 5.41 (s, 1H), 3.51(s, 3H), 3.27(s, 3H), 2.41(s, 3H), 1.92(s, 3H). | 496.15 |
| N-(5-(4-amino-5-(3-fluoro-4-((4-methylpyrimidin-2-yl)oxy)phenyl)-7-methyl-7H-pyrrolo[2,3-d]pyrimidin-6-yl)-1-methyl-1H-pyrazol-3-yl)methacrylamide | 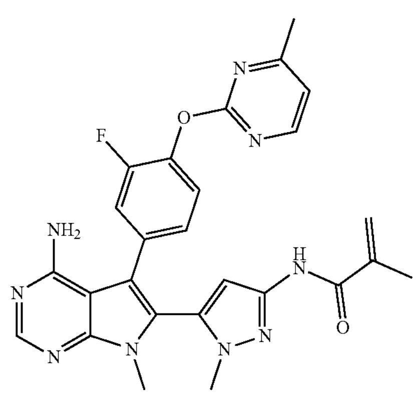 [SMILES: C=C(C)C(=O)Nc1cc(-c2c(-c3ccc(Oc4nccc(C)n4)c(F)c3)c3c(N)ncnc3n2C)n(C)n1] | $^1$H NMR (400 MHz, DMSO-d$_6$) δ 10.44 (s, 1H), 8.49 (d, J = 5.0 Hz, 1H), 8.26 (s, 1H), 7.41 (t, J = 8.4 Hz, 1H), 7.23-7.18 (m, 2H), 7.11 (m, 1H), 6.87 (s, 1H), 6.25 (s, 1H), 5.88 (s, 1H), 5.54-5.46 (s, 1H), 3.59 (s, 3H), 3.30 (s, 3H), 2.42 (s, 3H), 1.94 (s, 3H). | 514.20 |

Example 21

Scheme 18

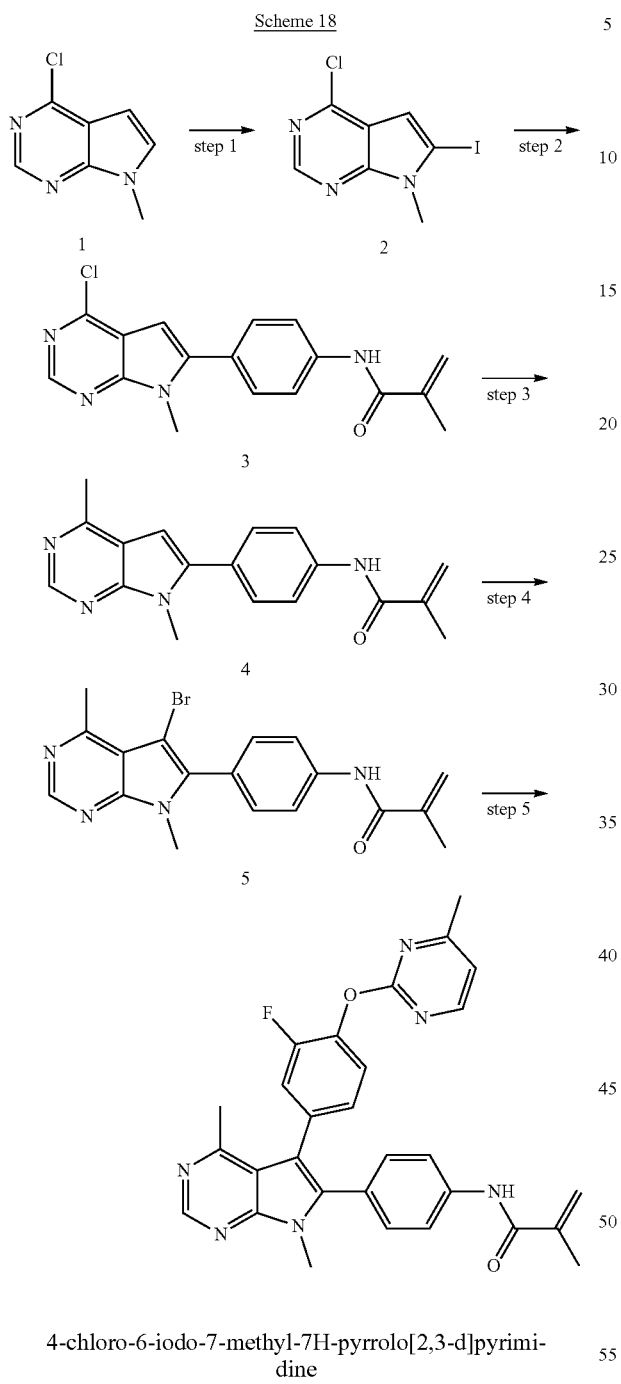

4-chloro-6-iodo-7-methyl-7H-pyrrolo[2,3-d]pyrimidine

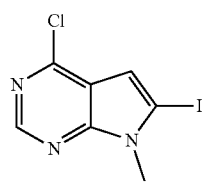

Step 1: A three-neck flask was charged with 4-chloro-7-methyl-7H-pyrrolo[2,3-d]pyrimidine (3 g, 17.96 mmol), THF (50 mL) and a stir bar before being evacuated and purged with nitrogen three times. LDA (13.5 mL, 26.9 mmol) was added dropwise at −78° C. The reaction mixture was stirred for 1 h at −78° C. Then 12 (5.9 g, 23.3 mmol) was added, the reaction mixture was stirred for 1 h at −78° C. The mixture was quenched with water, extracted with EA, dried over $Na_2SO_4$, evaporated in vacuo, the residue was purified by silica gel column chromatography, eluted with DCM/MeOH (50:1~10:1) to afford 4-chloro-6-iodo-7-methyl-7H-pyrrolo[2,3-d]pyrimidine(4 g, 76%) as a yellow solid.

N-(4-(4-chloro-7-methyl-7H-pyrrolo[2,3-d]pyrimidin-6-yl)phenyl)methacrylamide

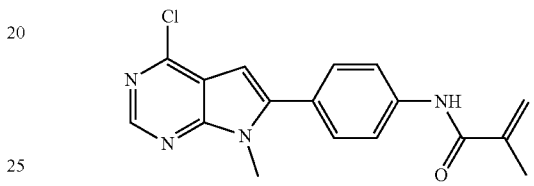

Step 2: A round bottomed flask was charged with 4-chloro-6-iodo-7-methyl-7H-pyrrolo[2,3-d]pyrimidine (1 g, 3.4 mmol), N-(4-(4,4,5,5-tetramethyl-1,3,2-dioxaborolan-2-yl)phenyl)methacrylamide (1.2 g, 4.1 mmol), Pd(PPh3)2Cl$_2$ (4.5 g, 6.2 mmol), K3PO4 (2.16 g, 10.2 mmol), DMF/H2O (16:1, 20 mL) and a stir bar before being evacuated and purged with nitrogen three times. The mixture was stirred for 1 h at 50° C. After cooling, the mixture was diluted with water, extracted with EA, dried over $Na_2SO_4$, evaporated in vacuo, the residue was purified by silica gel column chromatography, eluted with DCM/MeOH (100:1~10:1) to afford N-(4-(4-chloro-7-methyl-7H-pyrrolo[2,3-d]pyrimidin-6-yl)phenyl)methacrylamide (700 mg, 70%) as yellow solid.

N-(4-(4,7-dimethyl-7H-pyrrolo[2,3-d]pyrimidin-6-yl)phenyl)methacrylamide

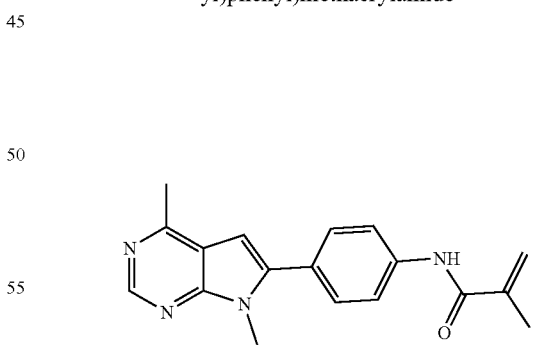

Step 3: A round bottomed flask was charged with N-(4-(4-chloro-7-methyl-7H-pyrrolo[2,3-d]pyrimidin-6-yl)phenyl)methacrylamide (0.7 g, 2.3 mmol), Pd(PPh$_3$)$_4$ (0.26 g, 0.23 mmol), DMF (10 mL) and a stir bar before being evacuated and purged with nitrogen three times. Zn(CH$_3$)$_2$ (1 M, 3.45 mL 3.45 mmol) was added. The mixture was stirred for 2 h at 90° C. After cooling, the mixture was diluted with water, extracted with DCM, dried over $Na_2SO_4$, evaporated in vacuo, the residue was purified by silica gel column chromatography, eluted with DCM/MeOH (100:1~10:1) to afford N-(4-(4,7-dimethyl-7H-pyrrolo[2,3-d]pyrimidin-6-yl)phenyl)methacrylamide (400 mg, 57%) as brown solid.

6-iodo-7-methyl-5-(4-((4-methylpyrimidin-2-yl)oxy)phenyl)-7H-pyrrolo[2,3-d]pyrimidin-4-amine

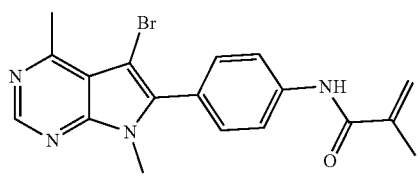 [SMILES: C=C(C)C(=O)Nc1ccc(-c2c(Br)c3c(C)ncnc3n2C)cc1]

Step 4: A round bottomed flask was charged with N-(4-(4,7-dimethyl-7H-pyrrolo[2,3-d]pyrimidin-6-yl)phenyl)methacrylamide (0.4 g, 1.3 mmol), DCM (10 mL) and a stir bar. NBS (7.43 g, 1.3 mmol) was added. The mixture was stirred for 1 h. The reaction was quenched with saturated NaHSO₃ aqueous solution until the pH to 8-9, extracted with DCM (100 mL*3), the organic phase was combined and washed with brine for two times, dried with Na₂SO₄, evaporated in vacuo, the residue was dissolved with ACN (25 mL), and filtered, the filter cake was washed with ACN, dried under reduced pressure to afford 6-iodo-7-methyl-5-(4-((4-methylpyrimidin-2-yl)oxy)phenyl)-7H-pyrrolo[2,3-d]pyrimidin amine(340 mg, 67%) as off-white solid.

N-(4-(5-(3-fluoro-4-((4-methylpyrimidin-2-yl)oxy)phenyl)-4,7-dimethyl-7H-pyrrolo[2,3-d]pyrimidin-6-yl)phenyl)methacrylamide

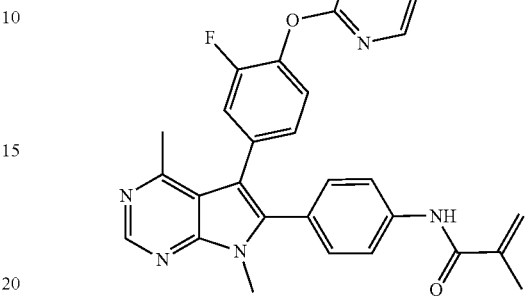

Step 5: A round bottomed flask was charged with 6-iodo-7-methyl-5-(4-((4-methylpyrimidin-2-yl)oxy)phenyl)-7H-pyrrolo[2,3-d]pyrimidin-4-amine (340 mg, 0.88 mmol), 2-(2-fluoro-4-(4,4,5,5-tetramethyl-1,3,2-dioxaborolan-2-yl)phenoxy)-4-methylpyrimidine (330 mg, 1 mmol), Pd(dppf)Cl₂ (66 mg, 0.09 mmol), K3PO4 (560 mg, 2.64 mmol), DMF/H2O (16:1, 10 mL) and a stir bar before being evacuated and purged with nitrogen three times. The mixture was stirred for 2 h at 90° C. After cooling, the mixture was diluted with water, extracted with DCM, dried over Na₂SO₄, evaporated in vacuo, the residue was purified by prep-HPLC to afford 6-(4-aminophenyl)-7-methyl-5-(4-((4-methylpyrimidin-2-yl)oxy)phenyl)-7H-pyrrolo[2,3-d]pyrimidin-4-amine (46.6 mg, 10.4%) as a white solid.

Additional compounds prepared according to the methods of Example 21 are depicted in Table 20 below.

TABLE 20

Additional Exemplary Compounds

| Compound | Structure | Proton NMR | MS [M + 1] |
|---|---|---|---|
| N-(4-(5-(3-fluoro-4-((4-methylpyrimidin-2-yl)oxy)phenyl)-4,7-dimethyl-7H-pyrrolo[2,3-d]pyrimidin-6-yl)phenyl)methacrylamide | 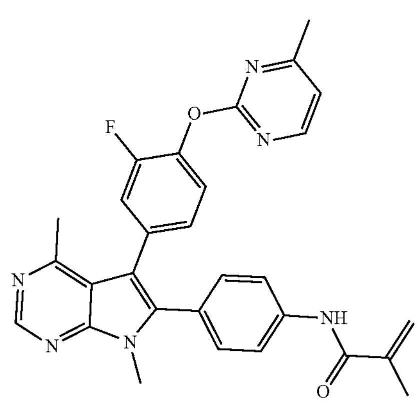 [SMILES: C=C(C)C(=O)Nc1ccc(-c2c(-c3ccc(Oc4nccc(C)n4)c(F)c3)c3c(C)ncnc3n2C)cc1] | ¹H NMR (400 MHz, DMSO-d₆) δ 9.95 (s, 1H), 8.74 (s, 1H), 8.48 (d, J = 5.0 Hz, 1H), 7.80-7.74 (m, 2H), 7.41-7.26 (m, 4H), 7.22-7.11 (m, 2H), 5.80 (s, 1H), 5.54 (t, J = 1.5 Hz, 1H), 3.70 (s, 3H), 2.40 (d, J = 11.0 Hz, 6H), 1.95 (d, J = 1.2 Hz, 3H). | 509.20 |

TABLE 20-continued

Additional Exemplary Compounds

| Compound | Structure | Proton NMR | MS [M + 1] |
|---|---|---|---|
| N-(4-(5-(3-fluoro-4-((4-methylpyrimidin-2-yl)oxy)phenyl)-4,7-dimethyl-7H-pyrrolo[2,3-d]pyrimidin-6-yl)-3-methylphenyl)acrylamide | (structure) | $^1$H NMR (400 MHz, DMSO-d$_6$) 10.24 (s, 1H), 8.74 (s, 1H), 8.47 (d, J = 5.0 Hz, 1H), 7.66-7.57 (m, 1H), 7.35 (d, J = 8.3 Hz, 1H), 7.33-7.24 (m, 2H), 7.17 (d, J = 5.1 Hz, 1H), 7.16-7.10 (m, 1H), 6.45 (dd, J = 17.0, 10.1 Hz, 1H), 6.28 (dd, J = 17.0, 2.1 Hz, 1H), 5.78 (dd, J = 10.1, 2.1 Hz, 1H), 3.52 (s, 3H), 2.41 (d, J = 8.1 Hz, 6H), 2.00 (s, 3H). | 509.35 |
| (S)-N-(4-(4,7-dimethyl-5-(4-(pyrrolidine-1-carbonyl)cyclohex-1-en-1-yl)-7H-pyrrolo[2,3-d]pyrimidin-6-yl)-3-methylphenyl)acrylamide | (structure) | $^1$H NMR (400 MHz, DMSO-d$_6$) 10.27 (s, 1H), 8.65 (s, 1H), 7.71 (dd, J = 4.9, 2.1 Hz, 1H), 7.66-7.58 (m, 1H), 7.24 (dd, J = 10.7, 8.3 Hz, 1H), 6.47 (dd, J = 17.0, 10.1 Hz, 1H), 6.29 (dd, J = 17.0, 2.1 Hz, 1H), 5.80 (dd, J = 10.1, 2.1 Hz, 1H), 5.66 (d, J = 14.9 Hz, 1H), 3.47-3.39 (m, 5H), 3.32 (s, 3H), 3.26 (t, J = 6.8 Hz, 2H), 2.65 (s, 3H), 2.27-2.16 (m, 1H), 2.07 (t, J = 3.8 Hz, 4H), 1.85 (p, J = 6.6 Hz, 2H), 1.74 (p, J = 6.5 Hz, 3H), 1.49-1.41 (m, 1H). | 484.45 |
| (R)-N-(4-(4,7-dimethyl-5-(4-(pyrrolidine-1-carbonyl)cyclohex-1-en-1-yl)-7H-pyrrolo[2,3-d]pyrimidin-6-yl)-3-methylphenyl)acrylamide | (structure) | $^1$H NMR (400 MHz, DMSO-d$_6$) 10.28 (s, 1H), 8.64 (s, 1H), 7.71 (dd, J = 5.1, 2.0 Hz, 1H), 7.62 (dt, J = 5.9, 3.2 Hz, 1H), 7.23 (dd, J = 10.6, 8.3 Hz, 1H), 6.47 (dd, J = 17.0, 10.1 Hz, 1H), 6.29 (dd, J = 17.0, 2.1 Hz, 1H), 5.79 (dd, J = 10.0, 2.0 Hz, 1H), 5.70-5.61 (m, 1H), 3.42 (s, 4H), 3.26 (t, J = 6.9 Hz, 2H), 2.65 (s, 3H), 2.18 (d, J = 10.3 Hz, 0H), 2.06 (d, J = 4.0 Hz, 4H), 1.85 (p, J = 6.7 Hz, 2H), 1.74 (p, J = 6.7 Hz, 3H), 1.45 (d, J = 12.9 Hz, 1H). | 484.45 |
| N-[4-(3-{3-fluoro-4-[(4-methylpyrimidin-2-yl)oxy]phenyl}-1,4-dimethyl-1H-pyrrolo[3,2-c]pyridin-2-yl)-3-methylphenyl]prop-2-enamide | (structure) | $^1$H NMR (400 MHz, DMSO-d$_6$) δ 10.23 (s, 1H), 8.47 (d, J = 5.1 Hz, 1H), 8.29 (s, 1H), 7.64 (s, 1H), 7.61 (s, 1H), 7.59 (s, 1H), 7.30 (dd, J = 12.2, 8.6 Hz, 3H), 7.15 (dd, J = 17.4, 6.6 Hz, 2H), 6.45 (dd, J = 16.9, 10.1 Hz, 1H), 6.36-6.09 (m, 1H), 5.78 (d, J = 11.8 Hz, 1H), 3.56 (s, 3H), 2.45 (s, 3H), 2.40 (s, 3H), 2.01 (s, 3H). | 508.25 |

TABLE 20-continued

Additional Exemplary Compounds

| Compound | Structure | Proton NMR | MS [M + 1] |
|---|---|---|---|
| N-(4-(4,7-dimethyl-5-(4-((4-methylpyrimidin-2-yl)oxy)phenyl)-7H-pyrrolo[2,3-d]pyrimidin-6-yl)-3-methylphenyl) acrylamide | 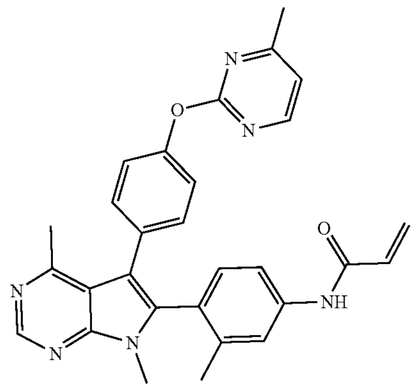 [SMILES: C=CC(=O)Nc1ccc(-c2c(-c3ccc(Oc4nccc(C)n4)cc3)c3c(C)ncnc3n2C)c(C)c1] | $^1$H NMR (400 MHz, DMSO-d6) 10.22 (s, 1H), 8.73 (s, 1H), 8.46 (d, J = 5.0 Hz, 1H), 7.64-7.55 (m, 2H), 7.36-7.26 (m, 3H), 7.17-7.08 (m, 3H), 6.44 (dd, J = 17.0, 10.1 Hz, 1H), 6.27 (dd, J = 17.0, 2.1 Hz, 1H), 5.78 (dd, J = 10.1, 2.1 Hz, 1H), 3.52 (s, 3H), 2.39 (d, J = 4.4 Hz, 6H), 1.99 (s, 3H). | 491.35 |
| N-[4-(5-{3-fluoro-4-[(4-methylpyrimidin-2-yl)oxy]phenyl}-4,7-dimethyl-7H-pyrrolo[2,3-d]pyrimidin-6-yl)-3-methylphenyl]-2-methylprop-2-enamide | 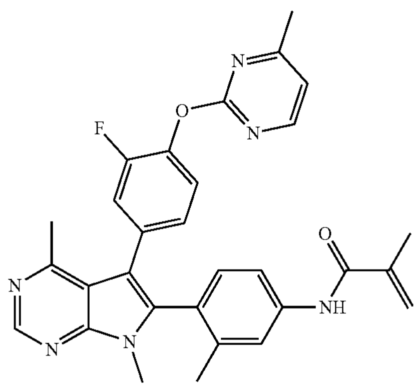 [SMILES: C=C(C)C(=O)Nc1ccc(-c2c(-c3ccc(Oc4nccc(C)n4)c(F)c3)c3c(C)ncnc3n2C)c(C)c1] | $^1$H NMR (400 MHz, DMSO-d$_6$) δ 9.87 (s, 1H), 8.74 (s, 1H), 8.47 (d, J = 5.0 Hz, 1H), 7.68 (d, J = 2.1 Hz, 1H), 7.65-7.61 (m, 1H), 7.34 (d, J = 8.3 Hz, 1H), 7.32-7.26 (m, 2H), 7.18 (d, J = 5.1 Hz, 1H), 7.16-7.10 (m, 1H), 5.81 (t, J = 1.1 Hz, 1H), 5.54 (s, 1H), 3.52 (s, 3H), 2.41 (d, J = 7.5 Hz, 6H), 1.99 (s, 3H), 1.97-1.91 (m, 3H). | 523.35 |
| N-[4-(4,7-dimethyl-5-{4-[(4-methylpyrimidin-2-yl)oxy]phenyl}-7H-pyrrolo[2,3-d]pyrimidin-6-yl)-3-methylphenyl]-2-methylprop-2-enamide | 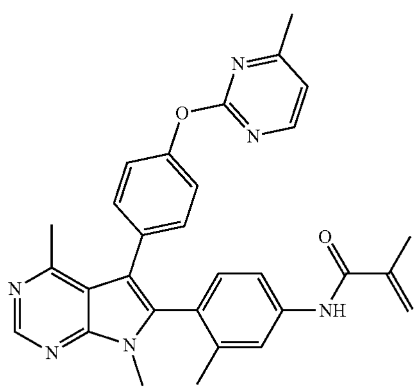 [SMILES: C=C(C)C(=O)Nc1ccc(-c2c(-c3ccc(Oc4nccc(C)n4)cc3)c3c(C)ncnc3n2C)c(C)c1] | $^1$H NMR (400 MHz, DMSO-d$_6$) δ 9.85 (s, 1H), 8.73 (s, 1H), 8.46 (d, J = 5.0 Hz, 1H), 7.65 (d, J = 2.1 Hz, 1H), 7.63-7.59 (m, 1H), 7.50-7.27 (m, 3H), 7.18-6.92 (m, 3H), 5.80 (t, J = 1.0 Hz, 1H), 5.53 (d, J = 1.9 Hz, 1H), 3.52 (s, 3H), 2.39 (d, J = 4.6 Hz, 6H), 1.98 (s, 3H), 1.95 (d, J = 1.3 Hz, 3H). | 505.35 |
| N-(4-(4,7-dimethyl-5-(4-phenoxyphenyl)-7H-pyrrolo[2,3-d]pyrimidin-6-yl)phenyl) acrylamide | 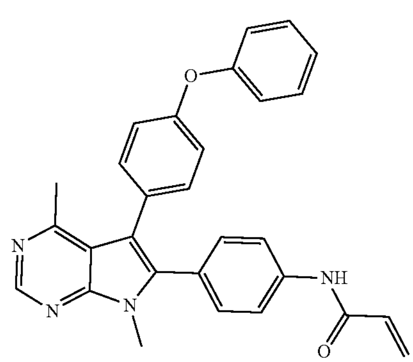 [SMILES: C=CC(=O)Nc1ccc(-c2c(-c3ccc(Oc4ccccc4)cc3)c3c(C)ncnc3n2C)cc1] | $^1$H NMR (400 MHz, DMSO-d$_6$) δ 10.28 (s, 1H), 8.72 (s, 1H), 7.71 (d, J = 8.6 Hz, 2H), 7.46-7.32 (m, 2H), 7.30 (s, 2H), 7.29 (d, J = 8.7 Hz, 2H), 7.16 (t, J = 7.4 Hz, 1H), 7.07-7.00 (m, 2H), 6.96 (d, J = 8.6 Hz, 2H), 6.45 (dd, J = 16.9, 10.1 Hz, 1H), 6.28 (dd, J = 17.1, 2.0 Hz, 0H), 5.79 (dd, J = 10.1, 2.0 Hz, 1H), 3.70 (s, 3H), 2.34 (s, 3H). | 461.30 |

TABLE 20-continued

Additional Exemplary Compounds

| Compound | Structure | Proton NMR | MS [M + 1] |
|---|---|---|---|
| N-(4-(4-methyl-5-(4-phenoxyphenyl)-7H-pyrrolo[2,3-d]pyrimidin-6-yl)phenyl)acrylamide | 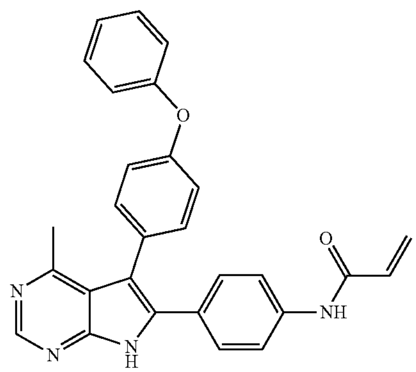 [SMILES: C=CC(=O)Nc1ccc(-c2[nH]c3ncnc(C)c3c2-c2ccc(Oc3ccccc3)cc2)cc1] | ¹H NMR (400 MHz, DMSO-d₆) δ 9.46 (s, 1H), 8.52 (t, J = 6.1 Hz, 1H), 8.22-7.98 (m, 4H), 7.96-7.76 (m, 4H), 7.42 (t, J = 7.8 Hz, 1H), 7.37-7.26 (m, 1H), 7.12 (d, J = 8.3 Hz, 2H), 6.88 (d, J = 8.3 Hz, 2H), 6.29 (dd, J = 17.1, 10.1 Hz, 1H), 6.14 (dd, J = 17.1, 2.3 Hz, 1H), 5.62 (dd, J = 10.0, 2.4 Hz, 1H), 4.28 (d, J = 5.9 Hz, 2H), 3.50 (s, 3H), 3.18 (s, 4H), 3.05 (s, 2H). | 447.30 |
| N-(4-(4,7-dimethyl-5-phenyl-7H-pyrrolo[2,3-d]pyrimidin-6-yl)phenyl)acrylamide | 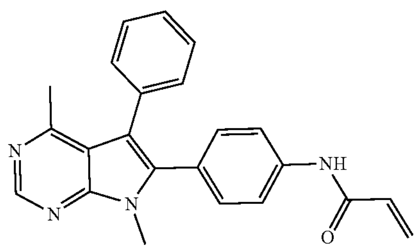 [SMILES: C=CC(=O)Nc1ccc(-c2c(-c3ccccc3)c3c(C)ncnc3n2C)cc1] | ¹H NMR (400 MHz, DMSO-d₆) δ 10.27 (s, 1H), 8.71 (s, 1H), 7.72-7.64 (m, 2H), 7.38-7.25 (m, 7H), 6.43 (dd, J = 17.0, 10.1 Hz, 1H), 6.27 (dd, J = 17.0, 2.1 Hz, 1H), 5.78 (dd, J = 10.0, 2.1 Hz, 1H), 3.70 (s, 3H), 2.28 (s, 3H). | 369.20 |
| N-(4-(4,7-dimethyl-5-(6-(4-methyl-1H-pyrazol-1-yl)pyridin-3-yl)-7H-pyrrolo[2,3-d]pyrimidin-6-yl)phenyl)acrylamide | 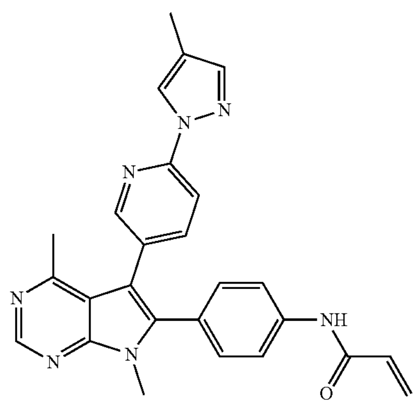 [SMILES: C=CC(=O)Nc1ccc(-c2c(-c3ccc(-n4cc(C)cn4)nc3)c3c(C)ncnc3n2C)cc1] | ¹H NMR (400 MHz, DMSO-d₆) δ 10.29 (s, 1H), 8.75 (s, 1H), 8.37 (t, J = 1.0 Hz, 1H), 8.29 (dd, J = 2.3, 0.8 Hz, 1H), 7.90 (dd, J = 8.4, 2.3 Hz, 1H), 7.84 (dd, J = 8.4, 0.8 Hz, 1H), 7.76-7.69 (m, 2H), 7.65 (s, 1H), 7.42-7.34 (m, 2H), 6.43 (dd, J = 16.9, 10.0 Hz, 1H), 6.27 (dd, J = 17.0, 2.1 Hz, 1H), 5.78 (dd, J = 10.1, 2.1 Hz, 1H), 3.72 (s, 3H), 2.39 (s, 3H), 2.11 (d, J = 1.0 Hz, 3H). | 450.30 |
| N-(4-(4,7-dimethyl-5-(4-((6-methylpyridin-2-yl)oxy)phenyl)-7H-pyrrolo[2,3-d]pyrimidin-6-yl)phenyl)acrylamide | 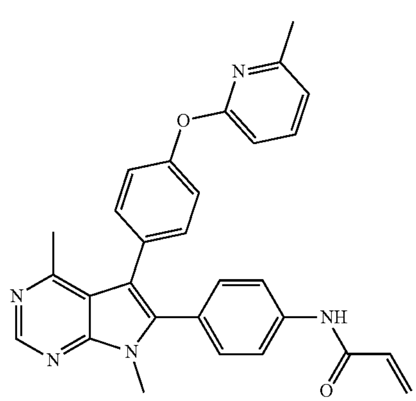 [SMILES: C=CC(=O)Nc1ccc(-c2c(-c3ccc(Oc4cccc(C)n4)cc3)c3c(C)ncnc3n2C)cc1] | ¹H NMR (400 MHz, DMSO-d₆) δ 10.29 (s, 1H), 8.72 (s, 1H), 7.78-7.69 (m, 3H), 7.36 (d, J = 8.2 Hz, 2H), 7.30 (d, J = 8.0 Hz, 2H), 7.06 (d, J = 8.0 Hz, 2H), 7.01 (d, J = 7.4 Hz, 1H), 6.75 (d, J = 8.2 Hz, 1H), 6.44 (dd, J = 17.0, 10.1 Hz, 1H), 6.33-6.23 (m, 1H), 5.78 (d, J = 10.1 Hz, 1H), 3.71 (s, 3H), 2.34 (s, 6H). | 476.15 |

TABLE 20-continued

Additional Exemplary Compounds

| Compound | Structure | Proton NMR | MS [M + 1] |
|---|---|---|---|
| N-(4-(7-isopropyl-4-methyl-5-(4-phenoxyphenyl)-7H-pyrrolo[2,3-d]pyrimidin-6-yl)phenyl) acrylamide | 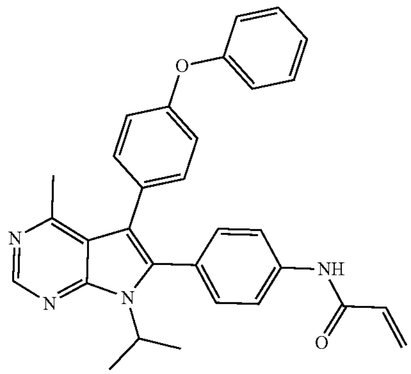 [SMILES: C=CC(=O)Nc1ccc(-c2c(-c3ccc(Oc4ccccc4)cc3)c3c(C)ncnc3n2C(C)C)cc1] | $^1$H NMR (400 MHz, DMSO-d$_6$) δ 10.29 (s, 1H), 8.69 (s, 1H), 7.72 (d, J = 8.2 Hz, 2H), 7.41 (t, J = 7.8 Hz, 2H), 7.29 (dd, J = 16.6, 8.3 Hz, 4H), 7.16 (t, J = 7.3 Hz, 1H), 7.02 (d, J = 8.0 Hz, 2H), 6.90 (d, J = 8.2 Hz, 2H), 6.45 (dd, J = 16.9, 10.0 Hz, 1H), 6.29 (dd, J = 16.8, 1.9 Hz, 1H), 5.79 (dd, J = 10.2, 2.0 Hz, 1H), 4.43 (p, J = 6.8 Hz, 1H), 2.30 (s, 3H), 1.63 (d, J = 6.8 Hz, 6H). | 489.15 |
| N-(4-(5-(benzo[b]thiophen-2-yl)-4,7-dimethyl-7H-pyrrolo[2,3-d]pyrimidin-6-yl)phenyl) acrylamide | 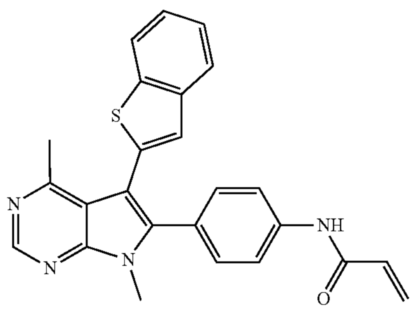 [SMILES: C=CC(=O)Nc1ccc(-c2c(-c3cc4ccccc4s3)c3c(C)ncnc3n2C)cc1] | $^1$H NMR (400 MHz, DMSO-d$_6$) δ 10.28 (s, 1H), 8.77 (s, 1H), 7.89 (d, J = 7.9 Hz, 1H), 7.86-7.79 (m, 1H), 7.75-7.68 (m, 2H), 7.52-7.43 (m, 3H), 7.42-7.29 (m, 2H), 6.42 (dd, J = 17.0, 10.1 Hz, 1H), 6.26 (dd, J = 16.9, 2.1 Hz, 1H), 5.77 (dd, J = 10.0, 2.1 Hz, 1H), 3.72 (s, 3H), 2.44 (s, 3H). | 425.25 |
| N-(4-(5-(benzo[b]thiophen-2-yl)-4-methyl-7H-pyrrolo[2,3-d]pyrimidin-6-yl)phenyl) acrylamide | 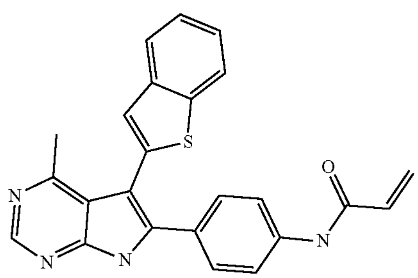 [SMILES: C=CC(=O)Nc1ccc(-c2[nH]c3ncnc(C)c3c2-c2cc3ccccc3s2)cc1] | $^1$H NMR (400 MHz, DMSO-d$_6$) δ 12.74 (s, 1H), 10.25 (s, 1H), 8.68 (s, 1H), 8.05-7.95 (m, 1H), 7.89 (dd, J = 6.8, 1.8 Hz, 1H), 7.63 (d, J = 8.8 Hz, 2H), 7.57-7.49 (m, 3H), 7.45-7.35 (m, 2H), 6.41 (dd, J = 17.0, 10.1 Hz, 1H), 6.25 (dd, J = 17.0, 2.1 Hz, 1H), 5.77 (dd, J = 10.1, 2.1 Hz, 1H), 2.36 (s, 3H). | 411.15 |

Example 22

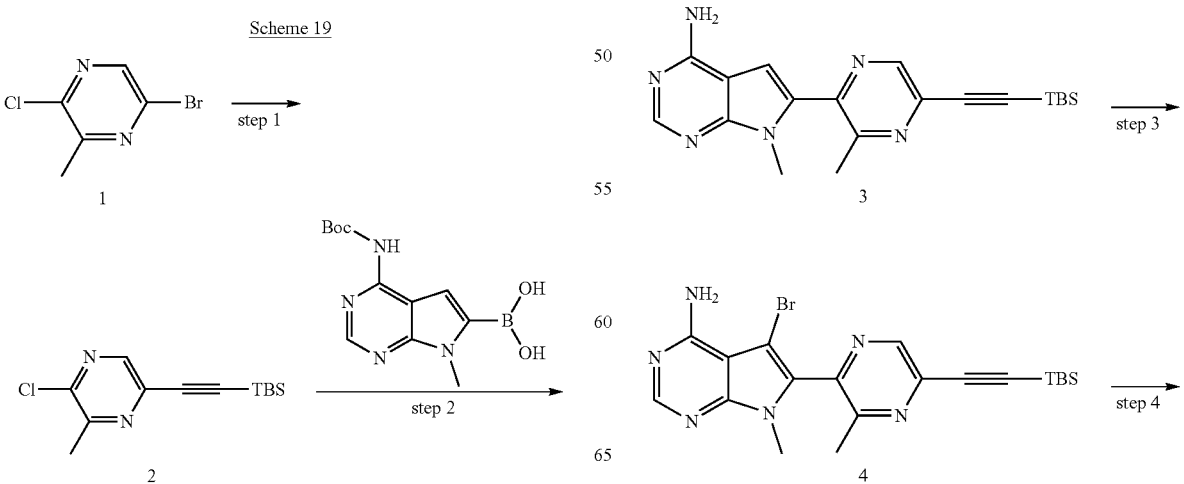

-continued

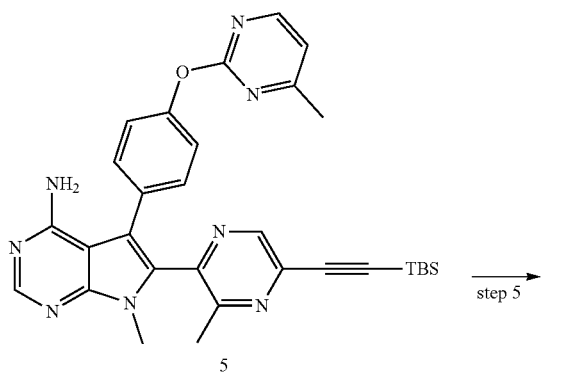

5

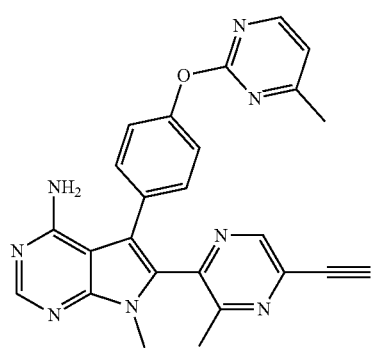

5-[2-(tert-butyldimethylsilyl)ethynyl]-2-chloro-3-methylpyrazine

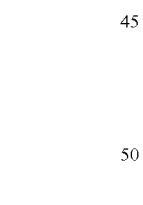

Step 1: A round bottomed flask was charged with 5-bromo-2-chloro methylpyrazine (1 g, 4.82 mmol), tert-butyl(ethynyl)dimethylsilane (810 mg, 5.78 mmol), Pd(PPh3)2Cl2 (675 mg, 964 µmol), CuI (364 mg, 1.92 mmol), TEA (2.43 g, 24.1 mmol) and a stir bar. Dimethylformamide (20 mL) was added, and the solution was stirred for 2 h at 50° C. The reaction mixture was quenched with water, extracted with DCM, dried over Na₂SO₄, concentrated in vacuo. The resulting crude material was purified by silica gel chromatography. Concentration in vacuo resulted in 5-[2-(tert-butyldimethylsilyl)ethynyl]-2-chloro-3-methylpyrazine (1 g, 77%) as an yellow oil.

6-{5-[2-(tert-butyldimethylsilyl)ethynyl]-3-methylpyrazin-2-yl}-7-methyl-7H-pyrrolo[2,3-d]pyrimidin-4-amine

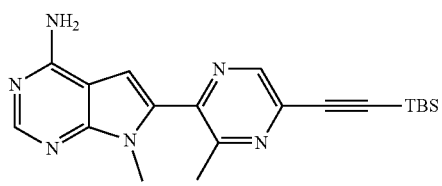

Step 2: A resealable reaction via was charged with 5-[2-(tert-butyldimethylsilyl)ethynyl]-2-chloro-3-methylpyrazine (600 mg, 2.24 mmol), (4-{[(tert-butoxy)carbonyl]amino}-7-methyl-7H-pyrrolo[2,3-d]pyrimidin-6-yl)boronic acid (1.30 g, 4.48 mmol), G3-X-phos (189 mg, 224 µmol), Xphos (213 mg, 448 µmol) Xphos (213 mg, 448 µmol) and a stir bar before being evacuated and purged with nitrogen three times. Dioxane:water=16:1 (20 mL) was added, and the solution was stirred for 2 h at 90° C. The reaction mixture was quenched with water, extracted with DCM, dried over Na₂SO₄, concentrated in vacuo. The resulting crude material was purified by silica gel chromatography. Concentration in vacuo resulted in 6-{5-[2-(tert-butyldimethylsilyl)ethynyl]-3-methylpyrazine-2-yl}-7-methyl-7H-pyrrolo[2,3-d]pyrimidin-4-amine (600 mg, 70%) as an off-white amorphous solid.

5-bromo-6-{5-[2-(tert-butyldimethylsilyl)ethynyl]-3-methylpyrazin-2-yl}-7-methyl-7H-pyrrolo[2,3-d]pyrimidin-4-amine

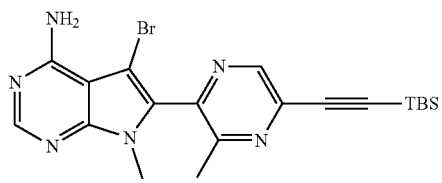

Step 3: A round bottomed flask was charged with 6-{5-[2-(tert-butyldimethylsilyl)ethynyl]-3-methylpyrazine-2-yl}-7-methyl-7H-pyrrolo[2,3-d]pyrimidin-4-amine (500 mg, 1.32 mmol), Dimethylformamide (5 mL) and a stir bar. NBS (234 mg, 1.32 mmol) was added, and the solution was stirred for 1 h at room temperature. The reaction mixture was quenched with water, extracted with DCM, dried over Na₂SO₄, concentrated in vacuo. The resulting crude material was purified by silica gel chromatography. Concentration in vacuo resulted in 5-bromo-6-{5-[2-(tert-butyldimethylsilyl)ethynyl]-3-methylpyrazin-2-yl}-7-methyl-7H-pyrrolo[2,3-d]pyrimidin-4-amine (500 mg, 82%) as an off-white amorphous solid.

1651
6-{5-[2-(tert-butyldimethylsilyl)ethynyl]-3-methylpyrazin-2-yl}-7-methyl-5-{4-[(4-methylpyrimidin-2-yl)oxy]phenyl}-7H-pyrrolo[2,3-d]pyrimidin-4-amine

1652
6-(5-ethynyl-3-methylpyrazin-2-yl)-7-methyl-5-{4-[(4-methylpyrimidin-2-yl)oxy]phenyl}-7H-pyrrolo[2,3-d]pyrimidin-4-amine

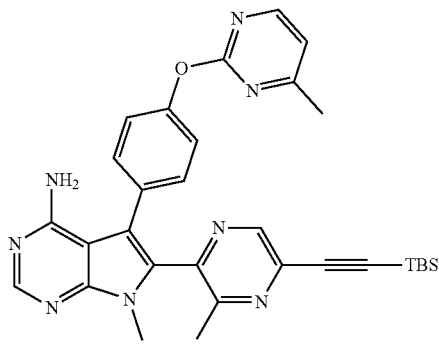

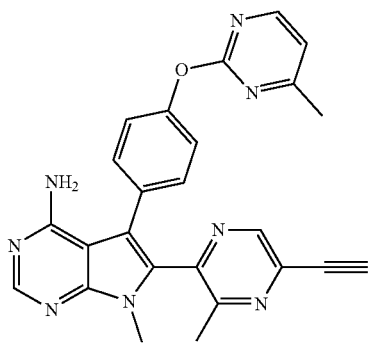

Step 4: A resealable reaction via was charged with 4-methyl-2-[4-(4,4,5,5-tetramethyl-1,3,2-dioxaborolan-2-yl)phenoxy]pyrimidine (374 mg, 1.20 mmol), 5-bromo-6-{5-[2-(tert-butyldimethylsilyl)ethynyl]-3-methylpyrazin-2-yl}-7-methyl-7H-pyrrolo[2,3-d]pyrimidin-4-amine (460 mg, 1.00 mmol), Pd(dppf)Cl2 (73.1 mg, 100 μmol), Cs2CO3 (975 mg, 3.00 mmol) and a stir bar before being evacuated and purged with nitrogen three times. Dioxane:water=16:1 (10 mL) was added, and the solution was stirred for 2 h at 90° C. The reaction mixture was quenched with water, extracted with DCM, dried over Na$_2$SO$_4$, concentrated in vacuo. The resulting crude material was purified by prep-TLC. Concentration in vacuo resulted in 6-{5-[2-(tert-butyldimethylsilyl)ethynyl]-3-methylpyrazin-2-yl}-7-methyl-5-{4-[(4-methylpyrimidin-2-yl)oxy]phenyl}-7H-pyrrolo[2,3-d]pyrimidin-4-amine (500 mg, 73%) as an off-white amorphous solid.

Step 5: A round bottomed flask was charged with 6-{5-[2-(tert-butyldimethylsilyl)ethynyl]-3-methylpyrazin-2-yl}-7-methyl-5-{4-[(4-methylpyrimidin-2-yl)oxy]phenyl}-7H-pyrrolo[2,3-d]pyrimidin-4-amine (480 mg, 852 μmol), CsF (387 mg, 2.55 mmol) and a stir bar. THF (10 mL) was added, and the solution was stirred for 2 h at 50° C. The reaction mixture was filtered, washed with DCM, concentrated in vacuo. The resulting crude material was purified by prep-HPLC. Lyophilization yielded 6-(5-ethynyl-3-methylpyrazin-2-yl)-7-methyl-5-{4-[(4-methylpyrimidin-2-yl)oxy]phenyl}-7H-pyrrolo[2,3-d]pyrimidin-4-amine (260 mg, 68%) as an off-white amorphous solid.

Additional compounds prepared according to the methods of Example 22 are depicted in Table 21 below.

TABLE 21

Additional Exemplary Compounds

| Compound | Structure | Proton NMR | MS [M + 1] |
|---|---|---|---|
| 6-(5-ethynylpyrazin-2-yl)-7-methyl-5-(4-((4-methylpyrimidin-2-yl)oxy)phenyl)-7H-pyrrolo[2,3-d]pyrimidin-4-amine | 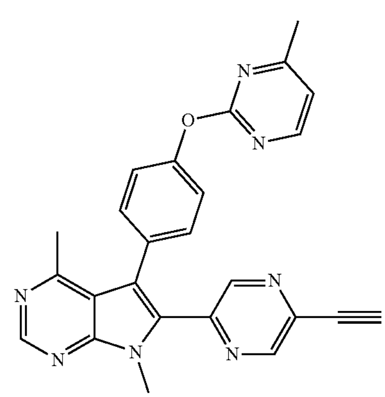 [SMILES: C#Cc1cnc(-c2c(-c3ccc(Oc4nccc(C)n4)cc3)c3c(C)ncnc3n2C)cn1] | $^1$H NMR (400 MHz, DMSO-d$_6$) δ 8.92 (d, J = 1.5 Hz, 1H), 8.50 (d, J = 5.0 Hz, 1H), 8.29-8.20 (m, 2H), 7.43-7.33 (m, 2H), 7.33-7.23 (m, 2H), 7.18 (d, J = 5.0 Hz, 1H), 6.10 (s, 2H), 4.75 (s, 1H), 3.85 (s, 3H), 2.43 (s, 3H). | 435.30 |

TABLE 21-continued

Additional Exemplary Compounds

| Compound | Structure | Proton NMR | MS [M + 1] |
|---|---|---|---|
| 6-(5-ethynyl-3-methylpyrazin-2-yl)-7-methyl-5-(4-((4-methylpyrimidin-2-yl)oxy)phenyl)-7H-pyrrolo[2,3-d]pyrimidin-4-amine | 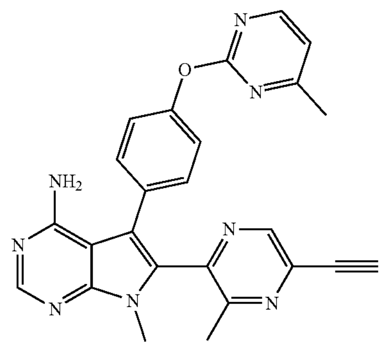 [SMILES: C#Cc1cnc(-c2c(-c3ccc(Oc4nccc(C)n4)cc3)c3c(N)ncnc3n2C)c(C)n1] | ¹H NMR (400 MHz, DMSO-d₆) δ 8.81 (d, J = 0.8 Hz, 1H), 8.45 (d, J = 5.0 Hz, 1H), 8.24 (s, 1H), 7.20-7.12 (m, 5H), 4.73 (s, 1H), 3.57 (s, 3H), 2.38 (s, 3H), 1.98-1.94 (m, 3H). | 449.20 |
| 6-(5-ethynyl-3-methylpyrazin-2-yl)-5-(3-fluoro-4-((4-methylpyrimidin-2-yl)oxy)phenyl)-7-methyl-7H-pyrrolo[2,3-d]pyrimidin-4-amine | 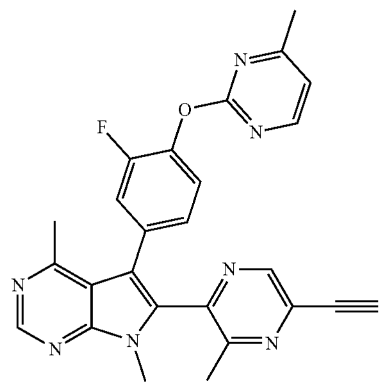 [SMILES: C#Cc1cnc(-c2c(-c3ccc(Oc4nccc(C)n4)c(F)c3)c3c(C)ncnc3n2C)c(C)n1] | ¹H NMR (400 MHz, DMSO-d₆) δ 8.85 (s, 1H), 8.49 (d, J = 5.0 Hz, 1H), 8.35 (s, 1H), 7.35 (t, J = 8.4 Hz, 2H), 7.20 (d, J = 5.0 Hz, 2H), 7.08 (s, 1H), 6.92 (d, J = 7.9 Hz, 1H), 4.78 (s, 1H), 3.62 (s, 3H), 2.42 (s, 3H), 2.02 (s, 3H). | 467.15 |
| 6-(6-ethynyl-5 fluoro-4-methylpyridin-3-yl)-7-methyl-5-(5-((4-methylpyrimidin-2-yl)oxy)pyridin-2-yl)-7H-pyrrolo[2,3-d]pyrimidin-4-amine | 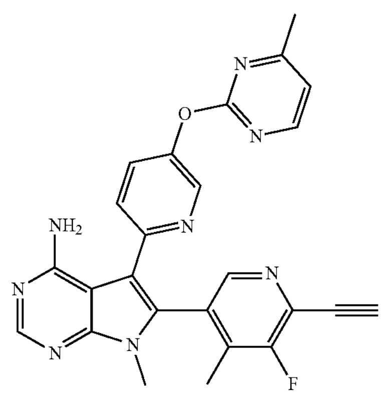 [SMILES: C#Cc1ncc(-c2c(-c3ccc(Oc4nccc(C)n4)cn3)c3c(N)ncnc3n2C)c(C)c1F] | ¹H NMR (400 MHz, DMSO-d₆) δ 8.64-8.59 (m, 1H), 8.48 (d, J = 5.0 Hz, 1H), 8.43 (s, 1H), 8.21 (s, 1H), 7.52 (dd, J = 8.8, 2.8 Hz, 1H), 7.19 (d, J = 5.1 Hz, 1H), 6.88-6.81 (m, 1H), 4.86 (d, J = 0.8 Hz, 1H), 3.47 (s, 3H), 2.41 (s, 3H), 2.02 (d, J = 2.1 Hz, 3H). | 467.30 |
| 5-(3-fluoro-4-(4-methylpyrimidin-2-yloxy)phenyl)-7-methyl-6-(3-methyl-5-(prop-1-ynyl)pyrazin-2-yl)-7H-pyrrolo[2,3-d]pyrimidin-4-amine | 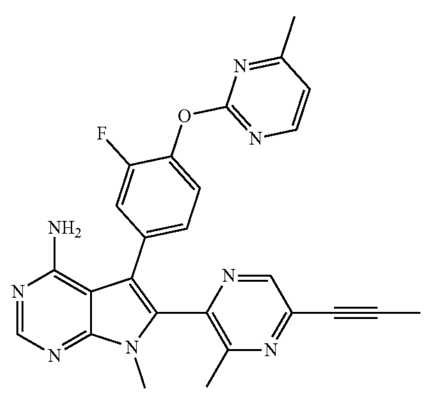 [SMILES: CC#Cc1cnc(-c2c(-c3ccc(Oc4nccc(C)n4)c(F)c3)c3c(N)ncnc3n2C)c(C)n1] | ¹H NMR (400 MHz, DMSO-d6) 8.72 (d, J = 0.8 Hz, 1H), 8.49 (d, J = 5.0 Hz, 1H), 8.26 (s, 1H), 7.34 (t, J = 8.4 Hz, 1H), 7.19 (d, J = 5.1 Hz, 1H), 7.11 (d, J = 11.2 Hz, 1H), 6.93 (d, J = 8.3 Hz, 1H), 6.27 (s, 1H), 3.58 (s, 3H), 2.42 (s, 3H), 2.16 (s, 3H), 2.00 (d, J = 0.6 Hz, 3H). | 481.15 |

TABLE 21-continued

Additional Exemplary Compounds

| Compound | Structure | Proton NMR | MS [M + 1] |
|---|---|---|---|
| (S)-(4-(4-amino-6-(6-ethynyl-5-fluoro-4-methylpyridin-3-yl)-7-methyl-7H-pyrrolo[2,3-d]pyrimidin-5-yl)cyclohex-3-en-1-yl)(pyrrolidin-1-yl)methanone | 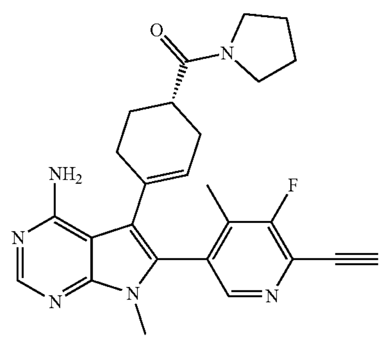 [SMILES: C#Cc1ncc(-c2c(C3=CC[C@@H](C(=O)N4CCCC4)CC3)c3c(N)ncnc3n2C)c(C)c1F] | $^1$H NMR (400 MHz, Methanol-d$_4$) δ 8.29 (d, J = 7.0 Hz, 1H), 8.18 (s, 1H), 5.93 (s, 1H), 4.21 (dd, J = 1.9, 0.9 Hz, 1H), 3.63-3.50 (m, 2H), 3.51 (s, 3H), 3.49-3.37 (m, 2H), 2.85 (q, J = 6.1 Hz, 1H), 2.45-2.28 (m, 2H), 2.21 (dd, J = 3.7, 2.2 Hz, 3H), 2.18-2.01 (m, 2H), 2.03-1.95 (m, 2H), 1.92-1.85 (m, 2H), 1.77 (dt, J = 12.1, 6.1 Hz, 2H). | 459.30 |
| (R)-(4-(4-amino-6-(6-ethynyl-5-fluoro-4-methylpyridin-3-yl)-7-methyl-7H-pyrrolo[2,3-d]pyrimidin-5-yl)cyclohex-3-en-1-yl)(pyrrolidin-1-yl)methanone | 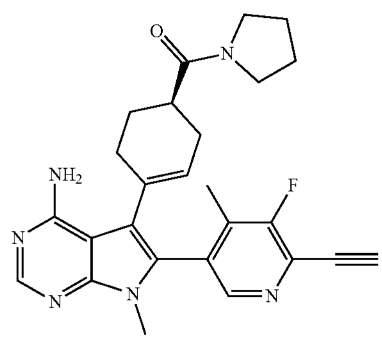 [SMILES: C#Cc1ncc(-c2c(C3=CC[C@H](C(=O)N4CCCC4)CC3)c3c(N)ncnc3n2C)c(C)c1F] | $^1$H NMR (400 MHz, Methanol-d$_4$) δ 8.29 (d, J = 7.0 Hz, 1H), 8.18 (s, 1H), 5.83 (dd, J = 3.8, 1.9 Hz, 1H), 4.21 (dd, J = 1.9, 0.8 Hz, 1H), 3.55 (dtd, J = 10.2, 6.6, 3.6 Hz, 2H), 3.51 (s, 3H), 3.43 (ddt, J = 9.3, 6.5, 3.7 Hz, 2H), 2.86 (p, J = 6.2 Hz, 1H), 2.44-2.31 (m, 1H), 2.28 (s, 1H), 2.21 (dd, J = 3.7, 2.2 Hz, 3H), 2.12 (d, J = 14.2 Hz, 2H), 2.04-1.96 (m, 2H), 1.94-1.86 (m, 2H), 1.79 (p, J = 6.9, 6.4 Hz, 2H). | 459.30 |
| 6-(4-(dimethylamino)-6-ethynylpyridin-3-yl)-5-(3-fluoro-4-((4-methylpyrimidin-2-yl)oxy)phenyl)-7-methyl-7H-pyrrolo[2,3-d]pyrimidin-4-amine | 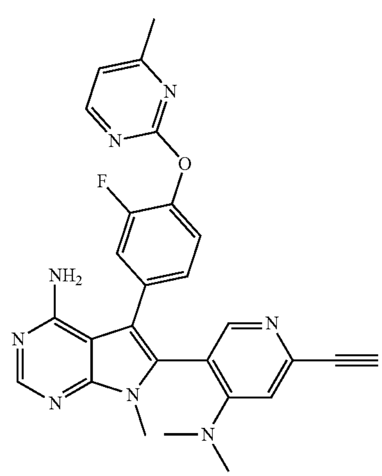 [SMILES: C#Cc1cc(N(C)C)c(-c2c(-c3ccc(Oc4nccc(C)n4)c(F)c3)c3c(N)ncnc3n2C)cn1] | $^1$H NMR (400 MHz, DMSO-d$_6$) δ 8.48 (d, J = 5.1 Hz, 1H), 8.22 (s, 1H), 8.06 (s, 1H), 7.36 (t, J = 8.4 Hz, 1H), 7.24-7.16 (m, 2H), 7.09 (d, J = 8.6 Hz, 1H), 6.91 (s, 1H), 6.14(s, 1H), 4.25 (s, 1H), 3.54 (s, 3H), 2.63 (s, 6H), 2.42 (s, 3H). | 495.20 |

Example 23
Scheme 20
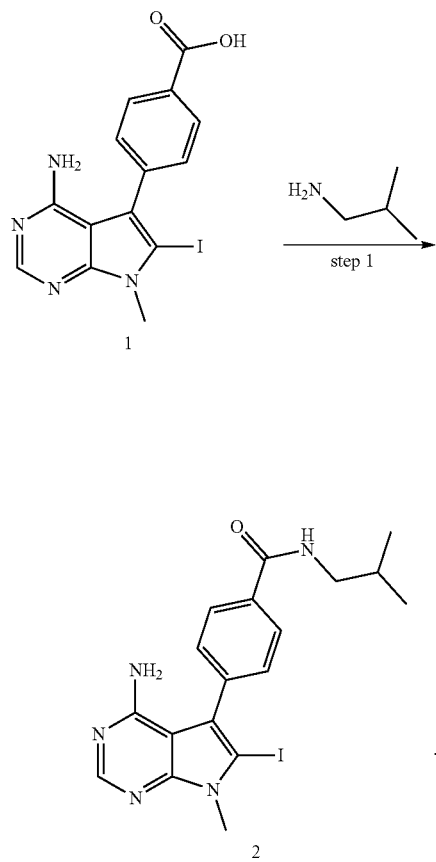
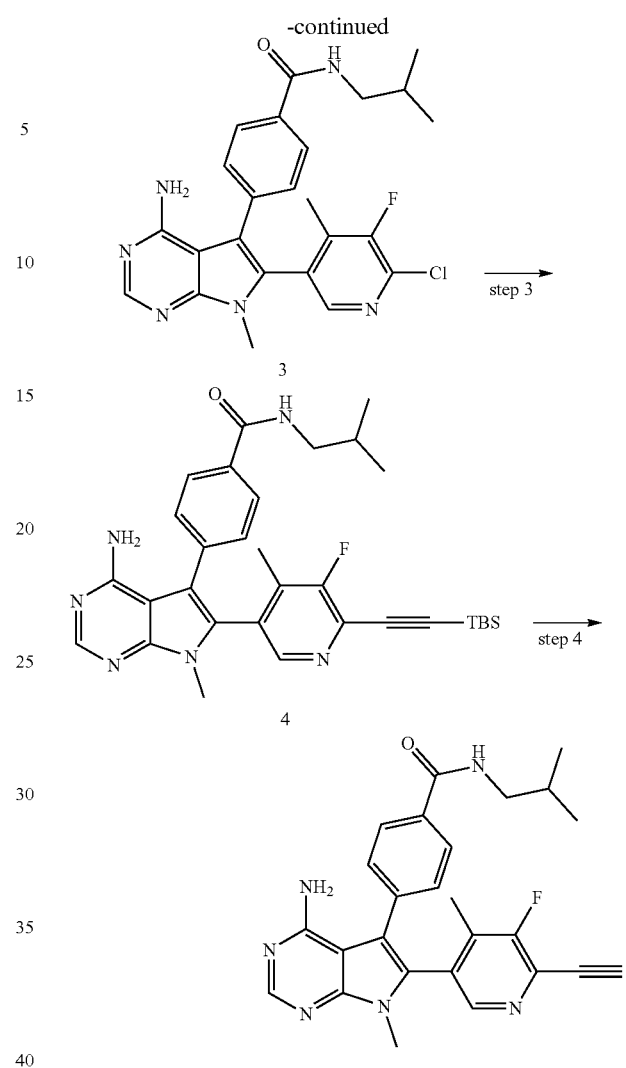
Additional compounds prepared according to the methods of Example 23 are depicted in Table 22 below.
TABLE 22
Additional Exemplary Compounds
| Compound | Structure | Proton NMR | MS [M + 1] |
|---|---|---|---|
| 7-methyl-6-(4-methyl-2-vinylpyrimidin-5-yl)-5-(4-((4-methylpyrimidin-2-yl)oxy)phenyl)-7H-pyrrolo[2,3-d]pyrimidin-4-amine | 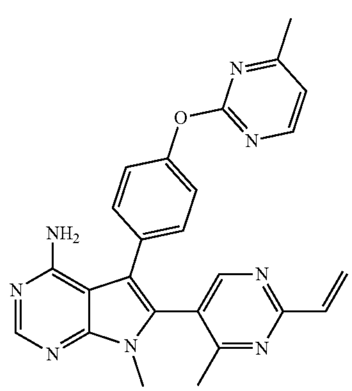 [SMILES: C=Cc1ncc(-c2c(-c3ccc(Oc4nccc(C)n4)cc3)c3c(N)ncnc3n2C)c(C)n1] | $^1$H NMR (400 MHz, DMSO-$d_6$) δ 8.76 (s, 1H), 8.46 (d, J = 5.1 Hz, 1H), 8.25 (s, 1H), 7.28 (d, J = 8.6 Hz, 2H), 7.19 (d, J = 8.7 Hz, 2H), 7.15 (d, J = 5.0 Hz, 1H), 6.81 (d, J = 10.7 Hz, 1H), 6.65 (d, J = 10.8 Hz, 1H), 5.82 (s, 1H), 3.54 (s, 3H), 2.40 (s, 3H), 2.17 (s, 3H). | 451.10 |

TABLE 22-continued

Additional Exemplary Compounds

| Compound | Structure | Proton NMR | MS [M + 1] |
|---|---|---|---|
| 7-methyl-5-(4-((4-methylpyrimidin-2-yl)oxy)phenyl)-6-(2-(prop-1-yn-1-yl)pyrimidin-5-yl)-7H-pyrrolo[2,3-d]pyrimidin-4-amine | 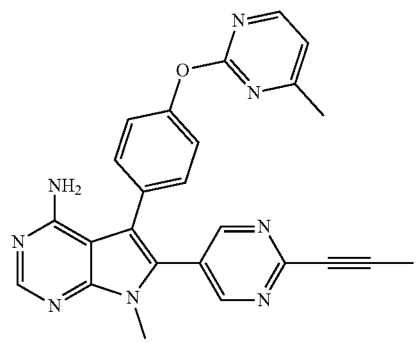 [SMILES: CC#Cc1ncc(-c2c(-c3ccc(Oc4nccc(C)n4)cc3)c3c(N)ncnc3n2C)cn1] | $^1$H NMR (400 MHz, DMSO-$d_6$) δ 8.75 (s, 2H), 8.48 (d, J = 5.0 Hz, 1H), 8.25 (s, 1H), 7.38-7.31 (m, 2H), 7.29-7.18 (m, 2H), 7.17 (s, 1H), 5.89 (d, J = 103.6 Hz, 1H), 3.71 (s, 3H), 2.43 (s, 3H), 2.12 (s, 3H). | 449.15 |
| 5-(4-amino-7-methyl-5-(4-((4-methylpyrimidin-2-yl)oxy)phenyl)-7H-pyrrolo[2,3-d]pyrimidin-6-yl)-2-ethynylnicotinonitrile | 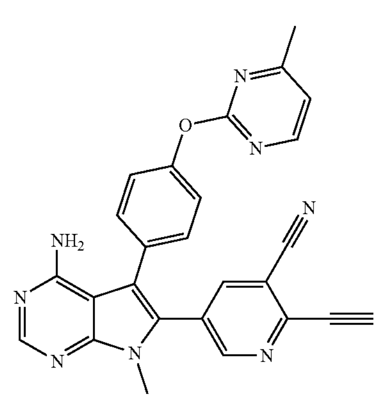 [SMILES: C#Cc1ncc(-c2c(-c3ccc(Oc4nccc(C)n4)cc3)c3c(N)ncnc3n2C)cc1C#N] | $^1$H NMR (400 MHz, DMSO-$d_6$) 8.63 (d, J = 2.2 Hz, 1H), 8.50 (d, J = 2.1 Hz, 1H), 8.45 (d, J = 5.0 Hz, 1H), 8.23 (s, 1H), 7.34-7.27 (m, 2H), 7.25-7.18 (m, 2H), 7.14 (d, J = 5.0 Hz, 1H), 5.03 (s, 1H), 3.68 (s, 3H), 2.40 (s, 3H). | 459.10 |
| 7-methyl-6-(4-methyl-2-(prop-1-yn-1-yl)pyrimidin-5-yl)-5-(4-((4-methylpyrimidin-2-yl)oxy)phenyl)-7H-pyrrolo[2,3-d]pyrimidin-4-amine | 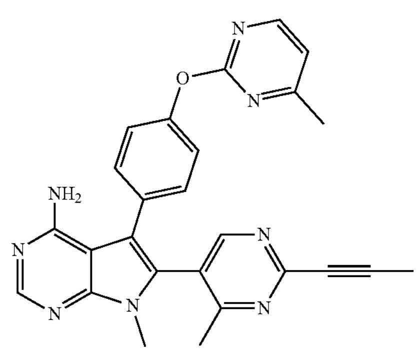 [SMILES: CC#Cc1ncc(-c2c(-c3ccc(Oc4nccc(C)n4)cc3)c3c(N)ncnc3n2C)c(C)n1] | $^1$H NMR (400 MHz, DMSO-$d_6$) δ 8.73 (s, 1H), 8.47 (d, J = 5.0 Hz, 1H), 8.25 (s, 1H), 7.25 (d, J = 8.6 Hz, 2H), 7.26-7.13 (m, 3H), 3.53 (s, 3H), 2.41 (s, 3H), 2.12 (d, J = 3.2 Hz, 6H). | 463.35 |
| 6-(2-(3-methoxyprop-1-yn-1-yl)-4-methylpyrimidin-5-yl)-7-methyl-5-(4-((4-methylpyrimidin-2-yl)oxy)phenyl)-7H-pyrrolo[2,3-d]pyrimidin-4-amine | 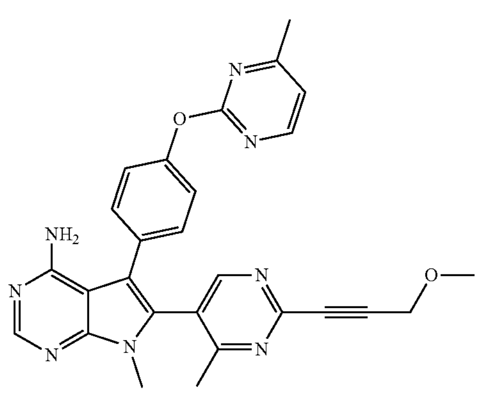 [SMILES: COCC#Cc1ncc(-c2c(-c3ccc(Oc4nccc(C)n4)cc3)c3c(N)ncnc3n2C)c(C)n1] | $^1$H NMR (400 MHz, DMSO-d6) δ 8.80 (s, 1H), 8.47 (d, J = 5.0 Hz, 1H), 8.25 (s, 1H), 7.29-7.17 (m, 5H), 4.40 (s, 2H), 3.55 (s, 3H), 3.36 (d, J = 1.4 Hz, 3H), 2.41 (s, 3H), 2.14 (s, 3H). | 493.15 |

TABLE 22-continued

Additional Exemplary Compounds

| Compound | Structure | Proton NMR | MS [M + 1] |
|---|---|---|---|
| 6-(6-ethynyl-2-fluoropyridin-3-yl)-5-(3-fluoro-4-((4-methylpyrimidin-2-yl)oxy)phenyl)-7-methyl-7H-pyrrolo[2,3-d]pyrimidin-4-amine | 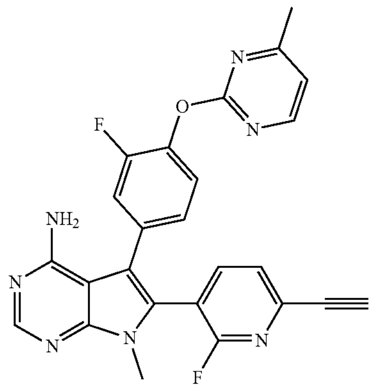 [SMILES: C#Cc1ccc(-c2c(-c3ccc(Oc4nccc(C)n4)c(F)c3)c3c(N)ncnc3n2C)c(F)n1] | $^1$HNMR (300 MHz, DMSO-$d_6$) 8.49 (d, J = 5.0 Hz, 1H), 8.25 (s, 1H), 8.08 (dd, J = 9.6, 7.6 Hz, 1H), 7.65 (dd, J = 7.5, 1.7 Hz, 1H), 7.37 (t, J = 8.4 Hz, 1H), 7.27-7.17 (m, 2H), 7.07 (d, J = 8.3 Hz, 1H), 4.64 (s, 1H), 3.60 (s, 3H), 2.42 (s, 3H), 2.08 (s, 1H). | 470.25 |
| 6-(6-ethynyl-5-fluoro-4-methylpyridin-3-yl)-5-(3-fluoro-4-((4-methylpyrimidin-2-yl)oxy)phenyl)-7-methyl-7H-pyrrolo[2,3-d]pyrimidin-4-amine | 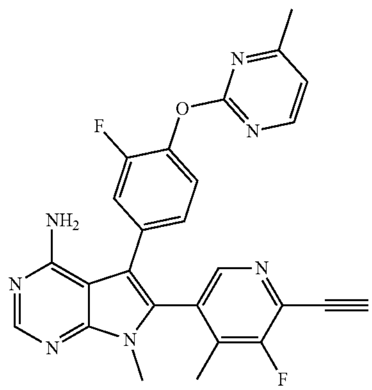 | 1H NMR(300 MHz, DMSO-d6) 8.47 (d, J = 5.0 Hz, 1H), 8.41 (s, 1H), 8.25 (s, 1H), 7.33 (t, J = 8.4 Hz, 1H), 7.24-7.12 (m, 2H), 7.03 (d, J = 9.4 Hz, 1H), 4.79 (s, 1H), 3.51 (s, 3H), 2.40 (s, 3H), 1.97 (d, J = 2.2 Hz, 3H). | 484.35 |
| 6-(6-ethynyl-5-methoxy-4-methylpyridin-3-yl)-5-(3-fluoro-4-((4-methylpyrimidin-2-yl)oxy)phenyl)-7-methyl-7H-pyrrolo[2,3-d]pyrimidin-4-amine | 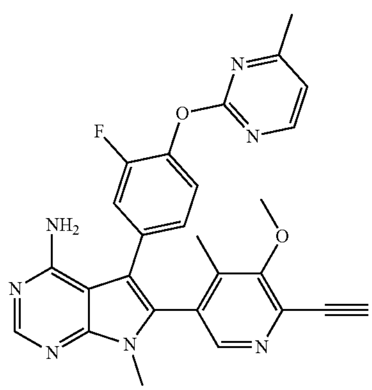 [SMILES: C#Cc1ncc(-c2c(-c3ccc(Oc4nccc(C)n4)c(F)c3)c3c(N)ncnc3n2C)c(C)c1OC] | $^1$H NMR (400 MHz, DMSO-$d_6$) δ 8.45 (d, J = 5.1 Hz, 1H), 8.32 (s, 1H), 8.24 (s, 1H), 7.32 (t, J = 8.4 Hz, 1H), 7.20-7.12 (m, 2H), 7.04-6.98 (m, 1H), 6.18 (s, 2H), 4.63 (s, 1H), 3.83 (s, 3H), 3.51 (s, 3H), 2.40 (s, 3H), 1.91 (s, 3H). | 496.30 |
| 4-(4-amino-6-(6-ethynyl-5-fluoro-4-methylpyridin-3-yl)-7-methyl-7H-pyrrolo[2,3-d]pyrimidin-5-yl)-N-isobutylbenzamide | 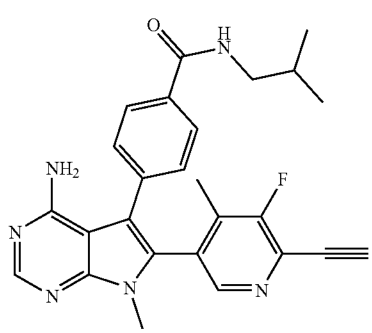 [SMILES: C#Cc1ncc(-c2c(-c3ccc(C(=O)NCC(C)C)cc3)c3c(N)ncnc3n2C)c(C)c1F] | $^1$H NMR (400 MHz, DMSO-$d_6$) δ 8.35 (s, 1H), 8.25 (s, 1H), 7.83-7.76 (m, 2H), 7.29-7.22 (m, 2H), 6.12 (s, 2H), 4.80 (s, 1H), 3.51 (s, 3H), 3.06 (t, J = 6.4 Hz, 2H), 1.94 (d, J = 2.1 Hz, 3H), 1.82 (dq, J = 13.3, 6.7 Hz, 1H), 0.88 (d, J = 6.7 Hz, 6H). | 457.20 |

TABLE 22-continued

Additional Exemplary Compounds

| Compound | Structure | Proton NMR | MS [M + 1] |
|---|---|---|---|
| 4-(4-amino-6-(6-ethynyl-5-fluoro-4-methylpyridin-3-yl)-7-methyl-7H-pyrrolo[2,3-d]pyrimidin-5-yl)-N-isobutyl-N-methylbenzamide | 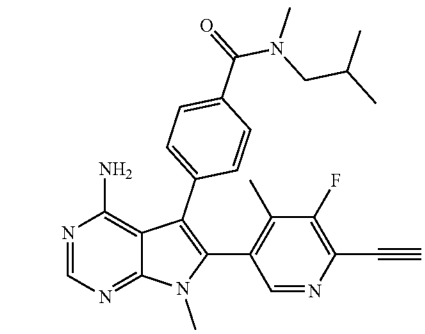 [SMILES: C#Cc1ncc(-c2c(-c3ccc(C(=O)N(C)CC(C)C)cc3)c3c(N)ncnc3n2C)c(C)c1F] | ¹H NMR (400 MHz, DMSO-d₆) δ 8.37 (s, 1H), 8.25 (s, 1H), 7.41-7.26 (m, 2H), 7.22 (d, J = 7.6 Hz, 2H), 6.16 (s, 2H), 4.78 (s, 1H), 3.53 (d, J = 7.5 Hz, 3H), 3.29 (d, J = 11.4 Hz, 1H), 3.05-2.80 (m, 4H), 1.89 (d, J = 26.0 Hz, 4H), 0.93 (dd, J = 17.7, 7.0 Hz, 3H), 0.63 (s, 3H). | 471.25 |
| 4-(4-amino-6-(6-ethynyl-5-fluoro-4-methylpyridin-3-yl)-7-methyl-7H-pyrrolo[2,3-d]pyrimidin-5-yl)-2-methoxy-N-(2,2,2-trifluoroethyl)benzamide | 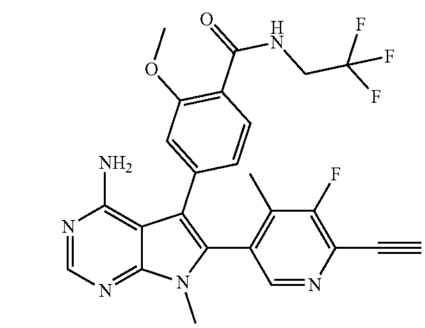 [SMILES: C#Cc1ncc(-c2c(-c3ccc(C(=O)NCC(F)(F)F)c(OC)c3)c3c(N)ncnc3n2C)c(C)c1F] | ¹H NMR (400 MHz, DMSO-d₆) 8.62 (t, J = 6.4 Hz, 1H), 8.39 (s, 1H), 8.26 (s, 1H), 7.70 (d, J = 7.9 Hz, 1H), 6.92 (d, J = 1.5 Hz, 1H), 6.83 (dd, J = 7.9, 1.5 Hz, 1H), 6.21 (s, 1H), 4.81 (d, J = 0.8 Hz, 1H), 4.08 (td, J = 9.7, 6.6 Hz, 2H), 3.75 (s, 3H), 3.52 (s, 3H), 1.97 (d, J = 2.1 Hz, 3H). | 513.35 |
| ((S)-4-(4-amino-6-(3-methoxyprop-1-yn-1-yl)-4-methylpyridin-3-yl)-7-methyl-7H-pyrrolo[2,3-d]pyrimidin-5-yl)cyclohex-3-en-1-yl)((R)-2-methylpyrrolidin-1-yl)methanone | | 1H NMR (400 MHz, DMSO-d6) δ 8.42-8.35 (m, 1H), 8.17-8.06 (m, 1H), 7.61 (d, J = 2.3 Hz, 1H), 6.67 (s, 2H), 5.69 (d, J = 36.7 Hz, 1H), 4.39 (s, 2H), 4.01 (t, J = 4.6 Hz, 1H), 3.45 (d, J = 6.6 Hz, 1H), 3.37 (s, 7H), 2.71 (d, J = 33.3 Hz, 1H), 2.24 (s, 1H), 2.18-2.03 (m, 4H), 2.00-1.42 (m, 8H), 1.13-1.01 (m, 3H). | 499.30 |
| ((R)-4-(4-amino-6-(3-methoxyprop-1-yn-1-yl)-4-methylpyridin-3-yl)-7-methyl-7H-pyrrolo[2,3-d]pyrimidin-5-yl)cyclohex-3-en-1-yl)((R)-2-methylpyrrolidin-1-yl)methanone | | 1H NMR (400 MHz, DMSO-d6) δ 8.47-8.34 (m, 1H), 8.13 (s, 1H), 7.61 (d, J = 2.2 Hz, 1H), 6.54 (s, 2H), 5.66 (d, J = 26.0 Hz, 1H), 4.39 (s, 2H), 4.04 (d, J = 37.4 Hz, 1H), 3.57-3.40 (m, 1H), 3.37 (s, 7H), 2.69 (s, 1H), 2.13 (d, J = 4.4 Hz, 5H), 2.05-1.42 (m, 8H), 1.08 (dd, J = 12.8, 6.5 Hz, 3H). | 499.30 |

TABLE 22-continued

Additional Exemplary Compounds

| Compound | Structure | Proton NMR | MS [M + 1] |
|---|---|---|---|
| 6-(6-(3-methoxyprop-1-yn-1-yl)-4-methylpyridin-3-yl)-7-methyl-5-(4-((4-methylpyrimidin-2-yl)oxy)phenyl)-7H-pyrrolo[2,3-d]pyrimidin-4-amine | 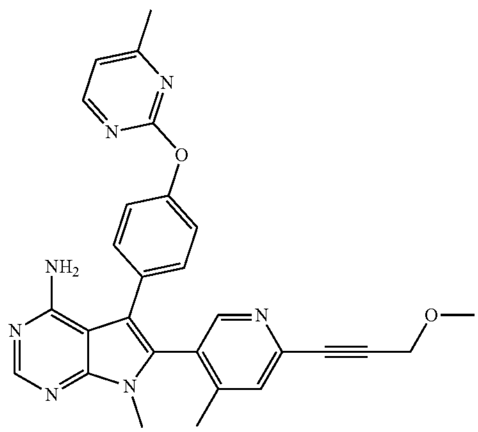 [SMILES: COCC#Cc1cc(C)c(-c2c(-c3ccc(Oc4nccc(C)n4)cc3)c3c(N)ncnc3n2C)cn1] | ¹H NMR (400 MHz, DMSO-d₆) δ 8.49 (s, 1H), 8.46 (d, J = 5.0 Hz, 1H), 8.23 (s, 1H), 7.53 (s, 1H), 7.27-7.20 (m, 2H), 7.2-7.11 (m, 3H), 6.03 (s, 2H), 4.37 (s, 2H), 3.47 (s, 3H), 3.35 (s, 3H), 2.40 (s, 3H), 2.01 (s, 3H). | 492.40 |
| 5-(3-fluoro-4-((4-methylpyrimidin-2-yl)oxy)phenyl)-6-(6-(3-methoxyprop-1-yn-1-yl)-4-methylpyridin-3-yl)-4,7-dimethyl-7H-pyrrolo[2,3-d]pyrimidine | 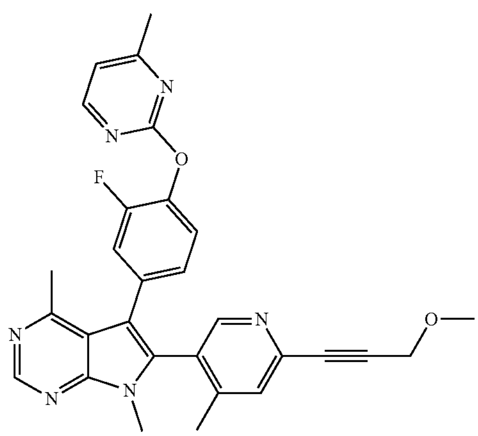 [SMILES: COCC#Cc1cc(C)c(-c2c(-c3ccc(Oc4nccc(C)n4)c(F)c3)c3c(C)ncnc3n2C)cn1] | ¹H NMR (400 MHz, DMSO-d₆) δ 8.78 (s, 1H), 8.54 (s, 1H), 8.48 (d, J = 5.0 Hz, 1H), 7.57 (s, 1H), 7.36-7.27 (m, 2H), 7.18 (d, J = 5.0 Hz, 1H), 7.17-7.09 (m, 1H), 4.38 (s, 2H), 3.57 (s, 3H), 3.35 (s, 3H), 2.41 (d, J = 9.6 Hz, 6H), 2.06 (s, 3H). | 509.25 |
| 5-(3-fluoro-4-((4-methylpyrimidin-2-yl)oxy)phenyl)-6-(2-(3-methoxyprop-1-yn-1-yl)quinolin-6-yl)-7-methyl-7H-pyrrolo[2,3-d]pyrimidin-4-amine | 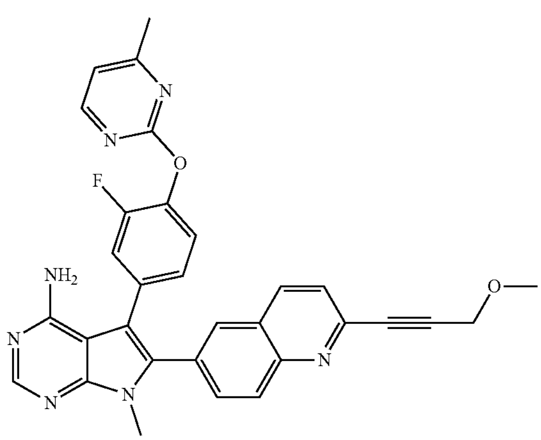 [SMILES: COCC#Cc1ccc2cc(-c3c(-c4ccc(Oc5nccc(C)n5)c(F)c4)c4c(N)ncnc4n3C)ccc2n1] | ¹H NMR (400 MHz, DMSO-d₆) δ 8.46 (d, J = 5.0 Hz, 1H), 8.40 (d, J = 8.5 Hz, 1H), 8.26 (s, 1H), 8.09 (d, J = 1.9 Hz, 1H), 8.00 (d, J = 8.7 Hz, 1H), 7.74 (dd, J = 8.7, 2.0 Hz, 1H), 7.68 (d, J = 8.5 Hz, 1H), 7.32 (t, J = 8.4 Hz, 1H), 7.25 (dd, J = 11.3, 2.0 Hz, 1H), 7.20-7.11 (m, 2H), 6.09 (s, 2H), 4.45 (s, 2H), 3.69 (s, 3H), 3.40 (s, 3H), 2.39 (s, 3H). | 546.25 |

TABLE 22-continued
Additional Exemplary Compounds
| Compound | Structure | Proton NMR | MS [M + 1] |
|---|---|---|---|
| 5-(3-fluoro-4-((4-methylpyrimidin-2-yl)oxy)phenyl)-6-(4-methoxy-6-(3-methoxyprop-1-yn-1-yl)pyridin-3-yl)-4,7-dimethyl-7H-pyrrolo[2,3-d]pyrimidine | 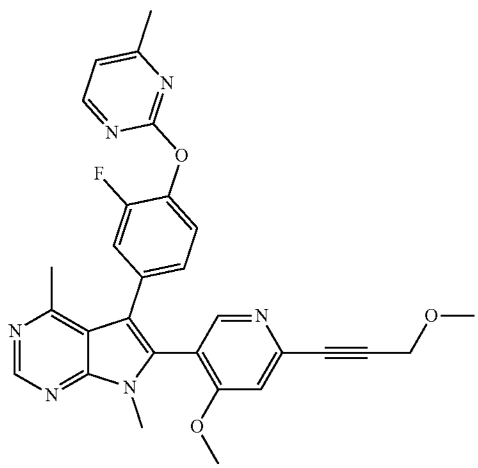 [SMILES: COCC#Cc1cc(OC)c(-c2c(-c3ccc(Oc4nccc(C)n4)c(F)c3)c3c(C)ncnc3n2C)cn1] | $^1$H NMR (400 MHz, DMSO-$d_6$) δ 8.76 (s, 1H), 8.49 (d, J = 5.0 Hz, 1H), 8.29 (s, 1H), 7.40 (s, 1H), 7.34-7.28 (m, 2H), 7.19 (d, J = 5.1 Hz, 1H), 7.10 (d, J = 8.3 Hz, 1H), 4.39 (s, 2H), 3.87 (s, 3H), 3.61 (s, 3H), 3.37 (s, 3H), 2.41 (d, J = 1.9 Hz, 7H). | 525.25 |
Example 24
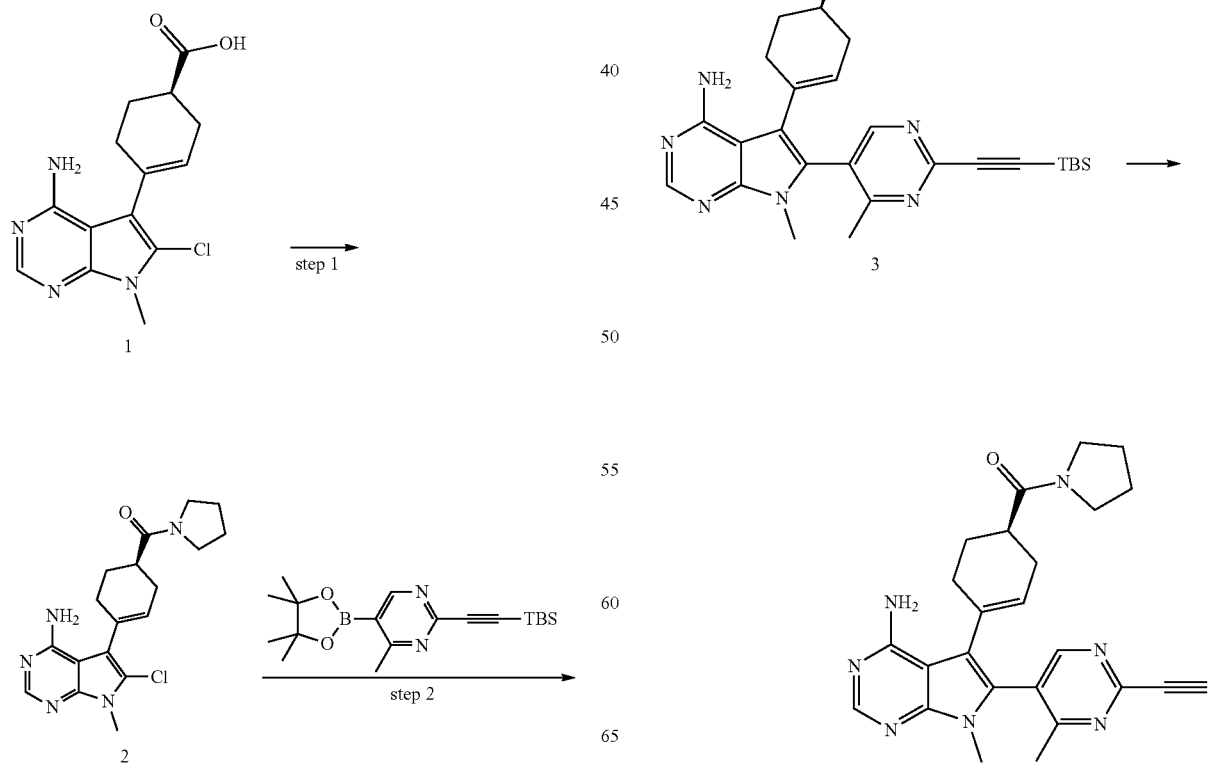
Scheme 21

(1R)-4-{4-amino-6-chloro-7-methyl-7H-pyrrolo[2,3-d]pyrimidin-5-yl}cyclohex-3-ene-1-carboxylic acid

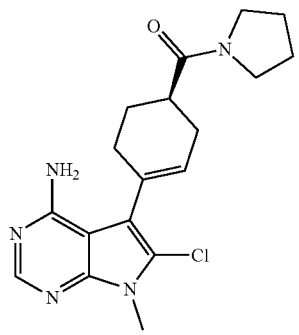 [SMILES: Cn1c(Cl)c(C2=CC[C@H](C(=O)N3CCCC3)CC2)c2c(N)ncnc21]

Step 1: A round bottomed flask was charged with (1R)-4-{4-amino-6-chloro-7-methyl-7H-pyrrolo[2,3-d]pyrimidin-5-yl}cyclohex-3-ene-1-carboxylic acid (1 g, 3.25 mmol), dimethylformamide (15 mL), pyrrolidine (462 mg, 6.50 mmol), HATU (2.47 g, 6.50 mmol), NaHCO3 (546 mg, 6.50 mmol) and a stir bar, and the solution was stirred at for 1 h 25° C. The reaction mixture was diluted with water (20 mL), and the aqueous phase was extracted with dichloromethane (20 mL) three times. The combined organic layers were washed with brine, dried over sodium sulfate, filtered, and concentrated in vacuo. The resulting crude material was purified by silica gel chromatography (eluting with dichloromethane/methanol; 40:1). Concentration in vacuo resulted in (1R)-4-{4-amino-6-chloro-7-methyl-7H-pyrrolo[2,3-d]pyrimidin-5-yl}cyclohex-3-ene-1-carboxylic acid (1 g, 85%) as a yellow amorphous solid.

6-{2-[2-(tert-butyldimethylsilyl)ethynyl]-4-methylpyrimidin-5-yl}-7-methyl-5-[(4R)-4-(pyrrolidine-1-carbonyl)cyclohex-1-en-1-yl]-7H-pyrrolo[2,3-d]pyrimidin-4-amine

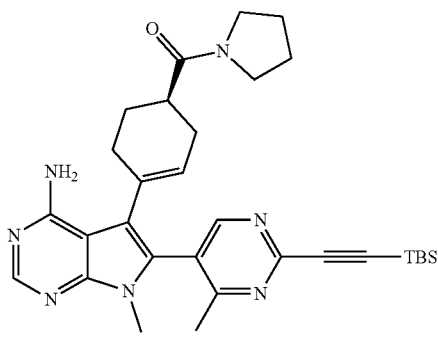

Step 2: A resealable reaction vial was charged with 6-chloro-7-methyl-5-[(4R)-4-(pyrrolidine-1-carbonyl)cyclohex-1-en-1-yl]-7H-pyrrolo[2,3-d]pyrimidin-4-amine (500 mg, 1.38 mmol), 2-[2-(tert-butyldimethylsilyl)ethynyl]-4-methyl-5-(4,4,5,5-tetramethyl-1,3,2-dioxaborolan-2-yl)pyrimidine (541 mg, 1.51 mmol), Na2CO3 (438 mg, 4.14 mmol), X-phos (131 mg, 276 µmol), X-phos G3 (116 mg, 138 µmol) and a stirbar before being evacuated and purged with nitrogen three times. Dioxane/H2O (10 mL) was added, and the mixture was stirred for 1 h at 90° C. The reaction mixture was diluted with water (30 mL), and the aqueous phase was extracted with dichloromethane (20 mL) three times. The combined organic layers were washed with brine, dried over sodium sulfate, filtered, and concentrated in vacuo. The resulting crude material was purified by silica gel chromatography (eluting with dichloromethane/methanol; 40:1). Concentration in vacuo resulted in 6-{2-[2-(tert-butyldimethylsilyl)ethynyl]-4-methylpyrimidin-5-yl}-7-methyl-5-[(4R)-4-(pyrrolidine-1-carbonyl)cyclohex-1-en-1-yl]-7H-pyrrolo[2,3-d]pyrimidin-4-amine (500 mg, 59%) as a yellow amorphous solid.

6-(2-ethynyl-4-methylpyrimidin-5-yl)-7-methyl-5-[(4R)-4-(pyrrolidine-1-carbonyl)cyclohex-1-en-1-yl]-7H-pyrrolo[2,3-d]pyrimidin-4-amine

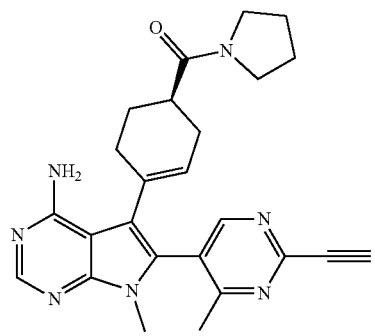 [SMILES: C#Cc1ncc(-c2c(C3=CC[C@H](C(=O)N4CCCC4)CC3)c3c(N)ncnc3n2C)c(C)n1]

Step 3: A round bottomed flask was charged with 6-{2-[2-(tert-butyldimethylsilyl)ethynyl]-4-methylpyrimidin-5-yl}-7-methyl-5-[(4R)-4-(pyrrolidine-1-carbonyl)cyclohex-1-en-1-yl]-7H-pyrrolo[2,3-d]pyrimidin-4-amine (600 mg, 1.07 mmol), TBAF (1.28 mL, 1.28 mmol), and a stirbar. Tetrahydrofuran (10 mL) was added, and the solution was stirred at for 1 h 25° C. The reaction mixture was diluted with water (20 mL), and the aqueous phase was extracted with dichloromethane (20 mL) three times. The combined organic layers were washed with brine, dried over sodium sulfate, filtered, and concentrated in vacuo. The resulting crude material was purified by HPLC. Lyophilization yielded 6-(2-ethynyl-4-methylpyrimidin-5-yl)-7-methyl-5-[(4R)-4-(pyrrolidine-1-carbonyl)cyclohex-1-en-1-yl]-7H-pyrrolo[2,3-d]pyrimidin-4-amine (109 mg, 23%) as an off-white amorphous solid.

Additional compounds prepared according to the methods of Example 24 are depicted in Table 23 below.

TABLE 23

Additional Exemplary Compounds

| Compound | Structure | Proton NMR | MS [M + 1] |
|---|---|---|---|
| (R)-(4-(4-amino-6-(2-ethynyl-4-methylpyrimidin-5-yl)-7-methyl-7H-pyrrolo[2,3-d]pyrimidin-5-yl)cyclohex-3-en-1-yl)(pyrrolidin-1-yl)methanone | 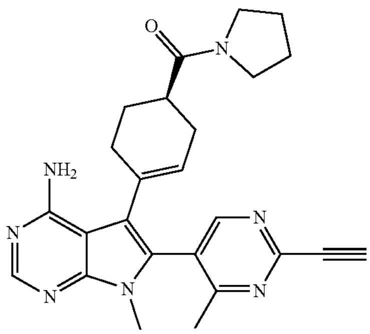 [SMILES: C#Cc1ncc(-c2c(C3=CC[C@H](C(=O)N4CCCC4)CC3)c3c(N)ncnc3n2C)c(C)n1] | $^1$H NMR (300 MHz, DMSO-$d_6$) δ 8.68 (d, J = 13.6 Hz, 1H), 8.14 (s, 1H), 6.65 (s, 2H), 5.67 (s, 1H), 4.51 (d, J = 0.8 Hz, 1H), 3.54-3.39 (m, 5H), 3.27 (tt, J = 8.3, 4.3 Hz, 2H), 2.82-2.73 (m, 1H), 2.33 (d, J = 1.0 Hz, 3H), 2.19 (s, 2H), 1.96 (s, 2H), 1.80 (dp, J = 27.0, 7.0 Hz, 4H), 1.63 (d, J = 6.5 Hz, 2H). | 442.35 |
| (S)-(4-(4-amino-6-(2-ethynyl-4-methylpyrimidin-5-yl)-7-methyl-7H-pyrrolo[2,3-d]pyrimidin-5-yl)cyclohex-3-en-1-yl)(pyrrolidin-1-yl)methanone | 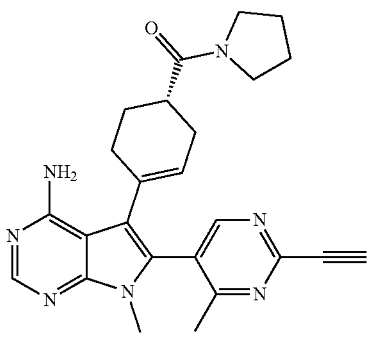 | $^1$H NMR (300 MHz, DMSO-$d_6$) δ 8.68 (d, J = 13.8 Hz, 1H), 8.14 (s, 1H), 6.66 (s, 2H), 5.70 (d, J = 19.4 Hz, 1H), 4.51 (d, J = 0.8 Hz, 1H), 3.58-3.39 (m, 5H), 3.26 (dd, J = 6.8, 3.2 Hz, 2H), 2.78 (t, J = 5.9 Hz, 1H), 2.33 (d, J = 1.0 Hz, 3H), 2.20 (s, 2H), 1.97 (s, 2H), 1.85 (q, J = 6.5 Hz, 2H), 1.77 (q, J = 6.6 Hz, 2H), 1.63 (d, J = 6.4 Hz, 2H). | 442.15 |
| (R)-(4-(4-amino-6-(6-ethynyl-4-methylpyridin-3-yl)-7-methyl-7H-pyrrolo[2,3-d]pyrimidin-5-yl)cyclohex-3-en-1-yl)(2-oxa-5-azaspiro[3.4]octan-5-yl)methanone | 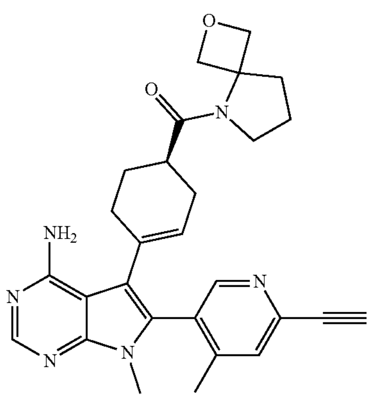 [SMILES: C#Cc1cc(C)c(-c2c(C3=CC[C@H](C(=O)N4CCCC45COC5)CC3)c3c(N)ncnc3n2C)cn1] | $^1$H NMR (400 MHz, DMSO-$d_6$) 8.38 (d, J = 7.1 Hz, 1H), 8.12 (d, J = 1.1 Hz, 1H), 7.61 (s, 1H), 6.52 (s, 2H), 5.68 (d, J = 24.1 Hz, 1H), 5.26 (dt, J = 15.3, 4.2 Hz, 2H), 4.41 (d, J = 1.2 Hz, 1H), 4.15 (d, J = 4.9 Hz, 2H), 3.53-3.34 (m, 3H), 3.3-3.25(m, 3H), 2.32-2.07 (m, 7H), 1.74-1.49 (m, 5H), 1.22 (s, 1H). | 483.15 |
| (R)-(4-(4-amino-6-(6-ethynyl-2-methylpyridin-3-yl)-7-methyl-7H-pyrrolo[2,3-d]pyrimidin-5-yl)cyclohex-3-en-1-yl)(2-oxa-5-azaspiro[3.4]octan-5-yl)methanone | 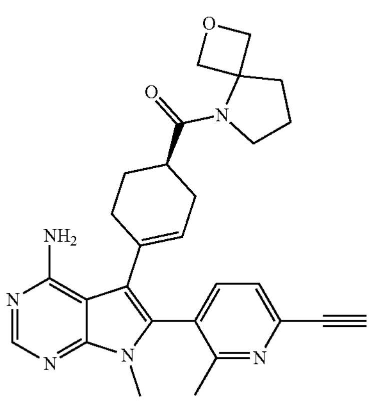 [SMILES: C#Cc1ccc(-c2c(C3=CC[C@H](C(=O)N4CCCC45COC5)CC3)c3c(N)ncnc3n2C)c(C)n1] | H NMR (400 MHz, Methanol-$d_4$) 8.16 (s, 1H), 7.78 (dd, J = 9.0, 7.9 Hz, 1H), 7.55 (dd, J = 7.9, 4.8 Hz, 1H), 5.88 (d, J = 14.9 Hz, 1H), 5.52-5.44 (m, 2H), 4.41 (dd, J = 5.3, 2.1 Hz, 2H), 3.89 (d, J = 0.9 Hz, 1H), 3.58 (f, J = 14.1, 7.1, 6.6, 3.0 Hz, 2H), 3.48 (s, 3H), 2.90 (d, J = 5.9 Hz, 1H), 2.43 (d, J = 18.4 Hz, 1H), 2.37 (s, 3H), 2.43-2.23 (m, 3H), 2.22 (dd, J = 45.1, 24.5 Hz, 2H), 1.94-1.67 (m, 4H). | 483.20 |

TABLE 23-continued

Additional Exemplary Compounds

| Compound | Structure | Proton NMR | MS [M + 1] |
|---|---|---|---|
| ((R)-4-(4-amino-6-(6-ethynyl-4-methylpyridin-3-yl)-7-methyl-7H-pyrrolo[2,3-d]pyrimidin-5-yl)cyclohex-3-en-1-yl)((S)-2-(methoxymethyl)pyrrolidin-1-yl)methanone | 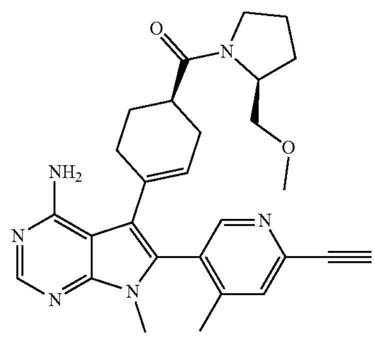 [SMILES: C#Cc1cc(C)c(-c2c(C3=CC[C@H](C(=O)N4CCC[C@H]4COC)CC3)c3c(N)ncnc3n2C)cn1] | $^1$H NMR (300 MHz, DMSO-d$_6$) δ 8.44-8.32 (m, 1H), 8.10 (d, J = 3.4 Hz, 1H), 7.60 (s, 1H), 6.63 (s, 2H), 5.72 (s, 1H), 4.40 (s, 1H), 4.04 (s, 1H), 3.51-3.32 (m, 5H), 3.24-3.14 (m, 5H), 2.76 (s, 1H), 2.21 (s, 1H), 2.12 (d, J = 4.3 Hz, 3H), 1.82 (d, J = 28.6 Hz, 6H), 1.57 (s, 2H). | 485.40 |
| ((S)-4-(4-amino-6-(6-ethynyl-4-methylpyridin-3-yl)-7-methyl-7H-pyrrolo[2,3-d]pyrimidin-5-yl)cyclohex-3-en-1-yl)((S)-2-(methoxymethyl)pyrrolidin-1-yl)methanone | 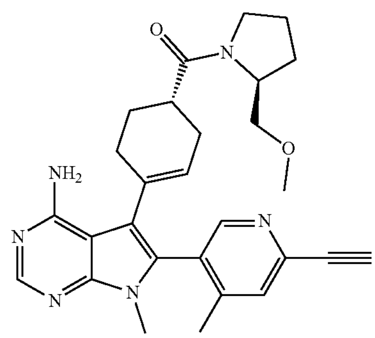 [SMILES: C#Cc1cc(C)c(-c2c(C3=CC[C@@H](C(=O)N4CCC[C@H]4COC)CC3)c3c(N)ncnc3n2C)cn1] | $^1$H NMR (400 MHz, DMSO-d$_6$) 8.40 (s, 1H), 8.14 (d, J = 3.8 Hz, 1H), 7.63 (s, 1H), 6.52 (s, 1H), 5.65 (d, J = 7.1 Hz, 1H), 4.43 (s, 1H), 4.10 (d, J = 37.6 Hz, 1H), 3.45 (m, J = 11.4, 4.6 Hz, 2H), 3.44-3.35 (m, 3H), 3.23 (d, J = 4.3 Hz, 5H), 2.70 (d, J = 15.0 Hz, 1H), 2.15 (d, J = 13.9 Hz, 5H), 1.93 (d, J = 23.9 Hz, 2H), 1.80 (s, 4H), 1.58 (s, 2H), | 485.25 |
| ((R)-4-(4-amino-6-(6-ethynyl-2-methylpyridin-3-yl)-7-methyl-7H-pyrrolo[2,3-d]pyrimidin-5-yl)cyclohex-3-en-1-yl)((S)-2-(methoxymethyl)pyrrolidin-1-yl)methanone | 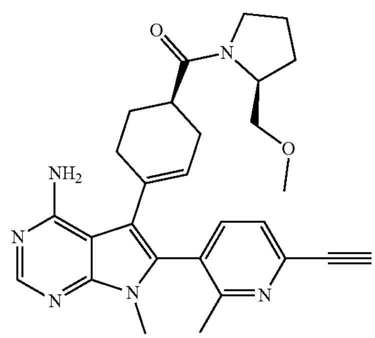 [SMILES: C#Cc1ccc(-c2c(C3=CC[C@H](C(=O)N4CCC[C@H]4COC)CC3)c3c(N)ncnc3n2C)c(C)n1] | $^1$H NMR (300 MHz, DMSO-d$_6$) δ 8.14-8.06 (m, 1H), 7.78-7.63 (m, 1H), 7.49 (dd, J = 8.0, 3.8 Hz, 1H), 6.58 (d, J = 30.8 Hz, 1H), 5.67 (d, J = 14.1 Hz, 1H), 4.43-4.37 (m, 1H), 4.03 (s, 1H), 3.35 (d, J = 1.2 Hz, 5H), 3.24-3.12 (m, 5H), 2.76 (s, 1H), 2.25 (d, J = 2.5 Hz, 3H), 2.11 (s, 1H), 1.81 (d, J = 21.3 Hz, 6H), 1.57 (s, 2H). | 485.40 |
| ((S)-4-(4-amino-6-(6-ethynyl-2-methylpyridin-3-yl)-7-methyl-7H-pyrrolo[2,3-d]pyrimidin-5-yl)cyclohex-3-en-1-yl)((S)-2-(methoxymethyl)pyrrolidin-1-yl)methanone | 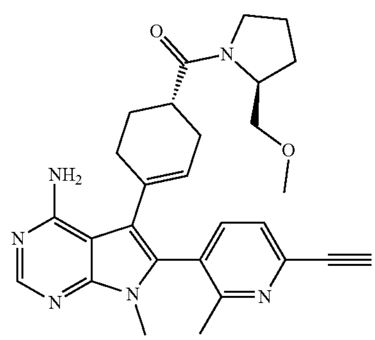 [SMILES: C#Cc1ccc(-c2c(C3=CC[C@@H](C(=O)N4CCC[C@H]4COC)CC3)c3c(N)ncnc3n2C)c(C)n1] | $^1$H NMR (400 MHz, DMSO-d$_6$) 8.14 (d, J = 3.7 Hz, 1H), 7.73 (d, J = 7.9 Hz, 1H), 7.52 (d, J = 7.9 Hz, 1H), 6.51 (s, 2H), 5.66 (d, J = 12.7 Hz, 1H), 4.43 (s, 1H), 4.08 (d, J = 37.6 Hz, 1H), 3.44 (m, J = 11.4, 4.6 Hz, 2H), 3.38 (d, J = 3.2 Hz, 3H), 3.23 (d, J = 4.9 Hz, 5H), 2.71 (t, J = 10.2 Hz, 1H), 2.28 (d, J = 3.2 Hz, 3H), 2.17 (s, 2H), 1.91 (d, J = 22.3 Hz, 3H), 1.80 (s, J = 7.7, 6.8 Hz, 3H), 1.58 (s, 2H). | 485.20 |

TABLE 23-continued

Additional Exemplary Compounds

| Compound | Structure | Proton NMR | MS [M + 1] |
|---|---|---|---|
| (S)-1-(4-(4-amino-6-(6-ethynyl-4-methylpyridin-3-yl)-7-methyl-7H-pyrrolo[2,3-d]pyrimidin-5-yl)cyclohex-3-ene-1-carbonyl)pyrrolidin-2-one | 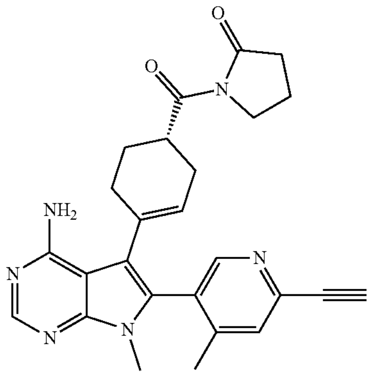 [SMILES: C#Cc1cc(C)c(-c2c(C3=CC[C@@H](C(=O)N4CCCC4=O)CC3)c3c(N)ncnc3n2C)cn1] | $^1$H NMR (400 MHz, DMSO-d$_6$) δ 8.40 (d, J = 11.4 Hz, 1H), 8.14 (s, 1H), 7.63 (d, J = 2.4 Hz, 1H), 6.46 (s, 2H), 5.72 (d, J = 24.8 Hz, 1H), 4.43 (s, 1H), 3.65 (m, J = 33.4 Hz, 3H), 3.37 (d, J = 2.7 Hz, 3H), 2.60-2.53 (m, 1H), 2.39-2.19 (m, 2H), 2.14 (s, 3H), 1.99-1.86 (m, 4H), 1.81-1.57 (m, 3H). | 455.30 |
| (R)-1-(4-(4-amino-6-(6-ethynyl-4-methylpyridin-3-yl)-7-methyl-7H-pyrrolo[2,3-d]pyrimidin-5-yl)cyclohex-3-ene-1-carbonyl)pyrrolidin-2-one | 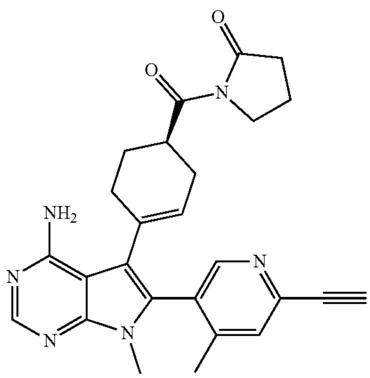 [SMILES: C#Cc1cc(C)c(-c2c(C3=CC[C@H](C(=O)N4CCCC4=O)CC3)c3c(N)ncnc3n2C)cn1] | $^1$H NMR (300 MHz, DMSO-d$_6$) δ 8.37 (d, J = 8.3 Hz, 1H), 8.12 (s, 1H), 7.64-7.57 (m, 1H), 6.43 (s, 2H), 5.70 (d, J = 18.3 Hz, 1H), 4.39 (s, 1H), 3.73-3.55 (m, 3H), 3.35 (d, J = 1.9 Hz, 3H), 2.57-2.48 (m, 1H), 2.28 (d, J = 23.1 Hz, 2H), 2.11 (s, 3H), 1.89 (p, J = 7.6 Hz, 4H), 1.79-1.42 (m, 3H). | 455.20 |
| ((S)-4-(4-amino-6-(6-ethynyl-4-methylpyridin-3-yl)-7-methyl-7H-pyrrolo[2,3-d]pyrimidin-5-yl)cyclohex-3-en-1-yl)((R)-2-methylpyrrolidin-1-yl)methanone | 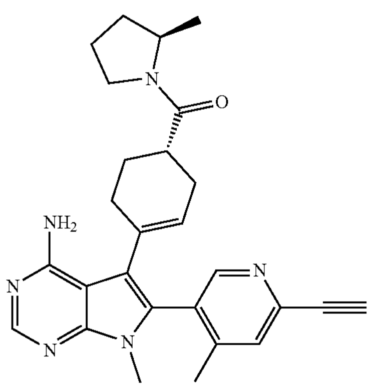 [SMILES: C#Cc1cc(C)c(-c2c(C3=CC[C@@H](C(=O)N4CCC[C@H]4C)CC3)c3c(N)ncnc3n2C)cn1] | $^1$H NMR (400 MHz, DMSO-d$_6$) δ 8.49-8.31 (m, 1H), 8.14 (d, J = 3.3 Hz, 1H), 7.63 (s, 1H), 6.54 (s, 2H), 5.67 (d, J = 26.6 Hz, 1H), 4.43 (s, 1H), 4.00 (s, 1H), 3.51 (s, 1H), 3.38 (d, J = 2.7 Hz, 3H), 3.37 (s, 3H), 2.68 (t, J = 1.9 Hz, 1H), 2.53 (s, 1H), 2.14 (d, J = 4.4 Hz, 4H), 2.07-1.44 (m, 8H), 1.07 (d, J = 6.2 Hz, 3H). | 455.25 |
| ((S)-4-(4-amino-6-(6-ethynyl-4-methylpyridin-3-yl)-7-methyl-7H-pyrrolo[2,3-d]pyrimidin-5-yl)cyclohex-3-en-1-yl)((S)-2-(hydroxymethyl)pyrrolidin-1-yl)methanone | 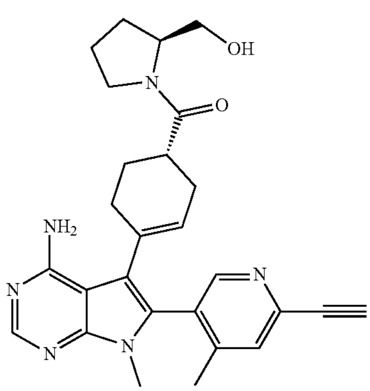 [SMILES: C#Cc1cc(C)c(-c2c(C3=CC[C@@H](C(=O)N4CCC[C@H]4CO)CC3)c3c(N)ncnc3n2C)cn1] | $^1$H NMR (400 MHz, DMSO-d$_6$) δ 8.45-8.36 (m, 1H), 8.14 (d, J = 2.7 Hz, 1H), 7.63 (s, 1H), 6.51 (s, 2H), 5.67 (d, J = 25.9 Hz, 1H), 4.95-4.67 (m, 1H), 4.42 (s, 1H), 3.95 (d, J = 15.4 Hz, 1H), 3.47 (dt, J = 10.0, 4.4 Hz, 2H), 3.37 (s, 3H), 3.29-3.19 (m, 1H), 2.70 (s, 1H), 2.14 (d, J = 5.2 Hz, 5H), 1.97-1.78 (m, 6H), 1.58 (s, 2H). | 471.35 |

TABLE 23-continued

Additional Exemplary Compounds

| Compound | Structure | Proton NMR | MS [M + 1] |
|---|---|---|---|
| (S)-(4-(4-amino-6-(6-ethynyl-4-methylpyridin-3-yl)-7-methyl-7H-pyrrolo[2,3-d]pyrimidin-5-yl)cyclohex-3-en-1-yl)(2-oxa-5-azaspiro[3.4]octan-5-yl)methanone | 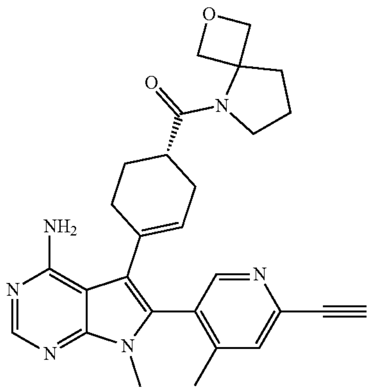 [SMILES: C#Cc1cc(C)c(-c2c(C3=CC[C@@H](C(=O)N4CCCC45COC5)CC3)c3c(N)ncnc3n2C)cn1] | 1H NMR: 1H NMR (400 MHz, DMSO-d6) 8.41 (d, J = 8.2 Hz, 1H), 8.15 (s, 1H), 7.71-7.56 (m, 1H), 6.59 (s, 1H), 5.71 (d, J = 24.5 Hz, 1H), 5.36-5.21 (m, 2H), 4.43 (s, 1H), 4.18 (d, J = 4.9 Hz, 2H), 3.53-3.41 (m, 2H), 3.38 (s, 3H), 2.77 (s, 1H), 2.39-2.18 (m, 4H), 2.14 (d, J = 2.8 Hz, 3H), 1.94 (d, J = 18.5 Hz, 2H), 1.71 (t, J = 6.8 Hz, 2H), 1.61 (s, 2H). | 483.20 |
| 6-(6-ethynyl-4-methylpyridin-3-yl)-7-methyl-5-[(4S)-4-[(2S)-2-methylpyrrolidine-1-carbonyl]cyclohex-1-en-1-yl]-7H-pyrrolo[2,3-d]pyrimidin-4-amine | 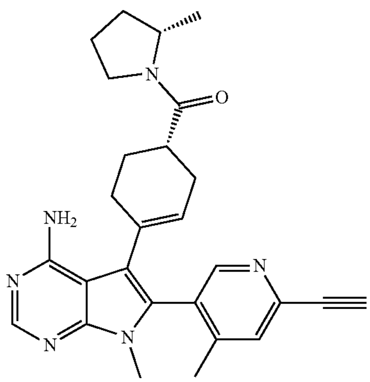 [SMILES: C#Cc1cc(C)c(-c2c(C3=CC[C@@H](C(=O)N4CCC[C@@H]4C)CC3)c3c(N)ncnc3n2C)cn1] | $^1$H NMR (400 MHz, DMSO-d$_6$) δ 8.43-8.24 (m, 1H), 8.10 (d, J = 3.2 Hz, 1H), 7.60 (s, 1H), 5.67 (d, J = 27.0 Hz, 1H), 4.40 (s, 1H), 3.99 (s, 1H), 3.44 (s, 2H), 3.35(s, 3H), 2.48 (s, 2H), 2.11 (d, J = 3.6 Hz, 2H), 1.88 (s, 5H), 1.77-1.57(m, 4H), 1.19-0.81 (m, 4H). | 455.20 |
| ((R)-4-(4-amino-6-(6-ethynyl-4-methylpyridin-3-yl)-7-methyl-7H-pyrrolo[2,3-d]pyrimidin-5-yl)cyclohex-3-en-1-yl)((R)-2-methylpyrrolidin-1-yl)methanone | 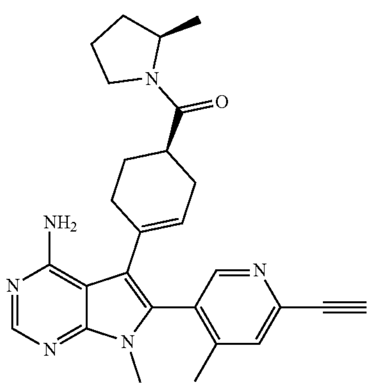 [SMILES: C#Cc1cc(C)c(-c2c(C3=CC[C@H](C(=O)N4CCC[C@H]4C)CC3)c3c(N)ncnc3n2C)cn1] | $^1$H NMR (400 MHz, DMSO-d$_6$) 8.45-8.37 (m, 1H), 8.13 (d, J = 4.3 Hz, 1H), 7.63 (s, 1H), 6.55 (s, 1H), 5.70 (d, J = 37.1 Hz, 1H), 4.42 (d, J = 2.0 Hz, 1H), 4.01 (s, 1H), 3.47 (t, J = 6.4 Hz, 1H), 3.4-3.35 (m, 4H), 2.72 (d, J = 33.0 Hz, 1H), 2.24 (s, 1H), 2.19-2.13 (m, 4H), 1.85 (d, J = 44.5 Hz, 5H), 1.57 (s, 2H), 1.47 (s, 1H), 1.13-1.03 (m, 3H). | 455.20 |
| ((R)-4-(4-amino-6-(6-ethynyl-4-methylpyridin-3-yl)-7-methyl-7H-pyrrolo[2,3-d]pyrimidin-5-yl)cyclohex-3-en-1-yl)((S)-2-methylpyrrolidin-1-yl)methanone | 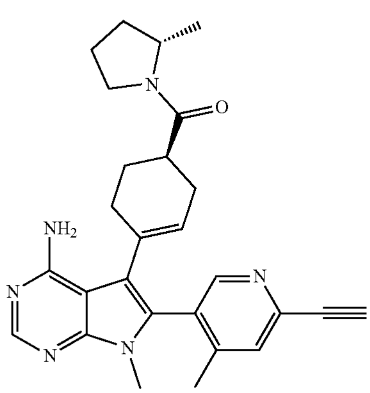 [SMILES: C#Cc1cc(C)c(-c2c(C3=CC[C@H](C(=O)N4CCC[C@@H]4C)CC3)c3c(N)ncnc3n2C)cn1] | $^1$H NMR (400 MHz, DMSO-d6) 8.42-8.37 (m, 1H), 8.14 (d, J = 3.2 Hz, 1H), 7.63 (d, J = 2.0 Hz, 1H), 6.54 (s, 1H), 5.67 (d, J = 26.1 Hz, 1H), 4.42 (s, 1H), 4.05 (d, J = 39.4 Hz, 1H), 3.57 (d, J = 42.9 Hz, 1H), 3.35-3.48 (m, 4H), 2.69 (d, J = 6.9 Hz, 1H), 2.14 (d, J = 4.3 Hz, 5H), 1.94 (d, J = 18.5 Hz, 3H), 1.82 (s, 2H), 1.57 (s, 2H), 1.49 (d, J = 5.7 Hz, 1H), 1.09 (dd, J = 12.6, 6.6 Hz, 3H). | 455.15 |

TABLE 23-continued

Additional Exemplary Compounds

| Compound | Structure | Proton NMR | MS [M + 1] |
|---|---|---|---|
| ((S)-4-(4-amino-6-(2-ethynyl-1H-benzo[d]imidazol-5-yl)-7-methyl-7H-pyrrolo[2,3-d]pyrimidin-5-yl)cyclohex-3-en-1-yl)((S)-2-(methoxymethyl)pyrrolidin-1-yl)methanone | 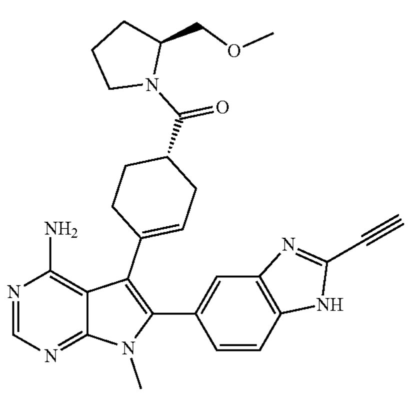 [SMILES: C#Cc1nc2cc(-c3c(C4=CC[C@@H](C(=O)N5CCC[C@H]5COC)CC4)c4c(N)ncnc4n3C)ccc2[nH]1] | 1H NMR (400 MHz, DMSO-d6) δ 13.32 (s, 1H), 8.12 (d, J = 3.9 Hz, 1H), 7.73 (s, 1H), 7.56 (s, 1H), 7.38 (s, 1H), 6.3(s, 2H), 5.79 (s, 1H), 4.71 (s, 1H), 4.02 (s, 1H), 3.59 (s, 3H), 3.53-3.37 (m, 3H), 3.24 (s, 4H), 2.72 (s, J = 32.8 Hz, 1H), 2.29 (d, J = 36.4 Hz, 2H), 1.90 (d, J = 13.4 Hz, 3H), 1.80 (d, J = 5.1 Hz, 3H), 1.54 (s, 2H). | 510.30 |
| ((R)-4-(4-amino-6-(2-ethynyl-1H-benzo[d]imidazol-5-yl)-7-methyl-7H-pyrrolo[2,3-d]pyrimidin-5-yl)cyclohex-3-en-1-yl)((S)-2-(methoxymethyl)pyrrolidin-1-yl)methanone | 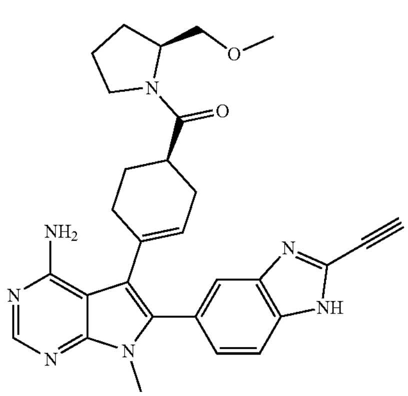 [SMILES: C#Cc1nc2cc(-c3c(C4=CC[C@H](C(=O)N5CCC[C@H]5COC)CC4)c4c(N)ncnc4n3C)ccc2[nH]1] | 1H NMR (400 MHz, DMSO-d6) δ 13.33 (d, J = 10.2 Hz, 1H), 8.13-8.08 (m, 1H), 7.72 (d, J = 8.0 Hz, 1H), 7.57 (d, J = 8.5 Hz, 1H), 7.38 (dd, J = 14.6, 8.7 Hz, 1H), 6.59 (s, 2H), 5.80 (s, 1H), 4.72 (d, J = 1.1 Hz, 1H), 4.05 (s, 1H), 3.59 (d, J = 6.7 Hz, 3H), 3.49 (d, J = 8.1 Hz, 1H), 3.27-3.22 (m, 1H), 3.17 (d, J = 1.3 Hz, 2H), 2.83 (s, 3H), 2.4(s, 1H), 2.20 (s, 1H), 1.87-1.83 (m, 1H), 1.78 (s, 6H), 1.54 (s, 2H). | 510.30 |
| ((S)-4-(4-amino-6-(6-ethynyl-4-methoxypyridin-3-yl)-7-methyl-7H-pyrrolo[2,3-d]pyrimidin-5-yl)cyclohex-3-en-1-yl)((R)-2-methylpyrrolidin-1-yl)methanone | 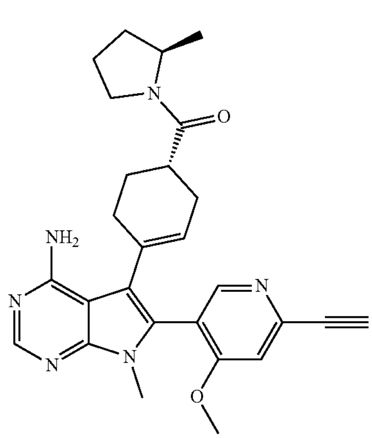 [SMILES: C#Cc1cc(OC)c(-c2c(C3=CC[C@@H](C(=O)N4CCC[C@H]4C)CC3)c3c(N)ncnc3n2C)cn1] | $^1$H NMR (400 MHz, DMSO-d$_6$) δ8.28-8.25 (m, 1H), 8.16-8.10 (m, 1H), 7.41 (d, J = 4.3 Hz, 1H), 6.54 (s, 2H), 5.66 (d, J = 33.7 Hz, 1H), 4.46 (s, 1H), 4.15-3.96 (m, 1H), 3.91 (d, J = 3.4 Hz, 3H), 3.42 (d, J = 3.4 Hz, 4H), 3.34 (s, 1H), 2.72(s, 1H), 2.17 (s, 2H), 2.04-1.72 (m, 5H), 1.66 (d, J = 30.2 Hz, 2H), 1.50 (d, J = 6.2 Hz, 1H), 1.13-1.04 (m, 3H). | 471.35 |

TABLE 23-continued

Additional Exemplary Compounds

| Compound | Structure | Proton NMR | MS [M + 1] |
|---|---|---|---|
| ((R)-4-(4-amino-6-(6-ethynyl-4-methoxypyridin-3-yl)-7-methyl-7H-pyrrolo[2,3-d]pyrimidin-5-yl)cyclohex-3-en-1-yl)((R)-2-methylpyrrolidin-1-yl)methanone | 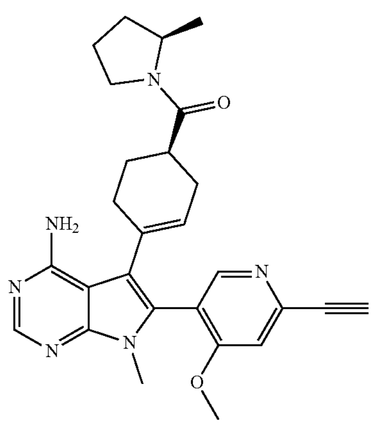 [SMILES: C#Cc1cc(OC)c(-c2c(C3=CC[C@H](C(=O)N4CCC[C@H]4C)CC3)c3c(N)ncnc3n2C)cn1] | $^1$H NMR (400 MHz, DMSO-d$_6$) δ8.26 (s, 1H), 8.16-8.06 (m, 1H), 7.41 (s, 1H), 6.59 (d, J = 95.2 Hz, 2H), 5.83-5.57 (m, 1H), 4.45 (d, J = 2.5 Hz, 1H), 4.03 (d, J = 8.5 Hz, 2H), 3.91 (s, 3H), 3.48 (s, 1H), 3.42 (d, J = 3.1 Hz, 3H), 2.84-2.65 (m, 1H), 2.36-2.04 (m, 2H), 2.02-1.72 (m, 5H), 1.56 (d, J = 60.9 Hz, 3H), 1.17-1.01 (m, 3H). | 471.35 |
| (R)-(4-(4-amino-6-(6-ethynyl-4-methylpyridin-3-yl)-7-methyl-7H-pyrrolo[2,3-d]pyrimidin-5-yl)cyclohex-3-en-1-yl)(4-azaspiro[2.4]heptan-4-yl)methanone | 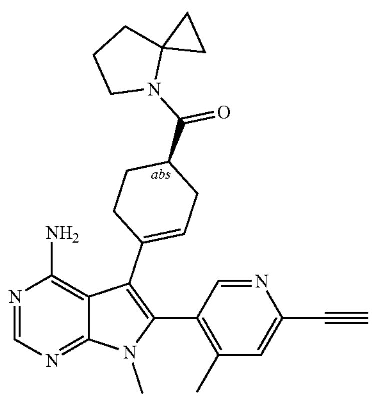 [SMILES: C#Cc1cc(C)c(-c2c(C3=CC[C@H](C(=O)N4CCCC45CC5)CC3)c3c(N)ncnc3n2C)cn1] | $^1$H NMR (400 MHz, DMSO-d6) 8.39 (d, J = 6.1 Hz, 1H), 8.13 (s, 1H), 7.62 (s, 1H), 6.53 (s, 1H), 5.66 (d, J = 28.0 Hz, 1H), 4.42 (s, 1H), 3.77-3.52 (m, 2H), 3.32(m, 3H), 2.70 (s, 1H), 2.36-2.03 (m, 5H), 1.97-1.51 (m, 8H), 1.36(s, 2H), 0.39 (s, 2H). | 467.25 |
| (S)-(4-(4-amino-6-(6-ethynyl-4-methylpyridin-3-yl)-7-methyl-7H-pyrrolo[2,3-d]pyrimidin-5-yl)cyclohex-3-en-1-y)(4-azaspiro[2.4]heptan-4-yl)methanone | 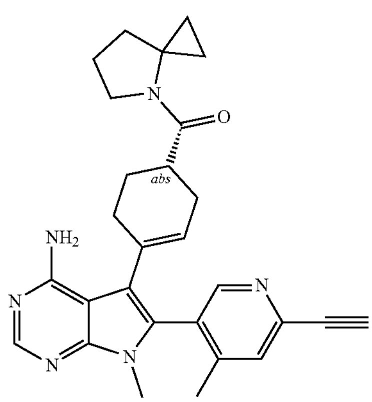 | $^1$H NMR (400 MHz, DMSO-d6) 8.39 (d, J = 6.1 Hz, 1H), 8.13 (s, 1H), 7.62 (s, 1H), 6.53 (s, 1H), 5.66 (d, J = 28.0 Hz, 1H), 4.42 (s, 1H), 3.77-3.52 (m, 2H), 3.32(m, 3H), 2.70 (s, 1H), 2.36-2.04 (m, 5H), 1.98-1.50 (m, 8H), 1.35(s, 2H), 0.39 (s, 2H). | 467.25 |

TABLE 23-continued
Additional Exemplary Compounds
| Compound | Structure | Proton NMR | MS [M + 1] |
|---|---|---|---|
| (S)-(4-(4-amino-6-(2-ethynyl-1-methyl-1H-benzo[d]imidazol-5-yl)-7-methyl-7H-pyrrolo[2,3-d]pyrimidin-5-yl)cyclohex-3-en-1-yl)(pyrrolidin-1-yl)methanone | 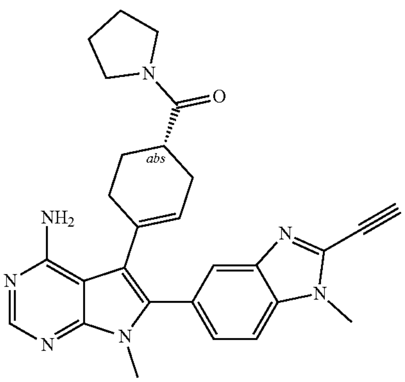 [SMILES: C#Cc1nc2cc(-c3c(C4=CC[C@@H](C(=O)N5CCCC5)CC4)c4c(N)ncnc4n3C)ccc2n1C] | ¹H NMR (400 MHz, DMSO-d6) 8.11 (s, 1H), 7.76 (d, J = 1.5 Hz, 1H), 7.71 (d, J = 8.5 Hz, 1H), 7.47 (dd, J = 8.5, 1.6 Hz, 1H), 6.56 (s, 1H), 5.80 (s, 1H), 5.00 (s, 1H), 3.93 (s, 3H), 3.58 (s, 3H), 3.49 (dt, J = 10.1, 6.6 Hz, 1H), 3.43-3.37 (m, 1H), 3.28 (d, J = 6.4 Hz, 0H), 3.23 (dd, J = 11.9, 6.6 Hz, 1H), 2.80 (t, J = 5.9 Hz, 1H), 2.26 (q, J = 20.5, 18.0 Hz, 2H), 1.84 (q, J = 6.6 Hz, 4H), 1.55 (s, 2H). | 480.25 |
Example 25
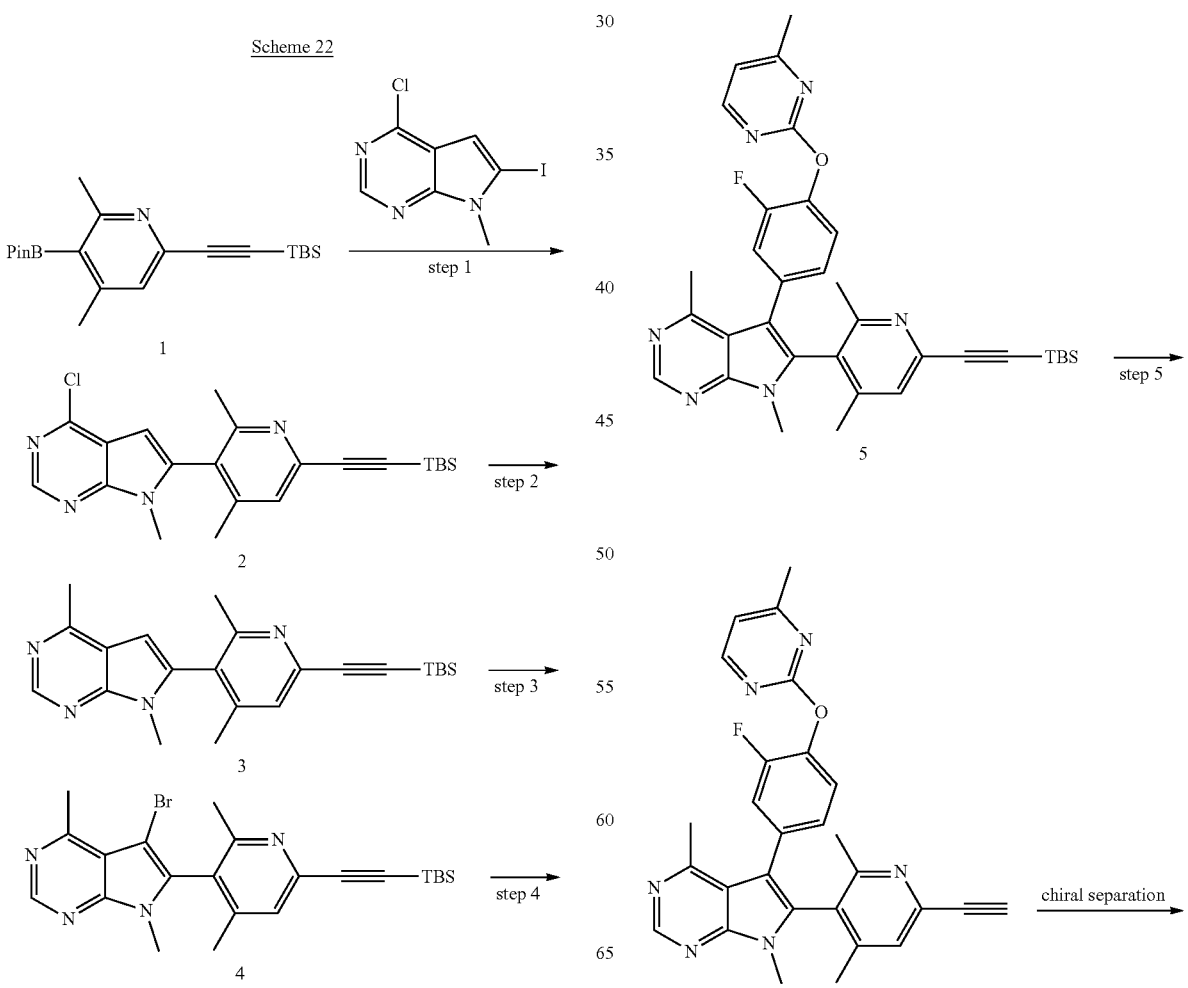
Scheme 22

-continued

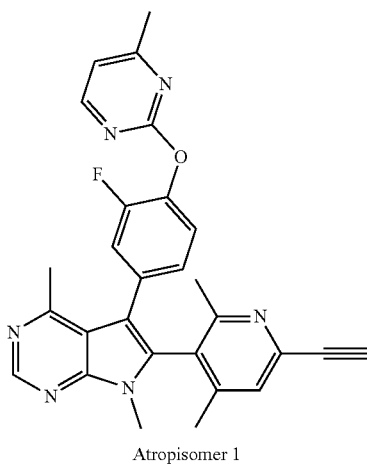

Atropisomer 1

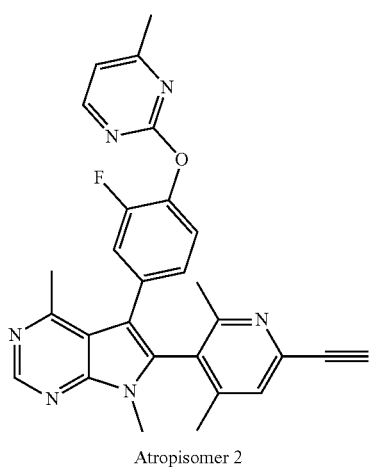

Atropisomer 2

6-(6-((tert-butyldimethylsilyl)ethynyl)-2,4-dimethylpyridin-3-yl)-4-chloro-7-methyl-7H-pyrrolo[2,3-d]pyrimidine

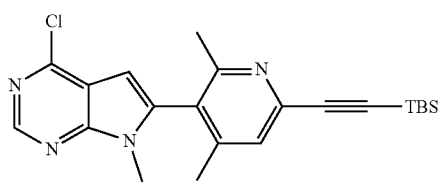

Step 1: A resealable reaction vial was charged with 4-chloro-6-iodo-7-methyl-7H-pyrrolo[2,3-d]pyrimidine (1.2 g, 4.1 mmol), N 6-((tert-butyldimethylsilyl)ethynyl)-2,4-dimethyl-3-(4,4,5,5-tetramethyl-1,3,2-dioxaborolan-2-yl)pyridine (1.82 g, 4.91 mmol), PAd2nBu Pd-G2 (0.27 g, 0.41 mmol), PAd2nBu (0.29 g, 0.82 mmol), K3PO4 (2.61 g, 12.3 mmol), dioxane (30 mL), H2O (3 mL) and a stir bar before being evacuated and purged with nitrogen three times. The mixture was stirred for 15 h at 70° C. The reaction mixture was concentrated in vacuo. The resulting crude material was purified silica gel chromatography (eluting with MeOH/DCM=1/100~1/20). Concentration in vacuo resulted in 6-(6-((tert-butyldimethylsilyl)ethynyl)-2,4-dimethylpyridin-3-yl)-4-chloro-7-methyl-7H-pyrrolo[2,3-d]pyrimidine (0.7 g, 42%) as brown solid.

6-(6-((tert-butyldimethylsilyl)ethynyl)-2,4-dimethylpyridin-3-yl)-4,7-dimethyl-7H-pyrrolo[2,3-d]pyrimidine

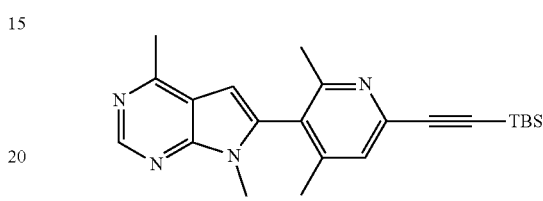

Step 2: A resealable reaction vial was charged with 6-(6-((tert-butyldimethylsilyl)ethynyl)-2,4-dimethylpyridin-3-yl)-4-chloro-7-methyl-7H-pyrrolo[2,3-d]pyrimidine (0.7 g, 1.7 mmol), Pd(PPh3)4 (0.2 g, 0.17 mmol), THF (20 mL) and a stir bar before being evacuated and purged with nitrogen three times. Zn(CH3)2 (1M, 2.04 mL, 2.04 mmol). The mixture was stirred for 2 h at 70° C. The reaction mixture was quenched with water, extracted with DCM, dried over Na2SO4, concentrated in vacuo. The resulting crude material was purified by silica gel chromatography (eluting with MeOH/DCM=1/100~1/30). Concentration in vacuo resulted in 6-(6-((tert-butyldimethylsilyl)ethynyl)-2,4-dimethylpyridin-3-yl)-4,7-dimethyl-7H-pyrrolo[2,3-d]pyrimidine (0.4 g, 60%) as brown solid.

5-bromo-6-(6-((tert-butyldimethylsilyl)ethynyl)-2,4-dimethylpyridin-3-yl)-4,7-dimethyl-7H-pyrrolo[2,3-d]pyrimidine

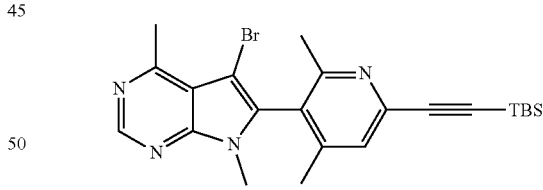

Step 3: A round bottomed flask was charged with 6-(6-((tert-butyldimethylsilyl)ethynyl)-2,4-dimethylpyridin-3-yl)-4,7-dimethyl-7H-pyrrolo[2,3-d]pyrimidine (0.4 g, 1 mmol), DMF (10 mL) and a stir bar. NBS (0.18 g, 1 mmol) was added. The mixture was stirred for 1 h. The reaction was quenched with saturated NaHSO3 aqueous solution, extracted with DCM (50 mL*3), the organic phase was combined and washed with brine for two times, dried with Na2SO4, evaporated in vacuo, the residue was dissolved with ACN (25 mL), and filtered, the filter cake was washed with ACN, dried under reduced pressure to afford 5-bromo-6-(6-((tert-butyldimethylsilyl)ethynyl)-2,4-dimethylpyridin-3-yl)-4,7-dimethyl-7H-pyrrolo[2,3-d]pyrimidine (440 mg, 94%) as yellow solid.

1687

6-(6-((tert-butyldimethylsilyl)ethynyl)-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine

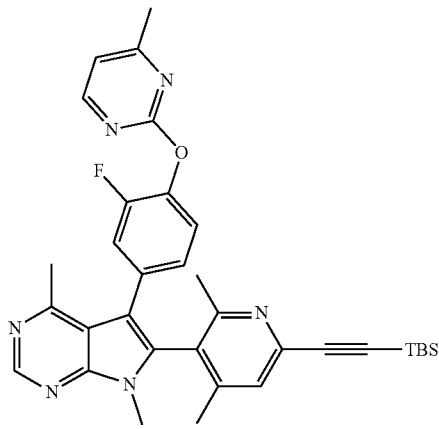

Step 4: A round bottomed flask was charged with 5-bromo-6-(6-((tert-butyldimethylsilyl)ethynyl)-2,4-dimethylpyridin-3-yl)-4,7-dimethyl-7H-pyrrolo[2,3-d]pyrimidine (440 mg, 0.94 mmol), 2-(2-fluoro-4-(4,4,5,5-tetramethyl-1,3,2-dioxaborolan-2-yl)phenoxy)-4-methylpyrimidine (371.5 mg, 1.1 mmol), Pd(PPh3)4 (104 mg, 0.09 mmol), K3PO4 (598 mg, 2.82 mmol), DME/H2O (10:1, 10 mL) and a stir bar before being evacuated and purged with nitrogen three times. The mixture was stirred for 2 h at 90° C. After cooling, the mixture was diluted with water, extracted with DCM, dried over Na₂SO₄, evaporated in vacuo, the residue was purified by silica gel chromatography (eluting with MeOH/DCM=1/100~1/10) to afford 6-(6-((tert-butyldimethylsilyl)ethynyl)-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine (300 mg, 54%) as brown solid.

1688

6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine

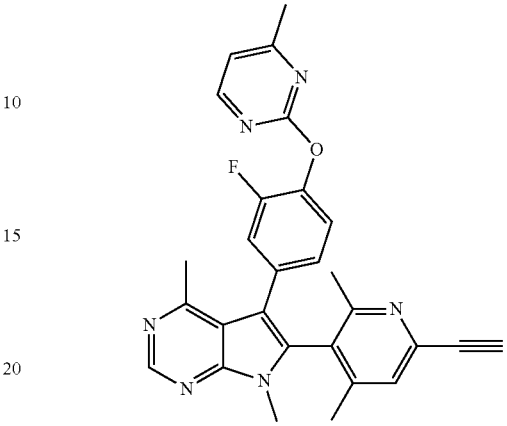

Step 5: A round bottomed flask was charged with 6-(6-((tert-butyldimethylsilyl)ethynyl)-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine (300 mg, 0.51 mmol), THF (10 mL) and a stir bar. TBAF (0.61 mL, 0.61 mmol) was added dropwise. The mixture was stirred for 0.5 h at r.t. The mixture was diluted with water, extracted with DCM, washed with brine, dried over Na₂SO₄, evaporated in vacuo, the residue was purified by prep-HPLC to afford (100 mg, 41%) as white solid. 100 mg of the target was sent to chiral separation (Column: CHIRALPAK IF, 2*25 cm, 5 um; Mobile Phase A:Hex (0.5% 2M NH3-MeOH), Mobile Phase B:EtOH:DCM=1:1-HPLC; Flow rate:20 mL/min; Gradient:20 B to 20 B in 15.5 min; 220/254 nm; RT1: 10.826; RT2:12.649; Injection Volumn:0.8 ml; Number Of Runs:5). Lyophilization afforded former peak (43.4 mg) and later peak (40.2 mg).

Additional compounds prepared according to the methods of Example 25 are depicted in Table 24 below.

TABLE 24

Additional Exemplary Compounds

| Compound | Structure | Proton NMR | MS [M + 1] |
|---|---|---|---|
| 6-(2-ethynylpyrimidin-5-yl)-4,7-dimethyl-5-(4-((4-methylpyrimidin-2-yl)oxy)phenyl)-7H-pyrrolo[2,3-d]pyrimidine | 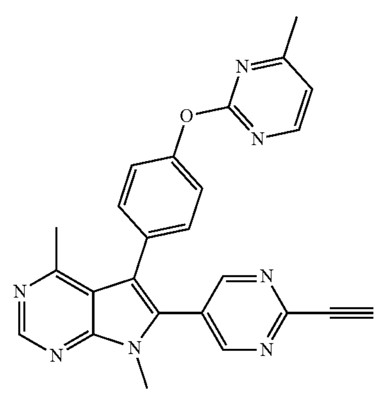 [SMILES: C#Cc1ncc(-c2c(-c3ccc(Oc4nccc(C)n4)cc3)c3c(C)ncnc3n2C)cn1] | ¹H NMR (400 MHz, DMSO-d₆) δ 8.87 (s, 2H), 8.79 (s, 1H), 8.49 (d, J = 5.0 Hz, 1H), 7.43-7.35 (m, 2H), 7.25-7.14 (m, 3H), 4.55 (s, 1H), 3.81 (s, 3H), 2.42 (s, 3H), 2.38 (s, 3H). | 434.15 |

TABLE 24-continued

Additional Exemplary Compounds

| Compound | Structure | Proton NMR | MS [M + 1] |
|---|---|---|---|
| 6-(2-ethynyl-4-methylpyrimidin-5-yl)-5-(3-fluoro-4-((4-methylpyrimidin-2-yl)oxy)phenyl)-4,7-dimethyl-7H-pyrrolo[2,3-d]pyrimidine | 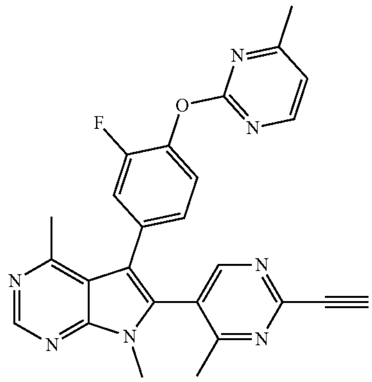 | $^1$H NMR (400 MHz, DMSO-d$_6$) δ 8.83 (d, J = 17.9 Hz, 2H), 8.49 (d, J = 5.0 Hz, 1H), 7.46-7.29 (m, 2H), 7.17 (dd, J = 18.9, 6.7 Hz, 2H), 4.52 (s, 1H), 3.64 (s, 3H), 2.44 (s, 3H), 2.41 (s, 3H), 2.21 (s, 3H). | 466.25 |
| 5-{4,7-dimethyl-5-[(4R)-4-(pyrrolidine-1-carbonyl)cyclohex-1-en-1-yl]-7H-pyrrolo[2,3-d]pyrimidin-6-yl}-2-ethynyl-4-methylpyrimidine | 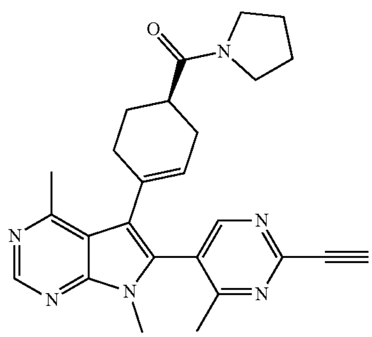 [SMILES: C#Cc1ncc(-c2c(C3=CC[C@H](C(=O)N4CCCC4)CC3)c3c(C)ncnc3n2C)c(C)n1] | $^1$H NMR (400 MHz, DMSO-d$_6$) δ 8.73 (d, J = 11.1 Hz, 2H), 5.85-5.20 (m, 1H), 4.53 (s, 1H), 3.53 (d, J = 1.3 Hz, 3H), 3.45 (td, J = 6.8, 2.9 Hz, 2H), 3.26 (d, J = 6.8 Hz, 2H), 2.67 (s, 3H), 2.33 (d, J = 3.2 Hz, 4H), 2.22-2.00 (m, 4H), 1.99-1.81 (m, 2H), 1.77 (q, J = 6.7 Hz, 3H), 1.49 (t, J = 11.9 Hz, 1H). | 441.35 |
| 5-{4,7-dimethyl-5-[(4S)-4-(pyrrolidine-1-carbonyl)cyclohex-1-en-1-yl]-7H-pyrrolo[2,3-d]pyrimidin-6-yl}-2-ethynyl-4-methylpyrimidine | 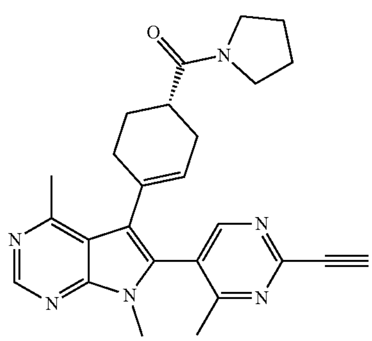 [SMILES: C#Cc1ncc(-c2c(C3=CC[C@@H](C(=O)N4CCCC4)CC3)c3c(C)ncnc3n2C)c(C)n1] | $^1$H NMR (400 MHz, DMSO-d$_6$) δ 8.73 (d, J = 11.0 Hz, 2H), 5.91-5.36 (m, 1H), 4.53 (s, 1H), 3.52 (d, J = 1.3 Hz, 3H), 3.45 (td, J = 6.7, 3.0 Hz, 2H), 3.26 (d, J = 6.9 Hz, 2H), 2.67 (s, 3H), 2.33 (t, J = 2.8 Hz, 4H), 2.15 (d, J = 30.9 Hz, 4H), 1.95-1.70 (m, 5H), 1.50 (s, 1H). | 441.35 |
| ((R)-4-(6-(6-ethynyl-4-methylpyridin-3-yl)-4,7-dimethyl-7H-pyrrolo[2,3-d]pyrimidin-5-yl)cyclohex-3-enyl)(pyrrolidin-1-yl)methanone | 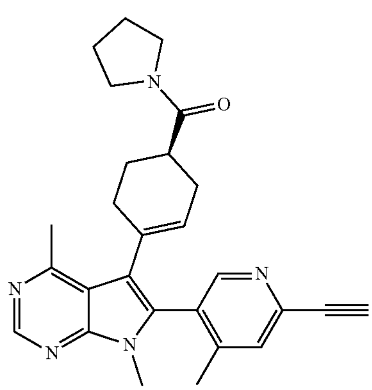 [SMILES: C#Cc1cc(C)c(-c2c(C3=CC[C@H](C(=O)N4CCCC4)CC3)c3c(C)ncnc3n2C)cn1] | 1H NMR (400 MHz, DMSO-d6) 8.69 (s, 1H), 8.44 (d, J = 11.8 Hz, 1H), 7.66 (s, 1H), 5.67 (d, J = 24.4 Hz, 1H), 4.45 (s, 1H), 3.45 (d, J = 11.5 Hz, 5H), 3.26 (t, J = 6.9 Hz, 2H), 2.67 (s, 3H), 2.47 (s, 1H), 2.26-2.02 (m, 7H), 1.92-1.81 (m, 2H), 1.77-1.75 (m, J = 6.7 Hz, 3H), 1.46-1.44 (m, 1H). | 440.30 |

TABLE 24-continued

Additional Exemplary Compounds

| Compound | Structure | Proton NMR | MS [M + 1] |
|---|---|---|---|
| ((S)-4-(6-(6-ethynyl-4-methylpyridin-3-yl)-4,7-dimethyl-7H-pyrrolo[2,3-d]pyrimidin-5-yl)cyclohex-3-enyl)(pyrrolidin-1-yl)methanone | 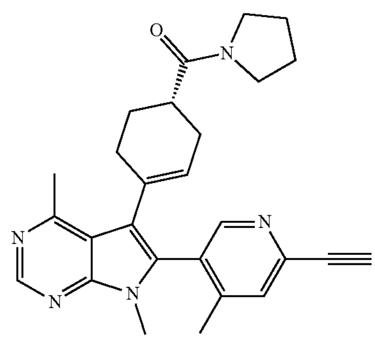 [SMILES: C#Cc1cc(C)c(-c2c(C3=CC[C@@H](C(=O)N4CCCC4)CC3)c3c(C)ncnc3n2C)cn1] | 1H NMR (400 MHz, DMSO-d6) 8.69 (s, 1H), 8.44 (d, J = 11.9 Hz, 1H), 7.66 (s, 1H), 5.67 (d, J = 24.4 Hz, 1H), 4.45 (s, 1H), 3.45 (d, J = 11.4 Hz, 5H), 3.26 (t, J = 7.0 Hz, 2H), 2.67 (s, 3H), 2.50 (s, 1H), 2.26-1.99 (m, 7H), 1.94-1.80 (m, 2H), 1.80-1.69 (m, 3H), 1.46-1.44 (m, 1H). | 440.25 |
| 2-{4-[6-(6-ethynyl-5-fluoro-4-methylpyridin-3-yl)-4,7-dimethyl-7H-pyrrolo[2,3-d]pyrimidin-5-yl]-2-fluorophenoxy}-4-methylpyrimidine | 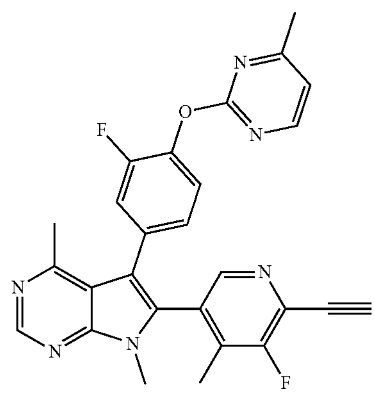 [SMILES: C#Cc1ncc(-c2c(-c3ccc(Oc4nccc(C)n4)c(F)c3)c3c(C)ncnc3n2C)c(C)c1F] | $^1$H NMR (400 MHz, DMSO-d$_6$) δ 8.78 (s, 1H), 8.49-8.40 (m, 2H), 7.39-7.24 (m, 2H), 7.20-7.06 (m, 2H), 4.80 (d, J = 0.9 Hz, 1H), 3.59 (s, 3H), 2.39 (d, J = 13.1 Hz, 6H), 2.00 (d, J = 2.2 Hz, 3H). | 483.30 |
| 4-chloro-6-(6-ethynyl-4-methylpyridin-3-yl)-5-(3-fluoro-4-((4-methylpyrimidin-2-yl)oxy)phenyl)-7-methyl-7H-pyrrolo[2,3-d]pyrimidine | 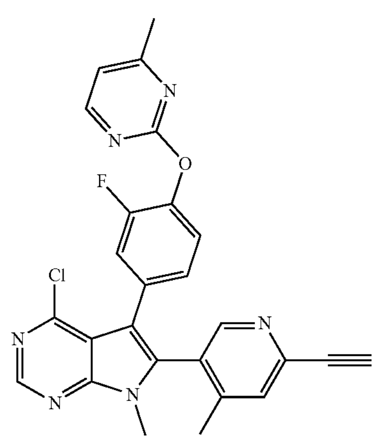 | 1H NMR (400 MHz, DMSO-d6) δ 8.78 (s, 1H), 8.58 (s, 1H), 8.47 (d, J = 5.0 Hz, 1H), 7.60 (s, 1H), 7.34-7.26 (m, 2H), 7.18 (d, J = 5.0 Hz, 1H), 7.10 (dt, J = 8.4, 1.4 Hz, 1H), 4.47 (s, 1H), 3.61 (s, 3H), 2.40 (s, 3H), 2.05 (s, 3H). | 485.10 |

TABLE 24-continued

Additional Exemplary Compounds

| Compound | Structure | Proton NMR | MS [M + 1] |
|---|---|---|---|
| 6-(6-ethynyl-2-fluoro-4-methylpyridin-3-yl)-5-(3-fluoro-4-((4-methylpyrimidin-2-yl)oxy)phenyl)-4,7-dimethyl-7H-pyrrolo[2,3-d]pyrimidine | | 1H NMR (400 MHz, DMSO-d6) δ 8.80 (s, 1H), 8.49 (d, J = 5.0 Hz, 1H), 7.62 (s, 1H), 7.37-7.29 (m, 2H), 7.19 (d, J = 5.0 Hz, 1H), 7.08 (d, J = 8.3 Hz, 1H), 4.61 (s, 1H), 3.61 (s, 3H), 2.45 (s, 3H), 2.41 (s, 3H), 2.09 (s, 3H). | 483.20 |
| 6-(6-ethynyl-2-fluoro-4-methylpyridin-3-yl)-5-(3-fluoro-4-((4-methylpyrimidin-2-yl)oxy)phenyl)-4,7-dimethyl-7H-pyrrolo[2,3-d]pyrimidine | 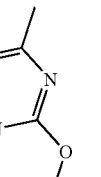 Atropisomer 1 | $^1$H NMR (400 MHz, DMSO-$d_6$) δ 8.80 (s, 1H), 8.49 (d, J = 5.0 Hz, 1H), 7.62 (s, 1H), 7.37-7.29 (m, 2H), 7.19 (d, J = 5.1 Hz, 1H), 7.11-7.06 (m, 1H), 4.62 (s, 1H), 3.61 (s, 3H), 2.45 (s, 3H), 2.40 (d, J = 5.3 Hz, 3H), 2.09 (s, 3H). | 483.25 |
| 6-(6-ethynyl-2-fluoro-4-methylpyridin-3-yl)-5-(3-fluoro-4-((4-methylpyrimidin-2-yl)oxy)phenyl)-4,7-dimethyl-7H-pyrrolo[2,3-d]pyrimidine | 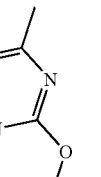 Atropisomer 2 | $^1$H NMR (400 MHz, DMSO-$d_6$) δ 8.81 (s, 1H), 8.49 (d, J = 5.0 Hz, 1H), 7.62 (s, 1H), 7.37-7.30 (m, 2H), 7.19 (d, J = 5.0 Hz, 1H), 7.11-7.06 (m, 1H), 4.62 (s, 1H), 3.61 (s, 3H), 2.46 (s, 3H), 2.41 (s, 3H), 2.09 (s, 3H). | 483.25 |

TABLE 24-continued

Additional Exemplary Compounds

| Compound | Structure | Proton NMR | MS [M + 1] |
|---|---|---|---|
| 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine | 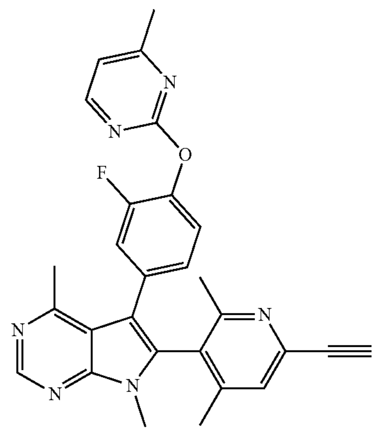 [SMILES: C#Cc1cc(C)c(-c2c(-c3ccc(Oc4nccc(C)n4)c(F)c3)c3c(C)ncnc3n2C)c(C)n1] | ¹H NMR (400 MHz, DMSO-d₆) δ 8.78 (s, 1H), 8.48 (d, J = 5.0 Hz, 1H), 7.45 (s, 1H), 7.34-7.25 (m, 2H), 7.18 (d, J = 5.0 Hz, 1H), 7.07 (d, J = 8.9 Hz, 1H), 4.39 (s, 1H), 3.51 (s, 3H), 2.44 (s, 3H), 2.40 (s, 3H), 2.19 (s, 3H), 2.05 (s, 3H). | 479.35 |
| 4-chloro-6-(6-ethynyl-2-fluoro-4-methylpyridin-3-yl)-5-(3-fluoro-4-((4-methylpyrimidin-2-yl)oxy)phenyl)-7-methyl-7H-pyrrolo[2,3-d]pyrimidine | | 1H NMR (400 MHz, DMSO-d6) δ 8.80 (s, 1H), 8.48 (d, J = 5.1 Hz, 1H), 7.63 (s, 1H), 7.31 (t, J = 8.5 Hz, 2H), 7.19 (d, J = 5.0 Hz, 1H), 7.05 (d, J = 8.3 Hz, 1H), 4.62 (s, 1H), 3.66 (s, 3H), 2.40 (s, 3H), 2.09 (s, 3H). | 503.15 |
| 4-chloro-6-(6-ethynyl-2-fluoro-4-methylpyridin-3-yl)-5-(3-fluoro-4-((4-methylpyrimidin-2-yl)oxy)phenyl)-7-methyl-7H-pyrrolo[2,3-d]pyrimidine | Atropisomer 1 | ¹H NMR (400 MHz, DMSO-d₆) δ 8.81 (s, 1H), 8.49 (d, J = 5.0 Hz, 1H), 7.63 (s, 1H), 7.36-7.29 (m, 2H), 7.19 (d, J = 5.0 Hz, 1H), 7.07-7.04 (m, 1H), 4.64 (s, 1H), 3.66 (s, 3H), 2.41 (s, 3H), 2.09 (s, 3H) | 503.25 |

TABLE 24-continued

Additional Exemplary Compounds

| Compound | Structure | Proton NMR | MS [M + 1] |
|---|---|---|---|
| 4-chloro-6-(6-ethynyl-2-fluoro-4-methylpyridin-3-yl)-5-(3-fluoro-4-((4-methylpyrimidin-2-yl)oxy)phenyl)-7-methyl-7H-pyrrolo[2,3-d]pyrimidine | Atropisomer 2 | $^1$H NMR (400 MHz, DMSO-d$_6$) δ 8.81 (s, 1H), 8.49 (d, J = 5.0 Hz, 1H), 7.63 (s, 1H), 7.34-7.29 (m, 2H), 7.19 (d, J = 5.1 Hz, 1H), 7.08-7.04 (m, 1H), 4.64 (s, 1H), 3.66 (s, 3H), 2.41 (s, 3H), 2.09 (s, 3H). | 503.25 |
| 2-{4-[4-chloro-6-(6-ethynyl-4-methoxypyridin-3-yl)-7-methyl-7H-pyrrolo[2,3-d]pyrimidin-5-yl]-2-fluorophenoxy}-4-methylpyrimidine | 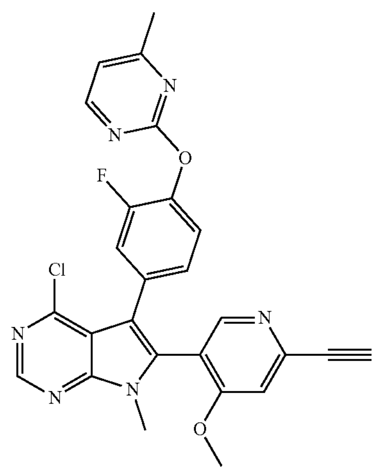 [SMILES: C#Cc1cc(OC)c(-c2c(-c3ccc(Oc4nccc(C)n4)c(F)c3)c3c(Cl)ncnc3n2C)cn1] | $^1$H NMR (400 MHz, DMSO-d$_6$) δ 8.76 (s, 1H), 8.49 (d, J = 5.0 Hz, 1H), 8.31 (s, 1H), 7.44 (s, 1H), 7.34-7.25 (m, 2H), 7.19 (d, J = 5.0 Hz, 1H), 7.11-7.03 (m, 1H), 4.50 (s, 1H), 3.87 (s, 3H), 3.67 (s, 3H), 2.41 (s, 3H). | 501.15 |
| 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine | Atropisomer 1 | $^1$H NMR (400 MHz, DMSO-d$_6$) δ 8.83 (s, 1H), 8.48 (d, J = 5.1 Hz, 1H), 7.46 (s, 1H), 7.36-7.24 (m, 2H), 7.19 (d, J = 5.0 Hz, 1H), 7.11-7.04 (m, 1H), 4.40 (s, 1H), 3.53 (s, 3H), 2.46 (s, 3H), 2.40 (s, 3H), 2.19 (s, 3H), 2.05 (s, 3H). | 479.25 |

TABLE 24-continued
Additional Exemplary Compounds
| Compound | Structure | Proton NMR | MS [M + 1] |
|---|---|---|---|
| 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine | 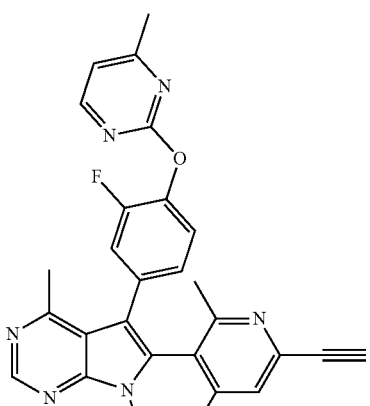/Atropisomer 2 | $^1$H NMR (400 MHz, DMSO-d$_6$) δ 8.79 (s, 1H), 8.48 (d, J = 5.0 Hz, 1H), 7.46 (s, 1H), 7.35-7.24 (m, 2H), 7.18 (d, J = 5.1 Hz, 1H), 7.11-7.04 (m, 1H), 4.39 (s, 1H), 3.51 (s, 3H), 2.45 (s, 3H), 2.40 (s, 3H), 2.19 (s, 3H), 2.06 (d, J = 14.0 Hz, 3H). | 479.25 |
Example 26
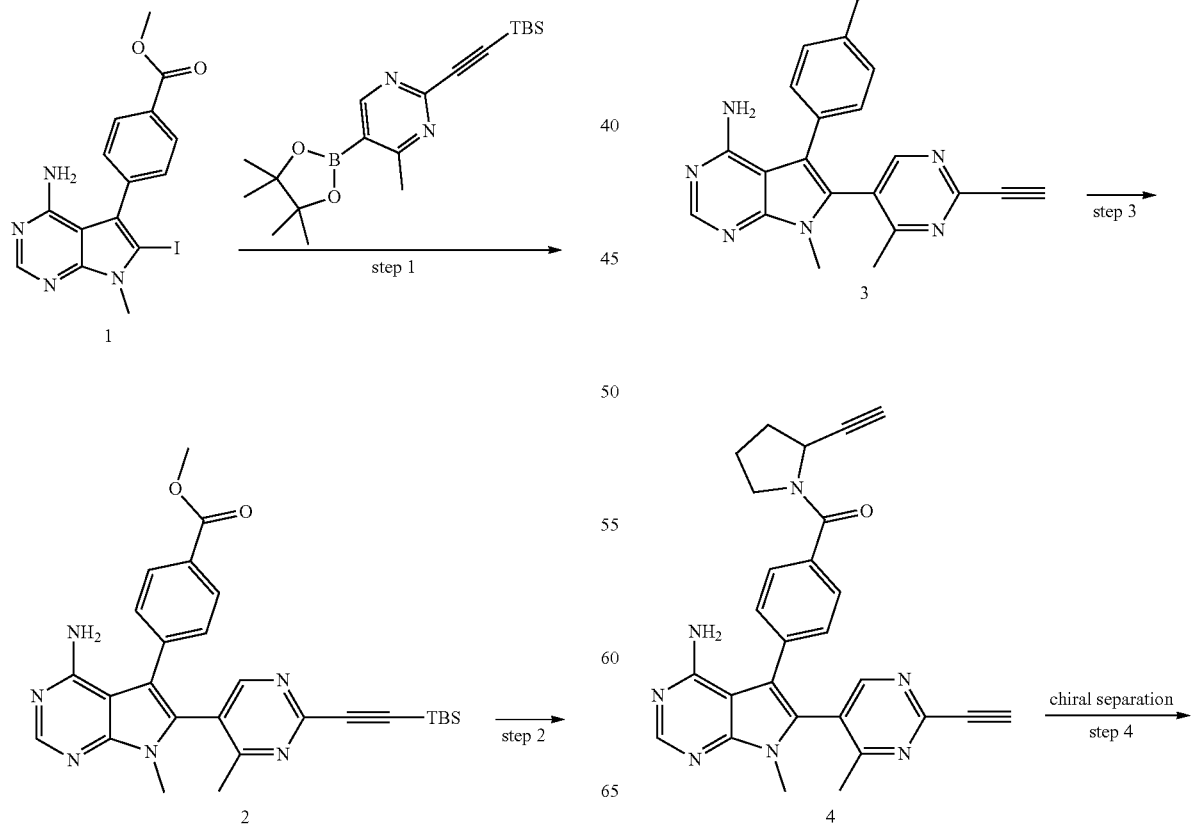

-continued

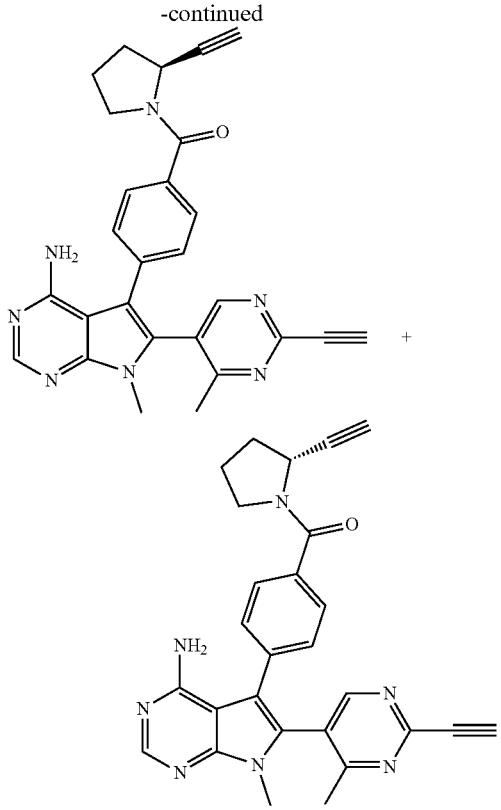

methyl 4-(4-amino-6-(2-((tert-butyldimethylsilyl)
ethynyl)-4-methylpyrimidin-5-yl)-7-methyl-7H-pyr-
rolo[2,3-d]pyrimidin-5-yl)benzoate

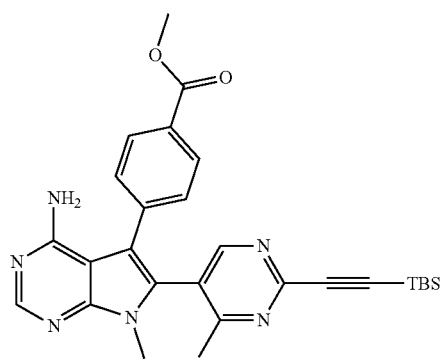

Step 1: A round bottomed flask was charged with methyl 4-(4-amino-6-iodo-7-methyl-7H-pyrrolo[2,3-d]pyrimidin-5-yl)benzoate (3 g, 7.35 mmol), 2-((tert-butyldimethylsilyl)ethynyl)-4-methyl-5-(4,4,5,5-tetramethyl-1,3,2-dioxaborolan-2-yl)pyrimidine (3.26 g, 8.82 mmol), Pd(dppf)Cl$_2$ (538 mg, 735 μmol), Cs$_2$CO$_3$ (4.79 g, 14.7 mmol), DME:water=10:1 (4 mL) and a stir bar before being evacuated and purged with nitrogen three times. The solution was stirred for 1 h at 90° C. The reaction mixture was quenched with water, extracted with DCM. The organic phase was dried over Na$_2$SO$_4$, filtered and evaporated in vacuo. The resulting crude material was purified by silica gel column chromatography. Concentration in vacuo resulted in methyl 4-(4-amino-6-(2-((tert-butyldimethylsilyl)ethynyl)-4-methylpyrimidin-5-yl)-7-methyl-7H-pyrrolo[2,3-d]pyrimidin-5-yl)benzoate (1.5 g, 39%) as a yellow amorphous solid.

4-(4-amino-6-(2-ethynyl-4-methylpyrimidin-5-yl)-7-methyl-7H-pyrrolo[2,3-d]pyrimidin-5-yl)benzoic acid

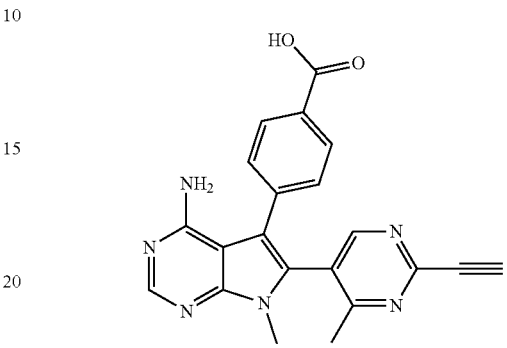

Step 2: A round bottomed flask was charged with methyl 4-(4-amino-6-(2-((tert-butyldimethylsilyl)ethynyl)-4-methylpyrimidin-5-yl)-7-methyl-7H-pyrrolo[2,3-d]pyrimidin-5-yl)benzoate (500 mg, 977 umol), THF (10 mL) and a stir bar. NaOH (2M, 1 mL, 1.95 mmol) was added, and the solution was stirred for 1 h at 60° C. The solvent was removed. The mixture was dissolved in water and adjusted to PH=2 with 1M HCl, and then extracted with ethyl acetate. The organic layers were combined and the solvent was removed under vacuum. This resulted in 4-(4-amino-6-(2-ethynyl-4-methylpyrimidin-5-yl)-7-methyl-7H-pyrrolo[2,3-d]pyrimidin-5-yl)benzoic acid (230 mg, 63%) as a yellow amorphous solid.

(4-(4-amino-6-(2-ethynyl-4-methylpyrimidin-5-yl)-7-methyl-7H-pyrrolo[2,3-d]pyrimidin-5-yl)phenyl)(2-ethynylpyrrolidin-1-yl)methanone

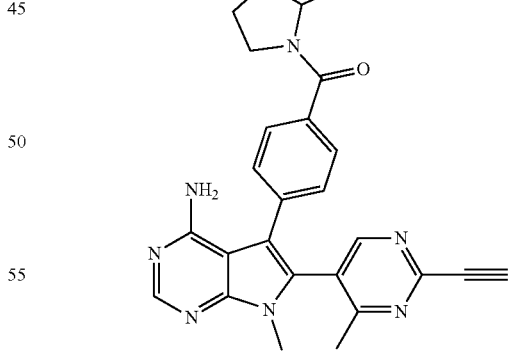

Step 3: A round bottomed flask was charged with (4-(4-amino-6-(2-ethynyl-4-methylpyrimidin-5-yl)-7-methyl-7H-pyrrolo[2,3-d]pyrimidin-5-yl)phenyl)(2-ethynylpyrrolidin-1-yl)methanone (210 mg, 0.55 mmol), 2-ethynylpyrrolidine (95 mg, 0.82 mmol), HATU (312 mg, 0.82 mmol), DIEA (211 mg, 1.64 mmol), dimethylformamide (5 mL). The solution was stirred for 1 h at room temperature. The reaction mixture was quenched with water, extracted with DCM. The organic phase was washed with brine three times, dried over Na₂SO₄, filtered and evaporated in vacuo. The resulting crude material was purified by prep-HPLC (Column: YMC-Actus Triart C18, 30*250, 5 um; Mobile Phase A:Water(10 MMOL/L NH₄HCO₃), Mobile Phase B:ACN; Flow rate:50 mL/min; Gradient:35 B to 53 B in 8 min; 220 nm; RT1:7.03). Concentration in vacuo resulted in (4-(4-amino-6-(2-ethynyl-4-methylpyrimidin-5-yl)-7-methyl-7H-pyrrolo[2,3-d]pyrimidin-5-yl)phenyl)(2-ethynylpyrrolidin-1-yl)methanone (60 mg, 24%) as an off-white amorphous solid.

(S)-(4-(4-amino-6-(2-ethynyl-4-methylpyrimidin-5-yl)-7-methyl-7H-pyrrolo[2,3-d]pyrimidin-5-yl)phenyl)(2-ethynylpyrrolidin-1-yl)methanone and (R)-(4-(4-amino-6-(2-ethynyl-4-methylpyrimidin-5-yl)-7-methyl-7H-pyrrolo[2,3-d]pyrimidin-5-yl)phenyl)(2-ethynylpyrrolidin-1-yl)methanone

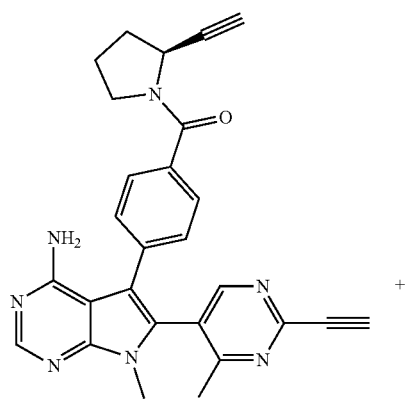

+

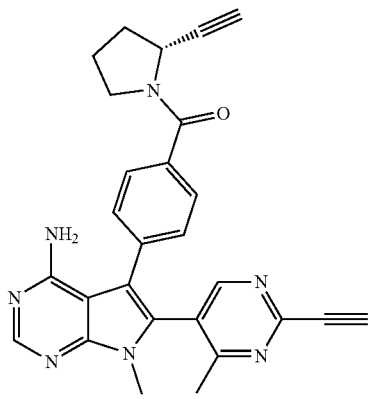 [SMILES: C#Cc1ncc(-c2c(-c3ccc(C(=O)N4CCCC4C#C)cc3)c3c(N)ncnc3n2C)c(C)n1]

Step 4: The racemic (4-(4-amino-6-(2-ethynyl-4-methylpyrimidin-5-yl)-7-methyl-7H-pyrrolo[2,3-d]pyrimidin-5-yl)phenyl)(2-ethynylpyrrolidin-1-yl)methanone (60 mg, 0.13 mmol) was purified by Chiral-HPLC (Column: CHIRAL ART Cellulose-SB, 4.6*100 mm, 3.0 um; Mobile Phase:Hex(0.2% IPAmine):(EtOH:DCM=1:1)=50:50) Lyophilization yielded (S)-(4-(4-amino-6-(2-ethynyl-4-methylpyrimidin-5-yl)-7-methyl-7H-pyrrolo[2,3-d]pyrimidin-5-yl)phenyl)(2-ethynylpyrrolidin-1-yl)methanone (3.9 mg, 13%) and (R)-(4-(4-amino-6-(2-ethynyl-4-methylpyrimidin-5-yl)-7-methyl-7H-pyrrolo[2,3-d]pyrimidin-5-yl)phenyl)(2-ethynylpyrrolidin-1-yl)methanone (13.5 mg, 45%) as an off-white amorphous solid.

Additional compounds prepared according to the methods of Example 26 are depicted in Table 25 below.

TABLE 25

Additional Exemplary Compounds

| Compound | Structure | Proton NMR | MS [M + 1] |
|---|---|---|---|
| (S)-(4-(4-amino-6-(6-ethynyl-4-methylpyridin-3-yl)-7-methyl-7H-pyrrolo[2,3-d]pyrimidin-5-yl)phenyl)(2-ethynylpyrrolidin-1-yl)methanone | 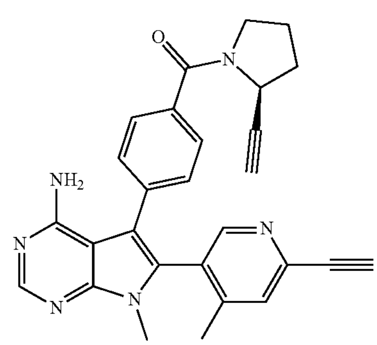 [SMILES: C#Cc1cc(C)c(-c2c(-c3ccc(C(=O)N4CCC[C@H]4C#C)cc3)c3c(N)ncnc3n2C)cn1] | ¹H NMR (400 MHz, DMSO-d₆) δ 8.47 (s, 1H), 8.24 (s, 1H), 7.53-7.42 (m, 3H), 7.22 (d, J = 7.8 Hz, 2H), 6.1-6.08 (m, 1H), 4.71-4.60 (m, 1H), 4.40 (s, 1H), 3.53-3.35 (m, 5H), 3.17 (s, 1H), 2.18-2.09 (m, 1H), 2.01-1.83 (m, 6H). | 461.35 |

TABLE 25-continued

Additional Exemplary Compounds

| Compound | Structure | Proton NMR | MS [M + 1] |
|---|---|---|---|
| (R)-(4-(4-amino-6-(6-ethynyl-4-methylpyridin-3-yl)-7-methyl-7H-pyrrolo[2,3-d]pyrimidin-5-yl)phenyl)(2-ethynylpyrrolidin-1-yl)methanone | 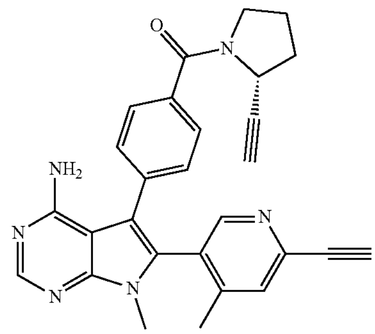 [SMILES: C#Cc1cc(C)c(-c2c(-c3ccc(C(=O)N4CCC[C@@H]4C#C)cc3)c3c(N)ncnc3n2C)cn1] | $^1$H NMR (400 MHz, DMSO-d$_6$) δ 8.48 (s, 1H), 8.24 (s, 1H), 7.59-7.46 (m, 3H), 7.22 (d, J = 7.8 Hz, 2H), 6.09-6.07 (m, 1H), 4.72-4.60 (m, 1H), 4.39 (s, 1H), 3.53-3.48 (m, 5H), 3.17 (s, 1H), 2.19-2.11 (m, 1H), 2.01-1.81 (m, 6H). | 461.35 |
| (S)-(4-(4-amino-6-(2-ethynyl-4-methylpyrimidin-5-yl)-7-methyl-7H-pyrrolo[2,3-d]pyrimidin-5-yl)phenyl)(2-ethynylpyrrolidin-1-yl)methanone | 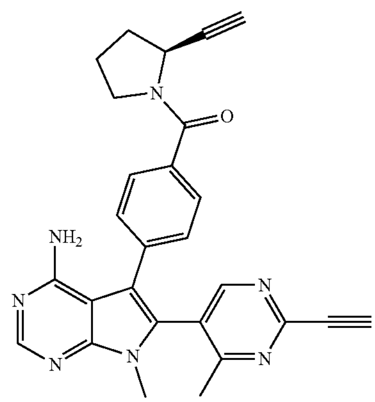 [SMILES: C#Cc1ncc(-c2c(-c3ccc(C(=O)N4CCC[C@H]4C#C)cc3)c3c(N)ncnc3n2C)c(C)n1] | 1H NMR (400 MHz, DMSO-d6) δ 8.78 (d, J = 4.8 Hz, 1H), 8.26 (s, 1H), 7.53 (d, J = 8.5 Hz, 2H), 7.24 (d, J = 7.7 Hz, 2H), 4.66 (d, J = 50.5 Hz, 1H), 4.48 (d, J = 1.1 Hz, 1H), 3.55 (s, 5H), 3.17 (d, J = 2.0 Hz, 1H), 2.09 (s, 4H), 2.03-1.76 (m, 3H). | 462.15 |
| (R)-(4-(4-amino-6-(2-ethynyl-4-methylpyrimidin-5-yl)-7-methyl-7H-pyrrolo[2,3-d]pyrimidin-5-yl)phenyl)(2-ethynylpyrrolidin-1-yl)methanone | 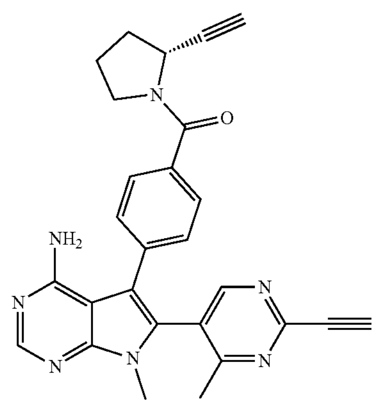 | 1H NMR (400 MHz, DMSO-d6) δ 8.78 (d, J = 4.8 Hz, 1H), 8.26 (s, 1H), 7.53 (d, J = 8.5 Hz, 2H), 7.24 (d, J = 7.7 Hz, 2H), 4.66 (d, J = 50.5 Hz, 1H), 4.48 (d, J = 1.1 Hz, 1H), 3.55 (s, 5H), 3.17 (d, J = 2.0 Hz, 1H), 2.09 (s, 4H), 2.03-1.76 (m, 3H). | 462.20 |
| (S)-(4-(4-amino-6-(6-ethynyl-5-fluoro-4-methylpyridin-3-yl)-7-methyl-7H-pyrrolo[2,3-d]pyrimidin-5-yl)phenyl)(2-ethynylpyrrolidin-1-yl)methanone | 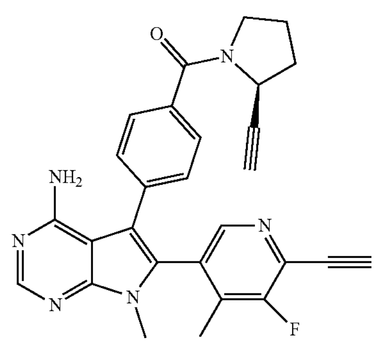 [SMILES: C#Cc1ncc(-c2c(-c3ccc(C(=O)N4CCC[C@H]4C#C)cc3)c3c(N)ncnc3n2C)c(C)c1F] | $^1$H NMR (400 MHz, DMSO-d$_6$) δ 8.36 (s, 1H), 8.25 (s, 1H), 7.51 (d, J = 10.3 Hz, 2H), 7.23 (d, J = 7.7 Hz, 2H), 6.13 (s, 2H), 4.80 (s, 1H), 4.65 (d, J = 49.4 Hz, 1H), 3.51 (s, 5H), 3.17 (s, 1H), 2.43-1.67 (m, 7H). | 479.35 |

TABLE 25-continued

Additional Exemplary Compounds

| Compound | Structure | Proton NMR | MS [M + 1] |
|---|---|---|---|
| (R)-(4-(4-amino-6-(6-ethynyl-5-fluoro-4-methylpyridin-3-yl)-7-methyl-7H-pyrrolo[2,3-d]pyrimidin-5-yl)phenyl)(2-ethynylpyrrolidin-1-yl)methanone | 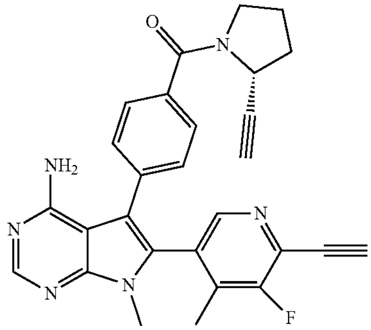 [SMILES: C#Cc1ncc(-c2c(-c3ccc(C(=O)N4CCC[C@@H]4C#C)cc3)c3c(N)ncnc3n2C)c(C)c1F] | $^1$H NMR (400 MHz, DMSO-d$_6$) δ 8.36 (s, 1H), 8.25 (s, 1H), 7.51 (d, J = 7.1 Hz, 2H), 7.23 (d, J = 7.8 Hz, 2H), 6.12 (s, 2H), 4.80 (s, 1H), 4.66 (d, J = 46.9 Hz, 1H), 3.52 (s, 5H), 3.17 (s, 1H), 2.36-1.72 (m, 7H). | 479.30 |
| 4-(6-(6-ethynyl-4-methoxypyridin-3-yl)-4,7-dimethyl-7H-pyrrolo[2,3-d]pyrimidin-5-yl)-N-((1-fluorocyclobutyl)methyl)-2-methoxybenzamide | 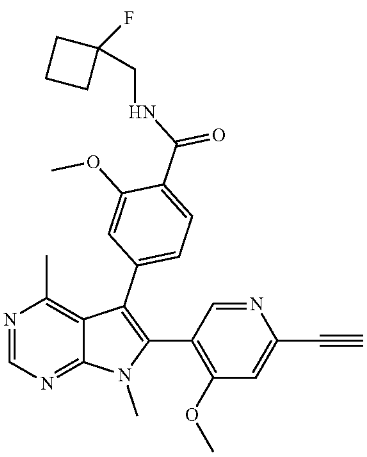 [SMILES: C#Cc1cc(OC)c(-c2c(-c3ccc(C(=O)NCC4(F)CCC4)c(OC)c3)c3c(C)ncnc3n2C)cn1] | $^1$H NMR (400 MHz, DMSO-d$_6$) δ 8.76 (s, 1H), 8.28 (t, J = 6.1Hz, 1H), 8.20 (s, 1H), 7.69 (d, J = 7.9 Hz, 1H), 7.41 (s, 1H), 7.02 (s, 1H), 6.91 (d, J = 7.9 Hz, 1H), 4.45 (s, 1H), 3.88 (s, 3H), 3.77 (s, 3H), 3.67 (d, J = 6.1 Hz, 1H), 3.62 (s, 1H), 3.60 (s, 3H), 2.40 (s, 3H), 2.23-2.14 (m, 4H), 1.76 (dd, J = 11.2, 7.1 Hz, 1H), 1.58-1.49 (m, 1H). | 514.25 |

Example 27

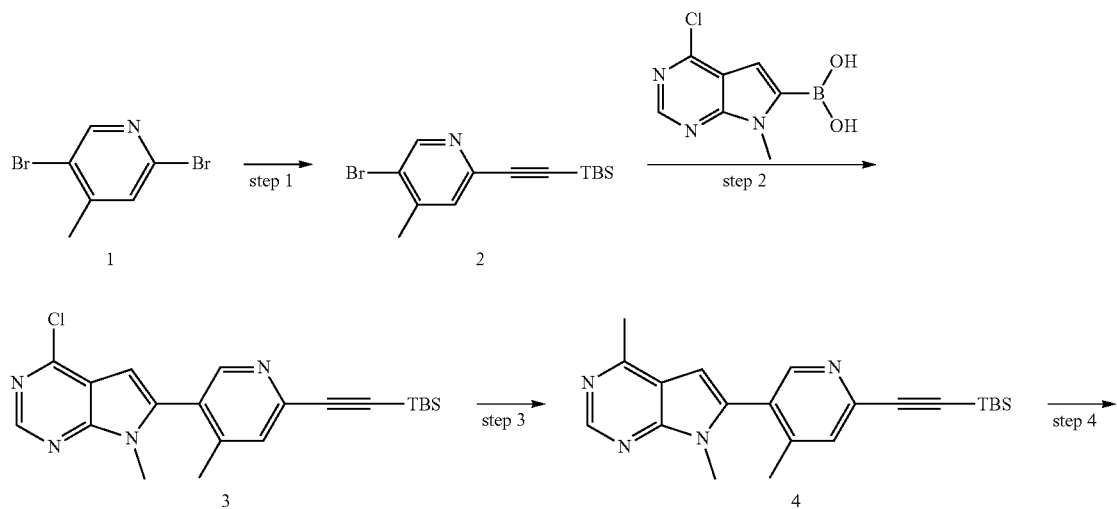

Scheme 24

-continued

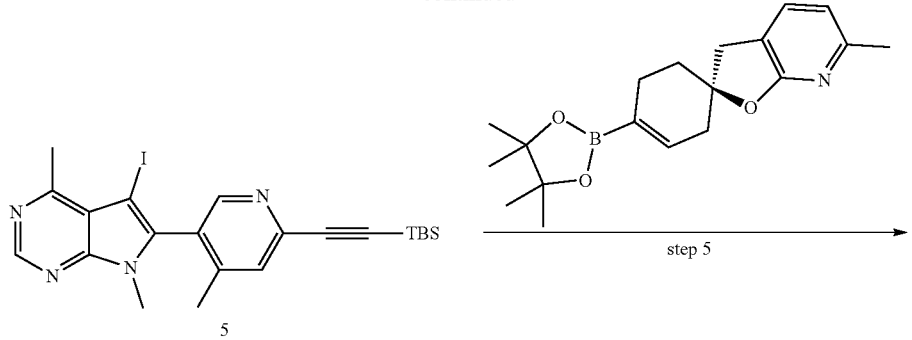

step 5

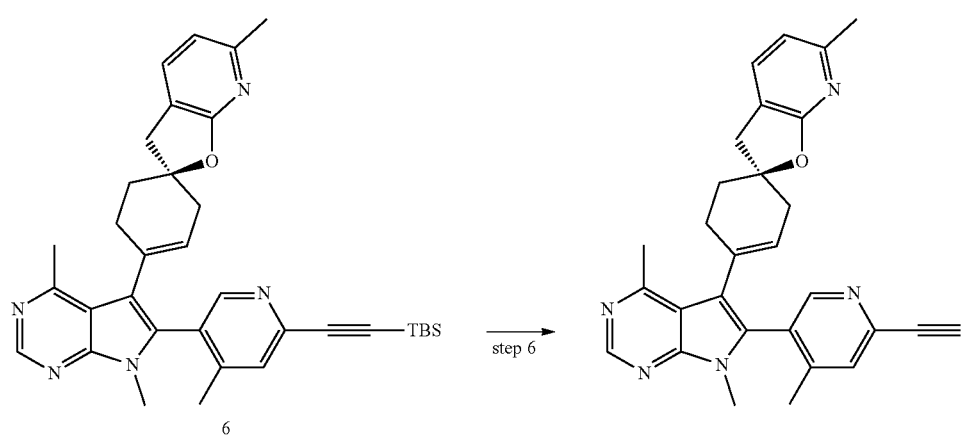

step 6

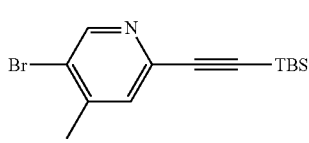

5-bromo-2-((tert-butyldimethylsilyl)ethynyl)-4-methylpyridine

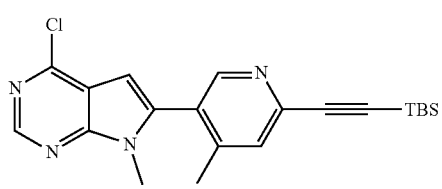

6-(6-((tert-butyldimethylsilyl)ethynyl)-4-methylpyridin-3-yl)-4-chloro-7-methyl-7H-pyrrolo[2,3-d]pyrimidine Step 1: A resealable reaction vial was charged with 2,5-dibromo-4-methylpyridine (3 g, 11.9 mmol), tert-butyl(ethynyl)dimethylsilane (1.82 g, 13.0 mmol), TEA (3.60 g, 35.7 mmol), CuI (452 mg, 2.38 mmol), dimethylformamide (40 mL), and a stirbar, Pd(PPh3)2Cl2 (834 mg, 1.19 mmol) was added, before being evacuated and purged with nitrogen three times. The mixture was stirred for 2 h at 50° C. The reaction mixture was diluted with H2O (20 mL), and the aqueous phase was extracted with EA (120 mL) three times. The combined organic layers were washed with brine, dried over sodium sulfate, filtered, and concentrated in vacuo. The resulting crude material was purified by silica gel chromatography (300 g column; eluting with PE/EA; 50/1-20/1). Concentration in vacuo resulted in 5-bromo-2 [2-(tert-butyldimethylsilyl)ethynyl]-4-methylpyridine (3.10 g, 83.9%) as a yellow amorphous solid.

Step 2: A resealable reaction vial was charged with 5-bromo-2-[2-(tert-butyldimethylsilyl) ethynyl]-4-methylpyridine (3 g, 9.66 mmol), {4-chloro-7-methyl-7H-pyrrolo[2,3-d]pyrimidin-6-yl}boronic acid (2.43 g, 11.5 mmol), K3PO4 (6.12 g, 28.9 mmol), Pd(dppf)Cl2 (706 mg, 966 μmol), and a stirbar before being evacuated and purged with nitrogen three times. dioxane/H2O (50 mL) was added, and the mixture was stirred for 2 h at 70° C. The aqueous phase was extracted with dimethylformamide (100 mL) for three times. The combined organic layers were washed with brine, dried over sodium sulfate, filtered, and concentrated in vacuo. The resulting crude material was purified by silica gel chromatography (300 g column; eluting with PE/EA; 10/1). Concentration in vacuo resulted in 2-[2-(tert-butyldimethylsilyl)ethynyl]-5-{4-chloro-7-methyl-7H-pyrrolo[2,3-d]pyrimidin-6-yl}-4-methylpyridine (1.60 g, 41.7%) as a orange amorphous solid.

1711

6-(6-((tert-butyldimethylsilyl)ethynyl)-4-methylpyridin-3-yl)-4,7-dimethyl-7H-pyrrolo[2,3-d]pyrimidine

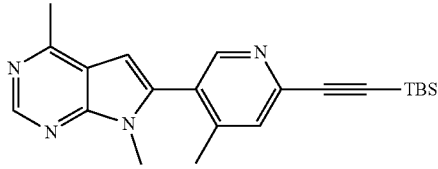

Step 3: A resealable reaction vial was charged with 2-[2-(tert-butyldimethylsilyl) ethynyl]-5-{4-chloro-7-methyl-7H-pyrrolo[2,3-d]pyrimidin-6-yl}-4-methylpyridine (1.5 g, 3.77 mmol), dimethylzinc (359 mg, 3.77 mmol), Pd(PPh3)4 (435 mg, 377 µmol), and a stirbar before being evacuated and purged with nitrogen three times. dimethylformamide (20 mL) was added, and the mixture was stirred for 1 h at 90° C. The reaction mixture was diluted with H₂O (10 mL), and the aqueous phase was extracted with EA (100 mL) three times. The combined organic layers were washed with brine, dried over sodium sulfate, filtered, and concentrated in vacuo. The resulting crude material was purified by silica gel chromatography (300 g column; eluting with dichloromethane/methanol; 40/1). Concentration in vacuo resulted in 2-[2-(tert-butyldimethylsilyl)ethynyl]-5-{4,7-dimethyl-7H-pyrrolo[2,3-d]pyrimidin-6-yl}-4-methylpyridine (1.2 g, 84.4%) as a off-white amorphous solid.

6-(6-((tert-butyldimethylsilyl)ethynyl)-4-methylpyridin-3-yl)-5-iodo-4,7-dimethyl-7H-pyrrolo[2,3-d]pyrimidine

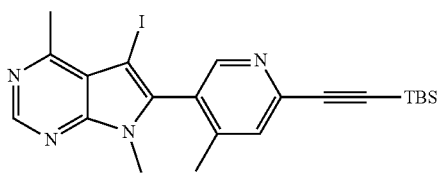

Step 4: A round bottomed flask was charged with 2-[2-(tert-butyldimethylsilyl) ethynyl]-5-{4,7-dimethyl-7H-pyrrolo[2,3-d]pyrimidin-6-yl}-4-methylpyridine (1.1 g, 2.92 mmol), TFA (849 mg, 8.76 mmol), DCM (15 mL) and a stirbar. NIS (722 mg, 3.21 mmol) was added at 0° C., warmed to r.t. The mixture was quenched with saturated NaHSO₃ aqueous solution until the pH to 8-9, extracted with DCM (100 mL*3), the organic phase was combined and dried with Na₂SO₄, Concentration in vacuo resulted in 2-[2-(tert-butyldimethylsilyl)ethynyl]-5-{5-iodo-4,7-dimethyl-7H-pyrrolo[2,3-d]pyrimidin-6-yl}-4-methylpyridine (1.20 g, 81.5%) as a yellow amorphous solid.

1712

(R)-4-(6-(6-((tert-butyldimethylsilyl)ethynyl)-4-methylpyridin-3-yl)-4,7-dimethyl-7H-pyrrolo[2,3-d]pyrimidin-5-yl)-6'-methyl-3'H-spiro[cyclohexane-1,2'-furo[2,3-b]pyridin]-3-ene

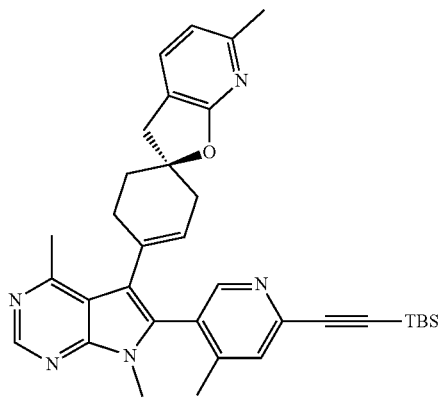

Step 5: A resealable reaction vial was charged with 1R)-6'-methyl-4-(4,4,5,5-tetramethyl-1,3,2-dioxaborolan-2-yl)-3'H-spiro[cyclohexane-1,2'-furo[2,3-b]pyridin]-3-ene (40 mg, 122 µmol), 2-[2-(tert-butyldimethylsilyl)ethynyl]-5-{5-iodo-4,7-dimethyl-7H-pyrrolo[2,3-d]pyrimidin-6-yl}-4-methylpyridine (73.3 mg, 146 µmol), K₃PO₄ (25.8 mg, 122 µmol), Pd(dppf)Cl₂ (89.2 mg, 122 µmol), and a stirbar before being evacuated and purged with nitrogen. DME/H₂O (2 mL) was added, and the mixture was stirred for 1 h at 90° C. The reaction mixture was diluted with H₂O (1 mL), and the aqueous phase was extracted with EA (10 mL) three times. The combined organic layers were washed with brine, dried over sodium sulfate, filtered, and concentrated in vacuo. The resulting crude material was purified by silica gel chromatography (10 g column; eluting with dichloromethane/methanol; 15/1). Concentration in vacuo resulted in (1R)-4-(6-{6-[2-(tert-butyl-dimethylsilyl)ethynyl]-4-methylpyridin-3-yl}-4,7-dimethyl-7H-pyrrolo[2,3-d]pyrimidin-5-yl)-6'-methyl-3'H-spiro[cyclohexane-1,2'-furo[2,3-b]pyridin]-3-ene (35 mg, 49.8%) as a black amorphous solid.

(R)-4-(6-(6-ethynyl-4-methylpyridin-3-yl)-4,7-dimethyl-7H-pyrrolo[2,3-d]pyrimidin-5-yl)-6'-methyl-3'H-spiro[cyclohexane-1,2'-furo[2,3-b]pyridin]-3-ene

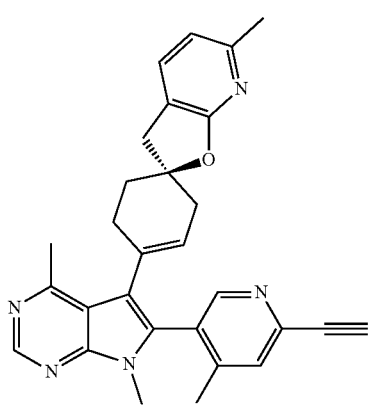 [SMILES: C#Cc1cc(C)c(-c2c(C3=CC[C@]4(CC3)Cc3ccc(C)nc3O4)c3c(C)ncnc3n2C)cn1]

Step 6: A round bottomed flask was charged with (1R)-4-(6-{6-[2-(tert-butyldimethylsilyl) ethynyl]-4-methylpyridin-3-yl}-4,7-dimethyl-7H-pyrrolo[2,3-d]pyrimidin-5-yl)-6'-methyl-3'H-spiro[cyclohexane-1,2'-furo[2,3-b]pyridin]-3-ene (30 mg, 52.0 µmol), fluorocaesium (23.6 mg, 156 µmol), and a stirbar. THF (2 mL) was added, and the solution was stirred for 2 h at 50° C. Filtered and evaporated. The resulting crude material was purified by HPLC (Column: XBridge Shield RP18 OBD Column, 30*150 mm, 5 um; Mobile Phase A: Water (10 MMOL/L NH$_4$HCO$_3$+0.1% NH$_3$·H$_2$O), Mobile Phase B:ACN; Flow rate:60 mL/min; Gradient:30 B to 55 B in 7 min; 220 nm; RT1:5.97; RT2). Lyophilization yielded (1R)-4-[6-(6-ethynyl-4-methylpyridin-3-yl)-4,7-dimethyl-7H-pyrrolo[2,3-d]pyrimidin-5-yl]-6'-methyl-3'H-spiro[cyclohexane-1,2'-furo[2,3-b]pyridin]-3-ene (3.90 mg, 16.9%) as a off-white amorphous solid.

Additional compounds prepared according to the methods of Example 27 are depicted in Table 26 below.

TABLE 26

Additional Exemplary Compounds

| Compound | Structure | Proton NMR | MS [M + 1] |
|---|---|---|---|
| N-(6-(5-(3-fluoro-4-((6-methylpyridin-2-yl)oxy)phenyl)-4,7-dimethyl-7H-pyrrolo[2,3-d]pyrimidin-6-yl)-5-methylpyridin-3-yl)methacrylamide; partial formic acid salt | 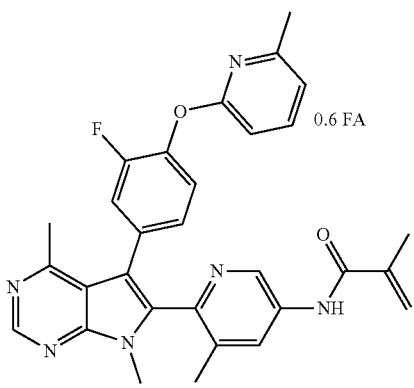 [SMILES: C=C(C)C(=O)Nc1cnc(-c2c(-c3ccc(Oc4cccc(C)n4)c(F)c3)c3c(C)ncnc3n2C)c(C)c1] 0.6 FA | 1H NMR (400 MHz, DMSO-d6) δ 10.12 (s, 1H), 8.90 (d, J = 2.4 Hz, 1H), 8.78 (s, 1H), 8.23 (d, J = 4.8 Hz, 1H), 8.06 (d, J = 2.4 Hz, 1H), 7.75 (ddd, J = 8.3, 7.3, 1.5 Hz, 1H), 7.68-7.63 (m, 1H), 7.27-7.16 (m, 2H), 7.02 (dd, J = 12.6, 8.1 Hz, 2H), 6.86 (t, J = 7.4 Hz, 1H), 5.87 (t, J = 1.0 Hz, 1H), 5.60 (d, J = 1.9 Hz, 1H), 3.61 (s, 3H), 3.33 (s, 3H), 2.28 (s, 3H), 1.97 (t, J = 1.2 Hz, 3H), 1.89 (s, 3H). | 523.25 |
| (1R)-4-[6-(6-ethynyl-4-methylpyridin-3-yl)-4,7-dimethyl-7H-pyrrolo[2,3-d]pyrimidin-5-yl]-6'-methyl-3'H-spiro[cyclohexane-1,2'-furo[2,3-b]pyridin]-3-ene | 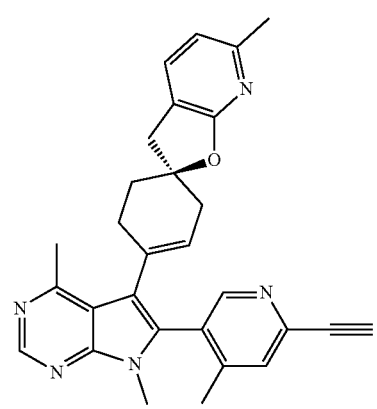 [SMILES: C#Cc1cc(C)c(-c2c(C3=CC[C@]4(CC3)Cc3ccc(C)nc3O4)c3c(C)ncnc3n2C)cn1] | $^1$H NMR (400 MHz, DMSO-d$_6$) δ 8.72 (s, 1H), 8.49 (d, J = 6.4 Hz, 1H), 7.69 (d, J = 4.4 Hz, 1H), 7.41 (dd, J = 7.3, 3.3 Hz, 1H), 6.68 (d, J = 7.3 Hz, 1H), 5.60 (d, J = 37.3 Hz, 1H), 4.47 (d, J = 2.1 Hz, 1H), 3.49 (s, 3H), 2.99-2.83 (m, 1H), 2.72 (s, 3H), 2.68 (p, J = 2.2 Hz, 1H), 2.47-2.31 (m, 2H), 2.30 (s, 3H), 2.25 (d, J = 18.4 Hz, 1H), 2.17 (d, J = 1.5 Hz, 3H), 2.12-1.94 (m, 1H), 1.89 (dd, J = 12.7, 6.2 Hz, 1H), 1.74 (dq, J = 14.0, 6.4 Hz, 1H). | 462.30 |
| (S)-4-(6-(6-ethynyl-4-methylpyridin-3-yl)-4,7-dimethyl-7H-pyrrolo[2,3-d]pyrimidin-5-yl)-6'-methyl-3'H-spiro[cyclohexane-1,2'-furo[2,3-b]pyridin]-3-ene | 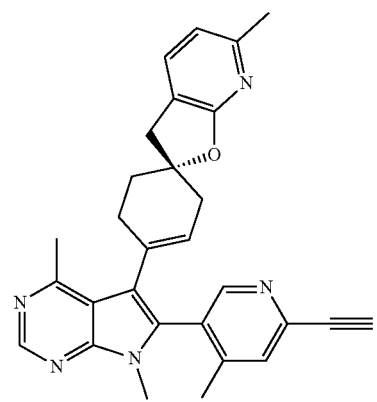 [SMILES: C#Cc1cc(C)c(-c2c(C3=CC[C@@]4(CC3)Cc3ccc(C)nc3O4)c3c(C)ncnc3n2C)cn1] | 1H NMR (400 MHz, DMSO-d6) δ8.71 (s, 1H), 8.49 (d, J = 6.4 Hz, 1H), 7.69 (d, J = 4.3 Hz, 1H), 7.41 (dd, J = 7.2, 3.4 Hz, 1H), 6.68 (d, J = 7.3 Hz, 1H), 5.65 (s, 1H), 4.47 (d, J = 2.1 Hz, 1H), 3.52-3.47 (m, 3H), 2.91 (dd, J = 29.8, 16.2 Hz, 1H), 2.72 (s, 3H), 2.38 (d, J = 16.3 Hz, 3H), 2.30 (s, 3H), 2.27 (s, 1H), 2.19-2.14 (m, 3H), 2.06 (s, 1H), 1.89 (dd, J = 12.5, 6.1 Hz, 1H), 1.74 (dq, J = 14.1, 6.4 Hz, 1H). | 462.20 |

Example 28

Scheme 25

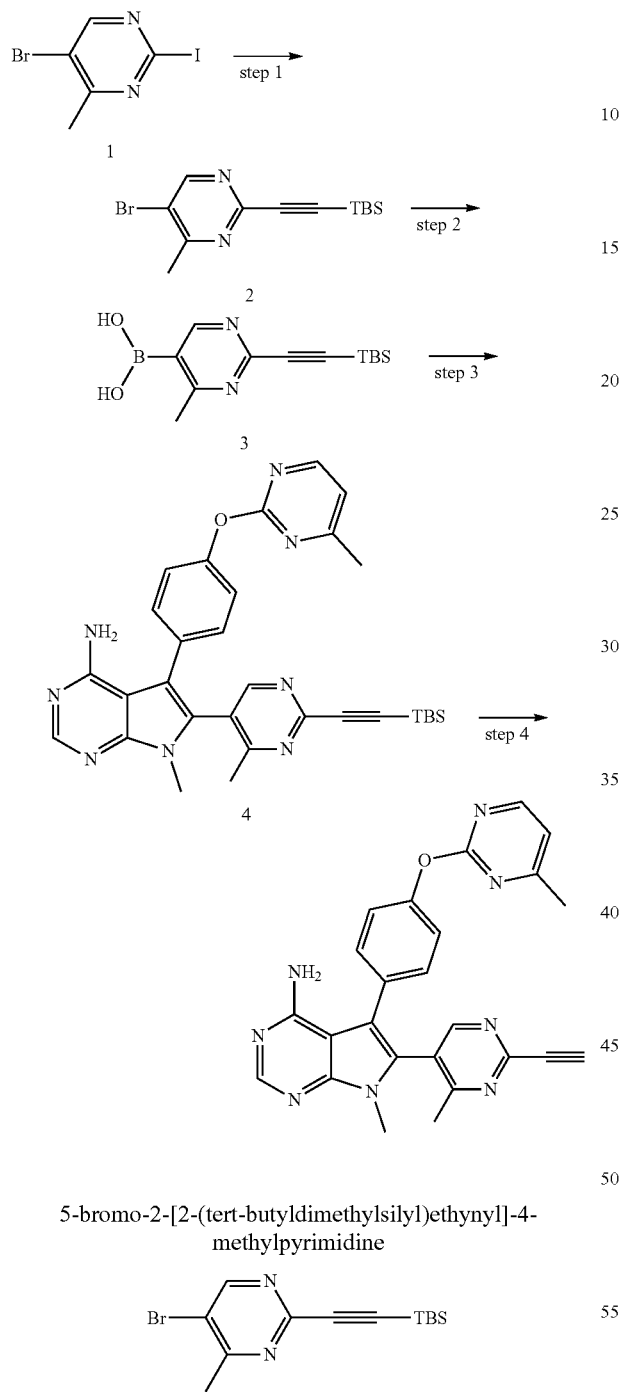

5-bromo-2-[2-(tert-butyldimethylsilyl)ethynyl]-4-methylpyrimidine

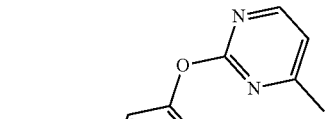

Step 1: A resealable reaction vial was charged with 5-bromo-2-iodo-4-methylpyrimidine (600 mg, 2.00 mmol), CuI (152 mg, 800 µmol), Et₃N (606 mg, 6.00 mmol), Pd(PPh₃)₂Cl₂ (280 mg, 400 µmol), DMF (15 mL), and a stir bar before being evacuated and purged with nitrogen three times, tert-butyl(ethynyl)dimethylsilane (280 mg, 2.00 mmol) was added, and the mixture was stirred at 50° C. for 2 h. The reaction mixture was diluted with water (20 mL), and the aqueous phase was extracted with ethyl acetate (20 mL) three times. The combined organic layers were washed with brine, dried over sodium sulfate, filtered, and concentrated in vacuo. The resulting crude material was purified by TLC (PE:EA=8:1). Concentration in vacuo resulted in 5-bromo-2-[2-(tert-butyldimethylsilyl)ethynyl]-4-methylpyrimidine (500 mg, 80%) as an off-white amorphous solid.

(2-((tert-butyldimethylsilyl)ethynyl)-4-methylpyrimidin-5-yl)boronic acid

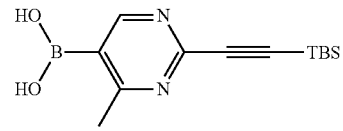

Step 2: A resealable reaction vial was charged with 5-bromo-2-[2-(tert-butyldimethylsilyl)ethynyl]-4-methylpyrimidine (480 mg, 1.54 mmol), 4,4,5,5-tetramethyl (4,4,5,5-tetramethyl-1,3,2-dioxaborolan-2-yl)-1,3,2-dioxaborolane (467 mg, 1.84 mmol), AcOK (452 mg, 4.62 mmol), Pd(dppf)Cl₂ (112 mg, 154 µmol), dioxane (10 mL) was added, and a stir bar before being evacuated and purged with nitrogen three times, and the mixture was stirred at 80° C. for 2 h. The reaction mixture was diluted with water (15 mL), and the aqueous phase was extracted with EA (15 mL) three times. The combined organic layers were washed with brine, dried over sodium sulfate, filtered, and concentrated in vacuo. The resulting crude material was purified by HPLC (acetonitrile/water 0%~60%, 30 min). Lyophilization yielded {2-[2-(tert-butyldimethylsilyl)ethynyl]-4-methylpyrimidin-5-yl}boronic acid (400 mg, 94%) as an off-white amorphous solid.

6-(2-((tert-butyldimethylsilyl)ethynyl)-4-methylpyrimidin-5-yl)-7-methyl-5-(4-((4-methylpyrimidin-2-yl)oxy)phenyl)-7H-pyrrolo[2,3-d]pyrimidin-4-amine Step 3: A resealable reaction vial was charged with 6-iodo-7-methyl-5-{4-[(4-methylpyrimidin-2-yl)oxy]phenyl}-7H-pyrrolo[2,3-d]pyrimidin-4-amine (520 mg, 1.13 mmol), {2-[2-(tert-butyldimethylsilyl)ethynyl]-4-methylpyrimidin-5-yl}boronic acid (380 mg, 1.37 mmol), Na₂CO₃ (358 mg, 3.38 mmol), Pd(dppf)Cl₂ (82.6 mg, 113 µmol), DMF/H2O=16/1 (15 mL) was added and a stir bar before being evacuated and purged with nitrogen three times, and the mixture was stirred at 90° C. for 1 h. The reaction mixture was diluted with water (15 mL), and the aqueous phase was extracted with DCM (15 mL) three times. The combined organic layers were washed with brine, dried over sodium sulfate, filtered, and concentrated in vacuo. The resulting crude material was purified by HPLC (DCM/MeOH=15/1). Lyophilization yielded 6-{2-[2-(tert-butyldimethylsilyl)ethynyl]-4-methylpyrimidin-5-yl}-7-methyl-5-{4-[(4-methylpyrimidin-2-yl)oxy]phenyl}-7H-pyrrolo[2,3-d]pyrimidin-4-amine (200 mg, 34%) as a yellow amorphous solid.

6-(2-ethynyl-4-methylpyrimidin-5-yl)-7-methyl-5-(4-((4-methylpyrimidin-2-yl)oxy)phenyl)-7H-pyrrolo[2,3-d]pyrimidin-4-amine

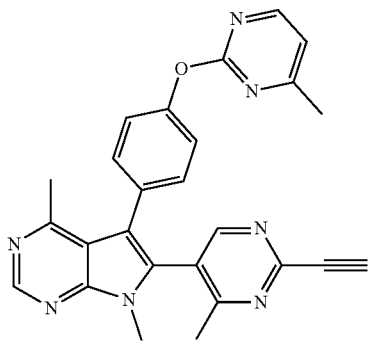 [SMILES: C#Cc1ncc(-c2c(-c3ccc(Oc4nccc(C)n4)cc3)c3c(C)ncnc3n2C)c(C)n1]

Step 4: A round bottomed flask was charged with 6-{2-[2-(tert-butyldimethylsilyl)ethynyl]-4-methylpyrimidin-5-yl}-7-methyl-5-{4-[(4-methylpyrimidin-2-yl)oxy]phenyl}-7H-pyrrolo[2,3-d]pyrimidin-4-amine (180 mg, 319 μmol), TBAF (638 μg, 638 μmol) and a stir bar. Tetrahydrofuran (5 mL) was added, and the solution was stirred at 25° C. for 1 h. The reaction mixture was diluted with water (10 mL), and the aqueous phase was extracted with dichloromethane (10 mL) three times. The combined organic layers were washed with brine ten times, dried over sodium sulfate, filtered, and concentrated in vacuo. The resulting crude material was purified by HPLC (Column: SunFire Prep C18 OBD Column, 19×150 mm 5 um 10 nm; Mobile Phase A:Water (0.05% FA), Mobile Phase B:ACN (0.1% DEA)-HPLC-; Flow rate:25 mL/min; Gradient:15 B to 38 B in 8 min; 220 nm; RT1:6.36). Lyophilization yielded 6-(2-ethynyl-4-methylpyrimidin-5-yl)-7-methyl-5-{4-[(4-methylpyrimidin-2-yl)oxy]phenyl}-7H-pyrrolo[2,3-d]pyrimidin-4-amine (31.1 mg, 21%) as a yellow amorphous solid.

Additional compounds prepared according to the methods of Example 28 are depicted in Table 27 below.

TABLE 27

| Compound | Structure | Proton NMR | MS [M + 1] |
|---|---|---|---|
| (4-(4-amino-6-(2-ethynylpyrimidin-5-yl)-7-methyl-7H-pyrrolo[2,3-d]pyrimidin-5-yl)phenyl)(pyrrolidin-1-yl)methanone | 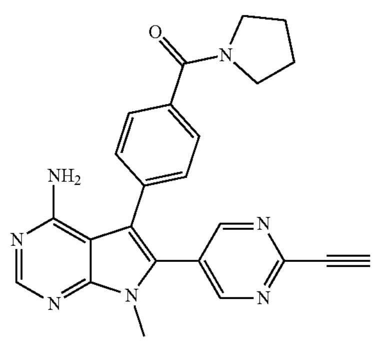 [SMILES: C#Cc1ncc(-c2c(-c3ccc(C(=O)N4CCCC4)cc3)c3c(N)ncnc3n2C)cn1] | 1H NMR (400 MHz, DMSO-d6) δ 8.75 (s, 2H), 8.25 (s, 1H), 7.60-7.43 (m, 2H), 7.38-7.21 (m, 2H), 5.81 (s, 1H), 4.52 (s, 1H), 3.72 (s, 3H), 3.45 (dt, J = 17.5, 6.5 Hz, 4H), 1.85 (dq, J = 18.0, 6.8 Hz, 4H). | 424.10 |
| 6-(2-ethynylpyrimidin-5-yl)-7-methyl-5-(4-((4-methylpyrimidin-2-yl)oxy)phenyl)-7H-pyrrolo[2,3-d]pyrimidin-4-amine | 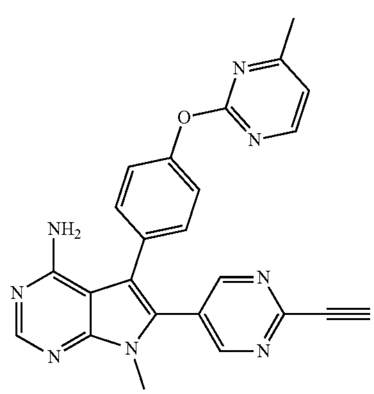 [SMILES: C#Cc1ncc(-c2c(-c3ccc(Oc4nccc(C)n4)cc3)c3c(N)ncnc3n2C)cn1] | $^1$H NMR (400 MHz, DMSO-d$_6$) δ 8.80 (s, 2H), 8.48 (d, J = 5.0 Hz, 1H), 8.25 (s, 1H), 7.38-7.31 (m, 2H), 7.28-7.21 (m, 2H), 7.17 (d, J = 5.0 Hz, 1H), 6.08 (s, 1H), 4.52 (s, 1H), 3.72 (s, 3H), 2.42 (s, 3H). | 435.20 |

TABLE 27-continued

Additional Exemplary Compounds

| Compound | Structure | Proton NMR | MS [M + 1] |
|---|---|---|---|
| (4-(4-amino-2-(6-ethynylpyridin-3-yl)-1-methyl-1H-pyrrolo[2,3-b]pyridin-3-yl)phenyl)(pyrrolidin-1-yl)methanone | 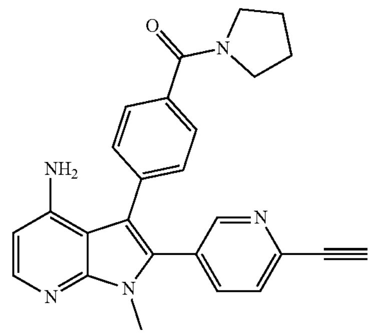 [SMILES: C#Cc1ccc(-c2c(-c3ccc(C(=O)N4CCCC4)cc3)c3c(N)ccnc3n2C)cn1] | ¹H NMR (400 MHz, DMSO-d₆) δ 8.47-8.41 (m, 1H), 8.24 (s, 1H), 7.84 (dd, J = 8.0, 2.3 Hz, 1H), 7.61 (dd, J = 8.1, 0.8 Hz, 1H), 7.52 (d, J = 8.1 Hz, 2H), 7.28 (d, J = 8.1 Hz, 2H), 4.44 (s, 1H), 3.66 (s, 3H), 3.44 (dt, J = 17.6, 6.4 Hz, 4H), 1.90-1.79 (m, 4H). | 423.10 |
| 6-(6-ethynylpyridin-3-yl)-7-methyl-5-(4-((4-methylpyrimidin-2-yl)oxy)phenyl)-7H-pyrrolo[2,3-d]pyrimidin-4-amine | 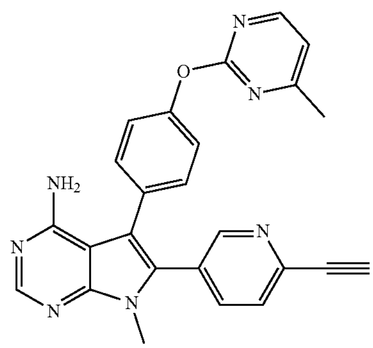 [SMILES: C#Cc1ccc(-c2c(-c3ccc(Oc4nccc(C)n4)cc3)c3c(N)ncnc3n2C)cn1] | ¹H NMR (400 MHz, DMSO-d₆) δ 8.51-8.45 (m, 2H), 8.23 (s, 1H), 7.89 (dd, J = 8.1, 2.3 Hz, 1H), 7.63 (dd, J = 8.1, 0.9 Hz, 1H), 7.34-7.27 (m, 2H), 7.25-7.18 (m, 2H), 7.16 (d, J = 5.1 Hz, 1H), 4.44 (s, 1H), 3.66 (s, 3H), 2.42 (s, 3H). | 434.10 |
| 6-(2-ethynyl-4-methylpyrimidin-5-yl)-7-methyl-5-(4-((4-methylpyrimidin-2-yl)oxy)phenyl)-7H-pyrrolo[2,3-d]pyrimidin-4-amine | 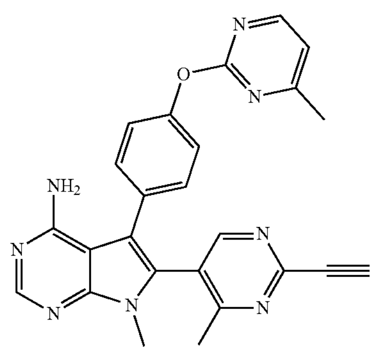 | ¹H NMR (400 MHz, DMSO-d₆) δ 8.80 (s, 1H), 8.47 (d, J = 5.0 Hz, 1H), 8.25 (s, 1H), 7.30-7.23 (m, 2H), 7.23-7.13 (m, 3H), 6.06 (s, 2H), 4.49 (s, 1H), 3.55 (s, 3H), 2.41 (s, 3H), 2.14 (s, 3H). | 449.20 |
| 6-(6-ethynyl-5-fluoropyridin-3-yl)-7-methyl-5-(4-((4-methylpyrimidin-2-yl)oxy)phenyl)-7H-pyrrolo[2,3-d]pyrimidin-4-amine | 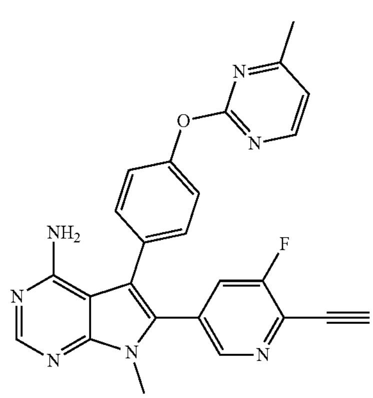 [SMILES: C#Cc1ncc(-c2c(-c3ccc(Oc4nccc(C)n4)cc3)c3c(N)ncnc3n2C)cc1F] | ¹H NMR (400 MHz, DMSO-d₆) δ 8.48 (d, J = 5.0 Hz, 1H), 8.31 (t, J = 1.6 Hz, 1H), 8.25 (s, 1H), 8.02 (dd, J = 10.0, 1.8 Hz, 1H), 7.37-7.29 (m, 2H), 7.28-7.20 (m, 2H), 7.17 (d, J = 5.0 Hz, 1H), 4.84 (d, J = 0.8 Hz, 1H), 3.71 (s, 3H), 2.42 (s, 3H). | 452.15 |

TABLE 27-continued

Additional Exemplary Compounds

| Compound | Structure | Proton NMR | MS [M + 1] |
|---|---|---|---|
| 6-(6-ethynyl-2-methylpyridin-3-yl)-7-methyl-5-(4-((4-methylpyrimidin-2-yl)oxy)phenyl)-7H-pyrrolo[2,3-d]pyrimidin-4-amine | 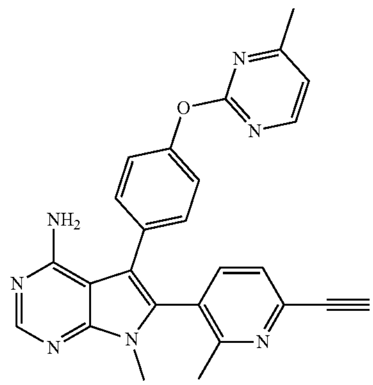 [SMILES: C#Cc1ccc(-c2c(-c3ccc(Oc4nccc(C)n4)cc3)c3c(N)ncnc3n2C)c(C)n1] | $^1$H NMR (400 MHz, DMSO-d$_6$) 8.46 (d, J = 5.0 Hz, 1H), 8.24 (s, 1H), 7.86 (d, J = 7.9 Hz, 1H), 7.50 (d, J = 7.8 Hz, 1H), 7.28-7.21 (m, 2H), 7.21-7.12 (m, 3H), 6.01 (s, 1H), 4.41 (s, 1H), 3.48 (s, 3H), 2.41 (s, 3H), 2.14 (s, 3H). | 448.20 |
| 6-(6-ethynyl-4-methylpyridin-3-yl)-7-methyl-5-(4-((4-methylpyrimidin-2-yl)oxy)phenyl)-7H-pyrrolo[2,3-d]pyrimidin-4-amine | 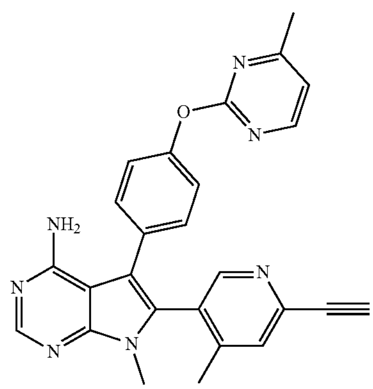 [SMILES: C#Cc1cc(C)c(-c2c(-c3ccc(Oc4nccc(C)n4)cc3)c3c(N)ncnc3n2C)cn1] | $^1$H NMR (400 MHz, DMSO-d$_6$) δ 8.52-8.44 (m, 2H), 8.24 (s, 1H), 7.56 (s, 1H), 7.28-7.21 (m, 2H), 7.21-7.12 (m, 3H), 4.41 (s, 1H), 3.48 (s, 3H), 2.41 (s, 3H), 2.02 (s, 3H). | 448.20 |
| 1-(4-(4-amino-7-methyl-5-(4-((4-methylpyrimidin-2-yl)oxy)phenyl)-7H-pyrrolo[2,3-d]pyrimidin-6-yl)phenyl)-1H-pyrrole-2,5-dione | 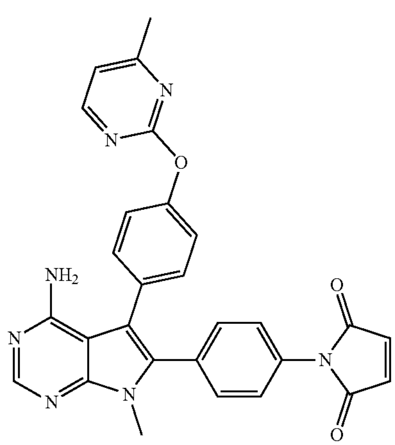 [SMILES: Cc1ccnc(Oc2ccc(-c3c(-c4ccc(N5C(=O)C=CC5=O)cc4)n(C)c4ncnc(N)c34)cc2)n1] | $^1$H NMR (400 MHz, DMSO-d$_6$) δ 8.47 (d, J = 5.2 Hz, 1H), 8.25 (s, 1H), 7.55-7.51 (m, 2H), 7.50-7.40 (m, 2H), 7.33 (dd, J = 2.0 Hz, 2H), 7.31-7.20 (m, 4H), 7.16 (d, J = 4.8 Hz, 1H), 3.65 (s, 3H), 2.40 (s, 3H). | 504.15 |

TABLE 27-continued

Additional Exemplary Compounds

| Compound | Structure | Proton NMR | MS [M + 1] |
|---|---|---|---|
| 6-(2-ethynyl-4-methylpyrimidin-5-yl)-5-(3-fluoro-4-((4-methylpyrimidin-2-yl)oxy)phenyl)-7-methyl-7H-pyrrolo[2,3-d]pyrimidin-4-amine | 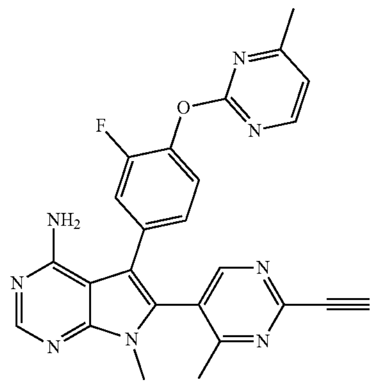 [SMILES: C#Cc1ncc(-c2c(-c3ccc(Oc4nccc(C)n4)c(F)c3)c3c(N)ncnc3n2C)c(C)n1] | $^1$H NMR (400 MHz, DMSO-d6) 8.81 (s, 1H), 8.48 (d, J = 5.0 Hz, 1H), 8.26 (s, 1H), 7.35 (t, J = 8.4 Hz, 1H), 7.26-7.16 (m, 2H), 7.08-7.01 (m, 1H), 6.19 (s, 2H), 4.49 (s, 1H), 3.54 (s, 3H), 2.41 (s, 3H), 2.15 (s, 3H). | 467.20 |
| 6-(6-ethynyl-4-methylpyridin-3-yl)-5-(3-fluoro-4-((4-methylpyrimidin-2-yl)oxy)phenyl)-7-methyl-7H-pyrrolo[2,3-d]pyrimidin-4-amine | 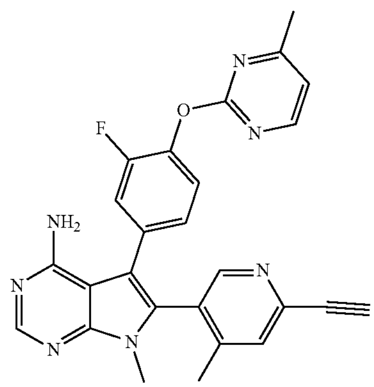 [SMILES: C#Cc1cc(C)c(-c2c(-c3ccc(Oc4nccc(C)n4)c(F)c3)c3c(N)ncnc3n2C)cn1] | $^1$H NMR (400 MHz, DMSO-d$_6$) δ 8.51 (s, 1H), 8.47 (S, 1H), 8.24 (s, 1H), 7.58 (s,1H), 7.36-7.30 (m, 1H), 7.19-7.16 (m, 2H), 7.06-7.03 (m, 1H), 4.42 (s, 1H), 3.47 (s, 3H), 2.41 (s, 3H), 2.02 (s, 3H). | 466.20 |
| 6-(6-ethynyl-5-fluoro-4-methylpyridin-3-yl)-7-methyl-5-(4-((4-methylpyrimidin-2-yl)oxy)phenyl)-7H-pyrrolo[2,3-d]pyrimidin-4-amine | 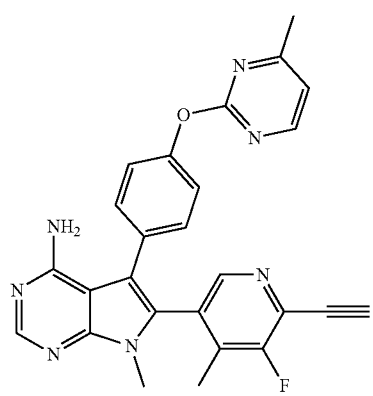 [SMILES: C#Cc1ncc(-c2c(-c3ccc(Oc4nccc(C)n4)cc3)c3c(N)ncnc3n2C)c(C)c1F] | $^1$H NMR (400 MHz, DMSO-d$_6$) 8.47 (d, J = 5.0 Hz, 1H), 8.40 (s, 1H), 8.25 (s, 1H), 7.28-7.22 (m, 2H), 7.22-7.12 (m, 3H), 4.80 (d, J = 0.8 Hz, 1H), 3.52 (s, 3H), 2.40 (s, 3H), 1.96 (d, J = 2.2 Hz, 3H). | 466.25 |
| 6-(6-ethynyl-5-fluoro-2-methylpyridin-3-yl)-7-methyl-5-(4-((4-methylpyrimidin-2-yloxy)phenyl)-7H-pyrrolo[2,3-d]pyrimidin-4-amine | 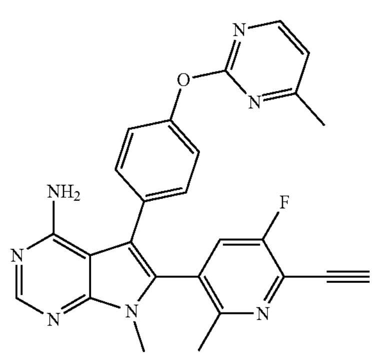 [SMILES: C#Cc1nc(C)c(-c2c(-c3ccc(Oc4nccc(C)n4)cc3)c3c(N)ncnc3n2C)cc1F] | 1H NMR (400 MHz, DMSO-d6) 8.47 (d, J = 5.0 Hz, 1H), 8.25 (s, 1H), 8.04 (d, J = 9.3 Hz, 1H), 7.30-7.23 (m, 2H), 7.23-7.16 (m, 2H), 7.15 (d, J = 5.0 Hz, 1H), 4.80 (d, J = 0.8 Hz, 1H), 3.52 (s, 3H), 2.41 (s, 3H), 2.08 (d, J = 1.1 Hz, 3H). | 466.20 |

TABLE 27-continued

Additional Exemplary Compounds

| Compound | Structure | Proton NMR | MS [M + 1] |
|---|---|---|---|
| 6-(6-ethynyl-4-methylpyridazin-3-yl)-7-methyl-5-(4-((4-methylpyrimidin-2-yl)oxy)phenyl)-7H-pyrrolo[2,3-d]pyrimidin-4-amine | 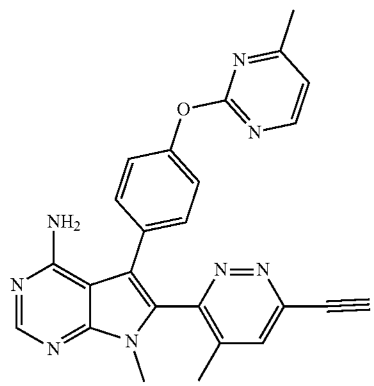 [SMILES: C#Cc1cc(C)c(-c2c(-c3ccc(Oc4nccc(C)n4)cc3)c3c(N)ncnc3n2C)nn1] | $^1$H NMR (400 MHz, DMSO-d$_6$) δ 8.47 (d, J = 5.0 Hz, 1H), 8.27 (s, 1H), 7.39-7.29 (m, 3H), 7.28-7.20 (m, 2H), 7.17 (d, J = 5.0 Hz, 1H), 6.08 (s, 2H), 4.97 (s, 1H), 3.83 (s, 3H), 2.42 (s, 3H), 2.28 (d, J = 0.9 Hz, 3H). | 449.20 |
| 6-(6-ethynyl-4-methylpyridin-3-yl)-7-methyl-5-(1-methyl-1H-pyrazol-4-yl)-7H-pyrrolo[2,3-d]pyrimidin-4-amine | 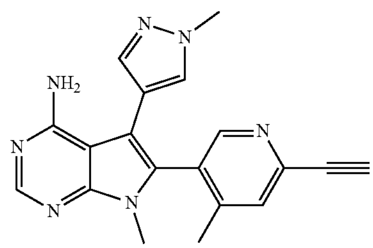 [SMILES: C#Cc1cc(C)c(-c2c(-c3cnn(C)c3)c3c(N)ncnc3n2C)cn1] | 1H NMR (400 MHz, DMSO-d6) 8.43 (s, 1H), 8.19 (s, 1H), 7.62 (d, J = 0.7 Hz,1H), 7.57 (s, 1H), 7.17 (d, J = 0.8 Hz,1H), 6.16 (s, 1H), 4.41 (s, 1H), 3.79 (s, 3H), 3.43 (s, 3H), 2.02 (s, 3H). | 344.15 |
| 6-(6-ethynyl-4-methylpyridin-3-yl)-7-methyl-5-[4-(trifluoromethoxy)phenyl]-7H-pyrrolo[2,3-d]pyrimidin-4-amine | 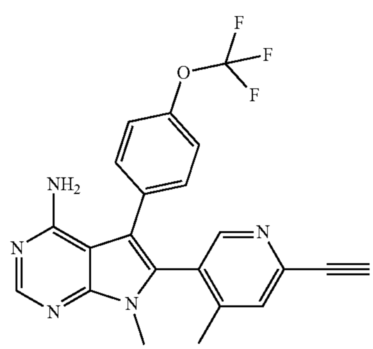 [SMILES: C#Cc1cc(C)c(-c2c(-c3ccc(OC(F)(F)F)cc3)c3c(N)ncnc3n2C)cn1] | 1H NMR: 1H NMR (400 MHz, DMSO-d6) δ 8.46 (s, 1H), 8.24 (s, 1H), 7.55 (s, 1H), 7.31 (q, J = 8.7 Hz, 4H), 6.05 (s, 1H), 4.41 (s, 1H), 3.47 (s, 3H), 1.97 (s, 3H). | 424.10 |
| 6-(6-ethynyl-4-methylpyridin-3-yl)-5-(4-isopropoxyphenyl)-7-methyl-7H-pyrrolo[2,3-d]pyrimidin-4-amine | 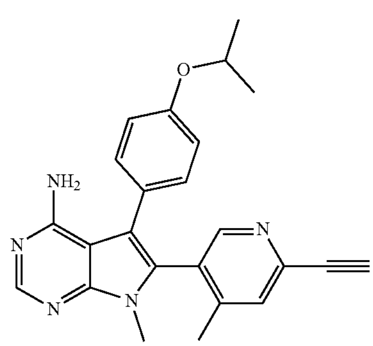 [SMILES: C#Cc1cc(C)c(-c2c(-c3ccc(OC(C)C)cc3)c3c(N)ncnc3n2C)cn1] | $^1$H NMR (400 MHz, DMSO-d$_6$) δ 8.44 (s, 1H), 8.21 (s, 1H), 7.53 (s, 1H), 7.12-7.04 (m, 2H), 6.91-6.84 (m, 2H), 5.95 (s, 2H), 4.58 (hept, J = 6.0 Hz, 1H), 4.39 (s, 1H), 3.46 (s, 3H), 1.98 (s, 3H), 1.25 (d, J = 6.0 Hz, 6H). | 398.30 |

TABLE 27-continued

Additional Exemplary Compounds

| Compound | Structure | Proton NMR | MS [M + 1] |
|---|---|---|---|
| 6-(4-ethynyl-3-fluorophenyl)-7-methyl-5-{4-[(4-methylpyrimidin-2-yl)oxy]phenyl}-7H-pyrrolo[2,3-d]pyrimidin-4-amine | 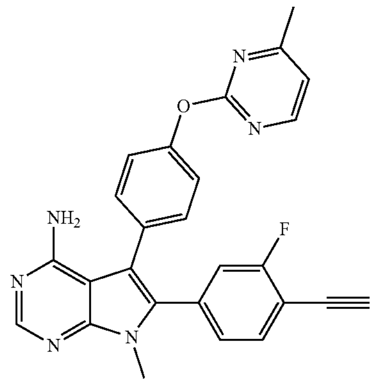 [SMILES: C#Cc1ccc(-c2c(-c3ccc(Oc4nccc(C)n4)cc3)c3c(N)ncnc3n2C)cc1F] | ¹H NMR (400 MHz, Chloroform-d) δ 8.40 (d, J = 5.6 Hz, 2H), 7.32 (s, 1H), 7.29 (s, 2H), 7.25-7.20 (m, 2H), 7.05 (d, J = 1.6 Hz, 1H), 7.04-7.02 (m, 1H), 6.95 (d, J = 5.0 Hz, 1H), 5.13 (s, 2H), 3.77 (s, 3H), 3.39 (s, 1H), 2.53 (s, 3H). | 451.05 |
| 6-(6-ethynyl-5-methoxypyridin-3-yl)-7-methyl-5-(4-((4-methylpyrimidin-2-yl)oxy)phenyl)-7H-pyrrolo[2,3-d]pyrimidin-4-amine | 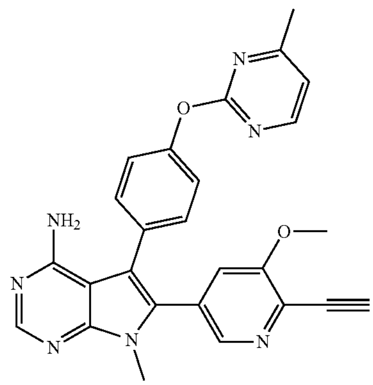 [SMILES: C#Cc1ncc(-c2c(-c3ccc(Oc4nccc(C)n4)cc3)c3c(N)ncnc3n2C)cc1OC] | ¹H NMR (300 MHz, DMSO-d₆) δ 8.45 (d, J = 5.0 Hz, 1H), 8.22 (s, 1H), 8.09 (d, J = 1.7 Hz, 1H), 7.45 (d, J = 1.7 Hz, 1H), 7.35-7.26 (m, 2H), 7.25-7.17 (m, 2H), 7.14 (d, J = 5.0 Hz, 1H), 4.50 (s, 1H), 3.75 (s, 3H), 3.70 (s, 3H), 2.40 (s, 3H). | 464.05 |
| 6-(4-ethynyl-3,5-difluorophenyl)-7-methyl-5-(4-((4-methylpyrimidin-2-yl)oxy)phenyl)-7H-pyrrolo[2,3-d]pyrimidin-4-amine | 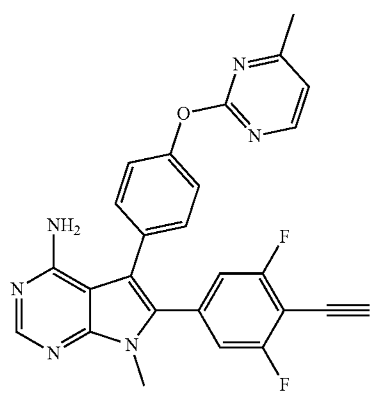 [SMILES: C#Cc1c(F)cc(-c2c(-c3ccc(Oc4nccc(C)n4)cc3)c3c(N)ncnc3n2C)cc1F] | ¹H NMR (300 MHz, DMSO-d6) 8.48 (d, J = 5.0 Hz, 1H), 8.24 (s, 1H), 7.36-7.30 (m, 2H), 7.28-7.21 (m, 4H), 7.19-7.13 (m, 1H), 4.91 (s, 1H), 3.69 (s, 3H), 2.41 (s, 3H). | 469.15 |
| 6-(3-ethynyl-1-methyl-1H-pyrazol-5-yl)-7-methyl-5-{4-[(4-methylpyrimidin-2-yl)oxy]phenyl}-7H-pyrrolo[2,3-d]pyrimidin-4-amine | 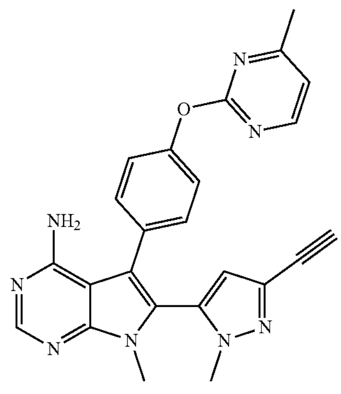 [SMILES: C#Cc1cc(-c2c(-c3ccc(Oc4nccc(C)n4)cc3)c3c(N)ncnc3n2C)n(C)n1] | ¹H NMR (300 MHz, DMSO-d6) δ 8.48 (d, J = 5.0 Hz, 1H), 8.26 (s, 1H), 7.34-7.20 (m, 4H), 7.16 (d, J = 5.0 Hz, 1H), 6.91 (s, 1H), 4.23 (s, 1H), 3.57 (s, 3H), 3.33 (s, 3H), 2.42 (s, 3H). | 437.25 |

TABLE 27-continued

Additional Exemplary Compounds

| Compound | Structure | Proton NMR | MS [M + 1] |
|---|---|---|---|
| 6-(2-ethynylbenzo[d]oxazol-6-yl)-7-methyl-5-(4-(4-methylpyrimidin-2-yl)oxy)phenyl)-7H-pyrrolo[2,3-d]pyrimidin-4-amine | 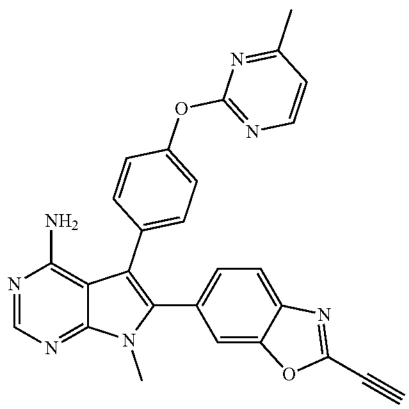 [SMILES: C#Cc1nc2ccc(-c3c(-c4ccc(Oc5nccc(C)n5)cc4)c4c(N)ncnc4n3C)cc2o1] | $^1$H NMR (400 MHz, DMSO-d$_6$) δ 8.46 (d, J = 5.0 Hz, 1H), 8.23 (s, 1H), 7.88-7.80 (m, 2H), 7.44 (dd, J = 8.3, 1.6 Hz, 1H), 7.35-7.27 (m, 2H), 7.20-7.12 (m, 3H), 5.75 (s, 1H), 5.16 (s, 1H), 3.64 (s, 3H), 2.40 (s, 3H). | 474.30 |
| 6-(6-ethynyl-4-methylpyridin-3-yl)-5-(3-fluoro-4-((4-methylpyrimidin-2-yl)oxy)phenyl)-4,7-dimethyl-7H-pyrrolo[2,3-d]pyrimidine | 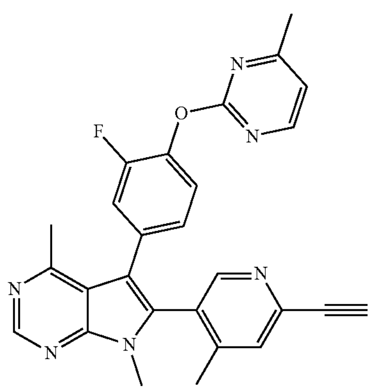 [SMILES: C#Cc1cc(C)c(-c2c(-c3ccc(Oc4nccc(C)n4)c(F)c3)c3c(C)ncnc3n2C)cn1] | $^1$H NMR (400 MHz, DMSO-d6) δ 8.78 (s, 1H), 8.55 (s, 1H), 8.48 (d, J = 5.0 Hz, 1H), 7.59 (t, J = 0.9 Hz, 1H), 7.38-7.26 (m, 2H), 7.18 (d, J = 5.0 Hz, 1H), 7.16-7.09 (m, 1H), 4.44 (s, 1H), 3.56 (s, 3H), 2.41 (d, J = 8.9 Hz, 6H), 2.06 (s, 3H). | 465.15 |
| 6-(6-ethynyl-4-methylpyridin-3-yl)-5-(2-fluoro-4-((4-methylpyrimidin-2-yl)oxy)phenyl)-7-methyl-7H-pyrrolo[2,3-d]pyrimidin-4-amine | 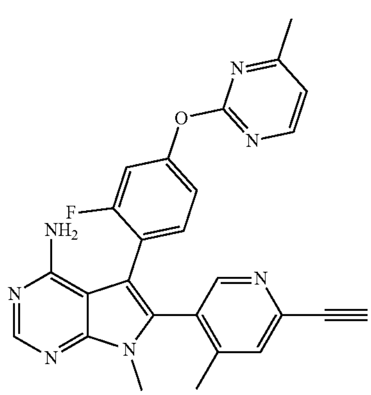 [SMILES: C#Cc1cc(C)c(-c2c(-c3ccc(Oc4nccc(C)n4)cc3F)c3c(N)ncnc3n2C)cn1] | $^1$H NMR (400 MHz, DMSO-d$_6$) δ 8.49 (d, J = 5.0 Hz, 1H), 8.40 (s, 1H), 8.24 (s, 1H), 7.56 (d, J = 7.9 Hz, 1H), 7.45-7.24 (m, 1H), 7.23-7.14 (m, 2H), 7.07 (dd, J = 8.4, 2.3 Hz, 1H), 6.01 (m, 2H), 4.40 (s, 1H), 3.49 (s, 3H), 2.42 (s, 3H), 2.06 (d, J = 19.2 Hz, 3H). | 466.20 |

TABLE 27-continued

Additional Exemplary Compounds

| Compound | Structure | Proton NMR | MS [M + 1] |
|---|---|---|---|
| 6-(6-ethynyl-2-methylpyridin-3-yl)-5-(2-fluoro-4-((4-methylpyrimidin-2-yl)oxy)phenyl)-7-methyl-7H-pyrrolo[2,3-d]pyrimidin-4-amine | 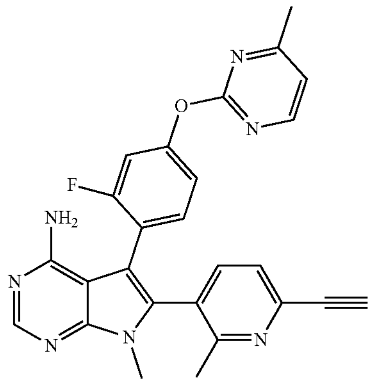 [SMILES: C#Cc1ccc(-c2c(-c3ccc(Oc4nccc(C)n4)cc3F)c3c(N)ncnc3n2C)c(C)n1] | ¹H NMR (400 MHz, DMSO-d₆) δ 8.49 (d = 4.8 Hz, 1H), 8.24 (s, 1H), 7.75 (d, J = 7.6 Hz, 1H), 7.53-7.44 (m, 1H), 7.31 (m, 1H), 7.18 (m, 2H), 7.12-7.01 (m, 1H), 6.01 (m, 2H), 4.40 (s, 1H), 3.49 (s, 3H), 2.42 (s, 3H), 2.18 (m, 3H). | 466.15 |
| 6-(6-ethynyl-4-fluoropyridin-3-yl)-5-(3-fluoro-4-((4-methylpyrimidin-2-yl)oxy)phenyl)-7-methyl-7H-pyrrolo[2,3-d]pyrimidin-4-amine | 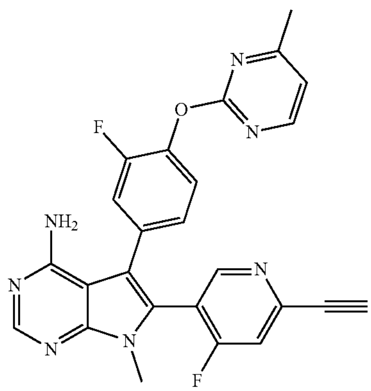 [SMILES: C#Cc1cc(F)c(-c2c(-c3ccc(Oc4nccc(C)n4)c(F)c3)c3c(N)ncnc3n2C)cn1] | ¹H NMR (400 MHz, DMSO-d₆) δ 8.58 (d, J = 10.1 Hz, 1H), 8.48 (d, J = 5.0 Hz, 1H), 8.25 (s, 1H), 7.76 (d, J = 10.0 Hz, 1H), 7.35 (d, J = 8.4 Hz, 1H), 7.27-7.23 (m, 1H), 7.23-7.17 (m, 1H), 7.10-6.99 (m, 1H), 6.17 (s, 1H), 4.63 (s, 1H), 3.63-3.56 (m, 3H), 2.42 (s, 3H). | 470.10 |
| 6-(6-ethynyl-2-methylpyridin-3-yl)-5-(3-fluoro-4-((4-methylpyrimidin-2-yl)oxy)phenyl)-7-methyl-7H-pyrrolo[2,3-d]pyrimidin-4-amine | 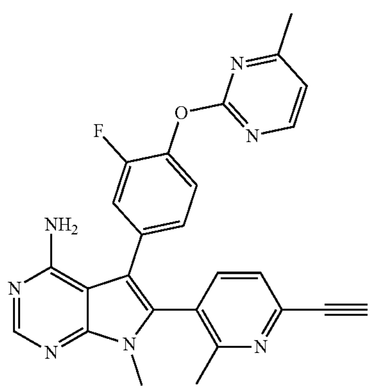 [SMILES: C#Cc1ccc(-c2c(-c3ccc(Oc4nccc(C)n4)c(F)c3)c3c(N)ncnc3n2C)c(C)n1] | 1H NMR (400 MHz, DMSO-d6) δ 8.48 (d, J = 5.0 Hz, 1H), 8.24 (s, 1H), 7.88 (d, J = 7.9 Hz, 1H), 7.52 (d, J = 7.8 Hz, 1H), 7.33 (t, J = 8.4 Hz, 1H), 7.20-7.11 (m, 2H), 7.06-6.99 (m, 1H), 6.13 (s, 1H), 4.42 (s, 1H), 4.42 (s, 5H), 3.47 (s, 1H), 2.41 (s, 1H), 2.14 (s, 1H), | 466.15 |
| 2-{4-[6-(6-ethynyl-2-methylpyridin-3-yl)-4,7-dimethyl-7H-pyrrolo[2,3-d]pyrimidin-5-yl]-2-fluorophenoxy}-4-methylpyrimidine | 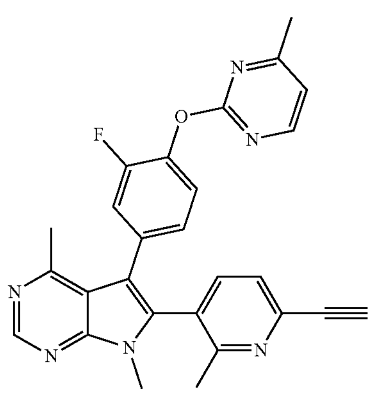 [SMILES: C#Cc1ccc(-c2c(-c3ccc(Oc4nccc(C)n4)c(F)c3)c3c(C)ncnc3n2C)c(C)n1] | ¹H NMR (400 MHz, DMSO-d₆) δ 8.78 (s, 1H), 8.48 (d, J = 5.0 Hz, 1H), 7.91 (d, J = 7.8 Hz, 1H), 7.54 (d, J = 7.9 Hz, 1H), 7.37-7.27 (m, 2H), 7.19 (d, J = 5.0 Hz, 1H), 7.12 (d, J = 8.2 Hz, 1H), 4.44 (s, 1H), 3.57 (s, 3H), 2.44 (s, 3H), 2.41 (s, 3H), 2.19 (s, 3H). | 465.25 |

TABLE 27-continued

Additional Exemplary Compounds

| Compound | Structure | Proton NMR | MS [M + 1] |
|---|---|---|---|
| (5-(4-amino-5-(3-fluoro-4-((4-methylpyrimidin-2-yl)oxy)phenyl)-7-methyl-7H-pyrrolo[2,3-d]pyrimidin-6-yl)-2-ethynylpyridin-4-yl)methanol | 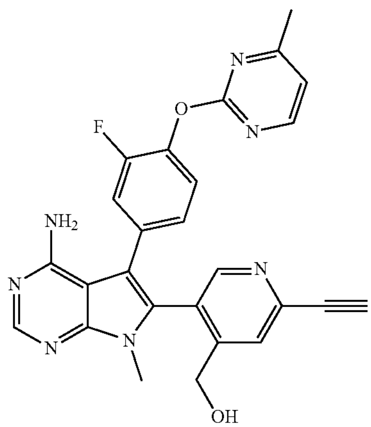 [SMILES: C#Cc1cc(CO)c(-c2c(-c3ccc(Oc4nccc(C)n4)c(F)c3)c3c(N)ncnc3n2C)cn1] | 1H NMR (400 MHz, DMSO-d6) δ 8.54 (d, J = 0.8 Hz, 1H), 8.47 (d, J = 5.0 Hz, 1H), 8.25 (s, 1H), 7.67 (s, 1H), 7.34 (t, J = 8.4 Hz, 1H), 7.23-7.16 (m, 2H), 7.06 (dd, J = 9.3, 1.6 Hz, 1H), 5.48 (t, J = 5.7 Hz, 1H), 4.46 (s, 1H), 4.25 (dd, J = 15.7, 5.8 Hz, 1H), 4.03 (dd, J = 15.6, 5.9 Hz, 1H), 3.46 (s, 3H), 2.41 (s, 3H). | 482.15 |
| 6-(4-((dimethylamino)methyl)-6-ethynylpyridin-3-yl)-5-(3-fluoro-4-((4-methylpyrimidin-2-yl)oxy)phenyl)-7-methyl-7H-pyrrolo[2,3-d]pyrimidin-4-amine | 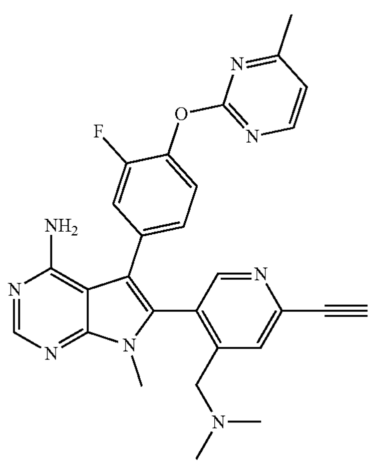 [SMILES: C#Cc1cc(CN(C)C)c(-c2c(-c3ccc(Oc4nccc(C)n4)c(F)c3)c3c(N)ncnc3n2C)cn1] | 1H NMR (400 MHz, DMSO-d6) δ 8.62 (d, J = 0.8 Hz, 1H), 8.46 (d, J = 5.0 Hz, 1H), 8.25 (s, 1H), 7.66 (s, 1H), 7.31 (d, J = 8.4 Hz, 1H), 7.19-7.13 (m, 2H), 4.46 (s, 1H), 3.46 (s, 3H), 3.23 (d, J = 15.1 Hz, 1H), 2.85 (d, J = 15.2 Hz, 1H), 2.40 (s, 3H), 1.97 (s, 6H). | 509.40 |
| 6-(4-(difluoromethyl)-6-ethynylpyridin-3-yl)-5-(3-fluoro-4-((4-methylpyrimidin-2-yl)oxy)phenyl)-7-methyl-7H-pyrrolo[2,3-d]pyrimidin-4-amine | 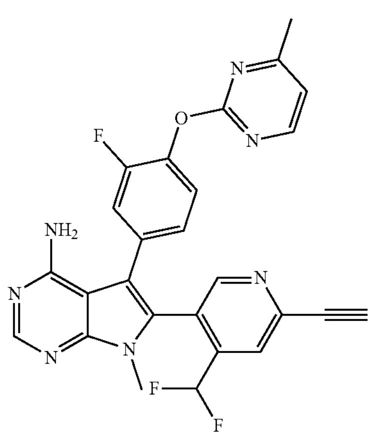 [SMILES: C#Cc1cc(C(F)F)c(-c2c(-c3ccc(Oc4nccc(C)n4)c(F)c3)c3c(N)ncnc3n2C)cn1] | $^1$H NMR (300 MHz, DMSO-d6) 8.81 (d, J = 0.9 Hz, 1H), 8.44 (d, J = 5.0 Hz, 1H), 8.24 (s, 1H), 7.82 (s, 1H), 7.30 (t, J = 8.4 Hz, 1H), 7.24-7.11 (m, 2H), 7.03 (ddd, J = 8.3, 2.1, 0.9 Hz, 1H), 6.73 (s, 1H), 6.12 (s, 1H), 4.62 (s, 1H), 3.46 (s, 3H), 2.37 (s, 3H). | 502.15 |

TABLE 27-continued

Additional Exemplary Compounds

| Compound | Structure | Proton NMR | MS [M + 1] |
|---|---|---|---|
| 6-(2-ethyl-6-ethynylpyridin-3-yl)-5-(3-fluoro-4-((4-methylpyrimidin-2-yl)oxy)phenyl)-7-methyl-7H-pyrrolo[2,3-d]pyrimidin-4-amine | 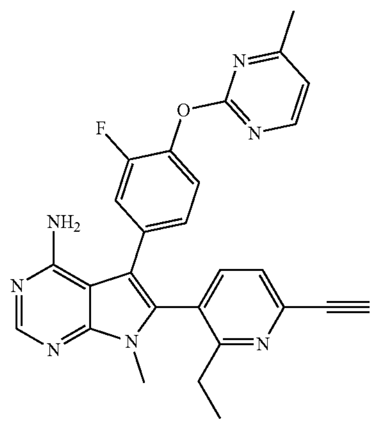 [SMILES: C#Cc1ccc(-c2c(-c3ccc(Oc4nccc(C)n4)c(F)c3)c3c(N)ncnc3n2C)c(CC)n1] | 1H NMR (300 MHz, DMSO-d6) δ 8.43 (d, J = 5.0 Hz, 1H), 8.21 (s, 1H), 7.89 (d, J = 7.9 Hz, 1H), 7.51 (d, J = 7.8 Hz, 1H), 7.30 (t, J = 8.4 Hz, 1H), 7.20-7.05 (m, 2H), 6.99 (d, J = 8.2 Hz, 1H), 6.11 (s, 1H), 4.38 (s, 1H), 3.35 (s, 3H), 2.42-2.21 (m, 4H), 0.90 (t, J = 7.5 Hz, 3H). | 480.15 |
| 6-(4-ethyl-6-ethynylpyridin-3-yl)-5-{3-fluoro-4-[(4-methylpyrimidin-2-yl)oxy]phenyl}-7-methyl-7H-pyrrolo[2,3-d]pyrimidin-4-amine | 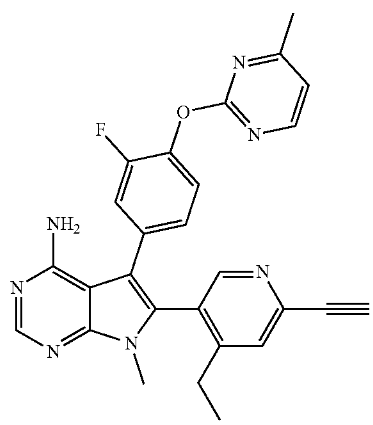 [SMILES: C#Cc1cc(CC)c(-c2c(-c3ccc(Oc4nccc(C)n4)c(F)c3)c3c(N)ncnc3n2C)cn1] | $^1$H NMR (400 MHz, DMSO-d$_6$) δ 8.58 (s, 1H), 8.47 (d, J = 5.0 Hz, 1H), 8.24 (s, 1H), 7.58 (s, 1H), 7.33 (t, J = 8.4 Hz, 1H), 7.22-7.12 (m, 2H), 7.04 (d, J = 8.3 Hz, 1H), 6.13 (s, 1H), 4.44 (s, 1H), 3.46 (s, 3H), 2.39 (d, J = 10.2 Hz, 4H), 2.22 (dt, J = 14.9, 7.6 Hz, 1H), 0.91 (t, J = 7.5 Hz, 3H). | 480.30 |
| 6-(6-ethynyl-4-methylpyridin-3-yl)-5-(3-fluoro-4-((4-methylpyrimidin-2-yl)oxy)phenyl)-7-isopropyl-7H-pyrrolo[2,3-d]pyrimidin-4-amine | 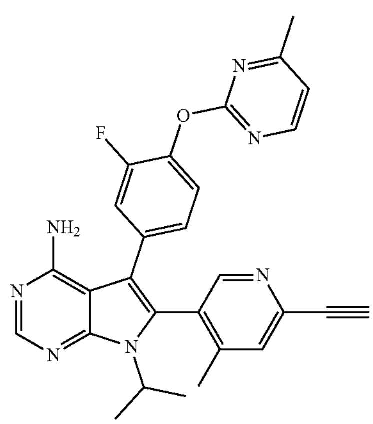 [SMILES: C#Cc1cc(C)c(-c2c(-c3ccc(Oc4nccc(C)n4)c(F)c3)c3c(N)ncnc3n2C(C)C)cn1] | 1H NMR (300 MHz, DMSO-d6) δ 8.53 (s, 1H), 8.47 (d, J = 5.0 Hz, 1H), 8.22 (s, 1H), 7.56 (s, 1H), 7.31 (t, J = 8.4 Hz, 1H), 7.22-7.11 (m, 2H), 7.03 (d, J = 8.6 Hz, 1H), 6.08 (s, 2H), 4.43 (s, 1H), 4.11-4.00 (m, 1H), 2.41 (s, 3H), 2.06 (d, J = 14.2 Hz, 3H), 1.62 (d, J = 6.8 Hz, 3H), 1.50 (d, J = 6.7 Hz, 3H). | 494.20 |

TABLE 27-continued

Additional Exemplary Compounds

| Compound | Structure | Proton NMR | MS [M + 1] |
|---|---|---|---|
| 6-(6-ethynyl-4-methylpyridin-3-yl)-5-(3-fluoro-4-((4-methylpyrimidin-2-yl)oxy)phenyl)-7-isopropyl-7H-pyrrolo[2,3-d]pyrimidin-4-amine | 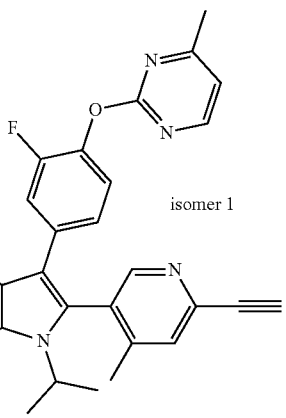 isomer 1 | $^1$H NMR (400 MHz, DMSO-d$_6$) δ 8.53 (s, 1H), 8.47 (d, J = 5.0 Hz, 1H), 8.23 (s, 1H), 7.56 (s, 1H), 7.31 (t, J = 8.4 Hz, 1H), 7.21-7.12 (m, 2H), 7.04 (dd, J = 8.2, 2.1 Hz, 1H), 6.10 (s, 1H), 4.42 (s, 1H), 4.07 (p, J = 6.8 Hz, 1H), 2.41 (s, 3H), 2.04 (s, 3H), 1.62 (d, J = 6.8 Hz, 3H), 1.50 (d, J = 6.8 Hz, 3H). | 494.35 |
| 6-(6-ethynyl-4-methylpyridin-3-yl)-5-(3-fluoro-4-((4-methylpyrimidin-2-yl)oxy)phenyl)-7-isopropyl-7H-pyrrolo[2,3-d]pyrimidin-4-amine | 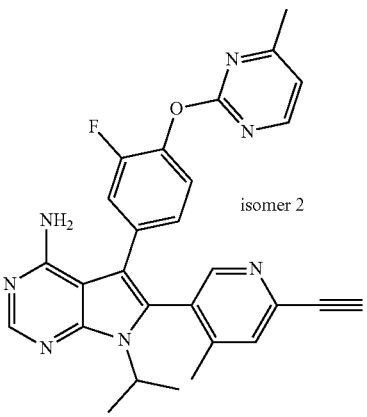 [SMILES: C#Cc1cc(C)c(-c2c(-c3ccc(Oc4nccc(C)n4)c(F)c3)c3c(N)ncnc3n2C(C)C)cn1] isomer 2 | $^1$H NMR (400 MHz, DMSO-d$_6$) δ 8.53 (s, 1H), 8.47 (d, J = 5.0 Hz, 1H), 8.23 (s, 1H), 7.56 (s, 1H), 7.31 (t, J = 8.4 Hz, 1H), 7.21-7.12 (m, 2H), 7.04 (dt, J = 8.3, 1.4 Hz, 1H), 6.09 (s, 1H), 4.42 (s, 1H), 4.07 (p, J = 6.8 Hz, 1H), 2.41 (s, 3H), 2.04 (s, 3H), 1.62 (d, J = 6.8 Hz, 3H), 1.50 (d, J = 6.8 Hz, 3H). | 494.35 |
| 6-(6-ethynyl-2-methylpyridin-3-yl)-5-(3-fluoro-4-((4-methylpyrimidin-2-yl)oxy)phenyl)-7-isopropyl-7H-pyrrolo[2,3-d]pyrimidin-4-amine | 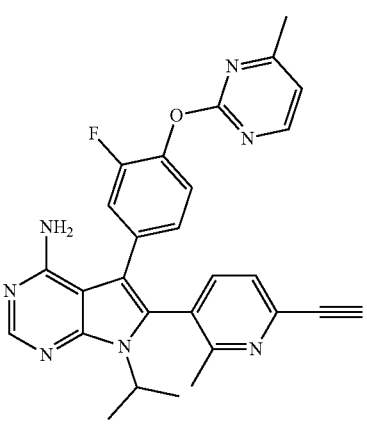 [SMILES: C#Cc1ccc(-c2c(-c3ccc(Oc4nccc(C)n4)c(F)c3)c3c(N)ncnc3n2C(C)C)c(C)n1] | $^1$H NMR (300 MHz, DMSO-d6) δ 8.47 (d, J = 5.0 Hz, 1H), 8.21 (s, 1H), 7.90 (d, J = 7.9 Hz, 1H), 7.53 (d, J = 7.8 Hz, 1H), 7.32 (t, J = 8.4 Hz, 1H), 7.22-7.10 (m, 2H), 7.02 (d, J = 8.6 Hz, 1H), 6.10 (s, 1H), 4.43 (s, 1H), 4.13-4.02 (m, 1H), 2.41 (s, 3H), 2.16 (s, 3H), 1.62 (d, J = 6.8 Hz, 3H), 1.50 (d, J = 6.8 Hz, 3H). | 494.20 |

TABLE 27-continued

Additional Exemplary Compounds

| Compound | Structure | Proton NMR | MS [M + 1] |
|---|---|---|---|
| 6-(6-ethynyl-2-methylpyridin-3-yl)-5-(3-fluoro-4-((4-methylpyrimidin-2-yl)oxy)phenyl)-7-isopropyl-7H-pyrrolo[2,3-d]pyrimidin-4-amine | 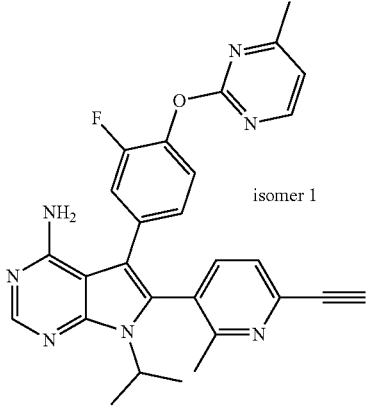 [SMILES: C#Cc1ccc(-c2c(-c3ccc(Oc4nccc(C)n4)c(F)c3)c3c(N)ncnc3n2C(C)C)c(C)n1] isomer 1 | $^1$H NMR (400 MHz, DMSO-$d_6$) δ 8.47 (d, J = 5.0 Hz, 1H), 8.22 (s, 1H), 7.89 (d, J = 7.9 Hz, 1H), 7.52 (dd, J = 7.9, 0.7 Hz, 1H), 7.32 (t, J = 8.4 Hz, 1H), 7.21-7.11 (m, 2H), 7.02 (ddd, J = 8.3, 2.1, 0.9 Hz, 1H), 6.04 (s, 2H), 4.42 (s, 1H), 4.08 (p, J = 6.7 Hz, 1H), 2.41 (s, 3H), 2.16 (s, 3H), 1.62 (d, J = 6.8 Hz, 3H), 1.50 (d, J = 6.8 Hz, 3H). | 494.35 |
| 6-(6-ethynyl-2-methylpyridin-3-yl)-5-(3-fluoro-4-((4-methylpyrimidin-2-yl)oxy)phenyl)-7-isopropyl-7H-pyrrolo[2,3-d]pyrimidin-4-amine | 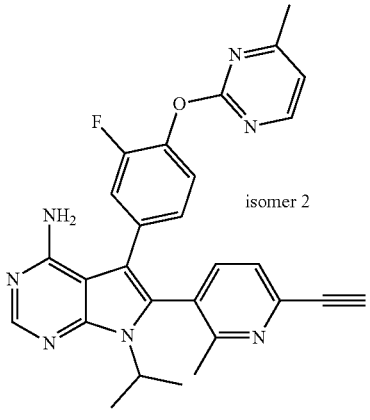 [SMILES: C#Cc1ccc(-c2c(-c3ccc(Oc4nccc(C)n4)c(F)c3)c3c(N)ncnc3n2C(C)C)c(C)n1] isomer 2 | $^1$H NMR (400 MHz, DMSO-$d_6$) δ 8.47 (d, J = 5.0 Hz, 1H), 8.22 (s, 1H), 7.89 (d, J = 7.8 Hz, 1H), 7.53 (d, J = 7.9 Hz, 1H), 7.32 (t, J = 8.4 Hz, 1H), 7.21-7.12 (m, 2H), 7.02 (d, J = 8.1 Hz, 1H), 6.04 (s, 1H) 4.42 (s, 1H), 4.08 (t, J = 6.8 Hz, 1H), 2.41 (s, 3H), 2.16 (s,3H), 1.62 (d, J = 6.8 Hz, 3H), 1.50 (d, J = 6.8 Hz, 3H) | 494.35 |
| 6-(6-ethynyl-4-methylpyridin-3-yl)-5-(3-fluoro-4-(pyrimidin-2-yloxy)phenyl)-7-methyl-7H-pyrrolo[2,3-d]pyrimidin-4-amine | 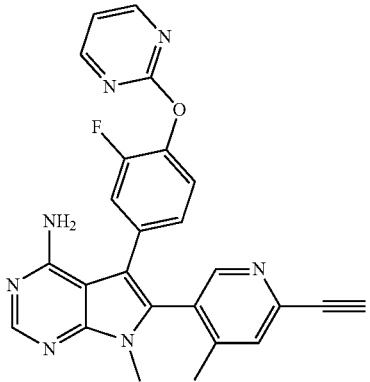 [SMILES: C#Cc1cc(C)c(-c2c(-c3ccc(Oc4ncccn4)c(F)c3)c3c(N)ncnc3n2C)cn1] | $^1$H NMR (400 MHz, DMSO-d6) δ 8.68 (d, J = 4.8 Hz, 2H), 8.52 (s, 1H), 8.27 (d, J = 2.7 Hz, 1H), 7.59 (s, 1H), 7.41-7.29 (m, 2H), 7.19-7.06 (m, J = 8.3 Hz, 2H), 6.15 (s, 1H), 4.43 (s, 1H), 3.47 (s, 3H), 2.04 (s, 3H). | 452.15 |

TABLE 27-continued

Additional Exemplary Compounds

| Compound | Structure | Proton NMR | MS [M + 1] |
|---|---|---|---|
| 6-(6-ethynyl-4-methylpyridin-3-yl)-5-(3-fluoro-4-((6-methylpyridin-2-yl)oxy)phenyl)-7-methyl-7H-pyrrolo[2,3-d]pyrimidin-4-amine | 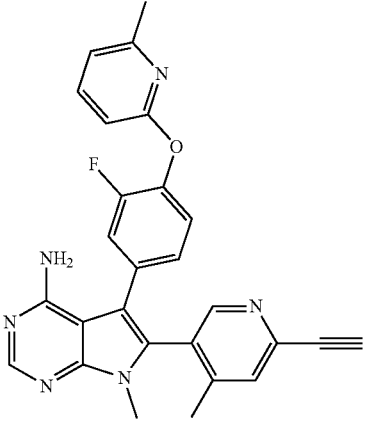 [SMILES: C#Cc1cc(C)c(-c2c(-c3ccc(Oc4cccc(C)n4)c(F)c3)c3c(N)ncnc3n2C)cn1] | ¹H NMR (300 MHz, DMSO-d6) δ 8.49 (s, 1H), 8.22 (s, 1H), 7.71 (dd, J = 8.2, 7.3 Hz, 1H), 7.53 (d, J = 0.8 Hz, 1H), 7.22 (t, J = 8.4 Hz, 1H), 7.10 (dd, J = 11.5, 2.0 Hz, 1H), 7.01-6.98 (m, 1H), 6.97 (d, J = 3.4 Hz, 1H), 6.83 (d, J = 8.1 Hz, 1H), 6.15 (s, 2H), 4.39 (s, 1H), 3.46 (s, 3H), 2.26 (s, 3H), 1.97 (s, 3H). | 465.35 |
| 6-(2-ethynylpyridin-4-yl)-5-(3-fluoro-4-((4-methylpyrimidin-2-yl)oxy)phenyl)-7-methyl-7H-pyrrolo[2,3-d]pyrimidin-4-amine | 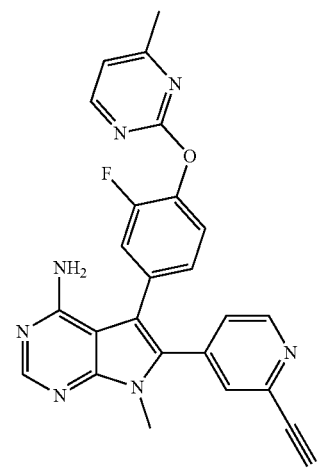 [SMILES: C#Cc1cc(-c2c(-c3ccc(Oc4nccc(C)n4)c(F)c3)c3c(N)ncnc3n2C)ccn1] | 1H NMR (300 MHz, DMSO-d6) δ 8.60 (dd, J = 5.2, 0.9 Hz, 1H), 8.49 (d, J = 5.0 Hz, 1H), 8.25 (s, 1H), 7.53 (t, J = 1.3 Hz, 1H), 7.46-6.99 (m, 5H), 4.39 (s, 1H), 3.68 (s, 3H), 2.43 (s, 3H). | 452.15 |
| 6-(6-ethynyl-4-methylpyridin-3-yl)-5-(3-fluoro-4-((1-methyl-1H-pyrazol-3-yl)oxy)phenyl)-7-methyl-7H-pyrrolo[2,3-d]pyrimidin-4-amine | 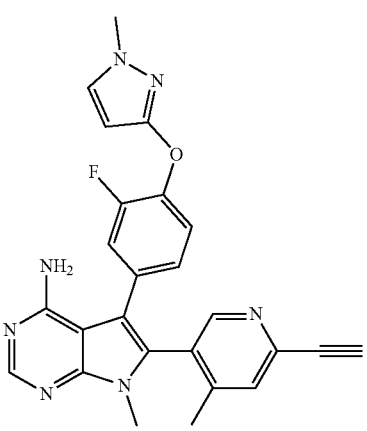 [SMILES: C#Cc1cc(C)c(-c2c(-c3ccc(Oc4ccn(C)n4)c(F)c3)c3c(N)ncnc3n2C)cn1] | 1H NMR (300 MHz, DMSO-d6) δ 8.45 (s, 1H), 8.20 (s, 1H), 7.60 (d, J = 2.3 Hz, 1H), 7.53 (d, J = 0.9 Hz, 1H), 7.17-7.04 (m, 2H), 6.92 (dt, J = 8.4, 1.5 Hz, 1H), 6.10 (s, 1H), 5.82 (d, J = 2.3 Hz, 1H), 4.39 (s, 1H), 3.70 (s, 3H), 3.43 (s, 3H), 1.97 (s, 3H). | 454.10 |

TABLE 27-continued

Additional Exemplary Compounds

| Compound | Structure | Proton NMR | MS [M + 1] |
|---|---|---|---|
| 6-(1-ethynylisoquinolin-4-yl)-5-(3-fluoro-4-((4-methylpyrimidin-2-yl)oxy)phenyl)-7-methyl-7H-pyrrolo[2,3-d]pyrimidin-4-amine | 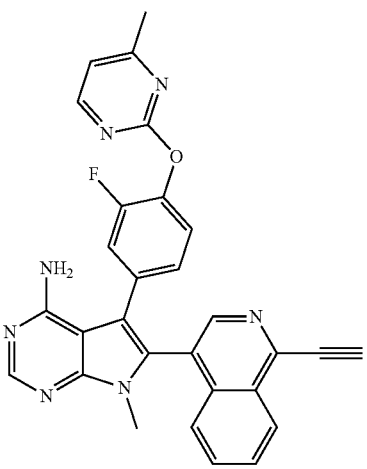 [SMILES: C#Cc1ncc(-c2c(-c3ccc(Oc4nccc(C)n4)c(F)c3)c3c(N)ncnc3n2C)c2ccccc12] | $^1$H NMR (400 MHz, DMSO-d$_6$) δ 8.61 (s, 1H), 8.48-8.37 (m, 2H), 8.29 (s, 1H), 7.87-7.80 (m, 2H), 7.63-7.56 (m, 1H), 7.26-7.17 (m, 2H), 7.14 (d, J = 5.1 Hz, 1H), 7.05-7.01 (m, 1H), 6.15 (s, 1H), 4.97 (s, 1H), 3.43 (s, 3H), 2.36 (s, 3H). | 502.20 |
| 6-(6-ethynyl-4-methylpyridin-3-yl)-7-methyl-5-(5-((4-methylpyrimidin-2-yl)oxy)pyridin-2-yl)-7H-pyrrolo[2,3-d]pyrimidin-4-amine | 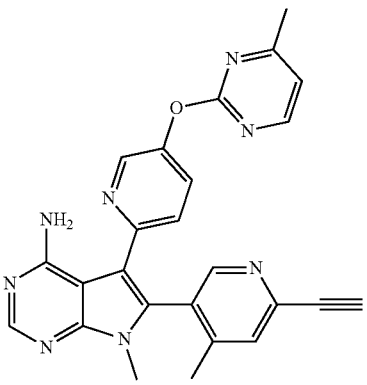 | $^1$H NMR (400 MHz, Methanol-d$_4$) δ 8.58 (d, J = 2.7 Hz, 1H), 8.50 (s, 1H), 8.43 (d, J = 5.1 Hz, 1H), 8.22 (s, 1H), 7.70 (s, 1H), 7.46 (dd, J = 8.8, 2.8 Hz, 1H), 7.15 (d, J = 5.1 Hz, 1H), 6.92 (d, J = 8.7 Hz, 1H), 4.58 (s, 1H), 3.55 (s, 3H), 2.48 (s, 3H), 2.17 (s, 3H). | 449.30 |
| 6-(4-chloro-6-ethynylpyridin-3-yl)-5-{3-fluoro-4-[(4-methylpyrimidin-2-yl)oxy]phenyl}-7-methyl-7H-pyrrolo[2,3-d]pyrimidin-4-amine | 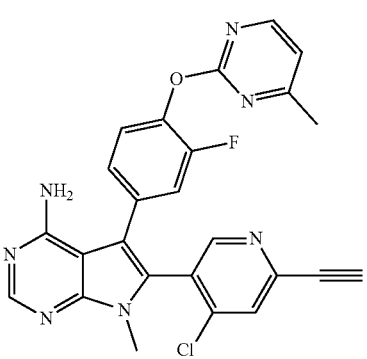 [SMILES: C#Cc1cc(Cl)c(-c2c(-c3ccc(Oc4nccc(C)n4)c(F)c3)c3c(N)ncnc3n2C)cn1] | $^1$H NMR (400 MHz, DMSO-d$_6$) δ 8.62 (s, 1H), 8.48 (d, J = 5.0 Hz, 1H), 8.26 (s, 1H), 7.98 (s, 1H), 7.35 (s, 1H), 7.23-7.15 (m, 2H), 7.09-6.99 (m, 1H), 6.18 (s, 1H), 4.63 (s, 1H), 3.53 (s, 3H), 2.42 (s, 3H). | 486.25 |

TABLE 27-continued

Additional Exemplary Compounds

| Compound | Structure | Proton NMR | MS [M + 1] |
|---|---|---|---|
| 6-(6-ethynyl-5-fluoro-4-methoxypyridin-3-yl)-5-{3-fluoro-4-[(4-methylpyrimidin-2-yl)oxy]phenyl}-7-methyl-7H-pyrrolo[2,3-d]pyrimidin-4-amine | 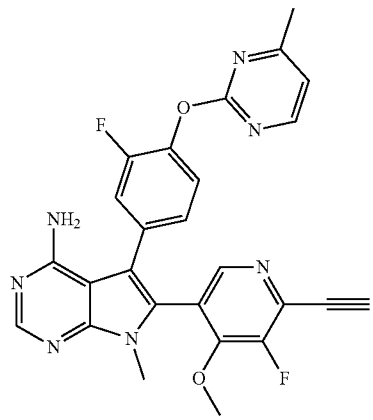 [SMILES: C#Cc1ncc(-c2c(-c3ccc(Oc4nccc(C)n4)c(F)c3)c3c(N)ncnc3n2C)c(OC)c1F] | $^1$H NMR (400 MHz, DMSO-d$_6$) δ8.48 (d, J = 5.0 Hz, 1H), 8.24 (s, 1H), 8.18 (s, 1H), 7.38-7.34 (m, 1H), 7.23-7.18 (m, 2H), 7.08-7.05 (m, 1H), 6.13 (s, 1H), 4.84 (d, J = 1.0 Hz, 1H), 3.91 (d, J = 4.5 Hz, 3H), 3.56 (s, 3H), 2.51 (s, 3H). | 500.15 |
| 4-(4-amino-6-(6-ethynyl-5-fluoro-4-methylpyridin-3-yl)-7-methyl-7H-pyrrolo[2,3-d]pyrimidin-5-yl)-2-fluoro-N-isobutylbenzamide | 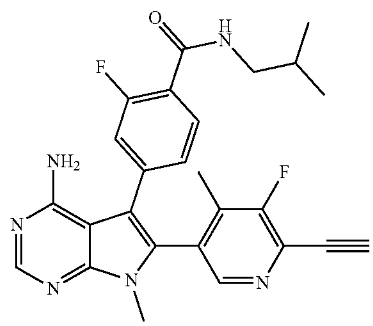 [SMILES: C#Cc1ncc(-c2c(-c3ccc(C(=O)NCC(C)C)c(F)c3)c3c(N)ncnc3n2C)c(C)c1F] | $^1$H NMR (300 MHz, DMSO-d$_6$) δ 8.34 (s, 1H), 8.23 (s, 2H), 7.51 (t, J = 7.9 Hz, 1H), 7.10-6.98 (m, 2H), 6.16 (s, 1H), 4.79 (d, J = 0.8 Hz, 1H), 3.48 (s, 3H), 3.09-2.98 (m, 2H), 1.95 (d, J = 2.1 Hz, 3H), 1.79 (dp, J = 13.4, 6.7 Hz, 1H), 0.86 (d, J = 6.7 Hz, 6H). | 475.30 |
| 5-(3-chloro-4-((4-methylpyrimidin-2-yl)oxy)phenyl)-6-(6-ethynyl-5-fluoro-4-methylpyridin-3-yl)-7-methyl-7H-pyrrolo[2,3-d]pyrimidin-4-amine | 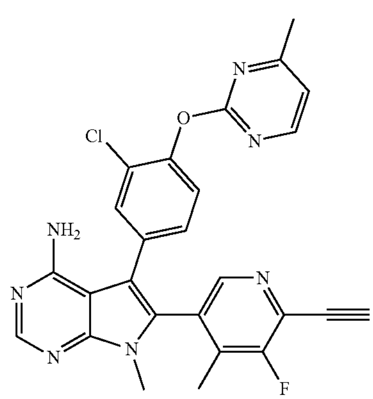 [SMILES: C#Cc1ncc(-c2c(-c3ccc(Oc4nccc(C)n4)c(Cl)c3)c3c(N)ncnc3n2C)c(C)c1F] | 1H NMR (400 MHz, DMSO-d6) δ 8.47 (d, J = 5.0 Hz, 1H), 8.44 (s, 1H), 8.26 (s, 1H), 7.38 (s, 1H), 7.33 (d, J = 8.3 Hz, 1H), 7.22-7.13 (m, 2H), 6.18 (s, 2H), 4.81 (d, J = 0.8 Hz, 1H), 3.52 (s, 3H), 2.41 (s, 3H), 1.96 (d, J = 2.1 Hz, 3H). | 500.15 |

TABLE 27-continued

Additional Exemplary Compounds

| Compound | Structure | Proton NMR | MS [M + 1] |
|---|---|---|---|
| 2-(4-amino-6-(6-ethynyl-4-methylpyridin-3-yl)-5-(3-fluoro-4-((4-methylpyrimidin-2-yl)oxy)phenyl)-7H-pyrrolo[2,3-d]pyrimidin-7-yl)ethan-1-ol | 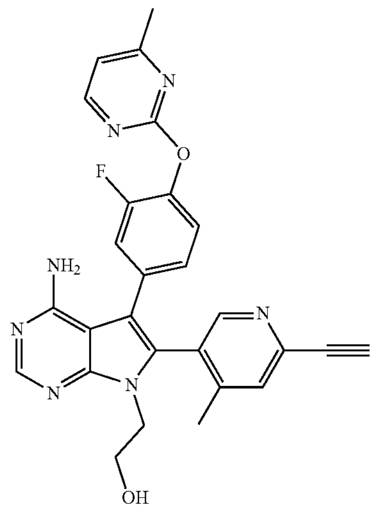 [SMILES: C#Cc1cc(C)c(-c2c(-c3ccc(Oc4nccc(C)n4)c(F)c3)c3c(N)ncnc3n2CCO)cn1] | ¹H NMR (300 MHz, DMSO-d6) δ 8.55 (s, 1H), 8.48 (d, J = 5.0 Hz, 1H), 8.24 (s, 1H), 7.54 (s, 1H), 7.33 (t, J = 8.4 Hz, 1H), 7.22-7.09 (m, 2H), 7.03 (d, J = 8.4 Hz, 1H), 6.14 (s, 1H), 4.79 (t, J = 5.6 Hz, 1H), 4.42 (s, 1H), 4.09 (dd, J = 13.3, 6.5 Hz, 1H), 3.85 (dt, J = 13.5, 6.2 Hz, 1H), 3.52 (q, J = 6.0 Hz, 2H), 2.41 (s, 3H), 1.97 (s, 3H). | 496.30 |
| (1S,3r)-3-(4-amino-6-(6-ethynyl-4-methylpyridin-3-yl)-5-(3-fluoro-4-((4-methylpyrimidin-2-yl)oxy)phenyl)-7H-pyrrolo[2,3-d]pyrimidin-7-yl)cyclobutan-1-ol | 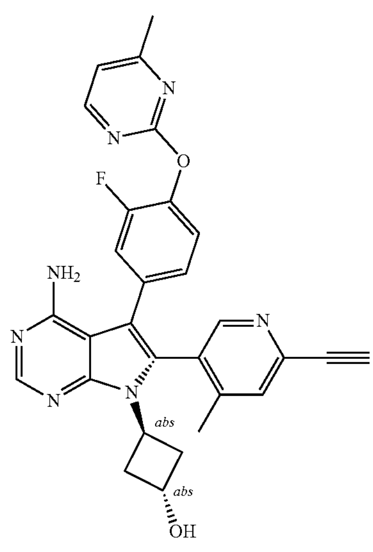 | 1H NMR (400 MHz, Chloroform-d) δ 8.44 (s, 1H), 8.41-8.33 (m, 2H), 7.42 (s, 1H), 7.28 (s, 2H), 7.23 (t, J = 8.2 Hz, 1H), 7.04-6.92 (m, 3H), 6.19 (s, 1H), 5.22 (s, 2H), 4.23-4.14 (m, 1H), 4.10 (p, J = 7.4 Hz, 1H), 3.24 (s, 1H), 3.03 (dt, J = 10.6, 6.5 Hz, 4H), 2.51 (s, 3H), 2.04 (s, 3H). | 522.20 |

TABLE 27-continued

Additional Exemplary Compounds

| Compound | Structure | Proton NMR | MS [M + 1] |
|---|---|---|---|
| 5-(3-chloro-4-((4-methylpyrimidin-2-yl)oxy)phenyl)-6-(6-ethynyl-4-methylpyridin-3-yl)-7-methyl-7H-pyrrolo[2,3-d]pyrimidin-4-amine | 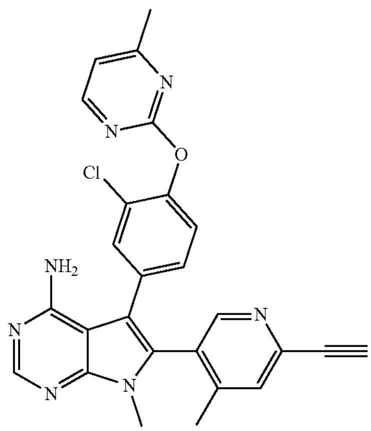 | ¹H NMR (400 MHz, DMSO-d6) δ 8.52 (s, 1H), 8.46 (d, J = 5.0 Hz, 1H), 8.25 (s, 1H), 7.58 (s, 1H), 7.41-7.27 (m, 2H), 7.25-7.13 (m, 2H), 6.14-6.11 (m, 1H), 4.43 (s, 1H), 3.47 (s, 3H), 2.42 (s, 3H), 2.02 (s, 3H). | 482.15 |
| 5-(4-amino-6-(6-ethynyl-4-methylpyridin-3-yl)-7-methyl-7H-pyrrolo[2,3-d]pyrimidin-5-yl)-2-((4-methylpyrimidin-2-yl)oxy)benzonitrile | 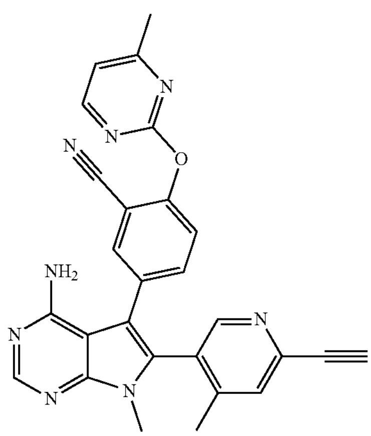 [SMILES: C#Cc1cc(C)c(-c2c(-c3ccc(Oc4nccc(C)n4)c(C#N)c3)c3c(N)ncnc3n2C)cn1] | ¹H NMR (400 MHz, DMSO-d₆) δ 8.52 (d, J = 5.1 Hz, 2H), 8.25 (s, 1H), 7.70 (d, J = 2.2 Hz, 1H), 7.58 (d, J = 0.8 Hz, 1H), 7.49 (dd, J = 8.6, 2.3 Hz, 1H), 7.40 (d, J = 8.6 Hz, 1H), 7.25 (d, J = 5.1 Hz, 1H), 6.21 (s, 2H), 4.43 (s, 1H), 3.47 (s, 3H), 2.44 (s, 3H), 2.01 (s, 3H). | 473.20 |
| 6-(6-ethynyl-5-fluoro-4-methylpyridin-3-yl)-5-{2-fluoro-4-[(4-methylpyrimidin-2-yl)oxy]phenyl}-7-methyl-7H-pyrrolo[2,3-d]pyrimidin-4-amine | 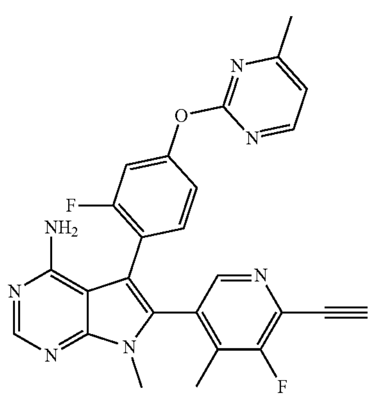 [SMILES: C#Cc1ncc(-c2c(-c3ccc(Oc4nccc(C)n4)cc3F)c3c(N)ncnc3n2C)c(C)c1F] | ¹H NMR (400 MHz, DMSO-d₆) δ 8.49 (d, J = 5.0 Hz, 1H), 8.32 (d, J = 6.6 Hz, 1H), 8.25 (s, 1H), 7.35 (t, J = 8.6 Hz, 1H), 7.26-7.16 (m, 2H), 7.12-7.02 (m, 1H), 6.08 (s, 1H), 4.79 (d, J = 0.8 Hz, 1H), 3.54 (s, 3H), 2.41 (s, 3H), 2.00 (d, J = 24.8 Hz, 3H). | 484.30 |

TABLE 27-continued

Additional Exemplary Compounds

| Compound | Structure | Proton NMR | MS [M + 1] |
|---|---|---|---|
| 6-(6-ethynyl-4-fluoropyridin-3-yl)-5-(3-fluoro-4-((4-methylpyrimidin-2-yl)oxy)phenyl)-4,7-dimethyl-7H-pyrrolo[2,3-d]pyrimidine | 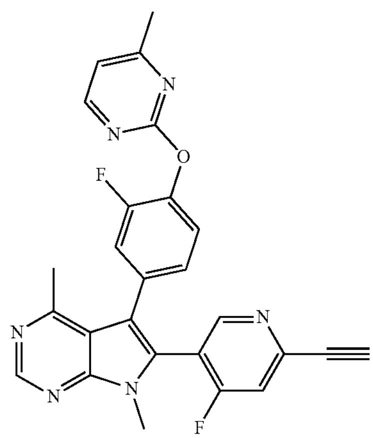 [SMILES: C#Cc1cc(F)c(-c2c(-c3ccc(Oc4nccc(C)n4)c(F)c3)c3c(C)ncnc3n2C)cn1] | $^{1}$H NMR (400 MHz, DMSO-d$_{6}$) δ 8.80 (s, 1H), 8.65 (d, J = 10.0 Hz, 1H), 8.49 (d, J = 5.0 Hz, 1H), 7.79 (d, J = 10.0 Hz, 1H), 7.43-7.30 (m, 2H), 7.17 (dd, J = 12.6, 6.7 Hz, 2H), 4.64 (s, 1H), 3.70 (s, 3H), 2.41 (d, J = 2.9 Hz, 6H). | 469.30 |
| 5-{4-[(4,6-dimethylpyrimidin-2-yl)oxy]-3-fluorophenyl}-6-(6-ethynyl-4-methylpyridin-3-yl)-7-methyl-7H-pyrrolo[2,3-d]pyrimidin-4-amine | 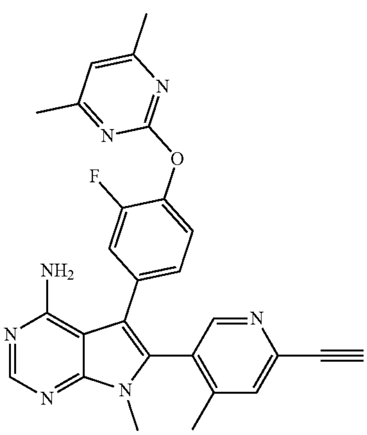 [SMILES: C#Cc1cc(C)c(-c2c(-c3ccc(Oc4nc(C)cc(C)n4)c(F)c3)c3c(N)ncnc3n2C)cn1] | $^{1}$H NMR (400 MHz, DMSO-d$_{6}$) δ 8.51 (d, J = 0.7 Hz, 1H), 8.24 (s, 1H), 7.56 (t, J = 0.8 Hz, 1H), 7.30 (t, J = 8.4 Hz, 1H), 7.14 (dd, J = 11.4, 2.0 Hz, 1H), 7.07-6.99 (m, 2H), 6.16 (s, 1H), 4.42 (s, 1H), 3.49 (s, 3H), 2.33 (s, 6H), 2.00 (s, 3H). | 480.35 |
| 6-(6-ethynyl-5-fluoro-4-methylpyridin-3-yl)-5-(3-fluoro-4-((4-methylpyrimidin-2-yl)oxy)phenyl)-7-isopropyl-7H-pyrrolo[2,3-d]pyrimidin-4-amine | 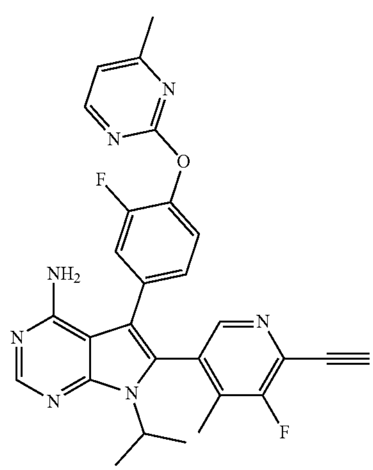 [SMILES: C#Cc1ncc(-c2c(-c3ccc(Oc4nccc(C)n4)c(F)c3)c3c(N)ncnc3n2C(C)C)c(C)c1F] | $^{1}$H NMR (400 MHz, DMSO-d$_{6}$) δ 8.47 (d, J = 5.0 Hz, 1H), 8.42 (s, 1H), 8.22 (s, 1H), 7.31 (t, J = 8.4 Hz, 1H), 7.22-7.14 (m, 2H), 7.02 (ddd, J = 8.4, 2.3, 0.9 Hz, 1H), 6.09 (s, 2H), 4.82 (d, J = 0.7 Hz, 1H), 4.13 (p, J = 6.7 Hz, 1H), 2.39 (s, 3H), 1.99 (d, J = 2.1 Hz, 3H), 1.61 (d, J = 6.8 Hz, 3H), 1.51 (d, J = 6.7 Hz, 3H). | 512.35 |

TABLE 27-continued

Additional Exemplary Compounds

| Compound | Structure | Proton NMR | MS [M + 1] |
|---|---|---|---|
| 6-(6-ethynyl-5-fluoro-4-methylpyridin-3-yl)-5-(3-fluoro-4-((4-methylpyrimidin-2-yl)oxy)phenyl)-7-isopropyl-7H-pyrrolo[2,3-d]pyrimidin-4-amine | Atropisomer 1 | $^1$H NMR (400 MHz, Methanol-$d_4$) δ 8.42 (d, J = 5.1 Hz, 1H), 8.36 (s, 1H), 8.23 (s, 1H), 7.29 (t, J = 8.2 Hz, 1H), 7.19-7.05 (m, 3H), 4.29 (p, J = 6.9 Hz, 1H), 4.19 (d, J = 0.8 Hz, 1H), 2.49 (s, 3H), 2.10 (d, J = 2.2 Hz, 3H), 1.72 (s, 3H), 1.60 (d, J = 6.8 Hz, 3H). | 512.35 |
| 6-(6-ethynyl-5-fluoro-4-methylpyridin-3-yl)-5-(3-fluoro-4-((4-methylpyrimidin-2-yl)oxy)phenyl)-7-isopropyl-7H-pyrrolo[2,3-d]pyrimidin-4-amine | Atropisomer 2 | $^1$H NMR (400 MHz, DMSO-$d_6$) δ 8.48 (d, J = 5.0 Hz, 1H), 8.43 (s, 1H), 8.23 (s, 1H), 7.32 (t, J = 8.4 Hz, 1H), 7.22-7.13 (m, 2H), 7.02 (dd, J = 8.3, 2.1 Hz, 1H), 5.93 (d, J = 130.2 Hz, 1H), 4.82 (s, 1H), 4.14 (p, J = 6.7 Hz, 1H), 2.40 (s, 3H), 2.00 (d, J = 2.1 Hz, 3H), 1.62 (d, J = 6.8 Hz, 3H), 1.51 (d, J = 6.8 Hz, 3H). | 512.40 |
| 6-(6-ethynyl-4,5-dimethylpyridin-3-yl)-5-{3-fluoro-4-[(4-methylpyrimidin-2-yl)oxy]phenyl}-7-methyl-7H-pyrrolo[2,3-d]pyrimidin-4-amine | 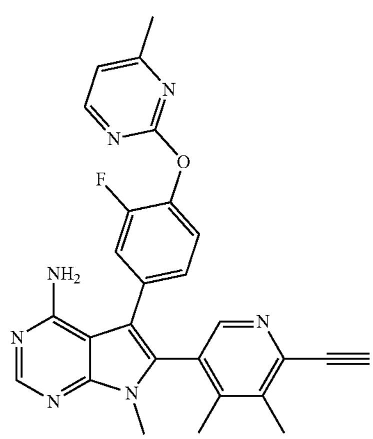 [SMILES: C#Cc1ncc(-c2c(-c3ccc(Oc4nccc(C)n4)c(F)c3)c3c(N)ncnc3n2C)c(C)c1C] | $^1$H NMR (400 MHz, DMSO-$d_6$) δ 8.47 (d, J = 5.0 Hz, 1H), 8.33 (s, 1H), 8.24 (s, 1H), 7.32 (t, J = 8.4 Hz, 1H), 7.21-7.13 (m, 2H), 7.07-6.99 (m, 1H), 6.14 (s, 1H), 4.58 (s, 1H), 3.44 (s, 3H), 2.40 (d, J = 3.2 Hz, 6H), 2.00 (s, 3H). | 480.30 |

TABLE 27-continued

Additional Exemplary Compounds

| Compound | Structure | Proton NMR | MS [M + 1] |
|---|---|---|---|
| 6-(6-ethynyl-5-methoxypyridin-3-yl)-5-(3-fluoro-4-((4-methylpyrimidin-2-yl)oxy)phenyl)-4,7-dimethyl-7H-pyrrolo[2,3-d]pyrimidine | 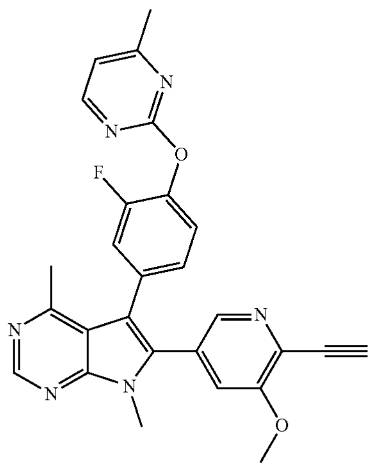 [SMILES: C#Cc1ncc(-c2c(-c3ccc(Oc4nccc(C)n4)c(F)c3)c3c(C)ncnc3n2C)cc1OC] | ¹H NMR (400 MHz, DMSO-d6) δ8.79 (s, 1H), 8.48 (d, J = 5.0 Hz, 1H), 8.18 (d, J = 1.7 Hz, 1H), 7.57 (d, J = 1.7 Hz, 1H), 7.41-7.36 (m, 2H), 7.22-7.14 (m, 2H), 4.56 (s, 1H), 3.80 (s, 6H), 2.41 (d, J = 6.3 Hz, 6H). | 481.20 |
| 6-(2-ethynylquinoxalin-6-yl)-5-(3-fluoro-4-((4-methylpyrimidin-2-yl)oxy)phenyl)-7-methyl-7H-pyrrolo[2,3-d]pyrimidin-4-amine | 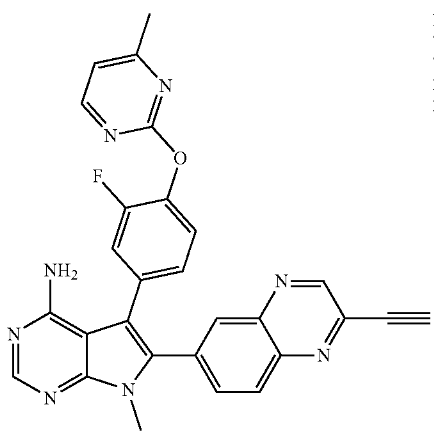 | ¹H NMR (400 MHz, DMSO-d₆) δ9.04 (s, 1H), 8.45 (d, J = 5.0 Hz, 1H), 8.26 (s, 1H), 8.16 (d, J = 1.8 Hz, 1H), 8.08 (d, J = 8.7 Hz, 1H), 7.85 (dd, J = 8.6, 2.0 Hz, 1H), 7.38-7.24 (m, 2H), 7.20-7.11 (m, 2H), 4.90 (s, 1H), 3.71 (s, 3H), 2.38 (s, 3H), 1.15 (s, 1H). | 503.15 |
| 6-(2-ethynylquinazolin-6-yl)-5-(3-fluoro-4-((4-methylpyrimidin-2-yl)oxy)phenyl)-7-methyl-7H-pyrrolo[2,3-d]pyrimidin-4-amine | 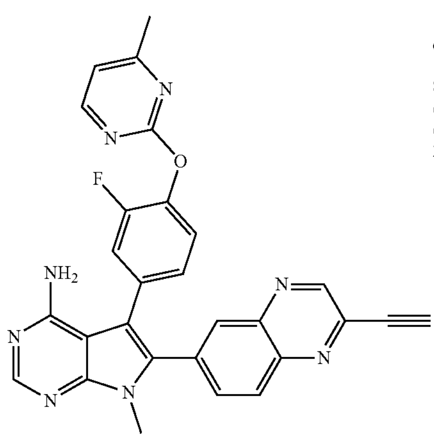 | 1H NMR (400 MHz, DMSO-d6) δ 9.59 (s, 1H), 8.45 (d, J = 5.0 Hz, 1H), 8.26 (d, J = 2.0 Hz, 2H), 8.05-7.91 (m, 2H), 7.35-7.21 (m, 2H), 7.20-7.09 (m, 2H), 6.12 (s, 2H), 4.51 (s, 1H), 3.70 (s, 3H), 2.38 (s, 3H). | 503.15 |

TABLE 27-continued

Additional Exemplary Compounds

| Compound | Structure | Proton NMR | MS [M + 1] |
|---|---|---|---|
| 6-(3-ethynylquinoxalin-6-yl)-5-(3-fluoro-4-((4-methylpyrimidin-2-yl)oxy)phenyl)-7-methyl-7H-pyrrolo[2,3-d]pyrimidin-4-amine | 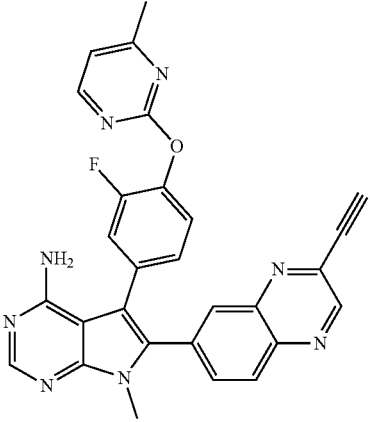 [SMILES: C#Cc1cnc2ccc(-c3c(-c4ccc(Oc5nccc(C)n5)c(F)c4)c4c(N)ncnc4n3C)cc2n1] | 1H NMR (400 MHz, DMSO-d6) δ 9.04 (s, 1H), 8.45 (d, J = 5.0 Hz, 1H), 8.26 (s, 1H), 8.15-8.08 (m, 2H), 7.83 (dd, J = 8.6, 1.9 Hz, 1H), 7.33 (t, J = 8.3 Hz, 1H), 7.28 (dd, J = 11.4, 2.0 Hz, 1H), 7.18-7.12 (m, 2H), 6.10 (s, 2H), 4.88 (s, 1H), 3.71 (s, 3H), 2.38 (s, 3H). | 503.15 |
| 6-(2-ethynylquinazolin-7-yl)-5-(3-fluoro-4-((4-methylpyrimidin-2-yl)oxy)phenyl)-7-methyl-7H-pyrrolo[2,3-d]pyrimidin-4-amine | 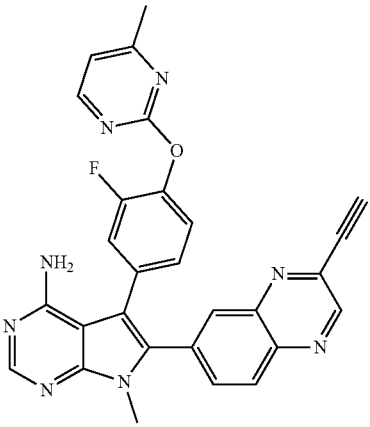 [SMILES: C#Cc1cnc2ccc(-c3c(-c4ccc(Oc5nccc(C)n5)c(F)c4)c4c(N)ncnc4n3C)cc2n1] | ¹H NMR (400 MHz, DMSO-d₆) δ 9.62 (s, 1H), 8.46 (d, J = 5.0 Hz, 1H), 8.26 (s, 1H), 8.20 (d, J = 8.4 Hz, 1H), 8.04 (s, 1H), 7.74 (dd, J = 8.4, 1.7 Hz, 1H), 7.38-7.24 (m, 2H), 7.20-7.10 (m, 2H), 6.12 (s, 1H), 4.49 (s, 1H), 3.71 (s, 3H), 2.38 (s, 3H). | 503.35 |
| 2'-ethynyl-5-(3-fluoro-4-((4-methylpyrimidin-2-yl)oxy)phenyl)-7,7'-dimethyl-7H,7'H-[6,6'-bipyrrolo[2,3-d]pyrimidin]-4-amine | 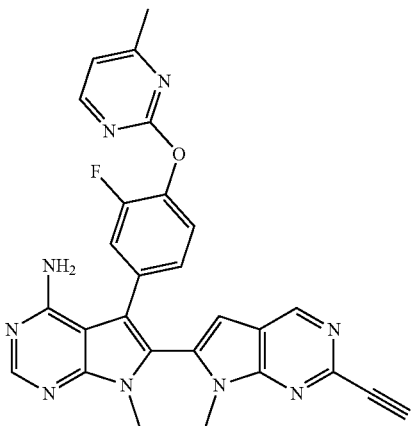 [SMILES: C#Cc1ncc2cc(-c3c(-c4ccc(Oc5nccc(C)n5)c(F)c4)c4c(N)ncnc4n3C)n(C)c2n1] | ¹H NMR (400 MHz, DMSO-d₆) 9.07 (s, 1H), 8.47 (d, J = 5.0 Hz, 1H), 8.29 (s, 1H), 7.34 (t, J = 8.2 Hz, 1H), 7.25 (d, J = 11.2 Hz, 1H), 7.18 (d, J = 5.1 Hz, 1H), 7.10 (d, J = 11.7 Hz, 2H), 4.25 (s, 1H), 3.62 (s, 3H), 3.31 (s, 3H), 2.41 (s, 3H). | 506.20 |

TABLE 27-continued

Additional Exemplary Compounds

| Compound | Structure | Proton NMR | MS [M + 1] |
|---|---|---|---|
| 6-(2-ethynyl-5-methyl-5H-pyrrolo[3,2-d]pyrimidin-6-yl)-5-(3-fluoro-4-((4-methylpyrimidin-2-yl)oxy)phenyl)-7-methyl-7H-pyrrolo[2,3-d]pyrimidin-4-amine | 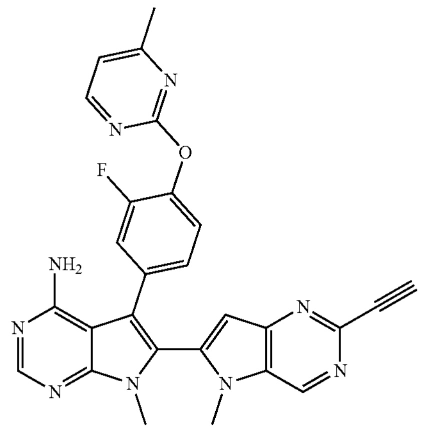 [SMILES: C#Cc1ncc2c(cc(-c3c(-c4ccc(Oc5nccc(C)n5)c(F)c4)c4c(N)ncnc4n3C)n2C)n1] | $^1$H NMR (400 MHz, DMSO-d$_6$) δ 9.07 (s, 1H), 8.47 (d, J = 5.0 Hz, 1H), 8.30 (s, 1H), 7.34 (t, J = 8.4 Hz, 1H), 7.26 (dd, J = 11.3, 2.1 Hz, 1H), 7.18 (d, J = 5.0 Hz, 1H), 7.11 (dd, J = 7.9, 1.9 Hz, 1H), 7.07 (s, 1H), 4.11 (s, 1H), 3.63 (s, 3H), 3.46 (s, 3H), 2.40 (s, 3H). | 506.25 |
| 6-(2-ethynyl-1H-benzo[d]imidazol-5-yl)-5-(3-fluoro-4-((4-methylpyrimidin-2-yl)oxy)phenyl)-4,7-dimethyl-7H-pyrrolo[2,3-d]pyrimidine | 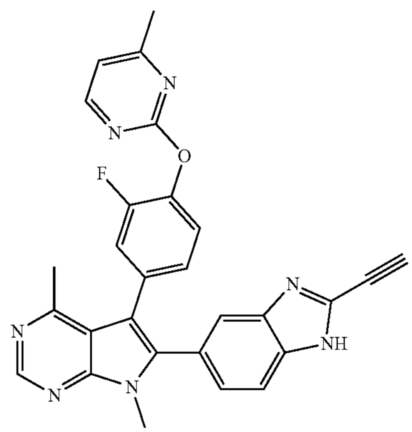 [SMILES: C#Cc1nc2cc(-c3c(-c4ccc(Oc5nccc(C)n5)c(F)c4)c4c(C)ncnc4n3C)ccc2[nH]1] | $^1$H NMR (400 MHz, DMSO-d$_6$) δ13.36 (d, J = 16.4 Hz, 1H), 8.75 (s, 1H), 8.46 (d, J = 5.0 Hz, 1H), 7.77-7.67 (m, 1H), 7.53 (d, J = 9.6 Hz, 1H), 7.38-7.23 (m, 3H), 7.17 (d, J = 5.0 Hz, 2H), 4.72 (s, 1H), 3.69 (d, J = 3.6 Hz, 3H), 2.38 (q, J = 2.0 Hz, 6H). | 490.30 |
| 6-(6-ethynyl-5-methoxy-4-methylpyridin-3-yl)-5-(3-fluoro-4-((4-methylpyrimidin-2-yl)oxy)phenyl)-4,7-dimethyl-7H-pyrrolo[2,3-d]pyrimidine | 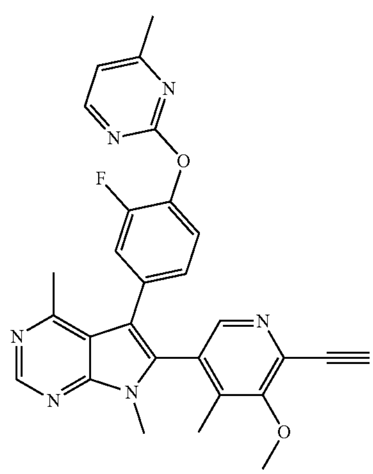 [SMILES: C#Cc1ncc(-c2c(-c3ccc(Oc4nccc(C)n4)c(F)c3)c3c(C)ncnc3n2C)c(C)c1OC] | $^1$H NMR (400 MHz, DMSO-d$_6$) 8.79 (s, 1H), 8.47 (d, J = 5.0 Hz, 1H), 8.35 (s, 1H), 7.38-7.27 (m, 2H), 7.18 (d, J = 5.0 Hz, 1H), 7.11 (dd, J = 8.4, 2.0 Hz, 1H), 4.64 (s, 1H), 3.85 (s, 3H), 3.60 (s, 3H), 2.44 (s, 3H), 2.40 (s, 3H), 1.97 (s, 3H). | 495.20 |

TABLE 27-continued

Additional Exemplary Compounds

| Compound | Structure | Proton NMR | MS [M + 1] |
|---|---|---|---|
| 6-(6-ethynyl-4-methoxypyridin-3-yl)-5-(3-fluoro-4-((4-methylpyrimidin-2-yl)oxy)phenyl)-4,7-dimethyl-7H-pyrrolo[2,3-d]pyrimidine | 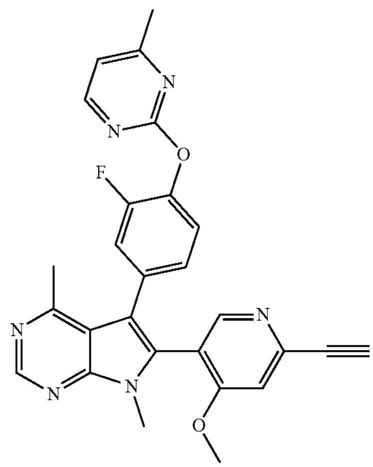 | $^1$H NMR (400 MHz, DMSO-d$_6$) δ 8.77 (s, 1H), 8.49 (d, J = 5.0 Hz, 1H), 8.29 (s, 1H), 7.42 (s, 1H), 7.36-7.27 (m, 2H), 7.19 (d, J = 5.0 Hz, 1H), 7.14-7.07 (m, 1H), 4.48 (s, 1H), 3.87 (s, 3H), 3.61 (s, 3H), 2.41 (s, 6H). | 481.15 |
| 6-(2-ethynylquinolin-6-yl)-5-(3-fluoro-4-((4-methylpyrimidin-2-yl)oxy)phenyl)-7-methyl-7H-pyrrolo[2,3-d]pyrimidin-4-amine | 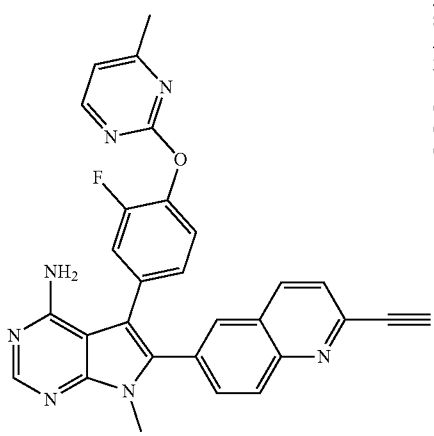 | $^1$H NMR (400 MHz, DMSO-d$_6$) δ 8.45 (d, J = 5.0 Hz, 1H), 8.40 (d, J = 8.5 Hz, 1H), 8.26 (s, 1H), 8.09 (d, J = 2.0 Hz, 1H), 8.00 (d, J = 8.7 Hz, 1H), 7.74 (dd, J = 8.8, 2.0 Hz, 1H), 7.69 (d, J = 8.4 Hz, 1H), 7.32 (t, J = 8.3 Hz, 1H), 7.24 (dd, J = 11.3, 2.0 Hz, 1H), 7.17 (d, J = 5.1 Hz, 1H), 7.15-7.09 (m, 1H), 6.08 (s, 1H), 4.56 (s, 1H), 3.69 (s, 3H), 2.39 (s, 3H). | 502.20 |
| 6-(2-ethynylquinolin-7-yl)-5-(3-fluoro-4-(4-methylpyrimidin-2-yl)oxy)phenyl)-7-methyl-7H-pyrrolo[2,3-d]pyrimidin-4-amine | 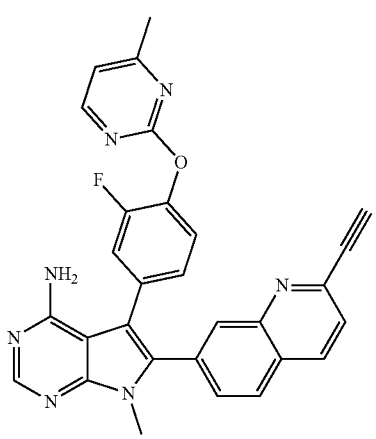 [SMILES: C#Cc1ccc2ccc(-c3c(-c4ccc(Oc5nccc(C)n5)c(F)c4)c4c(N)ncnc4n3C)cc2n1] | $^1$H NMR (400 MHz, DMSO-d6) 8.48-8.41 (m, 2H), 8.26 (s, 1H), 8.04 (dd, J = 5.1, 3.3 Hz, 2H), 7.69 (d, J = 8.4 Hz, 1H), 7.60 (dd, J = 8.5, 1.6 Hz, 1H), 7.33 (t, J = 8.4 Hz, 1H), 7.26 (dd, J = 11.3, 2.0 Hz, 1H), 7.19-7.11 (m, 2H), 6.08 (s, 1H), 4.54 (s, 1H), 3.69 (s, 3H), 2.38 (s, 3H). | 502.20 |

TABLE 27-continued

Additional Exemplary Compounds

| Compound | Structure | Proton NMR | MS [M + 1] |
|---|---|---|---|
| 6-(3-ethynylisoquinolin-7-yl)-5-(3-fluoro-4-((4-methylpyrimidin-2-yl)oxy)phenyl)-7-methyl-7H-pyrrolo[2,3-d]pyrimidin-4-amine | 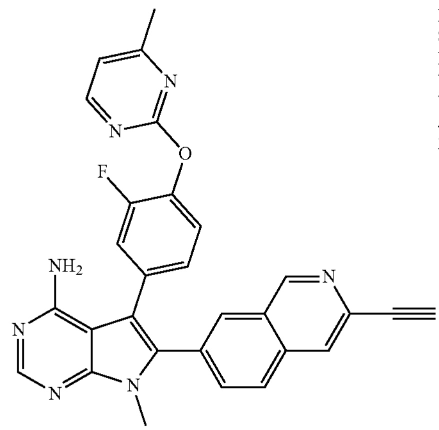 | 1H NMR (400 MHz, DMSO-d6) δ 9.28 (s, 1H), 8.45 (d, J = 5.0 Hz, 1H), 8.26 (s, 1H), 8.22 (d, J = 1.7 Hz, 1H), 8.14 (s, 1H), 8.01 (d, J = 8.5 Hz, 1H), 7.76 (dd, J = 8.5, 1.7 Hz, 1H), 7.32 (t, J = 8.4 Hz, 1H), 7.24 (dd, J = 11.4, 2.1 Hz, 1H), 7.18 (d, J = 5.1 Hz, 1H), 7.12 (dd, J = 8.4, 2.0 Hz, 1H), 4.39 (s, 1H), 3.69 (s, 3H), 2.39 (s, 3H) | 502.35 |
| 6-(3-ethynylisoquinolin-6-yl)-5-(3-fluoro-4-((4-methylpyrimidin-2-yl)oxy)phenyl)-7-methyl-7H-pyrrolo[2,3-d]pyrimidin-4-amine | 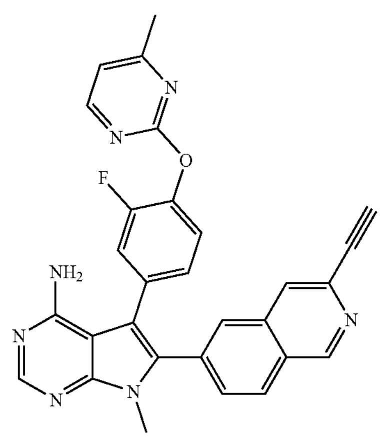 [SMILES: C#Cc1cc2cc(-c3c(-c4ccc(Oc5nccc(C)n5)c(F)c4)c4c(N)ncnc4n3C)ccc2cn1] | 1H NMR (400 MHz, DMSO-d6) δ 9.33 (s, 1H), 8.46 (d, J = 5.0 Hz, 1H), 8.26 (s, 1H), 8.19 (d, J = 8.4 Hz, 1H), 8.05 (d, J = 15.7 Hz, 2H), 7.69 (dd, J = 8.7, 1.5 Hz, 1H), 7.32 (t, J = 8.3 Hz, 1H), 7.24 (d, J = 11.0 Hz, 1H), 7.17 (d, J = 5.1 Hz, 1H), 7.14-7.08 (m, 1H), 6.2-5.4 (s, 1H), 4.37 (s, 1H), 3.69 (s, 3H), 2.39 (s, 3H). | 502.25 |
| 2-ethynyl-6-(5-(3-fluoro-4-((4-methylpyrimidin-2-yl)oxy)phenyl)-4,7-dimethyl-7H-pyrrolo[2,3-d]pyrimidin-6-yl)quinoxaline | 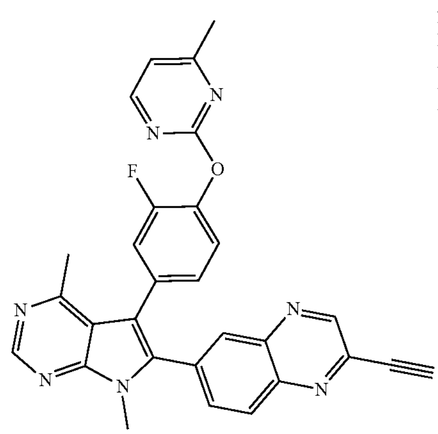 | $^1$H NMR (400 MHz, DMSO-d$_6$) δ 9.06 (s, 1H), 8.81 (s, 1H), 8.46 (d, J = 5.0 Hz, 1H), 8.24 (d, J = 1.9 Hz, 1H), 8.13 (d, J = 8.7 Hz, 1H), 7.92 (dd, J = 8.7, 2.0 Hz, 1H), 7.43 (dd, J = 11.3, 2.0 Hz, 1H), 7.31 (t, J = 8.3 Hz, 1H), 7.24-7.14 (m, 2H), 4.91 (s, 1H), 3.81 (s, 3H), 2.42 (s, 3H), 2.38 (s, 3H). | 502.35 |

TABLE 27-continued

Additional Exemplary Compounds

| Compound | Structure | Proton NMR | MS [M + 1] |
|---|---|---|---|
| 6-(3-ethynylquinolin-7-yl)-5-(3-fluoro-4-((4-methylpyrimidin-2-yl)oxy)phenyl)-7-methyl-7H-pyrrolo[2,3-d]pyrimidin-4-amine | 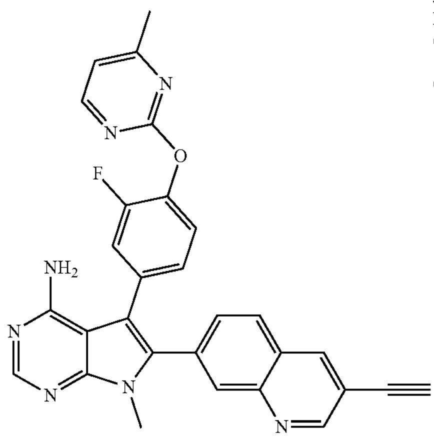 | ¹H NMR (400 MHz, DMSO-d₆) 8.93 (d, J = 2.1 Hz, 1H), 8.61 (d, J = 2.1 Hz, 1H), 8.45 (d, J = 5.0 Hz, 1H), 8.26 (s, 1H), 8.09-8.00 (m, 2H), 7.63 (dd, J = 8.5, 1.7 Hz, 1H), 7.36-7.24 (m, 2H), 7.21-7.11 (m, 2H), 6.07 (s, 2H), 4.58 (s, 1H), 3.69 (s, 3H), 2.38 (s, 3H). | 502.20 |
| 6-(7-ethynyl-1,8-naphthyridin-3-yl)-5-(3-fluoro-4-((4-methylpyrimidin-2-yl)oxy)phenyl)-7-methyl-7H-pyrrolo[2,3-d]pyrimidin-4-amine | 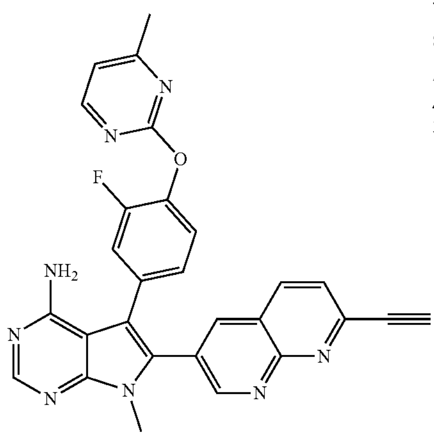 | ¹H NMR (400 MHz, DMSO-d6) 8.96 (d, J = 2.5 Hz, 1H), 8.66 (d, J = 2.5 Hz, 1H), 8.53 (d, J = 8.4 Hz, 1H), 8.47 (d, J = 5.1 Hz, 1H), 8.30 (s, 1H), 7.83 (d, J = 8.2 Hz, 1H), 7.39-7.27 (m, 2H), 7.21-7.11 (m, 2H), 6.00-6.72 (s, 1H), 4.70 (s, 1H), 3.75 (s, 3H), 2.40 (s, 3H). | 503.25 |
| 6-(6-(ethynyl-d)-4-methylpyridin-3-yl)-5-(3-fluoro-4-((4-methylpyrimidin-2-yl)oxy)phenyl)-7-methyl-7H-pyrrolo[2,3-d]pyrimidin-4-amine | 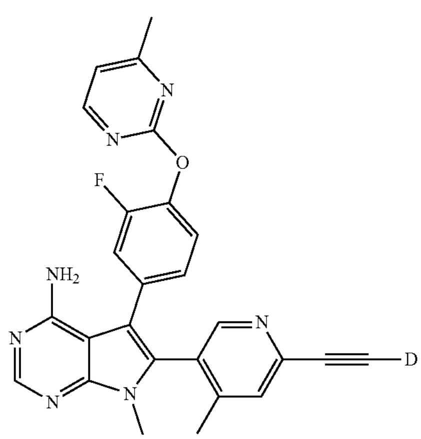 [SMILES: [2H]C#Cc1cc(C)c(-c2c(-c3ccc(Oc4nccc(C)n4)c(F)c3)c3c(N)ncnc3n2C)cn1] | ¹H NMR (400 MHz, DMSO-d₆) δ 8.51 (s, 1H), 8.47 (d, J = 5.0 Hz, 1H), 8.24 (s, 1H), 7.58 (d, J = 0.8 Hz, 1H), 7.33 (t, J = 8.4 Hz, 1H), 7.22-7.12 (m, 2H), 7.07-7.01 (m, 1H), 6.14 (s, 1H), 3.47 (s, 3H), 2.41 (s, 3H), 2.02 (s, 3H). | 467.20 |

TABLE 27-continued

Additional Exemplary Compounds

| Compound | Structure | Proton NMR | MS [M + 1] |
| --- | --- | --- | --- |
| 6-(2-ethynyl-7-methylquinoxalin-6-yl)-5-(3-fluoro-4-((4-methylpyrimidin-2-yl)oxy)phenyl)-7-methyl-7H-pyrrolo[2,3-d]pyrimidin-4-amine | 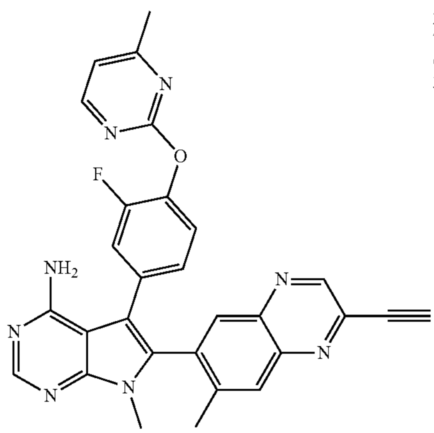 | $^1$H NMR (400 MHz, DMSO-d$_6$) δ 9.00 (s, 1H), 8.42 (d, J = 5.0 Hz, 1H), 8.26 (s, 1H), 7.30-7.20 (m, 2H), 7.15 (d, J = 5.1 Hz, 1H), 7.10 (dd, J = 8.4, 2.0 Hz, 1H), 6.12 (s, 1H), 4.88 (s, 1H), 3.48 (s, 3H), 2.35 (s, 3H), 2.23 (s, 3H). | 517.20 |
| 4-(difluoromethyl)-6-(6-ethynyl-4-methylpyridin-3-yl)-5-(3-fluoro-4-((4-methylpyrimidin-2-yl)oxy)phenyl)-7-methyl-7H-pyrrolo[2,3-d]pyrimidine | 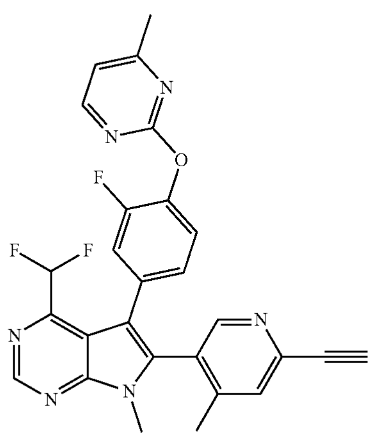 [SMILES: C#Cc1cc(C)c(-c2c(-c3ccc(Oc4nccc(C)n4)c(F)c3)c3c(C(F)F)ncnc3n2C)cn1] | 1H NMR (400 MHz, DMSO-d6) 9.06 (s, 1H), 8.49 (d, J = 5.0 Hz, 1H), 8.44 (s, 1H), 7.56 (dd, J = 11.2, 2.0 Hz, 1H), 7.50-7.41 (m, 2H), 7.28 (ddd, J = 8.3, 2.1, 0.9 Hz, 1H), 7.21 (d, J = 5.1 Hz, 1H), 6.73 (s, 1H), 4.34 (s, 1H), 3.84 (s, 3H), 2.42 (s, 3H), 1.96 (s, 3H). | 501.15 |
| 6-(6-ethynyl-4-methoxypyridin-3-yl)-5-(3-fluoro-4-((4-methylpyrimidin-2-yl)oxy)phenyl)-7-methyl-7H-pyrrolo[2,3-d]pyrimidin-4-amine | 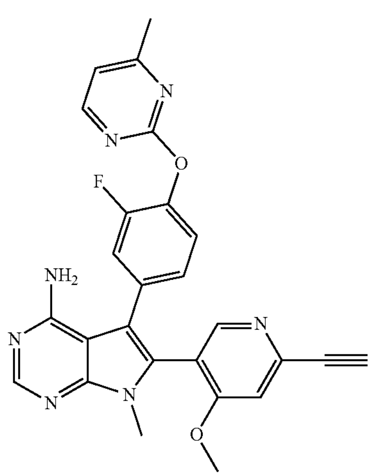 [SMILES: C#Cc1cc(OC)c(-c2c(-c3ccc(Oc4nccc(C)n4)c(F)c3)c3c(N)ncnc3n2C)cn1] | 1H NMR (400 MHz, DMSO-d6) δ 8.48 (d, J = 5.0 Hz, 1H), 8.22 (d, J = 1.6 Hz, 2H), 7.39 (s, 1H), 7.33 (t, J = 8.4 Hz, 1H), 7.22-7.12 (m, 2H), 7.03 (d, J = 7.9 Hz, 1H), 6.07 (s, 2H), 4.45 (s, 1H), 3.85 (s, 3H), 3.51 (s, 3H), 2.42 (s, 3H). | 482.15 |

Example 29

6-(4-aminophenyl)-7-methyl-5-(4-((4-methylpyrimidin-2-yl)oxy)phenyl)-7H-pyrrolo[2,3-d]pyrimidin-4-amine

Scheme 26

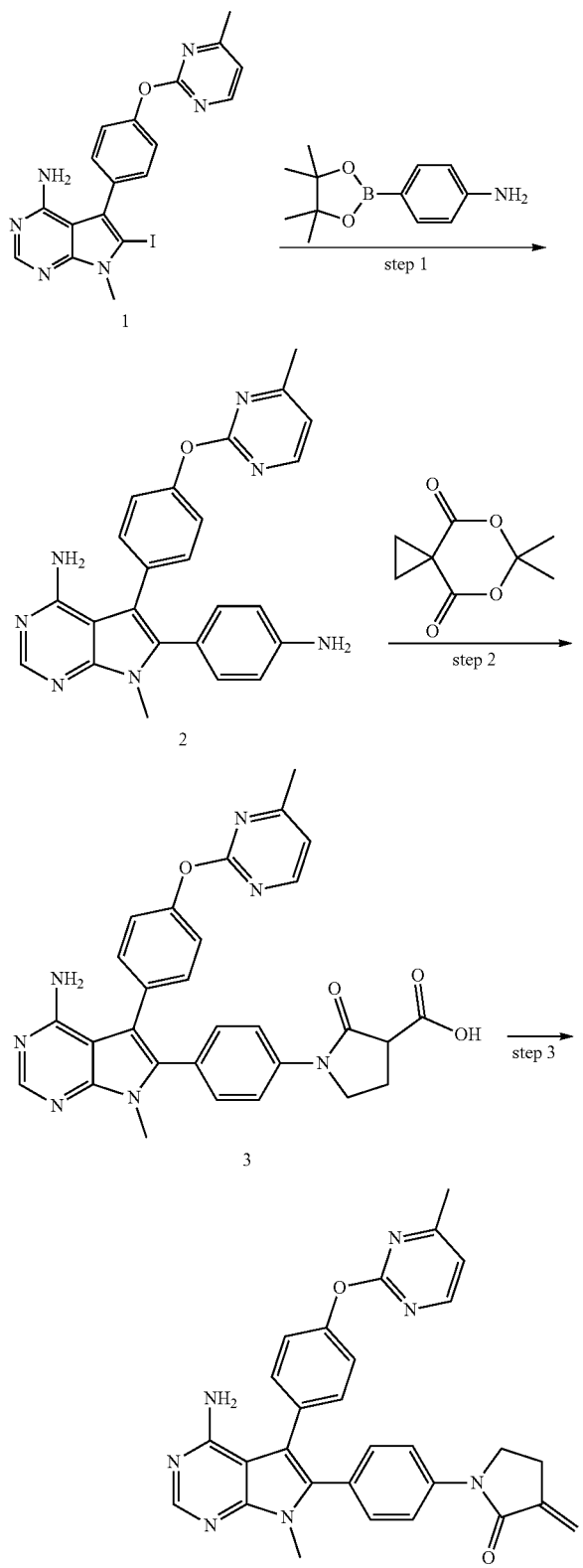

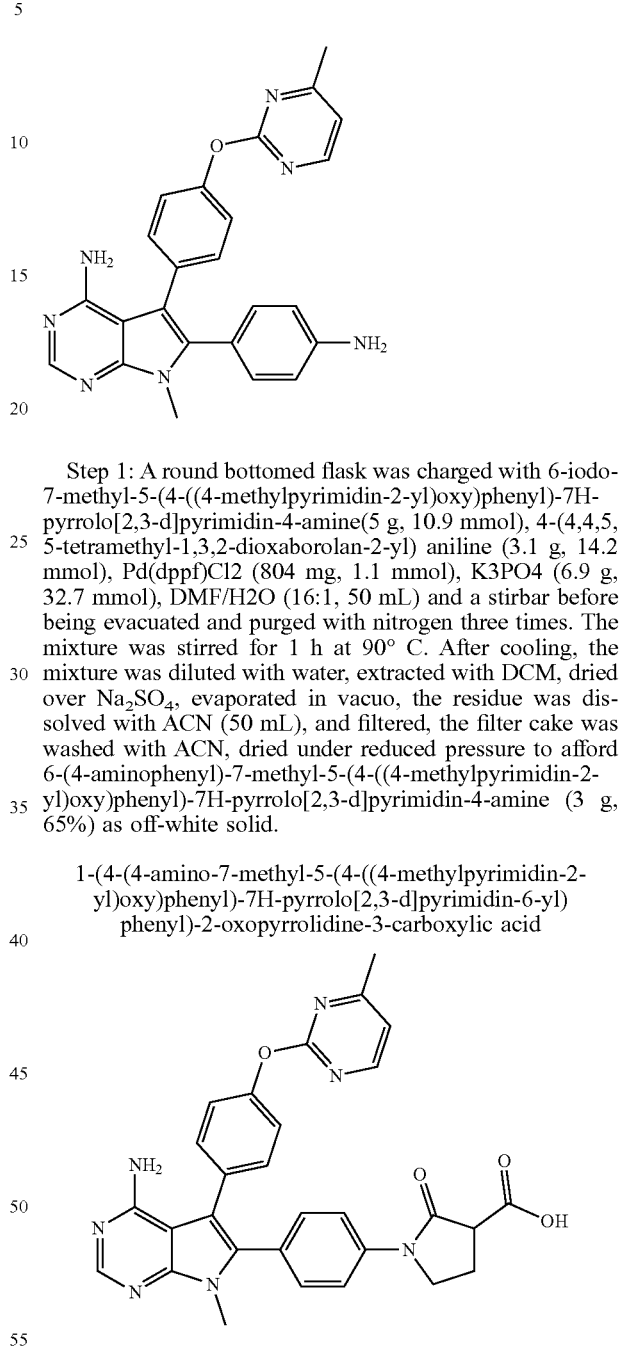

Step 1: A round bottomed flask was charged with 6-iodo-7-methyl-5-(4-((4-methylpyrimidin-2-yl)oxy)phenyl)-7H-pyrrolo[2,3-d]pyrimidin-4-amine(5 g, 10.9 mmol), 4-(4,4,5,5-tetramethyl-1,3,2-dioxaborolan-2-yl) aniline (3.1 g, 14.2 mmol), Pd(dppf)Cl2 (804 mg, 1.1 mmol), K3PO4 (6.9 g, 32.7 mmol), DMF/H2O (16:1, 50 mL) and a stirbar before being evacuated and purged with nitrogen three times. The mixture was stirred for 1 h at 90° C. After cooling, the mixture was diluted with water, extracted with DCM, dried over Na$_2$SO$_4$, evaporated in vacuo, the residue was dissolved with ACN (50 mL), and filtered, the filter cake was washed with ACN, dried under reduced pressure to afford 6-(4-aminophenyl)-7-methyl-5-(4-((4-methylpyrimidin-2-yl)oxy)phenyl)-7H-pyrrolo[2,3-d]pyrimidin-4-amine (3 g, 65%) as off-white solid.

1-(4-(4-amino-7-methyl-5-(4-((4-methylpyrimidin-2-yl)oxy)phenyl)-7H-pyrrolo[2,3-d]pyrimidin-6-yl)phenyl)-2-oxopyrrolidine-3-carboxylic acid Step 2: A round bottomed flask was charged with 6-(4-aminophenyl)-7-methyl-5-(4-((4-methylpyrimidin-2-yl)oxy)phenyl)-7H-pyrrolo[2,3-d]pyrimidin-4-amine (3 g, 7 mmol), 6,6-dimethyl-5,7-dioxaspiro[2.5]octane-4,8-dione (2.38 g, 14 mmol), EtOH (50 mL) and a stirbar. The mixture was stirred O/N at 90° C. The solvent was evaporated in vacuo, the residue was washed with EA (50 mL), and filtered, the filter cake was washed with ACN, dried under reduced pressure to afford 1-(4-(4-amino-7-methyl-5-(4-((4-methylpyrimidin-2-yl)oxy)phenyl)-7H-pyrrolo[2,3-d]pyrimidin-6-yl)phenyl)-2-oxopyrrolidine-3-carboxylic acid (2 g, 53%) as off-white solid.

1-(4-(4-amino-7-methyl-5-(4-((4-methylpyrimidin-2-yl)oxy)phenyl)-7H-pyrrolo[2,3-d]pyrimidin-6-yl)phenyl)-3-methylenepyrrolidin-2-one

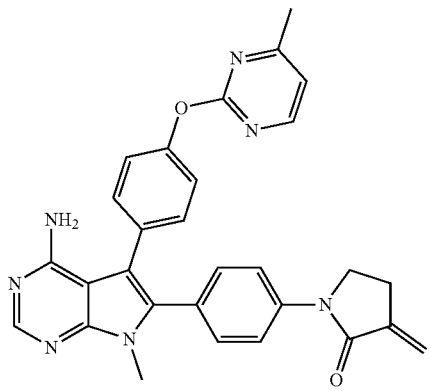 [SMILES: C=C1CCN(c2ccc(-c3c(-c4ccc(Oc5nccc(C)n5)cc4)c4c(N)ncnc4n3C)cc2)C1=O]

Step 3: A round bottomed flask was charged with 1-(4-(4-amino-7-methyl-5-(4-((4-methylpyrimidin-2-yl)oxy)phenyl)-7H-pyrrolo[2,3-d]pyrimidin-6-yl)phenyl)-2-oxopyrrolidine-3-carboxylic acid (2 g, 3.73 mmol), HCHO aq (0.46 g, 5.6 mmol), diethylamine(0.54 g, 7.46 mmol) and DMF (30 mL) a stirbar. The mixture was stirred for 2 h at 90° C. After cooling, the mixture was diluted with water, extracted with DCM, dried over $Na_2SO_4$, evaporated in vacuo, the residue was purified by silica gel column chromatography, eluted with DCM/MeOH (50:1~10:1). The crude product was purified by prep-HPLC to afford 1-(4-(4-amino-7-methyl-5-(4-((4-methylpyrimidin-2-yl)oxy)phenyl)-7H-pyrrolo[2,3-d]pyrimidin-6-yl)phenyl)-3-methylenepyrrolidin-2-one (150 mg,) as an off-white solid.

Additional compounds prepared according to the methods of Example 29 are depicted in Table 28 below.

TABLE 28

Additional Exemplary Compounds

| Compound | Structure | Proton NMR | MS [M + 1] |
|---|---|---|---|
| 1-(4-(4-amino-7-methyl-5-(4-((4-methylpyrimidin-2-yl)oxy)phenyl)-7H-pyrrolo[2,3-d]pyrimidin-6-yl)phenyl)-3-methylenepyrrolidin-2-one | 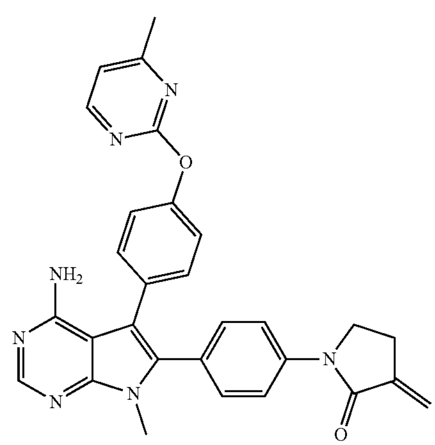 [SMILES: C=C1CCN(c2ccc(-c3c(-c4ccc(Oc5nccc(C)n5)cc4)c4c(N)ncnc4n3C)cc2)C1=O] | $^1$H NMR (400 MHz, Methanol-$d_4$) δ 8.41 (d, J = 5.1 Hz, 1H), 8.22 (s, 1H), 7.84 (t, J = 8.0 Hz, 2H), 7.44-7.34 (m, 4H), 7.20-7.11 (m, 3H), 6.06 (s, 1H), 5.53 (d, J = 2.7 Hz, 1H), 4.45 (d, J = 2.8 Hz, 1H), 3.97 (t, J = 6.9 Hz, 1H), 3.72 (s, 3H), 2.97 (s, 1H), 2.50 (s, 3H), 1.94 (d, J = 2.1 Hz, 1H), 1.32 (t, J = 7.3 Hz, 1H). | 504.20 |
| (R)-1-(3-chloro-4-(4,7-dimethyl-5-(4-(pyrrolidine-1-carbonyl)cyclohex-1-en-1-yl)-7H-pyrrolo[2,3-d]pyrimidin-6-yl)phenyl)-3-methylenepyrrolidin-2-one | 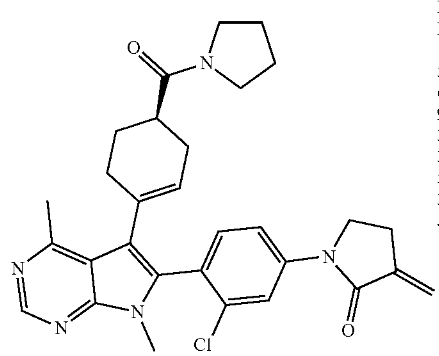 | 1H NMR (400 MHz, DMSO-d6) δ 8.68 (s, 1H), 8.23 (dd, J = 4.9, 2.2 Hz, 1H), 7.86 (ddd, J = 8.6, 2.3, 1.4 Hz, 1H), 7.54 (dd, J = 9.6, 8.5 Hz, 1H), 5.98 (td, J = 2.8, 1.0 Hz, 1H), 5.69 (dd, J = 9.5, 4.3 Hz, 1H), 5.55 (dt, J = 3.0, 1.5 Hz, 1H), 3.96 (qt, J = 9.7, 4.9 Hz, 2H), 3.50 (d, J = 6.3 Hz, 3H), 3.43 (td, J = 6.7, 5.1 Hz, 2H), 3.26 (t, J = 6.8 Hz, 2H), 2.91 (tt, J = 5.9, 2.6 Hz, 2H), 2.67 (d, J = 1.5 Hz, 3H), 2.36-1.69 (m, 10H), 1.48 (ddt, J = 29.8, 12.3, 6.6 Hz, 1H). | 530.25 |

TABLE 28-continued

Additional Exemplary Compounds

| Compound | Structure | Proton NMR | MS [M + 1] |
|---|---|---|---|
| (S)-1-(3-chloro-4-(4,7-dimethyl-5-(4-(pyrrolidine-1-carbonyl)cyclohex-1-en-1-yl)-7H-pyrrolo[2,3-d]pyrimidin-6-yl)phenyl)-3-methylenepyrrolidin-2-one | 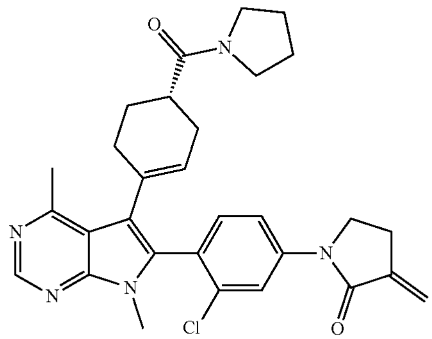 [SMILES: C=C1CCN(c2ccc(-c3c(C4=CC[C@@H](C(=O)N5CCCC5)CC4)c4c(C)ncnc4n3C)c(Cl)c2)C1=O] | 1H NMR (400 MHz, DMSO-d6) δ 8.68 (s, 1H), 8.23 (dd, J = 4.9, 2.2 Hz, 1H), 7.86 (ddd, J = 8.5, 2.3, 1.4 Hz, 1H), 7.54 (dd, J = 9.6, 8.5 Hz, 1H), 5.98 (td, J = 2.8, 1.0 Hz, 1H), 5.69 (dd, J = 10.6, 4.1 Hz, 1H), 5.55 (td, J = 2.6, 1.0 Hz, 1H), 3.96 (qt, J = 9.7, 4.9 Hz, 2H), 3.50 (d, J = 6.3 Hz, 3H), 3.47-3.39 (m, 2H), 3.26 (t, J = 6.9 Hz, 2H), 2.96-2.86 (m, 2H), 2.67 (d, J = 1.6 Hz, 3H), 2.29-1.69 (m, 10H), 1.46 (dtt, J = 29.5, 12.2, 6.7 Hz, 1H). | 530.25 |
| 1-(4-(4-amino-7-methyl-5-(4-((4-methylpyrimidin-2-yl)oxy)phenyl)-7H-pyrrolo[2,3-d]pyrimidin-6-yl)-3-methylphenyl)-3-methylenepyrrolidin-2-one | 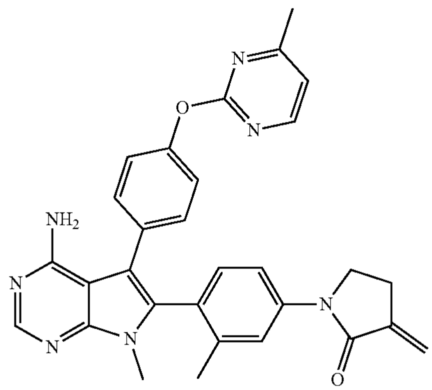 [SMILES: C=C1CCN(c2ccc(-c3c(-c4ccc(Oc5nccc(C)n5)cc4)c4c(N)ncnc4n3C)c(C)c2)C1=O] | $^1$H NMR (400 MHz, DMSO-d$_6$) δ 8.46 (s, 1H), 8.22 (s, 1H), 7.76-7.72 (m, 2H), 7.40 (d, J = 8.4 Hz, 1H), 7.26 (t, J = 8.4 Hz, 2H), 7.16-7.13 (m, 3H), 5.92 (s, 1H), 5.77 (s, 1H), 3.90 (t, J = 13.6 Hz, 2H), 3.43 (s, 3H), 2.87 (t, J = 13.6 Hz, 2H), 2.40 (s, 3H), 2.01 (s, 3H). | 518.20 |
| 1-(4-(5-(3-fluoro-4-((4-methylpyrimidin-2-yl)oxy)phenyl)-4,7-dimethyl-7H-pyrrolo[2,3-d]pyrimidin-6-yl)-3-methylphenyl)-3-methylenepyrrolidin-2-one | 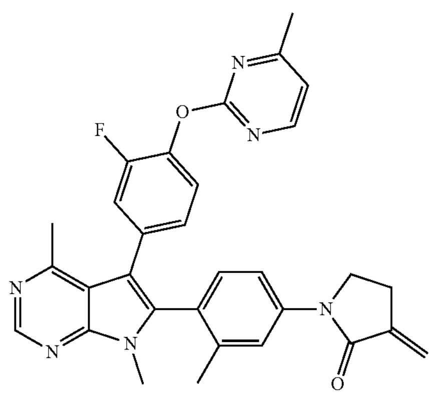 [SMILES: C=C1CCN(c2ccc(-c3c(-c4ccc(Oc5nccc(C)n5)c(F)c4)c4c(C)ncnc4n3C)c(C)c2)C1=O] | 1H NMR: 1H NMR (400 MHz, DMSO-d6) 8.75 (s, 1H), 8.47 (d, J = 5.0 Hz, 1H), 7.82-7.73 (m, 2H), 7.45 (d, J = 8.4 Hz, 1H), 7.35-7.25 (m, 2H), 7.20-7.11 (m, 2H), 5.96-5.90 (m, 1H), 5.52-5.47 (m, 1H), 3.90 (t, J = 6.8 Hz, 2H), 3.52 (s, 3H), 2.88 (d, J = 14.1 Hz, 0H), 2.88 (s, 2H), 2.41 (d, J = 6.4 Hz, 6H), 2.05 (s, 3H). | 535.40 |
| 1-(4-(4-amino-5-(3-fluoro-4-((4-methylpyrimidin-2-yl)oxy)phenyl)-7-methyl-7H-pyrrolo[2,3-d]pyrimidin-6-yl)phenyl)-3-methylenepyrrolidin-2-one | 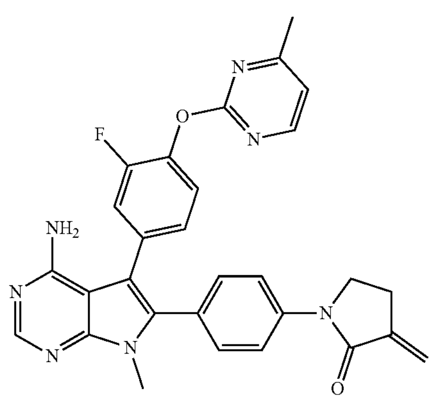 [SMILES: C=C1CCN(c2ccc(-c3c(-c4ccc(Oc5nccc(C)n5)c(F)c4)c4c(N)ncnc4n3C)cc2)C1=O] | $^1$H NMR (400 MHz, DMSO-d$_6$) δ 8.47 (d, J = 5.0 Hz, 1H), 8.22 (s, 1H), 7.89-7.84 (m, 2H), 7.48-7.40 (m, 2H), 7.35 (t, J = 8.4 Hz, 1H), 7.24-7.07 (m, 3H), 5.93 (dt, J = 2.8, 1.7 Hz, 1H), 5.49 (dt, J = 3.0, 1.5 Hz, 1H), 3.90 (t, J = 6.9 Hz, 2H), 3.61 (s, 3H), 2.88 (dt, J = 7.1, 3.6 Hz, 2H), 2.42 (s, 3H). | 522.20 |

TABLE 28-continued

Additional Exemplary Compounds

| Compound | Structure | Proton NMR | MS [M + 1] |
|---|---|---|---|
| (R)-1-(4-(4-amino-7-methyl-5-(4-(pyrrolidine-1-carbonyl)cyclohex-1-en-1-yl)-7H-pyrrolo[2,3-d]pyrimidin-6-yl)phenyl)-3-methylenepyrrolidin-2-one | 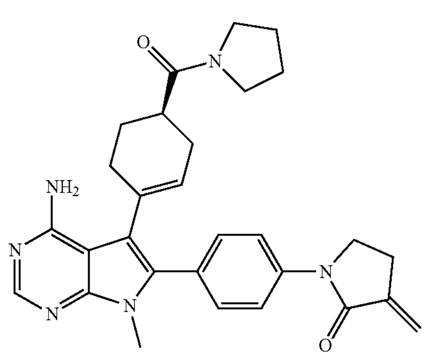 [SMILES: C=C1CCN(c2ccc(-c3c(C4=CC[C@H](C(=O)N5CCCC5)CC4)c4c(N)ncnc4n3C)cc2)C1=O] | $^1$H NMR (400 MHz, DMSO-d$_6$) δ 8.13 (d, J = 16.6 Hz, 1H), 7.98-7.91 (m, 2H), 7.60-7.50 (m, 2H), 6.55 (s, 1H), 5.94 (q, J = 2.4 Hz, 1H), 5.78 (d, J = 3.7 Hz, 1H), 5.50 (q, J = 1.9 Hz, 1H), 3.94 (t, J = 6.9 Hz, 2H), 3.59 (s, 3H), 3.51 (dt, J = 10.1, 6.7 Hz, 1H), 3.48-3.40 (m, 1H), 3.32-3.26 (m, 1H), 3.25 (d, J = 5.6 Hz, 1H), 2.91 (d, J = 6.8 Hz, 2H), 2.84 (t, J = 5.8 Hz, 1H), 2.36-2.17 (m, 2H), 1.88 (dd, J = 13.4, 6.7 Hz, 4H), 1.76 (p, J = 6.8 Hz, 2H), 1.64 (d, J = 6.0 Hz, 2H). | 497.20 |
| (S)-1-(4-(4-amino-7-methyl-5-(4-(pyrrolidine-1-carbonyl)cyclohex-1-en-1-yl)-7H-pyrrolo[2,3-d]pyrimidin-6-yl)phenyl)-3-methylenepyrrolidin-2-one | 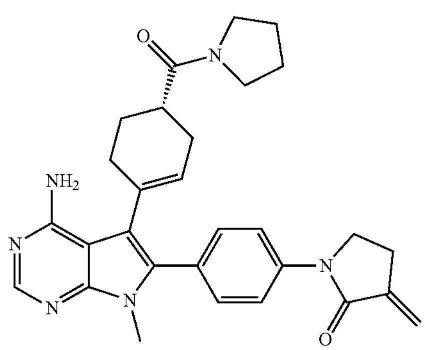 [SMILES: C=C1CCN(c2ccc(-c3c(C4=CC[C@@H](C(=O)N5CCCC5)CC4)c4c(N)ncnc4n3C)cc2)C1=O] | $^1$H NMR (400 MHz, DMSO-d$_6$) δ 8.16 (d, J = 14.7 Hz, 1H), 7.98-7.87 (m, 2H), 7.61-7.53 (m, 2H), 7.05 (d, J = 26.7 Hz, 1H), 5.94 (td, J = 2.8, 1.1 Hz, 1H), 5.86-5.73 (m, 1H), 5.51 (td, J = 2.5, 1.0 Hz, 1H), 3.94 (t, J = 6.9 Hz, 2H), 3.62 (s, 3H), 3.52 (dt, J = 10.1, 6.6 Hz, 1H), 3.43 (dt, J = 10.0, 6.8 Hz, 1H), 3.30 (d, J = 7.0 Hz, 1H), 3.28-3.21 (m, 1H), 2.95-2.80 (m, 3H), 2.38-2.15 (m, 2H), 1.88 (h, J = 6.5, 5.6 Hz, 4H), 1.81-1.55 (m, 4H). | 497.15 |

Example 30

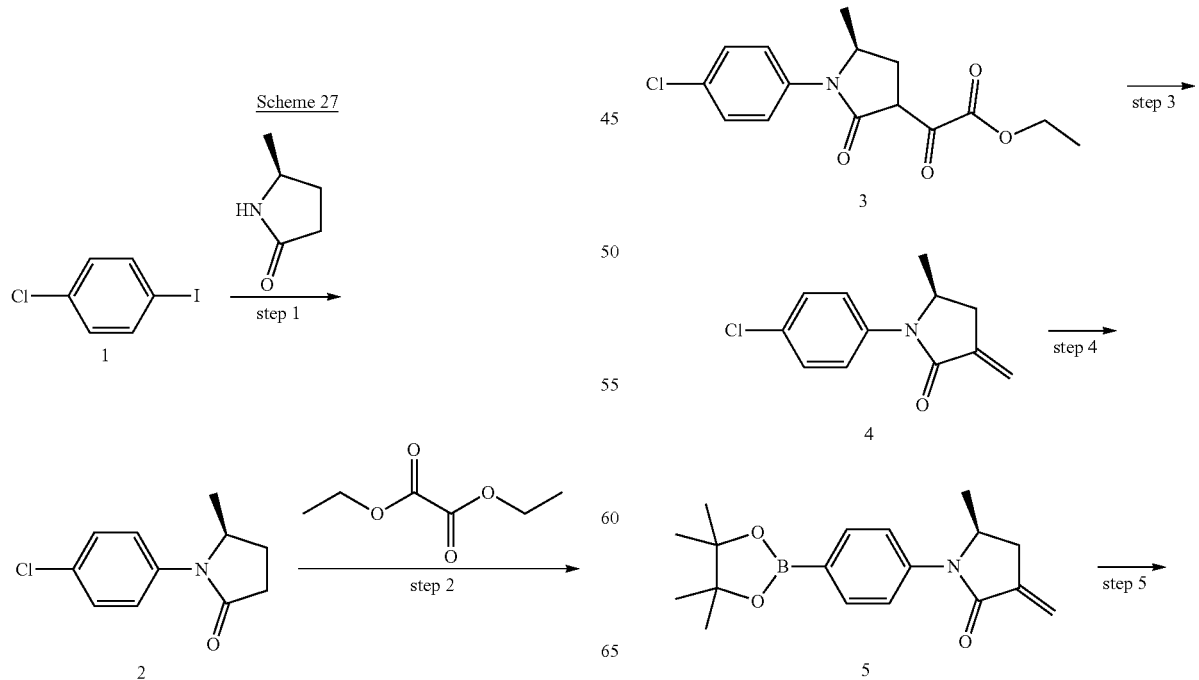

1777
-continued

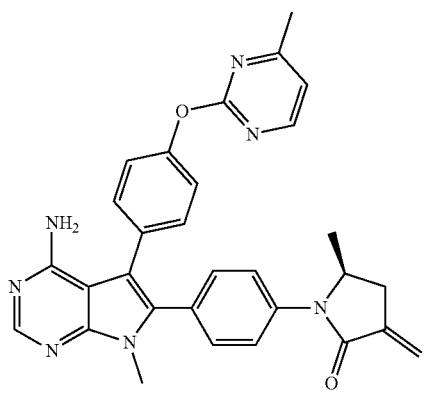 [SMILES: CC1=C[C@H](C)N(c2ccc(-c3c(-c4ccc(Oc5nccc(C)n5)cc4)c4c(N)ncnc4n3C)cc2)C1=O]

+

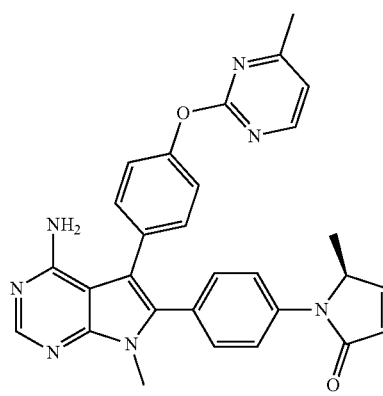

(S)-1-(4-chlorophenyl)-5-methylpyrrolidin-2-one

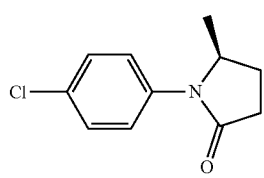

Step 1: A resealable reaction vial was charged with (5S)-5-methylpyrrolidin-2-one (1 g, 10.0 mmol), 1-chloro-4-iodobenzene (3.57 g, 15.0 mmol), N1,N2-dimethylethane-1,2-diamine (196 mg, 2.00 mmol), CuI (191 mg, 1.00 mmol), CsF (9.78 g, 30.00 mmol), THF (10 mL) and a stirbar before being evacuated and purged with nitrogen three times. The mixture was stirred at 25° C. overnight. The reaction mixture was diluted with H₂O (10 mL), and the aqueous phase was extracted with EtOAc (10 mL) three times. The combined organic layers were washed with brine, dried over sodium sulfate, filtered, and concentrated in vacuo. The residue was purified by silica gel column chromatography. This resulted in (S)-1-(4-chlorophenyl)-5-methylpyrrolidin-2-one (1.91 g, 91%).

1778
Ethyl 2-((5S)-1-(4-chlorophenyl)-5-methyl-2-oxopyrrolidin-3-yl)-2-oxoacetate

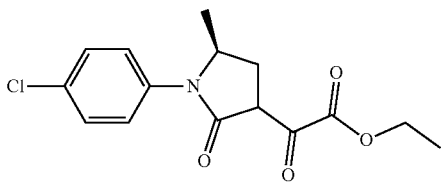 [SMILES: CCOC(=O)C(=O)C1C[C@H](C)N(c2ccc(Cl)cc2)C1=O]

Step 2: A resealable reaction vial was charged with (5S)-1-(4-chlorophenyl)-5-methylpyrrolidin-2-one (1 g, 4.76 mmol), diethyl oxalate (764 mg, 5.23 mmol), NaH (228 mg, 9.52 mmol), THF (10 mL) and a stirbar before being evacuated and purged with nitrogen three times. The mixture was stirred at 80° C. for 2 h. The reaction mixture was quenched with H₂O (10 mL), and the aqueous phase was extracted with EtOAc (20 mL) three times. The combined organic layers were washed with brine, dried over sodium sulfate, filtered, and concentrated in vacuo. The residue was purified by silica gel column chromatography. This resulted in ethyl 2-((5S)-1-(4-chlorophenyl)-5-methyl-2-oxopyrrolidin-3-yl)-2-oxoacetate (1.1 g, 74.8%).

(S)-1-(4-chlorophenyl)-5-methyl-3-methylenepyrrolidin-2-one

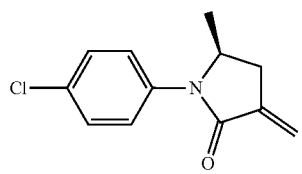

Step 3: A resealable reaction vial was charged with ethyl 2-[(5S)-1-(4-chlorophenyl)-5-methyl-2-oxopyrrolidin-3-yl]-2-oxoacetate (1.1 g, 3.55 mmol), (CH₂O)n (513 mg, 17.7 mmol), Et2NH (657 mg, 10.6 mmol), DMF (10 mL) and a stirbar before being evacuated and purged with nitrogen three times. The mixture was stirred at 100° C. for 1 h. The reaction mixture was diluted with H₂O (10 mL), and the aqueous phase was extracted with EtOAc (10 mL) three times. The combined organic layers were washed with brine, dried over sodium sulfate, filtered, and concentrated in vacuo. The residue was purified by silica gel column chromatography. This resulted in (S)-1-(4-chlorophenyl)-5-methyl-3-methylenepyrrolidin-2-one (300 mg, 38%).

(S)-5-methyl-3-methylene-1-(4-(4,4,5,5-tetramethyl-1,3,2-dioxaborolan-2-yl)phenyl)pyrrolidin-2-one

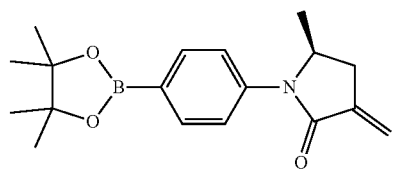

Step 4: A resealable reaction vial was charged with (5S)-1-(4-chlorophenyl)-5-methyl-3-methylidenepyrrolidin-2-one (300 mg, 1.35 mmol), AcOK (396 mg, 4.05 mmol), Xphos-2G (155 mg, 135 μmol), Xphos (212 mg, 270 μmol), and a stirbar before being evacuated and purged with nitrogen three times. dioxane (8 mL) was added, and the mixture was stirred at 90° C. for 2 h. The reaction mixture was diluted with H2O (8 mL), and the aqueous phase was extracted with EtOAc (10 mL) three times. The combined organic layers were washed with brine, dried over sodium sulfate, filtered, and concentrated in vacuo. The residue was purified by silica gel column chromatography. This resulted in (S)-5-methyl-3-methylene-1-(4-(4,4,5,5-tetramethyl-1,3,2-dioxaborolan-2-yl)phenyl)pyrrolidin-2-one (300 mg, 71%).

(S)-1-(4-(4-amino-7-methyl-5-(4-((4-methylpyrimidin-2-yl)oxy)phenyl)-7H-pyrrolo[2,3-d]pyrimidin-6-yl)phenyl)-5-methyl-3-methylenepyrrolidin-2-one and (S)-1-(4-(4-amino-7-methyl-5-(4-((4-methylpyrimidin-2-yl)oxy)phenyl)-7H-pyrrolo[2,3-d]pyrimidin-6-yl)phenyl)-3,5-dimethyl-1,5-dihydro-2H-pyrrol-2-one

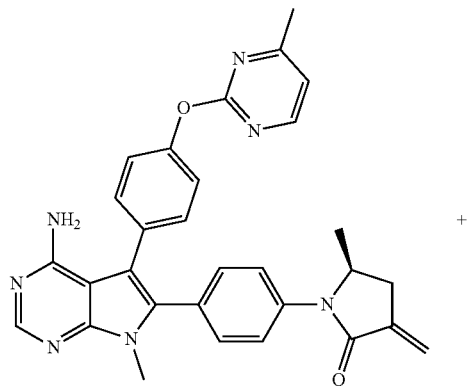

+

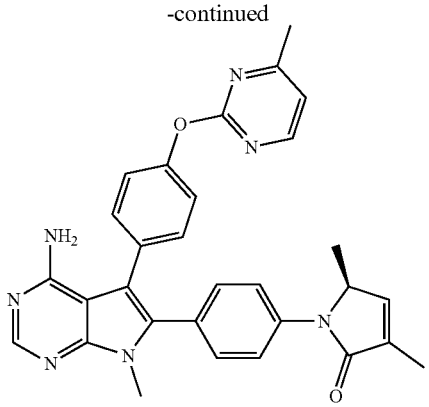

Step 5: A resealable reaction vial was charged with (5S)-5-methyl-3-methylidene-1-[4-(4,4,5,5-tetramethyl-1,3,2-dioxaborolan-2-yl)phenyl]pyrrolidin-2-one (200 mg, 638 μmol), 6-iodo-7-methyl-5-{4-[(4-methylpyrimidin-2-yl)oxy]phenyl}-7H-pyrrolo[2,3-d]pyrimidin-4-amine (350 mg, 765 μmol), K3PO4 (337 mg, 1.59 mmol), Pd(dppf)Cl2 (46.6 mg, 63.8 μmol), and a stirbar before being evacuated and purged with nitrogen three times. DME (5 mL) and H2O (1 mL) was added, and the mixture was stirred at 90° C. for 2 h. The reaction mixture was diluted with H2O (2 mL), and the aqueous phase was extracted with EtOAc (5 mL) three times. The combined organic layers were washed with brine, dried over sodium sulfate, filtered, and concentrated in vacuo. The resulting crude material was purified by Prep-HPLC (Hex(0.2% IPAmine):(EtOH:DCM=1:1)=50:50). Lyophilization yielded (5S)-1-[4-(4-amino-7-methyl-5-{4-[(4-methylpyrimidin-2-yl)oxy]phenyl}-7H-pyrrolo[2,3-d]pyrimidin-6-yl)phenyl]-5-methyl-3-methylidenepyrrolidin-2-one (2.5 mg, 0.7%) as a white amorphous solid and (5S)-1-[4-(4-amino-7-methyl-5-{4-[(4-methylpyrimidin-2-yl)oxy]phenyl}-7H-pyrrolo[2,3-d]pyrimidin-6-yl)phenyl]-3,5-dimethyl-2,5-dihydro-1H-pyrrol-2-one (120.7 mg, 36.5%) as a white amorphous solid.

Additional compounds prepared according to the methods of Example 30 are depicted in Table 29 below.

TABLE 29

Additional Exemplary Compounds

| Compound | Structure | Proton NMR | MS [M + 1] |
|---|---|---|---|
| 1-(5-(4-amino-7-methyl-5-(4-((4-methylpyrimidin-2-yl)oxy)phenyl)-7H-pyrrolo[2,3-d]pyrimidin-6-yl)pyridin-2-yl)-3-methylenepyrrolidin-2-one | 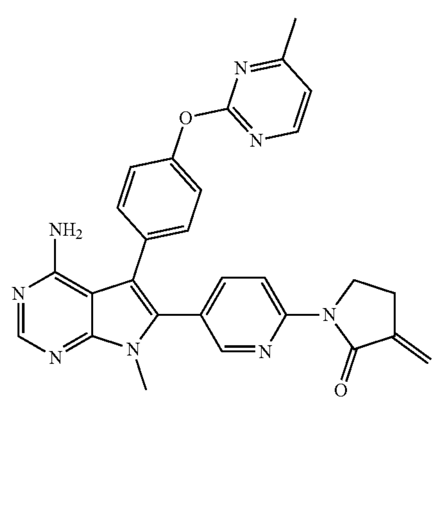 | ¹H NMR (400 MHz, DMSO-d6) δ 8.54-8.44 (m, 2H), 8.40-8.39 (m, 1H), 8.23 (s, 1H), 7.94-7.92 (m, 1H), 7.37-7.29 (m, 2H), 7.25-7.18 (m, 2H), 7.16 (d, J = 5.0 Hz, 1H), 6.02-5.96 (m, 2H), 5.57-5.52 (m, 1H), 4.05-3.97 (m, 2H), 3.65 (s, 3H), 2.86 (s, 2H), 2.41 (s, 3H). | 505.25 |

TABLE 29-continued

Additional Exemplary Compounds

| Compound | Structure | Proton NMR | MS [M + 1] |
| --- | --- | --- | --- |
| 1-(5-(4-amino-7-methyl-5-(4-((4-methylpyrimidin-2-yl)oxy)phenyl)-7H-pyrrolo[2,3-d]pyrimidin-6-yl)pyridin-2-yl)-3-methyl-1,5-dihydro-2H-pyrrol-2-one | 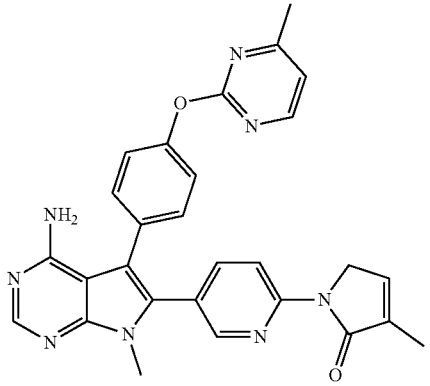 [SMILES: CC1=CCN(c2ccc(-c3c(-c4ccc(Oc5nccc(C)n5)cc4)c4c(N)ncnc4n3C)cn2)C1=O] | $^1$H NMR (400 MHz, DMSO-d$_6$) δ 8.47 (d, J = 5.0 Hz, 1H), 8.42-8.40 (m, 1H), 8.35-8.34 (m, 1H), 8.23 (s, 1H), 7.92-7.90 (m, 1H), 7.41-7.30 (m, 2H), 7.26-7.19 (m, 2H), 7.18-7.09 (m, 2H), 5.99 (s, 1H), 4.54 (q, J = 2.1 Hz, 2H), 3.64 (s, 3H), 2.41 (s, 3H), 1.86 (q, J = 1.9 Hz, 3H). | 505.25 |
| (S)-1-(4-(4-amino-7-methyl-5-(4-((4-methylpyrimidin-2-yl)oxy)phenyl)-7H-pyrrolo[2,3-d]pyrimidin-6-yl)phenyl)-5-methyl-3-methylene-pyrrolidin-2-one | 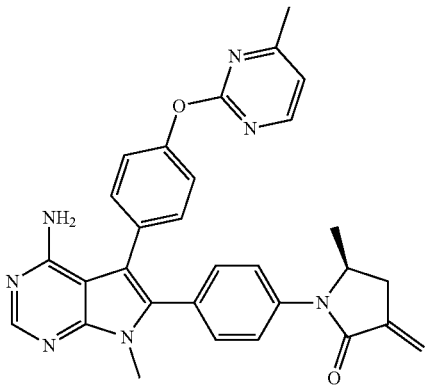 [SMILES: C=C1C[C@H](C)N(c2ccc(-c3c(-c4ccc(Oc5nccc(C)n5)cc4)c4c(N)ncnc4n3C)cc2)C1=O] | $^1$H NMR (400 MHz, Chloroform-d) δ 8.40-8.38 (m, 2H), 7.60 (d, J = 8.0 Hz, 2H), 7.34-7.17 (m, 3H), 6.94 (d, J = 5.2 Hz, 2H), 6.81 (s, 2H), 5.12 (s, 2H), 4.65 (s, 1H), 3.78 (s, 3H), 2.53 (s, 3H), 2.06-1.91 (m, 2H), 1.29 (d, J = 6.7 Hz, 3H). | 518.22 |
| (S)-1-(4-(4-amino-7-methyl-5-(4-((4-methylpyrimidin-2-yl)oxy)phenyl)-7H-pyrrolo[2,3-d]pyrimidin-6-yl)phenyl)-3,5-dimethyl-1,5-dihydro-2H-pyrrol-2-one | 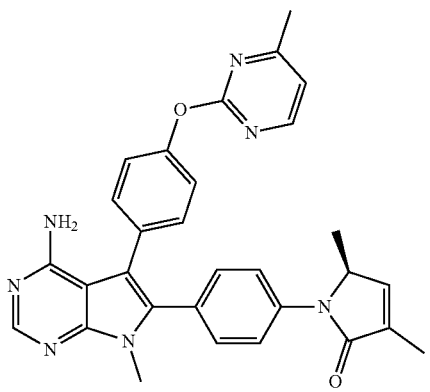 [SMILES: CC1=C[C@H](C)N(c2ccc(-c3c(-c4ccc(Oc5nccc(C)n5)cc4)c4c(N)ncnc4n3C)cc2)C1=O] | 1H NMR (400 MHz, Methanol-d4) δ 8.41 (d, J = 5.1 Hz, 1H), 8.22 (s, 1H), 7.62-7.59 (m, 2H), 7.47-7.36 (m, 4H), 7.18-7.02 (m, 3H), 7.03 (t, J = 1.8 Hz, 1H), 4.85-4.83(m, 1H), 3.73 (s, 3H), 2.50 (s, 3H), 1.94 (3, 3H), 1.25 (d, J = 6.7 Hz, 3H). | 518.22 |

TABLE 29-continued

Additional Exemplary Compounds

| Compound | Structure | Proton NMR | MS [M + 1] |
|---|---|---|---|
| (R)-1-(4-(4-amino-7-methyl-5-(4-((4-methylpyrimidin-2-yl)oxy)phenyl)-7H-pyrrolo[2,3-d]pyrimidin-6-yl)phenyl)-5-methyl-3-methylene-pyrrolidin-2-one | 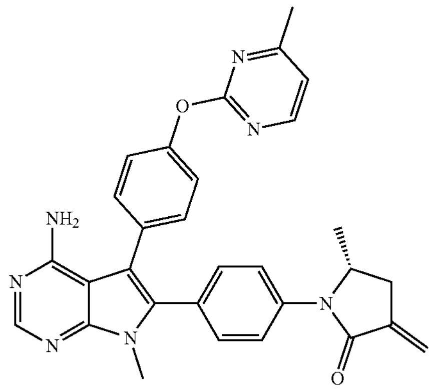 [SMILES: C=C1C[C@@H](C)N(c2ccc(-c3c(-c4ccc(Oc5nccc(C)n5)cc4)c4c(N)ncnc4n3C)cc2)C1=O] | 1H NMR (400 MHz, Chloroform-d) δ 8.42-8.36 (m, 2H), 7.64-7.56 (m, 2H), 7.37-7.29 (m, 4H), 7.23-7.15 (m, 2H), 6.94 (d, J = 5.0 Hz, 1H), 6.17 (s, 1H), 5.48 (s, 2H), 4.42-4.38 (m, 1H), 3.77 (s, 3H), 3.17-3.11 (m, 1H), 2.55-2.49 (m, 4H), 1.28 (d, J = 6.7 Hz, 3H). | 518.22 |
| (R)-1-(4-(4-amino-7-methyl-5-(4-((5-methylpyrimidin-2-yl)oxy)phenyl)-7H-pyrrolo[2,3-d]pyrimidin-6-yl)phenyl)-4-methyl-3-methylene-pyrrolidin-2-one | | 1H NMR (400 MHz, Chloroform-d) δ 8.42-8.36 (m, 2H), 7.65-7.57 (m, 2H), 7.37-7.28 (m, 4H), 7.23-7.15 (m, 2H), 6.94 (d, J = 5.0 Hz, 1H), 5.48 (t, J = 2.1 Hz, 1H), 5.13 (s, 1H), 4.47-4.35 (m, 1H), 3.77 (s, 3H), 3.14 (s, 1H), 2.58-2.47 (m, 3H), 1.29 (d, J = 6.2 Hz, 3H). | 518.22 |
| (R)-1-(4-(4-amino-7-methyl-5-(4-((5-methylpyrimidin-2-yl)oxy)phenyl)-7H-pyrrolo[2,3-d]pyrimidin-6-yl)phenyl)-4-methyl-3-methylene-pyrrolidin-2-one | | 1H NMR (400 MHz, Chloroform-d) δ 8.39 (d, J = 5.0 Hz, 2H), 7.83-7.76 (m, 2H), 7.36-7.28 (m, 4H), 7.23-7.16 (m, 2H), 6.94 (d, J = 5.0 Hz, 1H), 6.19 (d, J = 2.8 Hz, 1H), 5.45 (d, J = 2.5 Hz, 1H), 5.13 (s, 2H), 4.03 (dd, J = 9.4, 8.6 Hz, 1H), 3.75 (s,3H), 3.44 (dd, J = 9.5, 5.6 Hz, 1H), 3.13 (s, 1H), 2.53 (s, 3H), 1.37 (d, J = 6.9 Hz, 3H). | 518.35 |
| 1-(4-(4-amino-7-methyl-5-(4-(4-methylpyrimidin-2-yloxy)phenyl)-7H-pyrrolo[2,3-d]pyrimidin-6-yl)phenyl)-3-methylene-piperidin-2-one | 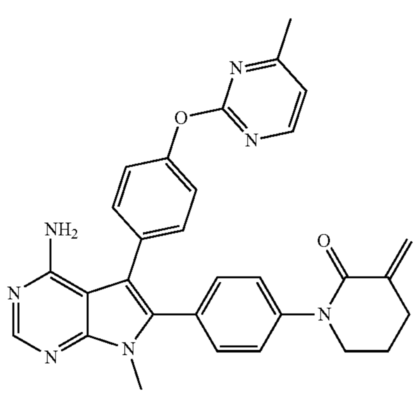 [SMILES: C=C1CCCN(c2ccc(-c3c(-c4ccc(Oc5nccc(C)n5)cc4)c4c(N)ncnc4n3C)cc2)C1=O] | 1H NMR (400 MHz, DMSO-d₆)8.47 (d, J = 5.0 Hz, 1H), 8.21 (s, 1H), 7.40 (s, 4H), 7.36-7.29 (m, 2H), 7.23-7.13 (m, 3H), 6.18-5.74 (m, 2H), 5.41 (d, J = 2.2 Hz, 1H), 3.75 (t, J = 5.7 Hz, 2H), 3.63 (s, 3H), 2.74-2.61 (m, 2H), 2.41 (s, 3H), 1.95-1.93 (m, 2H). | 518.25 |

TABLE 29-continued

Additional Exemplary Compounds

| Compound | Structure | Proton NMR | MS [M + 1] |
|---|---|---|---|
| 1-(4-(4-amino-7-methyl-5-(4-(4-methylpyrimidin-2-yloxy)phenyl)-7H-pyrrolo[2,3-d]pyrimidin-6-yl)phenyl)-3-methyl-5,6-dihydropyridin-2(1H)-one | 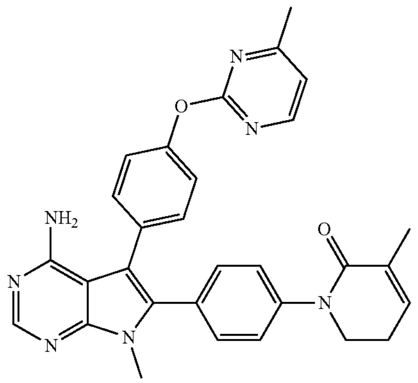 [SMILES: CC1=CCCN(c2ccc(-c3c(-c4ccc(Oc5nccc(C)n5)cc4)c4c(N)ncnc4n3C)cc2)C1=O] | $^1$H NMR (400 MHz, DMSO-$d_6$) 8.47 (d, J = 5.0 Hz, 1H), 8.21 (s, 1H), 7.38 (s, 4H), 7.36-7.29 (m, 2H), 7.23-7.17 (m, 2H), 7.16 (d, J = 5.0 Hz, 1H), 6.69-6.46 (m, 1H), 5.89 (s, 1H), 3.82 (t, J = 6.8 Hz, 2H), 3.63 (s, 3H), 2.42-2.36 (m, 5H), 1.82-1.80 (m, 3H). | 518.35 |
| (S)-1-(4-(4-amino-7-methyl-5-(4-((5-methylpyrimidin-2-yl)oxy)phenyl)-7H-pyrrolo[2,3-d]pyrimidin-6-yl)phenyl)-4-methyl-3-methylene-pyrrolidin-2-one | 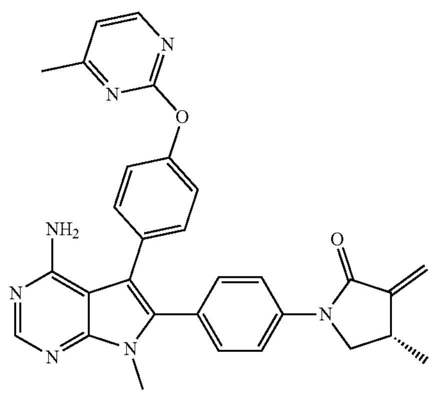 [SMILES: C=C1C(=O)N(c2ccc(-c3c(-c4ccc(Oc5nccc(C)n5)cc4)c4c(N)ncnc4n3C)cc2)C[C@H]1C] | 1H NMR (400 MHz, Chloroform-d) δ 8.39 (d, J = 5.3 Hz, 2H), 7.82-7.62 (m, 2H), 7.36-7.28 (m, 4H), 7.23-7.15 (m, 2H), 6.94 (d, J = 5.0 Hz, 1H), 6.18 (d, J = 2.9 Hz, 1H), 5.45 (d, J = 2.5 Hz, 1H), 5.11 (s, 2H), 4.03 (t, J = 9.0 Hz, 1H), 3.75 (s, 3H), 3.44 (dd, J = 9.4, 5.5 Hz, 1H), 3.12 (s, 1H), 2.52 (s, 3H), 1.36 (d, J = 6.9 Hz, 3H). | 518.35 |
| 1-(4-(4-amino-7-methyl-5-(4-((4-methylpyrimidin-2-yl)oxy)phenyl)-7H-pyrrolo[2,3-d]pyrimidin-6-yl)phenyl)-4,4-dimethyl-3-methylene-pyrrolidin-2-one | 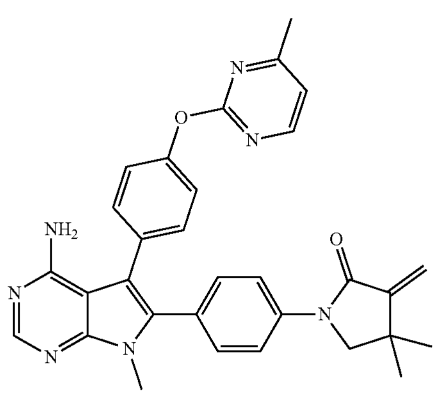 [SMILES: C=C1C(=O)N(c2ccc(-c3c(-c4ccc(Oc5nccc(C)n5)cc4)c4c(N)ncnc4n3C)cc2)CC1(C)C] | $^1$H NMR (400 MHz, DMSO-d) δ 8.47 (d, J = 5.0 Hz, 1H), 8.21 (s, 1H), 7.86-7.80 (m, 2H), 7.46-7.39 (m, 2H), 7.35-7.25 (m, 2H), 7.23-7.12 (m, 3H), 5.90 (s, 1H), 5.50 (s, 1H), 3.67 (s, 2H), 3.62 (s, 3H), 2.41 (s, 3H), 1.27 (s, 6H). | 532.20 |

TABLE 29-continued

Additional Exemplary Compounds

| Compound | Structure | Proton NMR | MS [M + 1] |
|---|---|---|---|
| 7-(4-amino-7-methyl-5-(4-((4-methylpyrimidin-2-yl)oxy)phenyl)-7H-pyrrolo[2,3-d]pyrimidin-6-yl)-2-methylene-3,4-dihydronaphthalen-1(2H)-one | 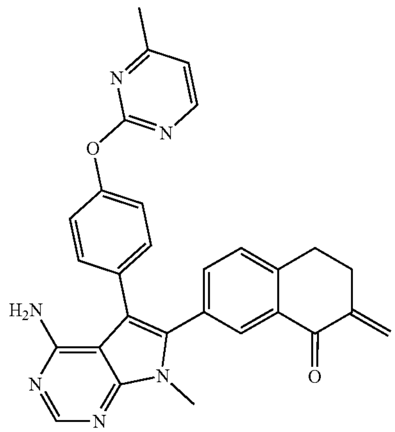 [SMILES: C=C1CCc2ccc(-c3c(-c4ccc(Oc5nccc(C)n5)cc4)c4c(N)ncnc4n3C)cc2C1=O] | 1H NMR (400 MHz, DMSO-d$_6$) δ 8.46 (1H, d), 8.22 (1H, s), 7.91 (1H, d), 7.60 (1H, dd), 7.44 (1H, d), 7.35-7.27 (2H, m), 7.22-7.10 (3H, m), 5.81 (3H, dd), 3.61 (3H, s), 3.02 (2H, t), 2.90-2.82 (2H, m), 2.40 (3H, s) | 489.30 |
| 6-(4-amino-7-methyl-5-(4-((4-methylpyrimidin-2-yl)oxy)phenyl)-7H-pyrrolo[2,3-d]pyrimidin-6-yl)-2-methylene-3,4-dihydronaphthalen-1(2H)-one | 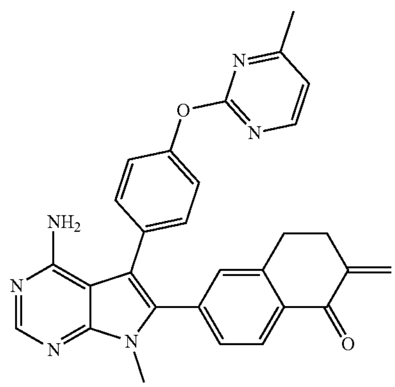 [SMILES: C=C1CCc2cc(-c3c(-c4ccc(Oc5nccc(C)n5)cc4)c4c(N)ncnc4n3C)ccc2C1=O] | 1H NMR (400 MHz, DMSO-d6) δ 8.46 (d, J = 5.0 Hz, 1H), 8.24 (s, 1H), 7.93 (d, J = 8.1 Hz, 1H), 7.42 (d, J = 1.7 Hz, 1H), 7.36 (dd, J = 8.0, 1.7 Hz, 1H), 7.35-7.27 (m, 2H), 7.24-7.13 (m, 3H), 6.06 (d, J = 2.1 Hz, 1H), 5.99 (s, 2H), 5.56 (d, J = 2.0 Hz, 1H), 3.68 (s, 3H), 2.96 (t, J = 6.3 Hz, 2H), 2.84 (t, J = 6.1 Hz, 2H), 2.41 (s, 3H). | 489.35 |

Example 31

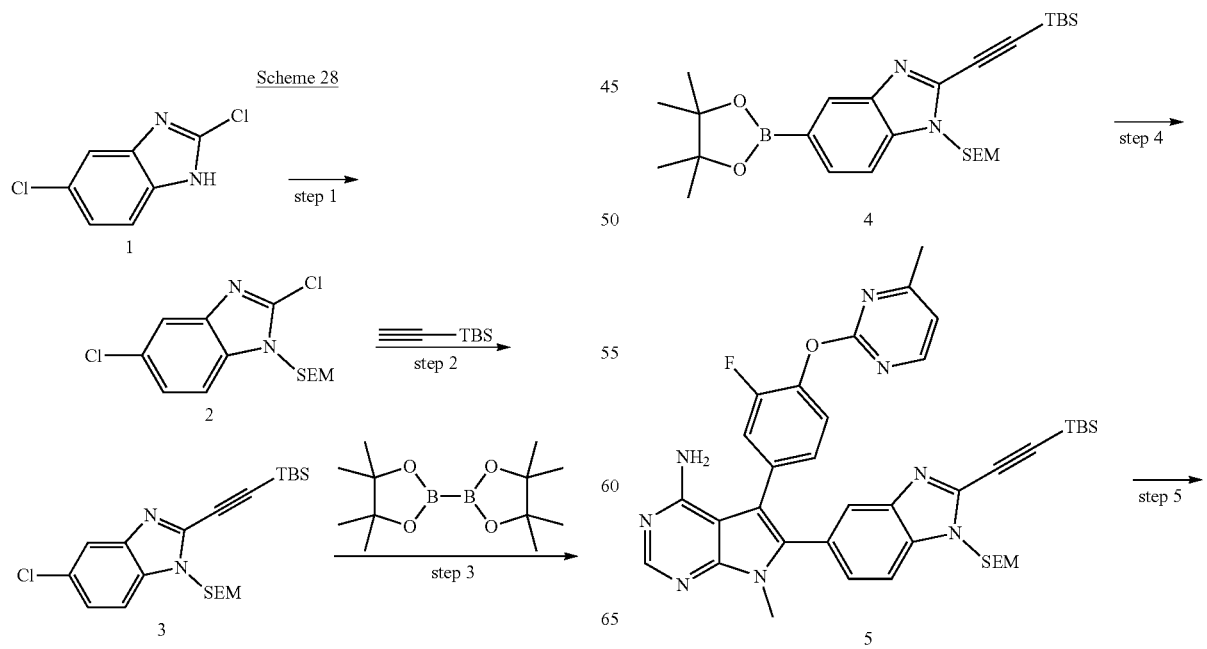

1789
-continued

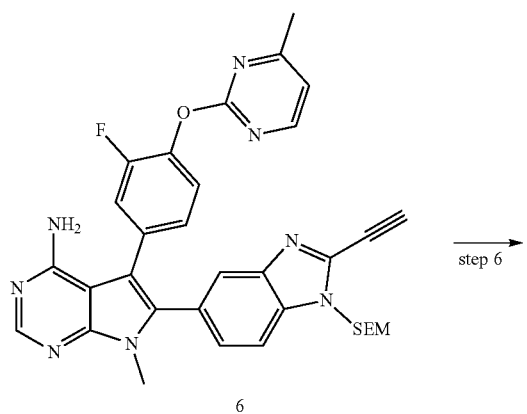

6

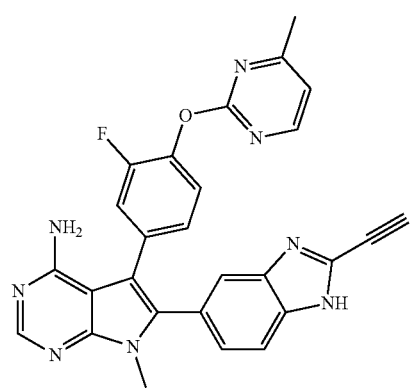 [SMILES: C#Cc1nc2cc(-c3c(-c4ccc(Oc5nccc(C)n5)c(F)c4)c4c(N)ncnc4n3C)ccc2[nH]1]

2,5-dichloro-1-((2-(trimethylsilyl)ethoxy)methyl)-1H-benzo[d]imidazole

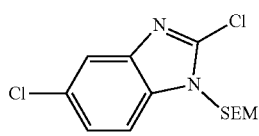

Step 1: A round bottomed flask was charged with 2,5-dichloro-1H-benzo[d]imidazole (1 g, 5.4 mmol), Dimethylformamide (5 mL) and a stir bar NaH (60%, 259 mg, 6.48 mmol) was added, and the solution was stirred for 10 min at 0° C. Added a SEMCl (896 mg, 5.4 mmol) was added, and the solution was stirred for 10 h at 0° C. The reaction mixture was quenched with water, extracted with DCM, dried over Na₂SO₄, concentrated in vacuo. The resulted mixture was purified through C18 Column. Concentration in vacuo resulted in in 2,5-dichloro-1-((2-(trimethylsilyl)ethoxy)methyl)-1H-benzo[d]imidazole (820 mg, 48%) as an yellow oil.

2-((tert-butyldimethylsilyl)ethynyl)-5-chloro-1-((2-(trimethylsilyl)ethoxy)methyl)-1H-benzo[d]imidazole

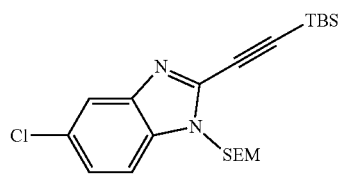

Step 2: A round bottomed flask was charged with 2,5-dichloro-1-((2-(trimethylsilyl)ethoxy)methyl)-1H-benzo[d]imidazole (800 mg, 1.30 mmol), tert-butyl(ethynyl)dimethylsilane (274 mg, 1.96 mmol), Pd(PPh₃)₂Cl₂ (183 mg, 261 μmol), CuI (99 mg, 0.52 mmol), TEA (395 mg, 3.09 mmol) and a stir bar. Dimethylformamide (20 mL) was added, and the solution was stirred for 2 h at 50° C. The reaction mixture was quenched with water, extracted with DCM, dried over Na₂SO₄, concentrated in vacuo. The resulted mixture was purified through C18 Column. Concentration in vacuo resulted in 2-((tert-butyldimethylsilyl)ethynyl)-5-chloro-1-((2-(trimethylsilyl)ethoxy)methyl)-1H-benzo[d]imidazole (500 mg, 47%) as an yellow oil.

2-((tert-butyldimethylsilyl)ethynyl)-5-(4,4,5,5-tetramethyl-1,3,2-dioxaborolan-2-yl)-1-((2-(trimethylsilyl)ethoxy)methyl)-1H-benzo[d]imidazole

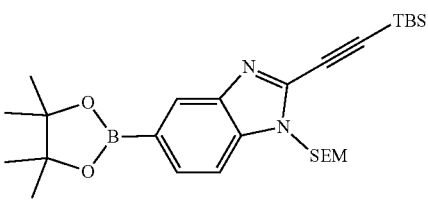

Step 3: A round bottomed flask was charged with 2-((tert-butyldimethylsilyl)ethynyl)-5-chloro-1-((2-(trimethylsilyl)ethoxy)methyl)-1H-benzo[d]imidazole (480 mg, 1.14 mmol), 4,4,4',4',5,5,5',5'-octamethyl-2,2'-bi(1,3,2-dioxaborolane) (579 mg, 2.28 mmol), Pd(dppf)Cl₂ (83 mg, 114 μmol), AcOK (335 mg, 3.42 mmol) and a stir bar. Dioxane (10 mL) was added, and the solution was stirred for 2 h at 90° C. The resulted mixture was purified through C18 Column. Concentration in vacuo resulted in 2-((tert-butyldimethylsilyl)ethynyl)-5-(4,4,5,5-tetramethyl-1,3,2-dioxaborolan-2-yl)-1-((2-(trimethylsilyl)ethoxy)methyl)-1H-benzo[d]imidazole (550 mg, 94%) as an white oil.

6-(2-((tert-butyldimethylsilyl)ethynyl)-1-((2-(trimethylsilyl)ethoxy)methyl)-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine

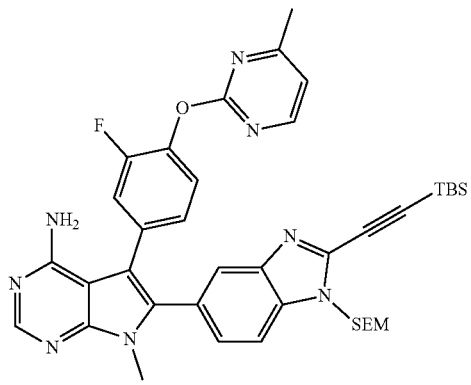

Step 4: A resealable reaction via was charged with 2-((tert-butyldimethylsilyl)ethynyl)-5-(4,4,5,5-tetramethyl-1,3,2-dioxaborolan-2-yl)-1-((2-(trimethylsilyl)ethoxy)methyl)-1H-benzo[d]imidazole (480 mg, 0.86 mmol), 5-(3-fluoro-4-((4-methylpyrimidin-2-yl)oxy)phenyl)-6-iodo-7-methyl-7H-pyrrolo[2,3-d]pyrimidin-4-amine (273 mg, 0.57 mmol), Pd(dppf)Cl$_2$ (42 mg, 57 μmol), K$_3$PO$_4$ (363 mg, 1.71 mmol) and a stir bar before being evacuated and purged with nitrogen three times. DME:water=10:1 (10 mL) was added, and the solution was stirred for 1 h at 90° C. The reaction mixture was quenched with water, extracted with DCM, dried over Na$_2$SO$_4$, concentrated in vacuo. The resulting crude material was purified by prep-TLC. Concentration in vacuo resulted in 6-(2-((tert-butyldimethylsilyl)ethynyl)-1-((2-(trimethylsilyl)ethoxy)methyl)-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine (260 mg, 62%) as an yellow amorphous solid.

6-(2-ethynyl-1-((2-(trimethylsilyl)ethoxy)methyl)-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine

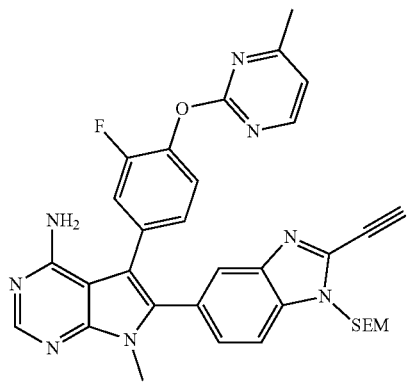 [SMILES: C#Cc1nc2cc(-c3c(-c4ccc(Oc5nccc(C)n5)c(F)c4)c4c(N)ncnc4n3C)ccc2n1COCC[Si](C)(C)C]

Step 5: A round bottomed flask was charged with 6-(2-ethynyl-1-((2-(trimethylsilyl)ethoxy)methyl)-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine (240 mg, 0.33 mmol), THF (4 mL) and a stir bar. TBAF (1 M, 0.7 mL, 0.66 mmol) was added, and the solution was stirred for 1 h at room temperature. The reaction mixture was quenched with water, extracted with DCM, dried over Na$_2$SO$_4$, concentrated in vacuo. The residue was purified by silica gel column chromatography, eluted with DCM/MeOH (8:1). Concentration in vacuo resulted in 6-(2-ethynyl-1-((2-(trimethylsilyl)ethoxy)methyl)-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine (100 mg, 49%) as an yellow oil.

6-(2-ethynyl-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine

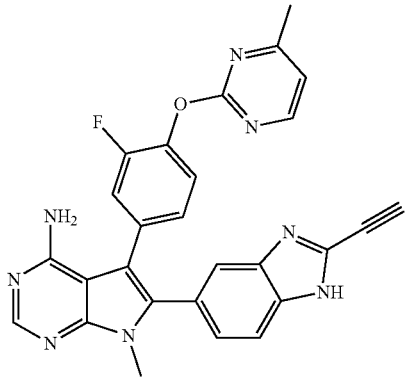 [SMILES: C#Cc1nc2cc(-c3c(-c4ccc(Oc5nccc(C)n5)c(F)c4)c4c(N)ncnc4n3C)ccc2[nH]1]

Step 6: A round bottomed flask was charged with 6-(2-ethynyl-1-((2-(trimethylsilyl)ethoxy)methyl)-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine (80 mg, 852 μmol), DCM (4 mL) and a stir bar. TFA (44 mg, 0.39 mmol) was added, and the solution was stirred for 1 h at room temperature. The reaction mixture was vacuo. The resulting crude material was purified by prep-HPLC (Column: YMC-Actus Triart C18, 30*250, 5 um; Mobile Phase A:Water(10 MMOL/L NH$_4$HCO$_3$+0.1% NH$_3$·H$_2$O), Mobile Phase B:ACN; Flow rate:50 mL/min; Gradient:30 B to 65 B in 8 min; 220 nm; RT1:7.22). Lyophilization yielded in 6-(2-ethynyl-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine (22.1 mg, 35%) as an off-white amorphous solid.

Additional compounds prepared according to the methods of Example 31 are depicted in Table 30 below.

TABLE 30

Additional Exemplary Compounds

| Compound | Structure | Proton NMR | MS [M + 1] |
|---|---|---|---|
| 6-(2-ethynyl-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine | 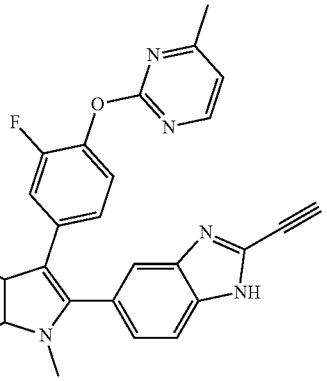 | $^1$H NMR (300 MHz, DMSO-d6) δ 13.29 (s, 1H), 8.44 (s, 1H), 8.20 (s, 1H), 7.67-7.18 (m, 4H), 7.15 (d, J = 5.0 Hz, 3H), 4.67 (s, 1H), 3.61 (s, 3H), 2.38 (s, 3H). | 491.20 |
| 6-(2-ethynyl-1,6-dimethyl-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine | 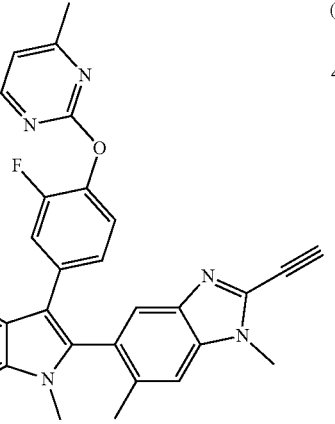 | 1H NMR (400 MHz, DMSO-d6) δ 8.43 (d, J = 5.1 Hz, 1H), 8.23 (s, 1H), 7.70 (s, 1H), 7.56 (s, 1H), 7.28 (t, J = 8.4 Hz, 1H), 7.21-7.13 (m, 2H), 7.12-7.05 (m, 1H), 6.03 (s, 2H), 4.95 (s, 1H), 3.87 (s, 3H), 2.38 (s, 3H), 2.12 (s, 3H). | 519.25 |
| 6-(2-ethynyl-1-methyl-1H-benzo[d]imidazol-5-yl)-5-(3-fluoro-4-((4-methylpyrimidin-2-yl)oxy)phenyl)-7-methyl-7H-pyrrolo[2,3-d]pyrimidin-4-amine | 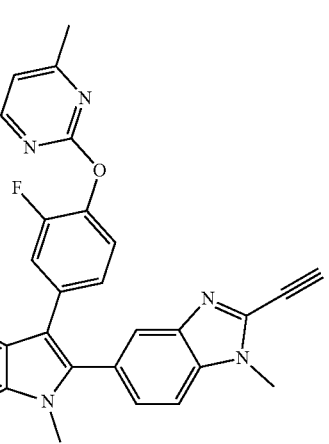 | $^1$H NMR (400 MHz, DMSO-d$_6$) δ 8.45 (d, J = 5.2 Hz, 1H), 8.22 (s, 1H), 7.70 (d, J = 1.5 Hz, 1H), 7.65 (d, J = 8.4 Hz, 1H), 7.40-7.26 (m, 2H), 7.24-7.06 (m, 3H), 5.99 (s, 2H), 4.98 (s, 1H), 3.89 (s, 3H), 3.58 (s, 3H), 2.40 (s, 3H). | 505.20 |

TABLE 30-continued

Additional Exemplary Compounds

| Compound | Structure | Proton NMR | MS [M + 1] |
|---|---|---|---|
| 6-(2-ethynyl-6-fluoro-1-methyl-1H-benzo[d]imidazol-5-yl)-5-(3-fluoro-4-(4-methylpyrimidin-2-yl)oxy)phenyl)-7-methyl-7H-pyrrolo[2,3-d]pyrimidin-4-amine | 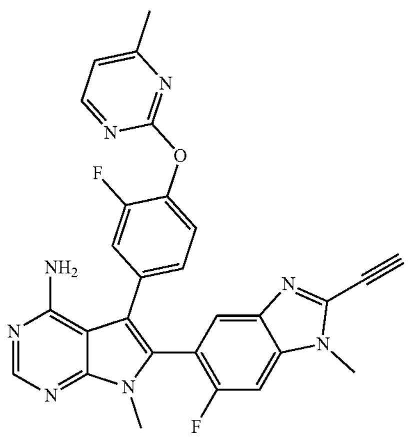 [SMILES: C#Cc1nc2cc(-c3c(-c4ccc(Oc5nccc(C)n5)c(F)c4)c4c(N)ncnc4n3C)c(F)cc2n1C] | $^1$H NMR (400 MHz, DMSO-$d_6$)8.44 (d, J = 5.0 Hz, 1H), 8.23 (s, 1H), 7.72 (dd, J = 9.8, 8.1 Hz, 2H), 7.30 (t, J = 8.4 Hz, 1H), 7.21 (dd, J = 11.3, 2.0 Hz, 1H), 7.16 (d, J = 5.1 Hz, 1H), 7.13-7.07 (m, 1H), 6.04 (s, 2H), 5.00 (s, 1H), 3.87 (s, 3H), 3.52 (s, 3H), 2.38 (s, 3H). | 523.20 |
| 6-(2-ethynyl-1-methyl-1H-benzo[d]imidazol-6-yl)-5-(3-fluoro-4-((4-methylpyrimidin-2-yl)oxy)phenyl)-7-methyl-7H-pyrrolo[2,3-d]pyrimidin-4-amine | 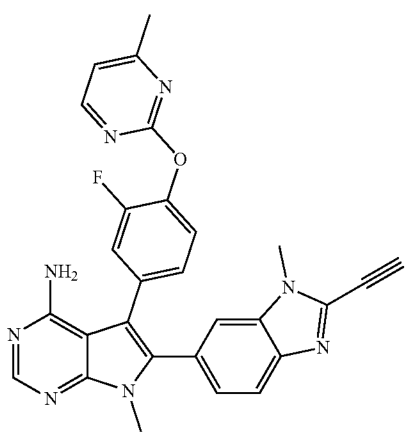 [SMILES: C#Cc1nc2ccc(-c3c(-c4ccc(Oc5nccc(C)n5)c(F)c4)c4c(N)ncnc4n3C)cc2n1C] | 1H NMR (400 MHz, DMSO-d6) δ 8.44 (d, J = 5.0 Hz, 1H), 8.23 (s, 1H), 7.70 (d, J = 1.6 Hz, 1H), 7.65 (s, 1H), 7.30 (t, J = 8.4 Hz, 1H), 7.26-7.14 (m, 3H), 7.14-7.08 (m, 1H), 6.02 (s, 2H), 4.99 (s, 1H), 3.85 (s, 3H), 3.62 (s, 3H), 2.39 (s, 3H). | 505.20 |
| 6-(2-ethynyl-6-methoxy-1-methyl-1H-benzo[d]imidazol-5-yl)-5-(3-fluoro-4-(4-methylpyrimidin-2-yl)oxy)phenyl)-7-methyl-7H-pyrrolo[2,3-d]pyrimidin-4-amine | 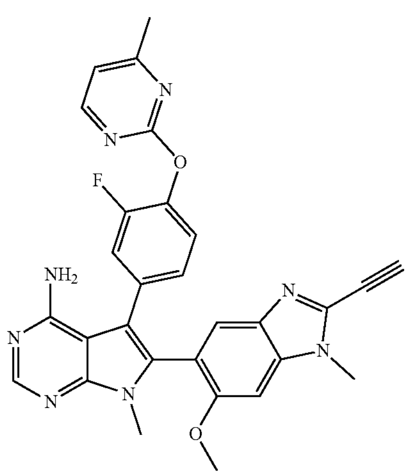 [SMILES: C#Cc1nc2cc(-c3c(-c4ccc(Oc5nccc(C)n5)c(F)c4)c4c(N)ncnc4n3C)c(OC)cc2n1C] | 1H NMR (400 MHz, DMSO-d6) 8.44 (d, J = 5.0 Hz, 1H), 8.21 (s, 1H), 7.48 (s, 1H), 7.34 (s, 1H), 7.28 (t, J = 8.4 Hz, 1H), 7.18-7.10 (m, 2H), 7.05 (dd, J = 8.4, 2.0 Hz, 1H), 5.99 (s, 2H), 4.91 (s, 1H), 3.88 (s, 3H), 3.84 (s, 3H), 3.44 (s, 3H), 2.38 (s, 3H). | 535.20 |

Example 32
Scheme 29
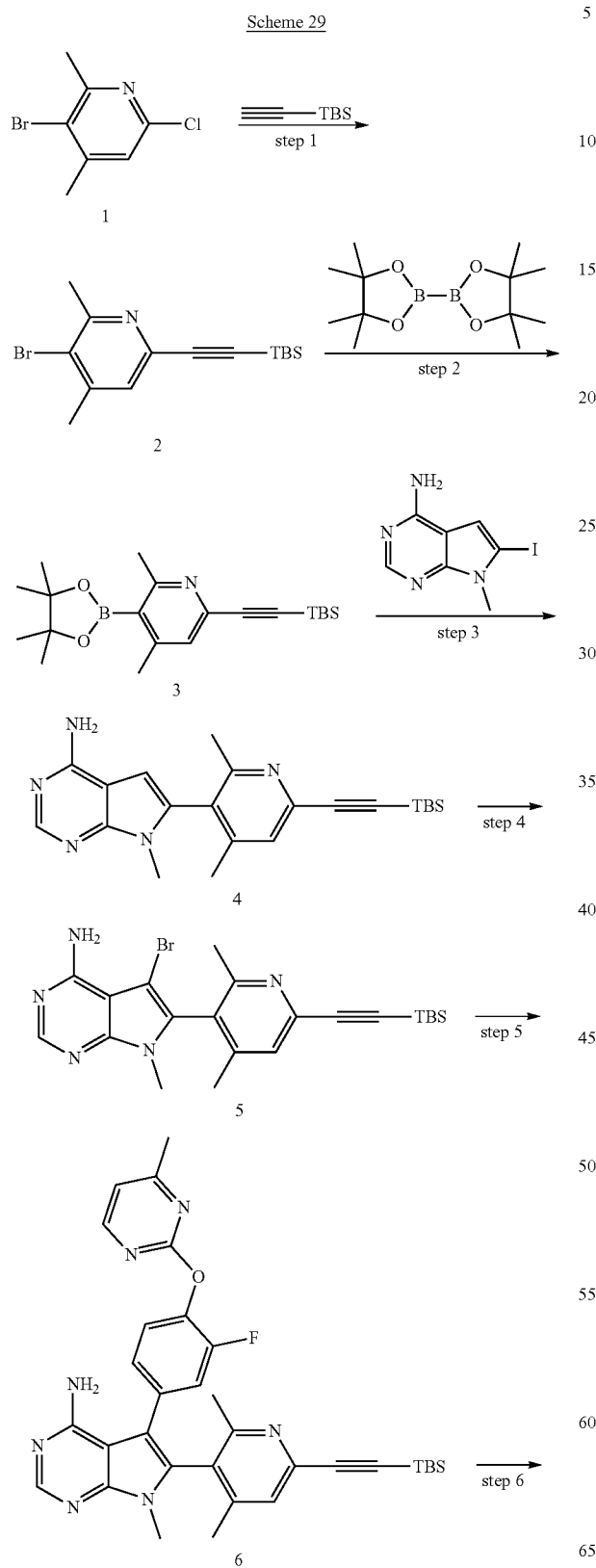
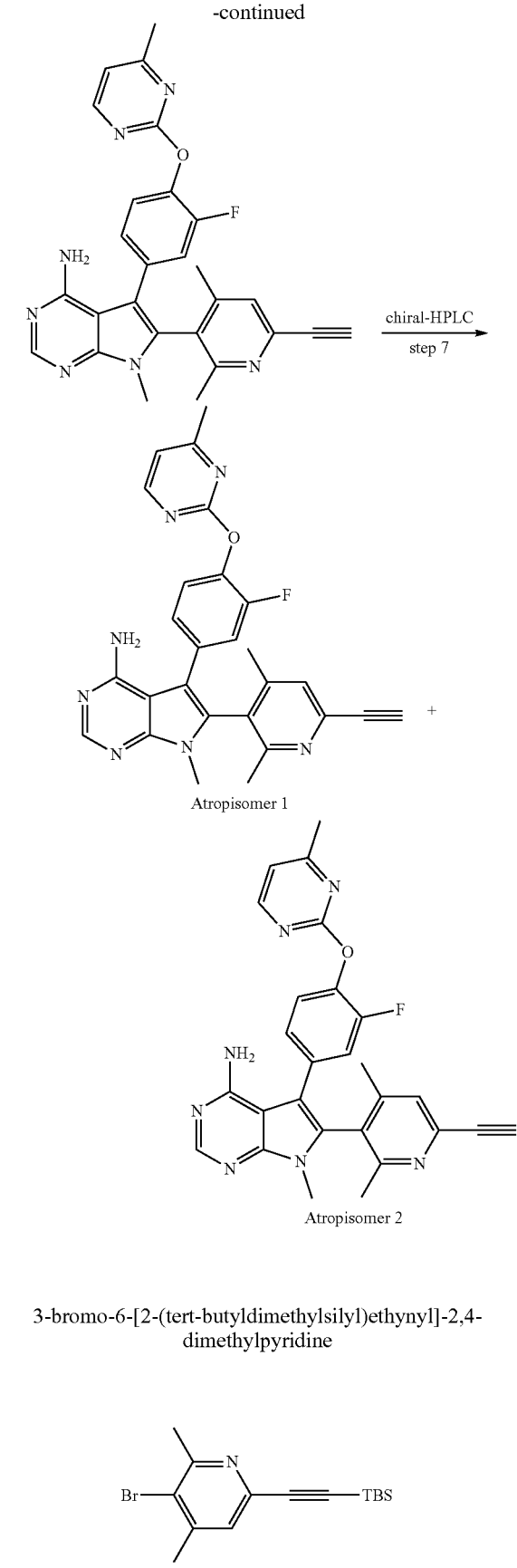
3-bromo-6-[2-(tert-butyldimethylsilyl)ethynyl]-2,4-dimethylpyridine Step 1: A resealable reaction vial was charged with 3-bromo-6-chloro-2,4-dimethylpyridine (8 g, 36.2 mmol), tert-butyl(ethynyl)dimethylsilane (5.58 g, 39.8 mmol), CuI (1.37 g, 7.24 mmol), Pd(PPh₃)₂Cl₂ (2.54 g, 3.62 mmol), TEA (10.9 g, 108 mmol), dimethylformamide (100 mL) and a stirbar before being evacuated and purged with nitrogen three times. The mixture was stirred for 2 h at 80° C. The reaction mixture was quenched with water, extracted with DCM. The organic phase was combined and washed with brine for three times, dried over Na₂SO₄, evaporated in vacuo. The resulting crude material was purified by silica gel chromatography. Concentration in vacuo resulted in 3-bromo-6-[2-(tert-butyldimethylsilyl)ethynyl]-2,4-dimethylpyridine (10.0 g, 85%) as an off-white oil.

6-[2-(tert-butyldimethylsilyl)ethynyl]-2,4-dimethyl-3-(4,4,5,5-tetramethyl-1,3,2-dioxaborolan-2-yl)pyridine

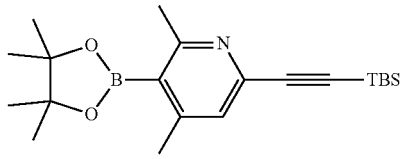

Step 2: A resealable reaction vial was charged with 3-bromo-6-[2-(tert-butyldimethylsilyl)ethynyl]-2,4-dimethylpyridine (9.6 g, 29.52 mmol), 4,4,5,5-tetramethyl-2-(4,4,5,5-tetramethyl-1,3,2-dioxaborolan-2-yl)-1,3,2-dioxaborolane (14.88 g, 59.04 mmol), Pd(dppf)Cl₂ (2.15 mg, 2.95 μmol), AcOK (8.66 g, 88.44 mmol), dimethylformamide (150 mL) and a stirbar before being evacuated and purged with nitrogen three times. The mixture was stirred at 90° C. for 12 h. The reaction mixture was quenched with water, extracted with DCM. The organic phase was washed with brine for three times, dried over Na₂SO₄, evaporated in vacuo. The resulting crude material was purified by silica gel chromatography. Concentration in vacuo resulted in 6-[2-(tert-butyldimethylsilyl)ethynyl]-2,4-dimethyl-3-(4,4,5,5-tetramethyl-1,3,2-dioxaborolan-2-yl)pyridine (2.5 g, 27%) as an off-white amorphous solid.

6-{6-[2-(tert-butyldimethylsilyl)ethynyl]-2,4-dimethylpyridin-3-yl}-7-methyl-7H-pyrrolo[2,3-d]pyrimidin-4-amine

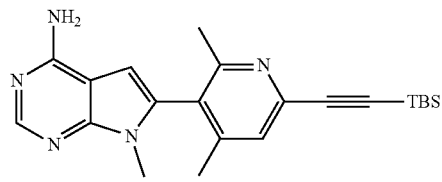

Step 3: A resealable reaction vial was charged with 6-[2-(tert-butyldimethylsilyl)ethynyl]-2,4-dimethyl-3-(4,4,5,5-tetramethyl-1,3,2-dioxaborolan-2-yl)pyridine (1.3 g, 3.49 mmol), 6-iodo-7-methyl-7H-pyrrolo[2,3-d]pyrimidin-4-amine (952 mg, 3.49 mmol), bis(adamantan-1-yl)(butyl)phosphane (125 mg, 349 μmol), palladium(1+) 2'-amino-1,1'-biphenyl-2-yl bis(adamantan-1-yl)(butyl)phosphane chloride (233 mg, 349 μmol), K₃PO₄ (2.2 g, 1.05 mmol), dioxane/H₂O (15 mL) and a stirbar before being evacuated and purged with nitrogen three times. The mixture was stirred at 90° C. for 6 h. The reaction mixture was quenched with water, extracted with DCM. The organic phase was washed with brine for three times, dried over Na₂SO₄, evaporated in vacuo. The resulting crude material was purified by silica gel chromatography. Concentration in vacuo resulted in 6-{6-[2-(tert-butyldimethylsilyl)ethynyl]-2,4-dimethylpyridin-3-yl}-7-methyl-7H-pyrrolo[2,3-d]pyrimidin-4-amine (500 mg, 37%) as a yellow amorphous solid.

5-bromo-6-{6-[2-(tert-butyldimethylsilyl)ethynyl]-2,4-dimethylpyridin-3-yl}-7-methyl-7H-pyrrolo[2,3-d]pyrimidin-4-amine

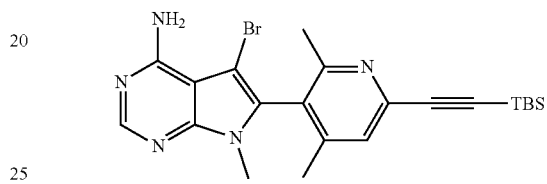

Step 4: A round bottomed flask was charged with 6-{6-[2-(tert-butyldimethylsilyl)ethynyl]-2,4-dimethylpyridin-3-yl}-7-methyl-7H-pyrrolo[2,3-d]pyrimidin-4-amine (500 mg, 1.27 mmol), NBS (272 mg, 1.53 mmol), dimethylformamide (20 mL) and a stirbar. The solution was stirred for 1 h at room temperature. The reaction mixture was quenched with water, extracted with DCM. The organic phase was washed with brine for three times, dried over Na₂SO₄, evaporated in vacuo. The resulting crude material was purified by silica gel chromatography (20 g column; eluting with dichloromethane/methanol; 12:1). Concentration in vacuo resulted in 5-bromo-6-{6-[2-(tert-butyldimethylsilyl)ethynyl]-2,4-dimethylpyridin-3-yl}-7-methyl-7H-pyrrolo[2,3-d]pyrimidin-4-amine (500 mg, 88.3%) as a red amorphous solid 6-{6-[2-(tert-butyldimethylsilyl)ethynyl]-2,4-dimethylpyridin-3-yl}-5-{3-fluoro-4-[(4-methylpyrimidin-2-yl)oxy]phenyl}-7-methyl-7H-pyrrolo[2,3-d]pyrimidin-4-amine

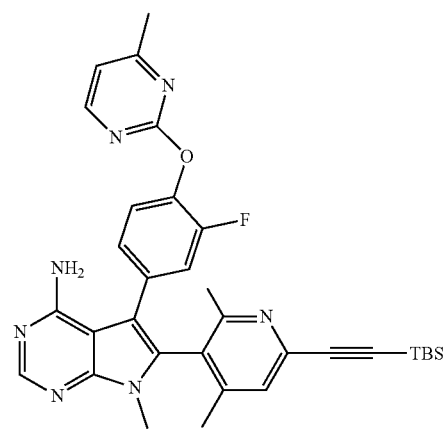

Step 5: A resealable reaction vial was charged with 5-bromo-6-{6-[2-(tert-butyldimethylsilyl)ethynyl]-2,4-dimethylpyridin-3-yl}-7-methyl-7H-pyrrolo[2,3-d]pyrimidin-4-amine (460 mg, 977 μmol), 2-[2-fluoro-4-(4,4,5,5-tetramethyl-1,3,2-dioxaborolan-2-yl)phenoxy]-4-methylpyrimidine (643 mg, 1.95 mmol), Pd(PPh$_3$)$_4$ (112 mg, 97.7 μmol), K$_3$PO$_4$ (621 mg, 2.93 mmol), DME/H$_2$O (10 mL) and a stirbar before being evacuated and purged with nitrogen three times. The mixture was stirred for 2 h at 90° C. The reaction mixture was quenched with water, extracted with DCM. The organic phase was washed with brine for three times, dried over Na$_2$SO$_4$, evaporated in vacuo. The resulting crude material was purified by silica gel chromatography. Concentration in vacuo resulted in 6-{6-[2-(tert-butyldimethylsilyl)ethynyl]-2,4-dimethylpyridin-3-yl}-5-{3-fluoro-4-[(4-methylpyrimidin-2-yl)oxy]phenyl}-7-methyl-7H-pyrrolo[2,3-d]pyrimidin-4-amine (250 mg, 43%) as an orange amorphous solid.

6-(6-ethynyl-2,4-dimethylpyridin-3-yl)-5-{3-fluoro-4-[(4-methylpyrimidin-2-yl)oxy]phenyl}-7-methyl-7H-pyrrolo[2,3-d]pyrimidin-4-amine

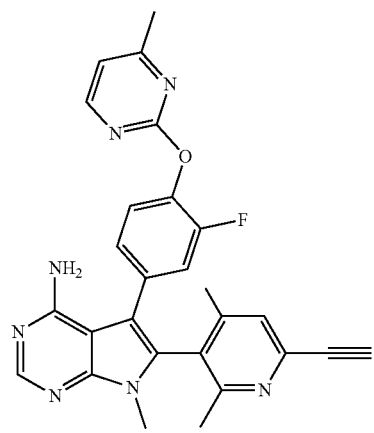 [SMILES: C#Cc1cc(C)c(-c2c(-c3ccc(Oc4nccc(C)n4)c(F)c3)c3c(N)ncnc3n2C)c(C)n1]

Step 6: A round bottomed flask was charged with 6-{6-[2-(tert-butyldimethylsilyl)ethynyl]-2,4-dimethylpyridin-3-yl}-5-{3-fluoro-4-[(4-methylpyrimidin-2-yl)oxy]phenyl}-7-methyl-7H-pyrrolo[2,3-d]pyrimidin-4-amine (230 mg, 387 μmol), CsF (176 mg, 1.16 mmol), and a stirbar. tetrahydrofuran (8 mL) was added, and the solution was stirred for 2 h at 50° C. The reaction mixture was quenched with water, extracted with DCM, dried over Na$_2$SO$_4$, concentrated in vacuo. The resulting crude material was purified by HPLC(Column: XBridge Shield RP18 OBD Column, 30*150 mm, 5 um; Mobile Phase A:Water(10 MMOL/L NH$_4$HCO$_3$), Mobile Phase B:ACN; Flow rate:60 mL/min; Gradient:20 B to 45 B in 8 min; 220 nm; RT1:7.12;). Lyophilization yielded 6-(6-ethynyl-2,4-dimethylpyridin-3-yl)-5-{3-fluoro-4-[(4-methylpyrimidin-2-yl)oxy]phenyl}-7-methyl-7H-pyrrolo[2,3-d]pyrimidin-4-amine (100 mg, 208 μmol) as an off-white amorphous solid.

6-(6-ethynyl-2,4-dimethylpyridin-3-yl)-5-{3-fluoro-4-[(4-methylpyrimidin-2-yl)oxy]phenyl}-7-methyl-7H-pyrrolo[2,3-d]pyrimidin-4-amine

PEAK 1

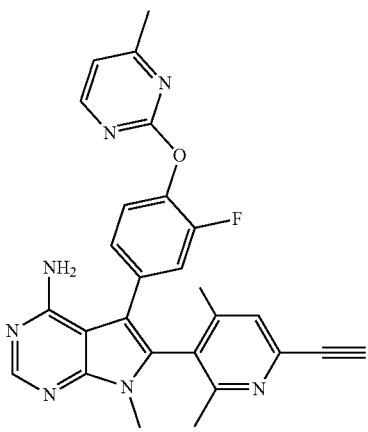 [SMILES: C#Cc1cc(C)c(-c2c(-c3ccc(Oc4nccc(C)n4)c(F)c3)c3c(N)ncnc3n2C)c(C)n1]

PEAK 2

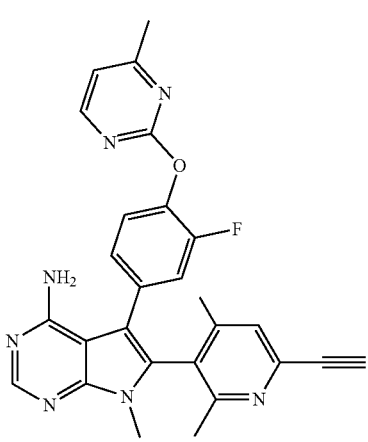 [SMILES: C#Cc1cc(C)c(-c2c(-c3ccc(Oc4nccc(C)n4)c(F)c3)c3c(N)ncnc3n2C)c(C)n1]

Step 7: The resulting crude material was purified by prep chiral HPLC (Column: DZ-CHIRALPAK IF-3, 4.6*50 mm, 3 um; Mobile Phase A:Hex(0.2% IPAmine):(EtOH:DCM=1:1)=75:25). Lyophilization yielded 6-(6-ethynyl-2,4-dimethylpyridin-3-yl)-5-{3-fluoro-4-[(4-methylpyrimidin-2-yl)oxy]phenyl}-7-methyl-7H-pyrrolo[2,3-d]pyrimidin-4-amine (PEAK 1) (33.7 mg, 70.2 μmol, 33.7%) as an off-white amorphous solid; 6-(6-ethynyl-2,4-dimethylpyridin-3-yl)-5-{3-fluoro-4-[(4-methylpyrimidin-2-yl)oxy]phenyl}-7-methyl-7H-pyrrolo[2,3-d]pyrimidin-4-amine(PEAK 2) (25 mg, 52.1 μmol, 25%) as an off-white amorphous solid.

Additional compounds prepared according to the methods of Example 32 are depicted in Table 31 below.

TABLE 31

Additional Exemplary Compounds

| Compound | Structure | Proton NMR | MS [M + 1] |
|---|---|---|---|
| 6-(6-ethynyl-2-fluoro-4-methylpyridin-3-yl)-5-(3-fluoro-4-((4-methylpyrimidin-2-yl)oxy)phenyl)-7-methyl-7H-pyrrolo[2,3-d]pyrimidin-4-amine | | 1H NMR (400 MHz, DMSO-d6) δ 8.48 (d, J = 5.0 Hz, 1H), 8.25 (s, 1H), 7.59 (s, 1H), 7.35 (t, J = 8.4 Hz, 1H), 7.19 (d, J = 5.1 Hz, 1H), 7.13 (dd, J = 11.3, 2.1 Hz, 1H), 7.01-6.96 (m, 1H), 6.21 (s, 1H), 4.59 (s, 1H), 3.49 (s, 3H), 2.41 (s, 3H), 2.02 (s, 3H). | 484.15 |
| 6-(6-ethynyl-2-fluoro-4-methylpyridin-3-yl)-5-(3-fluoro-4-((4-methylpyrimidin-2-yl)oxy)phenyl)-7-methyl-7H-pyrrolo[2,3-d]pyrimidin-4-amine | Atropisomer 1 | 1H NMR (400 MHz, DMSO-d6) δ 8.48 (d, J = 5.0 Hz, 1H), 8.25 (s, 1H), 7.59 (s, 1H), 7.36 (d, J = 8.4 Hz, 1H), 7.19 (d, J = 5.1 Hz, 1H), 7.14 (dd, J = 11.3, 2.1 Hz, 1H), 7.04-6.93 (m, 1H), 6.21 (s, 2H), 4.59 (s, 1H), 3.50 (s, 4H), 2.41 (s, 3H), 2.03 (s, 3H). | 484.15 |
| 6-(6-ethynyl-2-fluoro-4-methylpyridin-3-yl)-5-(3-fluoro-4-((4-methylpyrimidin-2-yl)oxy)phenyl)-7-methyl-7H-pyrrolo[2,3-d]pyrimidin-4-amine | Atropisomer 2 | 1H NMR (400 MHz, DMSO-d6) δ 8.48 (d, J = 5.0 Hz, 1H), 8.25 (s, 1H), 7.59 (s, 1H), 7.36 (d, J = 8.4 Hz, 1H), 7.19 (d, J = 5.1 Hz, 1H), 7.14 (dd, J = 11.3, 2.1 Hz, 1H), 7.04-6.93 (m, 1H), 6.21 (s, 2H), 4.59 (s, 1H), 3.50 (s, 4H), 2.41 (s, 3H), 2.03 (s, 3H). | 484.15 |

TABLE 31-continued

Additional Exemplary Compounds

| Compound | Structure | Proton NMR | MS [M + 1] |
|---|---|---|---|
| 6-(6-ethynyl-2,4-dimethylpyridin-3-yl)-5-(3-fluoro-4-((4-methylpyrimidin-2-yl)oxy)phenyl)-7-methyl-7H-pyrrolo[2,3-d]pyrimidin-4-amine | | 1H NMR (300 MHz, DMSO-d6) 8.45 (d, J = 5.0 Hz, 1H), 8.22 (s, 1H), 7.42 (s, 1H), 7.30 (t, J = 8.4 Hz, 1H), 7.16 (d, J = 5.0 Hz, 1H), 7.05 (dd, J = 11.5, 2.0 Hz, 1H), 6.94 (dt, J = 8.3, 1.4 Hz, 1H), 6.16 (s, 1H), 4.35 (s, 1H), 3.32(s, 3H), 2.38 (s, 3H), 2.14 (s, 3H), 2.00 (s, 3H). | 480.15 |
| 6-(6-ethynyl-2,4-dimethylpyridin-3-yl)-5-(3-fluoro-4-((4-methylpyrimidin-2-yl)oxy)phenyl)-7-methyl-7H-pyrrolo[2,3-d]pyrimidin-4-amine | Atropisomer 1 | 1H NMR (400 MHz, DMSO-d6) 8.47 (d, J = 5.0 Hz, 1H), 8.24 (s, 1H), 7.44 (s, 1H), 7.32 (t, J = 8.4 Hz, 1H), 7.18 (d, J = 5.1 Hz, 1H), 7.07 (dd, J = 11.4, 2.1 Hz, 1H), 7.00-6.93 (m, 1H), 6.15 (s, 2H), 4.36 (s, 1H), 3.34 (s, 3H), 2.41 (s, 3H), 2.16 (s, 3H), 2.02 (s, 3H). | 480.15 |
| 6-(6-ethynyl-2,4-dimethylpyridin-3-yl)-5-(3-fluoro-4-((4-methylpyrimidin-2-yl)oxy)phenyl)-7-methyl-7H-pyrrolo[2,3-d]pyrimidin-4-amine | Atropisomer 2 | 1H NMR (400 MHz, DMSO-d6) 8.47 (d, J = 5.0 Hz, 1H), 8.24 (s, 1H), 7.44 (s, 1H), 7.32 (t, J = 8.4 Hz, 1H), 7.18 (d, J = 5.0 Hz, 1H), 7.07 (dd, J = 11.4, 2.0 Hz, 1H), 6.97 (d, J = 8.5 Hz, 1H), 6.15 (s, 2H), 4.37 (s, 1H), 3.41 (s, 3H), 2.41 (s, 3H), 2.16 (s, 3H), 2.02 (s, 3H). | 480.15 |

TABLE 31-continued

Additional Exemplary Compounds

| Compound | Structure | Proton NMR | MS [M + 1] |
|---|---|---|---|
| N-(4-(4-amino-7-methyl-5-(4-((4-methylpyrimidin-2-yl)oxy)phenyl)-7H-pyrrolo[2,3-d]pyrimidin-6-yl)-3,5-dimethylphenyl)methacrylamide | 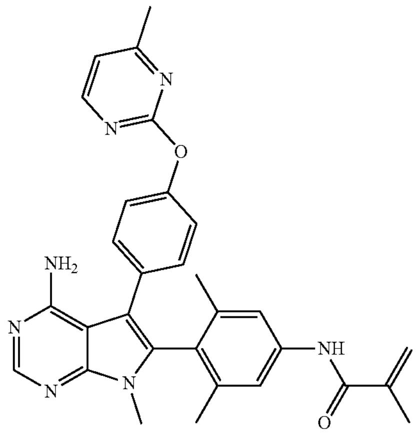 [SMILES: C=C(C)C(=O)Nc1cc(C)c(-c2c(-c3ccc(Oc4nccc(C)n4)cc3)c3c(N)ncnc3n2C)c(C)c1] | $^1$H NMR (400 MHz, DMSO-$d_6$) δ 9.74 (s, 1H), 8.45 (d, J = 5.0 Hz, 1H), 8.21 (s, 1H), 7.50 (s, 2H), 7.28-7.10 (m, 5H), 5.80 (m, 2H), 5.52 (s, 1H), 3.37 (s, 3H), 2.40 (s, 3H), 1.96 (m, 9H). | 520.40 |
| ((S)-4-(4-amino-6-(6-ethynyl-2-fluoro-4-methylpyridin-3-yl)-7-methyl-7H-pyrrolo[2,3-d]pyrimidin-5-yl)cyclohex-3-en-1-yl)((R)-2-methylpyrrolidin-1-yl)methanone | 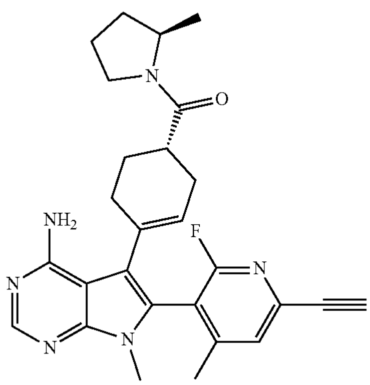 [SMILES: C#Cc1cc(C)c(-c2c(C3=CC[C@@H](C(=O)N4CCC[C@H]4C)CC3)c3c(N)ncnc3n2C)c(F)n1] | 1H NMR (400 MHz, DMSO-d6) δ 8.14 (t, J = 2.8 Hz, 1H), 7.65 (s, 1H), 6.61 (s, 2H), 5.61 (s, 1H), 4.60 (d, J = 1.1 Hz, 1H), 4.01(s, 1H), 3.51 (d, J = 8.6 Hz, 2H), 3.46-3.36 (m, 3H), 2.71 (s, 1H), 2.17 (s, 5H), 1.91-1.80 (s, 5H), 1.62 (s, 1H), 1.49 (d, J = 5.0 Hz, 1H), 1.17-1.03 (m, 3H). | 473.30 |

Example 33

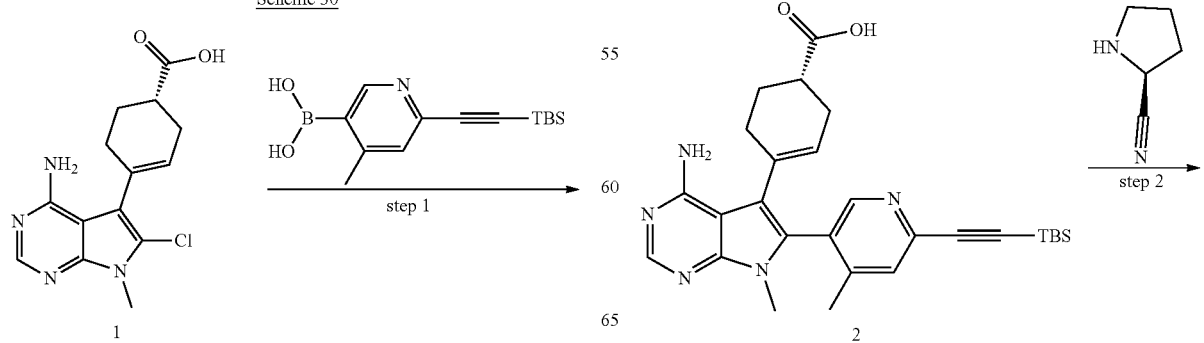

1809

-continued

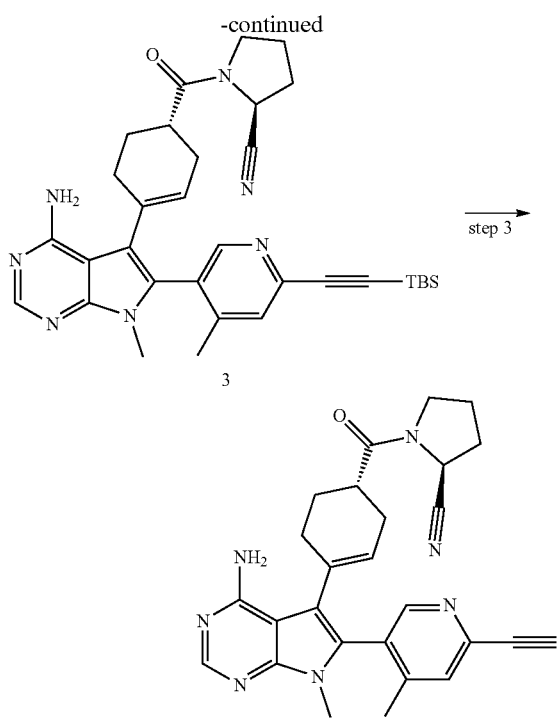

(S)-4-(4-amino-6-(6-((tert-butyldimethylsilyl)ethynyl)-4-methylpyridin-3-yl)-7-methyl-7H-pyrrolo[2,3-d]pyrimidin-5-yl)cyclohex-3-ene-1-carboxylic acid

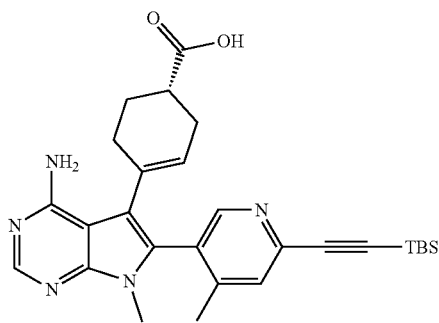

Step 1: A round bottomed flask was charged was charged with (1S)-4-{4-amino-6-chloro-7-methyl-7H-pyrrolo[2,3-d]pyrimidin-5-yl}cyclohex-3-ene-1-carboxylic acid (6 g, 19.5 mmol), {6-[2-(tert-butyldimethylsilyl)ethynyl]-4-methylpyridin-3-yl}boronic acid (10.7 g, 39.0 mmol), Na2CO3 (6.19 g, 58.4 mmol), Xphos Pd.G3. (1.65 g, 1.95 mmol), Xphos (928 mg, 1.95 mmol), dioxane/H2O (120 mL) and a stir bar before being evacuated and purged with nitrogen three times. The mixture was stirred for 1 h at 90° C. The reaction mixture was filtered, washed with DCM, the filtrate was concentrated in vacuo. and then the resulting crude material was purified by combiflash (A:0.1% of TFA in water, B:acetonitrile). Concentration in vacuo resulted in (1S)-4-(4-amino-6-{6-[2-(tert-butyldimethylsilyl)ethynyl]-4-methylpyridin-3-yl}-7-methyl-7H-pyrrolo[2,3-d]pyrimidin-5-yl)cyclohex-3-ene-1-carboxylic acid (6.20 g, 63%) as a yellow solid.

1810

(S)-1-((S)-4-(4-amino-6-(6-(((tert-butyldimethylsilyl)ethynyl)-4-methylpyridin-3-yl)-7-methyl-7H-pyrrolo[2,3-d]pyrimidin-5-yl)cyclohex-3-ene-1-carbonyl)pyrrolidine-2-carbonitrile

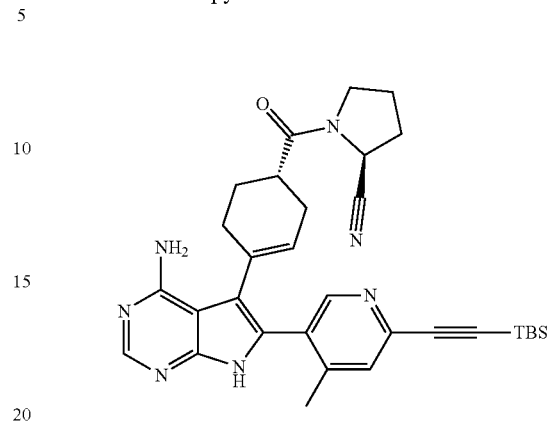

Step 2: A round bottomed flask was charged with (1S)-4-(4-amino-6-{6-[2-(tert-butyldimethylsilyl)ethynyl]-4-methylpyridin-3-yl}-7-methyl-7H-pyrrolo[2,3-d]pyrimidin-5-yl)cyclohex-3-ene-1-carboxylic acid (5 g, 9.96 mmol), (2S)-pyrrolidine-2-carbonitrile (2.86 g, 29.8 mmol), HATU (7.56 g, 19.9 mmol), DMF (100 mL) and a stir bar. DIEA (15.0 g, 116 mmol) was added, and the solution was stirred for 2 h at r.t. The reaction mixture was diluted with water (150 mL), and the aqueous phase was extracted with EA (300 mL) three times. The combined organic layers were washed with brine, dried over sodium sulfate, filtered, and concentrated in vacuo. The resulting crude material was purified by silica gel chromatography (200 g column; eluting with dichloromethane/methanol; ratio=30:1). Concentration in vacuo resulted in (2S)-1-[(1S)-4-(4-amino-6-{6-[2-(tert-butyldimethylsilyl)ethynyl]-4-methylpyridin-3-yl}-7-methyl-7H-pyrrolo[2,3-d]pyrimidin-5-yl)cyclohex-3-ene-1-carbonyl]pyrrolidine-2-carbonitrile (2.80 g, 48%) as dark oil.

(5)-1-((S)-4-(4-amino-6-(6-ethynyl-4-methylpyridin-3-yl)-7-methyl-7H-pyrrolo[2,3-d]pyrimidin-5-yl)cyclohex-3-ene-1-carbonyl)pyrrolidine-2-carbonitrile

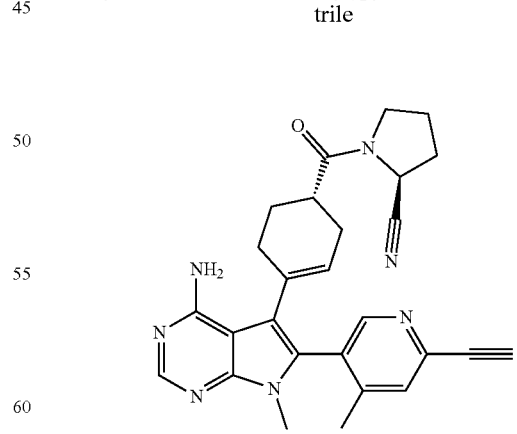

Step 3: A round bottomed flask was charged with (2S)-1-[(1S)-4-(4-amino-6-{6-[2-(tert-butyldimethylsilyl)ethynyl]-4-methylpyridin-3-yl}-7-methyl-7H-pyrrolo[2,3-d]pyrimidin-5-yl)cyclohex-3-ene-1-carbonyl]pyrrolidine-2-carbonitrile (2.7 g, 4.65 mmol), THF (10 mL) and a stir bar.

TBAF (1.21 g, 4.65 mmol) was added, and the solution was stirred for 30 min at r.t. The reaction mixture was diluted with water (150 mL), and the aqueous phase was extracted with DCM (100 mL) three times. The combined organic layers were washed with brine, dried over sodium sulfate, filtered, and concentrated in vacuo. The resulting crude material was purified by flash (Mobile Phase A:Water, Mobile Phase B:ACN). The resulting crude material was purified by HPLC (Column: Xselect CSH OBD Column 30*150 mm 5 um, n; Mobile Phase A:Water(0.1% FA), Mobile Phase B:MeOH-HPLC; Flow rate:60 mL/min; Gradient:20 B to 45 B in 7 min; 220 nm; RT1:7.13; RT2). Lyophilization yielded (2S)-1-[(1S)-4-[4-amino-6-(6-ethynyl-4-methylpyridin-3-yl)-7-methyl-7H-pyrrolo[2,3-d]pyrimidin-5-yl]cyclohex-3-ene-1-carbonyl]pyrrolidine-2-carbonitrile (520 mg, 24%) as off-white amorphous solid.

Additional compounds prepared according to the methods of Example 33 are depicted in Table 32 below.

TABLE 32

Additional Exemplary Compounds

| Compound | Structure | Proton NMR | MS [M + 1] |
|---|---|---|---|
| (2S)-1-[(1S)-4-[4-amino-6-(6-ethynyl-2-methylpyridin-3-yl)-7-methyl-7H-pyrrolo[2,3-d]pyrimidin-5-yl]cyclohex-3-ene-1-carbonyl]pyrrolidine-2-carbonitrile | 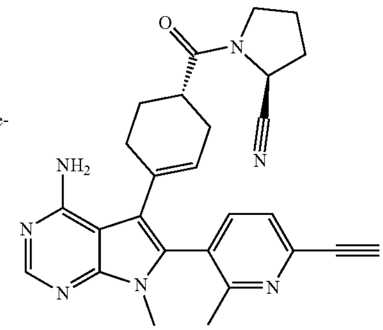 | $^1$H NMR (400 MHz, DMSO-d$_6$) δ 8.15 (s, 1H), 7.88-7.64 (m, 1H), 7.53 (d, J = 7.9 Hz, 1H), 6.57 (s, 1H), 5.70 (d, J = 11.1 Hz, 1H), 4.92-4.54 (m, 1H), 4.43 (s, 1H), 3.68 (d, J = 8.0 Hz, 1H), 3.53-3.43 (m, 1H), 3.38 (s, 3H), 2.81 (d, J = 6.4 Hz, 1H), 2.28 (d, J = 2.3 Hz, 3H), 2.23 (s, 2H), 2.13 (d, J = 6.5 Hz, 2H), 2.09-1.73 (m, 4H), 1.61 (s, 2H). | 466.30 |
| (2S)-1-[(1R)-4-[4-amino-6-(6-ethynyl-4-methylpyridin-3-yl)-7-methyl-7H-pyrrolo[2,3-d]pyrimidin-5-yl]cyclohex-3-ene-1-carbonyl]pyrrolidine-2-carbonitrile | 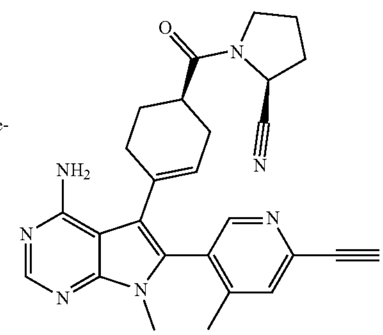 | $^1$H NMR (400 MHz, DMSO-d$_6$) δ 8.41 (d, J = 25.1 Hz, 1H), 8.17 (s, 1H), 7.64 (d, J = 3.9 Hz, 1H), 6.73 (s, 1H), 5.71 (d, J = 28.0 Hz, 1H), 4.71 (dd, J = 7.9, 3.8 Hz, 1H), 4.43 (s, 1H), 3.70-3.48 (m, 2H), 3.39 (d, J = 1.5 Hz, 3H), 2.86-2.74 (m, 1H), 2.28-2.20 (m, 2H), 2.14 (d, J = 7.2 Hz, 5H), 2.06-1.83 (m, 4H), 1.72-1.58 (m, 2H). | 466.20 |
| (2S)-1-[(1S)-4-[4-amino-6-(6-ethynyl-4-methylpyridin-3-yl)-7-methyl-7H-pyrrolo[2,3-d]pyrimidin-5-yl]cyclohex-3-ene-1-carbonyl]pyrrolidine-2-carbonitrile | 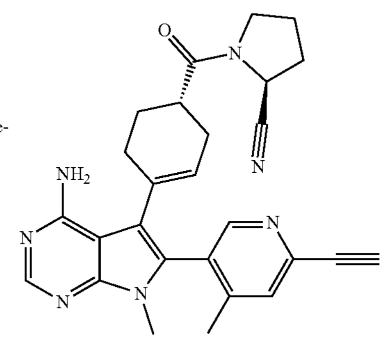 | $^1$H NMR (400 MHz, DMSO-d$_6$) δ 8.40 (d, J = 5.1 Hz, 1H), 8.14 (s, 1H), 7.64 (d, J = 1.9 Hz, 1H), 6.53 (s, 1H), 5.76 (s, 1H), 4.70 (dt, J = 7.3, 3.2 Hz, 1H), 4.43 (d, J = 1.2 Hz, 1H), 3.69 (s, 1H), 3.65-3.42 (m, 1H), 3.38 (d, J = 0.9 Hz, 3H), 2.80 (s, 1H), 2.24 (s, 2H), 2.14 (s, 5H), 2.07-1.81 (m, 4H), 1.60 (s, 2H). | 466.35 |

Example 34

Scheme 31

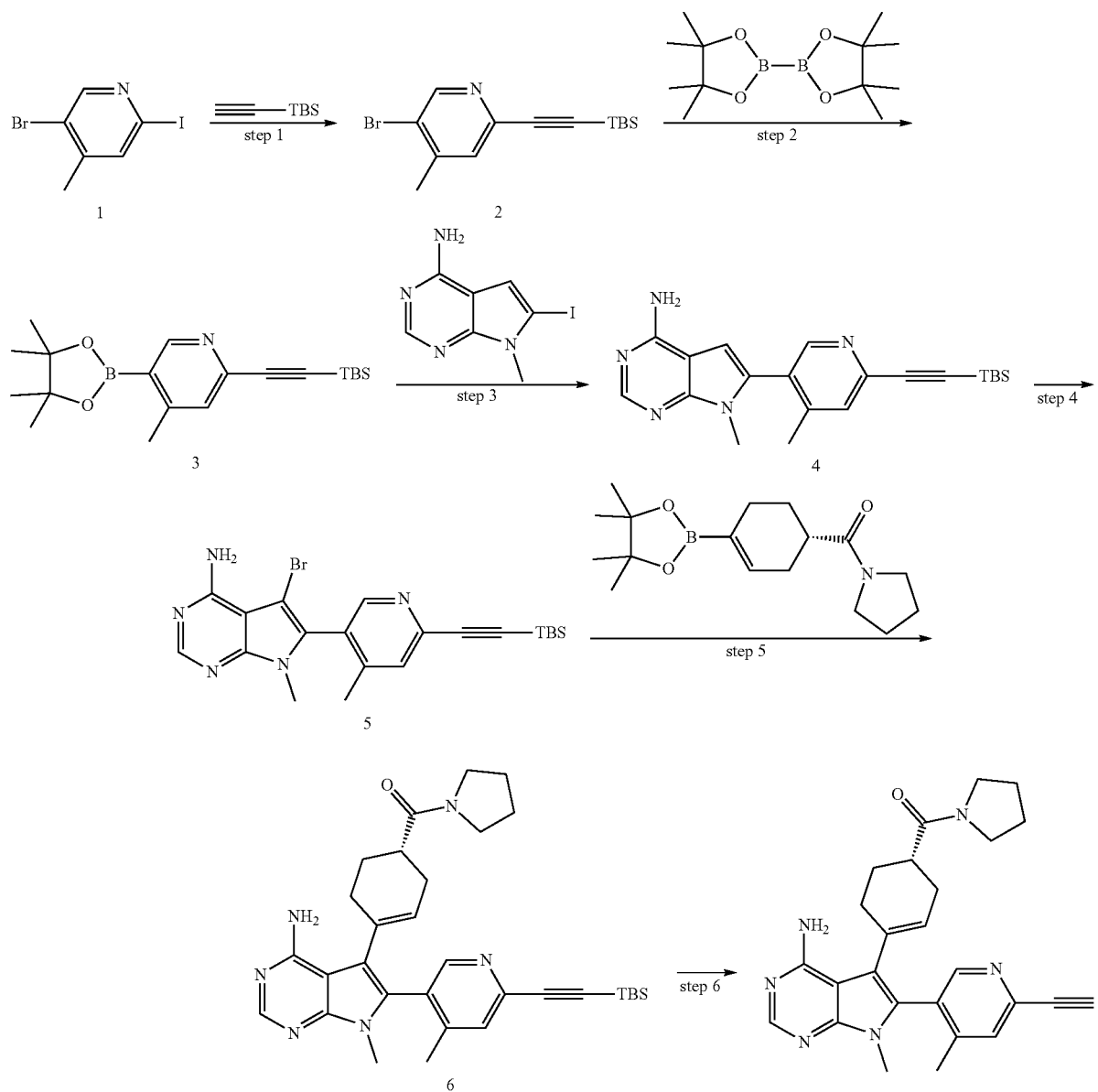

5-bromo-2-((tert-butyldimethylsilyl)ethynyl)-4-methylpyridine

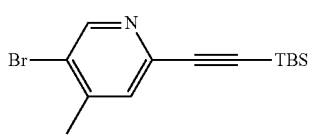

Step 1: A resealable reaction vial was charged with 5-bromo-2-iodo-4-methylpyridine (5.00 g, 16.8 mmol), dimethylformamide (50 mL), CuI (1.28 g, 6.72 mmol), Et₃N (8.48 g, 84 mmol), Pd(PPh₃)₂Cl₂ (2.36 g, 3.36 mmol), tert-butyl(ethynyl)dimethylsilane (2.35 g, 16.8 mmol) and a stir bar before being evacuated and purged with nitrogen three times. The mixture was stirred for 2 h at 50° C. The reaction mixture was diluted with water (200 mL), and the aqueous phase was extracted with EA (50 mL) three times. The combined organic layers were washed with brine, dried over sodium sulfate, filtered, and concentrated in vacuo. The resulting crude material was purified by silica gel chromatography (eluting with heptanes/ethyl acetate; 10:1). Concentration in vacuo resulted in 5-bromo-2-((tert-butyldimethylsilyl)ethynyl)-4-methylpyridine (4 g, 77%) as a yellow amorphous solid.

1815

2-((tert-butyldimethylsilyl)ethynyl)-4-methyl-5-(4,4,5,5-tetramethyl-1,3,2-dioxaborolan-2-yl)pyridine

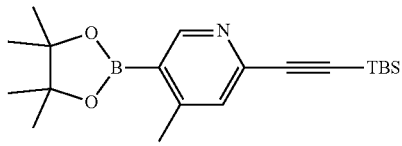

Step 2: A resealable reaction vial was charged with 5-bromo-2-((tert-butyldimethylsilyl)ethynyl)-4-methylpyridine (3.5 g, 11.3 mmol), 4,4,5,5-tetramethyl-2-(4,4,5,5-tetramethyl-1,3,2-dioxaborolan-2-yl)-1,3,2-dioxaborolane (3.07 g, 12.1 mmol), AcOK (2.37 g, 24.2 mmol), Pd(dppf)Cl$_2$ (589 mg, 807 µmol), dioxane (40 mL) and a stir bar before being evacuated and purged with nitrogen three times, and the mixture was stirred for 1 h at 80° C. The reaction mixture was diluted with water (100 mL), and the aqueous phase was extracted with EA (50 mL) three times. The combined organic layers were washed with brine, dried over sodium sulfate, filtered, and concentrated in vacuo. The resulting crude material was purified by HPLC (acetonitrile/water 0~50%). Lyophilization yielded 2-((tert-butyldimethylsilyl)ethynyl)-4-methyl-5-(4,4,5,5-tetramethyl-1,3,2-dioxaborolan-2-yl)pyridine (3.90 g, 90%) as an off-white amorphous solid.

6-(6-((tert-butyldimethylsilyl)ethynyl)-4-methylpyridin-3-yl)-7-methyl-7H-pyrrolo[2,3-d]pyrimidin-4-amine

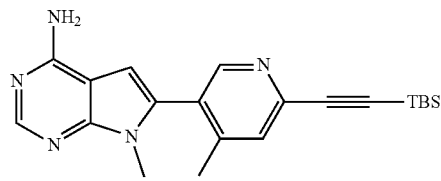

Step 3: A resealable reaction vial was charged with 2-((tert-butyldimethylsilyl)ethynyl)-4-methyl-5-(4,4,5,5-tetramethyl-1,3,2-dioxaborolan-2-yl)pyridine (2.6 g, 7.26 mmol), 6-iodo-7-methyl-7H-pyrrolo[2,3-d]pyrimidin-4-amine (1.67 g, 6.05 mmol), Pd(dppf)Cl$_2$ (442 mg, 605 µmol), K$_3$PO$_4$ (3.83 g, 18.1 mmol), DME:H$_2$O (10:1.25 mL) and a stir bar before being evacuated and purged with nitrogen three times, and the mixture was stirred for 3 h at 90° C. The reaction mixture was diluted with water (40 mL), and the aqueous phase was extracted with DCM (40 mL) three times. The combined organic layers were washed with saturated salt water, dried over sodium sulfate, filtered, and concentrated in vacuo. The resulting crude material was purified by HPLC (acetonitrile/water=0~50%). Lyophilization yielded 6-(6-((tert-butyldimethylsilyl)ethynyl)-4-methylpyridin-3-yl)-7-methyl-7H-pyrrolo[2,3-d]pyrimidin-4-amine (1.6 g, 70%) as a yellow amorphous solid.

1816

5-bromo-6-{6-[2-(tert-butyldimethylsilyl)ethynyl]-4-methylpyridin-3-yl}-7-methyl-7H-pyrrolo[2,3-d]pyrimidin-4-amine

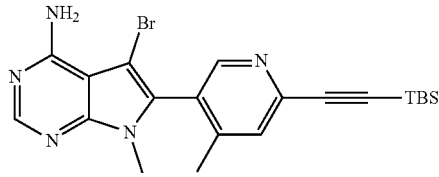

Step 4: A round bottomed flask was charged with 6-(6-((tert-butyldimethylsilyl)ethynyl)-4-methylpyridin-3-yl)-7-methyl-7H-pyrrolo[2,3-d]pyrimidin-4-amine (1.6 g, 4.24 mmol), DCM (20 mL) and a stir bar. NBS (754.7 mg, 4.24 mmol) was added. The mixture was stirred for 1 h at room temperature. The reaction mixture was quenched with saturated NaHSO$_3$ aqueous solution until the pH to 8-9, extracted with DCM (100 mL*3), the organic phase was combined and washed with brine, dried over Na$_2$SO$_4$, evaporated in vacuo, the residue was dissolved with ACN (25 mL), and filtered, the filter cake was washed with ACN, dried under reduced pressure to afford 5-bromo-6-{6-[2-(tert-butyldimethylsilyl)ethynyl]-4-methylpyridin-3-yl}-7-methyl-7H-pyrrolo[2,3-d]pyrimidin-4-amine (1.6 g, 83%) as an off-white solid.

(S)-(4-(4-amino-6-(6-((tert-butyldimethylsilyl)ethynyl)-4-methylpyridin-3-yl)-7-methyl-7H-pyrrolo[2,3-d]pyrimidin-5-yl)cyclohex-3-en-1-yl)(pyrrolidin-1-yl)methanone

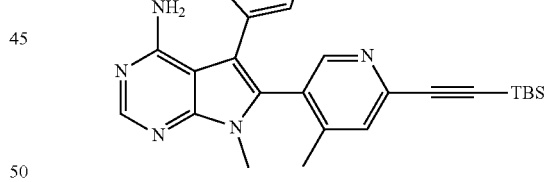

Step 5: A resealable reaction vial was charged with 5-bromo-6-{6-[2-(tert-butyldimethylsilyl)ethynyl]-4-methylpyridin-3-yl}-7-methyl-7H-pyrrolo[2,3-d]pyrimidin-4-amine (500 mg, 1.09 mmol), DME:H$_2$O (10:1.8 mL), [(4S)-4-(pyrrolidine-1-carbonyl)cyclohex-1-en-1-yl]boronic acid (290 mg, 1.30 mmol), Pd(dppf)Cl$_2$ (79.6 mg, 109 µmol), K$_3$PO$_4$ (693 mg, 3.27 mmol) and a stir bar before being evacuated and purged with nitrogen three times. The mixture was stirred for 2 h at 90° C. The reaction mixture was diluted with water (50 mL), and the aqueous phase was extracted with EA (30 mL) three times. The combined organic layers were washed with Saturated salt water, dried over sodium sulfate, filtered, and concentrated in vacuo. The crude material was purified by silica gel chromatography (1 g column; eluting with EA). Concentration in vacuo resulted in 6-{6-[2-(tert-butyldimethylsilyl)ethynyl]-4-methylpyridin-3-yl}-7-methyl-5-[(4S)-4-(pyrrolidine-1-carbonyl)cy-clohex-1-en-1-yl]-7H-pyrrolo[2,3-d]pyrimidin-4-amine (110 mg, 18%) as a brown solid.

(S)-(4-(4-amino-6-(6-ethynyl-4-methylpyridin-3-yl)-7-methyl-7H-pyrrolo[2,3-d]pyrimidin-5-yl)cyclohex-3-en-1-yl)(pyrrolidin-1-yl)methanone

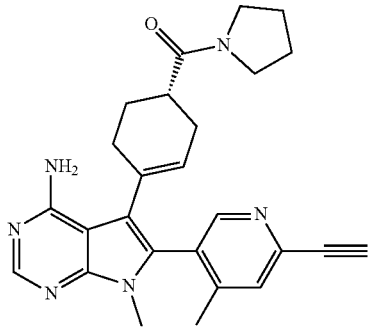

Step 6: A resealable reaction vial was charged with 6-{6-[2-(tert-butyldimethylsilyl)ethynyl]-4-methylpyridin-3-yl}-7-methyl-5-[(4S)-4-(pyrrolidine-1-carbonyl)cyclohex-1-en-1-yl]-7H-pyrrolo[2,3-d]pyrimidin-4-amine (100 mg, 180 μmol), THF (6 mL) and a stir bar. TBAF (2.2 mL, 216 μmol) was added, and the mixture was stirred for 30 min at room temperature. The reaction mixture was diluted with water (20 mL), and the aqueous phase was extracted with DCM (20 mL) three times. The combined organic layers were washed with brine five times, dried over sodium sulfate, filtered, and concentrated in vacuo. The resulting crude material was purified by prep-HPLC (acetonitrile/water/10 mmol NH$_4$HCO$_3$), Flow rate:60 mL/min; Gradient:40 B to 65 B in 8 min. Lyophilization yielded 6-(6-ethynyl-4-methylpyridin-3-yl)-7-methyl-5-[(4S)(pyrrolidine-1-carbonyl)cyclohex-1-en-1-yl]-7H-pyrrolo[2,3-d]pyrimidin-4-amine (27.6 mg, 35%) as an off-white amorphous solid.

Additional compounds prepared according to the methods of Example 34 are depicted in Table 33 below.

TABLE 33

Additional Exemplary Compounds

| Compound | Structure | Proton NMR | MS [M + 1] |
|---|---|---|---|
| (R)-(4-(4-amino-6-(6-ethynyl-4-methylpyridin-3-yl)-7-methyl-7H-pyrrolo[2,3-d]pyrimidin-5-yl)cyclohex-3-en-1-yl)(pyrrolidin-1-yl)methanone | 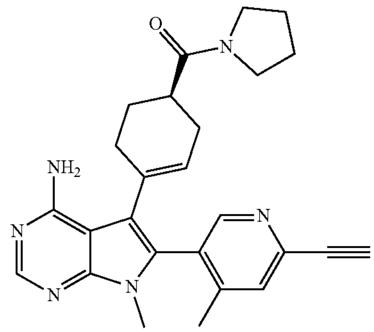 [SMILES: C#Cc1cc(C)c(-c2c(C3=CC[C@H](C(=O)N4CCCC4)CC3)c3c(N)ncnc3n2C)cn1] | 1H NMR (400 MHz, DMSO-d6) 8.40 (d, J = 11.7 Hz, 1H), 8.13 (s, 1H), 7.63 (d, J = 2.7 Hz, 1H), 6.59 (s, 1H), 5.69 (d, J = 30.0 Hz, 1H), 4.42 (d, J = 1.1 Hz, 1H), 3.51-3.38 (m, 2H), 3.37 (d, J = 1.4 Hz, 3H), 3.28 (s, 2H), 2.75 (s, 1H), 2.68 (p, J = 1.8 Hz, 2H), 2.34 (p, J = 1.9 Hz, 5H), 2.20 (d, J = 7.1 Hz, 1H), 1.93 (d, J = 9.1 Hz, 2H), 1.85 (q, J = 6.1 Hz, 2H), 1.60 (d, J = 7.0 Hz, 2H). | 441.35 |
| (S)-(4-(4-amino-6-(6-ethynyl-4-methylpyridin-3-yl)-7-methyl-7H-pyrrolo[2,3-d]pyrimidin-5-yl)cyclohex-3-en-1-yl)(pyrrolidin-1-yl)methanone | 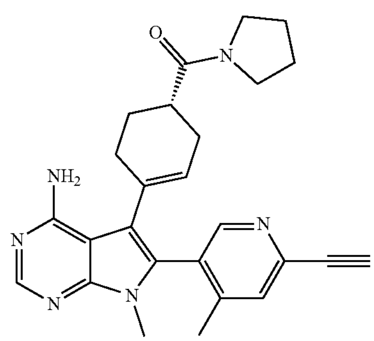 [SMILES: C#Cc1cc(C)c(-c2c(C3=CC[C@@H](C(=O)N4CCCC4)CC3)c3c(N)ncnc3n2C)cn1] | $^1$H NMR (400 MHz, Methanol-d$_4$) δ 8.39 (d, J = 6.7 Hz, 1H), 8.17 (s, 1H), 7.65 (d, J = 3.2 Hz, 1H), 5.99-5.76 (m, 1H), 3.89 (d, J = 1.8 Hz, 1H), 3.62-3.50 (m, 2H), 3.49 (s, 3H), 3.43 (ddt, J = 9.3, 6.4, 3.7 Hz, 2H), 2.90-2.78 (m, 1H), 2.44-2.30 (m, 1H), 2.24 (d, J = 3.1 Hz, 4H), 2.11 (s, 2H), 1.98 (qd, J = 6.4, 2.1 Hz, 2H), 1.90 (td, J = 6.5, 1.4 Hz, 2H), 1.76 (dq, J = 14.4, 6.3 Hz, 2H). | 441.35 |

TABLE 33-continued

Additional Exemplary Compounds

| Compound | Structure | Proton NMR | MS [M + 1] |
|---|---|---|---|
| 4-(4-amino-6-(6-ethynyl-4-methylpyridin-3-yl)-7-methyl-7H-pyrrolo[2,3-d]pyrimidin-5-yl)-N-cyclobutyl-2-methoxybenzamide | 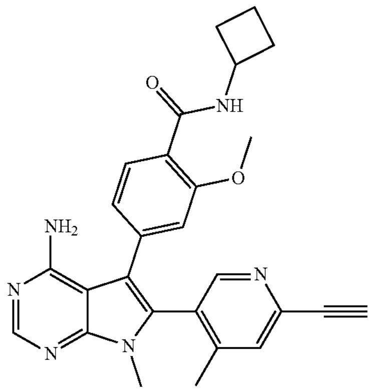 [SMILES: C#Cc1cc(C)c(-c2c(-c3ccc(C(=O)NC4CCC4)c(OC)c3)c3c(N)ncnc3n2C)cn1] | $^1$H NMR (400 MHz, Methanol-d$_4$) δ 8.45 (s, 1H), 8.27 (s, 1H), 7.77 (d, J = 7.8 Hz, 1H), 7.56 (s, 1H), 7.00-6.89 (m, 2H), 4.48 (p, J = 8.3 Hz, 1H), 3.86 (s, 1H), 3.81 (s, 3H), 3.60 (s, 3H), 2.38 (d, J = 8.2 Hz, 2H), 2.13-1.99 (m, 5H), 1.85-1.75 (m, 2H). | 467.15 |
| 6-(6-ethynyl-2-methylpyridin-3-yl)-5-(3-fluoro-4-((4-methylpyrimidin-2-yl)oxy)phenyl)-7-methyl-7H-pyrrolo[2,3-d]pyrimidine | 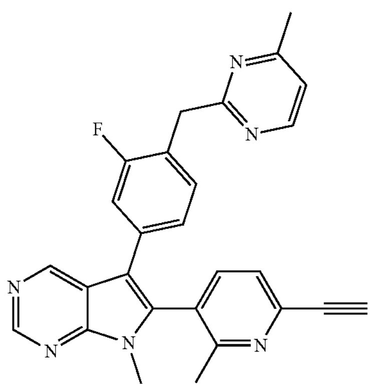 [SMILES: C#Cc1ccc(-c2c(-c3ccc(Cc4nccc(C)n4)c(F)c3)c3cncnc3n2C)c(C)n1] | $^1$H NMR (400 MHz, DMSO) 9.22 (s, 1H), 8.95 (s, 1H), 8.45 (d, J = 5.0 Hz, 1H), 7.99 (d, J = 7.9 Hz, 1H), 7.60 (d, J = 7.9 Hz, 1H), 7.38-7.23 (m, 2H), 7.17 (d, J = 5.1 Hz, 1H), 7.07 (ddd, J = 8.4, 2.2, 0.8 Hz, 1H), 4.47 (s, 1H), 3.57 (s, 3H), 2.40 (s, 3H), 2.14 (s, 3H). | 451.15 |
| (R)-(4-(6-(6-ethynyl-2-methylpyridin-3-yl)-7-methyl-7H-pyrrolo[2,3-d]pyrimidin-5-yl)cyclohex-3-en-1-yl)(pyrrolidin-1-yl)methanone | 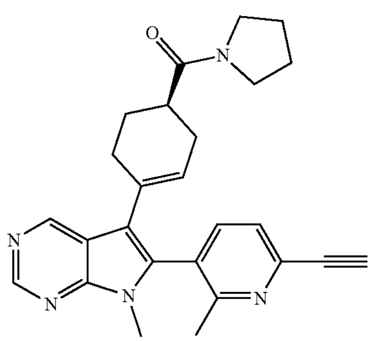 [SMILES: C#Cc1ccc(-c2c(C3=CC[C@H](C(=O)N4CCCC4)CC3)c3cncnc3n2C)c(C)n1] | $^1$H NMR (400 MHz, DMSO-d$_6$) 9.14 (s, 1H), 8.86 (s, 1H), 7.86 (dd, J = 20.9, 7.9 Hz, 1H), 7.58 (d, J = 7.9 Hz, 1H), 5.81 (s, 1H), 4.47 (d, J = 1.7 Hz, 1H), 3.51-3.42 (m, 5H), 3.27 (t, J = 6.8 Hz, 2H), 2.61 (d, J = 12.8 Hz, 1H), 2.26 (t, J = 14.0 Hz, 7H), 1.87 (p, J = 6.7 Hz, 2H), 1.78-1.73 (m, 3H), 1.50 (td, J = 12.1, 5.7 Hz, 1H). | 426.30 |
| (S)-(4-(6-(6-ethynyl-2-methylpyridin-3-yl)-7-methyl-7H-pyrrolo[2,3-d]pyrimidin-5-yl)cyclohex-3-en-1-yl)(pyrrolidin-1-yl)methanone | 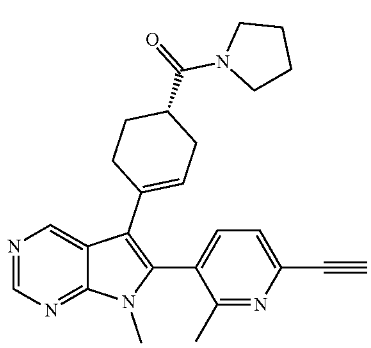 [SMILES: C#Cc1ccc(-c2c(C3=CC[C@@H](C(=O)N4CCCC4)CC3)c3cncnc3n2C)c(C)n1] | 1H NMR (400 MHz, DMSO-d6) 9.14 (s, 1H), 8.86 (s, 1H), 7.86 (dd, J = 20.9, 7.9 Hz, 1H), 7.58 (d, J = 7.8 Hz, 1H), 5.81 (s, 1H), 4.46 (d, J = 1.7 Hz, 1H), 3.47 (dd, J = 6.8, 4.7 Hz, 5H), 3.30 (s, 2H), 2.61 (d, J = 11.0 Hz, 1H), 2.28 (d, J = 7.5 Hz, 3H), 2.23 (s, 2H), 2.18 (s, 1H), 1.91-1.83 (m, 2H), 1.85-1.72 (m, 4H), 1.50 (td, J = 11.9, 5.5 Hz, 1H). | 426.30 |

TABLE 33-continued

Additional Exemplary Compounds

| Compound | Structure | Proton NMR | MS [M + 1] |
|---|---|---|---|
| 6-(6-ethynyl-2-methylpyridin-3-yl)-5-[(4S)-4-(2-ethynylpyrrolidine-1-carbonyl)cyclohex-1-en-1-yl]-7-methyl-7H-pyrrolo[2,3-d]pyrimidin-4-amine | 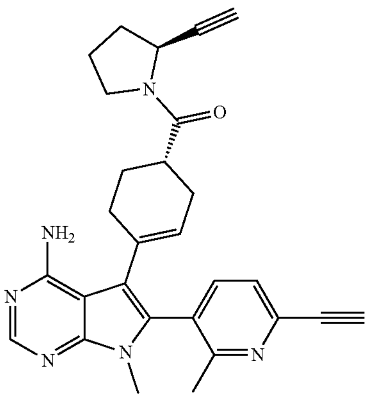 [SMILES: C#Cc1ccc(-c2c(C3=CC[C@@H](C(=O)N4CCC[C@H]4C#C)CC3)c3c(N)ncnc3n2C)c(C)n1] | $^1$H NMR (400 MHz, DMSO-d$_6$) δ 8.14 (d, J = 2.6 Hz, 1H), 7.73 (td, J = 6.7, 5.6, 2.4 Hz, 1H), 7.51 (s, 1H), 6.53 (s, 2H), 5.74-5.64 (m, 1H), 4.83 (d, J = 7.3 Hz, 1H), 4.43 (s, 1H), 3.61 (s, 1H), 3.38 (s, 3H), 3.26 (d, J = 11.8 Hz, 1H), 3.08 (d, J = 2.0 Hz, 1H), 2.96-2.63 (m, 1H), 2.32-2.15 (m, 3H), 2.15-2.06 (m, 2H), 2.04-1.80 (m, 6H), 1.75-1.53 (m, 2H). | 465.30 |
| 6-(6-ethynyl-2-methylpyridin-3-yl)-5-[(4S)-4-[(2R)-2-ethynylpyrrolidine-1-carbonyl]cyclohex-1-en-1-yl]-7-methyl-7H-pyrrolo[2,3-d]pyrimidin-4-amine | 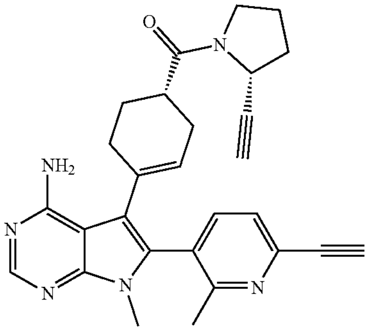 [SMILES: C#Cc1ccc(-c2c(C3=CC[C@@H](C(=O)N4CCC[C@@H]4C#C)CC3)c3c(N)ncnc3n2C)c(C)n1] | $^1$H NMR (400 MHz, DMSO-d6) δ 8.13 (d, J = 3.1 Hz, 1H), 7.80-7.66 (m, 1H), 7.52 (d, J = 7.8 Hz, 1H), 6.56 (s, 2H), 5.71 (dd, J = 24.3, 13.7 Hz, 1H), 4.87-4.52 (m, 1H), 4.43 (s, 1H), 3.57-3.48 (m, 1H), 3.38 (s, 3H), 3.30-3.19 (m, 1H), 3.11-2.99 (m, 1H), 2.97-2.60 (m, 1H), 2.38-2.31 (m, 3H), 2.18 (d, J = 46.6 Hz, 3H), 1.92 (dd, J = 39.2, 17.7 Hz, 6H), 1.61 (s, 2H). | 465.30 |
| ((S)-4-(4-amino-6-(6-ethynyl-4-methylpyridin-3-yl)pyrrolo[2,1-f][1,2,4]triazin-5-yl)cyclohex-3-en-1-yl)((R)-2-methylpyrrolidin-1-yl)methanone | 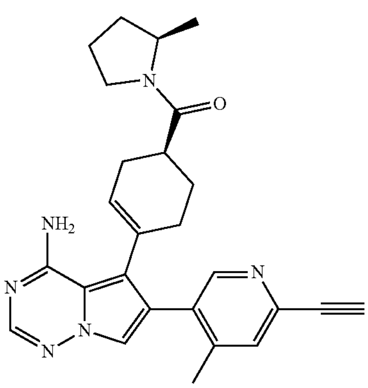 [SMILES: C#Cc1cc(C)c(-c2cn3ncnc(N)c3c2C2=CC[C@@H](C(=O)N3CCC[C@H]3C)CC2)cn1] | $^1$H NMR (400 MHz, DMSO-d$_6$) δ 8.34 (s, 1H), 7.86-7.81 (m, 2H), 7.53 (d, J = 22 Hz, 1H), 6.88 (s, 1H), 5.83 (s, 1H), 4.32 (s, 1H), 4.00 (t, J = 6.5 Hz, 1H), 3.58-3.50 (m, 1H), 3.40 (s, 1H), 2.82 (t, J = 5.7 Hz, 1H), 2.27 (s, 5H), 1.99-1.72 (m, 5H), 1.66-1.38 (m, 3H), 1.09 (dd, J = 6.4, 2.0 Hz, 3H). | 441.30 |
| ((R)-4-(4-amino-6-(6-ethynyl-4-methylpyridin-3-yl)pyrrolo[2,1-f][1,2,4]triazin-5-yl)cyclohex-3-en-1-yl)((R)-2-methylpyrrolidin-1-yl)methanone | 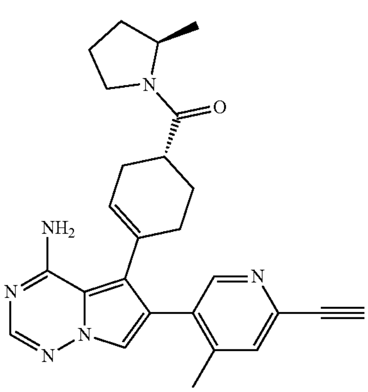 [SMILES: C#Cc1cc(C)c(-c2cn3ncnc(N)c3c2C2=CC[C@H](C(=O)N3CCC[C@H]3C)CC2)cn1] | $^1$H NMR (400 MHz, DMSO-d) δ 8.34 (d, J = 1.9 Hz, 1H), 7.83 (d, J = 3.2 Hz, 2H), 7.52 (s, 1H), 7.20 (s, 1H), 5.86 (s, 1H), 4.32 (s, 1H), 4.08-3.93 (m, 1H), 3.50 (d, J = 7.6 Hz, 1H), 3.46-3.39 (m, 1H), 2.88 (s, 1H), 2.27 (s, 5H), 2.07-1.26 (m, 8H), 1.08 (dd, J = 38.2, 6.3 Hz, 3H). | 441.30 |

TABLE 33-continued

Additional Exemplary Compounds

| Compound | Structure | Proton NMR | MS [M + 1] |
|---|---|---|---|
| 6-(6-ethynyl-4-methylpyridin-3-yl)-5-(3-fluoro-4-((4-methylpyrimidin-2-yl)oxy)phenyl)pyrrolo[2,1-f][1,2,4]triazin-4-amine | 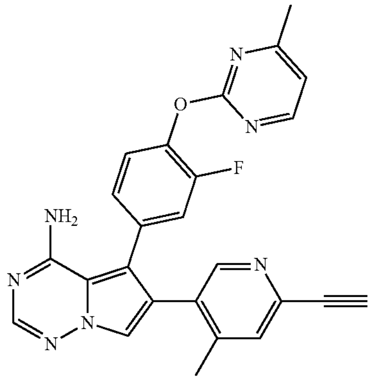 [SMILES: C#Cc1cc(C)c(-c2cn3ncnc(N)c3c2-c2ccc(Oc3nccc(C)n3)c(F)c2)cn1] | $^1$H NMR (400 MHz, DMSO-d) δ 8.49 (d, J = 5.0 Hz, 1H), 8.23 (s, 1H), 7.99 (d, J = 12.0 Hz, 2H), 7.45 (s, 1H), 7.37 (t, J = 8.3 Hz, 1H), 7.27-7.18 (m, 2H), 7.12-7.05 (m, 1H), 5.76 (s, 1H), 4.30 (s, 1H), 2.42 (s, 3H), 2.07 (s, 3H). | 452.20 |
| (R)-6-(6-ethynyl-4-methylpyridin-3-yl)-7-methyl-5-(6'-methyl-3'H-spiro[cyclohexane-1,2'-furo[2,3-b]pyridin]-3-en-4-yl)-7H-pyrrolo[2,3-d]pyrimidin-4-amine | 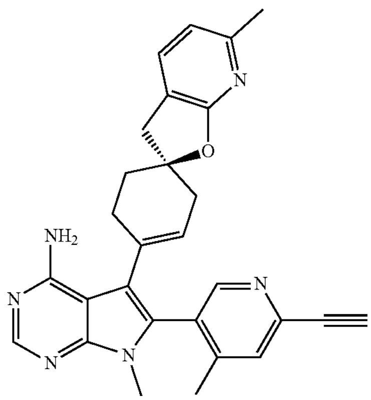 [SMILES: C#Cc1cc(C)c(-c2c(C3=CC[C@]4(CC3)Cc3ccc(C)nc3O4)c3c(N)ncnc3n2C)cn1] | $^1$H NMR (400 MHz, DMSO-d$_6$) δ 8.45 (d, J = 16.1 Hz, 1H), 8.17 (s, 1H), 7.66 (d, J = 5.6 Hz, 1H), 7.42 (dd, J = 7.3, 4.0 Hz, 1H), 6.68 (d, J = 7.3 Hz, 1H), 6.48 (d, J = 45.8 Hz, 2H), 5.64 (d, J = 52.5 Hz, 1H), 4.45 (d, J = 2.1 Hz, 1H), 3.49-3.37 (m, 3H), 2.98-2.62 (m, 2H), 2.30 (s, 6H), 2.17 (d, J = 4.3 Hz, 3H), 2.14-1.81 (m, 2H), 1.71 (ddd, J = 19.5, 12.6, 6.6 Hz, 1H). | 463.20 |
| (S)-6-(6-ethynyl-4-methylpyridin-3-yl)-7-methyl-5-(6-methyl-3'H-spiro[cyclohexane-1,2'-furo[2,3-b]pyridin]-3-en-4-yl)-7H-pyrrolo[2,3-d]pyrimidin-4-amine | 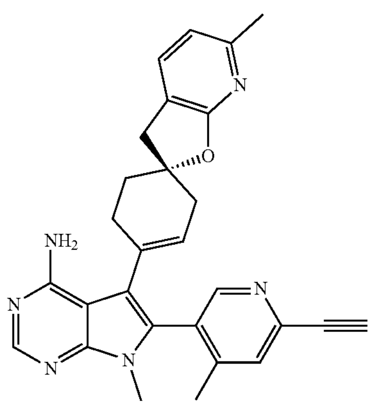 [SMILES: C#Cc1cc(C)c(-c2c(C3=CC[C@@]4(CC3)Cc3ccc(C)nc3O4)c3c(N)ncnc3n2C)cn1] | $^1$H NMR (400 MHz, DMSO-d$_6$) δ 8.45 (d, J = 16.2 Hz, 1H), 8.18 (s, 1H), 7.66 (d, J = 5.6 Hz, 1H), 7.41 (dd, J = 7.3, 4.0 Hz, 1H), 6.68 (d, J = 7.3 Hz, 1H), 6.51 (s, 1H), 5.64 (d, J = 52.2 Hz, 1H), 4.44 (d, J = 2.0 Hz, 1H), 3.40 (s, 3H), 2.92-2.63 (m, 2H), 2.49-2.32 (m, 1H), 2.30 (s, 6H), 2.17 (d, J = 4.4 Hz, 3H), 2.13-1.81 (m, 2H), 1.70 (td, J = 12.5, 6.8 Hz, 1H). | 463.25 |

TABLE 33-continued

Additional Exemplary Compounds

| Compound | Structure | Proton NMR | MS [M + 1] |
|---|---|---|---|
| (S)-4-(4-amino-6-(6-ethynyl-4-methylpyridin-3-yl)-7-methyl-7H-pyrrolo[2,3-d]pyrimidin-5-yl)-2'-methylspiro[cyclohexane-1,6'-cyclopenta[b]pyridin]-3-en-7'(5'H)-one | 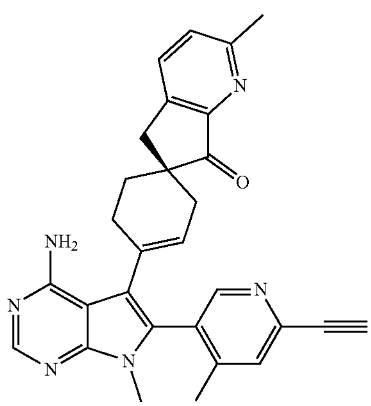 [SMILES: C#Cc1cc(C)c(-c2c(C3=CC[C@@]4(CC3)Cc3ccc(C)nc3C4=O)c3c(N)ncnc3n2C)cn1] | $^1$H NMR (400 MHz, DMSO-$d_6$) δ 8.45 (d, J = 5.7 Hz, 1H), 8.16 (s, 1H), 7.85 (t, J = 8.6 Hz, 1H), 7.66 (d, J = 4.8 Hz, 1H), 7.49 (d, J = 7.9 Hz, 1H), 6.63 (s, 1H), 5.73 (d, J = 62.3 Hz, 1H), 4.45 (d, J = 2.7 Hz, 1H), 3.40 (d, J = 1.7 Hz, 3H), 2.89-2.58 (m, 2H), 2.55 (s, 3H), 2.44-2.28 (m, 1H), 2.17 (d, J = 2.3 Hz, 4H), 2.12-1.65 (m, 3H), 1.49 (dd, J = 17.5, 6.5 Hz, 1H). | 475.25 |
| (R)-4-(4-amino-6-(6-ethynyl-4-methylpyridin-3-yl)-7-methyl-7H-pyrrolo[2,3-d]pyrimidin-5-yl)-2'-methylspiro[cyclohexane-1,6'-cyclopenta[b]pyridin]-3-en-7'(5'H)-one | 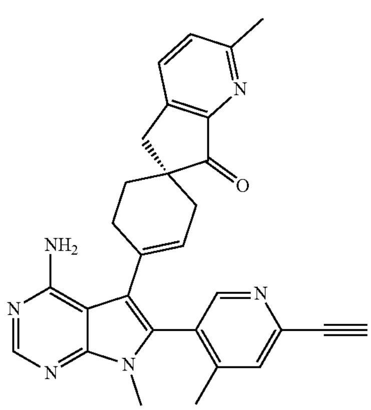 [SMILES: C#Cc1cc(C)c(-c2c(C3=CC[C@]4(CC3)Cc3ccc(C)nc3C4=O)c3c(N)ncnc3n2C)cn1] | $^1$H NMR (400 MHz, DMSO-$d_6$) δ 8.45 (d, J = 5.4 Hz, 1H), 8.16 (s, 1H), 7.85 (t, J = 8.6 Hz, 1H), 7.67 (d, J = 4.8 Hz, 1H), 7.49 (dd, J = 8.1, 1.5 Hz, 1H), 6.58 (d, J = 31.4 Hz, 2H), 5.74 (d, J = 62.1 Hz, 1H), 4.45 (d, J = 2.7 Hz, 1H), 3.41 (d, J = 1.7 Hz, 3H), 2.93-2.58 (m, 2H), 2.55 (s, 3H), 2.43-2.31 (m, 1H), 2.17 (d, J = 2.3 Hz, 4H), 2.16-1.63 (m, 3H), 1.49 (dt, J = 11.4, 6.8 Hz, 1H). | 475.30 |

Example 35

Scheme 32

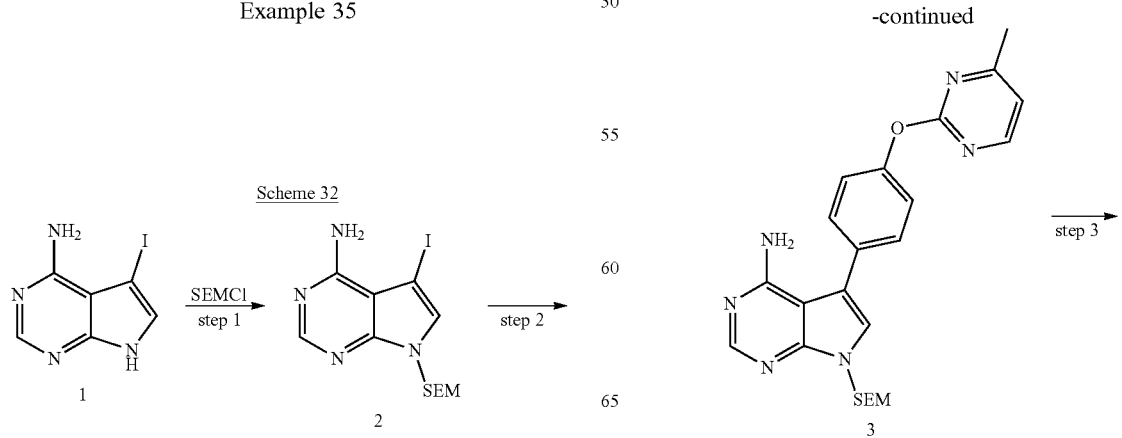

1827

-continued

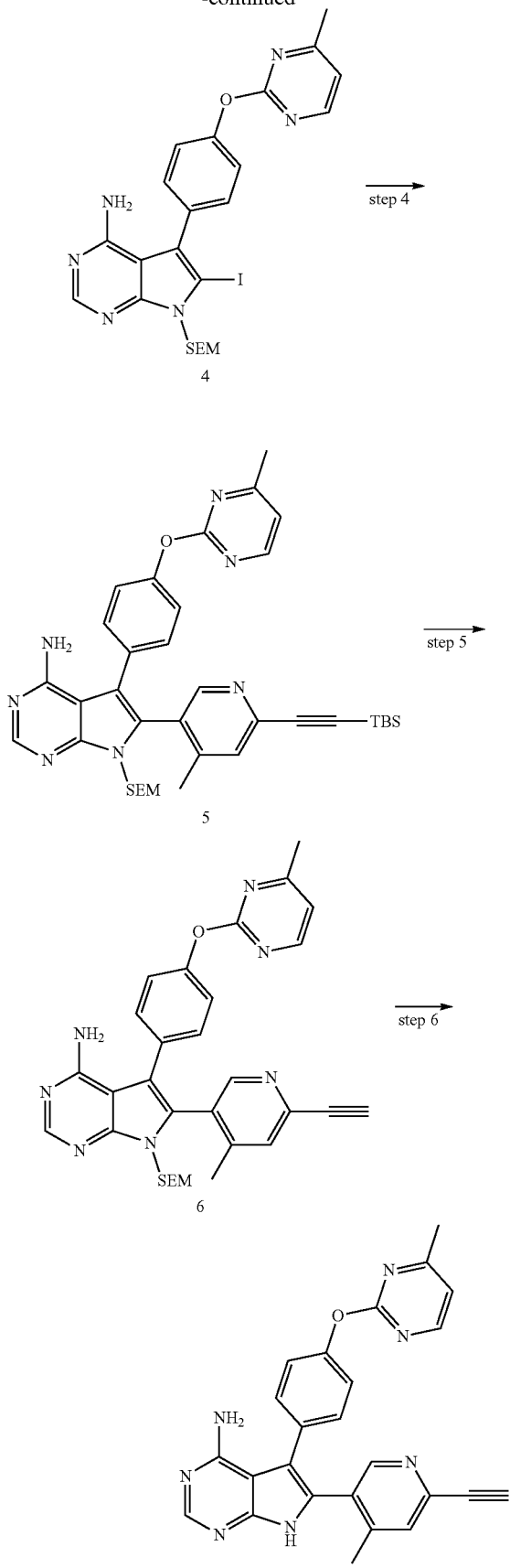

4

5

6

1828

5-iodo-7-((2-(trimethylsilyl)ethoxy)methyl)-7H-pyrrolo[2,3-d]pyrimidin-4-amine

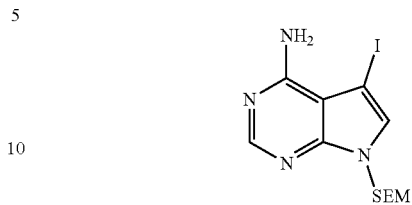

Step 1: A round bottomed flask was charged with 5-iodo-7H-pyrrolo[2,3-d]pyrimidin-4-amine (2 g, 7.69 mmol), $Cs_2CO_3$ (7.49 g, 23.0 mmol), and a stir bar. dimethylformamide (40 mL) was added, and the solution was stirred for 30 min at 0° C. Then added [2-(chloromethoxy)ethyl]trimethylsilane (1.53 g, 9.22 mmol). The reaction mixture was diluted with $H_2O$ (20 mL), and the aqueous phase was extracted with EA (100 mL) three times. The combined organic layers were washed with brine, dried over sodium sulfate, filtered, and concentrated in vacuo. The resulting crude material was purified by silica gel chromatography (50 g column; eluting with dichloromethane/methanol; 40/1-30/1). Concentration in vacuo resulted in 5-iodo-7-{[2-(trimethylsilyl)ethoxy]methyl}-7H-pyrrolo[2,3-d]pyrimidin-4-amine (1.60 g, 53.2%) as a off-white amorphous solid.

5-(4-((4-methylpyrimidin-2-yl)oxy)phenyl)-7-((2-(trimethylsilyl)ethoxy)methyl)-7H-pyrrolo[2,3-d]pyrimidin-4-amine

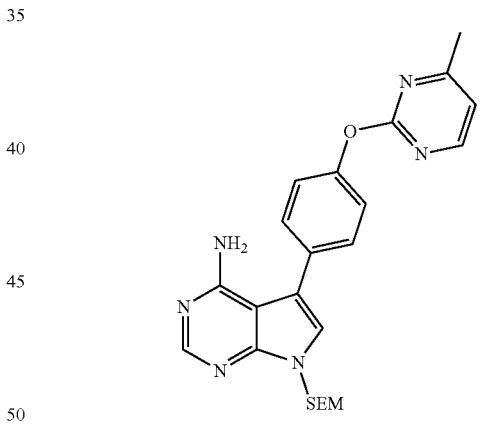

Step 2: A resealable reaction vial was charged with 5-iodo-7-{[2-(trimethylsilyl) ethoxy]methyl}-7H-pyrrolo[2,3-d]pyrimidin-4-amine (1.6 g, 4.09 mmol), 4-methyl-2-[4-(4,4,5,5-tetramethyl-1,3,2-dioxaborolan-2-yl)phenoxy]pyrimidine; bis(methane) (1.54 g, 4.49 mmol), $K_3PO_4$ (2.58 g, 12.2 mmol), DME/$H_2O$ (16 mL/2 mL), Pd(dppf)$Cl_2$ (298 mg, 409 μmol), and a stirbar before being evacuated and purged with nitrogen three times. The mixture was stirred for 1 h at 90° C. The reaction mixture was diluted with $H_2O$ (10 mL), and the aqueous phase was extracted with dichloromethane (80 mL) for three times. The combined organic layers were washed with brine, dried over sodium sulfate, filtered, and concentrated in vacuo. The resulting crude material was purified by silica gel chromatography (50 g column; eluting with dichloromethane/methanol; 20/1). Concentration in vacuo resulted in 5-{4-[(4-methylpyrimidin-2-yl)oxy]phenyl}-7-{[2-(trimethylsilyl)ethoxy]methyl}-7H-pyrrolo[2,3-d]pyrimidin-4-amine (1.60 g, 87.0%) as a orange amorphous solid.

6-iodo-5-{4-[(4-methylpyrimidin-2-yl)oxy]phenyl}-7-{[2-(trimethylsilyl)ethoxy]-methyl}-7H-pyrrolo[2,3-d]pyrimidin-4-amine

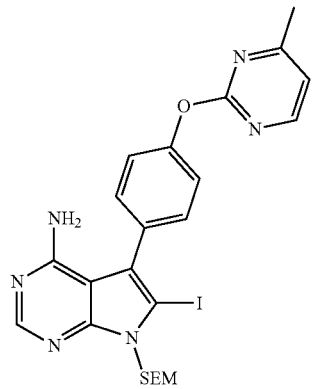 [SMILES: Cc1ccnc(Oc2ccc(-c3c(I)n(COCC[Si](C)(C)C)c4ncnc(N)c34)cc2)n1]

Step 3: A round bottomed flask was charged with 5-{4-[(4-methylpyrimidin-2-yl)oxy]phenyl}-7-{[2-(trimethylsilyl)ethoxy]methyl}-7H-pyrrolo[2,3-d]pyrimidin-4-amine (1.6 g, 3.56 mmol), iodo(sulfanyl)amine (680 mg, 3.91 mmol), dichloromethane (20 mL) and a stir bar, then TFA (1.02 g, 10.6 mmol) was added at 0° C. The mixture was stirred for 1 h at room temperature. The mixture was quenched with saturated NaHSO₃ aqueous solution until the pH to 8-9, extracted with DCM (100 mL) for three times, the organic phase was combined and dried with Na₂SO₄, Concentration in vacuo. The resulting crude material was purified by silica gel chromatography (50 g column; eluting with dichloromethane/methanol; 15/1). Concentration in vacuo resulted in 6-iodo-5-{4-[(4-methylpyrimidin-2-yl)oxy]phenyl}-7-{[2-(trimethylsilyl)ethoxy]methyl}-7H-pyrrolo[2,3-d]pyrimidin-4-amine (1.40 g, 68.5%) as a yellow amorphous solid.

6-(6-((tert-butyldimethylsilyl)ethynyl)-4-methylpyridin-3-yl)-5-(4-((4-methylpyrimidin-2-yl)oxy)phenyl)-7-((2-(trimethylsilyl)ethoxy)methyl)-7H-pyrrolo[2,3-d]pyrimidin-4-amine

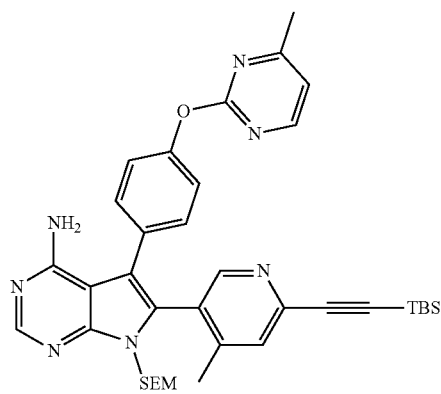

Step 4: A resealable reaction vial was charged with 6-iodo-5-{4-[(4-methylpyrimidin-2-yl)oxy]phenyl}-7-{[2-(trimethylsilyl)ethoxy]methyl}-7H-pyrrolo[2,3-d]pyrimidin-4-amine (400 mg, 696 µmol), 2-[2-(tert-butyldimethylsilyl)ethynyl]-4-methyl-5-(4,4,5,5-tetramethyl-1,3,2-dioxaborolan-2-yl)pyrimidine (274 mg, 765 µmol), K₃PO₄ (440 mg, 2.08 mmol), Pd(dppf)Cl₂ (50.8 mg, 69.6 µmol), and a stirbar before being evacuated and purged with nitrogen three times. DME/H₂O (8 mL/2 mL) was added, and the mixture was stirred for 1 h at 90° C. The reaction mixture was diluted with H₂O (3 mL), and the aqueous phase was extracted with dichloromethane (50 mL) for three times. The combined organic layers were washed with brine, dried over sodium sulfate, filtered, and concentrated in vacuo. The resulting crude material was purified by silica gel chromatography (10 g column; eluting with dichloromethane/methanol=15/1). Concentration in vacuo resulted in 6-{2-[2-(tert-butyldimethylsilyl)ethynyl]-4-methylpyrimidin-5-yl}-5-{4-[(4-methylpyrimidin-2-yl)oxy]phenyl}-7-{[2-(trimethylsilyl)ethoxy]methyl}-7H-pyrrolo[2,3-d]pyrimidin-4-amine (310 mg, 65.5%) as a yellow amorphous solid.

6-(6-ethynyl-4-methylpyridin-3-yl)-5-(4-((4-methylpyrimidin-2-yl)oxy)phenyl)-7-((2-(trimethylsilyl)ethoxy)methyl)-7H-pyrrolo[2,3-d]pyrimidin-4-amine

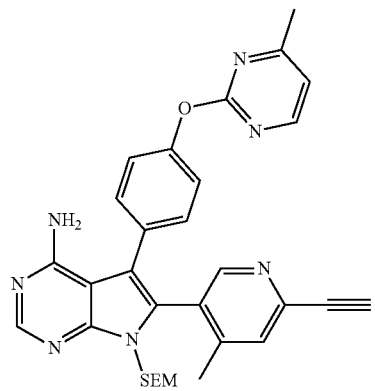 [SMILES: C#Cc1cc(C)c(-c2c(-c3ccc(Oc4nccc(C)n4)cc3)c3c(N)ncnc3n2COCC[Si](C)(C)C)cn1]

Step 5: A round bottomed flask was charged with 6-{6-[2-(tert-butyldimethylsilyl)ethynyl]-4-methylpyridin-3-yl}-5-{4-[(4-methylpyrimidin-2-yl)oxy]phenyl}-7-{[2-(trimethylsilyl)ethoxy]methyl}-7H-pyrrolo[2,3-d]pyrimidin-4-amine (290 mg, 427 µmol), TBAF (133 mg, 512 µmol), THF (3 mL) and a stir bar. and the solution was stirred at room temperature for 1 h. The resulting crude material was purified by silica gel chromatography (20 g column; eluting with dichloromethane/methanol; 15/1). Concentration in vacuo resulted in 6-(2-ethynyl-4-methylpyrimidin-5-yl)-5-{4-[(4-methylpyrimidin-2-yl)oxy]phenyl}-7-{[2-(trimethylsilyl)ethoxy]methyl}-7H-pyrrolo[2,3-d]pyrimidin-4-amine (230 mg, 95.3%) as a black amorphous solid.

6-(6-ethynyl-4-methylpyridin-3-yl)-5-(4-((4-methylpyrimidin-2-yl)oxy)phenyl)-7H-pyrrolo[2,3-d]pyrimidin-4-amine

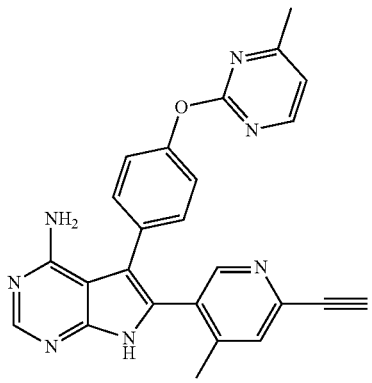 [SMILES: C#Cc1cc(C)c(-c2[nH]c3ncnc(N)c3c2-c2ccc(Oc3nccc(C)n3)cc2)cn1]

Step 6: A round bottomed flask was charged with 6-(6-ethynyl-4-methylpyridin-3-yl)-5-{4-[(4-methylpyrimidin-2-yl)oxy]phenyl}-7-{[2-(trimethylsilyl)ethoxy]methyl}-7H-pyrrolo[2,3-d]pyrimidin-4-amine (210 mg, 372 μmol), and a stirbar. TFA/DCM (40 ml) was added, and the solution was stirred at room temperature for 30 min. Concentration in vacuo. MeOH/EDA (20 mL) was added, and the solution was stirred at room temperature for 10 min. Concentration in vacuo. The resulting crude material was purified by silica gel chromatography (5 g column; eluting with dichloromethane/methanol; ratio=20:1). The resulting crude material was purified by HPLC (Column: YMC-Actus Triart C18, 30*250, 5 um). Lyophilization yielded 6-(6-ethynyl-4-methylpyridin-3-yl)-5-{4-[(4-methylpyrimidin-2-yl)oxy]phenyl}-7H-pyrrolo[2,3-d]pyrimidin-4-amine (37.0 mg, 22.9%) as a off-white amorphous solid.

Additional compounds prepared according to the methods of Example 35 are depicted in Table 34 below.

TABLE 34

| | Additional Exemplary Compounds | | |
| --- | --- | --- | --- |
| Compound | Structure | Proton NMR | MS [M + 1] |
| 6-(6-ethynyl-4-methylpyridin-3-yl)-5-(4-((4-methylpyrimidin-2-yl)oxy)phenyl)-7H-pyrrolo[2,3-d]pyrimidin-4-amine | | ¹H NMR (400 MHz, DMSO-d₆) δ 12.12 (s, 1H), 8.48 (d, J = 5.0 Hz, 1H), 8.34 (s, 1H), 8.18 (s, 1H), 7.51 (s, 1H), 7.31-7.24 (m, 2H), 7.24-7.18 (m, 2H), 7.16 (d, J = 5.0 Hz, 1H), 5.97 (s, 1H), 4.37 (s, 1H), 2.42 (s, 3H), 2.08 (s, 3H). | 434.25 |
| 6-(2-ethynyl-4-methylpyrimidin-5-yl)-5-(4-((4-methylpyrimidin-2-yl)oxy)phenyl)-7H-pyrrolo[2,3-d]pyrimidin-4-amine | | ¹H NMR (400 MHz, DMSO-d₆) δ 8.59 (s, 1H), 8.48 (d, J = 5.2 Hz, 1H), 8.20 (s, 1H), 7.31 (d, J = 8.2 Hz, 3H), 7.23 (d, J = 8.3 Hz, 4H), 7.16 (d, J = 5.1 Hz, 1H), 4.44 (s, 1H), 2.42 (s, 3H), 2.21 (s, 3H). | 435.25 |

Example 36

Scheme 33

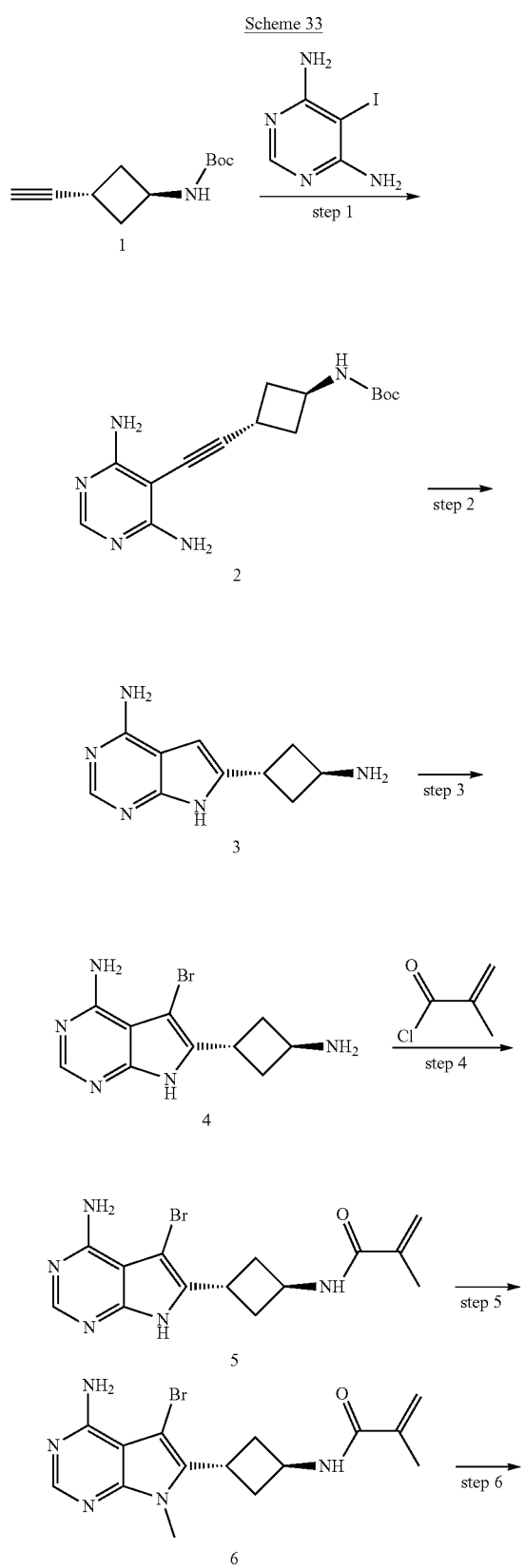

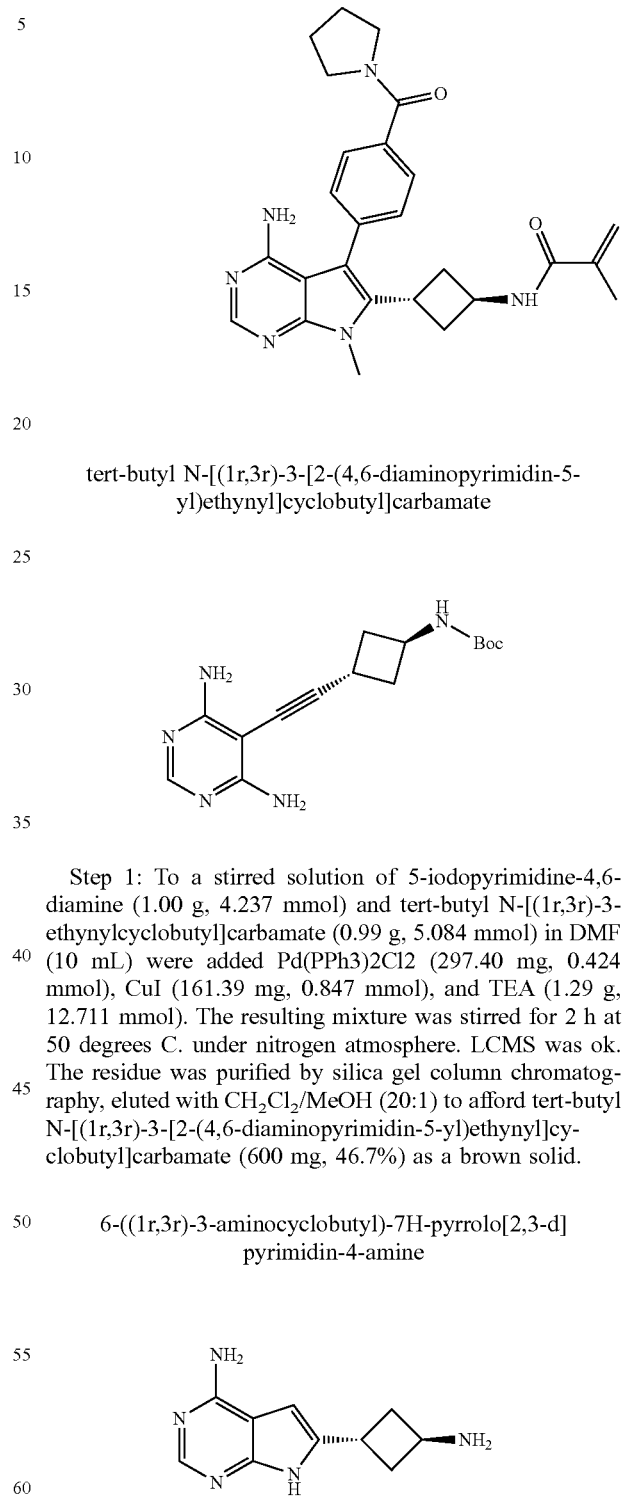

tert-butyl N-[(1r,3r)-3-[2-(4,6-diaminopyrimidin-5-yl)ethynyl]cyclobutyl]carbamate Step 1: To a stirred solution of 5-iodopyrimidine-4,6-diamine (1.00 g, 4.237 mmol) and tert-butyl N-[(1r,3r)-3-ethynylcyclobutyl]carbamate (0.99 g, 5.084 mmol) in DMF (10 mL) were added Pd(PPh3)2Cl2 (297.40 mg, 0.424 mmol), CuI (161.39 mg, 0.847 mmol), and TEA (1.29 g, 12.711 mmol). The resulting mixture was stirred for 2 h at 50 degrees C. under nitrogen atmosphere. LCMS was ok. The residue was purified by silica gel column chromatography, eluted with CH2Cl2/MeOH (20:1) to afford tert-butyl N-[(1r,3r)-3-[2-(4,6-diaminopyrimidin-5-yl)ethynyl]cyclobutyl]carbamate (600 mg, 46.7%) as a brown solid.

6-((1r,3r)-3-aminocyclobutyl)-7H-pyrrolo[2,3-d]pyrimidin-4-amine

Step 2: To a stirred solution of tert-butyl N-[(1r,3r)-3-[2-(4,6-diaminopyrimidin-5-yl)ethynyl]cyclobutyl]carbamate (600.00 mg, 1.978 mmol) in NMP (10 mL) was added tert-butoxypotassium (665.81 mg, 5.933 mmol). The resulting mixture was stirred for 3 h at 100 degrees C. LCMS was OK. The residue was purified by silica gel column chromatography, eluted with CH₂Cl₂/MeOH (1:1) to afford 6-[(1r,3r)-3-aminocyclobutyl]-7H-pyrrolo[2,3-d]pyrimidin-4-amine (300 mg, 74.6%) as a brown solid.

5-bromo-6-[(1r,3r)-3-aminocyclobutyl]-7H-pyrrolo[2,3-d]pyrimidin-4-amine

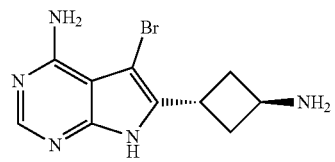 [SMILES: Nc1ncnc2[nH]c([C@H]3C[C@H](N)C3)c(Br)c12]

Step 3: To a stirred solution of 6-[(1r,3r)-3-aminocyclobutyl]-7H-pyrrolo[2,3-d]pyrimidin-4-amine (300.00 mg, 1.476 mmol) in DMF (5 mL) was added NBS (262.71 mg, 1.476 mmol). The resulting mixture was stirred for 1 h at 0 degrees C. LCMS was OK. The residue was purified by silica gel column chromatography, eluted with CH₂Cl₂/MeOH (1:1) to afford 5-bromo-6-[(1r,3r)-3-aminocyclobutyl]-7H-pyrrolo[2,3-d]pyrimidin-4-amine (200 mg, 48%) as a brown solid.

N-((1r,3r)-3-(4-amino-5-bromo-7H-pyrrolo[2,3-d]pyrimidin-6-yl)cyclobutyl)methacryl-amide

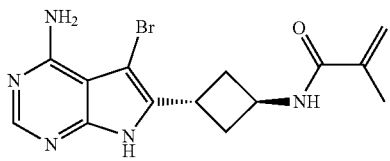 [SMILES: C=C(C)C(=O)N[C@H]1C[C@H](c2[nH]c3ncnc(N)c3c2Br)C1]

Step 4: To a stirred solution of 5-bromo-6-[(1r,3r)-3-aminocyclobutyl]-7H-pyrrolo[2,3-d]pyrimidin-4-amine (10.00 mg, 0.035 mmol) and TEA (10.76 mg, 0.106 mmol) in DCM (1 mL) was added methacryloyl chloride (3.70 mg, 0.035 mmol). The resulting mixture was stirred for 1 h at −30 degrees C. The reaction mixture was filtered through a pad of Celite®, the pad was washed with DCM, and the filtrate was concentrated in vacuo. The resulting crude material was purified by HPLC (acetonitrile/water/0.1% formic acid). Lyophilization yielded N-((1r,3r)-3-(4-amino-5-bromo-7H-pyrrolo[2,3-d]pyrimidin-6-yl)cyclobutyl)methacryl-amide (3.00 mg, 24.5%) as a white amorphous solid.

N-((1r,3r)-3-(4-amino-5-bromo-7-methyl-7H-pyrrolo[2,3-d]pyrimidin-6-yl)cyclobutyl) methacrylamide

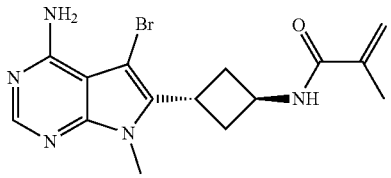 [SMILES: C=C(C)C(=O)N[C@H]1C[C@H](c2c(Br)c3c(N)ncnc3n2C)C1]

Step 5: To a stirred solution of 2-methyl-N-[(1r,3r)-3-[4-amino-5-bromo-7H-pyrrolo[2,3-d]pyrimidin-6-yl]cyclobutyl]prop-2-enamide (60 mg, 0.171 mmol) and Cs2CO3 (167.46 mg, 0.514 mmol) in DMF (2 mL) was added CH₃I (24.32 mg, 0.171 mmol). The resulting mixture was stirred for 1 h at 0 degrees C. The resulting mixture was filtered, the filter cake was washed with DMF. The crude was used in the next step directly without further purification.

N-((1r,3r)-3-(4-amino-7-methyl-5-(4-(pyrrolidine-1-carbonyl)phenyl)-7H-pyrrolo[2,3-d]pyrimidin-6-yl)cyclobutyl)methacrylamide

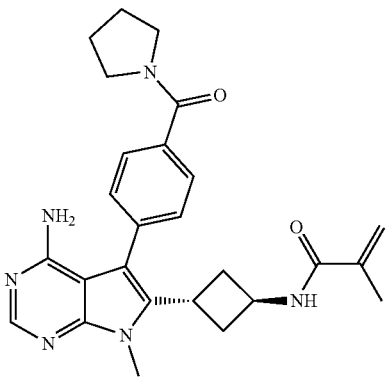 [SMILES: C=C(C)C(=O)N[C@H]1C[C@H](c2c(-c3ccc(C(=O)N4CCCC4)cc3)c3c(N)ncnc3n2C)C1]

Step 6: To a solution of 2-methyl-N-[(1r,3r)-3-[4-amino-5-bromo-7-methylpyrrolo[2,3-d]pyrimidin-6-yl]cyclobutyl]prop-2-enamide (10.00 mg, 0.027 mmol) and 4-(pyrrolidine-1-carbonyl)phenylboronic acid (7.22 mg, 0.033 mmol) in DMF (1 mL) and water (0.1 mL) were added CsF (12.51 mg, 0.082 mmol) and Pd(DtBPF)Cl2 (1.79 mg, 0.003 mmol). The residue was stirred for 2 h at 90 degrees C. under a nitrogen atmosphere. The reaction mixture was diluted with water (10 mL), and the aqueous phase was extracted with dichloromethane (10 mL) three times. The combined organic layers were washed with brine, dried over sodium sulfate, filtered, and concentrated in vacuo. The resulting crude material was purified by silica gel chromatography (5 g column; eluting with dichloromethane/methanol/0.1% triethylamine; ratio). Concentration in vacuo resulted in N-((1r,3r)-3-(4-amino-7-methyl-5-(4-(pyrrolidine-1-carbonyl)phenyl)-7H-pyrrolo[2,3-d]pyrimidin-6-yl)cyclobutyl)methacrylamide (3.0 mg, 24.2%) as a white amorphous solid.

Additional compounds prepared according to the methods of Example 36 are depicted in Table 35 below.

TABLE 35

Additional Exemplary Compounds

| Compound | Structure | Proton NMR | MS [M + 1] |
|---|---|---|---|
| 1-(4-(3-(4-amino-7-methyl-5-(4-(6-methylpyridin-2-yloxy)phenyl)-7H-pyrrolo[2,3-d]pyrimidin-6-yl)azetidin-1-yl)piperidin-1-yl)prop-2-en-1-one | 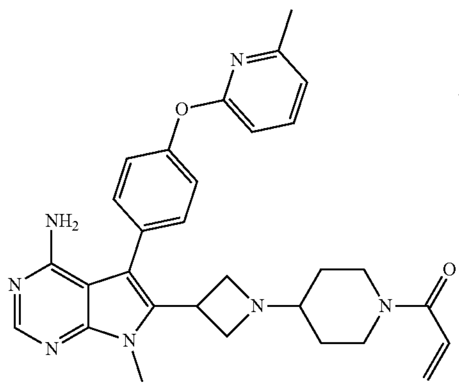 [SMILES: C=CC(=O)N1CCC(N2CC(c3c(-c4ccc(Oc5cccc(C)n5)cc4)c4c(N)ncnc4n3C)C2)CC1] | $^1$H NMR (400 MHz, DMSO-d$_6$) δ 8.11 (s, 1H), 7.75 (t, J = 7.7 Hz, 1H), 7.42-7.36 (m, 2H), 7.23-7.17 (m, 2H), 7.03 (d, J = 7.4 Hz, 1H), 6.82 (d, J = 81 Hz, 1H), 6.75 (dd, J = 16.7, 10.5 Hz, 1H), 6.05 (dd, J = 16.7, 2.4 Hz, 1H), 5.73 (s, 1H), 5.63 (dd, J = 10.5, 2.4 Hz, 1H), 3.99 (p, J = 8.0 Hz, 1H), 3.88 (d, J = 13.2 Hz, 1H), 3.75 (d, J = 13.4 Hz, 1H), 3.67 (s, 3H), 3.54 (t, J = 6.9 Hz, 2H), 3.15 (t, J = 11.5 Hz, 1H), 2.99 (t, J = 11.2 Hz, 1H), 2.77 (s, 2H), 2.35 (s, 3H), 2.07 (s, 1H), 1.48 (s, 2H), 1.03 (s, 2H). | 523.64 |
| 1-(4-(3-(4-amino-5-(3-methoxy-4-(6-methylpyridin-2-yloxy)phenyl)-7-methyl-7H-pyrrolo[2,3-d]pyrimidin-6-yl)azetidin-1-yl)piperidin-1-yl)prop-2-en-1-one | 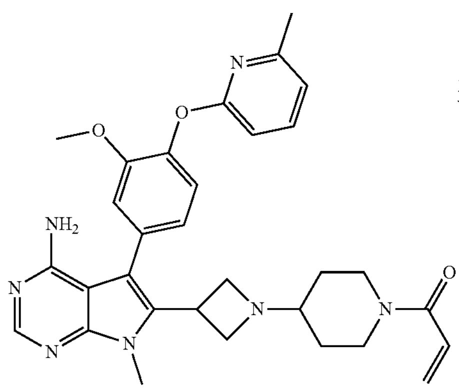 [SMILES: C=CC(=O)N1CCC(N2CC(c3c(-c4ccc(Oc5cccc(C)n5)c(OC)c4)c4c(N)ncnc4n3C)C2)CC1] | $^1$H NMR (400 MHz, DMSO-d$_6$) δ 8.11 (s, 1H), 7.68 (t, J = 7.7 Hz, 1H), 7.20 (d, J = 8.0 Hz, 1H), 7.10 (d, J = 1.9 Hz, 1H), 7.00-6.92 (m, 2H), 6.76 (dd, J = 16.7, 10.5 Hz, 1H), 6.69 (d, J = 8.2 Hz, 1H), 6.05 (dd, J = 16.7, 2.4 Hz, 2H), 5.63 (dd, J = 10.5, 2.5 Hz, 1H), 4.03 (p, J = 8.1 Hz, 1H), 3.90 (d, J = 12.9 Hz, 1H), 3.69 (d, J = 14.5 Hz, 5H), 3.59 (s, 2H), 3.15 (s, 1H), 2.97 (d, J = 11.5 Hz, 1H), 2.81 (s, 2H), 2.30 (s, 3H), 2.09 (s, 1H), 1.50 (s, 2H), 1.04 (s, 2H). | 553.66 |
| N-((1r,3r)-3-(4-amino-7-methyl-5-(4-(pyrrolidine-1-carbonyl)phenyl)-7H-pyrrolo[2,3-d]pyrimidin-6-yl)cyclobutyl)methacrylamide | 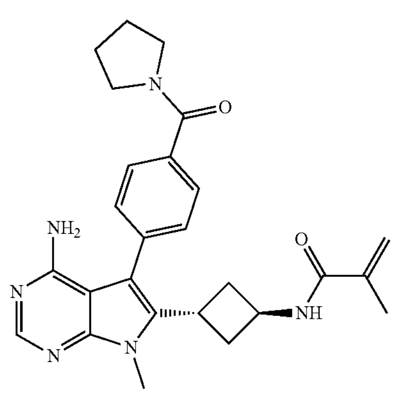 [SMILES: C=C(C)C(=O)N[C@H]1C[C@H](c2c(-c3ccc(C(=O)N4CCCC4)cc3)c3c(N)ncnc3n2C)C1] | $^1$H NMR (400 MHz, DMSO-d$_6$) δ 8.22 (d, J = 6.4 Hz, 1H), 8.11 (s, 1H), 7.62 (d, J = 7.7 Hz, 2H), 7.44 (d, J = 7.8 Hz, 2H), 5.64 (s, 2H), 5.36-5.31 (m, 1H), 4.08-4.00 (m, 2H), 3.70 (s, 3H), 3.54-3.44 (m, 4H), 2.29 (t, J = 7.5 Hz, 4H), 1.88 (dt, J = 11.3, 5.7 Hz, 3H), 1.84 (s, 4H). | 459.20 |

Example 37
Scheme 34
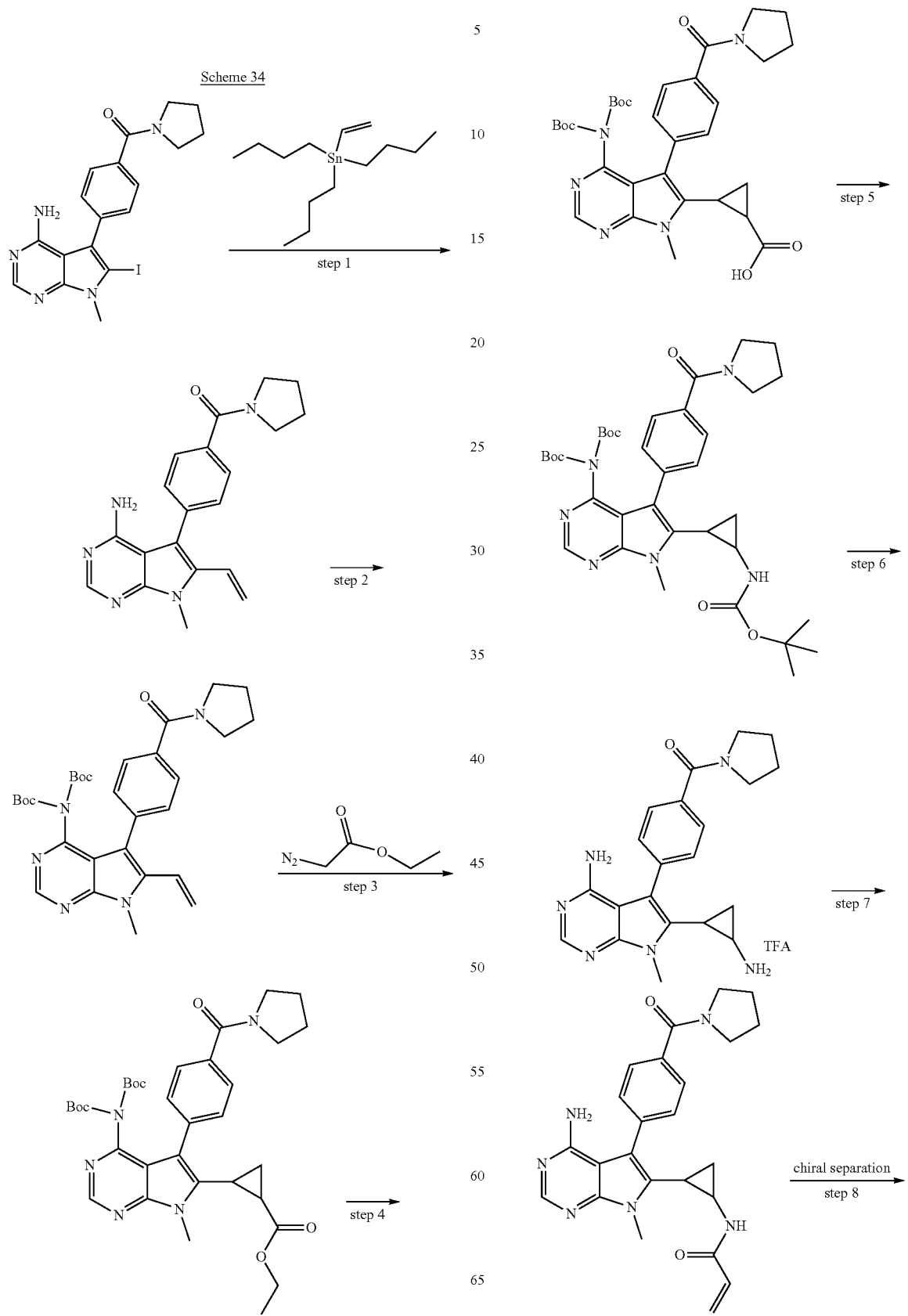

1841
-continued

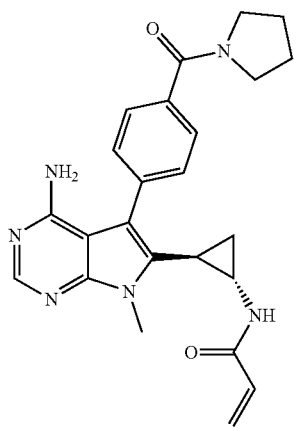

(4-(4-amino-7-methyl-6-vinyl-7H-pyrrolo[2,3-d]
pyrimidin-5 yl)phenyl)(pyrrolidin-1-yl)methanone

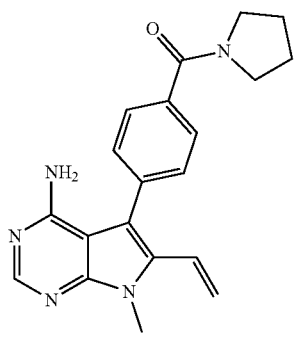 [SMILES: C=Cc1c(-c2ccc(C(=O)N3CCCC3)cc2)c2c(N)ncnc2n1C]

Step 1: A resealable reaction vial was charged with 6-iodo-7-methyl-5-[4-(pyrrolidine-1-carbonyl)phenyl]-7H-pyrrolo[2,3-d]pyrimidin-4-amine (1 g, 2.23 mmol), tributyl(ethenyl)stannane (846 mg, 2.67 mmol), Pd(PPh3)4 (257 mg, 223 µmol) and a stirbar before being evacuated and purged with nitrogen three times. Dimethylformamide (20 mL) was added, and the mixture was stirred O/N at 110° C. The reaction mixture was diluted with water (50 mL), and the aqueous phase was extracted with dichloromethane (20 mL) three times. The combined organic layers were washed with brine, dried over sodium sulfate, filtered, and concentrated in vacuo. The resulting crude material was purified by silica gel chromatography. Concentration in vacuo resulted in 6-ethenyl-7-methyl-5-[4-(pyrrolidine-1-carbonyl)phenyl]-7H-pyrrolo[2,3-d]pyrimidin-4-amine (700 mg, 90%) as a yellow amorphous solid.

1842 tert-butyl N-[(tert-butoxy)carbonyl]-N-{6-ethenyl-7-methyl-5-[4-(pyrrolidine-1-carbonyl)phenyl]-7H-pyrrolo[2,3-d]pyrimidin-4-yl}carbamate

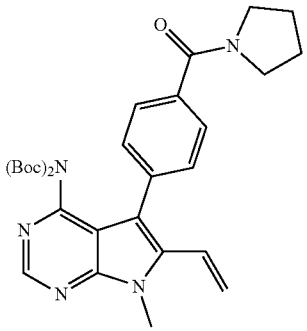

Step 2: A round bottomed flask was charged with 6-ethenyl-7-methyl-5-[4-(pyrrolidine-1-carbonyl)phenyl]-7H-pyrrolo[2,3-d]pyrimidin-4-amine (700 mg, 2.01 mmol), di-tert-butyl dicarbonate (1.75 g, 8.04 mmol), Et3N (813 mg, 8.04 mmol), DMAP (24.5 mg, 201 µmol), dichloromethane (20 mL) and a stir bar. The mixture was stirred O/N at room temperature. The reaction mixture was diluted with water (50 mL), and the aqueous phase was extracted with dichloromethane (20 mL) three times. The combined organic layers were washed with brine, dried over sodium sulfate, filtered, and concentrated in vacuo. The resulting crude material was purified by silica gel chromatography. Concentration in vacuo resulted in tert-butyl N-[(tert-butoxy)carbonyl]-N-{6-ethenyl-7-methyl-5-[4-(pyrrolidine-1-carbonyl)phenyl]-7H-pyrrolo[2,3-d]pyrimidin-4-yl}carbamate (990 mg, 89%) as a yellow amorphous solid.

2-(4-{bis[(tert-butoxy)carbonyl]amino}-7-methyl-5-[4-(pyrrolidine-1-carbonyl)phenyl]-7H-pyrrolo[2,3-d]pyrimidin-6-yl)cyclopropane-1-carboxylate

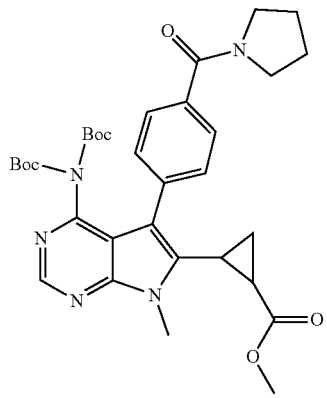 [SMILES: COC(=O)C1CC1c1c(-c2ccc(C(=O)N3CCCC3)cc2)c2c(N(C(=O)OC(C)(C)C)C(=O)OC(C)(C)C)ncnc2n1C]

Step 3: A resealable reaction vial was charged with tert-butyl N-[(tert-butoxy)carbonyl]-N-{6-ethenyl-7-methyl-5-[4-(pyrrolidine-1-carbonyl)phenyl]-7Hpyrrolo[2,3-d]pyrimidin-4-yl}carbamate (800 mg, 1.46 mmol), ethyl propanoate (149 mg, 1.46 mmol), 5,10,15,20-tetraphenyl-21H,23H-porphine (19.6 mg, 29.2 µmol), toluene (15 mL) and a stir bar before being evacuated and purged with nitrogen three times. The reaction mixture was stirred for 2 h at 110° C. The reaction mixture was filtered through a pad of Celite®, the pad was washed with dichloromethane, and the filtrate was concentrated in vacuo. The resulting crude material was purified by silica gel chromatography. Concentration in vacuo resulted in ethyl 2-(4-{bis[(tert-butoxy)carbonyl]amino}-7-methyl-5-[4-(pyrrolidine-1-carbonyl)phenyl]-7H-pyrrolo[2,3 d]pyrimidin-6-yl)cyclopropane-1-carboxylate (550 mg, 59%) as a yellow amorphous solid.

2-(4-{bis[(tert-butoxy)carbonyl]amino}-7-methyl-5-[4-(pyrrolidine-1-carbonyl)phenyl]-7H-pyrrolo[2,3-d]pyrimidin-6-yl)cyclopropane-1-carboxylic acid

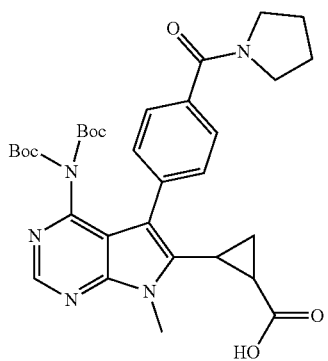 [SMILES: Cn1c(C2CC2C(=O)O)c(-c2ccc(C(=O)N3CCCC3)cc2)c2c(N(C(=O)OC(C)(C)C)C(=O)OC(C)(C)C)ncnc21]

Step 4: A round bottomed flask was charged with ethyl 2-(4-{bis[(tert-butoxy)carbonyl]amino}-7-methyl-5-[4-(pyrrolidine-1-carbonyl)phenyl]-7H-pyrrolo[2,3-d]pyrimidin-6-yl)cyclopropane-1-carboxylate (1.7 g, 2.68 mmol), MeOH (15 mL) and a stir bar. NaOH aq. (2M) (15 mL) was added, and the solution was stirred for 2 h at rt. The pH was adjusted to 3~4 with HCl aq. (2M), collected the solid, dried in vacuo resulted in 2-(4-{bis[(tert-butoxy)carbonyl]amino}-7-methyl-5-[4-(pyrrolidine-1-carbonyl)phenyl]-7H-pyrrolo[2,3-d]pyrimidin-6-yl)cyclopropane-1-carboxylic acid (1.30 g, 80%) as an off-white solid.

tert-butyl (tert-butoxycarbonyl)(6-(2-((tert-butoxycarbonyl)amino) cyclopropyl)-7-methyl-5-(4-(pyrrolidine-1-carbonyl)phenyl)-7H-pyrrolo[2,3-d]pyrimidin-4-yl)carbamate

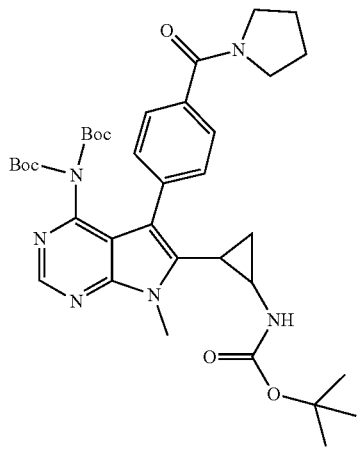 [SMILES: Cn1c(C2CC2NC(=O)OC(C)(C)C)c(-c2ccc(C(=O)N3CCCC3)cc2)c2c(N(C(=O)OC(C)(C)C)C(=O)OC(C)(C)C)ncnc21]

Step 5: A round bottomed flask was charged with 2-(4-{bis[(tert-butoxy)carbonyl]amino}-7-methyl-5-[4-(pyrrolidine-1-carbonyl)phenyl]-7H-pyrrolo[2,3-d]pyrimidin-6-yl)cyclopropane-1-carboxylic acid (400 mg, 660 μmol), TEA (73.3 mg, 726 μmol), DPPA (2.18 g, 7.92 mmol) and a stirbar. t-BuOH (10 mL) was added, and the solution was stirred for 4 h at 80° C. The reaction mixture was quenched with water, extracted with DCM, dried over $Na_2SO_4$, concentrated in vacuo. The resulting crude material was purified by prep-HPLC (acetonitrile/water/0.1% formic acid). Lyophilization yielded tert-butyl N-[2-(4-{bis[(tert-butoxy)carbonyl]amino}-7-methyl-5-[4-(pyrrolidine-1-carbonyl)phenyl]-7H-pyrrolo[2,3-d]pyrimidin-6-yl)cyclopropyl]carbamate (200 mg, 49%) as an off-white amorphous solid.

(4-(4-amino-6-(2-aminocyclopropyl)-7-methyl-7H-pyrrolo[2,3-d]pyrimidin-5-yl)phenyl)(pyrrolidin-1-yl)methanone

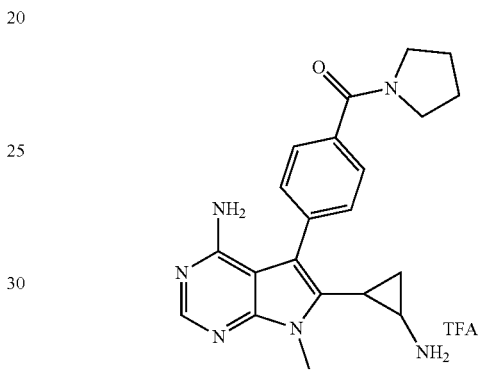

Step 6: A round bottomed flask was charged with tert-butyl N-[2-(4-{bis[(tert-butoxy)carbonyl]amino}-7-methyl-5-[4-(pyrrolidine-1-carbonyl)phenyl]-7H-pyrrolo[2,3-d]pyrimidin-6-yl)cyclopropyl]carbamate (200 mg, 295 μmol) and a stir bar. DCM:TFA=4:1 (11 mL) was added, and the solution was stirred for 1 h at rt. The solvent was removed, the crude product (200 mg) was used in the next step directly without further purification.

N-(2-(4-amino-7-methyl-5-(4-(pyrrolidine-1-carbonyl)phenyl)-7H-pyrrolo[2,3-d]pyrimidin-6-yl)cyclopropyl)acrylamide

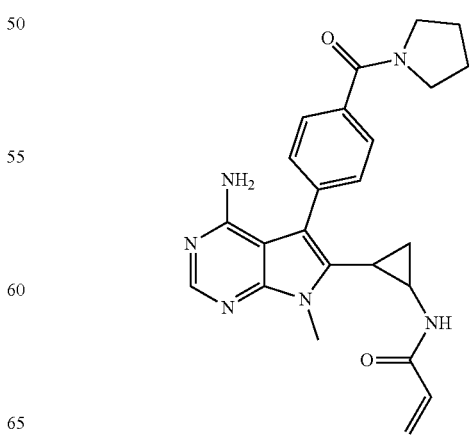

Step 7: A round bottomed flask was charged with 6-(2-aminocyclopropyl)-7-methyl-5-[4-(pyrrolidine-1-carbonyl)phenyl]-7H-pyrrolo[2,3-d]pyrimidin-4-amine (200 mg, 0.42 mmol), TEA (213 mg, 2.1 mmol), dichloromethane (10 mL) and a stir bar. prop-2-enoyl chloride (38 mg, 0.42 mmol) was added at 0° C. The reaction mixture was stirred for 0.5 h at 0° C. The solvent was removed, the resulting crude material was purified by prep-HPLC (Column: XBridge Prep OBD C18 Column, 30×150 mm 5 um; Mobile Phase A: undefined, Mobile Phase B:undefined; Flow rate:60 mL/min; Gradient: 11 B to 35 B in 7 min; 254 nm; RT1:6.75; RT2:; Injection Volumn: ml; Number Of Runs:;). Lyophilization yielded N-(2-{4-amino-7-methyl-5-[4-(pyrrolidine-1-carbonyl)phenyl]-7H-pyrrolo[2,3-d]pyrimidin-6-yl}cyclopropyl)prop-2-enamide (140 mg, 77%) as an off-white amorphous solid. The material was sent to chiral separation (Column: CHIRALPAK IG, 2*25 cm, 5 um; Mobile Phase A:Hex:DCM=3:1 (10 mM NH3-MEOH)-HPLC, Mobile Phase B:EtOH-HPLC; Flow rate:20 mL/min; Gradient:30 B to 30 B in 18 min; 220/254 nm; RT1:7.758; RT2:10.625; Injection Volumn:0.6 ml; Number Of Runs:10;), yield four peaks, peak 1 (16.7 mg), peak 2 (28.5 mg), peak 3 (18.1 mg), peak 4 (28.8 mg).

Additional compounds prepared according to the methods of Example 37 are depicted in Table 36 below.

TABLE 36

Additional Exemplary Compounds

| Compound | Structure | Proton NMR | MS [M + 1] |
|---|---|---|---|
| N-((1S,2S)-2-(4-amino-7-methyl-5-(4-(pyrrolidine-1-carbonyl)phenyl)-7H-pyrrolo[2,3-d]pyrimidin-6-yl)cyclopropyl) acrylamide | | $^1$H NMR (400 MHz, DMSO-d$_6$) δ 8.40 (d, J = 5.0 Hz, 1H), 8.22 (s, 1H), 7.70-7.56 (m, 2H), 7.51-7.37 (m, 2H), 6.50-5.89 (m, 3H), 5.61 (dd, J = 9.6, 2.6 Hz, 1H), 3.89 (s, 3H), 3.49 (t, J = 6.9 Hz, 2H), 3.44 (q, J = 6.4 Hz, 2H), 2.70 (dq, J = 8.8, 4.5 Hz, 1H), 2.19 (ddd, J = 9.8, 6.4, 3.8 Hz, 1H), 1.87 (ddq, J = 25.5, 13.0, 6.7, 5.8 Hz, 4H), 1.01 (dt, J = 9.8, 5.1 Hz, 1H), 0.57 (dt, J = 7.6, 5.7 Hz, 1H). | 431.20 |
| N-((1R,2S)-2-(4-amino-7-methyl-5-(4-(pyrrolidine-1-carbonyl)phenyl)-7H-pyrrolo[2,3-d]pyrimidin-6-yl)cyclopropyl) acrylamide | 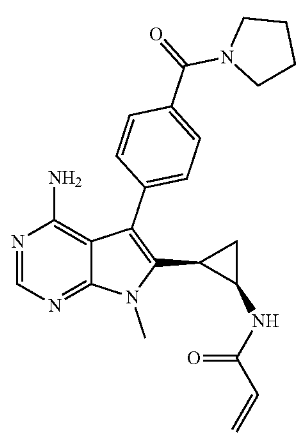 [SMILES: C=CC(=O)N[C@@H]1C[C@@H]1c1c(-c2ccc(C(=O)N3CCCC3)cc2)c2c(N)ncnc2n1C] | $^1$H NMR (400 MHz, DMSO-d$_6$) δ 8.20 (s, 1H), 7.70 (d, J = 6.5 Hz, 1H), 7.69-7.61 (m, 2H), 7.47-7.40 (m, 2H), 6.19 (s, 2H), 5.99 (d, J = 6.2 Hz, 2H), 5.48 (t, J = 6.2 Hz, 1H), 3.73 (s, 3H), 3.50 (td, J = 6.8, 3.0 Hz, 5H), 3.47-3.40 (m, 1H), 2.27 (dt, J = 9.1, 7.1 Hz, 1H), 1.88 (dp, J = 19.1, 6.7 Hz, 4H), 1.29-1.04 (m, 1H), 0.41 (q, J = 5.7 Hz, 1H). | 431.20 |

TABLE 36-continued

Additional Exemplary Compounds

| Compound | Structure | Proton NMR | MS [M + 1] |
|---|---|---|---|
| N-((1R,2R)-2-(4-amino-7-methyl-5-(4-(pyrrolidine-1-carbonyl)phenyl)-7H-pyrrolo[2,3-d]pyrimidin-6-yl)cyclopropyl)acrylamide | 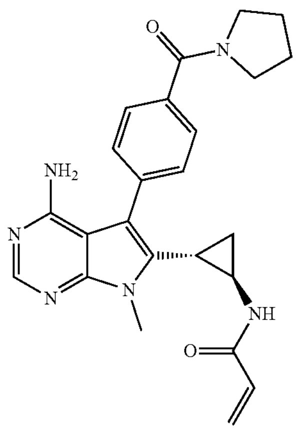 [SMILES: C=CC(=O)N[C@@H]1C[C@H]1c1c(-c2ccc(C(=O)N3CCCC3)cc2)c2c(N)ncnc2n1C] | $^1$H NMR (400 MHz, DMSO-d$_6$) δ 8.39 (d, J = 5.0 Hz, 1H), 8.20 (s, 1H), 7.67-7.53 (m, 2H), 7.49-7.40 (m, 2H), 6.45-5.98 (m, 3H), 5.61 (dd, J = 9.7, 2.7 Hz, 1H), 3.88 (s, 3H), 3.50 (d, J = 6.8 Hz, 2H), 3.49-3.40 (m, 2H), 2.70 (ddd, J = 8.7, 6.5, 3.1 Hz, 1H), 2.19 (ddd, J = 9.8, 6.4, 3.8 Hz, 1H), 1.89 (t, J = 6.6 Hz, 2H), 1.82 (q, J = 6.3 Hz, 2H), 1.01 (dt, J = 9.8, 5.2 Hz, 1H), 0.57 (dt, J = 7.6, 5.7 Hz, 1H). | 431.20 |
| N-((1S,2R)-2-(4-amino-7-methyl-5-(4-(pyrrolidine-1-carbonyl)phenyl)-7H-pyrrolo[2,3-d]pyrimidin-6-yl)cyclopropyl)acrylamide | 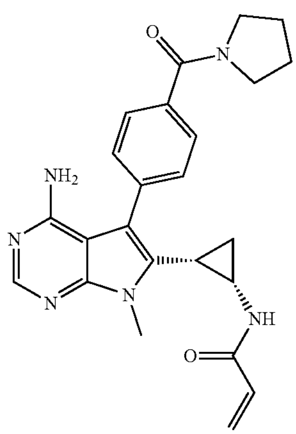 | $^1$H NMR (400 MHz, DMSO-d$_6$) δ 8.17 (s, 1H), 7.69 (d, J = 6.5 Hz, 1H), 7.67-7.59 (m, 2H), 7.48-7.41 (m, 2H), 5.99 (d, J = 6.2 Hz, 3H), 5.47 (t, J = 6.2 Hz, 1H), 3.72 (s, 3H), 3.50 (td, J = 7.0, 3.5 Hz, 4H), 3.47-3.40 (m, 1H), 2.27 (dt, J = 9.1, 7.1 Hz, 1H), 1.88 (dp, J = 18.9, 6.8 Hz, 4H), 1.16 (td, J = 8.5, 5.8 Hz, 1H), 0.41 (dt, J = 7.1, 5.5 Hz, 1H). | 431.20 |

Example 38

Scheme 35

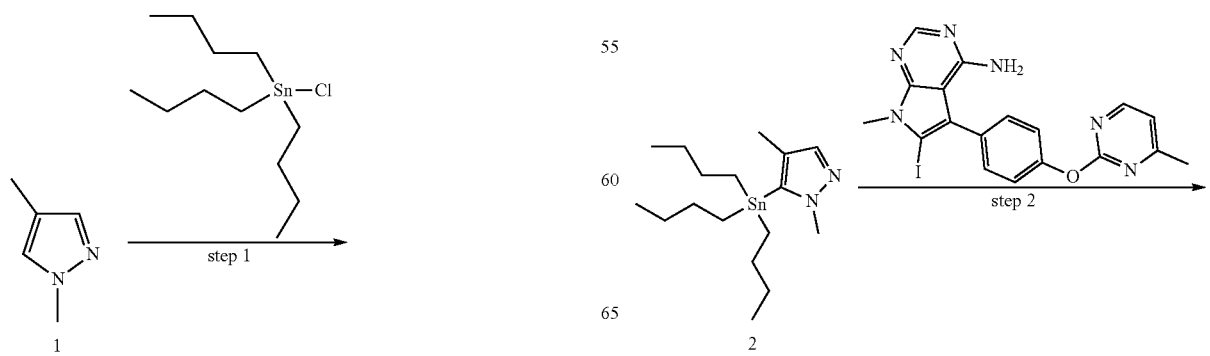

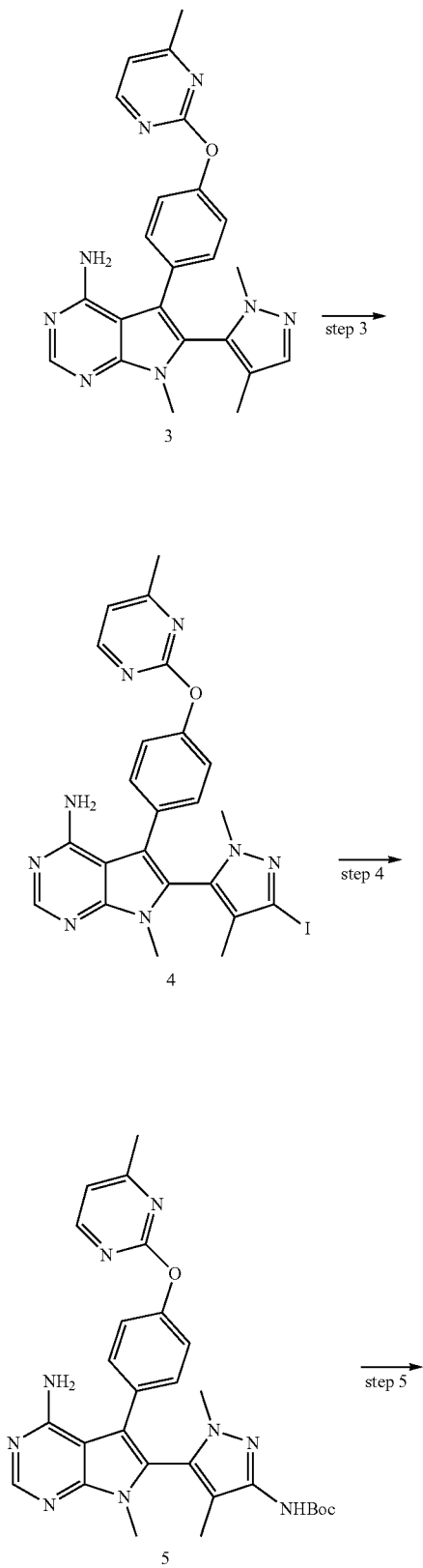

1,4-dimethyl-5-(tributylstannyl)-1H-pyrazole

Step 1: To a solution of 1,4-dimethylpyrazole (2.00 g, 20.805 mmol) in THF (15 mL) was added dropwise n-butyl-lithium solution (2.5 M in THF, 1.07 mL, 16.644 mmol) at −78 degrees C. under N2 atmosphere. The reaction mixture was stirred at −78 degrees C. for 30 mins. Then a solution of Bu3SnCl (10.16 g, 31.207 mmol) was added dropwise and the mixture was stirred for another 2 h. The reaction was quenched with sat. NH4Cl (100 mL), and then the mixture was extracted with EtOAc (3*50 mL). The combined organic extracts were washed with brine (50 mL), dried over anhydrous Na2SO4, and concentrated under vacuum to yield a crude product which was purified by silica gel column chromatography (PE/EA=4:1) resulted in 1,4-dimethyl-5-(tributylstannyl)pyrazole (5.6 g, 69.9%) as colorless oil.

6-(1,4-dimethyl-1H-pyrazol-5-yl)-7-methyl-5-(4-((4-methylpyrimidin-2-yl)oxy)phenyl)-7H-pyrrolo[2,3-d]pyrimidin-4-amine

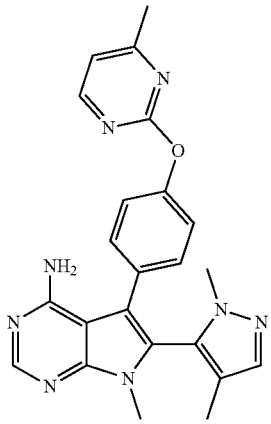 [SMILES: Cc1ccnc(Oc2ccc(-c3c(-c4c(C)cnn4C)n(C)c4ncnc(N)c34)cc2)n1]

Step 2: A solution/mixture of 6-iodo-7-methyl-5-[4-[(4-methylpyrimidin-2-yl)oxy]phenyl]pyrrolo[2,3-d]pyrimidin-4-amine (1.40 g, 3.055 mmol), 1,4-dimethyl-5-(tributylstannyl)pyrazole (2.94 g, 7.638 mmol), tetrakis(triphenylphosphine)palladium (353.03 mg, 0.306 mmol) and copper(I) iodide (116.37 mg, 0.611 mmol) in toluene was stirred for overnight at 110° C. under nitrogen atmosphere. The reaction mixture was diluted with water, extracted with $CH_2Cl_2$ (3×50 mL). The combined organic layers were washed with brine (1×70 mL), dried over anhydrous $Na_2SO_4$. After filtration, the filtrate was concentrated under reduced pressure. The residue was purified by silica gel column chromatography, eluted with $CH_2Cl_2$/MeOH (12:1) to afford 6-(2,4-dimethylpyrazol-3-yl)-7-methyl-5-[4-[(4-methylpyrimidin-2-yl)oxy]phenyl]pyrrolo[2,3-d]pyrimidin-4-amine(320 mg, 24.6%) as a light yellow solid.

6-(3-iodo-1,4-dimethyl-1H-pyrazol-5-yl)-7-methyl-5-(4-((4-methylpyrimidin-2-yl)oxy)phenyl)-7H-pyrrolo[2,3-d]pyrimidin-4-amine

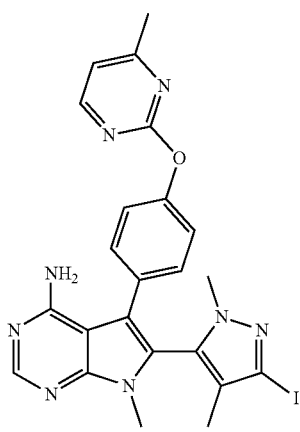 [SMILES: Cc1ccnc(Oc2ccc(-c3c(-c4c(C)c(I)nn4C)n(C)c4ncnc(N)c34)cc2)n1]

Step 3: A solution/mixture of 6-(3-iodo-1,4-dimethyl-1H-pyrazol-5-yl)-7-methyl-5-(4-((4-methylpyrimidin-2-yl)oxy)phenyl)-7H-pyrrolo[2,3-d]pyrimidin-4-amine (320 mg, 0.75 mmol), NIS (337 mg, 1.50 mmol) and trifluoroacetaldehyde (368 mg, 3.75 mmol) in DCM was stirred for 48 h at 60° C. The reaction mixture was diluted with water, extracted with $CH_2Cl_2$ (3×30 mL). The combined organic layers were washed with brine, dried over anhydrous $Na_2SO_4$. After filtration, the filtrate was concentrated under reduced pressure. The residue was purified by prep-TLC ($CH_2Cl_2$/MeOH 10:1) to afford 6-(3-iodo-1,4-dimethyl-1H-pyrazol-5-yl)-7-methyl-5-{4-[(4-methylpyrimidin-2-yl)oxy]phenyl}-7H-pyrrolo[2,3-d]pyrimidin-4-amine (171 mg, 41.3%) as a light yellow solid.

tert-butyl (5-(4-amino-7-methyl-5-(4-((4-methylpyrimidin-2-yl)oxy)phenyl)-7H-pyrrolo[2,3-d]pyrimidin-6-yl)-1,4-dimethyl-1H-pyrazol-3-yl)carbamate

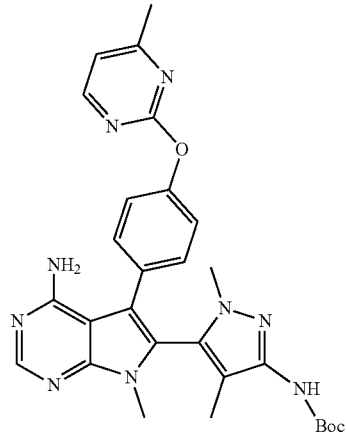 [SMILES: Cc1ccnc(Oc2ccc(-c3c(-c4c(C)c(NC(=O)OC(C)(C)C)nn4C)n(C)c4ncnc(N)c34)cc2)n1]

Step 4: A solution/mixture of 6-(5-iodo-2,4-dimethylpyrazol-3-yl)-7-methyl-5-[4-[(4-methylpyrimidin-2-yl)oxy]phenyl]pyrrolo[2,3-d]pyrimidin-4-amine (170 mg, 0.31 mmol), tert-butyl carbamate (72 mg, 0.62 mmol), copper(I) iodide (12 mg, 0.063 mmol), and potassium methaneperoxoate potassium (86 mg, 0.62 mmol) in dioxane was stirred overnight at 90° C. under nitrogen atmosphere. The reaction mixture was diluted with water, extracted with $CH_2Cl_2$ (3×30 mL). The combined organic layers were washed with brine (1×30 mL), dried over anhydrous $Na_2SO_4$. After filtration, the filtrate was concentrated under reduced pressure. The residue was purified by prep-TLC ($CH_2Cl_2$/MeOH 10:1) to afford tert-butyl N-[5-(4-amino-7-methyl-5-[4-[(4-methylpyrimidin-2-yl)oxy]phenyl]pyrrolo[2,3-d]pyrimidin-6-yl)-1,4-dimethylpyrazol-3-yl]carbamate (25 mg, 15%) as colorless oil.

1853

6-(3-amino-1,4-dimethyl-1H-pyrazol-5-yl)-7-methyl-5-(4-((4-methylpyrimidin-2-yl)oxy)phenyl)-7H-pyrrolo[2,3-d]pyrimidin-4-amine

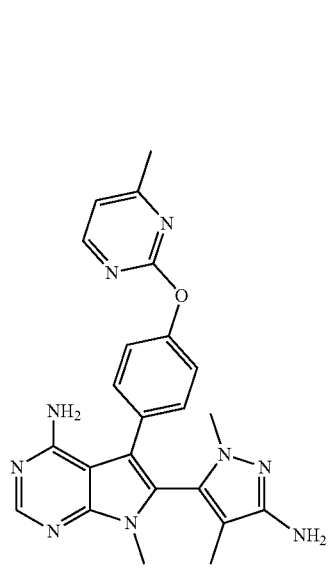 [SMILES: Cc1ccnc(Oc2ccc(-c3c(-c4c(C)c(N)nn4C)n(C)c4ncnc(N)c34)cc2)n1]

Step 5: A mixture of tert-butyl N-[5-(4-amino-7-methyl-5-[4-[(4-methylpyrimidin-2-yl)oxy]phenyl]pyrrolo[2,3-d]pyrimidin-6-yl)-1,4-dimethylpyrazol-3-yl]carbamate (25 mg, 0.046 mmol) in HCl(gas)/1,4-dioxane (1 mL) was stirred for 10 min at room temperature. The resulting mixture was concentrated under reduced pressure. This resulted in 5-(4-amino-7-methyl-5-[4-[(4-methylpyrimidin-2-yl)oxy]phenyl]pyrrolo[2,3-d]pyrimidin-6-yl)-1,4-dimethylpyrazol-3-amine (25 mg, 98%) as yellow oil.

1854

N-(5-(4-amino-7-methyl-5-(4-((4-methylpyrimidin-2-yl)oxy)phenyl)-7H-pyrrolo[2,3-d]pyrimidin-6-yl)-1,4-dimethyl-1H-pyrazol-3-yl)methacrylamide

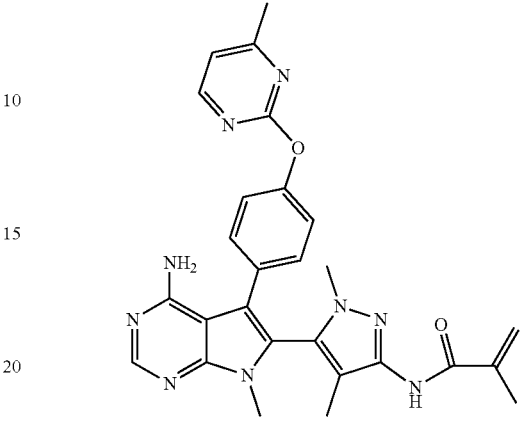

Step 6: A round bottomed flask was charged with 5-(4-amino-7-methyl-5-[4-[(4-methylpyrimidin-2-yl)oxy]phenyl]pyrrolo[2,3-d]pyrimidin-6-yl)-1,4-dimethylpyrazol-3-amine (17 mg, 0.039 mmol), TEA (11.7 mg, 0.116 mmol) in DCM (2 mL) at 0° C., then added methacryloyl chloride (3.62 mg, 0.035 mmol) stirred for 2 h. The resulting crude material was purified by prep-HPLC (Column: XBridge Prep OBD C18 Column, 30×150 mm 5 um; Mobile Phase A:Water(10 MMOL/L NH$_4$HCO$_3$), Mobile Phase B:ACN; Flow rate:60 mL/min; Gradient:20 B to 45 B in 8 min; 220 nm; RT1:5.78; RT2:; Injection Volume: ml; Number Of Runs:;). Lyophilization yielded N-[5-(4-amino-7-methyl-5-[4-[(4-methylpyrimidin-2-yl)oxy]phenyl]pyrrolo[2,3-d]pyrimidin-6-yl)-1,4-dimethylpyrazol-3-yl]-2-methylprop-2-enamide (2.1 mg, 10.7%) as an off-white amorphous solid.

TABLE 37

Exemplary Compound

| Compound | Structure | Proton NMR | MS [M + 1] |
|---|---|---|---|
| N-(5-(4-amino-7-methyl-5-(4-((4-methylpyrimidin-2-yl)oxy)phenyl)-7H-pyrrolo[2,3-d]pyrimidin-6-yl)-1,4-dimethyl-1H-pyrazol-3-yl)methacrylamide | 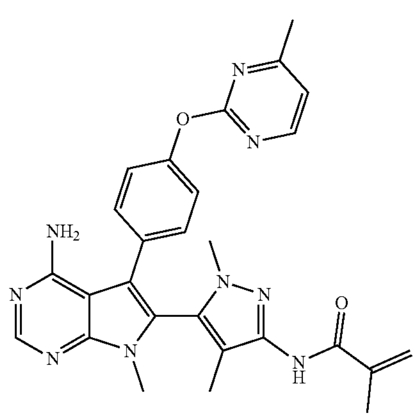 [SMILES: C=C(C)C(=O)Nc1nn(C)c(-c2c(-c3ccc(Oc4nccc(C)n4)cc3)c3c(N)ncnc3n2C)c1C] | $^1$H NMR (400 MHz, Chloroform-d) 8.44 (s, 1H), 8.39 (d, J = 5.0 Hz, 1H), 7.54 (s, 1H), 7.26 (q, J = 8.7 Hz, 4H), 6.95 (d, J = 5.0 Hz, 1H), 5.89 (s, 1H), 5.52 (s, 1H), 5.28 (s, 2H), 3.68 (s, 3H), 3.38 (s, 3H), 2.52 (s, 3H), 2.08 (s, 3H), 1.94 (s, 3H). | 510.25 |

Example 39

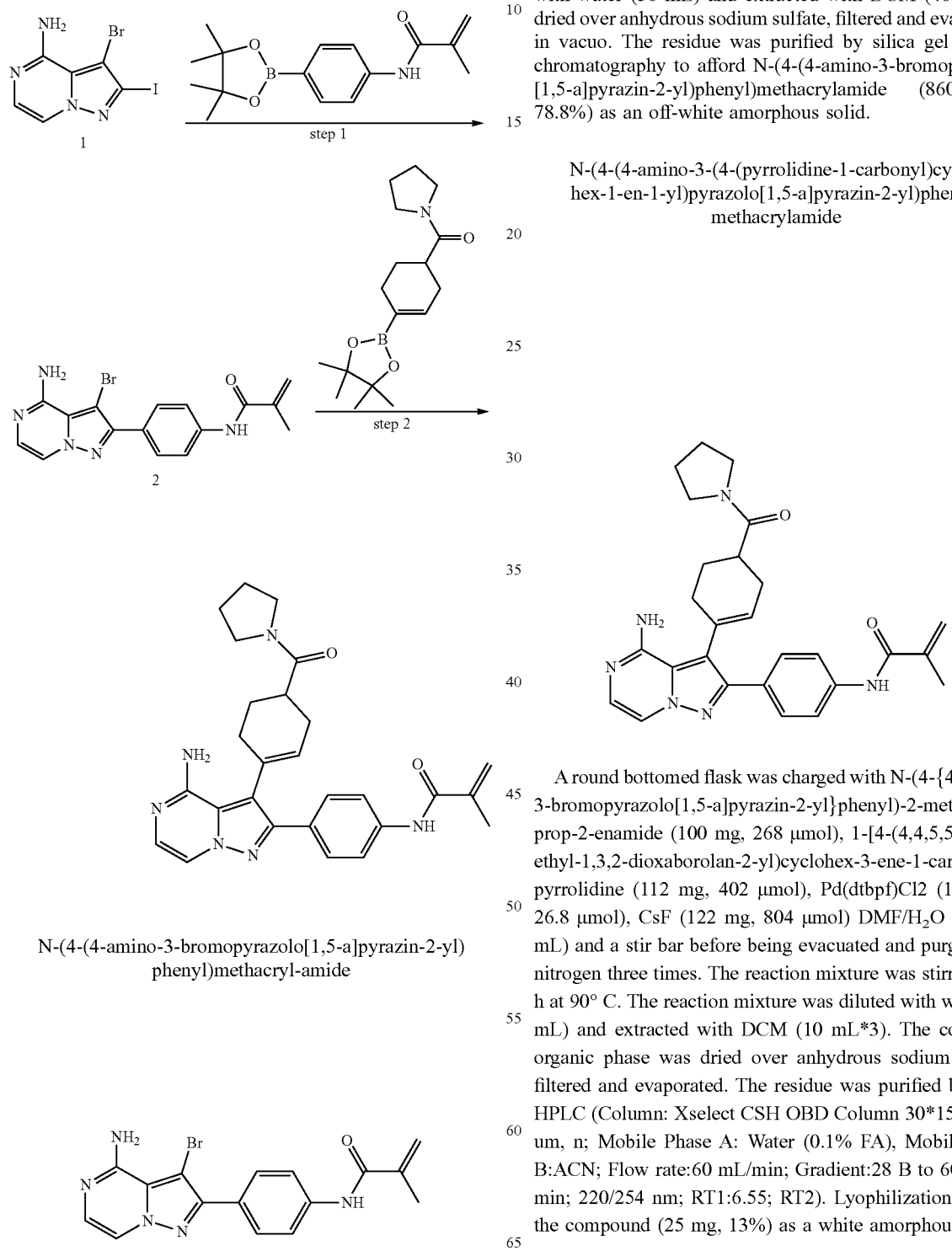

N-(4-(4-amino-3-bromopyrazolo[1,5-a]pyrazin-2-yl)phenyl)methacryl-amide

A round bottomed flask was charged with 3-bromo-2-iodopyrazolo[1,5-a]pyrazin-4-amine (1 g, 2.95 mmol), 2-methyl-N-[4-(4,4,5,5-tetramethyl-1,3,2-dioxaborolan-2-yl)phenyl]prop-2-enamide (1.26 g, 4.42 mmol), Pd(dppf)Cl2 (215 mg, 295 μmol), K3PO4 (1.87 g, 8.85 mmol), dioxane (15 mL) and a stir bar before being evacuated and purged with nitrogen three times. The reaction mixture was stirred for 1 h at 90° C. The reaction mixture was diluted with water (50 mL) and extracted with DCM (40 mL*3), dried over anhydrous sodium sulfate, filtered and evaporated in vacuo. The residue was purified by silica gel column chromatography to afford N-(4-(4-amino-3-bromopyrazolo[1,5-a]pyrazin-2-yl)phenyl)methacrylamide (860 mg, 78.8%) as an off-white amorphous solid.

N-(4-(4-amino-3-(4-(pyrrolidine-1-carbonyl)cyclohex-1-en-1-yl)pyrazolo[1,5-a]pyrazin-2-yl)phenyl)methacrylamide A round bottomed flask was charged with N-(4-{4-amino-3-bromopyrazolo[1,5-a]pyrazin-2-yl}phenyl)-2-methyl-prop-2-enamide (100 mg, 268 μmol), 1-[4-(4,4,5,5-tetramethyl-1,3,2-dioxaborolan-2-yl)cyclohex-3-ene-1-carbonyl]pyrrolidine (112 mg, 402 μmol), Pd(dtbpf)Cl2 (17.4 mg, 26.8 μmol), CsF (122 mg, 804 μmol) DMF/H2O (10:1, 5 mL) and a stir bar before being evacuated and purged with nitrogen three times. The reaction mixture was stirred for 1 h at 90° C. The reaction mixture was diluted with water (20 mL) and extracted with DCM (10 mL*3). The combined organic phase was dried over anhydrous sodium sulfate, filtered and evaporated. The residue was purified by prep-HPLC (Column: Xselect CSH OBD Column 30*150 mm 5 um, n; Mobile Phase A: Water (0.1% FA), Mobile Phase B:ACN; Flow rate:60 mL/min; Gradient:28 B to 60 B in 8 min; 220/254 nm; RT1:6.55; RT2). Lyophilization yielded the compound (25 mg, 13%) as a white amorphous solid.

Additional compounds prepared according to the methods of Example 39 are depicted in Table 38 below.

TABLE 38

Additional Exemplary Compounds

| Compound | Structure | Proton NMR | MS [M + 1] |
|---|---|---|---|
| N-(4-(4-amino-3-(4-((4-methylpyrimidin-2-yl)oxy)phenyl)pyrazolo[1,5-a]pyrazin-2-yl)phenyl)methacrylamide | 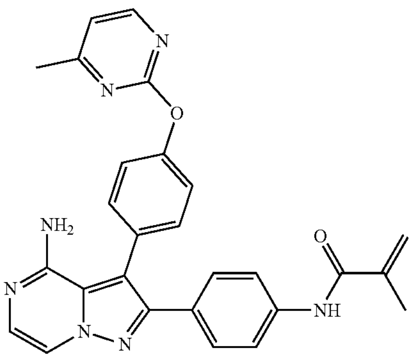 [SMILES: C=C(C)C(=O)Nc1ccc(-c2nn3ccnc(N)c3c2-c2ccc(Oc3nccc(C)n3)cc2)cc1] | $^1$H NMR (400 MHz, Methanol-d4) δ 8.46 (d, J = 5.0 Hz, 1H), 7.96 (d, J = 4.9 Hz, 1H), 7.63-7.56 (m, 2H), 7.55-7.45 (m, 4H), 7.38-7.30 (m, 2H), 7.30 (d, J = 4.9 Hz, 1H), 7.17 (d, J = 5.1 Hz, 1H), 5.83-5.78 (m, 1H), 5.55-5.50 (m, 1H), 2.53 (s, 3H), 2.04 (dd, J = 1.7, 0.9 Hz, 3H). | 478.20 |
| N-(4-(4-amino-3-(4-(pyrrolidine-1-carbonyl)phenyl)pyrazolo[1,5-a]pyrazin-2-yl)phenyl)methacrylamide | 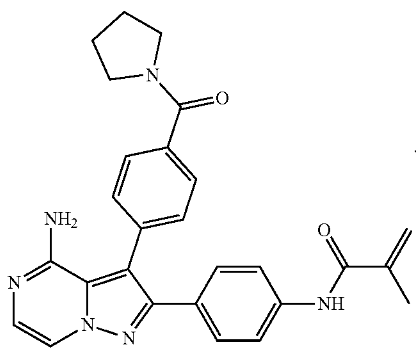 | $^1$H NMR (400 MHz, Methanol-d$_4$) δ 7.97 (d, J = 4.8 Hz, 1H), 7.68 (d, J = 7.9 Hz, 2H), 7.55 (dd, J = 11.1, 8.2 Hz, 4H), 7.42 (d, J = 8.7 Hz, 2H), 7.31 (d, J = 4.9 Hz, 1H), 5.80 (s, 1H), 5.53 (s, 1H), 3.65 (t, J = 6.9 Hz, 2H), 3.56 (t, J = 6.5 Hz, 2H), 2.05 (d, J = 6.5 Hz, 1H), 2.03 (s, 4H), 1.97 (p, J = 6.9 Hz, 2H). | 467.20 |
| (S)-N-(4-(4-amino-3-(4-(pyrrolidine-1-carbonyl)cyclohex-1-en-1-yl)pyrazolo[1,5-a]pyrazin-2-yl)phenyl)methacrylamide | 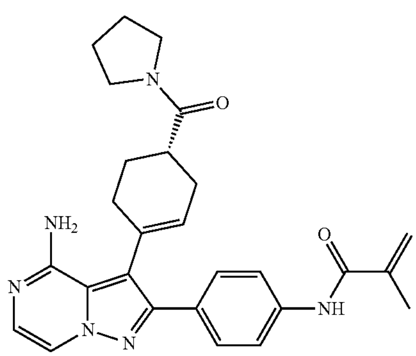 [SMILES: C=C(C)C(=O)Nc1ccc(-c2nn3ccnc(N)c3c2C2=CC[C@@H](C(=O)N3CCCC3)CC2)cc1] | $^1$H NMR (400 MHz, DMSO-d$_6$) δ 9.91 (s, 1H), 7.90 (d, J = 4.6 Hz, 1H), 7.77 (d, J = 2.7 Hz, 4H), 7.22 (d, J = 4.7 Hz, 1H), 6.74 (s, 2H), 5.95 (s, 1H), 5.83 (s, 1H), 5.54 (s, 1H), 3.63-3.53 (m, 1H), 3.49 (q, J = 8.7, 7.8 Hz, 1H), 3.39 (s, 1H), 3.36 (d, J = 5.0 Hz, 1H), 3.32-3.24 (m, 1H), 3.00 (s, 1H), 2.39 (s, 2H), 2.20-1.70 (m, 11H). | 471.25 |
| (R)-N-(4-(4-amino-3-(4-(pyrrolidine-1-carbonyl)cyclohex-1-en-1-yl)pyrazolo[1,5-a]pyrazin-2-yl)phenyl)methacrylamide | 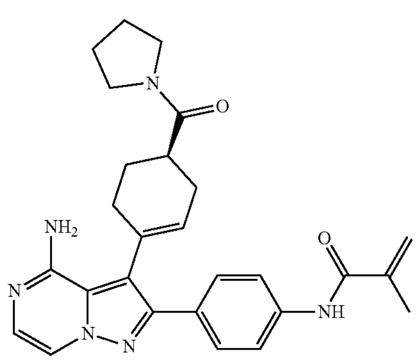 [SMILES: C=C(C)C(=O)Nc1ccc(-c2nn3ccnc(N)c3c2C2=CC[C@H](C(=O)N3CCCC3)CC2)cc1] | $^1$H NMR (400 MHz, DMSO-d$_6$) δ 9.91 (s, 1H), 7.90 (d, J = 4.6 Hz, 1H), 7.77 (d, J = 2.7 Hz, 4H), 7.22 (d, J = 4.7 Hz, 1H), 6.74 (s, 2H), 5.95 (s, 1H), 5.83 (s, 1H), 5.54 (s, 1H), 3.63-3.53 (m, 1H), 3.49 (q, J = 8.7, 7.8 Hz, 1H), 3.39 (s, 1H), 3.36 (d, J = 5.0 Hz, 1H), 3.32-3.24 (m, 1H), 3.00 (s, 1H), 2.39 (s, 2H), 2.20-1.70 (m, 11H). | 471.25 |

TABLE 38-continued

Additional Exemplary Compounds

| Compound | Structure | Proton NMR | MS [M + 1] |
|---|---|---|---|
| N-(4-(4-amino-3-(4-(pyrrolidine-1-carbonyl)cyclohex-1-en-1-yl)pyrazolo[1,5-a]pyrazin-2-yl)phenyl) methacrylamide | 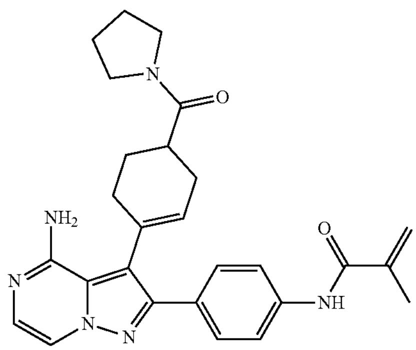 [SMILES: C=C(C)C(=O)Nc1ccc(-c2nn3ccnc(N)c3c2C2=CCC(C(=O)N3CCCC3)CC2)cc1] | $^1$H NMR (400 MHz, DMSO-d$_6$) δ 9.91 (s, 1H), 7.90 (d, J = 4.6 Hz, 1H), 7.77 (d, J = 2.7 Hz, 4H), 7.22 (d, J = 4.7 Hz, 1H), 6.74 (s, 2H), 5.95 (s, 1H), 5.83 (s, 1H), 5.54 (s, 1H), 3.63-3.53 (m, 1H), 3.49 (q, J = 8.7, 7.8 Hz, 1H), 3.39 (s, 1H), 3.36 (d, J = 5.0 Hz, 1H), 3.32-3.24 (m, 1H), 3.00 (s, 1H), 2.39 (s, 2H), 2.20-1.70 (m, 11H). | 471.25 |
| 2-(6-ethynyl-4-methylpyridin-3-yl)-3-(3-fluoro-4-((4-methylpyrimidin-2-yl)oxy)phenyl)-6,7-dihydro-4H-pyrazolo[5,1-c][1,4]oxazine | 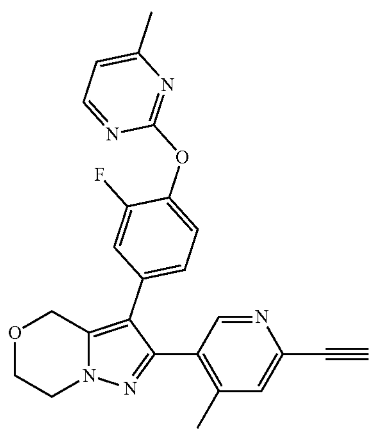 [SMILES: C#Cc1cc(C)c(-c2nn3c(c2-c2ccc(Oc4nccc(C)n4)c(F)c2)COCC3)cn1] | $^1$H NMR (400 MHz, DMSO-d$_6$) δ 8.47 (d, J = 5.0 Hz, 1H), 8.33 (s, 1H), 7.52 (d, J = 0.9 Hz, 1H), 7.29 (t, J = 8.4 Hz, 1H), 7.18 (d, J = 5.1 Hz, 1H), 7.02 (dd, J = 11.7, 2.1 Hz, 1H), 6.85-6.78 (m, 1H), 5.02 (s, 2H), 4.36 (s, 1H), 4.27 (t, J = 5.1 Hz, 2H), 4.17 (t, J = 5.2 Hz, 2H), 2.42 (s, 3H), 2.07 (s, 3H). | 442.15 |

Example 40

Scheme 37

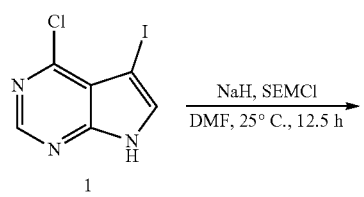

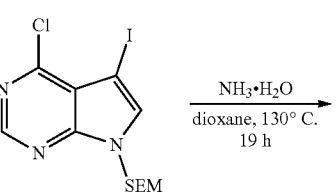

-continued

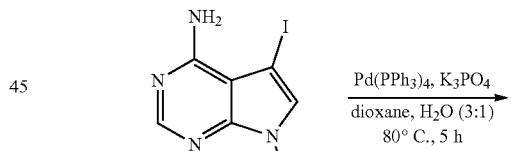

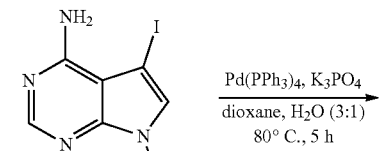

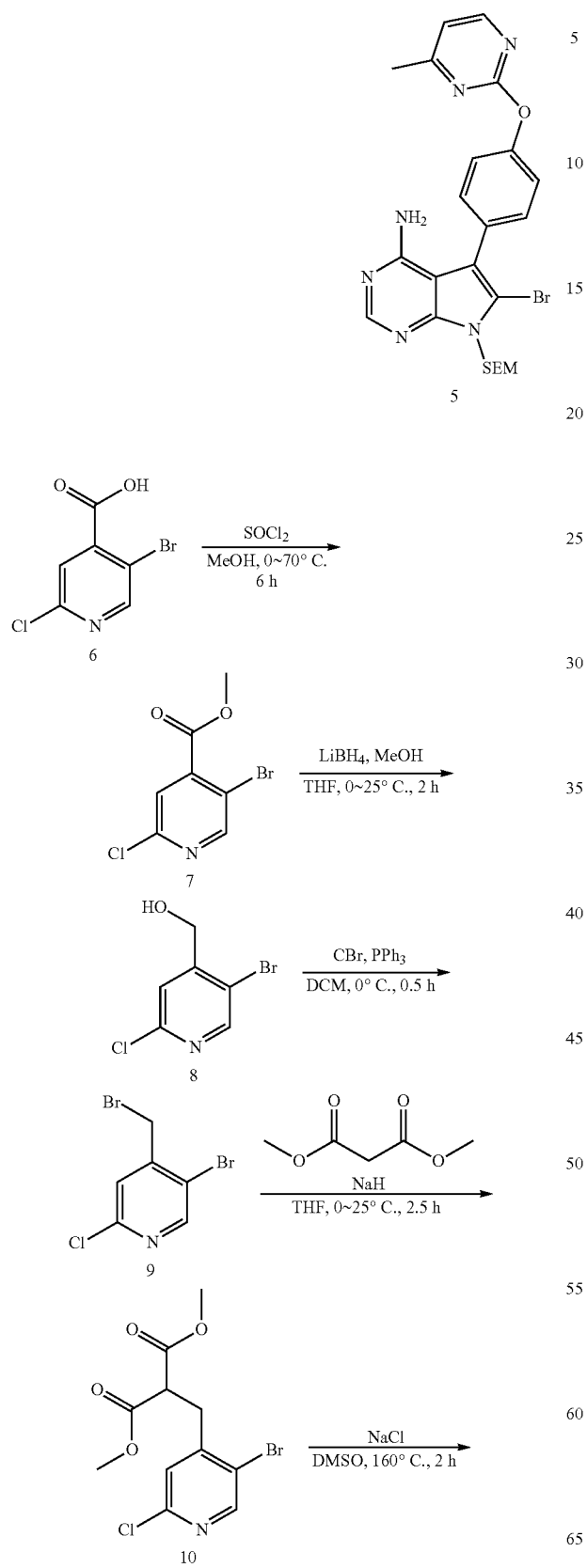
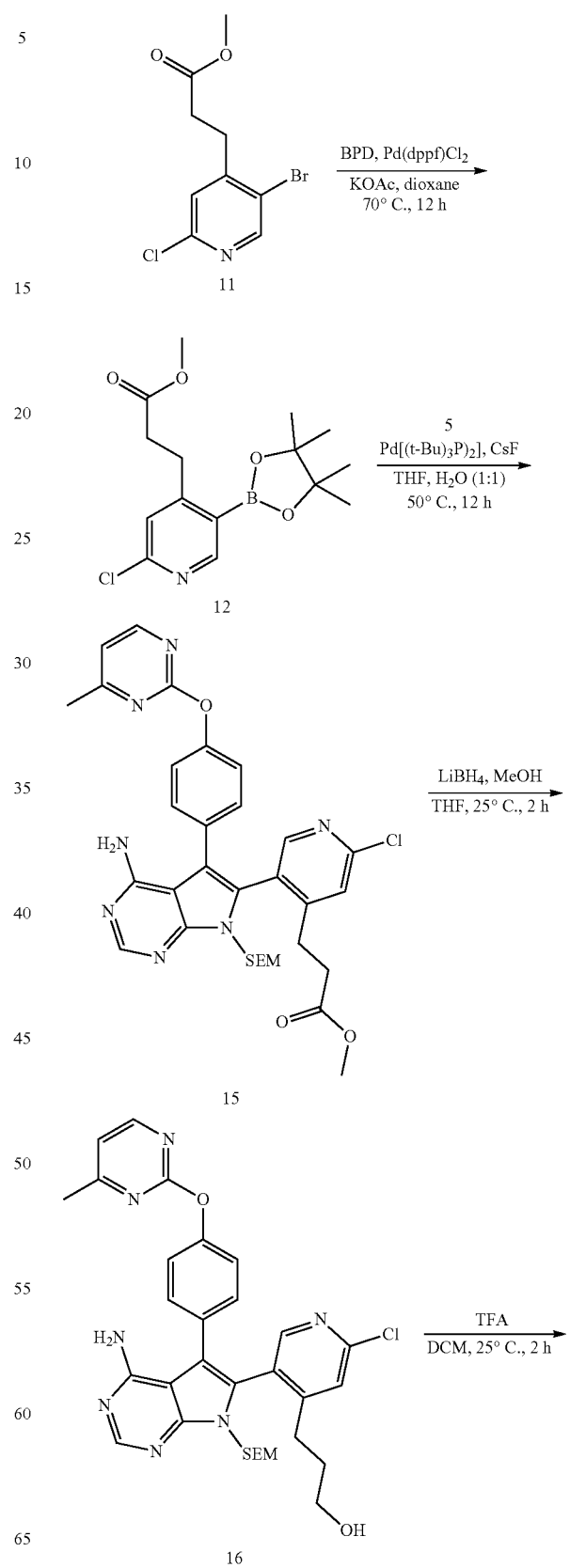

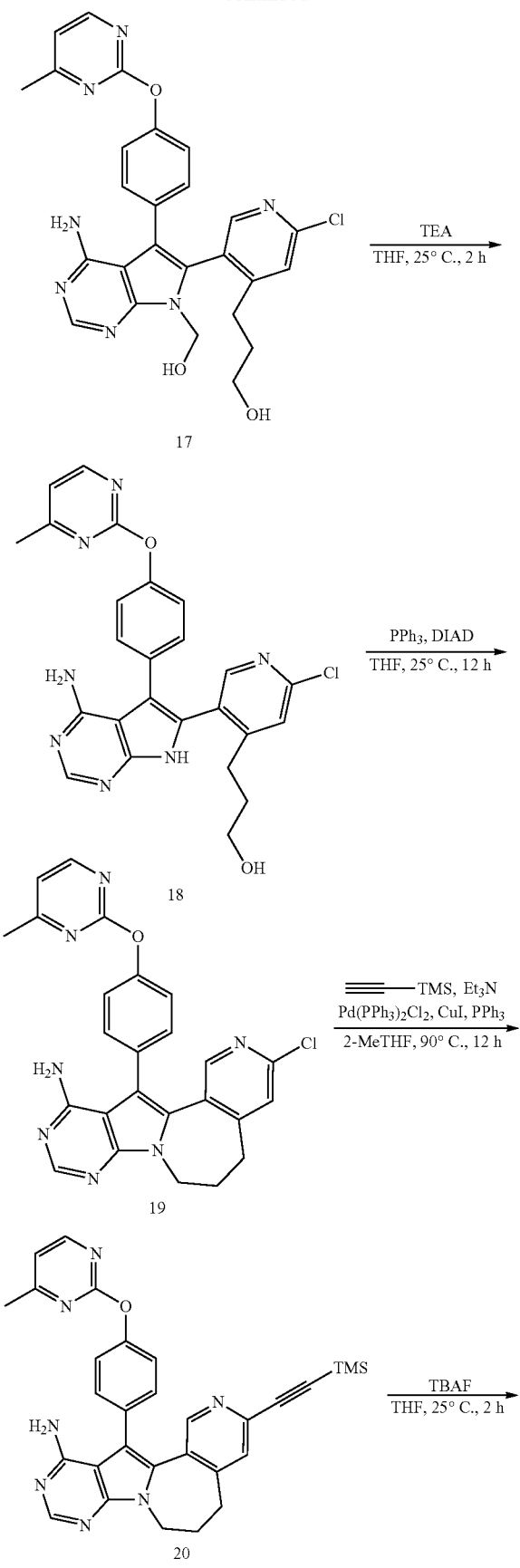

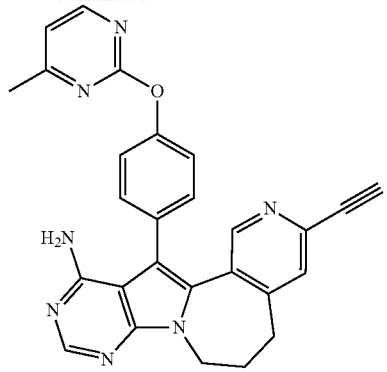

4-methyl-2-[4-(4,4,5,5-tetramethyl-1,3,2-dioxaborolan-2-yl)phenoxy]pyrimidine Step 1: The solution of 2-chloro-4-methylpyrimidine (5.00 g, 1.2 eq, 38.80 mmol) and 4-(4,4,5,5-tetramethyl-1,3,2-dioxaborolan-2-yl)phenol (7.10 g, 32.30 mmol) in DMF (30.0 mL) was added t-BuOK (7.24 g, 2.0 eq, 77.6 mmol) in portions, the solution was stirred at 120° C. for 12 h. The reaction mixture was cooled and diluted with water (50.0 mL), then extracted with EtOAc (30.0 mL×3), the combined organic layers were concentrated under reduced pressure. The residue was purified by column chromatography (Petroleum ether/EtOAc=10/1 to 4/1). 4-methyl-2-[4-(4,4,5,5-tetramethyl-1,3,2-dioxaborolan-2-yl)phenoxy]pyrimidine (2.90 g, 22.9% yield) was obtained as a mixture which will be used for the next step without further purification.

4-chloro-5-iodo-7-{[2-(trimethylsilyl)ethoxy]methyl}-7H-pyrrolo[2,3-d]pyrimidine Step 2: To a solution of 4-chloro-5-iodo-7H-pyrrolo[2,3-d]pyrimidine (5.00 g, 17.80 mmol) in DMF (20.0 mL) was added NaH (1.06 g, 1.5 eq, 26.70 mmol, 60% purity), the resulting mixture was stirred at 25° C. for 0.5 h, then SEMCl (3.85 g, 1.3 eq, 23.14 mmol) was added. The reaction mixture was stirred at 25° C. for 12 h. The reaction mixture was filtered and concentrated under reduced pressure. The residue was purified by column chromatography (Petroleum ether/EtOAc=10/1 to 4/1). 4-chloro-5-iodo-7-{[2-(trimethylsilyl)ethoxy]methyl}-7H-pyrrolo[2,3-d]pyrimidine (3.90 g, 53.4% yield) was obtained as a white solid.

5-iodo-7-{[2-(trimethylsilyl)ethoxy]methyl}-7H-pyrrolo[2,3-d]pyrimidin-4-amine Step 3: The solution of 4-chloro-5-iodo-7-{[2-(trimethylsilyl)ethoxy]methyl}-7H-pyrrolo[2,3-d]pyrimidine (3.90 g, 9.51 mmol) in dioxane (15.0 mL) and NH$_3$·H$_2$O (15.0 mL, 15.8 eq, 150.26 mmol, 25% purity) was stirred at 130° C. for 19 h in an autoclave. The reaction mixture was cooled and concentrated under reduced pressure. The residue was purified by column chromatography (Petrol ether/EtOAc=4/1 to 2/1). 5-iodo-7-{[2-(trimethylsilyl)ethoxy]methyl}-7H-pyrrolo[2,3-d]pyrimidin-4-amine (3.50 g, 94.3% yield) was obtained as a white solid.

5-{4-[(4-methylpyrimidin-2-yl)oxy]phenyl}-7-{[2-(trimethylsilyl)ethoxy]methyl}-7H-pyrrolo[2,3-d]pyrimidin-4-amine Step 4: The solution of 5-iodo-7-{[2-(trimethylsilyl)ethoxy]methyl}-7H-pyrrolo[2,3-d]pyrimidin-4-amine (2.58 g, 6.62 mmol), 4-methyl-2-(4-(4,4,5,5-tetramethyl-1,3,2-dioxaborolan-2-yl)phenoxy)pyrimidine (2.90 g, 1.4 eq, 9.27 mmol), Pd(PPh$_3$)$_4$ (764.0 mg, 0.1 eq, 0.66 mmol), K$_3$PO$_4$ (3.50 g, 2.5 eq, 16.55 mmol) in dioxane (30.0 mL) and H$_2$O (10.0 mL) was stirred at 80° C. for 5 h. The reaction was cooled and filtered, the filtrate was concentrated, the residue was purified by column chromatography (Petroleum ether/EtOAc=1/1 to 0/1). 5-{4-[(4-methylpyrimidin-2-yl)oxy]phenyl}-7-{[2-(trimethylsilyl)ethoxy]methyl}-7H-pyrrolo[2,3-d]pyrimidin-4-amine (1.70 g, 57.4% yield) was obtained as a yellow oil.

6-bromo-5-{4-[(4-methylpyrimidin-2-yl)oxy]phenyl}-7-{[2-(trimethylsilyl)ethoxy]methyl}-7H-pyrrolo[2,3-d]pyrimidin-4-amine Step 5: To a solution of 5-{4-[(4-methylpyrimidin-2-yl)oxy]phenyl}-7-{[2-(trimethylsilyl)ethoxy]methyl}-7H-pyrrolo[2,3-d]pyrimidin-4-amine (1.60 g, 3.56 mmol) in DMF (30.0 mL) was added NBS (695.0 mg, 1.1 eq, 3.92 mmol) in portions. The reaction was stirred at 25° C. for 0.5 h. Then the reaction was concentrated and the residue was purified by column chromatography (Petroleum ether/EtOAc=4/1 to 2/1). Product 6-bromo-5-{4-[(4-methylpyrimidin-2-yl)oxy]phenyl}-7-{[2-(trimethylsilyl)ethoxy]methyl}-7H-pyrrolo[2,3-d]pyrimidin-4-amine (1.20 g, 64.1% yield) was obtained as a light yellow solid.

Methyl 5-bromo-2-chloropyridine-4-carboxylate

Step 6: To a solution of 5-bromo-2-chloropyridine-4-carboxylic acid (15.00 g, 63.40 mmol) in MeOH (50.0 mL) was added SOCl$_2$ (11.30 g, 1.5 eq, 95.10 mmol) slowly at 0° C. Then the reaction mixture was heated to 70° C. and kept at this temperature for 6 h. The reaction mixture was concentrated under reduced pressure, the residue was purified by column chromatography (Petroleum ether/EtOAc=10/1 to 5/1) Methyl 5-bromo-2-chloropyridine-4-carboxylate (12.00 g, 75.9% yield) was obtained as a colorless oil.

(5-bromo-2-chloropyridin-4-yl)methanol

Step 7: To the solution of methyl 5-bromo-2-chloropyridine-4-carboxylate (11.5 g, 45.90 mmol) in THF (100.0 mL) was added LiBH$_4$ (1.49 g, 1.5 eq, 68.85 mmol) slowly at 0° C. The resulting solution was warmed to 25° C. and stirred at this temperature for 2 h before quenched by MeOH. The reaction mixture was concentrated under reduced pressure, the residue was purified by column chromatography (Petrol ether/EtOAc=10/1 to 3/1). (5-bromo-2-chloropyridin-4-yl)methanol (6.70 g, 65.6% yield) was obtained as a white solid.

5-bromo-4-(bromomethyl)-2-chloropyridine

Step 8: The solution of (5-bromo-2-chloropyridin-4-yl)methanol (1.00 g, 4.49 mmol), PPh$_3$ (1.76 g, 1.5 eq, 6.73 mmol) and CBr$_4$ (2.23 g, 1.5 eq, 6.73 mmol) in DCM (15.0 mL) was stirred at 0° C. for 0.5 h. The reaction mixture was concentrated under reduced pressure, the residue was purified by column chromatography (Petroleum ether/EtOAc=20/1 to 10/1). 5-bromo-4-(bromomethyl)-2-chloropyridine (1.20 g, 93.7% yield) was obtained as a colorless oil.

1,3-dimethyl 2-[(5-bromo-2-chloropyridin-4-yl)methyl]propanedioate

Step 9: NaH (1.07 g, 1.1 eq, 26.95 mmol, 60% purity) was suspended in dry THF (70.0 mL) at 0° C. and treated dropwise with a solution of dimethyl malonate (3.23 g, 1.0 eq, 24.50 mmol). After stirring for 30 min at 25° C., a solution of 5-bromo-4-(bromomethyl)-2-chloropyridine (7.00 g, 24.50 mmol) in dry THF (10.0 mL) was added and stirring was continued for further 2 h. The reaction mixture was quenched by water (1.0 mL) and concentrated under reduced pressure, the residue was purified by column chromatography (Petroleum ether/EtOAc=1/0 to 10/1). 1,3-dimethyl 2-[(5-bromo-2-chloropyridin-4-yl)methyl]propanedioate (5.80 g, 70.3% yield) was obtained as a white solid.

Methyl 3-(5-bromo-2-chloropyridin-4-yl)propanoate

Step 10: The solution of 1,3-dimethyl 2-[(5-bromo-2-chloropyridin-4-yl)methyl]propanedioate (5.3 g, 15.70 mmol), NaCl (912.0 mg, 1.0 eq, 15.70 mmol) and H$_2$O (563.0 mg, 2.0 eq, 31.40 mmol) in DMSO (80.0 mL) was stirred at 160° C. for 2 h. After cooling to room temperature, the reaction mixture was poured into EtOAc (70.0 mL). The resulting solution was washed with H$_2$O (500.0 mL), brine (300.0 mL), dried over anhydrous MgSO$_4$ and then concentrated under reduced pressure, the residue was purified by column chromatography (Petrol ether/EtOAc=20/1 to 10/1). Methyl 3-(5-bromo-2-chloropyridin-4-yl)propanoate (2.60 g, 59.9% yield) was obtained as a colorless oil.

Methyl 3-[2-chloro-5-(4,4,5,5-tetramethyl-1,3,2-dioxaborolan-2-yl)pyridin-4-yl]propanoate Step 11: The solution of methyl 3-(5-bromo-2-chloropyridin-4-yl)propanoate (1.00 g, 3.59 mmol), BPD (1.09 g, 1.2 eq, 4.30 mmol), KOAc (1.05 g, 3.0 eq, 10.77 mmol) and Pd(dppf)Cl$_2$ (525.0 mg, 0.2 eq, 0.72 mmol) in dioxane (20.0 mL) was stirred at 70° C. for 12 h under N$_2$. The reaction mixture was concentrated under reduced pressure, the residue was purified by column chromatography (Petroleum ether/EtOAc=20/1 to 10/1). Methyl 3-[2-chloro-5-(4,4,5,5-tetramethyl-1,3,2-dioxaborolan-2-yl)pyridin-4-yl]propanoate (0.90 g, 77.5% yield) was obtained as a white solid.

Methyl 3-[5-(4-amino-5-{4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]propanoate

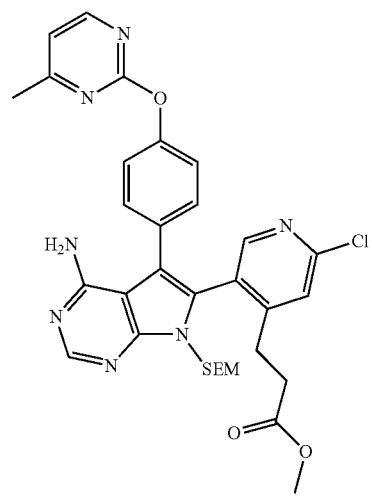 [SMILES: COC(=O)CCc1cc(Cl)ncc1-c1c(-c2ccc(Oc3nccc(C)n3)cc2)c2c(N)ncnc2n1COCC[Si](C)(C)C]

Step 12: The solution of 6-bromo-5-{4-[(4-methylpyrimidin-2-yl)oxy]phenyl}-7-{[2-(trimethylsilyl)ethoxy]methyl}-7H-pyrrolo[2,3-d]pyrimidin-4-amine (550.0 mg, 1.04 mmol), methyl 3-[2-chloro-5-(4,4,5,5-tetramethyl-1,3,2-dioxaborolan-2-yl)pyridin-4-yl]propanoate(403.0 mg, 1.2 eq, 1.24 mmol), Pd[Pd(t-Bu)$_3$]$_2$ (106.0 mg, 0.2 eq, 0.21 mmol) and CsF (521.0 mg, 3.3 eq, 3.43 mmol) in THF (20.0 mL) and H$_2$O (20.0 mL) was stirred at 50° C. for 12 h under N$_2$. The reaction mixture was concentrated under reduced pressure, the residue was purified by column chromatography (MeOH/EtOAc=0/1 to 1/10). Methyl 3-[5-(4-amino-5-{4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]propanoate (420.0 mg, 62.4% yield) was obtained as a brown solid.

3-[5-(4-amino-5-{4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]propan-1-ol

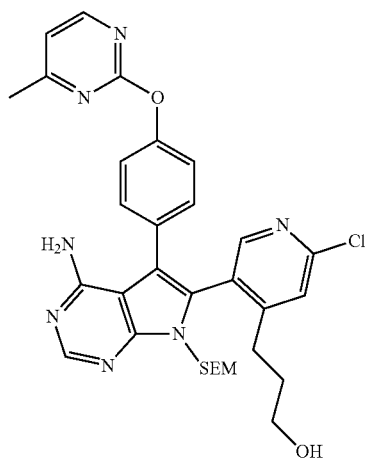 [SMILES: Cc1ccnc(Oc2ccc(-c3c(-c4cnc(Cl)cc4CCCO)n(COCC[Si](C)(C)C)c4ncnc(N)c34)cc2)n1]

Step 13: LiBH$_4$ (20.1 mg, 3.0 eq, 927.0 mmol) was slowly added to a solution of methyl 3-[5-(4-amino-5-{4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]propanoate (200.0 mg, 309.0 µmol) in THF (15.0 mL) and MeOH (24.7 mg, 2.0 eq, 618.0 mmol). The reaction mixture was stirred for 2 h at 25° C. before quenched by MeOH (0.2 mL), the reaction mixture was concentrated, the residue was purified by column chromatography (DCM/MeOH=1/0 to 10/1). 3-[5-(4-amino-5-{4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]propan-1-ol (180.0 mg, 94.2% yield) was obtained as a white solid.

3-{5-[4-amino-7-(hydroxymethyl)-5-{4-[(4-methylpyrimidin-2-yl)oxy]phenyl}-7H-pyrrolo[2,3-d]pyrimidin-6-yl]-2-chloropyridin-4-yl}propan-1-ol

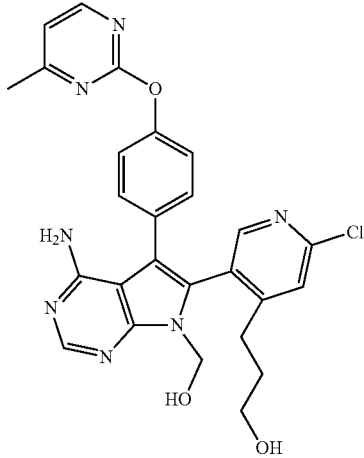 [SMILES: Cc1ccnc(Oc2ccc(-c3c(-c4cnc(Cl)cc4CCCO)n(CO)c4ncnc(N)c34)cc2)n1]

Step 14: The solution of 3-[5-(4-amino-5-{4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]propan-1-ol (190.0 mg, 307.0 µmol) in DCM (15.0 mL) and TFA (6.0 mL) was stirred at 25° C. for 2 h. The reaction mixture was concentrated under reduced pressure. 3-{5-[4-amino-7-(hydroxymethyl)-5-{4-[(4-methylpyrimidin-2-yl)oxy]phenyl}-7H-pyrrolo[2,3-d]pyrimidin-6-yl]-2-chloropyridin-4-yl}propan-1-ol (155.0 mg, 97.4% yield) was obtained as a colorless oil which can be used for the next step without further purification.

3-[5-(4-amino-5-{4-[(4-methylpyrimidin-2-yl)oxy]phenyl}-7H-pyrrolo[2,3-d]pyrimidin-6-yl)-2-chloropyridin-4-yl]propan-1-ol

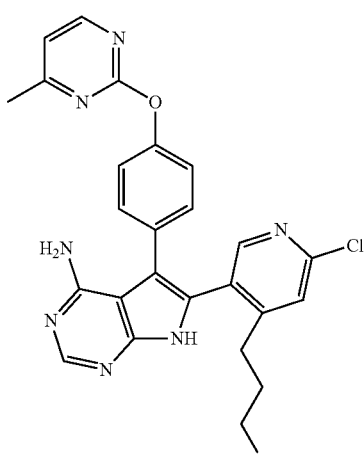

Step 15: The solution of 3-{5-[4-amino-7-(hydroxymethyl)-5-{4-[(4-methylpyrimidin-2-yl)oxy]phenyl}-7H-pyrrolo[2,3-d]pyrimidin-6-yl]-2-chloropyridin-4-yl}propan-1-ol (155.0 mg, 299.0 μmol) in THF (15.0 mL) and TEA (6.0 mL) was stirred at 25° C. for 2 h. The reactant mixture was concentrated, the residue was purified by column chromatography (DCM/MeOH=1/0 to 10/1). 3-[5-(4-amino-5-{4-[(4-methylpyrimidin-2-yl)oxy]phenyl}-7H-pyrrolo[2,3-d]pyrimidin-6-yl)-2-chloropyridin-4-yl]propan-1-ol (120.0 mg, 82.7% yield) was obtained as a white solid.

3-chloro-13-(4-((4-methylpyrimidin-2-yl)oxy)phenyl)-6,7-dihydro-5H-pyrido[3,4-c]pyrimido[5',4':4,5]pyrrolo[1,2-a]azepin-12-amine

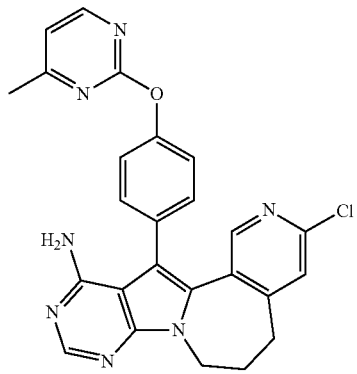 [SMILES: Cc1ccnc(Oc2ccc(-c3c4n(c5ncnc(N)c35)CCCc3cc(Cl)ncc3-4)cc2)n1]

Step 16: The solution of 3-[5-(4-amino-5-{4-[(4-methylpyrimidin-2-yl)oxy]phenyl}-7H-pyrrolo[2,3-d]pyrimidin-6-yl)-2-chloropyridin-4-yl]propan-1-ol (180.0 mg, 368.0 μmol), PPh₃ (193.0 mg, 2.0 eq, 736.0 μmol) and DIAD (148.0 mg, 2.0 eq, 736.0 μmol) in THF (5.0 mL) was stirred at 25° C. for 12 h under N₂. The reaction mixture was concentrated, the residue was purified by column chromatography (DCM/MeOH=20/1 to 10/1). 3-chloro-13-(4-((4-methylpyrimidin-2-yl)oxy)phenyl)-6,7-dihydro-5H-pyrido[3,4-c]pyrimido[5',4':4,5]pyrrolo[1,2-a]azepin-12-amine (90.0 mg, 52.3% yield) was obtained as a white solid.

13-(4-((4-methylpyrimidin-2-yl)oxy)phenyl)-3-((trimethylsilyl)ethynyl)-6,7-dihydro-5H-pyrido[3,4-c]pyrimido[5',4':4,5]pyrrolo[1,2-a]azepin-12-amine

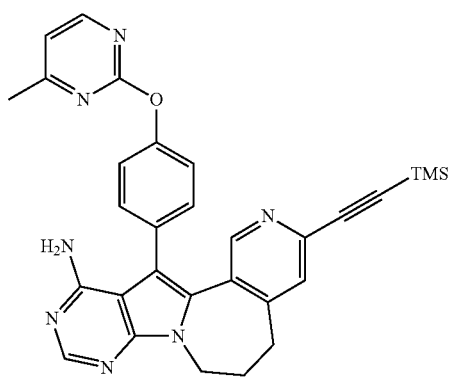 [SMILES: Cc1ccnc(Oc2ccc(-c3c4n(c5ncnc(N)c35)CCCc3cc(C#C[Si](C)(C)C)ncc3-4)cc2)n1]

Step 17: The solution of 3-chloro-13-(4-((4-methylpyrimidin-2-yl)oxy)phenyl)-6,7-dihydro-5H-pyrido[3,4-c]pyrimido[5',4':4,5]pyrrolo[1,2-a]azepin-12-amine (100.0 mg, 212.0 μmol), Trimethylsilacetylene (171.0 mg, 8.2 eq, 1.74 mmol), Pd(PPh₃)₂Cl₂ (61.7 mg, 0.4 eq, 84.8 μmol), PPh₃ (45.9 mg, 0.8 eq, 169.6 μmol), CuI (33.5 mg, 0.8 eq, 169.6 μmol) and Et₃N (443.0 mg, 20.0 eq, 4.24 mmol) in 2-Me-THF (4.0 mL) was stirred at 90° C. for 12 h under N₂. The reaction mixture was concentrated under reduced pressure, the residue was purified by column chromatography (DCM/MeOH=10/0 to 10/1). 13-(4-((4-methylpyrimidin-2-yl)oxy)phenyl)-3-((trimethylsilyl)ethynyl)-6,7-dihydro-5H-pyrido[3,4-c]pyrimido[5',4':4,5]pyrrolo[1,2-a]azepin-12-amine (120.0 mg, 107% crude yield) was obtained as a brown mixture which could be used for the next step without further purification.

3-ethynyl-13-(4-((4-methylpyrimidin-2-yl)oxy)phenyl)-6,7-dihydro-5H-pyrido[3,4-c]pyrimido[5',4':4,5]pyrrolo[1,2-a]azepin-12-amine

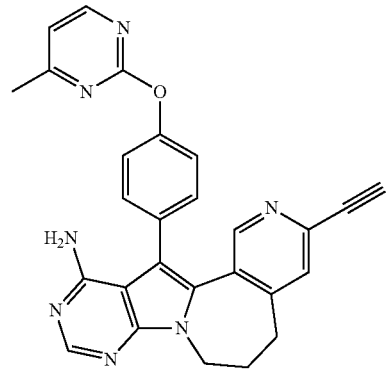 [SMILES: C#Cc1cc2c(cn1)-c1c(-c3ccc(Oc4nccc(C)n4)cc3)c3c(N)ncnc3n1CCC2]

Step 18: To the solution of 13-(4-((4-methylpyrimidin-2-yl)oxy)phenyl)-3-((trimethylsilyl)ethynyl)-6,7-dihydro-5H-pyrido[3,4-c]pyrimido[5',4':4,5]pyrrolo[1,2-a]azepin-12-amine (100.0 mg, 188.0 μmol) in THF (20.0 mL) was added a solution of TBAF in THF (376.0 μL, 2.0 eq, 376.0 mol). The resulting mixture was stirred at 25° C. for 2 h. The reaction mixture was concentrated under reduced pressure, the residue was purified by prep-HPLC (NH₃·H₂O). 3-ethynyl-13-(4-((4-methylpyrimidin-2-yl)oxy)phenyl)-6,7-dihydro-5H-pyrido[3,4-c]pyrimido[5',4':4,5]pyrrolo[1,2-a]azepin-12-amine (2.6 mg, 3.0% yield) was obtained as a white solid.

TABLE 39
Exemplary Compound
| Compound | Structure | Proton NMR | MS [M + 1] |
|---|---|---|---|
| 3-ethynyl-13-(4-((4-methylpyrimidin-2-yl)oxy)phenyl)-6,7-dihydro-5H-pyrido[3,4-c]pyrimido[5',4':4,5]pyrrolo[1,2-a]azepin-12-amine | 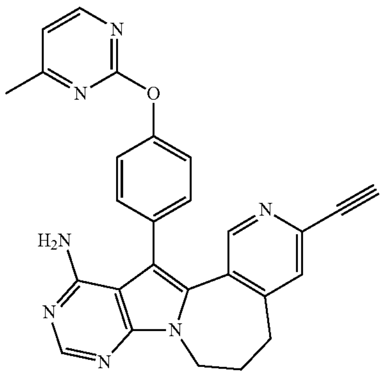 [SMILES: C#Cc1cc2c(cn1)-c1c(-c3ccc(Oc4nccc(C)n4)cc3)c3c(N)ncnc3n1CCC2] | ¹HNMR (400 MHz, CDCl₃): δ 8.41-8.36 (m, 2H), 8.21 (s, 1H), 7.48 (s, 1H), 7.41-7.38 (m, 2H), 7.31-7.28 (m, 2H), 6.96 (s, 1H), 5.14 (s, 2H), 4.28 (m, 2H), 3.21 (s, 1H), 2.85-2.81 (m, 2H), 2.54 (s, 3H), 2.40-2.36 (m, 2H). | 460.3. |
Example 41
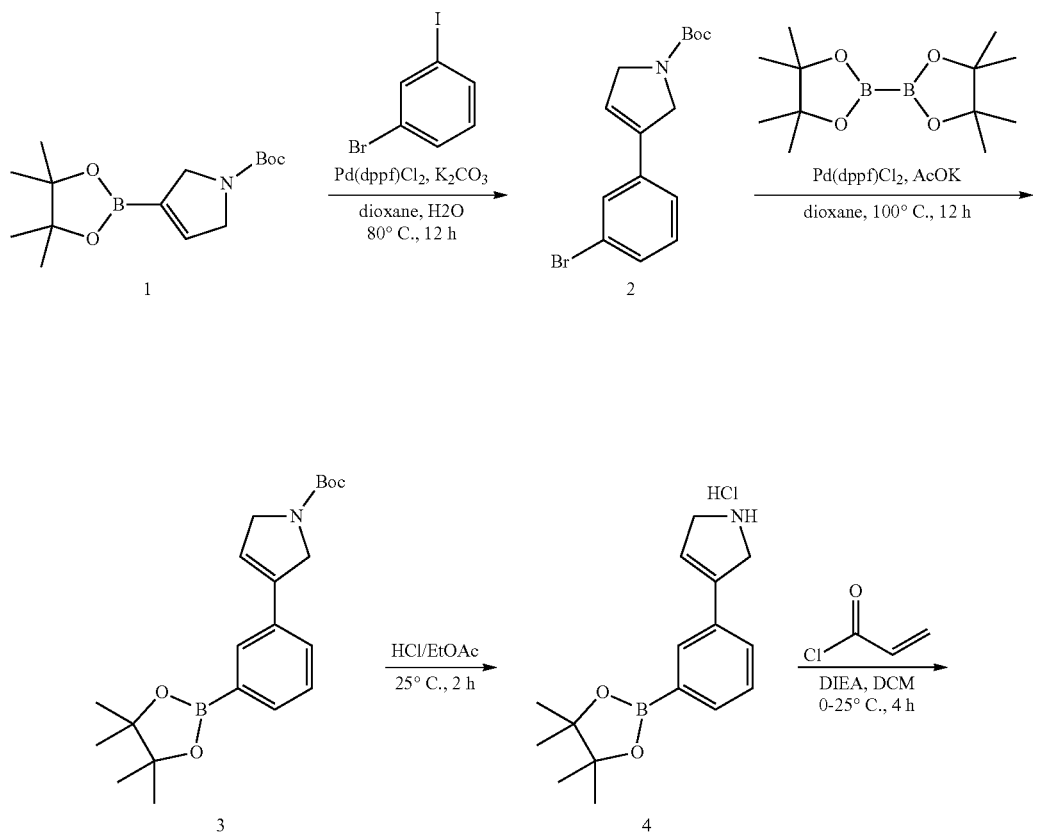

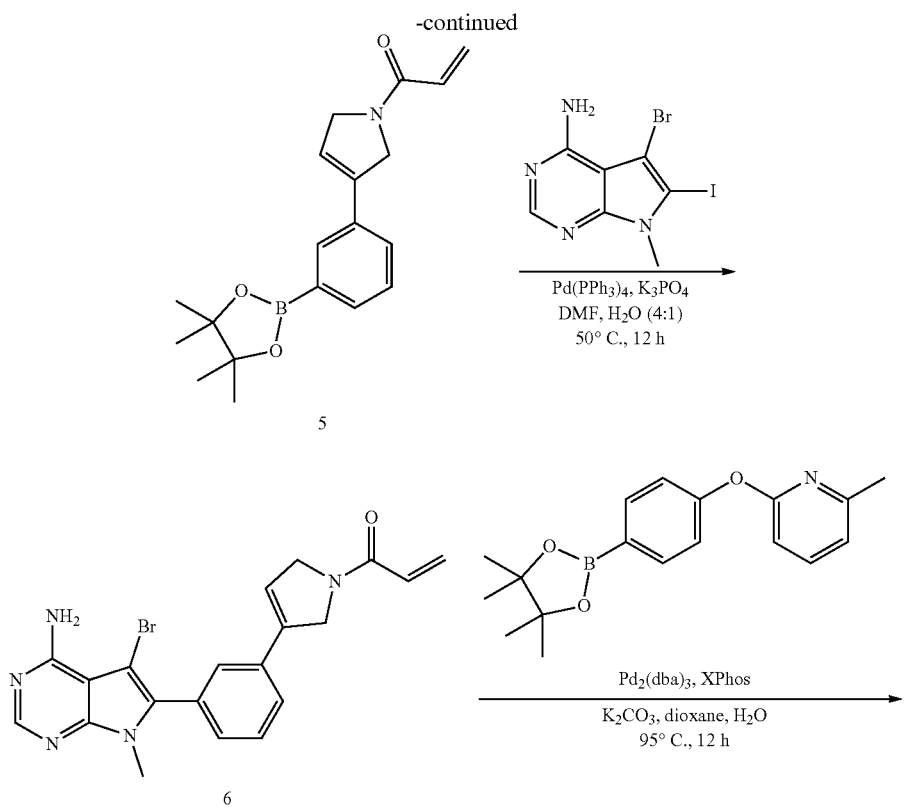

tert-butyl 3-(3-bromophenyl)-2,5-dihydro-1H-pyrrole-1-carboxylate

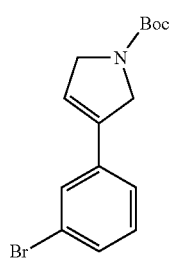

Step 1: The mixture of 1-bromo-3-iodobenzene (956.0 mg, 3.4 mmol), tert-butyl 3-(4,4,5,5-tetramethyl-1,3,2-di- oxaborolan-2-yl)-2,5-dihydro-1H-pyrrole-1-carboxylate (500.0 mg, 1.7 mmol), Pd(dppf)Cl₂ (123.0 mg, 169.0 µmol) and K₂CO₃ (466.0 mg, 3.4 mmol) in dioxane (20.00 mL) and H₂O (4.0 mL) was stirred at 80° C. for 12 hours under N₂ protection. The mixture was concentrated to give a residue which was dissolved in ethyl acetate (50 mL) and H₂O (30 mL). The aqueous layer was separated and extracted with ethyl acetate (30 mL×3). The combined organic layers were washed with brine (25 mL), dried over anhydrous Na₂SO₄, filtered and concentrated to give a residue, which was purified by silica gel chromatography (ethyl acetate in petroleum ether=0% to 11%) to afford the product of tert-butyl 3-(3-bromophenyl)-2,5-dihydro-1H-pyrrole-1-carboxylate (450.0 mg, 82.2% yield) as a yellow oil.

1875 tert-butyl 3-[3-(4,4,5,5-tetramethyl-1,3,2-dioxaborolan-2-yl)phenyl]-2,5-dihydro-1H-pyrrole-1-carboxylate

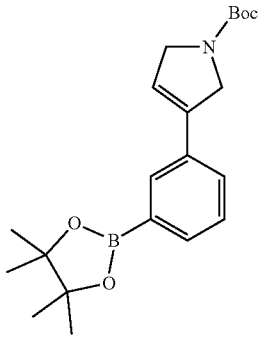 [SMILES: CC(C)(C)OC(=O)N1CC=C(c2cccc(B3OC(C)(C)C(C)(C)O3)c2)C1]

Step 2: The mixture of tert-butyl 3-(3-bromophenyl)-2,5-dihydro-1H-pyrrole-1-carboxylate (450.0 mg, 1.4 mmol), 4,4,5,5-tetramethyl-2-(4,4,5,5-tetramethyl-1,3,2-dioxaborolan-2-yl)-1,3,2-dioxaborolane (700.0 mg, 2.8 mmol), Pd(dppf)Cl$_2$ (101.0 mg, 138.0 μmol) and AcOK (202.0 mg, 2.1 mmol) in dioxane (20.00 mL) was stirred at 100° C. for 12 hours under N$_2$ protection. The mixture was concentrated to give a residue which was dissolved in ethyl acetate (50 mL) and H$_2$O (30 mL). The aqueous layer was separated and extracted with ethyl acetate (30 mL×3). The combined organic layers were washed with brine (25 mL), dried over anhydrous Na$_2$SO$_4$, filtered and concentrated to give a residue which was purified by silica gel chromatography (ethyl acetate in petroleum ether=0% to 12%) to afford the product of tert-butyl 3-[3-(4,4,5,5-tetramethyl-1,3,2-dioxaborolan-2-yl)phenyl]-2,5-dihydro-1H-pyrrole-1-carboxylate (450.0 mg, 87.8% yield) as a yellow oil.

3-[3-(4,4,5,5-tetramethyl-1,3,2-dioxaborolan-2-yl)phenyl]-2,5-dihydro-1H-pyrrole hydrochloride

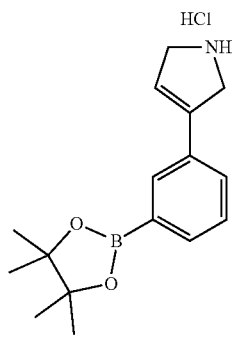 [SMILES: Cl ; CC1(C)OB(c2cccc(C3=CCNC3)c2)OC1(C)C]

Step 3: The tert-butyl 3-[3-(4,4,5,5-tetramethyl-1,3,2-dioxaborolan-2-yl)phenyl]-2,5-dihydro-1H-pyrrole-1-carboxylate (450.0 mg, 1.2 mmol) was added in HCl/EtOAc (6.00 mL, 4 M). The mixture was stirred at 25° C. for 2 hours. The mixture was concentrated to give 3-[3-(4,4,5,5-tetramethyl-1,3,2-dioxaborolan-2-yl)phenyl]-2,5-dihydro-1H-pyrrole hydrochloride (372.0 mg, 100% yield) as a yellow oil.

1876

1-{3-[3-(4,4,5,5-tetramethyl-1,3,2-dioxaborolan-2-yl)phenyl]-2,5-dihydro-1H-pyrrol-1-yl}prop-2-en-1-one

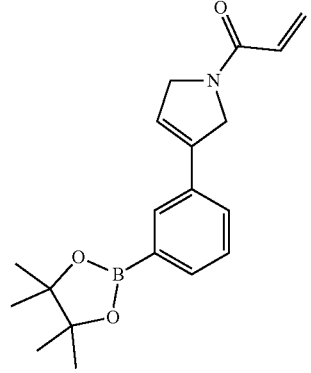 [SMILES: C=CC(=O)N1CC=C(c2cccc(B3OC(C)(C)C(C)(C)O3)c2)C1]

Step 4: The prop-2-enoyl chloride (140.0 mg, 1.6 mmol) in DCM (3.00 mL) was added in the mixture of 3-[3-(4,4,5,5-tetramethyl-1,3,2-dioxaborolan-2-yl)phenyl]-2,5-dihydro-1H-pyrrole hydrochloride (372.0 mg, 1.2 mmol) and DIEA (1.04 mL, 6.0 mmol) in DCM (12.00 mL) at 0° C. The mixture was stirred at 25° C. for 4 hours. The mixture was diluted with DCM (20 mL), washed with sat.NaHCO$_3$ (20 mL), brine (20 mL), dried over anhydrous Na$_2$SO$_4$, filtered and concentrated to give a residue which was purified by silica gel chromatography (ethyl acetate in petroleum ether=0% to 45%) to afford the product of 1-{3-[3-(4,4,5,5-tetramethyl-1,3,2-dioxaborolan-2-yl)phenyl]-2,5-dihydro-1H-pyrrol-1-yl}prop-2-en-1-one (210.0 mg, 53.8% yield) as a yellow oil.

1-[3-(3-{4-amino-5-bromo-7-methyl-7H-pyrrolo[2,3-d]pyrimidin-6-yl}phenyl)-2,5-dihydro-1H-pyrrol-1-yl]prop-2-en-1-one

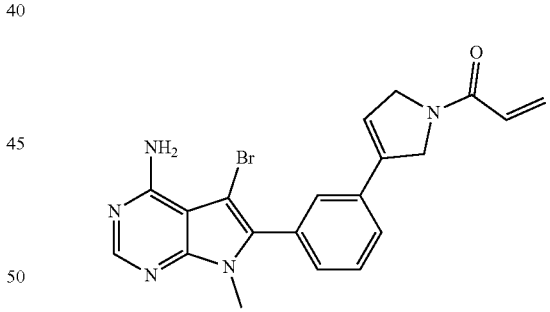

Step 5: The mixture of 1-{3-[3-(4,4,5,5-tetramethyl-1,3,2-dioxaborolan-2-yl)phenyl]-2,5-dihydro-1H-pyrrol-1-yl}prop-2-en-1-one (210.0 mg, 645.0 μmol), 5-bromo-6-iodo-7-methyl-7H-pyrrolo[2,3-d]pyrimidin-4-amine (250.0 mg, 709.0 μmol), Pd(PPh$_3$)$_4$ (74.4 mg, 64.5 μmol) and K$_3$PO$_4$ (271.0 mg, 1.28 mmol) in DMF (16.00 mL) and H$_2$O (4.00 mL) was stirred at 50° C. for 12 hours under N$_2$ protection. The mixture was diluted with ethyl acetate (30 mL), washed with H$_2$O (20 mL×3), brine (15 mL), dried over anhydrous Na$_2$SO$_4$, filtered and concentrated to give a residue which was purified by silica gel chromatography (methanol in dichloromethane=0% to 14%) to afford the product of 1-[3-(3-{4-amino-5-bromo-7-methyl-7H-pyrrolo[2,3-d]pyrimidin-6-yl}phenyl)-2,5-dihydro-1H-pyrrol-1-yl]prop-2-en-1-one (70.0 mg, 25.6% yield) as a yellow oil.

1-{3-[3-(4-amino-7-methyl-5-{4-[(6-methylpyridin-2-yl)oxy]phenyl}-7H-pyrrolo[2,3-d]pyrimidin-6-yl)phenyl]-2,5-dihydro-1H-pyrrol-1-yl}prop-2-en-1-one

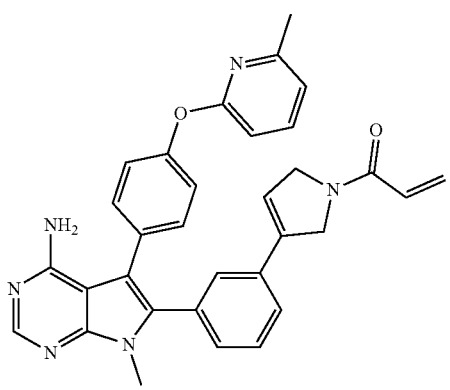 [SMILES: C=CC(=O)N1CC=C(c2cccc(-c3c(-c4ccc(Oc5cccc(C)n5)cc4)c4c(N)ncnc4n3C)c2)C1]

The mixture of 1-[3-(3-{4-amino-5-bromo-7-methyl-7H-pyrrolo[2,3-d]pyrimidin-6-yl}phenyl)-2,5-dihydro-1H-pyrrol-1-yl]prop-2-en-1-one (50.0 mg, 117.0 μmol), 2-methyl-6-[4-(4,4,5,5-tetramethyl-1,3,2-dioxaborolan-2-yl)phenoxy]pyridine (54.4 mg, 175.0 μmol), Pd$_2$(dba)$_3$ (10.7 mg, 117.0 μmol), XPhos (11.1 mg, 117.0 μmol), K$_2$CO$_3$ (48.4 mg, 117.0 μmol) in dioxane (4.00 mL) and H$_2$O (1.00 mL) was stirred at 95° C. for 12 hours under N$_2$ protection. The mixture was filtered and the filtrate was concentrated to give a residue which was purified by prep-HPLC (HCl) to afford the product of 1-{3-[3-(4-amino-7-methyl-5-{4-[(6-methylpyridin-2-yl)oxy]phenyl}-7H-pyrrolo[2,3-d]pyrimidin-6-yl)phenyl]-2,5-dihydro-1H-pyrrol-1-yl}prop-2-en-1-one (4.9 mg, 7.41% yield) as a white solid.

Additional compounds prepared according to the methods of Example 41 are depicted in Table 40 below.

TABLE 40

Exemplary Compounds

| Compound | Structure | Proton NMR | MS [M + 1] |
|---|---|---|---|
| 1-{3-[3-(4-amino-7-methyl-5-{4-[(6-methylpyridin-2-yl)oxy]phenyl}-7H-pyrrolo[2,3-d]pyrimidin-6-yl)phenyl]-2,5-dihydro-1H-pyrrol-1-yl}prop-2-en-1-one | 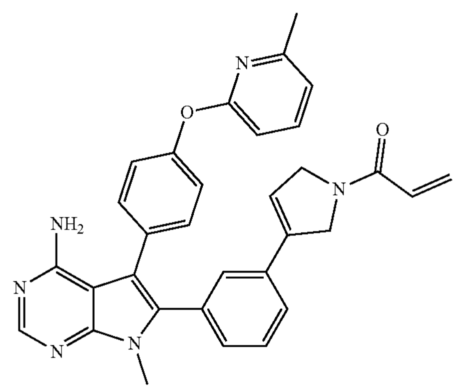 [SMILES: C=CC(=O)N1CC=C(c2cccc(-c3c(-c4ccc(Oc5cccc(C)n5)cc4)c4c(N)ncnc4n3C)c2)C1] | $^1$H NMR (400 MHz, DMSO-d$_6$) δ 8.57 (s, 1H), 7.73-7.70 (m, 1H), 7.63-7.60 (d, J = 8.0 Hz, 1H), 7.49-7.45 (m, 2H), 7.35-7.28 (m, 3H), 7.32-7.28 (m, 3H), 7.14-7.10 (m, 2H), 7.02-7.00 (d, J = 7.6 Hz, 1H), 6.79-6.76 (m, 1H), 6.69-6.59 (m, 1H), 6.49 (s, 1H), 6.23-6.15 (m, 1H), 5.75-5.70 (m, 1H), 4.69 (s, 1H), 4.55-4.47 (d, J = 32.4 Hz, 2H), 4.32 (s, 1H), 3.75-3.73 (d, J = 6.8 Hz, 3H), 2.31-2.29 (d, J = 7.2 Hz, 3H). | 529.3 |
| 1-{3-[4-(4-amino-7-methyl-5-{4-[(6-methylpyridin-2-yl)oxy]phenyl}-7H-pyrrolo[2,3-d]pyrimidin-6-yl)phenyl]-2,5-dihydro-1H-pyrrol-1-yl}prop-2-en-1-one hydrochloride | 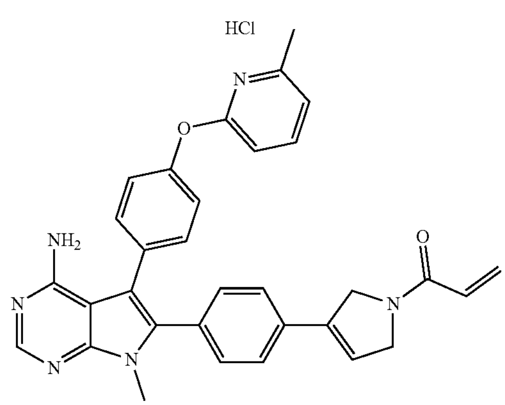 [SMILES: Cl ; C=CC(=O)N1CC=C(c2ccc(-c3c(-c4ccc(Oc5cccc(C)n5)cc4)c4c(N)ncnc4n3C)cc2)C1] | $^1$H NMR (400 MHz, DMSO-d$_6$): δ 8.43 (s, 1H), 8.13-8.07 (m, 1H), 7.6 (d, J = 7.6 Hz, 2H), 7.46 (d, J = 7.6 Hz, 2H), 7.41 (d, J = 8.0 Hz, 2H), 7.32-7.27 (m, 3H), 7.06 (d, J = 8.4 Hz, 1H), 6.81-6.64 (m, 1H), 6.49-6.36 (m, 2H), 5.87-5.82 (m, 1H), 4.79 (s, 1H), 4.67 (s, 2H), 4.49 (s, 1H), 3.83 (s, 3H), 2.61 (d, J = 32 Hz, 3H). | 529.1 |

Example 42
Scheme 39
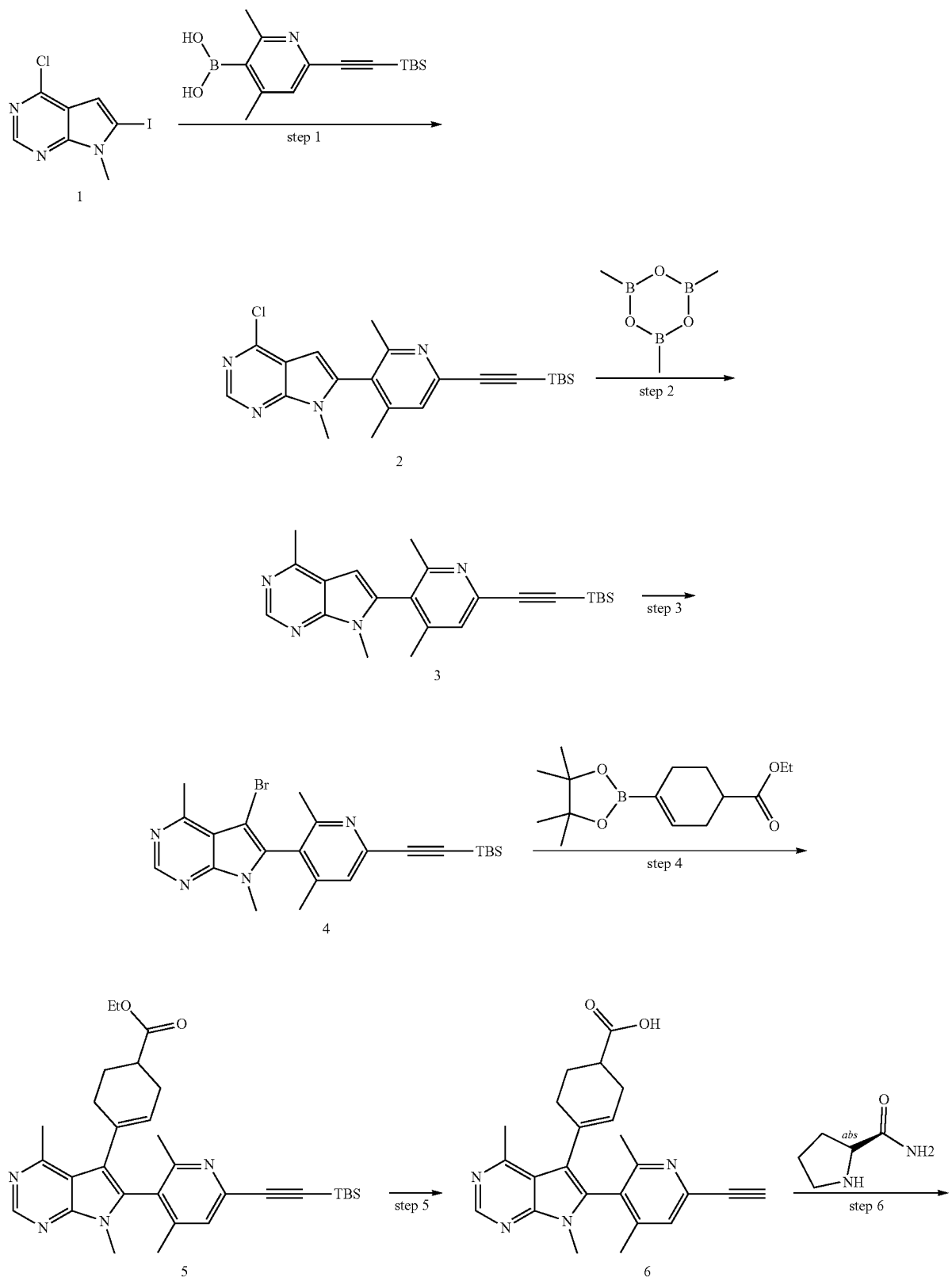

-continued
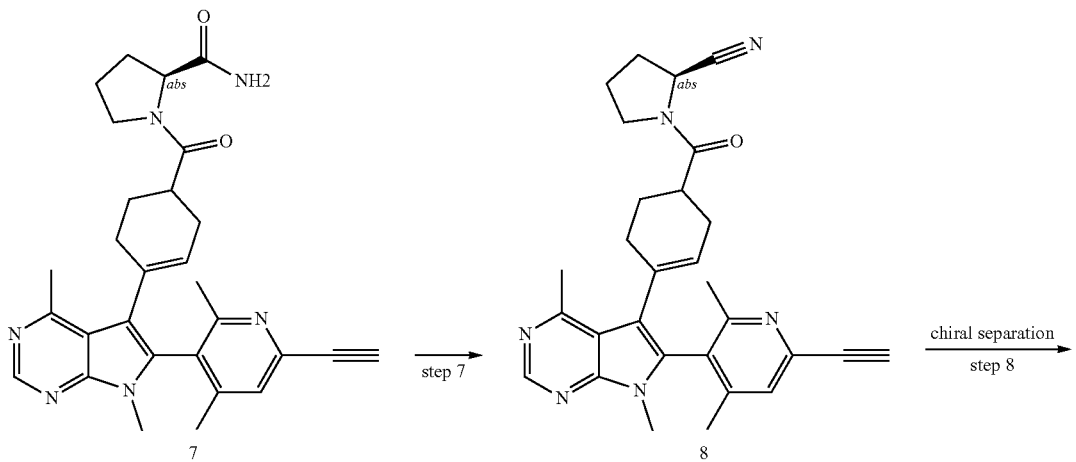
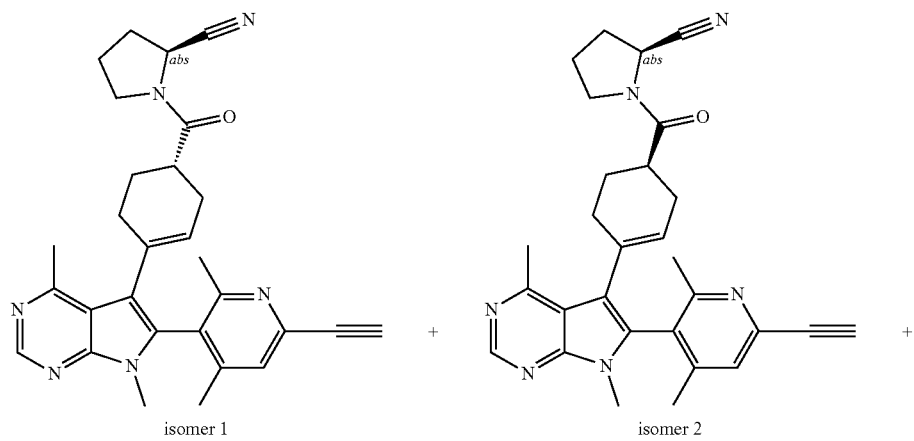
isomer 1   +   isomer 2   +
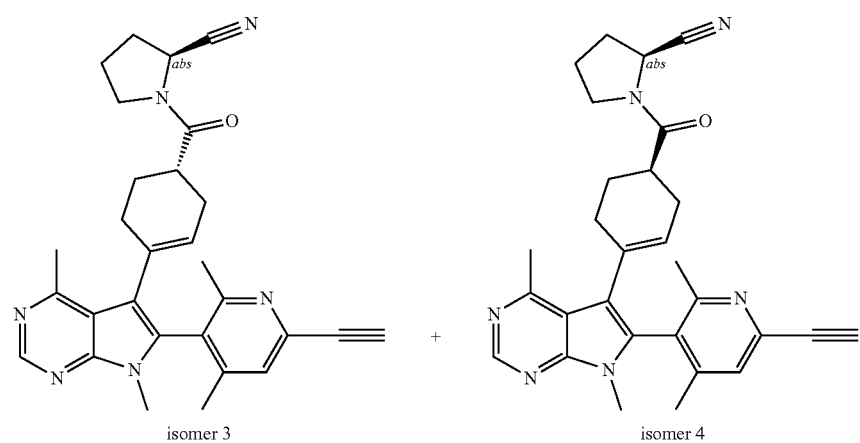
isomer 3   +   isomer 4

6-(6-((tert-butyldimethylsilyl)ethynyl)-2,4-dimethylpyridin-3-yl)-4-chloro-7-methyl-7H-pyrrolo[2,3-d]pyrimidine

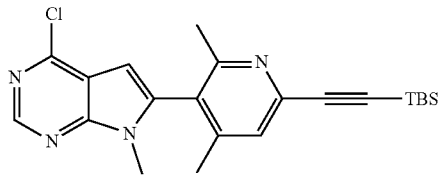

Step 1: A resealable reaction vial was charged with 4-chloro-6-iodo-7-methyl-7H-pyrrolo[2,3-d]pyrimidine (1.50 g, 5.11 mmol), {6-[2-(tert-butyldimethylsilyl)ethynyl]-2,4-dimethylpyridin-3-yl}boronic acid (1.62 g, 5.62 mmol), $K_3PO_4$ (3.24 g, 15.3 mmol), $PAd_2nBu$ (183 mg, 511 µmol), $PAd_2nBu$ Pd-G2 (341 mg, 511 µmol), $DME/H_2O$ (20 mL) and a stir bar before being evacuated and purged with nitrogen three times, and the mixture was stirred overnight at 70° C. The reaction mixture was diluted with water (30 mL), and the aqueous phase was extracted with dichloromethane (30 mL) three times. The combined organic layers were washed with brine, dried over sodium sulfate, filtered, and concentrated in vacuo. The resulting crude material was purified by silica gel chromatography (eluting with dichloromethane/methanol; 30:1). Concentration in vacuo resulted in 6-[2-(tert-butyldimethylsilyl)ethynyl]-3-{4-chloro-7-methyl-7H-pyrrolo[2,3-d]pyrimidin-6-yl}-2,4-dimethylpyridine (1.50 g, 65%) as a yellow amorphous solid.

6-(6-((tert-butyldimethylsilyl)ethynyl)-2,4-dimethylpyridin-3-yl)-4,7-dimethyl-7H-pyrrolo[2,3-d]pyrimidine

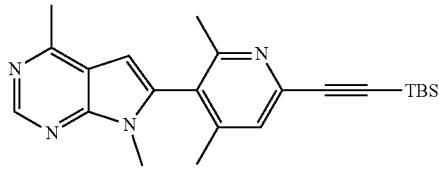

Step 2: A resealable reaction vial was charged with 6-[2-(tert-butyldimethylsilyl)ethynyl]-3-{4-chloro-7-methyl-7H-pyrrolo[2,3-d]pyrimidin-6-yl}-2,4-dimethylpyridine (3.50 g, 8.51 mmol), tetrahydrofuran (40 mL), $K_3PO_4$ (5.40 g, 25.5 mmol), Pd(dppf)$Cl_2$ (622 mg, 851 µmol), and a stir bar before being evacuated and purged with nitrogen three times. trimethyl-1,3,5,2,4,6-trioxatriborinane (50%) (6.4 g, 25.5 mmol) was added, and the mixture was stirred for 2 h at 70° C. The reaction mixture was diluted with water (50 mL), and the aqueous phase was extracted with DCM (50 mL) three times. The combined organic layers were washed with brine, dried over sodium sulfate, filtered, and concentrated in vacuo. The resulting crude material was purified by silica gel chromatography (eluting with dichloromethane/methanol; 80:1). Concentration in vacuo resulted in 6-[2-(tert-butyldimethylsilyl)ethynyl]-3-{4,7-dimethyl-7H-pyrrolo[2,3-d]pyrimidin-6-yl}-2,4-dimethylpyridine (2.80 g, 84%) as a yellow amorphous solid.

5-bromo-6-(6-((tert-butyldimethylsilyl)ethynyl)-2,4-dimethylpyridin-3-yl)-4,7-dimethyl-7H-pyrrolo[2,3-d]pyrimidine

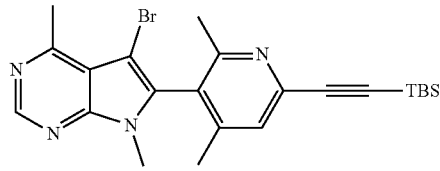

Step 3: A round bottomed flask was charged with 6-[2-(tert-butyldimethylsilyl)ethynyl]-3-{4,7-dimethyl-7H-pyrrolo[2,3-d]pyrimidin-6-yl}-2,4-dimethylpyridine (2.80 g, 7.16 mmol), dimethylformamide (30 mL) and a stir bar. Then NBS (1.39 g, 7.87 mmol) was added, and the solution was stirred for 1 h at 25° C. The reaction mixture was quenched with $Na_2SO_3$ (a.q.) (30 mL), and the reaction mixture was filtered through a pad of Celite, the pad was washed with water, and the filter cake was dried in vacuo resulted in 3-{5-bromo-4,7-dimethyl-7H-pyrrolo[2,3-d]pyrimidin-6-yl}-6-[2-(tert-butyldimethylsilyl)ethynyl]-2,4-dimethylpyridine (3.02 g, 90%) as a yellow amorphous solid.

ethyl 4-(6-(6-((tert-butyldimethylsilyl)ethynyl)-2,4-dimethylpyridin-3-yl)-4,7-dimethyl-7H-pyrrolo[2,3-d]pyrimidin-5-yl)cyclohex-3-ene-1-carboxylate

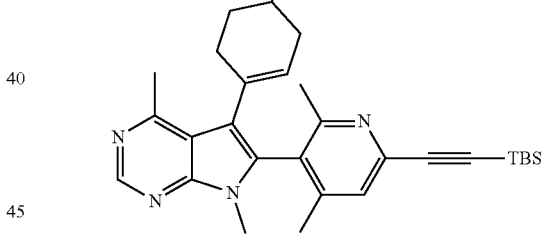

Step 4: A resealable reaction vial was charged with 3-{5-bromo-4,7-dimethyl-7H-pyrrolo[2,3-d]pyrimidin-6-yl}-6-[2-(tert-butyldimethylsilyl)ethynyl]-2,4-dimethylpyridine (3.00 g, 6.38 mmol), DME/$H_2O$ (30 mL), ethyl 4-(4,4,5,5-tetramethyl-1,3,2-dioxaborolan-2-yl)cyclohex-3-ene-1-carboxylate (1.96 g, 7.01 mmol), $K_3PO_4$ (4.04 g, 19.1 mmol), Pd(dppf)$Cl_2$ (466 mg, 638 µmol), and a stir bar before being evacuated and purged with nitrogen three times, and the mixture was stirred for 1 h at 70° C. The reaction mixture was diluted with water (30 mL), and the aqueous phase was extracted with dichloromethane (30 mL) three times. The combined organic layers were washed with brine, dried over sodium sulfate, filtered, and concentrated in vacuo. The resulting crude material was purified by silica gel chromatography (eluting with dichloromethane/methanol; 40:1). Concentration in vacuo resulted in ethyl 4-(6-{6-[2-(tert-butyldimethylsilyl)ethynyl]-2,4-dimethylpyridin-3-yl}-4,7-dimethyl-7H-pyrrolo[2,3-d]pyrimidin-5-yl)cyclohex-3-ene-1-carboxylate (2.50 g, 72%) as a yellow amorphous solid.

4-(6-(6-ethynyl-2,4-dimethylpyridin-3-yl)-4,7-dimethyl-7H-pyrrolo[2,3-d]pyrimidin-5-yl)cyclohex-3-ene-1-carboxylic acid

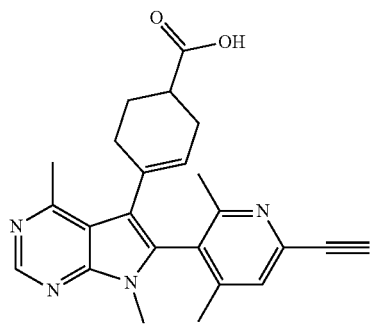 [SMILES: C#Cc1cc(C)c(-c2c(C3=CCC(C(=O)O)CC3)c3c(C)ncnc3n2C)c(C)n1]

Step 5: A round bottomed flask was charged with ethyl 4-(6-{6-[2-(tert-butyldimethylsilyl)ethynyl]-2,4-dimethylpyridin-3-yl}-4,7-dimethyl-7H-pyrrolo[2,3-d]pyrimidin-5-yl)cyclohex-3-ene-1-carboxylate (2.48 g, 4.56 mmol), NaOH (543 mg, 13.6 mmol) and a stir bar. MeOH/H$_2$O (20 mL) was added, and the solution was stirred for 1 h at 60° C. The reaction mixture was adjusted pH to 5~6, concentration in vacuo resulted in 4-[6-(6-ethynyl-2,4-dimethylpyridin-3-yl)-4,7-dimethyl-7H-pyrrolo[2,3-d]pyrimidin-5-yl]cyclohex-3-ene-1-carboxylic acid (2.2 g, crude) as a black amorphous solid.

(2S)-1-(4-(6-(6-ethynyl-2,4-dimethylpyridin-3-yl)-4,7-dimethyl-7H-pyrrolo[2,3-d]pyrimidin-5-yl)cyclohex-3-ene-1-carbonyl)pyrrolidine-2-carboxamide

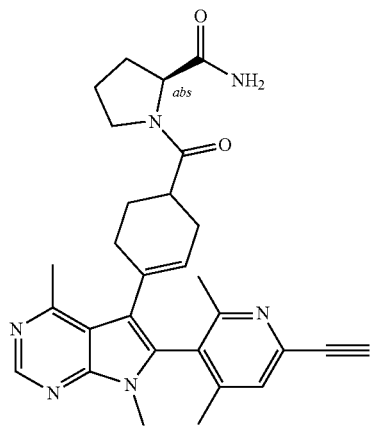 [SMILES: C#Cc1cc(C)c(-c2c(C3=CCC(C(=O)N4CCC[C@H]4C(N)=O)CC3)c3c(C)ncnc3n2C)c(C)n1]

Step 6: A round bottomed flask was charged with 4-[6-(6-ethynyl-2,4-dimethylpyridin-3-yl)-4,7-dimethyl-7H-pyrrolo[2,3-d]pyrimidin-5-yl]cyclohex-3-ene-1-carboxylic acid (1.7 g, 4.24 mmol), dimethylformamide (20 mL), T3P (5.38 g, 8.48 mmol), TEA (856 mg, 8.48 mmol) and a stir bar. (2S)-pyrrolidine-2-carboxamide (967 mg, 8.48 mmol) was added, and the solution was stirred for 1 h at 25° C. The reaction mixture was diluted with water (30 mL), and the aqueous phase was extracted with dichloromethane (30 mL) three times. The combined organic layers were washed with brine, dried over sodium sulfate, filtered, and concentrated in vacuo. The resulting crude material was purified by HPLC (acetonitrile/water/0.1% formic acid). Lyophilization yielded (2S)-1-{4-[6-(6-ethynyl-2,4-dimethylpyridin-3-yl)-4,7-dimethyl-7H-pyrrolo[2,3-d]pyrimidin-5-yl]cyclohex-3-ene-1-carbonyl}pyrrolidine-2-carboxamide (1.5 g, 71%) as a black amorphous solid.

(2S)-1-(4-(6-(6-ethynyl-2,4-dimethylpyridin-3-yl)-4,7-dimethyl-7H-pyrrolo[2,3-d]pyrimidin-5-yl)cyclohex-3-ene-1-carbonyl)pyrrolidine-2-carbonitrile

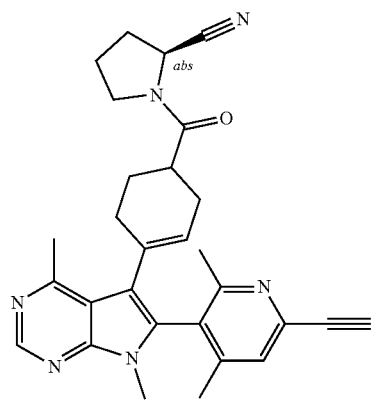 [SMILES: C#Cc1cc(C)c(-c2c(C3=CCC(C(=O)N4CCC[C@H]4C#N)CC3)c3c(C)ncnc3n2C)c(C)n1]

Step 7: A resealable reaction vial was charged with (2S)-1-{4-[6-(6-ethynyl-2,4-dimethylpyridin-3-yl)-4,7-dimethyl-7H-pyrrolo[2,3-d]pyrimidin-5-yl]cyclohex-3-ene-1-carbonyl}pyrrolidine-2-carbonitrile (320 mg, 668 μmol), tetrahydrofuran (5 mL) and a stirbar before being evacuated and purged with nitrogen three times, Burgess reagent (316 mg, 1.34 mmol) was added, and the mixture was stirred for 2 h at 25° C. The reaction mixture was diluted with water (20 mL), and the aqueous phase was extracted with dichloromethane (20 mL) three times. The combined organic layers were washed with brine, dried over sodium sulfate, filtered, and concentrated in vacuo. The resulting crude material was purified by prep-HPLC (Column: XBridge Prep OBD C18 Column, 30×150 mm 5 um; Mobile Phase A:Water(10 MMOL/L NH$_4$HCO$_3$+0.1% NH$_3$·H$_2$O), Mobile Phase B:ACN; Flow rate:60 mL/min; Gradient:20 B to 45 B in 8 min; 220 nm; RT1:7.23; RT2:; Injection Volumn: ml; Number Of Runs:;). Lyophilization yielded (2S)-1-{4-[6-(6-ethynyl-2,4-dimethylpyridin-3-yl)-4,7-dimethyl-7H-pyrrolo[2,3-d]pyrimidin-5-yl]cyclohex-3-ene-1-carbonyl}pyrrolidine-2-carbonitrile (160 mg, 50%) as an off-white amorphous solid.

isomer 1

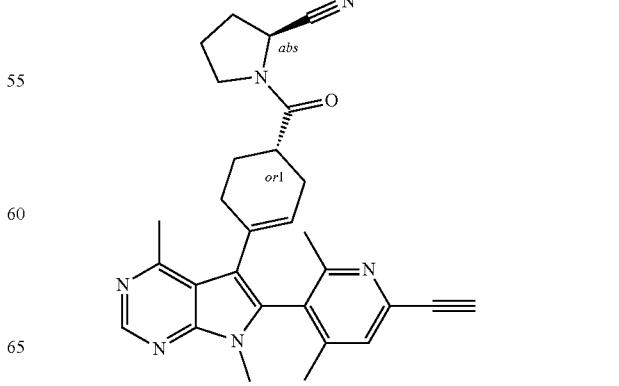

1887
-continued isomer 2

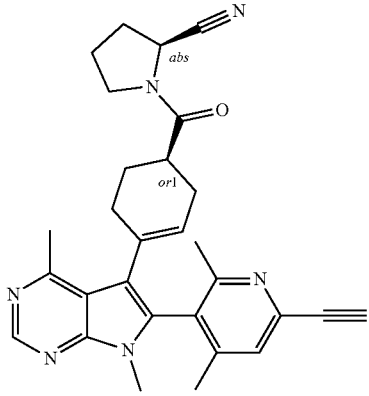 [SMILES: C#Cc1cc(C)c(-c2c(C3=CC[C@H](C(=O)N4CCC[C@H]4C#N)CC3)c3c(C)ncnc3n2C)c(C)n1]

isomer 3

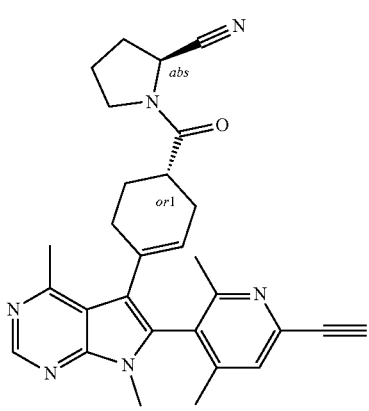

1888
-continued isomer 4

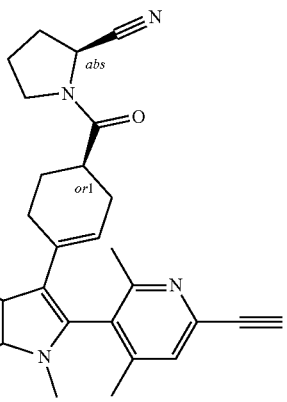

Step 8: The resulting material (160 mg) was sent to chiral separation (Column: CHIRALPAK IF, 2*25 cm, 5 um; Mobile Phase A:Hex(0.5% 2M NH3-MeOH)-HPLC, Mobile Phase B:EtOH:DCM=1:1-HPLC; Flow rate:20 mL/min; Gradient:35 B to 35 B in 11 min; 220/254 nm; RT1:6.855; RT2:8.514; Injection Volumn:0.7 ml; Number Of Runs:6;). Lyophilization yielded peak 1 (76 mg), peak 2 (67 mg). Then run chiral chiral separation again, peak 1 (Column: CHIRAL ART Cellulose-SB S-5 um, 2*25 cm, 5 um; Mobile Phase A:Hex(0.5% 2M NH3-MeOH)-HPLC, Mobile Phase B:EtOH:DCM=1:1-HPLC; Flow rate:20 mL/min; Gradient:20 B to 20 B in 17 min; 220/254 nm; RT1:13.481; RT2:15.128; Injection Volumn:0.65 ml; Number Of Runs:5; yield isomer 2(27.2 mg) and isomer 4(25 mg) an off-white amorphous solid. Peak 2(Column: CHIRAL ART Cellulose-SB, 2*25 cm, 5 um; Mobile Phase A:Hex (0.5% 2M $NH_3$-MeOH)-HPLC, Mobile Phase B:EtOH: DCM=1:1-HPLC; Flow rate:20 mL/min; Gradient:20 B to 20 B in 18 min; 220/254 nm; RT1:13.832; RT2:15.921; Injection Volumn:0.7 ml; Number Of Runs:6; yield isomer 1(25.7 mg) and isomer 3(21.4 mg) as an off-white amorphous solid.

TABLE 41

Exemplary Compounds

| Compound | Structure | Proton NMR | MS [M + 1] |
|---|---|---|---|
| (S)-1-((S)-4-(6-(6-ethynyl-2,4-dimethylpyridin-3-yl)-4,7-dimethyl-7H-pyrrolo[2,3-d]pyrimidin-5-yl)cyclohex-3-ene-1-carbonyl)pyrrolidine-2-carbonitrile | isomer 1 | $^1$H NMR (400 MHz, DMSO-$d_6$) δ 8.71 (s, 1H), 7.50 (s, 1H), 5.68 (s, 1H), 4.70 (dd, J = 7.7, 3.5 Hz, 1H), 4.39 (s, 1H), 3.67 (ddd, J = 9.6, 7.0, 4.5 Hz, 1H), 3.54-3.44 (m, 1H), 3.42 (s, 3H), 2.68 (d, J = 3.5 Hz, 3H), 2.60 (d, J = 9.3 Hz, 1H), 2.20 (d, J = 2.8 Hz, 5H), 2.18-2.07 (m, 3H), 2.06-1.94 (m, 6H), 1.76 (d, J = 13.1 Hz, 1H), 1.53-1.37 (m, 1H). | 479.25 |

TABLE 41-continued

Exemplary Compounds

| Compound | Structure | Proton NMR | MS [M + 1] |
|---|---|---|---|
| (S)-1-((R)-4-(6-(6-ethynyl-2,4-dimethylpyridin-3-yl)-4,7-dimethyl-7H-pyrrolo[2,3-d]pyrimidin-5-yl)cyclohex-3-ene-1-carbonyl)pyrrolidine-2-carbonitrile | isomer 2 | $^1$H NMR (400 MHz, DMSO-d$_6$) δ 8.73 (s, 1H), 7.50 (s, 1H), 5.67 (s, 1H), 4.71 (dd, J = 7.6, 3.7 Hz, 1H), 4.39 (s, 1H), 3.63 (ddd, J = 11.3, 7.0, 4.4 Hz, 1H), 3.56-3.46 (m, 1H), 3.42 (s, 3H), 2.69 (s, 3H), 2.59 (s, 1H), 2.19 (s, 6H), 2.18-2.06 (m, 3H), 2.04 (s, 3H), 2.00 (dd, J = 7.4, 3.4 Hz, 2H), 1.80 (d, J = 13.0 Hz, 1H), 1.57-1.45 (m, 1H). | 479.25 |
| (S)-1-((S)-4-(6-(6-ethynyl-2,4-dimethylpyridin-3-yl)-4,7-dimethyl-7H-pyrrolo[2,3-d]pyrimidin-5-yl)cyclohex-3-ene-1-carbonyl)pyrrolidine-2-carbonitrile | isomer 3 | $^1$H NMR (400 MHz, DMSO-d$_6$) δ 8.71 (s, 1H), 7.49 (s, 1H), 5.64 (s, 1H), 4.71 (dd, J = 7.6, 3.7 Hz, 1H), 4.39 (s, 1H), 3.64 (ddd, J = 11.4, 7.2, 4.6 Hz, 1H), 3.51 (q, J = 8.0 Hz, 1H), 3.41 (s, 3H), 2.68 (s, 3H), 2.60 (s, 1H), 2.19 (d, J = 2.2 Hz, 5H), 2.12 (tq, J = 13.0, 5.1, 3.3 Hz, 4H), 2.04 (s, 3H), 1.99 (dd, J = 10.0, 6.1 Hz, 2H), 1.81 (d, J = 13.2 Hz, 1H), 1.50 (dd, J = 12.0, 5.2 Hz, 1H). | 479.30 |
| (S)-1-((R)-4-(6-(6-ethynyl-2,4-dimethylpyridin-3-yl)-4,7-dimethyl-7H-pyrrolo[2,3-d]pyrimidin-5-yl)cyclohex-3-ene-1-carbonyl)pyrrolidine-2-carbonitrile | isomer 4 | $^1$H NMR (400 MHz, DMSO-d$_6$) δ 8.74 (s, 1H), 7.50 (s, 1H), 5.68 (s, 1H), 4.70 (dd, J = 7.7, 3.6 Hz, 1H), 4.40 (s, 1H), 3.71-3.61 (m, 1H), 3.55-3.44 (m, 1H), 3.42 (s, 3H), 2.70 (d, J = 3.5 Hz, 3H), 2.60 (d, J = 8.7 Hz, 1H), 2.19 (s, 5H), 2.17-2.07 (m, 4H), 2.04 (s, 3H), 2.01 (dd, J = 9.6, 5.3 Hz, 2H), 1.77 (d, J = 12.9 Hz, 1H), 1.48 (td, J = 11.8, 5.5 Hz, 1H). | 479.25 |

TABLE 41-continued

Exemplary Compounds

| Compound | Structure | Proton NMR | MS [M + 1] |
|---|---|---|---|
| (S)-1-((S)-4-(6-(6-ethynyl-4-methoxypyridin-3-yl)-4,7-dimethyl-7H-pyrrolo[2,3-d]pyrimidin-5-yl)cyclohex-3-ene-1-carbonyl)pyrrolidine-2-carbonitrile | 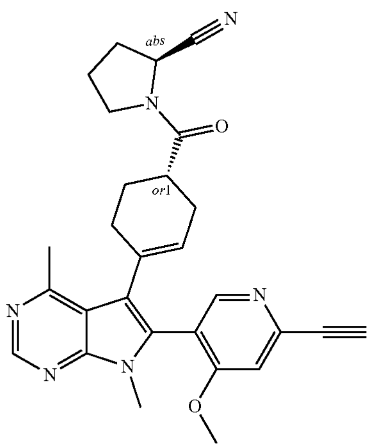 [SMILES: C#Cc1cc(OC)c(-c2c(C3=CC[C@@H](C(=O)N4CCC[C@H]4C#N)CC3)c3c(C)ncnc3n2C)cn1] | $^1$H NMR (400 MHz, DMSO-d$_6$) δ 8.67 (s, 1H), 8.33 (d, J = 8.8 Hz, 1H), 7.44 (d, J = 1.4 Hz, 1H), 5.64 (d, J = 23.1 Hz, 1H), 4.73 (dd, J = 7.6, 3.7 Hz, 1H), 4.47 (s, 1H), 3.91 (d, J = 1.7 Hz, 3H), 3.51 (s, 4H), 2.66 (d, J = 2.8 Hz, 3H), 2.28-2.11 (m, 4H), 2.08 (s, 2H), 2.02 (s, 2H), 1.83 (s, 1H), 1.66-1.45 (m, 2H), 1.45-1.34 (m, 1H), 1.24 (s, 1H). | 481.4 |
| S)-1-((R)-4-(6-(6-ethynyl-4-methoxypyridin-3-yl)-4,7-dimethyl-7H-pyrrolo[2,3-d]pyrimidin-5-yl)cyclohex-3-ene-1-carbonyl)pyrrolidine-2-carbonitrile | 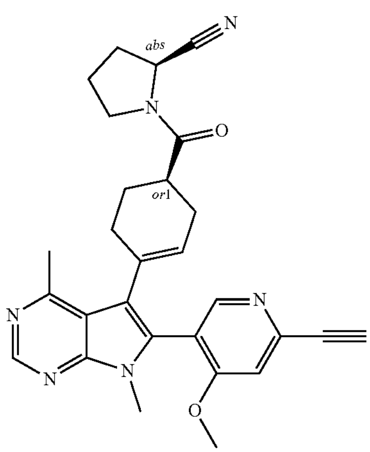 [SMILES: C#Cc1cc(OC)c(-c2c(C3=CC[C@H](C(=O)N4CCC[C@H]4C#N)CC3)c3c(C)ncnc3n2C)cn1] | $^1$H NMR (400 MHz, DMSO-d$_6$) δ 8.67 (s, 1H), 8.34 (d, J = 7.8 Hz, 1H), 7.45 (d, J = 3.4 Hz, 1H), 5.66 (d, J = 14.2 Hz, 1H), 4.72 (dd, J = 7.8, 3.5 Hz, 1H), 4.48 (d, J = 1.3 Hz, 1H), 3.91 (d, J = 2.0 Hz, 3H), 3.68 (s, 1H), 3.52 (s, 4H), 2.66 (s, 4H), 2.20 (s, 3H), 2.14 (d, J = 7.8 Hz, 2H), 2.08 (s, 1H), 2.02 (d, J = 8.5 Hz, 3H), 1.80 (s, 1H), 1.54 (d, J = 8.2 Hz, 1H), 1.45-1.39 (m, 1H), 1.24 (s, 1H), 1.16 (d, J = 7.2 Hz, 1H). | 481.25 |
| (S)-1-((S)-4-(4-amino-6-(6-ethynyl-2,4-dimethylpyridin-3-yl)-7-methyl-7H-pyrrolo[2,3-d]pyrimidin-5-yl)cyclohex-3-ene-1-carbonyl)pyrrolidine-2-carbonitrile | isomer 1 | $^1$H NMR (400 MHz, DMSO-d$_6$) δ 8.13 (s, 1H), 7.47 (s, 1H), 6.55 (s, 2H), 5.65 (q, J = 2.8, 2.2 Hz, 1H), 4.70 (dd, J = 7.4, 3.4 Hz, 1H), 4.38 (s, 1H), 3.69 (ddd, J = 10.9, 7.4, 3.8 Hz, 1H), 3.47 (td, J = 8.9, 6.7 Hz, 1H), 3.31 (s, 3H), 2.79 (t, J = 6.2 Hz, 1H), 2.24 (s, 2H), 2.19 (s, 3H), 2.13 (ddd, J = 9.8, 6.7, 3.5 Hz, 2H), 2.03 (s, 5H), 1.90 (s, 2H), 1.61 (s, 2H). | 480.25 |

TABLE 41-continued

Exemplary Compounds

| Compound | Structure | Proton NMR | MS [M + 1] |
|---|---|---|---|
| (S)-1-((S)-4-(4-amino-6-(6-ethynyl-2,4-dimethylpyridin-3-yl)-7-methyl-7H-pyrrolo[2,3-d]pyrimidin-5-yl)cyclohex-3-ene-1-carbonyl)pyrrolidine-2-carbonitrile | isomer 2 | $^1$H NMR (400 MHz, DMSO-d$_6$) δ 8.14 (s, 1H), 7.47 (s, 1H), 6.58 (s, 2H), 5.66 (s, 1H), 4.70 (dd, J = 7.4, 3.6 Hz, 1H), 4.38 (s, 1H), 3.74-3.65 (m, 1H), 3.47 (q, J = 8.6 Hz, 1H), 3.31 (s, 3H), 2.88 (s, 1H), 2.25 (s, 2H), 2.21-2.09 (m, 5H), 2.04 (s, 5H), 1.88 (s, 2H), 1.60 (d, J = 9.4 Hz, 2H). | 480.25 |
| (S)-1-((R)-4-(4-amino-6-(6-ethynyl-2,4-dimethylpyridin-3-yl)-7-methyl-7H-pyrrolo[2,3-d]pyrimidin-5-yl)cyclohex-3-ene-1-carbonyl)pyrrolidine-2-carbonitrile | isomer 3 | $^1$H NMR (400 MHz, DMSO-d$_6$) δ 8.16 (s, 1H), 7.48 (s, 1H), 6.72 (s, 2H), 5.66 (s, 1H), 4.71 (dd, J = 7.9, 3.7 Hz, 1H), 4.38 (s, 1H), 3.60 (t, J = 6.1 Hz, 1H), 3.53 (q, J = 8.1 Hz, 1H), 3.32 (s, 3H), 2.84-2.77 (m, 1H), 2.25 (s, 2H), 2.18 (s, 4H), 2.05 (s, 3H), 2.04-1.96 (m, 2H), 1.89 (s, 2H), 1.63 (d, J = 6.3 Hz, 2H), 1.16 (t, J = 7.3 Hz, 1H). | 480.25 |
| (S)-1-((R)-4-(4-amino-6-(6-ethynyl-2,4-dimethylpyridin-3-yl)-7-methyl-7H-pyrrolo[2,3-d]pyrimidin-5-yl)cyclohex-3-ene-1-carbonyl)pyrrolidine-2-carbonitrile | isomer 4 | $^1$H NMR (400 MHz, DMSO-d$_6$) δ 8.16 (s, 1H), 7.47 (s, 1H), 6.72 (s, 2H), 5.65 (s, 1H), 4.71 (dd, J = 7.9, 3.7 Hz, 1H), 4.39 (s, 1H), 3.61 (dd, J = 10.4, 4.6 Hz, 1H), 3.53 (q, J = 8.5, 8.0 Hz, 1H), 3.32 (s, 3H), 2.80 (t, J = 6.1 Hz, 1H), 2.24 (s, 1H), 2.20 (s, 5H), 2.05-1.95 (m, 5H), 1.91 (s, 2H), 1.64 (s, 2H), 1.16 (t, J = 7.3 Hz, 1H). | 480.25 |

TABLE 41-continued

Exemplary Compounds

| Compound | Structure | Proton NMR | MS [M + 1] |
| --- | --- | --- | --- |
| (S)-1-((R)-4-(6-(6-ethynyl-4-methoxy-2-methylpyridin-3-yl)-4,7-dimethyl-7H-pyrrolo[2,3-d]pyrimidin-5-yl)cyclohex-3-ene-1-carbonyl)pyrrolidine-2-carbonitrile | Atropisomer 1 | $^1$H NMR (400 MHz, DMSO-d$_6$) δ 8.65 (d, J = 1.4 Hz, 1H), 7.28 (s, 1H), 5.60 (s, 1H), 4.70 (t, J = 7.7, 3.5 Hz, 1H), 4.41 (d, J = 1.1 Hz, 1H), 3.81 (s, 3H), 3.70-3.57 (m, 1H), 3.51 (t, J = 8.5 Hz, 1H), 3.41 (s, 3H), 2.68-2.56 (m, 4H), 2.27-2.08 (m, 6H), 2.04 (d, J = 15.4 Hz, 6H), 1.79 (d, J = 13.1 Hz, 1H). | 495.25 |
| (S)-1-((R)-4-(6-(6-ethynyl-4-methoxy-2-methylpyridin-3-yl)-4,7-dimethyl-7H-pyrrolo[2,3-d]pyrimidin-5-yl)cyclohex-3-ene-1-carbonyl)pyrrolidine-2-carbonitrile | Atropisomer 2 | $^1$H NMR (400 MHz, DMSO-d$_6$) δ 8.65 (s, 1H), 7.28 (s, 1H), 5.58 (s, 1H), 4.71 (dd, J = 7.6, 3.7 Hz, 1H), 4.41 (s, 1H), 3.82 (d, J = 2.3 Hz, 3H), 3.70-3.59 (m, 1H), 3.51 (q, J = 8.2 Hz, 1H), 3.42 (s, 3H), 2.66 (d, J = 3.3 Hz, 3H), 2.56 (s, 1H), 2.17 (s, 5H), 2.15-2.05 (m, 4H), 2.02 (t, J = 7.0 Hz, 2H), 1.81 (d, J = 13.1 Hz, 1H), 1.56 (d, J = 6.6 Hz, 1H). | 495.30 |
| (S)-1-((S)-4-(6-(6-ethynyl-4-methoxy-2-methylpyridin-3-yl)-4,7-dimethyl-7H-pyrrolo[2,3-d]pyrimidin-5-yl)cyclohex-3-ene-1-carbonyl)pyrrolidine-2-carbonitrile | Atropisomer 1 | $^1$H NMR (400 MHz, DMSO-d$_6$) δ 8.66 (s, 1H), 7.28 (s, 1H), 5.60 (s, 1H), 4.71 (dd, J = 7.7, 3.5 Hz, 1H), 4.42 (s, 1H), 3.82 (s, 3H), 3.67 (ddd, J = 9.5, 7.2, 4.4 Hz, 1H), 3.49 (dd, J = 9.4, 7.3 Hz, 1H), 3.42 (s, 3H), 2.66 (d, J = 2.5 Hz, 3H), 2.62-2.56 (m, 1H), 2.17 (d, J = 2.2 Hz, 4H), 2.16-1.95 (m, 6H), 1.78 (dd, J = 13.1, 3.3 Hz, 1H), 1.61-1.43 (m, 2H). | 495.25 |

TABLE 41-continued
Exemplary Compounds
| Compound | Structure | Proton NMR | MS [M + 1] |
|---|---|---|---|
| (S)-1-((S)-4-(6-(6-ethynyl-4-methoxy-2-methylpyridin-3-yl)-4,7-dimethyl-7H-pyrrolo[2,3-d]pyrimidin-5-yl)cyclohex-3-ene-1-carbonyl)pyrrolidine-2-carbonitrile | Atropisomer 2 | $^1$H NMR (400 MHz, DMSO-d$_6$) δ 8.65 (s, 1H), 7.28 (s, 1H), 5.60 (d, J = 25.9 Hz, 1H), 4.71 (d, J = 6.4 Hz, 1H), 4.42 (s, 1H), 3.82 (s, 3H), 3.66 (s, 1H), 3.59-3.50 (m, 1H), 2.91 (s, 1H), 2.65 (s, 3H), 2.17 (s, 5H), 2.10 (d, J = 14.7 Hz, 2H), 2.01 (s, 2H), 1.79 (d, J = 24.2 Hz, 1H), 1.45 (s, 1H), 1.24 (s, 4H), 1.15 (d, J = 9.2 Hz, 1H). | 495.30 |
Example 43
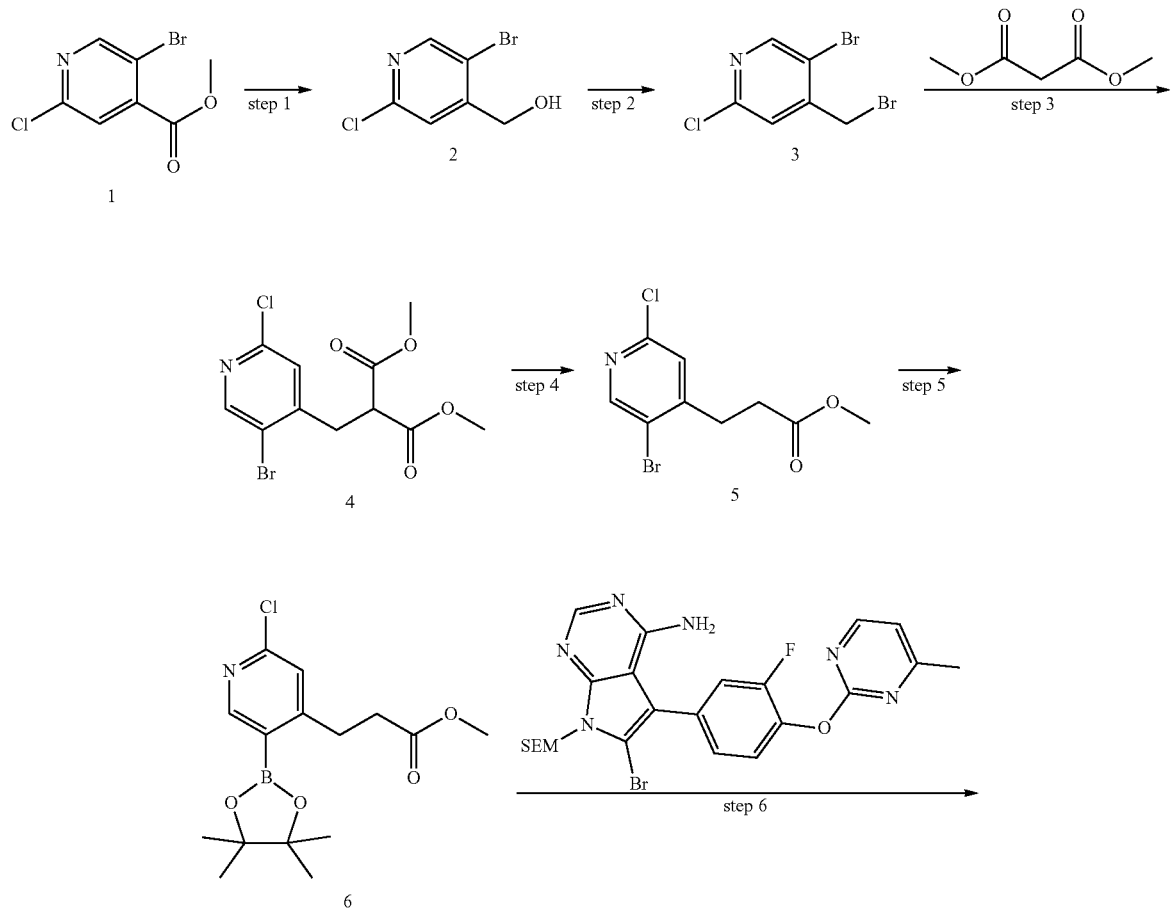

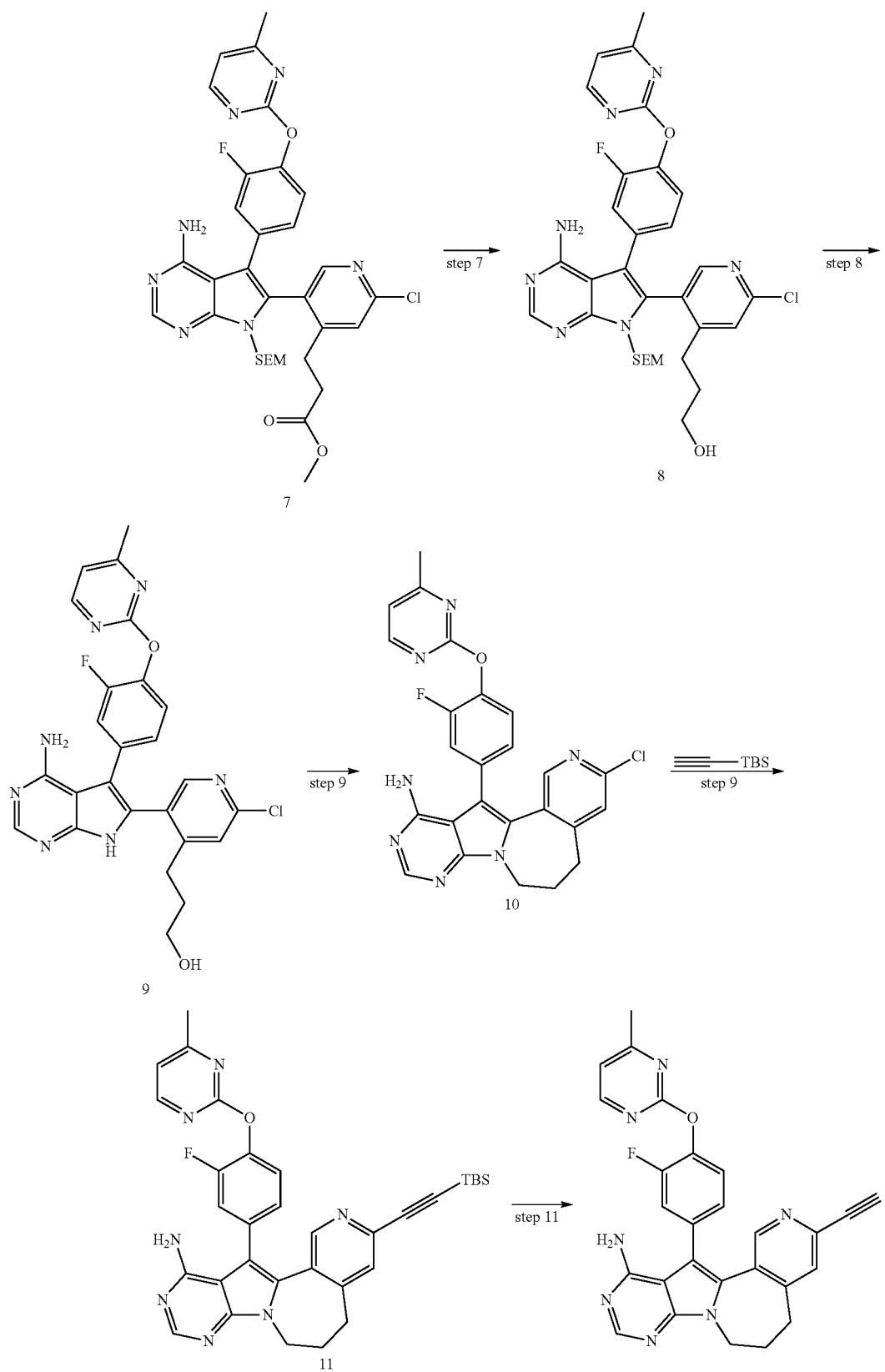

(5-bromo-2-chloropyridin-4-yl)methanol

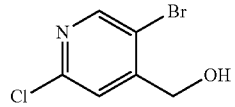

Step 1: A solution of methyl 5-bromo-2-chloropyridine-4-carboxylate (75.0 g, 299 mmol) in THF (1.5 L) was cooled to −20° C. LiBH₄ (179 mL, 358 mmol, 2 M in THF) was added drop-wise over a 1.5 h period while the temperature was maintained below −15° C. The solution was warmed to r.t. and stirred for 2 h at 25° C. and then carefully quenched by the drop-wise addition of Sat. NH₄Cl (200 mL), and the aqueous phase was extracted with EtOAc (1.2 L) for three times. The combined organic layers were washed with brine, dried over sodium sulfate, filtered, and concentrated in vacuo. The resulting crude material was purified by silica gel chromatography (450 g column; eluting with petroleum ether: ethyl acetate; 10:1). Concentration in vacuo resulted in (5-bromo-2-chloropyridin-4-yl)methanol (40 g, 60.1%) as an off-white amorphous solid.

5-bromo-4-(bromomethyl)-2-chloropyridine

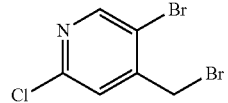

Step 2: To the mixture of (5-bromo-2-chloropyridin-4-yl)methanol (54.0 g, 242 mmol) and CBr₄ (87.2 g, 266 mmol) in DCM (1.5 L) was added PPh₃ (69.6 g, 266 mmol) in DCM (300 mL) drop-wise at 0° C., which was stirred at 0° C. for 1 h. The reaction was quenched with brine (500 mL). The partitioned layers were separated. The aqueous phase was extracted with DCM (1 L×3). The combined organic layers were washed with brine (1 L), dried over anhydrous Na₂SO₄, filtered and concentrated to give a residue. The residue was purified by flash silica gel chromatography (petroleum ether:ethyl acetate=30:1) to afford the product of 5-bromo-4-(bromomethyl)-2-chloropyridine (51 g, 73.9%) as a white solid.

1,3-dimethyl 2-[(5-bromo-2-chloropyridin-4-yl)methyl]propanedioate

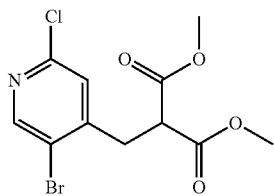

Step 3: To the mixture of 1,3-dimethyl propanedioate (62.0 g, 470 mmol) in THF (900 mL) was added NaH (18.6 g, 470 mmol) at −10° C., which was stirred for 30 min at −10° C., then 5-bromo-4-(bromomethyl)-2-chloropyridine (45.0 g, 157 mmol) in 300 mL THF was added dropwised into above solution and stirred for 2 h. The mixture was quenched with Sat. NH4Cl (600 mL). The aqueous phase was extracted with EtOAc(1 L) three times. The combined organic layers were washed with brine, dried over sodium sulfate, filtered, and concentrated in vacuo. The resulting crude material was purified by silica gel chromatography (500 g column; eluting with petroleum ether:ethyl acetate=15:1). Concentration in vacuo resulted in 1,3-dimethyl 2-[(5-bromo-2-chloropyridin yl)methyl]propanedioate (40 g, 75.7%) as an off-white amorphous solid.

Methyl 3-(5-bromo-2-chloropyridin-4-yl)propanoate

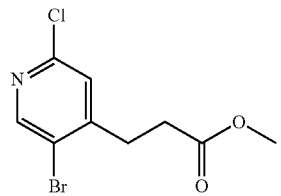

Step 4: A round bottomed flask was charged with 1,3-dimethyl 2-[(5-bromo-2-chloropyridin-4-yl)methyl]propanedioate (39.5 g, 117 mmol), NaCl (20.3 g, 351 mmol), H₂O (6.31 g, 351 mmol) and a stirbar. DMSO (800 mL) was added, and the solution was stirred for 1 h at 160° C. The reaction mixture was diluted with EtOAc (1.5 L), and the aqueous phase was washed with brine (600 mL) four times. The combined organic layers were dried over sodium sulfate, filtered, and concentrated in vacuo. The resulting crude material was purified by silica gel chromatography (300 g column; eluting with petroleum ether/ethyl acetate; 15:1). Concentration in vacuo resulted in methyl 3-(5-bromo-2-chloropyridin-4-yl) propanoate (22.0 g, 67%) as a white amorphous solid.

Methyl 3-(2-chloro-5-(4,4,5,5-tetramethyl-1,3,2-dioxaborolan-2-yl)pyridin-4-yl)propanoate

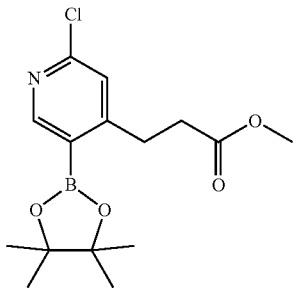

Step 5: A resealable reaction vial was charged with methyl 3-(5-bromo-2-chloropyridin-4-yl)propanoate (10 g, 35.9 mmol), 4,4,5,5-tetramethyl-2-(4,4,5,5-tetramethyl-1,3,2-dioxaborolan-2-yl)-1,3,2-dioxaborolane (11.8 g, 46.6 mmol), Pd(dppf)Cl₂ (2.62 g, 3.59 mmol), KOAc (10.4 g, 107 mmol), and a stirbar before being evacuated and purged with nitrogen three times. Dioxane (200 mL) was added, and the mixture was stirred for 12 h at 70° C. The catalyst and salt were collected by filtration through a celite pad and washed with EtOAc(100 mL) for three times. The combined organic layer was dried with Na$_2$SO$_4$, filtered and evaporated under reduced pressure. The resulting crude material was purified by silica gel chromatography (200 g column; eluting with petroleum ether/ethyl acetate; 15:1). Concentration in vacuo resulted in methyl 3-[2-chloro-5-(4,4,5,5-tetramethyl-1,3,2-dioxaborolan-2-yl)pyridin-4-yl]propanoate (6.5 g, 56.0%) as a white amorphous solid.

Methyl 3-(5-(4-amino-5-(3-fluoro-4-((4-methylpyrimidin-2-yl)oxy)phenyl)-7-((2-(trimethylsilyl)ethoxy)methyl)-7H-pyrrolo[2,3-d]pyrimidin-6-yl)-2-chloropyridin-4-yl)propanoate

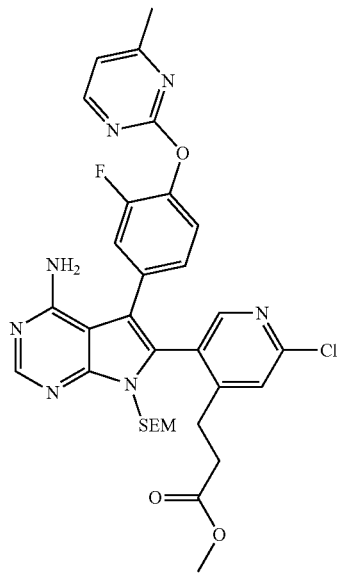 [SMILES: COC(=O)CCc1cc(Cl)ncc1-c1c(-c2ccc(Oc3nccc(C)n3)c(F)c2)c2c(N)ncnc2n1COCC[Si](C)(C)C]

Step 6: A resealable reaction vial was charged with 6-bromo-5-{3-fluoro-4-[(4-methylpyrimidin-2-yl)oxy]phenyl}-7-{[2-(trimethylsilyl)ethoxy]methyl}-7H-pyrrolo[2,3-d]pyrimidin-4-amine (14.5 g, 26.5 mmol), methyl 3-[2-chloro-5-(4,4,5,5-tetramethyl-1,3,2-dioxaborolan-2-yl)pyridin-4-yl]propanoate (12.9 g, 39.7 mmol), Pd(DTBPF)Cl2 (1.72 g, 2.65 mmol), CsF (12.0 g, 79.5 mmol), and a stirbar before being evacuated and purged with nitrogen three times. THF/H2O (300 mL) was added, and the mixture was stirred for 12 h at 70° C. The reaction mixture was diluted with water (100 mL), and the aqueous phase was extracted with dichloromethane (500 mL) three times. The combined organic layers were washed with brine, dried over sodium sulfate, filtered, and concentrated in vacuo. The resulting crude material was purified by silica gel chromatography (200 g column; eluting with dichloromethane/methanol; 20:1). Concentration in vacuo resulted in methyl 3-[5-(4-amino-5-{3-fluoro-4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]propanoate (7.00 g, 40%) as a brown amorphous solid.

3-(5-(4-amino-5-(3-fluoro-4-((4-methylpyrimidin-2-yl)oxy)phenyl)-7-((2-(trimethylsilyl)ethoxy)methyl)-7H-pyrrolo[2,3-d]pyrimidin-6-yl)-2-chloropyridin-4-yl)propan-1-ol

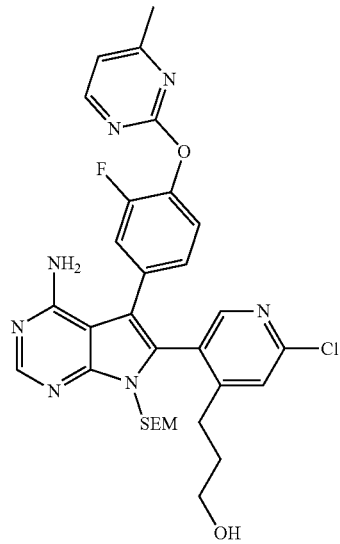 [SMILES: Cc1ccnc(Oc2ccc(-c3c(-c4cnc(Cl)cc4CCCO)n(COCC[Si](C)(C)C)c4ncnc(N)c34)cc2F)n1]

Step 7: A round bottomed flask was charged with methyl 3-[5-(4-amino-5-{3-fluoro-4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]propanoate (7.00 g, 10.5 mmol), DCM (120 mL) and a stirbar. DIBAL (8.39 mL, 12.6 mmol) was added at 0° C., and the solution was stirred for 3 h at 0° C. The reaction mixture was diluted with MeOH (10 mL) and water 60 mL, and the aqueous phase was to extracted with dichloromethane (100 mL) three times. The combined organic layers were filtered and washed with brine, dried over sodium sulfate, filtered, and concentrated in vacuo. The resulting crude material was purified by C18 flash (acetonitrile/water/0.1% formic acid). Lyophilization yielded 3-[5-(4-amino-5-{3-fluoro-4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]propan-1-ol (3.00 g, 45%) as a yellow amorphous solid.

3-(5-(4-amino-5-(3-fluoro-4-((4-methylpyrimidin-2-yl)oxy)phenyl)-7H-pyrrolo[2,3-d]pyrimidin-6-yl)-2-chloropyridin-4-yl)propan-1-ol

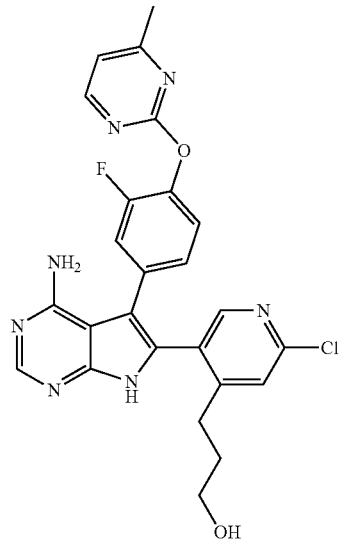 [SMILES: Cc1ccnc(Oc2ccc(-c3c(-c4cnc(Cl)cc4CCCO)[nH]c4ncnc(N)c34)cc2F)n1]

Step 8: A round bottomed flask was charged with 3-[5-(4-amino-5-{3-fluoro-4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]propan-1-ol (2.60 g, 4.08 mmol), CH3SO3H/THF (40 mL) and a stirbar. The solution was stirred for 1 h at 70° C. The reaction mixture was diluted with water (100 mL), and the aqueous phase was adjust pH value to 7 with Na2CO3, extracted with DCM (150 mL) three times. The combined organic layers were washed with brine, dried over sodium sulfate, filtered, and concentrated in vacuo. The resulting crude material was purified by silica gel chromatography (50 g column; eluting with dichloromethane/methanol; 12:1). Concentration in vacuo resulted in 3-[5-(4-amino-5-{3-fluoro-4-[(4-methylpyrimidin-2-yl)oxy]phenyl}-7H-pyrrolo[2,3-d]pyrimidin-6-yl)-2-chloropyridin-4-yl]propan-1-ol (800 mg, 39%) as an off-white amorphous solid.

3-chloro-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine

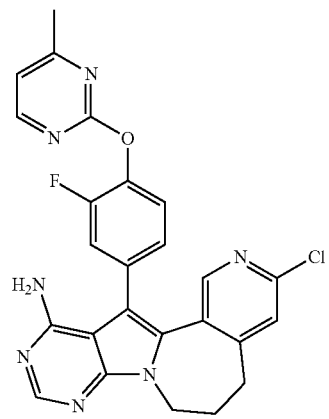 [SMILES: Cc1ccnc(Oc2ccc(-c3c4n(c5ncnc(N)c35)CCCc3cc(Cl)ncc3-4)cc2F)n1]

Step 9: A resealable reaction vial was charged with 3-[5-(4-amino-5-{3-fluoro-4-[(4-methylpyrimidin-2-yl)oxy]phenyl}-7H-pyrrolo[2,3-d]pyrimidin-6-yl)-2-chloropyridin-4-yl]propan-1-ol (680 mg, 1.34 mmol), DIAD (406 mg, 2.01 mmol) tetrahydrofuran (8 mL), and a stirbar before being evacuated and purged with nitrogen three times. PPh3 (526 mg, 2.01 mmol) in 2 mL THF was added, and the mixture was stirred for 1 h at 25° C. The reaction mixture was diluted with water (5 mL), and the aqueous phase was extracted with DCM (25 mL) three times. The combined organic layers were washed with brine, dried over sodium sulfate, filtered, and concentrated in vacuo. The resulting crude material was purified by prep-TLC(dichloromethane/methanol; 15:1). Concentration in vacuo resulted in 3-chloro-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine (450 mg, 69%) as a yellow amorphous solid.

3-((tert-butyldimethylsilyl)ethynyl)-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine

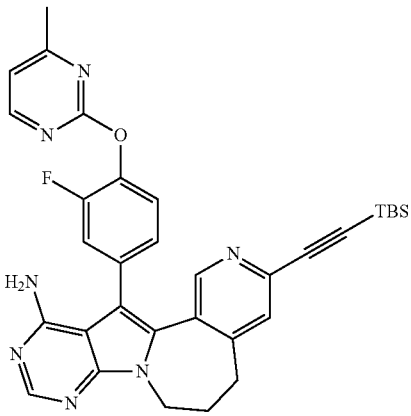

Step 10: A resealable reaction vial was charged with 3-chloro-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine (430 mg, 881 µmol), tert-butyl(ethynyl)dimethylsilane (246 mg, 1.76 mmol), Pd(dppf)Cl2 (128 mg, 176 µmol), CuI (66.8 mg, 352 µmol), TEA (266 mg, 2.64 mmol) and a stirbar before being evacuated and purged with nitrogen three times. dimethylformamide (1 mL) was added, and the mixture was stirred for 2 h at 50° C. The reaction mixture was diluted with water (5 mL), and the aqueous phase was extracted with DCM (25 mL) three times. The combined organic layers were washed with brine, dried over sodium sulfate, filtered, and concentrated in vacuo. The resulting crude material was purified by prep-TLC(dichloromethane/methanol; 15:1). Concentration in vacuo resulted in 3-((tert-butyldimethylsilyl)ethynyl)-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine (350 mg, 67%) as an off-white amorphous solid.

3-ethynyl-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine

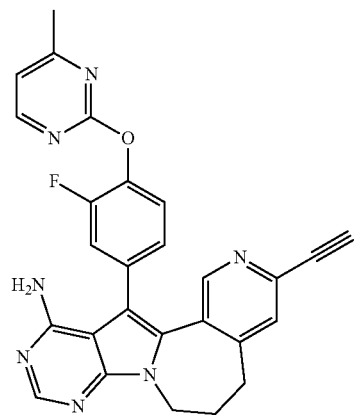 [SMILES: C#Cc1cc2c(cn1)-c1c(-c3ccc(Oc4nccc(C)n4)c(F)c3)c3c(N)ncnc3n1CCC2]

Step 11: A round bottomed flask was charged with 3-((tert-butyldimethylsilyl)ethynyl)-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine (340 mg, 574 μmol), tetrahydrofuran (2 mL) and a stirbar. TBAF (179 mg, 688 μmol) was added, and the solution was stirred at r.t. for 1 h. The reaction mixture was purified by silica gel chromatography (20 g column; eluting with dichloromethane/methanol; 10:1). Concentration in vacuo and the crude product was dissolved with DMF (3 mL), filtered and the the cake was washed with ACN (10 mL) and DCM (10 mL) for three times, dried under reduced pressure. Lyophilization yielded 3-ethynyl-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine (173.1 mg, 362 μmol, 63.1%) as a yellow amorphous solid.

TABLE 42

Exemplary Compounds

| Compound | Structure | Proton NMR | MS [M + 1] |
|---|---|---|---|
| 3-ethynyl-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine | 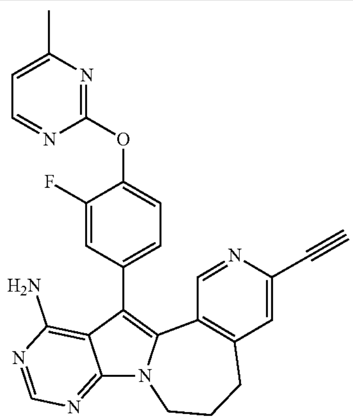 [SMILES: C#Cc1cc2c(cn1)-c1c(-c3ccc(Oc4nccc(C)n4)c(F)c3)c3c(N)ncnc3n1CCC2] | $^1$H NMR (400 MHz, DMSO-$d_6$) δ 8.51 (d, J = 5.0 Hz, 1H), 8.21 (s, 1H), 8.04 (s, 1H), 7.67 (s, 1H), 7.50-7.34 (m, 2H), 7.24-7.20 (m, 2H), 6.36-5.89 (m, 1H), 5.76 (s, 1H), 4.40 (s, 1H), 4.15 (s, 2H), 2.79 (t, J = 7.0 Hz, 2H), 2.44 (s, 3H), 2.25 (t, J = 7.1 Hz, 2H). | 478.10 |

Example 44

Scheme 41

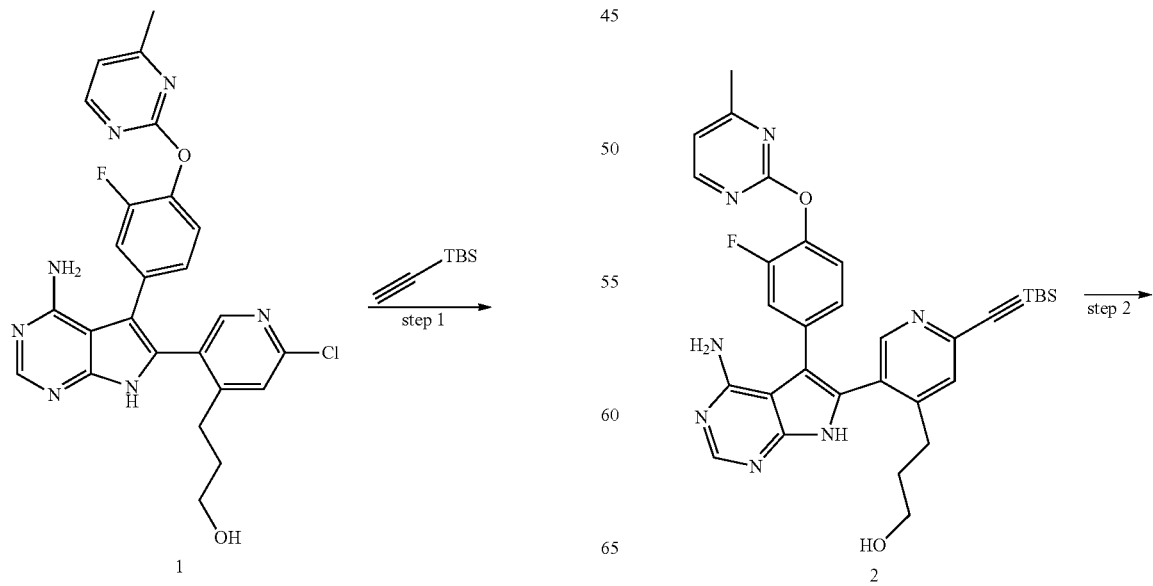

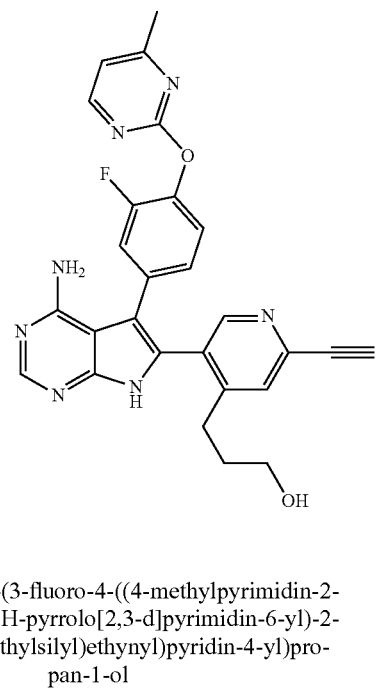

3-(5-(4-amino-5-(3-fluoro-4-((4-methylpyrimidin-2-yl)oxy)phenyl)-7H-pyrrolo[2,3-d]pyrimidin-6-yl)-2-((tert-butyldimethylsilyl)ethynyl)pyridin-4-yl)propan-1-ol

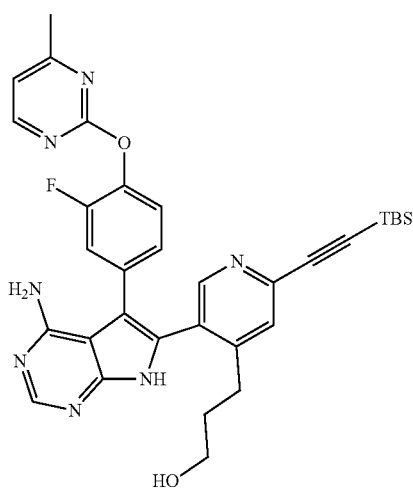

Step 1: A resealable reaction vial was charged with 3-[5-(4-amino-5-{3-fluoro-4-[(4-methylpyrimidin-2-yl)oxy]phenyl}-7H-pyrrolo[2,3-d]pyrimidin-6-yl)-2-chloropyridin-4-yl]propan-1-ol (90.0 mg, 177 μmol), Pd(dppf)Cl2 (25.9 mg, 35.4 μmol), CuI (13.4 mg, 70.8 μmol), TEA (53.6 mg, 531 μmol), tert-butyl(ethynyl)dimethylsilane (49.6 mg, 354 μmol) a stirbar before being evacuated and purged with nitrogen three times. Dimethylformamide (5 mL) was added, and the mixture was stirred for 2 h at 50° C. The reaction mixture was diluted with water (20 mL), and the aqueous phase was extracted with dichloromethane (25 mL) three times. The combined organic layers were washed with brine, dried over sodium sulfate, filtered, and concentrated in vacuo. The resulting crude material was purified by prep-TLC(dichloromethane/methanol; 15:1). Concentration in vacuo resulted in 3-[5-(4-amino-5-{3-fluoro-4-[(4-methylpyrimidin-2-yl)oxy]phenyl}-7H-pyrrolo[2,3-d]pyrimidin-6-yl)-2-[2-(tert-butyldimethylsilyl)ethynyl]pyridin-4-yl] propan-1-ol (80.0 mg, 74%) as a yellow amorphous solid.

3-(5-(4-amino-5-(3-fluoro-4-((4-methylpyrimidin-2-yl)oxy)phenyl)-7H-pyrrolo[2,3-d]pyrimidin-6-yl)-2-ethynylpyridin-4-yl)propan-1-ol

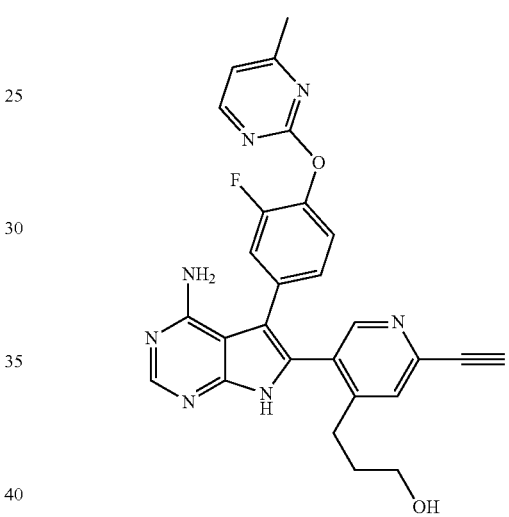

Step 2: A round bottomed flask was charged with 3-[5-(4-amino-5-{3-fluoro-4-[(4-methylpyrimidin-2-yl)oxy]phenyl}-7H-pyrrolo[2,3-d]pyrimidin-6-yl)-2-[2-(tert-butyldimethylsilyl)ethynyl]pyridin-4-yl]propan-1-ol (70.0 mg, 114 μmol), tetrahydrofuran (5 mL) and a stirbar. TBAF (35.3 mg, 136 μmol), was added, and the solution was stirred for 1 h at room temperature. The reaction material was purified by silica gel chromatography (10 g column; eluting with dichloromethane/methanol; 10:1). Concentration in vacuo and the crude product was washed with water for 5 times, the organic phase was concentrated and the resulting crude material was purified by prep-HPLC (Column: XBridge Prep OBD C18 Column, 30×150 mm 5 um; Mobile Phase A: Water(10 MMOL/L NH4HCO3+0.1% NH3·H2O), Mobile Phase B:ACN; Flow rate:60 mL/min; Gradient:15 B to 45 B in 8 min; 220 nm; RT1:7.23). Lyophilization yielded 3-[5-(4-amino-5-{3-fluoro-4-[(4-methylpyrimidin-2-yl)oxy]phenyl}-7H-pyrrolo[2,3-d]pyrimidin-6-yl)-2-ethynylpyridin-4-yl]propan-1-ol (11.2 mg, 19.8%) as a white amorphous solid.

TABLE 43
Exemplary Compound
| Compound | Structure | Proton NMR | MS [M + 1] |
|---|---|---|---|
| 3-(5-(4-amino-5-(3-fluoro-4-((4-methylpyrimidin-2-yl)oxy)phenyl)-7H-pyrrolo[2,3-d]pyrimidin-6-yl)-2-ethynylpyridin-4-yl)propan-1-ol | 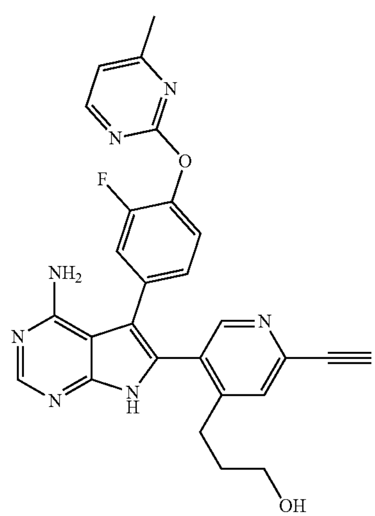 | $^1$H NMR (400 MHz, DMSO-d$_6$) δ 12.21 (s, 1H), 8.48 (d, J = 5.0 Hz, 1H), 8.37 (s, 1H), 8.19 (s, 1H), 7.51 (s, 1H), 7.35 (t, J = 8.4 Hz, 1H), 7.23-7.16 (m, 2H), 7.06 (dd, J = 8.0, 2.0 Hz, 1H), 6.10-6.00 (m, 1H), 4.44 (s, 1H), 4.39 (s, 1H), 3.30-3.10 (m, 4H), 2.42 (s, 3H), 1.53-1.47 (m, 2H). | 496.25 |
Example 45
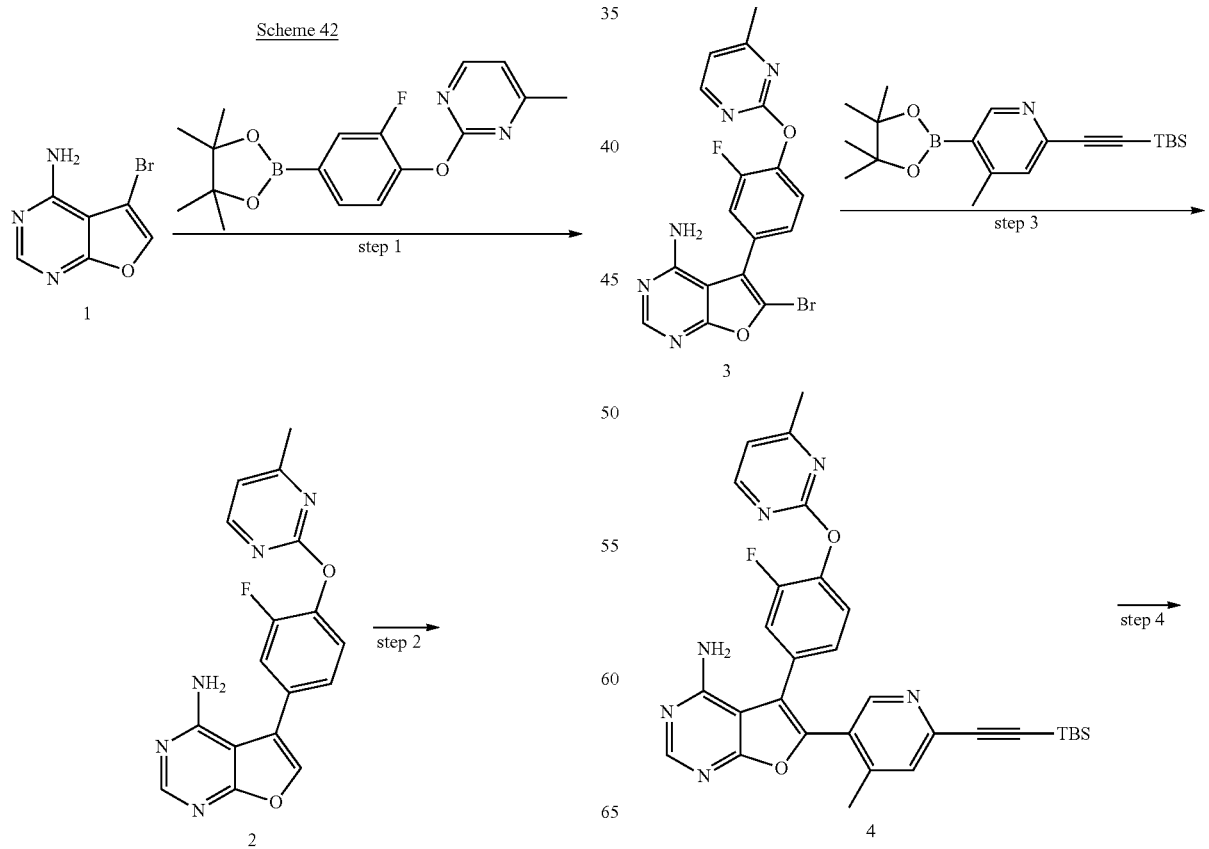

-continued

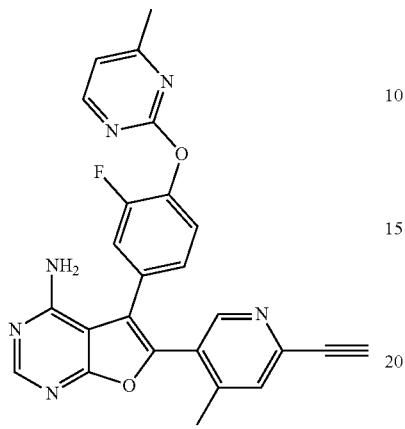

6-(6-((tert-butyldimethylsilyl)ethynyl)-4-methylpyri-
din-3-yl)furo[2,3-d]pyrimidin-4-amine

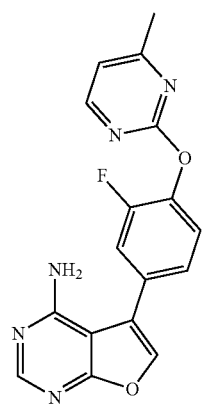 [SMILES: Cc1ccnc(Oc2ccc(-c3coc4ncnc(N)c34)cc2F)n1]

Step 1: A resealable reaction vial was charged with 5-bromofuro[2,3-d]pyrimidin-4-amine (800 mg, 3.73 mmol), 2-[2-fluoro-4-(4,4,5,5-tetramethyl-1,3,2-dioxaborolan-2-yl)phenoxy]-4-methylpyrimidine (1.84 g, 5.59 mmol), Pd(dppf)Cl₂ (2.72 g, 3.73 mmol), K₃PO₄ (790 mg, 3.73 mmol) and a stir bar before being evacuated and purged with nitrogen three times. DME/H₂O (15 mL) was added, and the mixture was stirred for 2 h at 90° C. The reaction mixture was diluted with water (100 mL), and the aqueous phase was extracted with DCM (50 mL) three times. The combined organic layers were washed with brine, dried over sodium sulfate, filtered, and concentrated in vacuo. The resulting crude material was purified by silica gel chromatography (100 g column; eluting with heptanes/ethyl acetate; ratio=1:1). Concentration in vacuo resulted in 5-{3-fluoro-4-[(4-methylpyrimidin-2-yl)oxy]phenyl}furo[2,3-d]pyrimidin-4-amine (800 mg, 64%) as an off-white amorphous solid.

6-6-bromo-5-(3-fluoro-4-((4-methylpyrimidin-2-yl)oxy)phenyl)furo[2,3-d]pyrimidin-4-amine

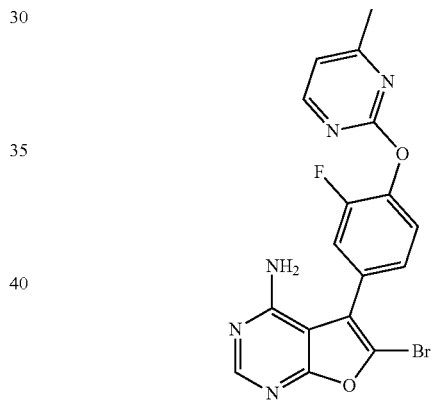

Step 2: A round bottomed flask was charged with 5-{3-fluoro-4-[(4-methylpyrimidin-2-yl)oxy]phenyl}furo[2,3-d]pyrimidin-4-amine (800 mg, 2.37 mmol), DCM (15 mL) and a stir bar. Br₂ (379 mg, 2.37 mmol) was added at 0° C., and the solution was stirred for 1 h at 0° C. The reaction was then quenched by saturated sodium thiosulfate aqueous. The reaction mixture was diluted with water (100 mL), and the aqueous phase was extracted with DCM (50 mL) three times. The combined organic layers were washed with brine, dried over sodium sulfate, filtered, and concentrated in vacuo. The resulting crude material was purified by prep-HPLC (acetonitrile/water/0.1% formic acid). Lyophilization yielded 6-bromo-5-{3-fluoro-4-[(4-methylpyrimidin-2-yl)oxy]phenyl}furo[2,3-d]pyrimidin-4-amine (700 mg, 71%) as an off-white amorphous solid.

1915
6-(6-((tert-butyldimethylsilyl)ethynyl)-4-methylpyridin-3-yl)-5-(3-fluoro-4-((4-methylpyrimidin-2-yl)oxy)phenyl)furo[2,3-d]pyrimidin-4-amine

1916
6-(6-ethynyl-4-methylpyridin-3-yl)-5-(3-fluoro-4-((4-methylpyrimidin-2-yl)oxy)phenyl)furo[2,3-d]pyrimidin-4-amine

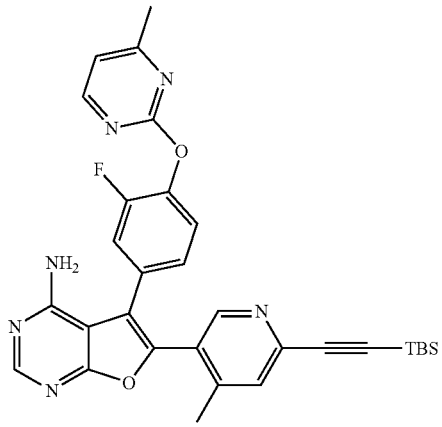

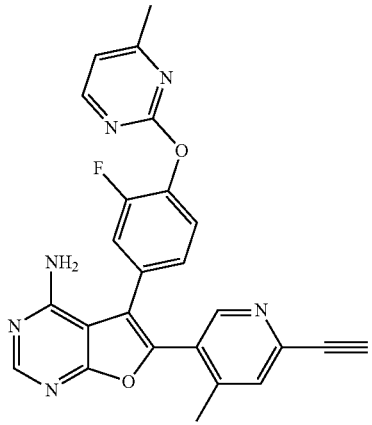 [SMILES: C#Cc1cc(C)c(-c2oc3ncnc(N)c3c2-c2ccc(Oc3nccc(C)n3)c(F)c2)cn1]

Step 3: A resealable reaction vial was charged with 6-bromo-5-{3-fluoro-4-[(4-methylpyrimidin-2-yl)oxy]phenyl}furo[2,3-d]pyrimidin-4-amine (680 mg, 1.63 mmol), 2-[2-(tert-butyldimethylsilyl)ethynyl]-4-methyl-5-(4,4,5,5-tetramethyl-1,3,2-dioxaborolan-2-yl)pyridine (872 mg, 2.44 mmol), Pd(dppf)Cl$_2$ (238 mg, 0.326 mmol), K$_3$PO$_4$ (1.03 g, 4.89 mmol), and a stir bar before being evacuated and purged with nitrogen three times. DME/H2O (20 mL) was added, and the mixture was stirred for 1 h at 90° C. The resulting crude material was purified by silica gel chromatography (50 g column; eluting with dichloromethane/methanol; ratio=30:1). Concentration in vacuo resulted in 6-{6-[2-(tert-butyldimethylsilyl)ethynyl]-4-methylpyridin-3-yl}-5-{3-fluoro-4-[(4-methylpyrimidin-2-yl)oxy]phenyl}furo[2,3-d]pyrimidin-4-amine (530 mg, 57%) as a black amorphous solid.

Step 4: A round bottomed flask was charged with 6-{6-[2-(tert-butyldimethylsilyl)ethynyl]-4-methylpyridin-3-yl}-5-{3-fluoro-4-[(4-methylpyrimidin-2-yl)oxy]phenyl}furo[2,3-d]pyrimidin-4-amine (500 mg, 0.88 mmol), tetrahydrofuran (10 mL) and a stir bar. TBAF (0.88 mL, 0.88 mmol) was added, and the solution was stirred for 30 min at room temperature. The resulting crude material was purified by silica gel chromatography (50 g column; eluting with dichloromethane/methanol; ratio=10:1). Concentration in vacuo resulted in crude product. The resulting crude material was purified by prep-HPLC (Column: XBridge Prep OBD C18 Column, 30×150 mm 5 um; Mobile Phase A:Water(10 MMOL/L NH$_4$HCO$_3$+0.1% NH$_3$·H$_2$O), Mobile Phase B:ACN; Flow rate:60 mL/min; Gradient:25 B to 55 B in 8 min; 220 nm; RT1:7.23). Lyophilization yielded 6-(6-ethynyl-4-methylpyridin-3-yl)-5-{3-fluoro-4-[(4-methylpyrimidin-2-yl)oxy]phenyl}furo[2,3-d]pyrimidin-4-amine (215 mg, 54%) as a white amorphous solid.

TABLE 44

Exemplary Compound

| Compound | Structure | Proton NMR | MS [M + 1] |
|---|---|---|---|
| 6-(6-ethynyl-4-methylpyridin-3-yl)-5-{3-fluoro-4-[(4-methylpyrimidin-2-yl)oxy]phenyl}furo[2,3-d]pyrimidin-4-amine | 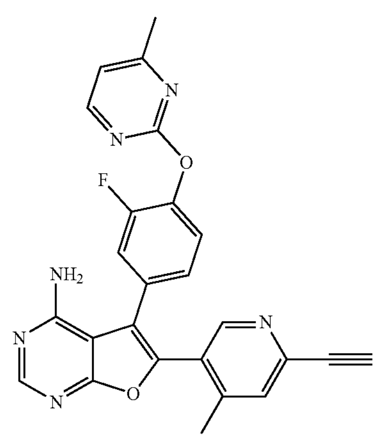 [SMILES: C#Cc1cc(C)c(-c2oc3ncnc(N)c3c2-c2ccc(Oc3nccc(C)n3)c(F)c2)cn1] | $^1$H NMR (400 MHz, DMSO-d$_6$) δ 8.50 (d, J = 5.0 Hz, 1H), 8.41 (s, 1H), 8.33 (s, 1H), 7.59 (s, 1H), 7.47-7.40 (m, 2H), 7.23-7.19 (m, 2H), 4.45 (s, 1H), 2.43 (s, 3H), 2.20 (s, 3H). | 453.15 |

Example 46
Scheme 43
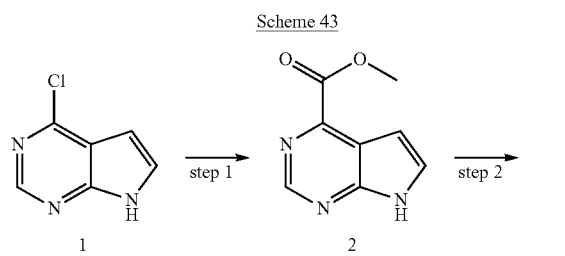
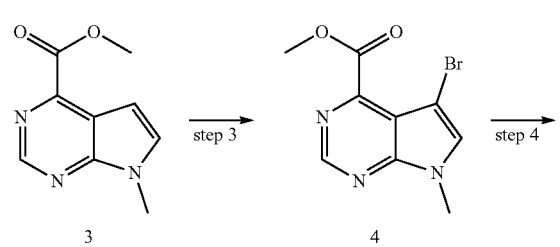
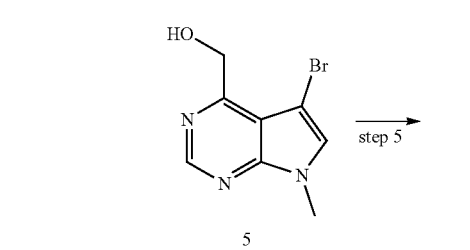
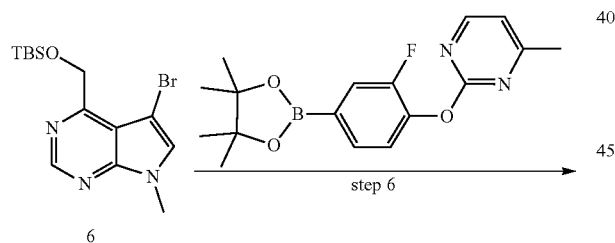
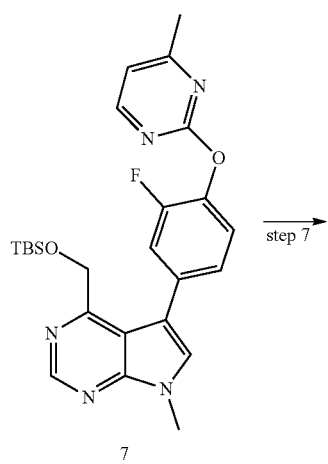
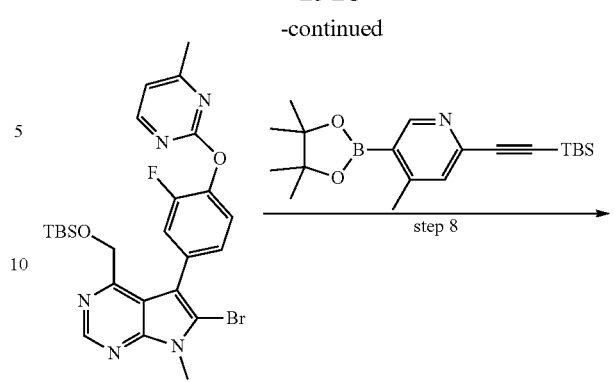
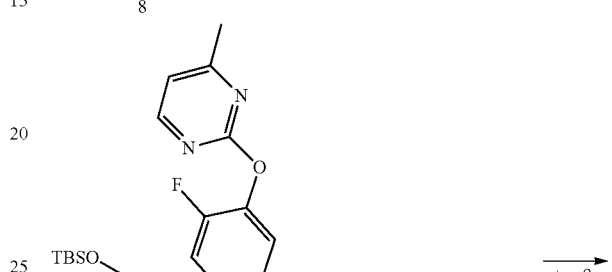
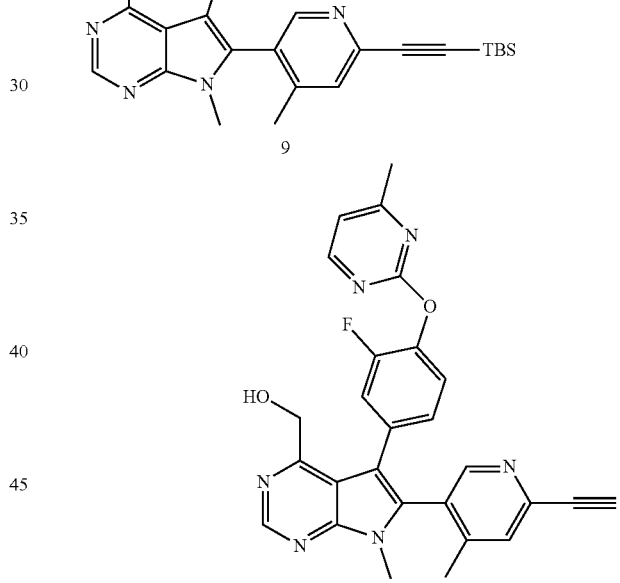
methyl 7H-pyrrolo[2,3-d]pyrimidine-4-carboxylate
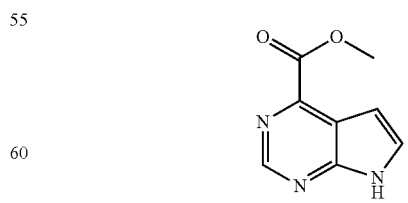
Step 1: A pressure tank reactor was charged with 4-chloro-7H-pyrrolo[2,3-d]pyrimidine (30 g, 195 mmol), TEA (59.1 g, 585 mmol), [(R)-(+)-2,2'-Bis(diphenylphosphino)-1,1'-binaphthyl]palladium(II) chloride (1.55 g, 1.95 mmol), MeOH (500 mL) and a stirbar. The mixture was stirred for 12 h at 100° C. under an atmosphere of CO (10 atm). The reaction mixture was filtered through a pad of Celite, the pad was washed with EA, and the filtrate was concentrated in vacuo resulted in methyl 7H-pyrrolo[2,3-d]pyrimidine-4-carboxylate (25.0 g, 72%) as a yellow amorphous solid.

methyl 7-methyl-7H-pyrrolo[2,3-d]pyrimidine-4-carboxylate

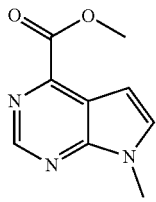

Step 2: A round bottomed flask was charged with methyl 7H-pyrrolo[2,3-d]pyrimidine-4-carboxylate (20 g, 112 mmol), DMF (100 mL) and a stir bar. NaH (10.7 g, 448 mmol) was added, and the reaction mixture was stirred for 30 min at 0° C. Then MeI (15.8 g, 112 mmol) was added and the solution was stirred for 1 h at 0° C. The reaction mixture was diluted with water (500 mL), and the aqueous phase was extracted with EA (100 mL) three times. The combined organic layers were washed with brine, dried over sodium sulfate, filtered, and concentrated in vacuo. The resulting crude material was purified by silica gel chromatography (100 g column; eluting with heptanes/ethyl acetate; ratio=3:1). Concentration in vacuo resulted in methyl 7-methyl-7H-pyrrolo[2,3-d]pyrimidine-4-carboxylate (13.0 g, 61%) as an off-white amorphous solid.

methyl 5-bromo-7-methyl-7H-pyrrolo[2,3-d]pyrimidine-4-carboxylate

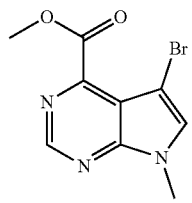

Step 3: A round bottomed flask was charged with methyl 7-methyl-7H-pyrrolo[2,3-d]pyrimidine-4-carboxylate (10 g, 52.3 mmol), DMF (200 mL) and a stir bar. NBS (11.1 g, 62.7 mmol) was added, and the solution was stirred for 1 h at r.t. The reaction mixture was diluted with water (300 mL), and the aqueous phase was extracted with EA (300 mL) three times. The combined organic layers were washed with brine, dried over sodium sulfate, filtered, and concentrated in vacuo. The resulting crude material was purified by silica gel chromatography (100 g column; eluting with dichloromethane/methanol; ratio=50:4-17561). Concentration in vacuo resulted in methyl 5-bromo-7-methyl-7H-pyrrolo[2,3-d]pyrimidine-4-carboxylate (10.0 g, 71%) as an off-white amorphous solid.

(5-bromo-7-methyl-7H-pyrrolo[2,3-d]pyrimidin-4-yl)methanol

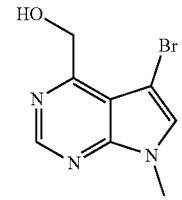

Step 4: A round bottomed flask was charged with methyl 5-bromo-7-methyl-7H-pyrrolo[2,3-d]pyrimidine-4-carboxylate (3 g, 11.1 mmol), THF (50 mL) and a stir bar. LiBH$_4$ (11.1 mL, 11.1 mmol) was added at −50° C. The reaction mixture was stirred for 1 h at −50° C. The reaction was quenched by the addition of 2 mL of EA. The reaction mixture was diluted with water (100 mL), and the aqueous phase was extracted with DCM (100 mL) three times. The combined organic layers were washed with brine, dried over sodium sulfate, filtered, and concentrated in vacuo. The resulting crude material was purified by silica gel chromatography (50 g column; eluting with heptanes/ethyl acetate; ratio=1:1). Concentration in vacuo resulted in {5-bromo-7-methyl-7H-pyrrolo[2,3-d]pyrimidin-4-yl}methanol (850 mg, 32%) as an off-white amorphous solid.

5-bromo-4-(((tert-butyldimethylsilyl)oxy)methyl)-7-methyl-7H-pyrrolo[2,3-d]pyrimidine

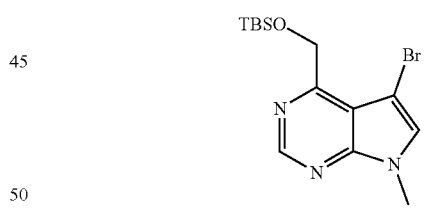

Step 5: A round bottomed flask was charged with {5-bromo-7-methyl-7H-pyrrolo[2,3-d]pyrimidin-4-yl}methanol (400 mg, 1.65 mmol), 1H-imidazole (561 mg, 8.25 mmol), THF (10 mL) and a stirbar. TBSCl (745 mg, 4.94 mmol) was added, and the solution was stirred for 12 h at r.t. The reaction mixture was diluted with water (100 mL), and the aqueous phase was extracted with EA (50 mL) three times. The combined organic layers were washed with brine, dried over sodium sulfate, filtered, and concentrated in vacuo. The resulting crude material was purified by silica gel chromatography (20 g column; eluting with heptanes/ethyl acetate; ratio=1:1). Concentration in vacuo resulted in 5-bromo-4-{[(tert-butyldimethylsilyl)oxy]methyl}-7-methyl-7H-pyrrolo[2,3-d]pyrimidine (330 mg, 56%) as a yellow amorphous solid.

4-(((tert-butyldimethylsilyl)oxy)methyl)-5-(3-fluoro-4-((4-methylpyrimidin-2-yl)oxy)phenyl)-7-methyl-7H-pyrrolo[2,3-d]pyrimidine

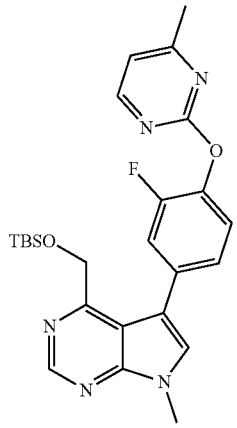 [SMILES: Cc1ccnc(Oc2ccc(-c3cn(C)c4ncnc(CO[Si](C)(C)C(C)(C)C)c34)cc2F)n1]

Step 6: A resealable reaction vial was charged with 5-bromo-4-{[(tert-butyldimethylsilyl)oxy]methyl}-7-methyl-7H-pyrrolo[2,3-d]pyrimidine (750 mg, 2.10 mmol), 2-[2-fluoro-4-(4,4,5,5-tetramethyl-1,3,2-dioxaborolan-2-yl)phenoxy]-4-methylpyrimidine (832 mg, 2.52 mmol), K₃PO₄ (1.33 g, 6.30 mmol), Pd(dppf)Cl₂ (307 mg, 0.42 mmol), and a stir bar before being evacuated and purged with nitrogen three times. DME/H₂O (20 mL) was added, and the mixture was stirred for 1 h at 90° C. The reaction mixture was diluted with water (50 mL), and the aqueous phase was extracted with DCM (50 mL) three times. The combined organic layers were washed with brine, dried over sodium sulfate, filtered, and concentrated in vacuo. The resulting crude material was purified by silica gel chromatography (50 g column; eluting with PE:EA; ratio=1:1). Concentration in vacuo resulted in 2-[4-(4-{[(tert-butyldimethylsilyl)oxy]methyl}-7-methyl-7H-pyrrolo[2,3-d]pyrimidin-5-yl)-2-fluorophenoxy]-4-methylpyrimidine (760 mg, 75%) as a yellow amorphous solid.

6-bromo-4-(((tert-butyldimethylsilyl)oxy)methyl)-5-(3-fluoro-4-((4-methylpyrimidin-2-yl)oxy)phenyl)-7-methyl-7H-pyrrolo[2,3-d]pyrimidine

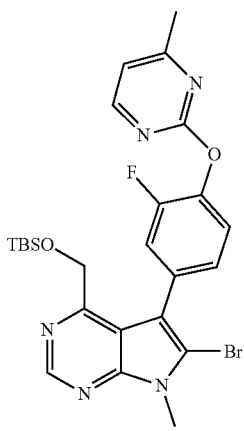 [SMILES: Cc1ccnc(Oc2ccc(-c3c(Br)n(C)c4ncnc(CO[Si](C)(C)C(C)(C)C)c34)cc2F)n1]

Step 7: A round bottomed flask was charged with 2-[4-(4-{[(tert-butyldimethylsilyl)oxy]methyl}-7-methyl-7H-pyrrolo[2,3-d]pyrimidin-5-yl)-2-fluorophenoxy]-4-methylpyrimidine (700 mg, 1.45 mmol), dimethylformamide (20 mL) and a stirbar. DBDMH (331 mg, 1.16 mmol) was added, and the solution was stirred for 2 h at 0° C. The reaction was then quenched with Na₂SO₃ aq. The reaction mixture was diluted with water (100 mL), and the aqueous phase was extracted with DCM (100 mL) three times. The resulting crude material was purified by prep-TLC (eluting with DCM:MeOH; ratio=20:1). Concentration in vacuo resulted in 2-[4-(6-bromo-4-{[(tert-butyldimethylsilyl)oxy]methyl}-7-methyl-7H-pyrrolo[2,3-d]pyrimidin-5-yl)-2-fluorophenoxy]-4-methylpyrimidine (400 mg, 49%) as a black amorphous solid.

6-(6-(((tert-butyldimethylsilyl)ethynyl)-4-methylpyridin-3-yl)-4-(((tert-butyldimethylsilyl)oxy)methyl)-5-(3-fluoro-4-((4-methylpyrimidin-2-yl)oxy)phenyl)-7-methyl-7H-pyrrolo[2,3-d]pyrimidine

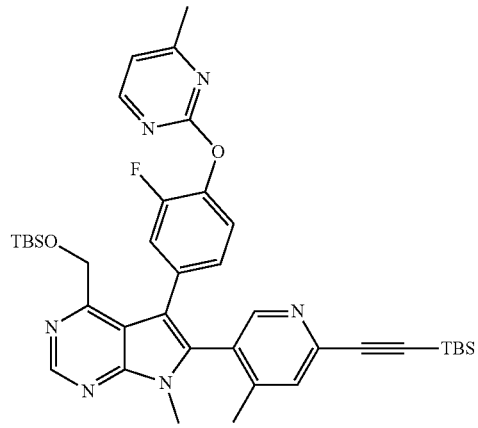

Step 8: A resealable reaction vial was charged with 2-[4-(6-bromo-4-{[(tert-butyldimethylsilyl)oxy]methyl}-7-methyl-7H-pyrrolo[2,3-d]pyrimidin-5-yl)-2-fluorophenoxy]-4-methylpyrimidine (350 mg, 0.63 mmol), 2-[2-(tert-butyldimethylsilyl)ethynyl]-4-methyl-5-(4,4,5,5-tetramethyl-1,3,2-dioxaborolan-2-yl)pyridine (893 mg, 2.50 mmol), Na2CO3 (198 mg, 1.87 mmol), Pd(PPh₃)₄ (144 mg, 0.1253 mmol) and a stirbar before being evacuated and purged with nitrogen three times. Dioxane/H₂O (20 mL) was added, and the mixture was stirred for 1 h at 90° C. The reaction mixture was diluted with water (50 mL), and the aqueous phase was extracted with DCM (50 mL) three times. The combined organic layers were washed with brine, dried over sodium sulfate, filtered, and concentrated in vacuo. The resulting crude material was purified by silica gel chromatography. Concentration in vacuo resulted in 2-[4-(6-{6-[2-(tert-butyldimethylsilyl)ethynyl]-4-methylpyridin-3-yl}-4-{[(tert-butyldimethylsilyl)oxy]methyl}-7-methyl-7H-pyrrolo[2,3-d]pyrimidin-5-yl)-2-fluorophenoxy]-4-methylpyrimidine (140 mg, 31%) as a yellow oil.

(6-(6-ethynyl-4-methylpyridin-3-yl)-5-(3-fluoro-4-((4-methylpyrimidin-2-yl)oxy)phenyl)-7-methyl-7H-pyrrolo[2,3-d]pyrimidin-4-yl)methanol Example 47

Scheme 44

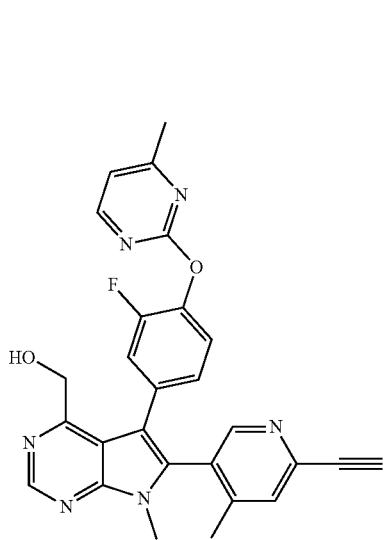 [SMILES: C#Cc1cc(C)c(-c2c(-c3ccc(Oc4nccc(C)n4)c(F)c3)c3c(CO)ncnc3n2C)cn1]

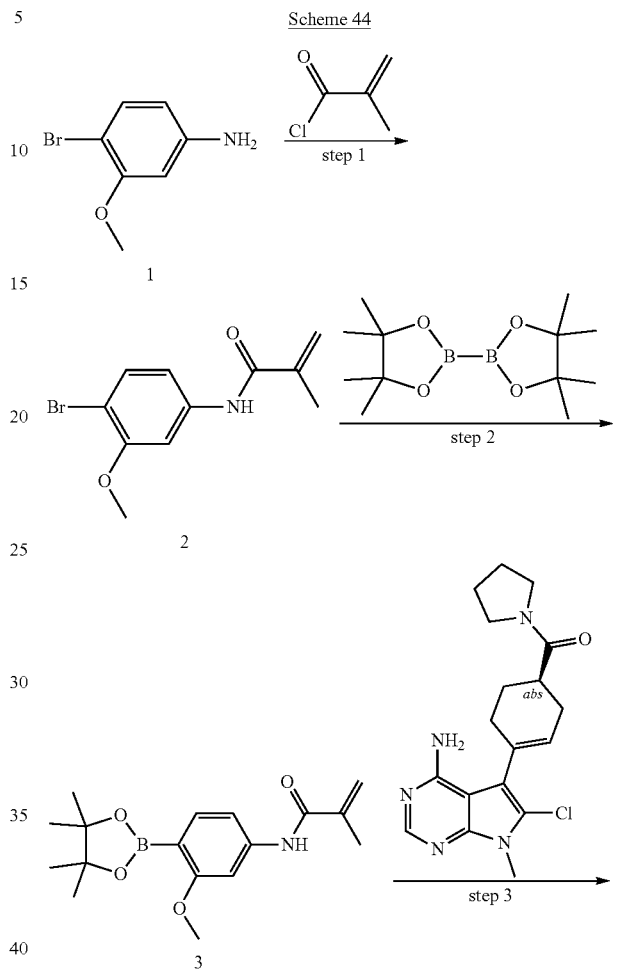

Step 9: A round bottomed flask was charged with 2-[4-(6-{6-[2-(tert-butyldimethylsilyl)ethynyl]-4-methylpyridin-3-yl}-4-{[(tert-butyldimethylsilyl)oxy]methyl}-7-methyl-7H-pyrrolo[2,3-d]pyrimidin-5-yl)-2-fluorophenoxy]-4-methylpyrimidine (130 mg, 0.18 mmol), THF (10 mL) and a stirbar. TBAF (0.45 mL, 0.45 mmol) was added, and the solution was stirred for 30 min at r.t. The resulting crude material was purified by prep-HPLC (Column: XBridge Shield RP18 OBD Column, 30*150 mm, 5 um; Mobile Phase A:Water(10 MMOL/L NH$_4$HCO$_3$+0.1% NH$_3$·H$_2$O), Mobile Phase B:ACN; Flow rate:60 mL/min; Gradient:20 B to 50 B in 8 min; 254/220 nm; RT1:7.28). Lyophilization yielded [6-(6-ethynyl-4-methylpyridin-3-yl)-5-{3-fluoro-4-[(4-methylpyrimidin-2-yl)oxy]phenyl}-7-methyl-7H-pyrrolo[2,3-d]pyrimidin-4-yl]methanol (39.4 mg, 46%) as an off-white amorphous solid.

TABLE 45

Exemplary Compound

| Compound | Structure | Proton NMR | MS [M + 1] |
|---|---|---|---|
| (6-(6-ethynyl-4-methylpyridin-3-yl)-5-(3-fluoro-4-((4-methylpyrimidin-2-yl)oxy)phenyl)-7-methyl-7H-pyrrolo[2,3-d]pyrimidin-4-yl)methanol | 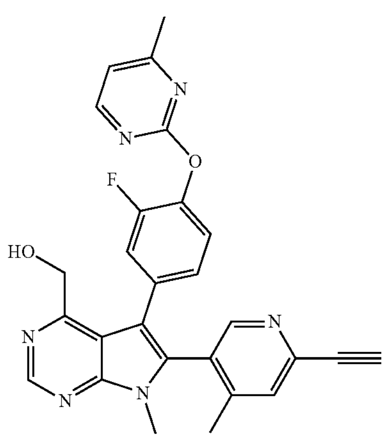 [SMILES: C#Cc1cc(C)c(-c2c(-c3ccc(Oc4nccc(C)n4)c(F)c3)c3c(CO)ncnc3n2C)cn1] | $^1$H NMR (400 MHz, DMSO-d$_6$) δ 8.92 (s, 1H), 8.55 (s, 1H), 8.49 (d, J = 5.0 Hz, 1H), 7.59 (s, 1H), 7.37-7.27 (m, 2H), 7.19 (d, J = 5.0 Hz, 1H), 7.13 (dd, J = 8.3, 2.2 Hz, 1H), 5.19 (s, 1H), 4.59-4.42 (m, 3H), 3.59 (s, 3H), 2.41 (s, 3H), 2.06 (s, 3H). | 481.25 |

-continued

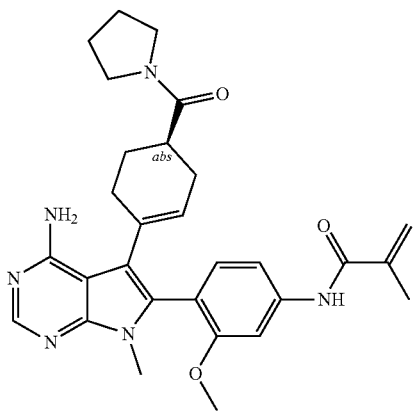

N-(4-bromo-3-methoxyphenyl)-2-methylprop-2-enamide

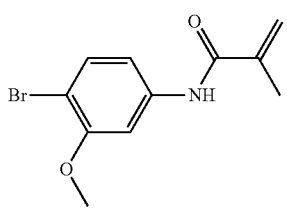

Step 1: A round bottomed flask was charged with 4-bromo-3-methoxyaniline (2.9 g, 14.3 mmol), dichloromethane (30 mL), TEA (4.33 g, 42.9 mmol) and a stir bar. 2-methylprop-2-enoyl chloride (1.64 g, 15.7 mmol) was added, and the solution was stirred for 1 h at 0° C. The reaction mixture was quenched with water, extracted with DCM, dried over Na$_2$SO$_4$, concentrated in vacuo. The resulting crude material was purified by silica gel chromatography. Concentration in vacuo resulted in N-(4-bromo-3-methoxyphenyl)-2-methylprop-2-enamide (3.1 g, 80.3%) as a yellow solid.

N-[3-methoxy-4-(4,4,5,5-tetramethyl-1,3,2-dioxaborolan-2-yl)phenyl]-2-methylprop-2-enamide

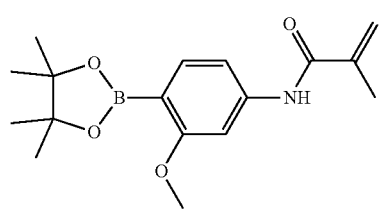 [SMILES: C=C(C)C(=O)Nc1ccc(B2OC(C)(C)C(C)(C)O2)c(OC)c1]

Step 2: A resealable reaction vial was charged with N-(4-bromo-3-methoxyphenyl)-2-methylprop-2-enamide (2.8 g, 10.3 mmol), 4,4,5,5-tetramethyl-2-(4,4,5,5-tetramethyl-1,3,2-dioxaborolan-2-yl)-1,3,2-dioxaborolane (5.23 g, 20.6 mmol), Pd(dppf)$_2$Cl$_2$ (753 mg, 1.03 mmol), AcOK (3.02 g, 30.9 mmol), and a stir bar before being evacuated and purged with nitrogen three times. Dioxane (30 mL) was added, and the mixture was stirred for 2 h at 90° C. The reaction mixture was quenched with water, extracted with DCM, dried over Na$_2$SO$_4$, concentrated in vacuo. The resulting crude material was purified by silica gel chromatography. Concentration in vacuo resulted in N-[3-methoxy-4-(4,4,5,5-tetramethyl-1,3,2-dioxaborolan-2-yl)phenyl]-2-methylprop-2-enamide (2.2 g, 67.4%) as a yellow solid.

N-(4-{4-amino-7-methyl-5-[(4R)-4-(pyrrolidine-1-carbonyl)cyclohex-1-en-1-yl]-7H-pyrrolo[2,3-d]pyrimidin-6-yl}-3-methoxyphenyl)-2-methylprop-2-enamide

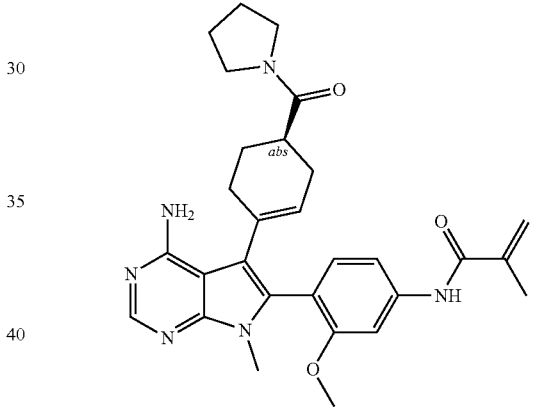

Step 3: A resealable reaction vial was charged with N-[3-methoxy-4-(4,4,5,5-tetramethyl-1,3,2-dioxaborolan-2-yl)phenyl]-2-methylprop-2-enamide (200 mg, 630 μmol), 6-chloro-7-methyl-5-[(4R)-4-(pyrrolidine-1-carbonyl)cyclohex-1-en-1-yl]-7H-pyrrolo[2,3-d]pyrimidin-4-amine (181 mg, 504 μmol), XPhos Pd G3 (53.3 mg, 63.0 μmol), XPhos (29.9 mg, 63.0 μmol), K$_3$PO$_4$ (398 mg, 1.88 mmol) and a stir bar before being evacuated and purged with nitrogen three times. DME/H$_2$O (6 mL) was added, and the mixture was stirred for 2 h at 90° C. The resulting crude material was purified by prep-HPLC (Column: XBridge Shield RP18 OBD Column, 30*150 mm, 5 um; Mobile Phase A:Water(10 MMOL/L NH$_4$HCO$_3$+0.1% NH$_3$·H$_2$O), Mobile Phase B:ACN; Flow rate:60 mL/min; Gradient:25 B to 50 B in 8 min; 254/220 nm; RT1:7.2). Lyophilization yielded N-(4-{4-amino-7-methyl-5-[(4R)-4-(pyrrolidine-1-carbonyl)cyclohex-1-en-1-yl]-7H-pyrrolo[2,3-d]pyrimidin-6-yl}-3-methoxyphenyl)-2-methylprop-2-enamide (70.0 mg, 27%) as an off-white amorphous solid.

TABLE 46

Exemplary Compounds

| Compound | Structure | Proton NMR | MS [M + 1] |
| --- | --- | --- | --- |
| (R)-N-(4-(4-amino-7-methyl-5-(4-(pyrrolidine-1-carbonyl)cyclohex-1-en-1-yl)-7H-pyrrolo[2,3-d]pyrimidin-6-yl)-3-methoxyphenyl)methacrylamide | 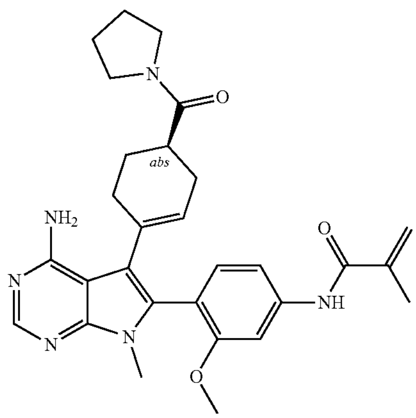 [SMILES: C=C(C)C(=O)Nc1ccc(-c2c(C3=CC[C@H](C(=O)N4CCCC4)CC3)c3c(N)ncnc3n2C)c(OC)c1] | ¹H NMR (400 MHz, DMSO-d₆) δ 9.94 (s, 1H), 8.08 (d, J = 1.0 Hz, 1H), 7.64 (dd, J = 7.0, 1.9 Hz, 1H), 7.39 (ddd, J = 8.0, 5.9, 1.9 Hz, 1H), 7.15 (dd, J = 8.2, 3.5 Hz, 1H), 6.54 (s, 1H), 6.35 (s, 1H), 5.85 (t, J = 1.1 Hz, 1H), 5.66 (d, J = 22.8 Hz, 1H), 5.56 (s, 1H), 3.76 (d, J = 2.7 Hz, 3H), 3.46 (ddt, J = 18.3, 11.7, 6.1 Hz, 2H), 3.39 (d, J = 3.0 Hz, 3H), 3.31 (s, 2H), 2.84-2.64 (m, 1H), 2.42-2.02 (m, 3H), 1.98 (t, J = 1.3 Hz, 3H), 1.94-1.80 (m, 3H), 1.78-1.68 (m, 3H), 1.64-1.36 (m, 1H). | 515.30 |
| N-(4-(4-amino-7-methyl-5-((R)-4-((R)-2-methylpyrrolidine-1-carbonyl)cyclohex-1-en-1-yl)-7H-pyrrolo[2,3-d]pyrimidin-6-yl)-3-methylphenyl)methacrylamide | 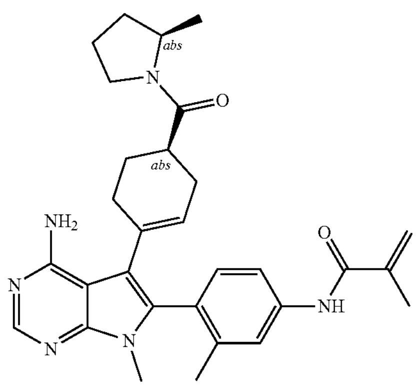 [SMILES: C=C(C)C(=O)Nc1ccc(-c2c(C3=CC[C@H](C(=O)N4CCC[C@H]4C)CC3)c3c(N)ncnc3n2C)c(C)c1] | ¹H NMR (400 MHz, DMSO-d₆) δ 9.85 (s, 1H), 8.16-8.01 (m, 1H), 7.71 (d, J = 2.3 Hz, 1H), 7.62 (dt, J = 8.3, 2.0 Hz, 1H), 7.25-7.12 (m, 1H), 6.56 (s, 2H), 5.83 (s, 1H), 5.67 (ddt, J = 17.5, 4.3, 2.2 Hz, 1H), 5.54 (t, J = 1.5 Hz, 1H), 4.10-3.93 (m, 1H), 3.46 (td, J = 6.9, 2.5 Hz, 2H), 3.34 (d, J = 2.7 Hz, 3H), 2.80-2.64 (m, 1H), 2.38-1.97 (t, J = 1.2 Hz, 3H), 1.90 (dddt, J = 10.3, 7.0, 5.3, 3.1 Hz, 3H), 1.83-1.70 (m, 2H), 1.67-1.41 (m, 3H), 1.15-1.00 (m, 3H). | 513.35 |
| (R)-N-(4-(4-amino-7-methyl-5-(4-(pyrrolidine-1-carbonyl)cyclohex-1-en-1-yl)-7H-pyrrolo[2,3-d]pyrimidin-6-yl)-3-fluoro-5-methylphenyl)methacrylamide | 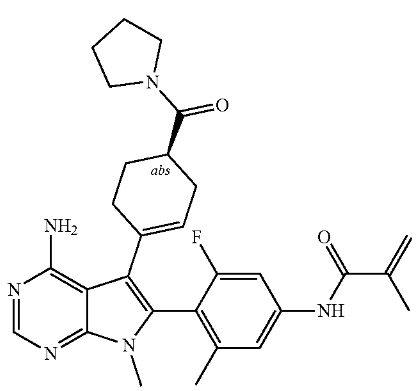 [SMILES: C=C(C)C(=O)Nc1cc(C)c(-c2c(C3=CC[C@H](C(=O)N4CCCC4)CC3)c3c(N)ncnc3n2C)c(F)c1] | ¹H NMR (400 MHz, DMSO-d₆) δ 10.05 (s, 1H), 8.13 (d, J = 2.9 Hz, 1H), 7.65 (dt, J = 11.8, 2.1 Hz, 1H), 7.52 (d, J = 2.3 Hz, 1H), 6.68-6.57 (s, 1H), 5.85 (s, 1H), 5.65 (d, J = 3.9 Hz, 1H), 5.59 (s, 1H), 3.51-3.41 (m, 2H), 3.42 (s, 3H), 3.26 (t, J = 6.9 Hz, 2H), 2.85-2.78 (m, 2H) 2.19 (s, 2H), 2.05 (s, 3H), 1.97 (d, J = 1.2 Hz, 5H), 1.86 (p, J = 6.8 Hz, 2H), 1.76 (q, J = 6.7 Hz, 2H), 1.61 (d, J = 4.1 Hz, 2H). | 517.30 |

TABLE 46-continued

Exemplary Compounds

| Compound | Structure | Proton NMR | MS [M + 1] |
|---|---|---|---|
| (S)-N-(4-(4-amino-7-methyl-5-(4-(pyrrolidine-1-carbonyl)cyclohex-1-en-1-yl)-7H-pyrrolo[2,3-d]pyrimidin-6-yl)-3-fluoro-5-methylphenyl)methacrylamide | 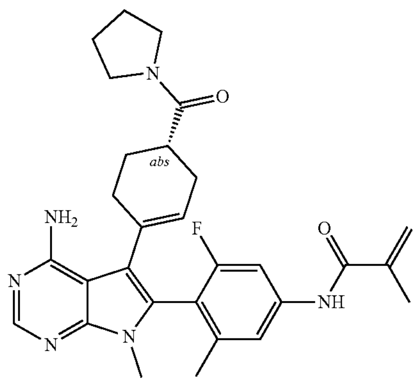 [SMILES: C=C(C)C(=O)Nc1cc(C)c(-c2c(C3=CC[C@@H](C(=O)N4CCCC4)CC3)c3c(N)ncnc3n2C)c(F)c1] | ¹H NMR (400 MHz, DMSO-d₆) δ 10.04 (s, 1H), 8.12 (d, J = 3.4 Hz, 1H), 7.64 (d, J = 11.6 Hz, 1H), 7.51 (s, 1H), 6.62 (s, 1H), 5.85 (s, 1H), 5.65 (s, 1H), 5.59 (d, J = 1.8 Hz, 1H), 2.75 (s, 1H), 2.19 (s, 2H), 2.05 (s, 3H), 2.00-1.94 (m, 5H), 1.85 (q, J = 6.7 Hz, 2H), 1.76 (q, J = 6.8 Hz, 2H), 1.61 (s, 2H). | 517.45 |

Example 48

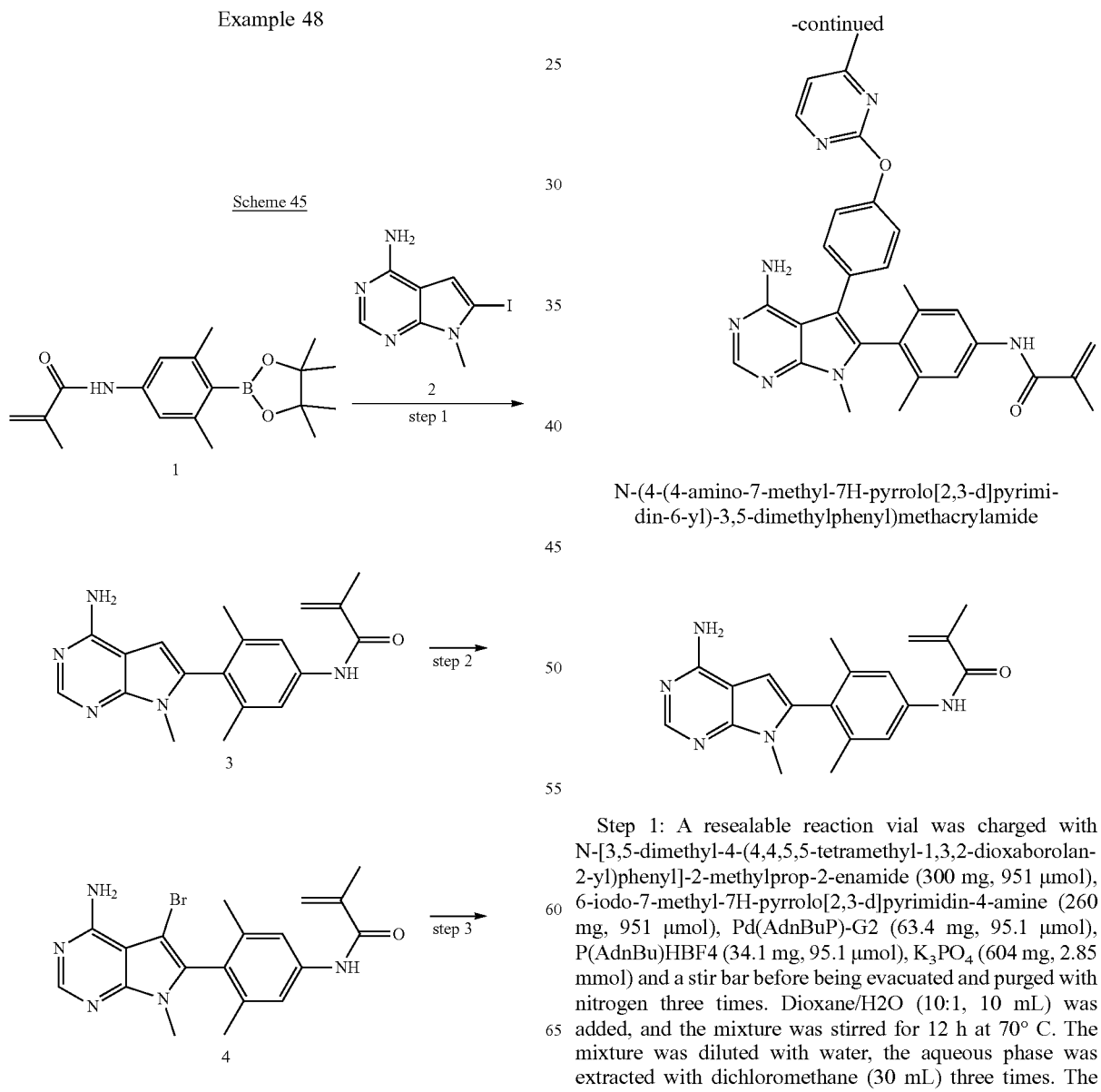

N-(4-(4-amino-7-methyl-7H-pyrrolo[2,3-d]pyrimidin-6-yl)-3,5-dimethylphenyl)methacrylamide Step 1: A resealable reaction vial was charged with N-[3,5-dimethyl-4-(4,4,5,5-tetramethyl-1,3,2-dioxaborolan-2-yl)phenyl]-2-methylprop-2-enamide (300 mg, 951 μmol), 6-iodo-7-methyl-7H-pyrrolo[2,3-d]pyrimidin-4-amine (260 mg, 951 μmol), Pd(AdnBuP)-G2 (63.4 mg, 95.1 μmol), P(AdnBu)HBF4 (34.1 mg, 95.1 μmol), K₃PO₄ (604 mg, 2.85 mmol) and a stir bar before being evacuated and purged with nitrogen three times. Dioxane/H2O (10:1, 10 mL) was added, and the mixture was stirred for 12 h at 70° C. The mixture was diluted with water, the aqueous phase was extracted with dichloromethane (30 mL) three times. The combined organic layers were washed with brine, dried over sodium sulfate, filtered, and concentrated in vacuo. The resulting crude material was purified by prep-TLC (dichloromethane/methanol; 15:1). Concentration in vacuo resulted in N-(4-{4-amino-7-methyl-7H-pyrrolo[2,3-d]pyrimidin-6-yl}-3,5-dimethylphenyl)-2-methylprop-2-enamide (180 mg, 59%) as a yellow solid.

N-(4-(4-amino-5-bromo-7-methyl-7H-pyrrolo[2,3-d]pyrimidin-6-yl)-3,5-dimethylphenyl)methacrylamide

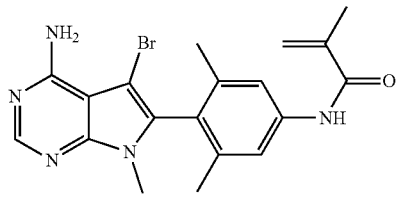 [SMILES: C=C(C)C(=O)Nc1cc(C)c(-c2c(Br)c3c(N)ncnc3n2C)c(C)c1]

Step 2: A round bottomed flask was charged with N-(4-{4-amino-7-methyl-7H-pyrrolo[2,3-d]pyrimidin-6-yl}-3,5-dimethylphenyl)-2-methylprop-2-enamide (180 mg, 536 μmol), dimethylformamide (5 mL) and a stir bar. NBS (95.4 mg, 536 μmol) was added, and the solution was stirred for 0.5 h at r.t. The mixture was quenched with NaHSO₃ aq., and extracted with DCM (3*20 mL), The organic phase was combined and concentrated. The resulting crude material was purified by prep-TLC (DCM/MeOH=15:1) resulted in N-(4-{4-amino-5-bromo-7-methyl-7H-pyrrolo[2,3-d]pyrimidin-6-yl}-3,5-dimethylphenyl)-2-methylprop-2-enamide (160 mg, 72%) as a brown solid.

N-(4-(4-amino-7-methyl-5-(4-((4-methylpyrimidin-2-yl)oxy)phenyl)-7H-pyrrolo[2,3-d]pyrimidin-6-yl)-3,5-dimethylphenyl)methacrylamide

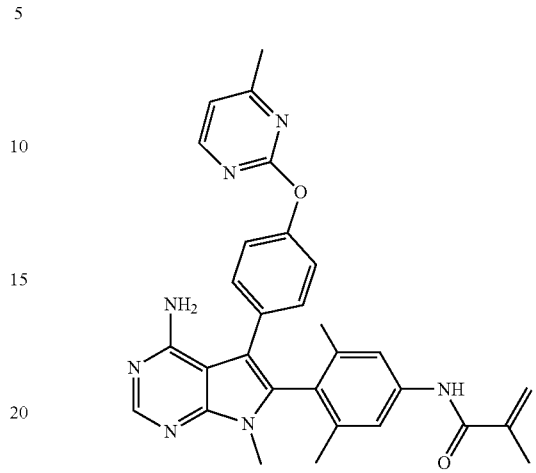

Step 3: A resealable reaction vial was charged with N-(4-{4-amino-5-bromo-7-methyl-7H-pyrrolo[2,3-d]pyrimidin-6-yl}-3,5-dimethylphenyl)-2-methylprop-2-enamide (150 mg, 362 μmol), 4-methyl-2-[4-(4,4,5,5-tetramethyl-1,3,2-dioxaborolan-2-yl)phenoxy]pyrimidine (113 mg, 362 μmol), Pd(dppf)Cl₂ (26.4 mg, 36.2 μmol), K₃PO₄ (228 mg, 1.08 mmol), and a stir bar before being evacuated and purged with nitrogen three times. DME/H₂O (8 mL) was added, and the mixture was stirred for 1 h at 90° C. The reaction mixture was diluted with water (50 mL), and the aqueous phase was extracted with EtOAc (30 mL) three times. The combined organic layers were washed with brine dried over sodium sulfate, filtered, and concentrated in vacuo. The resulting crude material was purified by HPLC (Column: YMC-Actus Triart C18, 30*250, 5 um; Mobile Phase A:undefined, Mobile Phase B:undefined; Flow rate:50 mL/min; Gradient:45 B to 70 B in 8 min; 220 nm; RT1: 7.23). Lyophilization yielded N-[4-(4-amino-7-methyl-5-{4-[(4-methylpyrimidin-2-yl)oxy]phenyl}-7H-pyrrolo[2,3-d]pyrimidin-6-yl)-3,5-dimethylphenyl]-2-methylprop-2-enamide (18.2 mg, 10%) as a white amorphous solid.

TABLE 47

Exemplary Compounds

| Compound | Structure | Proton NMR | MS [M + 1] |
|---|---|---|---|
| N-(4-(4-amino-7-methyl-5-(4-((4-methylpyrimidin-2-yl)oxy)phenyl)-7H-pyrrolo[2,3-d]pyrimidin-6-yl)-3,5-dimethylphenyl)methacrylamide | 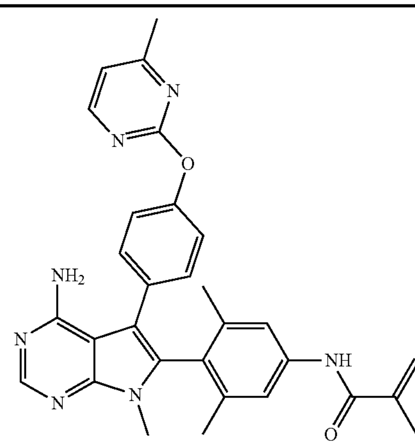 | ¹H NMR (400 MHz, DMSO-d₆) δ 9.74 (s, 1H), 8.45 (d, J = 5.0 Hz, 1H), 8.21 (s, 1H), 7.50 (s, 2H), 7.28-7.10 (m, 5H), 5.80 (m, 2H), 5.52 (s, 1H), 3.37 (s, 3H), 2.40 (s, 3H), 1.96 (m, 9H). | 520.40 |

TABLE 47-continued

Exemplary Compounds

| Compound | Structure | Proton NMR | MS [M + 1] |
|---|---|---|---|
| N-(4-(4-amino-5-(3-fluoro-4-((4-methylpyrimidin-2-yl)oxy)phenyl)-7-methyl-7H-pyrrolo[2,3-d]pyrimidin-6-yl)-3,5-dimethylphenyl)methacrylamide | | $^1$H NMR (400 MHz, DMSO-d6) δ 8.67 (d, J = 7.5 Hz, 1H), 8.48 (d, J = 5.0 Hz, 1H), 8.25-8.09 (m, 1H), 7.57-7.41 (m, 2H), 7.36-6.94 (m, 4H), 6.02-5.62 (m, 1H), 5.43 (s, 1H), 5.34 (t, J = 1.6 Hz, 1H), 3.78 (s, 3H), 2.42 (s, 3H), 2.10 (s, 3H), 1.85 (s, 3H), 1.78 (d, J = 1.2 Hz, 3H). | 538.30 |
| (S)-N-(4-(4-amino-7-methyl-5-(4-(pyrrolidine-1-carbonyl)cyclohex-1-en-1-yl)-7H-pyrrolo[2,3-d]pyrimidin-6-yl)-3,5-dimethylphenyl)methacrylamide<br><br>atropisomer 1 | | $^1$H NMR (400 MHz, DMSO-d$_6$) δ 8.64 (d, J = 5.8 Hz, 1H), 8.14 (d, J = 1.9 Hz, 1H), 7.74 (dd, J = 18.2, 10.8 Hz, 1H), 7.10 (d, J = 6.0 Hz, 1H), 5.84-5.74 (m, 1H), 5.65 (s, 1H), 5.54-5.47 (m, 1H), 3.76 (s, 3H), 3.59-3.43 (m, 2H), 2.78-2.62 (m, 1H), 2.37-2.14 (m, 3H), 2.10-1.99 (m, 9H), 1.99-1.91 (m, 5H), 1.88 (d, J = 14.7 Hz, 2H), 1.79 (p, J = 6.7 Hz, 1H), 1.24 (s, 1H). | 513.40 |
| (S)-N-(4-(4-amino-7-methyl-5-(4-(pyrrolidine-1-carbonyl)cyclohex-1-en-1-yl)-7H-pyrrolo[2,3-d]pyrimidin-6-yl)-3,5-dimethylphenyl)methacrylamide<br><br>atropisomer 2 | | $^1$H NMR (400 MHz, DMSO-d$_6$) δ 8.64 (s, 1H), 8.13 (s, 1H), 7.72 (d, J = 9.4 Hz, 1H), 7.08 (d, J = 1.3 Hz, 1H), 5.80 (d, J = 16.7 Hz, 1H), 5.76 (s, 1H), 5.66 (d, J = 23.7 Hz, 1H), 5.53-5.49 (m, 1H), 3.76 (s, 3H), 3.48 (dt, J = 24.2, 8.0 Hz, 2H), 3.17 (d, J = 5.2 Hz, 1H), 2.77-2.63 (m, 1H), 2.30 (d, J = 26.8 Hz, 3H), 2.08 (s, 2H), 2.01 (d, J = 6.9 Hz, 8H), 1.96 (d, J = 10.0 Hz, 5H), 1.92-1.81 (m, 2H), 1.78 (q, J = 6.7 Hz, 1H), 1.29-1.15 (m, 1H). | 513.40 |

TABLE 47-continued

Exemplary Compounds

| Compound | Structure | Proton NMR | MS [M + 1] |
|---|---|---|---|
| (R)-N-(4-(4-amino-7-methyl-5-(4-(pyrrolidine-1-carbonyl)cyclohex-1-en-1-yl)-7H-pyrrolo[2,3-d]pyrimidin-6-yl)-3,5-dimethylphenyl)methacrylamide | atropisomer 1 | $^1$H NMR (400 MHz, DMSO-$d_6$) δ 8.64 (d, J = 6.1 Hz, 1H), 8.13 (d, J = 1.6 Hz, 1H), 7.72 (d, J = 16.7 Hz, 1H), 7.08 (d, J = 6.0 Hz, 1H), 5.78 (t, J = 10.2 Hz, 1H), 5.65 (s, 1H), 5.51 (dt, J = 6.3, 1.5 Hz, 1H), 3.76 (s, 3H), 3.53-3.41 (m, 2H), 3.30-3.28 (m, 1H), 2.80-2.61 (m, 1H), 2.36-2.21 (m, 3H), 2.08 (s, 1H), 2.05-2.00 (m, 5H), 1.98-1.95 (m, 3H), 1.89 (q, J = 7.3, 6.8 Hz, 4H), 1.78 (q, J = 6.7 Hz, 2H), 1.67 (d, J = 8.6 Hz, 1H), 1.28-1.15 (m, 1H). | 513.35 |
| (R)-N-(4-(4-amino-7-methyl-5-(4-(pyrrolidine-1-carbonyl)cyclohex-1-en-1-yl)-7H-pyrrolo[2,3-d]pyrimidin-6-yl)-3,5-dimethylphenyl)methacrylamide | atropisomer 2 | $^1$H NMR (400 MHz, DMSO-$d_6$) δ 8.64 (d, J = 2.4 Hz, 1H), 8.13 (s, 1H), 7.73 (d, J = 7.9 Hz, 1H), 7.07 (d, J = 1.4 Hz, 1H), 5.82 (s, 1H), 5.77 (d, J = 6.7 Hz, 1H), 5.69 (s, 1H), 5.63 (s, 1H), 5.51 (d, J = 7.0 Hz, 1H), 3.76 (s, 3H), 3.57-3.38 (m, 3H), 2.76 (s, 1H), 2.67 (d, J = 1.9 Hz, 1H), 2.34-2.23 (m, 2H), 2.12 (s, 1H), 2.08 (s, 1H), 2.02 (s, 5H), 2.01-1.97 (m, 3H), 1.95 (s, 5H), 1.89 (d, J = 14.7 Hz, 2H), 1.79 (p, J = 6.7 Hz, 1H), 1.24 (s, 2H). | 513.35 |

Example 49

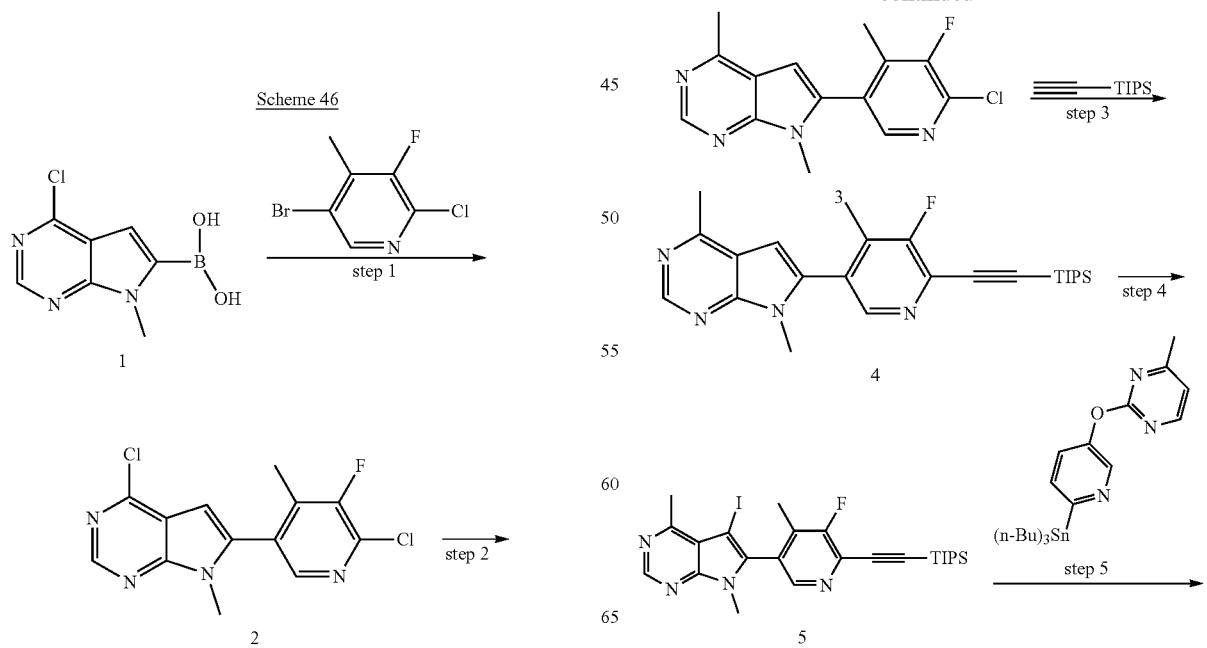

-continued

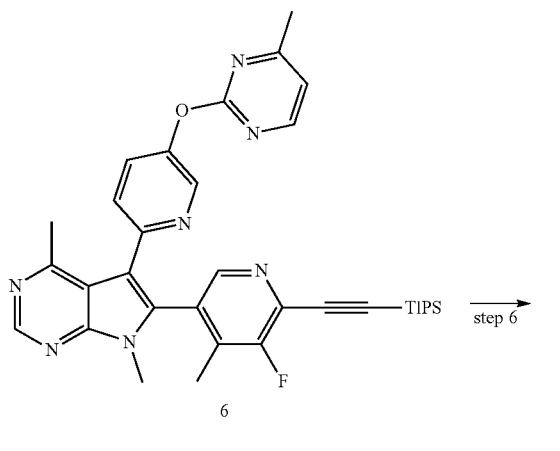

6

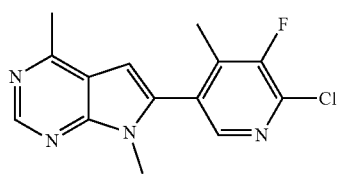 step 6

4-chloro-6-(6-chloro-5-fluoro-4-methylpyridin-3-yl)-7-methyl-7H-pyrrolo[2,3-d]pyrimidine

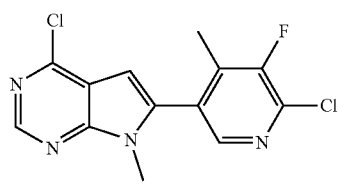

Step 1: A resealable reaction via was charged with (4-chloro-7-methyl-7H-pyrrolo[2,3-d]pyrimidin-6-yl)boronic acid (2 g, 9.48 mmol), 5-bromo-2-chloro-3-fluoro-4-methylpyridine (2.3 g, 10.4 mmol), Pd(dtbpf)Cl$_2$ (617 mg, 0.948 µmol), K$_3$PO$_4$ (6 g, 28.44 mmol) and a stir bar before being evacuated and purged with nitrogen three times. Dioxane:water=5:1 (40 mL) was added, and the solution was stirred for 2 h at 70° C. The reaction mixture was quenched with water, extracted with DCM, dried over Na$_2$SO$_4$, concentrated in vacuo. evaporated in vacuo, the residue was purified by silica gel column chromatography, eluted with PE/EA (30:1~1:1) to 4-chloro-6-(6-chloro-5-fluoro-4-methylpyridin-3-yl)-7-methyl-7H-pyrrolo[2,3-d]pyrimidine (1.3 g, 44%) as a yellow amorphous solid.

6-(6-chloro-5-fluoro-4-methylpyridin-3-yl)-4,7-dimethyl-7H-pyrrolo[2,3-d]pyrimidine

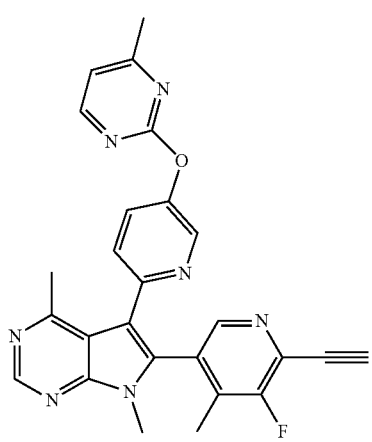 [SMILES: C#Cc1ncc(-c2c(-c3ccc(Oc4nccc(C)n4)cn3)c3c(C)ncnc3n2C)c(C)c1F]

Step 2: A resealable reaction via was charged with 4-chloro-6-(6-chloro-5-fluoro methylpyridin-3-yl)-7-methyl-7H-pyrrolo[2,3-d]pyrimidine (1.28 g, 4.13 mmol), Pd(PPh$_3$)$_4$ (478 mg, 0.413 mmol), DMF (20 mL) and a stir bar before being evacuated and purged with nitrogen three times. Zn(CH$_3$)$_2$ (2 M, 1.4 mL) was added, and the solution was stirred for 2 h at 90° C. The reaction mixture was quenched with water, extracted with DCM, dried over Na$_2$SO$_4$, concentrated in vacuo. The residue was purified by silica gel column chromatography, eluted with PE/EA (30:1~1:2) to 6-(6-chloro-5-fluoro-4-methylpyridin-3-yl)-4,7-dimethyl-7H-pyrrolo[2,3-d]pyrimidine (420 mg, 68%) as a yellow amorphous solid.

6-(5-fluoro-4-methyl-6-((triisopropylsilyl)ethynyl)pyridin-3-yl)-4,7-dimethyl-7H-pyrrolo[2,3-d]pyrimidine

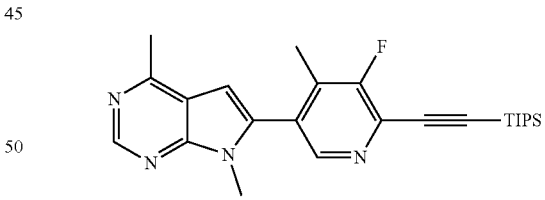

Step 3: A resealable reaction via was charged with 6-(6-chloro-5-fluoro-4-methylpyridin-3-yl)-4,7-dimethyl-7H-pyrrolo[2,3-d]pyrimidine (1.28 g, 4.13 mmol), Pd(PPh$_3$)$_2$Cl$_2$ (580 mg, 0.826 mmol), CuI (313 mg, 1.65 mmol), ethynyltriisopropylsilane (526 mg, 2.89 mmol), TEA (1.25 g, 12.39 mmol) and a stir bar before being evacuated and purged with nitrogen three times. DMF (20 mL) was added, and the solution was stirred for 2 h at 90° C. The reaction mixture was quenched with water, extracted with DCM, dried over Na$_2$SO$_4$, concentrated in vacuo. The resulted mixture was purified through C18 Column. Concentration in vacuo resulted in 6-(6-chloro-5-fluoro-4-methylpyridin-3-yl)-4,7-dimethyl-7H-pyrrolo[2,3-d]pyrimidine (720 mg, 40%) as a yellow amorphous solid.

6-(5-fluoro-4-methyl-6-((triisopropylsilyl)ethynyl)
pyridin-3-yl)-5-iodo-4,7-dimethyl-7H-pyrrolo[2,3-d]
pyrimidine

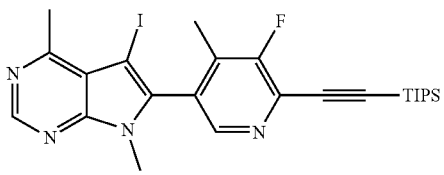

Step 4: A round bottomed flask was charged with 6-(5-fluoro-4-methyl-6-((triisopropylsilyl)ethynyl)pyridin-3-yl)-4,7-dimethyl-7H-pyrrolo[2,3-d]pyrimidine (400 mg, 1.60 mmol), DCM (8 mL), added TFA (547 mg, 4.8 mmol) and a stir bar. NIS (396 mg, 1.76 mmol) was added, and the solution was stirred for 1 h at room temperature. The reaction mixture was quenched with water, extracted with DCM, dried over Na$_2$SO$_4$, concentrated in vacuo. The resulting crude material was purified by silica gel chromatography. Concentration in vacuo resulted in 46-(5-fluoro-4-methyl-6-((triisopropylsilyl)ethynyl)pyridin-3-yl)-5-iodo-4,7-dimethyl-7H-pyrrolo[2,3-d]pyrimidine (760 mg, 85%) as a yellow amorphous solid.

6-(5-fluoro-4-methyl-6-((triisopropylsilyl)ethynyl)
pyridin-3-yl)-4,7-dimethyl-5-(5-((4-methylpyrimi-
din-2-yl)oxy)pyridin-2-yl)-7H-pyrrolo[2,3-d]pyrimi-
dine

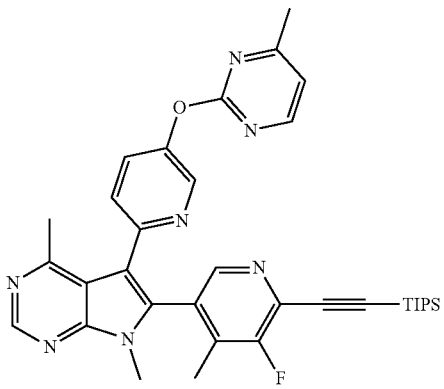

Step 5: A round bottomed flask was charged with 6-(5-fluoro-4-methyl-6-((triisopropylsilyl)ethynyl)pyridin-3-yl)-5-iodo-4,7-dimethyl-7H-pyrrolo[2,3-d]pyrimidine (740 mg, 1.32 mmol), 4-methyl-2-((6-(tributylstannyl)pyridin-3-yl)oxy)pyrimidine (1.26 g, 2.64 mmol), Pd(PPh$_3$)$_4$ (153 mg, 0.132 mmol), CuI (50 mg, 0.264 umol) and a stir bar before being evacuated and purged with nitrogen three times. DMF (15 mL) was added, and the solution was stirred for 2 h at 90° C. The reaction mixture in vacuo. The resulting crude material was purified by prep-TLC. Concentration in vacuo resulted in 6-(5-fluoro-4-methyl-6-((triisopropylsilyl)ethynyl)pyridin-3-yl)-4,7-dimethyl-5-(5-((4-methylpyrimidin yl)oxy)pyridin-2-yl)-7H-pyrrolo[2,3-d]pyrimidine (540 mg, 66%) as a yellow amorphous soli.

6-(6-ethynyl-5-fluoro-4-methylpyridin-3-yl)-4,7-
dimethyl-5-(5-((4-methylpyrimidin-2-yl)oxy)pyri-
din-2-yl)-7H-pyrrolo[2,3-d]pyrimidine

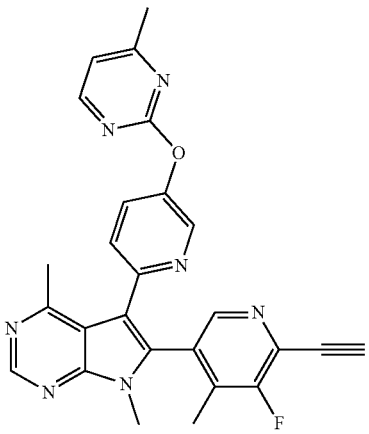

Step 6: A round bottomed flask was charged with 6-(5-fluoro-4-methyl-6-((triisopropylsilyl)ethynyl)pyridin-3-yl)-4,7-dimethyl-5-(5-((4-methylpyrimidin-2-yl)oxy)pyridin-2-yl)-7H-pyrrolo[2,3-d]pyrimidine (520 mg, 0.84 mmol), THF (8 mL) and a stir bar. TBAF (1 mL, 1 mmol) was added, and the solution was stirred for 1 h at room temperature. The reaction mixture was diluted with water, extracted with DCM, dried over Na$_2$SO$_4$, concentrated in vacuo. The residue was purified by prep-HPLC (Column: XBridge Shield RP18 OBD Column, 30*150 mm, 5 um; Mobile Phase A:Water(10 MMOL/L NH$_4$HCO$_3$+0.1% NH$_3$·H$_2$O), Mobile Phase B:ACN; Flow rate:60 mL/min; Gradient:20 B to 45 B in 8 min; 254/220 nm; RT1:7.77). Lyophilization yielded 6-(6-ethynyl-5-fluoro-4-methylpyridin-3-yl)-4,7-dimethyl-5-(5-((4-methylpyrimidin-2-yl)oxy)pyridin-2-yl)-7H-pyrrolo[2,3-d]pyrimidine (213.2 mg, 55%) as a white amorphous solid.

TABLE 48

Exemplary Compounds

| Compound | Structure | Proton NMR | MS [M + 1] |
|---|---|---|---|
| 6-(6-ethynyl-5-fluoro-4-methylpyridin-3-yl)-4,7-dimethyl-5-(5-((4-methylpyrimidin-2-yl)oxy)pyridin-2-yl)-7H-pyrrolo[2,3-d]pyrimidine | 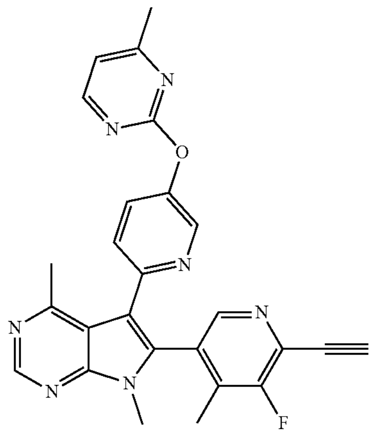 [SMILES: C#Cc1ncc(-c2c(-c3ccc(Oc4nccc(C)n4)cn3)c3c(C)ncnc3n2C)c(C)c1F] | 1H NMR (400 MHz, DMSO-d6) δ 8.81 (s, 1H), 8.54 (d, J = 2.7 Hz, 1H), 8.50 (d, J = 5.0 Hz, 1H), 8.43 (s, 1H), 7.61 (dd, J = 8.5, 2.8 Hz, 1H), 7.27 (d, J = 8.5 Hz, 1H), 7.19 (d, J = 5.0 Hz, 1H), 4.82 (d, J = 0.8 Hz, 1H), 3.63 (s, 3H), 2.40 (s, 3H), 1.98 (d, J = 2.1 Hz, 3H). | 446.15 |
| 6-(6-ethynyl-4-methoxypyridin-3-yl)-7-methyl-5-(5-((4-methylpyrimidin-2-yl)oxy)pyridin-2-yl)-7H-pyrrolo[2,3-d]pyrimidin-4-amine | 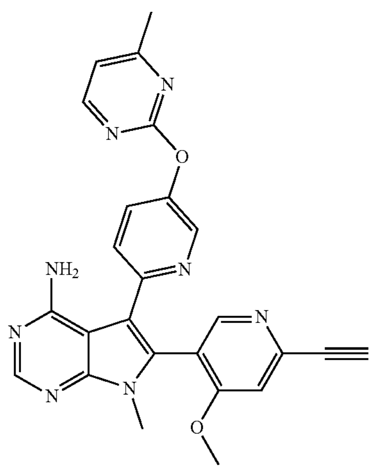 [SMILES: C#Cc1cc(OC)c(-c2c(-c3ccc(Oc4nccc(C)n4)cn3)c3c(N)ncnc3n2C)cn1] | $^1$H NMR (400 MHz, DMSO-$d_6$) δ 8.59 (d, J = 2.8 Hz, 1H), 8.48 (d, J = 5.0 Hz, 1H), 8.26 (s, 1H), 8.19 (s, 1H), 7.56-7.49 (m, 1H), 7.51 (s, 1H), 7.19 (d, J = 5.0 Hz, 1H), 6.88 (d, J = 8.7 Hz, 1H), 4.49 (s, 1H), 3.89 (s, 3H), 3.48 (s, 3H), 2.42 (s, 3H). | 465.20 |
| 6-(6-ethynyl-5-fluoro-4-methoxypyridin-3-yl)-7-methyl-5-(5-((4-methylpyrimidin-2-yl)oxy)pyridin-2-yl)-7H-pyrrolo[2,3-d]pyrimidin-4-amine | 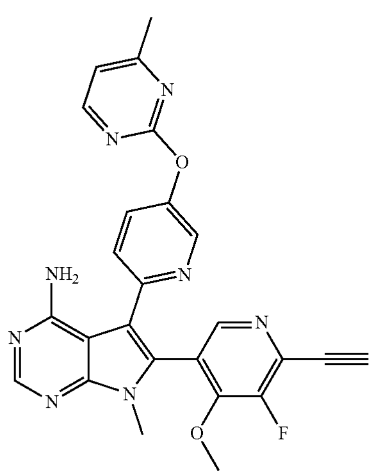 | $^1$H NMR (400 MHz, DMSO-$d_6$) δ 8.59 (d, J = 2.9 Hz, 1H), 8.49 (d, J = 5.0 Hz, 1H), 8.16 (s, 1H), 8.07 (s, 1H), 7.61 (dd, J = 8.8, 2.8 Hz, 1H), 7.27 (d, J = 9.0 Hz, 1H), 7.20 (d, J = 5.0 Hz, 1H), 5.60 (d, J = 0.9 Hz, 1H), 3.75 (s, 3H), 3.52 (s, 3H), 2.43 (s, 3H). | 483.15 |

TABLE 48-continued

Exemplary Compounds

| Compound | Structure | Proton NMR | MS [M + 1] |
|---|---|---|---|
| 6-(6-ethynyl-4-methoxypyridin-3-yl)-5-(2-fluoro-4-((4-methylpyrimidin-2-yl)oxy)phenyl)-4,7-dimethyl-7H-pyrrolo[2,3-d]pyrimidine | 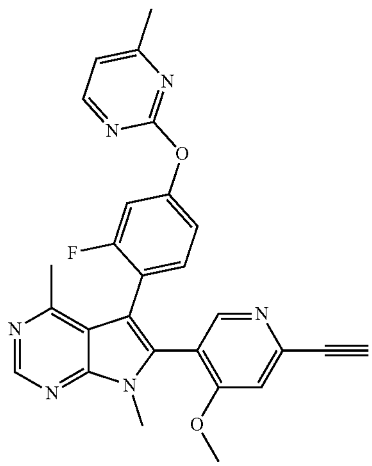 | $^1$H NMR (400 MHz, DMSO-d$_6$) δ 8.77 (s, 1H), 8.50 (d, J = 5.0 Hz, 1H), 8.23 (d, J = 97.8 Hz, 1H), 7.46 (d, J = 19.1 Hz, 1H), 7.38 (s, 1H), 7.33-6.95 (m, 3H), 4.47 (d, J = 3.7 Hz, 1H), 3.91 (s, 3H), 3.64 (d, J = 9.7 Hz, 3H), 2.42 (s, 3H), 2.38 (s, 3H). | 481.15 |
| 6-(6-ethynyl-4-methylpyridin-3-yl)-5-(3-fluoro-5-((4-methylpyrimidin-2-yl)oxy)pyridin-2-yl)-7-methyl-7H-pyrrolo[2,3-d]pyrimidin-4-amine | 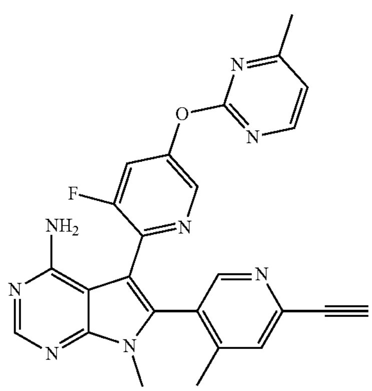 [SMILES: C#Cc1cc(C)c(-c2c(-c3ncc(Oc4nccc(C)n4)cc3F)c3c(N)ncnc3n2C)cn1] | $^1$H NMR (400 MHz, DMSO-d$_6$) δ 8.62-8.56 (m, 1H), 8.52 (d, J = 5.0 Hz, 1H), 8.36 (s, 1H), 8.28 (s, 1H), 7.77 (dd, J = 11.0, 2.3 Hz, 1H), 7.61 (s, 1H), 7.23 (d, J = 5.1 Hz, 1H), 7.02 (s, 1H), 4.42 (s, 1H), 3.52 (s, 3H), 2.43 (s, 3H), 2.05 (s, 3H). | 467.30 |
| 6-(6-ethynyl-4-methoxy-2-methylpyridin-3-yl)-5-(3-fluoro-5-((4-methylpyrimidin-2-yl)oxy)pyridin-2-yl)-7-methyl-7H-pyrrolo[2,3-d]pyrimidin-4-amine | 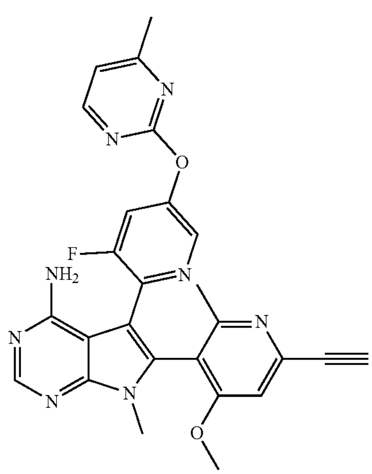 [SMILES: C#Cc1cc(OC)c(-c2c(-c3ncc(Oc4nccc(C)n4)cc3F)c3c(N)ncnc3n2C)c(C)n1] | $^1$H NMR (400 MHz, DMSO-d$_6$) δ 8.58 (s, 1H), 8.53 (d, J = 5.0 Hz, 1H), 8.23 (s, 1H), 7.76 (dd, J = 11.0, 2.3 Hz, 1H), 7.30 (s, 1H), 7.23 (d, J = 5.0 Hz, 1H), 6.87 (s, 1H), 4.41 (s, 1H), 3.84 (s, 3H), 3.46 (s, 3H), 2.43 (s, 3H), 1.92 (s, 3H), 1.24 (s, 1H). | 497.20 |

TABLE 48-continued

Exemplary Compounds

| Compound | Structure | Proton NMR | MS [M + 1] |
|---|---|---|---|
| 6-(6-ethynyl-4-methoxypyridin-3-yl)-5-(3-fluoro-5-((4-methylpyrimidin-2-yl)oxy)pyridin-2-yl)-7-methyl-7H-pyrrolo[2,3-d]pyrimidin-4-amine | 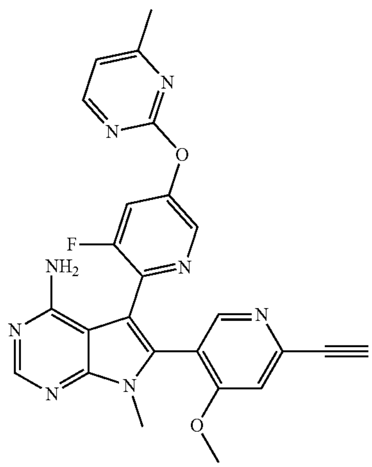 [SMILES: C#Cc1cc(OC)c(-c2c(-c3ncc(Oc4nccc(C)n4)cc3F)c3c(N)ncnc3n2C)cn1] | $^1$H NMR (400 MHz, DMSO-$d_6$) δ 8.59 (d, J = 2.3 Hz, 1H), 8.53 (d, J = 5.1 Hz, 1H), 8.23 (s, 1H), 8.04 (s, 1H), 7.80-7.72 (m, 1H), 7.45 (s, 1H), 7.24 (d, J = 5.0 Hz, 1H), 7.01-6.96 (m, 1H), 4.47 (s, 1H), 3.88 (s, 3H), 3.56 (s, 3H), 2.44 (s, 3H). | 483.20 |
| 6-(6-ethynyl-2,4-dimethylpyridin-3-yl)-5-(3-fluoro-5-((4-methylpyrimidin-2-yl)oxy)pyridin-2-yl)-7-methyl-7H-pyrrolo[2,3-d]pyrimidin-4-amine | Atropisomer 1 | $^1$H NMR (400 MHz, DMSO-$d_6$) δ 8.57 (dd, J = 2.3, 0.9 Hz, 1H), 8.52 (d, J = 5.0 Hz, 1H), 8.25 (s, 1H), 7.78 (dd, J = 11.0, 2.3 Hz, 1H), 7.43 (s, 1H), 7.23 (d, J = 5.0 Hz, 1H), 6.81 (s, 2H), 4.37 (s, 1H), 3.44 (s, 3H), 2.42 (s, 3H), 2.13 (s, 3H), 1.97 (s, 3H). | 491.20 |
| 6-(6-ethynyl-2,4-dimethylpyridin-3-yl)-5-(3-fluoro-5-((4-methylpyrimidin-2-yl)oxy)pyridin-2-yl)-7-methyl-7H-pyrrolo[2,3-d]pyrimidin-4-amine | Atropisomer 2 | $^1$H NMR (400 MHz, DMSO-$d_6$) δ 8.57 (d, J = 2.2 Hz, 1H), 8.52 (d, J = 5.0 Hz, 1H), 8.25 (s, 1H), 7.78 (dd, J = 11.0, 2.3 Hz, 1H), 7.43 (s, 1H), 7.22 (s, 1H), 6.81 (s, 2H), 4.37 (d, J = 0.8 Hz, 1H), 3.44 (s, 3H), 2.42 (s, 3H), 2.13 (s, 3H), 1.97 (s, 3H). | 481.20 |

TABLE 48-continued
Exemplary Compounds
| Compound | Structure | Proton NMR | MS [M + 1] |
|---|---|---|---|
| 6-(6-ethynyl-4-methoxypyridin-3-yl)-5-(3-fluoro-5-((4-methylpyrimidin-2-yl)oxy)pyridin-2-yl)-4,7-dimethyl-7H-pyrrolo[2,3-d]pyrimidine | 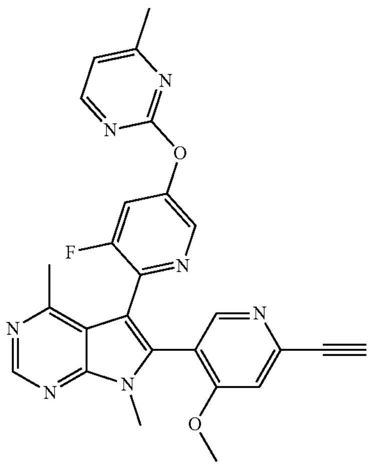 [SMILES: C#Cc1cc(OC)c(-c2c(-c3ncc(Oc4nccc(C)n4)cc3F)c3c(C)ncnc3n2C)cn1] | $^1$H NMR (400 MHz, DMSO-d$_6$) δ 8.79 (s, 1H), 8.53 (d, J = 5.0 Hz, 1H), 8.49 (d, J = 2.2 Hz, 1H), 8.19 (s, 1H), 7.86 (dd, J = 10.3, 2.3 Hz, 1H), 7.41 (s, 1H), 7.24 (d, J = 5.1 Hz, 1H), 4.47 (s, 1H), 3.84 (s, 3H), 3.68 (s, 3H), 2.42 (d, J = 11.5 Hz, 6H). | 482.10 |
Example 50
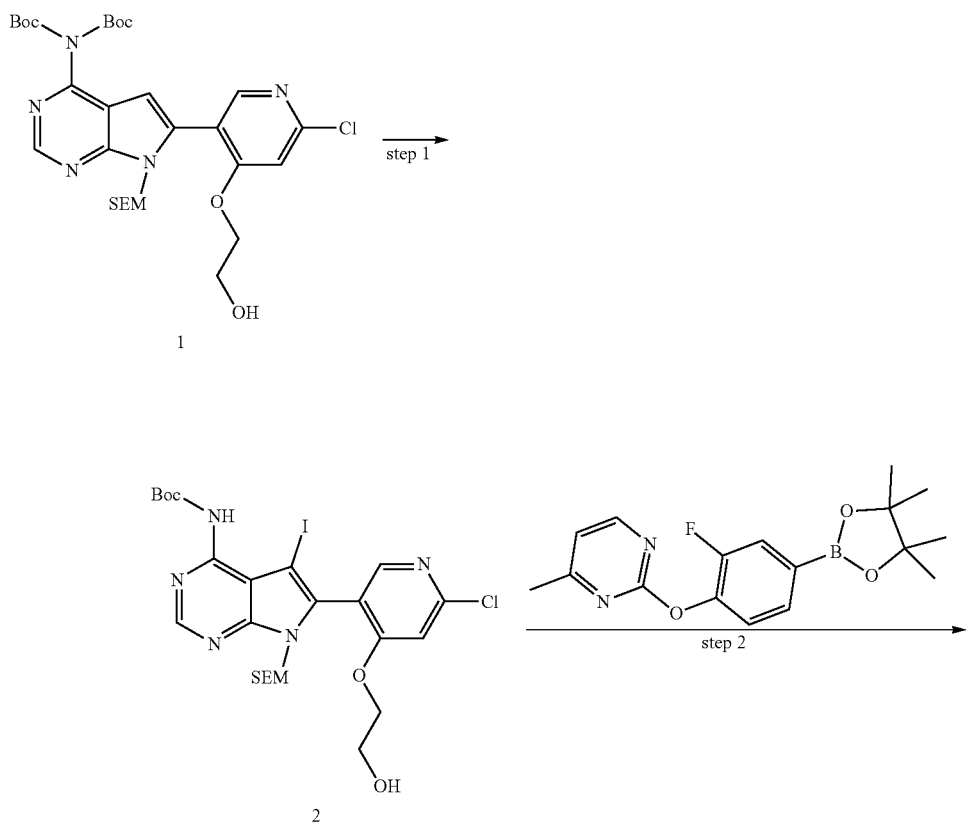

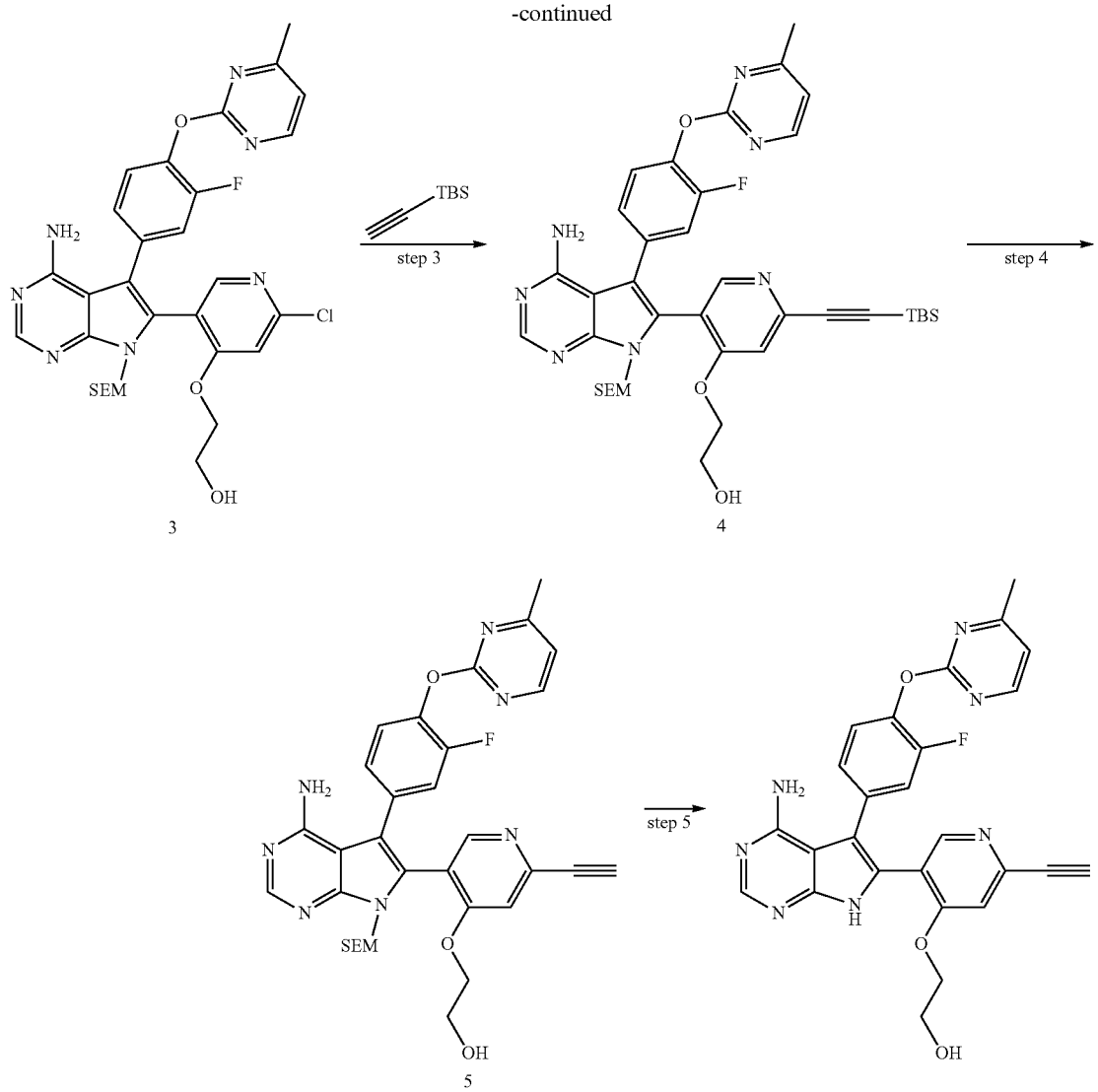

tert-butyl (6-(6-chloro-4-(2-hydroxyethoxy)pyridin-3-yl)-5-iodo-7-((2-(trimethylsilyl)ethoxy)methyl)-7H-pyrrolo[2,3-d]pyrimidin-4-yl)carbamate

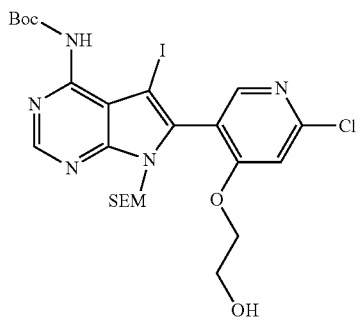 [SMILES: CC(C)(C)OC(=O)Nc1ncnc2c1c(I)c(-c1cnc(Cl)cc1OCCO)n2COCC[Si](C)(C)C]

Step 1: A round bottomed flask was charged with tert-butyl N-[(tert-butoxy)carbonyl]-N-{6-[6-chloro-4-(2-hydroxyethoxy)pyridin-3-yl]-7-{[2-(trimethylsilyl)ethoxy]methyl}-7H-pyrrolo[2,3-d]pyrimidin-4-yl}carbamate (3 g, 4.71 mmol), TFA (2.27 g, 23.5 mmol), dichloromethane (40 mL) and a stir bar. NIS (1.27 g, 5.65 mmol) was added, and the solution was stirred for 1 h at r.t. The reaction mixture was diluted with water (40 mL), and the aqueous phase was extracted with dichloromethane (60 mL) three times. The combined organic layers were washed with brine, dried over sodium sulfate, filtered, and concentrated in vacuo. The resulting crude material was purified by flash (acetonitrile/water), Concentrated in vacuo resulted in tert-butyl (6-(6-chloro-4-(2-hydroxyethoxy)pyridin-3-yl)-5-iodo-7-((2-(trimethylsilyl)ethoxy)methyl)-7H-pyrrolo[2,3-d]pyrimidin-4-yl)carbamate (600 mg) and tert-butyl N-[(tert-butoxy)carbonyl]-N-{6-[6-chloro-4-(2-hydroxyethoxy)pyridin-3-yl]-5-iodo-7-{[2-(trimethylsilyl)ethoxy]methyl}-7H-pyrrolo[2,3-d]pyrimidin-4-yl}carbamate (3.00 g, 83%) as a yellow amorphous solid.

2-((5-(4-amino-5-(3-fluoro-4-((4-methylpyrimidin-2-yl)oxy)phenyl)-7-((2-(trimethylsilyl)ethoxy)methyl)-7H-pyrrolo[2,3-d]pyrimidin-6-yl)-2-chloropyridin-4-yl)oxy)ethan-1-ol

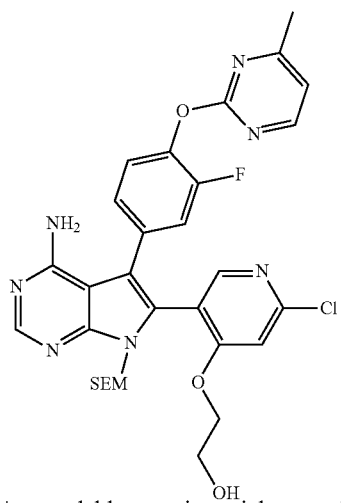

Step 2: A resealable reaction vial was charged with tert-butyl N-{6-[6-chloro-4-(2-hydroxyethoxy)pyridin-3-yl]-5-iodo-7-{[2-(trimethylsilyl)ethoxy]methyl}-7H-pyrrolo[2,3-d]pyrimidin-4-yl}carbamate (500 mg, 755 µmol), 2-[2-fluoro-4-(4,4,5,5-tetramethyl-1,3,2-dioxaborolan-2-yl)phenoxy]-4-methylpyrimidine (299 mg, 906 µmol), $K_3PO_4$ (479 mg, 2.26 mmol), Pd(dppf)Cl$_2$ (55.2 mg, 75.5 µmol), and a stir bar before being evacuated and purged with nitrogen three times. DME/H$_2$O (10 mL) was added, and the mixture was stirred for 1 h at 90° C. The reaction mixture was diluted with water (20 mL), and the aqueous phase was extracted with EA (30 mL) three times. The combined organic layers were washed with brine, dried over sodium sulfate, filtered, and concentrated in vacuo. The resulting crude material was purified by silica gel chromatography (10 g column; eluting with dichloromethane/methanol; ratio=15:1). Concentration in vacuo resulted in 2-((5-(4-amino-5-(3-fluoro-4-((4-methylpyrimidin-2-yl)oxy)phenyl)-7-((2-(trimethylsilyl)ethoxy)methyl)-7H-pyrrolo[2,3-d]pyrimidin-6-yl)-2-chloropyridin-4-yl)oxy)ethan-1-ol (320 mg, 66%) as a yellow amorphous solid.

2-((5-(4-amino-5-(3-fluoro-4-((4-methylpyrimidin-2-yl)oxy)phenyl)-7-((2-(trimethylsilyl)ethoxy)methyl)-7H-pyrrolo[2,3-d]pyrimidin-6-yl)-2-((tert-butyldimethylsilyl)ethynyl)pyridin-4-yl)oxy)ethan-1-ol

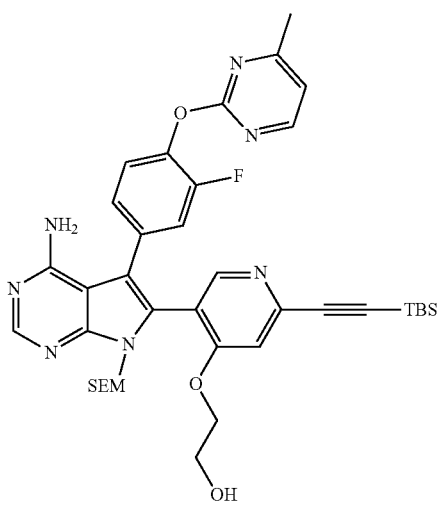

Step 3: A resealable reaction vial was charged with 2-{[5-(4-amino-5-{3-fluoro-4-[(4-methylpyrimidin-2-yl)oxy]phenyl}-7-{[2-(trimethylsilyl)ethoxy]methyl}-7H-pyrrolo[2,3-d]pyrimidin-6-yl)-2-chloropyridin-4-yl]oxy}ethan-1-ol (280 mg, 438 µmol), tert-butyl(ethynyl)dimethylsilane (122 mg, 876 µmol), CuI (33.2 mg, 175 µmol), TEA (132 mg, 1.31 mmol), Pd(dppf)Cl$_2$ (64.1 mg, 87.6 µmol) and a stir bar before being evacuated and purged with nitrogen three times. DMF (5 mL) was added, and the mixture was stirred for 2 h at 50° C. The reaction mixture was diluted with water (20 mL), and the aqueous phase was extracted with EA (30 mL) three times. The combined organic layers were washed with brine, dried over sodium sulfate, filtered, and concentrated in vacuo. The resulting crude material was purified by flash (acetonitrile/water). Concentration in vacuo resulted in 2-((5-(4-amino-5-(3-fluoro-4-((4-methylpyrimidin-2-yl)oxy)phenyl)-7-((2-(trimethylsilyl)ethoxy)methyl)-7H-pyrrolo[2,3-d]pyrimidin-6-yl)-2-((tert-butyldimethylsilyl)ethynyl)pyridin-4-yl)oxy)ethan-1-ol (110 mg, 34%) as an off-white amorphous solid.

2-((5-(4-amino-5-(3-fluoro-4-((4-methylpyrimidin-2-yl)oxy)phenyl)-7-((2-(trimethylsilyl)ethoxy)methyl)-7H-pyrrolo[2,3-d]pyrimidin-6-yl)-2-ethynylpyridin-4-yl)oxy)ethan-1-ol

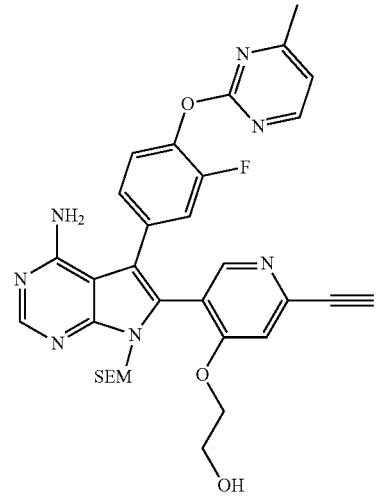 [SMILES: C#Cc1cc(OCCO)c(-c2c(-c3ccc(Oc4nccc(C)n4)c(F)c3)c3c(N)ncnc3n2COCC[Si](C)(C)C)cn1]

Step 4: A round bottomed flask was charged with 2-{[5-(4-amino-5-{3-fluoro-4-[(4-methylpyrimidin-2-yl)oxy]phenyl}-7-{[2-(trimethylsilyl)ethoxy]methyl}-7H-pyrrolo[2,3-d]pyrimidin-6-yl)-2-[2-(tert-butyldimethylsilyl)ethynyl]pyridin-4 yl]oxy}ethan-1-ol (100 mg, 134 µmol), THF (5 mL) and a stir bar. TBAF (35.0 mg, 134 µmol) was added, and the solution was stirred for 30 min at r.t. The resulting crude material was purified by silica gel chromatography (5 g column; eluting with dichloromethane/methanol; ratio=10:1). Concentration in vacuo resulted in 2-((5-(4-amino-5-(3-fluoro-4-((4-methylpyrimidin-2-yl)oxy)phenyl)-7-((2-(trimethylsilyl)ethoxy)methyl)-7H-pyrrolo[2,3-d]pyrimidin-6-yl)-2-ethynylpyridin-4-yl)oxy)ethan-1-ol (80.0 mg, 95%) as a brown amorphous solid.

2-((5-(4-amino-5-(3-fluoro-4-((4-methylpyrimidin-2-yl)oxy)phenyl)-7H-pyrrolo[2,3-d]pyrimidin-6-yl)-2-ethynylpyridin-4-yl)oxy)ethan-1-ol

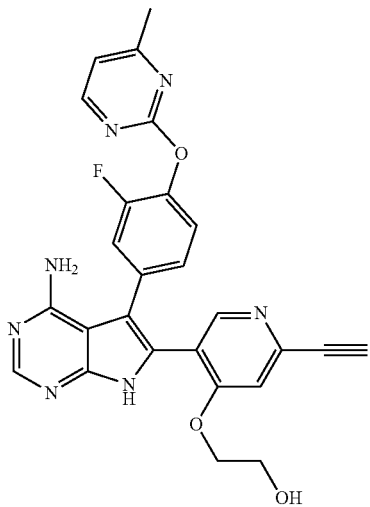 [SMILES: C#Cc1cc(OCCO)c(-c2[nH]c3ncnc(N)c3c2-c2ccc(Oc3nccc(C)n3)c(F)c2)cn1]

Step 5: A round bottomed flask was charged with 2-{[5-(4-amino-5{-3-fluoro-4-[(4-methylpyrimidin-2-yl)oxy]phenyl}-7-{[2-(trimethylsilyl)ethoxy]methyl}-7H-pyrrolo[2,3-d]pyrimidin-6-yl)-2-ethynylpyridin-4-yl]oxy}ethan-1-ol (70 mg, 111 μmol) and a stir bar. CH$_3$SO$_3$H/MeOH (1:2, 2 mL) was added, and the solution was stirred for 1 h at 70° C., and then the pH value of the solution was adjusted to 7 with TEA. The resulting crude material was purified by silica gel chromatography (5 g column; eluting with dichloromethane/methanol; ratio=10:1), Concentrated in vacuo. The resulting crude material was purified by HPLC (Column: YMC-Actus Triart C18, 30*250, 5 um; Mobile Phase A:Water(10 MMOL/L NH$_4$HCO$_3$), Mobile Phase B:ACN; Flow rate:60 mL/min; Gradient:15 B to 48 B in 7 min; 254/220 nm; RT1:6.48). Lyophilization yielded 2-((5-(4-amino-5-(3-fluoro-4-((4-methylpyrimidin-2-yl)oxy)phenyl)-7H-pyrrolo[2,3-d]pyrimidin-6-yl)-2-ethynylpyridin-4-yl)oxy)ethan-1-ol (9.20 mg, 17%) as an off-white amorphous solid.

TABLE 49

Exemplary Compound

| Compound | Structure | Proton NMR | MS [M + 1] |
|---|---|---|---|
| 2-((5-(4-amino-5-(3-fluoro-4-((4-methylpyrimidin-2-yl)oxy)phenyl)-7H-pyrrolo[2,3-d]pyrimidin-6-yl)-2-ethynylpyridin-4-yl)oxy)ethan-1-ol | 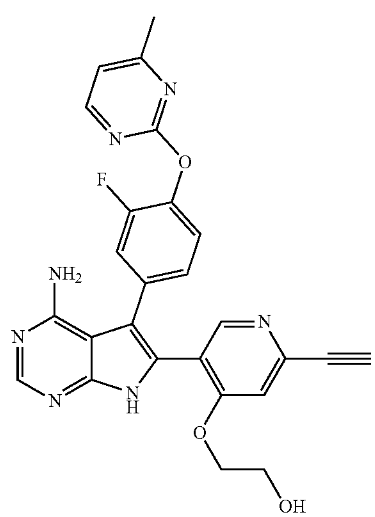 [SMILES: C#Cc1cc(OCCO)c(-c2[nH]c3ncnc(N)c3c2-c2ccc(Oc3nccc(C)n3)c(F)c2)cn1] | $^1$H NMR (400 MHz, DMSO-d$_6$) δ 12.07 (s, 1H), 8.49 (d, J = 5.0 Hz, 1H), 8.23 (s, 1H), 8.16 (s, 1H), 7.40-7.30 (m, 2H), 7.27-7.17 (m, 2H), 7.10 (dd, J = 8.2, 2.0 Hz, 1H), 6.06 (s, 1H), 4.87 (t, J = 5.4 Hz, 1H), 4.40 (s, 1H), 4.01 (t, J = 4.9 Hz, 2H), 3.56 (q, J = 5.1 Hz, 2H), 2.43 (s, 3H). | 498.30 |

1955
Example 51
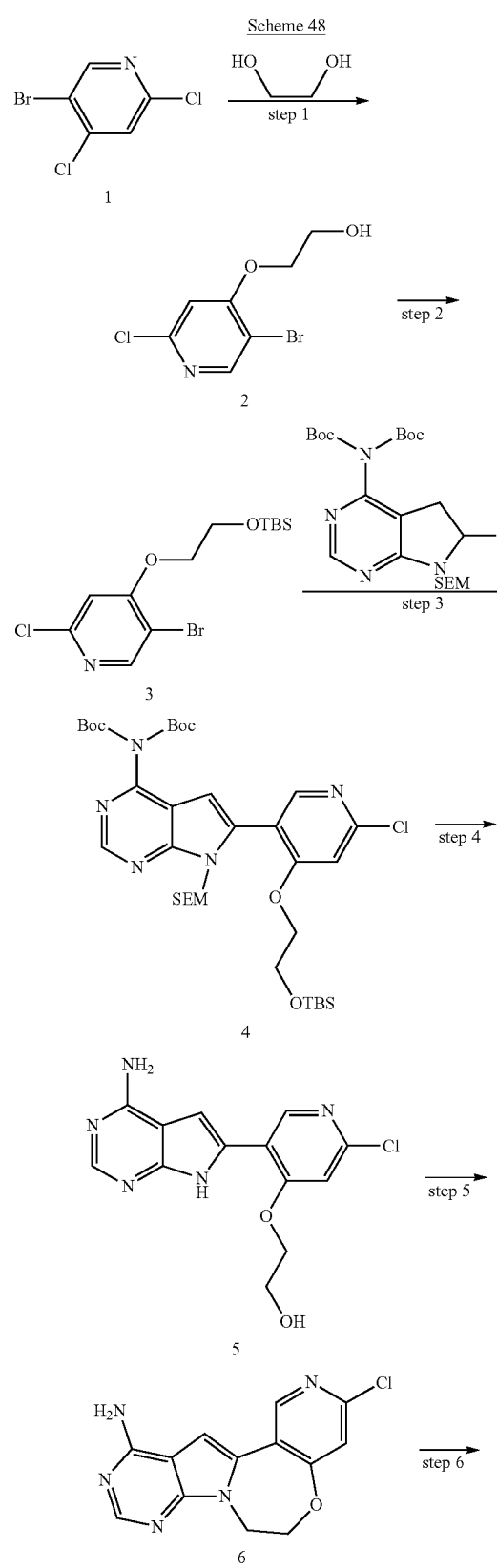
1956
-continued
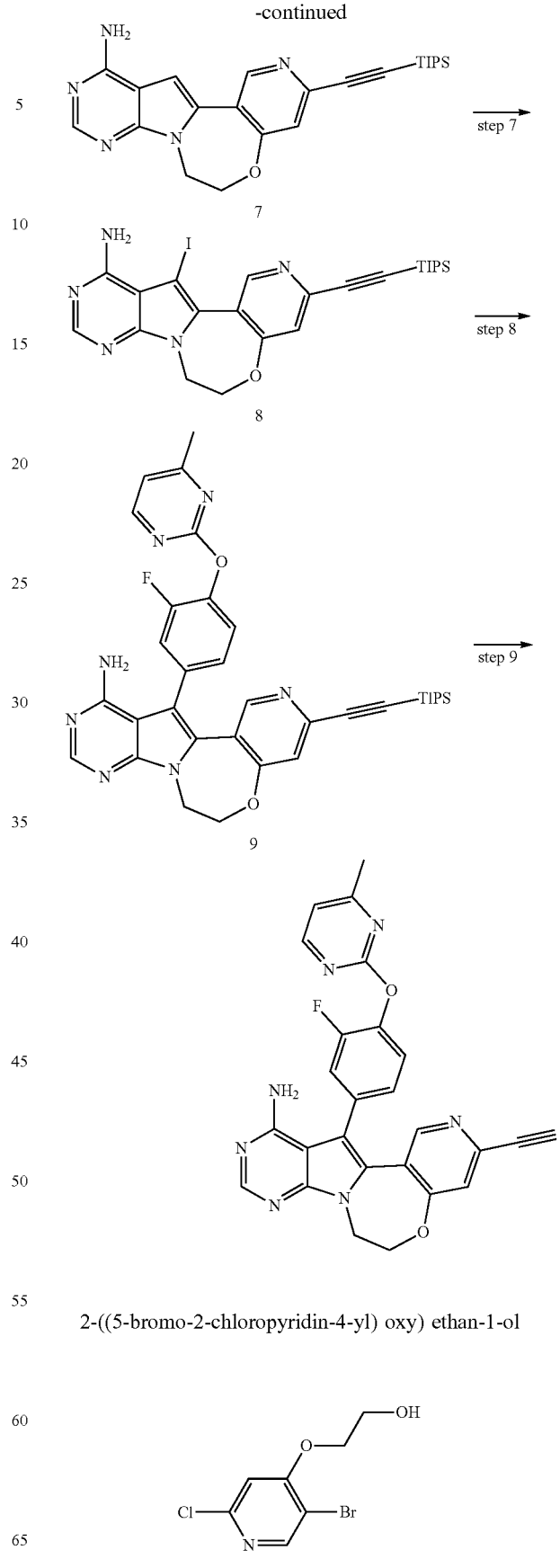
2-((5-bromo-2-chloropyridin-4-yl) oxy) ethan-1-ol Step 1: A round bottomed flask was charged with ethane-1,2-diol (81.9 g, 1.32 mol), DMSO (800 mL) and a stirbar. NaH (7.58 g, 316 mmol) was added, and the solution was stirred for 30 min at r.t., and then 5-bromo-2,4-dichloropyridine (60 g, 264 mmol) was added, and the solution was stirred for 1 h at 50° C. The reaction mixture was diluted with water(500 mL), and the aqueous phase was extracted with EA (500 mL) three times. The combined organic layers were washed with brine, dried over sodium sulfate, filtered, and concentrated in vacuo. The resulting crude material was purified by silica gel chromatography (500 g column; eluting with DCM/EA; ratio=1:1). Concentration in vacuo resulted in 2-[(5-bromo-2-chloropyridin-4-yl)oxy]ethan-1-ol (55.0 g, 82%) as yellow oil.

5-bromo-4-(2-((tert-butyldimethylsilyl)oxy)ethoxy)-2-chloropyridine

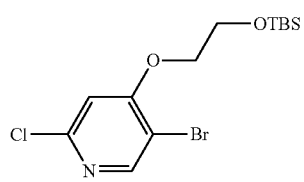 [SMILES: CC(C)(C)[Si](C)(C)OCCOc1cc(Cl)ncc1Br]

Step 2: A round bottomed flask was charged with 2-[(5-bromo-2-chloropyridin-4-yl)oxy]ethan-1-ol (55 g, 217 mmol), Imidazole (73.5 g, 1.08 mol), DMF (1000 mL) and a stirbar. TBSCl (65.4 g, 434 mmol) was added, and the solution was stirred for 16 h at r.t. The reaction mixture was extracted with EA (1000 mL), the combined organic layers were washed with brine, dried over sodium sulfate, filtered, and concentrated in vacuo. The resulting crude material was purified by silica gel chromatography (600 g column; eluting with PE/EA; ratio=40:1). Concentration in vacuo resulted in 5-bromo-4-(2-((tert-butyldimethylsilyl)oxy)ethoxy)-2-chloropyridine (82.4 g, 100%) as an off-white crystalline solid.

tert-butyl N-[(tert-butoxy)carbonyl]-N-[6-(4-{2-[(tert-butyldimethylsilyl)oxy]ethoxy}-6-chloropyridin-3-yl)-7-{[2-(trimethylsilyl)ethoxy]methyl}-7H-pyrrolo[2,3-d]pyrimidin-4-yl]carbamate

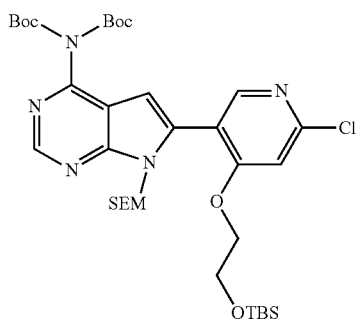 [SMILES: CC(C)(C)OC(=O)N(C(=O)OC(C)(C)C)c1ncnc2c1cc(-c1cnc(Cl)cc1OCCO[Si](C)(C)C(C)(C)C)n2COCC[Si](C)(C)C]

Step 3: A resealable reaction vial was charged with 5-bromo-4-{2-[(tert-butyldimethylsilyl)oxy]ethoxy}-2-chloropyridine (28 g, 76.3 mmol), (4-{bis[(tert-butoxy)carbonyl]amino}-7-{[2-(trimethylsilyl)ethoxy]methyl}-7H-pyrrolo[2,3-d]pyrimidin-6-yl)boronic acid (77.2 g, 152 mmol), CsF (34.6 g, 228 mmol), Pd(dtbpf)Cl₂ (4.97 g, 7.63 mmol) and a stirbar before being evacuated and purged with nitrogen three times. Dioxane/H₂O (600 mL) was added, and the mixture was stirred for 2 h at 70° C. The reaction mixture was diluted with water (400 mL), and the aqueous phase was extracted with DCM (500 mL) three times. The combined organic layers were washed with brine, dried over sodium sulfate, filtered, and concentrated in vacuo. The resulting crude material was purified by flash (acetonitrile/water). Concentration in vacuo resulted in tert-butyl N-[(tert-butoxy)carbonyl]-N-[6-(4-{2-[(tert-butyldimethylsilyl)oxy]ethoxy}-6-chloropyridin-3-yl)-7-{[2-(trimethylsilyl)ethoxy]methyl}-7H-pyrrolo[2,3-d]pyrimidin-4-yl]carbamate (30.0 g, 52%) as a yellow amorphous solid.

2-((5-(4-amino-7H-pyrrolo[2,3-d]pyrimidin-6-yl)-2-chloropyridin-4-yl)oxy)ethan-1-ol

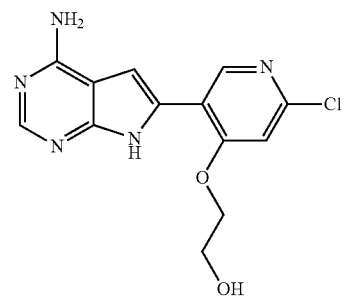 [SMILES: Nc1ncnc2[nH]c(-c3cnc(Cl)cc3OCCO)cc12]

Step 4: A round bottomed flask was charged with tert-butyl N-[(tert-butoxy)carbonyl]-N-[6-(4-{2-[(tert-butyldimethylsilyl)oxy]ethoxy}-6-chloropyridin-3-yl)-7-{[2-(trimethylsilyl)ethoxy]methyl}-7H-pyrrolo[2,3-d]pyrimidin-4-yl]carbamate (29 g, 38.6 mmol) and a stirbar. HCl(12M)/MeOH (1:1, 600 mL) was added, and the solution was stirred for 3 h at r.t., and then the pH value of the solution was adjusted to 8 with TEA at 0° C., then concentrated in vacuo. The precipitated solids were collected by filtration and washed with ACN (300 mL) three times, dried in vacuo resulted in 2-((5-(4-amino-7H-pyrrolo[2,3-d]pyrimidin-6-yl)-2-chloropyridin-4-yl)oxy)ethan-1-ol (8.00 g, 67%) as an off-white amorphous solid.

3-chloro-6,7-dihydropyrido[3,4-f]pyrimido[5',4':4,5]pyrrolo[1,2-d][1,4]oxazepin-12-amine

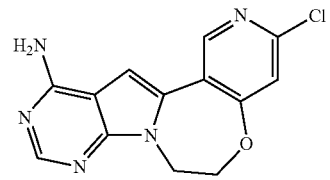 [SMILES: Nc1ncnc2c1cc1n2CCOc2cc(Cl)ncc2-1]

Step 5: A resealable reaction vial was charged with 2-[(5-{4-amino-7H-pyrrolo[2,3-d]pyrimidin-6-yl}-2-chloropyridin-4-yl)oxy]ethan-1-ol (7.9 g, 25.8 mmol), DIAD (10.4 g, 51.6 mmol), THF (80 mL) and a stirbar before being evacuated and purged with nitrogen three times. PPh₃ (13.5 g, 51.6 mmol) in THF (40 ml) was added, and the mixture was stirred for 3 h at 30° C. The solvent was removed in vacuo. The residue was washed with DCM (200 mL), dried in vacuo resulted in 3-chloro-6,7-dihydropyrido[3,4-f]pyrimido[5',4':4,5]pyrrolo[1,2-d][1,4]oxazepin-12-amine (5.00 g, 67%) as an off-white amorphous solid.

3-((triisopropylsilyl)ethynyl)-6,7-dihydropyrido[3,4-f]pyrimido[5',4':4,5]pyrrolo[1,2-d][1,4]oxazepin-12-amine

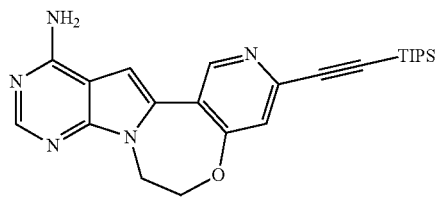

Step 6: A resealable reaction vial was charged with 3-chloro-6,7-dihydropyrido[3,4-f]pyrimido[5',4':4,5]pyrrolo[1,2-d][1,4]oxazepin-12-amine (4.9 g, 17.0 mmol), DMF (150 mL), TEA (5.15 g, 50.9 mmol), CuI (1.29 g, 6.80 mmol), Pd(dppf)Cl$_2$·CH$_2$Cl$_2$ (2.77 g, 3.40 mmol), and a stirbar before being evacuated and purged with nitrogen three times. Then ethynyltris(propan-2-yl)silane (6.20 g, 34.0 mmol) was added, and the mixture was stirred for 2 h at 70° C. The reaction mixture was diluted with water (500 mL), and the aqueous phase was extracted with dichloromethane (400 mL) three times. The combined organic layers were washed with brine, dried over sodium sulfate, filtered, and concentrated in vacuo. The resulting crude material was purified by silica gel chromatography (100 g column; eluting with dichloromethane/methanol; ratio=20:1). Concentration in vacuo resulted in 3-((triisopropylsilyl)ethynyl)-6,7-dihydropyrido[3,4-f]pyrimido[5',4':4,5]pyrrolo[1,2-d][1,4]oxazepin-12-amine (4.5 g, 61.0%) as a brown amorphous solid.

13-iodo-3-((triisopropylsilyl)ethynyl)-6,7-dihydropyrido[3,4-f]pyrimido[5',4':4,5]pyrrolo[1,2-d][1,4]oxazepin-12-amine

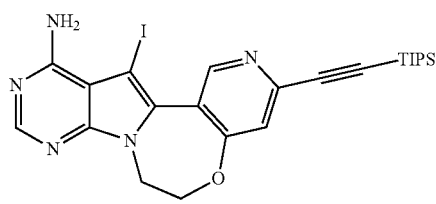

Step 7: A round bottomed flask was charged with 3-((triisopropylsilyl)ethynyl)-6,7-dihydropyrido[3,4-f]pyrimido[5',4':4,5]pyrrolo[1,2-d][1,4]oxazepin-12-amine (4.4 g, 10.1 mmol), TFA (3.45 g, 30.3 mmol), and a stirbar. Dichloromethane (100 mL) was added, and then NIS (3.39 g, 15.1 mmol) was added at 0° C. and the solution was stirred for 1 h at r.t., The reaction was quenched with NaHSO$_3$ aq., then adjusted PH to 6-7 with sodium bicarbonate. The reaction mixture was diluted with water (30 mL), the precipitated solids were collected by filtration and washed with ACN (300 mL). Dried in vacuo resulted in 13-iodo-3-((triisopropylsilyl)ethynyl)-6,7-dihydropyrido[3,4-f]pyrimido[5',4':4,5]pyrrolo[1,2-d][1,4]oxazepin-12-amine (5.50 g, 97%) as an off-white amorphous solid.

13-(3-fluoro-4-((4-methylpyrimidin-2-yl)oxy)phenyl)-3-((triisopropylsilyl)ethynyl)-6,7-dihydropyrido[3,4-f]pyrimido[5',4':4,5]pyrrolo[1,2-d][1,4]oxazepin-12-amine

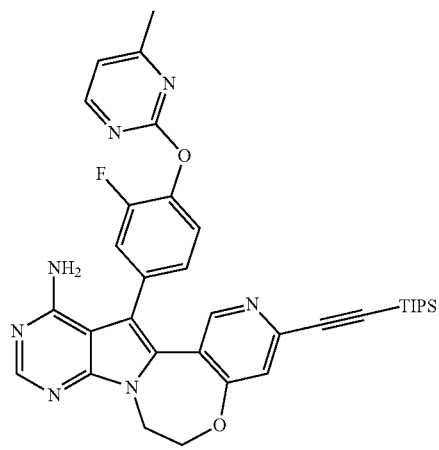

Step 8: A resealable reaction vial was charged with 13-iodo-3-((triisopropylsilyl)ethynyl)-6,7-dihydropyrido[3,4-f]pyrimido[5',4':4,5]pyrrolo[1,2-d][1,4]oxazepin-12-amine (5.4 g, 9.65 mmol), 2-[2-fluoro-4-(4,4,5,5-tetramethyl-1,3,2-dioxaborolan-2-yl)phenoxy]-4-methylpyrimidine (4.75 g, 14.4 mmol), K$_3$PO$_4$ (6.13 g, 28.9 mmol), Pd(dppf)Cl$_2$·CH$_2$Cl$_2$ (787 mg, 965 μmol), and a stirbar before being evacuated and purged with nitrogen three times. DME/H$_2$O (100 mL) was added, and the mixture was stirred for 1 h at 90° C. The reaction mixture was diluted with water (80 mL), and the aqueous phase was extracted with dichloromethane (100 mL) three times. The combined organic layers were washed with brine, dried over sodium sulfate, filtered, and concentrated in vacuo. The resulting crude material was purified by silica gel chromatography (100 g column; eluting with dichloromethane/methanol; ratio=20;1). Concentration in vacuo resulted in 13-(3-fluoro-4-((4-methylpyrimidin-2-yl)oxy)phenyl)-3-((triisopropylsilyl)ethynyl)-6,7-dihydropyrido[3,4-f]pyrimido[5',4':4,5]pyrrolo[1,2-d][1,4]oxazepin-12-amine (4.70 g, 76%) as a brown amorphous solid.

3-ethynyl-13-(3-fluoro-4-((4-methylpyrimidin-2-yl)oxy)phenyl)-6,7-dihydropyrido[3,4-f]pyrimido[5',4':4,5]pyrrolo[1,2-d][1,4]oxazepin-12-amine

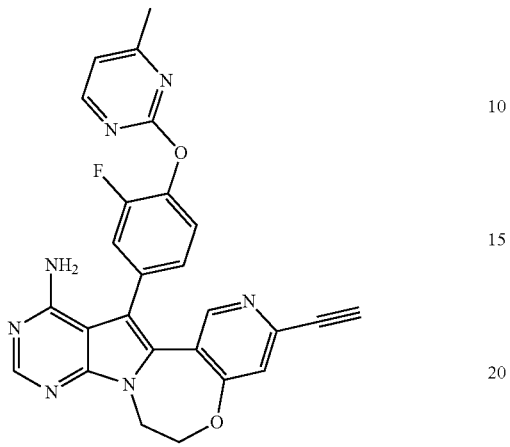

Step 9: A round bottomed flask was charged with 13-(3-fluoro-4-((4-methylpyrimidin-2-yl)oxy)phenyl)-3-((triisopropylsilyl)ethynyl)-6,7-dihydropyrido[3,4-f]pyrimido[5',4':4,5]pyrrolo[1,2-d][1,4]oxazepin-12-amine (4.6 g, 7.23 mmol), tetrahydrofuran (60 mL) and a stirbar. TBAF (1.89 g, 7.23 mmol) was added, and the solution was stirred for 30 min at r.t. The resulting crude material was purified by silica gel chromatography (100 g column; eluting with dichloromethane/methanol; ratio=20:1). Concentration in vacuo. and then the residue was washed with water (50 mL) and ACN (100 ml), resulted in 3-ethynyl-13-(3-fluoro-4-((4-methylpyrimidin-2-yl)oxy)phenyl)-6,7-dihydropyrido[3,4-f]pyrimido[5',4':4,5]pyrrolo[1,2-d][1,4]oxazepin-12-amine (3.00 g, 86%) as a light yellow amorphous solid.

TABLE 50

Exemplary Compounds

| Compound | Structure | Proton NMR | MS [M + 1] |
|---|---|---|---|
| 3-ethynyl-13-(3-fluoro-4-((4-methylpyrimidin-2-yl)oxy)phenyl)-6,7-dihydropyrido[3,4-f]pyrimido[5',4':4,5]pyrrolo[1,2-d][1,4]oxazepin-12-amine | 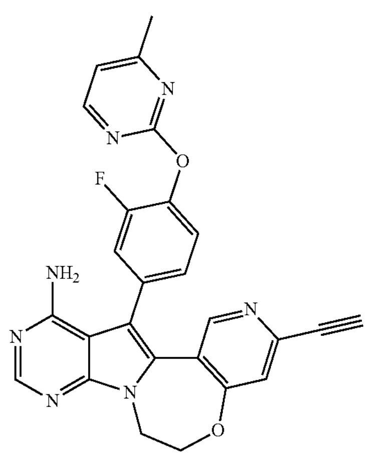 [SMILES: C#Cc1cc2c(cn1)-c1c(-c3ccc(Oc4nccc(C)n4)c(F)c3)c3c(N)ncnc3n1CCO2] | $^1$H NMR (400 MHz, DMSO-$d_6$) δ 8.53 (d, J = 5.0 Hz, 1H), 8.22 (s, 1H), 8.02 (s, 1H), 7.54-7.41 (m, 2H), 7.34-7.27 (m, 1H), 7.25 (s, 1H), 7.22 (d, J = 5.1 Hz, 1H), 6.11 (s, 1H), 4.67 (s, 4H), 4.39 (s, 1H), 2.46 (s, 3H). | 480.15 |

TABLE 50-continued

Exemplary Compounds

| Compound | Structure | Proton NMR | MS [M + 1] |
|---|---|---|---|
| (R)-3-ethynyl-13-(3-fluoro-4-((4-methylpyrimidin-2-yl)oxy)phenyl)-7-methyl-6,7-dihydropyrido[3,4-f]pyrimido[5',4':4,5]pyrrolo[1,2-d][1,4]oxazepin-12-amine | 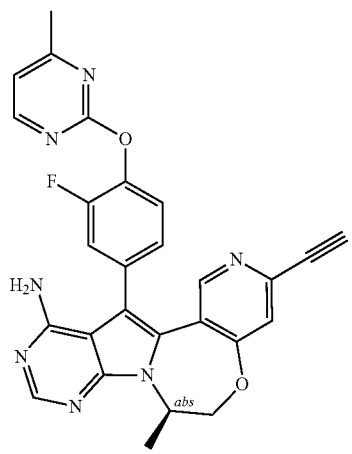 [SMILES: C#Cc1cc2c(cn1)-c1c(-c3ccc(Oc4nccc(C)n4)c(F)c3)c3c(N)ncnc3n1[C@H](C)CO2] | $^1$H NMR (400 MHz, DMSO-$d_6$) δ 8.54 (d, J = 5.0 Hz, 1H), 8.22 (s, 1H), 8.05 (s, 1H), 7.52 (d, J = 8.5 Hz, 2H), 7.36 (s, 1H), 7.29-7.17 (m, 2H), 5.76 (s, 1H), 5.62-5.37 (m, 1H), 4.73 (dd, J = 12.8,4.3 Hz, 1H), 4.60 (d, J = 12.6 Hz, 1H), 4.37 (s, 1H), 2.46 (s, 3H), 1.39 (d, J = 7.1 Hz, 3H). | 494.20 |
| (S)-3-ethynyl-13-(3-fluoro-4-((4-methylpyrimidin-2-yl)oxy)phenyl)-6-methyl-6,7-dihydropyrido[3,4-f]pyrimido[5',4':4,5]pyrrolo[1,2-d][1,4]oxazepin-12-amine | 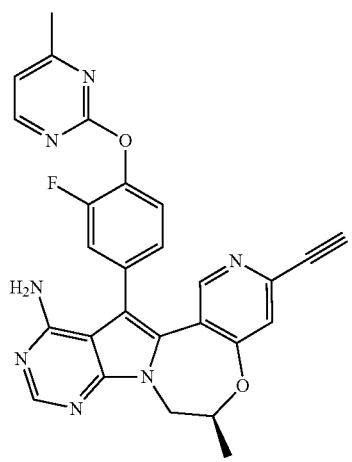 | $^1$H NMR (400 MHz, DMSO-$d_6$) δ 8.53 (d, J = 5.0 Hz, 1H), 8.23 (s, 1H), 8.04 (s, 1H), 7.51-7.41 (m, 2H), 7.30-7.20 (m, 3H), 5.76 (s, 1H), 4.94 (td, J = 6.4, 2.8 Hz, 1H), 4.64 (dd, J = 15.3, 2.8 Hz, 1H), 4.42 (s, 1H), 4.34 (dd, J = 15.3, 6.4 Hz, 1H), 2.46 (s, 3H), 1.32 (d, J = 6.4 Hz, 3H). | 494.20 |
| (S)-3-ethynyl-13-(3-fluoro-4-((4-methylpyrimidin-2-yl)oxy)phenyl)-7-methyl-6,7-dihydropyrido[3,4-f]pyrimido[5',4':4,5]pyrrolo[1,2-d][1,4]oxazepin-12-amine | 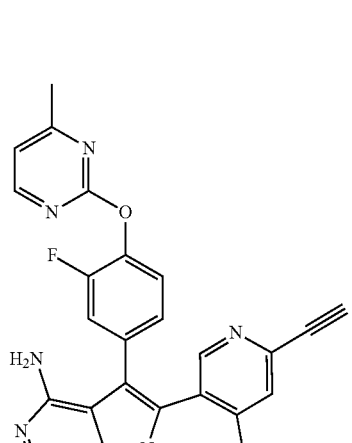 | $^1$H NMR (400 MHz, DMSO-$d_6$) δ 8.54 (d, J = 5.0 Hz, 1H), 8.23 (s, 1H), 8.05 (s, 1H), 7.52 (d, J = 8.6 Hz, 2H), 7.32 (d, J = 28.4 Hz, 1H), 7.23-7.16 (m, 2H), 6.12 (s, 1H), 5.54-5.39 (m, 1H), 4.73 (dd, J = 12.8, 4.3 Hz, 1H), 4.60 (d, J = 12.6 Hz, 1H), 4.37 (s, 1H), 2.46 (s, 3H), 1.39 (d, J = 12 Hz, 3H). | 494.15 |

TABLE 50-continued

Exemplary Compounds

| Compound | Structure | Proton NMR | MS [M + 1] |
|---|---|---|---|
| (R)-3-ethynyl-13-(3-fluoro-4-((4-methylpyrimidin-2-yl)oxy)phenyl)-6-methyl-6,7-dihydropyrido[3,4-f]pyrimido[5',4':4,5]pyrrolo[1,2-d][1,4]oxazepin-12-amine | 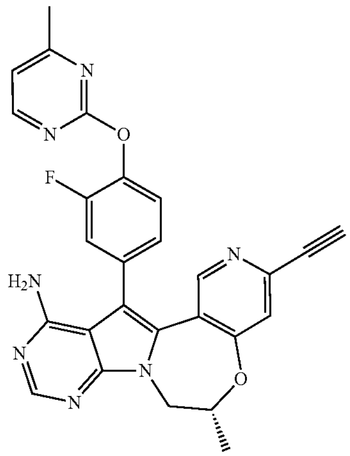 [SMILES: C#Cc1cc2c(cn1)-c1c(-c3ccc(Oc4nccc(C)n4)c(F)c3)c3c(N)ncnc3n1C[C@@H](C)O2] | $^1$H NMR (400 MHz, DMSO-d$_6$) δ 8.53 (d, J = 5.0 Hz, 1H), 8.24 (s, 1H), 8.04 (s, 1H), 7.57-7.35 (m, 2H), 7.34-7.17 (m, 3H), 6.21 (s, 1H), 4.94 (td, J = 6.4, 2.8 Hz, 1H), 4.65 (dd, J = 15.3, 2.9 Hz, 1H), 4.42 (s, 1H), 4.34 (dd, J = 15.3, 6.4 Hz, 1H), 2.46 (s, 3H), 1.32 (d, J = 6.4 Hz, 3H). | 494.20 |
| 3-ethynyl-13-(3-fluoro-4-((4-methylpyrimidin-2-yl)oxy)phenyl)-6,7-dihydropyrido[3,2-f]pyrimido[5',4':4,5]pyrrolo[1,2-d][1,4]oxazepin-12-amine | 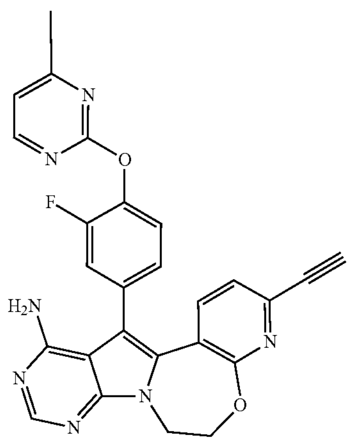 [SMILES: C#Cc1ccc2c(n1)OCCn1c-2c(-c2ccc(Oc3nccc(C)n3)c(F)c2)c2c(N)ncnc21] | $^1$H NMR (400 MHz, DMSO-d$_6$) δ 8.52 (d, J = 5.0 Hz, 1H), 8.23 (s, 1H), 7.49-7.34 (m, 3H), 7.29-7.20 (m, 3H), 6.15 (s, 1H), 4.64 (t, J = 5.1 Hz, 2H), 4.55 (t, J = 5.2 Hz, 2H), 4.44 (s, 1H), 2.45 (s, 3H). | 480.20 |

Example 52

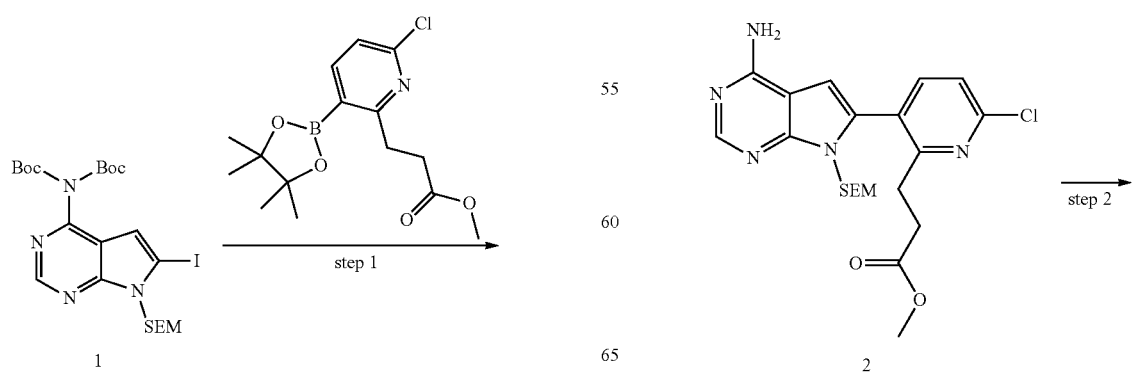

Scheme 49

-continued

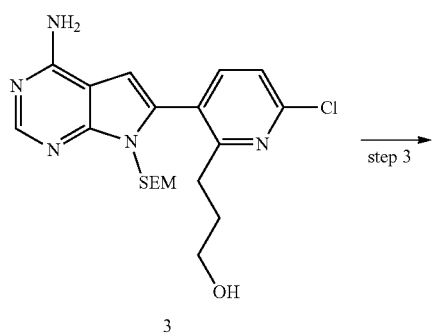

3

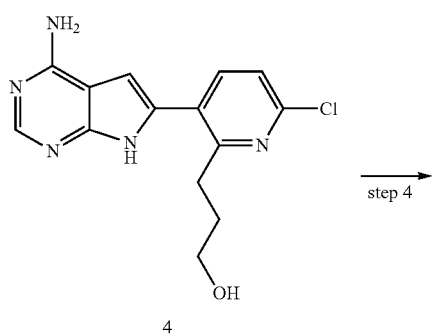

4 step 3 → step 4 →

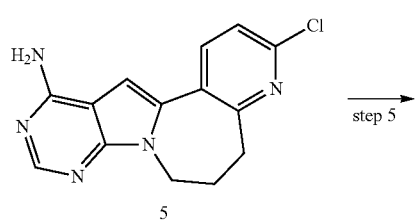

5 step 5 →

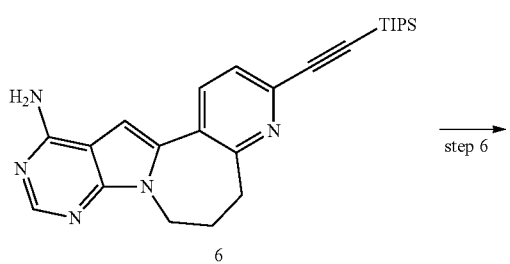

6 step 6 →

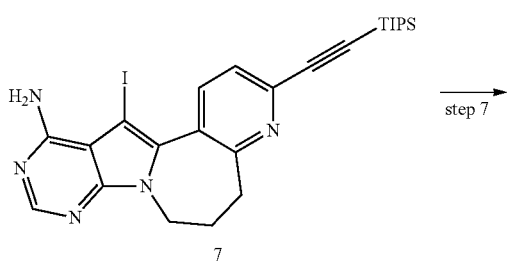

7 step 7 →

-continued

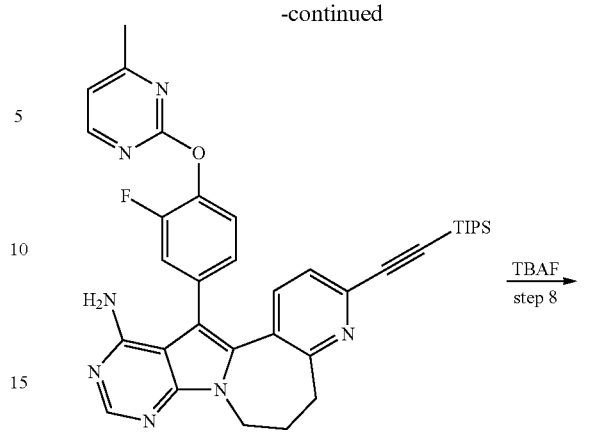

8

TBAF
step 8 →

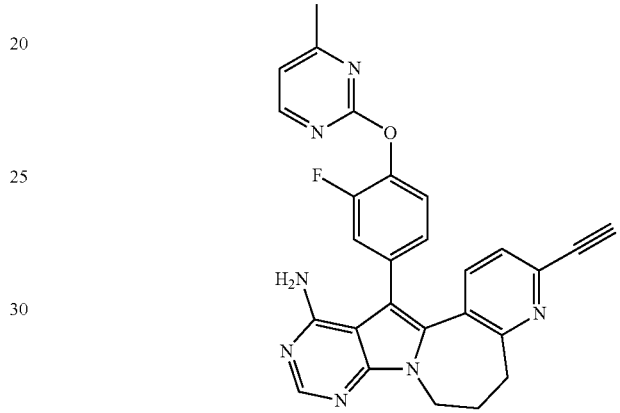

methyl 3-(3-(4-amino-7-((2-(trimethylsilyl)ethoxy)
methyl)-7H-pyrrolo[2,3-d]pyrimidin-6-yl)-6-chloro-
pyridin-2-yl)propanoate

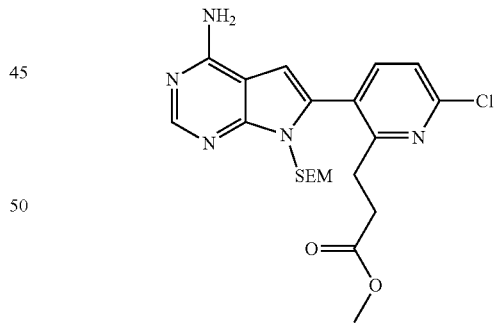

Step 1: A round bottomed flask was charged with 6-iodo-7-{[2-(trimethylsilyl)ethoxy]methyl}-7H-pyrrolo[2,3-d]pyrimidin-4-amine (23.8 g, 61.0 mmol), methyl 3-[6-chloro-3-(4,4,5,5-tetramethyl-1,3,2-dioxaborolan-2-yl)pyridin-2-yl]propanoate (21.8 g, 67.1 mmol), Pd(dtbpf)Cl$_2$ (3.97 g, 6.10 mmol), CsF (27.8 g, 183 mmol) and a stir bar. Dioxane/H$_2$O (500 mL) was added, and the solution was stirred for 2 h at 90° C. The reaction mixture was diluted with water (500 mL), and the aqueous phase was extracted with dichloromethane (800 mL) three times. The combined organic layers were washed with brine, dried over sodium sulfate, filtered, and concentrated in vacuo. The resulting crude material was purified by HPLC (MeCN/H₂O=0%-50%; 30 min). Concentration in vacuo resulted in methyl 3-[3-(4-amino-7-{[2-(trimethylsilyl)ethoxy]methyl}-7H-pyrrolo[2,3-d]pyrimidin-6-yl)-6-chloropyridin-2-yl]propanoate (13 g, 46%) as a yellow amorphous solid.

3-(3-(4-amino-7-((2-(trimethylsilyl)ethoxy)methyl)-7H-pyrrolo[2,3-d]pyrimidin-6-yl)-6-chloropyridin-2-yl)propan-1-ol

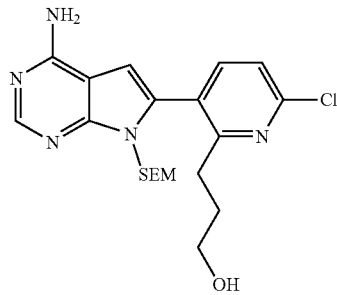 [SMILES: C[Si](C)(C)CCOCn1c(-c2ccc(Cl)nc2CCCO)cc2c(N)ncnc21]

Step 2: A round bottomed flask was charged with methyl 3-[3-(4-amino-7-{[2-(trimethylsilyl)ethoxy]methyl}-7H-pyrrolo[2,3-d]pyrimidin-6-yl)-6-chloropyridin-2-yl]propanoate (13.0 g, 28.1 mmol), tetrahydrofuran (200 mL) was added. At −30° C. LiAlH₄ (1.28 g, 33.7 mmol) was added and the solution was stirred for 2 h at −30° C. The reaction mixture was quenched with water (2.44 mL), and the reaction mixture was filtered through a pad of Celite, the pad was washed with DCM, and the filtrate was concentrated in vacuo. The resulting crude material was purified by silica gel chromatography (eluting with dichloromethane/methanol; 40:1). Concentration in vacuo resulted in 3-[3-(4-amino-7-{[2-(trimethylsilyl)ethoxy]methyl}-7H-pyrrolo[2,3-d]pyrimidin-6-yl)-6-chloropyridin yl]propan-1-ol (6.30 g, 52%) as a yellow amorphous solid.

3-(3-(4-amino-7H-pyrrolo[2,3-d]pyrimidin-6-yl)-6-chloropyridin-2-yl)propan-1-ol

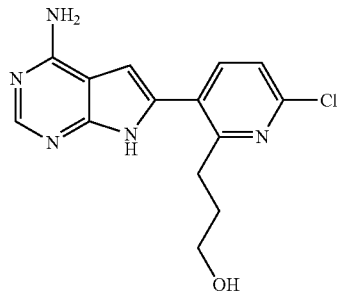 [SMILES: Nc1ncnc2[nH]c(-c3ccc(Cl)nc3CCCO)cc12]

Step 3: A round bottomed flask was charged with 3-[3-(4-amino-7-{[2-(trimethylsilyl)ethoxy]methyl}-7H-pyrrolo[2,3-d]pyrimidin-6-yl)-6-chloropyridin-2-yl]propan-1-ol (5.00 g, 11.5 mmol) and a stirbar. HCl/MeOH (50 mL) was added, and the solution was stirred for 1 h at 40° C. The reaction mixture was concentrated in vacuo. Then diluted with MeCN (20 mL), the reaction mixture was filtered through a pad of Celite, the pad was washed with MeCN, and the filter cake resulted in 3-(3-{4-amino-7H-pyrrolo[2,3-d]pyrimidin-6-yl}-6-chloropyridin-2-yl)propan-1-ol (3.00 g, 90%) as an off-white amorphous solid.

3-chloro-6,7-dihydro-5H-pyrido[3,2-c]pyrimido[5',4':4,5]pyrrolo[1,2-a]azepin-12-amine

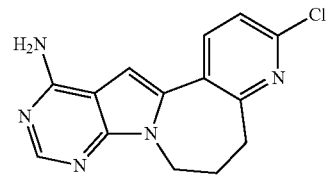 [SMILES: Nc1ncnc2c1cc1n2CCCc2nc(Cl)ccc2-1]

Step 4: A resealable reaction vial was charged with 3-(3-{4-amino-7H-pyrrolo[2,3-d]pyrimidin-6-yl}-6-chloro-pyridin-2-yl)propan-1-ol (3.50 g, 11.5 mmol), tetrahydrofuran (40 mL), and a stirbar before being evacuated and purged with nitrogen three times. DIAD (3.47 g, 17.2 mmol) and PPh₃ (4.52 g, 17.2 mmol) were added, and the mixture was stirred for 2 h at 25° C. The reaction mixture was diluted with water (40 mL), and the aqueous phase was extracted with dichloromethane (40 mL) three times. The combined organic layers were washed with brine, dried over sodium sulfate, filtered, and concentrated in vacuo. The resulting crude material was purified by silica gel chromatography (eluting with dichloromethane/methanol; 30:1). Concentration in vacuo resulted in 3-chloro-6,7-dihydro-5H-pyrido[3,2-c]pyrimido[5',4':4,5]pyrrolo[1,2-a]azepin-12-amine (2.00 g, 61%) as a yellow amorphous solid.

3-((triisopropylsilyl)ethynyl)-6,7-dihydro-5H-pyrido[3,2-c]pyrimido[5',4':4,5]pyrrolo[1,2-a]azepin-12-amine

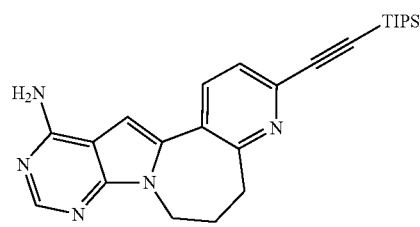

Step 5: A resealable reaction vial was charged with 3-chloro-6,7-dihydro-5H-pyrido[3,2-c]pyrimido[5',4':4,5]pyrrolo[1,2-a]azepin-12-amine (1.98 g, 6.92 mmol), dimethylformamide (20 mL), CuI (524 mg, 2.76 mmol), TEA (2.09 g, 20.7 mmol), Pd(dppf)Cl₂ (505 mg, 692 μmol), and a stirbar before being evacuated and purged with nitrogen three times. ethynyltris(propan-2-yl)silane (2.51 g, 13.8 mmol) was added, and the mixture was stirred for 2 h at 90° C. The reaction mixture was diluted with water (20 mL), and the aqueous phase was extracted with dichloromethane (20 mL) three times. The combined organic layers were washed with brine, dried over sodium sulfate, filtered, and concentrated in vacuo. The resulting crude material was purified by silica gel chromatography (eluting with dichloromethane/methanol; 40/1). Concentration in vacuo resulted in 3-((triisopropylsilyl)ethynyl)-6,7-dihydro-5H-pyrido[3,2-c]pyrimido[5',4':4,5]pyrrolo[1,2-a]azepin-12-amine (1.50 g, 50%) as a yellow amorphous solid.

13-iodo-3-((triisopropylsilyl)ethynyl)-6,7-dihydro-5H-pyrido[3,2-c]pyrimido[5',4':4,5]pyrrolo[1,2-a]azepin-12-amine

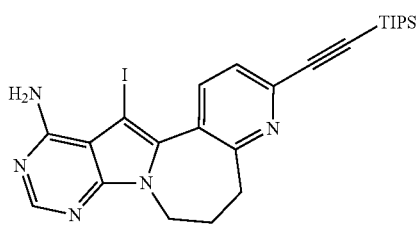

Step 6: A round bottomed flask was charged with 3-((triisopropylsilyl)ethynyl)-6,7-dihydro-5H-pyrido[3,2-c]pyrimido[5',4':4,5]pyrrolo[1,2-a]azepin-12-amine (1.88 g, 4.35 mmol), dimethylformamide (2 mL), NIS (978 mg, 4.35 mmol) and a stirbar, and the solution was stirred for 1 h at 25° C. The reaction mixture was diluted with Na$_2$SO$_3$ (aq.) (20 mL), and the aqueous phase was extracted with dichloromethane (20 mL) three times. The combined organic layers were washed with brine, dried over sodium sulfate, filtered, and concentrated in vacuo. The resulting crude material was purified by silica gel chromatography (eluting with dichloromethane/methanol; 40:1). Concentration in vacuo resulted in 13-iodo ((triisopropylsilyl)ethynyl)-6,7-dihydro-5H-pyrido[3,2-c]pyrimido[5',4':4,5]pyrrolo[1,2-a]azepin-12-amine (1.50 g, 62%) as a yellow amorphous solid.

13-(3-fluoro-4-((4-methylpyrimidin-2-yl)oxy)phenyl)-3-((triisopropylsilyl)ethynyl)-6,7-dihydro-5H-pyrido[3,2-c]pyrimido[5',4':4,5]pyrrolo[1,2-a]azepin-12-amine

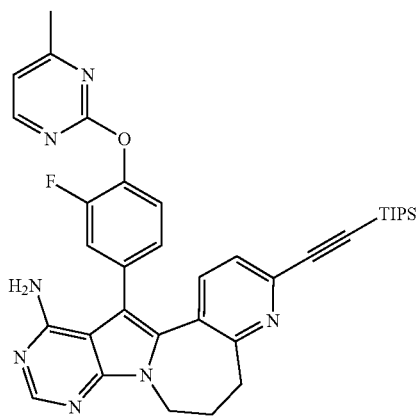

Step 7: A resealable reaction vial was charged with 13-iodo-3-((triisopropylsilyl)ethynyl)-6,7-dihydro-5H-pyrido[3,2-c]pyrimido[5',4':4,5]pyrrolo[1,2-a]azepin-12-amine (1.48 g, 2.65 mmol), 2-[2-fluoro-4-(4,4,5,5-tetramethyl-1,3,2-dioxaborolan-2-yl)phenoxy]-4-methylpyrimidine (960 mg, 2.91 mmol), K$_3$PO$_4$ (1.68 g, 7.95 mmol), Pd(dppf)Cl$_2$ (193 mg, 265 μmol), DME/H$_2$O (20 mL) was added, and a stirbar before being evacuated and purged with nitrogen three times, and the mixture was stirred for 1 h at 90° C. The reaction mixture was diluted with water (20 mL), and the aqueous phase was extracted with dichloromethane (20 mL) three times. The combined organic layers were washed with brine, dried over sodium sulfate, filtered, and concentrated in vacuo. The resulting crude material was purified by silica gel chromatography (eluting with dichloromethane/methanol; 30:1). Concentration in vacuo resulted in 13-(3-fluoro-4-((4-methylpyrimidin-2-yl)oxy)phenyl)-3-((triisopropylsilyl)ethynyl)-6,7-dihydro-5H-pyrido[3,2-c]pyrimido[5',4':4,5]pyrrolo[1,2-a]azepin-12-amine (1 g, 60%) as a yellow amorphous solid.

3-ethynyl-13-(3-fluoro-4-((4-methylpyrimidin-2-yl)oxy)phenyl)-6,7-dihydro-5H-pyrido[3,2-c]pyrimido[5',4':4,5]pyrrolo[1,2-a]azepin-12-amine

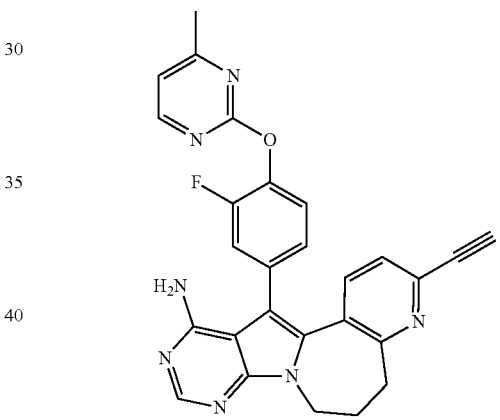

Step 8: A round bottomed flask was charged with 13-(3-fluoro-4-((4-methylpyrimidin-2-yl)oxy)phenyl)-3-((triisopropylsilyl)ethynyl)-6,7-dihydro-5H-pyrido[3,2-c]pyrimido[5',4':4,5]pyrrolo[1,2-a]azepin-12-amine (980 mg, 1.55 mmol), tetrahydrofuran (20 mL), TBAF (2.07 mL, 2.07 mmol), and a stirbar, and the solution was stirred for 1 h at 25° C. The reaction mixture was diluted with water (20 mL), and the aqueous phase was extracted with dichloromethane (20 mL) three times. The combined organic layers were washed with brine, dried over sodium sulfate, filtered, and concentrated in vacuo. The resulting crude material was purified by HPLC (Column: YMC-Actus Triart C18, 30*250, 5 um; Mobile Phase A:Water(10 MMOL/L NH$_4$HCO$_3$), Mobile Phase B:ACN; Flow rate:60 mL/min; Gradient:25 B to 60 B in 7 min; 254/220 nm; RT1:6.32). Lyophilization yielded 3-ethynyl-13-(3-fluoro-4-((4-methylpyrimidin-2-yl)oxy)phenyl)-6,7-dihydro-5H-pyrido[3,2-c]pyrimido[5',4':4,5]pyrrolo[1,2-a]azepin-12-amine (250 mg, 34%) as an off-white amorphous solid.

TABLE 51

Exemplary Compounds

| Compound | Structure | Proton NMR | MS [M + 1] |
|---|---|---|---|
| 3-ethynyl-13-(3-fluoro-4-((4-methylpyrimidin-2-yl)oxy)phenyl)-6,7-dihydro-5H-pyrido[3,2-c]pyrimido[5',4':4,5]pyrrolo[1,2-a]azepin-12-amine | 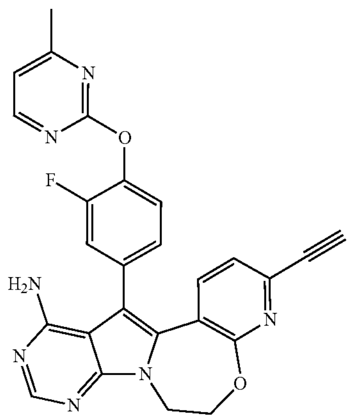 [SMILES: C#Cc1ccc2c(n1)OCCn1c-2c(-c2ccc(Oc3nccc(C)n3)c(F)c2)c2c(N)ncnc21] | ¹H NMR (400 MHz, DMSO-d₆) δ 8.50 (d, J = 5.0 Hz, 1H), 8.21 (s, 1H), 7.45-7.35 (m, 3H), 7.29-7.19 (m, 3H), 6.12 (s, 2H), 4.41 (s, 1H), 4.17 (d, J = 7.0 Hz, 2H), 2.92 (t, J = 7.1 Hz, 2H), 2.44 (s, 3H), 2.31 (q, J = 6.8 Hz, 2H). | 478.20 |
| (S)-1-((S)-4-(12-amino-3-ethynyl-6,7-dihydro-5H-pyrido[3,4-c]pyrimido[5',4':4,5]pyrrolo[1,2-a]azepin-13-yl)cyclohex-3-ene-1-carbonyl)pyrrolidine-2-carbonitrile | 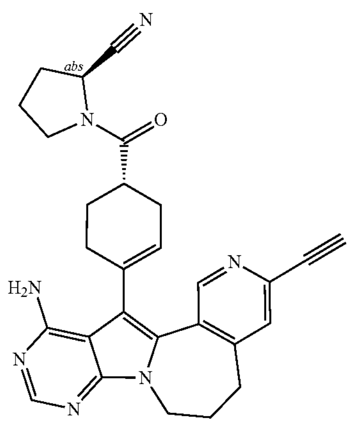 [SMILES: C#Cc1cc2c(cn1)-c1c(C3=CC[C@@H](C(=O)N4CCC[C@H]4C#N)CC3)c3c(N)ncnc3n1CCC2] | ¹H NMR (400 MHz, DMSO-d₆) δ 8.53 (s, 1H), 8.15 (s, 1H), 7.66 (s, 1H), 6.80 (s, 1H), 5.89 (s, 1H), 4.74 (dd, J = 7.4, 3.4 Hz, 1H), 4.43 (s, 1H), 4.09 (s, 2H), 3.77 (s, 1H), 3.53 (q, J = 8.4 Hz, 1H), 3.02-2.89 (m, 1H), 2.66 (d, J = 7.0 Hz, 2H), 2.34 (d, J = 6.1 Hz, 2H), 2.29-1.93 (m, 8H), 1.80-1.74 (m, 2H). | 478.25 |
| (S)-1-((R)-4-(12-amino-3-ethynyl-6,7-dihydro-5H-pyrido[3,4-c]pyrimido[5',4':4,5]pyrrolo[1,2-a]azepin-13-yl)cyclohex-3-ene-1-carbonyl)pyrrolidine-2-carbonitrile | 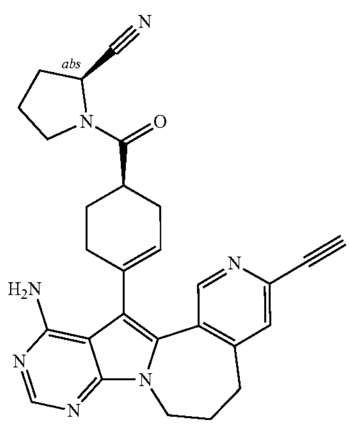 [SMILES: C#Cc1cc2c(cn1)-c1c(C3=CC[C@H](C(=O)N4CCC[C@H]4C#N)CC3)c3c(N)ncnc3n1CCC2] | ¹H NMR (400 MHz, DMSO-d₆) δ 8.53 (s, 1H), 8.11 (s, 1H), 7.65 (s, 1H), 6.61 (d, J = 46.1 Hz, 1H), 5.87 (s, 1H), 4.75 (dd, J = 7.9, 3.7 Hz, 1H), 4.42 (s, 1H), 4.20 (s, 1H), 3.96 (s, 1H), 3.83-3.47 (m, 2H), 2.98 (d, J = 5.9 Hz, 1H), 2.76-2.59 (m, 2H), 2.33 (s, 2H), 2.28-2.10 (m, 4H), 2.04 (d, J = 6.7 Hz, 4H), 1.80 (d, J = 6.2 Hz, 2H). | 478.25 |

1975
Example 53
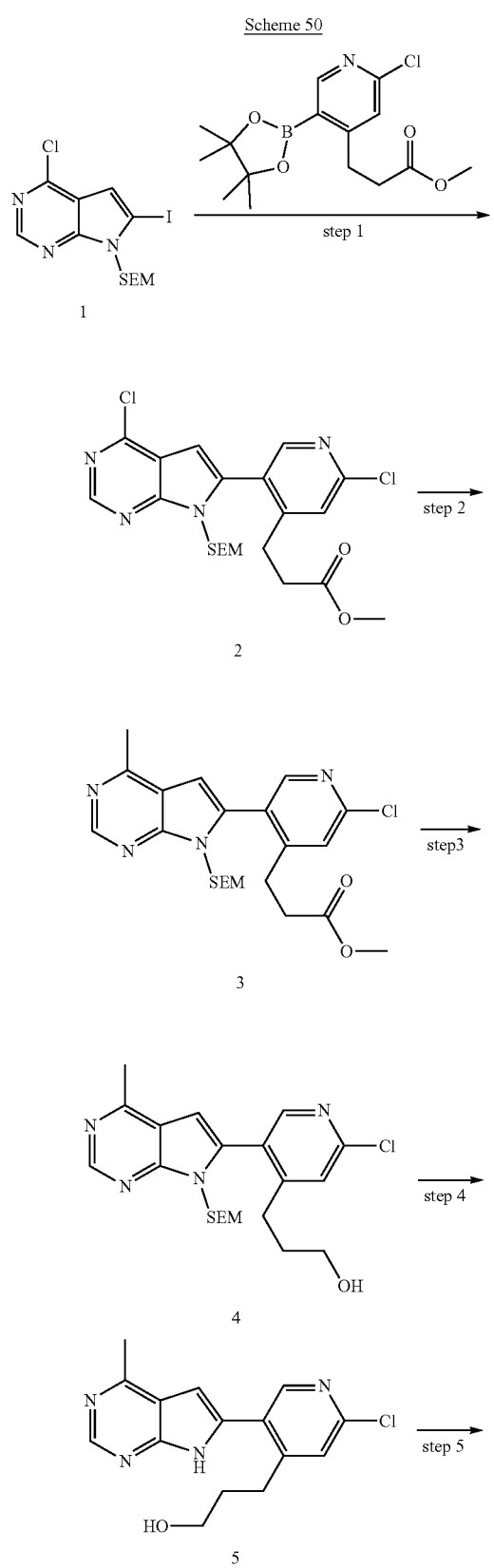
1976
-continued
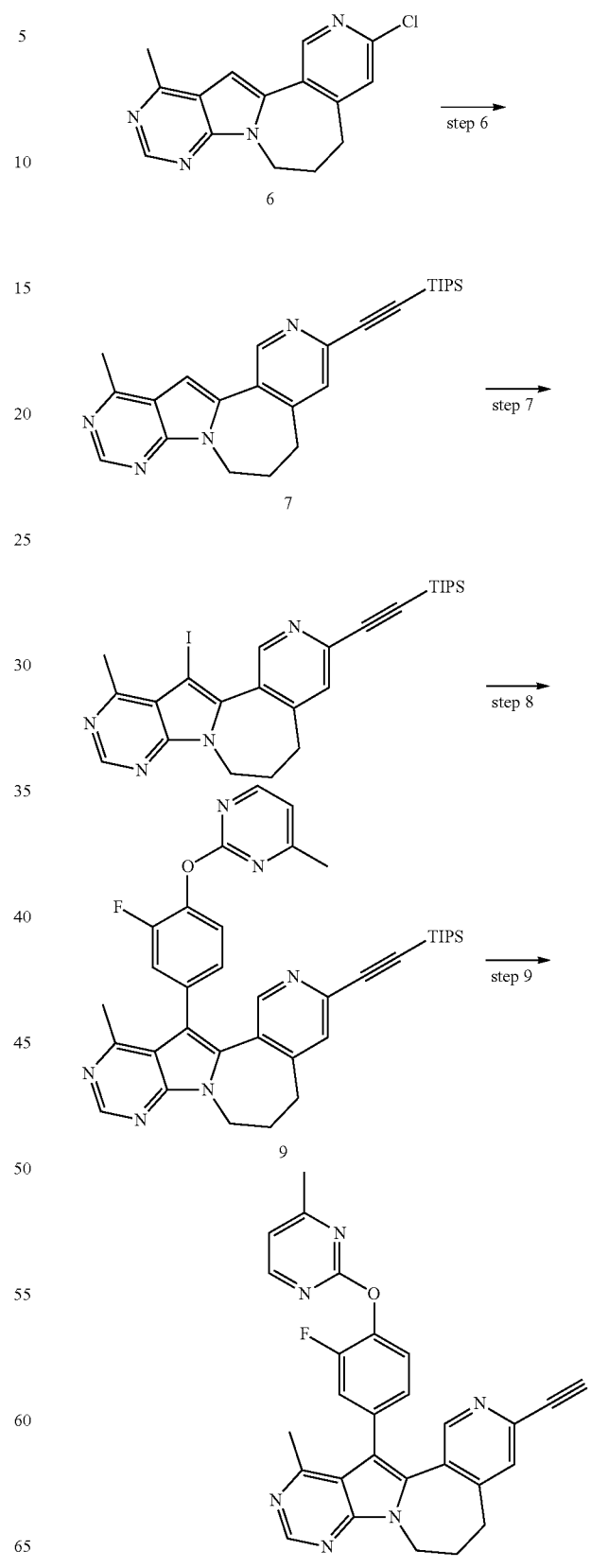

methyl 3-[2-chloro-5-(4-chloro-7-{[2-(trimethylsilyl)ethoxy]methyl}-7H-pyrrolo[2,3-d]pyrimidin-6-yl)pyridin-4-yl]propanoate

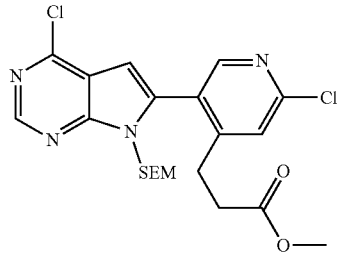 [SMILES: COC(=O)CCc1cc(Cl)ncc1-c1cc2c(Cl)ncnc2n1COCC[Si](C)(C)C]

Step 1: A resealable reaction vial was charged with 4-chloro-6-iodo-7-{[2-(trimethylsilyl)ethoxy]methyl}-7H-pyrrolo[2,3-d]pyrimidine (5 g, 12.2 mmol), {2-[6-chloro-4-(3-methoxy-3-oxopropyl)pyridin-3-yl]-4,5,5-trimethyl-1,3,2-dioxaborolan-4-yl}methylium (4.73 g, 14.6 mmol), CsF (5.54 g, 36.5 mmol), Pd(dtbpf)Cl$_2$ (795 mg, 1.22 mmol), and a stirbar before being evacuated and purged with nitrogen three times. Dioxane/H$_2$O (100 mL) was added, and the mixture was stirred for 1 h at 70° C. The reaction mixture was diluted with H$_2$O (400 mL), and the aqueous phase was extracted with dichloromethane (200 mL) three times. The combined organic layers were washed with brine, dried over sodium sulfate, filtered, and concentrated in vacuo. The resulting crude material was purified by silica gel chromatography (300 g column; eluting with PE/EA; 30/1). Concentration in vacuo resulted in methyl 3-[2-chloro-5-(4-chloro-7-{[2-(trimethylsilyl)ethoxy]methyl}-7H-pyrrolo[2,3-d]pyrimidin-6-yl)pyridin-4-yl]propanoate (2.00 g, 34.0%) as a black amorphous solid.

methyl 3-[2-chloro-5-(4-methyl-7-{[2-(trimethylsilyl)ethoxy]methyl}-7H-pyrrolo[2,3-d]pyrimidin-6-yl)pyridin-4-yl]propanoate

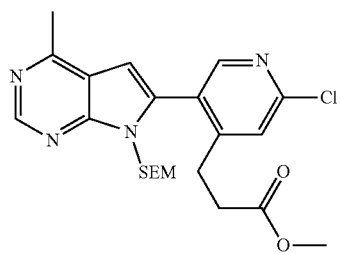 [SMILES: COC(=O)CCc1cc(Cl)ncc1-c1cc2c(C)ncnc2n1COCC[Si](C)(C)C]

Step 2: A resealable reaction vial was charged with methyl 3-[2-chloro-5-(4-chloro-7-{[2-(trimethylsilyl)ethoxy]methyl}-7H-pyrrolo[2,3-d]pyrimidin-6-yl)pyridin-4-yl]propanoate (1.9 g, 3.94 mmol), Pd(PPh$_3$)$_4$ (455 mg, 394 μmol), dimethylformamide (25 mL) and a stirbar before being evacuated and purged with nitrogen three times. Dimethylzinc (413 mg, 4.33 mmol) was added, and the mixture was stirred for 2 h at 90° C. The reaction mixture was diluted with H$_2$O (100 mL), and the aqueous phase was extracted with EA (80 mL) three times. The combined organic layers were washed with brine, dried over sodium sulfate, filtered, and concentrated in vacuo. The resulting crude material was purified by silica gel chromatography (300 g column; eluting with PE/EA; 10/1). Concentration in vacuo resulted in methyl 3-[2-chloro-5-(4-methyl-7-{[2-(trimethylsilyl)ethoxy]methyl}-7H-pyrrolo[2,3-d]pyrimidin-6-yl)pyridin-4-yl]propanoate (850 mg, 46.9%) as a black amorphous solid.

3-[2-chloro-5-(4-methyl-7-{[2-(trimethylsilyl)ethoxy]methyl}-7H-pyrrolo[2,3-d]pyrimidin-6-yl)pyridin-4-yl]propan-1-ol

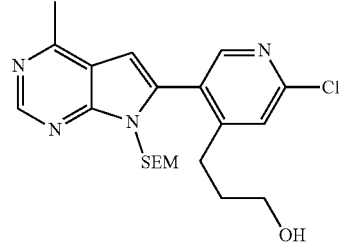 [SMILES: Cc1ncnc2c1cc(-c1cnc(Cl)cc1CCCO)n2COCC[Si](C)(C)C]

Step 3: A round bottomed flask was charged with methyl 3-[2-chloro-5-(4-methyl {[2-(trimethylsilyl)ethoxy]methyl}-7H-pyrrolo[2,3-d]pyrimidin-6-yl)pyridin-4-yl]propanoate (800 mg, 1.73 mmol), tetrahydrofuran (10 mL) and a stirbar. Alumane lithium hydride (98.2 mg, 2.59 mmol) was added, and the solution was stirred at −30° C. The reaction mixture was quenched with H$_2$O (50 mL), and the aqueous phase was extracted with dichloromethane (50 mL) three times. The combined organic layers were washed with brine, dried over sodium sulfate, filtered, and concentrated in vacuo resulted in 3-[2-chloro-5-(4-methyl-7-{[2-(trimethylsilyl)ethoxy]methyl}-7H-pyrrolo[2,3-d]pyrimidin-6-yl)pyridin-4-yl]propan-1-ol (570 mg, 76.1%) as an off-white amorphous solid.

3-(2-chloro-5-{4-methyl-7H-pyrrolo[2,3-d]pyrimidin-6-yl}pyridin-4-yl)propan-1-ol

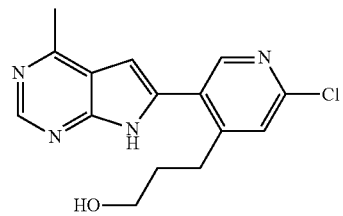 [SMILES: Cc1ncnc2[nH]c(-c3cnc(Cl)cc3CCCO)cc12]

Step 4: A round bottomed flask was charged with 3-[2-chloro-5-(4-methyl-7-{[2-(trimethylsilyl)ethoxy]methyl}-7H-pyrrolo[2,3-d]pyrimidin-6-yl)pyridin-4-yl]propan-1-ol (550 mg, 1.27 mmol) and a stirbar. MeOH/HCl (10 mL) was added, and the solution was stirred for 1 h at 40° C. The solution was concentrated in vacuo. Then MeOH (5 mL) was added, ethylenediamine (76.3 mg, 1.27 mmol) was added, and the solution was stirred for 30 min at r.t. The reaction mixture was diluted with H$_2$O (50 mL), and the aqueous phase was extracted with DCM (50 mL) three times. The combined organic layers were washed with brine, dried over sodium sulfate, filtered, and concentrated in vacuo resulted in 3-(2-chloro-5-{4-methyl-7H-pyrrolo[2,3-d]pyrimidin-6-yl}pyridin-4-yl)propan-1-ol (360 mg, 93.7%) as an off-white amorphous solid.

3-chloro-12-methyl-6,7-dihydro-5H-pyrido[3,4-c]pyrimido[5',4':4,5]pyrrolo[1,2-a]azepine

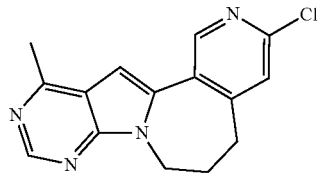 [SMILES: Cc1ncnc2c1cc1n2CCCc2cc(Cl)ncc2-1]

Step 5: A resealable reaction vial was charged with 3-(2-chloro-5-{4-methyl-7H-pyrrolo[2,3-d]pyrimidin-6-yl}pyridin-4-yl)propan-1-ol (340 mg, 1.12 mmol), PPh₃ (510 mg, 1.68 mmol), tetrahydrofuran (10 mL) and a stirbar before being evacuated and purged with nitrogen three times. DIAD (655 mg, 1.68 mmol) was added, and the mixture was stirred for 1 h at 40° C. The reaction mixture was diluted with H₂O (50 mL), and the aqueous phase was extracted with dichloromethane (50 mL) three times. The combined organic layers were washed with brine, dried over sodium sulfate, filtered, and concentrated in vacuo. The residue was purified by silica gel chromatography (300 g column; eluting with PE/EA; 1/1). Concentration in vacuo resulted in 3-chloro-12-methyl-6,7-dihydro-5H-pyrido[3,4-c]pyrimido[5',4':4,5]pyrrolo[1,2-a]azepine (180 mg, 56.6%) as an off-white amorphous solid.

12-methyl-3-((triisopropylsilyl)ethynyl)-6,7-dihydro-5H-pyrido[3,4-c]pyrimido[5',4':4,5]pyrrolo[1,2-a]azepine

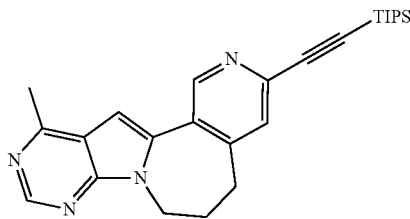

Step 6: A resealable reaction vial was charged with 3-chloro-12-methyl-6,7-dihydro-5H-pyrido[3,4-c]pyrimido[5',4':4,5]pyrrolo[1,2-a]azepine (160 mg, 561 µmol), TEA (169 mg, 1.68 mmol), CuI (42.5 mg, 224 µmol), Pd(pddf)Cl₂ (81.9 mg, 112 µmol), tris(propan-2-yl)silane (88.8 mg, 561 µmol) and a stirbar before being evacuated and purged with nitrogen three times. Dimethylformamide (10 mL) was added, and the mixture was stirred for 2 h at 70° C. The reaction mixture was diluted with H₂O (50 mL), and the aqueous phase was extracted with EA (20 mL) three times. The combined organic layers were washed with brine, dried over sodium sulfate, filtered, and concentrated in vacuo. The resulting crude material was purified by silica gel chromatography (50 g column; eluting with hexanes/ethyl acetate; 15/1). Concentration in vacuo resulted in 12-methyl-3-((triisopropylsilyl)ethynyl)-6,7-dihydro-5H-pyrido[3,4-c]pyrimido[5',4':4,5]pyrrolo[1,2-a]azepine (150 mg, 62.2%) as an orange amorphous solid.

13-iodo-12-methyl-3-((triisopropylsilyl)ethynyl)-6,7-dihydro-5H-pyrido[3,4-c]pyrimido[5',4':4,5]pyrrolo[1,2-a]azepine

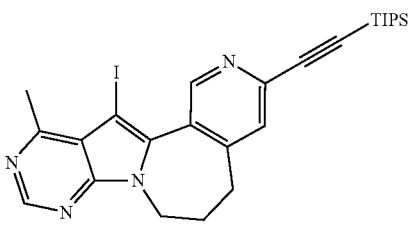

Step 7: A round bottomed flask was charged with 12-methyl-3-((triisopropylsilyl)ethynyl)-6,7-dihydro-5H-pyrido[3,4-c]pyrimido[5',4':4,5]pyrrolo[1,2-a]azepine (150 mg, 348 µmol), dichloromethane (5 mL), TFA (118 mg, 1.04 mmol) and a stirbar. 1-iodopyrrolidine-2,5-dione (85.9 mg, 382 µmol) was added at 0° C., and the solution was stirred for 30 min at room temperature. The mixture was quenched with saturated NaHSO₃ aqueous solution until the pH to 8-9, extracted with DCM (100 mL*3), the organic phase was combined and dried with Na₂SO₄, Concentration in vacuo resulted in 13-iodo-12-methyl-3-((triisopropylsilyl)ethynyl)-6,7-dihydro-5H-pyrido[3,4-c]pyrimido[5',4':4,5]pyrrolo[1,2-a]azepine (180 mg, 93.2%).

13-(3-fluoro-4-((4-methylpyrimidin-2-yl)oxy)phenyl)-12-methyl-3-((triisopropylsilyl)ethynyl)-6,7-dihydro-5H-pyrido[3,4-c]pyrimido[5',4':4,5]pyrrolo[1,2-a]azepine

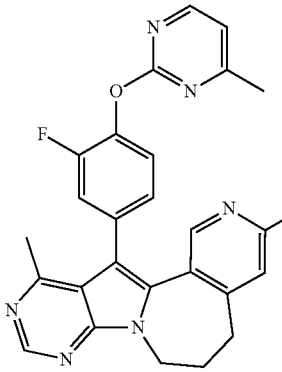

Step 8: A resealable reaction vial was charged with 13-iodo-12-methyl-3-((triisopropylsilyl)ethynyl)-6,7-dihydro-5H-pyrido[3,4-c]pyrimido[5',4':4,5]pyrrolo[1,2-a]azepine (160 mg, 287 µmol), 2-[2-fluoro-4-(4,4,5,5-tetramethyl-1,3,2-dioxaborolan-2-yl)phenoxy]-4-methylpyrimidine (113 mg, 344 µmol), K₃PO₄ (182 mg, 861 µmol), Pd(PPh₃)₄ (331 mg, 287 µmol), and a stirbar before being evacuated and purged with nitrogen three times. DME/H₂O (6 mL) was added, and the mixture was stirred for 1 h at 90° C. The reaction mixture was diluted with H₂O (50 mL), the aqueous phase was extracted with dichloromethane (30 mL) three times. The combined organic layers were washed with brine, dried over sodium sulfate, filtered, and concentrated in vacuo. The resulting crude material was purified by silica gel chromatography (50 g column; eluting with hexanes/ethyl acetate; 1/1). Concentration in vacuo resulted in 13-(3-fluoro-4-((4-methylpyrimidin-2-yl)oxy)phenyl)-12-methyl-3-((triisopropylsilyl)ethynyl)-6,7-dihydro-5H-pyrido[3,4-c]pyrimido[5',4':4,5]pyrrolo[1,2-a]azepine (100 mg, 55.2%) as a black amorphous solid.

3-ethynyl-13-(3-fluoro-4-((4-methylpyrimidin-2-yl)oxy)phenyl)-12-methyl-6,7-dihydro-5H-pyrido[3,4-c]pyrimido[5',4':4,5]pyrrolo[1,2-a]azepine

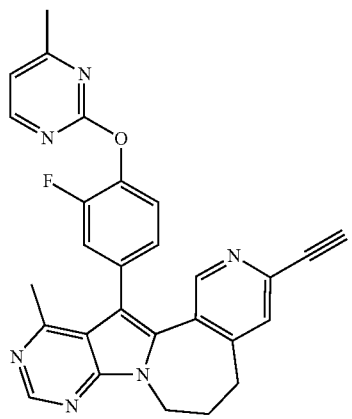 [SMILES: C#Cc1cc2c(cn1)-c1c(-c3ccc(Oc4nccc(C)n4)c(F)c3)c3c(C)ncnc3n1CCC2]

Step 9: A round bottomed flask was charged with 13-(3-fluoro-4-((4-methylpyrimidin-2-yl)oxy)phenyl)-12-methyl-3-((triisopropylsilyl)ethynyl)-6,7-dihydro-5H-pyrido[3,4-c]pyrimido[5',4':4,5]pyrrolo[1,2-a]azepine (90 mg, 142 μmol), tetrahydrofuran (1 mL) and a stirbar. TBAF (34.4 mg, 142 μmol) was added, and the solution was stirred at r.t. The reaction mixture was diluted with DCM (100 mL), The combined organic layers were washed with H₂O (200 ml) six times, dried over sodium sulfate, filtered, and concentrated in vacuo. The resulting crude material was purified by prep-HPLC (Column: YMC-Actus Triart C18, 20*250 MM, 5 um, 12 nm; Mobile Phase A:undefined, Mobile Phase B:undefined; Flow rate:60 mL/min; Gradient:40 B to 65 B in 8 min; 220/254 nm; RT1:7.07). Lyophilization yielded 3-ethynyl-13-(3-fluoro-4-((4-methylpyrimidin-2-yl)oxy)phenyl)-12-methyl-6,7-dihydro-5H-pyrido[3,4-c]pyrimido[5',4':4,5]pyrrolo[1,2-a]azepine (18.9 mg, 27.9%) as an off-white amorphous solid.

TABLE 52

Exemplary Compound

| Compound | Structure | Proton NMR | MS [M + 1] |
|---|---|---|---|
| 3-ethynyl-13-(3-fluoro-4-((4-methylpyrimidin-2-yl)oxy)phenyl)-12-methyl-6,7-dihydro-5H-pyrido[3,4-c]pyrimido[5',4':4,5]pyrrolo[1,2-a]azepine | 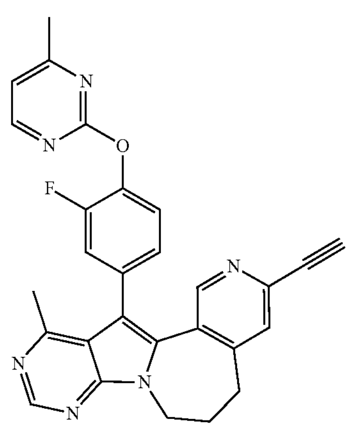 [SMILES: C#Cc1cc2c(cn1)-c1c(-c3ccc(Oc4nccc(C)n4)c(F)c3)c3c(C)ncnc3n1CCC2] | $^1$H NMR (400 MHz, DMSO-$d_6$) δ 8.75 (s, 1H), 8.51 (d, J = 5.1 Hz, 1H), 8.12 (s, 1H), 7.71 (s, 1H), 7.50 (d, J = 11.2 Hz, 1H), 7.42 (t, J = 8.3 Hz, 1H), 7.29 (d, J = 8.4 Hz, 1H), 7.21 (d, J = 5.0 Hz, 1H), 4.44 (s, 1H), 4.27 (t, J = 6.4 Hz, 2H), 2.80 (t, J = 1.0 Hz, 2H), 2.43 (d, J = 9.3 Hz, 6H), 2.29 (t, J = 6.9 Hz, 2H). | 477.25 |

Example 54

13-(3-fluoro-4-((4-methylpyrimidin-2-yl)oxy)phenyl)-3 ((triisopropylsilyl)ethynyl)-6,7-dihydro-5H-pyrido[3,4-c]pyrimido[5',4':4,5]pyrrolo[1,2-a]azepin-12-amine Scheme 51

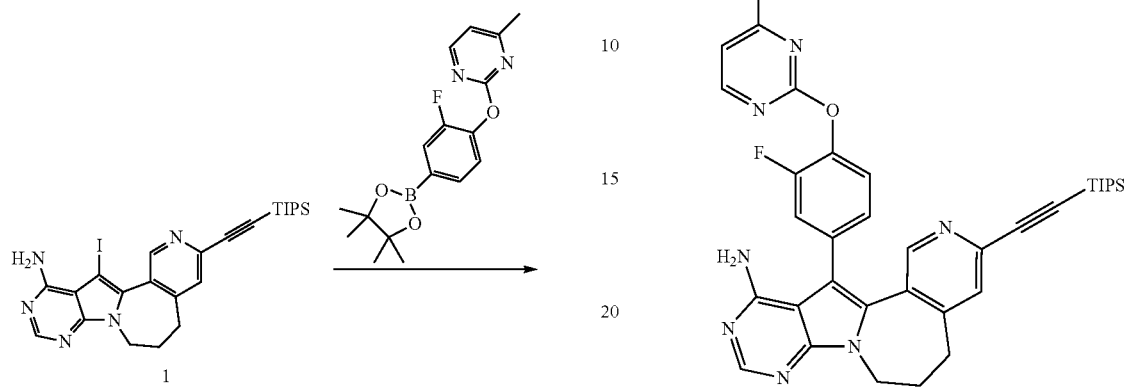

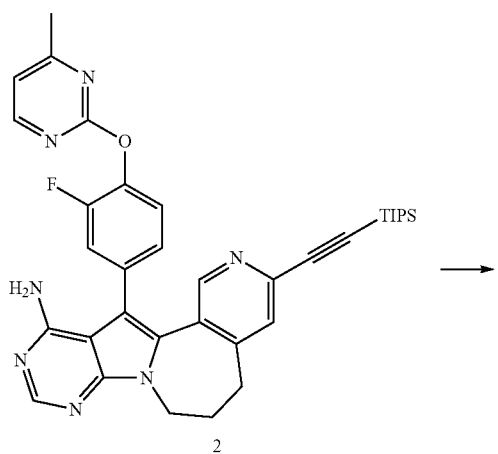

A resealable reaction vial was charged with 13-iodo-3-((triisopropylsilyl)ethynyl)-6,7-dihydro-5H-pyrido[3,4-c]pyrimido[5',4':4,5]pyrrolo[1,2-a]azepin-12-amine (180 mg, 322 µmol), 2-[2-fluoro-4-(4,4,5,5-tetramethyl-1,3,2-dioxaborolan-2-yl)phenoxy]-4-methylpyrimidine (159 mg, 482 µmol), K₃PO₄ (204 mg, 965 µmol), Pd(PPh₃)₄ (37.1 mg, 32.1 µmol) and a stirbar before being evacuated and purged with nitrogen three times. DME:H₂O=10:1(3 mL) was added, and the solution was stirred for 2 h at 90° C. The reaction mixture was quenched with water, extracted with DCM, dried over Na₂SO₄, concentrated in vacuo. The resulting crude material was purified by prep-TLC(DCM:MeOH=15:1). Concentration in vacuo resulted in 13-(3-fluoro-4-((4-methylpyrimidin-2-yl)oxy)phenyl)-3 ((triisopropylsilyl)ethynyl)-6,7-dihydro-5H-pyrido[3,4-c]pyrimido[5',4':4,5]pyrrolo[1,2-a]azepin-12-amine (90.0 mg, 44%) as a yellow amorphous solid.

3-(ethynyl-d)-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine

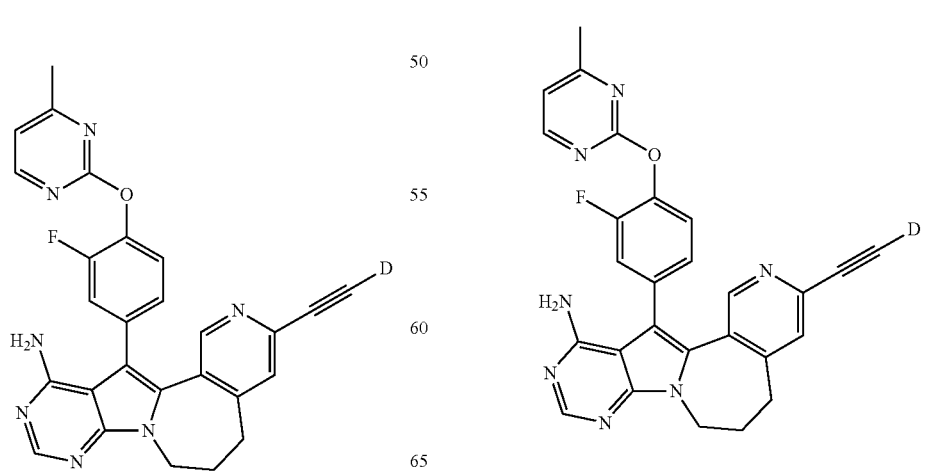

A resealable reaction vial was charged with 13-(3-fluoro-4-((4-methylpyrimidin-2-yl)oxy)phenyl)-3 ((triisopropylsilyl)ethynyl)-6,7-dihydro-5H-pyrido[3,4-c]pyrimido[5',4':4,5]pyrrolo[1,2-a]azepin-12-amine (90 mg, 141 μmol), TBAF (14.7 mg, 56.4 μmol), D2O (310 mg, 15.5 mmol) tetrahydrofuran (2 mL) and a stirbar. The reaction mixture was stirred for 30 min at 100° C. in microwave reactor. After cooling, the solvent was removed, the residue was purified by prep-TLC (DCM:MeOH=15:1). Then recrystallized from ACN resulted in 3-(ethynyl-d)-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine (11.8 mg, 17%) as an off-white amorphous solid.

TABLE 53

Exemplary Compound

| Compound | Structure | Proton NMR | MS [M + 1] |
|---|---|---|---|
| 3-(ethynyl-d)-13-(3-fluoro-4-((4-methylpyrimidin-2-yl)oxy)phenyl)-6,7-dihydro-5H-pyrido[3,4-c]pyrimido[5',4':4,5]pyrrolo[1,2-a]azepin-12-amine | 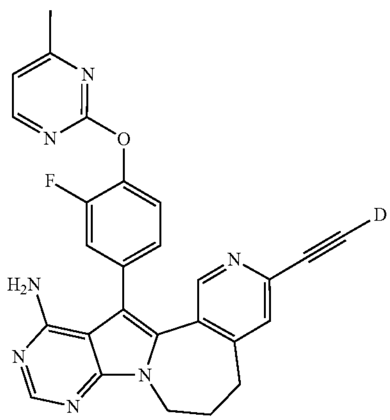 [SMILES: [2H]C#Cc1cc2c(cn1)-c1c(-c3ccc(Oc4nccc(C)n4)c(F)c3)c3c(N)ncnc3n1CCC2] | $^1$H NMR (400 MHz, DMSO-$d_6$) δ 8.51 (d, J = 5.0 Hz, 1H), 8.21 (s, 1H), 8.04 (s, 1H), 7.68 (s, 1H), 7.49-7.33 (m, 2H), 7.28-7.18 (m, 2H), 5.76 (s, 1H), 4.15 (t, J = 6.7 Hz, 2H), 2.80 (t, J = 7.2 Hz, 2H), 2.45 (s, 3H), 2.30-2.22 (m, 2H). | 479.15 |

Example 55

Compounds of the present invention were also tested in a FGFR2 Biochemical Caliper Assay. Compounds were prepared in 10 mM DMSO solution and serially diluted into 11 concentrations by 3-fold dilution. Into a 384 well plate were added 200 nL of compound solution and 15 uL of 1.3× enzyme solution (FGFR2 protein (0.06 nM), FLPeptide30 (1.5 uM), MgCl$_2$ (10 mM)) was added and the plate was incubated at room temperature for 30 minutes. 5 uL of ATP solution (100 uM) was added to start the reaction and the plate was incubated for 90 minutes, then 70 uL of stopping buffer (0.5M EDTA) was added to terminate the reaction. Each well was analyzed using EZ reader.

Results of the FGFR2 Biochemical Caliper Assay are presented in Table 1. Compounds having an IC50 less than or equal to 100 nM are represented as "A"; compounds having an IC50 greater than 100 nM but less than or equal to 250 nM are represented as "13"; compounds having an IC50 greater than 250 nM but less than or equal to 1 μM are represented as "C"; and compounds having an IC50 greater than 1 μM but less than or equal to 100 μM are represented as "D".

Example 56

Compounds of the present invention were also tested in a SNU16 Cancer Cell Line Proliferation Assay, Test compounds were prepared in a 10 mM DMSO stock solution. 45 uL of stock solution was transferred to a 384 well plate, and a 3-fold 11-point dolution was performed. SNU16 cells in a 384 well cell culture plate were seeded and incubated at 37 degrees for 24 hours. 40 nL of each concentration of compound was transferred from the compound plate to a corresponding well in the cell culture plate by Echo550 liquid handler. The plates were incubated for 96 hours, then equilibrated to room temperature for 15 minutes. 20 uL of CellTiter Glo reagent is added into each well, then the plate was shaken gently for 30 minutes at room temperature. Chemiluminescence was then read on an EnVision reader.

Results of the SNU16 Cancer Cell Line Proliferation Assay are presented in Table 1, Compounds having an IC50 less than or equal to 100 nM are represented as "A"; compounds having an IC50 greater than 100 nM but less than or equal to 250 nM are represented as "B"; compounds having an IC50 greater than 250 nM but less than or equal to 1 μM are represented as "C"; and compounds having an IC50 greater than 1 μM but less than or equal to 100 μM are represented as "D".

INCORPORATION BY REFERENCE

All publications and patents mentioned herein are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the present disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A compound, which is

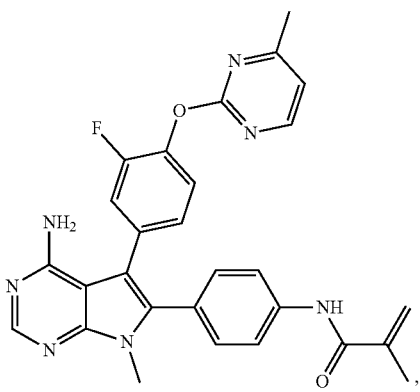 [SMILES: C=C(C)C(=O)Nc1ccc(-c2c(-c3ccc(Oc4nccc(C)n4)c(F)c3)c3c(N)ncnc3n2C)cc1]

or a pharmaceutically acceptable salt thereof.

2. A pharmaceutical composition comprising a compound:

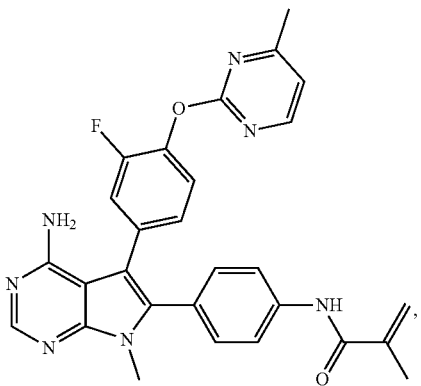 [SMILES: C=C(C)C(=O)Nc1ccc(-c2c(-c3ccc(Oc4nccc(C)n4)c(F)c3)c3c(N)ncnc3n2C)cc1]

or a pharmaceutically acceptable salt thereof, and a pharmaceutically acceptable carrier, adjuvant, or vehicle.

* * * * *

UNITED STATES PATENT AND TRADEMARK OFFICE
CERTIFICATE OF CORRECTION

| | | |
|---|---|---|
| PATENT NO. | : 11,780,845 B2 | Page 1 of 1 |
| APPLICATION NO. | : 18/162127 | |
| DATED | : October 10, 2023 | |
| INVENTOR(S) | : Bakary-Barry Touré | |

It is certified that error appears in the above-identified patent and that said Letters Patent is hereby corrected as shown below:

In the Specification

Please add the following section in Column 1, immediately after the "CROSS REFERENCE TO RELATED APPLICATIONS" section:
JOINT RESEARCH AGREEMENT
The present disclosure was made by or on behalf of the below listed parties to a joint research agreement. The joint research agreement was in effect on or before the date the present disclosure was made, and the present disclosure was made as a result of activities undertaken within the scope of the joint research agreement. The parties to the joint research agreement are 1) RELAY THERAPEUTICS, INC. and 2) D.E. SHAW RESEARCH, LLC.

Signed and Sealed this
Twenty-first Day of November, 2023

Katherine Kelly Vidal
*Director of the United States Patent and Trademark Office*